(12) United States Patent
Blake et al.

(10) Patent No.: US 10,689,377 B2
(45) Date of Patent: *Jun. 23, 2020

(54) KRAS G12C INHIBITORS

(71) Applicants: Mirati Therapeutics, Inc., San Diego, CA (US); Array BioPharma Inc., Boulder, CO (US)

(72) Inventors: James F. Blake, Boulder, CO (US); Laurence E. Burgess, Boulder, CO (US); Mark Joseph Chicarelli, Boulder, CO (US); James Gail Christensen, San Diego, CA (US); Adam Cook, Boulder, CO (US); Jay Bradford Fell, Boulder, CO (US); John P. Fischer, Boulder, CO (US); Matthew Arnold Marx, San Diego, CA (US); Macedonio J. Mejia, Boulder, CO (US); Pavel Savechenkov, Boulder, CO (US); Guy P. A. Vigers, Boulder, CO (US); Christopher Ronald Smith, San Diego, CA (US); Martha E. Rodriguez, Boulder, CO (US)

(73) Assignees: Mirati Therapeutics, Inc., San Diego, CA (US); Array Biopharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/191,190

(22) Filed: Nov. 14, 2018

(65) Prior Publication Data
US 2019/0144444 A1 May 16, 2019

Related U.S. Application Data

(60) Provisional application No. 62/586,775, filed on Nov. 15, 2017.

(51) Int. Cl.
*C07D 471/04* (2006.01)
*A61P 35/00* (2006.01)
*C07D 491/08* (2006.01)

(52) U.S. Cl.
CPC ........... *C07D 471/04* (2013.01); *A61P 35/00* (2018.01); *C07D 491/08* (2013.01)

(58) Field of Classification Search
CPC .................................................... C07D 471/04
USPC .................................................... 514/210.21
See application file for complete search history.

(56) References Cited

U.S. PATENT DOCUMENTS

| 8,163,763 | B2 | 4/2012 | Bergeron et al. |
| 9,562,019 | B2 | 2/2017 | Djaballah et al. |
| 9,840,516 | B2 | 12/2017 | Li et al. |
| 10,125,134 | B2 * | 11/2018 | Blake ............... C07D 519/00 |
| 2003/0191143 | A1 | 10/2003 | Pitts et al. |
| 2009/0253693 | A1 | 10/2009 | Koltun et al. |
| 2010/0081654 | A1 | 4/2010 | Stockwell et al. |
| 2011/0269244 | A1 | 11/2011 | Petter et al. |
| 2013/0029978 | A1 | 1/2013 | Kamino et al. |
| 2014/0288045 | A1 | 9/2014 | Ren et al. |
| 2015/0175558 | A1 | 6/2015 | Stockwell et al. |
| 2015/0239900 | A1 | 8/2015 | Li et al. |
| 2016/0031898 | A1 | 2/2016 | Ren et al. |
| 2016/0108019 | A1 | 4/2016 | Li et al. |
| 2016/0166571 | A1 | 6/2016 | Janes et al. |
| 2016/0229836 | A1 | 8/2016 | Stockwell et al. |
| 2016/0264627 | A1 | 9/2016 | Henning et al. |
| 2016/0297774 | A1 | 10/2016 | Li et al. |
| 2017/0022184 | A1 | 1/2017 | Li et al. |
| 2017/0115303 | A1 | 4/2017 | Cravatt et al. |
| 2017/0190672 | A1 | 7/2017 | Mani et al. |
| 2017/0197945 | A1 | 7/2017 | Li et al. |
| 2018/0015087 | A1 | 1/2018 | Liu et al. |
| 2018/0118757 | A1 | 5/2018 | Li et al. |
| 2018/0118761 | A1 | 5/2018 | Sebti et al. |
| 2018/0127396 | A1 | 5/2018 | Li et al. |
| 2018/0141927 | A1 | 5/2018 | Li et al. |
| 2018/0155348 | A1 | 6/2018 | Li et al. |
| 2018/0162812 | A1 | 6/2018 | Ren et al. |
| 2018/0177767 | A1 | 6/2018 | Lanman et al. |
| 2018/0194748 | A1 | 7/2018 | Li et al. |
| 2018/0201610 | A1 | 7/2018 | Tao et al. |
| 2018/0273515 | A1 | 9/2018 | Li et al. |
| 2018/0273523 | A1 | 9/2018 | Li et al. |
| 2018/0273577 | A1 | 9/2018 | Revenko et al. |
| 2018/0282307 | A1 | 10/2018 | Li et al. |

(Continued)

FOREIGN PATENT DOCUMENTS

WO 02/053558 A1 7/2002
WO 02/087513 A2 11/2002
(Continued)

OTHER PUBLICATIONS

Sung, Y. et al. "Mutagenesis of the H-ras p21 at Glycine-60 Residue Disrupts GTP-Induced Conformational Change", Biochemistry 1995, 34, 3470-3477, American Chemical Society.

Tape, C. et al., "Oncogenic KRAS Regulates Tumor Cell Signaling via Stromal Reciprocation", Cell 165, 1-11May 5, 2016.

Thierry, A. et al., "Clinical validation of the detection of KRAS and BRAF mutations from circulating tumor DNA", Nature Medicine, vol. 20, No. 4, pp. 430-436 , Apr. 2014.

Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.

Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.

(Continued)

*Primary Examiner* — Kahsay Habte
(74) *Attorney, Agent, or Firm* — Wood, Phillips, Katz, Clark & Mortimer

(57) ABSTRACT

The present invention relates to compounds that inhibit KRas G12C. In particular, the present invention relates to compounds that irreversibly inhibit the activity of KRas G12C, pharmaceutical compositions comprising the compounds and methods of use therefor.

57 Claims, No Drawings

(56) References Cited

U.S. PATENT DOCUMENTS

| | | |
|---|---|---|
| 2018/0282308 A1 | 10/2018 | Li et al. |
| 2018/0289683 A1 | 10/2018 | Mccormick et al. |

FOREIGN PATENT DOCUMENTS

| | | |
|---|---|---|
| WO | 2007/146122 A2 | 12/2007 |
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2019/051291 A1 | 3/2019 |
| WO | 2019/110751 A1 | 6/2019 |
| WO | 2019/150305 A1 | 8/2019 |
| WO | 2019/155399 A1 | 8/2019 |

OTHER PUBLICATIONS

Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.

Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.

Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.

Wood, K. et al., "Reply" Comments & Response, Letters JAMA Oncology Published online Jul. 21, 2016, American Medical Association.

Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.

Xiong, Y. et al., "Covalent Guanosine Mimetic Inhibitors of G12C KRAS" ACS Med. Chem. Lett. 2017, 8, 61-66, DOI: 10.1021/acsmedchemlett6b00373; 2016 American Chemical Society, ACS Publications.

Janes et al., "Targeting KRAS Mutant Cancers with a Covalent G12C-Specific Inhibitor", Cell 172, 578-589, Jan. 25, 2018.

Singh et al., "A Gene Expression Signature Associated with K-Ras Addiction" Reveals Regulators of EMT and Tumor Cell Survival, Cancer Cell 15, p. 489-500, Jun. 2, 2009.

Stephen et al., "Dragging Ras Back in the Ring", Cancer Cell 25, p. 272, Mar. 17, 2014.

Zhu et al., "Inhibition of KRAS-driven tumorigenicity by interruption of an autocrine cytokine circuit", doi:10.1158/2159-8290.CD-13/0646; Cancer Discovery Published OnlineFirst Jan. 20, 2014.

Simanshu et al., "RAS Proteins and Their Regulators in Human Disease", Cell 170, p. 17, Jun. 29, 2017.

Pacold et al., "Crystal Structure and Functional Analysis of Ras Binding to Its Effector Phosphoinositide 3-Kinase gamma", Cell, vol. 103, p. 931-943, Dec. 8, 2000.

Lech-Gustav et al., "The Renaissance of Ras", ACS Chem. Biol., 2014, 9, 2447-2458.

Karachaliou et al., "KRAS Mutations in Lung Cancer", Clinical Lung Cancer, vol. 14, No. 3, p. 2015-14, 2013.

Schwartz et al., "Covalent EGFR inhibitor analysis reveals importance of reversible interactions to potency and mechanisms of drug resistance", PNAS, vol. 111, No. 1, p. 173-178, Jan. 7, 2014.

Sun et al., "A method for the second-site screening of K-Ras in the presence of a covalently attached first-site ligand", J. Biomol. NMR (2014) vol. 60 p. 11-14.

Kyriakis, J., "Thinking Outside the Box about Ras", J. Biol. Chem. 2009, 284:10993-10994, published online Dec. 17, 2008.

Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.

Serafimova et al., "Reversible targeting of noncatalytic cysteines with chemically tuned electrophiles", Nat Chem Biol.; 8(5):471-476. doi:10.1038/nchembio.925.

Walker et al., "Structural insights into phosphoinositide 3-kinase catalysis and signalling", Nature vol. 402, p. 18 Nov. 1999; www.nature.com.

Barbie et al., "Systematic RNA interference reveals that oncogenic KRAS-driven cancers require TBK1", Nature, vol. 462, p. 108, Nov. 5, 2009; doi:10.1038/nature08460.

Zimmerman et al., "Small molecule inhibition of the KRAS-PDEdelta interaction impairs oncogenic KRAS signalling", Nature, vol. 497, p. 638, May 30, 2013.

Karnoub et al., "Ras oncogenes: split personalities", Nature Reviews, molecular Cell Biology, vol. 9, Jul. 2008 p. 517.

Nassar et al., "Ras/Rap effector specificity determined by charge reversal", Nature Structural Biology, vol. 3, No. 8, Aug. 1996.

de Rooij et al., "Minimal Ras-binding domain of Raf1 can be used as an activation-specific probe for Ras", Oncogene (1997)14, 623-625, 1997 Stockton Press.

Cox et al., "The dark side of RAs: regulation of apoptosis", Oncogene (2003) 22, 8999-9006, 2003 Nature Publishing Group.

Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.

Grant et al., "Novel Allosteric Sites on Ras for Lead Generation", PLOS One, vol. 6, Issue 10, Oct. 2011.

Maegley et al., "Ras-catalyzed hydrolysis of GTP: A new perspective from model studies", Proc. Natl. Acad. Sci. USA, vol. 93, pp. 8160-8166, Aug. 1996.

Ahmadian et al., "Guanosine triphosphatase stimulation of oncogenic Ras mutants", Proc. Natl. Acad. Sci. USA, vol. 96, pp. 7065-7070, Jun. 1999.

Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.

(56) References Cited

OTHER PUBLICATIONS

Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-affector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36(2): 65-77. doi:10.1016/j.tibs.2010.09.006.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
Martin, James S. et al., "Characterising covalent warhead reactivity", Bioorganic & Medicinal Chemistry, 27 (2019) 2066-2074.
Kessler et al., "Drugging and undruggable pocket on KRAS", PNAS, p. 1-7, www.pnas.org/cgi/doi/10.1073/pnas.1904529116.
Rajitha et al., "Synthesis and pharmacological evaluations of novel 2H-benzo[b](1,4)oxazin3(4H)-one derivatives as a new class of anti-cancer agents", European Journal of Medicinal Chemistry, 2011, vol. 46, pp. 4887-4896, Table 1.
International Search Report and Written Opinion for corresponding PCT application No. PCT/US18/61060 dated Feb. 7, 2019.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K inhibition, Downloaded from clincancerres.aacrjournals.org on Oct. 22, 2018. © 2018 American Association for Cancer Research.
Nabet, B. et al., "It Takes Two to Target: A Study in KRAS Dimerization", pubs.acs.org/biochemistry, DOI: 10.1021.
O'Bryan, J., "Pharmacological Targeting of RAS: Recent Success with Direct Inhibitors", Pharmacological Research (2018), https://doi.org/10.1016/j.phrs.2018.10.021.
Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.
Ruess, D. et al., "Mutant KRAS-driven cancers depend on PTPN11/SHP2 phosphatase", Nature Medicine, Letters, https://doi.org/10.1038/s41591-018-0024-8.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18/1640, Downloaded from clincancerres.aacrjournals.org on Oct. 29, 2018. © 2018 American Association for Cancer Research.
Wijeratne, A. et al., "Chemical Proteomic Characterization of a covalent KRASGI2C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer A Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/s41598-018-32683-w.
Pantar, T. et al., "Assessment of mutation probabilities of KRAS G12 missense mutants and their long-timescale dynamics by atomistic molecular simulations and Markov state modeling", PLOS Computational Biology, Sep. 10, 2018.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
International Search Report and Written Opinion for PCT Application No. PCT/US2017/33099 dated Aug. 24, 2017.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col, Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.
Costa-Cabral, S. et al., "CDK1 Is a Synthetic Lethal Target for KRAS Mutant Tumours", PLOS One | DOI:10.1371/journal.pone.0149099 Feb. 16, 2016.
Cully, "Closing the door on KRAS-mutant lung cancer", Nature Reviews Drug Discovery | Published online Nov. 3, 2016; doi:10.1038/nrd.2016.216, MacMillan Publishers.
Dharmaiah, S. et al., "Structural basis of recognition of farnesylated and methylated KRAS4b by PDEδ", E6766-E6775, PNAS, Published online Oct. 17, 2016.

(56) References Cited

OTHER PUBLICATIONS

Fiala, O. et al., "The dominant role of G12C over other KRAS mutation types in the negative prediction of efficacy of epidermal growth factor receptor tyrosine kinase inhibitors in nonesmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of Jul. 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer the End of the Beginning for Targeted Therapies", JAMA May 9, 2017 vol. 317, No. 18.
Kerr, E. et al., "Mutant Kras copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20.
Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S. et all., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6.
Nadal, E. et al., "Abstract C141: KRAS G12C mutation is prognostic of poor outcome in resected lung adenocarcinomas and predictive of poor response to MEK inhibition in vitro", Mol Cancer Ther Nov. 2013 12; C141, doi: 10.1158/1535-7163.TARG-13-C141.
Nussinov, R. et al., "Independent and core pathways in oncogenic KRAS signaling", Journal: Expert Review of Proteomics, DOI: 10.1080/14789450.2016.1209417, Published by Taylor & Francis.
Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J. et al., "K-Ras(G12C) inhibitors allosterically control GTP affinity and effector interactions", Nature, vol. 503: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15/1105.
Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15/1141, American Association for Cancer Research.
Rudoni, S. et al., "Role of guanine nucleotides in the regulation of the Ras/cAMP pathway in *Saccharomyces cerevisiae*", Biochimica et Biophysica Acta 1538 (2001) 181189.
Samatar, A. et al., "Targeting RAS-ERK signalling in cancer: promises and challenges", Nature Reviews Drug Discovery, vol. 13, pp. 928-942, Dec. 2014.
Sautier, B. et al., "Latest advances towards Ras inhibition—A medicinal chemistry perspective", Angewandte Chemie International Edition, 10.1002/anie.201608270.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag GmbH & Co. KGaA, Weinheim.
Sun, Q. et al., "A method for the second-site screening of K-Ras in the presence of a covalently attached first-site ligand", J Biomol NMR (2014) 60:11-14 DOI 10.1007/s10858-014-9849-8.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.

* cited by examiner

KRAS G12C INHIBITORS

FIELD OF THE INVENTION

The present invention relates to compounds that inhibit KRas G12C. In particular, the present invention relates to compounds that irreversibly inhibit the activity of KRas G12C, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18(22):6169-6177, published online 2012 Sep. 26. doi: 10.1158/1078-0432.CCR-11-3265).

The well-known role of KRAs in malignancy and the discovery of these frequent mutations in KRas in various tumor types made KRas a highly attractable target of the pharmaceutical industry for cancer therapy. Notwithstanding thirty years of large scale discovery efforts to develop inhibitors of KRas for treating cancer, no KRas inhibitor has demonstrated sufficient safety and/or efficacy to obtain regulatory approval (e.g., see McCormick (2015) Clin Cancer Res. 21 (8):1797-1801).

Despite many failed efforts to target KRas, compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well target KRas G12C (e.g., see Ostrem et al., (2013) Nature 503:548-551). Clearly there remains a continued interest and effort to develop inhibitors of KRas, particularly inhibitors of activating KRas mutants, including KRas G12C.

Thus, there is a need to develop new KRas G12C inhibitors that demonstrate sufficient efficacy, stability and/or safety for treating KRas G12C-mediated cancer. The compounds and compositions of the present invention advantageously overcome one or more of the previous shortcomings by providing selective KRas G12C inhibitors.

SUMMARY OF THE INVENTION

In one aspect of the invention, compounds are provided that inhibit KRas G12C activity. In certain embodiments, the compounds are represented by formula (I):

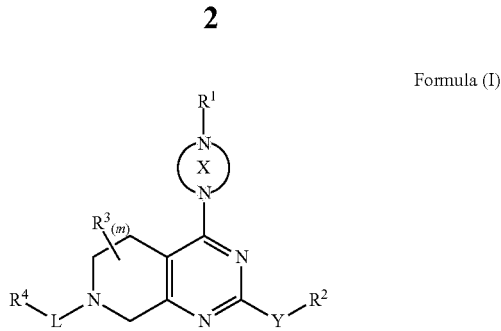

Formula (I)

or a pharmaceutically acceptable salt thereof, wherein:

X is a 4-12 membered saturated or partially saturated monocyclic, bridged or spirocyclic ring, wherein the saturated or partially saturated monocyclic ring is optionally substituted with one or more $R^8$;

Y is a bond, O, S or $NR^5$;

$R^1$ is $-C(O)C(R^A)\!=\!\!=\!C(R^B)_p$ or $-SO_2C(R^A)\!=\!\!=\!C(R^B)_p$;

$R^2$ is hydrogen, alkyl, hydroxyalkyl, dihydroxyalkyl, alkylaminylalkyl, dialkylaminylalkyl, $-Z-NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;

Z is C1-C4 alkylene;

each $R^3$ is independently C1-C3 alkyl, oxo, or haloalkyl;

L is a bond, $-C(O)-$, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$ or $R^7$;

each $R^5$ is independently hydrogen or C1-C3 alkyl;

$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;

each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;

$R^8$ is oxo, C1-C3 alkyl, C2-C4 alkynyl, heteroalkyl, cyano, $-C(O)OR^5$, $-C(O)N(R^5)_2$, $-N(R^5)_2$, wherein the C1-C3 alkyl may be optionally substituted with cyano, halogen, $-OR^5$, $-N(R^5)_2$, or heteroaryl each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;

each $R^{10}$ is independently hydrogen, acyl, C1-C3 alkyl, heteroalkyl or hydroxyalkyl;

$R^A$ is absent, hydrogen, or C1-C3 alkyl;

each $R^B$ is independently hydrogen, C1-C3 alkyl, alkylaminylalkyl, dialkylaminylalkyl or heterocyclylalkyl;

m is zero or an integer between 1 and 2;

p is one or two; and wherein, when $=\!\!=$ is a triple bond then $R^A$ is absent, $R^B$ is present and p equals one, or when $=\!\!=$ is a double bond then $R^A$ is present, $R^B$ is present and p equals two, or $R^A$, $R^B$ and the carbon atoms to which they are attached form a 5-8 membered partially saturated cycloalkyl optionally substituted with one or more $R^7$.

Also included are compounds of Formula I having the Formula I-A:

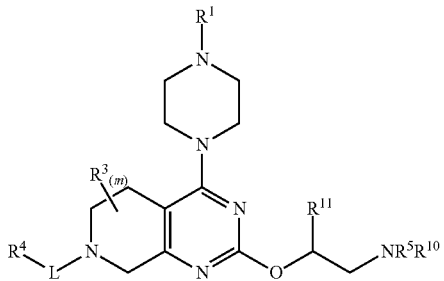

Formula I-A wherein $R^1$, $R^3$, $R^4$, $R^5$, $R^{10}$, L and m are as defined for Formula I, $R^{11}$ is hydrogen, C1-C3 alkyl or hydroxyalkyl, and the piperazinyl ring is optionally substituted with $R^8$ wherein $R^8$ is as defined for Formula I.

Also included are compounds of Formula I having the Formula I-B:

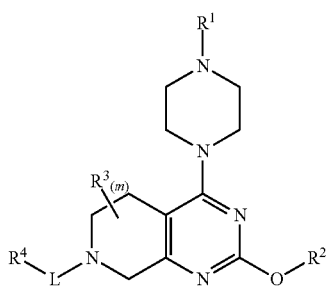

Formula I-B where $R^1$, $R^3$, $R^4$, L and m are as defined for Formula I, $R^2$ is heterocyclylalkyl optionally substituted with one or more $R^9$ where $R^9$ is as defined for Formula I, and the piperazinyl ring is optionally substituted with $R^8$, where $R^8$ is as defined for Formula I.

In certain embodiments, the compounds are represented by Formula (II):

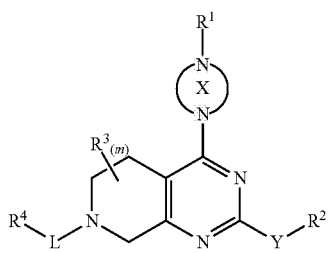

Formula (II)

or a pharmaceutically acceptable salt thereof:
wherein:
X is a 4-12 membered saturated or partially saturated monocyclic, bridged or spirocyclic ring, wherein the saturated or partially saturated monocyclic ring is optionally substituted with one or more $R^8$;
Y is a bond, O, S or $NR^5$;
$R^1$ is —C(O)C($R^A$)═══C($R^B$)$_p$ or —SO$_2$C($R^A$)═══C($R^B$)$_p$;

$R^2$ is hydrogen, alkyl, hydroxyalkyl, dihydroxyalkyl, alkylaminylalkyl, dialkylaminylalkyl, —Z—$NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;
each Z is C1-C4 alkylene;
each $R^3$ is independently C1-C3 alkyl, oxo, haloalkyl, hydroxyl or halogen;
L is a bond, —C(O)—, or C1-C3 alkylene;
$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$, $R^7$ or $R^8$;
each $R^5$ is independently hydrogen or C1-C3 alkyl;
$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;
each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;
$R^8$ is oxo, C1-C3 alkyl, C2-C4 alkynyl, heteroalkyl, cyano, —C(O)$OR^5$, —C(O)N($R^5$)$_2$, —N($R^5$)$_2$, wherein the C1-C3 alkyl may be optionally substituted with cyano, halogen, —$OR^5$, —N($R^5$)$_2$, or heteroaryl;
each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;
each $R^{10}$ is independently hydrogen, acyl, C1-C3 alkyl, heteroalkyl or hydroxyalkyl;
$R^{11}$ is haloalkyl;
$R^A$ is absent, hydrogen, deuterium, cyano, halogen, C1-C-3 alkyl, haloalkyl, heteroalkyl, —C(O)N($R^5$)$_2$, or hydroxyalkyl;
each $R^B$ is independently hydrogen, deuterium, cyano, C1-C3 alkyl, hydroxyalkyl, heteroalkyl, C1-C3 alkoxy, halogen, haloalkyl, —$ZNR^5R^{11}$, —C(O)N($R^5$)$_2$, —NHC(O) C1-C3 alkyl, —CH$_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;
or when ═══ is a double bond and p is two, one $R^B$ is hydrogen and $R^A$ and one $R^B$ and the carbon atoms to which they are attached form a 5-8 membered partially saturated cycloalkyl substituted with oxo;
m is zero or an integer between 1 and 2;
p is one or two; and wherein,
when ═══ is a triple bond then $R^A$ is absent, p equals one and $R^B$ is hydroxyalkyl,
or when ═══ is a double bond then $R^A$ is present, $R^B$ is present and p equals two, wherein when $R^A$ is hydrogen or C1-C3 alkyl at least one $R^B$ is deuterium, cyano, halogen, haloalkyl, hydroxyalkyl, heteroalkyl, heteroaryl, heteroarylalkyl, —$ZNR^5R^{11}$, —C(O)N($R^5$)$_2$, —NHC(O)C1-C3 alkyl, —CH$_2$NHC(O)C1-C3 alkyl or heterocyclylalkyl, wherein the heterocyclyl portion is substituted with one or more substituents independently selected from halogen, hydroxyl, alkoxy or C1-C3 alkyl; or when each $R^B$ is hydrogen, then $R^A$ is deuterium, cyano, halogen, haloalkyl, —C(O)N($R^5$)$_2$, hydroxyalkyl or heteroalkyl.

Also included are compounds of Formula II having the Formula II-A:

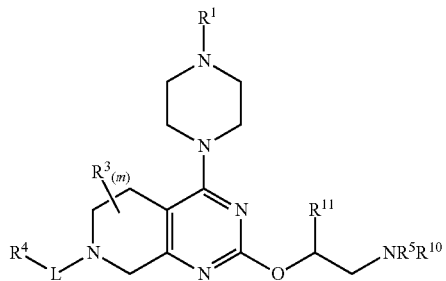

Formula II-A wherein $R^1$, $R^3$, $R^4$, $R^5$, $R^{10}$, L and m are as defined for Formula II, $R^{11}$ is hydrogen, C1-C3 alkyl or hydroxyalkyl, and the piperazinyl ring is optionally substituted with $R^8$ wherein $R^8$ is as defined for Formula II.

Also included are compounds of Formula II having the Formula II-B:

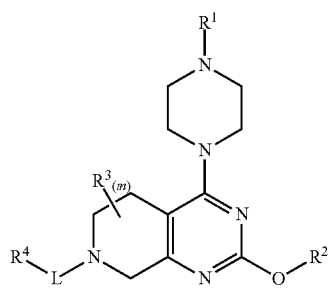

Formula II-B where $R^1$, $R^3$, $R^4$, $R^8$, L and m are as defined for Formula II, $R^2$ is heterocyclylalkyl optionally substituted with one or more $R^9$, and the piperazinyl ring is optionally substituted with $R^8$, where $R^8$ is as defined for Formula II.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting KRas G12C activity in a in a cell, comprising contacting the cell with a compound of Formula I, Formula I-A, Formula 1-B, Formula II, Formula II-A or Formula II-B. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula I, Formula I-A, Formula I-B, Formula II, Formula II-A or Formula II-B, or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas G12C-associated disease or disorder in a patient in need of such treatment, the method comprising administering to the patient a therapeutically effective amount of a compound of Formula I, Formula I-A, Formula I-B, Formula II, Formula II-A or Formula II-B, or a pharmaceutically acceptable salt or solvate thereof, or a pharmaceutical composition thereof as defined herein.

Also provided herein is a compound of Formula I, Formula I-A, Formula I-B, Formula II, Formula II-A or Formula II-B, or a pharmaceutically acceptable salt or solvate thereof, or a pharmaceutical composition thereof as defined herein for use in therapy.

Also provided herein is a compound of Formula I, Formula I-A, Formula I-B, Formula II, Formula II-A or Formula II-B, or a pharmaceutically acceptable salt or solvate thereof or a pharmaceutical composition thereof as defined herein for use in the treatment of cancer.

Also provided herein is a compound of Formula I, Formula I-A, Formula I-B, Formula II, Formula II-A or Formula II-B, or a pharmaceutically acceptable salt or solvate thereof for use in the inhibition of KRas G12C.

Also provided herein is a compound of Formula I, Formula I-A, Formula 1-B, Formula II, Formula II-A or Formula II-B, or a pharmaceutically acceptable salt or solvate thereof or a pharmaceutical composition thereof as defined herein, for use in the treatment of a KRas G12C-associated disease or disorder.

Also provided herein is the use of a compound of Formula I, Formula I-A, Formula I-B, Formula II, Formula II-A or Formula II-B, or a pharmaceutically acceptable salt or solvate thereof, as defined herein in the manufacture of a medicament for the treatment of cancer.

Also provided herein is a use of a compound of Formula I, Formula I-A, Formula 1-B, Formula II, Formula II-A or Formula II-B, or a pharmaceutically acceptable salt or solvate thereof, as defined herein in the manufacture of a medicament for the inhibition of activity of KRas G12C.

Also provided herein is the use of a compound of Formula I, Formula I-A, Formula 1-B, Formula II, Formula II-A or Formula II-B, or a pharmaceutically acceptable salt or solvate thereof, as defined herein, in the manufacture of a medicament for the treatment of a KRas G12C-associated disease or disorder.

Also provided herein is a method for treating cancer in a patient in need thereof, the method comprising (a) determining that the cancer is associated with a KRas G12C mutation (e.g., a KRas G12C-associated cancer); and (b) administering to the patient a therapeutically effective amount of a compound of Formula I, Formula I-A, Formula I-B, Formula II, Formula II-A or Formula II-B, or a pharmaceutically acceptable salt thereof, or a pharmaceutical composition thereof.

Also provided herein is a process for preparing a compound of Formula I, Formula I-A, Formula I-B, Formula II, Formula II-A or Formula II-B, or a pharmaceutically acceptable salt or solvate thereof.

Also provided herein is a compound of Formula I, Formula I-A, Formula I-B, Formula II, Formula II-A or Formula II-B, or a pharmaceutically acceptable salt thereof obtained by a process of preparing the compound as defined herein.

DETAILED DESCRIPTION OF THE INVENTION

The present invention relates to inhibitors of KRas G12C. In particular, the present invention relates to compounds that irreversibly inhibit the activity of KRas G12C, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, a "KRas G12C inhibitor" refers to compounds of the present invention that are represented by formulae (I) as described herein. These compounds are capable of negatively modulating or inhibiting all or a portion of the enzymatic activity of KRas G12C. The KRas G12C inhibitors of the present invention interact with and irreversibly bind to KRas G12C by forming a covalent adduct with the sulfhydryl side chain of the cysteine residue at position 12 resulting in the inhibition of the enzymatic activity of KRas G12C.

A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

In some embodiments of any of the methods or uses described herein, an assay is used to determine whether the patient has KRas G12C mutation using a sample (e.g., a biological sample or a biopsy sample (e.g., a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "amino" refers to —$NH_2$;

The term "acyl" refers to —$C(O)CH_3$.

The term "alkyl" as employed herein refers to straight and branched chain aliphatic groups having from 1 to 12 carbon atoms, 1-8 carbon atoms 1-6 carbon atoms, or 1-3 carbon atoms which is optionally substituted with one, two or three substituents. Examples of alkyl groups include, without limitation, methyl, ethyl, propyl, isopropyl, butyl, isobutyl, sec-butyl, tert-butyl, pentyl, and hexyl.

The term "haloalkyl" refers to an alkyl chain in which one or more hydrogen has been replaced by a halogen. Examples of haloalkyls are trifluoromethyl, difluoromethyl and fluoromethyl.

The term "haloalkyloxy" refers to —O-haloalkyl.

An "alkylene," group is an alkyl group, as defined hereinabove, that is positioned between and serves to connect two other chemical groups. Exemplary alkylene groups include, without limitation, methylene, ethylene, propylene, and butylene.

The term "alkoxy" refers to —OC1-C6 alkyl.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N.

As used herein, the term "hydroxyalkyl" refers to -alkyl-OH.

The term "dihydroxyalkyl" refers to an alkyl group as defined herein wherein two carbon atoms are each substituted with a hydroxyl group.

The term "alkylaminyl" refers to —$NR^x$-alkyl, wherein $R^x$ is hydrogen. In one embodiment, $R^x$ is hydrogen.

The term "dialkylaminyl" refers to —$N(R^y)_2$, wherein each $R^y$ is C1-C3 alkyl.

The term "alkylaminylalkyl" refers to -alkyl-NW-alkyl, wherein $R^x$ is hydrogen. In one embodiment, $R^x$ is hydrogen.

The term "dialkylaminylalkyl" refers to -alkyl-$N(R^y)_2$, wherein each $R^y$ is C1-C4 alkyl, wherein the alkyl of the -alkyl-$N(R^y)_2$ may be optionally substituted with hydroxy or hydroxyalkyl.

An "aryl" group is a C6-C14 aromatic moiety comprising one to three aromatic rings, which is optionally substituted. As one embodiment, the aryl group is a $C_6$-$C_{10}$ aryl group. Examples of aryl groups include, without limitation, phenyl, naphthyl, anthracenyl, fluorenyl, and dihydrobenzofuranyl.

An "aralkyl" or "arylalkyl" group comprises an aryl group covalently linked to an alkyl group, either of which may independently be optionally substituted or unsubstituted. An example of an aralkyl group is $(C_1-C_6)$alkyl$(C_6-C_{10})$aryl, including, without limitation, benzyl, phenethyl, and naphthylmethyl. An example of a substituted aralkyl is wherein the alkyl group is substituted with hydroxyalkyl.

A "heterocyclyl" or "heterocyclic" group is a ring structure having from about 3 to about 12 atoms, for example 4 to 8 atoms, wherein one or more atoms are selected from the group consisting of N, O, and S, the remainder of the ring atoms being carbon. The heterocyclyl may be a monocyclic, a bicyclic, a spirocyclic or a bridged ring system. The heterocyclic group is optionally substituted with $R^7$ on carbon or nitrogen at one or more positions, wherein $R^7$ is as defined for Formula I. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidinonyl, thiomorpholinyl, thiomorpholinyl 1,1 dioxide, morpholinyl, oxazepanyl, azabicyclohexanes, azabicycloheptanes and oxa azabiocycloheptanes. Specifically excluded from the scope of this term are compounds having adjacent annular O and/or S atoms.

The term "heterocyclylalkyl" refers to a heterocyclyl group as defined herein linked to the remaining portion of the molecule via an alkyl linker, wherein the alkyl linker of the heterocyclylalkyl may be optionally substituted with hydroxy or hydroxyalkyl.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroarylalkyl" group comprises a heteroaryl group covalently linked to an alkyl group, wherein the radical is on the alkyl group, either of which is independently optionally substituted or unsubstituted. Examples of heteroarylalkyl groups include a heteroaryl group having 5, 6, 9, or 10 ring atoms bonded to a C1-C6 alkyl group. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent annular O and/or S atoms.

As used herein, "an effective amount" of a compound is an amount that is sufficient to negatively modulate or inhibit the activity of KRas G12C. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of KRas G12C. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In one aspect of the invention, compounds are provided represented by formula (I):

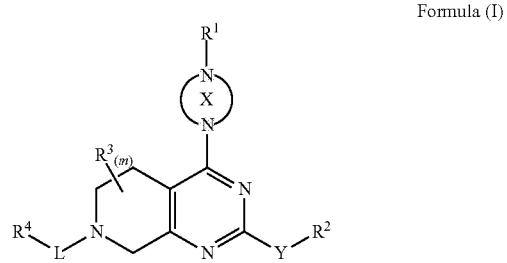

Formula (I)

or a pharmaceutically acceptable salt thereof, wherein:

X is a 4-12 membered saturated or partially saturated monocyclic, bridged or spirocyclic ring, wherein the saturated or partially saturated monocyclic ring is optionally substituted with one or more $R^8$;

Y is a bond, O, S or $NR^5$;

$R^1$ is —C(O)C($R^A$)=C($R^B$)$_p$ or —SO$_2$C($R^A$)=C($R^B$)$_p$;

$R^2$ is hydrogen, alkyl, hydroxyalkyl, dihydroxyalkyl, alkylaminylalkyl, dialkylaminylalkyl, —Z—NR$^5$R$^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;

Z is C1-C4 alkylene;

each $R^3$ is independently C1-C3 alkyl, oxo, or haloalkyl;

L is a bond, —C(O)—, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$ or $R^7$;

each $R^5$ is independently hydrogen or C1-C3 alkyl;

$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;

each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;

$R^8$ is oxo, C1-C3 alkyl, C2-C4 alkynyl, heteroalkyl, cyano, —C(O)OR$^5$, —C(O)N(R$^5$)$_2$, —N(R$^5$)$_2$, wherein the C1-C3 alkyl may be optionally substituted with cyano, halogen, —OR$^5$, —N(R$^5$)$_2$, or heteroaryl;

each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;

each $R^{10}$ is independently hydrogen, acyl, C1-C3 alkyl, heteroalkyl or hydroxyalkyl;

$R^A$ is absent, hydrogen, or C1-C3 alkyl;

each $R^B$ is independently hydrogen, C1-C3 alkyl, alkylaminylalkyl, dialkylaminylalkyl or heterocyclylalkyl;

m is zero or an integer between 1 and 2;

p is one or two; and wherein, when ≡ is a triple bond then $R^A$ is absent, $R^B$ is present and p equals one;

or when ≡ is a double bond then $R^A$ is present, $R^B$ is present and p equals two, or $R^A$, $R^B$ and the carbon atoms to which they are attached form a 5-8 membered partially saturated cycloalkyl optionally substituted with one or more $R^7$.

In certain embodiments, $R^1$—X is:

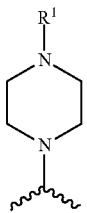

wherein $R^1$ is are defined for Formula I and the piperazinyl ring is optionally substituted with $R^8$, where $R^8$ is as defined for Formula I. In certain embodiments, $R^8$ is C1-C3 alkyl wherein the alkyl is optionally substituted with cyano or OR$^5$, or —C(O)N(R$^5$)$_2$, wherein each $R^5$ is independently hydrogen or C1-C3 alkyl.

In particular embodiments, $R^1$ is —C(O)C(R$^A$)≡C(R$^B$)$_p$ where $R^A$, $R^B$ and p are as defined for Formula I. In one embodiment, $R^1$ is —C(O)C(R$^A$)≡C(R$^B$)$_p$, wherein ≡ is a triple bond and $R^A$ is absent, p is one and $R^B$ is C1-C3 alkyl. In one embodiment, $R^1$ is —C(O)C(R$^A$)≡C(R$^B$)$_p$, wherein ≡ is a double bond and $R^A$ is hydrogen or C1-C3alkyl, p is two and each $R^B$ is independently hydrogen, C1-C3alkyl, dialkylaminylalkyl or heterocyclylalkyl. In one embodiment, $R^1$ is —C(O)C(R$^A$)=C(R$^B$)$_p$, wherein $R^A$ is hydrogen or C1-C3alkyl, p is two, one of said $R^B$ is hydrogen, C1-C3alkyl, dialkylaminylalkyl or heterocyclylalkyl and the other $R^B$ is hydrogen or C1-C3alkyl. In one embodiment, $R^1$ is —C(O)CH=CH$_2$.

In one embodiment, Y is O or NR$^5$ and $R^2$ is selected from the group consisting of alkyl, hydroxyalkyl, dihydroxyalkyl, alkylaminylalkyl, dialkylaminylalkyl, heterocyclyl, heterocyclylalkyl, and heteroaryl. In one embodiment, Y is O and $R^2$ is hydroxyalkyl, dihydroxyalkyl, alkylaminylalkyl, or dialkylaminylalkyl, wherein the alkylaminylalkyl or dialkylaminylalkyl is optionally substituted with one or more $R^9$. In one embodiment, the optionally substituted alkylaminylalkyl or dialkylaminylalkyl is independently selected from methylaminylpropan-2-yl, dimethylaminylethyl, methylethylaminylethyl, dimethylaminylpropanyl, dimethylaminylpropan-2-yl, dimethylaminylbutanyl, dimethylaminylbutan-2-yl, 2-dimethylaminylpropanol, or diethylaminylethyl. In one embodiment, Y is O or NR$^5$ and $R^2$ is heterocyclyl or heterocyclylalkyl optionally substituted with one or more $R^9$. Nonlimiting examples of one or more $R^9$ when $R^2$ is heterocyclyl or heterocyclylalkyl include C1-C3 alkyl, acyl, oxo, cyano, alkoxy, cycloalkyl, cycloalkylmethyl, halogen, and hydroxyl. Nonlimiting examples of $R^2$ heterocyclyls optionally substituted with one or more $R^9$ include azetidinyl, C1-C3alkyl-substituted azetidinyl (e.g., methylazetidinyl), halo-substituted azetidinyl (e.g., difluoroazetidinyl), tetrahydropyran, pyrrolidinyl, C1-C3 alkyl-substituted pyrrolidinyl (e.g., methylpyrrolidinyl, dimethylpyrrolidinyl, and isopropylpyrrolidinyl), cycloalkylalkylpyrrolidinyl, hydroxypyrrolindinyl, halo-substituted pyrrolidinyl (e.g., fluoropyrrolidinyl and difluoropyrrolidinyl), methoxyethylpyrrolidinyl, (N-methyl)methoxypyrrolidinyl, piperazinyl, dimethylaminylpyrrolidinyl, morpholinyl, methylmorpholinyl, 1,4-oxazepanyl, piperdinyl, C1-C3 alkyl-substituted piperidinyl (e.g., methylpiperidinyl), acylpiperdinyl, cyanopiperdinyl, cycloalkylpiperdinyl, halopiperdinyl (e.g., fluoropiperdinyl), dihalopiperdinyl (e.g., difluoropiperdinyl), alkoxypiperdinyl, pyrrolidonyl, piperidonyl, thiomorpholinyl-1,1-dioxide, 3-azabicyclo[3.1.0]hexanyl, oxa-5-azabicyclo[2.2.1]heptan-5-yl, and azabicyclo[2.2.1]heptan-2-yl.

In one embodiment, Y is O and $R^2$ is heteroarylalkyl optionally substituted with one or more $R^9$. In one embodiment, the heteroaryl portion of the heteroarylalkyl is pyridinyl.

In one embodiment, Y is O and $R^2$ is —ZR$^5$R$^{10}$. In one embodiment, $R^5$ is C1-C3 alkyl and $R^{10}$ is independently selected from acyl, hydroxyalkyl or alkoxy.

In one embodiment, Y is a bond and $R^2$ is hydrogen, heterocyclyl or aryl, wherein said heterocyclyl and aryl are optionally substituted with one or more $R^9$.

In one embodiment, Y is a bond and $R^2$ is hydrogen.

In one embodiment, Y is a bond and $R^2$ is heterocyclyl optionally substituted with one or more $R^9$. In one embodiment, Y is a bond and $R^2$ is heterocyclyl optionally substituted with methyl, halogen or dimethylamino. Nonlimiting examples of $R^2$ heterocyclyls include azetidinyl, piperidinyl, piperazinyl, morpholinyl, and pyrrolidinyl.

In one embodiment, Y is a bond and $R^2$ is aryl optionally substituted with one or more $R^9$. In one embodiment, the aryl is phenyl substituted with heterocyclylalkyl.

In certain other embodiments when X is a monocyclic ring, $R^4$ is aryl. In one embodiment, $R^4$ is selected from the group consisting of phenyl and naphthyl and is optionally substituted with one or more $R^6$ or $R^7$. Examples of $R^7$ substituents include halogen, hydroxyl, C1-C6 alkyl (e.g., C1-C3 alkyl), cycloalkyl, haloalkyl, Q-haloalkyl, amino, cyano, hydroxyalkyl and alkoxy. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, 2,2,2-trifluoroethyl, hydroxyl, trifluoromethoxy, hydroxyl, fluoro, chloro, isopropyl, cyclopropyl and trifluoromethylthio. In one embodiment, the aryl is phenyl substituted with one to three $R^7$ groups independently selected from hydroxyl, fluorine and chlorine. In one embodiment, the aryl is phenyl substituted with hydroxyl and C1-C3 alkyl or two C1-C3 alkyl. In one embodiment, the aryl is phenyl substituted with Q-haloalkyl and hydroxyl or fluorine.

In one embodiment, $R^4$ is aryl wherein aryl is naphthyl optionally substituted with one or more $R^7$. In one embodiment, the aryl is naphthyl substituted with one or more $R^7$ groups independently selected from halogen, hydroxyl, C1-C3 alkyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, amino, and haloalkyl. In one embodiment, $R^4$ is naphthyl optionally substituted with one to three $R^7$ substituents independently selected from difluoromethyl, methyl, hydroxyl, amino, fluoro, and chloro.

In one embodiment, the aryl is naphthyl optionally substituted with one or more halogen. In one embodiment, the aryl is naphthyl substituted with hydroxyl and trifluoromethyl or C1-C3alkyl. In one embodiment, the aryl is naphthyl substituted with hydroxyl.

In one embodiment, $R^4$ is heteroaryl optionally substituted with one or more $R^7$. In one embodiment, $R^4$ is heteroaryl optionally substituted with one or more $R^7$ independently selected from halogen, hydroxyl, C3 alkyl, haloalkyl, Q-haloalkyl, alkoxy and amino. In one embodiments, $R^4$ is indoyl, indazolyl, quinolinyl, isoquinolinyl, pyridinyl or benzo[d]thiazolyl optionally substituted with one or more $R^7$. In one embodiments, $R^4$ is indoyl, indazolyl, quinolinyl, isoquinolinyl, pyridinyl or benzo[d]thiazolyl optionally substituted with one or more $R^7$ independently selected from halogen, hydroxyl, C3 alkyl, haloalkyl, Q-haloalkyl, alkoxy and amino.

In yet other embodiments, $R^4$ is heteroaryl, optionally an indoyl or an indazolyl, each of which may be substituted with one or more $R^7$. In one embodiment, $R^4$ is heteroaryl optionally substituted with one or more $R^7$ substituents independently selected from the group consisting of halogen, hydroxyl, C3 alkyl, haloalkyl, Q-haloalkyl and alkoxy. In one embodiment, the $R^4$ heteroaryl is indazolyl optionally substituted with one or two $R^7$ independently selected from alkoxy, haloalkyl, and C1-C6 alkyl. In other embodiments, the $R^4$ heteroaryl is a quinolinyl or isoquinolinyl, each optionally substituted with one or more $R^7$. In one embodiment, the $R^4$ heteroaryl is a quinolinyl or isoquinolinyl, each optionally substituted with one or more $R^7$ independently selected from amino, hydroxyl, C1-C3 alkyl, and hydroxyl. In one embodiment, the $R^4$ heteroaryl is a quinolinyl or isoquinolinyl, each optionally substituted with $R^7$ selected from hydroxyl and amino. In one embodiment, the $R^4$ heteroaryl is a pyridinyl optionally substituted with one or more $R^7$. In one embodiment, the $R^4$ heteroaryl is pyridinyl optionally substituted with one or more $R^7$ independently selected from C1-C3 alkyl, halogen and haloalkyl. In other embodiments, the $R^4$ heteroaryl is benzo[d]thiazolyl optionally substituted with one or more $R^7$, such as hydroxyl, one or two C1-C3 alkyl, or hydroxyl and one or two C1-C3 alkyl. In one embodiment, the $R^4$ heteroaryl is indolyl optionally substituted with one or more $R^7$. In one embodiment, the $R^4$ heteroaryl is indolyl optionally substituted with one or two $R^7$ independently selected from hydroxyl and C1-C3alkyl.

In one embodiment, where X is a monocyclic ring, $R^4$ is aralkyl. In certain embodiments, the aralkyl is benzyl. In other embodiments, the alkyl of the benzyl group is optionally substituted with hydroxyalkyl.

In one embodiment, L is a bond.
In one embodiment, m is one and $R^3$ is C1-C3 alkyl.
In one embodiment, m is one and $R^3$ is oxo.
In one embodiment, $R^8$ is heteroalkyl, C2-C4 alkynyl or C1-C3 alkyl optionally substituted with —$OR^5$, cyano or heteroaryl. In one embodiment, $R^8$ is methyl, cyanomethyl, methoxymethyl, hydroxymethyl. In one embodiment, $R^8$ is methyl. In one embodiment, $R^8$ is cyanomethyl. In one embodiment, $R^8$ is hydroxymethyl.

In one embodiment, Formula I includes compounds having the Formula I-A:

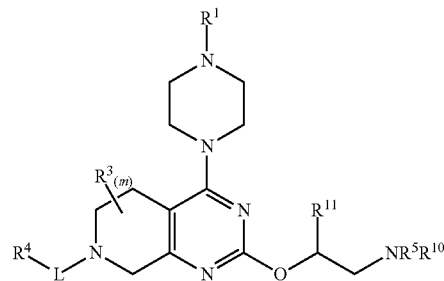

wherein $R^1$, $R^3$, $R^4$, $R^5$, $R^{10}$, L and m are as defined for Formula I, $R^{11}$ is hydrogen, methyl or hydroxyalkyl, and the piperidinyl ring is optionally substituted with $R^8$ wherein $R^8$ is as defined for Formula I. In one embodiment, L is a bond. In one embodiment, $R^4$ is aryl or heteroaryl, each of which is optionally substituted with one or more $R^6$ or $R^7$. In one embodiment, $R^4$ is aryl or heteroaryl, each of which is optionally substituted with one or more $R^7$. In one embodiment, each $R^7$ is independently selected from hydroxyl, amino, halogen, C1-C3 alkyl, haloalkyl, Q-haloalkyl, cycloalkyl and alkoxy. In one embodiment, $R^5$ and $R^{10}$ are each C1-C3 alkyl. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, 2,2,2-trifluoroethyl, hydroxyl, trifluoromethoxy, hydroxyl, fluoro, chloro, isopropyl, cyclopropyl and trifluoromethylthio. In one embodiment, the aryl is phenyl substituted with one to three $R^7$ groups independently selected from hydroxyl, fluorine and chlorine. In one embodiment, the aryl is phenyl substituted with hydroxyl and C1-C3 alkyl or two C1-C3 alkyl. In one embodiment, the aryl is phenyl substituted with Q-haloalkyl and hydroxyl or fluorine. In one embodiment, the aryl is naphthyl substituted with one or more $R^7$ groups independently selected from halogen, hydroxyl, C1-C3 alkyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, amino, and haloalkyl. In one embodiment, $R^4$ is naphthyl optionally substituted with one to three $R^7$ substituents independently selected from difluoromethyl, methyl, hydroxyl, amino, fluoro, and chloro. In one embodiment, the aryl is naphthyl optionally substituted with one or more halogen. In one embodiment, the aryl is naphthyl substituted with hydroxyl and trifluoromethyl or C1-C3 alkyl. In one embodiment, the aryl is naphthyl substituted with hydroxyl. In one embodiment, $R^4$ is heteroaryl, wherein the heteroaryl is indazolyl optionally substituted with one or two $R^7$ independently selected from alkoxy, haloalkyl, and C1-C6 alkyl. In one embodiment, $R^4$ is heteroaryl, wherein the heteroaryl is quinolinyl or isoquinolinyl, each optionally substituted with one or more $R^7$. In one embodiment, $R^4$ is heteroaryl, wherein the heteroaryl is quinolinyl or isoquinolinyl, each optionally substituted with one or more $R^7$ independently selected from amino, hydroxyl, C1-C3alkyl, and hydroxyl. In one embodiment, the $R^4$ heteroaryl is a pyridinyl optionally substituted with one or more $R^7$. In one embodiment, the $R^4$ heteroaryl is pyridinyl optionally substituted with one or more $R^7$ independently selected from C1-C3 alkyl, halogen and haloalkyl. In one embodiment, the $R^4$ heteroaryl is benzo[d]thiazolyl optionally substituted with one or more $R^7$, such as hydroxyl, one or two C1-C3 alkyl, or hydroxyl and one or two C1-C3 alkyl. In one embodiment, the $R^4$ heteroaryl is indolyl optionally substituted with one or more $R^7$. In one embodiment, the $R^4$ heteroaryl is indolyl optionally substituted with one or two $R^7$ independently selected from hydroxyl and C1-C3 alkyl. In one embodiment, $R^{11}$ is methyl. In one embodiment, the piperidinyl ring is unsubstituted. In one embodiment, the piperidinyl ring is substituted with $R^8$. In one embodiment, $R^8$ is C1-C3 alkyl optionally substituted with cyano or hydroxyl. In one embodiment, $R^8$ is methyl, cyanomethyl or hydroxymethyl. In one embodiment, $R^8$ is methyl. In one embodiment, $R^8$ is cyanomethyl. In one embodiment, $R^8$ is hydroxymethyl. In another embodiment, $R^5$ and $R^{10}$ are each C1-C3 alkyl, $R^{11}$ is methyl, $R^8$ is methyl, cyanomethyl or hydroxymethyl, L is a bond, and $R^4$ is aryl or heteroaryl, each optionally substituted with one or more $R^6$ or $R^7$.

In one embodiment, Formula I includes compounds having the Formula I-B:

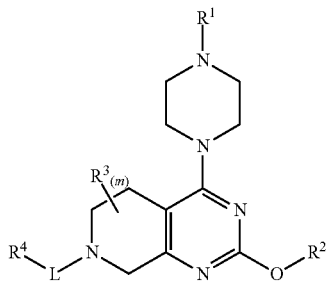

Formula I-B and $R^1$, $R^3$, $R^4$, $R^9$, L and m are as defined for Formula I, $R^2$ is heterocyclylalkyl optionally substituted with one or more $R^9$, and the piperidinyl ring is optionally substituted with $R^8$, where $R^8$ is as defined for Formula I. In one embodiment, the heterocyclyl portion of the $R^2$ heterocyclylalkyl is a monocyclic, bicyclic, or bridged ring system having one or two ring heteroatoms independently selected from N and O. In one embodiment, $R^2$ heterocyclyl is pyrrolidinyl, piperidinyl, piperazinyl, morpholinyl, 1,4-oxazepanyl, thiomorpholinyl-1,1-dioxide, 3-azabicyclo[3.1.0]hexanyl, 2-oxa-5-azabicyclo[2.2.1]heptan-5-yl, and azabicyclo[2.2.1]heptan-2-yl, optionally substituted with one or more $R^9$. In one embodiment, each $R^9$ is selected from acyl, oxo, halogen, cyano, C1-C3 alkyl, alkoxy, hydroxyalkyl, heteroalkyl, heterocyclyl, cycloalkyl, aralkyl and dialkylamidoalkyl. In one embodiment, L is a bond. In one embodiment, $R^4$ is aryl or heteroaryl, each of which is optionally substituted with one or more $R^6$ or $R^7$. In one embodiment, $R^4$ is aryl or heteroaryl, each of which is optionally substituted with one or more $R^7$. In one embodiment, each $R^7$ is independently selected from hydroxyl, amino, halogen, C1-C3 alkyl, haloalkyl, Q-haloalkyl, cycloalkyl and alkoxy. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, 2,2,2-trifluoroethyl, hydroxyl, trifluoromethoxy, hydroxyl, fluoro, chloro, isopropyl, cyclopropyl and trifluoromethylthio. In one embodiment, the aryl is phenyl substituted with one to three $R^7$ groups independently selected from hydroxyl, fluorine and chlorine. In one embodiment, the aryl is phenyl substituted with hydroxyl and C1-C3 alkyl or two C1-C3 alkyl. In one embodiment, the aryl is phenyl substituted with Q-haloalkyl and hydroxyl or fluorine. In one embodiment, the aryl is naphthyl substituted with one or more $R^7$ groups independently selected from halogen, hydroxyl, C1-C3 alkyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, amino, and haloalkyl. In one embodiment, $R^4$ is naphthyl optionally substituted with one to three $R^7$ substituents independently selected from difluoromethyl, methyl, hydroxyl, amino, fluoro, and chloro. In one embodiment, the aryl is naphthyl optionally substituted with one or more halogen. In one embodiment, the aryl is naphthyl substituted with hydroxyl and trifluoromethyl or C1-C3alkyl. In one embodiment, the aryl is naphthyl substituted with hydroxyl. In one embodiment, $R^4$ is heteroaryl, wherein the heteroaryl is indazolyl optionally substituted with one or two $R^7$ independently selected from alkoxy, haloalkyl, and C1-C6 alkyl. In one embodiment, $R^4$ is heteroaryl, wherein the heteroaryl is quinolinyl or isoquinolinyl, each optionally substituted with one or more $R^7$. In one embodiment, $R^4$ is heteroaryl, wherein the heteroaryl is quinolinyl or isoquinolinyl, each optionally substituted with one or more $R^7$ independently selected from amino, hydroxyl, C1-C3 alkyl, and hydroxyl. In one embodiment, the $R^4$ heteroaryl is a pyridinyl optionally substituted with one or more $R^7$. In one embodiment, the $R^4$ heteroaryl is pyridinyl optionally substituted with one or more R⁷ independently selected from C1-C3 alkyl, halogen and haloalkyl. In one embodiment, the R⁴ heteroaryl is benzo[d]thiazolyl optionally substituted with one or more R⁷, such as hydroxyl, one or two C1-C3 alkyl, or hydroxyl and one or two C1-C3 alkyl. In one embodiment, the R⁴ heteroaryl is indolyl optionally substituted with one or more R⁷. In one embodiment, the R⁴ heteroaryl is indolyl optionally substituted with one or two R⁷ independently selected from hydroxyl and C1-C3 alkyl. In one embodiment, R¹¹ is methyl. In one embodiment, the piperidinyl ring is unsubstituted. In one embodiment, the piperidinyl ring is substituted with R⁸. In one embodiment, the piperidinyl ring is unsubstituted. In one embodiment, the piperidinyl ring is substituted with R⁸. In one embodiment, R⁸ is C1-C3 alkyl optionally substituted with cyano, hydroxyl or methoxy. In one embodiment, R⁸ is methyl, cyanomethyl, hydroxymethyl or methoxymethyl.

In one embodiment, X is a saturated bridged ring system. Nonlimiting examples of bridged ring systems include diazabicycloheptanes and diazabicyclooctanes. In certain embodiments, when X is a saturated bridged ring system, R¹ is —C(O)CH=CH₂. In one embodiment, the bridged ring system is substituted with one or two groups independently selected from R⁸, where R⁸ is as defined for Formula I. In one embodiment, the bridged ring system is unsubstituted. In one embodiment, the bridged ring system is diazabicyclo[3.2.1]octan-8-yl or diazabicyclo[3.2.1]octan-3-yl.

In one embodiment, R¹—X is:

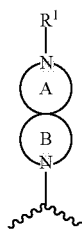

wherein A and B are a spirocyclic ring system, wherein A and B are the same or different and independently represent a 4-6 membered saturated ring systems, wherein the rings are optionally substituted with one or more R⁸, wherein R⁸ is as defined for Formula I. In certain embodiments, R¹ is —C(O)CH=CH₂. In certain embodiments, rings A and B are unsubstituted.

In one embodiment, the spirocyclic ring system is unsubstituted. Non-limiting examples of spirocyclic ring systems include:

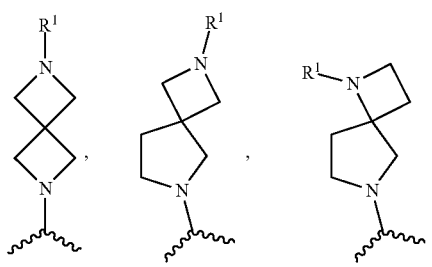

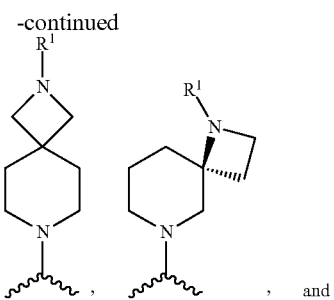

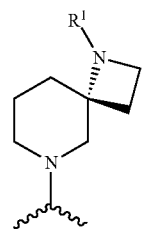

In certain embodiments when A and B represent a spirocyclic ring system, R¹ is —C(O)CH=CH₂.

In one embodiment of Formula I, R² is selected from the group consisting of hydroxyalkyl, dialkylaminylalkyl, heterocyclyl and heterocyclylalkyl, wherein each of the heterocyclyl or heterocyclylalkyl are independently optionally substituted with R⁹. In another embodiment, R² is heterocyclyl and heterocyclylalkyl, wherein each of the heterocyclyl or heterocyclylalkyl are independently optionally substituted with one or more R⁹. In certain embodiments, R² is dialkylaminylalkyl optionally substituted with one or more R⁹. Non-limiting examples include dimethylaminylethyl, dimethylaminylpropanyl, dimethylaminylpropan-2-yl, dimethylaminylbutanyl, dimethylaminylbutan-2-yl, 2-dimethylaminylpropanol, or diethylaminylethyl.

In one embodiment, Y is O and R² is selected from the group consisting of hydroxyalkyl, dialkylaminylalkyl, heterocyclyl, heterocyclylalkyl, and —ZR⁵R¹⁰, wherein R⁵ and R¹⁰ are as defined for Formula I.

In one embodiment, Y is O and R² is selected from the group consisting of hydroxyalkyl, dialkylaminylalkyl, heterocyclyl and heterocyclylalkyl, wherein each of the heterocyclyl or heterocyclylalkyl are independently optionally substituted with R⁹. In another embodiment, R² is heterocyclyl and heterocyclylalkyl, wherein each of the heterocyclyl or heterocyclylalkyl are independently optionally substituted with one or more R⁹. Non-limiting examples of R⁹ include acyl, oxo, halogen, cyano, C1-C6 alkyl, alkoxy, hydroxyalkyl, heteroalkyl, cycloalkyl, aralkyl or dialkylaminoalkyl. In certain embodiments, R² is dialkylaminylalkyl optionally substituted with one or more R⁹. Non-limiting examples include dimethylaminylethyl, dimethylaminylpropanyl, dimethylaminylpropan-2-yl, dimethylaminylbutanyl, dimethylaminylbutan-2-yl, 2-dimethylaminylpropanol, or diethylaminylethyl.

In one embodiment of Formula I, R⁴ is aryl optionally substituted with one or more R⁶ or R⁷. In one embodiment, R⁴ is phenyl or naphthyl optionally substituted with one or more R⁶ or R⁷. In one embodiment, R⁴ is phenyl or naphthyl optionally substituted with one or more R⁷. In one embodiment, R⁴ is phenyl or naphthyl optionally substituted with one or more R⁷ substituents independently selected from halogen, hydroxyl, C1-C3alkyl, cycloalkyl, alkoxy, haloalkyl, or Q-haloalkyl wherein Q is O or S. In one embodiment, R⁴ is phenyl or naphthyl optionally substituted with one or more $R^7$ substituents independently selected from methyl, trifluoromethyl, hydroxyl, trifluoromethoxy, hydroxyl, fluoro, chloro, isopropyl, cyclopropyl and methylthio.

In one embodiment, $R^4$ is isoquinolinyl which is optionally substituted with amino. In one embodiment, $R^4$ is aralkyl. In certain embodiments, the aralkyl is benzyl. In one embodiment, the aralkyl is benzyl wherein the alkyl portion is substituted with hydroxyl or hydroxyalkyl.

Nonlimiting examples of compounds of Formula (I), Formula I-A and Formula I-B are selected from the group consisting of:

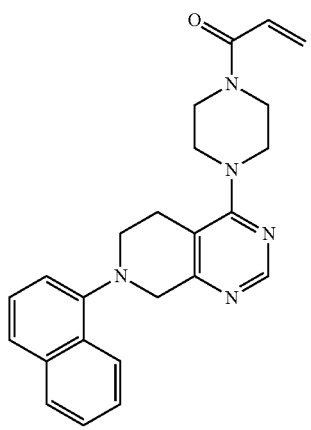

,

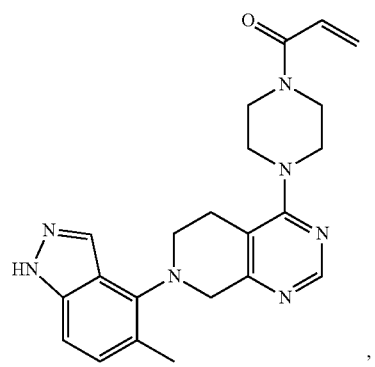

,

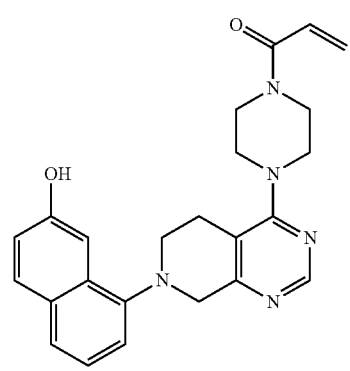

,

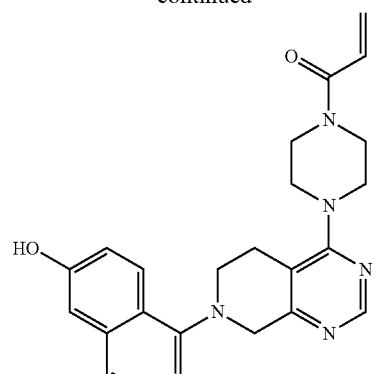

,

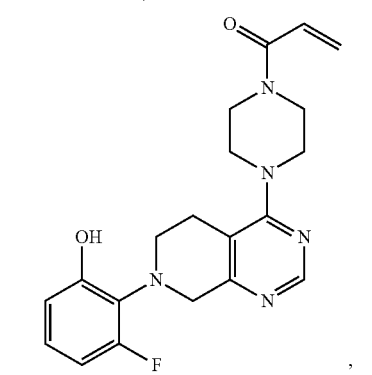

,

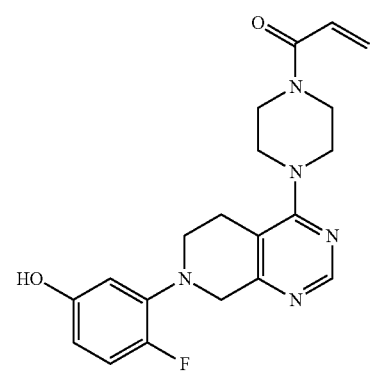

,

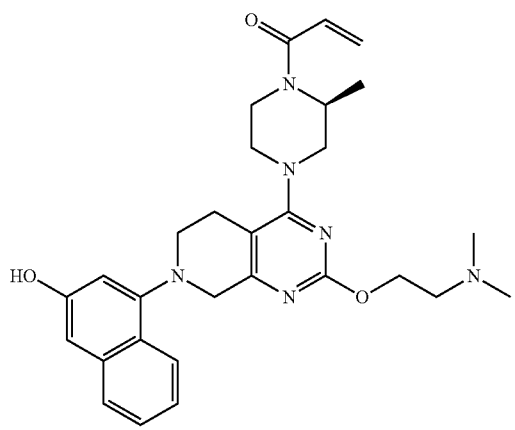

,

21
-continued
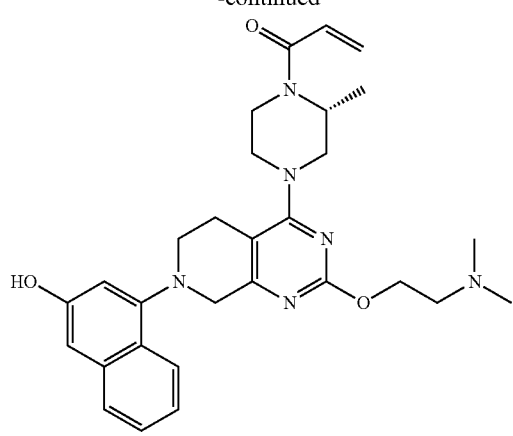
,
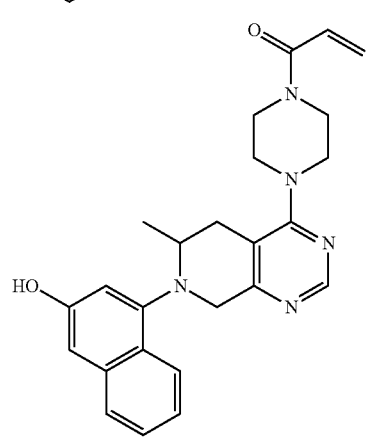
,
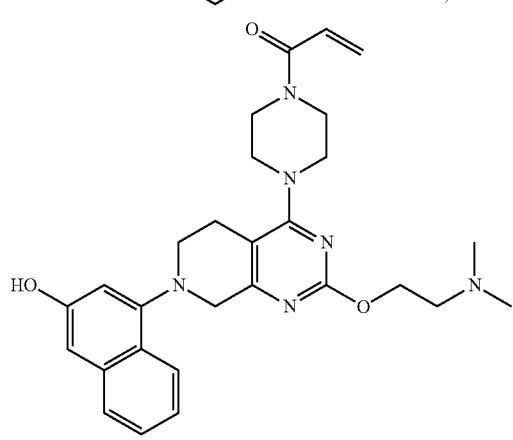
,
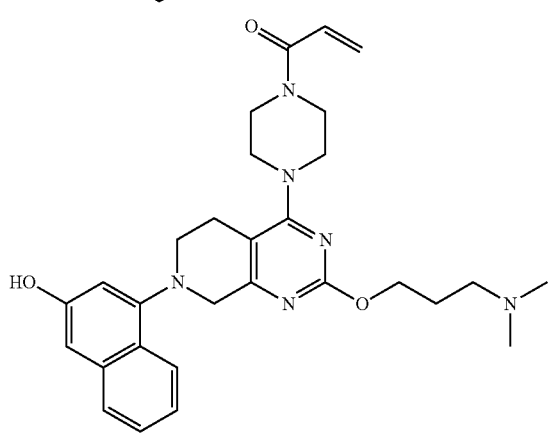
,
22
-continued
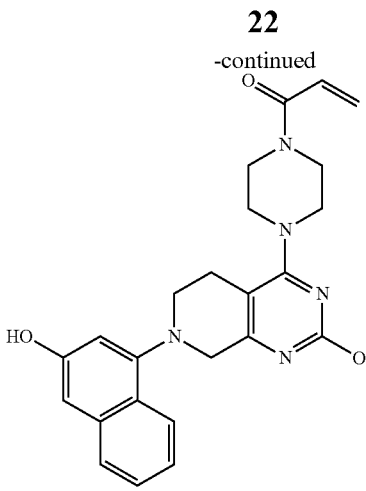
,
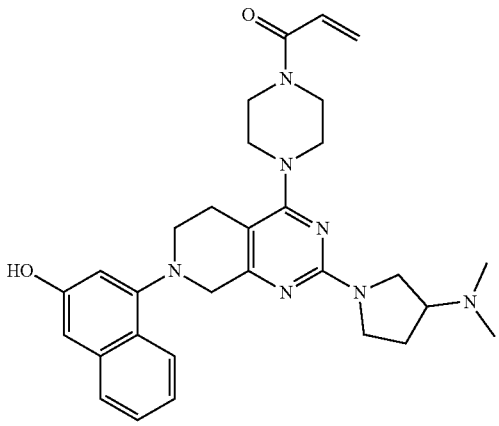
,
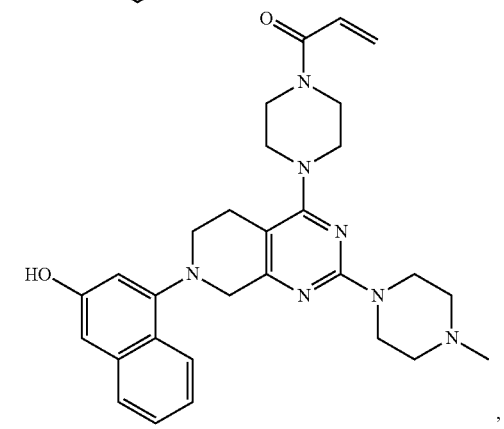
,
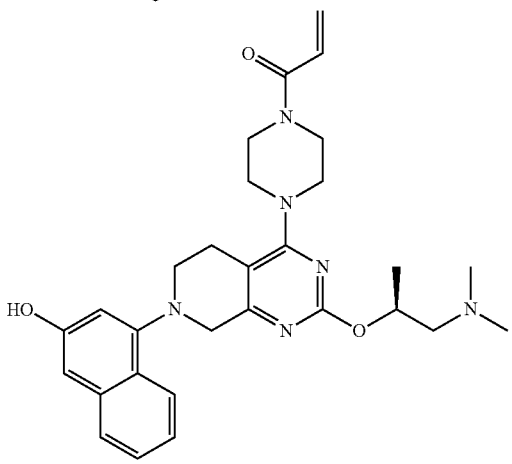
, 23
-continued
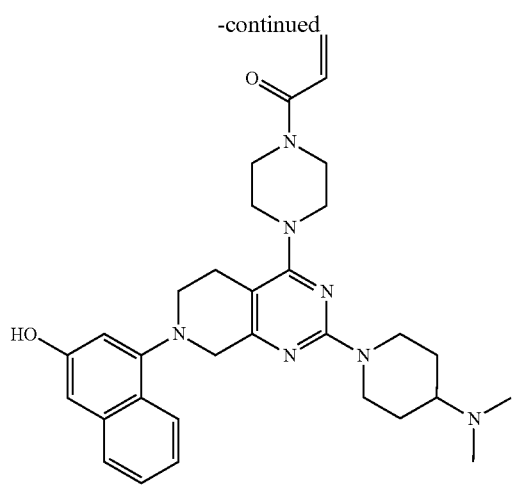
24
-continued
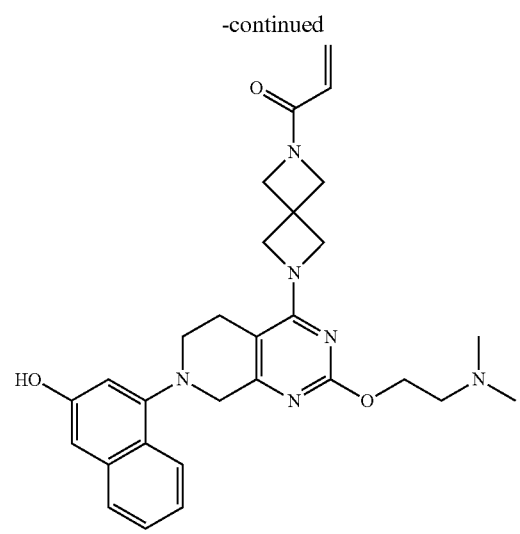
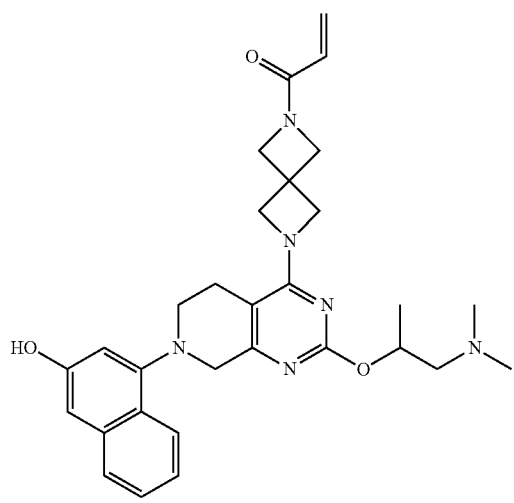
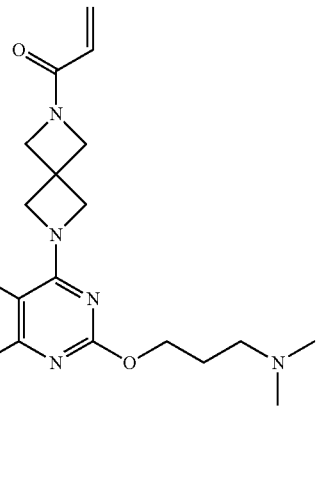
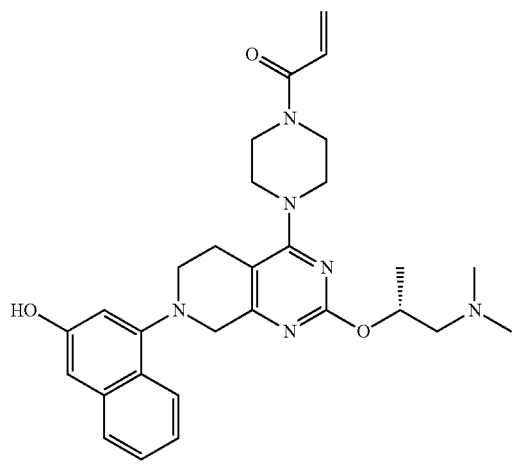
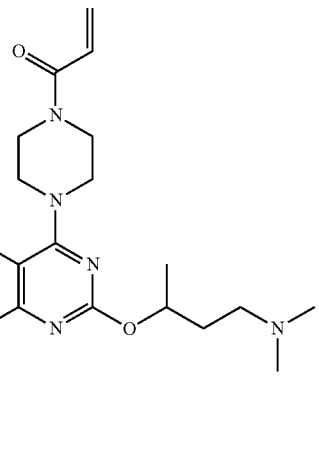

25
-continued
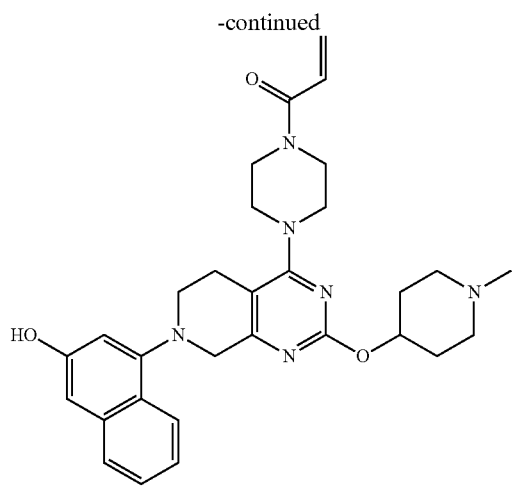
,
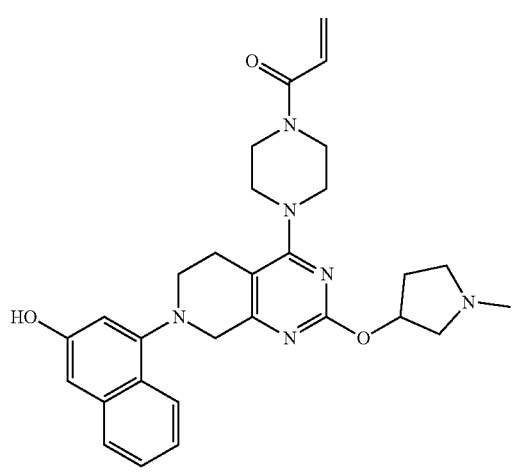
,
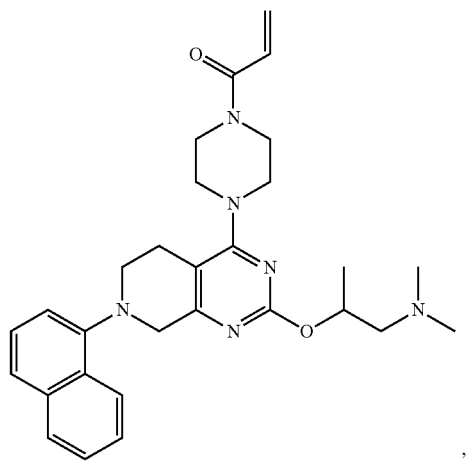
,
26
-continued
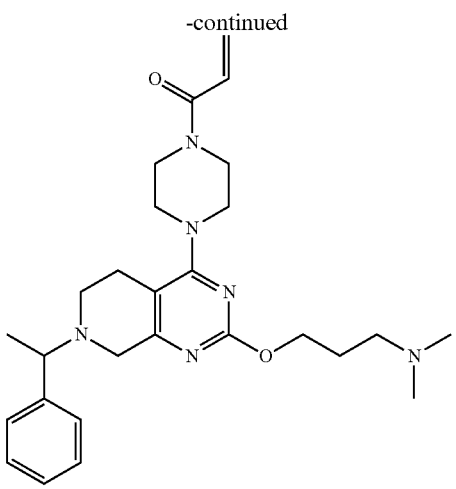
,
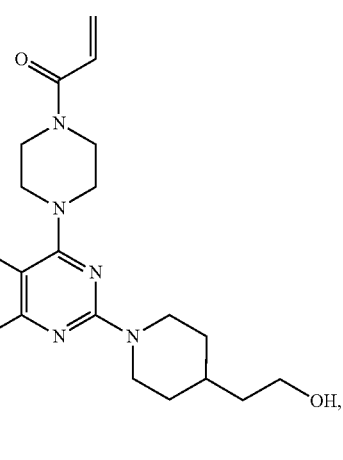
,
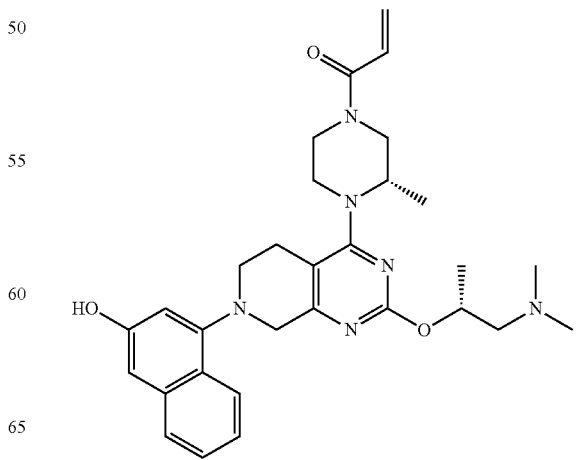
, 27
-continued
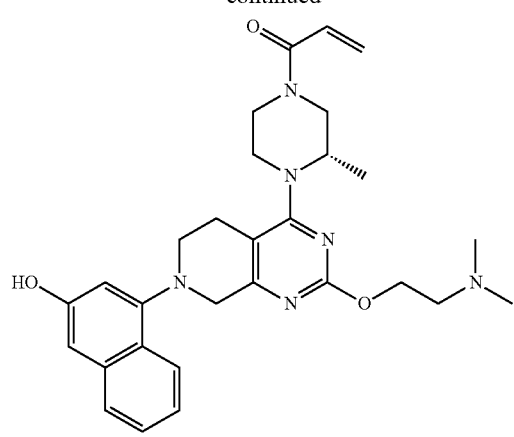
,
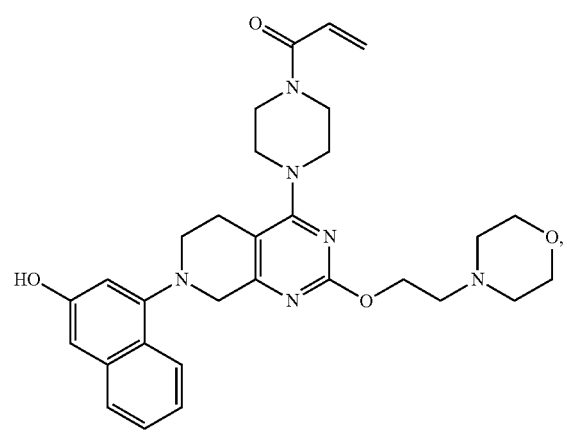
,
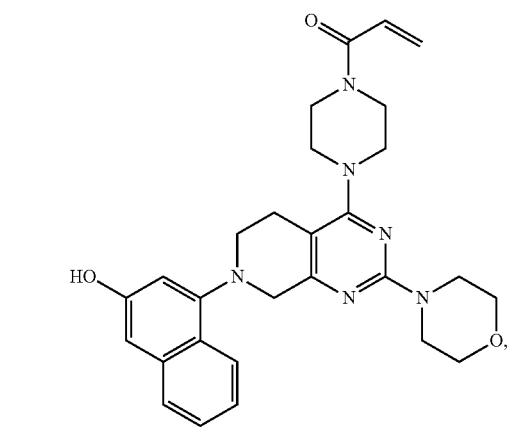
,
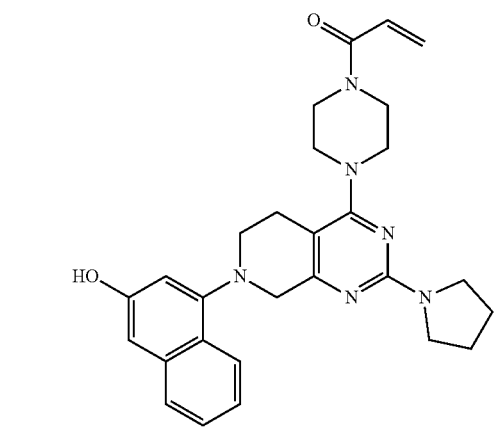
,
28
-continued

,

,
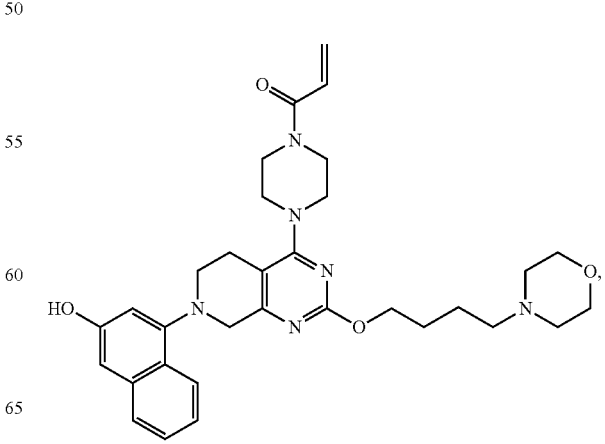
, 29
-continued
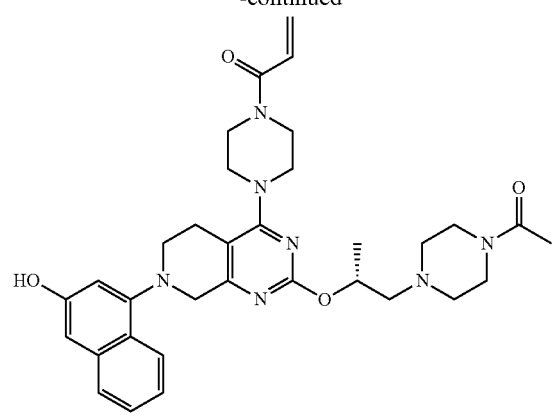
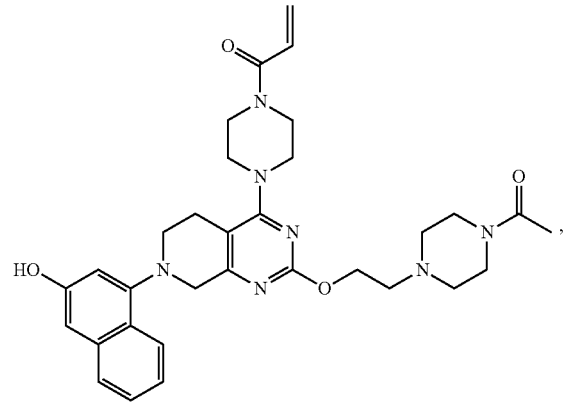
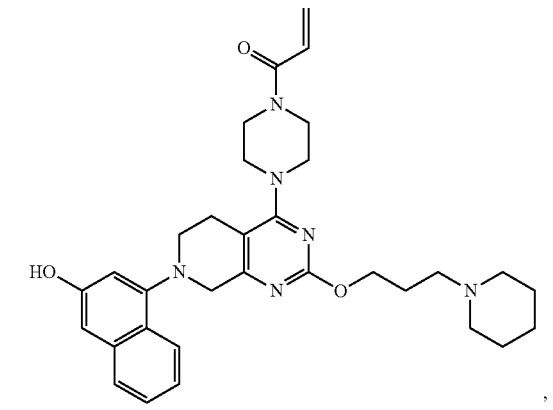
30
-continued
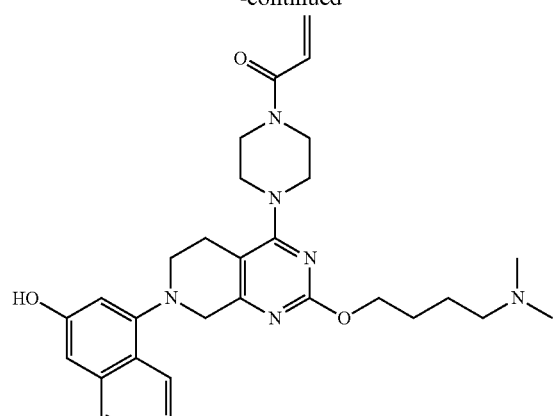
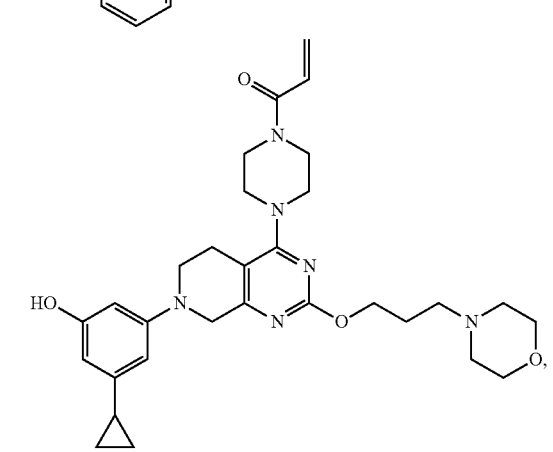
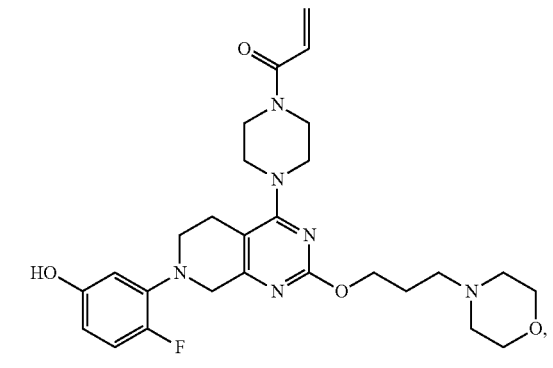
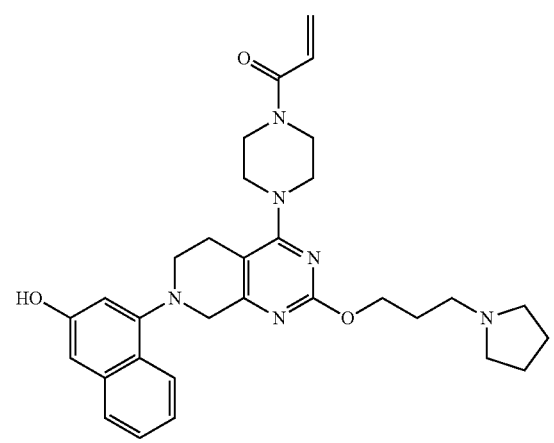

31
-continued
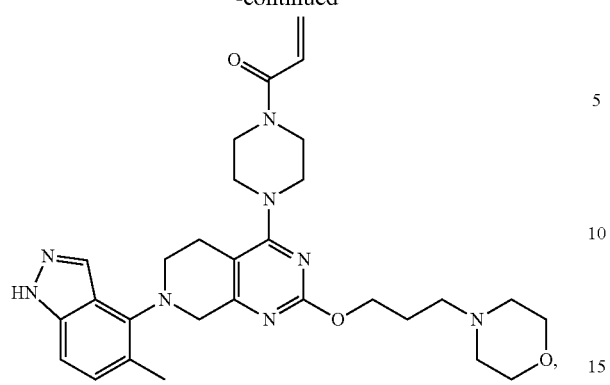
32
-continued
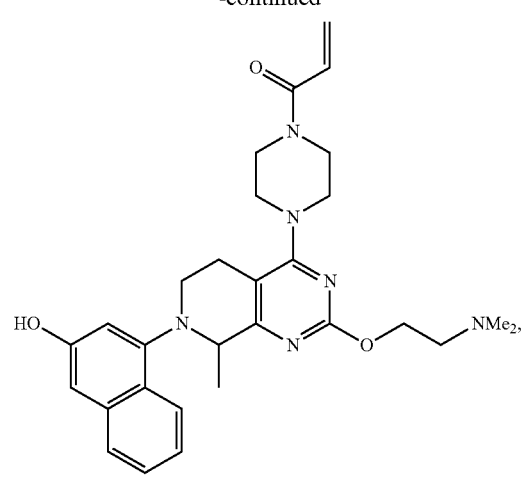
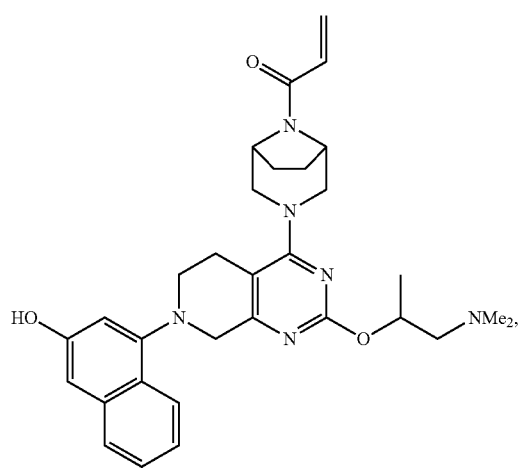
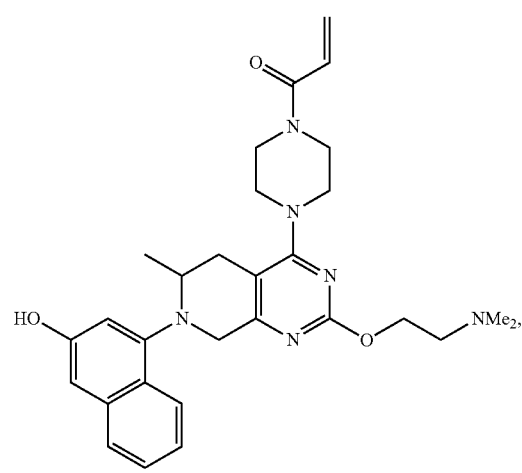
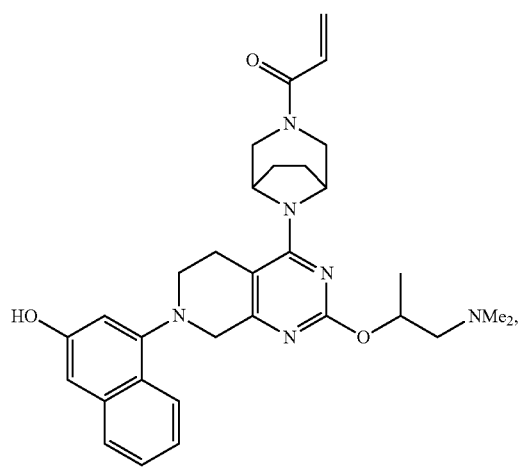
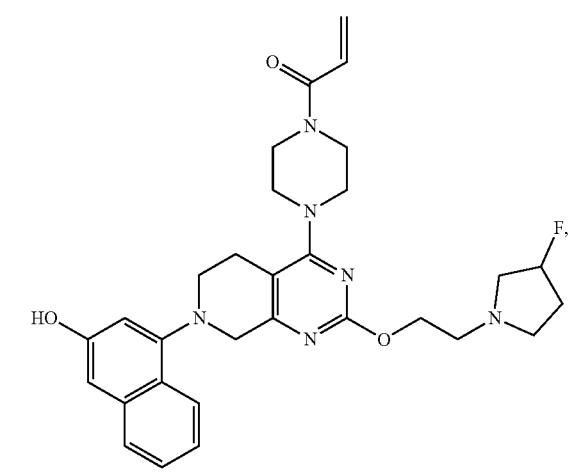

33
-continued
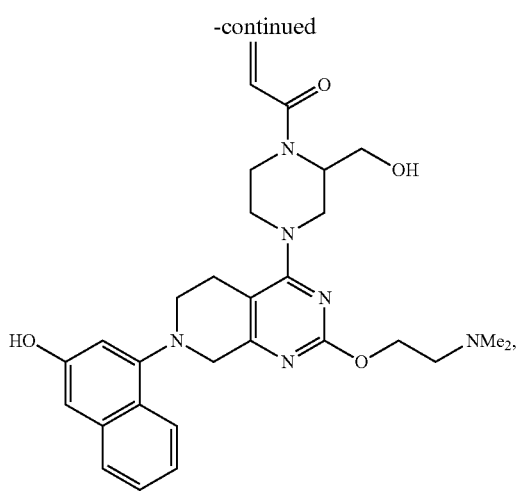
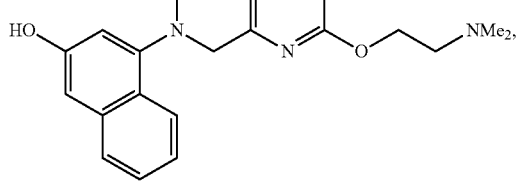
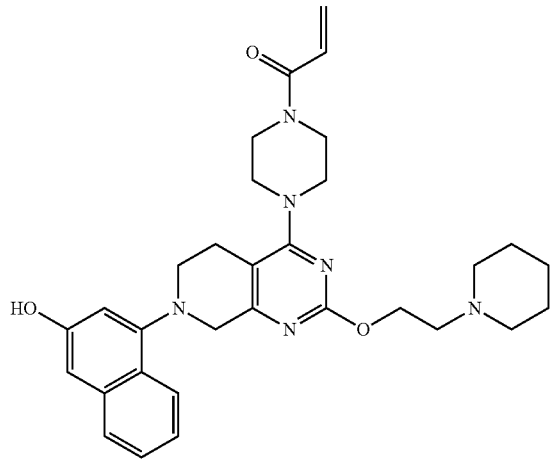
34
-continued
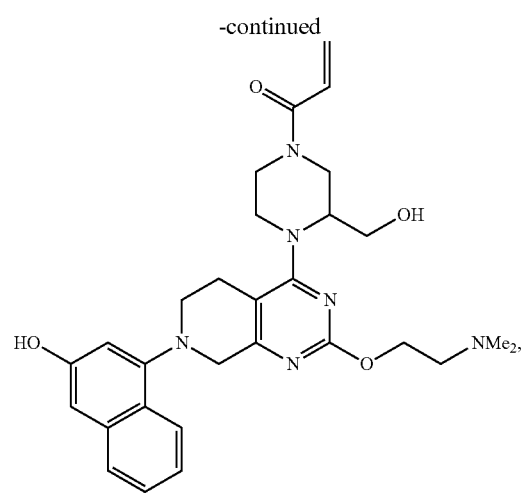
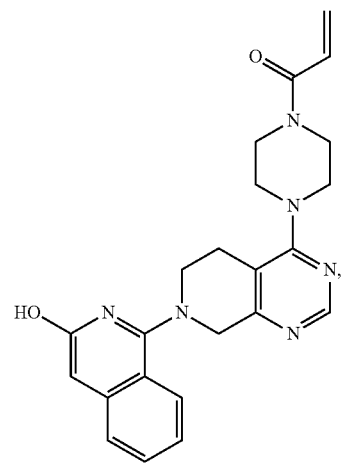
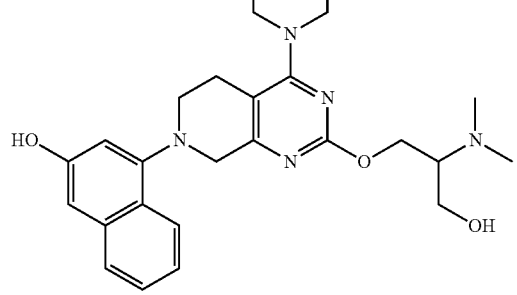

35
-continued
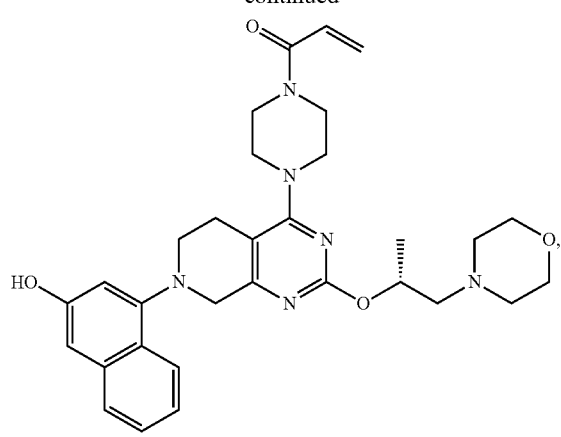
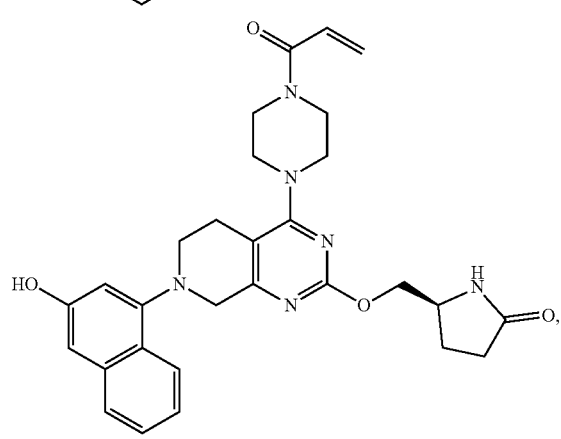
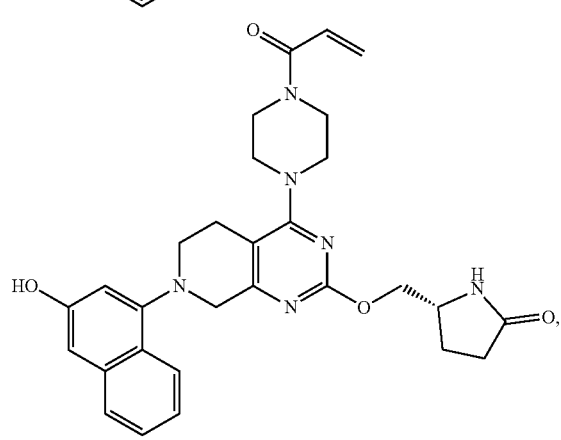
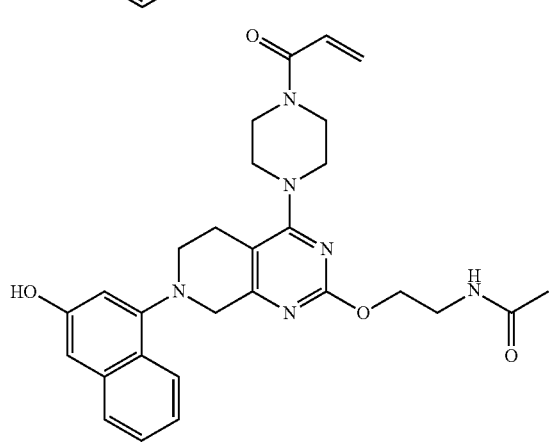
36
-continued
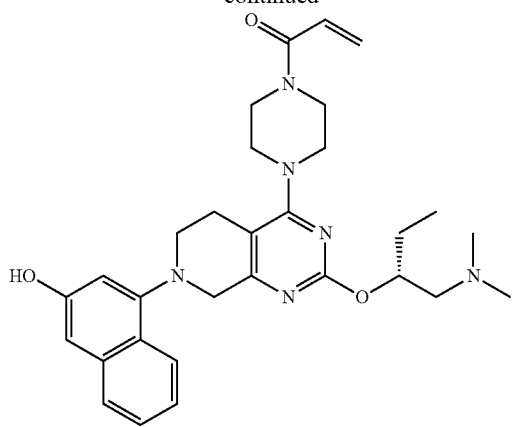
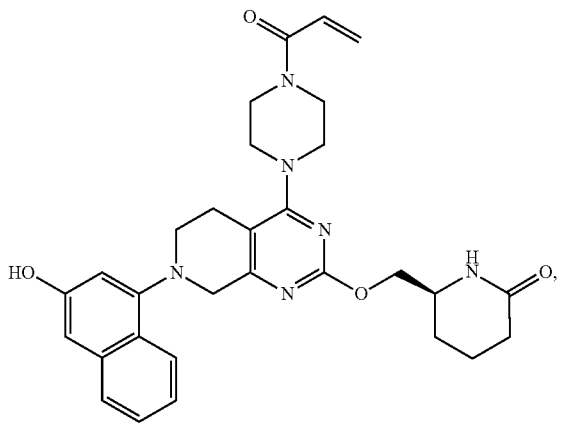
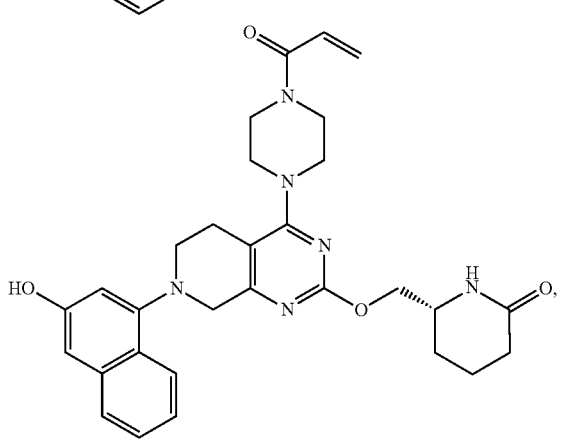
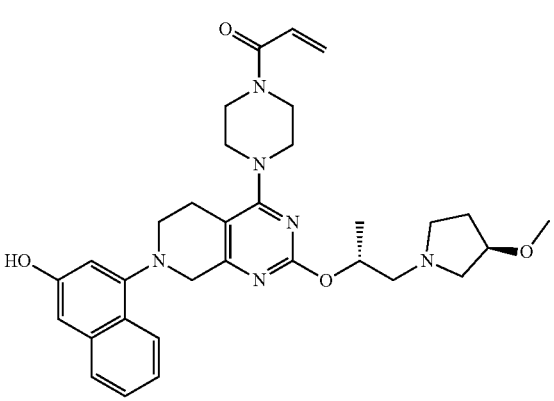

37
-continued
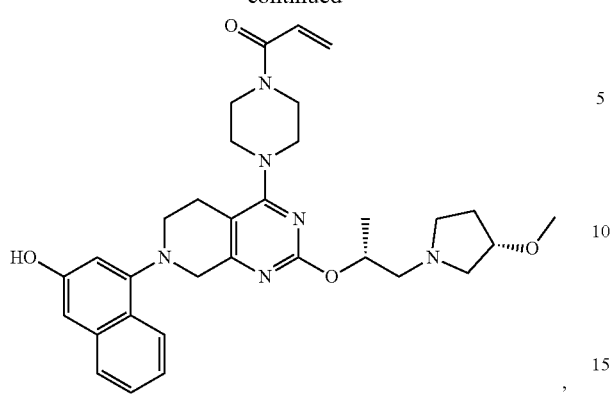
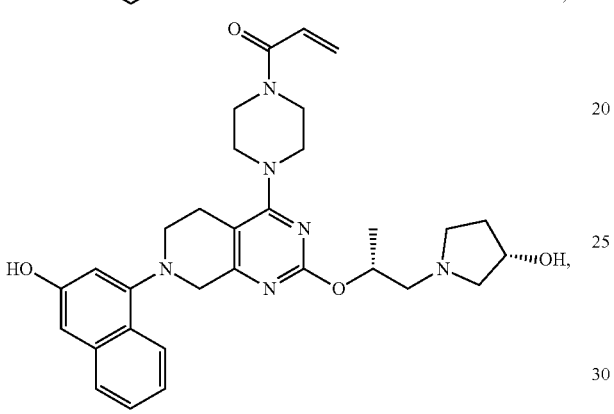
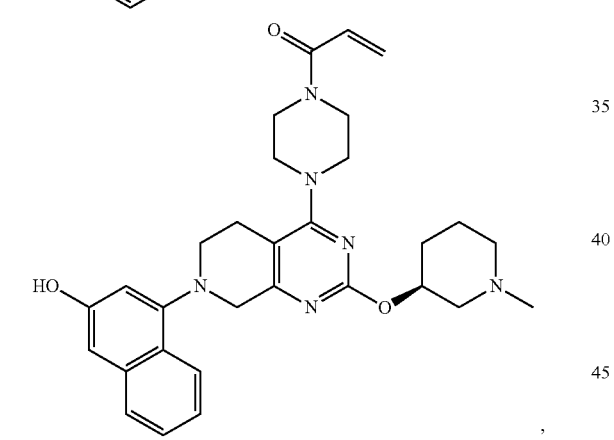
,
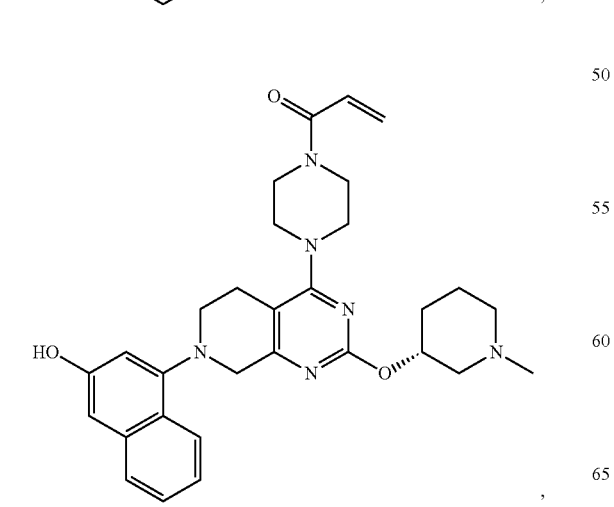
,
38
-continued
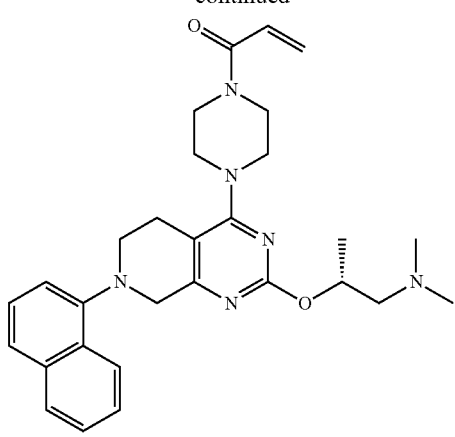
,
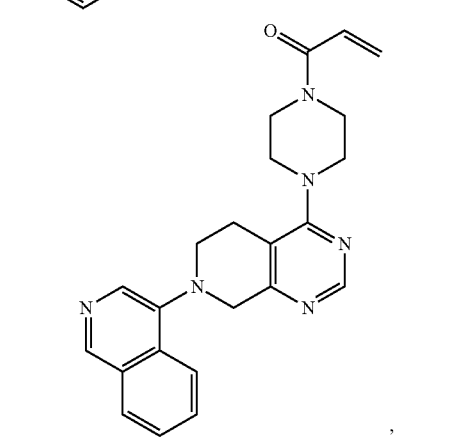
,
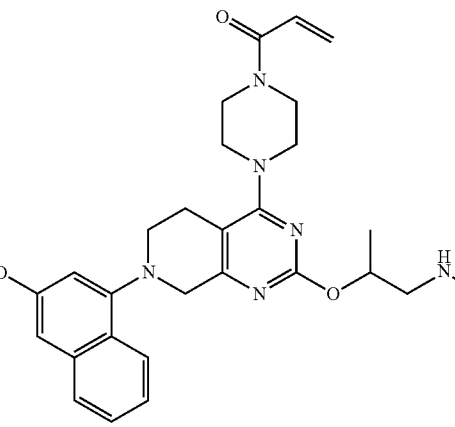
,
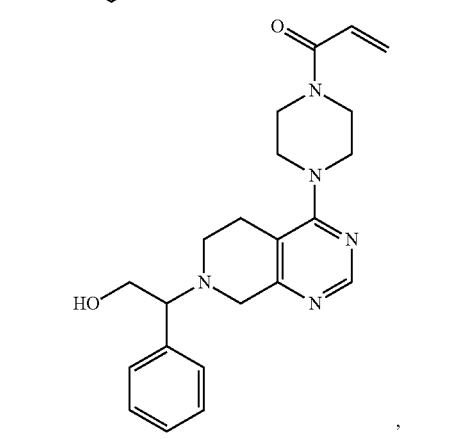
,

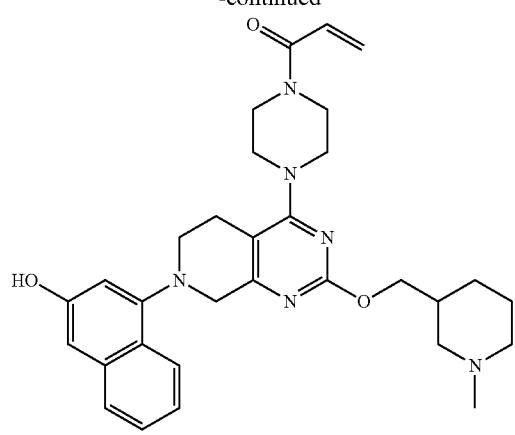
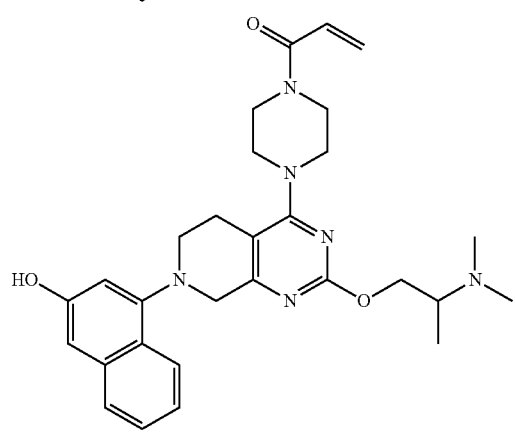
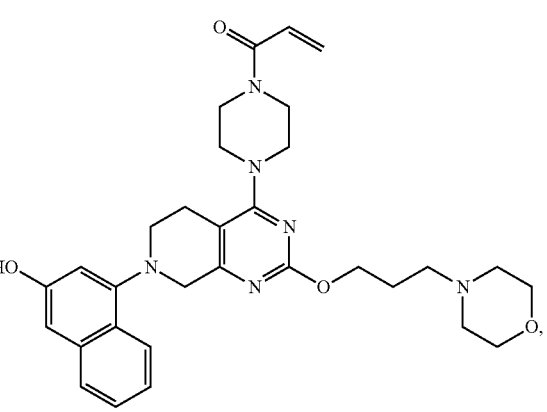
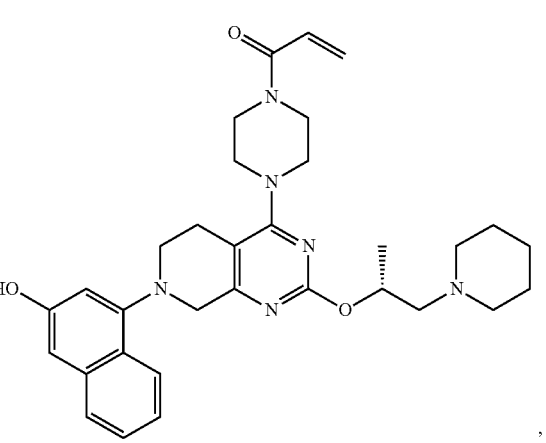
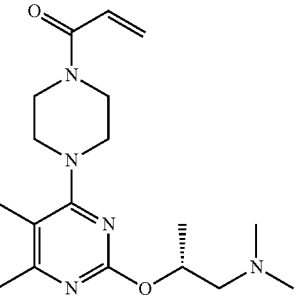
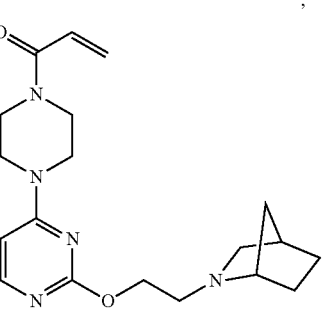
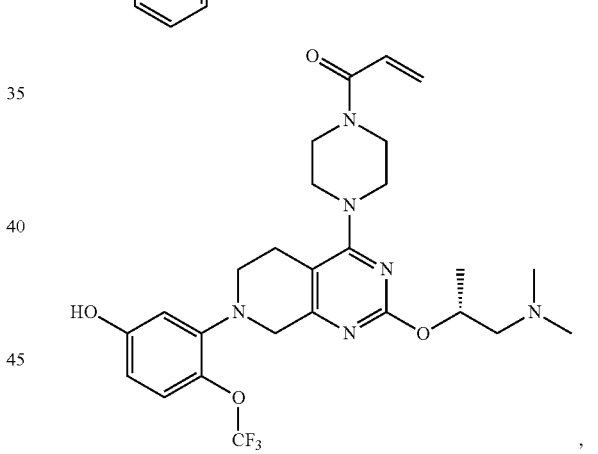
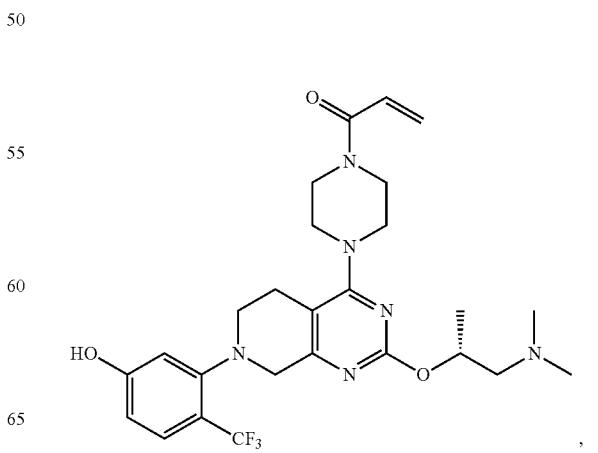

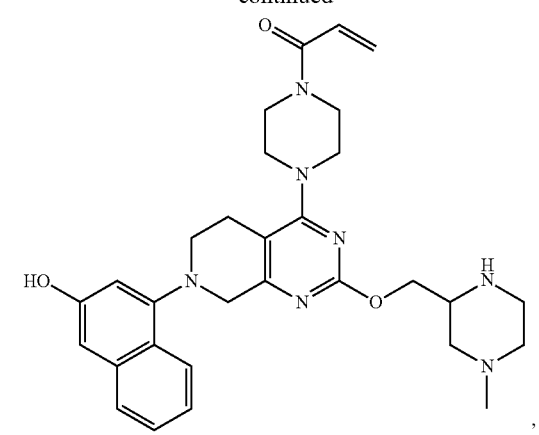
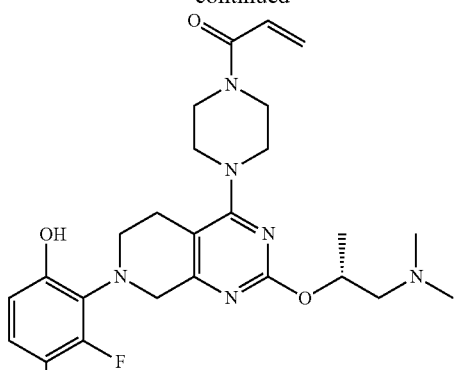
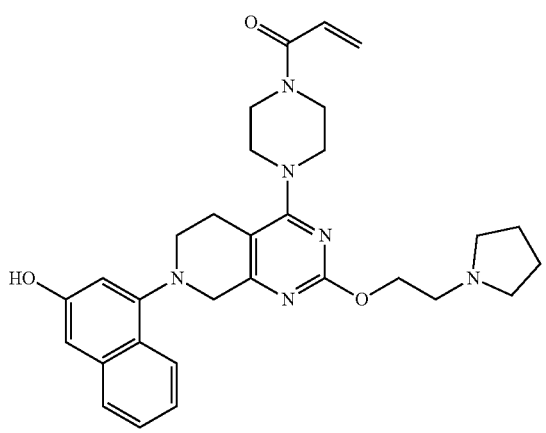
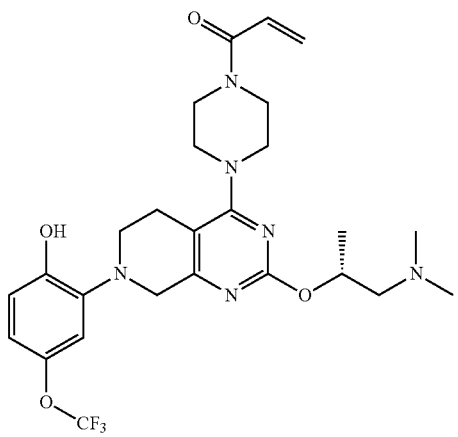
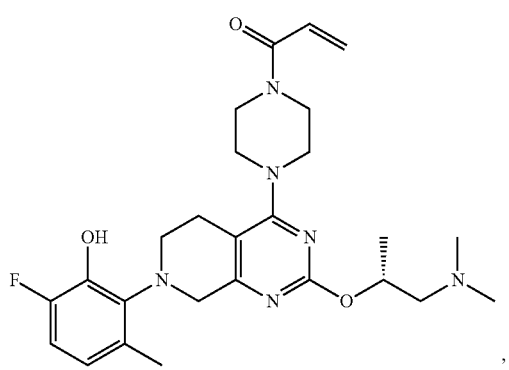

-continued
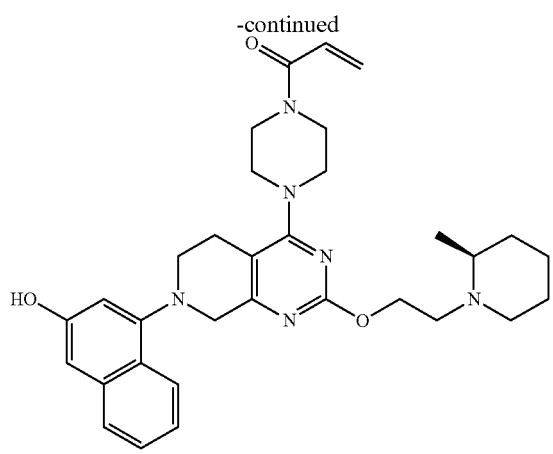
-continued
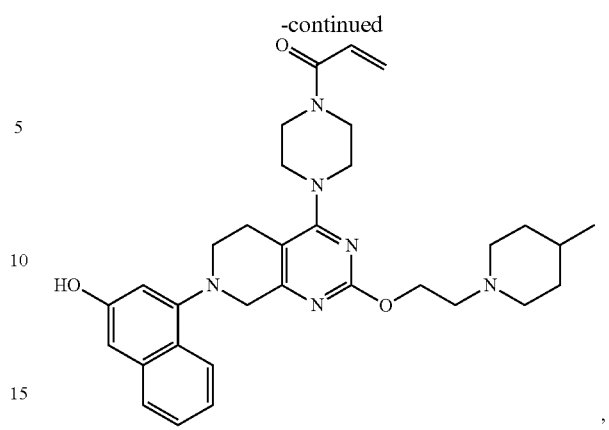

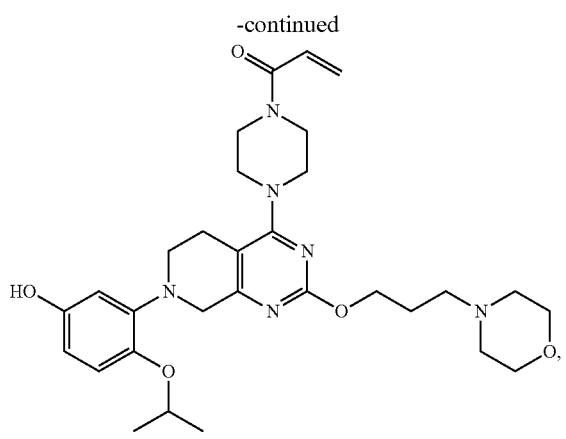
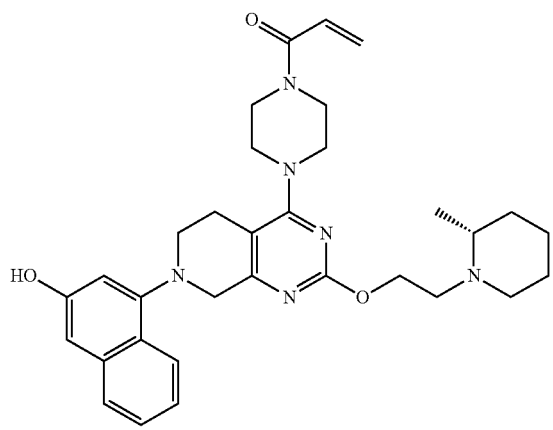
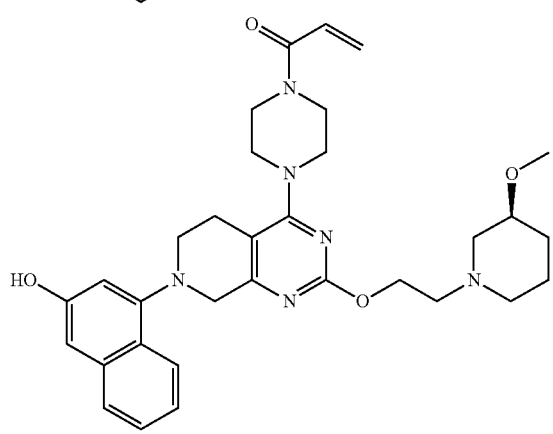
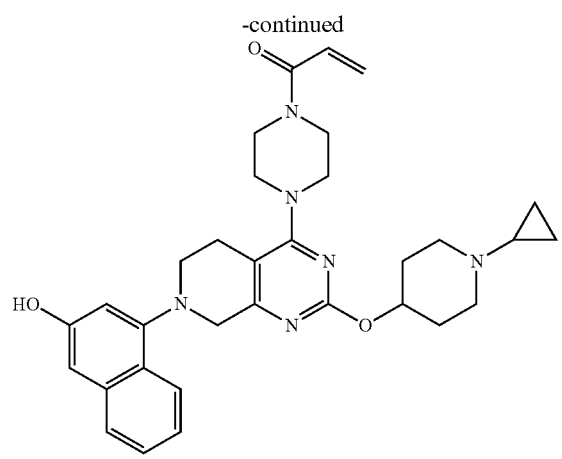
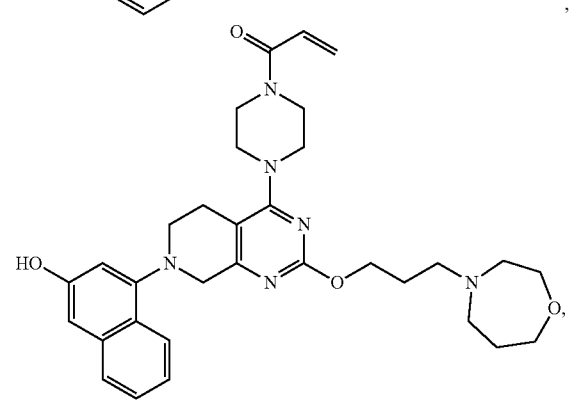
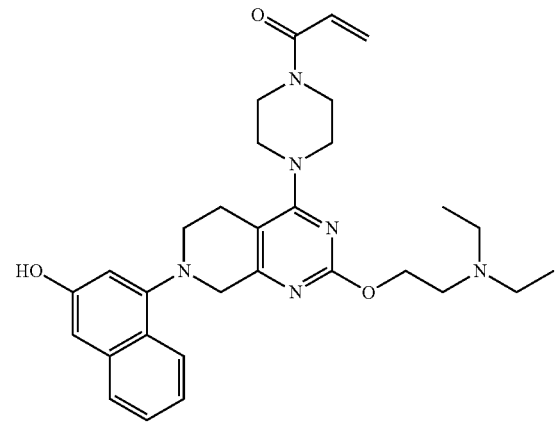
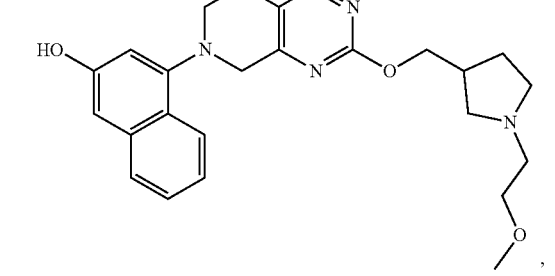

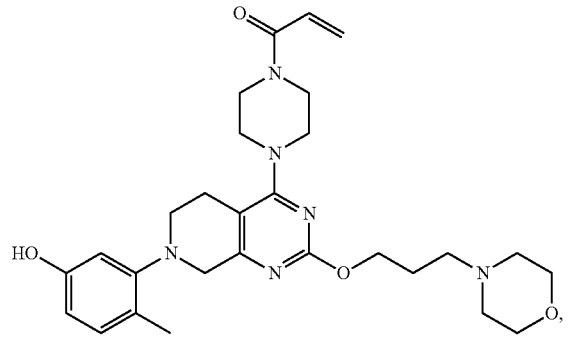
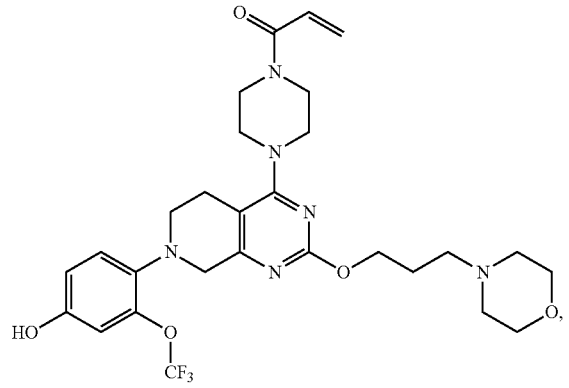

49

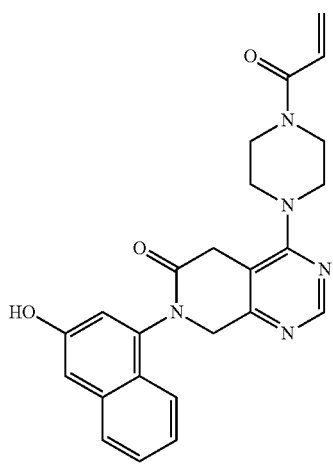
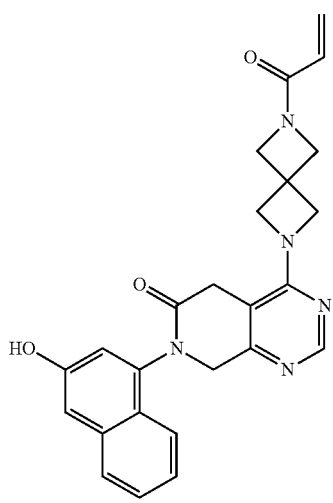
50
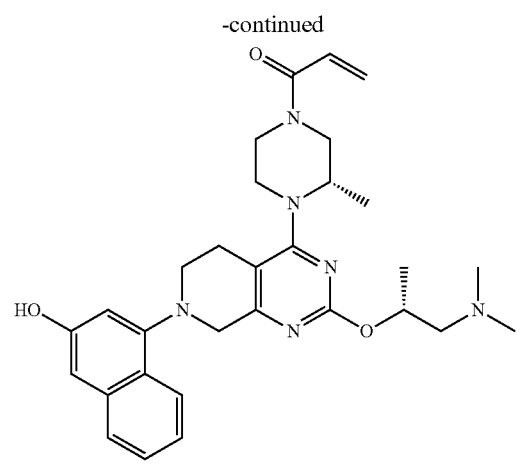
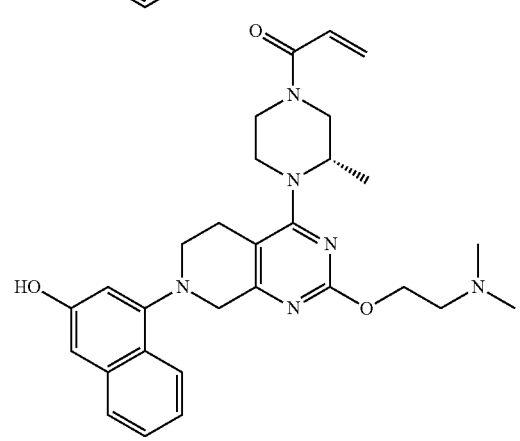
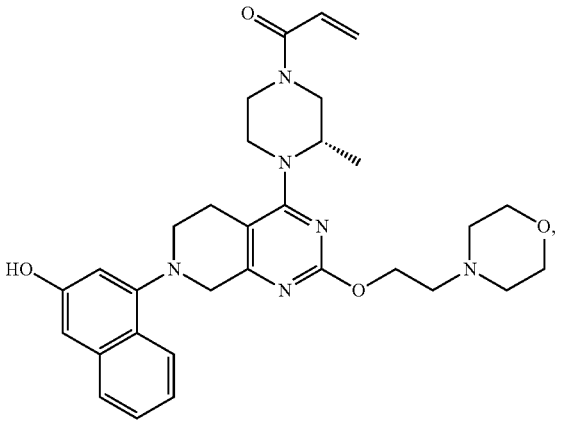
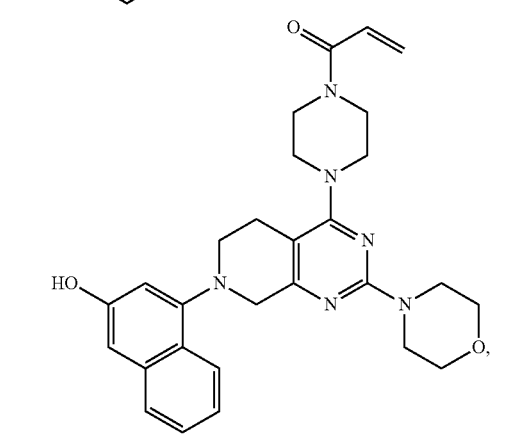

51
-continued
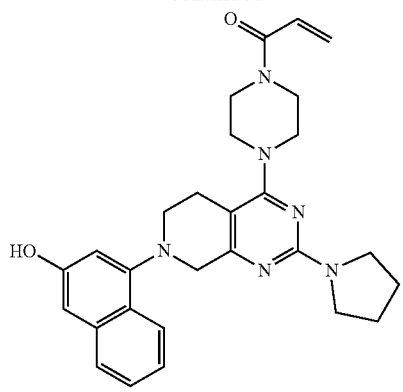
,
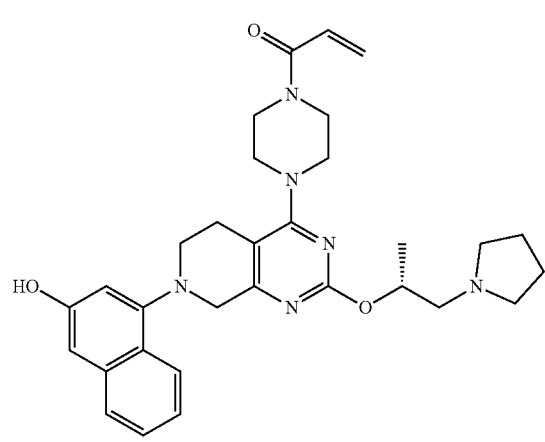
,
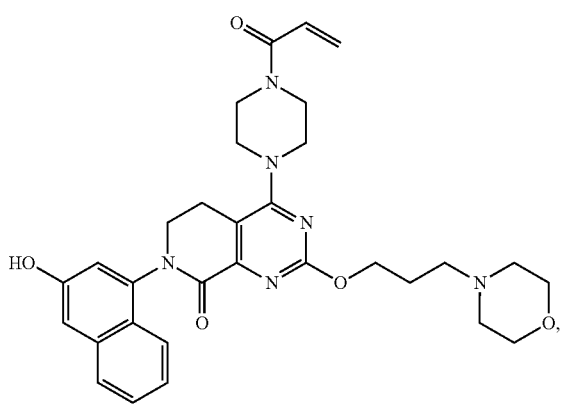
,
52
-continued
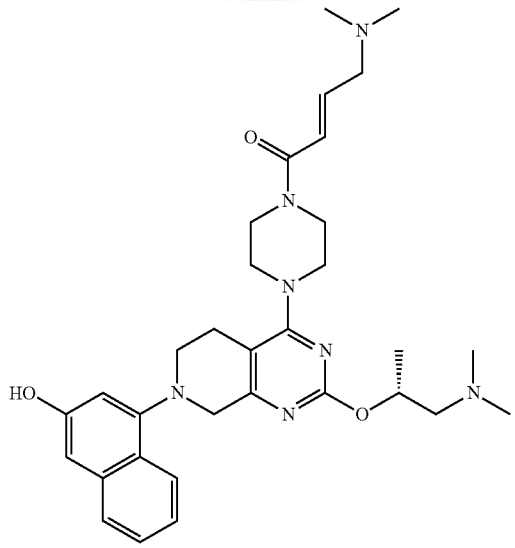
,
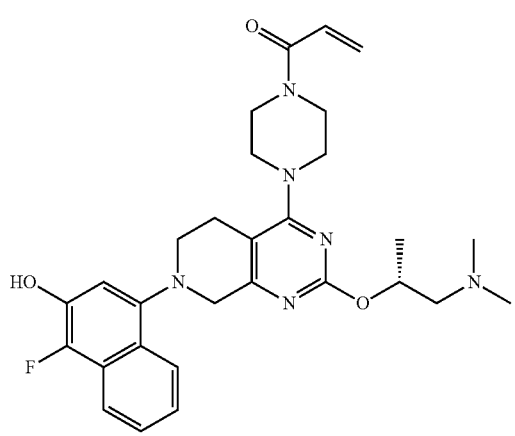
, 53
-continued
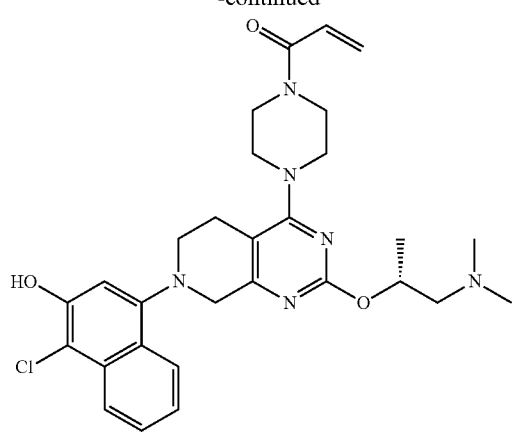
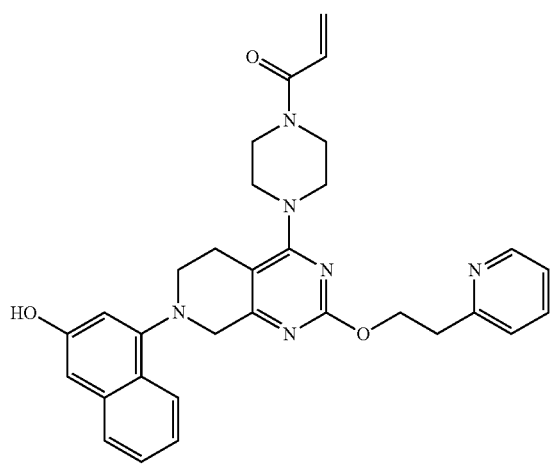
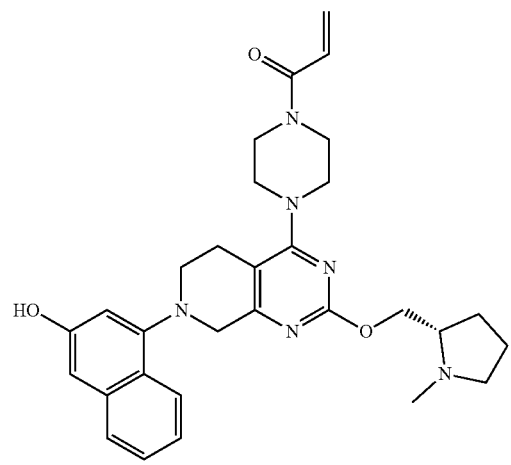
54
-continued
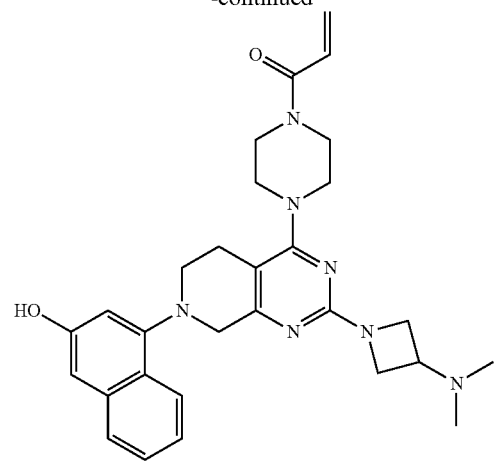
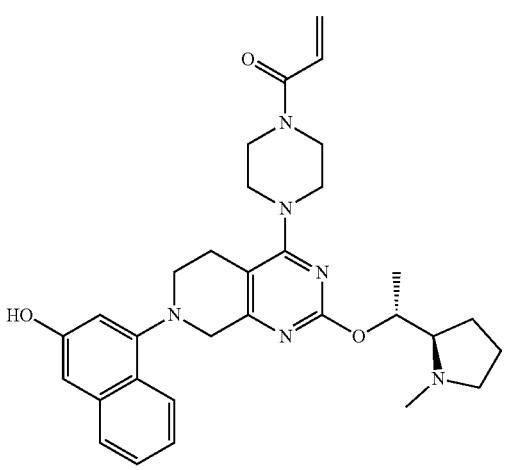
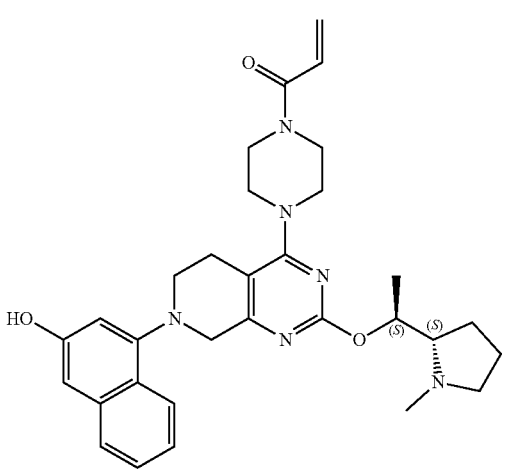

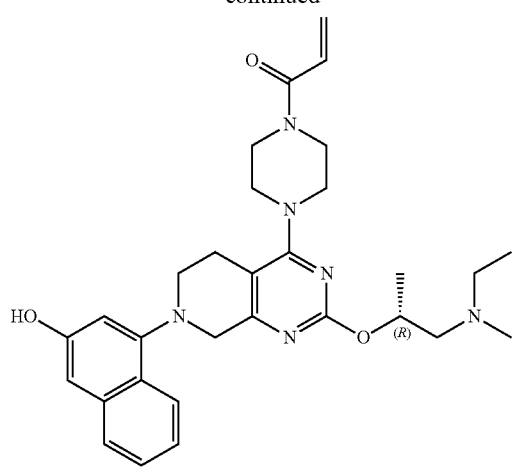
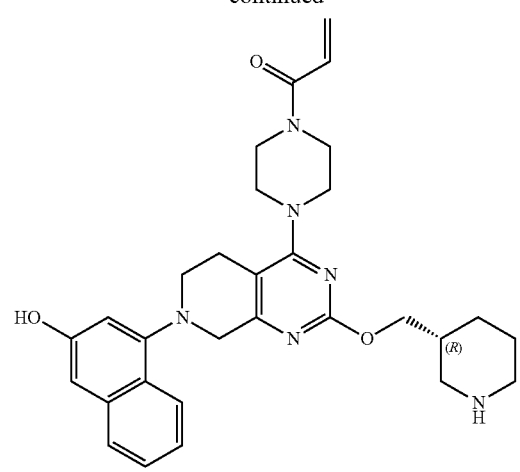
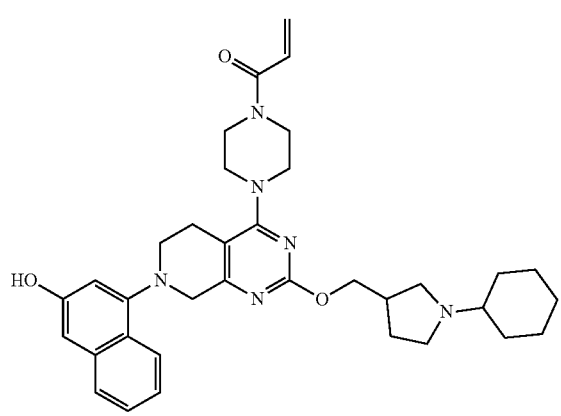
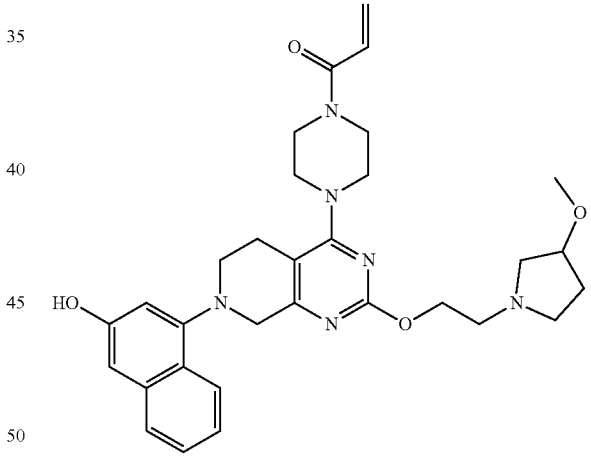
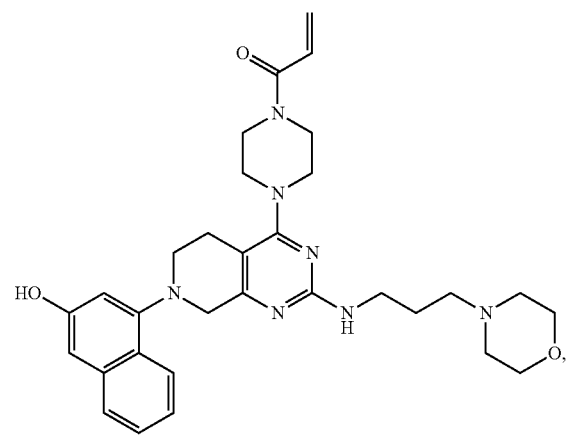
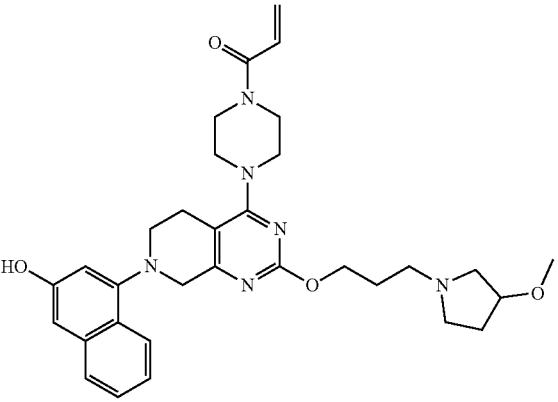

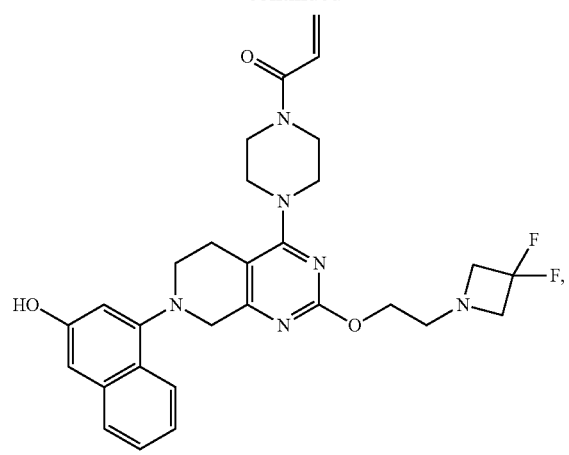
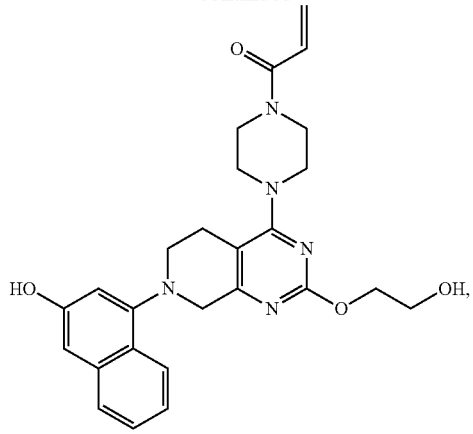

59
-continued
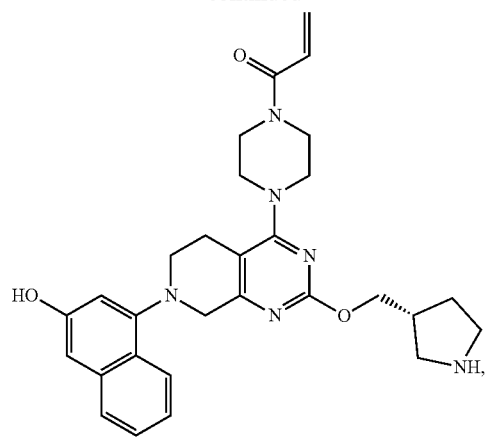
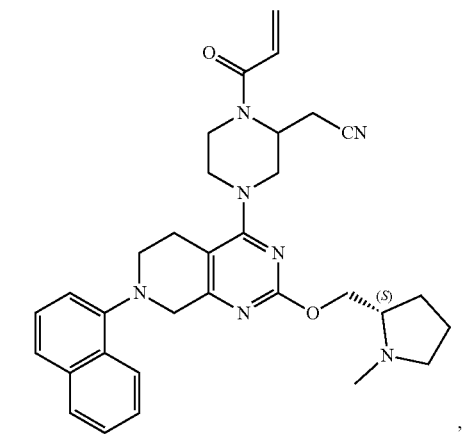
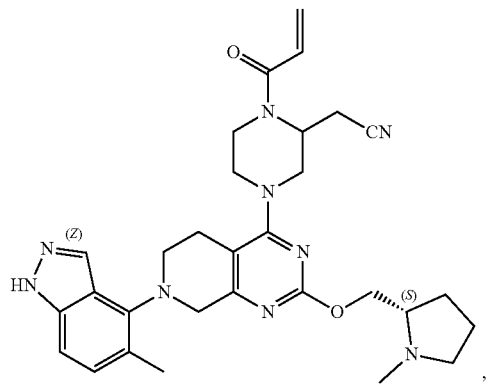
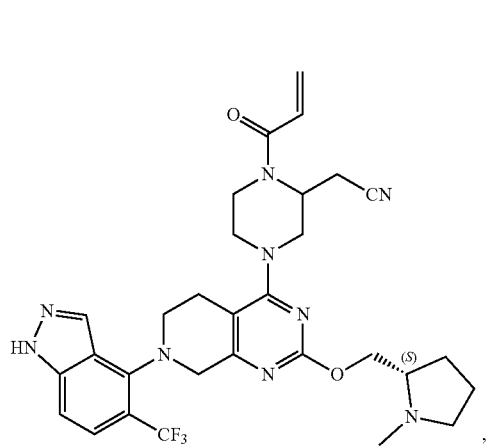
60
-continued
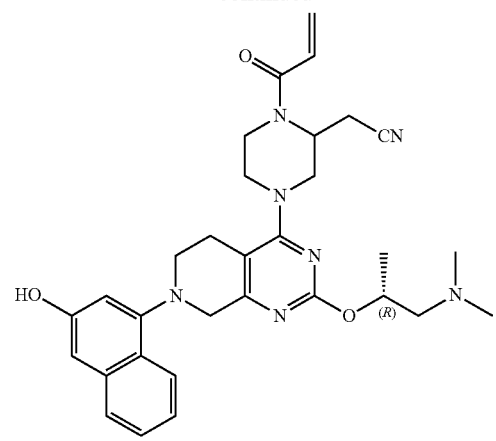
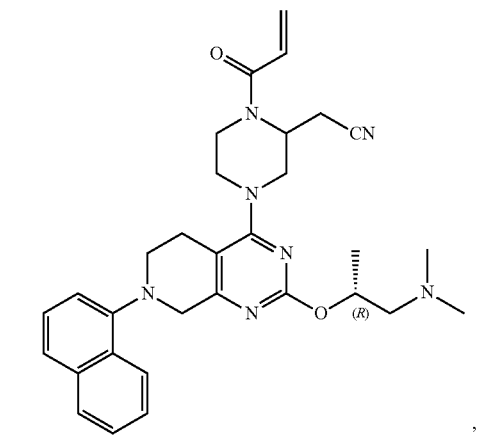
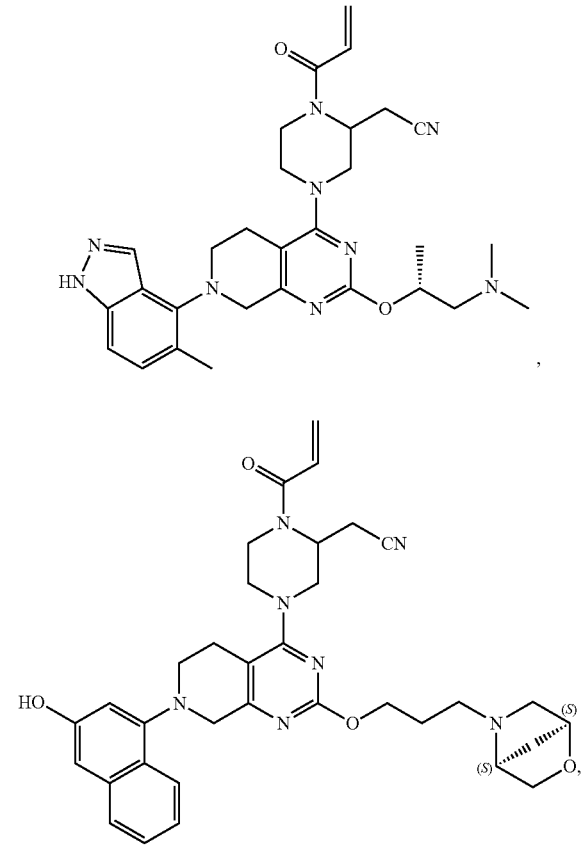

61
-continued
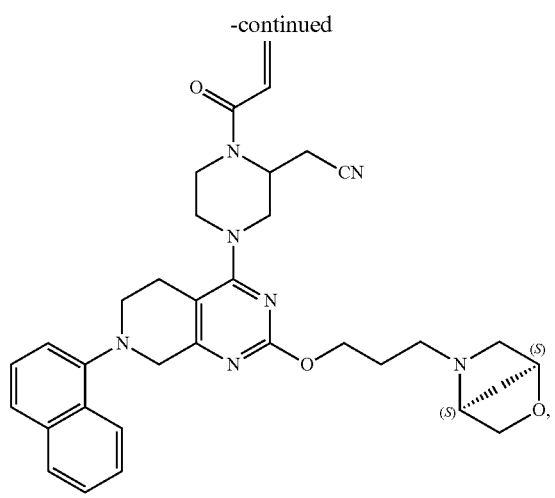
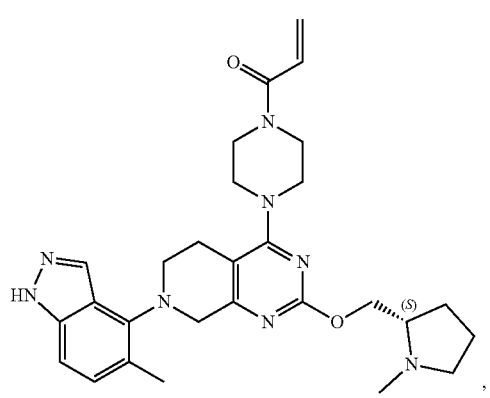
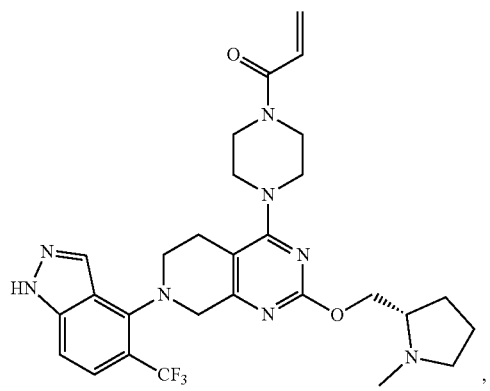
and pharmaceutically acceptable salts thereof.
Further nonlimiting examples of compounds of Formula (I), Formula I-A and Formula I-B are selected from the group consisting of:
62
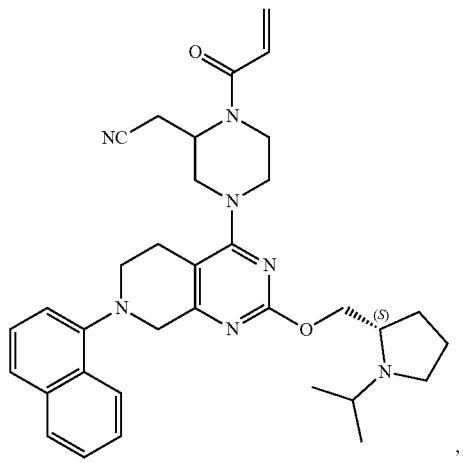
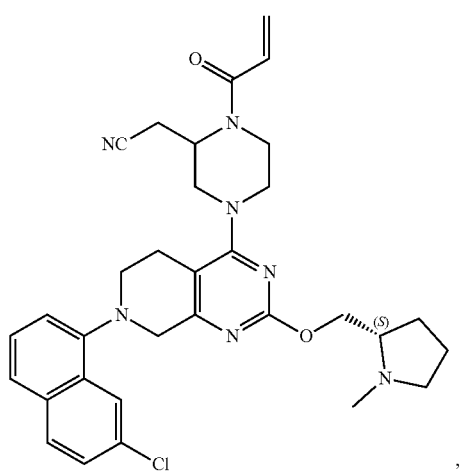
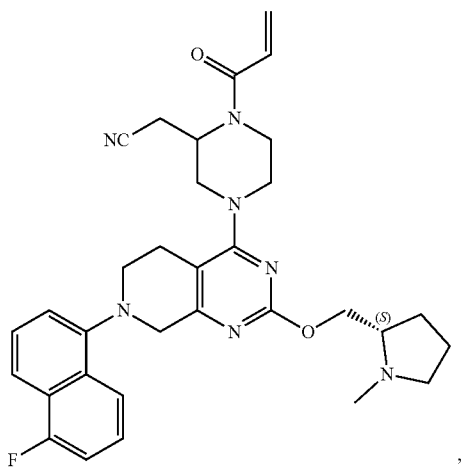

63
-continued
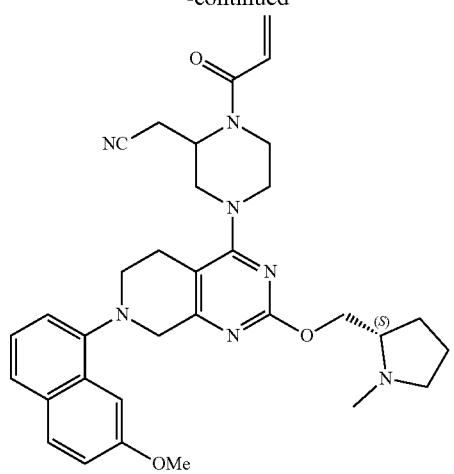
,
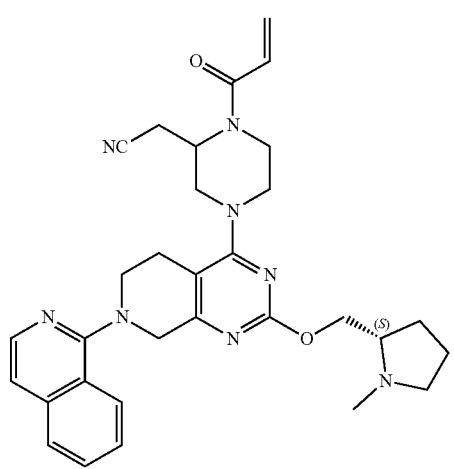
,
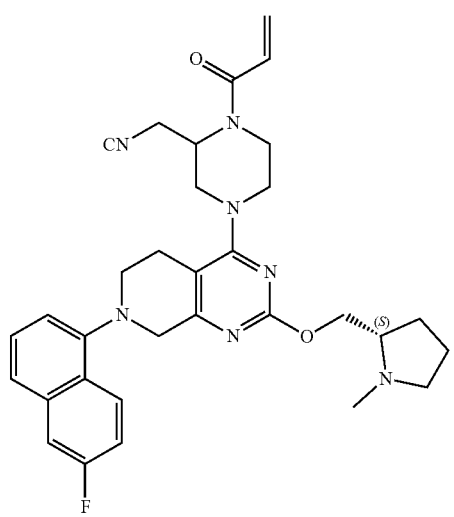
,
64
-continued
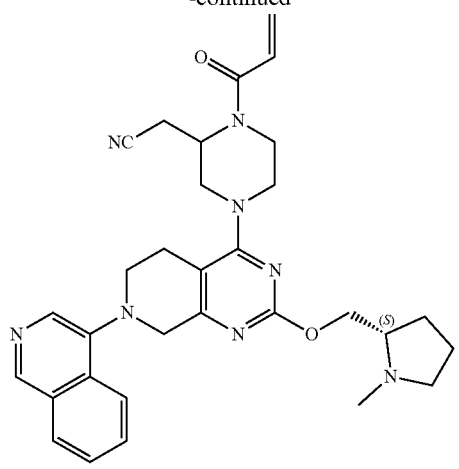
,
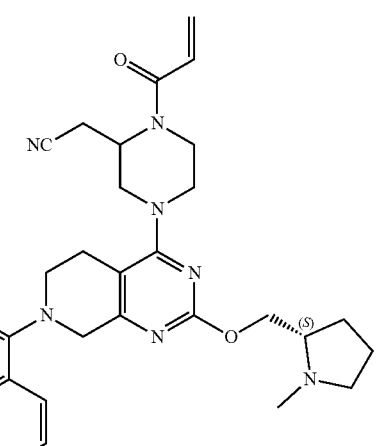
,
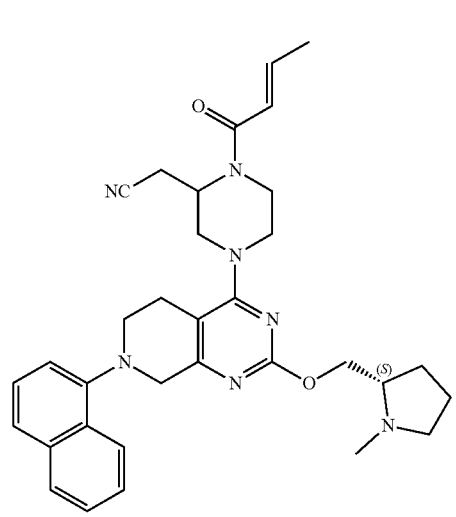
, 65
-continued
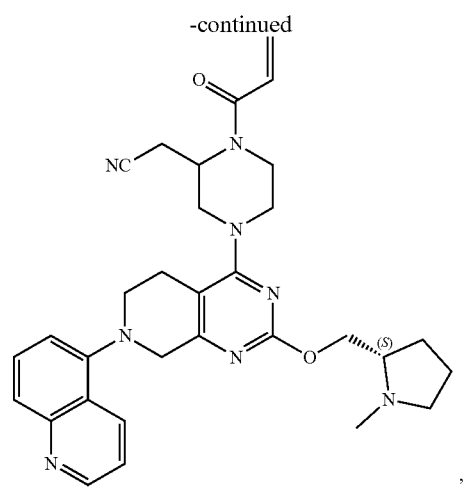
,
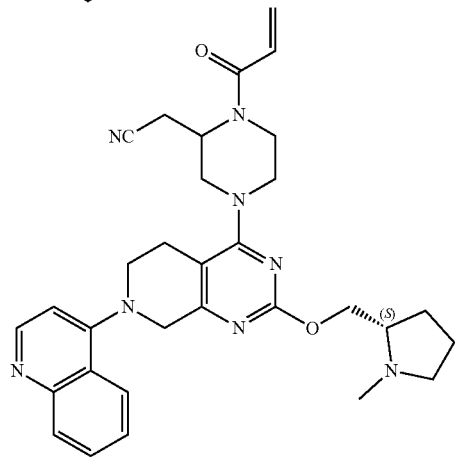
,
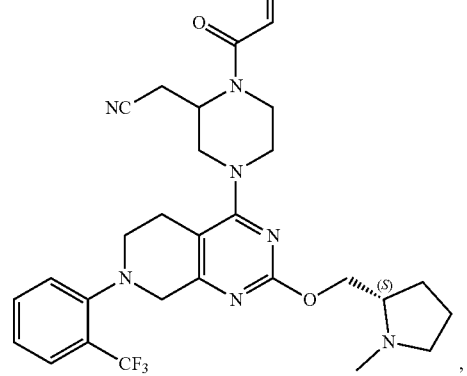
,
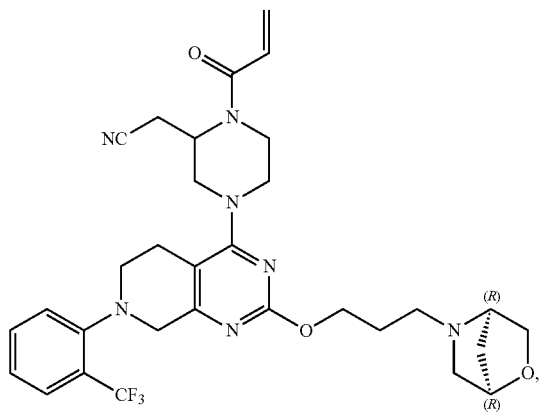
,
66
-continued
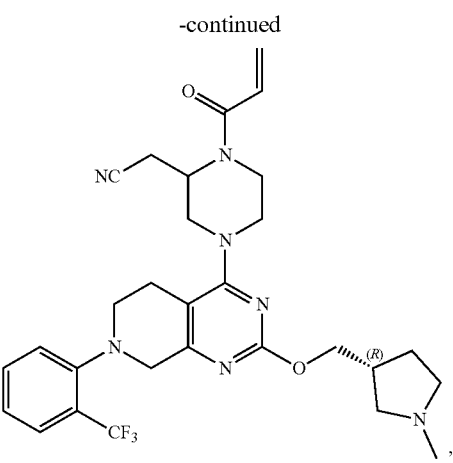
,
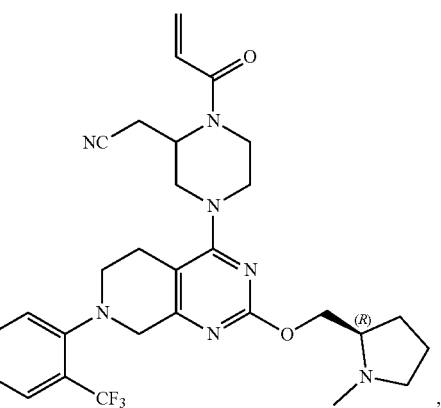
,
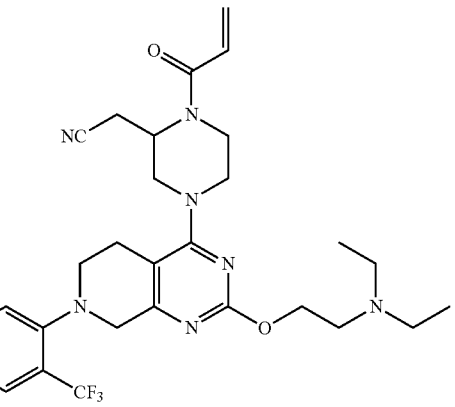
,
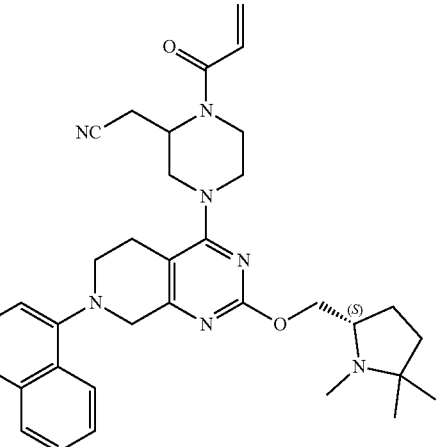
, -continued
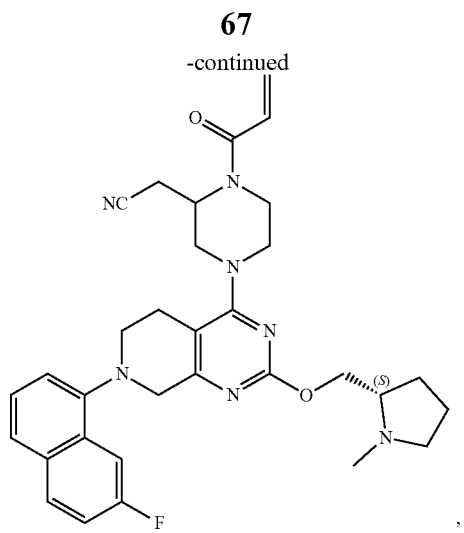
,
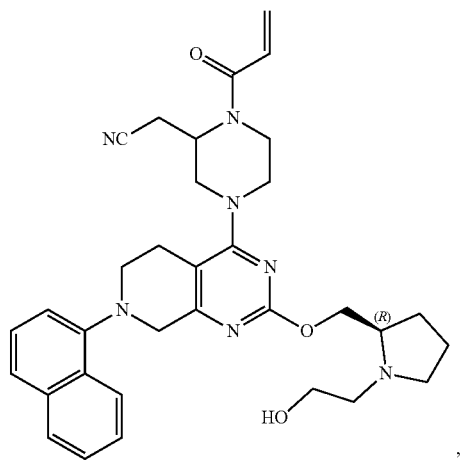
,
-continued
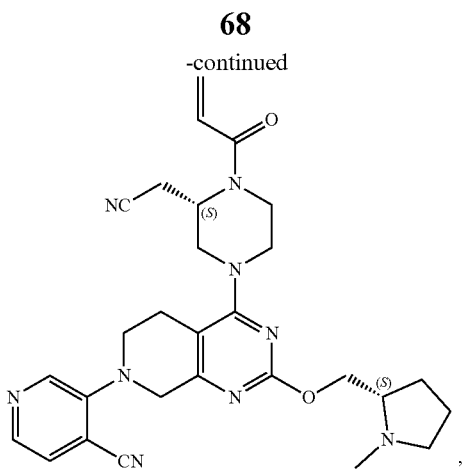
,
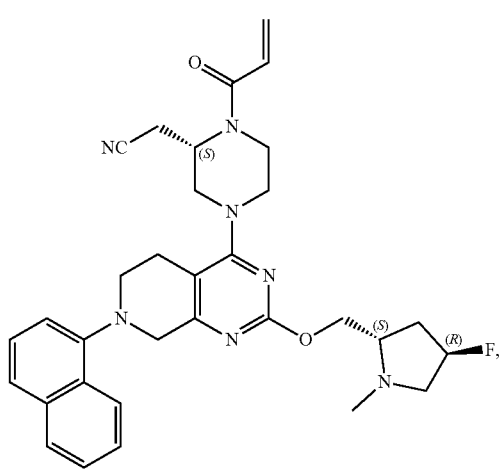
,
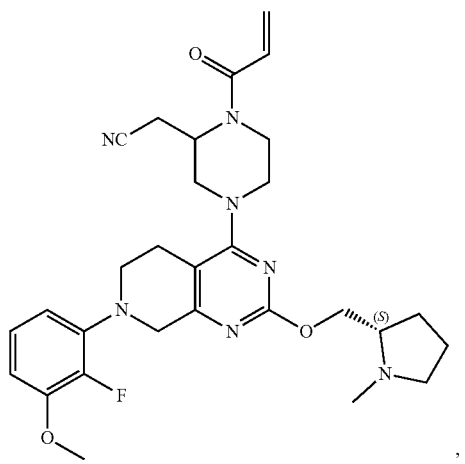
,

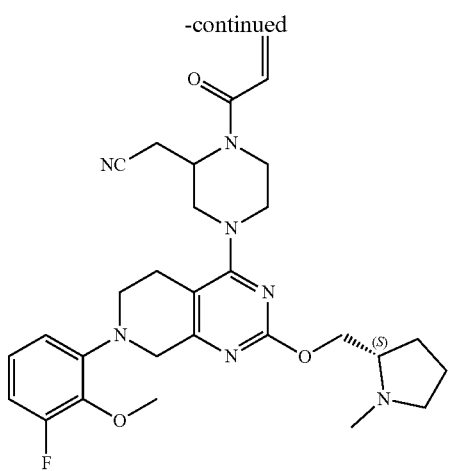
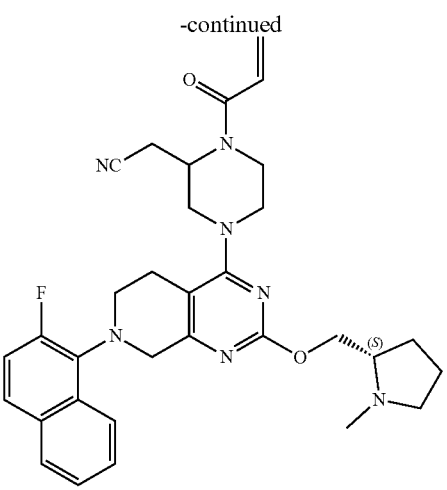
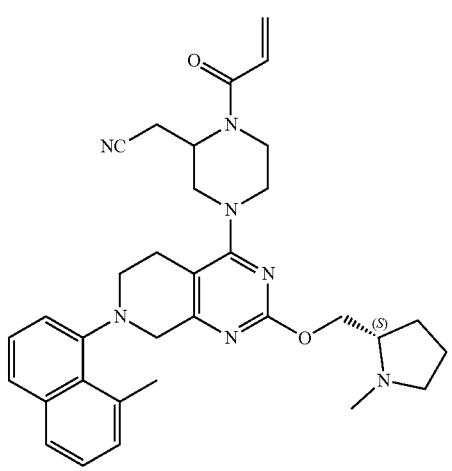
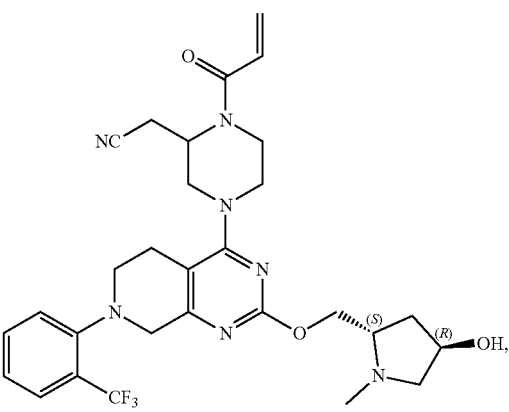
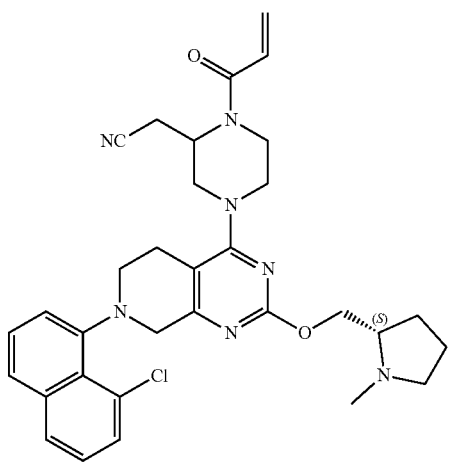
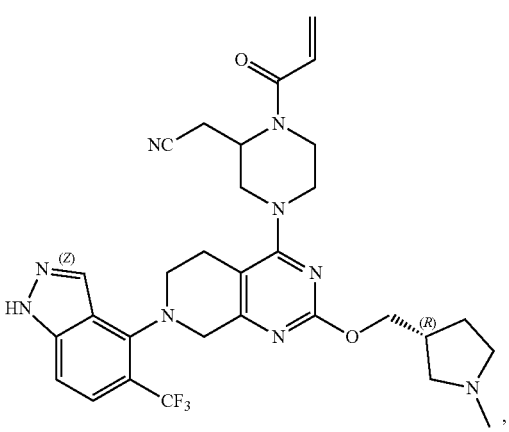

-continued
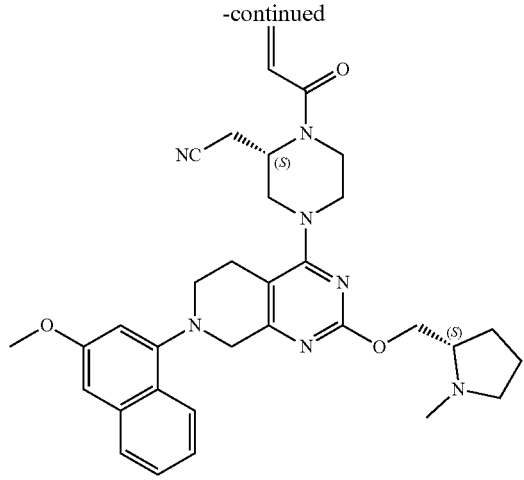
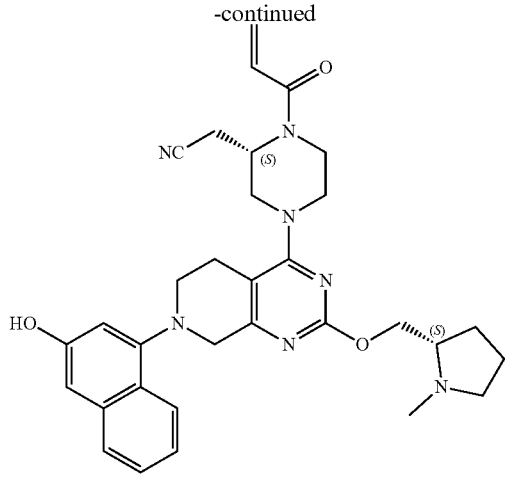
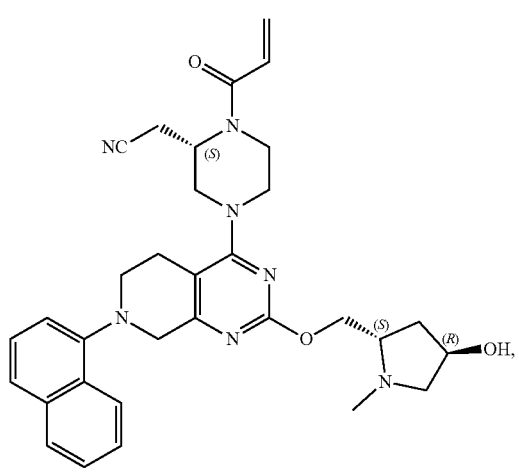
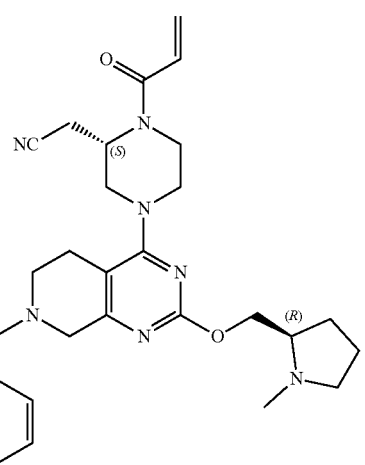
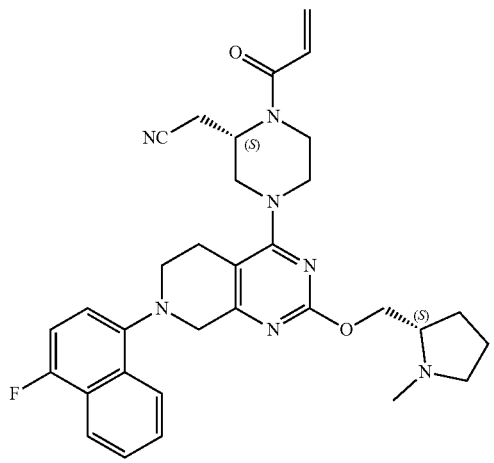
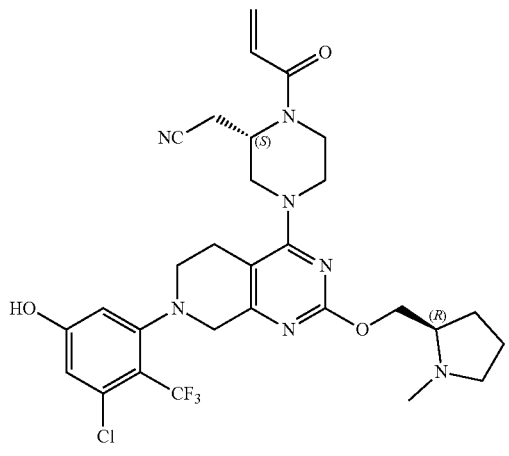

73
-continued
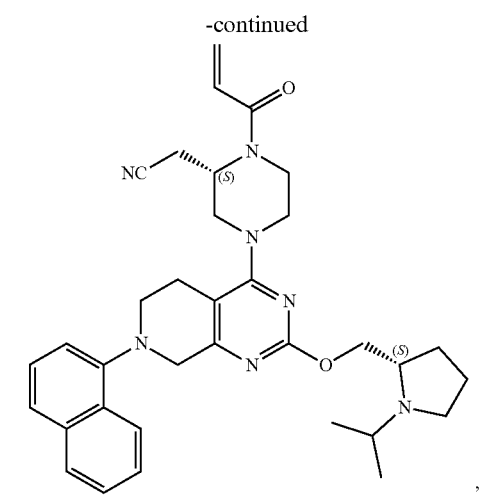
,
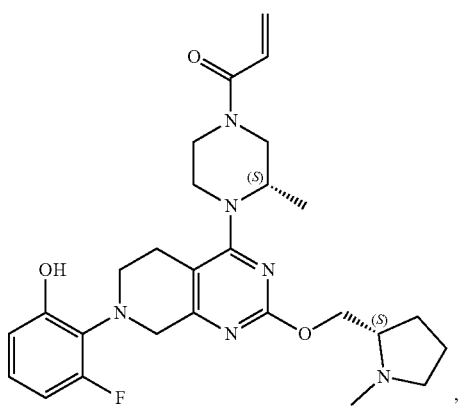
,
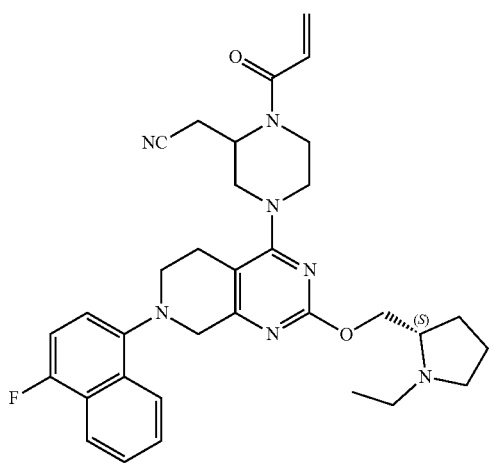
,
74
-continued
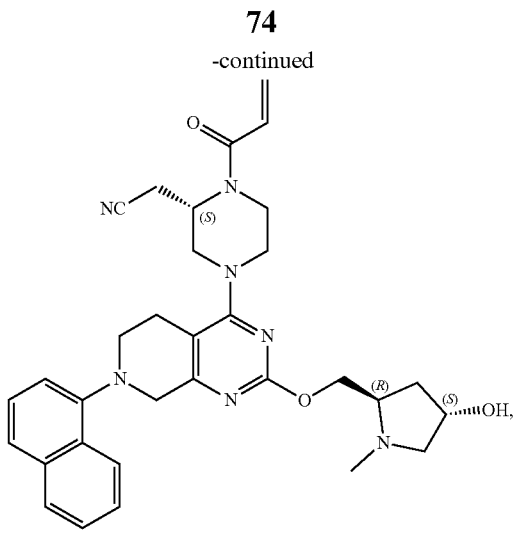
,
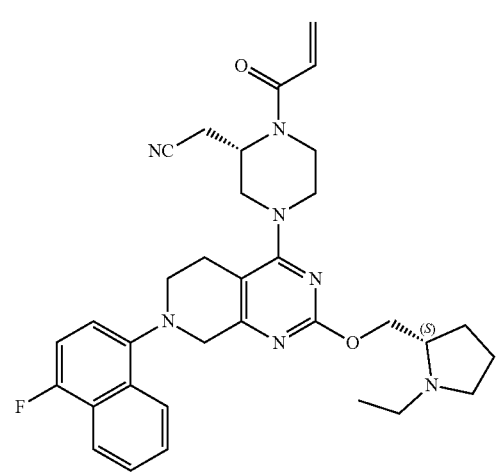
,
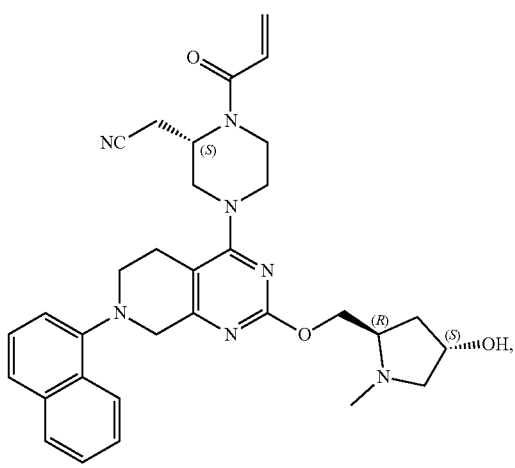
, 75
-continued
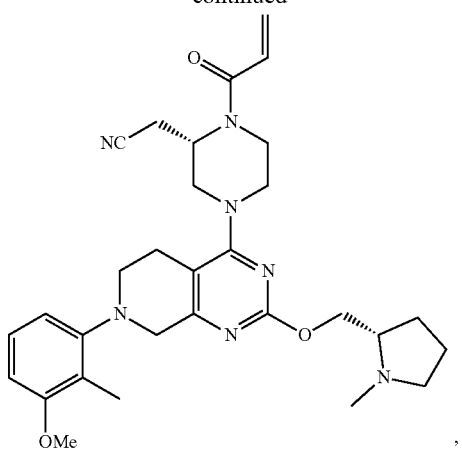
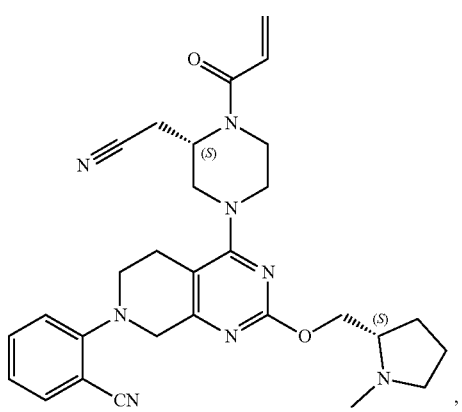
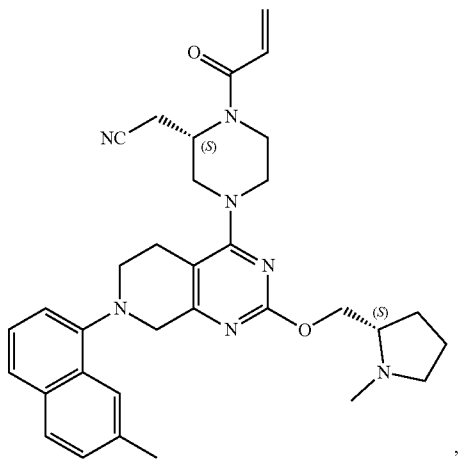
76
-continued
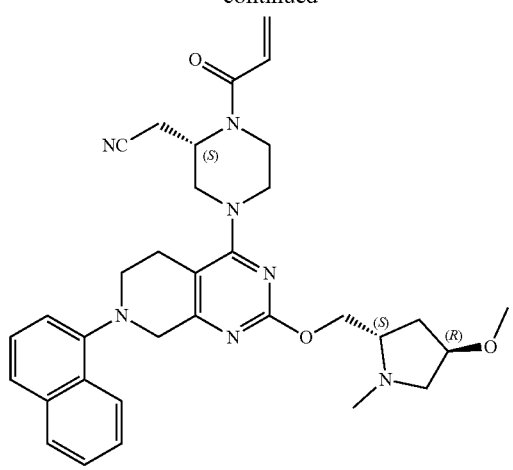
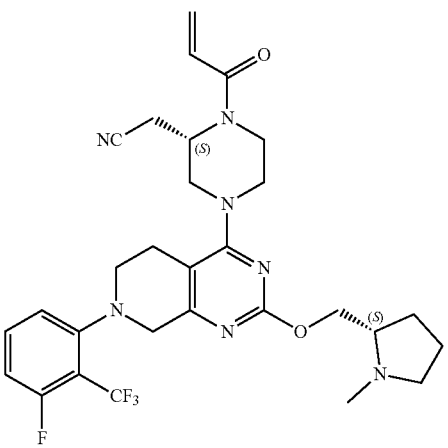
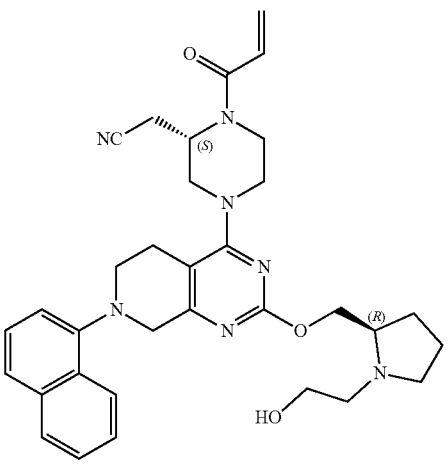

77
-continued
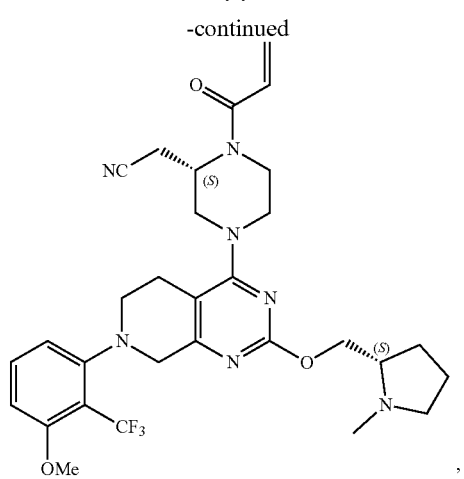
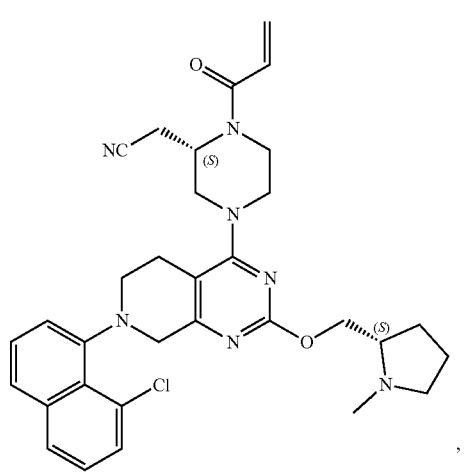
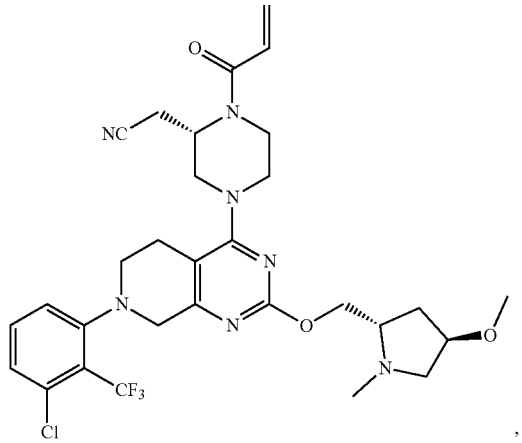
78
-continued
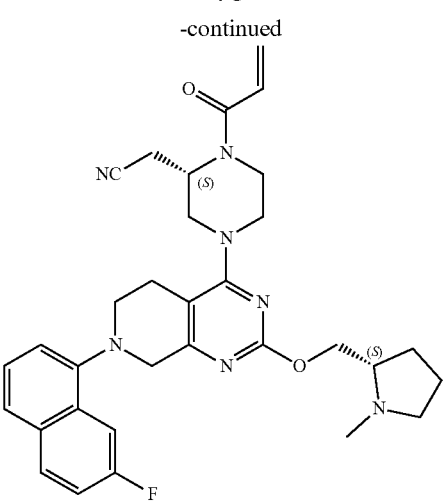
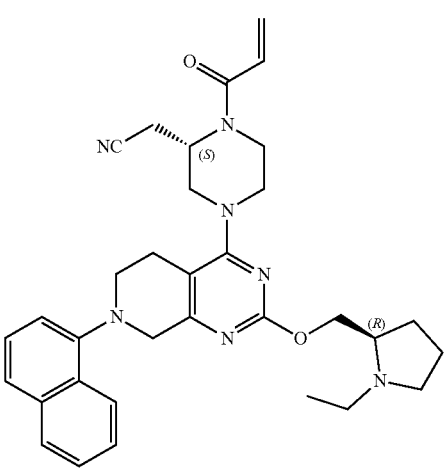
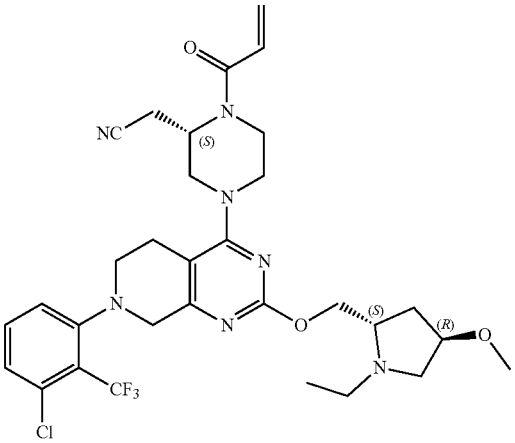

79
-continued

80
-continued

81
-continued
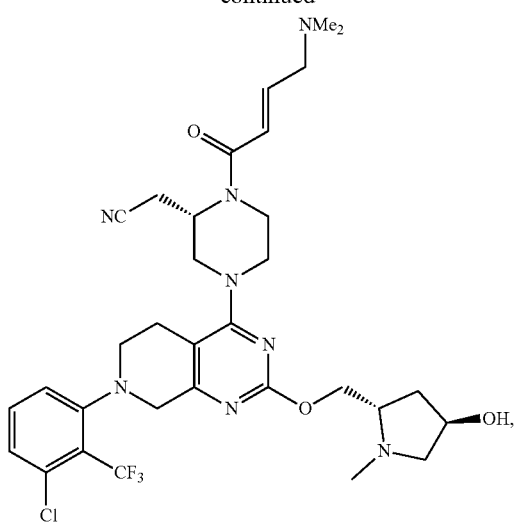
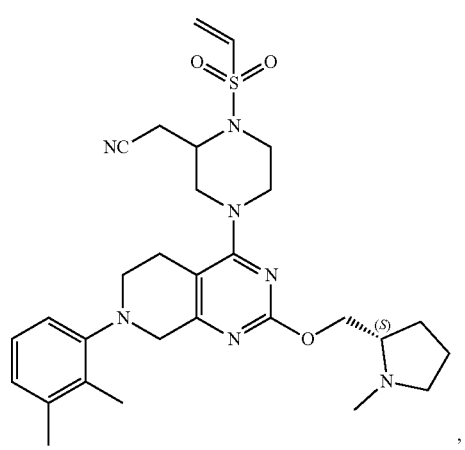
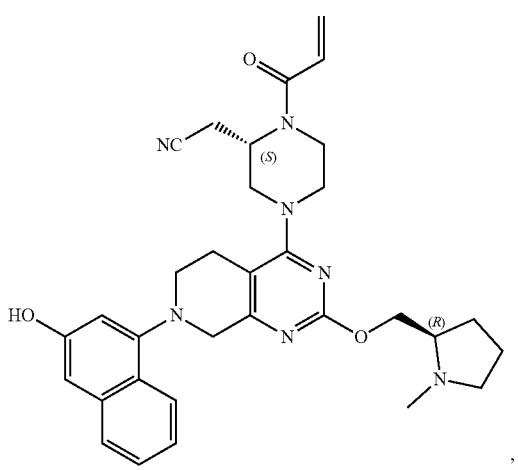
82
-continued
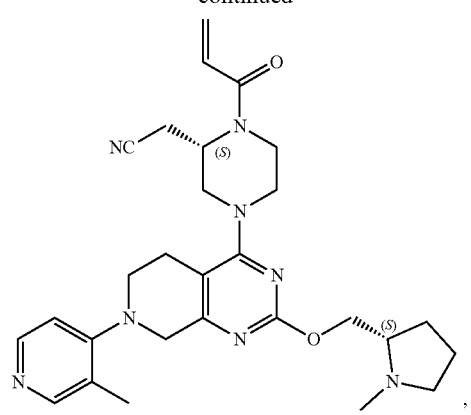
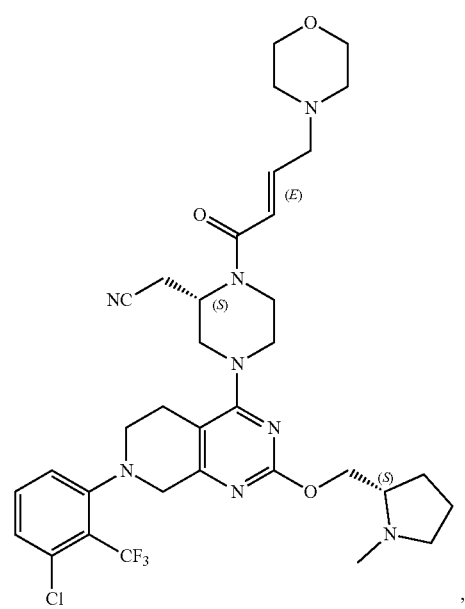
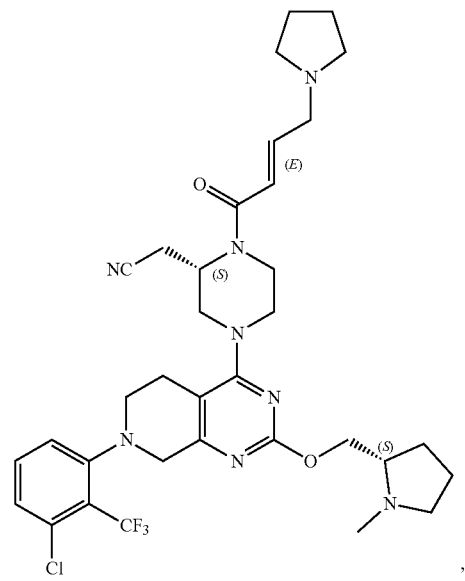

83
-continued
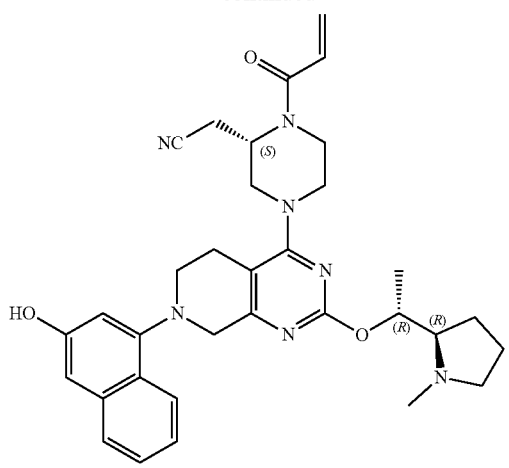
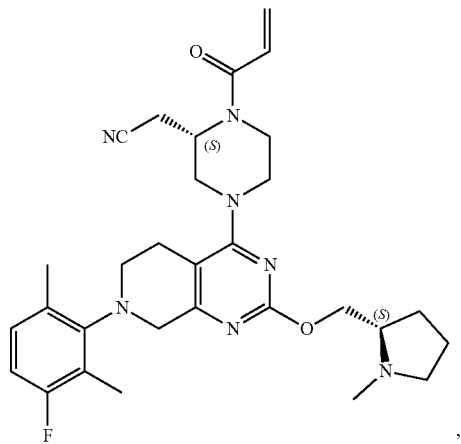
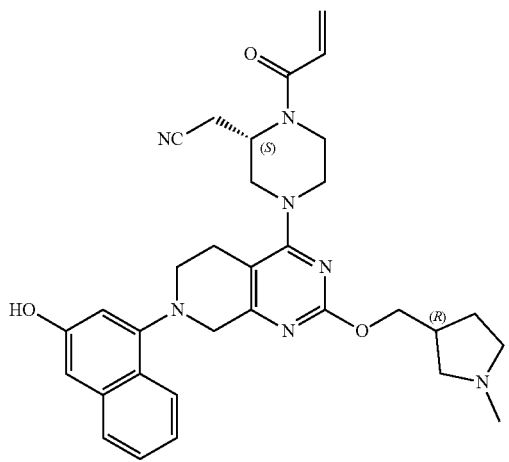
84
-continued
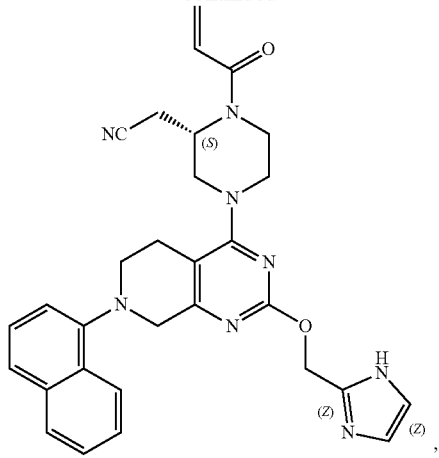
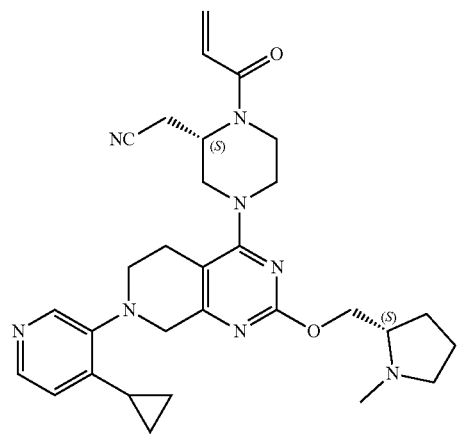
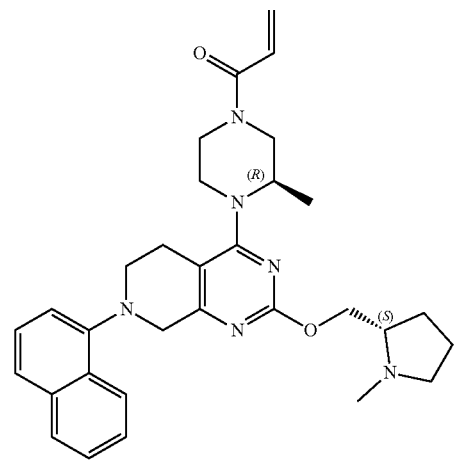

85
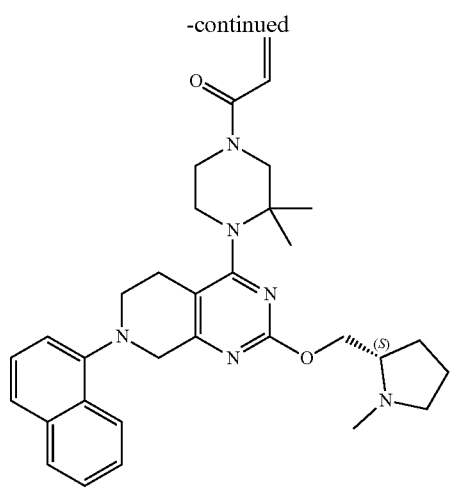
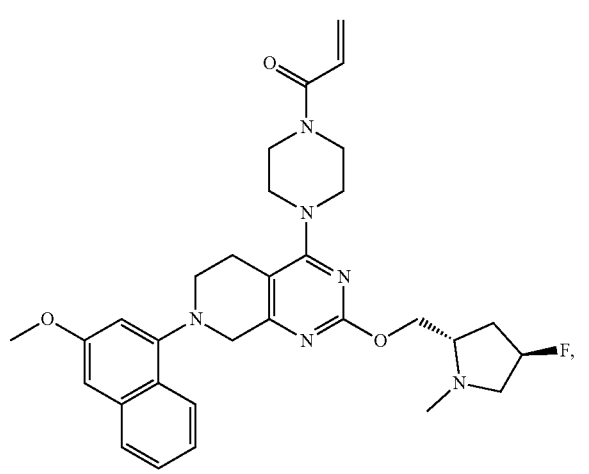
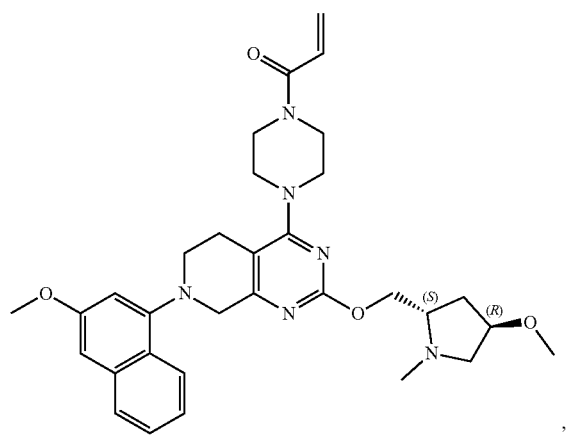
86
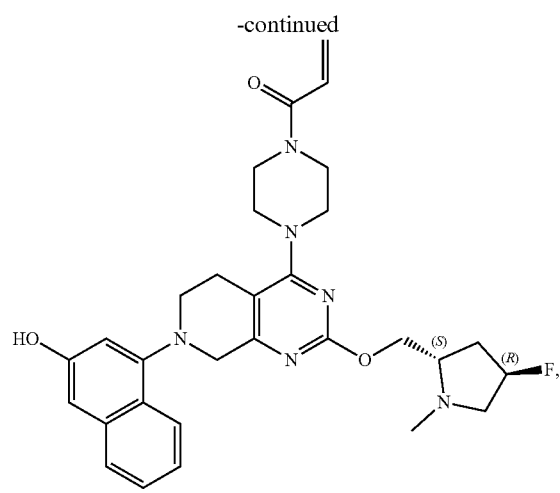
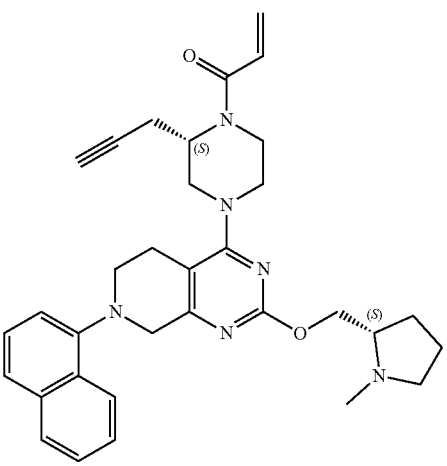
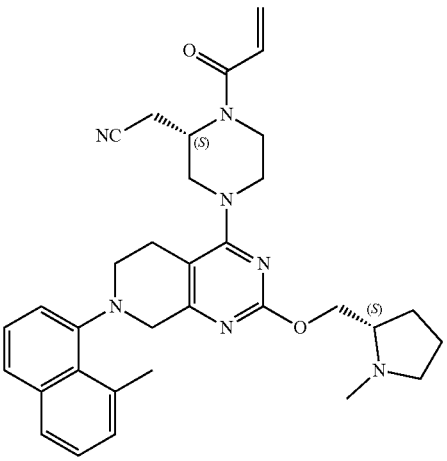

-continued

89
-continued
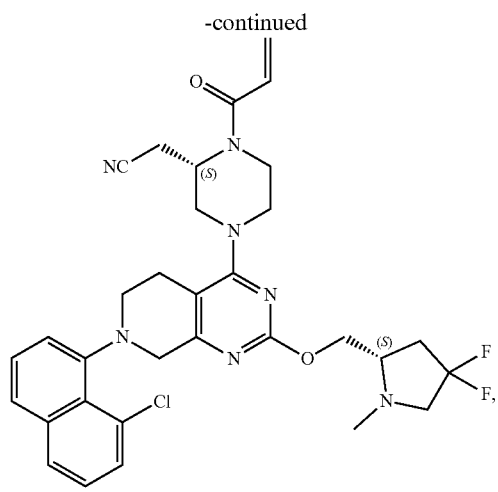
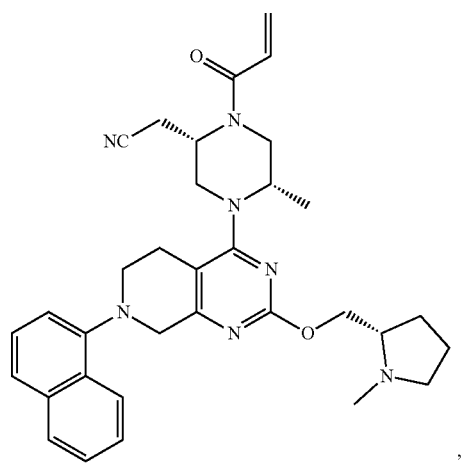
90
-continued
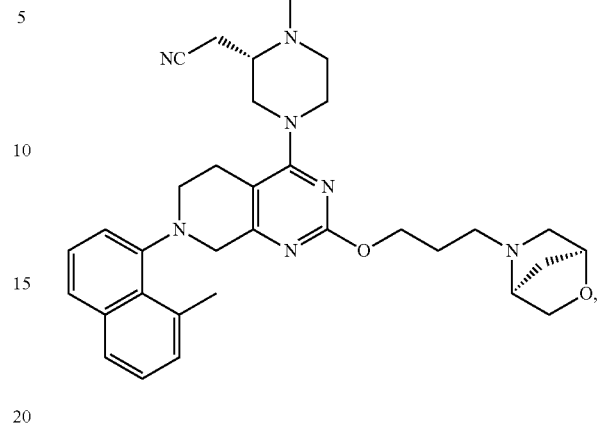
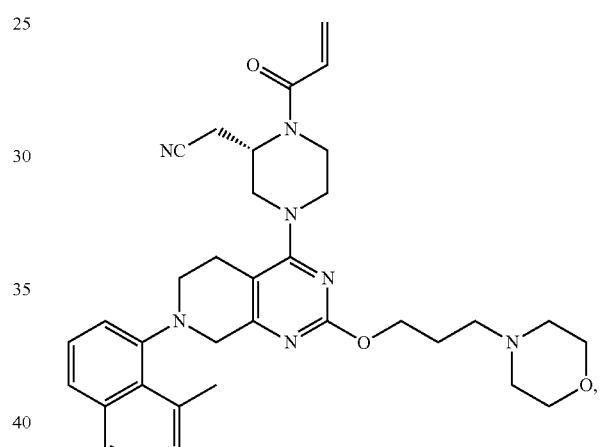
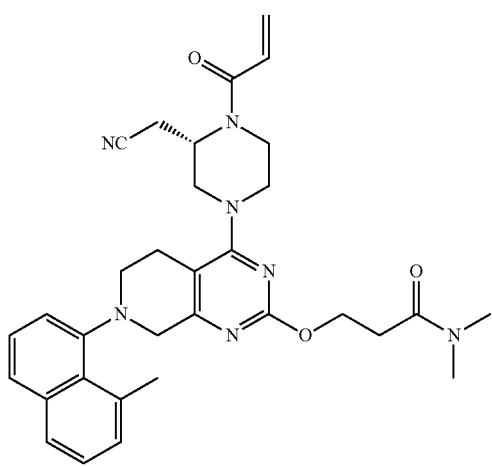

91
-continued
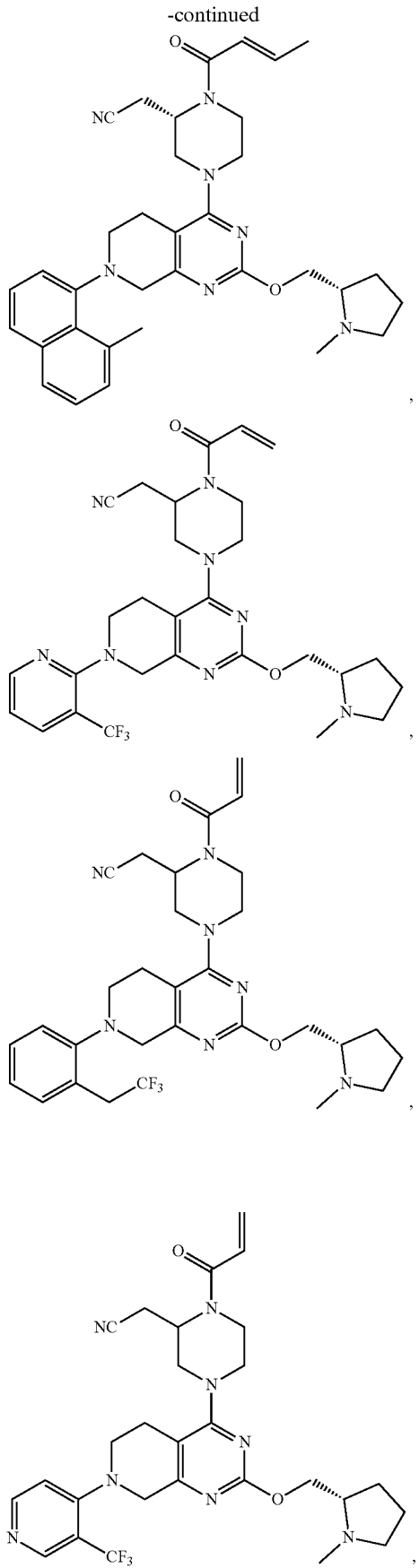
92
-continued
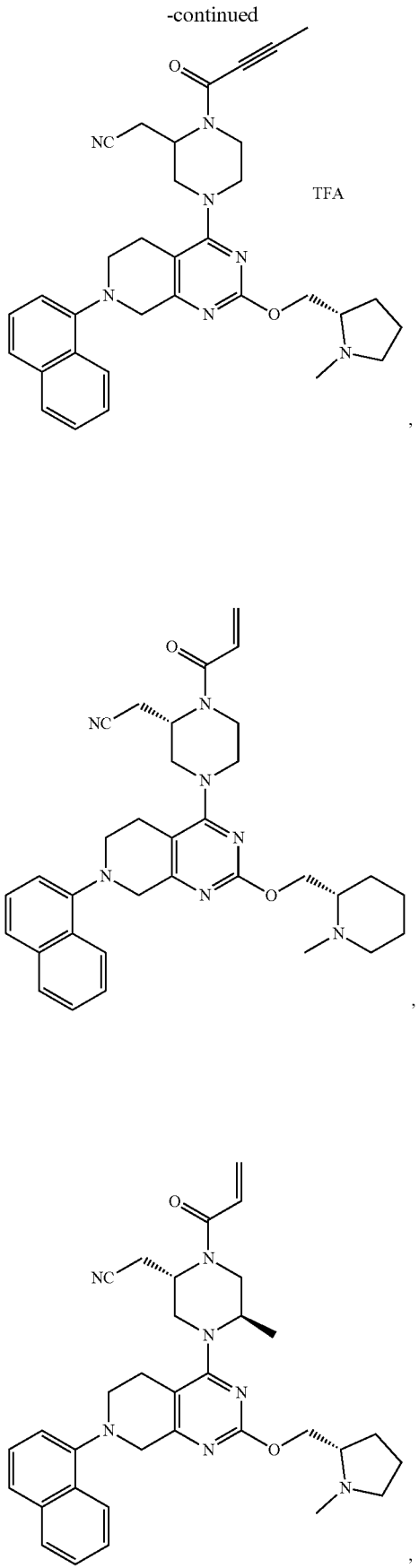

93
-continued
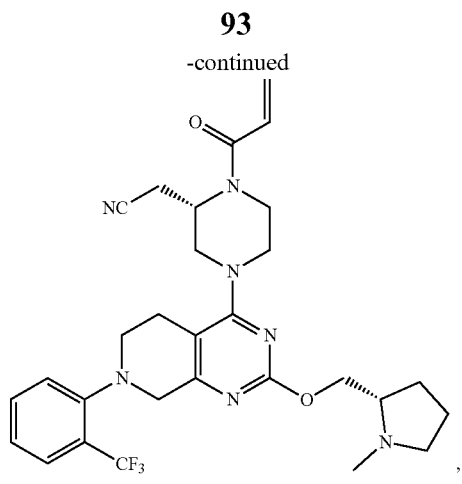
94
-continued
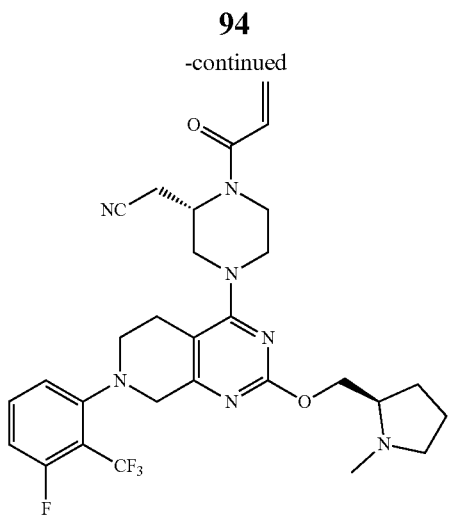
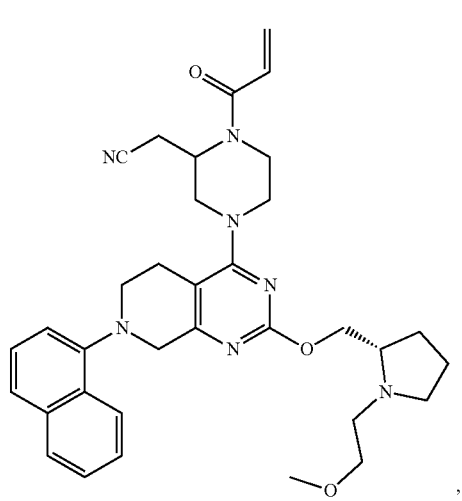
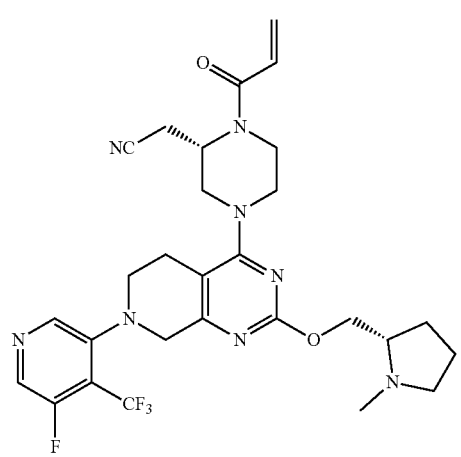
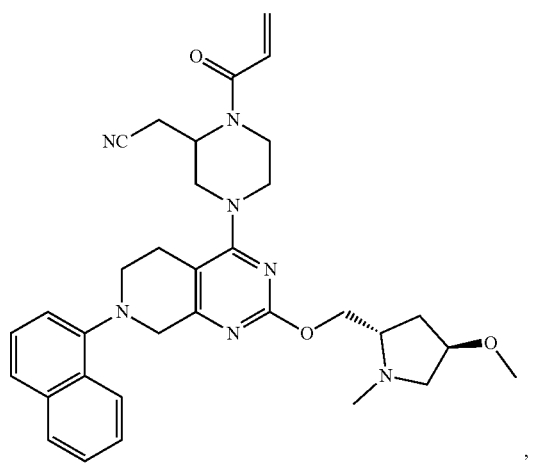
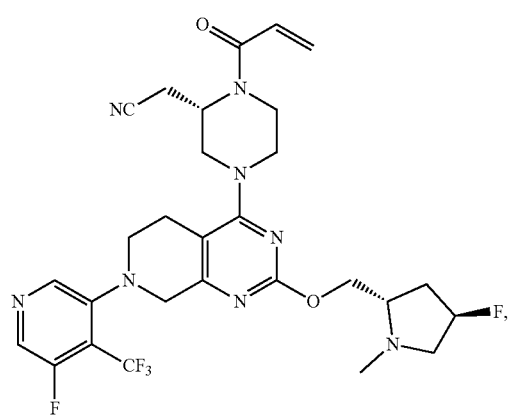

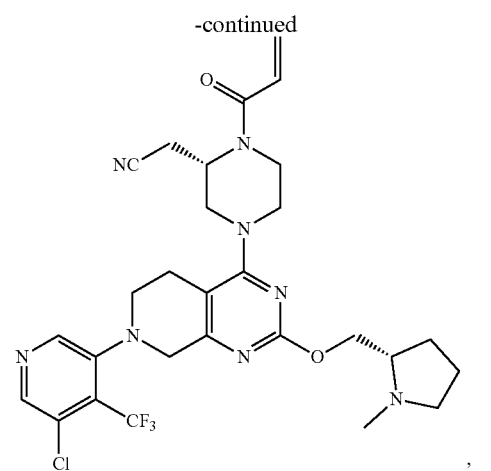
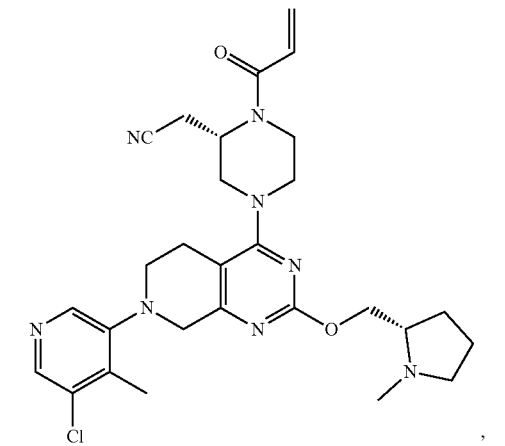

97
-continued
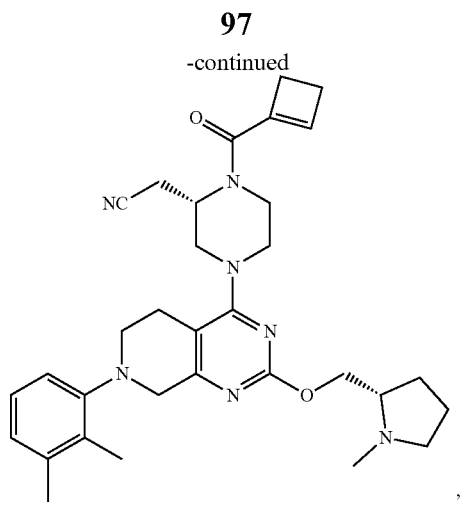
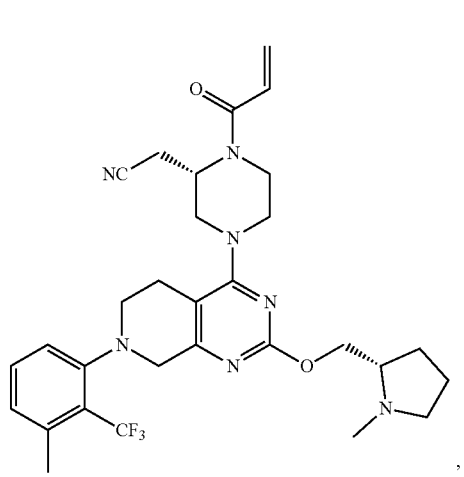
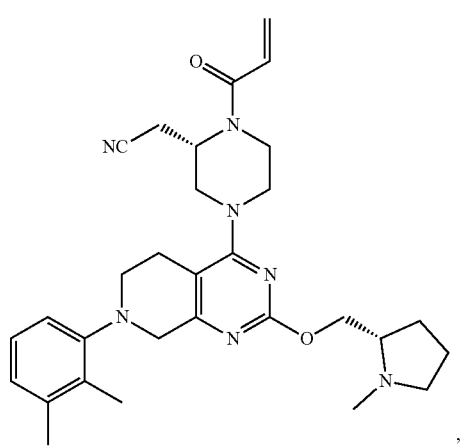
98
-continued
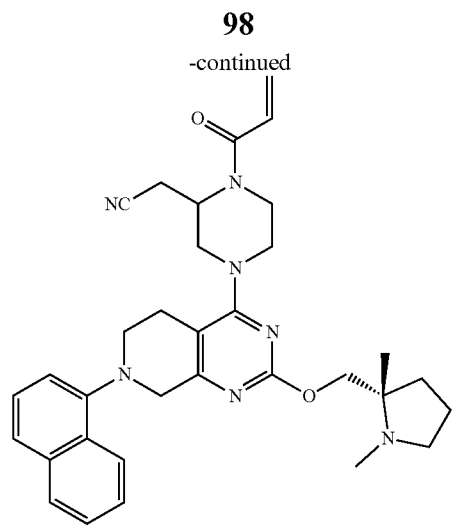
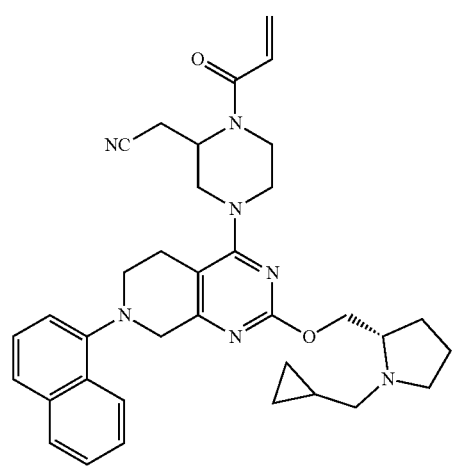
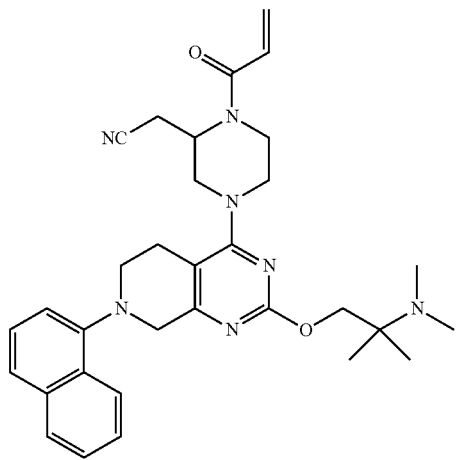

99
-continued
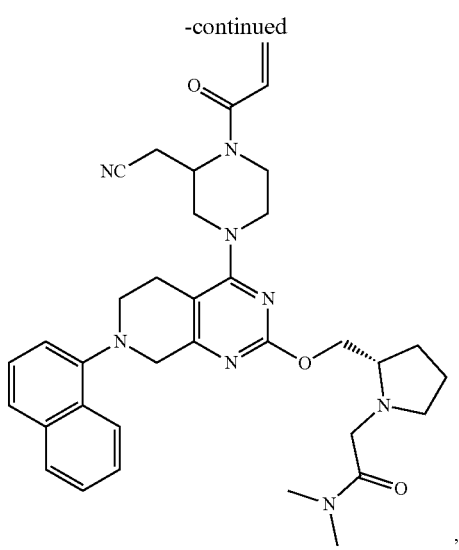
,
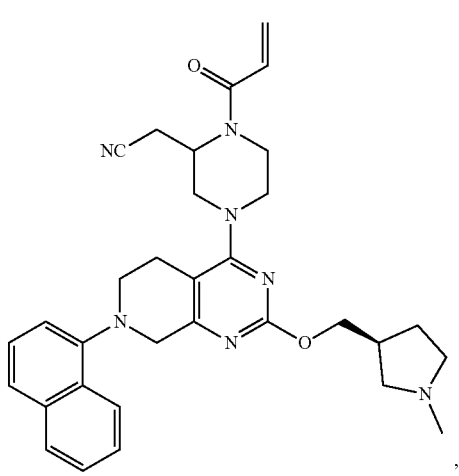
,
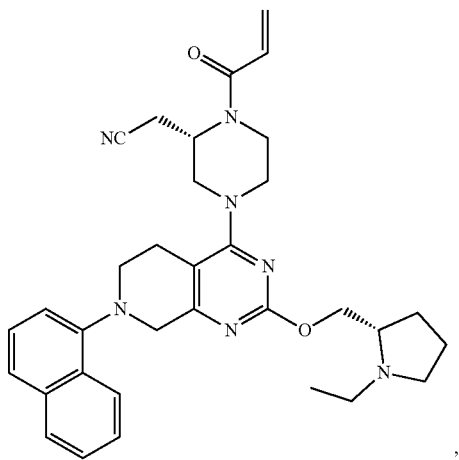
,
100
-continued
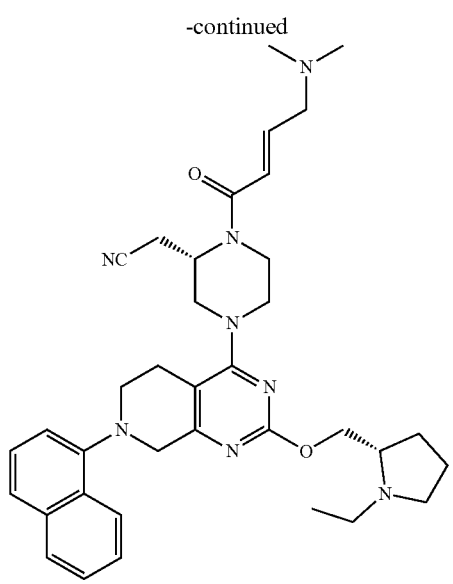
,
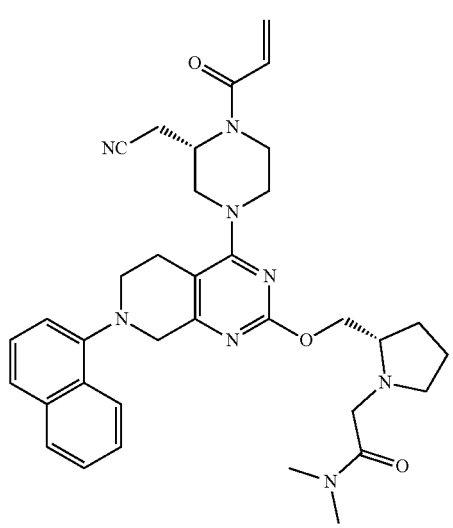
,
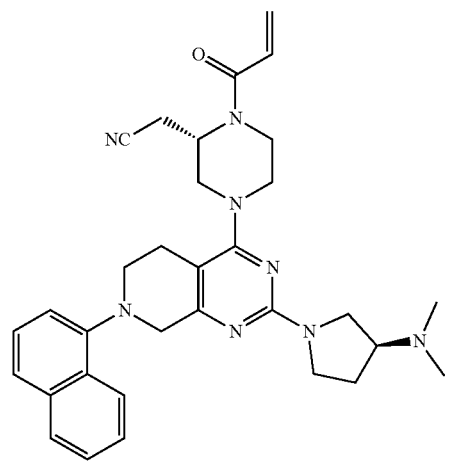
, 101
-continued
102
-continued
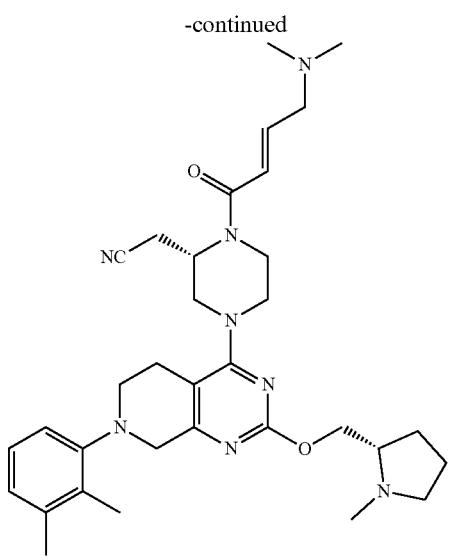
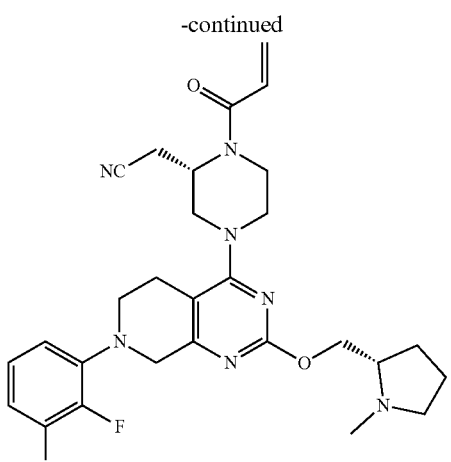

103
-continued
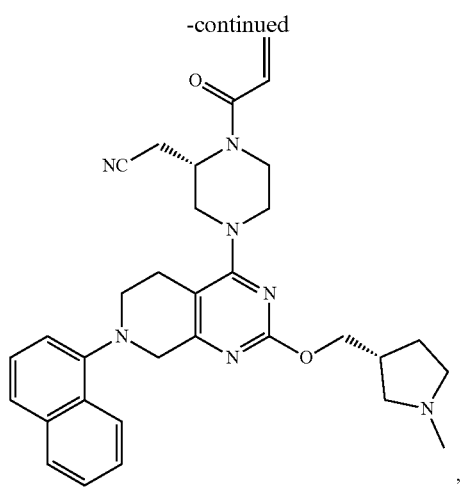
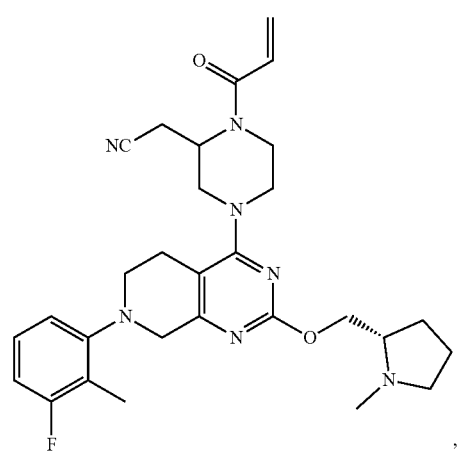
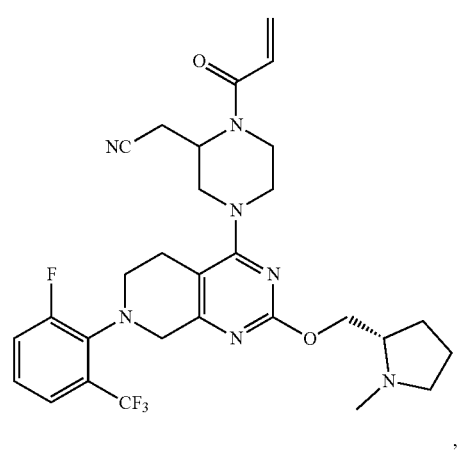
104
-continued
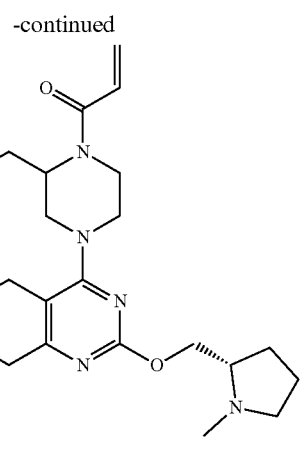
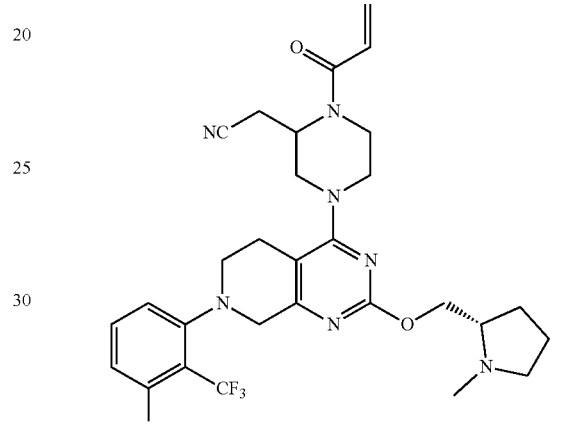
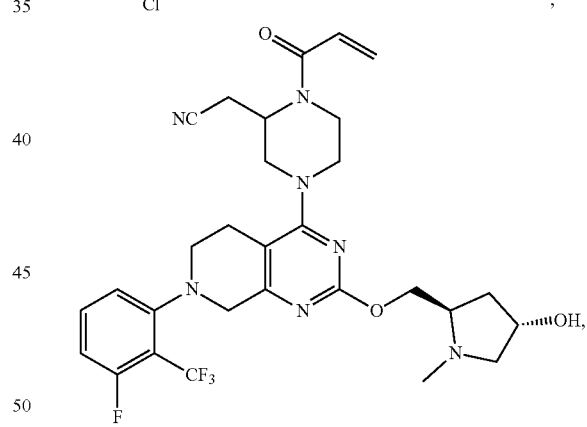
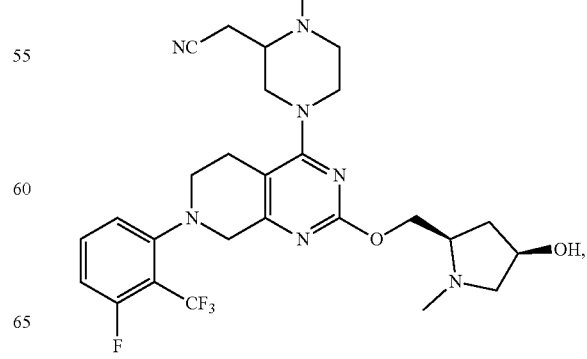

105
-continued
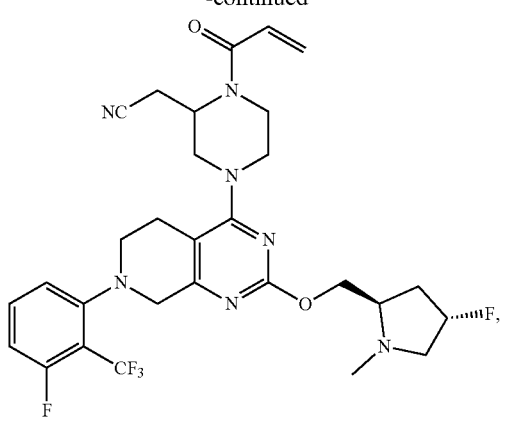
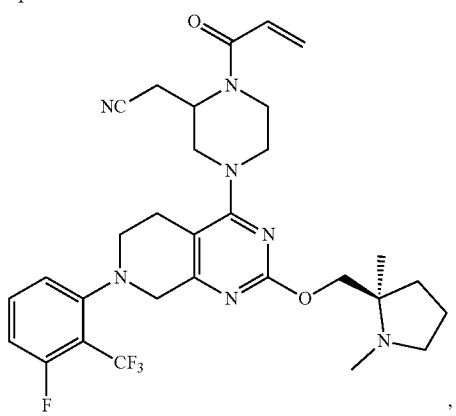
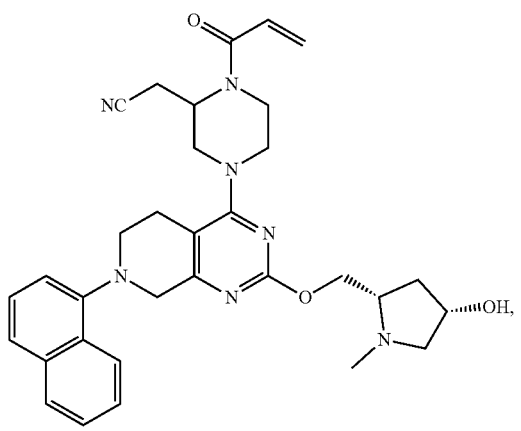
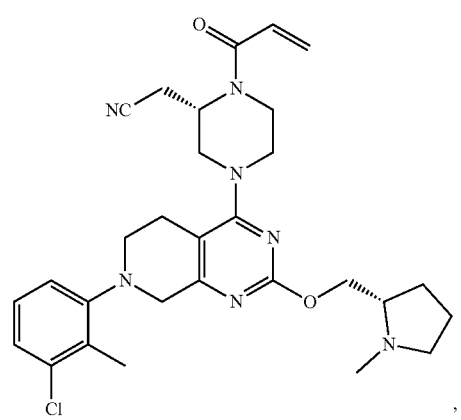
106
-continued
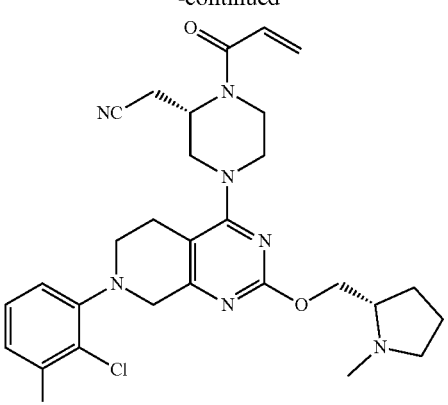
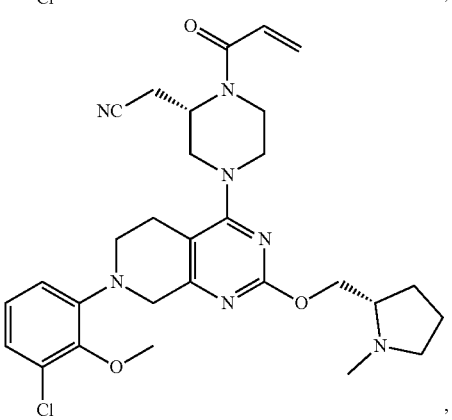
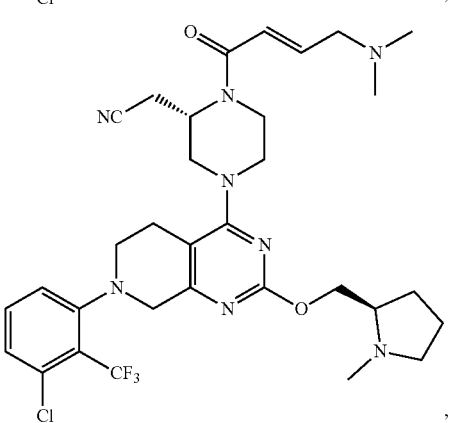
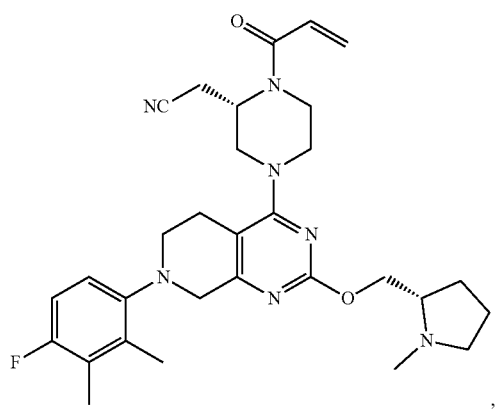

107
-continued
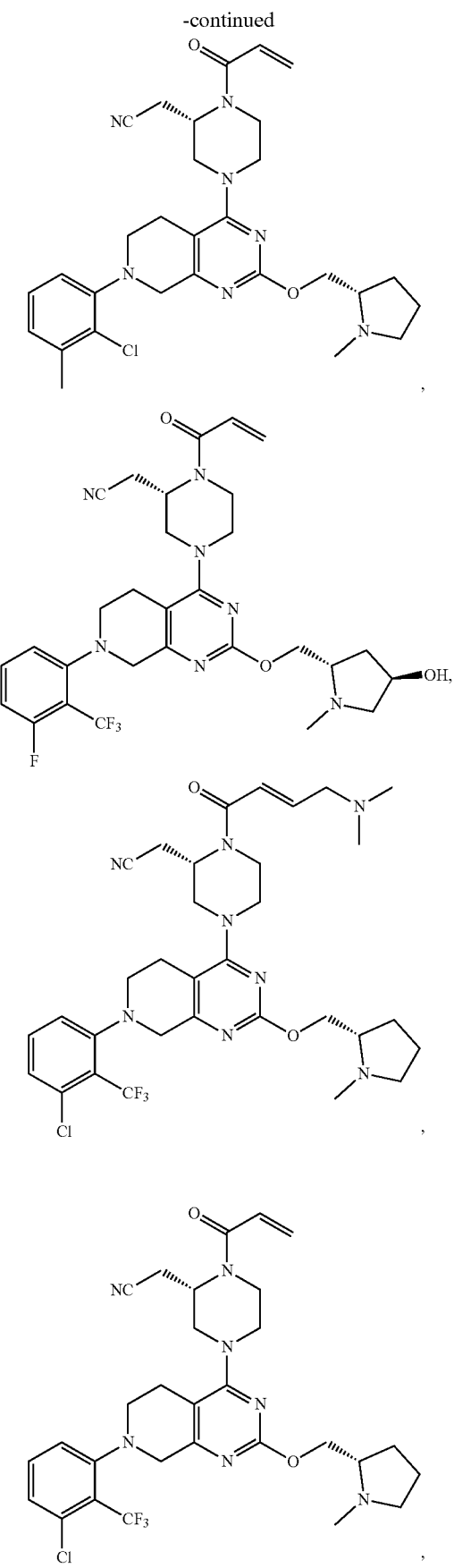
108
-continued
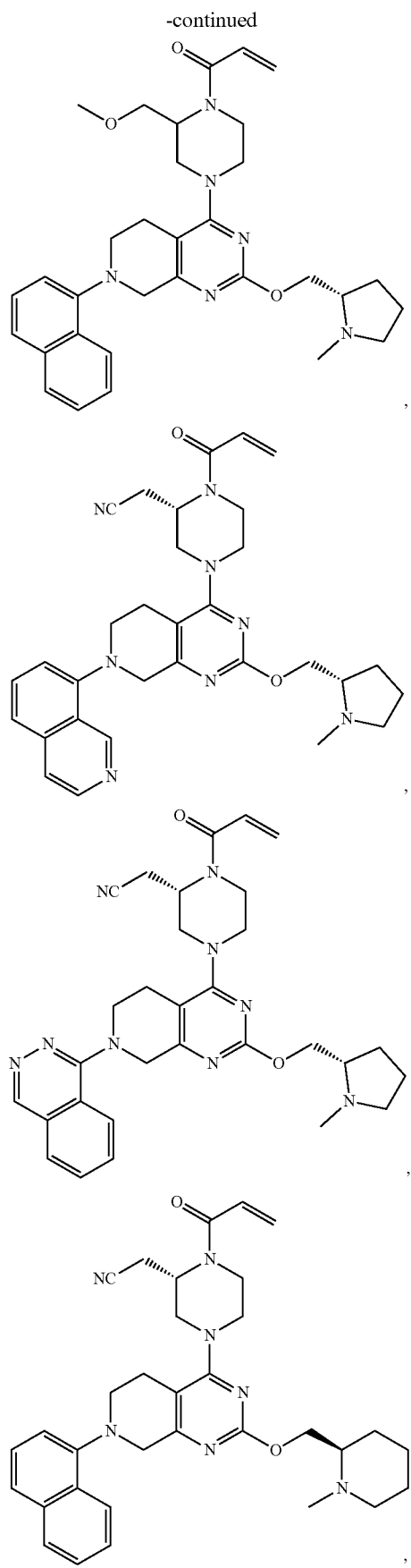

-continued
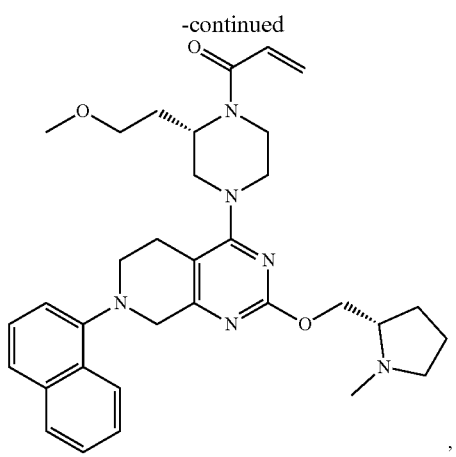
,
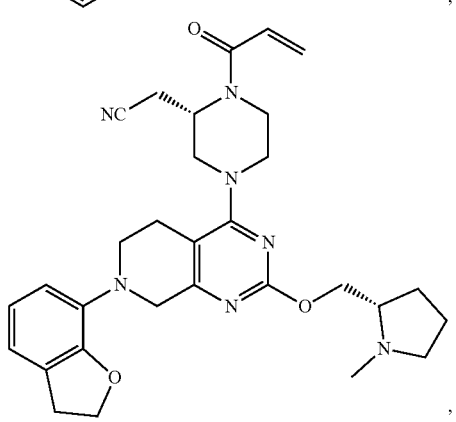
,
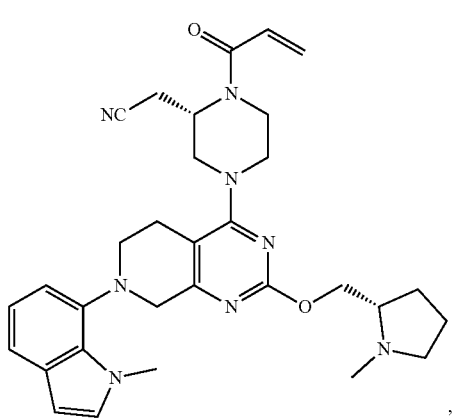
,
-continued
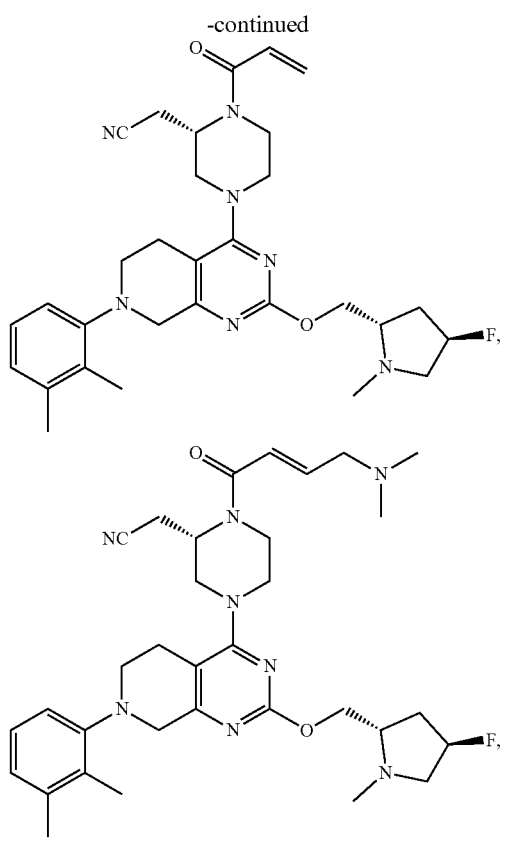
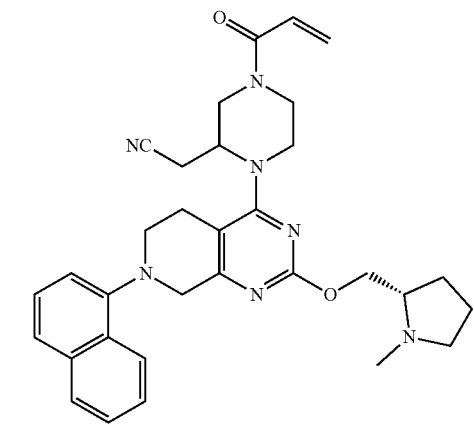
,
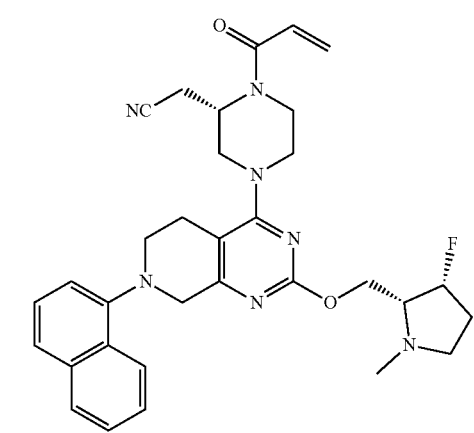
, 111
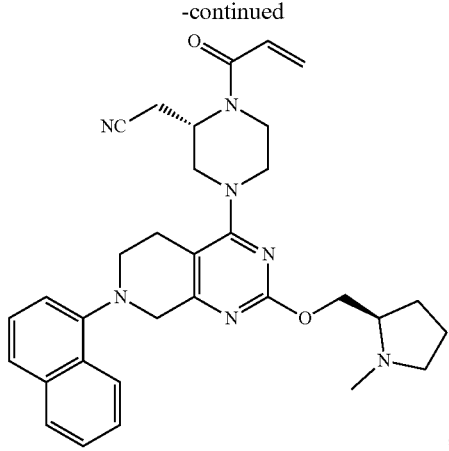
112
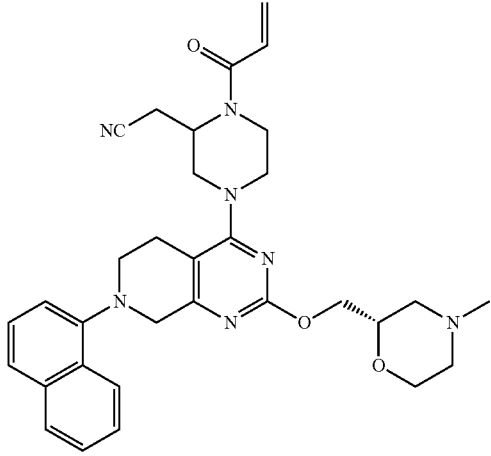
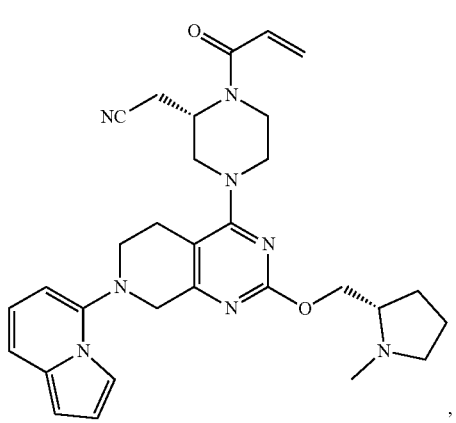
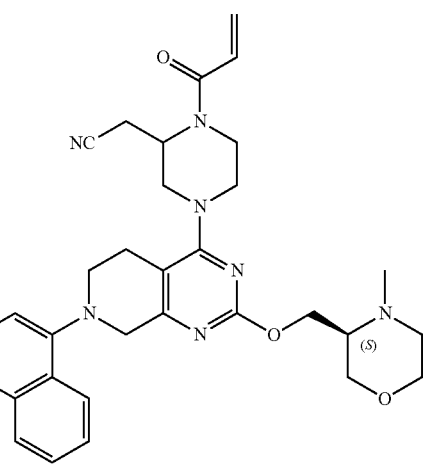
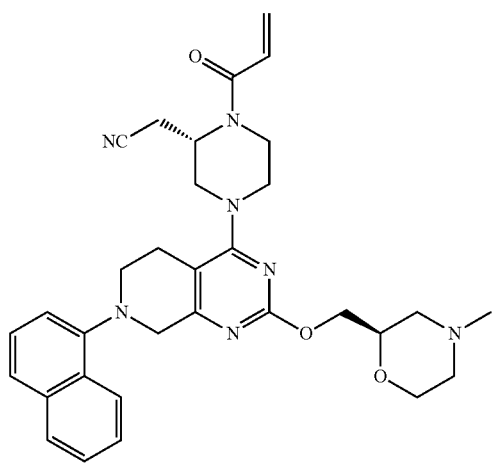
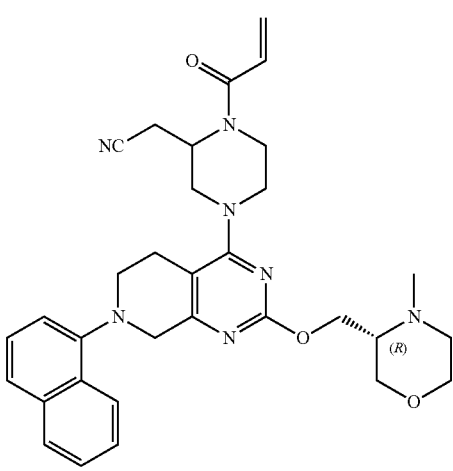

113
-continued
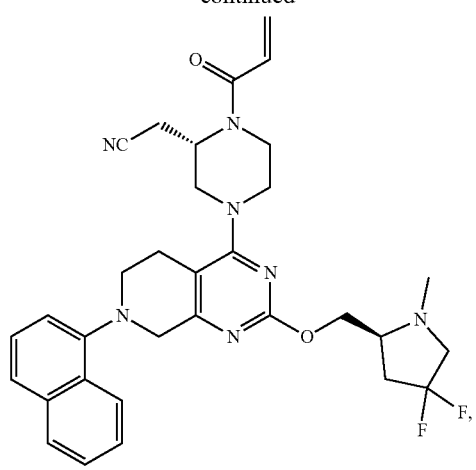
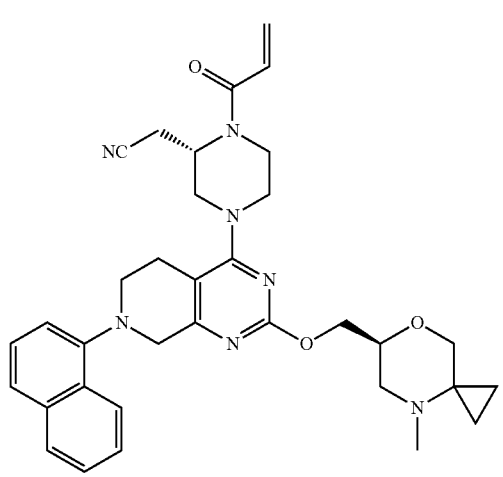
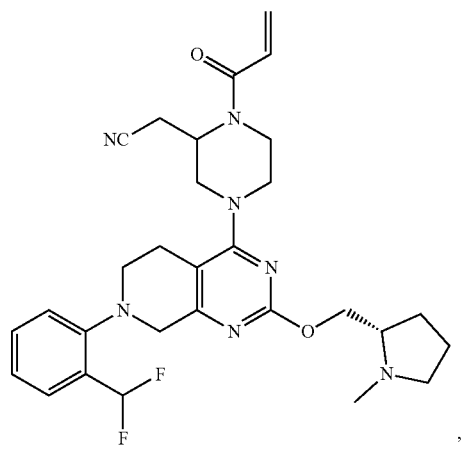
114
-continued
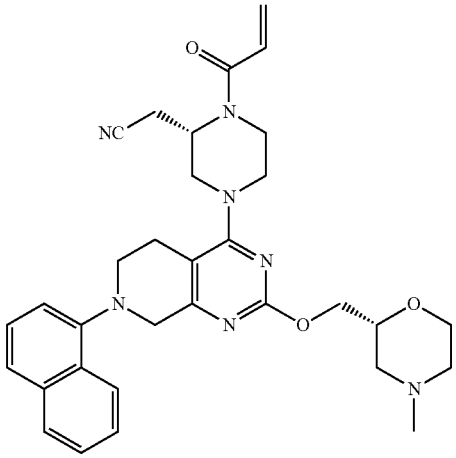
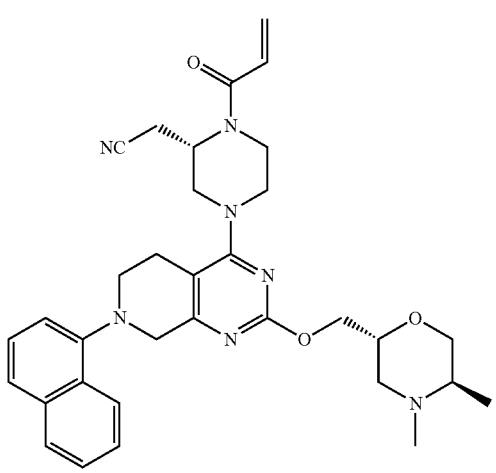
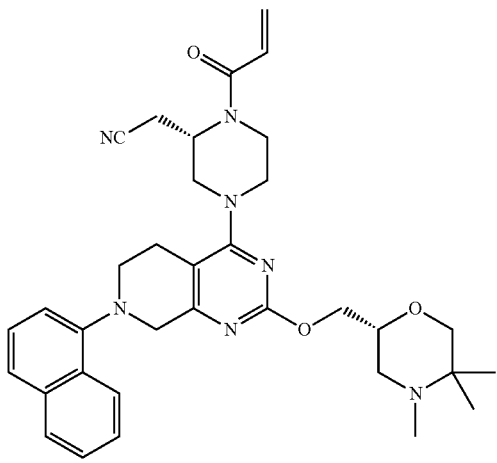

115
-continued
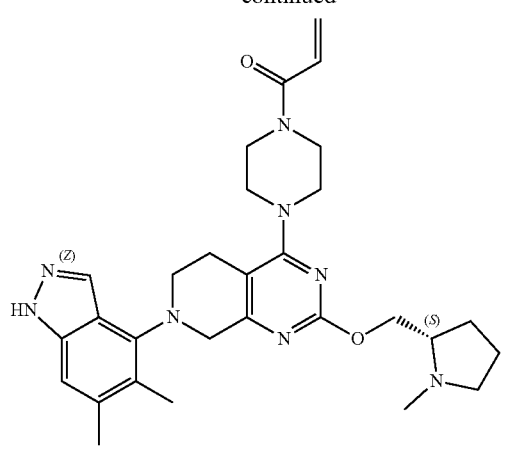
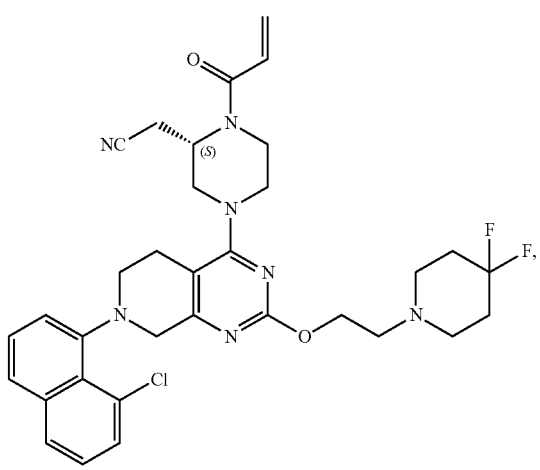
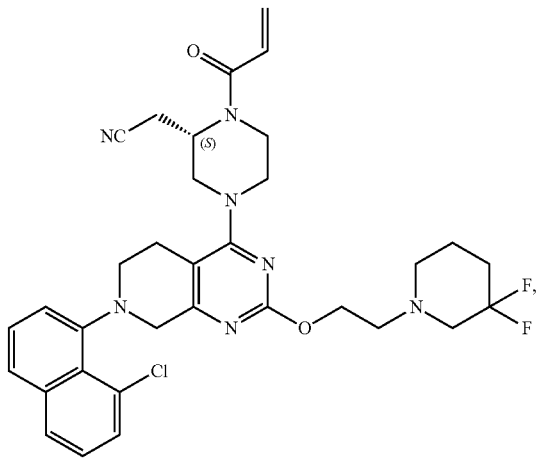
116
-continued
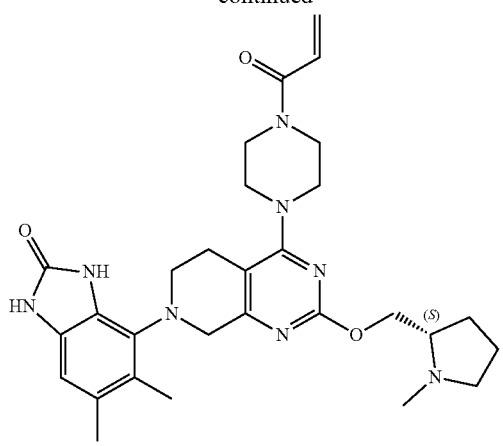
,
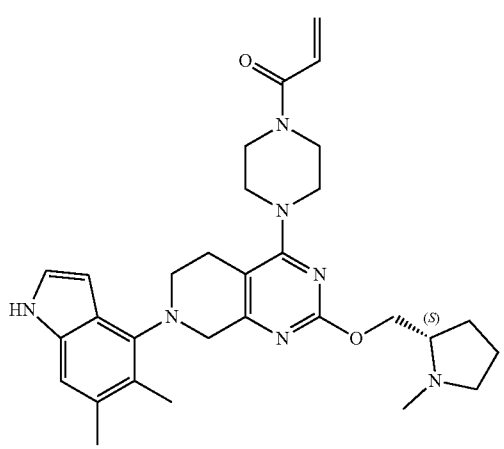
,
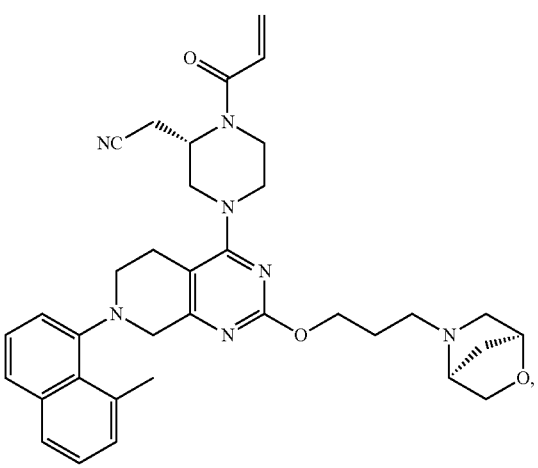

117
-continued
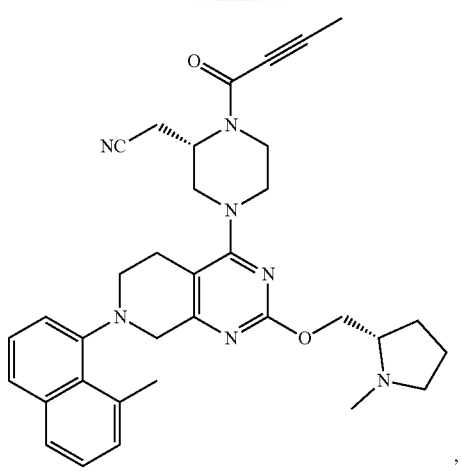
,
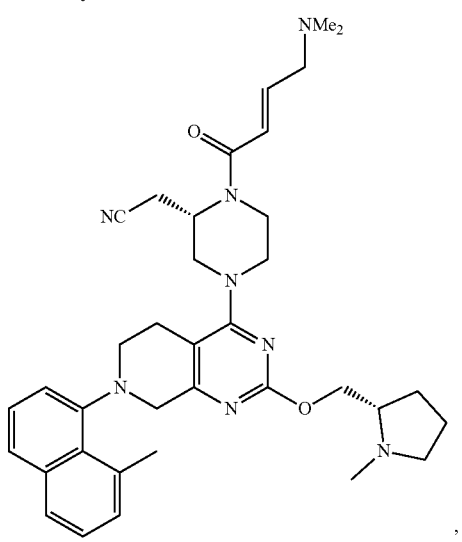
,
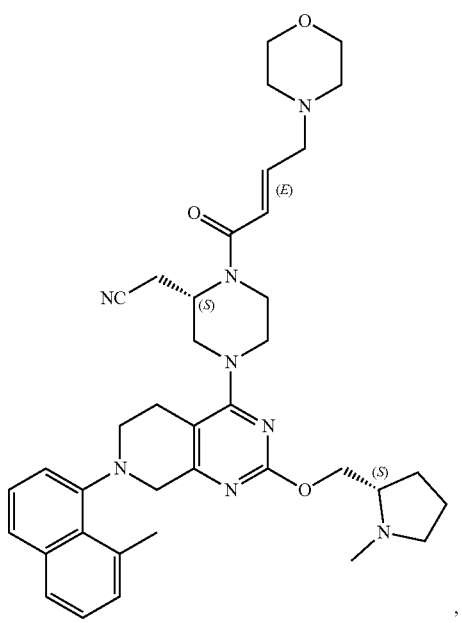
,
118
-continued
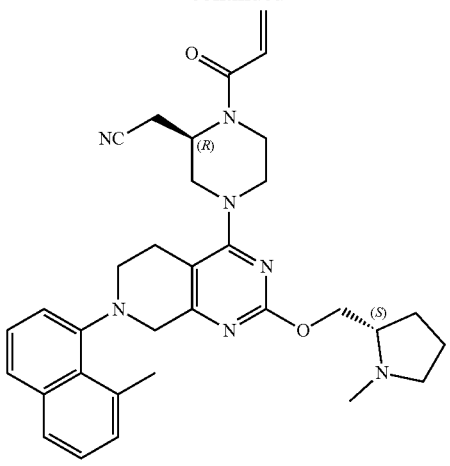
,
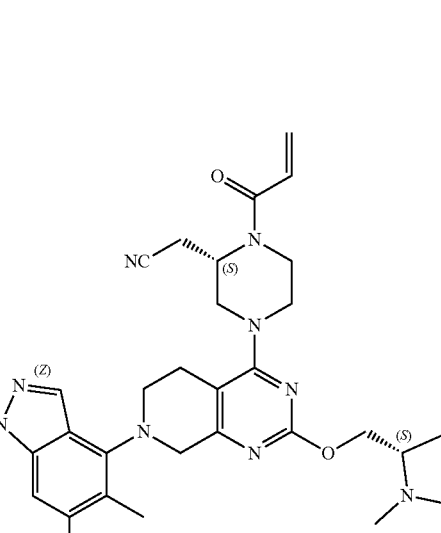
,
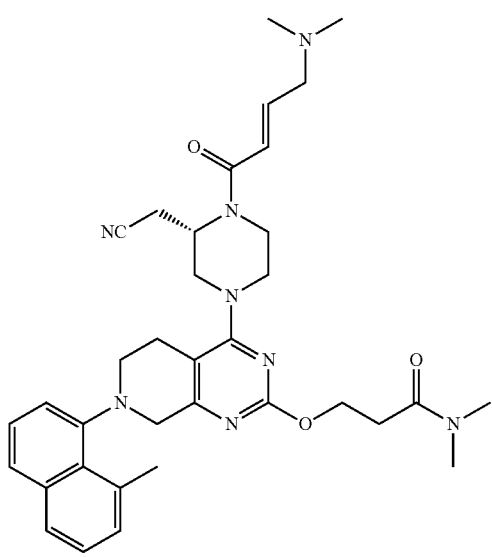
, 119
-continued
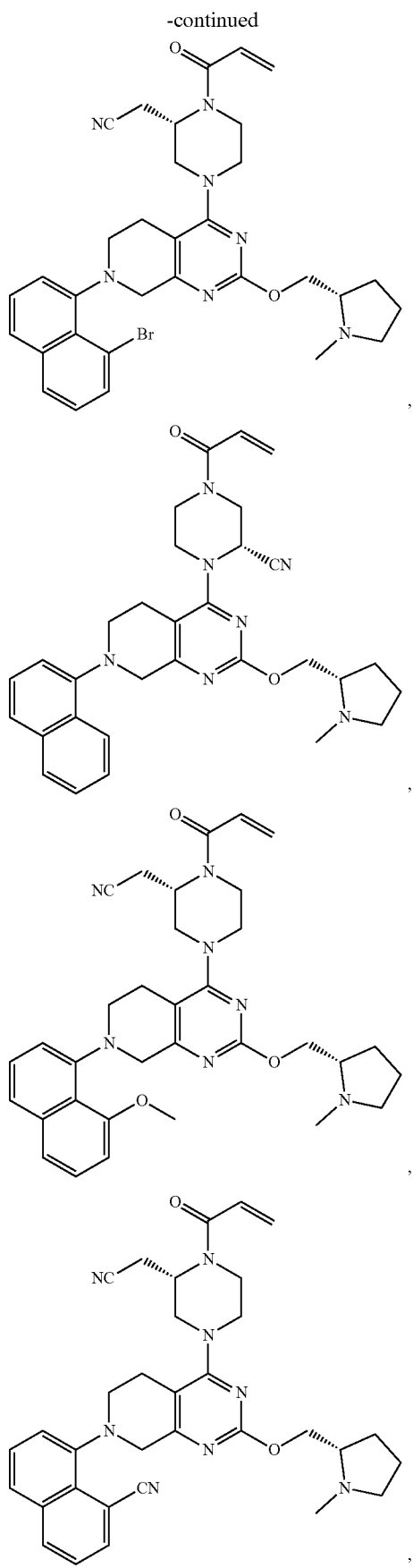
120
-continued
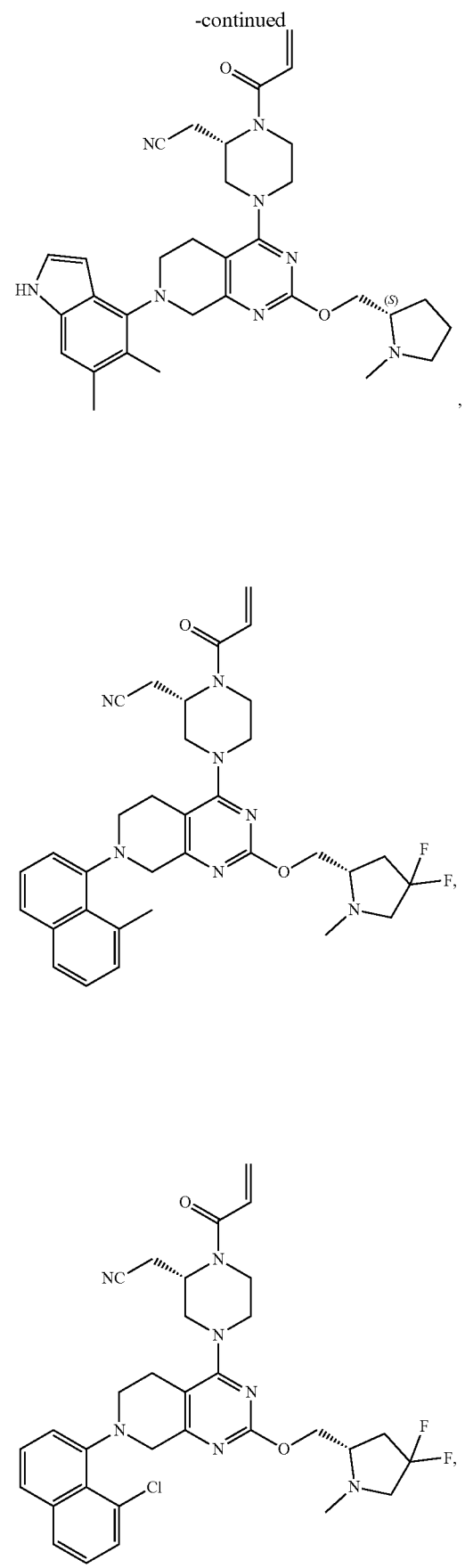

121
-continued
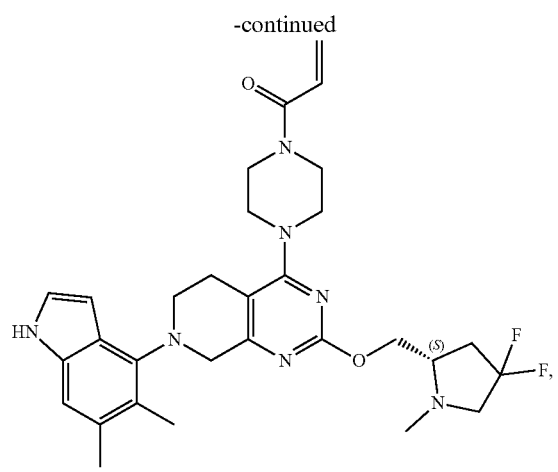
122
-continued
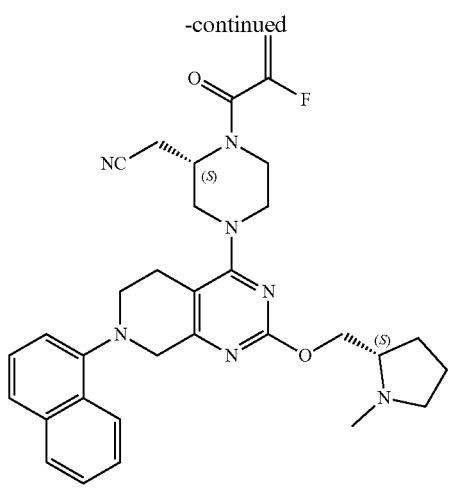
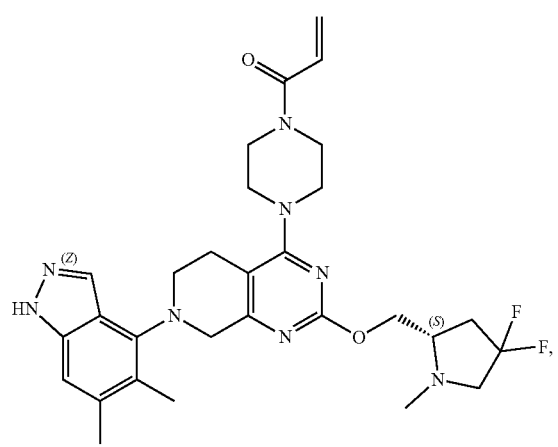
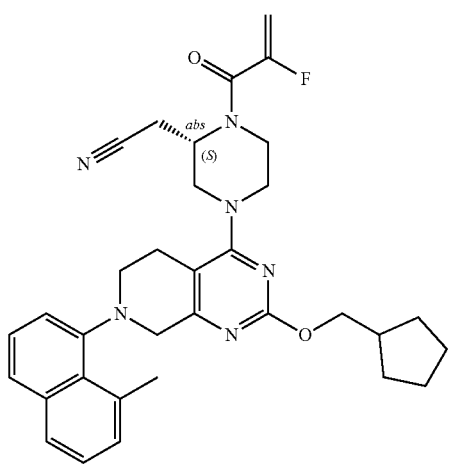
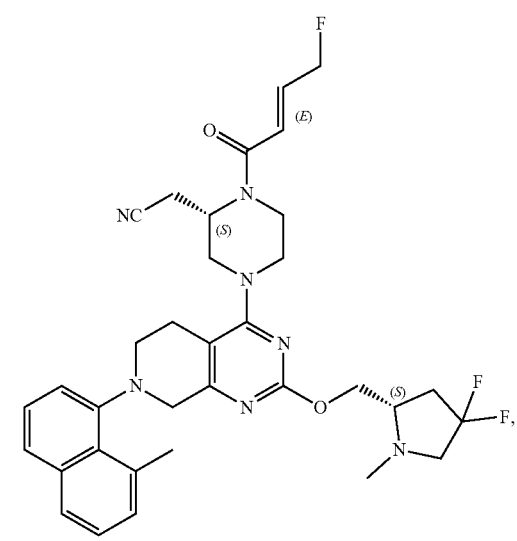
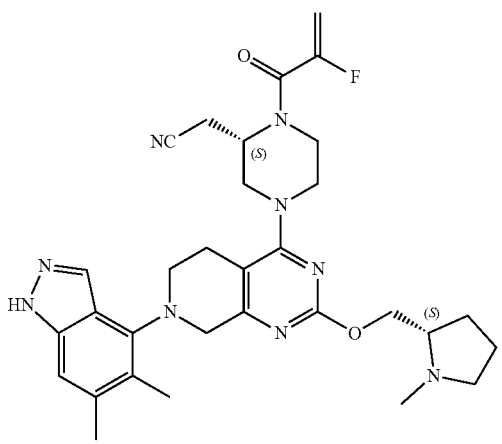

123
-continued
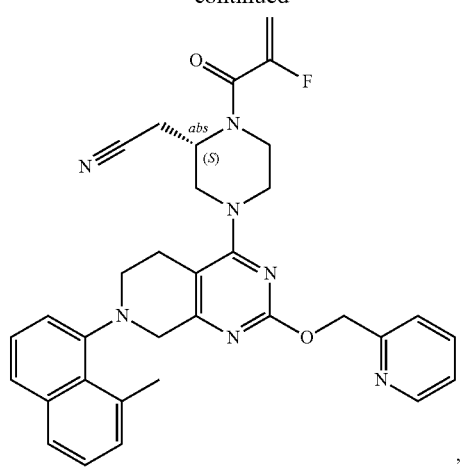
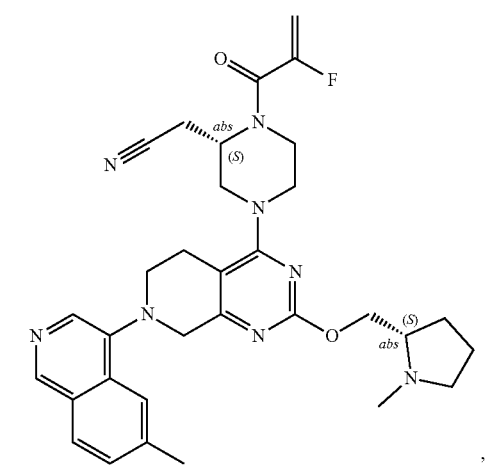
124
-continued
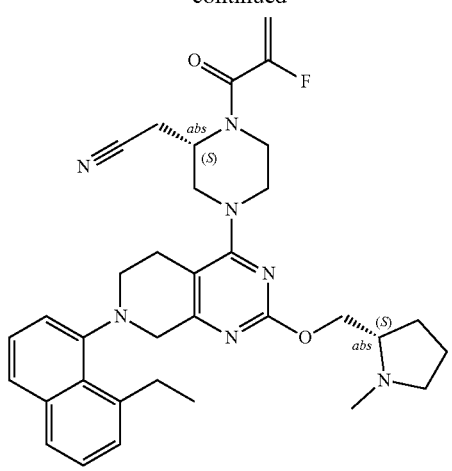
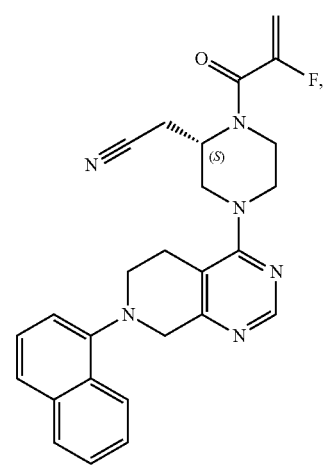

125
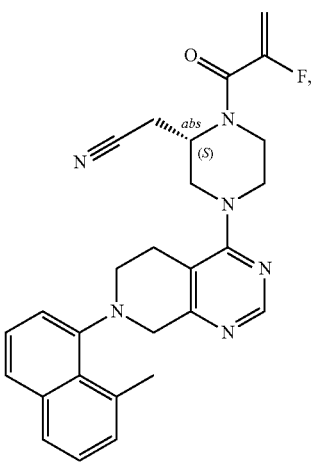
126
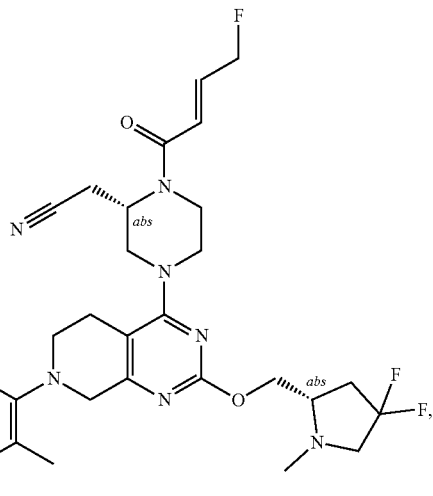
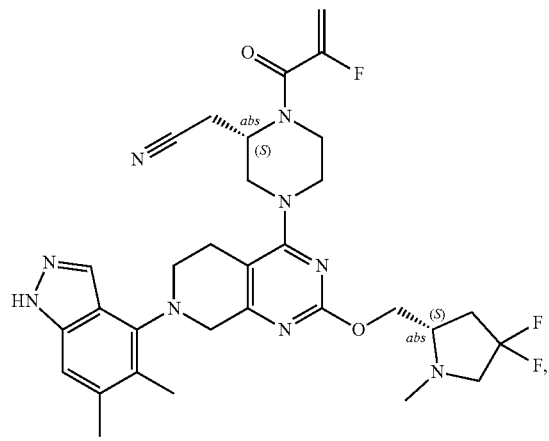
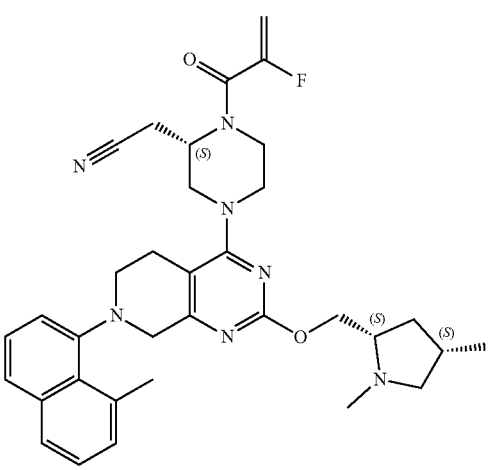

-continued

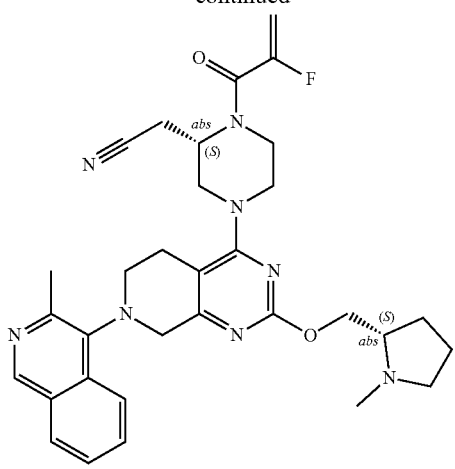

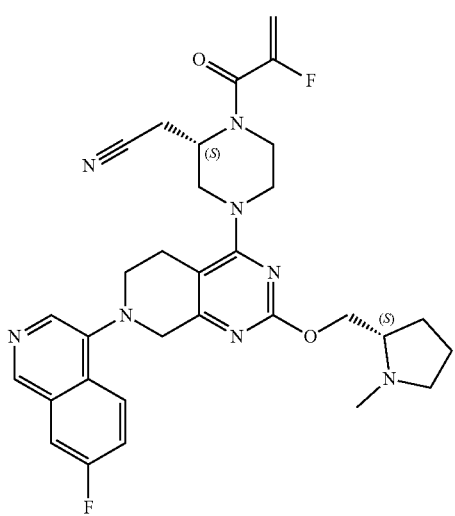

-continued

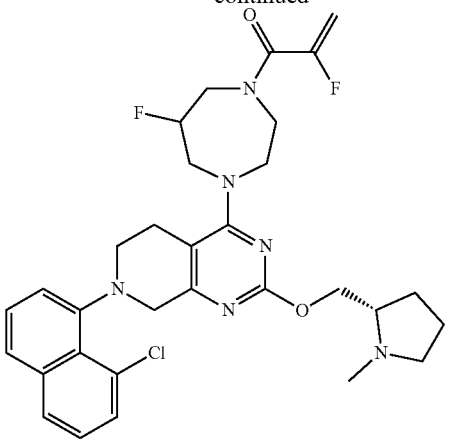

, and

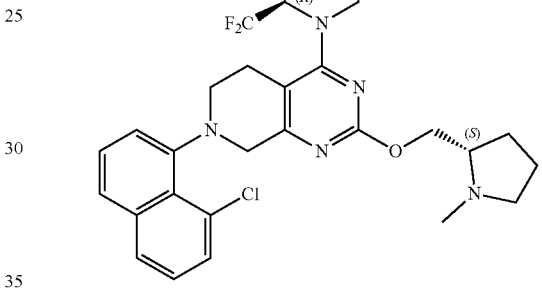

and pharmaceutically acceptable salts thereof.

In one aspect of the invention, compounds are provided represented by formula (II):

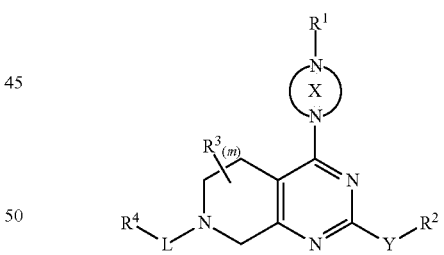

Formula (II)

or a pharmaceutically acceptable salt thereof:

wherein:

X is a 4-12 membered saturated or partially saturated monocyclic, bridged or spirocyclic ring, wherein the saturated or partially saturated monocyclic ring is optionally substituted with one or more $R^8$;

Y is a bond, O, S or $NR^5$;

$R^1$ is —C(O)C($R^A$)═C($R^B$)$_p$ or —SO$_2$C($R^A$)═C($R^B$)$_p$;

$R^2$ is hydrogen, alkyl, hydroxyalkyl, dihydroxyalkyl, alkylaminylalkyl, dialkylaminylalkyl, —Z—$NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;

each Z is C1-C4 alkylene;

each $R^3$ is independently C1-C3 alkyl, oxo, haloalkyl, hydroxyl or halogen;

L is a bond, —C(O)—, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$, $R^7$ or $R^8$;

each $R^5$ is independently hydrogen or C1-C3 alkyl;

$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;

each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;

$R^8$ is oxo, C1-C3 alkyl, C2-C4 alkynyl, heteroalkyl, cyano, —C(O)$OR^5$, —C(O)N($R^5$)$_2$, —N($R^5$)$_2$, wherein the C1-C3 alkyl may be optionally substituted with cyano, halogen, —$OR^5$, —N($R^5$)$_2$, or heteroaryl;

each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;

each $R^{10}$ is independently hydrogen, acyl, C1-C3 alkyl, heteroalkyl or hydroxyalkyl;

$R^{11}$ is haloalkyl;

$R^A$ is absent, hydrogen, deuterium, cyano, halogen, C1-C-3 alkyl, haloalkyl, heteroalkyl, —C(O)N($R^5$)$_2$, or hydroxyalkyl;

each $R^B$ is independently hydrogen, deuterium, cyano, C1-C3 alkyl, hydroxyalkyl, heteroalkyl, C1-C3 alkoxy, halogen, haloalkyl, —ZN$R^5R^{11}$, —C(O)N($R^5$)$_2$, —NHC(O) C1-C3 alkyl, —$CH_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;

or when ≐ is a double bond and p is two, one $R^B$ is hydrogen and $R^A$ and one $R^B$ and the carbon atoms to which they are attached form a 4-8 membered partially saturated cycloalkyl substituted with oxo;

m is zero or an integer between 1 and 2;

p is one or two; and wherein, when ≡ is a triple bond then $R^A$ is absent, p equals one and $R^B$ is hydroxyalkyl, or when ≐ is a double bond then $R^A$ is present, $R^B$ is present and p equals two, wherein when $R^A$ is hydrogen or C1-C3 alkyl, at least one $R^B$ is deuterium, cyano, halogen, haloalkyl, hydroxyalkyl, heteroalkyl, heteroaryl, heteroarylalkyl, —ZN$R^5R^{11}$, —C(O)N($R^5$)$_2$, —NHC(O)C1-C3 alkyl, —$CH_2$NHC(O)C1-C3 alkyl or heterocyclylalkyl, wherein the heterocyclyl portion is substituted with one or more substituents independently selected from halogen, hydroxyl, alkoxy and C1-C3 alkyl; or when each $R^B$ is hydrogen, then $R^A$ is deuterium, cyano, halogen, haloalkyl, —C(O)N($R^5$)$_2$, hydroxyalkyl or heteroalkyl.

In certain embodiments, $R^1$—X is:

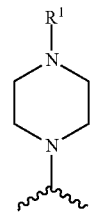

wherein $R^1$ is are defined for Formula II and the piperazinyl ring is optionally substituted with $R^8$, where $R^8$ is as defined for Formula II. In certain embodiments, $R^8$ is C1-C3 alkyl wherein the alkyl is optionally substituted with cyano or $OR^5$, or —C(O)N($R^5$)$_2$, wherein each $R^5$ is independently hydrogen or C1-C3 alkyl.

In particular embodiments, $R^1$ is —C(O)C($R^A$)≐C($R^B$)$_p$ where $R^A$, $R^B$ and p are as defined for Formula II. In one embodiment, $R^1$ is —C(O)C($R^A$)≐C($R^B$)$_p$, wherein ≡ is a triple bond and $R^A$ is absent, p is one and $R^B$ is hydroxyalkyl.

In one embodiment, $R^1$ is —C(O)C($R^A$)≐C($R^B$)$_p$, wherein ≐ is a double bond and $R^A$ is hydrogen or C1-C3 alkyl, p is two and at least one $R^B$ is deuterium, cyano, C1-C3 alkyl, hydroxyalkyl, heteroalkyl, C1-C3 alkoxy, halogen, haloalkyl, —ZN$R^5R^{11}$, —C(O)N($R^5$)$_2$, —NHC(O) C1-C3 alkyl, —$CH_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$. In one embodiment, when ≐ is a double bond, the double bond is in the E configuration. In one embodiment, the double bond is in the Z configuration.

In certain embodiments, one $R^B$ is heterocyclylalkyl substituted with one or more substituents independently selected from halogen, hydroxyl, alkoxy or C1-C3 alkyl and the other $R^B$ is hydrogen. In one embodiment, the heterocyclyl portion of the heterocyclylalkyl is azetidinyl substituted with a halogen. In certain embodiments, the halogen is fluorine. In one embodiment, the heterocyclyl portion of the heterocyclylalkyl is pyrrolidinyl substituted with one or more halogen. In certain embodiments, the halogen-substituted pyrrolidinyl is fluoropyrrolidinyl or difluorpyrrolidinyl.

In certain embodiments, one $R^B$ is halogen and the other $R^B$ is hydrogen. In one embodiment, the halogen is chlorine.

In certain embodiments, one $R^B$ is haloalkyl and the other $R^B$ is hydrogen. In one embodiment, the haloalkyl is chloromethyl, fluoromethyl, difluoromethyl or trifluoromethyl.

In certain embodiments, one $R^B$ is heteroalkyl and the other $R^B$ is hydrogen. In one embodiment, the heteroalkyl is methoxymethyl.

In certain embodiments, one $R^B$ is —ZN$R^5R^{11}$, wherein Z is methylene, $R^5$ is methyl and $R^{11}$ is trifluoromethyl or 2,2,2-trifluoroethyl, and the other $R^B$ is hydrogen.

In certain embodiments, one $R^B$ is hydroxyalkyl and the other $R^B$ is hydrogen.

In certain embodiments, one $R^B$ is heteroaryl optionally substituted with one or more $R^7$ and the other $R^B$ is hydrogen. In one embodiment, the heteroaryl is pyrrolyl, imidazolyl, pyrazolyl, triazolyl, pyridyl, pyridazinyl, pyrimidinyl, pyrazinyl or triazinyl, each substituted with one or more $R^7$.

In certain embodiments, one $R^B$ is heteroarylalkyl optionally substituted with one or more $R^7$, and the other $R^B$ is hydrogen. In one embodiment, the heteroaryl portion of the heteroarylalkyl is pyrrolyl, imidazolyl, pyrazolyl, triazolyl, pyridyl, pyridazinyl, pyrimidinyl, pyrazinyl or triazinyl, each optionally substituted with one or more $R^7$. In one embodiment, the one or more $R^7$ is C1-C3 alkyl.

In certain embodiments, one $R^B$ is —C(O)N($R^5$)$_2$ and the other $R^B$ is hydrogen. In one embodiment, each $R^5$ is hydrogen. In one embodiment, each $R^5$ is C1-C3 alkyl.

In certain embodiments, one $R^B$ is —NHC(O)C1-C3 alkyl or —CH$_2$NHC(O)C1-C3 alkyl and the other $R^B$ is hydrogen. In one embodiment, the C1-C3 alkyl is methyl.

In one embodiment, $R^1$ is —C(O)C($R^A$)=C($R^B$)$_p$, wherein $R^A$ is deuterium, cyano, halogen, C1-C-3 alkyl, haloalkyl, heteroalkyl, —C(O)N($R^5$)$_2$, or hydroxyalkyl, p is two, each $R^B$ is hydrogen. In one embodiment, $R^A$ is halogen. In one embodiment, the halogen is fluorine or chlorine. In one embodiment, $R^A$ is haloalkyl. In one embodiment, the haloalkyl is trifluoromethyl. In one embodiment, $R^A$ is cyano. In one embodiment, $R^A$ is heteroalkyl. In one embodiment, the heteroalkyl is methoxy. In one embodiment, $R^A$ is hydroxyalkyl.

In one embodiment, $R^1$ is —C(O)C($R^A$)≡C($R^B$)$_p$, wherein ≡ is a double bond and $R^A$ is deuterium, p is two and at least one $R^B$ is deuterium.

In one embodiment, $R^1$ is —C(O)C($R^A$)≡C($R^B$)$_p$, wherein ≡ is a double bond and p is two, one $R^B$ is hydrogen and $R^A$ and one $R^B$ and the carbon atoms to which they are attached form a 5-8 membered partially saturated cycloalkyl substituted with oxo.

In one embodiment, $R^1$ is —C(O)C($R^A$)≡C($R^B$)$_p$, wherein ≡ is a double bond and p is two, one $R^B$ is hydrogen, the second $R^B$ is dialkylaminylalkyl, and $R^A$ is halogen In one embodiment, Y is O or $NR^5$ and $R^2$ is heterocyclyl or heterocyclylalkyl optionally substituted with one or more $R^9$. Nonlimiting examples of one or more $R^9$ when $R^2$ is heterocyclyl or heterocyclylalkyl include C1-C3 alkyl, acyl, oxo, cyano, alkoxy, cycloalkyl, cycloalkylmethyl, halogen, and hydroxyl. Nonlimiting examples of $R^2$ heterocyclyls optionally substituted with one or more $R^9$ include azetidinyl, C1-C3 alkyl-substituted azetidinyl (e.g., methylazetidinyl), halo-substituted azetidinyl (e.g., difluoroazetidinyl), tetrahydropyran, pyrrolidinyl, C1-C3 alkyl-substituted pyrrolidinyl (e.g., methylpyrrolidinyl, dimethylpyrrolidinyl, and isopropylpyrrolidinyl), cycloalkylalkylpyrrolidinyl, hydroxypyrrolindinyl, halo-substituted pyrrolidinyl (e.g., fluoropyrrolidinyl and difluoropyrrolidinyl), halo-substituted N-methyl pyrrolidinyl (e.g., N-methylfluoropyrrolidinyl and N-methyldifluoropyrrolidinyl), methoxyethylpyrrolidinyl, alkoxy-substituted N-methylpyrrolidinyl (e.g., (N-methyl)methoxypyrrolidinyl), piperazinyl, dimethylaminylpyrrolidinyl, morpholinyl, methylmorpholinyl, 1,4-oxazepanyl, piperdinyl, C1-C3 alkyl-substituted piperidinyl (e.g., methylpiperidinyl), acylpiperdinyl, cyanopiperdinyl, cycloalkylpiperdinyl, halopiperdinyl (e.g., fluoropiperdinyl), dihalopiperdinyl (e.g., difluoropiperdinyl), alkoxypiperdinyl, pyrrolidonyl, piperidonyl, thiomorpholinyl-1,1-dioxide, 3-azabicyclo[3.1.0]hexanyl, oxa-5-azabicyclo[2.2.1]heptan-5-yl, and azabicyclo[2.2.1]heptan-2-yl.

In one embodiment, the heterocycyl portion of the heterocyclylalkyl is N-methylpyrrolidinyl. In one embodiment, the heterocycyl portion of the heterocyclylalkyl is 3,3-difluoro-1-methylpyrrolidinyl.

In certain other embodiments, $R^4$ is aryl. In one embodiment, $R^4$ is selected from the group consisting of phenyl and naphthyl and is optionally substituted with one or more $R^6$ or $R^7$. Examples of $R^7$ substituents include halogen, hydroxyl, C1-C6 alkyl (e.g., C1-C3 alkyl), cycloalkyl, haloalkyl, Q-haloalkyl, amino, cyano, hydroxyalkyl and alkoxy. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, hydroxyl, fluoro, and chloro. In one embodiment, the aryl is phenyl substituted with one to three $R^7$ groups independently selected from methyl, hydroxyl, trifluoromethyl, fluorine and chlorine. In one embodiment, the aryl is phenyl substituted with hydroxyl and C1-C3 alkyl or two C1-C3 alkyl. In one embodiment, the aryl is phenyl substituted with trifluoromethyl and C1-C3 alkyl or two C1-C3 alkyl.

In one embodiment, $R^4$ is aryl wherein aryl is naphthyl optionally substituted with one or more $R^7$. In one embodiment, the aryl is naphthyl substituted with one or more $R^7$ groups independently selected from halogen, hydroxyl, C1-C3 alkyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, amino, and haloalkyl. In one embodiment, $R^4$ is naphthyl optionally substituted with one to three $R^7$ substituents independently selected from difluoromethyl, methyl, hydroxyl, amino, fluoro, and chloro. In one embodiment, the substituted naphthyl is 8-chloronaphthyl or 8-methylnaphthyl.

In one embodiment, the aryl is naphthyl optionally substituted with one or more halogen. In one embodiment, the aryl is naphthyl substituted with hydroxyl and trifluoromethyl or C1-C3alkyl. In one embodiment, the aryl is naphthyl substituted with hydroxyl.

In one embodiment, $R^4$ is heteroaryl optionally substituted with one or more $R^6$, $R^7$ or $R^8$. In one embodiment, $R^4$ is heteroaryl optionally substituted with one or more $R^7$ or $R^8$ independently selected from halogen, hydroxyl, C3 alkyl, haloalkyl, Q-haloalkyl, alkoxy and amino. In one embodiments, $R^4$ is indoyl, indazolyl, quinolinyl, isoquinolinyl, pyridinyl or benzo[d]thiazolyl optionally substituted with one or more $R^6$, $R^7$ or $R^8$. In one embodiments, $R^4$ is indoyl, indazolyl, quinolinyl, isoquinolinyl, pyridinyl or benzo[d]thiazolyl optionally substituted with one or more $R^7$ or $R^8$ independently selected from oxo, halogen, hydroxyl, C1-C3 alkyl, haloalkyl, Q-haloalkyl, alkoxy and amino.

In yet other embodiments, $R^4$ is heteroaryl, optionally an indoyl or an indazolyl, each of which may be substituted with one or more $R^6$, $R^7$ or $R^8$. In one embodiment, $R^4$ is heteroaryl optionally substituted with one or more $R^7$ or $R^8$ substituents independently selected from the group consisting of halogen, hydroxyl, C3 alkyl, haloalkyl, Q-haloalkyl and alkoxy. In one embodiment, the $R^4$ heteroaryl is indazolyl optionally substituted with one or two $R^7$ or $R^8$ independently selected from oxo, trifluoromethyl, alkoxy, haloalkyl, and C1-C6 alkyl. In other embodiments, the $R^4$ heteroaryl is a quinolinyl or isoquinolinyl, each optionally substituted with one or more $R^7$. In one embodiment, the $R^4$ heteroaryl is a quinolinyl or isoquinolinyl, each optionally substituted with one or more $R^7$ independently selected from amino, hydroxyl, C1-C3 alkyl, and hydroxyl. In one embodiment, the $R^4$ heteroaryl is a quinolinyl or isoquinolinyl, each optionally substituted with $R^7$ selected from hydroxyl and amino. In one embodiment, the $R^4$ heteroaryl is a pyridinyl optionally substituted with one or more $R^6$, $R^7$ or $R^8$. In one embodiment, the $R^4$ heteroaryl is pyridinyl optionally substituted with one or more $R^7$ independently selected from C1-C3 alkyl, halogen and haloalkyl. In one embodiment, the $R^4$ heteroaryl is indolyl optionally substituted with one or more $R^6$, $R^7$ or $R^8$. In one embodiment, the $R^4$ heteroaryl is indolyl optionally substituted with one or two $R^7$ independently selected from hydroxyl, trifluoromethyl and C1-C3alkyl.

In one embodiment, L is a bond.

In one embodiment, m is zero.

In one embodiment, $R^8$ is heteroalkyl, C2-C4 alkynyl or C1-C3 alkyl optionally substituted with —$OR^5$, cyano or heteroaryl. In one embodiment, $R^8$ is methyl, cyanomethyl, methoxymethyl, hydroxymethyl. In one embodiment, $R^8$ is methyl. In one embodiment, $R^8$ is cyanomethyl. In one embodiment, $R^8$ is hydroxymethyl.

In one embodiment, Formula II includes compounds having the Formula II-A:

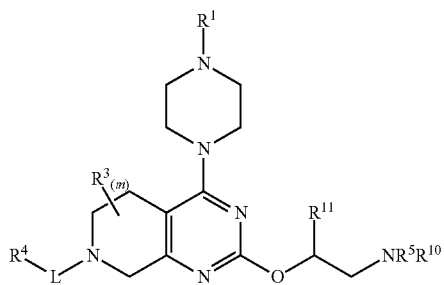

wherein $R^1$, $R^3$, $R^4$, $R^5$, $R^{10}$, L and m are as defined for Formula II, $R^{11}$ is hydrogen, methyl or hydroxyalkyl, and the piperazinyl ring is optionally substituted with $R^8$ wherein $R^8$ is as defined for Formula II.

In particular embodiments, $R^1$ is —$C(O)C(R^A)$=$C(R^B)_p$ where $R^A$, $R^B$ and p are as defined for Formula II. In one embodiment, $R^1$ is —$C(O)C(R^A)$≡$C(R^B)_p$, wherein ≡ is a triple bond and $R^A$ is absent, p is one and $R^B$ is hydroxyalkyl.

In one embodiment, $R^1$ is —$C(O)C(R^A)$=$C(R^B)_p$, wherein = is a double bond and $R^A$ is hydrogen or C1-C3 alkyl, p is two and at least one $R^B$ is deuterium, cyano, C1-C3 alkyl, hydroxyalkyl, heteroalkyl, C1-C3 alkoxy, halogen, haloalkyl, —$ZNR^5R^{11}$, —$C(O)N(R^5)_2$, —NHC(O) C1-C3 alkyl, —$CH_2NHC(O)$C1-C3 alkyl, heteroaryl, heteroarylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$.

In one embodiment, $R^1$ is —$C(O)C(R^A)$=$C(R^B)_p$, wherein $R^A$ is deuterium, cyano, halogen, haloalkyl, heteroalkyl, —$C(O)N(R^5)_2$, or hydroxyalkyl, p is two, and each $R^B$ is hydrogen. In one embodiment, $R^A$ is halogen. In one embodiment, the halogen is fluorine or chlorine. In one embodiment, $R^A$ is haloalkyl. In one embodiment, the haloalkyl is trifluoromethyl. In one embodiment, $R^A$ is cyano. In one embodiment, $R^A$ is heteroalkyl. In one embodiment, the heteroalkyl is methoxymethyl. In one embodiment, $R^A$ is hydroxyalkyl.

In one embodiment, $R^1$ is —$C(O)C(R^A)$=$C(R^B)_p$, wherein = is a double bond and $R^A$ is deuterium, p is two and at least one $R^B$ is deuterium.

In one embodiment, $R^1$ is —$C(O)C(R^A)$=$C(R^B)_p$, wherein = is a double bond and p is two, one $R^B$ is hydrogen and $R^A$ and one $R^B$ and the carbon atoms to which they are attached form a 5-8 membered partially saturated cycloalkyl substituted with oxo.

In one embodiment, $R^1$ is —$C(O)C(R^A)$=$C(R^B)_p$, wherein = is a double bond and p is two, one $R^B$ is hydrogen, the second $R^B$ is dialkylaminylalkyl, and $R^A$ is halogen.

In one embodiment, L is a bond. In one embodiment, $R^4$ is aryl or heteroaryl, each of which is optionally substituted with one or more $R^6$, $R^7$ or $R^8$. In one embodiment, $R^4$ is aryl or heteroaryl, each of which is optionally substituted with one or more $R^7$. In one embodiment, each $R^7$ or $R^8$ is independently selected from oxo, hydroxyl, amino, halogen, C1-C3 alkyl, haloalkyl, Q-haloalkyl, cycloalkyl and alkoxy. In one embodiment, $R^5$ and $R^{10}$ are each C1-C3 alkyl. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, 2,2,2-trifluoroethyl, hydroxyl, trifluoromethoxy, hydroxyl, fluoro, chloro, isopropyl, cyclopropyl and trifluoromethylthio. In one embodiment, the aryl is phenyl substituted with one to three $R^7$ groups independently selected from hydroxyl, fluorine and chlorine. In one embodiment, the aryl is phenyl substituted with hydroxyl and C1-C3 alkyl or two C1-C3 alkyl. In one embodiment, the aryl is phenyl substituted with Q-haloalkyl and hydroxyl or fluorine. In one embodiment, the aryl is naphthyl substituted with one or more $R^7$ groups independently selected from halogen, hydroxyl, C1-C3 alkyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, amino, and haloalkyl. In one embodiment, $R^4$ is naphthyl optionally substituted with one to three $R^7$ or $R^8$ substituents independently selected from difluoromethyl, methyl, hydroxyl, amino, fluoro, and chloro. In one embodiment, the aryl is naphthyl optionally substituted with one or more halogen. In one embodiment, the aryl is naphthyl substituted with hydroxyl and trifluoromethyl or C1-C3alkyl. In one embodiment, the aryl is naphthyl substituted with hydroxyl. In one embodiment, $R^4$ is heteroaryl, wherein the heteroaryl is indazolyl optionally substituted with one or two $R^7$ or $R^8$ independently selected from oxo, alkoxy, haloalkyl, and C1-C6 alkyl. In one embodiment, $R^4$ is heteroaryl, wherein the heteroaryl is quinolinyl or isoquinolinyl, each optionally substituted with one or more $R^7$. In one embodiment, $R^4$ is heteroaryl, wherein the heteroaryl is quinolinyl or isoquinolinyl, each optionally substituted with one or more $R^7$ independently selected from amino, hydroxyl, C1-C3alkyl, and hydroxyl. In one embodiment, the $R^4$ heteroaryl is a pyridinyl optionally substituted with one or more $R^6$, $R^7$ or $R^8$. In one embodiment, the $R^4$ heteroaryl is pyridinyl optionally substituted with one or more $R^7$ independently selected from C1-C3 alkyl, halogen and haloalkyl. In one embodiment, the $R^4$ heteroaryl is indolyl optionally substituted with one or more $R^7$. In one embodiment, the $R^4$ heteroaryl is indolyl optionally substituted with one or two $R^7$ independently selected from hydroxyl and C1-C3alkyl. In one embodiment, $R^{11}$ is methyl. In one embodiment, the piperazinyl ring is unsubstituted. In one embodiment, the piperazinyl ring is substituted with $R^8$. In one embodiment, $R^8$ is C1-C3 alkyl optionally substituted with cyano or hydroxyl. In one embodiment, $R^8$ is methyl, cyanomethyl or hydroxymethyl. In one embodiment, $R^8$ is methyl. In one embodiment, $R^8$ is cyanomethyl. In one embodiment, $R^8$ is hydroxymethyl. In another embodiment, $R^5$ and $R^{10}$ are each C1-C3 alkyl, $R^{11}$ is methyl, $R^8$ is methyl, cyanomethyl or hydroxymethyl, L is a bond, and $R^4$ is aryl or heteroaryl, each optionally substituted with one or more $R^6$ or $R^7$.

In one embodiment, Formula II includes compounds having the Formula II-B:

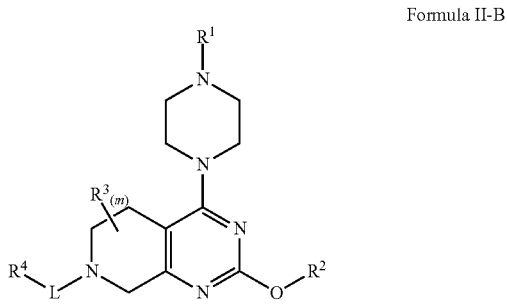

Formula II-B where $R^1$, $R^3$, $R^4$, L and m are as defined for Formula II, $R^2$ is heterocyclylalkyl optionally substituted with one or more $R^9$ wherein $R^9$ is as defined for Formula II, and the piperazinyl ring is optionally substituted with $R^8$, where $R^8$ is as defined for Formula II.

In particular embodiments, $R^1$ is —C(O)C($R^A$)≡C($R^B$)$_p$ where $R^A$, $R^B$ and p are as defined for Formula II. In one embodiment, $R^1$ is —C(O)C($R^A$)≡C($R^B$)$_p$, wherein ≡ is a triple bond and $R^A$ is absent, p is one and $R^B$ is hydroxyalkyl.

In one embodiment, $R^1$ is —C(O)C($R^A$)=C($R^B$)$_p$, wherein = is a double bond and $R^A$ is hydrogen or C1-C3 alkyl, p is two and at least one $R^B$ is deuterium, cyano, C1-C3 alkyl, hydroxyalkyl, heteroalkyl, C1-C3 alkoxy, halogen, haloalkyl, —ZN$R^5R^{11}$, —C(O)N($R^5$)$_2$, —NHC(O) C1-C3 alkyl, —CH$_2$NHC(O)C1-C3 alkyl, heteroaryl, heteroarylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$.

In one embodiment, $R^1$ is —C(O)C($R^A$)=C($R^B$)$_p$, wherein $R^A$ is deuterium, cyano, halogen, haloalkyl, heteroalkyl, —C(O)N($R^5$)$_2$, or hydroxyalkyl, p is two, and each $R^B$ is hydrogen. In one embodiment, $R^A$ is halogen. In one embodiment, the halogen is fluorine or chlorine. In one embodiment, $R^A$ is haloalkyl. In one embodiment, the haloalkyl is trifluoromethyl. In one embodiment, $R^A$ is cyano. In one embodiment, $R^A$ is heteroalkyl. In one embodiment, the heteroalkyl is methoxymethyl. In one embodiment, $R^A$ is hydroxyalkyl.

In one embodiment, $R^1$ is —C(O)C($R^A$)=C($R^{13}$)$_p$, wherein = is a double bond and $R^A$ is deuterium, p is two and at least one $R^B$ is deuterium.

In one embodiment, $R^1$ is —C(O)C($R^A$)=C($R^B$)$_p$, wherein = is a double bond and p is two, one $R^B$ is hydrogen and $R^A$ and one $R^B$ and the carbon atoms to which they are attached form a 5-8 membered partially saturated cycloalkyl substituted with oxo.

In one embodiment, $R^1$ is —C(O)C($R^A$)=C($R^B$)$_p$, wherein = is a double bond and p is two, one $R^B$ is hydrogen, the second $R^B$ is dialkylaminylalkyl, and $R^A$ is halogen.

In one embodiment, the heterocyclyl portion of the $R^2$ heterocyclylalkyl is a monocyclic, bicyclic, or bridged ring system having one or two ring heteroatoms independently selected from N and O. In one embodiment, $R^2$ heterocyclyl is azetidinyl, methylazetidinyl, ethylazetidinyl, isopropylazetidinyl, difluoroazetidinyl, cyclopropylazetidinyl, tetrahydropyranylazetidinyl, tetrahydropyran, pyrrolidinyl, methylpyrrolidinyl, diemethylpyrrolidinyl, isopropylpyrrolidinyl, cycloalkylalkylpyrrolidinyl, hydroxypyrrolindinyl, fluoropyrrolidinyl, difluoropyrrolidinyl, (N-methyl)fluoropyrrolidinyl, (N-methyl)difluoropyrrolidinyl, methoxyethylpyrrolidinyl, alkoxy-substituted N-methylpyrrolidinyl (e.g., (N-methyl)methoxypyrrolidinyl), piperazinyl, dimethylaminylpyrrolidinyl, pyrrolidinone, methylpyrrolidinone, morpholinyl, methylmorpholinyl, ethylmorpholinyl, isopropylmorpholinyl, oxetanyl, 1,4-oxazepanyl, piperdinyl, methylpiperidinyl acylpiperdinyl, cyanopiperdinyl, cycloalkylpiperdinyl, halopiperdinyl, dihalopiperdinyl, fluoropiperdinyl, difluoropiperdinyl, alkoxypiperdinyl, pyrrolidonyl, piperidinonyl, tetrahydropyrrolizinyl, thiomorpholinyl-1,1-dioxide, 3-azabicyclo[3.1.0]hexanyl, oxa-5-azabicyclo[2.2.1]heptan-5-yl, or azabicyclo[2.2.1]heptan-2-yl, optionally substituted with one or more $R^9$. In one embodiment, each $R^9$ is selected from acyl, oxo, halogen, cyano, C1-C3 alkyl, alkoxy, hydroxyalkyl, heteroalkyl, cycloalkyl, aralkyl, heterocyclyl and dialkylamidoalkyl. In one embodiment, L is a bond. In one embodiment, the heterocyclyl portion of the $R^2$ heterocyclylalkyl is (N-methyl)difluoropyrrolidinyl, including 3,3-difluoro-1-methylpyrrolidinyl. In one embodiment, the heterocyclyl portion of the $R^2$ heterocyclylalkyl is N-methylpyrrolidinyl.

In one embodiment, $R^4$ is aryl or heteroaryl, each of which is optionally substituted with one or more $R^6$, $R^7$ or $R^8$. In one embodiment, $R^4$ is aryl or heteroaryl, each of which is optionally substituted with one or more $R^7$. In one embodiment, each $R^7$ is independently selected from hydroxyl, amino, halogen, C1-C3 alkyl, haloalkyl, Q-haloalkyl, cycloalkyl and alkoxy. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more R⁷ groups independently selected from halogen, haloalkyl, methyl, isopropyl, methoxy, Q-haloalkyl and hydroxyl. In one embodiment, the aryl is phenyl substituted with one or more R⁷ groups independently selected from methyl, trifluoromethyl, 2,2,2-trifluoroethyl, hydroxyl, trifluoromethoxy, hydroxyl, fluoro, chloro, isopropyl, cyclopropyl and trifluoromethylthio. In one embodiment, the aryl is phenyl substituted with one to three R⁷ groups independently selected from hydroxyl, fluorine and chlorine. In one embodiment, the aryl is phenyl substituted with hydroxyl and C1-C3 alkyl or two C1-C3 alkyl. In one embodiment, the aryl is phenyl substituted with Q-haloalkyl and hydroxyl or fluorine. In one embodiment, the aryl is naphthyl substituted with one or more R⁷ groups independently selected from halogen, hydroxyl, C1-C3 alkyl, haloalkyl, Q-haloalkyl, and alkoxy. In one embodiment, the aryl is naphthyl substituted with one or more R⁷ groups independently selected from halogen, haloalkyl, methyl, isopropyl, methoxy, Q-haloalkyl and hydroxyl. In one embodiment, R⁴ is naphthyl optionally substituted with one or more R⁷ substituents independently selected from hydroxyl, halogen, C1-C3 alkyl, amino, and haloalkyl. In one embodiment, R⁴ is naphthyl optionally substituted with one to three R⁷ substituents independently selected from difluoromethyl, methyl, hydroxyl, amino, fluoro, and chloro. In one embodiment, the aryl is naphthyl optionally substituted with one or more halogen. In one embodiment, the aryl is naphthyl substituted with hydroxyl and trifluoromethyl or C1-C3alkyl. In one embodiment, the aryl is naphthyl substituted with hydroxyl. In one embodiment, R⁴ is heteroaryl, wherein the heteroaryl is indazolyl optionally substituted with one or two R⁷ independently selected from alkoxy, haloalkyl, and C1-C6 alkyl.

In one embodiment, R⁴ is heteroaryl, wherein the heteroaryl is quinolinyl or isoquinolinyl, each optionally substituted with one or more R⁶, R⁷ or R⁸. In one embodiment, R⁴ is heteroaryl, wherein the heteroaryl is quinolinyl or isoquinolinyl, each optionally substituted with one or more R⁶, R⁷ or R⁸ independently selected from oxo, amino, hydroxyl, C1-C3 alkyl, and hydroxyl. In one embodiment, the R⁴ heteroaryl is a pyridinyl optionally substituted with one or more R⁶, R⁷ or R⁸. In one embodiment, the R⁴ heteroaryl is pyridinyl optionally substituted with one or more R⁷ independently selected from C1-C3 alkyl, halogen and haloalkyl. In one embodiment, the R⁴ heteroaryl is indolyl optionally substituted with one or more R⁶, R⁷ or R⁸. In one embodiment, the R⁴ heteroaryl is indolyl optionally substituted with one or two R⁷ independently selected from hydroxyl and C1-C3 alkyl. In one embodiment, R¹¹ is methyl. In one embodiment, the piperazinyl ring is unsubstituted. In one embodiment, the piperazinyl ring of Formula II-B is substituted with R⁸. In one embodiment, R⁸ is C1-C3 alkyl optionally substituted with cyano, hydroxyl or methoxy. In one embodiment, R⁸ is methyl, cyanomethyl, hydroxymethyl or methoxymethyl.

Nonlimiting examples of compounds of Formula (II), Formula II-A and Formula II-B are selected from the group consisting of:

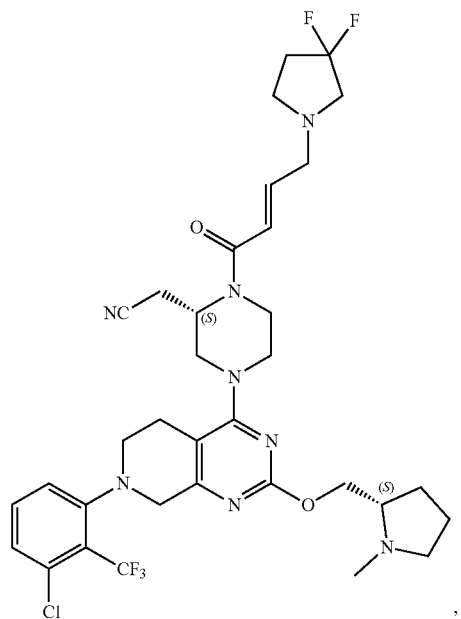

,

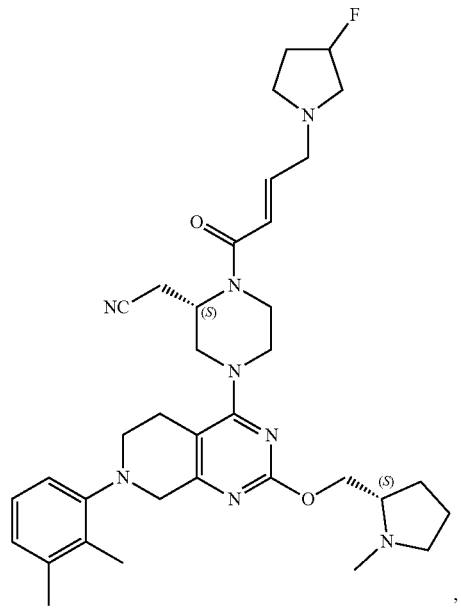

,

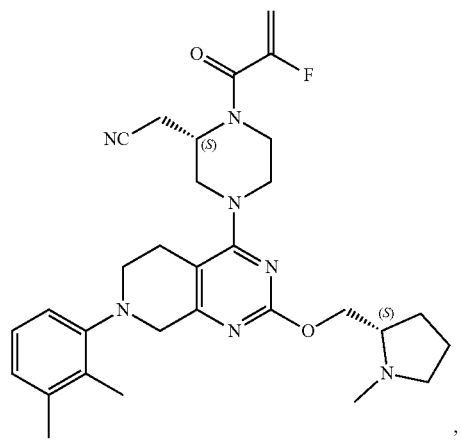

,

139
-continued
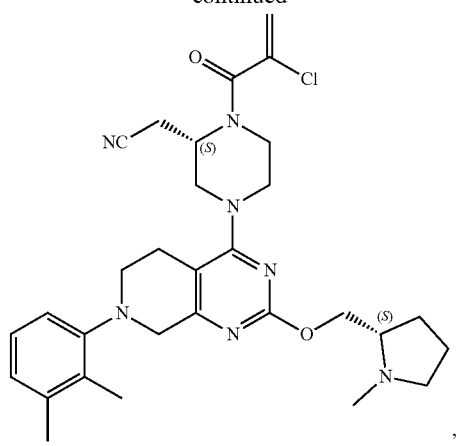
,
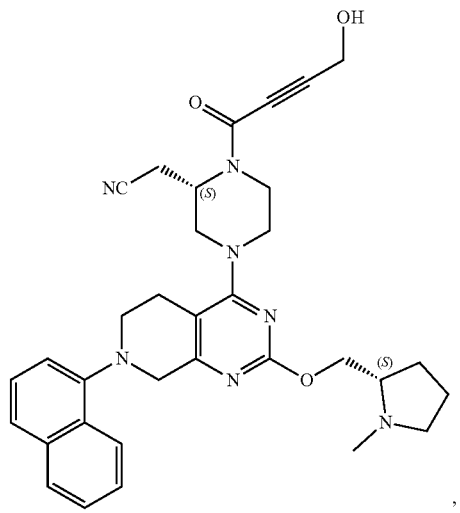
,
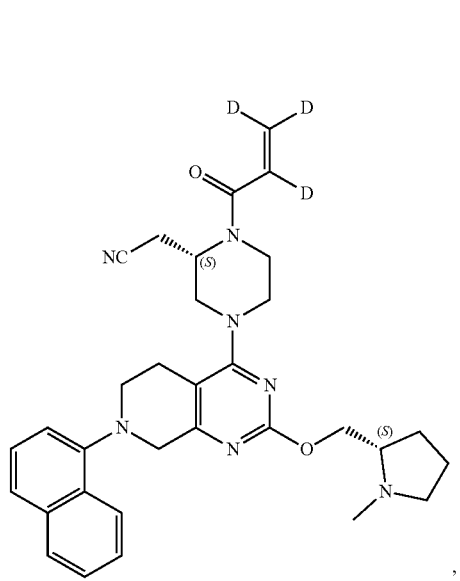
,
140
-continued
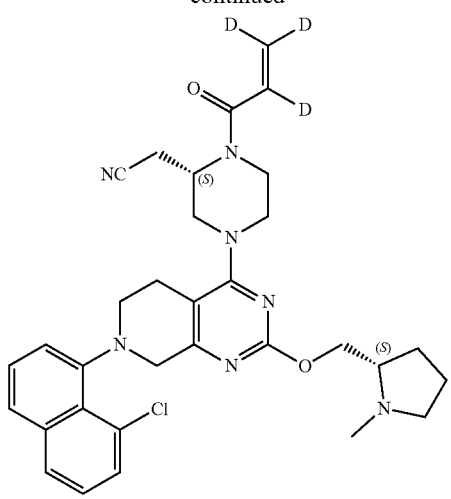
,
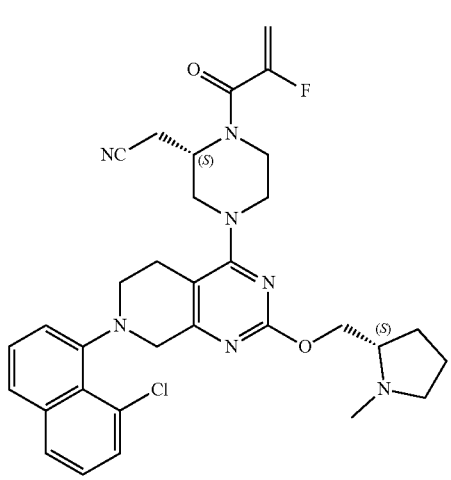
,
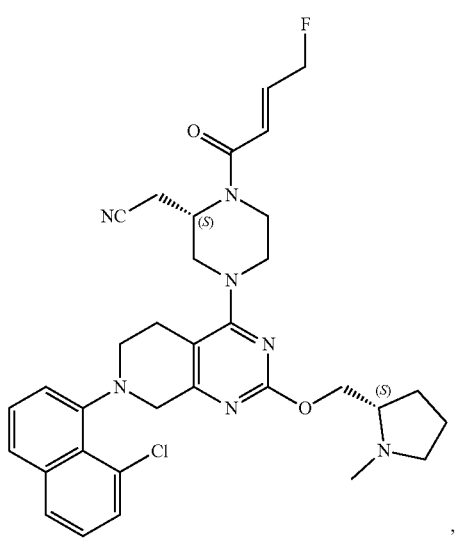
, 141
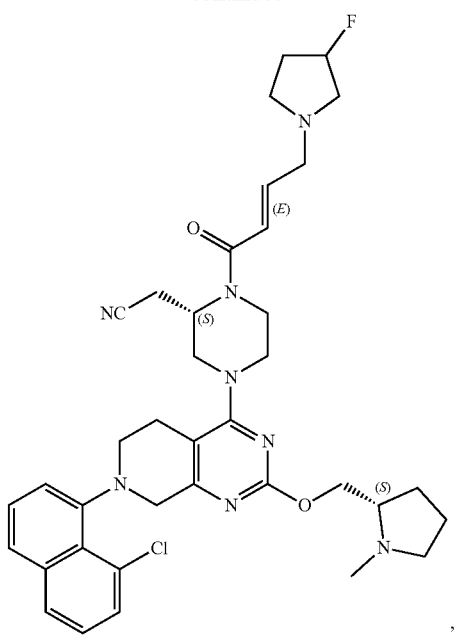
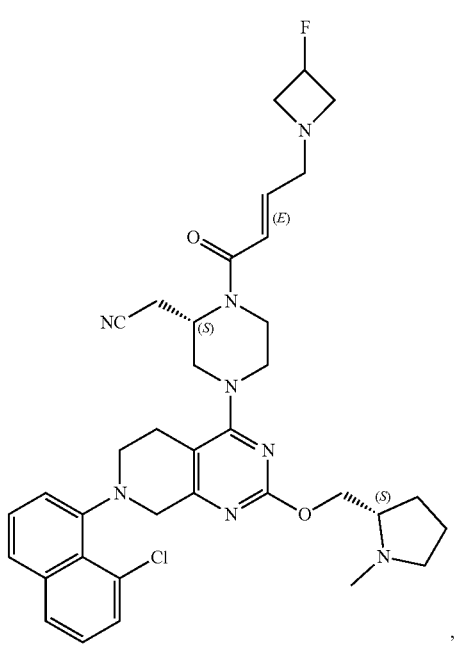
142
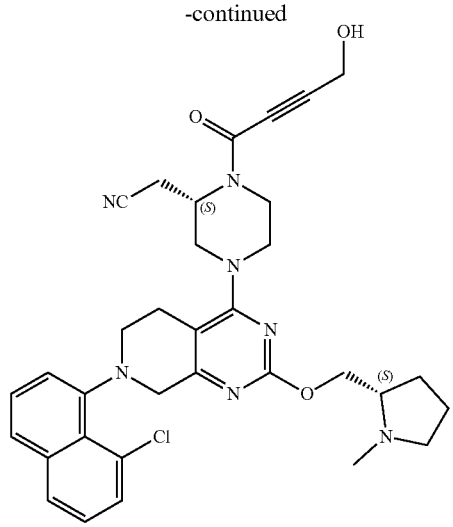
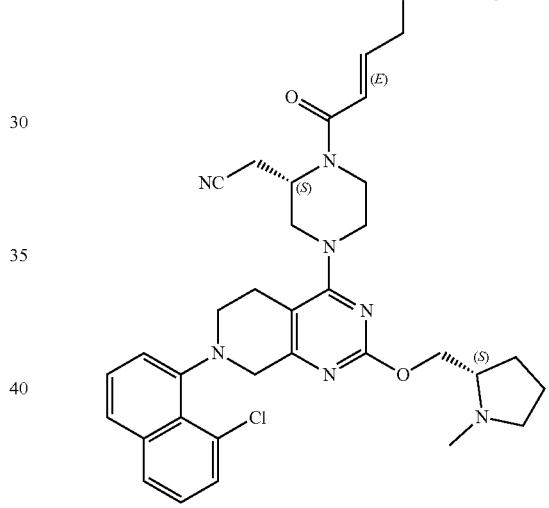
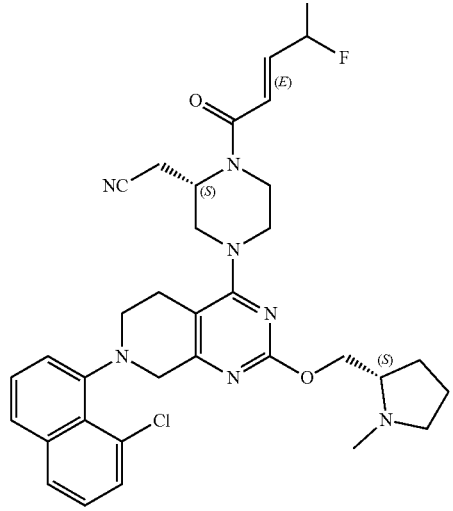

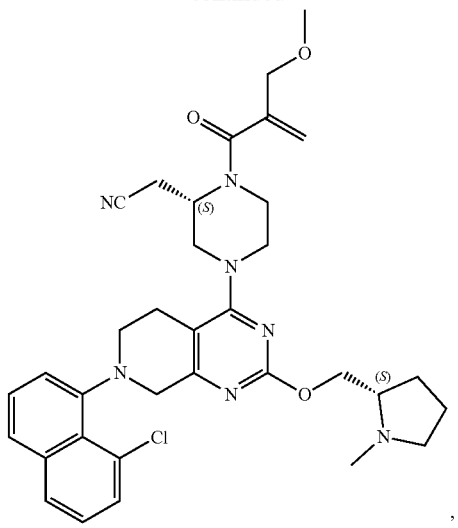
,
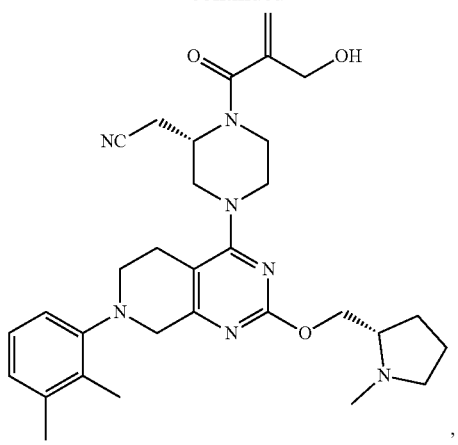
,
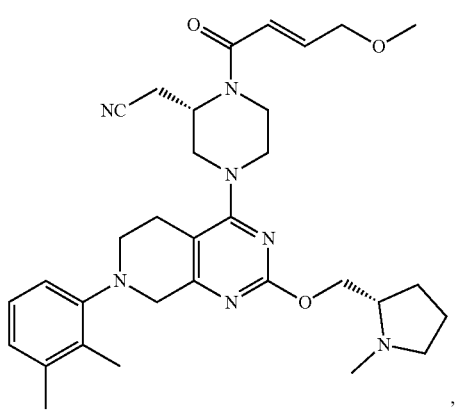
,
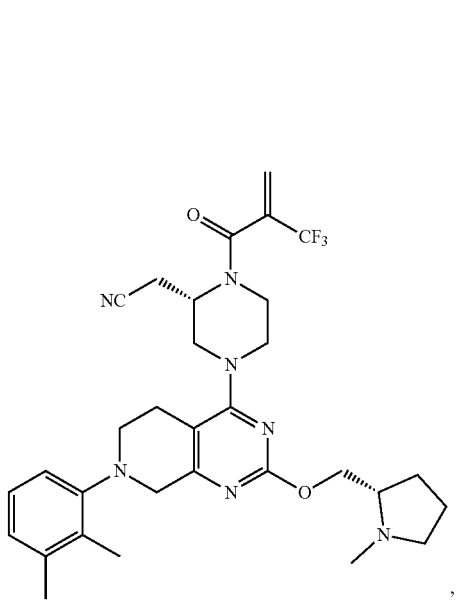
,

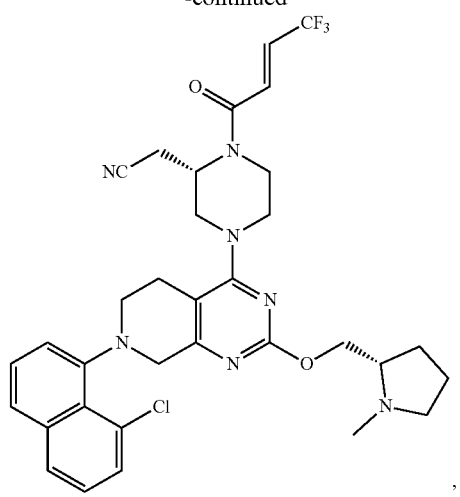
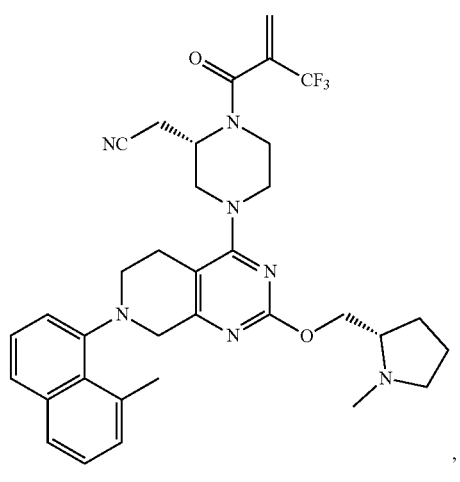
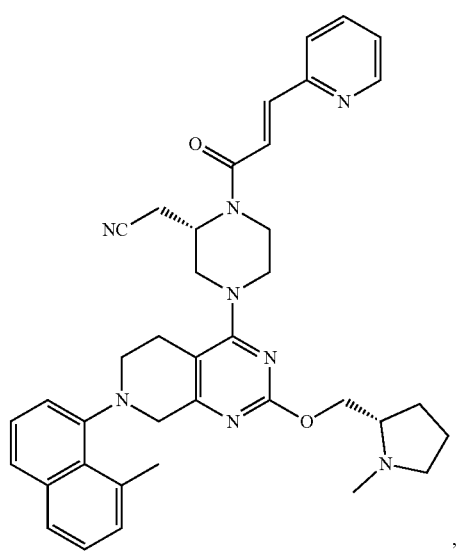
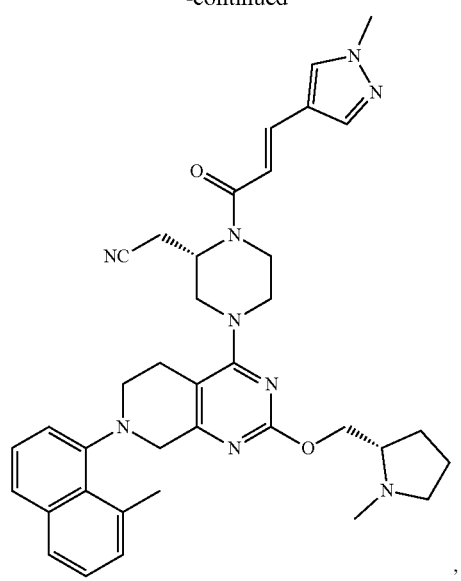
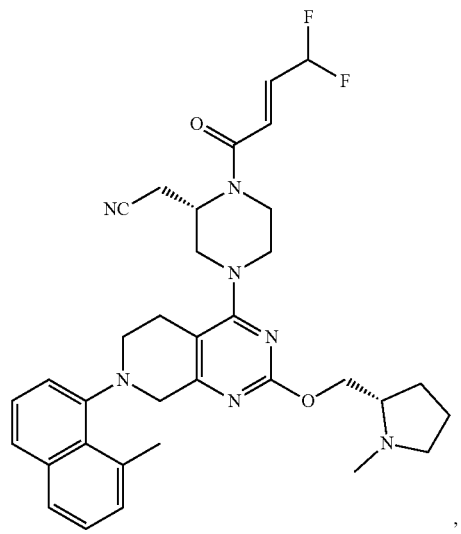
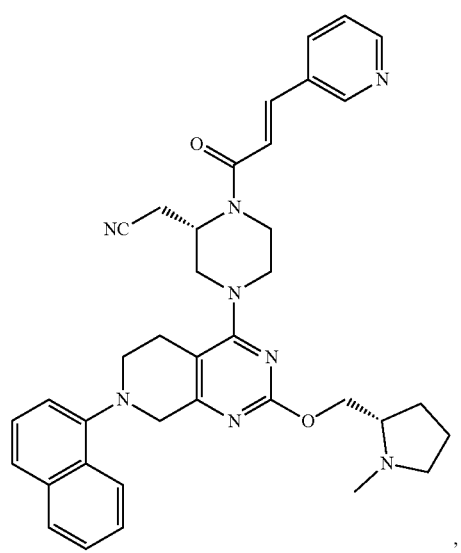

147
-continued
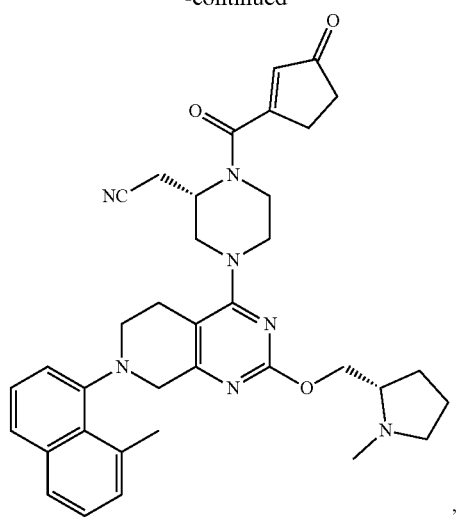
,
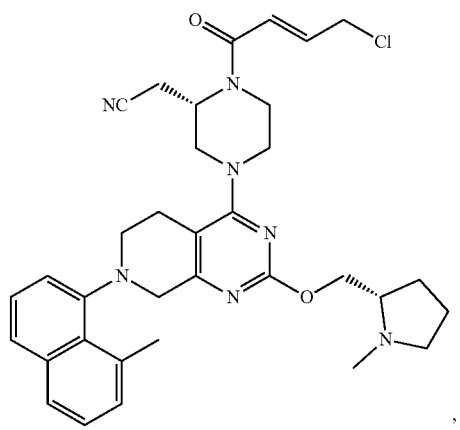 [SMILES: CCC1(COc2nc3c(c(N4CCN(C(=O)/C=C/CF)[C@@H](CC#N)C4)n2)CCN(c2cccc4cccc(Cl)c24)C3)CCCN1C]
,
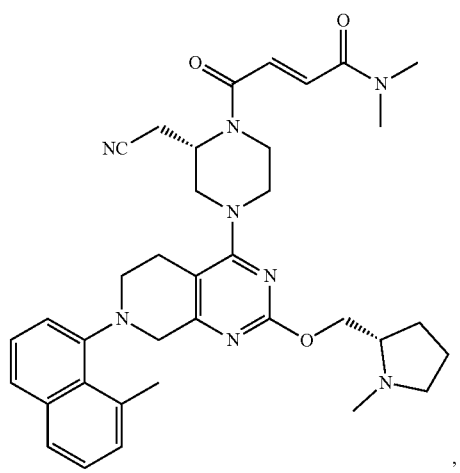
,
148
-continued
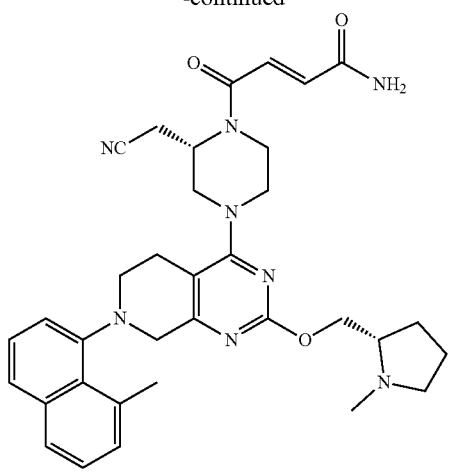
,
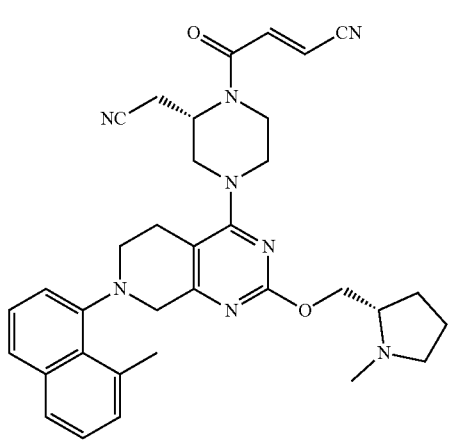
,
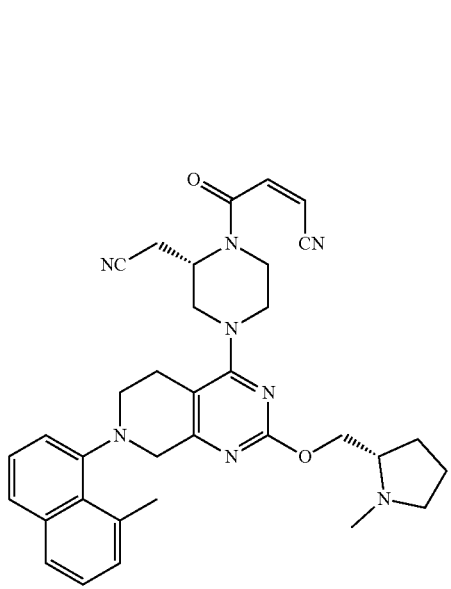
, 149
-continued
150
-continued
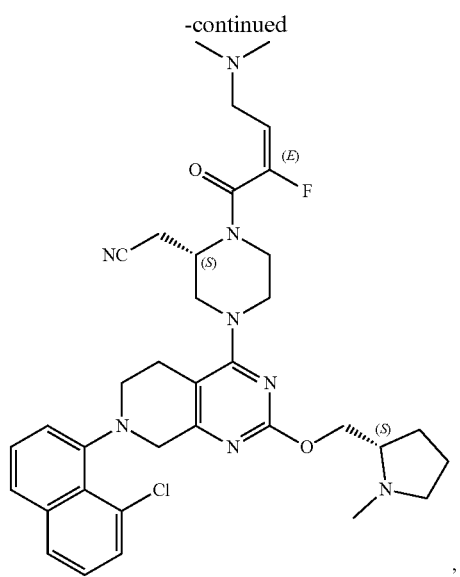
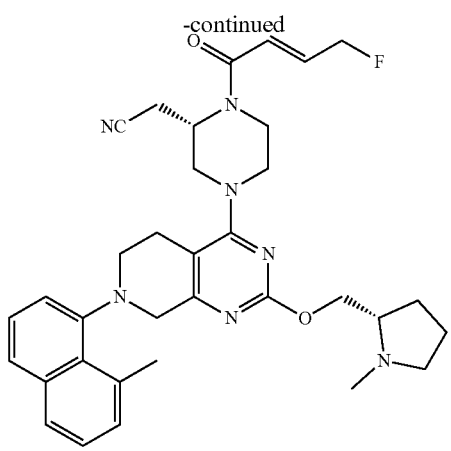
,
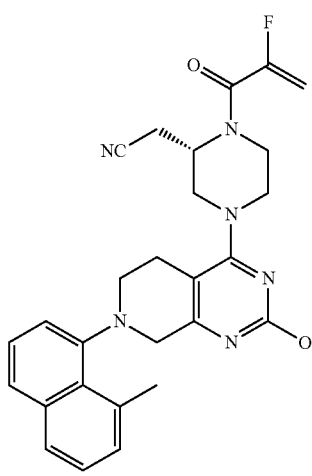
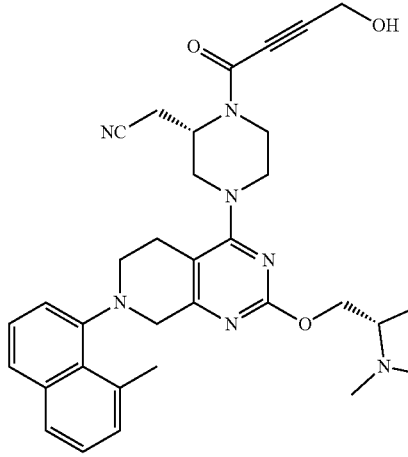
,
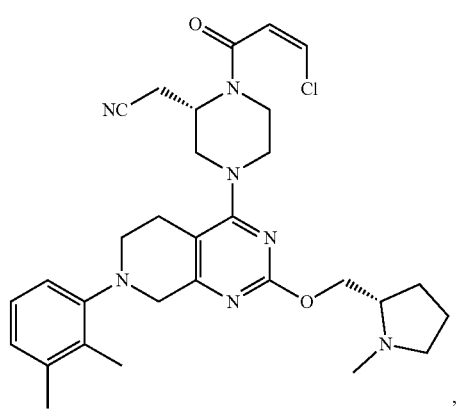
,
, 151
-continued
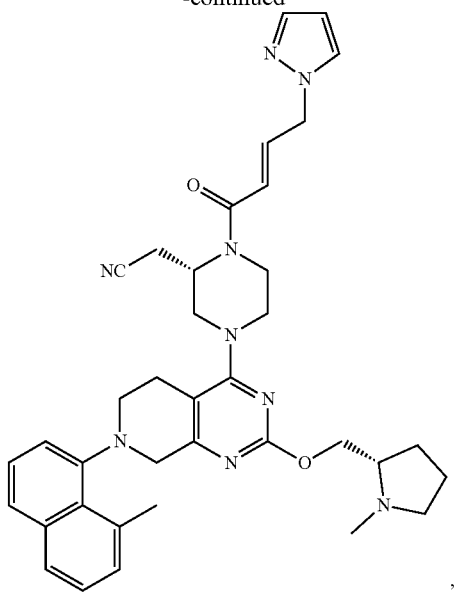
,
152
-continued
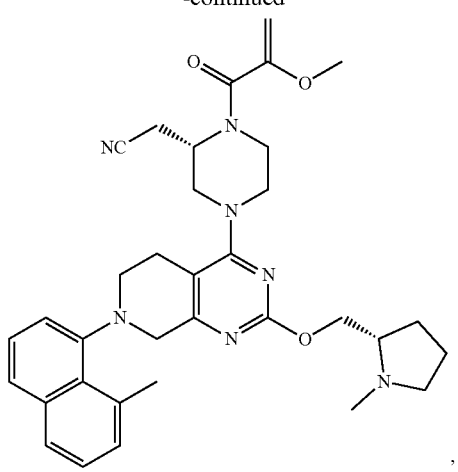
,
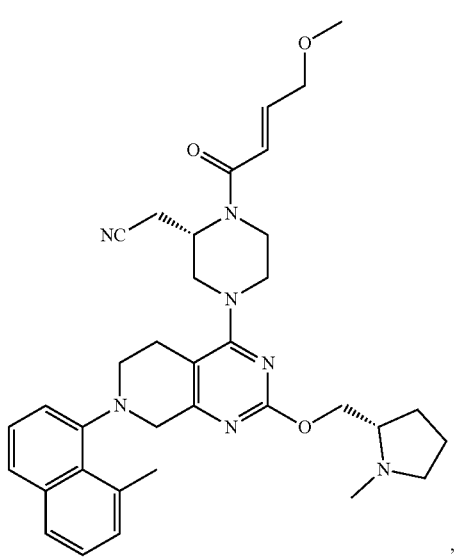
, 153
-continued
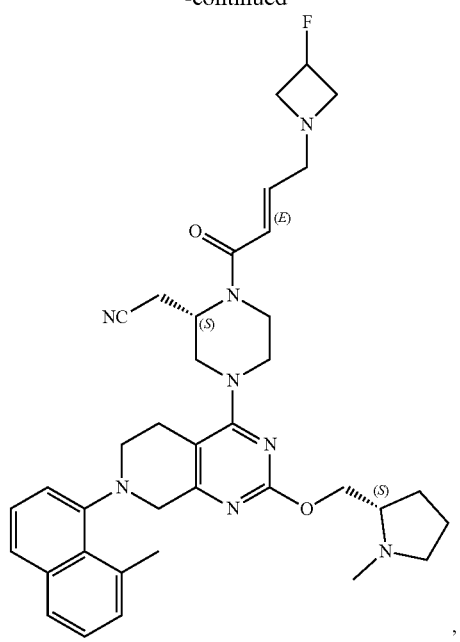
,
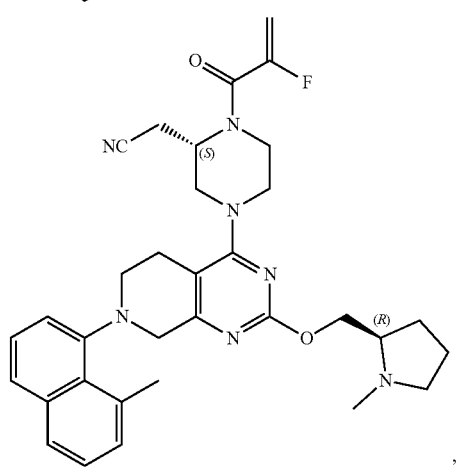
,
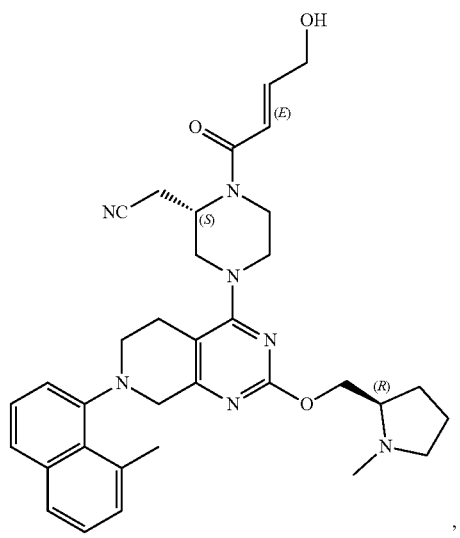
,
154
-continued
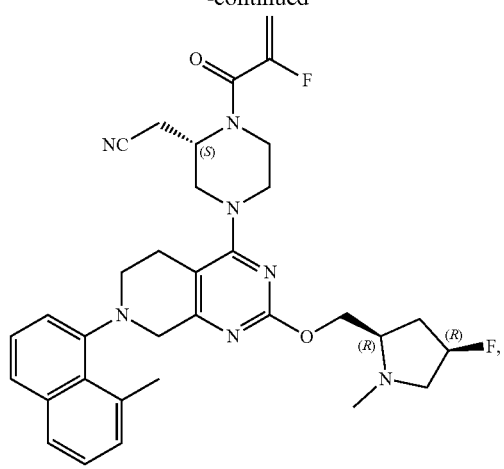
,
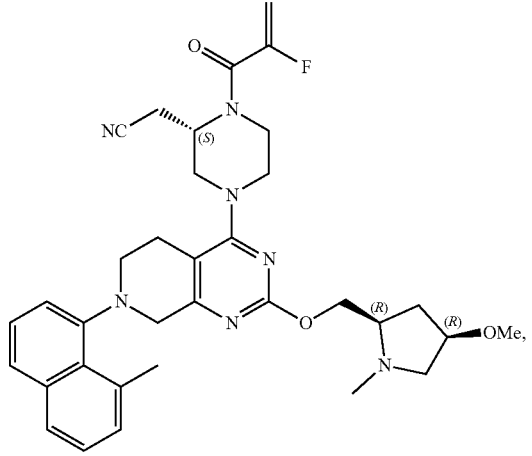
,
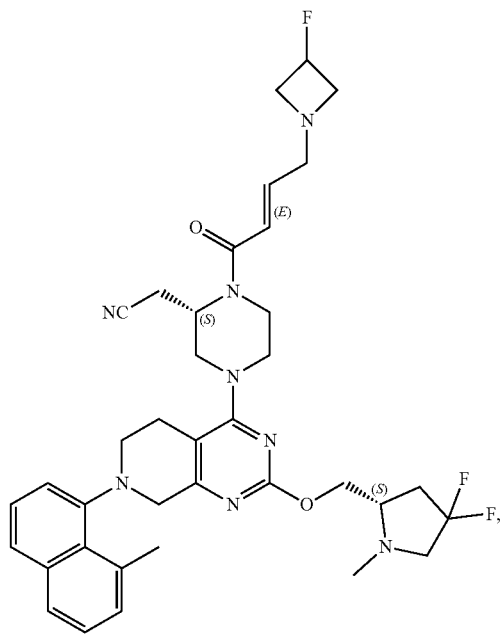

155
-continued
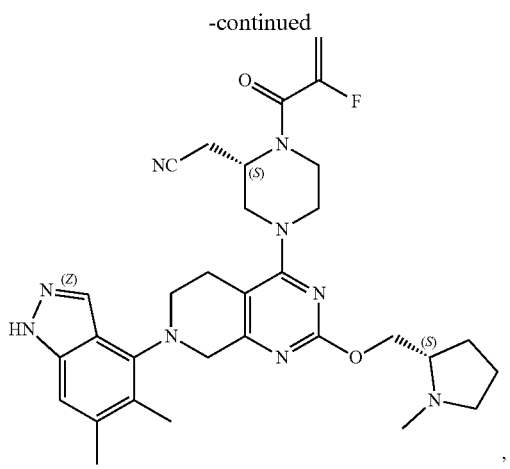
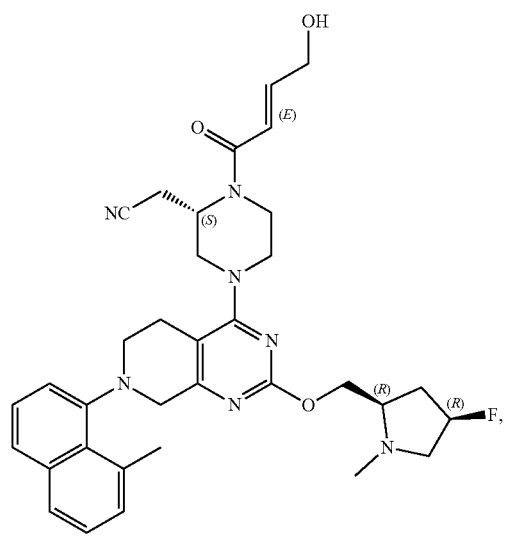
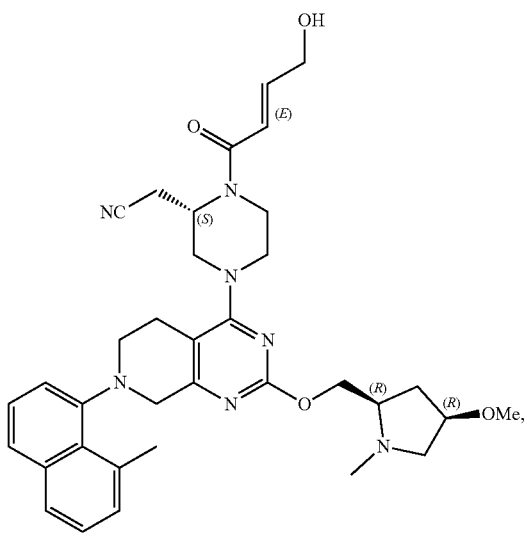
156
-continued
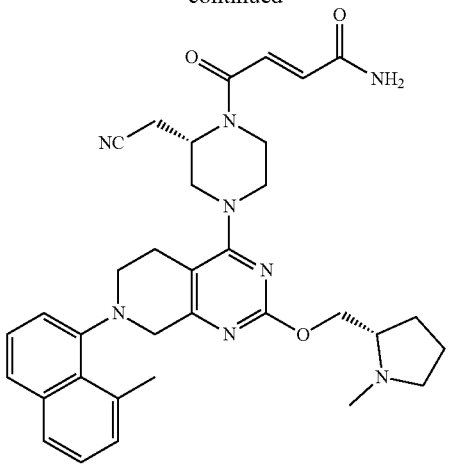
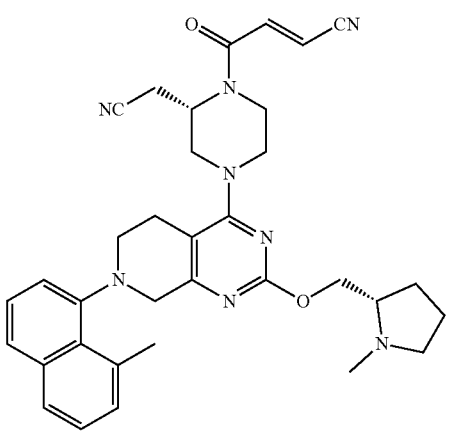
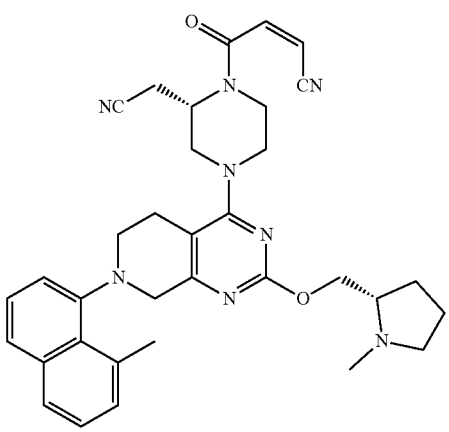

157
-continued
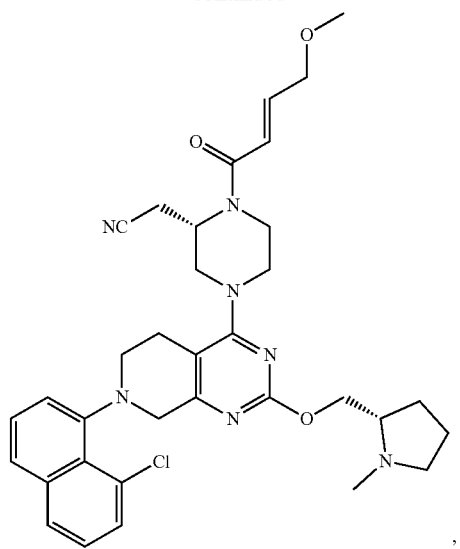
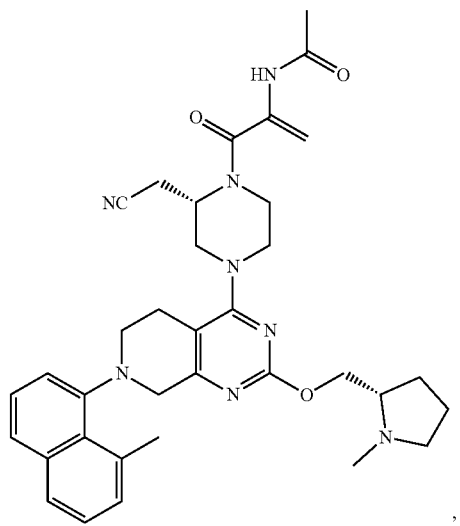
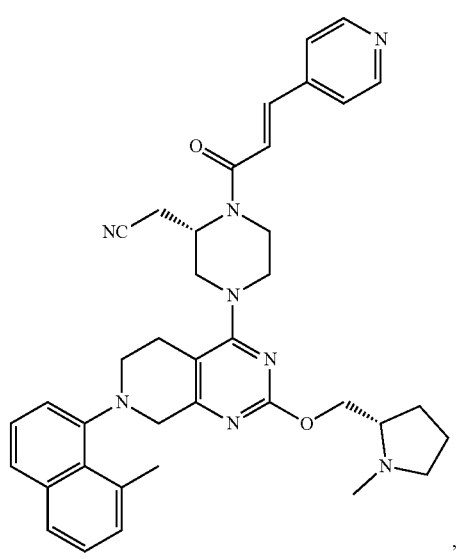
158
-continued
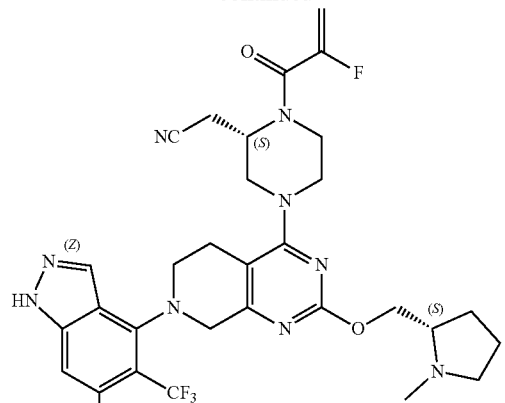
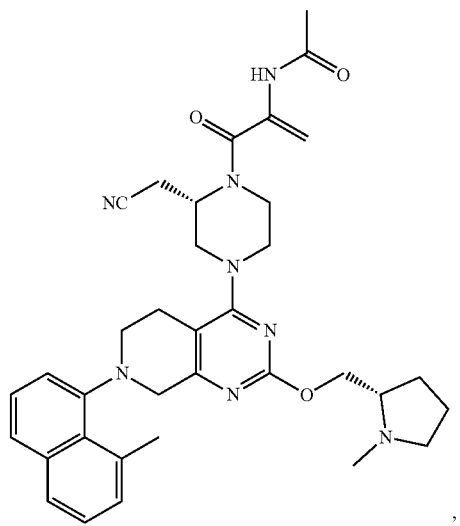

159
-continued
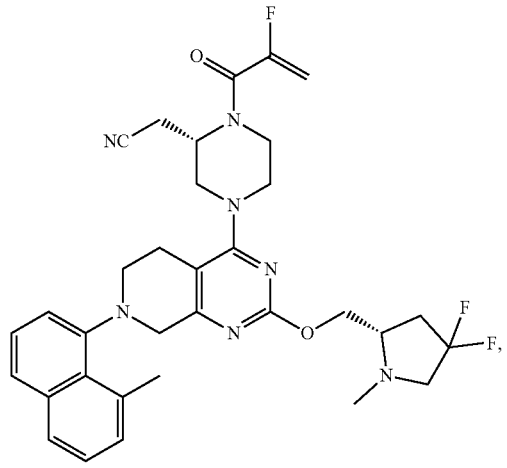
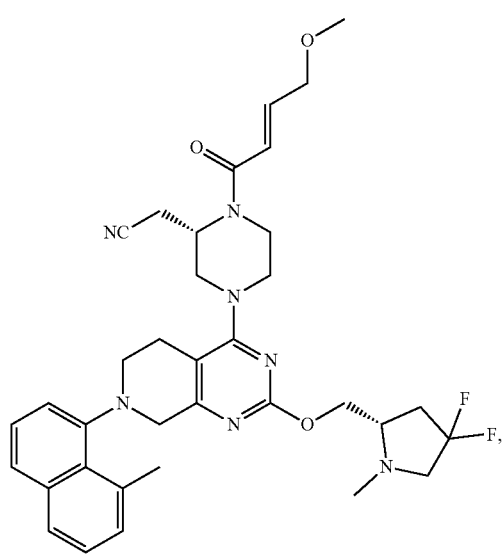
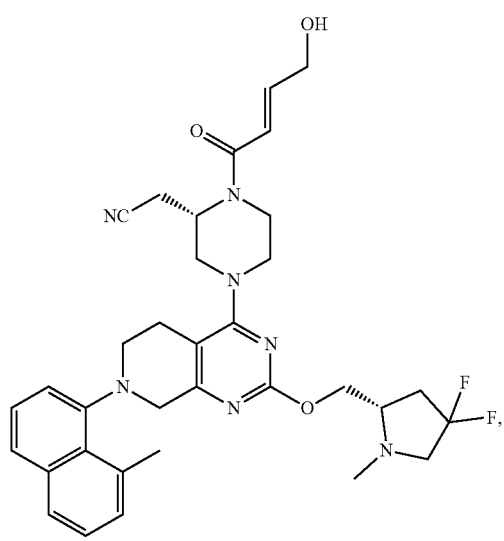
160
-continued
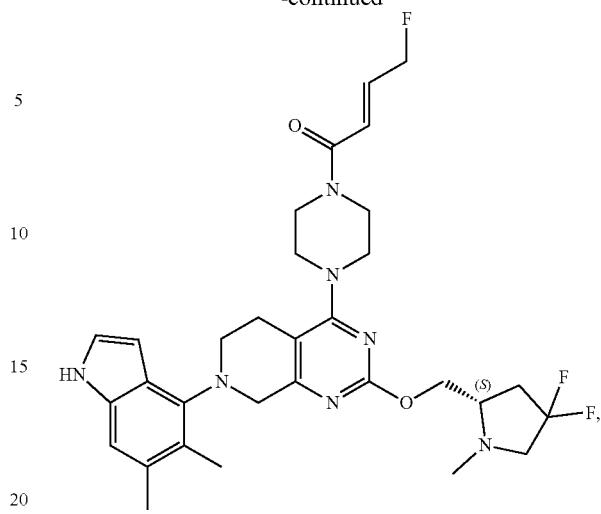
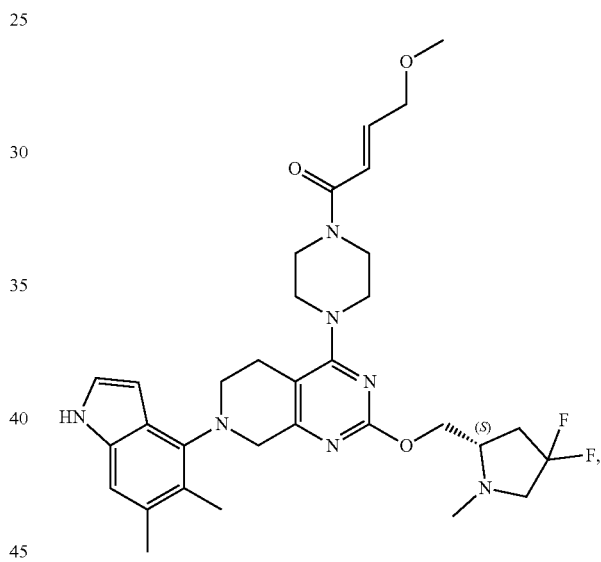
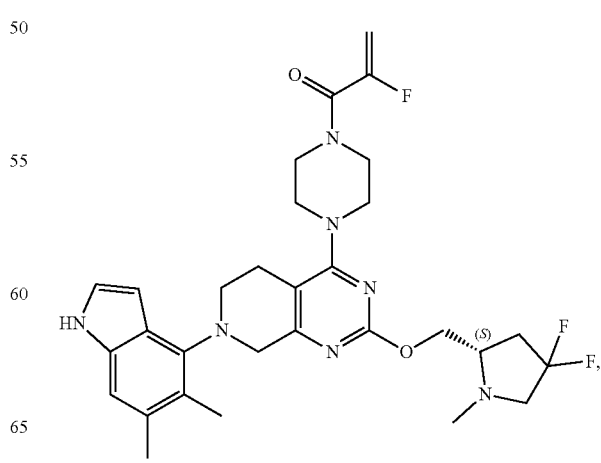

161
-continued
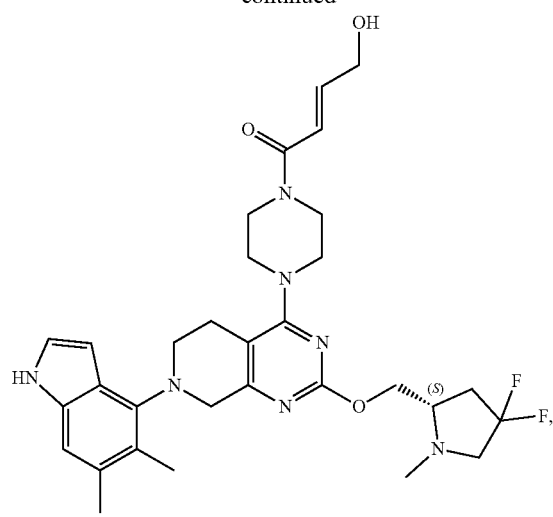
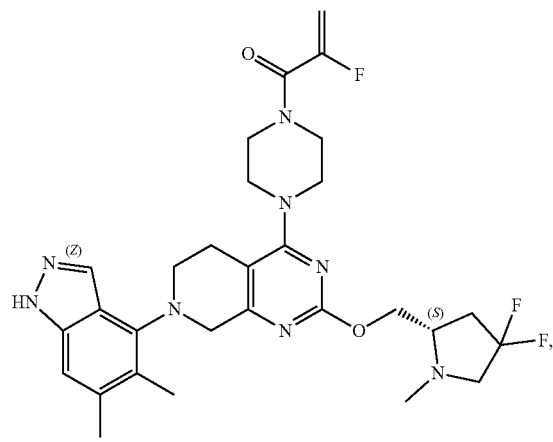
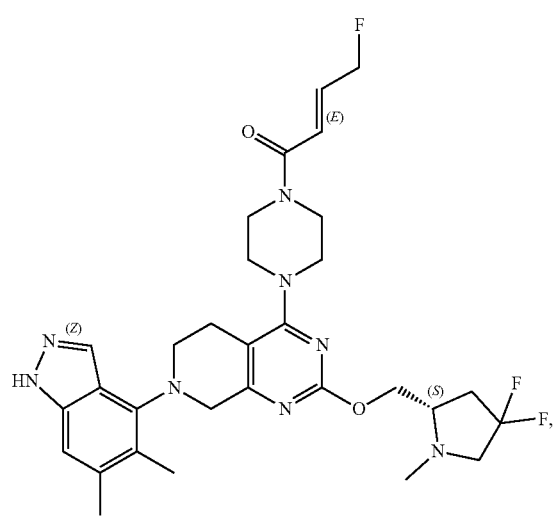
162
-continued
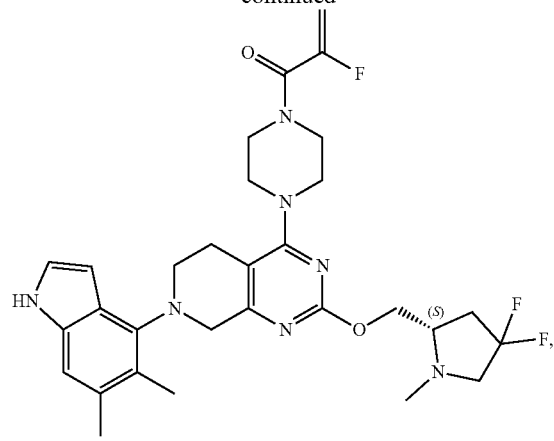
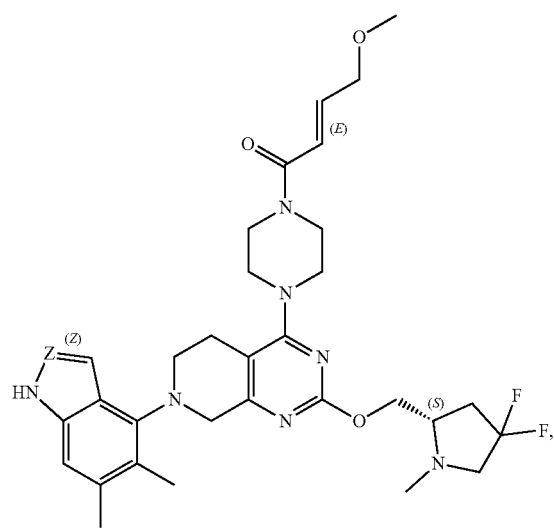
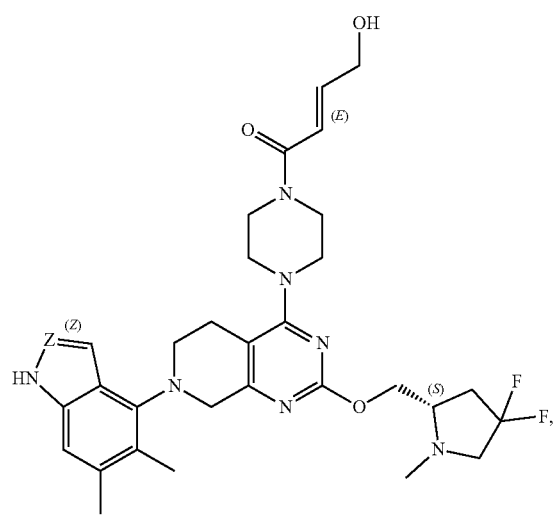

163
-continued
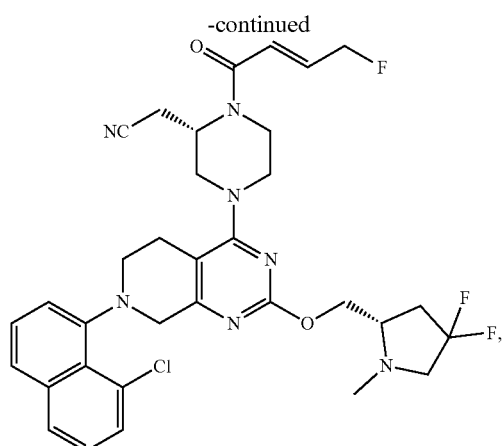
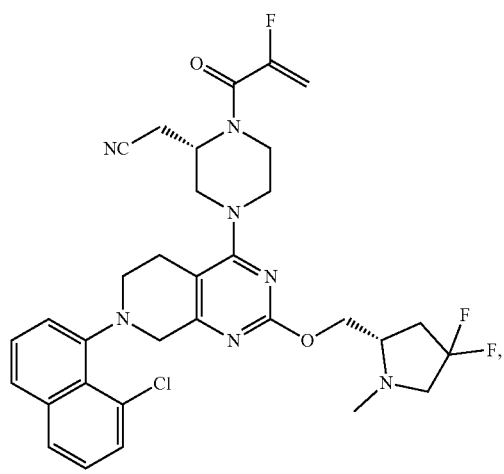
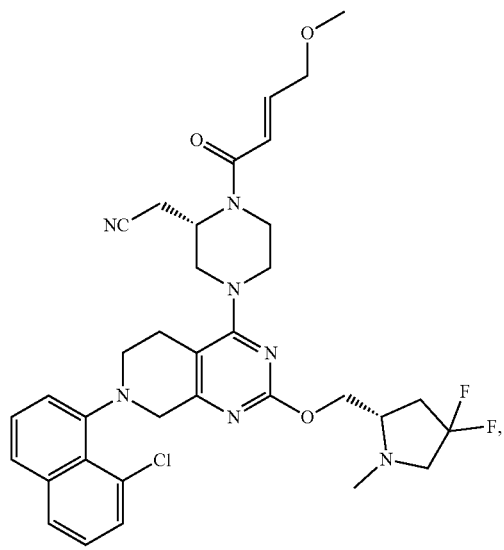
164
-continued
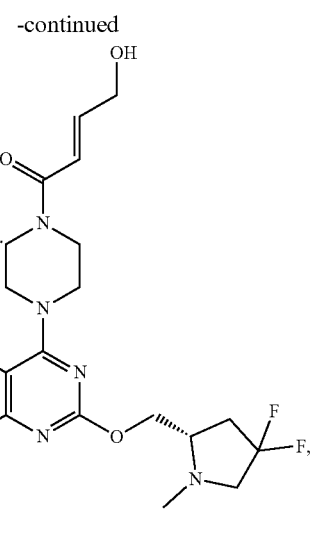
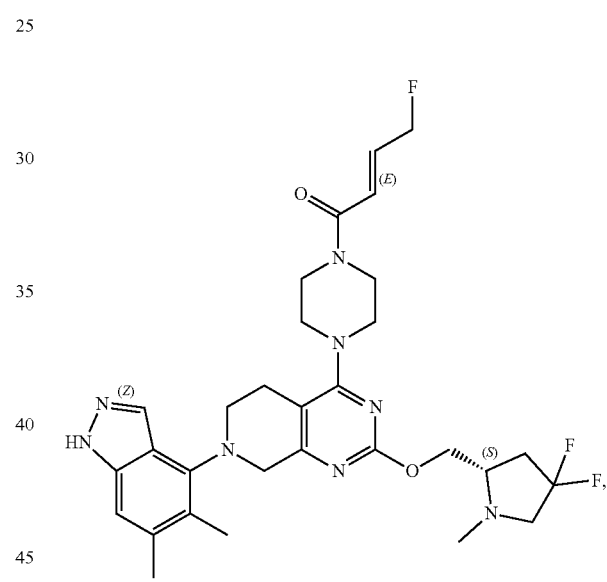
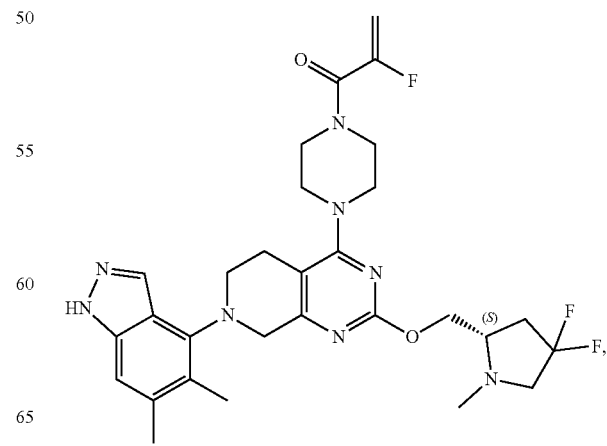

165
-continued
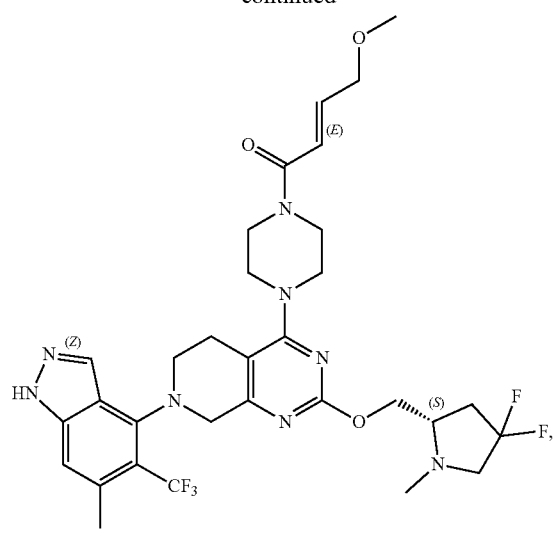
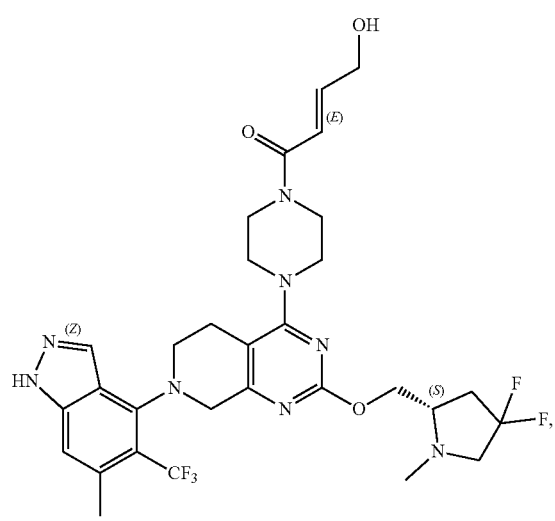
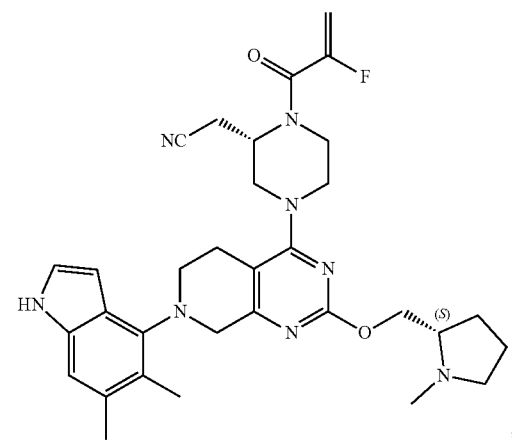
166
-continued
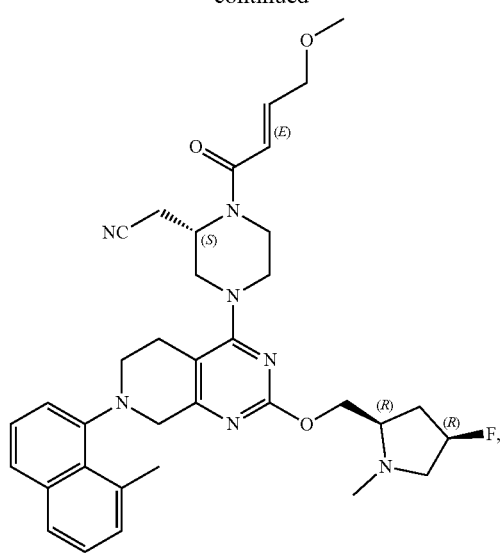
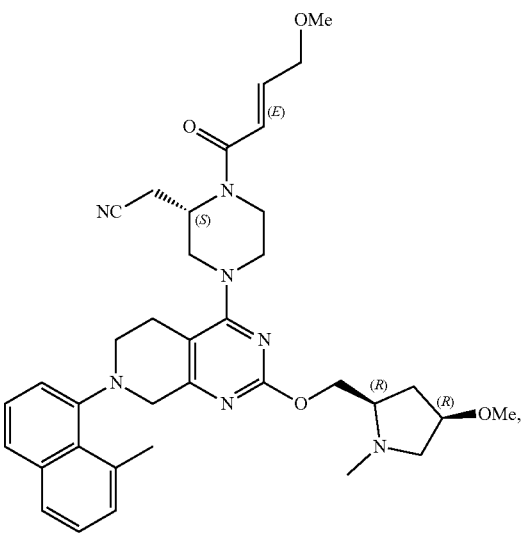
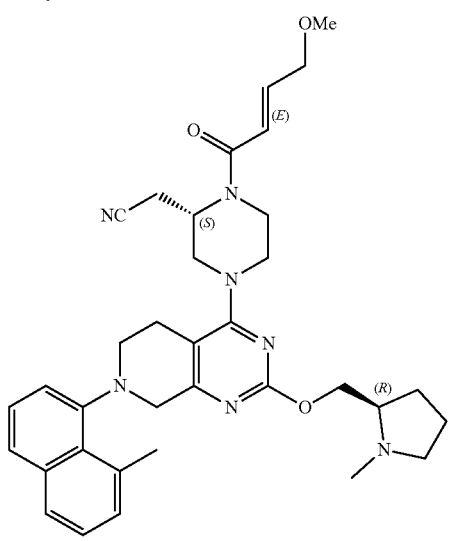

167
-continued
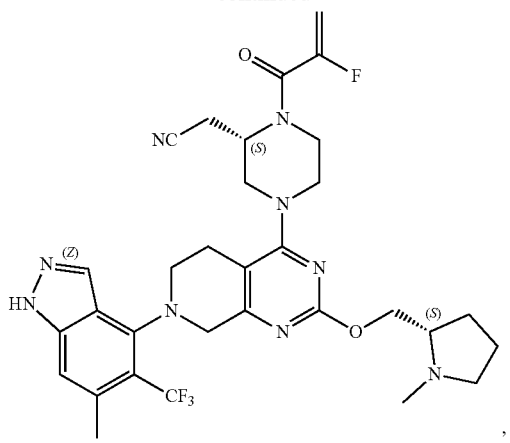
,
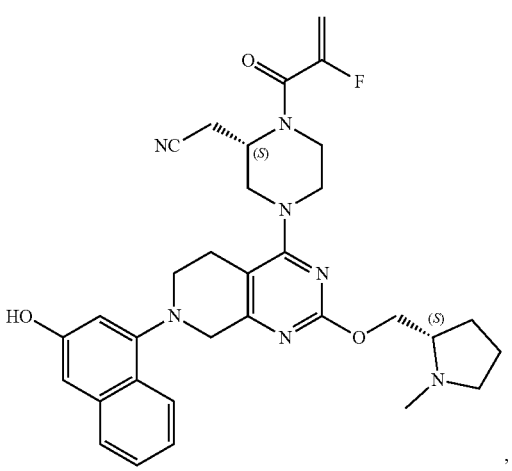
,
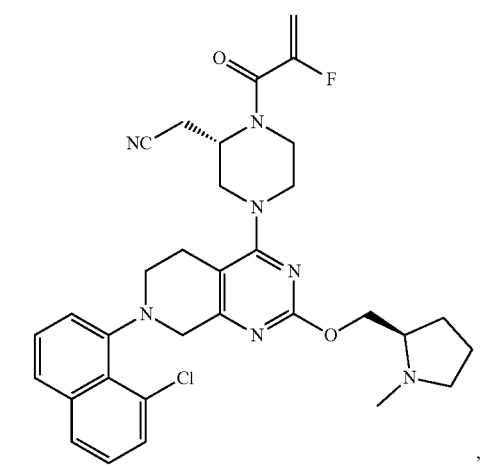
,
168
-continued
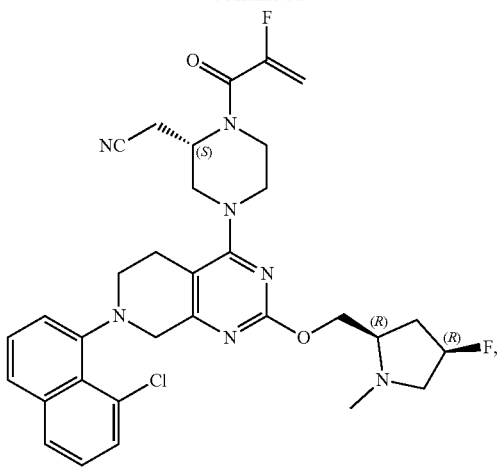
,
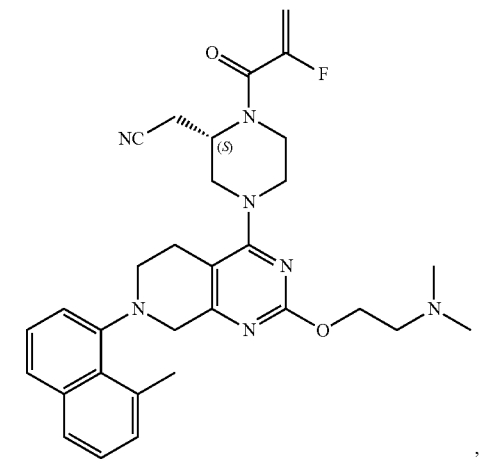
,
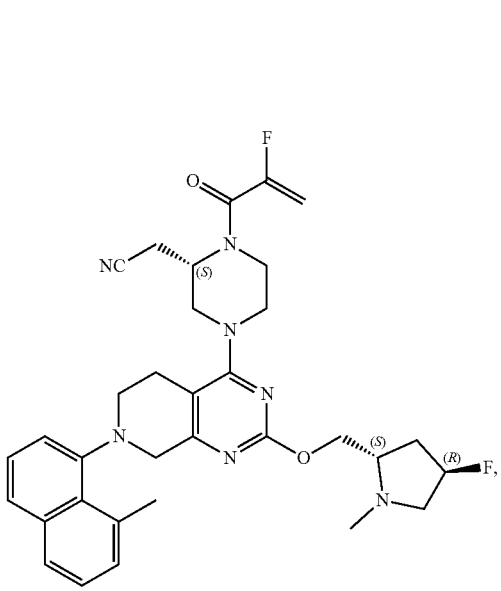

169
-continued
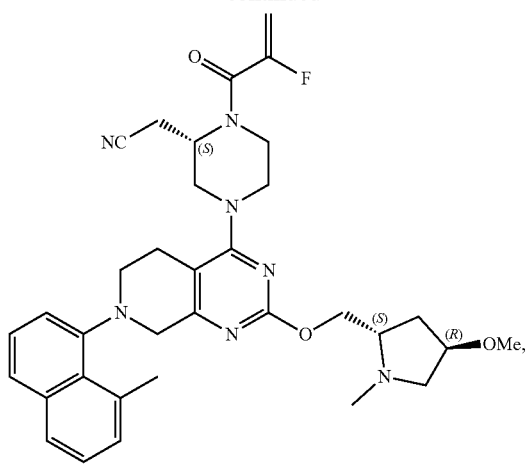
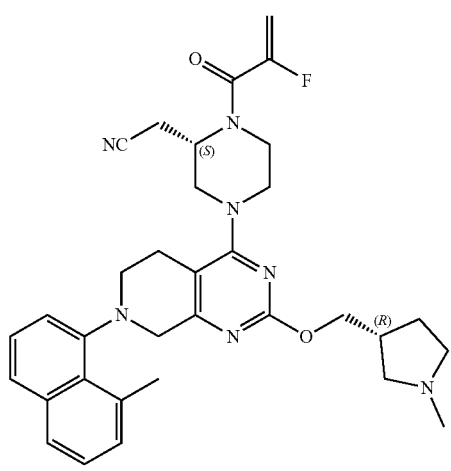
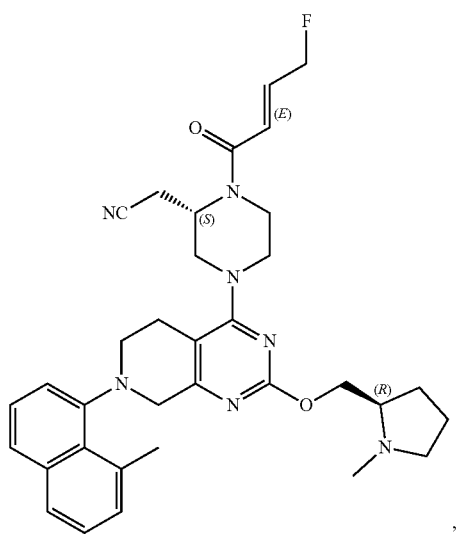
170
-continued
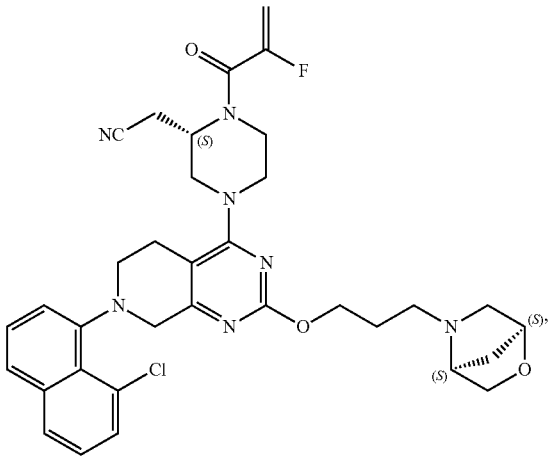
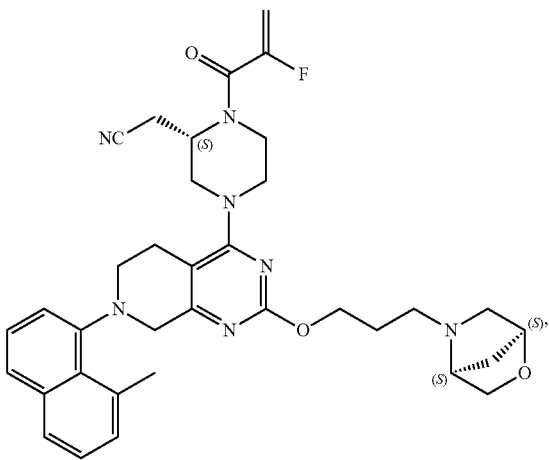

171
-continued
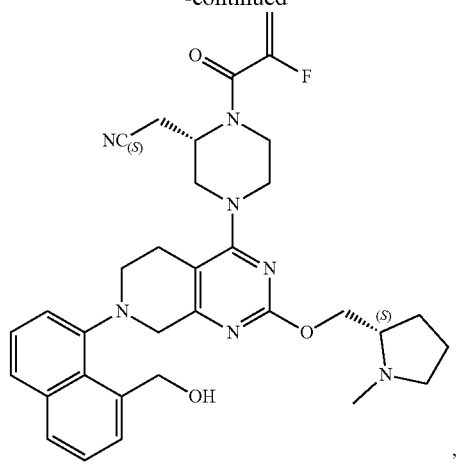
,
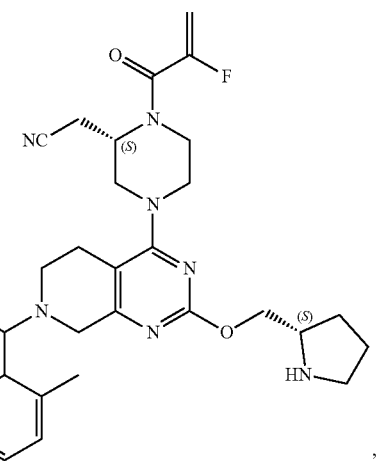
,
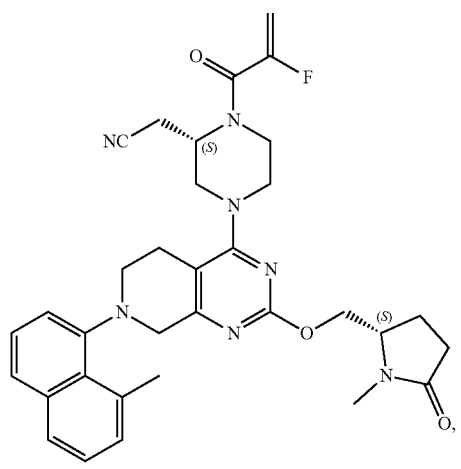
,
172
-continued
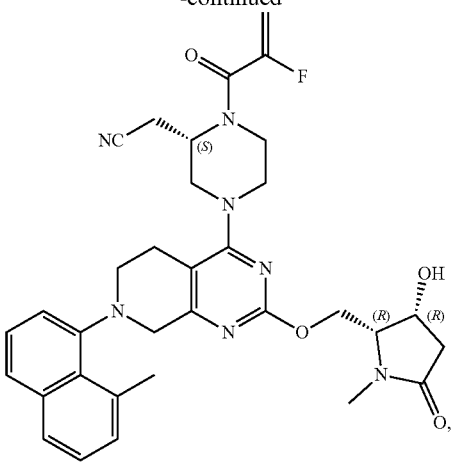
,
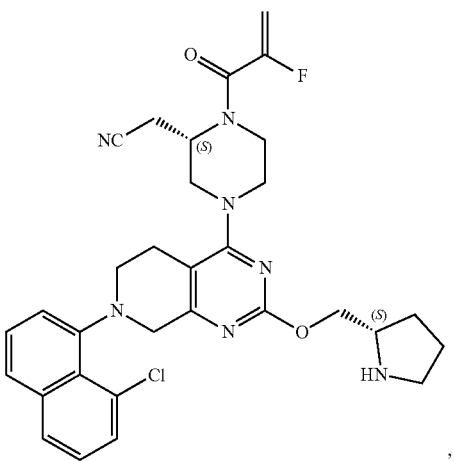
,
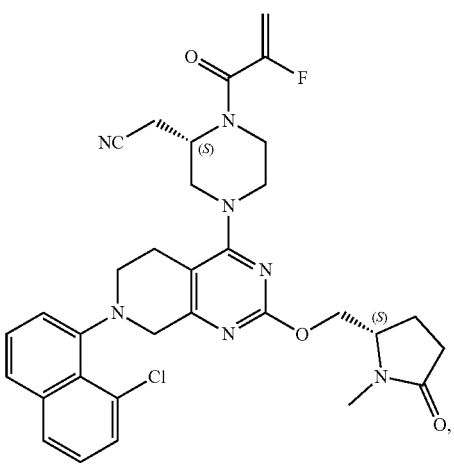
, 173
-continued
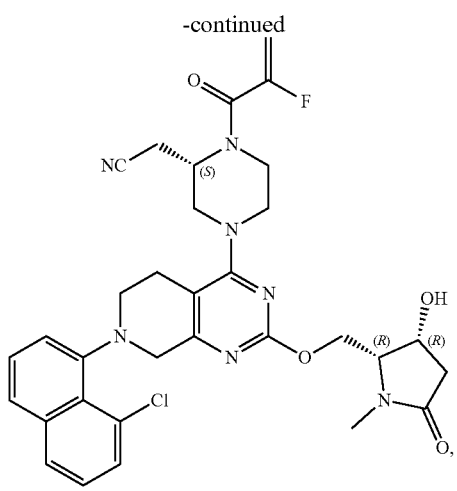
174
-continued
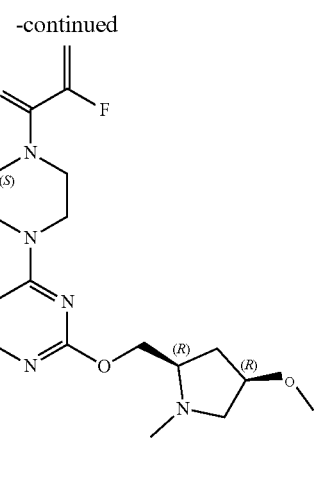
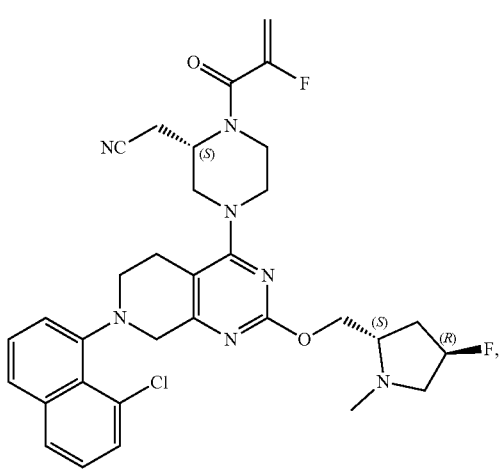
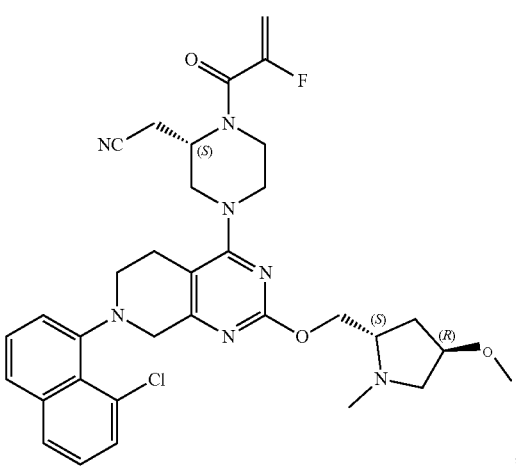
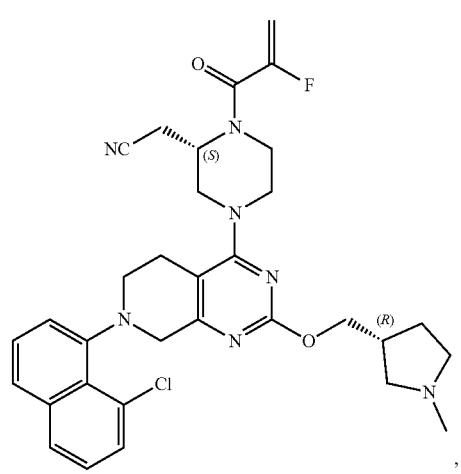
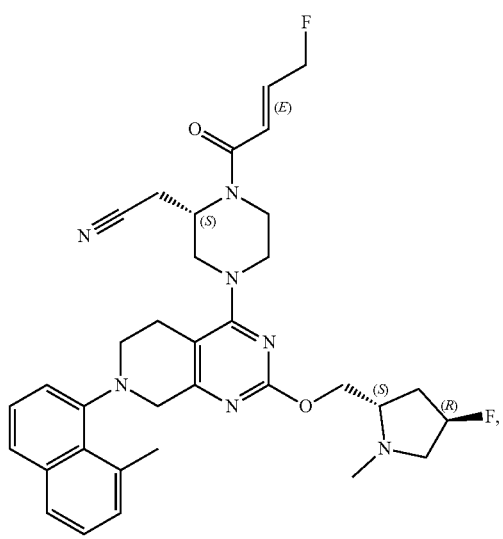

175
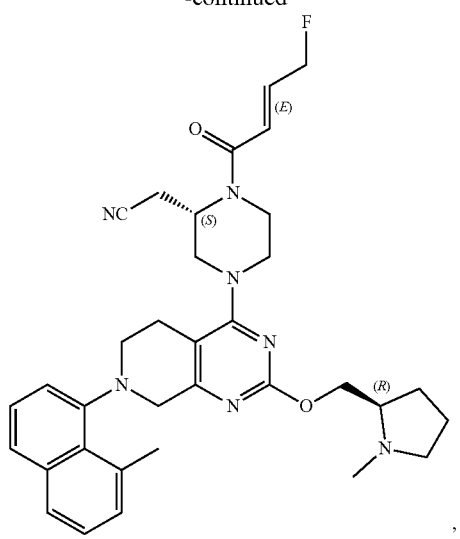
176
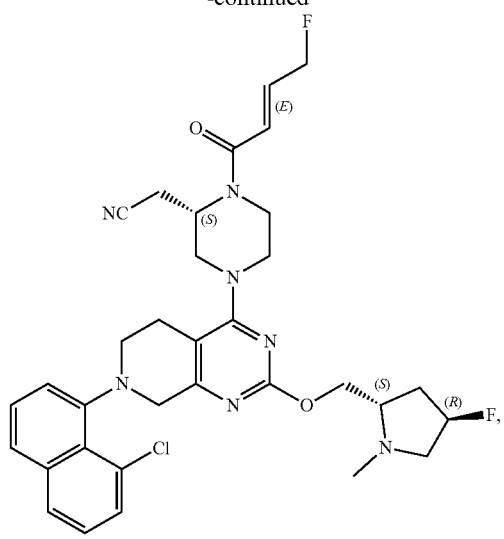

177
-continued
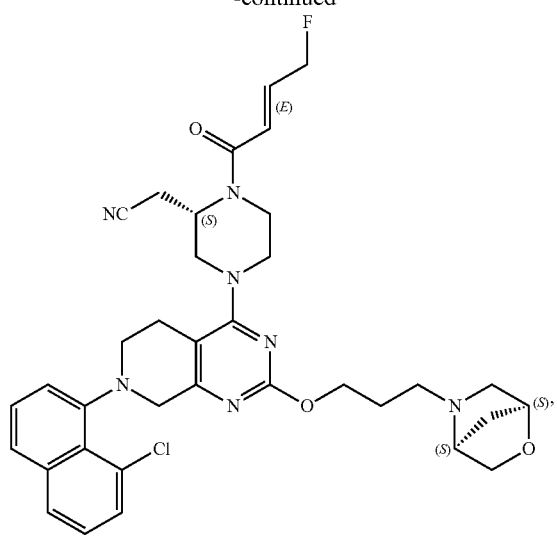
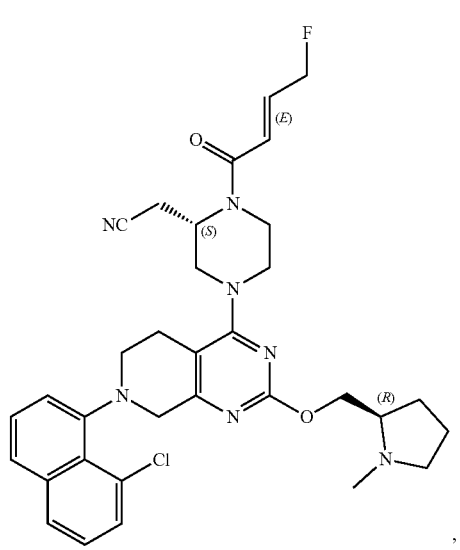
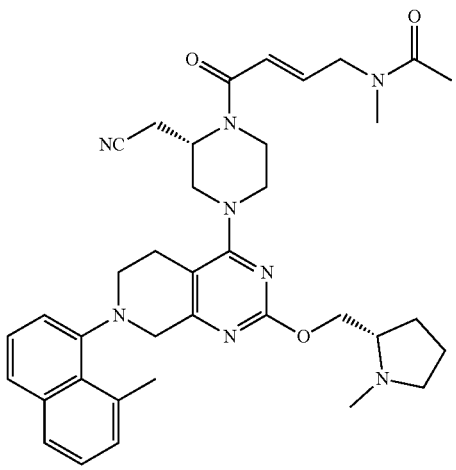
178
-continued
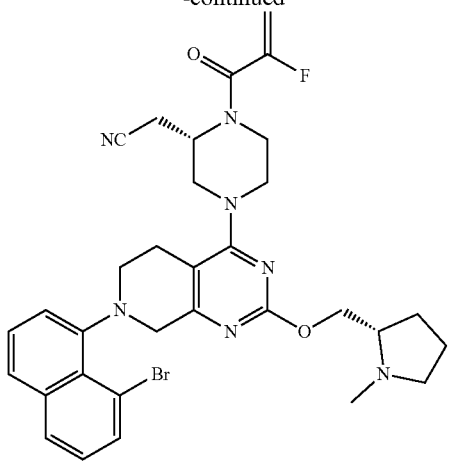
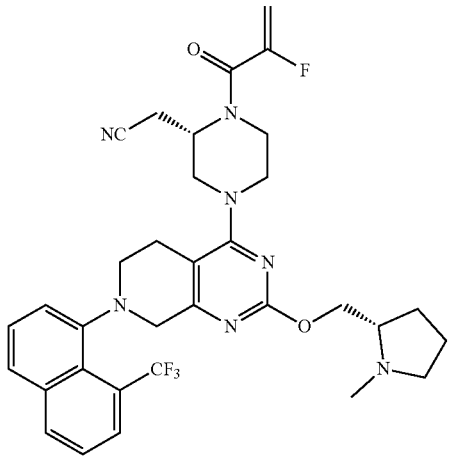
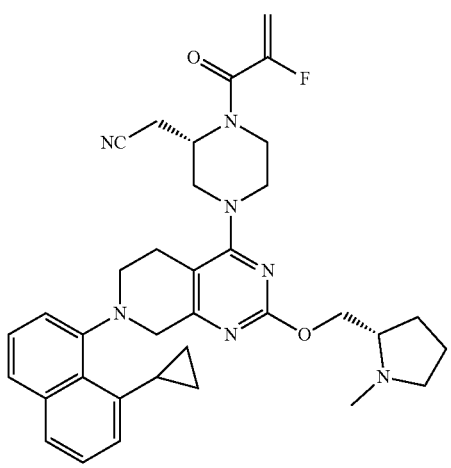

179
-continued
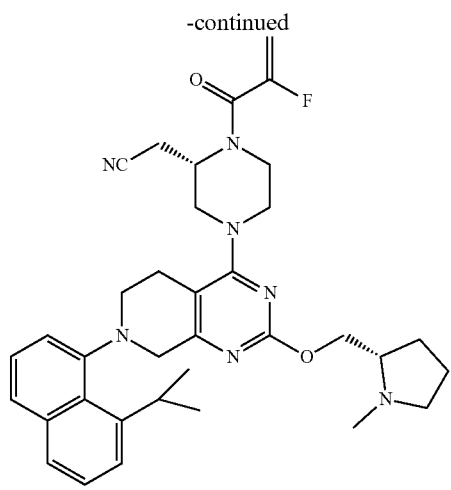
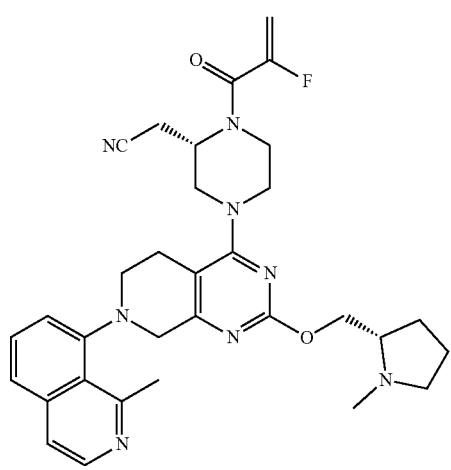
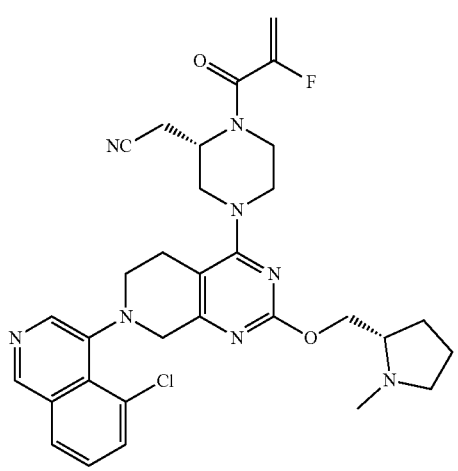
180
-continued
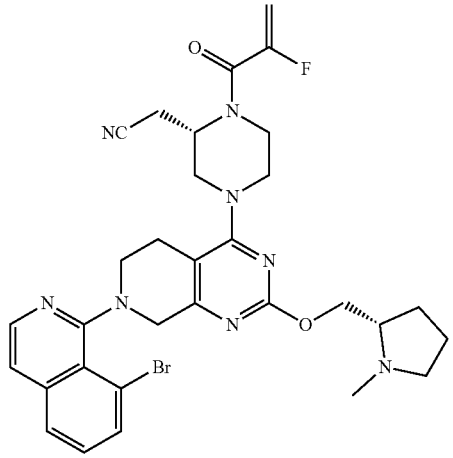
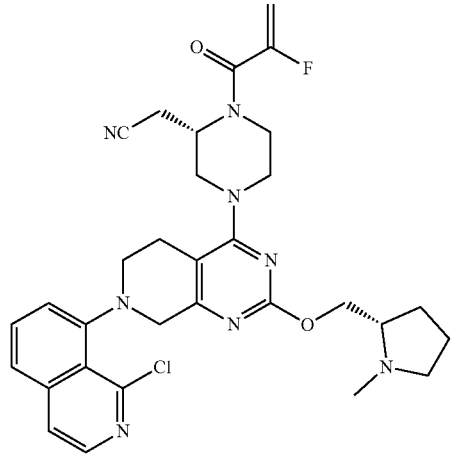
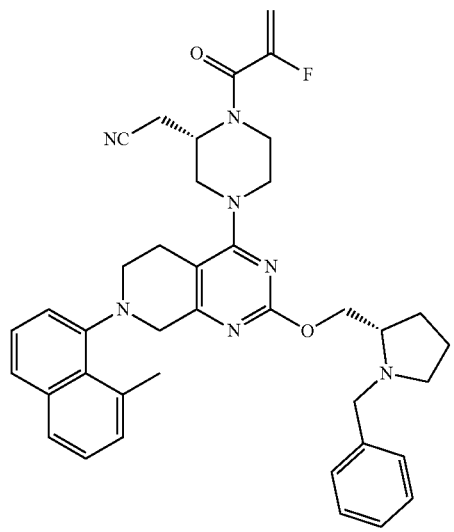

-continued
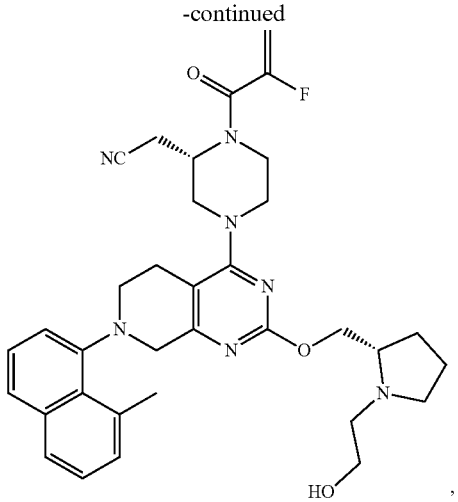
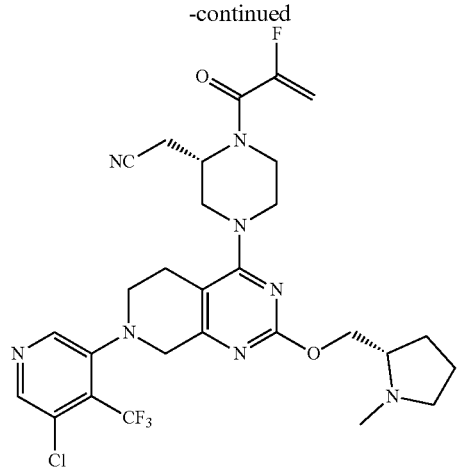
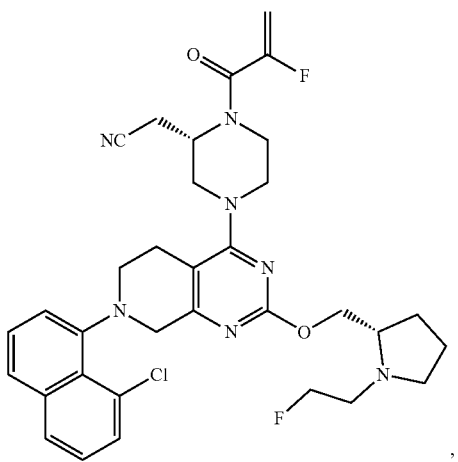
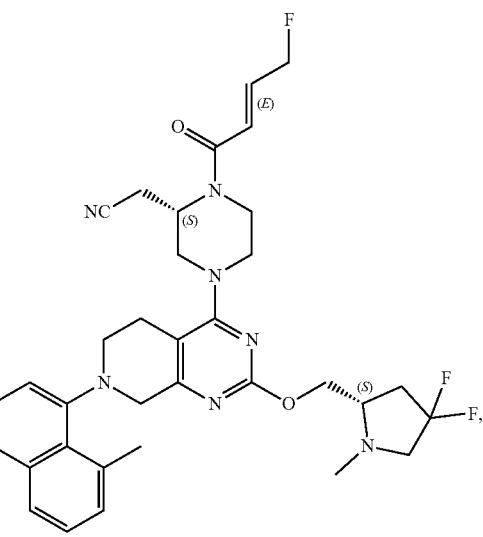

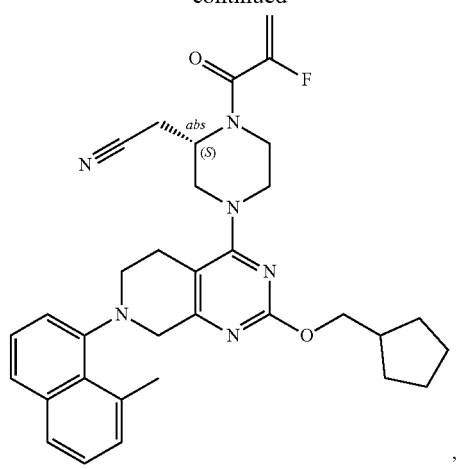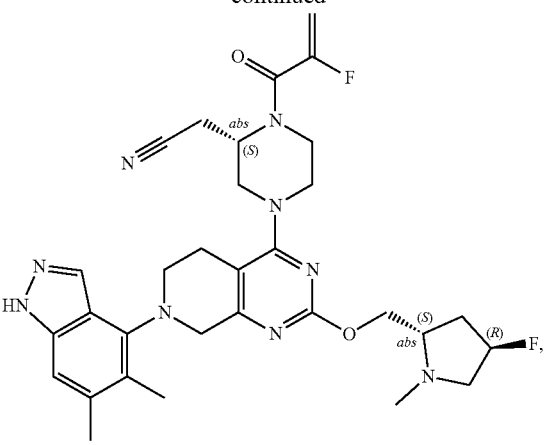

185
-continued
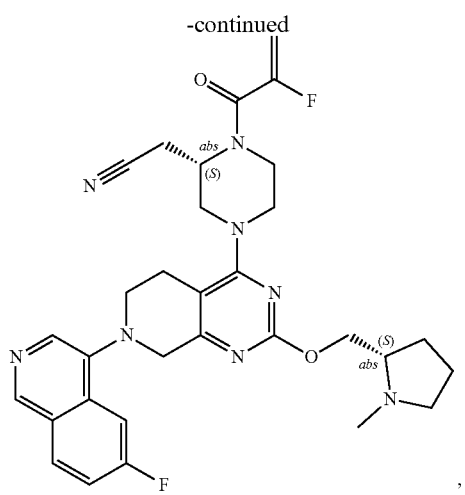
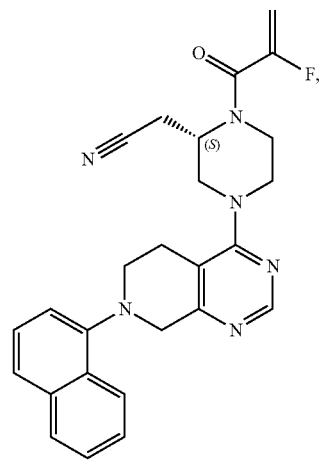
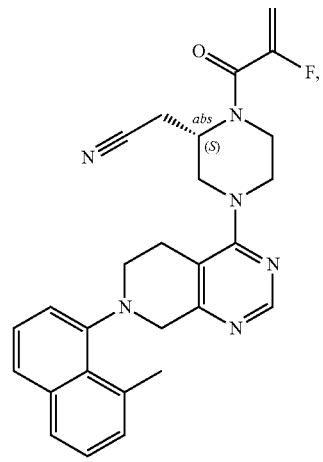
186
-continued
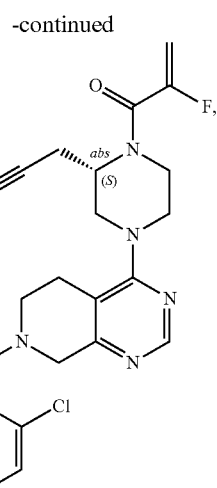
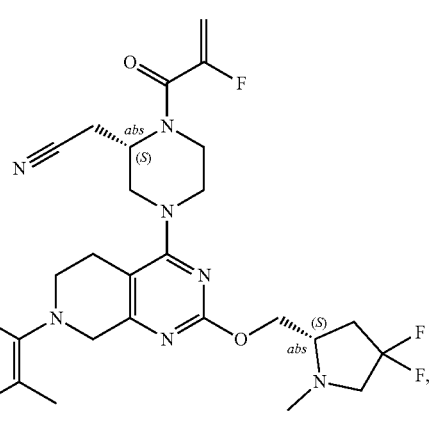
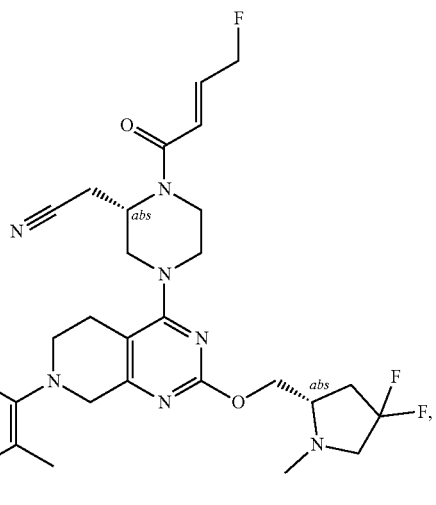

187
-continued
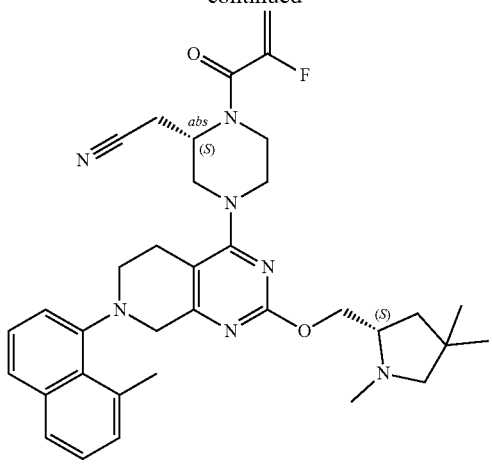
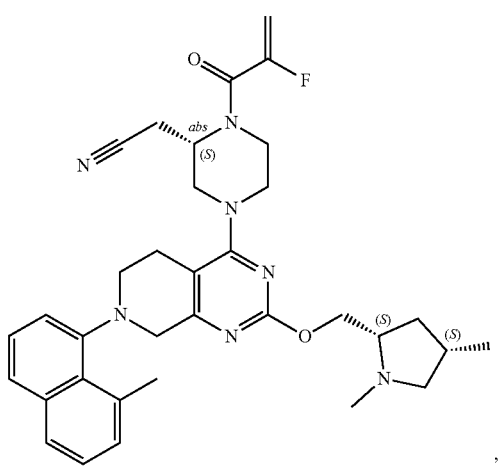
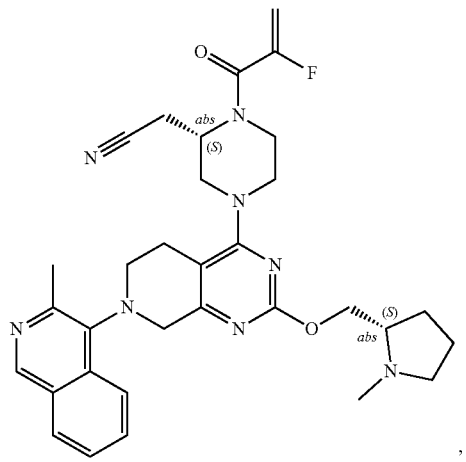
188
-continued
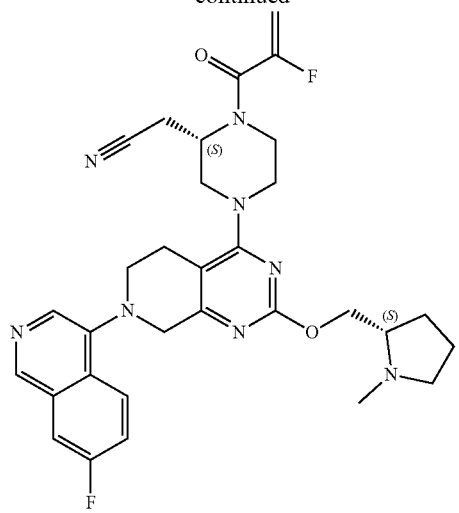
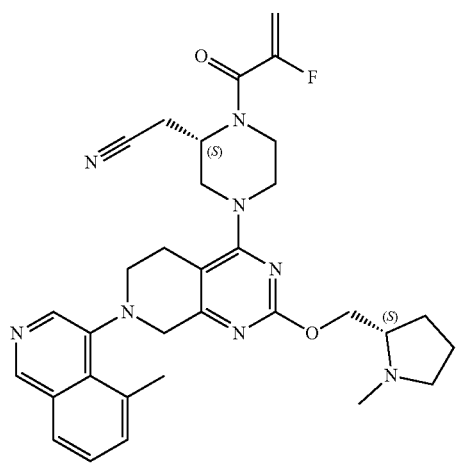
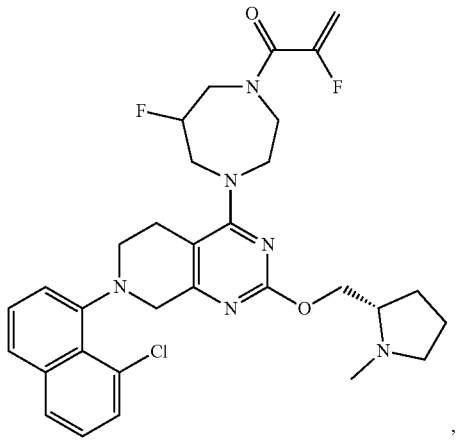

189
-continued
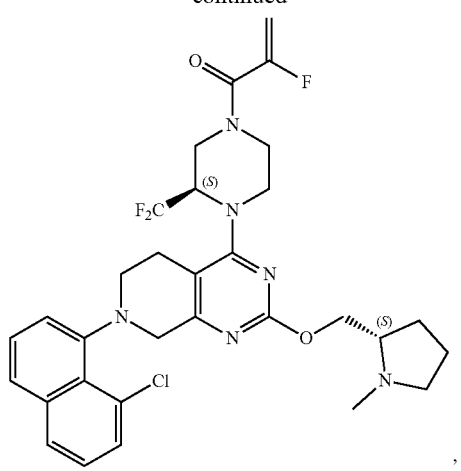
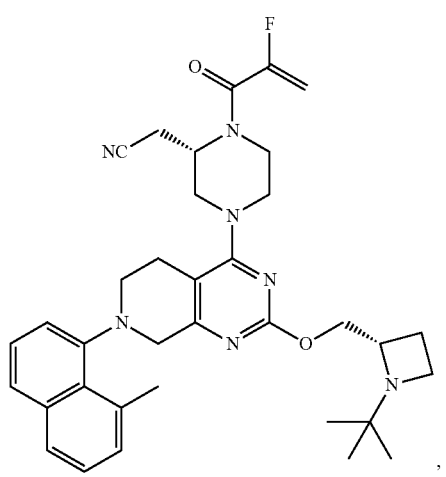
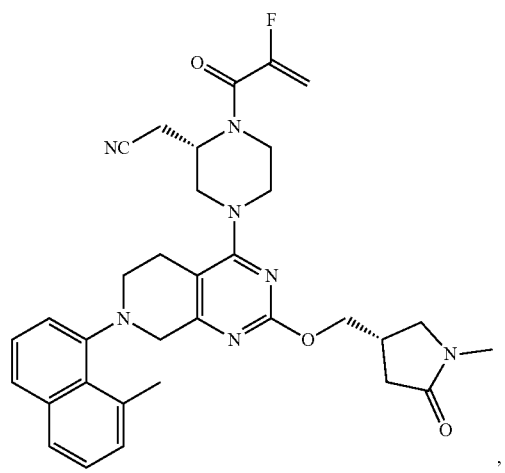
190
-continued
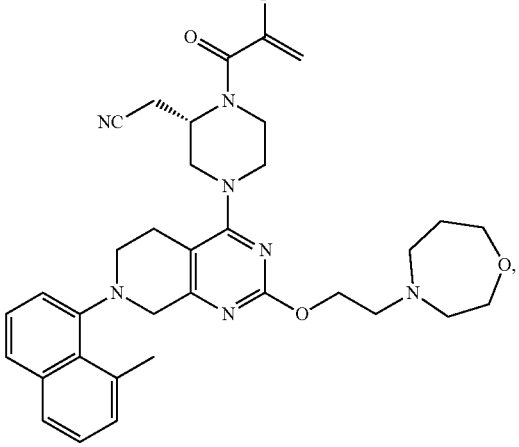
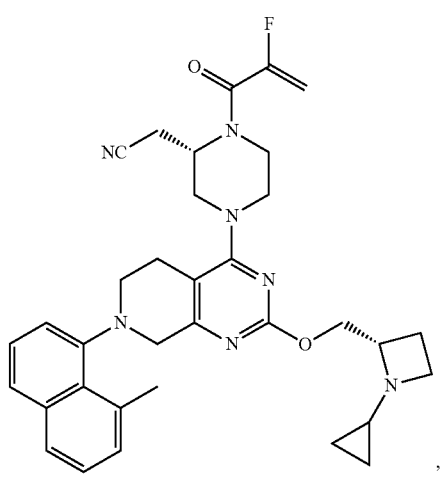

191
-continued
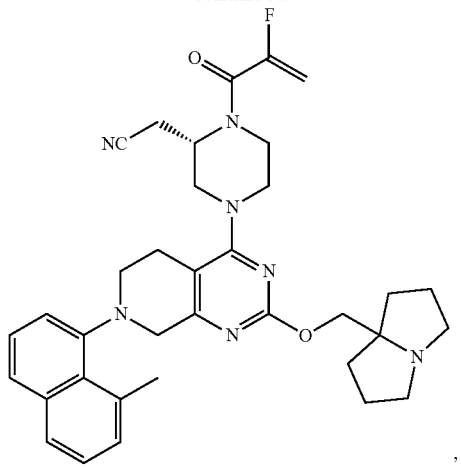
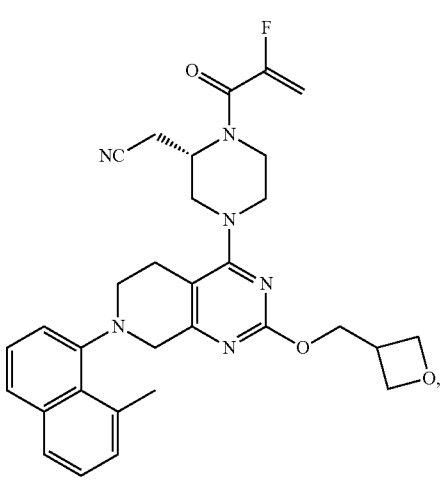
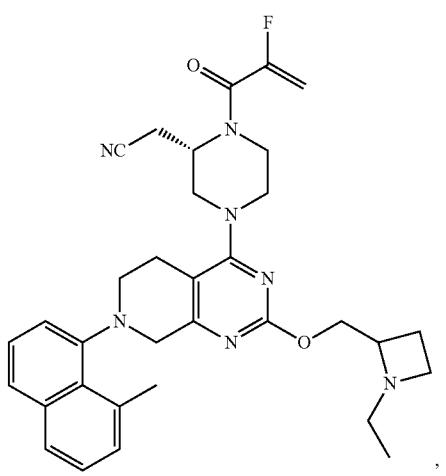
192
-continued
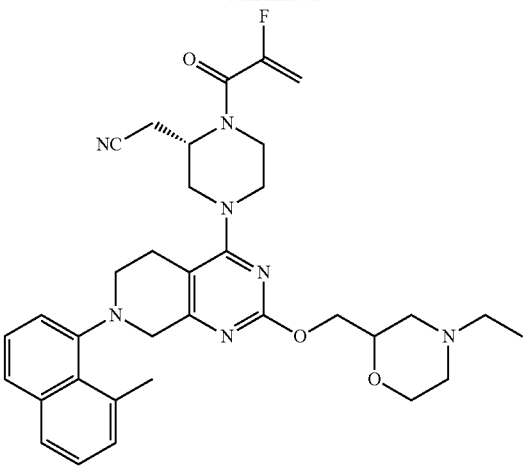

-continued

195
-continued
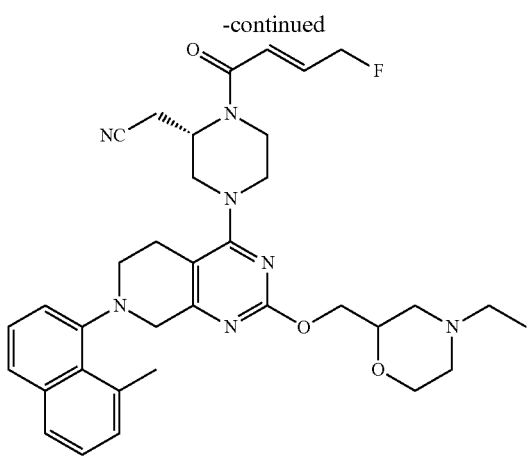
,
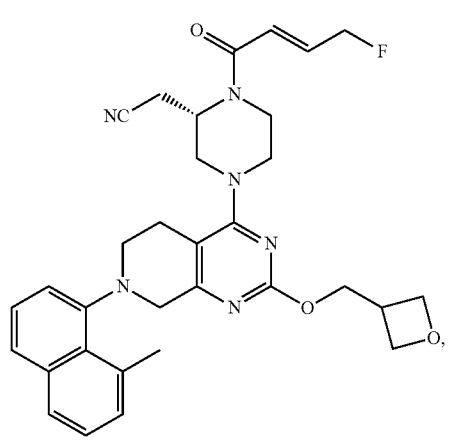
,
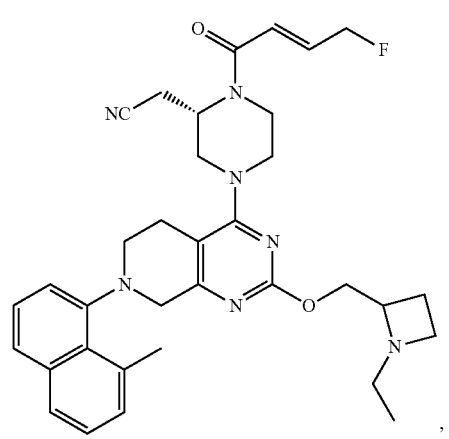
,
196
-continued
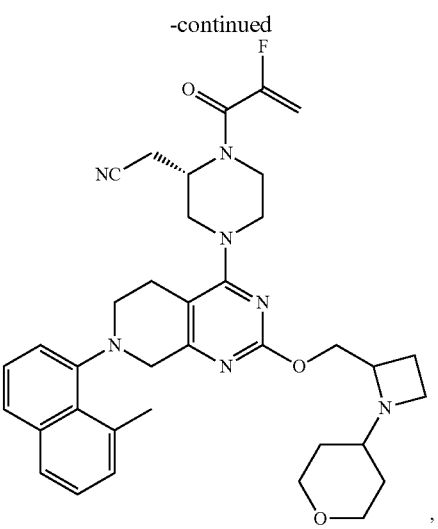
,
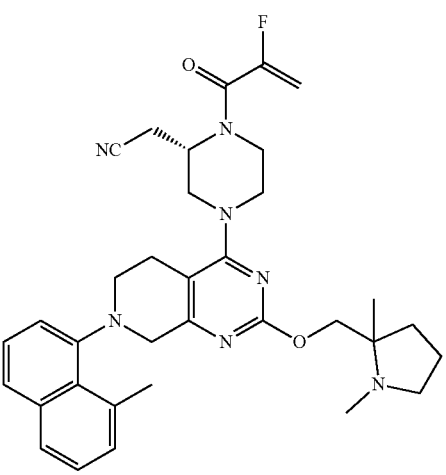
,
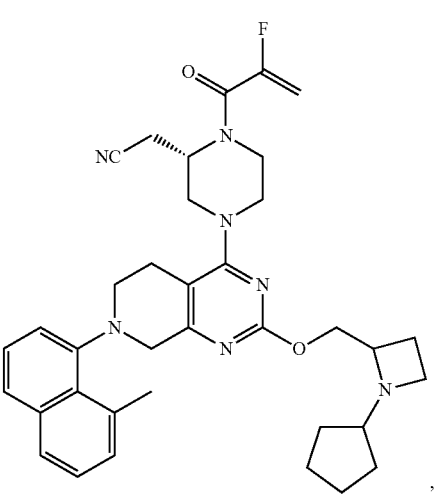
, 197                                             198
-continued                                      -continued
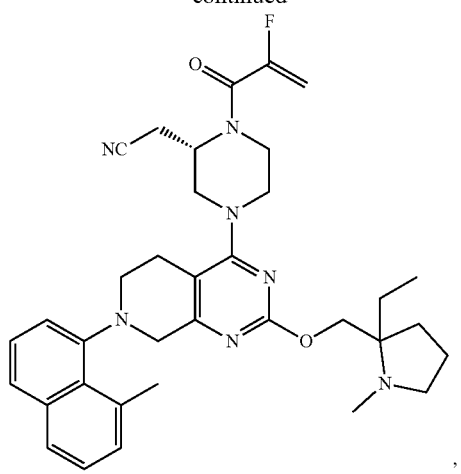,  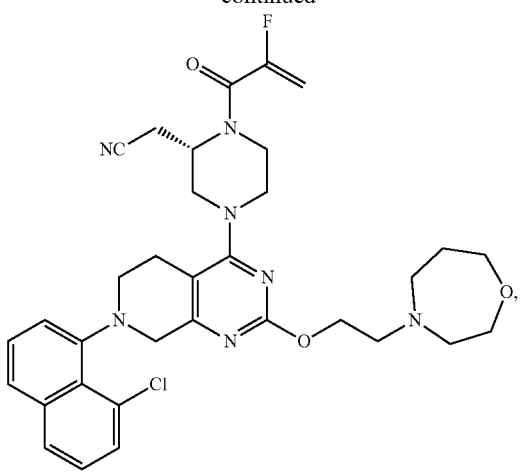,
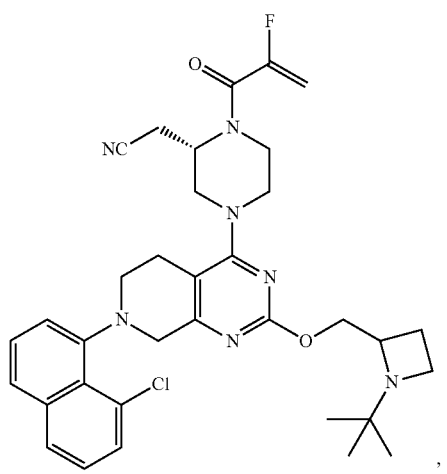,  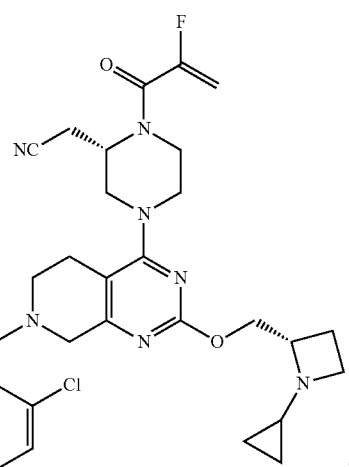,
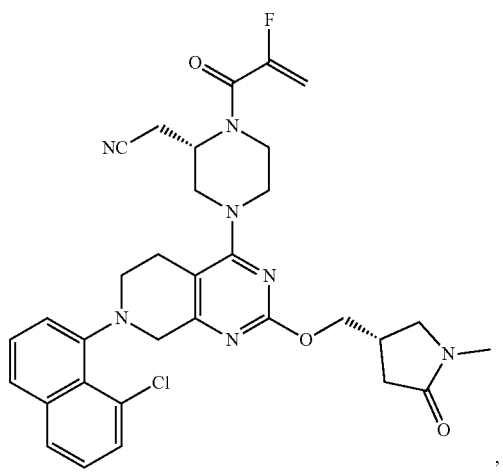,  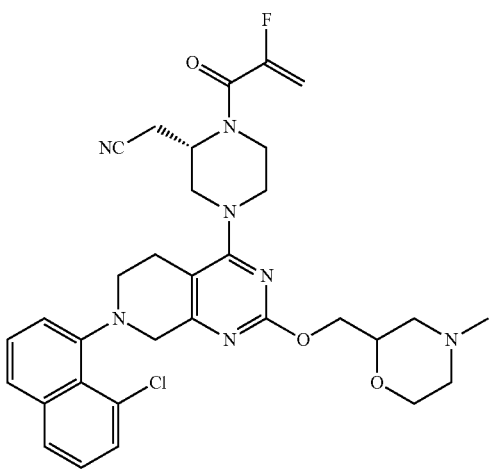,

199
-continued
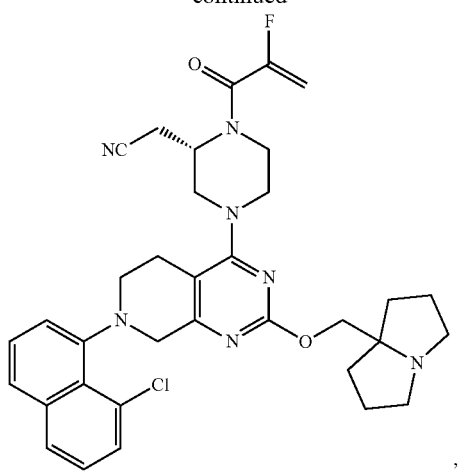
,
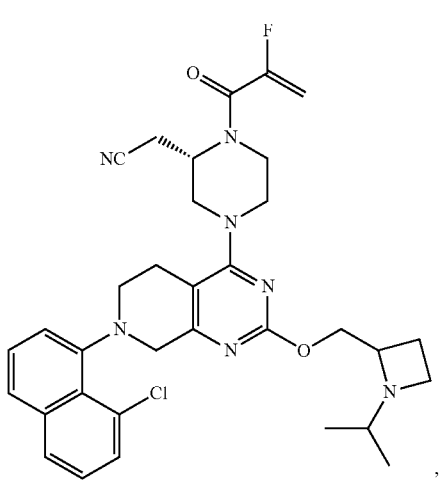
,
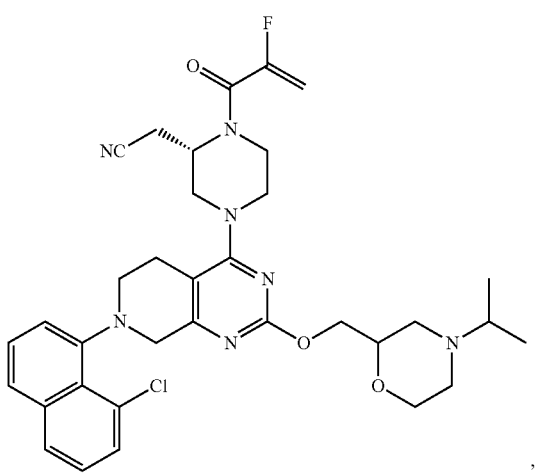
,
200
-continued
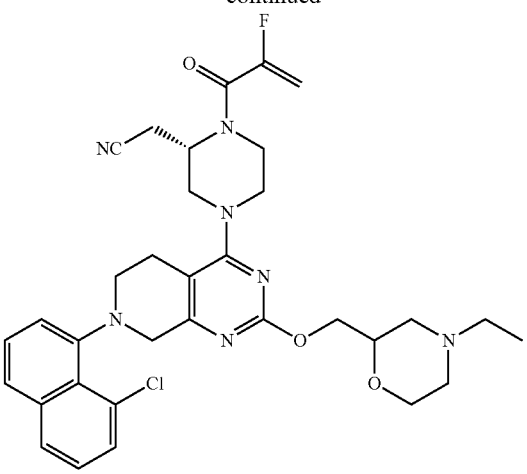
,
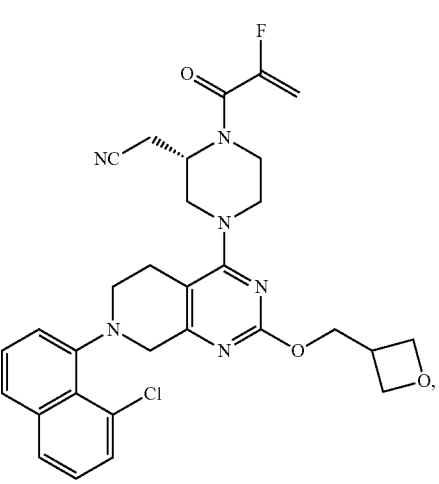
,
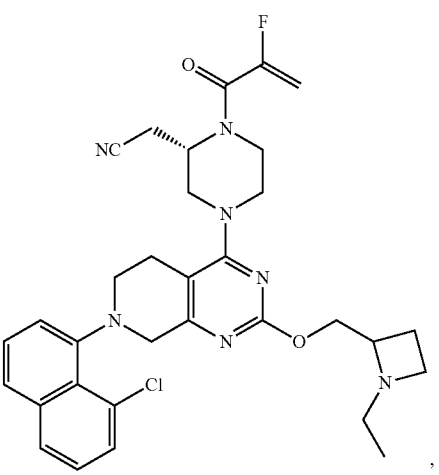
, 201 -continued 202 -continued 203
-continued 204
-continued

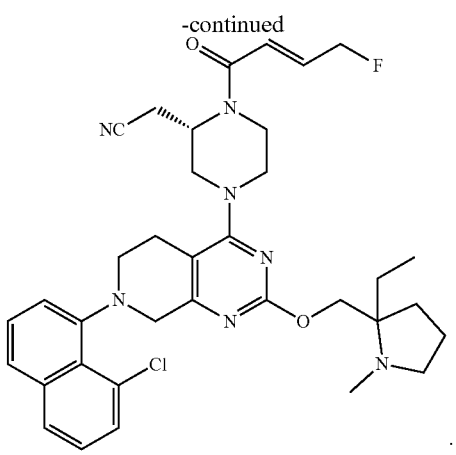

or a pharmaceutically acceptable salt thereof.

In one embodiment, the compounds of Formula I include trifluoroacetic acid salts of the above compounds. The compounds of Formula (I), Formula I-A, Formula I-B, Formula (II), Formula II-A, or Formula II-B may be formulated into pharmaceutical compositions.

Pharmaceutical Compositions

In another aspect, the invention provides pharmaceutical compositions comprising a KRas G12C inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting KRas G12C activity in a cell, comprising contacting the cell in which inhibition of KRas G12C activity is desired with an effective amount of a compound of Formula (II), Formula II-A, or Formula II-B, pharmaceutically acceptable salts thereof or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRas G12C with a compound provided herein includes the administration of a compound provided herein to an individual or patient, such as a human, having KRas G12C, as well as, for example, introducing a compound provided herein into a sample containing a cellular or purified preparation containing the KRas G12C.

In one embodiment, a cell in which inhibition of KRas G12C activity is desired is contacted with an effective amount of a compound of Formula (II), Formula II-A, or Formula II-B, to negatively modulate the activity of KRas G12C. In other embodiments, a therapeutically effective amount of pharmaceutically acceptable salt or pharmaceutical compositions containing the compound of Formula (II), Formula II-A, or Formula II-B, may be used.

By negatively modulating the activity of KRas G12C, the methods described herein are designed to inhibit undesired cellular proliferation resulting from enhanced KRas G12C activity within the cell. The cells may be contacted in a single dose or multiple doses in accordance with a particular treatment regimen to effect the desired negative modulation of KRas G12C. The degree of covalent modification of KRas G12C may be monitored in vitro using well known methods, including those described in Example A below. In addition, the inhibitory activity of exemplary compounds in cells may be monitored, for example, by measuring the inhibition of KRas G12C activity of the amount of phosphylated ERK, including those described in Example B below, to assess the effectiveness of treatment and dosages may be adjusted accordingly by the attending medical practitioner.

In another aspect, methods of treating cancer in a patient in need thereof, comprising administering to said patient a therapeutically effective amount of a compound of Formula (I), Formula II-A, or Formula II-B, pharmaceutically acceptable salts thereof or pharmaceutical compositions comprising the compound or pharmaceutically acceptable salts thereof are provided.

The compositions and methods provided herein may be used for the treatment of a KRas G12C-associated cancer in a patient in need thereof, comprising administering to said patient a therapeutically effective amount of a compound of Formula (II), Formula II-A, or Formula II-B, pharmaceutically acceptable salts thereof or pharmaceutical compositions comprising the compound or pharmaceutically acceptable salts thereof are provided. In one embodiment, the KRas G12C-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or post-operatively.

Also provided herein is a compound of Formula I, Formula I-A, Formula I-B, Formula II, Formula II-A or Formula II-B, or a pharmaceutically acceptable salt or solvate thereof, or a pharmaceutical composition thereof as defined herein for use in therapy.

Also provided herein is a compound of Formula I, Formula I-A, Formula I-B, Formula II, Formula II-A or Formula II-B, or a pharmaceutically acceptable salt or solvate thereof or a pharmaceutical composition thereof as defined herein for use in the treatment of cancer.

Also provided herein is a compound of Formula I, Formula I-A, Formula I-B, Formula II, Formula II-A or Formula II-B, or a pharmaceutically acceptable salt or solvate thereof for use in the inhibition of KRas G12C.

Also provided herein is a compound of Formula I, Formula I-A, Formula I-B, Formula II, Formula II-A or Formula II-B, or a pharmaceutically acceptable salt or solvate thereof or a pharmaceutical composition thereof as defined herein, for use in the treatment of a KRas G12C-associated disease or disorder.

Also provided herein is the use of a compound of Formula I, Formula I-A, Formula I-B, Formula II, Formula II-A or Formula II-B, or a pharmaceutically acceptable salt or solvate thereof, as defined herein in the manufacture of a medicament for the treatment of cancer.

Also provided herein is a use of a compound of Formula I, Formula I-A, Formula I-B, Formula II, Formula II-A or Formula II-B, or a pharmaceutically acceptable salt or solvate thereof, as defined herein in the manufacture of a medicament for the inhibition of activity of KRas G12C.

Also provided herein is the use of a compound of Formula I, Formula I-A, Formula I-B, Formula II, Formula II-A or Formula II-B, or a pharmaceutically acceptable salt or solvate thereof, as defined herein, in the manufacture of a medicament for the treatment of a KRas G12C-associated disease or disorder.

Also provided herein is a method for treating cancer in a patient in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a compound of Formula I, Formula I-A, Formula I-B, Formula II, Formula II-A or Formula II-B, or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

REACTION SCHEMES AND EXAMPLES

The compounds of the present invention may be prepared from commercially available reagents using the synthetic methods and reaction schemes described herein, or using other reagents and conventional methods well known to those skilled in the art.

For instance, compounds of the present invention may be prepared according to the General Reaction Schemes I and II.

General Reaction Schemes

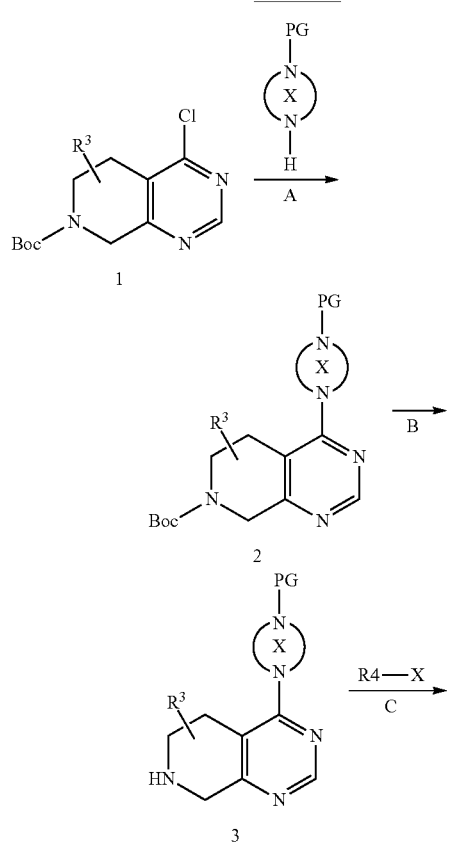

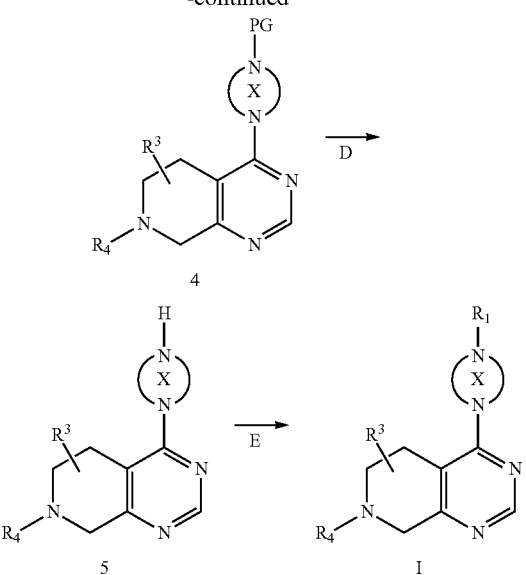

Compounds of Formula I wherein L and Y are bonds, $R^2$ is hydrogen and $R^4$ is aryl or heteroaryl can be prepared according to Scheme I. In step A, an appropriately functionalized dihydropyridopyrimidine (1) is coupled to a heterocycle containing one nucleophilic amine species, with the other bound to a protecting group to provide compound (2). This coupling proceeds in a solvent such as dichloromethane in the presence of a base such as triethylamine or Hunig's base. In step B, the Boc group of compound (2) is removed using conditions known in the art, for example with trifluoroacetic acid in a solvent such as dichloromethane, to provide compound (3). In step C, the substituent $R^4$ is introduced with a palladium coupling, using a suitable functionalized aryl or heteroaryl system, for example an aryl triflate, in the presence of a palladium catalyst such as Pd$_2$DBA$_3$/Xantphos in a solvent such as toluene with a base such as sodium tert-butoxide to provide compound (4). In step D, the protecting group of ring X compound (4) is removed, for example hydrogenolysis by Pd/C in the presence of H$_2$ in a polar solvent such as EtOH/THF to provide compound (5). In the final step, E, $R^1$ is introduced to provide a compound of Formula I, for example by treating with an acid chloride having the formula Cl—C(O)C($R^A$)═C($R^B$)$_p$ or Cl—SO$_2$C($R^A$)═C($R^B$)$_p$, or an anhydride having the formula C($R^B$)$_p$═C($R^A$)C(O)OC(O)C($R^A$)═C($R^B$)$_p$, where $R^A$, $R^B$ and p are as defined for Formula I. For example, in the case where $R^1$ is an acryloyl group, this reaction proceeds, for example, in a solvent such as methylene chloride in the presence of acryloyl chloride or an acryloyl anhydride and a base such as Hunig's base. In some cases, the species $R^4$ will also contain a protecting group, which can be removed at a subsequent step in the synthetic sequence.

Compounds (1), (2), (3), (4) and (5) as shown and described above for Scheme I are useful as intermediates for preparing compounds of Formula I and are provided as further aspects of the invention.

SCHEME II

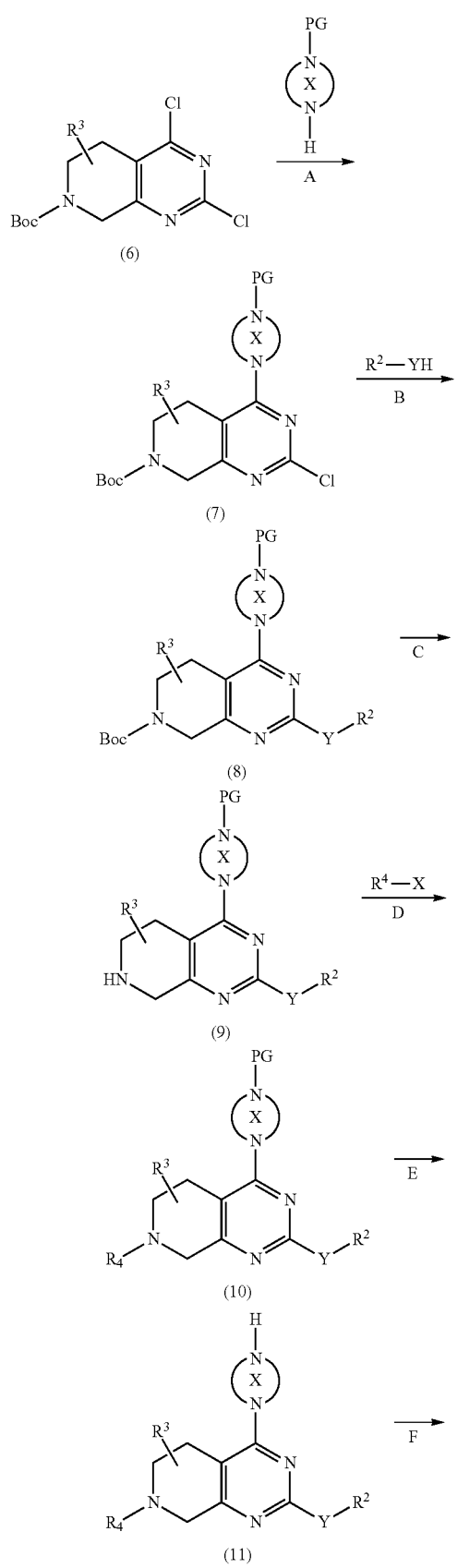

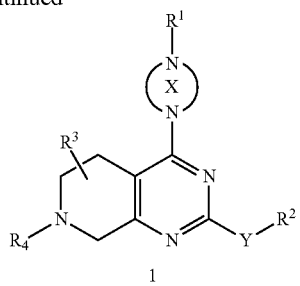

Compounds of Formula I wherein L is a bond, —Y—R² is other than hydrogen and R⁴ is aryl or heteroaryl can be prepared according to Scheme II. In step A, an appropriately functionalized dihydropyridopyrimidine (6) is coupled to a heterocycle containing one nucleophilic amine species, with the other bound to a protecting group to provide compound (7). This coupling proceeds in a solvent such as dichloromethane in the presence of a base such as triethylamine or Hunig's base. In step B, the substituent —Y—R² is introduced by substitution of the chlorine by a nucleophile, for example (S)-1-(dimethylamino-propan-2-ol in a polar solvent such as dioxane to provide compound (8). In step C, the Boc group is removed using conditions known in the art, for example with trifluoroacetic acid in a solvent such as dichloromethane to provide compound (9). In step D, the substituent R⁴ is introduced with a palladium coupling, using a suitable functionalized aryl or heteroaryl system, for example an aryl triflate, in the presence of a palladium catalyst such as Pd₂DBA₃/BINAP in a solvent such as toluene with a base such as sodium tert-butoxide to provide compound (10). In step E, the protecting group of ring X is removed, for example hydrogenolysis by Pd/C in the presence of H₂ in a polar solvent such as EtOH/THF to provide compound (11). In step F, R¹ is introduced to provide a compound of Formula I, for example by treating with an acid chloride having the formula Cl—C(O)C(R$^A$)═C(R$^B$)$_p$ or Cl—SO₂C(R$^A$)═C(R$^B$)$_p$, or an anhydride having the formula C(R$^B$)$_p$═C(R$^A$)C(O)OC(O)C(R$^A$)═C(R$^B$)$_p$, where R$^A$, R$^B$ and p are as defined for Formula I. For example, in the case where R¹ is an acryloyl group, this reaction proceeds, for example, in a solvent such as methylene chloride in the presence of acryloyl chloride acryloyl anhydride and a base such as Hunig's base. In some cases, the species R⁴ and R² may also contain protecting groups, which can be removed at a subsequent step in the synthetic sequence.

Compounds (6), (7), (8), (9), (10) and (11) as shown and described above for Scheme 2 are useful as intermediates for preparing compounds of Formula I, Formula I-A or Formula I-B and are provided as further aspects of the invention.

Accordingly, also provide is a process for preparing a compound of Formula I, comprising:

(a) for a compound of Formula I where Y is a bond and R² is hydrogen, reacting a compound of formula 5

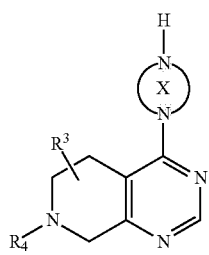

where X, R³ and R⁴ are as defined for Formula I, with an acid chloride having the formula Cl—C(O)C(R$^A$)═C(R$^B$)$_p$ or Cl—SO$_2$C(R$^A$)═C(R$^B$)$_p$ or an anhydride having the formula C(R$^B$)$_p$═C(R$^A$)C(O)OC(O)C(R$^A$)═C(R$^B$)$_p$, where R$^A$, R$^B$ and p are as defined for Formula I, in the presence of a base; or (b) for a compound of Formula I wherein L is a bond and —Y—R² is other than hydrogen, reacting a compound of formula (11)

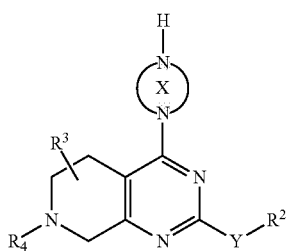
(11)

wherein L is a bond, —Y—R² is other than hydrogen, and X, R³ and R⁴ are as defined for Formula I, with an acid chloride having the formula Cl—C(O)C(R$^A$)═C(R$^B$)$_p$ or Cl—SO$_2$C(R$^A$)═C(R$^B$)$_p$, or an anhydride having the formula C(R$^B$)$_p$═C(R$^A$)C(O)OC(O)C(R$^A$)═C(R$^B$)$_p$, where R$^A$, R$^B$ and p are as defined for Formula I, in the presence of a base; and optionally forming a salt thereof.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The following Examples are intended to illustrate further certain embodiments of the invention and are not intended to limit the scope of the invention.

Intermediate 1

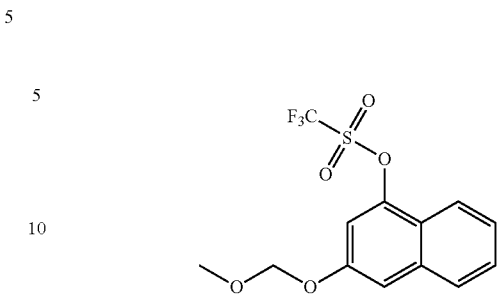

3-(methoxymethoxy)naphthalen-1-yl trifluoromethanesulfonate

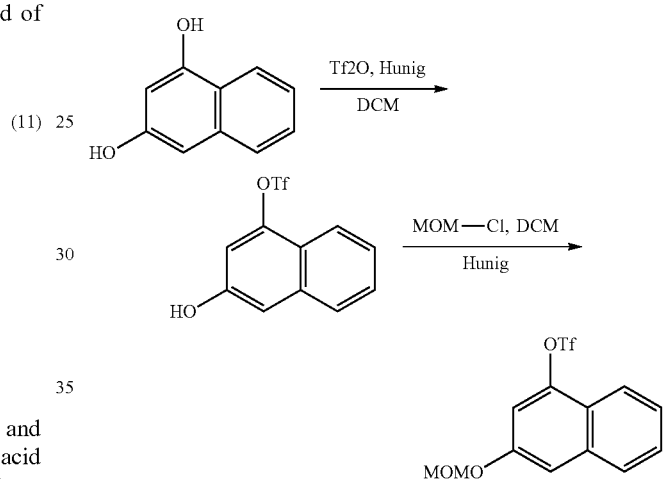

3-Hydroxynaphthalen-1-yl trifluoromethanesulfonate (13.101 g, 44.831 mmol) was dissolved in dichloromethane (100 mL) and stirred at 0° C. To this solution was added chloro(methoxy)methane (3.7456 ml, 49.315 mmol) and Hunig's base (11.745 mL, 67.247 mmol). The reaction was stirred at 0° C. for 4 hrs. The reaction was partitioned with 1M HCl and washed with saturated sodium bicarbonate. The combined organic layers were dried over magnesium sulfate and concentrated under vacuum. The concentrated material was loaded onto a 120 g RediSep® gold silica gel column with dichloromethane and purified by normal phase chromatography (CombiFlash®, 0%-20% ethyl acetate/hexanes as the eluent) to give 3-(methoxymethoxy)naphthalen-1-yl trifluoromethanesulfonate (11.785 g, 35.045 mmol, 78.171% yield).

Intermediate 2

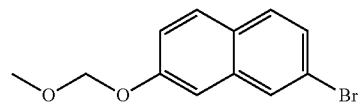

215

2-bromo-7-(methoxymethoxy)naphthalene

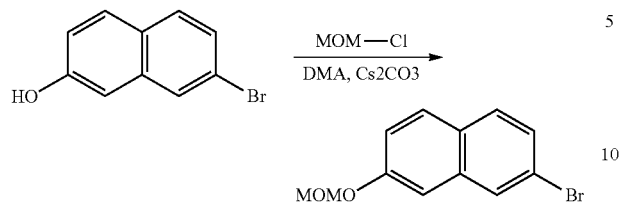

To a solution of 7-bromonaphthalen-2-ol (2.0 g, 9.0 mmol) in dimethyl acetamide (40 mL) was added chloro(methoxy)methane (1.4 g, 18 mmol) and cesium carbonate (5.8 g, 18 mmol) and the reaction mixture was stirred overnight at room temperature. The reaction was diluted with water and the aqueous layer washed with ethyl acetate. The combined organic layers were washed with water and brine, dried over magnesium sulfate and concentrated under vacuum. The crude material was purified by normal phase chromatography using 5-50% ethyl acetate/hexanes as the eluent to give 2-bromo-7-(methoxymethoxy)naphthalene (1.0 g, 3.7 mmol, 42% yield).

Intermediate 3

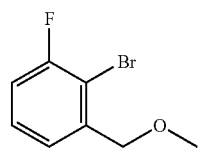

2-bromo-1-fluoro-3-(methoxymethyl)benzene

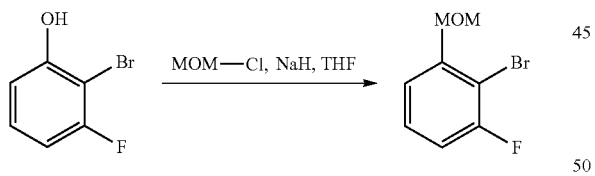

To a stirred solution of 2-bromo-3-fluorophenol (1422 mg, 7.445 mmol) in 22 mL tetrahydrofuran at room temperature under nitrogen was added NaH (327.6 mg, 8.190 mmol) neat as a solid portion wise. After 15 minutes, a solution had formed. Chloro(methoxy)methane (678.6 µL, 8.934 mmol) was added by syringe. After stirring for 2 hours, the reaction was quenched with saturated ammonium chloride solution and then partitioned between ethyl acetate (30 mL) and water (30 mL). The combined organic layers were isolated, washed with brine, dried over MgSO$_4$, filtered and concentrated. The crude product was loaded in a minimum of dichloromethane onto a 40 gram RediSep® column pre-wet with hexanes and eluted with an ethyl acetate/hexanes gradient (0% to 20% ethyl acetate). Fractions containing the product were combined and concentrated to provide the product as a clear oil (1.45 g, 83%).

216

Intermediate 4

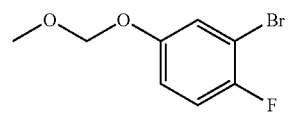

2-bromo-1-fluoro-4-(methoxymethoxy)benzene

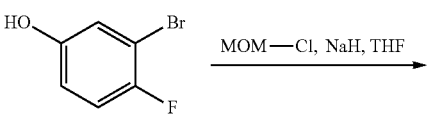

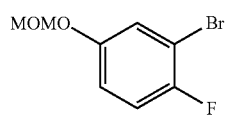

To a stirred solution of 3-bromo-4-fluorophenol (327 mg, 1.71 mmol) in 5.1 mL tetrahydrofuran at room temperature under nitrogen was added NaH (75.3 mg, 1.88 mmol) neat as a solid portion wise. After 15 minutes, a solution had formed. Chloro(methoxy)methane (156 µL, 2.05 mmol) was added by syringe. After stirring for 2 hours, the reaction was quenched with saturated ammonium chloride solution and partitioned between ethyl acetate and water. The combined organic layers were washed with brine, dried over MgSO$_4$, filtered and concentrated. The crude product was loaded in a minimum of dichloromethane onto a 24 gram RediSep® column pre-wet with hexanes and eluted with an ethyl acetate/hexanes gradient (0% to 20% ethyl acetate). Fractions containing the product were combined and concentrated to provide the product as a clear oil (120 mg, 29.8%)

Intermediate 5

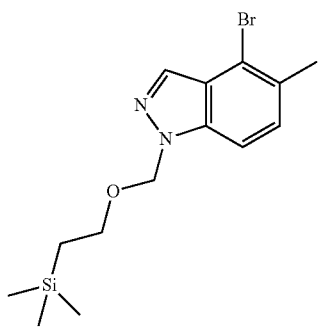

4-bromo-5-methyl-1-((2-(trimethylsilyl)ethoxy)methyl)-1H-indazole

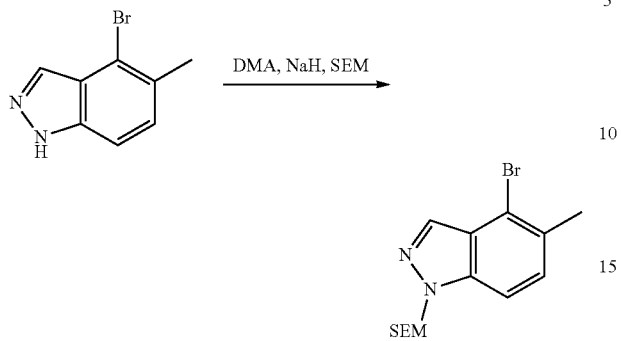

To a solution of 4-bromo-5-methyl-1H-indazole (0.7 g, 3.3 mmol) in dimethyl acetamide (30 mL) cooled to 0° C. was added NaH (0.19 g, 4.6 mmol) in portions and the reaction mixture was purged with nitrogen. The reaction was stirred for 20 minutes, and then (2-(chloromethoxy)ethyl)trimethylsilane (0.83 g, 5.0 mmol) was added and the reaction was stirred for 2 hours while warming to room temperature. The reaction was quenched by pouring into water and the aqueous layer was extracted into ethyl acetate. The combined organic layers were washed with water and brine, dried over MgSO$_4$ and concentrated under vacuum. The crude material was purified by chromatography using 10-50% ethyl acetate/hexanes as the eluent to give 4-bromo-5-methyl-1-((2-(trimethylsilyl)ethoxy)methyl)-1H-indazole (0.87 g, 79%).

Intermediate 6

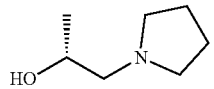

(R)-1-(pyrrolidin-1-yl)propan-2-ol

In a sealed tube, R-(+)-Propylene oxide (3.69 mL, 52.7 mmol) was cooled to −78° C. and then sparged with anhydrous dimethyl amine for a few minutes. The reaction mixture was heated to 70° C. for 16 hours. The reaction was cooled and concentrated in vacuo for 20 minutes to provide (R)-1-(pyrrolidin-1-yl)propan-2-ol (5.35 g, 41.4 mmol, 98.2% yield).

Intermediate 7

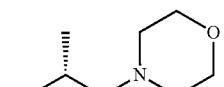

(R)-1-morpholinopropan-2-ol

In a sealed tube, R-(+)-Propylene oxide (2.111 mL, 30.13 mmol) and morpholine (1.490 mL, 17.22 mmol) were heated to 70° C. for 20 hours. The reaction was cooled and concentrated in vacuo to provide (R)-1-morpholinopropan-2-ol (2.47 g, 17.01 mmol, 98.80% yield).

Intermediate 8

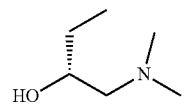

(R)-1-(dimethylamino)butan-2-ol

In a sealed tube, R-(+)-Propylene oxide (4.00 g, 55.5 mmol) and dimethylamine (1.00 g, 22.2 mmol), were heated to 65° C. for 18 hours. The reaction was cooled and concentrated in vacuo. The resulting residue was purified by silica gel (0-12% MeOH in DCM) to provide (R)-1-(dimethylamino)butan-2-ol (1.38 g, 11.8 mmol, 53.1% yield).

Intermediate 9

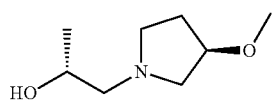

(R)-1-((R)-3-methoxypyrrolidin-1-yl)propan-2-ol

In a sealed tube, (R)-3-methoxypyrrolidine hydrochloride (1.00 g, 7.27 mmol), TEA (2.03 mL, 14.5 mmol) and R-(+)-Propylene oxide (1.27 mL, 18.2 mmol) were heated to 65° C. for 18 hours. The reaction was cooled and concentrated in vacuo. The resulting residue was purified by silica gel (0-12% MeOH in DCM) to provide (R)-1-((R)-3-methoxypyrrolidin-1-yl)propan-2-ol (775 mg, 4.87 mmol, 67.0% yield).

Intermediate 10

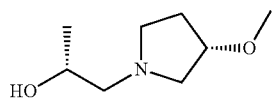

(R)-1-((S)-3-methoxypyrrolidin-1-yl)propan-2-ol

In a sealed tube, (S)-3-methoxypyrrolidine hydrochloride (1.00 g, 7.27 mmol), TEA (2.03 mL, 14.5 mmol) and R-(+)-Propylene oxide (1.27 mL, 18.2 mmol) were heated to 65° C. for 18 hours. The reaction was cooled and concentrated in vacuo. The resulting residue was purified by silica gel (0-12% MeOH in DCM) to provide (R)-1-((S)-3-methoxypyrrolidin-1-yl)propan-2-ol (781 mg, 4.90 mmol, 67.5% yield)

Intermediate 11

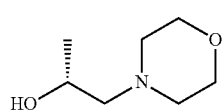

(R)-1-((S)-3-((tert-butyldimethylsilyl)oxy)pyrrolidin-1-yl)propan-2-ol

In a sealed tube, R-(+)-Propylene oxide (0.609 mL, 8.69 mmol) and (S)-3-((tert-butyldimethylsilyl)oxy)pyrrolidine (1.00 g, 4.97 mmol) were heated to 70° C. for 20 hours. The reaction was cooled and concentrated in vacuo to provide (R)-1-((S)-3-((tert-butyldimethylsilyl)oxy)pyrrolidin-1-yl)propan-2-ol (1.29 g, 4.20 mmol, 84.6% yield).

Intermediate 12

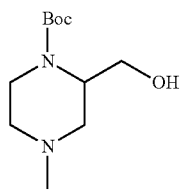

tert-butyl 2-(hydroxymethyl)-4-methylpiperazine-1-carboxylate

To a suspension of lithium chloride (246 mg, 5.81 mmol) and Lithium Borohydride (126 mg, 5.81 mmol) in ethanol (9 mL), at 0° C. under nitrogen, a solution of 1-(tert-butyl) 2-methyl 4-methylpiperazine-1,2-dicarboxylate (750 mg, 2.90 mmol) in dry THF (6 mL) was added dropwise. The reaction was stirred overnight forming a white precipitate. The precipitate was filtered and washed with ethanol. The combined filtrate and organic extracts were concentrated to provide a white residue which was extracted with ethyl acetate. The combined organic layers were washed with saturated sodium chloride solution, dried over sodium sulfate and concentrated in vacuo. The residue was purified by chromatography with isocratic 10% MeOH in DCM with 0.2% NH$_4$OH to provide tert-butyl 2-(hydroxymethyl)-4-methylpiperazine-1-carboxylate (104 mg, 0.452 mmol, 15.6% yield).

Intermediate 13

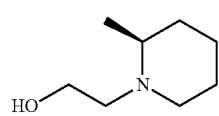

(S)-2-(2-methylpiperidin-1-yl)ethan-1-ol

A mixture of (S)-2-methylpiperidine (100 mg, 1.01 mmol), 2-bromoethanol (78 μL, 139 mg, 1.11 mmol, 1.1 eq.), sodium iodide (151 mg, 1 eq.), potassium carbonate (418 mg, 3 eq.) and acetonitrile (1 mL) in a 4-mL vial was purged with nitrogen, sealed and stirred at room temperature for 2 days. The reaction mixture was partitioned between diethyl ether (15 mL) and water (2 mL). The ether layer was washed with brine (2 mL), acidified with TFA and dried under high vacuum for 2 days. The residue was washed with ether (3 mL), diluted with water (0.5 mL) and basified with 10M NaOH (0.2 mL). The layers were separated and the upper layer was carefully dried over NaOH. The ether solution was evaporated under nitrogen to yield crude (S)-2-(2-methylpiperidin-1-yl)ethan-1-ol (100 mg, 0.698 mmol, 69.24% yield) as colorless oil.

Intermediate 14

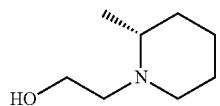

(R)-2-(2-methylpiperidin-1-yl)ethan-1-ol

Synthesized according to the method of Intermediate 13, using (R)-2-methylpiperidine (99 mg, 1 mmol) in place of (S)-2-methylpiperidine.

Intermediate 15

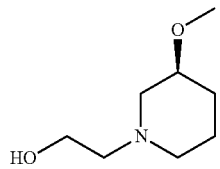

(S)-2-(3-methoxypiperidin-1-yl)ethan-1-ol

Synthesized according to the method of Intermediate 13, using (S)-3-methoxypiperidine (173 mg, 1.50 mmol) in place of (S)-2-methylpiperidine.

Intermediate 16

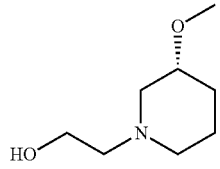

(R)-2-(3-methoxypiperidin-1-yl)ethan-1-ol

Synthesized according to the method of Intermediate 13, using R-3-methoxypiperidine (173 mg, 1.50 mmol) in place of (S)-2-methylpiperidine.

Intermediate 17

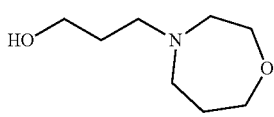

3-(1,4-oxazepan-4-yl)propan-1-ol

To a vial was added homomorpholine (0.250 g, 2.472 mmol), Acetonitrile (4.943 mL, 2.472 mmol) and 3-Bromo-1-propanol (0.2459 mL, 2.719 mmol). Potassium carbonate (0.6832 g, 4.943 mmol) was added and the mixture was warmed to 50° C. and stirred for 6 hours. The mixture was cooled to ambient temperature, diluted with DCM, filtered and the collected solids were washed with DCM. The filtrate was concentrated in vacuo and the crude oil was purified via column chromatography (Biotage Isolera, 12 g Isco RediSep Gold, 10-20% MeOH/DCM with 0.2% NH$_4$OH) to afford 3-(1,4-oxazepan-4-yl)propan-1-ol (0.272 g, 1.708 mmol) as a colorless oil.

Intermediate 18

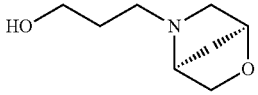 [SMILES: OCCCN1C[C@@H]2C[C@H]1CO2]

3-((1S,4S)-2-oxa-5-azabicyclo[2.2.1]heptan-5-yl)propan-1-ol

Synthesized according to the method of Intermediate 17, using (1S,4S)-2-Oxa-5-azabicyclo[2.2.1]heptane (0.250 g, 2.522 mmol) in place of homomorpholine.

Intermediate 19

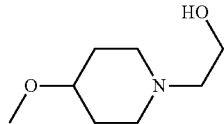

2-(4-methoxypiperidin-1-yl)ethan-1-ol

Synthesized according to the method of Intermediate 13, using 4-methoxypiperidine (173 mg, 1.50 mmol) in place of (S)-2-methylpiperidine.

Intermediate 20

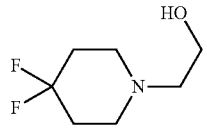 [SMILES: OCCN1CCC(F)(F)CC1]

2-((4,4-difluoropiperidin-1-yl)ethan-1-ol

Synthesized according to the method of Intermediate 13, using 4,4-difluoropiperidine hydrochloride (173 mg, 1.50 mmol) in place of (S)-2-methylpiperidine.

Intermediate 21

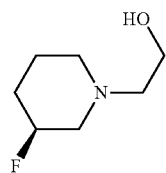

(S)-2-(3-fluoropiperidin-1-yl)ethan-1-ol

Synthesized according to the method of Intermediate 13, using S-3-fluoropiperidine hydrochloride (209 mg, 1.50 mmol) in place of (S)-2-methylpiperidine.

Intermediate 22

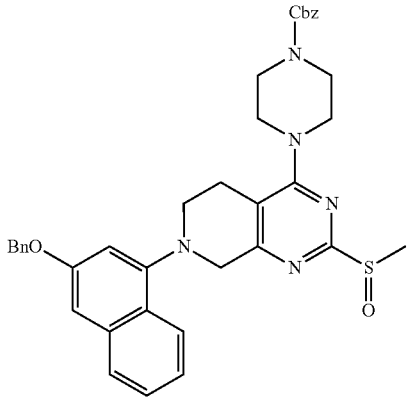 [SMILES: CS(=O)c1nc2c(c(N3CCN(C(=O)OCc4ccccc4)CC3)n1)CCN(c1cc(OCc3ccccc3)cc3ccccc13)C2]

benzyl 4-(7-(3-(benzyloxy)naphthalen-1-yl)-2-(methylsulfinyl)-5,6,7,8-tetrahydropyrido[3,4-d]pyrimidin-4-yl)piperazine-1-carboxylate Step A: tert-butyl 4-hydroxy-2-(methylthio)-5,8-dihydropyrido[3,4-d]pyrimidine-7(6H)-carboxylate To a stirred solution of 1-tert-butyl 4-ethyl 3-oxopiperidine-1,4-dicarboxylate (50.0 g, 184 mmol, 1.00 eq) in MeOH (1.00 L) at 25° C. under nitrogen was added NaOMe (49.8 g, 921 mmol, 5.00 eq), followed by 2-methylisothiourea (62.4 g, 331 mmol, 1.80 eq, H$_2$SO$_4$) as a solid. The reaction mixture was stirred at 25° C. for 16 hours. The reaction mixture was adjusted to pH 5 with HCl (2 M), and the mixture was concentrated under reduced pressure to removed MeOH. The residue was suspended in 300 mL of ethyl acetate and 300 mL of water and stirred rapidly. The suspension was filtered and the white solid was collected. The filtrate was separated and the organic layer was washed with water (1×300 mL) and brine (1×200 mL). The combined organic layers were isolated, dried over Na$_2$SO$_4$, filtered and concentrated to provide tert-butyl 4-hydroxy-2-methylsulfanyl-6,8-dihydro-5H-pyrido[3,4-d]pyrimidine-7-carboxylate (51.0 g, 138 mmol, 75.4% yield, 81.0% purity) as a white solid which as used directly in the next step without further purification. ESI MS m/z 298.2 [M+H]$^+$.

Step B: tert-butyl 2-methylsulfanyl-4-(trifluoromethylsulfonyloxy)-6,8-dihydro-5H-pyrido[3,4-d]pyrimidine-7-carboxylate To a stirred suspension of tert-butyl 4-hydroxy-2-methylsulfanyl-6,8-dihydro-5H-pyrido[3,4-d]pyrimidine-7-carboxylate (51.0 g, 171 mmol, 1.00 eq) in DCM (500 mL) at 0° C. was added DIEA (44.3 g, 343 mmol, 59.9 mL, 2.00 eq), followed by trifluoromethanesulfonic anhydride (72.6 g, 257 mmol, 42.4 mL, 1.50 eq) under nitrogen. Immediately a brown solution formed. After stirring at 25° C. for 16 hours, the reaction was concentrated to give a brown oil. The brown oil was purified by column chromatography (SiO$_2$, Petroleum ether/Ethyl acetate=1:0 to 10:1) to provide tert-butyl 2-methylsulfanyl-4-(trifluoromethylsulfonyloxy)-6,8-dihydro-5H-pyrido[3,4-d]pyrimidine-7-carboxylate (46.0 g, 107 mmol, 62.4% yield) as a yellow solid ESI MS m/z 430.2 [M+H]$^+$.

Step C: tert-butyl 4-(4-benzyloxycarbonylpiperazin-1-yl)-2-methylsulfanyl-6,8-dihydro-5H-pyrido[3,4-d]pyrimidine-7-carboxylate To a stirred solution of tert-butyl 2-methylsulfanyl-4-(trifluoromethylsulfonyloxy)-6,8-dihydro-5H-pyrido[3,4-d]pyrimidine-7-carboxylate (46.0 g, 107 mmol, 1.00 eq) in DMF (500 mL) was added DIEA (27.7 g, 214 mmol, 37.4 mL, 2.00 eq) followed by benzyl piperazine-1-carboxylate (25.9 g, 117 mmol, 22.7 mL, 1.10 eq). The reaction was heated to 100° C. for 1 hour under a nitrogen atmosphere. The reaction mixture was poured into ethyl acetate (300 mL), washed with H$_2$O (300 mL×3) and brine (200 mL), dried over anhydrous Na$_2$SO$_4$, filtered and concentrated under vacuum. The residue was purified by column chromatography (SiO$_2$, Petroleum ether/Ethyl acetate=1:0 to 5:1) to give tert-butyl 4-(4-benzyloxycarbonylpiperazin-1-yl)-2-methylsulfanyl-6,8-dihydro-5H-pyrido[3,4-d]pyrimidine-7-carboxylate (51.0 g, 96.9 mmol, 90.5% yield, 92.0% purity) as a white solid ESI MS m/z 500.3 [M+H]$^+$.

Step D: Benzyl 4-(2-methylsulfanyl-5,6,7,8-tetrahydropyrido[3,4-d]pyrimidin-4-yl) piperazine-1-carboxylate To a solution of tert-butyl 4-(4-benzyloxycarbonylpiperazin-1-yl)-2-methylsulfanyl-6,8-dihydro-5H-pyrido[3,4-d]pyrimidine-7-carboxylate (25.0 g, 50.0 mmol, 1.00 eq) in DCM (50.0 mL) was added TFA (85.6 g, 750 mmol, 55.6 mL, 15.0 eq). After stirring at 25° C. for 1 hour, the reaction mixture was concentrated under reduced pressure. The residue was dissolved in 300 mL of ethyl acetate and 300 mL of water and stirred rapidly. The mixture was adjusted to pH 8 with Na$_2$CO$_3$. The organic layer was washed with water (1×300 mL) and brine (1×200 mL), dried over Na$_2$SO$_4$, filtered and concentrated under reduced pressure to provide benzyl 4-(2-methylsulfanyl-5,6,7,8-tetrahydropyrido[3,4-d]pyrimidin-4-yl) piperazine-1-carboxylate (19.0 g, 46.6 mmol, 93.2% yield, 98.0% purity) as a yellow oil. ESI MS m/z 400.2 [M+H]$^+$.

Step E: Benzyl 4-[7-(3-benzyloxy-1-naphthyl)-2-methylsulfanyl-6,8-dihydro-5H-pyrido[3,4-d]pyrimidin-4-yl]piperazine-1-carboxylate A mixture of 3-benzyloxy-1-bromo-naphthalene (16.3 g, 52.1 mmol, 1.30 eq), benzyl 4-(2-methylsulfanyl-5,6,7,8-tetrahydropyrido[3,4-d]pyrimidin-4-yl)piperazine-1-carboxylate (16.0 g, 40.1 mmol, 1.00 eq), Cs$_2$CO$_3$ (32.6 g, 100 mmol, 2.50 eq), Pd$_2$(dba)$_3$ (5.50 g, 6.01 mmol, 0.15 eq) and 2-dicyclohexylphosphino-2',6'-diisopropoxybiphenyl (RuPhos) (3.74 g, 8.01 mmol, 0.20 eq) in dioxane (300 mL) was degassed and purged with nitrogen 3 times. The mixture was stirred at 85° C. for 5 hours under a nitrogen atmosphere. The reaction mixture was quenched by adding water (200 mL) at 0° C., and extracted with ethyl acetate (3×200 mL). The combined organic layers were washed with brine (3×150 mL), dried over Na$_2$SO$_4$, filtered and concentrated under reduced pressure. The residue was purified by column chromatography (SiO$_2$, DCM/MeOH=10/1 to 5/1) to provide benzyl 4-[7-(3-benzyloxy-1-naphthyl)-2-methylsulfanyl-6,8-dihydro-5H-pyrido[3,4-d]pyrimidin-4-yl]piperazine-1-carboxylate (16.0 g, 22.8 mmol, 56.9% yield, 90.0% purity) as a yellow solid. ESI MS m/z 632.5 [M+H]$^+$.

Step F: Benzyl 4-[7-(3-benzyloxy-1-naphthyl)-2-methylsulfinyl-6,8-dihydro-5H-pyrido [3,4-d]pyrimidin-4-yl]piperazine-1-carboxylate To a stirred solution of benzyl 4-[7-(3-benzyloxy-1-naphthyl)-2-methylsulfanyl-6,8-dihydro-5H-pyrido[3,4-d]pyrimidin-4-yl]piperazine-1-carboxylate (8.00 g, 12.7 mmol, 1.00 eq) in DCM (200 mL) was added m-CPBA (2.73 g, 12.7 mmol, 80.0% purity, 1.00 eq) at 0° C. under nitrogen. After stirring at 0° C. for 2 hours under a nitrogen atmosphere, the reaction mixture was quenched by adding Na$_2$S$_2$O$_3$ (10.0 mL) at 0° C., diluted with water (100 mL) and extracted with DCM (200 mL). The combined organic layers were washed with brine (200 mL), dried over Na$_2$SO$_4$, filtered and concentrated under reduced pressure to give a residue. The residue was purified by column chromatography (SiO$_2$, DCM/MeOH=1/0 to 10/1) to provide benzyl 4-[7-(3-benzyloxy-1-naphthyl)-2-methylsulfinyl-6,8-dihydro-5H-pyrido [3,4-d]pyrimidin-4-yl]piperazine-1-carboxylate (3.50 g, 4.92 mmol, 38.8% yield, 91.0% purity) as a yellow solid. ESI MS m/z 648.5 [M+H]$^+$.

Intermediate 23

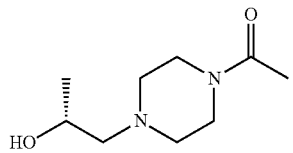

(R)-1-(4-(2-hydroxypropyl)piperazin-1-yl)ethan-1-one

Step A: 1-[4-[(2R)-2-hydroxypropyl]piperazin-1-yl]ethanone (2R)-2-methyloxirane (1.00 g, 17.2 mmol, 1.20 mL, 1.00 eq) and 1-piperazin-1-ylethanone (8.00 g, 62.4 mmol, 3.62 eq) were taken up into a microwave tube. The sealed tube was heated at 150° C. for 1 hour under microwave. The mixture was dissolved in DCM (80.0 mL), added (Boc)₂O (3.62 eq, 13.6 g) and stirred at 20° C. for 1 hour. The residue was purified by column chromatography (DCM/MeOH 100/1 to 10/1) to give 1-[4-[(2R)-2-hydroxypropyl]piperazin-1-yl]ethanone (3.80 g, 13.5 mmol, 78.2% yield, 66.0% purity) as a yellow oil.

Intermediate 24

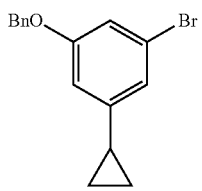

1-(benzyloxy)-3-bromo-5-cyclopropylbenzene

Step A: 1-benzyloxy-3,5-dibromo-benzene

To a mixture of 3,5-dibromophenol (1.50 g, 5.95 mmol, 1.00 eq) and K₂CO₃ (2.47 g, 17.9 mmol, 3.00 eq) in MeCN (30.0 mL) was added benzyl bromide (1.07 g, 6.25 mmol, 742 μL, 1.05 eq), the reaction mixture was stirred at 80° C. for 2 hours. The reaction mixture was filtered and concentrated. The residue was purified by column chromatography (SiO₂, Petroleum ether/Ethyl acetate=1:1 to give 1-benzyloxy-3,5-dibromobenzene (1.60 g, 4.68 mmol, 78.6% yield) as colorless oil.

Step B: 1-benzyloxy-3-bromo-5-cyclopropylbenzene

To a mixture of 1-benzyloxy-3,5-dibromobenzene (1.20 g, 3.51 mmol, 1.00 eq) and cyclopropylboronic acid (392 mg, 4.56 mmol, 1.30 eq) in H₂O (4.00 mL) and dioxane (20.0 mL) was added Pd(dppf)Cl₂ (513 mg, 702 μmol, 0.20 eq) and Cs₂CO₃ (2.29 g, 7.02 mmol, 2.00 eq). The reaction mixture was stirred at 90° C. for 12 hours under N₂. The reaction mixture was added to water (20 mL) and extracted with ethyl acetate (2×15 mL). The combined organic layers were dried over Na₂SO₄, filtered and concentrated. The residue was purified by column chromatography (SiO₂, Petroleum ether/Ethyl acetate=1:1 to give 1-benzyloxy-3-bromo-5-cyclopropyl-benzene (270 mg, 890 μmol, 25.4% yield) as colorless oil.

Intermediate 25

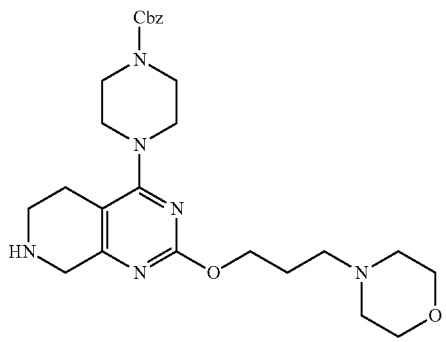 [SMILES: O=C(OCc1ccccc1)N1CCN(c2nc(OCCCN3CCOCC3)nc3c2CCNC3)CC1]

benzyl 4-(2-(3-morpholinopropoxy)-5,6,7,8-tetrahydropyrido[3,4-d]pyrimidin-4-yl)piperazine-1-carboxylate Step A: tert-butyl 4-(4-benzyloxycarbonylpiperazin-1-yl)-2-(3-morpholinopropoxy)-6,8-dihydro-5H-pyrido[3,4-d]pyrimidine-7-carboxylate To a mixture of 3-morpholinopropan-1-ol (5.46 g, 37.6 mmol, 2.00 eq) in THF (100 mL) was added NaH (2.26 g, 56.4 mmol, 60.0% purity, 3.00 eq) in portions at 0° C. After the mixture was stirred at 0° C. for 0.5 hour, a solution of tert-butyl 4-(4-benzyloxycarbonylpiperazin-1-yl)-2-methylsulfonyl-6,8-dihydro-5H-pyrido[3,4-d]pyrimidine-7-carboxylate (10.0 g, 18.8 mmol, 1.00 eq) in THF (100 mL) was added, and the reaction mixture was stirred at 0° C. for 1.5 hours under N₂. The mixture was poured into NH₄Cl aqueous (300 mL), and extracted with DCM (2×200 mL). The combined organic layers were dried over Na₂SO₄, filtered and concentrated. The residue was purified by column chromatography (SiO₂, Petroleum ether/Ethyl acetate=50:1 to 10:1) to give tert-butyl 4-(4-benzyloxycarbonylpiperazin-1-yl)-2-(3-morpholinopropoxy)-6,8-dihydro-5H-pyrido[3, 4-d]pyrimidine-7-carboxylate (7.70 g, 12.8 mmol, 67.8% yield, 98.8% purity) as a yellow oil. ESI MS m/z 597.4 [M+H]⁺.

Step B: benzyl 4-[2-(3-morpholinopropoxy)-5,6,7,8-tetrahydropyrido[3,4-d]pyrimidin-4-yl]piperazine-1-carboxylate To a mixture of tert-butyl 4-(4-benzyloxycarbonylpiperazin-1-yl)-2-(3-morpholinopropoxy)-6,8-dihydro-5H-pyrido[3,4-d]pyrimidine-7-carboxylate (7.70 g, 12.9 mmol, 1.00 eq) in DCM (80.0 mL) was added TFA (119 g, 1.04 mol, 76.9 mL, 80.6 eq), and the reaction mixture was stirred at 15° C. for 1 hour. The reaction mixture was concentrated, then diluted with DCM (100 mL) and adjusted to pH 8 with aqueous NaOH. The organic layer was separated, dried over Na₂SO₄, filtered and concentrated to give benzyl 4-[2-(3-morpholinopropoxy)-5,6,7,8-tetrahydropyrido[3,4-d]pyrimidin-4-yl]piperazine-1-carboxylate (6.00 g, 11.2 mmol, 86.9% yield, 92.8% purity) as yellow oil. ESI MS m/z 497.4 [M+H]⁺.

Intermediate 26

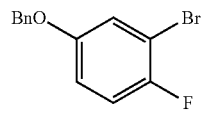

4-(benzyloxy)-2-bromo-1-fluorobenzene

To a solution of 3-bromo-4-fluorophenol (4.00 g, 20.9 mmol, 1.00 eq) and K₂CO₃ (8.68 g, 62.8 mmol, 3.00 eq) in ACN (80.0 mL) was added benzyl bromide (3.65 g, 21.4 mmol, 2.54 mL, 1.02 eq) and the reaction mixture was stirred at 60° C. for 2 hrs. The reaction mixture was filtered and concentrated in vacuum. The residue was purified by silica gel chromatography (petroleum ether:ethyl acetate; gradient from 1:0 to 10:1) to give 4-benzyloxy-2-bromo-1- fluoro-benzene (5.02 g, 17.0 mmol, 81.0% yield, 95% purity) was obtained as white solid.

Intermediate 27

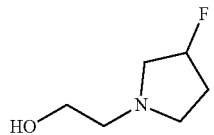

2-(3-fluoropyrrolidin-1-yl)ethan-1-ol

Step A: tert-butyl 3-fluoropyrrolidine-1-carboxylate

To a solution of tert-butyl 3-hydroxypyrrolidine-1-carboxylate (10.0 g, 53.4 mmol, 1.00 eq) in DCM (150.00 mL) was added diethylaminosulfur trifluoride (DAST) (12.9 g, 80.1 mmol, 10.6 mL, 1.50 eq) at −40° C. under a nitrogen atmosphere. After stirring at −40° C. for 2 hours, the mixture was warmed to 20° C. and stirred for 16 hours. The mixture was poured into 5% aqueous sodium bicarbonate (200 mL) and extracted with dichloromethane (2×100 mL). The organic layer was dried over sodium sulfate, filtered and concentrated under vacuum. The residue was purified by column chromatography over silica gel (petroleum ether/ethyl acetate 100:1 to 5:1). The desired fractions were collected and concentrated under vacuum to give tert-butyl 3-fluoropyrrolidine-1-carboxylate (4.30 g, 22.7 mmol, 42.6% yield) as a colorless oil. $^1$H NMR (400 MHz, Chloroform-d) δ=5.27 (t, J=3.6 Hz, 0.5H), 5.13 (t, J=3.6 Hz, 0.5H), 3.77-3.38 (m, 4H), 2.26-2.15 (m, 1H), 2.08-1.85 (m, 1H), 1.46 (s, 9H).

Step B: 3-fluoropyrrolidine

To a solution of tert-butyl 3-fluoropyrrolidine-1-carboxylate (4.30 g, 22.7 mmol, 1.00 eq) in DCM (50.00 mL) was added HCl/dioxane (4 M, 35.0 mL, 6.16 eq) dropwise at 0° C. The mixture was warmed to 20° C. and stirred for 1 hour. The mixture was concentrated under vacuum. The residue was triturated with diisopropyl ether (20 mL) and the precipitate was filtered and dried under vacuum to provide 3-fluoropyrrolidine (2.70 g, 21.5 mmol, 94.6% yield, HCl) as a white solid. $^1$H NMR (400 MHz, Methanol-d$_4$) δ=5.51 (t, J=3.6 Hz, 0.5H), 5.38 (t, J=3.6 Hz, 1H), 3.66-3.27 (m, 5H), 2.45-2.12 (m, 2H).

Step C: methyl 2-(3-fluoropyrrolidin-1-yl)acetate

A suspension of 3-fluoropyrrolidine (2.70 g, 21.5 mmol, 1.00 eq, HCl) in DCM (27.00 mL) was cooled to 0° C. Triethylamine (5.44 g, 53.8 mmol, 7.45 mL, 2.50 eq) and methyl 2-bromoacetate (3.62 g, 23.7 mmol, 2.23 mL, 1.10 eq) were added and the reaction mixture was stirred at 20° C. for 16 h. The reaction mixture was diluted with CH$_2$Cl$_2$ (100 mL) and water (50 mL). The organic layer was washed with 5% aqueous citric acid solution (1×50 mL). The water layer was basified by saturated aqueous sodium carbonate solution (20 mL) and extracted with ethyl acetate (3×100 mL). The combined organic layers were dried over sodium sulfate and concentrated in vacuo to give methyl 2-(3-fluoropyrrolidin-1-yl)acetate (2.20 g, 13.7 mmol, 63.5% yield). $^1$H NMR (400 MHz, Chloroform-d) δ=5.22-5.02 (m, 1H), 3.66 (s, 3H), 3.35 (s, 2H), 3.07-2.93 (m, 1H), 2.91-2.77 (m, 2H), 2.67 (dt, J=5.2, 8.4 Hz, 1H), 2.21-1.93 (m, 2H).

Step D: 2-(3-fluoropyrrolidin-1-yl)ethanol

To a solution of LiAlH$_4$ (706 mg, 18.6 mmol, 1.50 eq) in THF (20 mL) was added a solution of methyl 2-(3-fluoropyrrolidin-1-yl)acetate (2.00 g, 12.4 mmol, 1.00 eq) in THF (10 mL) dropwise at 0° C. The mixture was warmed up to 20° C. and stirred for 3 hours. The mixture was quenched with saturated aqueous sodium sulfate solution (1 mL). The mixture was filtered and the filtrate was concentrated under vacuum. The product was purified by silica gel chromatography using 5% MeOH in DMC. The desired fractions were collected and concentrated under vacuum to give 2-(3-fluoropyrrolidin-1-yl)ethanol (1.20 g, 9.01 mmol, 72.6% yield) as a colorless oil. $^1$H NMR (400 MHz, Chloroform-d) δ=5.28-5.05 (m, 1H), 3.68-3.61 (m, 2H), 2.99-2.73 (m, 4H), 2.72-2.67 (m, 2H), 2.58-2.45 (m, 1H), 2.28-1.97 (m, 2H).

Intermediate 28

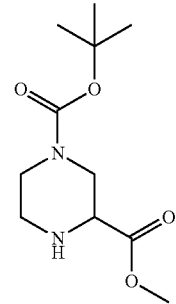

1-(tert-butyl) 3-methyl piperazine-1,3-dicarboxylate

Step A: methyl piperazine-2-carboxylate

To a mixture of 1-tert-butyl 2-methyl piperazine-1,2-dicarboxylate (5.0 g, 22.6 mmol, 1.00 eq) in MeOH (50.0 mL) was added HCl/dioxane (4.0 M, 134 mL). The reaction mixture was degassed and purged with nitrogen 3 times, and the mixture was stirred at 25° C. for 12 hours under a nitrogen atmosphere. The reaction mixture was concentrated under reduced pressure to dryness to give methyl piperazine-2-carboxylate (4.89 g, 2HCl, crude) as a white solid, which was used directly in the next step without further purification.

Step B: 1-(tert-butyl) 3-methyl piperazine-1,3-dicarboxylate

To a solution of methyl piperazine-2-carboxylate (4.30 g, crude) and TEA (8.02 g, 79.2 mmol, 11.0 mL) in MeOH (50.0 mL) was added di-tert-butyl dicarbonate (4.32 g, 19.8 mmol, 4.55 mL). After stirring at 25° C. for 12 hours, the reaction mixture was filtered and concentrated under reduced pressure to dryness. The residue was purified by column chromatography (SiO$_2$, DCM/MeOH=1:0 to 20:1) to give 1-(tert-butyl) 3-methyl piperazine-1,3-dicarboxylate (4.80 g, 19.7 mmol, two steps, 99.0% yield) as a colorless oil. $^1$H NMR (400 MHz, chloroform-d) δ=4.10-3.85 (m, 1H), 3.73 (s, 3H), 3.71-3.65 (m, 1H), 3.47-3.38 (m, 1H), 3.10-2.98 (m, 2H), 2.78-2.66 (m, 1H), 2.17 (s, 1H), 1.46 (s, 9H).

Intermediate 29

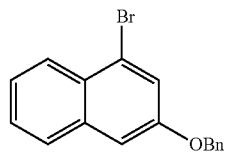 [SMILES: Brc1cc(OCc2ccccc2)cc2ccccc12]

4-bromonaphthalen-2-ol

Step A: 2,4-dibromonaphthalen-1-amine

To a solution of Br$_2$ (246 g, 1.54 mol, 79.3 mL, 2.18 eq) in AcOH (750 mL) was added a solution of naphthalen-1-amine (101 g, 705 mmol, 99.0 mL, 1.00 eq) in AcOH (500 mL) at ambient temperature, and the reaction was stirred at 70° C. for 1 hour. The reaction mixture was cooled at room temperature and filtered. The filter cake was washed with AcOH (300 mL), then added to 20% aqueous of NaOH (1.2 L). The mixture was stirred for 20 min and filtered. The isolated solid was washed with water (1 L) and dried under vacuum to provide 2,4-dibromonaphthalen-1-amine (200 g, 664 mmol, 94.2% yield) as gray solid. ESI MS m/z 301.9 [M+H]$^+$.

Step B: 4-bromo-1-diazonio-naphthalen-2-olate

To a solution of 2,4-dibromonaphthalen-1-amine (60.0 g, 199 mmol, 1.00 eq) in AcOH (900 mL) and propionic acid (150 mL) was added NaNO$_2$ (16.5 g, 239 mmol, 13.0 mL, 1.20 eq) portionwise at 5-8° C. over 30 min, and then the reaction mixture was stirred at 5-8° C. for 30 min. The reaction mixture was poured into ice-water (4000 mL), and the resulting solid was collected and washed with water (2×50 mL) to provide 4-bromo-1-diazonio-naphthalen-2-olate (150 g, wet crude) as gray solid which was used directly in the next step. $^1$H NMR (400 MHz, CDCl$_3$) δ 8.12-8.10 (d, J=8.4 Hz, 1H), 7.62-7.58 (t, J=7.6 Hz, 1H), 7.41-7.37 (t, J=7.6 Hz, 1H), 7.31-7.29 (d, J=8.0 Hz, 1H), 7.20 (s, 1H).

Step C: 4-bromonaphthalen-2-ol

To a solution of 4-bromo-1-diazonio-naphthalen-2-olate (100 g, 402 mmol, 1.00 eq) in EtOH (2.00 L) was added portionwise NaBH$_4$ (30.4 g, 803 mmol, 2.00 eq) at 13-15° C. over 1 h, and the reaction mixture was stirred at 15-18° C. for 3 hrs. The reaction was filtered and concentrated to dryness. The residue was dissolved in DCM (1000 mL) and washed with water (500 mL×2). The organic phase was dried over Na$_2$SO$_4$ and concentrated to dryness. The residue was purified by silica gel column chromatograph, eluting with diethyl ether/ethyl acetate (60:1 to 10:1). The isolated product was further purified by reversed phase HPLC to provide 4-bromonaphthalen-2-ol (40.0 g, 139 mmol, 17.3% yield, 77.4% purity) as a gray solid. $^1$H NMR (400 MHz, CDCl$_3$) δ 8.07-8.05 (d, J=8.0 Hz, 1H), 7.60-7.58 (d, J=7.6 Hz, 1H), 7.41-7.36 (m, 3H), 7.07 (s, 1H).

Step D: 3-benzyloxy-1-bromo-naphthalene

A mixture of 4-bromonaphthalen-2-ol (30.0 g, 134 mmol, 1.00 eq), benzyl bromide (25.3 g, 148 mmol, 17.6 mL, 1.10 eq) and K$_2$CO$_3$ (55.7 g, 403 mmol, 3.00 eq) in MeCN (500 mL) was heated at 80° C. for 1 hr. The reaction mixture was filtered and concentrated to dryness. The residue was purified by silica gel column chromatography, eluting with diethyl ether/ethyl acetate (100:1 to 60:1) to provide 3-benzyloxy-1-bromo-naphthalene (40.0 g, 128 mmol, 95% yield) as yellow oil. $^1$H NMR (400 MHz, CDCl$_3$) δ 8.19-8.17 (d, J=8.0 Hz, 1H), 7.75-7.32 (d, J=8.8 Hz, 1H), 7.64-7.63 (d, J=2.4 Hz, 1H), 7.52-7.37 (m, 7H), 7.23-7.21 (d, J=2.0 Hz, 1H), 5.2 (s, 2H).

Intermediate 30

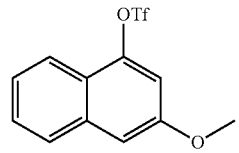

3-methoxynaphthalen-1-yl trifluoromethanesulfonate

Step A: 3-methoxynaphthalen-1-ol

To a solution of naphthalene-1,3-diol (3.00 g, 18.7 mmol, 1.00 eq) in MeOH (60.0 mL) was added HCl/MeOH (4 M, 60.0 mL, 12.8 eq) at 0° C. The mixture was stirred at 25° C. for 60 hours. The solvent was removed under vacuum. The residue was purified by silica gel chromatography (diethyl ether:ethyl acetate=10:1 to 5:1) to give 3-methoxynaphthalen-1-ol (2.10 g, 12.1 mmol, 64.4% yield) as a brown solid. $^1$H NMR (400 MHz, CDCl$_3$-d$_6$) δ=8.10-8.08 (d, J=8.4 Hz, 1H). 7.73-7.71 (d, J=8.4 Hz, 1H), 7.47-7.45 (m, 1H), 7.38-7.35 (m, 1H), 6.80-6.79 (d, J=2.0 Hz, 1H), 6.56-6.55 (d, J=2.4 Hz, 1H), 3.92 (s, 3H).

Step B: (3-methoxy-1-naphthyl) trifluoromethanesulfonate

To a solution of 3-methoxynaphthalen-1-ol (2.10 g, 12.0 mmol, 1.00 eq) in DCM (40.0 mL) was added DIEA (7.79 g, 60.3 mmol, 10.5 mL, 5.00 eq) and trifluoromethanesulfonic anhydride (5.10 g, 18.1 mmol, 2.98 mL, 1.50 eq) at 0° C. The mixture was stirred at 25° C. for 1 hour. The mixture was diluted with DCM (30 mL) and water (10 mL) and extracted with DCM (20 mL). The combined organic layers were washed with brine (5 mL), dried over Na$_2$SO$_4$ and concentrated under vacuum. The residue was purified by silica gel chromatography (diethyl ether:ethyl acetate=20:1 to 10:1) to give (3-methoxy-1-naphthyl) trifluoromethanesulfonate (3.00 g, 8.52 mmol, 70.7% yield, 87.0% purity) as a brown oil. ESI MS m/z 307.1 [M+H]$^+$.

Intermediate 31

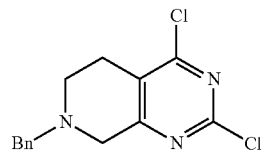

7-benzyl-2,4-dichloro-6,8-dihydro-5H-pyrido[3,4-d]pyrimidine

Step A: 7-benzyl-6,8-dihydro-5H-pyrido[3,4-d]pyrimidine-2,4-diol

To EtOH (600 mL) was added Na (5.56 g, 241 mmol, 5.73 mL, 2.40 eq) in portions. The reaction mixture was stirred for 1 hour. To the mixture was added ethyl 1-benzyl-3-oxopiperidine-4-carboxylate (30.0 g, 100 mmol, 1.00 eq, HCl) and urea (14.5 g, 242 mmol, 13.0 mL, 2.40 eq). The reaction mixture was stirred at 75° C. for 36 hours, and then the solvent was removed under vacuum. The residue was dissolved in water (50 mL) and acidified with HCl (120 mL, 2M). A white solid precipitated from the solution and was collected by filtration. The filter cake was dried under vacuum to provide 7-benzyl-6,8-dihydro-5H-pyrido[3,4-d]pyrimidine-2,4-diol (22.0 g, 83.8 mmol, 83.2% yield, 98% purity) as a white solid. $^1$HNMR (400 MHz, DMSO-$d_6$) δ=10.97 (br s, 1H), 10.66 (br s, 1H), 7.55-6.95 (m, 5H), 3.81-3.50 (m, 2H), 3.26-2.91 (m, 2H), 2.77-2.58 (m, 2H), 2.34-2.09 (m, 2H).

Step B: 7-benzyl-2,4-dichloro-6,8-dihydro-5H-pyrido[3,4-d]pyrimidine

To a solution of DIEA (30.1 g, 233 mmol, 40.7 mL, 3.00 eq) in POCl$_3$ (330 g, 2.15 mol, 200 mL) was added 7-benzyl-6,8-dihydro-5H-pyrido[3,4-d]pyrimidine-2,4-diol (20.0 g, 77.7 mmol, 1.00 eq). The reaction mixture was stirred at 110° C. for 5 hours. The reaction mixture was concentrated under vacuum. The residue was dissolved in DCM (400 mL) and poured into saturated NaHCO$_3$ (200 mL). The mixture was extracted with DCM (2×400 mL). The combined organic layers were washed with brine (100 mL), dried over Na$_2$SO$_4$ and concentrated under vacuum. The residue was purified by silica gel chromatography (diethyl ether:DCM=10:1 to 0:1) to give 7-benzyl-2,4-dichloro-6,8-dihydro-5H-pyrido[3,4-d]pyrimidine (7.70 g, 26.2 mmol, 33.7% yield) as a brown oil. $^1$HNMR (300 MHz, chloroform-d) δ=7.43-7.28 (m, 5H), 3.73 (s, 2H), 3.66 (br s, 2H), 2.84 (br s, 4H)

Intermediate 32 tert-butyl4-(4-((benzyloxy)carbonyl)piperazin-1-yl)-2-(methylsulfonyl)-5,6-dihydropyrido[3,4-d]pyrimidine-7(8H)-carboxylate

Step A: tert-butyl4-hydroxy-2-methylsulfanyl-6,8-dihydro-5H-pyrido[3,4-d]pyrimidine-7-carboxylate To a stirred solution of 1-tert-butyl 4-ethyl-3-oxopiperidine-1,4-dicarboxylate (44.0 g, 162 mmol, 1.00 eq) in MeOH (1.00 mL) at 25° C. under nitrogen was added a solution of NaOMe (35.0 g, 649 mmol, 4.00 eq) in MeOH (600 mL) by syringe followed by 2-methylisothiourea (61.1 g, 324 mmol, 2.00 eq, H$_2$SO$_4$). After stirring at 25° C. for 16 hours, the reaction mixture was concentrated under reduced pressure to removed MeOH. The residue was suspended in 500 mL of ethyl acetate and 500 mL of water and stirred rapidly. The reaction mixture was adjusted to pH 5 with HCl (2 M). The precipitate was filtered and the white solid was washed with ethyl acetate and dried under vacuum to give tert-butyl4-hydroxy-2-methylsulfanyl-6,8-dihydro-5H-pyrido[3,4-d]pyrimidine-7-carboxylate (33.0 g, 103 mmol, 63.8% yield, 93.2% purity) as a white solid, which was used directly in the next step without further purification. $^1$H NMR (400 MHz, DMSO-d6) δ=4.19 (s, 2H), 3.49 (br s, 2H), 2.46 (s, 3H), 2.35 (br t, J=5.2 Hz, 2H), 1.42 (s, 9H).

Step B: give tert-butyl 2-methylsulfanyl-4-(trifluoromethylsulfonyloxy)-6,8-dihydro-5H-pyrido [3,4-d]pyrimidine-7-carboxylate To a stirred suspension of tert-butyl 4-hydroxy-2-methylsulfanyl-6,8-dihydro-5H-pyrido[3,4-d]pyrimidine-7-carboxylate (15.0 g, 50.4 mmol, 1.00 eq) in DCM (200 mL) was added DIEA (26.1 g, 202 mmol, 35.2 mL, 4.00 eq) at 0° C. under nitrogen and followed by trifluoromethanesulfonic anhydride (28.5 g, 101 mmol, 16.6 mL, 2.00 eq) by syringe. Immediately a brown solution formed. The reaction mixture was stirred at 25° C. for 12 hours. The reaction mixture was purified by column chromatography (SiO$_2$, Petroleum ether/Ethyl acetate=1:0 to 10:1) to give tert-butyl 2-methylsulfanyl-4-(trifluoromethylsulfonyloxy)-6,8-dihydro-5H-pyrido[3,4-d]pyrimidine-7-carboxylate (16.7 g, 35.7 mmol, 70.9% yield, 91.9% purity) as a white solid. ESI MS m/z 374.0 [M+H]$^+$.

Step C: tert-butyl 4-(4-benzyloxycarbonylpiperazin-1-yl)-2-methylsulfanyl-6,8-dihydro-5H-pyrido[3,4-d]pyrimidine-7-carboxylate To a stirred solution of tert-butyl2-methylsulfanyl-4-(trifluoromethyl sulfonyloxy)-6,8-dihydro-5H-pyrido[3,4-d]pyrimidine-7-carboxylate (16.7 g, 38.9 mmol, 1.00 eq) in DMF (100 mL) was added DIEA (10.0 g, 77.9 mmol, 2.00 eq) and benzyl piperazine-1-carboxylate (9.41 g, 42.8 mmol, 1.10 eq). The reaction was heated to 100° C. and stirred for 1 hour under a nitrogen atmosphere. The reaction mixture was diluted with water (150 mL) and the reaction mixture was adjusted to pH 5 with HCl (2 M) and extracted with DCM (3×200 mL). The combined organic layers were washed with saturated NaHCO$_3$ (3×150 mL), brine (3×150 mL) and H$_2$O (3×150 mL), dried over Na$_2$SO$_4$, filtered and concentrated under reduced pressure to give tert-butyl 4-(4-benzyloxycarbonylpiperazin-1-yl)-2-methylsulfanyl-6,8-dihydro-5H-pyrido[3,4-d]pyrimidine-7-carboxylate (18.1 g, 36.2 mmol, 93.0% yield, 94.1% purity) as a yellow solid,

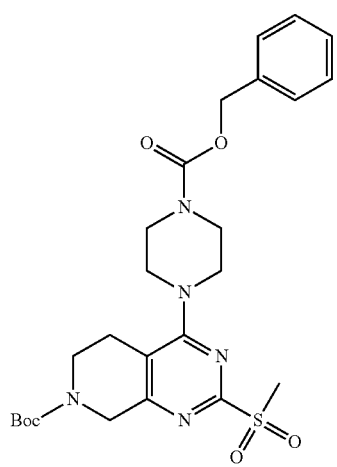 [SMILES: CC(C)(C)OC(=O)N1CCc2c(nc(S(C)(=O)=O)nc2N2CCN(C(=O)OCc3ccccc3)CC2)C1]

which was used directly in the next step without further purification. ESI MS m/z 500.1 [M+H]+.

Step D: tert-butyl 4-(4-benzyloxycarbonylpiperazin-1-yl)-2-methyl sulfonyl-6,8-dihydro-5H-pyrido[3,4-d]pyrimidine-7-carboxylate To a stirred solution of tert-butyl4-(4-benzyloxycarbonylpiperazin-1-yl)-2-methylsulfanyl-6,8-dihydro-5H-pyrido[3,4-d]pyrimidine-7-carboxylate (14.4 g, 28.9 mmol, 1.00 eq) in DCM (150 mL) at 0° C. under nitrogen was added meta-chloroperoxybenzoic acid (17.4 g, 101 mmol, 3.50 eq) as a solid. After stirring at 0° C. for 2 hours under a nitrogen atmosphere, the reaction mixture was diluted with water (300 mL) and the reaction mixture was adjusted to pH 8 with saturated aqueous NaHCO$_3$ and extracted with DCM (3×200 mL). The combined organic layers were washed with brine (3×200 mL), dried over Na$_2$SO$_4$, filtered and concentrated under reduced pressure to dryness. The residue was purified by column chromatography (SiO$_2$, Petroleum ether/Ethyl acetate=10:1 to 1:2) to give tert-butyl 4-(4-benzyloxycarbonylpiperazin-1-yl)-2-methylsulfonyl-6,8-dihydro-5H-pyrido[3,4-d]pyrimidine-7-carboxylate (11.0 g, 19.7 mmol, 68.6% yield, 95.4% purity) as a white solid. ESI MS m/z 532.1 [M+H]+.

Intermediate 33

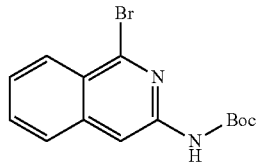 [SMILES: CC(C)(C)OC(=O)Nc1cc2ccccc2c(Br)n1]

tert-butyl (1-bromoisoquinolin-3-yl)carbamate

Step A: A mixture of 1-bromoisoquinolin-3-amine (400 mg, 1.79 mmol, 1.00 eq) and tert-butoxycarbonyl tert-butyl carbonate (3.91 g, 17.9 mmol, 4.12 mL, 10.0 eq) was stirred at 70° C. for 16 hours. The residue was purified by column chromatography (SiO$_2$, diethyl ether/ethyl acetate=5:1) to give tert-butyl N-(1-bromo-3-isoquinolyl) carbamate (400 mg, 1.24 mmol, 69.2% yield) as a yellow solid. ESI MS m/z 322.1, 324.1 [M+H]+.

Intermediate 34

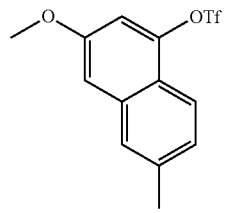 [SMILES: COc1cc(OS(=O)(=O)C(F)(F)F)c2ccc(C)cc2c1]

3-methoxy-6-methylnaphthalen-1-yl trifluoromethanesulfonate

Step A: 3-methoxynaphthalen-1-ol

To a solution of naphthalene-1,3-diol (40.0 g, 250 mmol, 1.00 eq) in MeOH (800 mL) was added HCl (4 M, 750 mL, 12.0 eq, 4 M in MeOH) at 0° C. The mixture was warmed up to 18° C. and stirred for 30 hours. The mixture was concentrated under vacuum. The residue was purified by column chromatography over silica gel (petroleum ether/ethyl acetate 100/1 to 1/1). The desired fractions were collected and concentrated under vacuum to give 3-methoxynaphthalen-1-ol (17.7 g, 96.5 mmol, 38.6% yield, 95% purity) as a red oil. $^1$H NMR (400 MHz, Chloroform-d) δ=8.17 (d, J=8.4 Hz, 1H), 7.74 (d, J=8.0 Hz, 1H), 7.50 (ddd, J=1.2, 6.8, 8.0 Hz, 1H), 7.38 (ddd, J=1.2, 6.8, 8.0 Hz, 1H), 6.81 (d, J=2.0 Hz, 1H), 6.76 (br s, 1H), 6.62 (d, J=2.4 Hz, 1H), 3.91 (s, 3H).

Step B: tert-butyl-[(3-methoxy-1-naphthyl)oxy]-dimethyl-silane

To a solution of 3-methoxynaphthalen-1-ol (20.0 g, 115 mmol, 1.00 eq) and imidazole (23.5 g, 344 mmol, 3.00 eq) in THF (400 mL) was added TBSCl (26.0 g, 172 mmol, 21.1 mL, 1.50 eq) dropwise at 0° C. The mixture was warmed up to 25° C. and stirred for 16 hours. The mixture was diluted with petroleum ether (600 mL) and ethyl acetate (200 mL), and then washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 10/1). tert-butyl-[(3-methoxy-1-naphthyl)oxy]-dimethyl-silane (28.0 g, 97.1 mmol, 84.6% yield) was obtained as a colorless oil. $^1$H NMR (400 MHz, Chloroform-d) δ=8.01 (d, J=8.4 Hz, 1H), 7.61 (d, J=8.0 Hz, 1H), 7.35 (dt, J=1.2, 7.6 Hz, 1H), 7.24 (dt, J=1.2, 7.6 Hz, 1H), 6.71 (d, J=2.0 Hz, 1H), 6.48 (d, J=2.4 Hz, 1H), 3.82 (s, 3H), 1.02 (s, 9H), 0.23 (s, 6H).

Step C: tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy)dimethylsilane A mixture of tert-butyl-[(3-methoxy-1-naphthyl) oxy]-dimethyl-silane (26.0 g, 90.1 mmol, 1.00 eq), 4,4,5,5-tetramethyl-2-((4,4,5,5-tetramethyl-1,3,2-dioxaborolan-2-yl)-1,3,2-dioxaborolane (45.8 g, 180 mmol, 2.00 eq), (1Z,5Z)-cycloocta-1,5-diene; 2,4-dimethyl-BLAHbicyclo[1.1.0]butane (2.39 g, 3.61 mmol, 0.04 eq) and 4-tert-butyl-2-(4-tert-butyl-2-pyridyl)pyridine (1.45 g, 5.41 mmol, 0.06 eq) in hexane (500 mL) was stirred at 100° C. under nitrogen atmosphere for 16 hours. The mixture was diluted with water (500 mL) and ethyl acetate (1000 mL). The separated organic layer was washed with brine (1×500 mL), dried over sodium sulfate, filtered and concentrated under vacuum. The residue was purified by column chromatography over silica gel (petroleum ether/ethyl acetate 100/1 to 10/1). The desired fractions were collected and concentrated under vacuum to give a mixture of tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy)

dimethylsilane (38.0 g, 85.3 mmol, 94.6% yield, 93% purity) as a light yellow oil. ESI MS m/z 415.5 [M+H]$^+$ Step D: 8-[tert-butyl(dimethyl)silyl]oxy-6-methoxy-naphthalen-2-ol To a solution of mixture (36.0 g, 86.9 mmol, 1.00 eq) of tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy)dimethylsilanein in acetone (400 mL) was added a solution of Oxone (58.7 g, 95.6 mmol, 1.10 eq) in H$_2$O (400 mL) at 0° C. The mixture was stirred at 0° C. for 1 hour. The mixture was quenched with 5% aqueous sodium thiosulfate solution (50 mL) and extracted with ethyl acetate (2×300 mL). The extracts were combined and washed with water (1×200 mL), brine (1×200 mL), dried over magnesium sulfate, filtered and the filtrate was concentrated under vacuum. The residue was purified by column chromatography over silica gel (petroleum ether/ethyl acetate 200/1 to 20/1). The desired fractions were collected and concentrated under vacuum to give 8-[tert-butyl(dimethyl)silyl]oxy-6-methoxy-naphthalen-2-ol (9.00 g, 28.4 mmol, 32.7% yield, 96% purity) as a colorless oil and 5-[tert-butyl(dimethyl)silyl]oxy-7-methoxy-naphthalen-2-ol (9.00 g, 29.0 mmol, 33.4% yield, 98% purity) as a white solid. ESI MS m/z 305.2 [M+H]$^+$ Step E: [5[tert-butyl(dimethyl)silyl]oxy-7-methoxy-2-naphthyl]trifluoromethanesulfonate To a solution of 5-[tert-butyl(dimethyl)silyl]oxy-7-methoxy-naphthalen-2-ol (11.0 g, 36.1 mmol, 1.00 eq) and DIEA (14.0 g, 108 mmol, 18.9 mL, 3.00 eq) in DCM (150 mL) was added Tf$_2$O (12.2 g, 43.4 mmol, 7.15 mL, 1.20 eq) dropwise at −40° C. The mixture was stirred for 1 hour. The mixture was diluted with dichloromethane (200 mL) and washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 10/1). The desired fractions were collected and concentrated under vacuum to give [5-[tert-butyl(dimethyl)silyl]oxy-7-methoxy-2-naphthyl]trifluoromethanesulfonate (13.0 g, 29.8 mmol, 82.4% yield, 100% purity) as a white solid. ESI MS m/z 436.9 [M+H]$^+$ Step F: tert-butyl-[(3-methoxy-6-methyl-1-naphthyl)oxy]-dimethyl-silane To a solution of [5[tert-butyl(dimethyl)silyl]oxy-7-methoxy-2-naphthyl]trifluoromethanesulfonate (12.5 g, 28.6 mmol, 1.00 eq) and K$_2$CO$_3$ (11.9 g, 85.9 mmol, 3.00 eq) in dioxane (160 mL) was added Pd(PPh$_3$)$_4$ (3.31 g, 2.86 mmol, 0.10 eq) and trimethylboroxine (14.4 g, 57.3 mmol, 16.0 mL, 2.00 eq) under nitrogen atmosphere. The reaction was heated to 100° C. for 16 hours. The mixture was diluted with ethyl acetate (200 mL) and then washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 5/1). The desired fractions were collected and concentrated under vacuum to give tert-butyl-[(3-methoxy-6-methyl-1-naphthyl)oxy]-dimethyl-silane (8.00 g, 24.6 mmol, 85.9% yield, 93% purity) as a colorless oil as red solid. ESI MS m/z 303.2 [M+H]$^+$ Step G: 3-methoxy-6-methyl-naphthalen-1-ol To a solution of tert-butyl-[(3-methoxy-6-methyl-1-naphthyl) oxy]-dimethyl-silane (8.00 g, 26.5 mmol, 1.00 eq) in THF (100 mL) was added TBAF (10.4 g, 39.7 mmol, 1.50 eq) at 0° C. The mixture was stirred at 0° C. for 3 hours. The mixture was diluted with water (100 mL) and ethyl acetate (200 mL). The separated organic layer was washed with brine (1×100 mL), dried over sodium sulfate, filtered and concentrated under vacuum. The residue was purified by column chromatography over silica gel (petroleum ether/ethyl acetate 50/1 to 5/1). The desired fractions were collected and concentrated under vacuum to give 3-methoxy-6-methyl-naphthalen-1-ol (4.70 g, 25.0 mmol, 94.4% yield) as a red solid. ESI MS m/z 188.4 [M+H]$^+$ Step H: 3-methoxy-6-methyl-1-naphthyl trifluoromethanesulfonate To a solution of 3-methoxy-6-methyl-naphthalen-1-ol (4.70 g, 25.0 mmol, 1.00 eq) and DIEA (9.68 g, 74.9 mmol, 13.1 mL, 3.00 eq) in DCM (3.00 mL) was added Tf$_2$O (8.45 g, 30.0 mmol, 4.94 mL, 1.20 eq) dropwise at −40° C. The mixture was stirred for 1 hour. The mixture was diluted with dichloromethane (200 mL) and washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 10/1). 3-methoxy-6-methyl-1-naphthyl trifluoromethanesulfonate (7.70 g, 24.0 mmol, 96.2% yield, 99.9% purity) was obtained as a colorless oil. ESI MS m/z 320.7 [M+H]$^+$.

The following intermediates were prepared according to the preparation for Intermediate 3, substituting the appropriate phenol for 2-bromo-3-fluorophenol.

| Intermediate No. | Structure | Name |
|---|---|---|
| Intermediate 35 | 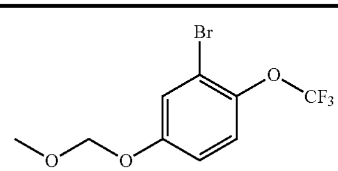 | 2-bromo-4-(methoxymethoxy)-1-(trifluoromethoxy)benzene |

-continued

| Intermediate No. | Structure | Name |
|---|---|---|
| Intermediate 36 | 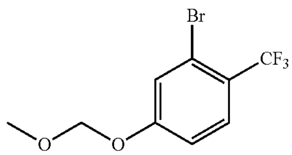 | 2-bromo-4-(methoxymethoxy)-1-(trifluoromethyl)benzene |
| Intermediate 37 | 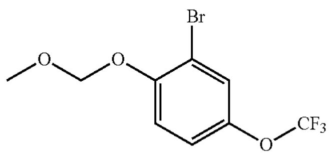 [SMILES: COCOc1ccc(OC(F)(F)F)cc1Br] | 2-bromo-1-(methoxymethoxy)-4-(trifluoromethoxy)benzene |
| Intermediate 38 | 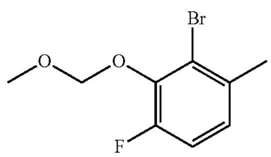 | 2-bromo-4-fluoro-3-(methoxymethoxy)-1-methylbenzene |
| Intermediate 39 | 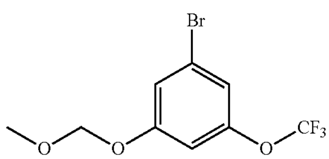 [SMILES: COCOc1cc(Br)cc(OC(F)(F)F)c1] | 1-bromo-3-(methoxymethoxy)-5-(trifluoromethoxy)benzene |
| Intermediate 40 | 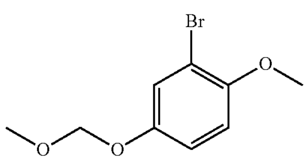 | 2-bromo-1-methoxy-4-(methoxymethoxy)benzene |
| Intermediate 41 | 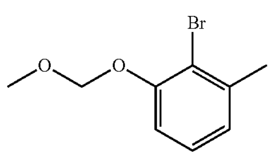 | 2-bromo-1-(methoxymethoxy)-3-methylbenzene |
| Intermediate 42 | 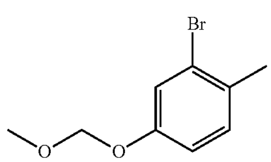 | 2-bromo-4-(methoxymethoxy)-1-methylbenzene |
| Intermediate 43 | 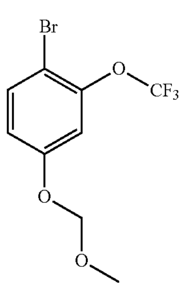 [SMILES: COCOc1ccc(Br)c(OC(F)(F)F)c1] | 1-bromo-4-(methoxymethoxy)-2-(trifluoromethoxy)benzene |

Intermediate 44

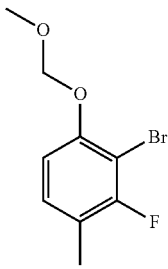

2-bromo-3-fluoro-1-(methoxymethoxy)-4-methyl-benzene

Step 1: 3-fluoro-4-methylphenol (1.016 g, 8.055 mmol) was placed in $Cs_2$ (3.9 mL, 64.44 mmol) and was cooled to 0° C. $Br_2$ (0.4150 mL, 8.055 mmol) was added and the mixture was stirred at room temperature for 2 hrs. 10% $Na_2S_2O_2$ was added and the mixture was extracted with DCM. The organic layers were combined, dried and filtered to provide 2-bromo-3-fluoro-4-methylphenol (1.389 g, 6.775 mmol, 84.10% yield) which was used directly in the next step.

Step 2: 2-bromo-3-fluoro-1-(methoxymethoxy)-4-methylbenzene was prepared according to the procedure for Intermediate 8 using 2-bromo-3-fluoro-4-methylphenol in place of 2-bromo-3-fluorophenol.

Intermediate 45

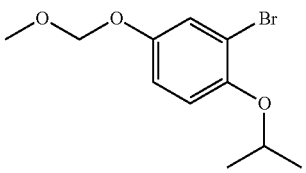

2-bromo-1-isopropoxy-4-(methoxymethoxy)benzene

Step 1: 4-isopropoxyphenol (1.00 g, 6.57 mmol) and TEA (1.83 mL, 13.1 mmol) were placed in DCM (25 mL). Acetyl chloride (7.56 mL, 7.56 mmol) was added dropwise and the reaction was stirred at room temperature for 2 hr. Water was added and the mixture was extracted with DCM. The organic layer was dried, filtered and concentrated to provide 4-isopropoxyphenyl acetate (1.24 g, 6.38 mmol, 97.2% yield) which was directly in the next step.

Step 2: 4-Isopropoxyphenyl acetate (1.24 g, 6.585 mmol) was placed in ACN (20 mL) and N-bromosuccinimide (1.173 g, 6.590 mmol) was added. The mixture was stirred for 18 hr. Water was added and the mixture was extracted with ether. The organic layers were combined, dried, and concentrated to provide 3-bromo-4-isopropoxyphenyl acetate (1.584 g, 5.800 mmol, 88.00% yield) which was directly in the next step.

Step 3: 3-Bromo-4-isopropoxyphenyl acetate (500 mg, 1.83 mmol) was placed in MeOH (7 mL). A solution of KOH (111 mg, 1.98 mmol) in water (2 mL) was added to mixture and was stirred for 1 hr at room temperature. The reaction mixture was adjusted to pH 3 by the addition of 1N HCl. The mixture was extracted with DCM. The extracts were combined, dried, filtered and concentrated to provide crude 3-bromo-4-isopropoxyphenol which was used directly the next reaction.

Step 4: 2-Bromo-1-isopropoxy-4-(methoxymethoxy)benzene was prepared according to the procedure for Intermediate 8 using 3-bromo-4-isopropoxyphenol in place of 2-bromo-3-fluorophenol

Intermediate 46

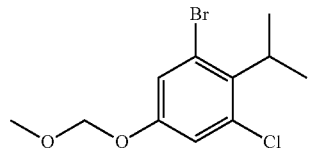

1-bromo-3-chloro-2-isopropyl-5-(methoxymethoxy) benzene

Step 1: 1-bromo-3-chloro-2-isopropyl-5-methoxybenzene (952 mg, 3.61 mmol) was placed in DCM (3 mL) and was cooled to 0° C. BBr3 (9030 μL, 9.03 mmol) was added and the reaction was stirred at 0° C. for 2 hr. Water was added and the mixture was extracted with DCM. The extracts were combined and concentrated. The resulting residue was purified by silica gel (0-20% EtOAc in hexane) to provide 3-bromo-5-chloro-4-isopropylphenol (575 mg, 2.30 mmol, 63.8% yield)

Step 2: 1-bromo-3-chloro-2-isopropyl-5-(methoxymethoxy)benzene was prepared according to the procedure for Intermediate 8 using 3-bromo-5-chloro-4-isopropylphenol in place of 2-

Intermediate 47

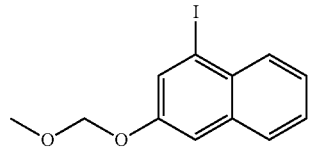

1-iodo-3-(methoxymethoxy)naphthalene

To a solution of 4-iodonaphthalen-2-ol (0.80 g, 3.0 mmol) in DCM (20 mL) was added N-ethyl-N-isopropylpropan-2-amine (1.1 mL, 5.9 mmol) and chloro(methoxy)methane (0.29 g, 3.6 mmol) and the reaction stirred at room temperature for 4 hours, with additional chloro(methoxy)methane (0.15 g) being added after 2 hours. The reaction was washed with brine and concentrated in vacuo. The material was purified by chromatography using a gradient of 0 to 10% EtOAc/hexanes as the eluent to give 1-iodo-3-(methoxymethoxy)naphthalene (0.80 g, 2.5 mmol, 86% yield).

Intermediate 48

3-benzyloxy-1-bromo-naphthalene

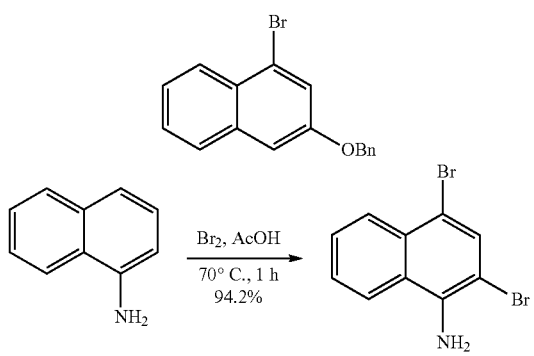

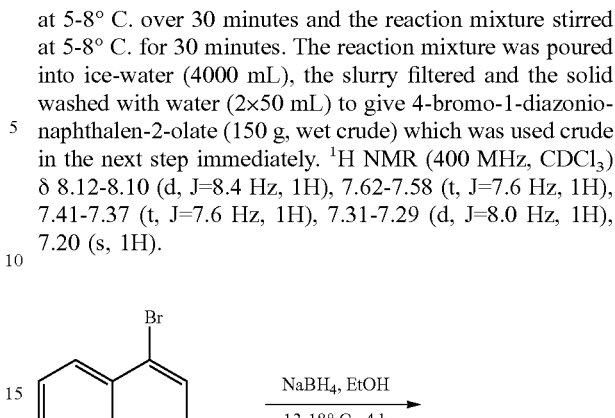

Step A: 2,4-dibromonaphthalen-1-amine

To a solution of Br₂ (246 g, 1.54 mol, 79.3 mL) in AcOH (750 mL) was added a solution of naphthalen-1-amine (101 g, 705 mmol, 99.0 mL) in AcOH (500 mL) at room temperature and the reaction stirred at 70° C. for 1 hour. The reaction mixture was cooled to room temperature and filtered. The filter cake was washed with AcOH (300 mL). The solid was next suspended in 20% aqueous of NaOH (1.2 L). The mixture was stirred for 20 minutes and filtered. The solid was washed with water (1 L) and dried under vacuum to give 2,4-dibromonaphthalen-1-amine (200 g, 664 mmol, 94.2% yield) as gray solid. ES+APCI MS m/z 301.9 [M+H]⁺.

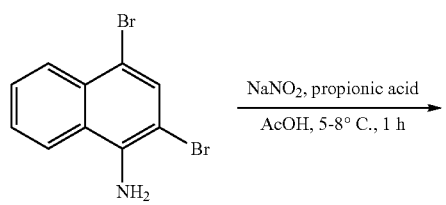

Step B: 4-bromo-1-diazonio-naphthalen-2-olate

To a solution of 2,4-dibromonaphthalen-1-amine (60.0 g, 199 mmol) in AcOH (900 mL) and propionic acid (150 mL) was added NaNO₂ (16.5 g, 239 mmol, 13.0 mL) portionwise at 5-8° C. over 30 minutes and the reaction mixture stirred at 5-8° C. for 30 minutes. The reaction mixture was poured into ice-water (4000 mL), the slurry filtered and the solid washed with water (2×50 mL) to give 4-bromo-1-diazonio-naphthalen-2-olate (150 g, wet crude) which was used crude in the next step immediately. ¹H NMR (400 MHz, CDCl₃) δ 8.12-8.10 (d, J=8.4 Hz, 1H), 7.62-7.58 (t, J=7.6 Hz, 1H), 7.41-7.37 (t, J=7.6 Hz, 1H), 7.31-7.29 (d, J=8.0 Hz, 1H), 7.20 (s, 1H).

Step C: 4-bromonaphthalen-2-ol

To a solution of 4-bromo-1-diazonio-naphthalen-2-olate (100 g, 402 mmol) in EtOH (2.00 L) was added portion-wise NaBH₄ (30.4 g, 803 mmol) at 13-15° C. over 1 hour and the reaction stirred at 15-18° C. for 3 hours. The reaction was filtered and concentrated to dryness. The residue was dissolved in DCM (1000 mL) and washed with water (500 mL×2). The organics were dried over Na₂SO₄ and concentrated to dryness. The residue was purified by chromtography eluting with petroleum ether/EtOAc (60/1→10/1) and material re-purified by reversed phase HPLC to give 4-bromonaphthalen-2-ol (40.0 g, 139 mmol, 17.3% yield, 77.4% purity) as a gray solid. ¹H NMR (400 MHz, CDCl₃) δ 8.07-8.05 (d, J=8.0 Hz, 1H), 7.60-7.58 (d, J=7.6 Hz, 1H), 7.41-7.36 (m, 3H), 7.07 (s, 1H).

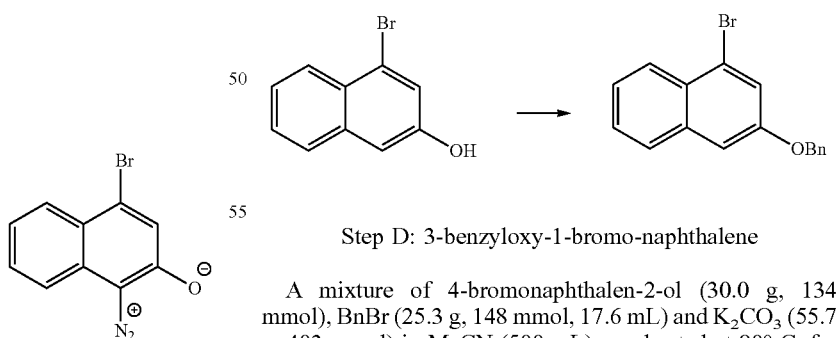

Step D: 3-benzyloxy-1-bromo-naphthalene

A mixture of 4-bromonaphthalen-2-ol (30.0 g, 134 mmol), BnBr (25.3 g, 148 mmol, 17.6 mL) and K₂CO₃ (55.7 g, 403 mmol) in MeCN (500 mL) was heated at 80° C. for 1 hr. The reaction mixture was filtered and concentrated to dryness. The residue was purified by silica gel column eluting with PE/EA (100/1 to 60/1) to give 3-benzyloxy-1-bromo-naphthalene (40.0 g, 128 mmol, 95% yield). ¹H NMR (400 MHz, CDCl₃) δ 8.19-8.17 (d, J=8.0 Hz, 1H), 7.75-7.32 (d, J=8.8 Hz, 1H), 7.64-7.63 (d, J=2.4 Hz, 1H), 7.52-7.37 (m, 7H), 7.23-7.21 (d, J=2.0 Hz, 1H), 5.2 (s, 2H).

Intermediate 49 benzyl 4-(7-(3-(benzyloxy)naphthalen-1-yl)-2-(methylsulfinyl)-5,6,7,8-tetrahydropyrido[3,4-d]pyrimidin-4-yl)piperazine-1-carboxylate

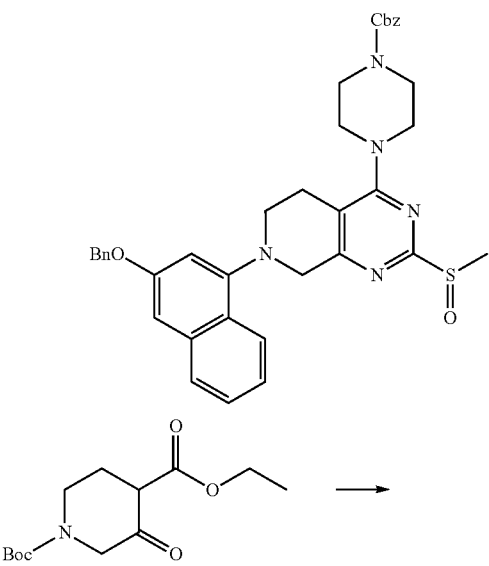

Step A: tert-butyl 4-hydroxy-2-methylsulfanyl-6,8-dihydro-5H-pyrido[3,4-d]pyrimidine-7-carboxylate To a solution of 1-tert-butyl 4-ethyl 3-oxopiperidine-1,4-dicarboxylate (50.0 g, 184 mmol) in MeOH (1.00 L) under nitrogen was added NaOMe (49.8 g, 921 mmol) and 2-methylisothiourea (62.4 g, 331 mmol, $H_2SO_4$). The reaction mixture was stirred at 25° C. for 16 hours. HCl (2 M) was added to the reaction mixture until pH ~5 and then the mixture was concentrated under reduced pressure. The residue was suspended in 300 mL of ethyl acetate and 300 mL of water. The suspension was filtered. The organic phase was washed with water (1×300 mL), brine (1×200 mL), dried over $Na_2SO_4$, filtered and concentrated to give tert-butyl 4-hydroxy-2-methylsulfanyl-6,8-dihydro-5H-pyrido[3,4-d]pyrimidine-7-carboxylate (51.0 g, 138 mmol, 75.4% yield, 81.0% purity) which was used directly in the next reaction. ES+APCI MS m/z 298.2 [M+H]+.

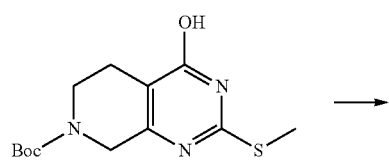

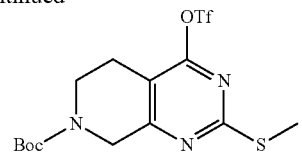

Step B: tert-butyl 2-methylsulfanyl-4-(trifluoromethylsulfonyloxy)-6,8-dihydro-5H-pyrido[3,4-d]pyrimidine-7-carboxylate To a solution of tert-butyl 4-hydroxy-2-methylsulfanyl-6,8-dihydro-5H-pyrido[3,4-d]pyrimidine-7-carboxylate (51.0 g, 171 mmol) in DCM (500 mL) was added DIEA (44.3 g, 343 mmol, 59.9 mL) and $Tf_2O$ (72.6 g, 257 mmol, 42.4 mL) sequentially at 0° C. under nitrogen. The reaction mixture was warmed up to 25° C. and stirred for 16 hours. The reaction mixture was concentrated and the residue purified by column chromatography eluting with EtOAc/Petroleum 0→10% to give tert-butyl 2-methylsulfanyl-4-(trifluoromethylsulfonyloxy)-6,8-dihydro-5H-pyrido[3,4-d]pyrimidine-7-carboxylate (46.0 g, 107 mmol, 62.4% yield). ES+APCI MS m/z 430.2 [M+H]+.

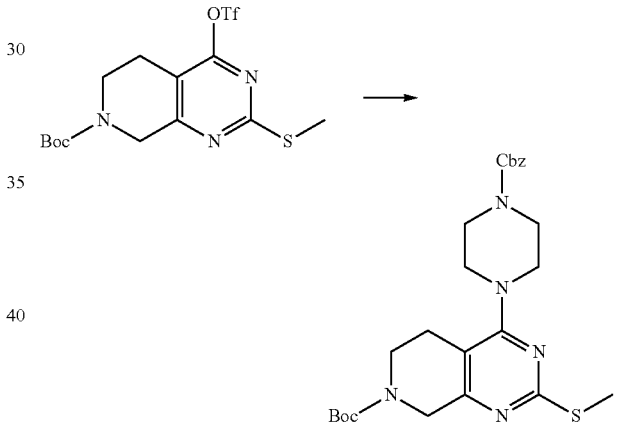

Step C: tert-butyl 4-(4-benzyloxycarbonylpiperazin-1-yl)-2-methylsulfanyl-6,8-dihydro-5H-pyrido[3,4-d]pyrimidine-7-carboxylate To a solution of tert-butyl 2-methylsulfanyl-4-(trifluoromethylsulfonyloxy)-6,8-dihydro-5H-pyrido[3,4-d]pyrimidine-7-carboxylate (46.0 g, 107 mmolin DMF (500 mL) was added DIEA (27.7 g, 214 mmol, 37.4 mL) and benzyl piperazine-1-carboxylate (25.9 g, 117 mmol, 22.7 mL). The reaction was heated to 100° C. for one hour under $N_2$ atmosphere. The reaction mixture was poured into ethyl acetate (300 mL). The mixture was washed with $H_2O$ (300 mL×3). The organic phase was washed with brine (200 mL), dried over anhydrous $Na_2SO_4$, concentrated in vacuo. The residue was purified by column chromatography using 0→20% EtOAc/Petroleum as eluent to give tert-butyl 4-(4-benzyloxycarbonylpiperazin-1-yl)-2-methylsulfanyl-6,8-dihydro-5H-pyrido[3,4-d]pyrimidine-7-carboxylate (51.0 g, 96.9 mmol, 90.5% yield, 92.0% purity) ES+APCI MS m/z 500.3 [M+H]+.

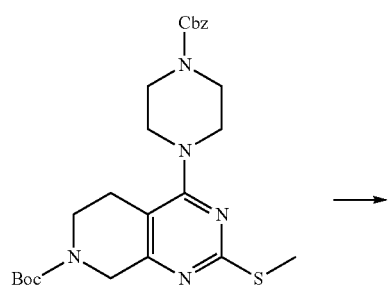

Step D: Benzyl 4-(2-methylsulfanyl-5,6,7,8-tetrahydropyrido[3,4-d]pyrimidin-4-yl)piperazine-1-carboxylate To a solution of tert-butyl 4-(4-benzyloxycarbonylpiperazin-1-yl)-2-methylsulfanyl-6,8-dihydro-5H-pyrido[3,4-d]pyrimidine-7-carboxylate (25.0 g, 50 mmol) in DCM (50 mL) was added TFA (85.6 g, 750 mmol, 55.6 mL). The mixture was stirred at 25° C. for 1 hour. The reaction mixture was concentrated under reduced pressure and the residue was dissolved in 300 mL of ethyl acetate and 300 mL of water and Na$_2$CO$_3$ added until pH ~8. The organic layer was washed with water (1×300 mL), brine (1×200 mL) and dried over Na$_2$SO$_4$, filtered and concentrated under reduced pressure to give benzyl 4-(2-methylsulfanyl-5,6,7,8-tetrahydropyrido[3,4-d]pyrimidin-4-yl)piperazine-1-carboxylate. The product was used directly to the next step without further purification. ES+APCI MS m/z 400.2 [M+H]$^+$.

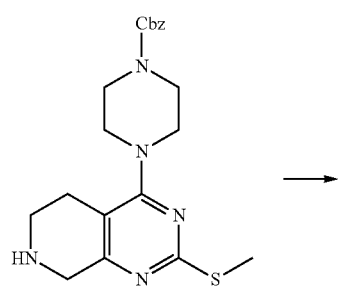

Step E: benzyl 4-[7-(3-benzyloxy-1-naphthyl)-2-methylsulfanyl-6,8-dihydro-5H-pyrido[3,4-d]pyrimidin-4-yl]piperazine-1-carboxylate A mixture of 3-benzyloxy-1-bromo-naphthalene (16.3 g, 52.1 mmol), benzyl 4-(2-methylsulfanyl-5,6,7,8-tetrahydropyrido[3,4-d]pyrimidin-4-yl)piperazine-1-carboxylate (16.0 g, 40.1 mmol), Cs$_2$CO$_3$ (32.6 g, 100 mmol), Pd$_2$(dba)$_3$ (5.50 g, 6.01 mmol) and RuPhos (3.74 g, 8.01 mmol) in dioxane (300 mL) was degassed with N$_2$ 3 times and the mixture stirred at 85° C. for 5 hour under N$_2$ atmosphere. The reaction mixture was quenched by addition water (200 mL) at 0° C., and extracted with EtOAc (3×200 mL). The combined organic layers were washed with brine (3×150 mL), dried over Na$_2$SO$_4$, filtered and concentrated under reduced pressure. The residue was purified by column chromatography eluting with 10→20% MeOH/DCM to give benzyl 4-[7-(3-benzyloxy-1-naphthyl)-2-methylsulfanyl-6,8-dihydro-5H-pyrido[3,4-d]pyrimidin-4-yl]piperazine-1-carboxylate (16.0 g, 22.8 mmol, 56.9% yield, 90.0% purity ES+APCI MS m/z 632.5 [M+H]$^+$.

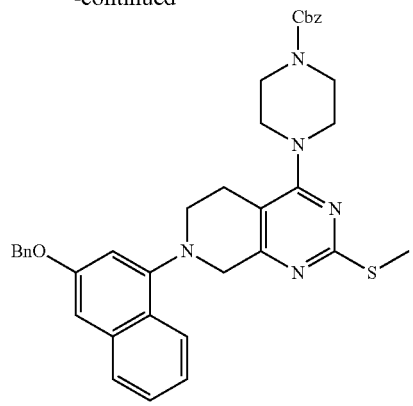

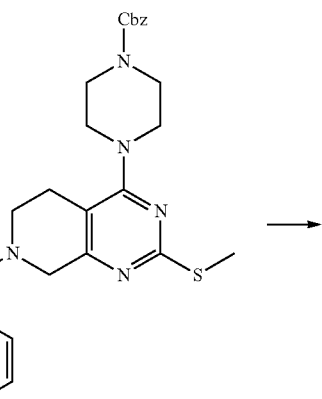

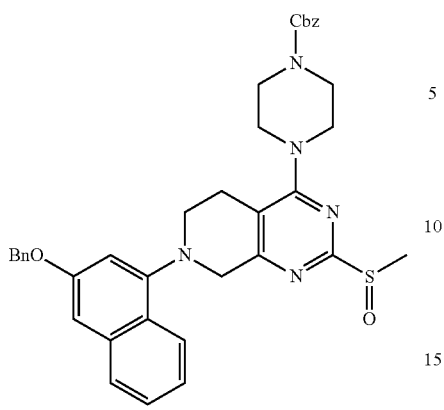

Step F: benzyl 4-[7-(3-benzyloxy-1-naphthyl)-2-methylsulfinyl-6,8-dihydro-5H-pyrido[3,4-d]pyrimidin-4-yl]piperazine-1-carboxylate To a solution of benzyl 4-[7-(3-benzyloxy-1-naphthyl)-2-methylsulfanyl-6,8-dihydro-5H-pyrido[3,4-d]pyrimidin-4-yl]piperazine-1-carboxylate (8.00 g, 12.7 mmol) in DCM (200 mL) was added m-CPBA (2.73 g, 12.7 mmol, 80.0% purity) at 0° C. under nitrogen atmosphere. The reaction mixture was stirred for two hours under 0° C. The reaction mixture was quenched by addition $Na_2S_2O_3$ (10 mL) at 0° C., and then diluted with water (100 mL) and extracted with DCM (200 mL). The combined organic layers were washed with brine (200 mL), dried over $Na_2SO_4$, filtered and concentrated under reduced pressure. The residue was purified by column chromatography eluting with 0→10% MeOH/DCM to benzyl 4-[7-(3-benzyloxy-1-naphthyl)-2-methylsulfinyl-6,8-dihydro-5H-pyrido[3,4-d]pyrimidin-4-yl]piperazine-1-carboxylate (3.50 g, 4.92 mmol, 38.8% yield, 91.0% purity) ES+APCI MS m/z 648.5 [M+H]$^+$.

Intermediate 50 tert-butyl 4-(4-benzyloxycarbonylpiperazin-1-yl)-2-methylsulfonyl-6,8-dihydro-5H-pyrido[3,4-d]pyrimidine-7-carboxylate

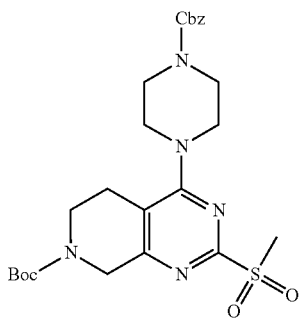

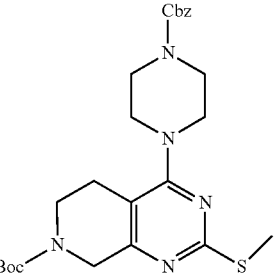

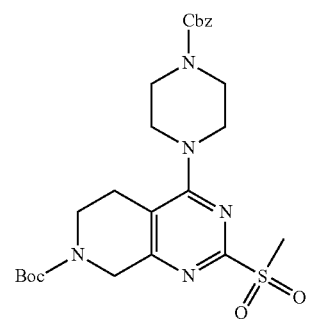

Step A: tert-butyl 4-(4-benzyloxycarbonylpiperazin-1-yl)-2-methylsulfonyl-6,8-dihydro-5H-pyrido[3,4-d]pyrimidine-7-carboxylate To a stirred solution of tert-butyl4-(4-benzyloxycarbonylpiperazin-1-yl)-2-methylsulfanyl-6,8-dihydro-5H-pyrido[3,4-d]pyrimidine-7-carboxylate (14.4 g, 28.9 mmol) in DCM (150 mL) was added m-CPBA solid (17.4 g, 101 mmol) at 0° C. under nitrogen. After stirring at 0° C. for 2 hours, the reaction mixture was diluted with water (300 mL) and basified with saturated $NaHCO_3$ aqueous solution to pH ~8 and then extracted with DCM (3×200 mL). The combined organic layers were washed with brine (3×200 mL), dried over $Na_2SO_4$, filtered and concentrated under reduced pressure. The residue was purified by column chromatography ($SiO_2$, Petroleum ether/Ethyl acetate 10/1 to 1/2) to give tert-butyl 4-(4-benzyloxycarbonylpiperazin-1-yl)-2-methylsulfonyl-6,8-dihydro-5H-pyrido[3,4-d]pyrimidine-7-carboxylate (11.0 g, 19.7 mmol, 68.6% yield, 95.4% purity). ES+APCI MS m/z 532.1 [M+H]$^+$.

Intermediate 51

4-bromo-5-methyl-1-tetrahydropyran-2-yl-indazole

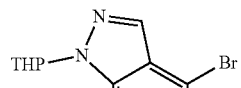
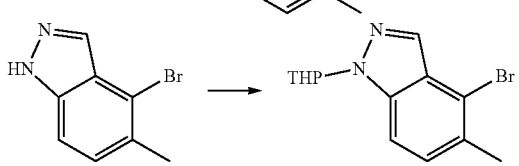

Step A:
4-bromo-5-methyl-1-tetrahydropyran-2-yl-indazole

To a mixture of 4-bromo-5-methyl-1H-indazole (3 g, 14.2 mmol) and 3,4-dihydro-2H-pyran (2.39 g, 28.4 mmol, 2.60 mL) in DCM (30 mL) was added TsOH*H₂O (270 mg, 1.42 mmol) and the mixture stirred at 15° C. for 2 hours. After completion, the reaction mixture was concentrated under vacuum and the residue purified by column chromatography using 5→20& EtOAc/Petroleum Ether as eluent to give 4-bromo-5-methyl-1-tetrahydropyran-2-yl-indazole (4 g, 13.6 mmol, 95.3% yield) as white solid. ¹H NMR (400 MHz, chloroform-d) δ 8.01 (s, 1H), 7.47 (d, J=8.4 Hz, 1H), 7.25 (d, J=8.4 Hz, 1H), 5.70 (dd, J=2.8, 9.2 Hz, 1H), 4.05-3.96 (m, 1H), 3.79-3.70 (m, 1H), 2.66-2.44 (m, 4H), 2.25-2.04 (m, 2H), 1.84-1.56 (m, 3H).

Intermediate 52

4-bromo-5-methoxy-1-(tetrahydro-2H-pyran-2-yl)-1H-indazole

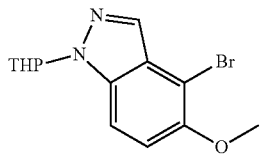

4-bromo-5-methoxy-1-(tetrahydro-2H-pyran-2-yl)-1H-indazole was prepared following Intermediate 51 substituting 4-bromo-5-methoxy-1H-indazole for 4-bromo-5-methyl-1H-indazole in Step A. ¹H NMR (400 MHz, chloroform-d) δ 8.00 (s, 1H), 7.53 (d, J=9.2 Hz, 1H), 7.16 (d, J=9.2 Hz, 1H), 5.70 (dd, J=2.8, 9.2 Hz, 1H), 4.04-3.98 (m, 1H), 3.96 (s, 3H), 2.55-2.49 (m, 1H), 2.23-2.05 (m, 2H), 1.83-1.69 (m, 3H).

Intermediate 53

3-(benzyloxy)-1-bromo-2-methylnaphthalene

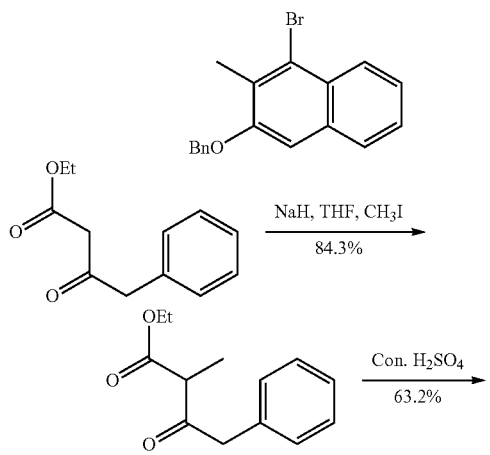

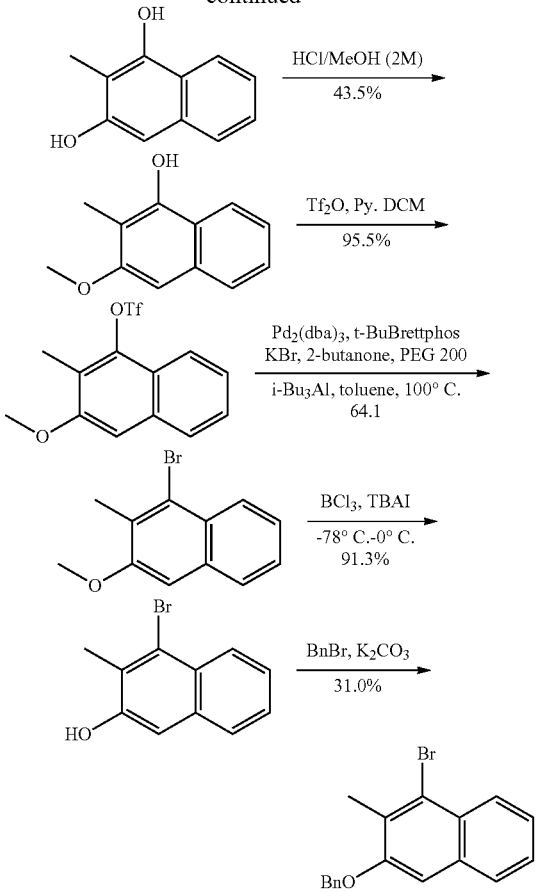

Step A: ethyl 2-methyl-3-oxo-4-phenyl-butanoate

To a dried 250 ml three-necked flask was added ethyl 3-oxo-4-phenyl-butanoate (4.00 g, 19.4 mmol), THF (50.0 mL), sodium hydride (931 mg, 23.3 mmol) and the reaction stirred for 0.5 hours at 0° C. A solution of methyl iodide (3.03 g, 21.3) was next added drop-wise. After addition was completed, the reaction mixture was warmed to 20° C. and stirred for two hours at 20° C. The reaction mixture was quenched by addition of water (10.0 mL) at 20° C. and then diluted with ethyl acetate (20.0 mL) and the layers separated. The aqueous layer was next extracted with ethyl acetate (20.0 mL×3). The combined organic layers were washed with brine (30.0 mL), dried over anhydrous sodium sulfate, filtered and concentrated under reduced pressure to give a residue. The residue was purified by column chromatography (SiO2, Petroleum ether: Ethyl acetate 20:1 to 10:1) to give ethyl 2-methyl-3-oxo-4-phenyl-butanoate (3.60 g, 16.3 mmol, 84.3% yield) as a colorless oil. ¹H NMR (400 MHz, CDCl₃) δ=7.38-7.28 (m, 3H), 7.25-7.19 (m, 2H), 4.22-4.15 (m, 2H), 3.87 (d, J=2.0 Hz, 2H), 3.65 (q, J=7.2 Hz, 1H), 1.34 (d, J=7.2 Hz, 3H), 1.30-1.26 (m, 3H).

Step B: 2-methylnaphthalene-1,3-diol

A solution of ethyl 2-methyl-3-oxo-4-phenyl-butanoate (3.60 g, 16.3 mmol) in concentrated sulfuric acid (19.9 g, 203 mmol) was stirred at 15° C. for 12 hours. The reaction mixture was poured into ice-water (30.0 mL) and the resulting solid collected by filtration and dried under vacuum to afford 2-methylnaphthalene-1,3-diol (1.80 g, 10.3 mmol, 63.2% yield) as a red solid. $^1$H NMR (400 MHz, CDCl$_3$) δ=8.02 (d, J=8.0 Hz, 1H), 7.65-7.54 (m, 1H), 7.41 (t, J=7.2 Hz, 1H), 7.36-7.31 (m, 1H), 6.80 (s, 1H), 4.29-4.20 (s, 2H), 2.41-2.24 (s, 3H).

Step C: 3-methoxy-2-methyl-naphthalen-1-ol 2-methylnaphthalene-1,3-diol (1.70 g, 9.76 mmol) was added to HCl/MeOH (2 M, 35.0 mL) and the result mixture was stirred at 30° C. for 3 days. The reaction was concentrated in vacuo and the residue purified by Prep-TLC (Petroleum ether: Ethyl acetate 1:1) to give 3-methoxy-2-methyl-naphthalen-1-ol (800 mg, 4.25 mmol, 43.5% yield) as a white solid. $^1$H NMR (400 MHz, CDCl$_3$) δ=8.02 (d, J=8.4 Hz, 1H), 7.69 (d, J=8.4 Hz, 1H), 7.44-7.38 (m, 1H), 7.37-7.31 (m, 1H), 6.79 (s, 1H), 5.14 (s, 1H), 3.94 (s, 3H), 2.29 (s, 3H).

Step D: (3-methoxy-2-methyl-1-naphthyl)trifluoromethanesulfonate

To a mixture of 3-methoxy-2-methyl-naphthalen-1-ol (800 mg, 4.25 mmol.) and pyridine (504 mg, 6.38 mmol) in DCM (10.0 mL) was added trifluoroacetic anhydride (1.44 g, 5.10 mmol) dropwise at 0° C. under N$_2$ atmosphere. The mixture was warmed to 20° C. and stirred for an additional 5 hours. The solvent was removed under vacuum and the residue purified by Prep-TLC (Petroleum ether:Ethyl acetate 1:1) to give (3-methoxy-2-methyl-1-naphthyl)trifluoromethanesulfonate (1.30 g, 4.06 mmol, 95.5% yield) as a white solid. $^1$H NMR (400 MHz, CDCl$_3$) δ=7.97 (d, J=7.6 Hz, 1H), 7.79-7.74 (m, 1H), 7.52-7.43 (m, 2H), 7.14 (s, 1H), 3.99 (s, 3H), 2.42 (s, 3H)

Step E: 1-bromo-3-methoxy-2-methyl-naphthalene

In a sealed tube was added (3-methoxy-2-methyl-1-naphthyl)trifluoromethanesulfonate (466 mg, 1.45 mmol), t-Bu-Brettphos (154 mg, 290 umol), potassium bromide (259 mg, 2.17 mmol), PEG-200 (175 mg), 2-butanone (157 mg, 2.17 mmol) and Pd$_2$(dba)$_3$ (133 mg, 145 umol) in toluene (10.0 mL) and the mixture de-gassed with N2 for 5 minutes. Next, triisobutylaluminum (431 mg, 2.17 mmol) was added dropwise at 20° C. The mixture was heated to 100° C. for 24 hrs. The reaction mixture was poured into water (30.0 mL) and the aqueous layer extracted with ethyl acetate (20.0 mL×3). The combined organics were washed with brine (30.0 mL), dried over anhydrous sodium sulfate and concentrated in vacuo to give a residue which was pre-purified by column chromatography (Petroleum ether:Ethyl acetate 10:1) and then by Prep-TLC (Petroleum ether: Ethyl acetate 10:1) to give 1-bromo-3-methoxy-2-methyl-naphthalene (700 mg, 2.79 mmol, 64.1% yield) as a white solid. $^1$H NMR (400 MHz, CDCl$_3$) δ=8.26-8.17 (m, 1H), 7.73-7.69 (m, 1H), 7.47-7.40 (m, 2H), 7.09 (s, 1H), 3.98-3.95 (m, 3H), 2.56 (s, 3H).

Step F: 4-bromo-3-methyl-naphthalen-2-ol

To a solution of 1-bromo-3-methoxy-2-methyl-naphthalene (580 mg, 2.31 mmol) and tetrabutylammonium iodide (2.13 g, 5.78 mmol) in DCM (11.0 mL) cooled to −78° C. was added a solution of BCl$_3$ (1 M, 5.78 mL) dropwise over a period of 10 minutes while under N$_2$. The reaction mixture was warmed to 0° C. and stirred for 2 hours at room temperature. Next the solvent was removed under vacuum and the residue was purified by Prep-TLC (Petroleum ether: Ethyl acetate 5:1) to give 4-bromo-3-methyl-naphthalen-2-ol (500 mg, 2.11 mmol, 91.3% yield) as a white solid. $^1$H NMR (400 MHz, CDCl$_3$) δ=8.26-8.15 (m, 1H), 7.63 (dd, J=3.6, 6.0 Hz, 1H), 7.45-7.38 (m, 2H), 7.11 (s, 1H), 5.09 (s, 1H), 2.60 (s, 3H), 1.56 (s, 3H).

Step G: 3-benzyloxy-1-bromo-2-methyl-naphthalene

To a mixture of 4-bromo-3-methyl-naphthalen-2-ol (265 mg, 1.12 mmol) and benzyl bromide (201 mg, 1.18 mmol) in acetonitrile (3.00 mL) was added potassium carbonate (310 mg, 2.24 mmol) in one portion at 20° C. under N$_2$. The mixture was next stirred at 60° C. for two hours. The solvent was removed under vacuum and the residue purified by Prep-TLC (Petroleum ether: Ethyl acetate 5:1) to give the 3-benzyloxy-1-bromo-2-methyl-naphthalene (250 mg, 695 umol, 31.0% yield, 91.0% purity) as a white solid. ES+APCI MS m/z 327.0, 329.0 [M+H]$^+$.

Intermediate 54 tert-butyl-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate

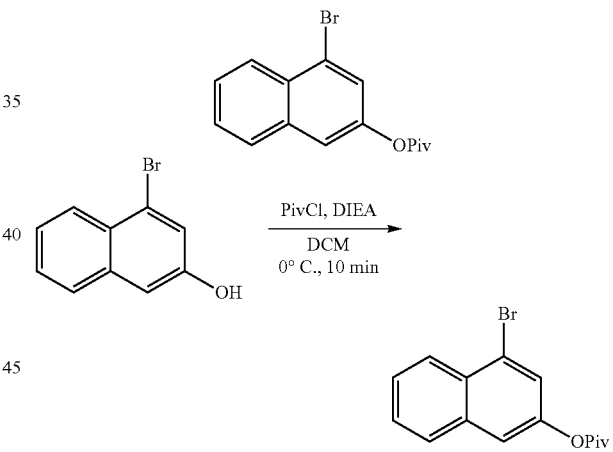

Step A: (4-bromo-2-naphthyl) 2,2-dimethylpropanoate

To a solution of 4-bromonaphthalen-2-ol (10 g, 44.8 mmol) and TEA (9.07 g, 89.7 mmol) in DCM (200 mL) was added 2,2-dimethylpropanoyl chloride (8.11 g, 67.2 mmol) at 0° C. The reaction mixture was stirred at 0° C. for 10 min. T reaction mixture was quenched by addition of water (50 mL) and the layers separated. The organic layer was washed with brine (30 mL), dried over Na$_2$SO$_4$ filtered and concentrated under vacuum. The residue was purified by silica gel chromatography (PE:EA=1:0 to 100:1) to give (4-bromo-2-naphthyl) 2,2-dimethylpropanoate (9 g, 29.3 mmol, 65.4% yield) as a red oil. $^1$H NMR (400 MHz, CHLOROFORM-d) δ=8.22 (d, J=8.0 Hz, 1H), 7.83-7.77 (m, 1H), 7.63-7.49 (m, 4H), 1.41 (s, 9H).

Intermediate 55 tert-butyl 4-(2-(3-morpholinopropoxy)-5,6,7,8-tetra-hydropyrido[3,4-d]pyrimidin-4-yl) piperazine-1-carboxylate

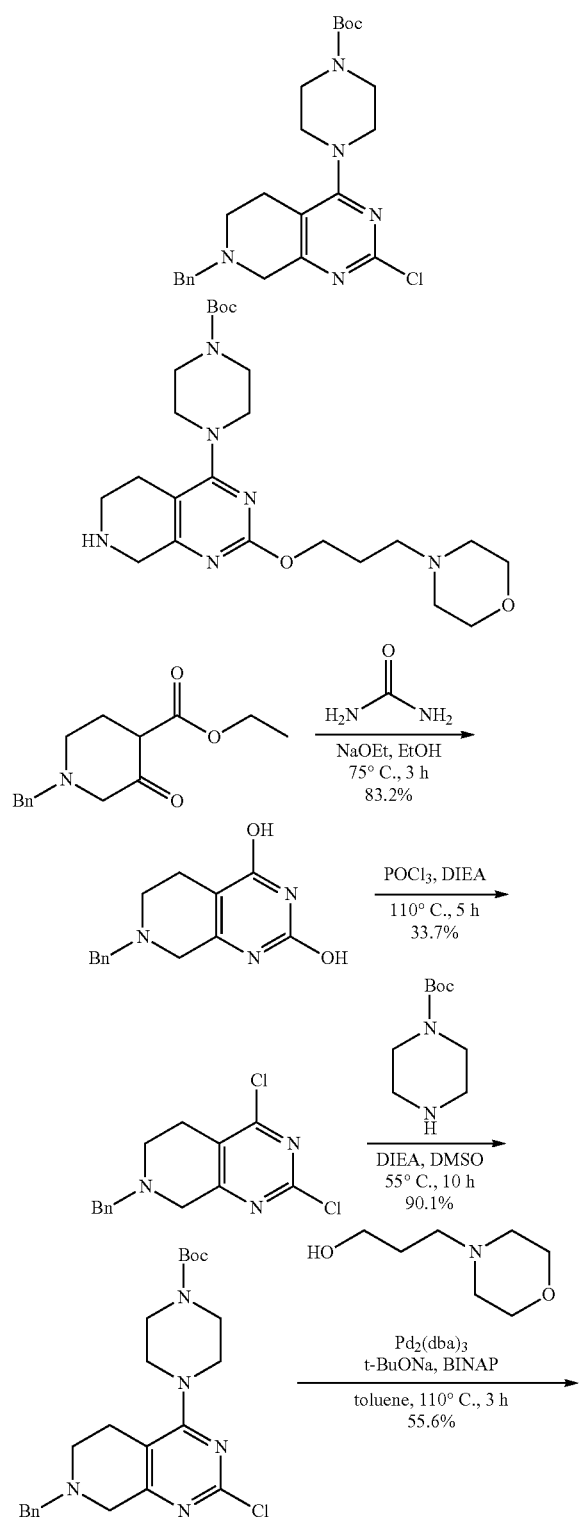

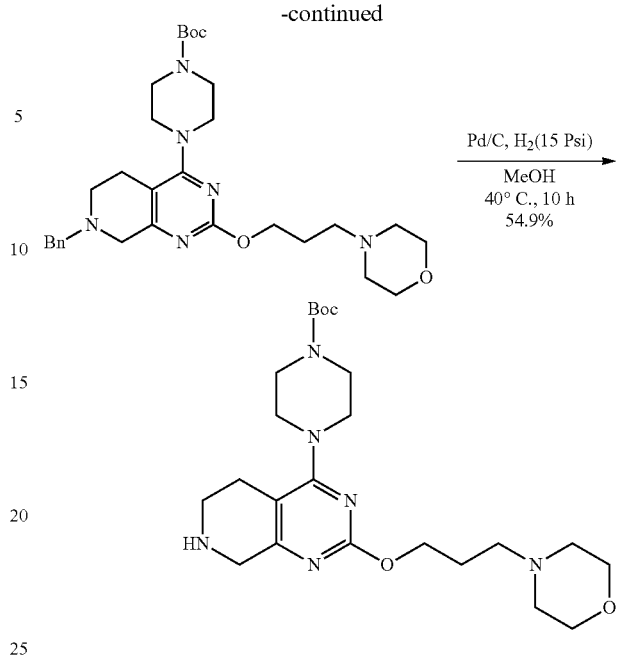

Step A: 7-benzyl-6,8-dihydro-5H-pyrido[3,4-d]pyrimidine-2,4-diol

To EtOH (600 mL) was added Na (5.56 g, 241 mmol) in portions and the mixture stirred for 1 hour. To this solution was added ethyl 1-benzyl-3-oxo-piperidine-4-carboxylate (30.0 g, 100 mmol) and urea (14.5 g, 242 mmol) and the reaction mixture stirred at 75° C. for 36 hours. The solvent was removed under vacuum and the residue dissolved in water (50 mL) and acidified by addition of HCl (120 mL, 2M) at which point a solid precipitated. The solid was filtered and the filter cake dried under vacuum to give 7-benzyl-6,8-dihydro-5H-pyrido[3,4-d]pyrimidine-2,4-diol (22.0 g, 83.8 mmol). (400 MHz, DMSO-$d_6$) δ=10.97 (br s, 1H), 10.66 (br s, 1H), 7.55-6.95 (m, 5H), 3.81-3.50 (m, 2H), 3.26-2.91 (m, 2H), 2.77-2.58 (m, 2H), 2.34-2.09 (m, 2H).

Step B: 7-benzyl-2,4-dichloro-6,8-dihydro-5H-pyrido[3,4-d]pyrimidine

To a solution of DIEA (30.1 g, 233 mmol) in POCl$_3$ (330 g, 2.15 mol) was added 7-benzyl-6,8-dihydro-5H-pyrido[3,4-d] pyrimidine-2,4-diol (20.0 g, 77.7 mmol) and the reaction mixture stirred at 110° C. for 5 hours. Upon completion, the reaction mixture was concentrated under vacuum. The residue was dissolved in DCM (400 mL) and poured into sat. NaHCO$_3$ (200 mL) and the layers separated. The aqueous layer was extracted with DCM (2×400 mL). The combined organics were washed with brine (100 mL), dried over Na$_2$SO$_4$ and concentrated under vacuum. The residue was purified by silica gel chromatography (PE/DCM=10/1 to 0/1) to give 7-benzyl-2,4-dichloro-6,8-dihydro-5H-pyrido [3,4-d]pyrimidine (7.70 g, 26.2 mmol). (300 MHz, chloroform-d) δ=7.43-7.28 (m, 5H), 3.73 (s, 2H), 3.66 (br s, 2H), 2.84 (br s, 4H).

Step C: tert-butyl 4-(7-benzyl-2-chloro-6,8-dihydro-5H-pyrido[3,4-d]pyrimidin-4-yl) piperazine-1-carboxylate To a solution of 7-benzyl-2,4-dichloro-6,8-dihydro-5H-pyrido[3,4-d]pyrimidine (17.3 g, 58.8 mmol) in DMSO (200 mL) was added DIEA (19.0 g, 147 mmol) and tert-butyl piperazine-1-carboxylate (11.5 g, 61.7 mmol) and the mixture stirred at 55° C. for 10 hours. The reaction mixture was poured into ethyl acetate (200 mL) and washed with water (3×200 mL). The combined organics were washed with brine (200 mL), dried over anhydrous Na$_2$SO$_4$ and concentrated under vacuum to give a residue. The residue was purified by trituration from MTBE (200 mL) to give tert-butyl 4-(7-benzyl-2-chloro-6,8-dihydro-5H-pyrido[3,4-d]pyrimidin-4-yl) piperazine-1-carboxylate (24 g, 52.9 mmol). ES+APCI MS m/z 444.2 [M+H]$^+$.

Step D: tert-Butyl 4-[7-benzyl-2-(3-morpholinopropoxy)-6,8-dihydro-5H-pyrido[3,4-d]pyrimidin-4-yl] piperazine-1-carboxylate A mixture of 3-morpholinopropan-1-ol (11.8 g, 81.1 mmol), tert-butyl 4-(7-benzyl-2-chloro-6,8-dihydro-5H-pyrido[3,4-d]pyrimidin-4-yl)piperazine-1-carboxylate (18 g, 40.5 mmol), BINAP (5.05 g, 8.11 mmol), t-BuONa (9.74 g, 101 mmol) and Pd$_2$(dba)$_3$ (3.71 g, 4.05 mmol) in toluene (300 mL) was degassed and purged with N$_2$ 3 times, and the mixture stirred at 110° C. for 3 hours under N$_2$ atmosphere. The reaction mixture was poured into H$_2$O (200 mL) and the aqueous layer extracted with ethyl acetate (3×300 mL). The combined organics were washed with brine (200 mL), dried over anhydrous Na$_2$SO$_4$ and concentrated under vacuum to give a residue. The residue was purified by column chromatography (SiO$_2$, Petroleum ether/Ethyl acetate=100/1 to 5/1) to give tert-Butyl 4-[7-benzyl-2-(3-morpholinopropoxy)-6,8-dihydro-5H-pyrido[3,4-d]pyrimidin-4-yl] piperazine-1-carboxylate (14 g, 22.5 mmol). ES+APCI MS m/z 553.4 [M+H]$^+$.

Step E: tert-butyl 4-[2-(3-morpholinopropoxy)-5,6,7,8-tetrahydropyrido[3,4-d]pyrimidin-4-yl] piperazine-1-carboxylate To a solution of tert-butyl 4-[7-benzyl-2-(3-morpholinopropoxy)-6,8-dihydro-5H-pyrido[3,4-d]pyrimidin-4-yl]piperazine-1-carboxylate (14 g, 25.3 mmol) in MeOH (1 L) was added dry Pd/C (3 g, 10% purity) under N$_2$. The suspension was degassed under vacuum and purged with H$_2$ several times. The mixture was stirred under H$_2$ (15 psi) at 40° C. for 10 hours. The mixture was filtered and the filtrate concentrated in vacuo to give a residue. The residue was purified by reversed phase flash [water (0.1 TFA)/acetonitrile] to give tert-butyl 4-[2-(3-morpholinopropoxy)-5,6,7,8-tetrahydropyrido[3,4-d]pyrimidin-4-yl] piperazine-1-carboxylate (6.5 g, 13.9 mmol). ES+APCI MS m/z 463.4 [M+H]$^+$.

Intermediate 56

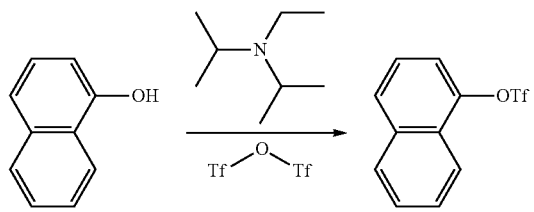

Naphthalen-1-yl trifluoromethanesulfonate alpha-Naphthol (4 g, 27.74 mmol) was dissolved in DCM (200 mL) in a 3 neck flask. The reaction was cooled to 10° C. in a water bath. N-ethyl-N-isopropylpropan-2-amine (4.846 ml, 27.74 mmol) and trifluoromethanesulfonic anhydride (4.668 ml, 27.74 mmol) were added to the solution dropwise. The reaction was stirred at 10° C. for 2 hours. TLC (25% EtOAc, UV vis) showed reaction complete. The organics were with water (2×) and brine (2×). The organics were dried over MgSO$_4$ and concentrated in vacuo. The concentrate was purified using normal phase chromatography on the CombiFlash (0%-12% EtOAc:Hexanes). All fractions containing clean product were combined and concentrated in vacuo to give naphthalen-1-yl trifluoromethanesulfonate (6.77 g, 24.51 mmol, 88.34% yield).

Intermediate 57

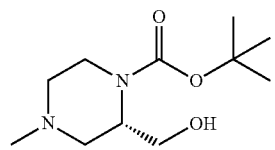 [SMILES: CN1CCN(C(=O)OC(C)(C)C)[C@H](CO)C1]

Tert-butyl (S)-2-(hydroxymethyl)-4-methylpiperazine-1-carboxylate

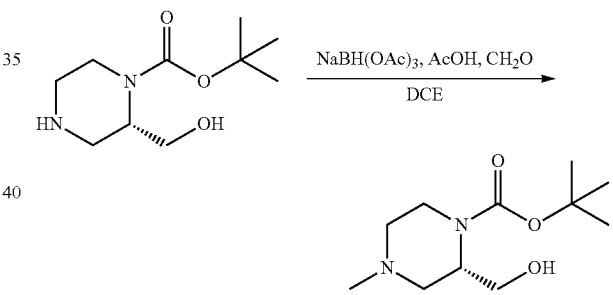

To a solution of (S)-1-Boc-2-hydroxymethylpiperazine (1.0 g, 4.62 mmol) in DCE (92.47 ml, 4.624 mmol) was added formaldehyde (3.474 ml, 46.24 mmol) (37% in water) followed by sodium triacetoxyborohydride (4.9 g, 23.12 mmol). The mixture was stirred vigorously at room temperature for 2.5 hours. The mixture was treated with saturated sodium bicarbonate (30 mL), stirred for 10 min then extracted with DCM (3×10 mL). The combined organic phases were dried over sodium sulfate, filtered and concentrated. ES+APCI MS m/z 231.1 [M+H]$^+$.

Intermediate 58

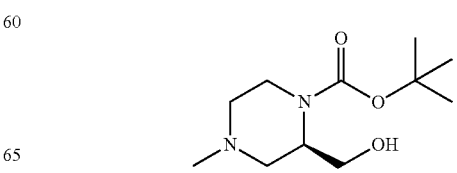

257

Tert-butyl (R)-2-(hydroxymethyl)-4-methylpiperazine-1-carboxylate

Title compound was prepared as in Intermediate 57, substituting tert-butyl (R)-2-(hydroxymethyl)piperazine-1-carboxylate for (S)-1-Boc-2-hydroxymethylpiperazine. ES+APCI MS m/z 231.1 [M+H]⁺

Intermediate 59

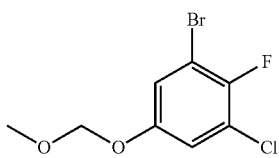

1-bromo-3-chloro-2-fluoro-5-(methoxymethoxy)benzene

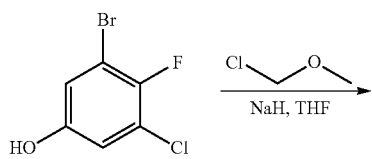

To a round bottom flask was added THF (8.87 ml, 4.44 mmol) followed by sodium hydride, 60% dispersion in mineral oil (0.213 g, 5.32 mmol). The mixture was cooled to 0° C. then 3-bromo-5-chloro-4-fluorophenol (1.0 g, 4.44 mmol) was added portionwise. Once the bubbling had ceased the resulting dark mixture was stirred at 0° C. for 30 min. Then chloromethyl methyl ether (0.421 ml, 5.54 mmol) was added and the mixture was warmed to ambient temperature where it was stirred for 2 hr. A saturated aqueous ammonium chloride solution was added and the mixture was extracted with DCM. The organic layer was dried over sodium sulfate, filtered and concentrated. Crude material was chromatographed (0-15% EtOAc in hexanes) to provide product as clear oil.

258

Intermediate 60

4-bromo-1-tetrahydropyran-2-yl-5-(trifluoromethyl)indazole

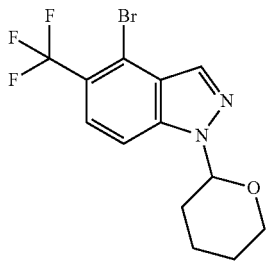 [SMILES: FC(F)(F)c1ccc2c(cnn2C2CCCCO2)c1Br]

Step A: 4-bromo-1-tetrahydropyran-2-yl-5-(trifluoromethyl)indazole

To a solution of 4-bromo-5-(trifluoromethyl)-1H-indazole (500 mg, 1.89 mmol, 1 eq) in DCM (10 mL) was added 3,4-dihydro-2H-pyran (476 mg, 5.66 mmol, 517 uL, 3 eq) and TsOH.H₂O (35.9 mg, 188 umol, 0.1 eq). The mixture was stirred at 15° C. for 1 hour. The mixture was concentrated. The residue was purified by column chromatography (SiO₂, PE:EA=10:1 to 1:1) to give 4-bromo-1-tetrahydropyran-2-yl-5-(trifluoromethyl)indazole (480 mg, 1.37 mmol, 72.9% yield) as yellow oil. ¹H NMR (400 MHz, chloroform-d) δ 8.20 (s, 1H), 7.69-7.63 (m, 2H), 5.70 (dd, J=2.8, 8.8 Hz, 1H), 4.05-3.96 (m, 1H), 3.79-3.70 (m, 1H), 2.56-2.50 (m, 1H), 2.27-2.04 (m, 2H), 1.80-1.74 (m, 2H), 1.60-1.54 (m, 1H).

Intermediate 61

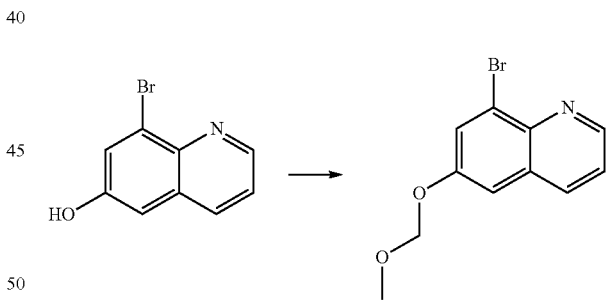

8-bromo-6-(methoxymethoxy)quinoline

A stirred suspension of 8-bromoquinolin-6-ol (1.00 g, 4.46 mmol) in DCM (20 mL) was cooled to 0° C. and diisopropylethylamine (1.2 mL, 6.7 mmol, 1.5 eq.) was added followed by chloro(methoxy)methane (0.41 mL, 5.4 mmol, 1.2 eq.) dropwise and the reaction mixture was warmed to room temperature overnight. Concentrated aqueous ammonia (0.5 mL, ~5 mmol) was next added and the resulted mixture was stirred for 1 hour at room temperature. The mixture was evaporated in vacuo and chromatographed on silica gel, Redisep 40 g, using 20% EtOAc/hexane as eluent to give a colorless powder (0.52 g, 44%). ES+APCI MS m/z 268.0, [M+H]⁺.

Intermediate 62

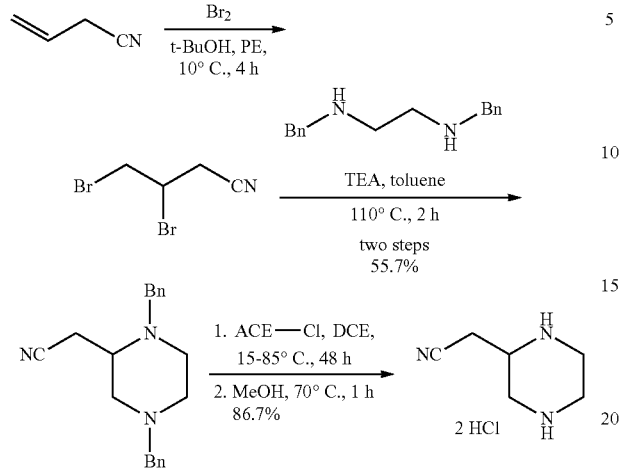

To a solution of but-3-enenitrile (80.0 g, 1.19 mol, 96.4 mL, 1.00 eq) in tert-butanol (130 mL) and petroleum ether (480 mL) was added a solution of Br$_2$ (191 g, 1.19 mol, 61.5 mL, 1.00 eq) in tert-butanol (130 mL). The mixture was stirred at 10° C. for 4 hours. The mixture was used into next step without any workup.

To the above mixture (274 mL) was added a solution of N,N-dibenzylethane-1,2-diamine (160 g, 445 mmol, 157 mL, 2 HOAc) and Et$_3$N (178 g, 1.76 mol, 245 mL) in toluene (300 mL). After was stirred at 110° C. for 2 hours, the mixture was filtered and the filtrate was concentrated under vacuum. The residue was purified by column chromatography (SiO$_2$, petroleum ether/ethyl acetate=3/1) to give 2-(1,4-dibenzylpiperazin-2-yl)acetonitrile (75.0 g, 246 mmol, two steps 55.7% yield) as a yellow solid. LCMS [ESI, M+1]: 306.

$^1$H NMR (400 MHz, chloroform-d) δ=7.37-7.23 (m, 10H), 3.80 (d, J=13.2 Hz, 1H), 3.60-3.42 (m, 3H), 3.06-2.96 (m, 1H), 2.95-2.83 (m, 1H), 2.69-2.53 (m, 4H), 2.52-2.35 (m, 3H).

To a solution of 2-(1,4-dibenzylpiperazin-2-yl)acetonitrile (160 g, 524 mmol, 1.00 eq) in dichloroethane (1.50 L) was added 1-chloroethyl carbonochloridate (300 g, 2.10 mol, 4.00 eq) at 15° C. After stirred at 85° C. for 48 h, the mixture was concentrated under vacuum. The residue was then taken up into methanol (1.50 L) and heated to reflux for 1 hour. The mixture was concentrated. The solid was treated with methyl tert-butyl ether (1.00 L), 2-piperazin-2-ylacetonitrile (Intermediate 62, 90.0 g, 454 mmol, 86.7% yield, 2HCl) was obtained as a white solid and used for next step without further purification.

$^1$H NMR (400 MHz, DMSO-d$_6$) δ=10.19 (br s, 2H), 4.01-3.73 (m, 1H), 3.69-3.41 (m, 4H), 3.32 (dt, J=2.8, 13.2 Hz, 1H), 3.27-3.10 (m, 3H).

Intermediate 63

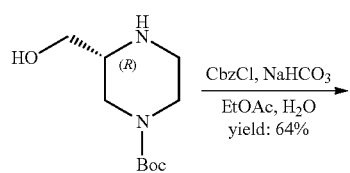

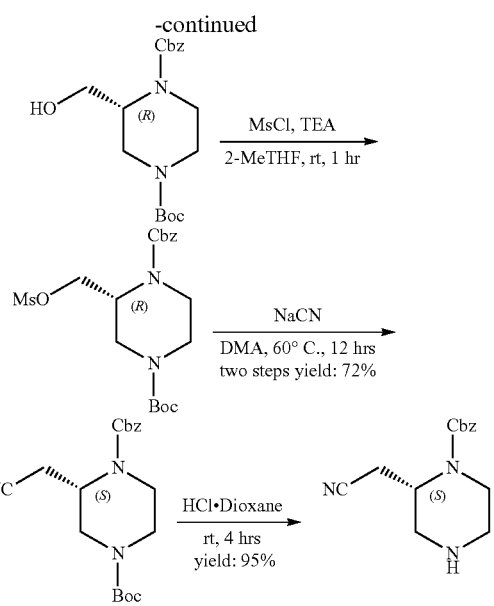

To a solution of tert-butyl (3R)-3-(hydroxymethyl)piperazine-1-carboxylate (80.0 g, 370 mmol, 1.0 eq) in Ethyl acetate (1400 mL) was added NaHCO$_3$ (93.2 g, 1.11 mol, 43.2 mL, 3.0 eq), H$_2$O (700 mL) and benzyl carbonochloridate (82.0 g, 481 mmol, 68.4 mL, 1.30 eq). The mixture was stirred at 25° C. for 12 hour. After completion, the organic phase was separated, washed with water (500 mL×2) dried over Na$_2$SO$_4$ and filtered. The solvent was removed under vacuum to give a residue. The residue was purified by column chromatography (SiO$_2$, Petroleum ether/Ethyl acetate=40/1 to 1/1). The product 1-benzyl 4-tert-butyl (2R)-2-(hydroxymethyl)piperazine-1,4-dicarboxylate (85.0 g, 235 mmol, 64% yield, 96% purity) was obtained as a yellow oil. LCMS [ESI, M-99]: 251.

To a solution of 1-benzyl 4-tert-butyl (2R)-2-(hydroxymethyl)piperazine-1,4-dicarboxylate (20.0 g, 57.1 mmol, 1.0 eq) in 2-Methyltetrahydrofuran (240 mL) was added TEA (17.3 g, 171.23 mmol, 23.8 mL, 3.0 eq) and methanesulfonyl chloride (7.74 g, 67.6 mmol, 5.23 mL, 1.18 eq). The mixture was stirred at 20° C. for 1 hour. The reaction mixture was quenched by addition H$_2$O 150 mL at 20° C. The reaction mixture was extracted with Ethyl acetate (300 mL×2). The organic layers were washed with H$_2$O (100 mL), dried over Na$_2$SO$_4$, and filtered. The solvent was removed under vacuum. 1-benzyl 4-tert-butyl (2R)-2-(methylsulfonyloxymethyl)piperazine-1,4-dicarboxylate (22.0 g, crude) was obtained as a yellow oil. The crude product was used directly to the next step without further purification.

To a solution of 1-benzyl 4-tert-butyl (2R)-2-(methylsulfonyloxymethyl)piperazine-1,4-dicarboxylate (22.0 g, 51.3 mmol) in DMA (150 mL) was added NaCN (10.4 g, 211 mmol). The mixture was stirred at 60° C. for 12 hour. The solvent was removed under vacuum to give a oil residue. The residue was diluted with H$_2$O (40.0 mL) and extracted with Ethyl acetate (50.0 mL×3). The combined organic layers were washed with saturated brine (80.0 mL), dried over Na$_2$SO$_4$, filtered and concentrated under reduced pressure to give a residue. The residue was purified by column chromatography (SiO$_2$, Petroleum ether/Ethyl acetate=40/1 to 5:1) The product 1-benzyl 4-tert-butyl (2S)-2-(cyanomethyl)piperazine-1,4-dicarboxylate (18.5 g, 46.4 mmol, two steps yield 72%) was obtained as a yellow oil. LCMS [ESI, M+1]: 360.

To a solution of 1-benzyl 4-tert-butyl (2S)-2-(cyanomethyl)piperazine-1,4-dicarboxylate (18.5 g, 43.3 mmol, 1.00 eq) in dioxane (40.0 mL) was added HCl.dioxane (4 M, 54.1 mL, 5.0 eq). The mixture was stirred at 20° C. for 1 hour. Then the reaction mixture was added NaHCO$_3$ to pH >7, and concentrated under reduced pressure to remove dioxane. The residue was diluted with H$_2$O (50.0 mL) and extracted with Ethyl acetate (50.0 mL×3). The combined organic layers were washed with H$_2$O (20.0 mL), dried over Na$_2$SO$_4$, filtered and concentrated under reduced pressure to give a residue. The product benzyl (2S)-2-(cyanomethyl)piperazine-1-carboxylate (Intermediate 63, 11.5 g, 91.8% purity, 95% yield) was obtained as a yellow oil. LCMS [ESI, M+1]: 260.

$^1$H NMR (400 MHz, CHLOROFORM-d) δ=7.37-7.31 (m, 5H), 5.14 (s, 2H), 4.49 (br, s, 1H), 3.93 (br, s, 1H), 3.07-2.81 (m, 5H), 2.78-2.54 (m, 2H).

Intermediate 64

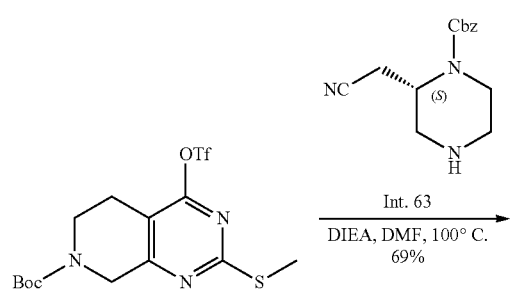

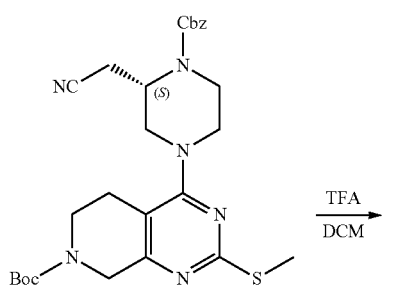

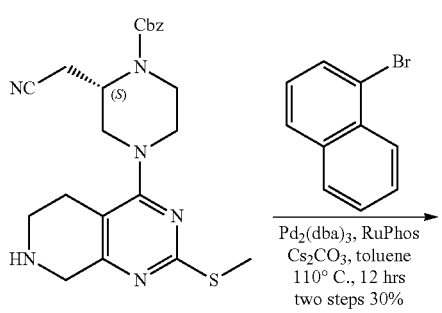

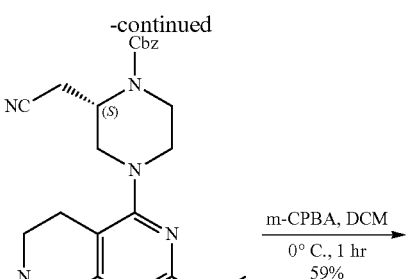

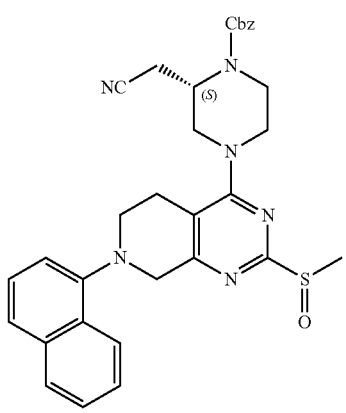

A mixture of tert-butyl 2-methylsulfanyl-4-(trifluoromethylsulfonyloxy)-6,8-dihydro-5H-pyrido[3,4-d]pyrimidine-7-carboxylate (3.81 g, 8.87 mmol, 1.0 eq), benzyl(2S)-2-(cyanomethyl)piperazine-1-carboxylate (Intermediate 63, 2.30 g, 8.87 mmol, 1.0 eq), DIEA (3.44 g, 26.6 mmol, 4.63 mL, 3.0 eq) in DMF (20.0 mL) was degassed and purged with N$_2$ for 3 times, and then the mixture was stirred at 100° C. for 1 hour under N$_2$ atmosphere. After completion, the solvent was removed under vacuum. The residue was purified by column chromatography (SiO$_2$, Petroleum ether/Ethyl acetate=3/1 to 1:1) to give tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (3.6 g, 6.16 mmol, 69% yield, 92.2% purity) as a yellow solid. LCMS [ESI, M+1]: 539.

A mixture of tert-butyl 4-[(3S)-4-benzyloxycarbonyl-3-(cyanomethyl)piperazin-1-yl]-2-methylsulfanyl-6,8-dihydro-5Hpyrido[3,4-d]pyrimidine-7-carboxylate (6.0 g, 11.1 mmol, 1.0 eq), TFA (30.8 g, 270 mmol, 20.0 mL, 24.3 eq) in DCM (20.0 mL) was degassed and purged with N$_2$ for 3 times, and then the mixture was stirred at 20° C. for 1 hour under N$_2$ atmosphere. After completion, the reaction mixture was quenched with saturated NaHCO$_3$ solution (500 mL). The mixture was extracted with ethyl acetate (3×300 mL) and the organic layer was dried over Na$_2$SO$_4$ and filtered. The solvent was removed under vacuum to give benzyl (2S)-2-(cyanomethyl)-4-(2-methylsulfanyl-5,6,7,8-tetrahydropyrido[3,4-d]pyrimidin-4-yl)piperazine-1-carboxylate (4.8 g, crude) as a yellow solid which was used for the next step without further purification.

A mixture of benzyl (2S)-2-(cyanomethyl)-4-(2-methylsulfanyl-5,6,7,8-tetrahydropyrido[3,4-d]pyrimidin-4-yl)piperazine-1-carboxylate (4.8 g), 1-bromonaphthalene (3.8 g, 18.35 mmol, 2.55 mL), Pd$_2$(dba)$_3$ (1.0 g, 1.09 mmol), RuPhos (1.02 g, 2.19 mmol) and Cs₂CO₃ (12.0 g, 36.8 mmol) in toluene (30.0 mL) was degassed and purged with N₂ for 3 times, and then the mixture was stirred at 100° C. for 12 hours under N₂ atmosphere. After completion, the reaction mixture was filtered. The organic solvent was removed under vacuum to give an oil residue. The residue was purified by column chromatography (SiO₂, Petroleum ether/Ethyl acetate=5/1 to 3:1) to give benzyl (2S)-2-(cyanomethyl)-4-[2-methylsulfanyl-7-(1-naphthyl)-6,8-dihydro-5H-pyrido[3,4-d]pyrimidin-4-yl]piperazine-1-carboxylate (2.2 g, 3.31 mmol, 85.3% purity, two steps yield 30%) was obtained as a yellow solid. LCMS [ESI, M+1]: 565.

A mixture of benzyl (2S)-2-(cyanomethyl)-4-[2-methylsulfanyl-7-(1-naphthyl)-6,8-dihydro-5H-pyrido[3,4-d]pyrimidin-4-yl]piperazine-1-carboxylate (2.8 g, 3.97 mmol, 1.0 eq), m-CPBA (1.05 g, 5.16 mmol, 1.3 eq) in DCM (4.0 mL) was degassed and purged with N₂ for 3 times, and then the mixture was stirred at 0° C. for 1 hour under N₂ atmosphere. After completion, the reaction is quenched by adding saturated Na₂SO₃ solution (50 mL). The mixture was extracted with ethyl acetate (3×10 mL). The combined organic layer was dried with Na₂SO₄ and filtered. The solvent was removed to give a oil residue. The residue was purified by column chromatography (SiO₂, Metheanol/Ethyl acetate=1/20 to 1:10) to give benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 1.5 g, 2.35 mmol, 59% yield, 90.8% purity) as a yellow solid. LCMS [ESI, M+1]: 581.

Intermediate 65

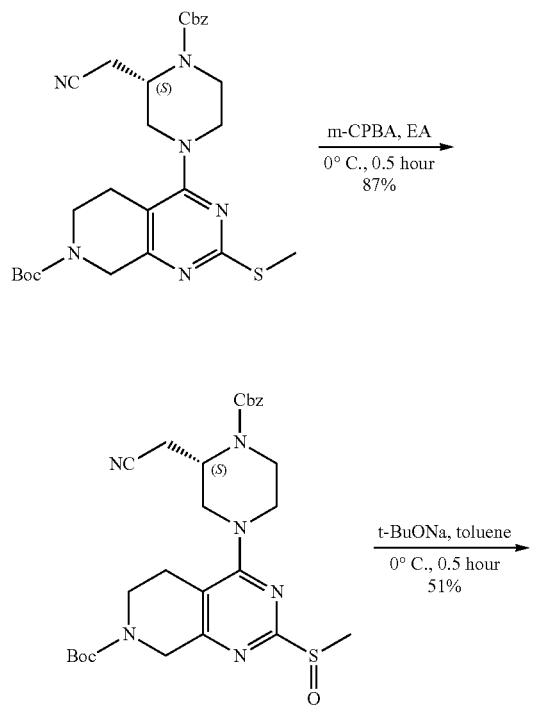

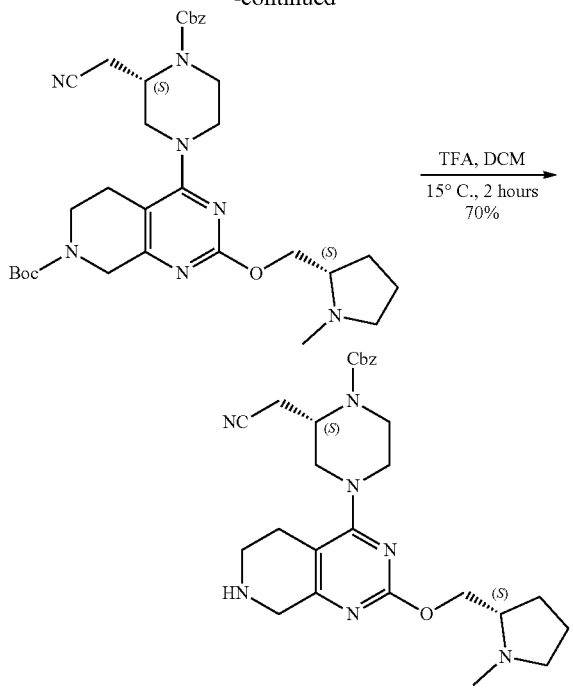

To a solution of tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (24.3 g, 45.0 mmol, 1.0 eq) in Ethyl acetate (480 mL) was added m-CPBA (8.69 g, 42.8 mmol, 85% purity, 0.95 eq) portionwise at 0° C. The mixture was stirred at 0° C. for 0.5 hour. Upon completion, the mixture was diluted with water (50.0 mL) and extracted with ethyl acetate (2×300 mL). The organic layers were dried over Na₂SO₄ and concentrated under vacuum. The residue was purified by reversed-phase flash [water (0.1% FA)/acetonitrile]. The mixture was neutralized with saturated sodium bicarbonate solution, concentrated under vacuum to remove MeCN and extracted with ethyl acetate (3×1000 mL). The organic layers were dried over Na₂SO₄ and concentrated under vacuum to give tert-butyl 4-[(3S)-4-benzyloxycarbonyl-3-(cyanomethyl)piperazin-1-yl]-2-methylsulfinyl-6,8-dihydro-5H-pyrido[3,4-d]pyrimidine-7-carboxylate (22.8 g, 39.3 mmol, 87% yield, 95.8% purity) as a yellow solid.

¹H NMR (400 MHz, chloroform-d) δ 7.37-7.23 (m, 5H), 5.12 (s, 2H), 4.75-4.41 (m, 3H), 4.17-4.05 (m, 2H), 3.86 (d, J=11.6 Hz, 1H), 3.81-3.62 (m, 1H), 3.46-3.18 (m, 3H), 3.10 (d, J=3.6, 12.0 Hz, 1H), 2.81 (d, J=3.2 Hz, 3H), 2.77-2.56 (m, 4H), 1.42 (s, 9H).

To a solution of tert-butyl 4-[(3S)-4-benzyloxycarbonyl-3-(cyanomethyl)piperazin-1-yl]-2-methylsulfinyl-6,8-dihydro-5H-pyrido[3,4-d]pyrimidine-7-carboxylate (5.0 g, 9.01 mmol, 1.0 eq) and [(2S)-1-methylpyrrolidin-2-yl]methanol (1.82 g, 15.8 mmol, 1.88 mL, 1.75 eq) in toluene (50.0 mL) was added t-BuONa (1.73 g, 18.0 mmol, 2.0 eq). The mixture was stirred at 0° C. for 0.5 hour. After completion, the mixture was added cold water (50.0 mL) and extracted with ethyl acetate (5×50.0 mL). The combined organic layer was dried over Na₂SO₄, filtered and concentrated. The obtained product was purified by column chromatography (SiO₂, PE:EA=10:1-EA:MeOH=5:1) to give tert-butyl 4-[(3S)-4-benzyloxycarbonyl-3-(cyanomethyl)piperazin-1-yl]-2-[[(2S)-1-methylpyrrolidin-2-yl]methoxy]-

6,8-dihydro-5H-pyrido[3,4-d]pyrimidine-7-carboxylate (2.80 g, 4.62 mmol, 51.0% yield) as yellow solid.

¹H NMR (400 MHz, chloroform-d) δ 7.44-7.35 (m, 5H), 5.21 (s, 2H), 4.73-4.54 (m, 2H), 4.44-4.33 (m, 2H), 4.22-4.10 (m, 2H), 3.41-3.93 (m, 1H), 3.82 (br d, J=11.6 Hz, 2H), 3.39-3.22 (m, 3H), 3.11 (br t, J=7.8 Hz, 1H), 2.99 (d, J=3.6, 12.8 Hz, 1H), 2.90-2.56 (m, 5H), 2.49 (s, 3H), 2.35-2.25 (m, 1H), 2.07-2.02 (m, 1H), 1.91-1.76 (m, 3H), 1.50 (s, 9H).

To a solution of tert-butyl 4-[(3S)-4-benzyloxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate (2.40 g, 3.96 mmol, 1.0 eq) in DCM (8.0 mL) was added TFA (13.9 g, 122 mmol, 9.0 mL, 30.7 eq). The mixture was stirred at 15° C. for 2 hours. After completion, the mixture was concentrated. The residue was added saturated NaHCO₃ aqueous (20.0 mL) and extracted with DCM (5×10.0 mL). The organic layer was dried over Na₂SO₄, filtered and concentrated. The product benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 1.40 g, 2.77 mmol, 70% yield) was obtained as yellow solid. LCMS [ESI, M+1]: 506.

Intermediate 66

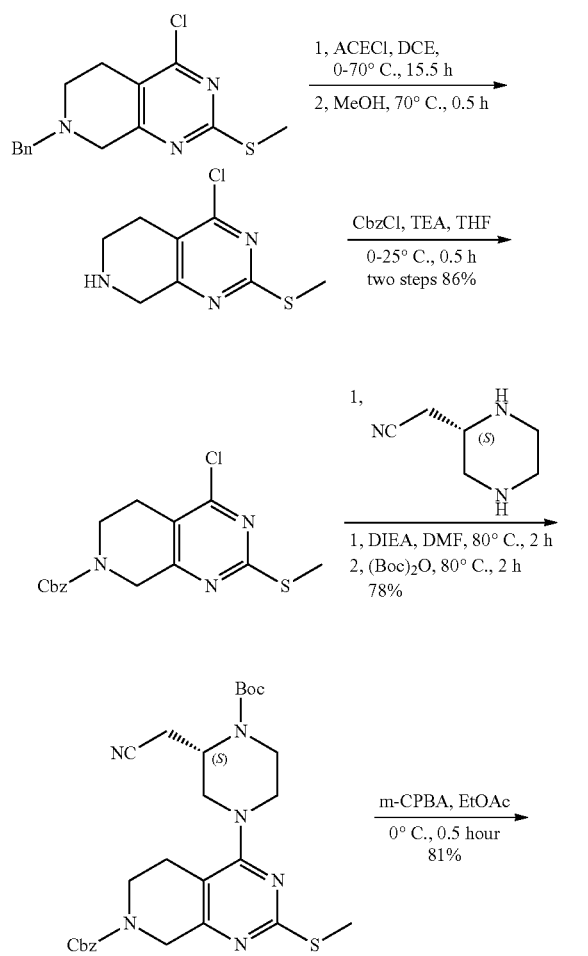

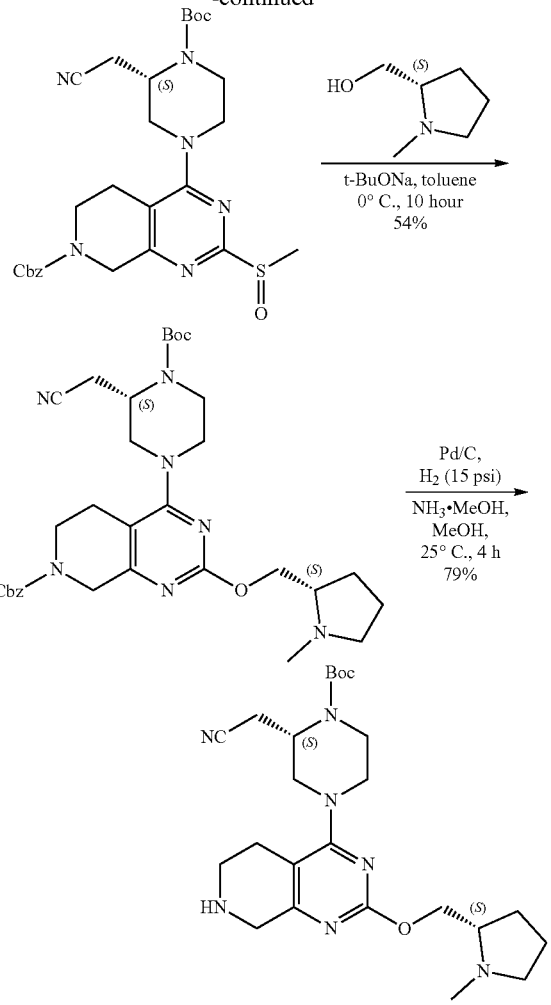

Step A: To a solution of 7-benzyl-4-chloro-2-methylsulfanyl-6,8-dihydro-5H-pyrido[3,4-d]pyrimidine (20.0 g, 65.4 mmol, 1 eq) in DCE (200 mL) was added 1-chloroethyl carbonochloridate (28.1 g, 196 mmol, 3 eq) at 0° C. The mixture was stirred at 0° C. for 30 minutes and 70° C. for 15 hours. The mixture was concentrated under vacuum. The residue was dissolved in MeOH (200 mL) and stirred at 70° C. for 0.5 hours. Upon completion, the mixture was concentrated under vacuum. The residue was triturated with methyl tert-butyl ether (60 mL). The precipitate was collected by filtration, washed with methyl tert-butyl ether (20 mL) and dried under vacuum to give 4-chloro-2-methylsulfanyl-5,6,7,8-tetrahydropyrido[3,4-d]pyrimidine (17.2 g, crude, HCl) as a yellow solid which was used directly in the next step without further purification.

¹H NMR (400 MHz, methanol-d₄) δ=4.35 (s, 2H), 3.60 (t, J=6.4 Hz, 2H), 3.05 (t, J=6.4 Hz, 2H), 2.55 (s, 3H).

Step B: To a solution of 4-chloro-2-methylsulfanyl-5,6,7,8-tetrahydropyrido[3,4-d]pyrimidine (16.5 g, crude, HCl) and TEA (20.0 g, 196 mmol, 27.3 mL) in THF (400 mL) was added benzyl carbonochloridate (16.7 g, 98.1 mmol, 13.9 mL) dropwise at 0° C. The mixture was stirred at 25° C. for 0.5 hour. Upon completion, the mixture was diluted with water (80 mL) and the organic layer was separated. The aqueous phase was extracted with EtOAc (200 mL). The combined organic layers were dried over MgSO₄, filtered and concentrated under vacuum. The residue was purified by silica gel chromatography (PE/EtOAc 80/1 to 5/1) to give benzyl 4-chloro-2-methylsulfanyl-6,8-dihydro-5H-pyrido [3,4-d]pyrimidine-7-carboxylate (19.6 g, 50.4 mmol, two steps 86% yield, 90% purity) as a yellow oil.

$^1$H NMR (300 MHz, chloroform-d) δ=7.37 (s, 5H), 5.18 (s, 2H), 4.63 (s, 2H), 3.877 (d, J=8.0, 2H), 2.80 (br s, 2H), 2.54 (s, 3H).

Step C: To a solution of benzyl 4-chloro-2-methylsulfanyl-6,8-dihydro-5H-pyrido[3,4-d]pyrimidine-7-carboxylate (21.5 g, 55.3 mmol, 1.00 eq) in DMF (400 mL) was added DIEA (35.7 g, 277 mmol, 48.2 mL, 5.00 eq) and 2-[(2S)-piperazin-2-yl]acetonitrile (6.92 g, 55.3 mmol, 1.00 eq). After stirred at 80° C. for 2 hours, (Boc)$_2$O (60.4 g, 277 mmol, 63.5 mL, 5.00 eq) was added into above mixture and stirred at 80° C. for another 2 hours. Upon completion, the mixture was diluted with water (800 mL) and extracted with EtOAc (2×400 mL). The organic layers were washed with brine (300 mL), dried over Na$_2$SO$_4$ and concentrated under vacuum. The residue was purified by silica gel chromatography (PE/EtOAc 10/1 to 1/1) to give benzyl 4-[(3S)-4-tert-butoxycarbonyl-3-(cyanomethyl) piperazin-1-yl]-2-methylsulfanyl-6,8-dihydro-5H-pyrido[3,4-d]pyrimidine-7-carboxylate (24.3 g, 43.0 mmol, 78% yield, 95% purity) as a yellow solid.

$^1$H NMR (400 MHz, chloroform-d) δ=7.43-7.29 (m, 5H), 5.18 (s, 2H), 4.76-4.54 (m, 2H), 4.46 (br d, J=18.4 Hz, 1H), 4.08-3.69 (m, 4H), 3.53-3.35 (m, 1H), 3.34-3.03 (m, 2H), 3.03-2.89 (m, 1H), 2.81-2.55 (m, 4H), 2.50 (s, 3H), 1.51 (s, 9H).

Step D: To a solution of benzyl 4-[(3S)-4-tert-butoxycarbonyl-3-(cyanomethyl) piperazin-1-yl]-2-methylsulfanyl-6,8-dihydro-5H-pyrido[3,4-d]pyrimidine-7-carboxylate (24.3 g, 45.1 mmol, 1 eq) in EtOAc (480 mL) was added m-CPBA (8.70 g, 42.9 mmol, 85% purity, 0.95 eq) portion wise at 0° C. The mixture was stirred at 0° C. for 0.5 hour. Upon completion, the mixture was diluted with water (800 mL). The pH was adjusted to 8 with NaHCO$_3$ and the organic layer was separated. The aqueous phase was extracted with EtOAc (2×400 mL). The organic layers were dried over Na$_2$SO$_4$ and concentrated under vacuum. The residue was purified by silica gel chromatography (EtOAc/MeOH 100/1 to 10/1) to give benzyl 4-[(3S)-4-tert-butoxycarbonyl-3-(cyanomethyl)piperazin-1-yl]-2-methylsulfinyl-6,8-dihydro-5H-pyrido[3,4-d]pyrimidine-7-carboxylate (20.9 g, 36.4 mmol, 81% yield, 96% purity) as a white solid. LCMS [ESI, M+1]: 555.

Step E: To a solution of benzyl 4-[(3S)-4-tert-butoxycarbonyl-3-(cyanomethyl) piperazin-1-yl]-2-methylsulfinyl-6,8-dihydro-5H-pyrido[3,4-d]pyrimidine-7-carboxylate (20.9 g, 37.6 mmol, 1 eq) and [(2S)-1-methylpyrrolidin-2-yl]methanol (8.67 g, 75.3 mmol, 8.94 mL, 2 eq) in toluene (400 mL) was added t-BuONa (7.23 g, 75.3 mmol, 2 eq) at 0° C. After stirred at 0° C. for 10 minutes, the mixture was concentrated under vacuum. The residue was diluted with water (200 mL) and extracted with EtOAc (2×400 mL). The organic layers were dried over Na$_2$SO$_4$ and concentrated under vacuum. The residue was purified by reversed-phase flash [water (0.1% FA)/acetonitrile]. The mixture was neutralized with saturated sodium bicarbonate solution, concentrated under vacuum to remove MeCN and extracted with EtOAc (2×1000 mL). The organic layers were dried over Na$_2$SO$_4$ and concentrated under vacuum to give benzyl 4-[(3S)-4-tert-butoxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate (13.5 g, 20.5 mmol, 54% yield, 92% purity) as a yellow solid. LCMS [ESI, M+1]: 606.

Step F: To a solution of benzyl 4-[(3S)-4-tert-butoxycarbonyl-3-(cyanomethyl) piperazin-1-yl]-2-[[(2S)-1-methylpyrrolidin-2-yl]methoxy]-6,8-dihydro-5H-pyrido[3,4-d]pyrimidine-7-carboxylate (3.50 g, 5.78 mmol, 1 eq) in MeOH (60.0 mL) was added NH$_3$/MeOH (60.0 mL), Pd/C (1.00 g, 10% purity) under N$_2$. The suspension was degassed under vacuum and purged with H$_2$ several times. The mixture was stirred under H$_2$ (15 psi) at 25° C. for 4 hours. Upon completion, the catalyst was filtered off and the filtrate was concentrated under vacuum to give tert-butyl (2S)-2-(cyanomethyl)-4-[2-[[(2S)-1-methylpyrrolidin-2-yl] methoxy]-5,6,7,8-tetrahydropyrido[3,4-d]pyrimidin-4-yl]piperazine-1-carboxylate (Intermediate 66, 2.33 g, 4.55 mmol, 79% yield, 92% purity) as a yellow solid which was used directly in the next step without further purification.

$^1$H NMR (400 MHz, chloroform-d) δ=4.58 (br s, 1H), 4.34 (dd, J=5.2, 10.8 Hz, 1H), 4.11 (dd, J=6.8, 10.8 Hz, 1H), 4.08-3.88 (m, 4H), 3.84 (br d, J=12.8 Hz, 1H), 3.25-3.03 (m, 4H), 3.01-2.88 (m, 2H), 2.82-2.51 (m, 5H), 2.47 (s, 3H), 2.27 (dt, J=7.2, 9.2 Hz, 1H), 2.11-1.97 (m, 1H), 1.92-1.75 (m, 3H), 1.50 (s, 9H).

Intermediate 67

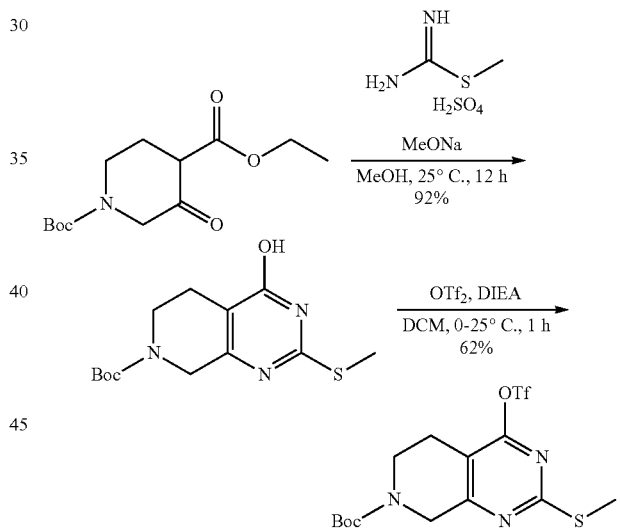

tert-butyl 2-methylsulfanyl-4-(trifluoromethylsulfonyloxy)-6,8-dihydro-5H-pyrido[3,4-d]pyrimidine-7-carboxylate Step A: tert-butyl 4-hydroxy-2-methylsulfanyl-6,8-dihydro-5H-pyrido[3,4-d]pyrimidine-7-carboxylate To a stirred solution of 1-tert-butyl 4-ethyl 3-oxopiperidine-1,4-dicarboxylate (50.0 g, 184 mmol, 1.00 eq) in MeOH (1.00 L) at 25° C. under nitrogen was added NaOMe (49.8 g, 921 mmol, 5.00 eq), followed by 2-methylisothiourea (62.4 g, 331 mmol, 1.80 eq, H$_2$SO$_4$) as a solid. The reaction mixture was stirred at 25° C. for 16 hours. The reaction mixture was acidified with HCl (2 M) until pH ~5, and then the mixture was concentrated under reduced pressure to removed MeOH. The residue was suspended in 300 mL of ethyl acetate and 300 mL of water and stirred rapidly. The suspension was filtered and the white solid was collected. The filtrate was separated and the organics washed with water (1×300 mL) and brine (1×200 mL). The organics were isolated, dried over Na$_2$SO$_4$, filtered and concentrated to a white solid. tert-butyl 4-hydroxy-2-methylsulfanyl-6,8-dihydro-5H-pyrido[3,4-d]pyrimidine-7-carboxylate (51.0 g, 138 mmol, 75.4% yield, 81% purity) was obtained as a white solid and used directly for next step without further purification. LCMS [M+1]: 298.

$^1$H NMR (400 MHz, chloroform-d) δ=4.33 (s, 2H), 3.61 (t, J=5.6 Hz, 2H), 2.68-2.49 (m, 5H), 1.50 (s, 9H).

Step B: tert-butyl 2-methylsulfanyl-4-(trifluoromethylsulfonyloxy)-6,8-dihydro-5H-pyrido[3,4-d]pyrimidine-7-carboxylate To a stirred suspension of tert-butyl 4-hydroxy-2-methylsulfanyl-6,8-dihydro-5H-pyrido[3,4-d]pyrimidine-7-carboxylate (51.0 g, 171 mmol, 1.00 eq) in DCM (500 mL) at 0° C. was added DIEA (44.3 g, 343 mmol, 59.9 mL, 2.00 eq), followed by Tf$_2$O (72.6 g, 257 mmol, 42.4 mL, 1.50 eq) under nitrogen. Immediately a brown solution formed. After stirring at 25° C. for 16 hours, the reaction was concentrated to give a brown oil. The brown oil was purified by column chromatography (SiO$_2$, Petroleum ether/Ethyl acetate=1/0 to 10/1). Title compound tert-butyl 2-methylsulfanyl-4-(trifluoromethylsulfonyloxy)-6,8-dihydro-5H-pyrido[3,4-d]pyrimidine-7-carboxylate (46.0 g, 107 mmol, 62% yield) was obtained as a yellow solid. LCMS [M+1]: 430.

Intermediate 68

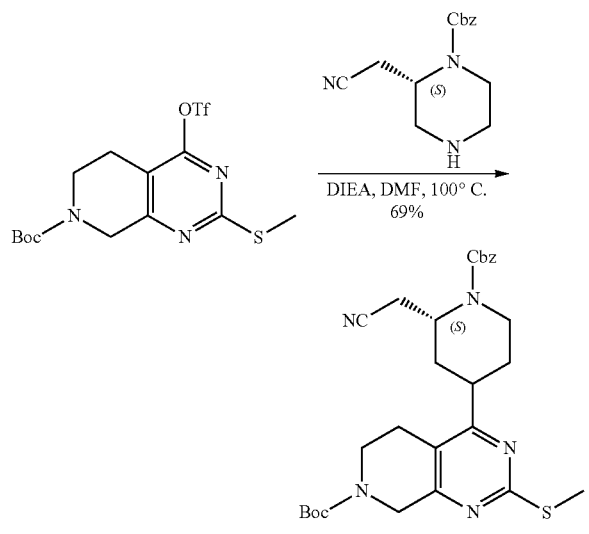

tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate Step A: tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate A mixture of tert-butyl 2-methylsulfanyl-4-(trifluoromethylsulfonyloxy)-6,8-dihydro-5H-pyrido[3,4-d]pyrimidine-7-carboxylate (3.81 g, 8.87 mmol, 1.0 eq), benzyl(2S)-2-(cyanomethyl)piperazine-1-carboxylate (Intermediate 63, 2.30 g, 8.87 mmol, 1.0 eq), DIEA (3.44 g, 26.6 mmol, 4.63 mL, 3.0 eq) in DMF (20.0 mL) was degassed and purged with N$_2$ for 3 times, and then the mixture was stirred at 100° C. for 1 hour under N$_2$ atmosphere. After completion, the solvent was removed under vacuum. The residue was purified by column chromatography (SiO$_2$, Petroleum ether/Ethyl acetate=3/1 to 1:1) to give title compound tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (3.6 g, 6.16 mmol, 69% yield, 92.2% purity) as a yellow solid.

Intermediate 69

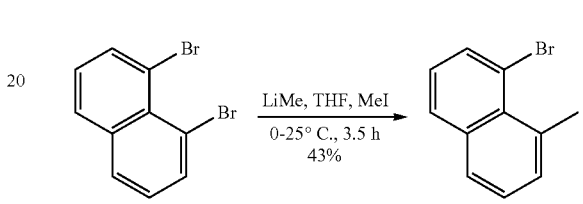

1-bromo-8-methylnaphthalene

Step A: 1-bromo-8-methyl-naphthalene

To a solution of 1,8-dibromonaphthalene (1 g, 3.50 mmol, 1 eq) in THF (20 mL) was added MeLi (1.6 M in diethyl ether, 2.62 mL, 1.2 eq) at 0° C. dropwise. After stirring for 30 minutes at 0° C., iodomethane (3.38 g, 23.8 mmol, 1.48 mL, 6.81 eq) was added dropwise. The mixture was warmed up to 25° C. and stirred for another 3 hours. The reaction mixture was quenched with water (20 mL) and extracted with ethyl acetate (20 mL×3). The combined organic layers were washed with brine (20 mL), dried over Na$_2$SO$_4$, filtered and concentrated under reduced pressure to give a residue. The residue was purified by prep-HPLC (column: Phenomenex Gemini C18 250*50 mm*10 um; mobile phase: [water (0.05% ammonia hydroxide v/v)-ACN]; B %: 45%-70%, 28 MIN; 40% min). Title compound 1-bromo-8-methyl-naphthalene (340 mg, 1.49 mmol, 43% yield, 97% purity) was obtained as a yellow solid after lyophilisation.

$^1$H NMR (400 MHz, chloroform-d) δ=7.75 (dd, J=0.8, 7.2 Hz, 1H), 7.69 (dd, J=0.8, 8.0 Hz, 1H), 7.66-7.59 (m, 1H), 7.30-7.22 (m, 2H), 7.13 (t, J=8.0 Hz, 1H), 3.05 (s, 3H).

Intermediate 70

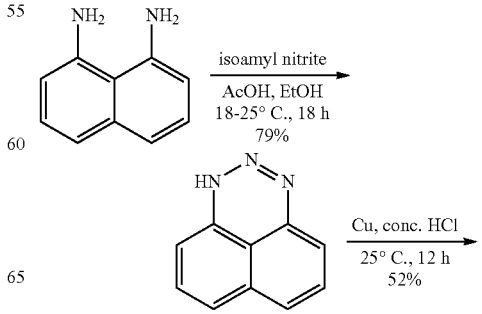

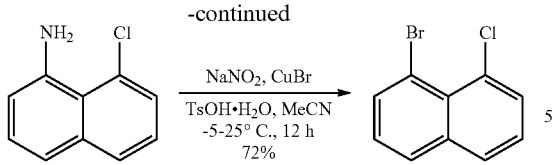

1-bromo-8-chloronaphthalene

Step A: 1H-naphtho[1,8-de][1,2,3]triazine

To a solution of naphthalene-1,8-diamine (100 g, 632 mmol, 1 eq) in AcOH (200 mL) and EtOH (1000 mL) was added isoamyl nitrite (72.6 g, 619 mmol, 83.4 mL, 0.98 eq) dropwise over a period of 2 h with temperature controlled between 18 and 21° C. under a cold-water bath. After the addition, the resulting red suspension was stirred at 25° C. for 16 hours. The solid was collected by filtration, washed with ethanol (2×500 mL) and dried under vacuum. Compound 1H-naphtho[1,8-de][1,2,3]triazine (84 g, 496 mmol, 79% yield) was obtained as a red crystalline solid and directly used next step without purification. LCMS [ESI, M+1]: 170.

Step B: 8-chloronaphthalen-1-amine

To a solution of 1H-naphtho[1,8-de][1,2,3]triazine (84 g, 496 mmol, 1 eq) in HCl (1.5 L) was added Cu (2.10 g, 33.1 mmol, 234 uL, 0.0665 eq). The mixture was stirred at 25° C. for 12 hours. The resulting mixture was diluted with water (500 mL) and heated at 85° C. for 30 mins. The resulting almost clear aqueous solution was filtered, cooled, basified with aqueous ammonia (until blue to litmus paper) and the solution was extracted with ether acetate (2×1000 mL). The combined extracts were dried over Na₂SO₄, filtered and concentrated under vacuum. The residue was purified by column chromatography (SiO₂, Petroleum ether/Ethyl acetate=200/1 to 5/1). Compound 8-chloronaphthalen-1-amine (57 g, 259 mmol, 52% yield, 81% purity) was obtained as a red solid. LCMS [ESI, M+1]: 178.

Step C: 1-bromo-8-chloro-naphthalene

To a solution of 8-chloronaphthalen-1-amine (57 g, 320 mmol, 1 eq) and TsOH.H₂O (219 g, 1.16 mol, 3.6 eq) in MeCN (1000 mL) was added a solution of NaNO₂ (39.8 g, 577 mmol, 1.8 eq) and CuBr (138 g, 963 mmol, 29.3 mL, 3 eq) in H₂O (120 mL) at −5° C., then the reaction mixture was stirred at 25° C. for 12 hours. The reaction mixture was added saturated Na₂SO₃ solution (100 mL) and stirred for 15 mins, then extracted with ethyl acetate (1000 mL×3). The combined organic layers were washed with brine (500 mL), dried over Na₂SO₄, filtered and concentrated under reduced pressure to give a residue. The residue was purified by column chromatography (SiO₂, Petroleum ether). Title compound 1-bromo-8-chloro-naphthalene (56 g, 229 mmol, 72% yield, 99% purity) was obtained as white solid.

¹H NMR (400 MHz, chloroform-d) δ=7.93 (dd, J=1.2, 7.6 Hz, 1H), 7.82 (dd, J=1.2, 8.4, 1H), 7.79 (dd, J=1.2, 8.4, 1H), 7.67 (dd, J=1.2, 7.6 Hz, 1H), 7.37 (t, J=8.0 Hz, 1H), 7.28 (t, J=8.0 Hz, 1H).

Intermediate 71

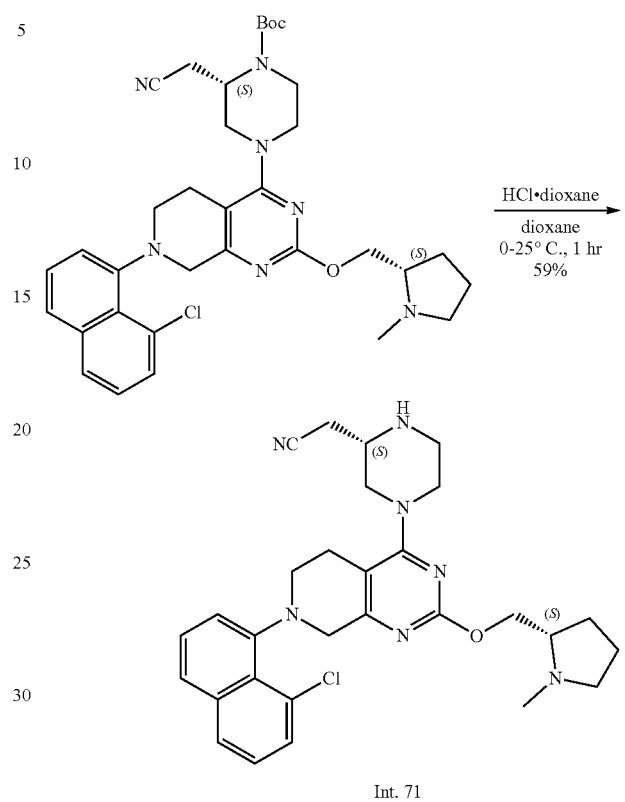

Int. 71

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile Step A: 2-[(2S)-4-[7-(8-chloro-1-naphthyl)-2-[[(2S)-1-methyl pyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl) piperazine-1-carboxylate (0.5 g, 791 umol, 1 eq) in dioxane (5 mL) was added HCl.dioxane (4 M, 5.00 mL, 25.3 eq) at 0° C. The mixture was stirred at 25° C. for 1 hour. Upon completion, the mixture was concentrated under vacuum to give an impure product (500 mg, crude, HCl) as a brown solid. 60 mg of the impure product was purified by prep-HPLC (column: Phenomenex Gemini 150*25 mm*10 um; mobile phase: [water (0.04% NH₃.H₂O+10 mM NH₄HCO₃)-ACN]; B %: 50%-80%, 10 min). The desired fractions were collected and lyophilized to give title compound 2-[(2S)-4-[7-(8-chloro-1-naphthyl)-2-[[(2S)-1-methyl pyrrolidin-2-yl]methoxy]-6,8-dihydro-5H-pyrido[3,4-d]pyrimidin-4-yl]piperazin-2-yl]acetonitrile (19.3 mg, 36.1 umol, 34% purification yield, 99.2% purity) as a off-white solid. LCMS [ESI, M+1]:532.

¹H NMR (400 MHz, chloroform-d) δ=7.75 (d, J=8.4 Hz, 1H), 7.60 (dd, J=1.6, 8.0 Hz, 1H), 7.52 (dd, J=0.8, 7.2 Hz, 1H), 7.44 (dt, J=3.6, 7.6 Hz, 1H), 7.36-7.29 (m, 1H), 7.22 (t, J=6.8 Hz, 1H), 4.46-4.34 (m, 2H), 4.15 (td, J=6.4, 10.6 Hz, 1H), 4.04 (br d, J=12.4 Hz, 0.5H), 3.95-3.79 (m, 2H), 3.74 (br d, J=12.8 Hz, 0.5H), 3.63-3.48 (m, 1H), 3.40-2.99 (m, 7H), 2.98-2.80 (m, 2H), 2.73-2.61 (m, 1H), 2.60-2.49 (m, 3H), 2.47 (d, J=2.4 Hz, 3H), 2.32-2.23 (m, 1H), 2.10-1.99 (m, 1H), 1.82-1.68 (m, 3H).

Intermediate 72

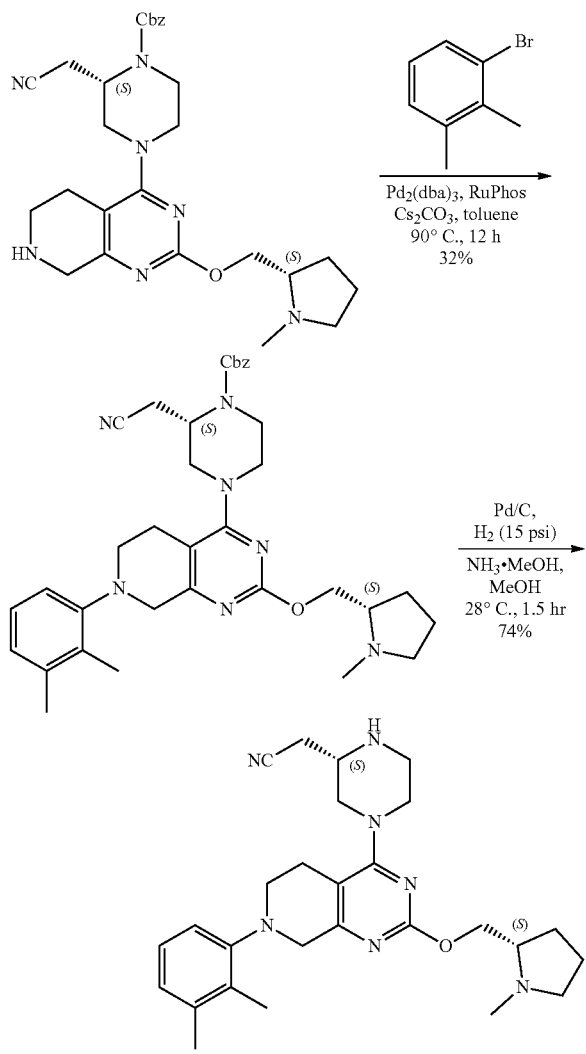

Int. 72

2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile Step A: (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate A mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (1.22 g, 1.98 mmol, 1.0 eq), 1-bromo-2,3-dimethyl-benzene (1.10 g, 5.93 mmol, 802 uL, 3.0 eq), Cs₂CO₃ (1.93 g, 5.93 mmol, 3 eq), RuPhos (185 mg, 396 umol, 0.2 eq) and Pd₂(dba)₃ (181 mg, 198 umol, 0.1 eq) in toluene (8 mL) was de-gassed and then heated to 90° C. for 12 hours under N₂. Upon completion, the mixture was concentrated under vacuum. The residue was diluted with water (20 mL) and extracted with EtOAc (3×30 mL). The organic layers were dried over Na₂SO₄, filtered and concentrated under vacuum. The residue was purified by reversed-phase flash [water (0.1% FA)/acetonitrile]. The collected desired fractions were neutralized with saturated aqueous sodium bicarbonate and concentrated under vacuum to remove MeCN, and then extracted with EtOAc (3×50 mL). The organic layers were dried over Na₂SO₄ and concentrated under vacuum to give (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (380 mg, 623 umol, 32% yield, 100% purity) as a yellow solid. LCMS [ESI, M+1]: 610.

Step B: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile NH₃ was bubbled into MeOH (20 mL) at −70° C. for 30 minutes. A solution of benzyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (380 mg, 623 umol, 1.0 eq) was added the above solution followed by Pd/C (200 mg, 10% purity) under N₂. The suspension was degassed under vacuum and purged with H₂ several times. The reaction was stirred under H₂ (15 psi) at 25° C. for 1 hour. Upon completion, the catalyst was filtered and the filtrate was concentrated to give title compound 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (230 mg, 459 umol, 74% yield, 95% purity) as a yellow solid.

¹H NMR (400 MHz, chloroform-d) δ=7.11 (t, J=8.0 Hz, 1H), 6.96 (d, J=8.0 Hz, 2H), 4.39 (dd, J=4.8, 10.4 Hz, 1H), 4.14 (dd, J=7.2, 9.6 Hz, 1H), 4.02-3.95 (m, 3H), 3.84-3.78 (m, 1H), 3.31-3.19 (m, 1H), 3.17-3.04 (m, 5H), 3.04-2.95 (m, 1H), 2.89 (dd, J=9.2, 11.6 Hz, 1H), 2.76-2.62 (m, 3H), 2.58-2.50 (m, 2H), 2.48 (s, 3H), 2.30 (s, 3H), 2.29-2.23 (m, 4H), 2.12-2.00 (m, 1H), 1.89-1.76 (m, 3H).

Intermediate 73

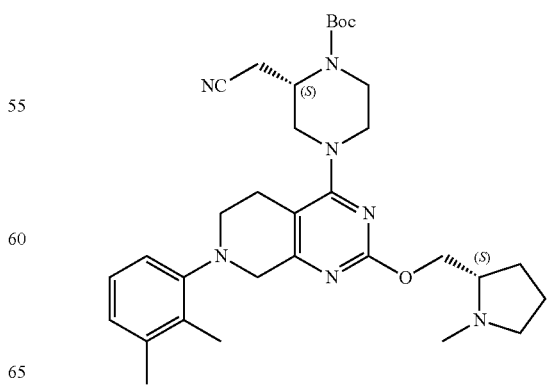

tert-butyl(2S)-2-(cyanomethyl)-4-[7-(2,3-dimethyl-phenyl)-2-[[(2S)-1-methylpyrrolidin-2-yl]methoxy]-6,8-dihydro-5H-pyrido[3,4-d]pyrimidin-4-yl]pipera-zine-1-carboxylate Step A: tert-butyl (2S)-2-(cyanomethyl)-4-[7-(2,3-dimethylphenyl)-2-methylsulfanyl-6,8-dihydro-5H-pyrido[3,4-d]pyrimidin-4-yl]piperazine-1-carboxylate A mixture of tert-butyl (2S)-2-(cyanomethyl)-4-(2-methylsulfanyl-5,6,7,8-tetrahydropyrido[3,4-d]pyrimidin-4-yl)piperazine-1-carboxylate (1.60 g, 3.96 mmol, 1.0 eq), 1-bromo-2,3-dimethyl-benzene (1.61 g, 8.70 mmol, 1.18 mL, 2.20 eq), Pd$_2$(dba)$_3$ (362 mg, 395 umol, 0.10 eq), RuPhos (369 mg, 791 umol, 0.20 eq) and Cs$_2$CO$_3$ (3.87 g, 11.9 mmol, 3.0 eq) in toluene (8.0 mL) was degassed and purged with N$_2$ for 3 times, and then the mixture was stirred at 90° C. for 12 hrs under N$_2$ atmosphere. The organic solvent was washed with water (20.0 mL). The aqueous phase was extracted with ethyl acetate (3×30.0 mL). Combine extracts were washed with brine (80.0 mL), dried with Na$_2$SO$_4$ the solvent was then removed under vacuum. The residue was purified by column chromatography (SiO$_2$, Petroleum ether: Ethyl acetate=3:1 to Ethyl acetate:Methanol=10:1). Compound tert-butyl (2S)-2-(cyanomethyl)-4-[7-(2,3-dimethylphenyl)-2-methylsulfanyl-6,8-dihydro-5H-pyrido[3,4-d]pyrimidin-4-yl]piperazine-1-carboxylate (900 mg, 1.59 mmol, 40% yield, 90% purity) was obtained as a yellow solid. LCMS [ESI, M+1]: 509.

$^1$H NMR (400 MHz, Chloroform-d) δ 7.11 (t, J=15.6 Hz, 1H), 6.95 (d, J=8.0 Hz, 2H), 4.63 (br s, 1H), 4.10-3.93 (m, 4H), 3.89 (br d, J=4.8 Hz, 1H), 3.27 (dd, J=3.6 Hz, J=13.6 Hz, 1H), 3.24-3.05 (m, 3H), 3.05-2.95 (m, 1H), 2.89-2.67 (m, 4H), 2.52 (s, 3H), 2.30 (s, 3H), 2.28 (s, 3H), 1.52 (s, 9H).

Step B: tert-butyl (2S)-2-(cyanomethyl)-4-[7-(2,3-dimethylphenyl)-2-methylsulfinyl-6,8-dihydro-5H-pyrido[3,4-d]pyrimidin-4-yl]piperazine-1-carboxylate A mixture of tert-butyl (2S)-2-(cyanomethyl)-4-[7-(2,3-dimethylphenyl)-2-methylsulfanyl-6,8-dihydro-5H-pyrido[3,4-d]pyrimidin-4-yl]piperazine-1-carboxylate (500 mg, 983 umol, 1.0 eq), 3-chlorobenzenecarboperoxoic acid (200 mg, 983 umol, 1.0 eq) in DCM (5.0 mL) was degassed and purged with N$_2$ for 3 times, and then the mixture was stirred at 0° C. for 30 min under N$_2$ atmosphere. The organic solvent was washed with water (10.0 mL). The aqueous phase was extracted with ethyl acetate (3×20.0 mL). Combine extracts were washed with brine (50.0 mL), dried with Na$_2$SO$_4$ the solvent was then removed under vacuum. The residue was purified by column chromatography (SiO$_2$, Petroleum ether: Ethyl acetate=3:1 to Ethyl acetate:Methanol=10:1). Compound tert-butyl (2S)-2-(cyanomethyl)-4-[7-(2,3-dimethylphenyl)-2-methylsulfinyl-6,8-dihydro-5H-pyrido[3,4-d]pyrimidin-4-yl]piperazine-1-carboxylate (450 mg, 793 umol, 81% yield, 93% purity) was obtained as a yellow solid. LCMS [ESI, M+1]:525.

Step C: tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl (2S)-2-(cyanomethyl)-4-[7-(2,3-dimethylphenyl)-2-methylsulfinyl-6,8-dihydro-5H-pyrido[3,4-d]pyrimidin-4-yl]piperazine-1-carboxylate (800 mg, 1.52 mmol, 1.0 eq), [(2S)-1-methylpyrrolidin-2-yl]methanol (369 mg, 3.20 mmol, 380 uL, 2.10 eq), t-BuONa (293 mg, 3.05 mmol, 2.0 eq) in toluene (10.0 mL) was degassed and purged with N$_2$ for 3 times, and then the mixture was stirred at 0° C. for 30 min under N$_2$ atmosphere. The reaction was quenched with water (20.0 mL). The crude mixture was extracted with ethyl acetate (3×30.0 mL). Combine extracts were washed with brine (80.0 mL), dried with Na$_2$SO$_4$ the solvent was then removed under vacuum. The residue was purified by column chromatography (SiO$_2$, Petroleum ether: Ethyl acetate=5:1 to Dichloromethane:Methanol=10:1). Title compound tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (740 mg, 1.22 mmol, 80% yield, 95% purity) was obtained as a yellow solid. LCMS [ESI, M+1]: 576.

$^1$H NMR (400 MHz, Chloroform-d) δ 7.10 (t, J=15.2 Hz, 1H), 6.95 (d, J=8.0 Hz, 2H), 4.61 (br s, 1H), 4.39 (dd, J=4.8 Hz, J=9.6 Hz, 1H), 4.13-4.00 (m, 4H), 3.89 (br d, J=12.4 Hz 1H), 3.27-3.13 (m, 3H), 3.13-2.95 (m, 3H), 2.87-2.65 (m, 5H), 2.49 (s, 3H), 2.30 (s, 3H), 2.27 (s, 3H), 2.09-2.06 (m, 1H), 2.06-2.04 (m, 1H), 1.93-1.62 (m, 4H), 1.51 (s, 9H).

Example 1

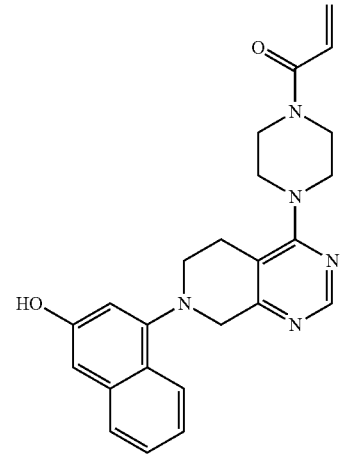 [SMILES: C=CC(=O)N1CCN(c2ncnc3c2CCN(c2cc(O)cc4ccccc24)C3)CC1]

1-(4-(7-(3-hydroxynaphthalen-1-yl)-5,6,7,8-tetrahy-dropyrido[3,4-d]pyrimidin-4-yl)piperazin-1-yl)prop-2-en-1-one

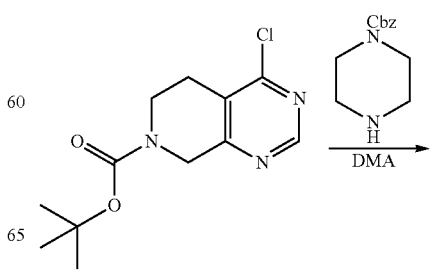

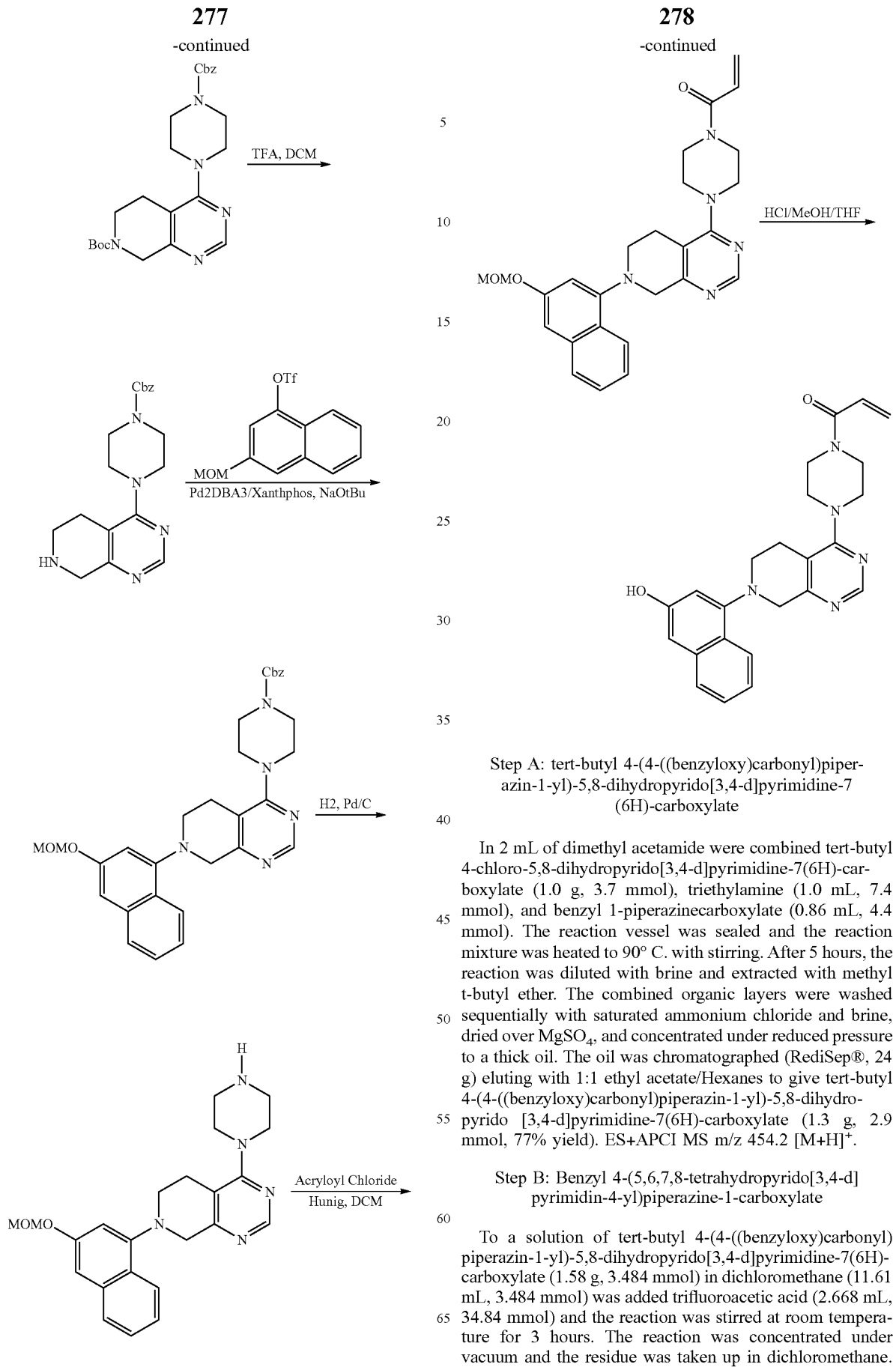

Step A: tert-butyl 4-(4-((benzyloxy)carbonyl)piper-azin-1-yl)-5,8-dihydropyrido[3,4-d]pyrimidine-7(6H)-carboxylate In 2 mL of dimethyl acetamide were combined tert-butyl 4-chloro-5,8-dihydropyrido[3,4-d]pyrimidine-7(6H)-carboxylate (1.0 g, 3.7 mmol), triethylamine (1.0 mL, 7.4 mmol), and benzyl 1-piperazinecarboxylate (0.86 mL, 4.4 mmol). The reaction vessel was sealed and the reaction mixture was heated to 90° C. with stirring. After 5 hours, the reaction was diluted with brine and extracted with methyl t-butyl ether. The combined organic layers were washed sequentially with saturated ammonium chloride and brine, dried over MgSO$_4$, and concentrated under reduced pressure to a thick oil. The oil was chromatographed (RediSep®, 24 g) eluting with 1:1 ethyl acetate/Hexanes to give tert-butyl 4-(4-((benzyloxy)carbonyl)piperazin-1-yl)-5,8-dihydropyrido [3,4-d]pyrimidine-7(6H)-carboxylate (1.3 g, 2.9 mmol, 77% yield). ES+APCI MS m/z 454.2 [M+H]$^+$.

Step B: Benzyl 4-(5,6,7,8-tetrahydropyrido[3,4-d]pyrimidin-4-yl)piperazine-1-carboxylate To a solution of tert-butyl 4-(4-((benzyloxy)carbonyl)piperazin-1-yl)-5,8-dihydropyrido[3,4-d]pyrimidine-7(6H)-carboxylate (1.58 g, 3.484 mmol) in dichloromethane (11.61 mL, 3.484 mmol) was added trifluoroacetic acid (2.668 mL, 34.84 mmol) and the reaction was stirred at room temperature for 3 hours. The reaction was concentrated under vacuum and the residue was taken up in dichloromethane.

The solution was washed with sequentially with 1M NaOH and brine, dried over Na$_2$SO$_4$, filtered and concentrated under vacuum. The crude product was purified by column chromatography (Biotage Isolera, 24G Isco RediSep® Gold, 10 to 20% methanol/dichloromethane) to afford the product (1.1 g, 89%) as an off-white foam. ES+APCI MS m/z 354.2 [M+H]$^+$.

Step C: benzyl 4-(7-(3-(methoxymethoxy)naphthalen-1-yl)-5,6,7,8-tetrahydropyrido[3,4-d]pyrimidin-4-yl)piperazine-1-carboxylate To a vial was added tris(dibenzylideneacetone)dipalladium (0) (0.0069 g, 0.0075 mmol), racemic-2,2'-bis(diphenylphosphino)-1,1'-binaphthyl (0.0096 g, 0.015 mmol) and toluene (0.62 mL, 0.19 mmol). Argon was bubbled through the mixture for 5 minutes and then the vial was capped and the mixture was heated to 100° C. for 15 minutes. The mixture was cooled to ambient temperature and then sodium tert-butoxide (0.036 g, 0.37 mmol) was added followed by 1-bromo-3-(methoxymethoxy)naphthalene (0.050 g, 0.19 mmol) and benzyl 4-(5,6,7,8-tetrahydropyrido[3,4-d]pyrimidin-4-yl)piperazine-1-carboxylate (0.13 g, 0.37 mmol). The vial was capped and the mixture heated to 100° C. for 20 hours. The mixture was cooled to ambient temperature, diluted with dichloromethane and filtered through GF/F paper. The filtrate was concentrated and purified by column chromatography (Biotage Isolera, 12G Isco RediSep®, 10-50% ethyl acetate/dichloromethane) to afford the product (0.062 g, 61%) as an off-white foam. ES+APCI MS m/z 540.3 [M+H]$^+$.

Step D: 7-(3-(methoxymethoxy)naphthalen-1-yl)-4-(piperazin-1-yl)-5,6,7,8-tetrahydropyrido[3,4-d]pyrimidine To a solution of benzyl 4-(7-(3-(methoxymethoxy)naphthalen-1-yl)-5,6,7,8-tetrahydropyrido[3,4-d]pyrimidin-4-yl)piperazine-1-carboxylate (0.061 g, 0.11 mmol) in ethanol (1.1 mL, 0.11 mmol) and tetrahydrofuran (1.1 mL, 0.11 mmol) was added palladium (0.024 g, 0.011 mmol) (Degussa Type, 10 wt. %, 50% H$_2$O). An atmosphere of H$_2$ was introduced into the reaction vessel by vacuum, and then the reaction mixture was maintained under an atmosphere of H$_2$. The mixture was stirred at ambient temperature for 2.5 hours, then diluted with methanol and filtered through GF/F paper. The colorless filtrate was concentrated under vacuum with toluene to provide an off-white foam (0.048 g, 105%) that was used directly in the next step. ES+APCI MS m/z 406.2 [M+H]$^+$.

Step E: 1-(4-(7-(3-(methoxymethoxy)naphthalen-1-yl)-5,6,7,8-tetrahydropyrido[3,4-d]pyrimidin-4-yl)piperazin-1-yl)prop-2-en-1-one To a suspension of 7-(3-(methoxymethoxy)naphthalen-1-yl)-4-(piperazin-1-yl)-5,6,7,8-tetrahydropyrido[3,4-d]pyrimidine (0.046 g, 0.11 mmol) in dichloromethane (1.1 mL, 0.11 mmol) at ambient temperature was added acryloyl chloride (1.2 mL, 0.12 mmol) (freshly prepared 0.1 M solution in dichloromethane) followed by triethylamine (0.032 mL, 0.23 mmol). The reaction was stirred at ambient temperature for 1 hour. The mixture was concentrated and the product was purified by column chromatography (Biotage Isolera, 12G Isco RediSep®, ethyl acetate) to afford the product (0.042 g, 79%) as an off-white solid foam. ES+APCI MS m/z 460.2 [M+H]$^+$.

Step F: 1-(4-(7-(3-hydroxynaphthalen-1-yl)-5,6,7,8-tetrahydropyrido[3,4-d]pyrimidin-4-yl)piperazin-1-yl)prop-2-en-1-one To a solution of 1-(4-(7-(3-(methoxymethoxy)naphthalen-1-yl)-5,6,7,8-tetrahydropyrido[3,4-d]pyrimidin-4-yl)piperazin-1-yl)prop-2-en-1-one (0.034 g, 0.074 mmol) in ethyl acetate (0.74 mL, 0.074 mmol) was added hydrochloric acid (5 to 6 N solution in 2-propanol (0.44 mL, 2.2 mmol). The mixture was stirred at ambient temperature for 5 hours. The mixture was diluted with ethyl acetate (10 mL), filtered through a polypropylene filter and the collected solid was washed with ethyl acetate and hexanes to provide the product as the HCl salt. The impure material was treated with 1 mL of ammonium hydroxide/methanol to quench the acid and the mixture was concentrated. The residue was dissolved in 10% methanol/dichloromethane and purified by column chromatography (Biotage Isolera, 12G Isco RediSep®, 2 to 5% methanol/ethyl acetate) to afford the product (0.008 g, 25%) as an off-white solid. ES+APCI MS m/z 416.2 [M+H]$^+$.

1H NMR (CD3OD, 400 MHz) δ 8.49 (s, 1H), 8.07 (app d, J=8.2 Hz, 1H), 7.61 (app d, J=8.2 Hz, 1H), 7.35 (m, 1H), 7.25 (m, 1H), 6.80 (m, 3H), 6.23 (dd, J=16.8, 1.6 Hz, 1H), 5.77 (dd, J=10.6, 2.0 Hz, 1H), 4.22 (br s, 2H), 3.80 (app t, J=4.7 Hz, 4H), 3.63 (br s, 4H), 3.35 (br s, 2H), 3.03 (br s, 2H).

Example 2

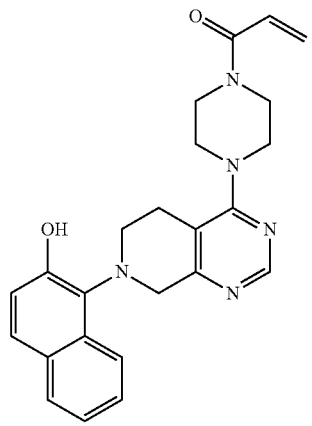 [SMILES: C=CC(=O)N1CCN(c2ncnc3c2CCN(c2c(O)ccc4ccccc24)C3)CC1]

1-(4-(7-(7-hydroxynaphthalen-1-yl)-5,6,7,8-tetrahydropyrido[3,4-d]pyrimidin-4-yl)piperazin-1-yl)prop-2-en-1-one Synthesized according to the method of Example 1, using 2-bromo-7-(methoxymethoxy)naphthalene in place of 1-bromo-3-(methoxymethoxy)naphthalene in Step C. ES+APCI MS m/z 416.1 [M+H]$^+$.

Example 3

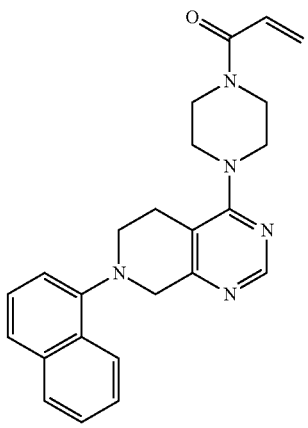 [SMILES: C=CC(=O)N1CCN(c2ncnc3c2CCN(c2cccc4ccccc24)C3)CC1]

1-(4-(7-(naphthalen-1-yl)-5,6,7,8-tetrahydropyrido[3,4-d]pyrimidin-4-yl)piperazin-1-yl)prop-2-en-1-one Synthesized according to the method of Example 1, using 1-iodonaphthalene in place of 1-bromo-3-(methoxymethoxy)naphthalene in Step C. ES+APCI MS m/z 400.2 [M+H]⁺.

Example 4

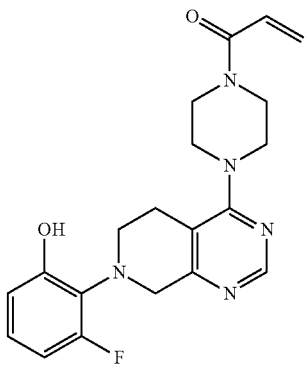 [SMILES: C=CC(=O)N1CCN(c2ncnc3c2CCN(c2c(O)cccc2F)C3)CC1]

1-(4-(7-(2-fluoro-6-hydroxyphenyl)-5,6,7,8-tetrahydropyrido[3,4-d]pyrimidin-4-yl)piperazin-1-yl)prop-2-en-1-one Synthesized according to the method of Example 1, using 2-bromo-1-fluoro-3-(methoxymethyl)benzene in place of 1-bromo-3-(methoxymethoxy)naphthalene in Step C. ES+APCI MS m/z 384.2 [M+H]⁺.

Example 5

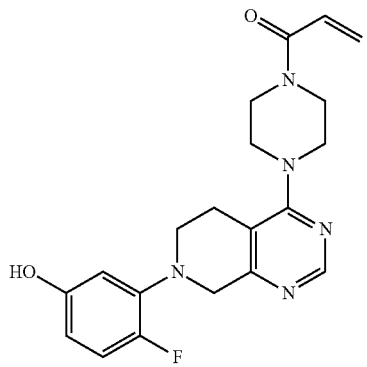 [SMILES: C=CC(=O)N1CCN(c2ncnc3c2CCN(c2cc(O)ccc2F)C3)CC1]

1-(4-(7-(2-fluoro-5-hydroxyphenyl)-5,6,7,8-tetrahydropyrido[3,4-d]pyrimidin-4-yl)piperazin-1-yl)prop-2-en-1-one Synthesized according to the method of Example 1, using 2-bromo-1-fluoro-4-(methoxymethoxy)benzene in place of 1-bromo-3-(methoxymethoxy)naphthalene in Step C. ES+APCI MS m/z 384.2 [M+H]⁺.

Example 6

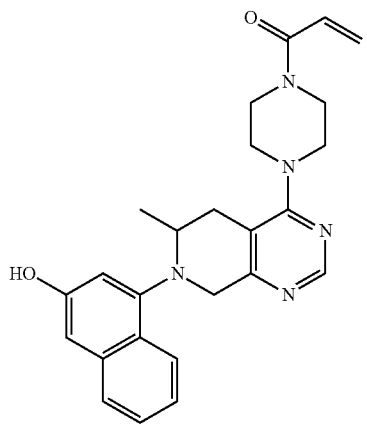 [SMILES: C=CC(=O)N1CCN(c2ncnc3c2CC(C)N(c2cc(O)cc4ccccc24)C3)CC1]

1-(4-(7-(3-hydroxynaphthalen-1-yl)-6-methyl-5,6,7,8-tetrahydropyrido[3,4-d]pyrimidin-4-yl)piperazin-1-yl)prop-2-en-1-one Steps A-C: benzyl 4-(7-(3-(methoxymethoxy)naphthalen-1-yl)-6-methyl-5,6,7,8-tetrahydropyrido[3,4-d]pyrimidin-4-yl)piperazine-1-carboxylate Synthesized according to the method of Example 1, Steps A-C, using tert-butyl 4-chloro-6-methyl-5,8-dihydropyrido[3,4-d]pyrimidine-7(6H)-carboxylate in place of 4-chloro-5,8-dihydropyrido[3,4-d]pyrimidine-7(6H)-carboxylate in Step A. ES+APCI MS m/z 430.2 [M+H]⁺.

Step D1: benzyl 4-(7-(3-hydroxynaphthalen-1-yl)-6-methyl-5,6,7,8-tetrahydropyrido[3,4-d]pyrimidin-4-yl)piperazine-1-carboxylate To a solution of benzyl 4-(7-(3-(methoxymethoxy)naphthalen-1-yl)-6-methyl-5,6,7,8-tetrahydropyrido[3,4-d]pyrimidin-4-yl)piperazine-1-carboxylate (0.05 g, 0.09 mmol) in isopropanol (10 mL) was added hydrogen chloride (5-6M in isopropanol) (0.02 mL, 0.09 mmol) and the reaction stirred at room temperature for 1 hour. The reaction was concentrated under vacuum and the concentrate was partitioned between ethyl acetate and water to convert the material to the free base. The combined organic layers were washed with brine, dried over MgSO$_4$ and concentrated under vacuum to give benzyl 4-(7-(3-hydroxynaphthalen-1-yl)-6-methyl-5,6,7,8-tetrahydropyrido[3,4-d]pyrimidin-4-yl)piperazine-1-carboxylate (0.005 g, 0.010 mmol, 11% yield). ES+APCI MS m/z 510.3 [M+H]$^+$.

Step D2: 4-(7-(3-hydroxynaphthalen-1-yl)-6-methyl-5,6,7,8-tetrahydropyrido[3,4-d]pyrimidin-4-yl)piperazin-1-ol: Prepared according to the method of Example 1, Step D.

Step E: 1-(4-(7-(3-hydroxynaphthalen-1-yl)-6-methyl-5,6,7,8-tetrahydropyrido[3,4-d]pyrimidin-4-yl)piperazin-1-yl)prop-2-en-1-one: Prepared according to the method of Example 1, Step E.

Example 7

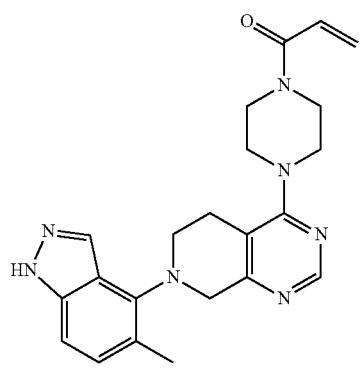 [SMILES: C=CC(=O)N1CCN(c2ncnc3c2CCN(c2c(C)ccc4[nH]ncc24)C3)CC1]

1-(4-(7-(5-methyl-1H-indazol-4-yl)-5,6,7,8-tetrahydropyrido[3,4-d]pyrimidin-4-yl)piperazin-1-yl)prop-2-en-1-one Steps A-D: benzyl 4-(7-(5-methyl-1-((2-(trimethylsilyl)ethoxy)methyl)-1H-indazol-4-yl)-5,6,7,8-tetrahydropyrido[3,4-d]pyrimidin-4-yl)piperazine-1-carboxylate: Synthesized according to General Scheme 1, Steps A-C, using 4-bromo-5-methyl-1-((2-(trimethylsilyl)ethoxy)methyl)-1H-indazole in place of 1-bromo-3-(methoxymethoxy)naphthalene in Step C Step D1: benzyl 4-(7-(5-methyl-1H-indazol-4-yl)-5,6,7,8-tetrahydropyrido[3,4-d]pyrimidin-4-yl)piperazine-1-carboxylate To a solution of benzyl 4-(7-(5-methyl-1-((2-(trimethylsilyl)ethoxy)methyl)-1H-indazol-4-yl)-5,6,7,8-tetrahydropyrido[3,4-d]pyrimidin-4-yl)piperazine-1-carboxylate (0.16 g, 0.26 mmol) in dichloromethane (10 mL) was added 2,2,2-trifluoroacetic acid (0.89 g, 7.8 mmol) followed by anisole (0.028 g, 0.26 mmol), and the reaction was stirred at room temperature for 3 hours at room temperature. The reaction was concentrated under vacuum and the concentrated material was taken up in ethyl acetate and washed with basic brine. The combined organic layers were dried over MgSO$_4$ and concentrated under vacuum. The crude material was chromatographed using 0 to 10% methanol/dichloromethane as the eluent to give benzyl 4-(7-(5-methyl-1H-indazol-4-yl)-5,6,7,8-tetrahydropyrido[3,4-d]pyrimidin-4-yl)piperazine-1-carboxylate (0.05 g, 38%). ES+APCI MS m/z 484.2 [M+H]$^+$.

Step D2: 7-(5-methyl-1H-indazol-4-yl)-4-(piperazin-1-yl)-5,6,7,8-tetrahydropyrido[3,4-d]pyrimidine: Prepared according to the method of Example 1, Step D.

Step E: 1-(4-(7-(5-methyl-1H-indazol-4-yl)-5,6,7,8-tetrahydropyrido[3,4-d]pyrimidin-4-yl)piperazin-1-yl)prop-2-en-1-one: Prepared according to the method of Example 1, Step E.

Example 8

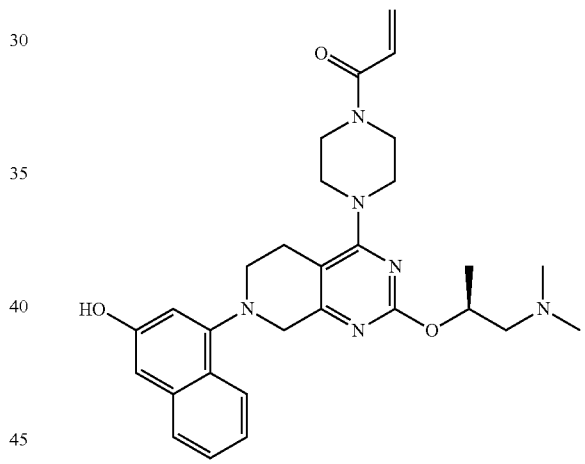

(S)-1-(4-(2-((1-(dimethylamino)propan-2-yl)oxy)-7-(3-hydroxynaphthalen-1-yl)-5,6,7,8-tetrahydropyrido[3,4-d]pyrimidin-4-yl)piperazin-1-yl)prop-2-en-1-one

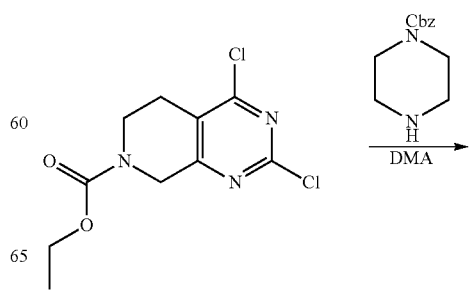

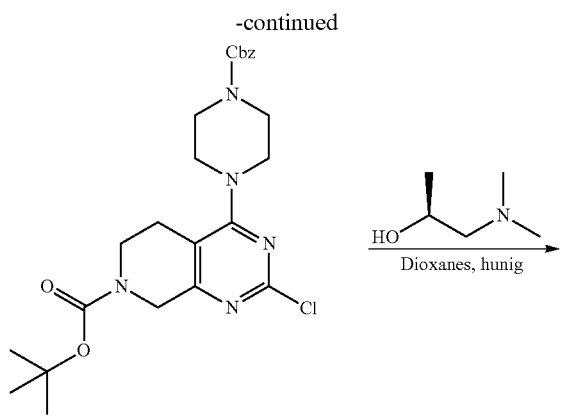
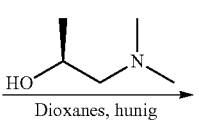
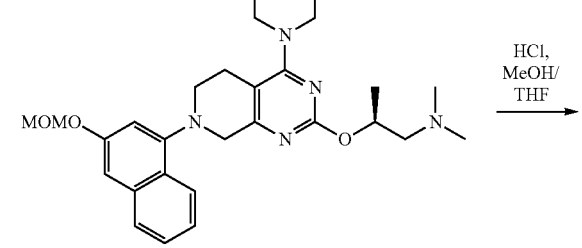
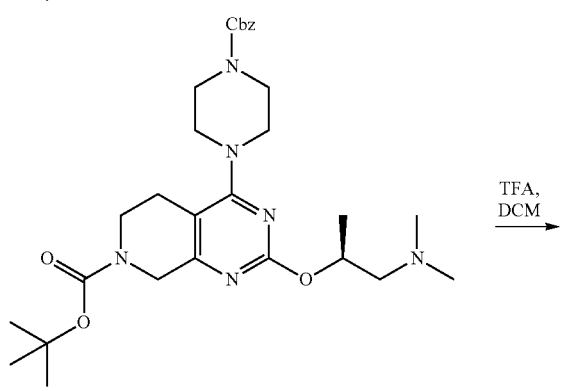
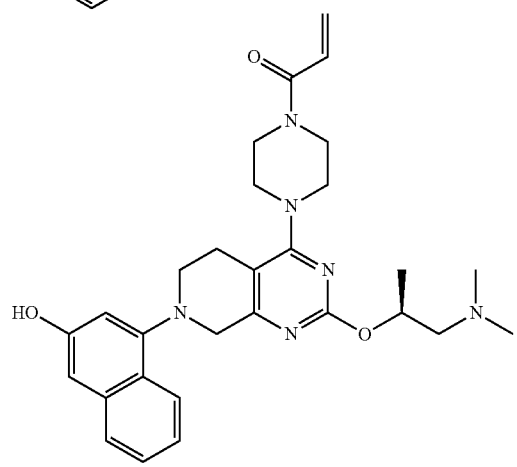
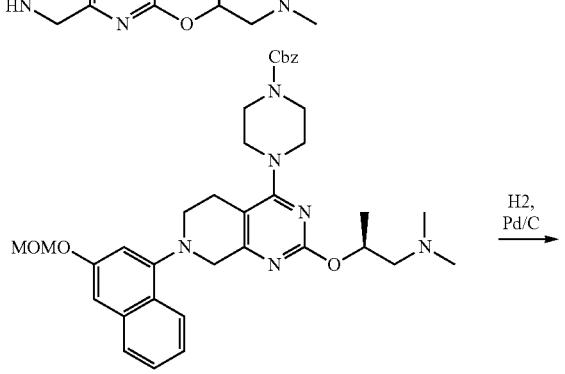
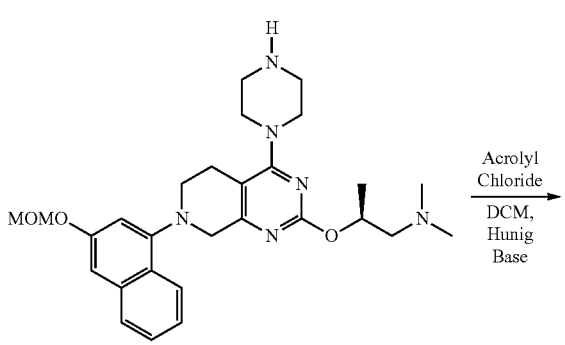

Step A: tert-butyl 4-(4-((benzyloxy)carbonyl)piperazin-1-yl)-2-chloro-5,8-dihydropyrido[3,4-d]pyrimidine-7(6H)-carboxylate Benzyl 1-piperazinecarboxylate (1.268 mL, 6.575 mmol) and tert-Butyl 2,4-dichloro-5,6-dihydropyrido[3,4-d]pyrimidine-7(8H)-carboxylate (2 g, 6.575 mmol) were dissolved in dimethyl acetamide (10 mL) and treated with N-ethyl-N-isopropylpropan-2-amine (3.445 mL, 19.73 mmol). The reaction mixture was stirred at 85° C. for 2 hours. The reaction mixture was cooled to room temperature, diluted with ethyl acetate, washed with water and brine, dried over MgSO$_4$, filtered and concentrated. The concentrate was purified by chromatography (CombiFlash®, 0%-50% ethyl acetate:Hexanes as the eluent to provide the product (2.69 g, 83%). ES+APCI MS m/z 488.2, 490.2 [M+H]$^+$.

Step B: tert-butyl (S)-4-(4-((benzyloxy)carbonyl)piperazin-1-yl)-2-((1-(dimethylamino)propan-2-yl)oxy)-5,8-dihydropyrido[3,4-d]pyrimidine-7(6H)-carboxylate: Tert-butyl 4-(4-((benzyloxy)carbonyl)piperazin-1-yl)-2-chloro-5,8-dihydropyrido[3,4-d]pyrimidine-7(6H)-carboxylate (235 mg, 0.482 mmol), and (S)-1-(dimethylamino)propan-2-ol (497 mg, 4.82 mmol) were added to dioxane (0.5 mL) and heated to 100° C. for 3 days. The reaction was concentrated and the resulting residue was purified by silica gel (Biotage Isolera, 0-12% methanol in dichloromethane) to provide tert-butyl (S)-4-(4-((benzyloxy)carbonyl)piperazin-1-yl)-2-((1-(dimethylamino)propan-2-yl)oxy)-5,8-dihydropyrido[3,4-d]pyrimidine-7(6H)-carboxylate (200 mg, 0.361 mmol, 74.9% yield). ES+APCI MS m/z 555.3 [M+H]$^+$.

Step C: benzyl (S)-4-(2-((1-(dimethylamino)propan-2-yl)oxy)-5,6,7,8-tetrahydropyrido[3,4-d]pyrimidin-4-yl)piperazine-1-carboxylate To a solution of tert-butyl (S)-4-(4-((benzyloxy)carbonyl)piperazin-1-yl)-2-((1-(dimethylamino)propan-2-yl)oxy)-5,8-dihydropyrido[3,4-d]pyrimidine-7(6H)-carboxylate (200 mg, 0.3606 mmol) in dichloromethane (1202 µL, 0.3606 mmol) was added trifluoroacetic acid (828.3 µL, 10.82 mmol) and the reaction was stirred at room temperature for 3 hours. The reaction was concentrated under vacuum and the residue was taken up in dichloromethane. The solution was washed with 1M NaOH followed by brine and then dried over $Na_2SO_4$, filtered and concentrated under vacuum. The crude product was purified by column chromatography (Biotage Isolera, 24G Isco RediSep® Gold, 10 to 20% methanol/dichloromethane) to afford the product as an off-white foam (0.135 g, 83%). ES+APCI MS m/z 455.2 $[M+H]^+$.

Step D: benzyl (S)-4-(2-((1-(dimethylamino)propan-2-yl)oxy)-7-(3-(methoxymethoxy)naphthalen-1-yl)-5,6,7,8-tetrahydropyrido[3,4-d]pyrimidin-4-yl)piperazine-1-carboxylate: To a vial was added tris(dibenzylideneacetone)dipalladium (0) (21.8 mg, 0.0238 mmol), racemic-2,2'-Bis(diphenylphosphino)-1,1'-binaphthyl (30.4 mg, 0.0488 mmol) and toluene (991 µL, 0.297 mmol). Argon was bubbled through the mixture for 5 minutes and then the vial was capped and the mixture was heated to 100° C. for 15 minutes. The mixture was cooled to ambient temperature and sodium tert-butoxide (57.2 mg, 0.595 mmol) was added followed by 3-(methoxymethoxy)naphthalen-1-yl trifluoromethanesulfonate (100 mg, 0.297 mmol) and benzyl (S)-4-(2-((1-(dimethylamino)propan-2-yl)oxy)-5,6,7,8-tetrahydropyrido[3,4-d]pyrimidin-4-yl)piperazine-1-carboxylate (135 mg, 0.297 mmol). The vial was capped and the mixture was heated to 100° C. for 18 hours. The mixture was cooled and concentrated. The crude material was purified by silica gel (Biotage Isolera, 0-11% methanol/dichloromethane to provide benzyl (S)-4-(2-((1-(dimethylamino)propan-2-yl)oxy)-7-(3-(methoxymethoxy)naphthalen-1-yl)-5,6,7,8-tetrahydropyrido[3,4-d]pyrimidin-4-yl)piperazine-1-carboxylate (68 mg, 0.106 mmol, 35.7% yield). ES+APCI MS m/z 641.3 $[M+H]^+$.

Step E: (S)-2-((7-(3-(methoxymethoxy)naphthalen-1-yl)-4-(piperazin-1-yl)-5,6,7,8-tetrahydropyrido[3,4-d]pyrimidin-2-yl)oxy)-N,N-dimethylpropan-1-amine: To a solution of benzyl (S)-4-(2-((1-(dimethylamino)propan-2-yl)oxy)-7-(3-(methoxymethoxy)naphthalen-1-yl)-5,6,7,8-tetrahydropyrido[3,4-d]pyrimidin-4-yl)piperazine-1-carboxylate (68 mg, 0.11 mmol) in ethanol (1061 µL, 0.11 mmol) and tetrahydrofuran (1061 µL, 0.11 mmol) was added Palladium (113 mg, 0.053 mmol) (Degussa Type, 10 wt. %, 50% $H_2O$). An atmosphere of $H_2$ was introduced by vacuum and then the reaction vessel was maintained under an atmosphere of $H_2$. The mixture was stirred at ambient temperature for 3 hours. The mixture was diluted with methanol and filtered through GF/F paper. The colorless filtrate was concentrated to provide (S)-2-((7-(3-(methoxymethoxy)naphthalen-1-yl)-4-(piperazin-1-yl)-5,6,7,8-tetrahydropyrido[3,4-d]pyrimidin-2-yl)oxy)-N,N-dimethylpropan-1-amine (54 mg, 100% yield) which was used in the next step without purification. ES+APCI MS m/z 507.3 $[M+H]^+$.

Step F: (S)-1-(4-(2-((1-(dimethylamino)propan-2-yl)oxy)-7-(3-(methoxymethoxy)naphthalen-1-yl)-5,6,7,8-tetrahydropyrido[3,4-d]pyrimidin-4-yl)piperazin-1-yl)prop-2-en-1-one: To a suspension of (S)-2-((7-(3-(methoxymethoxy)naphthalen-1-yl)-4-(piperazin-1-yl)-5,6,7,8-tetrahydropyrido[3,4-d]pyrimidin-2-yl)oxy)-N,N-dimethylpropan-1-amine (54 mg, 0.11 mmol) in dichloromethane (1066 µL, 0.11 mmol) at ambient temperature was added acryloyl chloride (1279 µL, 0.13 mmol) (freshly prepared 0.1 M solution in DCM) followed by triethylamine (30 µL, 0.21 mmol). The reaction was stirred at ambient temperature for 20 minutes. The mixture was concentrated and the product was purified by column chromatography (Biotage Isolera, 12G Isco RediSep®, 0-15% methanol/dichloromethane) to afford (S)-1-(4-(2-((1-(dimethylamino)propan-2-yl)oxy)-7-(3-(methoxymethoxy)naphthalen-1-yl)-5,6,7,8-tetrahydropyrido[3,4-d]pyrimidin-4-yl)piperazin-1-yl)prop-2-en-1-one (51 mg, 0.091 mmol, 85% yield). ES+APCI MS m/z 561.3 $[M+H]^+$.

Step G: 1-(4-(2-(2-(dimethylamino)ethoxy)-7-(3-hydroxynaphthalen-1-yl)-5,6,7,8-tetrahydropyrido[3,4-d]pyrimidin-4-yl)piperazin-1-yl)prop-2-en-1-one: (S)-1-(4-(2-((1-(dimethylamino)propan-2-yl)oxy)-7-(3-(methoxymethoxy)naphthalen-1-yl)-5,6,7,8-tetrahydropyrido[3,4-d]pyrimidin-4-yl)piperazin-1-yl)prop-2-en-1-one (51 mg, 0.091 mmol) was added to a vial containing 350 µL of methanol and a few drops of tetrahydrofuran and the reaction vial was capped. HCl (379 µL, 2.3 mmol) (6M aqueous) was added with stirring, and the mixture was heated to 55° C. for 3 hours. The reaction was cooled and concentrated under vacuum. A saturated bicarbonate solution was added and the reaction was extracted with 10% methanol in dichloromethane. The organic layers were combined and concentrated. The resulting residue was purified by silica gel (Biotage Isolera, 4-20% methanol in dichloromethane with 1% concentrated ammonium chloride) to provide the title product (25.3 mg, 54%). ES+APCI MS m/z 517.2 $[M+H]^+$.

$^1$H NMR (400 MHz, $CDCl_3$) δ 7.90 (d, 1H, J=8.314 Hz), 7.54 (d, 1H, J=8.021), 7.34 (m, 1H), 7.24 (m, 1H). 6.72 (m, 1H), 6.56-6.48 (m, 2H), 6.32 (dd, 1H, J=16.726, 1.858), 5.73 (dd, 1H, J=10.368, 1.858), 5.45 (m, 1H), 4.09-3.94 (m, 2H), 3.63 (bs, 2H), 3.47 (bs, 2H), 3.31 (m, 4H), 3.16 (bs, 2H), 2.84 (m, 1H), 2.60 (bs, 2H), 2.45 (m, 1H), 2.43 (s, 6H), 1.31 (d, 3H, J=6.162 Hz)

Example 9

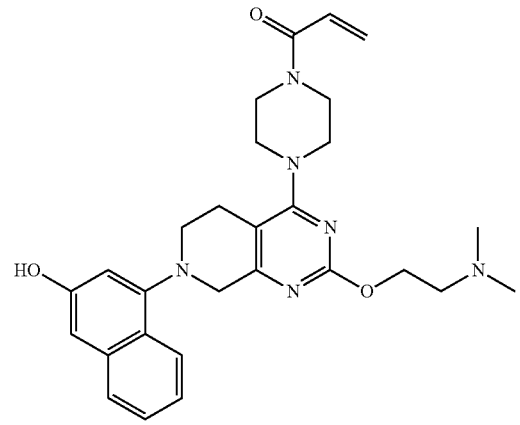 [SMILES: C=CC(=O)N1CCN(c2nc(OCCN(C)C)nc3c2CCN(c2cc(O)cc4ccccc24)C3)CC1]

289

1-(4-(2-(2-(dimethylamino)ethoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 2-(dimethylamino)ethan-1-ol in place of (S)-1-(dimethylamino)propan-2-ol in Step B. ES+APCI MS m/z 503.2 [M+H]$^+$.

Example 10

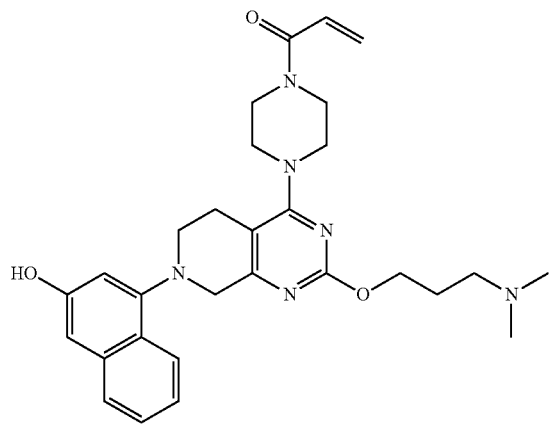 [SMILES: C=CC(=O)N1CCN(c2nc(OCCCN(C)C)nc3c2CCN(c2cc(O)cc4ccccc24)C3)CC1]

1-(4-(2-(3-(dimethylamino)propoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 3-(dimethylamino)propan-1-ol in place of (S)-1-(dimethylamino)propan-2-ol in Step B. ES+APCI MS m/z 517.3 [M+H]$^+$.

Example 11

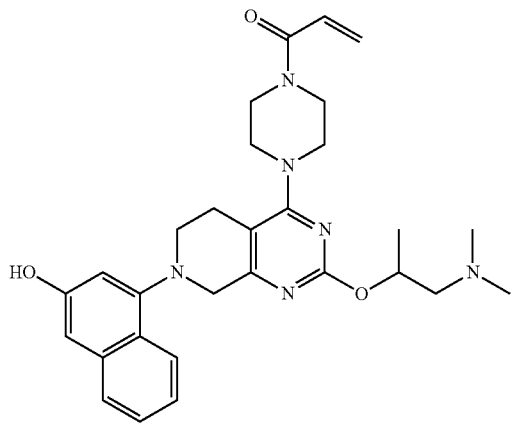 [SMILES: C=CC(=O)N1CCN(c2nc(OC(C)CN(C)C)nc3c2CCN(c2cc(O)cc4ccccc24)C3)CC1]

290

1-(4-(2-((1-(dimethylamino)propan-2-yl)oxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 1-(dimethylamino)propan-2-ol in place of (S)-1-(dimethylamino)propan-2-ol in Step B. ES+APCI MS m/z 517.3 [M+H]$^+$.

Example 12

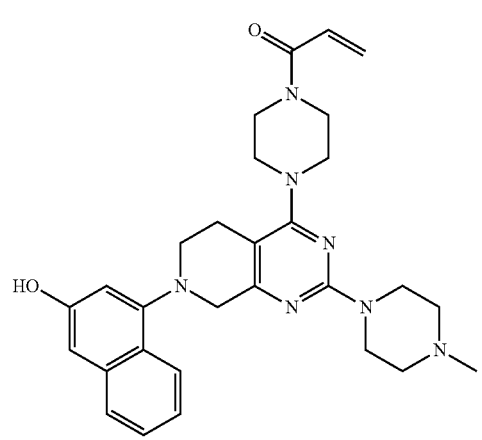 [SMILES: C=CC(=O)N1CCN(c2nc(N3CCN(C)CC3)nc3c2CCN(c2cc(O)cc4ccccc24)C3)CC1]

1-(4-(7-(3-hydroxynaphthalen-1-yl)-2-(4-methylpiperazin-1-yl)-5,6,7,8-tetrahydropyrido[3,4-d]pyrimidin-4-yl)piperazin-1-yl)prop-2-en-1-one Synthesized according to the method of Example 8, using 1-methylpiperazine in place of (S)-1-(dimethylamino)propan-2-ol in Step B. ES+APCI MS m/z 514.3 [M+H]$^+$.

Example 13

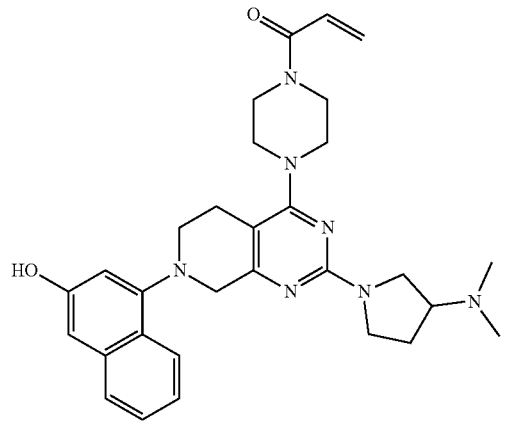

1-(4-(2-(3-(dimethylamino)pyrrolidin-1-yl)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using N,N-dimethylpyrrolidin-3-amine in place of (S)-1-(dimethylamino)propan-2-ol in Step B. ES+APCI MS m/z 528.3 [M+H]⁺.

Example 14

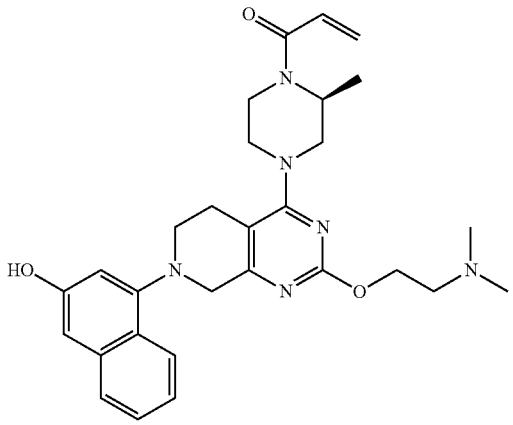 [SMILES: C=CC(=O)N1CCN(c2nc(OCCN(C)C)nc3c2CCN(c2cc(O)cc4ccccc24)C3)C[C@@H]1C]

(S)-1-(4-(7-(3-hydroxynaphthalen-1-yl)-5,6,7,8-tetrahydropyrido[3,4-d]pyrimidin-4-yl)-2-methylpiperazin-1-yl)prop-2-en-1-one Synthesized according to the method of Example 8, using benzyl (S)-2-methylpiperazine-1-carboxylate in place of benzyl piperazine-1-carboxylate in Step A and using 2-(dimethylamino)ethan-1-ol in place of (S)-1-(dimethylamino)propan-2-ol in Step B. ES+APCI MS m/z 517.3 [M+H]⁺.

Example 15

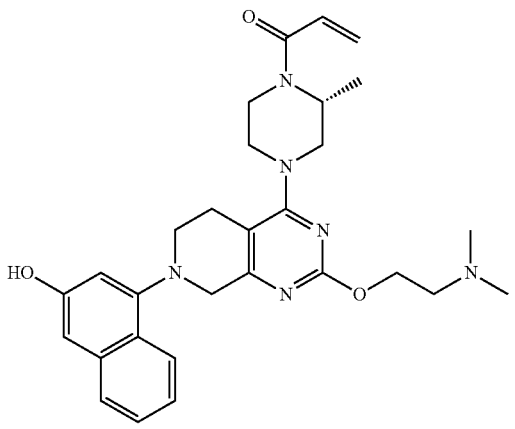 [SMILES: C=CC(=O)N1CCN(c2nc(OCCN(C)C)nc3c2CCN(c2cc(O)cc4ccccc24)C3)C[C@H]1C]

(R)-1-(4-(2-(2-(dimethylamino)ethoxy)-7-(3-hydroxynaphthalen-1-yl)-5,6,7,8-tetrahydropyrido[3,4-d]pyrimidin-4-yl)-2-methylpiperazin-1-yl)prop-2-en-1-one Synthesized according to the method of Example 8, substituting benzyl (R)-2-methylpiperazine-1-carboxylate for benzyl piperazine-1-carboxylate in Step A and 2-(dimethylamino)ethan-1-ol for (S)-1-(dimethylamino)propan-2-ol in Step B. ES+APCI MS m/z 517.3 [M+H]⁺.

Example 16

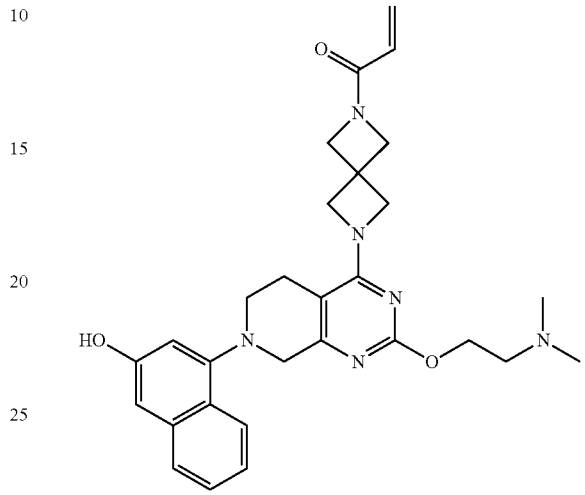

1-(6-(2-(2-(dimethylamino)ethoxy)-7-(3-hydroxynaphthalen-1-yl)-5,6,7,8-tetrahydropyrido[3,4-d]pyrimidin-4-yl)-2,6-diazaspiro[3.3]heptan-2-yl)prop-2-en-1-one Synthesized according to the method of Example 8, using benzyl 2,6-diazaspiro[3.3]heptane-2-carboxylate in place of benzyl piperazine-1-carboxylate in Step A and substituting 2-(dimethylamino)ethan-1-ol in place of (S)-1-(dimethylamino)propan-2-ol in Step B. ES+APCI MS m/z 515.3 [M+H]⁺.

Example 17

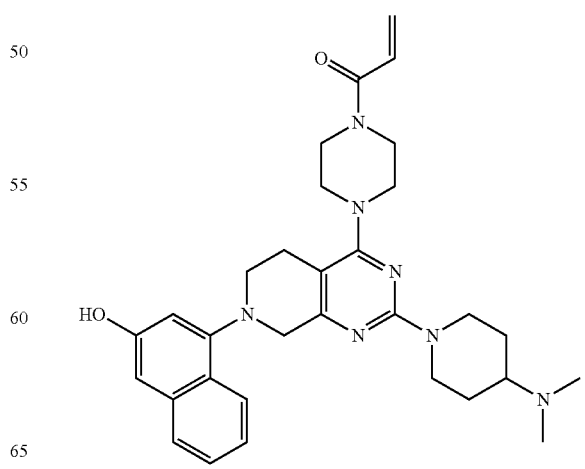

1-(4-(2-(4-(dimethylamino)piperidin-1-yl)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using N,N-dimethylpiperidin-4-amine in place of (S)-1-(dimethylamino)propan-2-ol in Step B. ES+APCI MS m/z 580.3 [M+H]+.

Example 18

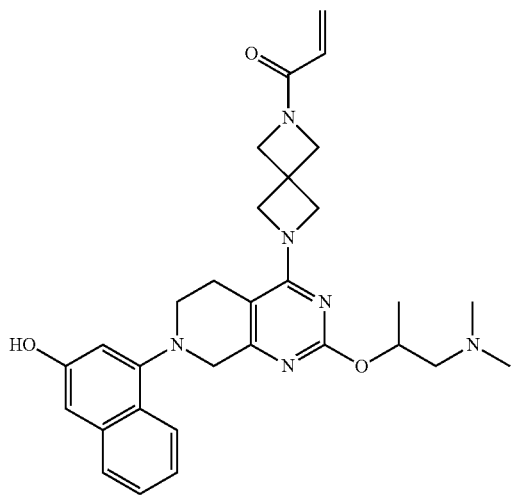 [SMILES: C=CC(=O)N1CC2(C1)CN(c1nc(OC(C)CN(C)C)nc3c1CCN(c1cc(O)cc4ccccc14)C3)C2]

1-(6-(2-((1-(dimethylamino)propan-2-yl)oxy)-7-(3-hydroxynaphthalen-1-yl)-5,6,7,8-tetrahydropyrido[3,4-d]pyrimidin-4-yl)-2,6-diazaspiro[3.3]heptan-2-yl)prop-2-en-1-one Synthesized according to the method of Example 8, using benzyl 2,6-diazaspiro[3.3]heptane-2-carboxylate in place of benzyl piperazine-1-carboxylate in Step A and substituting 1-(dimethylamino)propan-2-ol in place of (S)-1-(dimethylamino)propan-2-ol in Step B. ES+APCI MS m/z 529.3 [M+H]+.

Example 19

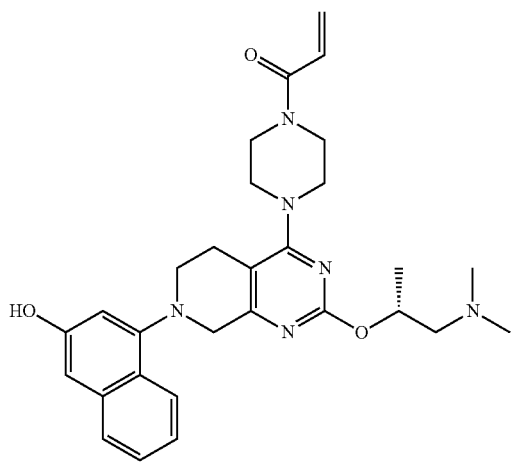 [SMILES: C=CC(=O)N1CCN(c2nc(O[C@H](C)CN(C)C)nc3c2CCN(c2cc(O)cc4ccccc24)C3)CC1]

(R)-1-(4-(2-((1-(dimethylamino)propan-2-yl)oxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using (R)-1-(dimethylamino)propan-2-ol in place of (S)-1-(dimethylamino)propan-2-ol in Step B. ES+APCI MS m/z 517.3 [M+H]+.

Example 20

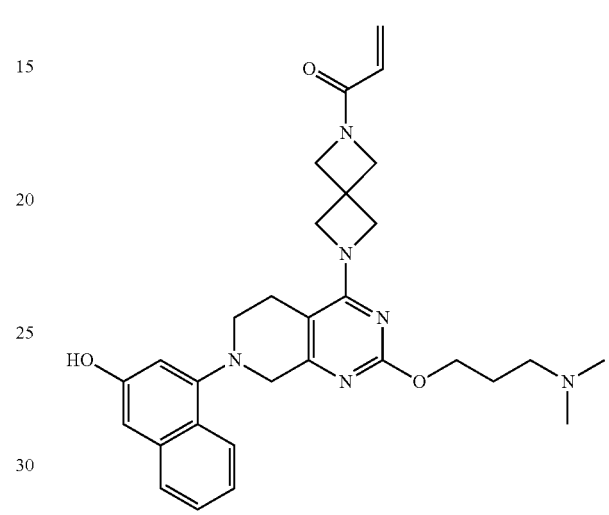

1-(6-(2-(3-(dimethylamino)propoxy)-7-(3-hydroxynaphthalen-1-yl)-5,6,7,8-tetrahydropyrido[3,4-d]pyrimidin-4-yl)-2,6-diazaspiro[3.3]heptan-2-yl)prop-2-en-1-one Synthesized according to the method of Example 8, using benzyl 2,6-diazaspiro[3.3]heptane-2-carboxylate in place of benzyl piperazine-1-carboxylate in Step A and substituting 3-(dimethylamino)propan-1-ol in place of (S)-1-(dimethylamino)propan-2-ol in Step B. ES+APCI MS m/z 529.3 [M+H]+.

Example 21

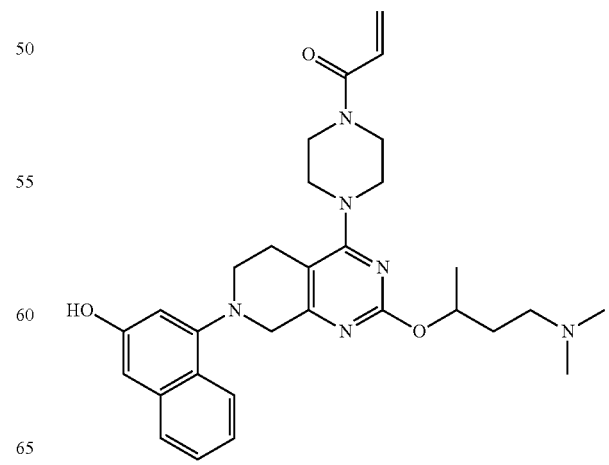

1-(4-(2-((4-(dimethylamino)butan-2-yl)oxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 4-(dimethylamino)butan-2-ol in place of (S)-1-(dimethylamino)propan-2-ol in Step B. ES+APCI MS m/z 531.3 [M+H]⁺.

Example 22

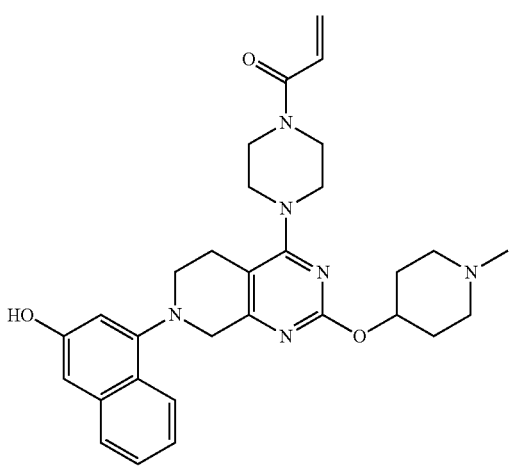 [SMILES: C=CC(=O)N1CCN(c2nc(OC3CCN(C)CC3)nc3c2CCN(c2cc(O)cc4ccccc24)C3)CC1]

1-(4-(7-(3-hydroxynaphthalen-1-yl)-2-((1-methylpiperidin-4-yl)oxy)-5,6,7,8-tetrahydropyrido[3,4-d]pyrimidin-4-yl)piperazin-1-yl)prop-2-en-1-one Synthesized according to the method of Example 8, using 1-methylpiperidin-4-ol in place of (S)-1-(dimethylamino)propan-2-ol in Step B. ES+APCI MS m/z 529.3 [M+H]⁺.

Example 23

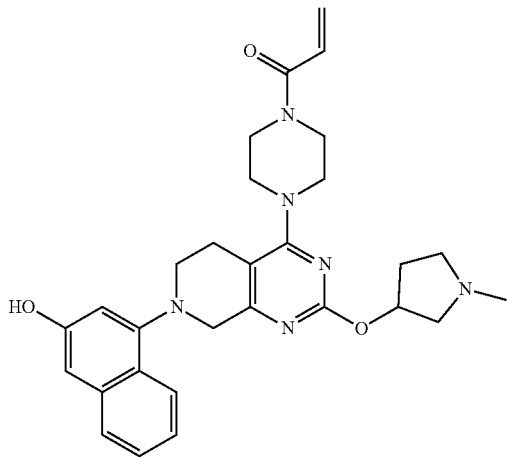 [SMILES: C=CC(=O)N1CCN(c2nc(OC3CCN(C)C3)nc3c2CCN(c2cc(O)cc4ccccc24)C3)CC1]

1-(4-(7-(3-hydroxynaphthalen-1-yl)-2-((1-methylpyrrolidin-3-yl)oxy)-5,6,7,8-tetrahydropyrido[3,4-d]pyrimidin-4-yl)piperazin-1-yl)prop-2-en-1-one Synthesized according to the method of Example 8, using 1-methylpyrrolidin-3-ol in place of (S)-1-(dimethylamino)propan-2-ol in Step B. ES+APCI MS m/z 515.3 [M+H]⁺.

Example 24

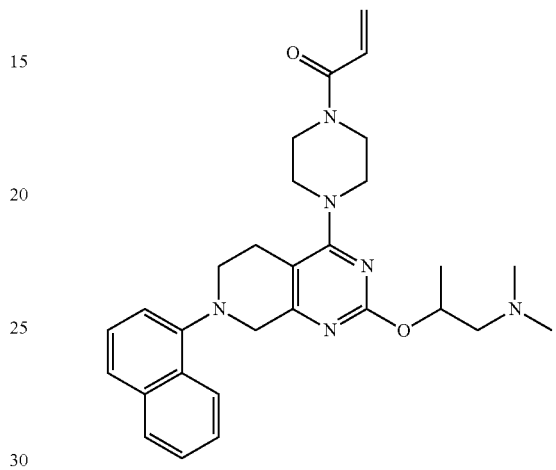

1-(4-(2-((1-(dimethylamino)propan-2-yl)oxy)-7-(naphthalen-1-yl)-5,6,7,8-tetrahydropyrido[3,4-d]pyrimidin-4-yl)piperazin-1-yl)prop-2-en-1-one Synthesized according to the method of Example 8, using 1-(dimethylamino)propan-2-ol in place of (S)-1-(dimethylamino)propan-2-ol in Step B, using 1-bromo naphthalene in place of 3-(methoxymethoxy)naphthalen-1-yl trifluoromethanesulfonate in step D, and eliminating Step G. ES+APCI MS m/z 501.3 [M+H]⁺.

Example 25

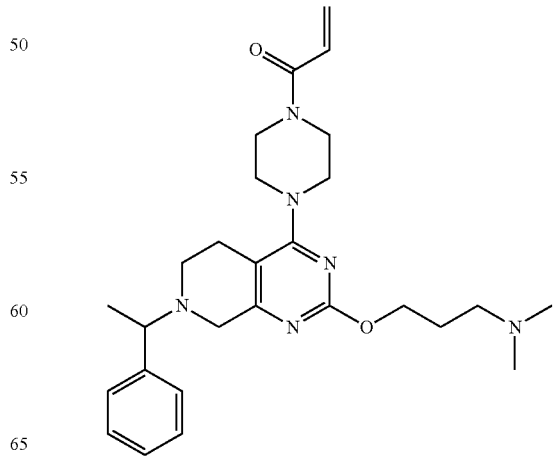

1-(4-(2-(3-(dimethylamino)propoxy)-7-(1-phenylethyl)-5,6,7,8-tetrahydropyrido[3,4-d]pyrimidin-4-yl)piperazin-1-yl)prop-2-en-1-one Synthesized according to the method of Example 8, using 3-(dimethylamino)propan-1-ol in place of (S)-1-(dimethylamino)propan-2-ol in Step B, using (1-bromoethyl)benzene in place of 3-(methoxymethoxy)naphthalen-1-yl trifluoromethanesulfonate in step D, and eliminating Step G. ES+APCI MS m/z 559.3 [M+H]⁺.

Example 26

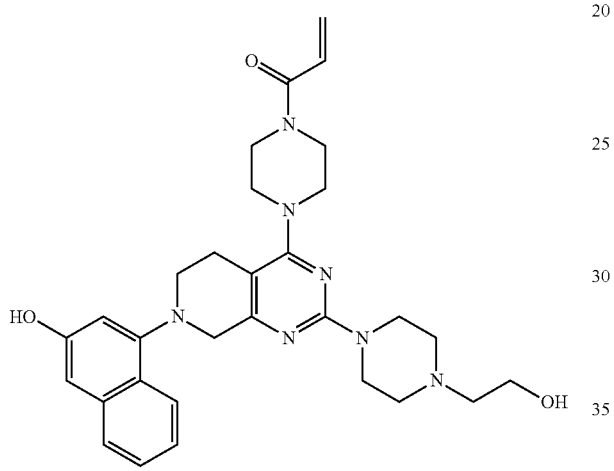

1-(4-(2-(4-(2-hydroxyethyl)piperazin-1-yl)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 2-(piperazin-1-yl)ethyl acetate in place of (S)-1-(dimethylamino)propan-2-ol in Step B. After Step D, the following saponification reaction was performed: Benzyl 4-(2-(4-(2-acetoxyethyl)piperazin-1-yl)-7-(3-(methoxymethoxy)naphthalen-1-yl)-5,6,7,8-tetrahydropyrido[3,4-d]pyrimidin-4-yl)piperazine-1-carboxylate was taken up in THF (5 mL) and 2 M LiOH (1 mL) was added. The mixture was stirred at ambient temperature for 24 hr. Saturated NH₄Cl was added and the reaction was extracted with DCM. The combined organic layers were concentrated and the resulting residue was purified by silica gel (Biotage Isolera Gold, eluting with 0-10% MeOH in DCM) to provide benzyl 4-(2-(4-(2-hydroxyethyl)piperazin-1-yl)-7-(3-(methoxymethoxy)naphthalen-1-yl)-5,6,7,8-tetrahydropyrido[3,4-d]pyrimidin-4-yl)piperazine-1-carboxylate. The remainder of the synthesis proceeded as in Example 8, step E. ES+APCI MS m/z 544.3 [M+H]⁺.

Example 27

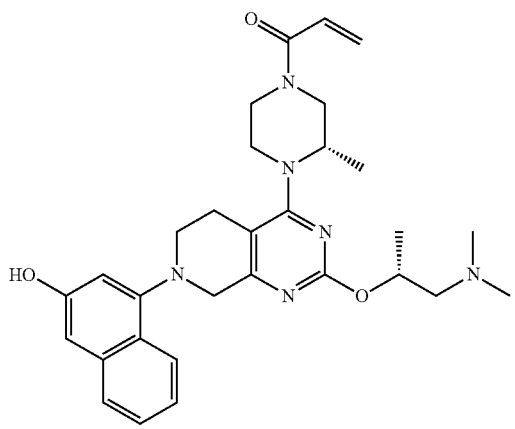 [SMILES: C=CC(=O)N1CCN(c2nc(O[C@H](C)CN(C)C)nc3c2CCN(c2cc(O)cc4ccccc24)C3)[C@@H](C)C1]

1-((S)-4-(2-(((R)-1-(dimethylamino)propan-2-yl)oxy)-7-(3-hydroxynaphthalen-1-yl)-5,6,7,8-tetrahydropyrido[3,4-d]pyrimidin-4-yl)-3-methylpiperazin-1-yl)prop-2-en-1-one Synthesized according to the method of Example 8, using benzyl (S)-3-methylpiperazine-1-carboxylate in place of benzyl piperazine-1-carboxylate in Step A and using (R)-1-(dimethylamino)propan-2-ol in place of (S)-1-(dimethylamino)propan-2-ol in Step B. ES+APCI MS m/z 531.3 [M+H]⁺.

Example 28

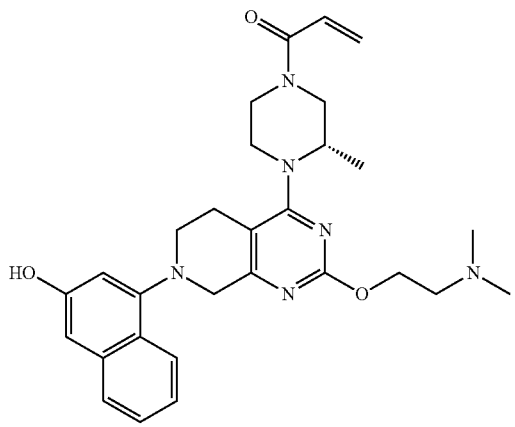 [SMILES: C=CC(=O)N1CCN(c2nc(OCCN(C)C)nc3c2CCN(c2cc(O)cc4ccccc24)C3)[C@@H](C)C1]

(S)-1-(4-(2-(2-(dimethylamino)ethoxy)-7-(3-hydroxynaphthalen-1-yl)-5,6,7,8-tetrahydropyrido[3,4-d]pyrimidin-4-yl)-3-methylpiperazin-1-yl)prop-2-en-1-one Synthesized according to the method of Example 8, using benzyl (S)-3-methylpiperazine-1-carboxylate in place of benzyl piperazine-1-carboxylate in Step A and using 2-(dimethylamino)ethan-1-ol in place of (S)-1-(dimethylamino)propan-2-ol in Step B. ES+APCI MS m/z 517.2 [M+H]⁺.

Example 29

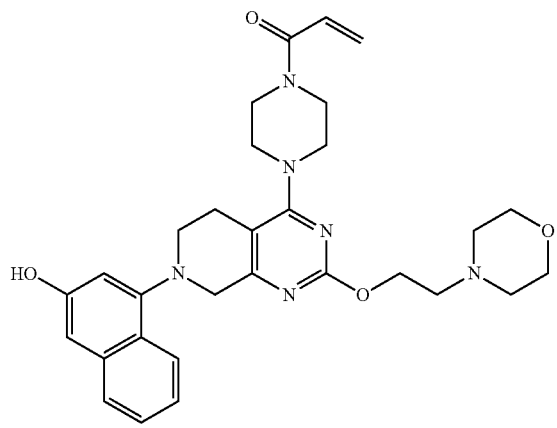 [SMILES: C=CC(=O)N1CCN(c2nc(OCCN3CCOCC3)nc3c2CCN(c2cc(O)cc4ccccc24)C3)CC1]

1-(4-(7-(3-hydroxynaphthalen-1-yl)-2-(2-morpholinoethoxy)-5,6,7,8-tetrahydropyrido[3,4-d]pyrimidin-4-yl)piperazin-1-yl)prop-2-en-1-one Synthesized according to the method of Example 8, using 2-morpholinoethan-1-ol in place of (S)-1-(dimethylamino)propan-2-ol in Step B. ES+APCI MS m/z 545.2 [M+H]$^+$.

Example 30

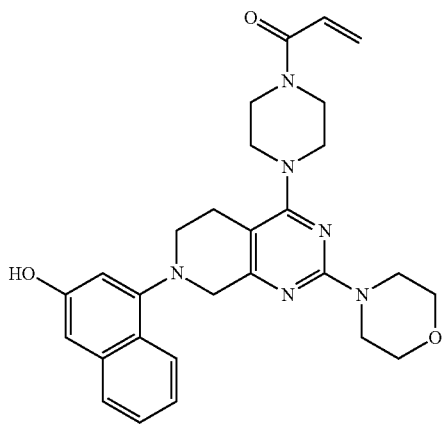 [SMILES: C=CC(=O)N1CCN(c2nc(N3CCOCC3)nc3c2CCN(c2cc(O)cc4ccccc24)C3)CC1]

1-(4-(7-(3-hydroxynaphthalen-1-yl)-2-morpholino-5,6,7,8-tetrahydropyrido[3,4-d]pyrimidin-4-yl)piperazin-1-yl)prop-2-en-1-one Synthesized according to the method of Example 8, using morpholine in place of (S)-1-(dimethylamino)propan-2-ol in Step B. ES+APCI MS m/z 501.3 [M+H]$^+$.

Example 31

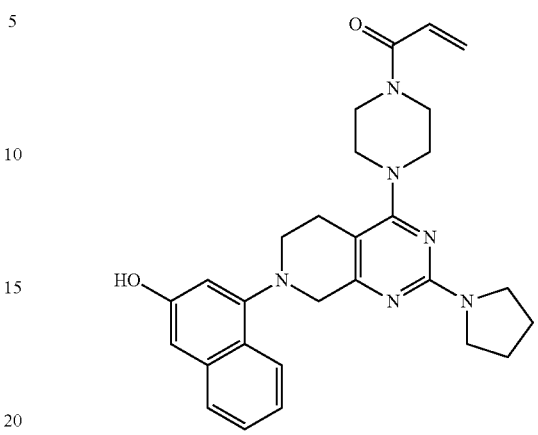

1-(4-(7-(3-hydroxynaphthalen-1-yl)-2-(pyrrolidin-1-yl)-5,6,7,8-tetrahydropyrido[3,4-d]pyrimidin-4-yl)piperazin-1-yl)prop-2-en-1-one Synthesized according to the method of Example 8, using pyrrolidine in place of (S)-1-(dimethylamino)propan-2-ol in Step B. ES+APCI MS m/z 485.2 [M+H]$^+$.

Example 32

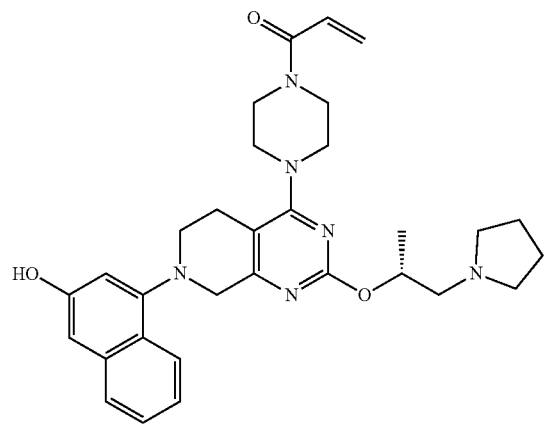 [SMILES: C=CC(=O)N1CCN(c2nc(O[C@H](C)CN3CCCC3)nc3c2CCN(c2cc(O)cc4ccccc24)C3)CC1]

(R)-1-(4-(7-(3-hydroxynaphthalen-1-yl)-2-((1-(pyrrolidin-1-yl)propan-2-yl)oxy)-5,6,7,8-tetrahydropyrido[3,4-d]pyrimidin-4-yl)piperazin-1-yl)prop-2-en-1-one Synthesized according to the method of Example 8, using (R)-1-(pyrrolidin-1-yl)propan-2-ol in place of (S)-1-(dimethylamino)propan-2-ol in Step B. ES+APCI MS m/z 543.4 [M+H]$^+$.

Example 33

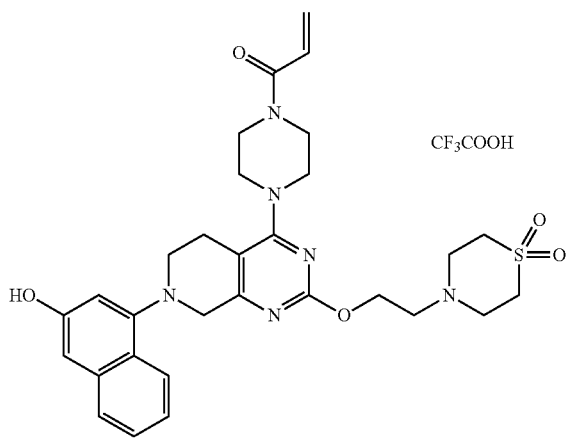 [SMILES: C=CC(=O)N1CCN(c2nc(OCCN3CCS(=O)(=O)CC3)nc3c2CCN(c2cc(O)cc4ccccc24)C3)CC1 ; "CF3COOH"]

1-(4-(2-(2-(1,1-dioxidothiomorpholino)ethoxy)-7-(3-hydroxynaphthalen-1-yl)-5,6,7,8-tetrahydropyrido[3,4-d]pyrimidin-4-yl)piperazin-1-yl)prop-2-en-1-one trifluoroacetate Step A: benzyl 4-[7-(3-benzyloxy-1-naphthyl)-2-[2-(1,1-dioxo-1,4-thiazinan-4-yl)ethoxy]-6,8-dihydro-5H-pyrido[3,4-d]pyrimidin-4-yl]piperazine-1-carboxylate: To a mixture of benzyl 4-[7-(3-benzyloxy-1-naphthyl)-2-methylsulfinyl-6,8-dihydro-5H-pyrido[3,4-d]pyrimidin-4-yl]piperazine-1-carboxylate (300 mg, 463.12 µmol, 1.00 eq) and 2-(1,1-dioxo-1,4-thiazinan-4-yl)ethanol (166 mg, 926 µmol, 2.00 eq) in toluene (10.0 mL) was added NaOBu-t (133 mg, 1.39 mmol, 3.00 eq), BINAP (57.7 mg, 92.6 µmol, 0.20 eq), Pd₂(dba)₃ (42.4 mg, 46.3 µmol, 0.10 eq). The reaction mixture was stirred at 90° C. for 12 hours under N₂. The reaction mixture was filtered and the filter cake was washed with DCM (3×10 mL). The filtrate was concentrated under vacuum. The residue was purified by reverse flash chromatography (40% MeCN in water (0.1% TFA) to give benzyl 4-[7-(3-benzyloxy-1-naphthyl)-2-[2-(1,1-dioxo-1,4-thiazinan-4-yl)ethoxy]-6,8-dihydro-5H-pyrido[3,4-d]pyrimidin-4-yl]piperazine-1-carboxylate (230 mg, 301 µmol, 65.1% yield) as a brown solid. ESI MS m/z 763.5 [M+H]⁺.

Step B: 4-[2-[2-(1,1-dioxo-1,4-thiazinan-4-yl)ethoxy]-4-piperazin-1-yl-6,8-dihydro-5H-pyrido[3,4-d]pyrimidin-7-yl]naphthalen-2-ol To a solution of benzyl 4-[7-(3-benzyloxy-1-naphthyl)-2-[2-(1,1-dioxo-1,4-thiazinan-4-yl)ethoxy]-6,8-dihydro-5H-pyrido[3,4-d]pyrimidin-4-yl]piperazine-1-carboxylate (190 mg, 249 µmol, 1.00 eq) in MeOH (10.0 mL) was added Pd/C (100 mg) under N₂. The suspension was degassed under vacuum and purged with hydrogen several times. The mixture was stirred under hydrogen (15 psi) at 40° C. for 4 hours. The reaction mixture was filtered and the filtrate was concentrated under vacuum to give 4-[2-[2-(1,1-dioxo-1,4-thiazinan-4-yl)ethoxy]-4-piperazin-1-yl-6,8-dihydro-5H-pyrido[3,4-d]pyrimidin-7-yl]naphthalen-2-ol (90.0 mg, 167 µmol, 67.1% yield) as a brown solid. ESI MS m/z 539.4 [M+H]⁺.

Step C: 1-[4-[2-[2-(1,1-dioxo-1,4-thiazinan-4-yl)ethoxy]-7-(3-hydroxy-1-naphthyl)-6,8-dihydro-5H-pyrido[3,4-d]pyrimidin-4-yl]piperazin-1-yl]prop-2-en-1-one: To a solution of 4-[2-[2-(1,1-dioxo-1,4-thiazinan-4-yl)ethoxy]-4-piperazin-1-yl-6,8-dihydro-5H-pyrido[3,4-d]pyrimidin-7-yl]naphthalen-2-ol (90.0 mg, 167 µmol, 1.00 eq) and DIEA (64.8 mg, 501 µmol, 87.5 µL, 3.00 eq) in DCM (2.00 mL) was added prop-2-enoyl prop-2-enoate (19.0 mg, 150 µmol, 0.90 eq) at −40° C. The reaction mixture was stirred at −40° C. for 0.5 h. The reaction mixture was quenched with 1 mL of MeOH and concentrated under vacuum. The residue was purified by preparative HPLC column: Phenomenex Synergi C18 150*25*, 10µ; mobile phase: [water (0.1% TFA)-ACN]; B %: 12%-42%, 11 min to give 1-[4-[2-[2-(1,1-dioxo-1,4-thiazinan-4-yl)ethoxy]-7-(3-hydroxy-1-naphthyl)-6,8-dihydro-5H-pyrido[3,4-d]pyrimidin-4-yl]piperazin-1-yl]prop-2-en-1-one trifluoroacetate (32.6 mg, 50.2 µmol, 30.0% yield, 91.3% purity) as a brown solid. ESI MS m/z 593.5 [M+H]⁺.

Example 34

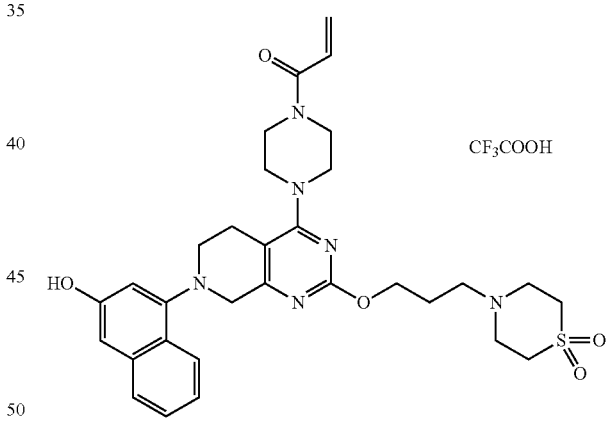

1-(4-(2-(3-(1,1-dioxidothiomorpholino)propoxy)-7-(3-hydroxynaphthalen-1-yl)-5,6,7,8-tetrahydropyrido[3,4-d]pyrimidin-4-yl)piperazin-1-yl)prop-2-en-1-one trifluoroacetate Synthesized according to the method of Example 33, using 3-(1,1-dioxo-1,4-thiazinan-4-yl)propan-1-ol in place of 2-(1,1-dioxo-1,4-thiazinan-4-yl)ethanol in Step A. ESI MS m/z 607.5 [M+H]⁺.

Example 35

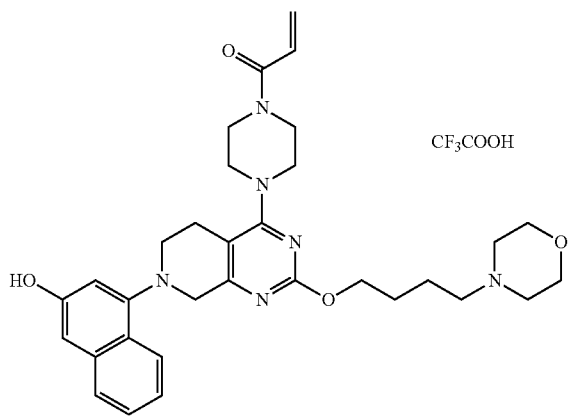 [SMILES: C=CC(=O)N1CCN(c2nc(OCCCCN3CCOCC3)nc3c2CCN(c2cc(O)cc4ccccc24)C3)CC1 ; "CF3COOH"]

1-(4-(7-(3-hydroxynaphthalen-1-yl)-2-(4-morpholinobutoxy)-5,6,7,8-tetrahydropyrido[3,4-d]pyrimidin-4-yl)piperazin-1-yl)prop-2-en-1-one trifluoroacetate Synthesized according to the method of Example 33, using 4-morpholinobutan-1-ol in place of 2-(1,1-dioxo-1,4-thiazinan-4-yl)ethanol in Step A. ESI MS m/z 573.4 [M+H]+.

Example 36

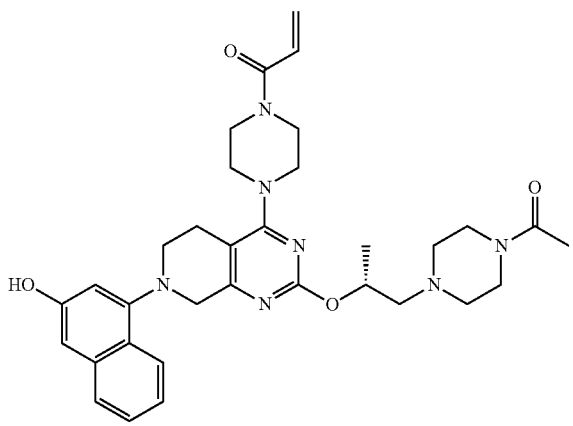 [SMILES: C=CC(=O)N1CCN(c2nc(O[C@H](C)CN3CCN(C(C)=O)CC3)nc3c2CCN(c2cc(O)cc4ccccc24)C3)CC1]

(R)-1-(4-(2-((1-(4-acetylpiperazin-1-yl)propan-2-yl)oxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 33, using 1-[4-[(2R)-2-hydroxypropyl]piperazin-1-yl]ethanone in place of 2-(1,1-dioxo-1,4-thiazinan-4-yl)ethanol in Step A. ESI MS m/z 600.6 [M+H]+.

Example 37

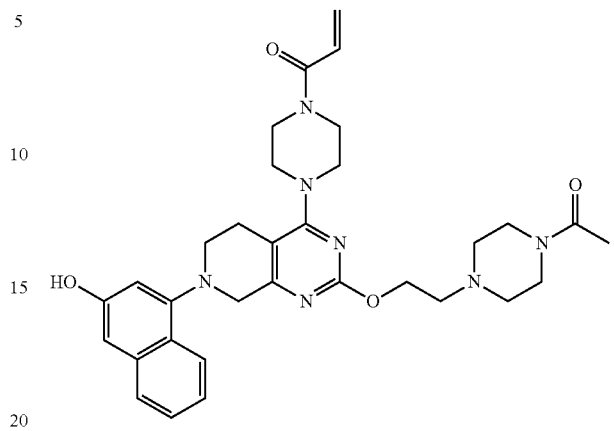

1-(4-(2-(2-(4-acetylpiperazin-1-yl)ethoxy)-7-(3-hydroxynaphthalen-1-yl)-5,6,7,8-tetrahydropyrido[3,4-d]pyrimidin-4-yl)piperazin-1-yl)prop-2-en-1-one Step A: benzyl 4-[2-[2-(4-acetylpiperazin-1-yl)ethoxy]-7-(3-benzyloxy-1-naphthyl)-6,8-dihydro-5H-pyrido[3,4-d]pyrimidin-4-yl]piperazine-1-carboxylate: To a solution of 1-[4-(2-hydroxyethyl)piperazin-1-yl]ethanone (277 mg, 1.61 mmol, 2.60 eq) in THF (8.00 mL) was added NaH (49.4 mg, 1.23 mmol, 60% purity, 2.00 eq) at 0° C. The reaction mixture was stirred at 0° C. for 15 minutes. To the mixture was added benzyl-4-[7-(3-benzyloxy-1-naphthyl)-2-methylsulfinyl-6,8-dihydro-5H-pyrido[3,4-d]pyrimidin-4-yl]piperazine-1-carboxylate (400 mg, 618 μmol, 1.00 eq) in THF (2.00 mL). The reaction mixture was stirred at 0° C. for 20 minutes. The reaction mixture was quenched with saturated NH4Cl (6 mL) and water (6 mL). The reaction mixture was extracted with ethyl acetate (3×30 mL). The combined organic layers were washed with brine (10 mL), dried over Na2SO4 and concentrated under vacuum to give benzyl 4-[2-[2-(4-acetylpiperazin-1-yl)ethoxy]-7-(3-benzyloxy-1-naphthyl)-6,8-dihydro-5H-pyrido[3,4-d]pyrimidin-4-yl]piperazine-1-carboxylate (450 mg, 534 μmol, 86.5% yield, 89.7% purity) as a brown solid. ESI MS m/z 756.3 [M+H]+.

Step B: 1-[4-[2-[[7-(3-hydroxy-1-naphthyl)-4-piperazin-1-yl-6,8-dihydro-5H-pyrido[3,4-d]pyrimidin-2-yl]oxy]ethyl]piperazin-1-yl]ethanone: To a solution of benzyl 4-[2-[2-(4-acetylpiperazin-1-yl)ethoxy]-7-(3-benzyloxy-1-naphthyl)-6,8-dihydro-5H-pyrido[3,4-d]pyrimidin-4-yl]piperazine-1-carboxylate (200 mg, 264 μmol, 1.00 eq) in THF (10.0 mL) was added Pd/C (100 mg, 10% purity) under N2. The suspension was degassed under vacuum and purged with hydrogen several times. The mixture was stirred under hydrogen (15 psi) at 40° C. for 12 hours. The reaction mixture was filtered and the filter cake was washed with THF (3×5 mL). The filtrate was concentrated under vacuum to give 1-[4-[2-[[7-(3-hydroxy-1-naphthyl)-4-piperazin-1-yl-6,8-dihydro-5H-pyrido[3,4-d]pyrimidin-2-yl]oxy]ethyl]piperazin-1-yl]ethanone (80.0 mg, 150 μmol, 56.9% yield) as a brown solid.

Step C: 1-[4-[2-[2-(4-acetylpiperazin-1-yl)ethoxy]-7-(3-hydroxy-1-naphthyl)-6,8-dihydro-5H-pyrido[3,4-d]pyrimidin-4-yl]piperazin-1-yl]prop-2-en-1-one: To a solution of 1-[4-[2-[[7-(3-hydroxy-1-naphthyl)-4-piperazin-1-yl-6,8-dihydro-5H-pyrido[3,4-d]pyrimidin-2-yl]oxy]ethyl]piperazin-1-yl]ethanone (80.0 mg, 150 μmol, 1.00 eq) and DIEA (58.3 mg, 451 μmol, 78.8 μL, 3.00 eq) in DCM (2.00 mL) was added prop-2-enoyl prop-2-enoate (14.2 mg, 113 μmol, 0.75 eq) at −40° C. for 0.5 h. The reaction mixture was quenched with MeOH (1 mL) and diluted by DCM (20 mL) next washed with water (5 mL). The combined organic layers were washed with brine (5 mL), dried over $Na_2SO_4$ and concentrated under vacuum. The reaction mixture was purified by preparative HPLC: Phenomenex Gemini 150*25 mm*, 10μ; mobile phase: [water (0.05% ammonia hydroxide v/v)-ACN]; B %: 30%-55%, 10 min to give 1-[4-[2-[2-(4-acetylpiperazin-1-yl)ethoxy]-7-(3-hydroxy-1-naphthyl)-6,8-dihydro-5H-pyrido[3,4-d]pyrimidin-4-yl]piperazin-1-yl]prop-2-en-1-one (13.8 mg, 23.3 μmol, 15.5% yield, 98.7% purity) as a yellow solid. ESI MS m/z 586.3 $[M+H]^+$.

Example 38

Example 39

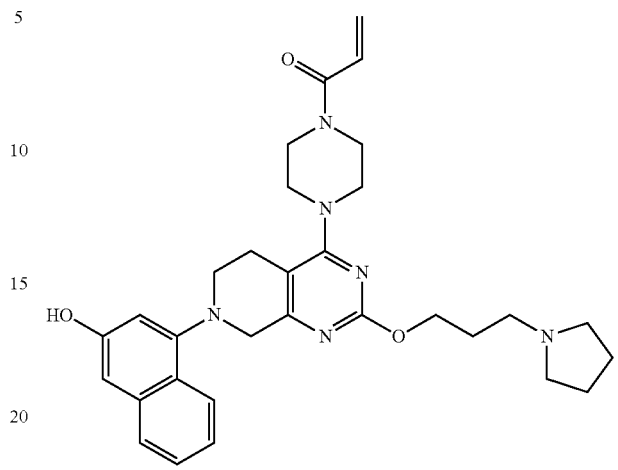

1-(4-(7-(3-hydroxynaphthalen-1-yl)-2-(3-(pyrrolidin-1-yl)propoxy)-5,6,7,8-tetrahydropyrido[3,4-d]pyrimidin-4-yl)piperazin-1-yl)prop-2-en-1-one Synthesized according to the method of Example 37, using 3-pyrrolidin-1-ylpropan-1-ol in place of 1-[4-(2-hydroxyethyl)piperazin-1-yl]ethanone in Step A. ESI MS m/z 543.3 $[M+H]^+$.

Example 40

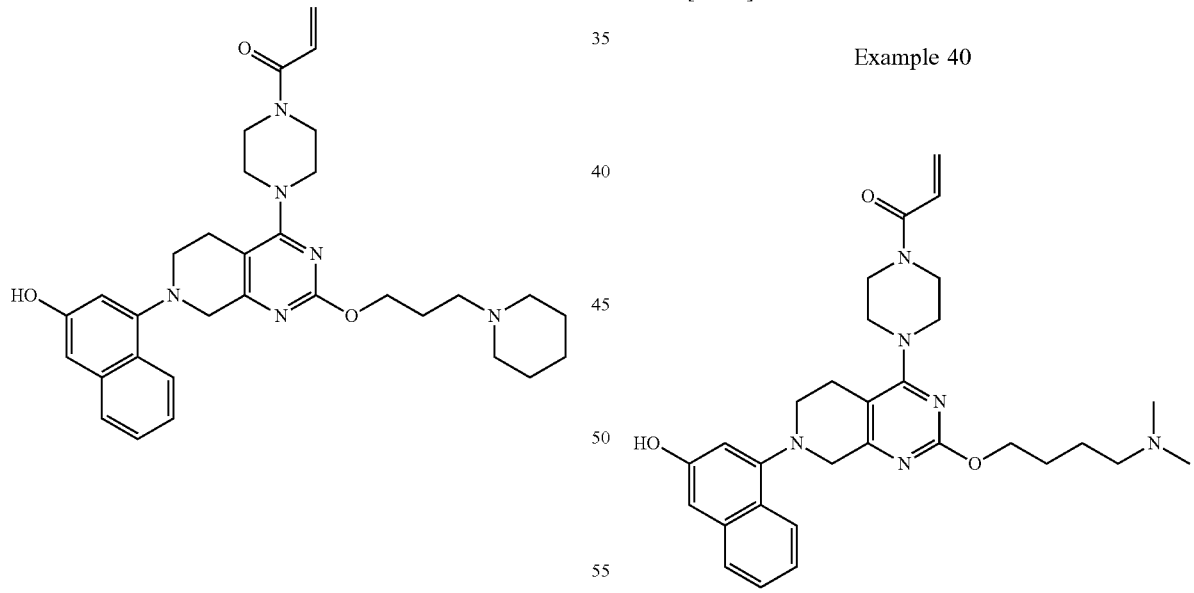

1-(4-(7-(3-hydroxynaphthalen-1-yl)-2-(3-(piperidin-1-yl)propoxy)-5,6,7,8-tetrahydropyrido[3,4-d]pyrimidin-4-yl)piperazin-1-yl)prop-2-en-1-one Synthesized according to the method of Example 37, using 3-(1-piperidyl)propan-1-ol in place of 1-[4-(2-hydroxyethyl)piperazin-1-yl]ethanone in Step A. ESI MS m/z 557.5 $[M+H]^+$.

1-(4-(2-(4-(dimethylamino)butoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 37, using 4-(dimethylamino)butan-1-ol in place of 1-[4-(2-hydroxyethyl)piperazin-1-yl]ethanone in Step A. ESI MS m/z 531.4 $[M+H]^+$.

Example 41

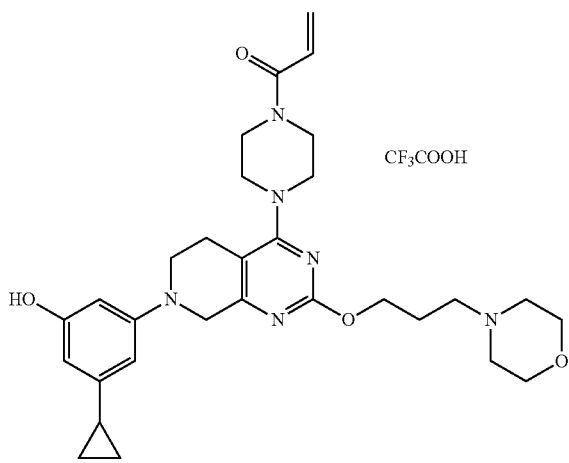 [SMILES: C=CC(=O)N1CCN(c2nc(OCCCN3CCOCC3)nc3c2CCN(c2cc(O)cc(C4CC4)c2)C3)CC1 ; "CF3COOH"]

1-(4-(7-(3-cyclopropyl-5-hydroxyphenyl)-2-(3-morpholinopropoxy)-5,6,7,8-tetrahydropyrido[3,4-d]pyrimidin-4-yl)piperazin-1-yl)prop-2-en-1-one trifluoroacetate Step A: 4-[7-(3-benzyloxy-5-cyclopropyl-phenyl)-2-(3-morpholinopropoxy)-6,8-dihydro-5H-pyrido[3,4-d]pyrimidin-4-yl]piperazine-1-carboxylate: To a mixture of benzyl 4-[2-(3-morpholinopropoxy)-5,6,7,8-tetrahydropyrido[3,4-d]pyrimidin-4-yl]piperazine-1-carboxylate (400 mg, 805 µmol, 1.00 eq) and 1-benzyloxy-3-bromo-5-cyclopropyl-benzene (268 mg, 886 µmol, 1.10 eq) in toluene (10.0 mL) was added 2-dicyclohexylphosphino-2',6'-diisopropoxybiphenyl (RuPhos) (75.2 mg, 161 µmol, 0.20 eq), Pd$_2$(dba)$_3$ (111 mg, 121 µmol, 0.15 eq) and Cs$_2$CO$_3$ (656 mg, 2.01 mmol, 2.50 eq). The reaction mixture was stirred at 90° C. for 12 hours under N$_2$. The mixture was added to water (15 mL) and extracted with DCM (2×15 mL). The combined organic layers were dried over Na$_2$SO$_4$, filtered and concentrated. The residue was purified by chromatography (SiO$_2$, Petroleum ether/Ethyl acetate=3:1 to Dichloromethane:Methanol=10:1) to give benzyl 4-[7-(3-benzyloxy-5-cyclopropyl-phenyl)-2-(3-morpholinopropoxy)-6,8-dihydro-5H-pyrido[3,4-d]pyrimidin-4-yl]piperazine-1-carboxylate (170 mg, 230 µmol, 28.5% yield, 97.2% purity) as brown oil. ESI MS m/z 719.6 [M+H]$^+$.

Step B: 3-cyclopropyl-5-[2-(3-morpholinopropoxy)-4-piperazin-1-yl-6,8-dihydro-5H-pyrido[3,4-d]pyrimidin-7-yl]phenol To a mixture of benzyl 4-[7-(3-benzyloxy-5-cyclopropyl-phenyl)-2-(3-morpholinopropoxy)-6,8-dihydro-5H-pyrido[3,4-d]pyrimidin-4-yl]piperazine-1-carboxylate (150 mg, 209 µmol, 1.00 eq) in MeOH (10.0 mL) was added Pd/C (150 mg, 10% purity) and CH$_3$COOH (25.1 mg, 417.3 µmol, 23.9 µL, 2.00 eq). The suspension was degassed under vacuum and purged with hydrogen several times. The mixture was stirred under hydrogen (15 Psi) at 40° C. for 2 hours. The reaction mixture was filtered through Celite® and the filtrate was concentrated. The product 3-cyclopropyl-5-[2-(3-morpholinopropoxy)-4-piperazin-1-yl-6,8-dihydro-5H-pyrido[3,4-d]pyrimidin-7-yl]phenol diacetate (80.0 mg, 130 µmol, 62.4% yield) was obtained as yellow solid. ESI MS m/z 495.2 [M+H]$^+$.

Step C: 1-[4-[7-(3-cyclopropyl-5-hydroxy-phenyl)-2-(3-morpholinopropoxy)-6,8-dihydro-5H-pyrido[3,4-d]pyrimidin-4-yl]piperazin-1-yl]prop-2-en-1-one To a mixture of 3-cyclopropyl-5-[2-(3-morpholinopropoxy)-4-piperazin-1-yl-6,8-dihydro-5H-pyrido[3,4-d]pyrimidin-7-yl]phenol diacetate (80.0 mg, 130 µmol, 1.00 eq) in DCM (2.00 mL) was added DIEA (168 mg, 1.30 mmol, 227 µL, 10.0 eq) and prop-2-enoyl prop-2-enoate (13.1 mg, 104 µmol, 0.80 eq) at −78° C., the reaction mixture was stirred at −78° C. for 0.5 hour. The reaction mixture was quenched with MeOH (2 eq, 10 mg), then concentrated. The residue was purified by preparative HPLC (Instrument: GX-K; Column: Phenomenex Synergi C18 150*25*, 10µ; Conditions: water (0.1% TFA)-ACN; Begin B: 8; End B: 38; Gradient Time (min): 11; 100% B Hold Time (min): 2; FlowRate (mL/min): 25). The isolated product was concentrated by lyophilization. The product 1-[4-[7-(3-cyclopropyl-5-hydroxy-phenyl)-2-(3-morpholinopropoxy)-6,8-dihydro-5H-pyrido[3,4-d]pyrimidin-4-yl]piperazin-1-yl]prop-2-en-1-one trifluoroacetate (21.5 mg, 31.1 µmol, 23.9% yield, 95.8% purity) was obtained as yellow solid. ESI MS m/z 549.5 [M+H]$^+$.

Example 42

1-(4-(7-(2-fluoro-5-hydroxyphenyl)-2-(3-morpholinopropoxy)-5,6,7,8-tetrahydropyrido[3,4-d]pyrimidin-4-yl)piperazin-1-yl)prop-2-en-1-one Synthesized according to the method of Example 41, using 4-(benzyloxy)-2-bromo-1-fluorobenzene in place of 1-benzyloxy-3-bromo-5-cyclopropyl-benzene in Step A. ESI MS m/z 527.4 [M+H]$^+$.

Example 43

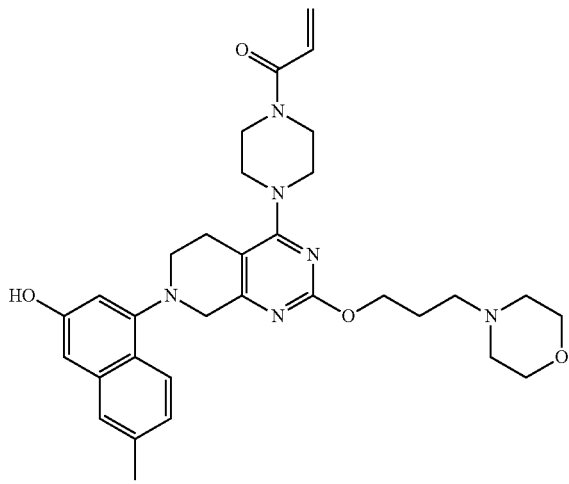 [SMILES: C=CC(=O)N1CCN(c2nc(OCCCN3CCOCC3)nc3c2CCN(c2cc(O)cc4cc(C)ccc24)C3)CC1]

1-(4-(7-(3-hydroxy-6-methylnaphthalen-1-yl)-2-(3-morpholinopropoxy)-5,6,7,8-tetrahydropyrido[3,4-d]pyrimidin-4-yl)piperazin-1-yl)prop-2-en-1-one Step A: benzyl 4-[7-(3-methoxy-6-methyl-1-naphthyl)-2-(3-morpholinopropoxy)-6,8-dihydro-5H-pyrido[3,4-d]pyrimidin-4-yl]piperazine-1-carboxylate: A mixture of benzyl 4-[2-(3-morpholinopropoxy)-5,6,7,8-tetrahydropyrido[3,4-d]pyrimidin-4-yl]piperazine-1-carboxylate (500 mg, 1.01 mmol, 1.00 eq), (3-methoxy-6-methyl-1-naphthyl)trifluoromethanesulfonate (483 mg, 1.51 mmol, 1.50 eq), $Cs_2CO_3$ (820 mg, 2.52 mmol, 2.50 eq), 2-dicyclohexylphosphino-2',6'-diisopropoxybiphenyl (RuPhos) (93.9 mg, 201.3 µmol, 0.20 eq) and $Pd_2(dba)_3$ (92.2 mg, 100 µmol, 0.10 eq) in toluene (3.00 mL) was stirred at 90° C. for 10 hours. The mixture was diluted with ethyl acetate (50.0 mL). The precipitate was removed by filtration, and the filtrate was concentrated under vacuum. The residue was purified by reversed phase column chromatography over silica gel (0.1% TFA water/acetonitrile). The desired fractions were combined and basified with saturated aqueous sodium bicarbonate (2.00 mL), then concentrated under vacuum. The residue was extracted with ethyl acetate (2×100 mL). The combined extracts were washed with brine (1×100 mL), dried over sodium sulfate, filtered and concentrated under vacuum to give benzyl 4-[7-(3-methoxy-6-methyl-1-naphthyl)-2-(3-morpholinopropoxy)-6,8-dihydro-5H-pyrido[3,4-d]pyrimidin-4-yl]piperazine-1-carboxylate (400. mg, 599 µmol, 59.4% yield, 100% purity) as a yellow solid. ESI MS m/z 667.6 [M+H]$^+$.

Step B: 4-[3-[[7-(3-methoxy-6-methyl-1-naphthyl)-4-piperazin-1-yl-6,8-dihydro-5H-pyrido[3,4-d]pyrimidin-2-yl]oxy]propyl]morpholine To a solution of benzyl 4-[7-(3-methoxy-6-methyl-1-naphthyl)-2-(3-morpholinopropoxy)-6,8-dihydro-5H-pyrido[3,4-d]pyrimidin-4-yl]piperazine-1-carboxylate (370 mg, 554 µmol, 1.00 eq) in MeOH (10.0 mL) was added Pd—C (100 mg, 10% purity) and AcOH (66.6 mg, 1.11 mmol, 2.00 eq) under $N_2$. The suspension was degassed under vacuum and purged with hydrogen several times. The mixture was stirred under hydrogen (15 psi) at 40° C. for 2 hours. The reaction mixture was filtered and concentrated in vacuum to provide 4-[3-[[7-(3-methoxy-6-methyl-1-naphthyl)-4-piperazin-1-yl-6,8-dihydro-5H-pyrido[3,4-d]pyrimidin-2-yl]oxy]propyl]morpholine (295 mg, 553 µmol, 99.8% yield) as a yellow solid which was used directly in the next step without purification. ESI MS m/z 533.6 [M+H]$^+$ Step C: 1-[4-[7-(3-methoxy-6-methyl-1-naphthyl)-2-(3-morpholinopropoxy)-6,8-dihydro-5H-pyrido[3,4-d]pyrimidin-4-yl]piperazin-1-yl]prop-2-en-1-one: To a mixture of prop-2-enoyl prop-2-enoate (56.8 mg, 450 µmol, 0.80 eq) and DIEA (727 mg, 5.63 mmol, 983 µL, 10.0 eq) in DCM (2.00 mL) was added a solution of 4-[3-[[7-(3-methoxy-6-methyl-1-naphthyl)-4-piperazin-1-yl-6,8-dihydro-5H-pyrido[3,4-d]pyrimidin-2-yl]oxy]propyl]morpholine (300 mg, 563 µmol, 1.00 eq) DCM (1.00 mL) at −40° C. under a nitrogen atmosphere. The mixture was stirred for 1 hour. The reaction mixture was quenched by addition of MeOH (50 µL) at −40° C., diluted with water (10.0 mL), extracted with DCM (10.0 mL), dried over $Na_2SO_4$, filtered and concentrated under reduced pressure to provide 1-[4-[7-(3-methoxy-6-methyl-1-naphthyl)-2-(3-morpholinopropoxy)-6,8-dihydro-5H-pyrido[3,4-d]pyrimidin-4-yl]piperazin-1-yl]prop-2-en-1-one (270 mg, 460 µmol, 81.7% yield) ESI MS m/z 587.6 [M+H]$^+$.

Step D: 1-[4-[7-(3-hydroxy-6-methyl-1-naphthyl)-2-(3-morpholinopropoxy)-6,8-dihydro-5H-pyrido[3,4-d]pyrimidin-4-yl]piperazin-1-yl]prop-2-en-1-one: To a solution of 1-[4-[7-(3-methoxy-6-methyl-1-naphthyl)-2-(3-morpholinopropoxy)-6,8-dihydro-5H-pyrido[3,4-d]pyrimidin-4-yl]piperazin-1-yl]prop-2-en-1-one (100 mg, 170 µmol, 1.00 eq) in DCM (3.00 mL) was added $BBr_3$ (213 mg, 852 µmol, 82.1 µL, 5.00 eq) at −78° C. The mixture was stirred at 0° C. for 1 hour. The mixture was cooled to −78° C. and diluted with DCM (20.0 mL), quenched by addition of saturated sodium bicarbonate solution (5.00 mL) and stirred at −78° C. for 10 mins, then warmed to 0° C. The mixture was extracted with DCM (2×15.0 mL), washed with brine (1×20.0 mL), dried over $Na_2SO_4$, filtered and concentrated under vacuum. The residue was purified by preparative HPLC (column: Phenomenex Gemini C18 250*50 mm*, 10µ; mobile phase: [water (0.05% ammonia hydroxide v/v)-ACN]; B %: 27%-57%, 12 min) to provide 1-[4-[7-(3-hydroxy-6-methyl-1-naphthyl)-2-(3-morpholinopropoxy)-6,8-dihydro-5H-pyrido[3,4-d]pyrimidin-4-yl]piperazin-1-yl]prop-2-en-1-one (11.0 mg, 18.6 µmol, 10.9% yield, 97.0% purity) as a brown solid. ESI MS m/z 573.6 [M+H]$^+$.

Example 44

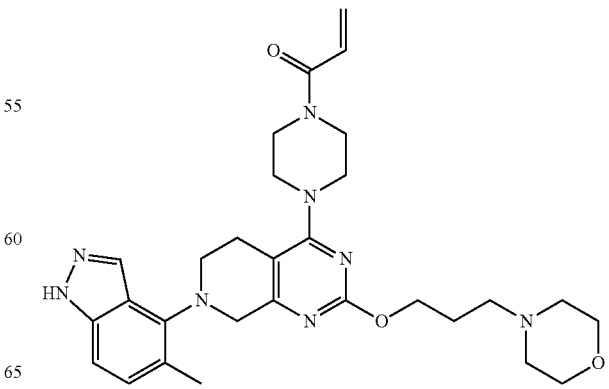

1-(4-(7-(5-methyl-1H-indazol-4-yl)-2-(3-morpholinopropoxy)-5,6,7,8-tetrahydropyrido[3,4-d]pyrimidin-4-yl)piperazin-1-yl)prop-2-en-1-one Step A: benzyl 4-[7-[5-methyl-1-(2-trimethylsilylethoxymethyl)indazol-4-yl]-2-(3-morpholinopropoxy)-6,8-dihydro-5H-pyrido[3,4-d]pyrimidin-4-yl]piperazine-1-carboxylate: A mixture of benzyl 4-[2-(3-morpholinopropoxy)-5,6,7,8-tetrahydropyrido[3,4-d]pyrimidin-4-yl]piperazine-1-carboxylate (500 mg, 1.01 mmol, 1.00 eq), 2-[(4-bromo-5-methyl-indazol-1-yl)methoxy] ethyl-trimethylsilane (448 mg, 1.31 mmol, 1.30 eq), Cs₂CO₃ (822 mg, 2.53 mmol, 2.50 eq), Pd₂(dba)₃ (138 mg, 151 μmol, 0.15 eq) and 2-dicyclohexylphosphino-2',6'-diisopropoxybiphenyl (RuPhos) (94.3 mg, 202 μmol, 0.20 eq) in toluene (20.0 mL) was degassed and purged with nitrogen 3 times, and stirred at 90° C. for 10 hours under a nitrogen atmosphere. The reaction mixture was diluted with water (50 mL) and extracted with ethyl acetate (3×100 mL). The combined organic layers were washed with brine (3×50.0 mL), dried over Na₂SO₄, filtered and concentrated under reduced pressure. The residue was purified by reversed phase HPLC (0.1% TFA water/acetonitrile) to provide benzyl 4-[7-[5-methyl-1-(2-trimethylsilylethoxymethyl)indazol-4-yl]-2-(3-morpholinopropoxy)-6,8-dihydro-5H-pyrido[3,4-d]pyrimidin-4-yl]piperazine-1-carboxylate (420 mg, 554 μmol, 54.9% yield) as a yellow oil. ESI MS m/z 757.6 [M+H]⁺.

Step B: tert-butyl 4-[7-[5-methyl-1-(2-trimethylsilylethoxymethyl)indazol-4-yl]-2-(3-morpholinopropoxy)-6,8-dihydro-5H-pyrido[3,4-d]pyrimidin-4-yl]piperazine-1-carboxylate: To a solution of benzyl 4-[7-[5-methyl-1-(2-trimethylsilylethoxymethyl) indazol-4-yl]-2-(3-morpholinopropoxy)-6,8-dihydro-5H-pyrido[3,4-d]pyrimidin-4-yl]piperazine-1-carboxylate (370 mg, 488 μmol, 1.00 eq) in MeOH (10.0 mL) was added triethylamine (98.9 mg, 977 μmol, 135 μL, 2.00 eq), Pd/C (100 mg, 10% purity) and tert-butoxycarbonyl tert-butyl carbonate (213 mg, 977 μmol, 224 μL, 2.00 eq) under N₂. The suspension was degassed under vacuum and purged with hydrogen several times. The mixture was stirred under hydrogen (15 psi) at 40° C. for 2 hours. The reaction mixture was filtrated and concentrated under vacuum. The residue was purified by column chromatography (SiO₂, DCM/MeOH=1:0 to 10:1) to provide tert-butyl 4-[7-[5-methyl-1-(2-trimethylsilylethoxymethyl)indazol-4-yl]-2-(3-morpholinopropoxy)-6,8-dihydro-5H-pyrido[3,4-d]pyrimidin-4-yl]piperazine-1-carboxylate (340 mg, 470 μmol, 96.2% yield) as a brown oil. ESI MS m/z 723.5 [M+H]⁺.

Step C: 4-[3-[[7-(5-methyl-1H-indazol-4-yl)-4-piperazin-1-yl-6,8-dihydro-5H-pyrido[3,4-d]pyrimidin-2-yl]oxy]propyl]morpholine trifluoroacetate To a solution of tert-butyl 4-[7-[5-methyl-1-(2-trimethylsilylethoxymethyl)indazol-4-yl]-2-(3-morpholinopropoxy)-6,8-dihydro-5H-pyrido[3,4-d]pyrimidin-4-yl]piperazine-1-carboxylate (150 mg, 207 μmol, 1.00 eq) in DCM (500 μL) was added TFA (354 mg, 3.11 mmol, 230 μL, 15.0 eq). The mixture was stirred at 25° C. for 1 hour. The reaction mixture was concentrated in vacuum to provide 4-[3-[[7-(5-methyl-1H-indazol-4-yl)-4-piperazin-1-yl-6,8-dihydro-5H-pyrido[3,4-d]pyrimidin-2-yl]oxy]propyl]morpholine trifluoroacetate (125 mg, 206 μmol, 99.3% yield) as a brown oil and used directly in the next step without purification. ESI MS m/z 493.4 [M+H]⁺.

Step D 1-[4-[7-(5-methyl-1H-indazol-4-yl)-2-(3-morpholinopropoxy)-6,8-dihydro-5H-pyrido[3,4-d]pyrimidin-4-yl]piperazin-1-yl]prop-2-en-1-one: To a mixture of 4-[3-[[7-(5-methyl-1H-indazol-4-yl)-4-piperazin-1-yl-6,8-dihydro-5H-pyrido[3,4-d]pyrimidin-2-yl]oxy]propyl] morpholine trifluoroacetate (120 mg, 197 μmol, 1.00 eq, TFA) and DIEA (255 mg, 1.98 mmol, 345 μL, 10.0 eq) in dichloromethane (2.00 mL) was added a solution of prop-2-enoyl prop-2-enoate (19.9 mg, 158 μmol, 0.80 eq) dichloromethane (1.00 mL) at −40° C. under nitrogen atmosphere. The mixture was stirred for 1 hour. The reaction mixture was quenched by addition of MeOH (50.0 μL) at −40° C., diluted with water (10.0 mL), extracted with dichloromethane (10.0 mL), dried over Na₂SO₄, filtered and concentrated under reduced pressure. The residue was purified by preparative HPLC (column: Phenomenex Gemini 150*25 mm*, 10μ; mobile phase: [water (0.05% ammonia hydroxide v/v)-ACN]; B %: 30%-60%, 10 min) to provide 1-[4-[7-(5-methyl-1H-indazol-4-yl)-2-(3-morpholinopropoxy)-6,8-dihydro-5H-pyrido[3,4-d]pyrimidin-4-yl]piperazin-1-yl]prop-2-en-1-one (19.0 mg, 34.4 μmol, 17.4% yield, 99.0% purity) as a white solid. ESI MS m/z 547.5 [M+H]⁺.

Example 45

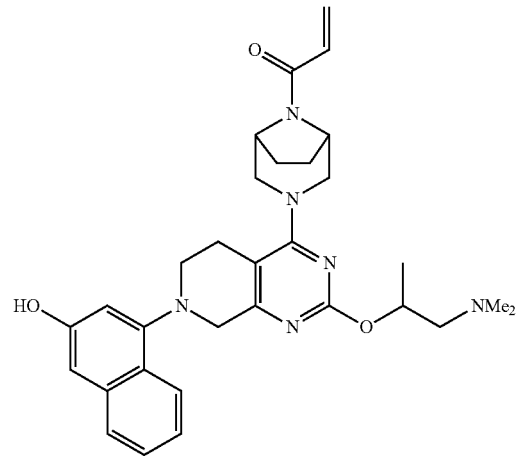 [SMILES: C=CC(=O)N1C2CCC1CN(c1nc(OC(C)CN(C)C)nc3c1CCN(c1cc(O)cc4ccccc14)C3)C2]

1-((1R,5S)-3-(2-((1-(dimethylamino)propan-2-yl)oxy)-7-(3-hydroxynaphthalen-1-yl)-5,6,7,8-tetrahydropyrido[3,4-d]pyrimidin-4-yl)-3,8-diazabicyclo[3.2.1]octan-8-yl)prop-2-en-1-one Step A: tert-butyl 3-(7-benzyl-2-chloro-6,8-dihydro-5H-pyrido[3,4-d]pyrimidin-4-yl)-3,8-diazabicyclo[3.2.1]octane-8-carboxylate To a mixture of 7-benzyl-2,4-dichloro-6,8-dihydro-5H-pyrido[3,4-d]pyrimidine (920 mg, 3.13 mmol, 1.00 eq) and tert-butyl 3,8-diazabicyclo[3.2.1]octane-8-carboxylate (677 mg, 3.19 mmol, 1.02 eq) in DMSO (18.0 mL) was added DIEA (1.21 g, 9.39 mmol, 1.64 mL, 3.00 eq). The reaction mixture was stirred at 60° C. for 1 hour. The mixture was diluted with extracted with EtOAc (3×20 mL), washed with water (10 mL), 1N HCl (5 mL), NaHCO₃ (15 mL), and brine (15 mL). The combined organic layers were dried over Na₂SO₄, filtered and concentrated under vacuum to give tert-butyl 3-(7-benzyl-2-chloro-6,8-dihydro-5H-pyrido[3,4-d]pyrimidin-4-yl)-3,8-diazabicyclo[3.2.1]octane-8-carboxylate (1.30 g, 2.41 mmol, 76.9% yield, 87.0% purity) as a brown oil which was used directly in the next step without further purification. ESI MS m/z 470.2 [M+H]+.

Step B: tert-butyl 3-[7-benzyl-2-[2-(dimethylamino)-1-methyl-ethoxy]-6,8-dihydro-5H-pyrido[3,4-d]pyrimidin-4-yl]-3,8-diazabicyclo[3.2.1]octane-8-carboxylate: To a solution of 1-(dimethylamino)propan-2-ol (857 mg, 8.31 mmol, 942 µL, 3.00 eq) in THF (40.0 mL) was added NaH (222 mg, 5.54 mmol, 60.0% purity, 2.00 eq) at 15° C. under $N_2$. After stirring at 15° C. for 0.5 hour, tert-butyl 3-(7-benzyl-2-chloro-6,8-dihydro-5H-pyrido[3,4-d]pyrimidin-4-yl)-3,8-diazabicyclo[3.2.1]octane-8-carboxylate (1.30 g, 2.77 mmol, 1.00 eq) was added. The mixture was stirred at 100° C. for 12 hours in a sealed tube. The reaction was slowly quenched with water (3 mL) and then concentrated under vacuum. The residue was purified by column chromatography (DCM/MeOH 60:1 to 10:1) to give tert-butyl 3-[7-benzyl-2-[2-(dimethylamino)-1-methyl-ethoxy]-6,8-dihydro-5H-pyrido[3,4-d]pyrimidin-4-yl]-3,8-diazabicyclo[3.2.1]octane-8-carboxylate (700 mg, 1.07 mmol, 38.8% yield, 82.4% purity) as a yellow oil.

Step C: tert-butyl 3-[2-[2-(dimethylamino)-1-methyl-ethoxy]-5,6,7,8-tetrahydropyrido[3,4-d]pyrimidin-4-yl]-3,8-diazabicyclo[3.2.1]octane-8-carboxylate: To a solution of tert-butyl 3-[7-benzyl-2-[2-(dimethylamino)-1-methyl-ethoxy]-6,8-dihydro-5H-pyrido[3,4-d]pyrimidin-4-yl]-3,8-diazabicyclo[3.2.1]octane-8-carboxylate (700 mg, 1.30 mmol, 1.00 eq) in MeOH (30.0 mL) was added Pd/C (200 mg) under $N_2$. The suspension was degassed under vacuum and purged with hydrogen 4 times. The mixture was stirred under hydrogen (50 psi) at 40° C. for 12 hours. The mixture was concentrated under vacuum. The residue was purified by column chromatography (DCM/MeOH 50:1 to 5:1) to give tert-butyl 3-[2-[2-(dimethylamino)-1-methyl-ethoxy]-5,6,7,8-tetrahydropyrido[3,4-d]pyrimidin-4-yl]-3,8-diazabicyclo[3.2.1]octane-8-carboxylate (500 mg, 952 µmol, 73.2% yield, 85.0% purity) as a yellow oil.

Step D: tert-butyl 3-[7-(3-benzyloxy-1-naphthyl)-2-[2-(dimethylamino)-1-methyl-ethoxy]-6,8-dihydro-5H-pyrido[3,4-d]pyrimidin-4-yl]-3,8-diazabicyclo[3.2.1]octane-8-carboxylate: $Pd_2(dba)_3$ (84.1 mg, 91.8 µmol, 0.10 eq) was added to a solution of tert-butyl 3-[2-[2-(dimethylamino)-1-methyl-ethoxy]-5,6,7,8-tetrahydropyrido[3,4-d]pyrimidin-4-yl]-3,8-diazabicyclo[3.2.1]octane-8-carboxylate (410 mg, 918 µmol, 1.00 eq), 3-benzyloxy-1-bromo-naphthalene (293 mg, 936 µmol, 1.02 eq), 2-dicyclohexylphosphino-2',6'-diisopropoxybiphenyl (RuPhos) (85.7 mg, 184 µmol, 0.20 eq) and $Cs_2CO_3$ (897 mg, 2.75 mmol, 3.00 eq) in dioxane (9.00 mL). The reaction mixture was stirred at 100° C. for 7 hours under $N_2$ and then concentrated under vacuum. The residue was diluted with water (5 mL) and extracted with DCM (2×20 mL). The organic layers were dried over $Na_2SO_4$, filtered and concentrated under vacuum. The residue was purified by column chromatography (DCM/MeOH 100:1 to 20:1) to give tert-butyl 3-[7-(3-benzyloxy-1-naphthyl)-2-[2-(dimethylamino)-1-methyl-ethoxy]-6,8-dihydro-5H-pyrido[3,4-d]pyrimidin-4-yl]-3,8-diazabicyclo[3.2.1]octane-8-carboxylate (317 mg, 441 µmol, 48.1% yield, 94.5% purity) as a yellow oil. ESI MS m/z 679.2 [M+H]+.

Step E: tert-butyl 3-[2-[2-(dimethylamino)-1-methyl-ethoxy]-7-(3-hydroxy-1-naphthyl)-6,8-dihydro-5H-pyrido[3,4-d]pyrimidin-4-yl]-3,8-diazabicyclo[3.2.1]octane-8-carboxylate: To a solution of tert-butyl 3-[7-(3-benzyloxy-1-naphthyl)-2-[2-(dimethylamino)-1-methyl-ethoxy]-6,8-dihydro-5H-pyrido[3,4-d]pyrimidin-4-yl]-3,8-diazabicyclo[3.2.1]octane-8-carboxylate (340 mg, 501 µmol, 1.00 eq) in MeOH (6.80 mL) was added Pd/C (120 mg). The suspension was degassed under vacuum and purged with hydrogen 4 times. The mixture was stirred under hydrogen (15 psi) at 40° C. for 1.5 hours. The mixture was concentrated under vacuum to give tert-butyl 3-[2-[2-(dimethylamino)-1-methyl-ethoxy]-7-(3-hydroxy-1-naphthyl)-6,8-dihydro-5H-pyrido[3,4-d]pyrimidin-4-yl]-3,8-diazabicyclo[3.2.1]octane-8-carboxylate (210 mg, 316 µmol, 63.1% yield, 88.6% purity) as a yellow solid which was used directly in the next step without further purification. ESI MS m/z 589.3 [M+H]+.

Step F: 4-[4-(3,8-diazabicyclo[3.2.1]octan-3-yl)-2-[2-(dimethylamino)-1-methyl-ethoxy]-6,8-dihydro-5H-pyrido[3,4-d]pyrimidin-7-yl]naphthalen-2-ol trifluoroacetate: To a solution of tert-butyl 3-[2-[2-(dimethylamino)-1-methyl-ethoxy]-7-(3-hydroxy-1-naphthyl)-6,8-dihydro-5H-pyrido[3,4-d]pyrimidin-4-yl]-3,8-diazabicyclo[3.2.1]octane-8-carboxylate (180 mg, 306 µmol, 1.00 eq) in DCM (230 µL) was added TFA (349 mg, 3.06 mmol, 226 µL, 10.0 eq). The reaction mixture was stirred at 18° C. for 0.5 hour. The mixture was concentrated under vacuum to give 4-[4-(3,8-diazabicyclo[3.2.1]octan-3-yl)-2-[2-(dimethylamino)-1-methyl-ethoxy]-6,8-dihydro-5H-pyrido[3,4-d]pyrimidin-7-yl]naphthalen-2-ol trifluoroacetate (528 mg, crude) as a red oil which was used directly in the next step without further purification. ESI MS m/z 489.2 [M+H]+.

Step G: 1-[3-[2-[2-(dimethylamino)-1-methyl-ethoxy]-7-(3-hydroxy-1-naphthyl)-6,8-dihydro-5H-pyrido[3,4-d]pyrimidin-4-yl]-3,8-diazabicyclo[3.2.1]octan-8-yl]prop-2-en-1-one: To a solution of 4-[4-(3,8-diazabicyclo[3.2.1]octan-3-yl)-2-[2-(dimethylamino)-1-methyl-ethoxy]-6,8-dihydro-5H-pyrido[3,4-d]pyrimidin-7-yl]naphthalen-2-ol trifluoroacetate (149 mg, 306 µmol, 1.00 eq) and DIEA (1.36 g, 10.5 mmol, 1.84 mL, 34.5 eq) in DCM (1.50 mL) was added prop-2-enoyl prop-2-enoate (30.9 mg, 245 µmol, 0.80 eq) dropwise at −50° C. The mixture was stirred at −40 and then −20° C. for 30 minutes. The reaction was quenched with MeOH (19.6 mg) and concentrated under vacuum. The residue was purified by preparative TLC (DCM/MeOH 7:1) to give 1-[3-[2-[2-(dimethylamino)-1-methyl-ethoxy]-7-(3-hydroxy-1-naphthyl)-6,8-dihydro-5H-pyrido[3,4-d]pyrimidin-4-yl]-3,8-diazabicyclo[3.2.1]octan-8-yl]prop-2-en-1-one (18.9 mg, 32.8 µmol, 10.7% yield, 94.3% purity) as a yellow solid. ESI MS m/z 543.3 [M+H]+.

Example 46

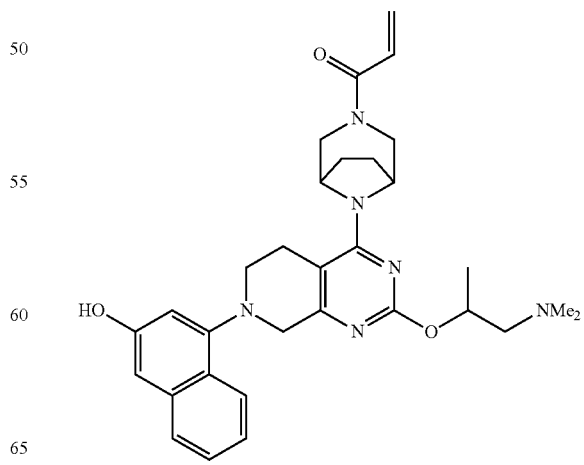

1-((1R,5S)-8-(2-((1-(dimethylamino)propan-2-yl)oxy)-7-(3-hydroxynaphthalen-1-yl)-5,6,7,8-tetrahydropyrido[3,4-d]pyrimidin-4-yl)-3,8-diazabicyclo[3.2.1]octan-3-yl)prop-2-en-1-one Synthesized according to the method of Example 4, using tert-butyl (1R,5S)-3,8-diazabicyclo[3.2.1]octane-3-carboxylate in place tert-butyl 3,8-diazabicyclo[3.2.1]octane-8-carboxylate in Step A. ESI MS m/z 543.4 [M+H]$^+$.

Example 47

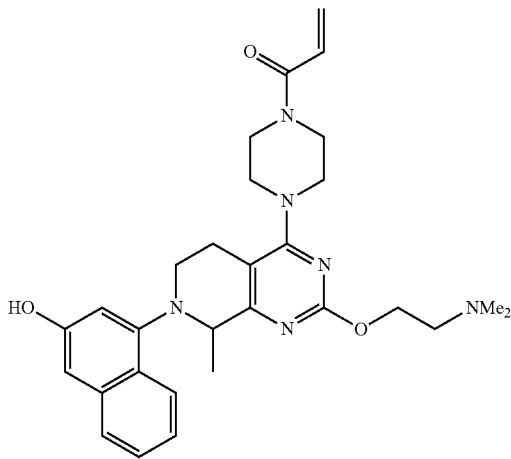 [SMILES: C=CC(=O)N1CCN(c2nc(OCCN(C)C)nc3c2CCN(c2cc(O)cc4ccccc24)C3C)CC1]

1-(4-(2-(2-(dimethylamino)ethoxy)-7-(3-hydroxynaphthalen-1-yl)-8-methyl-5,6,7,8-tetrahydropyrido[3,4-d]pyrimidin-4-yl)piperazin-1-yl)prop-2-en-1-one Step A: ethyl 2-(benzylamino)propanoate To a solution of ethyl 2-bromopropanoate (30.0 g, 165 mmol, 21.6 mL, 1.00 eq), BnNH$_2$ (23.1 g, 215 mmol, 23.6 mL, 1.30 eq) in MeCN (600 mL) was added K$_2$CO$_3$ (45.8 g, 331 mmol, 2.00 eq). The mixture was stirred at 80° C. for 2 hour. The reaction mixture was filtered and the filter cake was washed with DCM (300 mL). The filtrated was concentrated under vacuum. The residue was purified by silica gel chromatography (diethyl ether:ethyl acetate=10:1 to 4:1) to give ethyl 2-(benzylamino)propanoate (34.0 g, 163 mmol, 98.4% yield, 99.4% purity) a colorless oil.

Step B: ethyl 4-[benzyl-(2-ethoxy-1-methyl-2-oxo-ethyl)amino]butanoate

To a solution of ethyl 2-(benzylamino)propanoate (31.0 g, 150 mmol, 1.00 eq) and ethyl 4-bromobutanoate (87.5 g, 449 mmol, 64.4 mL, 3.00 eq) in MeCN (600 mL) and water (60.0 mL) was added Cs$_2$CO$_3$ (97.5 g, 299.12 mmol, 2.00 eq) and KI (4.97 g, 29.9 mmol, 0.20 eq). The reaction mixture was stirred at 80-90° C. for 40 hours. The reaction mixture was filtered and the filter cake was washed with DCM (2×100 mL). The filtrate was concentrated under vacuum. The residue was dissolved in DCM (300 mL) and washed with brine (80 mL), dried over Na$_2$SO$_4$ and concentrated under vacuum. The residue was purified by flash silica gel chromatography (diethyl ether:ethyl acetate=1:0 to 20:1) to give ethyl 4-[benzyl-(2-ethoxy-1-methyl-2-oxo-ethyl)amino]butanoate (28.0 g, 87.1 mmol, 58.3% yield) as a yellow oil.

Step C: ethyl 1-benzyl-2-methyl-3-oxo-piperidine-4-carboxylate

To a solution of ethyl 4-[benzyl-(2-ethoxy-1-methyl-2-oxo-ethyl)amino]butanoate (28.0 g, 87.1 mmol, 1.00 eq) in THF (600 mL) was added tBuOK (19.6 g, 174 mmol, 2.00 eq). The reaction mixture was stirred at 18° C. for 1 hour. The reaction mixture was quenched with water (100 mL) and extracted with MTBE (3×300 mL) and DCM (2×200 mL). The combined organic layers were washed with brine, dried over Na$_2$SO$_4$ and concentrated under vacuum. The crude product was purified by silica gel chromatography (diethyl ether:ethyl acetate=100:1 to 20:1) to give ethyl 1-benzyl-2-methyl-3-oxo-piperidine-4-carboxylate (20.0 g, 58.8 mmol, 67.5% yield, 81.0% purity) as a yellow oil. ESI MS m/z 276.0 [M+H]$^+$.

Step D: 7-benzyl-8-methyl-6,8-dihydro-5H-pyrido[3,4-d]pyrimidine-2,4-diol

To EtOH (400 mL) was added Na (3.76 g, 163 mmol, 3.88 mL, 2.50 eq). The reaction mixture was stirred at 20° C. for 0.5 hour. To the mixture was added ethyl 1-benzyl-2-methyl-3-oxo-piperidine-4-carboxylate (18.0 g, 65.4 mmol, 1.00 eq) and UREA (9.82 g, 163 mmol, 8.77 mL, 2.50 eq) and the reaction mixture was stirred at 80° C. for 80 hours. The solvent was removed under vacuum. The residue was dissolved in water (100 mL) and washed with MTBE (3×50 mL). The aqueous phase was adjusted to pH 6-7 with HCl (15 mL, 12 M). The mixture was filtered and the filter cake was washed with water (30 mL) and dried in vacuum to give 7-benzyl-8-methyl-6,8-dihydro-5H-pyrido[3,4-d]pyrimidine-2,4-diol (12.0 g, 44.2 mmol, 67.7% yield, 100% purity) was obtained as a brown solid. ESI MS m/z 272.0 [M+H]$^+$.

Step E: benzyl-2,4-dichloro-8-methyl-6,8-dihydro-5H-pyrido[3,4-d]pyrimidine

A mixture of 7-benzyl-8-methyl-6,8-dihydro-5H-pyrido[3,4-d]pyrimidine-2,4-diol (5.00 g, 18.4 mmol, 1.00 eq) in POCl$_3$ (305 g, 1.99 mol, 185 mL, 108 eq) was heated to 110° C. for 12 hours. The solvent was removed under vacuum. The residue was dissolved in DCM (500 mL) and poured into saturated NaHCO$_3$ (200 mL) while keeping the pH greater than 7. The organic layer was washed with brine (50 mL), dried over Na$_2$SO$_4$. The solution was filtered through a pad of silica gel and the filter cake was washed with DCM (3×400 mL). The combined organic layers were concentrated under vacuum to give 7-benzyl-2,4-dichloro-8-methyl-6,8-dihydro-5H-pyrido[3,4-d]pyrimidine (4.50 g, 14.6 mmol, 79.2% yield) as a brown oil.

Step F: 4-(7-benzyl-2-chloro-8-methyl-6,8-dihydro-5H-pyrido[3,4-d]pyrimidin-4-yl)piperazine-1-carboxylate To a solution of 7-benzyl-2,4-dichloro-8-methyl-6,8-dihydro-5H-pyrido[3,4-d]pyrimidine (3.00 g, 9.73 mmol, 1.00 eq) and DIEA (2.52 g, 19.5 mmol, 3.40 mL, 2.00 eq) in dioxane (60.0 mL) was added tert-butyl piperazine-1-carboxylate (1.90 g, 10.2 mmol, 1.05 eq). The reaction mixture was stirred at 60° C. for 12 hours. The solvent was removed under vacuum. The residue was purified by silica gel chromatography (diethyl ether:ethyl acetate=2:1) to give tert-butyl 4-(7-benzyl-2-chloro-8-methyl-6,8-dihydro-5H-pyrido[3,4-d]pyrimidin-4-yl)piperazine-1-carboxylate (3.30 g, 7.15 mmol, 73.5% yield, 99.3% purity) as a yellow solid. ESI MS m/z 458.1 [M+H]⁺.

Step G: tert-butyl-4-[7-benzyl-2-[2-(dimethylamino)ethoxy]-8-methyl-6,8-dihydro-5H-pyrido[3,4-d]pyrimidin-4-yl]piperazine-1-carboxylate: To a solution of 2-(dimethylamino)ethanol (583 mg, 6.54 mmol, 655 µL, 3.00 eq) in toluene (20.0 mL) was added Pd(OAc)₂ (48.9 mg, 218 µmol, 0.10 eq), tert-butyl-4-(7-benzyl-2-chloro-8-methyl-6,8-dihydro-5H-pyrido[3,4-d]pyrimidin-4-yl)piperazine-1-carboxylate (1.00 g, 2.18 mmol, 1.00 eq), Cs₂CO₃ (2.13 g, 6.54 mmol, 3.00 eq) and BINAP (272 mg, 436 µmol, 0.20 eq). The reaction mixture was stirred at 110° C. for 3 hours under N₂. The reaction mixture was concentrated under vacuum. The residue was dissolved in water (10 mL) and extracted with DCM (3×40 mL). The combined organic layers were washed with brine, dried over Na₂SO₄ and concentrated under vacuum. The residue was purified by silica gel chromatography (diethyl ether:ethyl acetate=5:1 to 2:1 then DCM:MeOH=50:1 to 5:1) to give tert-butyl-4-[7-benzyl-2-[2-(dimethylamino)ethoxy]-8-methyl-6,8-dihydro-5H-pyrido[3,4-d]pyrimidin-4-yl]piperazine-1-carboxylate (900 mg, 1.76 mmol, 80.8% yield) as a brown solid. ESI MS m/z 511.2 [M+H]⁺.

Step H: tert-butyl 4-[2-[2-(dimethylamino)ethoxy]-8-methyl-5,6,7,8-tetrahydropyrido[3,4-d]pyrimidin-4-yl]piperazine-1-carboxylate To a solution of tert-butyl 4-[7-benzyl-2-[2-(dimethylamino)ethoxy]-8-methyl-6,8-dihydro-5H-pyrido[3,4-d]pyrimidin-4-yl]piperazine-1-carboxylate (800 mg, 1.57 mmol, 1.00 eq) in MeOH (20.0 mL) was added Pd/C (100 mg) under N₂. The suspension was degassed under vacuum and purged with hydrogen several times. The mixture was stirred under hydrogen (50 psi) at 40° C. for 12 hours. The reaction mixture was filtered and the filter cake was washed with MeOH (3×200 mL). The filtrate was concentrated under vacuum to give tert-butyl 4-[2-[2-(dimethylamino)ethoxy]-8-methyl-5,6,7,8-tetrahydropyrido[3,4-d]pyrimidin-4-yl]piperazine-1-carboxylate (450 mg, 1.07 mmol, 68.2% yield) as a brown oil which was used for next step without further purification. ESI MS m/z 421.3 [M+H]⁺.

Step I: tert-butyl 4-[7-(3-benzyloxy-1-naphthyl)-2-[2-(dimethylamino)ethoxy]-8-methyl-6,8-dihydro-5H-pyrido[3,4-d]pyrimidin-4-yl]piperazine-1-carboxylate: To a mixture of tert-butyl 4-[2-[2-(dimethylamino)ethoxy]-8-methyl-5,6,7,8-tetrahydropyrido[3,4-d]pyrimidin-4-yl]piperazine-1-carboxylate (380 mg, 904 µmol, 1.00 eq) and 3-benzyloxy-1-bromo-naphthalene (311 mg, 994 µmol, 1.10 eq) in dioxane (8.00 mL), Cs₂CO₃ (883 mg, 2.71 mmol, 3.00 eq) and 2-dicyclohexylphosphino-2',6'-diisopropoxybiphenyl (RuPhos) (84.3 mg, 181 µmol, 0.20 eq) and Pd₂(dba)₃ (82.7 mg, 90.4 µmol, 0.10 eq) were added. The reaction mixture was stirred at 90° C. for 12 h under N₂. The reaction mixture was concentrated under vacuum. The residue was partitioned between DCM (50 mL) and water (20 mL). The reaction mixture was extracted with DCM (50 mL). The combined organic layers were washed with brine (10 mL), dried over Na₂SO₄ and concentrated under vacuum. The residue was purified by silica gel chromatography (diethyl ether:ethyl acetate=5:1 then DCM:MeOH=100:1 to 5:1), followed by purification of the isolated product by preparative TLC (DCM:MeOH=10:1) to give tert-butyl 4-[7-(3-benzyloxy-1-naphthyl)-2-[2-(dimethylamino)ethoxy]-8-methyl-6,8-dihydro-5H-pyrido[3,4-d]pyrimidin-4-yl]piperazine-1-carboxylate (200 mg, 306 µmol, 33.9% yield) as brown solid. ESI MS m/z 653.4 [M+H]⁺.

Step J: 4-[2-[2-(dimethylamino)ethoxy]-8-methyl-4-piperazin-1-yl-6,8-dihydro-5H-pyrido[3,4-d]pyrimidin-7-yl]naphthalen-2-ol bis-trifluoroacetate To a solution of tert-butyl 4-[2-[2-(dimethylamino)ethoxy]-7-(3-hydroxy-1-naphthyl)-8-methyl-6,8-dihydro-5H-pyrido [3,4-d]pyrimidin-4-yl]piperazine-1-carboxylate (100 mg, 177 µmol, 1.00 eq) in DCM (130.00 µL) was added TFA (202 mg, 1.78 mmol, 132 µL, 10.00 eq). The reaction mixture was stirred at 20° C. for 1 hour. The solvent was removed under vacuum to provide 4-[2-[2-(dimethylamino)ethoxy]-8-methyl-4-piperazin-1-yl-6,8-dihydro-5H-pyrido[3,4-d]pyrimidin-7-yl]naphthalen-2-ol bis-trifluoroacetate (175.00 mg) as a brown oil which was used in the next step without further purification.

Step K: 1-[4-[2-[2-(dimethylamino)ethoxy]-7-(3-hydroxy-1-naphthyl)-8-methyl-6,8-dihydro-5H-pyrido[3,4-d]pyrimidin-4-yl]piperazin-1-yl]prop-2-en-1-one: To a solution of 4-[2-[2-(dimethylamino)ethoxy]-8-methyl-4-piperazin-1-yl-6,8-dihydro-5H-pyrido[3,4-d]pyrimidin-7-yl]naphthalen-2-ol bis-trifluoroacetate (97.4 mg, 141 µmol, 1.00 eq) in DCM (500.00 µL) was added DIEA (222 mg, 1.72 mmol, 300 µL, 12.2 eq) and prop-2-enoyl prop-2-enoate (14.2 mg, 113 µmol, 0.80 eq) at −40° C. The reaction mixture was stirred at −40° C. for 0.5 h. The reaction mixture was quenched with a drop of MeOH and concentrated under vacuum. The residue was purified by preparative TLC (DCM:MeOH=10:1) and then by preparative HPLC (column: Phenomenex Synergi C18 150*25*, 10µ; mobile phase: [water (0.1% TFA)-ACN]; B %: 15%-45%, 13 min) to give 1-[4-[2-[2-(dimethylamino)ethoxy]-7-(3-hydroxy-1-naphthyl)-8-methyl-6,8-dihydro-5H-pyrido[3,4-d]pyrimidin-4-yl]piperazin-1-yl]prop-2-en-1-one (10.7 mg, 20.7 µmol, three steps 6.8% yield) as a brown oil. ESI MS m/z 517.2 [M+H]⁺.

Example 48

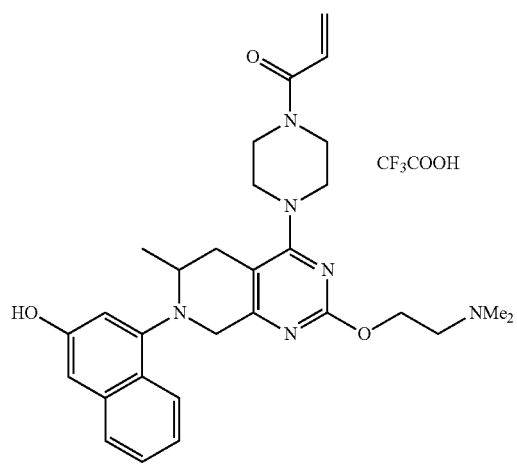 [SMILES: C=CC(=O)N1CCN(c2nc(OCCN(C)C)nc3c2CC(C)N(c2cc(O)cc4ccccc24)C3)CC1 ; "CF3COOH"]

1-(4-(2-(2-(dimethylamino)ethoxy)-7-(3-hydroxynaphthalen-1-yl)-6-methyl-5,6,7,8-tetrahydropyrido[3,4-d]pyrimidin-4-yl)piperazin-1-yl)prop-2-en-1-one trifluoroacetate

Step A: ethyl 4-[benzyl-(2-ethoxy-2-oxo-ethyl)amino]pentanoate

A solution of ethyl 4-oxopentanoate (47.0 g, 326 mmol, 46.5 mL, 1.50 eq), ethyl 2-(benzylamino)acetate (42.0 g, 217.3 mmol, 1.00 eq) and AcOH (13.0 g, 217 mmol, 12.4 mL, 1.00 eq) in DCM (800 mL) was stirred at 12-18° C. for 30 min, then cooled at 0-5° C., NaBH(OAc)$_3$ (138 g, 652 mmol, 3.00 eq) was added portion-wise. The mixture was warmed to 10-18° C. and stirred for 16 hours. The reaction mixture was quenched with water (1000 mL) and extracted with DCM (2×500 mL). The combined organic phases were dried and concentrated to dryness. The residue was purified by silica gel column eluting with diethyl ether/ethyl acetate (60:1 to 40:1) to provide ethyl 4-[benzyl-(2-ethoxy-2-oxo-ethyl)amino]pentanoate (42.0 g, 91.5 mmol, 42.1% yield, 70% purity) as colorless oil. ESI MS m/z 322.2 [M+H]$^+$.

Step B: ethyl 1-benzyl-2-methyl-5-oxo-piperidine-4-carboxylate

A solution of ethyl 4-[benzyl-(2-ethoxy-2-oxo-ethyl)amino]pentanoate (37.00 g, 115.12 mmol, 1.00 eq) and t-BuOK (16.8 g, 150 mmol, 1.30 eq) in toluene (30.0 mL) was stirred at 25° C. for 5 hours. The reaction was quenched with water (50 mL) and extracted with ethyl acetate (2×30 mL). The combined organic extracts were dried and concentrated to dryness to provide ethyl 1-benzyl-2-methyl-5-oxo-piperidine-4-carboxylate (14.6 g, 53.0 mmol, 46% yield) as yellow oil which was used directly in the next step.

Step C: 7-benzyl-6-methyl-6,8-dihydro-5H-pyrido[3,4-d]pyrimidine-2,4-diol

Na (3.05 g, 133 mmol, 3.14 mL, 2.50 eq) was dissolved in EtOH (280 mL), and then ethyl 1-benzyl-2-methyl-5-oxo-piperidine-4-carboxylate (14.6 g, 53.0 mmol, 1.00 eq) and urea (7.96 g, 133 mmol, 7.11 mL, 2.50 eq) were added. The reaction mixture was heated to reflux (78° C.) for 16 hrs under N$_2$. The reaction mixture was concentrated to dryness. The residue was dissolved in water (100 mL), washed with MTBE (100 mL). The pH of the water phase was adjusted to pH 6-7 with 6N HCl (2 mL). The resulting solid was collected by filtration and dried under vacuum at 60° C. to provide 7-benzyl-6-methyl-6,8-dihydro-5H-pyrido[3,4-d]pyrimidine-2,4-diol (5.00 g, 17.1 mmol, 32.3% yield, 93% purity) as light yellow solid.

Step D: 7-benzyl-2,4-dichloro-6-methyl-6,8-dihydro-5H-pyrido[3,4-d]pyrimidine POCl$_3$ (49.5 g, 323 mmol, 30.0 mL, 58.4 eq) and 7-benzyl-6-methyl-6,8-dihydro-5H-pyrido[3,4-d]pyrimidine-2,4-diol (1.50 g, 5.53 mmol, 1.00 eq) were heated to 100° C. under reflux for 12 hours. The reaction was concentrated to dryness to remove POCl$_3$. The residue was dissolved in DCM (40 mL) and washed with saturated NaHCO$_3$ aqueous/saturated aqueous Na$_2$CO$_3$ (1/1, 60 mL). The mixture was filtered and the organic layers were dried over Na$_2$SO$_4$, filtered and concentrated under vacuum to give 7-benzyl-2,4-dichloro-6-methyl-6,8-dihydro-5H-pyrido[3,4-d]pyrimidine (2.08 g, crude) as a brown solid which was used directly in the next step without further purification. ESI MS m/z 307.9, 309.9 [M+H]$^+$.

Step E: 4-(7-benzyl-2-chloro-6-methyl-6,8-dihydro-5H-pyrido[3,4-d]pyrimidin-4-yl)piperazine-1-carboxylate To a mixture of 7-benzyl-2,4-dichloro-6-methyl-6,8-dihydro-5H-pyrido[3,4-d]pyrimidine (2.50 g, 8.11 mmol, 1.00 eq) and tert-butyl piperazine-1-carboxylate (1.54 g, 8.27 mmol, 1.02 eq) in dioxane (50.0 mL) was added DIEA (3.14 g, 24.3 mmol, 4.25 mL, 3.00 eq). The mixture was stirred at 60° C. for 20 hours. The mixture was concentrated under vacuum. The residue was diluted with water (20 mL) and extracted with DCM (2×80 mL). The organic layers were dried over Na$_2$SO$_4$ and concentrated under vacuum. The residue was purified by automated flash chromatography system (diethyl ether/ethyl acetate 50:1 to 2:1) to give tert-butyl 4-(7-benzyl-2-chloro-6-methyl-6,8-dihydro-5H-pyrido[3,4-d]pyrimidin-4-yl)piperazine-1-carboxylate (2.59 g, 5.29 mmol, 65.2% yield, 93.5% purity) as a yellow solid.

Step F: tert-butyl 4-[7-benzyl-2-[2-(dimethylamino)ethoxy]-6-methyl-6,8-dihydro-5H-pyrido[3,4-d]pyrimidin-4-yl]piperazine-1-carboxylate: To a solution of 2-(dimethylamino)ethanol (701 mg, 7.86 mmol, 788 µL, 3.00 eq) in THF (45.0 mL) was added NaH (210 mg, 5.24 mmol, 60.0% purity, 2.00 eq) at 15° C. under N$_2$. After stirring at 15° C. for 0.5 hour, tert-butyl 4-(7-benzyl-2-chloro-6-methyl-6,8-dihydro-5H-pyrido[3,4-d]pyrimidin-4-yl)piperazine-1-carboxylate (1.20 g, 2.62 mmol, 1.00 eq) was added. The mixture was stirred at 110° C. for 18 hours in a sealed tube. The mixture was concentrated under vacuum. The residue was purified by column chromatography over Al$_2$O$_3$(DCM/MeOH 100:1 to 10:1) to give tert-butyl 4-[7-benzyl-2-[2-(dimethylamino)ethoxy]-6-methyl-6,8-dihydro-5H-pyrido[3,4-d]pyrimidin-4-yl]piperazine-1-carboxylate (1.38 g, 2.36 mmol, 90.3% yield, 87.5% purity) as a yellow oil. ESI MS m/z 511.3 [M+H]$^+$.

Step G: tert-butyl 4-[2-[2-(dimethylamino)ethoxy]-6-methyl-5,6,7,8-tetrahydropyrido[3,4-d]pyrimidin-4-yl]piperazine-1-carboxylate To a solution of tert-butyl 4-[7-benzyl-2-[2-(dimethylamino)ethoxy]-6-methyl-6,8-dihydro-5H-pyrido[3,4-d]pyrimidin-4-yl]piperazine-1-carboxylate (1.50 g, 2.94 mmol, 1.00 eq) in MeOH (80.0 mL) was added Pd/C (450 mg) under N$_2$. The suspension was degassed under vacuum and purged with hydrogen 4 times. The mixture was stirred under hydrogen (50 psi) at 40° C. for 12 hours. The reaction mixture was filtered and the filtrate was concentrated. The residue was purified by column chromatography (DCM/MeOH 40/1 to 10/1) to give tert-butyl 4-[2-[2-(dimethylamino)ethoxy]-6-methyl-5,6,7,8-tetrahydropyrido[3,4-d]pyrimidin-4-yl]piperazine-1-carboxylate (1.15 g, 2.46 mmol, 83.7% yield, 90.0% purity) as a yellow oil.

Step H: tert-butyl 4-[7-(3-benzyloxy-1-naphthyl)-2-[2-(dimethylamino)ethoxy]-6-methyl-6,8-dihydro-5H-pyrido[3,4-d]pyrimidin-4-yl]piperazine-1-carboxylate: Pd$_2$(dba)$_3$ (109 mg, 119 µmol, 0.10 eq) was added to a solution of tert-butyl 4-[2-[2-(dimethylamino)ethoxy]-6-methyl-5,6,7,8-tetrahydropyrido[3,4-d]pyrimidin-4-yl]piperazine-1-carboxylate (500 mg, 1.19 mmol, 1.00 eq), 3-benzyloxy-1-bromo-naphthalene (410 mg, 1.31 mmol, 1.10 eq), 2-dicyclohexylphosphino-2',6'-diisopropoxybiphenyl (RuPhos) (111 mg, 238 µmol, 0.20 eq) and Cs$_2$CO$_3$ (1.16 g, 3.57 mmol, 3.00 eq) in dioxane (10.0 mL). The reaction mixture was stirred at 90° C. for 12 hours under N₂. The mixture was concentrated under vacuum. The residue was diluted with water (5 mL) and extracted with DCM (2×20 mL). The combined organic layers were dried over Na₂SO₄, filtered and concentrated under vacuum. The residue was purified by column chromatography over Al₂O₃(DCM/MeOH 100/1 to 10/1) and by preparative TLC (DCM/MeOH 5:1) to give tert-butyl 4-[7-(3-benzyloxy-1-naphthyl)-2-[2-(dimethylamino)ethoxy]-6-methyl-6,8-dihydro-5H-pyrido[3,4-d]pyrimidin-4-yl]piperazine-1-carboxylate (309 mg, 453 µmol, 38.1% yield, 95.8% purity) as a yellow oil.

Step I: tert-butyl 4-[2-[2-(dimethylamino)ethoxy]-7-(3-hydroxy-1-naphthyl)-6-methyl-6,8-dihydro-5H-pyrido[3,4-d]pyrimidin-4-yl]piperazine-1-carboxylate: To a solution of tert-butyl 4-[7-(3-benzyloxy-1-naphthyl)-2-[2-(dimethylamino)ethoxy]-6-methyl-6,8-dihydro-5H-pyrido[3,4-d]pyrimidin-4-yl]piperazine-1-carboxylate (340 mg, 521 µmol, 1.00 eq) in MeOH (6.80 mL) was added Pd/C (120 mg) under N₂. The suspension was degassed under vacuum and purged with hydrogen 4 times. The mixture was stirred under hydrogen (15 psi) at 40° C. for 1.5 hours. The mixture was concentrated under vacuum to give tert-butyl 4-[2-[2-(dimethylamino)ethoxy]-7-(3-hydroxy-1-naphthyl)-6-methyl-6,8-dihydro-5H-pyrido[3,4-d]pyrimidin-4-yl]piperazine-1-carboxylate (210 mg, 312 µmol, 59.8% yield, 83.5% purity) as a pink solid which was used directly in the next step without further purification. ESI MS m/z 563.3 [M+H]⁺.

Step J: 4-[2-[2-(dimethylamino)ethoxy]-6-methyl-4-piperazin-1-yl-6,8-dihydro-5H-pyrido[3,4-d]pyrimidin-7-yl]naphthalen-2-ol trifluoroacetate: To a solution of tert-butyl 4-[2-[2-(dimethylamino)ethoxy]-7-(3-hydroxy-1-naphthyl)-6-methyl-6,8-dihydro-5H-pyrido[3,4-d]pyrimidin-4-yl]piperazine-1-carboxylate (180 mg, 320 µmol, 1.00 eq) in DCM (240 µL) was added TFA (365 mg, 3.20 mmol, 237 µL, 10.0 eq). The mixture was stirred at 18° C. for 0.5 hour. The mixture was concentrated under vacuum to give 4-[2-[2-(dimethylamino)ethoxy]-6-methyl-4-piperazin-1-yl-6,8-dihydro-5H-pyrido[3,4-d]pyrimidin-7-yl]naphthalen-2-ol trifluoroacetate (273 mg) as a yellow oil which was used directly in the next step without further purification.

Step K: 1-[4-[2-[2-(dimethylamino)ethoxy]-7-(3-hydroxy-1-naphthyl)-6-methyl-6,8-dihydro-5H-pyrido[3,4-d]pyrimidin-4-yl]piperazin-1-yl]prop-2-en-1-one: To a solution of 4-[2-[2-(dimethylamino)ethoxy]-6-methyl-4-piperazin-1-yl-6,8-dihydro-5H-pyrido[3,4-d]pyrimidin-7-yl]naphthalen-2-ol trifluoroacetate (148 mg, 320 µmol, 1.00 eq) and DIEA (494 mg, 3.83 mmol, 668 µL, 12.0 eq) in DCM (500 µL) was added prop-2-enoyl prop-2-enoate (32.3 mg, 256 µmol, 0.80 eq) dropwise at −50° C. The mixture was stirred at −40 to −20° C. for 30 minutes. The reaction was quenched with MeOH (20.5 mg) and concentrated under vacuum. The residue was purified by preparative HPLC (column: Phenomenex Synergi C18 150*25*, 10µ; mobile phase: [water (0.1% TFA)-ACN]; B %: 8%-38%, 13 min) to give 1-[4-[2-[2-(dimethylamino)ethoxy]-7-(3-hydroxy-1-naphthyl)-6-methyl-6,8-dihydro-5H-pyrido[3,4-d]pyrimidin-4-yl]piperazin-1-yl]prop-2-en-1-one trifluoroacetate (73.7 mg, 113 µmol, 35.2% yield, 96.3% purity) as a yellow solid. ESI MS m/z 517.3 [M+H]⁺.

Example 49

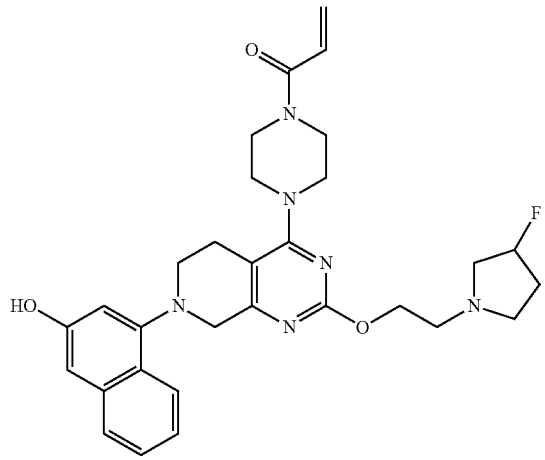 [SMILES: C=CC(=O)N1CCN(c2nc(OCCN3CCC(F)C3)nc3c2CCN(c2cc(O)cc4ccccc24)C3)CC1]

1-(4-(2-(2-(3-fluoropyrrolidin-1-yl)ethoxy)-7-(3-hydroxynaphthalen-1-yl)-5,6,7,8-tetrahydropyrido[3,4-d]pyrimidin-4-yl)piperazin-1-yl)prop-2-en-1-one Step A: tert-butyl 4-(4-benzyloxycarbonylpiperazin-1-yl)-2-[2-(3-fluoropyrrolidin-1-yl)ethoxy]-6,8-dihydro-5H-pyrido[3,4-d]pyrimidine-7-carboxylate: A mixture of 2-(3-fluoropyrrolidin-1-yl)ethanol (401 mg, 3.01 mmol, 1.60 eq), tert-butyl 4-(4-benzyloxycarbonylpiperazin-1-yl)-2-methylsulfonyl-6,8-dihydro-5H-pyrido[3,4-d]pyrimidine-7-carboxylate (1.00 g, 1.88 mmol, 1.00 eq), Cs₂CO₃ (1.84 g, 5.64 mmol, 3.00 eq), Pd(OAc)₂ (42.2 mg, 188 µmol, 0.10 eq) and BINAP (234 mg, 376 µmol, 0.20 eq) in toluene (50.00 mL) was stirred at 110° C. for 3 hours. The mixture was concentrated under vacuum. The residue was purified by column chromatography over silica gel (petroleum ether/ethyl acetate 10:1 to 100:1). The desired fractions were collected and concentrated under vacuum to give tert-butyl 4-(4-benzyloxycarbonylpiperazin-1-yl)-2-[2-(3-fluoropyrrolidin-1-yl)ethoxy]-6,8-dihydro-5H-pyrido[3,4-d]pyrimidine-7-carboxylate (1.20 g, 1.07 mmol, 56.8% yield, 52% purity) as a yellow solid. ESI MS m/z 585.3 [M+H]⁺.

Step B: benzyl 4-[2-[2-(3-fluoropyrrolidin-1-yl)ethoxy]-5,6,7,8-tetrahydropyrido [3,4-d]pyrimidin-4-yl]piperazine-1-carboxylate To a solution of tert-butyl 4-(4-benzyloxycarbonylpiperazin-1-yl)-2-[2-(3-fluoropyrrolidin-1-yl)ethoxy]-6,8-dihydro-5H-pyrido[3,4-d]pyrimidine-7-carboxylate (1.20 g, 2.05 mmol, 1.00 eq) in DCM (10.00 mL) was added TFA (3.51 g, 30.8 mmol, 2.28 mL, 15.00 eq) at 0° C. The mixture was warmed to 25° C. and stirred for 16 hours. The mixture was diluted with water (100 mL) and the solution was extracted with ethyl acetate (2×100 mL). The water layer was basified with saturated aqueous sodium carbonate solution (50 mL) and then extracted with ethyl acetate (2×100 mL). The combined organic layers were washed with brine (1×100 mL), dried over sodium sulfate, and filtered. The filtrate was concentrated under vacuum to provide benzyl 4-[2-[2-(3-fluoropyrrolidin-1-yl)ethoxy]-5,6,7,8-tetrahydropyrido [3,4-d]pyrimidin-4-yl]piperazine-1-carboxylate (800 mg, 1.65 mmol, 80.4% yield) as a yellow gum. ESI MS m/z 485.3 [M+H]⁺.

Step C: benzyl 4-[2-[2-(3-fluoropyrrolidin-1-yl)ethoxy]-7-(3-methoxy-1-naphthyl)-6,8-dihydro-5H-pyrido[3,4-d]pyrimidin-4-yl]piperazine-1-carboxylate: A mixture of benzyl 4-[2-[2-(3-fluoropyrrolidin-1-yl)ethoxy]-5,6,7,8-tetrahydropyrido[3,4-d]pyrimidin-4-yl]piperazine-1-carboxylate (750 mg, 1.55 mmol, 1.00 eq), (3-methoxy-1-naphthyl) trifluoromethanesulfonate (949 mg, 3.10 mmol, 2.00 eq), 2-dicyclohexylphosphino-2',6'-diisopropoxybiphenyl (RuPhos) (144.66 mg, 310.00 µmol, 0.20 eq), Pd$_2$(dba)$_3$ (141.94 mg, 155.00 µmol, 0.10 eq) and Cs$_2$CO$_3$ (1.52 g, 4.65 mmol, 3.00 eq) in toluene (70.00 mL) was stirred at 110° C. for 16 hours. The mixture was concentrated under vacuum and then diluted with ethyl acetate (100 mL) and water (100 mL). The separated organic layer was washed with brine (1×100 mL), dried over sodium sulfate, filtered and concentrated under vacuum. The residue was purified by column chromatography over silica gel (petroleum ether/ethyl acetate 10:1 to ethyl acetate/methanol 10:1). The desired fractions were collected and concentrated under vacuum to give benzyl 4-[2-[2-(3-fluoropyrrolidin-1-yl)ethoxy]-7-(3-methoxy-1-naphthyl)-6,8-dihydro-5H-pyrido[3,4-d]pyrimidin-4-yl]piperazine-1-carboxylate (700 mg, 961 µmol, 62.0% yield, 88% purity) as a brown solid. ESI MS m/z 641.3 [M+H]$^+$.

Step D: 2-[2-(3-fluoropyrrolidin-1-yl)ethoxy]-7-(3-methoxy-1-naphthyl)-4-piperazin-1-yl-6,8-dihydro-5H-pyrido[3,4-d]pyrimidine A mixture of benzyl 4-[2-[2-(3-fluoropyrrolidin-1-yl)ethoxy]-7-(3-methoxy-1-naphthyl)-6,8-dihydro-5H-pyrido[3,4-d]pyrimidin-4-yl]piperazine-1-carboxylate (700.00 mg, 1.09 mmol, 1.00 eq) in MeOH was hydrogenated (15 psi) at 40° C. with dry Pd/C (140 mg) as a catalyst for 4 hours. The catalyst was filtered through a Celite® pelt and the filtrate was concentrated under vacuum to provide 2-[2-(3-fluoropyrrolidin-1-yl)ethoxy]-7-(3-methoxy-1-naphthyl)-4-piperazin-1-yl-6,8-dihydro-5H-pyrido[3,4-d]pyrimidine (500 mg, 987 µmol, 90.6% yield) as a brown solid.

Step E: 1-[4-[2-[2-(3-fluoropyrrolidin-1-yl)ethoxy]-7-(3-methoxy-1-naphthyl)-6,8-dihydro-5H-pyrido[3,4-d]pyrimidin-4-yl]piperazin-1-yl]prop-2-en-1-one: To a mixture of 2-[2-(3-fluoropyrrolidin-1-yl)ethoxy]-7-(3-methoxy-1-naphthyl)-4-piperazin-1-yl-6,8-dihydro-5H-pyrido[3,4-d]pyrimidine (500 mg, 987 µmol, 1.00 eq) and DIEA (255 mg, 1.97 mmol, 345 µL, 2.00 eq) in dichloromethane (8 mL) was added a solution of prop-2-enoyl prop-2-enoate (124 mg, 987 µmol, 1.00 eq) in dichloromethane (2 mL) at −40° C. under nitrogen atmosphere. The mixture was warmed to 25° C. and stirred for 1 hour. The mixture was diluted with water (20 mL) and dichloromethane (30 mL). The separated organic layer was washed with brine (1×30 mL), dried over magnesium sulfate, filtered and concentrated under vacuum. The residue was purified by column chromatography over silica gel (dichloromethane/methanol 100/1 to 10/1). The desired fractions were collected and concentrated under vacuum to give 1-[4-[2-[2-(3-fluoropyrrolidin-1-yl)ethoxy]-7-(3-methoxy-1-naphthyl)-6,8-dihydro-5H-pyrido[3,4-d]pyrimidin-4-yl]piperazin-1-yl]prop-2-en-1-one (450 mg, 714 µmol, 72.4% yield, 89% purity) as a yellow solid. ESI MS m/z 561.2 [M+H]$^+$.

Step F: 1-[4-[2-[2-(3-fluoropyrrolidin-1-yl)ethoxy]-7-(3-hydroxy-1-naphthyl)-6,8-dihydro-5H-pyrido[3,4-d]pyrimidin-4-yl]piperazin-1-yl]prop-2-en-1-one: To a solution of 1-[4-[2-[2-(3-fluoropyrrolidin-1-yl) ethoxy]-7-(3-methoxy-1-naphthyl)-6,8-dihydro-5H-pyrido[3,4-d]pyrimidin-4-yl]piperazin-1-yl]prop-2-en-1-one (400 mg, 713 µmol, 1.00 eq) in DCM (2.00 mL) was added BBr$_3$ (1.30 g, 5.19 mmol, 500 µL, 7.27 eq) at −70° C. under nitrogen atmosphere. The mixture was warmed to 0° C. and stirred for 1 hour. The mixture was diluted with dichloromethane (20 mL), and then quenched with saturated aqueous sodium bicarbonate solution (20 mL). The separated organic layer was washed with brine (1×10 mL), dried over sodium sulfate, filtered and concentrated under vacuum. The residue was purified by preparative HPLC (Phenomenex Synergi C18 150*25*, 10µ; mobile phase: [water (0.1% TFA)-ACN]; B %: 18%-48%, 12 min.) The desired fractions were collected and lyophilized to give 1-[4-[2-[2-(3-fluoropyrrolidin-1-yl)ethoxy]-7-(3-hydroxy-1-naphthyl)-6,8-dihydro-5H-pyrido[3,4-d]pyrimidin-4-yl]piperazin-1-yl]prop-2-en-1-one (40.0 mg, 63.7 µmol, 8.92% yield, 87% purity) was a yellow solid. ESI MS m/z 547.3 [M+H]$^+$.

Example 50

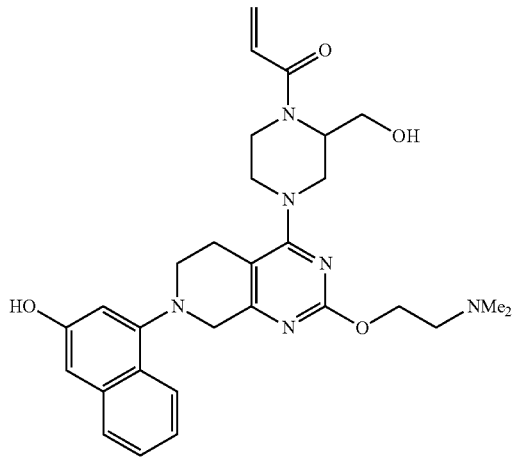 [SMILES: C=CC(=O)N1CCN(c2nc(OCCN(C)C)nc3c2CCN(c2cc(O)cc4ccccc24)C3)CC1CO]

1-(4-(2-(2-(dimethylamino)ethoxy)-7-(3-hydroxynaphthalen-1-yl)-5,6,7,8-tetrahydropyrido[3,4-d]pyrimidin-4-yl)-2-(hydroxymethyl)piperazin-1-yl)prop-2-en-1-one Step A: 1-tert-butyl 2-methyl4-(7-benzyl-2-chloro-6,8-dihydro-5H-pyrido[3,4-d]pyrimidin-4-yl)piperazine-1,2-dicarboxylate To a solution of 7-benzyl-2,4-dichloro-6,8-dihydro-5H-pyrido[3,4-d] pyrimidine (2.00 g, 6.80 mmol, 1.00 eq) in DMSO (40.0 mL) was added DIEA (1.76 g, 13.6 mmol, 2.38 mL, 2.00 eq) and 1-tert-butyl 2-methylpiperazine-1,2-dicarboxylate (1.74 g, 7.14 mmol, 1.05 eq). The mixture was stirred at 55° C. for 16 hours. The mixture was diluted with water (100 mL) and extracted with ethyl acetate (3×100 mL). The combined organic layers were washed with brine (3×100 mL), dried over Na$_2$SO$_4$, filtered and concentrated to dryness. The residue was purified by column chromatography (SiO$_2$, diethyl ether/ethyl acetate=1:0 to 3:1) to give 1-tert-butyl 2-methyl-4-(7-benzyl-2-chloro-6,8-dihydro-5H-pyrido[3,4-d]pyrimidin-4-yl)piperazine-1,2-dicarboxylate (3.10 g, 5.70 mmol, 83.8% yield, 92.3% purity) as a yellow semisolid. ESI MS m/z 502.2 [M+H]$^+$.

Step B: 1-tert-butyl 2-methyl4-[7-benzyl-2-[2-(dimethylamino)ethoxy]-6,8-dihydro-5H-pyrido[3,4-d] pyrimidin-4- yl]piperazine-1,2-dicarboxylate: A mixture of 1-tert-butyl 2-methyl-4-(7-benzyl-2-chloro-6,8-dihydro-5H-pyrido[3,4-d]pyrimidin-4-yl)piperazine-1,2-dicarboxylate (3.00 g, 5.98 mmol, 1.00 eq), 2-(dimethylamino)ethanol (1.07 g, 12.0 mmol, 1.20 mL, 2.00 eq), $Cs_2CO_3$ (4.87 g, 15.0 mmol, 2.50 eq), $Pd(OAc)_2$ (201 mg, 897 µmol, 0.15 eq) and BINAP (744 mg, 1.20 mmol, 0.20 eq) in toluene (60.0 mL) was degassed and purged with nitrogen 3 times, and then the mixture was stirred at 110° C. for 3 hours under a nitrogen atmosphere. The reaction mixture was diluted with water (50 mL) and extracted with ethyl acetate (3×50 mL). The combined organic layers were washed with brine (3×50 mL), dried over $Na_2SO_4$, filtered and concentrated to dryness. The residue was purified by column chromatography ($SiO_2$, DCM/MeOH=1:0 to 5:1) to give 1-tert-butyl 2-methyl-4-[7-benzyl-2-[2-(dimethylamino)ethoxy]-6,8-dihydro-5H-pyrido[3,4-d] pyrimidin-4-yl]piperazine-1,2-dicarboxylate (3.10 g, 4.45 mmol, 80.4% yield, 86.0% purity) as a black oil. ESI MS m/z 555.3 $[M+H]^+$.

Step C: 1-tert-butyl 2-methyl4-[2-[2-(dimethylamino)ethoxy]-5,6,7,8-tetrahydropyrido[3,4-d]pyrimidin-4-yl]piperazine-1,2-dicarboxylate To a solution of 1-tert-butyl 2-methyl-4-[7-benzyl-2-[2-(dimethyl amino)ethoxy]-6,8-dihydro-5H-pyrido[3,4-d]pyrimidin-4-yl]piperazine-1,2-dicarboxylate (2.33 g, 4.20 mmol, 1.00 eq) in MeOH (50.0 mL) was added Pd/C (233 mg) under $N_2$. The suspension was degassed under vacuum and purged with hydrogen several times. The mixture was stirred under hydrogen (50 psi) at 40° C. for 36 hours. The reaction mixture was filtered and the organic phase was concentrated to dryness to give 1-tert-butyl-2-methyl4-[2-[2-(dimethylamino)ethoxy]-5,6,7,8-tetrahydropyrido[3,4-d]pyrimidin-4-yl]piperazine-1,2-dicarboxylate (1.50 g, crude) as a colorless oil, which was used directly in the next step without further purification.

Step D: 1-tert-butyl2-methyl 4-[7-(3-benzyloxy-1-naphthyl)-2-[2-(dimethylamino)ethoxy]-6,8-dihydro-5H-pyrido[3,4-d]pyrimidin-4-yl]piperazine-1,2-dicarboxylate: A mixture of 1-tert-butyl-2-methyl4-[2-[2-(dimethylamino)ethoxy]-5,6,7,8-tetrahydropyrido[3,4-d]pyrimidin-4-yl]piperazine-1,2-dicarboxylate (1.50 g, crude), 3-benzyloxy-1-bromo-naphthalene (1.49 g, 4.76 mmol, 1.30 eq), $Cs_2CO_3$ (2.98 g, 9.15 mmol, 2.50 eq), $Pd_2(dba)_3$ (503 mg, 549 µmol, 0.15 eq) and 2-dicyclohexylphosphino-2',6'-diisopropoxybiphenyl (RuPhos) (342 mg, 732 µmol, 0.20 eq) in dioxane (100 mL) was degassed and purged with nitrogen 3 times, and the mixture was stirred at 85° C. for 5 hours under a nitrogen atmosphere. The reaction mixture was quenched by adding water (50 mL) at 0° C., and extracted with DCM (3×100 mL). The combined organic layers were washed with brine (3×150 mL), dried over $Na_2SO_4$, filtered and concentrated under reduced pressure to dryness. The residue was purified by column chromatography ($SiO_2$, DCM/MeOH=10:1 to 5:1) to give 1-tert-butyl2-methyl 4-[7-(3-benzyloxy-1-naphthyl)-2-[2-(dimethylamino)ethoxy]-6,8-dihydro-5H-pyrido[3,4-d]pyrimidin-4-yl]piperazine-1,2-dicarboxylate (1.72 g, 2.25 mmol, 53.5% yield, 91% purity) as a yellow. ESI MS m/z 697.3 $[M+H]^+$.

Step E: methyl 4-[7-(3-benzyloxy-1-naphthyl)-2-[2-(dimethylamino)ethoxy]-6,8-di hydro-5H-pyrido[3,4-d]pyrimidin-4-yl]piperazine-2-carboxylate: To a solution of 1-tert-butyl 2-methyl4-[7-(3-benzyloxy-1-naphthyl)-2-[2-(dimethylamino)ethoxy]-6,8-dihydro-5H-pyrido[3,4-d]pyrimidin-4-yl]piperazine-1,2-dicarboxylate (1.32 g, 1.89 mmol, 1.00 eq) in DCM (20.0 mL) was added TFA (4.31 g, 37.8 mmol, 2.80 mL, 20.0 eq) at 0° C. and the reaction mixture was stirred for 2 hours at 25° C. The reaction mixture was concentrated under reduced pressure to dryness. The residue was dissolved in DCM (50 mL) and $H_2O$ (20 mL) and the reaction mixture was adjusted to pH 8 with saturated $NaHCO_3$. The organic layer was dried over $Na_2SO_4$, filtered and concentrated under reduced pressure to give methyl 4-[7-(3-benzyloxy-1-naphthyl)-2-[2-(dimethylamino)ethoxy]-6,8-dihydro-5H-pyrido[3,4-d]pyrimidin-4-yl]piperazine-2-carboxylate (1.12 g, 1.87 mmol, 69.6% yield, 70% purity) as a brown oil, which was used directly in the next step without further purification. ESI MS m/z 597.4 $[M+H]^+$.

Step F: [4-[7-(3-benzyloxy-1-naphthyl)-2-[2-(dimethylamino)ethoxy]-6,8-dihydro-5H-pyrido[3,4-d]pyrimidin-4-yl]piperazin-2-yl]methanol A mixture of methyl-4-[7-(3-benzyloxy-1-naphthyl)-2-[2-(dimethyl amino)ethoxy]-6,8-dihydro-5H-pyrido[3,4-d]pyrimidin-4-yl]piperazine-2-carboxylate (400 mg, 0.670 mmol) in THF (5.00 mL) was added $LiAlH_4$ (102 mg, 2.68 mmol, 4.00 eq) at 0° C. The reaction mixture was degassed and purged with nitrogen 3 times, and stirred at 0° C. for 2 hours under a nitrogen atmosphere. The reaction mixture was quenched by addition of $Na_2SO_4.10H_2O$ (0.5 g) at 0° C., and then diluted with DCM (50 mL). The combined organic layers were filtered, dried over $Na_2SO_4$, and concentrated under reduced pressure to give [4-[7-(3-benzyloxy-1-naphthyl)-2-[2-(dimethylamino)ethoxy]-6,8-dihydro-5H-pyrido[3,4-d]pyrimidin-4-yl]piperazin-2-yl]methanol (280 mg, 0.493 mmol, 73.6% yield) as a yellow semisolid, which was used directly in the next step without further purification. ESI MS m/z 569.3 $[M+H]^+$.

Step G: 2-[[7-(3-benzyloxy-1-naphthyl)-4-[3-[[tert-butyl(dimethyl)silyl]oxymethyl] piperazin-1-yl]-6,8-dihydro-5H-pyrido[3,4-d]pyrimidin-2-yl]oxy]-N,N-dimethyl-ethanamine: To a stirred solution of [4-[7-(3-benzyloxy-1-naphthyl)-2-[2-(dimethyl amino)ethoxy]-6,8-dihydro-5H-pyrido[3,4-d]pyrimidin-4-yl]piperazin-2-yl]methanol (250 mg, 440 µmol, 1.00 eq) and NaH (176 mg, 4.40 mmol, 60.0% purity, 10.0 eq) in THF (10.0 mL) was added tert-butyldimethylsilyl chloride (232 mg, 1.54 mmol, 189 µL, 3.50 eq) at 0° C. The mixture was stirred at 25° C. for 12 hours under a nitrogen atmosphere. The reaction mixture was quenched by addition of water (25 mL) at 0° C. and extracted with DCM (3×30 mL). The combined organic layers were washed with brine (3×30 mL), dried over $Na_2SO_4$, filtered and concentrated under reduced pressure to dryness. The residue was purified by preparative TLC ($SiO_2$, DCM/MeOH=10:1) to give 2-[[7-(3-benzyloxy-1-naphthyl)-4-[3-[[tert-butyl(dimethyl)silyl]oxymethyl] piperazin-1-yl]-6,8-dihydro-5H-pyrido[3,4-d]pyrimidin-2-yl]oxy]-N,N-dimethyl-ethanamine (128 mg, 180 µmol, 40.9% yield, 96.0% purity) as a colorless semisolid. ESI MS m/z 683.3 $[M+H]^+$.

Step H: 1-[4-[7-(3-benzyloxy-1-naphthyl)-2-[2-(dimethylamino) ethoxy]-6,8-dihydro-5H-pyrido[3,4-d]pyrimidin-4-yl]-2-[[tert-butyl(dimethyl)silyl]oxymethyl]piperazin-1-yl]prop-2-en-1-one; To a solution of 2-[[7-(3-benzyloxy-1-naphthyl)-4-[3-[[tert-butyl (dimethyl)silyl]oxymethyl] piperazin-1-yl]-6,8-dihydro-5H-pyrido[3,4-d]pyrimidin-2-yl]oxy]-N,N-dimethyl-ethanamine (128 mg, 187 µmol, 1.00 eq) and triethylamine (47.4 mg, 469 µmol, 65.0 µL, 2.50 eq) in DCM (5.00 mL) was added prop-2-enoyl prop-2-enoate (35.5 mg, 281 µmol, 1.50 eq) dropwise at −40° C. and stirred for 30 minutes. The reaction mixture was concentrated under reduced pressure to dryness. The residue was purified by preparative TLC (SiO₂, DCM/MeOH=10:1) to give 1-[4-[7-(3-benzyloxy-1-naphthyl)-2-[2-(dimethylamino) ethoxy]-6,8-dihydro-5H-pyrido[3,4-d]pyrimidin-4-yl]-2-[[tert-butyl(dimethyl)silyl]oxymethyl]piperazin-1-yl]prop-2-en-1-one (92.0 mg, 101 μmol, 54.0% yield, 81.0% purity) as a yellow solid. ESI MS m/z 737.3 [M+H]⁺.

Step I: 1-[4-[2-[2-(dimethylamino)ethoxy]-7-(3-hydroxy-1-naphthyl)-6,8-dihydro-5H-pyrido[3,4-d]pyrimidin-4-yl]-2-(hydroxymethyl)piperazin-1-yl]prop-2-en-1-one: A mixture of 1-[4-[7-(3-benzyloxy-1-naphthyl)-2-[2-(dimethylamino) ethoxy]-6,8-dihydro-5H-pyrido[3,4-d]pyrimidin-4-yl]-2-[[tert-butyl(dimethyl)silyl]oxymethyl]piperazin-1-yl]prop-2-en-1-one (92.0 mg, 125 μmol, 1.00 eq) in DCM (8.00 mL) was added BBr₃ (17.0 mg, 67.8 μmol, 6.53 μL, 10.0 eq). The mixture was stirred at −40° C. for 30 minutes under a nitrogen atmosphere and then concentrated at 25° C. under reduced pressure to dryness. To the residue was added saturated NaHCO₃ aqueous (0.5 mL). The solution was adjusted to pH 7 at 0° C. and then MeOH (2.0 mL) was added. The solution was purified by preparative HPLC (column: Phenomenex Synergi C18 150*25*, 10μ; mobile phase: [water (0.1% TFA)-ACN]; B %: 15%-45%, 11 min). The desired fractions were collected and concentrated under reduced pressure to remove MeCN and lyophilized to give 1-[4-[2-[2-(dimethylamino)ethoxy]-7-(3-hydroxy-1-naphthyl)-6,8-dihydro-5H-pyrido[3,4-d]pyrimidin-4-yl]-2-(hydroxymethyl)piperazin-1-yl]prop-2-en-1-one (6.30 mg, 11.2 μmol, 9.00% yield, 95.0% purity) as a yellow solid. ESI MS m/z 533.2 [M+H]⁺.

Example 51

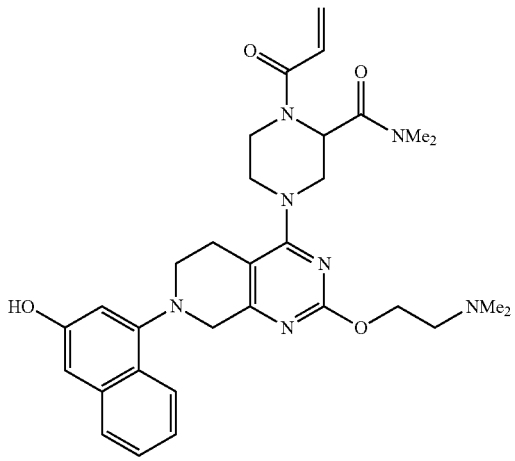 [SMILES: C=CC(=O)N1CCN(c2nc(OCCN(C)C)nc3c2CCN(c2cc(O)cc4ccccc24)C3)CC1C(=O)N(C)C]

1-acryloyl-4-(2-(2-(dimethylamino)ethoxy)-7-(3-hydroxynaphthalen-1-yl)-5,6,7,8-tetrahydropyrido[3,4-d]pyrimidin-4-yl)-N,N-dimethylpiperazine-2-carboxamide Step A: 4-[7-(3-benzyloxy-1-naphthyl)-2-[2-(dimethylamino)ethoxy]-6,8-dihydro-5H-pyrido[3,4-d]pyrimidin-4-yl]-1-tert-butoxycarbonyl-piperazine-2-carboxylic acid: To a solution of 1-tert-butyl 2-methyl 4-[7-(3-benzyloxy-1-naphthyl)-2-[2-(dimethylamino)ethoxy]-6,8-dihydro-5H-pyrido[3,4-d]pyrimidin-4-yl]piperazine-1,2-dicarboxylate (300 mg, 431 μmol, 1.00 eq) in THF (4.00 mL) and H₂O (1.00 mL) was added NaOH (68.9 mg, 1.72 mmol, 4.00 eq). The mixture was stirred at 25° C. for 12 hours under a nitrogen atmosphere. The reaction mixture was diluted with water (50 mL) and the reaction mixture was adjusted to pH 6 with HCl (6 M) and then extracted with DCM (3×50 mL). The combined organic layers were dried over Na₂SO₄, filtered and concentrated under reduced pressure to dryness to give 4-[7-(3-benzyloxy-1-naphthyl)-2-[2-(dimethylamino)ethoxy]-6,8-dihydro-5H-pyrido[3,4-d]pyrimidin-4-yl]-1-tert-butoxycarbonyl-piperazine-2-carboxylic acid (310 mg, crude) as a yellow solid which was used directly in the next step without further purification. ESI MS m/z 683.3 [M+H]⁺.

Step B: tert-butyl4-[7-(3-benzyloxy-1-naphthyl)-2-[2-(dimethylamino)ethoxy]-6,8-dihydro-5H-pyrido[3,4-d]pyrimidin-4-yl]-2-(dimethylcarbamoyl)piperazine-1-carboxylate
A mixture of 4-[7-(3-benzyloxy-1-naphthyl)-2-[2-(dimethylamino)ethoxy]-6,8-dihydro-5H-pyrido[3,4-d]pyrimidin-4-yl]-1-tert-butoxycarbonyl-piperazine-2-carboxylic acid (310 mg, crude) and DIEA (352 mg, 2.72 mmol, 476 μL) in DCM (10.0 mL) was added portionwise HATU (259 mg, 681 μmol) at 0° C. After stirring for 30 minutes, N-methylmethanamine (130 mg, 1.59 mmol, 146 HCl) was added in one portion. The reaction mixture was degassed and purged with nitrogen 3 times. After stirring at 25° C. for 12 hours under a nitrogen atmosphere, the reaction mixture was diluted with water (50 mL) at 0° C. and extracted with DCM (3×50 mL). The combined organic layers were adjusted to pH 6 with HCl (1 M), washed with brine (3×50 mL) and water (3×50 mL), dried over Na₂SO₄, filtered and concentrated under reduced pressure to dryness to give tert-butyl4-[7-(3-benzyloxy-1-naphthyl)-2-[2-(dimethylamino)ethoxy]-6,8-dihydro-5H-pyrido[3,4-d]pyrimidin-4-yl]-2-(dimethylcarbamoyl)piperazine-1-carboxylate (345 mg, 428 μmol, two steps 94.2% yield, 88.0% purity) as a yellow semi-solid. ESI MS m/z 710.3 [M+H]⁺.

Step C: tert-butyl 4-[2-[2-(dimethylamino)ethoxy]-7-(3-hydroxy-1-naphthyl)-6,8-dihydro-5H-pyrido [3,4-d]pyrimidin-4-yl]-2-(dimethylcarbamoyl)piperazine-1-carboxylate:
To a solution of tert-butyl 4-[7-(3-benzyloxy-1-naphthyl)-2-[2-(dimethylamino)ethoxy]-6,8-dihydro-5H-pyrido[3,4-d]pyrimidin-4-yl]-2-(dimethylcarbamoyl)piperazine-1-carboxylate (345 mg, 486 μmol, 1.00 eq) in MeOH (5.00 mL) was added Pd/C (80.0 mg) under N₂. The suspension was degassed under vacuum and purged with hydrogen several times. The mixture was stirred under hydrogen (15 psi) at 25° C. for 8 hours. The reaction mixture was filtered and the filtrate was concentrated under reduced pressure to dryness to give tert-butyl 4-[2-[2-(dimethylamino)ethoxy]-7-(3-hydroxy-1-naphthyl)-6,8-dihydro-5H-pyrido [3,4-d]pyrimidin-4-yl]-2-(dimethylcarbamoyl)piperazine-1-carboxylate (197 mg, crude) as a brown solid, which was used directly in the next step without further purification. ESI MS m/z 620.3 [M+H]⁺.

Step D: 4-[2-[2-(dimethylamino)ethoxy]-7-(3-hydroxy-1-naphthyl)-6,8-dihydro-5H-pyrido[3,4-d]pyrimidin-4-yl]-N,N-dimethyl-piperazine-2-carboxamide: A mixture of tert-butyl 4-[2-[2-(dimethylamino)ethoxy]-7-(3-hydroxy-1-naphthyl)-6,8-dihydro-5H-pyrido[3,4-d]pyrimidin-4-yl]-2-(dimethylcarbamoyl)piperazine-1-carboxylate (197 mg, crude) in DCM (5.00 mL) was added HCl/dioxane (4 M, 1.61 mL) at 0° C. The reaction mixture was degassed and purged with nitrogen 3 times and stirred at 25° C. for 2 hours under a nitrogen atmosphere. The reaction mixture was concentrated under reduced pressure to dryness. The residue was purified by preparative HPLC (column: Phenomenex Synergi C18 150*25*, 10μ; mobile phase: [water (0.05%

HCl)-ACN]; B %: 10%-30%, 7.8 min). The collected water phase was lyophilized to dryness to give 4-[2-[2-(dimethylamino)ethoxy]-7-(3-hydroxy-1-naphthyl)-6,8-dihydro-5H-pyrido[3,4-d]pyrimidin-4-yl]-N,N-dimethyl-piperazine-2-carboxamide (90.0 mg, 171 μmol, 53.1% yield, 99.0% purity) as a brown solid. ESI MS m/z 520.2 [M+H]$^+$.

Step E: 4-[2-[2-(dimethylamino)ethoxy]-7-(3-hydroxy-1-naphthyl)-6,8-dihydro-5H-pyrido[3,4-d]pyrimidin-4-yl]-N,N-dimethyl-1-prop-2-enoyl-piperazine-2-carboxamide: To a solution of 4-[2-[2-(dimethylamino)ethoxy]-7-(3-hydroxy-1-naphthyl)-6,8-dihydro-5H-pyrido[3,4-d]pyrimidin-4-yl]-N,N-dimethyl-piperazine-2-carboxamide (70.0 mg, 135 μmol, 1.00 eq) in DMAC (500 μL) was added triethylamine (40.9 mg, 404 μmol, 56.0 μL, 3.00 eq) at 0° C. and then prop-2-enoyl prop-2-enoate (2.55 mg, 20.2 μmol, 0.15 eq) was added. The mixture was stirred at 0° C. for 2 hours under a nitrogen atmosphere. The reaction mixture was filtered and the collected organic phase was purified by preparative HPLC (column: Phenomenex Synergi C18 150*25*, 10μ; mobile phase: [water (0.1% TFA)-ACN]; B %: 15%-45%, 12 min). The collected water phase was lyophilized to give 4-[2-[2-(dimethylamino)ethoxy]-7-(3-hydroxy-1-naphthyl)-6,8-dihydro-5H-pyrido[3,4-d]pyrimidin-4-yl]-N,N-dimethyl-1-prop-2-enoyl-piperazine-2-carboxamide (10.0 mg, 16.5 μmol, 12.2% yield, 94.6% purity) as a yellow semisolid. ESI MS m/z 574.2 [M+H]$^+$.

Example 52

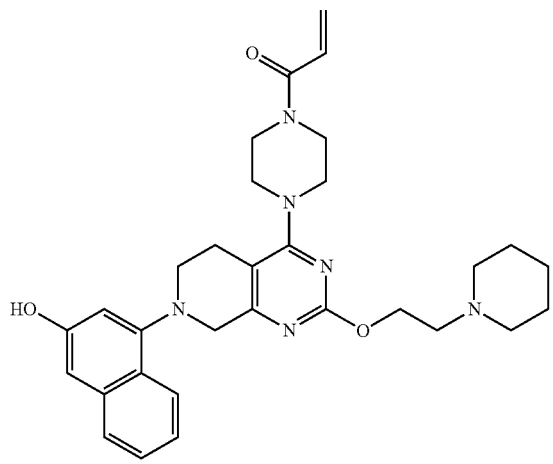 [SMILES: C=CC(=O)N1CCN(c2nc(OCCN3CCCCC3)nc3c2CCN(c2cc(O)cc4ccccc24)C3)CC1]

1-[4-[7-(3-hydroxy-1-naphthyl)-2-[2-(1-piperidyl)ethoxy]-6,8-dihydro-5H-pyrido[3,4-d]pyrimidin-4-yl]piperazin-1-yl]prop-2-en-1-one Step A: tert-butyl 4-[7-benzyl-2-[2-(1-piperidyl)ethoxy]-6,8-dihydro-5H-pyrido[3,4-d]pyrimidin-4-yl]piperazine-1-carboxylate To a solution of 2-(1-piperidyl)ethanol (872 mg, 6.75 mmol, 899 μL, 3.00 eq) in toluene (40.0 mL) was added Pd(OAc)$_2$ (50.5 mg, 225 μmol, 0.10 eq), Cs$_2$CO$_3$ (2.20 g, 6.75 mmol, 3.00 eq), BINAP (280 mg, 450 μmol, 0.20 eq) and tert-butyl 4-(7-benzyl-2-chloro-6,8-dihydro-5H-pyrido[3,4-d]pyrimidin-4-yl)piperazine-1-carboxylate (1.00 g, 2.25 mmol, 1.00 eq). The mixture was stirred at 110° C. for 12 hours under N$_2$ and then concentrated under vacuum. The residue was diluted with water (10.0 mL), extracted with ethyl acetate (3×20 mL), washed with brine (1×50 mL), dried over Na$_2$SO$_4$, filtered and concentrated under vacuum. The residue was purified by column chromatography (SiO$_2$, DCM/MeOH=10:1) to give tert-butyl 4-[7-benzyl-2-[2-(1-piperidyl)ethoxy]-6,8-dihydro-5H-pyrido[3,4-d]pyrimidin-4-yl]piperazine-1-carboxylate (700 mg, 1.30 mmol, 58.0% yield) as a red solid. ESI MS m/z 537.3 [M+H]$^+$.

Step B: tert-butyl 4-[2-[2-(1-piperidyl)ethoxy]-5,6,7,8-tetrahydropyrido[3,4-d]pyrimidin-4-yl] piperazine-1-carboxylate To a mixture of tert-butyl 4-[7-benzyl-2-[2-(1-piperidyl)ethoxy]-6,8-dihydro-5H-pyrido[3,4-d]pyrimidin-4-yl]piperazine-1-carboxylate (600 mg, 1.12 mmol, 1.00 eq) in MeOH (50.0 mL) was added Pd/C (67.2 mg, 10%). The mixture was stirred at 40° C. for 24 hours at 50 psi under H$_2$. The mixture was filtered and concentrated under vacuum to give tert-butyl 4-[2-[2-(1-piperidyl)ethoxy]-5,6,7,8-tetrahydropyrido[3,4-d]pyrimidin-4-yl] piperazine-1-carboxylate (500 mg, crude) as a brown oil and used in the next step without further purification. ESI MS m/z 447.3 [M+H]$^+$.

Step C: tert-butyl 4-[7-(3-methoxy-1-naphthyl)-2-[2-(1-piperidyl)ethoxy]-6,8-dihydro-5H-pyrido [3,4-d]pyrimidin-4-yl]piperazine-1-carboxylate: To a solution of tert-butyl 4-[2-[2-(1-piperidyl)ethoxy]-5,6,7,8-tetrahydropyrido[3,4-d]pyrimidin-4-yl]piperazine-1-carboxylate (250 mg) and (3-methoxy-1-naphthyl) trifluoromethanesulfonate (343 mg, 1.12 mmol) in toluene (6.00 mL) was added 2-dicyclohexylphosphino-2',6'-diisopropoxybiphenyl (RuPhos) (52.3 mg, 112 μmol), Pd$_2$(dba)$_3$ (32.19 mg, 55.98 μmol) and Cs$_2$CO$_3$ (548 mg, 1.68 mmol). After stirring at 110° C. for 72 hours under N$_2$, the mixture was concentrated under vacuum, diluted with water (20.0 mL), extracted with ethyl acetate (3×30.0 mL), washed with brine (1×50.0 mL), dried over Na$_2$SO$_4$, filtered and concentrated under vacuum. The residue was purified by column chromatography (SiO$_2$, DCM/MeOH=10:1) to give tert-butyl 4-[7-(3-methoxy-1-naphthyl)-2-[2-(1-piperidyl)ethoxy]-6,8-dihydro-5H-pyrido [3,4-d]pyrimidin-4-yl]piperazine-1-carboxylate (140 mg, 232 μmoL, two steps, 41.5% yield) as a yellow solid. ESI MS m/z 603.3 [M+H]$^+$.

Step D: 7-(3-methoxy-1-naphthyl)-4-piperazin-1-yl-2-[2-(1-piperidyl)ethoxy]-6,8-dihydro-5H-pyrido[3,4-d]pyrimidine A mixture of tert-butyl 4-[7-(3-methoxy-1-naphthyl)-2-[2-(1-piperidyl) ethoxy]-6,8-dihydro-5H-pyrido [3,4-d]pyrimidin-4-yl]piperazine-1-carboxylate (120 mg, 199 μmol, 1.00 eq) and TFA (340 mg, 2.99 mmol, 221 μL, 15.0 eq) in DCM (1.00 mL) was stirred at 25° C. for 1 hour. The mixture was concentrated under vacuum to give 7-(3-methoxy-1-naphthyl)-4-piperazin-1-yl-2-[2-(1-piperidyl)ethoxy]-6,8-dihydro-5H-pyrido [3,4-d]pyrimidine bis-trifluoroacetate (145 mg, crude) as a yellow solid which was used into next step without further purification. ESI MS m/z 503.3 [M+H]$^+$.

Step E: 1-[4-[7-(3-methoxy-1-naphthyl)-2-[2-(1-piperidyl) ethoxy]-6,8-dihydro-5H-pyrido[3,4-d]pyrimidin-4-yl] piperazin-1-yl]prop-2-en-1-one: To a solution of 7-(3-methoxy-1-naphthyl)-4-piperazin-1-yl-2-[2-(1-piperidyl) ethoxy]-6,8-dihydro-5H-pyrido[3,4-d]pyrimidine bis-trifluoroacetate (145 mg, crude) and Et$_3$N (221 mg, 2.18 mmol, 303 μL) in DCM (2.00 mL) was added prop-2-enoyl prop-2-enoate (25.0 mg, 198 μmol) at −78° C. After stirring at 0° C. for 0.5 h, the mixture quenched with MeOH and concentrated under vacuum. The mixture was purified by column chromatography (SiO₂, DCM/MeOH=10:1) to give 1-[4-[7-(3-methoxy-1-naphthyl)-2-[2-(1-piperidyl)ethoxy]-6,8-dihydro-5H-pyrido[3,4-d]pyrimidin-4-yl]piperazin-1-yl]prop-2-en-1-one (90.0 mg, 162 μmol, two steps 81.5% yield) a yellow solid. ESI MS m/z 557.3 [M+H]⁺.

Step F: 1-[4-[7-(3-hydroxy-1-naphthyl)-2-[2-(1-piperidyl)ethoxy]-6,8-dihydro-5H-pyrido[3,4-d]pyrimidin-4-yl]piperazin-1-yl]prop-2-en-1-one: To a solution of 1-[4-[7-(3-methoxy-1-naphthyl)-2-[2-(1-piperidyl) ethoxy]-6,8-dihydro-5H-pyrido[3,4-d]pyrimidin-4-yl]piperazin-1-yl] prop-2-en-1-one (90.0 mg, 162 μmol, 1.00 eq) in DCM (2.00 mL) was added BBr₃ (405 mg, 1.62 mmol, 156 μL, 10.0 eq) at −78° C. After stirring at 0° C. for 1 h, the mixture was quenched with saturated sodium bicarbonate solution at −78° C. and stirred at 0° C. for 0.5 h. The mixture was extracted with ethyl acetate (3×20.0 mL), washed with brine (1×40.0 mL), dried over Na₂SO₄, filtered and concentrated under vacuum. The residue was purified by preparative HPLC (Phenomenex Gemini 150*25 mm*, 10μ; mobile phase: [water (0.05% ammonia hydroxide v/v)-ACN]; B %: 55%-85%, 10 min) to give 1-[4-[7-(3-hydroxy-1-naphthyl)-2-[2-(1-piperidyl)ethoxy]-6,8-dihydro-5H-pyrido[3,4-d]pyrimidin-4-yl]piperazin-1-yl]prop-2-en-1-one (6.19 mg, 10.8 μmol, 6.71% yield, 95% purity) as a yellow oil. ESI MS m/z 543.2 [M+H]⁺.

Example 53

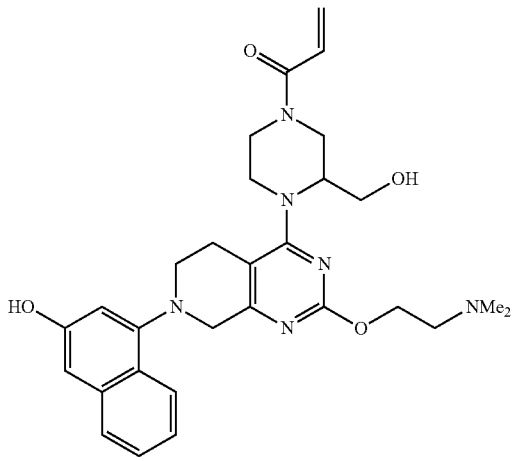 [SMILES: C=CC(=O)N1CCN(c2nc(OCCN(C)C)nc3c2CCN(c2cc(O)cc4ccccc24)C3)C(CO)C1]

1-(4-(2-(2-(dimethylamino)ethoxy)-7-(3-hydroxynaphthalen-1-yl)-5,6,7,8-tetrahydropyrido[3,4-d]pyrimidin-4-yl)-3-(hydroxymethyl)piperazin-1-yl)prop-2-en-1-one Step A: 1-tert-butyl 3-methyl 4-(7-benzyl-2-chloro-5,6,7,8-tetrahydropyrido[3,4-d]pyrimidin-4-yl)piperazine-1,3-dicarboxylate A mixture of 7-benzyl-2,4-dichloro-6,8-dihydro-5H-pyrido[3,4-d] pyrimidine (3.00 g, 10.2 mmol, 1.00 eq), 1-tert-butyl-3-methyl piperazine-1,3-dicarboxylate (2.62 g, 10.7 mmol, 1.05 eq), DIEA (3.30 g, 25.5 mmol, 4.45 mL, 2.50 eq) in DMSO (50.0 mL) was degassed and purged with nitrogen 3 times. The mixture was stirred at 100° C. for 12 hours under a nitrogen atmosphere. The reaction mixture was diluted with DCM (200 mL), washed with brine (3×50 mL), dried over Na₂SO₄, filtered and concentrated under reduced pressure to dryness. The residue was purified by column chromatography (SiO₂, Petroleum ether/Ethyl acetate=10:1 to 3:1) to give 1-tert-butyl 3-methyl 4-(7-benzyl-2-chloro-5,6,7,8-tetrahydropyrido[3,4-d]pyrimidin-4-yl)piperazine-1,3-dicarboxylate (2.10 g, 3.81 mmol, 37.4% yield, 91.0% purity) as a yellow oil. ESI MS m/z 502.1 [M+H]⁺.

Step B: 1-tert-butyl 3-methyl4-(7-benzyl-2-(2-(dimethylamino)ethoxy)-5,6,7,8-tetrahydropyrido[3,4-d]pyrimidin-4-yl)piperazine-1,3-dicarboxylate: A mixture of 1-tert-butyl 3-methyl 4-(7-benzyl-2-chloro-5,6,7,8-tetrahydropyrido[3,4-d]pyrimidin-4-yl)piperazine-1,3-dicarboxylate (2.10 g, 4.17 mmol, 1.00 eq), 2-(dimethylamino)ethanol (929 mg, 10.4 mmol, 1.04 mL, 2.50 eq), Pd(OAc)₂ (140 mg, 625 μmol, 0.15 eq), BINAP (519 mg, 833 μmol, 0.20 eq) and Cs₂CO₃ (3.39 g, 10.4 mmol, 2.50 eq) in toluene (60.0 mL) was degassed and purged with nitrogen for 3 times. The mixture was stirred at 110° C. for 3 hours under a nitrogen atmosphere. The reaction mixture was filtered and concentrated under reduced pressure to dryness. The residue was purified by column chromatography (SiO₂, DCM/MeOH=30:1 to 10:1) to give 1-tert-butyl 3-methyl4-(7-benzyl-2-(2-(dimethylamino)ethoxy)-5,6,7,8-tetrahydropyrido[3,4-d]pyrimidin-4-yl)piperazine-1,3-dicarboxylate (1.30 g, 1.67 mmol, 40.0% yield, 71.4% purity) as a yellow solid. ESI MS m/z 555.3 [M+H]⁺.

Step C: 1-tert-butyl 3-methyl 4-(2-(2-(dimethylamino)ethoxy)-5,6,7,8-tetrahydropyrido[3,4-d]pyrimidin-4-yl) piperazine-1,3-dicarboxylate: To a solution of 1-tert-butyl 3-methyl 4-(7-benzyl-2-(2-(dimethylamino)ethoxy)-5,6,7,8-tetrahydropyrido[3,4-d]pyrimidin-4-yl)piperazine-1,3-dicarboxylate (1.30 g, 2.34 mmol, 1.00 eq) in MeOH (15.0 mL) was added Pd/C (300 mg) under N₂. The suspension was degassed under vacuum and purged with hydrogen several times. The mixture was stirred under hydrogen (50 psi) at 45° C. for 48 hours. The catalyst was filtered off and the filtrate was concentrated under reduced pressure to give 1-tert-butyl 3-methyl 4-(2-(2-(dimethylamino)ethoxy)-5,6,7,8-tetrahydropyrido[3,4-d]pyrimidin-4-yl) piperazine-1,3-dicarboxylate (780 mg, crude) as a colorless oil, which was used directly in the next step without further purification.

Step D: 1-tert-butyl 3-methyl 4-(7-(3-(benzyloxy)naphthalen-1-yl)-2-(2-(dimethylamino)ethoxy)-5,6,7,8-tetrahydropyrido[3,4-d]pyrimidin-4-yl)piperazine-1,3-dicarboxylate: A mixture of 1-tert-butyl 3-methyl 4-(2-(2-(dimethylamino)ethoxy)-5,6,7,8-tetrahydropyrido[3,4-d]pyrimidin-4-yl)piperazine-1,3-dicarboxylate (780 mg, crude), 3-benzyloxy-1-bromo-naphthalene (684 mg, 2.18 mmol), Pd₂(dba)₃ (231 mg, 252 μmol), Cs₂CO₃ (1.37 g, 4.20 mmol) and 2-dicyclohexylphosphino-2',6'-diisopropoxybiphenyl (RuPhos) (157 mg, 336 μmol) in dioxane (20.0 mL) was degassed and purged with nitrogen 3 times. The mixture was stirred at 85° C. for 5 hours under a nitrogen atmosphere. The reaction mixture was filtered and concentrated under reduced pressure to dryness. The residue was purified by column chromatography (SiO₂, DCM/MeOH=10:1 to 5:1) to give 1-tert-butyl 3-methyl 4-(7-(3-(benzyloxy)naphthalen-1-yl)-2-(2-(dimethylamino)ethoxy)-5,6,7,8-tetrahydropyrido[3,4-d]pyrimidin-4-yl)piperazine-1,3-dicarboxylate (750 mg, 1.02 mmol, two steps 43.6% yield, 95.0% purity) as a yellow solid. ¹H NMR (400 MHz, chloroform-d) δ=8.10 (d, J=8.0 Hz, 1H), 7.73 (d, J=8.0 Hz, 1H), 7.58-7.31 (m, 8H), 7.00 (d, J=2.0 Hz, 1H), 6.89 (d, J=2.0 Hz, 1H), 5.18 (s, 2H), 4.75 (br s, 1H), 4.45 (br d, J=13.2 Hz, 1H), 4.42-4.34

(m, 1H), 4.34-4.28 (m, 1H), 4.15 (br s., 2H), 4.13-3.91 (m, 1H), 3.85-3.70 (m, 5H), 3.49-3.33 (m, 2H), 3.31-3.07 (m, 2H), 2.99 (br s, 1H), 2.83-2.68 (m, 3H), 2.35 (s, 6H), 1.48 (s, 9H).

Step E: methyl 1-(7-(3-(benzyloxy)naphthalen-1-yl)-2-(2-(dimethylamino)ethoxy)-5,6,7,8-tetrahydropyrido[3,4-d]pyrimidin-4-yl)piperazine-2-carboxylate: To a solution of 1-tert-butyl 3-methyl 4-(7-(3-(benzyloxy)naphthalen-1-yl)-2-(2-(dimethylamino)ethoxy)-5,6,7,8-tetrahydropyrido[3,4-d]pyrimidin-4-yl)piperazine-1,3-dicarboxylate (200 mg, 287 µmol, 1.00 eq) in DCM (5.00 mL) was added TFA (770 mg, 6.75 mmol, 500 µL, 23.5 eq) at 0° C. The mixture was stirred at 25° C. for 2 hours under a nitrogen atmosphere. The reaction mixture was concentrated under reduced pressure to dryness. The residue was dissolved in DCM (100 mL) and water (50 mL) and the solution was adjusted to pH 8 with saturated $Na_2CO_3$ aqueous and then extracted with DCM (3×50 mL). The combined organic layers were washed with brine (3×50 mL), dried over $Na_2SO_4$, filtered and concentrated under reduced pressure to give methyl 1-(7-(3-(benzyloxy)naphthalen-1-yl)-2-(2-(dimethylamino)ethoxy)-5,6,7,8-tetrahydropyrido[3,4-d]pyrimidin-4-yl)piperazine-2-carboxylate (171 mg, 263 µmol, 91.6% yield, 91.7% purity) as a yellow solid. ESI MS m/z 597.2 [M+H]⁺.

Step F: (1-(7-(3-(benzyloxy) naphthalen-1-yl)-2-(2-(dimethylamino)ethoxy)-5,6,7,8-tetrahydropyrido[3,4-d]pyrimidin-4-yl)piperazin-2-yl)methanol: To a mixture of methyl 1-(7-(3-(benzyloxy)naphthalen-1-yl)-2-(2-(dimethylamino)ethoxy)-5,6,7,8-tetrahydropyrido[3,4-d]pyrimidin-4-yl)piperazine-2-carboxylate (171 mg, 287 µmol, 1.00 eq) in THF (5.00 mL) was added LiAlH₄ (65.3 mg, 1.72 mmol, 6.00 eq) at 0° C. After stirring for 2 hours at 25° C., the reaction mixture was quenched by addition of water (30 mL) at 0° C., and extracted with DCM (3×30 mL). The combined organic layers were washed with brine (3×30 mL). The collected organic phase was dried over $Na_2SO_4$, filtered and concentrated under reduced pressure to give (1-(7-(3-(benzyloxy)naphthalen-1-yl)-2-(2-(dimethylamino)ethoxy)-5,6,7,8-tetrahydropyrido[3,4-d]pyrimidin-4-yl)piperazin-2-yl)methanol (160 mg, 281 µmol, 98.2% yield, 100% purity) as a colorless semisolid. ESI MS m/z 569.2 [M+H]⁺.

Step G: 2-((7-(3-(benzyloxy)naphthalen-1-yl)-4-(2-(((tert-butyldimethylsilyl)oxy)methyl)piperazin-1-yl)-5,6,7,8-tetrahydropyrido[3,4-d]pyrimidin-2-yl)oxy)-N,N-dimethylethanamine: To a mixture of (1-(7-(3-(benzyloxy) naphthalen-1-yl)-2-(2-(dimethyl amino)ethoxy)-5,6,7,8-tetrahydropyrido[3,4-d]pyrimidin-4-yl)piperazin-2-yl) methanol (160 mg, 281 µmol, 1.00 eq) in THF (5.00 mL) was added NaH (94.0 mg, 2.35 mmol, 60.0% purity, 8.00 eq) at 0° C. After stirring for 30 minutes, tert-butyldimethylsilyl chloride (133 mg, 881 µmol, 108 µL, 3.00 eq) was added dropwise. The mixture was stirred at 25° C. for 6 hours under a nitrogen atmosphere. The reaction mixture was concentrated under reduced pressure to give 2-((7-(3-(benzyloxy)naphthalen-1-yl)-4-(2-(((tert-butyldimethylsilyl)oxy)methyl)piperazin-1-yl)-5,6,7,8-tetrahydropyrido[3,4-d]pyrimidin-2-yl)oxy)-N,N-dimethylethanamine (133 mg, 165 µmol, 56.1% yield, 84.6% purity) as a slight yellow solid, which was used directly in the next step without further purification. ESI MS m/z 683.2 [M+H]⁺.

Step H: 1-(4-(7-(3-(benzyloxy) naphthalene-1-yl)-2-(2-(dimethylamino)ethoxy)-5,6,7,8-tetrahydropyrido[3,4-d]pyrimidin-4-yl)-3-(((tert-butyldimethylsilyl)oxy)methyl)piperazin-1-yl)prop-2-en-1-one: 1 To a solution of 2-((7-(3-(benzyloxy)naphthalen-1-yl)-4-(2-(((tert-butyl dimethylsilyl)oxy)methyl)piperazin-1-yl)-5,6,7,8-tetrahydropyrido[3,4-d]pyrimidin-2-yl)oxy)-N,N-dimethylethanamine (133 mg, 165 µmol, 1.00 eq) and TEA (39.4 mg, 389 µmol, 54.0 µL, 2.00 eq) in DCM (3.00 mL) was added prop-2-enoyl prop-2-enoate (31.9 mg, 253 µmol, 1.30 eq) at −40° C. After stirring at −40° C. for 2 hours, the reaction mixture was quenched with MeOH (1 M) and concentrated under reduced pressure to give 1-(4-(7-(3-(benzyloxy) naphthalene-1-yl)-2-(2-(dimethylamino)ethoxy)-5,6,7,8-tetrahydropyrido[3,4-d]pyrimidin-4-yl)-3-(((tert-butyldimethylsilyl)oxy)methyl)piperazin-1-yl)prop-2-en-1-one (140 mg, crude) as a yellow solid. ESI MS m/z 737.2 [M+H]⁺.

Step I: 1-(4-(2-(2-(dimethylamino)ethoxy)-7-(3-hydroxynaphthalen-1-yl)-5,6,7,8-tetrahydropyrido[3,4-d]pyrimidin-4-yl)-3-(hydroxymethyl)piperazin-1-yl)prop-2-en-1-one: To a solution of 1-(4-(7-(3-(benzyloxy)naphthalen-1-yl)-2-(2-(dimethylamino)ethoxy)-5,6,7,8-tetrahydropyrido[3,4-d]pyrimidin-4-yl)-3-(((tert-butyldimethylsilyl)oxy)methyl)piperazin-1-yl)prop-2-en-1-one (140 mg, crude) in DCM (5.00 mL) was added BBr₃ (476 mg, 1.90 mmol, 183 µL) at −40° C. After stirring for 2 hours at −40° C. under a nitrogen atmosphere, the mixture was concentrated under reduced pressure to dryness. Water (0.5 mL) and MeOH (2.5 mL) were added and the resulting solution was purified by preparative HPLC (column: Waters Xbridge 150*25 5 u; mobile phase: [water (10 mM NH₄HCO₃)-ACN]; B %: 27%-57%, 11 min). The desired fractions were collected and lyophilized to give 1-(4-(2-(2-(dimethylamino)ethoxy)-7-(3-hydroxynaphthalen-1-yl)-5,6,7,8-tetrahydropyrido[3,4-d]pyrimidin-4-yl)-3-(hydroxymethyl)piperazin-1-yl)prop-2-en-1-one (4.32 mg, 7.94 µmol, 4.18% yield, 97.9% purity) as a white solid. ESI MS m/z 533.4 [M+H]⁺.

Example 54

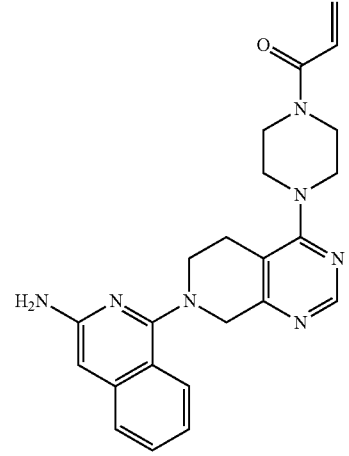 [SMILES: C=CC(=O)N1CCN(c2ncnc3c2CCN(c2nc(N)cc4ccccc24)C3)CC1]

1-[4-[7-(3-amino-1-isoquinolyl)-6,8-dihydro-5H-pyrido[3,4-d]pyrimidin-4-yl]piperazin-1-yl]prop-2-en-1-one Step A: tert-butyl 4-hydroxy-6,8-dihydro-5H-pyrido[3,4-d]pyrimidine-7-carboxylate To a solution of Na (4.24 g, 184 mmol, 4.37 mL, 2.50 eq) in EtOH (400 mL) was added 1-tert-butyl 4-ethyl 3-oxopiperidine-1,4-dicarboxylate (20.0 g, 73.7 mmol, 1.00 eq) and acetic acid methanimidamide (11.5 g, 111 mmol, 1.50 eq)

under N₂. The mixture was stirred at 70° C. for 5 hours. The reaction mixture was adjusted to pH 7 with HCl (1N), extracted with DCM (3×200 mL), washed with brine (1×400 mL), dried over Na₂SO₄, filtered and concentrated under vacuum to give tert-butyl 4-hydroxy-6,8-dihydro-5H-pyrido[3,4-d]pyrimidine-7-carboxylate (16.0 g, 63.7 mmol, 86.4% yield) as a brown solid. ESI MS m/z 274.0 [M+H]⁺.

Step B: tert-butyl 4-(4-benzyloxycarbonylpiperazin-1-yl)-6,8-dihydro-5H-pyrido[3,4-d]pyrimidine-7-carboxylate To a solution of tert-butyl 4-hydroxy-6,8-dihydro-5H-pyrido[3,4-d] pyrimidine-7-carboxylate (16.0 g, 63.7 mmol, 1.00 eq) in DMF (4.00 mL) was added DBU (29.1 g, 191 mmol, 28.8 mL, 3.00 eq) and benzotriazol-1-yl-oxytripyrrolidinophosphonium hexafluorophosphate (PYBOP) (39.8 g, 76.4 mmol, 1.20 eq). The mixture was stirred at 25° C. for 1 hour. Benzyl piperazine-1-carboxylate (21.0 g, 95.5 mmol, 18.5 mL, 1.50 eq) was added and the reaction mixture was stirred at 25° C. for 16 hours. The mixture was diluted with ethyl acetate (500 mL) and washed with water (3×400 mL), dried over Na₂SO₄, filtered and concentrated under vacuum. The residue was purified by column chromatography (SiO₂, diethyl ether/ethyl acetate=1:1) to give tert-butyl 4-(4-benzyloxycarbonylpiperazin-1-yl)-6,8-dihydro-5H-pyrido[3,4-d]pyrimidine-7-carboxylate (2.00 g, 4.41 mmol, 6.93% yield) as a yellow oil. ESI MS m/z 454.3 [M+H]⁺.

Step C: A mixture of tert-butyl 4-(4-benzyloxycarbonylpiperazin-1-yl)-6,8-dihydro-5H-pyrido[3,4-d]pyrimidine-7-carboxylate (1.20 g, 2.65 mmol, 1.00 eq) and TFA (4.53 g, 39.7 mmol, 2.94 mL, 15.0 eq) in DCM (2.00 mL) was stirred at 25° C. for 1 hour. The mixture was concentrated under vacuum. The concentrated material was adjusted to pH 8 with saturated aq. NaHCO₃, then extracted with ethyl acetate (3×30.0 mL), washed with brine (1×100 mL), dried over Na₂SO₄, filtered and concentrated under vacuum to give benzyl 4-(5,6,7,8-tetrahydropyrido[3,4-d]pyrimidin-4-yl)piperazine-1-carboxylate (800 mg, 2.26 mmol, 85.4% yield) as a yellow oil. ESI MS m/z 354.3 [M+H]⁺.

Step D: benzyl 4-[7-[3-(tert-butoxycarbonylamino)-1-isoquinolyl]-6,8-dihydro-5H-pyrido[3,4-d]pyrimidin-4-yl]piperazine-1-carboxylate A mixture of tert-butyl N-(1-bromo-3-isoquinolyl)carbamate (330 mg, 1.02 mmol, 1.00 eq), DIEA (264 mg, 2.04 mmol, 357 µL, 2.00 eq) and benzyl 4-(5,6,7,8-tetrahydropyrido[3,4-d]pyrimidin-4-yl)piperazine-1-carboxylate (541 mg, 1.53 mmol, 1.50 eq) in DMSO (3.00 mL) was stirred at 80° C. for 10 hours. The mixture was diluted with water (5.00 mL) and extracted with ethyl acetate (3×20 mL). The combined extracts were dried over sodium sulfate, filtered and concentrated under vacuum. The residue was purified by reverse-phase column (TFA, 0.1%) to give benzyl 4-[7-[3-(tert-butoxycarbonylamino)-1-isoquinolyl]-6,8-dihydro-5H-pyrido[3,4-d]pyrimidin-4-yl]piperazine-1-carboxylate (400 mg, 665 µmol, 65.2% yield) as a yellow solid. ESI MS m/z 596.3 [M+H]⁺.

Step E: tert-butyl N-[1-(4-piperazin-1-yl-6,8-dihydro-5H-pyrido[3,4-d]pyrimidin-7-yl)-3-isoquinolyl]carbamate A mixture of benzyl 4-[7-[3-(tert-butoxycarbonylamino)-1-isoquinolyl]-6,8-dihydro-5H-pyrido[3,4-d]pyrimidin-4-yl]piperazine-1-carboxylate (240 mg, 403 µmol, 1.00 eq), KOH (36.2 mg, 645 µmol, 1.60 eq) in H₂O (2.40 mL) and n-butyl alcohol (2.40 mL) was stirred at 100° C. for 12 hours. The mixture was diluted with ethyl acetate (3×5.00 mL), washed with brine (1×10.0 mL), dried over Na₂SO₄, filtered and concentrated under vacuum to give tert-butyl N-[1-(4-piperazin-1-yl-6,8-dihydro-5H-pyrido[3,4-d]pyrimidin-7-yl)-3-isoquinolyl]carbamate (150 mg, 325 µmol, 80.7% yield) as a yellow oil. ESI MS m/z 462.3 [M+H]⁺.

Step F: 1-(4-piperazin-1-yl-6,8-dihydro-5H-pyrido[3,4-d]pyrimidin-7-yl)isoquinolin-3-amine trifluoroacetate A solution of tert-butyl N-[1-(4-piperazin-1-yl-6,8-dihydro-5H-pyrido[3,4-d]pyrimidin-7-yl)-3-isoquinolyl]carbamate (150 mg, 325 µmol, 1.00 eq) and TFA (556 mg, 4.87 mmol, 361 µL, 15.0 eq) in DCM (360 µL) was stirred at 25° C. for 1 hours. The mixture was concentrated under vacuum to give 1-(4-piperazin-1-yl-6,8-dihydro-5H-pyrido[3,4-d]pyrimidin-7-yl)isoquinolin-3-amine trifluoroacetate (154.52 mg, crude) as a yellow solid which was used into next step without further purification.

Step G: 1-[4-[7-(3-amino-1-isoquinolyl)-6,8-dihydro-5H-pyrido[3,4-d]pyrimidin-4-yl]piperazin-1-yl]prop-2-en-1-one To a solution of 1-(4-piperazin-1-yl-6,8-dihydro-5H-pyrido[3,4-d] pyrimidin-7-yl)isoquinolin-3-amine trifluoroacetate (150 mg, crude) and Et₃N (319 mg, 3.15 mmol, 437 µL) in DCM (2.00 mL) was added prop-2-enoyl prop-2-enoate (31.8 mg, 252 µmol) at −40° C., then stirred at −40° C. for 0.5 h. The mixture was quenched by adding MeOH (20.22 mg, 630.96 µmol) and concentrated under vacuum. The residue was purified by preparative HPLC (Phenomenex Gemini 150*25 mm*, 10µ; mobile phase: [water (0.05% ammonia hydroxide v/v)-ACN]; B %: 26%-56%, 10 min) to give 1-[4-[7-(3-amino-1-isoquinolyl)-6,8-dihydro-5H-pyrido[3,4-d]pyrimidin-4-yl]piperazin-1-yl]prop-2-en-1-one (35.4 mg, 82.5 µmol, 26.2% yield, 96.8% purity) as a yellow solid. ESI MS m/z 416.3 [M+H]⁺.

Example 55

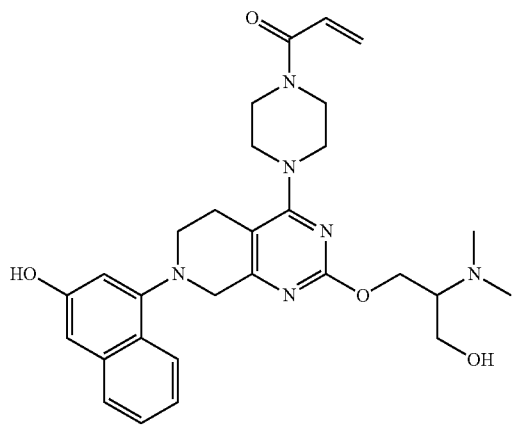 [SMILES: C=CC(=O)N1CCN(c2nc(OCC(CO)N(C)C)nc3c2CCN(c2cc(O)cc4ccccc24)C3)CC1]

337

1-(4-(2-(2-(dimethylamino)-3-hydroxypropoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 2-(dimethylamino)propane-1,3-diol in place of (S)-1-(dimethylamino)propan-2-ol in Step B. ES+APCI MS m/z 533.3 [M+H]+.

Example 56

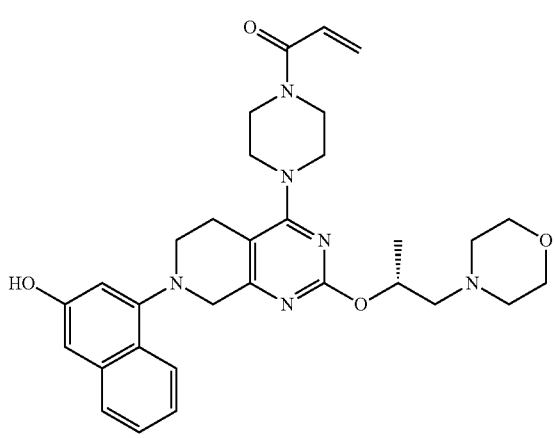 [SMILES: C=CC(=O)N1CCN(c2nc(O[C@H](C)CN3CCOCC3)nc3c2CCN(c2cc(O)cc4ccccc24)C3)CC1]

(R)-1-(4-(7-(3-hydroxynaphthalen-1-yl)-2-((1-morpholinopropan-2-yl)oxy)-5,6,7,8-tetrahydropyrido[3,4-d]pyrimidin-4-yl)piperazin-1-yl)prop-2-en-1-one Synthesized according to the method of Example 8, using (R)-1-morpholinopropan-2-ol in place of (S)-1-(dimethylamino)propan-2-ol in Step B. ES+APCI MS m/z 559.3 [M+H]+.

Example 57

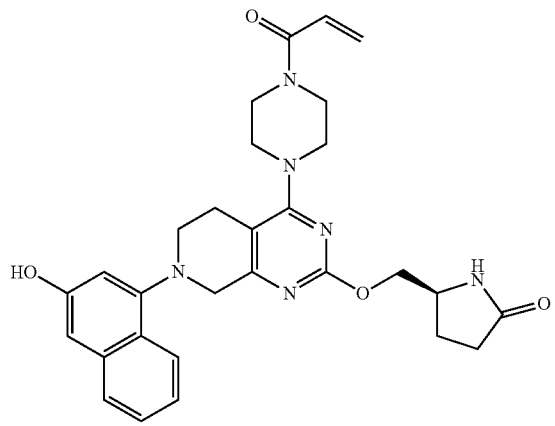 [SMILES: C=CC(=O)N1CCN(c2nc(OC[C@@H]3CCC(=O)N3)nc3c2CCN(c2cc(O)cc4ccccc24)C3)CC1]

338

(S)-5-(((4-(4-acryloylpiperazin-1-yl)-7-(3-hydroxynaphthalen-1-yl)-5,6,7,8-tetrahydropyrido[3,4-d]pyrimidin-2-yl)oxy)methyl)pyrrolidin-2-one Synthesized according to the method of Example 8, using (S)-5-(hydroxymethyl)pyrrolidin-2-one in place of (S)-1-(dimethylamino)propan-2-ol in Step B. ES+APCI MS m/z 529.3 [M+H]+.

Example 58

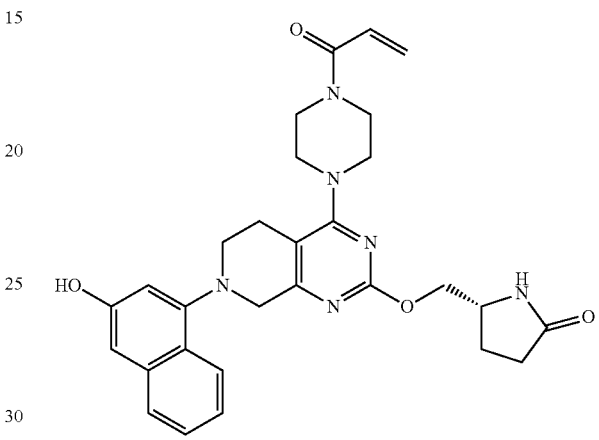

(R)-5-(((4-(4-acryloylpiperazin-1-yl)-7-(3-hydroxynaphthalen-1-yl)-5,6,7,8-tetrahydropyrido[3,4-d]pyrimidin-2-yl)oxy)methyl)pyrrolidin-2-one Synthesized according to the method of Example 8, using (R)-5-(hydroxymethyl)pyrrolidin-2-one in place of (S)-1-(dimethylamino)propan-2-ol in Step B. ES+APCI MS m/z 529.2 [M+H]+.

Example 59

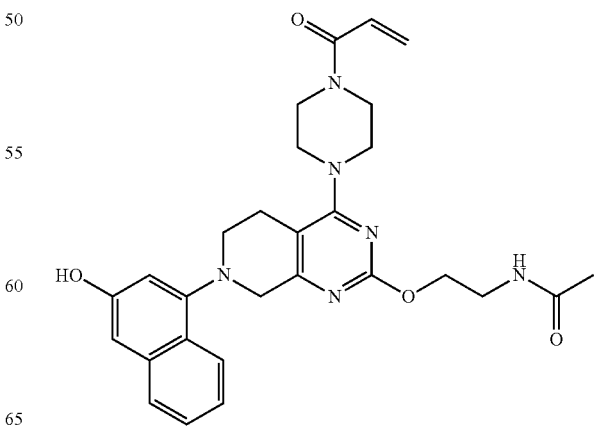

N-(2-((4-(4-acryloylpiperazin-1-yl)-7-(3-hy-droxynaphthalen-1-yl)-5,6,7,8-tetrahydropyrido[3,4-d]pyrimidin-2-yl)oxy)ethyl)acetamide Synthesized according to the method of Example 8, using N-(2-hydroxyethyl)acetamide in place of (S)-1-(dimethylamino)propan-2-ol in Step B. ES+APCI MS m/z 517.3 [M+H]+.

Example 60

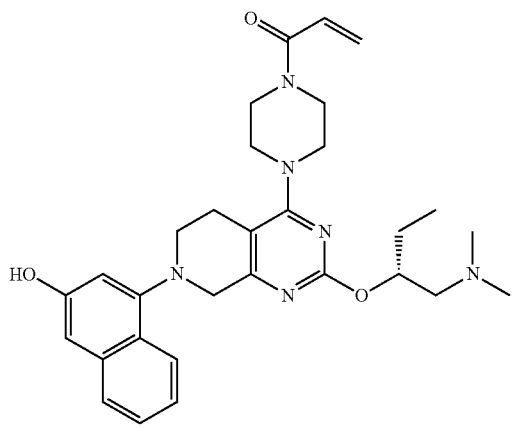

(R)-1-(4-(2-((1-(dimethylamino)butan-2-yl)oxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using (R)-1-(dimethylamino)butan-2-ol in place of (S)-1-(dimethylamino)propan-2-ol in Step B. ES+APCI MS m/z 545.3 [M+H]+.

Example 61

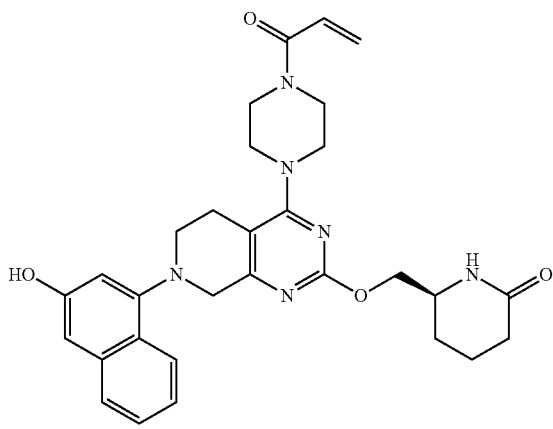 [SMILES: C=CC(=O)N1CCN(c2nc(OC[C@@H]3CCCC(=O)N3)nc3c2CCN(c2cc(O)cc4ccccc24)C3)CC1]

(S)-6-(((4-(4-acryloylpiperazin-1-yl)-7-(3-hydroxynaphthalen-1-yl)-5,6,7,8-tetrahydropyrido[3,4-d]pyrimidin-2-yl)oxy)methyl)piperidin-2-one Synthesized according to the method of Example 8, using 6-(hydroxymethyl)piperidin-2-one in place of (S)-1-(dimethylamino)propan-2-ol in Step B and the product was separated by chiral chromatography. Peak 2 was given the (S) stereochemistry and this was not confirmed. ES+APCI MS m/z 543.3 [M+H]+.

Example 62

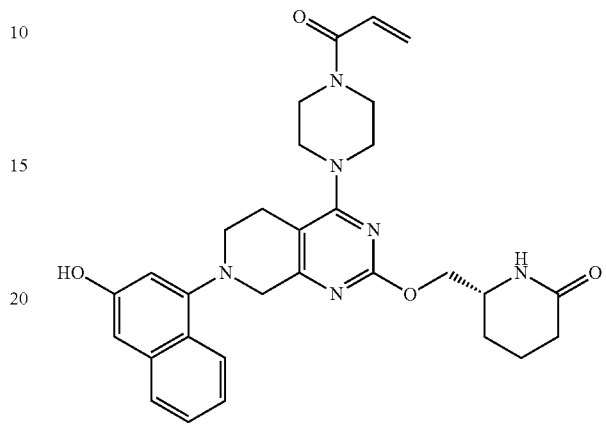

(R)-6-(((4-(4-acryloylpiperazin-1-yl)-7-(3-hydroxynaphthalen-1-yl)-5,6,7,8-tetrahydropyrido[3,4-d]pyrimidin-2-yl)oxy)methyl)piperidin-2-one Synthesized according to the method of Example 8, using 6-(hydroxymethyl)piperidin-2-one in place of (S)-1-(dimethylamino)propan-2-ol in Step B and separated by chiral chromatography. Peak 1 was assigned the (R) stereochemistry but this stereochemistry was not confirmed. ES+APCI MS m/z 543.2 [M+H]+.

Example 63

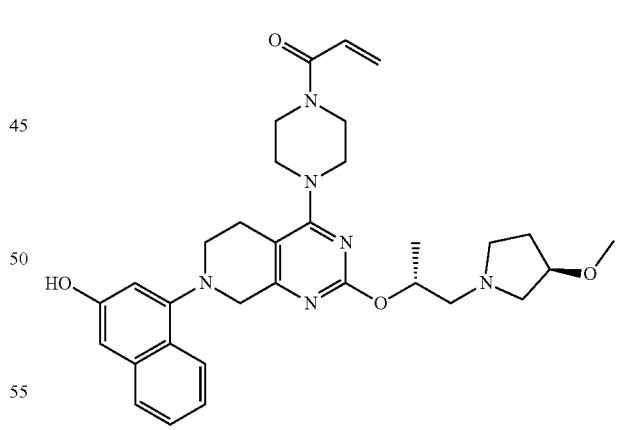

1-(4-(7-(3-hydroxynaphthalen-1-yl)-2-(((R)-1-((R)-3-methoxypyrrolidin-1-yl)propan-2-yl)oxy)-5,6,7,8-tetrahydropyrido[3,4-d]pyrimidin-4-yl)piperazin-1-yl)prop-2-en-1-one Synthesized according to the method of Example 8, using (R)-1-((R)-3-methoxypyrrolidin-1-yl)propan-2-ol in place of (S)-1-(dimethylamino)propan-2-ol in Step B. ES+APCI MS m/z 573.3 [M+H]+.

Example 64

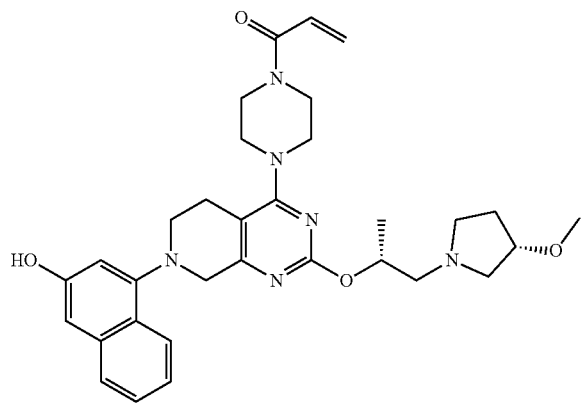 [SMILES: C=CC(=O)N1CCN(c2nc(O[C@H](C)CN3CC[C@H](OC)C3)nc3c2CCN(c2cc(O)cc4ccccc24)C3)CC1]

1-(4-(7-(3-hydroxynaphthalen-1-yl)-2-(((R)-1-((S)-3-methoxypyrrolidin-1-yl)propan-2-yl)oxy)-5,6,7,8-tetrahydropyrido[3,4-d]pyrimidin-4-yl)piperazin-1-yl)prop-2-en-1-one Synthesized according to the method of Example 8, using (R)-1-((S)-3-methoxypyrrolidin-1-yl)propan-2-ol in place of (S)-1-(dimethylamino)propan-2-ol in Step B. ES+APCI MS m/z 573.3 [M+H]+.

Example 66

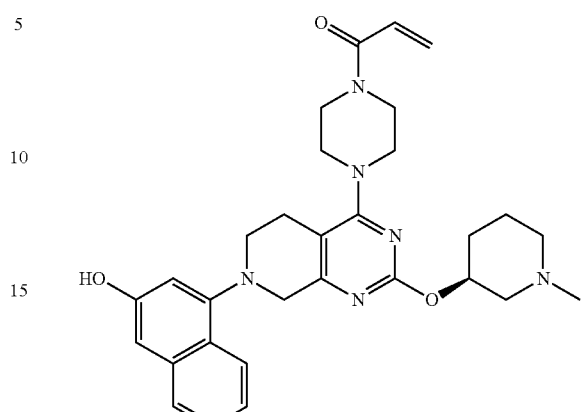

(S)-1-(4-(7-(3-hydroxynaphthalen-1-yl)-2-((1-methylpiperidin-3-yl)oxy)-5,6,7,8-tetrahydropyrido[3,4-d]pyrimidin-4-yl)piperazin-1-yl)prop-2-en-1-one Synthesized according to the method of Example 8, using (S)-1-methylpiperidin-3-ol in place of (S)-1-(dimethylamino)propan-2-ol in Step B. ES+APCI MS m/z 529.3 [M+H]+.

Example 65

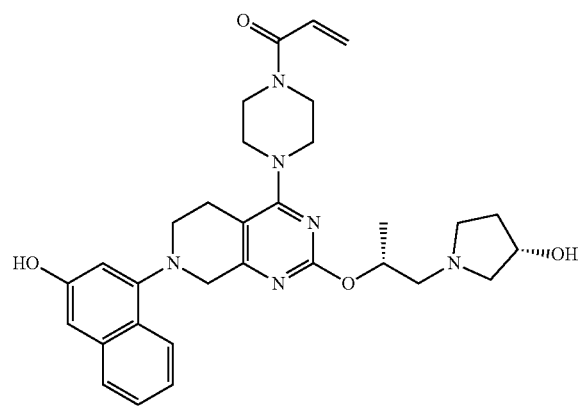 [SMILES: C=CC(=O)N1CCN(c2nc(O[C@H](C)CN3CC[C@H](O)C3)nc3c2CCN(c2cc(O)cc4ccccc24)C3)CC1]

1-(4-(7-(3-hydroxynaphthalen-1-yl)-2-(((R)-1-((S)-3-hydroxypyrrolidin-1-yl)propan-2-yl)oxy)-5,6,7,8-tetrahydropyrido[3,4-d]pyrimidin-4-yl)piperazin-1-yl)prop-2-en-1-one Synthesized according to the method of Example 8, using (R)-1-((S)-3-((tert-butyldimethylsilyl)oxy)pyrrolidin-1-yl)propan-2-ol in place of (S)-1-(dimethylamino)propan-2-ol in Step B. ES+APCI MS m/z 559.3 [M+H]+.

Example 67

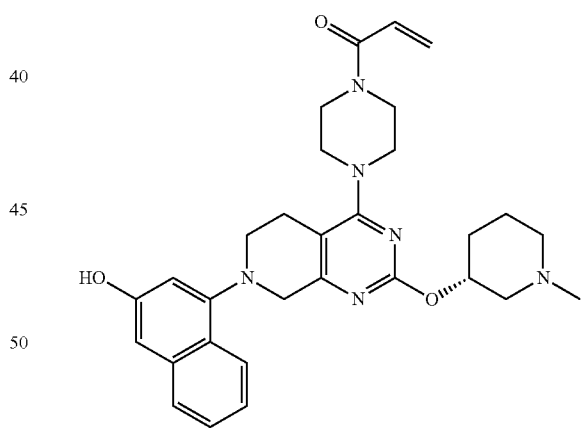

(R)-1-(4-(7-(3-hydroxynaphthalen-1-yl)-2-((1-methylpiperidin-3-yl)oxy)-5,6,7,8-tetrahydropyrido[3,4-d]pyrimidin-4-yl)piperazin-1-yl)prop-2-en-1-one Synthesized according to the method of Example 8, using (R)-1-methylpiperidin-3-ol in place of (S)-1-(dimethylamino)propan-2-ol in Step B. ES+APCI MS m/z 529.3 [M+H]+.

Example 68

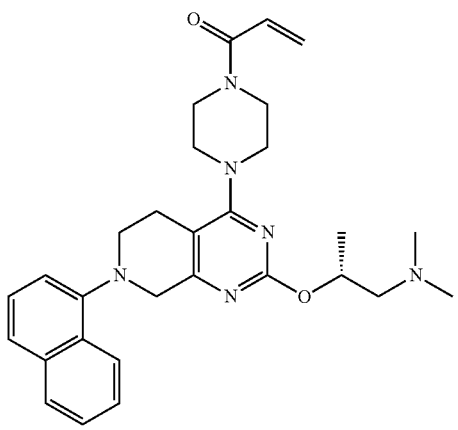 [SMILES: C=CC(=O)N1CCN(c2nc(O[C@H](C)CN(C)C)nc3c2CCN(c2cccc4ccccc24)C3)CC1]

(R)-1-(4-(2-((1-(dimethylamino)propan-2-yl)oxy)-7-(naphthalen-1-yl)-5,6,7,8-tetrahydropyrido[3,4-d]pyrimidin-4-yl)piperazin-1-yl)prop-2-en-1-one Synthesized according to the method of Example 8, using 1-iodonaphthalene in place of (3-(methoxymethoxy)naphthalen-1-yl trifluoromethanesulfonate in Step D. ES+APCI MS m/z 501.3 [M+H]+.

Example 69

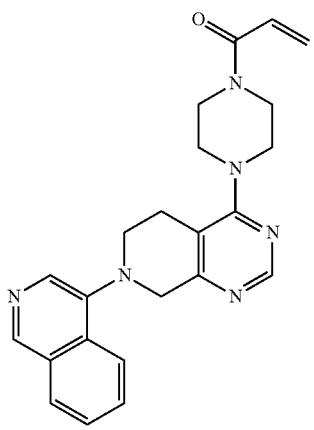 [SMILES: C=CC(=O)N1CCN(c2ncnc3c2CCN(c2cncc4ccccc24)C3)CC1]

1-(4-(7-(isoquinolin-4-yl)-5,6,7,8-tetrahydropyrido[3,4-d]pyrimidin-4-yl)piperazin-1-yl)prop-2-en-1-one Synthesized according to the method of Example 1, using 4-bromoisoquinoline in place of 1-bromo-3-(methoxymethoxy)naphthalene in Step C. ES+APCI MS m/z 401.2 [M+H]+.

Example 70

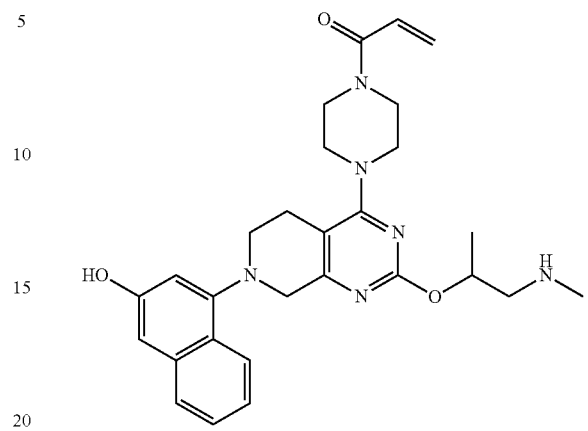

1-(4-(7-(3-hydroxynaphthalen-1-yl)-2-((1-(methylamino)propan-2-yl)oxy)-5,6,7,8-tetrahydropyrido[3,4-d]pyrimidin-4-yl)piperazin-1-yl)prop-2-en-1-one Synthesized according to the method of Example 8, using 1-(methylamino)propan-2-ol in place of (S)-1-(dimethylamino)propan-2-ol in Step B. ES+APCI MS m/z 503.3 [M+H]+.

Example 71

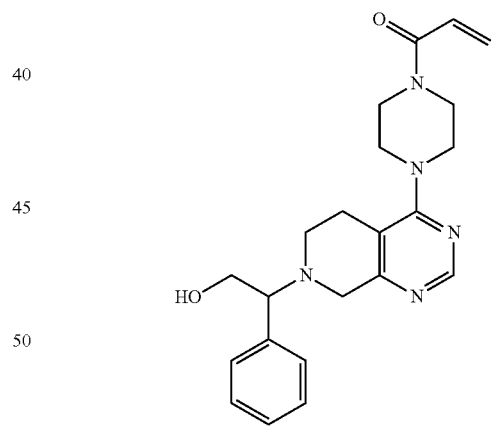

1-(4-(7-(2-hydroxy-1-phenylethyl)-5,6,7,8-tetrahydropyrido[3,4-d]pyrimidin-4-yl)piperazin-1-yl)prop-2-en-1-one Synthesized according to the method of Example 1, using 2-((tert-butyldimethylsilyl)oxy)-1-phenylethyl methanesulfonate in place of 1-bromo-3-(methoxymethoxy)naphthalene in Step C. ES+APCI MS m/z 394.2 [M+H]+.

Example 72

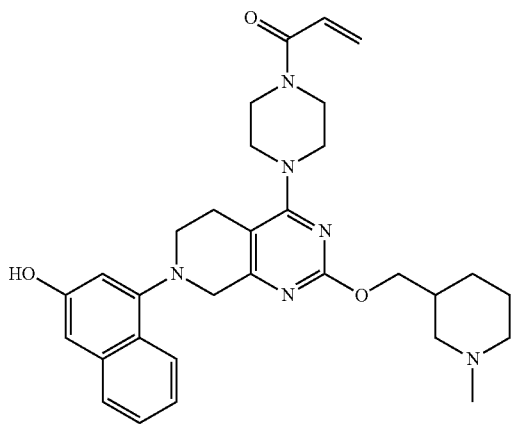 [SMILES: C=CC(=O)N1CCN(c2nc(OCC3CCCN(C)C3)nc3c2CCN(c2cc(O)cc4ccccc24)C3)CC1]

1-(4-(7-(3-hydroxynaphthalen-1-yl)-2-(1-methylpiperidin-3-yl)methoxy)-5,6,7,8-tetrahydropyrido[3,4-d]pyrimidin-4-yl)piperazin-1-yl)prop-2-en-1-one Synthesized according to the method of Example 8, using (1-methylpiperidin-3-yl)methanol in place of (S)-1-(dimethylamino)propan-2-ol in Step B. ES+APCI MS m/z 543.3 [M+H]$^+$.

Example 73

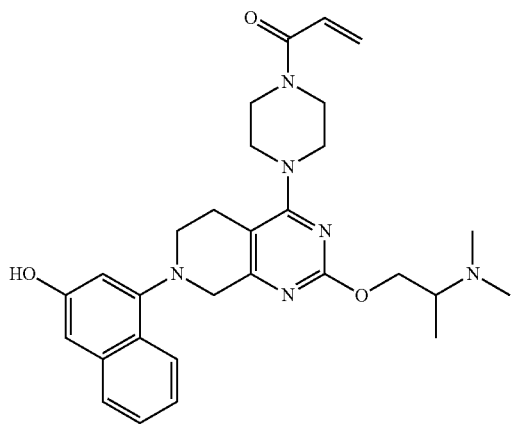

1-(4-(2-(2-(dimethylamino)propoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 2-(dimethylamino)propan-1-ol in place of (S)-1-(dimethylamino)propan-2-ol in Step B. ES+APCI MS m/z 517.2 [M+H]$^+$.

Example 74

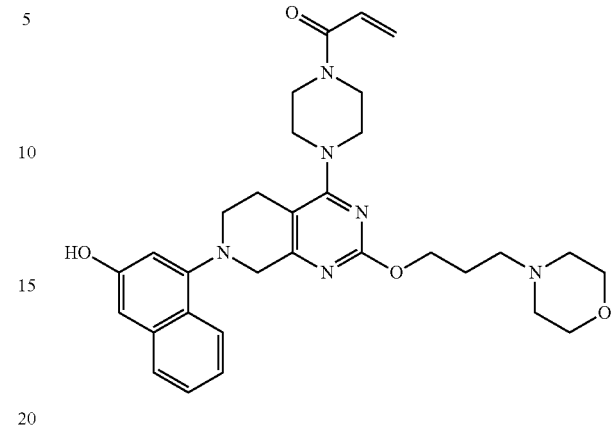

1-(4-(7-(3-hydroxynaphthalen-1-yl)-2-(3-morpholinopropoxy)-5,6,7,8-tetrahydropyrido[3,4-d]pyrimidin-4-yl)piperazin-1-yl)prop-2-en-1-one Synthesized according to the method of Example 8, using 3-morpholinopropan-1-ol in place of (S)-1-(dimethylamino)propan-2-ol in Step B. ES+APCI MS m/z 559.3 [M+H]$^+$.

Example 75

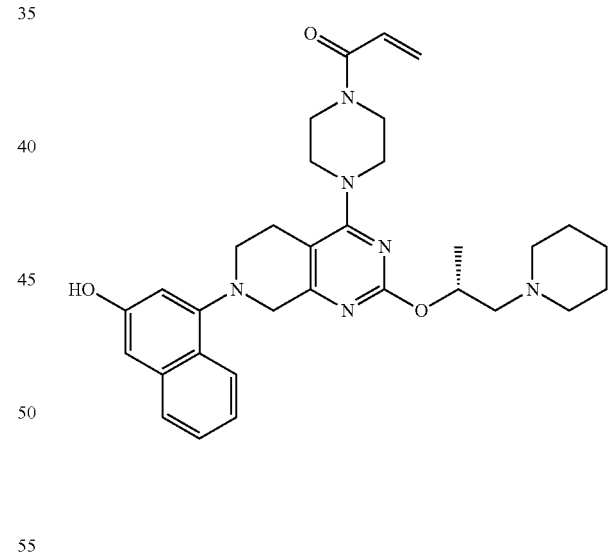

(R)-1-(4-(7-(3-hydroxynaphthalen-1-yl)-2-((1-(piperidin-1-yl)propan-2-yl)oxy)-5,6,7,8-tetrahydropyrido[3,4-d]pyrimidin-4-yl)piperazin-1-yl)prop-2-en-1-one Synthesized according to the method of Example 8, using (R)-1-(piperidin-1-yl)propan-2-ol in place of (S)-1-(dimethylamino)propan-2-ol in Step B. ES+APCI MS m/z 557.3 [M+H]$^+$.

Example 76

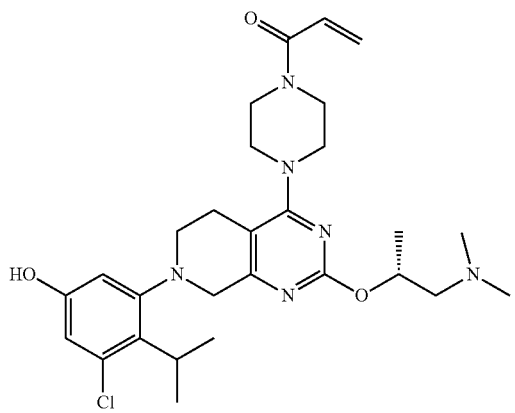 [SMILES: C=CC(=O)N1CCN(c2nc(O[C@H](C)CN(C)C)nc3c2CCN(c2cc(O)cc(Cl)c2C(C)C)C3)CC1]

(R)-1-(4-(7-(3-chloro-5-hydroxy-2-isopropylphenyl)-2-((1-(dimethylamino)propan-2-yl)oxy)-5,6,7,8-tetrahydropyrido[3,4-d]pyrimidin-4-yl)piperazin-1-yl)prop-2-en-1-one Synthesized according to the method of Example 8, using 1-bromo-3-chloro-2-isopropyl-5-(methoxymethoxy)benzene in place of (3-(methoxymethoxy)naphthalen-1-yl trifluoromethanesulfonate in Step D. ES+APCI MS m/z 545.3 [M+H]$^+$.

Example 77

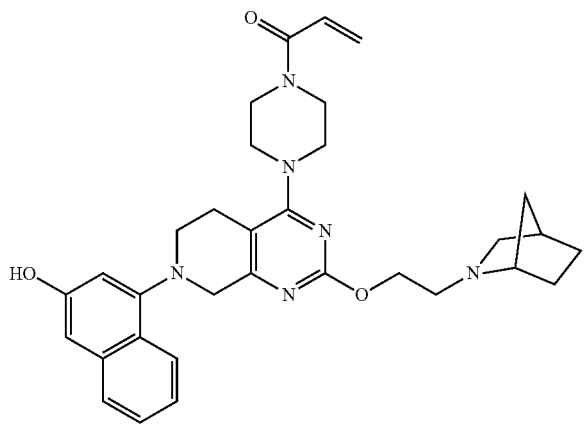 [SMILES: C=CC(=O)N1CCN(c2nc(OCCN3CC4CCC3C4)nc3c2CCN(c2cc(O)cc4ccccc24)C3)CC1]

1-(4-(2-(2-((1S,4R)-2-azabicyclo[2.2.1]heptan-2-yl)ethoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 2-((1S,4R)-2-azabicyclo[2.2.1]heptan-2-yl)ethan-1-ol in place of (S)-1-(dimethylamino)propan-2-ol in Step B. ES+APCI MS m/z 555.2 [M+H]$^+$.

Example 78

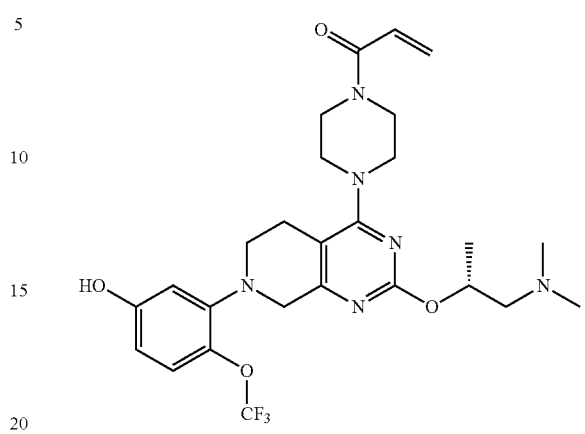

(R)-1-(4-(2-((1-(dimethylamino)propan-2-yl)oxy)-7-(5-hydroxy-2-(trifluoromethoxy)phenyl)-5,6,7,8-tetrahydropyrido[3,4-d]pyrimidin-4-yl)piperazin-1-yl)prop-2-en-1-one Synthesized according to the method of Example 8, using 2-bromo-4-(methoxymethoxy)-1-(trifluoromethoxy)benzene in place of (3-(methoxymethoxy)naphthalen-1-yl trifluoromethanesulfonate in Step D. ES+APCI MS m/z 551.2 [M+H]$^+$.

Example 79

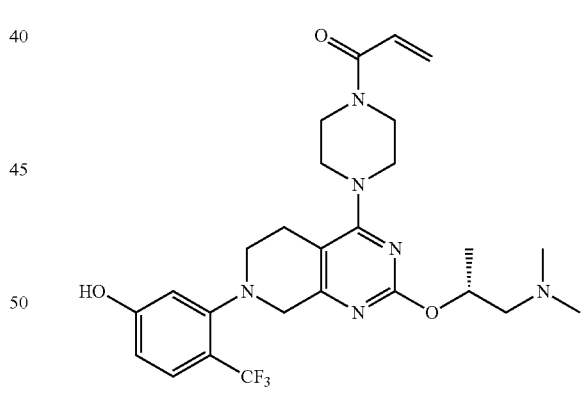

(R)-1-(4-(2-((1-(dimethylamino)propan-2-yl)oxy)-7-(5-hydroxy-2-(trifluoromethyl)phenyl)-5,6,7,8-tetrahydropyrido[3,4-d]pyrimidin-4-yl)piperazin-1-yl)prop-2-en-1-one Synthesized according to the method of Example 8, using 2-bromo-4-(methoxymethoxy)-1-(trifluoromethyl)benzene in place of (3-(methoxymethoxy)naphthalen-1-yl trifluoromethanesulfonate in Step D. ES+APCI MS m/z 535.2 [M+H]$^+$.

Example 80

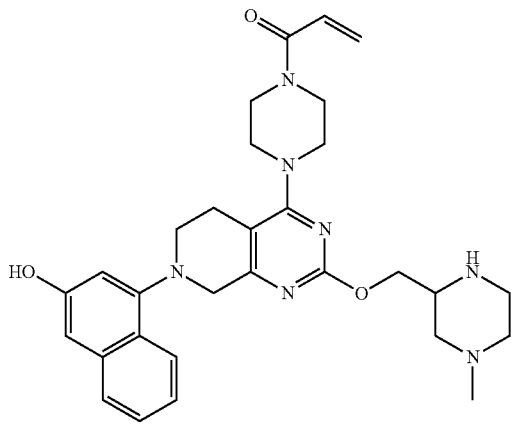 [SMILES: C=CC(=O)N1CCN(c2nc(OCC3CN(C)CCN3)nc3c2CCN(c2cc(O)cc4ccccc24)C3)CC1]

1-(4-(7-(3-hydroxynaphthalen-1-yl)-2-((4-methyl-piperazin-2-yl)methoxy)-5,6,7,8-tetrahydropyrido[3,4-d]pyrimidin-4-yl)piperazin-1-yl)prop-2-en-1-one Synthesized according to the method of Example 8, using (4-methylpiperazin-2-yl)methanol in place of (S)-1-(dimethylamino)propan-2-ol in Step B. ES+APCI MS m/z 544.3 [M+H]⁺.

Example 81

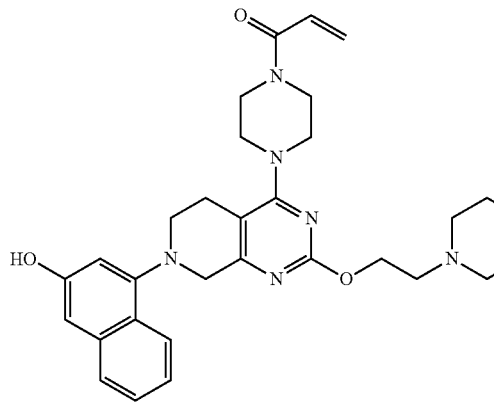

1-(2-((4-(4-acryloylpiperazin-1-yl)-7-(3-hydroxynaphthalen-1-yl)-5,6,7,8-tetrahydropyrido[3,4-d]pyrimidin-2-yl)oxy)ethyl)piperidine-4-carbonitrile Synthesized according to the method of Example 8, using 1-(2-hydroxyethyl)piperidine-4-carbonitrile in place of (S)-1-(dimethylamino)propan-2-ol in Step B. ES+APCI MS m/z 568.2 [M+H]⁺.

Example 82

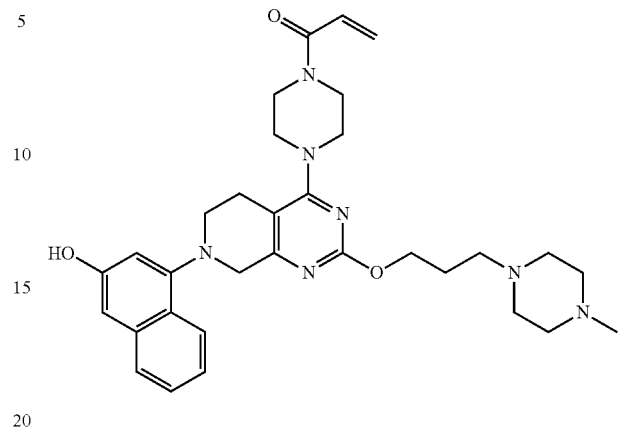

1-(4-(7-(3-hydroxynaphthalen-1-yl)-2-(3-(4-methyl-piperazin-1-yl)propoxy)-5,6,7,8-tetrahydropyrido[3,4-d]pyrimidin-4-yl)piperazin-1-yl)prop-2-en-1-one Synthesized according to the method of Example 8, 3-(4-methylpiperazin-1-yl)propan-1-ol in place of (S)-1-(dimethylamino)propan-2-ol in Step B. ES+APCI MS m/z 572.4 [M+H]⁺.

Example 83

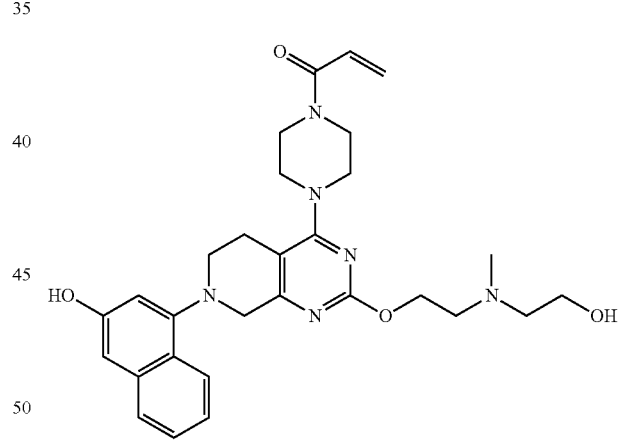

1-(4-(2-(2-((2-hydroxyethyl)(methyl)amino)ethoxy)-7-(3-hydroxynaphthalen-1-yl)-5,6,7,8-tetrahydro-pyrido[3,4-d]pyrimidin-4-yl)piperazin-1-yl)prop-2-en-1-one Synthesized according to the method of Example 8, using 2-((2-((tert-butyldimethylsilyl)oxy)ethyl)(methyl)amino)ethan-1-ol in place of (S)-1-(dimethylamino)propan-2-ol in Step B. ES+APCI MS m/z 533.3 [M+H]⁺.

Example 84

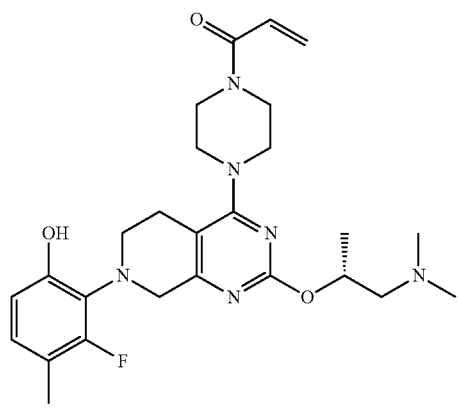 [SMILES: C=CC(=O)N1CCN(c2nc(O[C@H](C)CN(C)C)nc3c2CCN(c2c(O)ccc(C)c2F)C3)CC1]

(R)-1-(4-(2-((1-(dimethylamino)propan-2-yl)oxy)-7-(2-fluoro-6-hydroxy-3-methylphenyl)-5,6,7,8-tetrahydropyrido[3,4-d]pyrimidin-4-yl)piperazin-1-yl)prop-2-en-1-one Synthesized according to the method of Example 8, using 2-bromo-3-fluoro-1-(methoxymethoxy)-4-methylbenzene in place of (3-(methoxymethoxy)naphthalen-1-yl trifluoromethanesulfonate in Step D. ES+APCI MS m/z 499.3 [M+H]$^+$.

Example 85

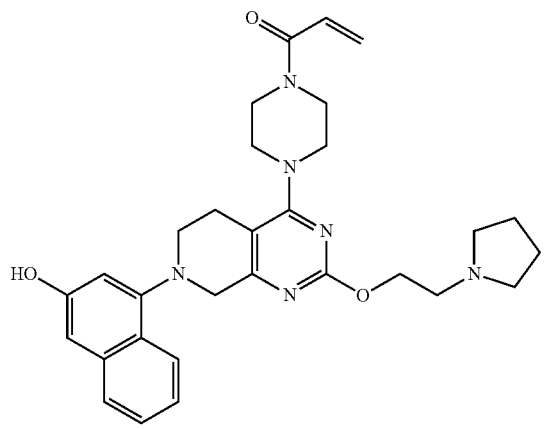 [SMILES: C=CC(=O)N1CCN(c2nc(OCCN3CCCC3)nc3c2CCN(c2cc(O)cc4ccccc24)C3)CC1]

1-(4-(7-(3-hydroxynaphthalen-1-yl)-2-(2-(pyrrolidin-1-yl)ethoxy)-5,6,7,8-tetrahydropyrido[3,4-d]pyrimidin-4-yl)piperazin-1-yl)prop-2-en-1-one Synthesized according to the method of Example 8, using 2-(pyrrolidin-1-yl)ethan-1-ol in place of (S)-1-(dimethylamino)propan-2-ol in Step B. ES+APCI MS m/z 529.2 [M+H]$^+$.

Example 86

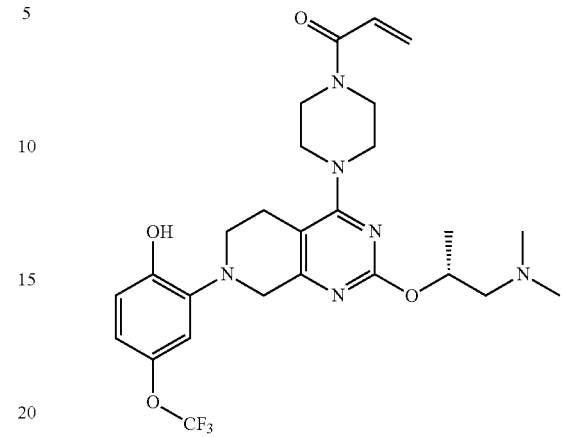

(R)-1-(4-(2-((1-(dimethylamino)propan-2-yl)oxy)-7-(2-hydroxy-5-(trifluoromethoxy)phenyl)-5,6,7,8-tetrahydropyrido[3,4-d]pyrimidin-4-yl)piperazin-1-yl)prop-2-en-1-one Synthesized according to the method of Example 8, using 2-bromo-1-(methoxymethoxy)-4-(trifluoromethoxy)benzene in place of (3-(methoxymethoxy)naphthalen-1-yl trifluoromethanesulfonate in Step D. ES+APCI MS m/z 551.2 [M+H]$^+$.

Example 87

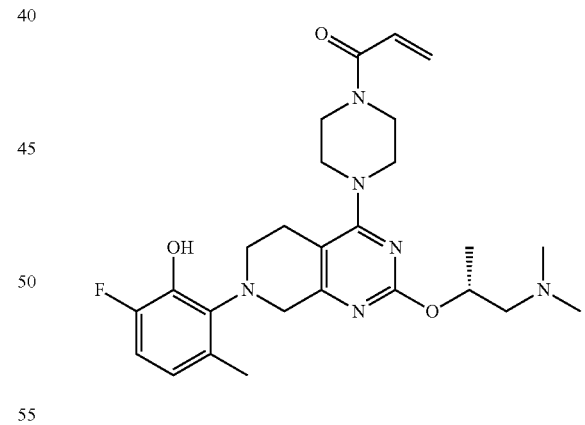

(R)-1-(4-(2-((1-(dimethylamino)propan-2-yl)oxy)-7-(3-fluoro-2-hydroxy-6-methylphenyl)-5,6,7,8-tetrahydropyrido[3,4-d]pyrimidin-4-yl)piperazin-1-yl)prop-2-en-1-one Synthesized according to the method of Example 8, using 2-bromo-4-fluoro-3-(methoxymethoxy)-1-methylbenzene in place of (3-(methoxymethoxy)naphthalen-1-yl trifluoromethanesulfonate in Step D. ES+APCI MS m/z 499.2 [M+H]$^+$.

Example 88

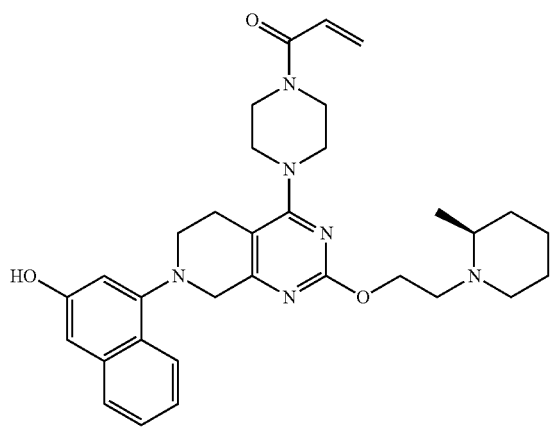 [SMILES: C=CC(=O)N1CCN(c2nc(OCCN3CCCC[C@@H]3C)nc3c2CCN(c2cc(O)cc4ccccc24)C3)CC1]

(S)-1-(4-(7-(3-hydroxynaphthalen-1-yl)-2-(2-(2-methylpiperidin-1-yl)ethoxy)-5,6,7,8-tetrahydropyrido[3,4-d]pyrimidin-4-yl)piperazin-1-yl)prop-2-en-1-one Synthesized according to the method of Example 8, using (S)-2-(2-methylpiperidin-1-yl)ethan-1-ol in place of (S)-1-(dimethylamino)propan-2-ol in Step B. ES+APCI MS m/z 557.2 [M+H]$^+$.

Example 89

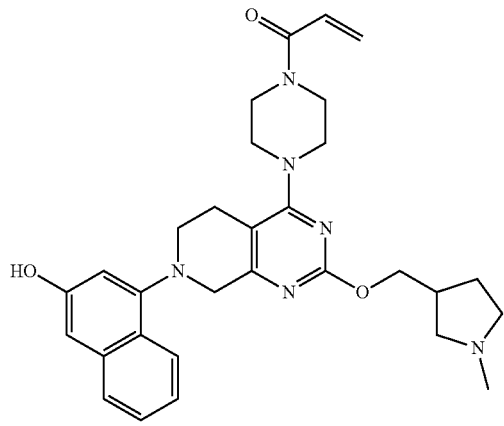 [SMILES: C=CC(=O)N1CCN(c2nc(OCC3CCN(C)C3)nc3c2CCN(c2cc(O)cc4ccccc24)C3)CC1]

1-(4-(7-(3-hydroxynaphthalen-1-yl)-2-((1-methylpyrrolidin-3-yl)methoxy)-5,6,7,8-tetrahydropyrido[3,4-d]pyrimidin-4-yl)piperazin-1-yl)prop-2-en-1-one Synthesized according to the method of Example 8, using (1-methylpyrrolidin-3-yl)methanol in place of (S)-1-(dimethylamino)propan-2-ol in Step B. ES+APCI MS m/z 529.3 [M+H]$^+$.

Example 90

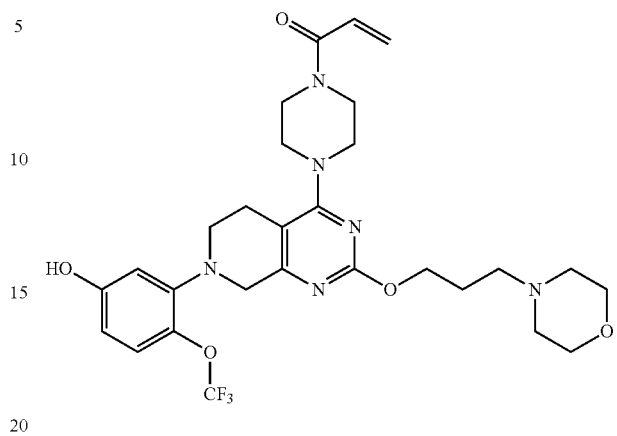

1-(4-(7-(5-hydroxy-2-(trifluoromethoxy)phenyl)-2-(3-morpholinopropoxy)-5,6,7,8-tetrahydropyrido[3,4-d]pyrimidin-4-yl)piperazin-1-yl)prop-2-en-1-one Synthesized according to the method of Example 8, using 3-morpholinopropan-1-ol in place of (S)-1-(dimethylamino) propan-2-ol in Step B, and using 2-bromo-4-(methoxymethoxy)-1-(trifluoromethoxy)benzene in place of (3-(methoxymethoxy)naphthalen-1-yl trifluoromethanesulfonate in Step D. ES+APCI MS m/z 593.2 [M+H]$^+$.

Example 91

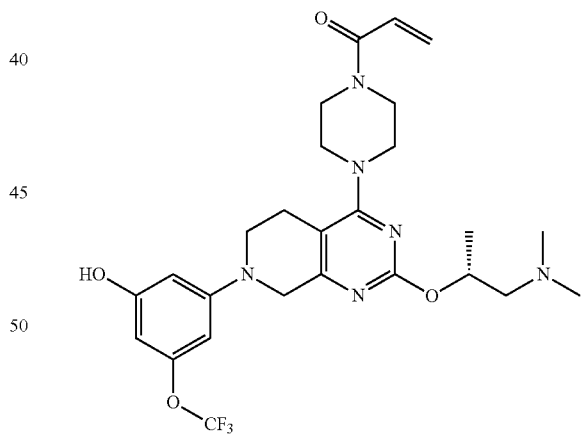

(R)-1-(4-(2-((1-(dimethylamino)propan-2-yl)oxy)-7-(3-hydroxy-5-(trifluoromethoxy)phenyl)-5,6,7,8-tetrahydropyrido[3,4-d]pyrimidin-4-yl)piperazin-1-yl)prop-2-en-1-one Synthesized according to the method of Example 8, using 3-bromo-1-(methoxymethoxy)-5-(trifluoromethoxy)benzene in place of (3-(methoxymethoxy)naphthalen-1-yl trifluoromethanesulfonate in Step D. ES+APCI MS m/z 551.2 [M+H]$^+$.

Example 92

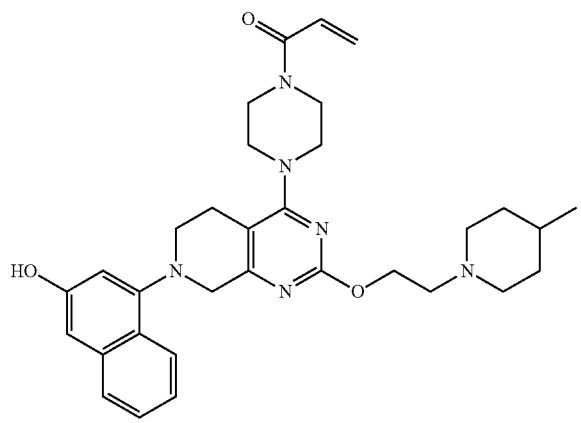 [SMILES: C=CC(=O)N1CCN(c2nc(OCCN3CCC(C)CC3)nc3c2CCN(c2cc(O)cc4ccccc24)C3)CC1]

1-(4-(7-(3-hydroxynaphthalen-1-yl)-2-(2-(4-methyl-piperidin-1-yl)ethoxy)-5,6,7,8-tetrahydropyrido[3,4-d]pyrimidin-4-yl)piperazin-1-yl)prop-2-en-1-one Synthesized according to the method of Example 8, using 2-(4-methylpiperidin-1-yl)ethan-1-ol in place of (S)-1-(dimethylamino)propan-2-ol in Step B. ES+APCI MS m/z 557.2 [M+H]+.

Example 93

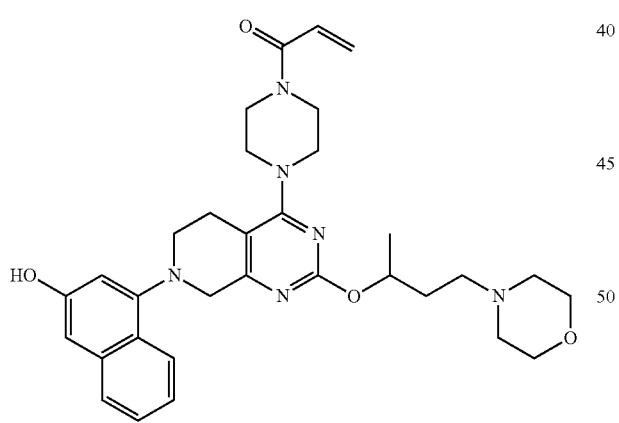

1-(4-(7-(3-hydroxynaphthalen-1-yl)-2-((4-morpholinobutan-2-yl)oxy)-5,6,7,8-tetrahydropyrido[3,4-d]pyrimidin-4-yl)piperazin-1-yl)prop-2-en-1-one Synthesized according to the method of Example 8, using 4-morpholinobutan-2-ol in place of (S)-1-(dimethylamino)propan-2-ol in Step B. ES+APCI MS m/z 573.3 [M+H]+.

Example 94

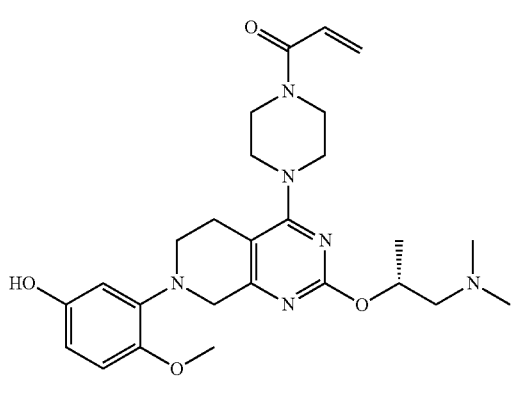 [SMILES: C=CC(=O)N1CCN(c2nc(O[C@H](C)CN(C)C)nc3c2CCN(c2cc(O)ccc2OC)C3)CC1]

(R)-1-(4-(2-((1-(dimethylamino)propan-2-yl)oxy)-7-(5-hydroxy-2-methoxyphenyl)-5,6,7,8-tetrahydro-pyrido[3,4-d]pyrimidin-4-yl)piperazin-1-yl)prop-2-en-1-one Synthesized according to the method of Example 8, using 3-bromo-1-(methoxymethoxy)-4-methoxybenzene in place of (3-(methoxymethoxy)naphthalen-1-yl trifluoromethane-sulfonate in Step D. ES+APCI MS m/z 497.2 [M+H]+.

Example 95

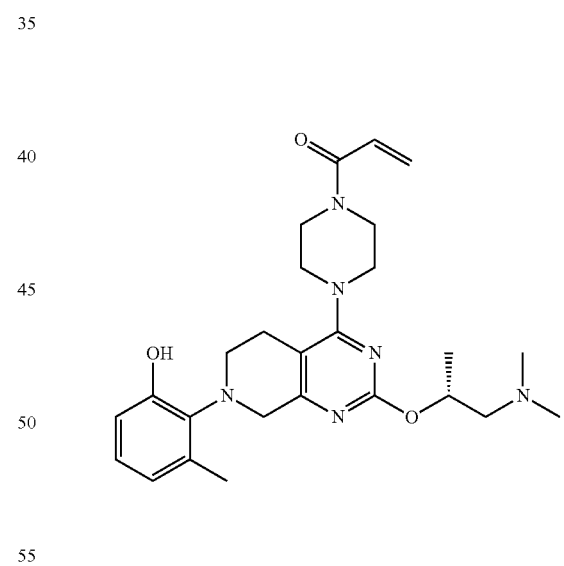

(R)-1-(4-(2-((1-(dimethylamino)propan-2-yl)oxy)-7-(2-hydroxy-6-methylphenyl)-5,6,7,8-tetrahydro-pyrido[3,4-d]pyrimidin-4-yl)piperazin-1-yl)prop-2-en-1-one Synthesized according to the method of Example 8, using 2-bromo-1-(methoxymethoxy)-3-methylbenzene in place of (3-(methoxymethoxy)naphthalen-1-yl trifluoromethanesulfonate in Step D. ES+APCI MS m/z 481.2 [M+H]+.

Example 96

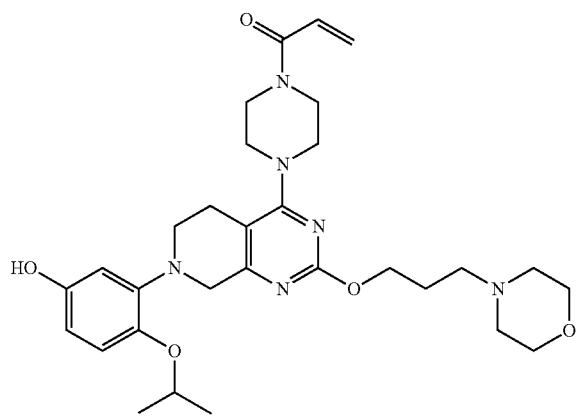 [SMILES: C=CC(=O)N1CCN(c2nc(OCCCN3CCOCC3)nc3c2CCN(c2cc(O)ccc2OC(C)C)C3)CC1]

1-(4-(7-(5-hydroxy-2-isopropoxyphenyl)-2-(3-morpholinopropoxy)-5,6,7,8-tetrahydropyrido[3,4-d]pyrimidin-4-yl)piperazin-1-yl)prop-2-en-1-one Synthesized according to the method of Example 8, using 3-morpholinopropan-1-ol in place of (S)-1-(dimethylamino)propan-2-ol in Step B, and using 2-bromo-4-(methoxymethoxy)-1-(isopropoxy)benzene in place of (3-(methoxymethoxy)naphthalen-1-yl trifluoromethanesulfonate in Step D. ES+APCI MS m/z 567.2 [M+H]+.

Example 97

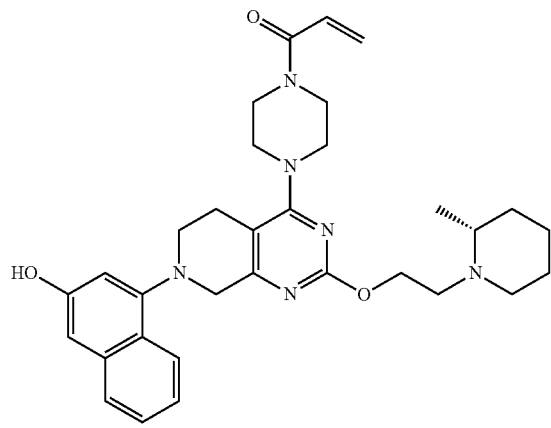 [SMILES: C=CC(=O)N1CCN(c2nc(OCCN3CCCC[C@H]3C)nc3c2CCN(c2cc(O)cc4ccccc24)C3)CC1]

(R)-1-(4-(7-(3-hydroxynaphthalen-1-yl)-2-(2-(2-methylpiperidin-1-yl)ethoxy)-5,6,7,8-tetrahydropyrido[3,4-d]pyrimidin-4-yl)piperazin-1-yl)prop-2-en-1-one Synthesized according to the method of Example 8, using (R)-2-(2-methylpiperidin-1-yl)ethan-1-ol in place of (S)-1-(dimethylamino)propan-2-ol in Step B. ES+APCI MS m/z 557.3

Example 98

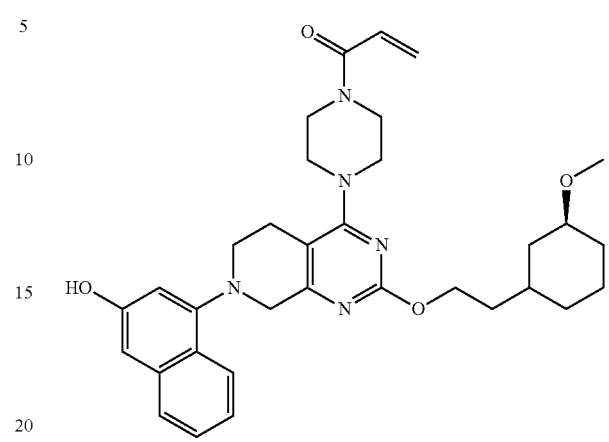

(S)-1-(4-(7-(3-hydroxynaphthalen-1-yl)-2-(2-(3-methoxypiperidin-1-yl)ethoxy)-5,6,7,8-tetrahydropyrido[3,4-d]pyrimidin-4-yl)piperazin-1-yl)prop-2-en-1-one Synthesized according to the method of Example 8, using (S)-2-(3-methoxypiperidin-1-yl)ethan-1-ol in place of (S)-1-(dimethylamino)propan-2-ol in Step B. ES+APCI MS m/z 557.3 [M+H]+.

Example 99

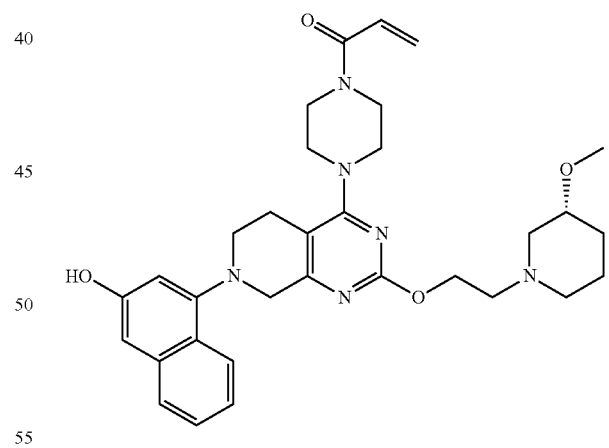

(R)-1-(4-(7-(3-hydroxynaphthalen-1-yl)-2-(2-(3-methoxypiperidin-1-yl)ethoxy)-5,6,7,8-tetrahydropyrido[3,4-d]pyrimidin-4-yl)piperazin-1-yl)prop-2-en-1-one Synthesized according to the method of Example 8, using (R)-2-(3-methoxypiperidin-1-yl)ethan-1-ol in place of (S)-1-(dimethylamino)propan-2-ol in Step B. ES+APCI MS m/z 557.3 [M+H]+.

Example 100

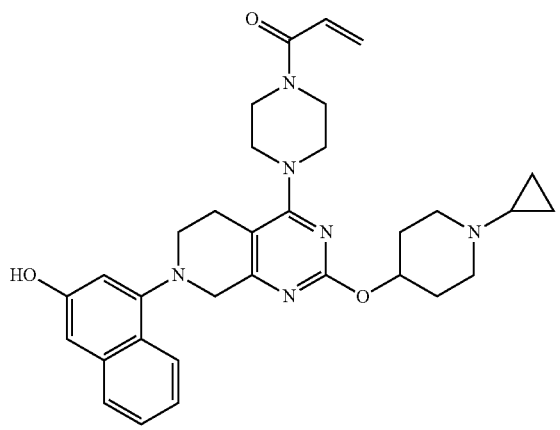 [SMILES: C=CC(=O)N1CCN(c2nc(OC3CCN(C4CC4)CC3)nc3c2CCN(c2cc(O)cc4ccccc24)C3)CC1]

1-(4-(2-((1-cyclopropylpiperidin-4-yl)oxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using (1-cyclopropylpiperidin-4-ol in place of (S)-1-(dimethylamino)propan-2-ol in Step B. ES+APCI MS m/z 555.3 [M+H]$^+$.

Example 101

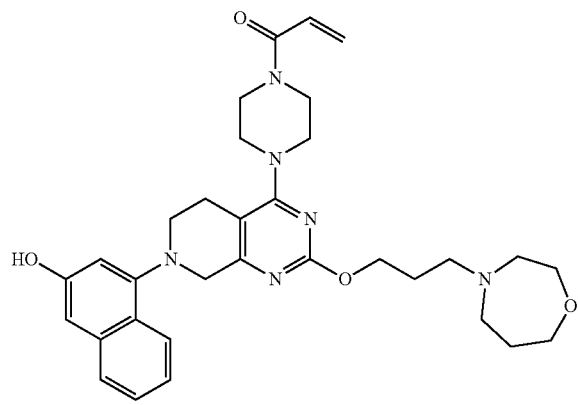 [SMILES: C=CC(=O)N1CCN(c2nc(OCCCN3CCCOCC3)nc3c2CCN(c2cc(O)cc4ccccc24)C3)CC1]

1-(4-(2-(3-(1,4-oxazepan-4-yl)propoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using (3-(1,4-oxazepan-4-yl)propan-1-ol in place of (S)-1-(dimethylamino)propan-2-ol in Step B. ES+APCI MS m/z 573.3 [M+H]$^+$.

Example 102

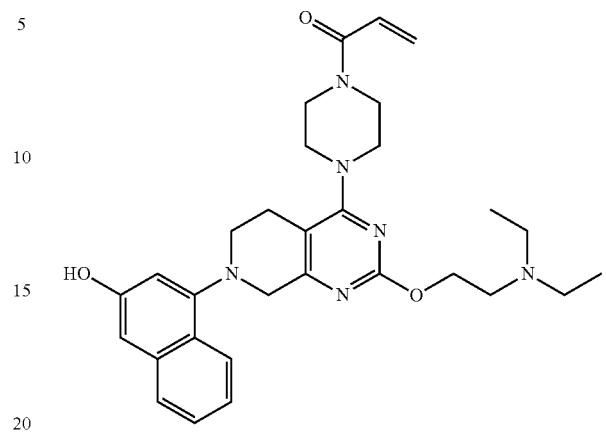

1-(4-(2-(3-(1,4-oxazepan-4-yl)propoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 2-(diethylamino)ethan-1-ol in place of (S)-1-(dimethylamino)propan-2-ol in Step B. ES+APCI MS m/z 531.3 [M+H]$^+$.

Example 103

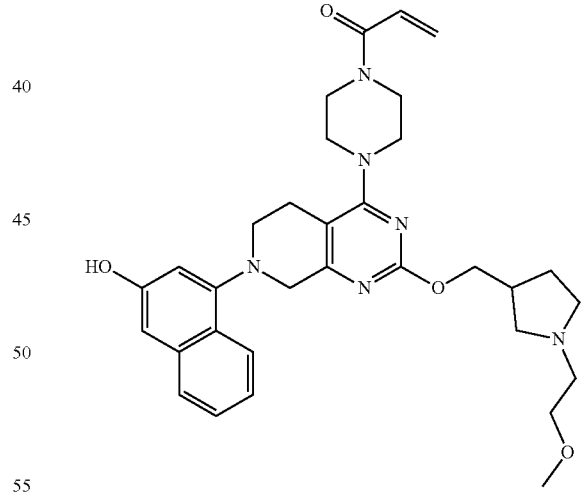

1-(4-(7-(3-hydroxynaphthalen-1-yl)-2-((1-(2-methoxyethyl)pyrrolidin-3-yl)methoxy)-5,6,7,8-tetrahydropyrido[3,4-d]pyrimidin-4-yl)piperazin-1-yl)prop-2-en-1-one Synthesized according to the method of Example 8, (1-(2-methoxyethyl)pyrrolidin-3-yl)methanol in place of (S)-1-(dimethylamino)propan-2-ol in Step B. ES+APCI MS m/z 573.3 [M+H]$^+$.

Example 104

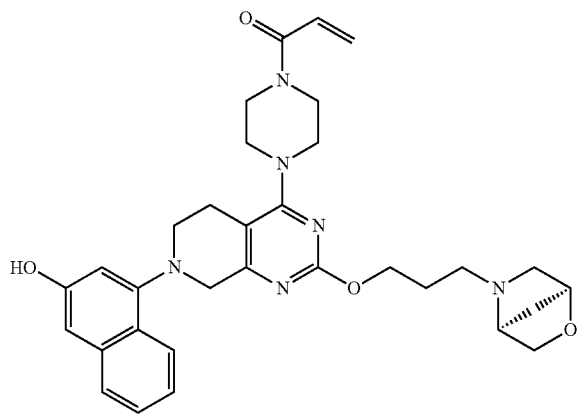 [SMILES: C=CC(=O)N1CCN(c2nc(OCCCN3C[C@@H]4C[C@H]3CO4)nc3c2CCN(c2cc(O)cc4ccccc24)C3)CC1]

1-(4-(2-(3-((1S,4S)-2-oxa-5-azabicyclo[2.2.1]heptan-5-yl)propoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 3-((1S,4S)-2-oxa-5-azabicyclo[2.2.1]heptan-5-yl)propan-1-ol in place of (S)-1-(dimethylamino)propan-2-ol in Step B. ES+APCI MS m/z 571.3 [M+H]$^+$.

Example 105

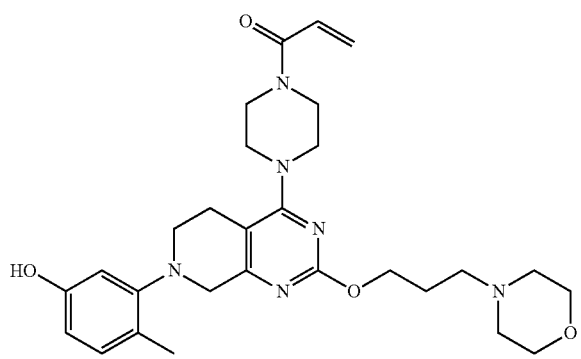 [SMILES: C=CC(=O)N1CCN(c2nc(OCCCN3CCOCC3)nc3c2CCN(c2cc(O)ccc2C)C3)CC1]

1-(4-(7-(5-hydroxy-2-methylphenyl)-2-(3-morpholinopropoxy)-5,6,7,8-tetrahydropyrido[3,4-d]pyrimidin-4-yl)piperazin-1-yl)prop-2-en-1-one Synthesized according to the method of Example 8, using 3-morpholinopropan-1-ol in place of (S)-1-(dimethylamino)propan-2-ol in Step B, and using 2-bromo-4-(methoxymethoxy)-1-methylbenzene in place of (3-(methoxymethoxy)naphthalen-1-yl trifluoromethanesulfonate in Step D. ES+APCI MS m/z 523.3 [M+H]$^+$.

Example 106

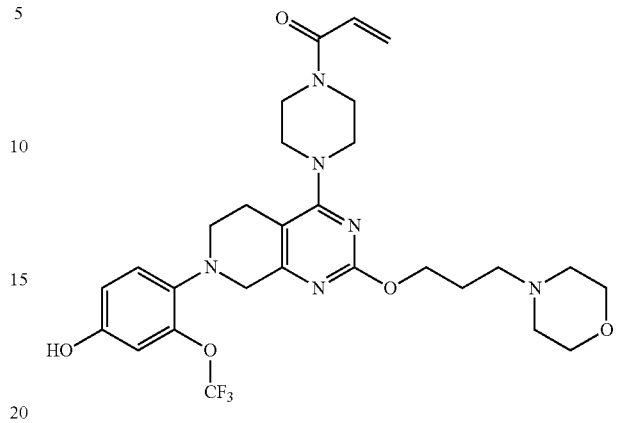

1-(4-(7-(4-hydroxy-2-(trifluoromethoxy)phenyl)-2-(3-morpholinopropoxy)-5,6,7,8-tetrahydropyrido[3,4-d]pyrimidin-4-yl)piperazin-1-yl)prop-2-en-1-one Synthesized according to the method of Example 8, using 3-morpholinopropan-1-ol in place of (S)-1-(dimethylamino)propan-2-ol in Step B, and using 2-bromo-5-(methoxymethoxy)-1-(trifluoromethoxy)benzene in place of (3-(methoxymethoxy)naphthalen-1-yl trifluoromethanesulfonate in Step D. ES+APCI MS m/z 593.2 [M+H]$^+$.

Example 107

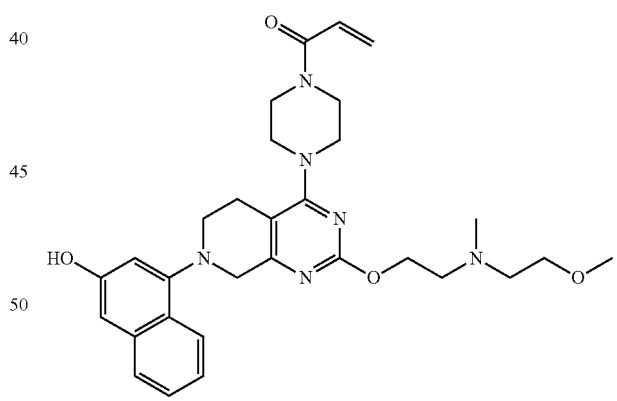

1-(4-(7-(3-hydroxynaphthalen-1-yl)-2-(2-((2-methoxyethyl)(methyl)amino)ethoxy)-5,6,7,8-tetrahydropyrido[3,4-d]pyrimidin-4-yl)piperazin-1-yl)prop-2-en-1-one Synthesized according to the method of Example 8, using 2-((2-methoxyethyl)(methyl)amino)ethan-1-ol in place of (S)-1-(dimethylamino)propan-2-ol in Step B. ES+APCI MS m/z 547.3 [M+H]$^+$.

Example 108

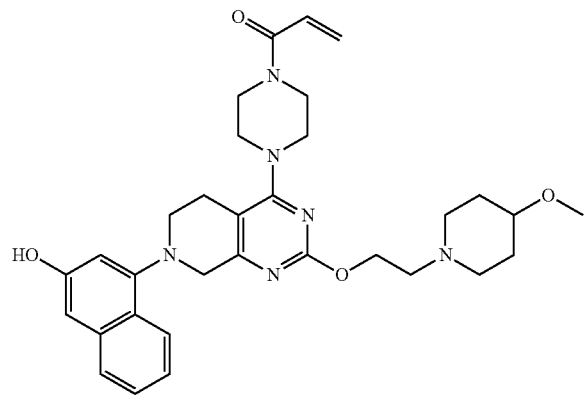 [SMILES: C=CC(=O)N1CCN(c2nc(OCCN3CCC(OC)CC3)nc3c2CCN(c2cc(O)cc4ccccc24)C3)CC1]

1-(4-(7-(3-hydroxynaphthalen-1-yl)-2-(2-(4-methoxypiperidin-1-yl)ethoxy)-5,6,7,8-tetrahydropyrido[3,4-d]pyrimidin-4-yl)piperazin-1-yl)prop-2-en-1-one Synthesized according to the method of Example 8, using 2-(4-methoxypiperidin-1-yl)ethan-1-ol in place of (S)-1-(dimethylamino)propan-2-ol in Step B. ES+APCI MS m/z 573.3 [M+H]+.

Example 109

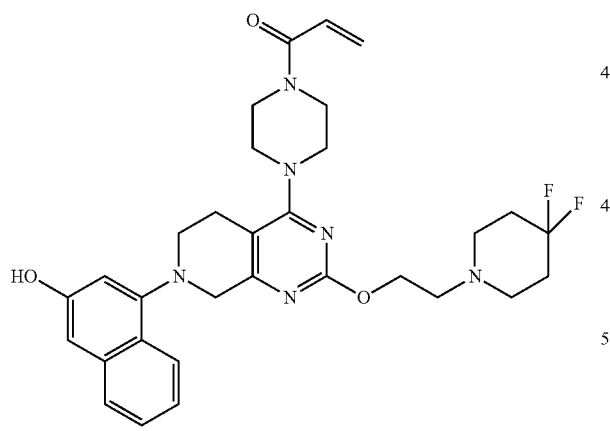

1-(4-(2-(2-((4,4-difluoropiperidin-1-yl)ethoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 2-((4,4-difluoropiperidin-1-yl)ethan-1-ol in place of (S)-1-(dimethylamino)propan-2-ol in Step B. ES+APCI MS m/z 579.2 [M+H]+.

Example 110

(R)-1-(4-(7-(3-hydroxynaphthalen-1-yl)-2-((1-methylpyrrolidin-3-yl)methoxy)-5,6,7,8-tetrahydropyrido[3,4-d]pyrimidin-4-yl)piperazin-1-yl)prop-2-en-1-one Synthesized according to the method of Example 8, using (R)-(1-methylpyrrolidin-3-yl)methanol in place of (S)-1-(dimethylamino)propan-2-ol in Step B. ES+APCI MS m/z 529.3 [M+H]+.

Example 111

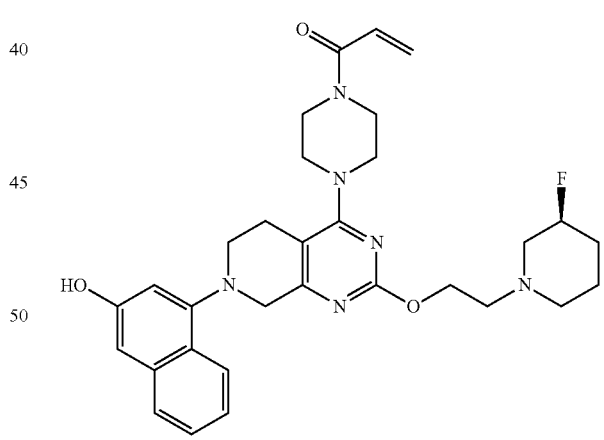

(S)-1-(4-(2-(2-(3-fluoropiperidin-1-yl)ethoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using (S)-2-(3-fluoropiperidin-1-yl)ethan-1-ol in place of (S)-1-(dimethylamino)propan-2-ol in Step B. ES+APCI MS m/z 561.3 [M+H]+.

Example 112

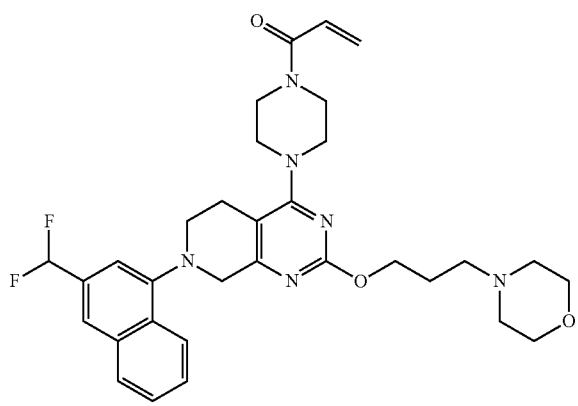 [SMILES: C=CC(=O)N1CCN(c2nc(OCCCN3CCOCC3)nc3c2CCN(c2cc(C(F)F)cc4ccccc24)C3)CC1]

1-(4-(7-(3-(difluoromethyl)naphthalen-1-yl)-2-(3-morpholinopropoxy)-5,6,7,8-tetrahydropyrido[3,4-d]pyrimidin-4-yl)piperazin-1-yl)prop-2-en-1-one Synthesized according to the method of Example 8, using 3-morpholinopropan-1-ol in place of (S)-1-(dimethylamino)propan-2-ol in Step B, and using 1-bromo-3-(difluoromethyl)naphthalene (0.129 g, 0.503 mmol) in place of (3-(methoxymethoxy)naphthalen-1-yl trifluoromethanesulfonate in Step D. ES+APCI MS m/z 593.2 [M+H]$^+$.

Example 113

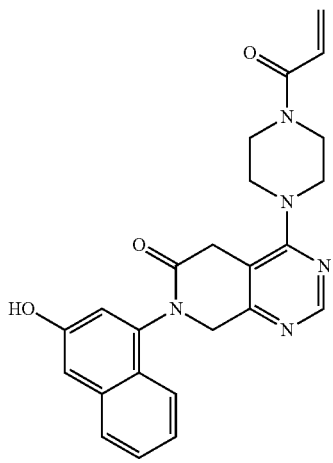 [SMILES: C=CC(=O)N1CCN(c2ncnc3c2CC(=O)N(c2cc(O)cc4ccccc24)C3)CC1]

4-(4-acryloylpiperazin-1-yl)-7-(3-hydroxynaphthalen-1-yl)-7,8-dihydropyrido[3,4-d]pyrimidin-6(5H)-one Step A: tert-butyl 4-(6-fluoropyrido[3,4-d]pyrimidin-4-yl)piperazine-1-carboxylate To a solution of 4-chloro-6-fluoropyrido[3,4-d]pyrimidine (1.07 g, 5.83 mmol) in DCM (20 mL) was added N-ethyl-N-isopropylpropan-2-amine (2.09 mL, 11.7 mmol) followed by tert-butyl piperazine-1-carboxylate (1.19 g, 6.41 mmol) and the reaction stirred at room temperature for 2 hours. The reaction mixture was washed with brine, dried over MgSO$_4$ and concentrated in vacuo to provide tert-butyl 4-(6-fluoropyrido[3,4-d]pyrimidin-4-yl)piperazine-1-carboxylate, which was used directly in the next step (1.8 g, 92.6%) ES+APCI MS m/z 334.1 [M+H]$^+$.

Step B: tert-butyl 4-(6-(benzyloxy)pyrido[3,4-d]pyrimidin-4-yl)piperazine-1-carboxylate To a solution of phenylmethanol (0.65 g, 6.0 mmol) in DMA (10 mL) was added sodium hydride (0.24 g, 6.0 mmol) in portions while degassing with nitrogen and the reaction mixture was stirred for 30 minutes at room temperature. To the reaction was added tert-butyl 4-(6-fluoropyrido[3,4-d]pyrimidin-4-yl)piperazine-1-carboxylate (1.0 g, 3.0 mmol) as a solid and the reaction mixture was stirred at room temperature for 3 hours. The reaction was poured into water (300 mL) and the aqueous layer extracted with ethyl acetate. The organic layer was washed with brine, dried over MgSO$_4$ and concentrated in vacuo. The crude material was chromatographed using a gradient of 0 to 100% ethyl acetate/DCM as the eluent to give tert-butyl 4-(6-(benzyloxy)pyrido[3,4-d]pyrimidin-4-yl)piperazine-1-carboxylate (0.4 g, 0.95 mmol, 32% yield). ES+APCI MS m/z 422.2 [M+H]$^+$.

Step C: tert-butyl 4-(6-oxo-5,6,7,8-tetrahydropyrido[3,4-d]pyrimidin-4-yl)piperazine-1-carboxylate To a solution of tert-butyl 4-(6-(benzyloxy)pyrido[3,4-d]pyrimidin-4-yl)piperazine-1-carboxylate (0.40 g, 0.95 mmol) in 95% ethanol (30 mL) purged with nitrogen was added Pd/C (0.10 g, 0.95 mmol). The reaction was evacuated with vacuum and backfilled with hydrogen three times. After the third backfill the reaction mixture was stirred at room temperature for 4 hours. The reaction was again degassed with nitrogen, the slurry filtered through Celite® and the filtrate was concentrated in vacuo to give tert-butyl 4-(6-oxo-5,6,7,8-tetrahydropyrido[3,4-d]pyrimidin-4-yl)piperazine-1-carboxylate (0.4 g, 126%). ES+APCI MS m/z 334.4 [M+H]$^+$.

Step D: tert-butyl 4-(7-(3-(methoxymethoxy)naphthalen-1-yl)-6-oxo-5,6,7,8-tetrahydropyrido[3,4-d]pyrimidin-4-yl)piperazine-1-carboxylate: To a solution of tert-butyl 4-(6-oxo-5,6,7,8-tetrahydropyrido[3,4-d]pyrimidin-4-yl)piperazine-1-carboxylate (0.28 g, 0.84 mmol) in dioxanes (4 mL) in a sealed tube was added potassium phosphate (0.36 g, 1.7 mmol), N1,N2-dimethylethane-1,2-diamine (0.074 g, 0.84 mmol) and 1-iodo-3-(methoxymethoxy)naphthalene (0.53 g, 1.7 mmol). The reaction sparged with argon for 20 minutes, followed by addition of copper(I) iodide (0.16 g, 0.84 mmol). The reaction vessel sealed and heated to 100° C. overnight. The reaction was diluted with water and the aqueous layer extracted with ethyl acetate (2×150 mL). The organics were washed with brine, dried over MgSO$_4$ and concentrated in vacuo. The material was chromatographed using a gradient of 0 to 100% ethyl acetate/DCM as the eluent to give tert-butyl 4-(7-(3-(methoxymethoxy)naphthalen-1-yl)-6-oxo-5,6,7,8-tetrahydropyrido[3,4-d]pyrimidin-4-yl)piperazine-1-carboxylate (0.30 g, 0.58 mmol, 69% yield) ES+APCI MS m/z 520.2 [M+H]$^+$.

Step E: 7-(3-hydroxynaphthalen-1-yl)-4-(piperazin-1-yl)-7,8-dihydropyrido[3,4-d]pyrimidin-6(5H)-one To a solution of tert-butyl 4-(7-(3-(methoxymethoxy)naphthalen-1-yl)-6-oxo-5,6,7,8-tetrahydropyrido[3,4-d]pyrimidin-4-yl)piperazine-1-carboxylate (0.30 g, 0.58 mmol) in methanol (10 mL) was added aqueous hydrogen chloride (0.38 mL, 2.3 mmol) and the reaction stirred over night at 50° C. The reaction was concentrated in vacuo to give 7-(3-hydroxynaphthalen-1-yl)-4-(piperazin-1-yl)-7,8-dihydropyrido[3,4-d]pyrimidin-6(5H)-one as the bis HCl salt (0.26 g, 100%). ES+APCI MS m/z 376.1 [M+H]$^+$.

Step F: 4-(4-acryloylpiperazin-1-yl)-7-(3-hydroxynaphthalen-1-yl)-7,8-dihydropyrido[3,4-d]pyrimidin-6(5H)-one To a slurry of 7-(3-hydroxynaphthalen-1-yl)-4-(piperazin-1-yl)-7,8-dihydropyrido[3,4-d]pyrimidin-6(5H)-one dihydrochloride (0.26 g, 0.58 mmol) in a 1:1 solution of DCM/acetonitrile (10 mL) was added N-ethyl-N-isopropylpropan-2-amine (0.45 g, 3.5 mmol) and acryloyl chloride (0.052 g, 0.58 mmol) and the reaction stirred at room temperature for 1 hour. The reaction was concentrated in vacuo and the material purified by reverse preparative HPLC (using a gradient of 5 to 95% ACN/water) to give 4-(4-acryloylpiperazin-1-yl)-7-(3-hydroxynaphthalen-1-yl)-7,8-dihydropyrido[3,4-d]pyrimidin-6(5H)-one (0.038 g, 0.088 mmol, 15% yield). ES+APCI MS m/z 430.2 [M+H]$^+$.

Example 114

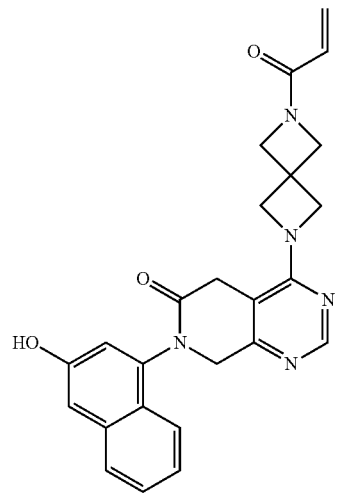 [SMILES: C=CC(=O)N1CC2(C1)CN(c1ncnc3c1CC(=O)N(c1cc(O)cc4ccccc14)C3)C2]

4-(6-acryloyl-2,6-diazaspiro[3.3]heptan-2-yl)-7-(3-hydroxynaphthalen-1-yl)-7,8-dihydropyrido[3,4-d]pyrimidin-6(5H)-one Synthesized according to the method of Example 8, using tert-butyl 2,6-diazaspiro[3.3]heptane-2-carboxylate hydrochloride (305 mg, 1.54 mmol) in place of tert-butyl piperazine-1-carboxylate (1.19 g, 6.41 mmol) in Step B. ES+APCI MS m/z 442.2 [M+H]$^+$ Example 115

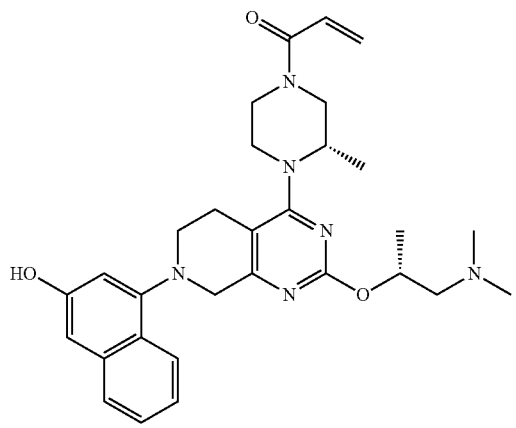 [SMILES: C=CC(=O)N1CCN(c2nc(O[C@H](C)CN(C)C)nc3c2CCN(c2cc(O)cc4ccccc24)C3)[C@@H](C)C1]

1-((S)-4-(2-(((R)-1-(dimethylamino)propan-2-yl)oxy)-7-(3-hydroxynaphthalen-1-yl)-5,6,7,8-tetrahydropyrido[3,4-d]pyrimidin-4-yl)-3-methylpiperazin-1-yl)prop-2-en-1-one Synthesized according to the method of Example 8, using benzyl (S)-3-methylpiperazine-1-carboxylate (1.155 g, 4.931 mmol) in place of Benzyl 1-piperazinecarboxylate in step A. ES+APCI MS m/z 531.3 [M+H]$^+$.

Example 116

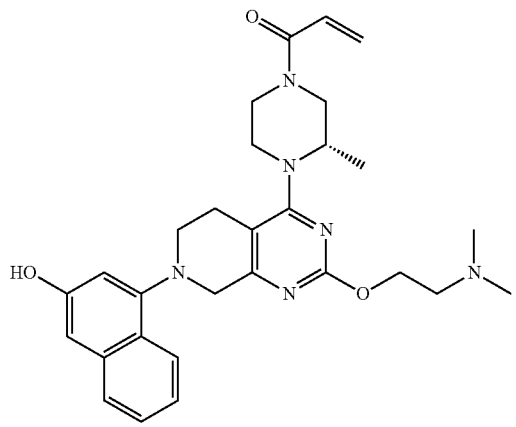 [SMILES: C=CC(=O)N1CCN(c2nc(OCCN(C)C)nc3c2CCN(c2cc(O)cc4ccccc24)C3)[C@@H](C)C1]

(S)-1-(4-(2-(2-(dimethylamino)ethoxy)-7-(3-hydroxynaphthalen-1-yl)-5,6,7,8-tetrahydropyrido[3,4-d]pyrimidin-4-yl)-3-methylpiperazin-1-yl)prop-2-en-1-one Synthesized according to the method of Example 8, using benzyl (S)-3-methylpiperazine-1-carboxylate (1.155 g, 4.931 mmol) in place of Benzyl 1-piperazinecarboxylate in step A. Also, using 2-(dimethylamino)ethan-1-ol in place of (S)-1-(dimethylamino)propan-2-ol in Step B. ES+APCI MS m/z 517.3 [M+H]$^+$.

Example 117

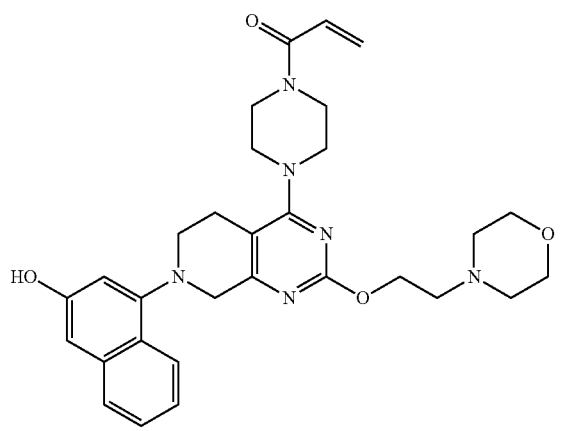

1-(4-(7-(3-hydroxynaphthalen-1-yl)-2-(2-morpholinoethoxy)-5,6,7,8-tetrahydropyrido[3,4-d]pyrimidin-4-yl)piperazin-1-yl)prop-2-en-1-one Synthesized according to the method of Example 8, using 2-morpholinoethan-1-ol in place of (S)-1-(dimethylamino)propan-2-ol in Step B. ES+APCI MS m/z 545.2 [M+H]+.

Example 118

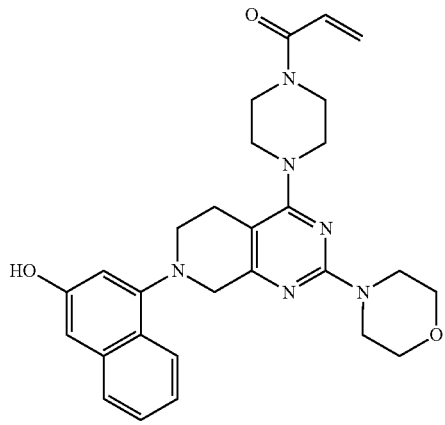 [SMILES: C=CC(=O)N1CCN(c2nc(N3CCOCC3)nc3c2CCN(c2cc(O)cc4ccccc24)C3)CC1]

1-(4-(7-(3-hydroxynaphthalen-1-yl)-2-morpholino-5,6,7,8-tetrahydropyrido[3,4-d]pyrimidin-4-yl)piperazin-1-yl)prop-2-en-1-one Synthesized according to the method of Example 8, using morpholine in place of (S)-1-(dimethylamino)propan-2-ol in Step B. ES+APCI MS m/z 501.3 [M+H]+.

Example 119

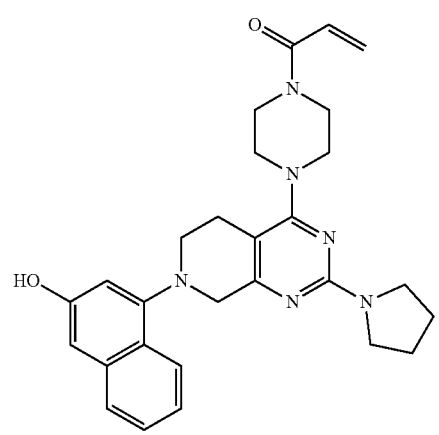 [SMILES: C=CC(=O)N1CCN(c2nc(N3CCCC3)nc3c2CCN(c2cc(O)cc4ccccc24)C3)CC1]

1-(4-(7-(3-hydroxynaphthalen-1-yl)-2-(pyrrolidin-1-yl)-5,6,7,8-tetrahydropyrido[3,4-d]pyrimidin-4-yl)piperazin-1-yl)prop-2-en-1-one Synthesized according to the method of Example 8, using pyrrolidine in place of (S)-1-(dimethylamino)propan-2-ol in Step B. ES+APCI MS m/z 485.2 [M+H]+.

Example 120

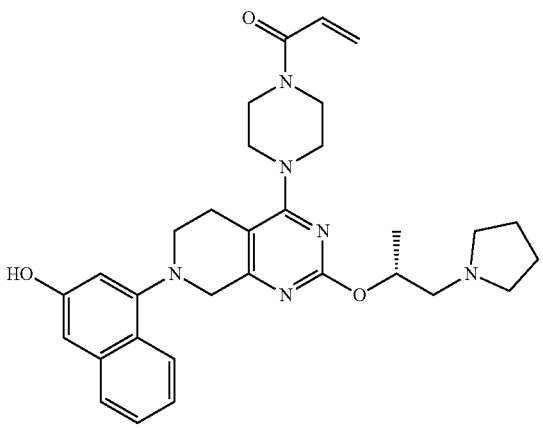 [SMILES: C=CC(=O)N1CCN(c2nc(O[C@H](C)CN3CCCC3)nc3c2CCN(c2cc(O)cc4ccccc24)C3)CC1]

(R)-1-(4-(7-(3-hydroxynaphthalen-1-yl)-2-((1-(pyrrolidin-1-yl)propan-2-yl)oxy)-5,6,7,8-tetrahydropyrido[3,4-d]pyrimidin-4-yl)piperazin-1-yl)prop-2-en-1-one Synthesized according to the method of Example 8, using (R)-1-(pyrrolidin-1-yl)propan-2-ol in place of (S)-1-(dimethylamino)propan-2-ol in Step B. ES+APCI MS m/z 543.4 [M+H]+.

Example 121

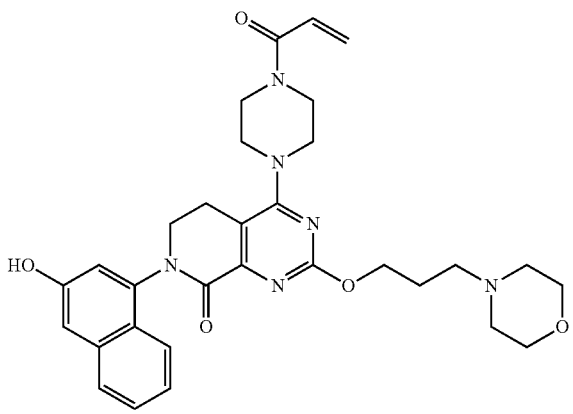 [SMILES: C=CC(=O)N1CCN(c2nc(OCCCN3CCOCC3)nc3c2CCN(c2cc(O)cc4ccccc24)C3=O)CC1]

4-(4-acryloylpiperazin-1-yl)-7-(3-hydroxynaphthalen-1-yl)-2-(3-morpholinopropoxy)-6,7-dihydropyrido[3,4-d]pyrimidin-8(5H)-one Step A: Tert-butyl 2,4-dichloro-8-oxo-5,8-dihydropyrido[3,4-d]pyrimidine-7(6H)-carboxylate. To a round bottom flask was added tert-Butyl 2,4-dichloro-5,6-dihydropyrido[3,4-d]pyrimidine-7(8H)-carboxylate (1.0 g, 3.29 mmol) and EtOAc (16.4 mL). A solution of sodium periodate (2.11 g, 9.86 mmol) in water (16.4 mL) was added. Ruthenium (III) chloride (0.102 g, 0.493 mmol) was added and the mixture was stirred loosely capped and vigorously stirred for 6 h at ambient temperature. The mixture was partitioned between water and EtOAc and the layers were separated. The aqueous layer was extracted further with EtOAc (2×20 mL) and the combined extracts were washed with brine and dried over $Na_2SO_4$, filtered and concentrated. The crude product was purified via column chromatography (10-30% EtOAc/hexanes, loading with $CH_2Cl_2$) to afford 0.864 g (82%) of the product as an off-white solid.

Step B: Tert-butyl 4-(4-((benzyloxy)carbonyl)piperazin-1-yl)-2-chloro-8-oxo-5,8-dihydropyrido[3,4-d]pyrimidine-7(6H)-carboxylate. To a solution of tert-butyl 2,4-dichloro-8-oxo-5,8-dihydropyrido[3,4-d]pyrimidine-7(6H)-carboxylate (0.400 g, 1.26 mmol) in $CH_2Cl_2$ (5.0 mL) was added N,N-Diisopropylethylamine (0.325 g, 2.51 mmol) followed by benzyl 1-piperazinecarboxylate (0.255 mL, 1.32 mmol) and the reaction stirred at ambient temperature for 1.5 h. The reaction mixture was diluted with $CH_2Cl_2$ (10 mL) and washed with a 0.5M $KHSO_4$ solution (5 mL), followed by a saturated aqueous $NaHCO_3$ solution and brine. The organic layer was dried over $Na_2SO_4$, filtered and concentrated. The crude product was sonicated in 10 mL MTBE and the resulting solid was isolated by vacuum filtration. The solid was dried in vacuo to provide 0.507 g (80%) of the desired product as an off-white solid which was used directly in the next step. ES+APCI MS m/z 502.1[M+H]$^+$.

Step C: Benzyl 4-(2-chloro-8-oxo-5,6,7,8-tetrahydropyrido[3,4-d]pyrimidin-4-yl)piperazine-1-carboxylate. A solution of tert-butyl 4-(4-((benzyloxy)carbonyl)piperazin-1-yl)-2-chloro-8-oxo-5,8-dihydropyrido[3,4-d]pyrimidine-7(6H)-carboxylate (0.255 g, 0.5080 mmol) in $CH_2Cl_2$ (1.0 mL) was cooled to 0° C. Trifluoroacetic acid (0.3890 mL, 5.080 mmol) was added and the mixture was warmed to ambient temperature. After 1 hour the mixture was diluted with $CH_2Cl_2$ and added to a mixture brine (10 mL) and 3.0 M aqueous NaOH (1.7 mL, 5.080 mmol). The layers were combined and adjusted to pH 8 with saturated aqueous $NaHCO_3$ solution. The layers were separated and the aqueous phase was extracted with 2×10 mL of $CH_2Cl_2$. The combined organic layers were dried over $Na_2SO_4$, filtered and concentrated under vacuum. The title compound (0.223 g, quant.) was obtained as a yellow/orange foam. ES+APCI MS m/z 402.1[M+H]$^+$.

Step D: Benzyl 4-(2-(3-morpholinopropoxy)-8-oxo-5,6,7,8-tetrahydropyrido[3,4-d]pyrimidin-4-yl)piperazine-1-carboxylate. To a vial was added N-Hydroxypropanylmorpholine (0.687 g, 4.73 mmol) and benzyl 4-(2-chloro-8-oxo-5,6,7,8-tetrahydropyrido[3,4-d]pyrimidin-4-yl)piperazine-1-carboxylate (0.190 g, 0.473 mmol) followed by dioxane (1.6 mL). Cesium carbonate (0.462 g, 1.42 mmol) was added and the mixture was stirred at 65° C. for 15 hours. The mixture was diluted with $CHCl_3$ and filtered, and the solid was washed with additional $CHCl_3$. The filtrate was concentrated in vacuo and was purified by column chromatography (2-10% MeOH/DCM with 1% $NH_4OH$) to afford 0.061 g (25%) of the desired product as a thick, colorless oil. ES+APCI MS m/z 511.2[M+H]$^+$.

Step E: Benzyl 4-(7-(3-(methoxymethoxy)naphthalen-1-yl)-2-(3-morpholinopropoxy)-8-oxo-5,6,7,8-tetrahydropyrido[3,4-d]pyrimidin-4-yl)piperazine-1-carboxylate. To a vial was added benzyl 4-(2-(3-morpholinopropoxy)-8-oxo-5,6,7,8-tetrahydropyrido[3,4-d]pyrimidin-4-yl)piperazine-1-carboxylate (0.060 g, 0.12 mmol), N,N'-Dimethylethylenediamine (0.010 g, 0.12 mmol) and 1-iodo-3-(methoxymethoxy)naphthalene (0.074 g, 0.24 mmol) followed by dioxane (0.78 mL) and Potassium phosphate tribasic (0.050 g, 0.24 mmol). The reaction was purged with bubbling Ar for 10 min, then Copper (I) Iodide (0.022 g, 0.12 mmol) was added and the vial was sealed. The mixture was heated to 110° C. and stirred for 16 hours. The mixture was cooled to ambient temperature, diluted with water and extracted with EtOAc (3×10 mL). The combined organic extracts were dried over $Na_2SO_4$, filtered and concentrated. The mixture was purified via column chromatography (2-8% MeOH/DCM) to afford 0.062 g (76%) of the product as a tan foam. ES+APCI MS m/z 697.3[M+H]$^+$.

Step F: 7-(3-(methoxymethoxy)naphthalen-1-yl)-2-(3-morpholinopropoxy)-4-(piperazin-1-yl)-6,7-dihydropyrido[3,4-d]pyrimidin-8(5H)-one. To a solution of benzyl 4-(7-(3-(methoxymethoxy)naphthalen-1-yl)-2-(3-morpholinopropoxy)-8-oxo-5,6,7,8-tetrahydropyrido[3,4-d]pyrimidin-4-yl)piperazine-1-carboxylate (0.062 g, 0.089 mmol) in EtOH (0.44 mL) and THF (0.44 mL) was added Palladium on Carbon (0.038 g, 0.018 mmol) (Degussa Type, 10 wt %, 50% $H_2O$) and then an atmosphere of hydrogen was introduced via vacuum followed by balloon pressure. The mixture was stirred at ambient temperature for 1.5 h, then warmed to 45° C. and stirred for 1 hour. The mixture was diluted with EtOAc and filtered through a nylon filter. The filtrate was concentrated in vacuo providing a light tan foam (0.052 g) that was dried overnight and resubmitted to the same reaction conditions above. After stirring at ambient temperature for 5 h additional Pd/C (0.050 g) was added and the reaction was stirred at ambient temperature for another 2 h. The mixture was diluted with EtOAc and filtered through a nylon filter. The solid was washed with EtOAc and MeOH and the filtrate was concentrated in vacuo providing 0.029 g (58%) of the desired product as a light tan foam. ES+APCI MS m/z 563.3[M+H]$^+$.

Step G: 4-(4-acryloylpiperazin-1-yl)-7-(3-(methoxymethoxy)naphthalen-1-yl)-2-(3-morpholinopropoxy)-6,7-dihydropyrido[3,4-d]pyrimidin-8(5H)-one. To a solution of 7-(3-(methoxymethoxy)naphthalen-1-yl)-2-(3-morpholinopropoxy)-4-(piperazin-1-yl)-6,7-dihydropyrido[3,4-d]pyrimidin-8(5H)-one (0.028 g, 0.050 mmol) in CH$_2$Cl$_2$ (0.50 mL) at −78° C. was added Triethylamine (0.014 mL, 0.100 mmol). Acryloyl chloride (0.55 mL, 0.055 mmol, freshly prepared 0.1M CH$_2$Cl$_2$) was added and the reaction was then stirred for 0.5 h. The mixture was diluted with CHCl$_3$ and a saturated aqueous NH$_4$Cl solution was added. The layers were separated and the aqueous layer was extracted with CHCl$_3$ (2×10 mL). The combined extracts were dried over Na$_2$SO$_4$, filtered and concentrated. The crude product was purified via column chromatography (4-6% MeOH/DCM) to afford 0.018 g (59%) to provide the title compound as a solid off-white foam. ES+APCI MS m/z 617.3[M+H]$^+$.

Step H: 4-(4-acryloylpiperazin-1-yl)-7-(3-hydroxynaphthalen-1-yl)-2-(3-morpholinopropoxy)-6,7-dihydropyrido[3,4-d]pyrimidin-8(5H)-one. To a solution of 4-(4-acryloylpiperazin-1-yl)-7-(3-(methoxymethoxy)naphthalen-1-yl)-2-(3-morpholinopropoxy)-6,7-dihydropyrido[3,4-d]pyrimidin-8(5H)-one (0.018 g, 0.0292 mmol) in 1/1 MeOH/THF (0.6 mL) was added HCl (0.0486 mL, 0.292 mmol, 6 N Aqueous). The mixture was stirred at 35° C. for 7 hours. The mixture was diluted with brine and adjusted to pH 8 with a saturated aqueous NaHCO$_3$ solution. The mixture was extracted with 10% IPA/CHCl$_3$ (2×10 mL) and CHCl$_3$ (10 mL). The combined organic layers were dried over Na$_2$SO$_4$, filtered and concentrated. The crude material was purified via column chromatography (6-10% MeOH/DCM) to afford 0.012 g (71%) of the product as an off-white solid. ES+APCI MS m/z 573.3[M+H]$^+$.

Example 122

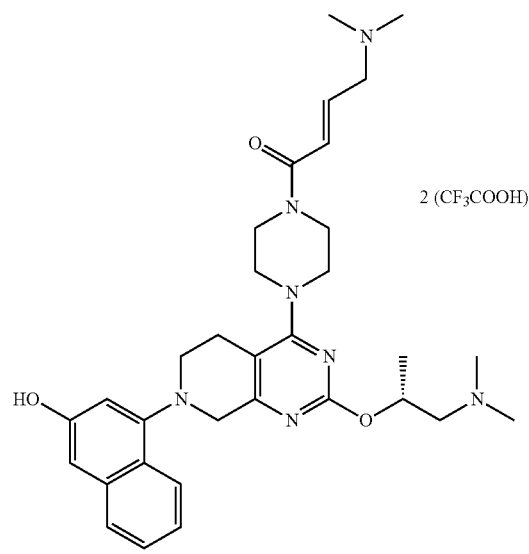 [SMILES: C[C@H](CN(C)C)Oc1nc2c(c(N3CCN(C(=O)/C=C/CN(C)C)CC3)n1)CCN(c1cc(O)cc3ccccc13)C2]

(R,E)-4-(dimethylamino)-1-(4-(2-((1-(dimethylamino)propan-2-yl)oxy)-7-(3-hydroxynaphthalen-1-yl)-5,6,7,8-tetrahydropyrido[3,4-d]pyrimidin-4-yl)piperazin-1-yl)but-2-en-1-one bis-trifluoroacetate

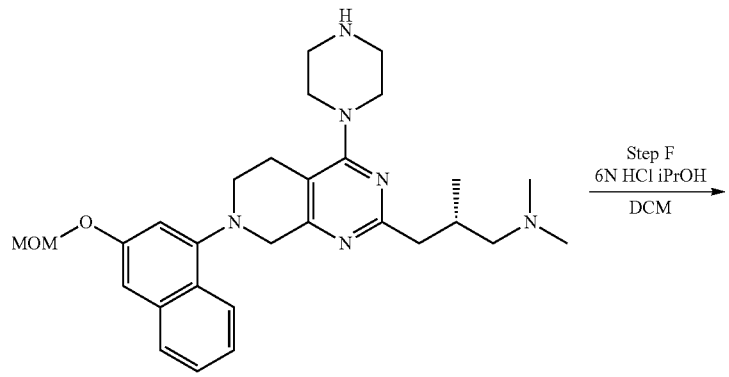

(As per Example 8, Step A-E)

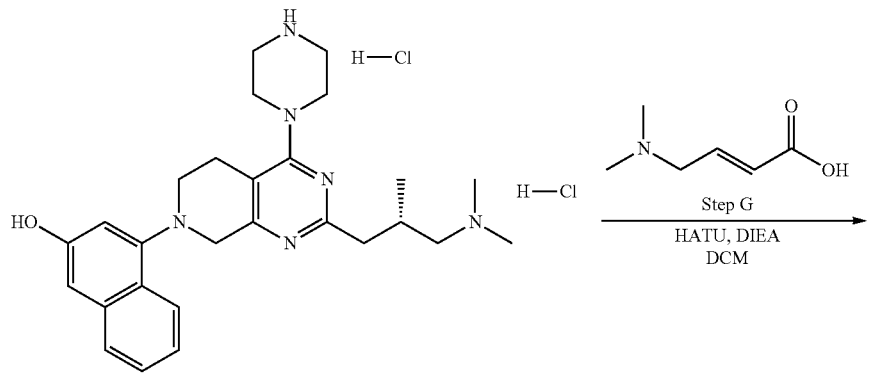

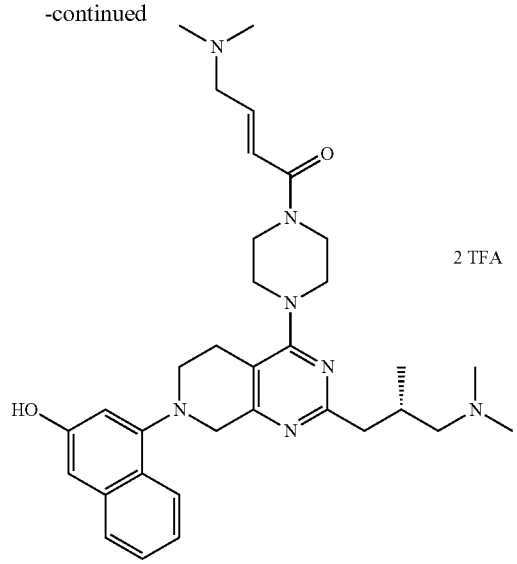

Steps A-E: (R)-2-((7-(3-(methoxymethoxy)naphthalen-1-yl)-4-(piperazin-1-yl)-5,6,7,8-tetrahydropyrido[3,4-d]pyrimidin-2-yl)oxy)-N,N-dimethylpropan-1-amine was synthesized according to the method of Example 8, Step A through Step E, using (R)-1-(dimethylamino)propan-2-ol in place of (S)-1-(dimethylamino)propan-2-ol in Step B.

Step F: (R)-4-(2-((1-(Dimethylamino)propan-2-yl)oxy)-4-(piperazin-1-yl)-5,8-dihydropyrido[3,4-d]pyrimidin-7(6H)-yl)naphthalen-2-ol dihydrochloride To a solution of (R)-2-((7-(3-(methoxymethoxy)naphthalen-1-yl)-4-(piperazin-1-yl)-5,6,7,8-tetrahydropyrido [3,4-d]pyrimidin-2-yl)oxy)-N,N-dimethylpropan-1-amine (75 mg, 0.15 mmol) in DCM (2.9 mL) was added 6N HCl in iPrOH (2470, 1.5 mmol) and the mixture was stirred at ambient temperature for 1 h. The reaction mixture was concentrated to dryness to provide (R)-4-(2-((1-(Dimethylamino)propan-2-yl)oxy)-4-(piperazin-1-yl)-5,8-dihydropyrido[3,4-d]pyrimidin-7(6H)-yl)naphthalen-2-ol dihydrochloride which was used directly in the next stop. ES+APCI MS m/z 463.2 [M+H]$^+$.

Step G: (R,E)-4-(Dimethylamino)-1-(4-(2-((1-(dimethylamino)propan-2-yl)oxy)-7-(3-hydroxynaphthalen-1-yl)-5,6,7,8-tetrahydropyrido[3,4-d]pyrimidin-4-yl)piperazin-1-yl)but-2-en-1-one bis-trifluoroacetate A solution of (R)-4-(2-((1-(Dimethylamino)propan-2-yl)oxy)-4-(piperazin-1-yl)-5,8-dihydropyrido[3,4-d]pyrimidin-7(6H)-yl)naphthalen-2-ol dihydrochloride (7 mg, 0.01 mmol), HATU (6.2 mg, 0.02 mmol), (2E)-4-(dimethylamino)but-2-enoic acid (2.1 mg, 0.02 mmol), DIEA (6.9 µl, 0.04 mmol) in DCM (131 µl) was stirred at ambient temperature for 1 h. The residue was filtered and the filtrate was loaded directly onto a Gilson C18 prep HPLC eluting with 5-95% acetonitrile/water with 0.1% TFA additive. The fractions containing the desired product were concentrated to provide (R,E)-4-(Dimethylamino)-1-(4-(2-((1-(dimethylamino)propan-2-yl)oxy)-7-(3-hydroxynaphthalen-1-yl)-5,6,7,8-tetrahydropyrido[3,4-d]pyrimidin-4-yl)piperazin-1-yl)but-2-en-1-one bis-trifluoroacetate. ES+APCI MS m/z 574.2 [M+H]$^+$.

Example 123

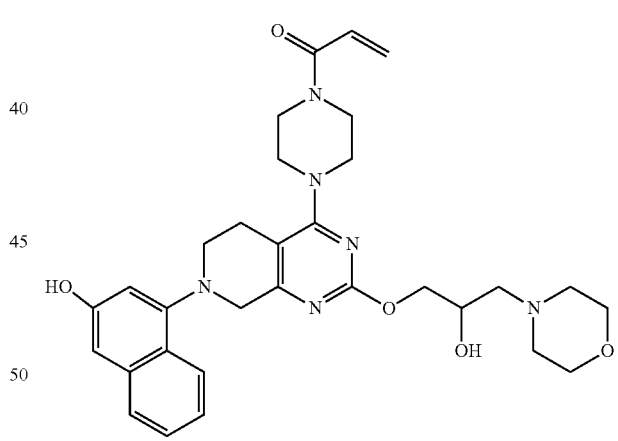

1-(4-(2-(2-hydroxy-3-morpholinopropoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 8, using 3-morpholinopropane-1,2-diol in place of (S)-1-(dimethylamino)propan-2-ol in Step B. ES+APCI MS m/z 575.2 [M+H]$^+$.

Example 124

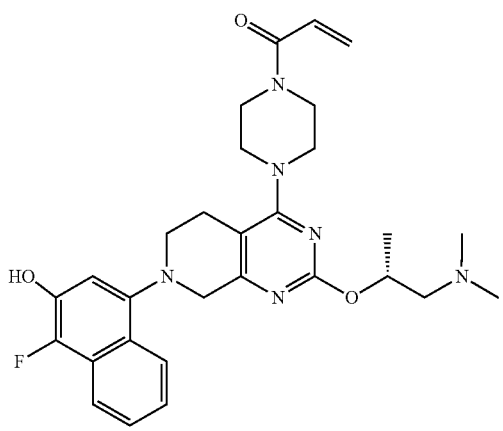 [SMILES: C=CC(=O)N1CCN(c2nc(O[C@H](C)CN(C)C)nc3c2CCN(c2cc(O)c(F)c4ccccc24)C3)CC1]

(R)-1-(4-(2-((1-(dimethylamino)propan-2-yl)oxy)-7-(4-fluoro-3-hydroxynaphthalen-1-yl)-5,6,7,8-tetrahydropyrido[3,4-d]pyrimidin-4-yl)piperazin-1-yl)prop-2-en-1-one Step A: Benzyl (R)-4-(2-((1-(dimethylamino)propan-2-yl)oxy)-7-(3-(methoxymethoxy)naphthalen-1-yl)-5,6,7,8-tetrahydropyrido[3,4-d]pyrimidin-4-yl)piperazine-1-carboxylate (221 mg, 0.345 mmol) was placed in ACN (2 mL) and the mixture was cooled to 0° C. SelectFluor (183 mg, 0.517 mmol) was added and the reaction was stirred at room temperature for 30 minutes. Water was added and the mixture was extracted with DCM. The organic layers were combined and concentrated. The resulting residue was purified by reverse phase chromatography (5-95% ACN:water with 0.1% TFA) to provide benzyl (R)-4-(2-((1-(dimethylamino)propan-2-yl)oxy)-7-(4-fluoro-3-(methoxymethoxy)naphthalen-1-yl)-5,6,7,8-tetrahydropyrido[3,4-d]pyrimidin-4-yl)piperazine-1-carboxylate trifluoroacetate (48 mg, 0.0729 mmol, 21.1% yield).

Step B: (R)-1-(4-(2-((1-(dimethylamino)propan-2-yl)oxy)-7-(4-fluoro-3-hydroxynaphthalen-1-yl)-5,6,7,8-tetrahydropyrido[3,4-d]pyrimidin-4-yl)piperazin-1-yl)prop-2-en-1-one was prepared following Example 33, Steps D-F substituting (R)-4-(2-((1-(dimethylamino)propan-2-yl)oxy)-7-(4-fluoro-3-(methoxymethoxy)naphthalen-1-yl)-5,6,7,8-tetrahydropyrido[3,4-d]pyrimidin-4-yl)piperazine-1-carboxylate trifluoroacetate for benzyl 4-(7-(3-(methoxymethoxy)naphthalen-1-yl)-5,6,7,8-tetrahydropyrido[3,4-d]pyrimidin-4-yl)piperazine-1-carboxylate. ES+APCI MS m/z 535.2 [M+H]+.

Example 125

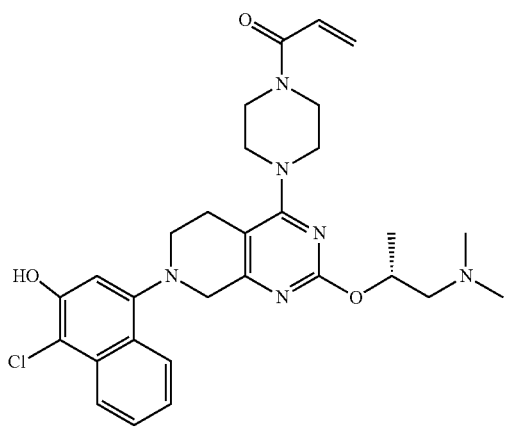 [SMILES: C=CC(=O)N1CCN(c2nc(O[C@H](C)CN(C)C)nc3c2CCN(c2cc(O)c(Cl)c4ccccc24)C3)CC1]

(R)-1-(4-(7-(4-chloro-3-hydroxynaphthalen-1-yl)-2-((1-(dimethyl amino)propan-2-yl)oxy)-5,6,7,8-tetrahydropyrido[3,4-d]pyrimidin-4-yl)piperazin-1-yl)prop-2-en-1-one Step A: Benzyl (R)-4-(2-((1-(dimethylamino)propan-2-yl)oxy)-7-(3-(methoxymethoxy)naphthalen-1-yl)-5,6,7,8-tetrahydropyrido[3,4-d]pyrimidin-4-yl)piperazine-1-carboxylate (83 mg, 0.130 mmol) and NCS (21.6 mg, 0.162 mmol) were placed in ACN (2 mL) and stirred at room temperature for 3 hours. Water was added and the mixture was extracted with DCM (3×15 mL). The organic layers were combined and concentrated. The resulting residue was purified by reverse phase chromatography (5-95% ACN:water with 0.1% TFA) to provide benzyl (R)-4-(7-(4-chloro-3-(methoxymethoxy)naphthalen-1-yl)-2-((1-(dimethylamino)propan-2-yl)oxy)-5,6,7,8-tetrahydropyrido[3,4-d]pyrimidin-4-yl)piperazine-1-carboxylate trifluoroacetate (17 mg, 0.0252 mmol, 19.4% yield).

Step B: (R)-1-(4-(7-(4-chloro-3-hydroxynaphthalen-1-yl)-2-((1-(dimethylamino)propan-2-yl)oxy)-5,6,7,8-tetrahydropyrido[3,4-d]pyrimidin-4-yl)piperazin-1-yl)prop-2-en-1-one was prepared following Example 33, Steps D-F substituting (R)-4-(7-(4-chloro-3-(methoxymethoxy)naphthalen-1-yl)-2-((1-(dimethylamino)propan-2-yl)oxy)-5,6,7,8-tetrahydropyrido[3,4-d]pyrimidin-4-yl)piperazine-1-carboxylate trifluoroacetate for benzyl 4-(7-(3-(methoxymethoxy)naphthalen-1-yl)-5,6,7,8-tetrahydropyrido[3,4-d]pyrimidin-4-yl)piperazine-1-carboxylate and using THF as the solvent in Step D. ES+APCI MS m/z 551.2 [M+H]+.

Example 126

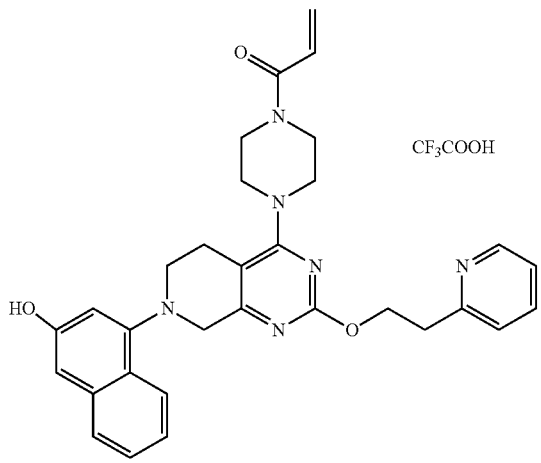 [SMILES: C=CC(=O)N1CCN(c2nc(OCCc3ccccn3)nc3c2CCN(c2cc(O)cc4ccccc24)C3)CC1 ; "CF3COOH"]

1-(4-(7-(3-hydroxynaphthalen-1-yl)-2-(2-(pyridin-2-yl)ethoxy)-5,6,7,8-tetrahydropyrido[3,4-d]pyrimidin-4-yl)piperazin-1-yl)prop-2-en-1-one trifluoroacetate

Step A: benzyl 4-(7-(3-(methoxymethoxy)naphthalen-1-yl)-2-(2-(pyridin-2-yl)ethoxy)-5,6,7,8-tetrahydropyrido[3,4-d]pyrimidin-4-yl)piperazine-1-carboxylate To a slurry of benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (0.20 g, 0.35 mmol) in dioxane in a microwave was added N-ethyl-N-isopropylpropan-2-amine (0.45 g, 3.5 mmol), Cs$_2$CO$_3$ (0.34 g, 1.0 mmol) and 2-(pyridin-2-yl)ethan-1-ol (0.43 g, 3.5 mmol) and the reaction heated to 15° C. for 1 hr in the microwave. The reaction was diluted with EtOAc and washed with water, brine, dried over MgSO$_4$ and concentrated in vacuo. The material was chromatographed using a gradient of 0 to 100% EtOAc/DCM as the eluent to give benzyl 4-(7-(3-(methoxymethoxy)naphthalen-1-yl)-2-(2-(pyridin-2-yl)ethoxy)-5,6,7,8-tetrahydropyrido[3,4-d]pyrimidin-4-yl)piperazine-1-carboxylate (0.16 g, 0.24 mmol, 70% yield).

Step B: 4-(4-(piperazin-1-yl)-2-(2-(pyridin-2-yl)ethoxy)-5,8-dihydropyrido[3,4-d]pyrimidin-7(6H)-yl)naphthalen-2-ol To the solid benzyl 4-(7-(3-(methoxymethoxy)naphthalen-1-yl)-2-(2-(pyridin-2-yl)ethoxy)-5,6,7,8-tetrahydropyrido[3,4-d]pyrimidin-4-yl)piperazine-1-carboxylate (0.12 g, 0.18 mmol) was added MeOH (20 mL). The solution was degassed with nitrogen 5 minutes, followed by addition of Pd/C (0.058 g, 0.54 mmol). The reaction vessel was evacuated by vacuum and backfilled with H$_2$. This procedure was performed three times, and after the third backfill the slurry was left to sir under an atmosphere of hydrogen for 1 hr. The reaction was again degassed with nitrogen for 5 minutes. The slurry was next filtered through Celite® and the Celite® was washed with MeOH (100 mL). The combined organic extracts were concentrated and treated with 10 mL of 1:1 TFA/DCM for 2 hrs. The reaction was again concentrated in vacuo to give 4-(4-(piperazin-1-yl)-2-(2-(pyridin-2-yl)ethoxy)-5,8-dihydropyrido[3,4-d]pyrimidin-7(6H)-yl)naphthalen-2-ol (0.096 g, 0.20 mmol, 110% yield).

Step C: 1-(4-(7-(3-hydroxynaphthalen-1-yl)-2-(2-(pyridin-2-yl)ethoxy)-5,6,7,8-tetrahydropyrido[3,4-d]pyrimidin-4-yl)piperazin-1-yl)prop-2-en-1-one To a solution of 4-(4-(piperazin-1-yl)-2-(2-(pyridin-2-yl)ethoxy)-5,8-dihydropyrido[3,4-d]pyrimidin-7(6H)-yl)naphthalen-2-ol (0.096 g, 0.20 mmol) in DCM was added Hunig's Base (0.17 mL, 0.99 mmol) and acryloyl chloride (0.018 g, 0.20 mmol) and the reaction stirred for 30 minutes at room temperature. The reaction was concentrated in vacuo and the crude material was purified by reverse preparative HPLC to give 1-(4-(7-(3-hydroxynaphthalen-1-yl)-2-(2-(pyridin-2-yl)ethoxy)-5,6,7,8-tetrahydropyrido[3,4-d]pyrimidin-4-yl)piperazin-1-yl)prop-2-en-1-one trifluoroacetate (0.0057 g, 0.011 mmol, 5.3% yield). ES+APCI MS m/z 537.2 [M+H]$^+$.

Example 127

(S)-7-(3-(methoxymethoxy)naphthalen-1-yl)-2-((1-methylpyrrolidin-2-yl)methoxy)-4-(piperazin-1-yl)-5,6,7,8-tetrahydropyrido[3,4-d]pyrimidine

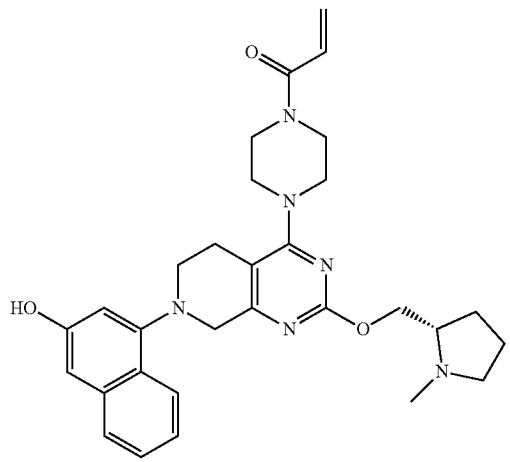

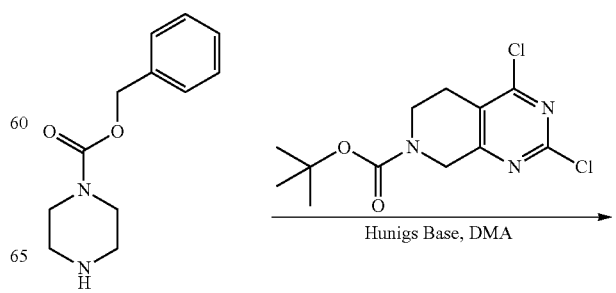

381

-continued

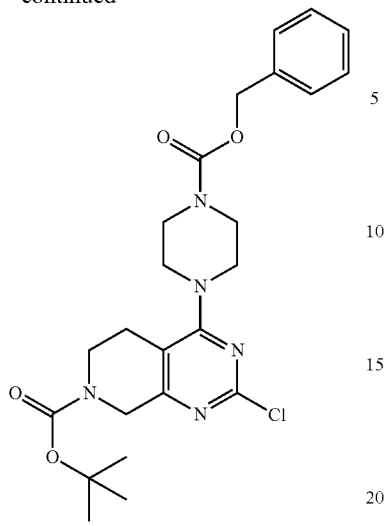

Step A: tert-butyl 4-(4-((benzyloxy)carbonyl)piper-azin-1-yl)-2-chloro-5,8-dihydropyrido[3,4-d]pyrimi-dine-7(6H)-carboxylate To a solution of tert-butyl 2,4-dichloro-5,8-dihydropyrido[3,4-d]pyrimidine-7(6H)-carboxylate (8 g, 26.30 mmol) in DMA (263.0 ml, 26.30 mmol) was added benzyl piperazine-1-carboxylate (5.793 g, 26.30 mmol) and N-ethyl-N-isopropylpropan-2-amine (4.721 ml, 26.30 mmol) and the reaction stirred at room temperature for 2 hours. TLC (20% EtOAc/DCM), UV visualization, showed reaction completion. The reaction was next poured into water and extracted into DCM. The organics were next washed with water (2×), brine, dried over MgSO₄ and concentrated in vacuo. The concentrate was loaded onto a 220 g RegiSep column and chromatagraphed on the CombiFlash (0%-10%, EtOAc:DCM). All fractions containing desired product were combined and concentrated to give tert-butyl 4-(4-((benzyloxy) carbonyl)piperazin-1-yl)-2-chloro-5,8-dihydropyrido[3,4-d] pyrimidine-7(6H)-carboxylate (9.768 g, 20.02 mmol, 76.11% yield) as a white foam. ES+APCI MS m/z 488.2 [M+H]⁺.

382

-continued

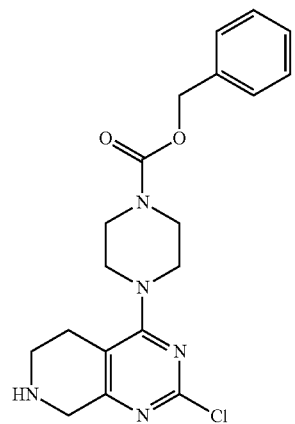

Step B: benzyl 4-(2-chloro-5,6,7,8-tetrahydropyrido [3,4-d]pyrimidin-4-yl)piperazine-1-carboxylate tert-butyl 4-(4-((benzyloxy)carbonyl)piperazin-1-yl)-2-chloro-5,8-dihydropyrido[3,4-d]pyrimidine-7(6H)-carboxylate (9.768 g, 20.02 mmol) was dissolved in dichloromethane (200.2 ml, 20.02 mmol) and treated with 2,2,2-trifluoroacetic acid (15.33 ml, 200.2 mmol). The reaction mixture stirred at room temp for 4 hours. After completion the reaction was next concentrated in vacuo and taken up in EtOAc and the organics washed with 1M NaOH (2×), brine, dried over MgSO₄ and concentrated in vacuo. benzyl 4-(2-chloro-5,6,7,8-tetrahydropyrido[3,4-d]pyrimidin-4-yl)piperazine-1-carboxylate (7.406 g, 19.09 mmol, 95.39% yield) was used crude in the next reaction. ES+APCI MS m/z 388.2 [M+H]⁺.

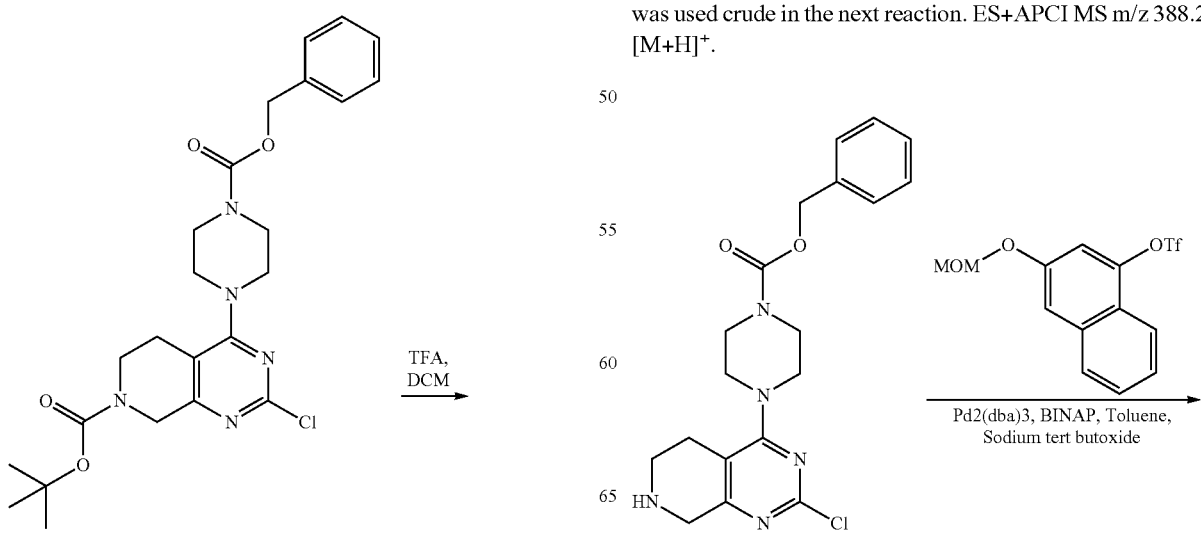

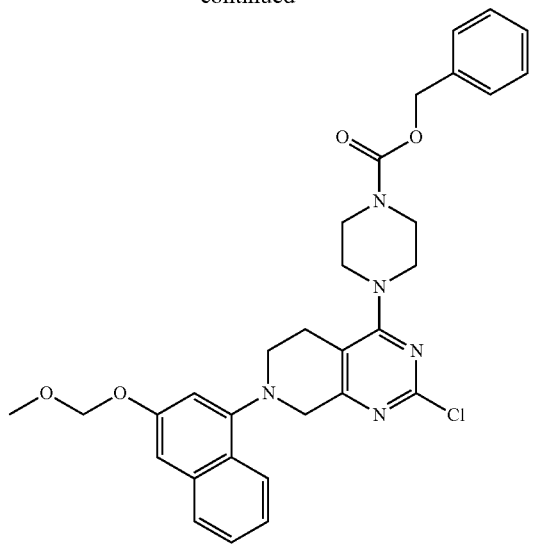

Step C: benzyl 4-(2-chloro-7-(3-(methoxymethoxy)naphthalen-1-yl)-5,6,7,8-tetrahydropyrido[3,4-d]pyrimidin-4-yl)piperazine-1-carboxylate To the benzyl 4-(2-chloro-5,6,7,8-tetrahydropyrido[3,4-d]pyrimidin-4-yl)piperazine-1-carboxylate, BINAP (0.275 g, 0.442 mmol) and $Pd_2(dba)_3$ (0.203 g, 0.221 mmol) under argon was added toluene (221 ml, 11.1 mmol) and the reaction bubbled with Ar for 10 minutes followed by heating to 100° C. for 10 minutes. The reaction was next cooled to room temperature and benzyl 4-(2-chloro-5,6,7,8-tetrahydropyrido[3,4-d]pyrimidin-4-yl)piperazine-1-carboxylate (4.29 g, 11.1 mmol) and Sodium Tert-Butoxide (2.13 g, 22.1 mmol) were added to the dark solution as solids. Finally, 3-(methoxymethoxy)naphthalen-1-yl trifluoromethanesulfonate (7.44 g, 22.1 mmol) was added (as the oil) and the reaction heated to 100° C. for 1 hour. The reaction was cooled to room temperature and concentrated in vacuo. The concentrate was dissolved with EtOAc and washed with water and brine. The combined organics were dried over $Na_2SO_4$ and concentrated in vacuo. The residue was then loaded on the CombiFlash and chromatographed using 0%→50% Hexane:EtOAc as eluent. Fractions containing clean product were combined and concentrated in vacuo to afford benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (2.6 g, 4.53 mmol, 40.9% yield). ES+APCI MS m/z 574.2 [M+H]+.

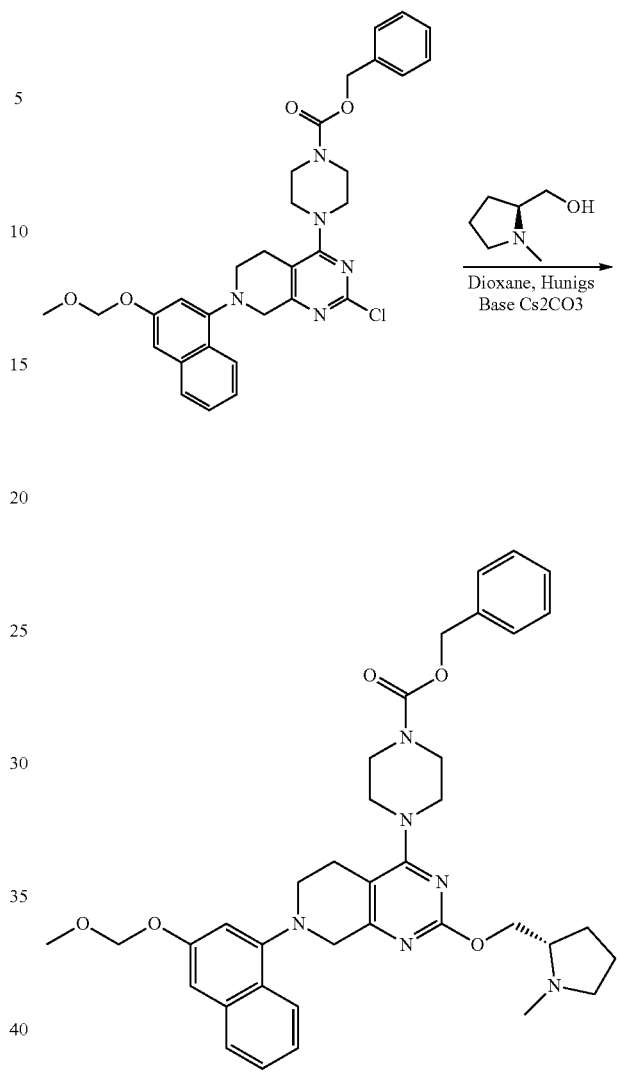

Step D: benzyl (S)-4-(7-(3-(methoxymethoxy)naphthalen-1-yl)-2-((1-methylpyrrolidin-2-yl)methoxy)-5,6,7,8-tetrahydropyrido[3,4-d]pyrimidin-4-yl)piperazine-1-carboxylate: In a microwave tube benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (300 mg, 0.523 mmol) was dissolved in Dioxane (6532 µl, 0.523 mmol) and treated with cesium carbonate (511 mg, 1.57 mmol), Hunig's base (913 µl, 5.23 mmol) and N-Methyl-L-prolinol (421 mg, 3.66 mmol). The tube was then capped and microwaved at 170° C. for 3 hours. The reaction was filtered through GF/F paper. The filtrate was concentrated in vacuo and the residue loaded onto a 12 g RegiSep gold column and chromatagraphed on the CombiFlash (0%-15%, DCM:MeOH). All fractions containing clean product were combined and concentrated in vacuo to give benzyl (S)-4-(7-(3-(methoxymethoxy)naphthalen-1-yl)-2-((1-methylpyrrolidin-2-yl)methoxy)-5,6,7,8-tetrahydropyrido[3,4-d]pyrimidin-4-yl)piperazine-1-carboxylate (220 mg, 0.337 mmol, 64.5% yield). ES+APCI MS m/z 653.3 [M+H]+.

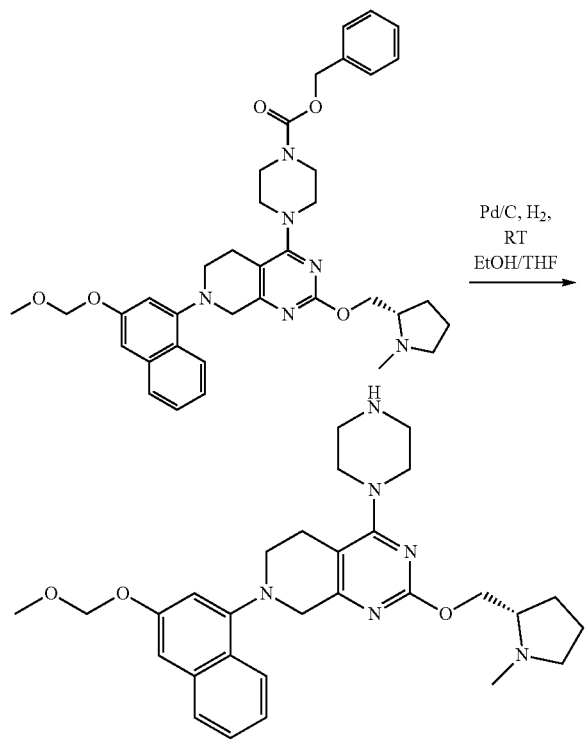

Step E: (S)-7-(3-(methoxymethoxy)naphthalen-1-yl)-2-((1-methylpyrrolidin-2-yl)methoxy)-4-(piperazin-1-yl)-5,6,7,8-tetrahydropyrido[3,4-d]pyrimidine: A solution of benzyl (S)-4-(7-(3-(methoxymethoxy)naphthalen-1-yl)-2-((1-methylpyrrolidin-2-yl)methoxy)-5,6,7,8-tetrahydropyrido[3,4-d]pyrimidin-4-yl)piperazine-1-carboxylate (220 mg, 0.337 mmol) in EtOH (3370 µl, 0.337 mmol) and THF (3370 µl, 0.337 mmol) was purged with N2 for 5 minutes. To this solution was added Palladium on carbon (179 mg, 0.0843 mmol) (Degussa Type, 10 wt %, 50% H2O), and was immediately capped and purged with N2 for an additional 5 min. The solution then stirred under H2 introduced via vacuum followed by balloon pressure. The mixture was then stirred at ambient temperature over night. LC/MS showed reaction completion. The mixture was diluted with MeOH and filtered through packed celite. The filtrate was then concentrated in vacuo and (S)-7-(3-(methoxymethoxy)naphthalen-1-yl)-2-((1-methylpyrrolidin-2-yl)methoxy)-4-(piperazin-1-yl)-5,6,7,8-tetrahydropyrido[3,4-d]pyrimidine (91 mg, 0.175 mmol, 52.1% yield) was taken forward as the crude. ES+APCI MS m/z 519.3 [M+H]+.

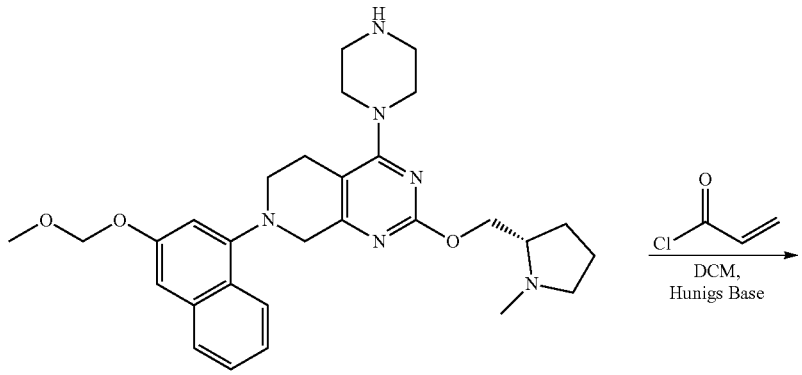

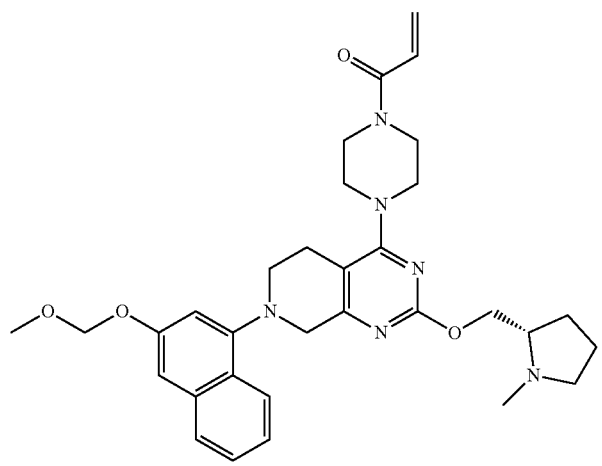

Step F: (S)-1-(4-(7-(3-(methoxymethoxy)naphthalen-1-yl)-2-((1-methylpyrrolidin-2-yl)methoxy)-5,6,7,8-tetrahydropyrido[3,4-d]pyrimidin-4-yl)piperazin-1-yl)prop-2-en-1-one: To a suspension of (S)-7-(3-(methoxymethoxy)naphthalen-1-yl)-2-((1-methylpyrrolidin-2-yl)methoxy)-4-(piperazin-1-yl)-5,6,7,8-tetrahydropyrido[3,4-d]pyrimidine (92 mg, 0.18 mmol) in dichloromethane (1774 µl, 0.18 mmol) at ambient temperature was added Acryloyl Chloride (1774 µl, 0.18 mmol) followed by Hunig's base (62 µl, 0.35 mmol). The reaction was then stirred at ambient temperature for 1 hour. The mixture was then concentrated and loaded onto a 4 g RegiSep gold column and chromatagraphed on the CombiFlash (0%-15%, DCM:MeOH). All fractions containing clean product were combined and concentrated in vacuo to give (S)-1-(4-(7-(3-(methoxymethoxy)naphthalen-1-yl)-2-((1-methylpyrrolidin-2-yl)methoxy)-5,6,7,8-tetrahydropyrido[3,4-d]pyrimidin-4-yl)piperazin-1-yl)prop-2-en-1-one (74 mg, 0.13 mmol, 73% yield). ES+APCI MS m/z 573.3 [M+H]$^+$.

[3,4-d]pyrimidin-4-yl)piperazin-1-yl)prop-2-en-1-one: (S)-1-(4-(7-(3-(methoxymethoxy)naphthalen-1-yl)-2-((1-methylpyrrolidin-2-yl)methoxy)-5,6,7,8-tetrahydropyrido[3,4-d]pyrimidin-4-yl)piperazin-1-yl)prop-2-en-1-one (74 mg, 0.13 mmol) was dissolved in methanol (4307 µl, 0.13 mmol) and treated with hydrogen chloride (1077 µl, 6.5 mmol) (aq). The reaction stirred at 55° C. for 1 hour. The reaction mixture was concentrated in vaccuo and was resuspended in 1.5 mL of MeOH. The suspension was loaded on to the Gilson (prep HPLC), which was eluted with 5→95% ACN/0.1% TFA in water/0.1% TFA. All fractions containing clean product were combined and lyophilized overnight to give (S)-1-(4-(7-(3-hydroxynaphthalen-1-yl)-2-((1-methylpyrrolidin-2-yl)methoxy)-5,6,7,8-tetrahydropyrido[3,4-d]pyrimidin-4-yl)piperazin-1-yl)prop-2-en-1-one (26 mg, 0.049 mmol, 38% yield). ES+APCI MS m/z 529.3 [M+H]$^+$.

Example 128

1-(4-(2-(3-(dimethylamino)azetidin-1-yl)-7-(3-hydroxynaphthalen-1-yl)-5,6,7,8-tetrahydropyrido[3,4-d]pyrimidin-4-yl)piperazin-1-yl)prop-2-en-1-one

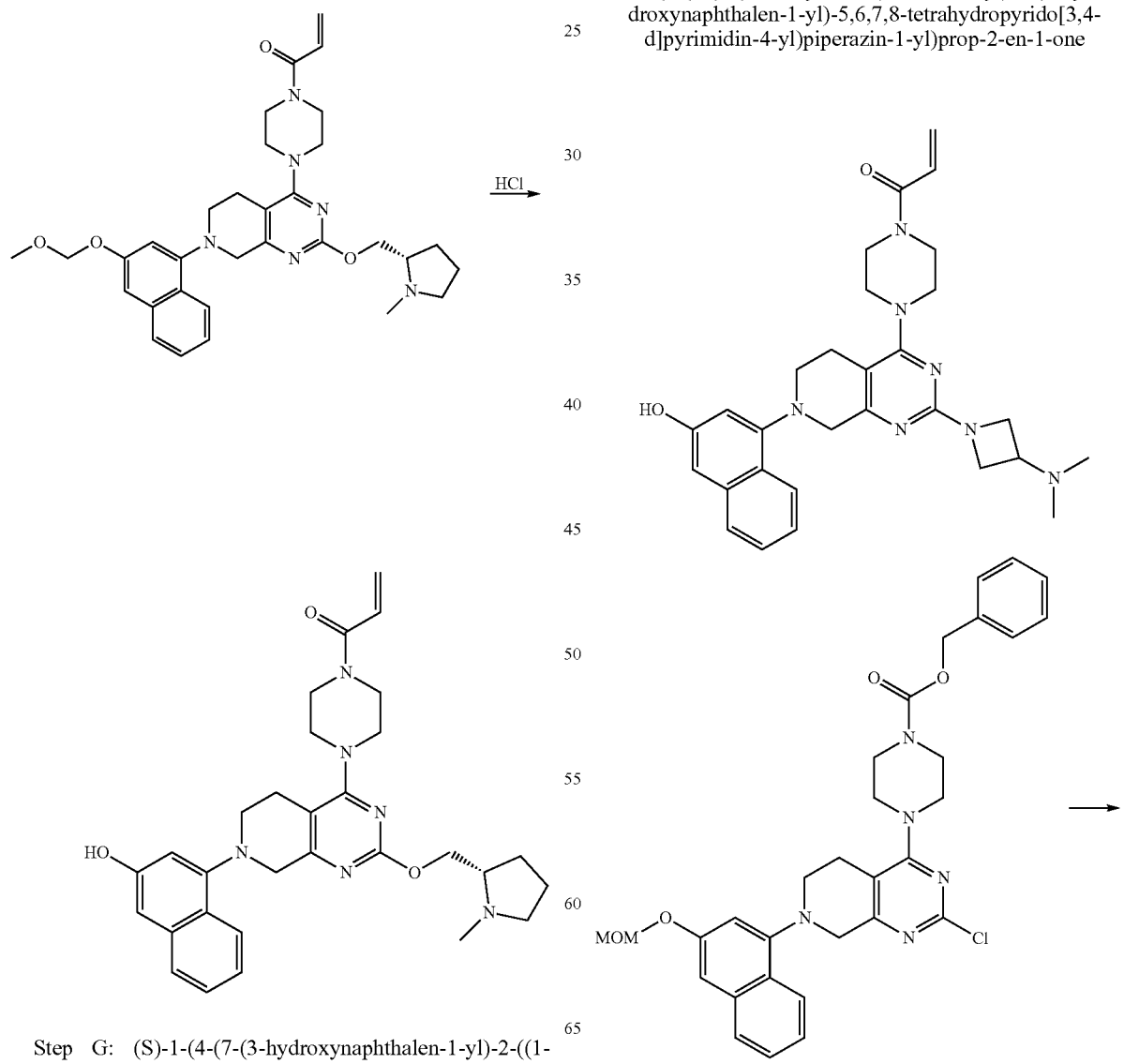

Step G: (S)-1-(4-(7-(3-hydroxynaphthalen-1-yl)-2-((1-methylpyrrolidin-2-yl)methoxy)-5,6,7,8-tetrahydropyrido

389
-continued

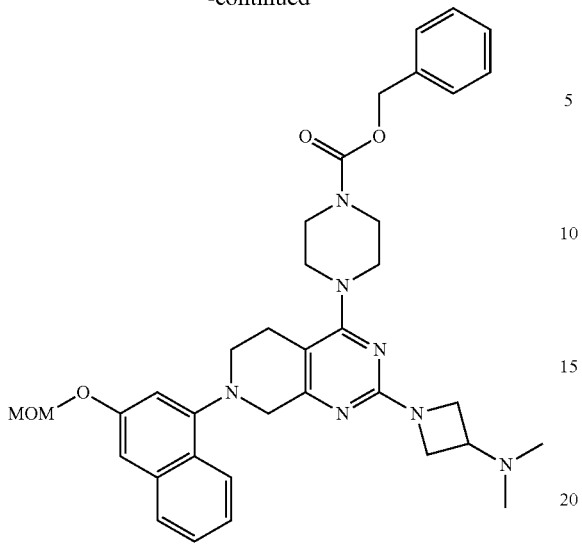

Step A: benzyl 4-(2-(3-(dimethylamino)azetidin-1-yl)-7-(3-(methoxymethoxy)naphthalen-1-yl)-5,6,7,8-tetrahydropyrido[3,4-d]pyrimidin-4-yl)piperazine-1-carboxylate: To a solution of benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (0.20 g, 0.35 mmol) in dioxanes was added N,N-dimethylazetidin-3-amine hydrochloride (0.24 g, 1.7 mmol) and N-ethyl-N-isopropylpropan-2-amine (0.45 g, 3.5 mmol) and the reaction was heated to 80 C for 72 hrs. The reaction was concentrated in vacuo and the residue chromatographed using 0→20% MeOH/DCM as eluent to give benzyl 4-(2-(3-(dimethylamino)azetidin-1-yl)-7-(3-(methoxymethoxy)naphthalen-1-yl)-5,6,7,8-tetrahydropyrido[3,4-d]pyrimidin-4-yl)piperazine-1-carboxylate (0.25 g, 105%). ES+APCI MS m/z 638.3 [M+H]$^+$.

1-(4-(2-(3-(dimethylamino)azetidin-1-yl)-7-(3-hydroxynaphthalen-1-yl)-5,6,7,8-tetrahydropyrido[3,4-d]pyrimidin-4-yl)piperazin-1-yl)prop-2-en-1-one was made according to Example 127 substituting benzyl 4-(2-(3-(dimethylamino)azetidin-1-yl)-7-(3-(methoxymethoxy)naphthalen-1-yl)-5,6,7,8-tetrahydropyrido[3,4-d]pyrimidin-4-yl)piperazine-1-carboxylate for benzyl (S)-4-(7-(3-(methoxymethoxy)naphthalen-1-yl)-2-((1-methylpyrrolidin-2-yl)methoxy)-5,6,7,8-tetrahydropyrido[3,4-d]pyrimidin-4-yl)piperazine-1-carboxylate in step E. ES+APCI MS m/z 514.2 [M+H]$^+$.

390

Example 129

1-[4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazin-1-yl]prop-2-en-1-one

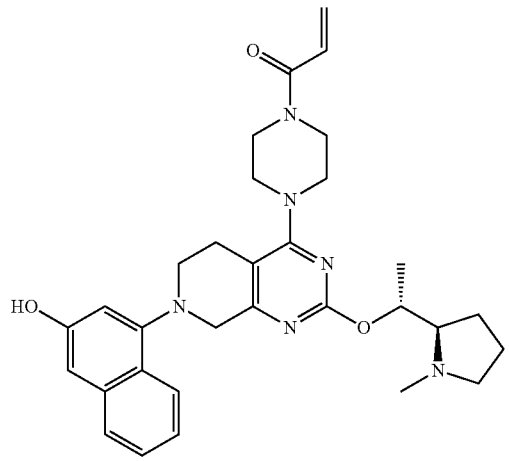

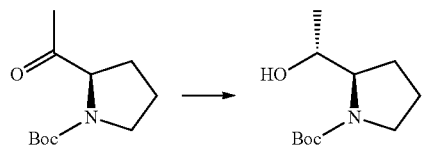

Step A: tert-butyl (2R)-2-[(1R)-1-hydroxyethyl]pyrrolidine-1-carboxylate

A mixture of BH$_3$-Me$_2$S (10 M, 549 uL) and (3aS)-1-methyl-3,3-diphenyl-3a,4,5,6-tetrahydropyrrolo[1,2-c][1,3,2]oxazaborole (1.00 M, 844 uL) in THF (10 mL) was stirred at 15° C. for 1 hour. To the mixture was added a solution of tert-butyl (2R)-2-acetylpyrrolidine-1-carboxylate (0.90 g, 4.22 mmol) in THF (10 mL) and the mixture stirred at 15° C. for 1 hour. The mixture was quenched by addition of methanol (2.00 mL) and the reaction concentrated under vacuum. The residue was purified by column chromatography (SiO$_2$, petroleum ether/ether acetate=50/1-5/1) to give tert-butyl (2R)-2-[(1R)-1-hydroxyethyl]pyrrolidine-1-carboxylate (0.60 g, 2.79 mmol, 66.0% yield) as a colorless oil. $^1$H NMR (400 MHz, CD3OD) δ=5.18 (br s, 1H), 3.73 (dt, J=4.8, 8.0 Hz, 1H), 3.70-3.43 (m, 2H), 3.28 (td, J=6.64, 10.8 Hz, 1H), 1.96 (qd, J=7.2, 12.8 Hz, 1H), 1.89-1.68 (m, 2H), 1.62 (br s, J=6.4 Hz, 1H), 1.47 (s, 9H), 1.15 (d, J=6.0 Hz, 3H).

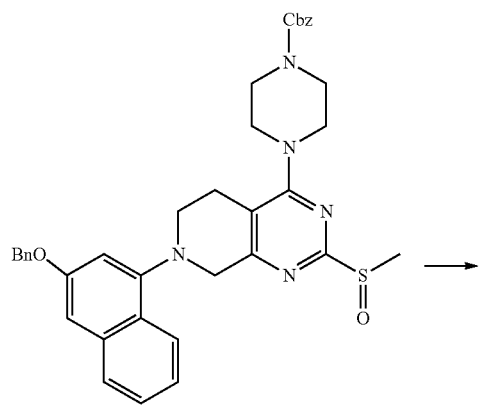

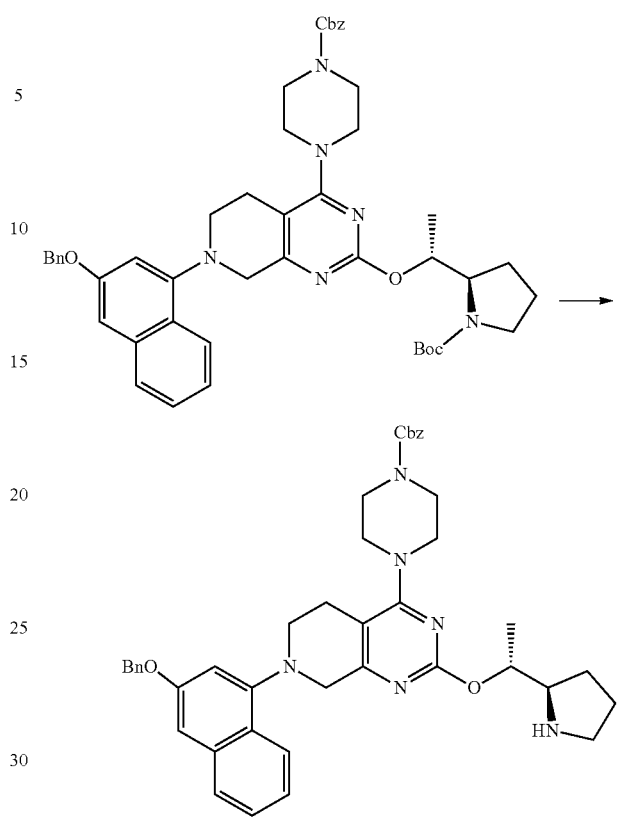

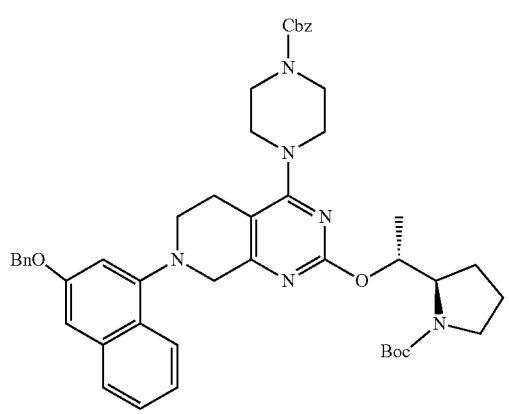

Step B: benzyl 4-[7-(3-benzyloxy-1-naphthyl)-2-[(1R)-1-[(2R)-1-tert-butoxycarbonylpyrrolidin-2-yl]ethoxy]-6,8-dihydro-5H-pyrido[3,4-d]pyrimidin-4-yl]piperazine-1-carboxylate: To a solution of benzyl 4-[7-(3-benzyloxy-1-naphthyl)-2-methylsulfinyl-6,8-dihydro-5H-pyrido[3,4-d]pyrimidin-4-yl]piperazine-1-carboxylate (0.70 g, 1.08 mmol) and tert-butyl (2R)-2-[(1R)-1-hydroxyethyl]pyrrolidine-1-carboxylate (349 mg, 1.62 mmol) in THF (10 mL) was added t-BuONa (312 mg, 3.24 mmol) and the mixture stirred at 10° C. for 1 hour. The mixture was diluted with water (10 mL) and the aqueous layer extracted with ethyl acetate (3×10 mL). The combined organics were washed brine (20 mL), dried over Na$_2$SO$_4$, filtered and concentrated under vacuum. The residue was purified by column chromatography (SiO$_2$, petroleum ether/ether acetate=3/1) to give benzyl 4-[7-(3-benzyloxy-1-naphthyl)-2-[(1R)-1-[(2R)-1-tert-butoxycarbonylpyrrolidin-2-yl]ethoxy]-6,8-dihydro-5H-pyrido[3,4-d]pyrimidin-4-yl]piperazine-1-carboxylate (0.35 g, 412 umol, 38.1% yield) as a yellow solid. ES+APCI MS m/z 799.4 [M+H]$^+$.

Step C: benzyl 4-[7-(3-benzyloxy-1-naphthyl)-2-[(1R)-1-[(2R)-pyrrolidin-2-yl]ethoxy]-6,8-dihydro-5H-pyrido[3,4-d]pyrimidin-4-yl]piperazine-1-carboxylate: A mixture of benzyl 4-[7-(3-benzyloxy-1-naphthyl)-2-[(1R)-1-[(2R)-1-tert-butoxycarbonylpyrrolidin-2-yl]ethoxy]-6,8-dihydro-5H-pyrido[3,4-d]pyrimidin-4-yl]piperazine-1-carboxylate (0.30 g, 375 umol) and TFA (642 mg, 5.63 mmol, 417 uL) in dichloromethane (0.42 mL) was stirred at 10° C. for 1 hour. The mixture was concentrated under vacuum to give benzyl 4-[7-(3-benzyloxy-1-naphthyl)-2-[(1R)-1-[(2R)-pyrrolidin-2-yl]ethoxy]-6,8-dihydro-5H-pyrido[3,4-d]pyrimidin-4-yl]piperazine-1-carboxylate (305 mg) LCMS [M+1]: ES+APCI MS m/z 699.2 [M+H]$^+$.

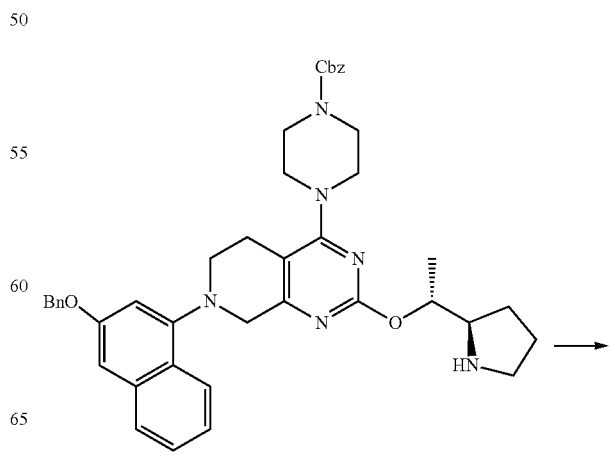

-continued

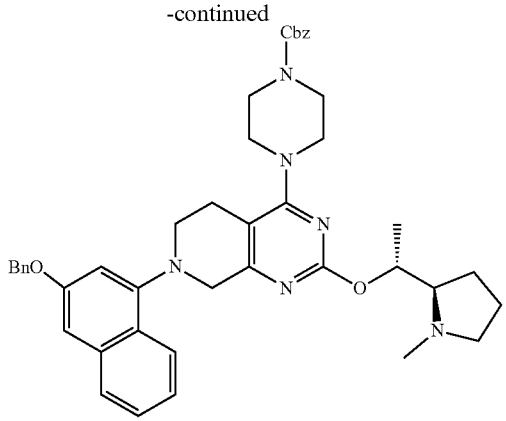

Step D: benzyl 4-[7-(3-benzyloxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazine-1-carboxylate: A mixture of benzyl 4-[7-(3-benzyloxy-1-naphthyl)-2-[(1R)-1-[(2R)-pyrrolidin-2-yl]ethoxy]-6,8-dihydro-5H-pyrido[3,4-d]pyrimidin-4-yl]piperazine-1-carboxylate (0.30 g, crude), formaldehyde (210 mg, 1.85 mmol, 192 uL, 37% water) and AcOH (22.16 mg, 369 umol, 21.1 uL) in methanol (3.00 mL) was stirred at 15° C. for 0.5 hours. To the mixture was added NaBH$_3$CN (58.0 mg, 923 umol) and the mixture stirred at 15° C. for 48 hours. The mixture was quenched by addition of H$_2$O (5 mL) at 0° C., and the aqueous layer extracted with ether acetate (3×10 mL). The combined organics were washed with brine (15.0 mL), dried over Na$_2$SO$_4$, filtered and concentrated under vacuum. The residue was purified by reverse phase flash [water (0.10% Formic Acid)/acetonitrile] to give benzyl 4-[7-(3-benzyloxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazine-1-carboxylate (0.10 g, 126 umol) as a yellow oil. ES+APCI MS m/z 713.4 [M+H]$^+$.

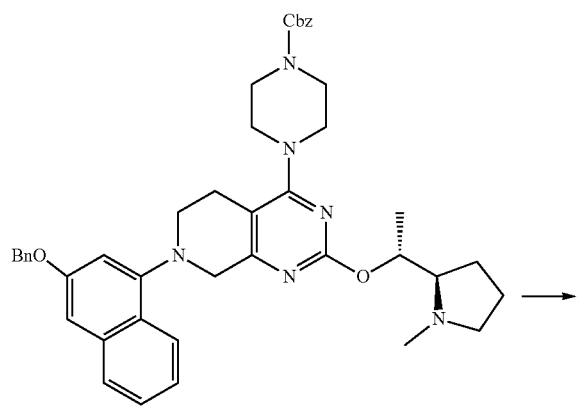

-continued

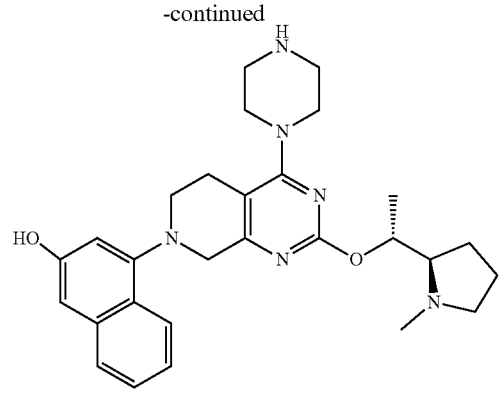

Step E: 4-[2-[(1R)-1-[(2R)-1-methylpyrrolidin-2-yl]ethoxy]-4-piperazin-1-yl-6,8-dihydro-5H-pyrido[3,4-d]pyrimidin-7-yl]naphthalen-2-ol Ammonia was bubbled into methanol (3 mL) at −78° C. for 30 minutes. benzyl 4-[7-(3-benzyloxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazine-1-carboxylate (0.09 g, 126 umol) and dry 10% Pd/C (0.10 g) were next added and the mixture stirred at 10° C. for 1 hour under H$_2$ (15 psi). The reaction was filtered and the filtrate was concentrated under vacuum to give 4-[2-[(1R)-1-[(2R)-1-methylpyrrolidin-2-yl]ethoxy]-4-piperazin-1-yl-6,8-dihydro-5H-pyrido[3,4-d]pyrimidin-7-yl]naphthalen-2-ol (0.04 g, crude) as a yellow oil. ES+APCI MS m/z 489.2 [M+H]$^+$.

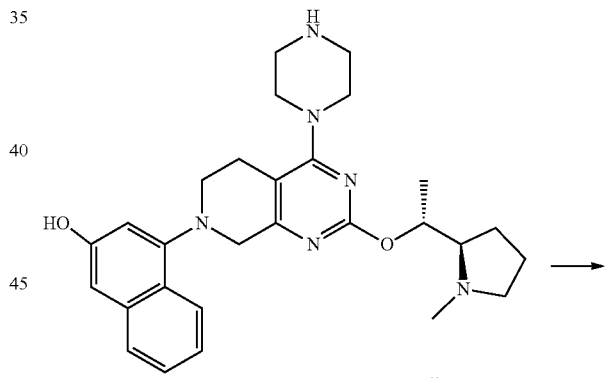

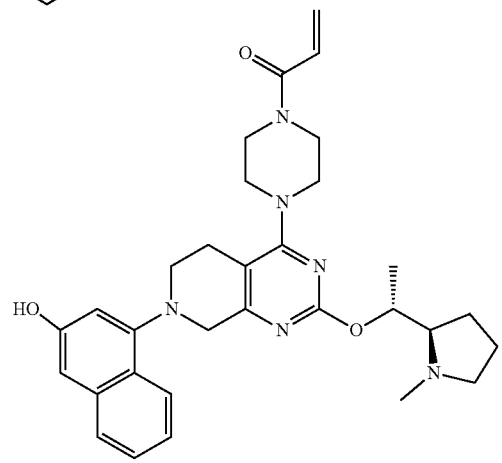

Step F: 1-[4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazin-1-yl]prop-2-en-1-one: To a solution of 4-[2-[(1R)-1-[(2R)-1-methylpyrrolidin-2-yl]ethoxy]-4-piperazin-1-yl-6,8-dihydro-5H-pyrido[3,4-d]pyrimidin-7-yl]naphthalen-2-ol (0.04 g) and Et₃N (124 mg, 1.23 mmol, 171 uL) in DCM (2.00 mL) at −40° C. was added prop-2-enoyl prop-2-enoate (7.23 mg, 57.3 umol) and the reaction stirred at −40° C. for 0.5 h. The mixture was quenched by addition of methanol (0.10 mL) and concentrated under vacuum. The residue was purified by prep-HPLC (column: Phenomenex Synergi C18 150*25*10 um; mobile phase: [water (0.225% Formic Acid)-ACN]; B %: 10%-37% over 10 minutes) to give 1-[4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazin-1-yl]prop-2-en-1-one (9.13 mg, 15.5 umol) as a yellow solid. ES+APCI MS m/z 543.4 [M+H]⁺.

Example 130

1-(4-(7-(3-hydroxynaphthalen-1-yl)-2-((S)-1-((S)-1-methylpyrrolidin-2-yl)ethoxy)-5,6,7,8-tetrahydropyrido[3,4-d]pyrimidin-4-yl)piperazin-1-yl)prop-2-en-1-one

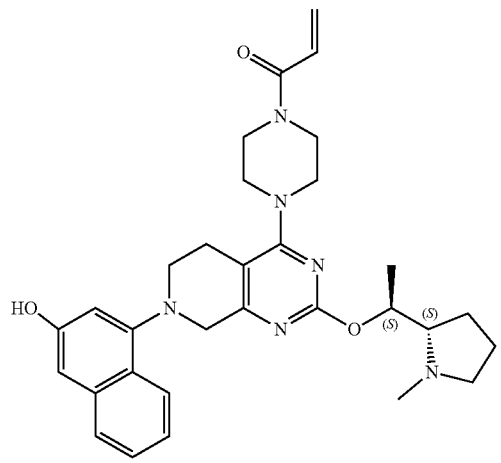

1-(4-(7-(3-hydroxynaphthalen-1-yl)-2-((S)-1-((S)-1-methylpyrrolidin-2-yl)ethoxy)-5,6,7,8-tetrahydropyrido[3,4-d]pyrimidin-4-yl)piperazin-1-yl)prop-2-en-1-one was prepared following Example 129 substituting (3aR)-1-methyl-3,3-diphenyl-3a,4,5,6-tetrahydro pyrrolo[1,2-c][1,3,2]oxazaborole for (3aS)-1-methyl-3,3-diphenyl-3a,4,5,6-tetrahydropyrrolo[1,2-c][1,3,2]oxazaborole in Step A while also substituting tert-butyl (2S)-2-acetylpyrrolidine-1-carboxylate for tert-butyl (2R)-2-acetylpyrrolidine-1-carboxylate in Step A. ES+APCI MS m/z 543.4 [M+H]⁺.

Example 131

1-[4-[2-[(1R)-2-[ethyl(methyl)amino]-1-methylethoxy]-7-(3-hydroxy-1-naphthyl)-6,8-dihydro-5H-pyrido[3,4-d]pyrimidin-4-yl]piperazin-1-yl]prop-2-en-1-one

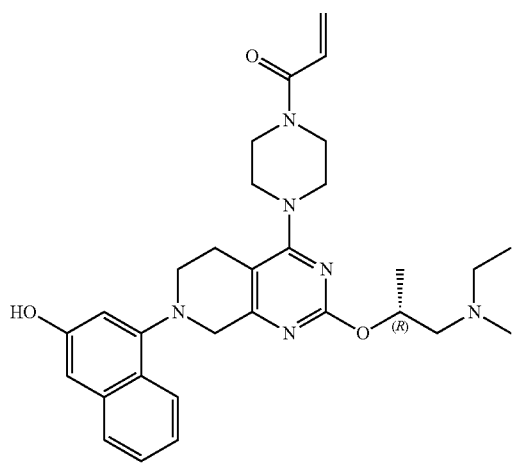

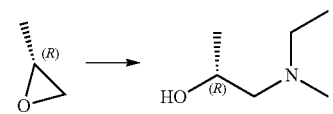

Step A: (2R)-1-[ethyl(methyl)amino]propan-2-ol (2R)-2-methyloxirane (540 mg, 9.31 mmol, 651 uL) was added to N-methylethanamine (500 mg, 8.46 mmol, 725 uL) in MeOH (10 mL). The resulting solution was stirred at 80° C. for 3 hours in a sealed tube. Upon completion, the mixture was concentrated under vacuum to give (2R)-[ethyl(methyl)amino]propan-2-ol (260 mg, crude) as a light yellow oil which was used directly in the next step without further purification.

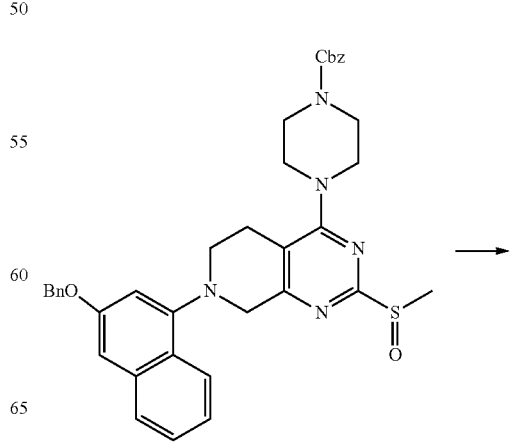

397
-continued

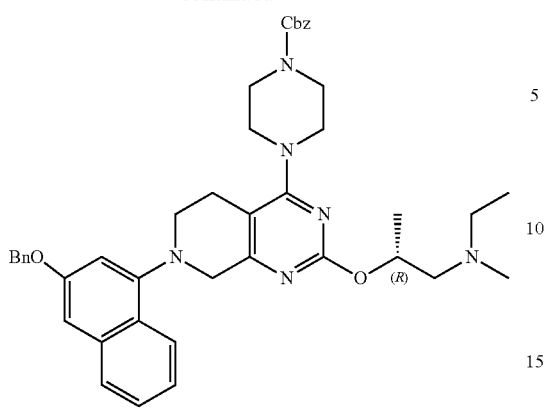

398
-continued

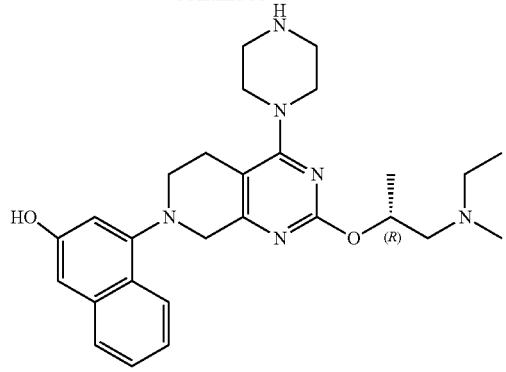

Step B: benzyl 4-[7-(3-benzyloxy-1-naphthyl)-2-[(1R)-2-[ethyl(methyl)amino]-1-methyl-ethoxy]-6,8-dihydro-5H-pyrido[3,4-d]pyrimidin-4-yl]piperazine-1-carboxylate: To a solution of (2R)-1-[ethyl(methyl)amino]propan-2-ol (217 mg, 1.85 mmol) in toluene (20 mL) was added benzyl 4-[7-(3-benzyloxy-1-naphthyl)-2-methylsulfinyl-6,8-dihydro-5H-pyrido[3,4-d]pyrimidin-4-yl]piperazine-1-carboxylate (400 mg, 617 umol), Pd$_2$(dba)$_3$ (56.6 mg, 61.8 umol), BINAP (76.9 mg, 124 umol) and NaOtBu (178 mg, 1.85 mmol) and the mixture de-gassed with N2 for 15 minutes and then heated to 90° C. for 16 hours under N$_2$. Upon completion, the reaction mixture was filtered and the filtrate concentrated under vacuum. The residue was purified by reversed-phase chromatography to give benzyl 4-[7-(3-benzyloxy-1-naphthyl)-2-[(1R)-2-[ethyl(methyl)amino]-1-methyl-ethoxy]-6,8-dihydro-5H-pyrido[3,4-d]pyrimidin-4-yl]piperazine-1-carboxylate (110 mg, 153 umol, 24.8% yield, 97.5% purity). ES+APCI MS m/z 701.4 [M+H]$^+$.

Step C: 4-[2-[(1R)-2-[ethyl(methyl)amino]-1-methyl-ethoxy]-4-piperazin-1-yl-6,8-dihydro-5H-pyrido[3,4-d]pyrimidin-7-yl]naphthalen-2-ol To a solution of benzyl 4-[7-(3-benzyloxy-1-naphthyl)-2-[(1R)-2-[ethyl(methyl)amino]-1-methyl-ethoxy]-6,8-dihydro-5H-pyrido[3,4-d]pyrimidin-4-yl]piperazine-1-carboxylate (100 mg, 143 umol) in MeOH (3.00 mL) was added HCl/MeOH (4 M, 143 uL), followed by Pd(OH)$_2$/C (50 mg) under N$_2$. The suspension was degassed under vacuum and purged with H$_2$ several times. The mixture was stirred under H$_2$ (15 psi) at 40° C. for 4 hours. Upon completion, the reaction mixture was filtered and the filtrate concentrated to give 4-[2-[(1R)-2-[ethyl(methyl)amino]-1-methyl-ethoxy]-4-piperazin-1-yl-6,8-dihydro-5H-pyrido[3,4-d]pyrimidin-7-yl]naphthalen-2-ol (76.0 mg, 125 umol, 87.5% yield, 90.3% purity, 2 HCl) which was used directly in the next step without further purification. ES+APCI MS m/z 477.2 [M+H]$^+$.

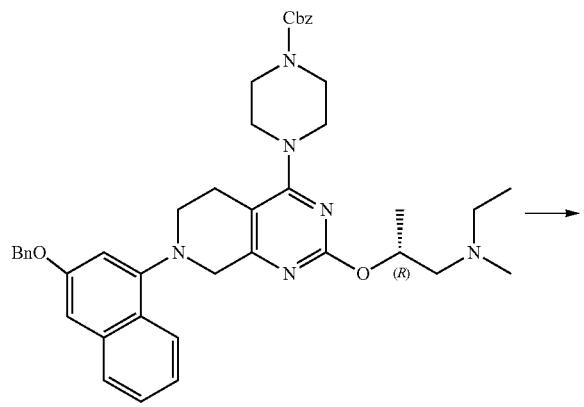

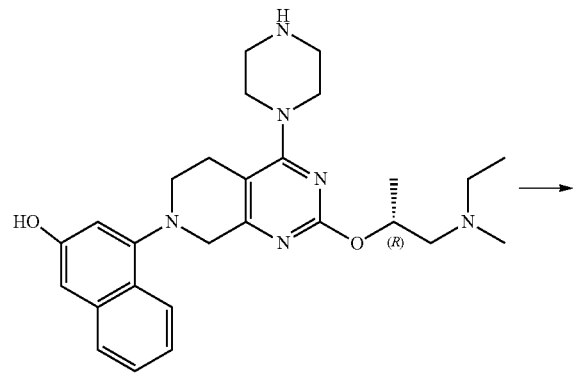

399

-continued

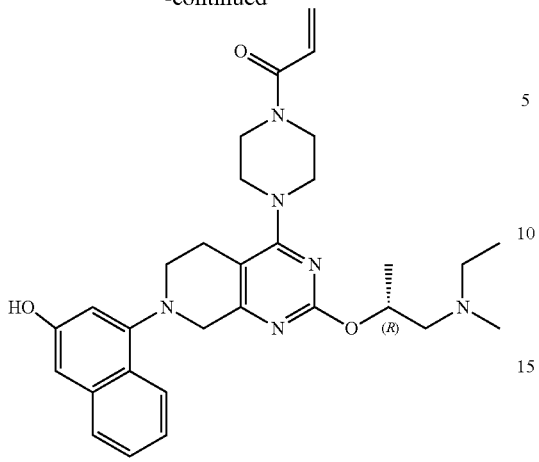

Step D: 1-[4-[2-[(1R)-2-[ethyl(methyl)amino]-1-methylethoxy]-7-(3-hydroxy-1-naphthyl)-6,8-dihydro-5H-pyrido[3,4-d]pyrimidin-4-yl]piperazin-1-yl]prop-2-en-1-one: To a solution of 4-[2-[(1R)-2-[ethyl(methyl)amino]-1-methylethoxy]-4-piperazin-1-yl-6,8-dihydro-5H-pyrido[3,4-d]pyrimidin-7-yl]naphthalen-2-ol (70 mg, 127 umol, 2 HCl) and DIEA (98.8 mg, 764 umol, 133 uL) in DCM (1.50 mL) was added prop-2-enoyl prop-2-enoate (12.9 mg, 102 umol) dropwise at −50° C. The mixture was stirred at −40 to −20° C. for 30 minutes. Upon completion, the mixture was quenched by addition of MeOH (17.0 mg) and concentrated under vacuum. The residue was diluted with water (1 mL) and extracted with DCM (3×6 mL). The organic layers were dried over $Na_2SO_4$ and concentrated under vacuum. The residue was purified by prep-HPLC (column: Phenomenex Gemini 150*25 mm*10 um; mobile phase: [water (0.05% ammonia hydroxide v/v)-ACN]; B %: 48%-78%,10 min) to give 1-[4-[2-[(1R)-2-[ethyl(methyl)amino]-1-methylethoxy]-7-(3-hydroxy-1-naphthyl)-6,8-dihydro-5H-pyrido[3,4-d]pyrimidin-4-yl]piperazin-1-yl]prop-2-en-1-one (9.23 mg, 17.2 umol, 13.5% yield, 98.7% purity) as a yellow solid. ES+APCI MS m/z 531.3 [M+H]+.

Example 132

1-[4-[2-[(1-cyclohexylpyrrolidin-3-yl)methoxy]-7-(3-hydroxy-1-naphthyl)-6,8-dihydro-5H-pyrido[3,4-d]pyrimidin-4-yl]piperazin-1-yl]prop-2-en-1-one

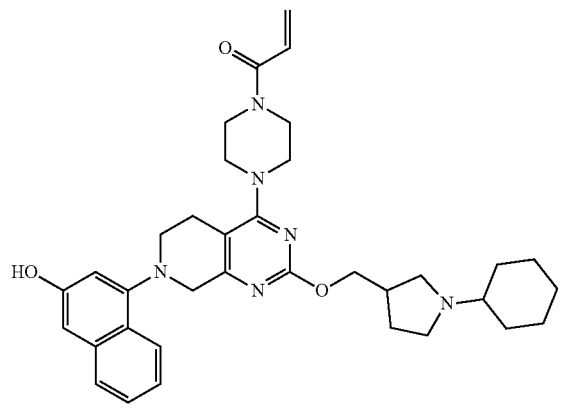

400

-continued

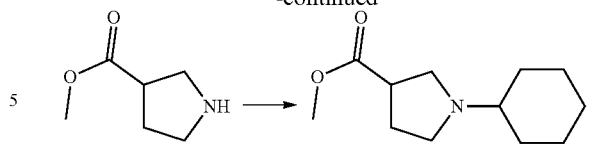

Step A: 1-cyclohexylpyrrolidine-3-carboxylate

To a solution of methyl pyrrolidine-3-carboxylate (1.00 g, 6.04 mmol, HCl) and DIEA (780 mg, 6.04 mmol, 1.05 mL) was added cyclohexanone (652 mg, 6.64 mmol, 686 uL) and HOAc (725 mg, 12.1 mmol, 691 uL) at 0° C. The reaction mixture was stirred at 0° C. for 0.5 h. To the reaction mixture was added $NaBH(OAc)_3$ (3.84 g, 18.12 mmol) in portions at 0° C. The reaction mixture was stirred at 0 to 15° C. for 12 hours. Upon completion, the reaction mixture was quenched by addition of water (5 mL) and organics concentrated under vacuum. The aqueous layer was extracted with DCM (10 mL×2) and the pH adjusted with sat $NaHCO_3$ (10 mL) and $Na_2CO_3$ (2 mL) to pH >8. The organic layers were combined, dried over $Na_2SO_4$ and concentrated under vacuum. The residue was triturated with MTBE/Petroleum Ether (1:3, 20 mL) and the filtrate concentrated under vacuum to give methyl 1-cyclohexylpyrrolidine-3-carboxylate (1.00 g, 4.73 mmol, 78.4% yield) as brown oil. ES+APCI MS m/z 212.2 [M+H]+.

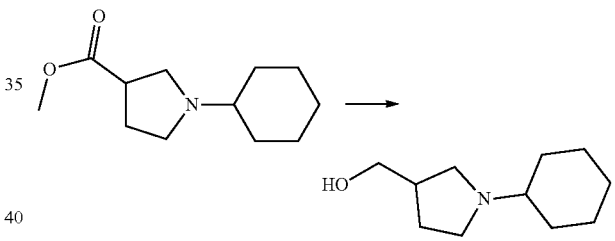

Step B: (1-cyclohexylpyrrolidin-3-yl)methanol

To a solution of methyl 1-cyclohexylpyrrolidine-3-carboxylate (1.00 g, 4.73 mmol) in THF (20 mL) was added $LiAlH_4$ (413 mg, 10.9 mmol) at −10° C. The reaction mixture was stirred at −10° C. for 0.5 hour. The reaction mixture was quenched by addition of saturated $Na_2SO_4$ (2 mL) and mixture filtered and the filter cake washed with THF (3×50 mL). The combined organics were concentrated under vacuum to give: (1-cyclohexylpyrrolidin-3-yl)methanol (800 mg, 4.36 mmol, 92.3% yield) as a colorless oil. $^1$H NMR (400 MHz, CHLOROFORM-d) δ=3.71 (dd, J=4.1, 10.0 Hz, 1H), 3.53 (dd, J=4.4, 10.0 Hz, 1H), 2.90 (dt, J=4.4, 8.8 Hz, 1H), 2.74 (dd, J=3.2, 8.8 Hz, 1H), 2.53 (dd, J=6.8, 8.8 Hz, 1H), 2.36-2.24 (m, 2H), 2.04-1.93 (m, 2H), 1.90 (br s, 2H), 1.78-1.64 (m, 3H), 1.61-1.52 (m, 1H), 1.33-1.12 (m, 5H)

1-[4-[2-[(1-cyclohexylpyrrolidin-3-yl)methoxy]-7-(3-hydroxy-1-naphthyl)-6,8-dihydro-5H-pyrido[3,4-d]pyrimidin-4-yl]piperazin-1-yl]prop-2-en-1-one was prepared following Example 131 substituting (1-cyclohexylpyrrolidin-3-yl)methanol for (2R)-1-[ethyl(methyl)amino]propan-2-ol in Step B. ES+APCI MS m/z 597.4 [M+H]+.

Example 133

1-[4-[7-(3-hydroxy-1-naphthyl)-2-(3-morpholinopropylamino)-6,8-dihydro-5H-pyrido[3,4-d]pyrimidin-4-yl]piperazin-1-yl]prop-2-en-1-one

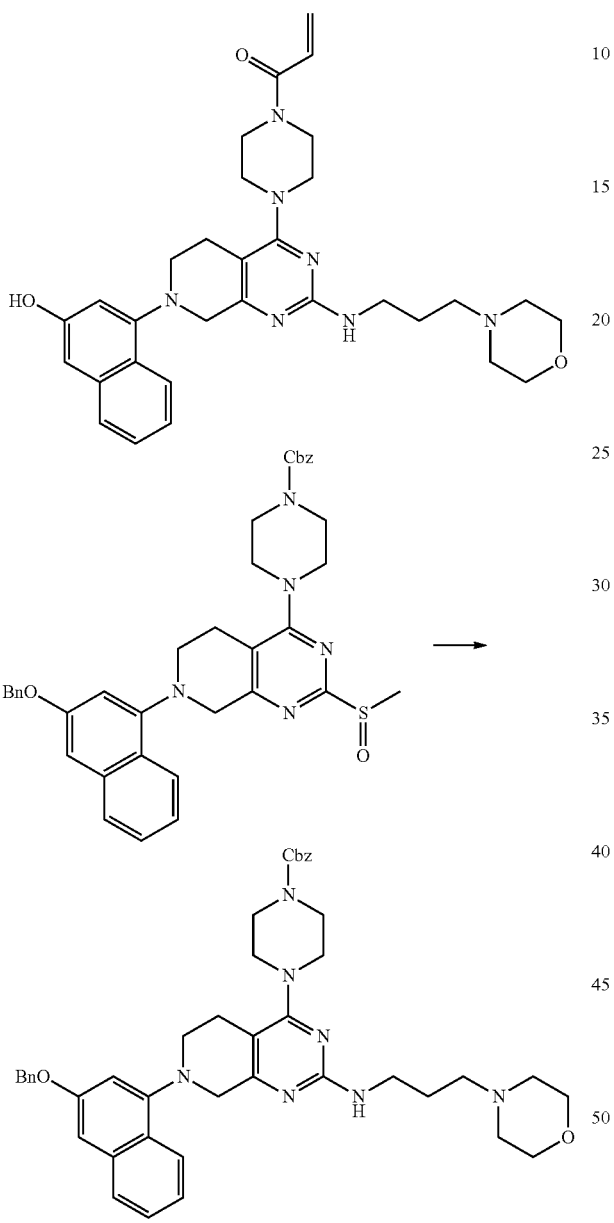

Step A: benzyl 4-[7-(3-benzyloxy-1-naphthyl)-2-(3-morpholinopropylamino)-6,8-dihydro-5H-pyrido[3,4-d]pyrimidin-4-yl]piperazine-1-carboxylate: A solution of benzyl 4-[7-(3-benzyloxy-1-naphthyl)-2-methylsulfinyl-6,8-dihydro-5H-pyrido[3,4-d]pyrimidin-4-yl]piperazine-1-carboxylate (400 mg, 617 umol) and 3-morpholinopropan-1-amine (534 mg, 3.70 mmol, 540 uL) in DMSO (4.00 mL) was heated to 100° C. for 12 hours. Upon completion, the mixture was diluted with water (4 mL) and extracted with EtOAc (3×20 mL). The organic layers were washed with brine (30 mL), dried over Na₂SO₄ and concentrated under vacuum. The residue was purified by column chromatography over Al₂O₃ eluting with Ethyl Acetate/Petroleum Ether (20→100%) to give benzyl 4-[7-(3-benzyloxy-1-naphthyl)-2-(3-morpholinopropylamino)-6,8-dihydro-5H-pyrido[3,4-d]pyrimidin-4-yl]piperazine-1-carboxylate (245 mg, 320 umol, 51.8% yield, 95.0% purity) as a yellow oil. ES+APCI MS m/z 728.6 [M+H]⁺.

1-[4-[7-(3-hydroxy-1-naphthyl)-2-(3-morpholinopropylamino)-6,8-dihydro-5H-pyrido[3,4-d]pyrimidin-4-yl]piperazin-1-yl]prop-2-en-1-one was prepared following Example 131 substituting benzyl 4-[7-(3-benzyloxy-1-naphthyl)-2-(3-morpholinopropylamino)-6,8-dihydro-5H-pyrido[3,4-d]pyrimidin-4-yl]piperazine-1-carboxylate for benzyl 4-[7-(3-benzyloxy-1-naphthyl)-2-[(1R)-2-[ethyl(methyl)amino]-1-methyl-ethoxy]-6,8-dihydro-5H-pyrido[3,4-d]pyrimidin-4-yl]piperazine-1-carboxylate in Step C. ES+APCI MS m/z 558.6 [M+H]⁺.

Example 134

(R)-1-(4-(7-(3-hydroxynaphthalen-1-yl)-2-(piperidin-3-ylmethoxy)-5,6,7,8-tetrahydropyrido[3,4-d]pyrimidin-4-yl)piperazin-1-yl)prop-2-en-1-one

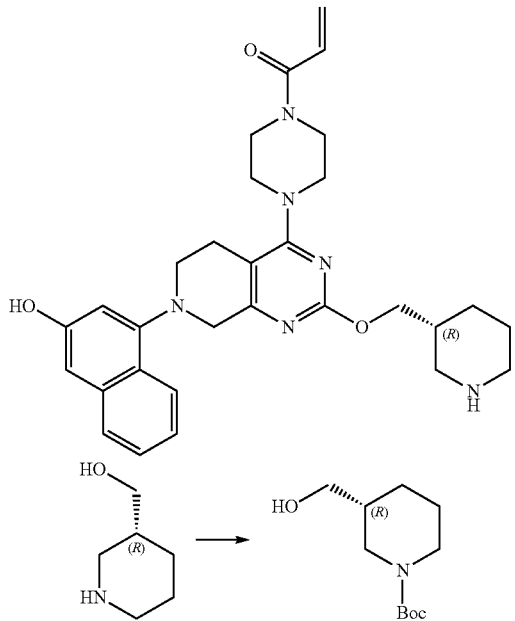

Step A: tert-butyl (3R)-3-(hydroxymethyl)piperidine-1-carboxylate

TEA (1.76 g, 17.4 mmol, 2.42 mL) was added to a solution of [(3R)-3-piperidyl]methanol (1.0 g, 8.68 mmol) in THF (25.0 mL), followed by the addition of a solution of Boc₂O (1.89 g, 8.68 mmol, 1.99 mL) in THF (5 mL) at 15° C. The mixture was stirred at 15° C. for 12 hours. The solvent was removed under vacuum and the residue dissolved in ethyl acetate (50 ml) and H₂O (30 mL). The solution was acidified with HCl (6 M) to pH ~6 and the layers separated. The organics were washed with brine (3×50 mL) and the combined organics concentrated to dryness to give tert-butyl (3R)-3-(hydroxymethyl)piperidine-1-carboxylate (1.68 g, 7.80 mmol, 89.9% yield, 100% purity) as colorless crystals. ¹H NMR (400 MHz, chloroform-d) δ=3.73 (br s, 2H), 3.51 (br d, J=6.8 Hz, 2H), 3.05 (br s, 2H), 1.83-1.71 (m, 2H), 1.62 (br s, 1H), 1.46 (s, 9H), 1.44-1.37 (m, 1H), 1.35-1.22 (m, 1H).

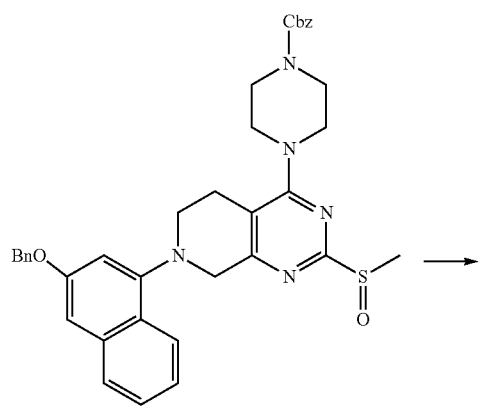

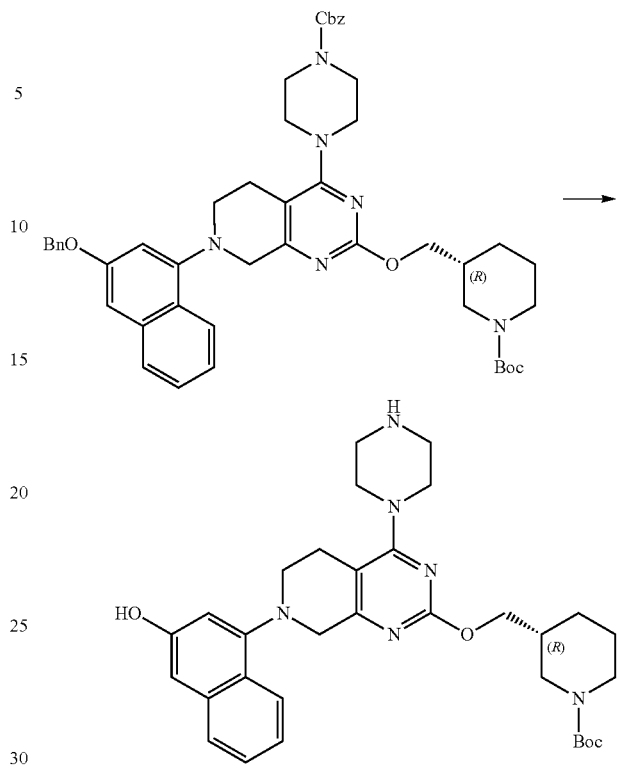

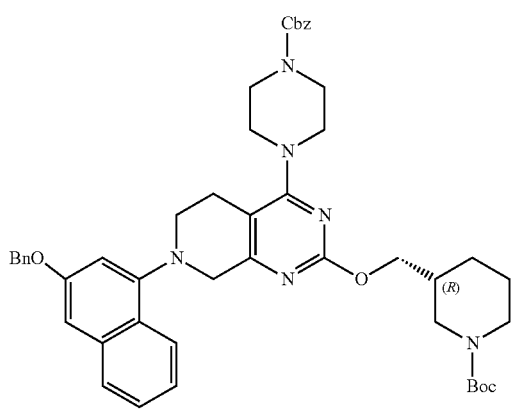

Step B: benzyl 4-[7-(3-benzyloxy-1-naphthyl)-2-[[(3R)-1-tert-butoxycarbonyl-3-piperidyl]methoxy]-6,8-dihydro-5H-pyrido[3,4-d]pyrimidin-4-yl]piperazine-1-carboxylate: To a solution of tert-butyl (3R)-3-(hydroxymethyl) piperidine-1-carboxylate (332 mg, 1.54 mmol) in THF (5 mL) was added t-BuONa (223 mg, 2.32 mmol). A solution of benzyl 4-[7-(3-benzyloxy-1-naphthyl)-2-methyl sulfinyl-6,8-dihydro-5H-pyrido[3,4-d]pyrimidin-4-yl]piperazine-1-carboxylate (500 mg, 772 umol) in THF (5 mL) was next added and the mixture stirred at 0° C. for 1 hour. The reaction mixture was filtered and concentrated under reduced pressure and the residue purified by column chromatography eluting with Petroleum ether/Ethyl Acetate (10/1 to 3/1) to give benzyl 4-[7-(3-benzyloxy-1-naphthyl)-2-[[(3R)-1-tert-butoxycarbonyl-3-piperidyl]methoxy]-6,8-dihydro-5H-pyrido[3,4-d]pyrimidin-4-yl]piperazine-1-carboxylate (510 mg, 628 umol, 81.4% yield, 98.4% purity) as a white solid. ES+APCI MS m/z 799.4 [M+H]⁺.

Step C: tert-butyl (3R)-3-[[7-(3-hydroxy-1-naphthyl)-4-piperazin-1-yl-6,8-dihydro-5H-pyrido[3,4-d]pyrimidin-2-yl]oxymethyl]piperidine-1-carboxylate: A solution of benzyl 4-[7-(3-benzyloxy-1-naphthyl)-2-[[(3R)-1-tert-butoxycarbonyl-3-piperidyl]methoxy]-6,8-dihydro-5H-pyrido[3,4-d]pyrimidin-4-yl]piperazine-1-carboxylate (250 mg, 313 umol) in MeOH (5 mL) was purged with NH₃ (10%, w/w) and then 10% Pd/C (50 mg) was added. The suspension was degassed under vacuum and the mixture stirred under H₂ (15 psi) at 15° C. for 12 hours. The reaction mixture was filtered and concentrated under reduced pressure to dryness to give tert-butyl (3R)-3-[[7-(3-hydroxy-1-naphthyl)-4-piperazin-1-yl-6,8-dihydro-5H-pyrido[3,4-d] pyrimidin-2-yl]oxymethyl]piperidine-1-carboxylate (126 mg, 211 umol, 67.4% yield, 96.2% purity) as a colorless oil. ES+APCI MS m/z 575.5 [M+H]⁺.

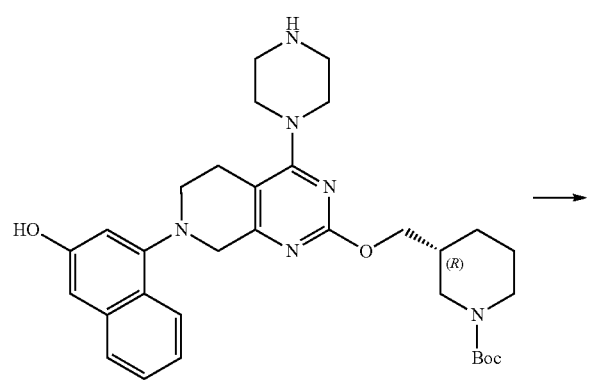

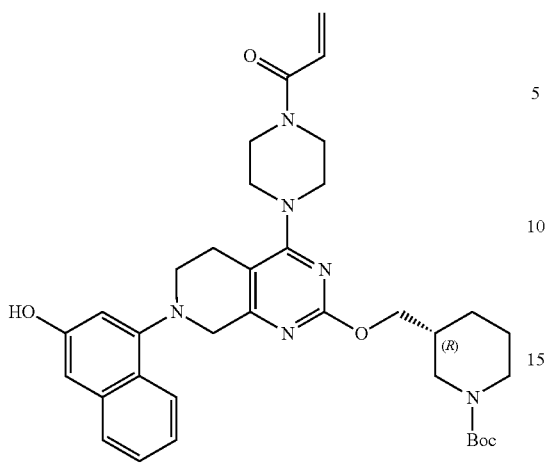

Step D: tert-butyl(3R)-3-[[7-(3-hydroxy-1-naphthyl)-4-(4-prop-2-enoyl piperazin-1-yl)-6,8-dihydro-5H-pyrido[3,4-d]pyrimidin-2-yl]oxymethyl]piperidine-1-carboxylate: To a solution of tert-butyl (3R)-3-[[7-(3-hydroxy-1-naphthyl)-4-piperazin-1-yl-6,8-dihydro-5H-pyrido[3,4-d]pyrimidin-2-yl]oxymethyl]piperidine-1-carboxylate (126 mg, 219 umol) and TEA (33.3 mg, 329 umol, 45.8 uL) in DCM (5.0 mL) was added prop-2-enoyl prop-2-enoate (24.9 mg, 197 umol) dropwise at −40° C. and the reaction stirred for 30 minutes at −40° C. The reaction mixture was quenched by addition MeOH (0.5 mL) and concentrated to dryness. The residue was dissolved into EtOAc (50 mL) and H₂O (20 mL). The resulting solution was acidified with HCl (1 M) to pH ~6 and the layers separated. The combined organics were dried over Na₂SO₄, filtered and concentrated under reduced pressure to give tert-butyl(3R)-3-[[7-(3-hydroxy-1-naphthyl)-4-(4-prop-2-enoyl piperazin-1-yl)-6,8-dihydro-5H-pyrido[3,4-d]pyrimidin-2-yl]oxymethyl]piperidine-1-carboxylate (120 mg, 172 umol, 78.5% yield, 90.2% purity) as a yellow oil, which was used directly for next step without further purification. ES+APCI MS m/z 629.6 [M+H]⁺.

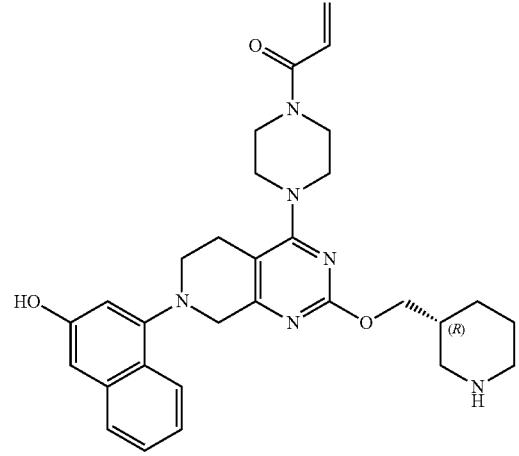

Step E: 1-[4-[7-(3-hydroxy-1-naphthyl)-2-[[(3R)-3-piperidyl] methoxy]-6,8-dihydro-5H-pyrido[3,4-d]pyrimidin-4-yl]piperazin-1-yl]prop-2-en-1-one: To a solution of tert-butyl(3R)-3-[[7-(3-hydroxy-1-naphthyl)-4-(4-prop-2-enoylpiperazin-1-yl)-6,8-dihydro-5H-pyrido [3,4-d] pyrimidin-2-yl]oxymethyl]piperidine-1-carboxylate (120 mg, 191 umol) in DCM (3.0 mL) was added TFA (326 mg, 2.86 mmol, 212 uL) at 0° C. The mixture was stirred at 15° C. for 2 hours under N₂ atmosphere. The reaction mixture was basified with NH₃ (30% in water, three drops) and concentrated to dryness. The residue was purified by prep-HPLC (column: Phenomenex Synergi C18 150*25*10 um; mobile phase:[water (0.225% Formic Acid)-ACN]; B %: 5%-35%,10 min) to give 1-[4-[7-(3-hydroxy-1-naphthyl)-2-[[(3R)-3-piperidyl] methoxy]-6,8-dihydro-5H-pyrido[3,4-d] pyrimidin-4-yl]piperazin-1-yl]prop-2-en-1-one (24.5 mg, 38.9 umol, 20.4% yield) as a yellow solid. ES+APCI MS m/z 529.4 [M+H]⁺.

Example 135

1-[4-[2-[3-(4-acetylpiperazin-1-yl)propoxy]-7-(3-hydroxy-1-naphthyl)-6,8-dihydro-5H-pyrido[3,4-d]pyrimidin-4-yl]piperazin-1-yl]prop-2-en-1-one

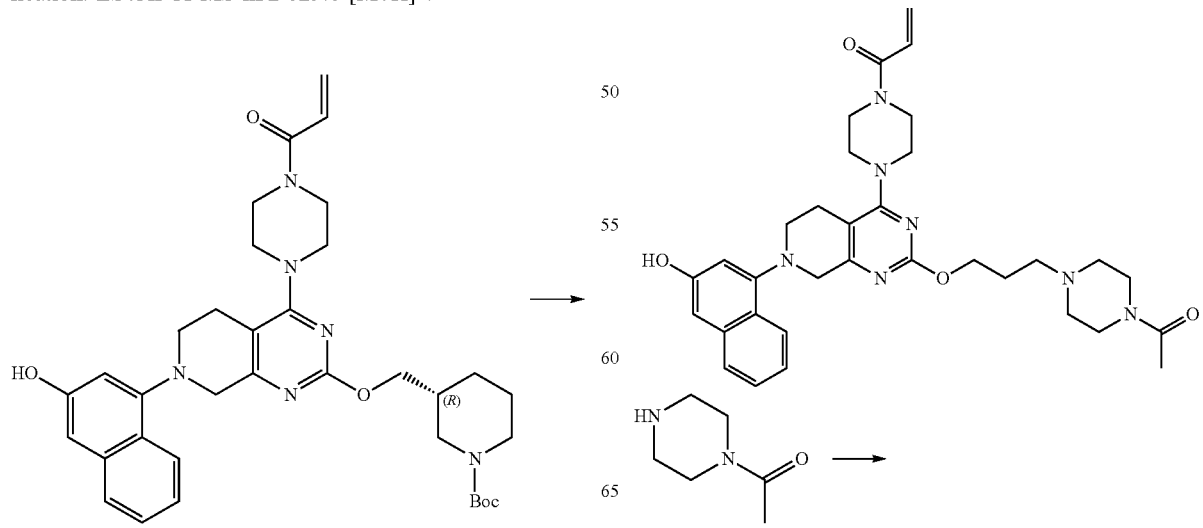

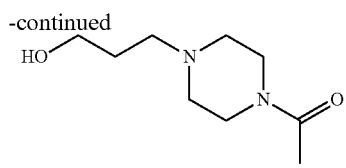

Step A: 1-[4-(3-hydroxypropyl)piperazin-1-yl]ethanone

To a solution of 1-piperazin-1-ylethanone (2.00 g, 15.6 mmol) and $K_2CO_3$ (4.31 g, 31.2 mmol) in $CH_3CN$ (50.0 mL) was added 3-bromopropan-1-ol (3.25 g, 23.4 mmol). The mixture was stirred at 80° C. for 5 hours. The solid was filtered and the filtrate was evaporated to give 1-[4-(3-hydroxypropyl)piperazin-1-yl]ethanone (2.00 g, 10.7 mmol, 68.8% yield) as a colorless oil.

1-[4-[2-[3-(4-acetylpiperazin-1-yl)propoxy]-7-(3-hydroxy-1-naphthyl)-6,8-dihydro-5H-pyrido[3,4-d]pyrimidin-4-yl]piperazin-1-yl]prop-2-en-1-one was prepared following Example 131 substituting 1-[4-(3-hydroxypropyl)piperazin-1-yl] ethanone for benzyl 4-[7-(3-benzyloxy-1-naphthyl)-2-[(1R)-2-[ethyl(methyl)amino]-1-methyl-ethoxy]-6,8-dihydro-5H-pyrido[3,4-d]pyrimidin-4-yl]piperazine-1-carboxylate in Step C. ES+APCI MS m/z 600.3 $[M+H]^+$.

Example 136

1-[4-[7-(3-hydroxy-1-naphthyl)-2-[2-(3-methoxypyrrolidin-1-yl)ethoxy]-6,8-dihydro-5H-pyrido[3,4-d]pyrimidin-4-yl]piperazin-1-yl]prop-2-en-1-one

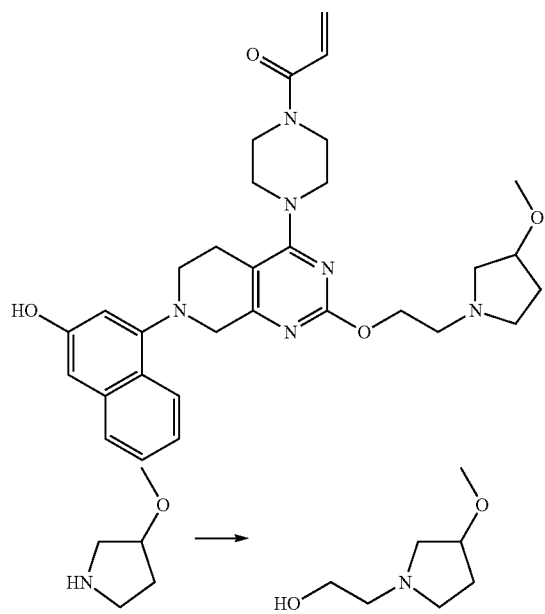

Step A: 2-(3-methoxypyrrolidin-1-yl)ethanol

To a solution of 3-methoxypyrrolidine (450 mg, 3.27 mmol, HCl) and 2-bromoethanol (408 mg, 3.27 mmol) in $CH_3CN$ (10 mL) was added $K_2CO_3$ (1.36 g, 9.81 mmol).

The mixture was stirred at 80° C. for 3 hours. The solid was filtered and the filtrate was evaporated to give 2-(3-methoxypyrrolidin-1-yl)ethanol (450 mg, 3.10 mmol, 94.8% yield) as a colorless oil.

Step B: benzyl 4-[7-(3-benzyloxy-1-naphthyl)-2-[2-(3-methoxypyrrolidin-1-yl)ethoxy]-6,8-dihydro-5H-pyrido[3,4-d]pyrimidin-4-yl]piperazine-1-carboxylate: A mixture of benzyl 4-[7-(3-benzyloxy-1-naphthyl)-2-methylsulfinyl-6,8-dihydro-5H-pyrido[3,4-d]pyrimidin-4-yl]piperazine-1-carboxylate (500 mg, 771 umol), 2-(3-methoxypyrrolidin-1-yl)ethanol (224 mg, 1.54 mmol), and t-BuONa (222 mg, 2.32 mmol) in toluene (10 mL) was stirred at 20° C. for 1 hour under $N_2$ atmosphere. The mixture was cooled to 0° C. and HCl (2M) was added until pH ~7. The mixture was filtered and filtrate was concentrated in vacuum. The residue was purified by column chromatography using 0410% MeOH/DCM as eluent to give benzyl 4-[7-(3-benzyloxy-1-naphthyl)-2-[2-(3-methoxypyrrolidin-1-yl)ethoxy]-6,8-dihydro-5H-pyrido[3,4-d]pyrimidin-4-yl]piperazine-1-carboxylate (110 mg, 147.9 umol, 19.1% yield) ES+APCI MS m/z 729.2 $[M+H]^+$.

1-[4-[7-(3-hydroxy-1-naphthyl)-2-[2-(3-methoxypyrrolidin-1-yl)ethoxy]-6,8-dihydro-5H-pyrido[3,4-d]pyrimidin-4-yl]piperazin-1-yl]prop-2-en-1-one was prepared following Example 131 substituting benzyl 4-[7-(3-benzyloxy-1-naphthyl)-2-[2-(3-methoxypyrrolidin-1-yl)ethoxy]-6,8-dihydro-5H-pyrido[3,4-d]pyrimidin-4-yl]piperazine-1-carboxylate for benzyl 4-[7-(3-benzyloxy-1-naphthyl)-2-[(1R)-2-[ethyl(methyl)amino]-1-methyl-ethoxy]-6,8-dihydro-5H-pyrido[3,4-d]pyrimidin-4-yl]piperazine-1-carboxylate in Step C. ES+APCI MS m/z 559.3 $[M+H]^+$.

Example 137

1-[4-[7-(3-hydroxy-1-naphthyl)-2-[3-(3-methoxypyrrolidin-1-yl)propoxy]-6,8-dihydro-5H-pyrido[3,4-d]pyrimidin-4-yl]piperazin-1-yl]prop-2-en-1-one

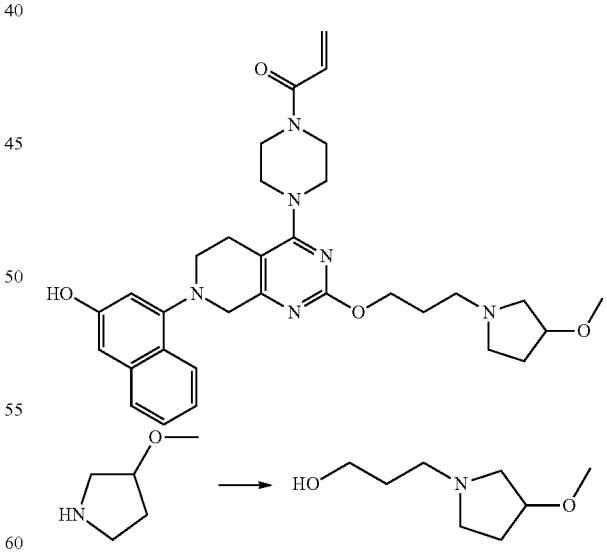

Step A: (3-methoxypyrrolidin-1-yl)propan-1-ol

To a solution of 3-methoxypyrrolidine (500 mg, 3.63 mmol, HCl) and 3-bromopropan-1-ol (505 mg, 3.63 mmol) in $CH_3CN$ (10 mL) was added $K_2CO_3$ (1.51 g, 10.9 mmol).

409

The mixture was stirred at 20° C. for 5 hours. The solid was filtered and the filtrate was evaporated to give 3-(3-methoxypyrrolidin-1-yl)propan-1-ol (540 mg, 3.39 mmol, 93.3% yield).

1-[4-[7-(3-hydroxy-1-naphthyl)-2-[3-(3-methoxypyrrolidin-1-yl)propoxy]-6,8-dihydro-5H-pyrido[3,4-d]pyrimidin-4-yl]piperazin-1-yl]prop-2-en-1-one was prepared following Example 131 substituting (3-methoxypyrrolidin-1-yl)propan-1-ol for (2R)-1-[ethyl(methyl)amino]propan-2-ol in Step B. ES+APCI MS m/z 573.3 [M+H]+.

Example 138

1-[4-[2-[2-(3,3-difluoroazetidin-1-yl)ethoxy]-7-(3-hydroxy-1-naphthyl)-6,8-dihydro-5H-pyrido[3,4-d]pyrimidin-4-yl]piperazin-1-yl]prop-2-en-1-one

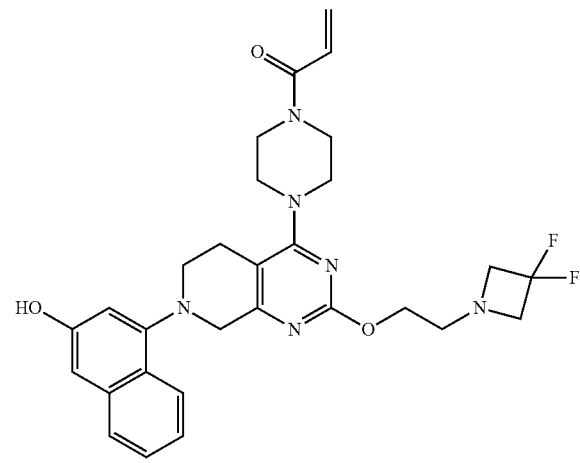

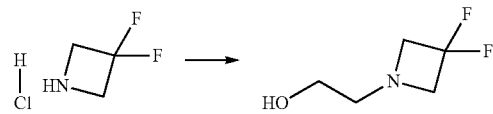

Step A: 2-(3,3-difluoroazetidin-1-yl)ethanol

To a solution of 3,3-difluoroazetidine (500 mg, 3.86 mmol, HCl) and 2-bromoethanol (482 mg, 3.86 mmol, 274 uL) in CH$_3$CN (10 mL) was added K$_2$CO$_3$ (1.60 g, 11.5 mmol) and the reaction stirred at 80° C. for 16 hours. The reaction was filtered and the filtrate evaporated to give 2-(3,3-difluoroazetidin-1-yl)ethanol (300 mg, 2.19 mmol, 56.7% yield).

1-[4-[2-[2-(3,3-difluoroazetidin-1-yl)ethoxy]-7-(3-hydroxy-1-naphthyl)-6,8-dihydro-5H-pyrido[3,4-d]pyrimidin-4-yl]piperazin-1-yl]prop-2-en-1-one was prepared following Example 131 substituting give 2-(3,3-difluoroazetidin-1-yl)ethanol for (2R)-1-[ethyl(methyl)amino]propan-2-ol in Step B. ES+APCI MS m/z 551.4 [M+H]+.

410

Example 139

1-[4-[2-[2-(3,3-difluoropyrrolidin-1-yl)ethoxy]-7-(3-hydroxy-1-naphthyl)-6,8-dihydro-5H-pyrido[3,4-d]pyrimidin-4-yl]piperazin-1-yl]prop-2-en-1-one

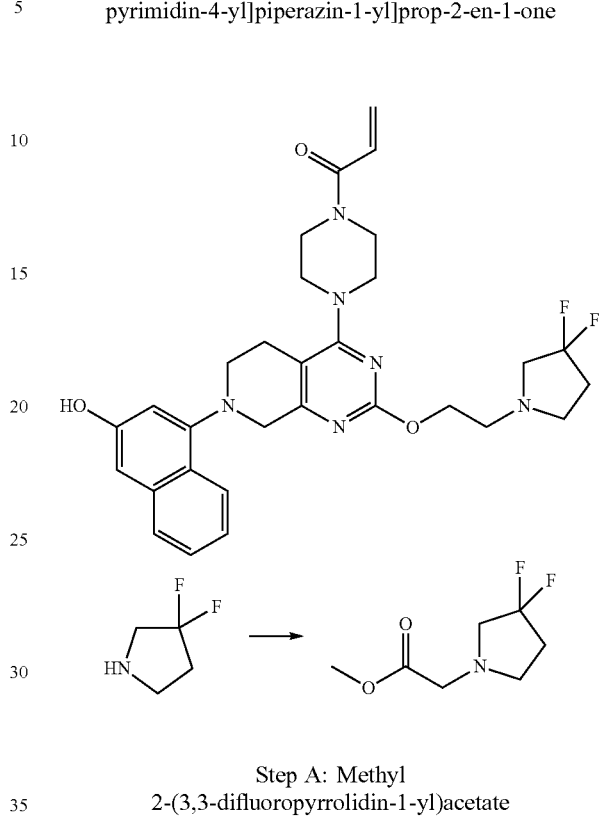

Step A: Methyl 2-(3,3-difluoropyrrolidin-1-yl)acetate

To a suspension of methyl 2-bromoacetate (1.17 g, 7.67 mmol, 723 uL) in DCM (10 mL) cooled to 0° C. was added TEA (1.76 g, 17.4 mmol, 2.42 mL) and 3,3-difluoropyrrolidine (1.00 g, 6.97 mmol, HCl) and the reaction mixture stirred at 20° C. for 16 hours. The reaction was filtered and filtrate was evaporated. The residue was purified by column chromatography with 0.5%→20% MeOH/DCM as eluent to give methyl 2-(3,3-difluoropyrrolidin-1-yl)acetate (580 mg, 3.24 mmol, 46.4% yield). $^1$H NMR (400 MHz, chloroform-d) δ=3.73 (s, 3H), 3.38 (s, 2H), 3.11 (t, J=13.6 Hz, 2H), 2.92 (t, J=6.8 Hz, 2H), 2.36-2.26 (m, 2H).

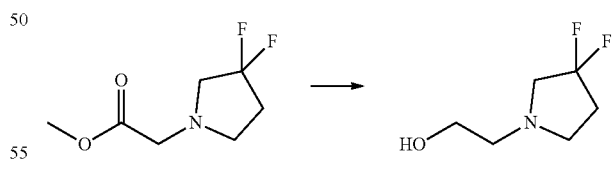

Step B: 2-(3,3-difluoropyrrolidin-1-yl)ethanol

To a solution of LiAlH$_4$ (184 mg, 4.86 mmol) in THF (5.0 mL) was added a solution of methyl 2-(3,3-difluoropyrrolidin-1-yl)acetate (580 mg, 3.24 mmol) in THF (5.0 mL) dropwise at 0° C. The mixture was warmed to 20° C. and stirred for 3 hours. The mixture was quenched by addition of saturated aqueous sodium sulfate solution (1.50 mL). The reaction was filtered and the filtrated was concentrated under vacuum to give 2-(3,3-difluoropyrrolidin-1-yl)ethanol (330 mg, 2.18 mmol, 67.4% yield) as a colourless oil. ¹H NMR (400 MHz, chloroform-d) δ=3.64 (t, J=5.2 Hz, 2H), 2.97 (t, J=13.2 Hz, 2H), 2.82 (t, J=7.2 Hz, 2H), 2.68 (t, J=5.2 Hz, 2H), 2.49 (br. s, 1H), 2.34-2.24 (m, 2H).

1-[4-[2-[2-(3,3-difluoropyrrolidin-1-yl)ethoxy]-7-(3-hydroxy-1-naphthyl)-6,8-dihydro-5H-pyrido[3,4-d]pyrimidin-4-yl]piperazin-1-yl]prop-2-en-1-one was prepared following Example 131 substituting 2-(3,3-difluoropyrrolidin-1-yl)ethanol for (2R)-1-[ethyl(methyl)amino]propan-2-ol in Step B. ES+APCI MS m/z 565.3 [M+H]⁺.

Example 140

2-[3-[[7-(3-hydroxy-1-naphthyl)-4-(4-prop-2-enoylpiperazin-1-yl)-6,8-dihydro-5H-pyrido[3,4-d]pyrimidin-2-yl]oxymethyl]pyrrolidin-1-yl]-N,N-dimethyl-acetamide

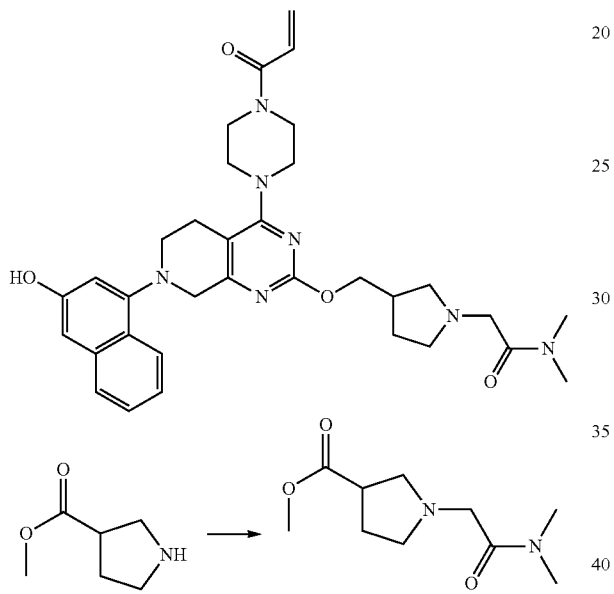

Step A: methyl 1-[2-(dimethylamino)-2-oxo-ethyl]pyrrolidine-3-carboxylate

A solution of methyl pyrrolidine-3-carboxylate (1.00 g, 6.04 mmol, HCl) and NaHCO₃ (1.01 g, 12.1 mmol, 470 uL) in ACN (200.0 mL) was stirred at 10° C. for 5 minutes. A solution of 2-bromo-N,N-dimethyl-acetamide (1.00 g, 6.04 mmol) in ACN (5.00 mL) was next added at 10° C. and the reaction stirred at 10° C. for 6 hours followed by and stirring at 50° C. for 2 hours. The mixture was filtered and solids washed with DCM (3×15 ml). The filtrate was concentrated under vacuum and the residue purified by column chromatography using 0410% MeOH/DCM as eluent to give methyl 1-[2-(dimethylamino)-2-oxo-ethyl]pyrrolidine-3-carboxylate (480 mg, 2.02 mmol, 33.4% yield).

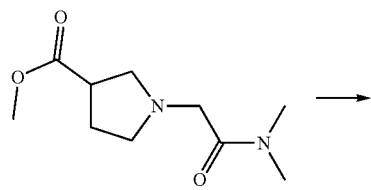

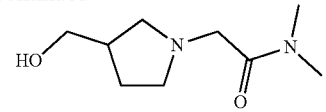

Step B: 2-[3-(hydroxymethyl)pyrrolidin-1-yl]-N,N-dimethyl-acetamide

To a solution of methyl 1-[2-(dimethylamino)-2-oxo-ethyl]pyrrolidine-3-carboxylate (500 mg, 2.33 mmol) in THF (10 mL) was added LiAlH₄ (203 mg, 5.36 mmol) at −60° C. and the reaction mixture stirred at −60° C. for 10 minutes. The reaction mixture was quenched by the addition of saturated Na₂SO₄ (0.4 mL) and the slurry was filtered. The filter cake was washed with THF (3×50 mL) and the filtrate concentrated under vacuum to give 2-[3-(hydroxymethyl)pyrrolidin-1-yl]-N,N-dimethyl-acetamide (400 mg, 2.15 mmol, 92.2% yield) as a brown oil. ES+APCI MS m/z 187.1 [M+H]⁺.

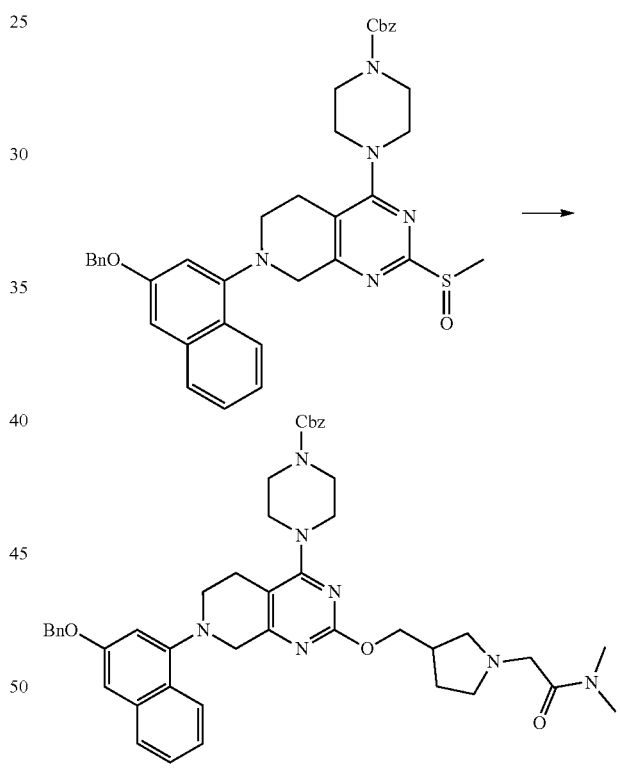

Step C: benzyl 4-[7-(3-benzyloxy-1-naphthyl)-2-[[1-[2-(dimethylamino)-2-oxo-ethyl]pyrrolidin-3-yl]methoxy]-6,8-dihydro-5H-pyrido[3,4-d]pyrimidin-4-yl]piperazine-1-carboxylate: A mixture of benzyl 4-[7-(3-benzyloxy-1-naphthyl)-2-methylsulfinyl-6,8-dihydro-5H-pyrido[3,4-d]pyrimidin-4-yl]piperazine-1-carboxylate (500 mg, 772 umol), 2-[3-(hydroxymethyl)pyrrolidin-1-yl]-N,N-dimethyl-acetamide (216 mg, 1.16 mmol) and NaOBu-t (148 mg, 1.54 mmol) in toluene (10 mL) was stirred at 15° C. for 15 minutes. The reaction mixture was purified directly by silica gel chromatography using 20→100% EtOAc/Petroleum Ether to give benzyl 4-[7-(3-benzyloxy-1-naphthyl)-2-[[1-[2-(dimethylamino)-2-oxo-ethyl]pyrrolidin-3-yl]

methoxy]-6,8-dihydro-5H-pyrido[3,4-d]pyrimidin-4-yl]piperazine-1-carboxylate (310 mg, 395 umol, 51.1% yield, 98% purity) as a brown solid. ES+APCI MS m/z 770.4 [M+H]+.

2-[3-[[7-(3-hydroxy-1-naphthyl)-4-(4-prop-2-enoylpiperazin-1-yl)-6,8-dihydro-5H-pyrido[3,4-d]pyrimidin-2-yl]oxymethyl]pyrrolidin-1-yl]-N,N-dimethyl-acetamide was prepared following Example 131 substituting benzyl 4-[7-(3-benzyloxy-1-naphthyl)-2-[[1-[2-(dimethylamino)-2-oxoethyl]pyrrolidin-3-yl]methoxy]-6,8-dihydro-5H-pyrido[3,4-d]pyrimidin-4-yl]piperazine-1-carboxylate for benzyl 4-[7-(3-benzyloxy-1-naphthyl)-2-[(1R)-2-[ethyl(methyl)amino]-1-methyl-ethoxy]-6,8-dihydro-5H-pyrido[3,4-d]pyrimidin-4-yl]piperazine-1-carboxylate in Step C. ES+APCI MS m/z 600.3 [M+H]+.

Example 141

1-[4-[2-[[1-(2-hydroxyethyl)pyrrolidin-3-yl]methoxy]-7-(3-hydroxy-1-naphthyl)-6,8-dihydro-5H-pyrido[3,4-d]pyrimidin-4-yl]piperazin-1-yl]prop-2-en-1-one

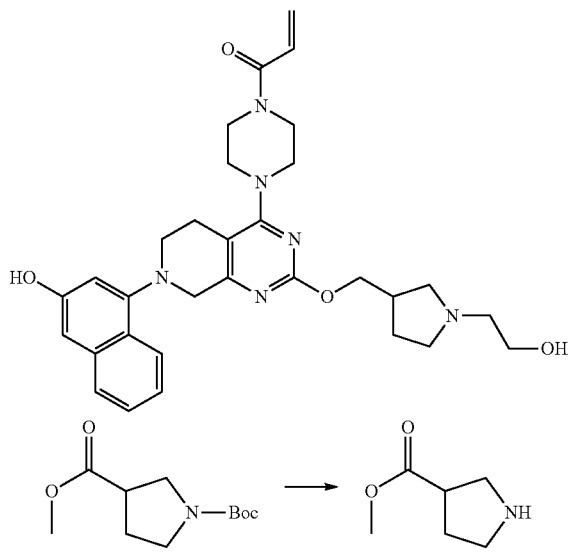

Step A: methyl pyrrolidine-3-carboxylate

To a solution of 1-(tert-butyl) 3-methyl pyrrolidine-1,3-dicarboxylate (10.0 g, 43.6 mmol) in DCM (50 mL) was added HCl/dioxane (4 M, 109 mL) at 0° C. and stirred at 0° C. for 1 hour. The mixture was concentrated under vacuum to give methyl pyrrolidine-3-carboxylate (7.00 g, crude, HCl) as brown oil. ¹H NMR (400 MHz, methanol-d₄) δ=3.77 (s, 3H), 3.56-3.53 (m, 2H), 3.41-3.37 (m, 3H), 2.40-2.24 (m, 2H).

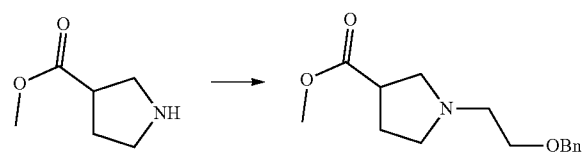

Step B: methyl 1-(2-benzyloxyethyl)pyrrolidine-3-carboxylate

A solution of methyl pyrrolidine-3-carboxylate (3.0 g, 18.1 mmol, HCl), Cs₂CO₃ (17.7 g, 54.3 mmol) and KI (301 mg, 1.81 mmol) in MeCN (60 mL) was stirred at 15° C. for 5 min. Then a solution of 2-bromoethoxymethylbenzene (4.67 g, 21.7 mmol, 3.43 mL) in ACN (15 mL) was added to the mixture at 15° C. and stirred at 15° C. for 1 hour. The mixture was next warmed to 50° C. and stirred at 50° C. for 12 hours. The reaction mixture was filtered and the filter cake washed with DCM (3×30 mL) and the filtrate concentrated under vacuum. The residue was purified by prep-HPLC (column: Phenomenex luna C18 250*50 mm*10 um; mobile phase: [water (0.1% TFA)-ACN]; B %: 10ACN %-40ACN %,30 min 40% min) to give methyl 1-(2-benzyloxyethyl)pyrrolidine-3-carboxylate (1.48 g, 5.06 mmol, 27.9% yield, 90.0% purity) as brown oil. ¹H NMR (400 MHz, chloroform-d) δ=7.36-7.28 (m, 5H), 4.56 (s, 2H), 3.70 (s, 3H), 3.61-3.58 (t, J=6.0 Hz, 2H), 3.02-3.00 (m, 2H), 2.78-2.67 (m, 4H), 2.58-2.49 (m, 1H), 2.11-2.08 (m, 2H)

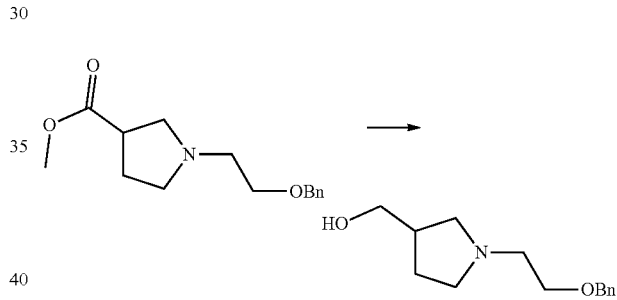

Step C: (1-(2-(benzyloxy)ethyl)pyrrolidin-3-yl)methanol

To the solution of methyl 1-(2-benzyloxyethyl)pyrrolidine-3-carboxylate (1.38 g, 5.24 mmol) in THF (27 mL) was added LiAlH₄ (457 mg, 12 mmol) at −10° C. and stirred at −10° C. for 0.5 hour. The reaction mixture was quenched by saturated Na₂SO₄ (1 mL) and filtered, the filter cake was washed with THF (5×30 mL), the filtrate was concentrated under vacuum to give (1-(2-(benzyloxy)ethyl)pyrrolidin-3-yl)methanol (1.30 g, 3.31 mmol, 63.3% yield, 60.0% purity) as brown oil. ES+APCI MS m/z 236.1 [M+H]+.

1-[4-[2-[[1-(2-hydroxyethyl)pyrrolidin-3-yl]methoxy]-7-(3-hydroxy-1-naphthyl)-6,8-dihydro-5H-pyrido[3,4-d]pyrimidin-4-yl]piperazin-1-yl]prop-2-en-1-one was prepared following Example 136 substituting (1-(2-(benzyloxy)ethyl)pyrrolidin-3-yl)methanol for 2-(3-methoxypyrrolidin-1-yl)ethanol in Step B. ES+APCI MS m/z 559.3 [M+H]+.

Example 142

1-[4-[2-(2-hydroxyethoxy)-7-(3-hydroxy-1-naphthyl)-6,8-dihydro-5H-pyrido[3,4-d]pyrimidin-4-yl]piperazin-1-yl]prop-2-en-1-one

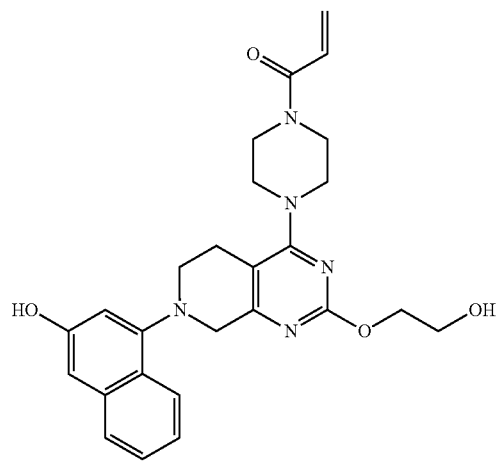 [SMILES: C=CC(=O)N1CCN(c2nc(OCCO)nc3c2CCN(c2cc(O)cc4ccccc24)C3)CC1]

1-[4-[2-(2-hydroxyethoxy)-7-(3-hydroxy-1-naphthyl)-6,8-dihydro-5H-pyrido[3,4-d]pyrimidin-4-yl]piperazin-1-yl]prop-2-en-1-one was prepared following Example 136 substituting 2-[tert-butyl(dimethyl)silyl]oxyethanol for 2-(3-methoxypyrrolidin-1-yl)ethanol in Step B. ES+APCI MS m/z 476.2 [M+H]+.

Example 143

1-[4-[2-(2,3-dihydroxypropoxy)-7-(3-hydroxy-1-naphthyl)-6,8-dihydro-5H-pyrido[3,4-d]pyrimidin-4-yl]piperazin-1-yl]prop-2-en-1-one

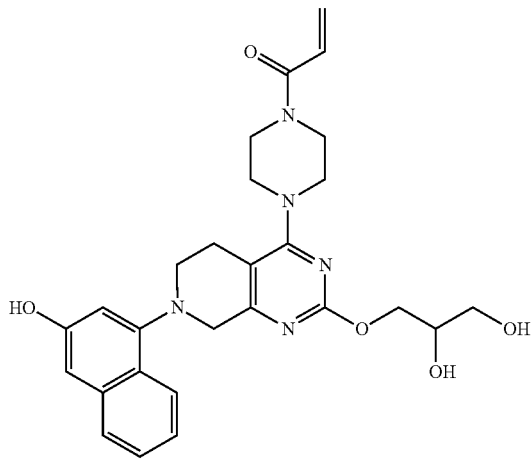 [SMILES: C=CC(=O)N1CCN(c2nc(OCC(O)CO)nc3c2CCN(c2cc(O)cc4ccccc24)C3)CC1]

1-[4-[2-(2,3-dihydroxypropoxy)-7-(3-hydroxy-1-naphthyl)-6,8-dihydro-5H-pyrido [3,4-d]pyrimidin-4-yl]piperazin-1-yl]prop-2-en-1-one was prepared following Example 136 substituting (2,2-dimethyl-1,3-dioxolan-4-yl)methanol for 2-(3-methoxypyrrolidin-1-yl)ethanol in Step B. ES+APCI MS m/z 506.3 [M+H]+.

Example 144

(S)-1-(4-(7-(3-hydroxynaphthalen-1-yl)-2-((1-(2-methoxyethyl)pyrrolidin-2-yl)methoxy)-5,6,7,8-tetrahydropyrido[3,4-d]pyrimidin-4-yl)piperazin-1-yl)prop-2-en-1-one

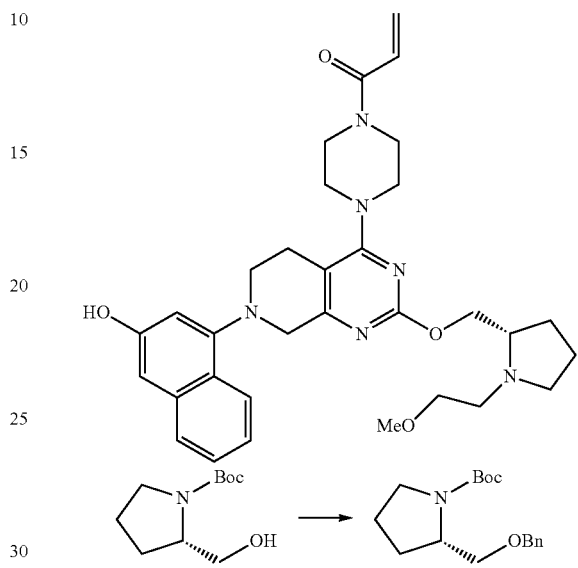

Step A: tert-butyl (2S)-2-(benzyloxymethyl)pyrrolidine-1-carboxylate

To a slurry of NaH (2.38 g, 59.6 mmol, 60% purity) in THF (50 mL) was added a solution of tert-butyl (2S)-2-(hydroxymethyl)pyrrolidine-1-carboxylate (10 g, 49.69 mmol) in THF (50 mL) at 0° C. and the mixture was stirred at 10° C. for 1 hour. Bromomethylbenzene (12.8 g, 74.5 mmol, 8.85 mL) was added dropwise at 0° C. and the mixture was stirred at 10° C. for 16 hours. The mixture was quenched by addition of saturated aqueous ammonia chloride solution (20 mL) and then diluted with ethyl acetate (200 mL) and water (100 mL). The separated organic layer was washed with water (100 mL) and brine (100 mL), dried over sodium sulfate, filtered and concentrated under vacuum. The residue was purified by column chromatography over silica gel (petroleum ether/ethyl acetate 100/1 to 5/1) to give tert-butyl (2S)-2-(benzyloxymethyl)pyrrolidine-1-carboxylate (8.2 g, 28.06 mmol, 56.5% yield, 99.7% purity) was obtained as a colorless oil. ES+APCI MS m/z 192.1 [M+H-Boc]+.

Step B: (2S)-2-(benzyloxymethyl)pyrrolidine

To a solution of tert-butyl (2S)-2-(benzyloxymethyl)pyrrolidine-1-carboxylate (8.2 g, 28.14 mmol) in CH2Cl2 (28 mL) was added TFA (43.1 g, 378 mmol, 28.0 mL) dropwise at 0° C. under nitrogen atmosphere. The mixture was stirred at 15° C. for 1 hour. The mixture was concentrated under vacuum. The residue was diluted with dichloromethane (100 mL) and then washed with 1M aqueous sodium hydroxide (10 mL) until the aqueous layer reached pH ~10. The separated organic layer was washed with brine (2×20 mL), dried over sodium sulfate, filtered and concentrated under vacuum to give (2S)-2-(benzyloxymethyl)pyrrolidine (4 g, 20.9 mmol, 74.3% yield LCMS ES+APCI MS m/z 192.2 [M+H]+.

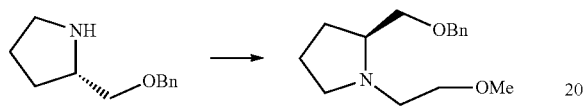

Step C: (2S)-2-(benzyloxymethyl)-1-(2-methoxy-ethyl)pyrrolidine

A mixture of 1-bromo-2-methoxy-ethane (0.9 g, 6.48 mmol, 608 uL), (2S)-2-(benzyloxymethyl)pyrrolidine (1.24 g, 6.48 mmol) and K$_2$CO$_3$ (2.68 g, 19.4 mmol) in CH$_3$CN (20 mL) was stirred at 15° C. for 1 hours and then at 78° C. for 12 hours. The mixture was diluted with ethyl acetate (50 mL) and water (50 mL). The separated organic layer was washed with brine (1×50 mL), dried over sodium sulfate, filtered and concentrated under vacuum. The residue was purified by column chromatography over silica gel (ethyl acetate/dichloromethane/methanol 1/1/0 to 10/10/2) to give (2S)-2-(benzyloxymethyl)-1-(2-methoxyethyl)pyrrolidine (900 mg, 3.61 mmol, 55.7% yield) as a colorless oil. ES+APCI MS m/z 250.2 [M+H]+.

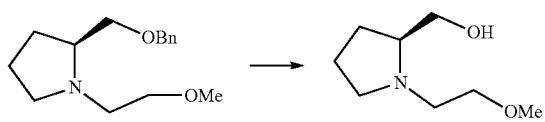 [SMILES: COCCN1CCC[C@H]1COCc1ccccc1 ; COCCN1CCC[C@H]1CO]

Step D: (S)-(1-(2-methoxyethyl)pyrrolidin-2-yl)methanol

A solution of (2S)-2-(benzyloxymethyl)-1-(2-methoxyethyl)pyrrolidine (900 mg, 3.61 mmol) in MeOH (20 mL) was added 10% Pd/C (721.88 umol) and the slurry stirred under H$_2$ (50 psi) at 10° C. for 16 hours. The reaction was filtered and the filtrate concentrated under vacuum to give (S)-(1-(2-methoxyethyl)pyrrolidin-2-yl)methanol (450 mg, 2.83 mmol, 78.30% yield).

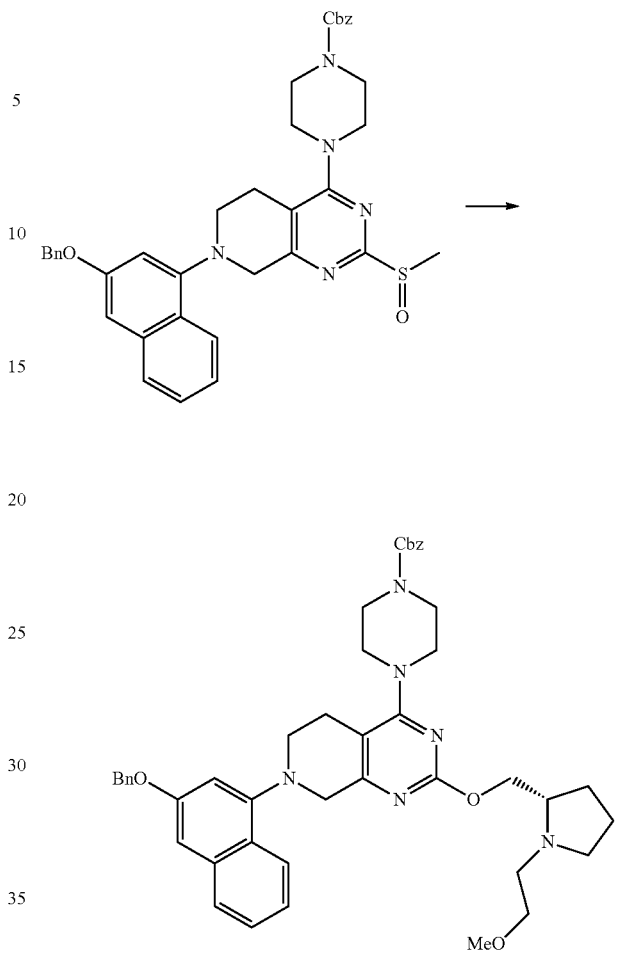

Step E: Benzyl 4-[7-(3-benzyloxy-1-naphthyl)-2-[[(2S)-1-(2-methoxyethyl)pyrrolidin-2-yl]methoxy]-6,8-dihydro-5H-pyrido[3,4-d]pyrimidin-4-yl]piperazine-1-carboxylate:

A mixture of [(2S)-1-(2-methoxyethyl)pyrrolidin-2-yl]methanol (245 mg, 1.54 mmol), benzyl 4-[7-(3-benzyloxy-1-naphthyl)-2-methylsulfinyl-6,8-dihydro-5H-pyrido[3,4-d]pyrimidin-4-yl]piperazine-1-carboxylate (500 mg, 772 umol), and t-BuONa (223 mg, 2.32 mmol) in THF (5 mL) was stirred at 20° C. for 0.5 hour under N$_2$ atmosphere. The reaction mixture was poured into H$_2$O (30 mL) and the aqueous layer extracted with ethyl acetate (3×30 mL). The combined organics were washed with brine (30 mL), dried over anhydrous Na$_2$SO$_4$ and concentrated under vacuum to give a residue. The residue was purified by column chromatography (SiO$_2$, DCM/MeOH=300/1 to 10:1) to give Benzyl 4-[7-(3-benzyloxy-1-naphthyl)-2-[[(2S)-1-(2-methoxyethyl)pyrrolidin-2-yl]methoxy]-6,8-dihydro-5H-pyrido[3,4-d]pyrimidin-4-yl]piperazine-1-carboxylate (260 mg, 349 umol, 45.3% yield). ES+APCI MS m/z 743.4 [M+H]+.

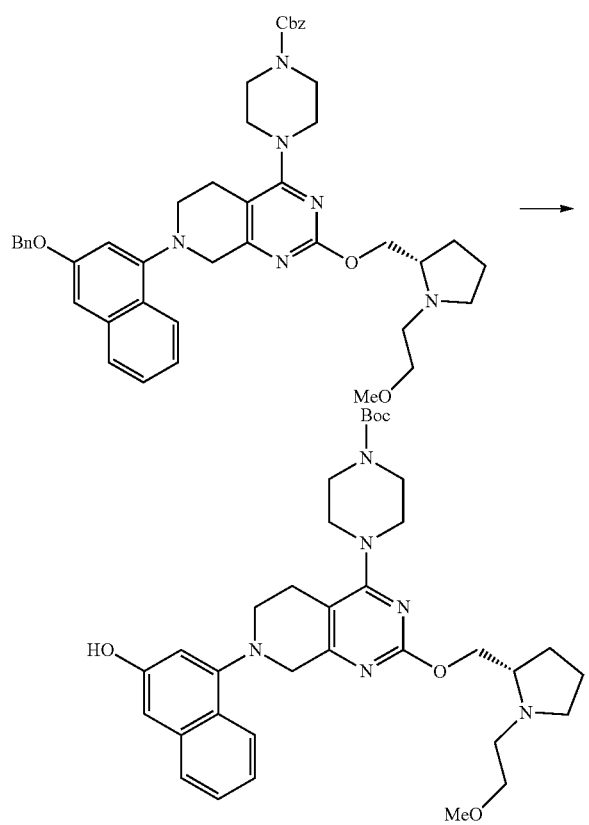

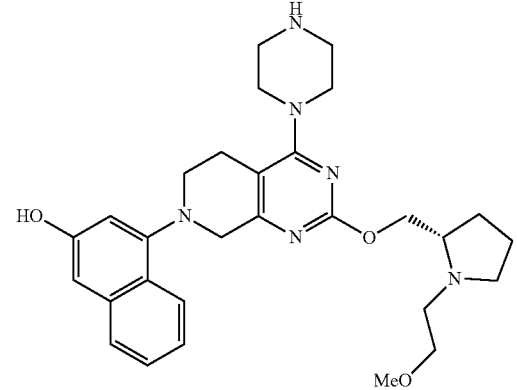

Step G: 4-[2-[[(2S)-1-(2-methoxyethyl)pyrrolidin-2-yl]methoxy]-4-piperazin-1-yl-6,8-dihydro-5H-pyrido[3,4-d]pyrimidin-7-yl]naphthalen-2-ol: To a solution of tert-butyl 4-[7-(3-hydroxy-1-naphthyl)-2-[[(2S)-1-(2-methoxyethyl)pyrrolidin-2-yl]methoxy]-6,8-dihydro-5H-pyrido[3,4-d]pyrimidin-4-yl]piperazine-1-carboxylate (215 mg, 347 umol) in DCM (500 uL) was added TFA (594 mg, 5.21 mmol, 385 uL) and the mixture stirred at 15° C. for 1 hour. The mixture was concentrated under vacuum to give 4-[2-[[(2S)-1-(2-methoxyethyl)pyrrolidin-2-yl]methoxy]-4-piperazin-1-yl-6,8-dihydro-5H-pyrido[3,4-d]pyrimidin-7-yl]naphthalen-2-ol (219 mg, 346 umol). ES+APCI MS m/z 519.4 [M+H]⁺.

Step F: tert-Butyl 4-[7-(3-hydroxy-1-naphthyl)-2-[[(2S)-1-(2-methoxyethyl)pyrrolidin-2-yl]methoxy]-6,8-dihydro-5H-pyrido[3,4-d]pyrimidin-4-yl]piperazine-1-carboxylate: To a solution of benzyl 4-[7-(3-benzyloxy-1-naphthyl)-2-[[(2S)-1-(2-methoxyethyl)pyrrolidin-2-yl]methoxy]-6,8-dihydro-5H-pyrido[3,4-d]pyrimidin-4-yl]piperazine-1-carboxylate (240 mg, 323 umol) and (Boc)₂O (141 mg, 646 umol, 148 uL) in MeOH (150 mL) was added 10% Pd/C (100 mg) under N₂ atmosphere. The suspension was degassed and purged with H₂ 3 times. The mixture was stirred under H₂ (15 PSI) at 40° C. for 12 hours. The reaction mixture was filtered and the filtrate concentrated to give tert-Butyl 4-[7-(3-hydroxy-1-naphthyl)-2-[[(2S)-1-(2-methoxyethyl)pyrrolidin-2-yl]methoxy]-6,8-dihydro-5H-pyrido[3,4-d]pyrimidin-4-yl]piperazine-1-carboxylate (215 mg, crude). ES+APCI MS m/z 619.1 [M+H]⁺.

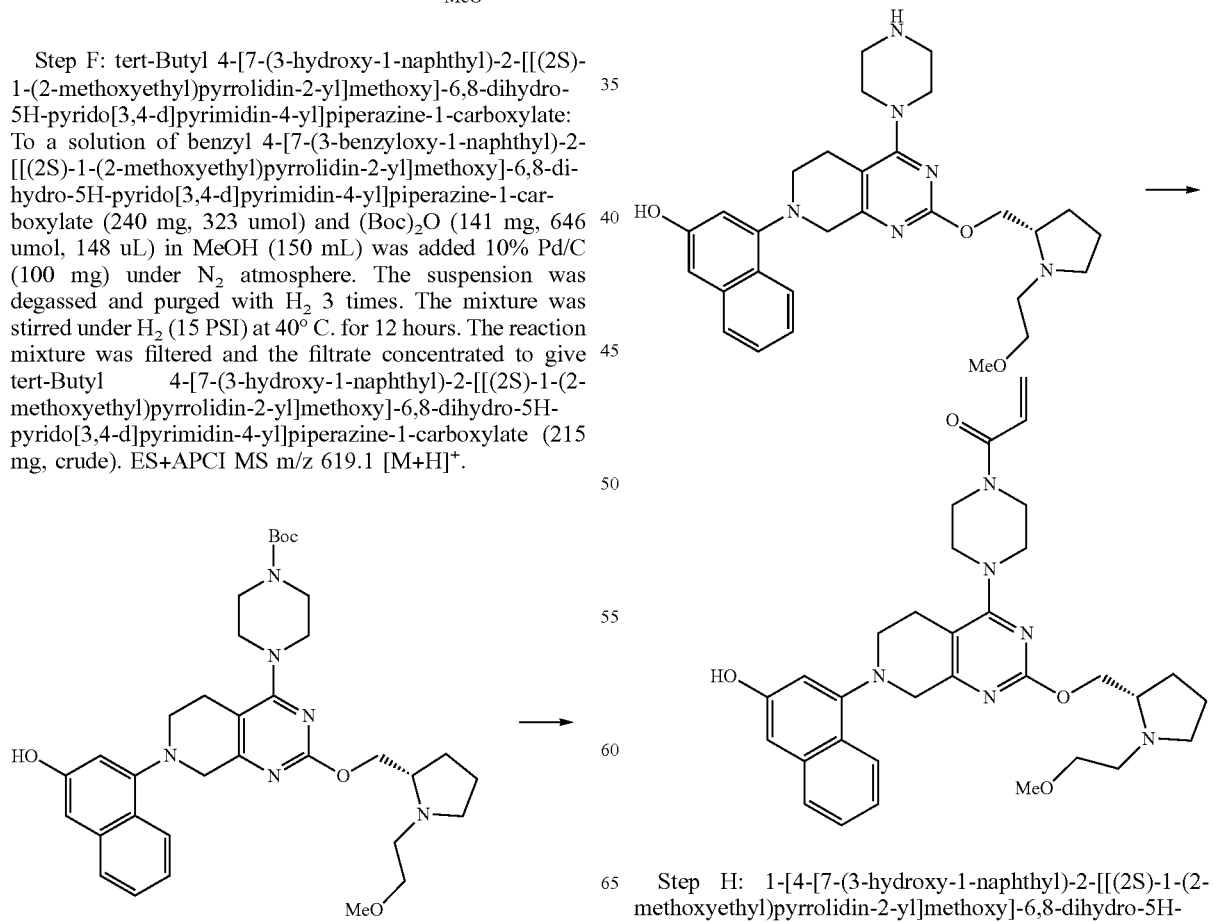

Step H: 1-[4-[7-(3-hydroxy-1-naphthyl)-2-[[(2S)-1-(2-methoxyethyl)pyrrolidin-2-yl]methoxy]-6,8-dihydro-5H-pyrido[3,4-d]pyrimidin-4-yl]piperazin-1-yl]prop-2-en-1- one: To a mixture of 4-[2-[[(2S)-1-(2-methoxyethyl)pyrrolidin-2-yl]methoxy]-4-piperazin-1-yl-6,8-dihydro-5H-pyrido[3,4-d]pyrimidin-7-yl]naphthalen-2-ol (219 mg, 346 umol) and DIEA (447 mg, 3.46 mmol, 603 uL) in dichloromethane (4.00 mL) cooled to −40° C. was added a solution of prop-2-enoyl prop-2-enoate (34.9 mg, 276.92 umol) in dichloromethane (1.00 mL) under a nitrogen atmosphere. The mixture was stirred at −40° C. for 1 hour. The reaction was quenched by addition of saturated NaHCO₃ (2.00 mL) and the mixture poured into ice-water (20 mL) and extracted with dichloromethane (20 mL×2). The combined organics were dried over sodium sulfate, filtered and concentrated in vacuo. The residue was purified by prep-HPLC (column: Gemini 150*25 5 u; mobile phase: [water (0.05% ammonia hydroxide v/v)-ACN]; B %: 32%-62%, 12 min) to give 1-[4-[7-(3-hydroxy-1-naphthyl)-2-[[(2S)-1-(2-methoxyethyl)pyrrolidin-2-yl]methoxy]-6,8-dihydro-5H-pyrido[3,4-d]pyrimidin-4-yl]piperazin-1-yl]prop-2-en-1-one (27 mg, 46.7 umol). ES+APCI MS m/z 573.3 [M+H]⁺.

Example 145

1-[4-[7-(3-hydroxy-1-naphthyl)-2-[[(2S)-1-isopropylpyrrolidin-2-yl]methoxy]-6,8-dihydro-5H-pyrido[3,4-d]pyrimidin-4-yl]piperazin-1-yl]prop-2-en-1-one

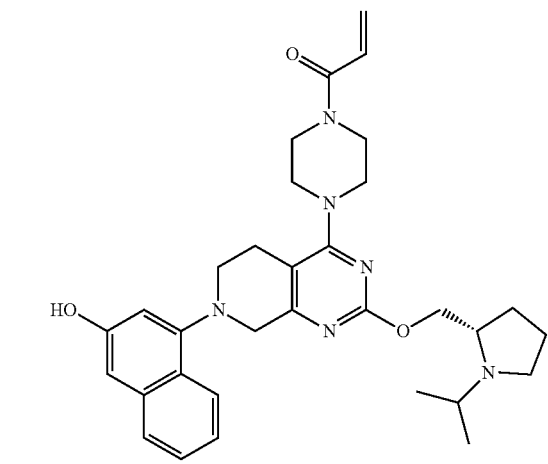

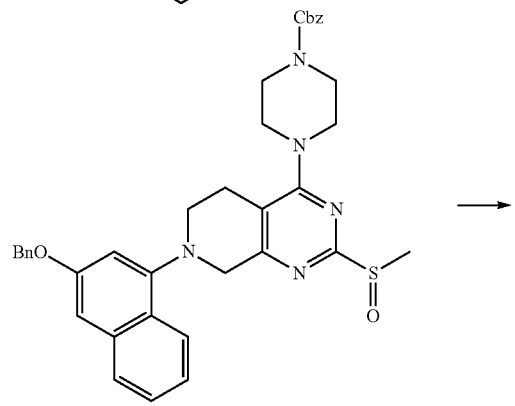

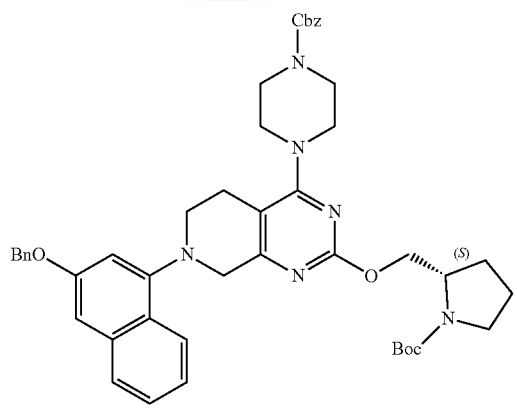

Step A: Benzyl 4-[7-(3-benzyloxy-1-naphthyl)-2-[[(2S)-1-tert-butoxycarbonylpyrrolidin-2-yl]methoxy]-6,8-dihydro-5H-pyrido[3,4-d]pyrimidin-4-yl]piperazine-1-carboxylate: To a solution of tert-butyl (2S)-2-(hydroxymethyl)pyrrolidine-1-carboxylate (1.24 g, 6.17 mmol) and benzyl 4-[7-(3-benzyloxy-1-naphthyl)-2-methylsulfinyl-6,8-dihydro-5H-pyrido[3,4-d]pyrimidin-4-yl]piperazine-1-carboxylate (2 g, 3.09 mmol) in THF (50 mL) was added t-BuONa (890 mg, 9.26 mmol) and the reaction stirred at 15° C. for 0.5 hour. The reaction mixture was poured into H₂O (100 mL) and extracted with ethyl acetate (3×100 mL). The combined organics were washed with brine (50 mL), dried over anhydrous Na₂SO₄ and concentrated under vacuum to give a residue. The residue was purified by column chromatography (SiO₂, Petroleum ether/Ethyl acetate=100/1 to 1:1) to give Benzyl 4-[7-(3-benzyloxy-1-naphthyl)-2-[[(2S)-1-tert-butoxycarbonylpyrrolidin-2-yl]methoxy]-6,8-dihydro-5H-pyrido[3,4-d]pyrimidin-4-yl]piperazine-1-carboxylate (1.62 g, 2.02 mmol, 65.5% yield). ES+APCI MS m/z 785.6 [M+H]⁺.

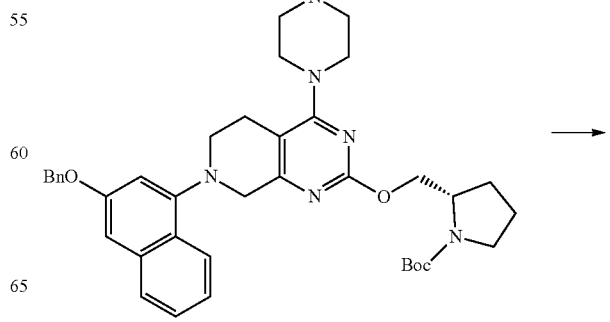

-continued

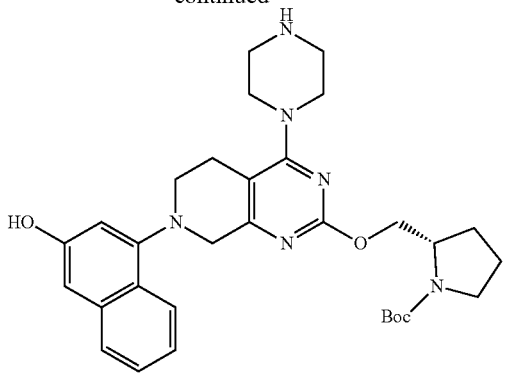

Step B: (2S)-2-[[7-(3-hydroxy-1-naphthyl)-4-piperazin-1-yl-6,8-dihydro-5H-pyrido[3,4-d]pyrimidin-2-yl]oxymethyl]pyrrolidine-1-carboxylate: NH₃ was bubbled into MeOH (50 mL) at 15° C. for 30 minutes. To this solution was added benzyl 4-[7-(3-benzyloxy-1-naphthyl)-2-[[(2S)-1-tert-butoxycarbonyl pyrrolidin-2-yl]methoxy]-6,8-dihydro-5H-pyrido[3,4-d]pyrimidin-4-yl]piperazine-1-carboxylate (1.6 g, 2.04 mmol) followed by dry 10% Pd/C (500 mg) under N₂. The suspension was degassed under vacuum and purged with H₂ several times. The mixture was stirred under H₂ (15 psi) at 40° C. for 1 hour. The mixture was then filtered and the filtrate concentrated under vacuum to give tert-butyl (2S)-2-[[7-(3-hydroxy-1-naphthyl)-4-piperazin-1-yl-6,8-dihydro-5H-pyrido[3,4-d]pyrimidin-2-yl]oxymethyl]pyrrolidine-1-carboxylate (1.00 g, 1.78 mmol). ES+APCI MS m/z 561.5 [M+H]⁺.

Step C: tert-butyl (2S)-2-[[7-(3-hydroxy-1-naphthyl)-4-[4-(2,2,2-trifluoroacetyl)piperazin-1-yl]-6,8-dihydro-5H-pyrido[3,4-d]pyrimidin-2-yl]oxymethyl]pyrrolidine-1-carboxylate: To a solution of tert-butyl (2S)-2-[[7-(3-hydroxy-1-naphthyl)-4-piperazin-1-yl-6,8-dihydro-5H-pyrido[3,4-d]pyrimidin-2-yl]oxymethyl]pyrrolidine-1-carboxylate (800 mg, 1.43 mmol) in DCM (5.00 mL) at 0° C. was added TFAA (599 mg, 2.85 mmol) and DIEA (737 mg, 5.71 mmol) and the reaction stirred at 0° C. for 0.5 hour. The reaction mixture was poured into H₂O (50 mL) and extracted with ethyl acetate (50 mL×3). The combined organics were washed with brine (30 mL), dried over anhydrous Na₂SO₄, filtered and concentrated under vacuum to give tert-butyl (2S)-2-[[7-(3-hydroxy-1-naphthyl)-4-[4-(2,2,2-trifluoroacetyl)piperazin-1-yl]-6,8-dihydro-5H-pyrido[3,4-d]pyrimidin-2-yl]oxymethyl]pyrrolidine-1-carboxylate (1.5 g, crude). ES+APCI MS m/z 657.5 [M+H]⁺.

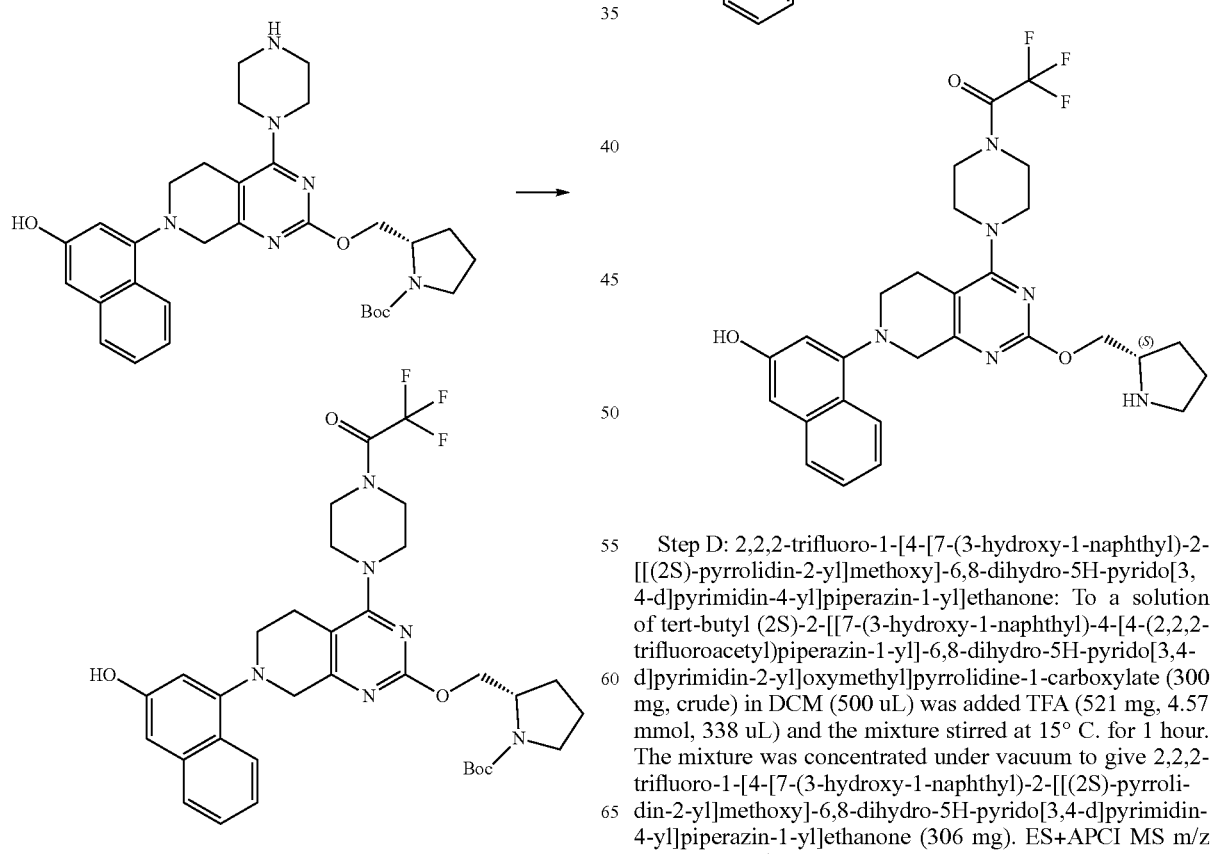

Step D: 2,2,2-trifluoro-1-[4-[7-(3-hydroxy-1-naphthyl)-2-[[(2S)-pyrrolidin-2-yl]methoxy]-6,8-dihydro-5H-pyrido[3,4-d]pyrimidin-4-yl]piperazin-1-yl]ethanone: To a solution of tert-butyl (2S)-2-[[7-(3-hydroxy-1-naphthyl)-4-[4-(2,2,2-trifluoroacetyl)piperazin-1-yl]-6,8-dihydro-5H-pyrido[3,4-d]pyrimidin-2-yl]oxymethyl]pyrrolidine-1-carboxylate (300 mg, crude) in DCM (500 uL) was added TFA (521 mg, 4.57 mmol, 338 uL) and the mixture stirred at 15° C. for 1 hour. The mixture was concentrated under vacuum to give 2,2,2-trifluoro-1-[4-[7-(3-hydroxy-1-naphthyl)-2-[[(2S)-pyrrolidin-2-yl]methoxy]-6,8-dihydro-5H-pyrido[3,4-d]pyrimidin-4-yl]piperazin-1-yl]ethanone (306 mg). ES+APCI MS m/z 557.3 [M+H]⁺.

425

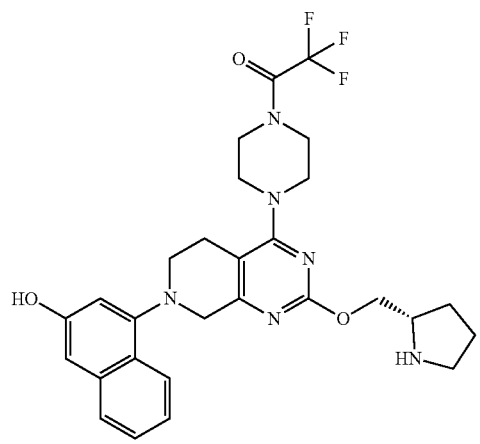

426

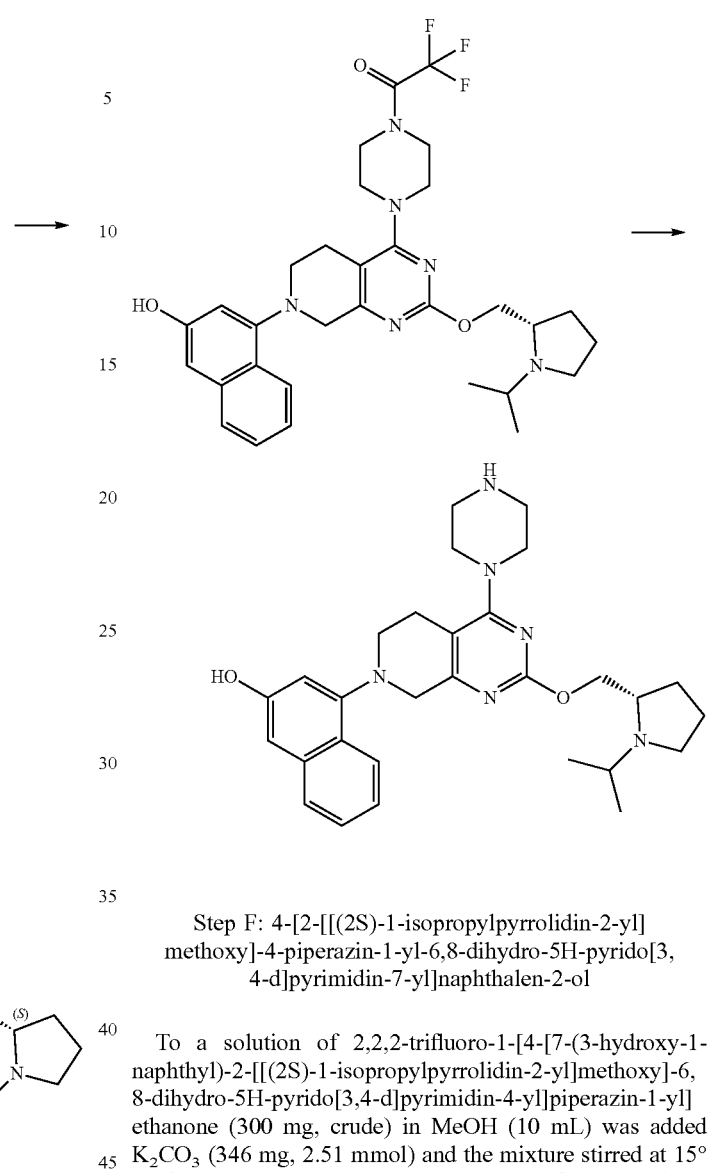

Step F: 4-[2-[[(2S)-1-isopropylpyrrolidin-2-yl] methoxy]-4-piperazin-1-yl-6,8-dihydro-5H-pyrido[3, 4-d]pyrimidin-7-yl]naphthalen-2-ol To a solution of 2,2,2-trifluoro-1-[4-[7-(3-hydroxy-1-naphthyl)-2-[[(2S)-1-isopropylpyrrolidin-2-yl]methoxy]-6, 8-dihydro-5H-pyrido[3,4-d]pyrimidin-4-yl]piperazin-1-yl] ethanone (300 mg, crude) in MeOH (10 mL) was added K$_2$CO$_3$ (346 mg, 2.51 mmol) and the mixture stirred at 15° C. for 1 hour. The reaction mixture was filtered and the filtrate concentrated to give 4-[2-[[(2S)-1-isopropylpyrrolidin-2-yl]methoxy]-4-piperazin-1-yl-6,8-dihydro-5H-pyrido [3,4-d]pyrimidin-7-yl]naphthalen-2-ol (250 mg). ES+APCI MS m/z 503.3 [M+H]$^+$.

Step E: 2,2,2-trifluoro-1-[4-[7-(3-hydroxy-1-naphthyl)-2-[[(2S)-1-isopropylpyrrolidin-2-yl] methoxy]-6,8-dihydro-5H-pyrido[3,4-d]pyrimidin-4-yl]piperazin-1-yl]ethanone:

To a solution of acetone (132 mg, 2.28 mmol, 167 uL) and 2,2,2-trifluoro-1-[4-[7-(3-hydroxy-1-naphthyl)-2-[[(2S)-pyrrolidin-2-yl]methoxy]-6,8-dihydro-5H-pyrido[3,4-d]pyrimidin-4-yl]piperazin-1-yl]ethanone (306 mg, crude, TFA) in MeOH (5.00 mL) was added AcOH (54.8 mg, 912 umol, 52.2 uL) and NaBH$_3$CN (115 mg, 1.83 mmol) and the mixture stirred at 15° C. for 16 hours. The reaction mixture was diluted with H$_2$O (20 mL) and extracted with ethyl acetate (20 mL×3). The combined organics were washed with brine (10 mL), dried over Na$_2$SO$_4$, filtered and concentrated under reduced pressure to give 2,2,2-trifluoro-1-[4-[7-(3-hydroxy-1-naphthyl)-2-[[(2S)-1-isopropylpyrrolidin-2-yl] methoxy]-6,8-dihydro-5H-pyrido [3,4-d] pyrimidin-4-yl]piperazin-1-yl]ethanone (300 mg, crude). ES+APCI MS m/z 599.5 [M+H]$^+$.

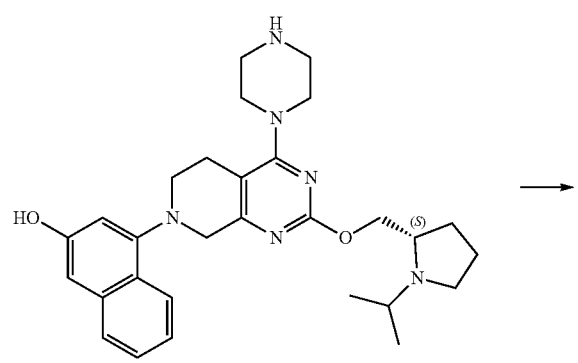

427

-continued

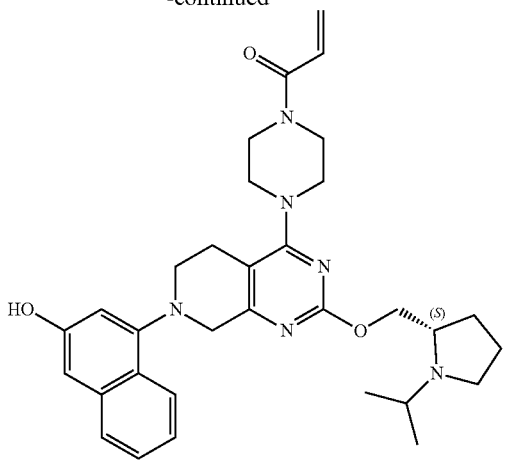

Step G: 1-[4-[7-(3-hydroxy-1-naphthyl)-2-[[(2S)-1-isopropylpyrrolidin-2-yl] methoxy]-6,8-dihydro-5H-pyrido[3,4-d]pyrimidin-4-yl]piperazin-1-yl]prop-2-en-1-one: To a mixture of 4-[2-[[(2S)-1-isopropylpyrrolidin-2-yl] methoxy]-4-piperazin-1-yl-6,8-dihydro-5H-pyrido[3,4-d] pyrimidin-7-yl]naphthalen-2-ol (250 mg, crude) and DIEA (643 mg, 4.97 mmol, 866 uL) in DCM (5.00 mL) cooled to −40° C. was added a solution of prop-2-enoyl prop-2-enoate (50.2 mg, 398 umol) in DCM (1 mL) under nitrogen atmosphere. The mixture was stirred at −40° C. for 1 hour. The reaction was quenched by addition of saturated NaHCO$_3$ (2.00 mL). The mixture was poured into ice-water (20 mL) and extracted with DCM (20 mL×2). The combined organics were dried over sodium sulfate, filtered and concentrated in vacuo. The residue was purified by prep-HPLC (column: Phenomenex Gemini 150*25 mm*10 um; mobile phase: [water (0.05% ammonia hydroxide v/v)-ACN]; B %: 52%-78%, 12 min). 1-[4-[7-(3-hydroxy-1-naphthyl)-2-[[(2S)-1-isopropylpyrrolidin-2-yl] methoxy]-6,8-dihydro-5H-pyrido[3,4-d]pyrimidin-4-yl]piperazin-1-yl]prop-2-en-1-one (10 mg, 17.6 umol). ES+APCI MS m/z 557.3 [M+H]$^+$.

Example 146

1-[4-[7-(3-hydroxy-1-naphthyl)-2-[[(3R)-pyrrolidin-3-yl]methoxy]-6,8-dihydro-5H-pyrido[3,4-d]pyrimidin-4-yl]piperazin-1-yl]prop-2-en-1-one

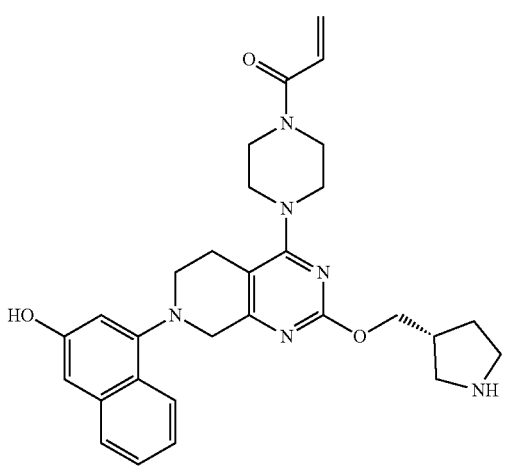

428

-continued

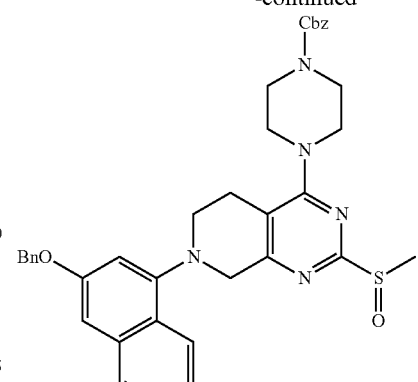 

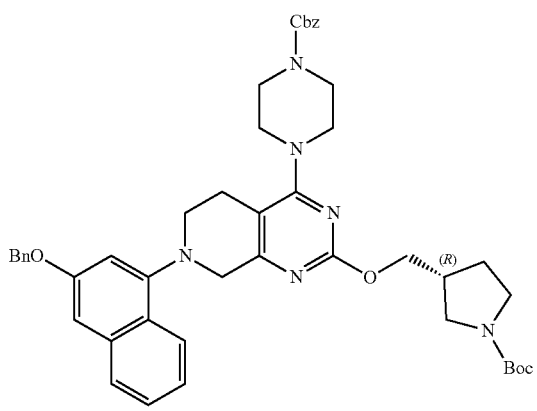

Step A: benzyl 4-[7-(3-benzyloxy-1-naphthyl)-2-[[(3R)-1-tert-butoxycarbonylpyrrolidin-3-yl]methoxy]-6,8-dihydro-5H-pyrido[3,4-d]pyrimidin-4-yl]piperazine-1-carboxylate: A mixture of benzyl 4-[7-(3-benzyloxy-1-naphthyl)-2-methylsulfinyl-6,8-dihydro-5H-pyrido[3,4-d] pyrimidin-4-yl]piperazine-1-carboxylate (0.50 g, 772 umol), tert-butyl (3R)-3-(hydroxymethyl)pyrrolidine-1-carboxylate (311 mg, 1.54 mmol) and t-BuONa (223 mg, 2.32 mmol) in THF (10 mL) was stirred at 20° C. for 1 hour. The mixture was diluted with water (10 mL) and the aqueous layer extracted with ether acetate (3×20 mL). The combined organics were washed with saturated sodium chloride (1×30 mL), dried over Na$_2$SO$_4$, filtered and concentrated under vacuum. The residue was purified by column chromatography (SiO$_2$, petroleum ether/ether acetate=3/1) to give benzyl 4-[7-(3-benzyloxy-1-naphthyl)-2-[[(3R)-1-tert-butoxycarbonylpyrrolidin-3-yl]methoxy]-6,8-dihydro-5H-pyrido[3,4-d]pyrimidin-4-yl]piperazine-1-carboxylate (0.40 g, 499 umol). ES+APCI MS m/z 785.2 [M+H]$^+$.

429

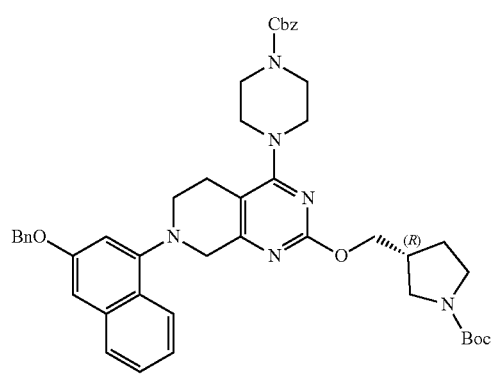

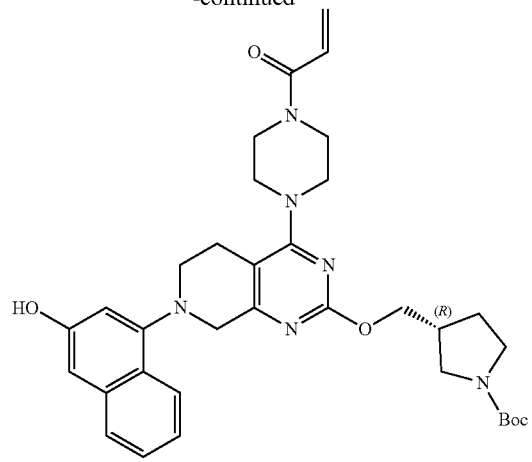

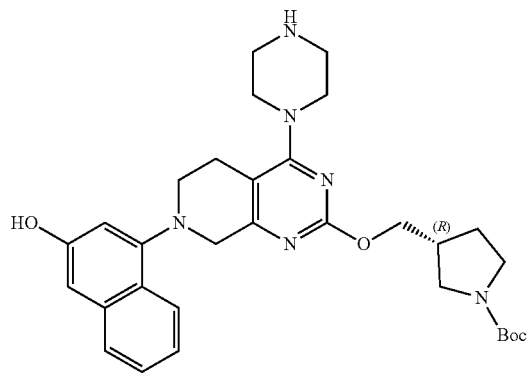

Step B: tert-butyl (3R)-3-[[7-(3-hydroxy-1-naphthyl)-4-piperazin-1-yl-6,8-dihydro-5H-pyrido[3,4-d] pyrimidin-2-yl]oxymethyl]pyrrolidine-1-carboxylate: NH$_3$ was bubbled into methanol (10 mL) at −78° C. for 30 minutes. Benzyl 4-[7-(3-benzyloxy-1-naphthyl)-2-[[(3R)-1-tert-butoxycarbonylpyrrolidin-3-yl] methoxy]-6,8-dihydro-5H-pyrido[3,4-d]pyrimidin-4-yl]piperazine-1-carboxylate (0.25 g, 319 umol) and 10% Pd/C (0.10 g) were added into the mixture and stirred at 10° C. for 1 hour under H$_2$ (15 psi). The mixture was filtered and concentrated under vacuum to give tert-butyl (3R)-3-[[7-(3-hydroxy-1-naphthyl)-4-piperazin-1-yl-6,8-dihydro-5H-pyrido[3,4-d] pyrimidin-2-yl]oxymethyl]pyrrolidine-1-carboxylate (0.17 g, 303 umol). ES+APCI MS m/z 561.3 [M+H]$^+$.

430
-continued

Step C: tert-butyl (3R)-3-[[7-(3-hydroxy-1-naphthyl)-4-(4-prop-2-enoylpiperazin-1-yl)-6,8-dihydro-5H-pyrido[3,4-d]pyrimidin-2-yl]oxymethyl]pyrrolidine-1-carboxylate: To a solution of tert-butyl (3R)-3-[[7-(3-hydroxy-1-naphthyl)-4-piperazin-1-yl-6,8-dihydro-5H-pyrido[3,4-d]pyrimidin-2-yl]oxymethyl]pyrrolidine-1-carboxylate (0.17 g, 303 umol) and Et$_3$N (153 mg, 1.52 mmol, 211 uL) in dichloromethane (4.00 mL) cooled to −40° C. was added prop-2-enoyl prop-2-enoate (26.8 mg, 212 umol) and the mixture stirred at −40° C. for 0.5 h. The mixture was quenched by addition of methanol (0.10 mL) and concentrated under vacuum. The residue was purified by column chromatography (Al$_2$O$_3$, dichloromethane/methane=10/1) to give tert-butyl (3R)-3-[[7-(3-hydroxy-1-naphthyl)-4-(4-prop-2-enoylpiperazin-1-yl)-6,8-dihydro-5H-pyrido[3,4-d]pyrimidin-2-yl]oxymethyl]pyrrolidine-1-carboxylate (0.12 g, 189 umol). ES+APCI MS m/z 615.5 [M+H]$^+$.

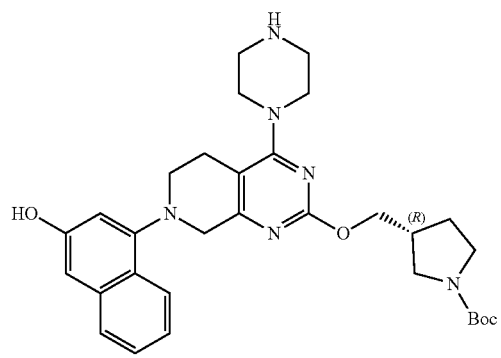

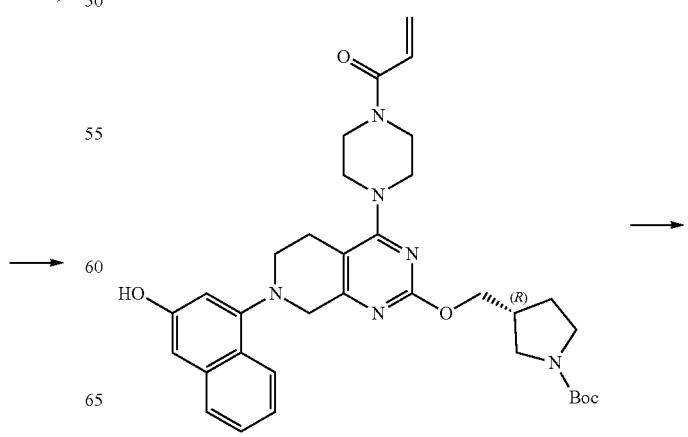

431
-continued

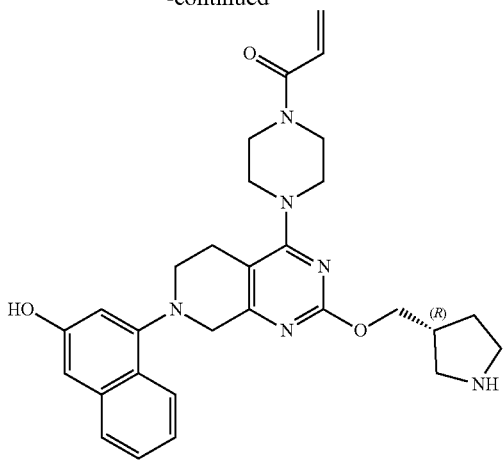

Step D: 1-[4-[7-(3-hydroxy-1-naphthyl)-2-[[(3R)-pyrrolidin-3-yl]methoxy]-6,8-dihydro-5H-pyrido[3,4-d]pyrimidin-4-yl]piperazin-1-yl]prop-2-en-1-one: A mixture of tert-butyl (3R)-3-[[7-(3-hydroxy-1-naphthyl)-4-(4-prop-2-enoylpiperazin-1-yl)-6,8-dihydro-5H-pyrido[3,4-d]pyrimidin-2-yl]oxymethyl]pyrrolidine-1-carboxylate (0.10 g, 163 umol) and TFA (278 mg, 2.44 mmol, 181 uL) in dichloromethane (0.20 mL) was stirred at 10° C. for 1 hour. The mixture was quenched by addition of NH$_3$.H$_2$O and the pH adjusted until the pH=7. The mixture was purified by prep-HPLC (column: Venusil XBP C8 150*25*10 um; mobile phase: [water (0.225% Formic Acid)-ACN]; B %: 15%-45%, 10 min) to give 1-[4-[7-(3-hydroxy-1-naphthyl)-2-[[(3R)-pyrrolidin-3-yl]methoxy]-6,8-dihydro-5H-pyrido[3,4-d]pyrimidin-4-yl]piperazin-1-yl]prop-2-en-1-one (22.8 mg, 42.9 umol). ES+APCI MS m/z 515.4 [M+H]$^+$.

Example 147

2-[4-[2-[[(2S)-1-methylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile

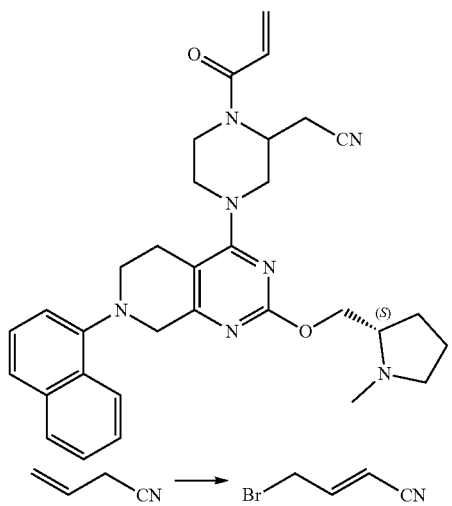

432

Step A: (Z) and (E)-4-bromobut-2-enenitrile

To a solution of but-3-enenitrile (98 g, 1.46 mol, 118 mL) in tert-butanol (150 mL) and petroleum ether (575 mL) was added a solution of Br$_2$ (233 g, 1.46 mol, 75.3 mL) in tert-butanol (150 mL) at 15° C. and the reaction stirred for 30 minutes. To the reaction was next added an ethanol solution of sodium ethoxide (100 g, 0.6 mol, 850 mL). The reaction mixture was stirred for 2 hours at the 15° C. The reaction was next filtered and the filtrate concentrated under vacuum. The residue was purified by column chromatography using 2→20% ethyl acetate/petroleum ether as eluent to give a mixture of (Z) and (E)-4-bromobut-2-enenitrile (141 g, E/Z=2.5/1, crude) as a slight yellow oil. $^1$H NMR (400 MHz, chloroform-d) (E), δ=6.79 (td, J=7.2, 16.0 Hz, 1H), 5.63 (d, J=16.0 Hz, 1H), 4.00 (dd, J=1.2, 6.8 Hz, 2H); (Z), δ=6.66 (td, J=8.0, 10.8 Hz, 1H), 5.44 (d, J=10.8 Hz, 1H), 4.16 (dd, J=0.8, 8.0 Hz, 2H).

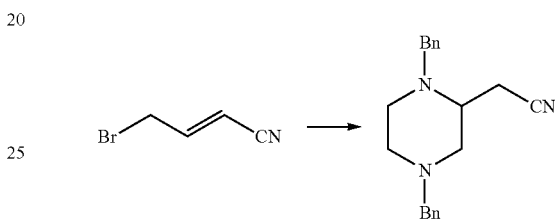

Step B: 2-(1,4-dibenzylpiperazin-2-yl)acetonitrile

To a mixture of N,N-dibenzylethane-1,2-diamine (115 g, 480 mmol, 113 mL) and TEA (97.0 g, 959 mmol, 133 mL) in toluene (1 L) was added 4-bromobut-2-enenitrile (70 g, crude) dropwise at 0° C. and the reaction stirred at 15° C. for 12 hours. The reaction mixture was filtered and the filtrate concentrated under reduced pressure. The residue was purified by column chromatography using 5450% EtOAc/Petroleum Ether as eluent to give 2-(1,4-dibenzylpiperazin-2-yl)acetonitrile (82 g, 240 mmol, two steps 37% yield, 89.3% purity) as a slight yellow semisolid. ES+APCI MS m/z 306.3 [M+H]$^+$. $^1$H NMR (400 MHz, chloroform-d) δ=7.40-7.23 (m, 10H), 3.85-3.76 (m, 1H), 3.54-3.44 (m, 3H), 3.07-2.96 (m, 1H), 2.94-2.84 (m, 1H), 2.68-2.35 (m, 7H).

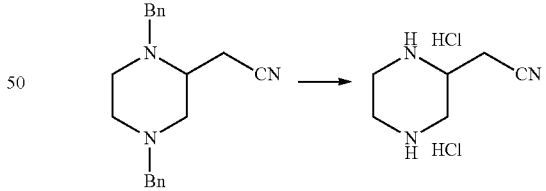

Step C: 2-piperazin-2-ylacetonitrile

To a solution of 2-(1,4-dibenzylpiperazin-2-yl)acetonitrile (164 g, 536 mmol) in DCE (1500 mL) was added 1-chloroethyl carbonochloridate (306 g, 2.14 mol) dropwise at 0° C. After addition, the reaction mixture was heated to 85° C. for approximately 48 hours. The dichloroethane was evaporated and the residue was taken up in MeOH (1500 mL) and heated to 70° C. for 1 hour. The reaction mixture was concentrated under reduced pressure and the solids triturated with MTBE (3×3 L) and the solids dried under reduced pressure to give 2-piperazin-2-ylacetonitrile. The crude product was purified by recrystallization with Ethanol and water (8:1, v:v) to give 2-piperazin-2-ylacetonitrile as an off-white solid (53 g, 428 mmol, 40.0% yield, 96.4% purity, 2 HCl). ES+APCI MS m/z 126.2 [M+H]+. 1H NMR (400 MHz, D2O) δ=4.01-3.96 (m, 1H), 3.81-3.67 (m, 3H), 3.46-3.27 (m, 3H), 3.09 (d, J=6.0 HZ, 2H).

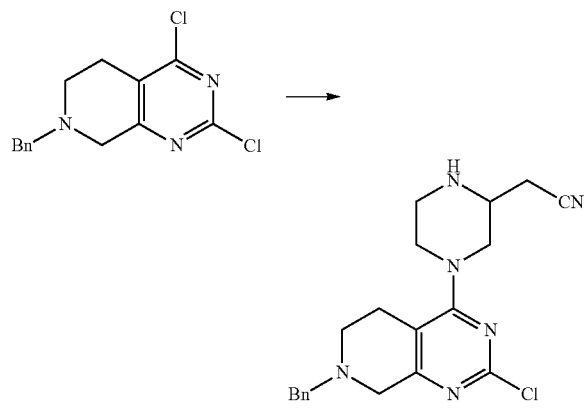

Step D: 2-[4-(7-benzyl-2-chloro-6,8-dihydro-5H-pyrido[3,4-d]pyrimidin-4-yl)piperazin-2-yl]acetonitrile To a mixture of 7-benzyl-2,4-dichloro-6,8-dihydro-5H-pyrido[3,4-d]pyrimidine (1.2 g, 4.08 mmol) and 2-piperazin-2-ylacetonitrile (808 mg, 4.08 mmol, 2HCl) in dioxane (24 mL) was added DIEA (2.64 g, 20.4 mmol, 3.55 mL). The reaction mixture was stirred at 50° C. for 3 hours. Upon completion, the reaction mixture was diluted with water (50 mL) and the aqueous layer extracted with EtOAc (3×80 mL). The combined organic layers were washed with brine (30 mL), dried over Na2SO4 and concentrated under vacuum to give 2-[4-(7-benzyl-2-chloro-6,8-dihydro-5H-pyrido[3,4-d]pyrimidin-4-yl)piperazin-2-yl]acetonitrile (1.56 g, 4.07 mmol, 100% yield) as a brown solid.

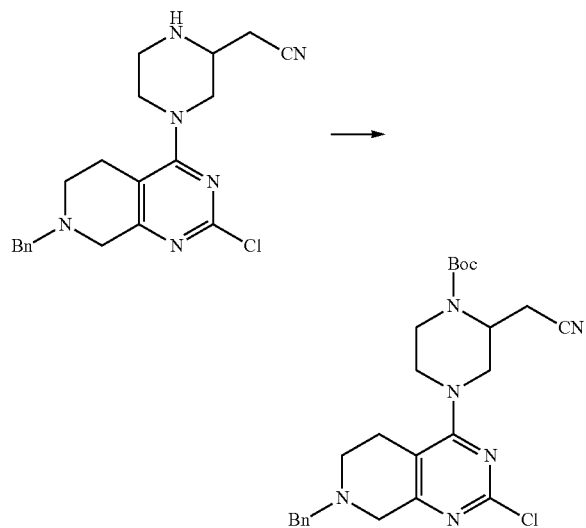

Step E: tert-butyl 4-(7-benzyl-2-chloro-6,8-dihydro-5H-pyrido[3,4-d]pyrimidin-4-yl)-2-(cyanomethyl)piperazine-1-carboxylate To 2-[4-(7-benzyl-2-chloro-6,8-dihydro-5H-pyrido[3,4-d]pyrimidin-4-yl)piperazin-2-yl]acetonitrile (1.56 g, 4.07 mmol) was added (Boc)2O (9.50 g, 43.5 mmol, 10 mL) and the mixture heated to 50° C. for 2 hours. Upon completion, the reaction mixture was purified by silica gel chromatography using 10→50% EtOAc/Petroleum Ether as eluent to give tert-butyl 4-(7-benzyl-2-chloro-6,8-dihydro-5H-pyrido[3,4-d]pyrimidin-4-yl)-2-(cyanomethyl)piperazine-1-carboxylate (1.2 g, 2.44 mmol, 59.9% yield, 98.3% purity) as brown solid. ES+APCI MS m/z 483.3 [M+H]+. 1H NMR (400 MHz, CHLOROFORM-d) δ=7.39-7.27 (m, 5H), 4.59 (br s, 1H), 4.06 (br d, J=13.6 Hz, 2H), 3.90 (br d, J=11.6 Hz, 1H), 3.74-3.49 (m, 4H), 3.29 (dd, J=4.0, 13.6 Hz, 1H), 3.18 (br s, 1H), 3.10-3.00 (m, 1H), 2.85-2.55 (m, 6H), 1.53-1.45 (m, 9H).

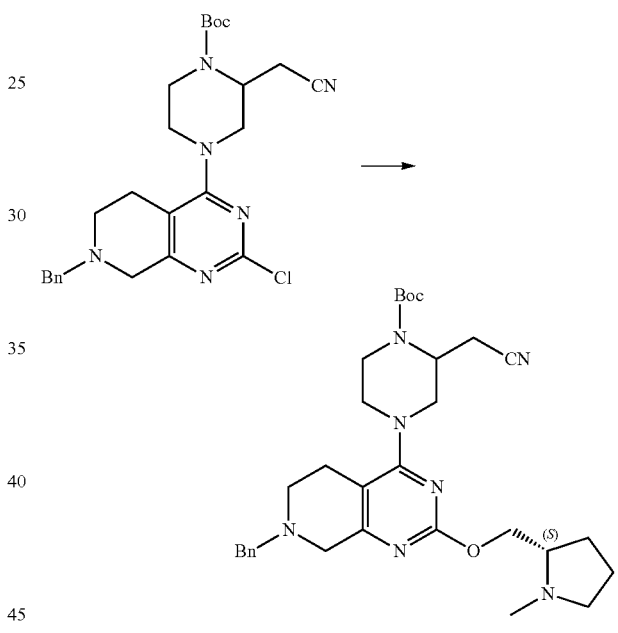

Step F: tert-butyl 4-[7-benzyl-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate: To a solution of [(2S)-1-methylpyrrolidin-2-yl]methanol (655.74 mg, 5.69 mmol, 676 uL in THF (25 mL) was added NaH (182 mg, 4.55 mmol, 60% purity) at 0° C. and the reaction mixture stirred at 0° C. for 0.5 h. To the mixture was added tert-butyl 4-(7-benzyl-2-chloro-6,8-dihydro-5H-pyrido[3,4-d]pyrimidin-4-yl)-2-(cyanomethyl) piperazine-1-carboxylate (1.1 g, 2.28 mmol) and the reaction mixture stirred at 70° C. for 12 hours in a sealed tube under N2. Upon completion, the reaction mixture was quenched by addition of saturated NH4Cl (20 mL) and the aqueous layer extracted with EtOAc (2×50 mL). The combined organics were washed with brine (10 mL), dried over Na2SO4, filtered and concentrated under vacuum to give tert-butyl 4-[7-benzyl-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (1.1 g, 1.86 mmol, 81.7% yield, 95% purity) as a brown solid. ES+APCI MS m/z 562.4 [M+H]+.

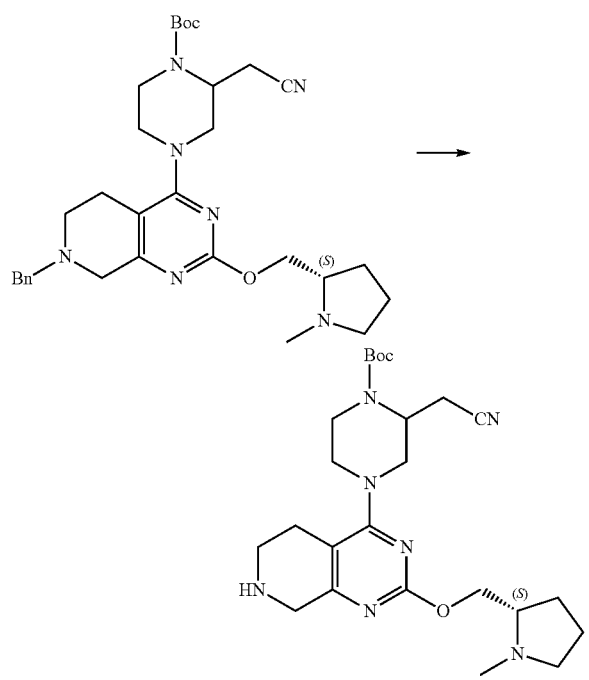

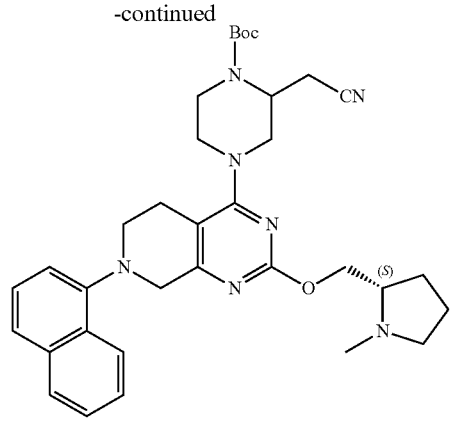

Step G: tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate: Ammonia was bubbled into MeOH (30 mL) for 5 minutes. To this solution was added tert-butyl 4-[7-benzyl-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (950 mg, 1.69 mmol) and 10% Pd/C (200 mg). The suspension was degassed under vacuum and purged with $H_2$ several times and the mixture stirred under $H_2$ (15 psi) at 40° C. for 9 hours. Upon completion, the reaction mixture was filtered and concentrated under vacuum. The residue was purified by prep-HPLC (column: Phenomenex Synergi Max-RP 250*50 mm*10 um; mobile phase: [water (0.225% Formic Acid)-ACN]; B %: 15%-40%,30; 58% min) to give tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (400 mg, 830 umol, 49.1% yield, 97.8% purity) was obtained as brown oil. ES+APCI MS m/z 472.4 [M+H]+. $^1$H NMR (400 MHz, CHLOROFORM-d) δ=4.59 (br s, 1H), 4.43-4.28 (m, 1H), 4.18-4.09 (m, 1H), 4.07-3.90 (m, 4H), 3.88-3.78 (m, 1H), 3.21 (br dd, J=3.2, 13.6 Hz, 2H), 3.16-3.05 (m, 2H), 3.03-2.90 (m, 2H), 2.82-2.55 (m, 4H), 2.48 (s, 3H), 2.33-2.22 (m, 1H), 2.11-2.00 (m, 1H), 1.91-1.62 (m, 4H), 1.51 (s, 9H).

Step H: tert-butyl 2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate: To a solution of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (150 mg, 318 umol), 1-bromonaphthalene (98.8 mg, 477 umol, 66.3 uL), $Cs_2CO_3$ (311 mg, 954 umol), and RuPhos (29.7 mg, 63.6 umol) in toluene (3 mL) was added $Pd_2(dba)_3$ (29.1 mg, 31.8 umol) and the suspension was degassed under vacuum and purged with $N_2$ 3 times. The reaction mixture was stirred at 100° C. for 12 hours. The mixture was partitioned between water (10 mL) and EtOAc (20 mL) and the layers separated. The aqueous layer was extracted subsequently with EtOAc (3×20 mL). The combined organics were washed with brine (20 mL), dried over anhydrous $Na_2SO_4$, filtered and concentrated under reduced pressure. The residue was purified by reverse flash to give tert-butyl 2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (70 mg, 111 umol, 35.0% yield, 95.0% purity) as brown solid. ES+APCI MS m/z 598.6 [M+H]+. $^1$H NMR (400 MHz, chloroform-d) δ=8.21-8.20 (m, 1H), 7.87-7.85 (m, 1H), 7.61-7.59 (d, J=8.0 Hz, 1H), 7.51-7.49 (m, 2H), 7.45-7.41 (t, J=7.6 Hz, 1H), 7.15-7.13 (d, J=7.2 Hz, 1H), 4.63 (br s, 1H), 4.46 (br s, 1H), 4.33-4.28 (m, 4H), 4.10-4.07 (m, 2H), 3.97-3.94 (br d, J=11.6 Hz, 1H), 3.46 (br s, 1H), 3.31-3.27 (br d, J=14.0 Hz, 1H), 3.07-3.01 (m, 2H), 2.77 (br s, 3H), 2.55 (br s, 3H), 2.35 (br s, 1H), 1.82 (br s, 7H), 1.52 (s, 9H).

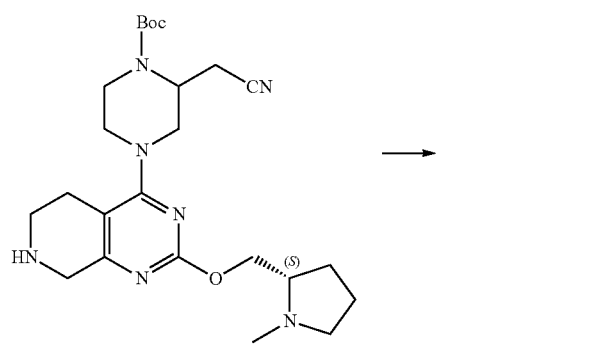

437

-continued

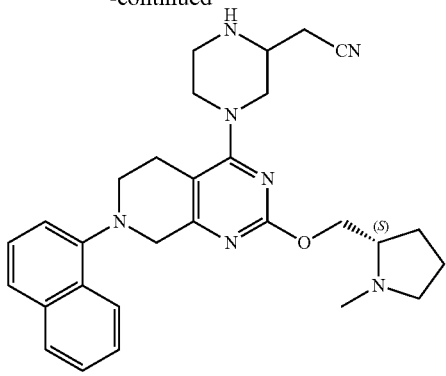

Step I: 2-[4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile: To a solution of tert-butyl 2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (60 mg, 100 umol) in DCM (0.1 mL) was added TFA (154 mg, 1.35 mmol, 0.1 mL) at 15° C. and stirred at 15° C. for 1 hour. The reaction mixture was concentrated under vacuum to give 2-[4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (50 mg) as brown oil.

Step J: 2-[4-[2-[[(2S)-1-methylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile: To a solution of 2-[4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (50 mg, 81.8 umol, TFA) and DIEA (106 mg, 817 umol, 142 uL) in DCM (0.2 mL) was added prop-2-enoyl prop-2-enoate (11.3 mg, 89.9 umol) at 0° C. and the reaction stirred at 0-15° C. for 1.5 hour. The reaction mixture was concentrated under vacuum. The residue was purified by prep-HPLC (column: Phenomenex Synergi C18 150*30 mm*4 um; mobile phase: [water (0.225% Formic Acid)-ACN]; B %: 15%-45%,10.5 min) to give 2-[4-[2-[[(2S)-1-methylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (9.16 mg, 15.1 umol, 18.5% yield, 98.7% purity, Formate) as yellow oil. ES+APCI MS m/z 552.5 [M+H]+. $^1$H NMR (400 MHz, chloroform-d) δ=8.45 (br s, 1H), 8.22-8.19 (m, 1H), 7.87-7.85 (m, 1H), 7.62-7.60 (d, J=8.0 Hz, 1H), 7.51-7.49 (m, 2H), 7.45-7.43 (t, J=7.6 Hz, 1H), 7.15-7.13 (d, J=7.2 Hz, 1H), 6.60 (br s, 1H), 6.42-6.38 (m, 1H), 5.84-5.82 (br d, J=10.8 Hz, 1H), 5.08 (br s, 1H), 4.78-4.53 (br dd, J=6.8, 11.6 Hz, 2H), 4.42-4.40 (m, 1H), 4.27 (br s, 2H), 4.21-4.18 (br d, J=14.0 Hz, 1H), 4.12-3.78 (br d, J=12.8 Hz, 2H), 3.68-3.07 (m, 7H), 3.05-2.84 (m, 3H), 2.77 (d, J=1.6 Hz, 3H), 2.71-2.64 (m, 1H), 2.26-2.17 (m, 1H), 2.11-2.03 (m, 1H), 2.02-1.88 (m, 2H).

Example 148

2-[4-[7-(5-methyl-1H-indazol-4-yl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

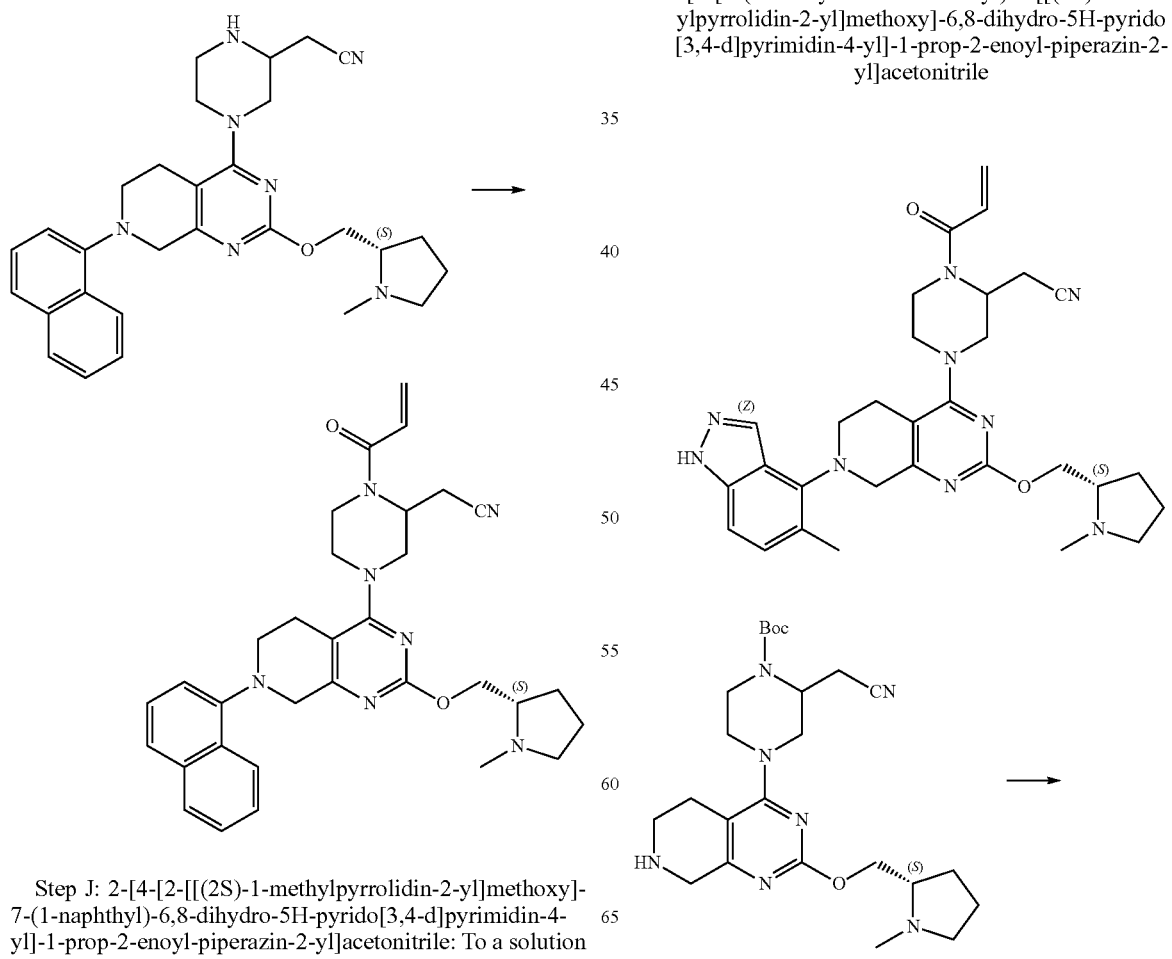

-continued

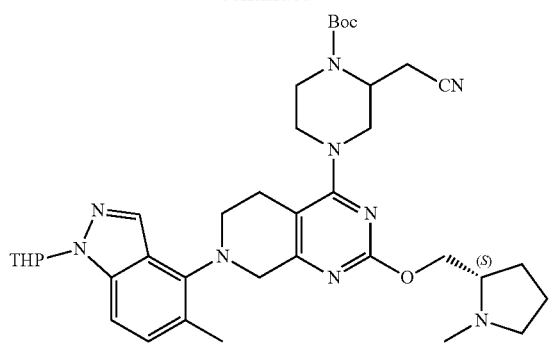

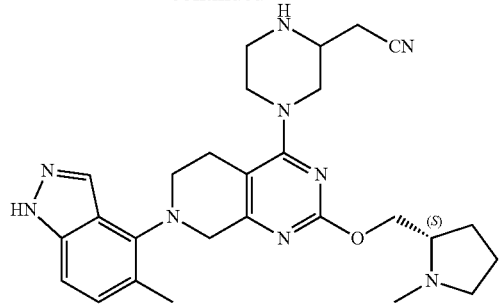

Step A: tert-butyl 2-(cyanomethyl)-4-[2-[[(2S)-1-methyl-pyrrolidin-2-yl]methoxy]-7-(5-methyl-1-tetrahydropyran-2-yl-indazol-4-yl)-6,8-dihydro-5H-pyrido[3,4-d]pyrimidin-4-yl]piperazine-1-carboxylate: To a solution of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (200 mg, 424 umol), 4-bromo-5-methyl-1-tetrahydropyran-2-yl-indazole (188 mg, 636 umol), RuPhos (39.6 mg, 84.8 umol) and Cs$_2$CO$_3$ (414 mg, 1.27 mmol) in toluene (6 mL) was added Pd$_2$(dba)$_3$ (38.8 mg, 42.4 umol) and the reaction stirred at 100° C. for 12 hours under N$_2$. Upon completion, the mixture was purified directly by silica gel chromatography (PE:EtOAc=3:1 to 0:1) to give tert-butyl 2-(cyanomethyl)-4-[2-[[(2S)-1-methylpyrrolidin-2-yl]methoxy]-7-(5-methyl-1-tetrahydropyran-2-yl-indazol-4-yl)-6,8-dihydro-5H-pyrido[3,4-d]pyrimidin-4-yl]piperazine-1-carboxylate (120 mg, 149 umol, 35.1% yield, 85.0% purity) as a brown solid. ES+APCI MS m/z 686.6 [M+H]$^+$. $^1$H NMR (400 MHz, CHLOROFORM-d) δ=8.04 (d, J=2.0 Hz, 1H), 7.33-7.29 (m, 2H), 5.70 (dd, J=2.4, 9.2 Hz, 1H), 4.62 (br s, 1H), 4.39 (br s, 1H), 4.34-4.28 (m, 2H), 4.20-4.14 (m, 1H), 4.05 (br d, J=12.0 Hz, 2H), 3.91 (br d, J=12.4 Hz, 1H), 3.81-3.72 (m, 1H), 3.53 (br t, J=4.8 Hz, 2H), 3.27 (br d, J=10.8 Hz, 2H), 3.10 (br d, J=6.8 Hz, 1H), 3.06-2.96 (m, 1H), 2.90-2.65 (m, 5H), 2.59 (br d, J=10.2 Hz, 1H), 2.50 (s, 3H), 2.43 (s, 3H), 2.35-2.26 (m, 1H), 2.23-2.15 (m, 1H), 2.11 (br s, 2H), 1.90-1.65 (m, 7H), 1.54 (s, 9H).

Step B: 2-[4-[7-(5-methyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile: To a solution of tert-butyl 2-(cyanomethyl)-4-[2-[[(2S)-1-methylpyrrolidin-2-yl]methoxy]-7-(5-methyl-1-tetrahydropyran-2-yl-indazol-4-yl)-6,8-dihydro-5H-pyrido[3,4-d]pyrimidin-4-yl]piperazine-1-carboxylate (150 mg, 219 umol) in DCM (0.2 mL) was added TFA (616 mg, 5.40 mmol, 0.4 mL) and the reaction mixture stirred at 15° C. for 12 hours. Upon completion, the solvent was removed under vacuum to give 2-[4-[7-(5-methyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile (159 mg, 218 umol, 99.6% yield, 2TFA) as a red oil.

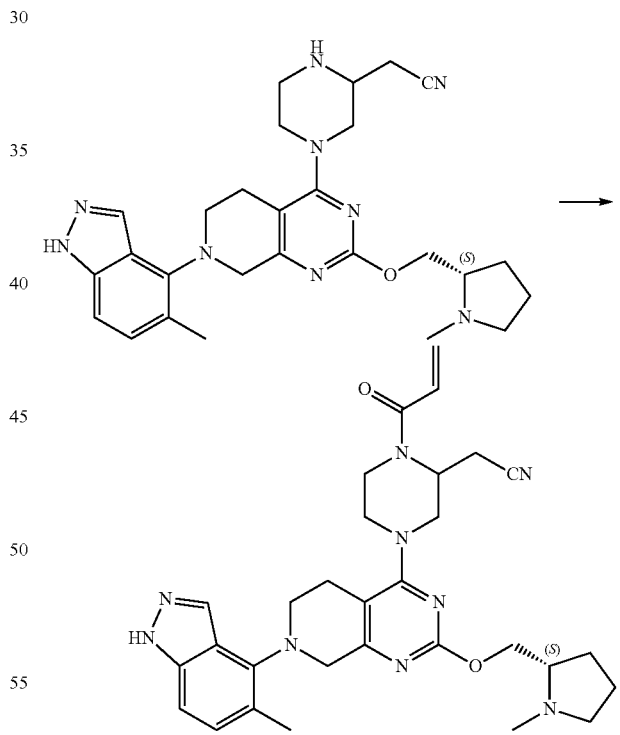

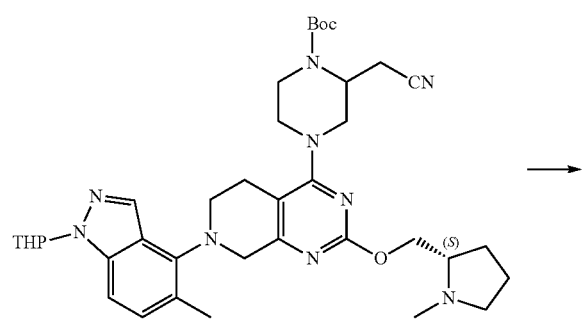

Step C: 2-[4-[7-(5-methyl-1H-indazol-4-yl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile: To a solution of 2-[4-[7-(5-methyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile (159 mg, 218 umol, 2TFA) and DIEA (366 mg, 2.83 mmol, 493 uL) in DCM (4 mL) at −40° C. was added prop-2-enoyl prop-2-enoate (24.7 mg, 196 umol) and the reaction mixture was stirred at −20° C. for 1 hour. Upon completion, the reaction mixture was quenched by addition of water (2 mL) and the aqueous layer separated and back extracted with DCM (2×10 mL). The combined organics were concentrated under vacuum and the residue purified by silica gel chromatography (DCM:MeOH=50:1 to 5:1) followed by purification by reverse prep HPCL (column: Phenomenex Synergi C18 150*25*10 um; mobile phase: [water (0.225% Formic Acid)-ACN]; B %: 4%-34% over 10 minutes) to give 2-[4-[7-(5-methyl-1H-indazol-4-yl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (1.77 mg, 3.10 umol). ES+APCI MS m/z 556.5 [M+H]+. 1H NMR (400 MHz, CHLOROFORM-d) δ=8.00 (s, 1H), 7.18 (br s, 1H), 7.16-7.11 (m, 1H), 6.52 (br s, 1H), 6.37-6.21 (m, 1H), 5.75 (br d, J=10.4 Hz, 1H), 4.99 (br s, 1H), 4.67 (br dd, J=6.4, 11.6 Hz, 1H), 4.34 (br dd, J=3.9, 11.6 Hz, 1H), 4.24 (s, 2H), 4.11 (br d, J=12.8 Hz, 1H), 3.94 (br s, 1H), 3.57-3.40 (m, 4H), 3.29 (br d, J=13.8 Hz, 1H), 3.19 (br s, 1H), 3.02 (br dd, J=12.4, 19.7 Hz, 2H), 2.87 (br dd, J=8.4, 16.4 Hz, 2H), 2.76-2.58 (m, 6H), 2.35 (s, 3H), 2.22-2.10 (m, 1H), 2.01 (br d, J=8.4 Hz, 1H), 1.89 (br s, 2H).

Example 149

2-[4-[2-[[(2S)-1-methylpyrrolidin-2-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile

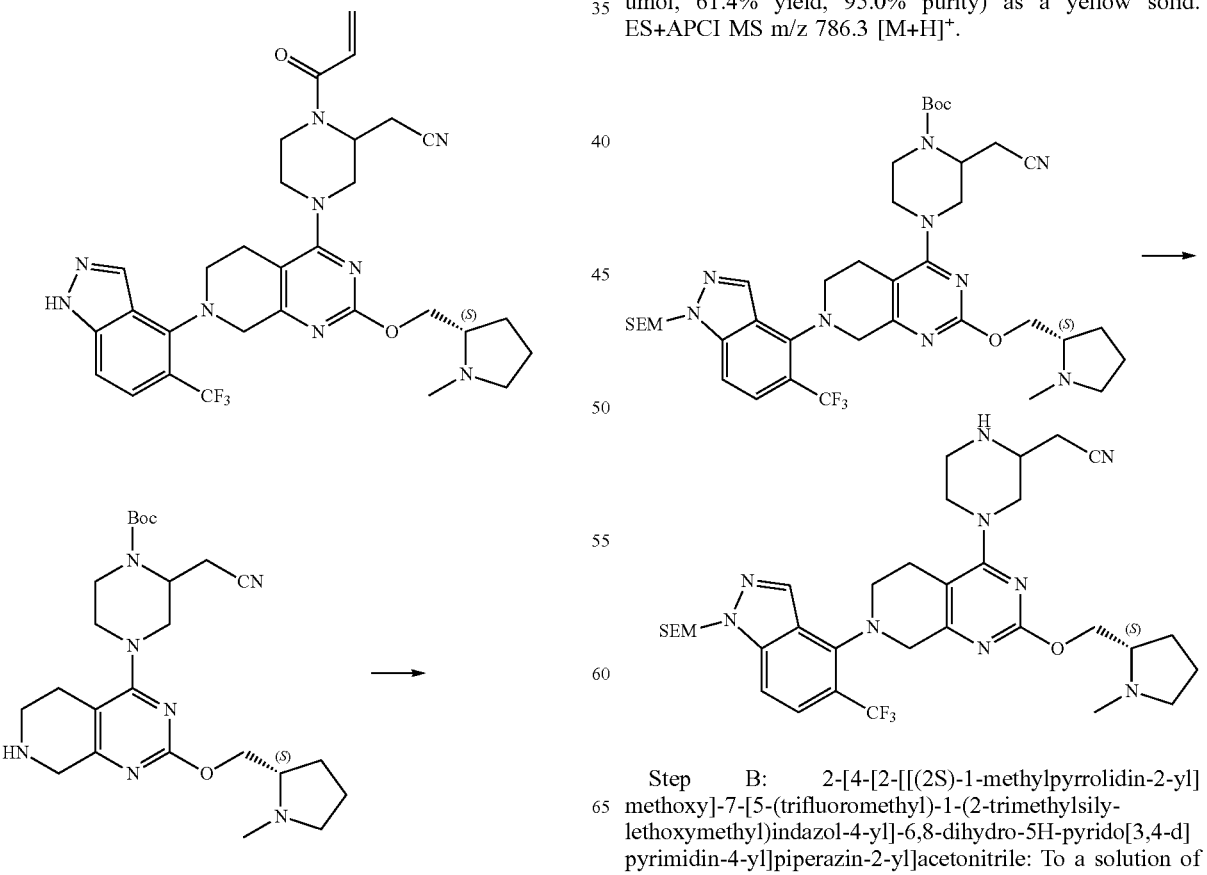

Step A: tert-butyl 2-(cyanomethyl)-4-[2-[[(2S)-1-methylpyrrolidin-2-yl] methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate: tert-butyl 2-(cyanomethyl)-4-[2-[[(2S)-1-methylpyrrolidin-2-yl] methoxy]-5,6,7,8-tetrahydropyrido[3,4-d]pyrimidin-4-yl] piperazine-1-carboxylate (130 mg, 276 umol), 2-[[4-bromo-5-(trifluoromethyl)indazol-1-yl]methoxy]ethyl-trimethyl-silane (120 mg, 303 umol), Pd2(dba)3 (50.5 mg, 55.1 umol), RuPhos (51.5 mg, 110 umol), Cs2CO3 (225 mg, 689 umol) in toluene (3.00 mL) was de-gassed with N2 and then heated to 90° C. for 12 hours under N2. Upon completion, the mixture was filtered and the filtrate was concentrated. The residue was purified by prep-TLC (EtOAc/MeOH 8/1) to give tert-butyl 2-(cyanomethyl)-4-[2-[[(2S)-1-methylpyrrolidin-2-yl] methoxy]-7-[5-(trifluoromethyl)-1-(2-trimethylsilylethoxymethyl)indazol-4-yl]-6,8-dihydro-5H-pyrido[3, 4-d]pyrimidin-4-yl]piperazine-1-carboxylate (140 mg, 169 umol, 61.4% yield, 95.0% purity) as a yellow solid. ES+APCI MS m/z 786.3 [M+H]+.

Step B: 2-[4-[2-[[(2S)-1-methylpyrrolidin-2-yl] methoxy]-7-[5-(trifluoromethyl)-1-(2-trimethylsilylethoxymethyl)indazol-4-yl]-6,8-dihydro-5H-pyrido[3,4-d] pyrimidin-4-yl]piperazin-2-yl]acetonitrile: To a solution of tert-butyl 2-(cyanomethyl)-4-[2-[[(2S)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (140 mg, 178 umol) in DCM (3.00 mL) was added 2,6-dimethylpyridine (229 mg, 2.14 mmol) and TMSOTf (238 mg, 1.07 mmol) at 0° C. The mixture was stirred at 15° C. for 2 hours. Upon completion, the mixture was quenched by addition of MeOH (0.5 mL) and concentrated under vacuum to give 2-[4-[2-[[(2S)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazin-2-yl]acetonitrile (200 mg, crude) as a yellow oil which was used directly in the next step without further purification. ES+APCI MS m/z 686.6 [M+H]⁺.

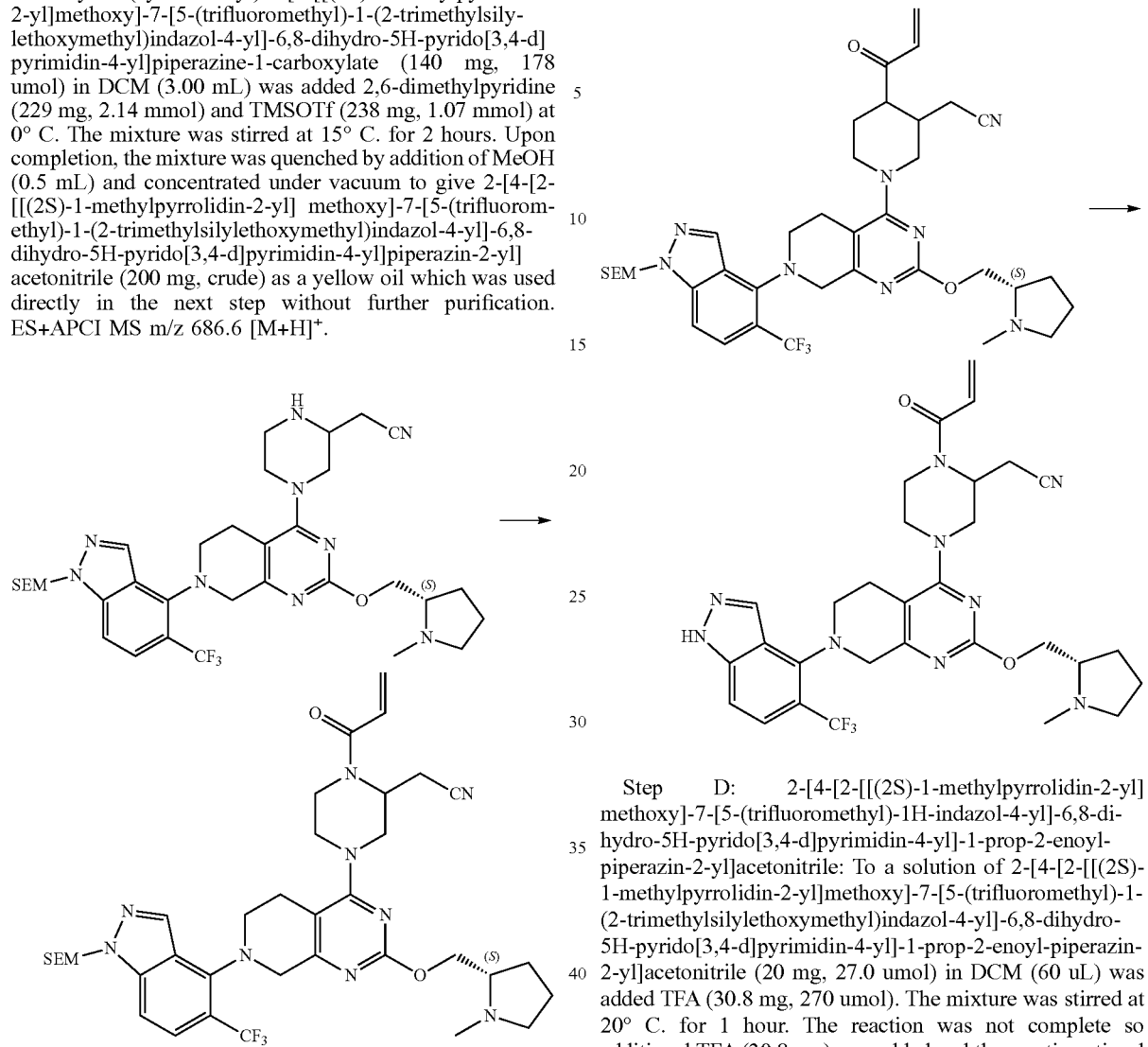

Step C: 2-[4-[2-[[(2S)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile: To a solution of 2-[4-[2-[[(2S)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazin-2-yl]acetonitrile (122 mg, 178 umol) and DIEA (138 mg, 1.07 mmol, 186 uL) in DCM (3.00 mL) was added prop-2-enoyl prop-2-enoate (18.0 mg, 143 umol) dropwise at 0° C. The mixture was stirred at 20° C. for 1.5 hours. Upon completion, the mixture was diluted with water (0.5 mL) and extracted with EtOAc (2×5 mL). The organic layers were dried over Na₂SO₄ and concentrated under vacuum. The residue was purified by prep-TLC (EA/MeOH 10/1) and prep-HPLC (column: Boston pH-lex 150*25 10 um; mobile phase: [water (0.1% TFA)-ACN]; B %: 39%-69%,10 min) to give 2-[4-[2-[[(2S)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile (54.0 mg, 43.8 umol). ES+APCI MS m/z 740.6 [M+H]⁺.

Step D: 2-[4-[2-[[(2S)-1-methylpyrrolidin-2-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile: To a solution of 2-[4-[2-[[(2S)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile (20 mg, 27.0 umol) in DCM (60 uL) was added TFA (30.8 mg, 270 umol). The mixture was stirred at 20° C. for 1 hour. The reaction was not complete so additional TFA (30.8 mg) was added and the reaction stirred at 20° C. for an additional 0.5 hour. Upon completion, the pH or the mixture was adjusted to 8 by addition of saturated aqueous NaHCO₃ (1 mL) and the aqueous layer extracted with EtOAc (2×5 mL). The combined organics were washed with brine (3 mL), dried over Na₂SO₄ and concentrated under vacuum. The residue was diluted with MeOH (0.5 mL) and NH₃.H₂O (0.5 mL) added and the mixture stirred at 20° C. for 0.5 hour. The mixture was purified by prep-HPLC (column: Phenomenex Synergi C18 150*30 mm*4 um; mobile phase: [water (0.225% Formic Acid)-ACN]; B %: 15%-45%,10.5 min) to give 2-[4-[2-[[(2S)-1-methylpyrrolidin-2-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile (2.68 mg, 3.99 umol) as a white solid. ES+APCI MS m/z 610.5 [M+H]⁺. ¹H NMR (400 MHz, chloroform-d) δ=8.22 (s, 1H), 7.68 (d, J=9.2 Hz, 1H), 7.45 (d, J=8.8 Hz, 1H), 6.60 (br s, 1H), 6.45-6.35 (m, 1H), 5.84 (br d, J=11.2 Hz, 1H), 5.09 (br s, 1H), 4.71-4.60 (m, 1H), 4.42-4.27 (m, 3H), 4.17 (br d, J=11.2 Hz, 1H), 4.01 (br d, J=12.4 Hz, 2H), 3.78-3.31 (m, 5H), 3.23-3.03 (m, 2H), 3.02-2.75 (m, 4H), 2.71 (s, 3H), 2.66-2.57 (m, 1H), 2.27-2.12 (m, 1H), 2.10-2.03 (m, 3H). ES+APCI MS m/z 610.1 [M+H]⁺.

Example 150

2-(1-acryloyl-4-(2-(((R)-1-(dimethylamino)propan-2-yl)oxy)-7-(3-hydroxynaphthalen-1-yl)-5,6,7,8-tetrahydropyrido[3,4-d]pyrimidin-4-yl)piperazin-2-yl)acetonitrile

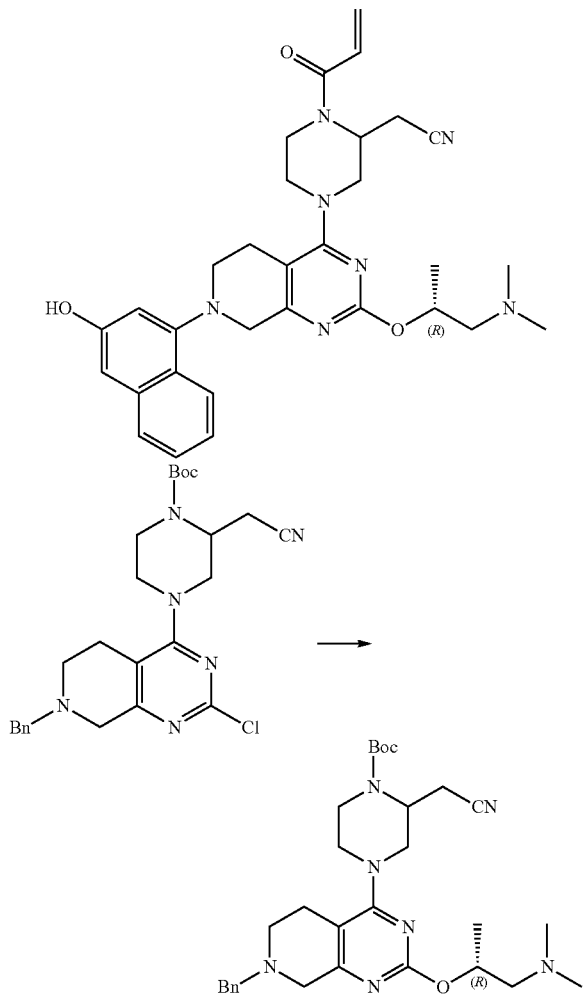

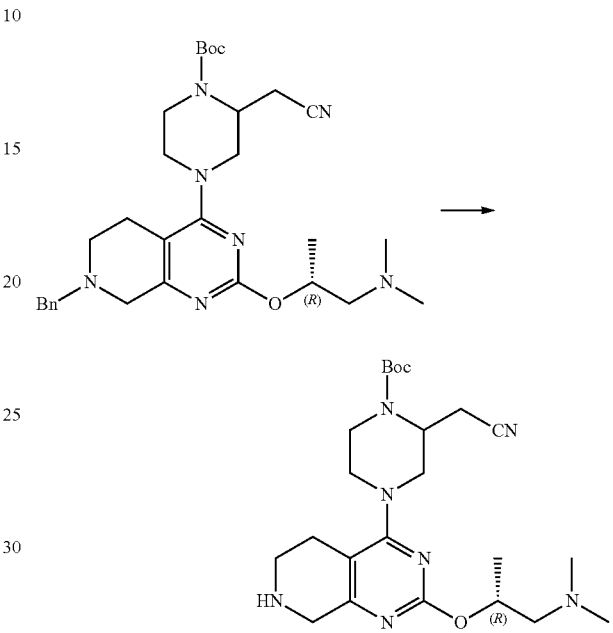

Step A: tert-Butyl 4-[7-benzyl-2-[(1R)-2-(dimethylamino)-1-methyl-ethoxy]-6,8-dihydro-5H-pyrido[3,4-d]pyrimidin-4-yl]-2-(cyanomethyl)piperazine-1-carboxylate: To a mixture of tert-butyl 4-(7-benzyl-2-chloro-6,8-dihydro-5H-pyrido[3,4-d]pyrimidin-4-yl)-2-(cyanomethyl)piperazine-1-carboxylate (500 mg, 1.04 mmol), (2R)-1-(dimethylamino)propan-2-ol (214 mg, 2.07 mmol and sodium tert-butoxide (298 mg, 3.11 mmol) in toluene (20 mL) was added BINAP (129 mg, 207 umol) and Pd$_2$(dba)$_3$ (94.8 mg, 104 umol) and the mixture was sparged with nitrogen followed by stirring at 90° C. for 5 hr. The mixture was diluted with ethyl acetate (100 mL) and water (100 mL) and the organic layer was separated and dried over sodium sulfate, filtered and concentrated under vacuum. The residue was purified by reversed phase flash chromatogaphy [water (0.1% Formic Acid water)/acetonitrile]. The desired fractions were collected and neutralized with saturated aqueous sodium carbonate solution (5 mL) and extracted with 10% MeOH/DCM (2×50 mL). The combined organics were dried over sodium sulfate, filtered and concentrated under vacuum to give tert-Butyl 4-[7-benzyl-2-[(1R)-2-(dimethylamino)-1-methyl-ethoxy]-6,8-dihydro-5H-pyrido[3,4-d]pyrimidin-4-yl]-2-(cyanomethyl)piperazine-1-carboxylate (300 mg, 480 umol) ES+APCI MS m/z 550.4 [M+H]$^+$.

Step B: tert-butyl 2-(cyanomethyl)-4-[2-[(1R)-2-(dimethylamino)-1-methyl-ethoxy]-5,6,7,8-tetrahydropyrido[3,4-d]pyrimidin-4-yl]piperazine-1-carboxylate: To a solution of tert-butyl 4-[7-benzyl-2-[(1R)-2-(dimethylamino)-1-methyl-ethoxy]-6,8-dihydro-5H-pyrido[3,4-d]pyrimidin-4-yl]-2-(cyanomethyl)piperazine-1-carboxylate (1.1 g, 2.00 mmol) in MeOH (10 mL) was added a solution of NH$_3$ (792 mg, 46.5 mmol) in MeOH (3.96 g, 123.56 mmol, 5 mL), followed by 10% Pd/C (500 mg). The mixture was stirred at 40° C. for 12 hr under H$_2$ (15 psi). The reaction was filtered and the filtrate was concentrated under reduced pressure to dryness to give tert-butyl 2-(cyanomethyl)-4-[2-[(1R)-2-(dimethylamino)-1-methyl-ethoxy]-5,6,7,8-tetrahydropyrido[3,4-d]pyrimidin-4-yl]piperazine-1-carboxylate (756 mg, crude) was obtained as a yellow solid. ES+APCI MS m/z 460.3 [M+H]$^+$.

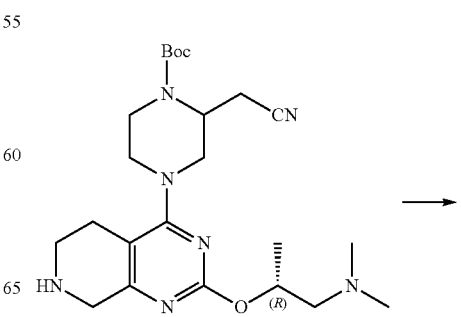

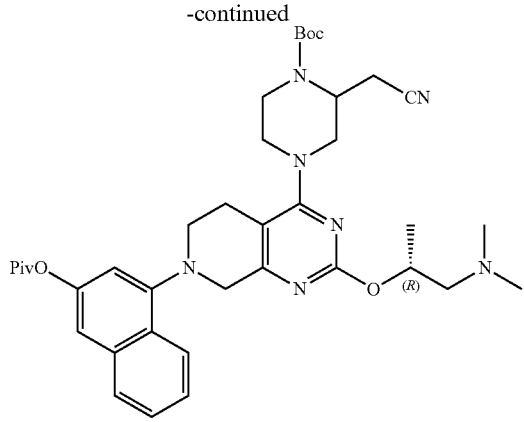

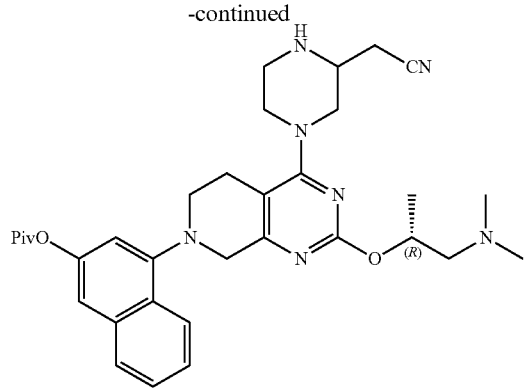

Step C: tert-butyl 2-(cyanomethyl)-4-[2-[(1R)-2-(dimethylamino)-1-methyl-ethoxy]-7-[3-(2,2-dimethylpropanoyloxy)-1-naphthyl]-6,8-dihydro-5H-pyrido[3,4-d]pyrimidin-4-yl]piperazine-1-carboxylate: A mixture of (4-bromo-2-naphthyl) 2,2-dimethylpropanoate (304 mg, 990 umol), tert-butyl 2-(cyanomethyl)-4-[2-[(1R)-2-(dimethylamino)-1-methyl-ethoxy]-5,6,7,8-tetrahydropyrido[3,4-d]pyrimidin-4-yl]piperazine-1-carboxylate (350 mg, 761 umol), [2-(2-aminoethyl)phenyl]-chloro-palladium, dicyclohexyl-[2-(2,4,6-triisopropylphenyl)phenyl]phosphane (84.4 mg, 114 umol) and Cs₂CO₃ (620 mg, 1.90 mmol in toluene (10 mL) was purged with N₂ 3 times and the mixture stirred at 70° C. for 16 hours under N₂ atmosphere. The reaction mixture was poured into H₂O (50 mL) and extracted with ethyl acetate (50 mL×3). The combined organics were washed with brine (30 mL), dried over anhydrous Na₂SO₄ and concentrated under vacuum to give a residue. The residue was purified by reversed phase flash [water (0.1% formic acid)/acetonitrile] to give tert-butyl 2-(cyanomethyl)-4-[2-[(1R)-2-(dimethylamino)-1-methyl-ethoxy]-7-[3-(2,2-dimethylpropanoyloxy)-1-naphthyl]-6,8-dihydro-5H-pyrido[3,4-d]pyrimidin-4-yl]piperazine-1-carboxylate (210 mg, 303 umol). ES+APCI MS m/z 686.4 [M+H]⁺.

Step D: [4-[4-[3-(cyanomethyl)piperazin-1-yl]-2-[(1R)-2-(dimethylamino)-1-methyl-ethoxy]-6,8-dihydro-5H-pyrido[3,4-d]pyrimidin-7-yl]-2-naphthyl] 2,2-dimethylpropanoate: To a solution of tert-butyl 2-(cyanomethyl)-4-[2-[(1R)-2-(dimethylamino)-1-methyl-ethoxy]-7-[3-(2,2-dimethylpropanoyloxy)-1-naphthyl]-6,8-dihydro-5H-pyrido[3,4-d]pyrimidin-4-yl]piperazine-1-carboxylate (210 mg, 306 umol) in dichloromethane (300 uL) was added TFA (523 mg, 4.59 mmol, 340 uL) and the mixture stirred at 15° C. for 2 hours. The mixture was concentrated under vacuum to give [4-[4-[3-(cyanomethyl)piperazin-1-yl]-2-[(1R)-2-(dimethylamino)-1-methyl-ethoxy]-6,8-dihydro-5H-pyrido[3,4-d]pyrimidin-7-yl]-2-naphthyl] 2,2-dimethylpropanoate (214 mg, 305 umol). ES+APCI MS m/z 586.4 [M+H]⁺.

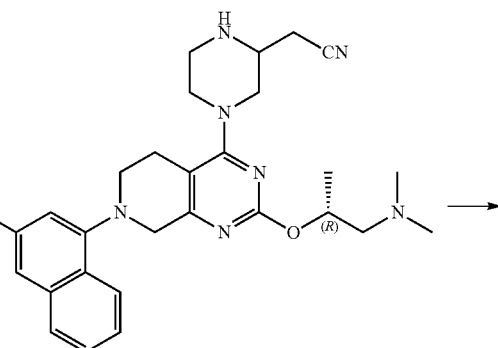

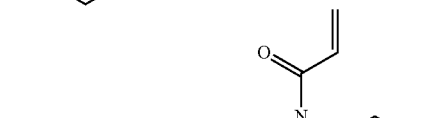

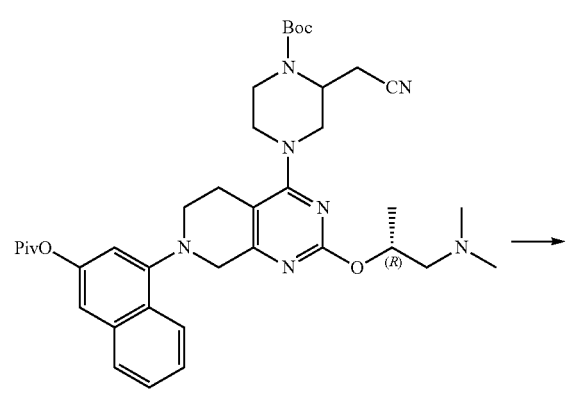

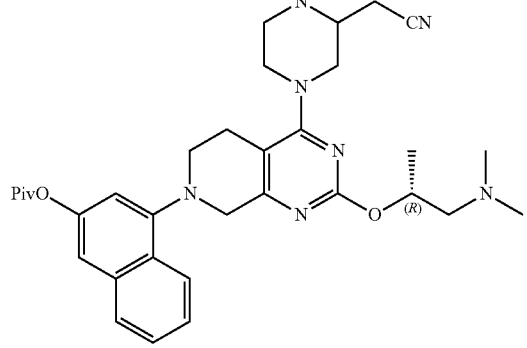

Step E: [4-[4-[3-(cyanomethyl)-4-prop-2-enoyl-piperazin-1-yl]-2-[(1R)-2-(dimethylamino)-1-methyl-ethoxy]-6,8-dihydro-5H-pyrido[3,4-d]pyrimidin-7-yl]-2-naphthyl]

2,2-dimethylpropanoate: To a mixture of [4-[4-[3-(cyanomethyl)piperazin-1-yl]-2-[(1R)-2-(dimethylamino)-1-methylethoxy]-6,8-dihydro-5H-pyrido[3,4-d]pyrimidin-7-yl]-2-naphthyl] 2,2-dimethylpropanoate (214 mg, 305 umol, TFA) and DIEA (395 mg, 3.06 mmol, 532 uL) in dichloromethane (5.00 mL) cooled to −40° C. was added a solution of prop-2-enoyl prop-2-enoate (38.6 mg, 305 umol) in dichloromethane (1.00 mL) under nitrogen atmosphere. The mixture was warmed up to 0° C. and stirred for 1 hour. The mixture was concentrated under vacuum to give a residue. The residue was purified by reversed phase flash [water (0.1% trifluoroacetic acid)\acetonitrile] to give [4-[4-[3-(cyanomethyl)-4-prop-2-enoyl-piperazin-1-yl]-2-[(1R)-2-(dimethylamino)-1-methyl-ethoxy]-6,8-dihydro-5H-pyrido[3,4-d]pyrimidin-7-yl]-2-naphthyl] 2,2-dimethylpropanoate (100 mg, 156 umol). ES+APCI MS m/z 640.7 [M+H]+.

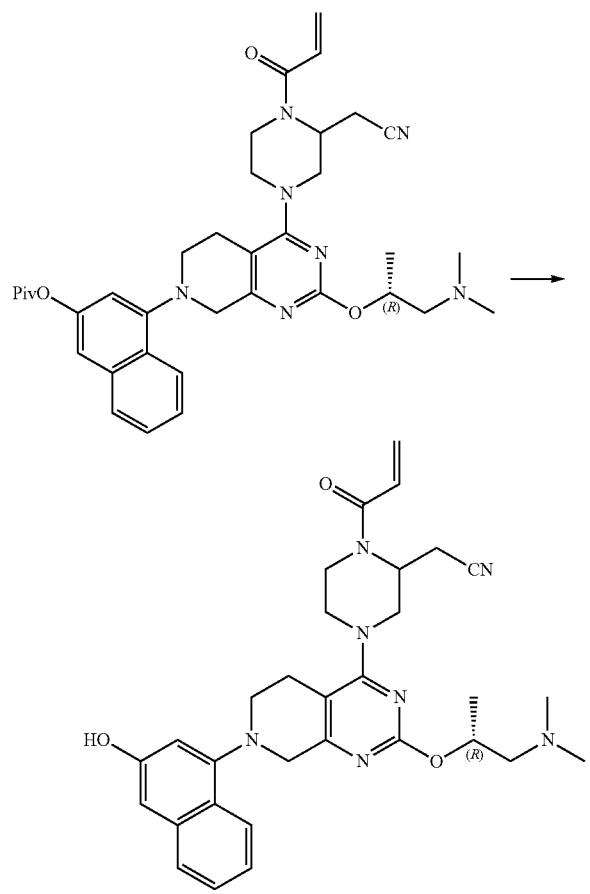

Step F: 2-[4-[2-[(1R)-2-(dimethylamino)-1-methylethoxy]-7-(3-hydroxy-1-naphthyl)-6,8-dihydro-5H-pyrido[3,4-d]pyrimidin-4-yl]-1-prop-2-enoyl-piperazin-2-yl]acetonitrile: To a solution of [4-[4-[3-(cyanomethyl)-4-prop-2-enoyl-piperazin-1-yl]-2-[(1R)-2-(dimethylamino)-1-methyl-ethoxy]-6,8-dihydro-5H-pyrido[3,4-d]pyrimidin-7-yl]-2-naphthyl] 2,2-dimethylpropanoate (90 mg, 141 umol) in THF (500 uL) cooled to 0° C. was added NaOH (2 M, 281.34 uL) and the mixture stirred at 15° C. for 16 hours. The pH of the mixture was adjusted to 7 by addition of a 20% with formic acid solution. The aqueous solution was next extracted with dichloromethane (3×10 mL). The combined organics were dried over Na$_2$SO$_4$, filtered and concentrated under vacuum. The residue was purified by prep-HPLC (column: Phenomenex Synergi C18 150*25*10 um; mobile phase: [water (0.225% Formic Acid)-ACN]; B %: 7%-37%, 10 min) to give 2-[4-[2-[(1R)-2-(dimethylamino)-1-methyl-ethoxy]-7-(3-hydroxy-1-naphthyl)-6,8-dihydro-5H-pyrido[3,4-d]pyrimidin-4-yl]-1-prop-2-enoyl-piperazin-2-yl]acetonitrile (5 mg, 8.82 umol, 6.27% yield, 98% purity) ES+APCI MS m/z 556.3 [M+H]+. $^1$H NMR (400 MHz, methanol-d$_4$) δ=8.54 (br s, 0.6H), 8.07 (d, J=8.4 Hz, 1H), 7.63 (d, J=8.4 Hz, 1H), 7.37 (t, J=7.2 Hz, 1H), 7.30-7.21 (m, 1H), 6.91-6.72 (m, 3H), 6.29 (br d, J=16.4 Hz, 1H), 5.84 (br d, J=11.2 Hz, 1H), 5.48 (br s, 1H), 5.26-4.96 (m, 1H), 4.57 (br s, 1H), 4.24-4.09 (m, 4H), 3.74-3.54 (m, 1H), 3.48 (m, 2H), 3.22 (m, 2H), 3.10-2.86 (m, 5H), 2.78 (br d, J=14.4 Hz, 1H), 2.53 (br s, 6H), 1.37 (dd, J=2.0, 6.4 Hz, 3H).

Example 151

2-(1-acryloyl-4-(2-(((R)-1-(dimethylamino)propan-2-yl)oxy)-7-(naphthalen-1-yl)-5,6,7,8-tetrahydropyrido[3,4-d]pyrimidin-4-yl)piperazin-2-yl)acetonitrile

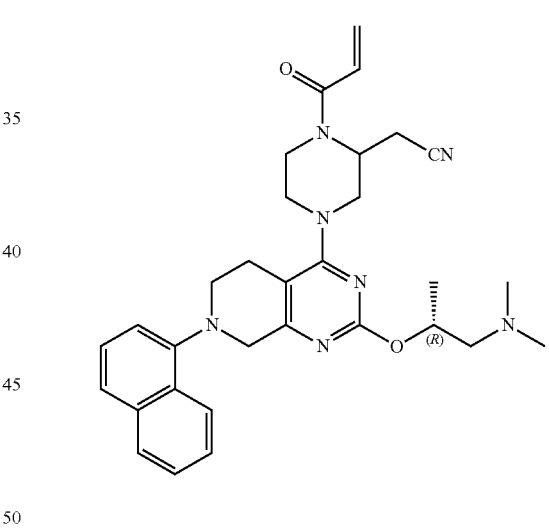

(2-(1-acryloyl-4-(2-(((R)-1-(dimethylamino)propan-2-yl)oxy)-7-(naphthalen-1-yl)-5,6,7,8-tetrahydropyrido[3,4-d]pyrimidin-4-yl)piperazin-2-yl)acetonitrile was prepared following Example 150 substituting 1-bromonaphthalene for (4-bromo-2-naphthyl) 2,2-dimethylpropanoate in Step C and omitting Step F. ES+APCI MS m/z 540.3 [M+H]+. $^1$H NMR (400 MHz, methanol-d$_4$) δ=8.51 (s, 1H), 8.26-8.19 (m, 1H), 7.90-7.84 (m, 1H), 7.62 (d, J=8.0 Hz, 1H), 7.53-7.47 (m, 2H), 7.46-7.39 (m, 1H), 7.25-7.18 (m, 1H), 6.82 (br s, 1H), 6.30 (br d, J=17.2 Hz, 1H), 5.84 (br d, J=10.4 Hz, 1H), 5.62-5.53 (m, 1H), 5.08 (br s, 1H), 4.70-4.39 (m, 1H), 4.26-4.11 (m, 4H), 3.94-3.59 (m, 1H), 3.48-3.34 (m, 2H), 3.28-3.18 (m, 3H), 3.13-2.92 (s, 5H), 2.79-2.61 (s, 6H), 1.48 (dd, J=2.0, 6.0 Hz, 3H).

Example 152

2-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]-1-prop-2-enoyl-piperazin-2-yl]acetonitrile

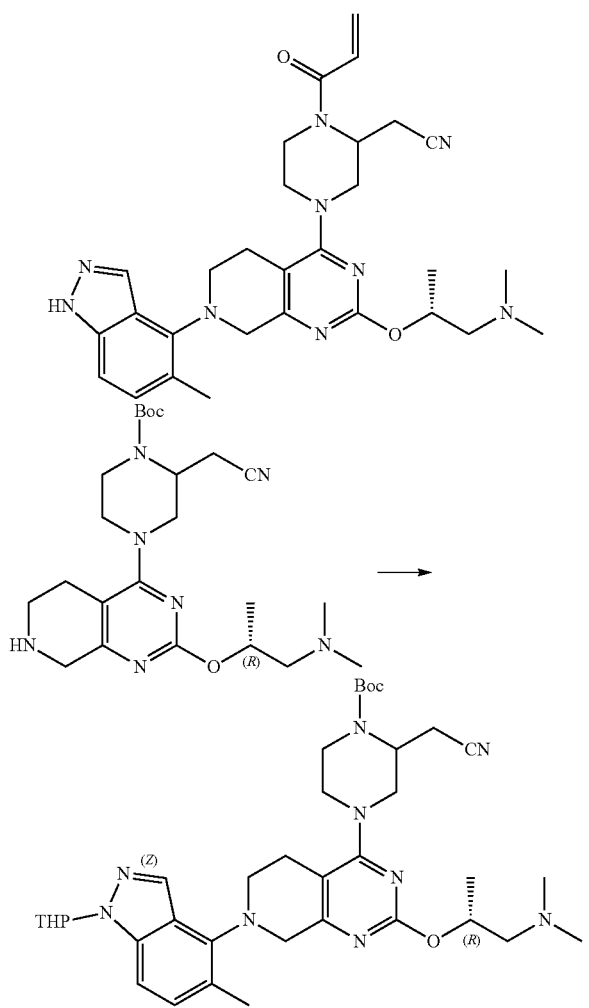

Step A: tert-butyl 2-(cyanomethyl)-4-[2-[(1R)-2-(dimethylamino)-1-methyl-ethoxy]-7-(5-methyl-1-tetrahydropyran-2-yl-indazol-4-yl)-6,8-dihydro-5H-pyrido [3,4-d]pyrimidin-4-yl]piperazine-1-carboxylate: A mixture of tert-butyl 2-(cyanomethyl)-4-[2-[(1R)-2-(dimethylamino)-1-methyl-ethoxy]-5,6,7,8-tetrahydropyrido[3,4-d]pyrimidin-4-yl]piperazine-1-carboxylate (0.50 g, 1.09 mmol), 4-bromo-5-methyl-1-tetrahydropyran-2-yl-indazole (482 mg, 1.63 mmol), t-BuONa (314 mg, 3.26 mmol) and [2-(2-aminoethyl)phenyl]-chloro-palladium; dicyclohexyl-[2-(2,4,6-triisopropylphenyl)phenyl]phosphane (80.4 mg, 109 umol) in toluene (30 mL) was stirred at 70° C. for 10 hours. The mixture was diluted with water (10 mL) and the aqueous layer extracted with ethyl acetate (3×20 mL). The organic layers were washed with saturated sodium chloride solution (30 mL), dried over Na$_2$SO$_4$, filtered and concentrated under vacuum. The residue was purified by reverse phase flash [water (Formic Acid, 0.1%.)/acetonitrile] to give tert-butyl 2-(cyanomethyl)-4-[2-[(1R)-2-(dimethylamino)-1-methyl-ethoxy]-7-(5-methyl-1-tetrahydropyran-2-yl-indazol-4-yl)-6,8-dihydro-5H-pyrido[3,4-d]pyrimidin-4-yl]piperazine-1-carboxylate (0.40 g, 522 umol, 48.0% yield) as a yellow solid. ES+APCI MS m/z 674.3 [M+H]$^+$. $^1$H NMR (400 MHz, chloroform-d) δ=8.03 (d, J=1.6 Hz, 1H), 7.31-7.27 (m, 2H), 5.68 (dd, J=2.4, 9.6 Hz, 1H), 5.31 (br s, 1H), 4.61 (br s, 1H), 4.28 (s, 2H), 4.08-3.94 (m, 3H), 3.86 (br d, J=11.6 Hz, 1H), 3.79-3.71 (m, 1H), 3.52 (br t, J=4.8 Hz, 2H), 3.24 (br d, J=12.8 Hz, 2H), 3.04-2.91 (m, 1H), 2.87-2.67 (m, 5H), 2.65-2.47 (m, 2H), 2.41 (s, 3H), 2.32 (br s, 6H), 2.17 (br d, J=4.0 Hz, 1H), 2.09 (br s, 1H), 1.77 (br t, J=10.8 Hz, 3H), 1.52 (s, 9H), 1.36 (d, J=6.0 Hz, 3H).

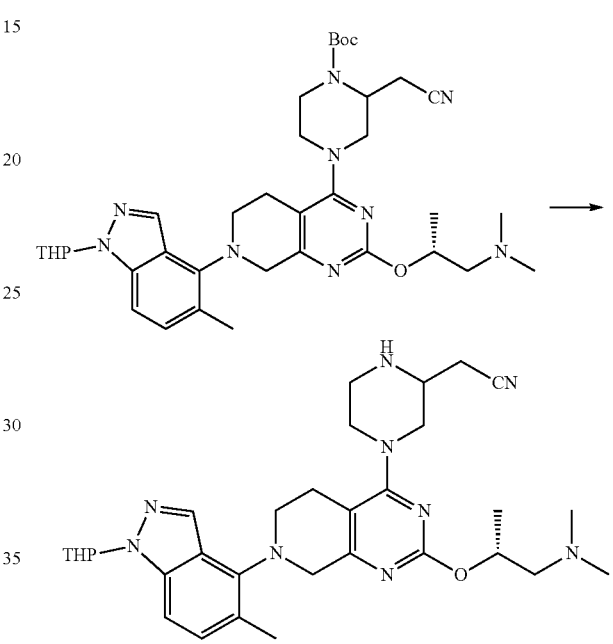

Step B: 2-[4-[2-[(1R)-2-(dimethylamino)-1-methyl-ethoxy]-7-(5-methyl-1-tetrahydropyran-2-yl-indazol-4-yl)-6,8-dihydro-5H-pyrido[3,4-d]pyrimidin-4-yl]piperazin-2-yl]acetonitrile: To a solution of tert-butyl 2-(cyanomethyl)-4-[2-[(1R)-2-(dimethylamino)-1-methyl-ethoxy]-7-(5-methyl-1-tetrahydropyran-2-yl-indazol-4-yl)-6,8-dihydro-5H-pyrido[3,4-d]pyrimidin-4-yl]piperazine-1-carboxylate (0.38 g, 564 umol) in dichloromethane (10 mL) was added TMSOTf (752 mg, 3.38 mmol) and 2,6-dimethylpyridine (725 mg, 6.77 mmol) at 0° C. and the mixture stirred at 10° C. for 1 hour. The mixture was quenched by addition of methanol (0.10 mL) and concentrated under vacuum. The residue was purified by reversed phase chromatography [water (Formic Acid, 0.1%)/acetonitrile]. The collected fractions were combined and the pH adjusted pH >7 by addition of saturated sodium bicarbonate solution and the aqueous layer extracted with dichloromethane/methanol (10/1) (3×10 mL). The extracts were washed with saturated sodium chloride solution (10 mL), dried over Na$_2$SO$_4$, filtered and concentrated under vacuum to give 2-[4-[2-[(1R)-2-(dimethylamino)-1-methyl-ethoxy]-7-(5-methyl-1-tetrahydropyran-2-yl-indazol-4-yl)-6,8-dihydro-5H-pyrido [3,4-d]pyrimidin-4-yl]piperazin-2-yl]acetonitrile (0.30 g, crude) as a yellow solid. ES+APCI MS m/z 574.1 [M+H]$^+$.

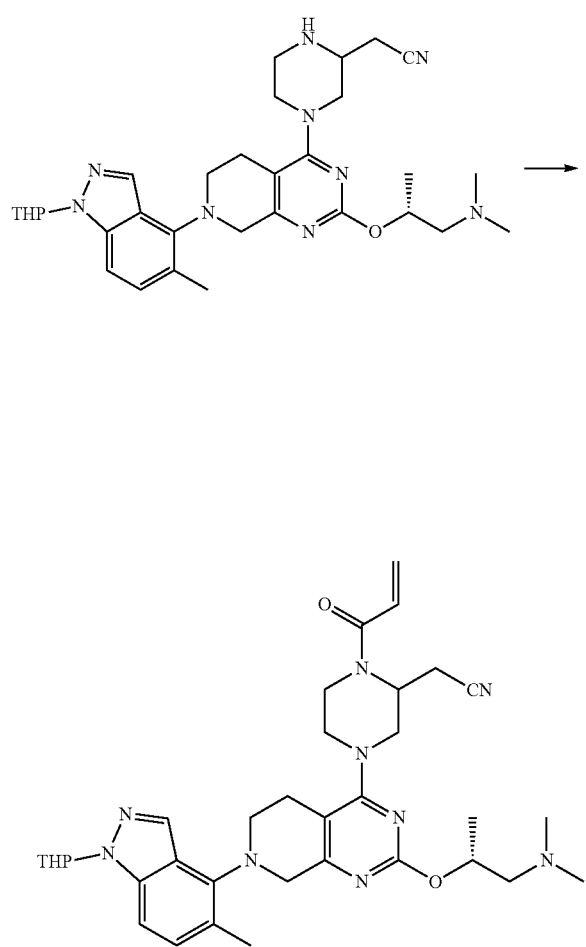

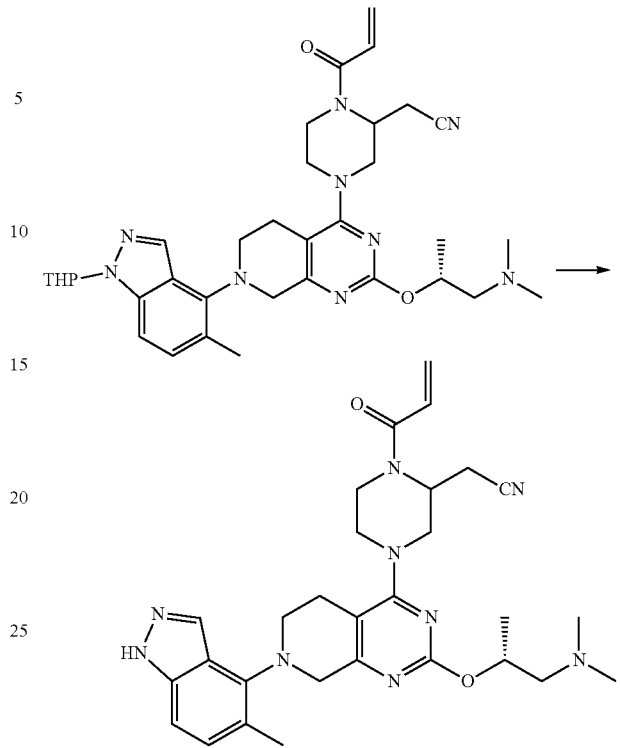

Step C: 2-[4-[2-[(1R)-2-(dimethylamino)-1-methyl-ethoxy]-7-(5-methyl-1-tetrahydropyran-2-yl-indazol-4-yl)-6,8-dihydro-5H-pyrido [3,4-d]pyrimidin-4-yl]-1-prop-2-enoyl-piperazin-2-yl]acetonitrile: To a solution of 2-[4-[2-[(1R)-2-(dimethylamino)-1-methyl-ethoxy]-7-(5-methyl-1-tetrahydropyran-2-yl-indazol-4-yl)-6,8-dihydro-5H-pyrido [3,4-d]pyrimidin-4-yl]piperazin-2-yl]acetonitrile (0.20 g, crude) and TEA (176 mg, 1.74 mmol, 243 uL) in dichloromethane (1.00 mL) was added prop-2-enoyl prop-2-enoate (44.0 mg, 349 umol) at 0° C. and the reaction stirred at 0° C. for 0.5 h. The mixture was quenched by addition of methanol (0.10 mL) and concentrated under vacuum. The residue was purified by reversed phase flash [water (Formic Acid, 0.1%)/acetonitrile]. The collected fractions were combined and the pH adjusted to pH >7 by addition of saturated sodium bicarbonate solution and the aqueous layer extracted with dichloromethane/methanol (10/1) (3×5.00 mL). The extracts were washed with saturated sodium chloride solution (1×10 mL), dried over $Na_2SO_4$, filtered and concentrated under vacuum to give 2-[4-[2-[(1R)-2-(dimethylamino)-1-methyl-ethoxy]-7-(5-methyl-1-tetrahydropyran-2-yl-indazol-4-yl)-6,8-dihydro-5H-pyrido [3,4-d]pyrimidin-4-yl]-1-prop-2-enoyl-piperazin-2-yl]acetonitrile (0.10 g, 127 umol, two steps 36.6% yield) as a yellow solid. ES+APCI MS m/z 628.6 $[M+H]^+$.

Step D: 2-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]-1-prop-2-enoyl-piperazin-2-yl]acetonitrile: A mixture of 2-[4-[2-[(1R)-2-(dimethylamino)-1-methyl-ethoxy]-7-(5-methyl-1-tetrahydropyran-2-yl-indazol-4-yl)-6,8-dihydro-5H-pyrido [3,4-d]pyrimidin-4-yl]-1-prop-2-enoyl-piperazin-2-yl]acetonitrile (40 mg, 63.7 umol) and TsOH (1.10 mg, 6.37 umol) in acetonitrile (3 mL) was stirred at 90° C. for 1 hour. The mixture was quenched by addition of saturated sodium bicarbonate (2 mL) at 0° C. and concentrated under vacuum. The residue was purified by column chromatography ($Al_2O_3$, dichloromethane/methanol=5/1). The collected desired fractions were concentrated under vacuum to give white solid. The residue was purified by prep-HPLC (column: Phenomenex Gemini 150*25 mm*10 um; mobile phase: [water (10 mM $NH_4HCO_3$)-ACN]; B %: 35%-65%, 3 min) and (column: Boston Green ODS 150*30 5 u; mobile phase: [water (0.225% Formic Acid)-ACN]; B %: 15%-45%, 10 min). The desired fractions were pooled and lyophilizated to give 2-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]-1-prop-2-enoyl-piperazin-2-yl]acetonitrile (2.99 mg, 5.50 umol). ES+APCI MS m/z 544.5 $[M+H]^+$. $^1$H NMR (400 MHz, chloroform-d) δ=8.36 (br s, 1H), 8.09 (s, 1H), 7.29 (br s, 1H), 7.24-7.20 (m, 1H), 6.62 (br d, J=13.6 Hz, 1H), 6.47-6.24 (m, 1H), 5.83 (br d, J=10.8 Hz, 1H), 5.50 (br s, 1H), 5.08 (br s, 1H), 4.60 (br s, 1H), 4.31 (s, 2H), 4.12 (br d, J=14.4 Hz, 1H), 3.99 (br d, J=10.8 Hz, 1H), 3.55 (br t, J=5.6 Hz, 2H), 3.42-3.29 (m, 1H), 3.10 (br s, 1H), 3.00-2.68 (m, 7H), 2.49 (s, 6H), 2.43 (s, 3H), 1.39 (d, J=6.0 Hz, 3H).

Example 153

2-[4-[7-(3-hydroxy-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl]acetonitrile

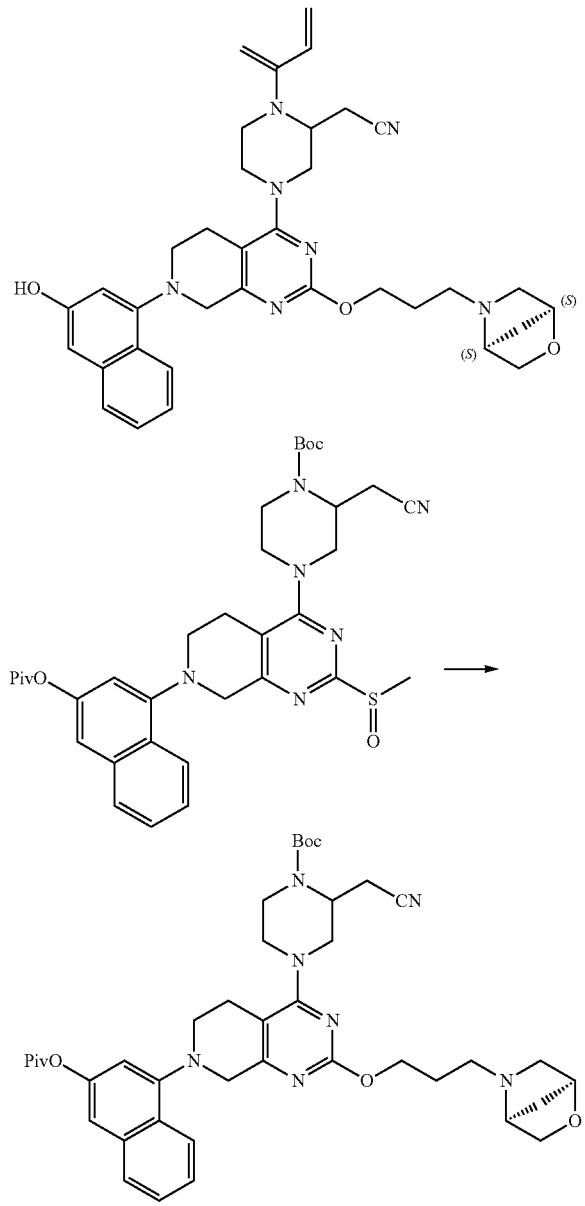

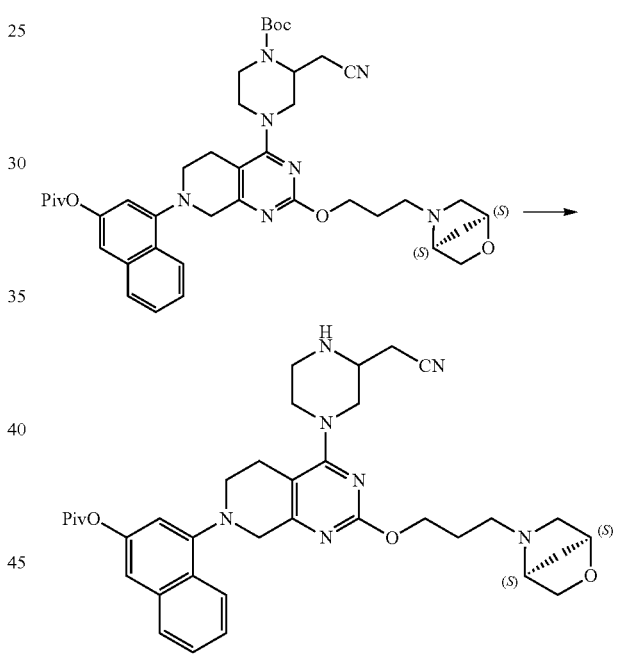

Step A: tert-butyl 2-(cyanomethyl)-4-[7-[3-(2,2-dimethylpropanoyloxy)-1-naphthyl]-2-[3-[(1S,4S)-2-oxa-5-azabicyclo[2.2.1]heptan-5-yl]propoxy]-6,8-dihydro-5H-pyrido[3,4-d]pyrimidin-4-yl]piperazine-1-carboxylate: To a solution of tert-butyl 2-(cyanomethyl)-4-[7-[3-(2,2-dimethylpropanoyloxy)-1-naphthyl]-2-methylsulfinyl-6,8-dihydro-5H-pyrido[3,4-d]pyrimidin-4-yl]piperazine-1-carboxylate (500 mg, 773 umol) and 3-[(1S,4S)-2-oxa-5-azabicyclo[2.2.1]heptan-5-yl]propan-1-ol (219 mg, 1.39 mmol) in toluene (10 mL) was added tBuONa (111 mg, 1.16 mmol) under $N_2$. The reaction mixture was stirred at 18° C. for 0.5 hour. Upon completion, the mixture was purified by silica gel chromatography (PE:EtOAc=3:1 to 0:1 then EA:MeOH=50:1 to 10:1) followed by reversed flash chromatography (50% to 90% MeCN in water, base condition) to give tert-butyl 2-(cyanomethyl)-4-[7-[3-(2,2-dimethylpropanoyloxy)-1-naphthyl]-2-[3-[(1S,4S)-2-oxa-5-azabicyclo[2.2.1]heptan-5-yl]propoxy]-6,8-dihydro-5H-pyrido[3,4-d]pyrimidin-4-yl]piperazine-1-carboxylate (120 mg, 156 umol, 20.5% yield, 97.9% purity) as a brown solid. $^1$H NMR (400 MHz, CHLOROFORM-d) δ=8.19-8.12 (m, 1H), 7.83-7.77 (m, 1H), 7.55-7.43 (m, 2H), 7.29 (d, J=1.6 Hz, 1H), 6.84 (d, J=2.0 Hz, 1H), 4.64 (br s, 1H), 4.42-4.35 (m, 3H), 4.26 (br d, J=5.2 Hz, 2H), 4.12-4.03 (m, 3H), 3.96 (br d, J=12.8 Hz, 1H), 3.62 (dd, J=1.6, 7.6 Hz, 1H), 3.50 (br s, 2H), 3.31 (br d, J=13.6 Hz, 3H), 3.11-2.97 (m, 2H), 2.94 (br d, J=8.8 Hz, 1H), 2.89-2.69 (m, 5H), 2.54 (br d, J=9.8 Hz, 1H), 2.00-1.92 (m, 2H), 1.90-1.83 (m, 1H), 1.73 (br d, J=10.0 Hz, 1H), 1.53 (s, 9H), 1.41 (s, 9H)

Step B: 4-[4-[3-(cyanomethyl)piperazin-1-yl]-2-[3-[(1S,4S)-2-oxa-5-azabicyclo[2.2.1]heptan-5-yl]propoxy]-6,8-dihydro-5H-pyrido[3,4-d]pyrimidin-7-yl]-2-naphthyl] 2,2-dimethylpropanoate: A solution of tert-butyl 2-(cyanomethyl)-4-[7-[3-(2,2-dimethylpropanoyloxy)-1-naphthyl]-2-[3-[(1S,4S)-2-oxa-5-azabicyclo[2.2.1]heptan-5-yl]propoxy]-6,8-dihydro-5H-pyrido[3,4-d]pyrimidin-4-yl]piperazine-1-carboxylate (120 mg, 162 umol) in TFA (370 mg, 3.24 mmol, 240 uL) was stirred at 18° C. for 1 hour. Upon completion, the solvent was removed under vacuum to give 4-[4-[3-(cyanomethyl)piperazin-1-yl]-2-[3-[(1S,4S)-2-oxa-5-azabicyclo[2.2.1]heptan-5-yl]propoxy]-6,8-dihydro-5H-pyrido[3,4-d]pyrimidin-7-yl]-2-naphthyl] 2,2-dimethylpropanoate (140 mg, 161 umol, 99.5% yield, 2TFA) as brown oil.

457

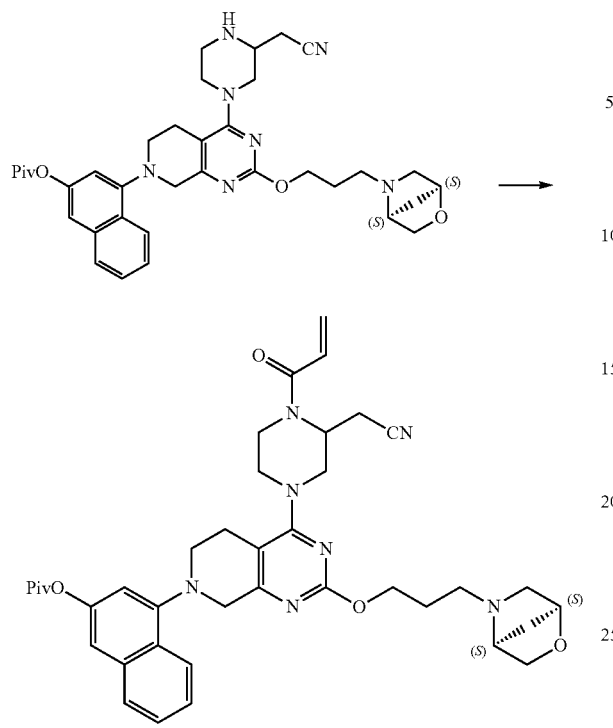

Step C: [4-[4-[3-(cyanomethyl)-4-prop-2-enoyl-piperazin-1-yl]-2-[3-[(1S,4S)-2-oxa-5-azabicyclo[2.2.1]heptan-5-yl]propoxy]-6,8-dihydro-5H-pyrido[3,4-d]pyrimidin-7-yl]-2-naphthyl] 2,2-dimethylpropanoate: To a solution of [4-[4-[3-(cyanomethyl)piperazin-1-yl]-2-[3-[(1S,4S)-2-oxa-5-azabicyclo[2.2.1]heptan-5-yl]propoxy]-6,8-dihydro-5H-pyrido[3,4-d]pyrimidin-7-yl]-2-naphthyl] 2,2-dimethylpropanoate (140 mg, 161 umol) and DIEA (167 mg, 1.29 mmol, 225 uL) in DCM (2 mL) was added prop-2-enoyl prop-2-enoate (30.5 mg, 242 umol) at 0° C. The reaction mixture was stirred at 18° C. for 1 hour. Upon completion, the reaction mixture was quenched by addition of water (5 mL) and the aqueous layer extracted with DCM (3×10 mL). The combined organic layers were dried over Na$_2$SO$_4$, filtered and concentrated under vacuum. The residue was purified by reversed flash (Base condition, MeCN/NH$_3$.H$_2$O in water: 50% to 80%) to give [4-[4-[3-(cyanomethyl)-4-prop-2-enoyl-piperazin-1-yl]-2-[3-[(1S,4S)-2-oxa-5-azabicyclo[2.2.1]heptan-5-yl]propoxy]-6,8-dihydro-5H-pyrido[3,4-d]pyrimidin-7-yl]-2-naphthyl] 2,2-dimethylpropanoate (60 mg, 86.5 umol, 53.6% yield). $^1$H NMR (400 MHz, CHLOROFORM-d) δ=8.22-8.13 (m, 1H), 7.84-7.78 (m, 1H), 7.56-7.45 (m, 2H), 7.31 (d, J=2.0 Hz, 1H), 6.86 (d, J=2.4 Hz, 1H), 6.62 (br s, 1H), 6.47-6.37 (m, 1H), 5.92-5.79 (m, 1H), 5.24-4.88 (m, 1H), 4.75 (br s, 1H), 4.45-4.36 (m, 3H), 4.31-4.20 (m, 2H), 4.15 (br d, J=13.6 Hz, 1H), 4.10-4.01 (m, 2H), 3.64 (dd, J=1.6, 7.6 Hz, 2H), 3.51 (br s, 2H), 3.38 (br s, 2H), 3.14 (br s, 1H), 3.08-2.73 (m, 7H), 2.56 (br d, J=10.0 Hz, 1H), 2.03-1.93 (m, 2H), 1.88 (br d, J=9.6 Hz, 1H), 1.78-1.70 (m, 1H), 1.61 (s, 9H), 1.43 (s, 9H).

458

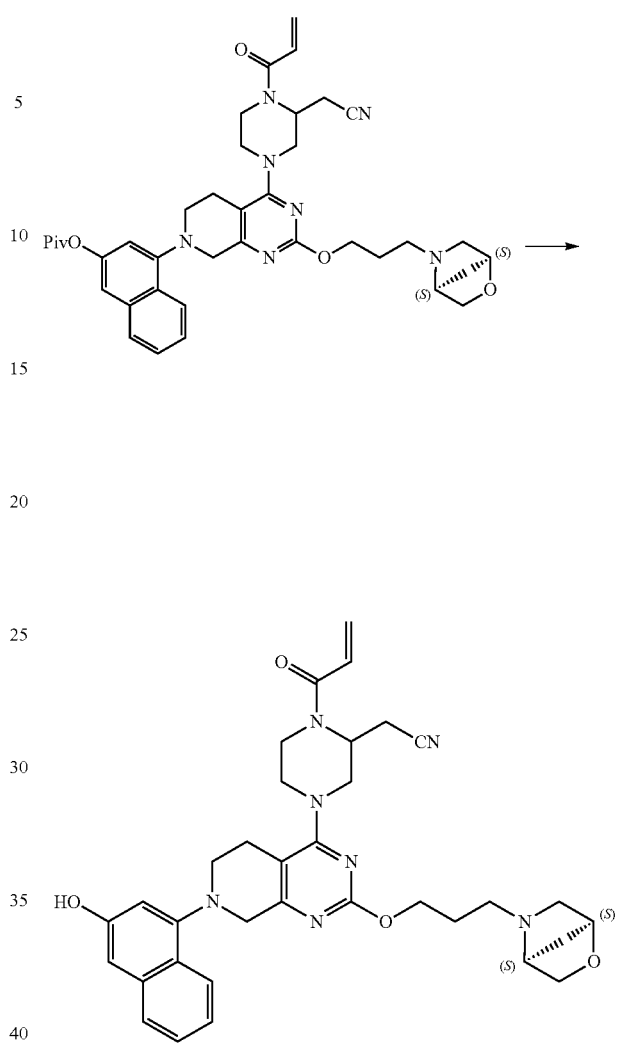

Step D: 2-[4-[7-(3-hydroxy-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl]acetonitrile: To a solution of [4-[4-[3-(cyanomethyl)-4-prop-2-enoyl-piperazin-1-yl]-2-[3-[(1S,4S)-2-oxa-5-azabicyclo[2.2.1]heptan-5-yl]propoxy]-6,8-dihydro-5H-pyrido[3,4-d]pyrimidin-7-yl]-2-naphthyl] 2,2-dimethylpropanoate (60 mg, 86.5 umol) in THF (0.5 mL) was added NaOH (2 M, 600 uL). The reaction mixture was stirred at 18° C. for 12 hours. Upon completion, the reaction mixture was acidified by addition of 4 drops of HCOOH (20% in water) and the aqueous layer was extracted with DCM (5×8 mL). The combined organics were dried over Na$_2$SO$_4$ and concentrated under vacuum. The residue was purified by prep-HPLC (column: Luna C18 150*25 5 u; mobile phase: [water (0.225% Formic Acid)-ACN]; B %: 10%-40%,10 min) to give 2-[4-[7-(3-hydroxy-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl]acetonitrile (19.8 mg, 28.3 umol, 32.8% yield, 93.8% purity, Formic Acid salt) was obtained as a brown solid. ES+APCI MS m/z 610.5 [M+H]$^+$.

Example 154

2-[4-[7-(1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl] acetonitrile

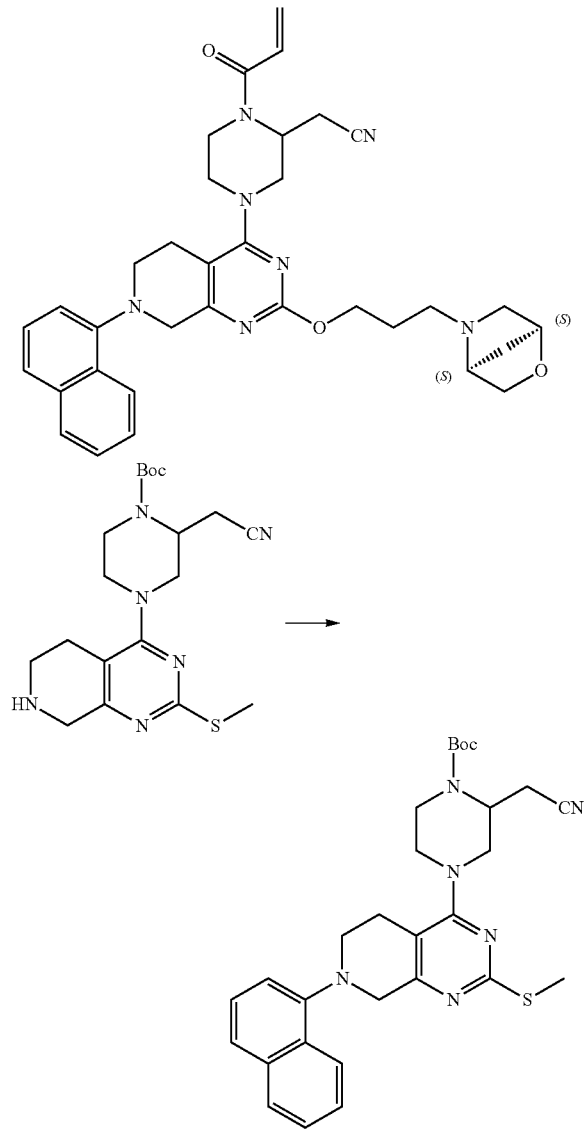

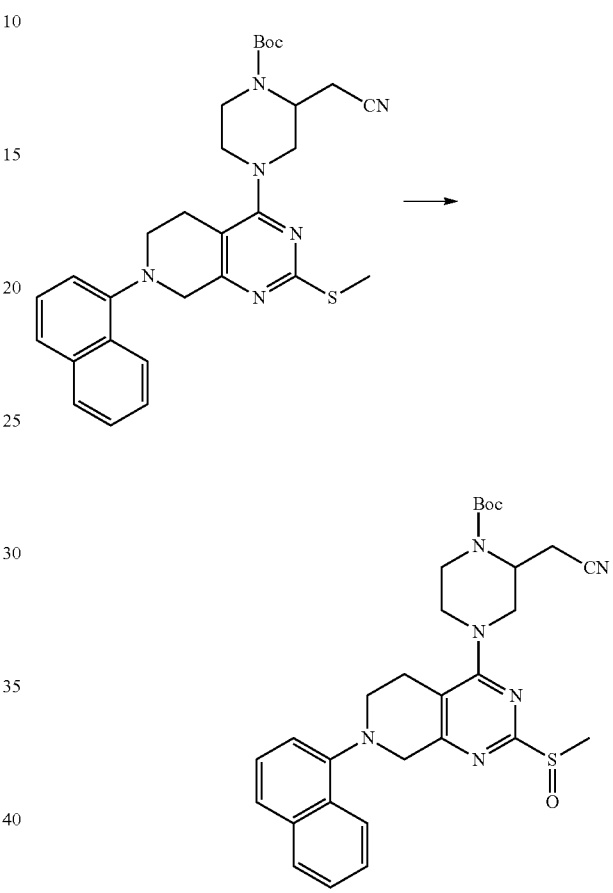

Step A: tert-butyl2-(cyanomethyl)-4-[2-methylsulfanyl-7-(1-naphthyl)-6,8-dihydro-5H-pyrido[3,4-d]pyrimidin-4-yl]piperazine-1-carboxylate: To the solution of tert-butyl 2-(cyanomethyl)-4-(2-methylsulfanyl-5,6,7,8-tetrahydropyrido[3,4-d]pyrimidin-4-yl)piperazine-1-carboxylate (3 g, 7.42 mmol), 1-bromonaphthalene (3.07 g, 14.8 mmol, 2.06 mL) and $Cs_2CO_3$ (7.25 g, 22.2 mmol) in toluene (60 mL) was added XPhos palladacycle gen 3 (628 mg, 742 umol) under $N_2$ and the suspension was degassed under vacuum and purged with $N_2$ several times. The mixture was warmed to 70° C. and stirred at 70° C. for 10 hours. The resulting mixture was filtered and the filter cake was washed with EtOAc (3×20 mL). The combined organics were concentrated under reduced pressure to give a residue. The residue was purified by silica gel chromatography (PE:EtOAc from 50:1 to 3:1) to give tert-butyl2-(cyanomethyl)-4-[2-methylsulfanyl-7-(1-naphthyl)-6,8-dihydro-5H-pyrido[3,4-d]pyrimidin-4-yl]piperazine-1-carboxylate (3.55 g, 6.02 mmol, 81.2% yield, 90.0% purity) as brown oil. ES+APCI MS m/z 531.4 $[M+H]^+$.

Step B: tert-butyl 2-(cyanomethyl)-4-[2-methylsulfinyl-7-(1-naphthyl)-6,8-dihydro-5H-pyrido[3,4-d]pyrimidin-4-yl]piperazine-1-carboxylate: To the solution of tert-butyl 2-(cyanomethyl)-4-[2-methylsulfanyl-7-(1-naphthyl)-6,8-dihydro-5H-pyrido[3,4-d]pyrimidin-4-yl]piperazine-1-carboxylate (2.95 g, 5.56 mmol) in DCM (60 mL) was added m-CPBA (1.13 g, 5.56 mmol, 85.0% purity) at 0° C. and stirred at 0° C. for 1 hour. The reaction mixture was quenched by addition of saturated $Na_2S_2O_3$ (20 mL) at 0° C. and layers were separated, and the aqueous layer diluted with water (20 mL) and extracted with EtOAc (60 mL). The combined organic layers were dried over anhydrous $Na_2SO_4$, filtered and concentrated under reduced pressure to give a residue. The residue was purified by reversed phase flash column (ACN/Water (0.1% Formic Acid)=100%) to give tert-butyl 2-(cyanomethyl)-4-[2-methylsulfinyl-7-(1-naphthyl)-6,8-dihydro-5H-pyrido[3,4-d]pyrimidin-4-yl]piperazine-1-carboxylate (1.7 g, 2.80 mmol, 50.3% yield, 90.0% purity) as brown solid. ES+APCI MS m/z 574.4 $[M+H]^+$.

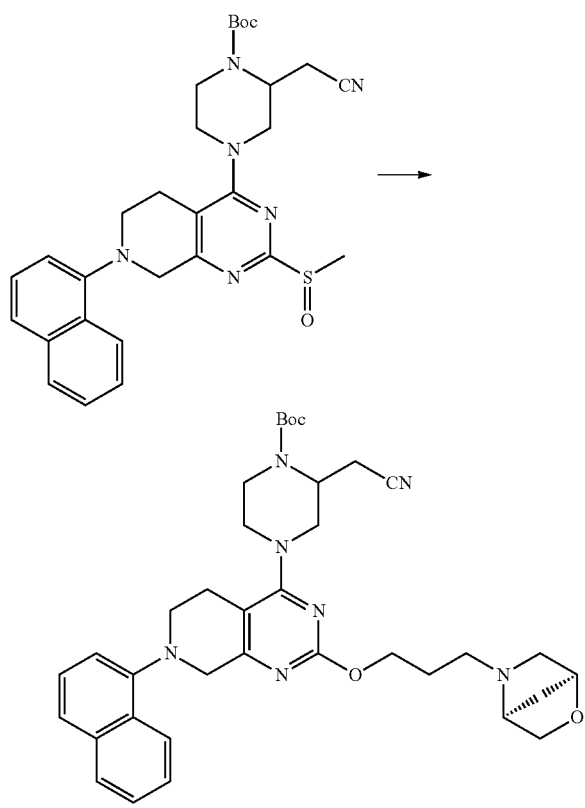

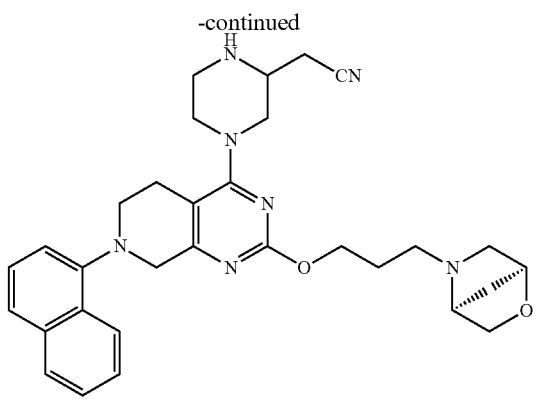

Step D: 2-[4-[7-(1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile: A reaction mixture of tert-butyl 2-(cyanomethyl)-4-[7-(1-naphthyl)-2-[3-[(1S,4S)-2-oxa-5-azabicyclo[2.2.1]heptan-5-yl]propoxy]-6,8-dihydro-5H-pyrido [3,4-d]pyrimidin-4-yl]piperazine-1-carboxylate (200 mg, 313 umol) in TFA (770 mg, 6.75 mmol, 500 uL) was stirred at 18° C. for 1 hour. Upon completion the solvent was removed under vacuum to give 2-[4-[7-(1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (271 mg, crude) as a brown oil.

Step C: tert-butyl 2-(cyanomethyl)-4-[7-(1-naphthyl)-2-[3-[(1S,4S)-2-oxa-5-azabicyclo[2.2.1]heptan-5-yl]propoxy]-6,8-dihydro-5H-pyrido [3,4-d]pyrimidin-4-yl]piperazine-1-carboxylate: To a solution of tert-butyl 2-(cyanomethyl)-4-[2-methylsulfinyl-7-(1-naphthyl)-6,8-dihydro-5H-pyrido[3,4-d]pyrimidin-4-yl]piperazine-1-carboxylate (300 mg, 549 umol) and 3-[(1S,4S)-2-oxa-5-azabicyclo[2.2.1]heptan-5-yl]propan-1-ol (160 mg, 1.02 mmol) in toluene (6 mL) was added tBuONa (79.1 mg, 823 umol). The reaction mixture was stirred at 18° C. for 0.5 hour. Upon completion, the reaction mixture was purified by silica gel chromatography (PE:EA=3:1 to 0:1 then EA:MeOH=50:1 to 10:1) to give tert-butyl 2-(cyanomethyl)-4-[7-(1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazine-1-carboxylate (200 mg, 249 umol, 45.3% yield, 79.6% purity) was obtained as a brown solid. ES+APCI MS m/z 640.5 [M+H]⁺.

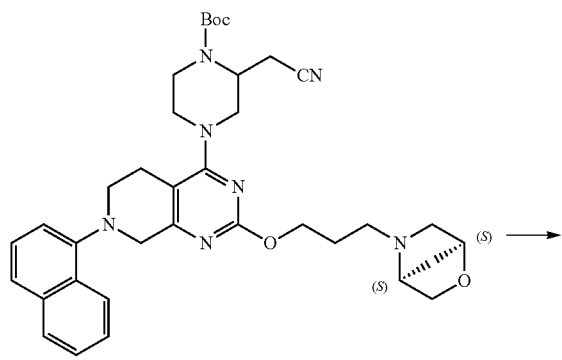

Step E: 2-[4-[7-(1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl]acetonitrile: To a solution of 2-[4-[7-(1-naphthyl)-2-[3-

[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (271 mg, 502 umol) and DIEA (323 mg, 2.50 mmol, 0.435 mL) in DCM (6 mL) was added prop-2-enoyl prop-2-enoate (60 mg, 476 umol) at 0° C. and the reaction mixture stirred at 18° C. for 1 hour. Upon completion, the reaction mixture was quenched by addition of a drop of water and purified by silica gel chromatography (PE:EtOAc=3:1 to 0:1) then prep HPLC (column: Gemini 150*25 5 u; mobile phase: [water (0.05% ammonia hydroxide v/v)-ACN]; B %: 33%-63%,12 min) to give 2-[4-[7-(1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl]acetonitrile (23.8 mg, 40.0 umol, 7.97% yield) as yellow solid. ES+APCI MS m/z 594.5 [M+H]+.

Example 155

(S)-1-(4-(7-(5-methyl-1H-indazol-4-yl)-2-((1-methylpyrrolidin-2-yl)methoxy)-5,6,7,8-tetrahydropyrido[3,4-d]pyrimidin-4-yl)piperazin-1-yl)prop-2-en-1-one

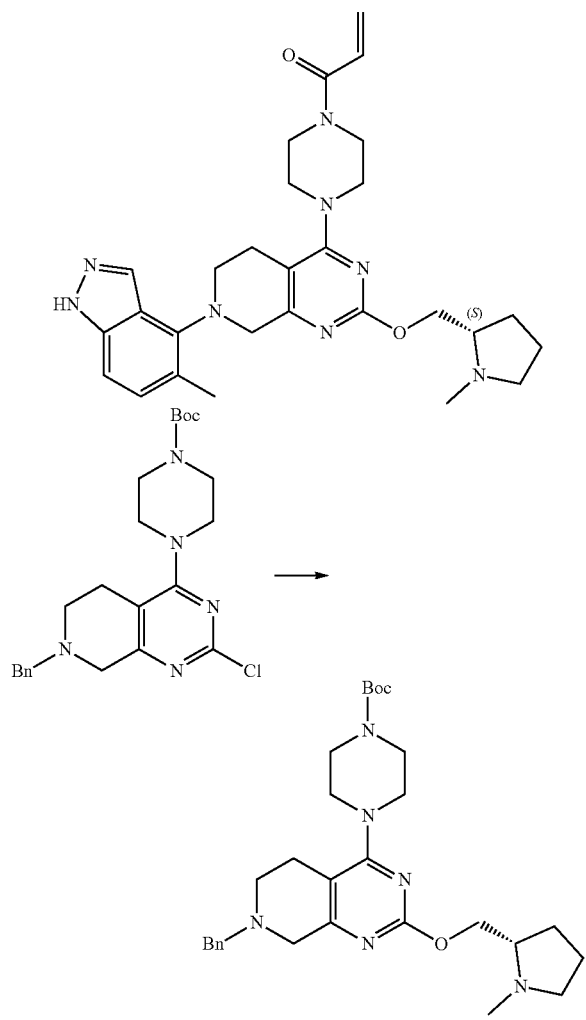

methylpyrrolidin-2-yl]methanol (4.15 g, 36.0 mmol, 4.28 mL) in THF (100 mL) was added NaH (2.16 g, 54.06 mmol, 60% purity) in portions at 0° C. After the mixture was stirred at 0° C. for 1 hour, a solution of tert-butyl4-(7-benzyl-2-chloro-6,8-dihydro-5H-pyrido[3,4-d]pyrimidin-4-yl)piperazine-1-carboxylate (8.0 g, 18.02 mmol) in THF (60 mL) was added and the mixture was stirred at 70° C. for 11 hours. After completion, the reaction mixture was poured into aqueous NH4Cl (160 mL), and the aqueous layer extracted with EtOAc (2×100 mL). The combined organics were dried over Na2SO4, filtered and concentrated in vacuo. The residue was purified by column chromatography (SiO2, Petroleum ether/Ethyl acetate=3/1 to Ethyl acetate/Methanol=10:1) to give tert-butyl 4-[7-benzyl-2-[[(2S)-1-methylpyrrolidin-2-yl]methoxy]-6,8-dihydro-5H-pyrido[3,4-d]pyrimidin-4-yl]piperazine-1-carboxylate (4.9 g, 8.70 mmol, 48.3% yield, 92.8% purity) as gray solid. ES+APCI MS m/z 523.2 [M+H]+

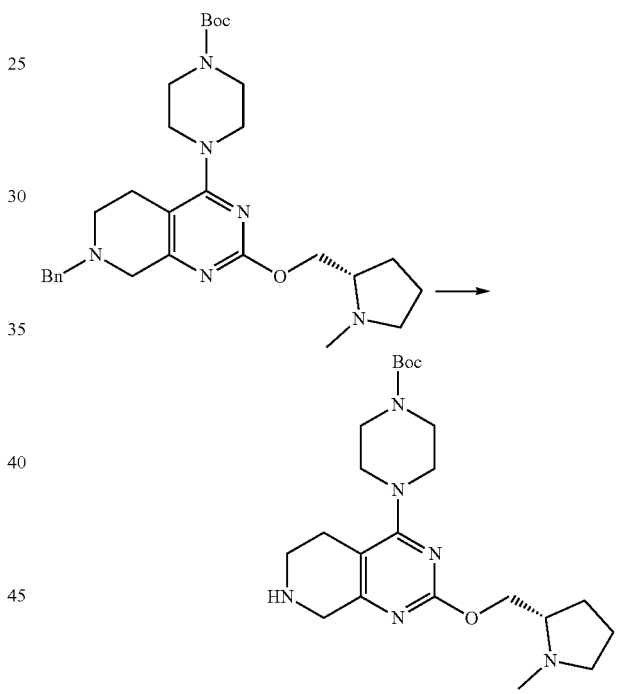

Step B: tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate: To a mixture of tert-butyl 4-[7-benzyl-2-[[(2S)-1-methylpyrrolidin-2-yl]methoxy]-6,8-dihydro-5H-pyrido[3,4-d]pyrimidin-4-yl]piperazine-1-carboxylate (2.20 g, 4.21 mmol) in MeOH (30 mL) was added Pd(OH)2/C (700 mg, 10% purity) and the mixture was degassed under vacuum and purged with H2 several times and the reaction stirred at 40° C. for 12 hours under H2 (15 Psi). After completion, the reaction mixture was filtered through celite and the filtrate concentrated to give tert-butyl 4-[2-[[(2S)-1-methylpyrrolidin-2-yl] methoxy]-5,6,7,8-tetrahydropyrido[3,4-d]pyrimidin-4-yl]piperazine-1-carboxylate (1.80 g, 4.02 mmol, 95.6% yield, 96.7% purity) as black solid. ES+APCI MS m/z 433.1 [M+H]+.

Step A: tert-butyl 4-[7-benzyl-2-[[(2S)-1-methylpyrrolidin-2-yl]methoxy]-6,8-dihydro-5H-pyrido[3,4-d]pyrimidin-4-yl]piperazine-1-carboxylate: To a mixture of [(2S)-1-

465

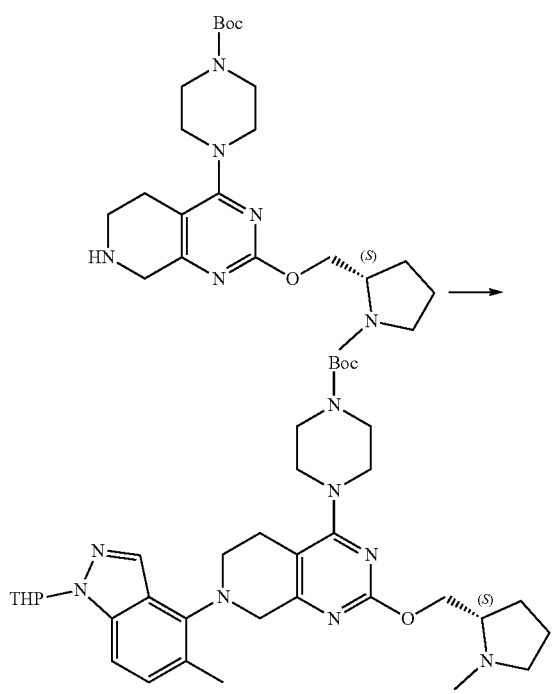

Step C: tert-butyl 4-[2-[[(2S)-1-methylpyrrolidin-2-yl]methoxy] tetrahydropyran-2-yl-indazol-4-yl)-6,8-dihydro-5H-pyrido[3,4-d]pyrimidin-4-yl]piperazine-1-carboxylate:
To a mixture of tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate (200 mg, 462 umol) and 4-bromo-5-methyl-1-tetrahydropyran-2-yl-indazole (204 mg, 694 umol) in toluene (4 mL) was added Pd$_2$(dba)$_3$ (63.5 mg, 69.4 umol), RuPhos (43.2 mg, 92.5 umol) and Cs$_2$CO$_3$ (301 mg, 925 umol) and the mixture stirred at 110° C. for 12 hours under N$_2$. After completion, the reaction mixture was partitioned between water (10 mL) and EtOAc and the layers separated. The aqueous layer was subsequently extracted with EtOAc (2×10 mL) and the combined organics were dried over Na$_2$SO$_4$, filtered and concentrated. The residue was purified by column chromatography (SiO$_2$, Petroleum ether/Ethyl acetate=5/1 to Ethyl acetate/MeOH=10/1) to give tert-butyl 4-[2-[[(2S)-1-methylpyrrolidin-2-yl]methoxy]-7-(5-methyl-1-tetrahydropyran-2-yl-indazol-4-yl)-6,8-dihydro-5H-pyrido[3,4-d]pyrimidin-4-yl]piperazine-1-carboxylate (240 mg, 310 umol, 67.1% yield, 83.6% purity) as brown oil. ES+APCI MS m/z 647.6 [M+H]$^+$.

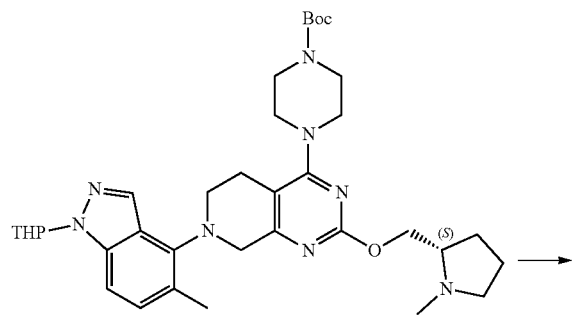

-continued

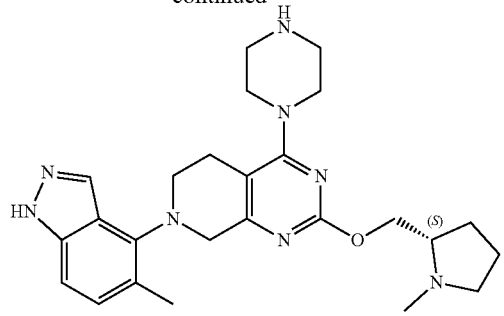

Step D: 7-(5-methyl-1H-indazol-4-yl)-2-[[(2S)-1-methylpyrrolidin-2-yl]methoxy]-4-piperazin-1-yl-6,8-dihydro-5H-pyrido[3,4-d]pyrimidine To a mixture of tert-butyl 4-[2-[[(2S)-1-methylpyrrolidin-2-yl]methoxy]-7-(5-methyl-1-tetrahydropyran-2-yl-indazol-4-yl)-6,8-dihydro-5H-pyrido[3,4-d]pyrimidin-4-yl]piperazine-1-carboxylate (240 mg, 371 umol) in DCM (1 mL) was added TFA (1.54 g, 13.5 mmol, 1 mL) and the mixture stirred at 15° C. for 1 hour. After completion, the reaction mixture was concentrated to give 7-(5-methyl-1H-indazol-4-yl)-2-[[(2S)-1-methylpyrrolidin-2-yl]methoxy]-4-piperazin-1-yl-6,8-dihydro-5H-pyrido[3,4-d]pyrimidine (250 mg, 309 umol, 83.4% yield, 85.5% purity, 2TFA) as brown solid which was used for the next step without further purification. ES+APCI MS m/z 463.4 [M+H]$^+$.

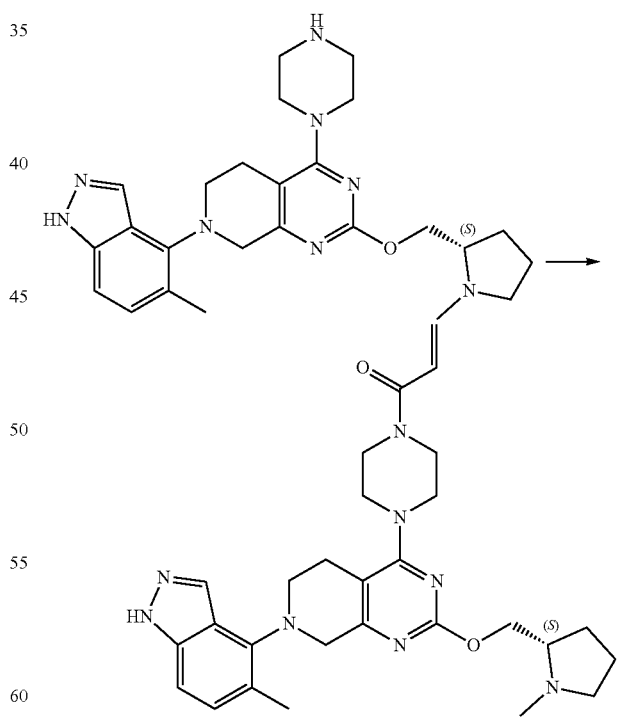

Step E: 1-[4-[7-(5-methyl-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one: To a mixture of 7-(5-methyl-1H-indazol-4-yl)-2-[[(2S)-1-methylpyrrolidin-2-yl]methoxy]-4-piperazin-1-yl-6,8-dihydro- 5H-pyrido[3,4-d]pyrimidine (250 mg, 362 umol, 2TFA) in DCM (2 mL) was added DIEA (702 mg, 5.43 mmol, 946 uL) and the mixture cooled to −50° C. Prop-2-enoyl prop-2-enoate (36.5 mg, 289 umol) was added in portions to the reaction at −50° C. and the mixture stirred at −50° C. for 30 minutes. After completion, the reaction mixture was quenched by addition of MeOH (1 mL) and the mixture concentrated. The residue was taken up in DCM (10 mL) and the organics washed with H₂O (2×8 mL). The organics were dried over Na₂SO₄, filtered and concentrated. The residue was purified by prep-HPLC ((Instrument: gx-1; Column: Phenomenex Gemini C18 250*50 mm*10 um; Condition: water (0.05% ammonia hydroxide v/v)-ACN; Begin B: 32; End B: 62; Gradient Time (min): 12; 100% B Hold Time (min): 2; FlowRate (ml/min): 25) to give 1-[4-[7-(5-methyl-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one (48.6 mg, 92.9 umol, 25.7% yield, 98.7% purity) as yellow solid. ES+APCI MS m/z 517.5 [M+H]⁺.

Example 156

(S)-1-(4-(2-((1-methylpyrrolidin-2-yl)methoxy)-7-(5-(trifluoromethyl)-1H-indazol-4-yl)-5,6,7,8-tetrahydropyrido[3,4-d]pyrimidin-4-yl)piperazin-1-yl)prop-2-en-1-one

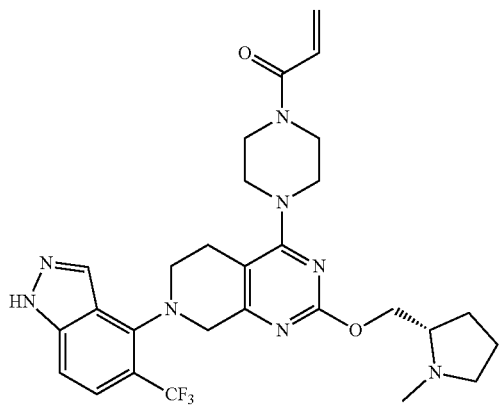 [SMILES: C=CC(=O)N1CCN(c2nc(OC[C@@H]3CCCN3C)nc3c2CCN(c2c(C(F)(F)F)ccc4[nH]ncc24)C3)CC1]

(S)-1-(4-(2-((1-methylpyrrolidin-2-yl)methoxy)-7-(5-(trifluoromethyl)-1H-indazol-4-yl)-5,6,7,8-tetrahydropyrido[3,4-d]pyrimidin-4-yl)piperazin-1-yl)prop-2-en-1-one was prepared following Example 155 substituting 4-bromo-1-tetrahydropyran-2-yl-5-(trifluoromethyl)indazole (Intermediate 60) for 4-bromo-5-methyl-1-tetrahydropyran-2-yl-indazole in Step C. ES+APCI MS m/z 571.4 [M+H]⁺.

Example 157

(S)-1-(4-(7-(5-methoxy-1H-indazol-4-yl)-2-(1-methylpyrrolidin-2-yl)methoxy)-5,6,7,8-tetrahydropyrido[3,4-d]pyrimidin-4-yl)piperazin-1-yl)prop-2-en-1-one

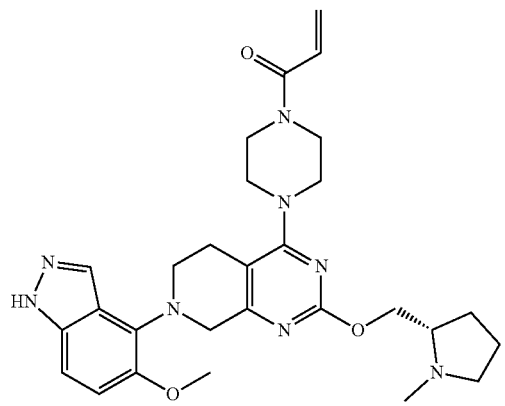 [SMILES: C=CC(=O)N1CCN(c2nc(OC[C@@H]3CCCN3C)nc3c2CCN(c2c(OC)ccc4[nH]ncc24)C3)CC1]

(S)-1-(4-(7-(5-methoxy-1H-indazol-4-yl)-2-((1-methylpyrrolidin-2-yl)methoxy)-5,6,7,8-tetrahydropyrido[3,4-d]pyrimidin-4-yl)piperazin-1-yl)prop-2-en-1-one was prepared following Example 155 substituting 4-bromo-5-methoxy-1-tetrahydropyran-2-yl-indazole for 4-bromo-5-methyl-1-tetrahydropyran-2-yl-indazole in Step C. ES+APCI MS m/z 533.4 [M+H]⁺.

Example 158

1-[4-[7-(2-isopropylphenyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one

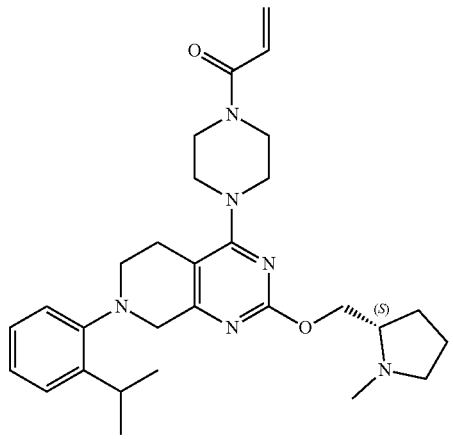

-continued

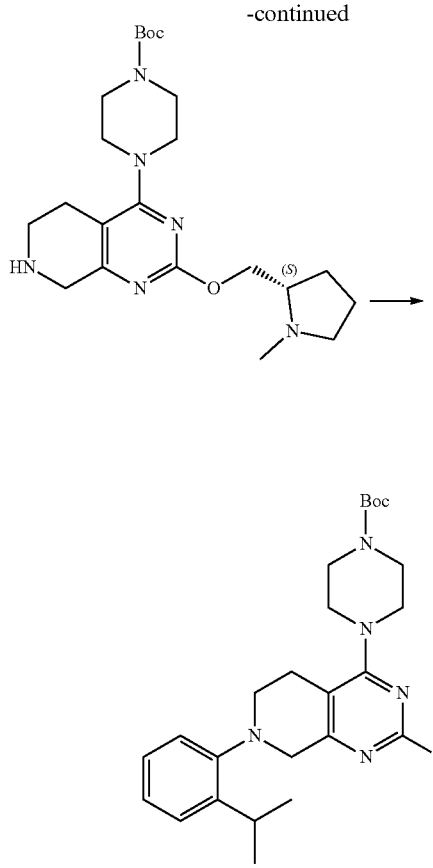

Step A: tert-butyl 4-[7-(2-isopropylphenyl)-2-[[(2S)-1-methylpyrrolidin-2-yl]methoxy]-6,8-dihydro-5H-pyrido[3,4-d]pyrimidin-4-yl]piperazine-1-carboxylate: tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate (200 mg, 462 umol), 1-bromo-2-isopropyl-benzene (120 mg, 601 umol), Cs$_2$CO$_3$ (452 mg, 1.39 mmol) and XPHOS PALLADACYCLE GEN 3 (78.3 mg, 92.5 umol) in toluene (4.00 mL) was de-gassed with N$_2$ and then heated to 100° C. for 10 hours under N$_2$. Upon completion, the mixture was filtered and the filtrate was concentrated. The crude product was purified by silica gel chromatography eluted with EtOAc/MeOH=50/1 to 5/1 to give tert-butyl 4-[7-(2-isopropylphenyl)-2-[[(2S)-1-methylpyrrolidin-2-yl]methoxy]-6,8-dihydro-5H-pyrido[3,4-d]pyrimidin-4-yl]piperazine-1-carboxylate (84.6 mg, 134 umol, 28.9% yield, 87.0% purity) as a yellow solid. ES+APCI MS m/z 551.2 [M+H]$^+$.

1-[4-[7-(2-isopropylphenyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one was prepared following Example 155 substituting tert-butyl 4-[7-(2-isopropylphenyl)-2-[[(2S)-1-methylpyrrolidin-2-yl]methoxy]-6,8-dihydro-5H-pyrido[3,4-d]pyrimidin-4-yl]piperazine-1-carboxylate for tert-butyl 4-[2-[[(2S)-1-methylpyrrolidin-2-yl]methoxy]-7-(5-methyl-1-tetrahydropyran-2-yl-indazol-4-yl)-6,8-dihydro-5H-pyrido[3,4-d]pyrimidin-4-yl]piperazine-1-carboxylate in Step D. ES+APCI MS m/z 505.6 [M+H]$^+$.

Example 159

(S)-1-(4-(2-((1-methylpyrrolidin-2-yl)methoxy)-7-(2-(trifluoromethyl)phenyl)-5,6,7,8-tetrahydropyrido[3,4-d]pyrimidin-4-yl)piperazin-1-yl)prop-2-en-1-one

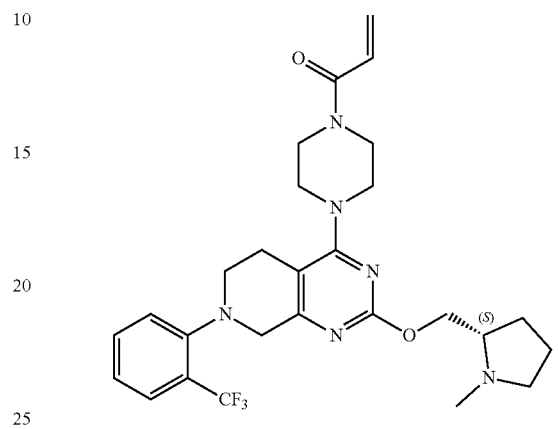

(S)-1-(4-(2-((1-methylpyrrolidin-2-yl)methoxy)-7-(2-(trifluoromethyl)phenyl)-5,6,7,8-tetrahydropyrido[3,4-d]pyrimidin-4-yl)piperazin-1-yl)prop-2-en-1-one was prepared following Example 155 substituting 1-bromo-2-(trifluoromethyl)benzene for 4-bromo-5-methyl-1-tetrahydropyran-2-yl-indazole in Step C. ES+APCI MS m/z 531.5 [M+H]$^+$.

Example 160

1-(4-(7-(5-methyl-1H-indazol-4-yl)-2-(3-(piperidin-1-yl)propoxy)-5,6,7,8-tetrahydropyrido[3,4-d]pyrimidin-4-yl)piperazin-1-yl)prop-2-en-1-one

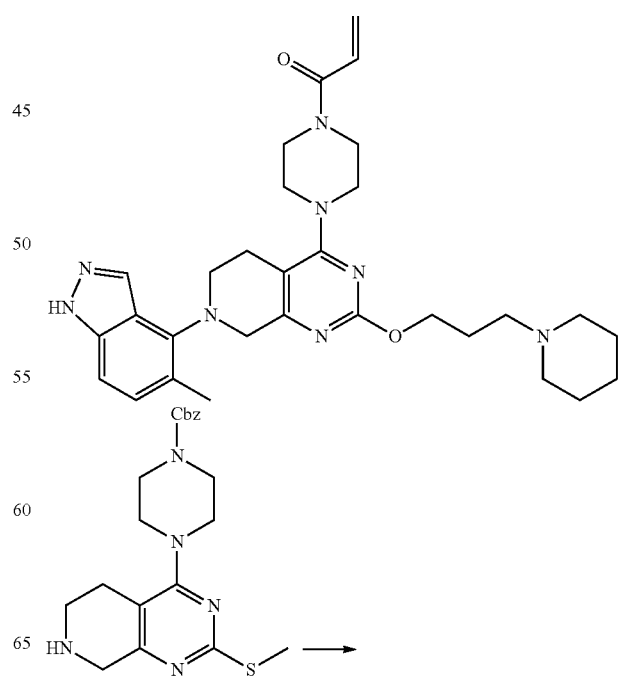

-continued

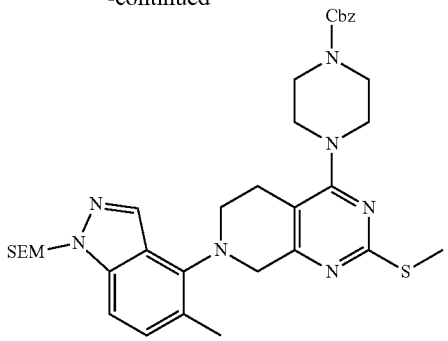

Step A: Benzyl 4-[2-methylsulfanyl-7-[5-methyl-1-(2-trimethylsilylethoxymethyl)indazol-4-yl]-6,8-dihydro-5H-pyrido[3,4-d]pyrimidin-4-yl]piperazine-1-carboxylate: A mixture of benzyl 4-(2-methylsulfanyl-5,6,7,8-tetrahydropyrido[3,4-d] pyrimidin-4-yl)piperazine-1-carboxylate (3.15 g, 7.88 mmol), 2-[(4-bromo-5-methyl-indazol-1-yl) methoxy]ethyl-trimethyl-silane (3.50 g, 10.2 mmol), Cs$_2$CO$_3$ (6.42 g, 19.70 mmol), Pd$_2$(dba)$_3$ (1.08 g, 1.18 mmol) and RuPhos (735 mg, 1.58 mmol) in toluene (50 mL) was degassed and with N$_2$ 3 times and the mixture stirred at 90° C. for 10 hours under N$_2$ atmosphere. The reaction mixture was quenched by addition of water (100 mL) and the aqueous layer extracted with ethyl acetate (3×100 mL). The combined organics were washed with brine (50 mL), dried over Na$_2$SO$_4$, filtered and concentrated under reduced. The residue was purified by column chromatography using 1→33% EtOAc/Petroleum Ether to give benzyl 4-[2-methylsulfanyl-7-[5-methyl-1-(2-trimethylsilylethoxymethyl)indazol-4-yl]-6,8-dihydro-5H-pyrido[3,4-d]pyrimidin-4-yl] piperazine-1-carboxylate (2.30 g, 2.93 mmol, 37.1% yield). ES+APCI MS m/z 660.3 [M+H]$^+$.

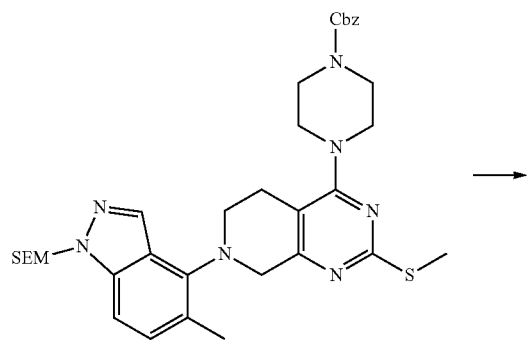

Step B: benzyl 4-[2-methylsulfinyl-7-[5-methyl-1-(2-trimethylsilyl ethoxymethyl)indazol-4-yl]-6,8-dihydro-5H-pyrido[3,4-d]pyrimidin-4-yl]piperazine-1-carboxylate: To a stirred solution of benzyl 4-[2-methylsulfanyl-7-[5-methyl-1-(2-trimethylsilylethoxymethyl)indazol-4-yl]-6,8-dihydro-5H-pyrido[3,4-d]pyrimidin-4-yl]piperazine-1-carboxylate (2.30 g, 3.49 mmol) in DCM (20 mL) was added m-CPBA (601 mg, 3.49 mmol) at 0° C. The reaction mixture was stirred at 0° C. for 1 hour under N$_2$ atmosphere. The reaction mixture was quenched by addition Na$_2$S$_2$O$_3$ (10 mL) at 0° C., and then diluted with water (100 mL) and the aqueous layer extracted with DCM (200 mL). The combined organics were washed with brine (200 mL), dried over Na$_2$SO$_4$, filtered and concentrated under reduced pressure. The residue was purified by column chromatography using 1→10% MeOH/DCM as eluent to give benzyl 4-[2-methylsulfinyl-7-[5-methyl-1-(2-trimethylsilyl ethoxymethyl)indazol-4-yl]-6,8-dihydro-5H-pyrido[3,4-d]pyrimidin-4-yl]piperazine-1-carboxylate (2.00 g, 2.84 mmol, 81.4% yield). ES+APCI MS m/z 676.3 [M+H]$^+$.

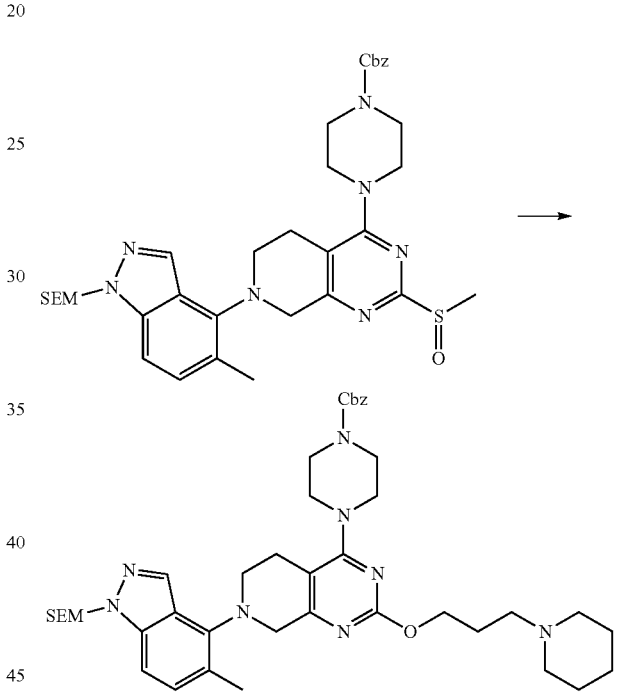

Step C: benzyl 4-[7-[5-methyl-1-(2-trimethylsilylethoxymethyl)indazol-4-yl]-2-[3-(1-piperidyl)propoxy]-6,8-dihydro-5H-pyrido[3,4-d]pyrimidin-4-yl]piperazine-1-carboxylate: To a mixture of benzyl 4-[2-methylsulfinyl-7-[5-methyl-1-(2-trimethylsilylethoxymethyl)indazol-4-yl]-6,8-dihydro-5H-pyrido[3,4-d]pyrimidin-4-yl]piperazine-1-carboxylate (500 mg, 739 umol) and 3-(1-piperidyl)propan-1-ol (211 mg, 1.48 mmol) in THF (10 mL) was added t-BuONa (213 mg, 2.22 mmol) portion wise and the mixture stirred at 20° C. for 1 hour under N$_2$ atmosphere. The mixture was cooled to 0° C. and HCl (2M) was added until the pH ~7. The mixture was filtered and filtrate was concentrated in vacuo. The residue was purified by reversed phase flash using water 5→95% 0.5% TFA/water/acetonitrile as eluent to give benzyl 4-[7-[5-methyl-1-(2-trimethylsilylethoxymethyl)indazol-4-yl]-2-[3-(1-piperidyl) propoxy]-6,8-dihydro-5H-pyrido[3,4-d]pyrimidin-4-yl] piperazine-1-carboxylate (300 mg, 385. umol, 52.1% yield). ES+APCI MS m/z 755.4 [M+H]$^+$.

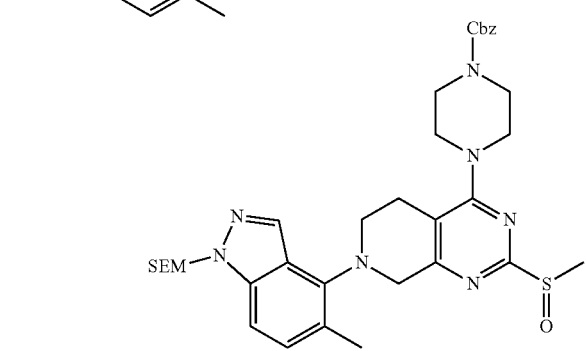

473

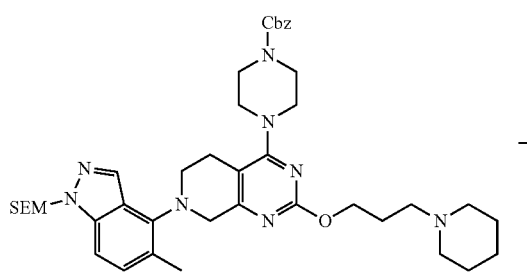

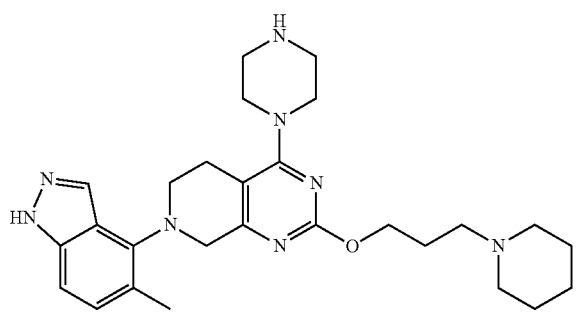

Step D: 7-(5-methyl-1H-indazol-4-yl)-4-(piperazin-1-yl)-2-(3-(piperidin-1-yl)propoxy)-5,6,7,8-tetrahydropyrido[3,4-d]pyrimidine To a solution of benzyl 4-[7-[5-methyl-1-(2-trimethylsilylethoxymethyl) indazol-4-yl]-2-[3-(1-piperidyl)propoxy]-6,8-dihydro-5H-pyrido[3,4-d]pyrimidin-4-yl]piperazine-1-carboxylate (300 mg, 397 umol) in MeOH (20 mL) was added HCl/MeOH (4 M, 1.99 mL) and Pd(OH)$_2$ (200 mg, 10% purity) under N$_2$. The suspension was degassed under vacuum and purged with H$_2$ several times. The mixture was stirred under H$_2$ (15 psi) at 25° C. for 1 hour. The reaction mixture was filtered and the filtrate was concentrated to give 7-(5-methyl-1H-indazol-4-yl)-4-(piperazin-1-yl)-2-(3-(piperidin-1-yl)propoxy)-5,6,7,8-tetrahydropyrido[3,4-d]pyrimidine (250 mg, 360 umol, 90.7% yield).

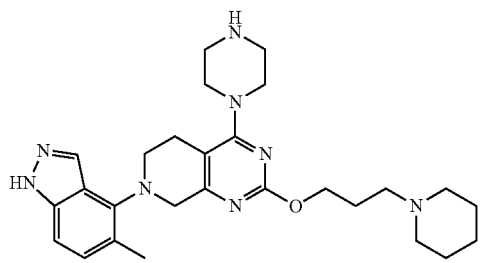

474

-continued

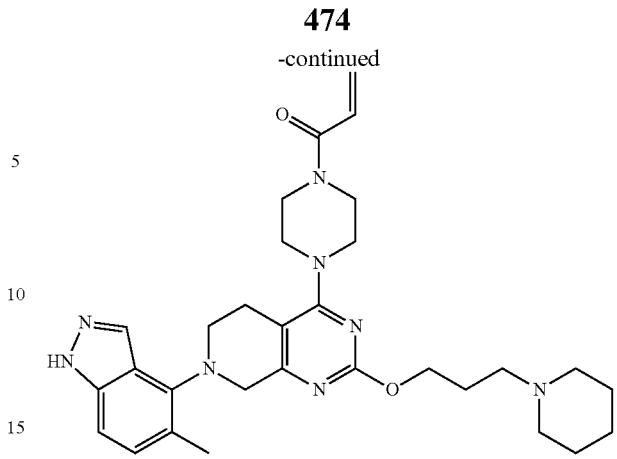

Step E: 1-[4-[7-(5-methyl-1H-indazol-4-yl)-2-[3-(1-piperidyl)propoxy]-6,8-dihydro-5H-pyrido[3,4-d]pyrimidin-4-yl]piperazin-1-yl]prop-2-en-1-one: To a mixture of 7-(5-methyl-1H-indazol-4-yl)-4-(piperazin-1-yl)-2-(3-(piperidin-1-yl)propoxy)-5,6,7,8-tetrahydropyrido[3,4-d]pyrimidine (250 mg, 360 umol, 2HCl) and DIEA (465 mg, 3.60 mmol, 629 uL) in DCM (8.00 mL) was added a solution of prop-2-enoyl prop-2-enoate (36.3 mg, 288 umol) in DCM (2.00 mL) at −40° C. under nitrogen atmosphere and the reaction stirred for 1 hour. The reaction mixture was quenched by addition NaHCO$_3$ (500 uL) at −40° C., and then diluted with water (10 mL) and the aqueous layer extracted with DCM (10 ml). The organics were dried over Na$_2$SO$_4$, filtered and concentrated under reduced pressure. The residue was purified by column chromatography (SiO$_2$, DCM/MeOH 1/0 to 5/1) and further purified by prep-HPLC (column: Phenomenex Synergi C18 150*25*10 um; mobile phase: [water (0.225% Formic Acid)-ACN]; B %: 8%-28%, 10 min) to give 1-[4-[7-(5-methyl-1H-indazol-4-yl)-2-[3-(1-piperidyl)propoxy]-6,8-dihydro-5H-pyrido[3,4-d]pyrimidin-4-yl]piperazin-1-yl]prop-2-en-1-one (16.0 mg, 29.1 umol, 8.07% yield). ES+APCI MS m/z 545.3 [M+H]$^+$.

Example 161

1-[4-[7-(5-methyl-1H-indazol-4-yl)-2-[(1-methylpyrrolidin-3-yl)methoxy]-6,8-dihydro-5H-pyrido[3,4-d]pyrimidin-4-yl]piperazin-1-yl]prop-2-en-1-one

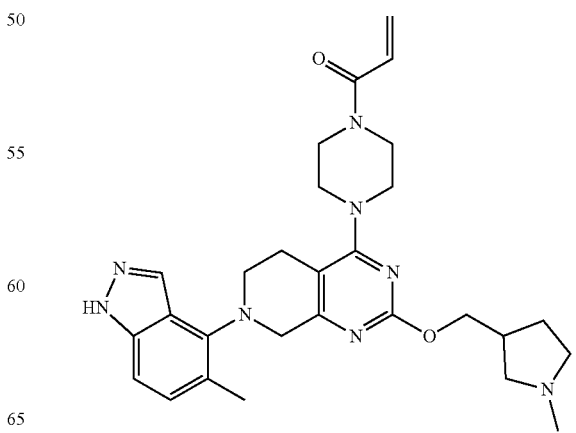

1-[4-[7-(5-methyl-1H-indazol-4-yl)-2-[(1-methylpyrrolidin-3-yl)methoxy]-6,8-dihydro-5H-pyrido[3,4-d]pyrimidin-4-yl]piperazin-1-yl]prop-2-en-1-one was prepared following Example 160 substituting (1-methylpyrrolidin-3-yl)methanol for 3-(1-piperidyl)propan-1-ol in Step C. ES+APCI MS m/z 517.4 [M+H]+.

Example 162

1-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]piperazin-1-yl]prop-2-en-1-one were stirred at 15° C. for 0.5 hour. The reaction mixture was filtered and the filtrate was concentrated under vacuum. The residue was purified by column chromatography over Al₂O₃ (Petroleum Ether/EthylAcetate 10/1 to 0/1) to give benzyl 4-[2-[(1R)-2-(dimethylamino)-1-methyl-ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate (280 mg, 352 umol). ¹H NMR (400 MHz, chloroform-d) δ=8.08 (s, 1H), 7.46-7.39 (m, 5H), 7.38-7.33 (m, 2H), 5.76 (s, 2H), 5.43-5.33 (m, 1H), 5.24 (s, 2H), 4.35 (s, 2H), 3.72-3.67 (m, 4H), 3.64-3.56 (m, 4H), 3.55-3.47 (m, 4H), 2.87-2.80 (m, 2H), 2.74 (dd, J=6.8, 12.8 Hz, 1H), 2.49 (s, 3H), 2.47-2.40 (m, 1H), 2.36 (s, 6H), 1.42 (d, J=6.4 Hz, 3H), 0.98-0.92 (m, 2H), 0.00 (s, 9H).

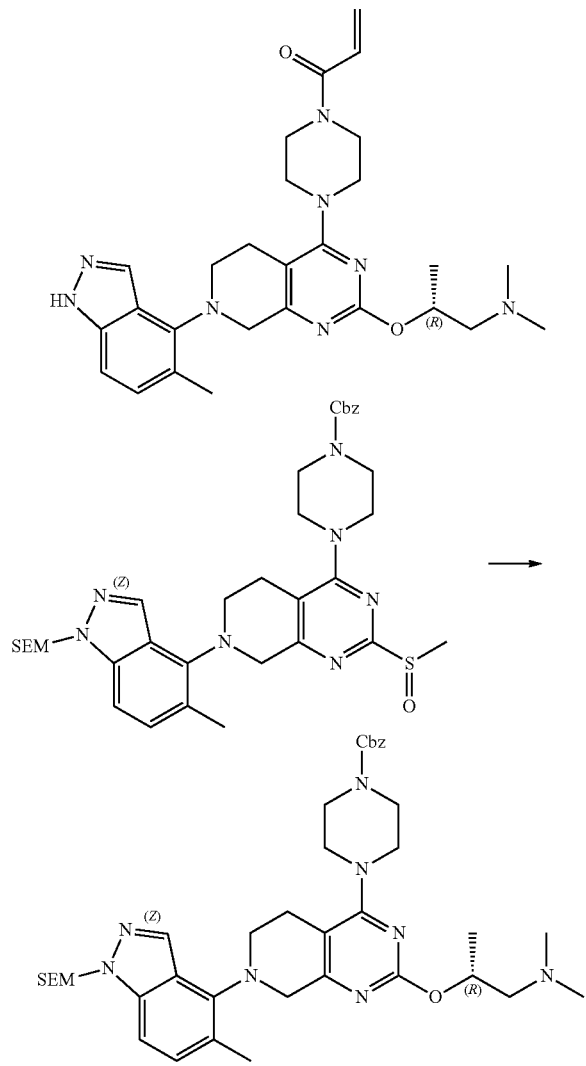

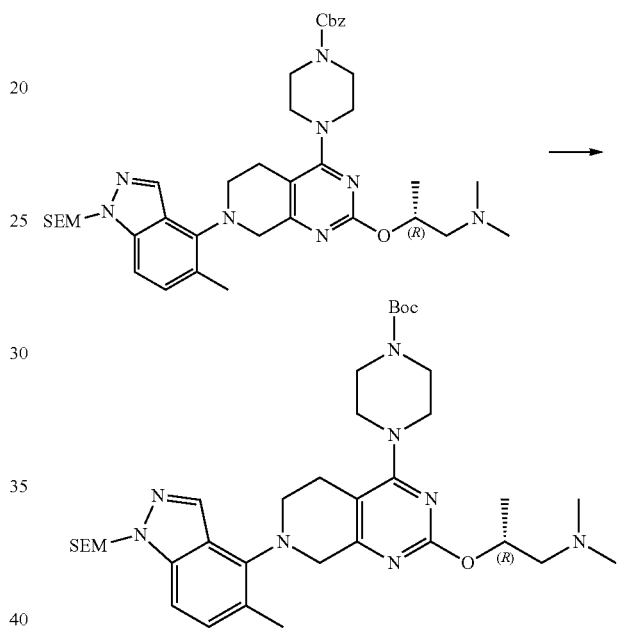

Step A: benzyl 4-[2-[(1R)-2-(dimethylamino)-1-methyl-ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate: A mixture of (2R)-1-(dimethylamino)propan-2-ol (183 mg, 1.78 mmol) (8.00 mL), benzyl 4-[2-methylsulfinyl-7-[5-methyl-1-(2-trimethylsilylethoxymethyl)indazol-4-yl]-6,8-dihydro-5H-pyrido[3,4-d]pyrimidin-4-yl]piperazine-1-carboxylate (400 mg, 592 umol) and NaOtBu (114 mg, 1.18 mmol) in toluene Step B: tert-butyl 4-[2-[(1R)-2-(dimethylamino)-1-methyl-ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate: To a solution of benzyl 4-[2-[(1R)-2-(dimethylamino)-1-methyl-ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate (200 mg, 280 umol) and (Boc)₂O (122 mg, 559 umol, 129 uL) in MeOH (6.00 mL) was added 10% Pd/C (80 mg) under N₂. The suspension was degassed under vacuum and purged with H₂ several times. The mixture was stirred under H₂ (15 psi) at 25° C. for 1 hour and 35° C. for 1 hour. Upon completion, the mixture was filtered and the filtrate concentrated under vacuum to give mixture of tert-butyl 4-[2-[(1R)-2-(dimethylamino)-1-methyl-ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate and (2R)—N,N-dimethyl-2-[[7-[5-methyl-1-(2-trimethylsilylethoxymethyl)indazol-4-yl]-4-piperazin-1-yl-6,8-dihydro-5H-pyrido[3,4-d]pyrimidin-2-yl]oxy]propan-1-amine as a mixture (110 mg). ES+APCI MS m/z 681.3 [M+H]+.

477

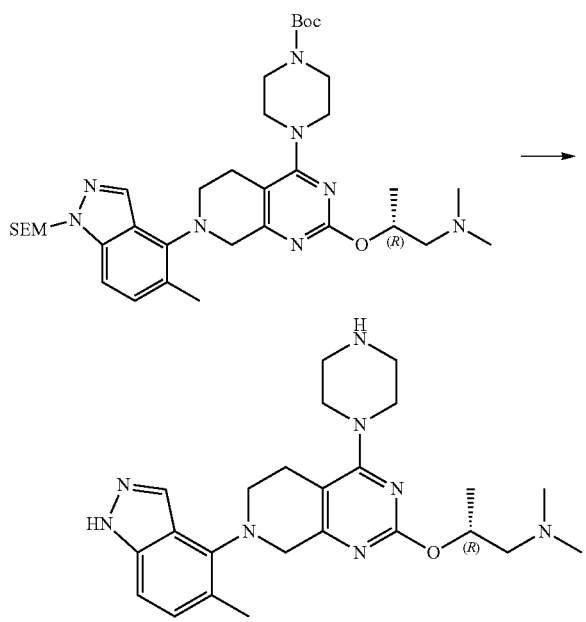

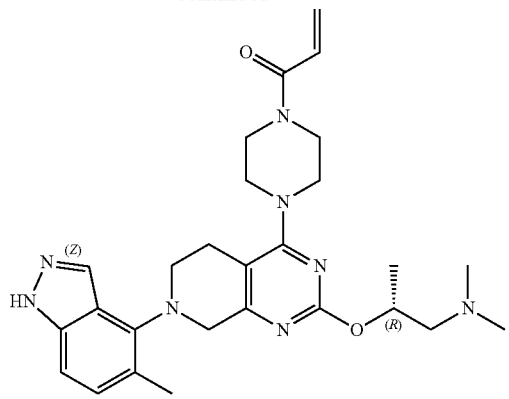

Step C: (2R)—N,N-dimethyl-2-[[7-(5-methyl-1H-indazol-4-yl)-4-piperazin-1-yl-6,8-dihydro-5H-pyrido[3,4-d]pyrimidin-2-yl]oxy]propan-1-amine: (2R)—N,N-dimethyl-2-[[7-(5-methyl-1H-indazol-4-yl)-4-piperazin-1-yl-6,8-dihydro-5H-pyrido[3,4-d]pyrimidin-2-yl]oxy]propan-1-amine (TFA) and [4-[2-[(1R)-2-(dimethylamino)-1-methyl-ethoxy]-4-piperazin-1-yl-6,8-dihydro-5H-pyrido[3,4-d]pyrimidin-7-yl]-5-methyl-indazol-1-yl]methanol. A solution of 110 mg mixture of tert-butyl 4-[2-[(1R)-2-(dimethyl-amino)-1-methyl-ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate and (2R)—N,N-dimethyl-2-[[7-[5-methyl-1-(2-trimethylsilylethoxymethyl)indazol-4-yl]-4-piperazin-1-yl-6,8-dihydro-5H-pyrido[3,4-d]pyrimidin-2-yl]oxy]propan-1-amine in TFA (3.08 g, 27.0 mmol) was stirred at 30° C. for 1 hour. Upon completion, the mixture was concentrated under vacuum to give 260 mg mixture of (2R)—N,N-dimethyl-2-[[7-(5-methyl-1H-indazol-4-yl)-4-piperazin-1-yl-6,8-dihydro-5H-pyrido[3,4-d]pyrimidin-2-yl]oxy]propan-1-amine and [4-[2-[(1R)-2-(dimethylamino)-1-methyl-ethoxy]-4-piperazin-1-yl-6,8-dihydro-5H-pyrido[3,4-d]pyrimidin-7-yl]-5-methyl-indazol-1-yl]methanol. ES+APCI MS m/z 451.3 [M+H]+.

478

-continued

Step D: 1-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]piperazin-1-yl]prop-2-en-1-one: To a solution of 260 mg mixture of (2R)—N,N-dimethyl-2-[[7-(5-methyl-1H-indazol-4-yl)-4-piperazin-1-yl-6,8-dihydro-5H-pyrido[3,4-d]pyrimidin-2-yl]oxy]propan-1-amine and [4-[2-[(1R)-2-(dimethylamino)-1-methyl-ethoxy]-4-piperazin-1-yl-6,8-dihydro-5H-pyrido[3,4-d]pyrimidin-7-yl]-5-methyl-indazol-1-yl]methanol in DCM (1.00 mL) cooled to −50° C. was added DIEA (594 mg, 4.59 mmol) followed by prop-2-enoyl prop-2-enoate (18.0 mg, 143 umol) dropwise and the mixture was stirred at between −50° C. to −40° C. for 30 minutes. Upon completion, the mixture was concentrated under vacuum to give 100 mg mixture of 1-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]piperazin-1-yl]prop-2-en-1-one and 1-[4-[2-[(1R)-2-(dimethylamino)-1-methyl-ethoxy]-7-[1-(hydroxymethyl)-5-methyl-indazol-4-yl]-6,8-dihydro-5H-pyrido[3,4-d]pyrimidin-4-yl]piperazin-1-yl]prop-2-en-1-one. ES+APCI MS m/z 505.4 [M+H]+.

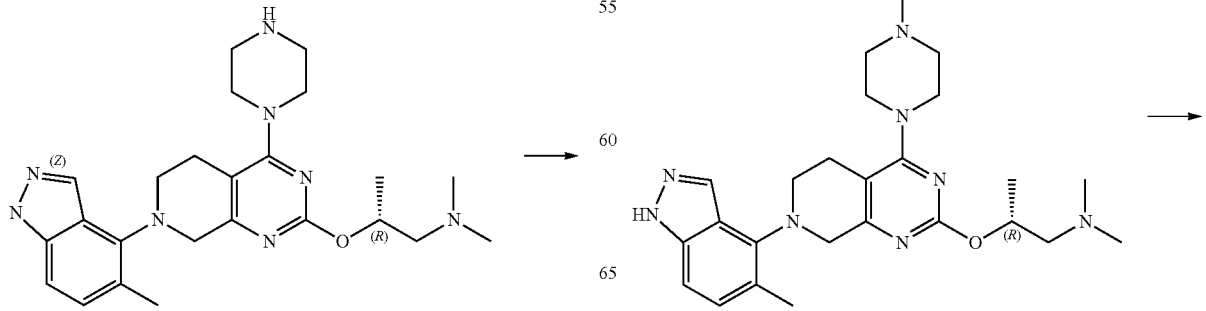

-continued

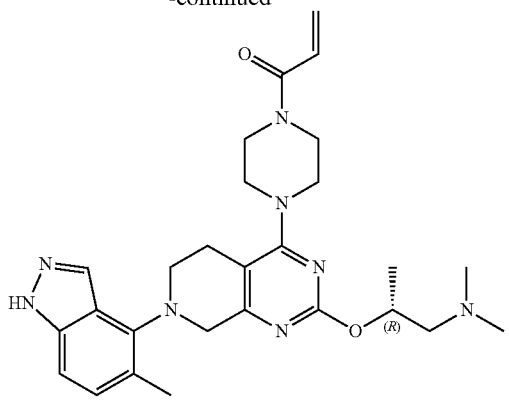

Step E: 1-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]piperazin-1-yl]prop-2-en-1-one: A mixture of 100 mg of 1-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]piperazin-1-yl]prop-2-en-1-one and 1-[4-[2-[(1R)-2-(dimethylamino)-1-methyl-ethoxy]-7-[1-(hydroxymethyl)-5-methyl-indazol-4-yl]-6,8-dihydro-5H-pyrido[3,4-d]pyrimidin-4-yl]piperazin-1-yl]prop-2-en-1-one in THF (22 mL) and water (550 uL) was added NaOH (44.8 mg, 1.12 mmol) and the mixture stirred at 10° C. for 3 hours. Upon completion, the mixture was concentrated under vacuum. The residue was diluted with water (1 mL) and extracted with DCM (3×5 mL). The combined organics were dried over Na$_2$SO$_4$ and concentrated under vacuum. The residue was purified by prep-HPLC (column: Phenomenex Synergi C18 150*25*10 um; mobile phase: [water (0.225% Formic Acid)-ACN]; B %: 10%-40%,12 min) to give 1-[4-[2-[(1R)-2-(dimethylamino)-1-methyl-ethoxy]-7-(5-methyl-1H-indazol-4-yl)-6,8-dihydro-5H-pyrido[3,4-d]pyrimidin-4-yl]piperazin-1-yl]prop-2-en-1-one (16.2 mg, 29.2 umol, 99.0% purity, Formic Acid Salt) as a off-white solid. ES+APCI MS m/z 505.2 [M+H]$^+$.

Example 163

1-(4-(2-(2-(diethylamino)ethoxy)-7-(5-methyl-1H-indazol-4-yl)-5,6,7,8-tetrahydropyrido[3,4-d]pyrimidin-4-yl)piperazin-1-yl)prop-2-en-1-one

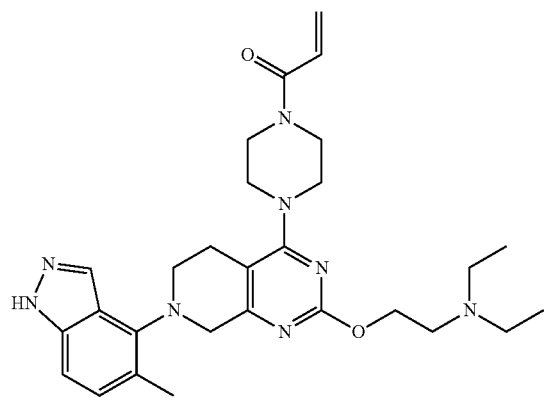

-continued

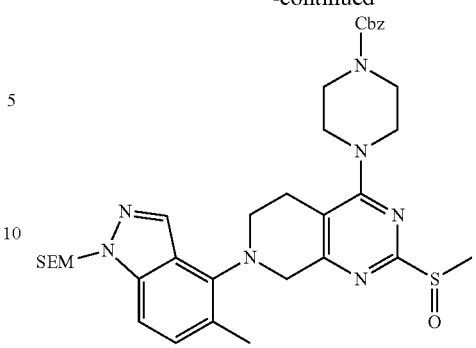

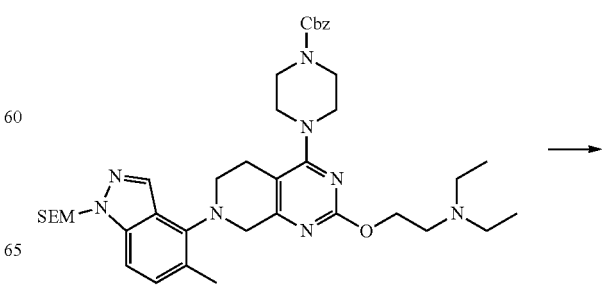

Step A: benzyl 4-[2-[2-(diethylamino)ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate: To a mixture of benzyl 4-[2-methylsulfinyl-7-[5-methyl-1-(2-trimethylsilylethoxymethyl)indazol-4-yl]-6,8-dihydro-5H-pyrido[3,4-d]pyrimidin-4-yl]piperazine-1-carboxylate (500 mg, 739 umol) and 2-(diethylamino)ethanol (173 mg, 1.48 mmol, 197 uL) in THF (10 mL) was added t-BuONa (213 mg, 2.22 mmol), and the mixture stirred at 20° C. for 1 hour under N$_2$ atmosphere. The mixture was cooled to 0° C. and HCl (2 M) was added until pH ~7. The mixture was filtered and the filtrate was concentrated in vacuo. The residue was purified by column chromatography using 0410% MeOH/DCM as eluent to give impure material which was further purified by reversed phase chromatography to give benzyl 4-[2-[2-(diethylamino)ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate (220 mg, 295 umol, 39.9% yield). ES+APCI MS m/z 729.3 [M+H]$^+$.

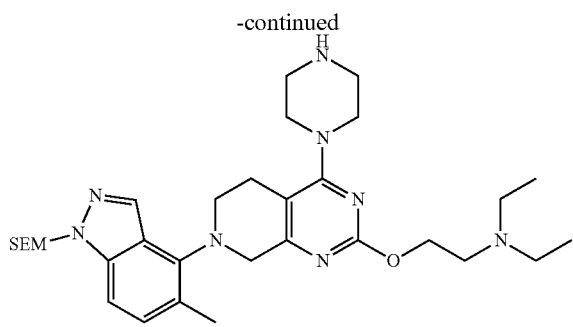

Step B: N,N-diethyl-2-[[7-[5-methyl-1-(2-trimethylsilylethoxymethyl)indazol-4-yl]-4-piperazin-1-yl-6,8-dihydro-5H-pyrido[3,4-d]pyrimidin-2-yl]oxy]ethanamine: To a solution of benzyl 4-[2-[2-(diethylamino)ethoxy]-7-[5-methyl-1-(2-trimethylsilylethoxymethyl)indazol-4-yl]-6,8-dihydro-5H-pyrido[3,4-d]pyrimidin-4-yl]piperazine-1-carboxylate (120 mg, 164 umol) in MeOH (10 mL) was added Pd(OH)$_2$ (99.4 mg, 10% purity) and HCl/MeOH (4 M, 823.05 uL) under N$_2$. The suspension was degassed under vacuum and purged with H$_2$ several times. The mixture was stirred under H$_2$ (15 psi) at 25° C. for 1 hour. The mixture was concentrated in vacuo to give N,N-diethyl-2-[[7-[5-methyl-1-(2-trimethylsilylethoxymethyl)indazol-4-yl]-4-piperazin-1-yl-6,8-dihydro-5H-pyrido[3,4-d]pyrimidin-2-yl]oxy]ethanamine (105 mg, 157.24 umol). ES+APCI MS m/z 595.4 [M+H]$^+$.

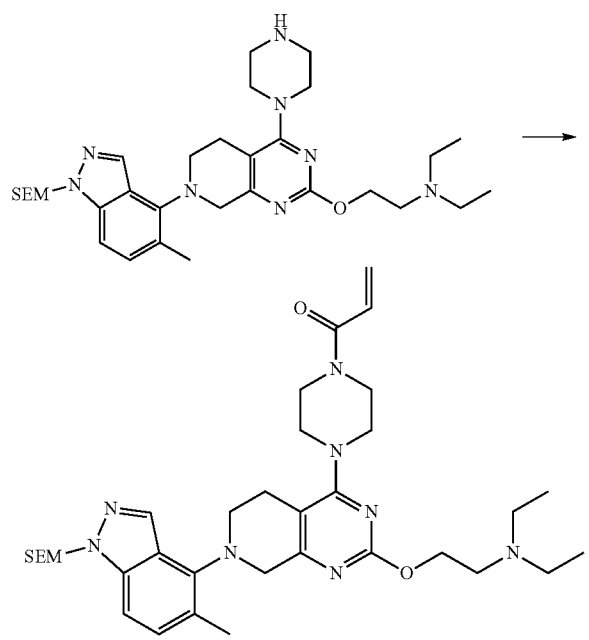

Step C: 1-[4-[2-[2-(diethylamino)ethoxy]-7-[5-methyl-1-(2-trimethylsilylethoxymethyl)indazol-4-yl]-6,8-dihydro-5H-pyrido[3,4-d]pyrimidin-4-yl]piperazin-1-yl]prop-2-en-1-one: To a mixture of N,N-diethyl-2-[[7-[5-methyl-1-(2-trimethylsilyl ethoxymethyl)indazol-4-yl]-4-piperazin-1-yl-6,8-dihydro-5H-pyrido[3,4-d]pyrimidin-2-yl]oxy]ethanamine (105 mg, 158 umol, 2 HCl) and DIEA (204 mg, 1.58 mmol, 276 uL) in DCM (8 mL) at −40° C. was added a solution of prop-2-enoyl prop-2-enoate (15.9 mg, 126.4 umol) in DCM (2 mL) under nitrogen atmosphere and the reaction stirred for 1 hour. The reaction mixture was quenched by addition NaHCO$_3$ (500 uL) at −40° C., and then diluted with water (10 mL). The aqueous layer was extracted with DCM (10 ml), dried over Na$_2$SO$_4$, filtered and concentrated under reduced pressure. The residue was purified by column chromatography using 0→20% MeOH/DCM as eluent to give 1-[4-[2-[2-(diethylamino)ethoxy]-7-[5-methyl-1-(2-trimethylsilylethoxymethyl)indazol-4-yl]-6,8-dihydro-5H-pyrido[3,4-d]pyrimidin-4-yl]piperazin-1-yl]prop-2-en-1-one (60.0 mg, 71.2 umol, 45.0% yield). ES+APCI MS m/z 649.3 [M+H]$^+$.

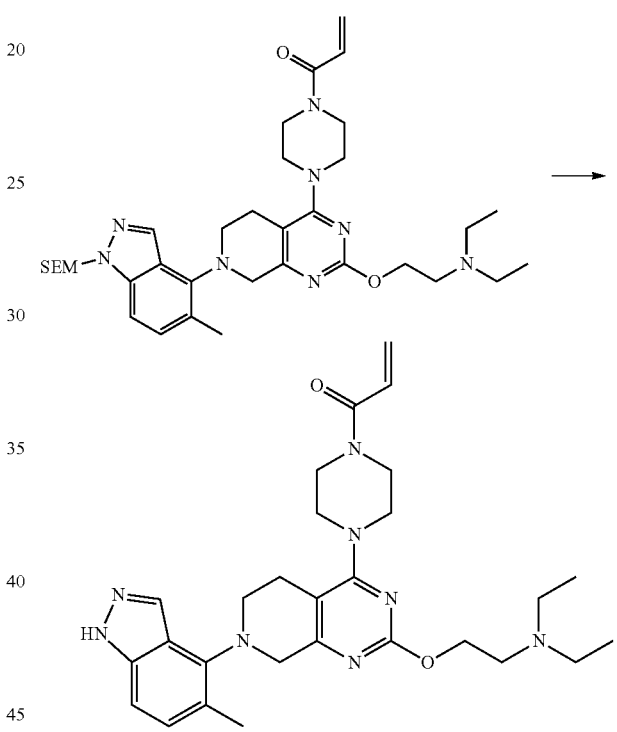

Step D: 1-[4-[2-[2-(diethylamino)ethoxy]-7-(5-methyl-1H-indazol-4-yl)-6,8-dihydro-5H-pyrido[3,4-d]pyrimidin-4-yl]piperazin-1-yl]prop-2-en-1-one: To a solution of 1-[4-[2-[2-(diethylamino)ethoxy]-7-[5-methyl-1-(2-trimethylsilylethoxymethyl)indazol-4-yl]-6,8-dihydro-5H-pyrido[3,4-d]pyrimidin-4-yl]piperazin-1-yl]prop-2-en-1-one (50 mg, 77.0 umol) in DCM (500 uL) was added TFA (175 mg, 1.54 mmol, 114 uL). The mixture was stirred at 15° C. for 16 hours. The reaction mixture was concentrated under vacuum and the residue purified by prep-HPLC (column: Phenomenex Gemini C18 250*50 mm*10 um; mobile phase: [water (0.05% ammonia hydroxide v/v)-ACN]; B %: 32%-62%, 12 min) to give 1-[4-[2-[2-(diethylamino)ethoxy]-7-(5-methyl-1H-indazol-4-yl)-6,8-dihydro-5H-pyrido[3,4-d]pyrimidin-4-yl]piperazin-1-yl]prop-2-en-1-one (16.0 mg, 30.2 umol, 39.2% yield). ES+APCI MS m/z 519.3 [M+H]$^+$.

Example 164

1-(4-(7-(5-methyl-1H-indazol-4-yl)-2-(2-(piperidin-1-yl)ethoxy)-5,6,7,8-tetrahydropyrido[3,4-d]pyrimidin-4-yl)piperazin-1-yl)ethanone

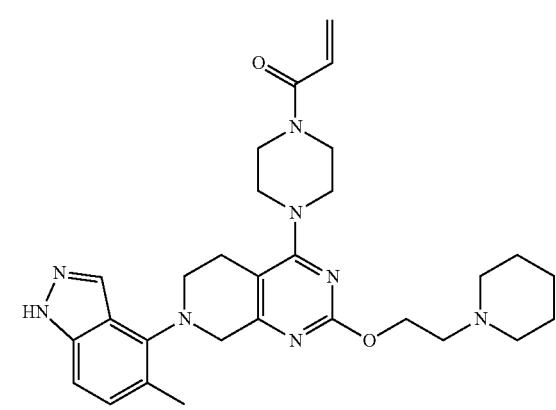

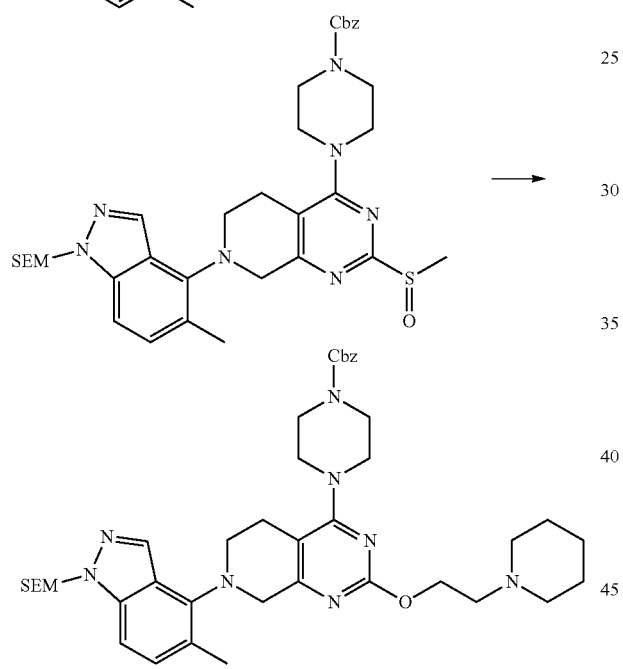

Step A: benzyl 4-[7-[5-methyl-1-(2-trimethylsilylethoxymethyl)indazol-4-yl]-2-[2-(1-piperidyl)ethoxy]-6,8-dihydro-5H-pyrido[3,4-d]pyrimidin-4-yl]piperazine-1-carboxylate: To a solution of benzyl 4-[2-methylsulfinyl-7-[5-methyl-1-(2-trimethylsilylethoxymethyl)indazol-4-yl]-6,8-dihydro-5H-pyrido[3,4-d]pyrimidin-4-yl]piperazine-1-carboxylate (500 mg, 739 umol) and 2-(1-piperidyl)ethanol (191 mg, 1.48 mmol, 197 uL) in toluene (20 mL) was added t-BuONa (213 mg, 2.22 mmol). The mixture was stirred at 20° C. for 1 hour under $N_2$ atmosphere. The mixture was cooled to 0° C. and HCl (2 M) was added until pH ~7. The mixture was filtered and the filtrate concentrated in vacuo. The residue was purified by column chromatography using 0→10% MeOH/DCM as eluent to give benzyl 4-[7-[5-methyl-1-(2-trimethylsilylethoxy methyl)indazol-4-yl]-2-[2-(1-piperidyl)ethoxy]-6,8-dihydro-5H-pyrido[3,4-d]pyrimidin-4-yl]piperazine-1-carboxylate (300 mg, 404 umol, 54.7% yield). ES+APCI MS m/z 741.4 [M+H]+.

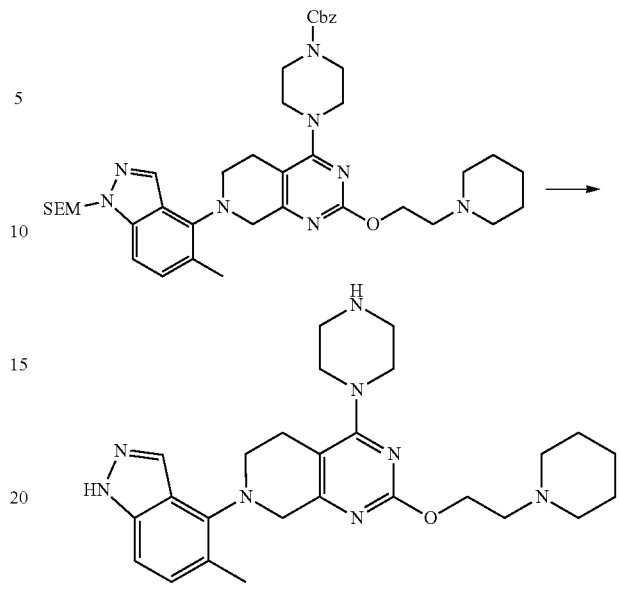

Step B: 7-(5-methyl-1H-indazol-4-yl)-4-piperazin-1-yl-2-[2-(1-piperidyl)ethoxy]-6,8-dihydro-5H-pyrido[3,4-d]pyrimidine A solution of benzyl 4-[7-[5-methyl-1-(2-trimethylsilylethoxymethyl) indazol-4-yl]-2-[2-(1-piperidyl)ethoxy]-6,8-dihydro-5H-pyrido[3,4-d]pyrimidin-4-yl]piperazine-1-carboxylate (250 mg, 337 umol) in TFA (10 mL) was stirred at 80° C. for 1 hour. The reaction mixture was concentrated under vacuum to give 7-(5-methyl-1H-indazol-4-yl)-4-piperazin-1-yl-2-[2-(1-piperidyl)ethoxy]-6,8-dihydro-5H-pyrido[3,4-d]pyrimidine (200 mg, 283 umol, 84.1% yield). ES+APCI MS m/z 477.3 [M+H]+.

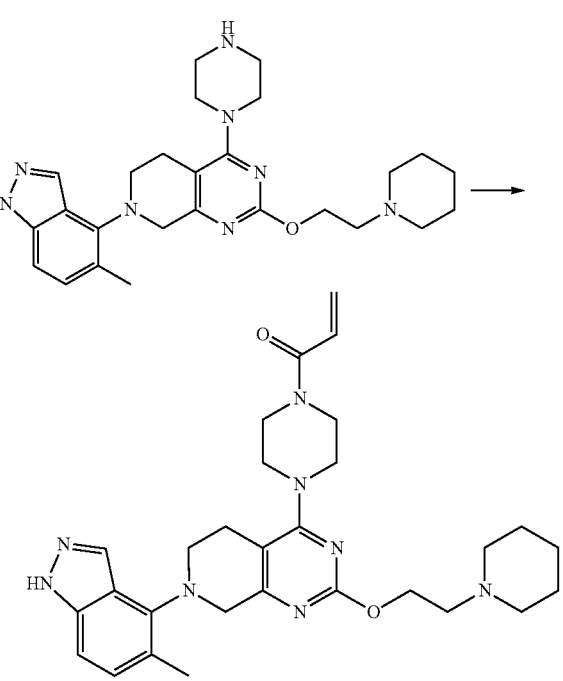

Step C: 1-[4-[7-(5-methyl-1H-indazol-4-yl)-2-[2-(1-piperidyl)ethoxy]-6,8-dihydro-5H-pyrido[3,4-d]pyrimidin-4-yl]piperazin-1-yl]prop-2-en-1-one: To a mixture of 7-(5-methyl-1H-indazol-4-yl)-4-piperazin-1-yl-2-[2-(1-piperidyl)ethoxy]-6,8-dihydro-5H-pyrido[3,4-d]pyrimidine (200 mg, 283 umol, 2TFA) and DIEA (366 mg, 2.84 mmol, 495 uL) in DCM (8 mL) at −40° C. was added a solution of prop-2-enoyl prop-2-enoate (28.6 mg, 227 umol) DCM (2 mL) under nitrogen atmosphere and the reaction stirred for 1 hour. The reaction mixture was quenched by addition NaHCO₃ (500 uL) at −40° C., and then diluted with water (10 mL) and DCM (10 ml). The separated organic layer was dried over Na₂SO₄, filtered and concentrated under reduced pressure. The residue was purified by prep-HPLC (column: Phenomenex Gemini C18 250*50 mm*10 um; mobile phase: [water (0.05% ammonia hydroxide v/v)-ACN]; B %: 30%-60%, 12 min). 1-[4-[7-(5-methyl-1H-indazol-4-yl)-2-[2-(1-piperidyl)ethoxy]-6,8-dihydro-5H-pyrido[3,4-d]pyrimidin-4-yl]piperazin-1-yl]prop-2-en-1-one (6.00 mg, 11.1 umol, 3.94% yield, 99.0% purity). ES+APCI MS m/z 531.4 [M+H]⁺.

Example 165

1-[4-[7-(2-fluoro-3-hydroxy-1-naphthyl)-2-(3-morpholinopropoxy)-6,8-dihydro-5H-pyrido[3,4-d]pyrimidin-4-yl]piperazin-1-yl]prop-2-en-1-one

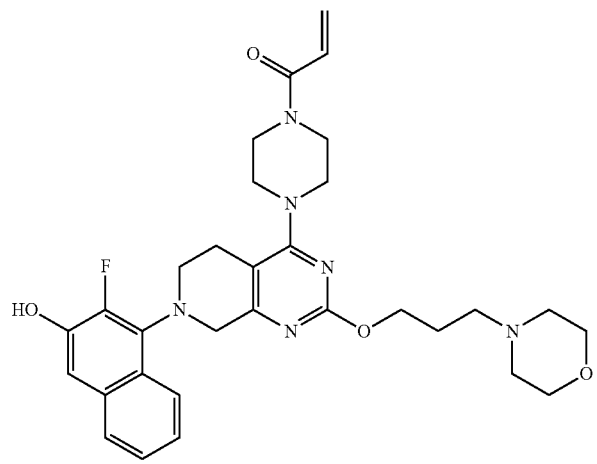

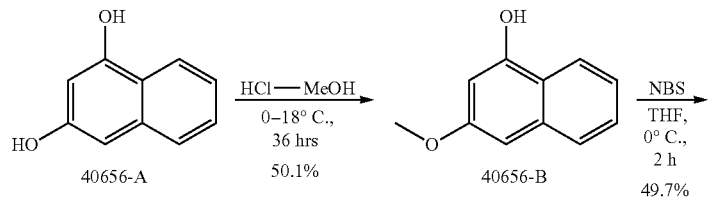

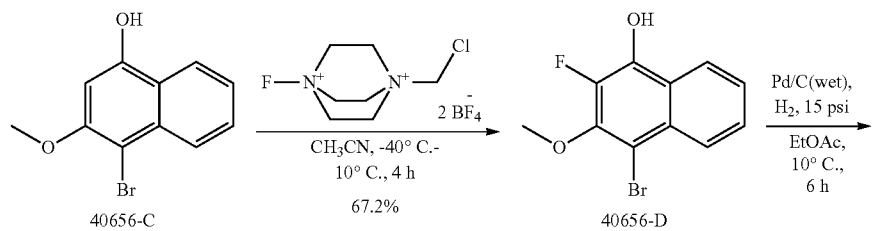

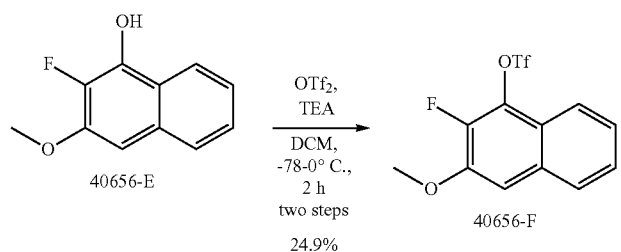

-continued
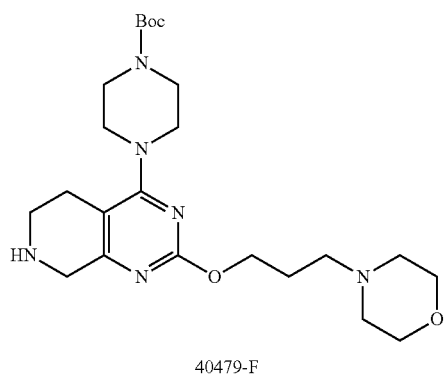 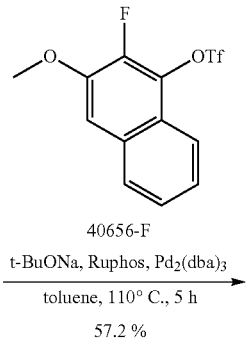
40479-F
40656-F
t-BuONa, Ruphos, Pd$_2$(dba)$_3$
toluene, 110° C., 5 h
57.2 %
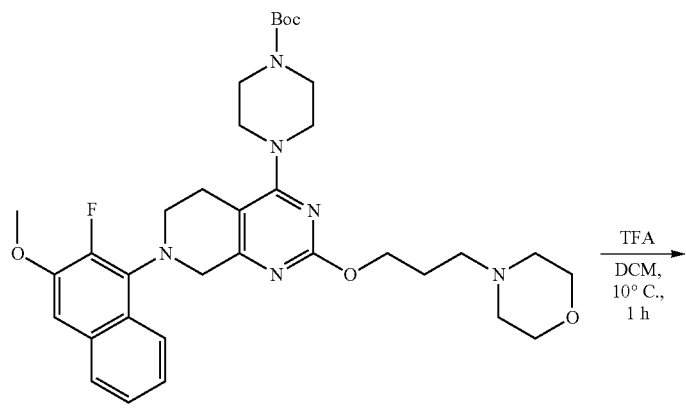
40656-1
TFA
DCM,
10° C.,
1 h
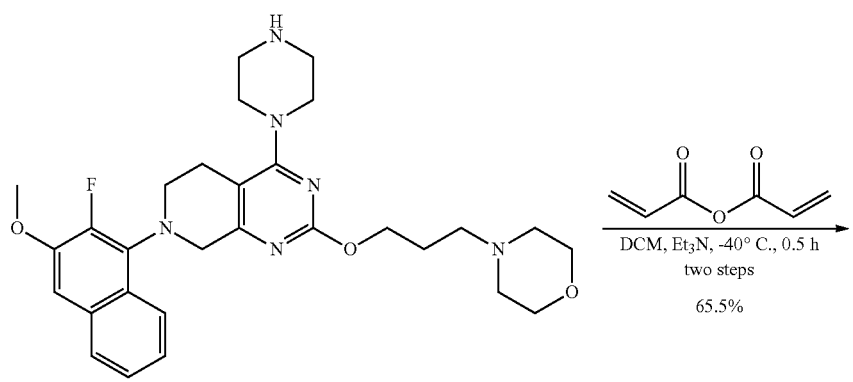
40656-2
DCM, Et$_3$N, -40° C., 0.5 h
two steps
65.5%

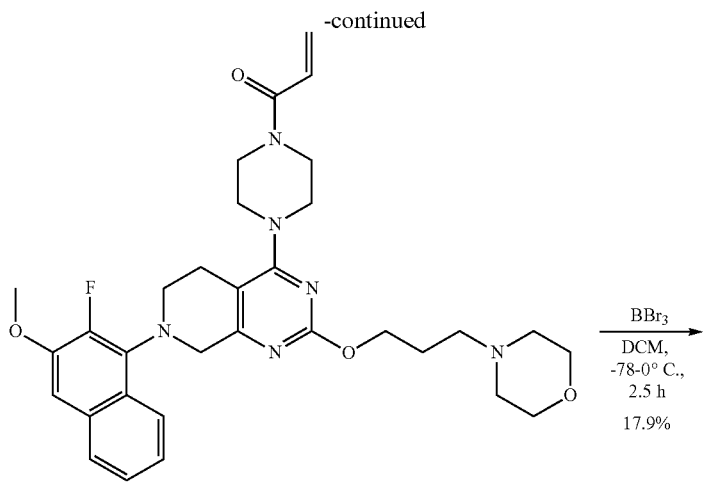

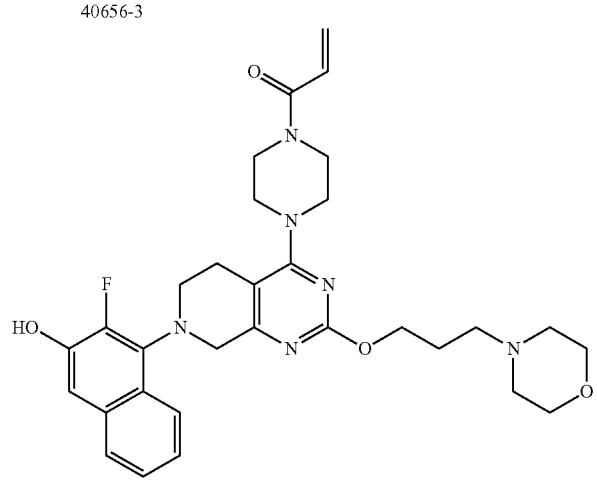

Step A: 3-methoxynaphthalen-1-ol

To a solution of naphthalene-1,3-diol (20 g, 125 mmol) in MeOH (150 mL) was added HCl/MeOH (4 M, 250 mL) at 0° C. The mixture was warmed up to 18° C. and stirred for 36 hours. The mixture was concentrated under vacuum. The residue was purified by column chromatography over silica gel (petroleum ether/ethyl acetate 100/1 to 1/1). The desired fractions were collected and concentrated under vacuum to give 3-methoxynaphthalen-1-ol (11 g, 62.5 mmol, 50.1% yield, 99% purity) as a light yellow solid. ES+APCI MS m/z 175.1 [M+H]$^+$.

Step B: 4-bromo-3-methoxy-naphthalen-1-ol

To a solution of 3-methoxynaphthalen-1-ol (0.50 g, 2.87 mmol) in THF (10 mL) was added a solution of NBS (562 mg, 3.16 mmol) in THF (3.00 mL) at 0° C. After stirring at 0° C. for 2 hours, the mixture was concentrated under vacuum, diluted with H$_2$O (5 mL), extracted with dichloromethane (3×10 mL). The combined extracts were washed with saturated sodium chloride (1×20 mL), dried over Na$_2$SO$_4$, filtered and concentrated under vacuum. The residue was purified by column chromatography (SiO$_2$, petroleum ether/ether acetate=3/1) to give 4-bromo-3-methoxy-naphthalen-1-ol (0.43 g, 1.43 mmol, 49.7% yield) as a yellow solid. ES+APCI MS m/z 253 [M+H]$^+$.

Step C: 4-bromo-2-fluoro-3-methoxy-naphthalen-1-ol

To a solution of 4-bromo-3-methoxy-naphthalen-1-ol (4.00 g, 15.8 mmol) in acetonitrile (20 mL) was added a solution of 1-(chloromethyl)-4-fluoro-1,4-diazoniabicyclo[2.2.2]octane; ditetrafluoroborate (6.72 g, 19.0 mmol) in acetonitrile (20 mL) at −40° C. After stirring at −40° C. for 1 hour and 10° C. for 3 hours, the mixture was concentrated under vacuum. The residue was purified by column chromatography (SiO$_2$, petroleum ether/ether acetate=3/1) to give 4-bromo-2-fluoro-3-methoxy-naphthalen-1-ol (4.00 g, 10.6 mmol, 67.2% yield) as a yellow solid. ES+APCI MS m/z 271.0 [M+H]$^+$.

Step D: 2-fluoro-3-methoxy-naphthalen-1-ol

A mixture of 4-bromo-2-fluoro-3-methoxy-naphthalen-1-ol (2.00 g, 7.38 mmol) and 10% Pd/C (0.01 g) in ethyl acetate (20 mL) was stirred at 10° C. for 1 hour under H$_2$ at 15 psi. The mixture was filtered and concentrated under vacuum to give 2-fluoro-3-methoxy-naphthalen-1-ol (1.60 g, crude) as yellow oil and used into next step without further purification. ES+APCI MS m/z 193.0 [M+H]$^+$.

Step E: (2-fluoro-3-methoxy-1-naphthyl) trifluoromethanesulfonate

To a solution of 2-fluoro-3-methoxy-naphthalen-1-ol (1.60 g, crude) and TEA (1.85 g, 18.3 mmol, 2.55 mL) in dichloromethane (30 mL) was added trifluoromethylsulfonyl trifluoromethanesulfonate (2.35 g, 8.33 mmol, 1.37 mL) at −78° C. for 1 hour. The mixture was quenched with saturated ammonium chloride (30 mL), extracted with ethyl acetate (3×20 mL), washed with saturated sodium chloride (1×50 mL), dried over $Na_2SO_4$, filtered and concentrated under vacuum. The residue was purified by column chromatography ($SiO_2$, petroleum ether/ether acetate=3/1) to give (2-fluoro-3-methoxy-1-naphthyl) trifluoromethanesulfonate (1.10 g, 2.07 mmol, two steps 24.9% yield) as a yellow solid. ES+APCI MS m/z 324.9 $[M+H]^+$.

Step F: tert-butyl 4-[7-(2-fluoro-3-methoxy-1-naphthyl)-2-(3-morpholinopropoxy)-6,8-dihydro-5H-pyrido[3,4-d]pyrimidin-4-yl]piperazine-1-carboxylate A mixture of tert-butyl 4-[2-(3-morpholinopropoxy)-5,6,7,8-tetrahydropyrido[3,4-d]pyrimidin-4-yl]piperazine-1-carboxylate (0.40 g, 865 umol), (2-fluoro-3-methoxy-1-naphthyl) trifluoromethanesulfonate (561 mg, 1.73 mmol), RuPhos (80.7 mg, 173 umol), $Pd_2(dba)_3$ (79.2 mg, 86.5 umol) and t-BuONa (249 mg, 2.59 mmol) in toluene (10 mL) was stirred at 110° C. for 5 hours under $N_2$. The mixture was diluted with water (10 mL), extracted with ether acetate (3×10 mL). The extracts were washed with saturated sodium chloride (1×20 mL), dried over $Na_2SO_4$, filtered and concentrated under vacuum. The residue was purified by reversed phase flash chromatography [water (0.1% Formic Acid)/acetonitrile] to give tert-butyl 4-[7-(2-fluoro-3-methoxy-1-naphthyl)-2-(3-morpholinopropoxy)-6,8-dihydro-5H-pyrido[3,4-d]pyrimidin-4-yl]piperazine-1-carboxylate (0.35 g, 495 umol, 57.2% yield) as a yellow oil. ES+APCI MS m/z 637.1 $[M+H]^+$.

Step G: 4-[3-[[7-(2-fluoro-3-methoxy-1-naphthyl)-4-piperazin-1-yl-6,8-dihydro-5H-pyrido[3,4-d]pyrimidin-2-yl]oxy]propyl]morpholine A mixture of tert-butyl 4-[7-(2-fluoro-3-methoxy-1-naphthyl)-2-(3-morpholinopropoxy)-6,8-dihydro-5H-pyrido[3,4-d]pyrimidin-4-yl]piperazine-1-carboxylate (0.40 g, 628. umol) and TFA (1.07 g, 9.42 mmol, 698 uL) in dichloromethane (0.70 mL) was stirred at 10° C. for 1 hour. The mixture was concentrated under vacuum to give 4-[3-[[7-(2-fluoro-3-methoxy-1-naphthyl)-4-piperazin-1-yl-6,8-dihydro-5H-pyrido[3,4-d]pyrimidin-2-yl]oxy]propyl]morpholine (0.41 g, crude, TFA) as a yellow oil and used into next step without further purification. ES+APCI MS m/z 537.5 $[M+H]^+$.

Step H: 1-[4-[7-(2-fluoro-3-methoxy-1-naphthyl)-2-(3-morpholinopropoxy)-6,8-dihydro-5H-pyrido[3,4-d]pyrimidin-4-yl]piperazin-1-yl]prop-2-en-1-one To a solution of 4-[3-[[7-(2-fluoro-3-methoxy-1-naphthyl)-4-piperazin-1-yl-6,8-dihydro-5H-pyrido[3,4-d]pyrimidin-2-yl]oxy]propyl]morpholine (0.41 g, crude, TFA salt) and TEA (635 mg, 6.27 mmol, 873 uL) in dichloromethane (5.0 mL) was added prop-2-enoyl prop-2-enoate (79.1 mg, 627 umol) at −40° C. After stirring at −40° C. for 0.5 h, the mixture was quenched with methanol (0.10 mL) and concentrated under vacuum. The residue was purified by column chromatography ($Al_2O_3$, dichloromethane/methanol=10/1) to give 1-[4-[7-(2-fluoro-3-methoxy-1-naphthyl)-2-(3-morpholinopropoxy)-6,8-dihydro-5H-pyrido[3,4-d]pyrimidin-4-yl]piperazin-1-yl]prop-2-en-1-one (0.25 g, 411 umol, two steps 65.5% yield) as a yellow oil. ES+APCI MS m/z 591.0 $[M+H]^+$.

Step I: 1-[4-[7-(2-fluoro-3-hydroxy-1-naphthyl)-2-(3-morpholinopropoxy)-6,8-dihydro-5H-pyrido[3,4-d]pyrimidin-4-yl]piperazin-1-yl]prop-2-en-1-one To a solution of 1-[4-[7-(2-fluoro-3-methoxy-1-naphthyl)-2-(3-morpholinopropoxy)-6,8-dihydro-5H-pyrido[3,4-d]pyrimidin-4-yl]piperazin-1-yl]prop-2-en-1-one (0.20 g, 339 umol) in dichloromethane (4.00 mL) was added $BBr_3$ (424 mg, 1.69 mmol, 163 uL) at −78° C. for 0.5 hour and stirred at 0° C. for 2 hours. The mixture was quenched with saturated sodium bicarbonate (5 mL) at −78° C. and stirred at 0° C. for 0.5 h. The mixture was extracted with dichloromethane (3×10 mL) and concentrated under vacuum. The residue was purified by prep-HPLC (column: Phenomenex Synergi C18 150*25*10 um; mobile phase: [water (0.225% Formic Acid)-ACN]; B %: 13%-45%,7 min) to give 1-[4-[7-(2-fluoro-3-hydroxy-1-naphthyl)-2-(3-morpholinopropoxy)-6,8-dihydro-5H-pyrido[3,4-d]pyrimidin-4-yl]piperazin-1-yl]prop-2-en-1-one (35.2 mg, 60.8 umol, 17.9% yield, 99.4% purity) as a yellow solid. ES+APCI MS m/z 577.0 $[M+H]^+$.

Example 166

1-[4-[7-(6-hydroxy-2-methyl-1,3-benzothiazol-4-yl)-2-(3-morpholinopropoxy)-6,8-dihydro-5H-pyrido[3,4-d]pyrimidin-4-yl]piperazin-1-yl]prop-2-en-1-one

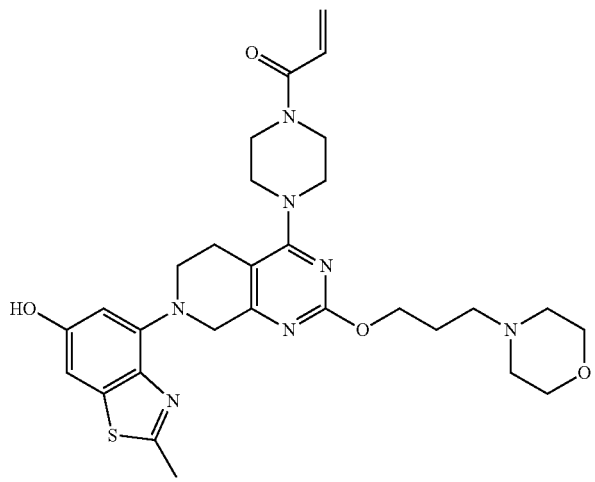

493  494
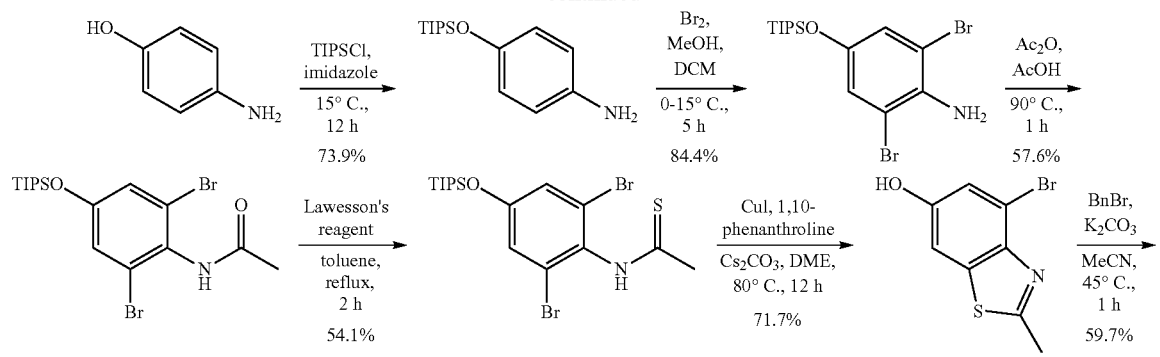
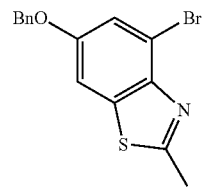
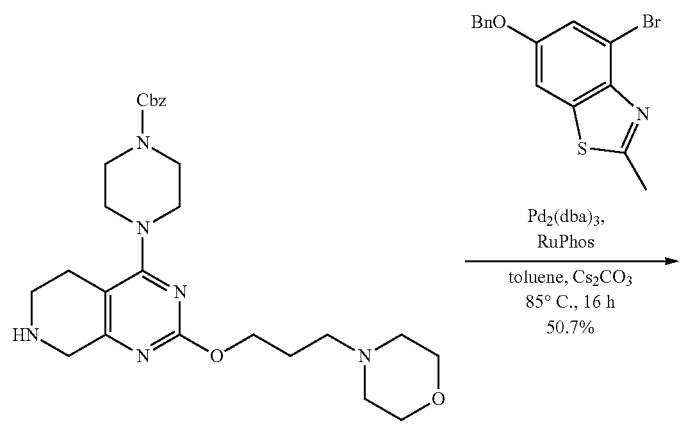
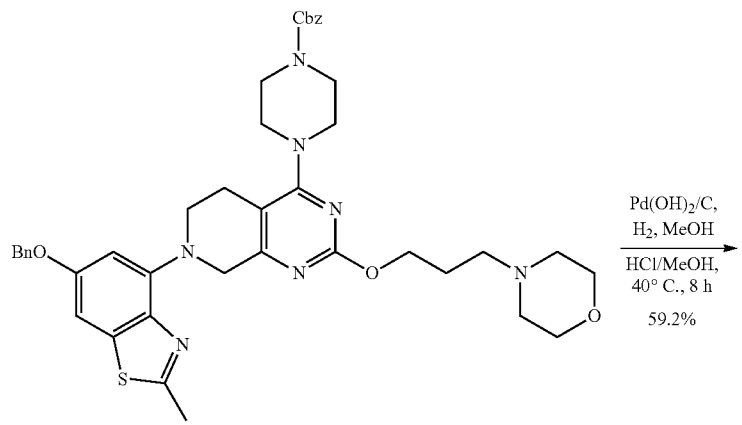

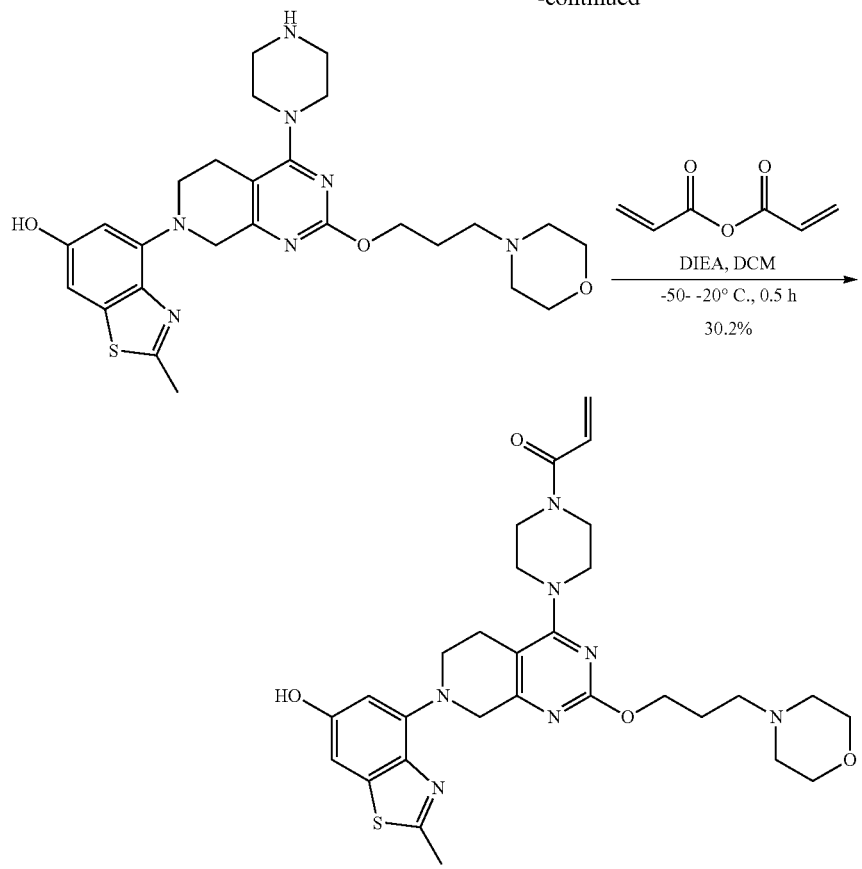

Step A: 4-triisopropylsilyloxyaniline

To a solution of 4-aminophenol (5.00 g, 45.8 mmol, 7.14 mL) in DCM (50.0 mL) was added imidazole (4.06 g, 59.6 mmol). TIPSCl (13.3 g, 68.7 mmol, 14.7 mL) was added to the mixture dropwise. The mixture was stirred at 15° C. for 12 hours. Upon completion, the reaction mixture was filtered and the filtrate was concentrated under vacuum. The residue was purified by automated flash chromatography system (PE/EA 100/1 to 3/1) to give 4-triisopropylsilyloxyaniline (9.46 g, 33.9 mmol, 73.9% yield, 95.0% purity) as a black oil.

$^1$H NMR (400 MHz, chloroform-d) δ=6.74-6.71 (m, 1H), 6.71-6.69 (m, 1H), 6.60-6.58 (m, 1H), 6.58-6.55 (m, 1H), 3.66-2.98 (m, 2H), 1.28-1.16 (m, 3H), 1.11-1.06 (m, 18H)

Step B: 2,6-dibromo-4-triisopropylsilyloxy-aniline

To a solution of 4-triisopropylsilyloxyaniline (7.30 g, 27.5 mmol) in DCM (73.0 mL) and MeOH (73.0 mL) was added Br$_2$ (11.0 g, 68.8 mmol, 3.55 mL) in DCM (5 mL) dropwise at 0° C. The mixture was stirred at 15° C. for 5 hours. Upon completion, the mixture was diluted with sodium sulfite solution (60 mL) and extracted with DCM (3×200 mL). The organic layers were dried over Na$_2$SO$_4$ and concentrated under vacuum. The residue was purified by column chromatography (PE/EA 50/1 to 1/1) to give 2,6-dibromo-4-triisopropylsilyloxy-aniline (10.8 g, 23.2 mmol, 84.4% yield, 90.8% purity) as a brown oil. ES+APCI MS m/z 423.9[M+H]$^+$.

Step C: N-(2,6-dibromo-4-triisopropylsilyloxy-phenyl)acetamide

To a solution of 2,6-dibromo-4-triisopropylsilyloxy-aniline (10.4 g, 24.6 mmol) and CH$_3$COOH (52 mL) was added acetic anhydride (10.9 g, 107 mmol, 10 mL). The reaction mixture was stirred at 90° C. for 1 hour. Upon completion, water (100 mL) and DCM (200 mL) were added and layers were separated. The aqueous phase was extracted with DCM (100 mL×2). The combined extracts were washed with 5% Na$_2$CO$_3$ (80 mL), washed with brine (100 mL), dried over Na$_2$SO$_4$ and concentrated under vacuum. The residue was purified by column chromatography (PE/EA 50/1 to 1:1) to give N-(2,6-dibromo-4-triisopropylsilyloxy-phenyl)acetamide (7.32 g, 14.2 mmol, 57.6% yield, 90.0% purity) as a brown solid.

$^1$H NMR (400 MHz, chloroform-d) δ=7.16 (s, 1H), 7.11 (s, 2H), 2.21 (s, 3H), 1.28-1.24 (m, 3H), 1.12-1.09 (m, 18H).

Step D: N-(2,6-dibromo-4-triisopropylsilyloxy-phenyl)thioacetamide

To a solution of N-(2,6-dibromo-4-triisopropylsilyloxy-phenyl)acetamide (7.22 g, 15.5 mmol) in toluene (116 mL) was added LAWESSON'S REAGENT (3.14 g, 7.76 mmol). The mixture was heated to 110° C. for 2 hours. Upon completion, the mixture was concentrated under vacuum. The residue was purified by column chromatography (PE/EA 100/1 to 1/1) N-(2,6-dibromo-4-triisopropylsilyloxy-phenyl)thioacetamide (5.41 g, 8.40 mmol, 54.1% yield, 74.7% purity) as a yellow oil. ES+APCI MS m/z 481.9[M+H]$^+$.

Step E: 4-bromo-2-methyl-1,3-benzothiazol-6-ol

CuI (94.2 mg, 494 umol) was added to a solution of N-(2,6-dibromo-4-triisopropylsilyloxy-phenyl)thioacetamide (2.38 g, 4.94 mmol), 1,10-phenanthroline (134 mg, 741 umol) and Cs₂CO₃ (4.83 g, 14.8 mmol) in DME (48.0 mL). Then the reaction mixture was stirred at 80° C. for 12 hours under N₂. Upon completion, the reaction mixture was filtered and the filtrate was concentrated. The residue was purified by column chromatography (PE/EA 50/1 to 0/1) to give 4-bromo-2-methyl-1,3-benzothiazol-6-ol (1.33 g, 3.54 mmol, 71.7% yield, 65.0% purity) as a brown oil.

$^1$H NMR (400 MHz, DMSO-d₆) δ=7.33 (d, J=2.4 Hz, 1H), 7.14 (d, J=2.4 Hz, 1H), 3.40-3.33 (m, 1H), 2.72 (s, 3H).

Step F:
6-benzyloxy-4-bromo-2-methyl-1,3-benzothiazole

To a mixture of 4-bromo-2-methyl-1,3-benzothiazol-6-ol (1.28 g, 5.24 mmol) and K₂CO₃ (2.17 g, 15.72 mmol) in ACN (26.0 mL) was added BnBr (988 mg, 5.76 mmol, 685 uL). The reaction mixture was stirred at 45° C. for 1 hour. Upon completion, the reaction mixture was filtered and the filtrate was concentrated. The residue was purified by column chromatography (PE/EA 200/1 to 10/1) to give 6-benzyloxy-4-bromo-2-methyl-1,3-benzothiazole (1.10 g, 3.13 mmol, 59.7% yield, 95.0% purity) as a light yellow solid. ES+APCI MS m/z 336.2 [M+H]⁺.

Step G: benzyl 4-[7-(6-benzyloxy-2-methyl-1,3-benzothiazol-4-yl)-2-(3-morpholinopropoxy)-6,8-dihydro-5H-pyrido[3,4-d]pyrimidin-4-yl]piperazine-1-carboxylate: Benzyl 4-[2-(3-morpholinopropoxy)-5,6,7,8-tetrahydropyrido[3,4-d]pyrimidin-4-yl]piperazine-1-carboxylate (400 mg, 805 umol), 6-benzyloxy-4-bromo-2-methyl-1,3-benzothiazole (323 mg, 967 umol), RuPhos (75.2 mg, 161 umol), Cs₂CO₃ (787 mg, 2.42 mmol) and Pd₂(dba)₃ (73.8 mg, 80.6 umol) in toluene (16 mL) was stirring at 85° C. for 16 hours under N₂. Upon completion, the reaction mixture was filtered and the filtrate was concentrated. The residue was purified by column chromatography over Al₂O₃(PE/EA 10/1 to 0/1) to give benzyl 4-[7-(6-benzyloxy-2-methyl-1,3-benzothiazol-4-yl)-2-(3-morpholinopropoxy)-6,8-dihydro-5H-pyrido[3,4-d]pyrimidin-4-yl]piperazine-1-carboxylate (340 mg, 408 umol, 50.7% yield, 90.0% purity) as a yellow oil. ES+APCI MS m/z 750.5[M+H]⁺.

Step H: 2-methyl-4-[2-(3-morpholinopropoxy)-4-piperazin-1-yl-6,8-dihydro-5H-pyrido[3,4-d]pyrimidin-7-yl]-1,3-benzothiazol-6-ol To a solution of benzyl 4-[7-(6-benzyloxy-2-methyl-1,3-benzothiazol-4-yl)-2-(3-morpholinopropoxy)-6,8-dihydro-5H-pyrido[3,4-d]pyrimidin-4-yl]piperazine-1-carboxylate (160 mg, 213 umol) in MeOH (4 mL) was added HCl/MeOH (4 M, 533 uL), followed by Pd(OH)₂/C (80 mg, 533 umol) under N₂. The suspension was degassed under vacuum and purged with H₂ several times. The mixture was stirred under H₂ (15 psi) at 40° C. for 8 hours. Upon completion, the reaction mixture was filtered and the filtrate was concentrated to give 2-methyl-4-[2-(3-morpholinopropoxy)-4-piperazin-1-yl-6,8-dihydro-5H-pyrido[3,4-d]pyrimidin-7-yl]-1,3-benzothiazol-6-ol (110 mg, 126 umol, 59.2% yield, 68.7% purity, 2 HCl) as a yellow solid which was used directly in the next step without further purification. ES+APCI MS m/z 526.2[M+H]⁺.

Step I: 1-[4-[7-(6-hydroxy-2-methyl-1,3-benzothiazol-4-yl)-2-(3-morpholinopropoxy)-6,8-dihydro-5H-pyrido[3,4-d]pyrimidin-4-yl]piperazin-1-yl]prop-2-en-1-one: To a solution of 2-methyl-4-[2-(3-morpholinopropoxy)-4-piperazin-1-yl-6,8-dihydro-5H-pyrido[3,4-d]pyrimidin-7-yl]-1,3-benzothiazol-6-ol (110 mg, 184 umol, 2 HCl) and DIEA (143 mg, 1.10 mmol, 193 uL) in DCM (2.00 mL) was added prop-2-enoyl prop-2-enoate (18.5 mg, 147 umol) dropwise at −50° C. The mixture was stirred at −40–−20° C. for 30 minutes. Upon completion, the mixture was quenched by MeOH (0.5 mL) and concentrated under vacuum. The residue was diluted with water (2 mL) and extracted with DCM (3×6 mL). The organic layers were dried over Na₂SO₄ and concentrated under vacuum. The residue was purified by column chromatography over Al₂O₃(DCM/MeOH 20/1 to 10/1), prep-HPLC (column: Gemini 150*25 5 u; mobile phase: [water (0.05% ammonia hydroxide v/v)-ACN]; B %: 21%-51%,12 min) to give 1-[4-[7-(6-hydroxy-2-methyl-1,3-benzothiazol-4-yl)-2-(3-morpholinopropoxy)-6,8-dihydro-5H-pyrido[3,4-d]pyrimidin-4-yl]piperazin-1-yl]prop-2-en-1-one (32.4 mg, 55.4 umol, 30.2% yield, 99.1% purity) as a yellow solid. ES+APCI MS m/z 580.4[M+H]⁺.

Example 167

1-(4-(7-(5-hydroxy-2-methyl-1H-indol-7-yl)-2-(3-morpholinopropoxy)-5,6,7,8-tetrahydropyrido[3,4-d]pyrimidin-4-yl)piperazin-1-yl)prop-2-en-1-one

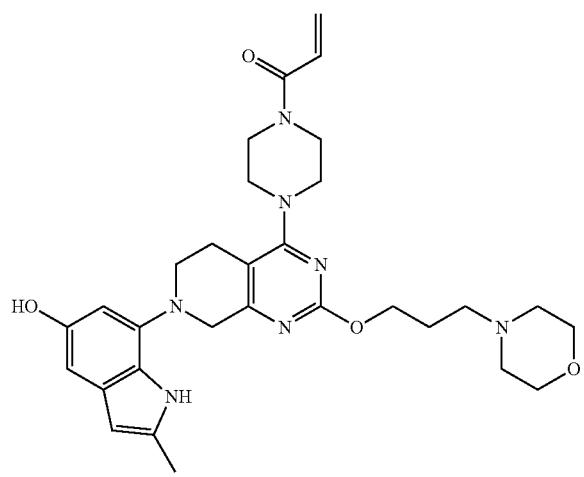

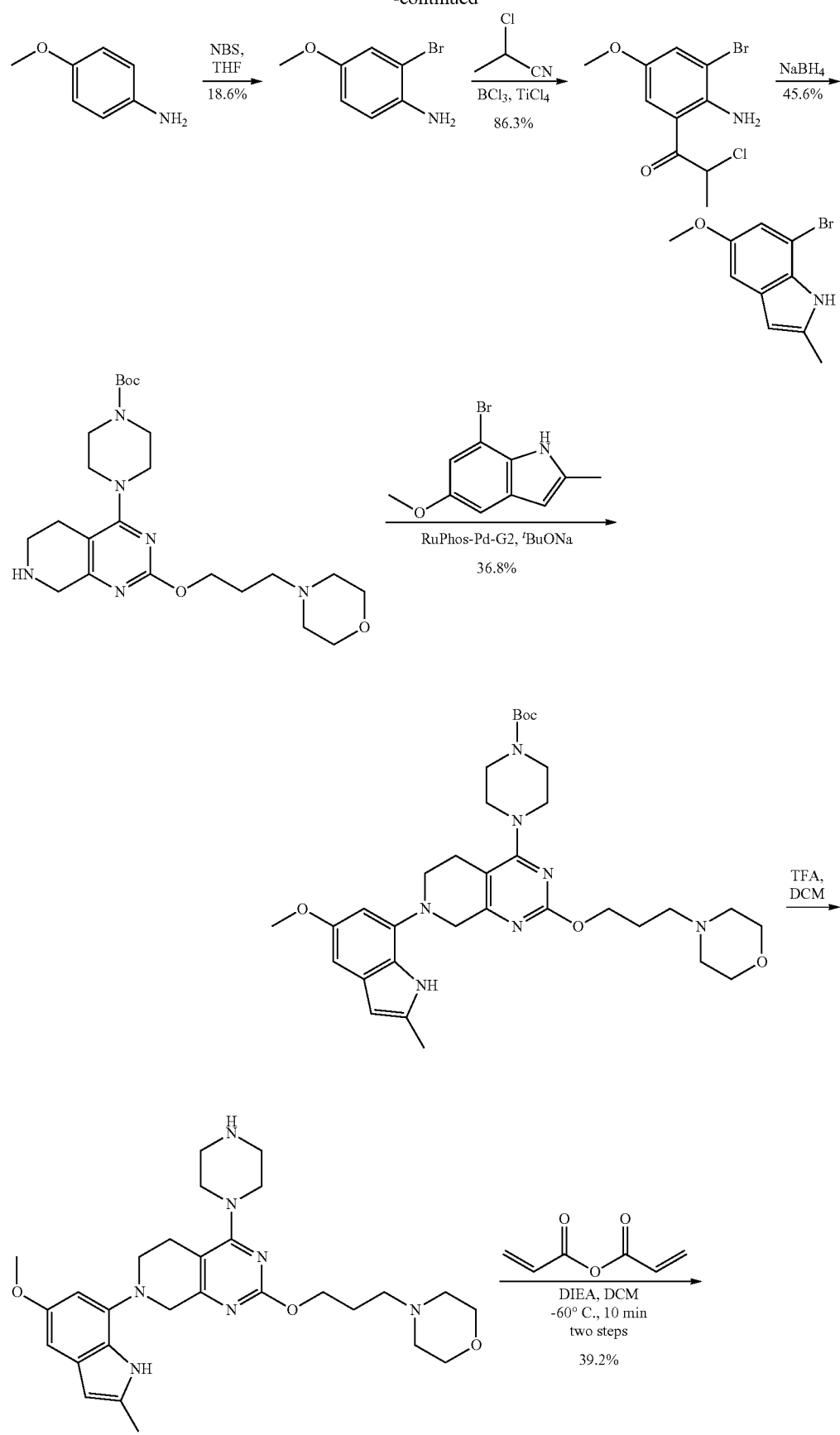

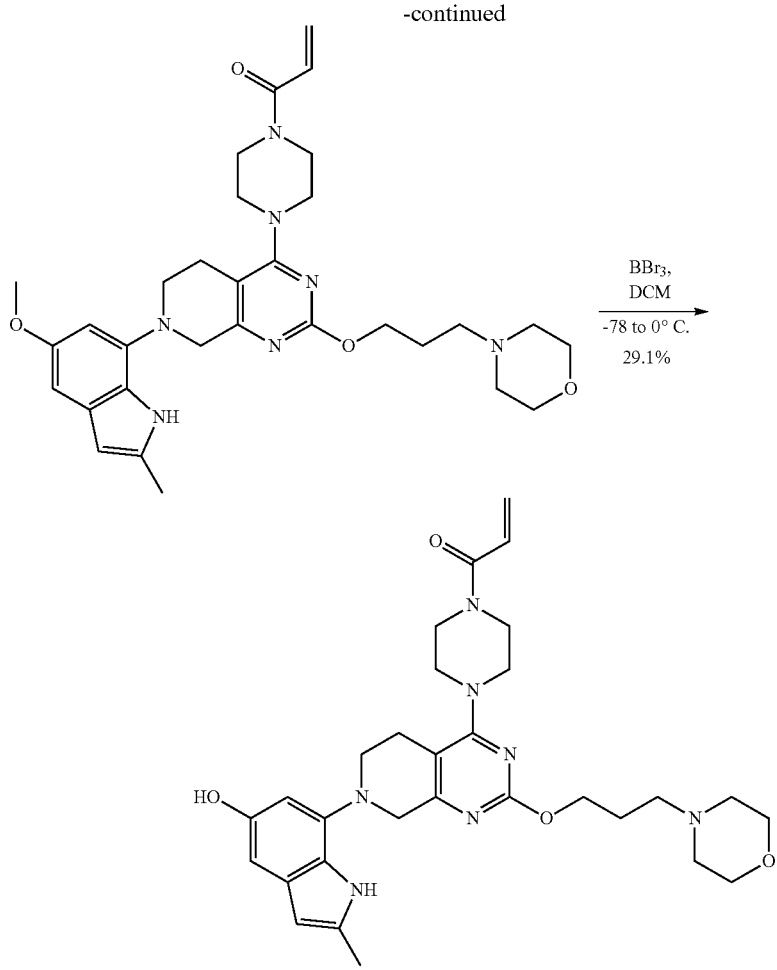

Step A: 2-bromo-4-methoxyaniline

At −10° C., to a solution of 4-methoxyaniline (100 g, 812 mmol) in THF (3 L) was added N-bromosuccinimide (152 g, 853 mmol) in three portions and the mixture was stirred at the same temperature for 30 min. The mixture was concentrated under reduced pressure. The residue was purified by column chromatography. (petroleum ether/ethyl acetate 15/1) to give 2-bromo-4-methoxyaniline as red oil (30.58 g, 18.6% yield). $^1$H NMR (400 MHz, CDCl$_3$) δ=7.01 (d, J=2.4 Hz, 1H), 6.74-6.70 (m, 2H), 3.85-3.74 (m, 2H), 3.73 (s, 3H).

Step B: 1-(2-amino-3-bromo-5-methoxyphenyl)-2-chloropropan-1-one

To a 0° C. solution of 2-bromo-4-methoxy-aniline (15.0 g, 74.2 mmol) in 1,1-dichloroethane (220 mL) was added boron trichloride (1.00 M, 89.1 mL), 2-chloropropanenitrile (9.97 g, 111 mmol) and titanium tetrachloride (16.9 g, 89.1 mmol). The mixture was heated at 85° C. for 24 hours. The mixture was poured into ice and hydrochloric acid (20%, 300 mL) at 0° C., concentrated and the residue was refluxed for 0.5 hour. This mixture was basified at 0° C. with sodium hydroxide (saturated aqueous, 120 mL) until pH 4 was attained and then extracted with ethyl acetate (300 mL×2). The combined organic extracts were washed with brine (200 mL), dried with anhydrous sodium sulfate and concentrated under reduced pressure. The residue was purified by column chromatography (petroleum ether/ethyl acetate/dichloromethane 50/1/1), to give 1-(2-amino-3-bromo-5-methoxyphenyl)-2-chloropropan-1-one as yellow solid (18.7 g, 86.3% yield). $^1$H NMR (400 MHz, CDCl$_3$) δ=7.37 (d, J=2.8 Hz, 1H), 7.32 (d, J=2.8 Hz, 1H), 6.60 (brs, 2H), 5.25 (q, J=6.4 Hz, 1H), 3.80 (s, 3H), 1.74 (d, J=6.4 Hz, 3H).

Step C: 7-bromo-5-methoxy-2-methyl-1H-indole

To a solution of 1-(2-amino-3-bromo-5-methoxy-phenyl)-2-chloro-propan-1-one (18.7 g, 64.1 mmol) in dioxane (500 mL) and H$_2$O (50 mL) was added NaBH$_4$ (2.67 g, 70.5 mmol) and this mixture stirred at 100° C. for 15 hours. The mixture was cooled, diluted with hydrochloric acid (aq., 0.10 M, 100 mL) and extracted with dichloromethane (300 mL×2). The organics were washed with brine (200 mL), dried with anhydrous sodium sulfate and concentrated under reduced pressure. The residue was purified by column chromatography (petroleum ether/ethyl acetate 25/1) to give 7-bromo-5-methoxy-2-methyl-1H-indole as yellow solid (7.01 g, 45.6% yield). $^1$H NMR (400 MHz, CDCl$_3$) δ=7.91 (brs, 1H), 7.03-6.91 (m, 2H), 6.23 (d, J=1.2 Hz, 1H), 3.84 (s, 3H), 2.46 (s, 3H).

Step D: tert-butyl 4-(7-(5-methoxy-2-methyl-1H-indol-7-yl)-2-(3-morpholinopropoxy)-5,6,7,8-tetrahydropyrido[3,4-d]pyrimidin-4-yl)piperazine-1-carboxylate: To a mixture of tert-butyl 4-[2-(3-morpholinopropoxy)-5,6,7,8-tetrahydropyrido[3,4-d]pyrimidin-4-yl]piperazine-1-carboxylate (275 mg, 594 umol) and 7-bromo-5-methoxy-2-methyl-1H-indole (130 mg, 540 umol) in 2-methyl-2-butanol (15.0 mL) was added $^t$BuONa (104 mg, 1.08 mmol) and chloro(2-dicyclohexylphosphino-2',6'-di-$^i$-propoxy-1,1'-biphenyl)[2-(2-aminoethylphenyl)]palladium(II) methyl-t-butyl ether adduct (44.1 mg, 54.0 umol). This mixture stirred at 90° C. for 8 hours under a $N_2$ atmosphere. The mixture was filtered, concentrated under reduced pressure. The residue was purified by prep-TLC (dichloromethane/methanol 10/1), to give tert-butyl 4-(7-(5-methoxy-2-methyl-1H-indol-7-yl)-2-(3-morpholinopropoxy)-5,6,7,8-tetrahydropyrido[3,4-d]pyrimidin-4-yl)piperazine-1-carboxylate as yellow oil (131 mg, 36.8% yield). ES+APCI MS m/z 622.4[M+H]$^+$.

Step E: 4-[3-[[7-(5-methoxy-2-methyl-1H-indol-7-yl)-4-piperazin-1-yl-6,8-dihydro-5H-pyrido[3,4-d]pyrimidin-2-yl]oxy]propyl]morpholine To a 0° C. solution of tert-butyl 4-[7-(5-methoxy-2-methyl-1H-indol-7-yl)-2-(3-morpholinopropoxy)-6,8-dihydro-5H-pyrido[3,4-d]pyrimidin-4-yl]piperazine-1-carboxylate (131 mg, 211 umol) in dichloromethane (10 mL) was added trifluoroacetic acid (2.00 mL) dropwise and the reaction stirred at 15° C. for 3 hours. The mixture was concentrated under reduced pressure, and the residue was used in the next step without further purification. (126 mg crude product). ES+APCI MS m/z 522.4[M+H]$^+$.

Step F: 1-(4-(7-(5-methoxy-2-methyl-1H-indol-7-yl)-2-(3-morpholinopropoxy)-5,6,7,8-tetrahydropyrido[3,4-d]pyrimidin-4-yl)piperazin-1-yl)prop-2-en-1-one: To a −60° C. solution of 4-[3-[[7-(5-methoxy-2-methyl-1H-indol-7-yl)-4-piperazin-1-yl-6,8-dihydro-5H-pyrido[3,4-d]pyrimidin-2-yl]oxy]propyl]morpholine (74 mg, 116 umol, trifluoroacetic acid salt) in dichloromethane (5 mL) was added diisopropylethylamine (45.1 mg, 349 umol, 60.8 uL) and the mixture stirred at the same temperature for 10 min. The mixture was quenched with citric acid (aq., 1.00 mL), extracted with dichloromethane (10 mL×2), washed with brine (15 mL), dried over anhydrous sodium sulfate and concentrated under vacuum. The residue was purified by prep-TLC to give 1-(4-(7-(5-methoxy-2-methyl-1H-indol-7-yl)-2-(3-morpholinopropoxy)-5,6,7,8-tetrahydropyrido[3,4-d]pyrimidin-4-yl)piperazin-1-yl)prop-2-en-1-one as yellow solid (31 mg, 39.2% yield). ES+APCI MS m/z 576.4[M+H]$^+$.

Step G: 1-(4-(7-(5-hydroxy-2-methyl-1H-indol-7-yl)-2-(3-morpholinopropoxy)-5,6,7,8-tetrahydropyrido[3,4-d]pyrimidin-4-yl)piperazin-1-yl)prop-2-en-1-one: To a −78° C. solution of 1-[4-[7-(5-methoxy-2-methyl-1H-indol-7-yl)-2-(3-morpholinopropoxy)-6,8-dihydro-5H-pyrido[3,4-d]pyrimidin-4-yl]piperazin-1-yl]prop-2-en-1-one (26 mg, 45.2 umol) in dichloromethane (5 mL) was added boron tribromide (56.6 mg, 226 umol, 21.8 uL). The reaction was allowed to warm to 0° C. and stirred for 12 hours. The mixture was neutralized with $NaHCO_3$ (aq., 3 mL) and extracted with dichloromethane (5 mL×2), washed with brine (10 mL), dried by anhydrous sodium sulfate, concentrated under vacuum. The residue was purified by prep-HPLC to give 1-(4-(7-(5-hydroxy-2-methyl-1H-indol-7-yl)-2-(3-morpholinopropoxy)-5,6,7,8-tetrahydropyrido[3,4-d]pyrimidin-4-yl)piperazin-1-yl)prop-2-en-1-one as yellow solid (8.16 mg, 29.1% yield, 90.3% purity). ES+APCI MS m/z 562.5[M+H]$^+$.

Example 168

1-(3-(hydroxymethyl)-4-(7-(3-hydroxynaphthalen-1-yl)-2-(3-morpholinopropoxy)-5,6,7,8-tetrahydropyrido[3,4-d]pyrimidin-4-yl)piperazin-1-yl)prop-2-en-1-one

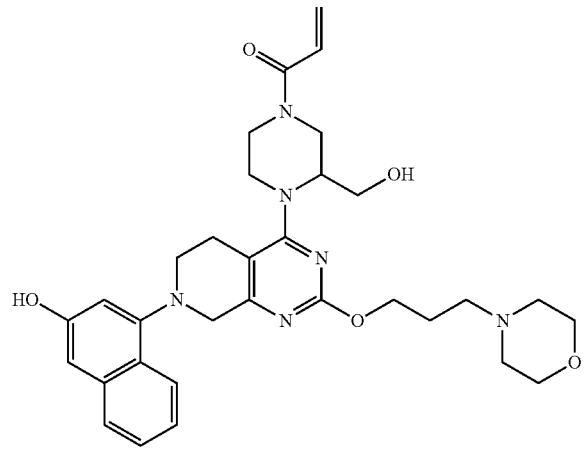

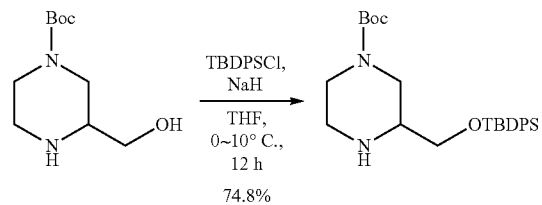

-continued
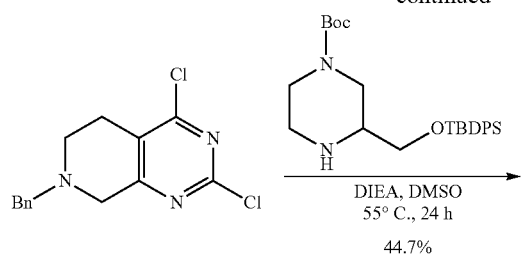
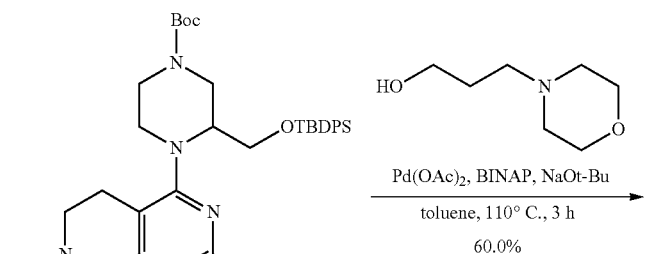
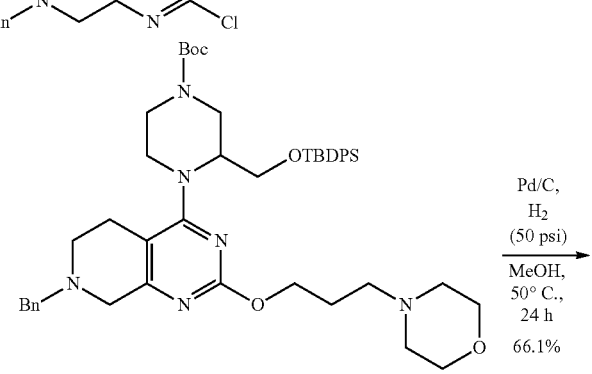
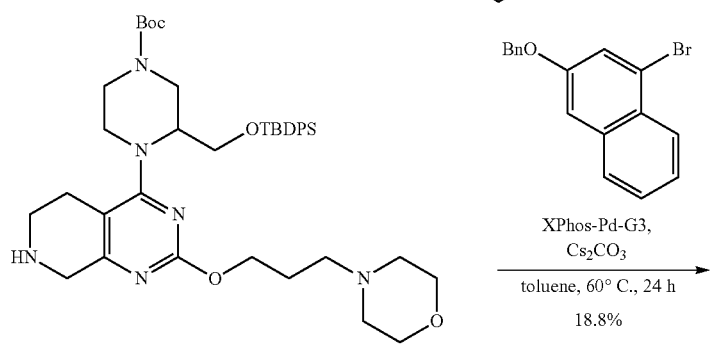
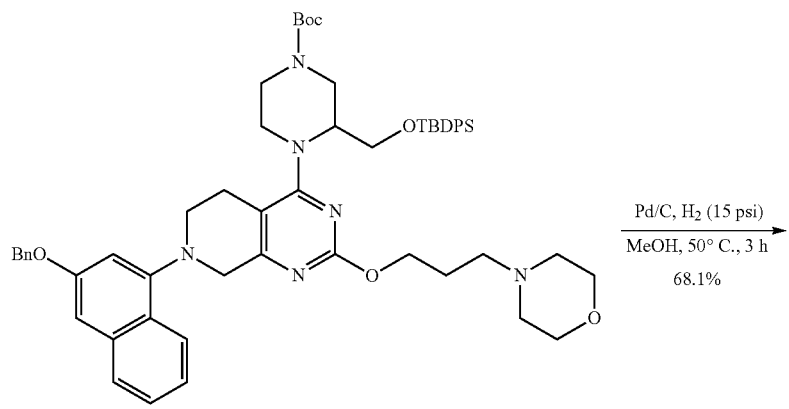

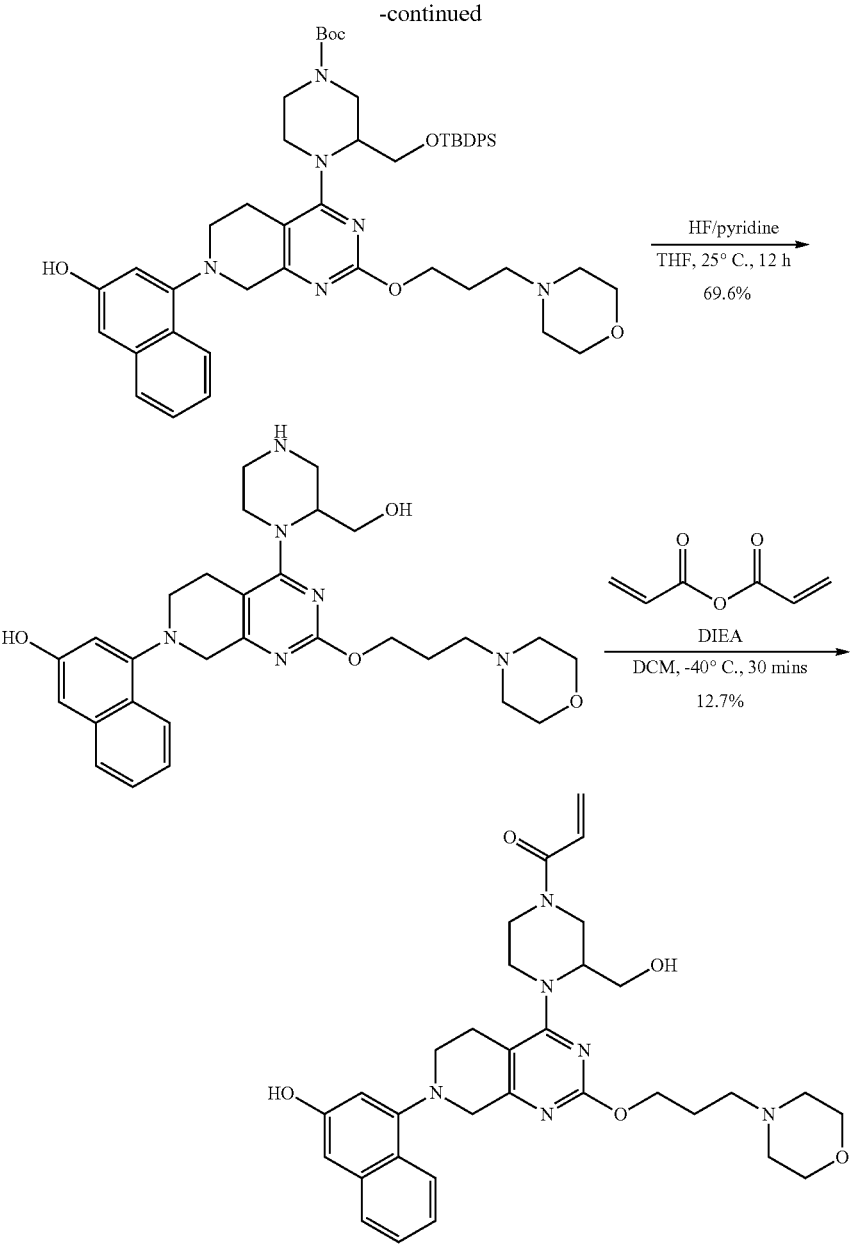

Step A: tert-butyl 3-[[tert-butyl(diphenyl)silyl]oxymethyl]piperazine-1-carboxylate To a solution of tert-butyl 3-(hydroxymethyl)piperazine-1-carboxylate (3.50 g, 16.2 mmol) in THF (30 mL) was added NaH (3.24 g, 80.9 mmol, 60.0% purity) at 0° C. After stirring for 30 minutes, TBDPSCl (6.67 g, 24.3 mmol, 6.23 mL) was added in one portion. The mixture was warmed to 10° C. and stirred for 12 hours under $N_2$ atmosphere. The reaction mixture was quenched by addition water at 0° C., and then extracted with DCM (200 mL). The organic layer was dried with $Na_2SO_4$, filtered and concentrated under reduced pressure. The residue was purified by column chromatography ($SiO_2$, Petroleum ether/Ethyl acetate 1/0 to 1/2) to give tert-butyl 3-[[tert-butyl(diphenyl)silyl]oxymethyl]piperazine-1-carboxylate (6.34 g, 12.1 mmol, 74.8% yield, 86.8% purity) as a colorless oil. ES+APCI MS m/z 455.3[M+H]+.

Step B: tert-butyl4-(7-benzyl-2-chloro-6,8-dihydro-5H-pyrido[3,4-d]pyrimidin-4-yl)-3-[[tert-butyl(diphenyl)silyl]oxymethyl]piperazine-1-carboxylate: A mixture of tert-butyl 3-[[tert-butyl(diphenyl)silyl]oxymethyl] piperazine-1-carboxylate (7.25 g, 13.9 mmol), 7-benzyl-2,4-dichloro-6,8-dihydro-5H-pyrido[3,4-d]pyrimidine (3.89 g, 13.2 mmol) and DIEA (4.27 g, 33.0 mmol, 5.77 mL) in DMSO (60 mL) was stirred at 55° C. for 24 hours under $N_2$ atmosphere. The reaction mixture was diluted with ethyl acetate (300 mL) and washed with brine (3×150 mL). The organic layer was dried over $Na_2SO_4$, filtered and concentrated under reduced pressure. The residue was purified by column chromatography ($SiO_2$, Petroleum ether/Ethyl acetate 1/0 to 3/1) to give tert-butyl4-(7-benzyl-2-chloro-6,8-dihydro-5H-pyrido[3,4-d]pyrimidin-4-yl)-3-[[tert-butyl(diphenyl)silyl]oxymethyl]piperazine-1-carboxylate (4.50 g, 5.91 mmol, 44.7% yield, 93.5% purity) as a yellow solid. ES+APCI MS m/z 721.3[M+H]+.

Step C: tert-butyl4-[7-benzyl-2-(3-morpholinopropoxy)-6,8-dihydro-5H-pyrido[3,4-d]pyrimidin-4-yl]-3-[[tert-butyl(diphenyl)silyl]oxymethyl]piperazine-1-carboxylate: A mixture of tert-butyl 4-(7-benzyl-2-chloro-6,8-dihydro-5H-pyrido [3,4-d]pyrimidin-4-yl)-3-[[tert-butyl(diphenyl)silyl]oxymethyl]piperazine-1-carboxylate (2.00 g, 2.81 mmol), 3-morpholinopropan-1-ol (815 mg, 5.62 mmol), Pd(OAc)$_2$ (94.6 mg, 422 umol), BINAP (350 mg, 562 umol) and t-BuONa (674 mg, 7.03 mmol) in toluene (30 mL) was degassed and purged with N$_2$ for 3 times, and then the mixture was heated to 110° C. and stirred for 3 hours under N$_2$ atmosphere. After completion, the reaction mixture was filtered and concentrated under reduced pressure. The residue was purified by column chromatography (SiO$_2$, DCM/MeOH 70/1 to 20/1) to give tert-butyl4-[7-benzyl-2-(3-morpholinopropoxy)-6,8-dihydro-5H-pyrido[3,4-d]pyrimidin-4-yl]-3-[[tert-butyl(diphenyl)silyl]oxymethyl]piperazine-1-carboxylate (1.50 g, 1.69 mmol, 60.0% yield, 92.3% purity) as a yellow solid. ES+APCI MS m/z 821.4 [M+H]$^+$.

Step D: tert-butyl 3-[[tert-butyl(diphenyl)silyl]oxymethyl]-4-[2-(3-morpholinopropoxy)-5,6,7,8-tetrahydropyrido[3,4-d]pyrimidin-4-yl]piperazine-1-carboxylate: To a solution of tert-butyl 4-[7-benzyl-2-(3-morpholinopropoxy)-6,8-dihydro-5H-pyrido [3,4-d]pyrimidin-4-yl]-3-[[tert-butyl(diphenyl)silyl] oxymethyl]piperazine-1-carboxylate (1.50 g, 1.83 mmol) in MeOH (20 mL) was added Pd—C (10%, 1.5 g) under N$_2$. The suspension was degassed under vacuum and purged with H$_2$ several times. The mixture was stirred under H$_2$ (50 psi) at 50° C. for 24 hours. The reaction mixture was filtered and concentrated under reduced pressure to give tert-butyl 3-[[tert-butyl(diphenyl)silyl]oxymethyl]-4-[2-(3-morpholinopropoxy)-5,6,7,8-tetrahydropyrido[3,4-d]pyrimidin-4-yl]piperazine-1-carboxylate (988 mg, 1.21 mmol, 66.1% yield, 89.5% purity) as a colorless oil, which was used directly for next step without further purification. ES+APCI MS m/z 731.5[M+H]$^+$.

Step E: tert-butyl4-[7-(3-benzyloxy-1-naphthyl)-2-(3-morpholinopropoxy)-6,8-dihydro-5H-pyrido[3,4-d]pyrimidin-4-yl]-3-[[tert-butyl(diphenyl)silyl]oxymethyl]piperazine-1-carboxylate: A mixture of tert-butyl 3-[[tert-butyl(diphenyl)silyl]oxymethyl]-4-[2-(3-morpholinopropoxy)-5,6,7,8-tetrahydropyrido[3,4-d]pyrimidin-4-yl]piperazine-1-carboxylate (731 mg, 1.00 mmol), 3-benzyloxy-1-bromo-naphthalene (783 mg, 2.50 mmol), [2-(2-aminophenyl)phenyl]palladium(1+); dicyclohexyl-[2-(2,4,6-triisopropylphenyl)phenyl]phosphane; methanesulfonate (169 mg, 200 umol), Cs$_2$CO$_3$ (815 mg, 2.50 mmol) in toluene (15 mL) was degassed and purged with N$_2$ 3 times, and then the mixture was stirred at 60° C. for 24 hours under N$_2$ atmosphere. The reaction mixture was filtered and concentrated under reduced pressure to dryness and purified by column chromatography (SiO$_2$, DCM/MeOH=70/1 to 30/1) to give tert-butyl4-[7-(3-benzyloxy-1-naphthyl)-2-(3-morpholinopropoxy)-6,8-dihydro-5H-pyrido[3,4-d]pyrimidin-4-yl]-3-[[tert-butyl(diphenyl)silyl]oxymethyl]piperazine-1-carboxylate (250 mg, 188 umol, 18.8% yield, 72.3% purity) as a yellow solid. ES+APCI MS m/z 963.4[M+H]$^+$.

Step F: tert-butyl 3-[[tert-butyl(diphenyl)silyl]oxymethyl]-4-[7-(3-hydroxy-1-naphthyl)-2-(3-morpholinopropoxy)-6,8-dihydro-5H-pyrido[3,4-d]pyrimidin-4-yl]piperazine-1-carboxylate: To a solution of tert-butyl 4-[7-(3-benzyloxy-1-naphthyl)-2-(3-morpholinopropoxy)-6,8-dihydro-5H-pyrido[3,4-d]pyrimidin-4-yl]-3-[[tert-butyl(diphenyl)silyl]oxymethyl]piperazine-1-carboxylate (250 mg, 188 umol) in MeOH (3 mL) was added 10% Pd/C (0.25 g) under N$_2$. The suspension was degassed under vacuum and purged with H$_2$ several times. The mixture was stirred under H$_2$ (15 psi) at 50° C. for 3 hours. After completion, the reaction mixture was filtered and concentrated under reduced pressure to dryness to give tert-butyl 3-[[tert-butyl(diphenyl)silyl]oxymethyl]-4-[7-(3-hydroxy-1-naphthyl)-2-(3-morpholinopropoxy)-6,8-dihydro-5H-pyrido[3,4-d]pyrimidin-4-yl]piperazine-1-carboxylate (180 mg, 128 umol, 68.1% yield, 62.0% purity) as a dark yellow solid, which was used directly for next step without further purification. ES+APCI MS m/z 873.4[M+H]$^+$.

Step G: 4-[4-[2-(hydroxymethyl)piperazin-1-yl]-2-(3-morpholinopropoxy)-6,8-dihydro-5H-pyrido[3,4-d]pyrimidin-7-yl]naphthalen-2-ol A mixture of tert-butyl 3-[[tert-butyl(diphenyl)silyl]oxymethyl]-4-[7-(3-hydroxy-1-naphthyl)-2-(3-morpholinopropoxy)-6,8-dihydro-5H-pyrido[3,4-d]pyrimidin-4-yl]piperazine-1-carboxylate (130 mg, 149 umol), pyridine hydrofluoride (123 mg, 744 umol, 112 uL, 60.0% purity) in THF (1.5 mL) was stirred at 25° C. for 12 hours under N$_2$ atmosphere. The reaction mixture was concentrated under reduced pressure to dryness. The residue was purified by reverse phase HPLC (TFA condition; MeCN in H$_2$O; 0~30%, flow rate; 40 mL/mins). The desired fractions were concentrated under reduced pressure to give 4-[4-[2-(hydroxymethyl)piperazin-1-yl]-2-(3-morpholinopropoxy)-6,8-dihydro-5H-pyrido[3,4-d]pyrimidin-7-yl]naphthalen-2-ol (84 mg, 104 umol, 69.6% yield, 94.1% purity, 2TFA) as a yellow semisolid. ES+APCI MS m/z 535.3 [M+H]$^+$.

Step H: 1-[3-(hydroxymethyl)-4-[7-(3-hydroxy-1-naphthyl)-2-(3-morpholinopropoxy)-6,8-dihydro-5H-pyrido[3,4-d]pyrimidin-4-yl]piperazin-1-yl]prop-2-en-1-one: To a mixture of 4-[4-[2-(hydroxymethyl)piperazin-1-yl]-2-(3-morpholinopropoxy)-6,8-dihydro-5H-pyrido[3,4-d]pyrimidin-7-yl]naphthalen-2-ol (84.0 mg, 114 umol, 2TFA), DIEA (36.9 mg, 285 umol, 49.8 uL) in DCM (3 mL) was added prop-2-enoyl prop-2-enoate (8.63 mg, 68.44 umol) drop wise at −40° C., and then stirred at −40° C. for 0.5 hours under N$_2$ atmosphere. The reaction mixture was quenched by addition MeOH (0.5 mL) and concentrated under reduced pressure to dryness. The residue was purified by prep-HPLC (column: Venusil XBP C8 150*25*10 um; mobile phase: [water (0.225% Formic Acid)-ACN]; B %: 10%-40%, 10 min). The desired fractions were collected and lyophilized to dryness to give 1-[3-(hydroxymethyl)-4-[7-(3-hydroxy-1-naphthyl)-2-(3-morpholinopropoxy)-6,8-dihydro-5H-pyrido[3,4-d]pyrimidin-4-yl]piperazin-1-yl]prop-2-en-1-one (9.75 mg, 14.5 umol, 12.7% yield, 94.4% purity, Formic Acid Salt) as a yellow solid. ES+APCI MS m/z 589.3[M+H]$^+$.

Example 169

1-[3-(hydroxymethyl)-4-[7-(3-hydroxy-1-naphthyl)-2-[[(2S)-1-methylpyrrolidin-2-yl]methoxy]-6,8-dihydro-5H-pyrido [3,4-d]pyrimidin-4-yl]piperazin-1-yl]prop-2-en-1-one

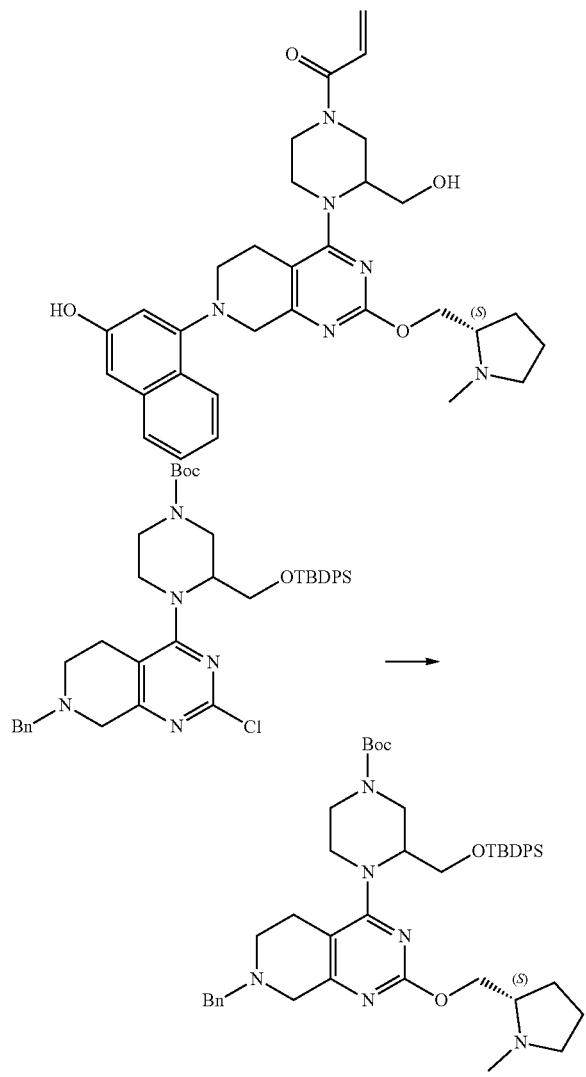

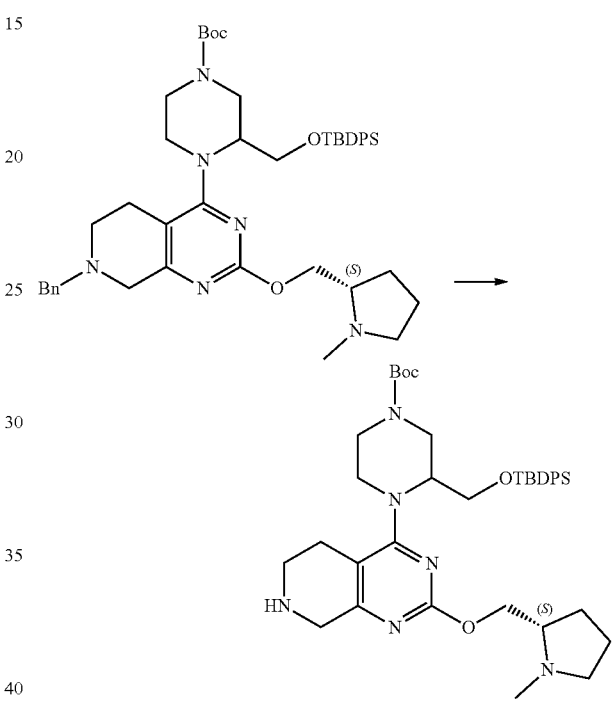

Step A: tert-butyl 4-[7-benzyl-2-[[(2S)-1-methylpyrrolidin-2-yl]methoxy]-6,8-dihydro-5H-pyrido[3,4-d]pyrimidin-4-yl]-3-[[tert-butyl(diphenyl)silyl]oxymethyl]piperazine-1-carboxylate: To a mixture of tert-butyl 4-(7-benzyl-2-chloro-6,8-dihydro-5H-pyrido[3,4-d]pyrimidin-4-yl)-3-[[tert-butyl(diphenyl)silyl]oxymethyl]piperazine-1-carboxylate (495 mg, 694 umol), [(2S)-1-methylpyrrolidin-2-yl]methanol (160 mg, 1.39 mmol, 165 uL) and sodium tert-butoxide (200 mg, 2.08 mmol) in toluene (25 mL) was added BINAP (86.5 mg, 139 umol) and $Pd_2(dba)_3$ (63.6 mg, 69.5 umol). The mixture was bubbled with nitrogen atmosphere and stirred at 80° C. for 6 h. The reaction mixture was diluted with water (10 mL) and extracted with ethyl acetate (2×15 mL). The combined organic layers were washed with water (2×30 mL), dried over $Na_2SO_4$, filtered and concentrated under reduced pressure to give a residue. The residue was purified by column chromatography ($SiO_2$, Petroleum ether/Ethyl acetate=30/1 to 1:1) to give tert-butyl 4-[7-benzyl-2-[[(2S)-1-methylpyrrolidin-2-yl]methoxy]-6,8-dihydro-5H-pyrido [3,4-d]pyrimidin-4-yl]-3-[[tert-butyl(diphenyl)silyl]oxymethyl]piperazine-1-carboxylate (207 mg, 262 umol, 37.7% yield) as a yellow solid. $^1$H NMR (400 MHz, chloroform-d) δ=7.62-7.53 (m, 4H), 7.43-7.28 (m, 11H), 4.42-4.29 (m, 1H), 4.26-3.87 (m, 4H), 3.81 (br d, J=13.2 Hz, 2H), 3.75-3.60 (m, 4H), 3.44 (dd, J=1.6, 17.2 Hz, 1H), 3.24-3.04 (m, 3H), 2.96 (br s, 1H), 2.75 (br s, 3H), 2.49 (s, 3H), 2.43-2.28 (m, 2H), 2.10-1.96 (m, 2H), 1.91-1.80 (m, 1H), 1.80-1.67 (m, 2H), 1.43 (s, 9H), 1.02-0.89 (m, 9H).

Step B: tert-butyl 3-[[tert-butyl(diphenyl)silyl] oxymethyl]-4-[2-[[(2S)-1-methylpyrrolidin-2-yl]methoxy]-5,6,7,8-tetrahydropyrido[3,4-d]pyrimidin-4-yl]piperazine-1-carboxylate: $NH_3$ was bubbled in methanol (30 mL) at −40° C. for 30 minutes. To a solution of tert-butyl 4-[7-benzyl-2-[[(2S)-1-methylpyrrolidin-2-yl]methoxy]-6,8-dihydro-5H-pyrido[3,4-d]pyrimidin-4-yl]-3-[[tert-butyl(diphenyl)silyl] oxymethyl]piperazine-1-carboxylate (530 mg, 670 umol) in above mixture was added dry 10% Pd/C (0.30 g) under $N_2$. The suspension was degassed under vacuum and purged with $H_2$ several times. The mixture was stirred at 40° C. for 10 hours under 15 psi of $H_2$. The reaction mixture was filtered and concentrated under reduced pressure to give tert-butyl 3-[[tert-butyl(diphenyl)silyl] oxymethyl]-4-[2-[[(2S)-1-methylpyrrolidin-2-yl]methoxy]-5,6,7,8-tetrahydropyrido[3,4-d]pyrimidin-4-yl]piperazine-1-carboxylate (394 mg, 427 umol, 63.8% yield) as a yellow solid. $^1$H NMR (400 MHz, chloroform-d) δ=7.57 (br t, J=6.0 Hz, 4H), 7.43-7.33 (m, 6H), 4.43 (br dd, J=5.2, 10.4 Hz, 1H), 4.32-4.00 (m, 4H), 3.99-3.89 (m, 2H), 3.88-3.65 (m, 4H), 3.27-2.89 (m, 6H), 2.81 (br d, J=8.4 Hz, 2H), 2.56-2.50 (m, 3H), 2.42 (br d, J=16.8 Hz, 2H), 2.13-2.03 (m, 1H), 1.88 (br d, J=6.8 Hz, 1H), 1.79 (br d, J=5.2 Hz, 2H), 1.43 (s, 9H), 0.95 (br s, 9H).

513

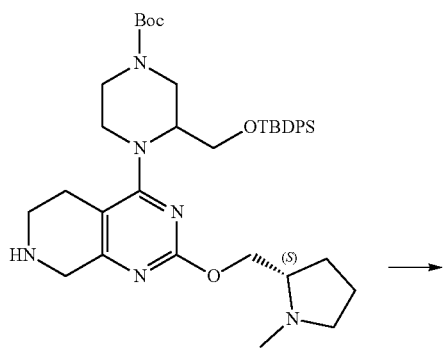

514

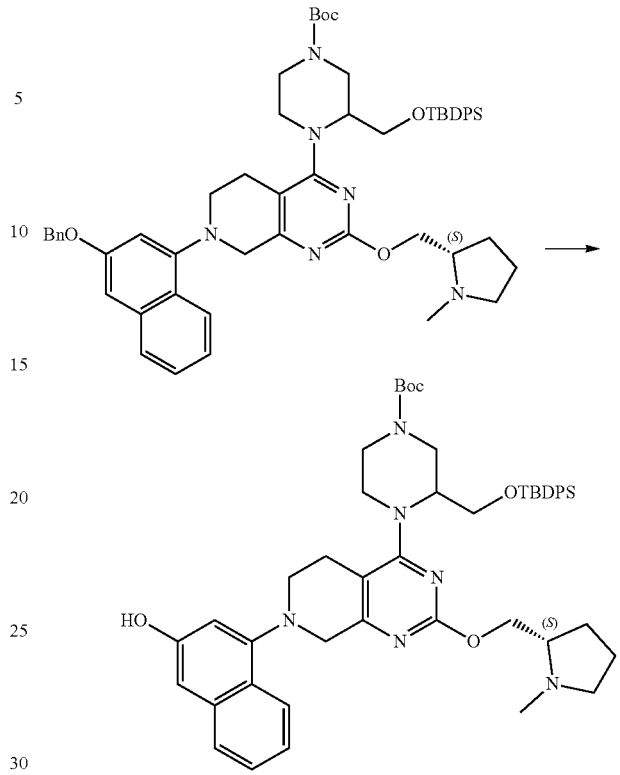

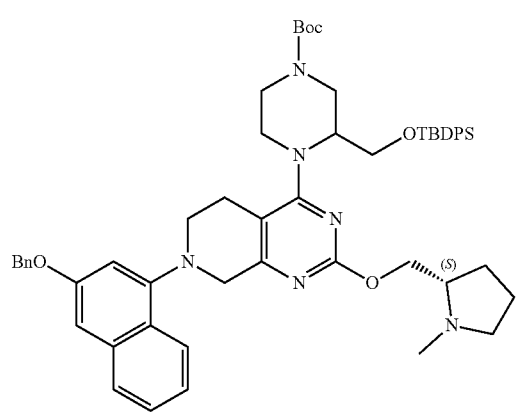

Step C: tert-butyl 4-[7-(3-benzyloxy-1-naphthyl)-2-[[(2S)-1-methylpyrrolidin-2-yl]methoxy]-6,8-dihydro-5H-pyrido[3,4-d]pyrimidin-4-yl]-3-[[tert-butyl(diphenyl) silyl] oxymethyl]piperazine-1-carboxylate: A mixture of tert-butyl 3-[[tert-butyl(diphenyl)silyl]oxymethyl]-4-[2-[[(2S)-1-methylpyrrolidin-2-yl]methoxy]-5,6,7,8-tetrahydropyrido [3,4-d]pyrimidin-4-yl]piperazine-1-carboxylate (0.16 g, 228 umol), 3-benzyloxy-1-bromo-naphthalene (143 mg, 457 umol), [2-(2-aminoethyl)phenyl]-chloro-palladium; dicyclohexyl-[2-(2,4,6-triisopropylphenyl)phenyl]phosphane (16.9 mg, 22.8 umol) and t-BuONa (43.9 mg, 457 umol) in toluene (4 mL) was stirred at 70° C. for 12 hours under N$_2$. The mixture was diluted with water (5.00 mL) and extracted with ether acetate (3×10 mL). The combined organics were washed with saturated sodium chloride (10 mL), dried over Na$_2$SO$_4$, filtered and concentrated under vacuum. The residue was purified by reversed phase flash [water (formic acid, 0.1%)/acetonitrile] to give tert-butyl 4-[7-(3-benzyloxy-1-naphthyl)-2-[[(2S)-1-methylpyrrolidin-2-yl]methoxy]-6,8-dihydro-5H-pyrido[3,4-d]pyrimidin-4-yl]-3-[[tert-butyl(diphenyl)silyl]oxymethyl]piperazine-1-carboxylate (0.15 g, 157 umol, 68.9% yield) as a yellow solid. ES+APCI MS m/z 933.1[M+H]$^+$.

Step D: tert-butyl 3-[[tert-butyl(diphenyl)silyl]oxymethyl]-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate: NH$_3$ was bubbled into methanol (10 mL) at −78° C. for 30 minutes. tert-butyl 4-[7-(3-benzyloxy-1-naphthyl)-2-[[(2S)-1-methylpyrrolidin-2-yl]methoxy]-6,8-dihydro-5H-pyrido[3,4-d]pyrimidin-4-yl]-3-[[tert-butyl(diphenyl)silyl] oxymethyl]piperazine-1-carboxylate (0.10 g, 107 umol) and dry 10% Pd/C (0.01 g) were added and the mixture was stirred at 10° C. for 1 hour under 15 psi of H$_2$. The slurry was filtered through a pad of celite and the filtrate concentrated under vacuum to give tert-butyl 3-[[tert-butyl(diphenyl)silyl]oxymethyl]-4-[7-(3-hydroxy-1-naphthyl)-2-[[(2S)-1-methylpyrrolidin-2-yl] methoxy]-6,8-dihydro-5H-pyrido[3,4-d]pyrimidin-4-yl]piperazine-1-carboxylate (0.09 g, crude) as a yellow oil and used into next step without further purification. ES+APCI MS m/z 843.0 [M+H]$^+$.

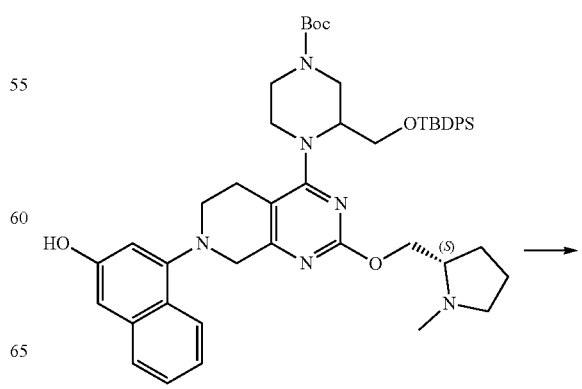

515

-continued

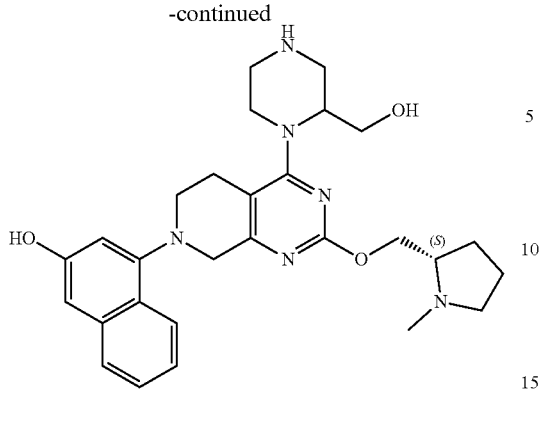

516

-continued

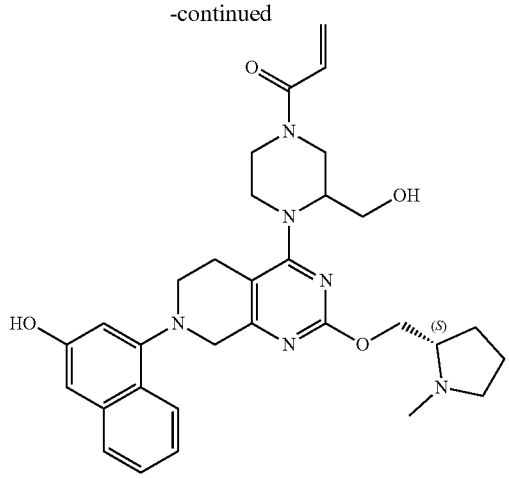

Step E: 4-[4-[2-(hydroxymethyl)piperazin-1-yl]-2-[[(2S)-1-methylpyrrolidin-2-yl]methoxy]-6,8-dihydro-5H-pyrido[3,4-d]pyrimidin-7-yl]naphthalen-2-ol: A mixture of tert-butyl 3-[[tert-butyl(diphenyl)silyl]oxymethyl]-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (0.04 g, crude) and pyridine; hydrofluoride (118 mg, 712 umol, 106 uL) in dichloromethane (2 mL) was stirred at 0° C. for 1 hour and stirred at 10° C. for 12 hours. The pH of the mixture was adjusted to pH >7 by addition of saturated sodium bicarbonate solution (3.00 mL) and concentrated under vacuum. The residue was purified by column chromatography (Al$_2$O$_3$, dichloromethane/methanol=5/1) to give 4-[4-[2-(hydroxymethyl)piperazin-1-yl]-2-[[(2S)-1-methylpyrrolidin-2-yl]methoxy]-6,8-dihydro-5H-pyrido[3,4-d]pyrimidin-7-yl]naphthalen-2-ol (0.04 g, crude) as a yellow solid. ES+APCI MS m/z 505.2 [M+H]$^+$.

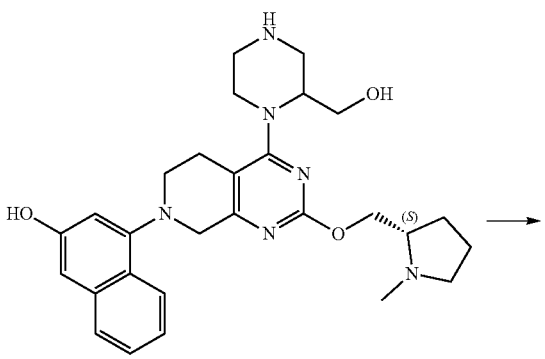

Step F: 1-[3-(hydroxymethyl)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one: To a solution of 4-[4-[2-(hydroxymethyl)piperazin-1-yl]-2-[[(2S)-1-methylpyrrolidin-2-yl]methoxy]-6,8-dihydro-5H-pyrido[3,4-d]pyrimidin-7-yl]naphthalen-2-ol (0.02 g, crude) and TEA (40.1 mg, 396 umol, 55.17 uL) in dichloromethane (2 mL) was added prop-2-enoyl prop-2-enoate (999 ug, 7.93 umol) at −40° C., then the mixture was stirred at −40° C. for 0.5 h. The mixture was quenched by addition of methanol (0.10 mL) and concentrated under vacuum. The residue was purified by column chromatography (Al$_2$O$_3$, dichloromethane/methanol=5/1). The desired fractions were collected and concentrated under vacuum. The residue was purified by prep-HPLC (column: Phenomenex Gemini 150*25 mm*10 um; mobile phase: [water (10 mM NH4HCO3)-ACN]; B %: 38%-68%, 3 min). The desired fractions were collected and lyophilized to give 1-[3-(hydroxymethyl)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one (1.08 mg, 1.73 umol). ES+APCI MS m/z 559.5 [M+H]$^+$.

Example 170
2-(1-acryloyl-4-(2-(2-(dimethylamino)ethoxy)-7-(3-hydroxynaphthalen-1-yl)-5,6,7,8-tetrahydropyrido[3,4-d]pyrimidin-4-yl)piperazin-2-yl)acetonitrile
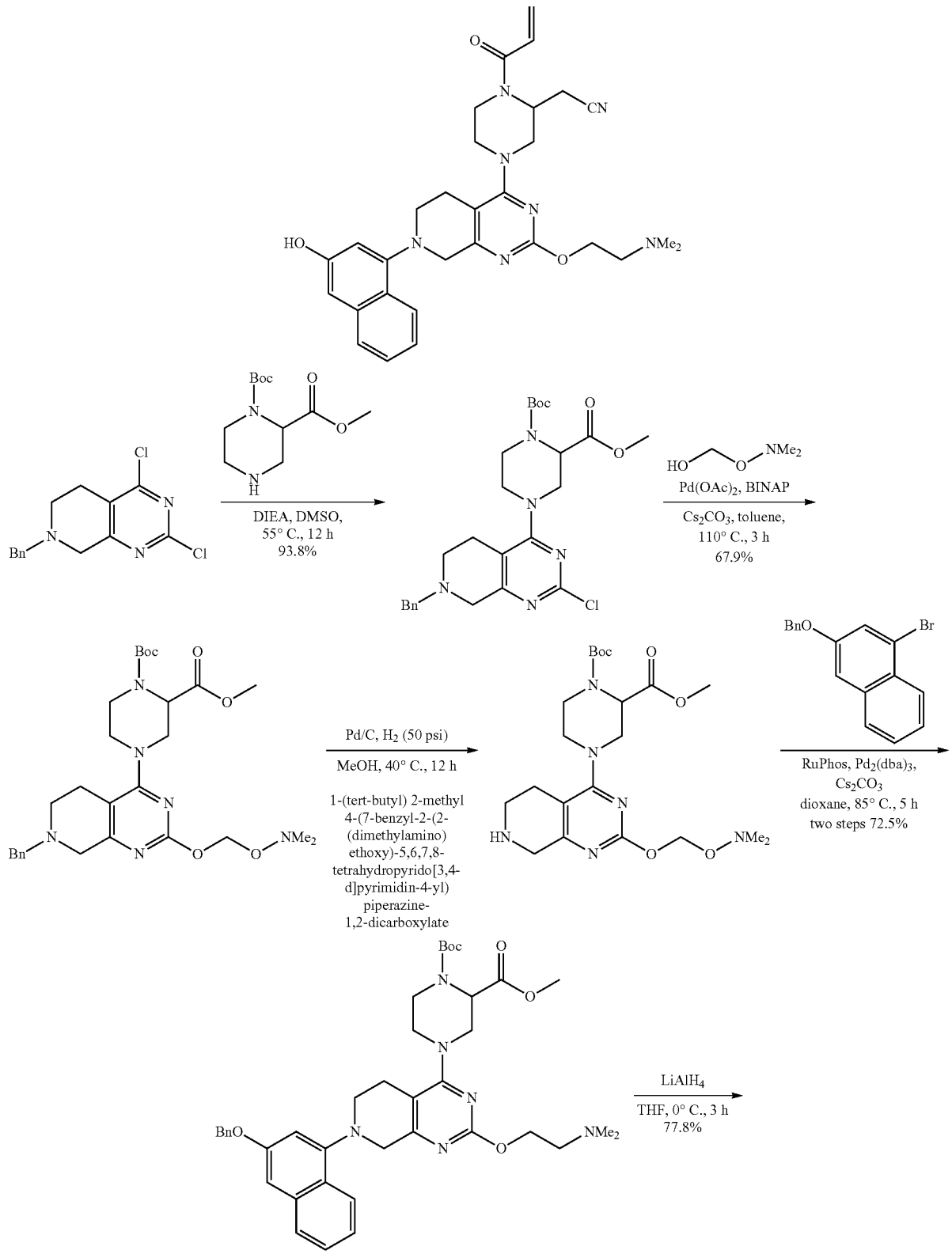

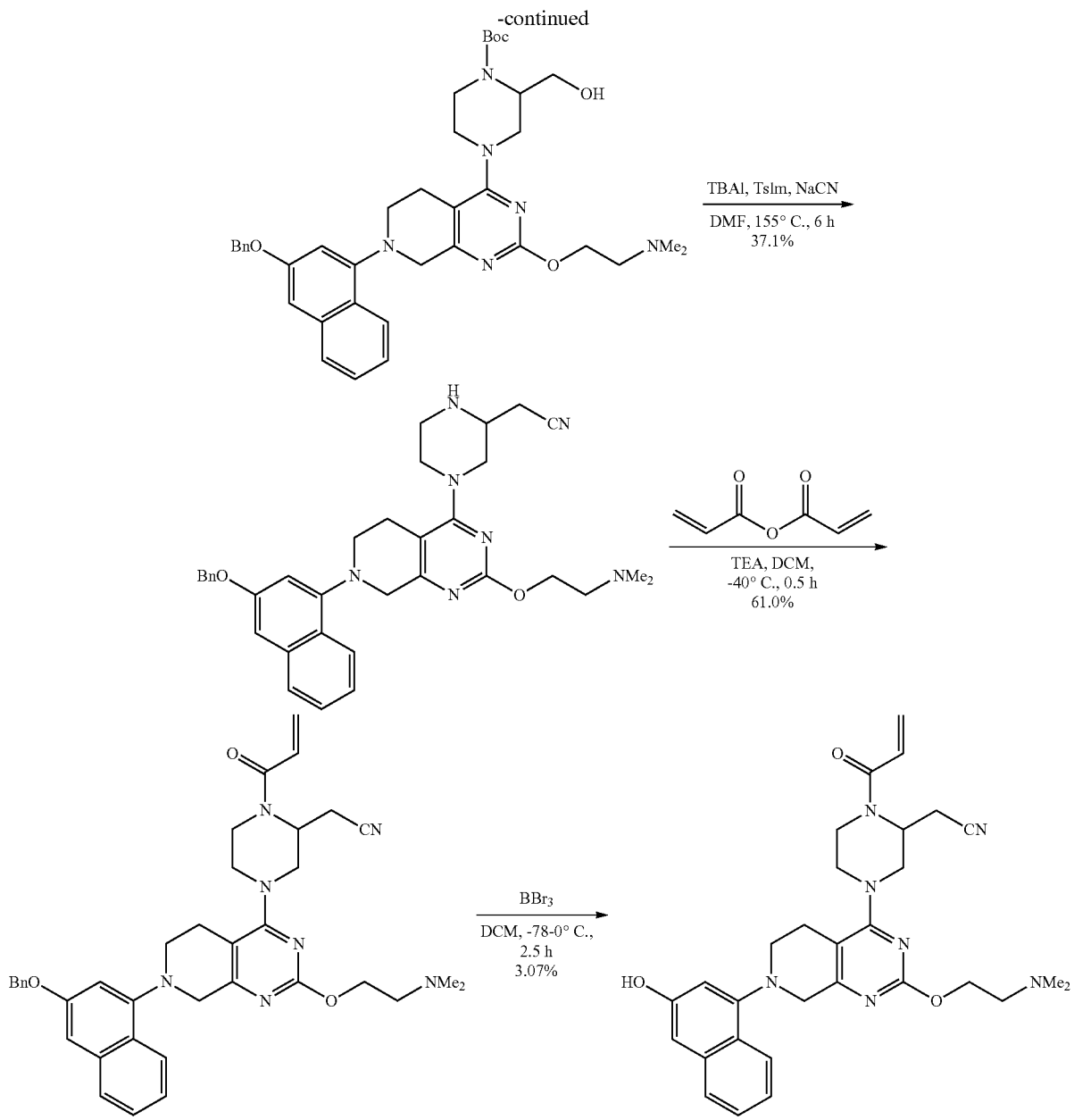

Step A: 1-(tert-butyl)2-methyl4-(7-benzyl-2-chloro-5,6,7,8-tetrahydropyrido[3,4-d]pyrimidin-4-yl) piperazine-1,2-dicarboxylate To a solution of 7-benzyl-2,4-dichloro-6,8-dihydro-5H-pyrido [3,4-d] pyrimidine (5.00 g, 17.0 mmol) and 1-tert-butyl 2-methylpiperazine-1,2-dicarboxylate (4.24 g, 17.3 mmol) in DMSO (80 mL) was added DIEA (5.49 g, 42.5 mmol, 7.42 mL). After stirring at 55° C. for 12 hours, the mixture was diluted with ethyl acetate (100 mL), washed with brine (3×150 mL), dried over $Na_2SO_4$, filtered and concentrated under vacuum. The residue was purified by column chromatography ($SiO_2$, PE/EA=3/1) to give 1-tert-butyl 2-methyl 4-(7-benzyl-2-chloro-6,8-dihydro-5H-pyrido [3,4-d] pyrimidin-4-yl)piperazine-1,2-dicarboxylate (8.00 g, 15.9 mmol, 93.8% yield) as a yellow oil. ES+APCI MS m/z 502.1[M+H]$^+$.

Step B: 1-(tert-butyl) 2-methyl 4-(7-benzyl-2-(2-(dimethylamino)ethoxy)-5,6,7,8-tetrahydropyrido [3,4-d]pyrimidin-4-yl) piperazine-1,2-dicarboxylate: A mixture of 1-tert-butyl 2-methyl 4-(7-benzyl-2-chloro-6,8-dihydro-5H-pyrido [3,4-d]pyrimidin-4-yl) piperazine-1,2-dicarboxylate (8.00 g, 15.9 mmol), 2-(dimethylamino)ethanol (2.84 g, 31.9 mmol, 3.19 mL), $Cs_2CO_3$ (13.0 g, 39.8 mmol), Pd(OAc)$_2$ (537 mg, 2.39 mmol) and BINAP (1.98 g, 3.19 mmol) in toluene (30 mL) was stirred at 110° C. for 3 hours under nitrogen. The mixture was diluted with water (30 mL) and then extracted with ethyl acetate (3×50 mL). The extracts were washed with brine (1×100 mL), dried over $Na_2SO_4$, filtered and concentrated under vacuum. The residue was purified by reverse phase HPLC (TFA, 0.1%) to give 1-tert-butyl 2-methyl 4-[7-benzyl-2-[2-(dimethylamino)ethoxy]-6,8-dihydro-5H-pyrido[3,4-d]pyrimidin-4-yl]piperazine-1,2-dicarboxylate (6.00 g, 10.8 mmol, 67.9% yield) as a yellow solid. ES+APCI MS m/z 555.3[M+H]$^+$.

Step C: 1-tert-butyl 2-methyl 4-[2-[2-(dimethylamino) ethoxy]-5,6,7,8-tetrahydropyrido[3,4-d]pyrimidin-4-yl]piperazine-1,2-dicarboxylate: A mixture of 1-tert-butyl 2-methyl 4-[7-benzyl-2-[2-(dimethylamino) ethoxy]-6,8-dihydro-5H-pyrido[3,4-d]pyrimidin-4-yl]piperazine-1,2-dicarboxylate (6.00 g, 10.8 mmol) and 10% Pd/C (600 mg, 10.8 mmol) in MeOH (100 mL) was stirred at 40° C. for 12 hours under $H_2$ at 50 psi. The mixture was filtered and the filtrate was concentrated under vacuum to give 1-tert-butyl 2-methyl 4-[2-[2-(dimethylamino)ethoxy]-5,6,7,8-tetrahydropyrido[3,4-d]pyrimidin-4-yl]piperazine-1,2-dicarboxylate (4.50 g, crude) was obtained as a yellow solid. ES+APCI MS m/z 465.3[M+H]$^+$.

Step D: 1-tert-butyl 2-methyl 4-[7-(3-benzyloxy-1-naphthyl)-2-[2-(dimethylamino)ethoxy]-6,8-dihydro-5H-pyrido[3,4-d]pyrimidin-4-yl]piperazine-1,2-dicarboxylate: A mixture of 1-tert-butyl 2-methyl 4-[2-[2-(dimethylamino) ethoxy]-5,6,7,8-tetrahydropyrido[3,4-d]pyrimidin-4-yl] piperazine-1,2-dicarboxylate (2.90 g, 6.24 mmol), 3-benzyloxy-1-bromo-naphthalene (2.54 g, 8.12 mmol), $Pd_2$(dba)$_3$ (857 mg, 936 umol), RuPhos (728 mg, 1.56 mmol) and $Cs_2CO_3$ (5.08 g, 15.6 mmol) in 1,4-dioxane (150 mL) was stirred at 85° C. for 5 hours under $N_2$. The mixture was diluted with water (100 mL), extracted with DCM (1×200 mL). The extracts were, washed with brine (1×300 mL), dried over $Na_2SO_4$, filtered and concentrated under vacuum. The residue was purified by reverse phase HPLC (TFA, 0.1%) to give 1-tert-butyl 2-methyl 4-[7-(3-benzyloxy-1-naphthyl)-2-[2-(dimethylamino)ethoxy]-6,8-dihydro-5H-pyrido[3,4-d]pyrimidin-4-yl]piperazine-1,2-dicarboxylate (3.50 g, 5.02 mmol, two steps 72.5% yield) as a brown solid. ES+APCI MS m/z 697.3 [M+H]$^+$.

Step E: tert-butyl 4-[7-(3-benzyloxy-1-naphthyl)-2-[2-(dimethylamino)ethoxy]-6,8-dihydro-5H-pyrido[3,4-d]pyrimidin-4-yl]-2-(hydroxymethyl)piperazine-1-carboxylate: To a solution of 1-tert-butyl 2-methyl 4-[7-(3-benzyloxy-1-naphthyl)-2-[2-(dimethylamino)ethoxy]-6,8-dihydro-5H-pyrido[3,4-d]pyrimidin-4-yl]piperazine-1,2-dicarboxylate (1.00 g, 1.44 mmol) in THF (10 mL) was added LiAlH$_4$ (219 mg, 5.76 mmol) in portions at −60° C. After stirring for 2 hours, the mixture was quenched with saturated sodium sulfate solution (0.3 mL), filtered and the filter cake washed with DCM (100 mL). The combined filtrate was concentrated under vacuum to give tert-butyl 4-[7-(3-benzyloxy-1-naphthyl)-2-[2-(dimethylamino)ethoxy]-6,8-dihydro-5H-pyrido[3,4-d] pyrimidin-4-yl]-2-(hydroxymethyl) piperazine-1-carboxylate (750 mg, 1.12 mmol, 77.8% yield) as a yellow solid. ES+APCI MS m/z 669.3 [M+H]$^+$.

Step F: 2-[4-[7-(3-benzyloxy-1-naphthyl)-2-[2-(dimethylamino)ethoxy]-6,8-dihydro-5H-pyrido[3,4-d]pyrimidin-4-yl]piperazin-2-yl]acetonitrile: A mixture of tert-butyl 4-[7-(3-benzyloxy-1-naphthyl)-2-[2-(dimethylamino)ethoxy]-6,8-dihydro-5H-pyrido[3,4-d]pyrimidin-4-yl]-2-(hydroxymethyl) piperazine-1-carboxylate (100 mg, 149 umol), TBAI (11.1 mg, 29.9 umol), 1-(p-tolylsulfonyl)imidazole (79.9 mg, 359 umol), NaCN (0.12 g, 2.45 mmol), and TEA (37.8 mg, 374 umol, 51.8 uL) in DMF was stirred at 155° C. for 6 hours. The mixture was concentrated under vacuum, diluted with water (1×5 mL) and then extracted with ethyl acetate (3×10 mL). The extracts were washed with brine (1×20 mL), dried over $Na_2SO_4$, filtered and concentrated under vacuum. The residue was purified by prep-HPLC column: Phenomenex Gemini C18 250*50 mm*10 um; mobile phase: [water (0.05% ammonia hydroxide v/v)-ACN]; B %: 50%-70%, 28 MIN) to give 2-[4-[7-(3-benzyloxy-1-naphthyl)-2-[2-(dimethylamino)ethoxy]-6,8-dihydro-5H-pyrido[3,4-d]pyrimidin-4-yl]piperazin-2-yl]acetonitrile (160 mg, 277 umol, 37.1% yield) as a yellow solid. ES+APCI MS m/z 578.5[M+H]$^+$.

Step G: 2-[4-[7-(3-benzyloxy-1-naphthyl)-2-[2-(dimethylamino)ethoxy]-6,8-dihydro-5H-pyrido[3,4-d]pyrimidin-4-yl]-1-prop-2-enoyl-piperazin-2-yl]acetonitrile: To a solution of 2-[4-[7-(3-benzyloxy-1-naphthyl)-2-[2-(dimethylamino)ethoxy]-6,8-dihydro-5H-pyrido[3,4-d] pyrimidin-4-yl]piperazin-2-yl]acetonitrile (60 mg, 104 umol) and DIEA (67.1 mg, 519 umol, 90.7 uL) in DCM (2 mL) was added prop-2-enoyl prop-2-enoate (13.1 mg, 104 umol) at 0° C. After stirred at 10° C. for 4 hours, the mixture was quenched with MeOH (0.1 mL), then concentrated under vacuum. The residue was purified by column chromatography (SiO$_2$, DCM/MeOH 10/1) to give 2-[4-[7-(3-benzyloxy-1-naphthyl)-2-[2-(dimethylamino)ethoxy]-6,8-dihydro-5H-pyrido [3,4-d]pyrimidin-4-yl]-1-prop-2-enoyl-piperazin-2-yl]acetonitrile (40.0 mg, 63.3 umol, 61.0% yield) as a yellow oil. ES+APCI MS m/z 632.3[M+H]$^+$.

Step H: 2-[4-[2-[2-(dimethylamino)ethoxy]-7-(3-hydroxy-1-naphthyl)-6,8-dihydro-5H-pyrido[3,4-d]pyrimidin-4-yl]-1-prop-2-enoyl-piperazin-2-yl]acetonitrile: To a solution of 2-[4-[7-(3-benzyloxy-1-naphthyl)-2-[2-(dimethylamino)ethoxy]-6,8-dihydro-5H-pyrido[3,4-d] pyrimidin-4-yl]-1-prop-2-enoyl-piperazin-2-yl]acetonitrile (30 mg, 47.5 umol) in DCM (2 mL) was added BBr$_3$ (35.7 mg, 142 umol, 13.7 uL) at −78° C. under 0.5 h. The mixture was warmed up to 0° C. and stirred for 2 hours. The mixture was concentrated under vacuum and then quenched with saturated sodium bicarbonate solution at −78-0° C. The mixture was purified by column chromatography (Al$_2$O$_3$, DCM/MeOH=5/1), then further purified by prep-HPLC (column: Gemini 150*25 5 u; mobile phase: [water (0.05% ammonia hydroxide v/v)-ACN]; B %: 30%-60%,12 min). The desired fractions were collected and lyophilized to give 2-[4-[2-[2-(dimethylamino)ethoxy]-7-(3-hydroxy-1-naphthyl)-6,8-dihydro-5H-pyrido[3,4-d]pyrimidin-4-yl]-1-prop-2-enoyl-piperazin-2-yl]acetonitrile (810 ug, 1.46 umol, 3.07% yield, 97.5% purity) as a yellow solid. ES+APCI MS m/z 542.5 [M+H]$^+$.

Example 171
1-(4-(2-(2-(dimethylamino)ethoxy)-7-(3-hydroxynaphthalen-1-yl)-5,6,7,8-tetrahydropyrido[3,4-d]pyrimidin-4-yl)-2-(2-hydroxyethyl)piperazin-1-yl)prop-2-en-1-one
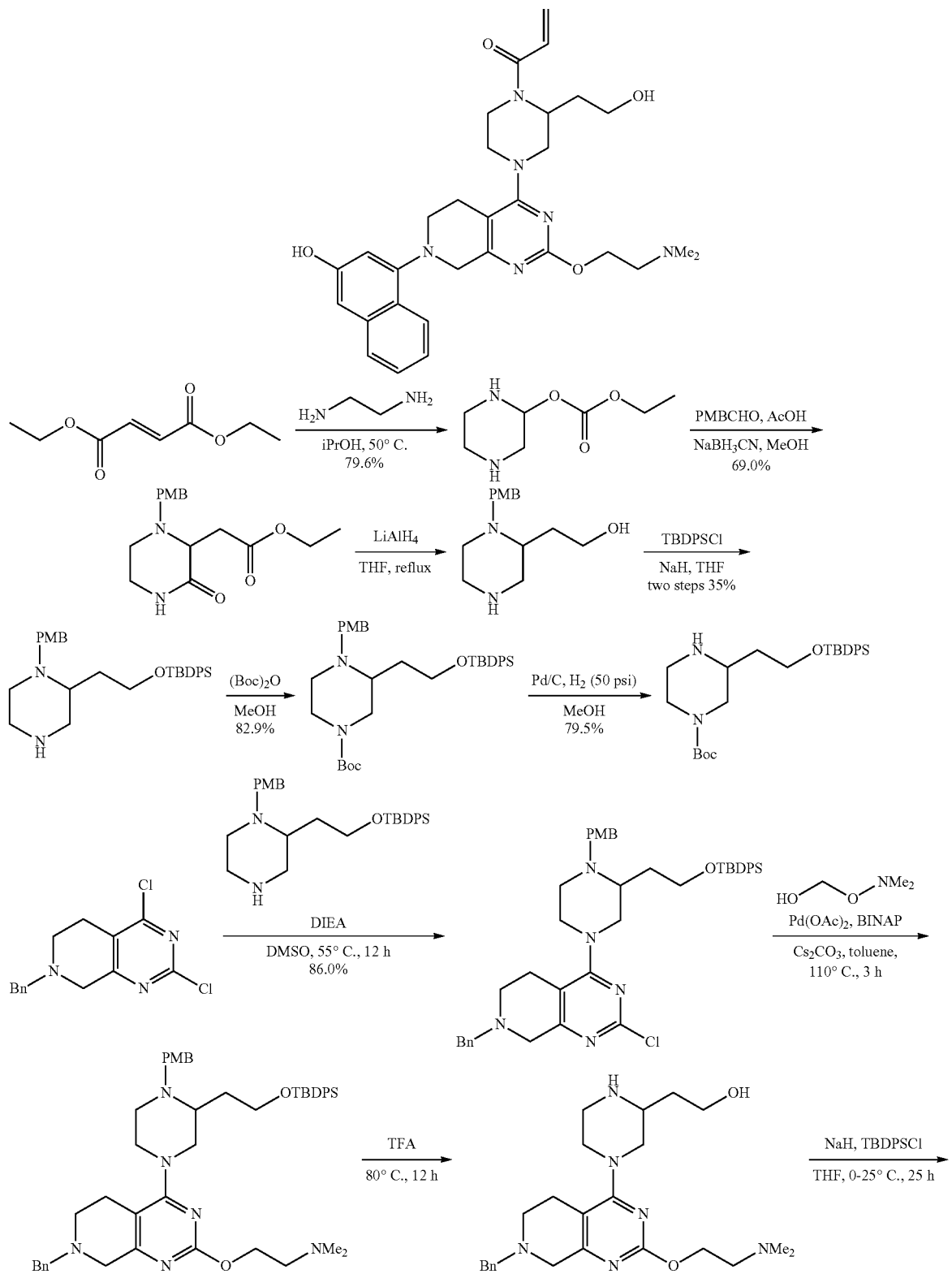

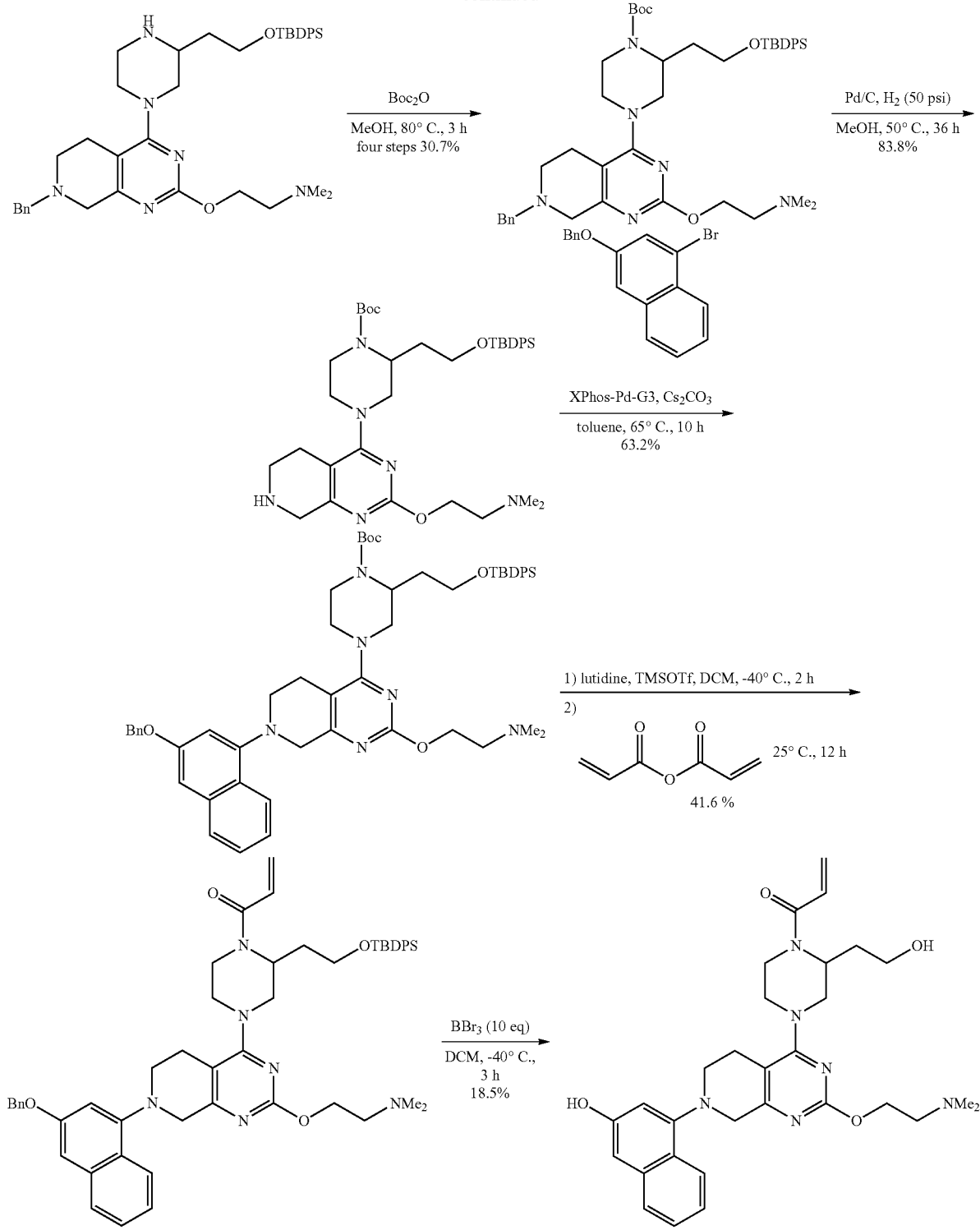

-continued

Step A: Ethyl 2-(3-oxopiperazin-2-yl)acetate

To a solution of diethyl (E)-but-2-enedioate (30.2 g, 175 mmol, 28.8 mL) in i-PrOH (300 mL) was added ethane-1,2-diamine (11.0 g, 183 mmol, 12.2 mL). After stirring at 25° C. for 12 hours, the reaction mixture was concentrated under reduced pressure to dryness. The crude white solid was washed with MTBE (500 mL) and dried under vacuum to give ethyl 2-(3-oxopiperazin-2-yl)acetate (26.0 g, 140 mmol, 79.6% yield, 100% purity) as a white solid. $^1$H NMR (400 MHz, Chloroform-d) δ=6.55 (br s, 1H), 4.15 (q, J=6.8 Hz, 2H), 3.80-3.72 (m, 1H), 3.47 (dt, J=4.8, 11.2 Hz, 1H), 3.36-3.22 (m, 1H), 3.18-3.08 (m, 1H), 3.07-2.95 (m, 2H), 2.76-2.70 (m, 1H), 1.25 (t, J=7.2 Hz, 3H).

Step B: Ethyl 2-[1-[(4-methoxyphenyl)methyl]-3-oxo-piperazin-2-yl]acetate

To a mixture of ethyl 2-(3-oxopiperazin-2-yl)acetate (23.6 g, 127 mmol) in methanol (400 mL) was added 4-methoxybenzaldehyde (18.9 g, 139 mmol, 16.9 mL) and $CH_3COOH$ (15.2 g, 253 mmol, 14.5 mL) at 0° C. After stirring at 0° C. for 1 hour, the reaction mixture was cooled to −10° C. $NaBH_3CN$ (23.9 g, 380 mmol) was added to the mixture in portions and the reaction mixture was warmed up to 15° C. and stirring for another 11 hours. The reaction was quenched by adding water (400 ML) and extracted with DCM (2×300 mL). The combined organic layers were dried over $Na_2SO_4$, filtered and concentrated. The residue was re-dissolved with ethyl acetate (300 mL), then washed with 0.5 M HCl solution (2×200 mL). The aqueous phase was adjusted to pH 7-8 with $Na_2CO_3$ solid, then extracted with DCM (2×300 mL). The combined organic layers were dried over $Na_2SO_4$, filtered and concentrated to give ethyl 2-[1-[(4-methoxyphenyl)methyl]-3-oxo-piperazin-2-yl]acetate (27.2 g, 87.6 mmol, 69.0% yield, 98.5% purity) as colorless oil. ES+APCI MS m/z 307.1 [M+H]$^+$.

Step C: 2-[1-[(4-methoxyphenyl)methyl]piperazin-2-yl]ethanol

To a mixture of ethyl 2-[1-[(4-methoxyphenyl)methyl]-3-oxo-piperazin-2-yl]acetate (27.2 g, 88.8 mmol) in THF (500 mL) was added $LiAlH_4$ (10.1 g, 266 mmol) in portions at 0° C. After stirring at 0° C. for 1 hour, the reaction mixture was heated to 70° C. and stirred for 11 hours. After completion, the reaction was quenched with sat.$Na_2SO_4$ aqueous (40 mL), filtered and then concentrated. The product 2-[1-[(4-methoxyphenyl)methyl]piperazin-2-yl]ethanol (20 g, crude) was obtained as yellow oil. ES+APCI MS m/z 251.1 [M+H]$^+$.

Step D: tert-butyl-[2-[1-[(4-methoxyphenyl)methyl]piperazin-2-yl]ethoxy]-diphenyl-silane To a mixture of 2-[1-[(4-methoxyphenyl)methyl]piperazin-2-yl]ethanol (20 g, crude) in THF (300 mL) was added NaH (15.9 g, 399 mmol, 60% purity) at 0° C. in portions, then a solution of TBDPSCl (65.9 g, 239 mmol, 61.6 mL) in THF (100 mL) was added. The mixture was warmed up to 15° C. and stirred for a further 12 hours. After completion, the reaction was poured into $NH_4Cl$ solution (300 mL), and extracted with DCM (2×300 mL). The combined organic layers were dried over $Na_2SO_4$, filtered and concentrated. The residue was purified by column chromatography ($SiO_2$, Petroleum ether: Ethyl acetate 3/1 to Dichloromethane/Methanol 10/1) to give tert-butyl-[2-[1-[(4-methoxyphenyl)methyl] piperazin-2-yl]ethoxy]-diphenyl-silane (29.5 g, 59.9 mmol, two steps 35%, 99.2% purity) as yellow oil. ES+APCI MS m/z 489.4[M+H]$^+$.

Step E: tert-butyl 3-[2-[tert-butyl(diphenyl)silyl]oxyethyl]-4-[(4-methoxyphenyl)methyl] piperazine-1-carboxylate To a mixture of tert-butyl-[2-[1-[(4-methoxyphenyl)methyl] piperazin-2-yl]ethoxy]-diphenyl-silane (11.0 g, 22.5 mmol) in MeOH (200 mL) was added TEA (6.83 g, 67.5 mmol, 9.36 mL) and $(Boc)_2O$ (9.82 g, 45.0 mmol, 10.3 mL). After stirring at 15° C. for 3 hours, the reaction was concentrated. The residue was purified by column chromatography ($SiO_2$, Petroleum: Ethyl acetate 1/0 to 5/1) to give tert-butyl 3-[2-[tert-butyl(diphenyl)silyl]oxyethyl]-4-[(4-methoxyphenyl)methyl] piperazine-1-carboxylate (11.0 g, 18.7 mmol, 82.9% yield, 100% purity) as colorless oil. ES+APCI MS m/z 589.4 [M+H]$^+$.

Step F: tert-butyl 3-[2-[tert-butyl(diphenyl) silyl]oxyethyl]piperazine-1-carboxylate To a mixture of tert-butyl 3-[2-[tert-butyl(diphenyl)silyl]oxyethyl]-4-[(4-methoxyphenyl)methyl]piperazine-1-carboxylate (9.00 g, 15.3 mmol) in MeOH (150 mL) was added 10% Pd/C (849 umol). The suspension was degassed under vacuum and purged with $H_2$ for three times. The mixture was stirred under $H_2$ (50 Psi) at 40° C. for 18 hours. After completion, the reaction mixture was filtered through a Celite plug and the filtrate was concentrated. The residue was purified by column chromatography ($SiO_2$, Petroleum ether/Ethyl acetate 10/1 to 3:1) to give tert-butyl 3-[2-[tert-butyl(diphenyl) silyl]oxyethyl]piperazine-1-carboxylate (5.80 g, 12.2 mmol, 79.5% yield, 98.2% purity) as colorless oil. ES+APCI MS m/z 469.4 [M+H]$^+$.

Step G: 2-[4-(7-benzyl-2-chloro-6,8-dihydro-5H-pyrido[3,4-d]pyrimidin-4-yl)-1-[(4-methoxyphenyl)methyl]piperazin-2-yl]ethoxy-tert-butyl-diphenyl-silane: A mixture of 7-benzyl-2,4-dichloro-6,8-dihydro-5H-pyrido[3,4-d]pyrimidine (4.00 g, 13.6 mmol), tert-butyl-[2-[1-[(4-methoxyphenyl)methyl] piperazin-2-yl]ethoxy]-diphenyl-silane (6.98 g, 14.3 mmol) and DIEA (4.39 g, 34.0 mmol, 5.93 mL) in DMSO (80 mL) was degassed and purged with $N_2$ for 3 times, and the mixture was heated to at 55° C. and stirred for 12 hours under $N_2$ atmosphere. The reaction mixture was diluted with water (300 mL) and extracted with ethyl acetate (3×200 mL). The combined organic layers were washed with brine (3×200 mL), dried over $Na_2SO_4$, filtered and concentrated under reduced pressure to dryness. The residue was purified by column chromatography ($SiO_2$, Petroleum ether/Ethyl acetate 1/0 to 3/1) to give 2-[4-(7-benzyl-2-chloro-6,8-dihydro-5H-pyrido[3,4-d]pyrimidin-4-yl)-1-[(4-methoxyphenyl)methyl]piperazin-2-yl]ethoxy-tert-butyl-diphenyl-silane (9.00 g, 11.7 mmol, 86.0% yield, 97.0% purity) as a yellow oil. ES+APCI MS m/z 746.4[M+H]$^+$.

Step H: 2-[[7-benzyl-4-[3-[2-[tert-butyl(diphenyl)silyl]oxyethyl]-4-[(4-methoxyphenyl) methyl]piperazin-1-yl]-6,8-dihydro-5H-pyrido[3,4-d]pyrimidin-2-yl]oxy]-N,N-dimethyl-ethanamine: A mixture of 2-(dimethylamino)ethanol (2.39 g, 26.8 mmol, 2.69 mL), 2-[4-(7-benzyl-2-chloro-6,8-dihydro-5H-pyrido[3,4-d]pyrimidin-4-yl)-1-[(4-methoxyphenyl)methyl]piperazin-2-yl]ethoxy-tert-butyl-diphenyl-silane (8.00 g, 10.7 mmol), $Pd(OAc)_2$ (361 mg, 1.61 mmol), BINAP (1.34 g, 2.14 mmol) and $Cs_2CO_3$ (8.73 g, 26.8 mmol) in toluene (100 mL) was degassed and purged with $N_2$ for 3 times. The mixture was heated to 110° C. and stirred for 3 hours under $N_2$ atmosphere. The reaction mixture was filtered and the filtrate was concentrated under reduced pressure to dryness. The residue was purified by column chromatography ($SiO_2$, DCM/MeOH 50/1 to 10/1) to give 2-[[7-benzyl-4-[3-[2-[tert-butyl(diphenyl)silyl]oxyethyl]-4-[(4-methoxyphenyl) methyl]piperazin-1-yl]-6,8-dihydro-5H-pyrido[3,4-d]pyrimidin-2-yl]oxy]-N,N-dimethyl-ethanamine (6.50 g, crude) as a yellow semisolid. ES+APCI MS m/z 799.4 [M+H]$^+$.

Step I: 2-[4-[7-benzyl-2-[2-(dimethyl amino) ethoxy]-6,8-dihydro-5H-pyrido [3,4-d]pyrimidin-4-yl]piperazin-2-yl]ethanol 2-[4-[7-benzyl-2-[2-(dimethyl amino)ethoxy]-6,8-dihydro-5H-pyrido [3,4-d]pyrimidin-4-yl]piperazin-2-yl]ethanol: A solution of 2-[[7-benzyl-4-[3-[2-[tert-butyl (diphenyl) silyl]oxyethyl]-4-[(4-methoxyphenyl)methyl]piperazin-1-yl]-6,8-dihydro-5H-pyrido[3,4-d]pyrimidin-2-yl]oxy]-N,N-dimethyl-ethanamine (6.50 g, crude) in TFA (80 mL) was stirred at 80° C. for 12 hours. The reaction mixture was concentrated under reduced pressure to dryness and the residue was re-dissolved into DCM (300 mL) and washed with water (200 mL). The water phase was collected and basified with saturated NaHCO$_3$ aqueous to pH ~8 and then extracted with DCM (3×200 mL). The combined organic phase was dried over Na$_2$SO$_4$, filtered and concentrated under reduced pressure to give 2-[4-[7-benzyl-2-[2-(dimethyl amino)ethoxy]-6,8-dihydro-5H-pyrido [3,4-d]pyrimidin-4-yl]piperazin-2-yl]ethanol (3.00 g, crude) as a yellow semisolid, which was used directly for next step without further purification.

Step J: 2-[[7-benzyl-4-[3-[2-[tert-butyl(diphenyl)silyl] oxyethyl]piperazin-1-yl]-6,8-dihydro-5H-pyrido[3,4-d]pyrimidin-2-yl]oxy]-N,N-dimethyl-ethanamine: A solution of 2-[4-[7-benzyl-2-[2-(dimethylamino)ethoxy]-6,8-dihydro-5H-pyrido[3,4-d]pyrimidin-4-yl] piperazin-2-yl]ethanol (3.0 g, crude) in THF (40 mL) was added NaH (1.36 g, 34.1 mmol, 60.0% purity) at 0° C. After stirring for 30 minutes, TBDPSCl (2.81 g, 10.2 mmol, 2.63 mL) was added by portions. The mixture was warmed to 25° C. and stirred for another 2 hours under N$_2$ atmosphere. The reaction mixture was quenched by addition water (30 mL) at 0° C. and extracted into ethyl acetate (3×100 mL). The combined organic layers were washed with brine (3×100 mL), dried over Na$_2$SO$_4$, filtered and concentrated under reduced pressure to dryness to give 2-[[7-benzyl-4-[3-[2-[tert-butyl(diphenyl)silyl]oxyethyl]piperazin-1-yl]-6,8-dihydro-5H-pyrido[3,4-d]pyrimidin-2-yl]oxy]-N,N-dimethyl-ethanamine (6.00 g, crude) as a yellow oil, which was used directly for next step without further purification. ES+APCI MS m/z 679.4 [M+H]$^+$.

Step K: tert-butyl4-[7-benzyl-2-[2-(dimethylamino) ethoxy]-6,8-dihydro-5H-pyrido[3,4-d]pyrimidin-4-yl]-2-[2-[tert-butyl(diphenyl)silyl]oxyethyl]piperazine-1-carboxylate: A mixture of 2-[[7-benzyl-4-[3-[2-[tert-butyl(diphenyl) silyl]oxyethyl] piperazin-1-yl]-6,8-dihydro-5H-pyrido[3,4-d]pyrimidin-2-yl]oxy]-N,N-dimethyl-ethanamine (6.0 g, crude), Boc$_2$O (18.5 g, 84.8 mmol, 19.5 mL) in MeOH (3 mL) was degassed and purged with N$_2$ for 3 times. The mixture was heated to 80° C. and stirred for 3 hours under N$_2$ atmosphere. The reaction mixture was concentrated under reduced pressure to dryness. The residue was purified by column chromatography (SiO$_2$, DCM/MeOH 1/0 to 10/1) to give tert-butyl4-[7-benzyl-2-[2-(dimethylamino)ethoxy]-6,8-dihydro-5H-pyrido[3,4-d]pyrimidin-4-yl]-2-[2-[tert-butyl(diphenyl)silyl]oxyethyl]piperazine-1-carboxylate (3.10 g, 3.28 mmol, four steps 30.7% yield, 82.2% purity) as a semisolid. ES+APCI MS m/z 779.4 [M+H]$^+$.

Step L: tert-butyl2-[2-[tert-butyl(diphenyl)silyl]oxyethyl]-4-[2-[2-(dimethylamino)ethoxy]-5,6,7,8-tetrahydropyrido[3,4-d]pyrimidin-4-yl]piperazine-1-carboxylate: To a solution of tert-butyl4-[7-benzyl-2-[2-(dimethylamino) ethoxy]-6,8-dihydro-5H-pyrido [3,4-d]pyrimidin-4-yl]-2-[2-[tert-butyl(diphenyl)silyl]oxyethyl]piperazine-1-carboxylate (3.10 g, 3.28 mmol, 82.2% purity) in MeOH (60 mL) was added Pd—C (10%, 2 g) under N$_2$. The suspension was degassed under vacuum and purged with H$_2$ for three times. The mixture was stirred under H$_2$ (50 psi) at 50° C. for 36 hours. The reaction mixture was filtered and concentrated under reduced pressure to dryness to give tert-butyl2-[2-[tert-butyl(diphenyl)silyl]oxyethyl]-4-[2-[2-(dimethylamino)ethoxy]-5,6,7,8-tetrahydropyrido[3,4-d]pyrimidin-4-yl]piperazine-1-carboxylate (2.20 g, 2.75 mmol, 83.8% yield, 86.0% purity) as a yellow solid, which was used directly for next step without further purification. ES+APCI MS m/z 689.4 [M+H]$^+$.

Step M: tert-butyl4-[7-(3-benzyloxy-1-naphthyl)-2-[2-(dimethylamino)ethoxy]-6,8-dihydro-5H-pyrido[3,4-d]pyrimidin-4-yl]-2-[2-[tert-butyl(diphenyl)silyl]oxyethyl]piperazine-1-carboxylate: A mixture of tert-butyl2-[2-[tert-butyl(diphenyl)silyl]oxyethyl]-4-[2-[2-(dimethylamino) ethoxy]-5,6,7,8-tetrahydropyrido[3,4-d]pyrimidin-4-yl] piperazine-1-carboxylate (1.85 g, 2.69 mmol), 3-benzyloxy-1-bromo-naphthalene (1.09 g, 3.49 mmol), Cs$_2$CO$_3$ (2.19 g, 6.71 mmol), [2-(2-aminophenyl)phenyl]palladium(1+); dicyclohexyl-[2-(2,4,6-triisopropylphenyl)phenyl]phosphane; methanesulfonate (341 mg, 403 umol) in toluene (40 mL) was degassed and purged with N$_2$ for 3 times, and the mixture was stirred at 65° C. for 10 hours under N$_2$ atmosphere. After completion, the reaction mixture was filtered and concentrated under reduced pressure to dryness. The residue was purified by column chromatography (SiO$_2$, DCM/MeOH 1/0 to 10/1) to give tert-butyl4-[7-(3-benzyloxy-1-naphthyl)-2-[2-(dimethylamino)ethoxy]-6,8-dihydro-5H-pyrido[3,4-d]pyrimidin-4-yl]-2-[2-[tert-butyl(diphenyl)silyl]oxyethyl]piperazine-1-carboxylate (1.85 g, 1.69 mmol, 63.2% yield, 84.3% purity) as a yellow solid. ES+APCI MS m/z 922.5 [M+H]$^+$.

Step N: 1-[4-[7-(3-benzyloxy-1-naphthyl)-2-[2-(dimethylamino)ethoxy]-6,8-dihydro-5H-pyrido[3,4-d]pyrimidin-4-yl]-2-[2-[tert-butyl(diphenyl)silyl]oxyethyl]piperazin-1-yl]prop-2-en-1-one: To a solution of tert-butyl 4-[7-(3-benzyloxy-1-naphthyl)-2-[2-(dimethylamino)ethoxy]-6,8-dihydro-5H-pyrido[3,4-d]pyrimidin-4-yl]-2-[2-[tert-butyl (diphenyl)silyl]oxyethyl]piperazine-1-carboxylate (500 mg, 543 umol), 2,6-lutidine (700 mg, 6.51 mmol, 759 uL) in DCM (10 mL) was added TMSOTf (724 mg, 3.26 mmol, 588 uL). After stirring at 40° C. for 2 hours under N$_2$ atmosphere, the reaction mixture was cooled to −40° C. and prop-2-enoyl prop-2-enoate (137 mg, 1.09 mmol) was added portionwise. The reaction mixture was warmed to 25° C. and stirred for another 12 hours under N$_2$ atmosphere. After completion, the reaction mixture was purified directly by column chromatography (SiO$_2$, DCM/MeOH 30/1 to 10/1) to give 1-[4-[7-(3-benzyloxy-1-naphthyl)-2-[2-(dimethylamino)ethoxy]-6,8-dihydro-5H-pyrido[3,4-d]pyrimidin-4-yl]-2-[2-[tert-butyl(diphenyl)silyl]oxyethyl]piperazin-1-yl]prop-2-en-1-one (256 mg, 226 umol, 41.6% yield, 77.2% purity) as a semisolid. ES+APCI MS m/z 875.5 [M+H]$^+$.

Step O: 1-[4-[2-[2-(dimethylamino)ethoxy]-7-(3-hydroxy-1-naphthyl)-6,8-dihydro-5H-pyrido [3,4-d]pyrimidin-4-yl]-2-(2-hydroxyethyl)piperazin-1-yl]prop-2-en-1-one: To a solution of 1-[4-[7-(3-benzyloxy-1-naphthyl)-2-[2-(dimethyl amino)ethoxy]-6,8-dihydro-5H-pyrido [3,4-d] pyrimidin-4-yl]-2-[2-[tert-butyl(diphenyl)silyl]oxyethyl] piperazin-1-yl]prop-2-en-1-one (133 mg, 152 umol) in DCM (5.00 mL) was added BBr$_3$ (571 mg, 2.28 mmol, 220 uL) dropwise at −40° C. The reaction mixture was warmed to 0° C. and stirred for 3 hours. The mixture was concentrated under reduced pressure to dryness. The crude material was washed with MTBE (25 mL) and the solid was collected. The solid was washed with saturated NaHCO$_3$ solution (0.5 mL) to pH ~8 at 0° C. then dissolved in MeOH (3 mL). The mixture was directly purified by prep-HPLC (column: Boston Green ODS 150*30 5 u; mobile phase: [water (0.225% Formic Acid)-ACN]; B %: 15-39%, 10 min) to give 1-[4-[2-[2-(dimethylamino)ethoxy]-7-(3-hydroxy-1-naphthyl)-6,8-dihydro-5H-pyrido [3,4-d]pyrimidin-4-yl]-2-(2-hydroxyethyl)piperazin-1-yl]prop-2-en-1-one (16.7 mg, 28.2 umol, 18.5% yield, 99.9% purity, Formic Acid Salt) as a yellow solid. ES+APCI MS m/z 547.3 [M+H]$^+$.

Example 172
1-(4-(2-(2-(dimethylamino)ethoxy)-7-(3-hy-droxynaphthalen-1-yl)-5,6,7,8-tetrahydropyrido[3,4-d]pyrimidin-4-yl)-3-(2-hydroxyethyl)piperazin-1-yl)prop-2-en-1-one
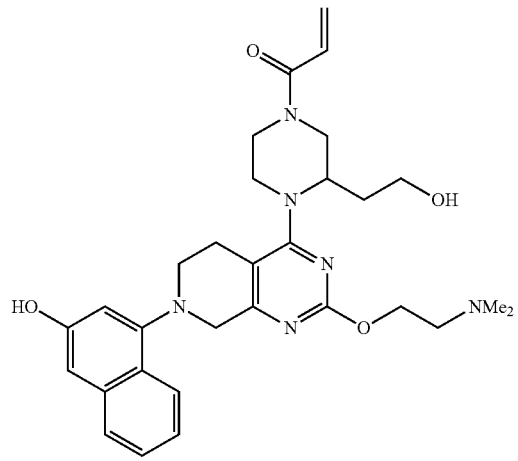
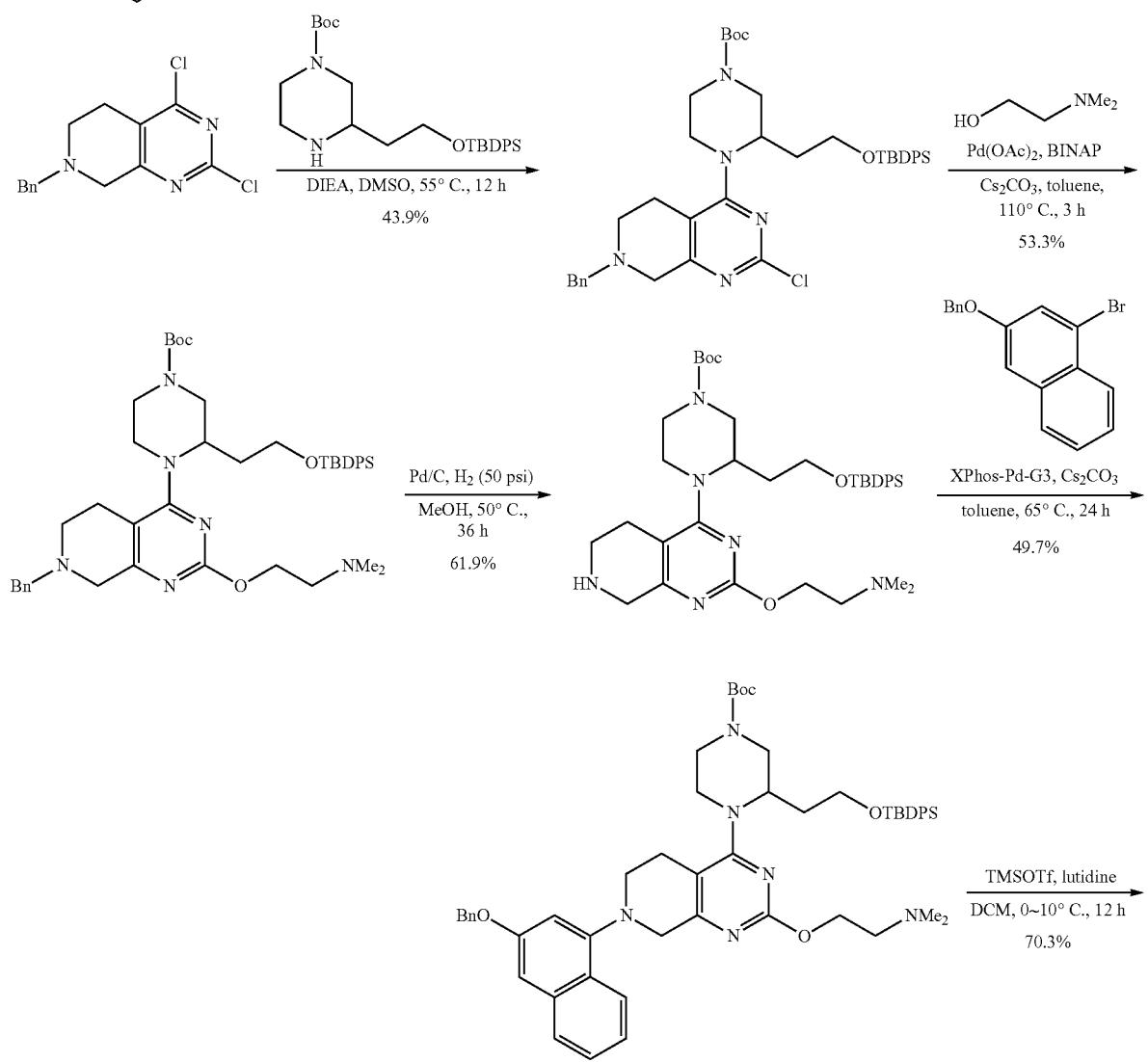

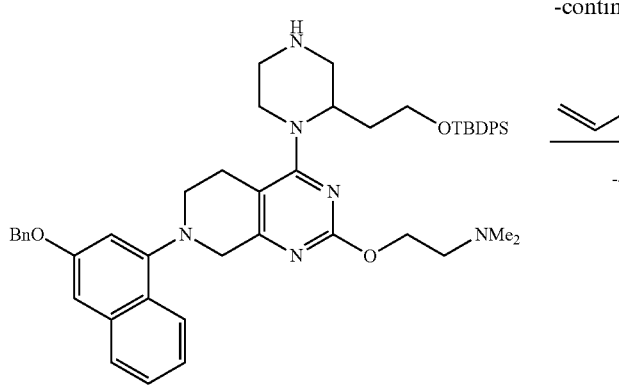

-continued

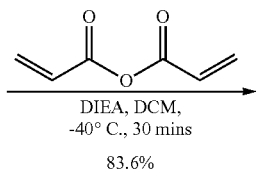

DIEA, DCM,
-40° C., 30 mins
83.6%

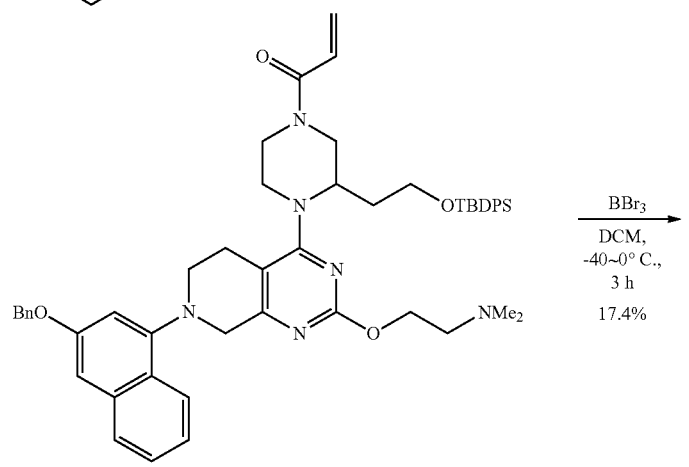

BBr₃
DCM,
-40~0° C.,
3 h
17.4%

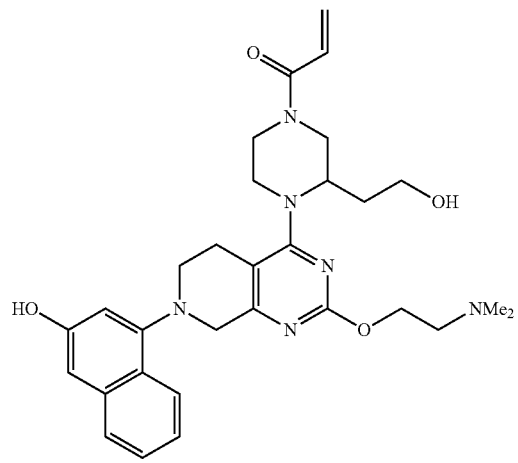

Step A: tert-butyl4-(7-benzyl-2-chloro-6,8-dihydro-5H-pyrido[3,4-d]pyrimidin-4-yl)-3-[2-[tert-butyl(diphenyl)silyl]oxyethyl]piperazine-1-carboxylate: A mixture of 7-benzyl-2,4-dichloro-6,8-dihydro-5H-pyrido[3,4-d] pyrimidine (3.04 g, 10.3 mmol), tert-butyl3-[2-[tert-butyl(diphenyl)silyl]oxyethyl] piperazine-1-carboxylate (5.08 g, 10.8 mmol), DIEA (3.34 g, 25.8 mmol, 4.51 mL) in DMSO (60 mL) was degassed and purged with $N_2$ for 3 times. The mixture heated to 55° C. and stirred for 16 hours under a $N_2$ atmosphere. After cooling to room temperature, the reaction mixture was diluted with water (100 mL) and extracted with ethyl acetate (3×100 mL). The combined organic layers were washed with brine (3×100 mL), dried over $Na_2SO_4$, filtered and concentrated under reduced pressure to dryness. The residue was purified by column chromatography ($SiO_2$, Petroleum ether/Ethyl acetate 1/0 to 3/1) to give tert-butyl4-(7-benzyl-2-chloro-6,8-dihydro-5H-pyrido[3,4-d]pyrimidin-4-yl)-3-[2-[tert-butyl(diphenyl)silyl]oxyethyl]piperazine-1-carboxylate (3.50 g, 4.53 mmol, 43.9% yield, 94.0% purity) as a yellow semisolid. ES+APCI MS m/z 726.4 $[M+H]^+$.

Step B: tert-butyl 4-[7-benzyl-2-[2-(dimethylamino)ethoxy]-6,8-dihydro-5H-pyrido[3,4-d]pyrimidin-4-yl]-3-[2-[tert-butyl(diphenyl)silyl]oxyethyl]piperazine-1-carboxylate: A mixture of 2-(dimethylamino)ethanol (1.07 g, 12.1 mmol, 1.21 mL), tert-butyl4-(7-benzyl-2-chloro-6,8-dihydro-5H-pyrido[3,4-d]pyrimidin-4-yl)-3-[2-[tert-butyl(diphenyl)silyl]oxyethyl]piperazine-1-carboxylate (3.50 g, 4.82 mmol), Pd(OAc)₂ (162 mg, 723 umol), BINAP (600 mg, 964 umol) and Cs₂CO₃ (3.92 g, 12.1 mmol) in toluene (40 mL) was degassed and purged with $N_2$ for 3 times. The mixture was heated to 110° C. with stirring for 3 hours under N₂ atmosphere. After cooling to the room temperature, the reaction mixture was filtered and concentrated under reduced pressure to dryness. The residue was purified by column chromatography (SiO₂, DCM/MeOH=1/0 to 10/1) to give tert-butyl 4-[7-benzyl-2-[2-(dimethylamino)ethoxy]-6,8-dihydro-5H-pyrido[3,4-d]pyrimidin-4-yl]-3-[2-[tert-butyl(diphenyl)silyl]oxyethyl]piperazine-1-carboxylate (2.30 g, 2.57 mmol, 53.3% yield, 87.0% purity) as a yellow solid. ES+APCI MS m/z 779.5 [M+H]⁺.

Step C: tert-butyl 3-[2-[tert-butyl(diphenyl)silyl]oxyethyl]-4-[2-[2-(dimethylamino)ethoxy]-5,6,7,8-tetrahydropyrido[3,4-d]pyrimidin-4-yl]piperazine-1-carboxylate: To a solution of tert-butyl 4-[7-benzyl-2-[2-(dimethylamino)ethoxy]-6,8-dihydro-5H-pyrido[3,4-d]pyrimidin-4-yl]-3-[2-[tert-butyl(diphenyl)silyl]oxyethyl] piperazine-1-carboxylate (2.30 g, 2.95 mmol) in MeOH (40 mL) was added Pd—C (10%, 1.5 g) under N₂. The suspension was degassed under vacuum and purged with H₂ several times. After stirring under H₂ (50 psi) at 50° C. for 36 hours, the reaction mixture was filtered and concentrated under reduced pressure to give tert-butyl 3-[2-[tert-butyl(diphenyl)silyl]oxyethyl]-4-[2-[2-(dimethylamino)ethoxy]-5,6,7,8-tetrahydropyrido[3,4-d]pyrimidin-4-yl]piperazine-1-carboxylate (1.58 g, 1.83 mmol, 61.9% yield, 79.6% purity) as a colorless oil, which was used directly for next step without further purification. ES+APCI MS m/z 689.4 [M+H]⁺.

Step D: tert-butyl4-[7-(3-benzyloxy-1-naphthyl)-2-[2-(dimethylamino)ethoxy]-6,8-dihydro-5H-pyrido[3,4-d]pyrimidin-4-yl]-3-[2-[tert-butyl(diphenyl)silyl]oxyethyl] piperazine-1-carboxylate: A mixture of tert-butyl 3-[2-[tert-butyl(diphenyl)silyl]oxyethyl]-4-[2-[2-(dimethylamino)ethoxy]-5,6,7,8-tetrahydropyrido[3,4-d]pyrimidin-4-yl] piperazine-1-carboxylate (1.48 g, 2.15 mmol), 3-benzyloxy-1-bromo-naphthalene (875 mg, 2.80 mmol), Cs₂CO₃ (1.75 g, 5.38 mmol), [2-(2-aminophenyl)phenyl]palladium(1+); dicyclohexyl-[2-(2,4,6-triisopropylphenyl)phenyl]phosphane; methanesulfonate (273 mg, 323 umol) in toluene (30 mL) was degassed and purged with N₂ for 3 times, and then the mixture was stirred at 65° C. for 24 hours under N₂ atmosphere. The reaction mixture was filtered and concentrated under reduced pressure to dryness. The residue was purified by column chromatography (Al₂O₃, DCM/MeOH=1/0 to 20/1) to give tert-butyl4-[7-(3-benzyloxy-1-naphthyl)-2-[2-(dimethylamino)ethoxy]-6,8-dihydro-5H-pyrido[3,4-d]pyrimidin-4-yl]-3-[2-[tert-butyl(diphenyl)silyl]oxyethyl]piperazine-1-carboxylate (1.20 g, 1.07 mmol, 49.7% yield, 82.0% purity) as a yellow solid. ES+APCI MS m/z 921.4 [M+H]⁺.

Step E: 2-[[7-(3-benzyloxy-1-naphthyl)-4-[2-[2-[tert-butyl (diphenyl)silyl]oxyethyl]piperazin-1-yl]-6,8-dihydro-5H-pyrido[3,4-d]pyrimidin-2-yl] oxy]-N,N-dimethyl-ethanamine: A mixture of tert-butyl4-[7-(3-benzyloxy-1-naphthyl)-2-[2-(dimethyl amino)ethoxy]-6,8-dihydro-5H-pyrido[3,4-d] pyrimidin-4-yl]-3-[2-[tert-butyl(diphenyl)silyl]oxyethyl]piperazine-1-carboxylate (300 mg, 326 umol) and 2,6-lutidine (419 mg, 3.91 mmol, 455 uL) in DCM (10 mL) was added TMSOTf (434 mg, 1.95 mmol, 353 uL) portionwise at 0° C. The mixture was warmed to 10° C. and stirred for 12 hours under N₂ atmosphere. The reaction mixture was purified directly by column chromatography (Al₂O₃, DCM/MeOH 1/0 to 50/1) to give 2-[[7-(3-benzyloxy-1-naphthyl)-4-[2-[2-[tert-butyl (diphenyl)silyl]oxyethyl] piperazin-1-yl]-6,8-dihydro-5H-pyrido[3,4-d]pyrimidin-2-yl]oxy]-N,N-dimethyl-ethanamine (210 mg, 229 umol, 70.3% yield, 89.5% purity) as a yellow semi-solid. ES+APCI MS m/z 821.5 [M+H]⁺.

Step F: 1-[4-[7-(3-benzyloxy-1-naphthyl)-2-[2-(dimethylamino)ethoxy]-6,8-dihydro-5H-pyrido [3,4-d]pyrimidin-4-yl]-3-[2-[tert-butyl(diphenyl)silyl] oxyethyl]piperazin-1-yl]prop-2-en-1-one: To a mixture of 2-[[7-(3-benzyloxy-1-naphthyl)-4-[2-[2-[tert-butyl(diphenyl)silyl] oxyethyl] piperazin-1-yl]-6,8-dihydro-5H-pyrido[3,4-d] pyrimidin-2-yl]oxy]-N,N-dimethyl-ethanamine (210 mg, 256 umol) and DIEA (49.6 mg, 384 umol, 67.0 uL) in DCM (10 mL) was added prop-2-enoyl prop-2-enoate (33.9 mg, 269 umol) portionwise at −40° C. under nitrogen atmosphere. After stirring for 30 minutes at the same temperature, the reaction mixture was purified directly by column chromatography (Al₂O₃, DCM/MeOH 1/0 to 50/1) to give 1-[4-[7-(3-benzyloxy-1-naphthyl)-2-[2-(dimethylamino)ethoxy]-6,8-dihydro-5H-pyrido [3,4-d]pyrimidin-4-yl]-3-[2-[tert-butyl(diphenyl)silyl] oxyethyl]piperazin-1-yl]prop-2-en-1-one (221 mg, 214 umol, 83.6% yield, 84.7% purity) as a slight yellow semi-solid. ES+APCI MS m/z 875.4 [M+H]⁺.

Step G: 1-[4-[2-[2-(dimethylamino)ethoxy]-7-(3-hydroxy-1-naphthyl)-6,8-dihydro-5H-pyrido[3,4-d]pyrimidin-4-yl]-3-(2-hydroxyethyl)piperazin-1-yl]prop-2-en-1-one: A mixture of 1-[4-[7-(3-benzyloxy-1-naphthyl)-2-[2-(dimethylamino) ethoxy]-6,8-dihydro-5H-pyrido [3,4-d]pyrimidin-4-yl]-3-[2-[tert-butyl(diphenyl)silyl]oxyethyl]piperazin-1-yl]prop-2-en-1-one (221 mg, 253 umol) in DCM (10 mL) was added BBr₃ (949 mg, 3.79 mmol, 365 uL) at −40° C. The mixture was stirred at 0° C. for 3 hours under N₂ atmosphere. The reaction mixture was concentrated under reduced pressure to dryness. The crude pdt was washed with MTBE (25 mL), saturated NaHCO₃ solution (0.5 mL) to pH ~8 at 0° C. and dissolved in MeOH (3 mL). The resulting solution was purified by prep-HPLC (column: Boston Green ODS 150*30 5 u; mobile phase: [water (0.225% Formic Acid)-ACN]; B %: 11%-41%, 10 min) to give 1-[4-[2-[2-(dimethylamino)ethoxy]-7-(3-hydroxy-1-naphthyl)-6,8-dihydro-5H-pyrido[3,4-d]pyrimidin-4-yl]-3-(2-hydroxyethyl) piperazin-1-yl]prop-2-en-1-one (26.7 mg, 44.0 umol, 17.4% yield, 97.8% purity, Formic Acid Salt) as a yellow solid. ES+APCI MS m/z 547.3 [M+H]⁺.

Example 173
1-(4-(7-(3-hydroxy-2-methylnaphthalen-1-yl)-2-(3-morpholinopropoxy)-5,6,7,8-tetrahydropyrido[3,4-d]pyrimidin-4-yl)piperazin-1-yl)prop-2-en-1-one
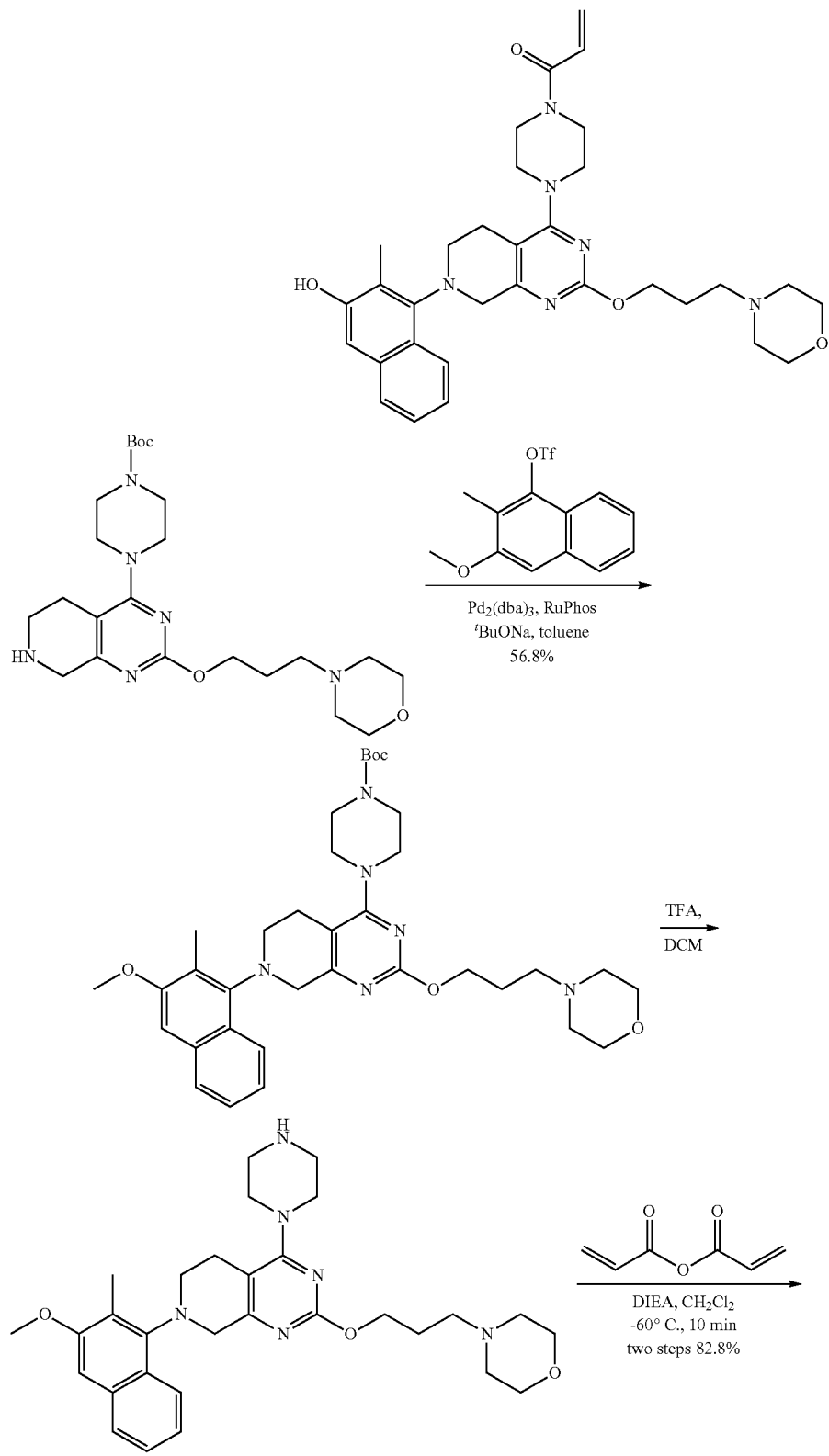

-continued

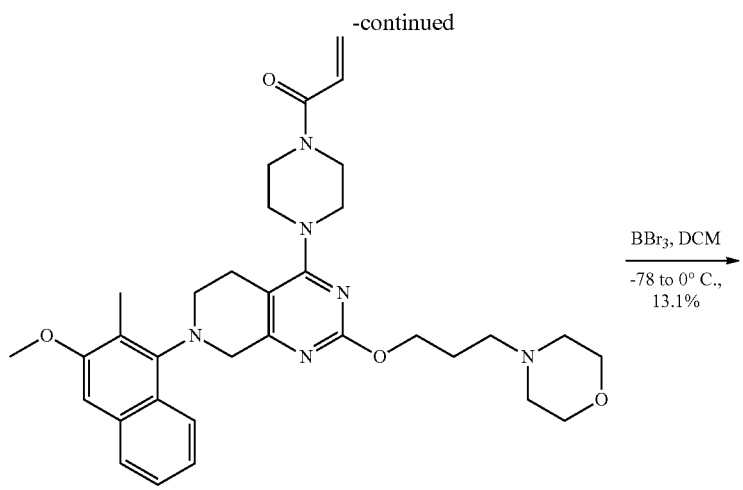

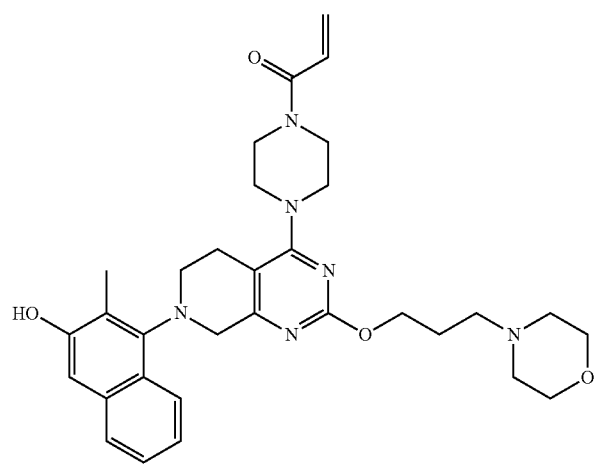

1-(4-(7-(3-hydroxy-2-methylnaphthalen-1-yl)-2-(3-morpholinopropoxy)-5,6,7,8-tetrahydropyrido[3,4-d]pyrimidin-4-yl)piperazin-1-yl)prop-2-en-1-one was prepared according to the procedure for Example 165 1-[4-[7-(2-fluoro-3-hydroxy-1-naphthyl)-2-(3-morpholinopropoxy)-6,8-dihydro-5H-pyrido[3,4-d]pyrimidin-4-yl]piperazin-1-yl]prop-2-en-1-one substituting (3-methoxy-2-methyl-1-naphthyl) trifluoromethanesulfonate for (2-fluoro-3-methoxy-1-naphthyl) trifluoromethanesulfonate in step F to give the desired product 1-(4-(7-(3-hydroxy-2-methylnaphthalen-1-yl)-2-(3-morpholinopropoxy)-5,6,7,8-tetrahydropyrido [3,4-d]pyrimidin-4-yl)piperazin-1-yl)prop-2-en-1-one as yellow solid (10.4 mg, 13.1% yield, 98.1% purity). ES+APCI MS m/z 573.5 [M+H]$^+$.

Example 174
(R)-1-(4-(2-((5,5-dimethylpyrrolidin-2-yl)methoxy)-7-(3-hydroxynaphthalen-1-yl)-5,6,7,8-tetrahydro-pyrido[3,4-d]pyrimidin-4-yl)piperazin-1-yl)prop-2-en-1-one
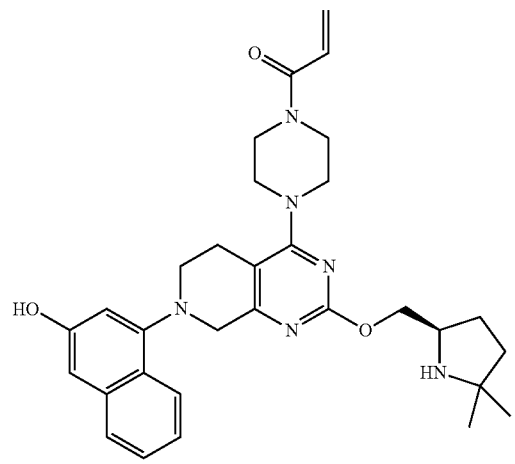
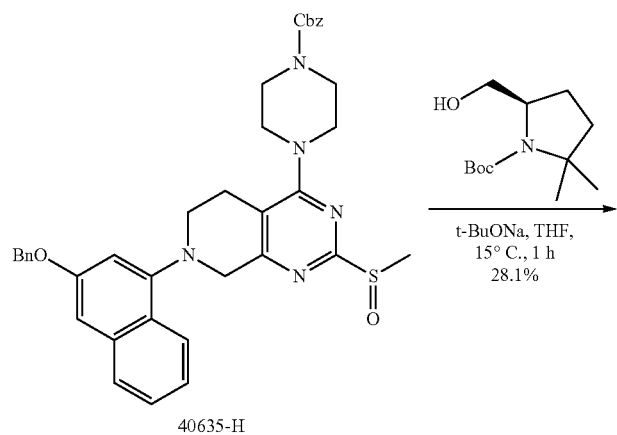
40635-H
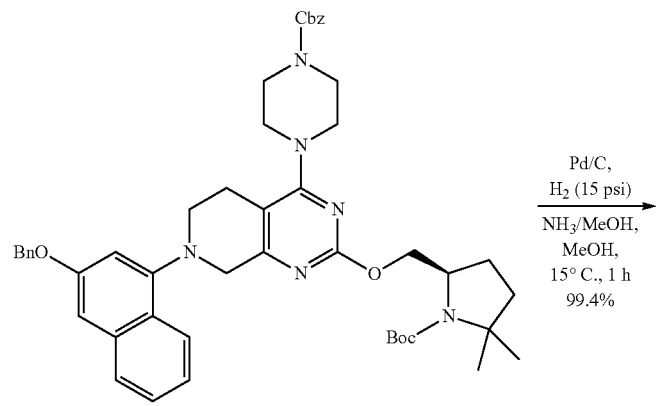
40758-1

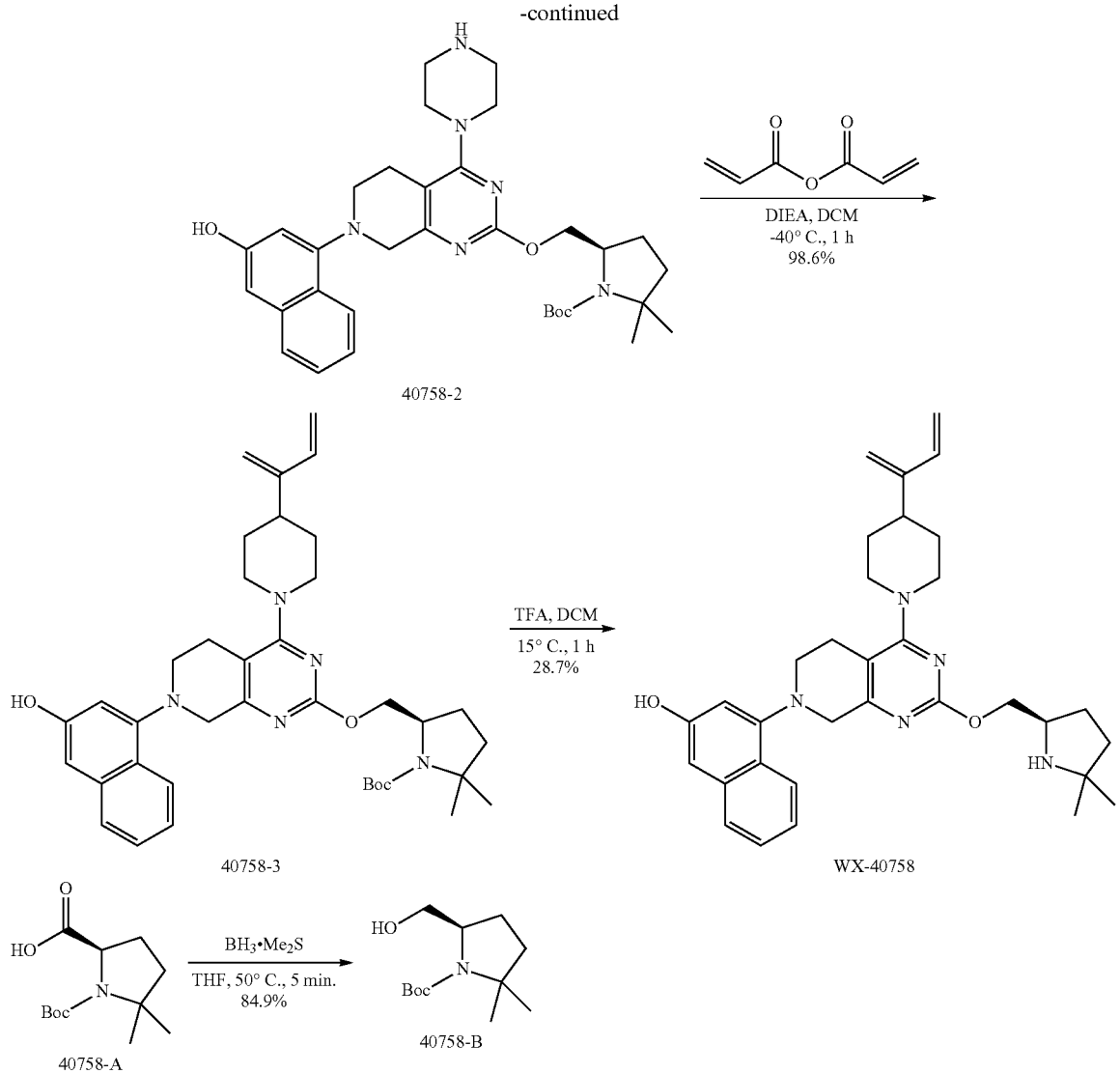

Step A: tert-Butyl (5R)-5-(hydroxymethyl)-2,2-dimethyl-pyrrolidine-1-carboxylate To a solution of (2R)-1-tert-butoxycarbonyl-5,5-dimethyl-pyrrolidine-2-carboxylic acid (500 mg, 2.06 mmol) in anhydrous THF (4 mL) was added BH₃-Me₂S (2 M, 1.23 mL) dropwise at 15° C. The reaction was heated at 50° C. for 5 minutes. After cooling in an ice-bath, to the mixture was added Methanol (20 mL). The reaction mixture was concentrated under reduced pressure at 25° C. tert-Butyl (5R)-5-(hydroxymethyl)-2,2-dimethyl-pyrrolidine-1-carboxylate (400 mg, 1.74 mmol, 84.9% yield) was obtained as a white solid.

$^1$H NMR (400 MHz, methanol-$d_4$) δ=3.97-3.81 (m, 1H), 3.62 (dd, J=3.6, 10.8 Hz, 1H), 3.45-3.33 (m, 1H), 2.02-1.79 (m, 3H), 1.79-1.67 (m, 1H), 1.49-1.41 (m, 12H), 1.32 (s, 3H).

Step B: Benzyl 4-[7-(3-benzyloxy-1-naphthyl)-2-[[(2R)-1-tert-butoxycarbonyl-5,5-dimethyl-pyrrolidin-2-yl]methoxy]-6,8-dihydro-5H-pyrido[3,4-d]pyrimidin-4-yl]piperazine-1-carboxylate: To a solution of tert-butyl (5R)-5-(hydroxymethyl)-2,2-dimethyl-pyrrolidine-1-carboxylate (212 mg, 926 umol) and benzyl 4-[7-(3-benzyloxy-1-naphthyl)-2-methylsulfinyl-6,8-dihydro-5H-pyrido[3,4-d]pyrimidin-4-yl]piperazine-1-carboxylate (300 mg, 463 umol) in THF (10 mL) was added t-BuONa (133 mg, 1.39 mmol). After stirring at 15° C. for 1 hour, the reaction mixture was poured into H₂O (20 mL) and extracted with ethyl acetate (20 mL×3). The organic phase was washed with brine (20 mL), dried over anhydrous Na₂SO₄, filtered and concentrated in vacuo. The residue was purified by reversed phase flash [water (0.1% formic acid)/acetonitrile]. The desired fractions were collected and concentrated under vacuum. Compound benzyl 4-[7-(3-benzyloxy-1-naphthyl)-2-[[(2R)-1-tert-butoxycarbonyl-5,5-dimethyl-pyrrolidin-2-yl]methoxy]-6,8-dihydro-5H-pyrido [3,4-d]pyrimidin-4-yl] piperazine-1-carboxylate (110 mg, 129 umol, 28.1% yield, 96% purity) was obtained as a yellow solid. ES+APCI MS m/z 813.5 [M+H]⁺.

Step C: tert-butyl (5R)-5-[[7-(3-hydroxy-1-naphthyl)-4-piperazin-1-yl-6,8-dihydro-5H-pyrido[3,4-d]pyrimidin-2-yl]oxymethyl]-2,2-dimethyl-pyrrolidine-1-carboxylate:
NH₃ was bubbled into MeOH (30 mL) at −40° C. for 30 minutes. To a solution of benzyl 4-[7-(3-benzyloxy-1-naphthyl)-2-[[(2R)-1-tert-butoxycarbonyl-5,5-dimethyl-pyrrolidin-2-yl]methoxy]-6,8-dihydro-5H-pyrido[3,4-d]pyrimidin-4-yl]piperazine-1-carboxylate (200 mg, 246 umol) in above the mixture (NH$_3$/MeOH) was added dry Pd—C (10%, 100 mg) under N$_2$. The suspension was degassed under vacuum and purged with H$_2$ several times. The mixture was stirred under H$_2$ (15 psi) at 15° C. for 1 hour. The catalyst was filtered off and the filtrate was concentrated to give the product tert-butyl (5R)-5-[[7-(3-hydroxy-1-naphthyl)-4-piperazin-1-yl-6,8-dihydro-5H-pyrido[3,4-d]pyrimidin-2-yl]oxymethyl]-2,2-dimethyl-pyrrolidine-1-carboxylate (150 mg, 244 umol, 99.4% yield, 96% purity) as a yellow solid and directly used next step without purification. ES+APCI MS m/z 589.3 [M+H]$^+$.

Step D: tert-Butyl (5R)-5-[[7-(3-hydroxy-1-naphthyl)-4-(4-prop-2-enoylpiperazin-1-yl)-6,8-dihydro-5H-pyrido[3,4-d]pyrimidin-2-yl]oxymethyl]-2,2-dimethyl-pyrrolidine-1-carboxylate: To a mixture of tert-butyl (5R)-5-[[7-(3-hydroxy-1-naphthyl)-4-piperazin-1-yl-6,8-dihydro-5H-pyrido[3,4-d]pyrimidin-2-yl]oxymethyl]-2,2-dimethyl-pyrrolidine-1-carboxylate (130 mg, 221 umol) and DIEA (285 mg, 2.21 mmol, 385 uL) in dichloromethane (3 mL) was added a solution of prop-2-enoyl prop-2-enoate (22.3 mg, 176 umol) in dichloromethane (1 mL) at −40° C. under nitrogen atmosphere. The mixture was stirred at −40° C. for 1 hour. The reaction was quenched by addition of saturated NaHCO$_3$ (2 mL) aqueous solution. Then the mixture was poured into water (20 mL) and extracted with dichloromethane (20 mL×2). The combined organics was dried over sodium sulfate, filtered and concentrated in vacuo. The residue was purified by column chromatography (SiO$_2$, dichloromethane/methanol=1/0 to 10/1). tert-Butyl (5R)-5-[[7-(3-hydroxy-1-naphthyl)-4-(4-prop-2-enoylpiperazin-1-yl)-6,8-dihydro-5H-pyrido[3,4-d]pyrimidin-2-yl]oxymethyl]-2,2-dimethyl-pyrrolidine-1-carboxylate (140 mg, 217 umol, 98.6% yield) was obtained as a brown oil. ES+APCI MS m/z 643.6 [M+H]$^+$.

Step E: 1-[4-[2-[[(2R)-5,5-dimethylpyrrolidin-2-yl]methoxy]-7-(3-hydroxy-1-naphthyl)-6,8-dihydro-5H-pyrido[3,4-d]pyrimidin-4-yl]piperazin-1-yl]prop-2-en-1-one: To a solution of tert-butyl (5R)-5-[[7-(3-hydroxy-1-naphthyl)-4-(4-prop-2-enoylpiperazin-1-yl)-6,8-dihydro-5H-pyrido[3,4-d]pyrimidin-2-yl]oxymethyl]-2,2-dimethyl-pyrrolidine-1-carboxylate (120 mg, 187 umol) in dichloromethane (200 uL) was added TFA (212 mg, 1.87 mmol, 138 uL). The mixture was stirred at 15° C. for 1 hour. The reaction mixture was concentrated under vacuum, then diluted with dichloromethane (5 mL) and adjusted PH=7 by addition saturated NaHCO$_3$ aqueous solution. The mixture was extracted with dichloromethane (10 mL×3). The combined organic phase was dried over anhydrous Na$_2$SO$_4$, filtered and concentrated in vacuo. The residue was purified by prep-HPLC (column: Phenomenex Gemini 150*25 mm*10 um; mobile phase: [water (0.05% ammonia hydroxide v/v)-ACN]; B %: 45%-75%, 12 min). 1-[4-[2-[[(2R)-5,5-dimethylpyrrolidin-2-yl]methoxy]-7-(3-hydroxy-1-naphthyl)-6,8-dihydro-5H-pyrido[3,4-d]pyrimidin-4-yl]piperazin-1-yl]prop-2-en-1-one (30 mg, 53.6 umol, 28.7% yield, 97% purity) was obtained as yellow solid by lyophilization. ES+APCI MS m/z 543.5 [M+H]$^+$.

Example 175

(S)-1-(4-(7-(3-hydroxy-2-methylnaphthalen-1-yl)-2-((1-methylpyrrolidin-2-yl)methoxy)-5,6,7,8-tetrahydropyrido[3,4-d]pyrimidin-4-yl)piperazin-1-yl)prop-2-en-1-one

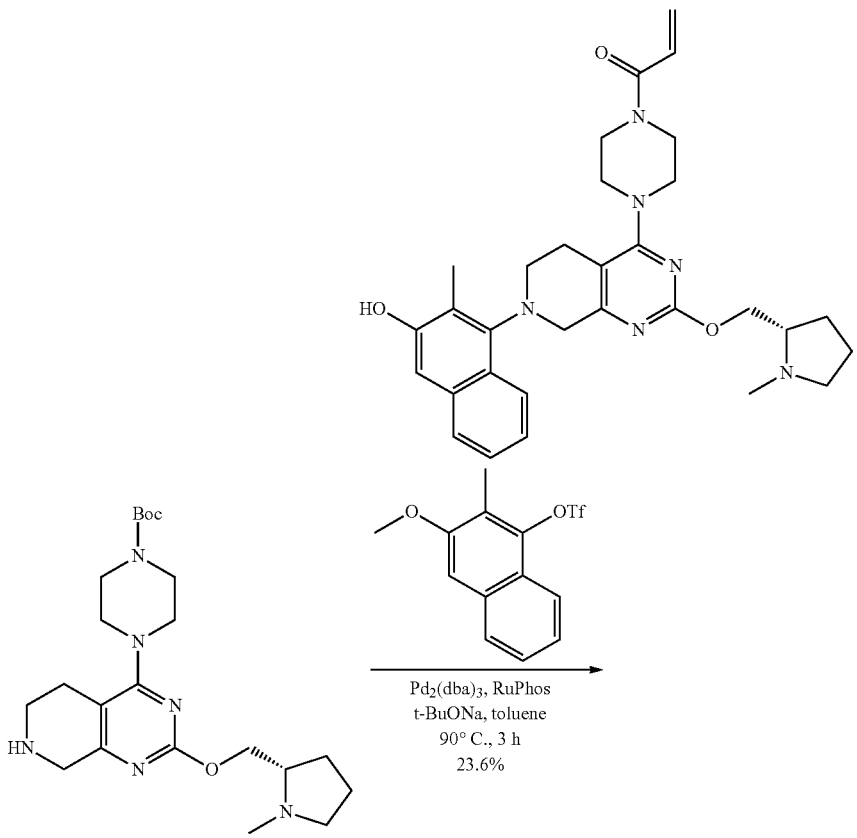

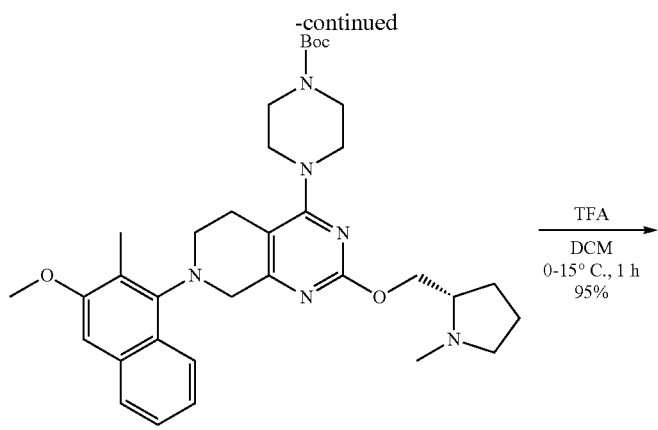

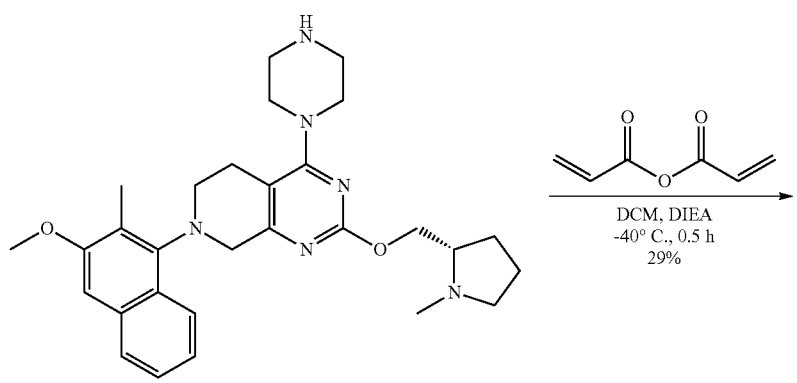

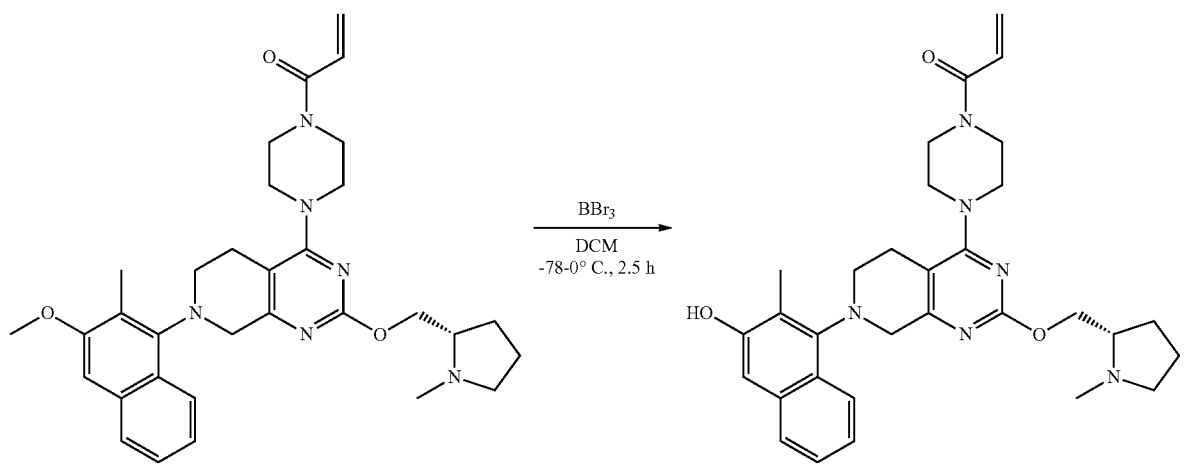 [SMILES: C=CC(=O)N1CCN(c2nc(OC[C@@H]3CCCN3C)nc3c2CCN(c2c(C)c(OC)cc4ccccc24)C3)CC1 ; "BBr3" ; C=CC(=O)N1CCN(c2nc(OC[C@@H]3CCCN3C)nc3c2CCN(c2c(C)c(O)cc4ccccc24)C3)CC1]

(S)-1-(4-(7-(3-hydroxy-2-methylnaphthalen-1-yl)-2-((1-methylpyrrolidin-2-yl)methoxy)-5,6,7,8-tetrahydropyrido[3,4-d]pyrimidin-4-yl)piperazin-1-yl)prop-2-en-1-one was synthesized according to the procedure for Example 165 substituting tert-butyl 4-[2-(3-morpholinopropoxy)-5,6,7,8-tetrahydropyrido[3,4-d]pyrimidin-4-yl]piperazine-1-carboxylate for tert-butyl 4-[7-(2-fluoro-3-methoxy-1-naphthyl)-2-(3-morpholinopropoxy)-6,8-dihydro-5H-pyrido[3,4-d]pyrimidin-4-yl]piperazine-1-carboxylate and (2-fluoro-3-methoxy-1-naphthyl) trifluoromethanesulfonate for (3-methoxy-2-methyl-1-naphthyl) trifluoromethanesulfonate in Step F. to give 1-[4-[7-(3-hydroxy-2-methyl-1-naphthyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one (10.2 mg, 17.3 umol, 21.4% yield, 100% purity, Formic Acid Salt) as a white solid. ES+APCI MS m/z 543.4 [M+H]+.

Example 176
2-[(2S)-4-[2-[2-(dimethylamino)ethoxy]-7-(3-hydroxy-1-naphthyl)-6,8-dihydro-5H-pyrido[3,4-d]pyrimidin-4-yl]-1-prop-2-enoyl-piperazin-2-yl]acetonitrile
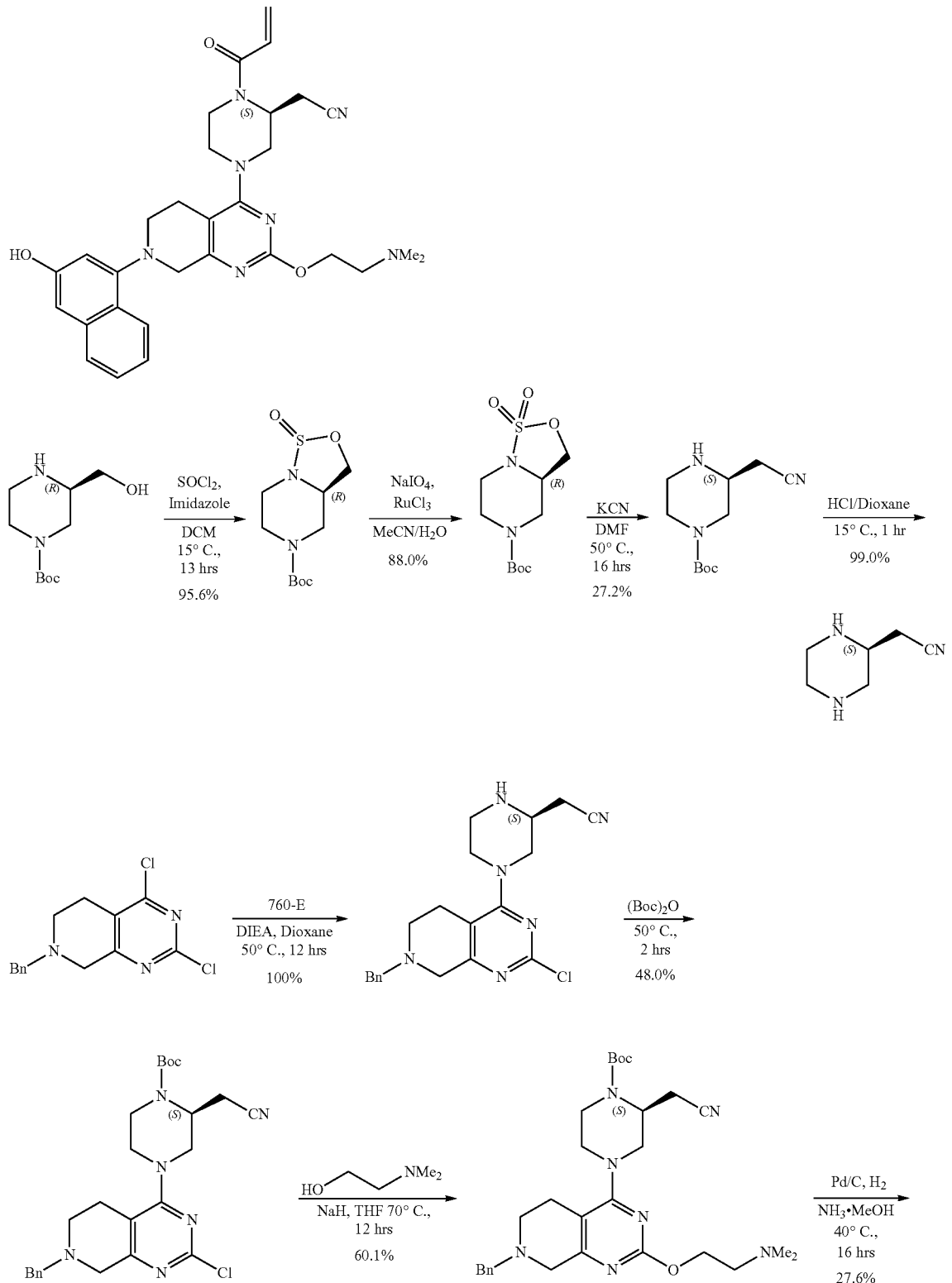

-continued
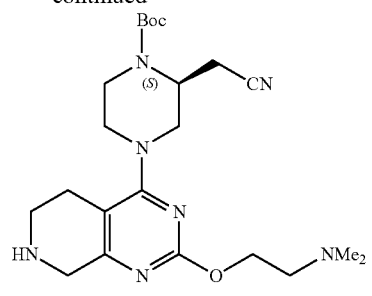
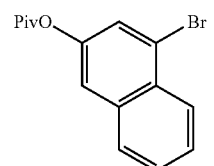
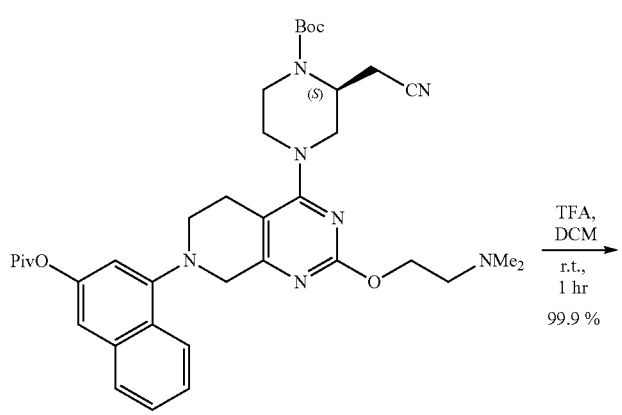
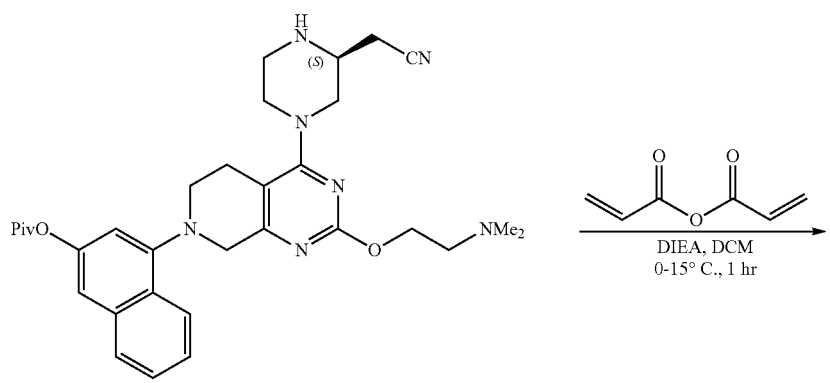
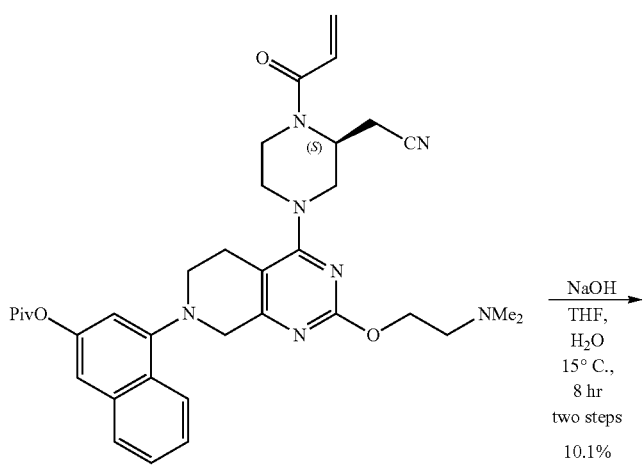

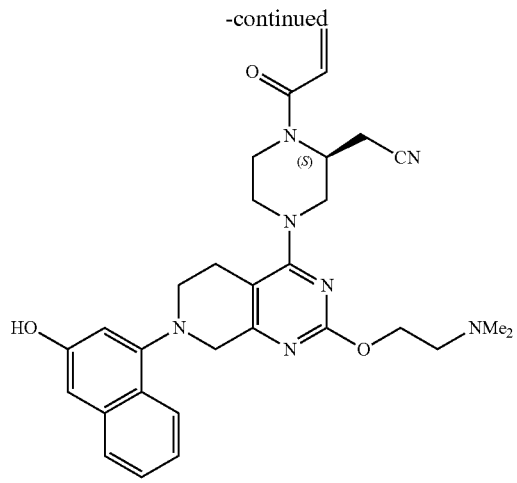

Step A: tert-butyl (3aR)-1-oxo-3a,4,6,7-tetrahydro-3H-oxathiazolo[3,4-a]pyrazine-5-carboxylate To a solution of imidazole (15.7 g, 231 mmol) in DCM (100 mL) was added SOCl$_2$ (8.25 g, 69.4 mmol, 5.03 mL) at 0° C. The reaction mixture was stirred at 15° C. for 1 hour. To the mixture was added tert-butyl (3R)-3-(hydroxymethyl)piperazine-1-carboxylate (5 g, 23.1 mmol) in DCM (100 mL) at −70° C. The reaction mixture was stirred at 15° C. for 12 hour. Upon completion, the reaction mixture was quenched by saturated NH$_4$Cl (100 mL) and separated, the aqueous layer was extracted with DCM (40 mL). The combined organic layers were washed with brine (20 mL), dried over Na$_2$SO$_4$, filtered and concentrated under vacuum to give tert-butyl (3aR)-1-oxo-3a,4,6,7-tetrahydro-3H-oxathiazolo[3,4-a]pyrazine-5-carboxylate (5.8 g, 22.1 mmol, 95.6% yield) as a brown solid.

Step B: tert-butyl (3aR)-1,1-dioxo-3a,4,6,7-tetrahydro-3H-oxathiazolo[3,4-a]pyrazine-5-carboxylate To a solution of tert-butyl (3aR)-1-oxo-3a,4,6,7-tetrahydro-3H-oxathiazolo[3,4-a]pyrazine-5-carboxylate (7.5 g, 28.6 mmol) in MeCN (225 mL) was added NaIO$_4$ (7.95 g, 37.2 mmol, 2.06 mL) in water (75 mL) followed by RuCl$_3$.H$_2$O (129 mg, 572 umol) at 0° C. The reaction mixture was stirred at 15° C. for 0.5 hour. Upon completion, the reaction mixture was quenched with saturated NH$_4$Cl (10 mL) and extracted with EtOAc (20 mL). The organic layer was washed with brine (10 mL), dried over Na$_2$SO$_4$, filtered and concentrated under vacuum. The residue was purified by silica gel chromatography (PE:EtOAc=3:1 to 1:1) to give tert-butyl (3aR)-1,1-dioxo-3a,4,6,7-tetrahydro-3H-oxathiazolo[3,4-a]pyrazine-5-carboxylate (7 g, 25.2 mmol, 88.0% yield) as a white solid. $^1$H NMR (400 MHz, CHLOROFORM-d) δ=4.64 (dd, J=6.4, 8.0 Hz, 1H), 4.36-3.94 (m, 3H), 3.64 (ddt, J=3.6, 6.0, 9.2 Hz, 1H), 3.46 (br d, J=11.6 Hz, 1H), 3.13 (br s, 1H), 2.96 (dt, J=3.2, 11.2 Hz, 2H), 1.48 (s, 9H)

Step C: tert-butyl (3S)-3-(cyanomethyl)piperazine-1-carboxylate

To a solution of tert-butyl (3aR)-1,1-dioxo-3a,4,6,7-tetrahydro-3H-oxathiazolo[3,4-a]pyrazine-5-carboxylate (5 g, 18.0 mmol) in DMF (100 mL) was added KCN (1.04 g, 16.0 mmol, 684.94 uL). The reaction mixture was heated to 50° C. for 16 hours. Upon completion, the reaction mixture was quenched by HCl (2 M, 50 mL) and stirred at 15° C. for 1 h. The mixture was basidified by NaOH (40%, 10 mL) and extracted with EtOAc (3×100 mL). The organic layer was dried over Na$_2$SO$_4$ and concentrated under vacuum. The residue was purified by silica gel chromatography (PE:EtOAc=3:1 to 0:1 then EtOAc:MeOH=100:1 to 10:1) to give tert-butyl (3S)-3-(cyanomethyl)piperazine-1-carboxylate (1.1 g, 4.88 mmol, 27.2% yield) as a brown oil. $^1$H NMR (400 MHz, CHLOROFORM-d) δ=4.05-3.71 (m, 2H), 3.08-2.88 (m, 3H), 2.84-2.62 (m, 2H), 2.56-2.37 (m, 2H), 1.47 (s, 9H).

Step D: 2-[(2S)-piperazin-2-yl]acetonitrile

A reaction mixture of tert-butyl (3S)-3-(cyanomethyl)piperazine-1-carboxylate (850 mg, 3.77 mmol) and HCl/dioxane (4 M, 20 mL) was stirred at 15° C. for 1 hour. Upon completion, the solvent was removed under vacuum to give 2-[(2S)-piperazin-2-yl]acetonitrile (740 mg, 3.74 mmol, 99.0% yield, 2HCl) as a white solid. $^1$H NMR (400 MHz, METHANOL-d$_4$) δ=4.04-3.90 (m, 1H), 3.81-3.70 (m, 2H), 3.69-3.61 (m, 2H), 3.53-3.36 (m, 2H), 3.13 (d, J=6.4 Hz, 2H).

Step E: 2-[(2S)-4-(7-benzyl-2-chloro-6,8-dihydro-5H-pyrido[3,4-d]pyrimidin-4-yl)piperazin-2-yl]acetonitrile To a mixture of 7-benzyl-2,4-dichloro-6,8-dihydro-5H-pyrido[3,4-d]pyrimidine (1.3 g, 4.42 mmol) and 2-[(2S)-piperazin-2-yl]acetonitrile (1.17 g, 5.91 mmol, 2HCl) in dioxane (25 mL) was added DIEA (2.86 g, 22.1 mmol, 3.85 mL). The reaction mixture was stirred at 50° C. for 12 hours. Upon completion, the reaction mixture was diluted with water (50 mL) and extracted with EtOAc (3×80 mL). The combined organic layers were washed with brine (30 mL), dried over Na$_2$SO$_4$ and concentrated under vacuum to give 2-[(2S)-4-(7-benzyl-2-chloro-6,8-dihydro-5H-pyrido[3,4-d]pyrimidin-4-yl)piperazin-2-yl]acetonitrile (1.69 g, 4.41 mmol, 100% yield) as a brown solid.

Step F: tert-butyl (2S)-4-(7-benzyl-2-chloro-6,8-dihydro-5H-pyrido[3,4-d]pyrimidin-4-yl)-2-(cyanomethyl)piperazine-1-carboxylate A reaction mixture of 2-[(2S)-4-(7-benzyl-2-chloro-6,8-dihydro-5H-pyrido[3,4-d]pyrimidin-4-yl)piperazin-2-yl]acetonitrile (1.69 g, 4.41 mmol) and (Boc)₂O (10.3 g, 47.2 mmol, 10.8 mL) was heated to 50° C. for 2 hours. Upon completion, the reaction mixture was purified by silica gel chromatography (PE:EtOAc=10:1 to 1:1) to give tert-butyl (2S)-4-(7-benzyl-2-chloro-6,8-dihydro-5H-pyrido[3,4-d]pyrimidin-4-yl)-2-(cyanomethyl)piperazine-1-carboxylate (1.1 g, 2.12 mmol, 48.0% yield, 93% purity) as brown solid. ES+APCI MS m/z 483.4 [M+H]⁺.

Step G: tert-butyl (2S)-4-[7-benzyl-2-[2-(dimethylamino)ethoxy]-6,8-dihydro-5H-pyrido[3,4-d]pyrimidin-4-yl]-2-(cyanomethyl)piperazine-1-carboxylate: To a solution of 2-(dimethylamino)ethanol (415 mg, 4.66 mmol, 468 uL) in THF (20 mL) was added NaH (149 mg, 3.73 mmol, 60% purity) 0° C. The reaction mixture was stirred at 0° C. for 0.5 h. To the mixture was added tert-butyl (2S)-4-(7-benzyl-2-chloro-6,8-dihydro-5H-pyrido[3,4-d]pyrimidin-4-yl)-2-(cyanomethyl)piperazine-1-carboxylate (900 mg, 1.86 mmol). The reaction mixture was stirred at 70° C. for 12 hours at sealed tube under N₂. Upon completion, the reaction mixture was quenched by water (10 mL) and extracted with EtOAc (3×40 mL). The combined organic layers were treated with activated carbon and filtered. The filtrate was concentrated under vacuum to give tert-butyl (2S)-4-[7-benzyl-2-[2-(dimethylamino)ethoxy]-6,8-dihydro-5H-pyrido[3,4-d]pyrimidin-4-yl]-2-(cyanomethyl)piperazine-1-carboxylate (600 mg, 1.12 mmol, 60.1% yield) as a brown solid.

Step H: tert-butyl (2S)-2-(cyanomethyl)-4-[2-[2-(dimethylamino)ethoxy]-5,6,7,8-tetrahydropyrido[3,4-d]pyrimidin-4-yl]piperazine-1-carboxylate: NH₃ was bubbled into MeOH (20 mL) for 5 min. To the solution was added tert-butyl (2S)-4-[7-benzyl-2-[2-(dimethylamino)ethoxy]-6,8-dihydro-5H-pyrido[3,4-d]pyrimidin-4-yl]-2-(cyanomethyl)piperazine-1-carboxylate (600 mg, 1.12 mmol) and 10% Pd/C (200 mg). The suspension was degassed under vacuum and purged with H₂ several times. The mixture was stirred under H₂ (15 psi) at 40° C. for 16 hours. Upon completion, the mixture was filtered and the filter cake was washed with MeOH (3×30 mL). The filtrate was concentrated under vacuum. The residue was purified by prep-HPLC (column: Phenomenex luna (2) C18 250*50 10 u; mobile phase: [water (0.225% Formic Acid)-ACN]; B %: %-%,30 MIN; 60% min) to give tert-butyl (2S)-2-(cyanomethyl)-4-[2-[2-(dimethylamino)ethoxy]-5,6,7,8-tetrahydropyrido[3,4-d]pyrimidin-4-yl]piperazine-1-carboxylate (167 mg, 331 umol, 29.6% yield, 88.3% purity) as a colorless oil. ES+APCI MS m/z 446.3 [M+H]⁺.

Step I: tert-butyl (2S)-2-(cyanomethyl)-4-[2-[2-(dimethylamino)ethoxy]-7-[3-(2,2-dimethylpropanoyloxy)-1-naphthyl]-6,8-dihydro-5H-pyrido[3,4-d]pyrimidin-4-yl]piperazine-1-carboxylate: To a solution of tert-butyl (2S)-2-(cyanomethyl)-4-[2-[2-(dimethylamino)ethoxy]-5,6,7,8-tetrahydropyrido[3,4-d]pyrimidin-4-yl]piperazine-1-carboxylate (180 mg, 404 umol), (4-bromo-2-naphthyl) 2,2-dimethylpropanoate (248 mg, 808 umol) and Cs₂CO₃ (395 mg, 1.21 mmol) in toluene (6 mL) was added XPHOS Palladacycle Gen 3 (34.20 mg, 40.4 umol). The reaction mixture was stirred at 70° C. for 4 hours under N₂. Upon completion, the reaction mixture was purified by silica gel chromatography (PE:EA=5:1 to 0:1) to give tert-butyl (2S)-2-(cyanomethyl)-4-[2-[2-(dimethylamino)ethoxy]-7-[3-(2,2-dimethylpropanoyloxy)-1-naphthyl]-6,8-dihydro-5H-pyrido[3,4-d]pyrimidin-4-yl]piperazine-1-carboxylate (200 mg, 272 umol, 67.3% yield, 91.3% purity) as a brown solid. ES+APCI MS m/z 672.0 [M+H]⁺.

Step J: [4-[4-[(3S)-3-(cyanomethyl)piperazin-1-yl]-2-[2-(dimethylamino)ethoxy]-6,8-dihydro-5H-pyrido[3,4-d]pyrimidin-7-yl]-2-naphthyl] 2,2-dimethylpropanoate: To a solution of tert-butyl (2S)-2-(cyanomethyl)-4-[2-[2-(dimethylamino)ethoxy]-7-[3-(2,2-dimethylpropanoyloxy)-1-naphthyl]-6,8-dihydro-5H-pyrido[3,4-d]pyrimidin-4-yl]piperazine-1-carboxylate (200 mg, 298 umol) in DCM (0.3 mL) was added TFA (420 mg, 3.68 mmol, 273 uL). The reaction mixture was stirred at 15° C. for 1 hour. Upon completion, the reaction mixture was concentrated under vacuum to give [4-[4-[(3S)-3-(cyanomethyl)piperazin-1-yl]-2-[2-(dimethylamino)ethoxy]-6,8-dihydro-5H-pyrido[3,4-d]pyrimidin-7-yl]-2-naphthyl] 2,2-dimethylpropanoate (238 mg, 298 umol, 99.9% yield, 2TFA) as a brown oil.

Step K: [4-[4-[(3S)-3-(cyanomethyl)-4-prop-2-enoyl-piperazin-1-yl]-2-[2-(dimethylamino)ethoxy]-6,8-dihydro-5H-pyrido[3,4-d]pyrimidin-7-yl]-2-naphthyl] 2,2-dimethylpropanoate: To a solution of [4-[4-[(3S)-3-(cyanomethyl)piperazin-1-yl]-2-[2-(dimethylamino)ethoxy]-6,8-dihydro-5H-pyrido[3,4-d]pyrimidin-7-yl]-2-naphthyl] 2,2-dimethylpropanoate (238 mg, 298 umol, 2TFA) and DIEA (308 mg, 2.38 mmol, 415 uL) in DCM (5 mL) was added prop-2-enoyl prop-2-enoate (56.3 mg, 446 umol) at 0° C. The reaction mixture was stirred at 15° C. for 1 hour. Upon completion, the reaction mixture was quenched with a drop of water. The mixture (was purified by silica gel chromatography (PE:EtOAc=1:1 to 0:1 then EtOAc:MeOH=50:1 to 3:1) to give [4-[4-[(3S)-3-(cyanomethyl)-4-prop-2-enoyl-piperazin-1-yl]-2-[2-(dimethylamino)ethoxy]-6,8-dihydro-5H-pyrido[3,4-d]pyrimidin-7-yl]-2-naphthyl] 2,2-dimethylpropanoate (300 mg, crude) as a brown oil. ES+APCI MS m/z 626.4 [M+H]⁺.

Step L: 2-[(2S)-4-[2-[2-(dimethylamino)ethoxy]-7-(3-hydroxy-1-naphthyl)-6,8-dihydro-5H-pyrido[3,4-d]pyrimidin-4-yl]-1-prop-2-enoyl-piperazin-2-yl]acetonitrile: To a solution of [4-[4-[(3S)-3-(cyanomethyl)-4-prop-2-enoyl-piperazin-1-yl]-2-[2-(dimethylamino)ethoxy]-6,8-dihydro-5H-pyrido[3,4-d]pyrimidin-7-yl]-2-naphthyl] 2,2-dimethylpropanoate (300 mg, 479 umol) in THF (3 mL) was added NaOH (2 M, 3 mL) in water. The reaction mixture was stirred at 15° C. for 8 hours. Upon completion, the reaction mixture was acidified by 0.5 mL of formic acid (20% in water) to PH=7 and extracted with DCM (5×10 mL). The combined organic layers were dried over Na₂SO₄, filtered and concentrated under vacuum.

The residue was purified by prep-HPLC (column: Boston Green ODS 150*30 5 u; mobile phase: [water (0.225% Formic Acid)-ACN]; B %: 25%-49%,10 min) to give 2-[(2S)-4-[2-[2-(dimethylamino)ethoxy]-7-(3-hydroxy-1-naphthyl)-6,8-dihydro-5H-pyrido[3,4-d]pyrimidin-4-yl]-1-prop-2-enoyl-piperazin-2-yl]acetonitrile (18.3 mg, 30.2 umol, two steps 10.1% yield, 96.7% purity, Formic Acid Salt) as a yellow solid. ES+APCI MS m/z 542.5 [M+H]⁺.

Example 177

2-[4-[2-[[(3R)-1-methylpyrrolidin-3-yl]methoxy]-7-(1-naphthyl)-6,8-dihydro-5H-pyrido[3,4-d]pyrimidin-4-yl]-1-prop-2-enoyl-piperazin-2-yl]acetonitrile

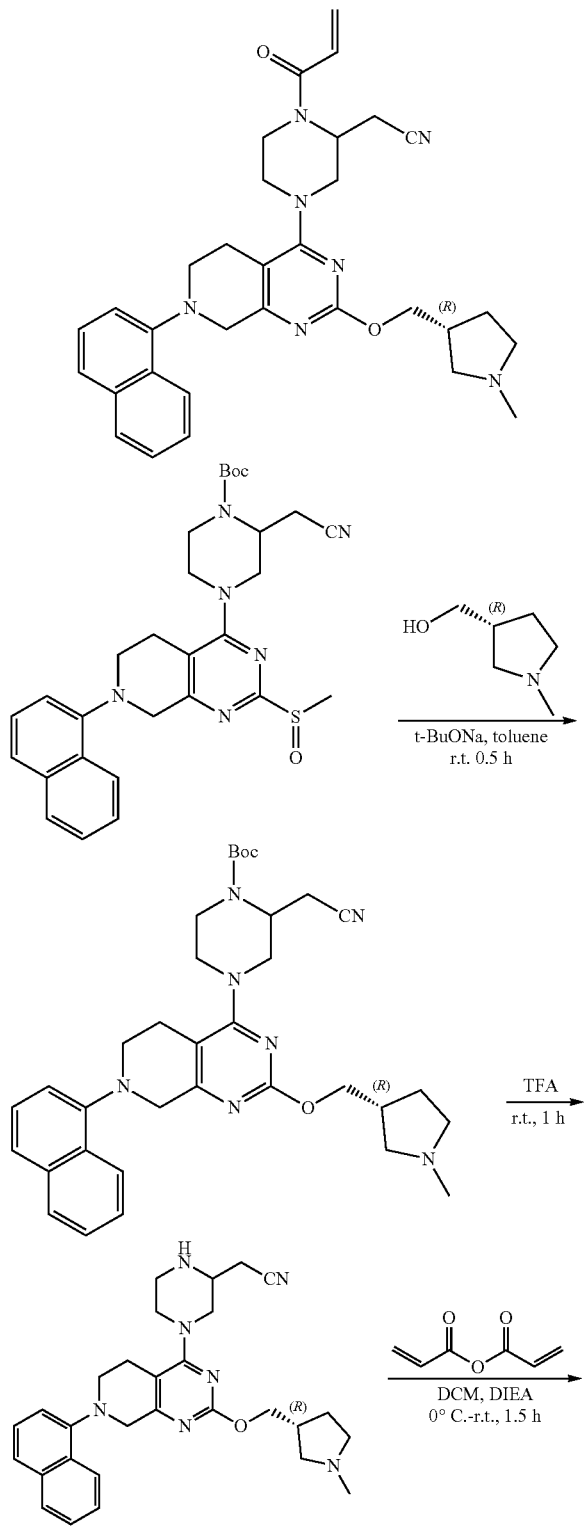

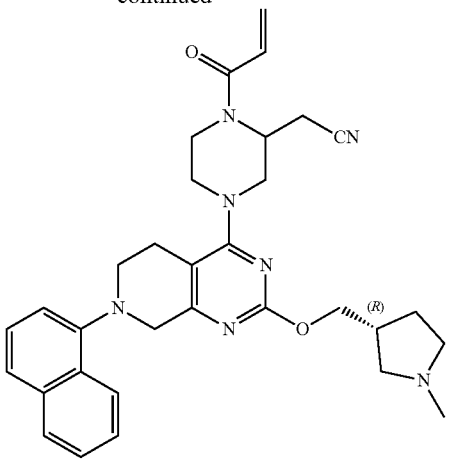

Step A: tert-butyl 2-(cyanomethyl)-4-[2-[[(3R)-1-methylpyrrolidin-3-yl]methoxy]-7-(1-naphthyl)-6,8-dihydro-5H-pyrido[3,4-d]pyrimidin-4-yl]piperazine-1-carboxylate: To a solution of tert-butyl 2-(cyanomethyl)-4-[2-methylsulfinyl-7-(1-naphthyl)-6,8-dihydro-5H-pyrido[3,4-d]pyrimidin-4-yl]piperazine-1-carboxylate (300 mg, 549 umol) and [(3R)-1-methylpyrrolidin-3-yl]methanol (126 mg, 1.10 mmol) in toluene (6 mL) was added t-BuONa (79.1 mg, 823 umol) at 18° C. and the reaction mixture stirred at 18° C. for 0.5 hour. To the mixture was then added EtOAc (20 mL) and water (15 mL), then extracted with EtOAc (3×20 mL). The combined organic layers were washed with brine (20 mL). The combined organic layers were dried over anhydrous $Na_2SO_4$, filtered and concentrated under reduced pressure. The residue was purified by reversed phase flash column (ACN/Water (0.1% Formic Acid)=42%) to give tert-butyl 2-(cyanomethyl)-4-[2-[[(3R)-1-methylpyrrolidin-3-yl]methoxy]-7-(1-naphthyl)-6,8-dihydro-5H-pyrido[3,4-d]pyrimidin-4-yl]piperazine-1-carboxylate (200 mg, 331 umol, 60.4% yield, 99.0% purity) as yellow solid. ES+APCI MS m/z 598.3[M+H]+.

Step B: 2-[4-[2-[[(3R)-1-methylpyrrolidin-3-yl]methoxy]-7-(1-naphthyl)-6,8-dihydro-5H-pyrido[3,4-d]pyrimidin-4-yl]piperazin-2-yl]acetonitrile: A mixture of tert-butyl 2-(cyanomethyl)-4-[2-[[(3R)-1-methylpyrrolidin-3-yl]methoxy]-7-(1-naphthyl)-6,8-dihydro-5H-pyrido[3,4-d]pyrimidin-4-yl]piperazine-1-carboxylate (200 mg, 334 umol) and TFA (763 mg, 6.69 mmol, 495 uL) was stirred at 18° C. for 1 hour. The reaction mixture was concentrated under vacuum to give 2-[4-[2-[[(3R)-1-methylpyrrolidin-3-yl]methoxy]-7-(1-naphthyl)-6,8-dihydro-5H-pyrido[3,4-d]pyrimidin-4-yl]piperazin-2-yl]acetonitrile (250 mg, crude, 2TFA) as brown oil.

Step C: 2-[4-[2-[[(3R)-1-methylpyrrolidin-3-yl]methoxy]-7-(1-naphthyl)-6,8-dihydro-5H-pyrido[3,4-d]pyrimidin-4-yl]-1-prop-2-enoyl-piperazin-2-yl]acetonitrile: To a solution of 2-[4-[2-[[(3R)-1-methylpyrrolidin-3-yl]methoxy]-7-(1-naphthyl)-6,8-dihydro-5H-pyrido[3,4-d]pyrimidin-4-yl]piperazin-2-yl]acetonitrile (250 mg, 344 umol, 2TFA) and DIEA (356 mg, 2.76 mmol, 480 uL) in DCM (5 mL) was added prop-2-enoyl prop-2-enoate (65.2 mg, 517 umol) at 0° C. and the mixture was stirred at 18° C. for 1.5 hours. The reaction mixture was quenched with water (3 mL) and then extracted with DCM (3×6 mL). The combined organic layers were dried over anhydrous $Na_2SO_4$, filtered and concentrated under reduced pressure. The residue was purified by prep-HPLC (column: Phenomenex Gemini 150*25 mm*10 um; mobile phase: [water (10 mM NH4HCO3)-ACN]; B %: 30%-60%,3 min) to give 2-[4-[2-[[(3R)-1-methylpyrrolidin-3-yl]methoxy]-7-(1-naphthyl)-6,8-dihydro-5H-pyrido[3,4-d]pyrimidin-4-yl]-1-prop-2-enoyl-piperazin-2-yl]acetonitrile (9.98 mg, 17.0 umol, 4.94% yield, 94.1% purity) as white solid. ES+APCI MS m/z 552.5[M+H]+.
Example 178
2-[4-[7-(3-hydroxy-1-naphthyl)-2-[[(2R)-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile
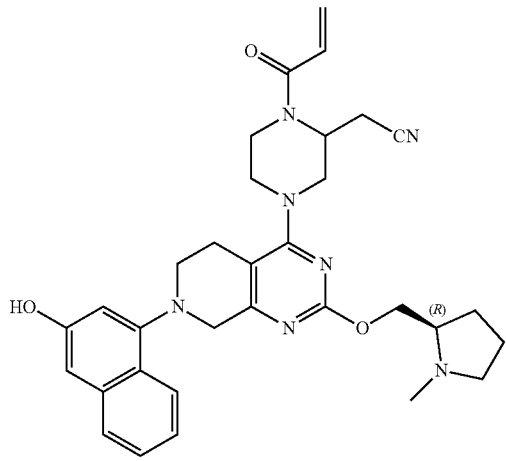
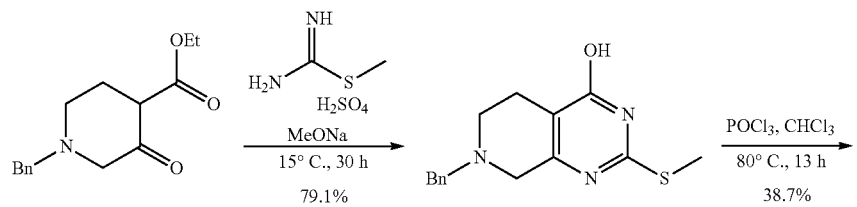
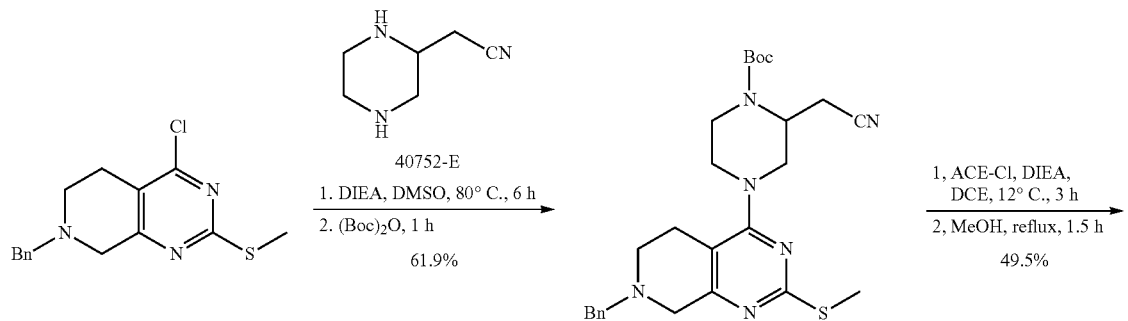
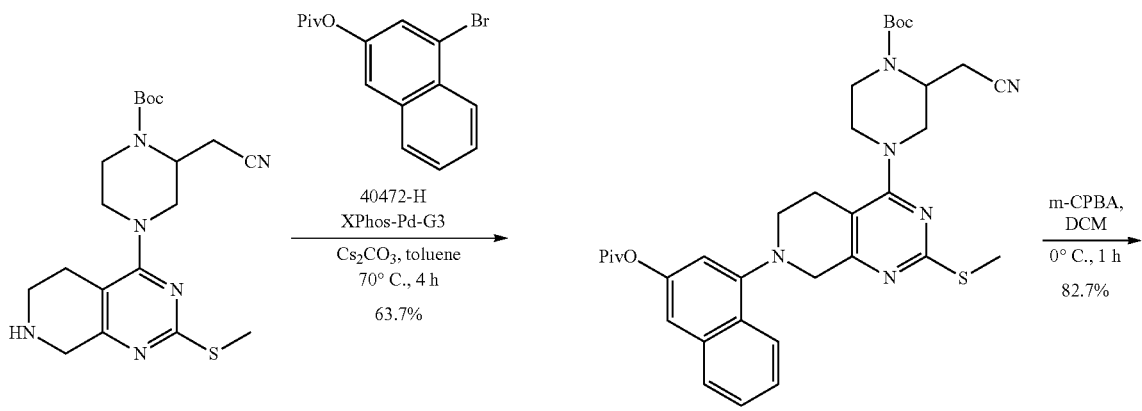

-continued
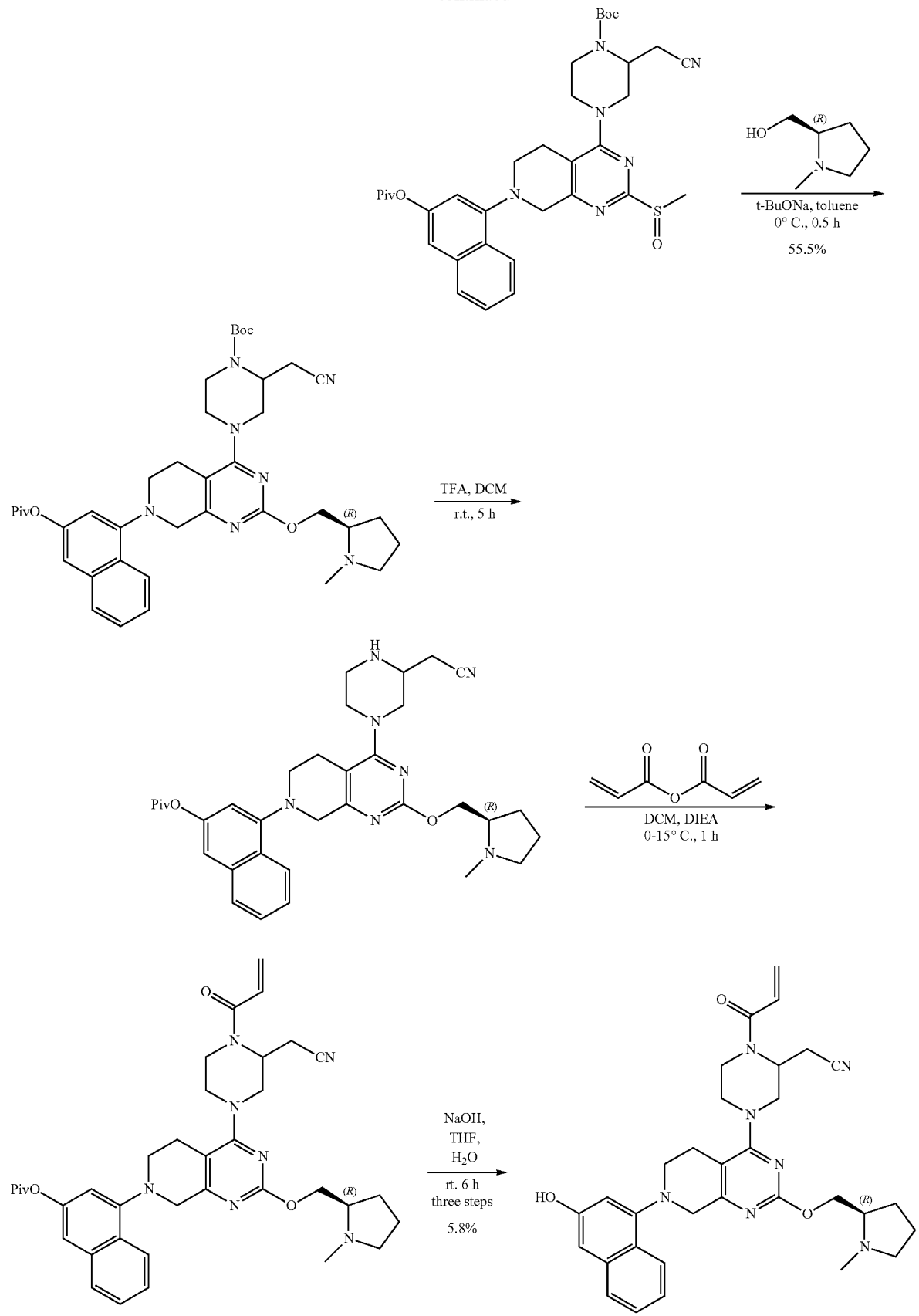

Step A: 7-benzyl-2-methylsulfanyl-6,8-dihydro-5H-pyrido[3,4-d]pyrimidin-4-ol A suspension of MeOH (1000 mL) and Na (22.0 g, 957 mmol, 22.7 mL) was stirred for 30 min. To this mixture was added ethyl 1-benzyl-3-oxo-piperidine-4-carboxylate (50 g, 191 mmol and 2-methylisothiourea (47.9 g, 344 mmol, 0.5 $H_2SO_4$) at 15° C. The reaction mixture was stirred at 15° C. for 30 hours. The reaction mixture was acidified by HCl (2 M) (300 mL) until pH=6 and concentrated under reduced pressure. The residue was suspended in 200 mL of water and stirred rapidly. The suspension was filtered and the white solid collected and washed with ethyl acetate. 7-benzyl-2-methylsulfanyl-6,8-dihydro-5H-pyrido[3,4-d]pyrimidin-4-ol (68 g, 151 mmol, 79.1% yield, 64.0% purity) was obtained as a white solid.

Step B: 7-benzyl-4-chloro-2-methylsulfanyl-6,8-dihydro-5H-pyrido[3,4-d]pyrimidine To a solution of 7-benzyl-2-methylsulfanyl-6,8-dihydro-5H-pyrido[3,4-d]pyrimidin-4-ol (50 g, 174 mmol) in $CHCl_3$ (1000 mL) was added $POCl_3$ (166 g, 1.08 mol, 100 mL) and the mixture stirred at 80° C. for 13 hours. Upon completion, the reaction mixture was concentrated under vacuum. The residue was diluted with EtOAc (500 mL) and basified using saturated $Na_2CO_3$ (800 mL) to PH=7. The mixture was extracted with ethyl acetate (3×400 mL). The combined organic layers were dried over anhydrous $Na_2SO_4$, filtered and concentrated under reduced pressure. The residue was purified by silica gel chromatography (PE:EA from 100:1 to 80:1) to give 7-benzyl-4-chloro-2-methylsulfanyl-6,8-dihydro-5H-pyrido[3,4-d]pyrimidine (21.7 g, 67.4 mmol, 38.7% yield, 95.0% purity) as brown oil. ES+APCI MS m/z 306.1[M+H]$^+$.

Step C: tert-butyl 4-(7-benzyl-2-methylsulfanyl-6,8-dihydro-5H-pyrido[3,4-d]pyrimidin-4-yl)-2-(cyanomethyl)piperazine-1-carboxylate To a solution of 7-benzyl-4-chloro-2-methylsulfanyl-6,8-dihydro-5H-pyrido[3,4-d]pyrimidine (2.6 g, 8.50 mmol) and 2-piperazin-2-ylacetonitrile (1.68 g, 8.50 mmol, 2HCl) in DMSO (52 mL) was added DIEA (5.49 g, 42.5 mmol, 7.40 mL). The mixture was warmed to 80° C. and stirred at 80° C. for 6 hours. To the mixture was added (Boc)$_2$O (18.5 g, 85.0 mmol, 19.5 mL) and the mixture stirred at 80° C. for 1 hour. Water (150 mL) was added and the mixture was extracted with ethyl acetate (3×200 mL). The combined organic phase was washed with brine (200 mL), dried with anhydrous $Na_2SO_4$, filtered and concentrated in vacuum. The residue was purified by silica gel chromatography (PE:EA from 10:1 to 0:1) to give tert-butyl 4-(7-benzyl-2-methylsulfanyl-6,8-dihydro-5H-pyrido[3,4-d]pyrimidin-4-yl)-2-(cyanomethyl)piperazine-1-carboxylate (2.74 g, 5.26 mmol, 61.9% yield, 95.0% purity) as brown solid. ES+APCI MS m/z 495.4[M+H]$^+$.

Step D: tert-butyl 2-(cyanomethyl)-4-(2-methylsulfanyl-5,6,7,8-tetrahydropyrido[3,4-d]pyrimidin-4-yl)piperazine-1-carboxylate To a solution of tert-butyl 4-(7-benzyl-2-methylsulfanyl-6,8-dihydro-5H-pyrido[3,4-d]pyrimidin-4-yl)-2-(cyanomethyl)piperazine-1-carboxylate (2.51 g, 5.07 mmol) and DIEA (1.97 g, 15.2 mmol, 2.65 mL) in DCE (50 mL) was added 1-chloroethyl carbonochloridate (1.81 g, 12.7 mmol) at 0° C., and the mixture stirred at 15° C. for 3 hours. The reaction mixture was concentrated under vacuum. The residue was dissolved in MeOH (50 mL) and the reaction mixture was stirred at 70° C. for 1.5 hours. The mixture was concentrated under vacuum. The residue was purified by prep-HPLC (column: Phenomenex Synergi Max-RP 250*50 mm*10 um; mobile phase: [water (0.225% FA)-ACN]; B %: 23%-48%,30; 50% min) to give tert-butyl 2-(cyanomethyl)-4-(2-methylsulfanyl-5,6,7,8-tetrahydropyrido[3,4-d]pyrimidin-4-yl)piperazine-1-carboxylate (1.13 g, 2.51 mmol, 49.5% yield, 90.0% purity) as pink solid. ES+APCI MS m/z 405.3[M+H]$^+$.

Step E: tert-butyl 2-(cyanomethyl)-4-[7-[3-(2,2-dimethylpropanoyloxy)-1-naphthyl]-2-methylsulfanyl-6,8-dihydro-5H-pyrido[3,4-d]pyrimidin-4-yl]piperazine-1-carboxylate:

To a solution of tert-butyl 2-(cyanomethyl)-4-(2-methylsulfanyl-5,6,7,8-tetrahydropyrido[3,4-d]pyrimidin-4-yl)piperazine-1-carboxylate (730 mg, 1.80 mmol), (4-bromo-2-naphthyl) 2,2-dimethylpropanoate (832 mg, 2.71 mmol) and $Cs_2CO_3$ (1.76 g, 5.41 mmol) in toluene (18 mL) was added [2-(2-aminophenyl)phenyl]palladium(1+); dicyclohexyl-[2-(2,4,6-triisopropylphenyl)phenyl]phosphane-methanesulfonate (153 mg, 180 umol), the suspension was degassed under vacuum and purged with $N_2$ several times. The reaction mixture was stirred at 70° C. for 4 hours. Upon completion, water (20 mL) was added to the mixture. The resulting mixture was extracted with EtOAc (4×20 mL). The combined organic layers were washed with brine (40 mL), dried over anhydrous $Na_2SO_4$, filtered and concentrated under reduced pressure The residue was purified by silica gel chromatography (PE:EtOAc from 30:1 to 0:1) to give tert-butyl 2-(cyanomethyl)-4-[7-[3-(2,2-dimethylpropanoyloxy)-1-naphthyl]-2-methylsulfanyl-6,8-dihydro-5H-pyrido[3,4-d]pyrimidin-4-yl]piperazine-1-carboxylate (740 mg, 1.15 mmol, 63.7% yield, 98.0% purity) as brown solid. ES+APCI MS m/z 631.5[M+H]$^+$.

Step F: tert-butyl 2-(cyanomethyl)-4-[7-[3-(2,2-dimethylpropanoyloxy)-1-naphthyl]-2-methylsulfinyl-6,8-dihydro-5H-pyrido[3,4-d]pyrimidin-4-yl]piperazine-1-carboxylate To a solution of tert-butyl 2-(cyanomethyl)-4-[7-[3-(2,2-dimethylpropanoyloxy)-1-naphthyl]-2-methylsulfanyl-6,8-dihydro-5H-pyrido[3,4-d]pyrimidin-4-yl]piperazine-1-carboxylate (100 mg, 158 umol) in DCM (2 mL) was added m-CPBA (32.2 mg, 158 umol, 85.0% purity) at 0° C. and the mixture stirred at 0° C. for 1 hours. The reaction mixture was quenched by saturated $Na_2S_2O_3$ (4 mL) at 0° C. and separated, then diluted with water (10 mL) and extracted with ethyl acetate (10 mL). The combined organic layers were washed with brine (20 mL), dried over anhydrous $Na_2SO_4$, filtered and concentrated under reduced pressure to give a residue. The residue was purified by silica gel chromatography (PE:EA from 10:1 to 0:1) to give tert-butyl 2-(cyanomethyl)-4-[7-[3-(2,2-dimethylpropanoyloxy)-1-naphthyl]-2-methylsulfinyl-6,8-dihydro-5H-pyrido[3,4-d] pyrimidin-4-yl]piperazine-1-carboxylate (90 mg, 125 umol, 79.0% yield, 90.0% purity) as brown solid. ES+APCI MS m/z 647.5[M+H]$^+$.

Step G: tert-butyl 2-(cyanomethyl)-4-[7-[3-(2,2-dimethylpropanoyloxy)-1-naphthyl]-2-[[(2R)-1-methylpyrrolidin-2-yl]methoxy]-6,8-dihydro-5H-pyrido[3,4-d]pyrimidin-4- yl]piperazine-1-carboxylate: To a solution of tert-butyl 2-(cyanomethyl)-4-[7-[3-(2,2-dimethylpropanoyloxy)-1-naphthyl]-2-methylsulfinyl-6,8-dihydro-5H-pyrido[3,4-d]pyrimidin-4-yl]piperazine-1-carboxylate (560 mg, 866 umol), [(2R)-1-methylpyrrolidin-2-yl]methanol (199 mg, 1.73 mmol) in toluene (10 mL) was added t-BuONa (125 mg, 1.30 mmol) at 0° C. and the mixture was stirred at 0° C. for 0.5 hour. The mixture was partitioned between EtOAc (20 mL) and water (15 mL) and separated. Then the aqueous layer was extracted with EtOAc (3×20 mL). The combined organic layers were washed with brine (20 mL), dried over anhydrous $Na_2SO_4$, filtered and concentrated under reduced pressure. The residue was purified by reverse phase flash column to give tert-butyl 2-(cyanomethyl)-4-[7-[3-(2,2-dimethylpropanoyloxy)-1-naphthyl]-2-[[(2R)-1-methylpyrrolidin-2-yl]methoxy]-6,8-dihydro-5H-pyrido[3,4-d]pyrimidin-4-yl]piperazine-1-carboxylate (340 mg, 481 umol, 55.5% yield, 98.7% purity) as brown oil. ES+APCI MS m/z 698.4[M+H]$^+$.

Step H: [4-[4-[3-(cyanomethyl)piperazin-1-yl]-2-[[(2R)-1-methylpyrrolidin-2-yl]methoxy]-6,8-dihydro-5H-pyrido[3,4-d]pyrimidin-7-yl]-2-naphthyl] 2,2-dimethylpropanoate: To a solution of tert-butyl 2-(cyanomethyl)-4-[7-[3-(2,2-dimethylpropanoyloxy)-1-naphthyl]-2-[[(2R)-1-methylpyrrolidin-2-yl]methoxy]-6,8-dihydro-5H-pyrido[3,4-d]pyrimidin-4-yl]piperazine-1-carboxylate (140 mg, 201 umol) in DCM (0.2 mL) was added TFA (229 mg, 2.01 mmol, 148 uL) at 15° C. and the mixture was stirred at 15° C. for 5 hours. The reaction mixture was concentrated under vacuum to give [4-[4-[3-(cyanomethyl)piperazin-1-yl]-2-[[(2R)-1-methylpyrrolidin-2-yl]methoxy]-6,8-dihydro-5H-pyrido[3,4-d]pyrimidin-7-yl]-2-naphthyl] 2,2-dimethylpropanoate (170 mg, crude, 2TFA) as brown oil.

Step I: [4-[4-[3-(cyanomethyl)-4-prop-2-enoyl-piperazin-1-yl]-2-[[(2R)-1-methylpyrrolidin-2-yl]methoxy]-6,8-dihydro-5H-pyrido[3,4-d]pyrimidin-7-yl]-2-naphthyl]2,2-dimethylpropanoate: To a solution of [4-[4-[3-(cyanomethyl)piperazin-1-yl]-2-[[(2R)-1-methylpyrrolidin-2-yl]methoxy]-6,8-dihydro-5H-pyrido[3,4-d]pyrimidin-7-yl]-2-naphthyl] 2,2-dimethylpropanoate (170 mg, 206 umol, 2TFA) and DIEA (213 mg, 1.65 mmol, 287 uL) in DCM (0.3 mL) was added prop-2-enoyl prop-2-enoate (38.9 mg, 309 umol) at 0° C. and this mixture was stirred at 15° C. for 1 hour. The reaction mixture was quenched by water (0.5 mL), then concentrated under vacuum. The residue (DCM:MeOH=10:1) was purified by silica gel chromatography (from PE:EtOAc=2:1 to EtOAc:MeOH=0:1) to give [4-[4-[3-(cyanomethyl)-4-prop-2-enoyl-piperazin-1-yl]-2-[[(2R)-1-methylpyrrolidin-2-yl]methoxy]-6,8-dihydro-5H-pyrido[3,4-d]pyrimidin-7-yl]-2-naphthyl]2,2-dimethylpropanoate (170 mg, 182 umol, 88.7% yield, 70.0% purity) as brown oil. ES+APCI MS m/z 652.6[M+H]$^+$.

Step J: 2-[4-[7-(3-hydroxy-1-naphthyl)-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile: To a solution of [4-[4-[3-(cyanomethyl)-4-prop-2-enoyl-piperazin-1-yl]-2-[[(2R)-1-methylpyrrolidin-2-yl]methoxy]-6,8-dihydro-5H-pyrido[3,4-d]pyrimidin-7-yl]-2-naphthyl]2,2-dimethylpropanoate (170 mg, 261 umol) in THF (1.5 mL) was added NaOH (2 M, 1.5 mL) and the reaction was stirred at 15° C. for 6 hours. The reaction mixture was neutralized by HCOOH (20%, 0.1 mL) to PH=7. The resulting mixture was extracted with DCM (3×5 mL), the combined organic layers were dried over anhydrous $Na_2SO_4$, filtered and concentrated under reduced pressure to give a residue. The residue was purified by prep-HPLC (column: Luna C18 150*25 5 u; mobile phase: [water (0.225% Formic Acid)-ACN]; B %:12%-39%,10 min) to give 2-[4-[7-(3-hydroxy-1-naphthyl)-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (6.88 mg, 11.6 umol, 4.44% yield, 95.6% purity) as yellow solid. ES+APCI MS m/z 568.5[M+H]$^+$.

Example 179

2-[4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]-1-prop-2-enoyl-piperazin-2-yl]acetonitrile

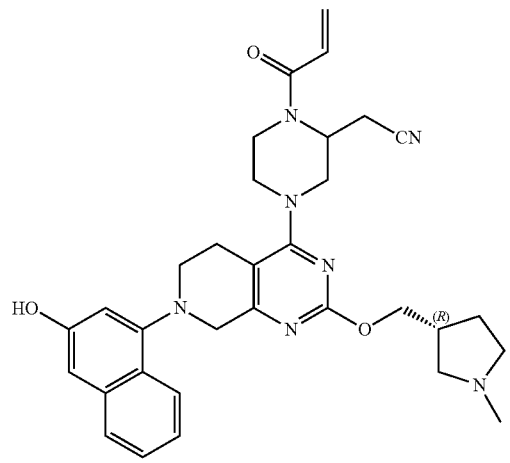

-continued
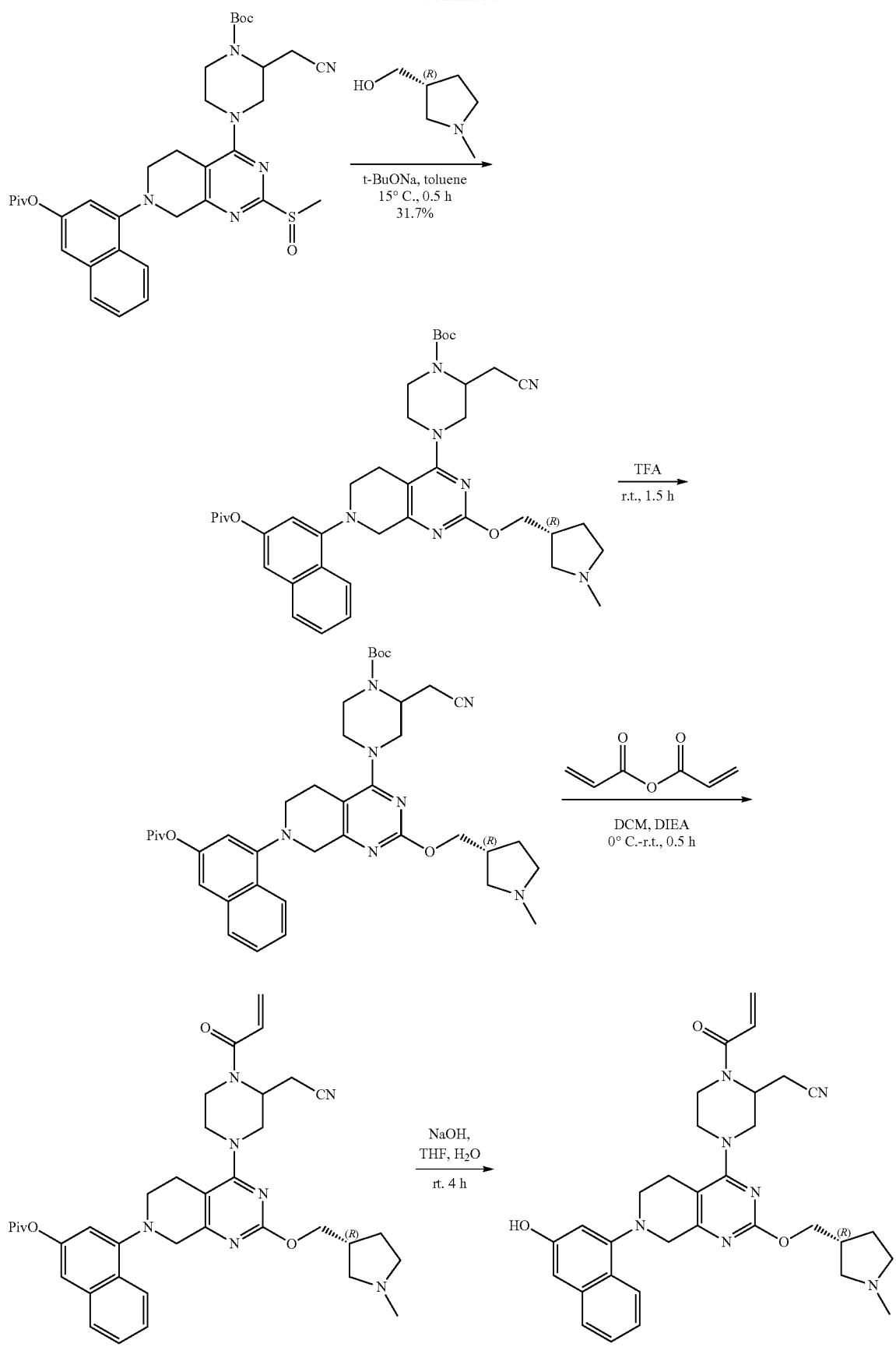

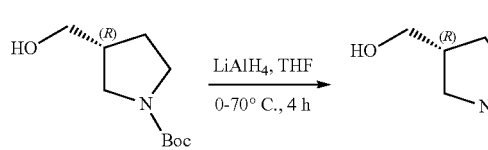

Step A: [(3R)-1-methylpyrrolidin-3-yl]methanol

To the solution of tert-butyl (3R)-3-(hydroxymethyl)pyrrolidine-1-carboxylate (1 g, 4.97 mmol) in THF (40 mL) was added LiAlH$_4$ (377 mg, 9.94 mmol) at 0° C., then the mixture was warmed to 70° C. and stirred at 70° C. for 4 hours. The reaction mixture was quenched by saturated Na$_2$SO$_4$ (3 mL) and filtered, the filter cake was washed with THF (5×20 mL). The combined organic phase was concentrated under vacuum to give [(3R)-1-methylpyrrolidin-3-yl] methanol (820 mg, crude) as yellow oil. $^1$H NMR (400 MHz, chloroform-d) δ=3.66-3.62 (dd, J=4.8, 10.0 Hz, 1H), 3.53-3.49 (dd, J=5.6, 10.0 Hz, 1H), 3.35-3.18 (m, 1H), 2.77-2.68 (m, 1H), 2.59-2.53 (m, 1H), 2.52-2.45 (m, 1H), 2.40-2.33 (m, 1H), 2.32 (s, 3H), 2.31-2.26 (m, 1H), 2.04-1.93 (m, 1H), 1.69-1.59 (m, 1H)

Step B: tert-butyl 2-(cyanomethyl)-4-[7-[3-(2,2-dimethylpropanoyloxy)-1-naphthyl]-2-[[(3R)-1-methylpyrrolidin-3-yl]methoxy]-6,8-dihydro-5H-pyrido[3,4-d]pyrimidin-4-yl]piperazine-1-carboxylate: To the solution of tert-butyl 2-(cyanomethyl)-4-[7-[3-(2,2-dimethylpropanoyloxy)-1-naphthyl]-2-methylsulfinyl-6,8-dihydro-5H-pyrido[3,4-d]pyrimidin-4-yl]piperazine-1-carboxylate (500 mg, 773 umol) and [(3R)-1-methylpyrrolidin-3-yl]methanol (178 mg, 1.55 mmol) in toluene (10 mL) was added t-BuONa (111 mg, 1.16 mmol) and this mixture stirred at 15° C. for 0.5 hour. To the mixture was added ethyl acetate (20 mL) and water (15 mL), then extracted with ethyl acetate (3×20 mL). The combined organic layers were washed with brine (20 mL). The combined organic layers were dried over anhydrous Na$_2$SO$_4$, filtered and concentrated under reduced pressure. The residue was purified by reversed phase flash column (ACN/Water (0.1% Formic Acid)=42%) to give tert-butyl 2-(cyanomethyl)-4-[7-[3-(2,2-dimethylpropanoyloxy)-1-naphthyl]-2-[[(3R)-1-methylpyrrolidin-3-yl]methoxy]-6,8-dihydro-5H-pyrido[3,4-d]pyrimidin-4-yl]piperazine-1-carboxylate (180 mg, 245 umol, 31.7% yield, 95.0% purity) as brown solid. ES+APCI MS m/z 698.6[M+H]$^+$.

Step C: [4-[4-[3-(cyanomethyl)piperazin-1-yl]-2-[[(3R)-1-methylpyrrolidin-3-yl]methoxy]-6,8-dihydro-5H-pyrido[3,4-d]pyrimidin-7-yl]-2-naphthyl] 2,2-dimethylpropanoate: A mixture of tert-butyl 2-(cyanomethyl)-4-[7-[3-(2,2-dimethylpropanoyloxy)-1-naphthyl]-2-[[(3R)-1-methylpyrrolidin-3-yl]methoxy]-6,8-dihydro-5H-pyrido[3,4-d]pyrimidin-4-yl]piperazine-1-carboxylate (180 mg, 258 umol) and TFA (588 mg, 5.16 mmol, 382 uL) was stirred at 20° C. for 1.5 hours. The reaction mixture was concentrated under vacuum to give [4-[4-[3-(cyanomethyl)piperazin-1-yl]-2-[[(3R)-1-methylpyrrolidin-3-yl]methoxy]-6,8-dihydro-5H-pyrido[3,4-d]pyrimidin-7-yl]-2-naphthyl] 2,2-dimethylpropanoate (200 mg, crude, 2TFA) as a brown oil.

Step D: [4-[4-[3-(cyanomethyl)-4-prop-2-enoyl-piperazin-1-yl]-2-[[(3R)-1-methylpyrrolidin-3-yl]methoxy]-6,8-dihydro-5H-pyrido[3,4-d]pyrimidin-7-yl]-2-naphthyl] 2,2-dimethylpropanoate: To the solution of [4-[4-[3-(cyanomethyl)piperazin-1-yl]-2-[[(3R)-1-methylpyrrolidin-3-yl]methoxy]-6,8-dihydro-5H-pyrido[3,4-d]pyrimidin-7-yl]-2-naphthyl] 2,2-dimethylpropanoate (200 mg, 242 umol, 2TFA) and DIEA (470 mg, 3.63 mmol, 633 uL) in DCM (0.6 mL) was added prop-2-enoyl prop-2-enoate (30.5 mg, 242 umol) at 0° C. and the reaction stirred at 15° C. for 1 hour. The reaction mixture was concentrated under vacuum. The residue was purified by silica gel chromatography (PE:EA=2:1~0:1 to DCM:MeOH=50:1~1:1) to give [4-[4-[3-(cyanomethyl)-4-prop-2-enoyl-piperazin-1-yl]-2-[[(3R)-1-methylpyrrolidin-3-yl]methoxy]-6,8-dihydro-5H-pyrido[3,4-d]pyrimidin-7-yl]-2-naphthyl] 2,2-dimethylpropanoate (630 mg, crude) as brown oil. ES+APCI MS m/z 652.6[M+H]$^+$.

Step E: 2-[4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]-1-prop-2-enoyl-piperazin-2-yl]acetonitrile: To a solution of [4-[4-[3-(cyanomethyl)-4-prop-2-enoyl-piperazin-1-yl]-2-[[(3R)-1-methylpyrrolidin-3-yl]methoxy]-6,8-dihydro-5H-pyrido[3,4-d]pyrimidin-7-yl]-2-naphthyl] 2,2-dimethylpropanoate (630 mg, 966 umol) in THF (3 mL) was added NaOH (2 M, 3 mL) at 18° C. and the mixture stirred at 18° C. for 2 hours. The reaction mixture was neutralized by HCOOH (20%, 0.5 mL) to PH=7. The resulting mixture was extracted with DCM (3×5 mL), the combined organic layers were dried over anhydrous Na$_2$SO$_4$, filtered and concentrated under reduced pressure. The residue was purified by prep-HPLC (column: Phenomenex Gemini 150*25 mm*10 um; mobile phase: [water (10 mM NH4HCO3)-ACN]; B %: 35%-65%,3 min) to give 2-[4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]-1-prop-2-enoyl-piperazin-2-yl]acetonitrile (9.4 mg, 15.8 umol, 1.64% yield, 95.5% purity) as yellow solid. ES+APCI MS m/z 568.5[M+H]$^+$.

Example 180
4-(3-(4-(piperazin-1-yl)-7-(5-(trifluoromethyl)-1H-indazol-4-yl)-5,6,7,8-tetrahydropyrido[3,4-d]pyrimidin-2-yloxy)propyl)morpholine
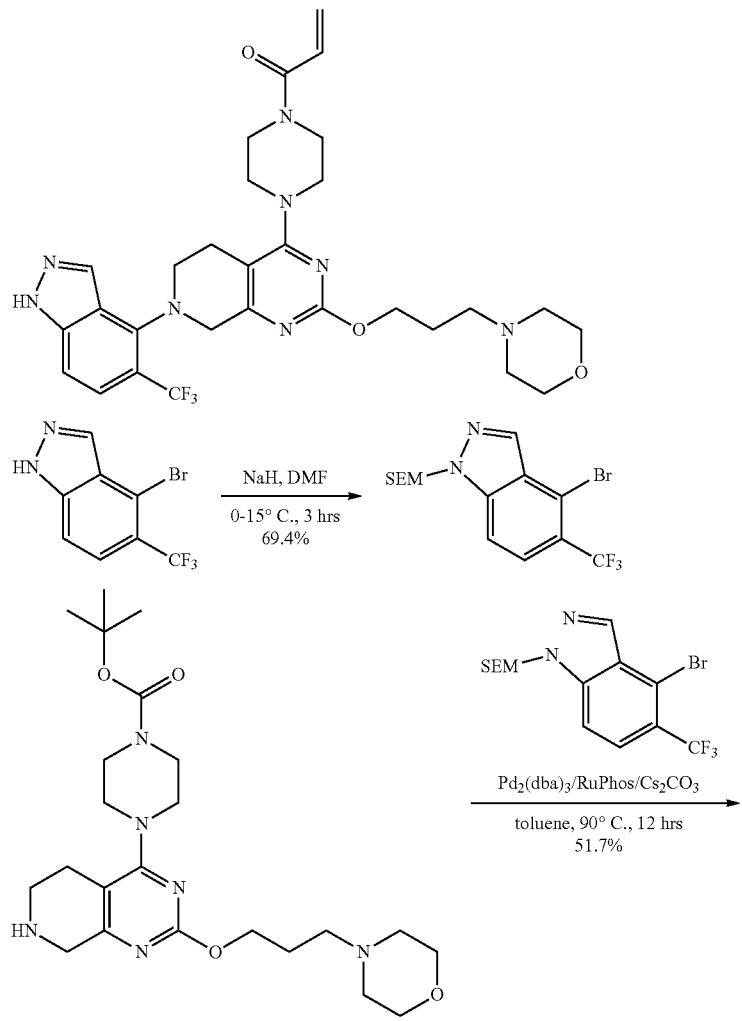
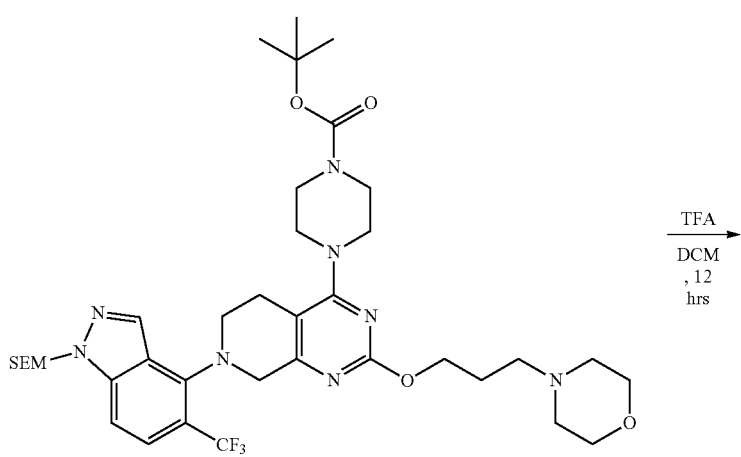

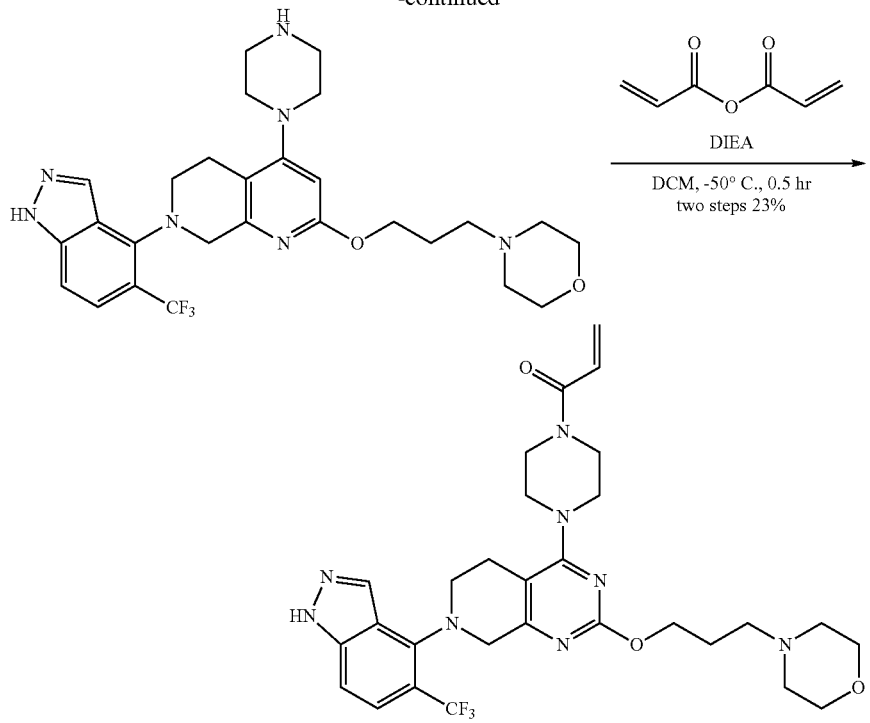

Step A. 2-[[4-bromo-5-(trifluoromethyl)indazol-1-yl]methoxy]ethyl-trimethyl-silane To a solution of 4-bromo-5-(trifluoromethyl)-1H-indazole (650 mg, 2.45 mmol, 1 eq) in DMF (30 mL) was added NaH (117.71 mg, 2.94 mmol, 60% purity, 1.2 eq) at 0° C. After being stirred at 0° C. for 1 hour, a solution of 2-(chloromethoxy)ethyltrimethyl-silane (531.56 mg, 3.19 mmol, 564.29 uL, 1.3 eq) in DMF (10 mL) was added dropwise. The mixture was warmed to 15° C. and stirred for 2 hours. The mixture was quenched with saturated aqueous ammonium chloride solution (50.0 mL), diluted with water (100.0 mL) and then extracted with ethyl acetate (3×100.0 mL). The organic layer was dried over $Na_2SO_4$, filtered and concentrated under vacuum to give a residue. The residue was purified by column chromatography ($SiO_2$, Petroleum ether/Ethyl acetate=10:1). 2-[[4-bromo-5-(trifluoromethyl)indazol-1-yl]methoxy]ethyl-trimethyl-silane (680 mg, 1.70 mmol, 69.44% yield, 99.0% purity) was obtained as a colorless oil. ES+APCI MS m/z 395.0[M+H]$^+$.

Step B. tert-butyl 4-[2-(3-morpholinopropoxy)-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate:

A mixture of 2-[[4-bromo-5-(trifluoromethyl)indazol-1-yl]methoxy]ethyl-trimethyl-silane (444.35 mg, 1.12 mmol, 1.3 eq), tert-butyl 4-[2-(3-morpholinopropoxy)-5,6,7,8-tetrahydropyrido[3,4-d]pyrimidin-4-yl]piperazine-1-carboxylate (400 mg, 864.71 umol, 1 eq), RuPhos (80.70 mg, 172.94 umol, 0.2 eq), $Pd_2(dba)_3$ (118.77 mg, 129.71 umol, 0.15 eq), and $Cs_2CO_3$ (845.21 mg, 2.59 mmol, 3 eq) in toluene (40 mL) was degassed and purged with $N_2$ 3 times, and the mixture was stirred at 90° C. for 12 hrs under nitrogen. The reaction mixture was concentrated under reduced pressure to remove toluene. The residue was diluted with water 100 mL and extracted with Ethyl acetate 300 mL (100 mL×3). The combined organic layers were washed with water 300 mL (100 mL×3), dried over $Na_2SO_4$, filtered and concentrated under reduced pressure to give a residue. The residue was purified by column chromatography ($SiO_2$, DCM: $CH_3OH$=30:1 to 20:1). tert-butyl 4-[2-(3-morpholinopropoxy)-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (400 mg, 446.87 umol, 51.68% yield, 86.8% purity) was obtained as a yellow solid. ES+APCI MS m/z 773.3[M+H]$^+$.

Step C. 4-[3-[[4-piperazin-1-yl-7-[5-(trifluoromethyl)-1H-indazol-4-yl]-6,8-dihydro-5H-pyrido[3,4-d]pyrimidin-2-yl]oxy]propyl]morpholine:

To a solution of tert-butyl 4-[2-(3-morpholinopropoxy)-7-[5-(trifluoromethyl)-1-(2-trimethylsilylethoxymethyl)indazol-4-yl]-6,8-dihydro-5Hpyrido[3,4-d]pyrimidin-4-yl]piperazine-1-carboxylate (100 mg, 111.72 umol, 1 eq) in DCM (2 mL) was added TFA (254.77 mg, 2.23 mmol, 165.43 uL, 20 eq) at 25° C. The reaction mixture was stirred at 25° C. for 12 hours. The reaction mixture was concentrated in vacuum. 4-[3-[[4-piperazin-1-yl-7-[5-(trifluoromethyl)-1H-indazol-4-yl]-6,8-dihydro-5H-pyrido[3,4-d]pyrimidin-2-yl]oxy]propyl]morpholine (200 mg, crude, TFA) was obtained as a brown color oil. The crude product was used directly to the next step without further purification. ES+APCI MS m/z 547.5[M+H]$^+$.

Step D. 1-[4-[2-(3-morpholinopropoxy)-7-[5-(trifluoromethyl)-1H-indazol-4-yl]-6,8-dihydro-5H-pyrido[3,4-d]pyrimidin-4-yl]piperazin-1-yl]prop-2-en-1-one:

To a solution of 4-[3-[[4-piperazin-1-yl-7-[5-(trifluoromethyl)-1H-indazol-4-yl]-6,8-dihydro-5H-pyrido[3,4-d]pyrimidin-2-yl]oxy]propyl]morpholine (200 mg, TFA) and DIEA (600 mg, 4.64 mmol, 808.63 uL) in DCM (2 mL) was added dropwise prop-2-enoyl prop-2-enoate (13 mg, 103.08 umol) at −50° C. The mixture was stirred at −50° C. for 30 min. The mixture was quenched with water and extracted with ethyl acetate (50 mL), the organic layer was washed with water (1×20 mL) and brine (1×20 mL). The separated organic layer was dried over sodium sulfate, filtered and concentrated under vacuum. The residue was purified by prep-HPLC (FA condition) column: Luna C18 150*25 5 u; mobile phase: [water (0.225% FA)-ACN]; B %: 15%-36%,10 min]. 1-[4-[2-(3-morpholinopropoxy)-7-[5-(trifluoromethyl)-1H-indazol-4-yl]-6,8-dihydro-5H-pyrido[3,4-d]pyrimidin-4-yl]piperazin-1-yl]prop-2-en-1-one (18.26 mg, 28.12 mmol, two steps 23%, 99.6% purity, FA) was obtained as a yellow solid. ES+APCI MS m/z 601.4[M+H]+.

Example 181

1-(4-(2-(3-((1S,4S)-2-oxa-5-azabicyclo[2.2.1]heptan-5-yl)propoxy)-7-(5-methyl-1H-indazol-4-yl)-5,6,7,8-tetrahydropyrido[3,4-d]pyrimidin-4-yl)piperazin-1-yl)prop-2-en-1-one

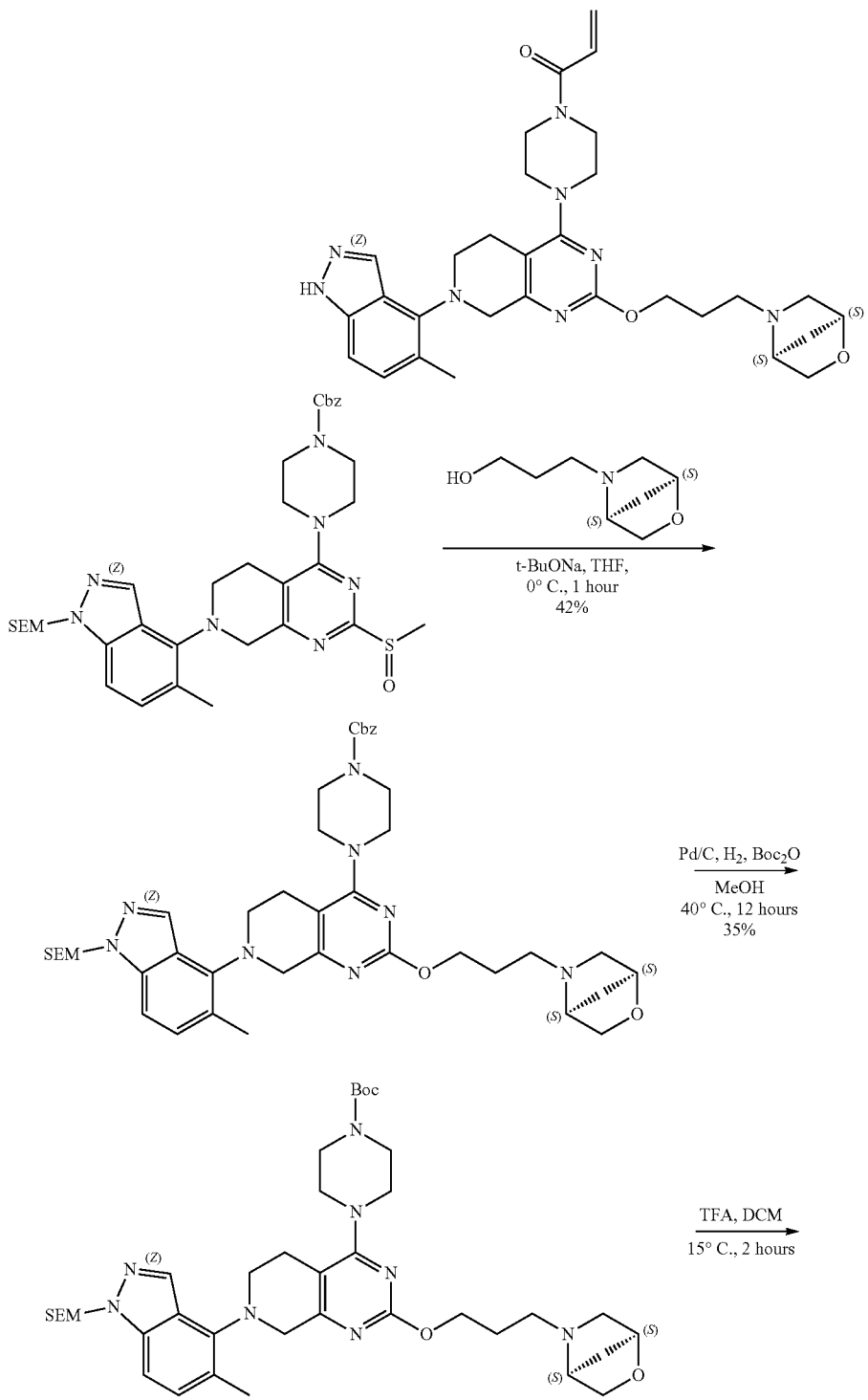

-continued

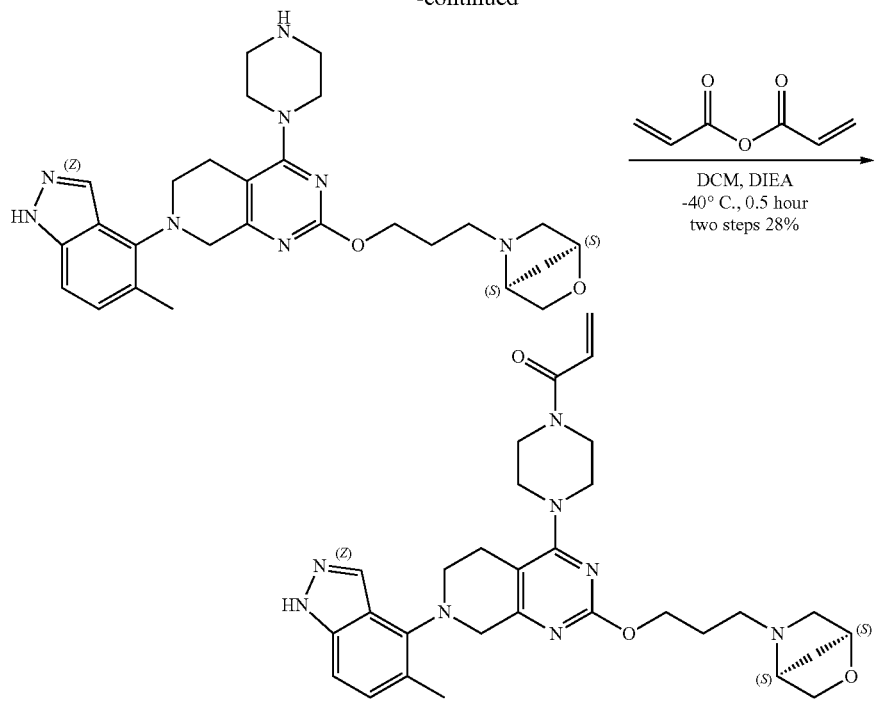

Step A. benzyl 4-(2-(3-((1S,4S)-2-oxa-5-azabicyclo[2.2.1]heptan-5-yl)propoxy)-7-(5-methyl-1-((2-(trimethylsilyl)ethoxy)methyl)-1H-indazol-4-yl)-5,6,7,8-tetrahydropyrido[3,4-d]pyrimidin-4-yl)piperazine-1-carboxylate: To a solution of 3-((1S,4S)-2-oxa-5-azabicyclo[2.2.1] heptan-5-yl)propan-1-ol (107 mg, 681 umol) in THF (2 mL) was added t-BuONa (98.1 mg, 1.02 mmol) followed by benzyl 4-[2-methylsulfinyl-7-[5-methyl-1-(2-trimethylsilylethoxymethyl)indazol-4-yl]-6,8-dihydro-5H-pyrido[3,4-d]pyrimidin-4-yl]piperazine-1-carboxylate (230 mg, 340 umol). The mixture was stirred at 0° C. for 1 hour. The mixture was poured into water (10 mL) and extracted with DCM (2×10 mL). The organic layer was dried over Na$_2$SO$_4$, filtered and concentrated. The obtained product was purified by prep-HPLC (column: Phenomenex Synergi C18 150*25*10 um; mobile phase: [water (0.1% TFA)-ACN]; B %: 25%-55%, 12 min) to give benzyl 4-(2-(3-((1S,4S)-2-oxa-5-azabicyclo[2.2.1]heptan-5-yl)propoxy)-7-(5-methyl-1-((2-(trimethylsilyl)ethoxy)methyl)-1H-indazol-4-yl)-5,6,7,8-tetrahydropyrido[3,4-d]pyrimidin-4-yl)piperazine-1-carboxylate (110 mg, 143 umol, 42.0% yield) was obtained as yellow solid. $^1$H NMR (400 MHz, Chloroform-d) δ 8.08-8.01 (m, 1H), 7.45-7.43 (m, 4H), 7.37-7.31 (m, 3H), 5.76 (s, 2H), 5.24 (s, 2H), 4.76-4.63 (m, 1H), 4.60-4.45 (m, 3H), 4.42 (s, 2H), 4.36-4.24 (m, 1H), 3.96-3.83 (m, 2H), 3.79-3.65 (m, 8H), 3.64-3.53 (m, 6H), 3.12-2.92 (m, 1H), 2.90-2.77 (m, 2H), 2.48 (s, 3H), 2.44-2.41 (m, 1H), 2.36-2.12 (m, 3H), 0.98-0.93 (m, 2H), 0.01-0.03 (m, 9H)

Step B. tert-butyl 4-(2-(3-((1S,4S)-2-oxa-5-azabicyclo[2.2.1]heptan-5-yl)propoxy)-7-(5-methyl-1-((2-(trimethylsilyl)ethoxy)methyl)-1H-indazol-4-yl)-5,6,7,8-tetrahydropyrido[3,4-d]pyrimidin-4-yl)piperazine-1-carboxylate: To a solution of benzyl 4-(2-(3-((1S,4S)-2-oxa-5-azabicyclo[2.2.1]heptan-5-yl)propoxy)-7-(5-methyl-1-((2-(trimethylsilyl)ethoxy)methyl)-1H-indazol-4-yl)-5,6,7,8-tetrahydropyrido[3,4-d]pyrimidin-4-yl)piperazine-1-carboxylate (90 mg, 117 umol) and BOC$_2$O (51.1 mg, 234.1 umol, 53.8 uL) in MeOH (2 mL) was added Pd/C (10%, 50 mg) under an N$_2$ atmosphere. The suspension was degassed under vacuum and purged with H$_2$ several times. The mixture was stirred under H$_2$ (15 psi) at 40° C. for 12 hours. The mixture was filtered and concentrated. The residue was purified by prep-TLC (SiO$_2$, DCM/MeOH=10:1) to give tert-butyl 4-(2-(3-((1S,4S)-2-oxa-5-azabicyclo[2.2.1]heptan-5-yl)propoxy)-7-(5-methyl-1-((2-(trimethylsilyl)ethoxy)methyl)-1H-indazol-4-yl)-5,6,7,8-tetrahydropyrido[3,4-d]pyrimidin-4-yl)piperazine-1-carboxylate (30 mg, 40.8 umol). ES+APCI MS m/z 735.6[M+H]$^+$.

Step C. (1S,4S)-5-(3-((7-(5-methyl-1H-indazol-4-yl)-4-(piperazin-1-yl)-5,6,7,8-tetrahydropyrido[3,4-d]pyrimidin-2-yl)oxy)propyl)-2-oxa-5-azabicyclo[2.2.1]heptane: To a solution of tert-butyl 4-(2-(3-((1S,4S)-2-oxa-5-azabicyclo[2.2.1]heptan-5-yl)propoxy)-7-(5-methyl-1-((2-(trimethylsilyl)ethoxy)methyl)-1H-indazol-4-yl)-5,6,7,8-tetrahydropyrido[3,4-d]pyrimidin-4-yl)piperazine-1-carboxylate (30 mg, 40.8 umol) in DCM (0.5 mL) was added TFA (770 mg, 6.75 mmol) dropwise. The mixture was stirred at 15° C. for 2 hours. The mixture was concentrated under vacuum to give (1S,4S)-5-(3-((7-(5-methyl-1H-indazol-4-yl)-4-(piperazin-1-yl)-5,6,7,8-tetrahydropyrido[3,4-d]pyrimidin-2-yl)oxy)propyl)-2-oxa-5-azabicyclo[2.2.1]heptane (30 mg, crude). ES+APCI MS m/z 505.5[M+H]$^+$.

Step D. 1-(4-(2-(3-((1S,4S)-2-oxa-5-azabicyclo[2.2.1]heptan-5-yl)propoxy)-7-(5-methyl-1H-indazol-4-yl)-5,6,7,8-tetrahydropyrido[3,4-d]pyrimidin-4-yl)piperazin-1-yl)prop-2-en-1-one: To a solution of (1S,4S)-5-(3-((7-(5-methyl-1H-indazol-4-yl)-4-(piperazin-1-yl)-5,6,7,8-tetrahydropyrido[3,4-d]pyrimidin-2-yl)oxy)propyl)-2-oxa-5-azabicyclo[2.2.1]heptane (20 mg, 39.6 umol, 1 eq) and DIEA (30.7 mg, 238 umol, 41.4 uL, 6 eq) in DCM (2 mL) was added prop-2-enoyl prop-2-enoate (4.00 mg, 31.7 umol, 0.8 eq) at −50° C. The mixture was stirred at −40-−20° C. for 0.5 hour. The mixture was concentrated under vacuum. The obtained product was purified by prep-HPLC (column:

Phenomenex Gemini 150*25 mm*10 um; mobile phase: [water (0.05% ammonia hydroxide v/v)-ACN]; B %: 35%-65%,12 min). The product 1-(4-(2-(3-((1S,4S)-2-oxa-5-azabicyclo[2.2.1]heptan-5-yl)propoxy)-7-(5-methyl-1H-indazol-4-yl)-5,6,7,8-tetrahydropyrido[3,4-d]pyrimidin-4-yl)piperazin-1-yl)prop-2-en-1-one (6.48 mg, 11.2 umol, two steps 28.3% yield, 96.8% purity) was obtained as white solid. ES+APCI MS m/z 559.5[M+H]+.

Example 182

2-[4-[7-(3-hydroxy-1-naphthyl)-2-[[(2S)-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile

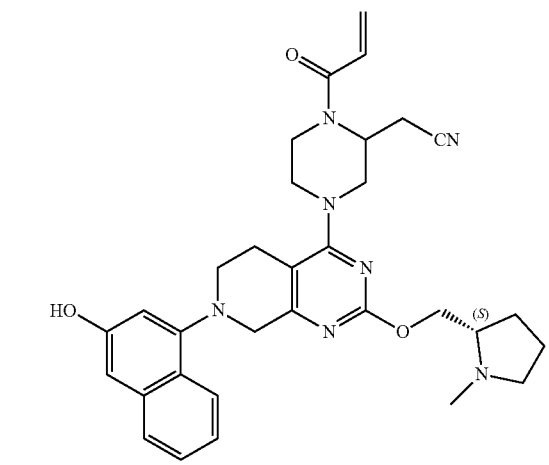

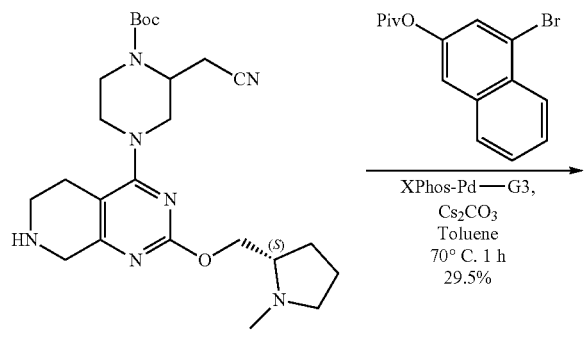

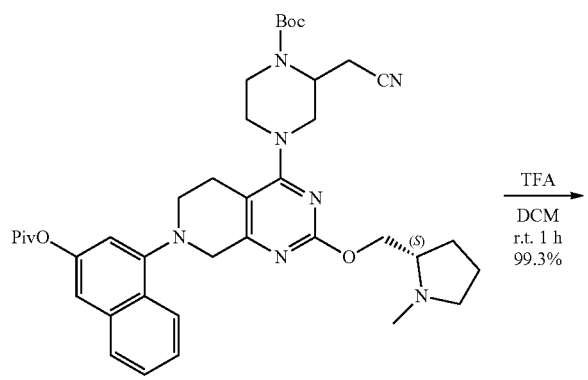

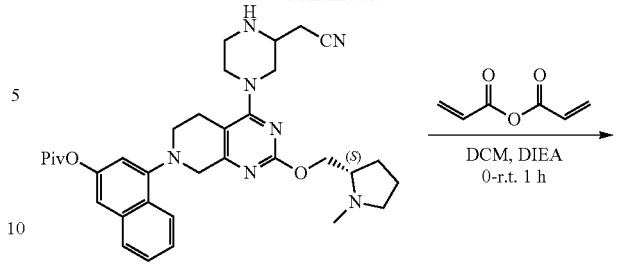

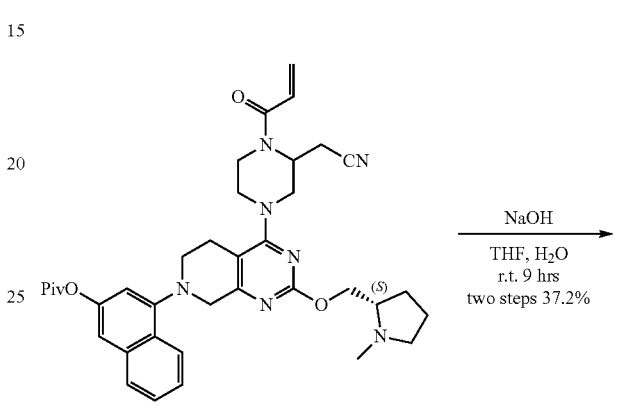

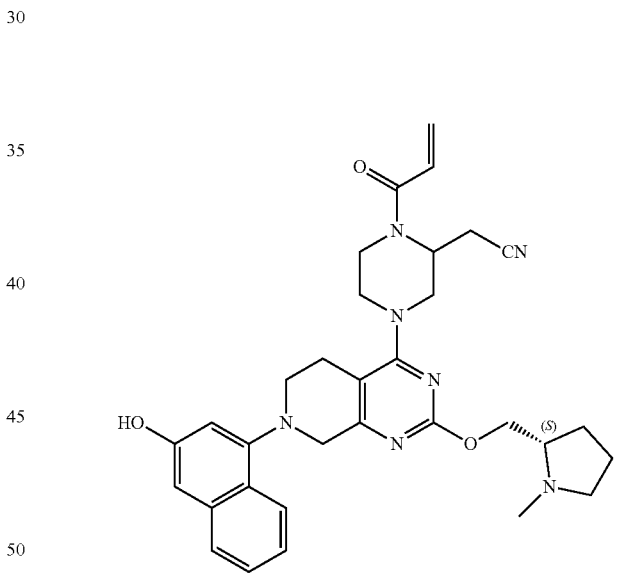

Step A: tert-butyl 2-(cyanomethyl)-4-[7-[3-(2,2-dimethylpropanoyloxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate. To a mixture of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (190 mg, 403 umol), (4-bromo-2-naphthyl) 2,2-dimethylpropanoate (248 mg, 806 umol) and Cs$_2$CO$_3$ (394 mg, 1.21 mmol) in toluene (5 mL) was added XPHOS Palladacycle Gen 3 (34.1 mg, 40.29 umol) and the reaction mixture stirred at 70° C. for 4 hours under N$_2$. Upon completion, the reaction mixture was purified by silica gel chromatography (PE:EA=3:1 to 0:1) to give tert-butyl 2-(cyanomethyl)-4-[7-[3-(2,2-dimethylpropanoyloxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate (95 mg, 118 umol). ES+APCI MS m/z 698.4 [M+H]⁺.

Step B: [4-[4-[3-(cyanomethyl)piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate. To a solution of tert-butyl 2-(cyanomethyl)-4-[7-[3-(2,2-dimethylpropanoyloxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate (40 mg, 57.3 umol) in DCM (0.1 mL) was added TFA (154 mg, 1.35 mmol) at 15° C. The reaction mixture was stirred at 15° C. for 1 hour. Upon completion, the solvent was removed under vacuum to give [4-[4-[3-(cyanomethyl)piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate (47 mg, 56.9 umol).

Step C: [4-[4-[3-(cyanomethyl)-4-prop-2-enoyl-piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate. To a solution of [4-[4-[3-(cyanomethyl)piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate (47 mg, 56.9 umol) and DIEA (58.9 mg, 455 umol) in DCM (1 mL) was added prop-2-enoyl prop-2-enoate (10.8 mg, 85.4 umol) at 0° C. The reaction mixture was stirred at 15° C. for 1 hour. Upon completion, the reaction mixture was quenched by addition of a drop of water. The residue was purified by silica gel chromatography (PE:EtOAc=3:1 to EtOAc:MeOH=3:1) to give [4-[4-[3-(cyanomethyl)-4-prop-2-enoyl-piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate (130 mg, crude). ES+APCI MS m/z 652.5 [M+H]⁺.

Step D: 2-[4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile. To a solution of [4-[4-[3-(cyanomethyl)-4-prop-2-enoyl-piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate (250 mg, 384 umol) in THF (1.5 mL) was added NaOH (2 M, 1.5 mL) in water. The reaction mixture was stirred at 15° C. for 9 hours. Upon completion, the reaction mixture was acidified by addition of two drops of formic acid (20% in water) to reach a pH=7 and the aqueous layer extracted with DCM (5×10 mL). The combined organic layers were dried over Na₂SO₄, filtered and concentrated under vacuum. The residue was purified by prep-HPLC (column: Boston Green ODS 150*30 5 u; mobile phase: [water (0.225% FA)-ACN]; B %: 20%-47%, 10 min) to give 2-[4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (13.1 mg, 21.2 umol). ES+APCI MS m/z 568.5 [M+H]⁺.

Example 183

2-[4-[2-[[(2R)-1-methylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile

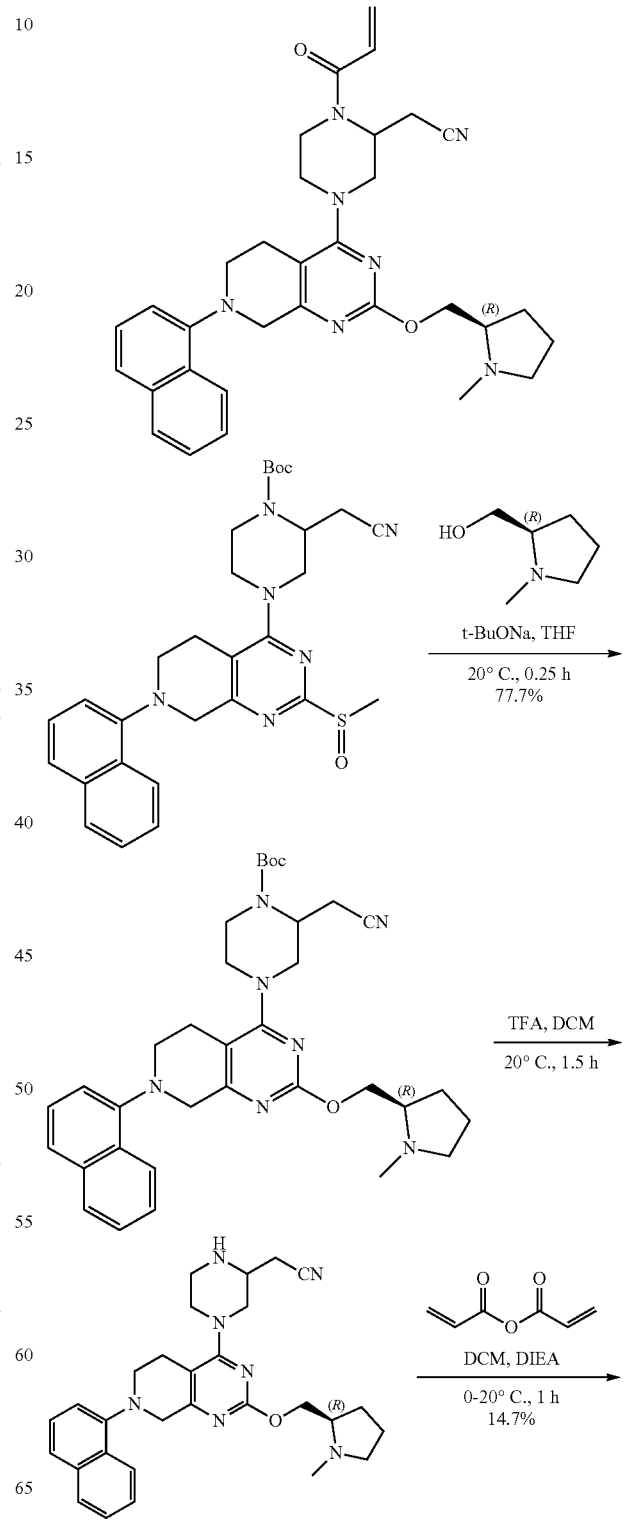

583
-continued

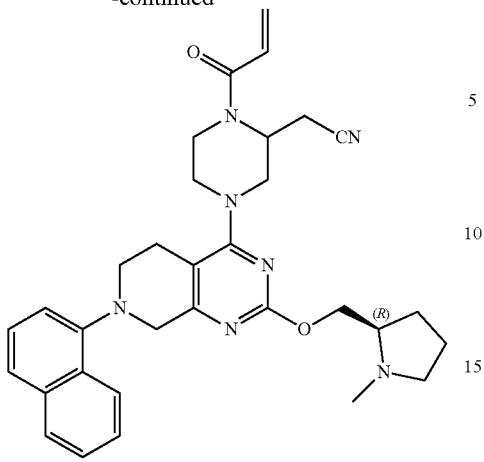

Step A: tert-butyl 2-(cyanomethyl)-4-[2-[[(2R)-1-methyl-pyrrolidin-2-yl]methoxy]-7-(1-naphthyl)-6,8-dihydro-5H-pyrido[3,4-d]pyrimidin-4-yl]piperazine-1-carboxylate. To a solution of tert-butyl 2-(cyanomethyl)-4-[2-methylsulfinyl-7-(1-naphthyl)-6,8-dihydro-5H-pyrido[3,4-d]pyrimidin-4-yl]piperazine-1-carboxylate (300 mg, 549 umol) and [(2S)-1-methylpyrrolidin-2-yl]methanol (126 mg, 1.10 mmol, 130 uL) in toluene (6.00 mL) was added t-BuONa (105 mg, 1.10 mmol). The mixture was stirred at 20° C. for 0.25 hour. Upon completion, the mixture was filtered and the filtrate was concentrated. The residue was purified by silica gel chromatography (EA/MeOH 50/1 to 10/1) to give tert-butyl 2-(cyanomethyl)-4-[2-[[(2R)-1-methylpyrrolidin-2-yl]methoxy]-7-(1-naphthyl)-6,8-dihydro-5H-pyrido[3,4-d]pyrimidin-4-yl]piperazine-1-carboxylate (300 mg, 427 umol). ES+APCI MS m/z 598.6 [M+H]+.

Step B: 2-[4-[2-[[(2R)-1-methylpyrrolidin-2-yl]methoxy]-7-(1-naphthyl)-6,8-dihydro-5H-pyrido[3,4-d]pyrimidin-4-yl]piperazin-2-yl]acetonitrile. To a solution of tert-butyl 2-(cyanomethyl)-4-[2-[[(2R)-1-methylpyrrolidin-2-yl]methoxy]-7-(1-naphthyl)-6,8-dihydro-5H-pyrido[3,4-d]pyrimidin-4-yl]piperazine-1-carboxylate (270 mg, 452 umol) in DCM (330 uL) was added TFA (515 mg, 4.52 mmol). The mixture was stirred at 20° C. for 0.5 hour and concentrated under vacuum. Then TFA (334 uL) was added. The mixture was stirred at 20° C. for 1 hour. Upon completion, the mixture was concentrated under vacuum to give 2-[4-[2-[[(2R)-1-methylpyrrolidin-2-yl]methoxy]-7-(1-naphthyl)-6,8-dihydro-5H-pyrido[3,4-d]pyrimidin-4-yl]piperazin-2-yl]acetonitrile (400 mg, crude). ES+APCI MS m/z 498.4 [M+H]+.

Step C: 2-[4-[2-[[(2R)-1-methylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile. To a solution of 2-[4-[2-[[(2R)-1-methylpyrrolidin-2-yl]methoxy]-7-(1-naphthyl)-6,8-dihydro-5H-pyrido[3,4-d]pyrimidin-4-yl]piperazin-2-yl]acetonitrile (276 mg, 451 umol) and DIEA (1.46 g, 11.3 mmol) in DCM (4.00 mL) was added prop-2-enoyl prop-2-enoate (51.2 mg, 406 umol) dropwise at 0° C. The mixture was stirred at 20° C. for 1 hour. Upon completion, the mixture was diluted with water (0.5 mL) and extracted with EtOAc (2×10 mL). The combined organic layers were dried over Na2SO4 and concentrated under vacuum. The residue was purified by prep-HPLC (column: Phenomenex Gemini 150*25 mm*10 um; mobile phase: [water (0.05% ammonia hydroxide v/v)-ACN]; B %: 55%-85%,12 min) to give 2-[4-[2-[[(2R)-1-methylpyrrolidin-2-

584 yl]methoxy]-7-(1-naphthyl)-6,8-dihydro-5H-pyrido[3,4-d]pyrimidin-4-yl]-1-prop-2-enoyl-piperazin-2-yl]acetonitrile (37.1 mg, 66.3 umol). ES+APCI MS m/z 552.4 [M+H]+.

Example 184

1-[4-[7-(3-hydroxy-1-naphthyl)-2-(3-hydroxy-propoxy)-6,8-dihydro-5H-pyrido[3,4-d]pyrimidin-4-yl]piperazin-1-yl]prop-2-en-1-one

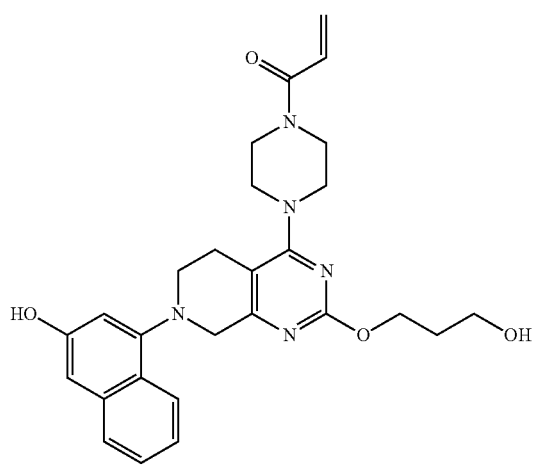 [SMILES: C=CC(=O)N1CCN(c2nc(OCCCO)nc3c2CCN(c2cc(O)cc4ccccc24)C3)CC1]

1-[4-[7-(3-hydroxy-1-naphthyl)-2-(3-hydroxypropoxy)-6,8-dihydro-5H-pyrido[3,4-d]pyrimidin-4-yl]piperazin-1-yl]prop-2-en-1-one was prepared following Example 136 substituting 3-[tert-butyl(dimethyl)silyl]oxypropan-1-ol for 2-(3-methoxypyrrolidin-1-yl)ethanol in Step B. ES+APCI MS m/z 490.3 [M+H]+.

Example 185

1-(4-(2-(3-((1R,4R)-2-oxa-5-azabicyclo[2.2.1]heptan-5-yl)propoxy)-7-(3-hydroxynaphthalen-1-yl)-5,6,7,8-tetrahydropyrido[3,4-d]pyrimidin-4-yl)piperazin-1-yl)prop-2-en-1-one

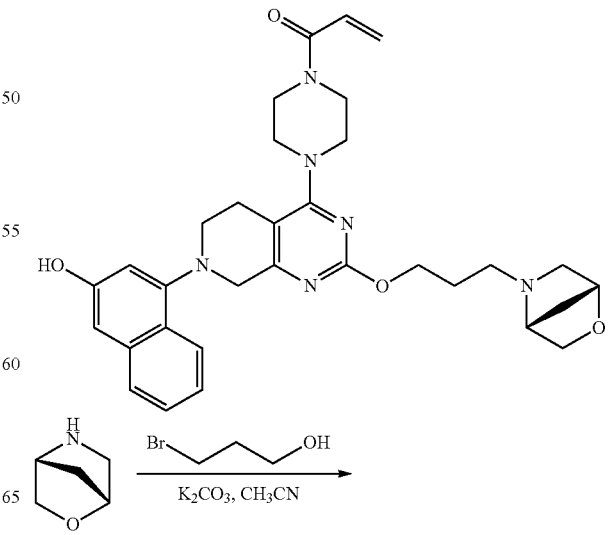

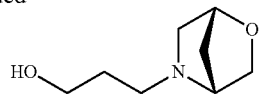

Step A: 3-((1R,4R)-2-oxa-5-azabicyclo[2.2.1]heptan-5-yl)propan-1-ol

To a vial was added (1R,4R)-2-Oxa-5-azabicyclo[2.2.1]heptane HCl salt (0.250 g, 2.522 mmol), $CH_3CN$ (5.04 mL) and 3-Bromo-1-propanol (0.274 mL, 3.026 mmol). Then $K_2CO_3$ (1.05 g, 7.57 mmol) was added and the mixture was warmed to 50° C. where it stirred for 16 hours. The mixture was then cooled to ambient temperature, diluted with $CH_2Cl_2$ and filtered and the solid was washed with $CH_2Cl_2$. The filtrate was then concentrated and the crude oil was purified via column chromatography (5% MeOH/DCM with 0.2% $NH_4OH$) to afford the product as a colorless oil.

Step B: 1-(4-(2-(3-((1R,4R)-2-oxa-5-azabicyclo[2.2.1]heptan-5-yl)propoxy)-7-(3-hydroxynaphthalen-1-yl)-5,6,7,8-tetrahydropyrido[3,4-d]pyrimidin-4-yl)piperazin-1-yl)prop-2-en-1-one Synthesized according to the method of Example 127 using the following procedure in place of that outlined in Step D. To a vial was added 3-((1R,4R)-2-oxa-5-azabicyclo[2.2.1]heptan-5-yl)propan-1-ol (0.171 g, 1.09 mmol) and benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (0.125 g, 0.218 mmol) followed by dioxane (0.435 mL). Then $Cs_2CO_3$ (0.213 g, 0.653 mmol) was added and the mixture was heated to 100° C. for 15 hours. The reaction was diluted with $CH_2Cl_2$, filtered and the residual solid was washed with $CH_2Cl_2$. The filtrate was then dried over $Na_2SO_4$, filtered and concentrated. The crude residue was purified by column chromatography (4% MeOH/DCM with 0.2% $NH_4OH$) to afford the product as a yellow foam. ES+APCI MS m/z 571.2 $[M+H]^+$.

Example 186

Benzyl 4-(7-(3-(methoxymethoxy)naphthalen-1-yl)-2-(3-(morpholinomethyl)phenyl)-5,6,7,8-tetrahydropyrido[3,4-d]pyrimidin-4-yl)piperazine-1-carboxylate

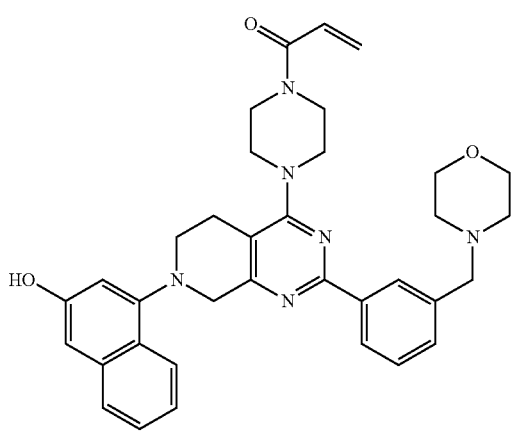 [SMILES: C=CC(=O)N1CCN(c2nc(-c3cccc(CN4CCOCC4)c3)nc3c2CCN(c2cc(O)cc4ccccc24)C3)CC1]

Benzyl 4-(7-(3-(methoxymethoxy)naphthalen-1-yl)-2-(3-(morpholinomethyl)phenyl)-5,6,7,8-tetrahydropyrido[3,4-d]pyrimidin-4-yl)piperazine-1-carboxylate Synthesized according to the method of Example 127 using the following procedure in place of that outlined in Step D. To a solution of benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (0.150 g, 0.261 mmol) and 3-(4-Morpholinomethyl)-phenylboronic acid pinacol ester hydrochloride (0.266 g, 0.784 mmol) in dioxane (2.61 mL) was added $Na_2CO_3$ (0.523 mL, 1.0452 mmol, 2.0M Aq). The mixture was degassed by argon bubbling for 5 min. Then Tetrakis(triphenylphosphine)palladium (0) (0.030 g, 0.026 mmol) was added and the mixture was heated to 95° C. where it stirred for 7 hours. The reaction was cooled to ambient temperature and then diluted with $CH_2Cl_2$ and filtered. The solid was washed with $CH_2Cl_2$. The filtrate was then dried over $Na_2SO_4$, filtered and concentrated. The crude residue was purified by column chromatography (30-50% EtOAc/DCM) to afford the product as a yellow foam. ES+APCI MS m/z 591.3 $[M+H]^+$.

Example 187

(R)-1-(4-(7-(3-hydroxynaphthalen-1-yl)-2-((1-methylpyrrolidin-2-yl)methoxy)-5,6,7,8-tetrahydropyrido[3,4-d]pyrimidin-4-yl)piperazin-1-yl)prop-2-en-1-one

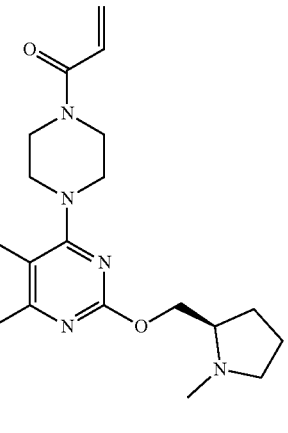

(R)-1-(4-(7-(3-hydroxynaphthalen-1-yl)-2-((1-methylpyrrolidin-2-yl)methoxy)-5,6,7,8-tetrahydropyrido[3,4-d]pyrimidin-4-yl)piperazin-1-yl)prop-2-en-1-one This compound was prepared following Example 127 substituting N-Methyl-D-prolinol for N-Methyl-L-prolinol in Step D. ES+APCI MS m/z 529.3 $[M+H]^+$.

Example 188

(S)-1-(4-(7-(3-hydroxynaphthalen-1-yl)-2-((1-methylpyrrolidin-3-yl)methoxy)-5,6,7,8-tetrahydropyrido[3,4-d]pyrimidin-4-yl)piperazin-1-yl)prop-2-en-1-one

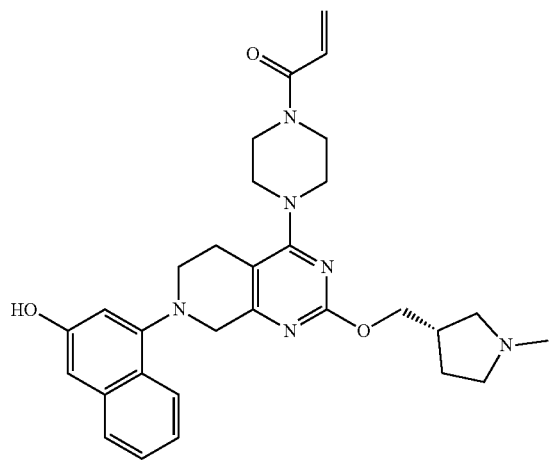 [SMILES: C=CC(=O)N1CCN(c2nc(OC[C@H]3CCN(C)C3)nc3c2CCN(c2cc(O)cc4ccccc24)C3)CC1]

(S)-1-(4-(7-(3-hydroxynaphthalen-1-yl)-2-((1-methylpyrrolidin-3-yl)methoxy)-5,6,7,8-tetrahydropyrido[3,4-d]pyrimidin-4-yl)piperazin-1-yl)prop-2-en-1-one This compound was prepared following Example 127 substituting (3S)-(1-Methyl-pyrrolidin-3-yl)-methanol for N-Methyl-L-prolinol in Step D. ES+APCI MS m/z 529.2 [M+H]$^+$.

Example 189

1-(4-(2-((1-benzylpyrrolidin-3-yl)methoxy)-7-(3-hydroxynaphthalen-1-yl)-5,6,7,8-tetrahydropyrido[3,4-d]pyrimidin-4-yl)piperazin-1-yl)prop-2-en-1-one

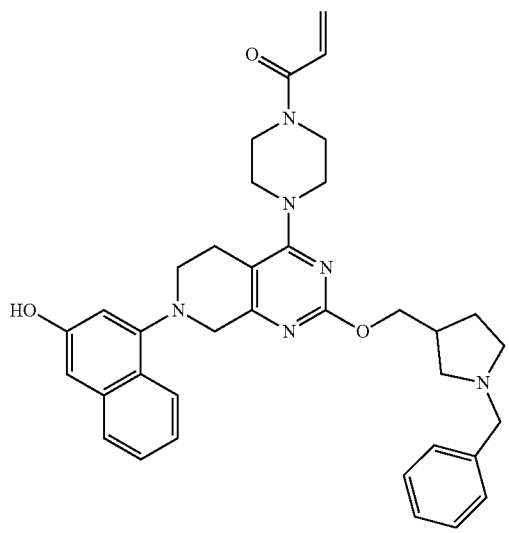 [SMILES: C=CC(=O)N1CCN(c2nc(OCC3CCN(Cc4ccccc4)C3)nc3c2CCN(c2cc(O)cc4ccccc24)C3)CC1]

1-(4-(2-((1-benzylpyrrolidin-3-yl)methoxy)-7-(3-hydroxynaphthalen-1-yl)-5,6,7,8-tetrahydropyrido[3,4-d]pyrimidin-4-yl)piperazin-1-yl)prop-2-en-1-one This compound was prepared following Example 127 substituting (1-Benzylpyrrolidin-3-yl)methanol for N-Methyl-L-prolinol in Step D. ES+APCI MS m/z 605.3 [M+H]$^+$.

Example 190

1-(4-(2-((1-cyclopropylpyrrolidin-3-yl)methoxy)-7-(3-hydroxynaphthalen-1-yl)-5,6,7,8-tetrahydropyrido[3,4-d]pyrimidin-4-yl)piperazin-1-yl)prop-2-en-1-one

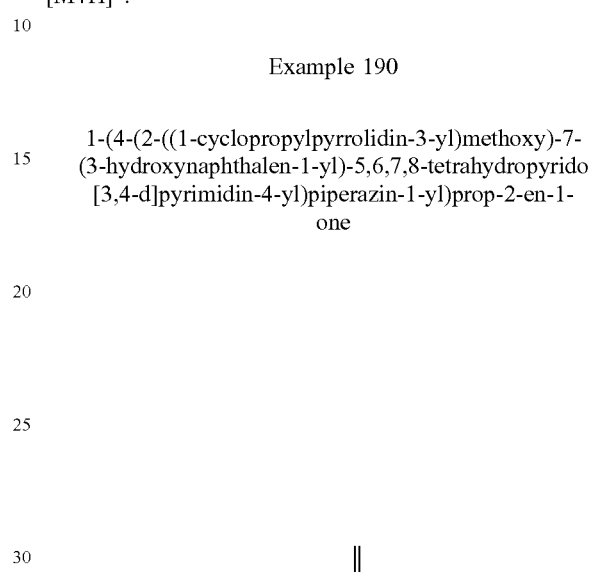

1-(4-(2-((1-cyclopropylpyrrolidin-3-yl)methoxy)-7-(3-hydroxynaphthalen-1-yl)-5,6,7,8-tetrahydropyrido[3,4-d]pyrimidin-4-yl)piperazin-1-yl)prop-2-en-1-one This compound was prepared following Example 127 substituting (1-Cyclopropyl-3-pyrrolidinyl)methanol for N-Methyl-L-prolinol in Step D. ES+APCI MS m/z 555.3 [M+H]$^+$.

Example 191

1-((2S,6R)-4-(7-(3-hydroxynaphthalen-1-yl)-2-(3-morpholinopropoxy)-5,6,7,8-tetrahydropyrido [3,4-d]pyrimidin-4-yl)-2,6-dimethylpiperazin-1-yl)prop-2-en-1-one

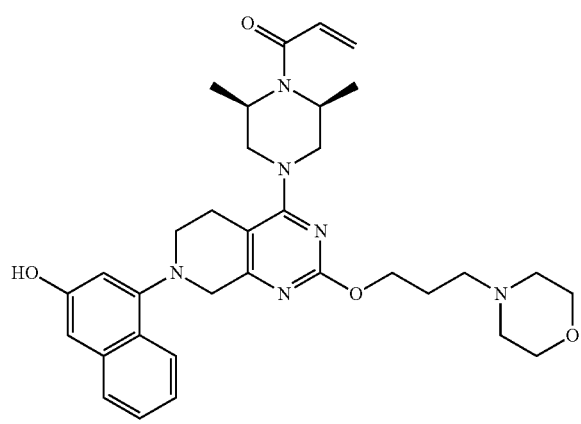

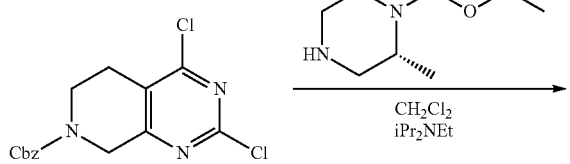

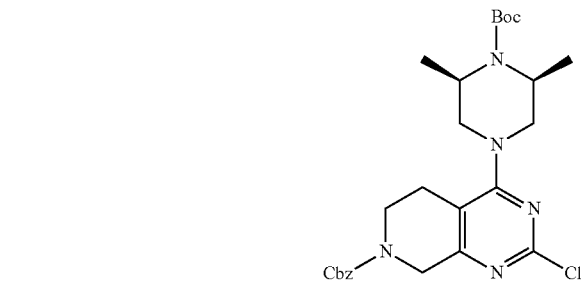

Step A: Benzyl 4-((3S,5R)-4-(tert-butoxycarbonyl)-3,5-dimethylpiperazin-1-yl)-2-chloro-5,8-dihydropyrido[3,4-d]pyrimidine-7(6H)-carboxylate A suspension of benzyl 2,4-dichloro-5,8-dihydropyrido[3,4-d]pyrimidine-7(6H)-carboxylate (500 mg, 1.48 mmol), tert-butyl cis-2,6-dimethylpiperazine-1-carboxylate (349 mg, 1.63 mmol) and DIEA (0.26 mL) in N,N-dimethylacetamide (1 mL) was stirred at r.t. overnight. The reaction mixture was divided between EtOAc (15 mL) and 1M NaHCO₃ (5 mL) and the layers separated. The organic layer was washed with 2M Na₂CO₃ and brine (2 mL each), dried over Na₂SO₄ and evaporated in vacuo. The residue was chromatographed on silica gel Redisep 24 g column using 20 to 50% EtOAc in hexane as eluent to give a colorless solid (0.440 g, 58%). ES+APCI MS m/z 516.2 [M+H]⁺.

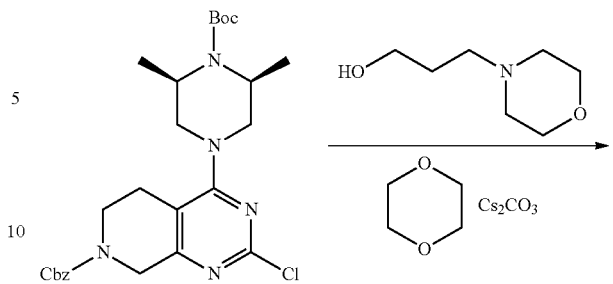

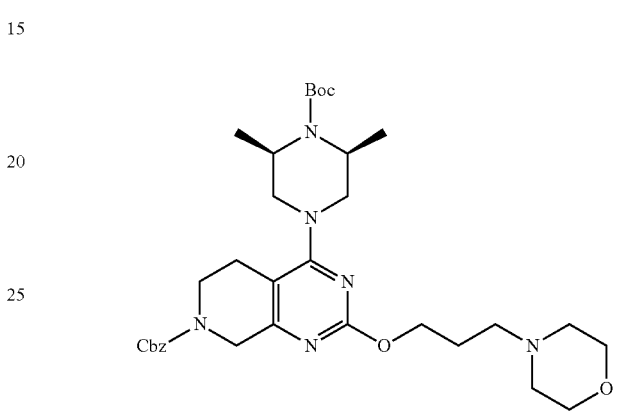

Step B: Benzyl 4-((3S,5R)-4-(tert-butoxycarbonyl)-3,5-dimethylpiperazin-1-yl)-2-(3-morpholinopropoxy)-5,8-dihydropyrido[3,4-d]pyrimidine-7(6H)-carboxylate A mixture of benzyl 4-((3S,5R)-4-(tert-butoxycarbonyl)-3,5-dimethylpiperazin-1-yl)-2-chloro-5,8-dihydropyrido[3,4-d]pyrimidine-7(6H)-carboxylate (400 mg, 0.775 mmol), 3-morpholinopropan-1-ol (400 mg, 2.33 mmol, 5 eq.), cesium carbonate (1.26 g, 3.88 mmol, 5 eq.) and dioxane (3 mL) in a 4-mL vial was purged with nitrogen. The vial was capped and the mixture stirred at 110° C. for 20 h, then at 120° C. overnight. The reaction was cooled, diluted with EtOAc (10 mL), filtered through Celite and evaporated in vacuo. The product was purified by chromatography on silica, Redisep 40 g, using 2 to 10% MeOH/DCM+0.2% NH₄OH as eluent to give a light-yellow amorphous solid (272 mg, 56%).

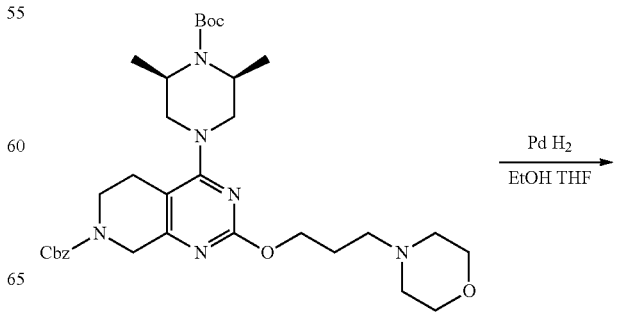

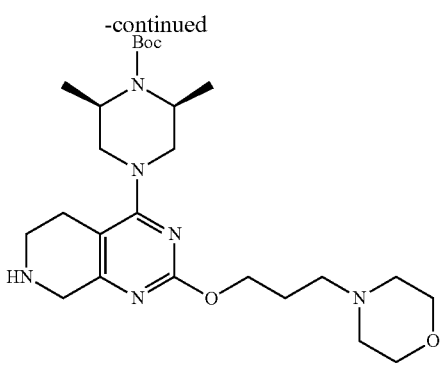

Step C: tert-butyl (2S,6R)-2,6-dimethyl-4-(2-(3-morpholinopropoxy)-5,6,7,8-tetrahydropyrido[3,4-d]pyrimidin-4-yl)piperazine-1-carboxylate A mixture of benzyl 4-((3 S, 5R)-4-(tert-butoxycarbonyl)-3,5-dimethylpiperazin-1-yl)-2-(3-morpholinopropoxy)-5,8-dihydropyrido[3,4-d]pyrimidine-7(6H)-carboxylate (272 mg, 0.095 mmol), palladium on carbon (50 mg, Degussa Type, 10 wt %, 50% H$_2$O), EtOH (5 mL) and THF (5 mL) was purged with hydrogen and stirred under H$_2$ atmosphere (rubber balloon) for 3 hours. The reaction mixture was diluted with EtOH (3 mL), filtered through Celite and the celite washed with EtOH (2×2 mL). The combined organics were evaporated in vacuo and dried under high vacuum over 2 days to give an off-white foam (205 mg, 96%). ES+APCI MS m/z 491.3 [M+H]$^+$.

Step D: tert-butyl (2S,6R)-4-(7-(3-(methoxymethoxy)naphthalen-1-yl)-2-(3-morpholinopropoxy)-5,6,7,8-tetrahydropyrido[3,4-d]pyrimidin-4-yl)-2,6-dimethylpiperazine-1-carboxylate To a stirred suspension of tris(dibenzylideneacetone)dipalladium (0) (19 mg, 0.020 mmol) in dry degassed toluene (0.5 mL) at room temperature under nitrogen was added (+/−)-2,2'-bis(diphenylphosphino)-1,1'-binaphthyl (24 mg, 0.038 mmol). The mixture was then heated to 100° C. for 15 minutes. The resulted dark mixture was cooled to room temperature and solid sodium-t-butoxide (39 mg, 0.41 mmol) was added, followed by a solution of 3-(methoxymethoxy)naphthalen-1-yl trifluoromethanesulfonate (82 mg, 0.25 mmol) and tert-butyl (2S,6R)-2,6-dimethyl-4-(2-(3-morpholinopropoxy)-5,6,7,8-tetrahydropyrido[3,4-d]pyrimidin-4-yl)piperazine-1-carboxylate (100 mg, 0.20 mmol) in degassed dry toluene (0.5 mL). The flask was closed and heated with stirring to 100° C. for 30 min. The reaction mixture was cooled and divided between EtOAc (20 mL) and water (10 mL). The organic layer was separated and washed with brine, dried over Na$_2$SO$_4$ and evaporated in vacuo. The product was purified by chromatography on silica, Redisep 40 g, using 4% MeOH+0.1% NH$_4$OH in DCM as eluent to give a colorless solid (87 mg, 63%). ES+APCI MS m/z 684.3 [M+H]$^+$.

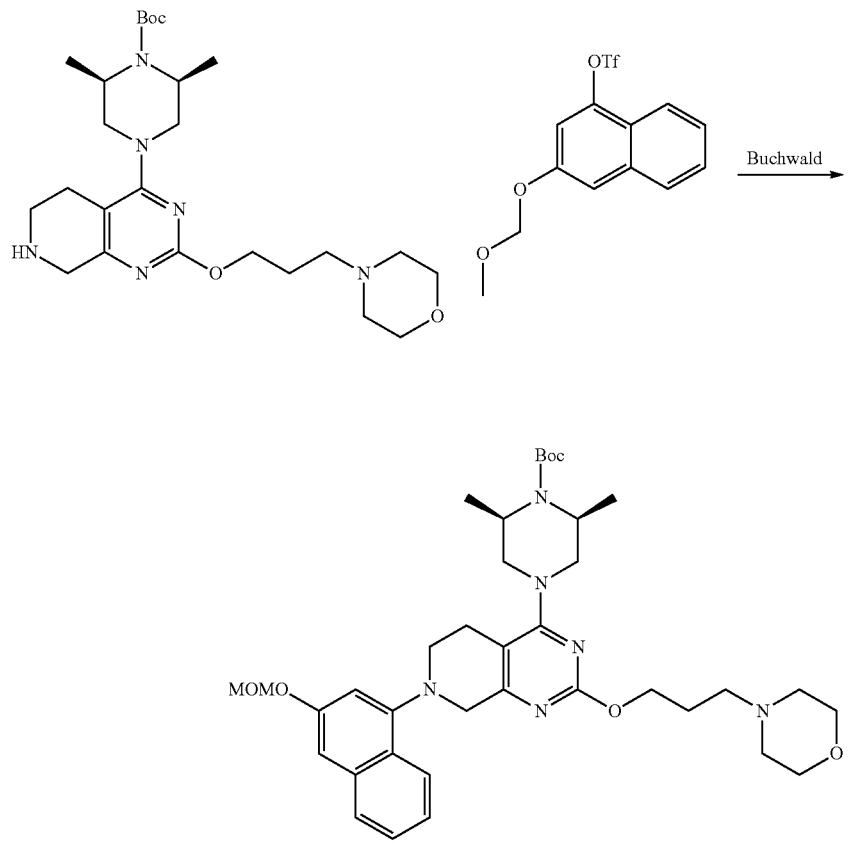

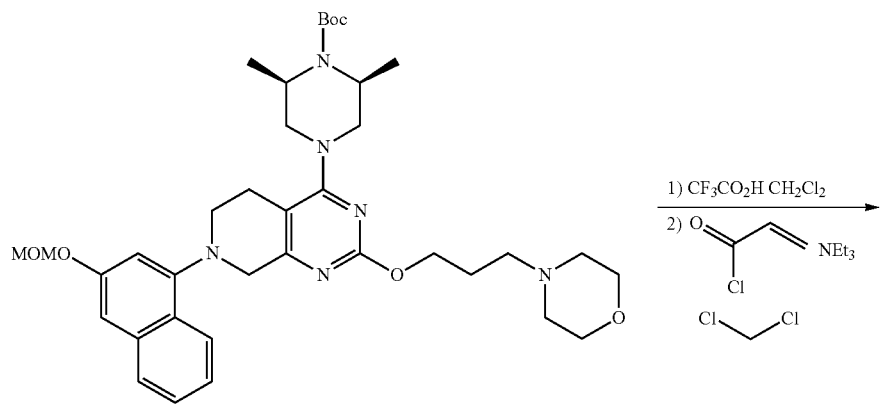

Step E: 1-((2S,6R)-4-(7-(3-hydroxynaphthalen-1-yl)-2-(3-morpholinopropoxy)-5,6,7,8-tetrahydropyrido[3,4-d]pyrimidin-4-yl)-2,6-dimethylpiperazin-1-yl)prop-2-en-1-one Tert-butyl (2S,6R)-4-(7-(3-(methoxymethoxy)naphthalen-1-yl)-2-(3-morpholinopropoxy)-5,6,7,8-tetrahydropyrido[3,4-d]pyrimidin-4-yl)-2,6-dimethylpiperazine-1-carboxylate (87 mg, 0.129 mmol) was dissolved in 1M TFA/DCM. The reaction mixture turned red-brown, then dark-red. LCMS indicated non-selective deprotection of Boc and MOM. After stirring 30 min at room temperature, 0.2 mL of additional TFA was added and the reaction mixture was left at room temperature for another 30 min. The resulted biphasic mixture was vaporated in vacuo, divided between water (5 mL) and DCM (10 mL)+NEt$_3$ (0.5 mL) and the organic layer separated. The organic layer was dried over Na$_2$SO$_4$ and evaporated in vacuo. The residue was purified by chromatography on silica, Redisep 40 g, using 6% MeOH in DCM+0.2% NH$_4$OH as eluent to give another residue which was repurified on reverse phase, C18, 5-95% MeCN—H$_2$O+0.1% TFA to give product assumed to be the bis-salt with TFA (1.35 mg, 1.3%). ES+APCI MS m/z 587.3 [M+H]$^+$.

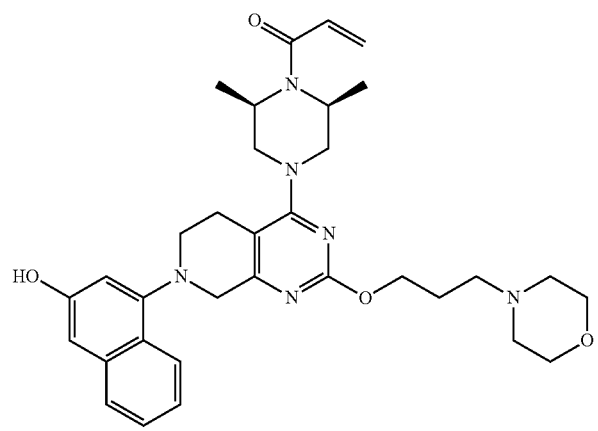

Example 192

(R)-1-(4-(7-(3-hydroxynaphthalen-1-yl)-2-((1-methylpiperidin-3-yl)methoxy)-5,6,7,8-tetrahydropyrido[3,4-d]pyrimidin-4-yl)piperazin-1-yl)prop-2-en-1-one

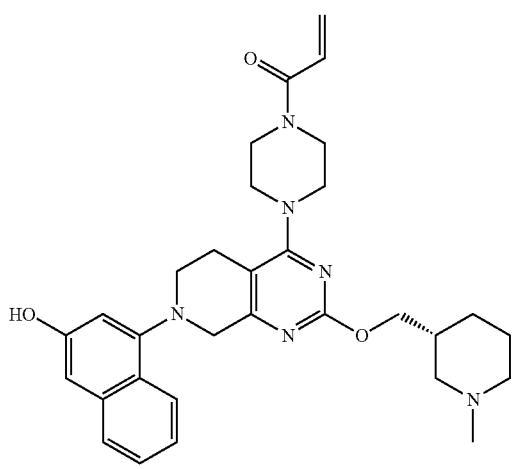 [SMILES: C=CC(=O)N1CCN(c2nc(OC[C@@H]3CCCN(C)C3)nc3c2CCN(c2cc(O)cc4ccccc24)C3)CC1]

(R)-1-(4-(7-(3-hydroxynaphthalen-1-yl)-2-(1-methylpiperidin-3-yl)methoxy)-5,6,7,8-tetrahydropyrido[3,4-d]pyrimidin-4-yl)piperazin-1-yl)prop-2-en-1-one This compound was prepared following Example 127 substituting 3-Piperidinemethanol,1-methyl-,(3R)- for N-Methyl-L-prolinol in Step D. ES+APCI MS m/z 543.3 [M+H]+.

Example 193

1-(4-(7-(3-hydroxynaphthalen-1-yl)-2-((4-methylmorpholin-2-yl)methoxy)-5,6,7,8-tetrahydropyrido[3,4-d]pyrimidin-4-yl)piperazin-1-yl)prop-2-en-1-one

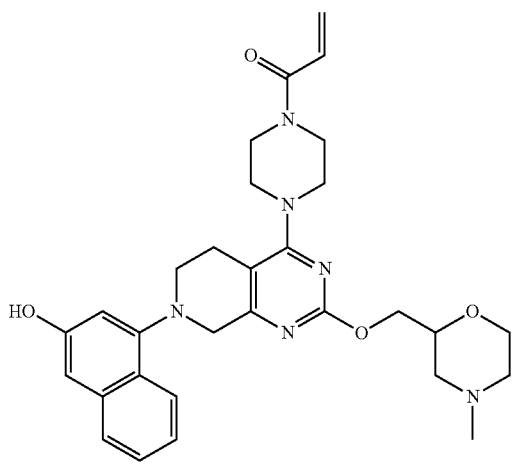 [SMILES: C=CC(=O)N1CCN(c2nc(OCC3CN(C)CCO3)nc3c2CCN(c2cc(O)cc4ccccc24)C3)CC1]

1-(4-(7-(3-hydroxynaphthalen-1-yl)-2-((4-methylmorpholin-2-yl)methoxy)-5,6,7,8-tetrahydropyrido[3,4-d]pyrimidin-4-yl)piperazin-1-yl)prop-2-en-1-one This compound was prepared following Example 127 substituting (4-methyl-2-morpholinyl)methanol for N-Methyl-L-prolinol in Step D. ES+APCI MS m/z 545.3 [M+H]+.

Example 194

1-(4-(7-(3-hydroxynaphthalen-1-yl)-2-((4-methylmorpholin-3-yl)methoxy)-5,6,7,8-tetrahydropyrido[3,4-d]pyrimidin-4-yl)piperazin-1-yl)prop-2-en-1-one

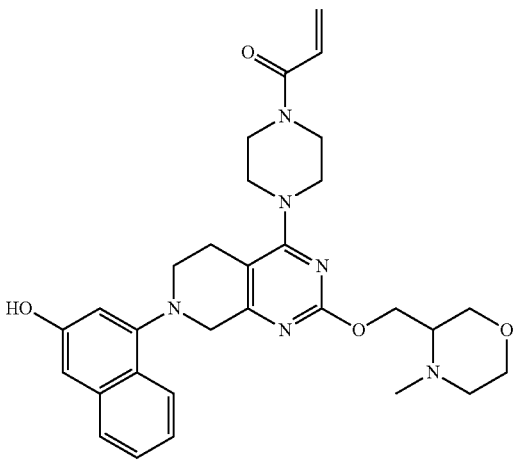 [SMILES: C=CC(=O)N1CCN(c2nc(OCC3COCCN3C)nc3c2CCN(c2cc(O)cc4ccccc24)C3)CC1]

1-(4-(7-(3-hydroxynaphthalen-1-yl)-2-((4-methylmorpholin-3-yl)methoxy)-5,6,7,8-tetrahydropyrido[3,4-d]pyrimidin-4-yl)piperazin-1-yl)prop-2-en-1-one This compound was prepared following Example 127 substituting 4-Methyl-3-(hydroxymethyl)morpholine for N-Methyl-L-prolinol in Step D. ES+APCI MS m/z 545.2 [M+H]+.

Example 195

(R)-1-(4-(7-(3-hydroxynaphthalen-1-yl)-2-((1-methylpiperidin-2-yl)methoxy)-5,6,7,8-tetrahydropyrido[3,4-d]pyrimidin-4-yl)piperazin-1-yl)prop-2-en-1-one

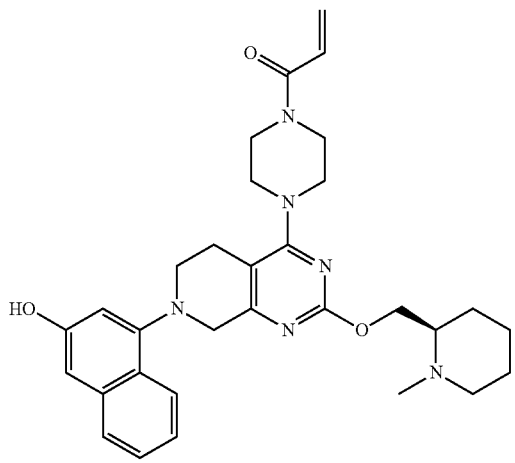 [SMILES: C=CC(=O)N1CCN(c2nc(OC[C@H]3CCCCN3C)nc3c2CCN(c2cc(O)cc4ccccc24)C3)CC1]

(R)-1-(4-(7-(3-hydroxynaphthalen-1-yl)-2-(1-methylpiperidin-2-yl)methoxy)-5,6,7,8-tetrahydropyrido[3,4-d]pyrimidin-4-yl)piperazin-1-yl)prop-2-en-1-one This compound was prepared following Example 127 substituting (R)-(1-Methylpiperidin-2-yl)methanol for N-Methyl-L-prolinol in Step D. ES+APCI MS m/z 543.3 [M+H]+.

Example 196

(S)-1-(4-(7-(3-hydroxynaphthalen-1-yl)-2-(1-methylpiperidin-2-yl)methoxy)-5,6,7,8-tetrahydropyrido[3,4-d]pyrimidin-4-yl)piperazin-1-yl)prop-2-en-1-one

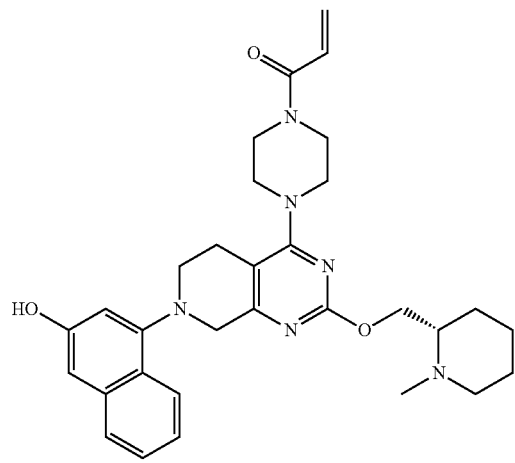 [SMILES: C=CC(=O)N1CCN(c2nc(OC[C@@H]3CCCCN3C)nc3c2CCN(c2cc(O)cc4ccccc24)C3)CC1]

(S)-1-(4-(7-(3-hydroxynaphthalen-1-yl)-2-((1-methylpiperidin-2-yl)methoxy)-5,6,7,8-tetrahydropyrido[3,4-d]pyrimidin-4-yl)piperazin-1-yl)prop-2-en-1-one This compound was prepared following Example 127 substituting (S)-(1-Methylpiperidin-2-yl)methanol for N-Methyl-L-prolinol in Step D. ES+APCI MS m/z 543.2 [M+H]+.

Example 197

(S)-1-(4-(2-((1-ethylpyrrolidin-2-yl)methoxy)-7-(3-hydroxynaphthalen-1-yl)-5,6,7,8-tetrahydropyrido[3,4-d]pyrimidin-4-yl)piperazin-1-yl)prop-2-en-1-one

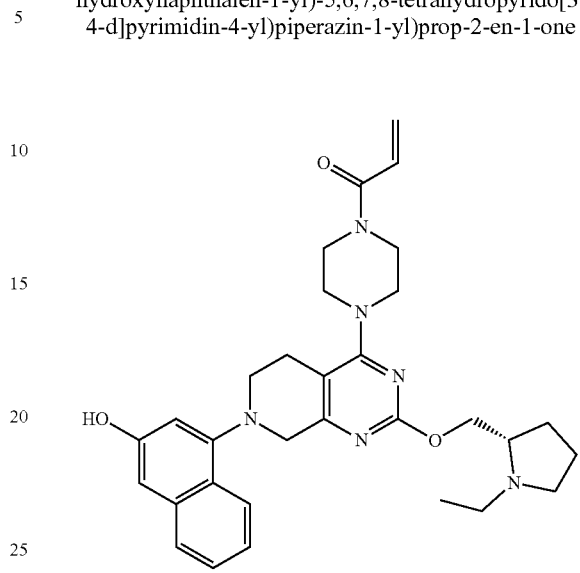

(S)-1-(4-(2-((1-ethylpyrrolidin-2-yl)methoxy)-7-(3-hydroxynaphthalen-1-yl)-5,6,7,8-tetrahydropyrido[3,4-d]pyrimidin-4-yl)piperazin-1-yl)prop-2-en-1-one This compound was prepared following Example 127 substituting [(2S)-1-Ethyl-2-pyrrolidinyl]methanol for N-Methyl-L-prolinol in Step D. ES+APCI MS m/z 543.3 [M+H]+.

Example 198

(S,E)-1-(4-(7-(3-hydroxynaphthalen-1-yl)-2-((1-methylpyrrolidin-2-yl)methoxy)-5,6,7,8-tetrahydropyrido[3,4-d]pyrimidin-4-yl)piperazin-1-yl)but-2-en-1-one

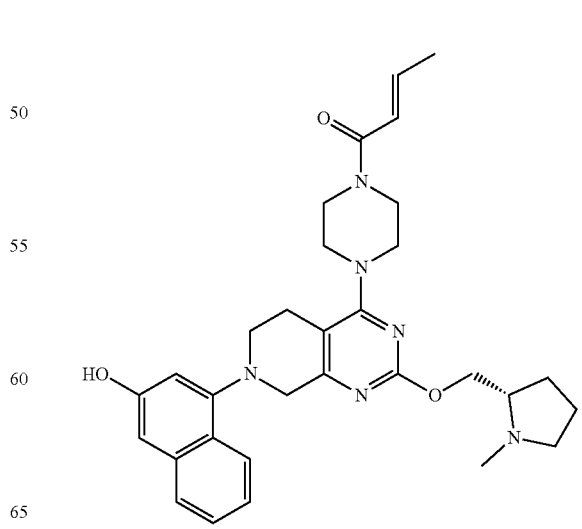

S,E)-1-(4-(7-(3-hydroxynaphthalen-1-yl)-2-((1-methylpyrrolidin-2-yl)methoxy)-5,6,7,8-tetrahydropyrido[3,4-d]pyrimidin-4-yl)piperazin-1-yl)but-2-en-1-one This compound was prepared following Example 127 substituting trans-Crotonyl chloride for Acryloyl Chloride in Step F. ES+APCI MS m/z 543.2[M+H]+.

Example 199

(S,E)-4-(dimethylamino)-1-(4-(7-(3-hydroxynaphthalen-1-yl)-2-((1-methylpyrrolidin-2-yl)methoxy)-5,6,7,8-tetrahydropyrido[3,4-d]pyrimidin-4-yl)piperazin-1-yl)but-2-en-1-one

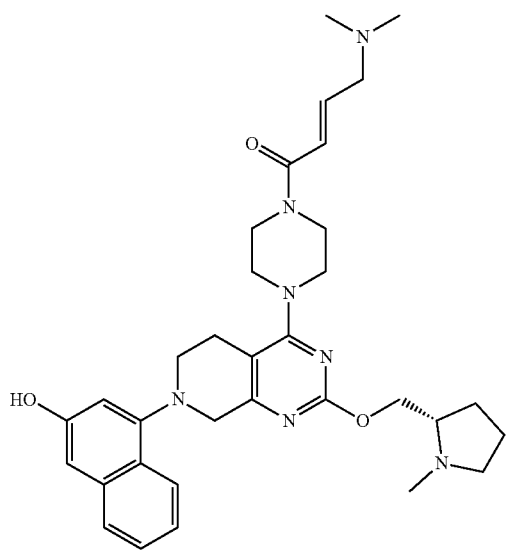 [SMILES: CN(C)C/C=C/C(=O)N1CCN(c2nc(OC[C@@H]3CCCN3C)nc3c2CCN(c2cc(O)cc4ccccc24)C3)CC1]

(S,E)-4-(dimethylamino)-1-(4-(7-(3-hydroxynaphthalen-1-yl)-2-((1-methylpyrrolidin-2-yl)methoxy)-5,6,7,8-tetrahydropyrido[3,4-d]pyrimidin-4-yl)piperazin-1-yl)but-2-en-1-one This compound was prepared following Example 127 substituting the following procedure for step F. 7-(3-(methoxymethoxy)naphthalen-1-yl)-2-(((S)-1-methylpyrrolidin-2-yl)methoxy)-4-(piperazin-1-yl)-4a,5,6,7,8,8a-hexahydropyrido[3,4-d]pyrimidine (150 mg, 0.288 mmol) was dissolved in DCM (5 mL) and treated with (2E)-4-(Dimethylamino)but-2-enoic acid (74.4 mg, 0.576 mmol) and Hunig's base (252 µl, 1.44 mmol). To this mixture was added EDC (55.2 mg, 0.288 mmol) and HOBT (38.9 mg, 0.288 mmol) neat as powders. The reaction mixture was stirred at room temperature for 1 hour and heated to 35° C. for an additional 3 hours. The reaction mixture was concentrated in vacuo and purified on the CombiFlash (0%-15% DCM/MeOH w/1% NH4OH modifier). All fractions containing clean desired product were combined and concentrated in vacuo to afford (E)-4-(dimethylamino)-1-(4-(7-(3-(methoxymethoxy)naphthalen-1-yl)-2-(((S)-1-methylpyrrolidin-2-yl)methoxy)-4a,5,6,7,8,8a-hexahydropyrido[3,4-d]pyrimidin-4-yl)piperazin-1-yl)but-2-en-1-one (105 mg, 0.166 mmol, 57.7% yield). The product followed the rest of Example 127 accordingly to give (S,E)-4-(dimethylamino)-1-(4-(7-(3-hydroxynaphthalen-1-yl)-2-((1-methylpyrrolidin-2-yl)methoxy)-5,6,7,8-tetrahydropyrido[3,4-d]pyrimidin-4-yl)piperazin-1-yl)but-2-en-1-one (14.8 mg, 0.025 mmol, 15.2% yield). ES+APCI MS m/z 586.3[M+H]+.

Example 200

(S)-1-(4-(2-((1-methylpyrrolidin-2-yl)methoxy)-7-(naphthalen-1-yl)-5,6,7,8-tetrahydropyrido[3,4-d]pyrimidin-4-yl)piperazin-1-yl)prop-2-en-1-one

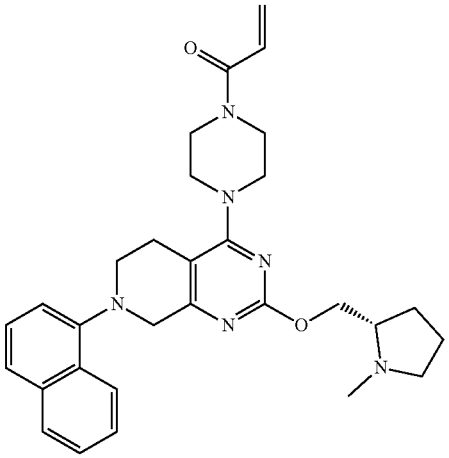 [SMILES: C=CC(=O)N1CCN(c2nc(OC[C@@H]3CCCN3C)nc3c2CCN(c2cccc4ccccc24)C3)CC1]

(S)-1-(4-(2-((1-methylpyrrolidin-2-yl)methoxy)-7-(naphthalen-1-yl)-5,6,7,8-tetrahydropyrido[3,4-d]pyrimidin-4-yl)piperazin-1-yl)prop-2-en-1-one This compound was prepared following Example 127 substituting naphthalen-1-yl trifluoromethanesulfonate for 3-(methoxymethoxy)naphthalen-1-yl trifluoromethanesulfonate in Step C and not performing step F. ES+APCI MS m/z 513.3 [M+H]+.

Example 201

1-((R)-2-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-1-yl)prop-2-en-1-one

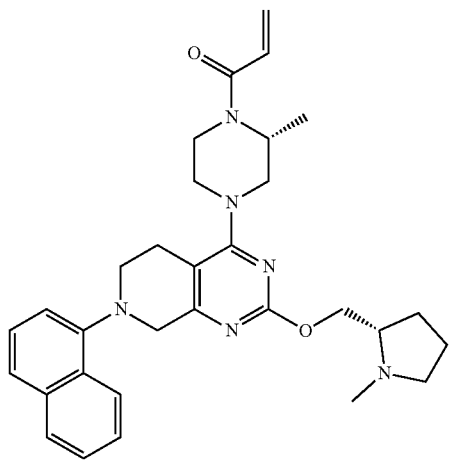 [SMILES: C=CC(=O)N1CCN(c2nc(OC[C@@H]3CCCN3C)nc3c2CCN(c2cccc4ccccc24)C3)C[C@H]1C]

1-((R)-2-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-1-yl)prop-2-en-1-one This compound was prepared following Example 127 substituting (R)-benzyl 2-methylpiperazine-1-carboxylate for benzyl piperazine-1-carboxylate in Step A and substituting naphthalen-1-yl trifluoromethanesulfonate for 3-(methoxymethoxy)naphthalen-1-yl trifluoromethanesulfonate in Step C and not performing step F. ES+APCI MS m/z 527.3 [M+H]

Example 202

1-((S)-4-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3-methylpiperazin-1-yl)prop-2-en-1-one

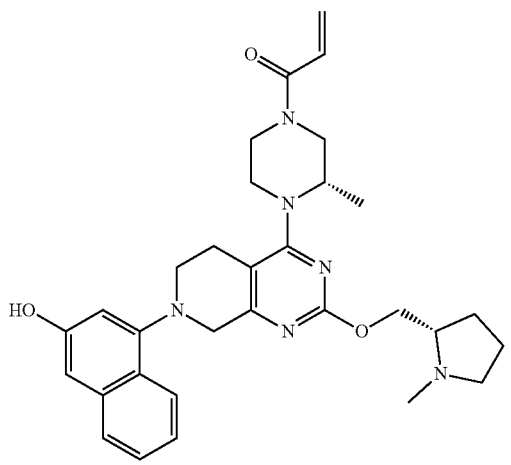 [SMILES: C=CC(=O)N1CCN(c2nc(OC[C@@H]3CCCN3C)nc3c2CCN(c2cc(O)cc4ccccc24)C3)[C@@H](C)C1]

1-((S)-4-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3-methylpiperazin-1-yl)prop-2-en-1-one This compound was prepared following Example 127 substituting benzyl (S)-3-methylpiperazine-1-carboxylate for benzyl piperazine-1-carboxylate in Step A. ES+APCI MS m/z 543.3 [M+H]+.

Example 203

1-((S)-4-(7-(3-hydroxynaphthalen-1-yl)-2-(((R)-1-methylpyrrolidin-2-yl)methoxy)-5,6,7,8-tetrahydropyrido[3,4-d]pyrimidin-4-yl)-3-methylpiperazin-1-yl)prop-2-en-1-one

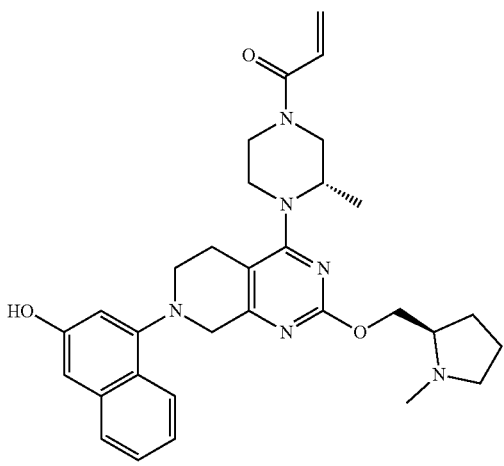

1-((S)-4-(7-(3-hydroxynaphthalen-1-yl)-2-(((R)-1-methylpyrrolidin-2-yl)methoxy)-5,6,7,8-tetrahydropyrido[3,4-d]pyrimidin-4-yl)-3-methylpiperazin-1-yl)prop-2-en-1-one This compound was prepared following Example 127 substituting benzyl (S)-3-methylpiperazine-1-carboxylate for benzyl piperazine-1-carboxylate in Step A and substituting N-Methyl-D-prolinol for N-Methyl-L-prolinol in Step D. ES+APCI MS m/z 543.3 [M+H]+

Example 204

1-(4-(2-((1-cyclopropylpiperidin-4-yl)amino)-7-(3-hydroxynaphthalen-1-yl)-5,6,7,8-tetrahydropyrido[3,4-d]pyrimidin-4-yl)piperazin-1-yl)prop-2-en-1-one

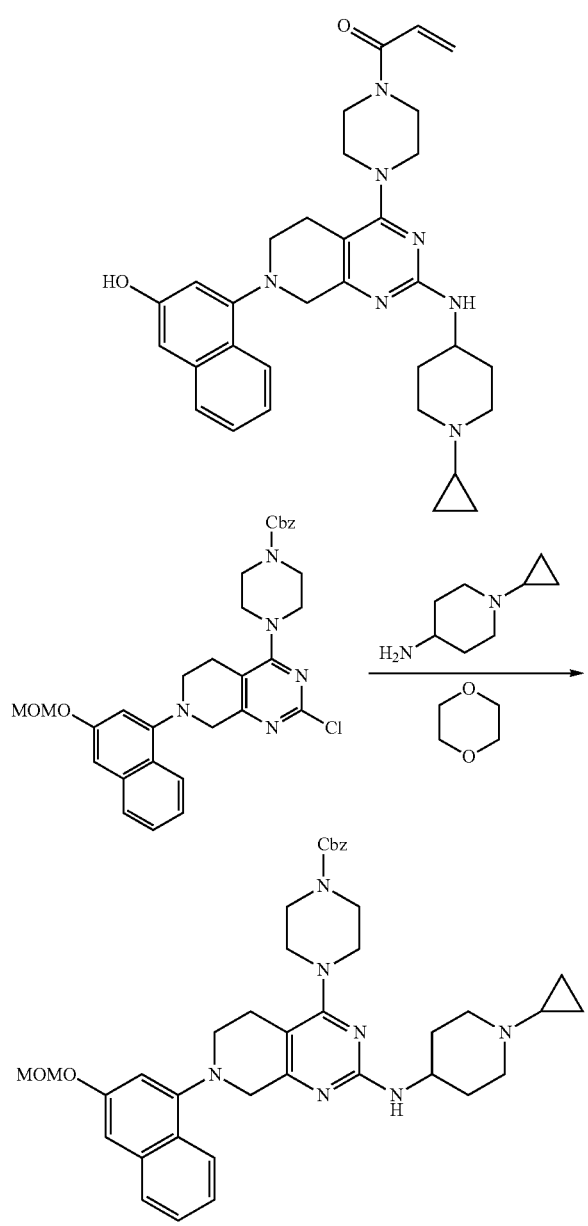

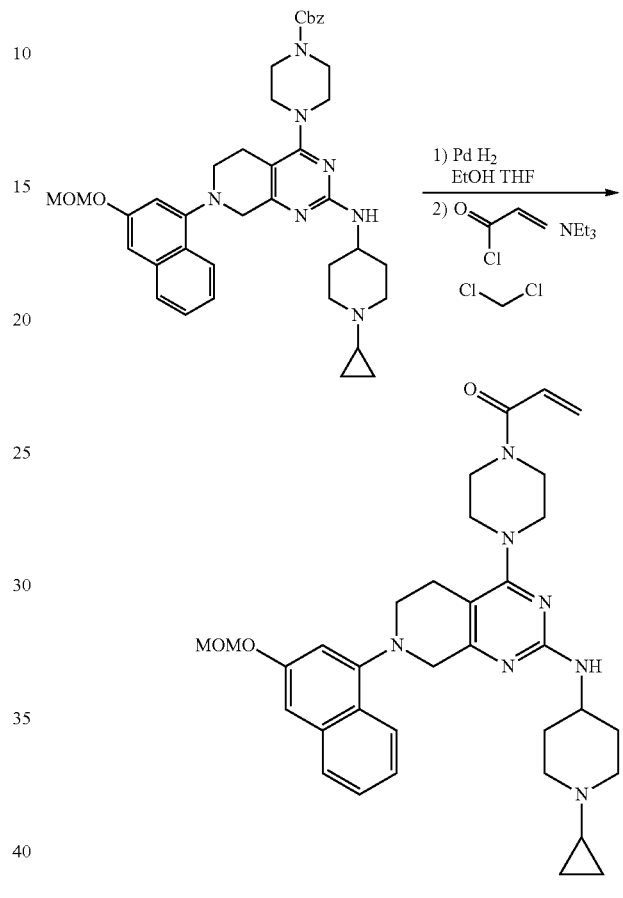

Step A: Benzyl 4-(2-(1-cyclopropylpiperidin-4-yl)amino)-7-(3-(methoxymethoxy)naphthalen-1-yl)-5,6,7,8-tetrahydropyrido[3,4-d]pyrimidin-4-yl)piperazine-1-carboxylate A mixture of benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (75 mg, 0.13 mmol), 1-cyclopropylpiperidin-4-amine (55 mg, 0.39 mmol) and dioxane (0.5 mL) was heated to 120° C. for 36 h. The reaction mixture was cooled to room temperature, divided between EtOAc (10 mL) and water (3 mL) and the layers separated. The organic layer was washed with brine, dried over $Na_2SO_4$ and evaporated in vacuo and the residue chromatographed on silica, Redisep 24 g, using 6 to 10% MeOH in DCM+0.2% $NH_4OH$ as eluent to give a colorless solid (43 mg, 49%). ES+APCI MS m/z 678.3 $[M+H]^+$.

Step B: 1-(4-(2-(1-cyclopropylpiperidin-4-yl)amino)-7-(3-(methoxymethoxy)naphthalen-1-yl)-5,6,7,8-tetrahydropyrido[3,4-d]pyrimidin-4-yl)piperazin-1-yl)prop-2-en-1-one A mixture of benzyl 4-(2-(1-cyclopropylpiperidin-4-yl)amino)-7-(3-(methoxymethoxy)-naphthalen-1-yl)-5,6,7,8-tetrahydropyrido[3,4-d]pyrimidin-4-yl)piperazine-1-carboxylate (43 mg, 0.063 mmol), palladium on carbon (20 mg, Degussa Type, 10 wt %, 50% $H_2O$), EtOH (1.5 mL) and THF (1.5 mL) was purged with hydrogen and stirred under $H_2$ atmosphere (rubber balloon) for 3 hours. The mixture was diluted with EtOH (3 mL), filtered through Celite and the celite washed with EtOH (2×2 mL). The combined organics were evaporated in vacuo. The residue was dissolved in DCM (5 mL) and cooled on ice-salt bath with stirring. Triethylamine (0.03 mL) was next added at once, followed by acryloyl chloride (10 µL). After 1 min at −5° C. the reaction was quenched with $NH_4OH$ (0.05 mL) and evaporated in vacuo. The residue was stirred 5 min with DCM (5 mL), filtered and chromatographed on silica gel, Redisep 12 g, using 6 to 20% MeOH in DCM+0.2% $NH_4OH$ as eluent to give a colorless solid (22 mg, 48%). ES+APCI MS m/z 598.3 $[M+H]^+$.

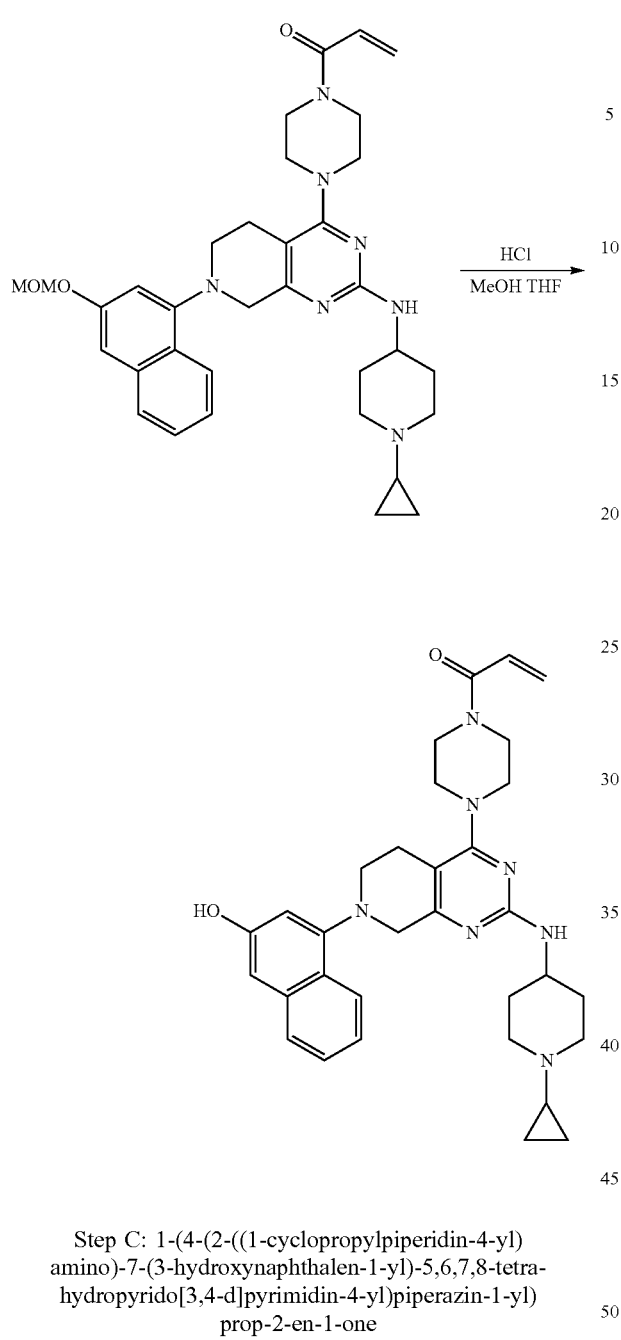

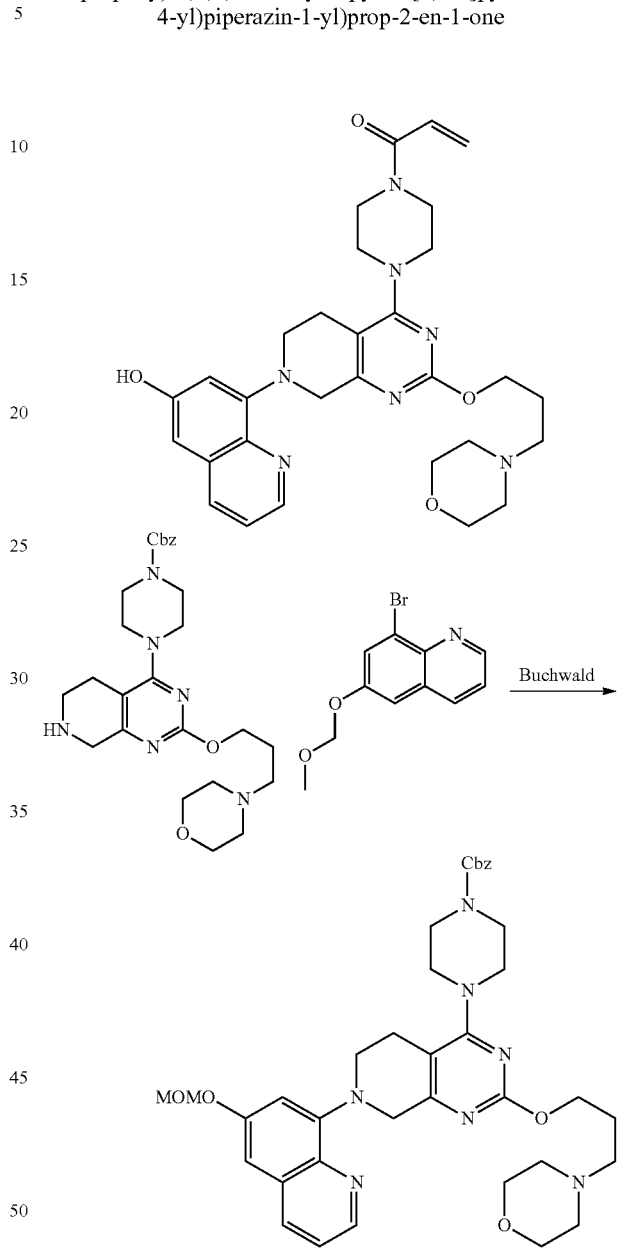

Example 205

1-(4-(7-(6-hydroxyquinolin-8-yl)-2-(3-morpholino-propoxy)-5,6,7,8-tetrahydropyrido[3,4-d]pyrimidin-4-yl)piperazin-1-yl)prop-2-en-1-one Step C: 1-(4-(2-((1-cyclopropylpiperidin-4-yl)amino)-7-(3-hydroxynaphthalen-1-yl)-5,6,7,8-tetrahydropyrido[3,4-d]pyrimidin-4-yl)piperazin-1-yl)prop-2-en-1-one To a stirred solution of 1-(4-(2-((1-cyclopropylpiperidin-4-yl)amino)-7-(3-(methoxymethoxy)naphthalen-1-yl)-5,6,7,8-tetrahydropyrido[3,4-d]pyrimidin-4-yl)piperazin-1-yl)prop-2-en-1-one (22 mg, 0.037 mmol) in a mixture of MeOH and THF 1:1 (3 mL) was added 6M aqueous HCl (0.3 mL, 34 eq.) all at once and the resulting solution was heated with stirring at 50° C. for 1.5 hours. The reaction mixture was cooled to room temperature, divided between EtOAc (15 mL) and 0.5M Na$_2$CO$_3$ (10 mL) and the organic layer separated. The combined organics were washed with brine (3 mL), dried over Na$_2$SO$_4$ and evaporated in vacuo. The residue was chromatographed on silica, Redisep 12 g, using 8 to 10% MeOH in DCM+0.2% NH$_4$OH as eluent to give a colorless solid (15 mg, 74%). ES+APCI MS m/z 554.3 [M+H]$^+$.

Step A: Benzyl 4-(7-(6-(methoxymethoxy)quinolin-8-yl)-2-(3-morpholinopropoxy)-5,6,7,8-tetrahydropyrido[3,4-d]pyrimidin-4-yl)piperazine-1-carboxylate To a stirred suspension of tris(dibenzylideneacetone)dipalladium (0) (17 mg, 0.019 mmol) in degassed dry toluene (0.5 mL) under nitrogen at room temperature was added (+/−)-2,2'-bis(diphenylphosphino)-1,1'-binaphthyl (24 mg, 0.038 mmol) and the mixture was heated to 100° C. for 15 minutes. The dark mixture was cooled to room temperature and solid sodium-t-butoxide (36 mg, 0.38 mmol) was then added, followed by a solution of 8-bromo-6-

(methoxymethoxy)quinoline (61 mg, 0.23 mmol) and benzyl 4-(2-(3-morpholinopropoxy)-5,6,7,8-tetrahydropyrido[3,4-d]pyrimidin-4-yl)piperazine-1-carboxylate (94 mg, 0.19 mmol) in degassed dry toluene (0.5 mL). The flask was closed and heated to 100° C. for 1 hour. The reaction mixture was cooled to room temperature, divided between EtOAc (15 mL) and water (5 mL) and the organic layers separated. The organic layer was washed with brine, dried over $Na_2SO_4$ and evaporated in vacuo. The residue was chromatographed on silica gel, Redisep 24 g, using 4 to 10% MeOH in dichloromethane (+0.2% $NH_4OH$) as eluent to give a yellow solid (28 mg, 22%). ES+APCI MS m/z 684.3 $[M+H]^+$.

mixture was filtered through a cotton plug, chromatographed on silica gel, Redisep 12 g, using 6 to 10% MeOH in DCM+0.2% $NH_4OH$ as eluent to give another residue which was repurified on reverse phase, C18, 5 to 95% MeCN, +0.1% $HCO_2H$ to give product which was assumed to be the bis-formate salt as a yellow solid (12 mg, 42%). ES+APCI MS m/z 604.2 $[M+H]^+$.

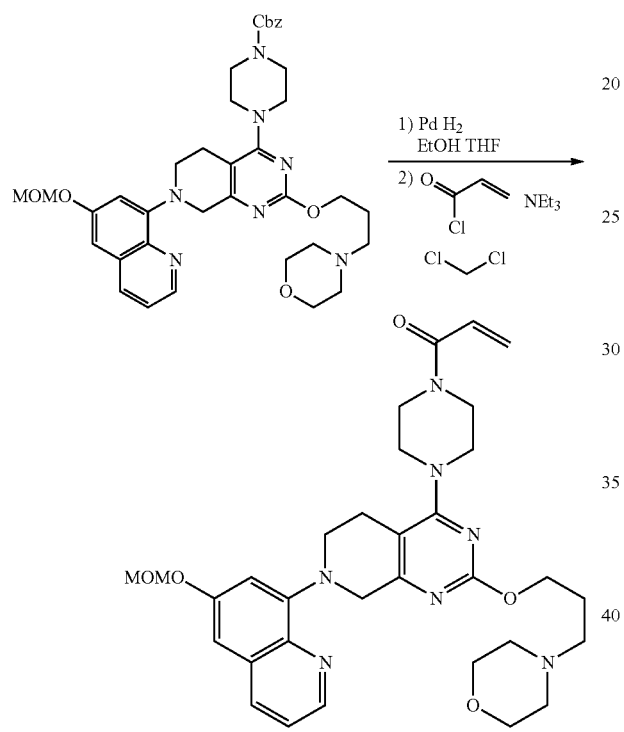

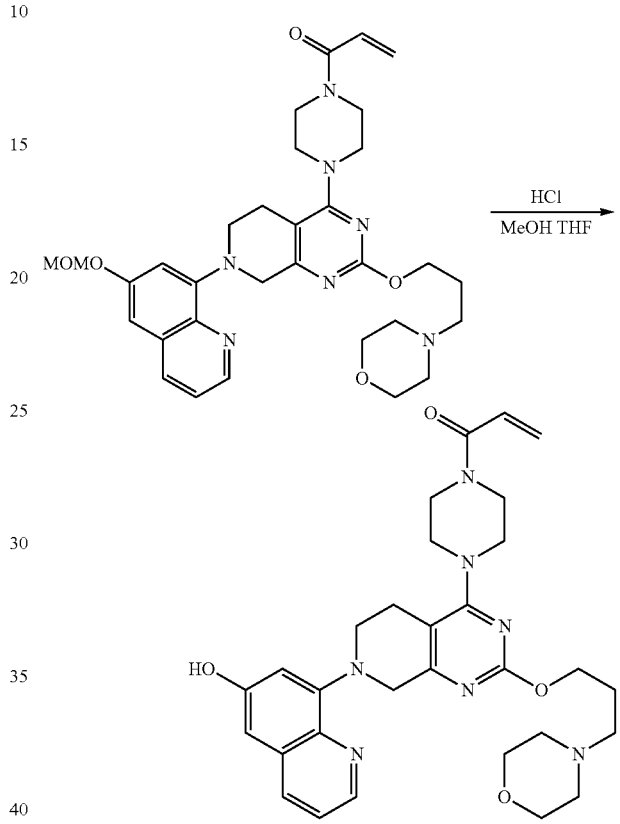

Step C: 1-(4-(7-(6-hydroxyquinolin-8-yl)-2-(3-morpholinopropoxy)-5,6,7,8-tetrahydropyrido[3,4-d]pyrimidin-4-yl)piperazin-1-yl)prop-2-en-1-one Step B: 1-(4-(7-(6-(methoxymethoxy)quinolin-8-yl)-2-(3-morpholinopropoxy)-5,6,7,8-tetrahydropyrido[3,4-d]pyrimidin-4-yl)piperazin-1-yl)prop-2-en-1-one A mixture of benzyl 4-(7-(6-(methoxymethoxy)quinolin-8-yl)-2-(3-morpholinopropoxy)-5,6,7,8-tetrahydropyrido[3,4-d]pyrimidin-4-yl)piperazine-1-carboxylate (28 mg, 0.095 mmol), Pd/C (15 mg, Degussa Type, 10 wt %, 50% $H_2O$), EtOH (2 mL) and THF (2 mL) was purged with hydrogen and stirred under $H_2$ atmosphere (rubber balloon) for 2 hours. The reaction mixture was diluted with EtOH (3 mL), filtered through Celite and the celite washed with EtOH (2×2 mL) and the combined organics evaporated in vacuo. The resulted solid was dissolved in DCM (5 mL) and cooled in an ice-salt bath with stirring. Triethylamine (0.04 mL, 3 eq.) was then added at once followed by acryloyl chloride (16 μL, 2 eq.). After 1 min at −5° C. the reaction was quenched with $NH_4OH$ (0.05 mL) and evaporated in vacuo. The To a stirred solution of 1-(4-(7-(6-(methoxymethoxy)quinolin-8-yl)-2-(3-morpholinopropoxy)-5,6,7,8-tetrahydropyrido[3,4-d]pyrimidin-4-yl)piperazin-1-yl)prop-2-en-1-one (12 mg, 0.017 mmol) in a mixture of MeOH and THF 1:1 (1 mL) was added 6M aqueous HCl (0.1 mL, 35 eq.) at once and the solution was heated with stirring at 50° C. for 1.5 h. The reaction mixture was cooled to room temperature, divided between EtOAc (15 mL) and 0.5M Na-phosphate buffer with pH 8 (5 mL) and the layers separated. The combined organics were washed with brine (1 mL), dried over $Na_2SO_4$ and evaporated in vacuo. The product was purified by chromatography on silica, Redisep 12 g, using 7 to 10% MeOH in DCM+0.2% $NH_4OH$ as eluent to give a residue which was repurified by reverse phase chromatograpy, C18, 5 to 95% MeOH+0.1% TFA) to give product as the tris TFA salt as a colorless solid (4.87 mg, 31%). ES+APCI MS m/z 560.3 $[M+H]^+$.

Example 206

1-(4-(2-(3-(3-azabicyclo[3.1.0]hexan-3-yl)propoxy)-7-(3-hydroxynaphthalen-1-yl)-5,6,7,8-tetrahydro-pyrido[3,4-d]pyrimidin-4-yl)piperazin-1-yl)prop-2-en-1-one

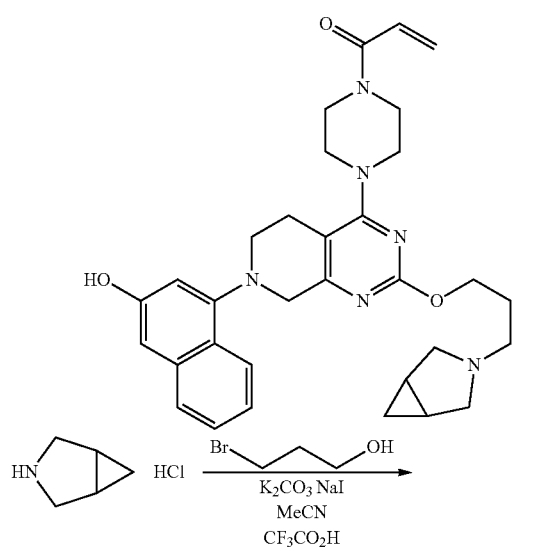

Step A: 3-(3-azabicyclo[3.1.0]hexan-3-yl)propan-1-ol

A mixture of 3-azabicyclo[3.1.0]hexane hydrochloride (200 mg, 1.67 mmol), 3-bromopropan-1-ol (166 μL, 1.84 mmol, 1.1 eq.), $K_2CO_3$ (0.69 g, 5.02 mmol, 3 eq.), NaI (251 mg, 1.67 mmol, 1 eq.) and acetonitrile (2 mL) in a 4-mL vial was flushed with $N_2$. The vial was capped and stirred at room temperature for 2 days. The mixture was diluted with water (2 mL) and extracted with ether (15 mL). The ether solution was washed with brine, dried over $Na_2SO_4$ and decanted into a pear-shaped flask and trifluoroacetic acid (128 μL, 1 eq) added and the mixture was concentrated to ~5 mL. The upper etherial layer was decanted and discarded, the residual oily liquid was dried under vacuum overnight. The oily liquid was diluted with water (0.5 mL) then ether (10 mL) was added with stirring followed by 50% NaOH (0.2 mL, 2.5 mmol, 2 eq.). The layers were separated, the organic solution was dried over KOH and carefully concentrated under nitrogen to yield crude 3-(3-azabicyclo[3.1.0]hexan-3-yl)propan-1-ol as colorless oil. Used on the next stage without further purification.

Step B: Benzyl 4-(2-(3-(3-azabicyclo[3.1.0]hexan-3-yl)propoxy)-7-(3-(methoxymethoxy)-naphthalen-1-yl)-5,6,7,8-tetrahydropyrido[3,4-d]pyrimidin-4-yl)piperazine-1-carboxylate A mixture of benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (75 mg, 0.13 mmol), crude 3-(3-azabicyclo[3.1.0]hexan-3-yl)propan-1-ol (55 mg, 0.39 mmol, 3 eq.), $Cs_2CO_3$ (213 mg, 0.65 mmol, 5 eq.) and dioxane (0.5 mL) in a 1.7-mL vial was purged with nitrogen. The vial was capped and stirred at 120° C. over the weekend. The reaction mixture was cooled, divided between EtOAc (15 mL) and water (5 mL) and the layers separated. The organic layer was washed with brine, dried over $Na_2SO_4$, evaporated in vacuo and the residue chromatographed on silica gel, Redisep 24 g, using 4 to 10% MeOH+1% $NH_4OH$ as eluent to give product. ES+APCI MS m/z 679.3 $[M+H]^+$.

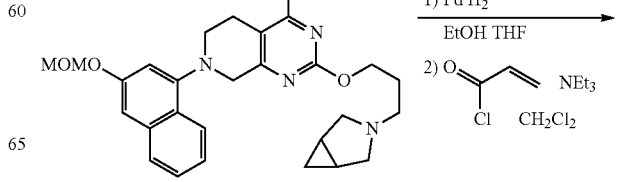

611
-continued

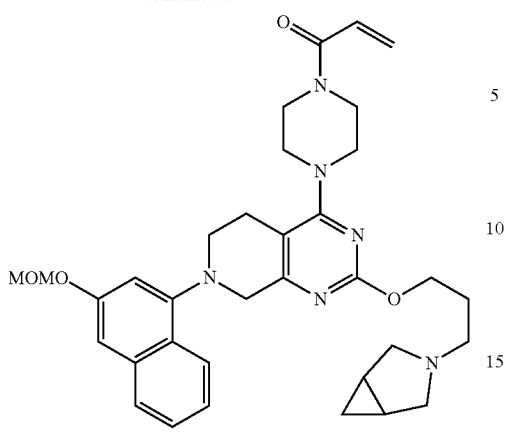

Step C: 1-(4-(2-(3-(3-azabicyclo[3.1.0]hexan-3-yl)propoxy)-7-(3-(methoxymethoxy)naphthalen-1-yl)-5,6,7,8-tetrahydropyrido[3,4-d]pyrimidin-4-yl)piperazin-1-yl)prop-2-en-1-one A mixture of benzyl 4-(2-(3-(3-azabicyclo[3.1.0]hexan-3-yl)propoxy)-7-(3-(methoxymethoxy)-naphthalen-1-yl)-5,6,7,8-tetrahydropyrido[3,4-d]pyrimidin-4-yl)piperazine-1-carboxylate (49 mg, 0.072 mmol), palladium on carbon (12 mg, Degussa Type, 10 wt %, 50% H₂O), EtOH (1.5 mL) and THF (1.5 mL) was purged with hydrogen and stirred under H₂ atmosphere (rubber balloon) for 3 hours. The reaction mixture was diluted with EtOH (3 mL), filtered through Celite and the celite washed with EtOH (2×2 mL). The combined organics were evaporated in vacuo. The resulted colorless solid was dissolved in DCM (5 mL), cooled in an ice-salt bath with stirring and triethylamine (0.04 mL, 3 eq.) was added at once followed by addition of acryloyl chloride (16 μL, 2 eq.). After 1 min at −5° C. the reaction was quenched with NH₄OH (0.05 mL) and evaporated in vacuo. The crude product was dissolved in DCM (5 mL), filtered through a cotton plug and chromatographed on silica gel, Redisep 12 g, using 6 to 10% MeOH in DCM+0.2% NH₄OH as eluent to give a colorless solid (30 mg, 69%). ES+APCI MS m/z 599.3 [M+H]⁺.

612
-continued

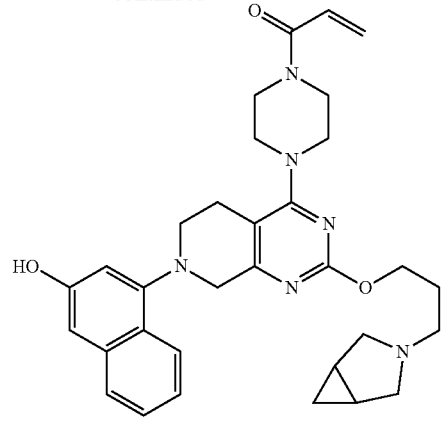

Step D: 1-(4-(2-(3-(3-azabicyclo[3.1.0]hexan-3-yl)propoxy)-7-(3-hydroxynaphthalen-1-yl)-5,6,7,8-tetrahydropyrido[3,4-d]pyrimidin-4-yl)piperazin-1-yl)prop-2-en-1-one To a stirred solution of 1-(4-(2-(3-(3-azabicyclo[3.1.0]hexan-3-yl)propoxy)-7-(3-(methoxymethoxy)naphthalen-1-yl)-5,6,7,8-tetrahydropyrido[3,4-d]pyrimidin-4-yl)piperazin-1-yl)prop-2-en-1-one (30 mg, 0.050 mmol) in a mixture of MeOH and THF 1:1 (3 mL) was added 6M aqueous HCl (0.3 mL, 36 eq.) and the solution was heated with stirring at 50° C. for 1.5 h. The reaction mixture was cooled to room temperature, divided between EtOAc (20 mL) and 0.5M Na₂CO₃ (5 mL) and the layers separated. The organic layer was washed with brine (1 mL), dried over Na₂SO₄ and evaporated in vacuo. The residue was chromatographed on silica, Redisep 12 g, using 6% MeOH in DCM+0.2% NH₄OH as eluent to give a colorless solid (20.62 mg, 74%). ES+APCI MS m/z 555.4 [M+H]⁺.

Example 207

(R)-1-(4-(2-(2-(3-fluoropiperidin-1-yl)ethoxy)-7-(3-hydroxynaphthalen-1-yl)-5,6,7,8-tetrahydropyrido[3,4-d]pyrimidin-4-yl)piperazin-1-yl)prop-2-en-1-one

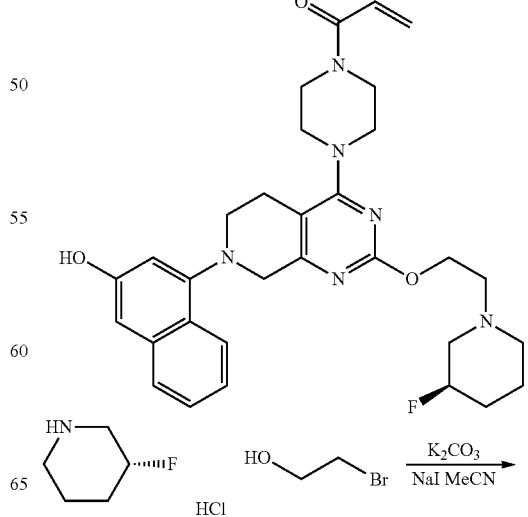

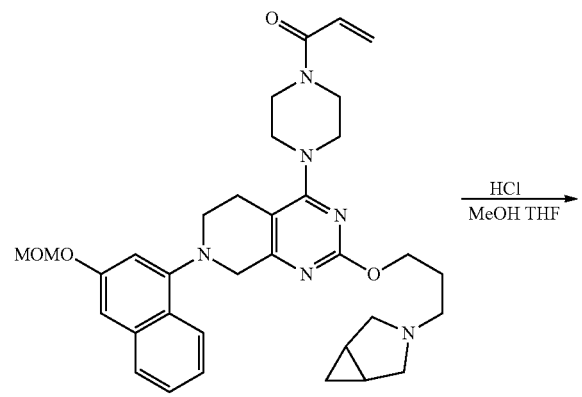

-continued

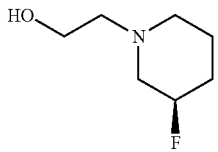

Step A: (R)-2-(3-fluoropiperidin-1-yl)ethan-1-ol

A mixture of R-3-fluoropiperidine hydrochloride (209 mg, 1.50 mmol), 2-bromoethan-1-ol (117 μL, 1.65 mmol, 1.1 eq.), K₂CO₃ (0.62 g, 4.5 mmol, 3 eq.), sodium iodide (225 mg, 1.5 mmol, 1 eq.) and acetonitrile (2 mL) in a 4-mL vial was flushed with N₂. The vial was capped and stirred at room temperature for 2 days. The resulted suspension was diluted with water (2 mL) and extracted with ether (15 mL). The ether solution was washed with brine, dried over Na₂SO₄ and decanted into a pear-shaped flask and trifluoroacetic acid (115 μL, 1 eq) was added and the mixture was concentrated to ~5 mL. The upper ethereal layer was decanted, the residual oily liquid was dried under vacuum overnight. The oily liquid was diluted with water (0.5 mL) and ether (10 mL) with stirring, followed by addition of 50% NaOH (0.2 mL, 2.5 mmol, 2 eq.). The layers were separated, the organic solution was dried over KOH, filtered and carefully concentrated under nitrogen to yield crude amino alcohol as a colorless oil (120 mg, 54%).

Step B: Benzyl (R)-4-(2-(2-(3-fluoropiperidin-1-yl)ethoxy)-7-(3-(methoxymethoxy)naphthalen-1-yl)-5,6,7,8-tetrahydropyrido[3,4-d]pyrimidin-4-yl)piperazine-1-carboxylate A mixture of benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (75 mg, 0.13 mmol), crude (R)-2-(3-fluoropiperidin-1-yl)ethan-1-ol (58 mg, 0.39 mmol), Cs₂CO₃ (213 mg, 0.65 mmol), and dioxane (0.5 mL) in a 1.7-mL vial was purged with nitrogen. The vial was capped and stirred at 110° C. for 48 hours. The reaction mixture was cooled, diluted with EtOAc (1 mL), filtered through Celite and the celite washed with EtOAc (2×2 mL) and the combined organics evaporated in vacuo. The residue was chromatographed on silica, Redisep 24 g, using 6% MeOH in DCM+0.2% NH₄OH as eluent to give a colorless solid (30 mg, 34%). ES+APCI MS m/z 685.4 [M+H]⁺.

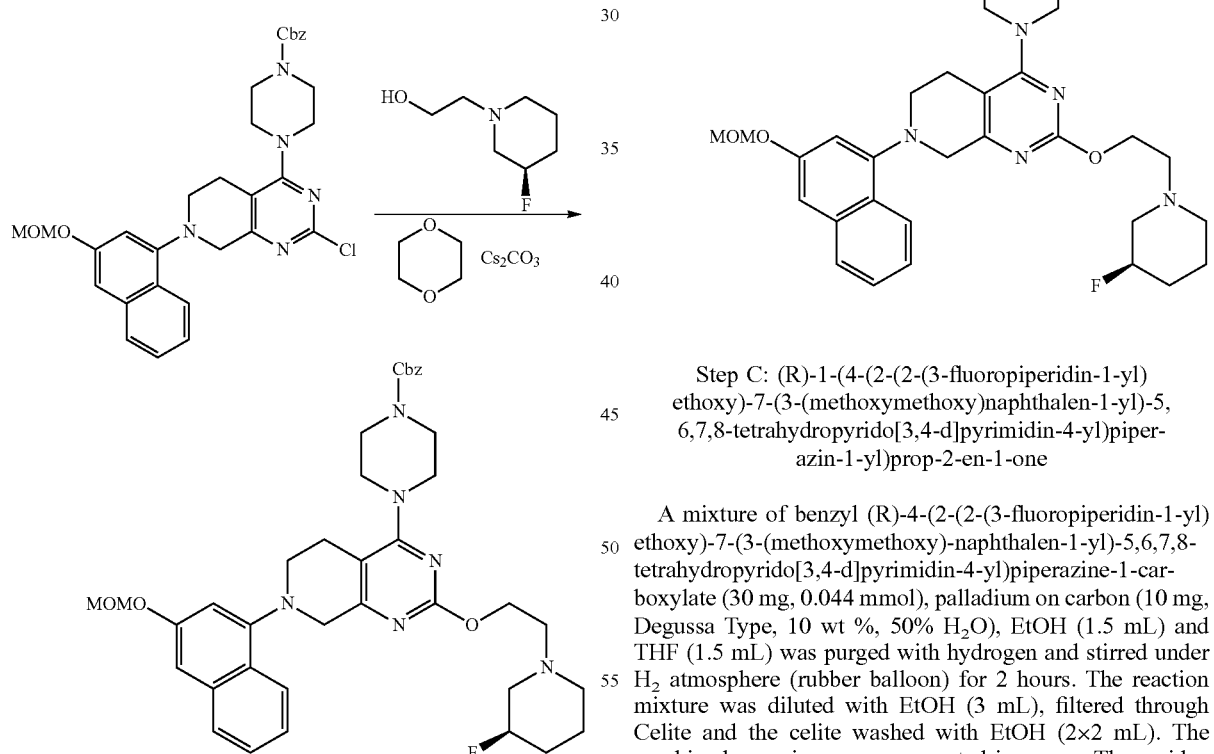

Step C: (R)-1-(4-(2-(2-(3-fluoropiperidin-1-yl)ethoxy)-7-(3-(methoxymethoxy)naphthalen-1-yl)-5,6,7,8-tetrahydropyrido[3,4-d]pyrimidin-4-yl)piperazin-1-yl)prop-2-en-1-one A mixture of benzyl (R)-4-(2-(2-(3-fluoropiperidin-1-yl)ethoxy)-7-(3-(methoxymethoxy)-naphthalen-1-yl)-5,6,7,8-tetrahydropyrido[3,4-d]pyrimidin-4-yl)piperazine-1-carboxylate (30 mg, 0.044 mmol), palladium on carbon (10 mg, Degussa Type, 10 wt %, 50% H₂O), EtOH (1.5 mL) and THF (1.5 mL) was purged with hydrogen and stirred under H₂ atmosphere (rubber balloon) for 2 hours. The reaction mixture was diluted with EtOH (3 mL), filtered through Celite and the celite washed with EtOH (2×2 mL). The combined organics were evaporated in vacuo. The residue was dissolved in DCM (3 mL) and cooled in an ice-salt bath with stirring. Triethylamine (0.02 mL, 3 eq.) was next added at once followed by addition of acryloyl chloride (7 μL, 2 eq.). After 1 min at −10° C. the reaction was quenched with NH₄OH (0.03 mL) and evaporated in vacuo. The residue was dissolved in DCM (5 mL), filtered, and chromatographed on silica gel, Redisep 12 g, using 6 to 10% MeOH in DCM+0.2% NH₄OH in DCM as eluent to give a colorless solid (22 mg, 83%). ES+APCI MS m/z 605.3 [M+H]⁺.

615

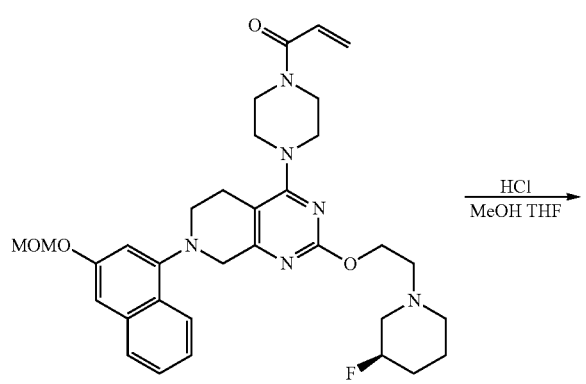

616

Example 208

1-(4-(2-(3-((3R,4S)-3,4-difluoropyrrolidin-1-yl)propoxy)-7-(3-hydroxynaphthalen-1-yl)-5,6,7,8-tetrahydropyrido[3,4-d]pyrimidin-4-yl)piperazin-1-yl)prop-2-en-1-one

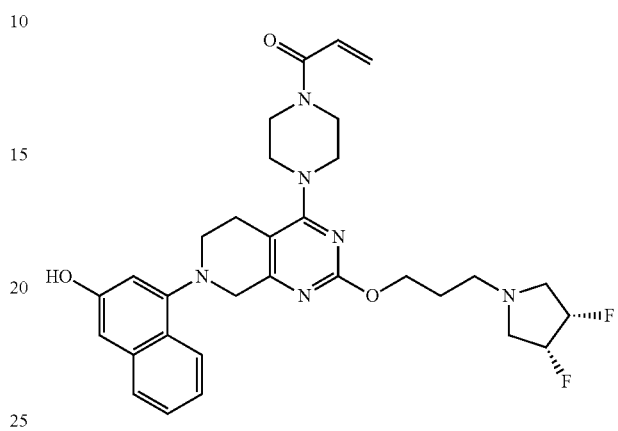

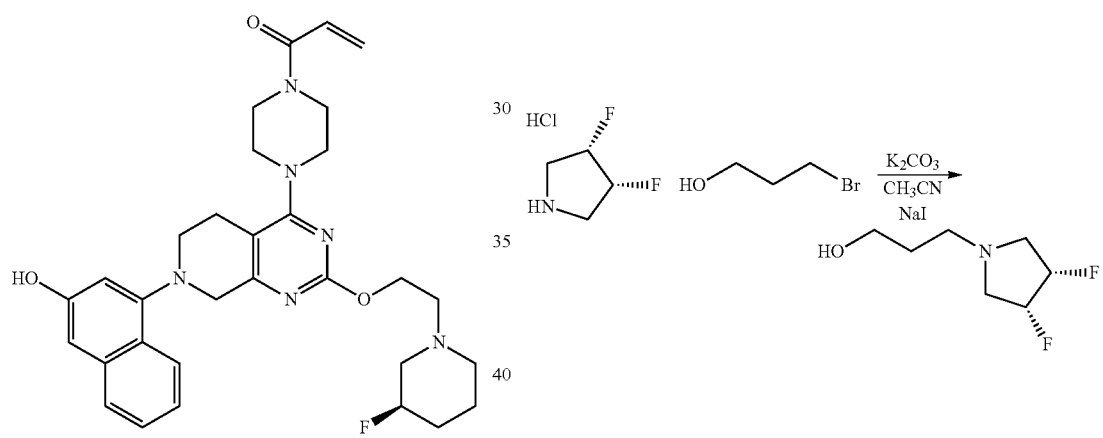

Step A: 3-((3R,4S)-3,4-difluoropyrrolidin-1-yl)propan-1-ol

Step D: (R)-1-(4-(2-(2-(3-fluoropiperidin-1-yl)ethoxy)-7-(3-hydroxynaphthalen-1-yl)-5,6,7,8-tetrahydropyrido[3,4-d]pyrimidin-4-yl)piperazin-1-yl)prop-2-en-1-one To a stirred solution of (R)-1-(4-(2-(2-(3-fluoropiperidin-1-yl)ethoxy)-7-(3-(methoxymethoxy)naphthalen-1-yl)-5,6,7,8-tetrahydropyrido[3,4-d]pyrimidin-4-yl)piperazin-1-yl)prop-2-en-1-one (22 mg, 0.036 mmol) in a mixture of MeOH and THF 1:1 (3 mL) was added 6M aqueous HCl (0.3 mL) and the solution was heated with stirring at 50° C. for 1.5 h. The reaction mixture was cooled to room temperature, divided between EtOAc (20 mL) and 0.5M Na$_2$CO$_3$ (5 mL) and the layers separated. The organic layer was washed with brine (1 mL), dried over Na$_2$SO$_4$ and evaporated in vacuo. The residue was chromatographed on silica gel, Redisep 12 g, using 6% MeOH in DCM+0.2% NH$_4$OH as eluent to give a colorless solid (16.86 mg, 83%). ES+APCI MS m/z 561.2 [M+H]$^+$.

A mixture of (3R,4S)-3,4-difluoropyrrolidine hydrochloride (200 mg, 1.39 mmol), 3-bromopropan-1-ol (126 µL, 1.39 mmol, 1.0 eq.), potassium carbonate (577 mg, 4.18 mmol, 3 eq.), sodium iodide (209 mg, 1.39 mmol, 1 eq.) and acetonitrile (2 mL) in a 7-mL vial was flushed with N$_2$. The vial was capped and the reaction mixture was stirred at room temperature for 2 days. The mixture was diluted with water (2 mL) and extracted with ether (15 mL). The ether solution was washed with brine, dried over Na$_2$SO$_4$ and decanted into a pear-shaped flask. Trifluoroacetic acid (107 µL, 1 eq) was next added and the mixture was evaporated and dried in vacuo. The residue was diluted with water (0.5 mL) and washed with ether (5 mL). To the aqueous layer was added diethyl ether (15 mL) followed by 10M NaOH (0.2 mL, 5 mmol) and the mixture was stirred for 1 hour. The organic layer was separated and dried over solid KOH, filtered through a cotton plug and evaporated under N$_2$ to give a colorless oil (80 mg, 35%) which was used crude in the next reaction.

617

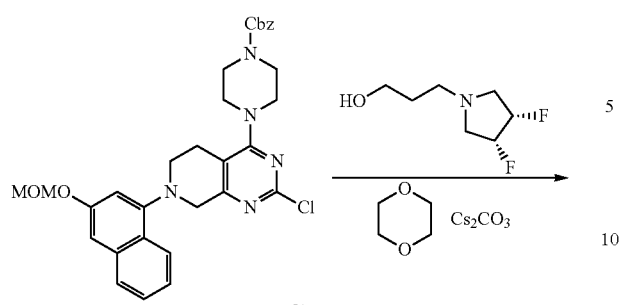

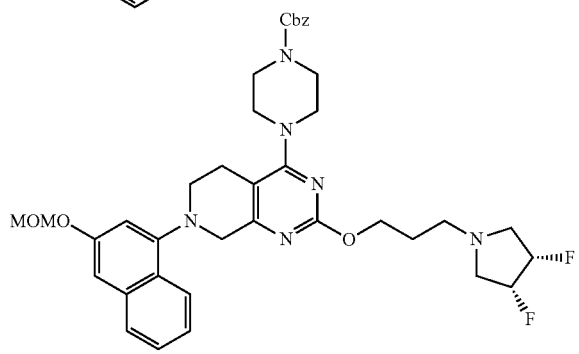

618

Step B: Benzyl 4-(2-(3-((3R,4S)-3,4-difluoropyrrolidin-1-yl)propoxy)-7-(3-(methoxymethoxy)naphthalen-1-yl)-5,6,7,8-tetrahydropyrido[3,4-d]pyrimidin-4-yl)piperazine-1-carboxylate A mixture of benzyl 4-(2-chloro-7-(3-(methoxymethoxy)naphthalen-1-yl)-5,6,7,8-tetrahydropyrido[3,4-d]pyrimidin-4-yl)piperazine-1-carboxylate (75 mg, 0.13 mmol), crude 2-((4,4-difluoropiperidin-1-yl)ethan-1-ol (65 mg, 0.39 mmol), cesium carbonate (213 mg, 0.65 mmol, 5 eq.) and dioxane (0.5 mL) in a 1.7-mL vial was purged with nitrogen. The vial was capped and stirred at 110° C. over the weekend. The reaction mixture was cooled to room temperature and divided between EtOAc (15 mL) and water (5 mL) and the layers separated. The organic layer was washed with brine, dried over Na$_2$SO$_4$ and evaporated in vacuo. The product was purified by chromatography on silica, Redisep 24 g, using 3% MeOH in DCM as eluent to give a colorless solid (46 mg, 50%). ES+APCI MS m/z 703.3 [M+H]$^+$.

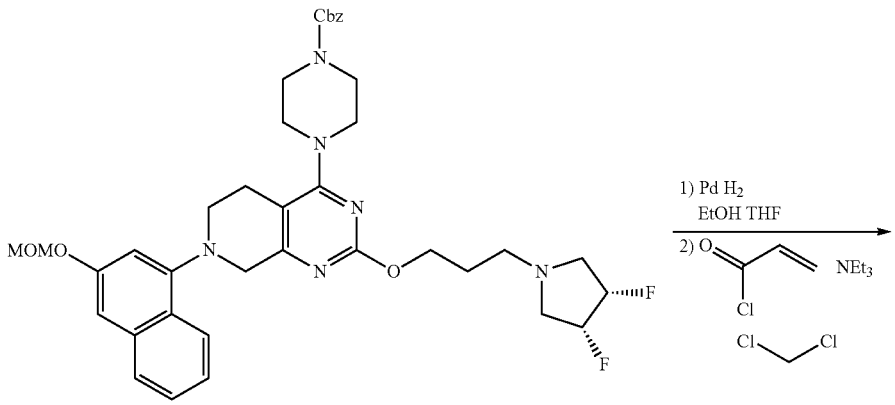

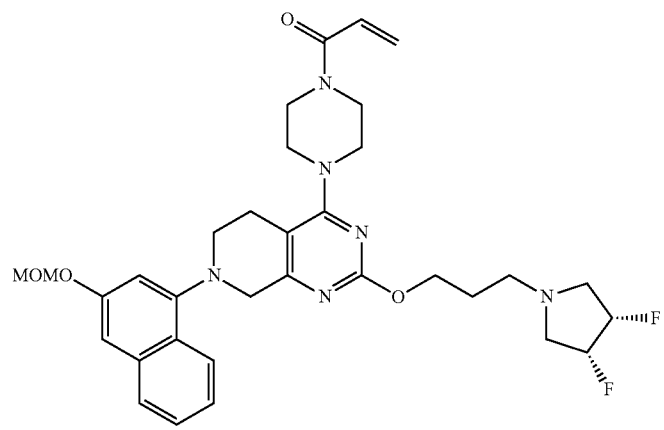

Step C: 1-(4-(2-(3-((3R,4S)-3,4-difluoropyrrolidin-1-yl)propoxy)-7-(3-(methoxymethoxy)naphthalen-1-yl)-5,6,7,8-tetrahydropyrido[3,4-d]pyrimidin-4-yl)piperazin-1-yl)prop-2-en-1-one A mixture of benzyl 4-(2-(3-((3R,4S)-3,4-difluoropyrrolidin-1-yl)propoxy)-7-(3-(methoxymethoxy)naphthalen-1-yl)-5,6,7,8-tetrahydropyrido[3,4-d]pyrimidin-4-yl)piperazine-1-carboxylate (46 mg, 0.065 mmol), palladium on carbon (15 mg, Degussa Type, 10 wt %, 50% $H_2O$), EtOH (1 mL) and THF (1 mL) was purged with hydrogen and stirred under $H_2$ atmosphere (rubber balloon) for 3 hours. The reaction mixture was diluted with EtOH (3 mL), filtered through Celite and the celite washed with EtOH (2×2 mL). The combined organics were evaporated in vacuo. The residue was dissolved in DCM (3 mL) and cooled in an ice-salt bath with stirring. Triethylamine (0.02 mL) was next added followed by addition of acryloyl chloride (7 µL, 2 eq.). After 1 min at −10° C. the reaction was quenched with $NH_4OH$ (0.03 mL) and evaporated in vacuo. The residue was dissolved in DCM (3 mL), filtered and purified by chromatography on silica gel, Redisep 12 g, using 5% MeOH in DCM as eluent to give a colorless solid (29 mg, 71%). ES+APCI MS m/z 623.3 [M+H]$^+$.

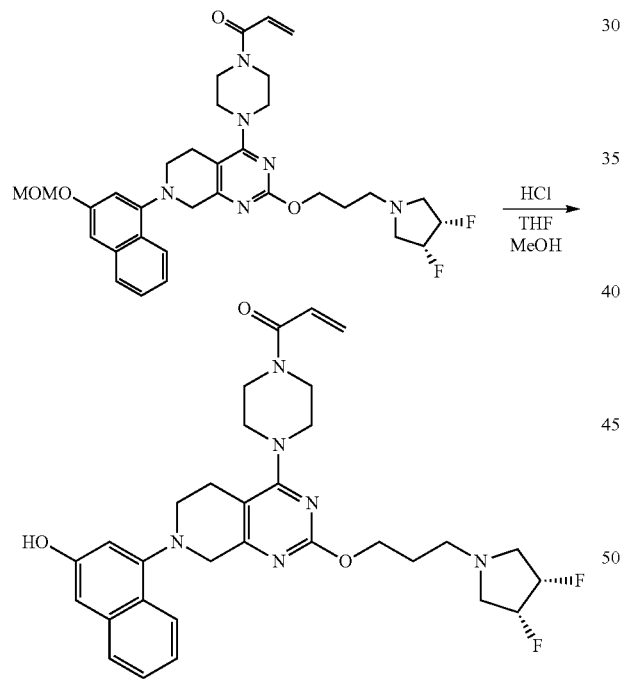

Step D: 1-(4-(2-(3-((3R,4S)-3,4-difluoropyrrolidin-1-yl)propoxy)-7-(3-hydroxynaphthalen-1-yl)-5,6,7,8-tetrahydropyrido[3,4-d]pyrimidin-4-yl)piperazin-1-yl)prop-2-en-1-one To a stirred solution of 1-(4-(2-(3-((3R,4S)-3,4-difluoropyrrolidin-1-yl)propoxy)-7-(3-(methoxymethoxy)naphthalen-1-yl)-5,6,7,8-tetrahydropyrido[3,4-d]pyrimidin-4-yl)piperazin-1-yl)prop-2-en-1-one (29 mg, 0.047 mmol) in a mixture of MeOH and THF 1:1 (2 mL) was added 6M aqueous HCl (0.2 mL) and the solution was heated with stirring at 50° C. for 1.5 h. The reaction mixture was cooled to room temperature, divided between EtOAc (15 mL) and 0.5M $Na_2CO_3$ (10 mL) and the layers separated. The organic layer was washed with brine (3 mL), dried over $Na_2SO_4$ and evaporated in vacuo. The residue was purified by chromatography on silica, Redisep 12 g, using 5% MeOH in DCM as eluent to give a colorless solid (12.87 mg, 48%). ES+APCI MS m/z 579.2 [M+H]$^+$.

Example 209

1-(4-(7-(5-methyl-1H-indol-4-yl)-2-(3-morpholinopropoxy)-5,6,7,8-tetrahydropyrido[3,4-d]pyrimidin-4-yl)piperazin-1-yl)prop-2-en-1-one

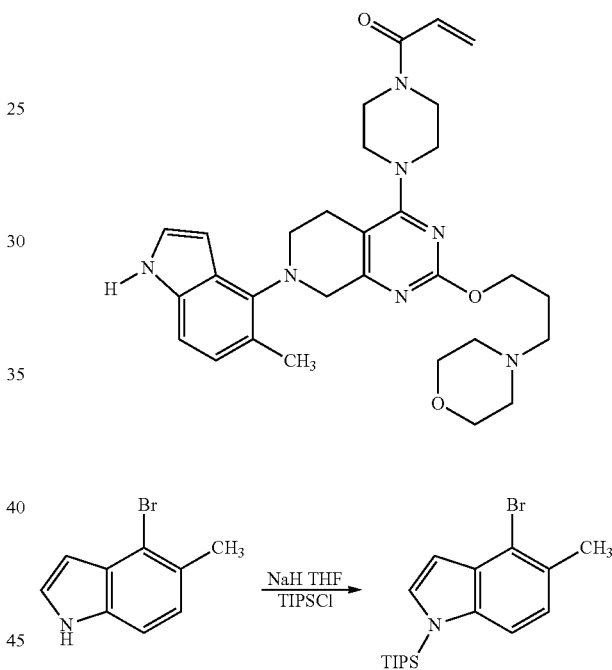

Step A:
4-bromo-5-methyl-1-(triisopropylsilyl)-1H-indole

A solution of 4-bromo-5-methyl-1H-indole (100 mg, 0.476 mmol) in dry THF (2 mL) under nitrogen was cooled with stirring in an ice-salt bath. Sodium hydride (23 mg 60% in oil, 0.57 mg, 1.2 eq.) was added and the mixture was stirred for 30 min at −5° C., then 1 h at room temperature (gas evolution ceased). Chlorotriisopropylsilane (0.10 mL, 0.48 mmol, 1 eq.) was next added and the reaction mixture was stirred at r.t. for 2 hours. The reaction was divided between EtOAc (15 mL) and water (10 mL) and the layers separated. The organic layer was washed with water (5 mL), brine (5 mL), dried over $Na_2SO_4$ and evaporated in vacuo. The residue was purified on silica gel using hexanes as eluent to give product. (107 mg, 63%).

621

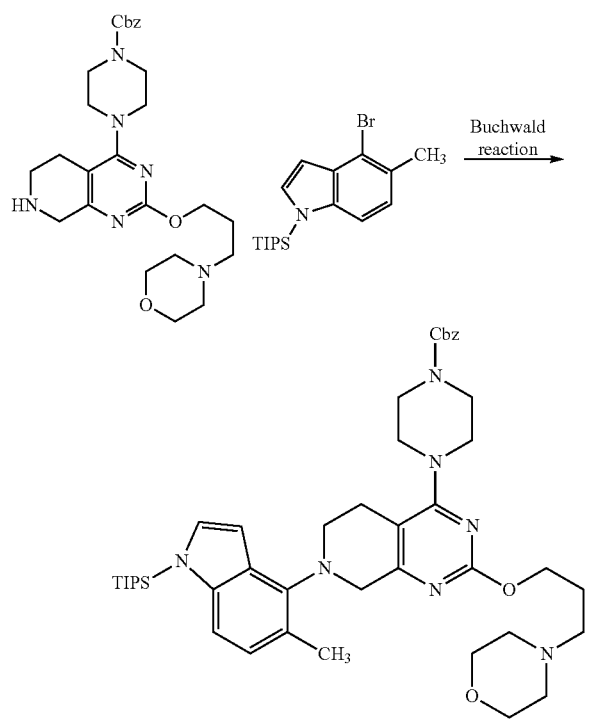

Buchwald reaction →

Step B: Benzyl 4-(7-(5-methyl-1-(triisopropylsilyl)-1H-indol-4-yl)-2-(3-morpholinopropoxy)-5,6,7,8-tetrahydropyrido[3,4-d]pyrimidin-4-yl)piperazine-1-carboxylate A stirred mixture of tris(dibenzylideneacetone)dipalladium (0) (17 mg, 0.019 mmol) and (+/−)-2,2'-bis(diphenylphosphino)-1,1'-binaphthyl (24 mg, 0.038 mmol) in dry degassed toluene (0.5 mL) under nitrogen was heated to 100° C. for 15 minutes. The mixture was cooled to room temperature and solid sodium-t-butoxide (37 mg, 0.38 mmol) added followed by addition of a solution of 4-bromo-5-methyl-1-(triisopropylsilyl)-1H-indole (90 mg, 0.25 mmol) and benzyl 4-(2-(3-morpholinopropoxy)-5,6,7,8-tetrahydropyrido[3,4-d]pyrimidin-4-yl)piperazine-1-carboxylate (94 mg, 0.19 mmol) in dry degassed toluene (0.5 mL). The reaction flask was closed and heated to 100° C. overnight. The reaction mixture was cooled to room temperature, divided between EtOAc (15 mL) and water (5 mL) and the layers separated. The organic layer was washed with brine, dried over Na$_2$SO$_4$ and evaporated in vacuo. The product was purified by chromatography on silica gel, Redisep 24 g, using 3 to 5% MeOH in dichloromethane as eluent to give a light-yellow solid (28 mg, 19%). ES+APCI MS m/z 782.3 [M]$^+$.

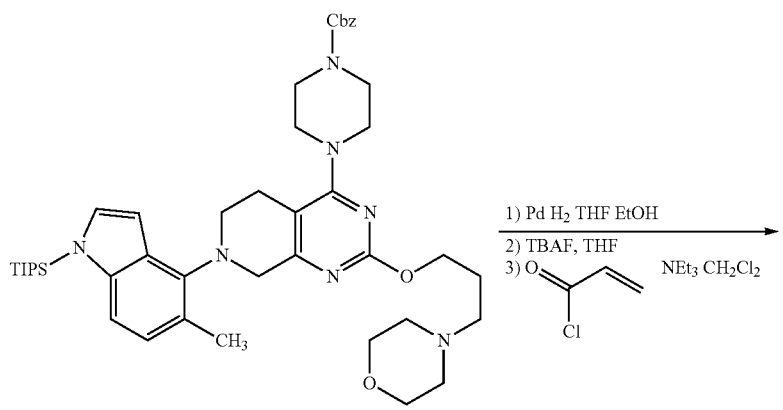

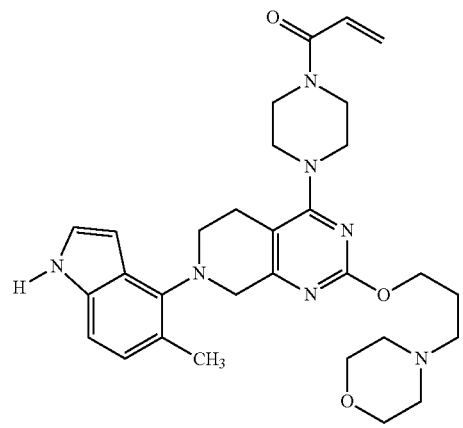

Step C: 1-(4-(7-(5-methyl-1H-indol-4-yl)-2-(3-morpholinopropoxy)-5,6,7,8-tetrahydropyrido[3,4-d]pyrimidin-4-yl)piperazin-1-yl)prop-2-en-1-one A mixture of benzyl 4-(7-(5-methyl-1-(triisopropylsilyl)-1H-indol-4-yl)-2-(3-morpholinopropoxy)-5,6,7,8-tetrahydropyrido[3,4-d]pyrimidin-4-yl)piperazine-1-carboxylate (46 mg, 0.065 mmol), palladium on carbon (35 mg, Degussa Type, 10 wt %, 50% H$_2$O) in EtOH (1 mL) and THF (1 mL) was purged with hydrogen and stirred under H$_2$ atmosphere (rubber balloon) overnight. The reaction mixture was diluted with dioxane (3 mL), filtered through celite and the celite washed with dioxane (2×2 mL). The combined organics were evaporated in vacuo and dried under high vacuum. The residue was dissolved in THF (1 mL) under N$_2$, then 1M tetra-n-butylammonium fluoride in THF (0.07 mL, 2 eq.) was added with stirring and the solution stirred at 0° C. for 15 minutes. The reaction mixture was divided between ether (15 mL) and water (5 mL) and the layers separated. The organic layer was washed with water (3 mL), brine (3 mL), dried over Na$_2$SO$_4$ and evaporated under nitrogen. The crude product was dissolved in DCM (3 mL) and cooled in an ice-salt-dry ice bath (−20° C.) with stirring. Triethylamine (10 µL, 2 eq.) was next added followed by acryloyl chloride (2 µL, 0.75 eq.). After 10 min at −20° C. the reaction was quenched with NH$_4$OH (0.03 mL). and evaporated in vacuo. The product was purified by chromatography on silica gel column using 5% MeOH/DCM+0.1% NH$_4$OH as eluent to give a colorless solid (3.69 mg, 19%). ES+APCI MS m/z 546.3 [M+H]$^+$.

Example 210

2-(1-acryloyl-4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazin-2-yl)acetonitrile

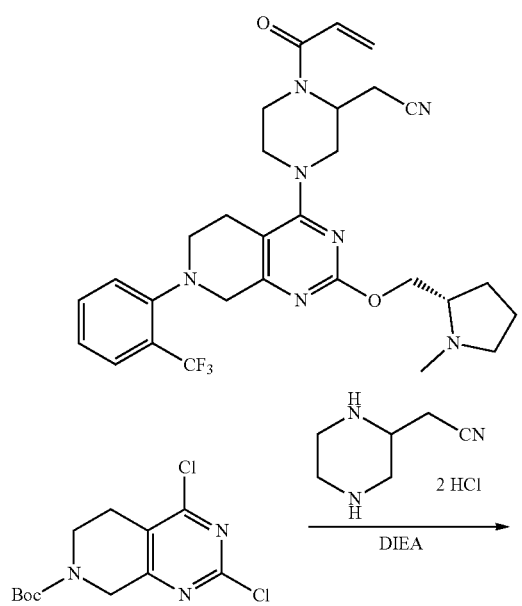

Step A: tert-butyl 2-chloro-4-(3-(cyanomethyl)piperazin-1-yl)-5,8-dihydropyrido[3,4-d]pyrimidine-7(6H)-carboxylate tert-butyl 2,4-dichloro-5,8-dihydropyrido[3,4-d]pyrimidine-7(6H)-carboxylate (8.00 g, 26.3 mmol), Hunig's base (22.9 ml, 132 mmol) and 2-(piperazin-2-yl)acetonitrile dihydrochloride (5.21 g, 26.3 mmol) were placed in DMA (75 mL) and stirred at room temperature for 20 minutes. Water was added to the reaction and the mixture was extracted with EtOAc (3×100 mL). The extracts were combined and washed with water (3×50 mL), dried with sodium sulfate, filtered and concentrated to provide crude material that was used as is. ES+APCI MS m/z 393.3 [M+H]$^+$.

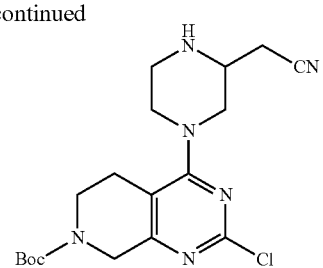

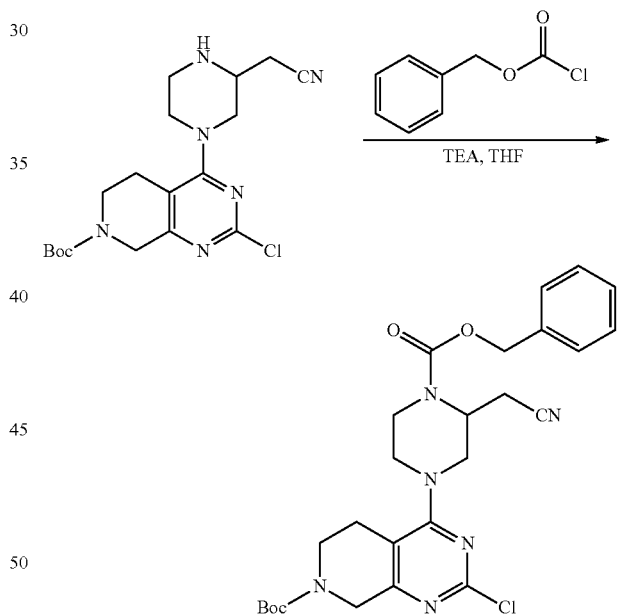

Step B: tert-butyl 4-(4-((benzyloxy)carbonyl)-3-(cyanomethyl)piperazin-1-yl)-2-chloro-5,8-dihydropyrido[3,4-d]pyrimidine-7(6H)-carboxylate tert-butyl 2-chloro-4-(3-(cyanomethyl)piperazin-1-yl)-5,8-dihydropyrido[3,4-d]pyrimidine-7(6H)-carboxylate (10.5 g, 26.7 mmol) and TEA (5.6 ml, 40.1 mmol) were placed in THF (100 mL) and cooled to 0° C. Benzyl carbonochloridate (5.7 ml, 40.1 mmol) was added and the reaction was stirred at 0° C. for 30 minutes. Water was added to the reaction and the mixture was extracted with DCM (3×50 mL) and the extracts were combined and concentrated. The residue was purified by silica gel (0-60% EtOAc in hexane as eluent) to provide tert-butyl 4-(4-((benzyloxy)carbonyl)-3-(cyanomethyl)piperazin-1-yl)-2-chloro-5,8-dihydropyrido [3,4-d]pyrimidine-7(6H)-carboxylate (12.9 g, 24.5 mmol, 92% yield). ES+APCI MS m/z 527.1 [M+H]+.

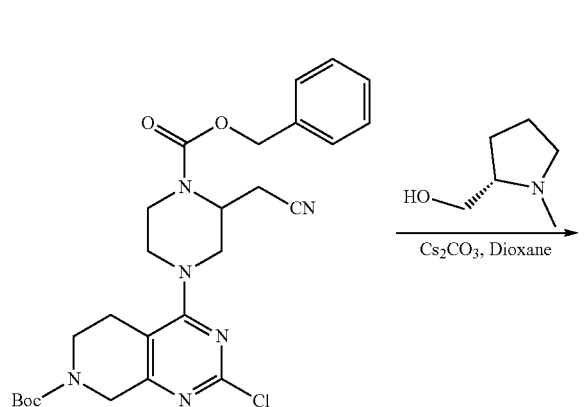

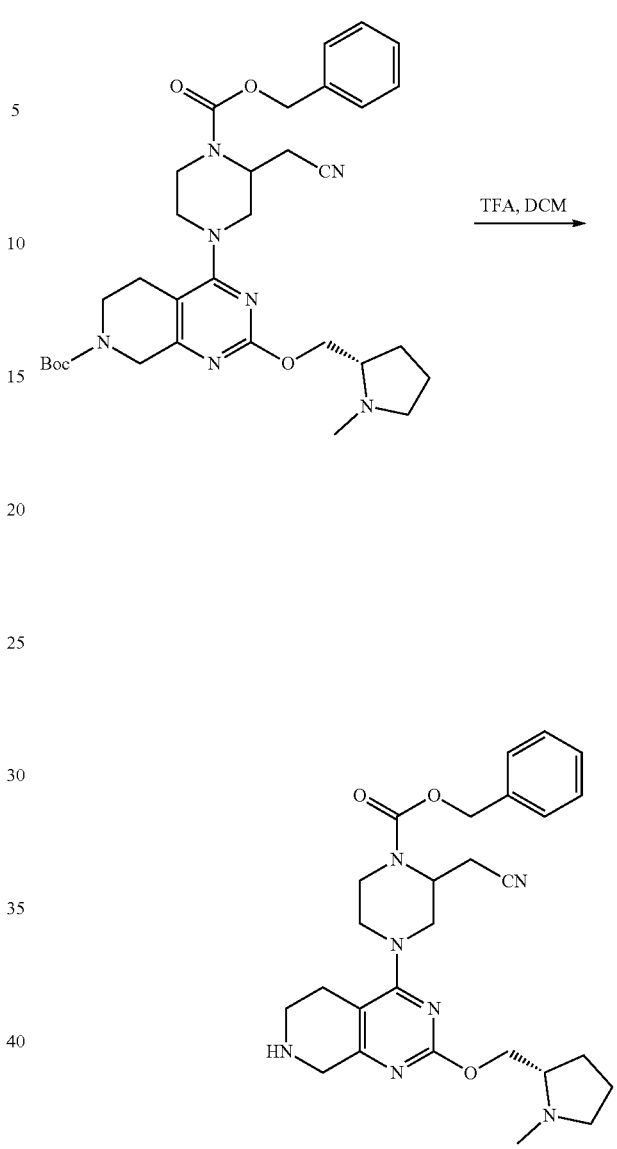

Step C: tert-butyl 4-(4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate In a sealed tube tert-butyl 4-(4-((benzyloxy)carbonyl)-3-(cyanomethyl)piperazin-1-yl)-2-chloro-5,8-dihydropyrido [3,4-d]pyrimidine-7(6H)-carboxylate (1.50 g, 2.85 mmol) was dissolved in dioxane (1.42 ml, 2.85 mmol) and treated with milled cesium carbonate (1.85 g, 5.69 mmol) and (2S)-1-Ethyl-2-pyrrolidinyl]methanol (1.64 g, 14.2 mmol). The tube was then capped and heated to 90° C. for 24 hr. The reaction was cooled to room temperature and water was added. The mixture was extracted with DCM (3×25 mL), and the combined organics concentrated in vacuo. The residue was purified by silica gel (0-12% MeOH in DCM w/0.2% NH4OH as eluent) to give tert-butyl 4-(4-((benzyloxy)carbonyl)-3-(cyanomethyl)piperazin-1-yl)-2-((S)-1-methylpyrrolidin-2-yl)methoxy)-5,8-dihydropyrido[3,4-d]pyrimidine-7(6H)-carboxylate (831 mg, 1.37 mmol, 48% yield). ES+APCI MS m/z 606.2 [M+H]+.

Step D: benzyl 2-(cyanomethyl)-4-(2-(((S)-1-methylpyrrolidin-2-yl)methoxy)-5,6,7,8-tetrahydropyrido [3,4-d]pyrimidin-4-yl)piperazine-1-carboxylate tert-butyl 4-(4-((benzyloxy)carbonyl)-3-(cyanomethyl) piperazin-1-yl)-2-(((S)-1-methylpyrrolidin-2-yl)methoxy)-5,8-dihydropyrido[3,4-d]pyrimidine-7(6H)-carboxylate (831 mg, 1.37 mmol) was placed in DCM (15 mL) and TFA (2114 μL, 27.4 mmol) was added and the reaction was stirred at rt for 1 hr. The reaction was concentrated. Saturated bicarbonate was added and the mixture was extracted with DCM (3×25 mL). The extracts were combined, dried with sodium sulfate, filtered and concentrated to give benzyl 2-(cyanomethyl)-4-(2-(((S)-1-methylpyrrolidin-2-yl) methoxy)-5,6,7,8-tetrahydropyrido[3,4-d]pyrimidin-4-yl) piperazine-1-carboxylate (665 mg, 1.32 mmol, 96% yield) which was used as is. ES+APCI MS m/z 506.2 [M+H]+.

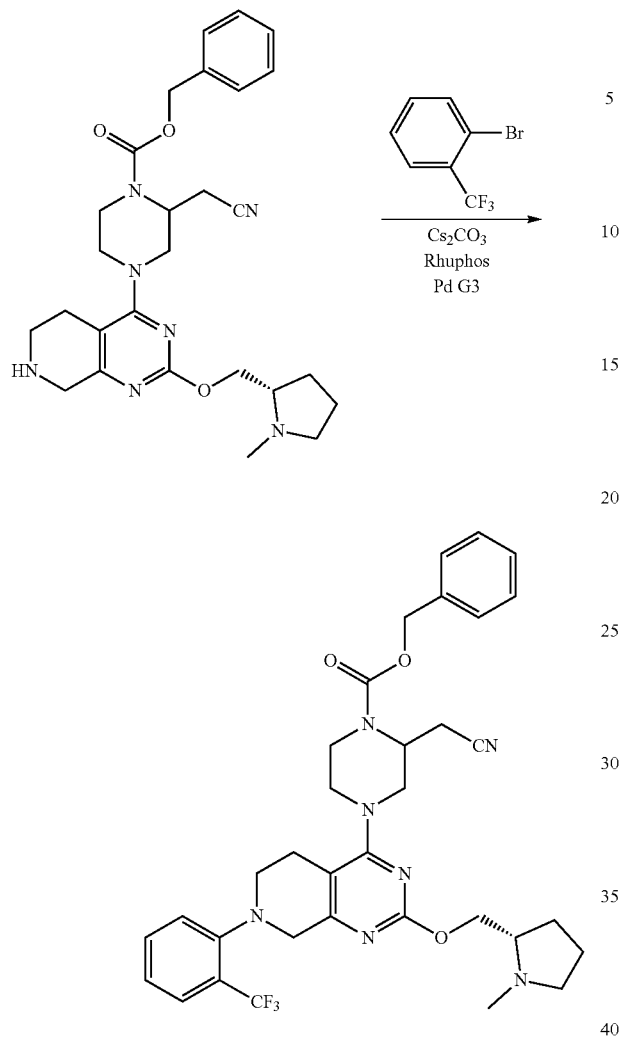

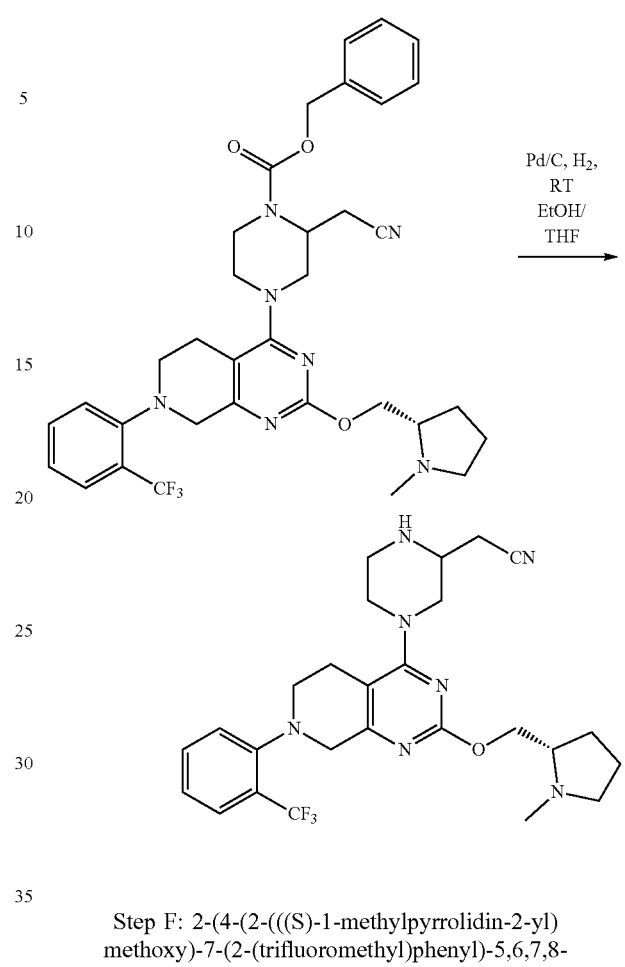

Step E: benzyl 2-(cyanomethyl)-4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazine-1-carboxylate To a vial was added cesium carbonate (103 mg, 0.316 mmol), benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (80 mg, 0.158 mmol), Rhuphos Pd G3 (13.2 mg, 0.016 mmol), 1-bromo-2-(trifluoromethyl)benzene (53.4 mg, 0.237 mmol) and 1,4-dioxane (1582 µL, 0.158 mmol) and the vial was degassed with Ar, sealed then heated to 70° C. for 24 hours. Water and saturated NH₄Cl were added to the reaction and the mixture was extracted with DCM. The organic layer concentrated in vacuo. The resulting residue was purified by silica gel (0-12% MeOH in DCM w/0.2% NH₄OH as eluent) to provide benzyl 2-(cyanomethyl)-4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazine-1-carboxylate (20.5 mg, 0.032 mmol, 20% yield). ES+APCI MS m/z 650.3 [M+H]⁺.

Step F: 2-(4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazin-2-yl)acetonitrile To a solution of benzyl 2-(cyanomethyl)-4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazine-1-carboxylate (20.5 mg, 0.032 mmol) in EtOH (316 µL, 0.0316 mmol) and THF (316 µL, 0.032 mmol) was added palladium (16.8 mg, 0.008 mmol) (Degussa Type, 10 wt %, 50% H₂O) and then an atmosphere of H₂ was introduced via vacuum followed by balloon pressure and was stirred for 2 hours. The mixture was then diluted with MeOH and filtered through GF/F paper. The filtrate was then concentrated to provide desired product which was used as is. ES+APCI MS m/z 516.2 [M+H]⁺.

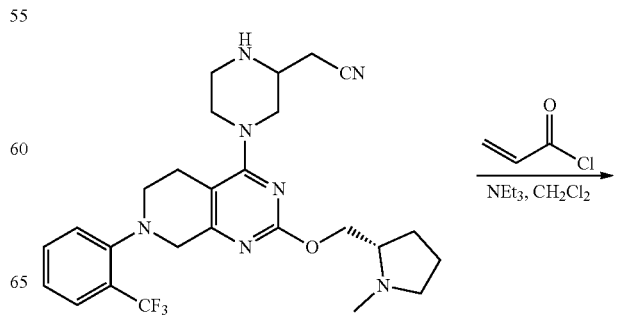

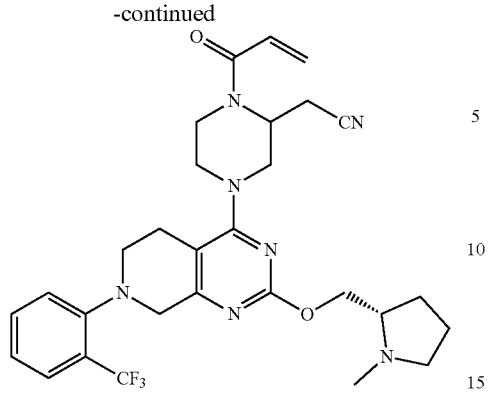

Step G: 2-(1-acryloyl-4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazin-2-yl)acetonitrile 2-(4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazin-2-yl)acetonitrile (16.3 mg, 0.032 mmol) and triethylamine (13.2 µL, 0.095 mmol) were placed in CH2Cl2 (316 µL, 0.032 mmol) and cooled to 0° C. Acryloyl chloride (632 µL, 0.063 mmol) was added (freshly prepared 0.1M solution in DCM) and the reaction was stirred for 1 hour at 0° C. The mixture was concentrated and the resulting residue was purified by reverse phase chromatography (0-50% ACN:water w/0.1% TFA) to provide desired product (18.9 mg, 0.027 mmol, 87% yield). ES+APCI MS m/z 570.3 [M+H]+.

Example 211

2-(1-acryloyl-4-(2-(((S)-1-methylpyrrolidin-2-yl)methoxy)-7-(2-(trifluoromethoxy)phenyl)-5,6,7,8-tetrahydropyrido[3,4-d]pyrimidin-4-yl)piperazin-2-yl)acetonitrile

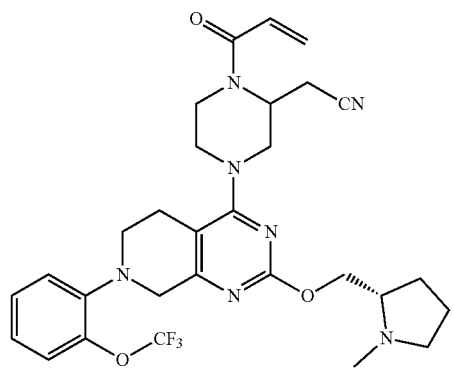 [SMILES: C=CC(=O)N1CCN(c2nc(OC[C@@H]3CCCN3C)nc3c2CCN(c2ccccc2OC(F)(F)F)C3)CC1CC#N]

Synthesized according to Example 210, Steps E-G using 1-bromo-2-(trifluoromethoxy)benzene in place of 1-bromo-2-(trifluoromethyl)benzene in Step E. ES+APCI MS m/z 586.3 [M+H]+.

Example 212

2-(1-acryloyl-4-(2-(((S)-1-methylpyrrolidin-2-yl)methoxy)-7-(4-(trifluoromethyl)pyridin-3-yl)-5,6,7,8-tetrahydropyrido[3,4-d]pyrimidin-4-yl)piperazin-2-yl)acetonitrile

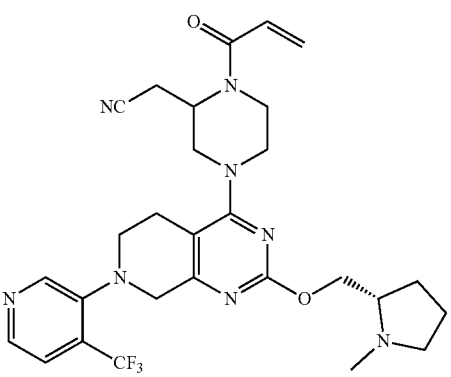 [SMILES: C=CC(=O)N1CCN(c2nc(OC[C@@H]3CCCN3C)nc3c2CCN(c2cnccc2C(F)(F)F)C3)CC1CC#N]

Synthesized according Example 210, Steps E-G using 3-bromo-4-(trifluoromethyl)pyridine in place of 1-bromo-2-(trifluoromethyl)benzene in Step E. ES+APCI MS m/z 571.3 [M+H]+.

Example 213

1-(4-(7-(5-hydroxy-2,3-dimethylphenyl)-2-(3-morpholinopropoxy)-5,6,7,8-tetrahydropyrido[3,4-d]pyrimidin-4-yl)piperazin-1-yl)prop-2-en-1-one

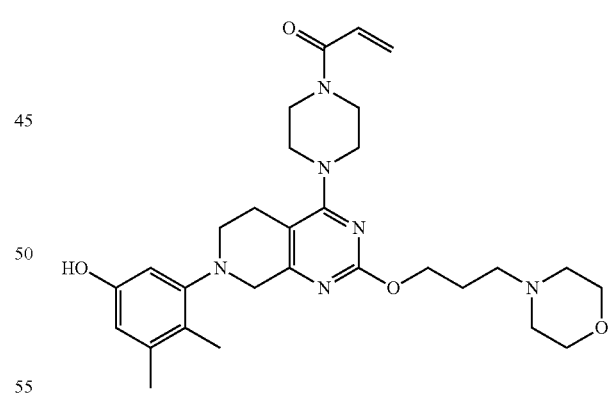

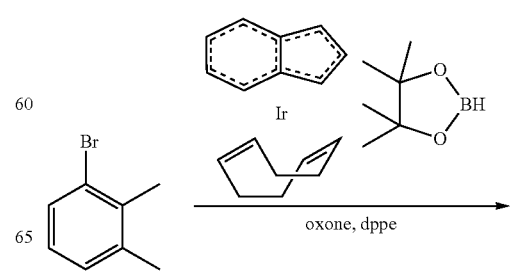

-continued

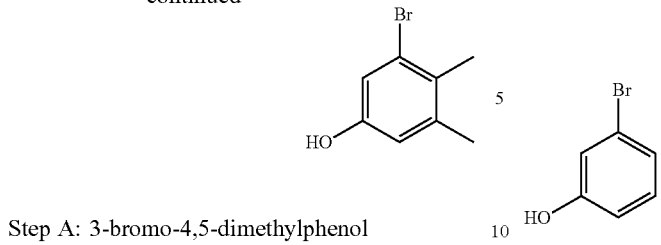

Step A: 3-bromo-4,5-dimethylphenol

In a sealed tube DPPE (0.431 g, 1.08 mmol), 4,4,5,5-tetramethyl-1,3,2-dioxaborolane (1.73 g, 13.5 mmol), (1,5-Cyclooctadiene)-eta5-indenyl)iridium(I) (0.449 g, 1.08 mmol) and 1-bromo-2,3-dimethylbenzene (1.00 g, 5.40 mmol) were placed in cyclohexane (6 mL) and was heated to 100° C. for 50 hr. The reaction was concentrated down and brought up in acetone (5 mL) and oxzone (3.32 g, 5.40 mmol) was added and stirred for 10 min. The reaction was quenched with saturated NaHSO3 and was extracted with DCM (3×20 ml). The extracts were washed with brine, water and concentrated. The residue was passed through a plug of silica eluting with DCM to provide 3-bromo-4,5-dimethylphenol (238 mg, 1.18 mmol, 22% yield).

Step B: 1-bromo-5-(methoxymethoxy)-2,3-dimethylbenzene

Was prepared according to the preparation for Intermediate 3 substituting the 3-bromo-4,5-dimethylphenol for 2-bromo-3-fluorophenol.

Step C: 1-(4-(7-(5-hydroxy-2,3-dimethylphenyl)-2-(3-morpholinopropoxy)-5,6,7,8-tetrahydropyrido[3,4-d]pyrimidin-4-yl)piperazin-1-yl)prop-2-en-1-one 2,2,2-trifluoroacetate was prepared according to Example 1 Steps C-F substituting Intermediate 25 for benzyl 4-(5,6,7,8-tetrahydropyrido[3,4-d]pyrimidin-4-yl)piperazine-1-carboxylate and 1-bromo-5-(methoxymethoxy)-2,3-dimethylbenzene for 1-bromo-3-(methoxymethoxy)naphthalene in Step C. ES+APCI MS m/z 537.3 [M+H]+.

Example 214

1-(4-(7-(5-hydroxy-2-((trifluoromethyl)thio)phenyl)-2-(3-morpholinopropoxy)-5,6,7,8-tetrahydropyrido[3,4-d]pyrimidin-4-yl)piperazin-1-yl)prop-2-en-1-one

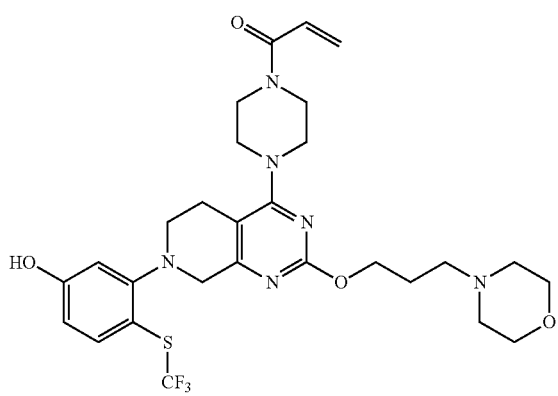

-continued

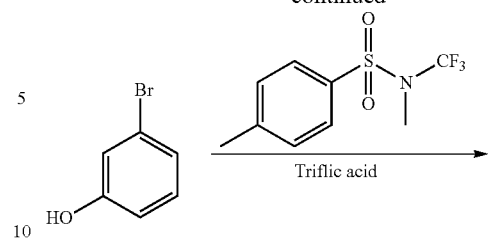

Step A: 3-bromo-4-((trifluoromethyl)thio)phenol

In a sealed tube 3-bromophenol (575 mg, 3.32 mmol) and N,4-dimethyl-N-(trifluoromethyl)benzenesulfonamide (1010 mg, 3.99 mmol) were placed in dry DCE (6 mL). Triflic acid (295 μL, 3.32 mmol) was added slowly and the reaction was then heated to 80° C. for 18 hours. The reaction was cooled and the solvent was removed under vacuum and the resulting residue was purified by silica gel (0-20% EtOAc in hexanes) to provide 3-bromo-4-((trifluoromethyl)thio)phenol (650 mg, 2.38 mmol, 72% yield)

Step B: (2-bromo-4-(methoxymethoxy)phenyl)(trifluoromethyl)sulfane

Was prepared according to the preparation for Intermediate 3 substituting the 3-bromo-4-((trifluoromethyl)thio)phenol for 2-bromo-3-fluorophenol.

Step C: 1-(4-(7-(5-hydroxy-2-((trifluoromethyl)thio)phenyl)-2-(3-morpholinopropoxy)-5,6,7,8-tetrahydropyrido[3,4-d]pyrimidin-4-yl)piperazin-1-yl)prop-2-en-1-one Synthesized according to Example 1 Step C-F substituting Intermediate 25 for benzyl 4-(5,6,7,8-tetrahydropyrido[3,4-d]pyrimidin-4-yl)piperazine-1-carboxylate and (2-bromo-4-(methoxymethoxy)phenyl)(trifluoromethyl)sulfane for 1-bromo-3-(methoxymethoxy)naphthalene in Step C. ES+APCI MS m/z 609.2 [M+H]+.

Example 215

(R)-1-(4-(2-(2-hydroxy-3-morpholinopropoxy)-7-(3-hydroxynaphthalen-1-yl)-5,6,7,8-tetrahydropyrido[3,4-d]pyrimidin-4-yl)piperazin-1-yl)prop-2-en-1-one

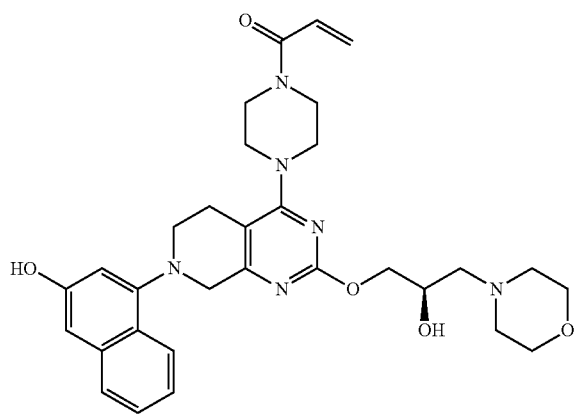 [SMILES: C=CC(=O)N1CCN(c2nc(OC[C@H](O)CN3CCOCC3)nc3c2CCN(c2cc(O)cc4ccccc24)C3)CC1]

Title compound was obtained by SFC chiral resolution of Example 123 using a Phenomenex OZ-H column (4.6 mm×250 mm, 5 u) and eluting with 40-60% MeOH:IPA:DEA (80:20:1) at 4 mL/min. Collecting the first eluting peak provided the desired compound where the stereochemistry was arbitrarily assigned. ES+APCI MS m/z 575.2 [M+H]$^+$.

Example 216

(S)-1-(4-(2-(2-hydroxy-3-morpholinopropoxy)-7-(3-hydroxynaphthalen-1-yl)-5,6,7,8-tetrahydropyrido[3,4-d]pyrimidin-4-yl)piperazin-1-yl)prop-2-en-1-one

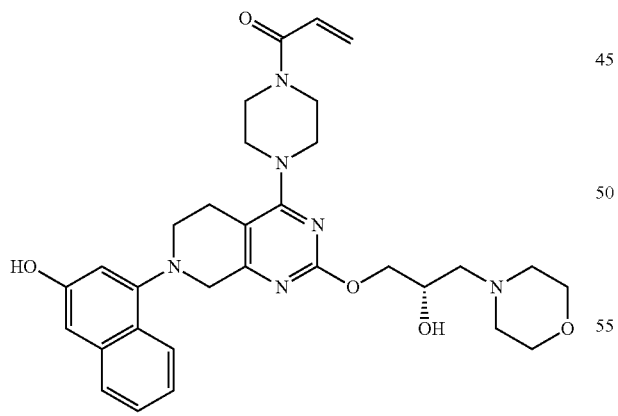

Title compound was obtained by SFC chiral resolution of Example 123 using a Phenomenex OZ-H column (4.6 mm×250 mm, 5 u) and eluting with 40-60% MeOH:IPA:DEA (80:20:1) at 4 mL/min. Collecting the second eluting peak provided the desired compound where the stereochemistry was arbitrarily assigned. ES+APCI MS m/z 575.2 [M+H]$^+$.

Example 217

1-(4-(2-((1-hydroxy-3-morpholinopropan-2-yl)oxy)-7-(3-hydroxynaphthalen-1-yl)-5,6,7,8-tetrahydropyrido[3,4-d]pyrimidin-4-yl)piperazin-1-yl)prop-2-en-1-one

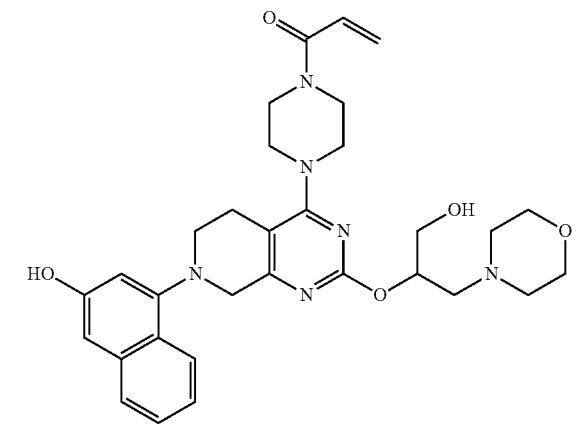 [SMILES: C=CC(=O)N1CCN(c2nc(OC(CO)CN3CCOCC3)nc3c2CCN(c2cc(O)cc4ccccc24)C3)CC1]

Synthesized according to the method of Example 8, using 3-morpholinopropane-1,2-diol in place of (S)-1-(dimethylamino)propan-2-ol in Step B. ES+APCI MS m/z 575.2 [M+H]$^+$.

Example 218

2-(1-acryloyl-4-(2-(((2S,4R)-4-hydroxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

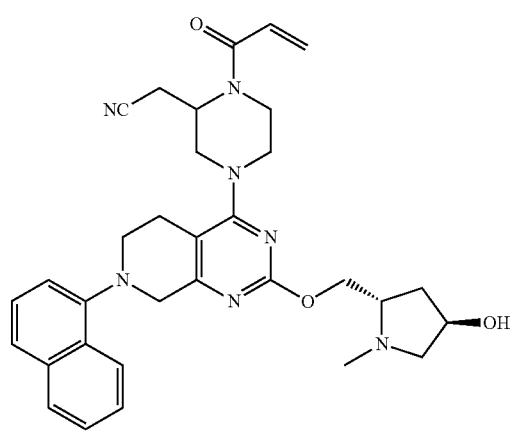 [SMILES: C=CC(=O)N1CCN(c2nc(OC[C@@H]3C[C@@H](O)CN3C)nc3c2CCN(c2cccc4ccccc24)C3)CC1CC#N]

Step A: benzyl 4-(2-(((2S,4R)-1-(tert-butoxycarbonyl)-4-((tert-butyldimethylsilyl)oxy)pyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate In a sealed vial, a solution of benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (150 mg, 0.27 mmol) in dioxane (2712 µL, 0.27 mmol) was sparged with argon and (2S,4R)-4-{[tert-Butyl(dimethyl)silyl]oxy}-2-(hydroxymethyl)pyrrolidine-1-carboxylate (270 mg, 0.81 mmol), Cs2CO3 (265 mg, 0.81 mmol), Rhuphos Pd G3 (22.7 mg, 0.027 mmol) were sequentially added under argon and sparged for an additional 5 min. The reaction mixture was capped and heated at 100° C. for 2 hr. Water was added and the mixture was extracted with DCM (3×15 mL). The extracts were combined and concentrated and the resulting residue was purified by silica gel (0-40% EtOAc in hexanes) to provide benzyl 4-(2-(((2S,4R)-1-(tert-butoxycarbonyl)-4-((tert-butyldimethylsilyl)oxy)pyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (113 mg, 0.13 mmol, 49% yield).

Step B: tert-butyl (2S,4R)-4-((tert-butyldimethylsilyl)oxy)-2-(((4-(3-(cyanomethyl)piperazin-1-yl)-7-(naphthalen-1-yl)-5,6,7,8-tetrahydropyrido[3,4-d]pyrimidin-2-yl)oxy)methyl)pyrrolidine-1-carboxylate To a solution of benzyl 4-(2-(((2S,4R)-1-(tert-butoxycarbonyl)-4-((tert-butyldimethyl silyl)oxy)pyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (113 mg, 0.133 mmol) in EtOH (1.3 mL, 0.133 mmol) and THF (1.3 mL, 0.133 mmol) was added palladium (70.9 mg, 0.033 mmol) (Degussa Type, 10 wt %, 50% H2O) and then an atmosphere of H2 was introduced via vacuum followed by balloon pressure. The mixture was then stirred at ambient temperature for 2 hours. The mixture was then diluted with 1:1 MeOH and THF and filtered through GF/F paper. The filtrate was then concentrated to provide crude product which was used as is.

Step C: tert-butyl (2S,4R)-2-(((4-(4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-4-((tert-butyldimethylsilyl)oxy)pyrrolidine-1-carboxylate tert-butyl (2S,4R)-4-((tert-butyldimethylsilyl)oxy)-2-(((4-(3-(cyanomethyl)piperazin-1-yl)-7-(naphthalen-1-yl)-5,6,7,8-tetrahydropyrido[3,4-d]pyrimidin-2-yl)oxy)methyl)pyrrolidine-1-carboxylate (95 mg, 0.13 mmol) and triethylamine (56 µL, 0.40 mmol) were placed in CH2Cl2 (1331 µL, 0.13 mmol) and cooled to 0° C. Acryloyl chloride (2661 µL, 0.27 mmol) (freshly prepared 0.1M solution in DCM) was added and the reaction was stirred for 30 min at 0° C. Water was added to the reaction and the mixture was extracted with DCM (3×15 mL). The extracts were combined and concentrated to provide crude material which was used as is.

Step D: 2-(1-acryloyl-4-(2-(((2S,4R)-4-((tert-butyldimethylsilyl)oxy)pyrrolidin-2-yl)methoxy)-7-(naphthalen-1-yl)-5,6,7,8-tetrahydropyrido[3,4-d]pyrimidin-4-yl)piperazin-2-yl)acetonitrile tert-butyl (2S,4R)-2-(((4-(4-acryloyl-3-(cyanomethyl)piperazin-1-yl)-7-(naphthalen-1-yl)-5,6,7,8-tetrahydropyrido[3,4-d]pyrimidin-2-yl)oxy)methyl)-4-((tert-butyldimethylsilyl)oxy)pyrrolidine-1-carboxylate (92 mg, 0.12 mmol) was placed in DCM (3 mL) and TFA (92 µL, 1.2 mmol) was added and the reaction was stirred at room temperature for 2 hours. Saturated bicarbonate was added to the reaction and the mixture was extracted with DCM (3×15 mL). The extracts were combined, dried with sodium sulfate, filtered and concentrated to give crude material that was used as is.

Step E: 2-(1-acryloyl-4-(2-(((2S,4R)-4-((tert-butyldimethylsilyl)oxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile 2-(1-acryloyl-4-(2-(((2S,4R)-4-((tert-butyldimethylsilyl)oxy)pyrrolidin-2-yl)methoxy)-7-(naphthalen-1-yl)-5,6,7,8-tetrahydropyrido[3,4-d]pyrimidin-4-yl)piperazin-2-yl)acetonitrile (80 mg, 0.12 mmol), formaldehyde (45.0 µL, 0.60 mmol) and Na(OAc)3BH (50.8 mg, 0.24 mmol) were placed in THF (2 mL) and stirred for 2 hrs. Saturated bicarbonate was added and the mixture was extracted with 10% MeOH in DCM (3×15 mL). The extracts were combined, dried with sodium sulfate, and concentrated to provide crude material which was used as is.

Step F: 2-(1-acryloyl-4-(2-(((2S,4R)-4-hydroxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile 2,2,2-trifluoroacetate 2-(1-acryloyl-4-(2-(((2S,4R)-4-((tert-butyldimethyl silyl)oxy)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (81 mg, 0.119 mmol) was placed in DCM (5 mL) and HCl (594 µL, 2.38 mmol) was added and the reaction was stirred for 1 hr. The reaction was concentrated and the material was purified by reverse phase chromatography (0-50% ACN:water with 0.1% TFA) to provide 2-(1-acryloyl-4-(2-(((2S,4R)-4-hydroxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (38.9 mg, 0.057 mmol, 48% yield). ES+APCI MS m/z 568.3 [M+H]+.

Example 219

1-(4-(2-((1,4-dimethylpiperazin-2-yl)methoxy)-7-(3-hydroxynaphthalen-1-yl)-5,6,7,8-tetrahydropyrido[3,4-d]pyrimidin-4-yl)piperazin-1-yl)prop-2-en-1-one

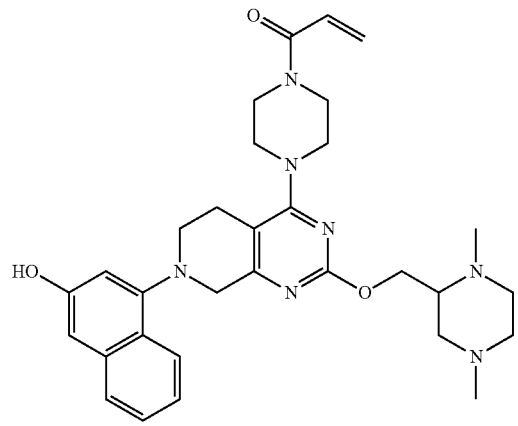

Title compound was prepared the same as Example 127, substituting (1,4-Dimethyl-2-piperazinyl)methanol in place of N-Methyl-L-prolinol in Step D. ES+APCI MS m/z 558.3 [M+H]+.

Example 220

2-(1-acryloyl-4-(2-(((2S,4R)-4-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

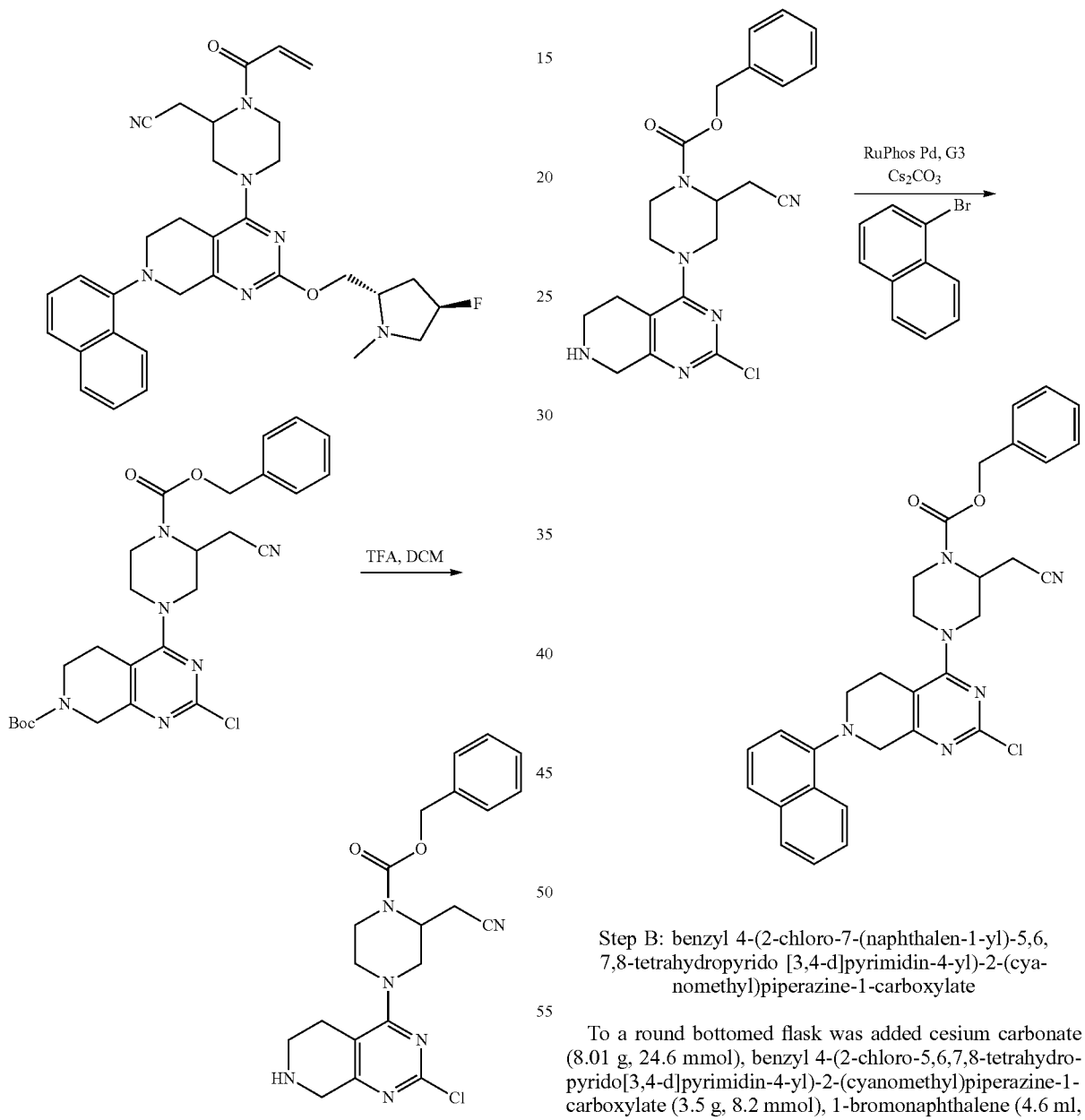

Step A: benzyl 4-(2-chloro-5,6,7,8-tetrahydropyrido[3,4-d]pyrimidin-4-yl)-2-(cyanomethyl)piperazine-1-carboxylate To a solution of tert-butyl 4-(4-((benzyloxy)carbonyl)-3-(cyanomethyl)piperazin-1-yl)-2-chloro-5,8-dihydropyrido[3,4-d]pyrimidine-7(6H)-carboxylate (4.00 g, 7.59 mmol) in DCM (25.3 ml, 7.59 mmol) was added trifluoroacetic acid (17.4 ml, 227.7 mmol) and the reaction was stirred at room temperature for 3 hours. The reaction was concentrated to a thick oil. Saturated bicarbonate was added slowly and the mixture was extracted with 10% MeOH in DCM (3×50 mL). The extracts were combined, dried with sodium sulfate and concentrated to provide the desired product (3.24 g, 7.6 mmol, 100% yield) which was used as is. ES+APCI MS m/z 506.2 [M]+.

Step B: benzyl 4-(2-chloro-7-(naphthalen-1-yl)-5,6,7,8-tetrahydropyrido [3,4-d]pyrimidin-4-yl)-2-(cyanomethyl)piperazine-1-carboxylate To a round bottomed flask was added cesium carbonate (8.01 g, 24.6 mmol), benzyl 4-(2-chloro-5,6,7,8-tetrahydropyrido[3,4-d]pyrimidin-4-yl)-2-(cyanomethyl)piperazine-1-carboxylate (3.5 g, 8.2 mmol), 1-bromonaphthalene (4.6 ml, 32.8 mmol) and RuPhos Pd G3 (1.0 g, 1.23 mmol). After evacuating the flask, 1,4-dioxane (82.0 ml, 8.20 mmol) was added through a septum under argon flow. Argon was bubbled through the mixture for 5 minutes and then the mixture was heated to 70° C. overnight. The reaction was cooled and water was added and extracted with ethyl acetate and the organics concentrated in vacuo. The yellow solids were dissolved in minimal DCM and purified by silica chromatography (25-60% EtOAc in hexanes) to provide benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (2.0 g, 3.6 mmol, 44.1% yield). ES+APCI MS m/z 553.2 [M]+.

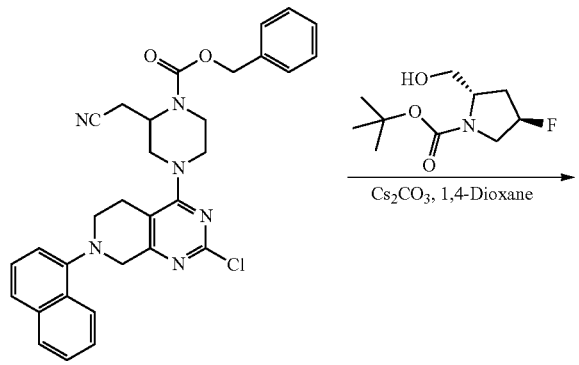
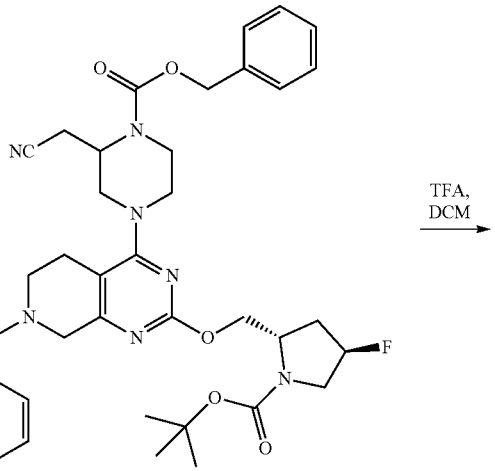
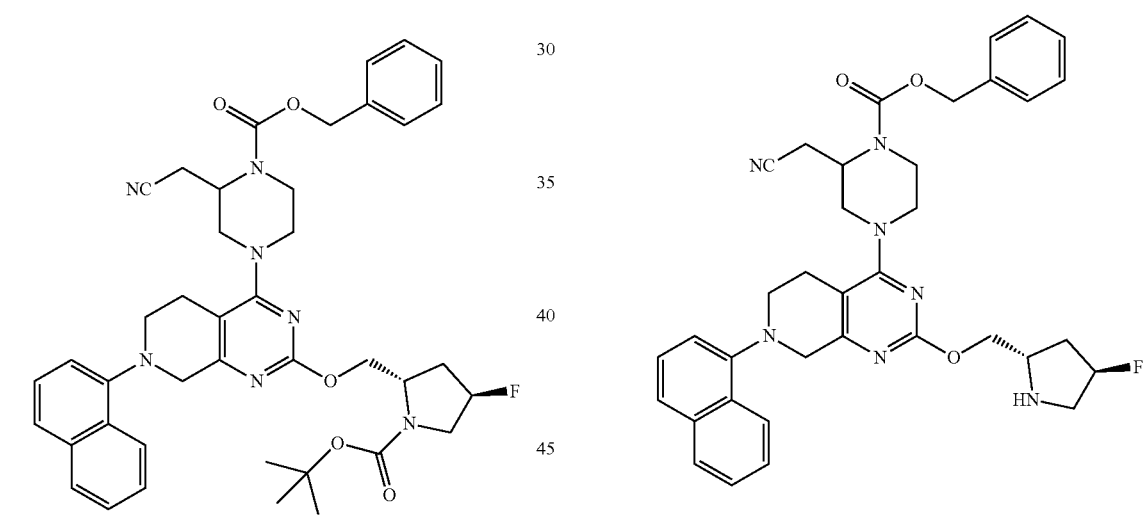

Step C: benzyl 4-(2-(((2S,4R)-1-(tert-butoxycarbonyl)-4-fluoropyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate In a vial benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (120 mg, 0.22 mmol) was dissolved in dioxane (108 µL, 0.217 mmol) and treated with cesium carbonate (141 mg, 0.434 mmol), and (2S,4R)-1-(tert-Butoxycarbonyl)-4-fluoro-2-hydroxymethylpyrrolidine (47.6 mg, 0.217 mmol). The tube was then capped and heated to 90° C. for 12 hours. The reaction was filtered through GF/F paper and concentrated. The residue was purified by silica chromatography (0-6% MeOH in DCM). ES+APCI MS m/z 736.3 [M+H]+.

Step D: benzyl 2-(cyanomethyl)-4-(2-(((2S,4R)-4-fluoropyrrolidin-2-yl)methoxy)-7-(naphthalen-1-yl)-5,6,7,8-tetrahydropyrido[3,4-d]pyrimidin-4-yl)piperazine-1-carboxylat To a solution of benzyl 4-(2-(((2S,4R)-1-(tert-butoxycarbonyl)-4-fluoropyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (125 mg, 0.170 mmol) in DCM (170 µL, 0.170 mmol) was added trifluoroacetic acid (195 µL, 2.55 mmol) and the reaction stirred at RT for 2 hr. The organics were washed with sodium bicarbonate and the aqueous layer was back extracted with DCM. The combined organic layers were concentrated and used without further purification. ES+APCI MS m/z 636.3 [M+H]+.

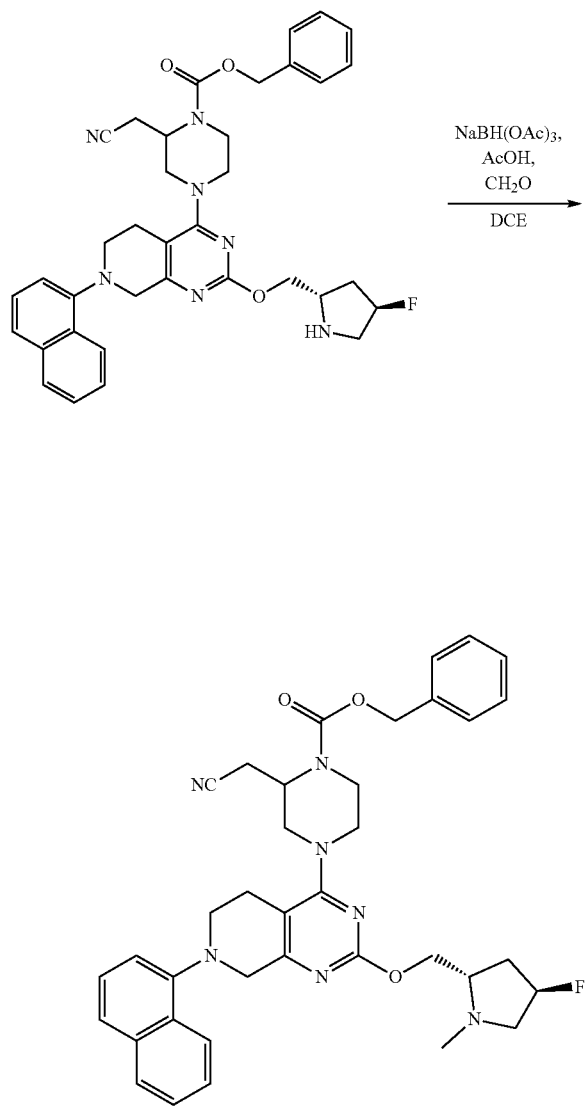

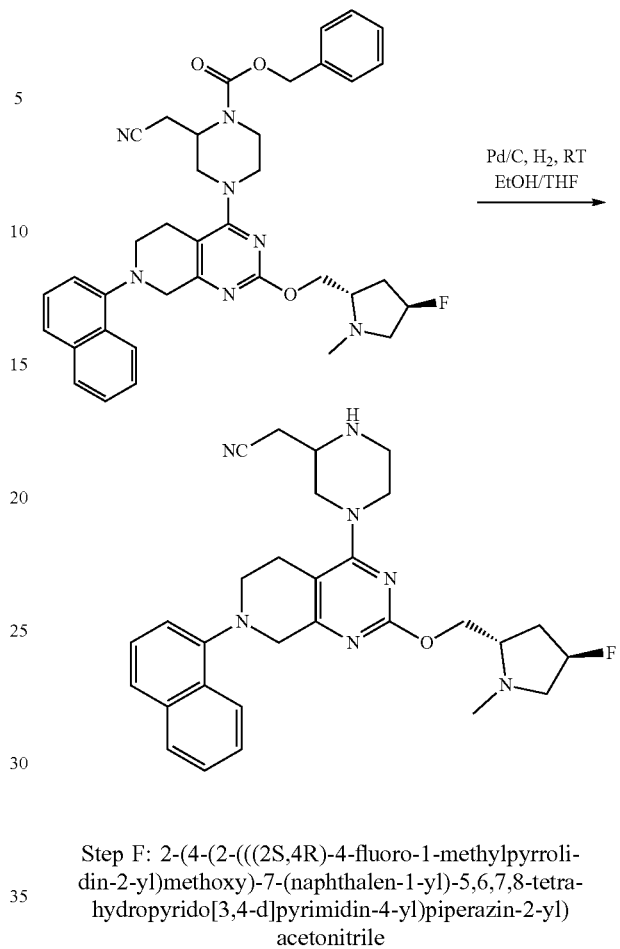

Step E: benzyl 2-(cyanomethyl)-4-(2-(((2S,4R)-4-fluoro-1-methylpyrrolidin-2-yl)methoxy)-7-(naphthalen-1-yl)-5,6,7,8-tetrahydropyrido[3,4-d]pyrimidin-4-yl)piperazine-1-carboxylate To a solution of benzyl 2-(cyanomethyl)-4-(2-(((2S,4R)-4-fluoropyrrolidin-2-yl)methoxy)-7-(naphthalen-1-yl)-5,6,7,8-tetrahydropyrido[3,4-d]pyrimidin-4-yl)piperazine-1-carboxylate (105 mg, 0.1652 mmol) in DCE (3303 µL, 0.1652 mmol) was added formaldehyde (124.1 µL, 1.652 mmol) (37% in water) followed by sodium triacetoxyborohydride (175.0 mg, 0.8258 mmol). The mixture was stirred vigorously at RT for 2.5 h. The mixture was treated with saturated sodium bicarbonate (30 mL), stirred for 10 min then extracted with DCM (3×10 mL). The combined organic phases were dried over sodium sulfate, filtered and concentrated and used as is in the next reaction. ES+APCI MS m/z 650.3 [M+H]⁺.

Step F: 2-(4-(2-(((2S,4R)-4-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile To a solution of benzyl 2-(cyanomethyl)-4-(2-(((2S,4R)-4-fluoro-1-methylpyrrolidin-2-yl)methoxy)-7-(naphthalen-1-yl)-5,6,7,8-tetrahydropyrido[3,4-d]pyrimidin-4-yl)piperazine-1-carboxylate (85 mg, 0.13 mmol) in EtOH (1308 µL, 0.13 mmol) and THF (1308 µL, 0.13 mmol) was added palladium (70 mg, 0.033 mmol) (Degussa Type, 10 wt %, 50% H₂O) and then an atmosphere of H₂ was introduced via vacuum followed by balloon pressure. The mixture was then stirred at ambient temperature overnight. The mixture was then diluted with MeOH and filtered through GF/F paper. The filtrate was then concentrated to provide 2-(4-(2-(((2S,4R)-4-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile. ES+APCI MS m/z 516.3 [M+H]⁺.

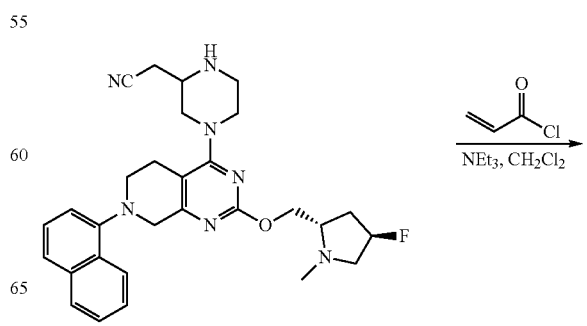

Step G: 2-(1-acryloyl-4-(2-(((2S,4R)-4-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

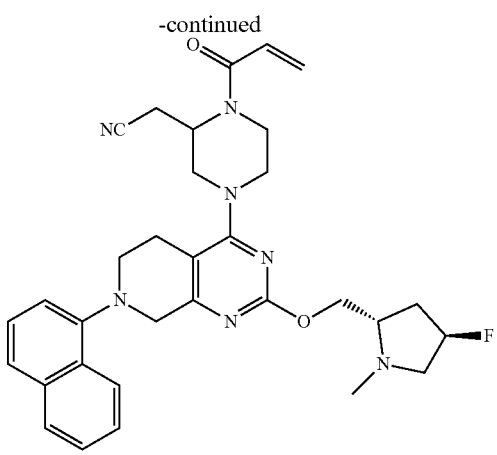

To a suspension of 2-(4-(2-(((2S,4R)-4-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (65 mg, 0.126 mmol) in DCM (1261 µL, 0.126 mmol) at 0° C. was added acryloyl chloride (2521 µL, 0.252 mmol) (freshly prepared 0.1M solution in DCM) followed by triethylamine (35.1 µL, 0.252 mmol). The reaction was then stirred at 0° C. for 45 minutes. The reaction was concentrated and purified by reverse phase chromatography (0-50% CAN:water with 0.1% TFA) to provide the title compound. ES+APCI MS m/z 570.3 [M+H]+.

Example 221

2-(1-acryloyl-4-(2-(((2S,4S)-4-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

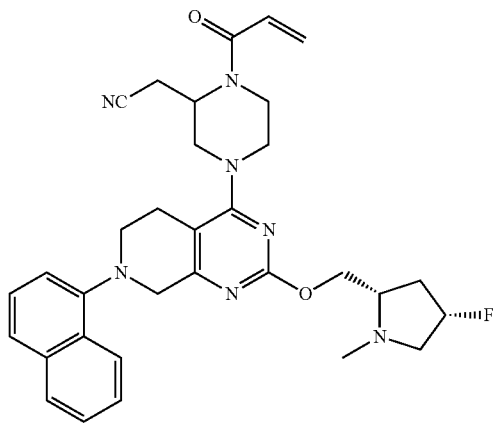 [SMILES: C=CC(=O)N1CCN(c2nc(OC[C@@H]3C[C@H](F)CN3C)nc3c2CCN(c2cccc4ccccc24)C3)CC1CC#N]

Synthesized according to the method of Example 220, Step C-G, using tert-butyl (2S,4S)-4-fluoro-2-(hydroxymethyl)pyrrolidine-1-carboxylate in place of tert-butyl (2S,4R)-4-fluoro-2-(hydroxymethyl)pyrrolidine-1-carboxylate in Step C. ES+APCI MS m/z 570.3 [M+H]+.

Example 222

2-(1-acryloyl-4-(2-(((2S,4S)-4-methoxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

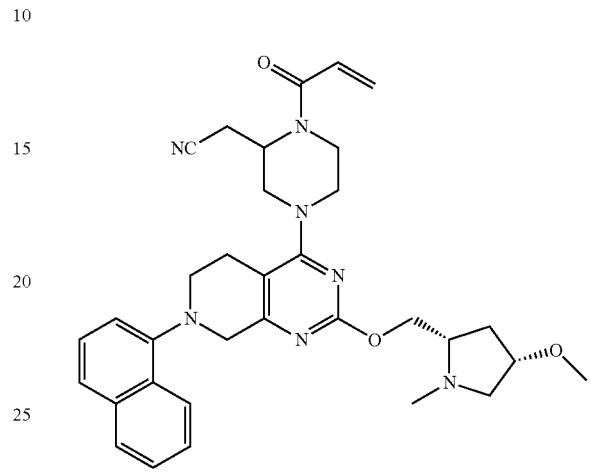

Title compound was prepared following Example 220 (Steps C-G), substituting tert-butyl (2S,4S)-2-(hydroxymethyl)-4-methoxypyrrolidine-1-carboxylate for (2S,4R)-1-(tert-Butoxycarbonyl)-4-fluoro-2-hydroxymethylpyrrolidine in Step C. ES+APCI MS m/z 582.3 [M+H]+.

Example 223

2-(1-acryloyl-4-(2-(((S)-4-methylpiperazin-2-yl)methoxy)-7-(naphthalen-1-yl)-5,6,7,8-tetrahydropyrido[3,4-d]pyrimidin-4-yl)piperazin-2-yl)acetonitrile

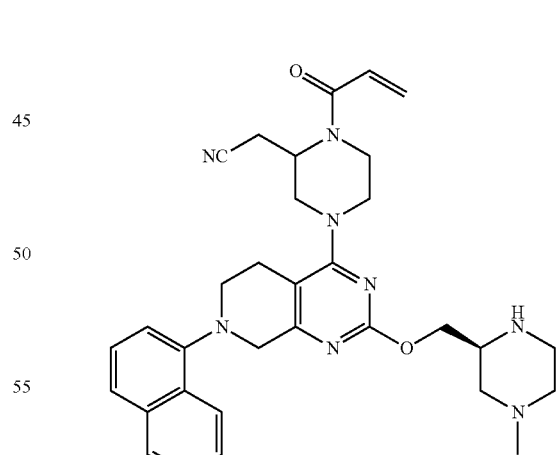

Steps A-F: 2-(1-acryloyl-4-(2-(((S)-4-methylpiperazin-2-yl)methoxy)-7-(naphthalen-1-yl)-5,6,7,8-tetrahydropyrido[3,4-d]pyrimidin-4-yl)piperazin-2-yl)acetonitrile Title compound was prepared following Example 220 (Steps C-G), substituting tert-butyl (S)-2-(hydroxymethyl)-

Example 224

2-(1-acryloyl-4-(2-(((R)-4-methylpiperazin-2-yl)methoxy)-7-(naphthalen-1-yl)-5,6,7,8-tetrahydropyrido[3,4-d]pyrimidin-4-yl)piperazin-2-yl)acetonitrile

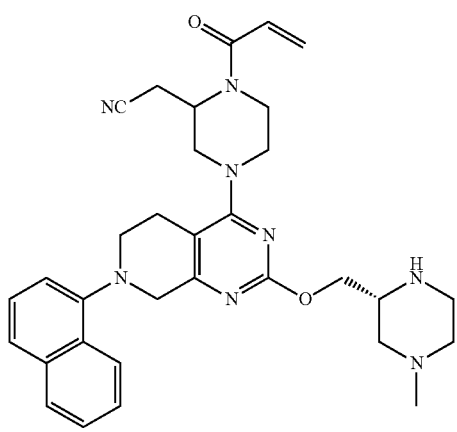 [SMILES: C=CC(=O)N1CCN(c2nc(OC[C@H]3CN(C)CCN3)nc3c2CCN(c2cccc4ccccc24)C3)CC1CC#N]

Title compound was prepared following Example 220 (Steps C-G), substituting tert-butyl (R)-2-(hydroxymethyl)-4-methylpiperazine-1-carboxylate for tert-butyl (S)-2-(hydroxymethyl)-4-methylpiperazine-1-carboxylate in Step C. ES+APCI MS m/z 567.3 [M+H]$^+$.

Example 225

2-(1-acryloyl-4-(7-(5-fluoro-2-(trifluoromethoxy)phenyl)-2-((S)-1-methylpyrrolidin-2-yl)methoxy)-5,6,7,8-tetrahydropyrido [3,4-d]pyrimidin-4-yl)piperazin-2-yl)acetonitrile

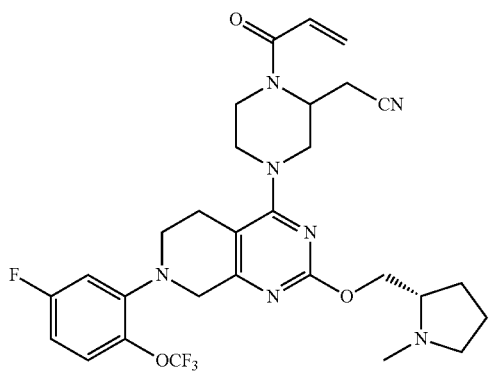 [SMILES: C=CC(=O)N1CCN(c2nc(OC[C@@H]3CCCN3C)nc3c2CCN(c2cc(F)ccc2OC(F)(F)F)C3)CC1CC#N]

Title compound was prepared as in Example 210 Steps E-G, substituting 2-bromo-4-fluoro-1-(trifluoromethoxy)benzene for 1-bromo-2-(trifluoromethyl)benzene in step E. ES+APCI MS m/z 604.3 [M+H]$^+$.

Example 226

2-(1-acryloyl-4-(2-(((S)-1-methylpyrrolidin-2-yl)methoxy)-7-(2-(trifluoromethyl)pyridin-3-yl)-5,6,7,8-tetrahydropyrido[3,4-d]pyrimidin-4-yl)piperazin-2-yl)acetonitrile

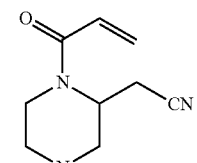

Title compound was prepared as in Example 210 Steps E-G, substituting 3-bromo-2-(trifluoromethyl)pyridine for 1-bromo-2-(trifluoromethyl)benzene in Step E. ES+APCI MS m/z 571.3 [M+H]$^+$.

Example 227

2-(1-acryloyl-4-(7-(2-fluorophenyl)-2-(((S)-1-methylpyrrolidin-2-yl)methoxy)-5,6,7,8-tetrahydropyrido[3,4-d]pyrimidin-4-yl)piperazin-2-yl)acetonitrile

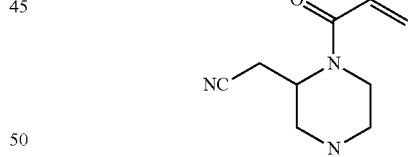
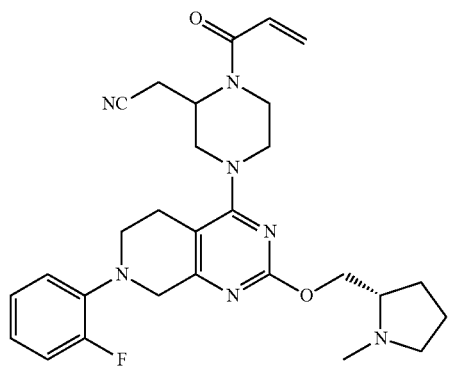 [SMILES: C=CC(=O)N1CCN(c2nc(OC[C@@H]3CCCN3C)nc3c2CCN(c2ccccc2F)C3)CC1CC#N]

Title compound was prepared as in Example 210 Steps E-G, substituting 1-bromo-2-fluorobenzene for 1-bromo-2-(trifluoromethyl)benzene in step E. ES+APCI MS m/z 520.3 [M+H]$^+$.

Example 228

2-(1-acryloyl-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile

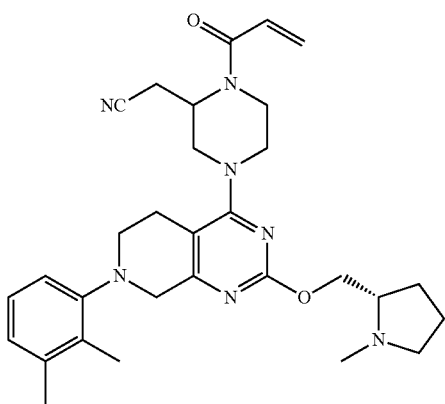 [SMILES: C=CC(=O)N1CCN(c2nc(OC[C@@H]3CCCN3C)nc3c2CCN(c2cccc(C)c2C)C3)CC1CC#N]

Title compound was prepared as in Example 210 Steps E-G, substituting 1-bromo-2,3-dimethylbenzene for 1-bromo-2-(trifluoromethyl)benzene in Step E. ES+APCI MS m/z 530.3 [M+H]+.

Example 229

2-(1-acryloyl-4-(7-(2-chlorophenyl)-2-((S)-1-methylpyrrolidin-2-yl)methoxy)-5,6,7,8-tetrahydropyrido[3,4-d]pyrimidin-4-yl)piperazin-2-yl)acetonitrile

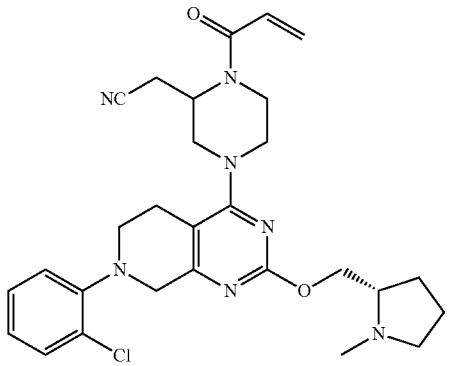 [SMILES: C=CC(=O)N1CCN(c2nc(OC[C@@H]3CCCN3C)nc3c2CCN(c2ccccc2Cl)C3)CC1CC#N]

Title compound was prepared as in Example 210 Steps E-G, substituting 1-bromo-2-chlorobenzene for 1-bromo-2-(trifluoromethyl)benzene in step E. ES+APCI MS m/z 536.2 [M]+.

Example 230

2-(1-acryloyl-4-(7-(3-fluoro-2-(trifluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile

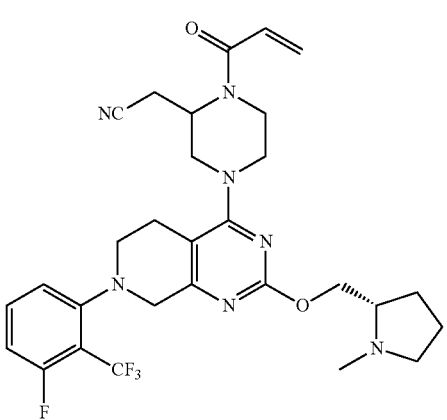 [SMILES: C=CC(=O)N1CCN(c2nc(OC[C@@H]3CCCN3C)nc3c2CCN(c2cccc(F)c2C(F)(F)F)C3)CC1CC#N]

Title compound was prepared as in Example 210 Steps E-G, substituting 1-bromo-3-fluoro-2-(trifluoromethyl)benzene for 1-bromo-2-(trifluoromethyl)benzene in Step E. ES+APCI MS m/z 588.3 [M+H]+.

Example 231

2-(1-acryloyl-4-(2-(3-hydroxypropoxy)-7-(naphthalen-1-yl)-5,6,7,8-tetrahydropyrido[3,4-d]pyrimidin-4-yl)piperazin-2-yl)acetonitrile

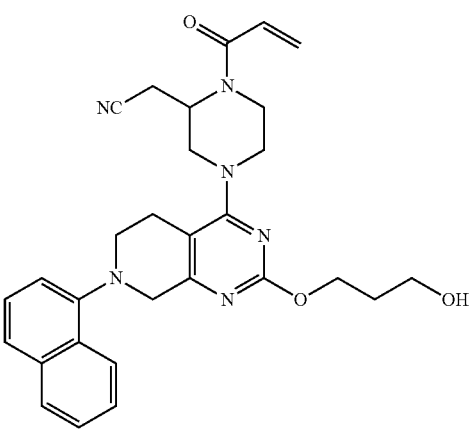

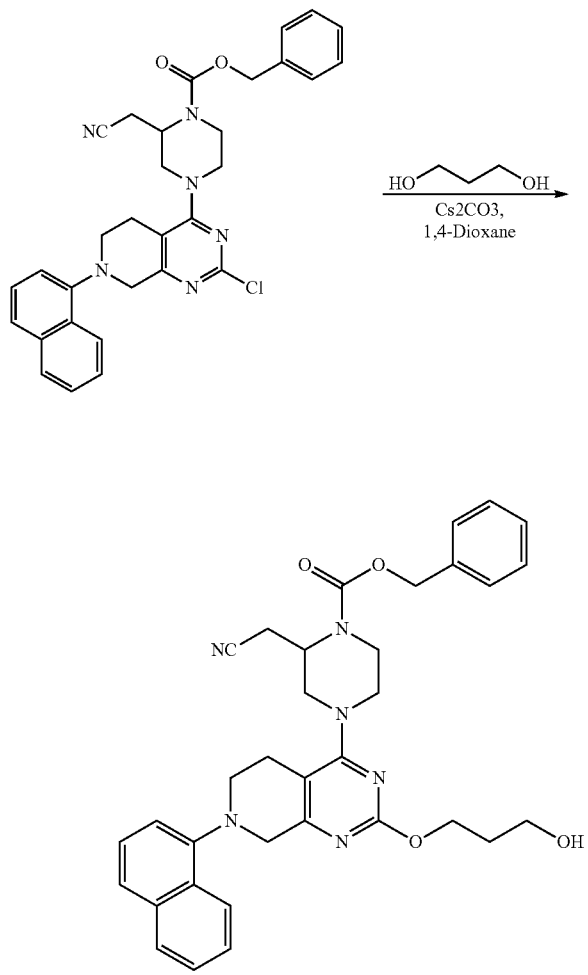

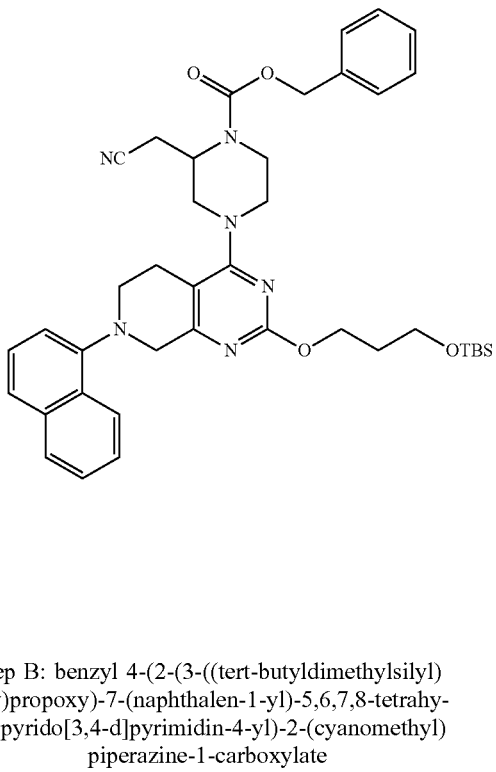

Step B: benzyl 4-(2-(3-((tert-butyldimethylsilyl)oxy)propoxy)-7-(naphthalen-1-yl)-5,6,7,8-tetrahydropyrido[3,4-d]pyrimidin-4-yl)-2-(cyanomethyl)piperazine-1-carboxylate To a vial was added benzyl 2-(cyanomethyl)-4-(2-(3-hydroxypropoxy)-7-(naphthalen-1-yl)-5,6,7,8-tetrahydropyrido[3,4-d]pyrimidin-4-yl)piperazine-1-carboxylate (77.6 mg, 0.131 mmol), which was dissolved in DCM (655 µL, 0.131 mmol). The mixture was cooled to 0° C. and then triethylamine (36.5 µL, 0.262 mmol) was added followed by 4-(dimethylamino)-pyridine (4.80 mg, 0.04 mmol). Then tert-butyldimethylsilyl chloride (29.6 mg, 0.196 mmol) was added and the mixture was stirred overnight while warming to room temperature. The reaction mixture was poured onto a saturated brine solution (5 ml) and the mixture extracted twice with EtOAc (10 mL). The organic phases were dried over sodium sulfate, filtered and concentrated. The crude reaction product was used as is. ES+APCI MS m/z 707.4 [M+H]+.

Step A: benzyl 2-(cyanomethyl)-4-(2-(3-hydroxypropoxy)-7-(naphthalen-1-yl)-5,6,7,8-tetrahydropyrido[3,4-d]pyrimidin-4-yl)piperazine-1-carboxylate Title compound was prepared as in Example 220 Step C, substituting propane-1,3-diol for (2S,4R)-1-(tert-Butoxycarbonyl)-4-fluoro-2-hydroxymethylpyrrolidine. ES+APCI MS m/z 593.3 [M+H]+.

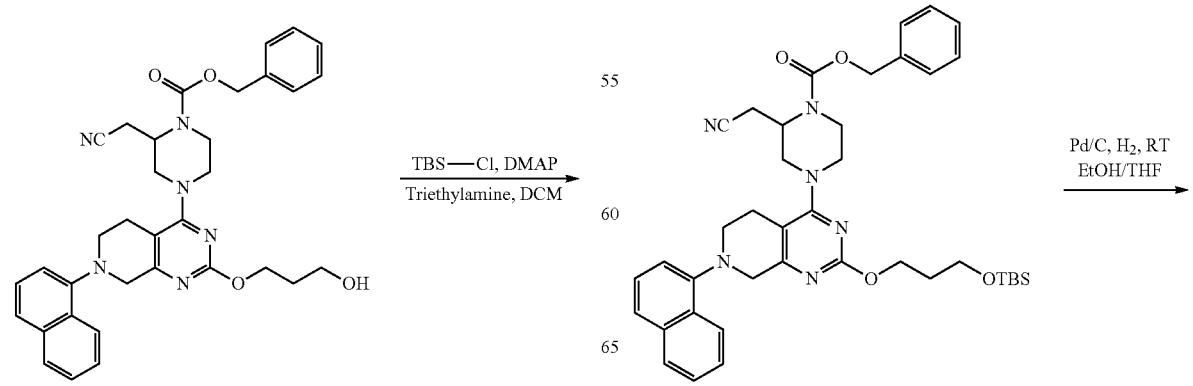

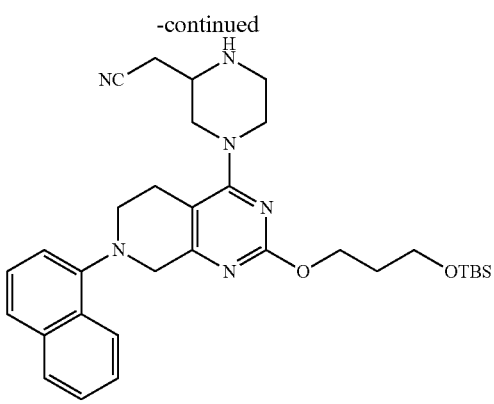

Step C: 2-(4-(2-(3-((tert-butyldimethylsilyl)oxy)propoxy)-7-(naphthalen-1-yl)-5,6,7,8-tetrahydropyrido[3,4-d]pyrimidin-4-yl)piperazin-2-yl)acetonitrile To a solution of benzyl 4-(2-(3-((tert-butyldimethylsilyl)oxy)propoxy)-7-(naphthalen-1-yl)-5,6,7,8-tetrahydropyrido[3,4-d]pyrimidin-4-yl)-2-(cyanomethyl)piperazine-1-carboxylate (106 mg, 0.150 mmol) in EtOH (1499 µL, 0.150 mmol) and THF (1499 µL, 0.150 mmol) was added palladium (79.8 mg, 0.0375 mmol) (Degussa Type, 10 wt %, 50% H₂O) and then an atmosphere of H₂ was introduced via vacuum followed by balloon pressure. The mixture was then stirred at ambient temperature overnight. The mixture was then diluted with MeOH and filtered through GF/F paper. The filtrate was then concentrated to a colorless solid that was used without further purification. ES+APCI MS m/z 573.3 [M+H]+.

Step D: 2-(1-acryloyl-4-(2-(3-((tert-butyldimethylsilyl)oxy)propoxy)-7-(naphthalen-1-yl)-5,6,7,8-tetrahydropyrido[3,4-d]pyrimidin-4-yl)piperazin-2-yl)acetonitrile To a suspension of 2-(4-(2-(3-((tert-butyldimethyl silyl)oxy)propoxy)-7-(naphthalen-1-yl)-5,6,7,8-tetrahydropyrido[3,4-d]pyrimidin-4-yl)piperazin-2-yl)acetonitrile (75 mg, 0.131 mmol) in DCM (1309 µL, 0.131 mmol) at −78° C. was added acryloyl chloride (2619 µL, 0.262 mmol) (freshly prepared 0.1M solution in DCM) followed by triethylamine (36.5 µL, 0.262 mmol). The reaction was then stirred at 0° C. for 30 minutes. The reaction was concentrated and used crude in the next reaction. ES+APCI MS m/z 627.4 [M+H]+.

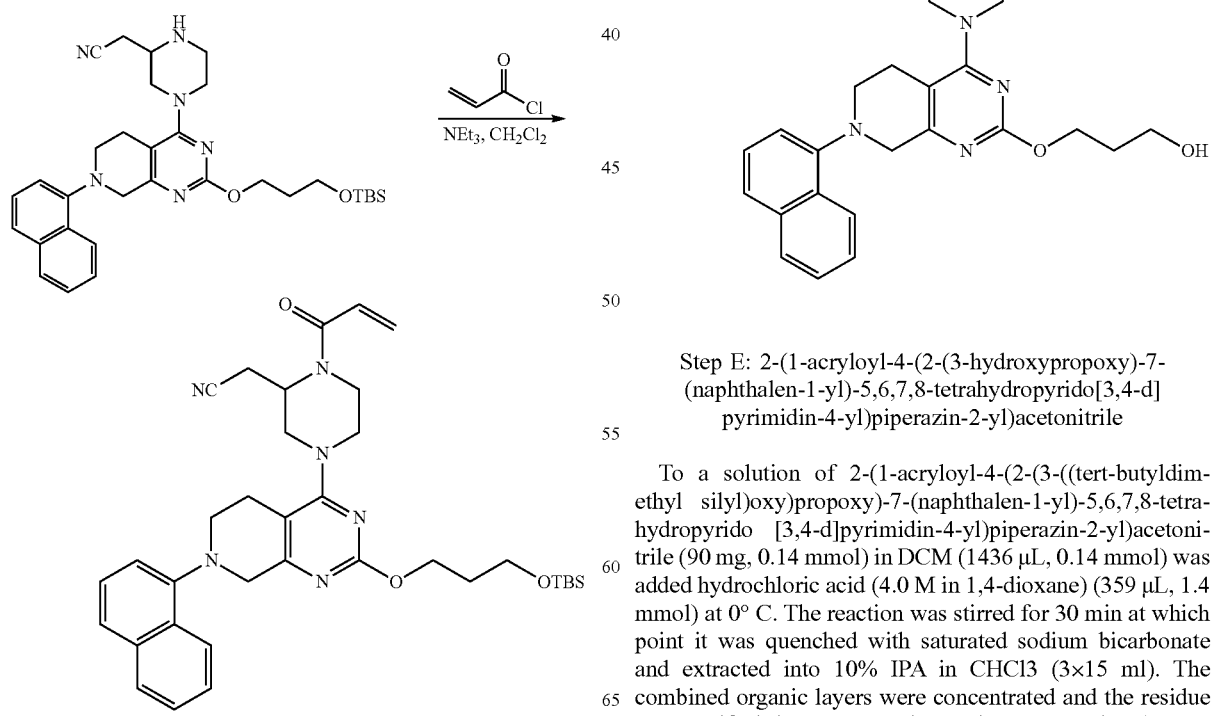

Step E: 2-(1-acryloyl-4-(2-(3-hydroxypropoxy)-7-(naphthalen-1-yl)-5,6,7,8-tetrahydropyrido[3,4-d]pyrimidin-4-yl)piperazin-2-yl)acetonitrile To a solution of 2-(1-acryloyl-4-(2-(3-((tert-butyldimethyl silyl)oxy)propoxy)-7-(naphthalen-1-yl)-5,6,7,8-tetrahydropyrido [3,4-d]pyrimidin-4-yl)piperazin-2-yl)acetonitrile (90 mg, 0.14 mmol) in DCM (1436 µL, 0.14 mmol) was added hydrochloric acid (4.0 M in 1,4-dioxane) (359 µL, 1.4 mmol) at 0° C. The reaction was stirred for 30 min at which point it was quenched with saturated sodium bicarbonate and extracted into 10% IPA in CHCl3 (3×15 ml). The combined organic layers were concentrated and the residue was purified by reverse phase chromatography (0-95% ACN:H2O with 0.1TFA). ES+APCI MS m/z 513.2 [M+H]+.

Example 232

1-(4-(7-(3-chloro-2-fluoro-5-hydroxyphenyl)-2-(3-morpholinopropoxy)-5,6,7,8-tetrahydropyrido[3,4-d]pyrimidin-4-yl)piperazin-1-yl)prop-2-en-1-one

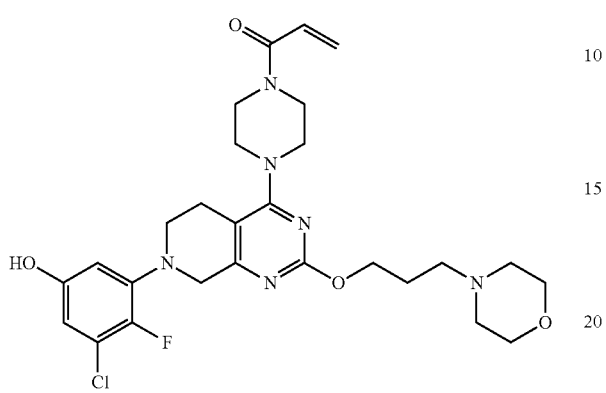

The title compound was prepared according to Example 1 Step C-F substituting Intermediate 25 for benzyl 4-(5,6,7,8-tetrahydropyrido[3,4-d]pyrimidin-4-yl)piperazine-1-carboxylate and 1-bromo-3-chloro-2-fluoro-5-(methoxymethoxy)benzene for 1-bromo-3-(methoxymethoxy)naphthalene in Step C. ES+APCI MS m/z 561.2 [M]+.

Example 233

2-(1-acryloyl-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile

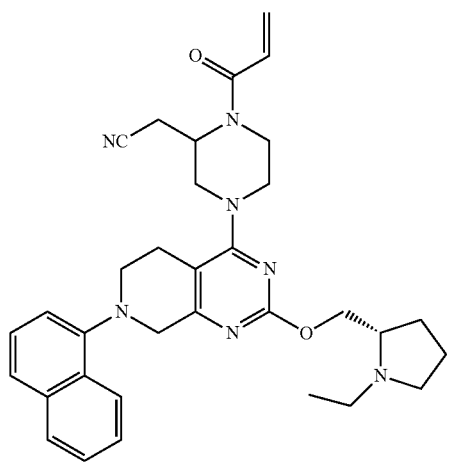 [SMILES: C=CC(=O)N1CCN(c2nc(OC[C@@H]3CCCN3CC)nc3c2CCN(c2cccc4ccccc24)C3)CC1CC#N]

2-(1-acryloyl-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile This compound was prepared following Example 147 substituting (S)-(1-ethylpyrrolidin-2-yl)methanol for N-Methyl-L-prolinol for [(2S)-1-methylpyrrolidin-2-yl]methanol in Step F. ES+APCI MS m/z 566.3 [M+H]+.

Example 234

2-((S)-1-acryloyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

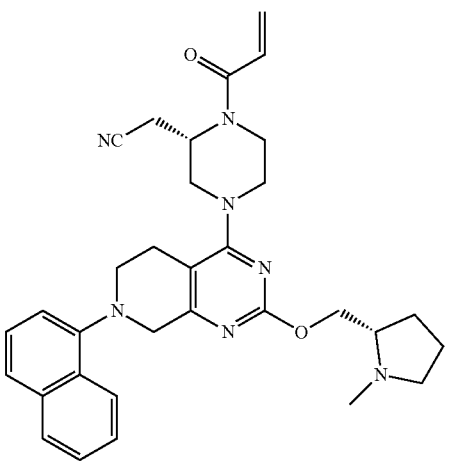

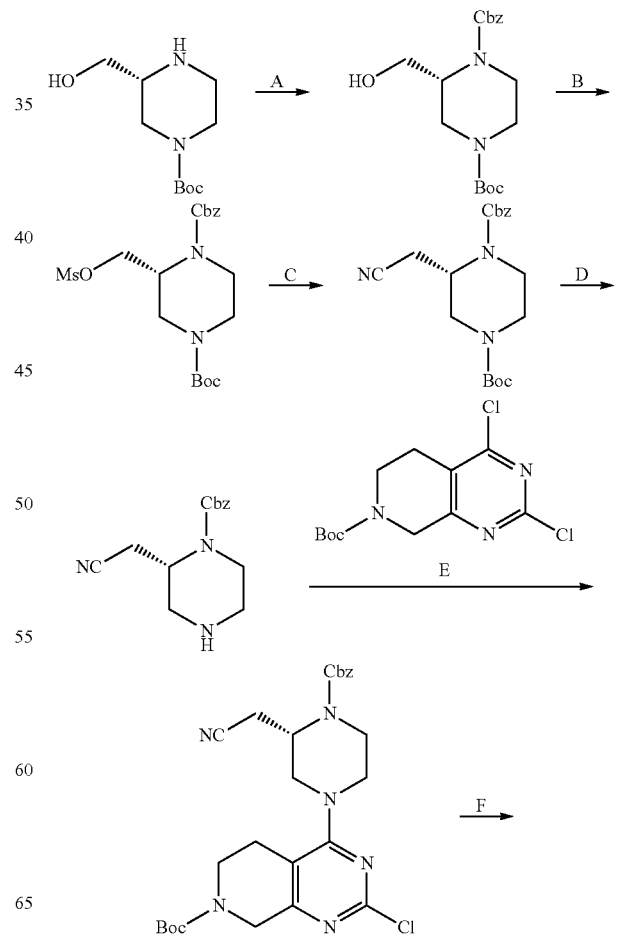

655

-continued

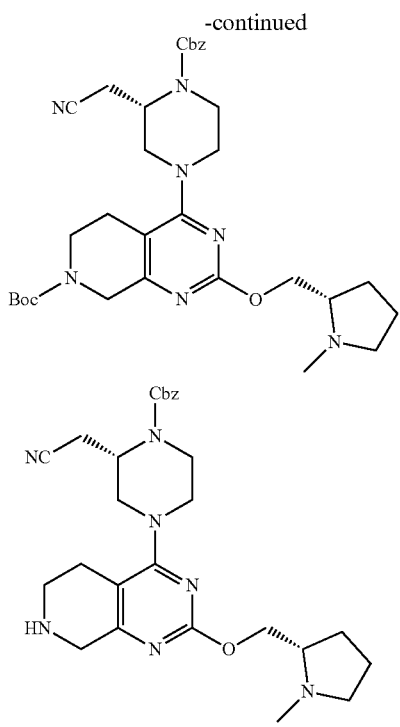

656

-continued

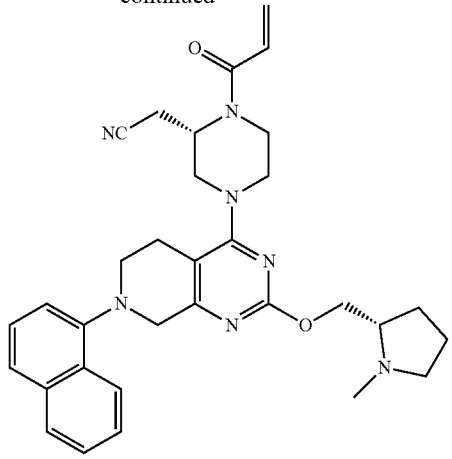

Step A: 1-Benzyl 4-(tert-butyl) (R)-2-(hydroxymethyl)piperazine-1,4-dicarboxylate To a stirred biphasic solution of (R)-1-Boc-3-hydroxymethylpiperazine (5.00 g, 23.1 mmol) and NaHCO₃ (5.83 g, 69.4 mmol) in ethyl acetate (46.2 ml) and water (46.2 ml) at 0° C. was added benzyl chloroformate (4.95 ml, 34.7 mmol) dropwise. The reaction mixture was stirred at ambient temperature overnight. The reaction mixture was diluted with EtOAc (50.0 ml) and the organic layer was separated, dried (Na₂SO₄) and concentrated. The crude product was purified by flash chromatography eluting with 10-50% EtOAc/hexanes gradient to afford the title compound (7.62 g, 21.7 mmol, 94.1%). ESI MS m/z 251.1 [M-Boc+H]+.

Step B. 1-Benzyl 4-(tert-butyl) (R)-2-(((methyl sulfonyl)oxy)methyl)piperazine-1,4-dicarboxylate To a solution of 1-benzyl 4-(tert-butyl) (R)-2-(hydroxymethyl)piperazine-1,4-dicarboxylate (1.69 g, 4.83 mmol) and triethylamine (1.01 ml, 7.25 mmol) in CH₂Cl₂ (32.2 ml) at 0° C. was added dropwise MsCl (0.561 ml, 7.25 mmol) neat and the resulting mixture was stirred at RT for 10 min. The reaction mixture was poured into a separatory funnel, diluted with ethyl acetate, then washed sequentially with 1N HCl, water, NaHCO₃ (sat.), and brine to afford the title compound (1.9 g, ~100%, used as crude material in next step). ESI MS m/z 329.1 [M-Boc+H]+.

Step C. 1-Benzyl 4-(tert-butyl) (S)-2-(cyanomethyl)piperazine-1,4-dicarboxylate

A solution of 1-benzyl 4-(tert-butyl) (R)-2-(((methylsulfonyl)oxy)methyl)piperazine-1,4-dicarboxylate (2.10 g, 4.90 mmol), sodium cyanide (0.480 g, 9.80 mmol) in DMA (49.0 ml) was heated at 55° C. for 1 day. The reaction was followed by HPLC (15 min method). The mixture was partitioned between EtOAc/brine, and the organic layer was washed with brine (3×), dried over MgSO₄ and concentrated. The residue was purified by flash chromatography eluting with 0-100% EtOAc/hexanes gradient to afford the title compound (1.40 g, 3.90 mmol, 79.5%). Aqueous layers were basified and disposed of in cyanide waste stream. ESI MS m/z 260.1 [M-Boc+H]+.

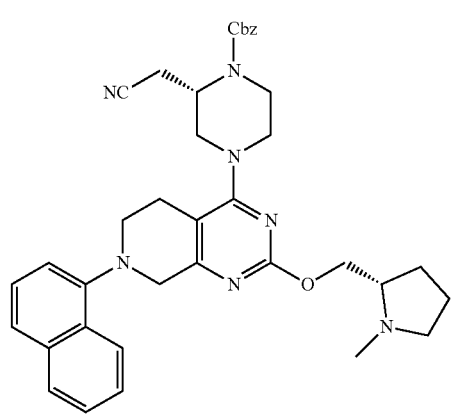

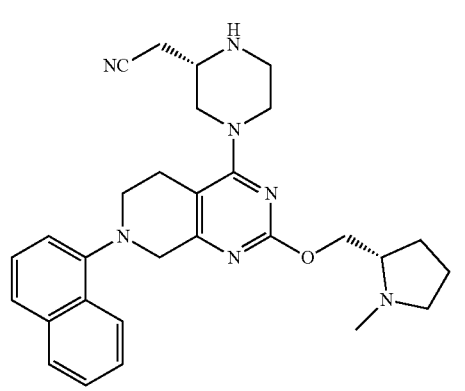

Step D. Benzyl (S)-2-(cyanomethyl)piperazine-1-carboxylate hydrochloride

1-Benzyl 4-(tert-butyl) (S)-2-(cyanomethyl)piperazine-1,4-dicarboxylate (5.32 g, 14.8 mmol) was placed in CH$_2$Cl$_2$ (25 mL) and HCl (4.0 N in dioxane, 18.5 ml, 74.0 mmol) was added and the reaction was stirred at ambient temperature for 1 d. The reaction mixture was concentrated to afford the title compound (4.3 g, 99%). ESI MS m/z 260.1 [M+H]+.

Step E. tert-Butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate A solution of benzyl (S)-2-(cyanomethyl)piperazine-1-carboxylate (1.01 g, 3.89 mmol), tert-butyl 2,4-dichloro-5,6-dihydropyrido[3,4-d]pyrimidine-7(8H)-carboxylate (1.18 g, 3.89 mmol) and DIEA (1.36 ml, 7.79 mmol) in DMSO (19.5 ml) was heated at 50° C. for 1 day. The reaction mixture was partitioned between ethyl acetate and brine and the organics separated. The organic phase was washed with brine (3×), dried over MgSO$_4$ and concentrated to afford the title compound (1.63 g, 3.09 mmol, 79.4%). ESI MS m/z 527.2 [M+H]+.

Step F. tert-butyl 4-((S)-4-((benzyloxy)carbonyl)-3-(cyanomethyl)piperazin-1-yl)-2-((S)-1-methylpyrrolidin-2-yl)methoxy)-5,8-dihydropyrido[3,4-d]pyrimidine-7(6H)-carboxylate In 250 mL heavy-wall round bottom flask with a PTFE screw cap was added a solution of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (1.64 g, 3.11 mmol) in dioxane (31.1 ml) and the mixture was sparged with argon. To the mixture was added sequentially (S)-(1-methylpyrrolidin-2-yl)methanol (1.08 g, 9.34 mmol), Cs$_2$CO$_3$ (3.04 g, 9.34 mmol) and Ruphos-Pd Gen3 catalyst (0.260 g, 0.311 mmol) under argon and sparged for an additional 5 min. The reaction mixture was capped and heated at 100° C. for 1 day. The reaction mixture was diluted with ethyl acetate and the organics washed with brine (2×). The organic layer was dried over MgSO$_4$ and concentrated to give a residue that was purified by flash chromatography eluting with 0-20% (MeOH+2% NH$_4$OH) in DCM to afford the title compound (1.42 g, 2.34 mmol, 75.3%). ESI MS m/z 606.3 [M+H]+.

Step G. Benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate bis-trifluoroacetate salt A solution of tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (38 mg, 0.063 mmol) in CH$_2$Cl$_2$ (627 µl) and TFA (242 µl, 3.1 mmol) was stirred at room temperature for 1 day. The reaction mixture was concentrated and used as bis-TFA salt in the next reaction (46 mg, 0.063 mmol, 100%). ESI MS m/z 506.3 [M+H]+.

Step H. Benzyl (S)-2-(cyanomethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate A suspension of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate bistrifluoroacetate salt (46 mg, 0.063 mmol), 1-bromonaphthalene (39.3 mg, 0.190 mmol) and Cs$_2$CO$_3$ (61.9 mg, 0.190 mmol) in dioxane (633 µl) was sparged with argon for 5 min. To this mixture was added Ruphos Pd Gen 3 (5.29 mg, 0.006 mmol) and the resulting suspension was sparged for an additional 1 minute with argon. The vial was capped and heated at 100° C. for 2 h. The reaction mixture was partitioned between EtOAc and water and the aqueous layer was extracted with EtOAc (3×). The combined organic layers were dried over MgSO$_4$ and concentrated. The residue was purified by flash chromatography eluting with 5% MeOH/1% NH$_4$OH/CH$_2$Cl$_2$ isocratic to afford the title compound (31.9 mg, 0.050 mmol, 79.8%). ESI MS m/z 632.3 [M+H]+.

Step I. 2-((S)-4-(2-(((S)-1-Methylpyrrolidin-2-yl)methoxy)-7-(naphthalen-1-yl)-5,6,7,8-tetrahydropyrido[3,4-d]pyrimidin-4-yl)piperazin-2-yl)acetonitrile To a solution of benzyl (S)-2-(cyanomethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (31 mg, 0.049 mmol) in methanol (981 µl) and THF (981 µl) sparged with nitrogen was added Pd/C (10.4 mg, 0.00491 mmol) and the mixture was stirred under balloon pressure atmosphere of H$_2$ for 1 day. The reaction mixture was filtered through a PTFE syringe filter (25 mm) and the filtrate was concentrated to afford the title compound (23.4 mg, 0.047 mmol, 95.8%). ESI MS m/z 498.3 [M+H]+.

Step J. 2-((S)-1-Acryloyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile To a solution of 2-((S)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (23.4 mg, 0.047 mmol) in CH$_2$Cl$_2$ (470 µl) was added DIEA (41.1 µl, 0.235 mmol) then acryloyl chloride (12 µl, 0.141 mmol). The resulting mixture was stirred at ambient temperature for 15 minutes. The reaction mixture was partitioned between EtOAc and 2N K$_2$CO$_3$ and brine. The aqueous layer was extracted with EtOAc (2×). The combined organic layers were dried over MgSO$_4$ and concentrated. The residue was purified by flash chromatography eluting with 5% MeOH/1% NH$_4$OH in CH$_2$Cl$_2$ to afford the title compound (19.2 mg, 0.035 mmol, 74.0%). ESI MS m/z 552.3 [M+H]+.

Example 235

2-((S)-1-((E)-4-(dimethylamino)but-2-enoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

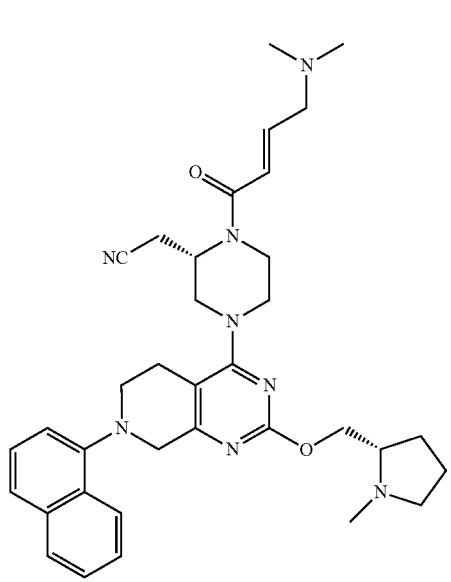 [SMILES: CN(C)C/C=C/C(=O)N1CCN(c2nc(OC[C@@H]3CCCN3C)nc3c2CCN(c2cccc4ccccc24)C3)C[C@@H]1CC#N]

Step A. 2-((S)-1-((E)-4-(dimethylamino)but-2-enoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile To a solution of 2-((S)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (25 mg, 0.0502 mmol) from Example 234 Step I, (2E)-4-(dimethylamino)but-2-enoic acid (13.0 mg, 0.100 mmol), DIEA (43.9 µl, 0.251 mmol) in $CH_2Cl_2$ (502 µl) was added HATU (28.7 mg, 0.0754 mmol) and the resulting mixture was stirred at ambient temperature for 1 hour. The reaction mixture was partitioned between EtOAc and brine. The aqueous layer was extracted with EtOAc (2×). The combined organic layers were dried over $MgSO_4$ and concentrated. The residue was purified by preparative-C18 eluting with 5-95% ACN/$H_2O$+0.1% TFA. The desired fractions were partitioned between EA/2M $K_2CO_3$. The aqueous was extracted with EtOAc (2×). The combined organic layers were dried over $MgSO_4$ and concentrated to afford the title compound (19.0 mg, 0.031 mmol, 62.1%). ESI MS m/z 609.4 [M+H]+.

Example 236

2-((S)-4-(2-(((S)-1-methylpyrrolidin-2-yl)methoxy)-7-(naphthalen-1-yl)-5,6,7,8-tetrahydropyrido[3,4-d]pyrimidin-4-yl)-1-(E-4-(piperidin-1-yl)but-2-enoyl)piperazin-2-yl)acetonitrile

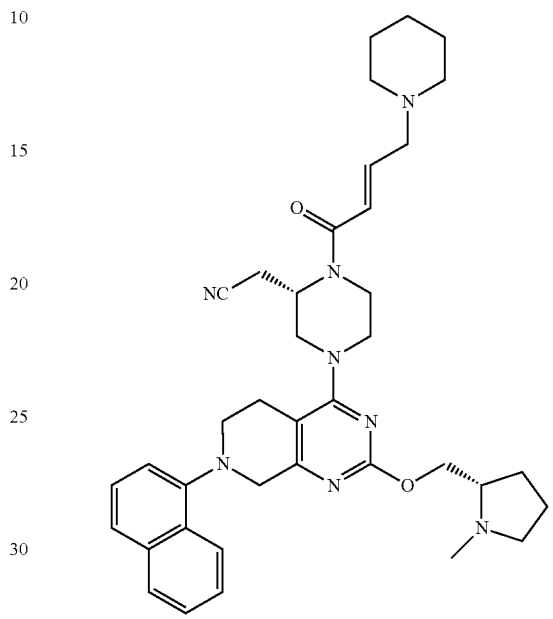

Step A. 2-((S)-4-(2-(((S)-1-methylpyrrolidin-2-yl)methoxy)-7-(naphthalen-1-yl)-5,6,7,8-tetrahydropyrido[3,4-d]pyrimidin-4-yl)-1-(E-4-(piperidin-1-yl)but-2-enoyl)piperazin-2-yl)acetonitrile was prepared according to Example 235, substituting (2E)-4-(1-piperidinyl)-2-butenoic acid HCl salt, to afford the title compound (30 mg, 0.046 mmol, 92.0%). ESI MS m/z 649.3 [M+H]+.

Example 237

2-((S)-1-acryloyl-4-(2-(((S)-1-methylpyrrolidin-2-yl)methoxy)-7-(2-(trifluoromethyl)phenyl)-5,6,7,8-tetrahydropyrido [3,4-d] pyrimidin-4-yl)piperazin-2-yl)acetonitrile 2,2,2-trifluoroacetate

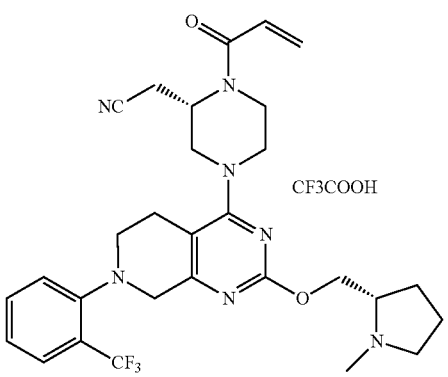

Synthesized according to Example 234 substituting 1-bromo-2-(trifluoromethyl)benzene for 1-bromonaphthalene. ES+APCI MS m/z 570.3 [M+H]+.

Example 238

2-(1-acryloyl-4-(7-(6-methyl-1H-indazol-7-yl)-2-((S)-1-methylpyrrolidin-2-yl)methoxy)-5,6,7,8-tetrahydropyrido[3,4-d]pyrimidin-4-yl)piperazin-2-yl)acetonitrile

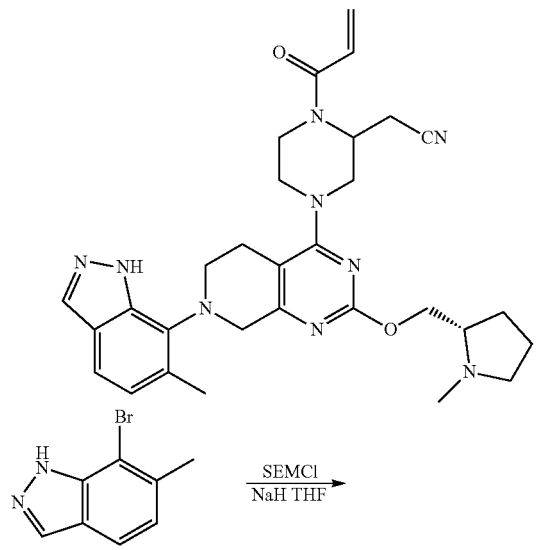

-continued

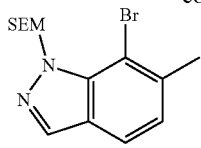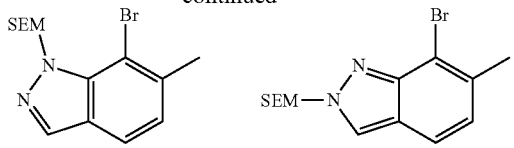

Step A: 7-bromo-6-methyl-2-((2-(trimethylsilyl)ethoxy)methyl)-2H-indazole

A solution of 7-bromo-6-methyl-1H-indazole (200 mg, 0.948 mmol) in tetrahydrofuran (2 ml, 0.948 mmol) was cooled with stirring in an ice bath. Sodium hydride (45.5 mg, 1.14 mmol) was added portionwise to the mixture and the reaction was stirred at 0° C. for 1 hour. (2-(chloromethoxy)ethyl)trimethylsilane (0.201 ml, 1.14 mmol) was next added and the reaction stirred for 2 hours while warming to room temperature. The mixture was divided between EtOAc (20 mL) and water (10 mL) and the layers separated. The organic layer was washed with water (2×10 mL), brine (10 mL), dried over Na$_2$SO$_4$ and evaporated in vacuo. The product was purified by chromatography on silica gel using 20 to 40% EtOAc/hexanes as eluent to give 7-bromo-6-methyl-2-((2-(trimethylsilyl)ethoxy)methyl)-2H-indazole (46 mg, 14%) along with isomer 7-bromo-6-methyl-1-((2-(trimethylsilyl)ethoxy)methyl)-1H-indazole (214 mg, 66%). ES+APCI MS m/z 341.1 [M]+.

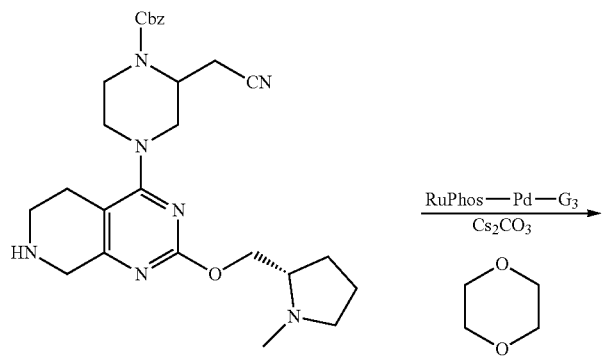

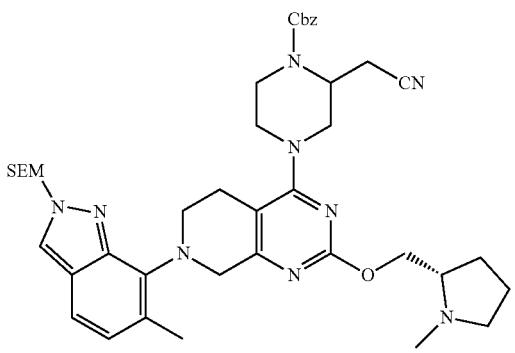

Step B: Benzyl 2-(cyanomethyl)-4-(7-(6-methyl-2-((2-(trimethylsilyl)ethoxy)methyl)-2H-indazol-7-yl)-2-((S)-1-methylpyrrolidin-2-yl)methoxy)-5,6,7,8-tetrahydropyrido[3,4-d]pyrimidin-4-yl)piperazine-1-carboxylate A mixture of benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (50 mg, 0.099 mmol), 7-bromo-6-methyl-2-((2-(trimethylsilyl)ethoxy)methyl)-2H-indazole (46 mg, 0.13 mmol), Cs$_2$CO$_3$ (97 mg, 0.30 mmol), Ruphos Pd G3 (83 mg, 0.099 mmol) and dioxane (1 mL) was purged with nitrogen and stirred at 70° C. for 6 hours. The reaction mixture was cooled to room temperature and divided between EtOAc (20 mL) and water (10 mL) and the layers separated. The organic layer was washed with water (5 mL), brine (5 mL), dried over Na$_2$SO$_4$ and evaporated in vacuo. The product was purified by chromatography on silica gel, Redisep 24 g, using 2 to 20% MeOH/DCM as eluent to give a colorless solid (50 mg, 66%). ES+APCI MS m/z 766.4 [M]$^+$.

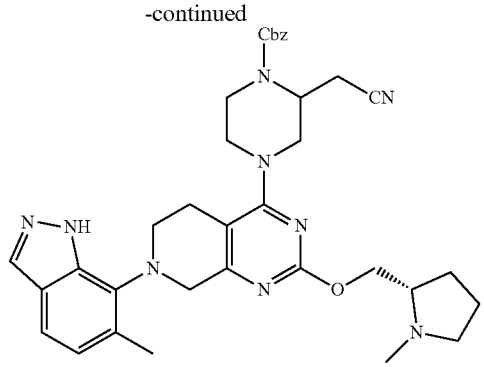

Step C: Benzyl 2-(cyanomethyl)-4-(7-(6-methyl-1H-indazol-7-yl)-2-(((S)-1-methylpyrrolidin-2-yl)methoxy)-5,6,7,8-tetrahydropyrido[3,4-d]pyrimidin-4-yl)piperazine-1-carboxylate Neat benzyl 2-(cyanomethyl)-4-(7-(6-methyl-2-((2-(trimethylsilyl)ethoxy)methyl)-2H-indazol-7-yl)-2-((S)-1-methylpyrrolidin-2-yl)methoxy)-5,6,7,8-tetrahydropyrido[3,4-d]pyrimidin-4-yl)piperazine-1-carboxylate (10 mg, 0.0131 mmol) (10 mg, 0.0131 mmol) was dissolved in trifluoroacetic acid (1 ml, 13.1 mmol) and the yellow-brow solution was stirred at room temperature for 1.5 hours. The reaction mixture was poured into ethyl acetate (20 mL) and the organics washed carefully with 2M Na$_2$CO$_3$ (10 mL, 20 mmol), water (2×3 mL), brine (5 mL), dried over Na$_2$SO$_4$ and evaporated in vacuo to give a yellowish solid (8 mg, 96%). ES+APCI MS m/z 636.3 [M+H]$^+$.

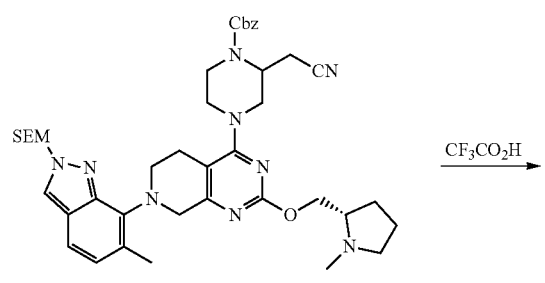

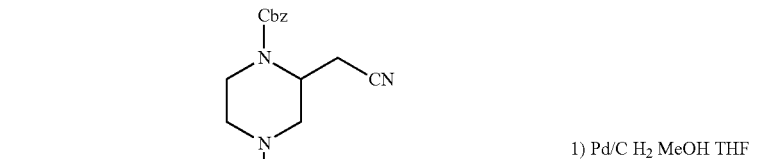

Step D: 2-(1-acryloyl-4-(7-(6-methyl-1H-indazol-7-yl)-2-(((S)-1-methylpyrrolidin-2-yl)methoxy)-5,6,7,8-tetrahydropyrido[3,4-d]pyrimidin-4-yl)piperazin-2-yl)acetonitrile A stirred mixture of benzyl 2-(cyanomethyl)-4-(7-(6-methyl-1H-indazol-7-yl)-2-(((S)-1-methylpyrrolidin-2-yl)methoxy)-5,6,7,8-tetrahydropyrido[3,4-d]pyrimidin-4-yl)piperazine-1-carboxylate (16 mg, 0.02517 mmol), methanol (1.5 ml, 0.02517 mmol), tetrahydrofuran (1.815 mg, 0.02517 mmol) and palladium on carbon (10 mg, 5%, Degussa type E101 NO/W) was degassed and stirred under hydrogen atmosphere for 1 hour. The mixture was filtered through Celite (2 mL) and the celite washed with THF (3×3 mL). The combined organics were concentrated in vacuo to ~0.5 mL, dissolved in DCM (5 mL), cooled to −30° C. with stirring in an EtOH-H$_2$O—CO$_2$ bath. Triethylamine (0.02 mL, 5 eq.) was next added followed by acryloyl chloride (0.006134 ml, 0.07550 mmol) and the reaction mixture was stirred 1 min at −30° C. The reaction was quenched with NH$_4$OH (0.03 mL) and concentrated in vacuo. The residue was divided between 1M NaHCO$_3$ (3 mL) and EtOAc (15 mL) and the layers separated. The organic layer was washed with water (3 mL), brine (3 mL), dried over Na$_2$SO$_4$ and evaporated in vacuo. The product was purified by chromatography on silica gel, Redisep 12 g, using 10 to 20% MeOH/DCM+0.2% NH$_4$OH as eluent to give a colorless solid (5.96 mg, 43%). ES+APCI MS m/z 556.3 [M+H]$^+$.

Example 239

2-(1-acryloyl-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazin-2-yl)acetonitrile

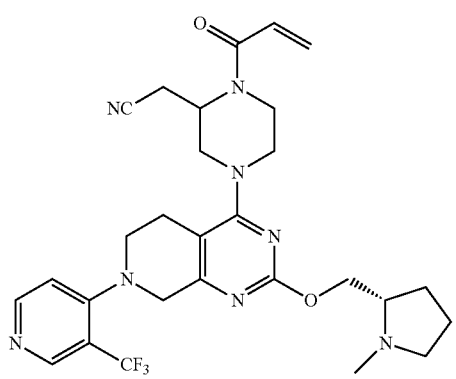 [SMILES: C=CC(=O)N1CCN(c2nc(OC[C@@H]3CCCN3C)nc3c2CCN(c2ccncc2C(F)(F)F)C3)CC1CC#N]

Synthesized according to Example 210, Steps E-G using 4-Bromo-3-(trifluoromethyl)pyridine hydrobromide in place of 1-bromo-2-(trifluoromethyl)benzene in Step E. ES+APCI MS m/z 571.3 [M+H]$^+$.

Example 240

2-(1-acryloyl-4-(2-(((S)-1-methylpyrrolidin-2-yl)methoxy)-7-(2-(2,2,2-trifluoroethyl)phenyl)-5,6,7,8-tetrahydropyrido[3,4-d]pyrimidin-4-yl)piperazin-2-yl)acetonitrile

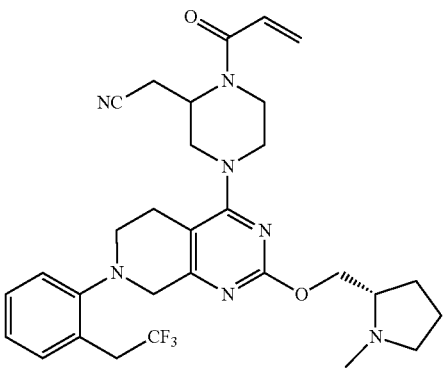 [SMILES: C=CC(=O)N1CCN(c2nc(OC[C@@H]3CCCN3C)nc3c2CCN(c2ccccc2CC(F)(F)F)C3)CC1CC#N]

Synthesized according to Example 210, Steps E-G using 1-bromo-2-(2,2,2-trifluoroethyl)benzene in place of 1-bromo-2-(trifluoromethyl)benzene in Step E. ES+APCI MS m/z 584.3 [M+H]$^+$.

Example 241 benzyl 2-(cyanomethyl)-4-(2-(((S)-1-methylpyrrolidin-2-yl)methoxy)-7-(3-(trifluoromethyl)pyridin-2-yl)-5,6,7,8-tetrahydropyrido[3,4-d]pyrimidin-4-yl)piperazine-1-carboxylate

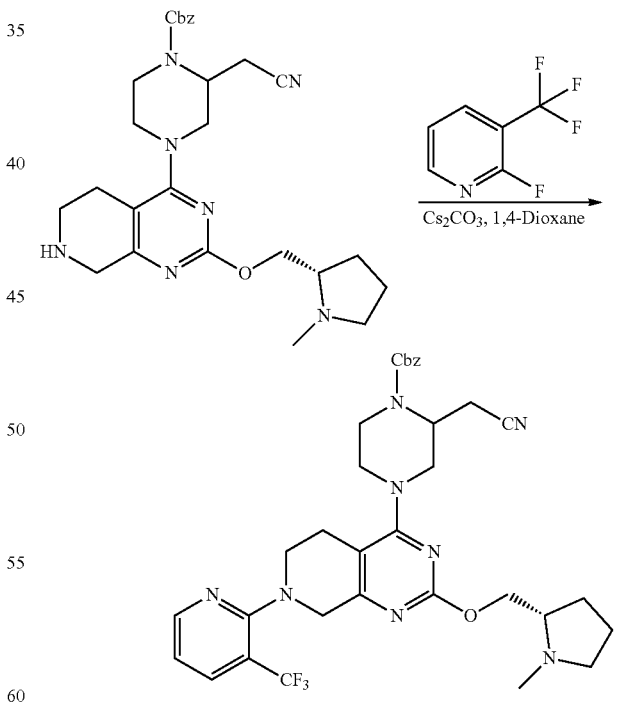

Step A: In a vial, benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (100 mg, 0.198 mmol) was dissolved in dioxane (98.9 µl, 0.198 mmol) and treated with cesium carbonate (129 mg, 0.396 mmol), and 2-Fluoro-3-(trifluoromethyl)pyridine (163 mg, 0.989 mmol) The tube was then capped and heated to 90° C. for 12 hr. Reaction was filtered through GF/F paper and concentrated. The residue was purified by silica chromatography (0-12% MeOH in DCM).

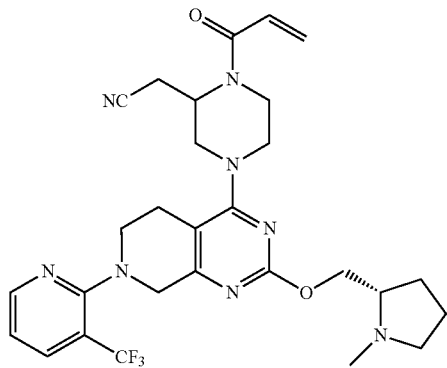 [SMILES: C=CC(=O)N1CCN(c2nc(OC[C@@H]3CCCN3C)nc3c2CCN(c2ncccc2C(F)(F)F)C3)CC1CC#N]

Step B: Synthesized according to Example 210, Steps F-G using benzyl 2-(cyanomethyl)-4-(2-(((S)-1-methylpyrrolidin-2-yl)methoxy)-7-(3-(trifluoromethyl)pyridin-2-yl)-5,6,7,8-tetrahydropyrido[3,4-d]pyrimidin-4-yl)piperazine-1-carboxylate in place of benzyl 2-(cyanomethyl)-4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazine-1-carboxylate in Step F. ES+APCI MS m/z 571.3 [M+H]+.

Example 242

2-(1-(but-2-ynoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

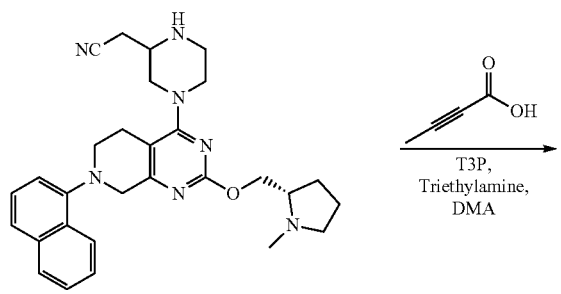

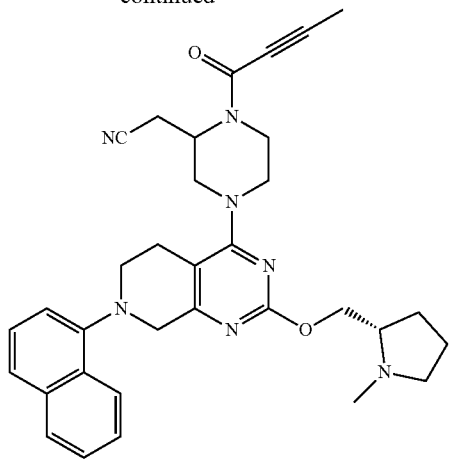

At 0° C., to a 25 mL RBF containing N,N-dimethylformamide (603 μL, 0.06 mmol) was added 2-(4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (30 mg, 0.06 mmol) and triethylamine (12.2 mg, 0.12 mmol). The reaction mixture was vigorously stirred while 2-Butynoic acid (6.08 mg, 0.07 mmol) was added in one portion. Next, 1-Propanephosphonic acid cyclic anhydride (26.9 μl, 0.09 mmol) was added to the stirring mixture. The reaction was allowed to stir for 2 h at 0° C. Water was added and the reaction extracted with EtOAc (2×25 mL). The organic layers were washed with saturated LiCl, NaCl, and water (10 mL each wash). Dried and concentrated to a solid that was purified by reverse phase prep HPLC (5-95% ACN:H2O, with 0.1% TFA) to provide the title compound.

Example 243

2-[4-[2-[[(2R)-1-methylpyrrolidin-2-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile

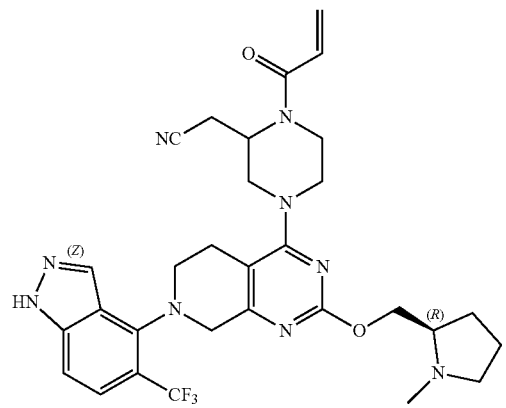

669                                             670
-continued
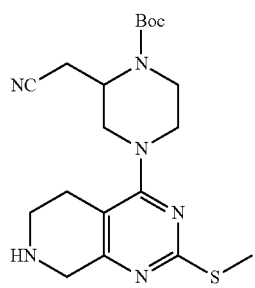 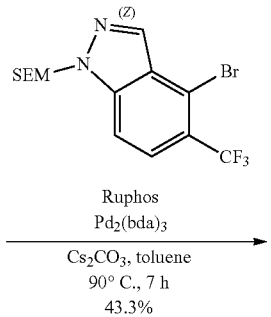 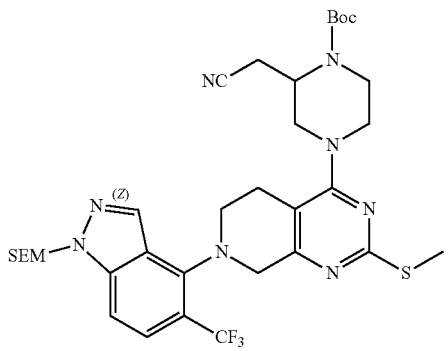
Ruphos
Pd$_2$(bda)$_3$
Cs$_2$CO$_3$, toluene
90° C., 7 h
43.3%
m-CPBA,
DCM
0° C.,
1 h
79.8%
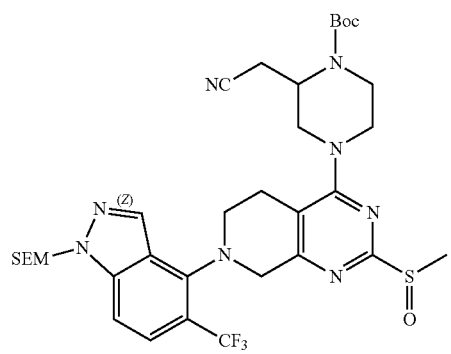 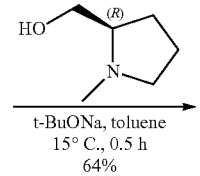
t-BuONa, toluene
15° C., 0.5 h
64%
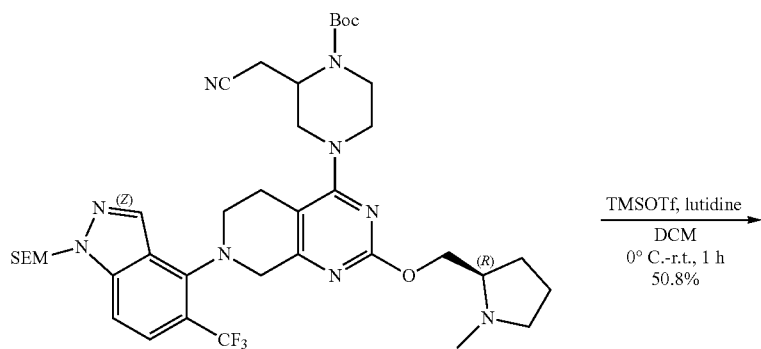
TMSOTf, lutidine
DCM
0° C.-r.t., 1 h
50.8%
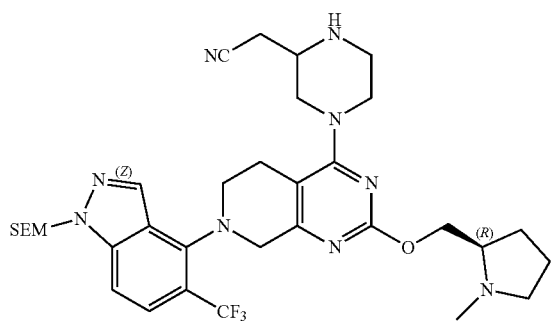 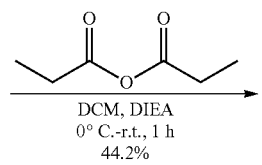
DCM, DIEA
0° C.-r.t., 1 h
44.2%

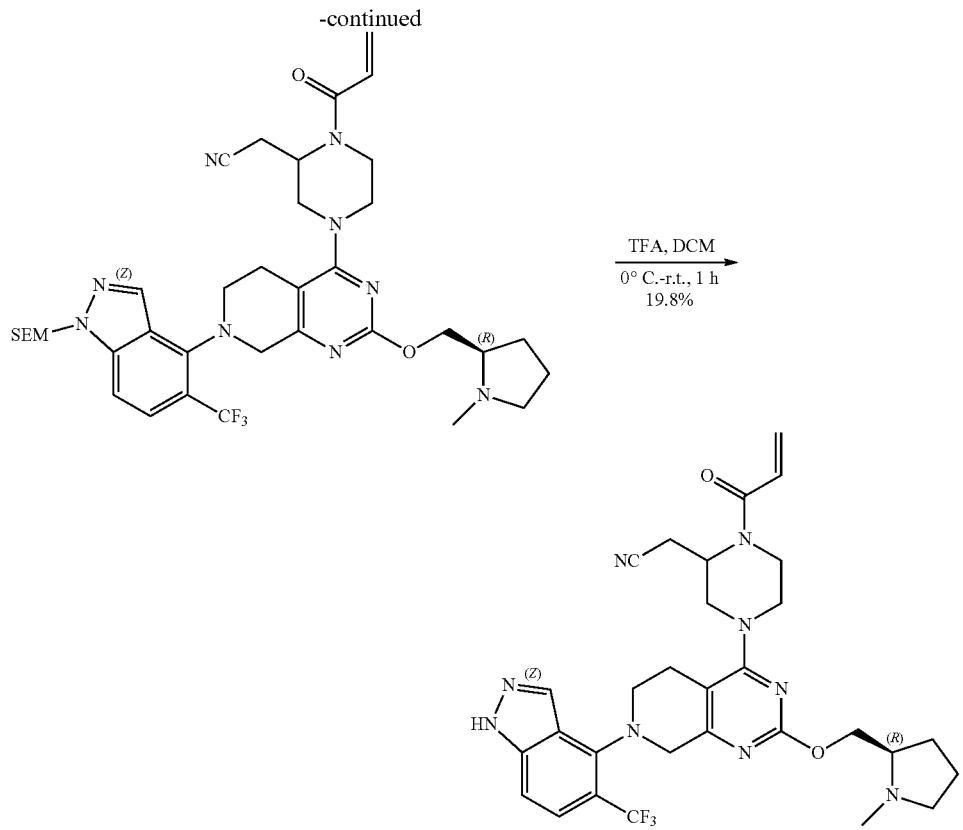

Step A: tert-butyl 2-(cyanomethyl)-4-[2-methylsulfanyl-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate To a solution of tert-butyl 2-(cyanomethyl)-4-(2-methylsulfanyl-5,6,7,8-tetrahydropyrido[3,4-d]pyrimidin-4-yl)piperazine-1-carboxylate (1.05 g, 2.60 mmol), 2-[[4-bromo-5-(trifluoromethyl)indazol-1-yl]methoxy]ethyl-trimethyl-silane (1.13 g, 2.86 mmol), RuPhos (484 mg, 1.04 mmol) and $Cs_2CO_3$ (2.11 g, 6.49 mmol) in toluene (20 mL) was added $Pd_2(dba)_3$ (475 mg, 519 umol) under $N_2$, the suspension was degassed under vacuum and purged with $N_2$ several times. The mixture was warmed to 90° C. and stirred at 90° C. for 7 hours. The reaction mixture was filtered and the filter cake was washed with EtOAc (3×20 mL). The combined organic layers were concentrated under vacuum. The residue was purified by silica gel chromatography (PE:EA from 30:1 to 4:1) and then by reversed phase flash column (ACN: 100%) to give tert-butyl 2-(cyanomethyl)-4-[2-methylsulfanyl-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (850 mg, 1.12 mmol, 43.3% yield, 95.0% purity) as a yellow solid. ESI MS m/z 719.5 [M+H]$^+$.

Step B: tert-butyl 2-(cyanomethyl)-4-[2-methylsulfinyl-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate To a solution of tert-butyl 2-(cyanomethyl)-4-[2-methylsulfanyl-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (850 mg, 1.18 mmol) in DCM (17 mL) was added m-CPBA (240 mg, 1.18 mmol, 85.0% purity) at 0° C. and stirred at 0° C. for 1 hour. The reaction mixture was quenched by saturated $Na_2S_2O_3$ (15 mL) at 0° C. and separated, then diluted with water (10 mL) and extracted with EtOAc (30 mL). The combined organic layers were dried over anhydrous $Na_2SO_4$, filtered and concentrated under vacuum. The residue was purified by reversed phase flash column (ACN/Water (0.1% FA)=80%) to give tert-butyl 2-(cyanomethyl)-4-[2-methylsulfinyl-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (730 mg, 944 umol, 79.8% yield, 95.0% purity) as yellow solid. ESI MS m/z 735.5 [M+H]$^+$.

Step C: tert-butyl 2-(cyanomethyl)-4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate To a solution of tert-butyl 2-(cyanomethyl)-4-[2-methylsulfinyl-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (300 mg, 408 umol) and [(2R)-1-methylpyrrolidin-2-yl]methanol (94.0 mg, 816 umol) in toluene (6 mL) was added t-BuONa (58.8 mg, 612 umol) at 15° C. and stirred at 15° C. for 0.5 hour. To the mixture was added EtOAc (15 mL) and water (5 mL), then extracted with EtOAc (3×10 mL). The combined organic layers were dried over anhydrous $Na_2SO_4$, filtered and concentrated under vacuum. The residue was purified by reversed phase flash column (ACN/Water (0.1% FA)=54%) to give tert-butyl 2-(cyanomethyl)-4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (216 mg, 261 umol, 64.0% yield, 95.0% purity) as brown solid. ESI MS m/z 786.6[M+H]+.

Step D: 2-[4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazin-2-yl]acetonitrile To a solution of tert-butyl 2-(cyanomethyl)-4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (190 mg, 242 umol) and 2,6-dimethylpyridine (311 mg, 2.90 mmol, 338 uL) in DCM (4 mL) was added TMSOTf (645 mg, 2.90 mmol, 524 uL) at 0° C. and stirred at 20° C. for 1 hour. The reaction mixture was quenched by MeOH (1 mL), then concentrated under vacuum. The residue was purified by reversed phase flash column (ACN/Water (0.1% FA)=40%). 2-[4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazin-2-yl]acetonitrile (85 mg, 123 umol, 50.8% yield, 99.0% purity) was obtained as a white solid. ESI MS m/z 686.5 [M+H]+.

Step E: 2-[4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile To a solution of 2-[4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazin-2-yl]acetonitrile (85.0 mg, 124 umol), DIEA (96.1 mg, 744 umol, 130 uL) in DCM (2 mL) was added prop-2-enoyl prop-2-enoate (23.4 mg, 186 umol) at 0° C. and the mixture stirred at 20° C. for 1 hour. The reaction mixture was quenched by water (2 mL). The resulting mixture was extracted with DCM (3×5 mL). The combined organic layers were dried over anhydrous Na2SO4, filtered and concentrated under vacuum The residue was purified by reversed phase flash column (ACN/Water (0.1% FA)=48%) to give 2-[4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile (45 mg, 54.7 umol, 44.2% yield, 90.0% purity) as white solid. 1H NMR (400 MHz, chloroform-d) δ=8.16 (s, 1H), 7.71 (d, J=8.8 Hz, 1H), 7.52 (d, J=8.8 Hz, 1H), 6.59 (br s, 1H), 6.45-6.36 (m, 1H), 5.84 (br d, J=10.4 Hz, 1H), 5.76 (s, 2H), 5.12 (s, 1H), 4.44-4.28 (m, 3H), 4.21-4.08 (m, 2H), 3.98 (br d, J=12.0 Hz, 1H), 3.63-3.54 (m, 2H), 3.48-3.39 (m, 2H), 3.32 (br s, 1H), 3.10 (br s, 2H), 2.99-2.86 (m, 2H), 2.80 (br s, 2H), 2.73-2.58 (m, 2H), 2.49 (s, 3H), 2.28 (br s, 1H), 2.05 (br s, 1H), 1.77 (br s, 4H), 0.94-0.88 (m, 2H), −0.04 (s, 9H).

Step F: 2-[4-[2-[[(2R)-1-methylpyrrolidin-2-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile To a solution of 2-[4-[2-[[(2R)-1-methylpyrrolidin-2-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile (45 mg, 60.8 umol) in DCM (0.15 mL) was added TFA (208 mg, 1.82 mmol, 135 uL) and the mixture stirred at 20° C. for 1 hour. The reaction mixture was basified by saturated NaHCO3 (2 mL) to pH=8. The resulting mixture was extracted with DCM:MeOH (10:1) (3×5 mL). The combined organic layers were dried over anhydrous Na2SO4, filtered and concentrated under vacuum. The residue was purified by prep-HPLC (column: Phenomenex Synergi C18 150*30 mm*4 um; mobile phase: [water (0.225% FA)-ACN]; B %: 10%-40%,10.5 min) to give 2-[4-[2-[[(2R)-1-methylpyrrolidin-2-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile (8.2 mg, 12.0 umol, 19.8% yield, 96.2% purity, FA) as yellow oil. ESI MS m/z 610.4 [M+H]+.

Example 244

2-[4-[7-(8-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

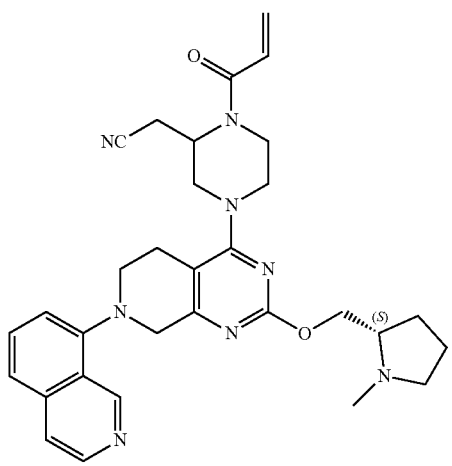

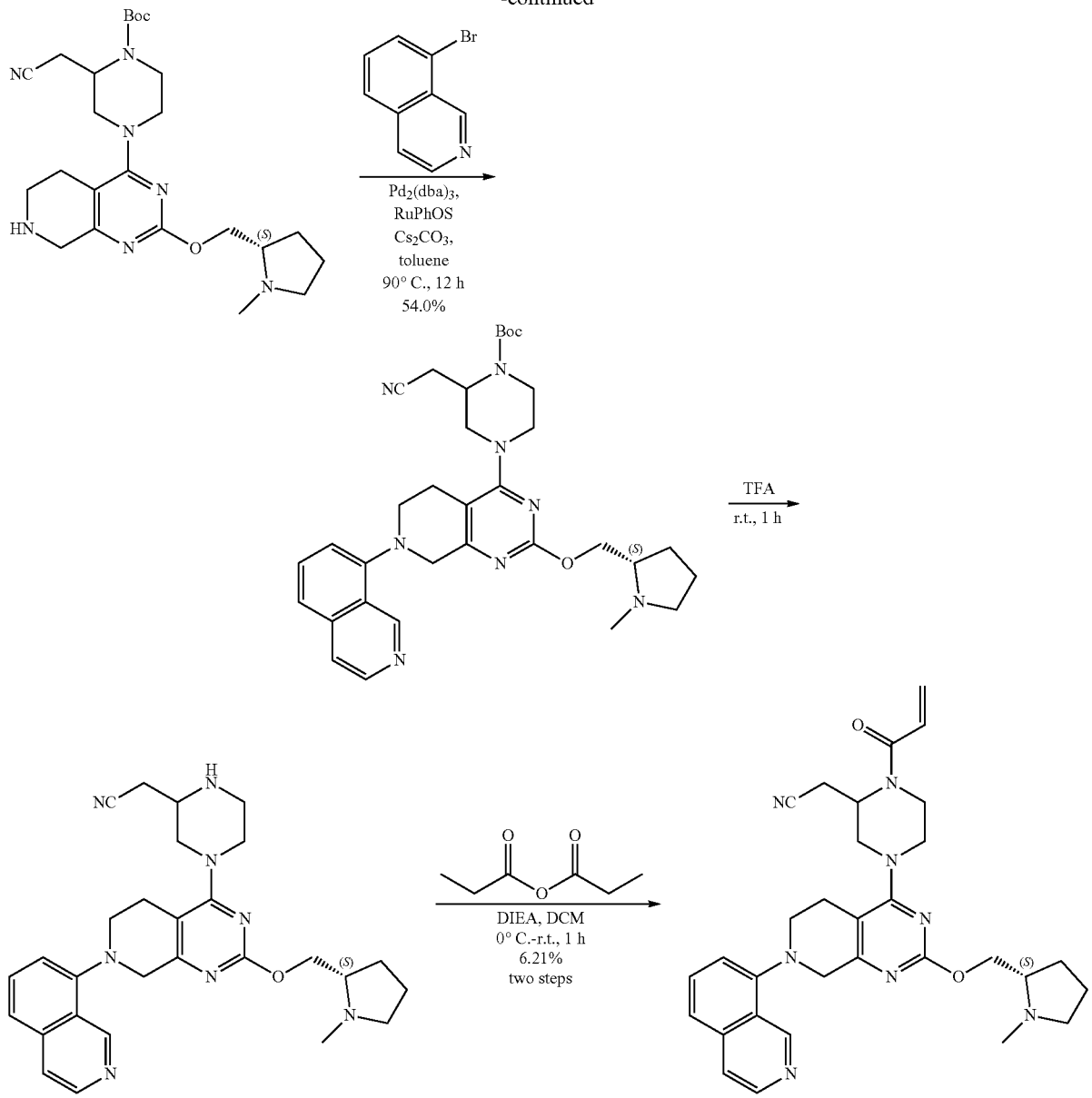

Step A: tert-butyl 2-(cyanomethyl)-4-[7-(8-isoquinolyl)-2-[[(2S)-1-methylpyrrolidin-2-yl]methoxy]-6,8-dihydro-5H-pyrido[3,4-d]pyrimidin-4-yl]piperazine-1-carboxylate To a solution of tert-butyl 2-(cyanomethyl)-4-[2-[((1-methylpyrrolidin-2-yl)methoxy]-5,6,7,8-tetrahydropyrido[3,4-d]pyrimidin-4-yl]piperazine-1-carboxylate (210 mg, 445 umol), 8-bromoisoquinoline (185 mg, 891 umol), RuPhos (41.6 mg, 89.1 umol) and Cs$_2$CO$_3$ (435 mg, 1.34 mmol) in toluene (4.5 mL) was added Pd$_2$(dba)$_3$ (40.8 mg, 44.5 umol) under N$_2$. The suspension was degassed under vacuum and purged with N$_2$ several times. The mixture was stirred under N$_2$ at 90° C. for 12 hours. The mixture was filtered and the filter cake was washed with EtOAc (3×10 mL). The combined organic layers were concentrated under vacuum. The residue was purified by reversed phase flash column (ACN/Water (0.1% FA)=20%) to give tert-butyl 2-(cyanomethyl)-4-[7-(8-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (160 mg, 240 umol, 54.0% yield, 90.0% purity) as brown solid. ESI MS m/z 599.4 [M+H]$^+$.

Step B: 2-[4-[7-(8-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile A solution of tert-butyl 2-(cyanomethyl)-4-[7-(8-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (190 mg, 317 umol) and TFA (724 mg, 6.35 mmol, 470 uL) was stirred at 20° C. for 1 hour. The reaction mixture was concentrated under vacuum to give 2-[4-[7-(8-isoquinolyl)-2-[[(2S)-1-methylpyrrolidin-2-yl]methoxy]-6, 8-dihydro-5H-pyrido[3,4-d]pyrimidin-4-yl]piperazin-2-yl] acetonitrile (230 mg, crude, 2TFA) as a brown oil.

Step C: 2-[4-[7-(8-isoquinolyl)-2-[[(2S)-1-methyl-pyrrolidin-2-yl]methoxy]-6,8-dihydro-5H-pyrido[3,4-d]pyrimidin-4-yl]-1-prop-2-enoyl-piperazin-2-yl] acetonitrile To a solution of 2-[4-[7-(8-isoquinolyl)-2-[[(2S)-1-methylpyrrolidin-2-yl]methoxy]-6,8-dihydro-5H-pyrido[3,4-d]pyrimidin-4-yl]piperazin-2-yl] acetonitrile (230 mg, 316 umol, 2TFA) and DIEA (409 mg, 3.17 mmol, 551 uL) in DCM (5 mL) was added prop-2-enoyl prop-2-enoate (47.9 mg, 380 umol) at 0° C., then the mixture was stirred at 20° C. for 1 hour. Water (5 mL) was added to the mixture. The resulting mixture was extracted with DCM (3×5 mL). The combined organic layers were dried over anhydrous Na$_2$SO$_4$, filtered and concentrated under vacuum. The residue was purified by prep-HPLC (column: Phenomenex Synergi C18 150*25*10 um; mobile phase: [water (0.225% FA)-ACN]; B %: 1%-20%,10 min) to give 2-[4-[7-(8-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (12.5 mg, 19.7 umol, 6.23% yield, 94.5% purity, FA) as yellow solid. ESI MS m/z 553.2 [M+H]$^+$.

Example 245

2-[4-[7-(7-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

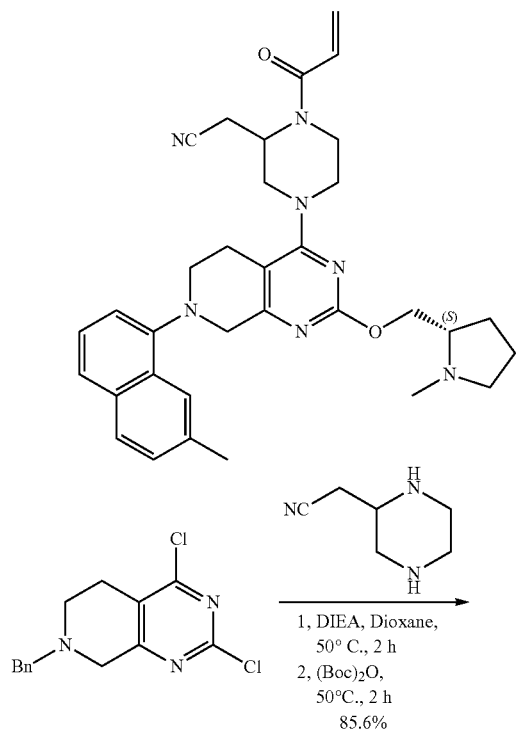

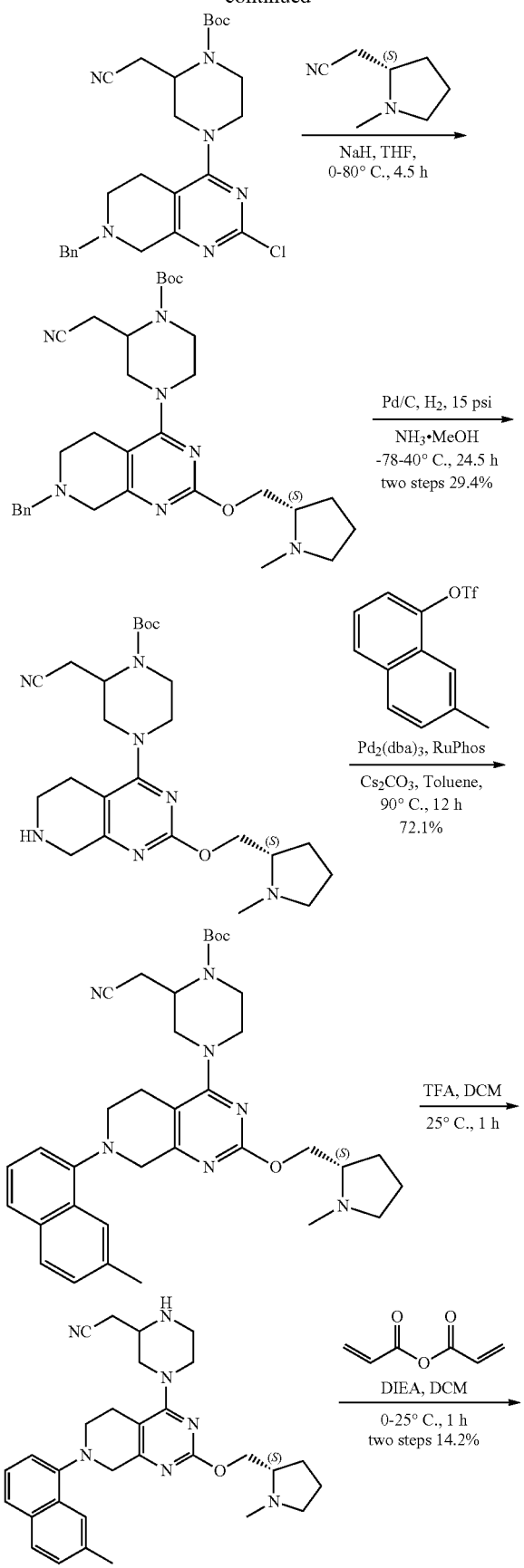

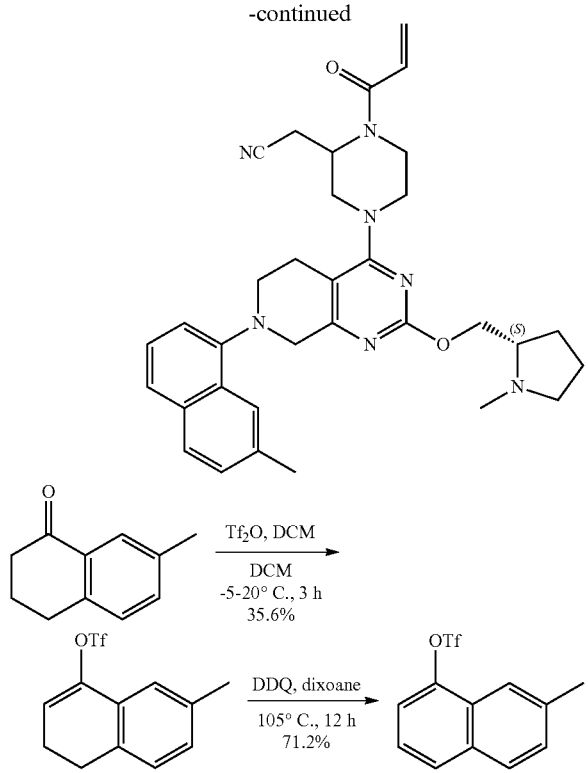

Step A: (7-methyl-3,4-dihydronaphthalen-1-yl) trifluoromethanesulfonate

To a solution of 7-methyltetralin-1-one (2.00 g, 12.5 mmol) and DIPEA (4.84 g, 37.5 mmol, 6.52 mL) in DCM (30 mL) was added Tf₂O (5.28 g, 18.7 mmol, 3.09 mL) dropwise at −5° C. The mixture was stirred at 20° C. for 3 hours. Upon completion, the mixture was concentrated under vacuum. The residue was purified by silica gel chromatography (PE/EA 1/0 to 100/1) to give (7-methyl-3,4-dihydronaphthalen-1-yl) trifluoromethanesulfonate (1.53 g, 4.45 mmol, 35.6% yield, 85.0% purity) as a yellow oil. $^1$H NMR (400 MHz, chloroform-d) δ=7.17 (s, 1H), 7.11-7.05 (m, 2H), 6.01 (t, J=4.8 Hz, 1H), 2.83 (t, J=8.0 Hz, 2H), 2.50 (dt, J=4.8, 8.0 Hz, 2H), 2.36 (s, 3H).

Step B: (7-methyl-1-naphthyl) trifluoromethanesulfonate

A mixture of (7-methyl-3,4-dihydronaphthalen-1-yl)trifluoro methanesulfonate (1.40 g, 4.79 mmol) and DDQ (2.17 g, 9.58 mmol) in dioxane (28 mL) was stirred at 105° C. for 12 hours. Upon completion, the mixture was concentrated under vacuum. The residue was purified by silica gel chromatography (PE/EA 1/0 to 100/1) to give (7-methyl-1-naphthyl) trifluoromethanesulfonate (1.10 g, 3.41 mmol, 71.2% yield, 90.0% purity) as a yellow oil. $^1$H NMR (400 MHz, chloroform-d) δ=7.87-7.79 (m, 3H), 7.49-7.38 (m, 3H), 2.59 (s, 3H).

Step C: tert-butyl 4-(7-benzyl-2-chloro-6,8-dihydro-5H-pyrido[3,4-d] pyrimidin-4-yl)-2-(cyanomethyl) piperazine-1-carboxylate A mixture of 7-benzyl-2,4-dichloro-6,8-dihydro-5H-pyrido [3,4-d]pyrimidine (10 g, 34.0 mmol), 2-piperazin-2-ylacetonitrile (10.1 g, 51.0 mmol, 2 HCl) and DIEA (17.6 g, 136 mmol, 23.7 mL) in dioxane (100 mL) was stirred at 50° C. for 2 hours. Boc₂O (14.8 g, 68.0 mmol, 15.6 mL) was added and the mixture was stirred at 50° C. for 2 hours. The mixture was concentrated under vacuum and the residue was diluted with ethyl acetate (500 mL). The separated organic layer was washed with water (1×300 mL), brine (1×200 mL), dried over sodium sulfate, filtered and concentrated under vacuum. The residue was triturated with ethyl acetate (100 mL). The precipitate was filtered and the filtered cake was washed with ethyl acetate (50 mL) and dried under vacuum to give a gray solid. The filtrate was concentrated under vacuum. The residue was purified by column chromatography over silica gel (petroleum ether/ethyl acetate 100/1 to 1/2). The desired fractions were collected and concentrated under vacuum to give solid then combined with above solid to give tert-butyl 4-(7-benzyl-2-chloro-6,8-dihydro-5H-pyrido[3,4-d] pyrimidin-4-yl)-2-(cyanomethyl)piperazine-1-carboxylate (15 g, 29.10 mmol, 85.6% yield, 93.7% purity) as yellow solid. ESI MS m/z 483.1 [M+H]⁺.

Step D: 4-[7-benzyl-2-[(1-methylpyrrolidin-2-yl) methoxy]-6,8-dihydro-5H-pyrido[3,4-d] pyrimidin-4-yl]-2-(cyanomethyl)piperazine-1-carboxylate To a solution of [(2S)-1-methylpyrrolidin-2-yl]methanol (1.19 g, 10.4 mmol, 1.23 mL, 2.5 eq) in THF (30.0 mL) was added NaH (331 mg, 8.28 mmol, 60% purity in mineral oil, 2.00 eq) at 0° C. and the mixture was stirred at 0° C. for 0.5 h. tert-Butyl 4-(7-benzyl-2-chloro-6,8-dihydro-5H-pyrido [3,4-d]pyrimidin-4-yl)-2-(cyanomethyl)piperazine-1-carboxylate (2.00 g, 4.14 mmol, 1.00 eq) was added into the mixture and the mixture was stirred at 80° C. for 4 hours. The mixture was poured into ice water (100 mL) and extracted with ether acetate (3×150 mL). The organic layers were washed with saturated sodium chloride solution (1×200 mL), dried over Na₂SO₄, filtered and concentrated under vacuum to give tert-butyl 4-[7-benzyl-2-[(1-methylpyrrolidin-2-yl)methoxy]-6,8-dihydro-5H-pyrido[3,4-d] pyrimidin-4-yl]-2-(cyanomethyl)piperazine-1-carboxylate (2.86 g, crude) as a black oil which was used in the next step without further purification. ESI MS m/z 562.3 [M+H]⁺.

Step E: tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate NH₃ was bubbled into methanol (70.0 mL) at −78° C. for 30 minutes. tert-Butyl 4-[7-benzyl-2-[(1-methylpyrrolidin-2-yl)methoxy]-6,8-dihydro-5H-pyrido [3,4-d] pyrimidin-4-yl]-2-(cyanomethyl)piperazine-1-carboxylate (2.00 g, crude) and Pd/C (0.20 g, 10% purity) were added into the mixture. The mixture was stirred at 40° C. for 24 hours under H₂ at 15 psi. The mixture was filtered and concentrated under vacuum. The residue was purified by reverse phase flash [water (FA, 0.1%)/ancetonitrile]. The desired fractions were adjusted to pH >7 by saturated sodium bicarbonate solution (5.00 mL) and the aqueous layer extracted with ether acetate (3×100 mL). The combined organic layers were washed with brine (1×100 mL), dried over Na₂SO₄, filtered and concentrated under vacuum to give tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate (0.40 g, 845 umol, two steps 29.4% yield) as a yellow solid. ESI MS m/z 472.2 [M+H]⁺.

Step F: tert-butyl 2-(cyanomethyl)-4-[2-[(1-methyl-pyrrolidin-2-yl)methoxy]-5,6,7,8-tetrahydropyrido[3,4-d]pyrimidin-4-yl]piperazine-1-carboxylate A solution of tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate (185 mg, 392 umol), (7-methyl-1-naphthyl) trifluoromethanesulfonate (159 mg, 549 umol), Pd$_2$(dba)$_3$ (35.9 mg, 39.2 umol), RuPhos (36.6 mg, 78.5 umol) and Cs$_2$CO$_3$ (320 mg, 981 umol) in toluene (30 mL) was de-gassed with N2 and then heated to 90° C. for 12 hours under N$_2$. Upon completion, the mixture was filtered and the filtrate was concentrated under vacuum. The residue was purified by reversed-phase flash [water (0.1% NH$_3$.H$_2$O)/acetonitrile] to give tert-butyl 2-(cyanomethyl)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (180 mg, 283 umol, 72.1% yield, 96.1% purity) as a yellow solid. ESI MS m/z 612.6 [M+H]$^+$.

Step G: 2-[4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile A solution of tert-butyl 2-(cyanomethyl)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (180 mg, 294 umol) in TFA (671 mg, 5.88 mmol, 436 uL) was stirred at 20° C. for 1 hour. Upon completion the mixture was concentrated under vacuum to give 2-[4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (0.37 g, crude, TFA) as a yellow oil which was used directly in the next step without further purification.

Step H: 2-[4-[7-(7-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(7-methyl-1-naphthyl)-2-[[(2S)-1-methyl pyrrolidin-2-yl]methoxy]-6,8-dihydro-5H-pyrido[3,4-d]pyrimidin-4-yl]piperazin-2-yl]acetonitrile (189 mg, crude, TFA) and DIEA (976 mg, 7.55 mmol, 1.32 mL) in DCM (4 mL) was added prop-2-enoyl prop-2-enoate (38.1 mg, 302 umol) dropwise at 0° C. The mixture was stirred at 25° C. for 1 hour. Upon completion, the reaction was quenched with MeOH (0.5 mL), diluted with water (1 mL) and extracted with DCM (3×5 mL). The organic layers were dried over Na$_2$SO$_4$ and concentrated under vacuum. The residue was purified by prep-HPLC (column: Phenomenex Synergi C18 150*30 mm*4 um; mobile phase: [water (0.225% FA)-ACN]; B %: 15%-45%,10.5 min) to give 2-[4-[7-(7-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (13.2 mg, 21.3 umol, two steps 14.2% yield, 98.4% purity, FA) as a yellow solid. ESI MS m/z 566.5 [M+H]$^+$.

Example 246

2-[4-[7-(4-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

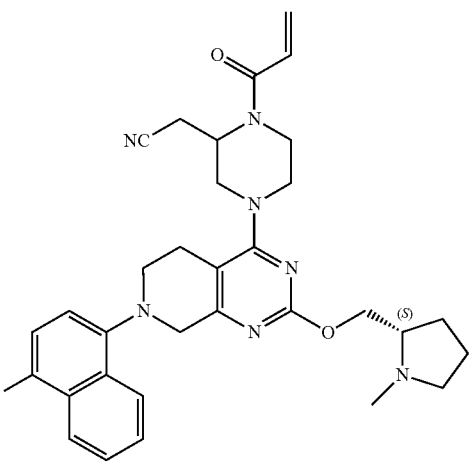

Synthesized according to the method for Example 147 substituting 1-bromo-4-fluoronaphthalene for 1-bromonaphthalene in step H. ESI MS m/z 570.5 [M+H]$^+$.

Example 247

2-(1-acryloyl-4-(2-(((S)-1-methylpyrrolidin-2-yl)methoxy)-7-(quinolin-8-yl)-5,6,7,8-tetrahydropyrido[3,4-d]pyrimidin-4-yl)piperazin-2-yl)acetonitrile

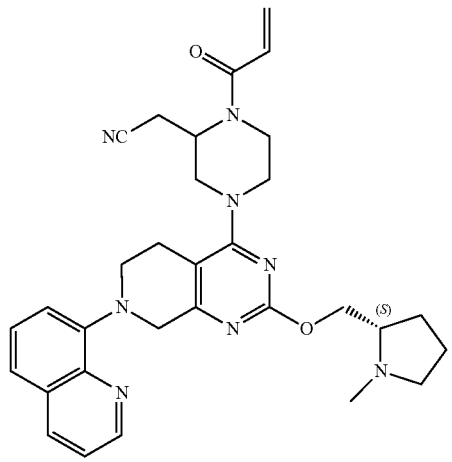

Synthesized according to the method for Example 147 substituting 8-bromoquinoline for 1-bromonaphthalene in Step H. ESI MS m/z 553.2 [M+H]$^+$.

Example 248
(S)-1-(4-(7-(5-isopropyl-1H-indazol-4-yl)-2-((1-methylpyrrolidin-2-yl)methoxy)-5,6,7,8-tetrahydropyrido[3,4-d]pyrimidin-4-yl)piperazin-1-yl)prop-2-en-1-one
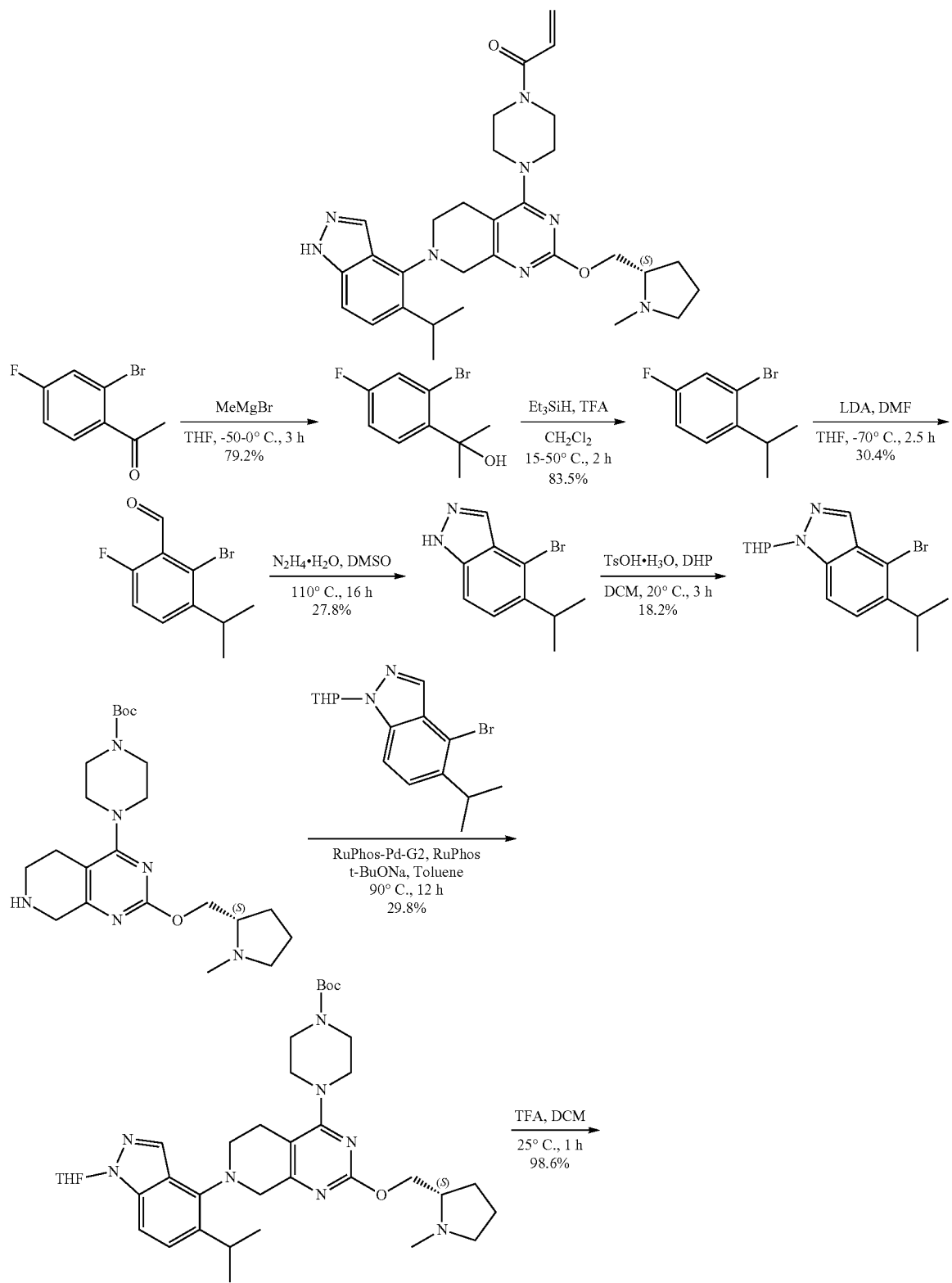

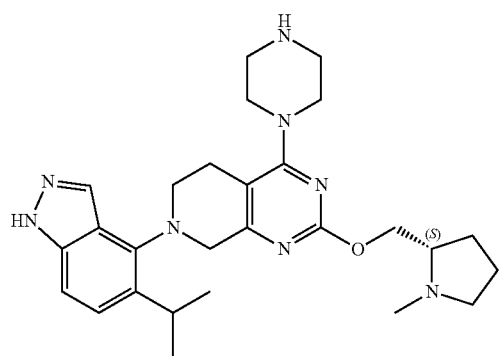
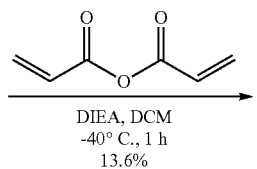

DIEA, DCM
-40° C., 1 h
13.6%

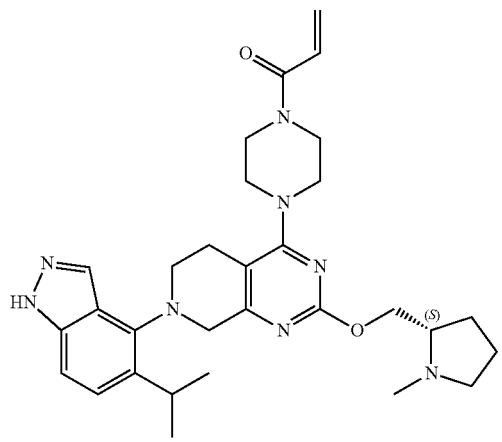

Step A: 2-(2-bromo-4-fluoro-phenyl)propan-2-ol

To a solution of 1-(2-bromo-4-fluoro-phenyl)ethanone (10 g, 46.1 mmol) in THF (100 mL) was added MeMgBr (in ether) (3 M, 46.08 mL) at −50° C. The mixture was warmed up to 0° C. and stirred for 3 hours. The mixture was quenched with saturated aqueous ammonium chloride solution (10 mL) at −50° C. The mixture was warmed up to 15° C. and was then diluted with ethyl acetate (500 mL). The separated organic layer was washed with water (1×500 mL) and brine (1×500 mL), dried over sodium sulfate, filtered and concentrated under vacuum to give 2-(2-bromo-4-fluoro-phenyl)propan-2-ol (10 g, 36.5 mmol, 79.2% yield, 85% purity) as a colorless oil.

Step B: 2-bromo-4-fluoro-1-isopropyl-benzene

To a solution of 2-(2-bromo-4-fluoro-phenyl)propan-2-ol (9 g, 38.6 mmol) in dichloromethane (100 mL) was added Et$_3$SiH (8.98 g, 77.2 mmol, 12.3 mL) and TFA (65.1 g, 571 mmol, 42.3 mL). The mixture was stirred at 15° C. for 1 hour and then heated to 50° C. for 1 hour. The reaction mixture was concentrated under vacuum and then diluted with ethyl acetate (100 mL). The aqueous layer pH was adjusted to pH=7 by addition of saturated NaHCO$_3$ aqueous solution and extracted with ethyl acetate (50 mL×3). The combined organic phase was washed with brine (30 mL), dried with anhydrous Na$_2$SO$_4$, filtered and concentrated under vacuum. The residue was purified by silica gel chromatography (Petroleum ether/Ethyl acetate=1/0 to 100/1). The desired fractions were collected and concentrated under vacuum. 2-bromo-4-fluoro-1-isopropyl-benzene (7 g, 32.2 mmol, 83.5% yield) was obtained as colorless oil. $^1$H NMR (400 MHz, chloroform-d) δ=7.36-7.27 (m, 2H), 7.09-7.02 (m, 1H), 3.46-3.31 (m, 1H), 1.28 (d, J=6.8 Hz, 6H).

Step C: 2-bromo-6-fluoro-3-isopropyl-benzaldehyde

To a mixture of 2-bromo-4-fluoro-1-isopropyl-benzene (7 g, 32.2 mmol in THF (100 mL) was added LDA (2 M in toluene, 24.2 mL) at −70° C. under nitrogen atmosphere. The mixture was stirred for 0.5 hour, and then DMF (7.07 g, 96.7 mmol, 7.44 mL) was added. The mixture was stirred at −70° C. for 2 hours. The reaction was quenched with water (100 mL) and extracted with ethyl acetate (2×100 mL). The combined organic layers were washed with brine (50 mL), dried over Na$_2$SO$_4$, filtered and concentrated under reduced pressure. The residue was purified by column chromatography (SiO$_2$, PE\EA=1\0 to 10\1). The desired fractions were collected and concentrated under vacuum to give 2-bromo-6-fluoro-3-isopropyl-benzaldehyde (2.4 g, 9.79 mmol, 30.4% yield) as a yellow oil. $^1$H NMR (400 MHz, chloroform-d) δ=10.41 (s, 1H), 7.48 (dd, J=5.6, 8.8 Hz, 1H), 7.13 (t, J=9.2, 1H), 3.57-3.46 (m, 1H), 1.26 (d, J=7.2 Hz, 6H).

Step D: 4-bromo-5-isopropyl-1H-indazole 2-bromo-6-fluoro-3-isopropyl-benzaldehyde (2.4 g, 9.79 mmol) in DMSO (3 mL) was added N$_2$H$_4$.H$_2$O (15.4 g, 302 mmol, 15 mL, 98% purity) and the mixture was heated to 110° C. and stirred for 16 hours. The reaction mixture was poured into H$_2$O (10 mL) and extracted with ethyl acetate (20 mL×3). The organic phase was washed with brine (10 mL), dried over anhydrous Na$_2$SO$_4$ and concentrated under vacuum to give the residue. The residue was purified by column chromatography (SiO$_2$, Petroleum ether/Ethyl acetate=1/0 to 5/1) to give 4-bromo-5-isopropyl-1H-indazole (650 mg, 2.72 mmol, 27.8% yield) as a yellow solid. $^1$H NMR (400 MHz, chloroform-d) δ=10.24 (br s, 1H), 8.08 (d, J=0.8 Hz, 1H), 7.43 (d, J=8.8 Hz, 1H), 7.34 (d, J=8.8 Hz, 1H), 3.56 (td, J=6.8, 13.6 Hz, 1H), 1.29 (d, J=6.8 Hz, 6H).

Step E: 4-bromo-5-isopropyl-1-tetrahydropyran-2-yl-indazole

To a solution of 3,4-dihydro-2H-pyran (457 mg, 5.44 mmol, 497 uL, 2 eq) in dichloromethane (15 mL) was added TsOH.H₂O (51.7 mg, 271 umol) and 4-bromo-5-isopropyl-1H-indazole (650 mg, 2.72 mmol). The mixture was stirred at 20° C. for 3 hours. The reaction mixture was diluted with water (20 mL) and extracted with ethyl acetate (20 mL×2). The combined organic layers were washed with brine (20 mL), dried over Na₂SO₄, filtered and concentrated under reduced pressure to give a residue. The residue was purified by column chromatography (SiO₂, Petroleum ether/Ethyl acetate=1/0 to 5/1) and further purificated by reversed phase flash [water (0.1% formic acid)/acetonitrile] to give 4-bromo-5-isopropyl-1-tetrahydropyran-2-yl-indazole (170 mg, 494 umol, 18.2% yield, 94% purity) as a yellow oil. ESI MS m/z 323.0 [M+H]⁺.

Step F: tert-butyl 4-[7-(5-isopropyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate A mixture of 4-bromo-5-isopropyl-1-tetrahydropyran-2-yl-indazole (136 mg, 420 umol), tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate (140 mg, 323 umol), RuPhos (15.1 mg, 32.4 umol), RuPhos-Pd-G2 (25.1 mg, 32.4 umol) and t-BuONa (77.7 mg, 809 umol) in toluene (3 mL) was degassed and purged with N₂ 3 times and the mixture was stirred at 90° C. for 12 hours under N₂ atmosphere. The mixture was diluted with ethyl acetate (20 mL) and washed with water (20 mL). The organic layers were washed with brine (10 mL), dried over Na₂SO₄, filtered and concentrated under reduced pressure to give a residue. The residue was purified by column chromatography (SiO₂, DCM/MeOH=100/1 to 10/1) and the desired fractions were collected and concentrated under vacuum to give tert-butyl 4-[7-(5-isopropyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (70 mg, 96.5 umol, 29.8% yield, 93% purity) was as a yellow solid. ESI MS m/z 675.3 [M+H]⁺.

Step G: 7-(5-isopropyl-1H-indazol-4-yl)-2-[[(2S)-1-methylpyrrolidin-2-yl]methoxy]-4-piperazin-1-yl-6,8-dihydro-5H-pyrido[3,4-d]pyrimidine To a solution of tert-butyl 4-[7-(5-isopropyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (40 mg, 59.3 umol) in dichloromethane (100 uL) was added TFA (101 mg, 889 umol, 65.8 uL). The mixture was stirred at 25° C. for 1 hour. The mixture was concentrated under vacuum to give 7-(5-isopropyl-1H-indazol-4-yl)-2-[[(2S)-1-methylpyrrolidin-2-yl]methoxy]-4-piperazin-1-yl-6,8-dihydro-5H-pyrido[3,4-d]pyrimidine (42 mg, 58.4 umol, 98.6% yield, 2 TFA) as a brown oil which was used in next step directly without purification. ESI MS m/z 491.4 [M+H]⁺.

Step H: 1-[4-[7-(5-isopropyl-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one To a mixture of 7-(5-isopropyl-1H-indazol-4-yl)-2-[[(2S)-1-methylpyrrolidin-2-yl]methoxy]-4-piperazin-1-yl-6,8-dihydro-5H-pyrido[3,4-d]pyrimidine (42 mg, 58.4 umol) and DIEA (75.5 mg, 584 umol, 102 uL) in dichloromethane (2 mL) was added a solution of prop-2-enoyl prop-2-enoate (7.37 mg, 58.4 umol, 1 eq) in dichloromethane (1 mL) at −40° C. under nitrogen atmosphere. The mixture was stirred at −40° C. for 1 hour. The reaction was quenched by adding saturated NaHCO₃ (2 mL) aqueous solution. Then the mixture was poured into water (20 mL) and extracted with dichloromethane (20 mL×2). The combined organics were dried over sodium sulfate, filtered and concentrated in vacuo. The residue was purified by prep-HPLC (column: Luna C18 150*25 5 u; mobile phase: [water (0.225% FA)-ACN]; B %: 5%-38%, 10 min) to give 1-[4-[7-(5-isopropyl-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one (4.5 mg, 7.93 umol, 13.6% yield, 96% purity) as a yellow solid. ESI MS m/z 545.2 [M+H]⁺.

Example 249

1-[4-[7-(2-fluoro-3-hydroxy-1-naphthyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one

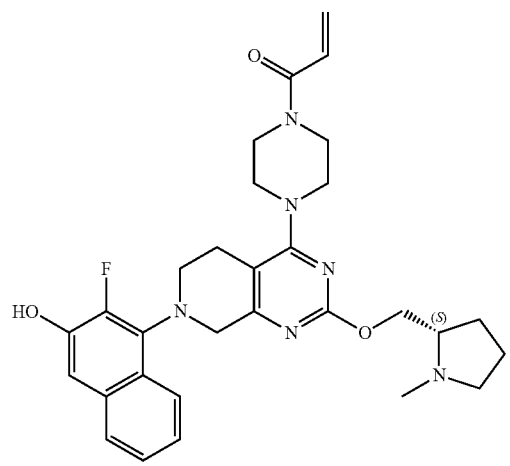

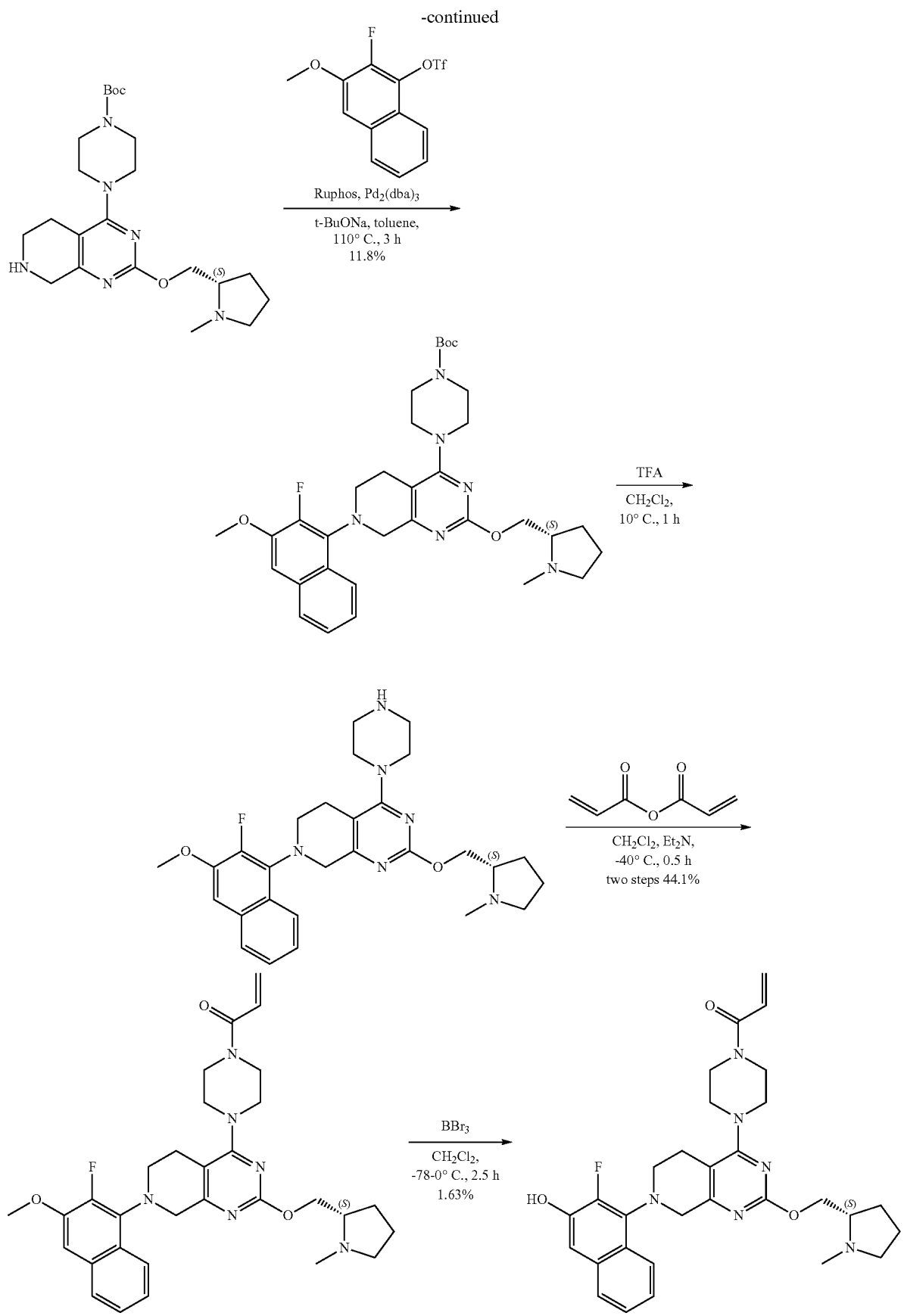

Step A: tert-butyl 4-[7-(2-fluoro-3-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate (0.50 g, 1.16 mmol), (2-fluoro-3-methoxy-1-naphthyl) trifluoromethanesulfonate (562 mg, 1.73 mmol), RuPhos (108 mg, 231 umol), Pd$_2$(dba)$_3$ (106 mg, 116 umol) and t-BuONa (333 mg, 3.47 mmol) in toluene (7 mL) was stirred at 110° C. for 3 hours under nitrogen atmosphere. The mixture was cooled and the pH of the aqueous layer adjusted to 7 by addition of saturated sodium bicarbonate solution and the aqueous layer extracted with ether acetate (3×20 mL). The combined organic layers were washed with saturated sodium chloride solution, dried over Na$_2$SO$_4$, filtered and concentrated under vacuum. The residue was purified by column chromatography (SiO$_2$, dichloromethane/methanol=10/1) and the mixture was concentrated to give tert-butyl 4-[7-(2-fluoro-3-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (0.20 g, 274 umol, 11.8% yield) as a yellow solid. ESI MS m/z 607.0 [M+H]$^+$.

Step B: 7-(2-fluoro-3-methoxy-1-naphthyl)-2-[[(2S)-1-methylpyrrolidin-2-yl]methoxy]-4-piperazin-1-yl-6,8-dihydro-5H-pyrido[3,4-d]pyrimidine A mixture tert-butyl 4-[7-(2-fluoro-3-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (0.20 g, 330 umol) and TFA (564 mg, 4.94 mmol, 366 uL) in dichloromethane (0.4 mL) was stirred at 10° C. for 1 hour. The mixture was concentrated under vacuum to give 7-(2-fluoro-3-methoxy-1-naphthyl)-2-[[(2S)-1-methylpyrrolidin-2-yl] methoxy]-4-piperazin-1-yl-6,8-dihydro-5H-pyrido[3,4-d]pyrimidine (205 mg, crude) as a yellow oil which was used in the next step without further purification. ESI MS m/z 507.0 [M+H]$^+$.

Step C: 1-[4-[7-(2-fluoro-3-methoxy-1-naphthyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one To a solution of 7-(2-fluoro-3-methoxy-1-naphthyl)-2-[[(2S)-1-methyl pyrrolidin-2-yl]methoxy]-4-piperazin-1-yl-6,8-dihydro-5H-pyrido[3,4-d]pyrimidine (0.20 g, crude) and TEA (399 mg, 3.95 mmol, 549 uL) in dichloromethane (5 mL) was added prop-2-enoyl prop-2-enoate (49.8 mg, 394 umol) at −40° C., then stirred at −40° C. for 0.5 h. The mixture was quenched with methanol (0.10 mL) and concentrated under vacuum. The residue was purified by reversed phase flash [water (0.1% TFA)/acetonitrile]. The aqueous layer pH was to 7 by addition of saturated sodium bicarbonate solution and the aqueous layer extracted with dichloromethane/methanol (10/1) (3×10 mL). The combined organic layers were washed with saturated sodium chloride (1×5 mL), dried over Na$_2$SO$_4$, filtered and concentrated under vacuum to give 1-[4-[7-(2-fluoro-3-methoxy-1-naphthyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one (0.10 g, 174 umol, 44.1% yield) as a yellow oil. ESI MS m/z 561.5 [M+H]$^+$.

Step D: 1-[4-[7-(2-fluoro-3-hydroxy-1-naphthyl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one To a solution of 1-[4-[7-(2-fluoro-3-methoxy-1-naphthyl)-2-[[(2S)-1-methylpyrrolidin-2-yl]methoxy]-6,8-dihydro-5H-pyrido [3,4-d]pyrimidin-4-yl]piperazin-1-yl] prop-2-en-1-one (0.10 g, 174 umol) in dichloromethane (3 mL) was added BBr$_3$ (223 mg, 892 umol, 85.9 uL) at −78° C. The mixture was stirred at −78° C. for 0.5 h and 0° C. for 2 hours. The mixture was concentrated under vacuum, diluted with dichloromethane (3 mL) and water and the aqueous layer pH adjusted to >7 by addition of saturated sodium bicarbonate solution at −78-0° C. The aqueous layer was next extracted with dichloromethane (3×5.00 mL). The combined organics were concentrated under vacuum. The residue was purified by column chromatography (Al$_2$O$_3$, dichloromethane/methanol=10/1) and the mixture was concentrated under vacuum. The residue was purified by prep-HPLC (column: Phenomenex Gemini 150*25 mm*10 um; mobile phase: [water (10 mM NH$_4$HCO$_3$)-ACN]; B %: 30%-60%, 3 min) and further purified by prep-HPLC (column: Luna C18 150*25 5 u; mobile phase: [water (0.225% FA)-ACN]; B %: 20%-50%, 10 min). The desired fractions were collected and lyophilized to give 1-[4-[7-(2-fluoro-3-hydroxy-1-naphthyl)-2-[[(2S)-1-methylpyrrolidin-2-yl] methoxy]-6,8-dihydro-5H-pyrido[3,4-d]pyrimidin-4-yl]piperazin-1-yl]prop-2-en-1-one (1.59 mg, 2.91 umol, 1.63% yield, 100% purity, FA) as a yellow solid. ESI MS m/z 547.2[M+H]$^+$.

Example 250

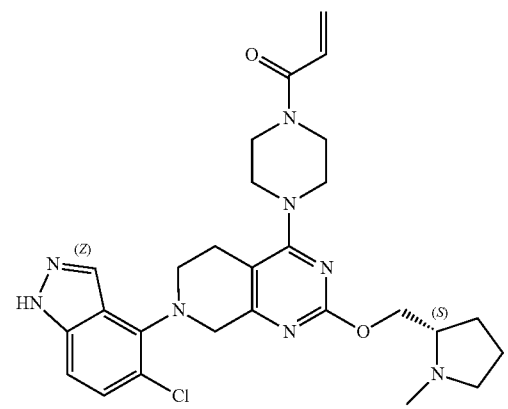

1-[4-[7-(5-chloro-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one
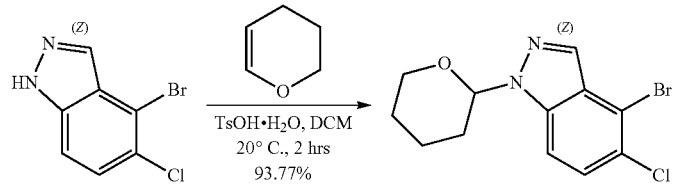
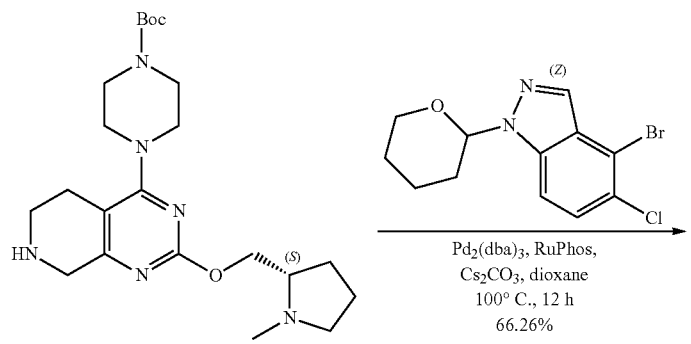
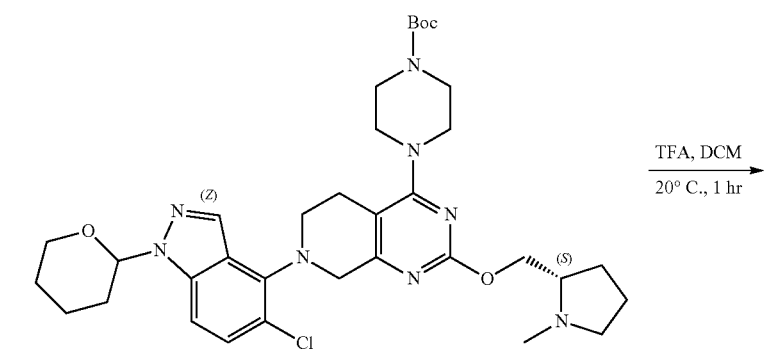
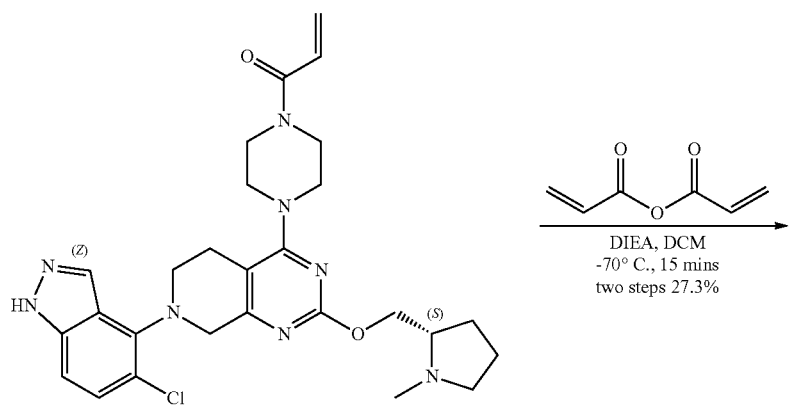

-continued

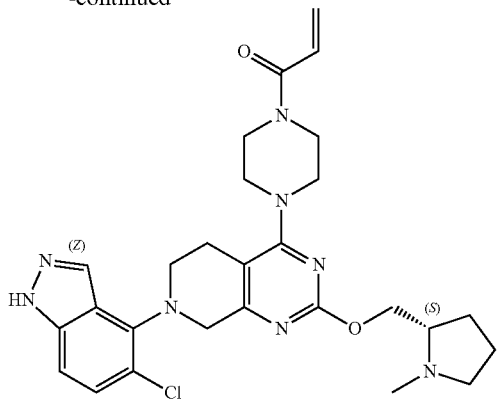

Step A: 4-bromo-5-chloro-1-tetrahydropyran-2-yl-indazole

To a solution of 4-bromo-5-chloro-1H-indazole (100 mg, 432.0 umol) in DCM (3 mL) was added TsOH.H$_2$O (8.22 mg, 43.2 umol) and 3,4-dihydro-2H-pyran (72.7 mg, 864 umol, 79.0 uL). The mixture was stirred at 20° C. for 2 hours. The reaction was washed by water (20 mL) and the aqueous layer extracted with ethyl acetate (20 mL×2). The combined organics were dried with Na$_2$SO$_4$ and the solvent removed under vacuum. The residue was purified by column chromatography (SiO$_2$, Petroleum ether/Ethyl acetate=10:1) to give 4-bromo-5-chloro-1-tetrahydropyran-2-yl-indazole (270 mg, 810 umol, 93.8% yield) as a white solid. ESI MS m/z 547.2[M+H]$^+$.

Step B: tert-butyl-4-[7-(5-chloro-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate (123 mg, 284.4 umol), 4-bromo-5-chloro-1-tetrahydropyran-2-yl-indazole (135 mg, 427 umol), Pd$_2$(dba)$_3$ (26.0 mg, 28.4 umol), RuPhos (20.0 mg, 42.9 umol) and Cs$_2$CO$_3$ (278 mg, 853 umol) in dioxane (10 mL) was degassed and purged with N$_2$ and then the mixture was stirred at 100° C. for 12 hrs under N$_2$ atmosphere. The reaction was quenched by adding water (20 mL). The mixture was extracted with ethyl acetate (20 mL×3). The combined organics were dried with Na$_2$SO$_4$ and the solvent was concentrated under vacuum. The residue was purified by column chromatography (SiO$_2$, Ethyl acetate/MeOH=10/1) to give tert-butyl-4-[7-(5-chloro-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (130.0 mg, 188.4 umol, 66.3% yield) as a white solid. ESI MS m/z 668.2[M+H]$^+$.

Step C: 7-(5-chloro-1H-indazol-4-yl)-2-[[(2S)-1-methylpyrrolidin-2-yl]methoxy]-4-piperazin-1-yl-6,8-dihydro-5H-pyrido[3,4-d]pyrimidine To a solution of tert-butyl 4-[7-(5-chloro-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (50.0 mg, 74.9 umol) in DCM (2 mL) was added TFA (1.95 mL). The mixture was stirred at 20° C. for 1 hr. The organic solvent was removed under vacuum to give 7-(5-chloro-1H-indazol-4-yl)-2-[[(2S)-1-methylpyrrolidin-2-yl]methoxy]-4-piperazin-1-yl-6,8-dihydro-5H-pyrido[3,4-d]pyrimidine (40.0 mg, crude, 2TFA) as a yellow oil which was used directly in the next step without further purification. ESI MS m/z 483.4 [M+H]$^+$.

Step D: 1-[4-[7-(5-chloro-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one To a solution of 7-(5-chloro-1H-indazol-4-yl)-2-[[(2S)-1-methylpyrrolidin-2-yl]methoxy]-4-piperazin-1-yl-6,8-dihydro-5H-pyrido[3,4-d]pyrimidine (40.0 mg, 2TFA) and DIEA (50 mg, 387 umol, 67.4 uL) in DCM (3 mL) was added dropwise acrylic anhydride (9.0 mg, 71.4 umol) under N$_2$ atmosphere. The mixture was stirred at −70° C. for 15 mins. The reaction was quenched by adding water (10 mL). The mixture was extracted with ethyl acetate (10 mL×3). The organic layer was dried with Na$_2$SO$_4$ and the solvent removed under vacuum. The residue was purified by prep-HPLC (column: Luna C18 150*25 5 u; mobile phase: [water (0.225% FA)-ACN]; B %: 10%-37%, 10 mins) and lyophilized to give 1-[4-[7-(5-chloro-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one (11.9 mg, 20.8 umol, two steps 27.3%,100% e.e.) as a yellow solid. ESI MS m/z 537.2 [M+H]$^+$.

Example 251

2-(1-acryloyl-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile Step A: benzyl 4-(2-(((S)-1-(tert-butoxycarbonyl)-2-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate In a microwave tube benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (200 mg, 0.362 mmol) was dissolved in dioxane (181 μl, 0.362 mmol) and treated with cesium carbonate (236 mg, 0.723 mmol) and (S)-tert-butyl 2-(hydroxymethyl)-2-methylpyrrolidine-1-carboxylate (389 mg, 1.81 mmol). The tube was then capped and heated to 90° C. for 2 hours. LC/MS showed reaction completion. The reaction was cooled to room temperature and filtered through GF/F paper. The filtrate was concentrated in vacuo and chromatographed on the CombiFlash (0%-10% DCM:MeOH). All fractions containing clean product were combined and concentrated to give benzyl 4-(2-(((S)-1-(tert-butoxycarbonyl)-2-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (264 mg, 0.361 mmol, 99.7% yield). ES+APCI MS m/z 732.4 [M+H]+.

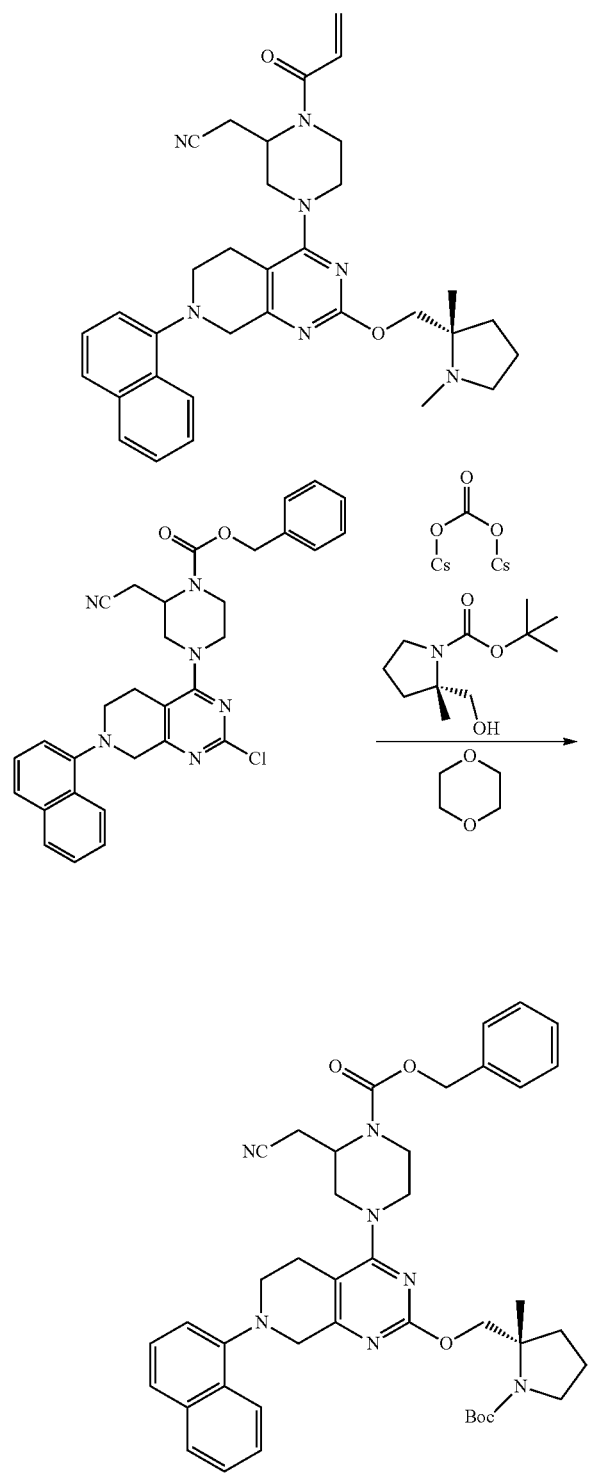

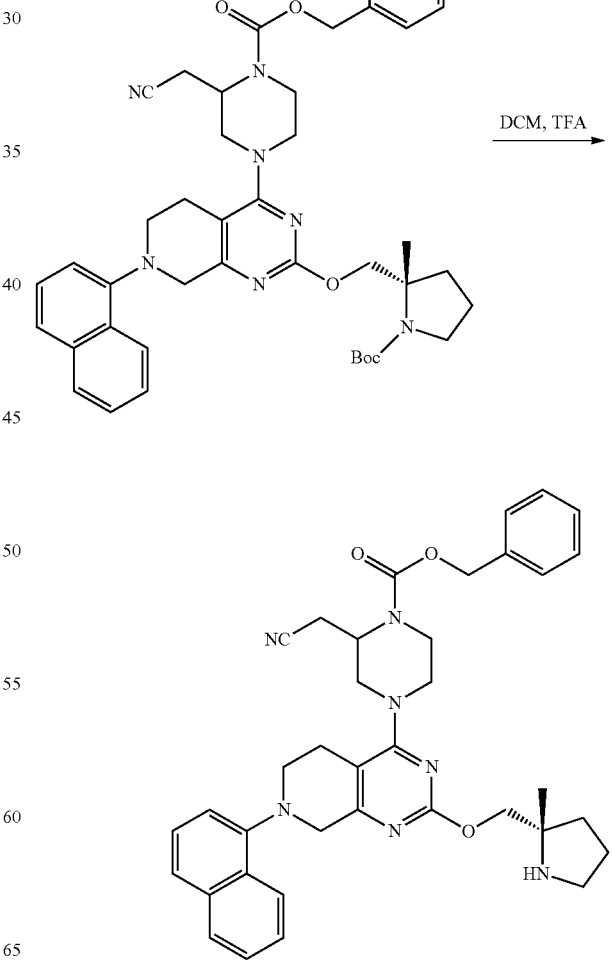

Step B: benzyl 2-(cyanomethyl)-4-(2-(((S)-2-methylpyrrolidin-2-yl)methoxy)-7-(naphthalen-1-yl)-5,6,7,8-tetrahydropyrido[3,4-d]pyrimidin-4-yl)piperazine-1-carboxylate benzyl 4-(2-(((S)-1-(tert-butoxycarbonyl)-2-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (264 mg, 0.361 mmol) was dissolved in dichloromethane (3607 µl, 0.361 mmol) and treated with TFA (556 µl, 7.21 mmol). The reaction stirred at room temperature for 1 hour. LC/MS showed reaction completion. The reaction was concentrated in vacuo and treated with saturated bicarb. The aqueous layer was extracted with DCM (2×) and the combined organics dried over Na$_2$SO$_4$ and concentrated in vacuo to give benzyl 2-(cyanomethyl)-4-(2-(((S)-2-methylpyrrolidin-2-yl)methoxy)-7-(naphthalen-1-yl)-5,6,7,8-tetrahydropyrido[3,4-d]pyrimidin-4-yl)piperazine-1-carboxylate (210 mg, 0.332 mmol, 92.2% yield). ES+APCI MS m/z 632.3 [M+H]$^+$.

[3,4-d]pyrimidin-4-yl)piperazine-1-carboxylate (105 mg, 0.1662 mmol) was dissolved in formic acid (94.05 µl, 2.493 mmol) and treated with Formaldehyde (1868 µl, 24.93 mmol). The reaction mixture stirred at 85° C. for 1 hour. LC/MS showed reaction completion. The reaction was cooled to room temperature and treated with saturated bicarb and the mixture was extracted with DCM (2×) and the organics combined and dried over Na$_2$SO$_4$. The combined organics were concentrated in vacuo and chromatographed on the CombiFlash (0%-10% DCM:MeOH). All fractions containing clean product were combined and concentrated in vacuo to give benzyl 2-(cyanomethyl)-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazine-1-carboxylate (75 mg, 0.1161 mmol, 69.88% yield). ES+APCI MS m/z 646.4 [M+H]$^+$.

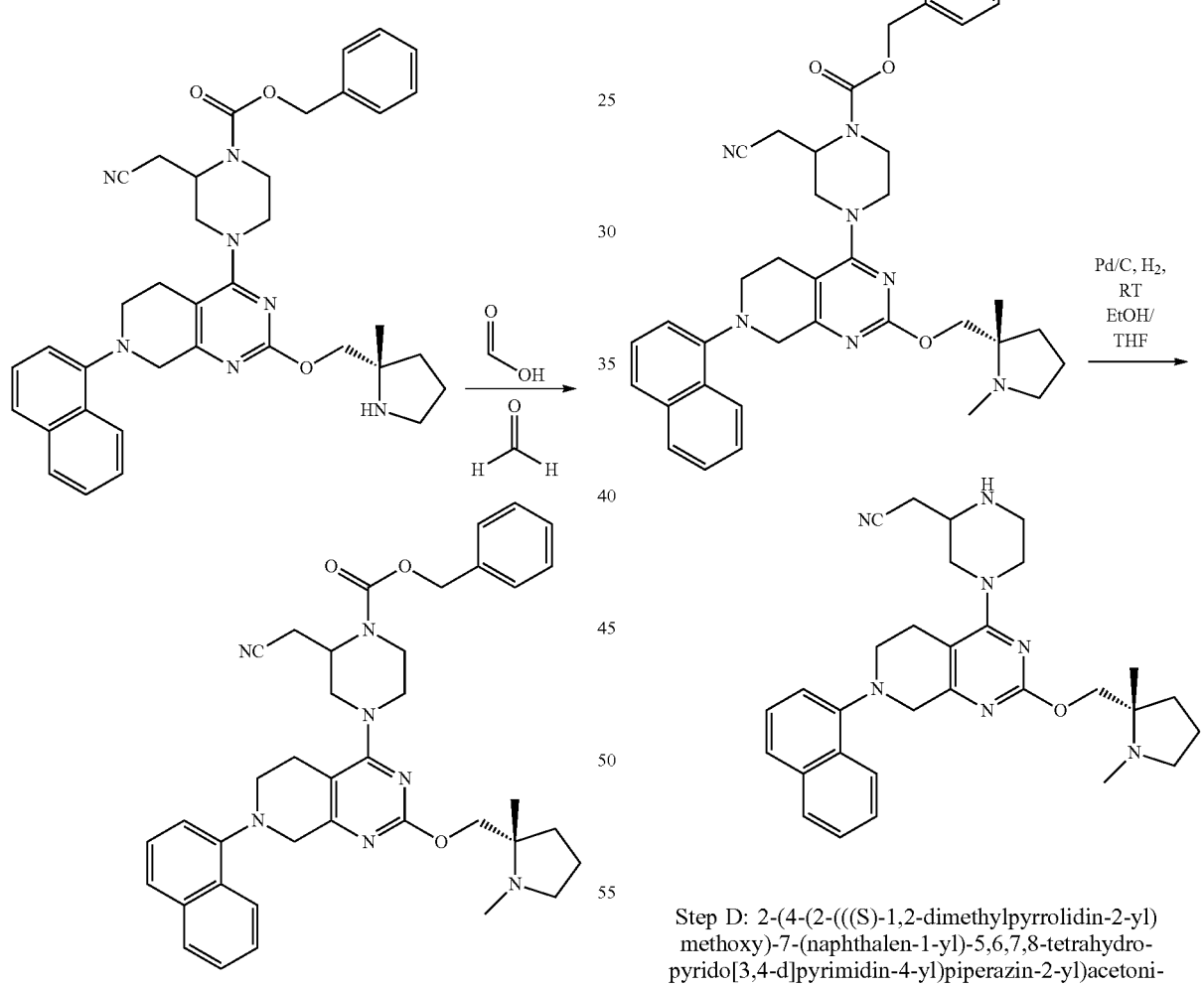

Step C: benzyl 2-(cyanomethyl)-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazine-1-carboxylate benzyl 2-(cyanomethyl)-4-(2-(((S)-2-methylpyrrolidin-2-yl)methoxy)-7-(naphthalen-1-yl)-5,6,7,8-tetrahydropyrido

Step D: 2-(4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile A solution of benzyl 2-(cyanomethyl)-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazine-1-carboxylate (117 mg, 0.181 mmol) in EtOH (1812 µl, 0.181 mmol) and THF (1812 µl, 0.181 mmol) was purged with N$_2$ for 5 minutes. To this solution was added Palladium (96.4 mg, 0.0453 mmol) (Degussa Type, 10 wt %, 50% H$_2$O), and was immediately capped and purged with $N_2$ for an additional 5 min. The solution was then stirred under $H_2$ atmosphere for 1 hour. LC/MS showed clean desired product. The mixture was diluted with MeOH and filtered through packed celite. The filtrate was then concentrated in vacuo to provide 2-(4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile (88 mg, 0.172 mmol, 94.9% yield). ES+APCI MS m/z 512.3 [M+H]+.

Step E: 2-(1-acryloyl-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile To a suspension of 2-(4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile (88 mg, 0.17 mmol) in dichloromethane (1720 μl, 0.17 mmol) at ambient temperature was added Acyloyl Chloride (14 μl, 0.17 mmol) followed by Hunig's base (60 μl, 0.34 mmol). The reaction was then stirred at ambient temperature for 30 minutes. LC/MS showed reaction completion. The reaction mixture was concentrated in vacuo. The concentrate was resuspended in a 60:40 mixture of ACN:H2O and purified on the Gilson (prep HPLC) using 5→95% ACN/0.1% TFA in water/0.1% TFA as eluent. Fractions containing product were combined and free based with saturated bicarb and the organics extracted with DCM. The organics were dried over $MgSO_4$ and concentrated in vacuo to give 2-(1-acryloyl-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile (14 mg, 0.025 mmol, 14% yield). ES+APCI MS m/z 566.3 [M+H]+.

Example 252 tert-butyl 2-(cyanomethyl)-4-[2-[[(2S)-1-isopropylpyrrolidin-2-yl]methoxy]-7-(1-naphthyl)-6,8-dihydro-5H-pyrido[3,4-d]pyrimidin-4-yl]piperazine-1-carboxylate

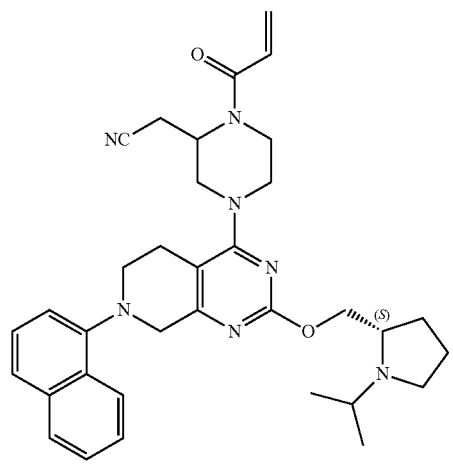

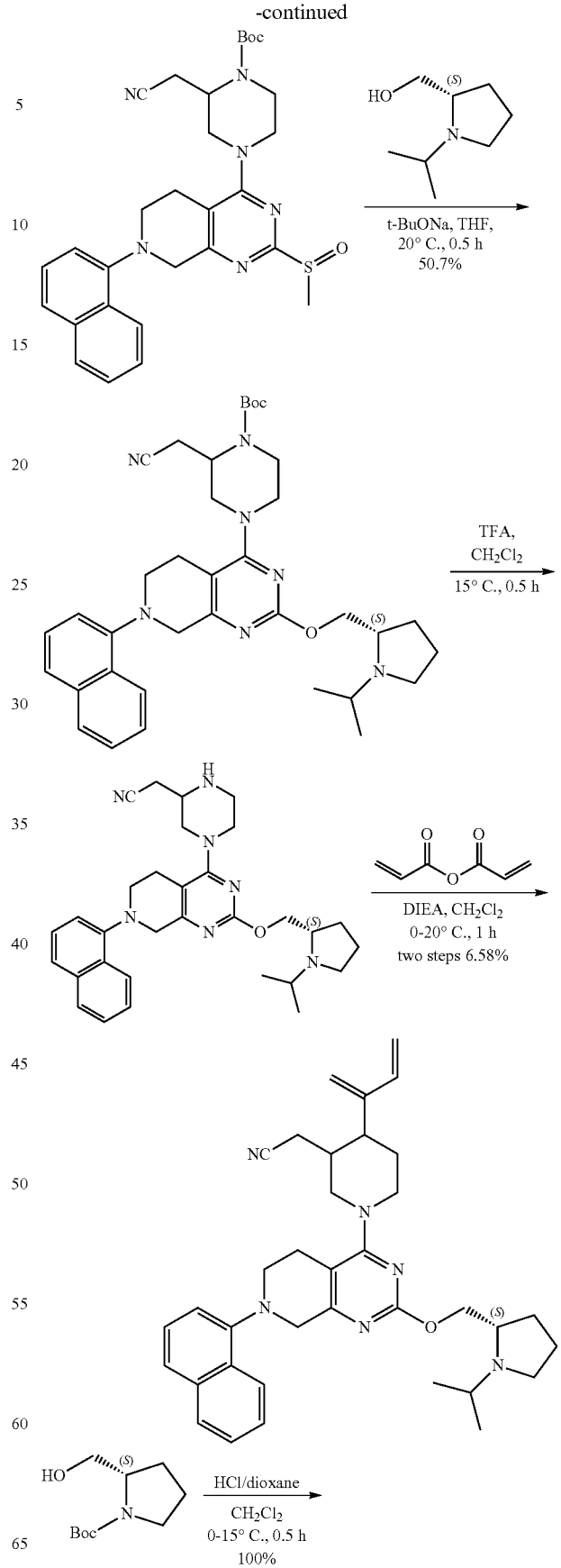

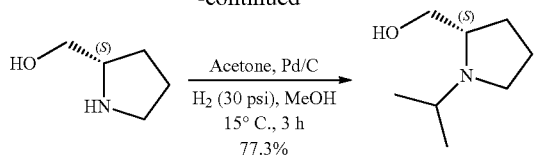

Step A: (S)-pyrrolidin-2-ylmethanol

To a solution of (S)-tert-butyl 2-(hydroxymethyl) pyrrolidine-1-carboxylate (2 g, 9.94 mmol) in CH$_2$Cl$_2$ (40 mL) was added HCl (4 M in dioxane, 49.69 mL) at 0° C. under a nitrogen atmosphere. After stirring at 15° C. for 30 min, the mixture was concentrated under vacuum. (S)-pyrrolidin-2-ylmethanol (1.37 g, 9.96 mmol, 100% yield, HCl) was obtained as a yellow solid.

Step B: [(2S)-1-isopropylpyrrolidin-2-yl] methanol

A mixture of [(2S)-pyrrolidin-2-yl]methanol (750 mg, 7.41 mmol, 724 uL) and acetone (4.31 g, 74.2 mmol, 5.46 mL) in MeOH (20 mL) was hydrogenated under H$_2$ (30 psi) with Pd/C (100 mg, 7.41 mmol, 10% purity) at 15° C. for 3 hours. The mixture was filtered and concentrated under vacuum. [(2S)-1-isopropylpyrrolidin-2-yl]methanol (0.821 g, 5.73 mmol, 77.3% yield) was obtained as a yellow oil. $^1$H NMR (400 MHz, methanol-d$_4$) δ=3.54 (dd, J=4.0, 10.8 Hz, 1H), 3.40-3.35 (m, 1H), 2.99-2.86 (m, 3H), 2.60-2.50 (m, 1H), 1.94-1.82 (m, 1H), 1.82-1.66 (m, 3H), 1.15 (d, J=6.4 Hz, 3H), 1.08 (d, J=6.4 Hz, 3H).

Step C: tert-butyl 2-(cyanomethyl)-4-[2-[[(2S)-1-isopropylpyrrolidin-2-yl]methoxy]-7-(1-naphthyl)-6,8-dihydro-5H-pyrido[3,4-d]pyrimidin-4-yl] piperazine-1-carboxylatete To a mixture of tert-butyl 2-(cyanomethyl)-4-[2-methylsulfinyl-7-(1-naphthyl)-6,8-dihydro-5H-pyrido[3,4-d]pyrimidin-4-yl]piperazine-1-carboxylate (300 mg, 549 umol) and [(2S)-1-isopropylpyrrolidin-2-yl]methanol (157 mg, 1.10 mmol) in THF (5 mL) was added t-BuONa (158 mg, 1.65 mmol). After stirring at 20° C. for 0.5 hour, the reaction mixture was neutralized with HCl (1 M) to pH=7 while holding the solution temperature to 0° C., and then the mixture was concentrated under reduced pressure. The residue was purified by reversed phase flash [water (0.1% TFA)/acetonitrile]. The desired fractions were collected and neutralized with saturated NaHCO$_3$ solution and extracted with ethyl acetate (200 mL). The organic layer was dried over sodium sulfate, filtered and concentrated under vacuum. tert-butyl 2-(cyanomethyl)-4-[2-[[(2S)-1-isopropylpyrrolidin-2-yl]methoxy]-7-(1-naphthyl)-6,8-dihydro-5H-pyrido[3,4-d]pyrimidin-4-yl]piperazine-1-carboxylate (174 mg, 278 umol, 50.7% yield, 100% purity) was obtained as a yellow oil. ESI MS m/z 626.2 [M+H]$^+$.

Step D: 2-[4-[2-[[(2S)-1-isopropylpyrrolidin-2-yl]methoxy]-7-(1-naphthyl)-6,8-dihydro-5H-pyrido[3,4-d]pyrimidin-4-yl]piperazin-2-yl]acetonitrile To a solution of tert-butyl 2-(cyanomethyl)-4-[2-[[(2S)-1-isopropyl pyrrolidin-2-yl]methoxy]-7-(1-naphthyl)-6,8-dihydro-5H-pyrido[3,4-d]pyrimidin-4-yl]piperazine-1-carboxylate (174 mg, 278 umol) in CH$_2$Cl$_2$ (5 mL) was added TFA (7.70 g, 67.5 mmol, 5.00 mL) at 0° C. under nitrogen atmosphere. After stirring at 15° C. for 0.5 h, the mixture was concentrated under vacuum. 2-[4-[2-[[(2S)-1-isopropylpyrrolidin-2-yl] methoxy]-7-(1-naphthyl)-6,8-dihydro-5H-pyrido[3,4-d]pyrimidin-4-yl]piperazin-2-yl] acetonitrile (178 mg, crude, TFA) was obtained as a yellow oil. ESI MS m/z 526.1 [M+H]$^+$.

Step E: 2-[4-[2-[[(2S)-1-isopropylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a mixture of 2-[4-[2-[[(2S)-1-isopropylpyrrolidin-2-yl]methoxy]-7-(1-naphthyl)-6,8-dihydro-5H-pyrido[3,4-d]pyrimidin-4-yl]piperazin-2-yl]acetonitrile (178 mg, crude, TFA salt) and DIEA (360 mg, 2.78 mmol, 485 uL) in CH$_2$Cl$_2$ (5 mL) was added prop-2-enoyl prop-2-enoate (28.1 mg, 223 umol) at 0° C. The mixture was stirred at 20° C. for 1 hour. The reaction mixture was quenched with NaHCO$_3$ saturated solution (5 mL) at 0° C., and then extracted with CH$_2$Cl$_2$ (2×25 mL). The combined organic layers were washed with brine (1×50 mL), dried over sodium sulfate, filtered and concentrated under vacuum. The residue was purified by prep-HPLC (column: Boston Green ODS 150*30 5 u; mobile phase: [water (0.225% FA)-ACN]; B %: 27%-54%, 10 min). 2-[4-[2-[[(2S)-1-isopropylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (11.7 mg, 18.3 umol, two steps 6.58% yield, 97.9% purity, FA) was obtained as a brown solid. ESI MS m/z 580.2 [M+H]$^+$.

Example 253

2-(1-acryloyl-4-(7-(7-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

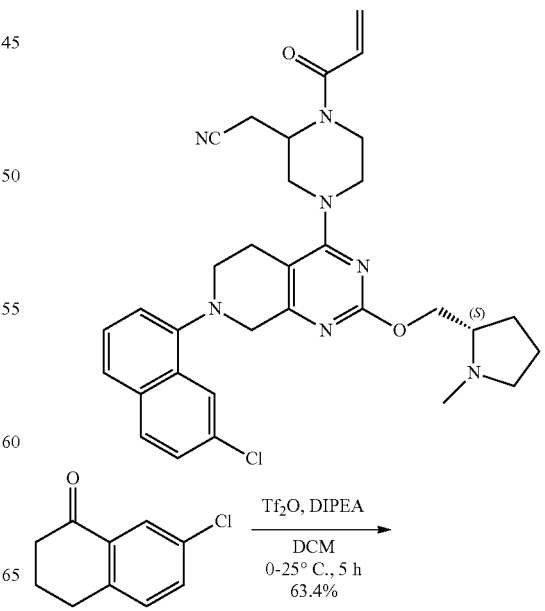

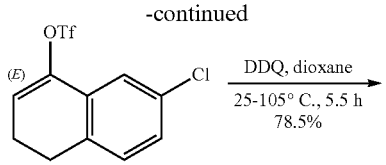

Step A: (7-chloro-3,4-dihydronaphthalen-1-yl) trifluoromethanesulfonate

To a mixture of 7-chlorotetralin-1-one (2 g, 11.1 mmol, 1 eq) and DIEA (4.29 g, 33.2 mmol, 5.79 mL) in DCM (35 mL) was added Tf$_2$O (4.69 g, 16.6 mmol, 2.74 mL) in one portion at 0° C. under N$_2$. The mixture was stirred at 25° C. for 5 hours. The reaction mixture was concentrated under reduced pressure. The residue was purified by column chromatography (SiO$_2$, Petroleum ether/Ethyl acetate=200/1 to 50/1). (7-chloro-3,4-dihydronaphthalen-1-yl) trifluoromethanesulfonate (2.25 g, 7.02 mmol, 63.4% yield, 97.6% purity) was obtained as a colorless oil. $^1$H NMR (400 MHz, chloroform-d) δ=7.32 (d, J=2.0 Hz, 1H), 7.24 (dd, J=2.0, 8.0 Hz, 1H), 7.12 (d, J=8.0 Hz, 1H), 6.10 (t, J=4.8 Hz, 1H), 2.88-2.80 (m, 2H), 2.53 (dt, J=4.8, 8.0 Hz, 2H).

Step B: (7-chloro-1-naphthyl) trifluoromethanesulfonate

To a mixture of (7-chloro-3,4-dihydronaphthalen-1-yl) trifluoromethanesulfonate (1.57 g, 5.02 mmol) in dioxane (35 mL) was added DDQ (2.28 g, 10.0 mmol) in one portion under N$_2$. The mixture was stirred at 25° C. for 30 min, then heated to 105° C. and stirred for 5 hours. The reaction mixture was concentrated under reduced pressure to remove 1,4-dioxane. The residue was purified by column chromatography (SiO$_2$, Petroleum ether/Ethyl acetate=200/1 to 50/1). (7-chloro-1-naphthyl) trifluoromethanesulfonate (1.24 g, 3.94 mmol, 78.5% yield, 98.7% purity) was obtained as a colorless oil. $^1$H NMR (400 MHz, chloroform-d) δ=8.05 (d, J=2.0 Hz, 1H), 7.87-7.83 (m, 2H), 7.57-7.47 (m, 3H).

Title compound was prepared as in Example 210 Steps E-G, substituting (7-chloro-1-naphthyl) trifluoromethanesulfonate for 1-bromo-2-(trifluoromethyl)benzene in step E and also substituting prop-2-enoyl prop-2-enoate for acryloyl chloride in step G. ESI MS m/z 586.1 [M+H]$^+$.

Example 254

2-[4-[7-(5-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

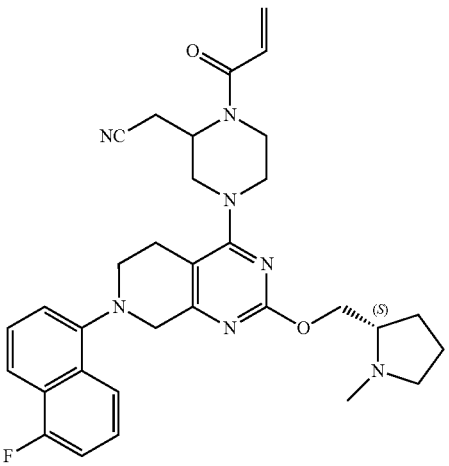

Title compound was prepared as in Example 210 Steps E-G, substituting 1-bromo-5-fluoronaphthalene for 1-bromo-2-(trifluoromethyl)benzene in step E and also substituting prop-2-enoyl prop-2-enoate for acryloyl chloride in step G. ESI MS m/z 570.3 [M+H]$^+$.

Example 255

2-[4-[7-(7-methoxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

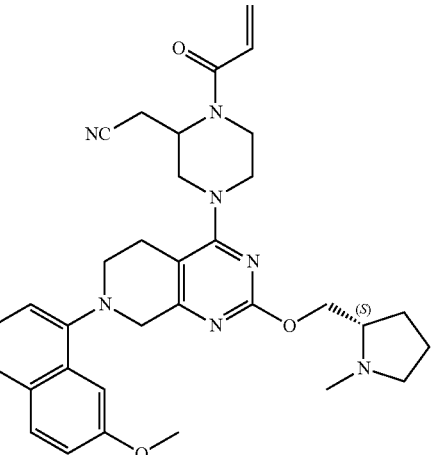

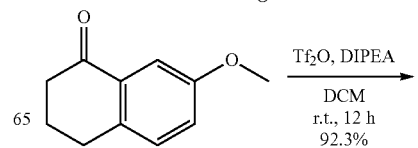

-continued

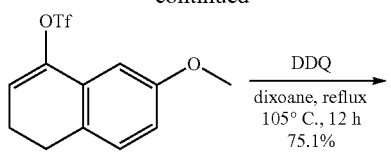

Step A: (7-methoxy-3,4-dihydronaphthalen-1-yl) trifluoromethanesulfonate

To the solution of 7-methoxytetralin-1-one (1 g, 5.67 mmol) and DIEA (2.20 g, 17.0 mmol, 2.97 mL) in DCM (15 mL) was added Tf₂O (2.40 g, 8.51 mmol, 1.40 mL) dropwise, then the mixture was stirred at 20° C. for 12 hours. The reaction mixture was concentrated under vacuum. The residue was purified by silica gel chromatography (PE:EtOAc from 1:0 to 100:1) to give (7-methoxy-3,4-dihydronaphthalen-1-yl) trifluoromethanesulfonate (1.7 g, 5.24 mmol, 92.3% yield, 95.0% purity) as yellow oil. ¹H NMR (400 MHz, chloroform-d) δ=7.06 (d, J=8.4 Hz, 1H), 6.75 (dd, J=2.4, 8.4 Hz, 1H), 6.66 (d, J=2.4 Hz, 1H), 6.45 (s, 1H), 3.80 (s, 3H), 3.04-2.96 (m, 2H), 2.68 (t, J=8.4 Hz, 2H).

Step 2: (7-methoxy-1-naphthyl) trifluoromethanesulfonate

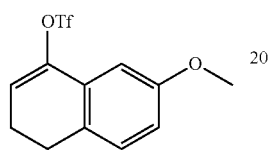

A mixture of (7-methoxy-3,4-dihydronaphthalen-1-yl) trifluoromethanesulfonate (1.7 g, 5.51 mmol) and DDQ (2.50 g, 11.0 mmol) in dioxane (30 mL) was stirred at 105° C. for 12 hours. The reaction mixture was concentrated under vacuum. The residue was purified by silica gel chromatography (PE:EtOAc from 1:0 to 50:1) to give (7-methoxy-1-naphthyl) trifluoromethanesulfonate (1.41 g, 4.14 mmol, 75.1% yield, 90.0% purity) as a colourless oil. ¹H NMR (400 MHz, chloroform-d) δ=7.84 (d, J=9.2 Hz, 1H), 7.78 (d, J=8.8 Hz, 1H), 7.65 (d, J=2.4 Hz, 1H), 7.24-7.21 (m, 2H), 7.15 (d, J=2.4 Hz, 1H), 3.94 (s, 3H).

Title compound was prepared as in Example 210 Steps E-G, substituting (7-methoxy-1-naphthyl) trifluoromethanesulfonate for 1-bromo-2-(trifluoromethyl)benzene in step E and also substituting prop-2-enoyl prop-2-enoate for acryloyl chloride in step G. ESI MS m/z 582.4 [M+H]⁺.

Example 256

1-(2-(methoxymethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-1-yl) prop-2-en-1-one

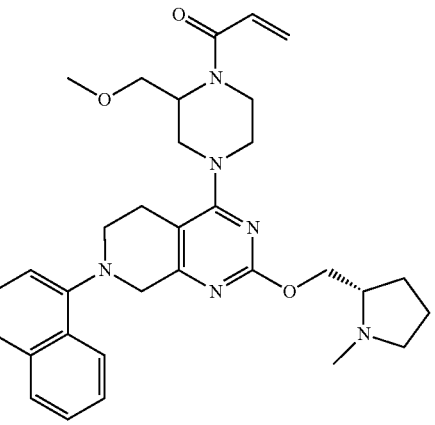

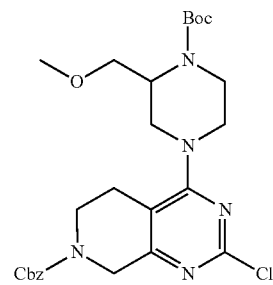

Step A: benzyl 4-(4-(tert-butoxycarbonyl)-3-(methoxymethyl)piperazin-1-yl)-2-chloro-5,8-dihydropyrido[3,4-d]pyrimidine-7(6H)-carboxylate A solution of tert-butyl 2-(methoxymethyl)piperazine-1-carboxylate (0.715 g, 3.10 mmol) in N,N-dimethylacetamide (3 ml) was cooled on an ice bath with stirring and solid benzyl 2,4-dichloro-5,8-dihydropyrido[3,4-d]pyrimidine-7(6H)-carboxylate (1.00 g, 2.96 mmol) was added in small portions, followed by DIPEA (0.57 mL, 3.25 mmol, 1.1 eq.). The resulting solution was allowed to warm up to r.t. over 1 hour, and then divided between water (15 mL) and MTBE (50 mL). The organic layer was washed with water (2×10 mL), brine (10 mL), dried over Na₂SO₄ and evaporated in vacuo to give a yellow solid (1.54 g, 98%). ES+APCI MS m/z 532.3, [M+H]⁺.

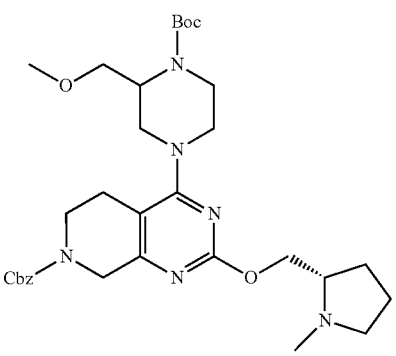 [SMILES: COCC1CN(c2nc(OC[C@@H]3CCCN3C)nc3c2CCN(C(=O)OCc2ccccc2)C3)CCN1C(=O)OC(C)(C)C]

Step B: benzyl 4-(4-(tert-butoxycarbonyl)-3-(methoxymethyl)piperazin-1-yl)-2-(((S)-1-methylpyrrolidin-2-yl)methoxy)-5,8-dihydropyrido[3,4-d]pyrimidine-7(6H)-carboxylate A mixture of crude benzyl 4-(4-(tert-butoxycarbonyl)-3-(methoxymethyl)piperazin-1-yl)-2-chloro-5,8-dihydropyrido[3,4-d]pyrimidine-7(6H)-carboxylate (500 mg, 0.940 mmol), (S)-(1-methylpyrrolidin-2-yl)methanol (216 mg, 1.88 mmol), Cs$_2$CO$_3$ (612 mg, 1.88 mmol) and dioxane (0.5 mL) was flushed with nitrogen. The vial was capped and stirred at 120° C. overnight. The reaction mixture was cooled, divided between EtOAc (20 mL) and water (10 mL), the organic layer was washed with water and brine (5 mL each), dried over Na$_2$SO$_4$ and evaporated in vacuo. The compound was purified by silica gel chromatography, Redisep 40 g, eluting with 4 to 10% MeOH/DCM+0.2% NH$_4$OH to give a yellow solid (197 mg, 34%). ES+APCI MS m/z 611.4 [M+H]$^+$.

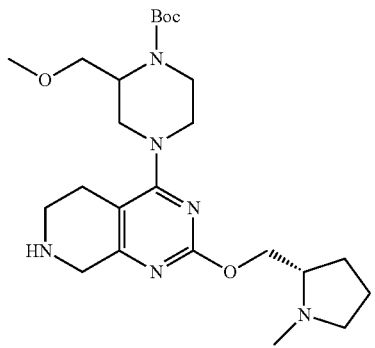 [SMILES: COCC1CN(c2nc(OC[C@@H]3CCCN3C)nc3c2CCNC3)CCN1C(=O)OC(C)(C)C]

Step C: tert-butyl 2-(methoxymethyl)-4-(2-(((S)-1-methylpyrrolidin-2-yl)methoxy)-5,6,7,8-tetrahydropyrido[3,4-d]pyrimidin-4-yl)piperazine-1-carboxylate A mixture of benzyl 4-(4-(tert-butoxycarbonyl)-3-(methoxymethyl)piperazin-1-yl)-2-(((S)-1-methylpyrrolidin-2-yl)methoxy)-5,8-dihydropyrido[3,4-d]pyrimidine-7(6H)-carboxylate (197 mg, 0.323 mmol), methanol (10 mL) and palladium on carbon (10 mg, 5%, Degussa type E101 NO/W) was degassed and stirred under hydrogen atmosphere (balloon) for 1 hour. The reaction mixture was filtered through Celite (2 mL), washed with MeOH (3×3 mL), evaporated in vacuo, and dried by evaporation with toluene in vacuo and under high vacuum to give a colorless solid (150 mg, 98%). ES+APCI MS m/z 477.2 [M+H]$^+$.

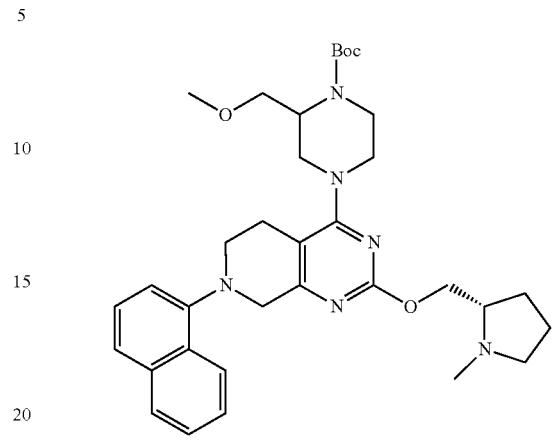

Step D: tert-butyl 2-(methoxymethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate A mixture of tert-butyl 2-(methoxymethyl)-4-(2-(((S)-1-methylpyrrolidin-2-yl)methoxy)-5,6,7,8-tetrahydropyrido[3,4-d]pyrimidin-4-yl)piperazine-1-carboxylate (150 mg, 0.315 mmol), Cs$_2$CO$_3$ (308 mg, 0.944 mmol), dioxane (1 mL), 1-iodonaphthalene (0.0689 ml, 0.472 mmol) and methanesulfonato(2-dicyclohexylphosphino-2',6'-di-i-propoxy-1,1'-biphenyl)(2-amino-1,1'-biphenyl-2-yl)palladium(II) (26.3 mg, 0.0315 mmol) (RuPhos-Pd-G3) was purged with nitrogen, the flask was capped and stirred at 70° C. overnight. The reaction mixture was cooled, divided between EtOAc (15 mL) and water (5 mL), the organic layer was washed with water and brine (5 mL each), dried over Na$_2$SO$_4$ and evaporated in vacuo. The compound was purified by silica gel chromatography, Redisep 40 g, using 4 to 10% MeOH+0.5% NH$_4$OH as eluent to give a colorless solid, 131 mg. ES+APCI MS m/z 603.3 [M+H]$^+$.

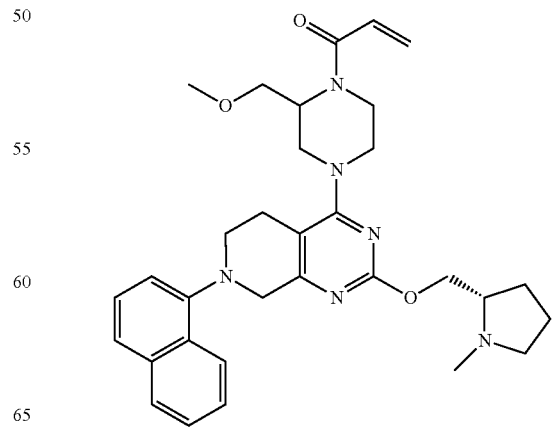

Step E: 1-(2-(methoxymethyl)-4-(2-(((S)-1-methyl-pyrrolidin-2-yl)methoxy)-7-(naphthalen-1-yl)-5,6,7,8-tetrahydropyrido[3,4-d]pyrimidin-4-yl)piperazin-1-yl)prop-2-en-1-one Tert-butyl 2-(methoxymethyl)-4-(2-(((S)-1-methylpyrrolidin-2-yl)methoxy)-7-(naphthalen-1-yl)-5,6,7,8-tetrahydropyrido [3,4-d]pyrimidin-4-yl)piperazine-1-carboxylate (130 mg, 0.2157 mmol) was dissolved in 1M trifluoroacetic acid in DCM, and the resulted solution was allowed to stay at r.t. for 1 h. The reaction mixture was divided between 2M $Na_2CO_3$ (5 mL) and DCM (15 mL), and the organic layer was evaporated in vacuo. The solid residue was dissolved in DCM (5 mL), cooled on ice-EtOH—$CO_2$ bath with stirring to −30° C. and triethylamine (0.09 ml, 0.64 mmol) was added, followed by acryloyl chloride (0.035 ml, 0.43 mmol). After 1 min at −30° C. the reaction mixture was quenched with $NH_4OH$ (0.05 mL) and evaporated in vacuo and dried under high vacuum. The residue was dissolved in DCM (5 mL), filtered through a cotton plug and purified by silica gel chromatography, Redisep 40 g, eluting with 5 to 10% MeOH/DCM+0.25% $NH_4OH$ to give a colorless solid (19.6 mg, 16%). ES+APCI MS m/z 557.3, [M+H]⁺.

Example 257

2-(1-acryloyl-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile

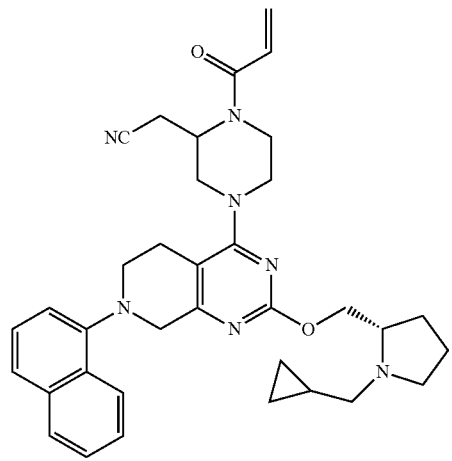

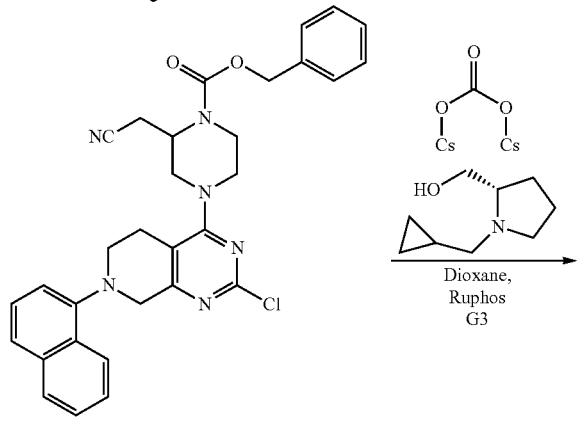

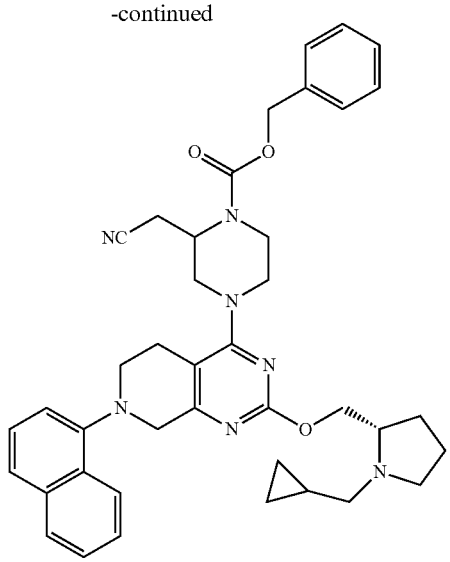

Step A: benzyl 2-(cyanomethyl)-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazine-1-carboxylate In a conical bottom vial, a solution of benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (200 mg, 0.362 mmol) in dioxane (3616 µl, 0.362 mmol) was sparged with Argon for 5 minutes. (S)-(1-(cyclopropylmethyl)pyrrolidin-2-yl)methanol (168 mg, 1.08 mmol), $Cs_2CO_3$ (353 mg, 1.08 mmol), Rhuphos Pd G3 (30.2 mg, 0.0362 mmol) were sequentially added under Argon and sparged for an additional 5 minutes. The reaction mixture was capped and heated at 100° C. for 1 hour. LC/MS showed reaction completion. EtOAc was added and washed with brine (2×). The combined organics were dried over Na2SO4 and concentrated in vacuo. The concentrate was purified by flash chromatography eluting with 0-20% DCM/MeOH+2% $NH_4OH$. All fractions containing clean desired product were combined and concentrated to give benzyl 2-(cyanomethyl)-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazine-1-carboxylate (90 mg, 0.134 mmol, 37.0% yield). ES+APCI MS m/z 672.4 [M+H]⁺.

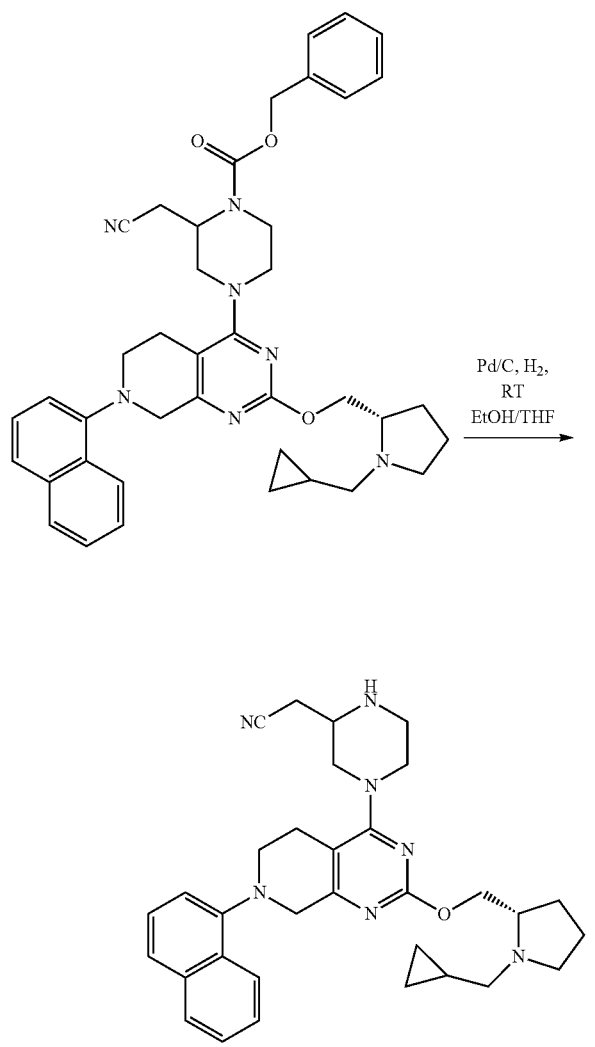 [SMILES: N#CCC1CN(c2nc(OC[C@@H]3CCCN3CC3CC3)nc3c2CCN(c2cccc4ccccc24)C3)CCN1C(=O)OCc1ccccc1 ; N#CCC1CN(c2nc(OC[C@@H]3CCCN3CC3CC3)nc3c2CCN(c2cccc4ccccc24)C3)CCN1]

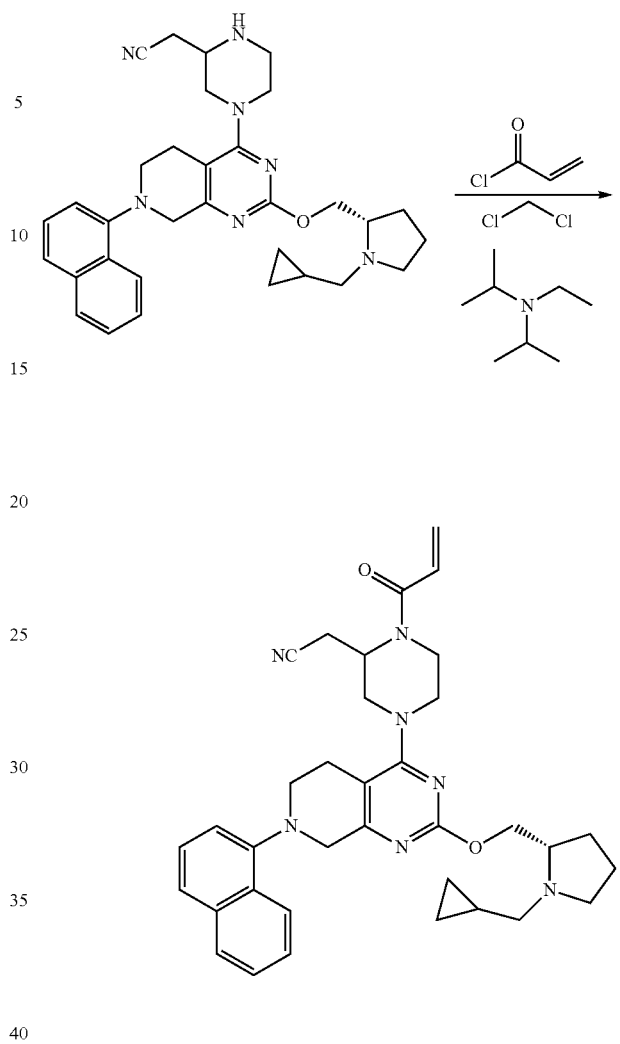

Step B: 2-(4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile A solution of benzyl 2-(cyanomethyl)-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazine-1-carboxylate (90 mg, 0.13 mmol) in EtOH (1340 µl, 0.13 mmol) and THF (1340 µl, 0.13 mmol) was purged with N2 for 5 min. To this solution was added Palladium (36 mg, 0.033 mmol) (Degussa Type, 10 wt %, 50% H₂O), and was immediately capped and purged with N2 for an additional 5 min. The solution was then stirred under H₂ introduced via vacuum followed by balloon pressure. The mixture was then stirred at ambient temperature for 1 hour. LC/MS showed desired product. The mixture was diluted with MeOH and filtered through packed celite. The filtrate was then concentrated in vacuo to provide 2-(4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile (71 mg, 0.13 mmol, 99% yield). ES+APCI MS m/z 538.3 [M+H]⁺.

Step C: 2-(1-acryloyl-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile To a suspension of 2-(4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile (71 mg, 0.132 mmol) in dichloromethane (1320 µl, 0.132 mmol) at ambient temperature was added Acryloyl Chloride (10.7 µl, 0.132 mmol) followed by Hunig's base (46.1 µl, 0.264 mmol). The reaction was then stirred at ambient temperature for 1 hour. LC/MS showed reaction completion. The reaction mixture was concentrated in vacuo. The concentrate was resuspended in a 60:40 mixture of ACN:H2O and purified on the Gilson (prep HPLC) eluting with 5→95% ACN/0.1% TFA in water/0.1% TFA. Fractions containing product were combined and free based with saturated bicarb and the organics extracted with DCM. The organics were dried over MgSO₄ and concentrated in vacuo to give 2-(1-acryloyl-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile (15.7 mg, 0.0265 mmol, 20.1% yield). ES+APCI MS m/z 592.4[M+H]⁺.

Example 258

2-[4-[7-(1-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

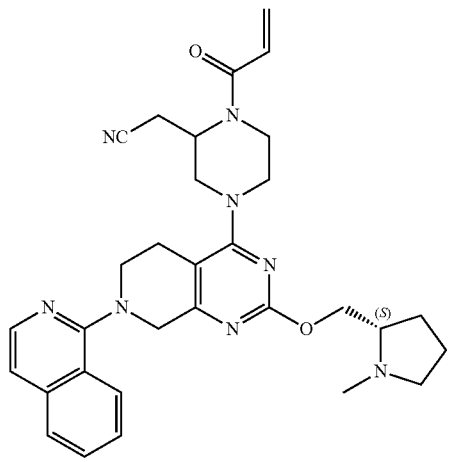

Title compound was prepared as in Example 210 Steps E-G, substituting 1-bromoisoquinoline for 1-bromo-2-(trifluoromethyl)benzene in step E and also substituting prop-2-enoyl prop-2-enoate for acryloyl chloride in step G. ESI MS m/z 553.3 [M+H]⁺.

Example 259

2-[4-[7-(6-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

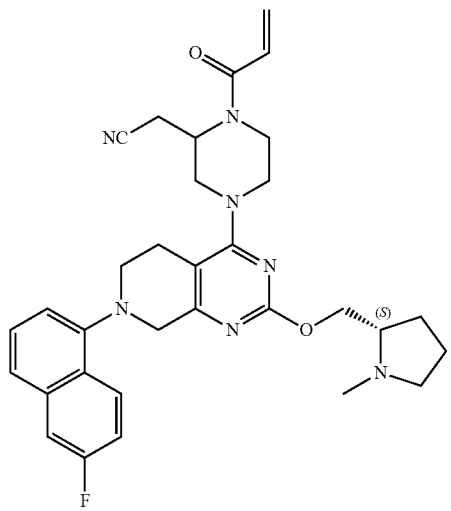

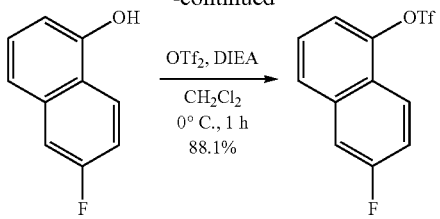

Step A: (6-fluoro-1-naphthyl) trifluoromethanesulfonate

To a solution of 6-fluoronaphthalen-1-ol (0.10 g, 617 umol) and DIEA (159 mg, 1.23 mmol, 215 uL) in dichloromethane (3 mL) was added trifluoromethylsulfonyl trifluoromethanesulfonate (191 mg, 678 umol, 112 uL) at 0° C. After stirred at 0° C. for 1 hour, the mixture was diluted with water (5 mL) and extracted with dichloromethane (3×5 mL). The organic layers were washed with brine (1×5 mL), dried over Na₂SO₄, filtered and concentrated under vacuum. The residue was purified by column chromatography (SiO₂, petroleum ether/ethyl acetate=3/1) to give (6-fluoro-1-naphthyl) trifluoromethanesulfonate (0.17 g, 543 umol, 88.1% yield) as a colourless oil. ¹H NMR (400 MHz, chloroform-d) δ=8.10 (dd, J=5.2, 8.8 Hz, 1H), 7.83 (d, J=8.4 Hz, 1H), 7.58-7.50 (m, 2H), 7.48-7.40 (m, 2H).

Title compound was prepared as in Example 210 Steps E-G, substituting 1(6-fluoro-1-naphthyl) trifluoromethanesulfonate for 1-bromo-2-(trifluoromethyl)benzene in step E and also substituting prop-2-enoyl prop-2-enoate for acryloyl chloride in step G. ESI MS m/z 570.3 [M+H]⁺.

Example 260

2-[4-[7-(4-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

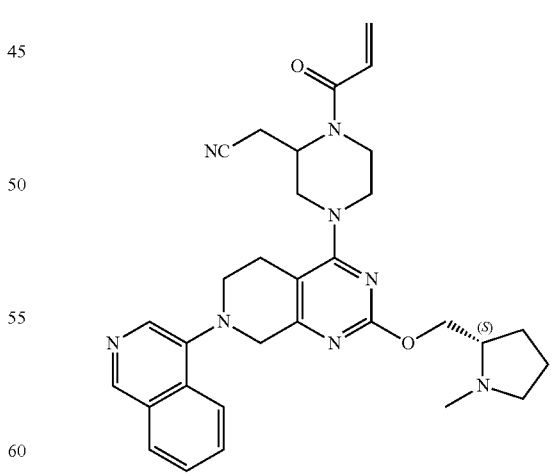

Title compound was prepared as in Example 210 Steps E-G, substituting 4-bromoisoquinoline for 1-bromo-2-(trifluoromethyl)benzene in step E and also substituting prop-2-enoyl prop-2-enoate for acryloyl chloride in step G. ESI MS m/z 553.1 [M+H]⁺.

Example 261

2-[1-(2-methylprop-2-enoyl)-4-[2-[[(2S)-1-methyl-pyrrolidin-2-yl]methoxy]-7-(1-naphthyl)-6,8-di-hydro-5H-pyrido[3,4-d]pyrimidin-4-yl]piperazin-2-yl]acetonitrile

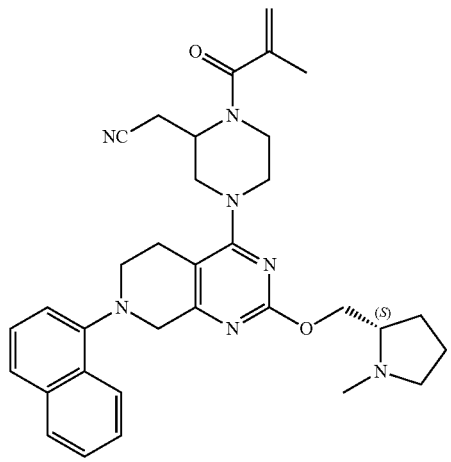

Title compound was prepared as in Example 210 Steps E-G, substituting 1-bromonaphthalene for 1-bromo-2-(trifluoromethyl)benzene in step E and also substituting 2-methylprop-2-enoyl chloride for acryloyl chloride in step G. ESI MS m/z 566.4 [M+H]+.

Example 262

2-[4-[7-(5-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

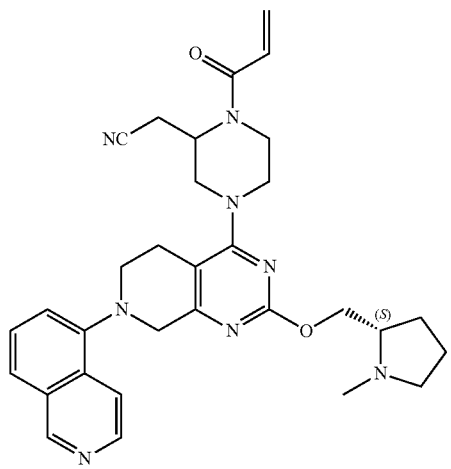

Title compound was prepared as in Example 210 Steps E-G, substituting 5-bromoisoquinoline for 1-bromo-2-(trifluoromethyl)benzene in step E and also substituting prop-2-enoyl prop-2-enoate for acryloyl chloride in step G. ESI MS m/z 553.4 [M+H]+.

Example 263

2-[1-[(E)-but-2-enoyl]-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile

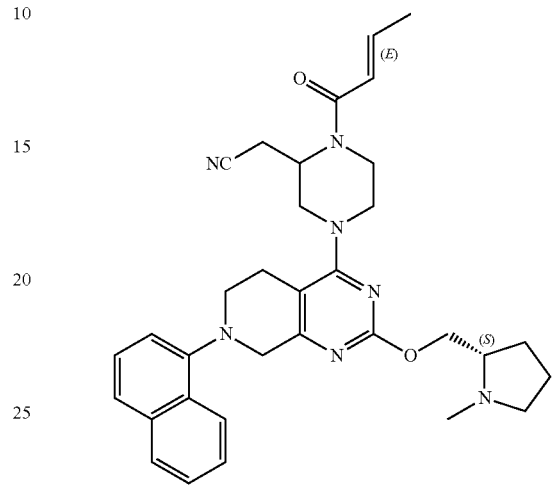

Title compound was prepared as in Example 210 Steps E-G, substituting 1-bromonaphthalene for 1-bromo-2-(trifluoromethyl)benzene in step E and (E)-but-2-enoyl chloride for acryloyl chloride in step G. ESI MS m/z 566.4 [M+H]+.

Example 264

2-[4-[2-[[(2S)-1-methylpyrrolidin-2-yl]methoxy]-7-(5-quinolyl)-6,8-dihydro-5H-pyrido[3,4-d]pyrimidin-4-yl]-1-prop-2-enoyl-piperazin-2-yl]acetonitrile

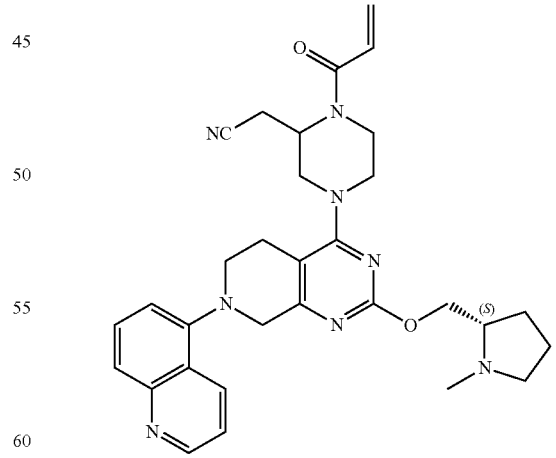

Title compound was prepared as in Example 210 Steps E-G, substituting 5-bromoquinoline for 1-bromo-2-(trifluoromethyl)benzene in step E and also substituting prop-2-enoyl prop-2-enoate for acryloyl chloride in step G. ESI MS m/z 553.4 [M+H]+.

Example 265

2-(1-acryloyl-4-(7-(3-methyl-2-(trifluoromethyl)phenyl)-2-((S)-1-methylpyrrolidin-2-yl)methoxy)-5,6,7,8-tetrahydropyrido [3,4-d]pyrimidin-4-yl)piperazin-2-yl)acetonitrile

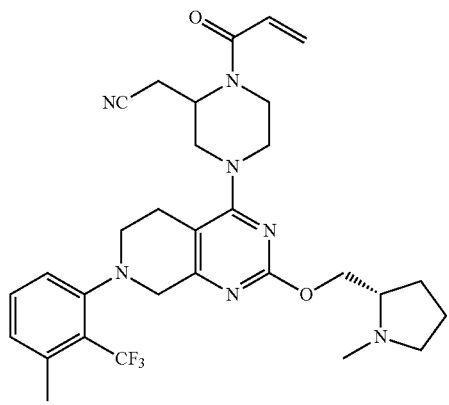 [SMILES: C=CC(=O)N1CCN(c2nc(OC[C@@H]3CCCN3C)nc3c2CCN(c2cccc(C)c2C(F)(F)F)C3)CC1CC#N]

Title compound was synthesized according to Example 210, Steps E-G using 1-bromo-3-methyl-2-(trifluoromethyl)benzene for 1-bromonaphthalene in Step E ES+APCI MS m/z 584.3 [M+H]+.

Example 266

2-(1-acryloyl-4-(2-(((S)-1-(2-methoxyethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile

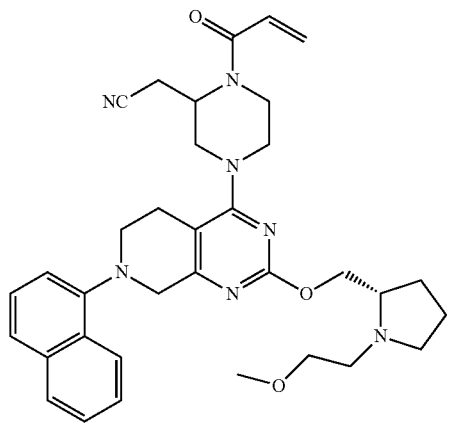 [SMILES: C=CC(=O)N1CCN(c2nc(OC[C@@H]3CCCN3CCOC)nc3c2CCN(c2cccc4ccccc24)C3)CC1CC#N]

Title compound was synthesized according to Example 147, Steps F-J, using (S)-(1-(2-methoxyethyl)pyrrolidin-2-yl)methanol in place of (S)-(1-methylpyrrolidin-2-yl)methanol in Step F. ES+APCI MS m/z 596.3 [M+H]+.

Example 267

2-((S)-1-acryloyl-4-(2-(((R)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

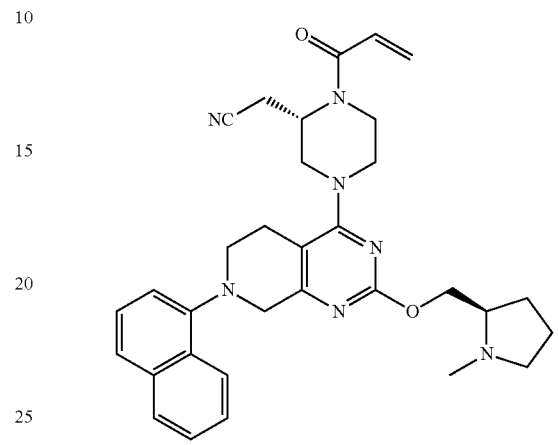

Title compound was synthesized according to Example 234 using (R)-(1-methylpyrrolidin-2-yl)methanol in place of (S)-(1-methylpyrrolidin-2-yl)methanol in Step F. ES+APCI MS m/z 552.3 [M+H]+.

Example 268

2-(1-acryloyl-4-(2-(((2S,4R)-4-methoxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

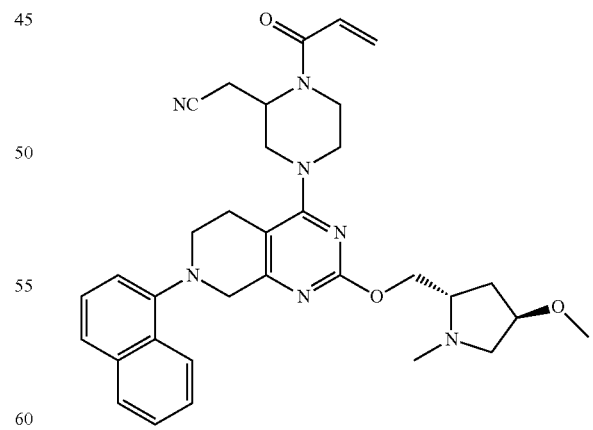

Title compound was synthesized according to Example 220, (Steps C-G), using tert-butyl (2S,4R)-2-(hydroxymethyl)-4-methoxypyrrolidine-1-carboxylate in place of (2S,4R)-1-(tert-Butoxycarbonyl)-4-fluoro-2-hydroxymethylpyrrolidine in Step C. ES+APCI MS m/z 582.3 [M+H]+.

Example 269

2-(1-acryloyl-4-(2-(2-(dimethylamino)-2-methyl-propoxy)-7-(naphthalen-1-yl)-5,6,7,8-tetrahydro-pyrido[3,4-d]pyrimidin-4-yl)piperazin-2-yl)acetonitrile

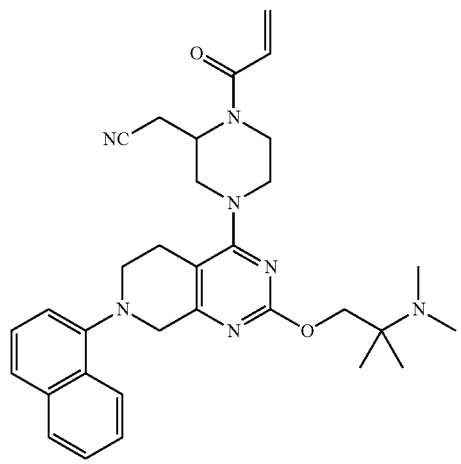 [SMILES: C=CC(=O)N1CCN(c2nc(OCC(C)(C)N(C)C)nc3c2CCN(c2cccc4ccccc24)C3)CC1CC#N]

The title compound was synthesized following Example 147 substituting 2-Dimethylamino-2-methyl-1-propanol for (S)-(1-(cyclopropylmethyl)pyrrolidin-2-yl)methanol in Step F. ES+APCI MS m/z 554.4 [M+H]⁺.

Example 270

2-(1-acryloyl-4-(2-(((R)-4-methylmorpholin-2-yl)methoxy)-7-(naphthalen-1-yl)-5,6,7,8-tetrahydro-pyrido[3,4-d]pyrimidin-4-yl)piperazin-2-yl)acetonitrile

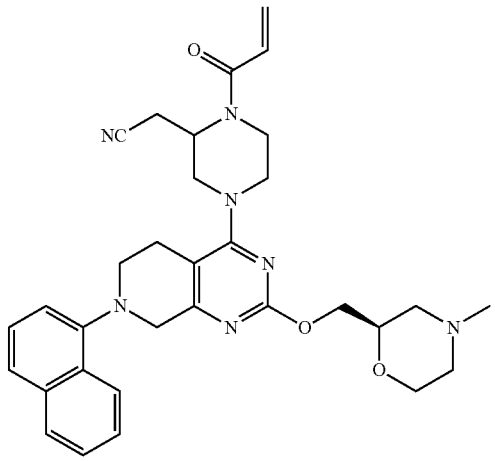 [SMILES: C=CC(=O)N1CCN(c2nc(OC[C@H]3CN(C)CCO3)nc3c2CCN(c2cccc4ccccc24)C3)CC1CC#N]

Title compound was synthesized according to Example 147, Steps F-J, using (R)—N-Boc-2-hydroxymethylmorpholine in place of (S)-(1-methylpyrrolidin-2-yl)methanol in Step F. ES+APCI MS m/z 568.3 [M+H]⁺.

Example 271

2-(1-acryloyl-4-(2-(((S)-4-methylmorpholin-2-yl)methoxy)-7-(naphthalen-1-yl)-5,6,7,8-tetrahydro-pyrido[3,4-d]pyrimidin-4-yl)piperazin-2-yl)acetonitrile

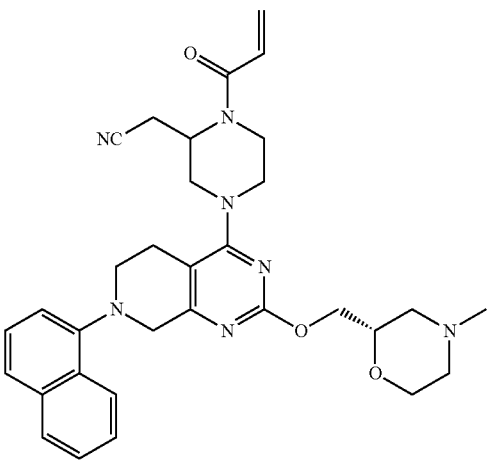 [SMILES: C=CC(=O)N1CCN(c2nc(OC[C@@H]3CN(C)CCO3)nc3c2CCN(c2cccc4ccccc24)C3)CC1CC#N]

Title compound was synthesized according to Example 147, Steps F-J, using (S)—N-Boc-2-hydroxymethylmorpholine in place of (S)-(1-methylpyrrolidin-2-yl)methanol in Step F. ES+APCI MS m/z 568.3 [M+H]⁺.

Example 272

2-(1-acryloyl-4-(2-(((S)-4-methylmorpholin-3-yl)methoxy)-7-(naphthalen-1-yl)-5,6,7,8-tetrahydro-pyrido[3,4-d]pyrimidin-4-yl)piperazin-2-yl)acetonitrile

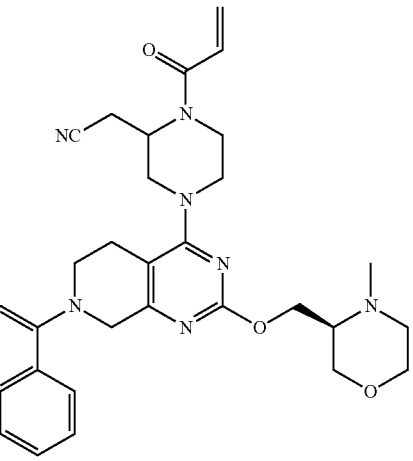

Title compound was synthesized according to Example 147, Steps F-J, using tert-butyl (R)-3-(hydroxymethyl)morpholine-4-carboxylate in place of (S)-(1-methylpyrrolidin-2-yl)methanol in Step F. ES+APCI MS m/z 568.3 [M+H]⁺.

Example 273

2-(1-acryloyl-4-(2-(((R)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile

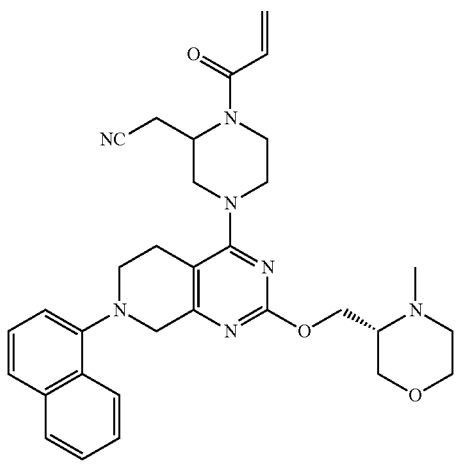 [SMILES: C=CC(=O)N1CCN(c2nc(OC[C@H]3COCCN3C)nc3c2CCN(c2cccc4ccccc24)C3)CC1CC#N]

Title compound was synthesized according to Example 147, Steps F-J, using tert-butyl (S)-3-(hydroxymethyl)morpholine-4-carboxylate in place of (S)-(1-methylpyrrolidin-2-yl)methanol in Step F. ES+APCI MS m/z 568.3 [M+H]+.

Example 274

2-((S)-1-acryloyl-4-(7-(3-fluoro-2-(trifluoromethyl)phenyl)-2-(((R)-1-methylpyrrolidin-2-yl)methoxy)-5,6,7,8-tetrahydropyrido[3,4-d]pyrimidin-4-yl)piperazin-2-yl)acetonitrile

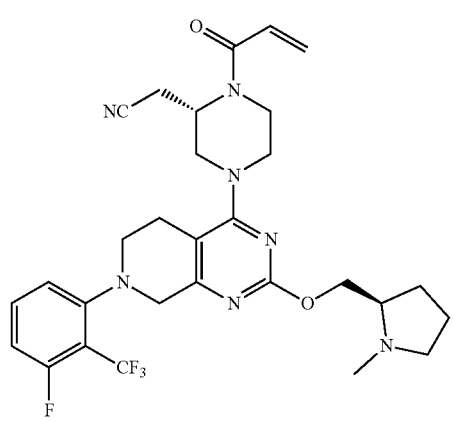 [SMILES: C=CC(=O)N1CCN(c2nc(OC[C@H]3CCCN3C)nc3c2CCN(c2cccc(F)c2C(F)(F)F)C3)C[C@@H]1CC#N]

Title compound was synthesized according to Example 234, Steps G-J using (R)-(1-methylpyrrolidin-2-yl)methanol in place of (S)-(1-methylpyrrolidin-2-yl)methanol in Step F and 1-bromo-3-fluoro-2-(trifluoromethyl)benzene for 1-bromonaphthalene in Step H ES+APCI MS m/z 588.3 [M+H]+.

Example 275

2-(1-acryloyl-4-(7-(2-fluoro-6-(trifluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile

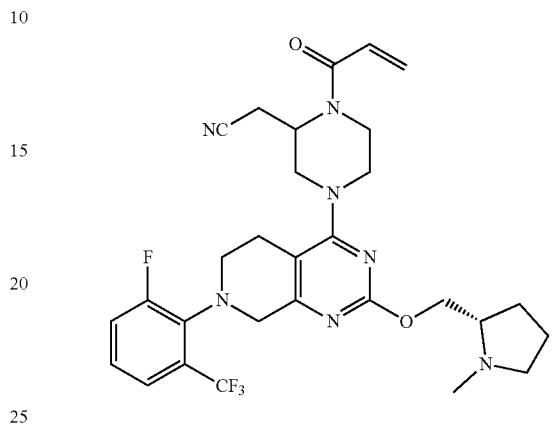

Title compound was synthesized according to Example 210, Steps E-G using 2-bromo-1-fluoro-3-(trifluoromethyl)benzene for 1-bromonaphthalene in Step E. ES+APCI MS m/z 588.3 [M+H]+.

Example 276

2-(1-acryloyl-4-(7-(4-fluoro-2-(trifluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile

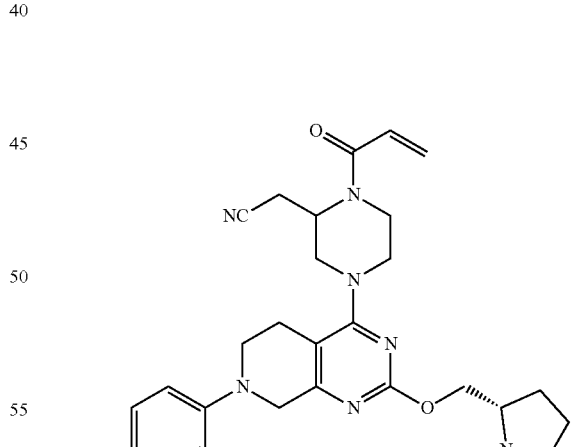

Title compound was synthesized according to Example 210, Steps E-G using 1-bromo-4-fluoro-2-(trifluoromethyl)benzene for 1-bromonaphthalene in Step E. ES+APCI MS m/z 588.3 [M+H]+.

Example 277

2-(1-acryloyl-4-(7-(3-chloro-2-(trifluoromethyl)phenyl)-2-(((S)-1-methylpyrrolidin-2-yl)methoxy)-5,6,7,8-tetrahydropyrido [3,4-d]pyrimidin-4-yl)piperazin-2-yl)acetonitrile

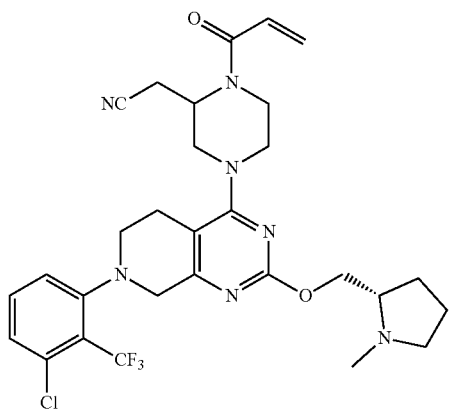

Title compound was synthesized according to Example 210, Steps E-G using 1-bromo-3-chloro-2-(trifluoromethyl)benzene for 1-bromonaphthalene in Step E and THF in place EtOH/THF in Step F. ES+APCI MS m/z 604.3 [M+H]+.

Example 278

2-(1-acryloyl-4-(2-(((S)-1-methylpyrrolidin-2-yl)methoxy)-7-(quinolin-4-yl)-5,6,7,8-tetrahydropyrido [3,4-d]pyrimidin-4-yl)piperazin-2-yl)acetonitrile

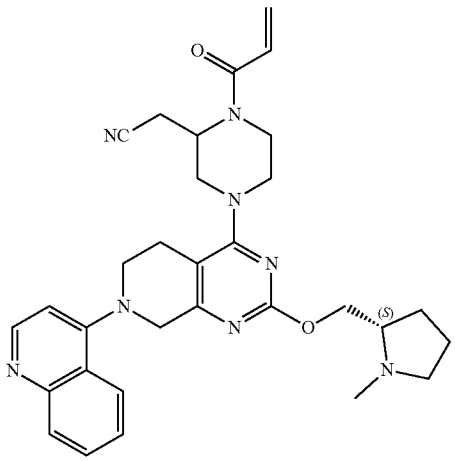

Title compound was prepared as in Example 210 Steps E-G, substituting 4-bromoquinoline for 1-bromo-2-(trifluoromethyl)benzene in step E and also substituting prop-2-enoyl prop-2-enoate for acryloyl chloride in step G.

Example 279

2-(1-acryloyl-4-(2-(2-(dimethylamino)ethoxy)-7-(2-(trifluoromethyl)phenyl)-5,6,7,8-tetrahydropyrido[3,4-d]pyrimidin-4-yl)piperazin-2-yl)acetonitrile

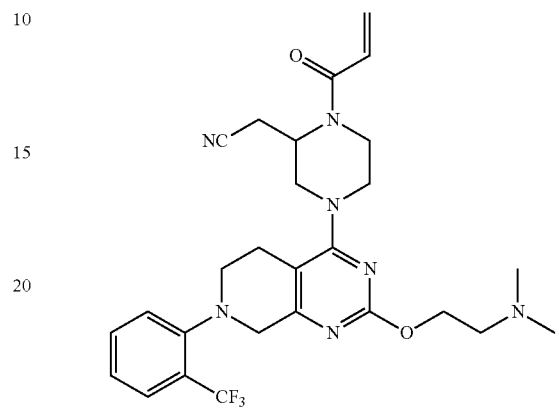

Title compound was prepared as in Example 210, substituting N, N-dimethyl-ethanolamine for (2S)-1-Ethyl-2-pyrrolidinyl]methanol in step C and also substituting prop-2-enoyl prop-2-enoate for acryloyl chloride in step G.

Example 280

2-(4-(2-(3-((1R,4R)-2-oxa-5-azabicyclo[2.2.1]heptan-5-yl)propoxy)-7-(2-(trifluoromethyl)phenyl)-5,6,7,8-tetrahydropyrido [3,4-d]pyrimidin-4-yl)-1-acryloylpiperazin-2-yl)acetonitrile

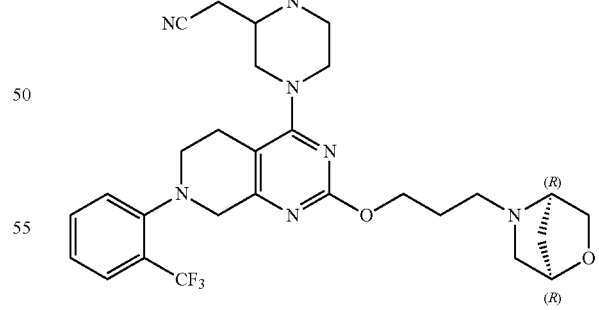

Title compound was prepared as in Example 210, substituting 3-((1R,4R)-2-oxa-5-azabicyclo[2.2.1]heptan-5-yl) propan-1-ol for (2S)-1-Ethyl-2-pyrrolidinyl]methanol in step C and also substituting prop-2-enoyl prop-2-enoate for acryloyl chloride in step G.

Example 281

2-(1-acryloyl-4-(2-(((R)-1-methylpyrrolidin-3-yl)methoxy)-7-(2-(trifluoromethyl)phenyl)-5,6,7,8-tetrahydropyrido[3,4-d]pyrimidin-4-yl)piperazin-2-yl)acetonitrile

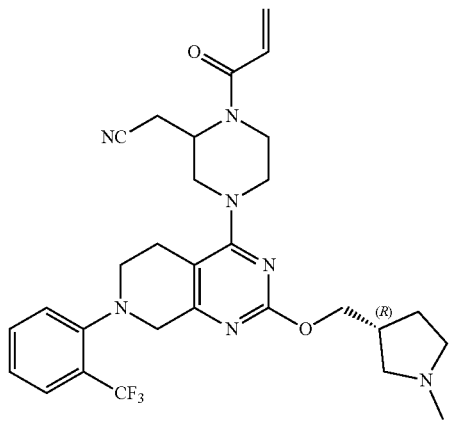

Title compound was prepared as in Example 210, substituting (R)-(1-methylpyrrolidin-3-yl)methanol for (2S)-1-Ethyl-2-pyrrolidinyl]methanol in step C and also substituting prop-2-enoyl prop-2-enoate for acryloyl chloride in step G.

Example 282

2-(1-(3-methylbut-2-enoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

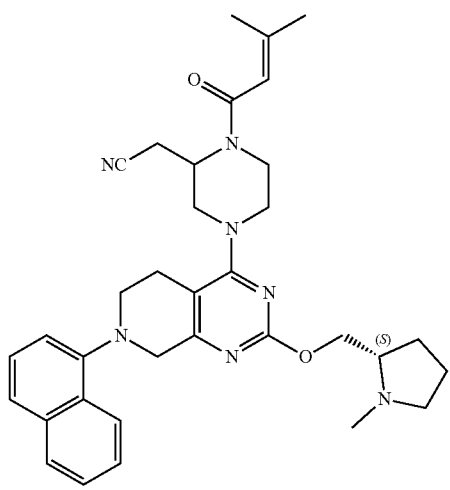

Title compound was prepared as in Example 210, substituting 1-bromonaphthalene for 1-bromo-2-(trifluoromethyl)benzene in step E and 3-methylbut-2-enoyl chloride for acryloyl chloride in step G.

Example 283

2-(1-acryloyl-4-(2-(((R)-1-methylpyrrolidin-2-yl)methoxy)-7-(2-(trifluoromethyl)phenyl)-5,6,7,8-tetrahydropyrido[3,4-d]pyrimidin-4-yl)piperazin-2-yl)acetonitrile

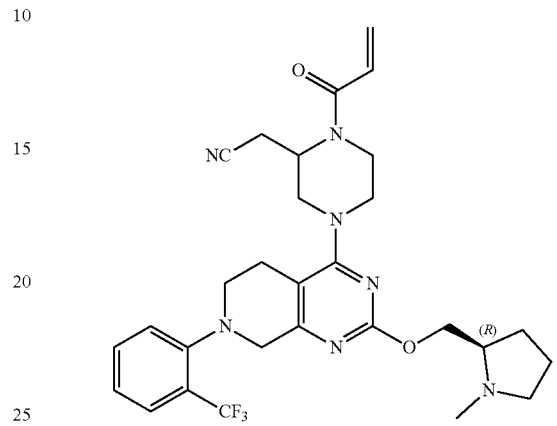

Title compound was prepared as in Example 210, substituting (2R)-1-Ethyl-2-pyrrolidinyl]methanol for (2S)-1-Ethyl-2-pyrrolidinyl]methanol in step C and also substituting prop-2-enoyl prop-2-enoate for acryloyl chloride in step G.

Example 284

2-(1-acryloyl-4-(2-(2-(diethylamino)ethoxy)-7-(2-(trifluoromethyl)phenyl)-5,6,7,8-tetrahydropyrido[3,4-d]pyrimidin-4-yl)piperazin-2-yl)acetonitrile

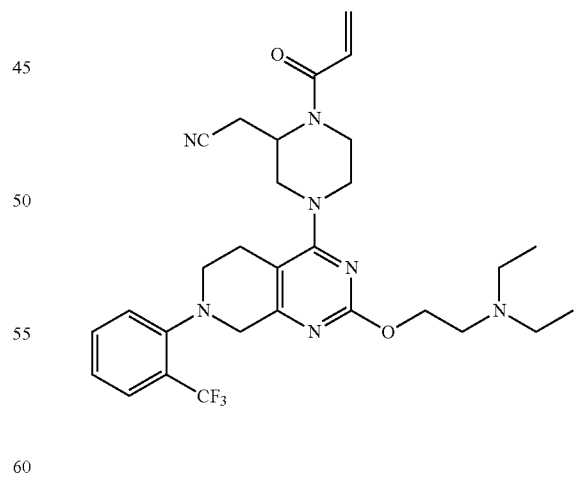

Title compound was prepared as in Example 210, substituting N,N-diethyl-ethanolamine for (2S)-1-Ethyl-2-pyrrolidinyl]methanol in step C and also substituting prop-2-enoyl prop-2-enoate for acryloyl chloride in step G.

Example 285

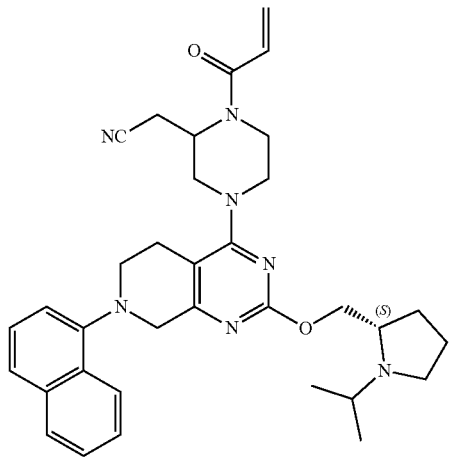

tert-butyl 2-(cyanomethyl)-4-[2-[[(2S)-1-isopropylpyrrolidin-2-yl]methoxy]-7-(1-naphthyl)-6,8-dihydro-5H-pyrido[3,4-d]pyrimidin-4-yl]piperazine-1-carboxylate

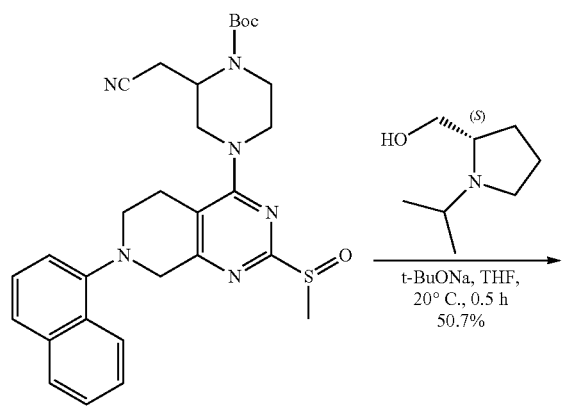

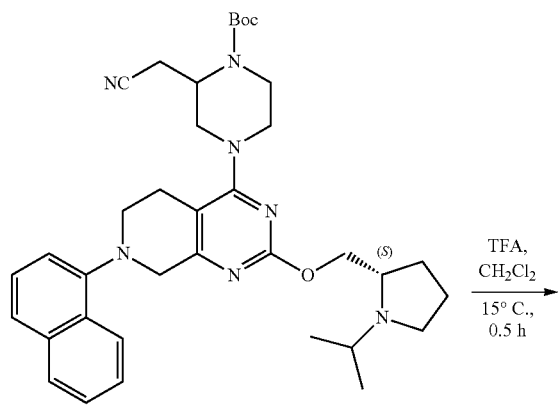

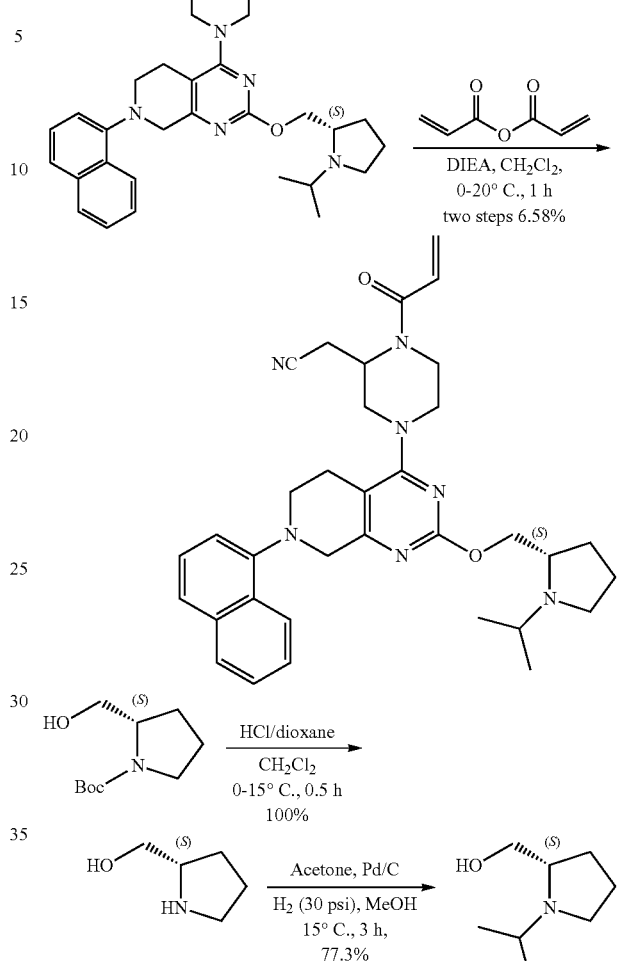

Step 1: (S)-pyrrolidin-2-ylmethanol

To a solution of (S)-tert-butyl 2-(hydroxymethyl) pyrrolidine-1-carboxylate (2 g, 9.94 mmol, 1 eq) in CH$_2$Cl$_2$ (40 mL) was added HCl (4 M in dioxane, 49.69 mL, 20 eq) at 0° C. under nitrogen atmosphere. After stirred at 15° C. for 30 min, the mixture was concentrated under vacuum. Compound (S)-pyrrolidin-2-ylmethanol (1.37 g, 9.96 mmol, 100% yield, HCl) was obtained as a yellow solid.

Step 2: [(2S)-1-isopropylpyrrolidin-2-yl]methanol

A mixture of [(2S)-pyrrolidin-2-yl]methanol (750 mg, 7.41 mmol, 724 uL, 1 eq) and acetone (4.31 g, 74.2 mmol, 5.46 mL, 10 eq) in MeOH (20 mL) was hydrogenated under H$_2$ (30 psi) with Pd/C (100 mg, 7.41 mmol, 10% purity, 1 eq) as a catalyst at 15° C. for 3 hours. The mixture was filtered and concentrated under vacuum. Compound [(2S)-1-isopropylpyrrolidin-2-yl]methanol (0.821 g, 5.73 mmol, 77.3% yield) was obtained as a yellow oil.
$^1$H NMR (400 MHz, methanol-d$_4$) δ=3.54 (dd, J=4.0, 10.8 Hz, 1H), 3.40-3.35 (m, 1H), 2.99-2.86 (m, 3H), 2.60-2.50 (m, 1H), 1.94-1.82 (m, 1H), 1.82-1.66 (m, 3H), 1.15 (d, J=6.4 Hz, 3H), 1.08 (d, J=6.4 Hz, 3H).

Step A: tert-butyl 2-(cyanomethyl)-4-[2-[[(2S)-1-isopropylpyrrolidin-2-yl]methoxy]-7-(1-naphthyl)-6,8-dihydro-5H-pyrido[3,4-d]pyrimidin-4-yl]piperazine-1-carboxylate To a mixture of tert-butyl 2-(cyanomethyl)-4-[2-methylsulfinyl-7-(1-naphthyl)-6,8-dihydro-5H-pyrido[3,4-d]pyrimidin-4-yl]piperazine-1-carboxylate (300 mg, 549 umol, 1 eq) and [(2S)-1-isopropylpyrrolidin-2-yl]methanol (157 mg, 1.10 mmol, 2 eq) in THF (5 mL) was added t-BuONa (158 mg, 1.65 mmol, 3 eq). After stirred at 20° C. for 0.5 hour, the reaction mixture was neutralized with HCl (1 mol/L) to pH=7 at 0° C., and then the mixture was concentrated under reduced pressure. The residue was purified by reversed phase flash [water (0.1% TFA)/acetonitrile]. The desired fractions were collected and neutralized with saturated NaHCO$_3$ solution and extracted with ethyl acetate (200 mL). The organic layer was dried over sodium sulfate, filtered and concentrated under vacuum. Compound tert-butyl 2-(cyanomethyl)-4-[2-[[(2S)-1-isopropylpyrrolidin-2-yl]methoxy]-7-(1-naphthyl)-6,8-dihydro-5H-pyrido[3,4-d]pyrimidin-4-yl]piperazine-1-carboxylate (174 mg, 278 umol, 50.7% yield, 100% purity) was obtained as a yellow oil. LCMS [ESI, M+1]: 626.

Step B: 2-[4-[2-[[(2S)-1-isopropylpyrrolidin-2-yl]methoxy]-7-(1-naphthyl)-6,8-dihydro-5H-pyrido[3,4-d]pyrimidin-4-yl]piperazin-2-yl]acetonitrile To a solution of tert-butyl 2-(cyanomethyl)-4-[2-[[(2S)-1-isopropyl pyrrolidin-2-yl]methoxy]-7-(1-naphthyl)-6,8-dihydro-5H-pyrido[3,4-d]pyrimidin-4-yl]piperazine-1-carboxylate (174 mg, 278 umol, 1 eq) in CH$_2$Cl$_2$ (5 mL) was added TFA (7.70 g, 67.5 mmol, 5.00 mL, 243 eq) at 0° C. under nitrogen atmosphere. After stirred at 15° C. for 0.5 h, the mixture was concentrated under vacuum. Compound 2-[4-[2-[[(2S)-1-isopropylpyrrolidin-2-yl] methoxy]-7-(1-naphthyl)-6,8-dihydro-5H-pyrido[3,4-d]pyrimidin-4-yl]piperazin-2-yl]acetonitrile (178 mg, crude, TFA) was obtained as a yellow oil. LCMS [ESI, M+1]: 526.

Step C: 2-[4-[2-[[(2S)-1-isopropylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a mixture of 2-[4-[2-[[(2S)-1-isopropylpyrrolidin-2-yl]methoxy]-7-(1-naphthyl)-6,8-dihydro-5H-pyrido[3,4-d]pyrimidin-4-yl]piperazin-2-yl]acetonitrile (178 mg, crude, TFA) and DIEA (360 mg, 2.78 mmol, 485 uL) in CH$_2$Cl$_2$ (5 mL) was added prop-2-enoyl prop-2-enoate (28.1 mg, 223 umol) at 0° C. The mixture was stirred at 20° C. for 1 hour. The reaction mixture was quenched with NaHCO$_3$ saturated solution (5 mL) at 0° C., and then extracted with CH$_2$Cl$_2$ (2×25 mL). The combined organic layers were washed with brine (1×50 mL), dried over sodium sulfate, filtered and concentrated under vacuum. The residue was purified by prep-HPLC (column: Boston Green ODS 150*30 5 u; mobile phase: [water (0.225% FA)-ACN]; B %: 27%-54%, 10 min). Title compound 2-[4-[2-[[(2S)-1-isopropylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (11.7 mg, 18.3 umol, two steps 6.58% yield, 97.9% purity, FA) was obtained as a brown solid. LCMS [ESI, M+1]: 580.

$^1$H NMR (400 MHz, Acetic acid-d4) δ=8.28-8.19 (m, 1H), 8.08 (s, 1H), 7.91-7.83 (m, 1H), 7.63 (d, J=8.4 Hz, 1H), 7.56-7.47 (m, 2H), 7.44 (t, J=7.6 Hz, 1H), 7.20 (d, J=7.2 Hz, 1H), 6.94-6.71 (m, 1H), 6.38 (br d, J=16.8 Hz, 1H), 5.87 (br d, J=10.4 Hz, 1H), 5.15 (br s, 1H), 4.92-4.54 (m, 4H), 4.42 (br d, J=12.0 Hz, 1H), 4.34 (br s, 2H), 4.13 (br s, 2H), 3.95 (br s, 1H), 3.85-3.21 (m, 7H), 3.20-2.84 (m, 3H), 2.42-2.25 (m, 1H), 2.24-2.07 (m, 3H), 1.43 (d, J=6.4 Hz, 3H), 1.39 (d, J=6.4 Hz, 3H).

Example 286

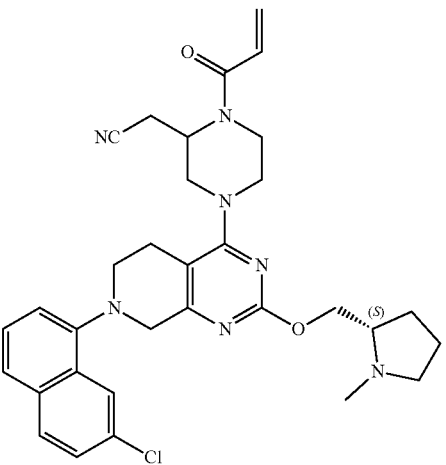

2-(1-acryloyl-4-(7-(7-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

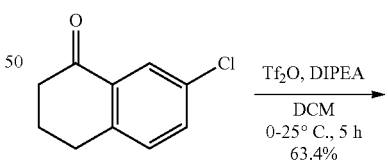

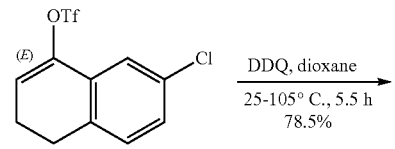

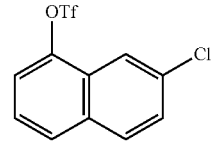

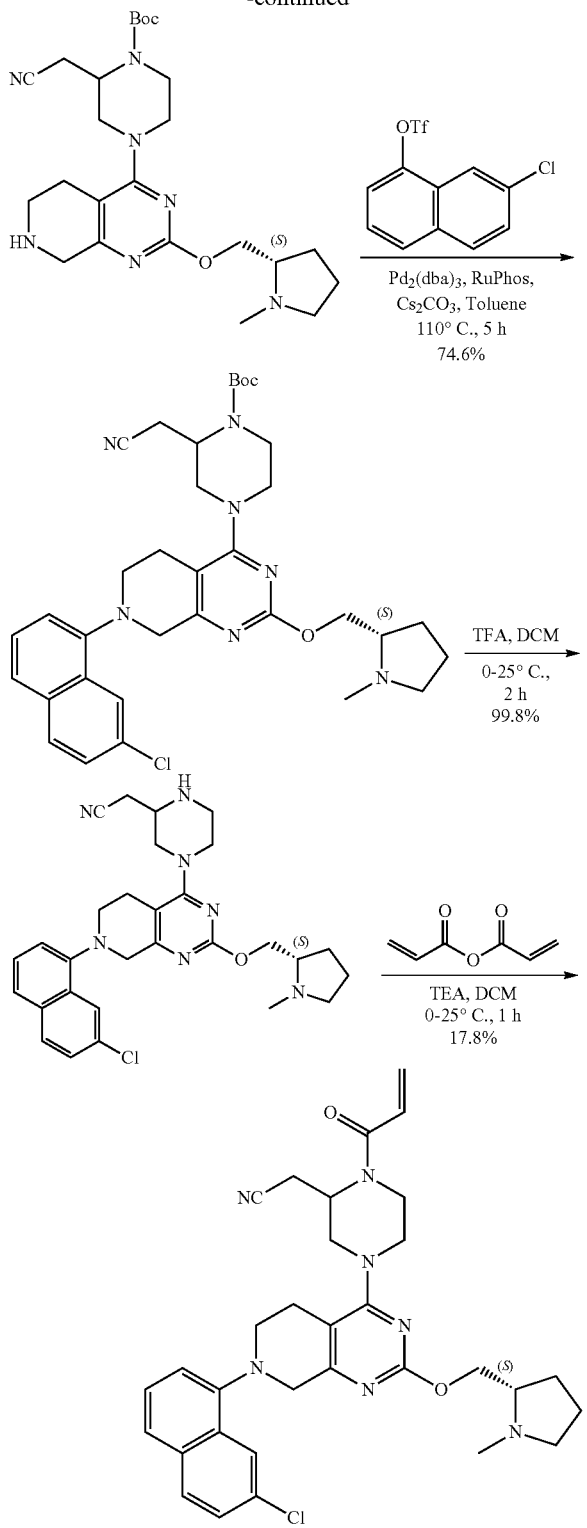

Step 1: (7-chloro-3,4-dihydronaphthalen-1-yl) trifluoromethanesulfonate

To a mixture of 7-chlorotetralin-1-one (2 g, 11.1 mmol, 1 eq) and DIEA (4.29 g, 33.2 mmol, 5.79 mL, 3 eq) in DCM (35 mL) was added Tf₂O (4.69 g, 16.6 mmol, 2.74 mL, 1.5 eq) in one portion at 0° C. under N₂. The mixture was stirred at 25° C. for 5 hours. The reaction mixture was concentrated under reduced pressure. The residue was purified by column chromatography (SiO₂, Petroleum ether/Ethyl acetate=200/1 to 50/1). Compound (7-chloro-3,4-dihydronaphthalen-1-yl) trifluoromethanesulfonate (2.25 g, 7.02 mmol, 63.4% yield, 97.6% purity) was obtained as a colorless oil.

¹H NMR (400 MHz, chloroform-d) δ=7.32 (d, J=2.0 Hz, 1H), 7.24 (dd, J=2.0, 8.0 Hz, 1H), 7.12 (d, J=8.0 Hz, 1H), 6.10 (t, J=4.8 Hz, 1H), 2.88-2.80 (m, 2H), 2.53 (dt, J=4.8, 8.0 Hz, 2H).

Step 2: (7-chloro-1-naphthyl) trifluoromethanesulfonate

To a mixture of (7-chloro-3,4-dihydronaphthalen-1-yl) trifluoromethanesulfonate (1.57 g, 5.02 mmol, 1 eq) in dioxane (35 mL) was added DDQ (2.28 g, 10.0 mmol, 2 eq) in one portion under N₂. The mixture was stirred at 25° C. for 30 min, then heated to 105° C. and stirred for 5 hours. The reaction mixture was concentrated under reduced pressure to remove 1,4-dioxane. The residue was purified by column chromatography (SiO₂, Petroleum ether/Ethyl acetate=200/1 to 50/1). Compound (7-chloro-1-naphthyl) trifluoromethanesulfonate (1.24 g, 3.94 mmol, 78.5% yield, 98.7% purity) was obtained as a colorless oil.

¹H NMR (400 MHz, chloroform-d) δ=8.05 (d, J=2.0 Hz, 1H), 7.87-7.83 (m, 2H), 7.57-7.47 (m, 3H).

Step A: tert-butyl 4-[7-(7-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate. To a mixture of tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate (200 mg, 424 umol, 1 eq) and (7-chloro-1-naphthyl) trifluoromethanesulfonate (264 mg, 848 umol, 2 eq) in toluene (20 mL) was added Pd₂(dba)₃ (38.8 mg, 42.4 umol, 0.1 eq), RuPhos (39.6 mg, 84.8 umol, 0.2 eq) and Cs₂CO₃ (414 mg, 1.27 mmol, 3 eq) under N₂. The mixture was heated to 110° C. and stirred for 5 hours. The mixture was diluted with water (10.0 mL) and extracted with ethyl acetate (3×15.0 mL). The extracts were washed with brine (1×20.0 mL), dried over Na₂SO₄, filtered and concentrated under vacuum. The residue was purified by reversed phase flash [water (0.1% TFA)/acetonitrile]. The desired fractions were collected and neutralized with saturated NaHCO₃ solution and extracted with ethyl acetate (1×30 mL). The organic layer was dried over sodium sulfate, filtered and concentrated under vacuum. Compound tert-butyl 4-[7-(7-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (200 mg, 316 umol, 74.6% yield, 100% purity) was obtained as a yellow solid. LCMS [ESI, M+1]: 632.

¹H NMR (400 MHz, chloroform-d) δ=8.20 (d, J=2.0 Hz, 1H), 7.80 (d, J=8.8 Hz, 1H), 7.59 (d, J=8.2 Hz, 1H), 7.48-7.38 (m, 2H), 7.18 (d, J=7.2 Hz, 1H), 4.63 (br s, 1H), 4.43 (br dd, J=4.8, 10.3 Hz, 1H), 4.29-4.16 (m, 3H), 4.09-3.89 (m, 2H), 3.42 (br s, 1H), 3.35-3.20 (m, 3H), 3.17-2.65 (m, 7H), 2.52 (s, 3H), 2.33 (br d, J=7.6 Hz, 1H), 2.14-2.06 (m, 1H), 1.88-1.71 (m, 4H).

Step B: 2-[4-[7-(7-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a mixture of tert-butyl 4-[7-(7-chloro-1-naphthyl)-2-[[(2S)-1-methylpyrrolidin-2-yl]methoxy]-6,8-dihydro-5H- pyrido[3,4-d]pyrimidin-4-yl]-2-(cyanomethyl)piperazine-1-carboxylate (200 mg, 316 umol, 1 eq) in DCM (2.5 mL) was added TFA (541 mg, 4.75 mmol, 351 uL, 15 eq) in one portion at 0° C. under N₂. Then the mixture was stirred at 25° C. for 2 hours. The reaction mixture was concentrated under reduced pressure. Compound 2-[4-[7-(7-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (204 mg, 316 umol, 99.8% yield, TFA) was obtained as a brown solid. LCMS [ESI, M+1]: 532.

Step C: 2-[4-[7-(7-chloro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[4-[7-(7-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (204 mg, 316 umol, 1 eq, TFA) and TEA (160 mg, 1.58 mmol, 220 uL, 5 eq) in DCM (1.5 mL) was added prop-2-enoyl prop-2-enoate (39.8 mg, 316 umol, 1 eq) in one portion at 0° C. After stirred at 25° C. for 1 h, the reaction mixture was quenched with saturated NaHCO₃ solution (1 mL) at 0° C., then diluted with water (2 mL) and extracted with DCM (5 mL×3). The combined organic layers were washed with water (5 mL×1), dried over Na₂SO₄, filtered and concentrated under reduced pressure. The residue was purified by prep-HPLC (column: Boston Green ODS 150×30 5 u; mobile phase: [water (0.225% FA)-ACN]; B %: 30%-54%, 10 min). Title compound 2-[4-[7-(7-chloro-1-naphthyl)-2-[[(2S)-1-methylpyrrolidin-2-yl] methoxy]-6,8-dihydro-5H-pyrido[3,4-d]pyrimidin-4-yl]-1-prop-2-enoyl-piperazin-2-yl]acetonitrile (36.0 mg, 56.1 umol, 17.8% yield, 98.7% purity, FA) was obtained as a white solid. LCMS [ESI, M+1]: 586.

¹H NMR (400 MHz, chloroform-d) δ=8.42 (br s, 1H), 8.19 (d, J=1.6 Hz, 1H), 7.80 (d, J=8.8 Hz, 1H), 7.60 (d, J=8.0 Hz, 1H), 7.47-7.41 (m, 2H), 7.19 (d, J=7.2 Hz, 1H), 6.61 (br s, 1H), 6.40 (br d, J=16.8 Hz, 1H), 5.84 (br d, J=10.8 Hz, 1H), 5.08 (br s, 1H), 4.91-4.75 (m, 2H), 4.48 (td, J=4.4, 12.0 Hz, 1H), 4.23 (br s, 3H), 4.07 (br d, J=11.2 Hz, 1H), 3.82-3.58 (m, 2H), 3.56-3.08 (m, 6H), 3.08-2.92 (m, 2H), 2.89 (d, J=1.6 Hz, 3H), 2.85-2.70 (m, 2H), 2.28 (qd, J=8.4, 12.5 Hz, 1H), 2.22-2.11 (m, 1H), 2.11-1.94 (m, 2H).

Example 287

2-[4-[7-(5-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

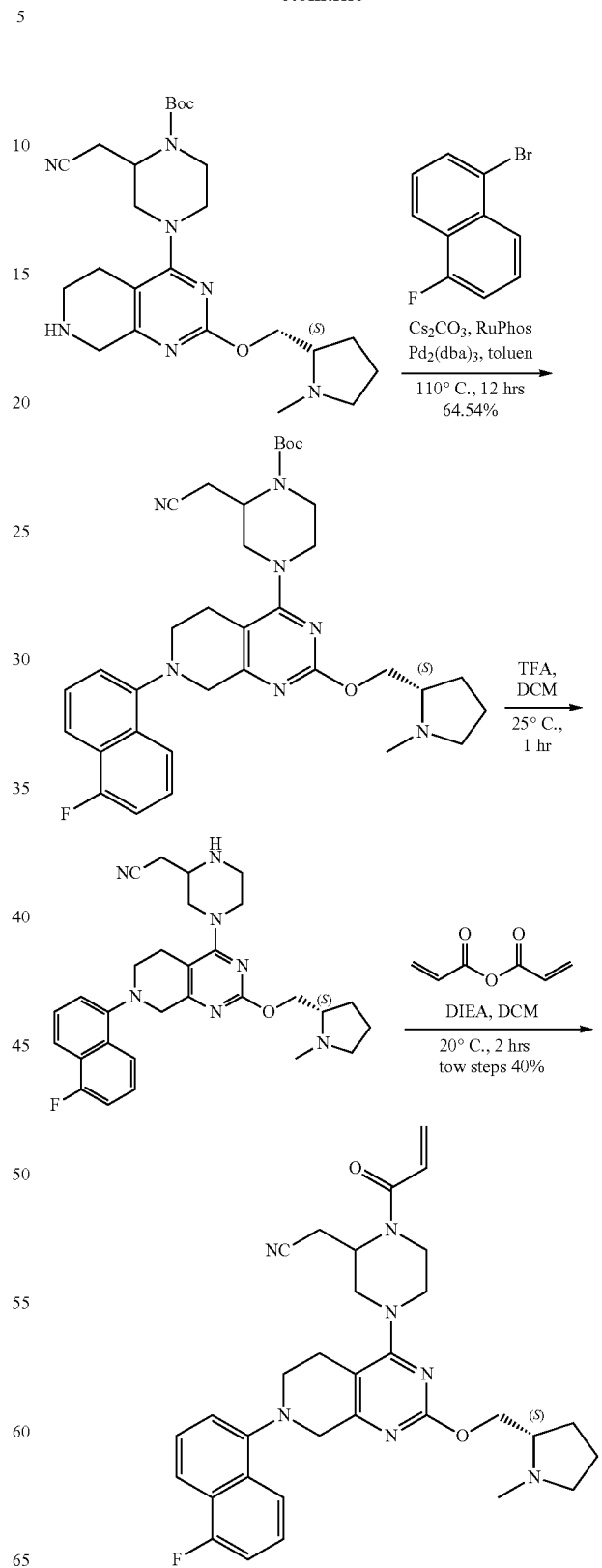

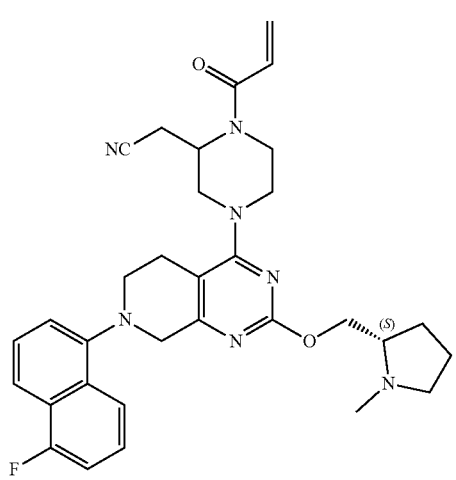

Step A: tert-butyl 2-(cyanomethyl)-4-[7-(5-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a solution of tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate (200 mg, 424 umol, 1.30 eq) and 1-bromo-5-fluoro-naphthalene (73.4 mg, 326 umol, 1.0 eq) in toluene (5.0 mL) was added Cs$_2$CO$_3$ (319 mg, 979 umol, 3.0 eq), Pd$_2$(dba)$_3$ (29.9 mg, 32.6 umol, 0.10 eq) and RuPhos (22.8 mg, 48.9 umol, 0.15 eq). The mixture was stirred at 110° C. for 12 hrs. The reaction mixture was concentrated under reduced pressure to remove toluene. The residue was diluted with H$_2$O (10.0 mL) and extracted with Ethyl acetate (10.0 mL*3). The combined organic layers were washed with H$_2$O (10.0 mL), and concentrated under reduced pressure to give a residue. The residue was purified by reversed phase flash [water (0.100% formic acid)/acetonitrile]. Compound tert-butyl 2-(cyanomethyl)-4-[7-(5-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (140 mg, 211 umol, 64.5% yield) was obtained as a white solid. LCMS [ESI, M+1]: 616.

Step B: 2-[4-[7-(5-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl 2-(cyanomethyl)-4-[7-(5-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (130 mg, 211 umol, 1.0 eq) in DCM (2.0 mL) was added TFA (3.08 g, 27.0 mmol, 2.00 mL, 128 eq). The mixture was stirred at 25° C. for 1 hr under N$_2$ atmosphere. The organic solvent was removed under vacuum. Compound 2-[4-[7-(5-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, crude) was obtained as a yellow oil. The crude product was used directly to the next step without further purification. LCMS [ESI, M+1]: 517.

Step C: 2-[4-[7-(5-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(5-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, TFA) in DCM (3.0 mL) was added Et$_3$N (200 mg, 1.98 mmol, 275 uL) and prop-2-enoyl prop-2-enoate (40.0 mg, 317 umol) at 0° C. The mixture was stirred at 20° C. for 2 hrs. The reaction was washed with water (10.0 mL). The crude mixture was extracted with ethyl acetate (20.0 mL*3). Combine extracts were washed with brine (50.0 mL), dried with Na$_2$SO$_4$ the solvent was then removed under vacuum. The residue was purified by prep-HPLC (column: Boston Green ODS 150*30 5 u; mobile phase: [water (0.225% FA)-ACN]; B %: 26%-53%,10 min) and lyophilization. Title compound 2-[4-[7-(5-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (48.4 mg, 82.6 umol, two steps 40.0% yield, FA) was obtained as a off-white solid. LCMS [ESI, M+1]: 570.

$^1$H NMR (400 MHz, CDCl$_3$) δ=8.41 (s, 1H), 7.91 (d, J=7.6 Hz, 1H), 7.80 (d, J=8.4 Hz, 1H), 7.42 (t, J=7.8 Hz, 1H), 7.38-7.32 (m, 1H), 7.13-7.07 (m, 2H), 6.54-6.52 (m, 1H), 6.33 (m, 1H), 5.76 (d, J=10.4 Hz, 1H), 5.10-4.98 (br, 4H), 4.74-4.69 (m, 1H), 4.41-4.36 (m, 1H), 4.16 (m, 3H), 3.99 (d, J=12.0 Hz, 1H), 3.61-3.60 (m, 1H), 3.14-3.29 (m, 4H), 3.11 (br, 2H), 2.92-2.85 (m, 1H), 2.78 (s, 3H), 2.74-2.67 (m, 2H), 2.21-2.16 (m, 1H), 2.09-2.04 (m, 1H), 1.98-1.91 (m, 2H).

Example 288

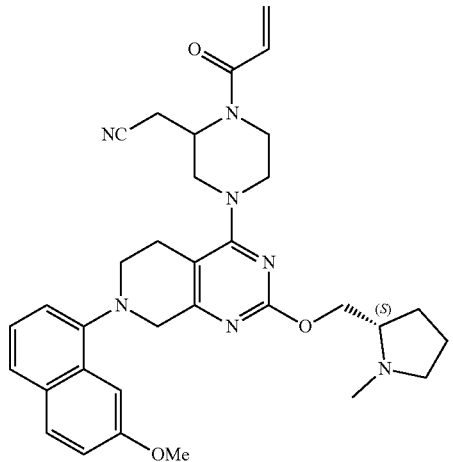

2-[4-[7-(7-methoxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

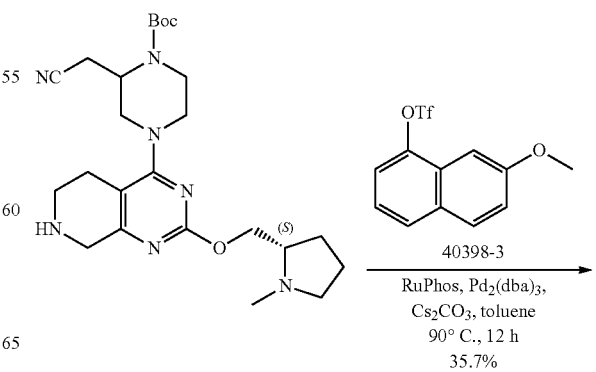

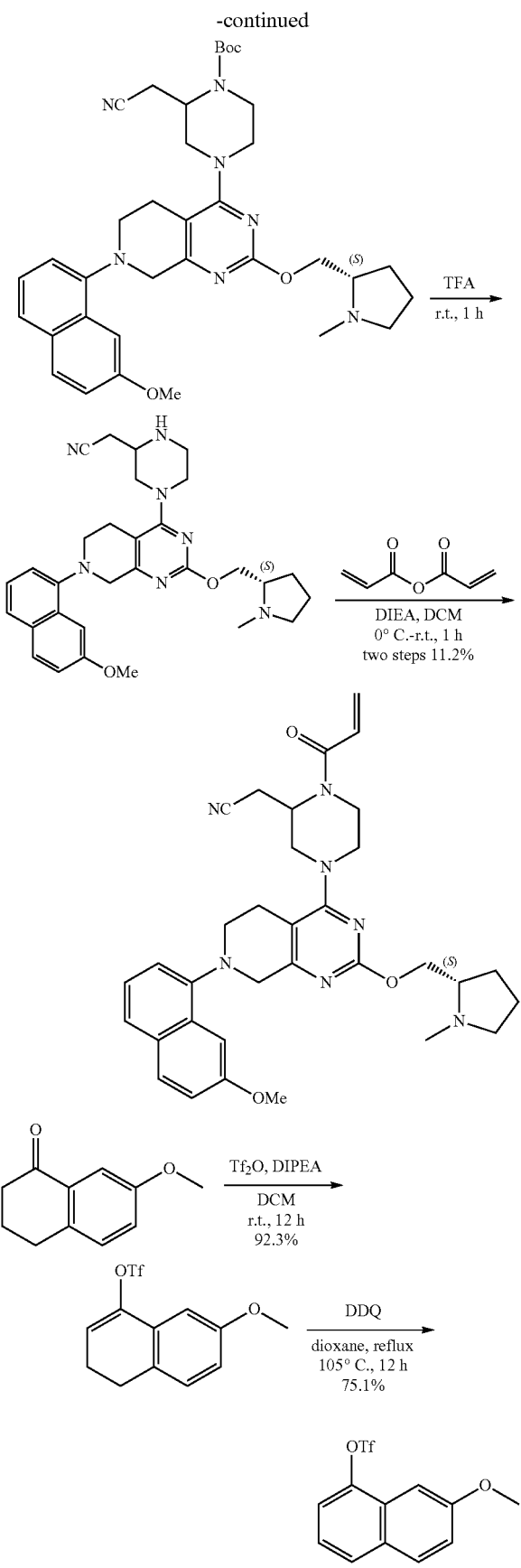

Step 1: (7-methoxy-3,4-dihydronaphthalen-1-yl) trifluoromethanesulfonate

To the solution of 7-methoxytetralin-1-one (1 g, 5.67 mmol, 1 eq), DIEA (2.20 g, 17.0 mmol, 2.97 mL, 3 eq) in DCM (15 mL) was added Tf$_2$O (2.40 g, 8.51 mmol, 1.40 mL, 1.5 eq) dropwise, then the mixture was stirred at 20° C. for 12 hours. The reaction mixture was concentrated under vacuum. The residue was purified by silica gel chromatography (PE:EtOAc from 1:0 to 100:1) to give (7-methoxy-3,4-dihydronaphthalen-1-yl) trifluoromethanesulfonate (1.7 g, 5.24 mmol, 92.3% yield, 95.0% purity) as yellow oil.

$^1$H NMR (400 MHz, chloroform-d) δ=7.06 (d, J=8.4 Hz, 1H), 6.75 (dd, 8.4 Hz, 1H), 6.66 (d, J=2.4 Hz, 1H), 6.45 (s, 1H), 3.80 (s, 3H), 3.04-2.96 (m, 2H), 2.68 (t, J=8.4 Hz, 2H).

Step 2: (7-methoxy-1-naphthyl) trifluoromethanesulfonate

A mixture of (7-methoxy-3,4-dihydronaphthalen-1-yl) trifluoromethanesulfonate (1.7 g, 5.51 mmol, 1 eq) and DDQ (2.50 g, 11.0 mmol, 2 eq) in dioxane (30 mL) was stirred at 105° C. for 12 hours. The reaction mixture was concentrated under vacuum. The residue was purified by silica gel chromatography (PE:EtOAc from 1:0 to 50:1) to give (7-methoxy-1-naphthyl) trifluoromethanesulfonate (1.41 g, 4.14 mmol, 75.1% yield, 90.0% purity) as a colorless oil.

$^1$H NMR (400 MHz, chloroform-d) δ=7.84 (d, J=9.2 Hz, 1H), 7.78 (d, J=8.8 Hz, 1H), 7.65 (d, J=2.4 Hz, 1H), 7.24-7.21 (m, 2H), 7.15 (d, J=2.4 Hz, 1H), 3.94 (s, 3H).

Step A: tert-butyl 2-(cyanomethyl)-4-[7-(7-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To the solution of tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate (Intermediate 66, 200 mg, 424 umol, 1 eq), (7-methoxy-1-naphthyl) trifluoromethanesulfonate (260 mg, 848 umol, 2 eq), RuPhos (39.6 mg, 84.8 umol, 0.2 eq), Cs$_2$CO$_3$ (414 mg, 1.27 mmol, 3 eq) in toluene (6 mL) was added Pd$_2$(dba)$_3$ (38.8 mg, 42.4 umol, 0.1 eq) under N$_2$. The suspension was degassed under vacuum and purged with N$_2$ several times. The mixture was stirred under N$_2$ at 90° C. for 12 hours. Water (5 mL) was added into the mixture. The resulting mixture was diluted with EtOAc (5 mL) and extracted with EtOAc (3×10 mL). The combined organic layers were dried over anhydrous Na$_2$SO$_4$, filtered and concentrated under vacuum. The residue was purified by reversed phase flash column (ACN/Water (0.1% FA)=34%) to give tert-butyl 2-(cyanomethyl)-4-[7-(7-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (100 mg, 151 umol, 35.7% yield, 95.0% purity) as brown solid. LCMS [ESI, M+1]: 628.

$^1$H NMR (400 MHz, chloroform-d) δ=7.69 (d, J=9.2 Hz, 1H), 7.63 (d, J=8.8 Hz, 1H), 7.17 (dd, J=2.4, 9.2 Hz, 1H), 7.09 (d, J=2.0 Hz, 1H), 7.03 (d, J=2.4 Hz, 1H), 6.96 (dd, J=2.4, 8.8 Hz, 1H), 4.61 (br s, 1H), 4.52-4.30 (m, 3H), 4.20 (ddd, J=3.2, 6.8, 10.4 Hz, 1H), 4.02 (br d, J=13.6 Hz, 2H), 3.92 (s, 3H), 3.87 (br d, J=13.2 Hz, 1H), 3.76-3.68 (m, 1H), 3.55-3.43 (m, 1H), 3.25 (br dd, J=3.6, 13.6 Hz, 2H), 3.12 (br t, J=7.6 Hz, 1H), 3.05-2.94 (m, 1H), 2.92-2.77 (m, 3H), 2.76-2.65 (m, 2H), 2.51 (s, 3H), 2.35-2.26 (m, 1H), 2.14-2.06 (m, 1H), 1.92-1.74 (m, 3H), 1.52 (s, 9H).

Step B: 2-[4-[7-(7-methoxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile A mixture of tert-butyl 2-(cyanomethyl)-4-[7-(7-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (100 mg, 159 umol, 1 eq) and TFA (363 mg, 3.19 mmol, 236 uL, 20 eq) was stirred at 18° C. for 1 hour. The reaction mixture was concentrated under vacuum to give 2-[4-[7-(7-methoxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (120 mg, crude, 2TFA) as brown oil.

Step C: 2-[4-[7-(7-methoxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To the solution of 2-[4-[7-(7-methoxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (120 mg, 159 umol, 1 eq, 2TFA), DIEA (205 mg, 1.59 mmol, 276 uL, 10 eq) in DCM (2.5 mL) was added prop-2-enoyl prop-2-enoate (24.0 mg, 190 umol, 1.2 eq) at 0° C. and stirred at 18° C. for 1 hour. Water (5 mL) was added into the mixture. The resulting mixture was extracted with DCM (3×5 mL). The combined organic layers were dried over anhydrous Na₂SO₄, filtered and concentrated under vacuum. The residue was purified by prep-HPLC (column: Gemini 150*25 5 u; mobile phase: [water (0.05% ammonia hydroxide v/v)-ACN]; B %: 45%-75%,10 min) to give title compound 2-[4-[7-(7-methoxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (10.6 mg, 17.8 umol, two steps 11.2% yield, 97.6% purity) as off-white solid. LCMS [ESI, M+1]: 582.

¹H NMR (400 MHz, chloroform-d) δ=7.70 (d, J=8.8 Hz, 1H), 7.63 (d, J=8.8 Hz, 1H), 7.17 (dd, J=2.4, 8.8 Hz, 1H), 7.09 (d, J=2.0 Hz, 1H), 7.03 (d, J=2.4 Hz, 1H), 6.97 (dd, J=2.4, 8.8 Hz, 1H), 6.57 (br d, J=10.4 Hz, 1H), 6.43-6.36 (m, 1H), 5.83 (br d, J=10.8 Hz, 1H), 5.09 (br s, 1H), 4.52-4.31 (m, 3H), 4.25-4.15 (m, 1H), 4.08 (br d, J=12.4 Hz, 1H), 3.96 (br s, 1H), 3.92 (s, 3H), 3.72 (br d, J=12.4 Hz, 1H), 3.54 (br d, J=5.6 Hz, 2H), 3.30 (br d, J=12.4 Hz, 1H), 3.22-2.95 (m, 3H), 2.93 (d, J=8.4 Hz, 1H), 2.86 (br d, J=4.8 Hz, 2H), 2.79-2.65 (m, 1H), 2.51 (s, 3H), 2.36-2.26 (m, 1H), 2.16-2.02 (m, 1H), 1.91-1.67 (m, 4H).

Example 289

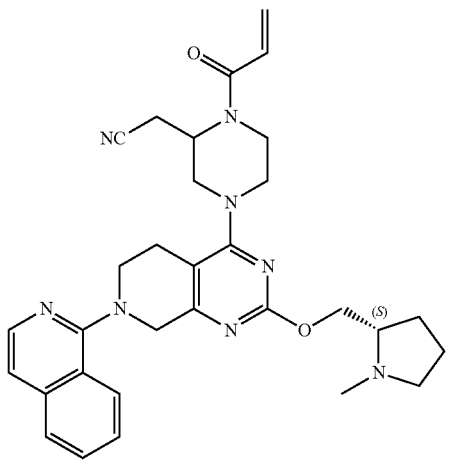

2-[4-[7-(1-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

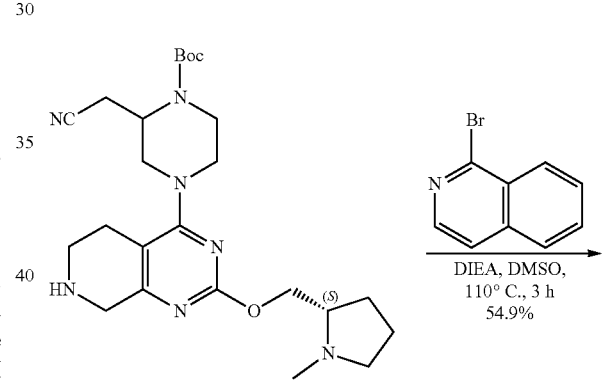

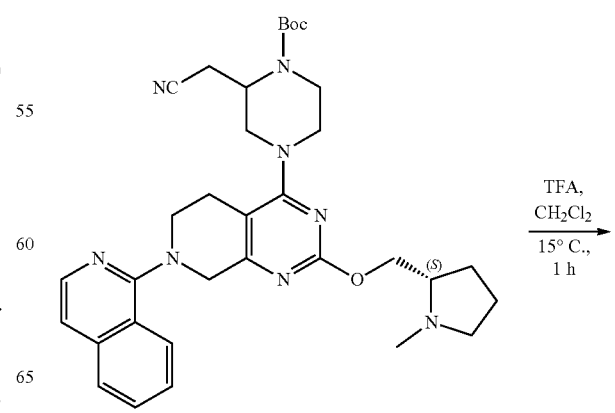

-continued

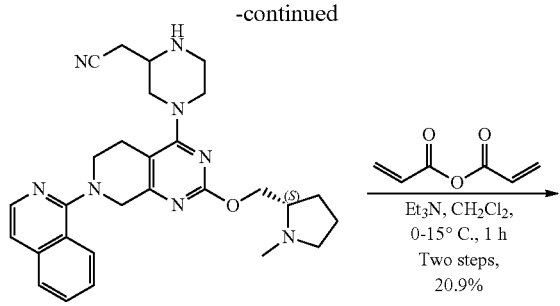

$\xrightarrow{\text{Et}_3\text{N, CH}_2\text{Cl}_2,}_{\substack{0\text{-}15°\text{ C., 1 h} \\ \text{Two steps,} \\ 20.9\%}}$

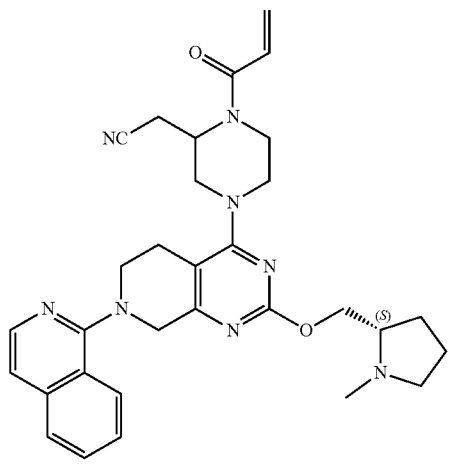

Step A: tert-butyl 2-(cyanomethyl)-4-[7-(1-isoquinolyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (0.20 g, 424 umol, 1.00 eq), 1-bromoisoquinoline (132 mg, 636 umol, 1.50 eq) and DIEA (109 mg, 848 umol, 148 uL, 2.00 eq) in DMSO (4.00 mL) was stirred at 110° C. for 3 hours. The mixture was diluted with water (5.00 mL), extracted with ethyl acetate (3×5.00 mL). The organic layers were washed with brine (1×10.0 mL), dried over Na$_2$SO$_4$, filtered and concentrated under vacuum. The residue was purified by reversed phase flash [water (FA, 0.10%)/acetonitrile]. The desired fractions were collected and adjust pH >7 with saturated sodium bicarbonate solution (6.00 mL), and extracted with ethyl acetate (3×20.0 mL). The organic layers were washed brine (1×30.0 mL), dried over Na$_2$SO$_4$, filtered and concentrated under vacuum to give tert-butyl 2-(cyanomethyl)-4-[7-(1-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (0.15 g, 233 umol, 54.9% yield) as a yellow solid. LCMS [ESI, M+1]: 599.

$^1$H NMR (400 MHz, chloroform-d) δ=8.17-8.11 (m, 2H), 7.78 (d, J=8.0 Hz, 1H), 7.64 (t, J=7.2 Hz, 1H), 7.57-7.51 (m, 1H), 7.28 (s, 1H), 4.69-4.55 (m, 3H), 4.42-4.35 (m, 1H), 4.15-4.01 (m, 3H), 3.96-3.81 (m, 2H), 3.57 (ddd, J=4.0, 8.0, 16.8 Hz, 1H), 3.27 (dd, J=4.0, 13.6 Hz, 1H), 3.18-3.16 (m, 1H), 3.16-2.95 (m, 3H), 2.91-2.73 (m, 3H), 2.70-2.62 (m, 1H), 2.48 (s, 3H), 2.34-2.24 (m, 1H), 2.07-2.01 (m, 1H), 1.91-1.73 (m, 3H), 1.52 (s, 9H).

Step B: 2-[4-[7-(1-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile A mixture of tert-butyl 2-(cyanomethyl)-4-[7-(1-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (0.15 g, 250.53 umol, 1.00 eq) and TFA (428 mg, 3.76 mmol, 278 uL, 15.0 eq) in dichloromethane (0.40 mL) was stirred at 15° C. for 1 hour. The mixture was concentrated under vacuum to give 2-[4-[7-(1-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (153 mg, crude, TFA) as a black oil and used into next step without further purification. LCMS [ESI, M+1]: 499.

Step C: 2-[4-[7-(1-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(1-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (153 mg, crude, TFA) and TEA (253 mg, 2.50 mmol, 348 uL) in dichloromethane (4.00 mL) was added prop-2-enoyl prop-2-enoate (31.5 mg, 250 umol) at 0° C., then stirred at 15° C. for 1 hour. The mixture was quenched with saturated sodium bicarbonate solution (1.00 mL) and concentrated under vacuum. The residue was purified by prep-HPLC column: (Phenomenex Synergi C18 150*25*10 um; mobile phase: [water (0.225%, FA)-ACN]; B %: 10%-24%, 7 min) and (column: Phenomenex Synergi C18 150*25*10 um; mobile phase: [water (0.225%, FA)-ACN]; B %: 10%-24%, 7 min). The desired fractions were collected and lyophilized to give title compound 2-[4-[7-(1-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (31.2 mg, 52.1 umol, two steps 20.9% yield, FA) as a yellow solid. LCMS [ESI, M+1]: 553.

$^1$H NMR (400 MHz, acetic) δ=8.44 (d, J=8.4 Hz, 1H), 8.04-7.95 (m, 2H), 7.89 (d, J=6.4 Hz, 1H), 7.82 (br t, J=6.8 Hz, 1H), 7.49 (d, J=6.8 Hz, 1H), 6.91-6.69 (m, 1H), 6.37 (br d, J=16.4 Hz, 1H), 5.87 (br d, J=9.2 Hz, 1H), 5.10 (br s, 2H), 4.78 (br s, 3H), 4.53 (br d, J=10.8 Hz, 1H), 4.32 (br d, J=12.8 Hz, 1H), 4.13 (br s, 3H), 3.90 (br s, 2H), 3.79-3.40 (m, 3H), 3.26 (br s, 3H), 3.12 (br s, 3H), 3.07-2.84 (m, 2H), 2.45-2.34 (m, 1H), 2.23-2.09 (m, 3H).

Example 290

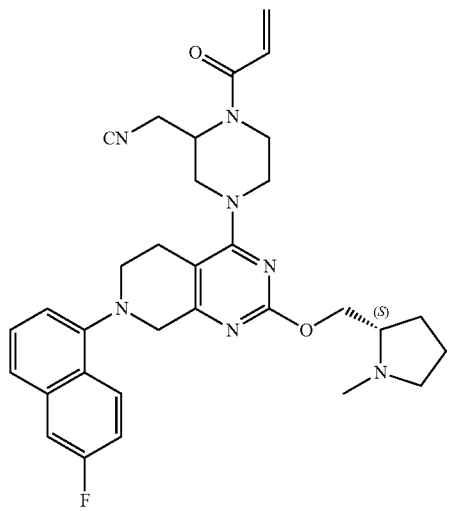

2-[4-[7-(6-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

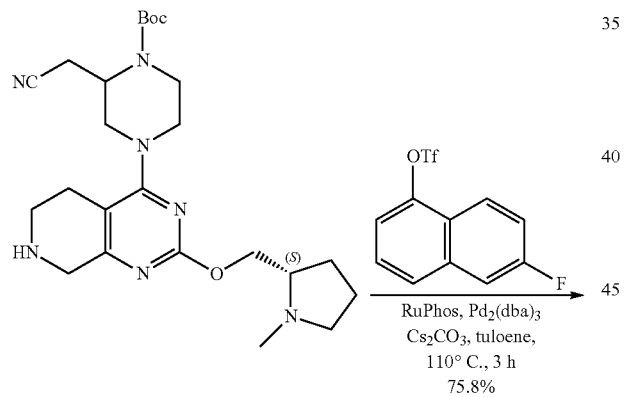

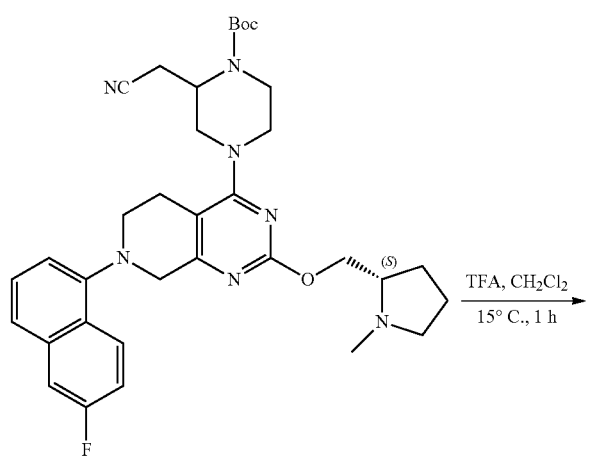

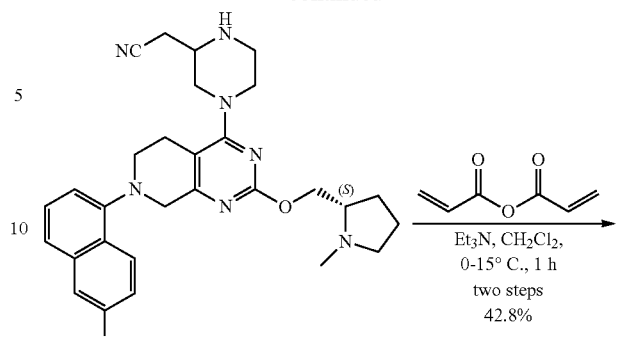

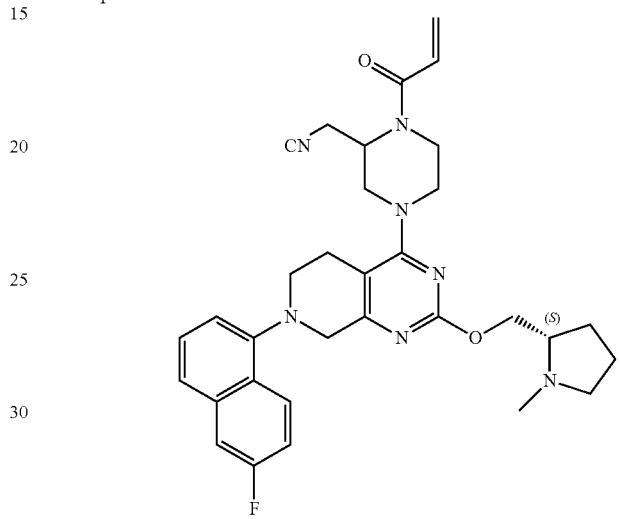

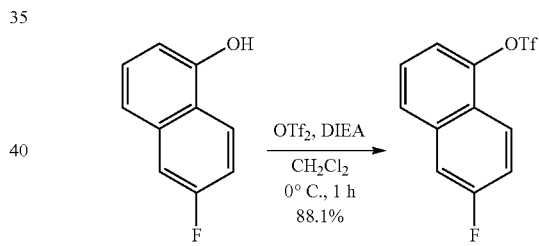

Insert: (6-fluoro-1-naphthyl) trifluoromethanesulfonate

To a solution of 6-fluoronaphthalen-1-ol (0.10 g, 617 umol, 1.00 eq) and DIEA (159 mg, 1.23 mmol, 215 uL, 2.00 eq) in dichloromethane (3.00 mL) was added trifluoromethylsulfonyl trifluoromethanesulfonate (191 mg, 678 umol, 112 uL, 1.10 eq) at 0° C. After stirred at 0° C. for 1 hour, the mixture was diluted with water (5.00 mL) and extracted with dichloromethane (3×5.00 mL). The organic layers were washed with brine (1×5.00 mL), dried over $Na_2SO_4$, filtered and concentrated under vacuum. The residue was purified by column chromatography ($SiO_2$, petroleum ether/ethyl acetate=3/1) to give (6-fluoro-1-naphthyl) trifluoromethanesulfonate (0.17 g, 543 umol, 88.1% yield) as a colorless oil.

$^1$H NMR (400 MHz, chloroform-d) δ=8.10 (dd, J=5.2, 8.8 Hz, 1H), 7.83 (d, J=8.4 Hz, 1H), 7.58-7.50 (m, 2H), 7.48-7.40 (m, 2H).

Step A: tert-butyl 2-(cyanomethyl)-4-[7-(6-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate (0.20 g, 424 umol, 1.00 eq), (6-fluoro-1-naphthyl) trifluoromethanesulfonate (150 mg, 509 umol, 1.20 eq), RuPhos (39.6 mg, 84.8 umol, 0.20 eq), Pd$_2$(dba)$_3$ (38.8 mg, 42.4 umol, 0.10 eq) and Cs$_2$CO$_3$ (415 mg, 1.27 mmol, 3.00 eq) in toluene (2.00 mL) was stirred at 110° C. for 3 hours under N$_2$. The mixture was diluted with water (5.00 mL), extracted with ethyl acetate (3×5.00 mL). The organic layers were washed with brine (1×10.0 mL), dried over Na$_2$SO$_4$, filtered and concentrated under vacuum. The residue was purified by reversed phase flash [water (FA, 0.10%)/acetonitrile]. The desired fractions were collected and adjust pH >7 with saturated sodium bicarbonate solution (5.00 mL), and then extracted with ethyl acetate (3×20.0 mL), the organic layers were washed brine (1×30.0 mL), dried over Na$_2$SO$_4$, filtered and concentrated under vacuum to give tert-butyl 2-(cyanomethyl)-4-[7-(6-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (0.20 g, 322 umol, 75.8% yield) as a yellow solid. LCMS [ESI, M+1]: 616.

$^1$H NMR (400 MHz, chloroform-d) δ=8.22 (dd, J=5.6, 9.2 Hz, 1H), 7.57-7.52 (m, 1H), 7.48-7.42 (m, 2H), 7.29-7.24 (m, 1H) 7.10 (d, J=7.6 Hz, 1H), 4.62 (br s, 1H), 4.39 (dd, J=4.8, 10.4 Hz, 1H), 4.31-4.22 (m, 2H), 4.14-4.00 (m, 3H), 3.95 (br d, J=12.8 Hz, 1H), 3.44 (br s, 1H), 3.35-3.25 (m, 2H), 3.23-2.90 (m, 4H), 2.86-2.63 (m, 4H), 2.49 (s, 3H), 2.33-2.24 (m, 1H), 2.13-2.00 (m, 1H) 1.89-1.74 (m, 3H), 1.53 (s, 9H).

Step B: 2-[4-[7-(6-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile A mixture of tert-butyl 2-(cyanomethyl)-4-[7-(6-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (0.20 g, 322 umol, 1.00 eq) and TFA (556 mg, 4.87 mmol, 361 uL, 15.0 eq) in dichloromethane (0.40 mL) was stirred at 15° C. for 1 hour. The mixture was concentrated under vacuum to give 2-[4-[7-(6-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (205 mg, crude, TFA) as a black oil and used into next step without further purification. LCMS [ESI, M+1]: 516.

Step C: 2-[4-[7-(6-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(6-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (205 mg, crude, TFA) and TEA (328 mg, 3.24 mmol, 451 uL) in dichloromethane (4.00 mL) was added prop-2-enoyl prop-2-enoate (40.9 mg, 324 umol) at 0° C., then stirred at 15° C. for 1 hour. The mixture was quenched with saturated sodium bicarbonate solution (1.00 mL) and concentrated under vacuum. The residue was purified by prep-HPLC (column: Phenomenex Synergi C18 150*25*10 um; mobile phase: [water (0.225%, FA)-ACN]; B %: 17%-44%, 9 min). The desired fractions were collected and lyophilized to give title compound 2-[4-[7-(6-fluoro-1-naphthyl)-2-[[(2S)-1-methylpyrrolidin-2-yl] methoxy]-6,8-dihydro-5H-pyrido[3,4-d]pyrimidin-4-yl]-1-prop-2-enoyl-piperazin-2-yl]acetonitrile (85.6 mg, 139 umol, 42.8% yield, FA) as a off-white solid. LCMS [ESI, M+1]: 570.

$^1$H NMR (400 MHz, acetic) δ=8.28 (dd, J=5.6, 9.2 Hz, 1H), 7.60 (d, J=8.0 Hz, 1H), 7.55-7.45 (m, 2H), 7.31 (dt, J=2.4, 8.8 Hz, 1H), 7.18 (d, J=7.2 Hz, 1H), 6.94-6.68 (m, 1H), 6.38 (br d, J=16.8 Hz, 1H), 5.87 (br d, J=10.0 Hz, 1H), 5.16 (br s, 1H), 4.84 (br s, 2H), 4.74-4.54 (m, 1H), 4.42 (br d, J=12.8 Hz, 1H), 4.33 (br s, 2H), 4.25-4.08 (m, 1H), 3.92 (br s, 2H), 3.81-3.47 (m, 3H), 3.46-3.16 (m, 4H), 3.11 (br s, 3H), 3.08-2.87 (m, 3H), 2.46-2.32 (m, 1H), 2.25-2.11 (m, 3H).

Example 291

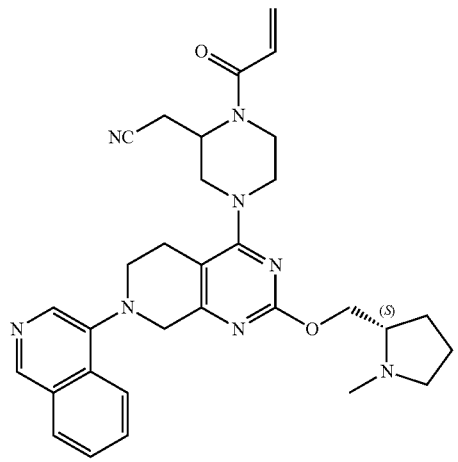

2-[4-[7-(4-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

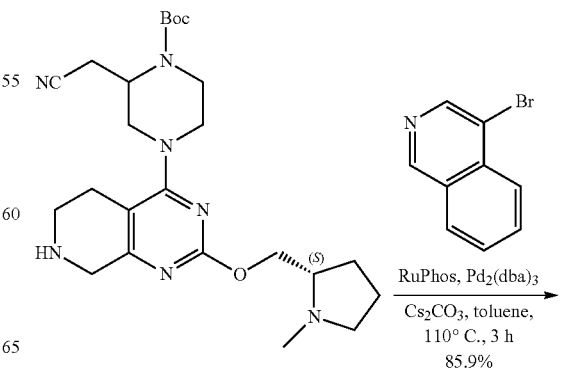

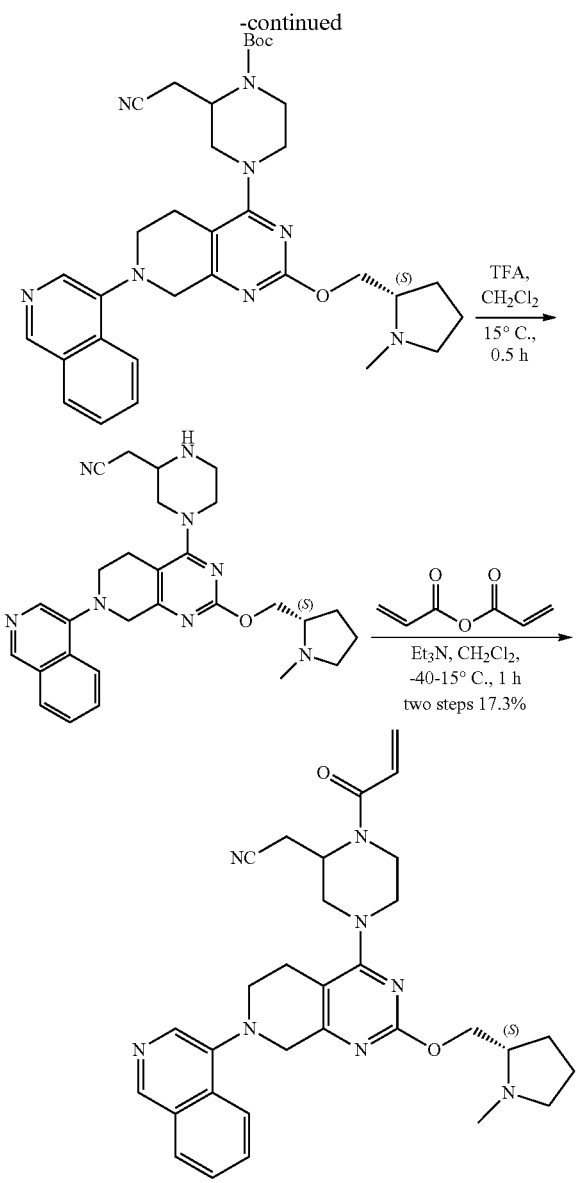

Step A: tert-butyl 2-(cyanomethyl)-4-[7-(4-isoquinolyl)-2-[[(2S)-1-methyl pyrrolidin-2-yl]methoxy]]-6,8-dihydro-5H-pyrido[3,4-d]pyrimidin-4-yl]piperazine-1-carboxylate A mixture of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (0.15 g, 318 umol, 1.00 eq), 4-bromoisoquinoline (99.3 mg, 477 umol, 1.50 eq), RuPhos (29.7 mg, 63.6 umol, 0.20 eq), Pd$_2$(dba)$_3$ (29.1 mg, 31.8 umol, 0.10 eq) and Cs$_2$CO$_3$ (311 mg, 954 umol, 3.00 eq) in toluene (5.00 mL) was stirred at 110° C. for 3 hours under N$_2$. The mixture was diluted with water (6.00 mL), extracted with ethyl acetate (3×5.00 mL). The organic layers were washed with brine (1×10.0 mL), dried over Na$_2$SO$_4$, filtered and concentrated under vacuum. The residue was purified by reversed phase flash [water (FA, 0.1%)/acetonitrile]. The desired fractions were collected and adjust pH >7 with saturated sodium bicarbonate solution (5.00 mL), and extracted with ethyl acetate (3×20.0 mL). The combined organic layers were washed brine (1×30.0 mL), dried over Na$_2$SO$_4$, filtered and concentrated under vacuum to give tert-butyl 2-(cyanomethyl)-4-[7-(4-isoquinolyl)-2-[[(2S)-1-methyl pyrrolidin-2-yl]methoxy]-6,8-dihydro-5H-pyrido[3,4-d]pyrimidin-4-yl]piperazine-1-carboxylate (0.17 g, 273 umol, 85.9% yield) as a yellow solid. LCMS [ESI, M+1]: 599.

$^1$H NMR (400 MHz, chloroform-d) δ=9.03 (s, 1H), 8.26 (s, 1H), 8.14 (d, J=8.4 Hz, 1H), 8.00 (d, J=8.0 Hz, 1H), 7.73 (dt, J=1.2, 7.2 Hz, 1H), 7.67-7.60 (m, 1H), 4.63 (br s, 1H), 4.44-4.31 (m, 3H), 4.15-4.03 (m, 2H), 3.95 (br d, J=12.8 Hz, 1H), 3.59-3.49 (m, 1H), 3.40 (br d, J=7.2 Hz, 1H), 3.34-3.19 (m, 2H), 3.18-2.93 (m, 4H), 2.90-2.79 (m, 2H), 2.77-2.66 (m, 2H), 2.50 (s, 3H), 2.35-2.24 (m, 1H), 2.10-2.02 (m, 1H), 1.92-1.79 (m, 3H), 1.52 (s, 9H).

Step B: 2-[4-[7-(4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile A mixture of tert-butyl 2-(cyanomethyl)-4-[7-(4-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (0.15 g, 251 umol, 1.00 eq) and TFA (428 mg, 3.76 mmol, 278 uL, 15.0 eq) in dichloromethane (0.30 mL) was stirred at 15° C. for 0.5 h. The mixture was concentrated under vacuum to give 2-[4-[7-(4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (153 mg, crude, TFA) as a black oil and used into next step without further purification. LCMS [ESI, M+1]: 499.

Step C: 2-[4-[7-(4-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (153 mg, crude, TFA) and Et$_3$N (254 mg, 2.51 mmol, 349 uL) in dichloromethane (2.00 mL) was added prop-2-enoyl prop-2-enoate (31.6 mg, 251 umol) at −40° C. After stirred at 15° C. for 1 hour, the mixture was quenched with saturated sodium bicarbonate solution (0.10 mL) and concentrated under vacuum. The residue was purified by column chromatography (Al$_2$O$_3$, methanol/ethyl acetate=1/1) and prep-HPLC (column: Boston Green ODS 150*30 5 u; mobile phase: [water (0.225%, FA)-ACN]; B %: 12%-36%, 10 min). The desired fractions were collected and lyophilized to give title compound 2-[4-[7-(4-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (28.3 g, 43.4 umol, two steps 17.3% yield, FA) as a yellow solid. LCMS [ESI, M+1]: 553.

$^1$H NMR (400 MHz, acetic) δ=9.45 (s, 1H), 8.51-8.36 (m, 3H), 8.17 (br t, J=8.0 Hz, 1H), 8.03-7.97 (m, 1H), 6.92-6.67 (m, 1H), 6.37 (br d, J=16.0 Hz, 1H), 5.87 (br d, J=10.0 Hz, 1H), 5.14 (br s, 1H), 4.82 (br s, 2H), 4.66-4.48 (m, 3H), 4.40 (br d, J=12.0 Hz, 1H), 4.22-3.80 (m, 3H), 3.79-3.49 (m, 4H), 3.32-3.09 (m, 7H), 3.07-2.88 (m, 2H), 2.47-2.36 (m, 1H), 2.24-2.11 (m, 3H).

Example 292

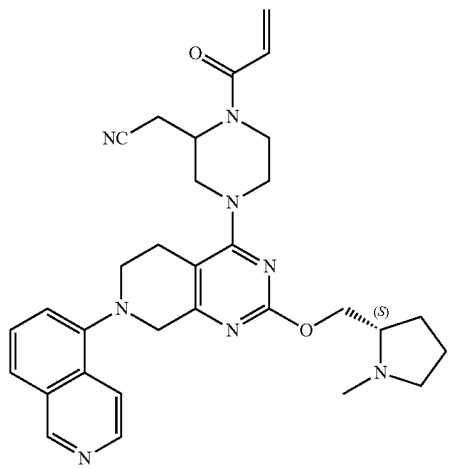

2-[4-[7-(5-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

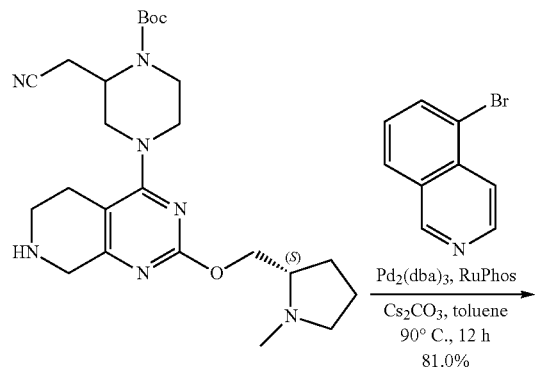

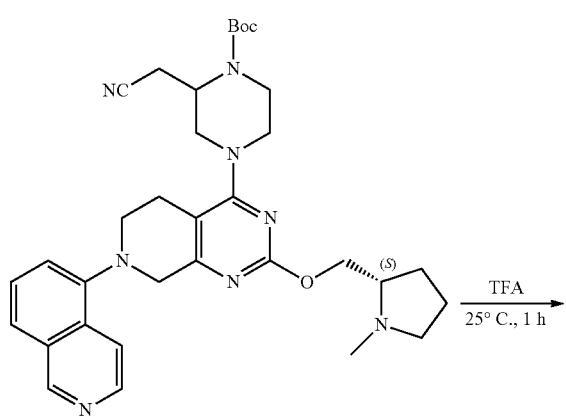

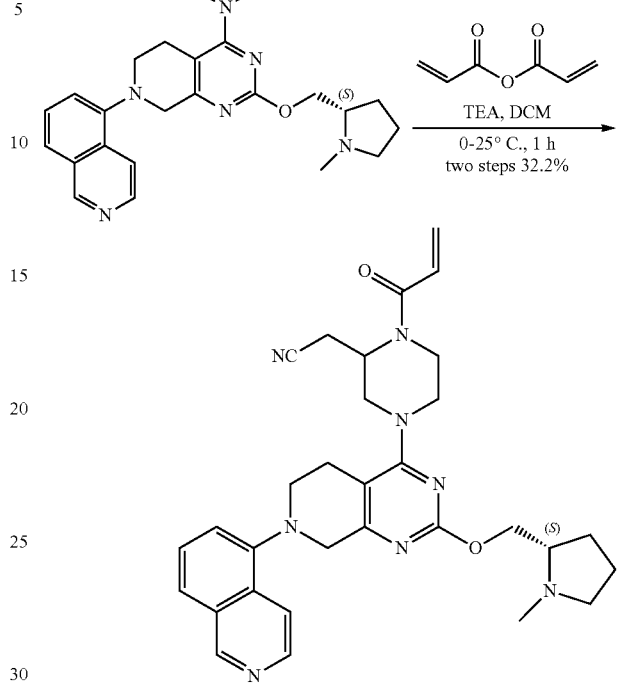

Step A: tert-butyl 2-(cyanomethyl)-4-[7-(5-isoquinolyl)-2-[[(2S)-1-methylpyrrolidin-2-yl]methoxy]-6,8-dihydro-5H-pyrido[3,4-d]pyrimidin-4-yl]piperazine-1-carboxylate tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate (200 mg, 424 umol, 1.00 eq), 5-bromoisoquinoline (115 mg, 551 umol, 1.30 eq), RuPhos (39.6 mg, 84.8 umol, 0.20 eq), Cs$_2$CO$_3$ (415 mg, 1.27 mmol, 3.00 eq) and Pd$_2$(dba)$_3$ (38.8 mg, 42.4 umol, 0.10 eq) in toluene (6.00 mL) was de-gassed and then heated to 90° C. for 12 hours under N$_2$. Upon completion, the reaction mixture was filtered and the filtrate was concentrated. The residue was purified by reversed-phase flash [water (0.1% FA)/acetonitrile] to give tert-butyl 2-(cyanomethyl)-4-[7-(5-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (217 mg, 344 umol, 81.0% yield, 94.8% purity) as a yellow solid. LCMS [ESI, M+1]: 599.

Step B: 2-[4-[7-(5-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile A solution of tert-butyl 2-(cyanomethyl)-4-[7-(5-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (217 mg, 362 umol, 1.00 eq) in TFA (620 mg, 5.44 mmol, 403 uL, 15.0 eq) was stirred at 25° C. for 1 hour. Upon completion, the reaction mixture was concentrated under vacuum to give 2-[4-[7-(5-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (222 mg, crude, TFA) as a yellow oil which was used directly in the next step without further purification. LCMS [ESI, M+1]: 499.

Step C: 2-[4-[7-(5-isoquinolyl)-2-[[(2S)-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(5-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (222 mg, 362 umol, TFA) and TEA (367 mg, 3.62 mmol, 504 uL) in DCM (4.50 mL) was added prop-2-enoyl prop-2-enoate (45.7 mg, 362 umol) dropwise at 0° C. The mixture was stirred at 25° C. for 1 hour. Upon completion, the reaction was quenched by MeOH (0.5 mL), diluted with water (2 mL) and extracted with EtOAc (2×5 mL). The organic layers were dried over Na$_2$SO$_4$ and concentrated under vacuum. The residue was purified by prep-HPLC (column: Phenomenex Synergi C18 150*25*10 um; mobile phase: [water (0.225% FA)-ACN]; B %: 4%-20%, 8 min) and lyophilized to give title compound 2-[4-[7-(5-isoquinolyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (73.0 mg, 117 umol, two steps 32.2% yield, 95.6% purity, FA) as a yellow solid. LCMS [ESI, M+1]:553.

$^1$H NMR (400 MHz, Acetic) δ=9.71 (s, 1H), 8.69 (d, J=6.4 Hz, 1H), 8.53 (d, J=6.8 Hz, 1H), 8.15 (d, J=8.0 Hz, 1H), 7.91 (t, J=7.8 Hz, 1H), 7.78 (d, J=7.2 Hz, 1H), 6.97-6.68 (m, 1H), 6.38 (br d, J=16.8 Hz, 1H), 5.87 (br d, J=10.4 Hz, 1H), 5.15 (br s, 1H), 4.81 (br d, J=4.4 Hz, 2H), 4.67-4.51 (m, 1H), 4.49-4.31 (m, 3H), 4.28-4.04 (m, 1H), 3.91 (br s, 2H), 3.78-3.64 (m, 1H), 3.63-3.37 (m, 4H), 3.36-3.20 (m, 1H), 3.11 (br s, 5H), 3.08-2.86 (m, 2H), 2.46-2.33 (m, 1H), 2.24-2.10 (m, 3H).

Example 293

2-[1-[(E)-but-2-enoyl]-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile

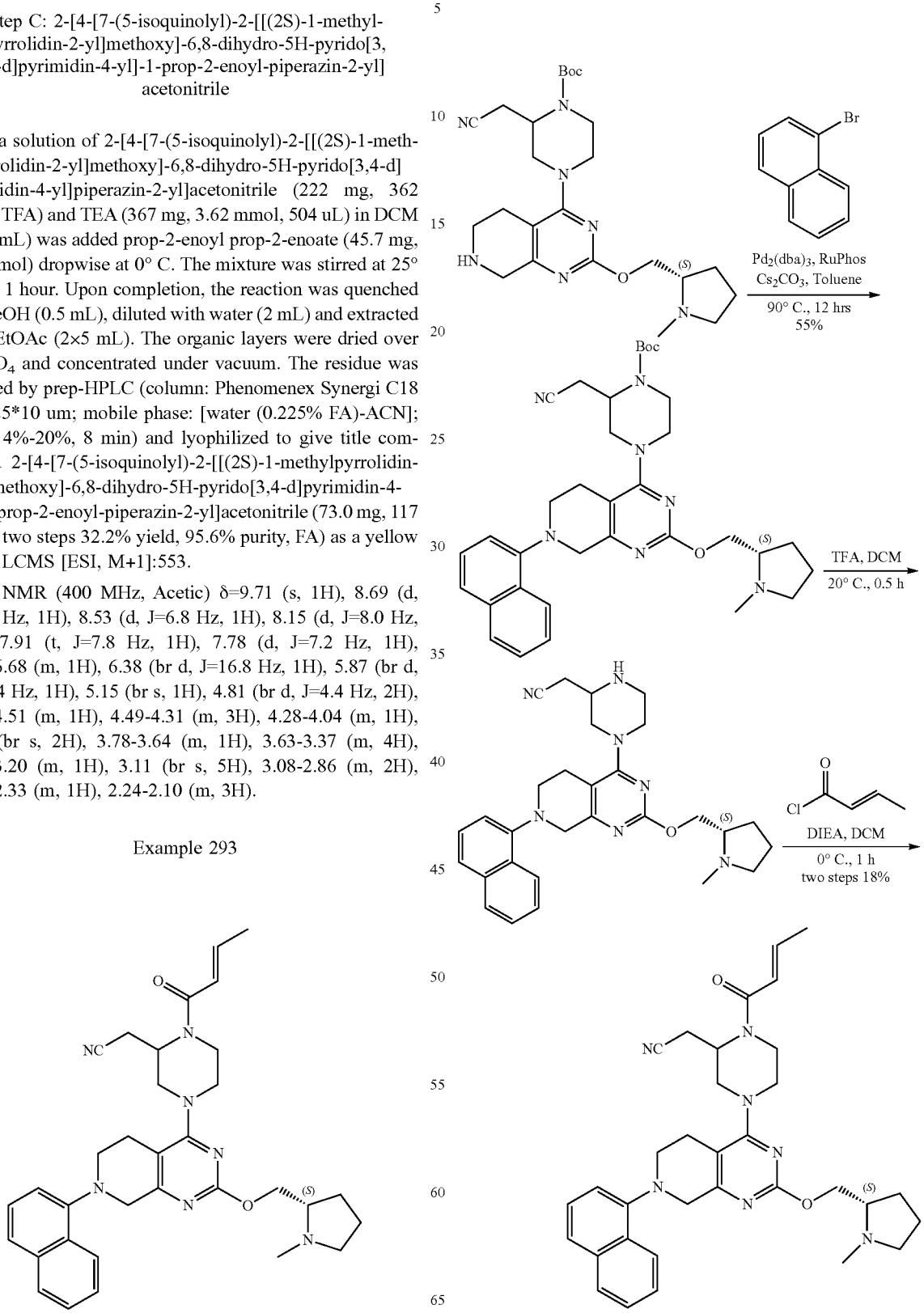

Step A: tert-butyl 2-(cyanomethyl)-4-[2-[[(2S)-1-methylpyrrolidin-2-yl]methoxy]-7-(1-naphthyl)-6,8-dihydro-5H-pyrido [3,4-d]pyrimidin-4-yl]piperazine-1-carboxylate A mixture of tert-butyl 2-(cyanomethyl)-4-[2-[[(2S)-1-methylpyrrolidin-2-yl]methoxy]-5,6,7,8-tetrahydropyrido [3,4-d]pyrimidin-4-yl]piperazine-1-carboxylate (100 mg, 212 umol, 1.0 eq), Pd$_2$(dba)$_3$ (19.4 mg, 21.2 umol, 0.10 eq), RuPhos (14.8 mg, 31.8 umol, 0.15 eq) and Cs$_2$CO$_3$ (207 mg, 636 umol, 3.0 eq) in toluene (3.0 mL) was dropwise added 1-bromonaphthalene (65.9 mg, 318 umol, 44.2 uL, 1.5 eq). The reaction mixture was degassed and purged with N$_2$ for 3 times, and the mixture was stirred at 110° C. for 4 hours under N$_2$ atmosphere. The reaction was washed with water (20.0 mL). The aqueous phase was extracted with ethyl acetate (20.0 mL×3). Combine extracts were washed with brine (50.0 mL), dried with Na$_2$SO$_4$ the solvent was then removed under vacuum. The residue was purified by reversed phase flash (C18, 0.1% FA in water, 0-80% MeCN). Compound tert-butyl 2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (80.0 mg, 116 umol, 54.6% yield) was obtained as a off-white solid. LCMS [ESI, M+1]: 598.

Step B: 2-[4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile To a solution of tert-butyl 2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (80.0 mg, 134 umol, 1.0 eq) in DCM (2.0 mL) was added TFA (3.08 g, 27.0 mmol, 2.0 mL, 202 eq). The mixture was stirred at 20° C. for 30 min under N$_2$ atmosphere. The organic solvent was removed under vacuum. The crude product 2-[4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (110 mg, crude, 2TFA) was obtained as a yellow oil and was used into the next step without further purification. LCMS [ESI, M+1]: 498.

Step C: 2-[1-[(E)-but-2-enoyl]-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile To a solution of 2-[4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (110 mg, 152 umol, 2TFA) in DCM (2.00 mL) was added DIEA (100 mg, 774 umol, 135 uL) and (E)-but-2-enoyl chloride (35.0 mg, 335 umol, 32.1 uL) at 0° C. The mixture was stirred at 0° C. for 1 hour. The reaction was quenched with water (10.0 mL). The crude mixture was extracted with ethyl acetate (20.0 mL×3). Combine extracts were washed with brine (50.0 mL), dried with Na$_2$SO$_4$ the solvent was then removed under vacuum. The residue was purified by prep-HPLC (column: Boston Green ODS 150*30 5 u; mobile phase: [water (0.225% FA)-ACN]; B %: 20%-50%,10 min) and lyophilization. Title compound 2-[1-[(E)-but-2-enoyl]-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (13.3 mg, 23.4 umol, 99.7% purity, FA) was obtained as a white solid. LCMS [ESI, M+1]: 566.

$^1$H NMR (400 MHz, Chloroform-d) δ 8.37 (s, 1H), 8.14-8.13 (m, 1H), 7.80-7.78 (m, 1H), 7.54 (d, J=8.0 Hz, 1H), 7.46-7.42 (m, 2H), 7.36 (m, 1H), 7.07 (d, J=7.6 Hz, 1H), 6.95-6.90 (m, 1H), 6.22 (d, J=15.6 Hz, 1H), 5.05-4.91 (br, 1H), 4.67-4.63 (m, 1H), 4.37-4.32 (m, 1H), 4.24-4.20 (m, 2H), 4.12 (d, J=14.8 Hz, 1H), 3.96 (d, J=11.6 Hz, 1H), 3.51-3.49 (m, 1H), 3.39-3.29 (m, 2H), 3.18-3.12 (m, 7H), 2.90-2.76 (m, 2H), 2.71 (s, 3H), 2.65-2.58 (m, 1H), 2.18-2.12 (m, 1H), 2.00-1.95 (m, 1H), 1.90-1.86 (m, 5H).

Example 294

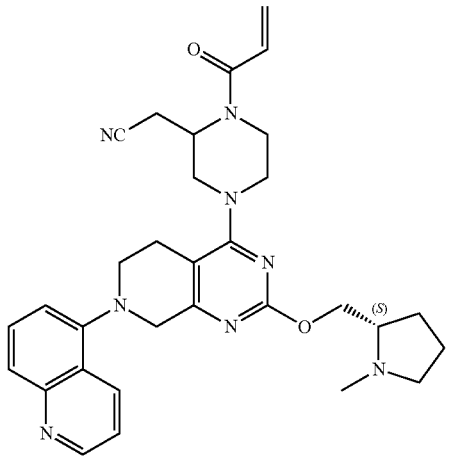

2-[4-[2-[[(2S)-1-methylpyrrolidin-2-yl]methoxy]-7-(5-quinolyl)-6,8-dihydro-5H-pyrido[3,4-d] pyrimidin-4-yl]-1-prop-2-enoyl-piperazin-2-yl]acetonitrile

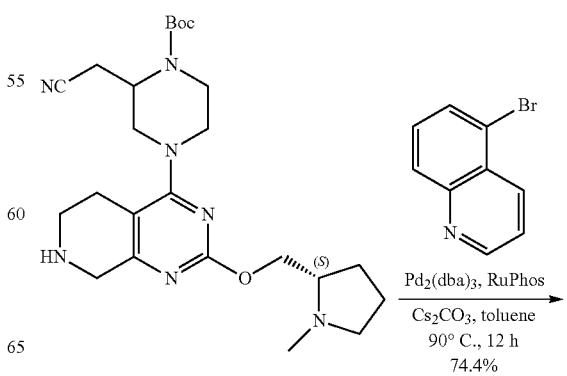

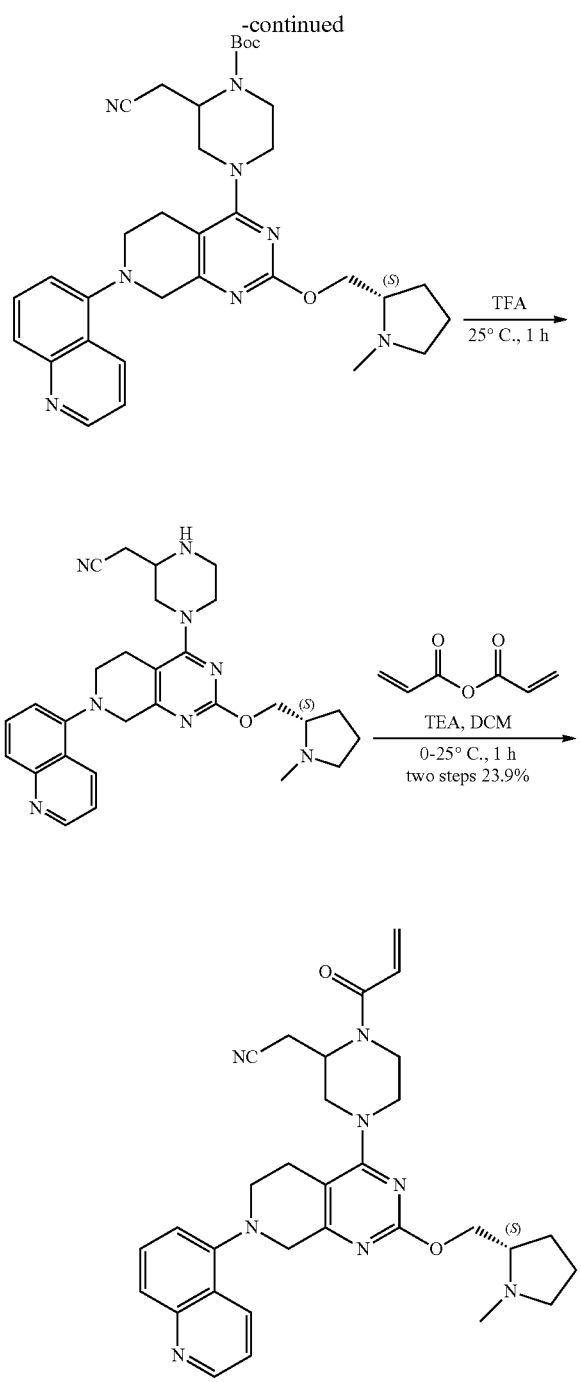

Step A: tert-butyl 2-(cyanomethyl)-4-[2-[[(2S)-1-methylpyrrolidin-2-yl]methoxy]-7-(5-quinolyl)-6,8-dihydro-5H-pyrido[3,4-d]pyrimidin-4-yl]piperazine-1-carboxylate tert-butyl 2-(cyanomethyl)-4-[2-[(1-methylpyrrolidin-2-yl)methoxy]-5,6,7,8-tetrahydropyrido[3,4-d]pyrimidin-4-yl]piperazine-1-carboxylate (200 mg, 424 umol, 1.00 eq), 5-bromoquinoline (115 mg, 551 umol, 1.30 eq), RuPhos (39.6 mg, 84.8 umol, 0.20 eq), $Cs_2CO_3$ (415 mg, 1.27 mmol, 3.00 eq) and $Pd_2(dba)_3$ (38.8 mg, 42.4 umol, 0.10 eq) in toluene (6.00 mL) was de-gassed and then heated to 90° C. for 12 hours under $N_2$. Upon completion, the reaction mixture was filtered and the filtrate was concentrated. The residue was purified by reversed-phase flash [water (0.1% FA)/acetonitrile] to give tert-butyl 2-(cyanomethyl)-4-[2-[[(2S)-1-methylpyrrolidin-2-yl]methoxy]-7-(5-quinolyl)-6,8-dihydro-5H-pyrido[3,4-d]pyrimidin-4-yl]piperazine-1-carboxylate (200 mg, 315 umol, 74.4% yield, 94.4% purity) as a brown oil. LCMS [ESI, M+1]: 599.

Step B: 2-[4-[2-[[(2S)-1-methylpyrrolidin-2-yl]methoxy]-7-(5-quinolyl)-6,8-dihydro-5H-pyrido[3,4-d]pyrimidin-4-yl]piperazin-2-yl]acetonitrile A solution of tert-butyl 2-(cyanomethyl)-4-[2-[[(2S)-1-methylpyrrolidin-2-yl]methoxy]-7-(5-quinolyl)-6,8-dihydro-5H-pyrido[3,4-d]pyrimidin-4-yl]piperazine-1-carboxylate (200 mg, 334 umol, 1.00 eq) in TFA (571 mg, 5.01 mmol, 371 uL, 15.0 eq) was stirred at 25° C. for 1 hour. Upon completion, the reaction mixture was concentrated under vacuum to give 2-[4-[2-[[(2S)-1-methylpyrrolidin-2-yl] methoxy]-7-(5-quinolyl)-6,8-dihydro-5H-pyrido[3,4-d] pyrimidin-4-yl]piperazin-2-yl]acetonitrile (204 mg, crude, TFA) as a yellow oil which was used directly in the next step without further purification. LCMS [ESI, M+1]: 499.

Step C: 2-[4-[2-[[(2S)-1-methylpyrrolidin-2-yl]methoxy]-7-(5-quinolyl)-6,8-dihydro-5H-pyrido[3,4-d]pyrimidin-4-yl]-1-prop-2-enoyl-piperazin-2-yl]acetonitrile To a solution of 2-[4-[2-[[(2S)-1-methylpyrrolidin-2-yl]methoxy]-7-(5-quinolyl)-6,8-dihydro-5H-pyrido[3,4-d]pyrimidin-4-yl]piperazin-2-yl]acetonitrile (204 mg, 333 umol, 1.00 eq, TFA) and TEA (337 mg, 3.33 mmol, 463 uL) in DCM (4.00 mL) was added prop-2-enoyl prop-2-enoate (42.0 mg, 333 umol) dropwise at 0° C. The mixture was stirred at 25° C. for 1 hour. Upon completion, the reaction was quenched with MeOH (0.5 mL), diluted with water (2 mL) and extracted with EtOAc (2×5 mL). The organic layers were dried over $Na_2SO_4$, filtered and concentrated under vacuum. The residue was purified by prep-TLC (DCM/MeOH 8/1) and prep-HPLC (column: Boston Green ODS 150*30 5 u; mobile phase: [water (0.225% FA)-ACN]; B %: 7%-34%,10 min). The desired fractions were collected and lyophilized to give title compound 2-[4-[2-[[(2S)-1-methylpyrrolidin-2-yl]methoxy]-7-(5-quinolyl)-6,8-dihydro-5H-pyrido[3,4-d]pyrimidin-4-yl]-1-prop-2-enoyl-piperazin-2-yl]acetonitrile (49.1 mg, 79.5 umol, two steps 23.9% yield, 96.9% purity, FA) as a yellow solid. LCMS [ESI, M+1]:553.

$^1$H NMR (400 MHz, Acetic) δ=9.22 (d, J=4.8 Hz, 1H), 9.15 (d, J=8.4 Hz, 1H), 8.09 (d, J=8.8 Hz, 1H), 7.98 (d, J=8.0 Hz, 1H), 7.96-7.90 (m, 1H), 7.50 (d, J=7.6 Hz, 1H), 6.98-6.71 (m, 1H), 6.37 (br d, J=17.2 Hz, 1H), 5.88 (br d, J=10.4 Hz, 1H), 5.15 (br s, 1H), 4.81 (br s, 2H), 4.77-4.52 (m, 1H), 4.50-4.33 (m, 3H), 4.14 (br d, J=12.4 Hz, 1H), 3.91 (br s, 2H), 3.79-3.66 (m, 1H), 3.65-3.32 (m, 4H), 3.12 (br s, 6H), 3.05 (br d, J=16.8 Hz, 2H), 2.46-2.34 (m, 1H), 2.23-2.09 (m, 3H).

Example 295

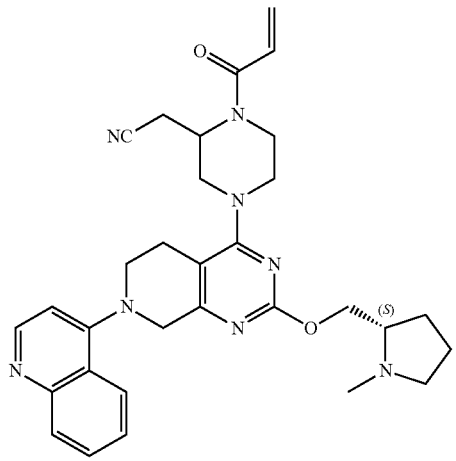

2-[4-[2-[[(2S)-1-methylpyrrolidin-2-yl]methoxy]-7-(4-quinolyl)-6,8-dihydro-5H-pyrido[3,4-d]pyrimidin-4-yl]-1-prop-2-enoyl-piperazin-2-yl]acetonitrile

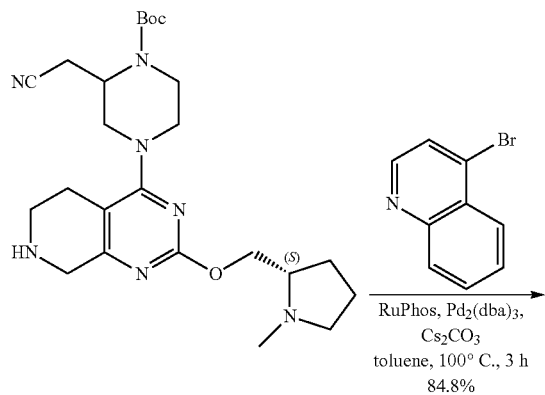

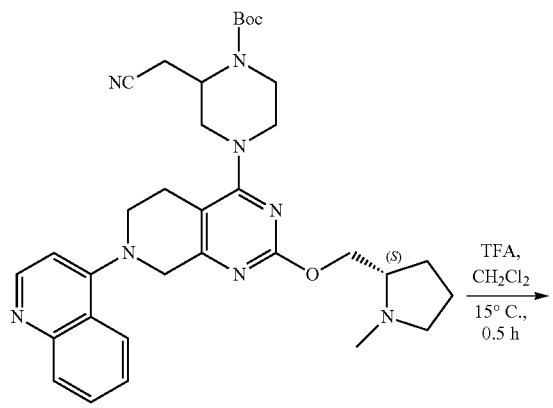

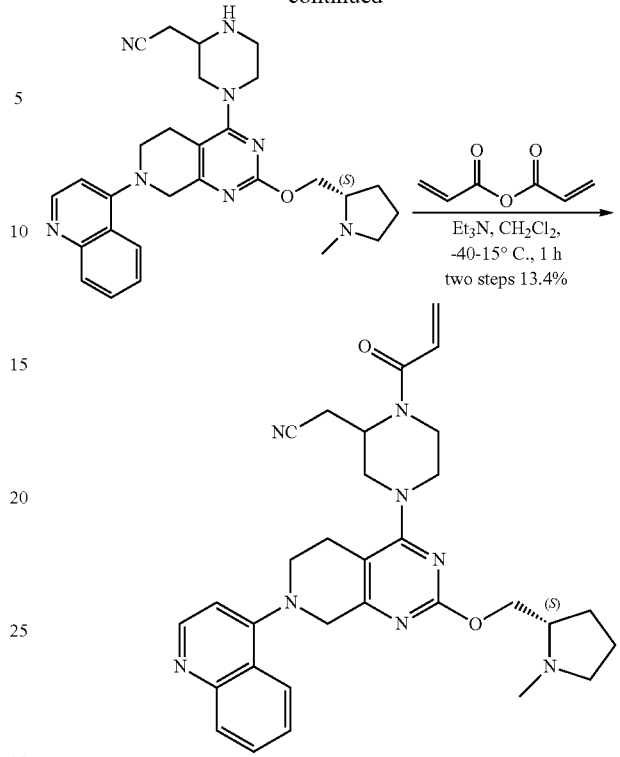

Step A: [2-[[(2S)-1-methylpyrrolidin-2-yl]methoxy]-7-(4-quinolyl)-6,8-dihydro-5H-pyrido[3,4-d]pyrimidin-4-yl]piperazine-1-carboxylate A mixture of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 0.15 g, 318 umol, 1.00 eq), 4-bromoquinoline (99.3 mg, 477 umol, 1.50 eq), RuPhos (29.7 mg, 63.6 umol, 0.20 eq), Pd$_2$(dba)$_3$ (29.1 mg, 31.8 umol, 0.10 eq) and Cs$_2$CO$_3$ (311 mg, 954 umol, 3.00 eq) in toluene (5 mL) was stirred at 100° C. for 3 hours under N$_2$. The mixture was diluted with water (5.00 mL), extracted with ethyl acetate (3×5.00 mL). The organic layers were washed with brine (1×10.0 mL), dried over Na$_2$SO$_4$, filtered and concentrated under vacuum. The residue was purified by reversed phase flash [water (FA, 0.1%)/acetonitrile]. The desired fractions were collected and adjust pH >7 with saturated sodium bicarbonate (5.00 mL) and extracted with ethyl acetate (3×20.0 mL). The organic layers were washed brine (1×30.0 mL), dried over Na$_2$SO$_4$, filtered and concentrated under vacuum to give tert-butyl 2-(cyanomethyl)-4-[2-[[(2S)-1-methylpyrrolidin-2-yl]methoxy]-7-(4-quinolyl)-6,8-dihydro-5H-pyrido[3,4-d]pyrimidin-4-yl]piperazine-1-carboxylate (0.17 g, 269 umol, 84.8% yield) as a yellow solid. LCMS [ESI, M+1]: 599.

$^1$H NMR (400 MHz, chloroform-d) δ=8.77 (d, J=4.8 Hz, 1H), 8.07 (dd, J=8.0, 16.0 Hz, 2H), 7.70 (dt, J=1.2, 7.2 Hz, 1H), 7.56-7.50 (m, 1H), 6.92 (d, J=4.8 Hz, 1H), 4.62 (br s, 1H), 4.44-4.33 (m, 3H), 4.15-4.04 (m, 2H), 3.95 (br d, J=12.0 Hz, 1H), 3.74-3.64 (m, 1H), 3.46 (br d, J=7.2 Hz, 1H), 3.37-3.21 (m, 2H), 3.18-2.93 (m, 4H), 2.93-2.79 (m, 2H), 2.72 (br dd, J=6.0, 16.8 Hz, 2H), 2.51 (s, 3H), 2.36-2.26 (m, 1H), 2.13-2.06 (m, 1H), 1.93-1.79 (m, 3H), 1.53 (s, 9H).

Step B: 2-[4-[2-[[(2S)-1-methylpyrrolidin-2-yl]methoxy]-7-(4-quinolyl)-6,8-dihydro-5H-pyrido[3,4-d]pyrimidin-4-yl]piperazin-2-yl]acetonitrile A mixture of tert-butyl 2-(cyanomethyl)-4-[2-[[(2S)-1-methylpyrrolidin-2-yl]methoxy]-7-(4-quinolyl)-6,8-dihydro-5H-pyrido[3,4-d]pyrimidin-4-yl]piperazine-1-carboxylate (165 mg, 276 umol, 1.00 eq) and TFA (471 mg, 4.13 mmol, 306 uL, 15.0 eq) in dichloromethane (0.30 mL) was stirred at 15° C. for 0.5 hour. The mixture was concentrated under vacuum to give 2-[4-[2-[[(2S)-1-methylpyrrolidin-2-yl]methoxy]-7-(4-quinolyl)-6,8-dihydro-5H-pyrido[3,4-d]pyrimidin-4-yl]piperazin-2-yl]acetonitrile (168 mg, crude, TFA) as a black oil and used into next step without further purification. LCMS [ESI, M+1]: 499.

Step C: 2-[4-[2-[[(2S)-1-methylpyrrolidin-2-yl]methoxy]-7-(4-quinolyl)-6,8-dihydro-5H-pyrido[3,4-d]pyrimidin-4-yl]-1-prop-2-enoyl-piperazin-2-yl]acetonitrile To a solution of 2-[4-[2-[[(2S)-1-methylpyrrolidin-2-yl]methoxy]-7-(4-quinolyl)-6,8-dihydro-5H-pyrido[3,4-d]pyrimidin-4-yl]piperazin-2-yl]acetonitrile (168 mg, crude, TFA) and Et$_3$N (277 mg, 2.74 mmol, 382 uL) in dichloromethane (3.00 mL) was added prop-2-enoyl prop-2-enoate (34.6 mg, 274.22 umol) at −40° C. After stirred at 15° C. for 1 hour, the mixture was quenched with saturated sodium bicarbonate (0.10 mL) and concentrated under vacuum. The residue was purified by column chromatography (Al$_2$O$_3$, methanol/ethyl acetate=1/1) and prep-HPLC (column: Phenomenex Synergi C18 150*25*10 um; mobile phase: [water (0.225%, FA)-ACN]; B %: 1%-21%, 7 min). The desired fractions were collected and lyophilized to give 2-[4-[2-[[(2S)-1-methylpyrrolidin-2-yl]methoxy]-7-(4-quinolyl)-6,8-dihydro-5H-pyrido[3,4-d]pyrimidin-4-yl]-1-prop-2-enoyl-piperazin-2-yl]acetonitrile (EXAMPLE 295, 23.4 mg, 39.6 umol, two steps 13.4% yield, 93.6% purity, FA) as a yellow oil. LCMS [ESI, M+1]: 553.

SFC condition: OD-3S_3_40_3 ML Column: Chiralcel OD-3 100×4.6 mm I.D., 3 um, mobile phase: 40% methanol (0.05% DEA) in CO$_2$, flow rate: 3 mL/min, wavelength: 220 nm.

$^1$H NMR (400 MHz, acetic) δ=8.65 (d, J=7.2 Hz, 1H), 8.35 (d, J=8.4 Hz, 1H), 8.15 (s, 1H), 7.99 (t, J=7.2 Hz, 1H), 7.77 (t, J=7.6 Hz, 1H), 7.28 (d, J=6.8 Hz, 1H), 6.74 (dd, J=10.8, 16.8 Hz, 1H), 6.32 (dd, J=1.2, 16.8 Hz, 1H), 5.85 (dd, J=1.2, 10.8 Hz, 1H), 5.01 (br s, 1H), 4.85-4.74 (m, 2H), 4.42 (br d, J=14.0 Hz, 1H), 4.35-4.19 (m, 3H), 4.16-3.76 (m, 4H), 3.66 (br d, J=14.0 Hz, 2H), 3.51-3.40 (m, 1H), 3.39-3.16 (m, 4H), 3.13 (s, 3H), 3.07-2.90 (m, 2H), 2.49-2.39 (m, 1H), 2.26-2.17 (m, 3H).

Example 296

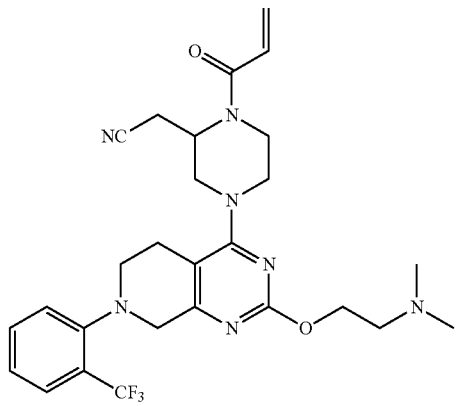 [SMILES: C=CC(=O)N1CCN(c2nc(OCCN(C)C)nc3c2CCN(c2ccccc2C(F)(F)F)C3)CC1CC#N]

2-[4-[2-[2-(dimethylamino)ethoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile

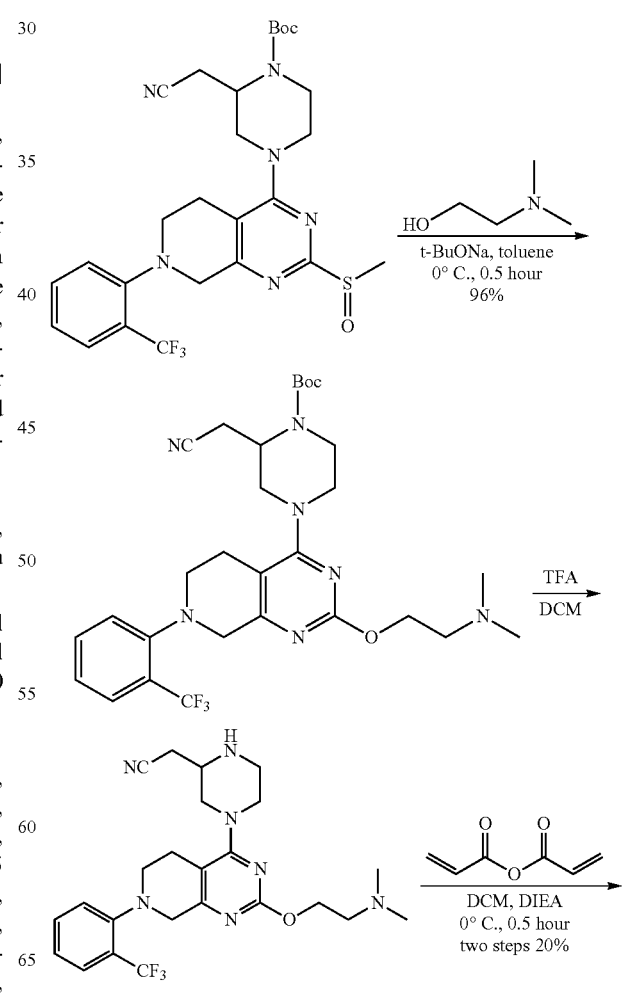

-continued

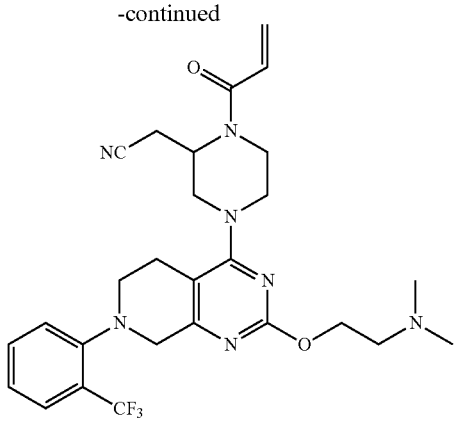

Step A: tert-butyl 2-(cyanomethyl)-4-[2-[2-(dimethylamino)ethoxy]-7-[2-(trifluoromethyl)phenyl]-6,8-dihydro-5H-pyrido[3,4-d]pyrimidin-4-yl]piperazine-1-carboxylate To a solution of tert-butyl 2-(cyanomethyl)-4-[2-methylsulfinyl-7-[2-(trifluoromethyl)phenyl]-6,8-dihydro-5H-pyrido[3,4-d]pyrimidin-4-yl]piperazine-1-carboxylate (150 mg, 266 umol, 1.0 eq) and 2-(dimethylamino)ethanol (47.4 mg, 531 umol, 53.3 uL, 2.0 eq) in toluene (1.0 mL) was added t-BuONa (51.1 mg, 531 umol, 2.0 eq). The mixture was stirred at 0° C. for 0.5 hour. After completion, the mixture was added water (10.0 mL) and extracted with EA (10 mL×3). The organic layer was dried over Na₂SO₄, filtered and concentrated. The obtained product was purified by reversed phase flash column (C18, 0.1% FA in water, 0-40% MeCN). The desired fraction was collected and adjusted with saturated NaHCO₃ aqueous to pH ~7, then concentrated under vacuum. The remained liquid was extracted with EA (10 mL×3). The organic layer was dried over Na₂SO₄, filtered and concentrated. The product tert-butyl 2-(cyanomethyl)-4-[2-[2-(dimethylamino)ethoxy]-7-[2-(trifluoromethyl)phenyl]-6,8-dihydro-5H-pyrido[3,4-d]pyrimidin-4-yl]piperazine-1-carboxylate (150 mg, 254 umol, 95.8% yield) was obtained as yellow oil. LCMS [ESI, M+1]: 590.

Step B: 2-[4-[2-[2-(dimethylamino)ethoxy]-7-[2-(trifluoromethyl)phenyl]-6,8-dihydro-5H-pyrido[3,4-d]pyrimidin-4-yl]piperazin-2-yl]acetonitrile To a solution of tert-butyl 2-(cyanomethyl)-4-[2-[2-(dimethylamino)ethoxy]-7-[2-(trifluoromethyl)phenyl]-6,8-dihydro-5H-pyrido[3,4-d]pyrimidin-4-yl]piperazine-1-carboxylate (150 mg, 254 umol, 1.0 eq) in DCM (1.0 mL) was added TFA (29.0 mg, 254 umol, 18.8 uL, 1.0 eq). The mixture was stirred at 0° C. for 0.5 hour. After completion, the mixture was concentrated under vacuum. The residue was added saturated NaHCO₃ aqueous (5 mL) and extracted with DCM (10 mL×3). The organic layer was dried over Na₂SO₄, filtered and concentrated to give 2-[4-[2-[2-(dimethylamino)ethoxy]-7-[2-(trifluoromethyl)phenyl]-6,8-dihydro-5H-pyrido[3,4-d]pyrimidin-4-yl]piperazin-2-yl]acetonitrile (200 mg, crude) as yellow oil. LCMS [ESI, M+1]: 490.

Step C: To a solution of 2-[4-[2-[2-(dimethylamino) ethoxy]-7-[2-(trifluoromethyl)phenyl]-6,8-dihydro-5H-pyrido[3,4-d]pyrimidin-4-yl]piperazin-2-yl]acetonitrile (125 mg, 255 umol, 1.0 eq) and DIEA (198 mg, 1.53 mmol, 267 uL, 6.0 eq) in DCM (1.00 mL) was added prop-2-enoyl prop-2-enoate (32.2 mg, 255 umol, 1.0 eq) at 0° C. The mixture was stirred at 0° C. for 0.5 hour. After completion, the mixture was concentrated under vacuum. The obtained product was purified by prep-HPLC (column: Phenomenex Synergi C18 150*30 mm*4 um; mobile phase: [water (0.225% FA)-ACN]; B %: 10%-40%, 10 min). Then concentrated and lyophilized. The product 2-[4-[2-[2-(dimethylamino)ethoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile (EXAMPLE 296, 30.7 mg, 51.8 umol, 20.3% yield, 99.5% purity, FA) was obtained as white solid. LCMS [ESI, M+1]: 544.

¹H NMR (400 MHz, Chloroform-d) δ 8.45 (br s, 1H), 7.67 (br d, J=8.0 Hz, 1H), 7.57 (t, J=7.2 Hz, 1H), 7.41 (d, J=8.0 Hz, 1H), 7.30 (d, J=7.6 Hz, 1H), 6.71-6.49 (m, 1H), 6.47-6.29 (m, 1H), 5.82 (br d, J=10.4 Hz, 1H), 5.07-4.97 (m, 1H), 4.54 (t, J=5.4 Hz, 2H), 4.12 (br d, J=13.6 Hz, 1H), 4.07 (s, 2H), 3.98 (br d, J=12.0 Hz, 1H), 3.40-3.30 (m, 2H), 3.22-3.09 (m, 4H), 3.05 (t, J=5.4 Hz, 2H), 2.92 (dd, J=8.0, 16.8 Hz, 1H), 2.86-2.81 (m, 1H), 2.79-2.70 (m, 2H), 2.56 (s, 6H).

Example 297

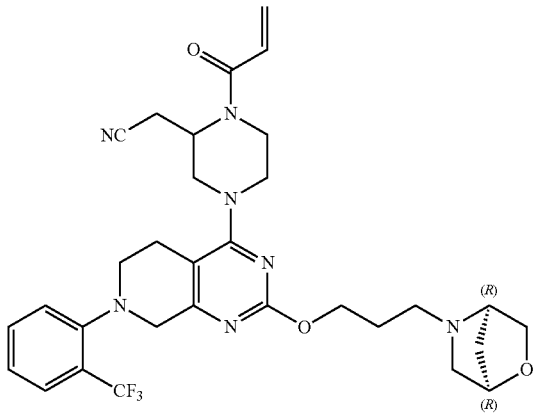

2-(1-acryloyl-4-(2-(((R)-1-methylpyrrolidin-3-yl)methoxy)-7-(2-(trifluoromethyl)phenyl)-5,6,7,8-tetrahydropyrido[3,4-d]pyrimidin-4-yl)piperazin-2-yl)acetonitrile

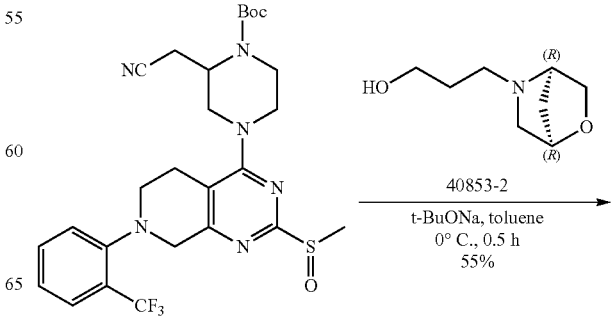

-continued

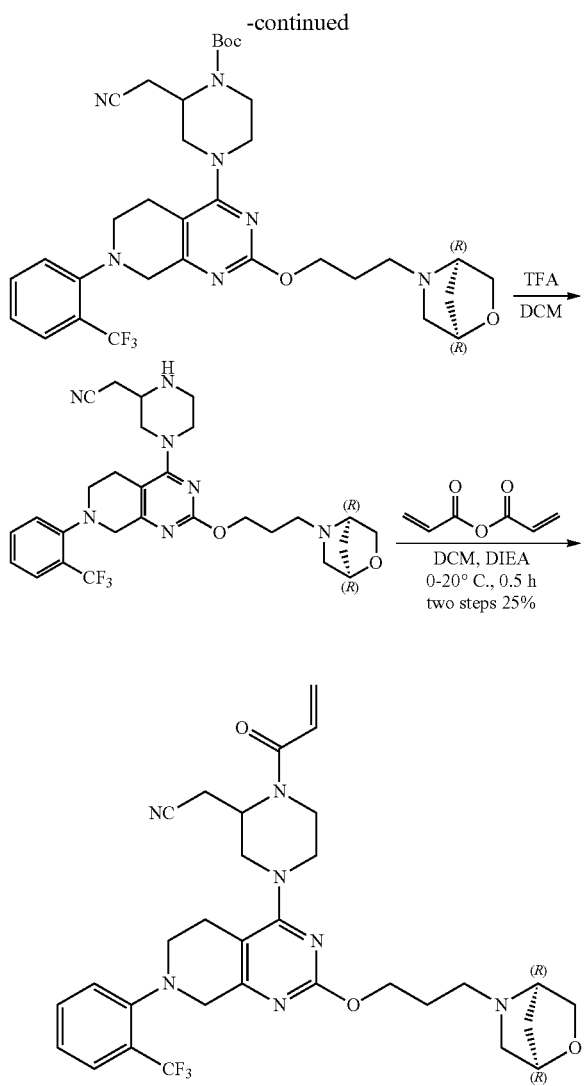

Step A: tert-butyl 2-(cyanomethyl)-4-[2-[3-[(1R,4R)-2-oxa-5-azabicyclo [2.2.1]heptan-5-yl]propoxy]-7-[2-(trifluoromethyl)phenyl]-6,8-dihydro-5H-pyrido[3,4-d]pyrimidin-4-yl]piperazine-1-carboxylate To a solution of tert-butyl 2-(cyanomethyl)-4-[2-methylsulfinyl-7-[2-(trifluoromethyl)phenyl]-6,8-dihydro-5H-pyrido[3,4-d]pyrimidin-4-yl]piperazine-1-carboxylate (200 mg, 354 umol, 1.0 eq) and 3-[(1R,4R)-2-oxa-5-azabicyclo[2.2.1]heptan-5-yl]propan-1-ol (Intermediate 18, 111 mg, 708 umol, 2.0 eq) in toluene (3.0 mL) was added t-BuONa (68.1 mg, 708 umol, 2.0 eq) at 0° C., the reaction was stirred at 0° C. for 0.5 hour. After completion, the reaction mixture was added water (10 mL), then extracted with EA (2×10 mL), the combined organic layer was dried over Na$_2$SO$_4$, filtered and concentrated. The residue was purified by reversed phase flash (C18, 60% MeCN in water), the obtained product was adjusted with saturated NaHCO$_3$ aqueous to pH ~8, then concentrated, extracted with EA (2×10.0 mL), the combined organic layer was dried over Na$_2$SO$_4$, filtered and concentrated to give tert-butyl 2-(cyanomethyl)-4-[2-[3-[(1R,4R)-2-oxa-5-azabicyclo [2.2.1]heptan-5-yl]propoxy]-7-[2-(trifluoromethyl)phenyl]-6,8-dihydro-5H-pyrido[3,4-d]pyrimidin-4-yl]piperazine-1-carboxylate (130 mg, 197 umol, 55.7% yield, 99.8% purity) as white solid. LCMS [ESI, M+1]: 658.

Step B: 2-[4-[2-[3-[(1R,4R)-2-oxa-5-azabicyclo [2.2.1]heptan-5-yl]propoxy]-7-[2-(trifluoromethyl) phenyl]-6,8-dihydro-5H-pyrido[3,4-d]pyrimidin-4-yl]piperazin-2-yl]acetonitrile To a mixture of tert-butyl 2-(cyanomethyl)-4-[2-[3-[(1R,4R)-2-oxa-5-azabicyclo[2.2.1]heptan-5-yl]propoxy]-7-[2-(trifluoromethyl)phenyl]-6,8-dihydro-5H-pyrido[3,4-d]pyrimidin-4-yl]piperazine-1-carboxylate (70.0 mg, 106 umol, 1.0 eq) in DCM (0.5 mL) was added TFA (770 mg, 6.75 mmol, 0.5 mL, 63.5 eq). The reaction mixture was stirred at 20° C. for 0.5 hour. After completion, the reaction mixture was concentrated to give 2-[4-[2-[3-[(1R,4R)-2-oxa-5-azabicyclo[2.2.1]heptan-5-yl]propoxy]-7-[2-(trifluoromethyl)phenyl]-6,8-dihydro-5H-pyrido[3,4-d]pyrimidin-4-yl]piperazin-2-yl]acetonitrile (83.0 mg, crude, 2TFA) as yellow oil which was used for the next step without further purification. LCMS [ESI, M+1]: 558.

Step C: 2-[4-[2-[3-[(1R,4R)-2-oxa-5-azabicyclo [2.2.1]heptan-5-yl]propoxy]-7-[2-(trifluoromethyl) phenyl]-6,8-dihydro-5H-pyrido[3,4-d]pyrimidin-4-yl]-1-prop-2-enoyl-piperazin-2-yl]acetonitrile To a mixture of 2-[4-[2-[3-[(1R,4R)-2-oxa-5-azabicyclo [2.2.1]heptan-5-yl]propoxy]-7-[2-(trifluoromethyl)phenyl]-6,8-dihydro-5H-pyrido[3,4-d]pyrimidin-4-yl]piperazin-2-yl]acetonitrile (83.0 mg, 106 umol, 1.0 eq, 2TFA) in DCM (1.0 mL) was added DIEA (81.9 mg, 634 umol, 110 uL, 6.0 eq) and prop-2-enoyl prop-2-enoate (13.3 mg, 106 umol, 1.0 eq) at 0° C., the reaction mixture was stirred at 20° C. for 0.5 hour. After completion, the reaction mixture was quenched with MeOH (0.5 mL), and concentrated. The residue was purified by prep-HPLC ((Instrument: ACSWH-GX-G; Column: Phenomenex Gemini 150*25 mm*10 um; Condition: water (0.225% FA)-ACN; Begin B:12; End B:42; Gradient Time (min): 10.5; 100% B Hold Time (min): 2; FlowRate (ml/min): 2), the obtained product was concentrated and then under lyophilization. The product 2-[4-[2-[3-[(1R,4R)-2-oxa-5-azabicyclo[2.2.1]heptan-5-yl]propoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile (EXAMPLE 297, 17.6 mg, 26.3 umol, two steps yield 24.9% yield, 98.1% purity, FA) was obtained as yellow solid. LCMS [ESI, M+1]: 612.

$^1$H NMR (400 MHz, chloroform-d) δ 7.69 (d, J=7.6 Hz, 1H), 7.59 (t, J=7.6 Hz, 1H), 7.42 (d, J=7.6 Hz, 1H), 7.31 (t, J=7.6 Hz, 1H), 6.72-6.52 (m 1H), 6.40 (d, J=16.4 Hz, 1H), 5.84 (br d, J=10.4 Hz, 1H), 5.16-5.02 (m, 1H), 4.58-4.51 (m, 1H), 4.38 (br t, J=5.8 Hz, 2H), 4.21 (br d, J=9.2 Hz, 1H), 4.18-4.06 (m, 4H), 3.99 (br d, J=11.6 Hz, 1H), 3.74 (br d, J=8.4 Hz, 1H), 3.42-3.29 (m, 2H), 3.27-3.04 (m, 6H), 3.04-2.61 (m, 6H), 2.28-2.07 (m, 3H), 2.04-1.92 (m, 1H).

Example 298

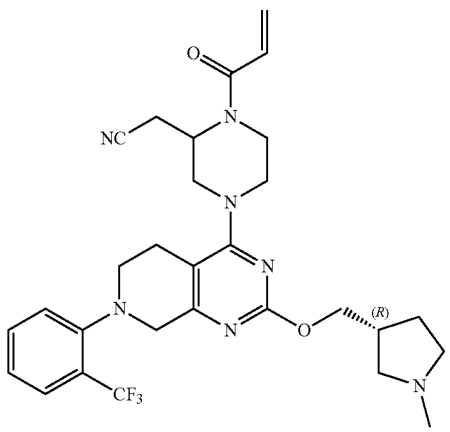

2-(1-acryloyl-4-(2-(((R)-1-methylpyrrolidin-3-yl)methoxy)-7-(2-(trifluoromethyl)phenyl)-5,6,7,8-tetrahydropyrido[3,4-d]pyrimidin-4-yl)piperazin-2-yl)acetonitrile

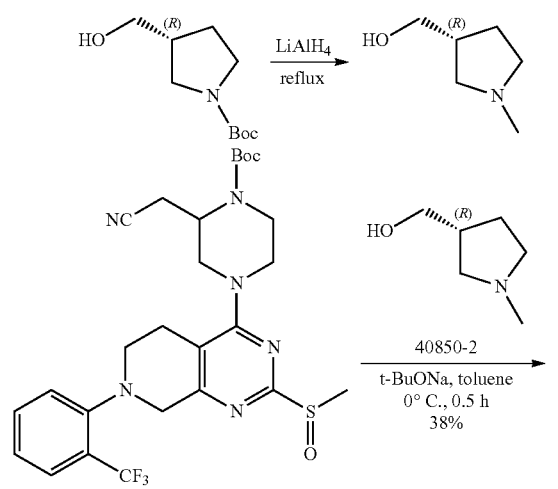

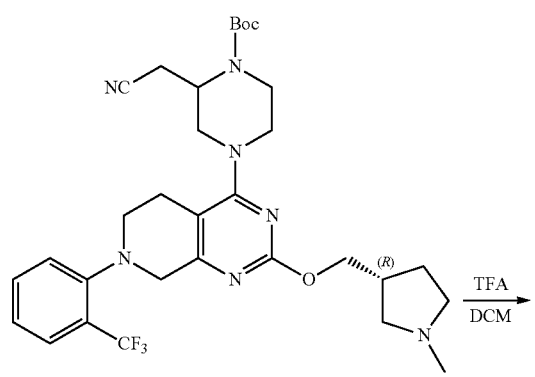

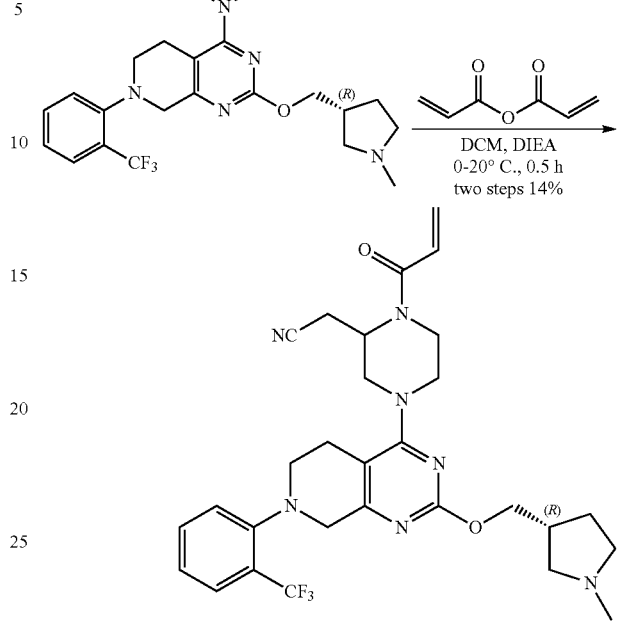

Step A: [(3R)-1-methylpyrrolidin-3-yl]methanol

To a solution of tert-butyl (3R)-3-(hydroxymethyl) pyrrolidine-1-carboxylate (2.0 g, 9.94 mmol, 1.0 eq) in THF (30.0 mL) was added LiAlH$_4$ (754 mg, 19.9 mmol, 2.0 eq) in portions at 0° C. After addition, the reaction was stirred at 70° C. for 3 hours. After completion, the reaction mixture was quenched with saturated Na$_2$SO$_4$ aqueous (2.4 mL), then extracted with Ethyl acetate (100 mL). The organic layer was dried with Na$_2$SO$_4$ and filtrated. The solvent was removed under vacuum to give [(3R)-1-methylpyrrolidin-3-yl]methanol (1.0 g, crude) as yellow oil which was used for the next step without further purification.

$^1$H NMR (400 MHz, chloroform-d) δ 3.64 (dd, J=4.8, 10.0 Hz, 1H), 3.52 (dd, J=5.6, 10.0 Hz, 1H), 2.78-2.67 (m, 1H), 2.60-2.45 (m, 2H), 2.42-2.23 (m, 5H), 2.08-1.91 (m, 1H), 1.72-1.57 (m, 1H).

Step B: tert-butyl 2-(cyanomethyl)-4-[2-[[(3R)-1-methylpyrrolidin-3-yl]methoxy]-7-[2-(trifluoromethyl)phenyl]-6,8-dihydro-5H-pyrido[3,4-d]pyrimidin-4-yl]piperazine-1-carboxylate To a solution of tert-butyl 2-(cyanomethyl)-4-[2-methylsulfinyl-7-[2-(trifluoromethyl)phenyl]-6,8-dihydro-5H-pyrido[3,4-d]pyrimidin-4-yl]piperazine-1-carboxylate (100 mg, 177 umol, 1.0 eq) and [(3R)-1-methylpyrrolidin-3-yl]methanol (61.2 mg, 531 umol, 3.0 eq) in toluene (1.0 mL) was added t-BuONa (34.0 mg, 354 umol, 2.0 eq) at 0° C., the reaction was stirred at 0° C. for 0.5 hour. After completion, the reaction mixture was added water (10.0 mL), then extracted with Ethyl acetate (2×10 mL), the combined organic layer was dried over Na$_2$SO$_4$, filtered and concentrated. The residue was purified by reversed phase flash (C18, 50% MeCN in water). tert-butyl 2-(cyanomethyl)-4-[2-[[(3R)-1-methylpyrrolidin-3-yl]methoxy]-7-[2-(trifluoromethyl)phenyl]-6,8-dihydro-5H-pyrido[3,4-d]pyrimidin- 4-yl]piperazine-1-carboxylate (40.0 mg, 63.4 umol, 35.8% yield, 97.6% purity) was obtained as white solid. LCMS [ESI, M+1]: 616.

Step C: 2-[4-[2-[[(3R)-1-methylpyrrolidin-3-yl]methoxy]-7-[2-(trifluoromethyl)phenyl]-6,8-dihydro-5H-pyrido[3,4-d]pyrimidin-4-yl]piperazin-2-yl]acetonitrile To a mixture of tert-butyl 2-(cyanomethyl)-4-[2-[[(3R)-1-methylpyrrolidin-3-yl]methoxy]-7-[2-(trifluoromethyl)phenyl]-6,8-dihydro-5H-pyrido[3,4-d]pyrimidin-4-yl]piperazine-1-carboxylate (40.0 mg, 64.9 umol, 1.0 eq) in DCM (0.5 mL) was added TFA (770 mg, 6.75 mmol, 500 uL, 104 eq). The reaction mixture was stirred at 20° C. for 0.5 hour. After completion, the reaction mixture was concentrated to give 2-[4-[2-[[(3R)-1-methylpyrrolidin-3-yl]methoxy]-7-[2-(trifluoromethyl)phenyl]-6,8-dihydro-5H-pyrido[3,4-d]pyrimidin-4-yl]piperazin-2-yl]acetonitrile (48.0 mg, crude, 2TFA) as yellow oil which was used for the next step without further purification. LCMS [ESI, M+1]: 516.

Step D: 2-[4-[2-[[(3R)-1-methylpyrrolidin-3-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile To a mixture of 2-[4-[2-[[(3R)-1-methylpyrrolidin-3-yl]methoxy]-7-[2-(trifluoromethyl)phenyl]-6,8-dihydro-5H-pyrido[3,4-d]pyrimidin-4-yl]piperazin-2-yl]acetonitrile (48.0 mg, 64.6 umol, 1.0 eq, 2TFA) in DCM (1.0 mL) was added DIEA (25.0 mg, 194 umol, 33.7 uL, 3.0 eq) and prop-2-enoyl prop-2-enoate (8.14 mg, 64.6 umol, 1.0 eq) at 0° C., the reaction mixture was stirred at 20° C. for 0.5 hour. After completion, the reaction mixture was quenched with methanol (0.5 mL), and concentrated. The residue was purified by prep-HPLC ((Instrument: ACSWH-GX-M; Column: Gemini 150*25 5 u; Condition: water (0.04% NH$_3$H$_2$O)-ACN; Begin B: 60; End B: 81; Gradient Time (min): 10; 100% B Hold Time (min):3; FlowRate (ml/min): 25), the obtained product was concentrated and then under lyophilization to give 2-[4-[2-[[(3R)-1-methylpyrrolidin-3-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile (5.48 mg, 9.26 umol, 14.4% yield, 96.3% purity) as brown solid. LCMS [ESI, M+1]: 570.

$^1$H NMR (400 MHz, chloroform-d) δ 7.61 (d, J=8.0 Hz, 1H), 7.50 (t, J=7.6 Hz, 1H), 7.33 (d, J=7.6 Hz, 1H), 7.22 (t, J=7.6 Hz, 1H), 6.54-6.44 (m, 1H), 6.32 (dd, J=1.6, 16.8 Hz, 1H), 5.75 (br d, J=10.8 Hz, 1H), 5.12-4.92 (m, 1H), 4.13 (d, J=6.8 Hz, 2H), 4.07-3.97 (m, 3H), 3.92-3.84 (m, 1H), 3.62-3.42 (m, 1H), 3.31-3.22 (m, 1H), 3.16-2.95 (m, 3H), 2.89-2.49 (m, 7H), 2.47-2.35 (m, 2H), 2.28 (s, 3H), 2.05-1.92 (m, 1H), 1.57-1.46 (m, 2H).

Example 299

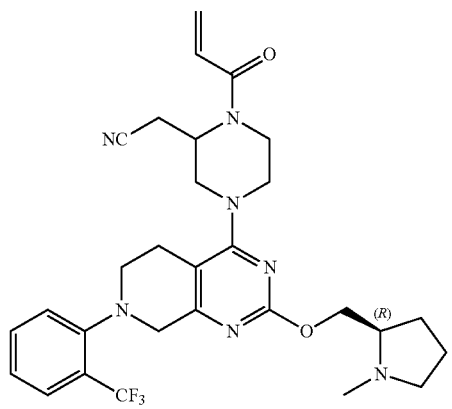

2-[4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile

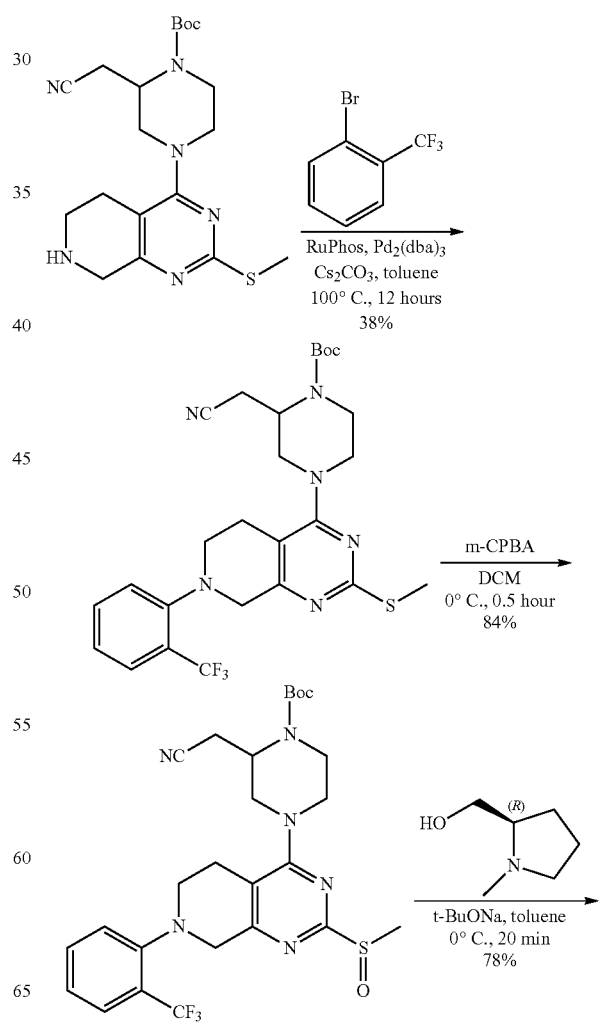

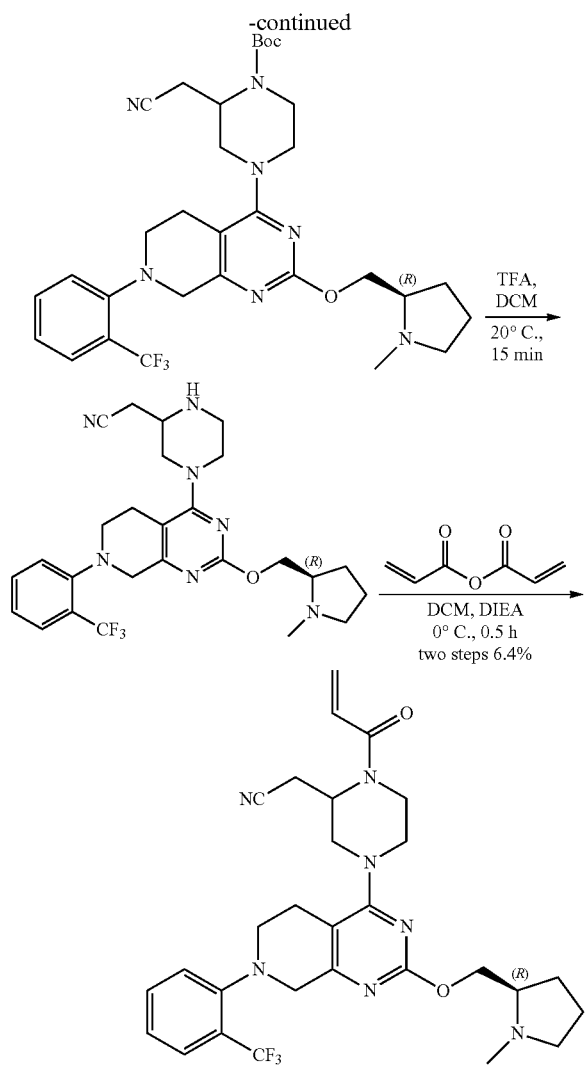

Step A: tert-butyl 2-(cyanomethyl)-4-[2-methylsulfanyl-7-[2-(trifluoromethyl)phenyl]-6,8-dihydro-5H-pyrido[3,4-d]pyrimidin-4-yl]piperazine-1-carboxylate To a solution of tert-butyl 2-(cyanomethyl)-4-(2-methylsulfanyl-5,6,7,8-tetrahydropyrido[3,4-d]pyrimidin-4-yl)piperazine-1-carboxylate (3.70 g, 9.15 mmol, 1.0 eq), Pd$_2$(dba)$_3$ (1.26 g, 1.37 mmol, 0.15 eq), RuPhos (854 mg, 1.83 mmol, 0.2 eq) and Cs$_2$CO$_3$ (7.45 g, 22.9 mmol, 2.50 eq) in toluene (74.0 mL) was added 1-bromo-2-(trifluoromethyl)benzene (4.12 g, 18.3 mmol, 2.49 mL, 2.0 eq). The mixture was stirred at 100° C. for 12 hours. After completion, the mixture was added water (100 mL) and extracted with Ethyl acetate (100 mL×3). The organic layer was dried over Na$_2$SO$_4$, filtered and concentrated. The residue was purified by reversed phase flash column (C18, 0.1% FA in water, 0-90% MeCN). The product tert-butyl 2-(cyanomethyl)-4-[2-methylsulfanyl-7-[2-(trifluoromethyl)phenyl]-6,8-dihydro-5H-pyrido[3,4-d]pyrimidin-4-yl]piperazine-1-carboxylate (1.90 g, 3.46 mmol, 37.8% yield) was obtained as yellow solid.

$^1$H NMR (400 MHz, Chloroform-d) δ 7.69 (d, J=8.0 Hz, 1H), 7.57 (t, J=7.6 Hz, 1H), 7.46-7.37 (m, 2H), 7.22-7.11 (m, 1H), 4.67-4.55 (m, 1H), 4.03 (br d, J=13.6 Hz, 2H), 3.88 (br d, J=12.0 Hz, 1H), 3.68-3.47 (m, 1H), 3.30-3.08 (m, 4H), 3.02 (dt, J=3.2, 12.4 Hz, 1H), 2.94-2.69 (m, 4H), 2.51 (s, 3H), 1.52 (s, 9H).

Step B: tert-butyl 2-(cyanomethyl)-4-[2-methylsulfinyl-7-[2-(trifluoromethyl)phenyl]-6,8-dihydro-5H-pyrido[3,4-d]pyrimidin-4-yl]piperazine-1-carboxylate To a solution of tert-butyl 2-(cyanomethyl)-4-[2-methylsulfanyl-7-[2-(trifluoromethyl)phenyl]-6,8-dihydro-5H-pyrido[3,4-d]pyrimidin-4-yl]piperazine-1-carboxylate (1.50 g, 2.46 mmol, 1.0 eq) in DCM (15.0 mL) was added m-CPBA (593 mg, 2.75 mmol, 1.12 eq, 80% purity) at 0° C. The mixture was stirred at 0° C. for 0.5 hour. After completion, the mixture was added saturated Na$_2$S$_2$O$_3$ aqueous (30.0 mL) and extracted with ethyl acetate (30.0 mL×3). The organic layer was dried over Na$_2$SO$_4$, filtered and concentrated. The residue was purified by reversed phase flash column (C18, 0.1% FA in water, 0-90% MeCN) to give tert-butyl 2-(cyanomethyl)-4-[2-methylsulfinyl-7-[2-(trifluoromethyl)phenyl]-6,8-dihydro-5H-pyrido[3,4-d]pyrimidin-4-yl]piperazine-1-carboxylate (1.16 g, 2.05 mmol, 83.6% yield) as yellow solid. LCMS [ESI, M+1]:565.

Step C: tert-butyl (2S)-2-(cyanomethyl)-4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]piperazine-1-carboxylate To a solution of tert-butyl (2S)-2-(cyanomethyl)-4-[2-methylsulfinyl-7-[2-(trifluoromethyl)phenyl]-6,8-dihydro-5H-pyrido[3,4-d]pyrimidin-4-yl]piperazine-1-carboxylate (200 mg, 354 umol, 1.0 eq) in toluene (3.0 mL) was added [(2R)-1-methylpyrrolidin-2-yl]methanol (81.6 mg, 708.4 umol, 2.0 eq) and t-BuONa (68.1 mg, 708 umol, 2.0 eq) at 0° C. The mixture was stirred at 0° C. for 20 min. After completion, the reaction was quenched with water (10.0 mL). The crude mixture was extracted with ethyl acetate (15 mL×3). The combined organic layer were washed with brine (50.0 mL), dried with Na$_2$SO$_4$ and filtrated. The solvent was then removed under vacuum. The residue was purified by reversed phase flash (C18, 0.1% FA in water, 0-80% MeCN). Compound tert-butyl (2S)-2-(cyanomethyl)-4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]piperazine-1-carboxylate (170 mg, 275 umol, 77.7% yield) was obtained as a white solid. LCMS [ESI, M+1]:616.

$^1$H NMR (400 MHz, CHLOROFORM-d) 8.08 (s, 1H), 7.61 (d, J=7.6 Hz, 1H), 7.51 (t, J=7.7 Hz, 1H), 7.34 (d, J=8.0 Hz, 1H), 7.25-7.19 (m, 1H), 5.02-4.78 (m, 1H), 4.58-4.43 (m, 2H), 4.17 (br t, J=12.5 Hz, 1H), 4.08-3.86 (m, 5H), 3.64-3.51 (m, 1H), 3.23 (br dd, J=3.8, 13.8 Hz, 1H), 3.11-3.01 (m, 3H), 2.96 (s, 3H), 2.84-2.58 (m, 4H), 2.31-2.03 (m, 2H), 2.02-1.94 (m, 3H), 1.44 (s, 9H), 1.19 (t, J=7.2 Hz, 1H).

Step D: 2-[4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]piperazin-2-yl]acetonitrile To a solution of tert-butyl 2-(cyanomethyl)-4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]piperazine-1-carboxylate (170 mg, 276 umol, 1.0 eq) in DCM (1.50 mL) was added TFA (2.31 g, 20.3 mmol, 1.50 mL, 73.4 eq). The mixture was stirred at 20° C. for 15 min under N$_2$ atmosphere. After completion, the organic solvent was removed under vacuum. The crude product 2-[4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]piperazin-2-yl]acetonitrile (240 mg, crude, 2TFA) was obtained as a yellow oil and used into the next step without further purification. LCMS [ESI, M+1]: 516.

Step E: 2-[4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile To a solution of 2-[4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]piperazin-2-yl]acetonitrile (240 mg, 2TFA) in DCM (3.0 mL) was added prop-2-enoyl prop-2-enoate (40.0 mg, 317 umol) and DIEA (130 mg, 1.01 mmol, 175 uL) at 0° C. The mixture was stirred at 0° C. for 30 mins. The reaction was quenched with water (20.0 mL). The crude mixture was extracted with ethyl acetate (20.0 mL×3). The combine extracts were washed with brine (50.0 mL), dried with Na$_2$SO$_4$ and filtrated. The solvent was then removed under vacuum. The residue was purified by prep-HPLC (column: Phenomenex Gemini 150×25 mm×10 um; mobile phase: [water (0.05% ammonia hydroxide v/v)-ACN]; B %: 55%-85%,3 min). Compound 2-[4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile (EXAMPLE 299, 10.2 mg, 16.8 umol, 94.3% purity) was obtained as a white solid. LCMS [ESI, M+1]: 570.

$^1$H NMR (400 MHz, CHLOROFORM-d) δ=7.68 (d, J=7.2 Hz, 1H), 7.58 (t, J=7.6 Hz, 1H), 7.41 (d, J=8.0 Hz, 1H), 7.30 (d, J=7.6 Hz, 1H), 6.59 (br s, 1H), 6.40 (d, J=16.4 Hz, 1H), 5.83 (d, J=10.4 Hz, 1H), 5.07 (br s, 1H), 4.85 (d, J=7.1 Hz, 1H), 4.66-4.39 (m, 1H), 4.20 (d, J=11.1 Hz, 1H), 4.13-3.95 (m, 4H), 3.70-3.55 (m, 2H), 3.45-3.20 (m, 2H), 3.16-2.99 (m, 3H), 2.98-2.91 (m, 4H), 2.85-2.70 (m, 4H), 2.33-2.14 (m, 2H), 2.10-2.01 (m, 2H).

Example 300

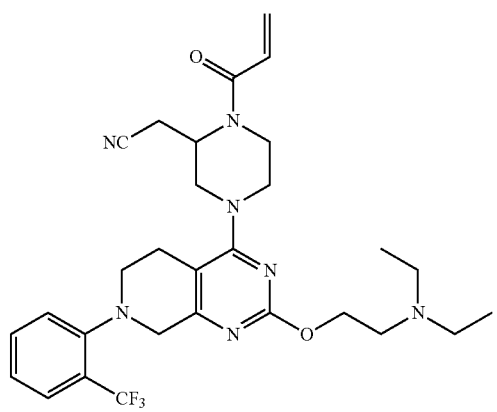 [SMILES: C=CC(=O)N1CCN(c2nc(OCCN(CC)CC)nc3c2CCN(c2ccccc2C(F)(F)F)C3)CC1CC#N]

2-[4-[2-[2-(diethylamino)ethoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile

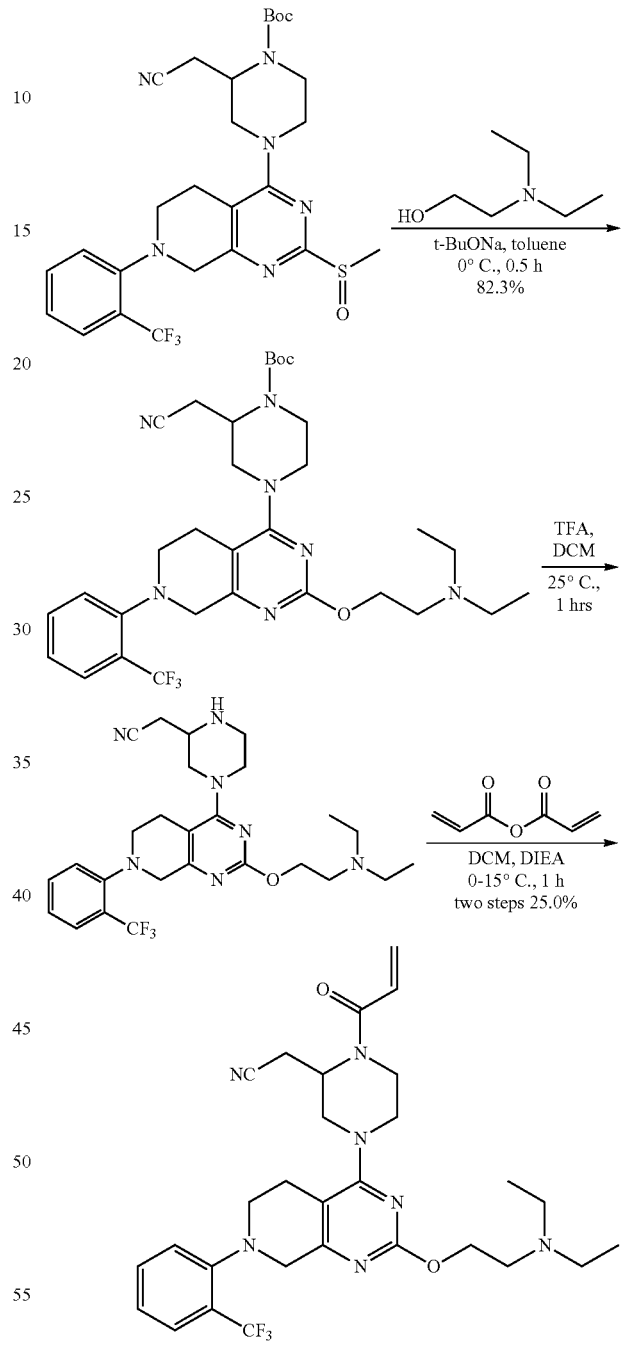

Step A: tert-butyl 2-(cyanomethyl)-4-[2-[2-(diethylamino)ethoxy]-7-[2-(trifluoromethyl)phenyl]-6,8-dihydro-5H-pyrido[3,4-d]pyrimidin-4-yl]piperazine-1-carboxylate To a solution of tert-butyl 2-(cyanomethyl)-4-[2-methylsulfinyl-7-[2-(trifluoromethyl)phenyl]-6,8-dihydro-5H-pyrido[3,4-d]pyrimidin-4-yl]piperazine-1-carboxylate (200 mg, 354 umol, 1.0 eq) and 2-(diethylamino)ethanol (83.0 mg, 708 umol, 93.9 uL, 2.0 eq) in toluene (3.0 mL) was added t-BuONa (68.1 mg, 708 umol, 2.0 eq). The mixture was stirred at 0° C. for 0.5 hour. After completion, the mixture was added water (10.0 mL) and extracted with ethyl acetate (10.0 mL×3). The organic layer was dried over Na$_2$SO$_4$, filtered and concentrated. The residue was purified by reversed phase flash column (C18, 0.1% FA in water, 0-40% MeCN). The product tert-butyl 2-(cyanomethyl)-4-[2-[2-(diethylamino)ethoxy]-7-[2-(trifluoromethyl)phenyl]-6,8-dihydro-5H-pyrido[3,4-d]pyrimidin-4-yl]piperazine-1-carboxylate (180 mg, 291 umol, 82.3% yield) was obtained as a colorless oil. LCMS [ESI, M+1]: 618.

Step B: 2-(4-(2-(2-(diethylamino)ethoxy)-7-(2-(trifluoromethyl)phenyl)-5,6,7,8-tetrahydropyrido[3,4-d]pyrimidin-4-yl)piperazin-2-yl)acetonitrile To a solution of tert-butyl 2-(cyanomethyl)-4-(2-(2-(diethylamino)ethoxy)-7-(2-(trifluoromethyl)phenyl)-5,6,7,8-tetrahydropyrido[3,4-d]pyrimidin-4-yl)piperazine-1-carboxylate (180 mg, 291 umol, 1.0 eq) in DCM (2.0 mL) was added TFA (33.2 mg, 291 umol, 21.6 uL, 1.0 eq). The mixture was stirred at 25° C. for 0.5 hour. After completion, the reaction mixture was added ethyl acetate (10.0 mL) and adjusted with saturated NaHCO$_3$ solution to pH >7. The mixture was extracted with ethyl acetate (30 ml×3) and the organic layer was dried with Na$_2$SO$_4$ and filtered. The solvent was removed under vacuum. The product 2-(4-(2-(2-(diethylamino)ethoxy)-7-(2-(trifluoromethyl)phenyl)-5,6,7,8-tetrahydropyrido[3,4-d]pyrimidin-4-yl)piperazin-2-yl)acetonitrile (150 mg, crude) was obtained as yellow oil. LCMS [ESI, M+1]: 518.

Step C: 2-[4-[2-[2-(diethylamino)ethoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile To a solution of 2-[4-[2-[2-(diethylamino)ethoxy]-7-[2-(trifluoromethyl)phenyl]-6,8-dihydro-5H-pyrido[3,4-d]pyrimidin-4-yl]piperazin-2-yl]acetonitrile (150 mg, crude) in DCM (3.0 mL) was added DIEA (129 mg, 1.0 mmol, 174 uL) and prop-2-enoyl prop-2-enoate (44.1 mg, 0.35 mmol). The mixture was stirred at 0° C. for 1 hour. After completion, the reaction mixture was quenched by addition methanol (10.0 mL) at 20° C. To the reaction mixture, water (10.0 mL) was added, and extracted with DCM (10.0 mL×3). The combined organic layers were dried over Na$_2$SO$_4$, filtered and concentrated under vacuum to give a residue. The residue was purified by prep-HPLC (column: Gemini 150*25 5 u; mobile phase: [water (0.04% NH3H2O)-ACN]; B %: 65%-83%,10 min). The product 2-[4-[2-[2-(diethylamino)ethoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile (EXAMPLE 300, 41.6 mg, 72.7 umol, 100% purity, two steps yield 25.0%) was obtained as a white solid. LCMS [ESI, M+1]: 572.

$^1$H NMR (400 MHz, CHLOROFORM-d) δ=7.68 (d, J=7.8 Hz, 1H), 7.58 (t, J=7.4 Hz, 1H), 7.41 (d, J=8.0 Hz, 1H), 7.32-7.28 (m, 1H), 6.70-6.49 (m, 1H), 6.39 (dd, J=1.2, 16.8 Hz, 1H), 5.82 (d, J=10.8 Hz, 1H), 5.08 (br, s, 1H), 4.39 (t, J=6.8 Hz, 2H), 4.14-4.00 (m, 3H), 4.02-3.84 (m, 1H), 3.32 (br d, J=12.0 Hz, 1H), 3.24-3.16 (m, 1H), 3.15-3.04 (m, 2H), 2.96-2.88 (m, 4H), 2.87-2.70 (m, 1H), 2.68-2.61 (m, 4H), 1.89 (br s, 3H), 1.07 (t, J=7.0 Hz, 6H).

Example 301

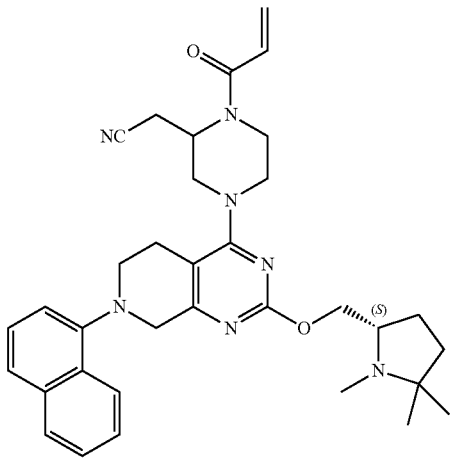

2-[4-[7-(1-naphthyl)-2-[[(2S)-1,5,5-trimethylpyrrolidin-2-yl]methoxy]-6,8-dihydro-5H-pyrido[3,4-d]pyrimidin-4-yl]-1-prop-2-enoyl-piperazin-2-yl]acetonitrile

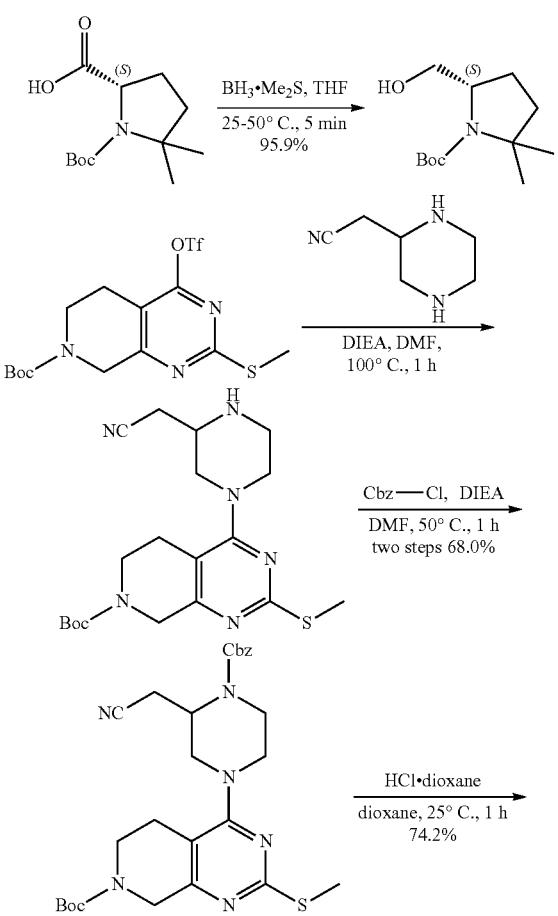

777
-continued
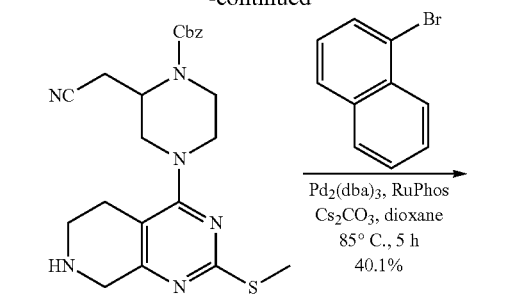
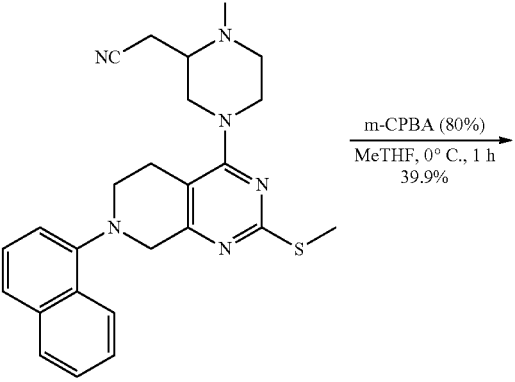
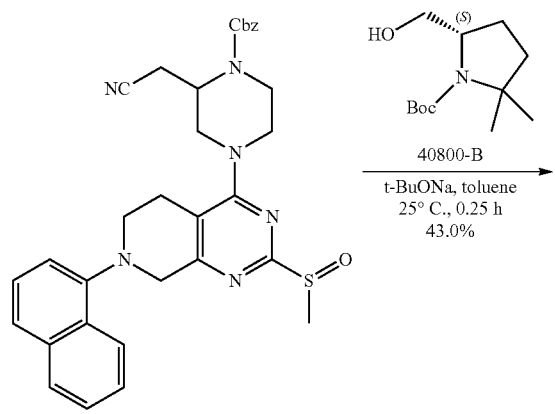
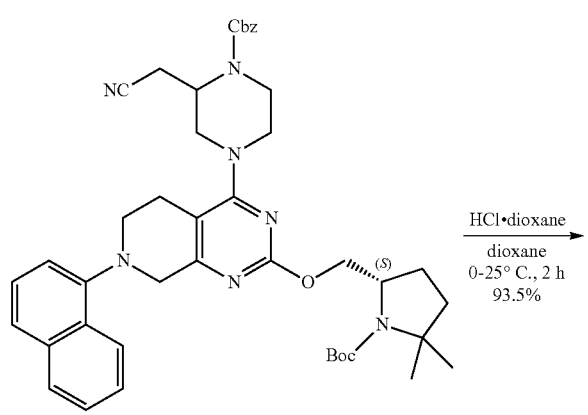
778
-continued
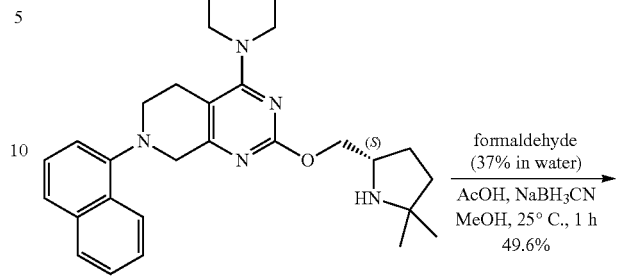
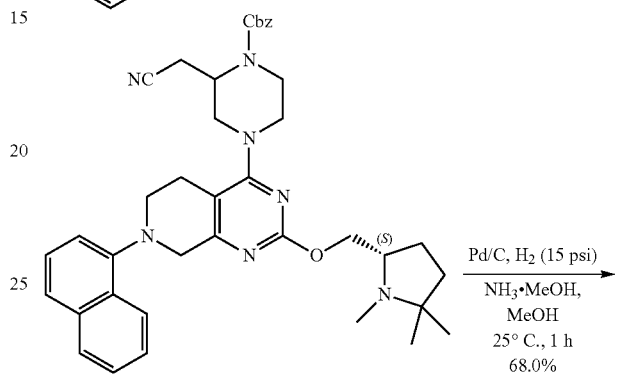
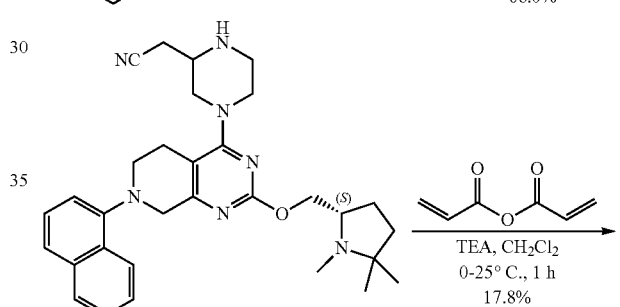
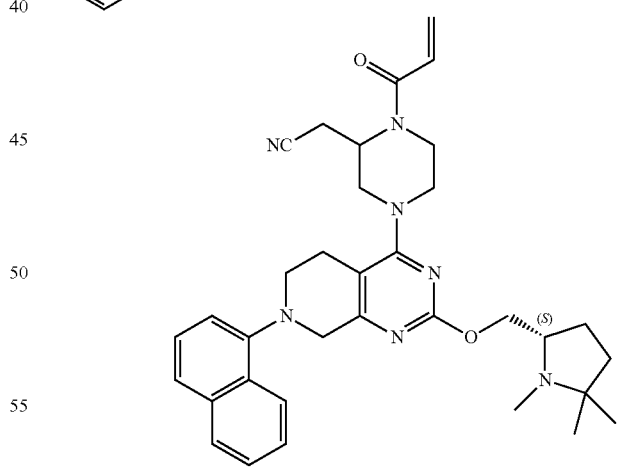
Step A: tert-butyl (5S)-5-(hydroxymethyl)-2,2-dimethyl-pyrrolidine-1-carboxylate
To a solution of (2S)-1-tert-butoxycarbonyl-5,5-dimethyl-pyrrolidine-2-carboxylic acid (400 mg, 1.64 mmol, 1.00 eq) in anhydrous THF (7.00 mL) was added $BH_3 \cdot Me_2S$ (10 M, 493 uL, 3.00 eq) dropwise at 25° C. The reaction was heated at 50° C. for 5 minutes. Upon completion, after cooled by an ice-bath, the mixture was quenched with Methanol (10 mL). The reaction mixture was concentrated under reduced pressure to give tert-butyl (5S)-5-(hydroxymethyl)-2,2-dimethyl-pyrrolidine-1-carboxylate (360 mg, 1.57 mmol, 95.9%) as a colorless oil which was used directly into the next step without further purification.

Step B: tert-butyl 4-[3-(cyanomethyl)piperazin-1-yl]-2-methylsulfanyl-6,8-dihydro-5H-pyrido[3,4-d]pyrimidine-7-carboxylate To a stirred solution of tert-butyl 2-methylsulfanyl-4-(trifluoromethylsulfonyloxy)-6,8-dihydro-5H-pyrido[3,4-d]pyrimidine-7-carboxylate (20 g, 46.5 mmol, 1.00 eq) in DMF (300 mL) was added DIEA (18.1 g, 139 mmol, 24.3 mL, 3 eq) and 2-piperazin-2-ylacetonitrile (10.2 g, 51.2 mmol, 495 uL, 1.10 eq, 2 HCl). The reaction was heated to 100° C. and stirred for 1 hour under $N_2$ atmosphere. tert-butyl 4-[3-(cyanomethyl)piperazin-1-yl]-2-methylsulfanyl-6,8-dihydro-5H-pyrido[3,4-d]pyrimidine-7-carboxylate (18.8 g, crude) was obtained and used to next step directly without work-up and purification.

Step C: tert-butyl 4-[4-benzyloxycarbonyl-3-(cyanomethyl)piperazin-1-yl]-2-methylsulfanyl-6,8-dihydro-5H-pyrido[3,4-d]pyrimidine-7-carboxylate To a solution of tert-butyl 4-[3-(cyanomethyl)piperazin-1-yl]-2-methylsulfanyl-6,8-dihydro-5H-pyrido[3,4-d]pyrimidine-7-carboxylate (18.8 g, crude) in DMF (200 mL) was added DIEA (12.0 g, 92.9 mmol, 16.2 mL) and benzyl carbonochloridate (11.9 g, 69.7 mmol, 9.91 mL). The mixture was stirred at 50° C. for 1 hour. The reaction mixture was diluted with water (300 mL) and extracted with ethyl acetate (200 mL×3). The combined organic layers were washed with brine (200 mL), dried over $Na_2SO_4$, filtered and concentrated under reduced pressure to give a residue. The residue was purified by column chromatography ($SiO_2$, Petroleum ether/Ethyl acetate=30/1 to 3/1). tert-butyl 4-[4-benzyloxycarbonyl-3-(cyanomethyl)piperazin-1-yl]-2-methylsulfanyl-6,8-dihydro-5H-pyrido[3,4-d]pyrimidine-7-carboxylate (20 g, 31.6 mmol, two steps 68.0% yield, 85% purity) was obtained as a yellow oil. LCMS [ESI, M+1]:539.
$^1$H NMR (400 MHz, chloroform-d) δ=7.40-7.36 (m, 5H), 5.21-5.15 (m, 2H), 4.73-4.55 (m, 2H), 4.39 (d, J=18.8 Hz, 1H), 3.97 (d, J=12.8 Hz, 1H), 3.90-3.69 (m, 2H), 3.41-3.16 (m, 3H), 3.00 (dt, J=3.6, 12.4 Hz, 1H), 2.86-2.53 (m, 5H), 2.51 (s, 3H), 1.49 (s, 9H).

Step D: benzyl 2-(cyanomethyl)-4-(2-methylsulfanyl-5,6,7,8-tetrahydropyrido[3,4-d]pyrimidin-4-yl)piperazine-1-carboxylate To a solution of tert-butyl 4-[4-benzyloxycarbonyl-3-(cyanomethyl) piperazin-1-yl]-2-methylsulfanyl-6,8-dihydro-5H-pyrido[3,4-d]pyrimidine-7-carboxylate (11 g, 20.4 mmol, 1.00 eq) in dioxane (100 mL) was added HCl.dioxane (4 M, 102 mL, 20 eq). After stirred at 25° C. for 1 hour, the reaction mixture was concentrated under reduced pressure to give a residue. The residue was dissolved in 300 mL of ethyl acetate and 300 mL of water and stirred rapidly. Then saturated $Na_2CO_3$ aqueous solution was added until the pH ~9. The organics was washed with water (1×300 mL) and brine (1×200 mL), dried over $Na_2SO_4$, filtered and concentrated under reduced pressure. benzyl 2-(cyanomethyl)-4-(2-methylsulfanyl-5,6,7,8-tetrahydropyrido[3,4-d]pyrimidin-4-yl)piperazine-1-carboxylate (8.2 g, 15.2 mmol, 74.2% yield, 81% purity) was obtained as a yellow oil and used to next step directly without purification. LCMS [ESI, M+1]:439.

Step E: Benzyl 2-(cyanomethyl)-4-[2-methylsulfanyl-7-(1-naphthyl)-6,8-dihydro-5H-pyrido[3,4-d]pyrimidin-4-yl]piperazine-1-carboxylate A mixture of benzyl 2-(cyanomethyl)-4-(2-methylsulfanyl-5,6,7,8-tetrahydropyrido[3,4-d]pyrimidin-4-yl)piperazine-1-carboxylate (5.07 g, 11.6 mmol, 1.1 eq), 1-bromonaphthalene (2.83 g, 13.7 mmol, 1.90 mL, 1.3 eq), $Cs_2CO_3$ (8.57 g, 26.3 mmol, 2.50 eq), $Pd_2(dba)_3$ (1.45 g, 1.58 mmol, 0.15 eq) and RuPhos (982 mg, 2.11 mmol, 0.20 eq) in dioxane (100 mL) was degassed and purged with $N_2$ for 3 times, and then the mixture was stirred at 85° C. for 5 hours under $N_2$ atmosphere. The reaction mixture was diluted with water (200 mL) and extracted with ethyl acetate (200 mL×3). The combined organic layers were washed with brine (200 mL), dried over $Na_2SO_4$, filtered and concentrated under reduced pressure to give a residue. The residue was purified by column chromatography ($SiO_2$, Petroleum ether/Ethyl acetate=100/1 to 2/1). Benzyl 2-(cyanomethyl)-4-[2-methylsulfanyl-7-(1-naphthyl)-6,8-dihydro-5H-pyrido[3,4-d]pyrimidin-4-yl]piperazine-1-carboxylate (3.6 g, 4.65 mmol, 40.1% yield, 73% purity) was obtained as a yellow oil. LCMS [ESI, M+1]:565.

Step F: benzyl 2-(cyanomethyl)-4-[2-methylsulfinyl-7-(1-naphthyl)-6,8-dihydro-5H-pyrido[3,4-d]pyrimidin-4-yl]piperazine-1-carboxylate To a stirred solution of benzyl 2-(cyanomethyl)-4-[2-methylsulfanyl-7-(1-naphthyl)-6,8-dihydro-5H-pyrido [3,4-d]pyrimidin-4-yl]piperazine-1-carboxylate (3.1 g, 5.49 mmol, 1 eq) in methyltetrahydrofuran (50 mL) at 0° C. under nitrogen was added m-CPBA (1.18 g, 5.49 mmol, 80% purity, 1 eq) neat as a solid. After stirred at 0° C. for 1 hour under $N_2$ atmosphere, the reaction mixture was quenched by addition 10% of $Na_2S_2O_3$ (100 mL) aqueous solution at 0° C., and then diluted with water (200 mL) and extracted with ethyl acetate (200 mL). The combined organic layers were washed with brine (200 mL), dried over $Na_2SO_4$, filtered and concentrated under reduced pressure to give a residue. The residue was purified by column chromatography ($SiO_2$, Ethyl acetate/Methanol=100/1 to 10/1) and further purified by reversed phase flash [water (0.1% formic acid)/acetonitrile)]. The desired fractions were adjusted pH=7 by addition saturated $NaHCO_3$ aqueous solution and extracted with ethyl acetate (100 mL×3). The combined organic layers were washed with brine (50 mL), dried over $Na_2SO_4$, filtered and concentrated under reduced pressure to give benzyl 2-(cyanomethyl)-4-[2-methylsulfinyl-7-(1-naphthyl)-6,8-dihydro-5H-pyrido[3,4-d]pyrimidin-4-yl]piperazine-1-carboxylate (1.3 g, 2.19 mmol, 39.9% yield, 98% purity) was obtained as a yellow solid. LCMS [ESI, M+1]: 581.
$^1$H NMR (400 MHz, chloroform-d) δ=8.22-8.13 (m, 1H), 7.92-7.83 (m, 1H), 7.63 (d, J=8.0 Hz, 1H), 7.56-7.48 (m, 2H), 7.45 (t, J=8.0 Hz, 1H), 7.41-7.32 (m, 5H), 7.15 (d, J=7.2 Hz, 1H), 5.22 (s, 2H), 4.70 (br s, 1H), 4.54-4.36 (m, 2H), 4.34-4.17 (m, 2H), 4.12-4.04 (m, 1H), 3.58-3.17 (m, 5H), 3.01 (m, 2H), 2.93 (d, J=2.8 Hz, 3H), 2.90-2.79 (m, 1H), 2.77-2.65 (m, 1H).

Step G: To a solution of benzyl 2-(cyanomethyl)-4-[2-methylsulfinyl-7-(1-naphthyl)-6,8-dihydro-5H-pyrido[3,4-d]pyrimidin-4-yl]piperazine-1-carboxylate (430 mg, 741 umol, 1.00 eq) and tert-butyl (5S)-5-(hydroxymethyl)-2,2-dimethyl-pyrrolidine-1-carboxylate (340 mg, 1.48 mmol, 2.00 eq) in toluene (8.00 mL) was added t-BuONa (142 mg, 1.48 mmol, 2.00 eq). The mixture was stirred at 20° C. for 0.25 hour. Upon completion, the reaction mixture was filtered and the filtrate was concentrated. The residue was purified by reversed-phase flash [water (0.1% FA)/acetonitrile] to give benzyl 4-[2-[[(2S)-1-tert-butoxycarbonyl-5,5-dimethyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (250 mg, 318 umol, 43.0% yield, 95.0% purity) as a yellow solid. LCMS [ESI, M+1]: 746.

Step H: benzyl 2-(cyanomethyl)-4-[2-[[(2S)-5,5-dimethylpyrrolidin-2-yl]methoxy]-7-(1-naphthyl)-6,8-dihydro-5H-pyrido[3,4-d]pyrimidin-4-yl]piperazine-1-carboxylate To a solution of benzyl 4-[2-[[(2S)-1-tert-butoxycarbonyl-5,5-dimethyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (200 mg, 268 umol, 1.00 eq) in dioxane (4.00 mL) was added HCl.dioxane (4 M, 4.00 mL, 59.7 eq) at 0° C. The mixture was stirred at 25° C. for 2 hours. Upon completion, the mixture was concentrated under vacuum to give benzyl 2-(cyanomethyl)-4-[2-[[(2S)-5,5-dimethylpyrrolidin-2-yl]methoxy]-7-(1-naphthyl)-6,8-dihydro-5H-pyrido[3,4-d]pyrimidin-4-yl]piperazine-1-carboxylate (180 mg, 251 umol, 93.5% yield, 95.0% purity, HCl) as a yellow oil which was used directly into the next step without further purification.

Step I: benzyl 2-(cyanomethyl)-4-[7-(1-naphthyl)-2-[[(2S)-1,5,5-trimethylpyrrolidin-2-yl]methoxy]-6,8-dihydro-5H-pyrido[3,4-d]pyrimidin-4-yl]piperazine-1-carboxylate To a solution of benzyl 2-(cyanomethyl)-4-[2-[[(2S)-5,5-dimethylpyrrolidin-2-yl]methoxy]-7-(1-naphthyl)-6,8-dihydro-5H-pyrido[3,4-d]pyrimidin-4-yl]piperazine-1-carboxylate (180 mg, 264 umol, 1.00 eq, HCl) and formaldehyde (107 mg, 1.32 mmol, 98.2 uL, 5.00 eq, 37% in water) in MeOH (3.00 mL) was added CH$_3$COOH (31.7 mg, 528 umol, 30.2 uL, 2.00 eq) and NaBH$_3$CN (66.3 mg, 1.06 mmol, 4.00 eq). The mixture was stirred at 25° C. for 1 hour. Upon completion, the mixture was quenched with 1 M HCl (0.2 mL), diluted with water (1 mL) and extracted with EtOAc (3×6 mL). The organic layers were dried over Na$_2$SO$_4$ and concentrated under vacuum. The residue was purified by reversed-phase flash [water (0.1% FA)/acetonitrile] to give benzyl 2-(cyanomethyl)-4-[7-(1-naphthyl)-2-[[(2S)-1,5,5-trimethylpyrrolidin-2-yl]methoxy]-6,8-dihydro-5H-pyrido[3,4-d]pyrimidin-4-yl]piperazine-1-carboxylate (96.0 mg, 131 umol, 49.6% yield, 90.0% purity) as a yellow solid.

$^1$H NMR (400 MHz, chloroform-d) δ=8.23-8.17 (m, 1H), 7.89-7.83 (m, 1H), 7.61 (d, J=8.0 Hz, 1H), 7.53-7.47 (m, 2H), 7.46-7.42 (m, 1H), 7.42-7.33 (m, 5H), 7.14 (d, J=7.2 Hz, 1H), 5.27-5.16 (m, 2H), 4.70 (br s, 1H), 4.41 (dd, J=4.4, 10.4 Hz, 1H), 4.34-4.22 (m, 2H), 4.20-4.01 (m, 3H), 3.95 (br d, J=11.2 Hz, 1H), 3.40-3.21 (m, 3H), 3.13-2.91 (m, 2H), 2.91-2.69 (m, 3H), 2.32 (s, 3H), 2.13-1.96 (m, 1H), 1.75-1.54 (m, 5H), 1.15 (s, 3H), 0.92 (s, 3H).

Step J: 2-[4-[7-(1-naphthyl)-2-[[(2S)-1,5,5-trimethylpyrrolidin-2-yl]methoxy]-6,8-dihydro-5H-pyrido[3,4-d]pyrimidin-4-yl]piperazin-2-yl]acetonitrile NH$_3$ was bubbled into MeOH (6.00 mL) for 3 minutes at −40° C. A solution of benzyl 2-(cyanomethyl)-4-[7-(1-naphthyl)-2-[[(2S)-1,5,5-trimethylpyrrolidin-2-yl] methoxy]-6,8-dihydro-5H-pyrido[3,4-d]pyrimidin-4-yl]piperazine-1-carboxylate (0.10 g, 152 umol, 1.00 eq) in MeOH (6.00 mL) was added to the NH$_3$ solution and Pd/C (0.05 g, 10% purity) under N$_2$. The suspension was degassed under vacuum and purged with H$_2$ several times. The reaction was stirred under H$_2$ (15 psi) at 25° C. for 1 hour. Upon completion, the catalyst was filtered off and the filtrate was concentrated under vacuum to give 2-[4-[7-(1-naphthyl)-2-[[(2S)-1,5,5-trimethylpyrrolidin-2-yl]methoxy]-6,8-dihydro-5H-pyrido[3,4-d]pyrimidin-4-yl]piperazin-2-yl]acetonitrile (63.0 mg, 103 umol, 68.0% yield, 86.0% purity) as a yellow solid which was used directly into the next step without further purification. LCMS [ESI, M+1]: 526.

Step K: 2-[4-[7-(1-naphthyl)-2-[[(2S)-1,5,5-trimethylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(1-naphthyl)-2-[[(2S)-1,5,5-trimethyl pyrrolidin-2-yl]methoxy]-6,8-dihydro-5H-pyrido[3,4-d]pyrimidin-4-yl]piperazin-2-yl]acetonitrile (75.0 mg, 143 umol, 1.00 eq) and TEA (72.2 mg, 713 umol, 99.3 uL, 5.00 eq) in DCM (2.00 mL) was added prop-2-enoyl prop-2-enoate (18.0 mg, 143 umol, 1.00 eq) dropwise at 0° C. The mixture was stirred at 25° C. for 1 hour. Upon completion, the reaction was quenched with MeOH (0.5 mL), diluted with water (2 mL) and extracted with EtOAc (2×5 mL). The organic layers were dried over Na$_2$SO$_4$, filtered and concentrated under vacuum. The residue was purified by prep-TLC (EtOAc/MeOH 9/1) and prep-HPLC (column: Phenomenex Gemini 150*25 mm*10 um; mobile phase: [water (0.05% ammonia hydroxide v/v)-ACN]; B %: 60%-90%, 12 min) and lyophilized to give 2-[4-[7-(1-naphthyl)-2-[[(2S)-1,5,5-trimethylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 301, 14.7 mg, 25.3 umol, 17.8% yield, 100% purity) as a white solid. LCMS [ESI, M+1]:580.

$^1$H NMR (400 MHz, chloroform-d) δ=8.25-8.17 (m, 1H), 7.90-7.83 (m, 1H), 7.61 (d, J=8.4 Hz, 1H), 7.55-7.48 (m, 2H), 7.44 (t, J=7.6 Hz, 1H), 7.14 (d, J=7.2 Hz, 1H), 6.60 (br s, 1H), 6.45-6.36 (m, 1H), 5.84 (br d, J=10.8 Hz, 1H), 5.10 (br s, 1H), 4.44 (br s, 1H), 4.34-4.19 (m, 2H), 4.17-3.80 (m, 4H), 3.79-3.21 (m, 4H), 3.19-2.63 (m, 6H), 2.34 (br s, 3H), 2.15-2.03 (m, 1H), 1.69 (br s, 3H), 1.16 (br s, 3H), 0.94 (s, 3H).

Example 302

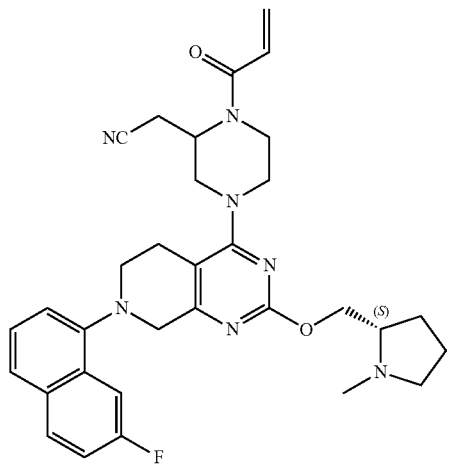

2-[4-[7-(7-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-2-piperidyl]acetonitrile

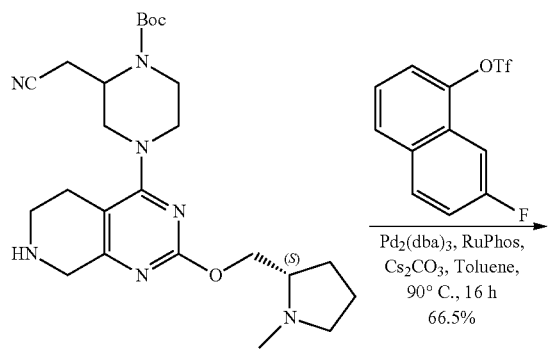

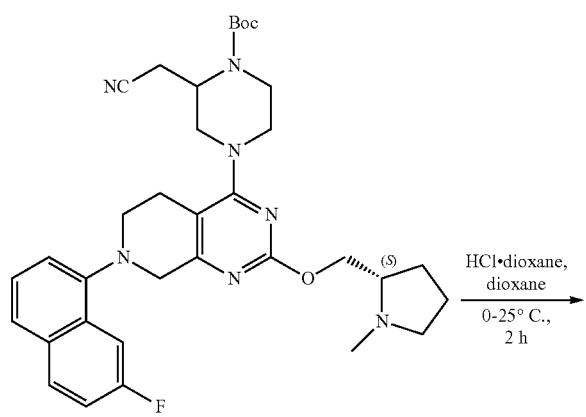

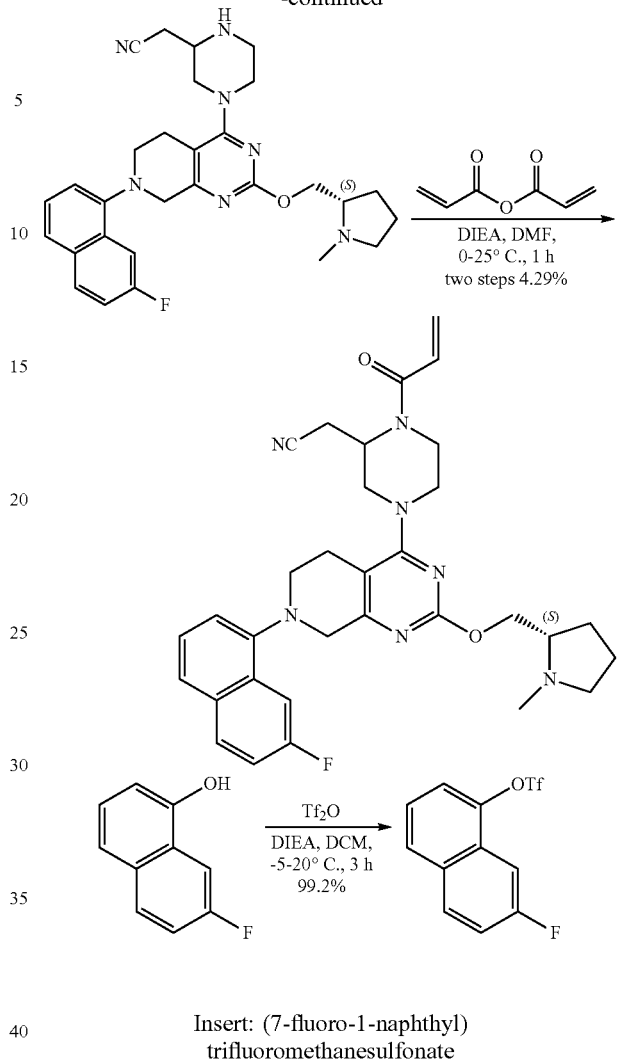

Insert: (7-fluoro-1-naphthyl) trifluoromethanesulfonate

To a solution of 7-fluoronaphthalen-1-ol (250 mg, 1.54 mmol, 1 eq) and DIEA (598 mg, 4.63 mmol, 806 uL, 3 eq) in DCM (10 mL) was added Tf$_2$O (652 mg, 2.31 mmol, 382 uL, 1.5 eq) dropwise at −5° C. The mixture was stirred at 20° C. for 3 hours. After that, the mixture was concentrated under vacuum. The residue was purified by silica gel chromatography (Petroleum ether/Ethyl acetate=100/1 to 10/1). (7-fluoro-1-naphthyl) trifluoromethanesulfonate (450 mg, 1.53 mmol, 99.2% yield) was obtained as a colourless oil.
$^1$H NMR (400 MHz, methanol-d$_4$) δ=8.08 (dd, J=5.6, 9.2 Hz, 1H), 8.01 (d, J=8.4 Hz, 1H), 7.73-7.39 (m, 4H).

Step A: tert-Butyl 2-(cyanomethyl)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a mixture of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (182 mg, 386 umol, 1 eq), (7-fluoro-1-naphthyl) trifluoromethanesulfonate (227 mg, 772 umol, 2 eq), Pd$_2$(dba)$_3$ (35.3 mg, 38.6 umol, 0.1 eq), RuPhos (36.0 mg, 77.2 umol, 0.2 eq) and Cs$_2$CO$_3$ (377 mg, 1.16 mmol, 3 eq) in toluene (20 mL) was degassed and purged with N$_2$ for 3 times, and then the mixture was stirred at 90° C. for 16 hours under N₂ atmosphere. The mixture was quenched with H₂O (30 mL), and then the mixture was diluted with ethyl acetate (20 mL). The separated organic layer was dried over sodium sulfate, filtered and concentrated under vacuum. The residue was purified by reversed phase flash [water (0.1% FA)/acetonitrile]. The desired fractions were collected and neutralized with saturated NaHCO₃ solution and extracted with ethyl acetate (1×100 mL). The organic layer was dried over sodium sulfate, filtered and concentrated under vacuum. tert-Butyl 2-(cyanomethyl)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (158 mg, 257 umol, 66.5% yield, 100% purity) was obtained as a yellow oil. LCMS [ESI, M+1]: 616.

¹H NMR (400 MHz, chloroform-d) δ=7.92-7.79 (m, 2H), 7.61 (d, J=8.0 Hz, 1H), 7.40 (t, J=7.8 Hz, 1H), 7.30-7.25 (m, 1H), 7.19 (d, J=7.2 Hz, 1H), 4.63 (br d, J=2.1 Hz, 1H), 4.40 (br dd, J=4.8, 10.4 Hz, 1H), 4.24 (br s, 2H), 4.20-4.00 (m, 4H), 3.95 (br d, J=12.4 Hz, 1H), 3.52-3.37 (m, 1H), 3.36-3.16 (m, 3H), 3.15-2.63 (m, 6H), 2.50 (s, 3H), 2.36-2.22 (m, 1H), 2.12-2.05 (m, 1H), 1.92-1.70 (m, 3H), 1.53 (s, 9H).

Step B: 2-[4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl 2-(cyanomethyl)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (100 mg, 162 umol, 1 eq) in dioxane (10 mL) was added HCl.dioxane (4 M, 1.62 mL, 40 eq) at 0° C. under nitrogen atmosphere. The mixture was stirred at 25° C. for 2 hours. After that, the mixture was concentrated under vacuum. 2-[4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (100 mg, crude, HCl) was obtained as a yellow oil. LCMS [ESI, M+1]: 516.

Step C: 2-[4-[7-(7-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-2-piperidyl]acetonitrile To a mixture of 2-[4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (100 mg, crude, HCl) and DIEA (234 mg, 1.81 mmol, 315 uL) in DMF (5 mL) was added prop-2-enoyl prop-2-enoate (18.3 mg, 145 umol) at 0° C. After stirred at 25° C. for 1 h, the reaction mixture was quenched by NaHCO₃ saturated solution (5 mL), and then extracted with ethyl acetate (2×25 mL). The combined organic layers were washed with brine (1×50 mL), dried over sodium sulfate, filtered and concentrated under vacuum. The residue was purified by silica gel chromatography (Ethyl acetate/MeOH=50/1 to 1/1). The collected liquid was concentrated under vacuum. The residue was purified by prep-HPLC (column: Phenomenex Synergi C18 150*25*10 um; mobile phase: [water (0.225% FA)-ACN]; B %: 12%-42%, 10 min) and (column: Phenomenex Gemini 150*25 mm*10 um; mobile phase: [water (0.05% ammonia hydroxide v/v)-ACN]; B %: 55%-85%,12 min) 2-[4-[7-(7-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-2-piperidyl]acetonitrile (EXAMPLE 302, 4.23 mg, 7.19 umol, two steps 4.29% yield, 96.7% purity) was obtained as a white solid. LCMS [ESI, M+1]: 570.

¹H NMR (400 MHz, chloroform-d) δ=7.93-7.77 (m, 2H), 7.61 (d, J=8.0 Hz, 1H), 7.40 (t, J=7.8 Hz, 1H), 7.32-7.25 (m, 1H), 7.19 (d, J=7.3 Hz, 1H), 6.59 (br d, J=10.8 Hz, 1H), 6.41 (dd, J=1.6, 16.8 Hz, 1H), 5.84 (br d, J=10.4 Hz, 1H), 5.23-4.52 (m, 1H), 4.40 (dd, J=4.8, 10.6 Hz, 1H), 4.24 (br s, 2H), 4.21-4.11 (m, 2H), 4.03 (br d, J=12.0 Hz, 2H), 3.86-3.04 (m, 6H), 3.03-2.58 (m, 5H), 2.49 (s, 3H), 2.37-2.23 (m, 1H), 2.16-1.98 (m, 1H), 1.91-1.69 (m, 3H).

Example 303

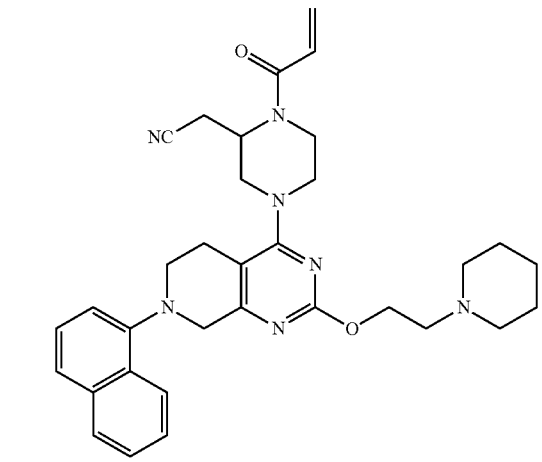 [SMILES: C=CC(=O)N1CCN(c2nc(OCCN3CCCCC3)nc3c2CCN(c2cccc4ccccc24)C3)CC1CC#N]

2-[4-[7-(1-naphthyl)-2-[2-(1-piperidyl)ethoxy]-6,8-dihydro-5H-pyrido[3,4-d]pyrimidin-4-yl]-1-prop-2-enoyl-piperazin-2-yl]acetonitrile

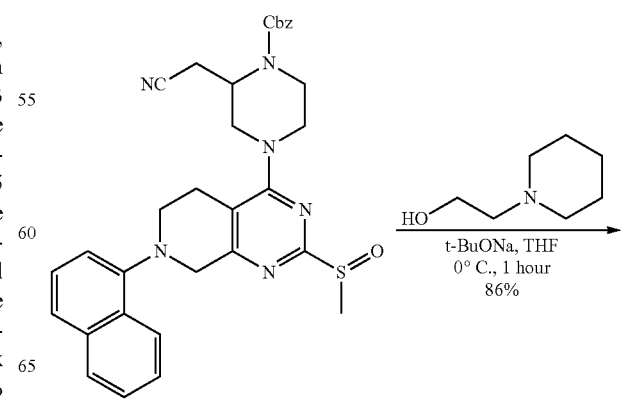

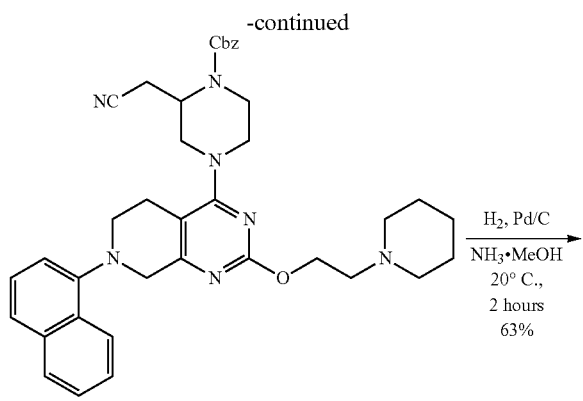

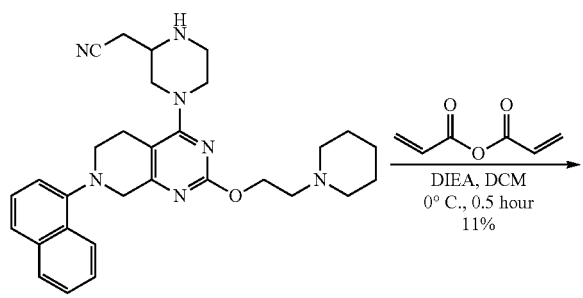

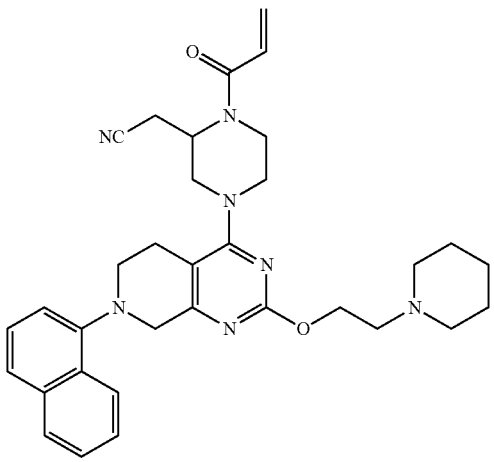

Step A: benzyl (2S)-2-(cyanomethyl)-4-[7-(1-naphthyl)-2-[2-(1-piperidyl)ethoxy]-6,8-dihydro-5H-pyrido[3,4-d]pyrimidin-4-yl]piperazine-1-carboxylate To a solution of 2-(1-piperidyl)ethanol (89.0 mg, 689 umol, 91.5 uL, 2.0 eq) in toluene (2.0 mL) was added t-BuONa (66.2 mg, 689 umol, 2.0 eq) at 0° C. Then the mixture was added benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (200 mg, 344 umol, 1.0 eq), the mixture was stirred at 0° C. for 1 hour. After completion, the mixture was added water (10.0 mL) and extracted with EA (10 mL×3). The organic layer was dried over $Na_2SO_4$, filtered and concentrated. The obtained product was purified by column chromatography ($SiO_2$, PE:EA=10:1-EA:MeOH=20:1) to give benzyl (2S)-2-(cyanomethyl)-4-[7-(1-naphthyl)-2-[2-(1-piperidyl)ethoxy]-6,8-dihydro-5H-pyrido[3,4-d]pyrimidin-4-yl]piperazine-1-carboxylate (200 mg, 296 umol, 86% yield, 95.7% purity) as yellow oil. LCMS [ESI, M+1]: 646.

Step B: 2-[(2S)-4-[7-(1-naphthyl)-2-[2-(1-piperidyl)ethoxy]-6,8-dihydro-5H-pyrido[3,4-d]pyrimidin-4-yl]piperazin-2-yl]acetonitrile $NH_3$ was bubbled into MeOH (10.0 mL) at −78° C. for 30 minutes. Then benzyl (2S)-2-(cyanomethyl)-4-[7-(1-naphthyl)-2-[2-(1-piperidyl) ethoxy]-6,8-dihydro-5H-pyrido[3,4-d]pyrimidin-4-yl]piperazine-1-carboxylate (180 mg, 279 umol, 1.0 eq) and Pd/C (100 mg, 10.0% purity) was added to the above liquid under $N_2$ atmosphere. The suspension was degassed and purged with $H_2$ for 3 times. The mixture was stirred under $H_2$ (15 Psi) at 20° C. for 0.5 hour. After completion, the mixture was filtered with Celite and concentrated under vacuum. The obtained product was purified by reversed phase flash column (C18, 0.1% FA in water, 0-40% MeCN) to give 2-[(2S)-4-[7-(1-naphthyl)-2-[2-(1-piperidyl)ethoxy]-6,8-dihydro-5H-pyrido[3,4-d]pyrimidin-4-yl]piperazin-2-yl]acetonitrile (90.0 mg, 176 umol, 63% yield) as white solid. LCMS [ESI, M+1]: 512.

Step C: 2-[4-[7-(1-naphthyl)-2-[2-(1-piperidyl)ethoxy]-6,8-dihydro-5H-pyrido[3,4-d]pyrimidin-4-yl]-1-prop-2-enoyl-piperazin-2-yl]acetonitrile To a solution of 2-[4-[7-(1-naphthyl)-2-[2-(1-piperidyl)ethoxy]-6,8-dihydro-5H-pyrido[3,4-d]pyrimidin-4-yl]piperazin-2-yl]acetonitrile (90.0 mg, 176 umol, 1.0 eq) and DIEA (136 mg, 1.06 mmol, 184 uL, 6.0 eq) in DCM (1.0 mL) was added prop-2-enoyl prop-2-enoate (22.2 mg, 176 umol, 1.0 eq). The mixture was stirred at 0° C. for 0.5 hour. After completion, the mixture was quenched with MeOH (20.0 mg) and concentrated under vacuum. The obtained product was purified by prep-HPLC (column: Phenomenex Gemini 150*25 mm*10 um; mobile phase: [water (0.05% ammonia hydroxide v/v)-ACN]; B %: 60%-90%, 12 min) to give 2-[4-[7-(1-naphthyl)-2-[2-(1-piperidyl)ethoxy]-6,8-dihydro-5H-pyrido[3,4-d]pyrimidin-4-yl]-1-prop-2-enoyl-piperazin-2-yl]acetonitrile (EXAMPLE 303, 11.2 mg, 19.7 umol, 11% yield, 99.5% purity) as white solid. LCMS [ESI, M+1]: 566.

$^1$H NMR (400 MHz, Chloroform-d) δ 8.24-8.19 (m, 1H), 7.89-7.84 (m, 1H), 7.62 (d, J=8.4 Hz, 1H), 7.55-7.47 (m, 2H), 7.44 (t, J=8.0 Hz, 1H), 7.15 (d, J=7.6 Hz, 1H), 6.70-6.53 (m, 1H), 6.41 (dd, J=1.2, 16.8 Hz, 1H), 5.84 (br d, J=10.4 Hz, 1H), 5.19-5.01 (m, 1H), 4.47 (br t, J=6.0 Hz, 2H), 4.33-4.21 (m, 2H), 4.12 (br d, J=14.0 Hz, 1H), 4.06-3.98 (m, 1H), 3.55-3.45 (m, 1H), 3.43-3.24 (m, 2H), 3.22-3.09 (m, 1H), 3.04-2.72 (m, 6H), 2.68-2.42 (m, 4H), 1.61-1.56 (m, 6H), 1.50-1.40 (m, 2H).

Example 304

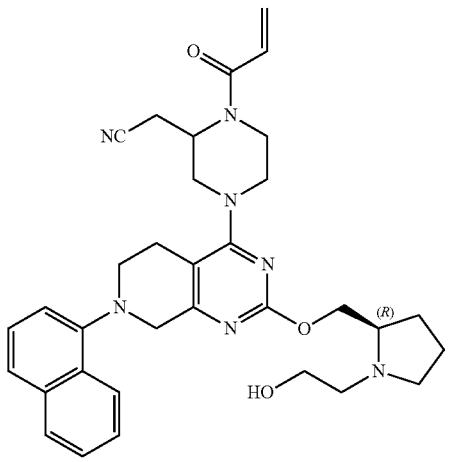

2-[4-[2-[[(2R)-1-(2-hydroxyethyl)pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile

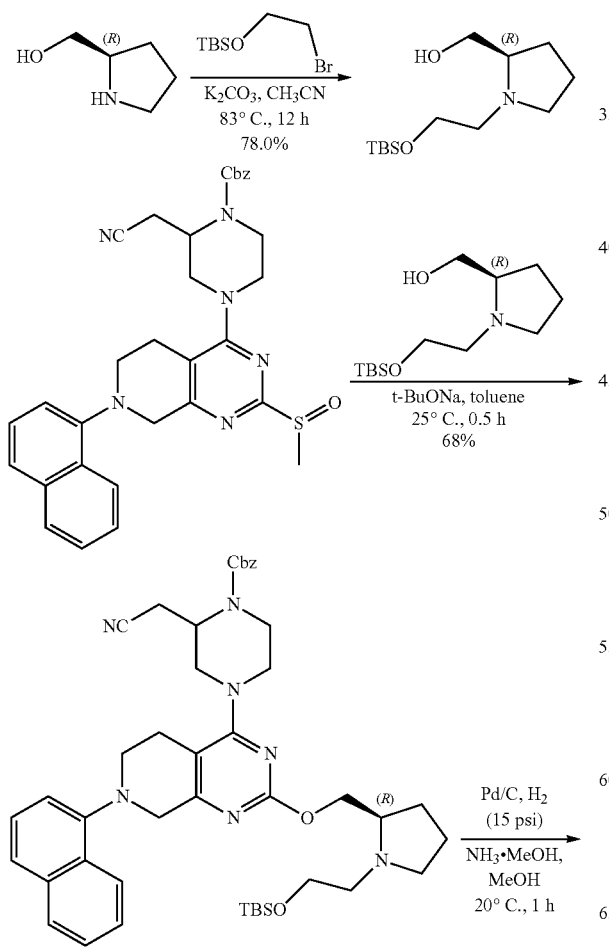

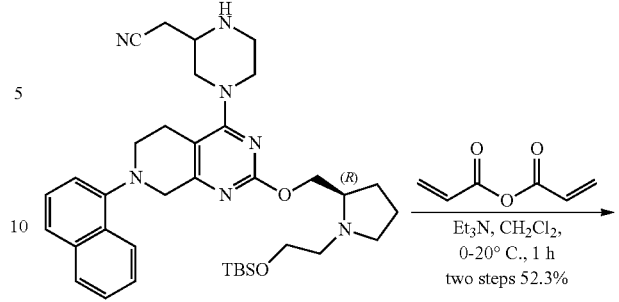


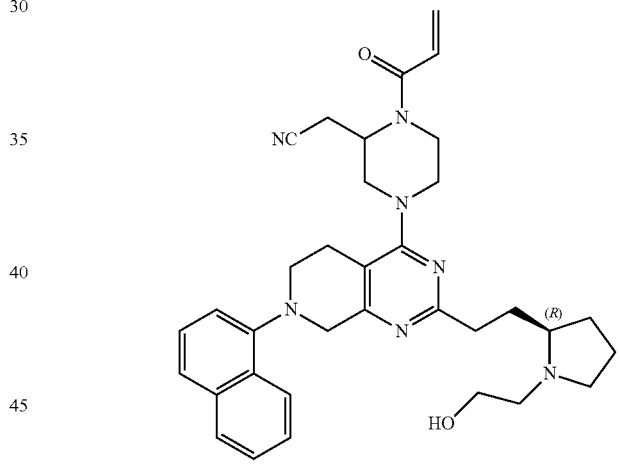

[(2R)-1-[2-[tert-butyl(dimethyl) silyl]oxyethyl]pyrrolidin-2-yl] methanol

A mixture of [(2R)-pyrrolidin-2-yl]methanol (0.70 g, 6.92 mmol, 673 uL, 1.00 eq), 2-bromoethoxy-tert-butyl-dimethyl-silane (1.66 g, 6.92 mmol, 1.00 eq) and $K_2CO_3$ (4.78 g, 34.6 mmol, 5.00 eq) in acetonitrile (70.0 mL) was refluxed at 83° C. for 12 hours. Then the mixture was filtered and the filter cake was washed with methanol. The organic layers were concentrated under vacuum to give a residue. The residue was purified by silica gel chromatography (ethyl acetate/methanol=50/1 to 1/1). Compound [(2R)-1-[2-[tert-butyl(dimethyl) silyl]oxyethyl]pyrrolidin-2-yl] methanol (1.40 g, 5.40 mmol, 78.0% yield, 100% purity) was obtained as a colorless oil.

$^1$H NMR (400 MHz, chloroform-d) δ=3.68 (dd, J=5.2, 6.4 Hz, 2H), 3.57 (dd, J=3.6, 10.8 Hz, 1H), 3.42-3.25 (m, 1H), 3.23-2.96 (m, 2H), 2.95-2.82 (m, 1H), 2.72-2.61 (m, 1H), 2.48 (td, J=5.2, 12.8 Hz, 1H), 2.40-2.27 (m, 1H), 1.90-1.77 (m, 1H), 1.77-1.62 (m, 3H), 0.83 (s, 9H), 0.00 (s, 6H).

Step A: benzyl 4-[2-[[(2R)-1-[2-[tert-butyl(dimethyl)silyl]oxyethyl]pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate To a solution of benzyl 2-(cyanomethyl)-4-[2-methylsulfinyl-7-(1-naphthyl)-6,8-dihydro-5H-pyrido[3,4-d]pyrimidin-4-yl]piperazine-1-carboxylate (500 mg, 861 umol, 1 eq) and [(2R)-1-[2-[tert-butyl(dimethyl)silyl]oxyethyl]pyrrolidin-2-yl]methanol (447 mg, 1.72 mmol, 2 eq) in toluene (10 mL) was added t-BuONa (248 mg, 2.58 mmol, 3 eq) in one portion at 25° C. and the mixture was stirred at 25° C. for 0.5 hour. The mixture was acidified with 1 M HCl solution to pH=8 and the mixture diluted with ethyl acetate (100 mL) and water (10 mL). The separated organic layer was washed with brine (1×50 mL), dried over sodium sulfate, filtered and concentrated under vacuum. The residue was purified by column chromatography over silica gel (ethyl acetate/methanol 100/1 to 10/1). The desired fractions were collected and concentrated under vacuum to give benzyl 4-[2-[[(2R)-1-[2-[tert-butyl(dimethyl)silyl]oxyethyl] pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (480 mg, 582 umol, 68% yield, 94.1% purity) as a light yellow solid. LCMS [ESI, M+1]: 776.

$^1$H NMR (400 MHz, chloroform-d) δ=8.28-8.11 (m, 1H), 7.95-7.77 (m, 1H), 7.61 (d, J=8.0 Hz, 1H), 7.55-7.29 (m, 8H), 7.14 (d, J=7.2 Hz, 1H), 5.29-5.15 (m, 2H), 4.70 (br s, 1H), 4.41-3.88 (m, 7H), 3.83-3.68 (m, 2H), 3.57-2.69 (m, 12H), 2.67-2.49 (m, 1H), 2.37 (q, J=8.4 Hz, 1H), 2.03-1.93 (m, 1H), 1.83-1.74 (m, 3H), 1.00-0.79 (m, 9H), 0.13-0.01 (m, 6H).

Step B: 2-[4-[2-[[(2R)-1-[2-[tert-butyl(dimethyl) silyl]oxyethyl]pyrrolidin-2-yl]methoxy]-7-(1-naphthyl)-6,8-dihydro-5H-pyrido[3,4-d]pyrimidin-4-yl] piperazin-2-yl]acetonitrile NH$_3$ was bubbled in methanol (60.0 mL) at −78° C. for 30 minutes. Benzyl 4-[2-[[(2R)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]-2-(cyanomethyl) piperazine-1-carboxylate (0.20 g, 258 umol, 1.00 eq) and Pd/C (0.10 g, 10.0% purity) was added into the mixture. The mixture was stirred at 20° C. for 1 hour under H$_2$ at 15 psi. Then the mixture was filtered and concentrated under vacuum to give 2-[4-[2-[[(2R)-1-[2-[tert-butyl(dimethyl) silyl]oxyethyl]pyrrolidin-2-yl]methoxy]-7-(1-naphthyl)-6, 8-dihydro-5H-pyrido[3,4-d]pyrimidin-4-yl]piperazin-2-yl] acetonitrile (0.15 g, crude) as a yellow oil and used into next step without further purification. LCMS [ESI, M+1]: 642.

Step C: 2-[4-[2-[[(2R)-1-[2-[tert-butyl(dimethyl) silyl] oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a solution of 2-[4-[2-[[(2R)-1-[2-[tert-butyl(dimethyl) silyl] oxyethyl]pyrrolidin-2-yl]methoxy]-7-(1-naphthyl)-6, 8-dihydro-5H-pyrido[3,4-d]pyrimidin-4-yl]piperazin-2-yl] acetonitrile (0.15 g, crude) and Et$_3$N (236 mg, 2.34 mmol, 325 uL) in dichloromethane (2.00 mL) was added prop-2-enoyl prop-2-enoate (29.5 mg, 234 umol) at 0° C. After stirred at 20° C. for 1 hour, the mixture was quenched with saturated sodium bicarbonate solution (0.50 mL) and concentrated under vacuum. The residue was purified by column chromatography (Al$_2$O$_3$, methanol/ethyl acetate=1/10) to give 2-[4-[2-[[(2R)-1-[2-[tert-butyl(dimethyl)silyl]oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (0.10 g, 135 umol, two steps 52.3% yield) as a yellow solid. LCMS [ESI, M+1]: 696.

$^1$H NMR (400 MHz, chloroform-d) δ=8.25-8.18 (m, 1H), 7.90-7.82 (m, 1H), 7.61 (d, J=8.0 Hz, 1H), 7.54-7.47 (m, 2H), 7.43 (t, J=7.6 Hz, 1H), 7.15 (d, J=7.2 Hz, 1H), 6.59 (br d, J=12.0 Hz, 1H), 6.40 (dd, J=1.2, 16.8 Hz, 1H), 5.84 (br d, J=10.4 Hz, 1H), 5.22-4.94 (m, 1H), 4.36 (td, J=3.6, 10.4 Hz, 1H), 4.31-4.20 (m, 2H), 4.15-4.05 (m, 2H), 4.04-3.97 (m, 1H), 3.75 (t, J=6.8 Hz, 2H), 3.63 (br s, 1H), 3.46 (br s, 1H), 3.35 (br d, J=11.2 Hz, 2H), 3.21-3.15 (m, 1H), 3.08-2.99 (m, 2H), 2.99-2.92 (m, 2H), 2.63-2.54 (m, 1H), 2.42-2.33 (m, 1H), 2.04-1.95 (m, 1H), 1.84-1.73 (m, 3H), 1.66 (br s, 4H), 0.88 (s, 9H), 0.05 (s, 6H).

Step D: 2-[4-[2-[[(2R)-1-(2-hydroxyethyl) pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile A mixture of 2-[4-[2-[[(2R)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (0.09 g, 129 umol, 1 eq) and TBAF (1.00 M in THF, 1.29 mL, 10 eq) in THF (0.10 mL) was stirred at 10° C. for 1 hour. The mixture was concentrated under vacuum. The residue was purified by reverse phase flash [water (FA, 0.1%)/acetonitrile], column chromatography (Al$_2$O$_3$, methanol/ethyl acetate=1/3) and prep-HPLC (column: Boston pH-lex 150*25 10 um; mobile phase: [water (0.10% TFA)-ACN]; B %: 22%-52%, 10 min and column: Phenomenex Gemini 150*25 mm*10 um; mobile phase: [water (0.05% ammonia hydroxide v/v)-ACN]; B %: 47%-77%, 12 min). The desired fractions were collected and lyophilized to give title compound 2-[4-[2-[[(2R)-1-(2-hydroxyethyl) pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (23.9 mg, 41.0 umol, 31.7% yield, 99.7% purity) as a white solid. LCMS [ESI, M+1]: 582.

$^1$H NMR (400 MHz, chloroform-d) δ=8.25-8.18 (m, 1H), 7.89-7.83 (m, 1H), 7.61 (d, J=8.4 Hz, 1H), 7.54-7.47 (m, 2H), 7.43 (t, J=7.6 Hz, 1H), 7.14 (d, J=7.2 Hz, 1H), 6.59 (br s, 1H), 6.44-6.35 (m, 1H), 5.83 (br d, J=10.4 Hz, 1H), 5.10-4.50 (m, 1H), 4.38-4.24 (m, 3H), 4.22-4.09 (m, 2H), 4.00 (br d, J=11.5 Hz, 2H), 3.73-3.57 (m, 2H), 3.45 (br s, 1H), 3.36 (br d, J=12.0 Hz, 2H), 3.23-2.77 (m, 9H), 2.62 (td, J=3.6, 12.4 Hz, 1H), 2.38-2.26 (m, 1H), 2.05-1.99 (m, 1H), 1.90-1.73 (m, 3H).

Example 305

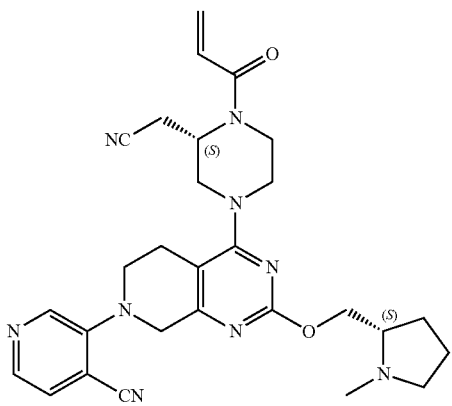

3-(4-((S)-4-acryloyl-3-(cyanomethyl)piperazin-1-yl)-2-(((S)-1-methylpyrrolidin-2-yl)methoxy)-5,6-dihydropyrido[3,4-d]pyrimidin-7(8H)-yl)isonicotinonitrile

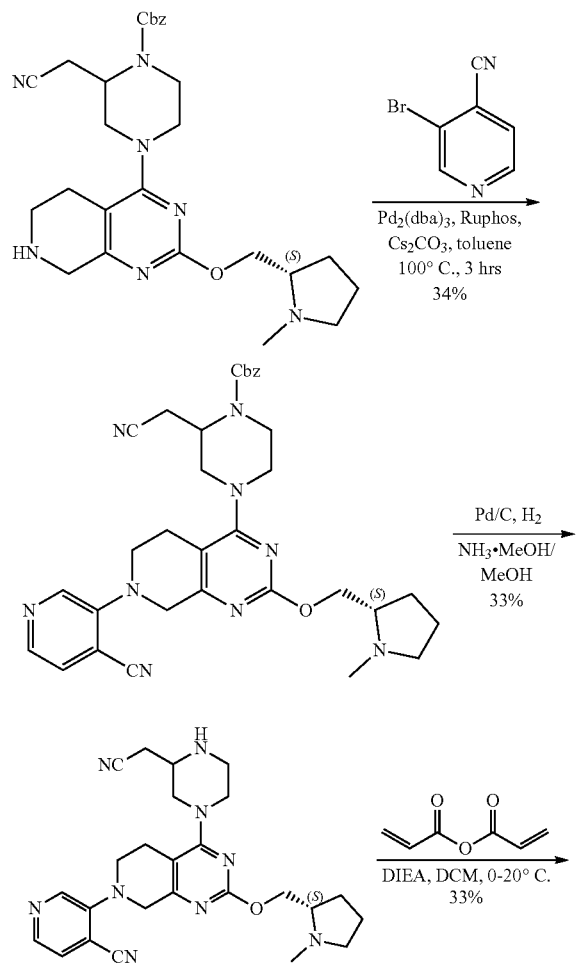

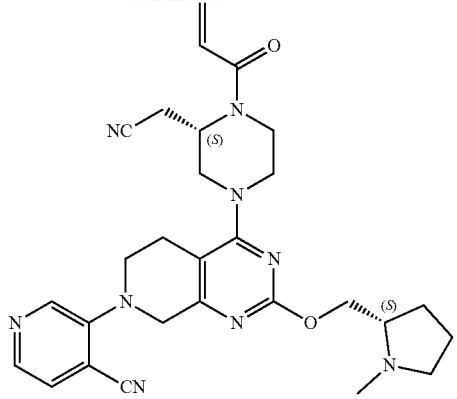

Step A: benzyl 2-(cyanomethyl)-4-[7-(4-cyano-3-pyridyl)-2-[[(2S)-1-methylpyrrolidin-2-yl]methoxy]-6,8-dihydro-5H-pyrido[3,4-d]pyrimidin-4-yl]piperazine-1-carboxylate To a solution of benzyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (400 mg, 791 umol, 1.0 eq) and 3-bromopyridine-4-carbonitrile (289 mg, 1.58 mmol, 2.0 eq) in toluene (10.0 mL) was added $Cs_2CO_3$ (516 mg, 1.58 mmol, 2.0 eq), $Pd_2(dba)_3$ (72.4 mg, 79.1 umol, 0.1 eq) and RuPhos (73.8 mg, 158 umol, 0.2 eq), the reaction mixture was stirred at 100° C. for 3 hours under $N_2$. After completion, the reaction mixture was added water (15 mL), then extracted with EA (2×15.0 mL), the combined organic layer was dried over $Na_2SO_4$, filtered and concentrated. The residue was purified by column chromatography (Base $Al_2O_3$, Petroleum ether/Ethyl acetate=5/1 to Petroleum ether/Ethyl acetate/Methanol=5/1/0.1) to give benzyl 2-(cyanomethyl)-4-[7-(4-cyano-3-pyridyl)-2-[[(2S)-1-methylpyrrolidin-2-yl]methoxy]-6,8-dihydro-5H-pyrido[3,4-d]pyrimidin-4-yl]piperazine-1-carboxylate (200 mg, 266 umol, 34% yield, 80.9% purity) as yellow solid. LCMS [ESI, M+1]: 608.

Step B: 3-[4-[3-(cyanomethyl)piperazin-1-yl]-2-[[(2S)-1-methyl pyrrolidin-2-yl]methoxy]-6,8-dihydro-5H-pyrido[3,4-d]pyrimidin-7-yl]pyridine-4-carbonitrile To a solution of benzyl 2-(cyanomethyl)-4-[7-(4-cyano-3-pyridyl)-2-[[(2S)-1-methylpyrrolidin-2-yl]methoxy]-6,8-dihydro-5H-pyrido[3,4-d]pyrimidin-4-yl]piperazine-1-carboxylate (170 mg, 226 umol, 1.0 eq) in MeOH (5.0 mL) was added $NH_3$.MeOH (49.4 ug, 49.4 umol, 5.0 mL) and Pd/C (150 mg, 10% purity), the suspension was degassed under vacuum and purged with $H_2$ several times. The mixture was stirred under $H_2$ (15 Psi) at 20° C. for 1 hour. After completion, the reaction was filtered through a Celite, and the filtrate was concentrated. The residue was purified by reversed phase flash (C18, 30% MeCN in water), the obtained product was adjusted with saturated $NaHCO_3$ aqueous to pH ~8, then concentrated until no solvent remained, the solid was then added DCM (10.0 mL) and stirred at 20° C. for 0.5 h, the solid was filtered and the filtrate was concentrated to give 3-[4-[3-(cyanomethyl)piperazin-1-yl]-2-[[(2S)-1-methyl pyrrolidin-2-yl] methoxy]-6,8-dihydro-5H-pyrido[3,4-d]pyrimidin-7-yl]pyridine-4-carbonitrile (35.0 mg, 73.9 umol, 33% yield, 100% purity) as white solid. LCMS [ESI, M+1]: 474.

Step C: 3-[4-[3-(cyanomethyl)-4-prop-2-enoyl-piperazin-1-yl]-2-[[(2S)-1-methylpyrrolidin-2yl]methoxy]-6,8-dihydro-5H-pyrido[3,4-d]pyrimidin-7-yl]pyridine-4-carbonitrile To a mixture of 3-[4-[3-(cyanomethyl)piperazin-1-yl]-2-[[(2S)-1-methylpyrrolidin-2-yl]methoxy]-6,8-dihydro-5H-pyrido[3,4-d]pyrimidin-7-yl]pyridine-4-carbonitrile (35.0 mg, 73.9 umol, 1.0 eq) in DCM (1.0 mL) was added DIEA (28.7 mg, 222 umol, 38.6 uL, 3.0 eq) and prop-2-enoyl prop-2-enoate (9.32 mg, 73.9 umol, 1.0 eq) at 0° C., the reaction mixture was stirred at 20° C. for 0.5 hour. After completion, the reaction mixture was quenched with MeOH (0.5 mL), and concentrated. The residue was purified by prep-HPLC ((Instrument: ACSWH-GX-M; Column: Gemini 150*25 5 u; Condition: water (0.04% $NH_3.H_2O$)-ACN; Begin B:32; End B:56; Gradient Time (min): 10; 100% B Hold Time (min):3; FlowRate (ml/min):100), the obtained product was concentrated, and then under lyophilization. The product 3-[4-[3-(cyanomethyl)-4-prop-2-enoyl-piperazin-1-yl]-2-[[(2S)-1-methylpyrrolidin-2yl]methoxy]-6,8-dihydro-5H-pyrido[3,4-d]pyrimidin-7-yl]pyridine-4-carbonitrile (EXAMPLE 305, 13.0 mg, 24.5 umol, 33% yield, 99.3% purity) was obtained as yellow solid. LCMS [ESI, M+1]: 528.

$^1$H NMR (400 MHz, chloroform-d) δ 8.52 (s, 1H), 8.33 (d, J=4.8 Hz, 1H), 7.46 (d, J=4.8 Hz, 1H), 6.69-6.53 (m, 1H), 6.42 (dd, J=1.6, 16.8 Hz, 1H), 5.85 (br d, J=11.6 Hz, 1H), 5.19-5.01 (m, 1H), 4.48-4.36 (m, 3H), 4.27-4.08 (m, 2H), 4.07-3.81 (m, 3H), 3.78-3.33 (m, 3H), 3.23-2.99 (m, 3H), 2.97-2.83 (m, 2H), 2.81-2.61 (m, 2H), 2.52 (s, 3H), 2.40-2.27 (m, 1H), 2.16-1.99 (m, 1H), 1.95-1.76 (m, 3H).

Example 306

2-((S)-1-acryloyl-4-(2-(((2S,4R)-4-fluoro-1-methyl-pyrrolidin-2-yl)methoxy)-7-(naphthalen-1-yl)-5,6,7,8-tetrahydropyrido[3,4-d]pyrimidin-4-yl)piperazin-2-yl)acetonitrile

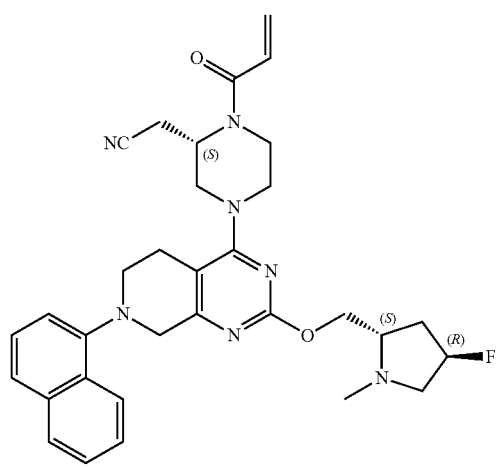

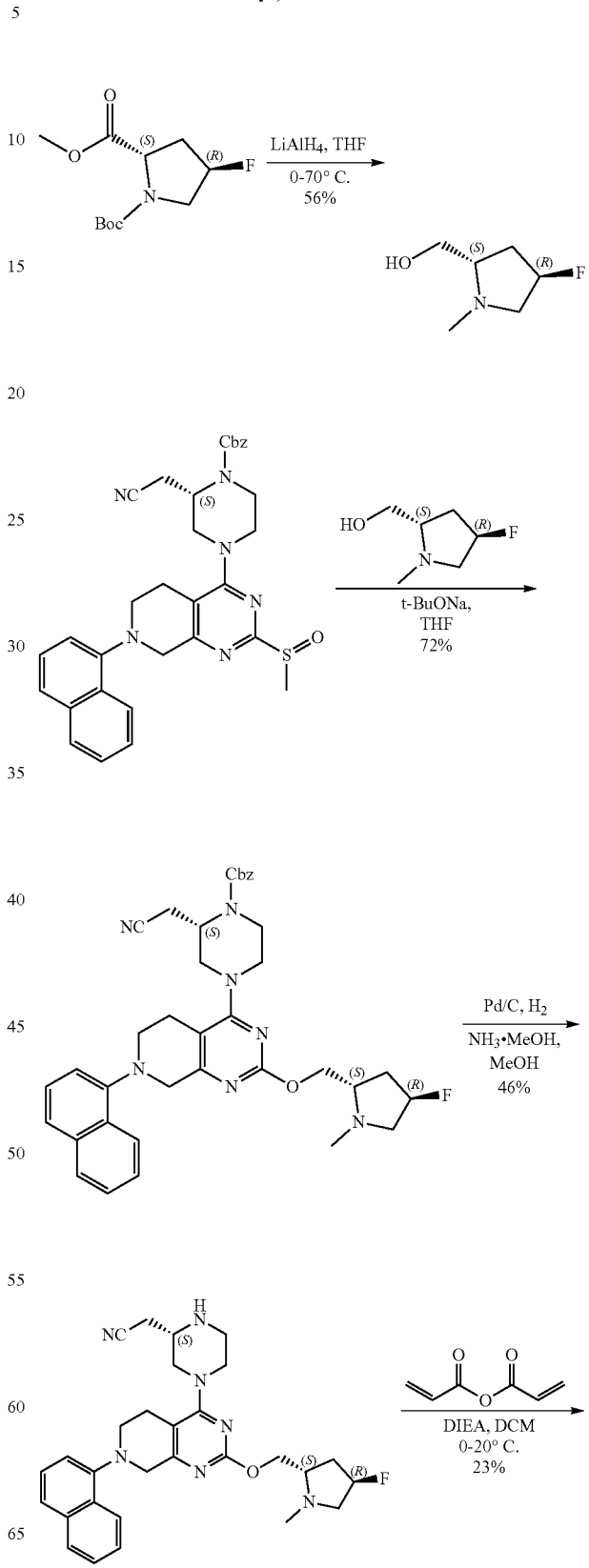

-continued

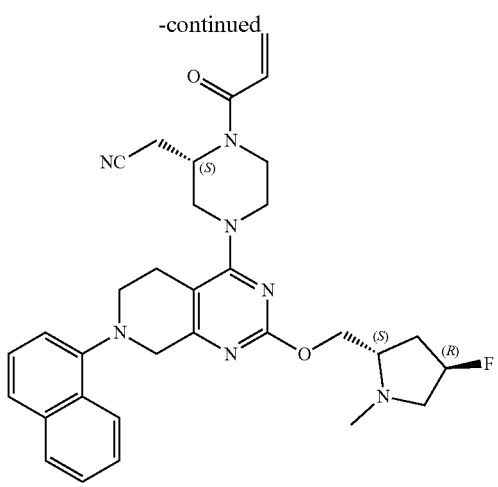

Step A: [(2S,4R)-4-fluoro-1-methyl-pyrrolidin-2-yl] methanol

To a solution of 1-tert-butyl 2-methyl (2S,4R)-4-fluoropyrrolidine-1,2-dicarboxylate (5.0 g, 20.2 mmol, 1.0 eq) in THF (100 mL) was added LiAlH$_4$ (1.53 g, 40.4 mmol, 2.0 eq) in portions at 0° C. After the reaction mixture was stirred at 0° C. for 1 hour under N$_2$, the reaction mixture was heated to 70° C. and stirred at 70° C. for 2 hours under N$_2$. After completion, the reaction mixture was quenched with saturated Na$_2$SO$_4$ aqueous (4.5 mL), then filtered, the filtrate was concentrated. The residue was purified by column chromatography (Base Al$_2$O$_3$, Petroleum ether/Ethyl acetate=5/1 to Petroleum ether/Ethyl acetate/Methanol=3/1/0.1) to give [(2S,4R)-4-fluoro-1-methyl-pyrrolidin-2-yl] methanol (1.5 g, 11.3 mmol, 56% yield) as yellow oil.

$^1$H NMR (400 MHz, chloroform-d) δ 5.24-4.97 (m, 1H), 3.73 (dd, J=3.2, 11.2 Hz, 1H), 3.61-3.40 (m, 2H), 2.86-2.74 (m, 1H), 2.69 (ddd, J=0.8, 2.8, 12.0 Hz, 1H), 2.61 (dd, J=2.4, 12.0 Hz, 1H), 2.41 (s, 3H), 2.18-1.98 (m, 2H).

Step B: benzyl (2S)-2-(cyanomethyl)-4-[2-[[(2S,4R)-4-fluoro-1-methyl-pyrrolidin-2-yl]methoxy]-7-(1-naphthyl)-6,8-dihydro-5H-pyrido[3,4-d]pyrimidin-4-yl]piperazine-1-carboxylate To a solution of benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 800 mg, 1.38 mmol, 1.0 eq) and [(2S,4R)-4-fluoro-1-methyl-pyrrolidin-2-yl]methanol (367 mg, 2.76 mmol, 2.0 eq) in toluene (15.0 mL) was added t-BuONa (265 mg, 2.76 mmol, 2.0 eq) at 0° C., the reaction was stirred at 0° C. for 0.5 hour. After completion, the reaction mixture was added water (30 mL), then extracted with EA (2×15 mL), the combined organic layer was washed with saturated brine (1×30 mL), then dried over Na$_2$SO$_4$, filtered and concentrated. The residue was purified by column chromatography (SiO$_2$, Petroleum ether/Ethyl acetate=5/1 to Petroleum ether/Ethyl acetate/Methanol=3/1/0.1) to give benzyl (2S)-2-(cyanomethyl)-4-[2-[[(2S,4R)-4-fluoro-1-methyl-pyrrolidin-2-yl]methoxy]-7-(1-naphthyl)-6,8-dihydro-5H-pyrido[3,4-d]pyrimidin-4-yl]piperazine-1-carboxylate (720 mg, 997 umol, 72% yield, 90.0% purity) as light yellow solid. LCMS [ESI, M+1]: 650.

Step C: 2-[(2S)-4-[2-[[(2S,4R)-4-fluoro-1-methyl-pyrrolidin-2-yl]methoxy]-7-(1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-[[(2S,4R)-4-fluoro-1-methyl-pyrrolidin-2-yl]methoxy]-7-(1-naphthyl)-6,8-dihydro-5H-pyrido[3,4-d]pyrimidin-4-yl]piperazine-1-carboxylate (670 mg, 1.03 mmol, 1.0 eq) in MeOH (15.0 mL) was added NH$_3$.MeOH (1.03 mmol, 15.0 mL, 1.0 eq) and Pd/C (400 mg, 10% purity), the suspension was degassed under vacuum and purged with H$_2$ several times. The mixture was stirred under H$_2$ (15 Psi) at 20° C. for 1 hour. After completion, the reaction was filtered through a Celite, and the filtrate was concentrated to give 2-[(2S)-4-[2-[[(2S,4R)-4-fluoro-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (260 mg, 478 umol, 46% yield, 94.9% purity) as white solid. LCMS [ESI, M+1]: 516.

Step D: 2-[(2S)-4-[2-[[(2S,4R)-4-fluoro-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a mixture of 2-[(2S)-4-[2-[[(2S,4R)-4-fluoro-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (260 mg, 504 umol, 1.0 eq) in DCM (5.0 mL) was added DIEA (196 mg, 1.51 mmol, 263 uL, 3.0 eq) and prop-2-enoyl prop-2-enoate (63.6 mg, 504 umol, 1.0 eq) at 0° C., the reaction mixture was stirred at 20° C. for 0.5 hour. After completion, the reaction mixture was quenched with MeOH (5 mL), and concentrated. The residue was purified by prep-HPLC ((Instrument: ACSWH-GX-H; Column: Gemini 150*25 5 u; Condition: water (0.05% ammonia hydroxide v/v)-ACN; Begin B:42; End B:72; Gradient Time (min): 12; 100% B Hold Time (min):1.8; FlowRate (ml/min): 25), the obtained product was concentrated, and then under lyophilization. The product 2-[(2S)-4-[2-[[(2S,4R)-4-fluoro-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (EXAMPLE 306, 65.6 mg, 115 umol, 23% yield, 99.8% purity) was obtained as yellow solid. LCMS [ESI, M+1]: 570.

$^1$H NMR (400 MHz, chloroform-d) δ 8.27-8.17 (m, 1H), 7.92-7.84 (m, 1H), 7.63 (d, J=8.0 Hz, 1H), 7.56-7.49 (m, 2H), 7.45 (t, J=8.0 Hz, 1H), 7.17 (d, J=6.8 Hz, 1H), 6.68-6.56 (m, 1H), 6.42 (dd, J=1.6, 16.8 Hz, 1H), 5.86 (br d, J=10.4 Hz, 1H), 5.30-4.99 (m, 2H), 4.45 (dd, J=4.8, 10.8 Hz, 1H), 4.35-4.21 (m, 3H), 4.15 (br d, J=13.6 Hz, 1H), 4.03 (br d, J=11.6 Hz, 2H), 3.70-2.72 (m, 11H), 2.68-2.56 (m, 1H), 2.54 (s, 3H), 2.41-2.27 (m, 1H), 2.10-1.90 (m, 1H).

Example 307

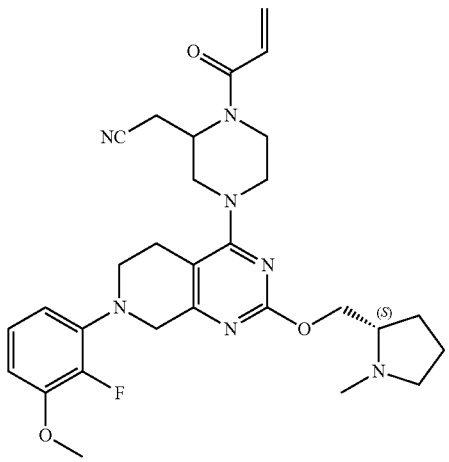

2-[4-[7-(2-fluoro-3-methoxy-phenyl)-2-[[(2S)-1-methylpyrrolidin-2-yl] methoxy]-6,8-dihydro-5H-pyrido[3,4-d]pyrimidin-4-yl]-1-prop-2-enoyl-piperazin-2-yl]acetonitrile

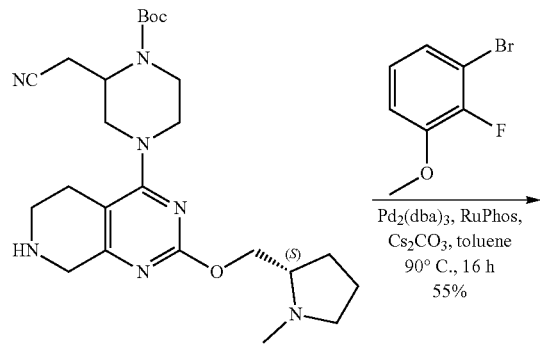

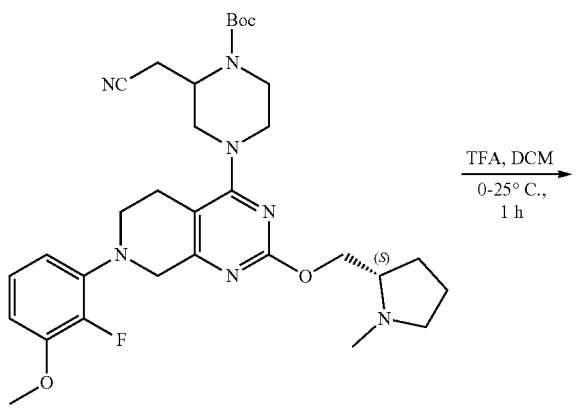

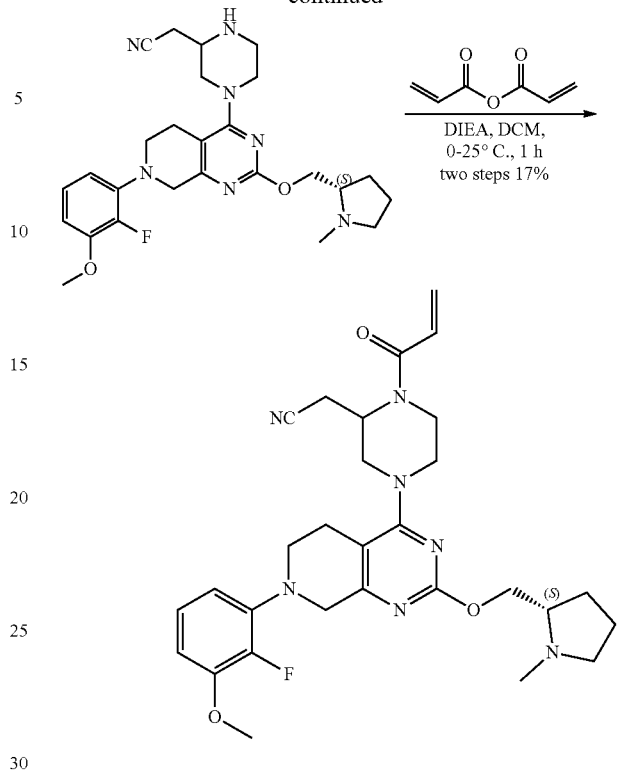

Step A: tert-butyl 2-(cyanomethyl)-4-[7-(2-fluoro-3-methoxy-phenyl)-2-[[(2S)-1-methylpyrrolidin-2-yl]methoxy]-6,8-dihydro-5H-pyrido[3,4-d]pyrimidin-4-yl]piperazine-1-carboxylate To a mixture of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 300 mg, 636 umol, 1.00 eq), 1-bromo-2-fluoro-3-methoxy-benzene (261 mg, 1.27 mmol, 2.00 eq), $Pd_2(dba)_3$ (117 mg, 127 umol, 0.20 eq), RuPhos (89.1 mg, 191 umol, 0.30 eq) and $Cs_2CO_3$ (622 mg, 1.91 mmol, 3.00 eq) in toluene (30 mL) was degassed and purged with $N_2$ for 3 times, and then the mixture was stirred at 90° C. for 16 hours under $N_2$ atmosphere. To the reaction mixture was added $H_2O$ (200 mL) and ethyl acetate (250 mL). The separated organic phase was washed with brine (1×200 mL), dried over sodium sulfate, filtered and concentrated under reduced pressure to give a residue. The residue was purified by reversed phase flash [water (0.1% FA)/acetonitrile]. The desired fractions were collected and neutralized with saturated $NaHCO_3$ solution and extracted with ethyl acetate (100 mL). The separated organic layer was dried over sodium sulfate, filtered and concentrated under vacuum. tert-butyl 2-(cyanomethyl)-4-[7-(2-fluoro-3-methoxy-phenyl)-2-[[(2S)-1-methylpyrrolidin-2-yl]methoxy]-6,8-dihydro-5H-pyrido[3,4-d]pyrimidin-4-yl]piperazine-1-carboxylate (210 mg, 353 umol, 55.4% yield, 100% purity) was obtained as a faint yellow solid. LCMS [ESI, M+1]: 596.

$^1$H NMR (400 MHz, chloroform-d) δ=7.00 (dt, J=1.6, 8.4 Hz, 1H), 6.74-6.56 (m, 2H), 4.61 (br s, 1H), 4.44-4.34 (m, 1H), 4.28-4.10 (m, 3H), 4.01 (br d, J=13.6 Hz, 1H), 3.90 (s, 4H), 3.56-3.40 (m, 1H), 3.25 (br dd, J=3.6, 13.6 Hz, 2H), 3.12 (br t, J=7.6 Hz, 1H), 2.98 (dt, J=2.8, 12.4 Hz, 1H), 2.89-2.63 (m, 5H), 2.50 (s, 3H), 2.35-2.26 (m, 1H), 2.21-2.06 (m, 3H), 1.90-1.68 (m, 3H), 1.60-1.42 (m, 9H).

Step B: 2-[4-[7-(2-fluoro-3-methoxy-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl 2-(cyanomethyl)-4-[7-(2-fluoro-3-methoxy-phenyl)-2-[[(2S)-1-methylpyrrolidin-2-yl]methoxy]-6,8-dihydro-5H-pyrido[3,4-d]pyrimidin-4-yl]piperazine-1-carboxylate (100 mg, 168 umol, 1.00 eq) in DCM (1 mL) was added TFA (1.63 g, 14.3 mmol, 1.06 mL, 85.0 eq) at 0° C. under nitrogen atmosphere. The mixture was stirred at 25° C. for 1 h and then the mixture was concentrated under vacuum. 2-[4-[7-(2-fluoro-3-methoxy-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (210 mg, crude, TFA) was obtained as a yellow oil. LCMS [ESI, M+1]: 496.

Step C: 2-[4-[7-(2-fluoro-3-methoxy-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[4-[7-(2-fluoro-3-methoxy-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (102 mg, crude TFA) and DIEA (216 mg, 1.67 mmol, 291 uL) in DCM (3 mL) was added prop-2-enoyl prop-2-enoate (16.9 mg, 134 umol) at 0° C. After stirring at 25° C. for 1 hour, the reaction mixture was quenched with saturated NaHCO₃ solution (5 mL) at 0° C., and then extracted with CH₂Cl₂ (2×25 mL). The combined organic layers were washed with brine (1×50 mL), dried over sodium sulfate, filtered and concentrated under vacuum to give a residue. The residue was purified by prep-HPLC (column: Phenomenex Gemini 150*25 mm*10 um; mobile phase: [water (0.05% ammonia hydroxide v/v)-ACN]; B %: 38%-68%, 12 min). 2-[4-[7-(2-fluoro-3-methoxy-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 307, 7.47 mg, 13.6 umol, two steps 17% yield, 100% purity) was obtained as a white solid. LCMS [ESI, M+1]: 550.

¹H NMR (400 MHz, chloroform-d) δ=7.07-6.95 (m, 1H), 6.74-6.51 (m, 3H), 6.45-6.34 (m, 1H), 5.83 (br d, J=10.6 Hz, 1H), 5.08 (br s, 1H), 4.38 (dd, J=4.8, 10.5 Hz, 1H), 4.31-4.12 (m, 3H), 4.07 (br d, J=13.6 Hz, 1H), 4.03-3.82 (m, 5H), 3.68-3.44 (m, 2H), 3.39-3.21 (m, 2H), 3.10 (br t, J=7.8 Hz, 2H), 2.95-2.61 (m, 5H), 2.48 (s, 3H), 2.33-2.23 (m, 1H), 2.13-1.99 (m, 1H), 1.92-1.62 (m, 3H).

Example 308

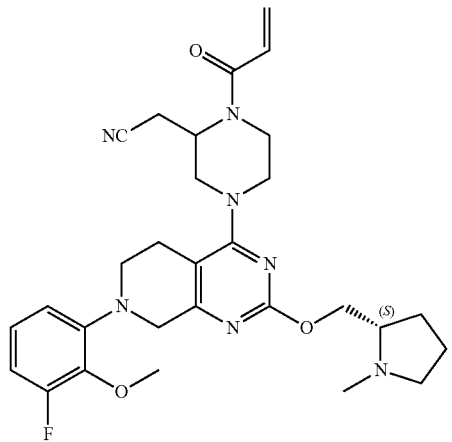

2-(1-acryloyl-4-(7-(3-fluoro-2-methoxyphenyl)-2-(((S)-1-methylpyrrolidin-2-yl)methoxy)-5,6,7,8-tetrahydropyrido[3,4-d]pyrimidin-4-yl)piperazin-2-yl)acetonitrile

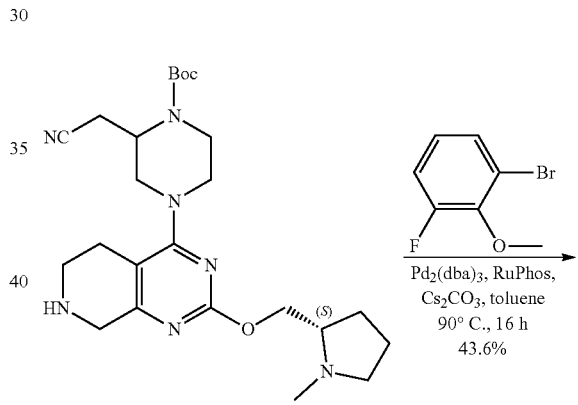

Pd₂(dba)₃, RuPhos, Cs₂CO₃, toluene
90° C., 16 h
43.6%

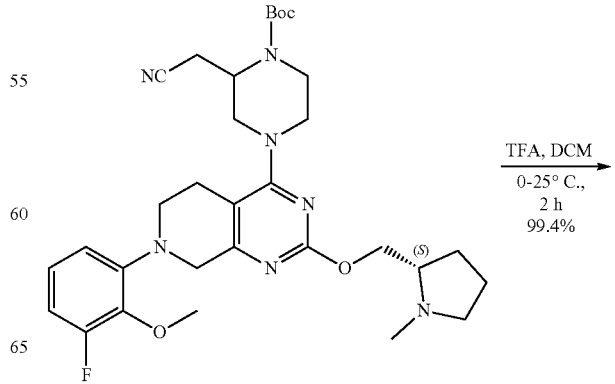

TFA, DCM
0-25° C.,
2 h
99.4%

-continued

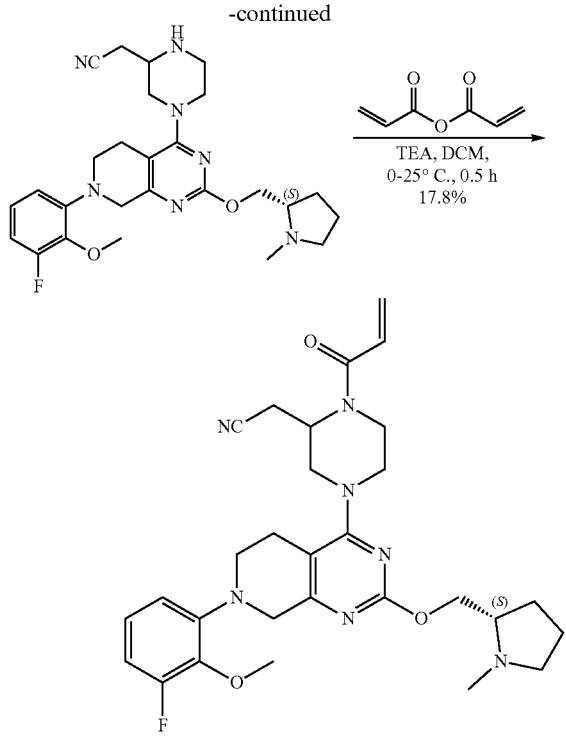

Step A: tert-butyl 2-(cyanomethyl)-4-[7-(3-fluoro-2-methoxy-phenyl)-2-[[(2S)-1-methyl pyrrolidin-2-yl]methoxy]-6,8-dihydro-5H-pyrido[3,4-d]pyrimidin-4-yl]piperazine-1-carboxylate To a mixture of tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 300 mg, 636 umol, 1 eq), 1-bromo-3-fluoro-2-methoxy-benzene (261 mg, 1.27 mmol, 2 eq), Pd$_2$(dba)$_3$ (117 mg, 127 umol, 0.2 eq), RuPhos (89.1 mg, 191 umol, 0.3 eq) and Cs$_2$CO$_3$ (622 mg, 1.91 mmol, 3 eq) in toluene (30 mL) was degassed and purged with N$_2$ for 3 times, and then the mixture was stirred at 90° C. for 16 hours under N$_2$ atmosphere. To the reaction mixture, H$_2$O (200 mL) and ethyl acetate (250 mL) were added. The organic phase was separated, washed with brine (200 mL), dried over sodium sulfate, filtered and concentrated under reduced pressure to give a residue. The residue was purified by reversed phase flash [water (0.1% FA)/acetonitrile]. The desired fractions were collected, neutralized with saturated NaHCO$_3$ solution and extracted with ethyl acetate (1×100 mL). The organic layer was dried over sodium sulfate, filtered and concentrated under vacuum. Compound tert-butyl 2-(cyanomethyl)-4-[7-(3-fluoro-2-methoxy-phenyl)-2-[[(2S)-1-methyl pyrrolidin-2-yl]methoxy]-6,8-dihydro-5H-pyrido[3,4-d]pyrimidin-4-yl]piperazine-1-carboxylate (170 mg, 277 umol, 43.6% yield, 97.1% purity) was obtained as a yellow solid. LCMS [ESI, M+1]: 596.

$^1$H NMR (400 MHz, chloroform-d) δ=6.96 (dt, J=6.0, 8.0 Hz, 1H), 6.83-6.69 (m, 1H), 6.83-6.68 (m, 1H), 4.60 (br s, 1H), 4.39 (dd, J=4.8, 10.4 Hz, 1H), 4.31-4.14 (m, 3H), 4.04 (br d, J=13.6 Hz, 2H), 3.94 (d, J=0.8 Hz, 4H), 3.62-3.47 (m, 1H), 3.26 (br dd, J=4.0, 13.6 Hz, 2H), 3.12 (br t, J=7.6 Hz, 1H), 2.99 (dt, J=2.8, 12.0 Hz, 1H), 2.88-2.64 (m, 5H), 2.50 (s, 3H), 2.36-2.24 (m, 1H), 2.22-2.07 (m, 2H), 1.94-1.64 (m, 3H), 1.56-1.46 (m, 9H).

Step B: 2-[4-[7-(3-fluoro-2-methoxy-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a mixture of tert-butyl 2-(cyanomethyl)-4-[7-(3-fluoro-2-methoxy-phenyl)-2-[[(2S)-1-methylpyrrolidin-2-yl]methoxy]-6,8-dihydro-5H-pyrido[3,4-d]pyrimidin-4-yl]piperazine-1-carboxylate (170 mg, 285 umol, 1 eq) in DCM (2.50 mL) was added TFA (651 mg, 5.71 mmol, 423 uL, 20 eq) in one portion at 0° C. under N$_2$. After stirred at 25° C. for 2 hours, the reaction mixture was concentrated under reduced pressure to give a residue. The crude product was used directly into the next step without further purification. Compound 2-[4-[7-(3-fluoro-2-methoxy-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (173 mg, 284 umol, 99.4% yield, TFA) was obtained as a brown solid. LCMS [ESI, M+1]: 496.

Step C: 2-[4-[7-(3-fluoro-2-methoxy-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[4-[7-(3-fluoro-2-methoxy-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (173 mg, 284 umol, 1 eq, TFA) and prop-2-enoyl prop-2-enoate (35.8 mg, 284 umol, 1 eq) in DCM (3 mL) was added TEA (144 mg, 1.42 mmol, 198 uL, 5 eq) in portion at 0° C. under N$_2$. After stirred at 25° C. for 0.5 hour, the reaction mixture was quenched by adding saturated NaHCO$_3$ (1.5 mL) at 0° C., and then diluted with water (2 mL) and extracted with DCM (20 mL×3). The combined organic layers were washed with water (15 mL×1), dried over sodium sulfate, filtered and concentrated under reduced pressure to give a residue. The crude product was purified by column chromatography (Al$_2$O$_3$, Petroleum ether/Ethyl acetate=100/1 to MeOH/EA=1/2). The desired fractions were collected and concentrated under reduced pressure. Then the residue was purified by prep-HPLC (column: Phenomenex Gemini 150×25 mm×10 um; mobile phase: [water (0.05% ammonia hydroxide v/v)-ACN]; B %: 48%-78%, 12 min). Title compound 2-[4-[7-(3-fluoro-2-methoxy-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 308, 28.2 mg, 50.4 umol, 17.8% yield, 98.1% purity) was obtained as a white solid. LCMS [ESI, M+1]: 550.

$^1$H NMR (400 MHz, chloroform-d) δ=6.97 (dt, J=6.0, 8.4 Hz, 1H), 6.83-6.76 (m, 1H), 6.72 (d, J=8.0 Hz, 1H), 6.57 (br d, J=12.0 Hz, 1H), 6.40 (dd, J=1.6, 16.8 Hz, 1H), 5.83 (br d, J=10.8 Hz, 1H), 5.07 (br s, 1H), 4.56 (br s, 1H), 4.39 (br dd, J=5.2, 10.4 Hz, 1H), 4.30-4.18 (m, 2H), 4.18-4.06 (m, 2H), 4.04-3.96 (m, 1H), 3.95 (d, J=0.8 Hz, 3H), 3.73-3.46 (m, 2H), 3.38-3.22 (m, 2H), 3.16-2.99 (m, 2H), 2.96-2.59 (m, 5H), 2.50 (s, 3H), 2.36-2.22 (m, 1H), 2.16-1.98 (m, 1H), 1.94-1.68 (m, 3H).

Example 309

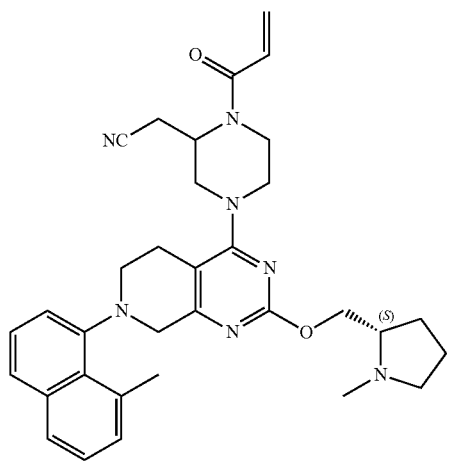

2-(1-acryloyl-4-(7-(8-methylnaphthalen-1-yl)-2-
(((S)-1-methylpyrrolidin-2-yl)methoxy)-5,6,7,8-
tetrahydropyrido[3,4-d]pyrimidin-4-yl)piperazin-2-
yl)acetonitrile

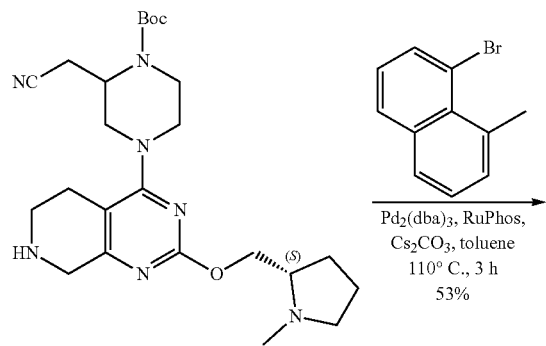

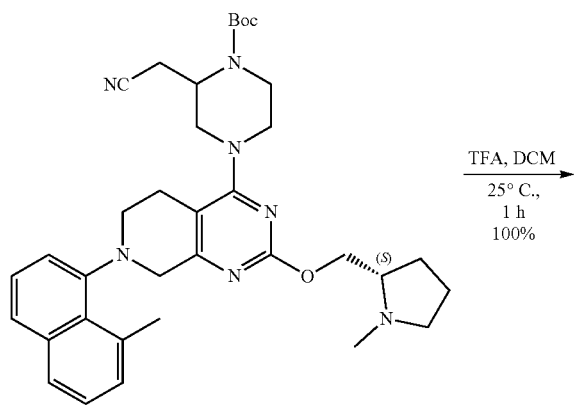

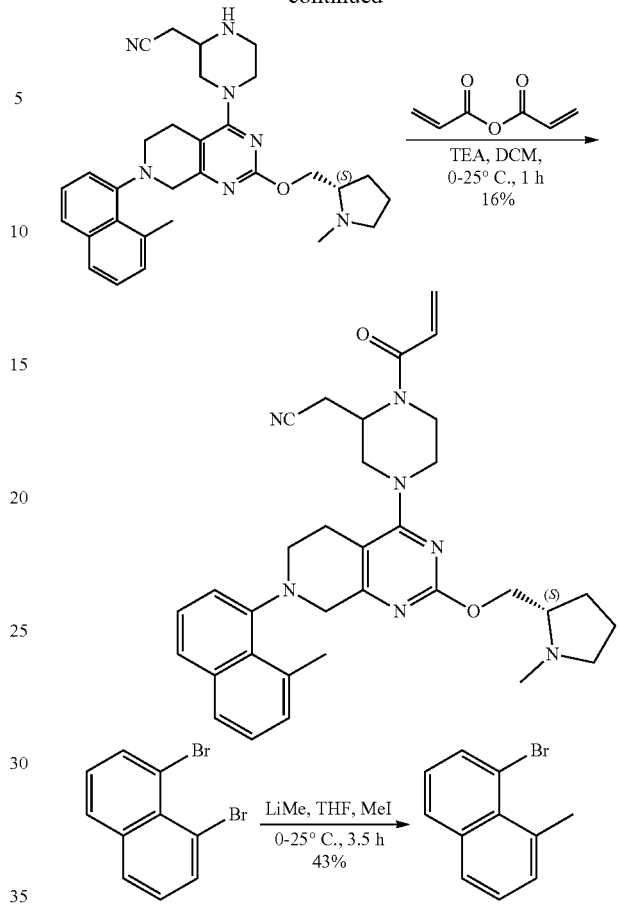

Insert: 1-bromo-8-methyl-naphthalene

To a solution of 1,8-dibromonaphthalene (1 g, 3.50 mmol, 1 eq) in THF (20 mL) was added MeLi (1.6 M in diethyl ether, 2.62 mL, 1.2 eq) at 0° C. dropwise. After stirring for 30 minutes at 0° C., iodomethane (3.38 g, 23.8 mmol, 1.48 mL, 6.81 eq) was added dropwise. The mixture was warmed up to 25° C. and stirred for another 3 hours. The reaction mixture was quenched with water (20 mL) and extracted with ethyl acetate (20 mL×3). The combined organic layers were washed with brine (20 mL), dried over $Na_2SO_4$, filtered and concentrated under reduced pressure to give a residue. The residue was purified by prep-HPLC (column: Phenomenex Gemini C18 250*50 mm*10 um; mobile phase: [water (0.05% ammonia hydroxide v/v)-ACN]; B %: 45%-70%, 28 MIN; 40% min). 1-bromo-8-methyl-naphthalene (340 mg, 1.49 mmol, 43% yield, 97% purity) was obtained as a yellow solid after lyophilisation.

$^1$H NMR (400 MHz, chloroform-d) δ=7.75 (dd, J=0.8, 7.2 Hz, 1H), 7.69 (dd, J=0.8, 8.0 Hz, 1H), 7.66-7.59 (m, 1H), 7.30-7.22 (m, 2H), 7.13 (t, J=8.0 Hz, 1H), 3.05 (s, 3H).

Step A: tert-butyl 2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate A mixture of 1-bromo-8-methyl-naphthalene (122 mg, 551 umol, 1.3 eq), tert-butyl 2-(cyanomethyl)-4-[2-[[(2S)-

1-methylpyrrolidin-2-yl]methoxy]-5,6,7,8-tetrahydropyrido[3,4-d]pyrimidin-4-yl]piperazine-1-carboxylate (Intermediate 66, 200 mg, 424 umol, 1 eq), Cs₂CO₃ (345 mg, 1.06 mmol, 2.5 eq), RuPhos (39.6 mg, 84.8 umol, 0.2 eq) and Pd₂(dba)₃ (77.7 mg, 84.8 umol, 0.2 eq) in toluene (10 mL) was degassed and purged with N₂ for 3 times, and then the mixture was stirred at 110° C. for 3 hours under N₂ atmosphere. The reaction mixture was diluted with water (20 mL) and extracted with ethyl acetate (20 mL×3). The combined organic layers were washed with brine (20 mL), dried over Na₂SO₄, filtered and concentrated under reduced pressure to give a residue. The residue was purified by reversed phase flash [water (0.1% formic acid)/acetonitrile)]. The mixture was adjusted pH=7 by addition saturated NaHCO₃ aqueous solution and extracted with ethyl acetate (20 mL×3). The combined organic layers were washed with brine (20 mL), dried over Na₂SO₄, filtered and concentrated under reduced pressure to give tert-butyl 2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (140 mg, 224 umol, 53% yield, 98% purity) as a yellow solid. LCMS [ESI, M+1]: 612.

¹H NMR (400 MHz, chloroform-d) δ=7.73-7.60 (m, 2H), 7.42 (dd, J=8.0, 16.0 Hz, 1H), 7.34 (t, J=7.6 Hz, 1H), 7.26-7.16 (m, 2H), 4.61 (br s, 1H), 4.40 (br s, 1H), 4.30-4.16 (m, 2H), 4.10-3.71 (m, 4H), 3.58-3.45 (m, 1H), 3.43-3.25 (m, 1H), 3.23-3.04 (m, 4H), 3.03-2.85 (m, 5H), 2.83-2.55 (m, 4H), 2.49 (br s, 3H), 2.40-2.20 (m, 1H), 2.14-2.06 (m, 1H), 1.92-1.71 (m, 2H), 1.55-1.44 (m, 9H).

Step B: 2-[4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl 2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (110 mg, 179 umol, 1 eq) in DCM (200 uL) was added TFA (307 mg, 2.70 mmol, 199 uL, 15 eq). After stirred at 25° C. for 1 hour, the mixture was concentrated under vacuum. 2-[4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (112 mg, 179 umol, 100% yield, TFA) was obtained as a yellow oil and used to next step directly without purification. LCMS [ESI, M+1]: 512.

Step C: 2-[4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (112 mg, 179 umol, 1 eq, TFA) in DCM (2 mL) was added TEA (181 mg, 1.79 mmol, 249 uL, 10 eq) at 0° C. And then prop-2-enoyl prop-2-enoate (18.1 mg, 143 umol, 0.8 eq) in DCM (1 mL) was added dropwise at 0° C. The resulting mixture was stirred at 25° C. for 1 hour. The reaction mixture was quenched with saturated NaHCO₃ aqueous solution (1 mL), diluted with water (10 mL) and extracted with ethyl acetate (20 mL×3). The combined organic layers were washed with brine (20 mL), dried over Na₂SO₄, filtered and concentrated under reduced pressure to give a residue. The residue was purified by column chromatography (Al₂O₃, Petroleum ether/Ethyl acetate=10/1 to 1/3) and further purified by prep-HPLC (column: Phenomenex Gemini 150*25 mm*10 um; mobile phase: [water (0.05% ammonia hydroxide v/v)-ACN]; B %: 55%-85%, 12 min). Title compound 2-[4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 309, 16.2 mg, 28.4 umol, 16% yield, 99% purity) was obtained as a white solid after lyophilisation. LCMS [ESI, M+1]: 566.

SFC condition: "OJ-3S_5_5_40_3ML Column: Chiralcel OJ-3 100×4.6 mm I.D., 3 um Mobile phase: ethanol (0.05% DEA) in CO₂ from 5% to 40% Flow rate: 3 mL/min Wavelength: 220 nm".

¹H NMR (400 MHz, chloroform-d) δ=7.70 (br d, J=8.0 Hz, 1H), 7.65 (t, J=8.4 Hz, 1H), 7.46-7.38 (m, 1H), 7.34 (t, J=6.4 Hz, 1H), 7.27-7.17 (m, 2H), 6.68-6.52 (m J=9.9 Hz, 1H), 6.46-6.35 (m, 1H), 5.83 (br d, J=10.4 Hz, 1H), 5.08 (br s, 1H), 4.59 (br s, 1H), 4.41-4.33 (m, 1H), 4.32-4.21 (m, 1H), 4.20-4.04 (m, 3H), 4.03-3.82 (m, 2H), 3.85-3.67 (m, 1H), 3.61-3.33 (m, 2H), 3.24-2.99 (m, 4H), 2.92 (s, 3H), 2.87-2.77 (m, 1H), 2.71-2.59 (m, 2H), 2.47 (d, J=4.0 Hz, 3H), 2.34-2.20 (m, 1H), 2.13-1.98 (m, 1H), 1.85-1.74 (m, 3H).

Example 310

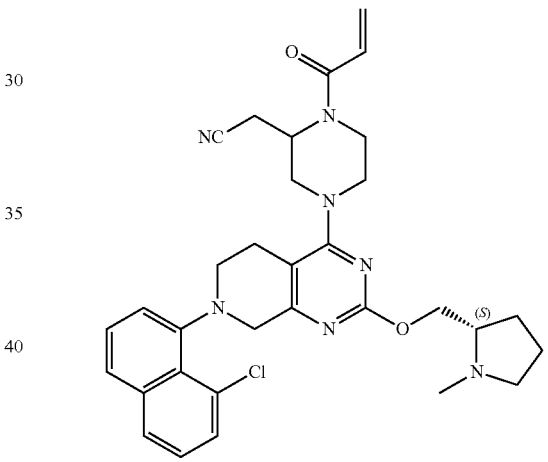

2-(1-acryloyl-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

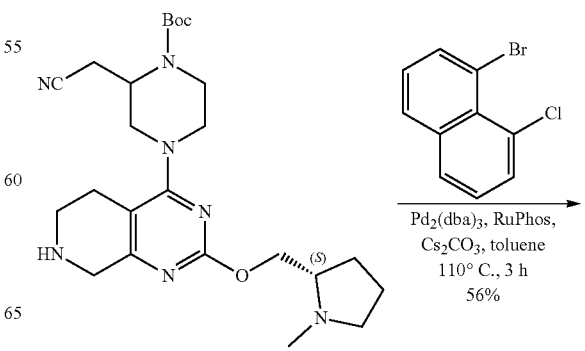

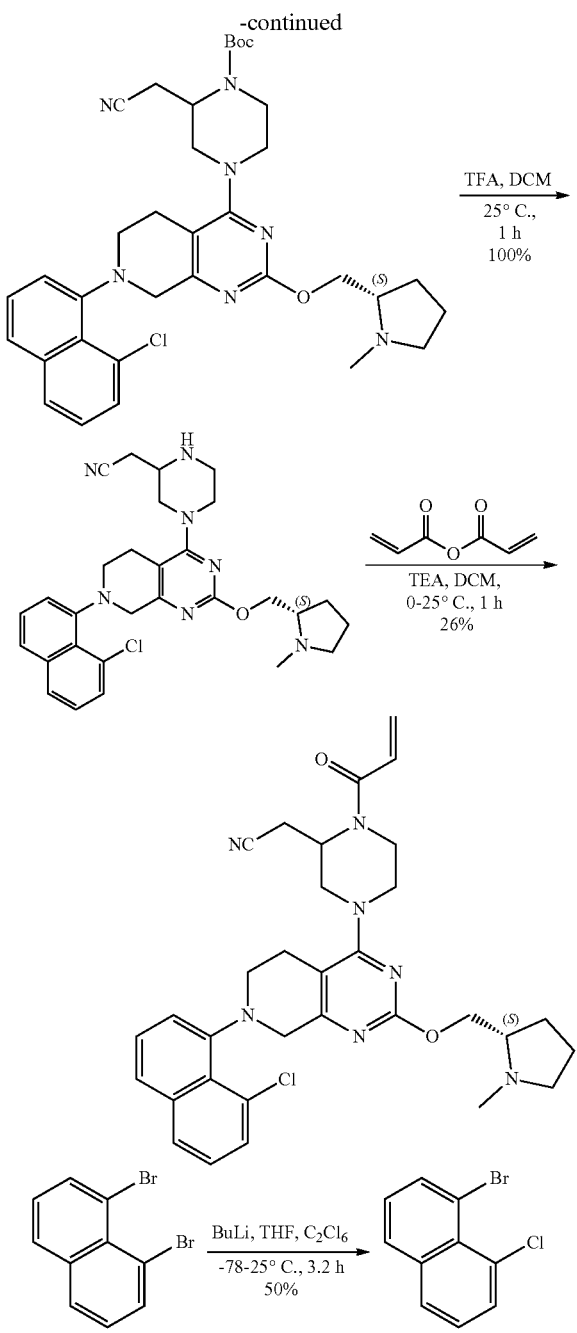

Insert: 1-bromo-8-chloronaphthalene

To a solution of perchloroethane (1.66 g, 6.99 mmol, 792 uL, 1 eq) in THF (30 mL) was added n-BuLi (2.5 M in hexane, 4.20 mL, 1.5 eq) at −78° C. dropwise. After stirring for an additional 10 minutes at −78° C., 1,8-dibromonaphthalene (2 g, 6.99 mmol, 1 eq) in THF (10 mL) was added. The mixture was warmed up to 25° C. and stirred for 3 hours. The reaction mixture was quenched with water (100 mL) and extracted with ethyl acetate (50 mL×3). The combined organic layers were washed with brine (50 mL), dried over Na₂SO₄, filtered and concentrated under reduced pressure to give a residue. The residue was purified by prep-HPLC (column: Phenomenex Synergi Max-RP 250*50 mm*10 um; mobile phase: [water (0.225% FA)-ACN]; B %: 41 ACN %-71 ACN %, 30 min; 50% min). The mixture was adjusted PH=7 by adding saturated NaHCO₃ aqueous solution and extracted with ethyl acetate (50 mL×3). The combined organic layers were washed with brine (20 mL), dried over Na₂SO₄, filtered and concentrated under reduced pressure to give 1-bromo-8-chloronaphthalene (850 mg, 3.52 mmol, 50% yield, 100% purity) as a yellow solid.

¹H NMR (400 MHz, chloroform-d) δ=7.92 (dd, J=1.2, 7.2 Hz, 1H), 7.80 (ddd, J=0.8, 8.0, 12.4 Hz, 2H), 7.67 (dd, J=1.2, 7.6 Hz, 1H), 7.38 (t, J=8.0 Hz, 1H), 7.32-7.25 (t, J=8.0 Hz, 1H).

Step A: tert-butyl 4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate A mixture of 1-bromo-8-chloro-naphthalene (133 mg, 551 umol, 1.3 eq), tert-butyl 2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (200 mg, 424 umol, 1 eq), Cs₂CO₃ (345 mg, 1.06 mmol, 2.5 eq), RuPhos (39.6 mg, 84.8 umol, 0.2 eq) and Pd₂(dba)₃ (77.7 mg, 84.8 umol, 0.2 eq) in toluene (10 mL) was degassed and purged with N₂ for 3 times, and then the mixture was stirred at 110° C. for 3 hours under N₂ atmosphere. The reaction mixture was diluted with water (20 mL) and extracted with ethyl acetate (20 mL×3). The combined organic layers were washed with brine (20 mL), dried over Na₂SO₄, filtered and concentrated under reduced pressure to give a residue. The residue was purified by reversed phase flash [water (0.1% formic acid)/acetonitrile)]. The mixture was adjusted pH=7 by adding saturated NaHCO₃ aqueous solution and extracted with ethyl acetate (20 mL×3). The combined organic layers were washed with brine (20 mL), dried over Na₂SO₄, filtered and concentrated under reduced pressure. Compound tert-butyl 4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (150 mg, 237 umol, 56% yield, 100% purity) was obtained as a yellow solid. LCMS [ESI, M+1]: 632.

¹H NMR (400 MHz, chloroform-d) δ=7.76 (d, J=8.4 Hz, 1H), 7.61 (t, J=7.6 Hz, 1H), 7.52 (d, J=7.6 Hz, 1H), 7.49-7.39 (m, 1H), 7.34 (t, J=7.6 Hz, 1H), 7.27-7.17 (m, 1H), 4.61 (br s, 1H), 4.51-4.33 (m, 2H), 4.22-4.15 (m, 1H), 4.10-3.77 (m, 4H), 3.57 (br s, 1H), 3.41-3.01 (m, 6H), 3.01-2.86 (m, 1H), 2.85-2.63 (m, 3H), 2.62-2.43 (m, 4H), 2.31 (br s, 1H), 2.13-2.06 (m, 1H), 1.78 (br s, 2H), 1.52 (s, 9H).

Step B: 2-[4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl 4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (150 mg, 237 umol, 1 eq) in DCM (200 uL) was added TFA (405 mg, 3.56 mmol, 263 uL, 15 eq). The mixture was stirred at 25° C. for 1 hour. The reaction mixture was concentrated under vacuum. Compound 2-[4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (153 mg, 236 umol, 100% yield,

811

TFA) was obtained as a yellow oil and used to next step directly without purification. LCMS [ESI, M+1]: 532.

Step C: 2-[4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (153 mg, 237 umol, 1 eq, TFA) in DCM (2 mL) was added TEA (239 mg, 2.37 mmol, 329 uL, 10 eq) at 0° C. After addition, the prop-2-enoyl prop-2-enoate (23.9 mg, 189 umol, 0.8 eq) in DCM (1 mL) was added dropwise at 0° C. The resulting mixture was stirred at 25° C. for 1 hour. The reaction mixture was quenched with saturated NaHCO₃ aqueous solution (1 mL) and diluted with water (20 mL), extracted with ethyl acetate (20 mL×3). The combined organic layers were washed with brine (20 mL), dried over Na₂SO₄, filtered and concentrated under reduced pressure. The residue was purified by prep-HPLC (column: Phenomenex Gemini 150*25 mm*10 um; mobile phase: [water (0.05% ammonia hydroxide v/v)-ACN]; B %: 52%-82%, 12 min). Title compound 2-[4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 310, 37 mg, 61.2 umol, 26% yield, 97% purity) was obtained after loyphilization as a white solid. LCMS [ESI, M+1]: 586.

SFC condition: "AD-3S_4_40_3ML Column: Chiralpak AD-3 100×4.6 mm I.D., 3 um Mobile phase: 40% isopropanol (0.05% DEA) in CO₂ Flow rate: 3 mL/min Wavelength: 220 nm".

¹H NMR (400 MHz, chloroform-d) δ=7.76 (d, J=8.0 Hz, 1H), 7.62 (t, J=7.2 Hz, 1H), 7.53 (d, J=7.6 Hz, 1H), 7.49-7.39 (m, 1H), 7.34 (t, J=8.0 Hz, 1H), 7.27-7.18 (m, 1H), 6.59 (br s, 1H), 6.45-6.35 (m, 1H), 5.83 (br d, J=10.8 Hz, 1H), 5.07 (s, 1H), 4.84-4.25 (m, 3H), 4.22-3.72 (m, 5H), 3.71-3.53 (m, 1H), 3.50-3.34 (m, 1H), 3.32-2.96 (m, 5H), 2.91-2.76 (m, 1H), 2.70-2.52 (m, 2H), 2.48 (d, J=2.8 Hz, 3H), 2.33-2.20 (m, 1H), 2.13-1.96 (m, 1H), 1.86-1.72 (m, 3H).

Example 311

812

2-(1-acryloyl-4-(7-(2-fluoronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

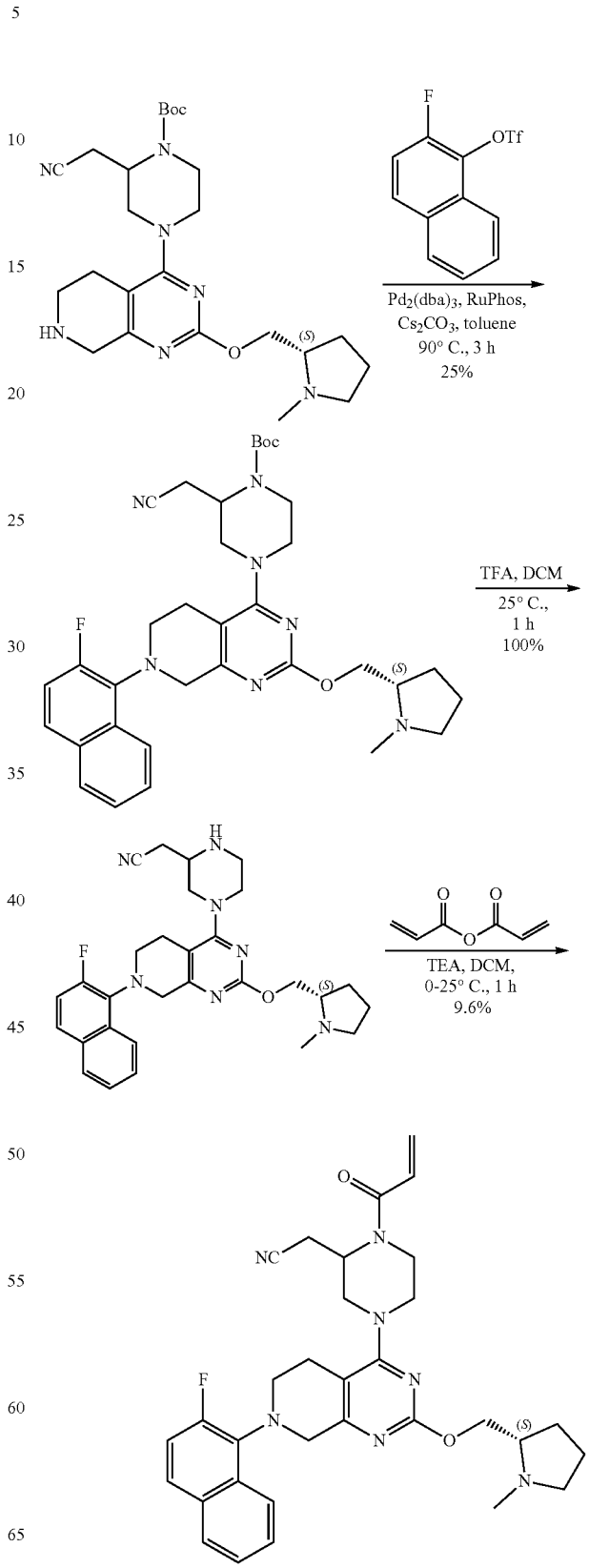

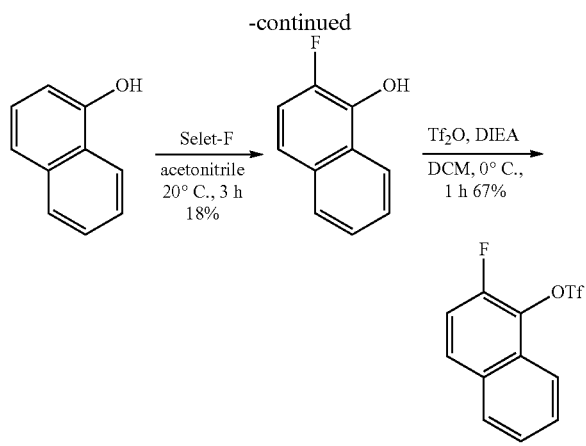

Step 1: 2-fluoronaphthalen-1-ol

To a solution of naphthalen-1-ol (2 g, 13.9 mmol, 5.00 mL, 1 eq) in CH$_3$CN (50 mL) was added Select-F (4.91 g, 13.9 mmol, 1 eq). The mixture was stirred at 20° C. for 3 hours. The mixture was concentrated under vacuum. The residue was purified by column chromatography (SiO$_2$, PE/EA=3/1) and further purified by prep-HPLC (column: Phenomenex Synergi C18 150*25*10 um; mobile phase: [water (0.225% FA)-ACN]; B %: 40%-70%, 10 min). The mixture was adjusted PH=7 with saturated NaHCO$_3$ aqueous solution and extracted with ethyl acetate (20 mL×3). The combined organic layers were washed with brine (20 mL), dried over Na$_2$SO$_4$, filtered and concentrated under reduced pressure. Compound 2-fluoronaphthalen-1-ol (400 mg, 2.44 mmol, 18% yield, 99% purity) was obtained as a yellow solid.

$^1$H NMR (400 MHz, chloroform-d) δ=8.21 (d, J=8.4 Hz, 1H), 7.80 (d, J=8.4 Hz, 1H), 7.52 (t, J=7.2 Hz, 1H), 7.47 (t, J=7.6 Hz, 1H), 7.39 (dd, J=5.2, 8.8 Hz, 1H), 7.31 (d, J=9.6 Hz, 1H), 5.58 (br s, 1H).

Step 2: (2-fluoro-1-naphthyl) trifluoromethanesulfonate: To a solution of 2-fluoronaphthalen-1-ol (400 mg, 2.47 mmol, 1 eq) in DCM (10 mL) was added Tf$_2$O (765 mg, 2.71 mmol, 448 uL, 1.1 eq) and DIEA (637 mg, 4.93 mmol, 859 uL, 2 eq) at 0° C. After stirred at 0° C. for 1 hour, the reaction mixture was diluted with ethyl acetate (20 mL) and washed with water (20 mL×3). The combined organic layer was washed with brine (20 mL), dried over Na$_2$SO$_4$, filtered and concentrated under reduced pressure to give a residue. The residue was purified by column chromatography (SiO$_2$, Petroleum ether/Ethyl acetate=50/1 to 3/1). Compound (2-fluoro-1-naphthyl) trifluoromethanesulfonate (500 mg, 1.65 mmol, 67% yield, 97% purity) was obtained as a colorless oil.

$^1$H NMR (400 MHz, chloroform-d) δ=8.07 (d, J=8.4 Hz, 1H), 7.95-7.85 (m, 2H), 7.70 (t, J=7.6 Hz, 1H), 7.62-7.54 (m, 1H), 7.41 (t, J=9.2 Hz, 1H).

Step A: tert-butyl 2-(cyanomethyl)-4-[7-(2-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate A mixture of (2-fluoro-1-naphthyl) trifluoromethanesulfonate (243 mg, 827 umol, 1.3 eq), tert-butyl 2-(cyanomethyl)-4-[2-[[(2S)-1-methyl pyrrolidin-2-yl]methoxy]-5,6,7,8-tetrahydropyrido[3,4-d]pyrimidin-4-yl]piperazine-1-carboxylate (300 mg, 636 umol, 1 eq), Cs$_2$CO$_3$ (518 mg, 1.59 mmol, 2.5 eq), RuPhos (59.4 mg, 127 umol, 0.2 eq) and Pd$_2$(dba)$_3$ (116 mg, 127 umol, 0.2 eq) in toluene (10 mL) was degassed and purged with N$_2$ for 3 times, and then the mixture was stirred at 90° C. for 3 hours under N$_2$ atmosphere. The reaction mixture was diluted with water (20 mL) and extracted with ethyl acetate (20 mL×3). The combined organic layers were washed with brine (20 mL), dried over Na$_2$SO$_4$, filtered and concentrated under reduced pressure to give a residue. The residue was purified by reversed phase flash [water (0.1% formic acid)/acetonitrile)]. The mixture was adjusted PH=7 by adding saturated NaHCO$_3$ aqueous solution and extracted with ethyl acetate (20 mL×3). The combined organic layers were washed with brine (20 mL), dried over Na$_2$SO$_4$, filtered and concentrated under reduced pressure. Compound tert-butyl 2-(cyanomethyl)-4-[7-(2-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (100 mg, 155 umol, 25% yield, 96% purity) was obtained as a yellow solid. LCMS [ESI, M+1]: 616.

$^1$H NMR (400 MHz, chloroform-d) δ=8.33 (br s, 1H), 7.84 (d, J=7.76 Hz, 1H), 7.75-7.64 (m, 1H), 7.57-7.41 (m, 2H), 7.25-7.21 (m, 1H), 4.63 (br s, 1H), 4.47-4.16 (m, 4H), 4.13-3.82 (m, 4H), 3.61-3.25 (m, 3H), 3.20-2.90 (m, 4H), 2.81-2.56 (m, 4H), 2.49 (s, 3H), 2.38-2.19 (m, 1H), 2.14-2.06 (m, 1H), 1.88-1.69 (m, 2H), 1.53 (s, 9H).

Step B: 2-[4-[7-(2-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl 2-(cyanomethyl)-4-[7-(2-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (100 mg, 162 umol, 1 eq) in DCM (200 uL) was added TFA (278 mg, 2.44 mmol, 180 uL, 15 eq). The mixture was stirred at 25° C. for 1 hour. The reaction mixture was concentrated under vacuum. Compound 2-[4-[7-(2-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (102 mg, 162 umol, 100% yield, TFA) was obtained as a yellow oil and used to next step directly without purification. LCMS [ESI, M+1]: 516.

Step C: 2-[4-[7-(2-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[4-[7-(2-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (102 mg, 197 umol, 1 eq, TFA) in DCM (2 mL) was added TEA (200 mg, 1.98 mmol, 275 uL, 10 eq) at 0° C. After addition, the prop-2-enoyl prop-2-enoate (19.9 mg, 158 umol, 0.8 eq) in DCM (1 mL) was added dropwise at 0° C. After stirred at 25° C. for 1 hour, the reaction mixture was quenched with saturated NaHCO$_3$ aqueous solution (1 mL) and diluted with water (20 mL), extracted with ethyl acetate (20 mL×3). The combined organic layers were washed with brine (20 mL), dried over $Na_2SO_4$, filtered and concentrated under reduced pressure to give a residue. The residue was purified by prep-HPLC (column: Phenomenex Gemini 150*25 mm*10 um; mobile phase: [water (0.05% ammonia hydroxide v/v)-ACN]; B %: 52%-82%, 12 min). Title compound 2-[4-[7-(2-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 311, 11 mg, 18.9 umol, 9.6% yield, 98% purity) was obtained after lyophilization as a white solid. LCMS [ESI, M+1]: 570.

SFC condition: "OD-3S_3_40_3ML Column: Chiralcel OD-3 100×4.6 mm I.D., 3 um Mobile phase: 40% methanol (0.05% DEA) in $CO_2$ Flow rate: 3 mL/min Wavelength: 220 nm".

$^1$H NMR (400 MHz, chloroform-d) δ=8.34 (br s, 1H), 7.84 (d, J=8.0 Hz, 1H), 7.69 (dd, J=4.4, 8.8 Hz, 1H), 7.52 (t, J=7.2 Hz, 1H), 7.47 (t, J=6.8 Hz, 1H), 7.29-7.25 (m, 1H), 6.65-6.50 (m, J=10.5 Hz, 1H), 6.40 (dd, J=1.2, 16.8 Hz, 1H), 5.84 (br d, J=10.4 Hz, 1H), 5.11 (br s, 1H), 4.65 (s, 1H), 4.43-3.85 (m, 7H), 3.81-3.30 (m, 3H), 3.24-2.95 (m, 3H), 2.94-2.56 (m, 4H), 2.47 (s, 3H), 2.36-2.20 (m, 1H), 2.13-1.97 (m, 1H), 1.93-1.75 (m, 3H).

Example 312

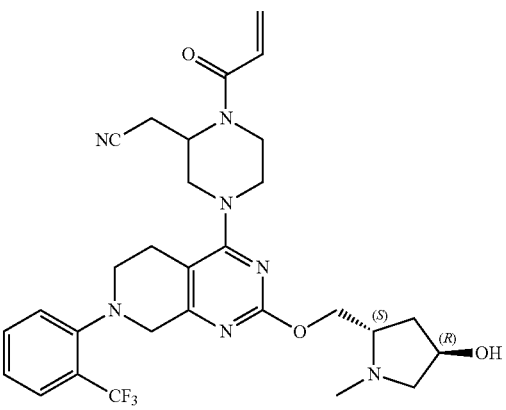

2-[4-[2-[[(2S,4R)-4-hydroxy-1-methyl-pyrrolidin-2-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile

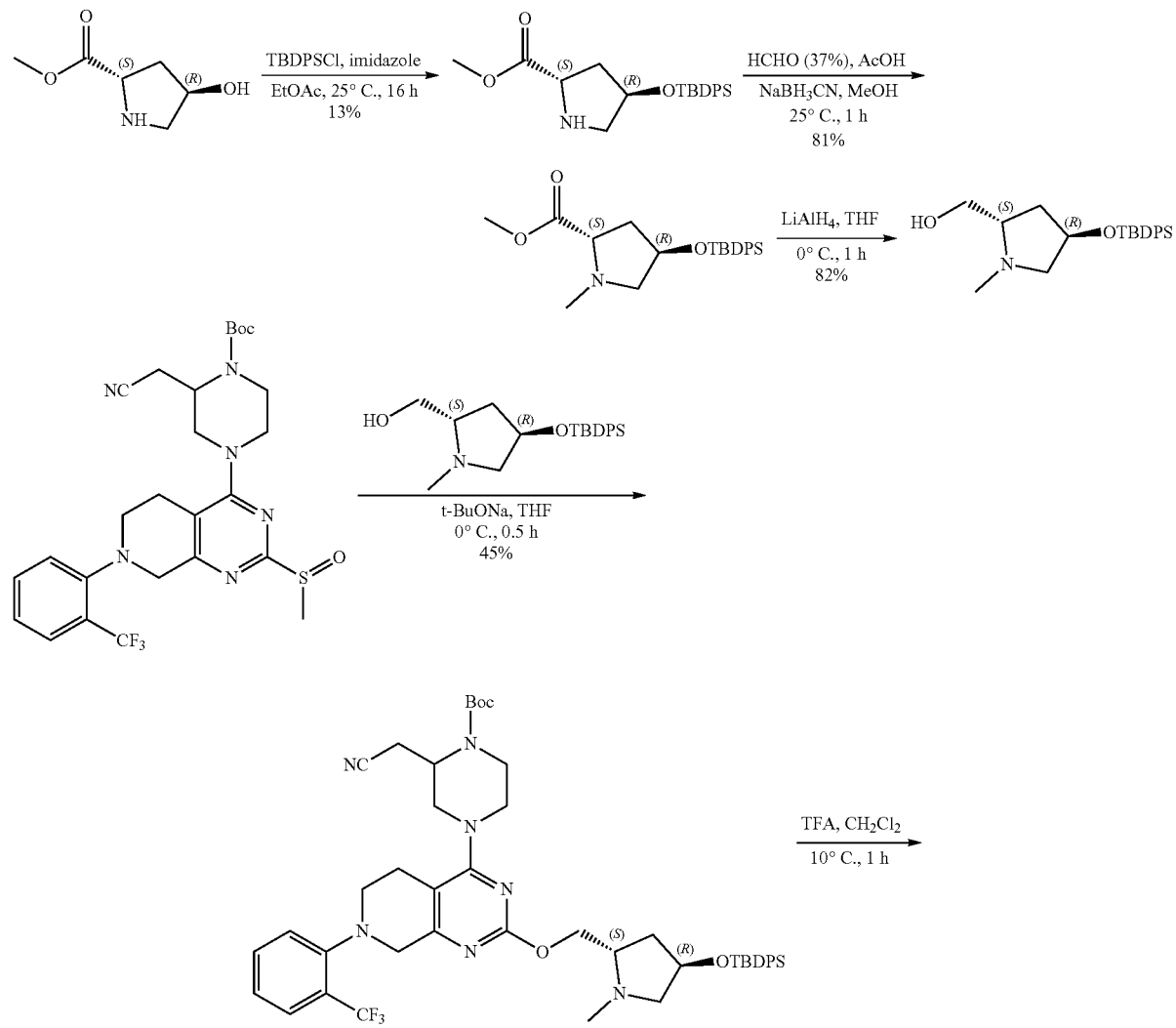

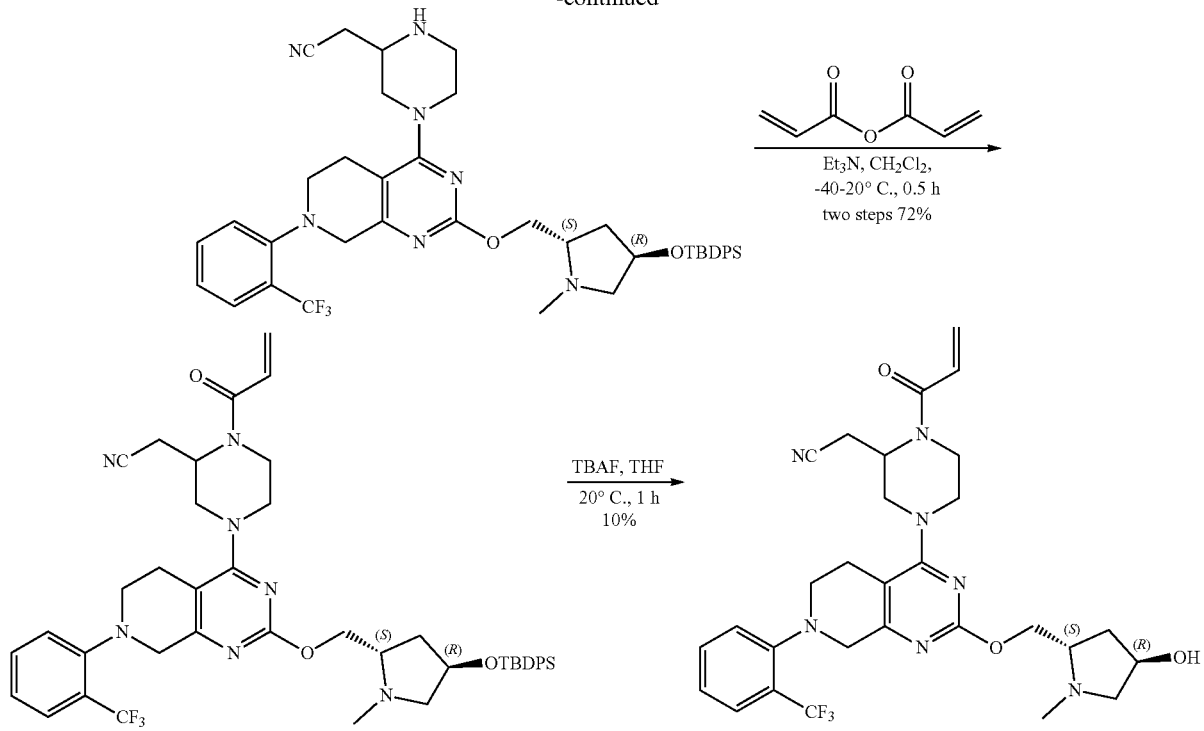

Step A: methyl (2S,4R)-4-[tert-butyl(diphenyl)silyl]oxypyrrolidine-2-carboxylate To a solution of methyl (2S,4R)-4-hydroxypyrrolidine-2-carboxylate (10 g, 55.1 mmol, 1 eq, HCl) in ethyl acetate (10 mL) were added imidazole (7.50 g, 110 mmol, 2 eq) and TBDPSCl (16.7 g, 60.6 mmol, 15.6 mL, 1.1 eq). The mixture was stirred at 25° C. for 16 hours. The precipitate was filtered off. The filtrate was concentrated under reduced pressure and the residue was dissolved with ethyl acetate (200 mL) and water (100 mL). The organic phase was washed with brine (1×100 mL), dried over magnesium sulfate, filtered and concentrated under reduced pressure. The residue was purified by column chromatography over silica gel (petroleum ether/ethyl acetate 10/1 to 1/1). The desired fractions were collected and concentrated under vacuum to give methyl (2S,4R)-4-[tert-butyl(diphenyl)silyl] oxypyrrolidine-2-carboxylate (2.9 g, 7.41 mmol, 13% yield, 98% purity) as a colorless oil. LCMS [ESI, M+1]: 384.

$^1$H NMR (400 MHz, chloroform-d) δ=7.64 (dt, J=1.2, 7.2 Hz, 4H), 7.47-7.35 (m, 6H), 4.40 (td, J=2.4, 4.8 Hz, 1H), 4.07 (t, J=8.0 Hz, 1H), 3.70 (s, 3H), 3.03-2.96 (m, 1H), 2.96-2.89 (m, 1H), 2.17-2.07 (m, 1H), 1.84-1.77 (m, 1H), 1.07 (s, 9H).

Step B: methyl (2S,4R)-4-[tert-butyl(diphenyl)silyl]oxy-1-methyl-pyrrolidine-2-carboxylate To a solution of methyl (2S,4R)-4-[tert-butyl(diphenyl) silyl] oxypyrrolidine-2-carboxylate (2.7 g, 7.04 mmol, 1 eq) and formaldehyde (37% aqueous, 2.86 g, 35.2 mmol, 2.62 mL, 5 eq) in MeOH (20 mL) was added CH$_3$COOH (423 mg, 7.04 mmol, 403 uL, 1 eq) and NaBH$_3$CN (1.77 g, 28.2 mmol, 4 eq). The mixture was stirred at 25° C. for 1 hr. The mixture was diluted with ethyl acetate (200 mL) and washed with water (2×100 mL) and brine (1×100 mL). The separated organic layer was dried over sodium sulfate, filtered and concentrated under vacuum. The residue was purified by column chromatography over silica gel (petroleum ether/ethyl acetate 20/1 to 3/1). The desired fractions were collected and concentrated under vacuum to give methyl (2S,4R)-4-[tert-butyl(diphenyl)silyl] oxy-1-methyl-pyrrolidine-2-carboxylate (2.4 g, 5.71 mmol, 81% yield, 94.6% purity) as a colorless oil. LCMS [ESI, M+1]: 398.

$^1$H NMR (400 MHz, chloroform-d) δ=7.63 (ddd, J=1.2, 4.0, 7.6 Hz, 4H), 7.46-7.32 (m, 6H), 4.47-4.39 (m, 1H), 3.71 (s, 3H), 3.32 (t, J=8.4 Hz, 1H), 3.24 (dd, J=6.0, 9.6 Hz, 1H), 2.43-2.40 (m, 1H), 2.40 (s, 3H), 2.23-2.00 (m, 2H), 1.07 (s, 9H).

Step C: [(2S,4R)-4-[tert-butyl(diphenyl)silyl]oxy-1-methyl-pyrrolidin-2-yl]methanol To a solution of methyl (2S,4R)-4-[tert-butyl(diphenyl) silyl]oxy-1-methyl-pyrrolidine-2-carboxylate (2.20 g, 5.53 mmol, 1.00 eq) in THF (40 mL) was added LiAlH$_4$ (840 mg, 22.1 mmol, 4.00 eq) at 0° C. The mixture was stirred at 0° C. for 1 hour. The mixture was quenched with water (1.00 mL), sodium hydroxide solution (15.0%, 2.00 mL) and water (3.00 mL). The precipitate was filtered off and the filtrate was concentrated under vacuum. The residue was purified by column chromatography (Al$_2$O$_3$, methanol/ethyl acetate=1/10) to give [(2S,4R)-4-[tert-butyl(diphenyl)silyl] oxy-1-methyl-pyrrolidin-2-yl]methanol (1.70 g, 4.55 mmol, 82% yield) as a colorless oil. LCMS [ESI, M+1]: 370.

$^1$H NMR (400 MHz, chloroform-d) δ=7.68-7.61 (m, 4H), 7.46-7.35 (m, 6H), 4.35-4.26 (m, 1H), 3.62 (dd, J=3.2, 10.8 Hz, 1H), 3.34 (dd, J=2.0, 10.8 Hz, 1H), 3.14 (dd, J=5.6, 10.0 Hz, 1H), 2.78-2.70 (m, 1H), 2.43 (dd, J=6.0, 9.6 Hz, 1H), 2.33 (s, 3H), 2.02-1.93 (m, 1H), 1.92-1.84 (m, 1H), 1.06 (s, 9H).

Step D: tert-butyl 4-[2-[[(2S,4R)-4-[tert-butyl(diphenyl)silyl]oxy-1-methyl-pyrrolidin-2-yl]methoxy]-7-[2-(trifluoromethyl)phenyl]-6,8-dihydro-5H-pyrido[3,4-d]pyrimidin-4-yl]-2-(cyanomethyl)piperazine-1-carboxylate To a solution of tert-butyl 2-(cyanomethyl)-4-[2-methylsulfinyl-7-[2-(trifluoromethyl)phenyl]-6,8-dihydro-5H-pyrido[3,4-d]pyrimidin-4-yl]piperazine-1-carboxylate (0.30 g, 531 umol, 1.00 eq) and [(2S,4R)-4-[tert-butyl(diphenyl)silyl]oxy-1-methyl-pyrrolidin-2-yl]methanol (295 mg, 797 umol, 1.50 eq) in THF (5 mL) was added t-BuONa (102 mg, 1.06 mmol, 2.00 eq) at 0° C. After stirred at 0° C. for 0.5 h, the mixture was adjusted to pH=7 by HCl solution (1.00 M, 0.40 mL) and extracted with ethyl acetate (3×10.0 mL). The organic layers were washed with brine (1×10.0 mL), dried over Na$_2$SO$_4$, filtered and concentrated under vacuum. The residue was purified by column chromatography (Al$_2$O$_3$, petroleum ether/ethyl acetate=1/3) to give tert-butyl 4-[2-[[(2S,4R)-4-[tert-butyl(diphenyl)silyl]oxy-1-methyl-pyrrolidin-2-yl]methoxy]-7-[2-(trifluoromethyl)phenyl]-6,8-dihydro-5H-pyrido[3,4-d]pyrimidin-4-yl]-2-(cyanomethyl)piperazine-1-carboxylate (0.22 g, 238 umol, 45% yield) as a white solid. LCMS [ESI, M+1]: 870.

$^1$H NMR (400 MHz, chloroform-d) δ=7.68 (br d, J=8.0 Hz, 1H), 7.66-7.61 (m, 4H), 7.57 (br t, J=7.2 Hz, 1H), 7.44-7.34 (m, 7H), 7.33-7.28 (m, 1H), 4.61 (br s, 1H), 4.45-4.28 (m, 2H), 4.09-3.95 (m, 4H), 3.87 (br d, J=12.8 Hz, 1H), 3.28-3.15 (m, 4H), 3.10 (ddd, J=3.6, 7.2, 12.0 Hz, 2H), 3.02-2.93 (m, 1H), 2.88-2.67 (m, 4H), 2.48 (s, 3H), 2.45-2.34 (m, 2H), 2.14-2.07 (m, 1H), 1.94-1.80 (m, 1H), 1.52 (s, 9H), 1.06 (s, 9H).

Step E: 2-[4-[2-[[(2S,4R)-4-[tert-butyl(diphenyl)silyl]oxy-1-methyl-pyrrolidin-2-yl]methoxy]-7-[2-(trifluoromethyl)phenyl]-6,8-dihydro-5H-pyrido[3,4-d]pyrimidin-4-yl]piperazin-2-yl]acetonitrile A mixture of tert-butyl 4-[2-[[(2S,4R)-4-[tert-butyl(diphenyl) silyl]oxy-1-methyl-pyrrolidin-2-yl]methoxy]-7-[2-(trifluoromethyl)phenyl]-6,8-dihydro-5H-pyrido[3,4-d]pyrimidin-4-yl]-2-(cyanomethyl)piperazine-1-carboxylate (0.08 g, 91.9 umol, 1.00 eq) and TFA (157 mg, 1.38 mmol, 102 uL, 15.0 eq) in dichloromethane (150 uL) was stirred at 10° C. for 1 hour. The mixture was concentrated under vacuum to give 2-[4-[2-[[(2S,4R)-4-[tert-butyl(diphenyl)silyl]oxy-1-methyl-pyrrolidin-2-yl]methoxy]-7-[2-(trifluoromethyl)phenyl]-6,8-dihydro-5H-pyrido[3,4-d]pyrimidin-4-yl]piperazin-2-yl]acetonitrile (81.3 mg, crude, TFA) as a yellow oil and used into next step without further purification. LCMS [ESI, M+1]: 770.

Step F: 2-[4-[2-[[(2S,4R)-4-[tert-butyl(diphenyl)silyl]oxy-1-methyl-pyrrolidin-2-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile To a solution of 2-[4-[2-[[(2S,4R)-4-[tert-butyl(diphenyl) silyl] oxy-1-methyl-pyrrolidin-2-yl]methoxy]-7-[2-(trifluoromethyl)phenyl]-6,8-dihydro-5H-pyrido[3,4-d]pyrimidin-4-yl]piperazin-2-yl]acetonitrile (0.08 g, crude, TFA) and Et$_3$N (91.6 mg, 905 umol, 125.96 uL) in dichloromethane (2.00 mL) was added prop-2-enoyl prop-2-enoate (11.4 mg, 90.5 umol) at −40° C. After stirred at 20° C. for 0.5 h, the mixture was quenched with water (0.20 mL) and concentrated under vacuum. The residue was purified by column chromatography (Al$_2$O$_3$, methanol/ethyl acetate=1/10). The desired fractions were collected and concentrated under vacuum to give 2-[4-[2-[[(2S,4R)-4-[tert-butyl(diphenyl)silyl]oxy-1-methyl-pyrrolidin-2-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile (0.06 g, 65.5 umol, two steps 72% yield) as a yellow oil. LCMS [ESI, M/2+1]: 412.

Step G: 2-[4-[2-[[(2S,4R)-4-hydroxy-1-methyl-pyrrolidin-2-yl]methoxy]-7-[2-(trifluoromethyl) phenyl]-6,8-dihydro-5H-pyrido[3,4-d]pyrimidin-4-yl]-1-prop-2-enoyl-piperazin-2-yl]acetonitrile A mixture of 2-[4-[2-[[(2S,4R)-4-[tert-butyl(diphenyl)silyl] oxy-1-methyl-pyrrolidin-2-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile (0.05 g, 60.7 umol, 1.00 eq) and TBAF (1.00 M, 607 uL, 10.0 eq) in THF (0.50 mL) was stirred at 20° C. for 1 hour. The mixture was concentrated under vacuum. The residue was purified by column chromatography (Al$_2$O$_3$, ethyl acetate/methanol=3/1) and reversed phase flash [water (FA, 0.10%)/acetonitrile], then further purified by prep-HPLC column: Boston pH-lex 150*25 10 um; mobile phase: [water (0.10%, TFA)-ACN]; B %: 31%-61%,10 min and column: Phenomenex Gemini 150*25 mm*10 um; mobile phase: [water (0.05% ammonia hydroxide v/v)-ACN]; B %: 42%-72%, 12 min. The desired fractions were collected and lyophilized to give title compound 2-[4-[2-[[(2S,4R)-4-hydroxy-1-methyl-pyrrolidin-2-yl]methoxy]-7-[2-(trifluoromethyl) phenyl]-6, 8-dihydro-5H-pyrido[3,4-d]pyrimidin-4-yl]-1-prop-2-enoyl-piperazin-2-yl]acetonitrile (EXAMPLE 312, 3.70 mg, 6.30 umol, 10% yield, 99.7% purity) as a white solid. LCMS [ESI, M+1]: 586.

$^1$H NMR (400 MHz, chloroform-d) δ=7.69 (d, J=8.0 Hz, 1H), 7.58 (t, J=8.0 Hz, 1H), 7.41 (d, J=8.0 Hz, 1H), 7.30 (t, J=8.0 Hz, 1H), 6.57 (br d, J=10.8 Hz, 1H), 6.39 (dd, J=1.6, 16.4 Hz, 1H), 5.83 (br d, J=10.8 Hz, 1H), 5.06 (br s, 1H), 4.49-4.42 (m, 1H), 4.37 (ddd, J=3.2, 4.8, 10.8 Hz, 1H), 4.25-4.17 (m, 1H), 4.15-4.06 (m, 3H), 3.97 (br d, J=10.8 Hz, 1H), 3.60 (br s, 1H), 3.43 (dd, J=6.0, 10.0 Hz, 1H), 3.33 (br s, 1H), 3.23-3.16 (m, 1H), 3.15-3.06 (m, 2H), 3.04-2.89 (m, 3H), 2.88-2.66 (m, 4H), 2.48 (s, 3H), 2.33 (dd, J=6.0, 10.0 Hz, 1H), 2.13-1.93 (m, 2H).

Example 313

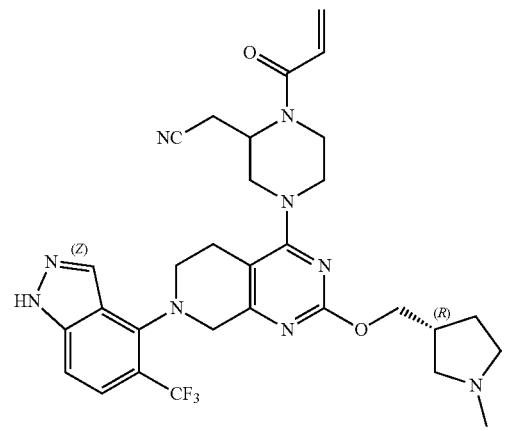

821
2-[4-[2-[[(3R)-1-methylpyrrolidin-3-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile
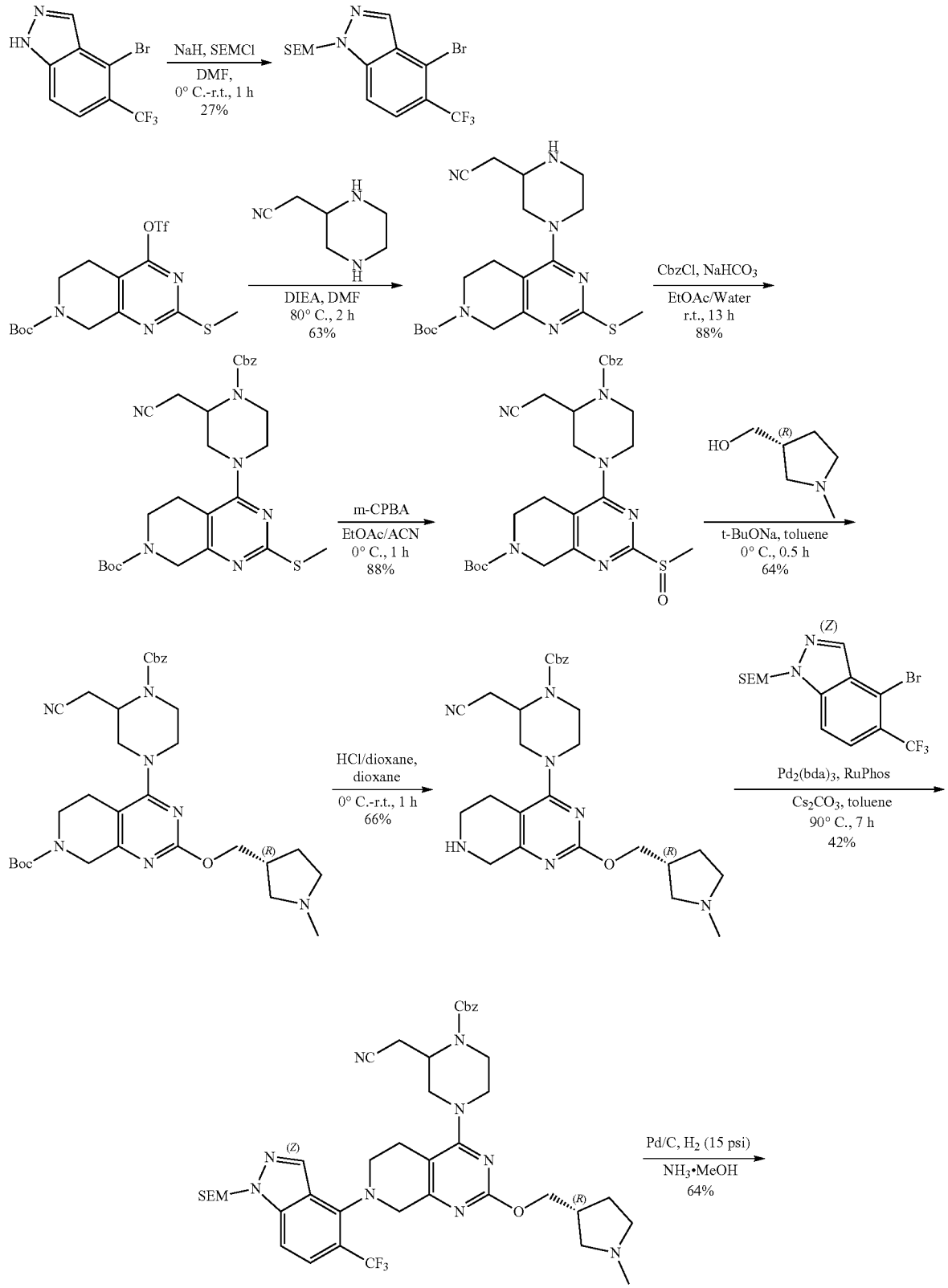

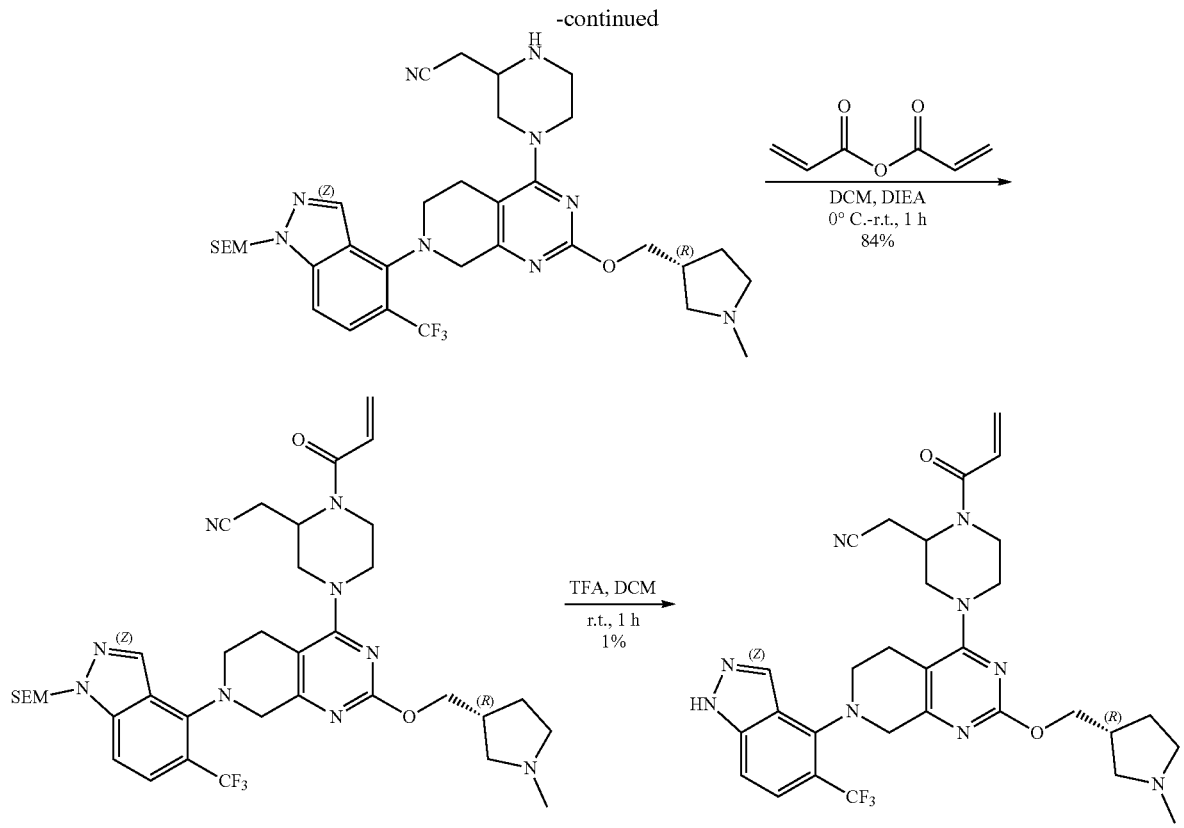

Step A: 2-[[4-bromo-5-(trifluoromethyl)indazol-1-yl]methoxy]ethyl-trimethyl-silane To a solution of 4-bromo-5-(trifluoromethyl)-1H-indazole (1 g, 3.77 mmol, 1 eq) in DMF (45 mL) was added NaH (181 mg, 4.53 mmol, 60.0% purity, 1.2 eq) at 0° C. After being stirred at 0° C. for 1 hour, a solution of SEM-Cl (818 mg, 4.91 mmol, 868 uL, 1.3 eq) in DMF (15 mL) was added dropwise. The mixture was warmed to 20° C. and stirred for 1 hour. The mixture was quenched with saturated aqueous ammonium chloride solution (50 mL), diluted with water (100 mL) and then extracted with ethyl acetate (2×50 mL). The combined organic layers were dried over Na$_2$SO$_4$, filtered and concentrated under vacuum. The residue was purified by silica gel chromatography (PE:EtOAc from 1:0 to 100:1) to give 2-[[4-bromo-5-(trifluoromethyl)indazol-1-yl]methoxy]ethyl-trimethyl-silane (430 mg, 1.03 mmol, 27.4% yield, 95.0% purity) as a colorless oil.

$^1$H NMR (400 MHz, chloroform-d) δ=8.18 (s, 1H), 7.74-7.66 (m, 1H), 7.63-7.56 (m, 1H), 5.76 (s, 2H), 3.59-3.49 (m, 2H), 0.93-0.86 (m, 2H), −0.01-−0.08 (m, 9H).

Step B: tert-butyl 4-[3-(cyanomethyl)piperazin-1-yl]-2-methylsulfanyl-6,8-dihydro-5H-pyrido[3,4-d]pyrimidine-7-carboxylate To the solution of tert-butyl 2-methylsulfanyl-4-(trifluoromethylsulfonyloxy)-6,8-dihydro-5H-pyrido[3,4-d]pyrimidine-7-carboxylate (3.59 g, 8.36 mmol, 1 eq), 2-piperazin-2-ylacetonitrile (Intermediate 62, 1.99 g, 10.0 mmol, 1.2 eq, 2HCl) in DMF (30 mL) was added DIEA (2.16 g, 16.7 mmol, 2.91 mL, 2 eq), then the mixture was heated to 80° C. and stirred at 80° C. for 2 hours. Water (80 mL) was added into the mixture. The resulting mixture was diluted with EtOAc (20 mL) and extracted with EtOAc (5×60 mL). The combined organic layers were washed with brine (80 mL), dried over anhydrous Na$_2$SO$_4$, filtered and concentrated under vacuum. The residue was purified by reversed phase flash column (ACN/Water (0.1% FA)=40%) to give tert-butyl 4-[3-(cyanomethyl)piperazin-1-yl]-2-methylsulfanyl-6,8-dihydro-5H-pyrido[3,4-d]pyrimidine-7-carboxylate (2.37 g, 5.27 mmol, 63.1% yield, 90.0% purity) as a brown solid. LCMS [ESI, M+1]: 405.

Step C: tert-butyl 4-[4-benzyloxycarbonyl-3-(cyanomethyl)piperazin-1-yl]-2-methylsulfanyl-6,8-dihydro-5H-pyrido[3,4-d]pyrimidine-7-carboxylate To the solution of tert-butyl 4-[3-(cyanomethyl)piperazin-1-yl]-2-methylsulfanyl-6,8-dihydro-5H-pyrido[3,4-d]pyrimidine-7-carboxylate (2.37 g, 5.86 mmol, 1 eq), NaHCO$_3$ (1.48 g, 17.6 mmol, 684 uL, 3 eq) in EtOAc (30 mL) and Water (15 mL) was added CbzCl (2.00 g, 11.7 mmol, 1.67 mL, 2 eq) dropwise, then the mixture was stirred at 25° C. for 13 hours. The mixture was diluted with EtOAc (15 mL) and extracted with EtOAc (2×15 mL). The combined organic layers were washed with brine (15 mL). The combined organic layers were dried over anhydrous Na$_2$SO$_4$, filtered and concentrated under vacuum. The residue was purified by silica gel chromatography (PE:EtOAc=20:1~0:1) to give tert-butyl 4-[4-benzyloxycarbonyl-3-(cyanomethyl)piperazin-1-yl]-2-methylsulfanyl-6,8-dihydro-5H-pyrido[3,4-d]pyrimidine-7-carboxylate (2.91 g, 5.13 mmol, 87.6% yield, 95.0% purity) as a yellow solid. LCMS [ESI, M+1]: 539.

Step D: tert-butyl 4-[4-benzyloxycarbonyl-3-(cyanomethyl)piperazin-1-yl]-2-methylsulfinyl-6,8-dihydro-5H-pyrido[3,4-d]pyrimidine-7-carboxylate To the solution of tert-butyl 4-[4-benzyloxycarbonyl-3-(cyanomethyl)piperazin-1-yl]-2-methylsulfanyl-6,8-dihydro-5H-pyrido[3,4-d]pyrimidine-7-carboxylate (2.91 g, 5.40 mmol, 1 eq) in EtOAc (60 mL) and ACN (20 mL) was added m-CPBA (1.10 g, 5.40 mmol, 85.0% purity, 1 eq) at 0° C., then the mixture was stirred at 0° C. for 1 hour. The reaction mixture was quenched by saturated $Na_2S_2O_3$ (30 mL) at 0° C., then extracted with EtOAc (50 mL). The organic layer was dried over anhydrous $Na_2SO_4$, filtered and concentrated under vacuum. The residue was purified by reversed phase flash column (ACN/Water (0.1% $NH_3.H_2O$) =62%) to give tert-butyl 4-[4-benzyloxycarbonyl-3-(cyanomethyl)piperazin-1-yl]-2-methylsulfinyl-6,8-dihydro-5H-pyrido[3,4-d]pyrimidine-7-carboxylate (2.65 g, 4.73 mmol, 87.6% yield, 99.0% purity) as a white solid. LCMS [ESI, M+1]: 555.

Step E: tert-butyl 4-[4-benzyloxycarbonyl-3-(cyanomethyl)piperazin-1-yl]-2-[[(3R)-1-methylpyrrolidin-3-yl]methoxy]-6,8-dihydro-5H-pyrido[3,4-d]pyrimidine-7-carboxylate To the solution of tert-butyl 4-[4-benzyloxycarbonyl-3-(cyanomethyl)piperazin-1-yl]-2-methylsulfinyl-6,8-dihydro-5H-pyrido[3,4-d]pyrimidine-7-carboxylate (2.2 g, 3.97 mmol, 1 eq), [(3R)-1-methylpyrrolidin-3-yl]methanol (914 mg, 7.93 mmol, 2 eq) in toluene (44 mL) was added t-BuONa (572 mg, 5.95 mmol, 1.5 eq) at 0° C., then the mixture was stirred at 0° C. for 0.5 hour. Water (15 mL) was added into the mixture. The resulting mixture was diluted with EtOAc (10 mL) and extracted with EtOAc (2×20 mL). The combined organic layers were washed with brine (20 mL). The combined organic layers were dried over anhydrous $Na_2SO_4$, filtered and concentrated under vacuum. The residue was purified by reversed phase flash column (ACN/Water (0.1% FA)=45%) to give tert-butyl 4-[4-benzyloxycarbonyl-3-(cyanomethyl)piperazin-1-yl]-2-[[(3R)-1-methylpyrrolidin-3-yl]methoxy]-6,8-dihydro-5H-pyrido[3,4-d]pyrimidine-7-carboxylate (1.64 g, 2.52 mmol, 63.5% yield, 93.0% purity) as a white solid. LCMS [ESI, M+1]: 605.
$^1$H NMR (400 MHz, chloroform-d) δ=7.44-7.31 (m, 5H), 5.19 (s, 2H), 4.71-4.54 (m, 2H), 4.35 (br d, J=19.2 Hz, 1H), 4.24-4.16 (m, 2H), 4.11-3.92 (m, 2H), 3.79 (br d, J=12.4 Hz, 2H), 3.28 (br d, J=12.8 Hz, 3H), 2.98 (dt, J=3.2, 12.4 Hz, 1H), 2.87-2.44 (m, 8H), 2.36 (s, 3H), 2.12-2.06 (m, 1H), 1.87 (br s, 2H), 1.49 (s, 9H).

Step F: benzyl 2-(cyanomethyl)-4-[2-[[(3R)-1-methylpyrrolidin-3-yl]methoxy]-5,6,7,8-tetrahydropyrido[3,4-d]pyrimidin-4-yl]piperazine-1-carboxylate To the solution of tert-butyl 4-[4-benzyloxycarbonyl-3-(cyanomethyl)piperazin-1-yl]-2-[[(3R)-1-methylpyrrolidin-3-yl]methoxy]-6,8-dihydro-5H-pyrido[3,4-d]pyrimidine-7-carboxylate (1.64 g, 2.71 mmol, 1 eq) in dioxane (30 mL) was added HCl/dioxane (4 M, 30 mL, 44.32 eq) at 0° C., then the mixture was stirred at 25° C. for 1 hour. The reaction mixture was concentrated under vacuum. The residue was purified by reversed phase flash column (ACN/Water (0.1% FA)=35.5%) to give benzyl 2-(cyanomethyl)-4-[2-[[(3R)-1-methylpyrrolidin-3-yl]methoxy]-5,6,7,8-tetrahydropyrido[3,4-d]pyrimidin-4-yl]piperazine-1-carboxylate (0.95 g, 1.78 mmol, 65.9% yield, 95.0% purity) as a white solid. LCMS [ESI, M+1]: 506.
$^1$H NMR (400 MHz, chloroform-d) δ=7.43-7.32 (m, 5H), 5.19 (s, 2H), 4.66 (br s, 1H), 4.25-4.07 (m, 3H), 4.01-3.91 (m, 3H), 3.83 (br d, J=13.6 Hz, 1H), 3.38-3.18 (m, 2H), 3.16-3.07 (m, 1H), 3.03-2.92 (m, 2H), 2.81 (br s, 1H), 2.75-2.65 (m, 3H), 2.60 (br d, J=5.6 Hz, 3H), 2.55-2.45 (m, 2H), 2.36 (s, 3H), 2.14-1.97 (m, 1H), 1.68-1.54 (m, 2H).

Step G: benzyl 2-(cyanomethyl)-4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate To the solution of benzyl 2-(cyanomethyl)-4-[2-[[(3R)-1-methylpyrrolidin-3-yl]methoxy]-5,6,7,8-tetrahydropyrido[3,4-d]pyrimidin-4-yl]piperazine-1-carboxylate (510 mg, 1.01 mmol, 1 eq), 2-[[4-bromo-5-(trifluoromethyl)indazol-1-yl]methoxy]ethyl-trimethyl-silane (399 mg, 1.01 mmol, 1 eq), RuPhos (188 mg, 403 umol, 0.4 eq) and $Cs_2CO_3$ (986 mg, 3.03 mmol, 3 eq) in toluene (10 mL) was added $Pd_2(dba)_3$ (185 mg, 202 umol, 0.2 eq) under $N_2$, the suspension was degassed under vacuum and purged with $N_2$ several times. The mixture was warmed to 90° C. and stirred at 90° C. for 14 hours. The reaction mixture filtered, the filter cake was washed with EtOAc (2×15 mL). The filtrate was concentrated under vacuum. The residue was purified by reversed phase flash column (ACN/Water (0.1% FA)=55%) to give benzyl 2-(cyanomethyl)-4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (365 mg, 423 umol, 41.9% yield, 95.0% purity) as a brown solid. LCMS [ESI, M+1]: 820.
$^1$H NMR (400 MHz, chloroform-d) δ=8.15 (s, 1H), 7.70 (d, J=8.8 Hz, 1H), 7.52 (d, J=8.8 Hz, 1H), 7.42-7.33 (m, 5H), 5.76 (s, 2H), 5.24-5.16 (m, 2H), 4.70 (br s, 1H), 4.42-4.27 (m, 2H), 4.21 (br d, J=6.8 Hz, 2H), 4.06 (br d, J=10.8 Hz, 1H), 3.90 (br d, J=12.4 Hz, 1H), 3.61-3.54 (m, 2H), 3.50-3.38 (m, 2H), 3.31 (br d, J=11.6 Hz, 2H), 3.10-2.99 (m, 1H), 2.86 (br s, 2H), 2.81-2.66 (m, 4H), 2.65-2.57 (m, 1H), 2.56-2.44 (m, 2H), 2.36 (s, 3H), 2.12-2.06 (m, 1H), 2.04-1.96 (m, 1H), 1.69-1.56 (m, 1H), 0.95-0.87 (m, 2H), −0.03-−0.10 (m, 9H).

Step H: 2-[4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazin-2-yl]acetonitrile $NH_3$ was bubbled into MeOH (6 mL) for 5 minutes. To the solution was added benzyl 2-(cyanomethyl)-4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazine-1-carboxylate (310 mg, 378 umol, 1 eq), Pd/C (150 mg, 10.0% purity) under $N_2$. The suspension was degassed under vacuum and purged with $H_2$ several times. The mixture was stirred under $H_2$ (15 psi) at 28° C. for 1 hour. The mixture filtered, the filtrate was concentrated under vacuum. The residue was used to next step directly without further purification. Compound 2-[4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]

piperazin-2-yl]acetonitrile (165 mg, 240 umol, 63.6% yield, 100% purity) was obtained as a yellow solid. LCMS [ESI, M+1]: 686.

Step I: 2-[4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile To the solution of 2-[4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]piperazin-2-yl]acetonitrile (190 mg, 277 umol, 1 eq), DIEA (107 mg, 831 umol, 145 uL, 3 eq) in DCM (4 mL) was added prop-2-enoyl prop-2-enoate (41.9 mg, 332 umol, 1.2 eq) at 0° C., then the mixture was stirred at 28° C. for 1 hour. The reaction mixture was quenched by Water (1 mL) and extracted with DCM (3×4 mL). The combined organic layers were dried over anhydrous $Na_2SO_4$, filtered and concentrated under vacuum. The residue was used to next step directly without further purification. Compound 2-[4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile (230 mg, 233 umol, 84.2% yield, 75.0% purity) was obtained as a yellow solid. LCMS [ESI, M+1]: 740.

Step J: 2-[4-[2-[[(3R)-1-methylpyrrolidin-3-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile To the solution of 2-[4-[2-[[(3R)-1-methylpyrrolidin-3-yl]methoxy]-7-[5-(trifluoromethyl)-1-(2-trimethylsilylethoxymethyl)indazol-4-yl]-6,8-dihydro-5H-pyrido[3,4-d]pyrimidin-4-yl]-1-prop-2-enoyl-piperazin-2-yl]acetonitrile (220 mg, 297 umol, 1 eq) in DCM (1 mL) was added TFA (1.70 g, 14.9 mmol, 1.10 mL, 50 eq), the mixture was stirred at 28° C. for 1 hour. The reaction mixture was basified by saturated $NaHCO_3$ (12 mL) to PH=8. The resulting mixture was extracted with DCM:MeOH (10:1) (3×15 mL). The combined organic layers were dried over anhydrous $Na_2SO_4$, filtered and concentrated under vacuum. The residue was purified by silica gel chromatography (EtOAc: MeOH=100:1~10:1), then the residue was purified by prep-HPLC (column: Gemini 150*25 5 u; mobile phase: [water (0.05% ammonia hydroxide v/v)-ACN]; B %: 44%-74%,12 min) to give 2-[4-[2-[[(3R)-1-methylpyrrolidin-3-yl]methoxy]-7-[5-(trifluoromethyl)-1H-indazol-4-yl]-6,8-dihydro-5H-pyrido[3,4-d]pyrimidin-4-yl]-1-prop-2-enoyl-piperazin-2-yl]acetonitrile (EXAMPLE 313, 1.23 mg, 2.01 umol, 6.74e−1% yield, 99.4% purity) as a white solid. LCMS [ESI, M+1]: 610.

$^1$H NMR (400 MHz, methanol-$d_4$) δ=8.38 (s, 1H), 7.70 (d, J=8.8 Hz, 1H), 7.57 (d, J=8.8 Hz, 1H), 6.84 (br s, 1H), 6.31 (br d, J=16.8 Hz, 1H), 5.86 (br d, J=10.8 Hz, 1H), 5.13 (br s, 1H), 4.62 (br s, 1H), 4.37-4.20 (m, 5H), 4.14 (br d, J=11.6 Hz, 1H), 3.64 (br s, 1H), 3.50 (br d, J=4.8 Hz, 2H), 3.41-3.34 (m, 1H), 3.29-3.16 (m, 2H), 3.03 (br d, J=6.4 Hz, 1H), 2.94 (br s, 2H), 2.88-2.80 (m, 1H), 2.80-2.72 (m, 1H), 2.69 (br t, J=6.8 Hz, 2H), 2.58-2.51 (m, 1H), 2.43 (s, 3H), 2.17-2.06 (m, 1H), 1.75-1.64 (m, 1H).

Example 314

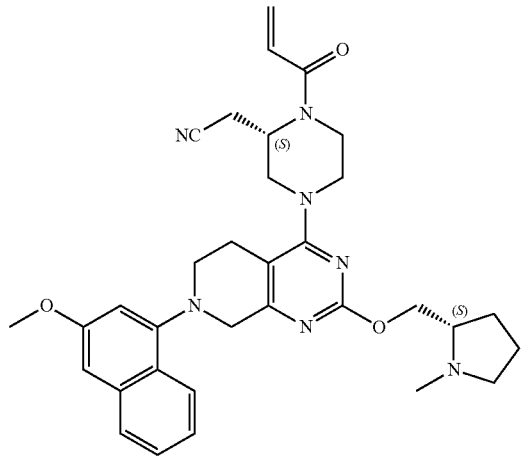

2-[(2S)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

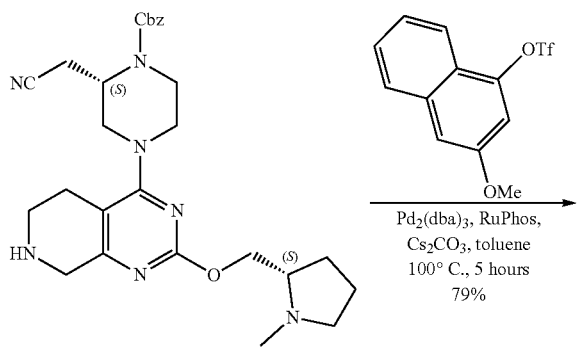

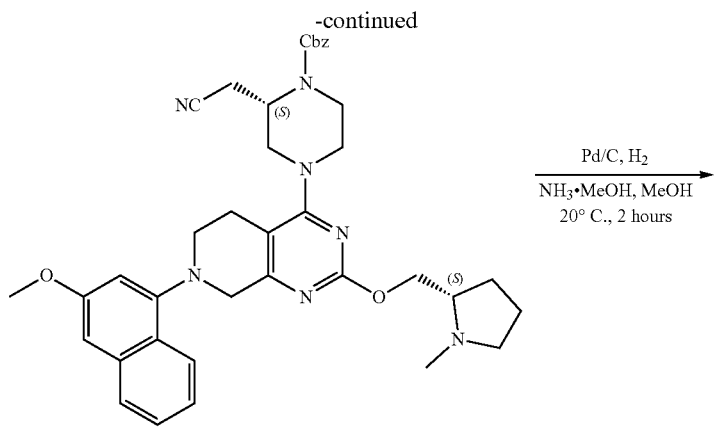

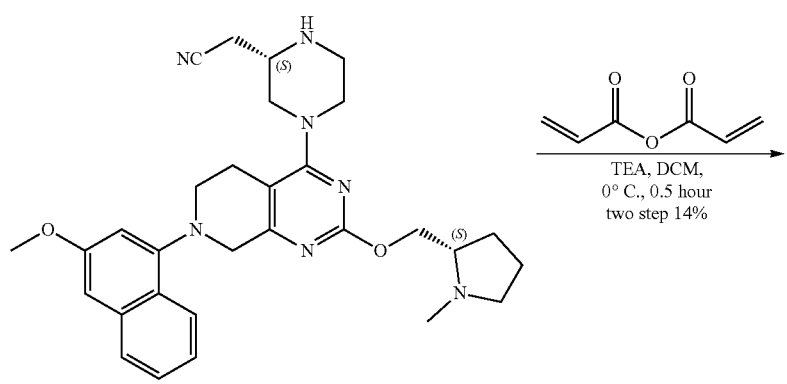

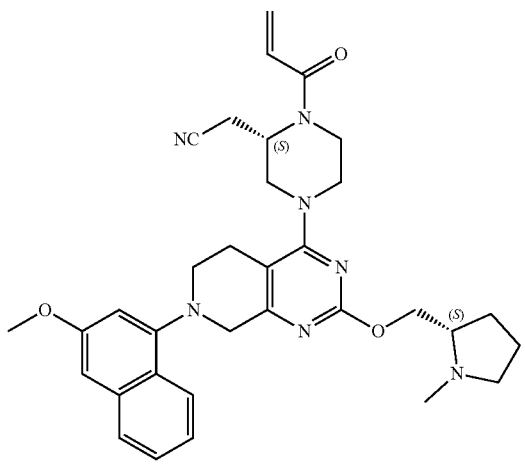

Step A: benzyl (2S)-2-(cyanomethyl)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a solution of benzyl(2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 900 mg, 1.78 mmol, 1.0 eq), $Pd_2(dba)_3$ (245 mg, 267 umol, 0.15 eq), RuPhos (166 mg, 356 umol, 0.20 eq) and $Cs_2CO_3$ (1.16 g, 3.56 mmol, 2.0 eq) in toluene (10.0 mL) was added (3-methoxy-1-naphthyl) trifluoromethanesulfonate (Intermediate 30, 1.09 g, 3.56 mmol, 2.0 eq). The mixture was stirred at 100° C. for 5 hours. After completion, the mixture was added water (20.0 mL) and extracted with EA (20 mL×3). The organic layer was dried over $Na_2SO_4$, filtered and concentrated. The obtained product was purified by column chromatography (SiO$_2$, PE:EA=10:1-EA:MeOH=10:1) to give benzyl (2S)-2-(cyanomethyl)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (1.0 g, 1.42 mmol, 79% yield, 93.8% purity) as yellow solid.

$^1$H NMR (400 MHz, Chloroform-d) δ 8.08 (d, J=8.4 Hz, 1H), 7.74 (d, J=8.0 Hz, 1H), 7.48-7.32 (m, 7H), 6.91 (d, J=2.0 Hz, 1H), 6.80 (d, J=2.0 Hz, 1H), 5.27-5.15 (m, 2H), 4.70 (br s, 1H), 4.51-4.33 (m, 1H), 4.30-4.03 (m, 5H), 3.94-3.87 (m, 3H), 3.53-3.40 (m, 1H), 3.32 (br d, J=12.4 Hz, 3H), 3.16 (br t, J=7.6 Hz, 1H), 3.06 (dt, J=3.6, 12.6 Hz, 1H), 2.97-2.72 (m, 6H), 2.52 (s, 3H), 2.39-2.28 (m, 1H), 2.15-2.06 (m, 1H), 1.93-1.74 (m, 3H).

Step B: 2-[(2S)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile NH$_3$ was bubbled into MeOH (50.0 mL) at −60° C. for 30 minutes. Then benzyl (2S)-2-(cyanomethyl)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (1.0 g, 1.51 mmol, 1.0 eq) and Pd/C (1.0 g, 10% purity) was added to the above liquid under N$_2$ atmosphere. The suspension was degassed and purged with H$_2$ for 3 times. The mixture was stirred under H$_2$ (15 Psi) at 20° C. for 2 hours. After completion, the mixture was filtered with Celite and concentrated under vacuum. The product 2-[(2S)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (600 mg, crude) as yellow oil. LCMS [ESI, M+1]: 528.

Step C: 2-[(2S)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (600 mg, 1.14 mmol, 1.0 eq) and DIEA (882 mg, 6.82 mmol, 1.19 mL, 6.0 eq) in DCM (6.0 mL) was added prop-2-enoyl prop-2-enoate (143 mg, 1.14 mmol, 1.0 eq). The mixture was stirred at 0° C. for 0.5 hour. After completion, the mixture was quenched with MeOH (100 mg) and concentrated under vacuum. The obtained product was purified by prep-HPLC (column: Phenomenex Gemini 150*25 mm*10 um; mobile phase: [water (0.05% ammonia hydroxide v/v)-ACN]; B %: 52%-80%, 12 min). to give the title compound 2-[(2S)-4-[7-(3-methoxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 314, 90.5 mg, 155 umol, 14.0% yield, 99.5% purity) as white solid. LCMS [ESI, M+1]: 582.

$^1$H NMR (400 MHz, Chloroform-d) δ 8.09 (d, J=8.4 Hz, 1H), 7.75 (d, J=8.4 Hz, 1H), 7.45 (t, J=7.2 Hz, 1H), 7.36 (t, J=7.6 Hz, 1H), 6.91 (d, J=2.0 Hz, 1H), 6.81 (d, J=2.4 Hz, 1H), 6.68-6.53 (m, 1H), 6.41 (dd, J=1.6, 16.8 Hz, 1H), 5.84 (br d, J=10.4 Hz, 1H), 5.19-4.50 (m, 1H), 4.40 (dd, J=4.8, 10.4 Hz, 1H), 4.31-4.08 (m, 4H), 4.07-3.85 (m, 5H), 3.79-3.41 (m, 2H), 3.41-3.22 (m, 2H), 3.20-3.04 (m, 2H), 3.02-2.75 (m, 4H), 2.72-2.65 (m, 1H), 2.49 (s, 3H), 2.33-2.24 (m, 1H), 2.11-2.01 (m, 1H), 1.90-1.71 (m, 3H).

Example 315

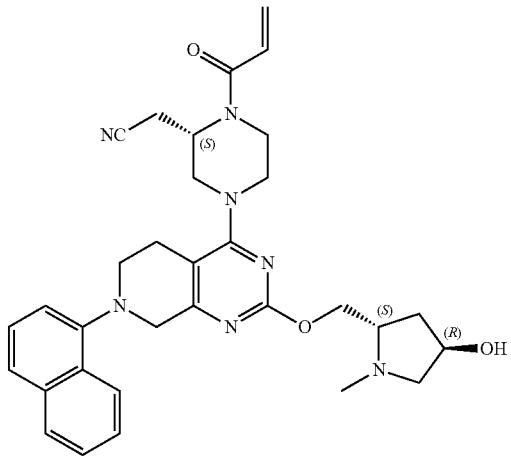

2-[(2S)-4-[2-[[(2S,4R)-4-hydroxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile

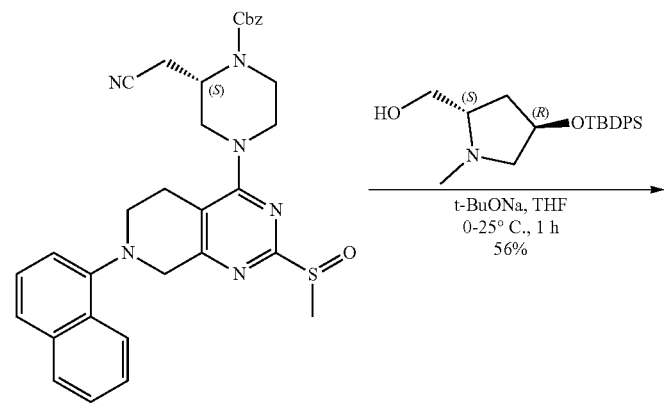

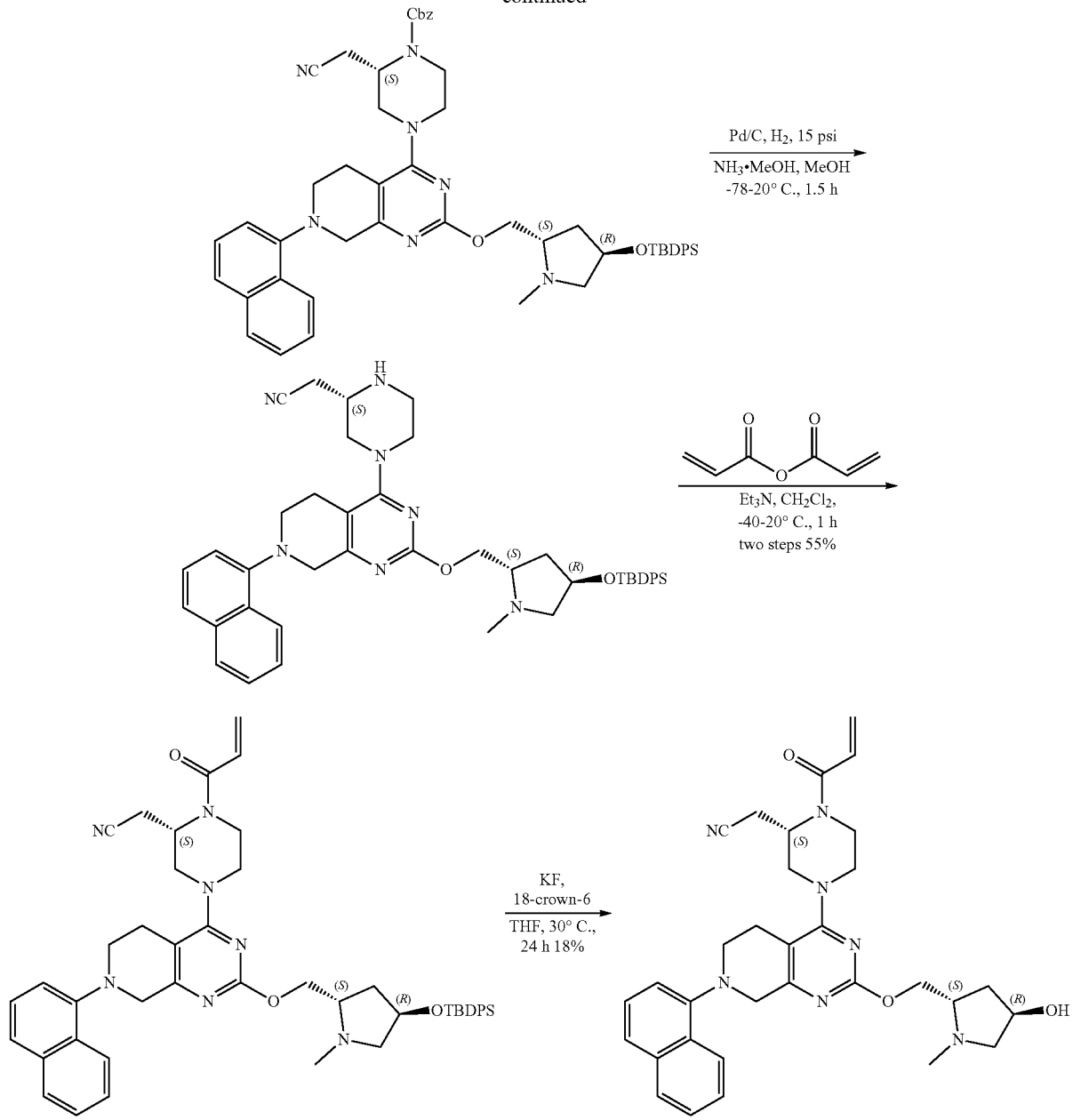

Step A: benzyl (2S)-4-[2-[[(2S,4R)-4-[tert-butyl (diphenyl)silyl]oxy-1-methyl-pyrrolidin-2-yl] methoxy]-7-(1-naphthyl)-6,8-dihydro-5H-pyrido[3,4-d]pyrimidin-4-yl]-2-(cyanomethyl)piperazine-1-carboxylate To a solution of benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 0.90 g, 1.55 mmol, 1.00 eq) and [(2S,4R)-4-[tert-butyl (diphenyl)silyl]oxy-1-methyl-pyrrolidin-2-yl]methanol (687 mg, 1.86 mmol, 1.20 eq) in THF (20.0 mL) was added t-BuONa (298 mg, 3.10 mmol, 2.00 eq) at 0° C. After stirred at 25° C. for 1 hour, the mixture was diluted with ethyl acetate (50.0 mL), washed with water (30.0 mL) and brine (1×30.0 mL), dried over Na$_2$SO$_4$, filtered and concentrated under vacuum. The residue was purified by column chromatography (Al$_2$O$_3$, methanol/ethyl acetate=1/10) to give benzyl (2S)-4-[2-[[(2S,4R)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-2-(cyanomethyl) piperazine-1-carboxylate (0.90 g, 873 umol, 56% yield) as a yellow solid. LCMS [ESI, M/2+1]: 443.

$^1$H NMR (400 MHz, chloroform-d) δ=8.24-8.18 (m, 1H), 7.90-7.83 (m, 1H), 7.71-7.57 (m, 5H), 7.53-7.47 (m, 2H), 7.45-7.35 (m, 12H), 7.14 (br d, J=7.6 Hz, 1H), 5.21 (s, 2H), 4.68 (br s, 1H), 4.43-4.36 (m, 1H), 4.33 (br dd, J=4.8, 10.8 Hz, 1H), 4.26 (br s, 2H), 4.16-4.03 (m, 3H), 3.93 (br d, J=12.8 Hz, 1H), 3.47 (br s, 1H), 3.30 (br d, J=10.4 Hz, 3H), 3.17 (br dd, J=6.0, 10.0 Hz, 1H), 3.11-2.96 (m, 3H), 2.84 (br s, 2H), 2.78-2.70 (m, 1H), 2.48-2.37 (m, 4H), 2.11 (ddd, J=4.8, 8.4, 12.8 Hz, 1H), 1.96-1.82 (m, 1H), 1.06 (s, 9H).

Step B: 2-[(2S)-4-[2-[[(2S,4R)-4-[tert-butyl(diphenyl)silyl]oxy-1-methyl-pyrrolidin-2-yl]methoxyl]-7-(1-naphthyl)-6,8-dihydro-5H-pyrido[3,4-d]pyrimidin-4-yl]piperazin-2-yl]acetonitrile $NH_3$ was bubbled in methanol (50 mL) at −60° C. for 0.5 h. To the mixture was added benzyl (2S)-4-[2-[[(2S,4R)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (0.90 g, 1.02 mmol, 1.00 eq) and Pd/C (0.10 g, 10.0% purity). After stirred at 20° C. for 1 hour under $H_2$ at 15 psi, the mixture was filtered and concentrated under vacuum to give 2-[(2S)-4-[2-[[(2S,4R)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (763 mg, crude) as a yellow oil and used into next step without further purification. LCMS [ESI, M+1]: 752.

Step C: 2-[(2S)-4-[2-[[(2S,4R)-4-[tert-butyl(diphenyl)silyl]oxy-1-methyl-pyrrolidin-2-yl]methoxyl]-7-(1-naphthyl)-6,8-dihydro-5H-pyrido[3,4-d]pyrimidin-4-yl]-1-prop-2-enoyl-piperazin-2-yl]acetonitrile To a solution of 2-[(2S)-4-[2-[[(2S,4R)-4-[tert-butyl(diphenyl) silyl]oxy-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (0.76 g, crude) and $Et_3N$ (511 mg, 5.05 mmol, 703 uL) in dichloromethane (5.00 mL) was added prop-2-enoyl prop-2-enoate (127 mg, 1.01 mmol) at −40° C. After stirred at 20° C. for 1 hour, the mixture was quenched with saturated sodium bicarbonate (0.20 mL) and concentrated under vacuum. The residue was purified by column chromatography ($Al_2O_3$, methanol/ethyl acetate=1/10) to give 2-[(2S)-4-[2-[[(2S,4R)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (0.50 g, 552 umol, two steps 55% yield) as a yellow oil. LCMS [ESI, M+1]: 806.

$^1$H NMR (400 MHz, chloroform-d) δ=8.25-8.17 (m, 1H), 7.90-7.82 (m, 1H), 7.68-7.58 (m, 5H), 7.50 (td, J=2.4, 5.2 Hz, 2H), 7.46-7.35 (m, 7H), 7.14 (d, J=7.6 Hz, 1H), 6.67-6.51 (m, 1H), 6.46-6.31 (m, 1H), 5.83 (br d, J=10.8 Hz, 1H), 5.08 (br s, 1H), 4.43-4.31 (m, 2H), 4.27 (br s, 2H), 4.16-4.00 (m, 4H), 3.67-3.55 (m, 1H), 3.46 (br s, 1H), 3.31 (br dd, J=8.4, 14.4 Hz, 2H), 3.17 (br dd, J=6.0, 9.6 Hz, 1H), 3.11-2.73 (m, 6H), 2.47 (s, 3H), 2.42 (br dd, J=6.0, 9.6 Hz, 1H), 2.11 (tt, J=4.0, 8.4 Hz, 1H), 1.96-1.84 (m, 1H), 1.06 (s, 9H).

Step D: 2-[(2S)-4-[2-[[(2S,4R)-4-hydroxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile A mixture of 2-[(2S)-4-[2-[[(2S,4R)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (0.40 g, 496 umol, 1.00 eq), KF (57.7 mg, 992 umol, 23.3 uL, 2.00 eq) and 18-crown-6 (262 mg, 992 umol, 2.00 eq) in THF (10.0 mL) was stirred at 30° C. for 24 hours. The mixture was concentrated under vacuum. The residue was purified by reversed phase flash [water (TFA, 0.10%)/acetonitrile]. The desired fractions were adjust pH >7 by saturated sodium bicarbonate (2.00 mL) and extracted with ethyl acetate (3×30.0 mL). The organic layers were dried over $Na_2SO_4$, filtered and concentrated under vacuum. The residue was purified prep-HPLC (column: Phenomenex Gemini 150*25 mm*10 um; mobile phase: [water (0.05% ammonia hydroxide v/v)-ACN]; B %: 37%-67%,12 min). The desired fractions were concentrated and lyophilized to give title compound 2-[(2S)-4-[2-[[(2S,4R)-4-hydroxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (EXAMPLE 315, 51.5 mg, 90.7 umol, 18% yield, 96.3% purity) as a white solid. LCMS [ESI, M+1]: 568.

SFC: "AS-3S_3_5_40_3ML Column: Chiralpak AS-3 100×4.6 mm I.D., 3 um Mobile phase: methanol (0.05%, DEA) in $CO_2$ from 5% to 40% Flow rate: 3 mL/min Wavelength: 220 nm".

$^1$H NMR (400 MHz, chloroform-d) δ=8.26-8.17 (m, 1H), 7.91-7.83 (m, 1H), 7.61 (d, J=8.0 Hz, 1H), 7.55-7.48 (m, 2H), 7.44 (t, J=8.0 Hz, 1H), 7.15 (d, J=7.2 Hz, 1H), 6.59 (br s, 1H), 6.47-6.36 (m, 1H), 5.84 (br d, J=10.8 Hz, 1H), 5.11 (br s, 1H), 4.52-4.43 (m, 1H), 4.39 (dd, J=4.8, 10.8 Hz, 1H), 4.34-4.20 (m, 3H), 4.15 (br d, J=14.0 Hz, 1H), 4.02 (br d, J=12.0 Hz, 2H), 3.61 (br s, 1H), 3.53-3.41 (m, 2H), 3.34 (br s, 2H), 3.12 (br s, 1H), 3.05-2.89 (m, 3H), 2.88-2.66 (m, 2H), 2.50 (s, 3H), 2.34 (dd, J=5.6, 10.0 Hz, 1H), 2.16-1.94 (m, 2H).

Example 316

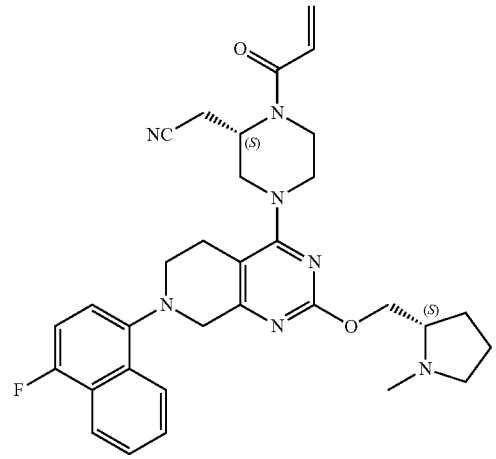

837

2-((S)-1-acryloyl-4-(7-(4-fluoronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

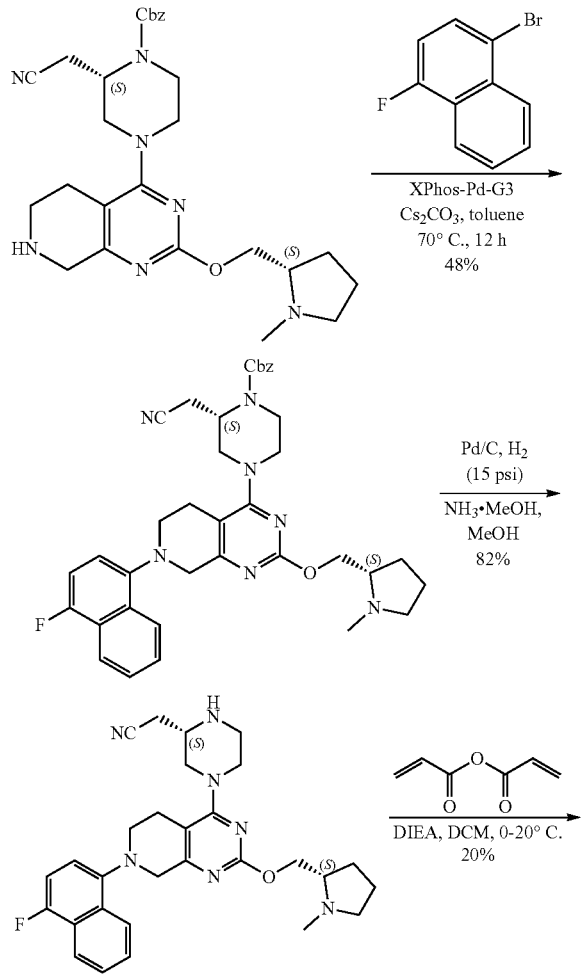

838

Step A: benzyl (2S)-2-(cyanomethyl)-4-[7-(4-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a solution of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 1.0 g, 1.98 mmol, 1.0 eq) and 1-bromo-4-fluoro-naphthalene (2.23 g, 9.89 mmol, 5.0 eq) in toluene (20.0 mL) was added $Cs_2CO_3$ (1.93 g, 5.93 mmol, 3.0 eq), XPhos-Pd-G3 (335 mg, 396 umol, 0.2 eq), the reaction mixture was stirred at 70° C. for 24 hours under $N_2$. After completion, the reaction was added water (20.0 mL), extracted with EA (2×20.0 mL), the organic layer was dried over $Na_2SO_4$, filtered and concentrated. The residue was purified by column chromatography ($SiO_2$, Petroleum ether/Ethyl acetate=3/1 to Ethyl acetate:Methanol=20:1) to give benzyl (2S)-2-(cyanomethyl)-4-[7-(4-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (680 mg, 957 umol, 48% yield, 91.4% purity) as white solid. LCMS [ESI, M+1]: 650.

Step B: 2-[(2S)-4-[7-(4-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(4-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (650 mg, 1.0 mmol, 1.0 eq) in MeOH (15 mL) was added $NH_3$.MeOH (1.0 mmol, 15.0 mL, 1.0 eq) and Pd/C (500 mg, 10% purity), the suspension was degassed under vacuum and purged with $H_2$ several times. The mixture was stirred under $H_2$ (15 Psi) at 20° C. for 0.5 hour. After completion, the reaction was filtered through a Celite, and the filtrate was concentrated to give 2-[(2S)-4-[7-(4-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (460 mg, 824 umol, 82% yield, 92.4% purity) as white solid which was used for the next step without further purification. LCMS [ESI, M+1]: 516.

Step C: 2-[(2S)-4-[7-(4-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2S)-4-[7-(4-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (460 mg, 892 umol, 1.0 eq) in DCM (10 mL) was added DIEA (461 mg, 3.57 mmol, 622 uL, 4.0 eq) and prop-2-enoyl prop-2-enoate (113 mg, 892 umol, 1.0 eq) at 0° C., the reaction mixture was stirred at 20° C. for 0.5 hour. After completion, the reaction mixture was quenched with MeOH (5.0 mL), and concentrated. The residue was purified by prep-HPLC ((Phenomenex Gemini 150*25 mm*10 um; mobile phase: [water (0.05% ammonia hydroxide v/v)-ACN]; B %: 53%-83%, 12 min), the obtained product was concentrated and then under lyophilization. The title compound 2-[(2S)-4-[7-(4-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl] acetonitrile (EXAMPLE 316, 100 mg, 175 umol, 20% yield, 100% purity) was obtained as white solid. LCMS [ESI, M+1]: 570.
¹H NMR (400 MHz, chloroform-d) δ 8.28-8.22 (m, 1H), 8.17-8.10 (m, 1H), 7.63-7.55 (m, 2H), 7.14-7.05 (m, 2H), 6.70-6.55 (m, 1H), 6.42 (dd, J=1.6, 16.8 Hz, 1H), 5.86 (br d, J=10.4 Hz, 1H), 5.20-4.48 (m, 1H), 4.41 (dd, J=4.8, 10.4 Hz, 1H), 4.33-4.10 (m, 4H), 4.09-3.92 (m, 2H), 3.78-3.20 (m, 4H), 3.19-3.07 (m, 2H), 3.05-2.64 (m, 5H), 2.50 (s, 3H), 2.36-2.25 (m, 1H), 2.13-2.02 (m, 1H), 1.92-1.73 (m, 3H).

Example 317

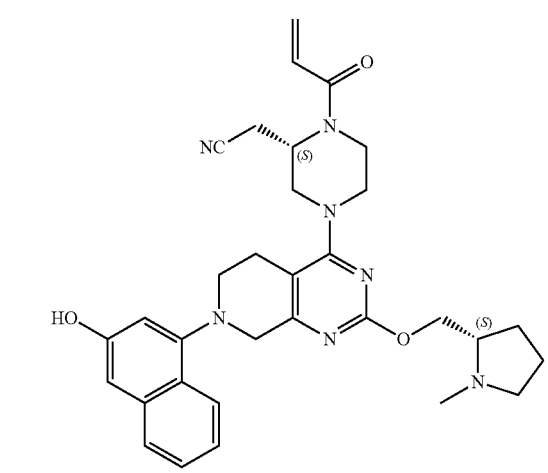

2-((S)-1-acryloyl-4-(7-(3-hydroxynaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile

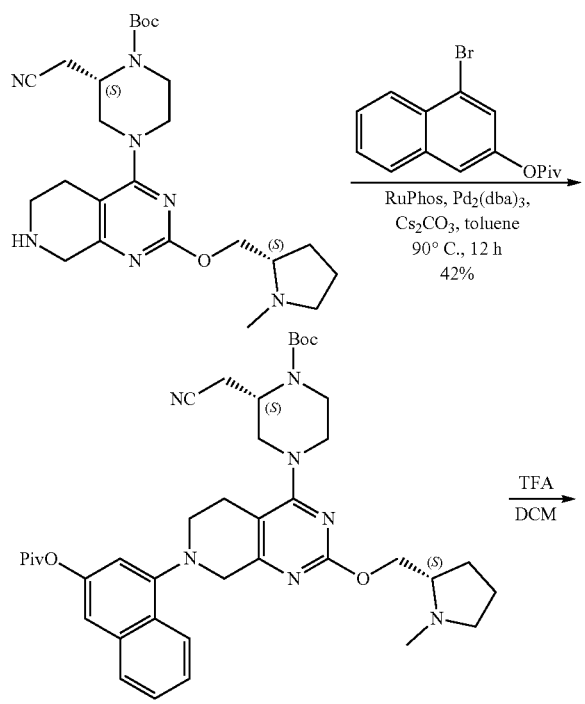

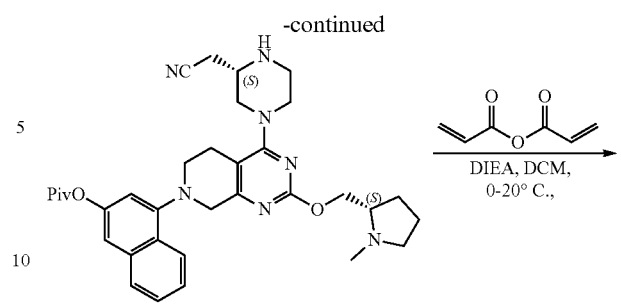

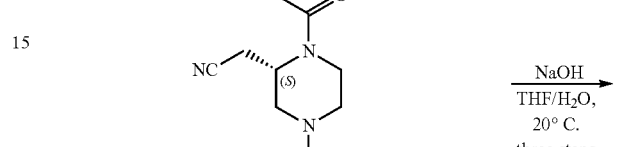

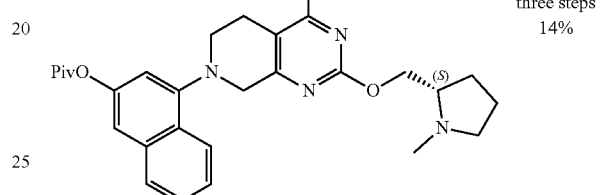

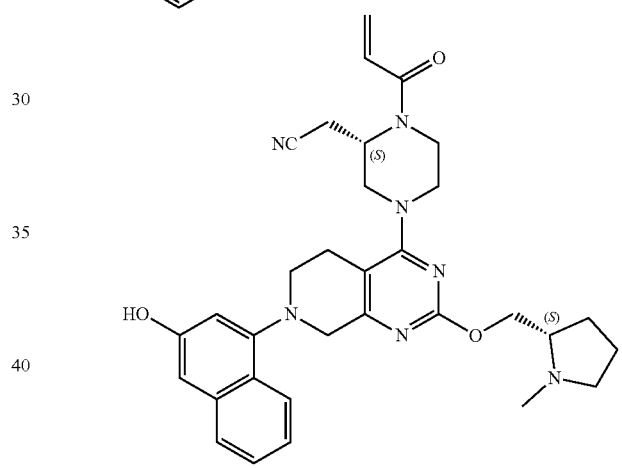

Step A: tert-butyl (2S)-2-(cyanomethyl)-4-[7-[3-(2,2-dimethylpropanoyloxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate To a mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 880 mg, 1.87 mmol, 1.0 eq) and (4-bromo-2-naphthyl)2,2-dimethylpropanoate (Intermediate 54, 745 mg, 2.43 mmol, 1.3 eq) in toluene (20.0 mL) was added Cs₂CO₃ (1.22 g, 3.73 mmol, 2.0 eq), RuPhos (174 mg, 373 umol, 0.2 eq) and Pd₂(dba)₃ (171 mg, 187 umol, 0.1 eq), the mixture was stirred at 90° C. for 12 hours under N₂. After completion, the reaction mixture was added water (30 mL), then extracted with EA (2×20 mL), the combined organic layer was dried over Na₂SO₄, filtered and concentrated. The residue was purified by column chromatography (SiO₂, Petroleum ether/Ethyl acetate=3/1 to Ethyl acetate:Methanol=20/1) to give tert-butyl (2S)-2-(cyanomethyl)-4-[7-[3-

(2,2-dimethylpropanoyloxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate (750 mg, 774 umol, 41% yield, 72.9% purity) as brown solid. LCMS [ESI, M+1]: 698.

Step B: [4-[4-[(3S)-3-(cyanomethyl)piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate To a solution of tert-butyl (2S)-2-(cyanomethyl)-4-[7-[3-(2,2-dimethylpropanoyloxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate (750 mg, 774 umol, 1.0 eq) in DCM (5.0 mL) was added TFA (7.70 g, 67.5 mmol, 5.0 mL, 87.3 eq), the reaction mixture was stirred at 20° C. for 1 hour. After completion, the reaction was concentrated to give [4-[4-[(3S)-3-(cyanomethyl)piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate (550 mg, crude, TFA) as brown oil which was used for the next step without further purification. LCMS [ESI, M+1]: 598.

Step C: [4-[4-[(3S)-3-(cyanomethyl)-4-prop-2-enoyl-piperazin-1-yl]-2-[[(2S)-1-methylpyrrolidin-2-yl]methoxy]-6,8-dihydro-5H-pyrido[3,4-d]pyrimidin-7-yl]-2-naphthyl]2,2-dimethylpropanoate To a mixture of [4-[4-[(3S)-3-(cyanomethyl)piperazin-1-yl]-2-[[(2S)-1-methylpyrrolidin-2-yl]methoxy]-6,8-dihydro-5H-pyrido[3,4-d]pyrimidin-7-yl]-2-naphthyl] 2,2-dimethylpropanoate (550 mg, 773 umol, 1.0 eq, TFA) in DCM (5 mL) was added TEA (469 mg, 4.64 mmol, 645 uL, 6.0 eq) and prop-2-enoyl prop-2-enoate (97.5 mg, 773 umol, 1.0 eq) at 0° C., the reaction mixture was stirred at 20° C. for 0.5 hour. After completion, the reaction mixture was quenched with MeOH (5.0 mL), and concentrated. The residue was purified by column chromatography (SiO₂, Petroleum ether/Ethyl acetate=3/1 to Ethyl acetate/Methanol=10/1) to give [4-[4-[(3S)-3-(cyanomethyl)-4-prop-2-enoyl-piperazin-1-yl]-2-[[(2S)-1-methylpyrrolidin-2-yl]methoxy]-6,8-dihydro-5H-pyrido[3,4-d]pyrimidin-7-yl]-2-naphthyl]2,2-dimethylpropanoate (270 mg, 323 umol, 42% yield, 78.2% purity) as yellow solid. LCMS [ESI, M+1]: 652.

Step D: 2-[(2S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of [4-[4-[(3S)-3-(cyanomethyl)-4-prop-2-enoyl-piperazin-1-yl]-2-[[(2S)-1-methylpyrrolidin-2-yl]methoxy]-6,8-dihydro-5H-pyrido[3,4-d]pyrimidin-7-yl]-2-naphthyl]2,2-dimethylpropanoate (270 mg, 323 umol, 1.0 eq) in THF (2.0 mL) was added a solution of NaOH (38.8 mg, 969 umol, 3.0 eq) in H₂O (2.0 mL), the reaction mixture was stirred at 20° C. for 4 hours. After completion, the reaction mixture was added water (10 mL), then extracted with EA (2×10 mL), the combined organic layer was dried over Na₂SO₄, filtered and concentrated. The residue was purified by prep-HPLC (column: Phenomenex Luna Phenyl-Hexyl 150_30_5 um; mobile phase: [water (0.05% ammonia hydroxide v/v)-ACN]; B %: 35%-62%, 3 min), the obtained product was concentrated, and then under lyophilization. The title compound 2-[(2S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 317, 26.6 mg, 46.3 umol, 14% yield, 98.8% purity) was obtained as pink solid. LCMS [ESI, M+1]: 568.

¹H NMR (400 MHz, chloroform-d) δ 8.01-7.93 (m, 1H), 7.64 (br d, J=8.4 Hz, 1H), 7.41 (br t, J=7.2 Hz, 1H), 7.33-7.29 (m, 2H), 6.88 (s, 1H), 6.66-6.50 (m, 2H), 6.39 (br d, J=16.4 Hz, 1H), 5.84 (br d, J=10.8 Hz, 1H), 5.04-4.89 (br s, 1H), 4.64-4.49 (m, 1H), 4.32-4.21 (m, 1H), 4.11 (br s, 2H), 4.00 (br d, J=14.0 Hz, 1H), 3.94-3.71 (m, 2H), 3.47-3.08 (m, 4H), 2.93-2.61 (m, 10H), 2.47-2.33 (m, 1H), 2.25-2.06 (m, 1H), 2.00-1.89 (m, 3H).

Example 318

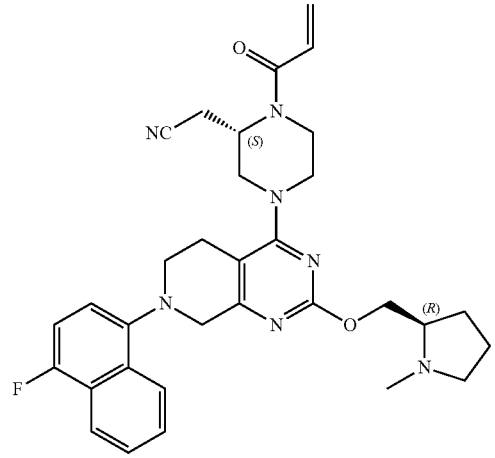

2-[(2S)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

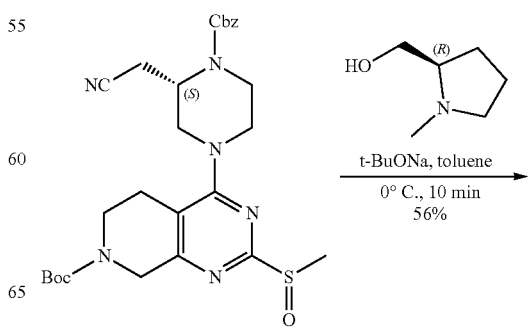

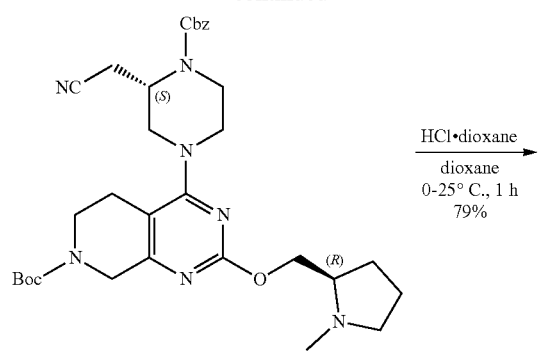

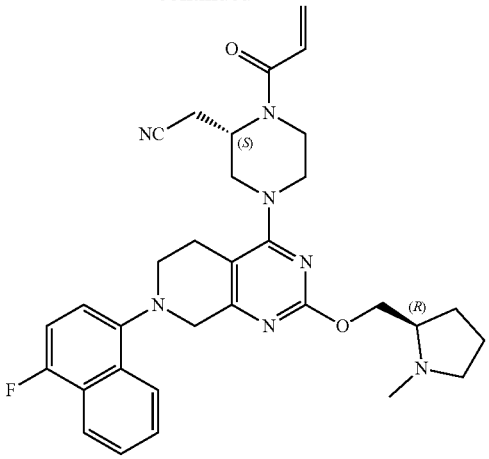

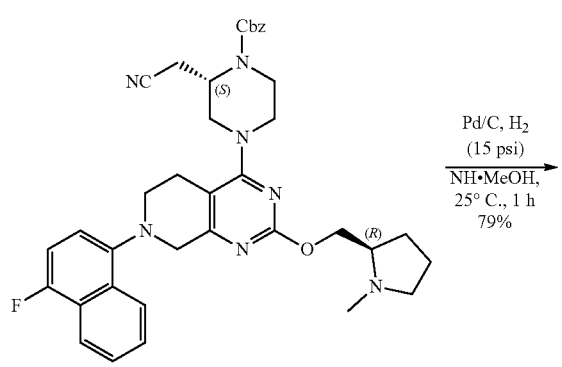

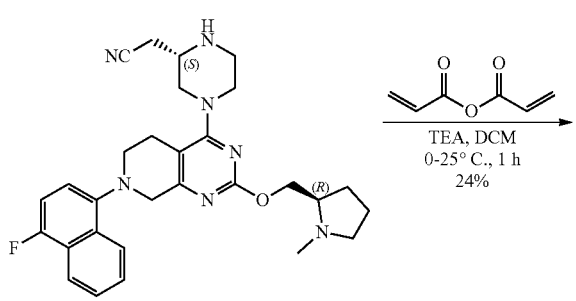

Step A: tert-butyl 4-[(3S)-4-benzyloxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate To a solution of tert-butyl 4-[(3S)-4-benzyloxycarbonyl-3-(cyanomethyl) piperazin-1-yl]-2-methylsulfinyl-6,8-dihydro-5H-pyrido[3,4-d]pyrimidine-7-carboxylate (Intermediate 64, 500 mg, 901 umol, 1.00 eq) and [(2R)-1-methylpyrrolidin-2-yl]methanol (208 mg, 1.80 mmol, 2.00 eq) in toluene (10.0 mL) was added t-BuONa (173 mg, 1.80 mmol, 2.00 eq). The mixture was stirred at 0° C. for 10 minutes. Upon completion, the mixture was diluted with water (5 mL) and extracted with EtOAc (2×30 mL). The organic layers were dried over $Na_2SO_4$ and concentrated under vacuum. The residue was purified by reversed-phase flash [water (0.1% FA)/acetonitrile]. The pH was adjusted to 7 with saturated sodium bicarbonate solution and the mixture was extracted with ethyl acetate (2×30 mL). The organic layers were dried over $Na_2SO_4$ and concentrated under vacuum to give tert-butyl 4-[(3S)-4-benzyloxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (340 mg, 505 umol, 56% yield, 90.0% purity) as a yellow solid.

$^1$H NMR (400 MHz, chloroform-d) δ=7.45-7.32 (m, 5H), 5.28-5.12 (m, 2H), 4.70-4.55 (m, 2H), 4.42-4.29 (m, 2H), 4.15-3.93 (m, 3H), 3.90-3.75 (m, 2H), 3.43-3.16 (m, 3H), 3.09 (br t, J=7.6 Hz, 1H), 2.98 (dt, J=3.6, 12.4 Hz, 1H), 2.89-2.54 (m, 5H), 2.47 (s, 3H), 2.33-2.22 (m, 1H), 2.05-1.96 (m, 1H), 1.90-1.74 (m, 3H), 1.49 (s, 9H).

Step B: benzyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate To a solution of tert-butyl 4-[(3S)-4-benzyloxycarbonyl-3-(cyanomethyl) piperazin-1-yl]-2-[[(2R)-1-methylpyrrolidin-2-yl]methoxy]-6,8-dihydro-5H-pyrido[3,4-d]pyrimidine-7-carboxylate (340 mg, 561 umol, 1.00 eq) in dioxane (4.00 mL) was added HCl/dioxane (4 M, 4.00 mL) at 0° C. The mixture was stirred at 25° C. for 1 hour. Upon completion, the mixture was concentrated under vacuum. The pH was adjusted to 8 with saturated sodium bicarbonate aqueous solution and the mixture was extracted with the mixed solvent (DCM/i-PrOH 2/1, 2×9 mL). The organic layers were dried over $Na_2SO_4$ and concentrated under vacuum to give benzyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (255 mg, 444 umol, 79% yield, 88.0% purity) as a yellow solid which was used directly in the next step without further purification. LCMS [ESI, M+1]: 506.

Step C: benzyl (2S)-2-(cyanomethyl)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]piperazine-1-carboxylate Benzyl (2S)-2-(cyanomethyl)-4-[2-[[(2R)-1-methylpyrrolidin-2-yl] methoxy]-5,6,7,8-tetrahydropyrido[3,4-d]pyrimidin-4-yl]piperazine-1-carboxylate (210 mg, 366 umol, 1.00 eq), 1-bromo-4-fluoro-naphthalene (247 mg, 1.10 mmol, 3.00 eq), RuPhos (68.2 mg, 146 umol, 0.40 eq), t-BuONa (87.8 mg, 914 umol, 2.50 eq) and $Pd_2(dba)_3$ (66.9 mg, 73.1 umol, 0.20 eq) in toluene (2.00 mL) was de-gassed and then heated to 90° C. for 15 hours under $N_2$. Upon completion, the mixture was concentrated under vacuum, diluted with water (3 mL) and extracted with EtOAc (2×10 mL). The organic layers were dried over $Na_2SO_4$ and concentrated under vacuum. The residue was purified by reversed-phase flash [water (0.1% FA)/acetonitrile]. The mixture was neutralized with saturated sodium bicarbonate solution, concentrated under vacuum to remove MeCN and extracted with ethyl acetate (3×30 mL). The organic layers were dried over $Na_2SO_4$ and concentrated under vacuum to give benzyl (2S)-2-(cyanomethyl)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (120 mg, 175 umol, 48% yield, 95.0% purity) as a yellow oil.

$^1$H NMR (400 MHz, chloroform-d) δ=8.23 (dd, J=2.0, 4.4 Hz, 1H), 8.16-8.08 (m, 1H), 7.60-7.52 (m, 2H), 7.44-7.33 (m, 5H), 7.14-7.02 (m, 2H), 5.28-5.16 (m, 2H), 4.69 (br s, 1H), 4.39 (dd, J=4.8, 10.8 Hz, 1H), 4.29-4.14 (m, 4H), 4.07 (br s, 1H), 3.95 (br d, J=12.4 Hz, 1H), 3.54-3.15 (m, 4H), 3.14-3.03 (m, 2H), 3.00-2.61 (m, 5H), 2.48 (s, 3H), 2.35-2.23 (m, 1H), 1.97-2.05 (m, 1H), 1.92-1.83 (m, 3H).

Step D: 2-[(2S)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile $NH_3$ was bubbled into MeOH (5.00 mL) for 3 minutes at −40° C. To the solution was added a solution of benzyl (2S)-2-(cyanomethyl)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (120 mg, 185 umol, 1.00 eq) in MeOH (5.00 mL) and Pd/C (60.0 mg, 10% purity) under $N_2$. The suspension was degassed under vacuum and purged with $H_2$ several times. The reaction was stirred under $H_2$ (15 psi) at 25° C. for 1 hour. Upon completion, the reaction mixture was filtered and the filtrate was concentrated to give 2-[(2S)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (80.0 mg, 147 umol, 79% yield, 94.6% purity) as a yellow solid which was used directly in the next step without further purification. LCMS [ESI, M+1]: 516.

Step E: 2-[(2S)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (80.0 mg, 155 umol, 1.00 eq) and TEA (78.5 mg, 776 umol, 108 uL, 5.00 eq) in DCM (2.00 mL) was added prop-2-enoyl prop-2-enoate (19.6 mg, 155 umol, 1.00 eq) dropwise at 0° C. The mixture was stirred at 25° C. for 1 hour. Upon completion, the reaction was quenched with MeOH (0.5 mL), diluted with water (2 mL) and extracted with EtOAc (2×5 mL). The organic layers were dried over $Na_2SO_4$ and concentrated under vacuum. The residue was purified by prep-TLC (EtOAc/MeOH 7/1) and prep-HPLC (column: Phenomenex Gemini 150*25 mm*10 um; mobile phase: [water (0.05% ammonia hydroxide v/v)-ACN]; B %: 52%-82%, 12 min). The desired fractions were collected and lyophilized to give title compound 2-[(2S)-4-[7-(4-fluoro-1-naphthyl)-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 318, 21.0 mg, 36.7 umol, 24% yield, 99.8% purity) as a white solid. LCMS [ESI, M+1]: 570.

SFC condition: OD-3S_3_40_3ML Column: Chiralcel OD-3 100×4.6 mm I.D., 3 um Mobile phase: 40% methanol (0.05% DEA) in $CO_2$, Flow rate: 3 mL/min, Wavelength: 220 nm.

$^1$H NMR (400 MHz, chloroform-d) δ=8.33-8.22 (m, 1H), 8.16-8.08 (m, 1H), 7.62-7.52 (m, 2H), 7.14-7.02 (m, 2H), 6.59 (br s, 1H), 6.46-6.36 (m, 1H), 5.84 (br d, J=10.4 Hz, 1H), 5.10 (br s, 1H), 4.87-4.33 (m, 2H), 4.30-4.10 (m, 4H), 4.09-3.78 (m, 2H), 3.77-3.23 (m, 2H), 3.22-2.53 (m, 8H), 2.48 (s, 3H), 2.34-2.23 (m, 1H), 2.13-2.00 (m, 1H), 1.92-1.76 (m, 3H).

Example 319

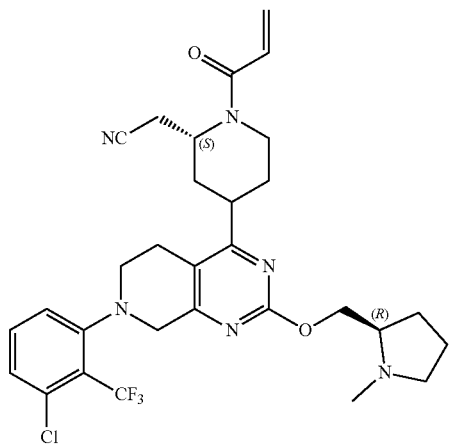

847

2-((S)-1-acryloyl-4-(7-(3-chloro-2-(trifluoromethyl)phenyl)-2-(((R)-1-methylpyrrolidin-2-yl)methoxy)-5,6,7,8-tetrahydropyrido[3,4-d]pyrimidin-4-yl)piperazin-2-yl)acetonitrile

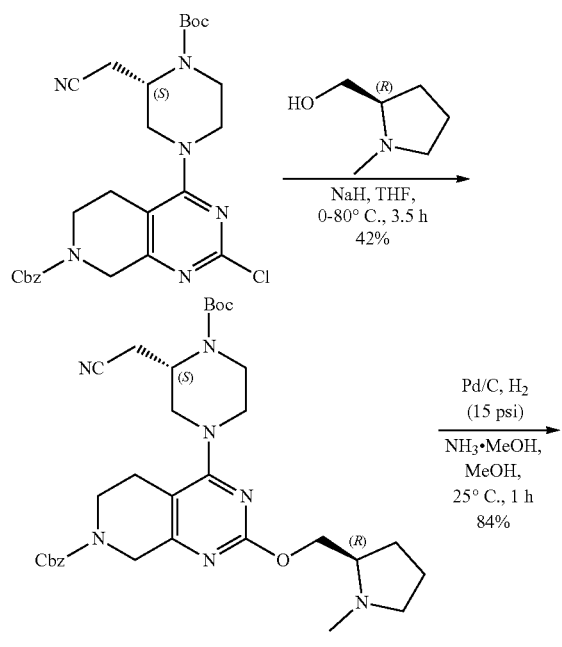

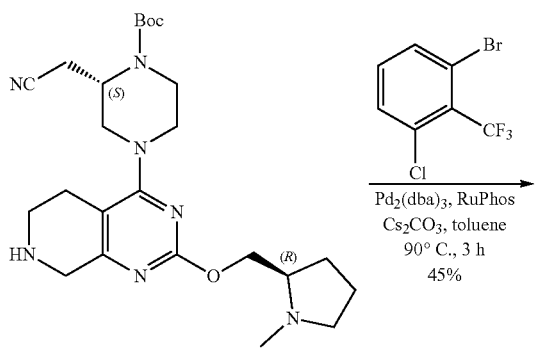

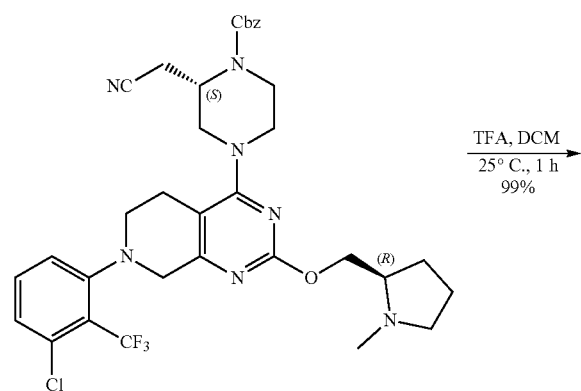

848

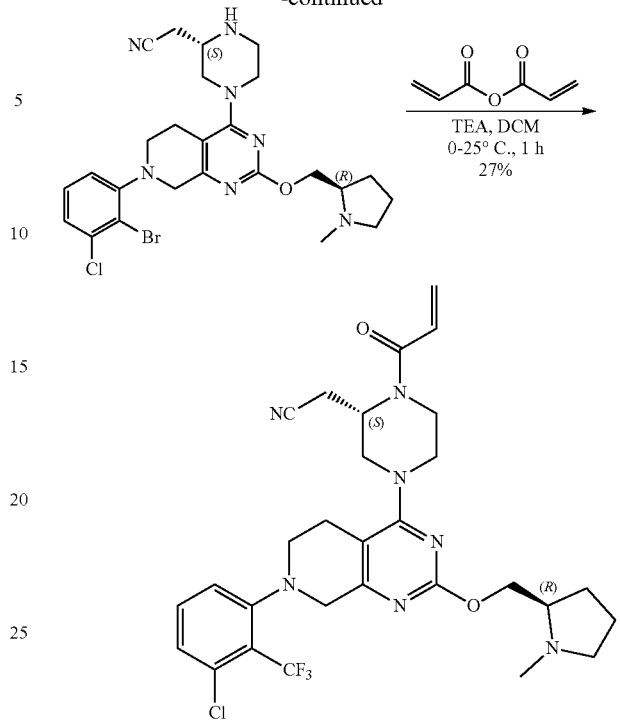

Step A: benzyl 4-[(3S)-4-tert-butoxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate To a solution of [(2R)-1-methylpyrrolidin-2-yl]methanol (1.31 g, 11.4 mmol, 3 eq) in THF (10 mL) was added NaH (304 mg, 7.59 mmol, 60% purity in mineral oil, 2 eq) at 0° C., the mixture was stirred at 0° C. for 0.5 hour. Benzyl 4-[(3S)-4-tert-butoxycarbonyl-3-(cyanomethyl)piperazin-1-yl]-2-chloro-6,8-dihydro-5H-pyrido[3,4-d]pyrimidine-7-carboxylate (2 g, 3.79 mmol, 1 eq) was added into the mixture and the mixture was stirred at 80° C. for 3 hours. The reaction mixture was quenched with ice water (20 mL) and extracted with ethyl acetate (50 mL×3). The combined organic layers were washed with brine (20 mL), dried over $Na_2SO_4$, filtered and concentrated under reduced pressure to give a residue. The residue was purified by reversed phase flash [water (0.1% formic acid)/acetonitrile)]. The desired fractions were collected and adjusted pH=7 with saturated $NaHCO_3$ aqueous solution and extracted with ethyl acetate (30 mL×3). The combined organic layers were washed with brine (20 mL), dried over $Na_2SO_4$, filtered and concentrated under reduced pressure. Benzyl 4-[(3S)-4-tert-butoxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (1 g, 1.60 mmol, 42% yield, 97% purity) was obtained as a yellow oil. LCMS [ESI, M+1]: 606.

$^1$H NMR (400 MHz, chloroform-d) δ=7.43-7.31 (m, 5H), 5.19 (s, 2H), 4.75-4.64 (m, 1H), 4.59 (br s, 1H), 4.44 (d, J=18.8 Hz, 1H), 4.35 (br s, 1H), 4.21-4.11 (m, 1H), 4.07-3.64 (m, 4H), 3.43 (br s, 1H), 3.30-3.15 (m, 2H), 3.10 (br t, J=7.6 Hz, 1H), 3.03-2.91 (m, 1H), 2.83-2.55 (m, 5H), 2.53-2.42 (m, 3H), 2.35-2.22 (m, 1H), 2.11-2.01 (m, 1H), 1.88-1.74 (m, 3H), 1.51 (s, 9H).

Step B: tert-Butyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate NH$_3$ was bubbled in MeOH (100 mL) at −60° C. for 30 minutes. To a solution of benzyl 4-[(3S)-4-tert-butoxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (900 mg, 1.49 mmol, 1 eq) in above mixture was added dry Pd/C (500 mg, 10% purity) under N$_2$. The suspension was degassed under vacuum and purged with H$_2$ several times. The mixture was stirred under H$_2$ (15 psi) at 25° C. for 1 hour. The mixture was concentrated under vacuum. The residue was purified by reversed phase flash [water (0.1% formic acid)/acetonitrile)]. The mixture was adjusted pH=7 with saturated NaHCO$_3$ aqueous solution and extracted with ethyl acetate (20 mL×3). The combined organic layers were washed with brine (20 mL), dried over Na$_2$SO$_4$, filtered and concentrated under reduced pressure to give the product. tert-Butyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (650 mg, 1.24 mmol, 84% yield, 90% purity) was obtained as a yellow solid. LCMS [ESI, M+1]: 472.

Step C: tert-Butyl (2S)-4-[7-[3-chloro-2-(trifluoromethyl)phenyl]-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate A mixture of 1-bromo-3-chloro-2-(trifluoromethyl)benzene (1.32 g, 5.09 mmol, 4 eq), tert-butyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (600 mg, 1.27 mmol, 1 eq), Cs$_2$CO$_3$ (1.04 g, 3.18 mmol, 2.5 eq), Pd$_2$(dba)$_3$ (233 mg, 254 umol, 0.2 eq) and RuPhos (118 mg, 254 umol, 0.2 eq) in toluene (10 mL) was degassed and purged with N$_2$ for 3 times, and then the mixture was stirred at 90° C. for 3 hours under N$_2$ atmosphere. The reaction mixture was diluted with water (20 mL) and extracted with ethyl acetate (50 mL×3). The combined organic layers were washed with brine (30 mL), dried over Na$_2$SO$_4$, filtered and concentrated under reduced pressure to give a residue. The residue was purified by column chromatography (SiO$_2$, Ethyl acetate/MeOH=100/1 to 10:1) and further purified by reversed phase flash [water (0.1% formic acid)/acetonitrile)]. The mixture was adjusted PH=7 with saturated NaHCO$_3$ aqueous solution and extracted with ethyl acetate (20 mL×3). The combined organic layers were washed with brine (20 mL), dried over Na$_2$SO$_4$, filtered and concentrated under reduced pressure to give the product. tert-Butyl (2S)-4-[7-[3-chloro-2-(trifluoromethyl)phenyl]-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate (370 mg, 569 umol, 45% yield, 100% purity) was obtained as a yellow solid. LCMS [ESI, M+1]: 650

$^1$H NMR (400 MHz, chloroform-d) δ=7.40 (t, J=8.0 Hz, 1H), 7.30-7.24 (m, 1H), 7.19 (d, J=8.4 Hz, 1H), 4.61 (br s, 1H), 4.40 (br s, 1H), 4.24-4.14 (m, 1H), 4.13-3.98 (m, 4H), 3.95-3.80 (m, 1H), 3.39-2.95 (m, 6H), 2.93-2.62 (m, 5H), 2.52 (br s, 3H), 2.32 (br s, 1H), 2.14-2.05 (m, 1H), 1.85-1.71 (m, 3H), 1.52 (s, 9H).

Step D: 2-[(2S)-4-[7-[3-chloro-2-(trifluoromethyl)phenyl]-2-[[(2R)-1-methylpyrrolidin-2-yl]methoxy]-6,8-dihydro-5H-pyrido[3,4-d]pyrimidin-4-yl]piperazin-2-yl] acetonitrile To a solution of tert-butyl (2S)-4-[7-[3-chloro-2-(trifluoromethyl) phenyl]-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate (370 mg, 569 umol, 1 eq) in DCM (700 uL) was added TFA (973 mg, 8.54 mmol, 632 uL, 15 eq). The mixture was stirred at 25° C. for 1 hour. The mixture was concentrated under vacuum. Compound 2-[(2S)-4-[7-[3-chloro-2-(trifluoromethyl)phenyl]-2-[[(2R)-1-methylpyrrolidin-2-yl]methoxy]-6,8-dihydro-5H-pyrido[3,4-d]pyrimidin-4-yl]piperazin-2-yl]acetonitrile (377 mg, 567 umol, 99% yield, TFA) was obtained as a yellow oil and used to next step directly without purification. LCMS [ESI, M+1]: 550.

Step E: 2-[(2S)-4-[7-[3-chloro-2-(trifluoromethyl)phenyl]-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-[3-chloro-2-(trifluoromethyl) phenyl]-2-[[(2R)-1-methylpyrrolidin-2-yl]methoxy]-6,8-dihydro-5H-pyrido[3,4-d]pyrimidin-4-yl]piperazin-2-yl]acetonitrile (377 mg, 567 umol, 1 eq, TFA) in DCM (5 mL) was added TEA (574 mg, 5.68 mmol, 790 uL, 10 eq) at 0° C. After addition, the prop-2-enoyl prop-2-enoate (57.3 mg, 454 umol, 0.8 eq) in DCM (1 mL) was added dropwise at 0° C. After stirred at 25° C. for 1 hour, the reaction mixture was quenched with saturated NaHCO$_3$ aqueous solution (1 mL). Then diluted with water (20 mL) and extracted with ethyl acetate (20 mL×3). The combined organic layers were washed with brine (20 mL), dried over Na$_2$SO$_4$, filtered and concentrated under reduced pressure to give a residue. The residue was purified by column chromatography (Al$_2$O$_3$, EA/MeOH=100/1 to 10:1) and further purified by prep-HPLC (column: Phenomenex Gemini 150*25 mm*10 um; mobile phase: [water (0.05% ammonia hydroxide v/v)-ACN]; B %: 50%-80%, 12 min). Title compound 2-[(2S)-4-[7-[3-chloro-2-(trifluoromethyl)phenyl]-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 319, 95 mg, 154 umol, 27% yield, 98% purity) was obtained as a white solid after lyophilisation. LCMS [ESI, M+1]: 604.

SFC condition: "OD-3S_3_5_40_3ML Column: Chiralcel OD-3 100×4.6 mm I.D., 3 um Mobile phase: methanol (0.05% DEA) in CO$_2$ from 5% to 40% Flow rate: 3 mL/min Wavelength: 220 nm".

$^1$H NMR (400 MHz, chloroform-d) δ=7.40 (d, J=8.0 Hz, 1H), 7.29-7.25 (m, 1H), 7.19 (d, J=8.0 Hz, 1H), 6.71-6.51 (m, 1H), 6.45-6.34 (m, 1H), 5.83 (d, J=10.4 Hz, 1H), 5.25-4.52 (m, 1H), 4.38 (dd, J=4.8, 10.4 Hz, 1H), 4.22-4.04 (m, 4H), 3.96 (br d, J=11.6 Hz, 2H), 3.74-3.02 (m, 5H), 2.99-2.61 (m, 6H), 2.48 (s, 3H), 2.35-2.23 (m, 1H), 2.14-1.97 (m, 1H), 1.92-1.79 (m, 3H).

851

Example 320

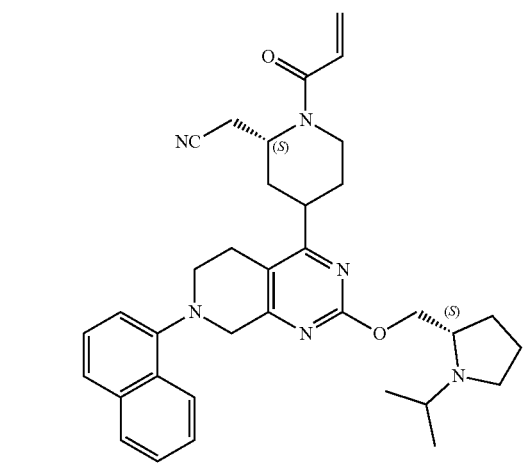

2-[(2S)-4-[2-[[(2S)-1-isopropylpyrrolidin-2-yl]
methoxy]-7-(1-naphthyl)-6,8-dihydro-5H-pyrido[3,
4-d]pyrimidin-4-yl]piperazin-2-yl]acetonitrile

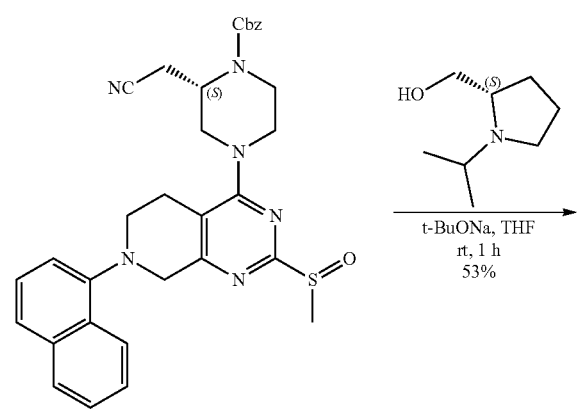

t-BuONa, THF
rt, 1 h
53%

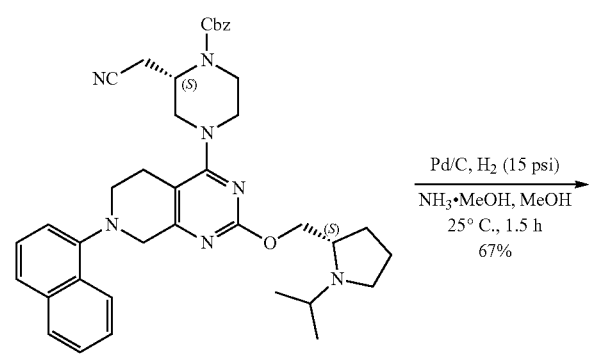

Pd/C, H₂ (15 psi)
―――――――――
NH₃·MeOH, MeOH
25° C., 1.5 h
67%

852

-continued

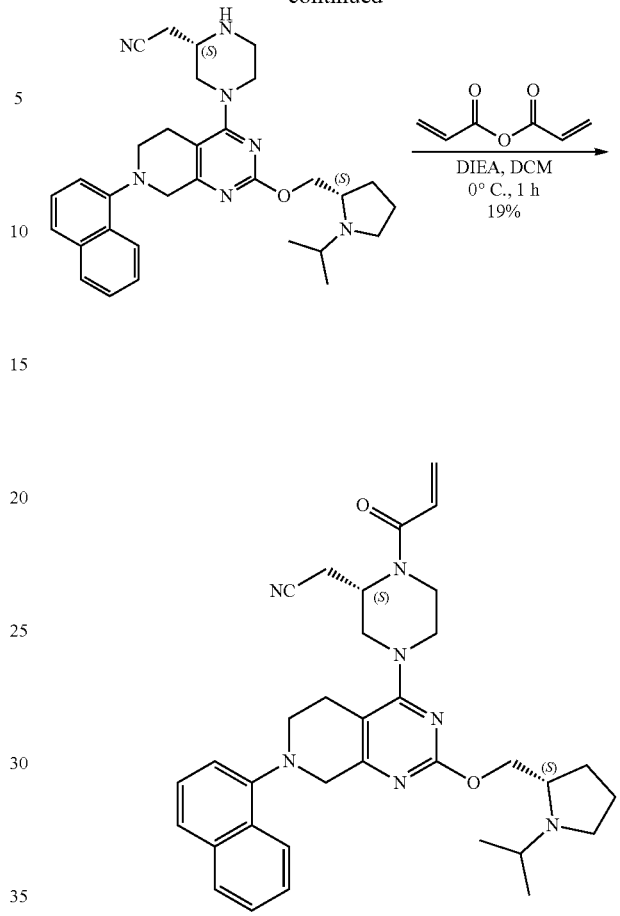

DIEA, DCM
0° C., 1 h
19%

Step A: benzyl(2S)-2-(cyanomethyl)-4-[2-[[(2S)-1-isopropylpyrrolidin-2-yl]methoxy]-7-(1-naphthyl)-6,8-dihydro-5H-pyrido[3,4-d]pyrimidin-4-yl]piperazine-1-carboxylate To a mixture of benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 300 mg, 517 umol, 1.0 eq), [(2S)-1-isopropylpyrrolidin-2-yl]methanol (148 mg, 1.03 mmol, 2.0 eq) in toluene (15.0 mL) was added t-BuONa (99.3 mg, 1.03 mmol, 2.0 eq) in portions at 0° C., the reaction mixture was degassed and purged with N₂ for 3 times, and then the mixture was stirred at 0° C. for 30 min under N₂ atmosphere. After completion, the organic solvent was washed with water (10.0 mL). The aqueous phase was extracted with ethyl acetate (3×20.0 mL). Combined extracts were washed with brine (50.0 mL), dried with Na₂SO₄, the solvent was then removed under vacuum. The residue was purified by reversed phase flash (C18, 0.1% FA in water, 0-60% MeCN). The obtained product was adjusted with saturated NaHCO₃ aqueous to pH ~8 and then concentrated, the aqueous was extracted with ethyl acetate (3×20.0 mL) and the combined organic layer was dried over Na₂SO₄, filtered and concentrated. Compound benzyl(2S)-2-(cyanomethyl)-4-[2-[[(2S)-1-isopropylpyrrolidin-2-yl]methoxy]-7-(1-naphthyl)-6,8-dihydro-5H-pyrido[3,4-d]pyrimidin-4-yl]piperazine-1-carboxylate (180 mg, 272 umol, 53% yield, 99.7% purity) was obtained as a white solid. LCMS [ESI, M+1]: 660.

Step B: 2-[(2S)-4-[2-[[(2S)-1-isopropylpyrrolidin-2-yl]methoxy]-7-(1-naphthyl)-6,8-dihydro-5H-pyrido[3,4-d]pyrimidin-4-yl]piperazin-2-yl]acetonitrile NH₃ was bubbled into methanol (20.0 mL) at −60° C. for 30 minutes. Benzyl (2S)-2-(cyanomethyl)-4-[2-[[(2S)-1-isopropylpyrrolidin-2-yl] methoxy]-7-(1-naphthyl)-6,8-dihydro-5H-pyrido[3,4-d]pyrimidin-4-yl]piperazine-1-carboxylate (130 mg, 197 umol, 1.0 eq) and Pd/C (80.0 mg, 197 umol, 10% purity, 1.0 eq) was added to the above mixture, then the mixture was degassed and purged with H₂ for 3 times, and then the mixture was stirred at 25° C. for 1 hour under H₂ atmosphere. After completion, the crude mixture was filtered through a pad of celite. The cake was washed with methanol (30.0 mL) and the filtrate was dried under high vacuum. Compound 2-[(2S)-4-[2-[[(2S)-1-isopropylpyrrolidin-2-yl]methoxy]-7-(1-naphthyl)-6,8-dihydro-5H-pyrido[3,4-d]pyrimidin-4-yl]piperazin-2-yl]acetonitrile (75.0 mg, 132 umol, 67% yield, 92.6% purity) was obtained as a gray solid. LCMS [ESI, M+1]: 526.

Step C: 2-[(2S)-4-[2-[[(2S)-1-isopropylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a solution of 2-[(2S)-4-[2-[[(2S)-1-isopropylpyrrolidin-2-yl]methoxy]-7-(1-naphthyl)-6,8-dihydro-5H-pyrido[3,4-d]pyrimidin-4-yl]piperazin-2-yl]acetonitrile (100 mg, 190 umol, 1.0 eq) in DCM (5.00 mL) was added DIEA (73.8 mg, 571 umol, 99.4 uL, 3.0 eq) and dropwise added prop-2-enoyl prop-2-enoate (36.0 mg, 285 umol, 1.50 eq) at 0° C. under N₂ atmosphere. The mixture was stirred at 0° C. for 1 hour. After completion, the reaction was quenched with water (10.0 mL). The crude mixture was extracted with ethyl acetate (3×15.0 mL). Combined extracts were washed with brine (30.0 mL), the combined organic layer was dried over Na₂SO₄, filtered and concentrated under reduced pressure to give a residue. The residue was purified by prep-HPLC (column: Phenomenex Luna Phenyl-Hexyl 150_30_5 um; mobile phase: [water (10 mM NH₄HCO₃)-ACN]; B %: 52%-82%, 3 min) and lyophilization. Title compound 2-[(2S)-4-[2-[[(2S)-1-isopropylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (EXAMPLE 320, 21.3 mg, 36.1 umol, 19% yield, 98.1% purity) was obtained as a yellow solid. LCMS [ESI, M+1]: 580.

¹H NMR (400 MHz, chloroform-d) δ 8.24-8.21 (m, 1H), 7.89-7.87 (m, 1H), 7.63 (d, J=8.0 Hz, 1H), 7.54-7.50 (m, 2H), 7.45 (t, J=7.8 Hz, 1H), 7.16 (d, J=7.2 Hz, 1H), 6.65-6.57 (m, 1H), 6.42 (dd, J=1.8, 16.8 Hz, 1H), 5.86 (d, J=10.0 Hz, 1H), 5.16-4.51 (m, 1H), 4.35-4.22 (m, 3H), 4.15-3.95 (m, 4H), 3.68-3.47 (m, 1H), 3.42-2.77 (m, 11H), 2.58-2.52 (m, 1H), 1.90-1.75 (m, 3H), 1.17 (d, J=6.4 Hz, 3H), 1.10 (d, J=6.4 Hz, 3H).

Example 321

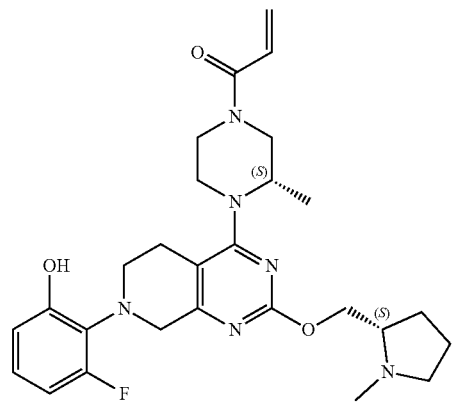

1-[(3S)-4-[7-(2-fluoro-6-hydroxy-phenyl)-2-[[(2S)-1-methylpyrrolidin-2-yl]methoxy]-6,8-dihydro-5H-pyrido[3,4-d]pyrimidin-4-yl]-3-methyl-piperazin-1-yl]prop-2-en-1-one

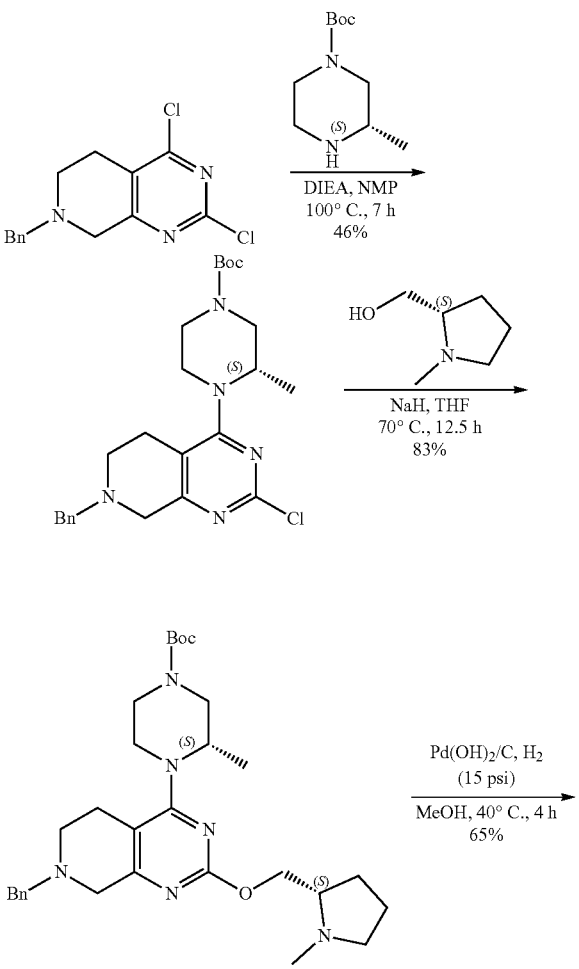

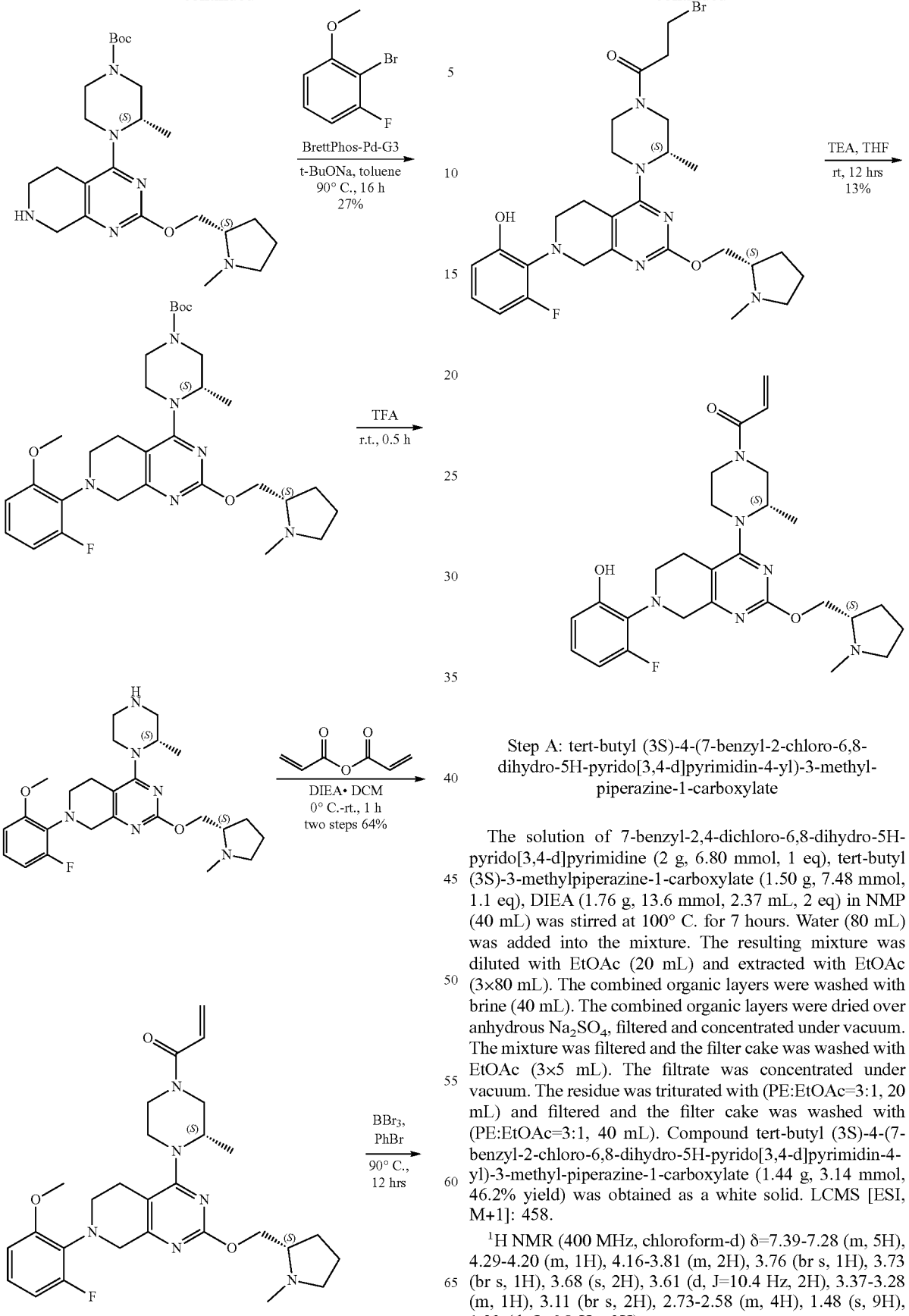

Step A: tert-butyl (3S)-4-(7-benzyl-2-chloro-6,8-dihydro-5H-pyrido[3,4-d]pyrimidin-4-yl)-3-methyl-piperazine-1-carboxylate The solution of 7-benzyl-2,4-dichloro-6,8-dihydro-5H-pyrido[3,4-d]pyrimidine (2 g, 6.80 mmol, 1 eq), tert-butyl (3S)-3-methylpiperazine-1-carboxylate (1.50 g, 7.48 mmol, 1.1 eq), DIEA (1.76 g, 13.6 mmol, 2.37 mL, 2 eq) in NMP (40 mL) was stirred at 100° C. for 7 hours. Water (80 mL) was added into the mixture. The resulting mixture was diluted with EtOAc (20 mL) and extracted with EtOAc (3×80 mL). The combined organic layers were washed with brine (40 mL). The combined organic layers were dried over anhydrous Na$_2$SO$_4$, filtered and concentrated under vacuum. The mixture was filtered and the filter cake was washed with EtOAc (3×5 mL). The filtrate was concentrated under vacuum. The residue was triturated with (PE:EtOAc=3:1, 20 mL) and filtered and the filter cake was washed with (PE:EtOAc=3:1, 40 mL). Compound tert-butyl (3S)-4-(7-benzyl-2-chloro-6,8-dihydro-5H-pyrido[3,4-d]pyrimidin-4-yl)-3-methyl-piperazine-1-carboxylate (1.44 g, 3.14 mmol, 46.2% yield) was obtained as a white solid. LCMS [ESI, M+1]: 458.

$^1$H NMR (400 MHz, chloroform-d) δ=7.39-7.28 (m, 5H), 4.29-4.20 (m, 1H), 4.16-3.81 (m, 2H), 3.76 (br s, 1H), 3.73 (br s, 1H), 3.68 (s, 2H), 3.61 (d, J=10.4 Hz, 2H), 3.37-3.28 (m, 1H), 3.11 (br s, 2H), 2.73-2.58 (m, 4H), 1.48 (s, 9H), 1.23 (d, J=6.8 Hz, 3H).

Step B: tert-butyl (3S)-4-[7-benzyl-2-[[(2S)-1-methylpyrrolidin-2-yl]methoxy]-6,8-dihydro-5H-pyrido[3,4-d]pyrimidin-4-yl]-3-methyl-piperazine-1-carboxylate To the solution of [(2S)-1-methylpyrrolidin-2-yl]methanol (830 mg, 7.21 mmol, 855 uL, 2.5 eq) in THF (25 mL) was added NaH (230 mg, 5.76 mmol, 60% purity, 2 eq) at 0° C. and stirred at 0° C. for 0.5 hour. Then tert-butyl (3S)-4-(7-benzyl-2-chloro-6,8-dihydro-5H-pyrido[3,4-d]pyrimidin-4-yl)-3-methyl-piperazine-1-carboxylate (1.32 g, 2.88 mmol, 1 eq) was added to the mixture. The reaction mixture was heated to 70° C. for 12 hours in a tube under $N_2$. The reaction mixture was quenched by water (10 mL). The resulting mixture was diluted with EtOAc (20 mL) and extracted with EtOAc (3×30 mL). The combined organic layers were washed with brine (30 mL). The combined organic layers were dried over anhydrous $Na_2SO_4$, filtered and concentrated under vacuum. The residue was purified by reversed phase flash column (ACN/Water (0.1% FA)=40%) to give tert-butyl (3S)-4-[7-benzyl-2-[[(2S)-1-methylpyrrolidin-2-yl]methoxy]-6,8-dihydro-5H-pyrido[3,4-d]pyrimidin-4-yl]-3-methyl-piperazine-1-carboxylate (1.35 g, 2.39 mmol, 82.9% yield, 95% purity) as a brown solid. LCMS [ESI, M+1]: 537.

$^1$H NMR (400 MHz, chloroform-d) δ=7.40-7.27 (m, 5H), 4.37 (br dd, J=5.2, 10.8 Hz, 1H), 4.22-4.14 (m, 2H), 4.07-3.73 (m, 2H), 3.71-3.64 (m, 3H), 3.63-3.49 (m, 2H), 3.34-3.24 (m, 1H), 3.21-2.92 (m, 3H), 2.79-2.64 (m, 2H), 2.63-2.56 (m, 3H), 2.51 (s, 3H), 2.33 (br d, J=7.6 Hz, 1H), 2.12-2.05 (m, 1H), 1.92-1.69 (m, 3H), 1.48 (s, 9H), 1.20 (d, J=6.8 Hz, 3H).

Step C: tert-butyl (3S)-3-methyl-4-[2-[[(2S)-1-methylpyrrolidin-2-yl]methoxy]-5,6,7,8-tetrahydropyrido[3,4-d]pyrimidin-4-yl]piperazine-1-carboxylate To the solution of tert-butyl (3S)-4-[7-benzyl-2-[[(2S)-1-methylpyrrolidin-2-yl]methoxy]-6,8-dihydro-5H-pyrido[3,4-d]pyrimidin-4-yl]-3-methyl-piperazine-1-carboxylate (1.43 g, 2.66 mmol, 1 eq) in MeOH (28 mL) was added Pd(OH)$_2$/C (500 mg, 10% purity) under $N_2$. The suspension was degassed under vacuum and purged with $H_2$ several times. The mixture was stirred under $H_2$ (15 psi) at 40° C. for 4 hours. The reaction mixture was filtered, the filter cake was washed with MeOH (3×20 mL). The filtrate was concentrated under vacuum. The residue was purified by reversed phase flash column (ACN/Water (0.1% FA)=40%) to give tert-butyl (3S)-3-methyl-4-[2-[[(2S)-1-methylpyrrolidin-2-yl]methoxy]-5,6,7,8-tetrahydropyrido[3,4-d]pyrimidin-4-yl]piperazine-1-carboxylate (810 mg, 1.72 mmol, 64.7% yield, 95.0% purity) as a yellow solid. LCMS [ESI, M+1]: 447.

Step D: tert-butyl (3S)-4-[7-(2-fluoro-6-methoxy-phenyl)-2-[[(2S)-1-methylpyrrolidin-2-yl]methoxy]-6,8-dihydro-5H-pyrido[3,4-d]pyrimidin-4-yl]-3-methyl-piperazine-1-carboxylate To the solution of tert-butyl (3S)-3-methyl-4-[2-[[(2S)-1-methylpyrrolidin-2-yl]methoxy]-5,6,7,8-tetrahydropyrido[3,4-d]pyrimidin-4-yl]piperazine-1-carboxylate (500 mg, 1.12 mmol, 1 eq), 2-bromo-1-fluoro-3-methoxy-benzene (459 mg, 2.24 mmol, 2 eq) and t-BuONa (323 mg, 3.36 mmol, 3 eq) in toluene (10 mL) was added BrettPhos-Pd-G3 (304 mg, 336 umol, 0.3 eq) under $N_2$. The suspension was degassed under vacuum and purged with $N_2$ several times. The mixture was stirred under $N_2$ at 90° C. for 16 hours. Water (10 mL) was added into the mixture. The resulting mixture was diluted with EtOAc (10 mL) and extracted with EtOAc (3×20 mL). The combined organic layers were dried over anhydrous $Na_2SO_4$, filtered and concentrated under vacuum. The residue was purified by silica gel chromatography (from PE:EtOAc 2:1~0:1 to EtOAc:MeOH 1:0~5:1), then the residue purified by prep-HPLC (column: Phenomenex Synergi Max-RP 250*50 mm*10 um; mobile phase: [water (0.225% FA)-ACN]; B %: 32%-57%,30; 80% min) to give tert-butyl (3S)-4-[7-(2-fluoro-6-methoxy-phenyl)-2-[[(2S)-1-methylpyrrolidin-2-yl]methoxy]-6,8-dihydro-5H-pyrido[3,4-d]pyrimidin-4-yl]-3-methyl-piperazine-1-carboxylate (180 mg, 300 umol, 26.8% yield, 95.0% purity) as a brown oil. LCMS [ESI, M+1]: 571.

$^1$H NMR (400 MHz, chloroform-d) δ=7.02 (dt, J=6.4, 8.4 Hz, 1H), 6.75-6.65 (m, 2H), 4.36 (dd, J=4.8, 10.4 Hz, 1H), 4.27 (s, 2H), 4.24-4.17 (m, 1H), 4.12-4.09 (m, 1H), 3.84 (s, 3H), 3.74-3.65 (m, 1H), 3.38-3.27 (m, 3H), 3.24-2.94 (m, 3H), 2.67 (br d, J=4.4 Hz, 3H), 2.48 (s, 3H), 2.32-2.23 (m, 1H), 2.08 (br d, J=3.2 Hz, 1H), 2.04-1.98 (m, 1H), 1.87-1.69 (m, 4H), 1.49 (s, 9H), 1.25-1.21 (m, 3H).

Step E: 7-(2-fluoro-6-methoxy-phenyl)-4-[(2S)-2-methylpiperazin-1-yl]-2-[[(2S)-1-methylpyrrolidin-2-yl]methoxy]-6,8-dihydro-5H-pyrido[3,4-d]pyrimidine The solution of tert-butyl (3S)-4-[7-(2-fluoro-6-methoxy-phenyl)-2-[[(2S)-1-methylpyrrolidin-2-yl]methoxy]-6,8-dihydro-5H-pyrido[3,4-d]pyrimidin-4-yl]-3-methyl-piperazine-1-carboxylate (210 mg, 368 umol, 1 eq) and TFA (839 mg, 7.36 mmol, 545 uL, 20 eq) was stirred at 25° C. for 0.5 hour. The reaction mixture was concentrated under vacuum. Compound 7-(2-fluoro-6-methoxy-phenyl)-4-[(2S)-2-methylpiperazin-1-yl]-2-[[(2S)-1-methylpyrrolidin-2-yl]methoxy]-6,8-dihydro-5H-pyrido[3,4-d]pyrimidine (260 mg, crude, 2TFA) was obtained as a yellow oil.

Step F: 1-[(3S)-4-[7-(2-fluoro-6-methoxy-phenyl)-2-[[(2S)-1-methylpyrrolidin-2-yl]methoxy]-6,8-dihydro-5H-pyrido[3,4-d]pyrimidin-4-yl]-3-methyl-piperazin-1-yl]prop-2-en-1-one To the solution of 7-(2-fluoro-6-methoxy-phenyl)-4-[(2S)-2-methylpiperazin-1-yl]-2-[[(2S)-1-methylpyrrolidin-2-yl]methoxy]-6,8-dihydro-5H-pyrido[3,4-d]pyrimidine (260 mg, crude, 2TFA), DIEA (481 mg, 3.72 mmol, 648 uL) in DCM (5 mL) was added prop-2-enoyl prop-2-enoate (46.9 mg, 372 umol) at 0° C., then the mixture was stirred at 25° C. for 1 hour. The reaction mixture was quenched by water (1 mL). The resulting mixture was concentrated under vacuum. The residue was purified by reversed phase flash column (ACN/Water (0.1% FA)=33%) to give 1-[(3S)-4-[7-(2-fluoro-6-methoxy-phenyl)-2-[[(2S)-1-methylpyrrolidin-2-yl]methoxy]-6,8-dihydro-5H-pyrido[3,4-d]pyrimidin-4-yl]-3-methyl-piperazin-1-yl]prop-2-en-1-one (130 mg, 235 umol, 63.2% yield, 95.0% purity) as a white solid. LCMS [ESI, M+1]: 525.

Step G: 3-bromo-1-[(3S)-4-[7-(2-fluoro-6-hydroxy-phenyl)-2-[[(2S)-1-methylpyrrolidin-2-yl]methoxy]-6,8-dihydro-5H-pyrido[3,4-d]pyrimidin-4-yl]-3-methyl-piperazin-1-yl]propan-1-one To a solution of 1-[(3S)-4-[7-(2-fluoro-6-methoxy-phenyl)-2-[[(2S)-1-methylpyrrolidin-2-yl]methoxy]-6,8-dihydro-5H-pyrido[3,4-d]pyrimidin-4-yl]-3-methyl-piper-azin-1-yl]prop-2-en-1-one (80 mg, 152 umol, 1 eq) in PhBr (2 mL) was added BBr₃ (764 mg, 3.05 mmol, 294 uL, 20 eq). The reaction mixture was stirred at 90° C. for 12 hours. Upon completion, the reaction mixture was concentrated under vacuum. The residue was quenched with saturated NaHCO₃ (2 mL) and extracted with EtOAc (2×20 mL). 3-bromo-1-[(3S)-4-[7-(2-fluoro-6-hydroxy-phenyl)-2-[[(2S)-1-methylpyrrolidin-2-yl]methoxy]-6,8-dihydro-5H-pyrido[3,4-d]pyrimidin-4-yl]-3-methyl-piperazin-1-yl]pro-pan-1-one (90 mg, crude) was obtained as a brown oil. The crude product was used for next step without further purification.

Step H: 1-[(3S)-4-[7-(2-fluoro-6-hydroxy-phenyl)-2-[[(2S)-1-methylpyrrolidin-2-yl]methoxy]-6,8-di-hydro-5H-pyrido[3,4-d]pyrimidin-4-yl]-3-methyl-piperazin-1-yl]prop-2-en-1-one To a solution of 3-bromo-1-[(3S)-4-[7-(2-fluoro-6-hy-droxy-phenyl)-2-[[(2S)-1-methylpyrrolidin-2-yl]methoxy]-6,8-dihydro-5H-pyrido[3,4-d]pyrimidin-4-yl]-3-methyl-piperazin-1-yl]propan-1-one (90 mg, 152 umol, 1 eq) in THF (2 mL) was added TEA (154 mg, 1.52 mmol, 212 uL, 10 eq). The reaction mixture was stirred at 20° C. for 12 hours. Upon completion, the reaction mixture concentrated under vacuum. The residue was purified by prep-TLC (DCM:MeOH=10:1) then prep-HPLC (column: Phenom-enex Gemini 150*25 mm*10 um; mobile phase: [water (0.05% ammonia hydroxide v/v)-ACN]; B %: 48%-78%,12 min) to give title compound 1-[(3S)-4-[7-(2-fluoro-6-hy-droxy-phenyl)-2-[[(2S)-1-methylpyrrolidin-2-yl]methoxy]-6,8-dihydro-5H-pyrido[3,4-d]pyrimidin-4-yl]-3-methyl-piperazin-1-yl]prop-2-en-1-one (EXAMPLE 321, 10.6 mg, 20.1 umol, 13% yield, 96.9% purity) was obtained as a yellow solid. LCMS [ESI, M+1]: 511.

¹H NMR (400 MHz, Methanol-d₄) δ=7.17-6.97 (m, 1H), 6.93-6.76 (m, 1H), 6.71 (d, J=8.4 Hz, 1H), 6.61 (dd, J=8.8, 11.2 Hz, 1H), 6.29 (br dd, J=4.8, 16.4 Hz, 1H), 5.82 (br d, J=10.8 Hz, 1H), 4.58-4.27 (m, 4H), 4.20-4.04 (m, 3H), 4.03-3.87 (m, 1H), 3.68-3.39 (m, 2H), 3.30 (br s, 2H), 3.25-3.05 (m, 2H), 2.82 (br s, 2H), 2.75 (td, J=6.8, 13.6 Hz, 1H), 2.51 (s, 3H), 2.36 (q, J=9.2 Hz, 1H), 2.13-2.08 (m, 1H), 1.89-1.78 (m, 2H), 1.77-1.67 (m, 1H), 1.28 (br d, J=5.2 Hz, 3H).

Example 322

2-(1-acryloyl-4-(2-(((S)-1-ethylpyrrolidin-2-yl)methoxy)-7-(4-fluoronaphthalen-1-yl)-5,6,7,8-tetra-hydropyrido[3,4-d]pyrimidin-4-yl)piperazin-2-yl)acetonitrile

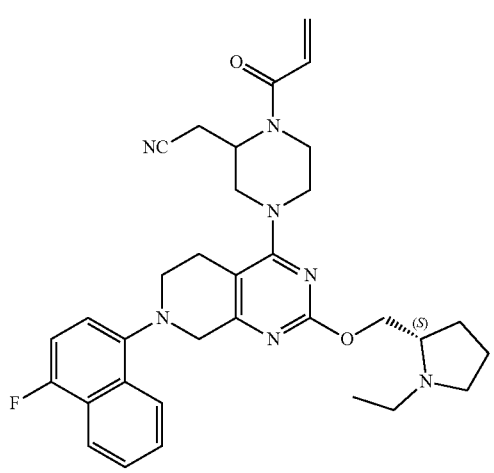

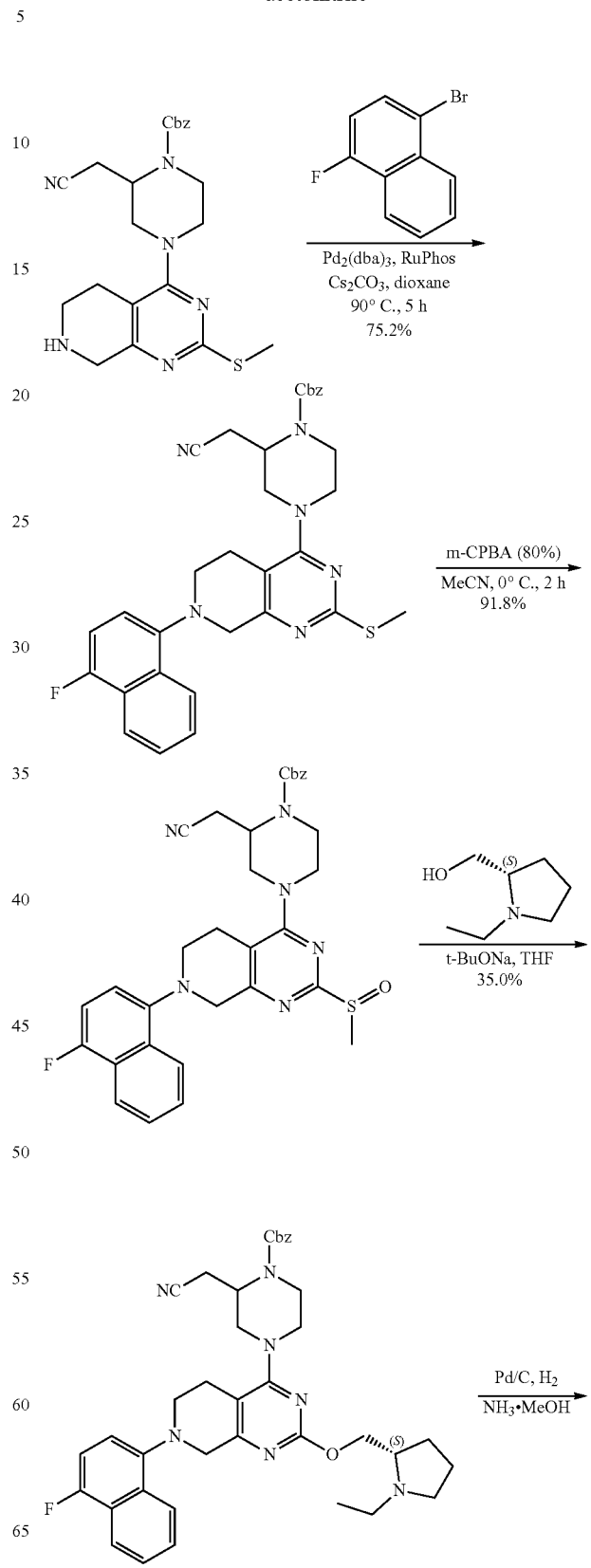

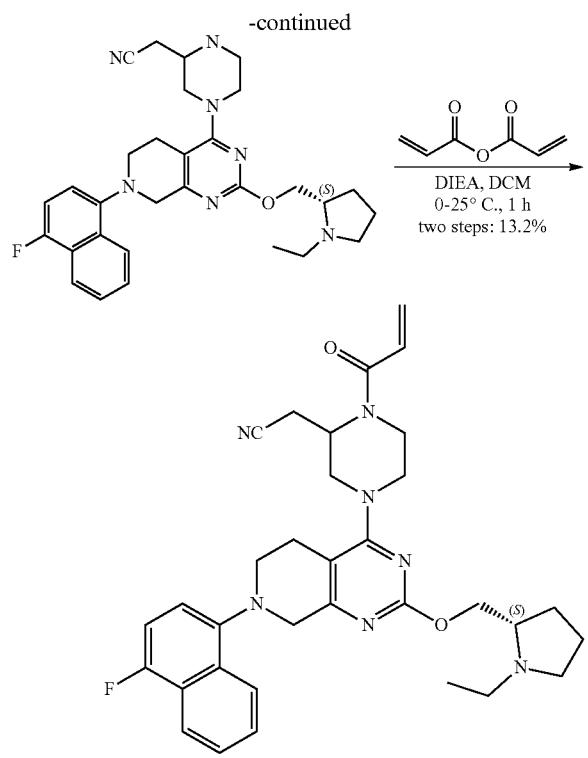

Step A: benzyl 2-(cyanomethyl)-4-[7-(4-fluoro-1-naphthyl)-2-methylsulfanyl-6,8-dihydro-5H-pyrido[3,4-d]pyrimidin-4-yl]piperazine-1-carboxylate benzyl 2-(cyanomethyl)-4-(2-methylsulfanyl-5,6,7,8-tetrahydropyrido[3,4-d]pyrimidin-4-yl)piperazine-1-carboxylate (2.00 g, 4.56 mmol, 1.00 eq.), 1-bromo-4-fluoro-naphthalene (1.54 g, 6.84 mmol, 1.50 eq.), Pd$_2$(dba)$_3$ (418 mg, 456 umol, 0.100 eq.), RuPhos (426 mg, 912 umol, 0.20 eq.) and cesium carbonate (4.46 g, 13.7 mmol, 3.00 eq.) in toluene (40.0 mL) was de-gassed and then heated to 110° C. for 3 hours under N$_2$ atmosphere. The reaction mixture was quenched by addition water (20.0 mL) at 20° C., then diluted with ethyl acetate (30 mL) and extracted with ethyl acetate (20.0 mL×3). The combined organic layers were washed with brine (50.0 mL), dried over anhydrous sodium sulfate, filtered and concentrated under reduced pressure to give a residue. The residue was purified by column chromatography (SiO$_2$, Petroleum ether/Ethyl acetate=1/1 to 0/1) to give benzyl 2-(cyanomethyl)-4-[7-(4-fluoro-1-naphthyl)-2-methylsulfanyl-6,8-dihydro-5H-pyrido[3,4-d]pyrimidin-4-yl]piperazine-1-carboxylate (2.00 g, 3.43 mmol, 75.2% yield) as a yellow solid.

$^1$H NMR (400 MHz, CDCl$_3$) δ=8.24 (dt, J=1.6, 4.8 Hz, 1H), 8.16-8.08 (m, 1H), 7.64-7.53 (m, 2H), 7.47-7.34 (m, 5H), 7.15-7.03 (m, 2H), 5.22 (s, 2H), 4.72 (br s, 1H), 4.29-4.17 (m, 2H), 4.12-4.04 (m, 1H), 3.95 (br d, J=12.0 Hz, 1H), 3.51-3.19 (m, 3H), 3.14-2.68 (m, 5H), 2.54 (s, 3H).

Step B: benzyl 2-(cyanomethyl)-4-[7-(4-fluoro-1-naphthyl)-2-methylsulfinyl-6,8-dihydro-5H-pyrido[3,4-d]pyrimidin-4-yl]piperazine-1-carboxylate To a mixture of benzyl 2-(cyanomethyl)-4-[7-(4-fluoro-1-naphthyl)-2-methylsulfanyl-6,8-dihydro-5H-pyrido[3,4-d]pyrimidin-4-yl]piperazine-1-carboxylate (1.06 g, 1.82 mmol, 1.00 eq.) in ethyl acetate (33.0 mL) was added m-CPBA (332 mg, 1.64 mmol, 85.0% purity, 0.90 eq.) in one portion at 20° C. under N$_2$ atmosphere. The mixture was stirred at 20° C. for 5 hours. The reaction was quenched by saturated sodium thiosulfate (20.0 mL) and then extracted with ethyl acetate (20.0 mL×3), the combined organic phase was washed by brine (30.0 mL), concentrated to give benzyl 2-(cyanomethyl)-4-[7-(4-fluoro-1-naphthyl)-2-methylsulfinyl-6,8-dihydro-5H-pyrido[3,4-d]pyrimidin-4-yl]piperazine-1-carboxylate (1.00 g, 1.67 mmol, 91.8% yield) as a yellow solid which was used for the next step without further purification. LCMS [M+1]: 599.1.

Step C: benzyl-2-(cyanomethyl)-4-[2-[[(2S)-1-ethylpyrrolidin-2-yl]methoxy]-7-(4-fluoro-1-naphthyl)-6,8-dihydro-5H-pyrido[3,4-d]pyrimidin-4-yl]piperazine-1-carboxylate To a mixture of benzyl 2-(cyanomethyl)-4-[7-(4-fluoro-1-naphthyl)-2-methylsulfinyl-6,8-dihydro-5H-pyrido[3,4-d]pyrimidin-4-yl]piperazine-1-carboxylate (500 mg, 835.16 umol, 1.00 eq.) and [(2S)-1-ethylpyrrolidin-2-yl]methanol (216 mg, 1.67 mmol, 2.00 eq.) in toluene (10.0 mL) was added sodium tert-butoxide (120 mg, 1.25 mmol, 1.50 eq.) in one portion at 0° C. under N$_2$ atmosphere. The mixture was stirred at 0° C. for 30 min, The reaction mixture was quenched by addition water (10.0 mL) at 0° C., and then diluted with ethyl acetate (10.0 mL) and extracted with ethyl acetate (10 mL×3). The combined organic layers were washed with brine (20.0 mL), dried over anhydrous sodium sulfate, filtered and concentrated under reduced pressure to give a residue which purified by Prep-HPLC (TFA condition) to give benzyl-2-(cyanomethyl)-4-[2-[[(2S)-1-ethylpyrrolidin-2-yl]methoxy]-7-(4-fluoro-1-naphthyl)-6,8-dihydro-5H-pyrido[3,4-d]pyrimidin-4-yl]piperazine-1-carboxylate (200 mg, 292 umol, 35.0% yield, 97.0% purity) as a colorless solid. LCMS [M+1]: 664.5.

Step D: 2-[4-[2-[[(2S)-1-ethylpyrrolidin-2-yl]methoxy]-7-(4-fluoro-1-naphthyl)-6,8-dihydro-5H-pyrido[3,4-d]pyrimidin-4-yl]piperazin-2-yl]acetonitrile NH$_3$ (g) was bubbled into methanol (2 mL) for 5 min at 0° C., then added into a solution of benzyl 2-(cyanomethyl)-4-[2-[[(2S)-1-ethylpyrrolidin-2-yl]methoxy]-7-(4-fluoro-1-naphthyl)-6,8-dihydro-5H-pyrido [3,4-d]pyrimidin-4-yl] piperazine-1-carboxylate (200 mg, 301 umol, 1.00 eq.) in methanol (2.00 mL), then Pd/C (100 mg, 10% purity) was added under N$_2$ atmosphere. The suspension was degassed under vacuum and purged with H$_2$ several times. The mixture was stirred under H$_2$ (15 psi) at 20° C. for 1 hours. Filtered and concentrated to give 2-[4-[2-[[(2S)-1-ethylpyrrolidin-2-yl]methoxy]-7-(4-fluoro-1-naphthyl)-6,8-dihydro-5H-pyrido[3,4-d]pyrimidin-4-yl]piperazin-2-yl]acetonitrile (200 mg, crude) as a black solid which used for the next step without further purification. LCMS [M+1]: 530.5.

Step E: 2-[4-[2-[[(2S)-1-ethylpyrrolidin-2-yl]methoxy]-7-(4-fluoro-1-naphthyl)-6,8-dihydro-5H-pyrido[3,4-d]pyrimidin-4-yl]-1-prop-2-enoyl-piperazin-2-yl]acetonitrile To a mixture of 2-[4-[2-[[(2S)-1-ethylpyrrolidin-2-yl]methoxy]-7-(4-fluoro-1-naphthyl)-6,8-dihydro-5H-pyrido

[3,4-d]pyrimidin-4-yl]piperazin-2-yl]acetonitrile (100 mg, 189 umol, 1.00 eq.) and DIEA (73.2 mg, 566 umol, 98.7 uL, 3.00 eq.) in DCM (2.00 mL) was added prop-2-enoyl prop-2-enoate (47.6 mg, 378 umol, 2.00 eq.) in DCM (1.00 mL) drop-wise at 0° C. under $N_2$ atmosphere. The mixture was stirred at 20° C. for 30 min, methanol (1.00 mL) was added the reaction mixture and then the solvent was removed to give a residue which purified by Prep-TLC (SiO$_2$, DCM:MeOH=10:1, one drop of NH$_4$OH was added) to give a crude product. Then by Prep-HPLC (base condition) to give title compound 2-[4-[2-[[(2S)-1-ethylpyrrolidin-2-yl]methoxy]-7-(4-fluoro-1-naphthyl)-6,8-dihydro-5H-pyrido[3,4-d]pyrimidin-4-yl]-1-prop-2-enoyl-piperazin-2-yl]acetonitrile (14.9 mg, 25.0 umol, 13.2% yield, 97.9% purity) as a white solid. LCMS [M+1]: 584.5.

$^1$H NMR (400 MHz, CDCl$_3$) δ=8.25 (dd, J=2.4, 4.8 Hz, 1H), 8.19-8.08 (m, 1H), 7.63-7.54 (m, 2H), 7.15-7.03 (m, 2H), 6.61 (br s, 1H), 6.47-6.38 (m, 1H), 5.86 (br d, J=10.2 Hz, 1H), 5.12 (br s, 1H), 4.38 (dd, J=4.4, 10.6 Hz, 1H), 4.24 (br s, 2H), 4.20-4.10 (m, 2H), 4.04 (br d, J=12.0 Hz, 2H), 3.76-2.67 (m, 12H), 2.52-2.37 (m, 1H), 2.32-2.21 (m, 1H), 2.09-1.97 (m, 1H), 1.90-1.74 (m, 3H), 1.16 (t, J=7.2 Hz, 3H).

Example 323

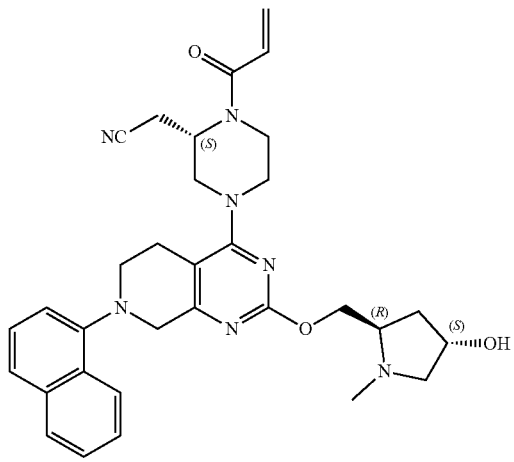

2-[(2S)-4-[2-[[(2R,4S)-4-hydroxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile

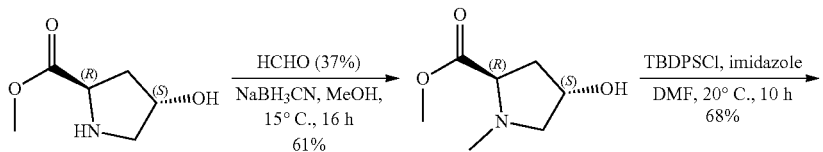

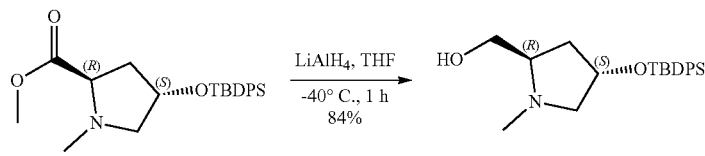

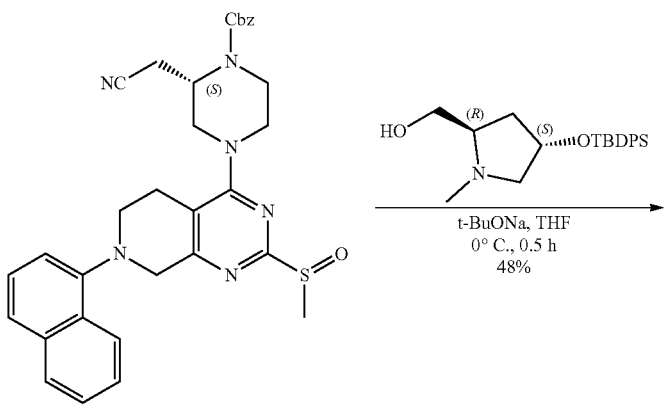

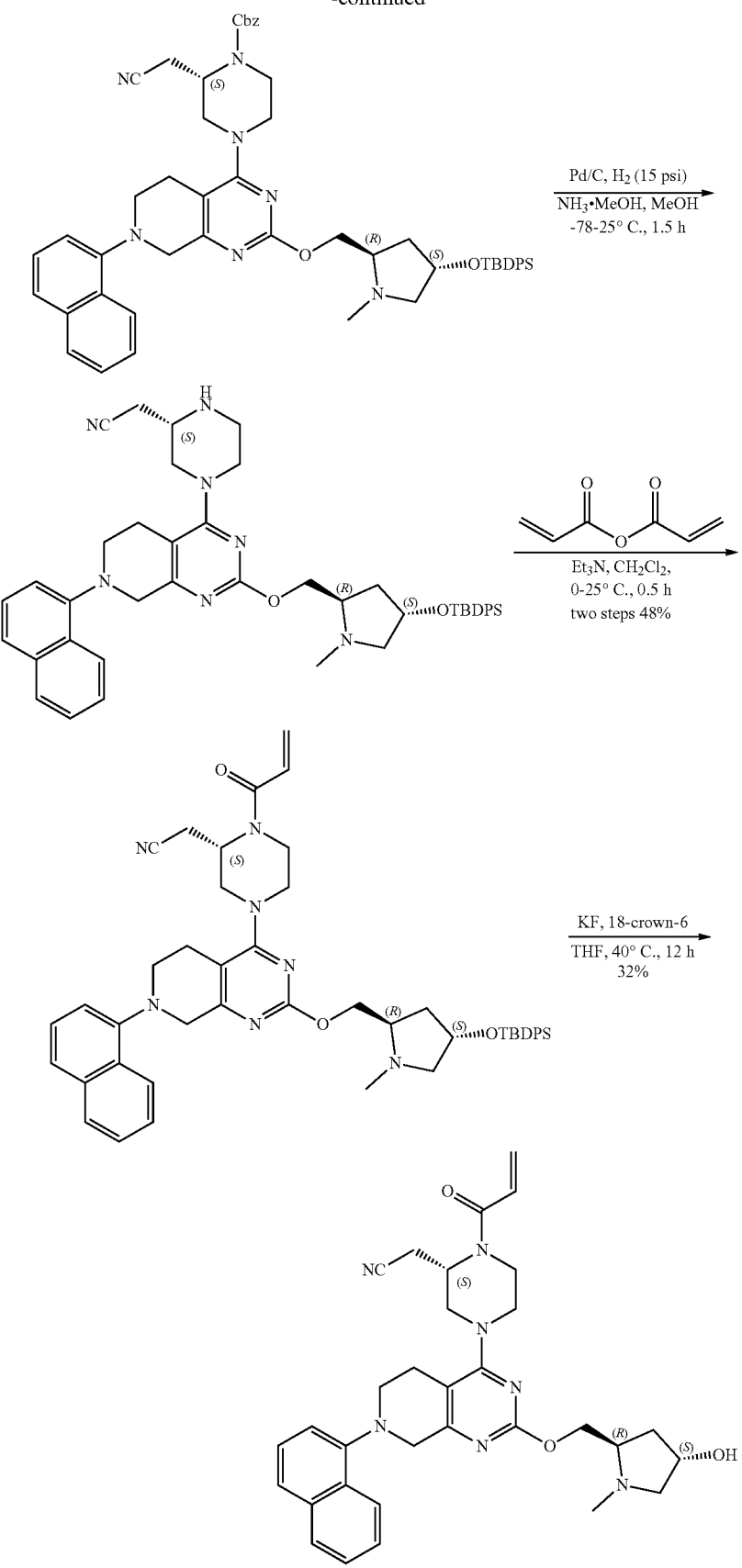

Step A: methyl (2R,4S)-4-hydroxy-1-methyl-pyrrolidine-2-carboxylate

To a solution of methyl (2R,4S)-4-hydroxypyrrolidine-2-carboxylate (3 g, 20.7 mmol, 1 eq, HCl) and formaldehyde (8.39 g, 103 mmol, 7.69 mL, 37% purity, 5 eq) in MeOH (30 mL) was added AcOH (1.24 g, 20.7 mmol, 1.18 mL, 1 eq) at 15° C. After stirring for 30 minutes, NaBH$_3$CN (3.25 g, 51.7 mmol, 2.5 eq) was added. The mixture was stirred for 16 hours. To the mixture was added saturated aqueous sodium carbonate solution (50 mL), and then extracted with dichloromethane/methanol 10/1 (3×50 mL). The combined organic layers were dried over sodium sulfate, filtered and concentrated under vacuum. Methyl (2R,4S)-4-hydroxy-1-methyl-pyrrolidine-2-carboxylate (2 g, 12.6 mmol, 61% yield) was obtained as a yellow oil.

Step B: methyl (2R,4S)-4-[tert-butyl(diphenyl)silyl]oxy-1-methyl-pyrrolidine-2-carboxylate To a solution of methyl (2R,4S)-4-hydroxy-1-methyl-pyrrolidine-2-carboxylate (1.70 g, 10.7 mmol, 1.00 eq) in DMF (10.0 mL) was added imidazole (1.67 g, 24.6 mmol, 2.30 eq) and tert-butylchlorodiphenylsilane (3.52 g, 12.8 mmol, 3.29 mL, 1.20 eq). The mixture was stirred at 20° C. for 10 hours. The mixture was diluted with ethyl acetate (20.0 mL), washed with brine (3×30.0 mL), dried over Na$_2$SO$_4$, filtered and concentrated under vacuum. The residue was purified by column chromatography (Al$_2$O$_3$, methanol/ethyl acetate=1/10) to give methyl (2R,4S)-4-[tert-butyl(diphenyl)silyl]oxy-1-methyl-pyrrolidine-2-carboxylate (3.00 g, 7.24 mmol, 68% yield) as a colorless oil. LCMS [ESI, M+1]: 398.

$^1$H NMR (400 MHz, chloroform-d) δ=7.63 (ddd, J=1.6, 3.6, 7.6 Hz, 4H), 7.46-7.35 (m, 6H), 4.47-4.40 (m, 1H), 3.71 (s, 3H), 3.32 (t, J=8.4 Hz, 1H), 3.25 (dd, J=6.0, 10.0 Hz, 1H), 2.42 (br d, J=5.2 Hz, 1H), 2.40 (s, 3H), 2.18-2.01 (m, 2H), 1.07 (s, 9H).

Step C: [(2R,4S)-4-[tert-butyl(diphenyl)silyl]oxy-1-methyl-pyrrolidin-2-yl]methanol To a solution of methyl (2R,4S)-4-[tert-butyl(diphenyl)silyl]oxy-1-methyl-pyrrolidine-2-carboxylate (1.50 g, 3.77 mmol, 1.00 eq) in THF (10.0 mL) was added LiAlH$_4$ (573 mg, 15.1 mmol, 4.00 eq) at −40° C. After stirred at −40° C. for 1 hour, the mixture was quenched with water (0.50 mL), NaOH solution (15.0%, 1.00 mL), water (1.50 mL). The formed precipitate was filtered off and the filter cake was washed with ethyl acetate (40.0 mL). The filtrate was concentrated under vacuum. The residue was purified by column chromatography (Al$_2$O$_3$, methanol/ethyl acetate 1/10) to give [(2R,4S)-4-[tert-butyl (diphenyl)silyl]oxy-1-methyl-pyrrolidin-2-yl]methanol (1.20 g, 3.18 mmol, 84% yield) as a yellow oil. LCMS [ESI, M+1]: 370.

$^1$H NMR (400 MHz, chloroform-d) δ=7.67-7.62 (m, 4H), 7.46-7.36 (m, 6H), 4.37-4.24 (m, 1H), 3.63 (dd, J=3.2, 11.2 Hz, 1H), 3.35 (dd, J=2.0, 10.8 Hz, 1H), 3.15 (dd, J=6.0, 9.6 Hz, 1H), 2.76 (br t, J=8.0 Hz, 1H), 2.44 (dd, J=6.0, 9.6 Hz, 1H), 2.33 (s, 3H), 2.04-1.85 (m, 2H), 1.06 (s, 9H).

Step D: benzyl (2S)-4-[2-[[(2R,4S)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate To a solution of [(2R,4S)-4-[tert-butyl(diphenyl)silyl]oxy-1-methyl-pyrrolidin-2-yl]methanol (305 mg, 827 umol, 1.20 eq) in THF (5.00 mL) was added t-BuONa (132 mg, 1.38 mmol, 2.00 eq) at 0° C. followed by benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 0.40 g, 689 umol, 1.00 eq). After stirring at 0° C. for 0.5 h, the mixture was diluted with ethyl acetate (30.0 mL), washed with water (1×20.0 mL), dried over Na$_2$SO$_4$, filtered and concentrated under vacuum. The residue was purified by column chromatography (Al$_2$O$_3$, petroleum ether/ethyl acetate=1/3) to give benzyl (2S)-4-[2-[[(2R,4S)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (0.35 g, 328 umol, 48% yield) as a yellow solid. LCMS [ESI, M/2+1]: 444.

$^1$H NMR (400 MHz, chloroform-d) δ=8.24-8.18 (m, 1H), 7.90-7.84 (m, 1H), 7.69-7.59 (m, 5H), 7.52-7.48 (m, 2H), 7.44-7.36 (m, 12H), 7.14 (d, J=7.2 Hz, 1H), 5.21 (s, 2H), 4.68 (br s, 1H), 4.42-4.36 (m, 1H), 4.32 (br dd, J=4.8, 10.4 Hz, 1H), 4.26 (br d, J=6.8 Hz, 2H), 4.17-4.06 (m, 3H), 3.98-3.88 (m, 1H), 3.47 (br s, 1H), 3.29 (br d, J=10.8 Hz, 3H), 3.16 (br dd, J=6.0, 9.6 Hz, 1H), 3.11-2.95 (m, 3H), 2.91-2.73 (m, 3H), 2.47-2.36 (m, 4H), 2.11 (ddd, J=4.8, 8.4, 13.2 Hz, 1H), 1.95-1.82 (m, 1H), 1.06 (s, 9H).

Step E: 2-[(2S)-4-[2-[[(2R,4S)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]piperazin-2-yl]acetonitrile NH$_3$ was bubbled in methanol (40.0 mL) at −78° C. for 0.5 h. Benzyl (2S)-4-[2-[[(2R,4S)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (0.32 g, 361 umol, 1.00 eq) and Pd/C (0.10 g, 10.0% purity) was added into the mixture. After stirring at 25° C. under H$_2$ at 15 psi for 1 hour, the mixture was filtered and filtrate was concentrated under vacuum to give 2-[(2S)-4-[2-[[(2R,4S)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (0.27 g, crude) as a yellow oil and used into next step without further purification. LCMS [ESI, M/2+1]: 377.

Step F: 2-[(2S)-4-[2-[[(2R,4S)-4-[tert-butyl(diphenyl)silyl]oxy-1-methyl-pyrrolidin-2-yl]methoxyl]-7-(1-naphthyl)-6,8-dihydro-5H-pyrido[3,4-d]pyrimidin-4-yl]-1-prop-2-enoyl-piperazin-2-yl]acetonitrile To a solution of 2-[(2S)-4-[2-[[(2R,4S)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (0.27 g, crude) and TEA (182 mg, 1.80 mmol, 250 uL) in dichloromethane (2.00 mL) was added prop-2-enoyl prop-2-enoate (45.3 mg, 359 umol) at 0° C. After stirring at 25° C. for 0.5 h, the mixture was quenched with methanol (0.10 mL) and concentrated under vacuum. The residue was purified by column chromatography (Al$_2$O$_3$, petroleum ether/ethyl acetate=1/3) to give 2-[(2S)-4-[2-[[(2R,4S)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (0.16 g, 171 umol, two steps 48% yield) as a yellow solid. LCMS [ESI, M+1]: 806.

Step G: 2-[(2S)-4-[2-[[(2R,4S)-4-hydroxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile A mixture of 2-[(2S)-4-[2-[[(2R,4S)-4-[tert-butyl(diphenyl)silyl]oxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (0.16 g, 198 umol, 1.00 eq), KF (46.1 mg, 794 umol, 18.6 uL, 4.00 eq) and 18-crown-6 (210 mg, 794 umol, 4.00 eq) in THF (2.00 mL) was stirred at 40° C. for 12 hours. The mixture was concentrated under vacuum. The residue was purified by reversed phase flash [water (TFA, 0.10%)/acetonitrile]. The desired fraction was collected and adjust pH >7 by saturated sodium bicarbonate (2.00 mL) and then extracted with ethyl acetate (3×30.0 mL), dried over $Na_2SO_4$, filtered and concentrated under vacuum. The residue was purified by prep-HPLC (Phenomenex Gemini 150*25 mm*10 um; mobile phase: [water (0.05% ammonia hydroxide v/v)-ACN]; B %: 38%-66%, 12 min). The desired fractions were collected and lyophilized to give title compound 2-[(2S)-4-[2-[[(2R,4S)-4-hydroxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (EXAMPLE 323, 36.3 mg, 63.9 umol, 32% yield, 98.1% purity) as a white solid. LCMS [ESI, M+1]: 568.

SFC: "OJ-3S_3_5_40_3ML Column: Chiralcel OJ-3 100×4.6 mm I.D., 3 um Mobile phase: methanol (0.05% DEA) in $CO_2$ from 5% to 40% Flow rate: 3 mL/min Wavelength: 220 nm".

$^1$H NMR (400 MHz, chloroform-d) δ=8.25-8.18 (m, 1H), 7.91-7.83 (m, 1H), 7.62 (d, J=8.0 Hz, 1H), 7.55-7.48 (m, 2H), 7.44 (t, J=8.0 Hz, 1H), 7.15 (d, J=7.2 Hz, 1H), 6.60 (br s, 1H), 6.46-6.35 (m, 1H), 5.84 (br d, J=9.6 Hz, 1H), 5.20-4.53 (m, 1H), 4.47 (quin, J=5.6 Hz, 1H), 4.41 (dd, J=4.8, 10.8 Hz, 1H), 4.34-4.19 (m, 3H), 4.14 (br d, J=13.2 Hz, 1H), 4.02 (br d, J=11.6 Hz, 2H), 3.63 (br s, 1H), 3.46 (br dd, J=6.0, 9.6 Hz, 2H), 3.36 (br s, 2H), 3.12 (br s, 1H), 3.07-2.90 (m, 3H), 2.90-2.67 (m, 2H), 2.51 (s, 3H), 2.35 (dd, J=5.2, 9.6 Hz, 1H), 2.14-2.04 (m, 1H), 2.04-1.96 (m, 1H).

Example 324

2-[(2S)-4-[7-(3-methoxy-2-methyl-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

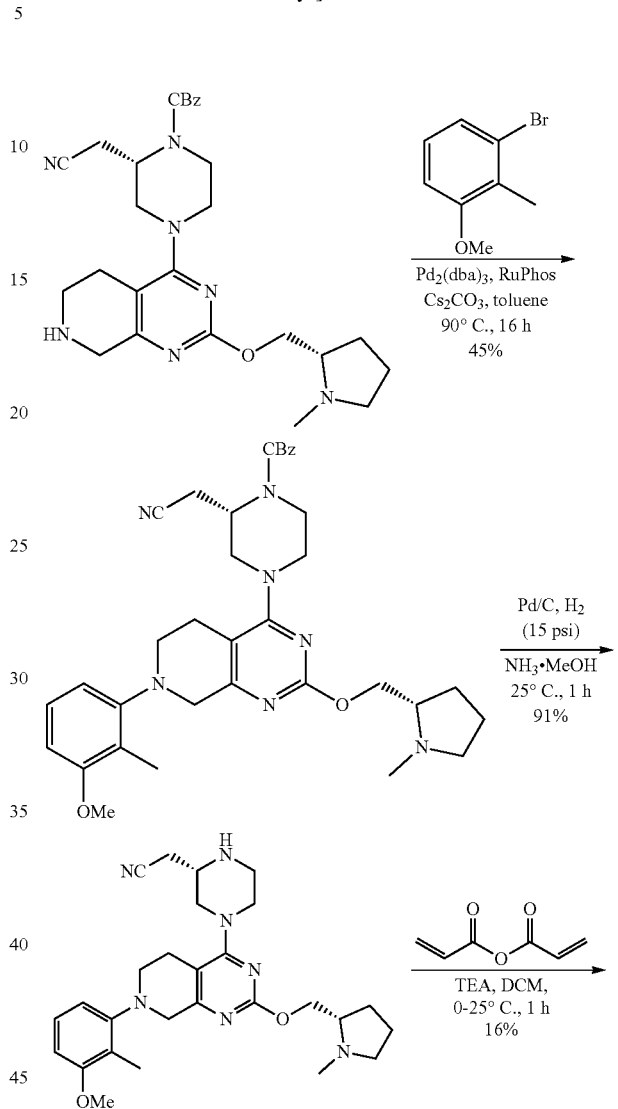

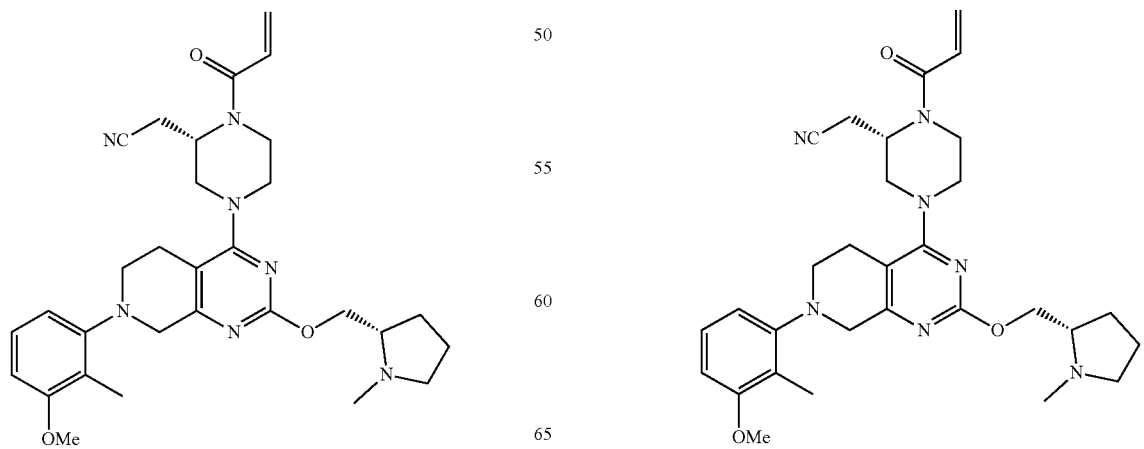

Step A: Benzyl (2S)-2-(cyanomethyl)-4-[7-(3-methoxy-2-methyl-phenyl)-2-[[(2S)-1-methyl pyrrolidin-2-yl]methoxy]-6,8-dihydro-5H-pyrido[3,4-d]pyrimidin-4-yl]piperazine-1-carboxylate To a mixture of benzyl (2S)-2-(cyanomethyl)-4-[2-[[(2S)-1-methyl pyrrolidin-2-yl]methoxy]-5,6,7,8-tetrahydro-pyrido[3,4-d]pyrimidin-4-yl]piperazine-1-carboxylate (Intermediate 65, 300 mg, 593 umol, 1.00 eq), 1-bromo-3-methoxy-2-methyl-benzene (239 mg, 1.19 mmol, 2 eq), Cs$_2$CO$_3$ (580 mg, 1.78 mmol, 3 eq), Pd$_2$(dba)$_3$ (109 mg, 119 umol, 0.2 eq) and RuPhos (83.1 mg, 178 umol, 0.3 eq) in toluene (30 mL) was degassed and purged with N$_2$ for 3 times, and then the mixture was stirred at 90° C. for 16 hours under N$_2$ atmosphere. To the reaction mixture was added H$_2$O (1×200 mL) and Ethyl acetate (1×250 mL). The organic phase was separated, washed with brine (1×200 mL), dried over sodium sulfate, filtered and concentrated under reduced pressure to give a residue. The residue was purified by reversed phase flash [water (0.1% FA)/acetonitrile]. The desired fractions were collected and neutralized to pH=7 with saturated NaHCO$_3$ solution and extracted with ethyl acetate (100 mL). The extracts were dried over sodium sulfate, filtered and concentrated under vacuum. Benzyl (2S)-2-(cyanomethyl)-4-[7-(3-methoxy-2-methyl-phenyl)-2-[[(2S)-1-methyl pyrrolidin-2-yl]methoxy]-6,8-dihydro-5H-pyrido[3,4-d]pyrimidin-4-yl]piperazine-1-carboxylate (170 mg, 270 umol, 45% yield, 99.2% purity) was obtained as a yellow solid. LCMS [ESI, M+1]: 626.

$^1$H NMR (400 MHz, chloroform-d) δ=7.43-7.33 (m, 5H), 7.16 (t, J=8.0 Hz, 1H), 6.72 (d, J=8.0 Hz, 1H), 6.68 (d, J=8.0 Hz, 1H), 5.20 (s, 2H), 4.80 (br dd, J=6.8, 11.6 Hz, 1H), 4.68 (br s, 1H), 4.45 (br dd, J=4.4, 12.0 Hz, 1H), 4.21-4.08 (m, 3H), 4.05 (s, 2H), 3.94 (br d, J=12.8 Hz, 1H), 3.85 (s, 3H), 3.67-3.56 (m, 1H), 3.32 (br d, J=11.2 Hz, 3H), 3.24-3.01 (m, 3H), 2.95-2.67 (m, 8H), 2.32-2.10 (m, 5H), 2.00 (br s, 1H).

Step B: 2-[(2S)-4-[7-(3-methoxy-2-methyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a mixture of benzyl (2S)-2-(cyanomethyl)-4-[7-(3-methoxy-2-methyl-phenyl)-2-[[(2S)-1-methylpyrrolidin-2-yl]methoxy]-6,8-dihydro-5H-pyrido[3,4-d]pyrimidin-4-yl]piperazine-1-carboxylate (260 mg, 416 umol, 1.00 eq), Pd/C (130 mg, 10% purity) and NH$_3$ in MeOH (50 mL) was degassed and purged with H$_2$ for 3 times, and then the mixture was stirred at 25° C. for 1 hr under H$_2$ atmosphere at 15 psi pressure. After that, the catalyst was filtered off and the filtrate was concentrated under vacuum. Compound 2-[(2S)-4-[7-(3-methoxy-2-methyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 376 umol, 91% yield, 92.4% purity) was obtained as a yellow oil. LCMS [ESI, M+1]: 492.

Step C: 2-[(2S)-4-[7-(3-methoxy-2-methyl-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2S)-4-[7-(3-methoxy-2-methyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 407 umol, 1.00 eq) and TEA (206 mg, 2.03 mmol, 283 uL, 5.00 eq) in DCM (10 mL) was added prop-2-enoyl prop-2-enoate (41.0 mg, 325 umol, 0.800 eq) at 0° C. The mixture was stirred at 25° C. for 1 hour. The reaction mixture was quenched with NaHCO$_3$ saturated solution (5 mL) at 0° C., and then extracted with CH$_2$Cl$_2$ (2×25 mL). The combined organic layers were washed with brine (1×50 mL), dried over sodium sulfate, filtered and concentrated under vacuum to give a residue. The residue was purified by silica gel chromatography (Ethyl acetate/Methanol=20/1 to 3/1). The residue was further purified by prep-HPLC (column: Phenomenex Gemini 150*25 mm*10 um; mobile phase: [water (0.05% ammonia hydroxide v/v)-ACN]; B %: 48%-78%, 12 min). Title compound 2-[(2S)-4-[7-(3-methoxy-2-methyl-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 324, 35.2 mg, 63.6 umol, 16% yield, 98.7% purity) was obtained as a white solid. LCMS [ESI, M+1]: 546.

SFC condition: "OD-3S_3_40_3ML Column: Chiralcel OD-3 100×4.6 mm I.D., 3 um, Mobile phase: 40% methanol (0.05% DEA) in CO$_2$ Flow rate: 3 mL/min Wavelength: 220 nm".

$^1$H NMR (400 MHz, chloroform-d) δ=7.17 (t, J=8.4 Hz, 1H), 6.73 (d, J=8.0, 1H) 6.68 (d, J=8.4, 1H), 6.59 (br s, 1H), 6.46-6.34 (m, 1H), 5.83 (br d, J=10.0 Hz, 1H), 5.10 (br s, 1H), 4.39 (dd, J=5.2, 10.4 Hz, 1H), 4.20-4.09 (m, 2H), 4.06 (s, 2H), 4.02-3.92 (m, 2H), 3.85 (s, 3H), 3.59 (br s, 1H), 3.31 (br d, J=12.0 Hz, 1H), 3.22 (br d, J=11.6 Hz, 1H), 3.17-3.02 (m, 3H), 3.02-2.62 (m, 6H), 2.49 (s, 3H), 2.36-2.25 (m, 1H), 2.22 (s, 3H), 2.13-1.99 (m, 1H), 1.91-1.70 (m, 2H).

Example 325

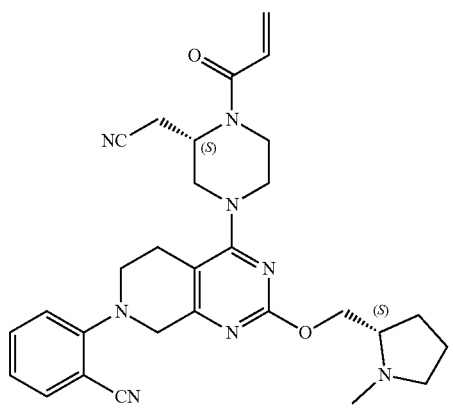

2-(1-acryloyl-4-(7-(7-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

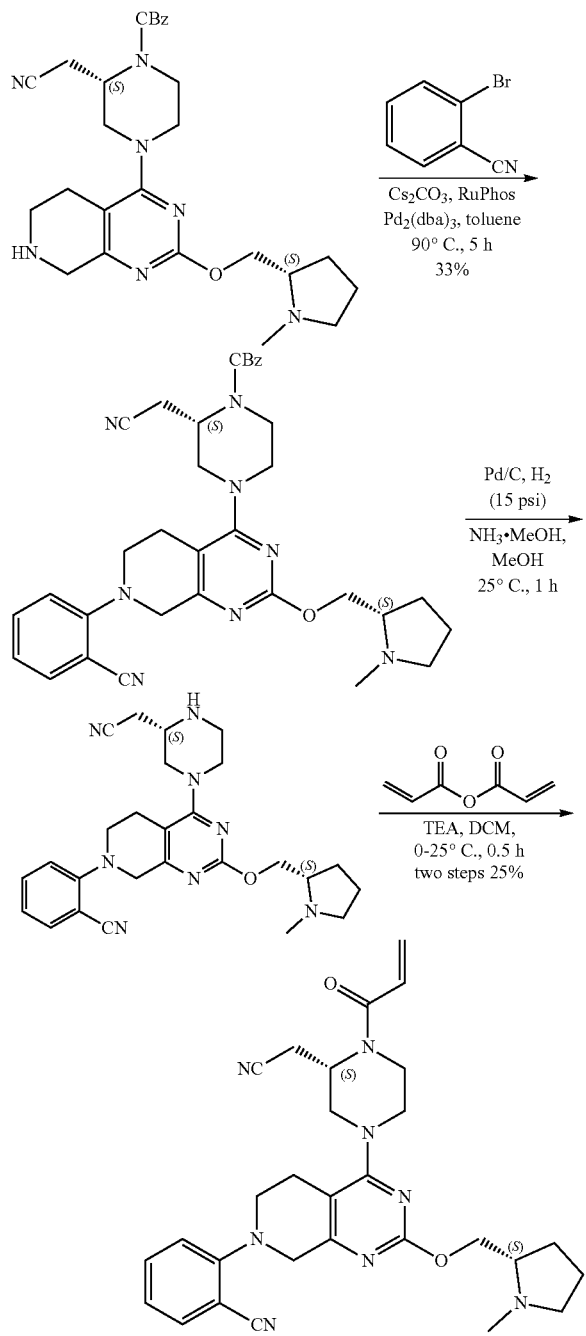

Step A: benzyl (2S)-2-(cyanomethyl)-4-[7-(2-cyanophenyl)-2-[[(2S)-1-methylpyrrolidin-2-yl]methoxy]-6,8-dihydro-5H-pyrido[3,4-d]pyrimidin-4-yl]piperazine-1-carboxylate To a mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 320 mg, 633 umol, 1 eq) and 2-bromobenzonitrile (230 mg, 1.27 mmol, 2 eq) in toluene (30 mL) was added Cs$_2$CO$_3$ (619 mg, 1.90 mmol, 3 eq), RuPhos (59.1 mg, 127 umol, 0.2 eq), Pd$_2$(dba)$_3$ (58.0 mg, 63.3 umol, 0.1 eq) in one portion. The mixture was degassed and purged with N$_2$ for 3 times, then heated to 90° C. and stirred for 5 hours. The reaction mixture was diluted with water (10 mL) and extracted with ethyl acetate (30 mL×3). The combined organic layers were washed with water (30 mL×1), dried over sodium sulfate, filtered and concentrated under reduced pressure to give a residue. The residue was purified by reversed phase flash [water (0.1% FA)/acetonitrile]. The desired fractions were collected and neutralized with saturated NaHCO$_3$ solution (5 mL) and extracted with ethyl acetate (100 mL). The separated organic layer was dried over sodium sulfate, filtered and concentrated under vacuum. Compound benzyl (2S)-2-(cyanomethyl)-4-[7-(2-cyanophenyl)-2-[[(2S)-1-methylpyrrolidin-2-yl]methoxy]-6,8-dihydro-5H-pyrido[3,4-d]pyrimidin-4-yl]piperazine-1-carboxylate (139 mg, 210 umol, 33% yield, 91.5% purity) was obtained as a yellow solid. LCMS [ESI, M+1]: 607.

$^1$H NMR (400 MHz, chloroform-d) δ=7.62 (dd, J=1.2, 7.6 Hz, 1H), 7.56-7.49 (m, 1H), 7.42-7.33 (m, 5H), 7.09-7.00 (m, 2H), 5.21 (s, 2H), 4.68 (br s, 1H), 4.38 (br dd, J=4.8, 10.4 Hz, 1H), 4.26 (s, 2H), 4.19-4.01 (m, 3H), 3.92 (br d, J=11.6 Hz, 1H), 3.78 (br d, J=12.0 Hz, 1H), 3.44-3.21 (m, 3H), 3.15-2.95 (m, 3H), 2.85-2.61 (m, 4H), 2.49 (s, 3H), 2.34-2.23 (m, 1H), 2.12-2.00 (m, 1H), 1.92-1.72 (m, 3H).

Step B: 2-[4-[(3S)-3-(cyanomethyl)piperazin-1-yl]-2-[[(2S)-1-methylpyrrolidin-2-yl]methoxy]-6,8-dihydro-5H-pyrido[3,4-d]pyrimidin-7-yl]benzonitrile To a solution of benzyl (2S)-2-(cyanomethyl)-4-[7-(2-cyanophenyl)-2-[[(2S)-1-methylpyrrolidin-2-yl]methoxy]-6,8-dihydro-5H-pyrido[3,4-d]pyrimidin-4-yl]piperazine-1-carboxylate (160 mg, 264 umol, 1 eq) in MeOH (12 mL) was added NH$_3$.MeOH (20 mL) and Pd/C (20 mg, 10% purity) under N$_2$. The suspension was degassed under vacuum and purged with H$_2$ several times. The mixture was stirred under H$_2$ (15 psi) at 25° C. for 1 hour. The catalyst was filtered off and the filtrate was concentrated under reduced pressure to give a residue. The crude product was used directly in the next step without purification. Compound 2-[4-[(3S)-3-(cyanomethyl)piperazin-1-yl]-2-[[(2S)-1-methylpyrrolidin-2-yl]methoxy]-6,8-dihydro-5H-pyrido[3,4-d]pyrimidin-7-yl]benzonitrile (119 mg, crude) was obtained as a green solid. LCMS [ESI, M+1]: 473, Step C: 2-[4-[(3S)-3-(cyanomethyl)-4-prop-2-enoyl-piperazin-1-yl]-2-[[(2S)-1-methylpyrrolidin-2-yl]methoxy]-6,8-dihydro-5H-pyrido[3,4-d]pyrimidin-7-yl]benzonitrile To a mixture of 2-[4-[(3S)-3-(cyanomethyl)piperazin-1-yl]-2-[[(2S)-1-methylpyrrolidin-2-yl]methoxy]-6,8-dihydro-5H-pyrido[3,4-d]pyrimidin-7-yl]benzonitrile (119 mg, crude) and prop-2-enoyl prop-2-enoate (31.8 mg, 252 umol) in DCM (5 mL) was added TEA (127 mg, 1.26 mmol, 175 uL) in portion at 0° C. under N$_2$. The mixture was heated to 25° C. and stirred for 0.5 hour. The reaction mixture was quenched by addition saturated NaHCO$_3$ (5 mL) at 0° C., and then extracted with DCM (10 mL×3). The combined organic layers were washed with water (15 mL×1), dried over Na$_2$SO$_4$, filtered and concentrated under reduced pressure to give a residue. The residue was purified by prep-HPLC (column: Phenomenex Gemini 150*25 mm*10 um;

mobile phase: [water (0.05% ammonia hydroxide v/v)-ACN]; B %: 43%-73%, 12 min). Title compound 2-[4-[(3S)-3-(cyanomethyl)-4-prop-2-enoyl-piperazin-1-yl]-2-[[(2S)-1-methylpyrrolidin-2-yl]methoxy]-6,8-dihydro-5H-pyrido[3,4-d]pyrimidin-7-yl]benzonitrile (EXAMPLE 325, 35.1 mg, 65.1 umol, two steps 25% yield, 97.5% purity) was obtained as a colorless oil. LCMS [ESI, M+1]: 527.

$^1$H NMR (400 MHz, chloroform-d) δ=7.62 (d, J=8.0 Hz, 1H), 7.54 (t, J=8.4 Hz, 1H), 7.10-7.00 (m, 2H), 6.59 (br s, 1H), 6.45-6.34 (m, 1H), 5.84 (br d, J=10.4 Hz, 1H), 5.09 (br s, 1H), 4.38 (dd, J=5.2, 10.4 Hz, 1H), 4.27 (s, 2H), 4.21-4.08 (m, 2H), 3.99 (br d, J=12.0 Hz, 2H), 3.86-3.52 (m, 2H), 3.39 (br s, 2H), 3.18-2.99 (m, 3H), 2.97-2.59 (m, 5H), 2.49 (s, 3H), 2.37-2.21 (m, 1H), 2.17-1.98 (m, 1H), 1.94-1.79 (m, 2H).

Example 326

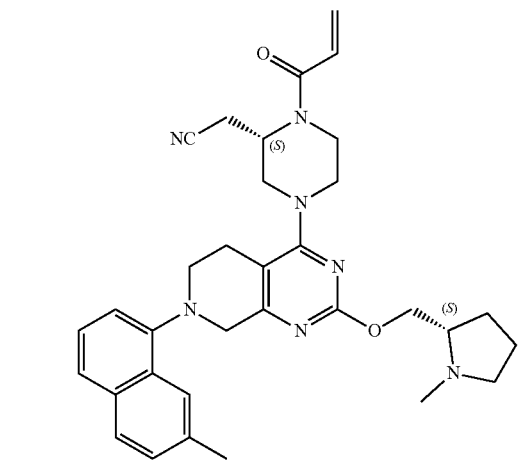

2-((S)-1-acryloyl-4-(7-(7-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

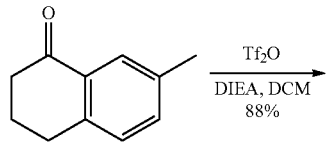

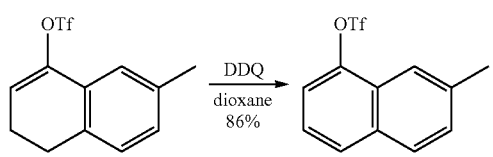

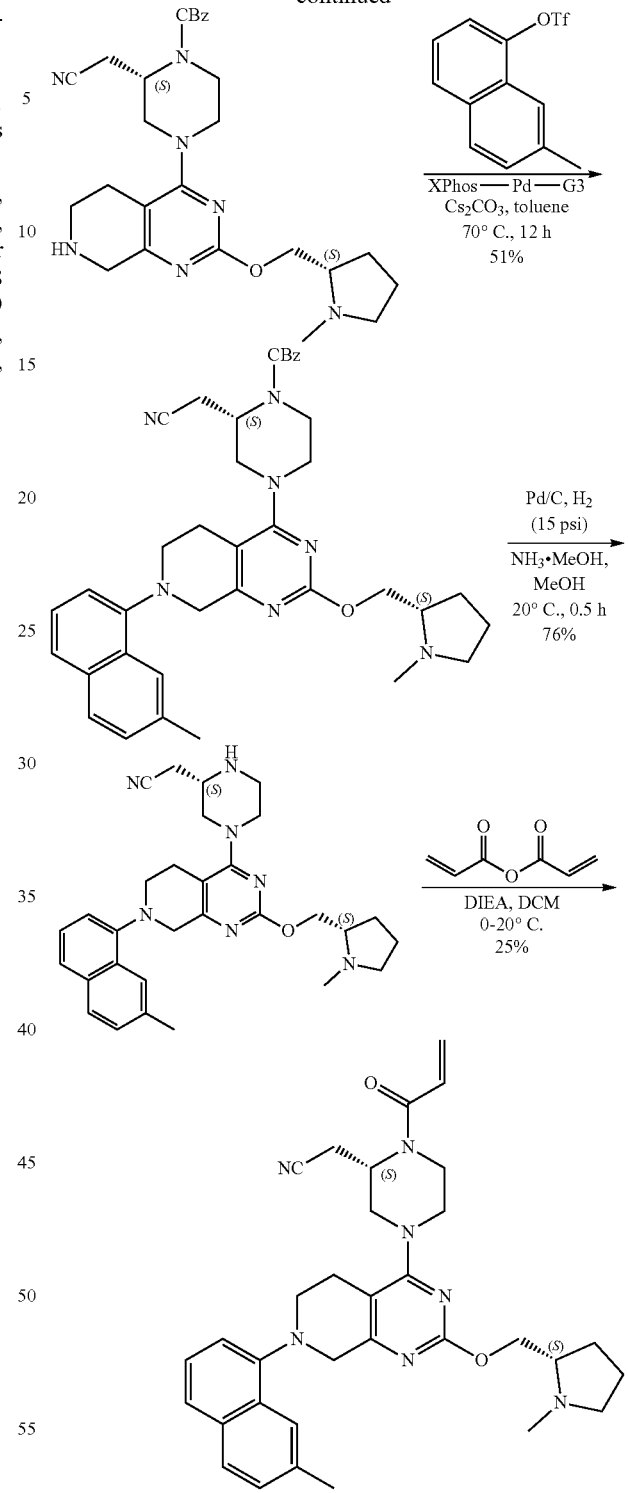

Step A: methyl-3,4-dihydronaphthalen-1-yl) trifluoromethanesulfonate

To a solution of 7-methyltetralin-1-one (2.5 g, 15.6 mmol, 1.0 eq) in DCM (40 mL) was added DIEA (6.05 g, 46.8 mmol, 8.15 mL, 3.0 eq) and Tf$_2$O (6.60 g, 23.4 mmol, 3.86 mL, 1.5 eq) in portions at 0° C., the reaction mixture was stirred at 0-20° C. for 3 hours under N$_2$. After completion, the reaction was added ice water (40 mL) slowly; the organic layer was separated, and then dried over Na$_2$SO$_4$, filtered and concentrated. The residue was purified by column chromatography (SiO$_2$, Petroleum ether/Ethyl acetate=1:0) to give (7-methyl-3,4-dihydronaphthalen-1-yl) trifluoromethanesulfonate (4.0 g, 13.7 mmol, 88% yield) as yellow oil.

$^1$H NMR (400 MHz, chloroform-d) δ 7.18 (s, 1H), 7.12-7.06 (m, 2H), 6.02 (t, J=4.8 Hz, 1H), 2.85 (t, J=8.2 Hz, 2H), 2.54-2.45 (m, 2H), 2.37 (s, 3H).

Step B: (7-methyl-1-naphthyl) trifluoromethanesulfonate

To a solution of (7-methyl-3,4-dihydronaphthalen-1-yl) trifluoromethanesulfonate (4.0 g, 13.7 mmol, 1.0 eq) in dioxane (80.0 mL) was added DDQ (6.21 g, 27.4 mmol, 2.0 eq), the reaction mixture was stirred at 105° C. for 12 hours. After completion, the reaction was concentrated. The residue was purified by column chromatography (SiO$_2$, Petroleum ether/Ethyl acetate=1:0). The product (7-methyl-1-naphthyl) trifluoromethanesulfonate (3.4 g, 11.7 mmol, 86% yield) was obtained as yellow oil.

$^1$H NMR (400 MHz, chloroform-d) δ 7.89-7.81 (m, 3H), 7.49-7.40 (m, 3H), 2.60 (s, 3H).

Step C: benzyl(2S)-2-(cyanomethyl)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 1.20 g, 2.37 mmol, 1.0 eq) and (7-methyl-1-naphthyl) trifluoromethanesulfonate (1.03 g, 3.56 mmol, 1.50 eq) in toluene (20.0 mL) was added Cs$_2$CO$_3$ (1.55 g, 4.75 mmol, 2.0 eq), and Xphos-Pd-G3 (301 mg, 356 umol, 0.15 eq), the mixture was stirred at 70° C. for 12 hours under N$_2$. After completion, the reaction mixture was added water (20.0 mL), then extracted with ethyl acetate (2×15.0 mL), the combined organic layer was dried over Na$_2$SO$_4$, filtered and concentrated. The residue was purified by column chromatography (SiO$_2$, Petroleum ether/Ethyl acetate=3/1 to ethyl acetate:Methanol=20:1). The product benzyl(2S)-2-(cyanomethyl)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (820 mg, 1.22 mmol, 51% yield, 95.9% purity) was obtained as brown solid. LCMS [ESI, M+1]: 646.

Step D: 2-[(2S)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (790 mg, 1.22 mmol, 1.0 eq) in MeOH (15.0 mL) was added NH$_3$.MeOH (1.22 mmol, 15.0 mL, 1.0 eq) and Pd/C (500 mg, 10% purity), the suspension was degassed under vacuum and purged with H$_2$ several times. The mixture was stirred under H$_2$ (15 Psi) at 20° C. for 0.5 hour. After completion, the reaction mixture was filtered through a pad of Celite, and the filter cake was washed with DCM (2×20 mL), the filtrate was concentrated. The product 2-[(2S)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (490 mg, 934 umol, 76% yield, 97.5% purity) was obtained as white solid which was used for the next step without further purification. LCMS [ESI, M+1]: 512.

Step E: 2-[(2S)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2S)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (490 mg, 958 umol, 1.0 eq) in DCM (8.0 mL) was added DIEA (495 mg, 3.83 mmol, 667 uL, 4.0 eq) and prop-2-enoyl prop-2-enoate (121 mg, 958 umol, 1.0 eq) at 0° C., the reaction mixture was stirred at 20° C. for 0.5 hour. After completion, the reaction mixture was quenched with MeOH (5.0 mL), and concentrated. The residue was purified by column chromatography (Base Al$_2$O$_3$, Ethyl acetate/Methanol=20/1), the obtained crude product was concentrated and re-purified by prep-HPLC ((column: Phenomenex Gemini 150*25 mm*10 um; mobile phase: [water (0.05% ammonia hydroxide v/v)-ACN]; B %: 57%-87%, 12 min), the obtained product was concentrated. and then under lyophilization. Title compound 2-[(2S)-4-[7-(7-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 326, 133 mg, 235 umol, 25% yield, 99.6% purity) was obtained as white solid. LCMS [ESI, M+1]: 566.

$^1$H NMR (400 MHz, chloroform-d) δ 8.00 (s, 1H), 7.78 (d, J=8.4 Hz, 1H), 7.59 (d, J=8.0 Hz, 1H), 7.43-7.32 (m, 2H), 7.13 (d, J=7.2 Hz, 1H), 6.69-6.49 (m, 1H), 6.42 (dd, J=1.2, 16.8 Hz, 1H), 5.85 (br d, J=10.8 Hz, 1H), 5.20-4.52 (m, 1H), 4.42 (dd, J=4.8, 10.4 Hz, 1H), 4.36-4.24 (m, 2H), 4.22-4.10 (m, 2H), 4.06-3.95 (m, 2H), 3.76-3.22 (m, 4H), 3.21-3.07 (m, 2H), 3.04-2.63 (m, 5H), 2.56 (s, 3H), 2.51 (s, 3H), 2.35-2.26 (m, 1H), 2.14-2.02 (m, 1H), 1.92-1.75 (m, 3H).

Example 327

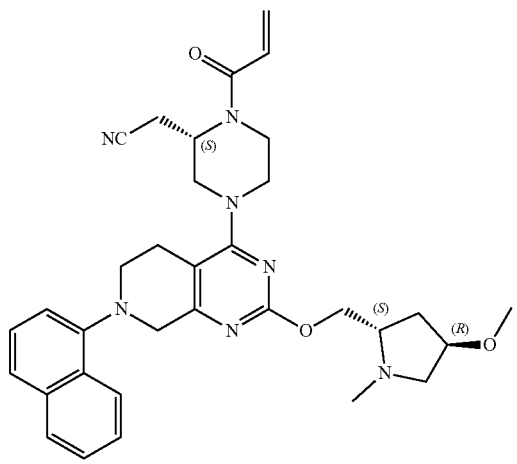

879

2-((S)-1-acryloyl-4-(2-(((2S,4R)-4-methoxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

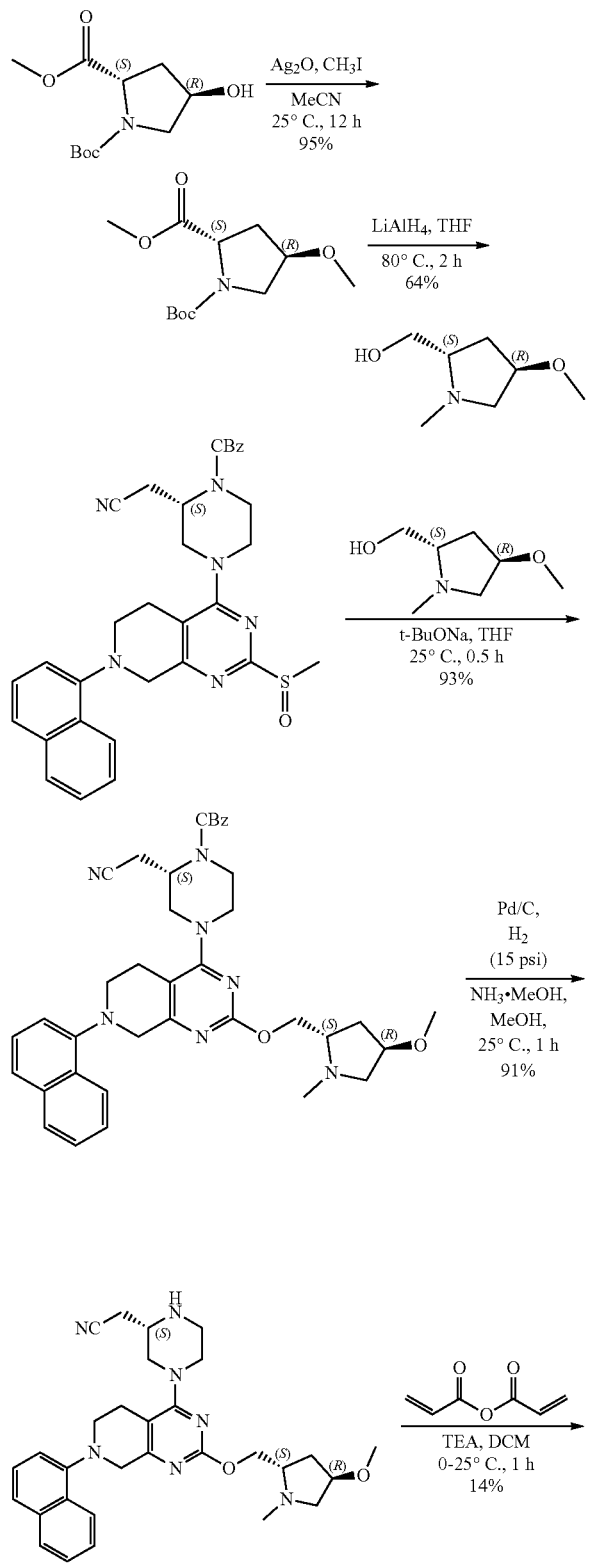

880

-continued

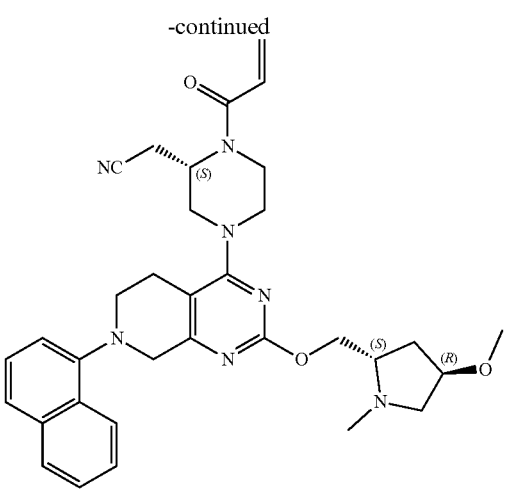

Step 1: 1-tert-butyl 2-methyl (2S,4R)-4-methoxypyrrolidine-1,2-dicarboxylate To a solution of 1-tert-butyl 2-methyl(2S,4R)-4-hydroxypyrrolidine-1,2-dicarboxylate (9 g, 36.7 mmol, 1 eq) in $CH_3CN$ (150 mL) was added $Ag_2O$ (25.5 g, 110 mmol, 3 eq) and $CH_3I$ (54.3 g, 383 mmol, 23.8 mL, 10.4 eq). The mixture was stirred at 25° C. for 12 hours. The reaction mixture was filtered and the filter was concentrated. The residue was purified by column chromatography ($SiO_2$, Petroleum ether/Ethyl acetate=20/1 to 3:1). Compound 1-tert-butyl 2-methyl (2S,4R)-4-methoxypyrrolidine-1,2-dicarboxylate (9 g, 34.7 mmol, 95% yield) was obtained as a colorless oil.

$^1$H NMR (400 MHz, chloroform-d) δ=3.94-3.79 (m, 1H), 3.66 (dd, J=3.2, 11.2 Hz, 1H), 3.44-3.34 (m, 2H), 3.28 (s, 3H), 2.92-2.53 (m, 2H), 2.40-2.25 (m, 4H), 2.12-1.99 (m, 1H), 1.89-1.79 (m, 1H).

Step 2: [(2S,4R)-4-methoxy-1-methyl-pyrrolidin-2-yl]methanol

To a solution of 1-tert-butyl 2-methyl (2S,4R)-4-methoxypyrrolidine-1,2-dicarboxylate (5 g, 19.28 mmol, 1 eq) in THF (100 mL) was added $LiAlH_4$ (2.20 g, 57.8 mmol, 3 eq). The mixture was stirred at 80° C. for 2 hours. The reaction mixture was quenched with saturated $Na_2SO_4$ aqueous solution (6 mL). Then the mixture was filtered and the filter was concentrated. Compound [(2S,4R)-4-methoxy-1-methyl-pyrrolidin-2-yl]methanol (1.8 g, 12.4 mmol, 64% yield) was obtained as a colourless oil and used to next step directly without purification.

$^1$H NMR (400 MHz, chloroform-d) δ=4.43-4.23 (m, 1H), 3.45-3.90 (m, 1H), 3.78-3.69 (m, 3H), 3.68-3.43 (m, 2H), 3.32 (s, 3H), 2.43-2.24 (m, 1H), 2.12-1.95 (m, 1H), 1.52-1.33 (m, 9H).

Step A: benzyl (2S)-2-(cyanomethyl)-4-[2-[[(2S,4R)-4-methoxy-1-methyl-pyrrolidin-2-yl]methoxyl]-7-(1-naphthyl)-6,8-dihydro-5H-pyrido[3,4-d]pyrimidin-4-yl]piperazine-1-carboxylate To a solution of [(2S,4R)-4-methoxy-1-methyl-pyrrolidin-2-yl]methanol (600 mg, 4.13 mmol, 3 eq) and benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (800 mg, 1.38 mmol, 1 eq) in THF (10 mL) was added t-BuONa (397 mg, 4.13 mmol, 3 eq). The mixture was stirred at 25° C. for 0.5 hour. The reaction mixture was diluted with ethyl acetate (30 mL) and washed with water (20 mL). The organic layers was washed with brine (20 mL), dried over $Na_2SO_4$, filtered and concentrated under reduced pressure to give a residue. The residue was purified by column chromatography ($SiO_2$, Ethyl acetate/MeOH=200/1 to 20:1). Compound benzyl (2S)-2-(cyanomethyl)-4-[2-[[(2S,4R)-4-methoxy-1-methyl-pyrrolidin-2-yl]methoxy]-7-(1-naphthyl)-6,8-dihydro-5H-pyrido[3,4-d]pyrimidin-4-yl]piperazine-1-carboxylate (910 mg, 1.28 mmol, 93% yield, 93% purity) was obtained as a yellow oil. LCMS [ESI, M+1]: 662.

Step B: 2-[(2S)-4-[2-[[(2S,4R)-4-methoxy-1-methyl-pyrrolidin-2-yl]methoxy]-7-(1-naphthyl)-6,8-dihydro-5H-pyrido[3,4-d]pyrimidin-4-yl]piperazin-2-yl]acetonitrile $NH_3$ was bubbled in MeOH (80 mL) at −60° C. for 10 minutes. To a solution of benzyl (2S)-2-(cyanomethyl)-4-[2-[[(2S,4R)-4-methoxy-1-methyl-pyrrolidin-2-yl]methoxy]-7-(1-naphthyl)-6,8-dihydro-5H-pyrido[3,4-d]pyrimidin-4-yl]piperazine-1-carboxylate (850 mg, 1.28 mmol, 1 eq) in MeOH (30 mL) was added above $NH_3$.MeOH (20 mL) and dry Pd/C (500 mg, 10% purity) under $N_2$. The suspension was degassed under vacuum and purged with $H_2$ several times. The mixture was stirred under $H_2$ (15 psi) at 25° C. for 1 hour. The reaction mixture was filtered and the filter was concentrated. Compound 2-[(2S)-4-[2-[[(2S,4R)-4-methoxy-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (620 mg, 1.18 mmol, 91% yield) was obtained as a colourless oil and used to next step directly without purification. LCMS [ESI, M+1]: 528.

Step C: 2-[(2S)-4-[2-[[(2S,4R)-4-methoxy-1-methyl-pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a solution of 2-[(2S)-4-[2-[[(2S,4R)-4-methoxy-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (620 mg, 1.18 mmol, 1 eq) in dichloromethane (10 mL) was added TEA (1.19 g, 11.7 mmol, 1.64 mL, 10 eq) at 0° C. After addition, and prop-2-enoyl prop-2-enoate (118 mg, 940 umol, 0.8 eq) in dichloromethane (1 mL) was added dropwise at 0° C. The resulting mixture was stirred at 25° C. for 1 hour. The reaction mixture was quenched with saturated $NaHCO_3$ aqueous solution (1 mL). Then diluted with water (20 mL) and extracted with dichloromethane (20 mL×3). The combined organic layers were washed with brine (20 mL), dried over $Na_2SO_4$, filtered and concentrated under reduced pressure to give a residue. The residue was purified by column chromatography ($Al_2O_3$, EA/MeOH=100/1 to 10:1) and further purified by prep-HPLC (column: Phenomenex Gemini 150*25 mm*10 um; mobile phase: [water (0.05% ammonia hydroxide v/v)-ACN]; B %: 45%-75%, 12 min). Title compound 2-[(2S)-4-[2-[[(2S,4R)-4-methoxy-1-methyl-pyrrolidin-2-yl]methoxy]-7-(1-naphthyl)-6,8-dihydro-5H-pyrido [3,4-d] pyrimidin-4-yl]-1-prop-2-enoyl-piperazin-2-yl]acetonitrile (101 mg, 167 umol, 14% yield, 96.6% purity) was obtained as a white solid by lyophilisation. LCMS [ESI, M+1]: 582.

SFC condition: Column: Chiralcel OJ-3 100×4.6 mm I.D., 3 um, Mobile phase: methanol (0.05% DEA) in $CO_2$ from 5% to 40%, Flow rate: 3 mL/min, Wavelength: 220 nm.

$^1$H NMR (400 MHz, chloroform-d) δ=8.26-8.17 (m, 1H), 7.91-7.82 (m, 1H), 7.61 (d, J=8.0 Hz, 1H), 7.55-7.47 (m, 2H), 7.44 (t, J=8.0 Hz, 1H), 7.15 (d, J=7.6 Hz, 1H), 6.60 (br s, 1H), 6.41 (d, J=16.8 Hz, 1H), 5.84 (br d, J=10.8 Hz, 1H), 5.21-4.53 (m, 1H), 4.42 (dd, J=4.4, 10.4 Hz, 1H), 4.34-4.17 (m, 3H), 4.13 (br d, J=13.6 Hz, 1H), 4.04-3.93 (m, 2H), 3.70-3.42 (m, 3H), 3.31 (s, 5H), 3.22-2.69 (m, 7H), 2.48 (s, 3H), 2.33 (dd, J=5.6, 9.6 Hz, 1H), 2.14-2.04 (m, 1H), 2.02-1.91 (m, 1H).

Example 328

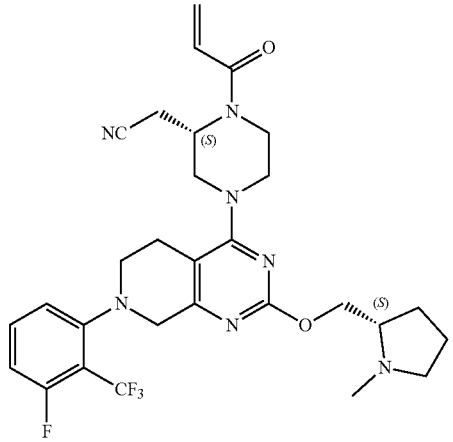

2-((S)-1-acryloyl-4-(7-(3-fluoro-2-(trifluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile

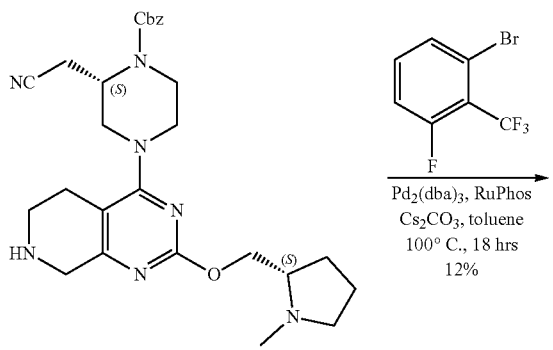

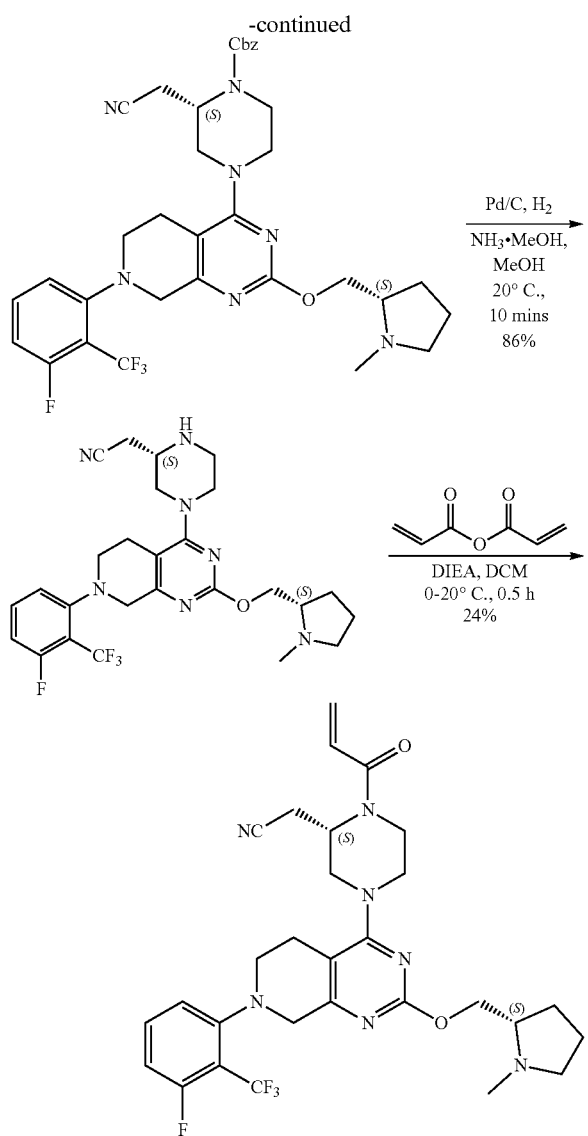

Step A: benzyl (2S)-2-(cyanomethyl)-4-[7-[3-fluoro-2-(trifluoromethyl)phenyl]-2-[[(2S)-1-methyl-pyrrolidin-2-yl]methoxy]-6,8-dihydro-5H-pyrido[3,4-d]pyrimidin-4-yl]piperazine-1-carboxylate To a mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (1.0 g, 1.98 mmol, 1.0 eq) and 1-bromo-3-fluoro-2-(trifluoromethyl)benzene (2.88 g, 11.9 mmol, 6.0 eq) in toluene (20.0 mL) was added Cs$_2$CO$_3$ (1.29 g, 3.96 mmol, 2.0 eq), RuPhos (185 mg, 396 umol, 0.2 eq) and Pd$_2$(dba)$_3$ (272 mg, 297 umol, 0.15 eq), the mixture was stirred at 100° C. for 18 hours under N$_2$. After completion, the reaction mixture was added water (30.0 mL), then extracted with ethyl acetate (2×20.0 mL), the combined organic layer was dried over Na$_2$SO$_4$, filtered and concentrated. The residue was purified by column chromatography (SiO$_2$, Petroleum ether/Ethyl acetate=3/1 to Ethyl acetate:Methanol=20:1). The obtained product was then purified by reversed phase flash again (C18, 0.1% FA in MeCN), the obtained product was adjusted with NaHCO$_3$ solid to pH ~7, the mixture was extracted with ethyl acetate (2×15.0 mL), and the organic layer was dried over Na$_2$SO$_4$, filtered and concentrated. The product benzyl (2S)-2-(cyanomethyl)-4-[7-[3-fluoro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazine-1-carboxylate (160 mg, 236 umol, 12% yield, 98% purity) was obtained as brown oil. LCMS [ESI, M+1]: 668.

Step B: 2-[(2S)-4-[7-[3-fluoro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-[3-fluoro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazine-1-carboxylate (460 mg, 689 umol, 1.0 eq) in MeOH (10 mL) was added Pd/C (300 mg, 10% purity) and NH$_3$.MeOH (10 mL), the suspension was degassed under vacuum and purged with H$_2$ several times. The mixture was stirred under H$_2$ (15 Psi) at 20° C. for 10 mins. After completion, the reaction was filtered through a pad of Celite, and the filtrate was concentrated to give 2-[(2S)-4-[7-[3-fluoro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (320 mg, 591 umol, 86% yield, 98% purity) as yellow solid. LCMS [ESI, M+1]: 534.

Step C: 2-[(2S)-4-[7-[3-fluoro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2S)-4-[7-[3-fluoro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (320 mg, 599 umol, 1.0 eq) in DCM (8.0 mL) was added DIEA (310 mg, 2.40 mmol, 418 uL, 4.0 eq) and prop-2-enoyl prop-2-enoate (75.6 mg, 599 umol, 1.0 eq) at 0° C., the reaction mixture was stirred at 20° C. for 0.5 hour. After completion, the reaction mixture was quenched with MeOH (5.0 mL), and concentrated. The residue was purified by column chromatography (Base Al$_2$O$_3$, Ethyl acetate/Methanol=20/1), then the obtained product was concentrated and purified again by prep-HPLC (column: Gemini 150*25 5 u; mobile phase: [water (0.05% ammonia hydroxide v/v)-ACN]; B %: 51%-81%, 12 min). Title compound 2-[(2S)-4-[7-[3-fluoro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (86.8 mg, 145 umol, 24% yield, 98% purity) was obtained as white solid. LCMS [ESI, M+1]: 588.

$^1$H NMR (400 MHz, chloroform-d) δ 7.55-7.45 (m, 1H), 7.08 (d, J=8.4 Hz, 1H), 7.02-6.91 (m, 1H), 6.68-6.53 (m, 1H), 6.41 (dd, J=1.6, 16.8 Hz, 1H), 5.85 (br d, J=10.8 Hz, 1H), 5.11-4.52 (m, 1H), 4.39 (dd, J=4.8, 10.4 Hz, 1H), 4.17 (dd, J=6.8, 10.4 Hz, 1H), 4.14-4.07 (m, 3H), 3.98 (br d, J=11.6 Hz, 1H), 3.72-3.52 (m, 1H), 3.42-3.25 (m, 2H), 3.23-2.58 (m, 9H), 2.49 (s, 3H), 2.35-2.25 (m, 1H), 2.13-2.01 (m, 1H), 1.91-1.73 (m, 3H).

Example 329

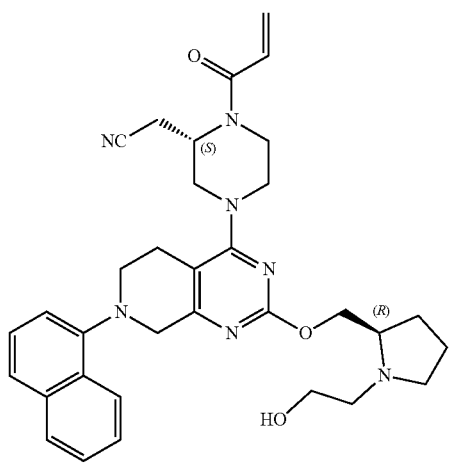

2-[(2S)-4-[2-[[(2R)-1-(2-hydroxyethyl)pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile

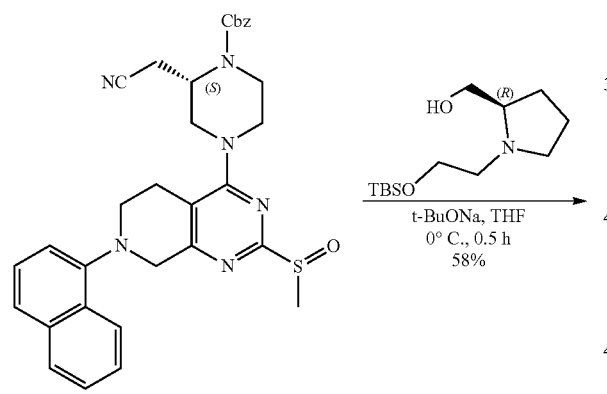

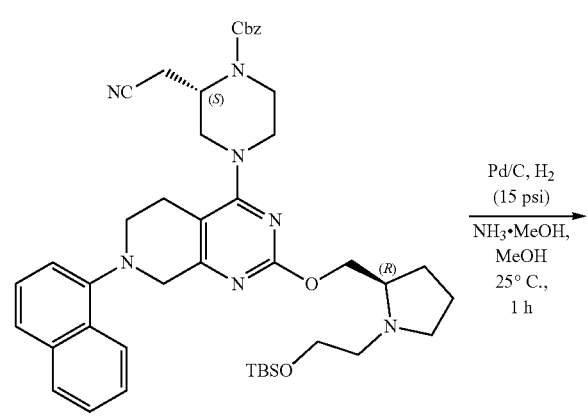

Insert: [(2R)-1-[2-[tert-butyl(dimethyl)silyl]oxy-ethyl]pyrrolidin-2-yl]methanol A mixture of [(2R)-pyrrolidin-2-yl]methanol (0.50 g, 4.94 mmol, 481 uL, 1.00 eq), 2-bromoethoxy-tert-butyl-dimethyl-silane (1.18 g, 4.94 mmol, 1.00 eq) and K₂CO₃ (3.42 g, 24.7 mmol, 5.00 eq) in acetonitrile (30.0 mL) was stirred at 83° C. for 12 hours. The mixture was filtered and the filtrate was concentrated under vacuum. The residue was purified by column chromatography (SiO₂, ethyl acetate/methanol=10/1) to give [(2R)-1-[2-[tert-butyl(dimethyl)silyl]oxyethyl]pyrrolidin-2-yl]methanol (0.50 g, 1.93 mmol, 39% yield) as a colorless oil.

¹H NMR (400 MHz, chloroform-d) δ=3.70 (t, J=6.0 Hz, 2H), 3.60 (dd, J=3.6, 10.8 Hz, 1H), 3.36 (dd, J=3.6, 10.8 Hz, 1H), 3.20 (td, J=4.4, 9.2 Hz, 1H), 2.89 (td, J=6.4, 12.8 Hz, 1H), 2.74-2.65 (m, 1H), 2.50 (td, J=5.2, 12.8 Hz, 1H), 2.42-2.32 (m, 1H), 1.92-1.81 (m, 1H), 1.78-1.66 (m, 3H), 0.90 (d, J=0.8 Hz, 9H), 0.07 (d, J=0.4 Hz, 6H).

Step A: benzyl (2S)-4-[2-[[(2R)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate To a solution of [(2R)-1-[2-[tert-butyl(dimethyl)silyl]oxyethyl]pyrrolidin-2-yl]methanol (344 mg, 1.33 mmol, 1.10 eq) in THF (10.0 mL) was added t-BuONa (232 mg, 2.41 mmol, 2.00 eq) and benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 0.70 g, 1.21 mmol, 1.00 eq) at 0° C. After stirred at 0° C. for 0.5 h, the mixture was diluted with ethyl acetate (10.0 mL), washed with water (1×10.0 mL), dried over Na₂SO₄, filtered and concentrated under vacuum. The residue was purified by column chromatography (Al₂O₃, ethyl acetate/petroleumethyl=3/1) to give benzyl (2S)-4-[2-[[(2R)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (0.60 g, 704 umol, 58% yield) as a yellow solid. LCMS [ESI, M+1]: 776.

¹H NMR (400 MHz, chloroform-d) δ=8.23-8.18 (m, 1H), 7.90-7.83 (m, 1H), 7.61 (d, J=8.4 Hz, 1H), 7.54-7.47 (m, 2H), 7.46-7.34 (m, 6H), 7.14 (d, J=7.2 Hz, 1H), 5.21 (s, 2H), 4.70 (br s, 1H), 4.34 (br dd, J=4.2, 10.6 Hz, 1H), 4.30-4.20 (m, 2H), 4.17-3.89 (m, 4H), 3.75 (t, J=6.8 Hz, 2H), 3.49 (br d, J=8.4 Hz, 1H), 3.38-3.13 (m, 4H), 3.10-2.90 (m, 4H), 2.89-2.70 (m, 3H), 2.63-2.52 (m, 1H), 2.41-2.31 (m, 1H), 2.04-1.94 (m, 1H), 1.87-1.73 (m, 3H), 0.88 (s, 9H), 0.05 (d, J=1.2 Hz, 6H).

Step B: 2-[(2S)-4-[2-[[(2R)-1-[2-[tert-butyl(dimethyl)silyl]oxyethyl]pyrrolidin-2-yl]methoxy]-7-(1-naphthyl)-6,8-dihydro-5H-pyrido[3,4-d]pyrimidin-4-yl]piperazin-2-yl]acetonitrile NH₃ was bubbled in methanol (50.0 mL) at −78° C. for 10 minutes. Benzyl (2S)-4-[2-[[(2R)-1-[2-[tert-butyl(dimethyl) silyl]oxyethyl]pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (0.60 g, 773 umol, 1.00 eq) and Pd/C (0.1 g, 10% purity) were added into the above solution. After stirred at 25° C. for 1 hour under H₂ at 15 psi, the catalyst was filtered off and the filter cake was wash with THF (10.0 mL). The filtrate was concentrated under vacuum to give 2-[(2S)-4-[2-[[(2R)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]piperazin-2-yl]acetonitrile (0.50 g, crude) as a yellow oil and used into next step without further purification. LCMS [ESI, M/2+1]: 321.

Step C: 2-[(2S)-4-[2-[[(2R)-1-[2-[tert-butyl(dimethyl)silyl]oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a solution of 2-[(2S)-4-[2-[[(2R)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]piperazin-2-yl]acetonitrile (0.50 g, crude) and TEA (394 mg, 3.89 mmol, 542 uL) in dichloromethane (5.00 mL) was added prop-2-enoyl prop-2-enoate (98.2 mg, 779 umol) at −40° C. After stirred at 25° C. for 1 hour, the mixture was quenched with saturated sodium bicarbonate (0.10 mL) and concentrated under vacuum. The residue was purified by column chromatography (Al₂O₃, methanol/ethyl acetate=10/1) to give 2-[(2S)-4-[2-[[(2R)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (0.35 g, 427 umol, two steps 55% yield) as a yellow solid. LCMS [ESI, M+1]: 696.

Step D: 2-[(2S)-4-[2-[[(2R)-1-(2-hydroxyethyl)pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile A mixture of 2-[(2S)-4-[2-[[(2R)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (0.35 g, 503 umol, 1.00 eq), KF (146 mg, 2.51 mmol, 58.9 uL, 5.00 eq) and 18-CROWN-6 (665 mg, 2.51 mmol, 5.00 eq) in THF (5.00 mL) was stirred at 40° C. for 12 hours. The mixture was concentrated under vacuum. The residue was purified by reverse phase flash [water (TFA, 0.10%)/acetonitrile] and prep-HPLC (column: Phenomenex Gemini 150*25 mm*10 um; mobile phase: [water (0.05% ammonia hydroxide v/v)-ACN]; B %: 45%-75%, 12 min). The desired fractions were collected and lyophilized to give title compound 2-[(2S)-4-[2-[[(2R)-1-(2-hydroxyethyl)pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (EXAMPLE 329, 146 mg, 245 umol, 49% yield, 97.7% purity) as a white solid. LCMS [ESI, M+1]:582.

SFC condition: "Column: Chiralcel OJ-3 100×4.6 mm I.D., 3 um, Mobile phase: methanol (0.05% DEA) in CO₂ from 5% to 40%, Flow rate: 3 mL/min, Wavelength: 220 nm".

¹H NMR (400 MHz, chloroform-d) δ=8.29-8.18 (m, 1H), 7.95-7.82 (m, 1H), 7.61 (d, J=8.0 Hz, 1H), 7.56-7.47 (m, 2H), 7.44 (t, J=7.6 Hz, 1H), 7.15 (d, J=7.2 Hz, 1H), 6.60 (br s, 1H), 6.46-6.31 (m, 1H), 5.83 (br d, J=10.8 Hz, 1H), 5.19-4.47 (m, 1H), 4.38-4.22 (m, 3H), 4.21-4.09 (m, 2H), 4.02 (br d, J=11.2 Hz, 2H), 3.71-3.57 (m, 2H), 3.53-3.27 (m, 3H), 3.22-2.76 (m, 9H), 2.62 (td, J=3.6, 12.4 Hz, 1H), 2.41-2.28 (m, 1H), 2.11-1.95 (m, 1H), 1.89-1.77 (m, 3H).

Example 330

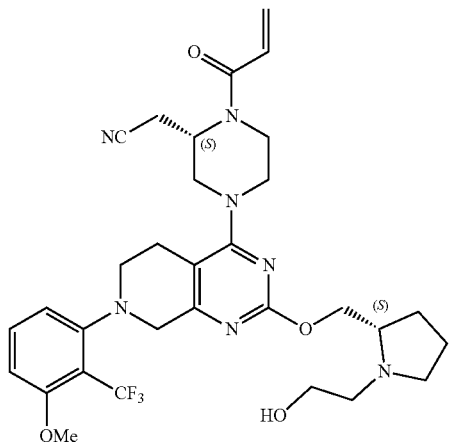

2-[(2S)-4-[7-[3-methoxy-2-(trifluoromethyl)phenyl]-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

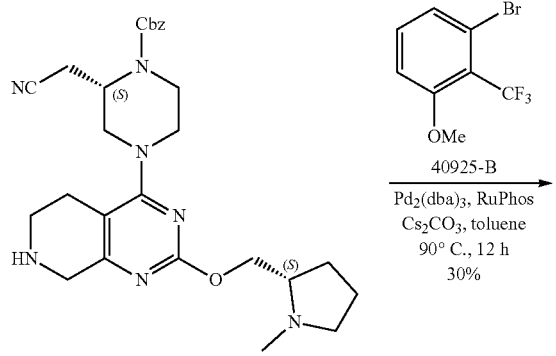

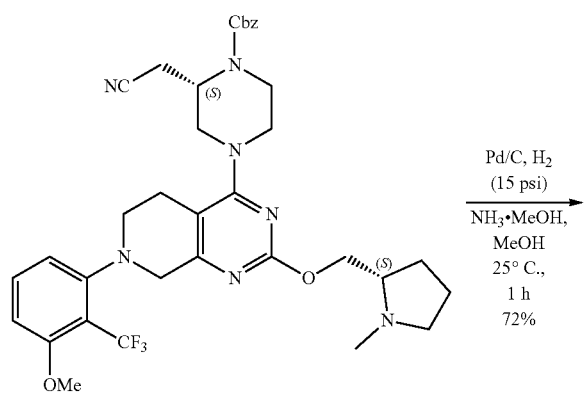

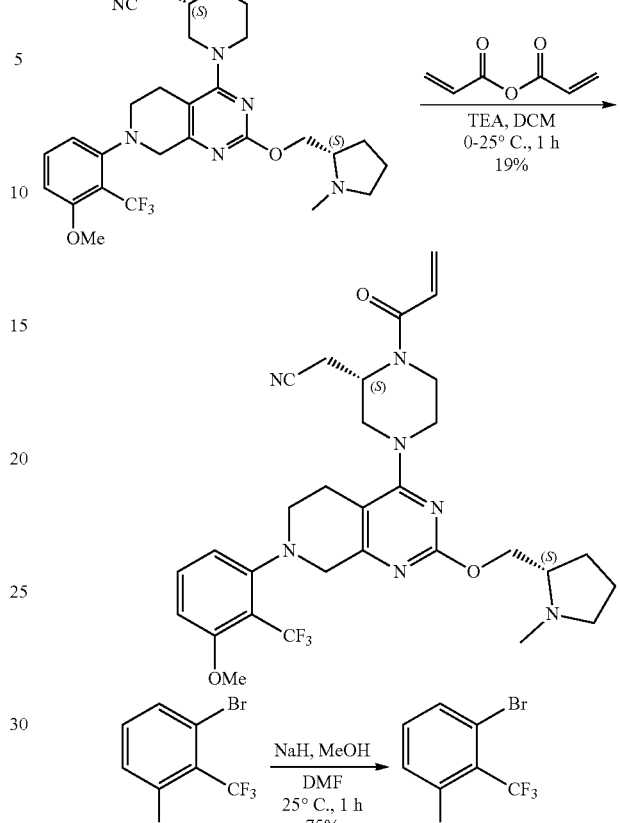

Insert:
1-bromo-3-methoxy-2-(trifluoromethyl)benzene

To a solution of MeOH (264 mg, 8.23 mmol, 333 uL, 2.00 eq) in DMF (25.0 mL) was added NaH (329 mg, 8.23 mmol, 60% purity in mineral oil, 2.00 eq). The solution was mixed at room temperature (25° C.) for 30 minutes after which time 1-bromo-3-fluoro-2-(trifluoromethyl)benzene (1.00 g, 4.12 mmol, 1.00 eq) was added. The solution was then stirred at 25° C. for 0.5 hour. Upon completion, the mixture was diluted with water (50 mL) and extracted with EtOAc (2×50 mL). The organic layers were washed with brine (30 mL), dried over Na$_2$SO$_4$ and concentrated under vacuum. The residue was purified by silica gel chromatography (PE/EtOAc 1/0 to 100/1) to give 1-bromo-3-methoxy-2-(trifluoromethyl)benzene (880 mg, 3.11 mmol, 75% yield, 90.0% purity) as a colorless oil.

$^1$H NMR (400 MHz, chloroform-d) δ=7.34-7.27 (m, 2H), 6.99 (br d, J=7.2 Hz, 1H), 3.91 (s, 3H).

Step A: (2S)-2-(cyanomethyl)-4-[7-[3-methoxy-2-(trifluoromethyl)phenyl]-2-[[(2S)-1-methylpyrrolidin-2-yl]methoxy]-6,8-dihydro-5H-pyrido[3,4-d]pyrimidin-4-yl]piperazine-1-carboxylate benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 550 mg, 1.09 mmol, 1.00 eq), 1-bromo-3-methoxy-2-(trifluoromethyl)benzene (416 mg, 1.63 mmol, 1.50 eq), RuPhos (152 mg, 326 umol, 0.30 eq), Cs₂CO₃ (1.06 g, 3.26 mmol, 3.00 eq) and Pd₂(dba)₃ (149 mg, 163 umol, 0.15 eq) in toluene (30.0 mL) was de-gassed and then heated to 90° C. for 12 hours under N₂. Upon completion, the mixture was concentrated under vacuum. The residue was diluted with water (10 mL) and extracted with EtOAc (2×40 mL). The organic layers were dried over Na₂SO₄ and concentrated under vacuum. The residue was purified by reversed-phase flash [water (0.1% FA)/acetonitrile]. The collected desired fractions were neutralized with saturated sodium bicarbonate solution, concentrated under vacuum to remove MeCN and extracted with EtOAc (2×100 mL). The organic layers were dried over Na₂SO₄ and concentrated under vacuum to give benzyl (2S)-2-(cyanomethyl)-4-[7-[3-methoxy-2-(trifluoromethyl)phenyl]-2-[[(2S)-1-methylpyrrolidin-2-yl]methoxy]-6,8-dihydro-5H-pyrido[3,4-d]pyrimidin-4-yl]piperazine-1-carboxylate (230 mg, 321 umol, 30% yield, 94.9% purity) as a yellow solid. LCMS [ESI, M+1]: 680.

Step B: 2-[(2S)-4-[7-[3-methoxy-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-[3-methoxy-2-(trifluoromethyl)phenyl]-2-[[(2S)-1-methylpyrrolidin-2-yl]methoxy]-6,8-dihydro-5H-pyrido[3,4-d]pyrimidin-4-yl]piperazine-1-carboxylate (230 mg, 338 umol, 1.00 eq) in MeOH (4.00 mL) was added NH₃/MeOH (7 M, 4.00 mL), Pd/C (70.0 mg, 10% purity) under N₂. The suspension was degassed under vacuum and purged with H₂ several times. The mixture was stirred under H₂ (15 psi) at 25° C. for 1 hour. Upon completion, the catalyst was filtered off and the filtrate was concentrated to give 2-[(2S)-4-[7-[3-methoxy-2-(trifluoromethyl) phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 242 umol, 72% yield, 88.1% purity) as a yellow solid which was used directly in the next step without further purification. LCMS [ESI, M+1]: 546.

Step C: 2-[(2S)-4-[7-[3-methoxy-2-(trifluoromethyl)phenyl]-2-[[(2S)-1-methyl pyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-[3-methoxy-2-(trifluoromethyl) phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 242 umol, 1.00 eq) and TEA (122 mg, 1.21 mmol, 168 uL, 5.00 eq) in DCM (3.00 mL) was added prop-2-enoyl prop-2-enoate (30.5 mg, 242 umol, 1.00 eq) dropwise at 0° C. The mixture was stirred at 25° C. for 1 hour. Upon completion, the mixture was quenched with MeOH (0.1 mL) and water (2 mL). Layers were separated. The aqueous phase was extracted with EtOAc (2×8 mL). The combined organic layers were dried over Na₂SO₄ and concentrated under vacuum. The residue was purified by prep-TLC (EtOAc/MeOH 7/1) and then prep-HPLC (column: Gemini 150*25 5 u; mobile phase: [water (0.05% ammonia hydroxide v/v)-ACN]; B %: 50%-80%, 12 min) and lyophilized to give 2-[(2S)-4-[7-[3-methoxy-2-(trifluoromethyl)phenyl]-2-[[(2S)-1-methyl pyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 330, 28.2 mg, 45.6 umol, 19% yield, 96.8% purity) as a white solid. LCMS [ESI, M+1]: 600.

SFC condition: Column: Chiralcel OD-3 100×4.6 mm I.D., 3 um Mobile phase: methanol (0.05% DEA) in CO₂ from 5% to 40% Flow rate: 3 mL/min Wavelength: 220 nm.

¹H NMR (400 MHz, chloroform-d) δ=7.42 (t, J=8.4 Hz, 1H), 6.84 (d, J=8.0 Hz, 1H), 6.79 (d, J=8.4 Hz, 1H), 6.59 (br s, 1H), 6.46-6.34 (m, 1H), 5.83 (br d, J=10.4 Hz, 1H), 5.09 (br s, 1H), 4.37 (dd, J=5.2, 10.8 Hz, 1H), 4.21-4.02 (m, 4H), 4.01-3.77 (m, 5H), 3.75-3.21 (m, 3H), 3.20-2.98 (m, 3H), 2.97-2.56 (m, 5H), 2.48 (s, 3H), 2.35-2.23 (m, 1H), 2.12-1.98 (m, 1H), 1.91-1.72 (m, 3H).

Example 331

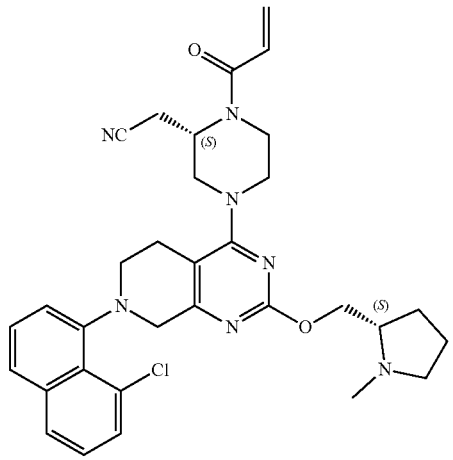

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

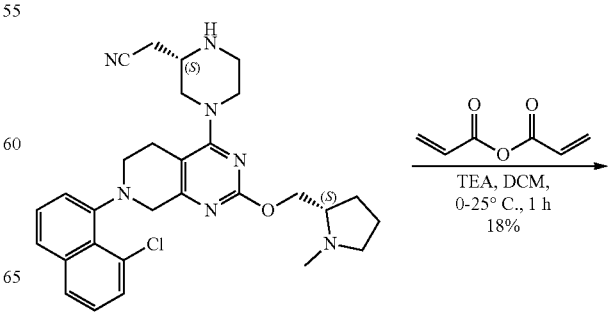

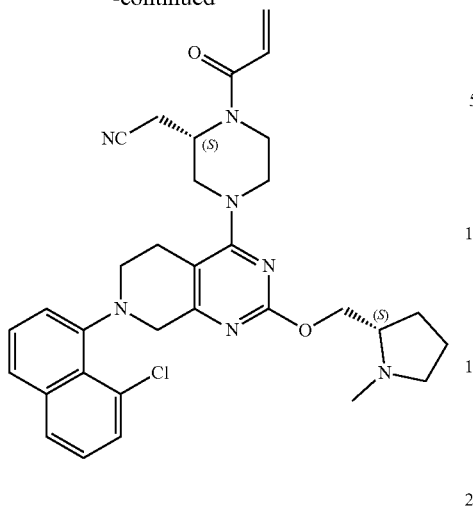

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (700 mg, 1.16 mmol, 1.00 eq, 2 HCl) and TEA (1.76 g, 17.4 mmol, 2.42 mL, 15.0 eq) in anhydrous DCM (17.0 mL) was added prop-2-enoyl prop-2-enoate (146 mg, 1.16 mmol, 1.00 eq) at 0° C. The mixture was stirred for 1 hour at 25° C. Upon completion, the mixture was quenched with MeOH (1 mL) and water (10 mL). The separated aqueous phase was extracted with EtOAc (2×20 mL). The combined organic layers were dried over $Na_2SO_4$ and concentrated under vacuum. The residue was purified by silica gel chromatography (petroleum ether/ethyl acetate 2/1 to 0/1) and then prep-HPLC (column: Phenomenex Gemini 150*25 mm*10 um; mobile phase: [water (0.05% ammonia hydroxide v/v)-ACN]; B %: 52%-82%, 12 min). The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 331, 122 mg, 205 umol, 18% yield, 98.5% purity) as a white solid. LCMS [ESI, M+1]:586.

SFC condition: Column: Chiralpak AD-3 100×4.6 mm I.D., 3 um, Mobile phase: 40% iso-propanol (0.05% DEA) in $CO_2$ Flow rate: 3 mL/min Wavelength: 220 nm.

$^1$H NMR (400 MHz, chloroform-d) δ=7.76 (br d, J=8.4 Hz, 1H), 7.62 (t, J=7.6 Hz, 1H), 7.53 (d, J=7.2 Hz, 1H), 7.45 (td, J=7.6, 13.2 Hz, 1H), 7.37-7.31 (m, 1H), 7.27-7.17 (m, 1H), 6.59 (br s, 1H), 6.45-6.33 (m, 1H), 5.83 (br d, J=10.4 Hz, 1H), 5.08 (br s, 1H), 4.49-4.30 (m, 2H), 4.22-3.66 (m, 5H), 3.63-3.32 (m, 2H), 3.32-2.97 (m, 5H), 2.91-2.52 (m, 4H), 2.48 (d, J=2.4 Hz, 3H), 2.36-2.21 (m, 1H), 2.12-1.96 (m, 1H), 1.86-1.70 (m, 3H).

Example 332

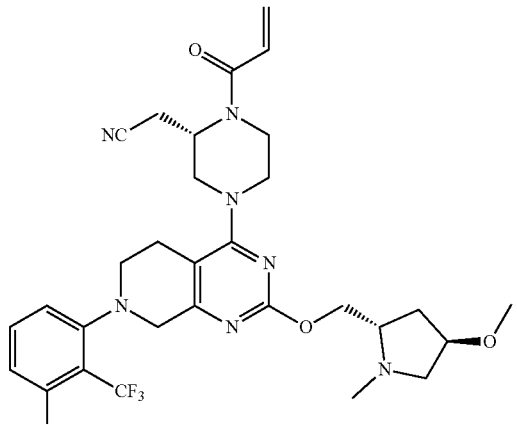

2-[(2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile

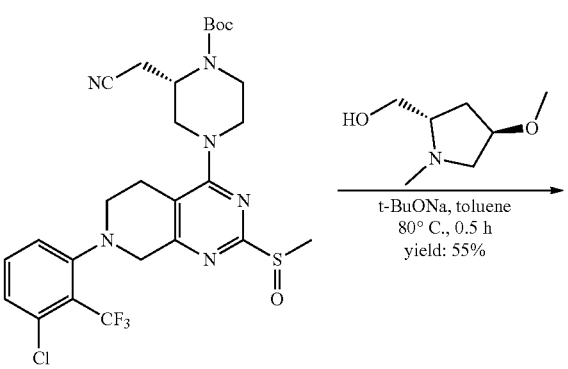

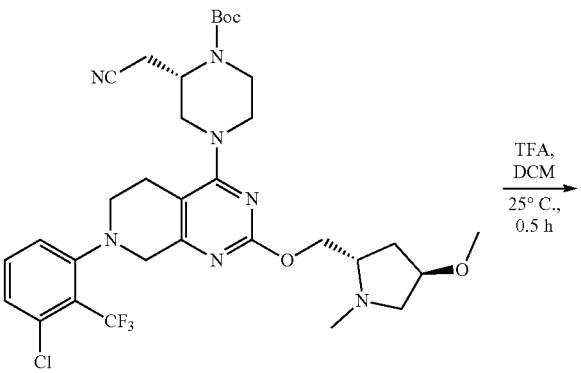

-continued

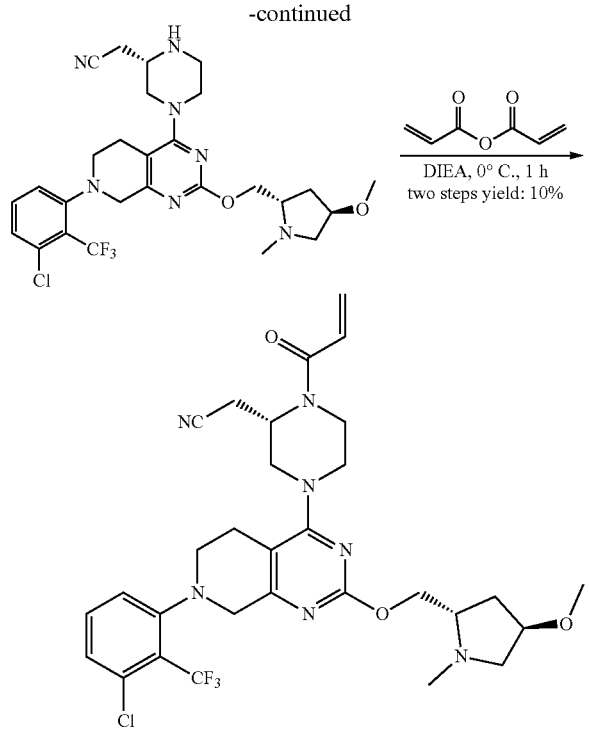

Step A: tert-butyl (2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido[3,4-d]pyrimidin-4-yl]-2-(cyanomethyl)piperazine-1-carboxylate To a solution of tert-butyl (2S)-4-[7-[3-chloro-2-(trifluoromethyl)phenyl]-2-methylsulfinyl-6,8-dihydro-5H-pyrido[3,4-d]pyrimidin-4-yl]-2-(cyanomethyl)piperazine-1-carboxylate (450 mg, 751 umol, 1.0 eq) and [(2S,4R)-4-methoxy-1-methyl-pyrrolidin-2-yl]methanol (218 mg, 1.50 mmol, 2.0 eq) in toluene (20.0 mL) was added t-BuONa (144 mg, 1.50 mmol, 2.0 eq). The mixture was stirred at 0° C. for 10 min. The reaction mixture was quenched by addition H$_2$O (10.0 mL) at 20° C., and the reaction mixture was extracted with EA (20.0 mL×3). The combined organic layers were dried over Na$_2$SO$_4$, filtered and concentrated under reduced pressure to give a residue. The residue was purified by column chromatography (SiO$_2$, Petroleum ether/Ethyl acetate=1/1 to EA/MeOH=10/1). The product tert-butyl (2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido[3,4-d]pyrimidin-4-yl]-2-(cyanomethyl)piperazine-1-carboxylate (0.30 g, 413 umol, 55% yield, 93.7% purity) was obtained as a white solid. LCMS [ESI, M+1]: 680.

Step B: 2-[(2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido [3,4-d]pyrimidin-4-yl]-2-(cyanomethyl)piperazine-1-carboxylate (270 mg, 397 umol, 1.0 eq) in DCM (2.0 mL) was added TFA (3.08 g, 27.0 mmol, 2.0 mL, 68.1 eq). The mixture was stirred at 20° C. for 10 min. The reaction mixture was concentrated under reduced pressure to give a residue. The product 2-[(2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido[3,4-d]pyrimidin-4-yl]piperazin-2-yl]acetonitrile (300 mg, crude, 2TFA) was obtained as a yellow solid. LCMS [ESI, M+1]: 580.

Step C: 2-[(2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido[3,4-d]pyrimidin-4-yl]piperazin-2-yl]acetonitrile (300 mg, 371 umol, 1.0 eq, 2TFA) in DCM (3.0 mL) was added DIEA (480 mg, 3.71 mmol, 647 uL, 10.0 eq). The mixture was stirred at 0° C. for 1 hour. The reaction mixture was quenched by addition MeOH (10.0 mL) at 20° C., and concentrated under reduced pressure to give a residue. The residue was purified by prep-HPLC (column: Phenomenex Gemini 150*25 mm*10 um; mobile phase: [water (0.05% ammonia hydroxide v/v)-ACN]; B %: 50%-80%, 12 min). The residue was concentrated under reduced pressure to remove ACN, and then lyophilization. Title compound 2-[(2S)-4-[7-[3-chloro-2-(trifluoromethyl)phenyl]-2-[[(2S,4R)-4-methoxy-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile (27.6 mg, 43.5 umol, two steps 10% yield, 100% purity) was obtained as a white solid. LCMS [ESI, M+1]: 634.

$^1$H NMR (400 MHz, Chloroform-d) δ=7.44-7.37 (m, 1H), 7.32-7.40 (m, 1H) 7.19 (d, J=8.4 Hz, 1H), 6.57 (br, d, J=14.1 Hz, 1H), 6.44-6.37 (m, 1H), 5.84 (br, d, J=10.8 Hz, 1H), 5.1 (br, s, 1H), 4.45-4.35 (m, 1H), 4.19 (br, dd, J=5.9, 10.9 Hz, 1H), 4.10 (s, 3H), 4.00-3.90 (m, 2H), 3.75-3.4 (m, 2H), 3.40-3.00 (m, 8H), 3.00-2.65 (m, 5H), 2.45 (s, 3H), 2.38-2.28 (m, 1H), 2.15-2.00 (m, 1H), 2.00-1.90 (m, 1H).

Example 333

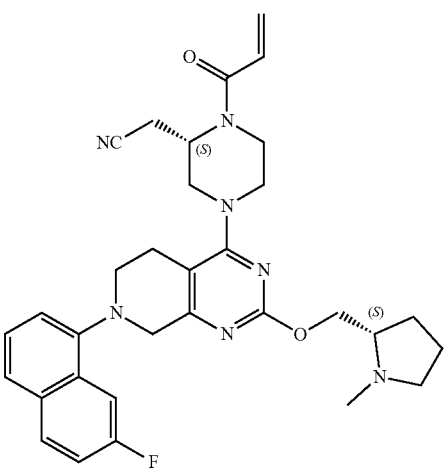

897

2-[(2S)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

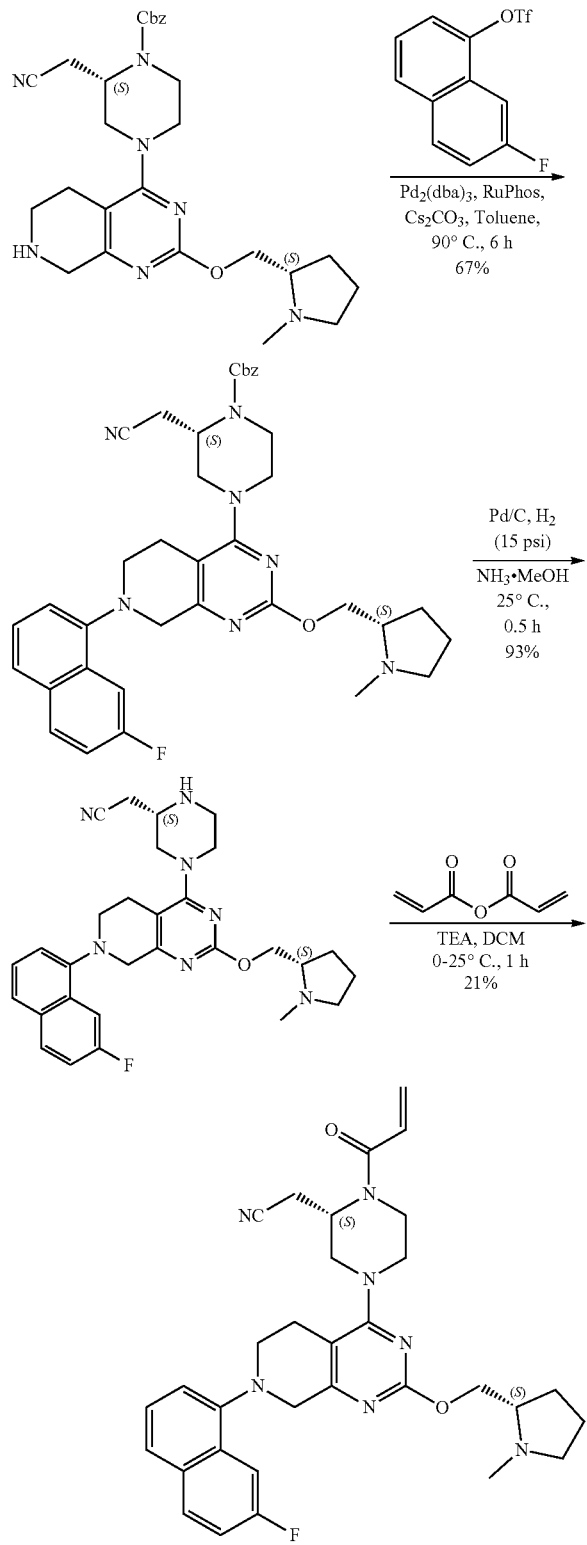

898

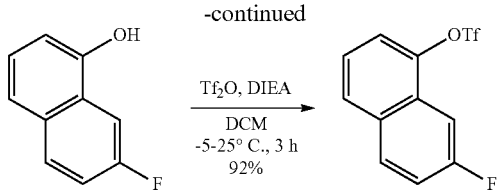

Insert: (7-fluoro-1-naphthyl) trifluoromethanesulfonate

To a solution of 7-fluoronaphthalen-1-ol (980 mg, 6.04 mmol, 1 eq) and DIEA (2.34 g, 18.1 mmol, 3.16 mL, 3 eq) in DCM (40 mL) was added Tf$_2$O (2.56 g, 9.07 mmol, 1.50 mL, 1.5 eq) dropwise at −5° C. The mixture was stirred at 25° C. for 3 hours. Then the mixture was concentrated under vacuum. The residue was purified by silica gel chromatography (Petroleum ether/Ethyl acetate=100/1 to 10/1). Compound (7-fluoro-1-naphthyl) trifluoromethanesulfonate (1.63 g, 5.54 mmol, 92% yield) was obtained as a colorless oil.

$^1$H NMR (400 MHz, chloroform-d) δ=7.92 (dd, J=5.6, 9.0 Hz, 1H), 7.87 (d, J=8.0 Hz, 1H), 7.70 (dd, J=2.4, 9.9 Hz, 1H), 7.56-7.50 (m, 1H), 7.49-7.43 (m, 1H), 7.42-7.34 (m, 1H).

Step A: benzyl (2S)-2-(cyanomethyl)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 330 mg, 463 umol, 1 eq), (7-fluoro-1-naphthyl) trifluoromethanesulfonate (273 mg, 927 umol, 2 eq), Pd$_2$(dba)$_3$ (84.9 mg, 92.7 umol, 0.2 eq), RuPhos (64.9 mg, 139 umol, 0.3 eq) and Cs$_2$CO$_3$ (453 mg, 1.39 mmol, 3 eq) in toluene (30 mL) was degassed and purged with N$_2$ for 3 times, and then the mixture was stirred at 90° C. for 6 hours under N$_2$ atmosphere. The reaction mixture was added H$_2$O (1×200 mL) and ethyl acetate (1×250 mL). The organic phase was separated, washed with brine (1×200 mL), dried over sodium sulfate, filtered and concentrated under reduced pressure to give a residue. The residue was purified by reversed phase flash [water (0.1% FA)/acetonitrile]. The desired fractions were collected and neutralized to pH=7 with saturated NaHCO$_3$ solution, and then extracted with ethyl acetate (1×200 mL). The separated organic layer was dried over sodium sulfate, filtered and concentrated under vacuum. Compound benzyl (2S)-2-(cyanomethyl)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (200 mg, 308 umol, 100% purity, 67% yield) was obtained as a yellow oil. LCMS [ESI, M+1]: 650.

$^1$H NMR (400 MHz, chloroform-d) δ=7.80-7.70 (m, 2H), 7.53 (d, J=8.4 Hz, 1H), 7.36-7.24 (m, 6H), 7.24-7.16 (m, 1H), 7.10 (d, J=7.2 Hz, 1H), 5.19-5.09 (m, 2H), 4.62 (br s, 1H), 4.51 (dd, J=6.0, 11.2 Hz, 1H), 4.26 (dd, J=5.6, 11.3 Hz, 1H), 4.15 (s, 2H), 4.11-3.99 (m, 2H), 3.90 (br d, J=12.8 Hz, 1H), 3.38-3.11 (m, 5H), 3.08-2.95 (m, 2H), 2.93-2.71 (m, 3H), 2.70-2.62 (m, 1H), 2.60 (s, 3H), 2.53-2.42 (m, 1H), 2.15-2.02 (m, 1H), 1.96-1.75 (m, 3H).

Step B: 2-[(2S)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile A mixture of benzyl (2S)-2-(cyanomethyl)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (810 mg, 1.25 mmol, 1 eq), Pd/C (400 mg, 10% purity) and NH$_3$ in MeOH (7 M, 150 mL) was degassed and purged with H$_2$ for 3 times, and then the mixture was stirred at 25° C. for 0.5 hr under H$_2$ atmosphere at 15 psi pressure. The mixture was filtered and concentrated under vacuum. 2-[(2S)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (600 mg, 1.16 mmol, 93% yield, 99.4% purity) was obtained as a yellow oil. LCMS [ESI, M+1]: 516.

$^1$H NMR (400 MHz, chloroform-d) δ=7.89-7.79 (m, 2H), 7.61 (br d, J=8.4 Hz, 1H), 7.40 (t, J=7.8 Hz, 1H), 7.32-7.24 (m, 1H), 7.19 (br d, J=7.6 Hz, 1H), 4.51 (dd, J=5.6, 10.9 Hz, 1H), 4.30-4.19 (m, 3H), 4.05 (br d, J=12.4 Hz, 1H), 3.88 (br d, J=12.0 Hz, 1H), 3.37-3.21 (m, 4H), 3.19-3.09 (m, 2H), 3.06-2.84 (m, 5H), 2.61-2.53 (m, 5H), 2.47-2.36 (m, 1H), 2.19-2.08 (m, 1H), 1.97-1.76 (m, 3H).

Step C: 2-[(2S)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2S)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (600 mg, 1.16 mmol, 1 eq) and TEA (589 mg, 5.82 mmol, 810 uL, 5 eq) in DCM (30 mL) was added prop-2-enoyl prop-2-enoate (117 mg, 931 umol, 0.8 eq) at 0° C. The mixture was stirred at 25° C. for 1 hour. The reaction mixture was quenched with saturated NaHCO$_3$ solution (10 mL) at 0° C., and then extracted with CH$_2$Cl$_2$ (2×30 mL). The combined organic layers were washed with brine (1×50 mL), dried over sodium sulfate, filtered and concentrated under vacuum to give a residue. The residue was purified by column chromatography (Al$_2$O$_3$, Ethyl acetate/Methanol=20/1 to 3/1). The residue was purified by prep-HPLC (column: waters xbridge 150*25 5 u; mobile phase: [water (0.05% ammonia hydroxide v/v)-ACN]; B %: 50%-80%, 10 min). Title compound 2-[(2S)-4-[7-(7-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl] acetonitrile (EXAMPLE 333, 139 mg, 244 umol, 21% yield, 100% purity) was obtained as a white solid. LCMS [ESI, M+1]: 570.

SFC condition: "Column: Chiralpak AD-3 100×4.6 mm I.D., 3 um, Mobile phase: methanol (0.05% DEA) in CO$_2$ from 5% to 40%, Flow rate: 3 mL/min, Wavelength: 220 nm".

$^1$H NMR (400 MHz, chloroform-d) δ=7.92-7.80 (m, 2H), 7.63 (d, J=8.0 Hz, 1H), 7.42 (t, J=7.6 Hz, 1H), 7.33-7.25 (m, 1H), 7.20 (d, J=7.2 Hz, 1H), 6.62 (br s, 1H), 6.47-6.37 (m, 1H), 5.85 (br d, J=10.8 Hz, 1H), 5.27-4.52 (m, 1H), 4.41 (dd, J=4.8, 10.4 Hz, 1H), 4.25 (br s, 2H), 4.22-4.10 (m, 2H), 4.09-3.87 (m, 2H), 3.77-3.25 (m, 2H), 3.24-3.06 (m, 3H), 3.05-2.59 (m, 6H), 2.50 (s, 3H), 2.38-2.23 (m, 1H), 2.15-2.00 (m, 1H), 1.99-1.81 (m, 3H).

Example 334

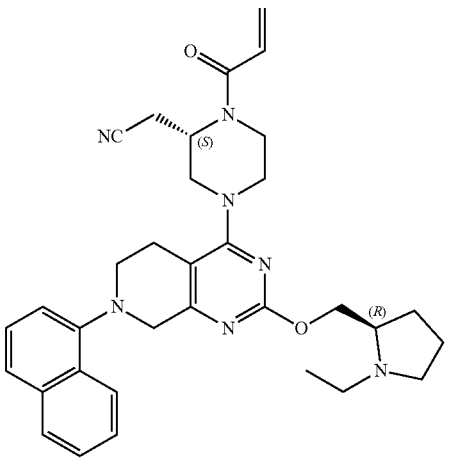

2-(1-acryloyl-4-(7-(7-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

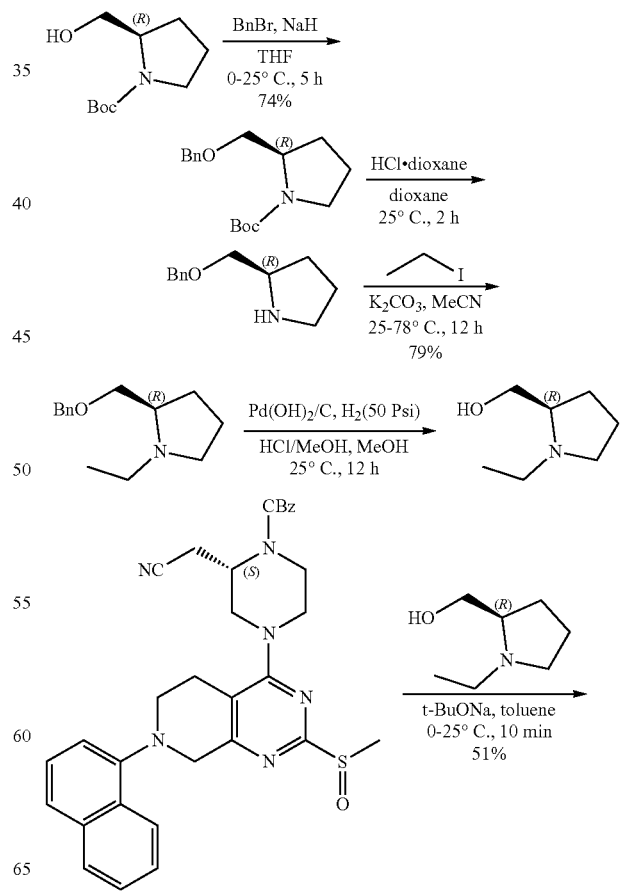

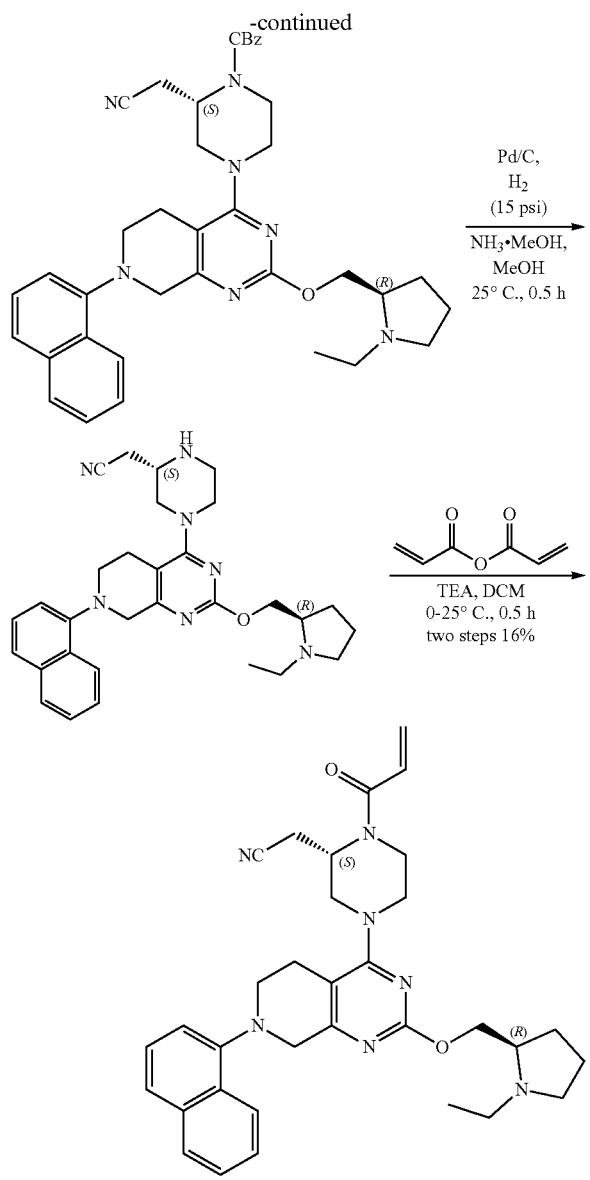

Step A: tert-butyl (2R)-2-(benzyloxymethyl)pyrrolidine-1-carboxylate

To a solution of NaH (1.11 g, 27.8 mmol, 60% purity, 1.2 eq) in THF (80 mL) was added a solution of tert-butyl (2R)-2-(hydroxymethyl)pyrrolidine-1-carboxylate (4.67 g, 23.2 mmol, 1 eq) in THF (20 mL) at 0° C. and the mixture was stirred at 0° C. for 1 hour. BnBr (5.95 g, 34.8 mmol, 4.13 mL, 1.5 eq) was added dropwise at 0° C. and the mixture was stirred at 25° C. for 4 hours. The reaction mixture was quenched with saturated ammonium chloride solution (20 mL) at 0° C., and then diluted with ethyl acetate (2×100 mL). The organic layers were washed with water (1×150 mL) and brine (1×150 mL), dried over sodium sulfate, filtered and concentrated under reduced pressure to give a residue. The residue was purified by column chromatography (SiO$_2$, Petroleum ether/Ethyl acetate=100/1 to 2/1). Compound tert-butyl (2R)-2-(benzyloxymethyl)pyrrolidine-1-carboxylate (5.03 g, 17.3 mmol, 74% yield) was obtained as a colorless oil.

$^1$H NMR (400 MHz, chloroform-d) δ=7.37-7.14 (m, 5H), 4.47 (br s, 2H), 4.07-3.77 (m, 1H), 3.67-3.07 (m, 4H), 2.08-1.68 (m, 4H), 1.38 (s, 9H).

Step B: (2R)-2-(benzyloxymethyl)pyrrolidine

To a mixture of tert-butyl (2R)-2-(benzyloxymethyl)pyrrolidine-1-carboxylate (4 g, 13.7 mmol, 1 eq) in dioxane (80 mL) was added HCl/dioxane (4 M, 120 mL, 35 eq). The mixture was stirred at 25° C. for 2 hours. The reaction mixture was concentrated under reduced pressure to give a residue. The crude product was used directly into next step without further purification. Compound (2R)-2-(benzyloxymethyl)pyrrolidine (3.13 g, crude, HCl) was obtained as a white solid.

$^1$H NMR (400 MHz, DMSO-d$_6$) δ=9.76 (br s, 1H), 9.11 (br s, 1H), 7.43-7.23 (m, 5H), 4.55 (s, 2H), 3.75-3.61 (m, 3H), 3.13 (br d, J=4.4 Hz, 2H), 2.07-1.76 (m, 3H), 1.66-1.56 (m, 1H).

Step C: (2R)-2-(benzyloxymethyl)-1-ethyl-pyrrolidine

To a mixture of (2R)-2-(benzyloxymethyl)pyrrolidine (3 g, crude, HCl) and iodoethane (2.05 g, 13.2 mmol, 1.05 mL) in CH$_3$CN (65 mL) was added K$_2$CO$_3$ (1.82 g, 13.2 mmol) in portion at 25° C. The mixture was stirred at 25° C. for 1 h, then heated to 78° C. and stirred for 11 hours. The reaction mixture was diluted with water (20 mL) and extracted with ethyl acetate (50 mL×3). The combined organic layers were washed with water (30 mL×2), dried over sodium sulfate, filtered and concentrated under reduced pressure to give a residue. The residue was purified by column chromatography (SiO$_2$, Petroleum ether/Ethyl acetate=100/1 to Ethyl acetate/Methanol=5/1). Compound (2R)-2-(benzyloxymethyl)-1-ethyl-pyrrolidine (2.41 g, 10.4 mmol, two steps 79% yield, 95% purity) was obtained as a brown oil.

$^1$H NMR (400 MHz, chloroform-d) δ=7.30-7.18 (m, 5H), 4.47 (s, 2H), 3.46 (dd, J=4.8, 9.2 Hz, 1H), 3.30 (dd, J=6.4, 9.2 Hz, 1H), 3.10 (ddd, J=2.4, 6.8, 8.8 Hz, 1H), 2.88 (qd, J=7.6, 12.4 Hz, 1H), 2.62-2.49 (m, 1H), 2.24 (qd, J=7.2, 12.4 Hz, 1H), 2.14-2.03 (m, 1H), 1.92-1.80 (m, 1H), 1.78-1.51 (m, 3H), 1.04 (t, J=7.2 Hz, 3H).

Step D: [(2R)-1-ethylpyrrolidin-2-yl]methanol

To a solution of (2R)-2-(benzyloxymethyl)-1-ethyl-pyrrolidine (2 g, 9.12 mmol, 1 eq) in MeOH (60 mL) was added HCl/MeOH (4 M, 30 mL, 13.2 eq) to adjusting the pH to 3-4, and then Pd(OH)$_2$/C (300 mg, 20% purity) was added under N$_2$. The suspension was degassed under vacuum and purged with H$_2$ three times. The mixture was stirred under H$_2$ (50 psi) at 25° C. for 12 hours. The catalyst was filtered and concentrated under reduced pressure to give a residue. The crude product was used directly into the next step without further purification. Compound [(2R)-1-ethylpyrrolidin-2-yl]methanol (1.68 g, crude, HCl) was obtained as a yellow solid.

$^1$H NMR (400 MHz, methanol-d$_4$) δ=3.88 (dd, J=3.6, 12.4 Hz, 1H), 3.75-3.45 (m, 4H), 3.21-3.08 (m, 2H), 2.30-1.82 (m, 4H), 1.37 (t, J=7.2 Hz, 3H).

Step E: benzyl (2S)-2-(cyanomethyl)-4-[2-[[(2R)-1-ethylpyrrolidin-2-yl]methoxy]-7-(1-naphthyl)-6,8-dihydro-5H-pyrido[3,4-d]pyrimidin-4-yl]piperazine-1-carboxylate

[(2R)-1-ethylpyrrolidin-2-yl]methanol (334 mg, 2.01 mmol, 1.95 eq, HCl) was dissolved into saturated sodium carbonate solution (5 mL) and then extracted ethyl acetate (2×10 mL). The extracts were dried over sodium sulfate, filtered and concentrated under vacuum. To a mixture of benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 600 mg, 1.03 mmol, 1 eq) and the above residue in toluene (35 mL) was added t-BuONa (298 mg, 3.10 mmol, 3 eq) in portion at 0° C. under $N_2$. The mixture was warmed to 25° C. and stirred for 10 min. The reaction mixture was diluted with ethyl acetate (20 mL) and adjusted PH to 8-9 with 2M HCl at 0° C., then extracted with ethyl acetate (20 mL×2). The combined organic layers were washed with water (15 mL×1), dried over sodium sulfate, filtered and concentrated under reduced pressure to give a residue. The residue was purified by reversed phase flash [water (0.1% FA)/acetonitrile]. The desired fractions were collected and neutralized with saturated $NaHCO_3$ solution (3 ml) and extracted with ethyl acetate (100 mL×2). The separated organic layer was dried over sodium sulfate, filtered and concentrated under vacuum. Compound benzyl (2S)-2-(cyanomethyl)-4-[2-[[(2R)-1-ethylpyrrolidin-2-yl]methoxy]-7-(1-naphthyl)-6,8-dihydro-5H-pyrido[3,4-d]pyrimidin-4-yl]piperazine-1-carboxylate (350 mg, 526 umol, 51% yield, 97.1% purity) was obtained as a white solid. LCMS [ESI, M+1]: 646.

Step F: 2-[(2S)-4-[2-[[(2R)-1-ethylpyrrolidin-2-yl]methoxy]-7-(1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-[[(2R)-1-ethylpyrrolidin-2-yl]methoxy]-7-(1-naphthyl)-6,8-dihydro-5H-pyrido[3,4-d]pyrimidin-4-yl]piperazine-1-carboxylate (305 mg, 472 umol, 1 eq) in MeOH (40 mL) and $NH_3$.MeOH (20 mL) was added Pd/C (300 mg, 10% purity) under $N_2$. The suspension was degassed under vacuum and purged with $H_2$ three times. The mixture was stirred under $H_2$ (15 psi) at 25° C. for 0.5 hour. The reaction mixture was filtered and concentrated under reduced pressure to give a residue. The crude product was used to next step directly without further purification. Compound 2-[(2S)-4-[2-[[(2R)-1-ethylpyrrolidin-2-yl]methoxy]-7-(1-naphthyl)-6,8-dihydro-5H-pyrido[3,4-d]pyrimidin-4-yl]piperazin-2-yl]acetonitrile (240 mg, crude) was obtained as a green solid. LCMS [ESI, M+1]: 512.

Step G: 2-[(2S)-4-[2-[[(2R)-1-ethylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a mixture of 2-[(2S)-4-[2-[[(2R)-1-ethylpyrrolidin-2-yl]methoxy]-7-(1-naphthyl)-6,8-dihydro-5H-pyrido[3,4-d]pyrimidin-4-yl]piperazin-2-yl]acetonitrile (240 mg, crude) in DCM (10 mL) was added TEA (237 mg, 2.35 mmol, 326 uL), then prop-2-enoyl prop-2-enoate (59.2 mg, 469 umol) was added in portion at 0° C. under $N_2$. The mixture was warmed to 25° C. and stirred for 0.5 hour. The reaction mixture was quenched by adding saturated $NaHCO_3$ solution (2 mL) at 0° C., and then extracted with DCM mL (20 mL×3). The combined organic layers were washed with brine (15 mL×1), dried over sodium sulfate, filtered and concentrated under reduced pressure to give a residue. The residue was purified by column chromatography ($Al_2O_3$, Petroleum ether/Ethyl acetate=50/1 to Ethyl acetate/Methanol=5/1) and further purified by prep-HPLC (column: Phenomenex Gemini 150*25 mm*10 um; mobile phase: [water (0.05% ammonia hydroxide v/v)-ACN]; B %: 59%-89%, 12 min). Title compound 2-[(2S)-4-[2-[[(2R)-1-ethylpyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (EXAMPLE 334, 44.2 mg, 75.2 umol, two steps 16% yield, 96.4% purity) was obtained as a white solid. LCMS [ESI, M+1]: 566.

$^1$H NMR (400 MHz, chloroform-d) δ=8.24-8.18 (m, 1H), 7.90-7.83 (m, 1H), 7.62 (d, J=8.0 Hz, 1H), 7.54-7.48 (m, 2H), 7.44 (t, J=7.6 Hz, 1H), 7.15 (d, J=7.6 Hz, 1H), 6.60 (br s, 1H), 6.47-6.35 (m, 1H), 5.84 (br d, J=10.4 Hz, 1H), 5.11 (br s, 1H), 4.39 (br d, J=8.4 Hz, 1H), 4.35-4.21 (m, 2H), 4.19-4.09 (m, 2H), 4.02 (br d, J=12.4 Hz, 1H), 3.47 (br s, 2H), 3.34 (br s, 2H), 3.26-3.07 (m, 3H), 3.05-2.63 (m, 5H), 2.44 (br dd, J=6.8, 12.0 Hz, 1H), 2.26 (br d, J=8.0 Hz, 1H), 2.12-1.94 (m, 1H), 1.80 (br d, J=4.0 Hz, 4H), 1.15 (br t, J=7.2 Hz, 3H).

Example 335

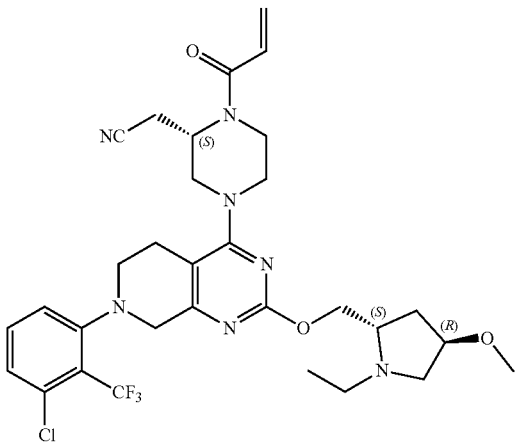

2-[(2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]-1-prop-2-enoyl-piperazin-2-yl]acetonitrile

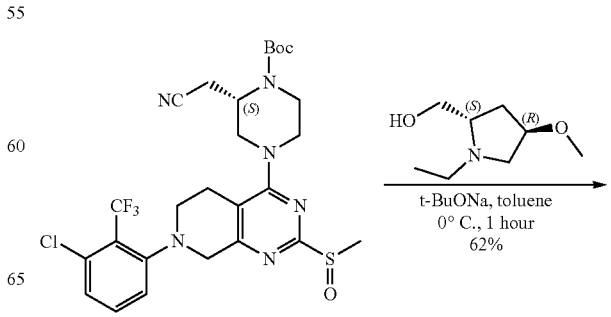

905

-continued

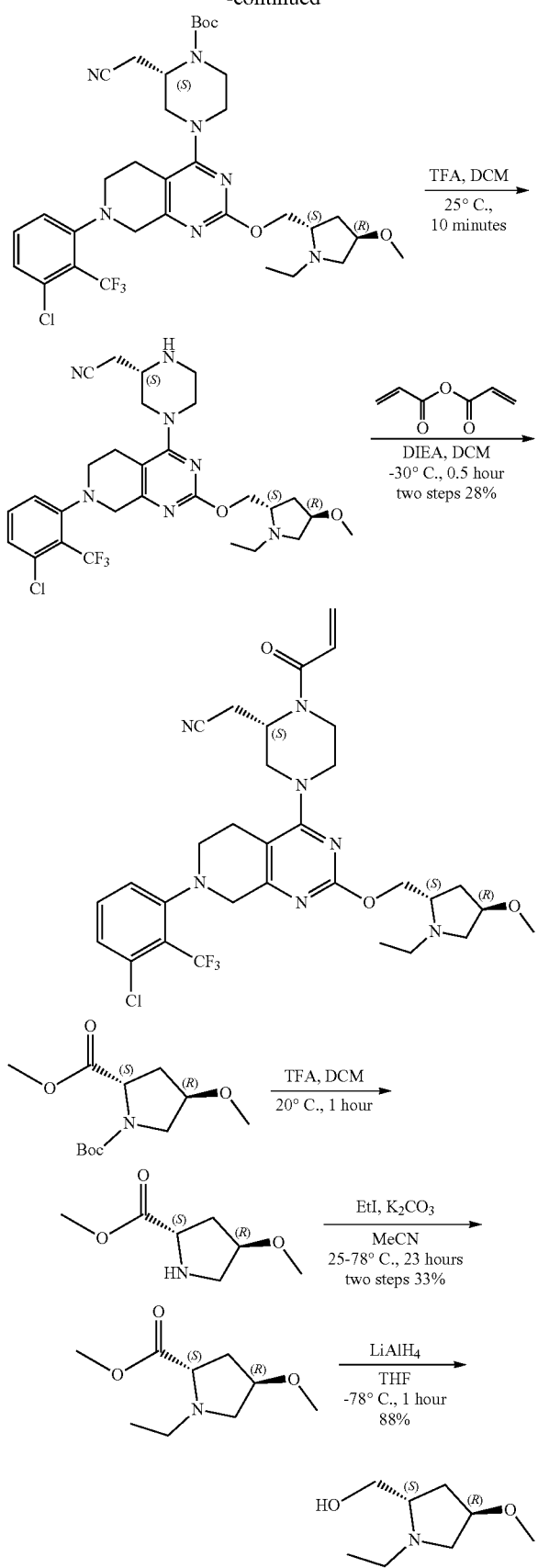

906

Step 1: methyl (2S,4R)-4-methoxypyrrolidine-2-carboxylate

To a solution of O1-tert-butyl-O2-methyl (2S,4R)-4-methoxypyrrolidine-1,2-dicarboxylate (5.00 g, 19.3 mmol, 1.0 eq) in DCM (5.0 mL) was added TFA (7.70 g, 67.5 mmol, 5.0 mL, 3.50 eq). The mixture was stirred at 20° C. for 1 hour. After completion, the mixture was concentrated. The product methyl (2S,4R)-4-methoxypyrrolidine-2-carboxylate (3.0 g, crude, TFA) was obtained as yellow oil.

Step 2: methyl (2S,4R)-1-ethyl-4-methoxy-pyrrolidine-2-carboxylate

To a solution of methyl (2S,4R)-4-methoxypyrrolidine-2-carboxylate (3.0 g, 11.0 mmol, 1.0 eq, TFA) and K₂CO₃ (4.55 g, 32.9 mmol, 3.0 eq) in MeCN (30.0 mL) was added iodoethane (1.71 g, 11.0 mmol, 878 uL, 1.0 eq) in portions. The mixture was stirred at 25° C. for 1 hour and heated to 78° C., then stirred at 78° C. for 11 hours. After completion, the mixture was filtered and concentrated. The obtained product was purified by column chromatography (SiO₂, PE:EA=10:1-EA:MeOH=10:1) to give methyl (2S,4R)-1-ethyl-4-methoxy-pyrrolidine-2-carboxylate (1.20 g, 6.41 mmol, two steps 33% yield) as yellow oil.
¹H NMR (400 MHz, Chloroform-d) δ 4.04-3.95 (m, 1H), 3.73 (s, 3H), 3.55-3.33 (m, 2H), 3.29 (s, 3H), 2.83-2.70 (m, 1H), 2.53-2.35 (m, 2H), 2.14 (dd, J=5.6, 8.0 Hz, 2H), 1.09 (t, J=7.2 Hz, 3H).

Step 3: [(2S,4R)-1-ethyl-4-methoxy-pyrrolidin-2-yl]methanol

To a solution of methyl (2S,4R)-1-ethyl-4-methoxy-pyrrolidine-2-carboxylate (1.20 g, 6.41 mmol, 1.0 eq) in THF (15.0 mL) was added LiAlH₄ (730 mg, 19.2 mmol, 3.0 eq). The mixture was stirred at −78° C. for 1 hour. After completion, the mixture was quenched with saturated Na₂SO₄ aqueous (0.30 mL) and filtered, washed with THF (10.0 mL). The mother liquid was concentrated. The obtained product was purified by column chromatography (SiO₂, PE:EA=10:1-EA; MeOH=5:1) to give [(2S,4R)-1-ethyl-4-methoxy-pyrrolidin-2-yl]methanol (600 mg, 3.77 mmol, 59% yield) as yellow oil.
¹H NMR (400 MHz, Chloroform-d) δ 3.92-3.83 (m, 1H), 3.66 (dd, J=3.2, 10.8 Hz, 1H), 3.49-3.35 (m, 2H), 3.30 (s, 3H), 2.89-2.76 (m, 2H), 2.40-2.27 (m, 2H), 2.07-1.97 (m, 1H), 1.93-1.82 (m, 1H), 1.08 (t, J=7.2 Hz, 3H).

Step A: tert-butyl (2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]-2-(cyanomethyl)piperazine-1-carboxylate To a solution of [(2S,4R)-1-ethyl-4-methoxy-pyrrolidin-2-yl]methanol (266 mg, 1.67 mmol, 2.00 eq) in THF (5.0 mL) was added t-BuONa (241 mg, 2.50 mmol, 3.0 eq). The mixture was stirred at 0° C. for 0.5 hour. Then tert-butyl (2S)-4-[7-[3-chloro-2-(trifluoromethyl)phenyl]-2-methylsulfinyl-6,8-dihydro-5H-pyrido[3,4-d]pyrimidin-4-yl]-2-(cyanomethyl)piperazine-1-carboxylate (500 mg, 835 umol, 1.0 eq) was added to the above liquid. After addition, the mixture was stirred at 0° C. for 0.5 hour. Upon completion, the mixture was added water (10.0 mL) and extracted with ethyl acetate (10.0 mL×3). The organic layer was dried over Na₂SO₄, filtered and concentrated. The obtained product was purified by column chromatography (SiO$_2$, PE:EA=20:1-EA:MeOH=10:1) to give tert-butyl (2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]-2-(cyanomethyl)piperazine-1-carboxylate (440 mg, 513 umol, 62% yield, 81% purity) as yellow solid. LCMS [ESI, M+1]: 694.

$^1$H NMR (400 MHz, Chloroform-d) δ 7.41 (t, J=8.0 Hz, 1H), 7.28 (d, J=8.0 Hz, 1H), 7.20 (d, J=8.4 Hz, 1H), 4.63 (br s, 1H), 4.42 (br dd, J=4.4, 10.8 Hz, 1H), 4.18-4.06 (m, 4H), 4.06-3.96 (m, 2H), 4.06-3.96 (m, 1H), 3.92-3.86 (m, 1H), 3.36-3.20 (m, 6H), 3.18-2.96 (m, 4H), 2.94-2.66 (m, 4H), 2.58-2.39 (m, 1H), 2.37-2.30 (m, 1H), 2.14-2.07 (m, 1H), 2.02-1.91 (m, 1H), 1.53 (s, 9H), 1.13 (t, J=7.4 Hz, 3H).

Step B: 2-[(2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]-2-(cyanomethyl)piperazine-1-carboxylate (390 mg, 455 umol, 1.0 eq) in DCM (1.00 mL) was added TFA (1.54 g, 13.5 mmol, 1.0 mL, 29.7 eq). The mixture was stirred at 25° C. for 10 minutes. After completion, the mixture was concentrated under vacuum. The product 2-[(2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]piperazin-2-yl]acetonitrile (400 mg, crude, 2 TFA) was obtained as yellow oil. LCMS [ESI, M+1]: 594.

Step C: 2-[(2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]piperazin-2-yl]acetonitrile (400 mg, 487 umol, 1.0 eq, 2 TFA) in DCM (2.0 mL) was added DIEA (629 mg, 4.87 mmol, 847 uL, 10.0 eq) at −30° C. Then prop-2-enoyl prop-2-enoate (92.0 mg, 730 umol, 1.50 eq) was added to the above liquid at −30° C. and the mixture was stirred at −30° C. for 0.5 hour. After completion, the mixture was quenched with MeOH (0.50 mL) and concentrated under vacuum. The title compound was purified by prep-HPLC (column: Phenomenex Gemini 150*25 mm*10 um; mobile phase: [water (0.05% ammonia hydroxide v/v)-ACN]; B %: 50%-80%, 12 min) to give 2-[(2S)-4-[7-[3-chloro-2-(trifluoromethyl)phenyl]-2-[[(2S,4R)-1-ethyl-4-methoxy-pyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 335, 120 mg, 182 umol, two steps 28% yield, 99% purity) as white solid. LCMS [ESI, M+1]: 648.

$^1$H NMR (400 MHz, Chloroform-d) δ 7.42 (t, J=8.0 Hz, 1H), 7.29 (d, J=6.4 Hz, 1H), 7.21 (d, J=8.0 Hz, 1H), 6.68-6.55 (m, 1H), 6.42 (dd, J=1.6, 16.4 Hz 1H), 5.85 (br d, J=10.8 Hz, 1H), 5.20-4.51 (m, 1H), 4.42 (dd, J=4.4, 10.8 Hz, 1H), 4.19-4.04 (m, 4H), 4.04-3.72 (m, 3H), 3.70-3.41 (m, 2H), 3.39-3.22 (m, 5H), 3.20-2.79 (m, 7H), 2.76 (br s, 1H), 2.50-2.40 (m, 1H), 2.33 (dd, J=5.2, 10.0 Hz, 1H), 2.15-2.05 (m, 1H), 2.03-1.90 (m, 1H), 1.13 (t, J=7.2 Hz, 3H).

Example 336

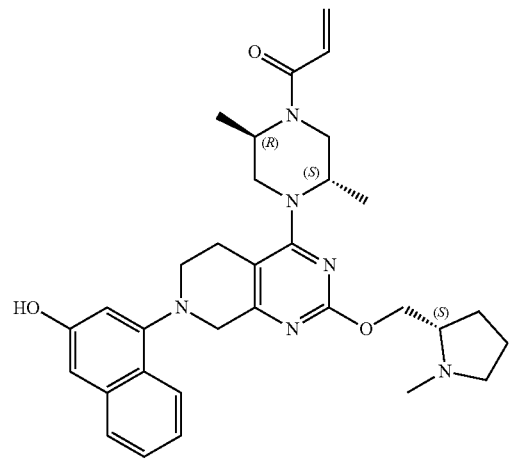

1-[(2R,5S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-2,5-dimethyl-piperazin-1-yl]prop-2-en-1-one

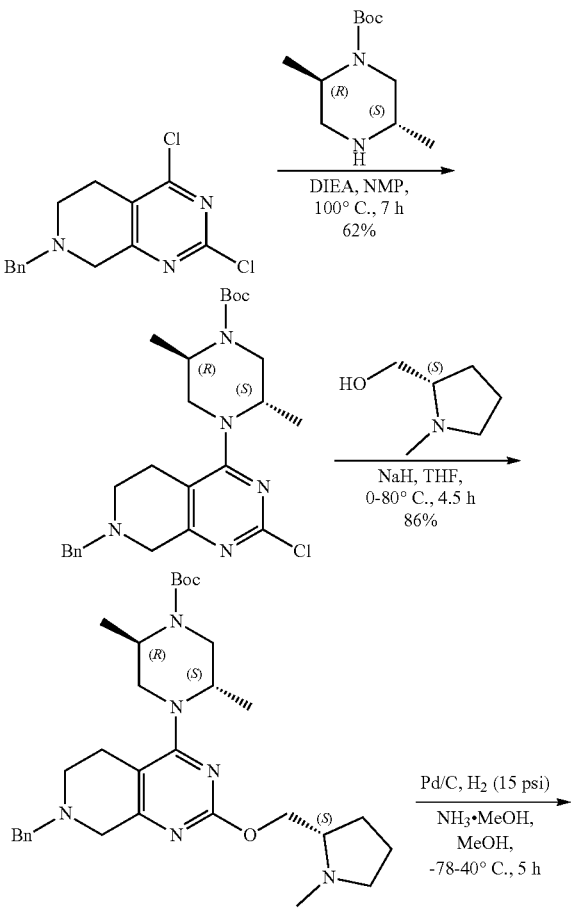

909
-continued

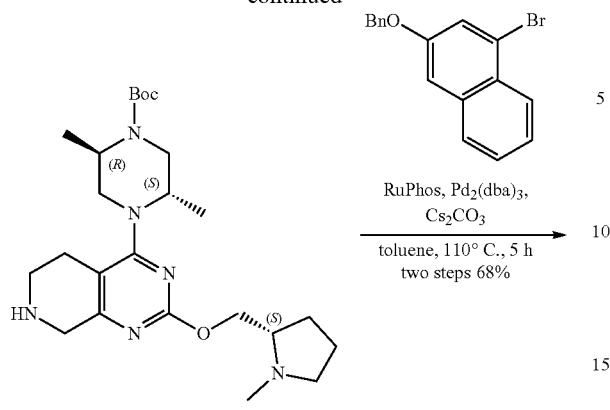

910
-continued

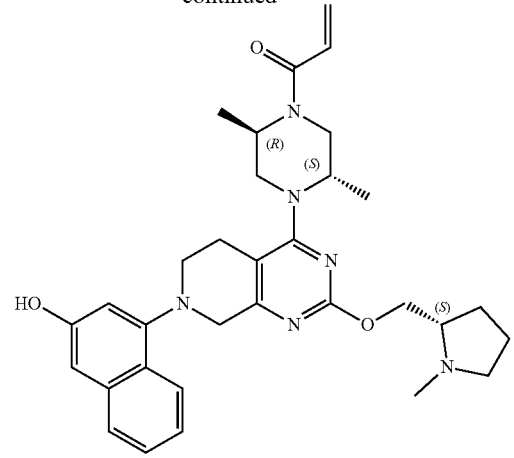

Step A: tert-butyl (2R,5S)-4-(7-benzyl-2-chloro-6,8-dihydro-5H-pyrido[3,4-d]pyrimidin-4-yl)-2,5-dimethyl-piperazine-1-carboxylate A solution of 7-benzyl-2,4-dichloro-6,8-dihydro-5H-pyrido[3,4-d] pyrimidine (2.70 g, 9.18 mmol, 1.00 eq), tert-butyl (2R,5S)-2,5-dimethylpiperazine-1-carboxylate (1.77 g, 8.26 mmol, 0.90 eq) and DIEA (2.37 g, 18.4 mmol, 3.20 mL, 2.00 eq) in NMP (30.0 mL) was stirred at 100° C. for 7 hours. The mixture was diluted with ethyl acetate (50.0 mL), washed with brine (3×100 mL). The organic layer was dried over Na$_2$SO$_4$, filtered and concentrated under vacuum. The residue was purified by column chromatography (SiO$_2$, petroleum ether/ethyl acetate=3/1) to give tert-butyl (2R, 5S)-4-(7-benzyl-2-chloro-6,8-dihydro-5H-pyrido[3,4-d]pyrimidin-4-yl)-2,5-dimethyl-piperazine-1-carboxylate (2.80 g, 5.69 mmol, 62% yield) as a yellow solid. LCMS [ESI, M+1]: 472.

$^1$H NMR (400 MHz, chloroform-d) δ=7.40-7.29 (m, 5H), 4.45-4.19 (m, 2H), 3.71-3.61 (m, 4H), 3.54-3.43 (m, 3H), 3.41-3.36 (m, 1H), 2.81-2.67 (m, 2H), 2.64-2.49 (m, 2H), 1.48 (s, 9H), 1.20 (d, J=6.8 Hz, 3H), 1.17 (d, J=6.8 Hz, 3H).

Step B: tert-butyl (2R,5S)-4-[7-benzyl-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate To a solution of [(2S)-1-methylpyrrolidin-2-yl]methanol (854 mg, 7.41 mmol, 880 uL, 2.50 eq) in THF (20.0 mL) was added NaH (237 mg, 5.93 mmol, 60.0% purity, 2.00 eq) at 0° C. After stirred at 0° C. for 0.5 h, tert-butyl (2R,5S)-4-(7-benzyl-2-chloro-6,8-dihydro-5H-pyrido[3,4-d]pyrimidin-4-yl)-2,5-dimethyl-piperazine-1-carboxylate (1.40 g, 2.97 mmol, 1.00 eq) was added. The mixture was stirred at 80° C. for 4 hours. The mixture was diluted with water (20.0 mL), extracted with ethyl acetate (3×30.0 mL), the organic layer was washed with brine (1×40.0 mL), dried over Na$_2$SO$_4$, filtered and concentrated under vacuum. The residue was purified by column chromatography (Al$_2$O$_3$, methanol/ethyl acetate=1/10) to give tert-butyl (2R,5S)-4-[7-benzyl-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate (1.55 g, 2.56 mmol, 86% yield) as a yellow solid. LCMS [ESI, M+1]: 551.

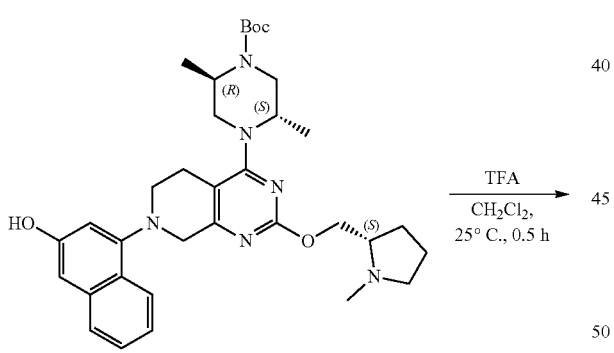

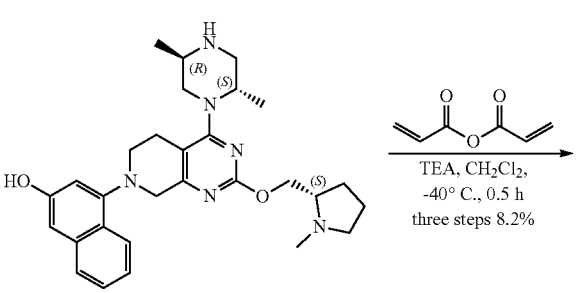

¹H NMR (400 MHz, chloroform-d) δ=7.39-7.28 (m, 5H), 4.31 (br dd, J=4.8, 10.4 Hz, 2H), 4.16-4.08 (m, 1H), 3.72-3.62 (m, 4H), 3.61-3.56 (m, 1H), 3.52-3.43 (m, 2H), 3.38 (br s, 1H), 3.08 (br t, J=8.0 Hz, 1H), 2.81-2.48 (m, 6H), 2.45 (s, 3H), 2.33-2.20 (m, 1H), 2.04-1.95 (m, 1H), 1.78-1.65 (m, 3H), 1.48 (s, 9H), 1.17 (br d, J=6.4 Hz, 6H).

Step C: tert-butyl (2R,5S)-2,5-dimethyl-4-[2-[[(2S)-1-methylpyrrolidin-2-yl]methoxy]-5,6,7,8-tetrahydropyrido[3,4-d]pyrimidin-4-yl]piperazine-1-carboxylate NH₃ was bubbled in methanol (150 mL) at −78° C. for 15 mins. tert-Butyl (2R,5S)-4-[7-benzyl-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate (2.80 g, 5.08 mmol, 1.00 eq) and Pd/C (0.50 g, 10.0% purity) was added into the mixture. After stirred at 40° C. for 5 hours under H₂ at 15 psi, the mixture was filtered and concentrated under vacuum to give tert-butyl (2R,5S)-2,5-dimethyl-4-[2-[[(2S)-1-methylpyrrolidin-2-yl]methoxy]-5,6,7,8-tetrahydropyrido[3,4-d]pyrimidin-4-yl]piperazine-1-carboxylate (2.20 g, crude) as a yellow oil and used into next step without further purification. LCMS [ESI, M+1]: 461.

Step D: tert-butyl (2R,5S)-4-[7-(3-benzyloxy-1-naphthyl)-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate A mixture of tert-butyl (2R,5S)-2,5-dimethyl-4-[2-[[(2S)-1-methylpyrrolidin-2-yl]methoxy]-5,6,7,8-tetrahydropyrido[3,4-d]pyrimidin-4-yl]piperazine-1-carboxylate (1.00 g, crude), 3-benzyloxy-1-bromo-naphthalene (1.02 g, 3.26 mmol, 1.50 eq), RuPhos (203 mg, 434 umol), Pd₂(dba)₃ (199 mg, 217 umol) and Cs₂CO₃ (2.12 g, 6.51 mmol) in toluene (30.0 mL) was stirred at 110° C. for 5 hours under N₂. The mixture was diluted with water (20.0 mL), extracted with ethyl acetate (3×40.0 mL). The organic layer was washed with brine (1×50.0 mL), dried over Na₂SO₄, filtered and concentrated under vacuum. The residue was purified by reversed phase flash [water (TFA, 0.10%)/acetonitrile]. The desired fraction was collected and adjusted pH >7 by saturated sodium bicarbonate (5.00 mL), and then extracted with ethyl acetate (3×30.0 mL). The organic layer was washed with brine (1×30.0 mL), dried over Na₂SO₄, filtered and concentrated under vacuum to give tert-butyl (2R,5S)-4-[7-(3-benzyloxy-1-naphthyl)-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate (1.06 g, 1.47 mmol, two steps 68% yield) as a yellow solid. LCMS [ESI, M/2+1]: 347.

¹H NMR (400 MHz, chloroform-d) δ=8.11 (d, J=8.4 Hz, 1H), 7.77-7.71 (m, 1H), 7.52-7.40 (m, 5H), 7.39-7.33 (m, 2H), 6.99 (d, J=2.0 Hz, 1H), 6.90 (d, J=2.0 Hz, 1H), 5.18 (s, 2H), 4.48-4.42 (m, 1H), 4.38 (dd, J=4.8, 10.4 Hz, 1H), 4.32-4.25 (m, 1H), 4.20 (br d, J=5.6 Hz, 1H), 4.16-4.09 (m, 1H), 3.76 (br s, 1H), 3.70-3.61 (m, 1H), 3.60-3.52 (m, 1H), 3.45 (br s, 2H), 3.24 (br s, 1H), 3.10 (br t, J=7.6 Hz, 1H), 2.93 (br s, 1H), 2.80-2.61 (m, 2H), 2.49 (s, 3H), 2.33-2.25 (m, 1H), 2.12-2.03 (m, 1H), 1.91-1.76 (m, 4H), 1.50 (s, 9H), 1.27-1.22 (m, 6H).

Step E: tert-butyl (2R,5S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate A mixture of tert-butyl (2R,5S)-4-[7-(3-benzyloxy-1-naphthyl)-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate (0.90 g, 1.30 mmol, 1.00 eq) and Pd/C (0.10 g, 10.0% purity) in methanol (40.0 mL) was stirred at 25° C. for 1 hour under H₂ at 15 psi. The mixture was filtered and concentrated under vacuum to give tert-butyl (2R,5S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate (0.72 g, crude) as a yellow solid which was used into next step without further purification. LCMS [ESI, M+1]: 603.

Step F: 4-[4-[(2S,5R)-2,5-dimethylpiperazin-1-yl]-2-[[(2S)-1-methylpyrrolidin-2-yl]methoxy]-6,8-dihydro-5H-pyrido[3,4-d]pyrimidin-7-yl]naphthalen-2-ol A mixture of tert-butyl (2R,5S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-2,5-dimethyl-piperazine-1-carboxylate (0.70 g, crude) and TFA (1.99 g, 17.42 mmol, 1.29 mL) in dichloromethane (1.20 mL) was stirred at 25° C. for 0.5 h. The mixture was concentrated under vacuum to give 4-[4-[(2S,5R)-2,5-dimethylpiperazin-1-yl]-2-[[(2S)-1-methylpyrrolidin-2-yl]methoxy]-6,8-dihydro-5H-pyrido[3,4-d]pyrimidin-7-yl]naphthalen-2-ol (849 mg, crude, 2TFA) as a yellow oil and used into next step without further purification. LCMS [ESI, M+1]: 503.

Step G: 1-[(2R,5S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]-2,5-dimethyl-piperazin-1-yl]prop-2-en-1-one To a solution of 4-[4-[(2S,5R)-2,5-dimethylpiperazin-1-yl]-2-[[(2S)-1-methylpyrrolidin-2-yl]methoxy]-6,8-dihydro-5H-pyrido[3,4-d]pyrimidin-7-yl]naphthalen-2-ol (0.84 g, crude, 2TFA) and TEA (1.16 g, 11.5 mmol, 1.60 mL) in dichloromethane (3.00 mL) was added prop-2-enoyl prop-2-enoate (102 mg, 805 umol) at −40° C. After stirred at −40° C. for 0.5 h, the mixture was quenched with water (0.10 mL) and concentrated under vacuum. The residue was purified by reversed phase flash [water (0.1% TFA)-acetonitrile] and prep-HPLC (column: Phenomenex Luna Phenyl-Hexyl 150_30_5 um; mobile phase: [water (10 mM NH₄HCO₃)-ACN]; B %: 45%-75%, 3 min). The desired fraction was collected and lyophilized to give title compound 1-[(2R,5S)-4-[7-(3-hydroxy-1-naphthyl)-2-[[(2S)-1-methylpyrrolidin-2-yl] methoxy]-6,8-dihydro-5H-pyrido[3,4-d]pyrimidin-4-yl]-2,5-dimethyl-piperazin-1-yl]prop-2-en-1-one (EXAMPLE 336, 55.8 mg, 94.1 umol, three steps 8.2% yield, 93.9% purity) as a off-white solid. LCMS [ESI, M+1]:557.

SFC: "Column: Chiralpak AS-3 50×4.6 mm I.D., 3 um, Mobile phase: methanol (0.05% DEA) in CO₂ from 5% to 40%, Flow rate: 3 mL/min, Wavelength: 220 nm".

¹H NMR (400 MHz, chloroform-d) δ=7.97 (br d, J=8.0 Hz, 1H), 7.63 (d, J=8.0 Hz, 1H), 7.40-7.34 (m, 1H), 7.26 (dt, J=1.6, 8.4 Hz, 1H), 6.90 (d, J=1.6 Hz, 1H), 6.65 (br s, 1H), 6.61-6.43 (m, 1H), 6.39-6.26 (m, 1H), 5.73 (br t, J=8.8 Hz, 1H), 4.83 (br s, 1H), 4.55 (br d, J=5.6 Hz, 1H), 4.43-4.04 (m, 4H), 3.91 (br d, J=17.2 Hz, 1H), 3.77-3.26 (m, 5H), 3.19 (br t, J=8.0 Hz, 1H), 3.06-2.68 (m, 3H), 2.63 (br s, 3H), 2.57 (br d, J=13.2 Hz, 1H), 2.41-2.33 (m, 1H), 2.15-1.83 (m, 4H), 1.11-0.96 (m, 6H).

Example 337

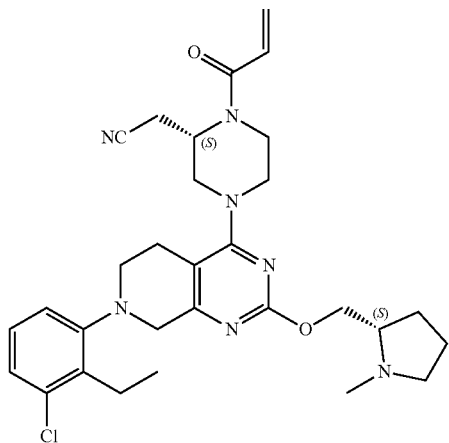

2-[(2S)-4-[7-(3-chloro-2-ethyl-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

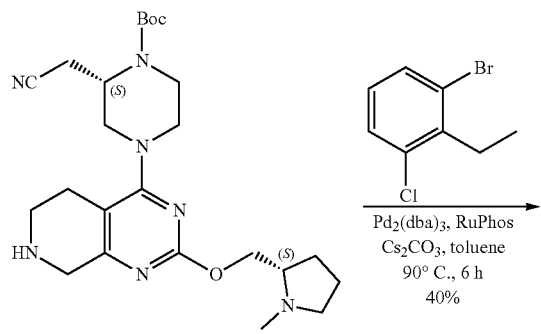

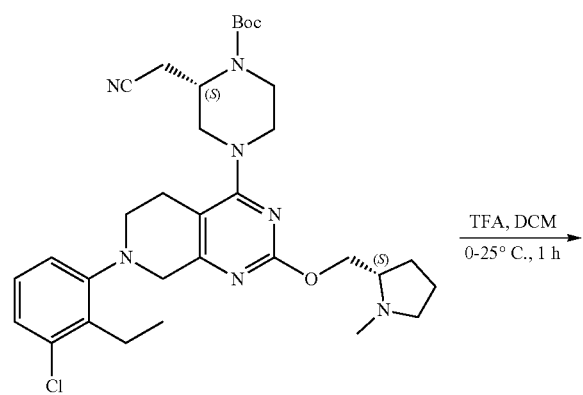

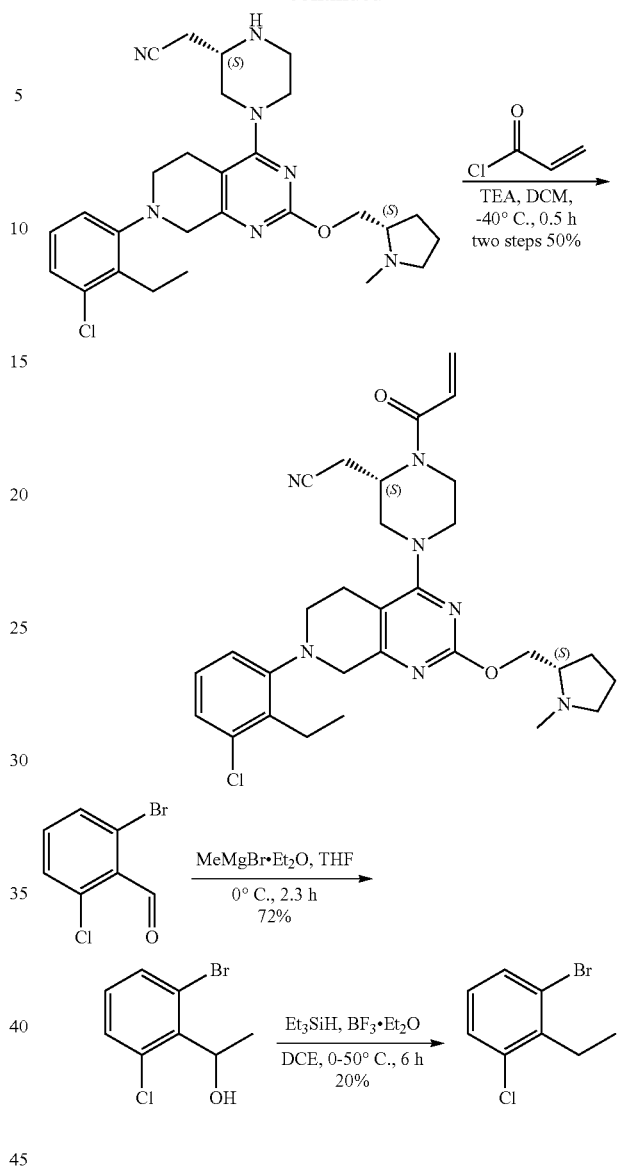

Step 1: 1-(2-bromo-6-chloro-phenyl) ethanol

Into a flame-dried 100 mL round-bottom flask equipped with a magnetic stir bar and under $N_2$ was added 2-bromo-6-chloro-benzaldehyde (10.0 g, 45.6 mmol, 1 eq) and THF (100 mL). The mixture was cooled to 0° C. and then MeMgBr (3 M in $Et_2O$, 22.8 mL, 1.5 eq) was added dropwise over 20 min. The resulting suspension was stirred at 0° C. for 2 h. The reaction mixture was quenched by dropwise addition of a saturated aqueous $NH_4Cl$ solution (10 mL). The mixture was cooled, poured into a 100 mL separatory funnel containing water (150 mL) and the mixture was extracted with ethyl acetate (2×150 mL). The combined organic layers were washed with brine, dried over $MgSO_4$, filtered and concentrated under reduced pressure. The residue was purified by silica gel chromatography (Petroleum ether/Ethyl acetate=100/1 to 10/1). Compound 1-(2-bromo-6-chloro-phenyl) ethanol (8.00 g, 32.6 mmol, 72% yield, 96% purity) was obtained as a yellow oil. LCMS [ESI, M-17]: 219.

¹H NMR (400 MHz, chloroform-d) δ=7.46 (br d, J=8.0 Hz, 1H), 7.31 (br d, J=8.0 Hz, 1H), 7.07-6.96 (m, 1H), 5.68-5.44 (m, 1H), 3.24 (br d, J=8.0 Hz, 1H), 1.61 (d, J=4.4 Hz, 3H).

Step 2: 1-bromo-3-chloro-2-ethyl-benzene

To a mixture of 1-(2-bromo-6-chloro-phenyl)ethanol (8.00 g, 34.0 mmol, 1 eq) in DCE (150 mL) was added $BF_3 \cdot Et_2O$ (14.5 g, 102 mmol, 12.6 mL, 3 eq) and $Et_3SiH$ (19.8 g, 170 mmol, 27.1 mL, 5 eq) in portions at 0° C. The mixture was stirred at 50° C. for 6 hours. The reaction mixture was washed with saturated $NaHCO_3$ aqueous (2×75 mL) and saturated brine (1×75 mL), then dried over $Na_2SO_4$, filtered and concentrated under vacuum. The residue was purified by silica gel chromatography (Petroleum ether). The residue was purified by prep-HPLC (column: Phenomenex Synergi Max-RP 250*50 mm*10 um; mobile phase: [water (0.225% FA)-ACN]; B %: 65ACN %-95ACN %, 30 min; 60% min). Compound 1-bromo-3-chloro-2-ethyl-benzene (1.50 g, 6.83 mmol, 20% yield, 100% purity) was obtained as a yellow oil.

Step A: tert-butyl (2S)-4-[7-(3-chloro-2-ethyl-phenyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate To a mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 300 mg, 636 umol, 1 eq), 1-bromo-3-chloro-2-ethyl-benzene (279 mg, 1.27 mmol, 2 eq), $Pd_2(dba)_3$ (117 mg, 127 umol, 0.2 eq), RuPhos (89.1 mg, 191 umol, 0.3 eq) and $Cs_2CO_3$ (622 mg, 1.91 mmol, 3 eq) in toluene (30 mL) was degassed and purged with $N_2$ for 3 times, and then the mixture was stirred at 90° C. for 6 hours under $N_2$ atmosphere. The reaction mixture was added $H_2O$ (1×200 mL) and Ethyl acetate (1×250 mL). The organic phase was separated, washed with brine (1×200 mL), dried over sodium sulfate, filtered and concentrated under reduced pressure to give a residue. The residue was purified by reversed phase flash [water (0.1% FA)/acetonitrile]. The desired fractions were collected and neutralized to pH=7 with saturated $NaHCO_3$ solution and extracted with ethyl acetate (1×200 mL). The separated organic layer was dried over sodium sulfate, filtered and concentrated under vacuum. tert-butyl (2S)-4-[7-(3-chloro-2-ethyl-phenyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (155 mg, 0.254 mmol, 100% purity, 40% yield) was obtained as a yellow solid. LCMS [ESI, M+1]: 610.

¹H NMR (400 MHz, chloroform-d) δ=7.20-7.16 (m, 1H), 7.13 (t, J=8.0 Hz, 1H), 7.07-7.03 (m, 1H), 4.61 (br s, 1H), 4.39 (dd, J=5.2, 10.6 Hz, 1H), 4.16 (dd, J=6.8, 10.4 Hz, 1H), 4.09-3.95 (m, 4H), 3.91 (br d, J=13.2 Hz, 1H), 3.26 (dd, J=3.6, 13.7 Hz, 1H), 3.22-2.96 (m, 5H), 2.90 (q, J=7.4 Hz, 2H), 2.84-2.63 (m, 5H), 2.48 (s, 3H), 2.35-2.23 (m, 1H), 2.13-2.00 (m, 1H), 1.83-1.70 (m, 3H), 1.52 (s, 9H), 1.22 (t, J=7.4 Hz, 3H).

Step B: 2-[(2S)-4-[7-(3-chloro-2-ethyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(3-chloro-2-ethyl-phenyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (310 mg, 508 umol, 1 eq) in DCM (600 uL) was added TFA (869 mg, 7.62 mmol, 564 uL, 15 eq) at 0° C. under nitrogen atmosphere. The mixture was stirred at 25° C. for 1 h. After that, the mixture was concentrated under vacuum. 2-[(2S)-4-[7-(3-chloro-2-ethyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (850 mg, crude, 2 TFA) was obtained as a yellow oil. LCMS [ESI, M+1]: 510.

Step C: 2-[(2S)-4-[7-(3-chloro-2-ethyl-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2S)-4-[7-(3-chloro-2-ethyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (850 mg, crude, 2 TFA) and prop-2-enoyl chloride (59.8 mg, 660 umol, 53.8 uL) in DCM (8 mL) was added TEA (514 mg, 5.08 mmol, 707 uL) in portion. The mixture was stirred at −40° C. for 30 min. The reaction mixture was quenched by $NaHCO_3$ saturated solution (2 mL) at 0° C., and then extracted with $CH_2Cl_2$ (2×30 mL). The combined organic layers were washed with brine (1×30 mL), dried over sodium sulfate, filtered and concentrated under vacuum to give a residue. The residue was purified by column chromatography ($Al_2O_3$; Ethyl acetate/Methanol=20/1 to 3/1). The residue was purified by prep-HPLC (column: Gemini 150*25 5 u; mobile phase: [water (0.04% $NH_3 \cdot H_2O$)-ACN]; B %: 65%-95%, 10 min). Title compound 2-[(2S)-4-[7-(3-chloro-2-ethyl-phenyl)-2-[[(2S)-1-methylpyrrolidin-2-yl]methoxy]-6,8-dihydro-5H-pyrido [3,4-d]pyrimidin-4-yl]-1-prop-2-enoyl-piperazin-2-yl] acetonitrile (EXAMPLE 337, 142 mg, 252 umol, two steps 50% yield, 100% purity) was obtained as a white solid. LCMS [ESI, M+1]: 564.

SFC condition: "Column: Chiralpak AD-3 100×4.6 mm I.D., 3 um, Mobile phase: methanol (0.05% DEA) in $CO_2$ from 5% to 40%, Flow rate: 3 mL/min, Wavelength: 220 nm".

¹H NMR (400 MHz, dmso-$d_6$) δ=7.21 (s, 3H), 6.78 (dd, J=10.4, 16.8 Hz, 1H), 6.15 (dd, J=2.0, 16.8 Hz, 1H), 5.74 (dd, J=2.0, 10.6 Hz, 1H), 4.84 (br s, 1H), 4.28 (dd, J=5.2, 10.8 Hz, 1H), 4.23-4.07 (m, 2H), 4.05-3.90 (m, 4H), 3.39 (br s, 1H), 3.27 (br dd, J=3.6, 13.6 Hz, 1H), 3.20-3.05 (m, 3H), 2.99-2.93 (m, 2H), 2.93-2.76 (m, 4H), 2.61-2.52 (m, 2H), 2.40-2.31 (m, 3H), 2.22 (q, J=8.4 Hz, 1H), 2.00-1.87 (m, 1H), 1.77-1.54 (m, 3H), 1.19 (t, J=7.2 Hz, 3H).

Example 338

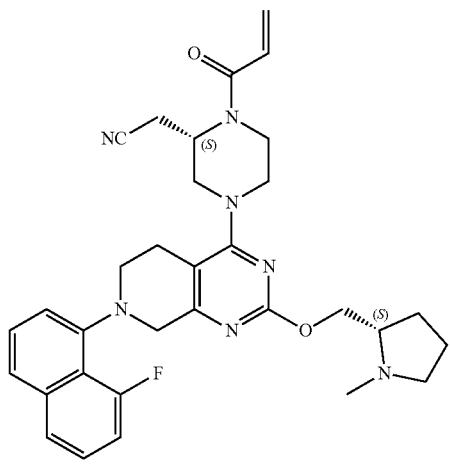

2-((S)-1-acryloyl-4-(7-(8-fluoronaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile

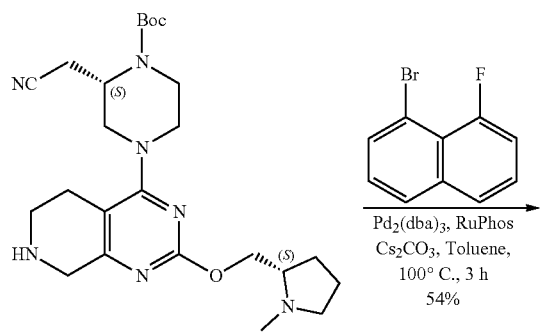

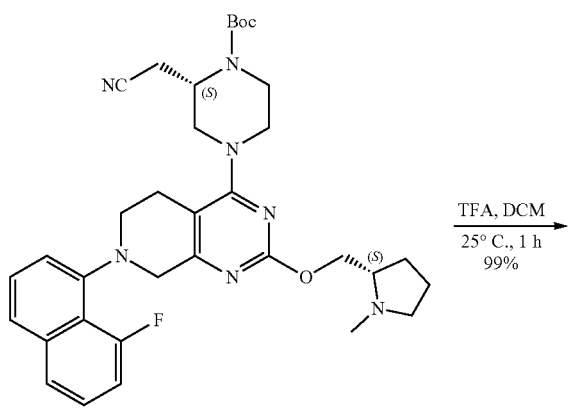

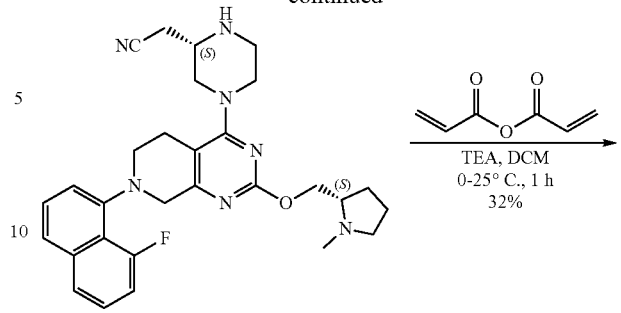

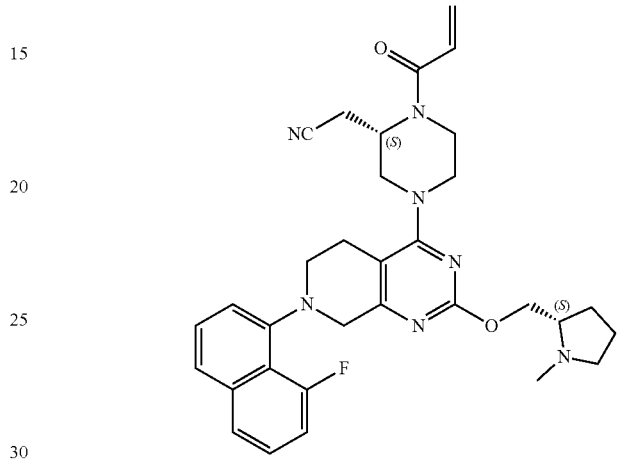

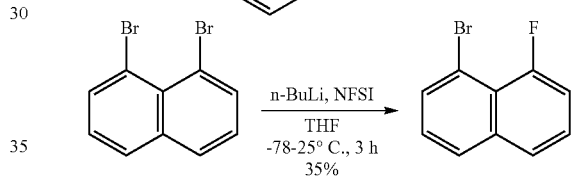

Insert: 1-bromo-8-fluoro-naphthalene

To a solution of 1,8-dibromonaphthalene (2 g, 6.99 mmol, 1 eq) in THF (50 mL) was added n-BuLi (2.5 M in hexane, 4.20 mL, 1.5 eq) at −78° C. dropwise. After stirring for 10 minutes at −78° C., a solution of N-(benzenesulfonyl)-N-fluoro-benzenesulfonamide (4.41 g, 13.9 mmol, 2 eq) in THF (10 mL) was added dropwise. The mixture was warmed up to 25° C. and stirred for 3 hours. The reaction mixture was quenched with water (10 mL) and extracted with ethyl acetate (30 mL×3). The combined organic layers were washed with brine (50 mL), dried over $Na_2SO_4$, filtered and concentrated under reduced pressure to give a residue. The residue was purified by prep-HPLC (column: Phenomenex Synergi Max-RP 250*50 mm*10 um; mobile phase: [water (0.225% FA)-ACN]; B %: 50%-75%, 25 min). The mixture was adjusted pH=7 by addition saturated $NaHCO_3$ aqueous solution and extracted with ethyl acetate (50 mL×3). The combined organic layers were washed with brine (20 mL), dried over $Na_2SO_4$, filtered and concentrated under reduced pressure. 1-bromo-8-fluoro-naphthalene (560 mg, 2.46 mmol, 35% yield, 99% purity) was obtained as a yellow solid.

$^1$H NMR (400 MHz, chloroform-d) δ=7.81 (d, J=7.2 Hz, 2H), 7.66 (d, J=8.4 Hz, 1H), 7.49-7.39 (m, 1H), 7.31 (t, J=7.6 Hz, 1H), 7.23 (td, J=0.8, 5.2 Hz, 1H).

Step A: tert-butyl (2S)-2-(cyanomethyl)-4-[7-(8-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate A mixture of 1-bromo-8-fluoro-naphthalene (310 mg, 1.38 mmol, 1.3 eq), tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 500 mg, 1.06 mmol, 1 eq), Cs$_2$CO$_3$ (863 mg, 2.65 mmol, 2.5 eq), RuPhos (98.9 mg, 212 umol, 0.2 eq) and Pd$_2$(dba)$_3$ (194 mg, 212 umol, 0.2 eq) in toluene (10 mL) was degassed and purged with N$_2$ for 3 times, and then the mixture was stirred at 100° C. for 3 hours under N$_2$ atmosphere. The reaction mixture was diluted with water (20 mL) and extracted with ethyl acetate (20 mL×3). The combined organic layers were washed with brine (20 mL), dried over Na$_2$SO$_4$, filtered and concentrated under reduced pressure to give a residue. The residue was purified by reversed phase flash [water (0.1% formic acid)/acetonitrile)]. The desired fractions were adjusted pH=7 with saturated NaHCO$_3$ aqueous solution and extracted with ethyl acetate (20 mL×3). The combined organic layers were washed with brine (20 mL), dried over Na$_2$SO$_4$, filtered and concentrated under reduced pressure. Compound tert-butyl (2S)-2-(cyanomethyl)-4-[7-(8-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (370 mg, 570 umol, 54% yield, 95% purity) was obtained as a yellow solid. LCMS [ESI, M+1]: 616.

$^1$H NMR (400 MHz, chloroform-d) δ=7.64 (d, J=7.6 Hz, 1H), 7.56 (br d, J=8.8 Hz, 1H), 7.47-7.42 (m, 1H), 7.20-7.08 (m, 3H), 4.64 (br s, 1H), 4.47-4.27 (m, 2H), 4.23-4.14 (m, 2H), 4.11-3.82 (m, 3H), 3.81-3.65 (m, 1H), 3.44-3.23 (m, 2H), 3.19-3.07 (m, 2H), 3.02-2.79 (m, 3H), 2.77-2.66 (m, 2H), 2.56 (br s, 1H), 2.50 (s, 3H), 2.34-2.25 (m, 1H), 2.13-2.06 (m, 1H), 1.82-1.72 (m, 3H), 1.53 (s, 9H).

Step B: 2-[(2S)-4-[7-(8-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(8-fluoro-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (370 mg, 600 umol, 1 eq) in DCM (600 uL) was added TFA (1.03 g, 9.01 mmol, 667 uL, 15 eq). The mixture was stirred at 25° C. for 1 hour. The reaction mixture was concentrated under vacuum. Compound 2-[(2S)-4-[7-(8-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (378 mg, 600 umol, 99% yield, TFA) was obtained as a yellow oil and used next step directly without purification. LCMS [ESI, M+1]: 516.

Step C: 2-[(2S)-4-[7-(8-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-fluoro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (261 mg, 506 umol, 1 eq, TFA) in DCM (5 mL) was added TEA (512 mg, 5.07 mmol, 705 uL, 10 eq) at 0° C. After addition, and prop-2-enoyl prop-2-enoate (51.1 mg, 405 umol, 0.8 eq) in DCM (1 mL) was added dropwise at 0° C. After stirred at 25° C. for 1 hour, the reaction mixture was quenched with saturated NaHCO$_3$ aqueous solution (1 mL) and extracted with ethyl acetate (20 mL×3). The combined organic layers were washed with brine (20 mL), dried over Na$_2$SO$_4$, filtered and concentrated under reduced pressure to give a residue. The residue was purified by prep-HPLC (column: Phenomenex Gemini 150*25 mm*10 um; mobile phase: [water (0.05% ammonia hydroxide v/v)-ACN]; B %: 48%-78%, 12 min). Title compound 2-[(2S)-4-[7-(8-fluoro-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 338, 93.5 mg, 163 umol, 32% yield, 99.4% purity) was obtained as a white solid. LCMS [ESI, M+1]: 570.

SFC condition: "OD-3 MeOH (DEA)_40_3 mL-35T Column: Chiralcel OD-3 50×4.6 mm I.D., 3 um Mobile phase: 40% methanol (0.05% DEA) in CO$_2$ Flow rate: 3 mL/min Wavelength: 220 nm".

$^1$H NMR (400 MHz, chloroform-d) δ=7.64 (d, J=8.0 Hz, 1H), 7.56 (d, J=8.4 Hz, 1H), 7.47-7.35 (m, 2H), 7.19-7.09 (m, 2H), 6.60 (br s, 1H), 6.40 (dd, J=1.6, 16.8 Hz, 1H), 5.83 (br d, J=10.4 Hz, 1H), 5.30-4.48 (m, 1H), 4.46-4.28 (m, 2H), 4.27-3.85 (m, 5H), 3.73 (br s, 1H), 3.56-2.54 (m, 10H), 2.49 (s, 3H), 2.37-2.21 (m, 1H), 2.12-1.97 (m, 1H), 1.95-1.79 (m, 3H).

Example 339

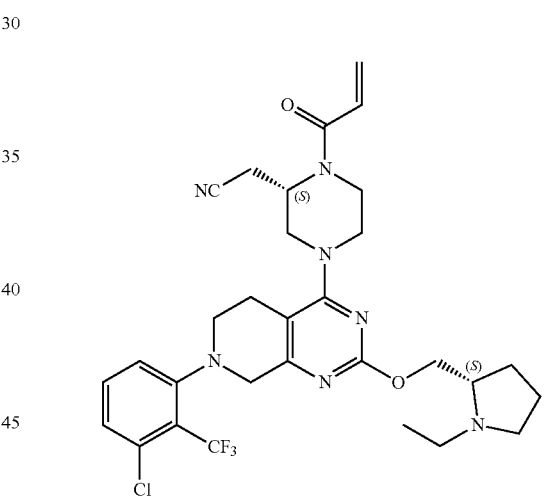

2-((S)-1-acryloyl-4-(7-(3-chloro-2-(trifluoromethyl)phenyl)-2-(((S)-1-ethylpyrrolidin-2-yl)methoxy)-5,6,7,8-tetrahydropyrido[3,4-d]pyrimidin-4-yl)piperazin-2-yl)acetonitrile

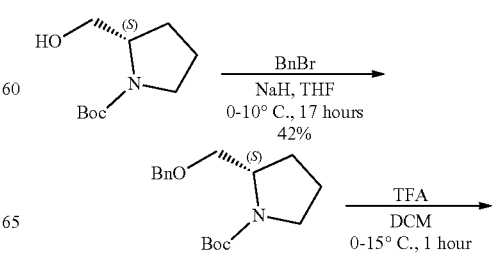

921

-continued

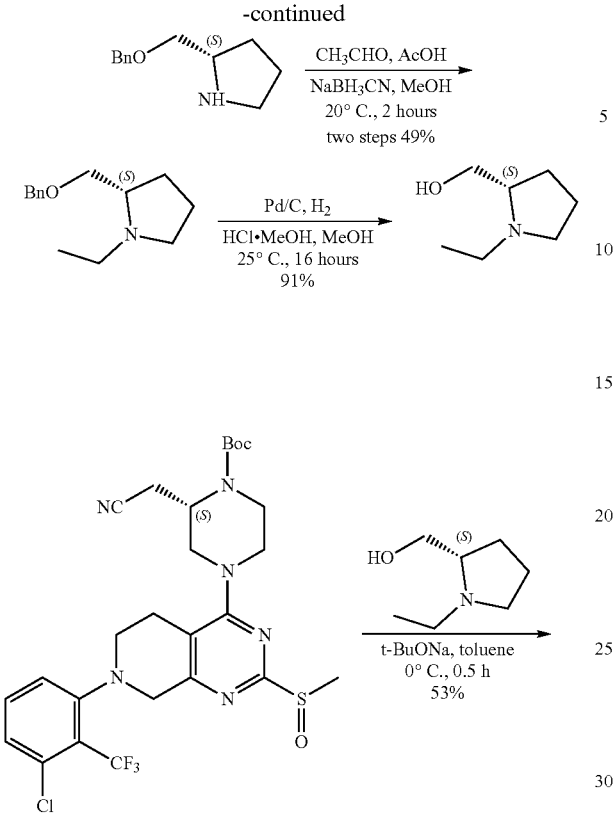

922

-continued

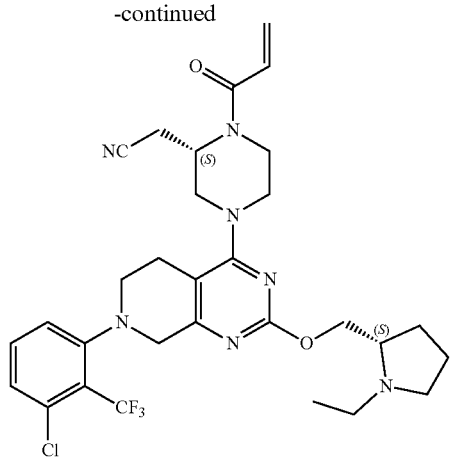

Step A: tert-butyl (2S)-2-(benzyloxymethyl)pyrrolidine-1-carboxylate

To a solution of NaH (1.19 g, 49.6 mmol, 2.0 eq) in THF (50.0 mL) was added a solution of tert-butyl (2S)-2-(hydroxymethyl)pyrrolidine-1-carboxylate (5.00 g, 24.8 mmol, 1.0 eq) in THF (50.0 mL) at 0° C. and the mixture was stirred at 10° C. for 1 hour. Bromomethylbenzene (6.38 g, 37.3 mmol, 4.43 mL, 1.50 eq) was added dropwise to the above mixture at 0° C. and the mixture was stirred at 10° C. for 16 hours. After completion, the mixture was quenched with saturated NH$_4$Cl aqueous (20.0 mL) and diluted with ethyl acetate (50.0 ml). The separated organic layer was washed with brine (1×30.0 mL) and dried over sodium sulfate, filtered and concentrated under vacuum. The obtained product was purified by column chromatography (SiO$_2$, Petroleum ether:Ethyl acetate=10:1-3:1) to give tert-butyl (2S)-2-(benzyloxymethyl)pyrrolidine-1-carboxylate (6.60 g, 10.4 mmol, 42% yield) as yellow oil.

$^1$H NMR (400 MHz, Methanol-d$_4$) δ 7.44-7.26 (m, 5H), 4.53 (s, 2H), 4.00-3.85 (m, 1H), 3.61-3.39 (m, 2H), 3.38-3.33 (m, 2H), 2.04-1.77 (m, 4H), 1.50-1.36 (m, 9H).

Step B: (2S)-2-(benzyloxymethyl)pyrrolidine

To a solution of tert-butyl (2S)-2-(benzyloxymethyl)pyrrolidine-1-carboxylate (6.60 g, 22.7 mmol, 1.0 eq) in DCM (23.0 mL) was added TFA (34.7 g, 304 mmol, 22.5 mL, 13.4 eq) dropwise at 0° C. under nitrogen atmosphere. The mixture was stirred at 15° C. for 1 hour. After completion, the mixture was concentrated under vacuum to give (2S)-2-(benzyloxymethyl)pyrrolidine (10.0 g, crude, TFA) as yellow oil. LCMS [ESI, M+1]: 192.

Step C: (2S)-2-(benzyloxymethyl)-1-ethylpyrrolidine

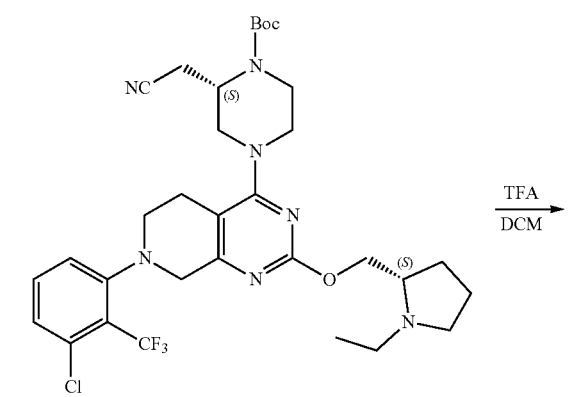

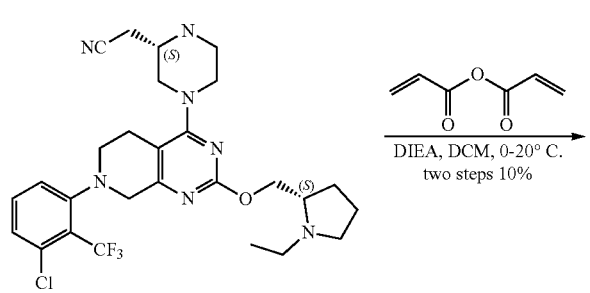

To a solution of (2S)-2-(benzyloxymethyl)pyrrolidine (2.0 g, 6.55 mmol, 1.0 eq, TFA) and acetaldehyde (1.44 g, 32.8 mmol, 1.84 mL, 5.0 eq) in MeOH (30.0 mL) was added CH$_3$COOH (787 mg, 13.1 mmol, 749 uL, 2.0 eq) and NaBH$_3$CN (1.65 g, 26.2 mmol, 4.0 eq). The mixture was stirred at 20° C. for 2 hours. After completion, the pH was adjusted to 3 with 1 M HCl aqueous (15.0 mL) and concentrated under vacuum to remove MeOH. The mixture was extracted with mixed solvent (PE/EA=10:1, 2×60.0 mL). The aqueous phase was adjusted to the pH ~9 with saturated Na₂CO₃ aqueous (10.0 mL) and extracted with mixed solvent (EA/MeOH=10:1, 4×60.0 mL). The organic layers were dried over Na₂SO₄ and concentrated under vacuum. The obtained product was purified by reversed-phase flash (0.1% TFA condition) to give (2S)-2-(benzyloxymethyl)-1-ethylpyrrolidine (707 mg, 3.18 mmol, 49% yield, 99.0% purity) as colorless oil.

¹H NMR (400 MHz, Chloroform-d) δ 7.36-7.31 (m, 4H), 7.31-7.26 (m, 1H), 4.58-4.54 (s, 2H), 3.52 (dd, J=4.8, 9.2 Hz, 1H), 3.37 (dd, J=6.4, 9.2 Hz, 1H), 3.20-3.12 (m, 1H), 3.01-2.89 (m, 1H), 2.66-2.58 (m, 1H), 2.35-2.25 (m, 1H), 2.21-2.05 (m, 1H), 2.03-1.87 (m, 1H), 1.83-1.62 (m, 3H), 1.11 (t, J=7.2 Hz, 3H).

Step D: [(2S)-1-ethylpyrrolidin-2-yl]methanol

To a solution of (2S)-2-(benzyloxymethyl)-1-ethyl-pyrrolidine (860 mg, 3.92 mmol, 1.00 eq) in MeOH (3.00 mL) was added HCl.MeOH (4 M, 0.80 mL) and Pd(OH)₂/C (300 mg, 20% purity). The suspension was degassed under vacuum and purged with H₂ several times. The mixture was stirred under H₂ (50 Psi) at 25° C. for 16 hours. After completion, the mixture was filtered and concentrated. The product [(2S)-1-ethylpyrrolidin-2-yl]methanol (460 mg, 3.56 mmol, 91% yield) was obtained as white solid. LCMS [ESI, M+1]: 130.

Step E: tert-butyl (2S)-4-[7-[3-chloro-2-(trifluoromethyl)phenyl]-2-[[(2S)-1-ethylpyrrolidin-2-yl]methoxy]-6,8-dihydro-5H-pyrido[3,4-d]pyrimidin-4-yl]-2-(cyanomethyl)piperazine-1-carboxylate To a solution of tert-butyl (2S)-4-[7-[3-chloro-2-(trifluoromethyl)phenyl]-2-methylsulfinyl-6,8-dihydro-5H-pyrido[3,4-d]pyrimidin-4-yl]-2-(cyanomethyl)piperazine-1-carboxylate (400 mg, 668 umol, 1.0 eq) and [(2S)-1-ethylpyrrolidin-2-yl]methanol (173 mg, 1.34 mmol, 2.0 eq) in toluene (8.0 mL) was added t-BuONa (128 mg, 1.34 mmol, 2.0 eq) at 0° C., the reaction was stirred at 0° C. for 0.5 hour. After completion, the reaction mixture was added water (30.0 mL), then extracted with EA (2×20.0 mL), the combined organic layer was washed with saturated brine (1×30.0 mL), then dried over Na₂SO₄, filtered and concentrated. The residue was purified by column chromatography (SiO₂, Petroleum ether/Ethyl acetate=5/1 to Ethyl acetate/Methanol=20/1) to give tert-butyl (2S)-4-[7-[3-chloro-2-(trifluoromethyl)phenyl]-2-[[(2S)-1-ethylpyrrolidin-2-yl]methoxy]-6,8-dihydro-5H-pyrido[3,4-d]pyrimidin-4-yl]-2-(cyanomethyl)piperazine-1-carboxylate (240 mg, 353 umol, 53% yield, 97.6% purity) as light yellow solid. LCMS [ESI, M+1]: 664.

Step F: 2-[(2S)-4-[7-[3-chloro-2-(trifluoromethyl)phenyl]-2-[[(2S)-1-ethylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-[3-chloro-2-(trifluoromethyl)phenyl]-2-[[(2S)-1-ethylpyrrolidin-2-yl]methoxy]-6,8-dihydro-5H-pyrido[3,4-d]pyrimidin-4-yl]-2-(cyanomethyl)piperazine-1-carboxylate (240 mg, 361 umol, 1.0 eq) in DCM (2.0 mL) was added TFA (3.08 g, 27.0 mmol, 2.0 mL, 74.8 eq), the mixture was stirred at 20° C. for 0.5 hour. After completion, the reaction mixture was concentrated to give 2-[(2S)-4-[7-[3-chloro-2-(trifluoromethyl)phenyl]-2-[[(2S)-1-ethylpyrrolidin-2-yl]methoxy]-6,8-dihydro-5H-pyrido[3,4-d]pyrimidin-4-yl]piperazin-2-yl]acetonitrile (280 mg, crude, 2TFA) as yellow oil which was used for the next step without further purification. LCMS [ESI, M+1]: 564.

Step G: 2-[(2S)-4-[7-[3-chloro-2-(trifluoromethyl)phenyl]-2-[[(2S)-1-ethylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2S)-4-[7-[3-chloro-2-(trifluoromethyl)phenyl]-2-[[(2S)-1-ethylpyrrolidin-2-yl]methoxy]-6,8-dihydro-5H-pyrido[3,4-d]pyrimidin-4-yl]piperazin-2-yl]acetonitrile (280 mg, 496 umol, 1.0 eq, 2TFA) in DCM (5.0 mL) was added DIEA (642 mg, 4.96 mmol, 865 uL, 10.0 eq) and prop-2-enoyl prop-2-enoate (62.6 mg, 496 umol, 1.0 eq) at 0° C., the reaction mixture was stirred at 20° C. for 0.5 hour. After completion, the reaction mixture was quenched with MeOH (5.0 mL), and concentrated. The residue was purified by column chromatography (Base Al₂O₃, Ethyl acetate/Methanol=20/1), then the crude product was concentrated and re-purified by prep-HPLC ((column: Phenomenex Gemini 150*25 mm*10 um; mobile phase: [water (0.05% ammonia hydroxide v/v)-ACN]; B %: 55%-85%, 12 min), the obtained product was concentrated, and then under lyophilization. The title compound 2-[(2S)-4-[7-[3-chloro-2-(trifluoromethyl)phenyl]-2-[[(2S)-1-ethylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 339, 31.9 mg, 50.2 umol, 10% yield, 97.2% purity) was obtained as yellow solid. LCMS [ESI, M+1]: 618.

¹H NMR (400 MHz, Chloroform-d) δ 7.37-7.29 (m, 1H), 7.23-7.18 (m, 1H), 7.11 (d, J=8.0 Hz, 1H), 6.58-6.46 (m, 1H), 6.32 (dd, J=0.8, 16.4 Hz, 1H), 5.76 (br d, J=10.4 Hz, 1H), 5.11-4.37 (m, 1H), 4.28 (dd, J=4.8, 10.4 Hz, 1H), 4.09-3.96 (m, 4H), 3.89 (br d, J=12.4 Hz, 2H), 3.69-3.41 (m, 1H), 3.33-2.51 (m, 12H), 2.38-2.28 (m, 1H), 2.20-2.11 (m, 1H), 2.00-1.80 (m, 3H), 1.06 (t, J=7.2 Hz, 3H).

Example 340

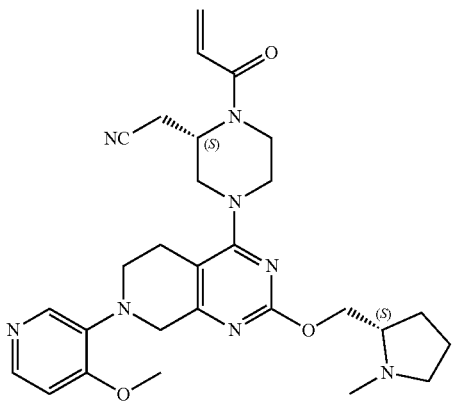

925

2-((S)-1-acryloyl-4-(7-(4-methoxypyridin-3-yl)-2-
(((S)-1-methylpyrrolidin-2-yl)methoxy)-5,6,7,8-
tetrahydropyrido[3,4-d]pyrimidin-4-yl)piperazin-2-
yl)acetonitrile

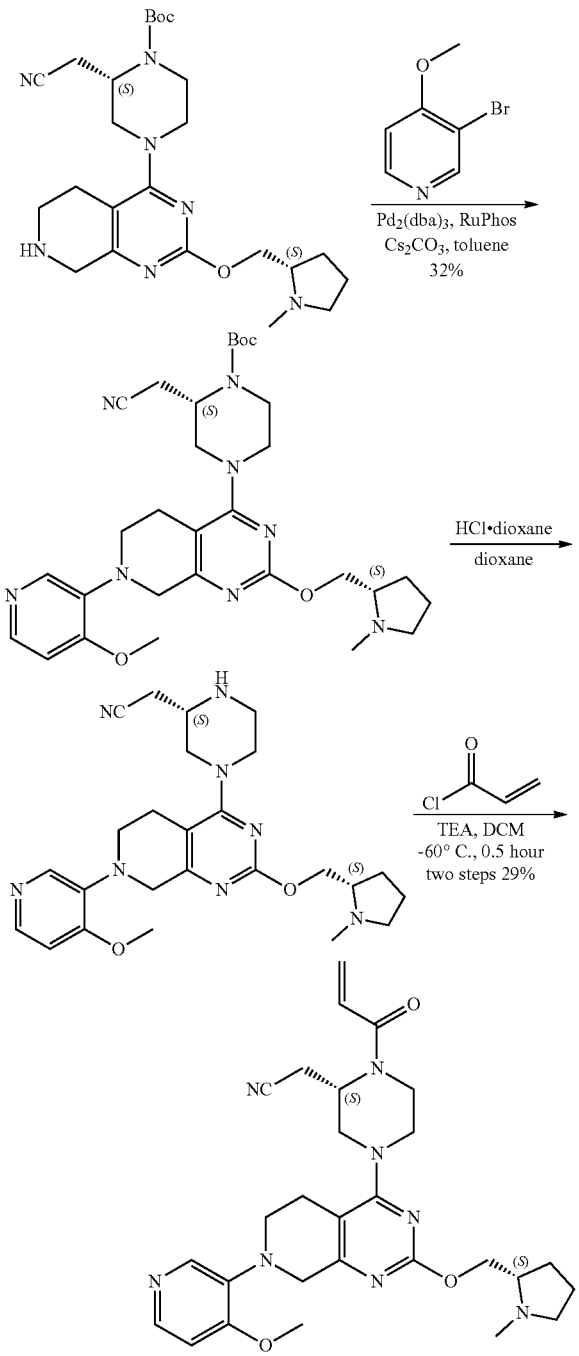

Step A: tert-butyl (2S)-2-(cyanomethyl)-4-[7-(4-
methoxy-3-pyridyl)-2-[[(2S)-1-methylpyrrolidin-2-
yl]methoxy]-6,8-dihydro-5H-pyrido[3,4-d]pyrimi-
din-4-yl]piperazine-1-carboxylate A mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (580 mg, 1.23 mmol, 1.0 eq), 3-bromo-4-methoxy-pyridine (694 mg, 3.69 mmol, 3.0 eq), $Pd_2(dba)_3$ (113 mg, 123 umol, 0.1 eq), RuPhos (115 mg, 246 umol, 0.2 eq) and $Cs_2CO_3$ (1.20 g, 3.69 mmol, 3.0 eq) in toluene (25.0 mL) was degassed and purged with $N_2$ for 3 times, and then the mixture was stirred at 90° C. for 6 hours under $N_2$ atmosphere. After completion, the organic solvent was removed under vacuum, and washed with water (20.0 mL). The aqueous phase was extracted with ethyl acetate (2×30.0 mL). Combined extracts were washed with brine (100 mL), dried over $Na_2SO_4$, the solvent was then removed under vacuum. The residue was purified by reversed phase flash HPLC [C18, 0.1% FA in water, 0-70% MeCN]. The obtained product was adjusted with saturated $NaHCO_3$ aqueous to pH ~8, then concentrated, the aqueous was extracted with ethyl acetate (2×50.0 mL), the combined organic layer was dried over $Na_2SO_4$, filtered and concentrated. Compound tert-butyl (2S)-2-(cyanomethyl)-4-[7-(4-methoxy-3-pyridyl)-2-[[(2S)-1-methylpyrrolidin-2-yl]methoxy]-6,8-dihydro-5H-pyrido[3,4-d]pyrimidin-4-yl]piperazine-1-carboxylate (230 mg, 397 umol, 32% yield, 100% purity) was obtained as yellow solid. LCMS [ESI, M+1]: 579.

Step B: 2-[(2S)-4-[7-(4-methoxy-3-pyridyl)-2-
[[(2S)-1-methylpyrrolidin-2-yl]methoxy]-6,8-di-
hydro-5H-pyrido[3,4-d]pyrimidin-4-yl]piperazin-2-
yl]acetonitrile To a solution of tert-butyl (2S)-2-(cyanomethyl)-4-[7-(4-methoxy-3-pyridyl)-2-[[(2S)-1-methylpyrrolidin-2-yl]methoxy]-6,8-dihydro-5H-pyrido[3,4-d]pyrimidin-4-yl]piperazine-1-carboxylate (350 mg, 605 umol, 1.0 eq) in dioxane (3.0 mL) was added 4M HCl/dioxane (5.0 mL), the mixture was stirred at 20° C. for 0.5 hour. After completion, the reaction mixture was concentrated, then extracted with DCM (10.0 mL), the organic layer was washed with saturated $NaHCO_3$ aqueous (2×10.0 mL), the organic layer was dried over $Na_2SO_4$, filtered and concentrated to give 2-[(2S)-4-[7-(4-methoxy-3-pyridyl)-2-[[(2S)-1-methylpyrrolidin-2-yl]methoxy]-6,8-dihydro-5H-pyrido[3,4-d]pyrimidin-4-yl]piperazin-2-yl]acetonitrile (260 mg, crude) as yellow oil which was used for the next step without further purification. LCMS [ESI, M+1]: 479.

Step C: 2-[(2S)-4-[7-(4-methoxy-3-pyridyl)-2-
[[(2S)-1-methylpyrrolidin-2-yl]methoxy]-6,8-di-
hydro-5H-pyrido[3,4-d]pyrimidin-4-yl]-1-prop-2-
enoyl-piperazin-2-yl]acetonitrile To a mixture of 2-[(2S)-4-[7-(4-methoxy-3-pyridyl)-2-[[(2S)-1-methylpyrrolidin-2-yl]methoxy]-6,8-dihydro-5H-pyrido[3,4-d]pyrimidin-4-yl]piperazin-2-yl]acetonitrile (260 mg, 543 umol, 1.0 eq) in DCM (5.0 mL) was added TEA (220 mg, 2.17 mmol, 302 uL, 4.0 eq) and prop-2-enoyl chloride (63.9 mg, 706 umol, 57.6 uL, 1.3 eq) at −60° C., the reaction mixture was stirred at −60° C. for 0.5 hour. After completion, the reaction mixture was quenched with MeOH (2.0 mL), and concentrated. The residue was purified by column chromatography (Base $Al_2O_3$, Petroleum ether: Ethyl acetate=3:1 to Ethyl acetate/Methanol=20/1), then the crude product was concentrated and re-purified by prep-HPLC (column: Gemini 150*25 5 u; mobile phase: [water (0.04% $NH_3H_2O$)-ACN]; B %: 30%-54%,10 min), the obtained product was concentrated, and then under lyophilization Title compound 2-[(2S)-4-[7-(4-methoxy-3-pyridyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 340, 83.6 mg, 155 umol, 29% yield, 98.8% purity) was obtained as white solid. LCMS [ESI, M+1]: 533.

$^1$H NMR (400 MHz, Chloroform-d) δ 8.25 (d, J=5.2 Hz, 1H), 8.17 (s, 1H), 6.82 (d, J=5.2 Hz, 1H), 6.38 (dd, J=1.2, 16.8 Hz, 1H), 6.44-6.33 (m, 1H), 5.82 (br d, J=10.4 Hz, 1H), 5.21-4.52 (m, 1H), 4.37 (dd, J=4.8 Hz, 10.4 Hz, 1H), 4.33-4.26 (m, 1H), 4.24-4.13 (m, 2H), 4.06 (br d, J=13.6 Hz, 1H), 4.02-3.88 (m, 5H), 3.72-3.37 (m, 2H), 3.36-3.23 (m, 2H), 3.16-3.02 (m, 2H), 2.98-2.88 (m, 1H), 2.87-2.72 (m, 3H), 2.70-2.60 (m, 1H), 2.47 (s, 3H), 2.33-2.27 (m, 1H), 2.10-1.99 (m, 1H), 1.91-1.69 (m, 3H).

Example 341

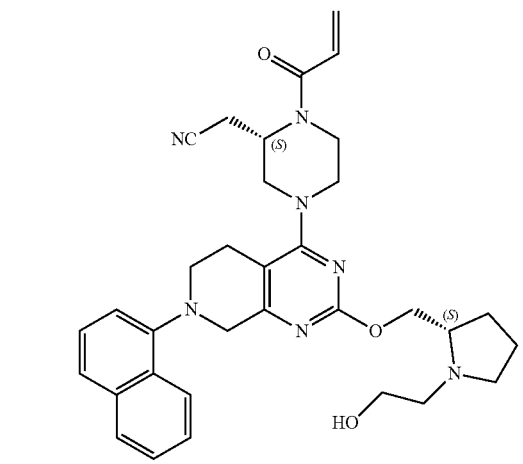

2-((S)-1-acryloyl-4-(2-(((S)-1-(2-hydroxyethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile

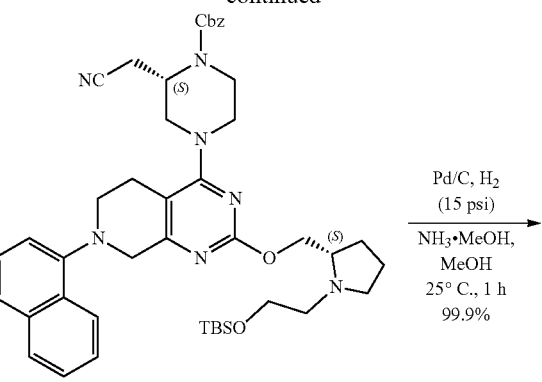

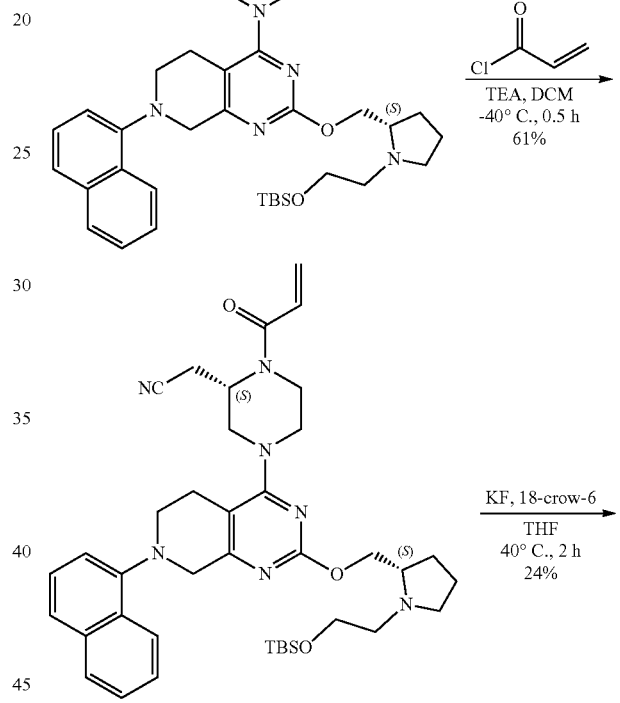

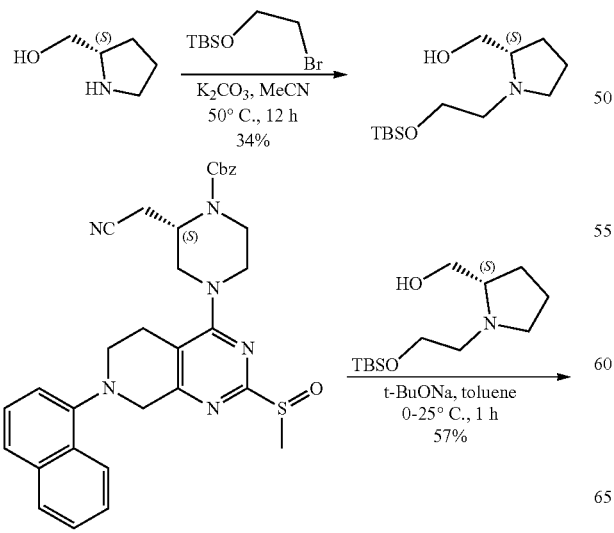

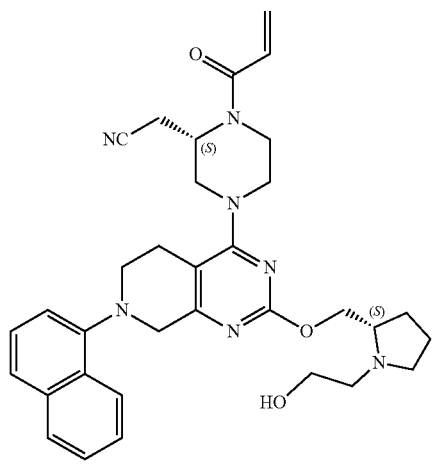

[(2S)-1-[2-[tert-butyl(dimethyl)silyl]oxyethyl] pyrrolidin-2-yl]methanol

To a mixture of [(2S)-pyrrolidin-2-yl]methanol (500 mg, 4.94 mmol, 481 uL, 1 eq) and 2-bromoethoxy-tert-butyl-dimethyl-silane (1.30 g, 5.44 mmol, 1.1 eq) in MeCN (30 mL) was added K$_2$CO$_3$ (3.42 g, 24.7 mmol, 5 eq) in portion under N$_2$. The mixture was stirred at 50° C. for 12 hours. The reaction mixture was filtered and the filtrate was concentrated under reduced pressure to give a residue. The residue was purified by column chromatography (Al$_2$O$_3$, Ethyl acetate/Methanol=100/1 to 5/1). Compound [(2S)-1-[2-[tert-butyl(dimethyl)silyl]oxyethyl] pyrrolidin-2-yl]methanol (437 mg, 1.68 mmol, 34.0% yield) was obtained as a brown oil.
$^1$H NMR (400 MHz, chloroform-d) δ=3.71 (dd, J=5.2, 6.4 Hz, 2H), 3.63-3.58 (m, 1H), 3.37 (dd, J=3.2, 10.8 Hz, 1H), 3.21 (td, J=4.8, 10.0 Hz, 1H), 2.90 (td, J=6.4, 12.8 Hz, 1H), 2.74-2.67 (m, 1H), 2.52 (td, J=5.2, 10.4 Hz, 1H), 2.41-2.31 (m, 1H), 1.97-1.80 (m, 1H), 1.79-1.55 (m, 3H), 0.92-0.87 (m, 9H), 0.11-0.00 (m, 6H).

Step A: benzyl (2S)-4-[2-[[(2S)-1-[2-[tert-butyl(dimethyl)silyl]oxyethyl]pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate To a mixture of [(2S)-1-[2-[tert-butyl(dimethyl)silyl]oxyethyl] pyrrolidin-2-yl]methanol (447 mg, 1.72 mmol, 2 eq) in toluene (35 mL) was added t-BuONa (248 mg, 2.58 mmol, 3 eq) in portion, then to the solution was added benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 66, 500 mg, 861 umol, 1 eq) at 0° C. The mixture was warmed to 25° C. and stirred for 1 hour. The reaction mixture was diluted with ethyl acetate 20 mL and adjusted PH to 8-9 with 2M HCl at 0° C., then extracted with ethyl acetate (20 mL×3). The combined organic layers were washed with water (15 mL×1), dried over sodium sulfate, filtered and concentrated under reduced pressure to give a residue. The residue was purified by column chromatography (SiO$_2$, Petroleum ether/Ethyl acetate=100/1 to 1/2). Compound benzyl (2S)-4-[2-[[(2S)-1-[2-[tert-butyl(dimethyl)silyl]oxyethyl]pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (400 mg, 494 umol, 57.4% yield, 95.8% purity) was obtained as a colorless oil. LCMS [ESI, M+1]: 776.

Step B: 2-[(2S)-4-[2-[[(2S)-1-[2-[tert-butyl(dimethyl)silyl]oxyethyl] pyrrolidin-2-yl]methoxy]-7-(1-naphthyl)-6,8-dihydro-5H-pyrido[3,4-d]pyrimidin-4-yl]piperazin-2-yl]acetonitrile To a solution of benzyl (2S)-4-[2-[[(2S)-1-[2-[tert-butyl(dimethyl)silyl]oxyethyl]pyrrolidin-2-yl]methoxy]-7-(1-naphthyl)-6,8-dihydro-5H-pyrido[3,4-d]pyrimidin-4-yl]-2-(cyanomethyl)piperazine-1-carboxylate (380 mg, 490 umol, 1 eq) in MeOH (30 mL) was added Pd/C (230 mg, 490 umol, 10% purity, 1.00 eq) and NH$_3$.MeOH (25 mL). The suspension was degassed under vacuum and purged with H$_2$ three times. The mixture was stirred under H$_2$ (15 psi) at 25° C. for 1 hour. The reaction mixture was filtered and concentrated under reduced pressure to give a residue. Compound 2-[(2S)-4-[2-[[(2S)-1-[2-[tert-butyl(dimethyl)silyl] oxyethyl] pyrrolidin-2-yl]methoxy]-7-(1-naphthyl)-6,8-dihydro-5H-pyrido[3,4-d]pyrimidin-4-yl]piperazin-2-yl]acetonitrile (314 mg, 489 umol, 99.9% yield) was obtained as a yellow oil and used directly into the next step without further purification. LCMS [ESI, M+1]: 642.

Step C: 2-[(2S)-4-[2-[[(2S)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a mixture of 2-[(2S)-4-[2-[[(2S)-1-[2-[tert-butyl(dimethyl) silyl]oxyethyl]pyrrolidin-2-yl]methoxy]-7-(1-naphthyl)-6,8-dihydro-5H-pyrido[3,4-d]pyrimidin-4-yl]piperazin-2-yl]acetonitrile (314 mg, 489 umol, 1 eq) in DCM (15 mL) was added TEA (148 mg, 1.47 mmol, 204 uL, 3 eq) and prop-2-enoyl chloride (57.6 mg, 636 umol, 51.9 uL, 1.3 eq) in portion at −40° C. under N$_2$. The mixture was stirred at −40° C. for 30 min. The reaction mixture was quenched by adding saturated NaHCO$_3$ solution 3 mL at −40° C., and then extracted with DCM (20 mL×3). The combined organic layers were washed with brine (15 mL×1), dried over sodium sulfate, filtered and concentrated under reduced pressure to give a residue. The residue was purified by column chromatography (Al$_2$O$_3$, Petroleum ether/Ethyl acetate=100/1 to 1/3). Compound 2-[(2S)-4-[2-[[(2S)-1-[2-[tert-butyl(dimethyl)silyl] oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (210 mg, 300 umol, 61.4% yield, 99.5% purity) was obtained as a colorless oil. LCMS [ESI, M+1]: 696.

Step D: 2-[(2S)-4-[2-[[(2S)-1-(2-hydroxyethyl) pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile To a mixture of 2-[(2S)-4-[2-[[(2S)-1-[2-[tert-butyl(dimethyl) silyl]oxyethyl]pyrrolidin-2-yl]methoxy]-7-(1-naphthyl)-6,8-dihydro-5H-pyrido[3,4-d]pyrimidin-4-yl]-1-prop-2-enoyl-piperazin-2-yl]acetonitrile (205 mg, 295 umol, 1 eq) in THF (3 mL) was added KF (171 mg, 2.95 mmol, 69.0 uL, 10 eq) and 18-crown-6 (779 mg, 2.95 mmol, 10 eq) in portion. The mixture was stirred at 40° C. for 2 hours. The reaction mixture was filtered and concentrated under reduced pressure to give a residue. The residue was purified by prep-HPLC (column: Phenomenex Gemini 150*25 mm*10 um; mobile phase: [water (0.05% ammonia hydroxide v/v)-ACN]; B %: 45%-75%, 12 min). Title compound 2-[(2S)-4-[2-[[(2S)-1-(2-hydroxyethyl) pyrrolidin-2-yl] methoxy]-7-(1-naphthyl)-6,8-dihydro-5H-pyrido[3,4-d]pyrimidin-4-yl]-1-prop-2-enoyl-piperazin-2-yl]acetonitrile (EXAMPLE 341, 43.4 mg, 71.6 umol, 24.3% yield, 95.9% purity) was obtained as a white solid. LCMS [ESI, M+1]: 582.
SFC: "OJ-3S_3_5_40_3ML Column: Chiralcel OJ-3 100×4.6 mm I.D., 3 um Mobile phase: methanol (0.05% DEA) in CO$_2$ from 5% to 40% Flow rate: 3 mL/min Wavelength: 220 nm".
$^1$H NMR (400 MHz, chloroform-d) δ=8.24-8.18 (m, 1H), 7.89-7.83 (m, 1H), 7.61 (d, J=8.4 Hz, 1H), 7.54-7.47 (m, 2H), 7.44 (t, J=7.2 Hz, 1H), 7.15 (d, J=6.8 Hz, 1H), 6.60 (br s, 1H), 6.40 (dd, J=1.6, 16.8 Hz, 1H), 5.84 (br d, J=10.4 Hz, 1H), 5.11 (br s, 1H), 4.36-4.22 (m, 3H), 4.16 (dd, J=6.8, 10.4 Hz, 2H), 4.01 (br d, J=11.6 Hz, 1H), 3.72-3.55 (m, 3H), 3.53-3.26 (m, 3H), 3.24-2.68 (m, 10H), 2.62 (td, J=4.0, 12.5 Hz, 1H), 2.39-2.28 (m, 1H), 2.07-1.96 (m, 1H), 1.90-1.75 (m, 3H).

Example 342
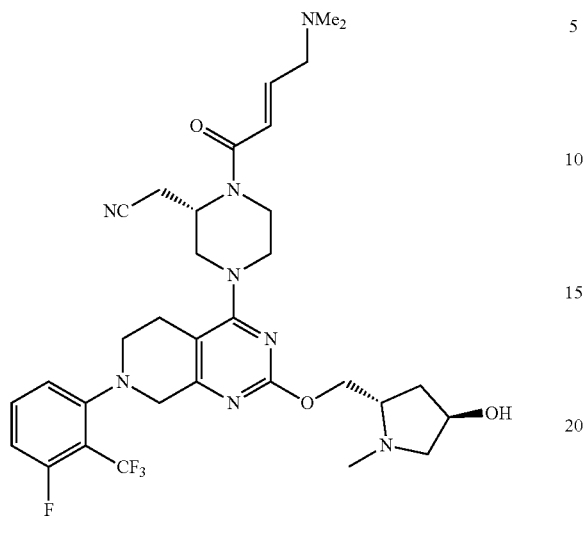
2-[(2S)-1-[(E)-4-(dimethylamino)but-2-enoyl]-4-[7-
[3-fluoro-2-(trifluoromethyl)phenyl]-2-[[(2S,4R)-4-
hydroxy-1-methyl-pyrrolidin-2-yl]methoxy]-6,8-
dihydro-5H-pyrido[3,4-d]pyrimidin-4-yl]piperazin-
2-yl]acetonitrile
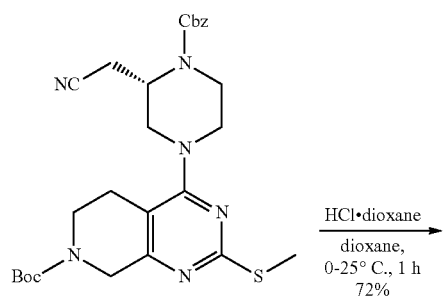
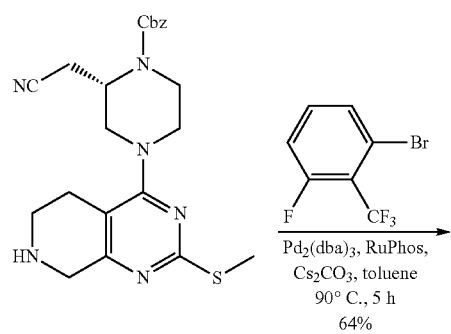

-continued
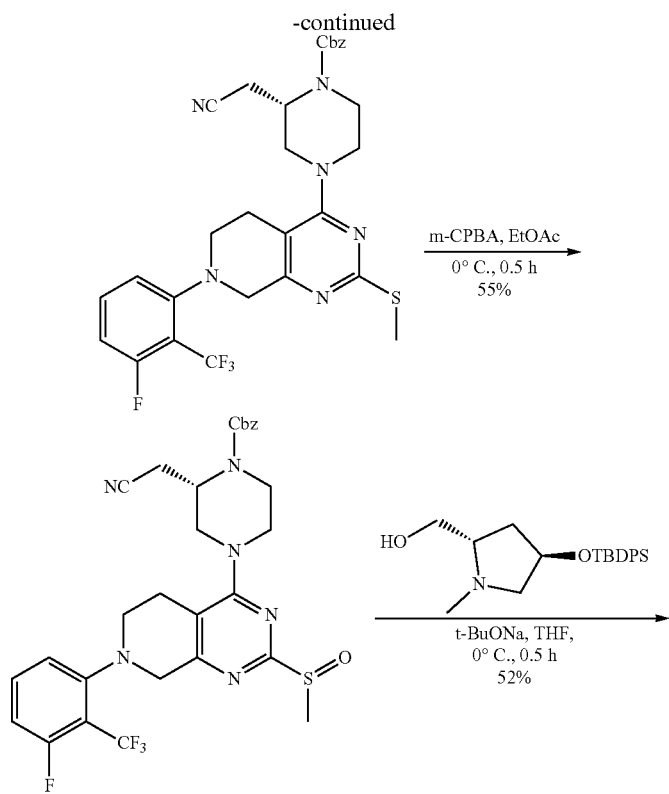
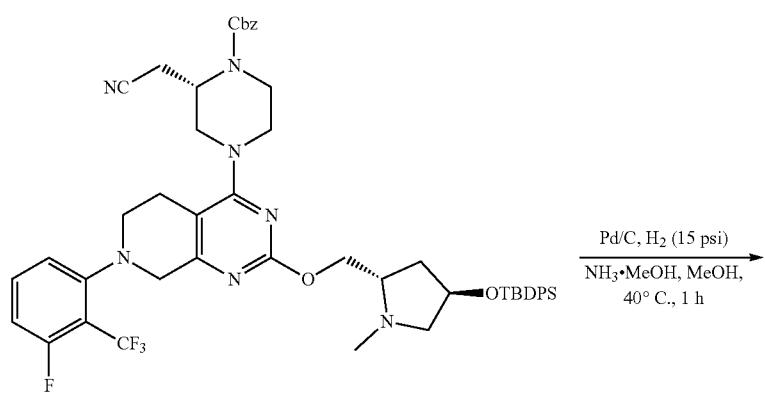
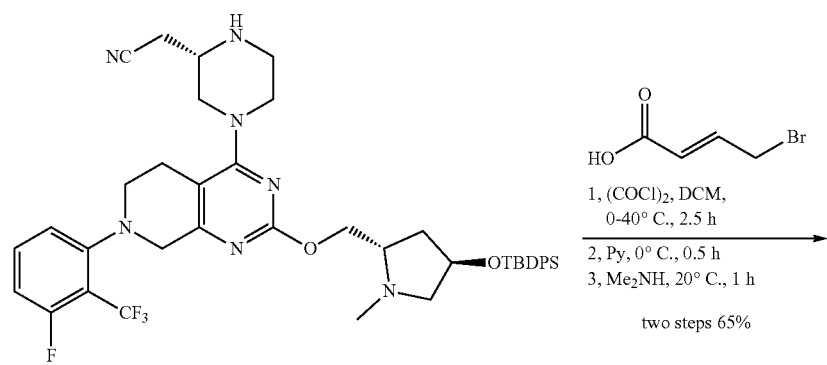

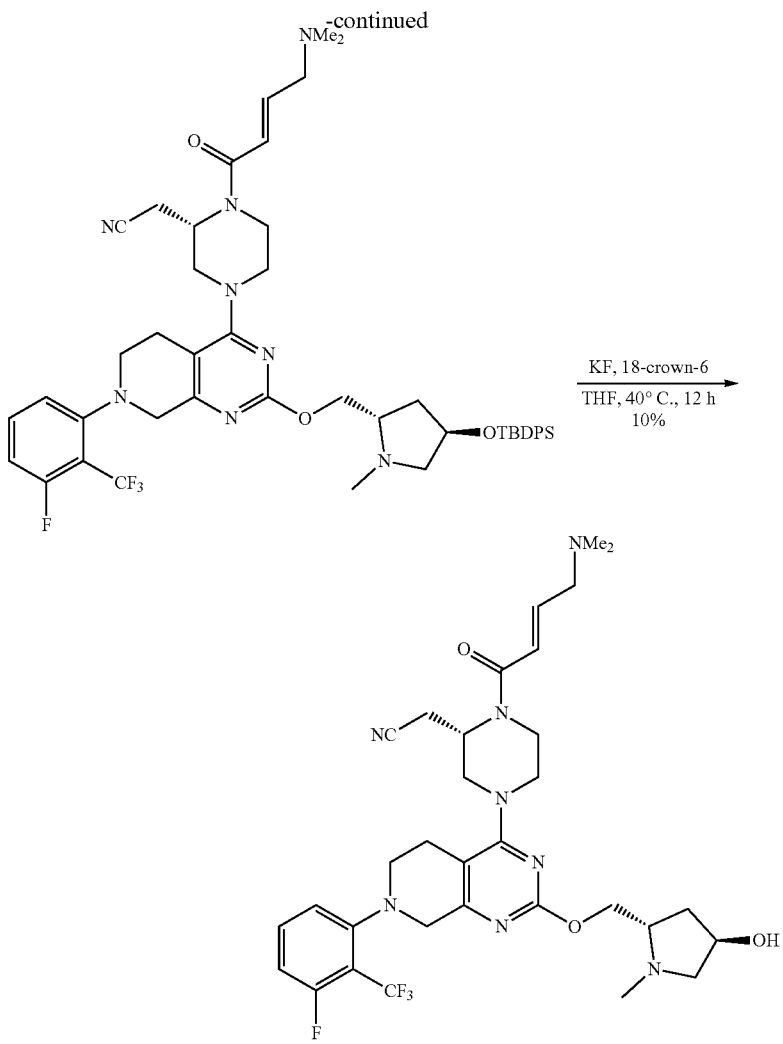

Step A: benzyl (2S)-2-(cyanomethyl)-4-(2-methylsulfanyl-5,6,7,8-tetrahydropyrido[3,4-d]pyrimidin-4-yl)piperazine-1-carboxylate To a solution tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (3.00 g, 5.57 mmol, 1.00 eq) in dioxane (30.0 mL) was added HCl/dioxane (4.00 M, 30.0 mL, 21.6 eq) at 0° C. After stirred at 25° C. for 1 hour, the mixture was concentrated under vacuum. The residue was diluted with water (4.00 mL), adjusted pH >8 by saturated sodium bicarbonate (10.0 mL) and extracted with ethyl acetate (3×30.0 mL). The extracts were dried over $Na_2SO_4$, filtered and concentrated under vacuum. The residue was purified by column chromatography ($Al_2O_3$, methanol/ethyl acetate=10/1) to give benzyl (2S)-2-(cyanomethyl)-4-(2-methylsulfanyl-5,6,7,8-tetrahydropyrido[3,4-d]pyrimidin-4-yl)piperazine-1-carboxylate (2.10 g, 4.02 mmol, 72% yield) as a yellow solid. LCMS [ESI, M+1]: 439.

$^1$H NMR (400 MHz, chloroform-d) δ=7.46-7.30 (m, 5H), 5.25-5.14 (m, 2H), 4.66 (br s, 1H), 4.14-4.05 (m, 1H), 4.04-3.90 (m, 3H), 3.84 (br d, J=12.4 Hz, 1H), 3.26 (br d, J=11.6 Hz, 2H), 3.12 (td, J=5.2, 12.4 Hz, 1H), 3.05-2.91 (m, 2H), 2.79 (br s, 1H), 2.74-2.56 (m, 3H), 2.49 (s, 3H).

Step B: benzyl (2S)-2-(cyanomethyl)-4-[7-[3-fluoro-2-(trifluoromethyl)phenyl]-2-methylsulfanyl-6,8-dihydro-5H-pyrido[3,4-d]pyrimidin-4-yl]piperazine-1-carboxylate A mixture of benzyl (2S)-2-(cyanomethyl)-4-(2-methylsulfanyl-5,6,7,8-tetrahydropyrido[3,4-d]pyrimidin-4-yl)piperazine-1-carboxylate (2.00 g, 4.56 mmol, 1.00 eq), 1-bromo-3-fluoro-2-(trifluoromethyl)benzene (1.66 g, 6.84 mmol, 1.50 eq), $Pd_2(dba)_3$ (418 mg, 456 umol, 0.10 eq), RuPhos (426 mg, 912 umol, 0.20 eq) and $Cs_2CO_3$ (2.97 g, 9.12 mmol, 2.00 eq) in toluene (30.0 mL) was stirred at 90° C. for 5 hours. The mixture was diluted with water (20.0 mL), extracted with ethyl acetate (3×30.0 mL). The organic layers were washed with brine (1×40.0 mL), dried over $Na_2SO_4$, filtered and concentrated under vacuum. The residue was purified by reversed phase flash [water (TFA, 0.10%)/acetonitrile]. The desired fractions were collected and adjusted pH >7 by saturated sodium bicarbonate (5.00 mL), extracted with ethyl acetate (3×30.0 mL), dried over $Na_2SO_4$, filtered and concentrated under vacuum to give benzyl (2S)-2-(cyanomethyl)-4-[7-[3-fluoro-2-(trifluoromethyl)phenyl]-2-methylsulfanyl-6,8-dihydro-5H-pyrido[3,4-d]pyrimidin-4-yl]piperazine-1-carboxylate (2.00 g, 2.90 mmol, 64% yield) as a yellow solid. LCMS [ESI, M+1]: 601.

¹H NMR (400 MHz, chloroform-d) δ=7.53-7.44 (m, 1H), 7.43-7.29 (m, 5H), 7.07 (d, J=8.0 Hz, 1H), 7.00-6.91 (m, 1H), 5.26-5.13 (m, 2H), 4.69 (br s, 1H), 4.16-4.10 (m, 3H), 4.04 (br d, J=13.2 Hz, 1H), 3.87 (br d, J=12.4 Hz, 1H), 3.39-3.22 (m, 3H), 3.19-3.09 (m, 1H), 3.04 (dt, J=3.6, 12.4 Hz, 1H), 2.83 (br s, 2H), 2.76-2.67 (m, 2H), 2.51 (s, 3H).

Step C: benzyl (2S)-2-(cyanomethyl)-4-[7-[3-fluoro-2-(trifluoromethyl)phenyl]-2-methylsulfinyl-6,8-dihydro-5H-pyrido[3,4-d]pyrimidin-4-yl]piperazine-1-carboxylate To a solution of benzyl (2S)-2-(cyanomethyl)-4-[7-[3-fluoro-2-(trifluoromethyl)phenyl]-2-methylsulfanyl-6,8-dihydro-5H-pyrido[3,4-d]pyrimidin-4-yl]piperazine-1-carboxylate (1.90 g, 3.16 mmol, 1.00 eq) in ethyl acetate (50.0 mL) was added m-CPBA (610 mg, 3.01 mmol, 85% purity, 0.95 eq) at 0° C. After stirred at 0° C. for 0.5 h, the mixture was diluted with water (30.0 mL), adjusted pH >7 by saturated sodium bicarbonate (10.0 mL) and extracted with ethyl acetate (3×20.0 mL). The organic layers were washed with brine (1×40.0 mL), dried over Na₂SO₄, filtered and concentrated under vacuum. The residue was purified by column chromatography (SiO₂, petroleum ether/ethyl acetate=1/3) to give benzyl (2S)-2-(cyanomethyl)-4-[7-[3-fluoro-2-(trifluoromethyl)phenyl]-2-methylsulfinyl-6,8-dihydro-5H-pyrido[3,4-d]pyrimidin-4-yl]piperazine-1-carboxylate (1.20 g, 1.73 mmol, 55% yield) as a yellow solid. LCMS [ESI, M+1]: 617.

¹H NMR (400 MHz, chloroform-d) δ=7.55-7.47 (m, 1H), 7.44-7.33 (m, 5H), 7.08 (d, J=8.0 Hz, 1H), 7.03-6.94 (m, 1H), 5.20 (s, 2H), 4.68 (br s, 1H), 4.31-4.09 (m, 4H), 4.02 (br d, J=12.0 Hz, 1H), 3.46 (br d, J=13.2 Hz, 1H), 3.40-3.09 (m, 4H), 2.90 (br d, J=2.8 Hz, 6H), 2.74-2.64 (m, 1H).

Step D: benzyl (2S)-4-[2-[[(2S,4R)-4-[tert-butyl(diphenyl)silyl]oxy-1-methyl-pyrrolidin-2-yl]methoxy]-7-[3-fluoro-2-(trifluoromethyl)phenyl]-6,8-dihydro-5H-pyrido[3,4-d]pyrimidin-4-yl]-2-(cyanomethyl)piperazine-1-carboxylate To a solution of [(2S,4R)-4-[tert-butyl(diphenyl)silyl]oxy-1-methyl-pyrrolidin-2-yl]methanol (145 mg, 392 umol, 1.10 eq) in THF (5.00 mL) was added t-BuONa (68.6 mg, 714 umol, 2.00 eq) at 0° C. Then benzyl (2S)-2-(cyanomethyl)-4-[7-[3-fluoro-2-(trifluoromethyl)phenyl]-2-methylsulfinyl-6,8-dihydro-5H-pyrido[3,4-d]pyrimidin-4-yl]piperazine-1-carboxylate (0.22 g, 357 umol, 1.00 eq) was added into the mixture. After stirred at 0° C. for 0.5 h, the mixture was diluted with ethyl acetate (10.0 mL) and water (10.0 mL), and then extracted with ethyl acetate (3×10.0 mL). The extracts were washed with brine (1×20.0 mL), dried over Na₂SO₄, filtered and concentrated under vacuum. The residue was purified by column chromatography (Al₂O₃, petroleum ether/ethyl acetate=1/3) to give benzyl (2S)-4-[2-[[(2S,4R)-4-[tert-butyl(diphenyl)silyl]oxy-1-methyl-pyrrolidin-2-yl]methoxy]-7-[3-fluoro-2-(trifluoromethyl)phenyl]-6,8-dihydro-5H-pyrido[3,4-d]pyrimidin-4-yl]-2-(cyanomethyl)piperazine-1-carboxylate (0.18 g, 185 umol, 52% yield) as a yellow solid. LCMS [ESI, M/2+1]: 462.

Step E: 2-[(2S)-4-[2-[[(2S,4R)-4-[tert-butyl(diphenyl)silyl]oxy-1-methyl-pyrrolidin-2-yl]methoxyl]-7-[3-fluoro-2-(trifluoromethyl)phenyl]-6,8-dihydro-5H-pyrido[3,4-d]pyrimidin-4-yl]piperazin-2-yl]acetonitrile NH₃ was bubbled in methanol (30.0 mL) at −78° C. for 15 minutes. Benzyl (2S)-4-[2-[[(2S,4R)-4-[tert-butyl(diphenyl)silyl]oxy-1-methyl-pyrrolidin-2-yl]methoxy]-7-[3-fluoro-2-(trifluoromethyl)phenyl]-6,8-dihydro-5H-pyrido[3,4-d]pyrimidin-4-yl]-2-(cyanomethyl)piperazine-1-carboxylate (0.18 g, 195 umol, 1.00 eq) and Pd/C (0.10 g, 10% purity) was added into the mixture. After stirred at 40° C. for 1 hour under H₂ at 15 psi, the catalyst was filtered and concentrated under vacuum to give 2-[(2S)-4-[2-[[(2S,4R)-4-[tert-butyl(diphenyl)silyl]oxy-1-methyl-pyrrolidin-2-yl]methoxy]-7-[3-fluoro-2-(trifluoromethyl)phenyl]-6,8-dihydro-5H-pyrido[3,4-d]pyrimidin-4-yl]piperazin-2-yl]acetonitrile (0.13 g, crude) as a yellow solid. LCMS [ESI, M/2+1]: 395.

Step F: 2-[(2S)-4-[2-[[(2S,4R)-4-[tert-butyl(diphenyl)silyl]oxy-1-methyl-pyrrolidin-2-yl]methoxy]-7-[3-fluoro-2-(trifluoromethyl)phenyl]-6,8-dihydro-5H-pyrido[3,4-d]pyrimidin-4-yl]-1-[(E)-4-(dimethylamino)but-2-enoyl]piperazin-2-yl]acetonitrile A mixture of (E)-4-bromobut-2-enoic acid (0.50 g, 3.03 mmol, 1.00 eq) and oxalyl dichloride (3.85 g, 30.31 mmol, 2.65 mL, 10.0 eq) in dichloromethane (5 mL) was stirred at 0° C. for 0.5 h and 40° C. for 2 hours. The mixture was concentrated under vacuum. The above residue (93.0 mg, crude) was added into the mixture of 2-[(2S)-4-[2-[[(2S,4R)-4-[tert-butyl(diphenyl)silyl]oxy-1-methyl-pyrrolidin-2-yl]methoxy]-7-[3-fluoro-2-(trifluoromethyl)phenyl]-6,8-dihydro-5H-pyrido[3,4-d]pyrimidin-4-yl]piperazin-2-yl]acetonitrile (80.0 mg, crude) and Py (80.3 mg, 1.02 mmol, 82.0 uL) in dichloromethane (0.50 mL) at 0° C. After stirred at 0° C. for 0.5 h, N-methylmethanamine (69.4 mg, 508 umol, 77.9 uL) was added and the mixture was stirred at 20° C. for 1 hour. Then the mixture was concentrated under vacuum. The residue was purified by reversed phase flash [water (TFA, 0.10%)]. The desired fractions were adjusted pH >7 by saturated sodium bicarbonate (1×5.00 mL) and extracted with ethyl acetate (3×10.0 mL). The extracts were washed with brine (1×10.0 mL), dried over Na₂SO₄, filtered and concentrated under vacuum to give 2-[(2S,4R)-4-[tert-butyl(diphenyl)silyl]oxy-1-methyl-pyrrolidin-2-yl]methoxy]-7-[3-fluoro-2-(trifluoromethyl)phenyl]-6,8-dihydro-5H-pyrido[3,4-d]pyrimidin-4-yl]-1-[(E)-4-(dimethylamino)but-2-enoyl]piperazin-2-yl]acetonitrile (0.06 g, 48.05 umol, two steps 65% yield) was obtained as a yellow oil. LCMS [ESI, M+1]: 899.

Step G: 2-[(2S)-1-[(E)-4-(dimethylamino)but-2-enoyl]-4-[7-[3-fluoro-2-(trifluoromethyl)phenyl]-2-[[(2S,4R)-4-hydroxy-1-methyl-pyrrolidin-2-yl]methoxy]-6,8-dihydro-5H-pyrido[3,4-d]pyrimidin-4-yl]piperazin-2-yl]acetonitrile A mixture of 2-[(2S)-4-[2-[[(2S,4R)-4-[tert-butyl(diphenyl)silyl]oxy-1-methyl-pyrrolidin-2-yl]methoxy]-7-[3-fluoro-2-(trifluoromethyl)phenyl]-6,8-dihydro-5H-pyrido[3,4-d]pyrimidin-4-yl]-1-[(E)-4-(dimethylamino)but-2-enoyl]piperazin-2-yl]acetonitrile (0.06 g, 66.7 umol, 1.00 eq), KF (38.8 mg, 667 umol, 15.6 uL, 10.0 eq) and 18-crown-6 (176 mg, 667 umol, 10.0 eq) in THF (0.10 mL) was stirred at 40° C. for 12 hours. The mixture was concentrated under vacuum. The residue was purified by reversed phase flash [water (TFA, 0.10%/acetonitrile)] and prep-HPLC column: Gemini 150*25 5 u; mobile phase: [water (0.05% ammonia hydroxide v/v)-ACN]; B %: 30%-60%, 12 min. The desired fractions were collected and lyophilized to give title compound 2-[(2S)-1-[(E)-4-(dimethylamino)but-2-enoyl]-4-[7-[3-fluoro-2-(trifluoromethyl)

phenyl]-2-[[(2S,4R)-4-hydroxy-1-methyl-pyrrolidin-2-yl]methoxy]-6,8-dihydro-5H-pyrido[3,4-d]pyrimidin-4-yl]piperazin-2-yl]acetonitrile (EXAMPLE 342, 4.60 mg, 6.91 umol, 10% yield, 99.2% purity) as a white solid. LCMS [ESI, M+1]:661.

$^1$H NMR (400 MHz, chloroform-d) δ=7.52-7.44 (m, 1H), 7.07 (d, J=8.4 Hz, 1H), 7.00-6.90 (m, 2H), 6.46 (br d, J=15.2 Hz, 1H), 5.07 (br s, 1H), 4.50-4.42 (m, 1H), 4.36 (dd, J=4.8, 10.8 Hz, 1H), 4.22 (dd, J=5.6, 10.8 Hz, 1H), 4.16-4.06 (m, 3H), 3.96 (br d, J=11.6 Hz, 2H), 3.60 (br s, 1H), 3.43 (dd, J=6.0, 10.0 Hz, 1H), 3.39-3.23 (m, 2H), 3.20-3.05 (m, 4H), 3.05-2.79 (m, 4H), 2.78-2.62 (m, 2H), 2.48 (s, 3H), 2.35-2.26 (m, 7H), 2.12-1.92 (m, 2H).

Example 343

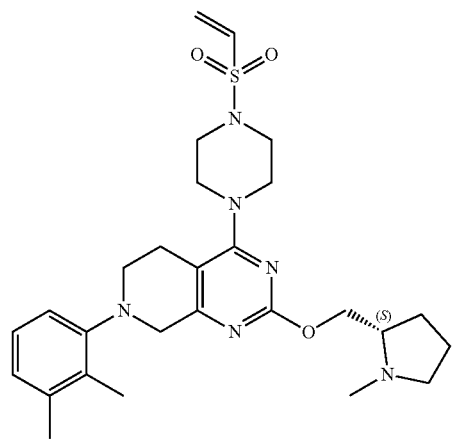

(S)-7-(2,3-dimethylphenyl)-2-((1-methylpyrrolidin-2-yl)methoxy)-4-(4-(vinylsulfonyl)piperazin-1-yl)-5,6,7,8-tetrahydropyrido[3,4-d]pyrimidine

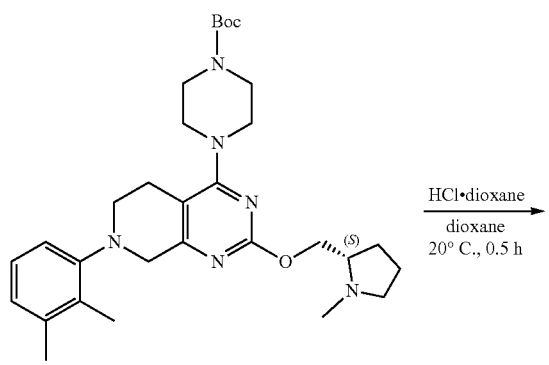

HCl•dioxane
dioxane
20° C., 0.5 h

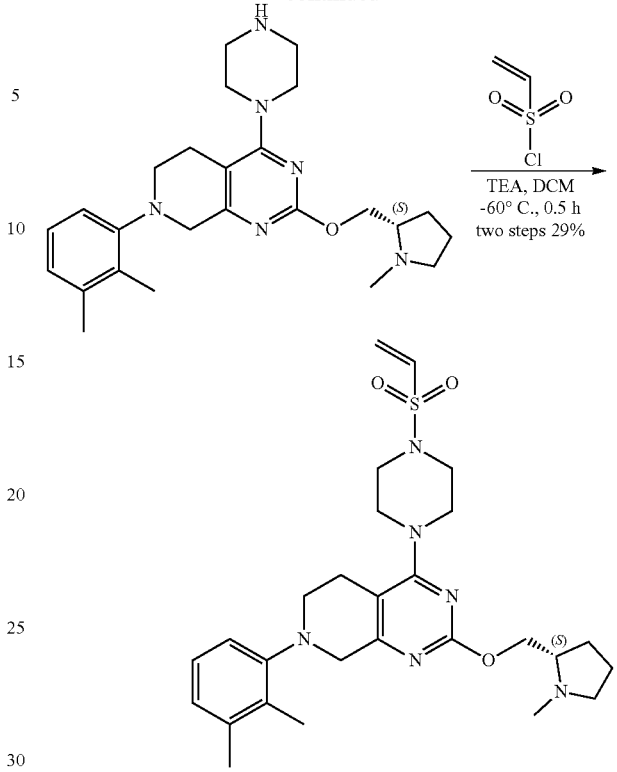

TEA, DCM
-60° C., 0.5 h
two steps 29%

Step A: 7-(2,3-dimethylphenyl)-2-[[(2S)-1-methyl-pyrrolidin-2-yl]methoxy]-4-piperazin-1-yl-6,8-dihydro-5H-pyrido[3,4-d]pyrimidine To a solution of tert-butyl 4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (350 mg, 652 umol, 1.0 eq) in dioxane (3.0 mL) was added 4M HCl/dioxane (5.0 mL), the mixture was stirred at 20° C. for 0.5 hour. After completion, the reaction mixture was concentrated, then added DCM (10.0 mL), the organic layer was washed with saturated NaHCO$_3$ aqueous (2×10.0 mL), the organic layer was dried over Na$_2$SO$_4$, filtered and concentrated to give 7-(2,3-dimethylphenyl)-2-[[(2S)-1-methylpyrrolidin-2-yl]methoxy]-4-piperazin-1-yl-6,8-dihydro-5H-pyrido[3,4-d]pyrimidine (280 mg, crude) as yellow oil which was used for the next step without further purification. LCMS [ESI, M+1]: 437.

Step B: 7-(2,3-dimethylphenyl)-2-[[(2S)-methylpyrrolidin-2-yl]methoxy]-4-(4-vinylsulfonylpiperazin-1-yl)-6,8-dihydro-5H-pyrido[3,4-d]pyrimidine To a mixture of 7-(2,3-dimethylphenyl)-2-[[(2S)-1-methylpyrrolidin-2-yl]methoxy]-4-piperazin-1-yl-6,8-dihydro-5H-pyrido[3,4-d]pyrimidine (280 mg, 641 umol, 1.0 eq) in DCM (5.0 mL) was added TEA (195 mg, 1.92 mmol, 268 uL, 3.0 eq) and ethenesulfonyl chloride (122 mg, 962 umol, 1.5 eq) at −60° C., the reaction mixture was stirred at −60° C. for 0.5 hour. After completion, the reaction mixture was quenched with MeOH (1.0 mL), and concentrated. The residue was purified by column chromatography (Base Al$_2$O$_3$, Petroleum ether: Ethyl acetate=3:1~Ethyl acetate/Methanol=20/1), then the crude product was concentrated and repurified by prep-HPLC (column: Phenomenex Gemini 150*25 mm*10 um; mobile phase: [water (0.05% ammonia hydroxide v/v)-ACN]; B %: 62%-92%,12 min), the obtained product was concentrated, and then under lyophilization. Title compound 7-(2,3-dimethylphenyl)-2-[[(2S)-methyl-pyrrolidin-2-yl]methoxy]-4-(4-vinylsulfonylpiperazin-1-yl)-6,8-dihydro-5H-pyrido[3,4-d]pyrimidine (EXAMPLE 343, 98.2 mg, 185 umol, 29% yield, 99.3% purity) was obtained as white solid. LCMS [ESI, M+1]: 527.

$^1$H NMR (400 MHz, chloroform-d) δ 7.12 (t, J=7.6 Hz, 1H), 7.00-6.94 (m, 2H), 6.47 (dd, J=10.0 Hz, 16.8 Hz, 1H), 6.30 (d, J=16.8 Hz, 1H), 6.11 (d, J=10.0 Hz, 1H), 4.39 (dd, J=4.8, 10.4 Hz, 1H), 4.15 (dd, J=6.8, 10.4 Hz, 1H), 4.03 (s, 2H), 3.62 (t, J=4.6 Hz, 4H), 3.30 (t, J=4.6 Hz, 4H), 3.19-3.05 (m, 3H), 2.80-2.62 (m, 3H), 2.49 (s, 3H), 2.32-2.25 (m, 7H), 2.13-2.00 (m, 1H), 1.92-1.72 (m, 3H).

Example 344

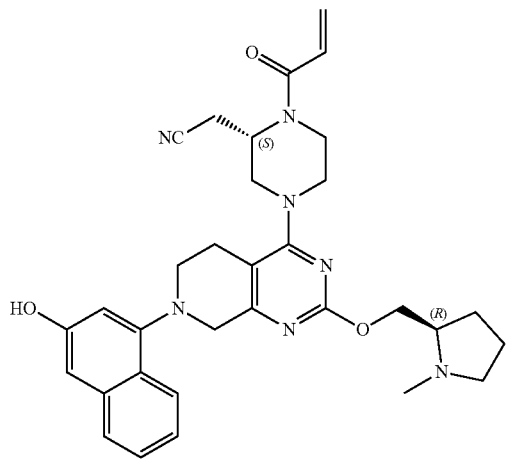

2-[(2S)-4-[7-(3-hydroxy-1-naphthyl)-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

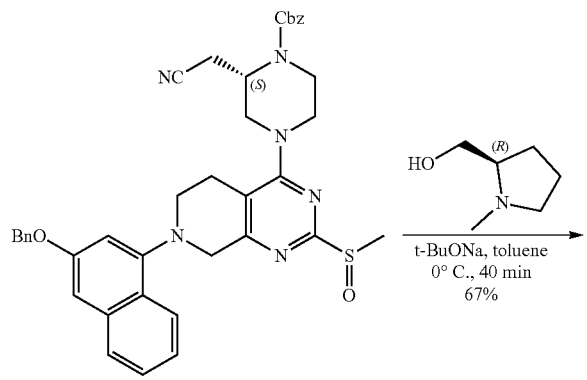

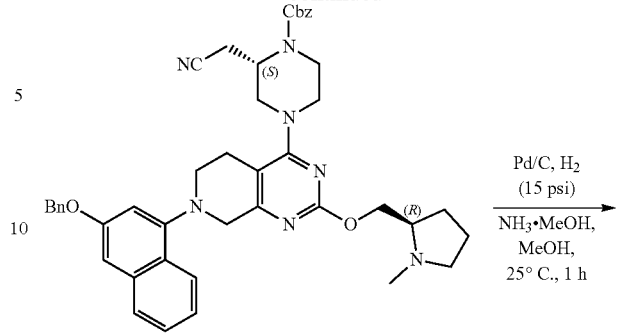

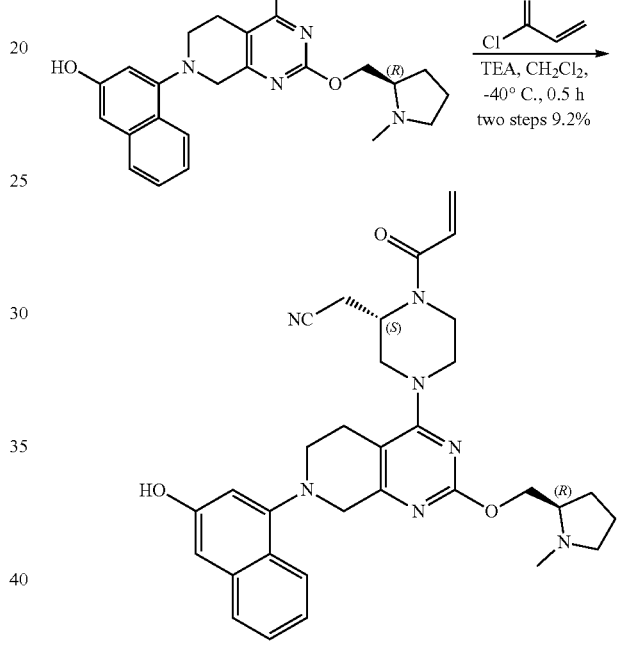

Step A: benzyl (2S)-4-[7-(3-benzyloxy-1-naphthyl)-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate To a solution of [(2R)-1-methylpyrrolidin-2-yl]methanol (101 mg, 874 umol, 1.2 eq) in toluene (15 mL) was added t-BuONa (140 mg, 1.46 mmol, 2 eq) at 0° C. under 10 minutes. Then to the mixture was added a solution of benzyl (2S)-4-[7-(3-benzyloxy-1-naphthyl)-2-methylsulfinyl-6,8-dihydro-5H-pyrido[3,4-d]pyrimidin-4-yl]-2-(cyanomethyl)piperazine-1-carboxylate (Intermediate 64, 500 mg, 728 umol, 1 eq) in toluene (10 mL) dropwise at 0° C. After stirred at 0° C. for 0.5 h, the reaction mixture was diluted with H$_2$O (1×7 mL) and Ethyl acetate (1×25 mL). The organic phase was separated, washed with brine (1×20 mL), dried over sodium sulfate, filtered and concentrated under reduced pressure to give a residue. The residue was purified by column chromatography (Al$_2$O$_3$; Petroleum ether/Ethyl acetate=10/1 to 0/1). Compound benzyl (2S)-4-[7-(3-benzyloxy-1-naphthyl)-2-[[(2R)-1-methylpyrrolidin-2-yl]methoxy]-6,8-dihydro-5H-pyrido[3,4-d]pyrimidin-4-yl]-2-

(cyanomethyl)piperazine-1-carboxylate (390 mg, 489 umol, 67% yield, 92.6% purity) was obtained as a yellow solid. LCMS [ESI, M+1]: 738.

$^1$H NMR (400 MHz, chloroform-d) δ=8.09 (d, J=8.4 Hz, 1H), 7.74 (d, J=8.0 Hz, 1H), 7.50 (d, J=7.2 Hz, 2H), 7.46-7.34 (m, 10H), 7.00 (d, J=2.0 Hz, 1H), 6.89 (d, J=2.4 Hz, 1H), 5.24-5.15 (m, 4H), 4.70 (br s, 1H), 4.39 (dd, J=4.8, 10.7 Hz, 1H), 4.33-4.22 (m, 2H), 4.20-4.11 (m, 3H), 3.93 (br d, J=12.0 Hz, 1H), 3.56-3.19 (m, 4H), 3.14-2.61 (m, 7H), 2.48 (s, 3H), 2.34-2.23 (m, 1H), 2.11-2.06 (m, 1H), 1.84-1.69 (m, 3H).

Step B: 2-[(2S)-4-[7-(3-hydroxy-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile NH$_3$ was bubbled into MeOH (100 mL) at −60° C. for 20 minutes. To a solution of benzyl (2S)-4-[7-(3-benzyloxy-1-naphthyl)-2-[[(2R)-1-methylpyrrolidin-2-yl] methoxy]-6,8-dihydro-5H-pyrido[3,4-d]pyrimidin-4-yl]-2-(cyanomethyl) piperazine-1-carboxylate (360 mg, 488 umol, 1 eq) in MeOH (25 mL) was added Pd/C (300 mg, 10% purity) and the above solution (NH$_3$.MeOH, 25 mL) under N$_2$. The suspension was degassed under vacuum and purged with H$_2$ several times. The mixture was stirred under H$_2$ (15 psi) at 25° C. for 1 hour. The catalyst was filtered off and concentrated under vacuum. Compound 2-[(2S)-4-[7-(3-hydroxy-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (230 mg, crude) was obtained as a yellow oil. LCMS [ESI, M+1]: 514.

Step C: 2-[(2S)-4-[7-(3-hydroxy-1-naphthyl)-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2S)-4-[7-(3-hydroxy-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (230 mg, crude) and TEA (453 mg, 4.48 mmol, 623 uL) in DCM (8 mL) was added prop-2-enoyl chloride (40.5 mg, 448 umol, 36.5 uL) in portion at −40° C. The mixture was stirred at −40° C. for 30 min. The reaction mixture was quenched with NaHCO$_3$ saturated solution (2 mL) at 0° C., and then extracted with CH$_2$Cl$_2$ (2×30 mL). The combined organic layers were washed with brine (1×30 mL), dried over sodium sulfate, filtered and concentrated under vacuum to give a residue. The residue was purified by column chromatography (Al$_2$O$_3$; Ethyl acetate/Methanol=20/1 to 3/1). The residue was purified by prep-HPLC (column: Phenomenex Gemini 150*25 mm*10 um; mobile phase: [water (0.05% ammonia hydroxide v/v)-ACN]; B %: 38%-68%, 12 min). Title compound 2-[(2S)-4-[7-(3-hydroxy-1-naphthyl)-2-[[(2R)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 344, 25.6 mg, 44.8 umol, two steps 9.2% yield, 99.5% purity) was obtained as a yellow solid. LCMS [ESI, M+1]: 568.

SFC condition: "AS-3_MeOH (DEA)_5_40_3 mL-35T Column: Chiralpak AS-3 50×4.6 mm I.D., 3 um Mobile phase: methanol (0.05% DEA) in CO$_2$ from 5% to 40% Flow rate: 3 mL/min Wavelength: 220 nm".

$^1$H NMR (400 MHz, acetic) δ=8.08 (d, J=8.4 Hz, 1H), 7.66 (d, J=8.0 Hz, 1H), 7.39 (t, J=7.6 Hz, 1H), 7.29 (t, J=7.2 Hz, 1H), 6.96 (s, 1H), 6.90-6.68 (m, 2H), 6.38 (br d, J=17.6 Hz, 1H), 5.87 (br d, J=10.8 Hz, 1H), 5.17 (br s, 1H), 4.82 (br s, 2H), 4.59 (br s, 1H), 4.45-4.25 (m, 3H), 4.21-3.61 (m, 4H), 3.60-3.19 (m, 5H), 3.17-2.83 (m, 7H), 2.45-2.31 (m, 1H), 2.23-2.10 (m, 3H).

Example 345

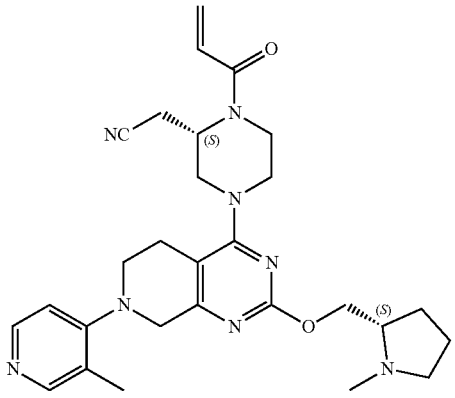

2-[(2S)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

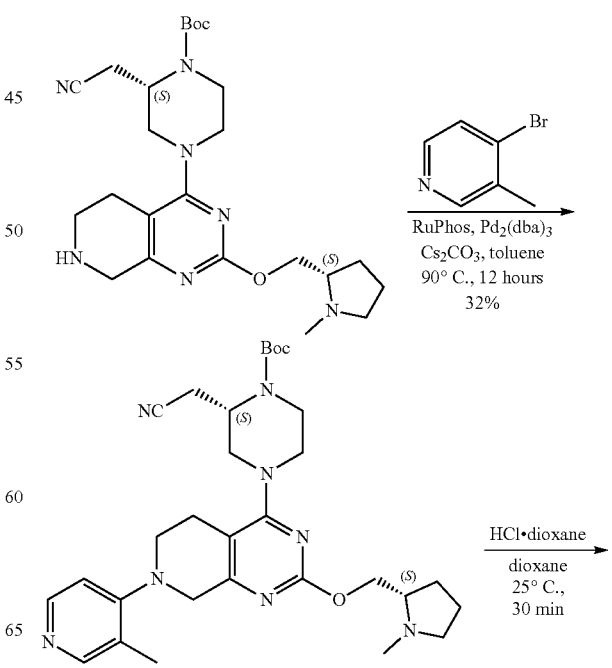

-continued

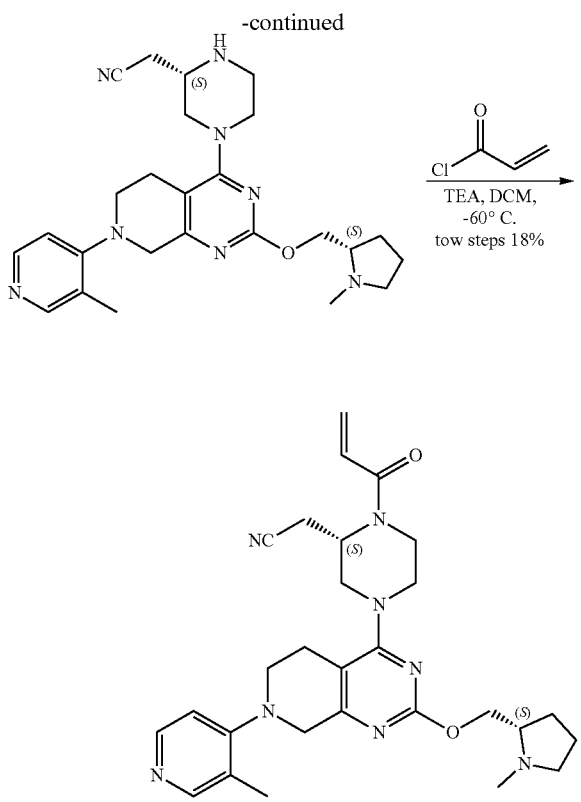

Step A: tert-butyl(2S)-2-(cyanomethyl)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (700 mg, 1.48 mmol, 1.0 eq), 4-chloro-3-methyl-pyridine (379 mg, 2.97 mmol, 2.0 eq), Pd$_2$(dba)$_3$ (204 mg, 223 umol, 0.15 eq), RuPhos (139 mg, 297 umol, 0.2 eq) and Cs$_2$CO$_3$ (1.45 g, 4.45 mmol, 3.0 eq) in toluene (10.0 mL) was degassed and purged with N$_2$ for 3 times, and then the mixture was stirred at 90° C. for 12 hrs under N$_2$ atmosphere. The organic solvent was removed under vacuum, and washed with water (15.0 mL). The aqueous phase was extracted with ethyl acetate (3×25.0 mL). Combine extracts were washed with brine (60.0 mL), dried with Na$_2$SO$_4$ the solvent was then removed under vacuum. The residue was purified by reversed phase flash HPLC [C18, 0.1% FA in water, 0-45% MeCN]. The obtained product was adjusted with saturated NaHCO$_3$ aqueous to pH ~8, then concentrated, the aqueous was extracted with ethyl acetate (3×50.0 mL), the combined organic layer was dried over Na$_2$SO$_4$, filtered and concentrated. Compound tert-butyl(2S)-2-(cyanomethyl)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]piperazine-1-carboxylate (270 mg, 475 umol, 32% yield, 99.0% purity) was obtained as yellow solid. LCMS [ESI, M+1]:563.

Step B: 2-[(2S)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]piperazine-1-carboxylate (200 mg, 355 umol, 1.0 eq) in dioxane (3.0 mL) was added HCl.dioxane (4 M, 3.0 mL, 33.8 eq). The mixture was stirred at 25° C. for 30 min under N$_2$ atmosphere. The organic solvent was removed under vacuum. The obtained product was adjusted with saturated NaHCO$_3$ aqueous to pH ~8, then concentrated, the aqueous was extracted with ethyl acetate (3×15.0 mL), the combined organic layer was dried over Na$_2$SO$_4$, filtered and concentrated. The crude product 2-[(2S)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]piperazin-2-yl]acetonitrile (125 mg, crude) was obtained as a yellow solid and used into the next step without further purification. LCMS [ESI, M+1]:463.

Step C: 2-[(2S)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]piperazin-2-yl]acetonitrile (125 mg, crude) in DCM (3.0 mL) was added TEA (137 mg, 1.35 mmol, 188 uL) and prop-2-enoyl chloride (36.7 mg, 405 umol, 33.1 uL) at −60° C. The mixture was stirred at −60° C. for 30 min. The reaction was quenched with methanol (10.0 mL) and the mixture was removed under vacuum. The residue was purified by prep-HPLC (column: Phenomenex Gemini 150*25 mm*10 um; mobile phase: [water (0.05% ammonia hydroxide v/v)-ACN]; B %: 32%-62%,12 min) and lyophilization. Title compound 2-[(2S)-4-[7-(3-methyl-4-pyridyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 345, 25.3 mg, 48.4 umol, 18% yield, 99% purity) was obtained as a white solid. LCMS [ESI, M+1]:517.

$^1$H NMR (400 MHz, CHLOROFORM-d) δ=8.33-8.29 (m, 2H), 6.83 (d, J=5.6 Hz, 1H), 6.65-6.50 (m, 1H), 6.38 (dd, J=1.6 Hz, J=16.8 Hz, 1H), 5.82 (d, J=10.8 Hz 1H), 5.41 (br s, 1H), 4.36 (dd, J=4.8 Hz, J=10.4 Hz, 1H), 4.20-4.06 (m, 4H), 4.97 (br d, J=11.6 Hz 2H),3.68-3.45 (m, 1H), 3.40-3.31 (m, 2H), 3.26-3.15 (m, 1H), 3.15-3.03 (m, 2H), 2.97-2.60 (m, 5H), 2.31 (s, 3H), 2.29-2.21 (m, 3H) 2.15-2.10 (m, 1H), 2.09-2.00 (m, 1H) 1.88-1.70 (m, 3H).

947

Example 346

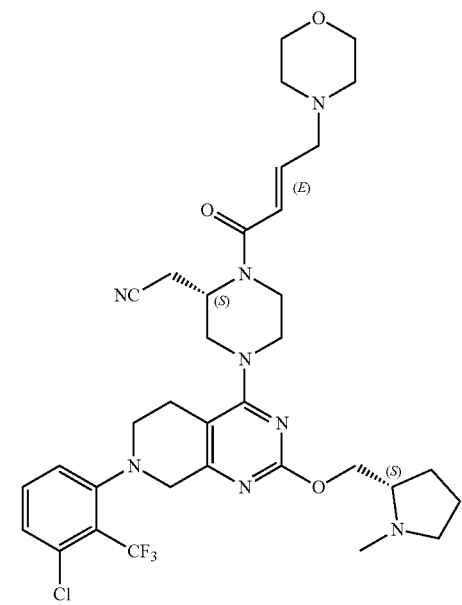

2-[4-[2-[[(2R)-1-methylpyrrolidin-2-yl]methoxy]-7-[2-(trifluoromethyl)phenyl]-6,8-dihydro-5H-pyrido[3,4-d]pyrimidin-4-yl]-1-prop-2-enoyl-piperazin-2-yl]acetonitrile

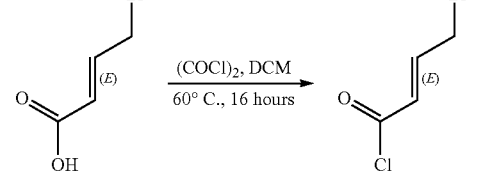

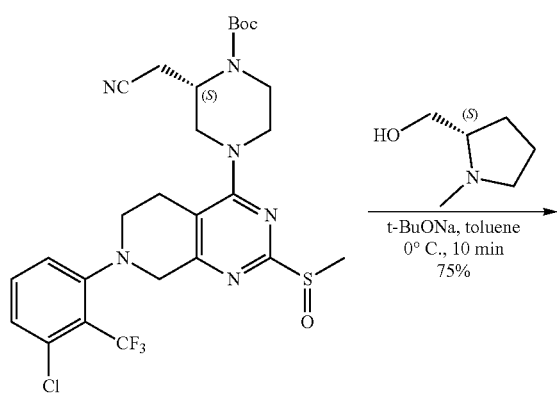

948

-continued

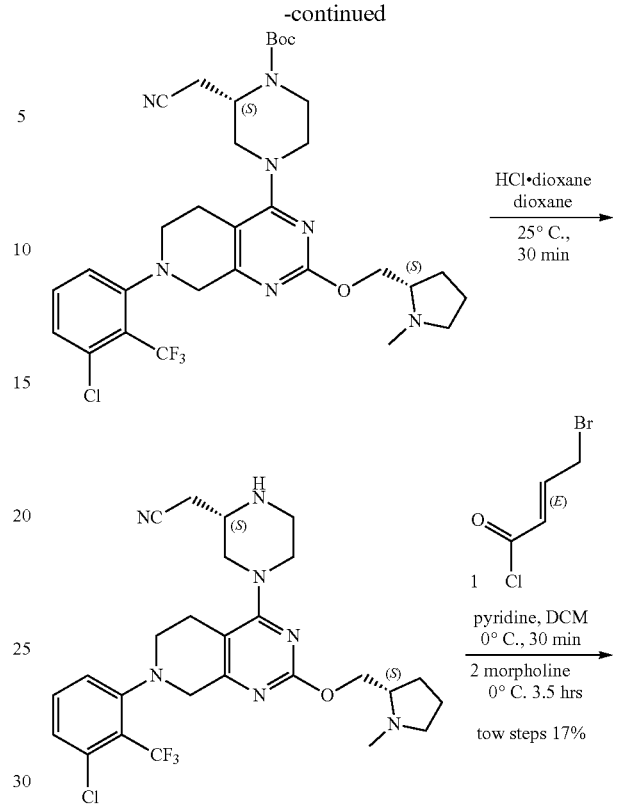

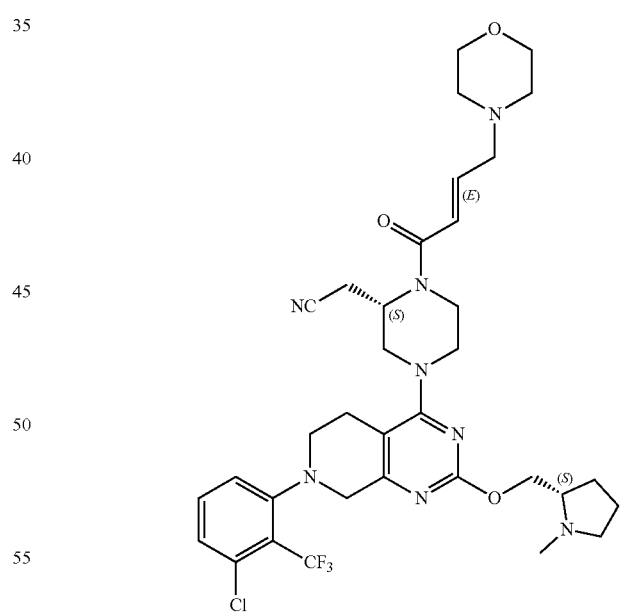

Step 1: To a solution of (E)-4-bromobut-2-enoic acid (1.0 g, 6.06 mmol, 1.0 eq) in DCM (5.0 mL) was added (COCl)$_2$ (8.70 g, 68.5 mmol, 6 mL, 11.3 eq). The mixture was stirred at 60° C. for 16 hrs under N$_2$ atmosphere. The organic solvent was removed under vacuum. The crude product (E)-4-bromobut-2-enoyl chloride (1.3 g, crude) was obtained as a yellow liquid and used into the next step without further purification.

Step A: tert-butyl (2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate To a solution of tert-butyl (2S)-4-[7-[3-chloro-2-(trifluoromethyl)phenyl]-2-methylsulfinyl-6,8-dihydro-5H-pyrido[3,4-d]pyrimidin-4-yl]-2-(cyanomethyl)piperazine-1-carboxylate (1.30 g, 2.17 mmol, 1.0 eq) and [(2S)-1-methylpyrrolidin-2-yl]methanol (500 mg, 4.34 mmol, 515 uL, 2.0 eq) in toluene (20.0 mL) was added t-BuONa (417 mg, 4.34 mmol, 2.0 eq). The mixture was stirred at 0° C. for 10 min. The reaction mixture was quenched by adding saturated brine (30 mL) at 20° C., and extracted with EA (3×30.0 mL). The combined organic layers were washed with saturated brine (30.0 mL), dried over $Na_2SO_4$, filtered and concentrated under reduced pressure to give a residue. The residue was purified by column chromatography ($SiO_2$, Petroleum ether/Ethyl acetate=3/1 to EA/MeOH=10/1). The product tert-butyl (2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (1.10 g, 1.62 mmol, 75% yield, 96% purity) was obtained as a yellow solid. LCMS [ESI, M+1]: 650.

Step B: 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (200 mg, 308 umol, 1.0 eq) in dioxane (2.0 mL) was added HCl/dioxane (4 M, 2.0 mL, 26.0 eq). The mixture was stirred at 25° C. for 30 min under $N_2$ atmosphere. The organic solvent was removed under vacuum. The obtained product was adjusted with saturated $NaHCO_3$ aqueous to pH ~8, then concentrated, the aqueous was extracted with ethyl acetate (3×20.0 mL), the combined organic layer was dried over $Na_2SO_4$, filtered and concentrated. The crude product 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (130 mg, crude) was obtained as a yellow solid and used into the next step without further purification. LCMS [ESI, M+1]:551.

Step C: 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-[(E)-4-morpholinobut-2-enoyl]piperazin-2-yl]acetonitrile To a solution of 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (100 mg, 1812 umol, 1.0 eq) and PYRIDINE (115 mg, 1.45 mmol, 117 uL, 8.0 eq) in DCM (3.0 mL) was added (E)-4-bromobut-2-enoyl chloride (133 mg, 727 umol, 4.0 eq). The mixture was stirred at 0° C. for 0.5 hr. After the starting material was consumed, morpholine (79.2 mg, 909 umol, 80.0 uL, 5.0 eq) was added to the above mixture and stirred at 0° C. for 3.5 hrs. The organic solvent was removed under vacuum. The obtained product was adjusted with saturated $NaHCO_3$ aqueous to pH ~8, then concentrated, the aqueous was extracted with ethyl acetate (3×15.0 mL), the combined organic layer was dried over $Na_2SO_4$, filtered and concentrated. Title compound 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-[(E)-4-morpholinobut-2-enoyl]piperazin-2-yl]acetonitrile (EXAMPLE 346, 21.7 mg, 30.6 umol, 16.9% yield, 99% purity) was obtained as a yellow solid. LCMS [ESI, M+1]: 703.

$^1$H NMR (400 MHz, CHLOROFORM-d) δ=7.40 (t, J=8.0 Hz, J=8.0 Hz 1H), 7.28 (s, 1H), 7.19 (d, J=8.0 Hz, 1H), 7.00-6.93 (m, 1H), 6.59 (br s, 1H), 6.57-6.40 (m, 1H), 5.18-5.03 (m, 1H), 4.38 (dd, J=4.8 Hz, J=10.4 Hz, 1H), 4.16 (d d, J=6.8 Hz, J=10.4 Hz, 1H), 4.14-4.04 (m, 3H), 4.04-3.88 (m, 2H), 3.74 (t, J=4.4 Hz, J=4.8 Hz, 4H), 3.52 (br s, 1H), 3.41-3.23 (m, 2H), 3.18 (d, J=5.6 Hz, 3H), 3.12-3.08 (m, 2H), 2.95-2.85 (m, 2H), 2.30-2.15 (m, 3H), 2.55-2.45 (m, 7H), 2.34-2.24 (m, 1H), 2.13-2.00 (m, 1H), 1.90-1.75 (m, 3H).

Example 347

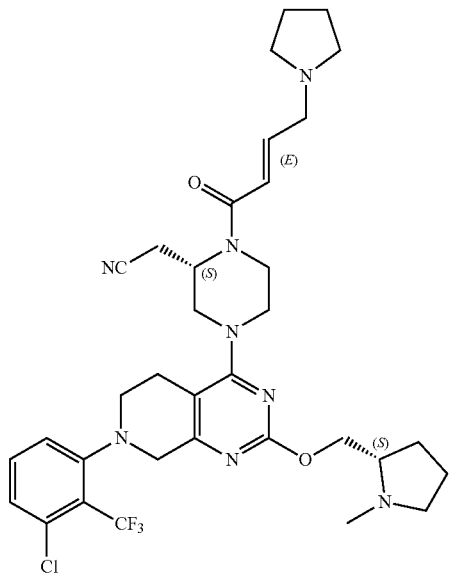

2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-[(E)-4-pyrrolidin-1-ylbut-2-enoyl]piperazin-2-yl]acetonitrile

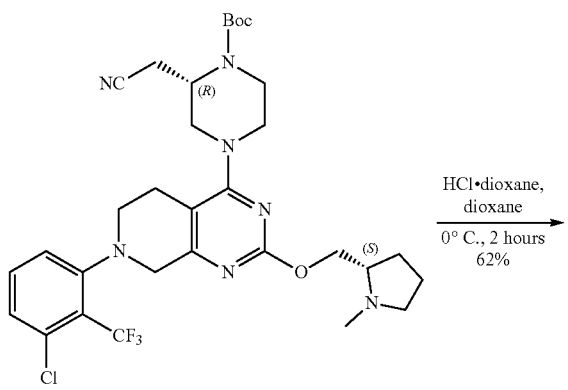

-continued

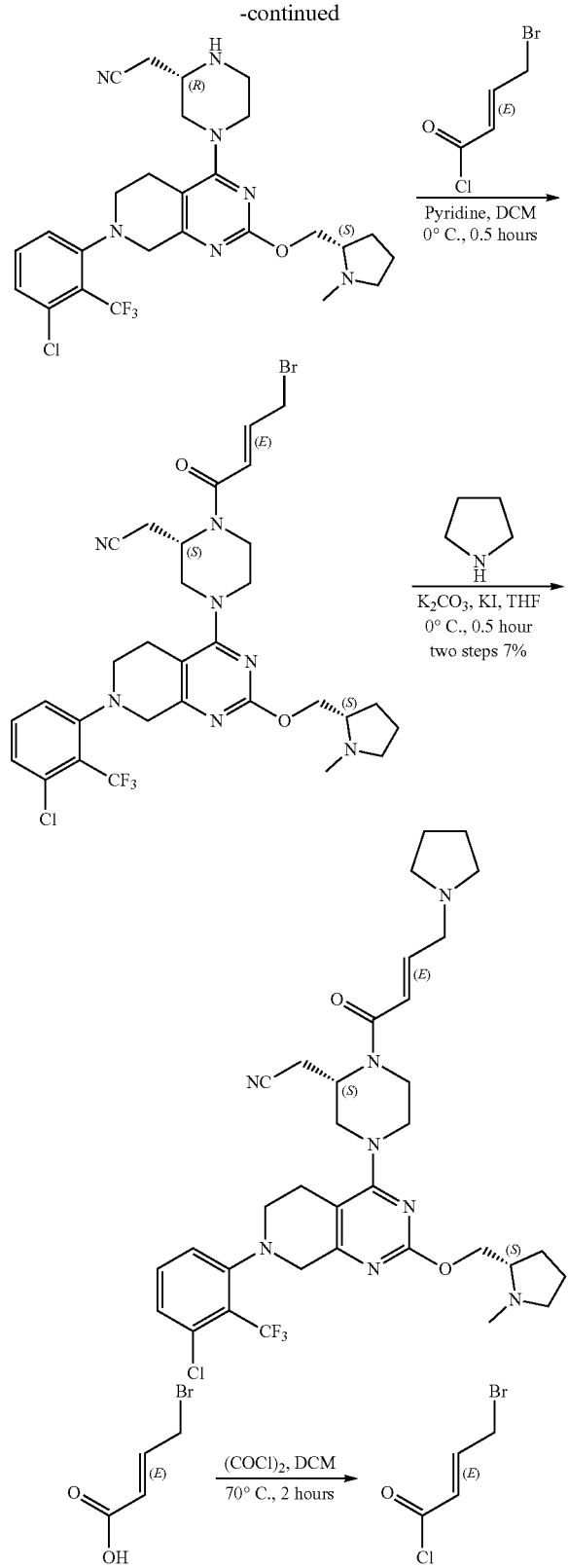

Insert: (E)-4-bromobut-2-enoyl chloride

A solution of (E)-4-bromobut-2-enoic acid (1.00 g, 6.06 mmol, 1.00 eq) in (COCl)₂ (14.5 g, 114 mmol, 10.0 mL, 18.9 eq) and DCM (10.0 mL) was stirred at 70° C. for 2 hours. After completion, the mixture was concentrated under vacuum. The product (E)-4-bromobut-2-enoyl chloride (1.00 g, crude) was obtained as yellow oil. The crude compound was used directly to the next step without further purification.

Step A: 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (700 mg, 1.08 mmol, 1.0 eq) in dioxane (5.0 mL) was added HCl.dioxane (4 M, 7.0 mL, 26.0 eq) at 0° C. The mixture was stirred at 0° C. for 2 hours. After completion, the mixture was concentrated and adjusts with saturated NaHCO₃ aqueous to pH ~7, then extracted with EA (10.0 mL×3). The organic layer was dried over Na₂SO₄, filtered and concentrated. The product 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (400 mg, 669 umol, 62% yield, 92% purity) was obtained as yellow oil. LCMS [ESI, M+1]: 550.

Step B: 2-[(2S)-1-[(E)-4-bromobut-2-enoyl]-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 364 umol, 1.00 eq) and Pyridine (230 mg, 2.91 mmol, 235 uL, 8.0 eq) in DCM (2.0 mL) was added (E)-4-bromobut-2-enoyl chloride (267 mg, 1.45 mmol, 4.0 eq). The mixture was stirred at 0° C. for 0.5 hour. After completion, the mixture was added water (10.0 mL) and extracted with DCM (10.0 mL×2). The organic layer was dried over Na₂SO₄, filtered and concentrated. The product 2-[(2S)-1-[(E)-4-bromobut-2-enoyl]-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, crude) was obtained as brown oil.

Step C: 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-[(E)-4-pyrrolidin-1-ylbut-2-enoyl]piperazin-2-yl]acetonitrile To a solution of pyrrolidine (306 mg, 4.30 mmol, 359 uL, 10.0 eq), K₂CO₃ (297 mg, 2.15 mmol, 5.0 eq) and KI (21.4 mg, 129 umol, 0.30 eq) in THF (2.0 mL) was added 2-[(2S)-1-[(E)-4-bromobut-2-enoyl]-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, 430 umol, 1.0 eq) in portions at 0° C. The mixture was stirred at 0° C. for 0.5 hour. After completion, water (10.0 mL) was added to the mixture and extracted with DCM (10.0 mL×3). The organic layer was dried over Na₂SO₄, filtered and concentrated. The obtained product was purified by prep-HPLC (column:

Phenomenex Gemini C18 250*50 mm*10 um; mobile phase: [water (10 mM NH₄HCO₃)-ACN]; B %: 70%-100%,3 min) to give title compound 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-[(E)-4-pyrrolidin-1-ylbut-2-enoyl]piperazin-2-yl]acetonitrile (EXAMPLE 347, 17.1 mg, 24.5 umol, two steps 7% yield, 99% purity) as yellow oil. LCMS [ESI, M+1]: 687.

¹H NMR (400 MHz, Chloroform-d) δ 7.41 (t, J=8.0 Hz, 1H), 7.28 (d, J=8.0 Hz, 1H), 7.20 (d, J=8.4 Hz, 1H), 7.06-6.95 (m, 1H), 6.47 (br d, J=14.0 Hz, 1H), 5.20-4.60 (m, 1H), 4.39 (dd, J=5.2, 10.8 Hz, 1H), 4.22-4.07 (m, 4H), 3.97 (br d, J=12.0 Hz, 2H), 3.42-3.23 (m, 3H), 3.21-3.04 (m, 3H), 2.96-2.86 (m, 2H), 2.79-2.64 (m, 5H), 2.62-2.54 (m, 4H), 2.49 (s, 3H), 2.35-2.25 (m, 1H), 2.13-2.01 (m, 1H), 1.83-1.70 (m, 7H).

Example 348

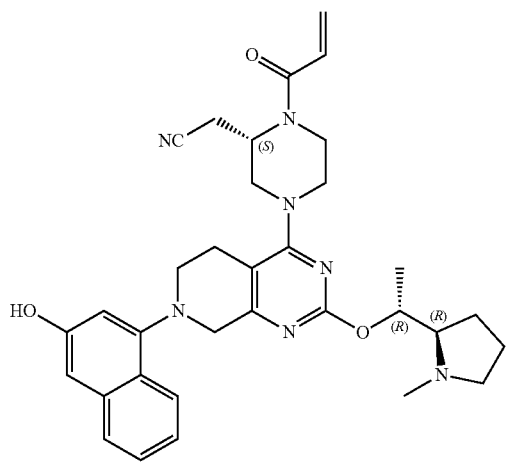

2-[(2S)-4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]-1-prop-2-enoyl-piperazin-2-yl]acetonitrile

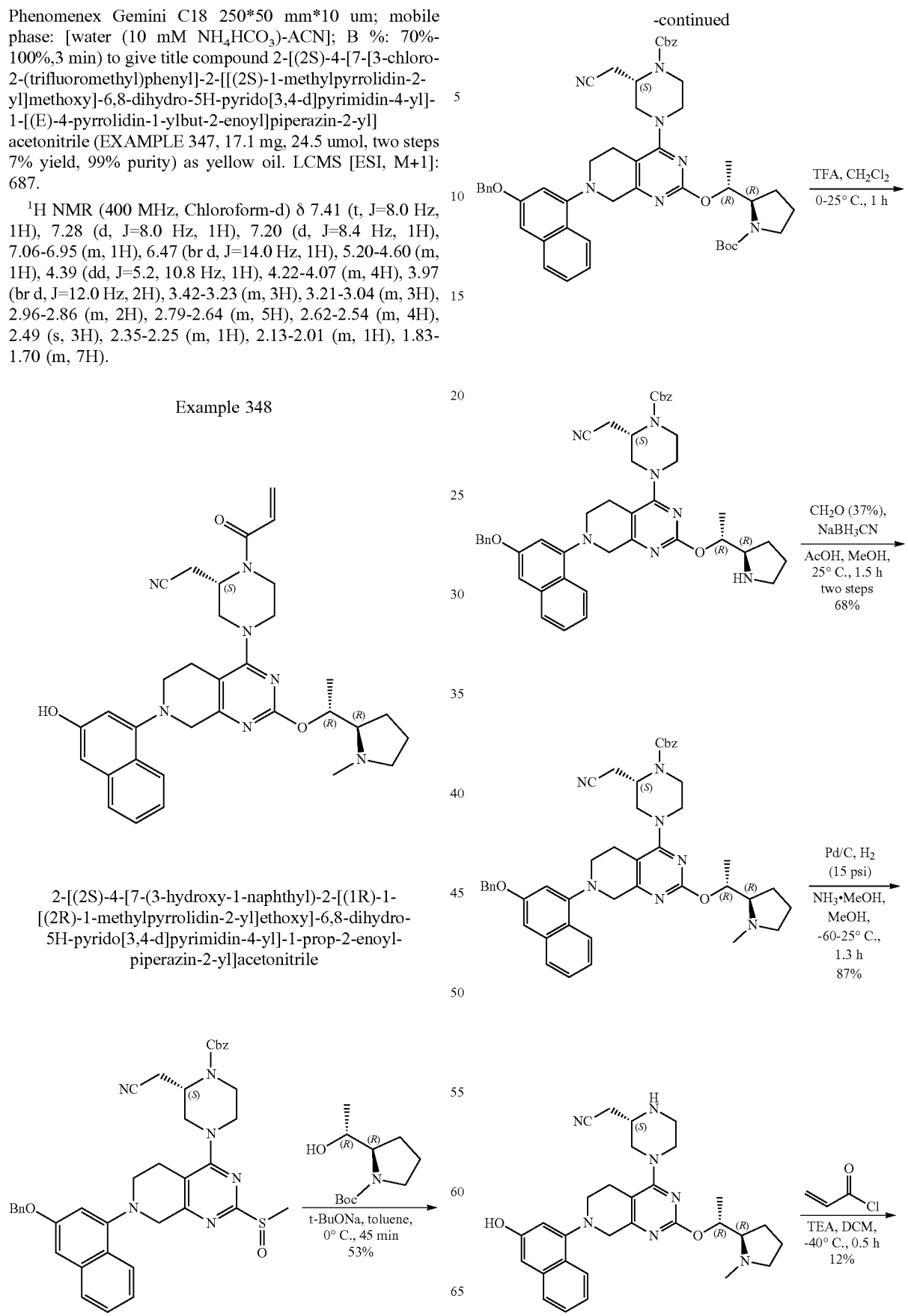

-continued

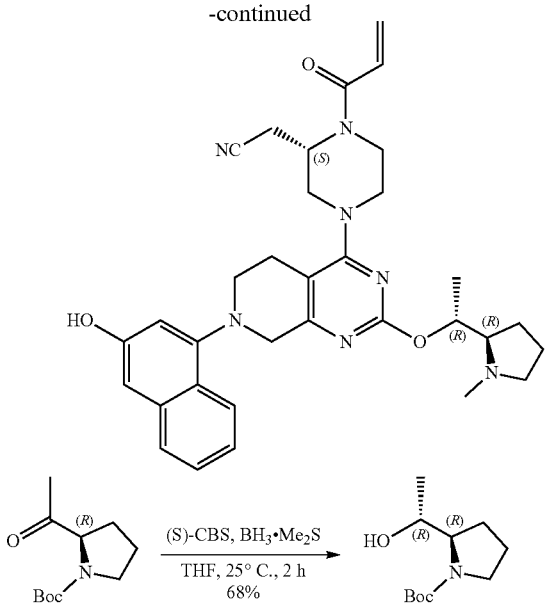

Insert: tert-Butyl (2R)-2-[(1R)-1-hydroxyethyl]pyrrolidine-1-carboxylate

A mixture of BH$_3$·Me$_2$S (10 M in DMS, 610 uL, 1.3 eq) and (3aS)-1-methyl-3,3-diphenyl-3a,4,5,6-tetrahydropyrrolo[1,2-c][1,3,2]oxazaborole (1 M in toluene, 938 uL, 0.2 eq) in THF (10 mL) was stirred at 25° C. for 1 hour. Then a solution of tert-butyl (2R)-2-acetylpyrrolidine-1-carboxylate (1.00 g, 4.69 mmol, 1 eq) in THF (10 mL) was added and the mixture stirred at 25° C. for 1 hour. The mixture was quenched with MeOH (4 mL), concentrated under vacuum. The residue was purified by column chromatography (SiO$_2$, PE/EtOAC=50/1 to 5/1). tert-Butyl (2R)-2-[(1R)-1-hydroxyethyl]pyrrolidine-1-carboxylate (690 mg, 3.21 mmol, 68% yield) was obtained as a white solid.

$^1$H NMR (400 MHz, chloroform-d) δ=5.19 (br s, 1H), 3.79-3.59 (m, 2H), 3.49 (br s, 1H), 3.35-3.18 (m, 1H), 2.04-1.90 (m, 1H), 1.88-1.68 (m, 3H), 1.47 (d, J=0.8 Hz, 9H), 1.20-1.11 (m, 3H).

Step A: benzyl (2S)-4-[7-(3-benzyloxy-1-naphthyl)-2-[(1R)-1-[(2R)-1-tert-butoxycarbonylpyrrolidin-2-yl]ethoxy]-6,8-dihydro-5H-pyrido[3,4-d]pyrimidin-4-yl]-2-(cyanomethyl)piperazine-1-carboxylate To a solution of tert-butyl (2R)-2-[(1R)-1-hydroxyethyl]pyrrolidine-1-carboxylate (263 mg, 1.22 mmol, 1.2 eq) in toluene (15 mL) was added t-BuONa (196 mg, 2.04 mmol, 2 eq) at 0° C. for 10 minutes. To the mixture was added benzyl (2S)-4-[7-(3-benzyloxy-1-naphthyl)-2-methylsulfinyl-6,8-dihydro-5H-pyrido[3,4-d]pyrimidin-4-yl]-2-(cyanomethyl)piperazine-1-carboxylate (700 mg, 1.02 mmol, 1 eq) in toluene (15 mL) dropwise at 0° C. After stirred at 0° C. for 0.5 h, the reaction mixture was added H$_2$O (1×7 mL) and ethyl acetate (1×35 mL). The organic phase was separated, washed with brine (1×20 mL), dried over sodium sulfate, filtered and concentrated under reduced pressure to give a residue. The residue was purified by reversed phase flash [water (0.1% FA)/acetonitrile]. The desired fractions were collected and neutralized to pH=7 with saturated NaHCO$_3$ solution and extracted with ethyl acetate (1×100 mL). The separated organic layer was dried over sodium sulfate, filtered and concentrated under vacuum. Compound benzyl (2S)-4-[7-(3-benzyloxy-1-naphthyl)-2-[(1R)-1-[(2R)-1-tert-butoxycarbonylpyrrolidin-2-yl]ethoxy]-6,8-dihydro-5H-pyrido[3,4-d]pyrimidin-4-yl]-2-(cyanomethyl)piperazine-1-carboxylate (470 mg, 536 umol, 53% yield, 95.6% purity) was obtained as a yellow solid. LCMS [ESI, M+1]: 838.

$^1$H NMR (400 MHz, chloroform-d) δ=8.09 (d, J=8.4 Hz, 1H), 7.73 (d, J=8.0 Hz, 1H), 7.53-7.48 (m, 2H), 7.46-7.31 (m, 10H), 7.00 (d, J=1.6 Hz, 1H), 6.89 (d, J=2.0 Hz, 1H), 5.78-5.44 (m, 1H), 5.30-5.08 (m, 4H), 4.70 (br s, 1H), 4.35-4.20 (m, 3H), 4.08-3.79 (m, 2H), 3.72-3.13 (m, 7H), 3.12-2.64 (m, 4H), 2.01-1.71 (m, 5H), 1.46 (s, 9H), 1.26-1.23 (m, 3H).

Step B: benzyl (2S)-4-[7-(3-benzyloxy-1-naphthyl)-2-[(1R)-1-[(2R)-pyrrolidin-2-yl]ethoxy]-6,8-dihydro-5H-pyrido[3,4-d]pyrimidin-4-yl]-2-(cyanomethyl)piperazine-1-carboxylate To a solution of benzyl (2S)-4-[7-(3-benzyloxy-1-naphthyl)-2-[(1R)-1-[(2R)-1-tert-butoxycarbonylpyrrolidin-2-yl]ethoxy]-6,8-dihydro-5H-pyrido[3,4-d]pyrimidin-4-yl]-2-(cyanomethyl)piperazine-1-carboxylate (450 mg, 537 umol, 1 eq) in DCM (600 uL) was added TFA (918 mg, 8.05 mmol, 596 uL, 15 eq) at 0° C. under nitrogen atmosphere. The mixture was stirred at 25° C. for 1 hour. Then the mixture was concentrated under vacuum. Compound benzyl (2S)-4-[7-(3-benzyloxy-1-naphthyl)-2-[(1R)-1-[(2R)-pyrrolidin-2-yl]ethoxy]-6,8-dihydro-5H-pyrido[3,4-d]pyrimidin-4-yl]-2-(cyanomethyl)piperazine-1-carboxylate (700 mg, crude, TFA) was obtained as a yellow oil.

Step C: benzyl (2S)-4-[7-(3-benzyloxy-1-naphthyl)-2-[(1R)-1-[(2R)-1-methylpyrrolidin-2-yl]ethoxy]-6,8-dihydro-5H-pyrido[3,4-d]pyrimidin-4-yl]-2-(cyanomethyl)piperazine-1-carboxylate A mixture of benzyl (2S)-4-[7-(3-benzyloxy-1-naphthyl)-2-[(1R)-1-[(2R)-pyrrolidin-2-yl]ethoxy]-6,8-dihydro-5H-pyrido[3,4-d]pyrimidin-4-yl]-2-(cyanomethyl)piperazine-1-carboxylate (650 mg, 763 umol, 1 eq, TFA), formaldehyde (310 mg, 3.81 mmol, 284 uL, 5 eq, 37% in water) and AcOH (45.8 mg, 763 umol, 43.6 uL, 1 eq) in MeOH (15 mL) was stirred at 25° C. for 0.5 h. Then NaBH$_3$CN (120 mg, 1.91 mmol, 2.5 eq) was added and the mixture was stirred at 25° C. for 1 hour. The mixture was quenched with H$_2$O (10 mL) at 0° C., then extracted with ethyl acetate (3×15 mL), washed with brine (1×15 mL), dried over Na$_2$SO$_4$, filtered and concentrated under vacuum. The residue was purified by reversed phase flash [water (0.1% FA)/acetonitrile]. The desired fractions were collected and neutralized to pH=7 with saturated NaHCO$_3$ solution and extracted with ethyl acetate (2×50 mL). The separated organic layer was dried over sodium sulfate, filtered and concentrated under vacuum. Compound benzyl (2S)-4-[7-(3-benzyloxy-1-naphthyl)-2-[(1R)-1-[(2R)-1-methylpyrrolidin-2-yl]ethoxy]-6,8-dihydro-5H-pyrido[3,4-d]pyrimidin-4-yl]-2-(cyanomethyl)piperazine-1-carboxylate (260 mg, 339 umol, two steps 68% yield, 97.9% purity) was obtained as a yellow solid.

Step D: 2-[(2S)-4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazin-2-yl]acetonitrile NH$_3$ was bubbled into MeOH (100 mL) at −60° C. for 20 minutes. To a solution of benzyl (2S)-4-[7-(3-benzyloxy-1- naphthyl)-2-[(1R)-1-[(2R)-1-methylpyrrolidin-2-yl]ethoxy]-6,8-dihydro-5H-pyrido[3,4-d]pyrimidin-4-yl]-2-(cyanomethyl)piperazine-1-carboxylate (260 mg, 346 umol, 1 eq) in MeOH (15 mL) was added Pd/C (200 mg, 10% purity) and above mixture (NH₃.MeOH, 15 mL) under N₂. The suspension was degassed under vacuum and purged with H₂ several times. The mixture was stirred under H₂ (15 psi) at 25° C. for 1 hour. The catalyst was filtered off and concentrated under vacuum. Compound 2-[(2S)-4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazin-2-yl]acetonitrile (180 mg, 300 umol, 87% yield, 88.0% purity) was obtained as a yellow oil. LCMS [ESI, M+1]: 528.

Step E: 2-[(2S)-4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]-1-prop-2-enoyl-piperazin-2-yl]acetonitrile To a mixture of 2-[(2S)-4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]piperazin-2-yl]acetonitrile (180 mg, 341 umol, 1 eq) and TEA (345 mg, 3.41 mmol, 475 uL, 10 eq) in DCM (8 mL) was added prop-2-enoyl chloride (30.9 mg, 341 umol, 27.8 uL, 1 eq) in portion at −40° C. and the mixture was stirred at −40° C. for 30 min. The reaction mixture was quenched with NaHCO₃ saturated solution (2 mL) at 0° C., and then extracted with CH₂Cl₂ (2×30 mL). The combined organic layers were washed with brine (1×30 mL), dried over sodium sulfate, filtered and concentrated under vacuum to give a residue. The residue was purified by column chromatography (Al₂O₃; Ethyl acetate/Methanol=20/1 to 3/1). The residue was purified by prep-HPLC (column: Phenomenex Gemini 150*25 mm*10 um; mobile phase: [water (0.05% ammonia hydroxide v/v)-ACN]; B %: 42%-72%, 12 min). Title compound 2-[(2S)-4-[7-(3-hydroxy-1-naphthyl)-2-[(1R)-1-[(2R)-1-methylpyrrolidin-2-yl]ethoxy]-6,8-dihydro-5H-pyrido[3,4-d]pyrimidin-4-yl]-1-prop-2-enoyl-piperazin-2-yl]acetonitrile (EXAMPLE 348, 23.5 mg, 39.9 umol, 12% yield, 99.0% purity) was obtained as a white solid. LCMS [ESI, M+1]: 582.

SFC condition: "OJ-3S_3_5_40_3ML Column: Chiralcel OJ-3 100×4.6 mm I.D., 3 um Mobile phase: methanol (0.05% DEA) in CO₂ from 5% to 40% Flow rate: 3 mL/min Wavelength: 220 nm".

¹H NMR (400 MHz, methanol-d₄) δ=8.09 (d, J=8.4 Hz, 1H), 7.64 (d, J=8.0 Hz, 1H), 7.39 (t, J=7.6 Hz, 1H), 7.32-7.23 (m, 1H), 6.98-6.74 (m, 3H), 6.31 (br d, J=16.4 Hz, 1H), 5.85 (br d, J=10.4 Hz, 1H), 5.27-5.15 (m, 1H), 5.11 (br s, 1H), 4.62 (br s, 1H), 4.33-4.00 (m, 5H), 3.75-3.38 (m, 2H), 3.27-2.81 (m, 7H), 2.75-2.62 (m, 1H), 2.55 (s, 3H), 2.47-2.31 (m, 1H), 2.11-1.96 (m, 1H), 1.86-1.69 (m, 3H), 1.34 (d, J=6.4 Hz, 3H).

Example 349

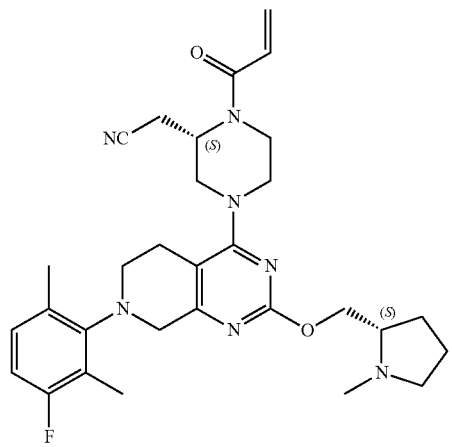

2-((S)-1-acryloyl-4-(7-(3-fluoro-2,6-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile

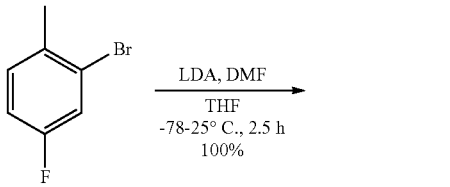

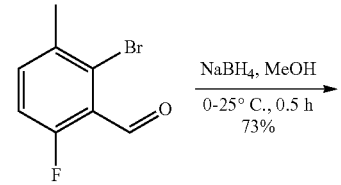

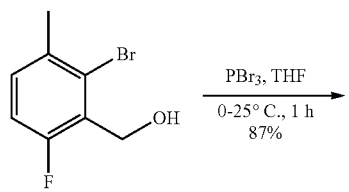

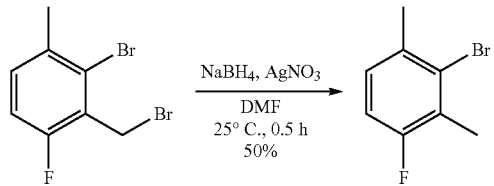

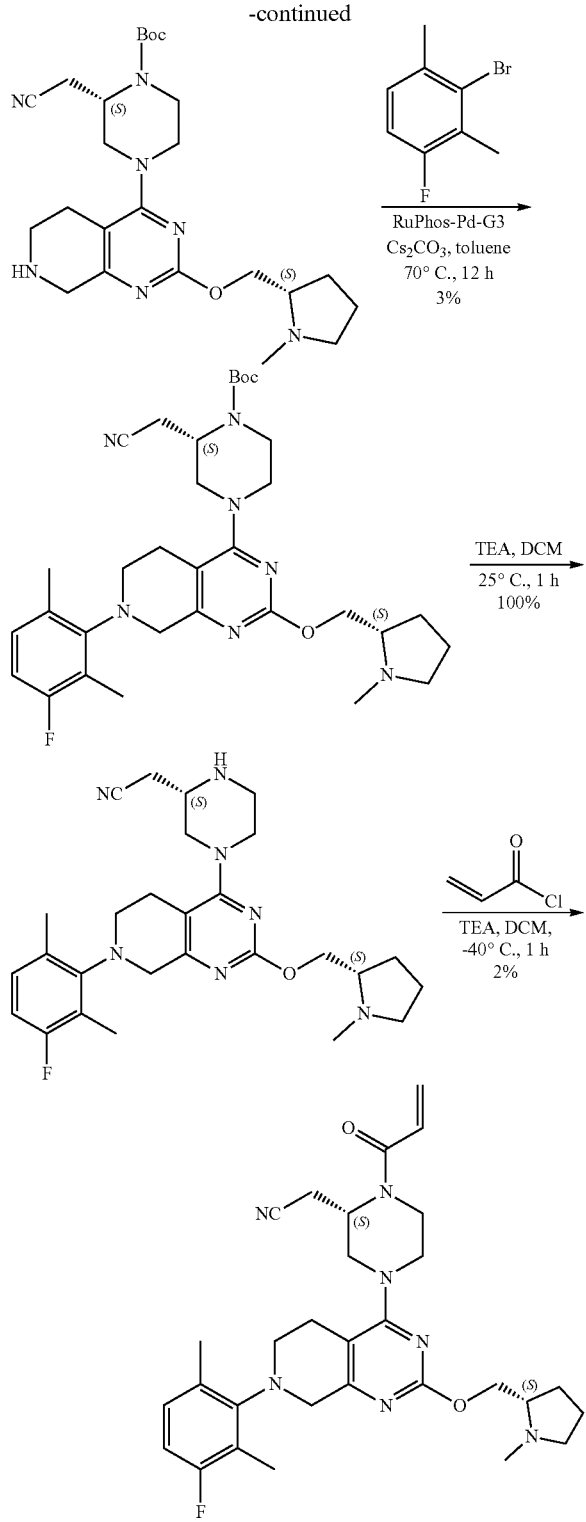

-78° C. The mixture was warmed up to 25° C. carefully and stirred for 0.5 hours. The mixture was quenched with water (5 mL) and the mixture was diluted with petroleum ether/ethyl acetate (50 mL/5 mL) and water (50 mL). The separated organic layer was dried over sodium sulfate, filtered and concentrated under vacuum. Compound 2-bromo-6-fluoro-3-methyl-benzaldehyde (11.5 g, 52.9 mmol, 100% yield) was obtained as a colorless oil.

Step 2:
(2-bromo-6-fluoro-3-methyl-phenyl)methanol

To a solution of 2-bromo-6-fluoro-3-methyl-benzaldehyde (11.5 g, 52.9 mmol, 1 eq) in MeOH (100 mL) was added $NaBH_4$ (2.20 g, 58.2 mmol, 1.1 eq) at 0° C. The mixture was stirred at 25° C. for 0.5 hour. The mixture was quenched with water at 0° C. and the mixture was concentrated under vacuum. The residue was purified by column chromatography over silica gel (petroleum ether/ethyl acetate 50/1 to 3/1). The desired fractions were collected and concentrated under vacuum. Compound (2-bromo-6-fluoro-3-methyl-phenyl)methanol (8.5 g, 38.4 mmol, 73% yield, 99% purity) was obtained as a white solid. LCMS [ESI, M-17]: 201.

$^1$H NMR (400 MHz, chloroform-d) δ=7.20 (dd, J=6.4, 8.4 Hz, 1H), 6.98 (t, J=8.8 Hz, 1H), 4.88 (d, J=2.0 Hz, 2H), 2.41 (s, 3H), 2.35-2.11 (m, 1H).

Step 3:
3-bromo-2-(bromomethyl)-1-fluoro-4-methyl-benzene

To a mixture of (2-bromo-6-fluoro-3-methyl-phenyl)methanol (5 g, 22.8 mmol, 1 eq) in THF (100 mL) was added $PBr_3$ (12.4 g, 45.6 mmol, 2 eq) in portions at 0° C. After stirred at 25° C. for 1 hour, the mixture was concentrated under vacuum. The residue was diluted with ethyl acetate (100 mL) and washed with ice water (1×50 mL), 10% aqueous sodium bicarbonate solution (2×50 mL) and brine (1×20 mL). The separated organic layer was dried over sodium sulfate, filtered and concentrated under vacuum. The residue was purified by column chromatography ($SiO_2$, Petroleum ether/Ethyl acetate=1/0 to 10/1). Compound 3-bromo-2-(bromomethyl)-1-fluoro-4-methyl-benzene (5.6 g, 19.9 mmol, 87% yield) was obtained as a colorless oil.

$^1$H NMR (400 MHz, chloroform-d) δ=7.20 (dd, J=6.4, 8.0 Hz, 1H), 6.97 (t, J=8.8 Hz, 1H), 4.70 (d, J=2.0 Hz, 2H), 2.41 (s, 3H).

Step 4: 3-bromo-1-fluoro-2,4-dimethyl-benzene

To a solution of 3-bromo-2-(bromomethyl)-1-fluoro-4-methyl-benzene (5.6 g, 19.9 mmol, 1 eq) in DMF (50 mL) was added $NaBH_4$ (1.50 g, 39.7 mmol, 2 eq) and $AgNO_3$ (6.75 g, 39.7 mmol, 6.68 mL, 2 eq) at 25° C. The mixture was stirred at 25° C. for 0.5 hour. The reaction mixture was diluted with water (20 mL) and extracted with ethyl acetate (50 mL×3). The combined organic layers were washed with brine (20 mL), dried over $Na_2SO_4$, filtered and concentrated under reduced pressure to give a residue. The residue was purified by reversed phase flash [water (0.1% formic acid)/acetonitrile)]. The mixture was concentrated under reduced pressure. Compound 3-bromo-1-fluoro-2,4-dimethyl-benzene (2.1 g, 9.93 mmol, 50% yield, 96% purity) was obtained as a colorless oil.

$^1$H NMR (400 MHz, chloroform-d) δ=7.05 (dd, J=6.0, 8.4 Hz, 1H), 6.91 (t, J=8.8 Hz, 1H), 2.38 (s, 3H), 2.35 (d, J=2.4 Hz, 3H).

Step 1: 2-bromo-6-fluoro-3-methyl-benzaldehyde

To a solution of 2-bromo-4-fluoro-1-methyl-benzene (10 g, 52.9 mmol, 1 eq) in THF (200 mL) was added LDA (2 M in toluene, 31.7 mL, 1.2 eq) at -78° C. under nitrogen atmosphere. After stirred at -78° C. for 2 hours, a solution of DMF (4.64 g, 63.5 mmol, 4.88 mL, 1.2 eq) was added at

Step A: tert-Butyl (2S)-2-(cyanomethyl)-4-[7-(3-fluoro-2,6-dimethyl-phenyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (500 mg, 1.06 mmol, 1 eq), 3-bromo-1-fluoro-2,4-dimethyl-benzene (430 mg, 2.12 mmol, 2 eq), RuPhos-Pd-G3 (177 mg, 212 umol, 0.2 eq), $Cs_2CO_3$ (863 mg, 2.65 mmol, 2.5 eq) in toluene (10 mL) was degassed and purged with $N_2$ for 3 times, and then the mixture was stirred at 70° C. for 12 hours under $N_2$ atmosphere. The reaction mixture was diluted with water (20 mL) and extracted with ethyl acetate (20 mL×3). The combined organic layers were washed with brine (20 mL), dried over $Na_2SO_4$, filtered and concentrated under reduced pressure to give a residue. The residue was purified by column chromatography ($Al_2O_3$, ethyl acetate/methanol=100/1 to 10/1) and further purified by reversed phase flash [water (0.1% formic acid)/acetonitrile)]. The mixture was adjusted pH=7 with saturated $NaHCO_3$ aqueous solution and extracted with ethyl acetate (20 mL×3). The combined organic layers were washed with brine (20 mL), dried over $Na_2SO_4$, filtered and concentrated under reduced pressure. Compound tert-Butyl (2S)-2-(cyanomethyl)-4-[7-(3-fluoro-2,6-dimethyl-phenyl)-2-[[(2S)-1-methylpyrrolidin-2-yl]methoxy]-6,8-dihydro-5H-pyrido[3,4-d]pyrimidin-4-yl]piperazine-1-carboxylate (20 mg, 28.6 umol, 3% yield, 85% purity) was obtained as a yellow oil. LCMS [ESI, M+1]: 594.

Step B: 2-[(2S)-4-[7-(3-fluoro-2,6-dimethyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(3-fluoro-2,6-dimethyl-phenyl)-2-[[(2S)-1-methylpyrrolidin-2-yl]methoxy]-6,8-dihydro-5H-pyrido[3,4-d]pyrimidin-4-yl]piperazine-1-carboxylate (20 mg, 33.7 umol, 1 eq) in DCM (100 uL) was added TFA (57.6 mg, 505 umol, 37.4 uL, 15 eq). After stirred at 25° C. for 1 hour, the reaction mixture was concentrated under vacuum. Compound 2-[(2S)-4-[7-(3-fluoro-2,6-dimethyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (20.5 mg, 33.7 umol, 100% yield, TFA) was obtained as a yellow oil.

Step C: 2-[(2S)-4-[7-(3-fluoro-2,6-dimethyl-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(3-fluoro-2,6-dimethyl-phenyl)-2-[[(2S)-1-methylpyrrolidin-2-yl]methoxy]-6,8-dihydro-5H-pyrido[3,4-d]pyrimidin-4-yl]piperazin-2-yl]acetonitrile (20.5 mg, 33.7 umol, 1 eq, TFA) in DCM (1 mL) was added TEA (34.1 mg, 337 umol, 46.9 uL, 10 eq) at −40° C. Then prop-2-enoyl chloride (3.05 mg, 33.7 umol, 2.75 uL, 1 eq) in DCM (1 mL) was added dropwised and the mixture was stirred at −40° C. for 1 hour. The reaction mixture was quenched with saturated $NaHCO_3$ aqueous solution (0.1 mL) and concentrated under vacuum. The residue was purified by prep-TLC ($SiO_2$, dichloromethane/methanol=10/1) and further purified by prep-HPLC (column: Phenomenex Synergi C18 150*25*10 um; mobile phase: [water (0.225% FA)-ACN]; B %: 16%-43%, 9 min). Title compound 2-[(2S)-4-[7-(3-fluoro-2,6-dimethyl-phenyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 349, 0.39 mg, 0.693 umol, 2% yield, 97.3% purity) was obtained as a colorless solid. LCMS [ESI, M+1]: 548.

$^1$H NMR (400 MHz, chloroform-d) δ=7.06-6.92 (m, 1H), 6.84 (t, J=8.8 Hz, 1H), 6.70-6.49 (m, 1H), 6.42 (d, J=15.2 Hz, 1H), 5.85 (d, J=10.4 Hz, 1H), 5.09 (br s, 1H), 4.60 (br s, 1H), 4.39-4.27 (m, 1H), 4.25-3.83 (m, 5H), 3.75-3.22 (m, 5H), 3.19-2.47 (m, 10H), 2.34-2.21 (m, 6H), 2.21-1.89 (m, 4H).

Example 350

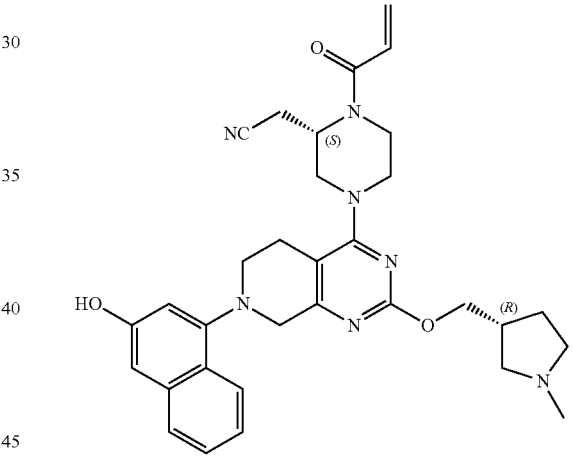

2-((S)-1-acryloyl-4-(7-(3-hydroxynaphthalen-1-yl)-2-(((R)-1-methylpyrrolidin-3-yl)methoxy)-5,6,7,8-tetrahydropyrido[3,4-d]pyrimidin-4-yl)piperazin-2-yl)acetonitrile

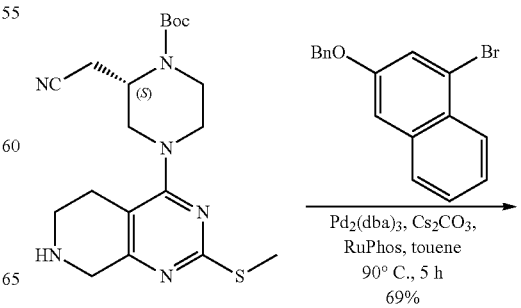

963

-continued

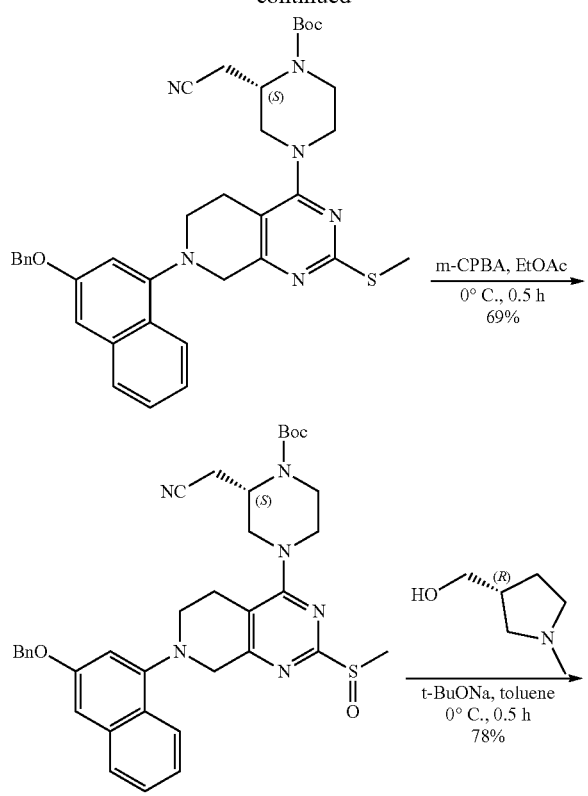

964

-continued

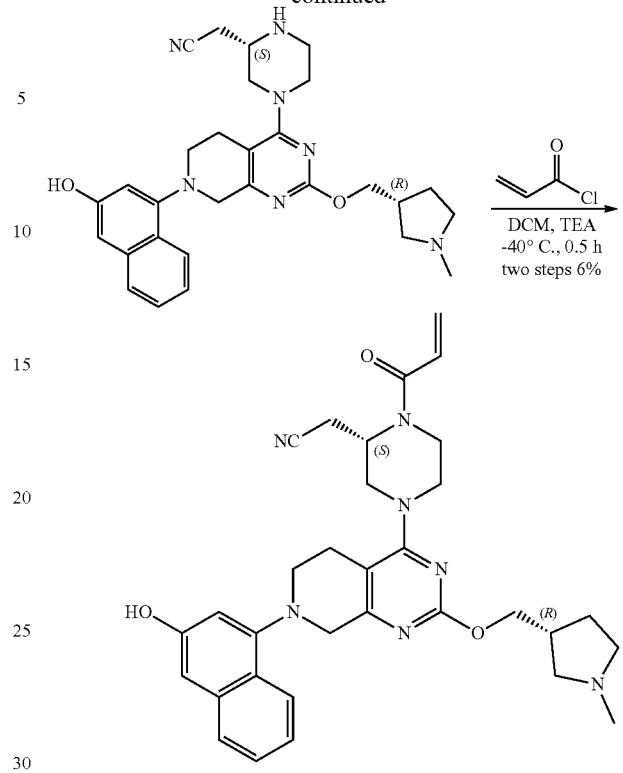

Step A: tert-butyl (2S)-4-[7-(3-benzyloxy-1-naphthyl)-2-methylsulfanyl-6,8-dihydro-5H-pyrido[3,4-d]pyrimidin-4-yl]-2-(cyanomethyl)piperazine-1-carboxylate A mixture of 3-benzyloxy-1-bromo-naphthalene (Intermediate 29, 1.01 g, 3.21 mmol, 1.3 eq), tert-butyl (2S)-2-(cyanomethyl)-4-(2-methylsulfanyl-5,6,7,8-tetrahydropyrido[3,4-d]pyrimidin-4-yl)piperazine-1-carboxylate (Intermediate 66, 1 g, 2.47 mmol, 1 eq), $Cs_2CO_3$ (2.01 g, 6.18 mmol, 2.5 eq), RuPhos (230 mg, 494 umol, 0.2 eq) and $Pd_2(dba)_3$ (452 mg, 494 umol, 0.2 eq) in toluene (50 mL) was degassed and purged with $N_2$ for 3 times, and then the mixture was stirred at 90° C. for 5 hours under $N_2$ atmosphere. The reaction mixture was diluted with water (50 mL) and extracted with ethyl acetate (50 mL×3). The combined organic layers were washed with brine (20 mL), dried over $Na_2SO_4$, filtered and concentrated under reduced pressure to give a residue. The residue was purified by column chromatography ($SiO_2$, Petroleum ether/Ethyl acetate=100/1 to 3/1). Compound tert-butyl (2S)-4-[7-(3-benzyloxy-1-naphthyl)-2-methylsulfanyl-6,8-dihydro-5H-pyrido[3,4-d]pyrimidin-4-yl]-2-(cyanomethyl)piperazine-1-carboxylate (1.2 g, 1.71 mmol, 69% yield, 91% purity) was obtained as a yellow solid. LCMS [ESI, M+1]: 637.

Step B: tert-butyl (2S)-4-[7-(3-benzyloxy-1-naphthyl)-2-methylsulfinyl-6,8-dihydro-5H-pyrido[3,4-d]pyrimidin-4-yl]-2-(cyanomethyl)piperazine-1-carboxylate To a solution of tert-butyl (2S)-4-[7-(3-benzyloxy-1-naphthyl)-2-methylsulfanyl-6,8-dihydro-5H-pyrido[3,4-d]pyrimidin-4-yl]-2-(cyanomethyl)piperazine-1-carboxylate (1.2 g, 1.88 mmol, 1 eq) in ethyl acetate (50 mL) was added

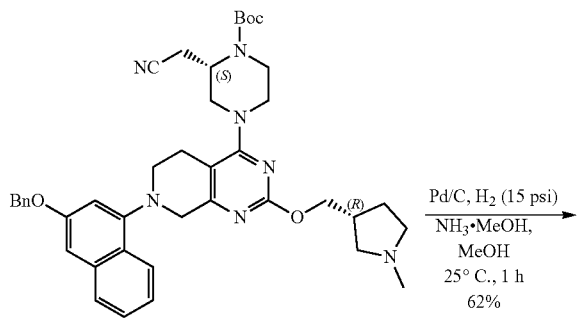

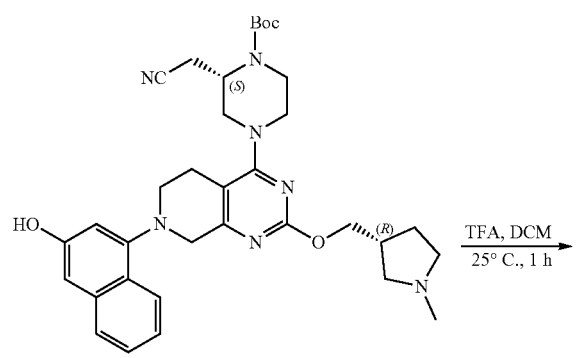

m-CPBA (382 mg, 1.88 mmol, 85% purity, 1 eq) at 0° C. After stirred at 0° C. for 0.5 hour, the reaction mixture was quenched with saturated Na$_2$S$_2$O$_3$ aqueous solution (20 mL), and then extracted with ethyl acetate (50 mL×3). The combined organic layers were washed with brine (50 mL), dried over Na$_2$SO$_4$, filtered and concentrated under reduced pressure to give a residue. The residue was purified by column chromatography (SiO$_2$, Ethyl acetate/MeOH=100/1 to 10/1). Compound tert-butyl (2S)-4-[7-(3-benzyloxy-1-naphthyl)-2-methylsulfinyl-6,8-dihydro-5H-pyrido[3,4-d]pyrimidin-4-yl]-2-(cyanomethyl)piperazine-1-carboxylate (900 mg, 1.30 mmol, 69% yield, 94% purity) was obtained as a yellow solid. LCMS [ESI, M+1]: 653.

Step C: tert-butyl (2S)-4-[7-(3-benzyloxy-1-naphthyl)-2-[[(3R)-1-methyl pyrrolidin-3-yl]methoxy]-6,8-dihydro-5H-pyrido[3,4-d]pyrimidin-4-yl]-2-(cyanomethyl)piperazine-1-carboxylate To a solution of tert-butyl (2S)-4-[7-(3-benzyloxy-1-naphthyl)-2-methylsulfinyl-6,8-dihydro-5H-pyrido[3,4-d]pyrimidin-4-yl]-2-(cyanomethyl)piperazine-1-carboxylate (793 mg, 1.22 mmol, 1 eq) in toluene (10 mL) was added t-BuONa (350 mg, 3.65 mmol, 3 eq) and [(3R)-1-methylpyrrolidin-3-yl]methanol (420 mg, 3.65 mmol, 3 eq) at 0° C. The mixture was stirred at 0° C. for 0.5 hour. The reaction mixture was diluted with water (30 mL) and extracted with ethyl acetate (50 mL×3). The combined organic layers were washed with brine (20 mL), dried over Na$_2$SO$_4$, filtered and concentrated under reduced pressure to give a residue. The residue was purified by column chromatography (SiO$_2$, Petroleum ether/Ethyl acetate=10/1 to 0/1). Compound tert-butyl (2S)-4-[7-(3-benzyloxy-1-naphthyl)-2-[[(3R)-1-methyl pyrrolidin-3-yl]methoxy]-6,8-dihydro-5H-pyrido[3,4-d]pyrimidin-4-yl]-2-(cyanomethyl)piperazine-1-carboxylate (700 mg, 944 umol, 78% yield, 95% purity) was obtained as a yellow solid. LCMS [ESI, M+1]: 704.

Step D: tert-butyl (2S)-2-(cyanomethyl)-4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]piperazine-1-carboxylate NH$_3$ was bubbled into MeOH (100 mL) at −60° C. for 10 minutes. To a solution of tert-butyl (2S)-4-[7-(3-benzyloxy-1-naphthyl)-2-[[(3R)-1-methylpyrrolidin-3-yl]methoxy]-6,8-dihydro-5H-pyrido[3,4-d]pyrimidin-4-yl]-2-(cyanomethyl)piperazine-1-carboxylate (700 mg, 994 umol, 1 eq) in MeOH (20 mL) was added dry Pd/C (300 mg, 10% purity) and the above NH$_3$.MeOH solution (20 mL) under N$_2$. The suspension was degassed under vacuum and purged with H$_2$ several times. The mixture was stirred under H$_2$ (15 psi) at 25° C. for 1 hour. The catalyst was filtered off and the filtrate was concentrated under vacuum. The residue was purified by reversed phase flash [water (0.1% formic acid)/acetonitrile)]. The mixture was adjusted pH=7 with saturated NaHCO$_3$ aqueous solution and extracted with ethyl acetate (20 mL×3). The combined organic layers were washed with brine (20 mL), dried over Na$_2$SO$_4$, filtered and concentrated under reduced pressure to give the product. Compound tert-butyl (2S)-2-(cyanomethyl)-4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]piperazine-1-carboxylate (400 mg, 619 umol, 62% yield, 95% purity) was obtained as a yellow solid. LCMS [ESI, M+1]: 614.

$^1$H NMR (400 MHz, chloroform-d) δ=8.02 (d, J=8.4 Hz, 1H), 7.62 (d, J=8.4 Hz, 1H), 7.38 (t, J=7.2 Hz, 1H), 7.29 (t, J=7.2 Hz, 1H), 6.88 (d, J=2.0 Hz, 1H), 6.70 (d, J=2.0 Hz, 1H), 4.57 (br s, 1H), 4.36-4.22 (m, 2H), 4.17-4.14 (m, 1H), 4.02 (br d, J=13.6 Hz, 2H), 3.85 (br d, J=12.8 Hz, 1H), 3.47-3.08 (m, 3H), 3.07-2.64 (m, 12H), 2.56 (s, 3H), 2.27-2.14 (m, 1H), 1.89-1.75 (m, 1H), 1.52 (s, 9H).

Step E: 2-[(2S)-4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]piperazine-1-carboxylate (400 mg, 651 umol, 1 eq) in DCM (500 uL) was added TFA (743 mg, 6.52 mmol, 482 uL, 10 eq). After stirred at 25° C. for 1 hour, the reaction mixture was concentrated under vacuum. Compound 2-[(2S)-4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (409 mg, crude, TFA) was obtained as a brown oil and used next step directly without purification. LCMS [ESI, M+1]: 514.

Step F: 2-[(2S)-4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (409 mg, 651 umol, 1 eq, TFA) in DCM (10 mL) was added TEA (659 mg, 6.52 mmol, 907 uL, 10 eq) at 0° C. After addition, prop-2-enoyl chloride (53.1 mg, 586 umol, 47.8 uL, 0.9 eq) in DCM (1 mL) was added dropwise at −40° C. The resulting mixture was stirred at −40° C. for 0.5 hour. The reaction mixture was quenched with saturated NaHCO$_3$ aqueous solution (1 mL) and extracted with ethyl acetate (10 mL×3). The combined organic layers were washed with brine (10 mL), dried over Na$_2$SO$_4$, filtered and concentrated under reduced pressure to give a residue. The residue was purified by column chromatography (SiO$_2$, Ethyl acetate/MeOH=100/1 to 5/1) and further purified by prep-HPLC (column: Boston Green ODS 150*30 5 u; mobile phase: [water (0.225% FA)-ACN]; B %: 11%-41%, 10 min). The mixture was adjusted pH=8 with saturated NaHCO$_3$ aqueous solution and extracted with dichloromethane (50 mL×3). The combined organic layers were washed with brine (20 mL), dried over Na$_2$SO$_4$, filtered and concentrated under reduced pressure. Title compound 2-[(2S)-4-[7-(3-hydroxy-1-naphthyl)-2-[[(3R)-1-methylpyrrolidin-3-yl]methoxy]-6,8-dihydro-5H-pyrido[3,4-d]pyrimidin-4-yl]-1-prop-2-enoyl-piperazin-2-yl]acetonitrile (EXAMPLE 350, 25.5 mg, 39.9 umol, 6% yield, 89% purity) was obtained as a brown solid. LCMS [ESI, M+1]: 568.

$^1$H NMR (400 MHz, Acetic acid-d$_4$) δ=8.07 (d, J=8.4 Hz, 1H), 7.66 (d, J=8.0 Hz, 1H), 7.39 (t, J=7.2 Hz, 1H), 7.29 (t, J=7.2 Hz, 1H), 6.96 (d, J=2.0 Hz, 1H), 6.87 (d, J=1.6 Hz, 1H), 6.75 (br s, 1H), 6.38 (d, J=16.8 Hz, 1H), 5.87 (d, J=10.0 Hz, 1H), 5.23-5.01 (m, 1H), 4.98-4.49 (m, 4H), 4.43 (s, 1H), 4.33 (s, 2H), 4.23-4.00 (m, 1H), 3.99-3.51 (m, 5H), 3.50-3.23 (m, 4H), 3.17-2.91 (m, 8H), 2.63-2.24 (m, 1H).

967
Example 351
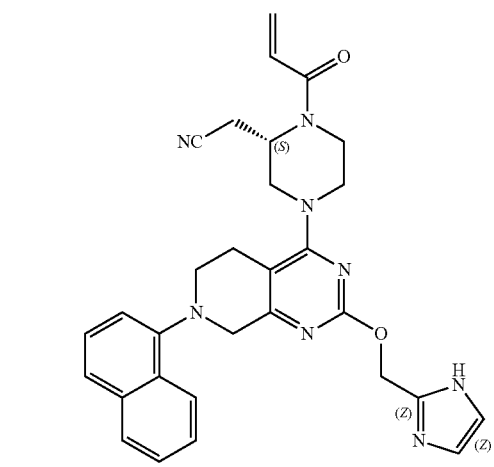
2-[(2S)-4-[2-(1H-imidazol-2-ylmethoxy)-7-(1-naphthyl)-6,8-dihydro-5H-pyrido[3,4-d]pyrimidin-4-yl]-1-prop-2-enoyl-piperazin-2-yl]acetonitrile
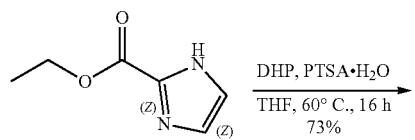
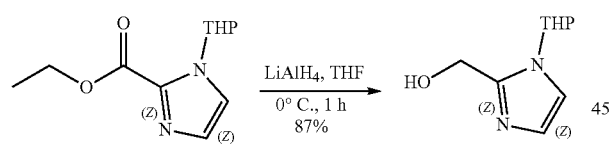
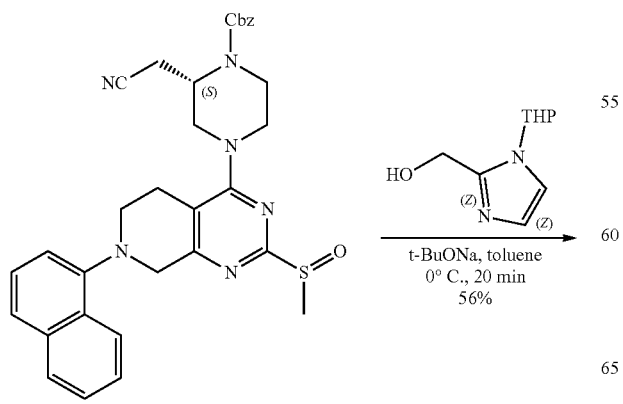
968
-continued
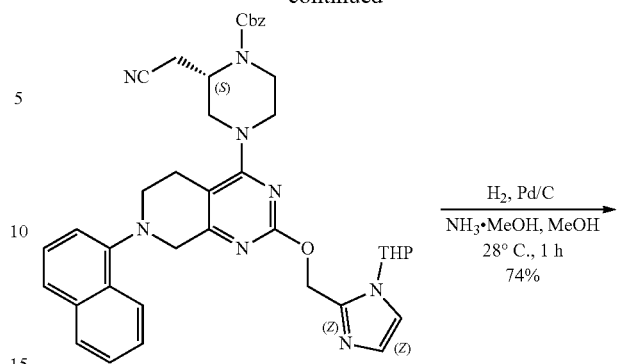
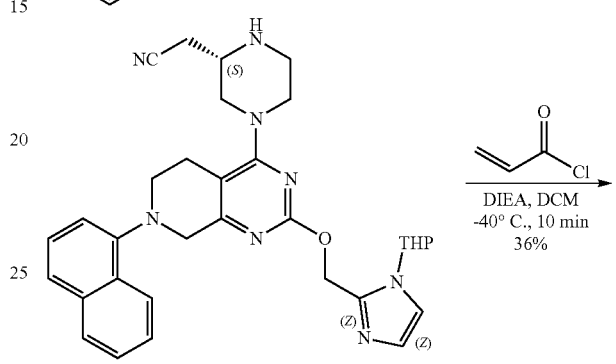
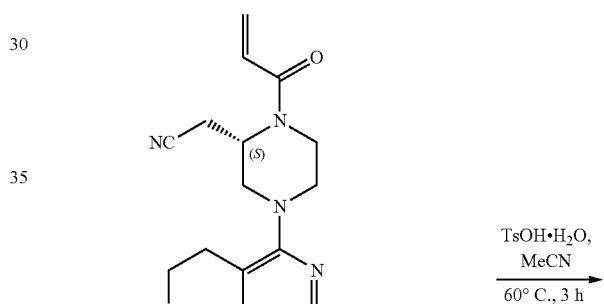
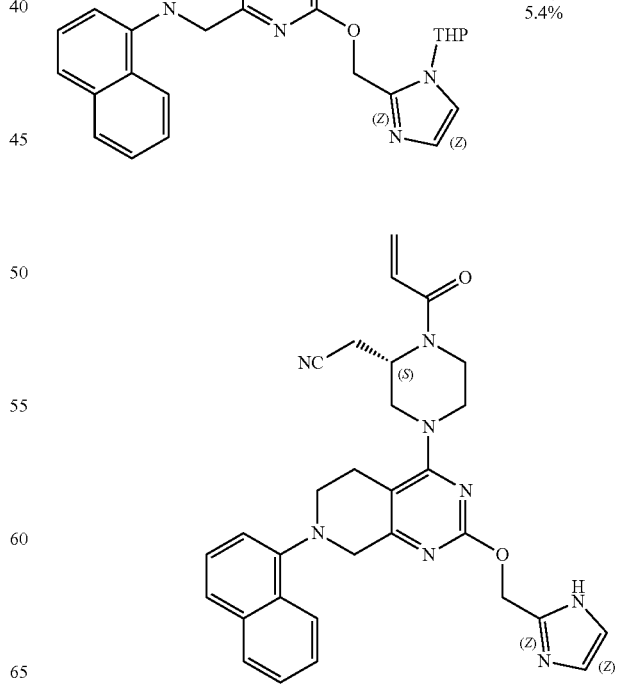

Step 1: ethyl 1-tetrahydropyran-2-ylimidazole-2-carboxylate

A mixture of ethyl 1H-imidazole-2-carboxylate (5 g, 35.7 mmol, 1 eq), DHP (33.0 g, 392 mmol, 35.9 mL, 11.0 eq) and PTSA.H$_2$O (400 mg, 2.32 mmol, 6.51e-2 eq) in THF (100 mL) was stirred at 60° C. (oil bath temperature) for 16 hours. Upon completion, the mixture was concentrated under vacuum and then diluted with ethyl acetate (100 mL) and water (100 mL). The separated organic layer was washed with brine (1×100 mL), dried over sodium sulfate, filtered and concentrated under vacuum. The residue was purified by column chromatography over silica gel (petroleum ether/ethyl acetate 20/1 to 1/1) to give ethyl 1-tetrahydropyran-2-ylimidazole-2-carboxylate (6.2 g, 26.0 mmol, 73% yield, 94% purity) as a light yellow oil.

$^1$H NMR (400 MHz, chloroform-d) δ=7.40 (d, J=0.8 Hz, 1H), 7.16 (d, J=0.8 Hz, 1H), 6.21 (dd, J=2.0, 10.0 Hz, 1H), 4.39 (dq, J=0.8, 7.2 Hz, 2H), 4.20-4.10 (m, 1H), 3.71 (dt, J=2.8, 11.6 Hz, 1H), 2.13-2.03 (m, 1H), 2.03-1.88 (m, 1H), 1.80-1.55 (m, 4H), 1.42 (t, J=7.2 Hz, 3H).

Step 2: (1-tetrahydropyran-2-ylimidazol-2-yl)methanol

A solution of ethyl 1-tetrahydropyran-2-ylimidazole-2-carboxylate (2 g, 8.92 mmol, 1 eq) in THF (40 mL) was added LiAlH$_4$ (758 mg, 20.0 mmol, 2.24 eq) in 3 portions at 0° C. The mixture was stirred at 0° C. for 1 hour. Upon completion, the mixture was quenched with saturated aqueous Na$_2$SO$_4$ (2.89 mL), filtered and the filtrate was concentrated. The residue was purified by chromatography (Al$_2$O$_3$, EtOAc/MeOH 1/0 to 10/1) to give (1-tetrahydropyran-2-ylimidazol-2-yl)methanol (1.57 g, 7.75 mmol, 87% yield, 90% purity) as a yellow oil.

$^1$H NMR (400 MHz, methanol-d$_4$) δ=7.27 (d, J=1.6 Hz, 1H), 6.89 (d, J=1.2 Hz, 1H), 5.54 (dd, J=2.4, 10.0 Hz, 1H), 4.74-4.61 (m, 2H), 4.15-3.99 (m, 1H), 3.76-3.68 (m, 1H), 2.06-1.88 (m, 3H), 1.84-1.60 (m, 3H).

Step A: benzyl (2S)-2-(cyanomethyl)-4-[7-(1-naphthyl)-2-[(1-tetrahydropyran-2-ylimidazol-2-yl)methoxy]-6,8-dihydro-5H-pyrido[3,4-d]pyrimidin-4-yl]piperazine-1-carboxylate To a solution of benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 380 mg, 654 umol, 1 eq) and (1-tetrahydropyran-2-ylimidazol-2-yl)methanol (238 mg, 1.31 mmol, 2 eq) in toluene (0.4 mL) was added t-BuONa (126 mg, 1.31 mmol, 2 eq) at 0° C. The mixture was stirred at 0° C. for 20 minutes. Upon completion, the mixture was concentrated under vacuum. The residue was diluted with water (10 mL) and extracted with EtOAc (2×20 mL). The organic layers were dried over Na$_2$SO$_4$ and concentrated under vacuum. The residue was purified by chromatography (SiO$_2$, PE/EtOAc 3/1 to 1/3) to give benzyl (2S)-2-(cyanomethyl)-4-[7-(1-naphthyl)-2-[(1-tetrahydropyran-2-ylimidazol-2-yl)methoxy]-6,8-dihydro-5H-pyrido[3,4-d]pyrimidin-4-yl]piperazine-1-carboxylate (270 mg, 363.19 umol, 56% yield, 94% purity) as a yellow solid. LCMS [ESI, M+1]: 699.

Step B: 2-[(2S)-4-[7-(1-naphthyl)-2-[(1-tetrahydropyran-2-ylimidazol-2-yl)methoxy]-6,8-dihydro-5H-pyrido[3,4-d]pyrimidin-4-yl]piperazin-2-yl]acetonitrile NH$_3$ was bubbled into MeOH (3 mL) at −40° C. for 10 minutes. A solution of benzyl (2S)-2-(cyanomethyl)-4-[7-(1-naphthyl)-2-[(1-tetrahydropyran-2-ylimidazol-2-yl)methoxy]-6,8-dihydro-5H-pyrido[3,4-d]pyrimidin-4-yl]piperazine-1-carboxylate (260 mg, 372 umol, 1 eq) in MeOH (3 mL) was added above solution, then Pd/C (100 mg, 10% purity) under N$_2$. The suspension was degassed under vacuum and purged with H$_2$ 6 times. The reaction was stirred under H$_2$ (15 psi) at 28° C. for 1 hour. Upon completion, the mixture was filtered and the filtrate was concentrated under vacuum to give 2-[(2S)-4-[7-(1-naphthyl)-2-[(1-tetrahydropyran-2-ylimidazol-2-yl)methoxy]-6,8-dihydro-5H-pyrido[3,4-d]pyrimidin-4-yl]piperazin-2-yl]acetonitrile (160 mg, 275 umol, 74% yield, 97% purity) as a yellow solid which was used directly into the next step without further purification. LCMS [ESI, M+1]: 565.

Step C: 2-[(2S)-4-[7-(1-naphthyl)-2-[(1-tetrahydropyran-2-ylimidazol-2-yl)methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(1-tetrahydropyran-2-ylimidazol-2-yl)methoxy]-6,8-dihydro-5H-pyrido[3,4-d]pyrimidin-4-yl]piperazin-2-yl]acetonitrile (160 mg, 283 umol, 1.00 eq) and DIEA (73.2 mg, 567 umol, 98.7 uL, 2.00 eq) in DCM (3 mL) was added prop-2-enoyl chloride (38.5 mg, 425 umol, 34.7 uL, 1.50 eq) dropwise at −40° C. The mixture was stirred at −40° C. for 10 minutes. Upon completion, to the mixture was added saturated aqueous NaHCO$_3$ (1 mL) and water (3 mL). Layers were separated. The aqueous phase was extracted with EtOAc (2×5 mL). The combined organic layers were dried over Na$_2$SO$_4$ and concentrated under vacuum. The residue was purified by column chromatography (Al$_2$O$_3$, EtOAc/MeOH 50/1 to 10/1) to give 2-[(2S)-4-[7-(1-naphthyl)-2-[(1-tetrahydropyran-2-ylimidazol-2-yl)methoxy]-6,8-dihydro-5H-pyrido[3,4-d]pyrimidin-4-yl]-1-prop-2-enoyl-piperazin-2-yl]acetonitrile (80 mg, 101 umol, 36% yield, 78% purity) as a yellow solid. LCMS [ESI, M+1]: 619.

Step D: 2-[(2S)-4-[2-(1H-imidazol-2-ylmethoxy)-7-(1-naphthyl)-6,8-dihydro-5H-pyrido[3,4-d]pyrimidin-4-yl]-1-prop-2-enoyl-piperazin-2-yl]acetonitrile A solution of 2-[(2S)-4-[7-(1-naphthyl)-2-[(1-tetrahydropyran-2-ylimidazol-2-yl)methoxy]-6,8-dihydro-5H-pyrido[3,4-d]pyrimidin-4-yl]-1-prop-2-enoyl-piperazin-2-yl]acetonitrile (67 mg, 84.5 umol, 1 eq) and TsOH.H$_2$O (48.2 mg, 253 umol, 3 eq) in MeCN (1.5 mL) was stirred at 60° C. for 3 hours. Upon completion, the mixture was quenched with saturated aqueous NaHCO$_3$ (1 mL) at 0° C. The residue was purified by reversed-phase flash [water (0.1% NH$_3$.H$_2$O)/acetonitrile]. The desired fractions were collected and lyophilized. The crude product was purified by prep-HPLC (column: PhenomenexSynergi C18 150*30 mm*4 um; mobile phase: [water (0.225% FA)-ACN]; B %: 20%-50%, 10.5 min). The desired fractions were collected and lyophilized. to give title compound 2-[(2S)-4-[2-(1H-imidazol-2-ylmethoxy)-7-(1-naphthyl)-6,8-dihydro-5H-pyrido[3,4-d]pyrimidin-4-yl]-1-prop-2-enoyl-piperazin-2-yl]acetonitrile (EXAMPLE 351, 2.55 mg, 4.22 umol, 5.4% yield, 96% purity, FA) as a white solid. LCMS [ESI, M+1]: 535.

SFC Condition: Column: Chiralpak AS-3 50×4.6 mm I.D., 3 um, Mobile phase: methanol (0.05% DEA) in CO$_2$ from 5% to 40%, Flow rate: 3 mL/min, Wavelength: 220 nm $^1$H NMR (400 MHz, chloroform-d) δ=8.26-8.20 (m, 1H), 7.92-7.82 (m, 1H), 7.63 (d, J=8.4 Hz, 1H), 7.56-7.48 (m, 2H), 7.45 (t, J=8.0 Hz, 1H), 7.17 (d, J=7.2 Hz, 1H), 7.08-6.99 (m, 2H), 6.69-6.52 (m, 1H), 6.46-6.32 (m, 1H), 5.84 (br d, J=11.2 Hz, 1H), 5.56-5.44 (m, 2H), 5.24-4.90 (m, 1H), 4.88-4.14 (m, 4H), 4.14-3.79 (m, 2H), 3.79-3.37 (m, 3H), 3.35-2.64 (m, 4H), 2.61-2.49 (m, 1H).

Example 352

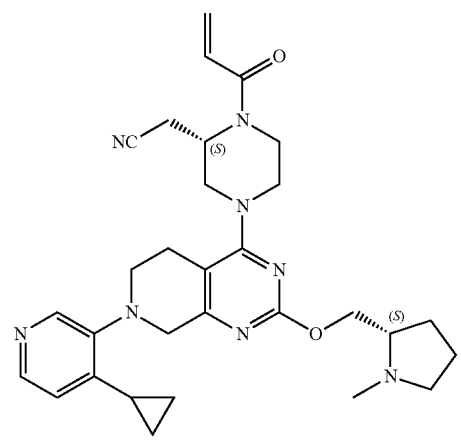

2-[(2S)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

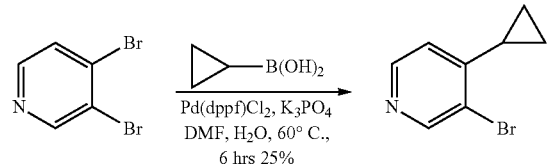

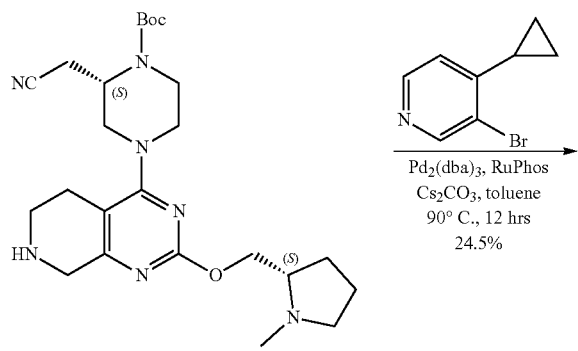

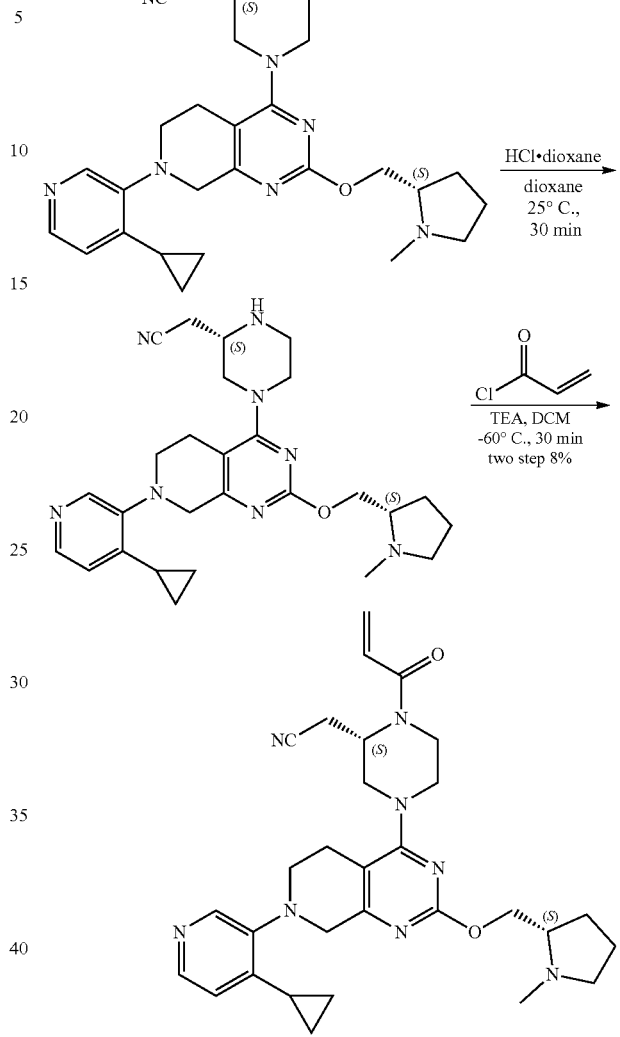

3-bromo-4-cyclopropyl-pyridine

A mixture of 3,4-dibromopyridine (3.0 g, 12.7 mmol, 1.0 eq), cyclopropylboronic acid (1.09 g, 12.7 mmol, 1.0 eq), Pd(dppf)Cl$_2$ (927 mg, 1.27 mmol, 0.10 eq), K$_3$PO$_4$ (8.06 g, 38.0 mmol, 3.0 eq) in DMF (15.0 mL) and H$_2$O (3.0 mL) was degassed and purged with N$_2$ for 3 times, and then the mixture was stirred at 60° C. for 6 hrs under N$_2$ atmosphere. The organic solvent was washed with water (80.0 mL). The aqueous phase was extracted with ethyl acetate (3×100 mL). Combine extracts were washed with brine (300 mL), dried with Na$_2$SO$_4$ the solvent was then removed under vacuum. The residue was purified by column chromatography (SiO$_2$, Petroleum ether: Ethyl acetate=30:1 to 20:1). Compound 3-bromo-4-cyclopropyl-pyridine (630 mg, 3.17 mmol, 25% yield, 99.6% purity) was obtained as a yellow oil. LCMS [ESI, M+1]: 198.

$^1$H NMR (400 MHz, CHLOROFORM-d) δ=8.69-8.61 (m, 1H), 8.39-8.32 (m, 1H), 6.75-6.71 (m, 1H), 2.29-2.18 (m, 1H), 1.20-1.12 (m, 2H), 0.84-0.77 (m, 2H).

Step A: tert-butyl (2S)-2-(cyanomethyl)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 500 mg, 1.06 mmol, 1.0 eq), 3-bromo-4-cyclopropyl-pyridine (315 mg, 1.59 mmol, 1.50 eq), $Pd_2(dba)_3$ (97.09 mg, 106 umol, 0.10 eq), RuPhos (99.0 mg, 212 umol, 0.20 eq) and $Cs_2CO_3$ (1.04 g, 3.18 mmol, 3.0 eq) in toluene (5.0 mL) was degassed and purged with $N_2$ for 3 times, and then the mixture was stirred at 90° C. for 12 hrs under $N_2$ atmosphere. The organic solvent was washed with water (15.0 mL). The aqueous phase was extracted with ethyl acetate (3×20 mL). Combine extracts were washed with brine (50.0 mL), dried with $Na_2SO_4$ the solvent was then removed under vacuum. The residue was purified by reversed phase flash HPLC [C18, 0.1% $NH_3.H_2O$ in water, 0-60% MeCN]. The obtained product was then concentrated, the aqueous was extracted with EA (3×50 mL), the combined organic layer was dried over $Na_2SO_4$, filtered and concentrated. Compound tert-butyl (2S)-2-(cyanomethyl)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]piperazine-1-carboxylate (180 mg, 260 umol, 24.5% yield, 85% purity) was obtained as a yellow solid. LCMS [ESI, M+1]:589.

Step B: 2-[(2S)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]piperazine-1-carboxylate (30.0 mg, 43.3 umol, 1.0 eq) in dioxane (1.0 mL) was added HCl.dioxane (4 M, 1.0 mL, 92.4 eq). The mixture was stirred at 25° C. for 30 min under $N_2$ atmosphere. The organic solvent was removed under vacuum. The obtained product was adjusted with saturated $NaHCO_3$ aqueous to pH ~8, then concentrated, the aqueous was extracted with ethyl acetate (3×10 mL), the combined organic layer was dried over $Na_2SO_4$, filtered and concentrated. The crude product 2-[(2S)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]piperazin-2-yl]acetonitrile (30.0 mg, crude) was obtained as a yellow solid and used into the next step without further purification. LCMS [ESI, M+1]: 489.

Step C: 2-[(2S)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]piperazin-2-yl]acetonitrile (30.0 mg, 61.4 umol, 1.0 eq) in DCM (1.50 mL) was added TEA (31.1 mg, 307 umol, 42.7 uL, 5.0 eq) and prop-2-enoyl chloride (8.34 mg, 92.1 umol, 7.51 uL, 1.50 eq) at −60° C.

The mixture was stirred at −60° C. for 30 min under $N_2$ atmosphere. The reaction was quenched with methanol (6.0 mL) and was removed under vacuum. The residue was purified by prep-HPLC (column: Gemini 150*25 5 u; mobile phase: [water (0.05% ammonia hydroxide v/v)-ACN]; B %: 33%-63%,12 min) and lyophilization. Title compound 2-[(2S)-4-[7-(4-cyclopropyl-3-pyridyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 352, 2.71 mg, 4.97 umol, 8.1% yield, 99.5% purity) was obtained as a white solid. LCMS [ESI, M+1]: 543.

$^1$H NMR (400 MHz, CHLOROFORM-d) δ=8.29 (s 1H), 8.26 (d, J=5.2 Hz, 1H), 6.68 (d, J=5.2 Hz, 1H), 6.64-6.53 (m, 1H), 6.40 (dd, J=0.8 Hz, J=16.8 Hz, 1H), 5.52 (d, J=10.4 Hz, 1H), 5.07 (br s, 1H), 4.39 (dd, J=4.8 Hz, J=10.4 Hz, 1H), 4.29-4.23 (m, 1H), 4.21-4.15 (m, 2H), 4.13-4.07 (m, 1H), 4.00-3.95 (m, 1H), 3.57 (br s, 1H), 3.44-3.24 (m, 4H), 3.17-3.03 (m, 2H), 2.94 (dd, J=8.8 Hz, J=16.8 Hz, 1H), 2.87-2.80 (m, 2H), 2.73-2.64 (m, 1H), 2.49 (s, 3H), 2.35-2.22 (m, 3H), 2.11-2.00 (m, 1H), 1.89-1.76 (m, 3H), 1.17-1.11 (m, 2H), 0.90-0.77 (m, 3H).

Example 353

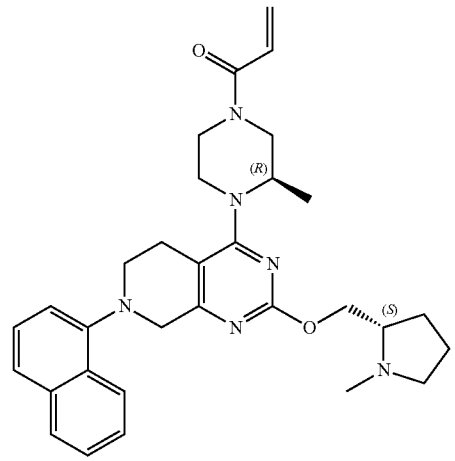

1-[(3R)-3-methyl-4-[2-[[(2S)-1-methylpyrrolidin-2-yl]methoxy]-7-(1-naphthyl)-6,8-dihydro-5H-pyrido[3,4-d]pyrimidin-4-yl]piperazin-1-yl]prop-2-en-1-one

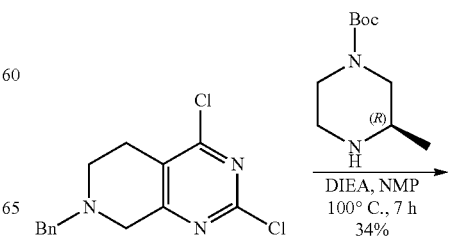

DIEA, NMP
100° C., 7 h
34%

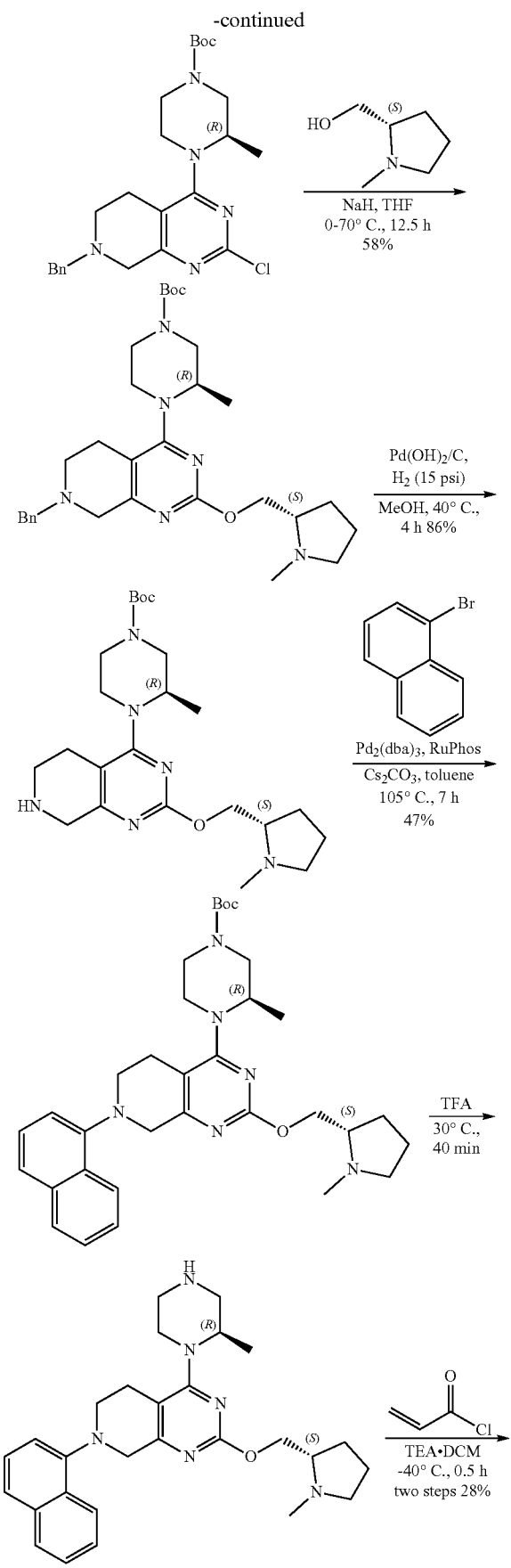

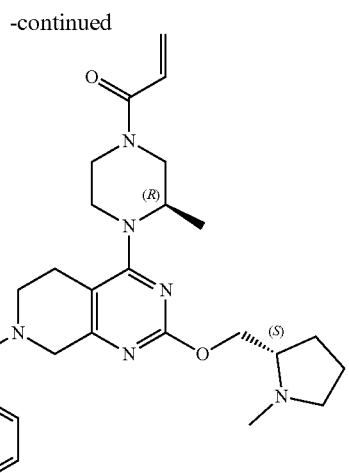

Step A: tert-butyl (3R)-4-(7-benzyl-2-chloro-6,8-dihydro-5H-pyrido[3,4-d]pyrimidin-4-yl)-3-methyl-piperazine-1-carboxylate The solution of 7-benzyl-2,4-dichloro-6,8-dihydro-5H-pyrido[3,4-d]pyrimidine (1.5 g, 5.10 mmol, 1 eq), tert-butyl (3R)-3-methylpiperazine-1-carboxylate (1.12 g, 5.61 mmol, 1.1 eq), DIEA (1.32 g, 10.2 mmol, 1.78 mL, 2 eq) in NMP (30 mL) was stirred at 100° C. for 7 hours. Water (90 mL) was added into the mixture. The resulting mixture was diluted with EtOAc (20 mL) and extracted with EtOAc (3×50 mL). The combined organic layers were washed with brine (40 mL). The combined organic layers were dried over anhydrous Na$_2$SO$_4$, filtered and concentrated under vacuum. The residue was slurried with (PE:EtOAc=3:1, 20 mL) and filtered and the filter cake was washed with (PE:EtOAc=3:1, 40 mL) to give tert-butyl (3R)-4-(7-benzyl-2-chloro-6,8-dihydro-5H-pyrido[3,4-d]pyrimidin-4-yl)-3-methyl-piperazine-1-carboxylate (0.9 g, 1.73 mmol, 34% yield, 88.0% purity) as a gray solid. LCMS [ESI, M+1]: 458.

$^1$H NMR (400 MHz, chloroform-d) δ=7.38-7.27 (m, 5H), 4.28-4.18 (m, 1H), 4.16-3.80 (m, 2H), 3.74 (br d, J=13.6 Hz, 1H), 3.68 (s, 2H), 3.65-3.52 (m, 2H), 3.41-3.27 (m, 1H), 3.21-2.89 (m, 2H), 2.74-2.58 (m, 4H), 1.48 (s, 9H), 1.23 (d, J=6.8 Hz, 3H).

Step B: tert-butyl (3R)-4-[7-benzyl-2-[[(2S)-1-methylpyrrolidin-2-yl]methoxy]-6,8-dihydro-5H-pyrido[3,4-d]pyrimidin-4-yl]-3-methyl-piperazine-1-carboxylate To the solution of [(2S)-1-methylpyrrolidin-2-yl]methanol (566 mg, 4.91 mmol, 583 uL, 2.5 eq) in THF (20 mL) was added NaH (157 mg, 3.93 mmol, 60.0% purity, 2 eq) at 0° C. and stirred at 0° C. for 0.5 hour. Then tert-butyl (3R)-4-(7-benzyl-2-chloro-6,8-dihydro-5H-pyrido[3,4-d]pyrimidin-4-yl)-3-methyl-piperazine-1-carboxylate (900 mg, 1.97 mmol, 1 eq) was added to the mixture. The reaction mixture was heated to 70° C. for 12 hours in a tube under N$_2$. The mixture was quenched by Water (15 mL). The mixture was diluted with EtOAc (10 mL) and extracted with EtOAc (3×50 mL). The combined organic layers were washed with brine (40 mL). The combined organic layers were dried over anhydrous Na$_2$SO$_4$, filtered and concentrated under vacuum. The residue was purified by reversed phase flash column (ACN/Water (0.1% FA)=35%) to give tert-butyl (3R)-4-[7- benzyl-2-[[(2S)-1-methylpyrrolidin-2-yl]methoxy]-6,8-dihydro-5H-pyrido[3,4-d]pyrimidin-4-yl]-3-methyl-piperazine-1-carboxylate (680 mg, 1.14 mmol, 58% yield, 90.0% purity) as a brown solid. LCMS [ESI, M+1]: 537.

Step C: tert-butyl (3R)-3-methyl-4-[2-[[(2S)-1-methylpyrrolidin-2-yl]methoxy]-5,6,7,8-tetrahydropyrido[3,4-d]pyrimidin-4-yl]piperazine-1-carboxylate To the solution of tert-butyl (3R)-4-[7-benzyl-2-[[(2S)-1-methylpyrrolidin-2-yl]methoxy]-6,8-dihydro-5H-pyrido[3,4-d]pyrimidin-4-yl]-3-methyl-piperazine-1-carboxylate (680 mg, 1.27 mmol, 1 eq) in MeOH (14 mL) was added Pd(OH)$_2$/C (340 mg, 10% purity) under N$_2$. The suspension was degassed under vacuum and purged with H$_2$ several times. The mixture was stirred under H$_2$ (15 psi) at 40° C. for 4 hours. The reaction mixture was filtered, the filter cake was washed with MeOH (3×10 mL), and the filtrate was concentrated under vacuum to give tert-butyl (3R)-3-methyl-4-[2-[[(2S)-1-methylpyrrolidin-2-yl]methoxy]-5,6,7,8-tetrahydropyrido[3,4-d]pyrimidin-4-yl]piperazine-1-carboxylate (540 mg, 1.09 mmol, 86% yield, 90.0% purity) as a brown solid which was used for next step without further purification.

Step D: tert-butyl (3R)-3-methyl-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate To the solution of tert-butyl (3R)-3-methyl-4-[2-[[(2S)-1-methylpyrrolidin-2-yl]methoxy]-5,6,7,8-tetrahydropyrido[3,4-d]pyrimidin-4-yl]piperazine-1-carboxylate (520 mg, 1.16 mmol, 1 eq), 1-bromonaphthalene (482 mg, 2.33 mmol, 324 uL, 2 eq), RuPhos (109 mg, 233 umol, 0.2 eq) and Cs$_2$CO$_3$ (1.14 g, 3.49 mmol, 3 eq) in toluene (11 mL) was added Pd$_2$(dba)$_3$ (107 mg, 116 umol, 0.1 eq) under N$_2$. The suspension was degassed under vacuum and purged with N$_2$ several times. The mixture was stirred under N$_2$ at 105° C. for 7 hours. Water (10 mL) was added into the mixture. The mixture was diluted with EtOAc (10 mL) and extracted with EtOAc (3×20 mL). The combined organic layers were washed with brine (20 mL), dried over anhydrous Na$_2$SO$_4$, filtered and concentrated under vacuum. The residue was purified by silica gel chromatography (PE:EtOAc from 5:1 to 0:1). Then the residue was purified by reversed phase flash column (ACN/Water (0.1% FA)=61%). Compound tert-butyl (3R)-3-methyl-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (330 mg, 547 umol, 47% yield, 95.0% purity) was obtained as a yellow solid. LCMS [ESI, M+1]: 573.

$^1$H NMR (400 MHz, chloroform-d) δ=8.26-8.18 (m, 1H), 7.89-7.84 (m, 1H), 7.60 (d, J=8.4 Hz, 1H), 7.54-7.47 (m, 2H), 7.43 (t, J=7.6 Hz, 1H), 7.14 (d, J=7.2 Hz, 1H), 4.41 (dd, J=5.2, 10.4 Hz, 1H), 4.26 (s, 3H), 4.18-4.14 (m, 1H), 4.03-3.68 (m, 2H), 3.45-3.00 (m, 6H), 2.84 (br s, 2H), 2.69 (br d, J=6.4 Hz, 1H), 2.50 (s, 3H), 2.35-2.24 (m, 1H), 2.12-2.06 (m, 1H), 1.91-1.70 (m, 4H), 1.50 (s, 9H), 1.32-1.27 (m, 3H).

Step E: 4-[(2R)-2-methylpiperazin-1-yl]-2-[[(2S)-1-methylpyrrolidin-2-yl]methoxy]-7-(1-naphthyl)-6,8-dihydro-5H-pyrido[3,4-d]pyrimidine The mixture of tert-butyl (3R)-3-methyl-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (330 mg, 576 umol, 1 eq) and TFA (657 mg, 5.76 mmol, 427 uL, 10 eq) was stirred at 30° C. for 40 mins. The mixture was concentrated under vacuum to give 4-[(2R)-2-methylpiperazin-1-yl]-2-[[(2S)-1-methylpyrrolidin-2-yl]methoxy]-7-(1-naphthyl)-6,8-dihydro-5H-pyrido[3,4-d]pyrimidine (340 mg, crude, TFA) as a brown oil which was used for next step without further purification.

Step F: 1-[(3R)-3-methyl-4-[2-[[(2S)-1-methylpyrrolidin-2-yl]methoxy]-7-(1-naphthyl)-6,8-dihydro-5H-pyrido[3,4-d]pyrimidin-4-yl]piperazin-1-yl]prop-2-en-1-one To the solution of 4-[(2R)-2-methylpiperazin-1-yl]-2-[[(2S)-1-methylpyrrolidin-2-yl]methoxy]-7-(1-naphthyl)-6,8-dihydro-5H-pyrido[3,4-d]pyrimidine (340 mg, crude, TFA), TEA (586 mg, 5.80 mmol, 807 uL) in DCM (6 mL) was added prop-2-enoyl chloride (78.7 mg, 869 umol, 70.9 uL) at −40° C., the mixture was stirred at −40° C. for 0.5 hour. The mixture was quenched by saturated NaHCO$_3$ (2 mL). The mixture was diluted with EtOAc (5 mL) and extracted with EtOAc (10 mL). The organic layer was dried over anhydrous Na$_2$SO$_4$, filtered and concentrated under vacuum. The residue was purified by prep-HPLC (column: Gemini 150*25 5 u; mobile phase: [water (0.05% ammonia hydroxide v/v)-ACN]; B %: 55%-85%,12 min) to give title compound 1-[(3R)-3-methyl-4-[2-[[(2S)-1-methylpyrrolidin-2-yl]methoxy]-7-(1-naphthyl)-6,8-dihydro-5H-pyrido[3,4-d]pyrimidin-4-yl]piperazin-1-yl]prop-2-en-1-one (EXAMPLE 353, 85.5 mg, 162 umol, two steps 28% yield, 99.8% purity) as a white solid. LCMS [ESI, M+1]: 527.

$^1$H NMR (400 MHz, chloroform-d) δ=8.23 (br d, J=9.2 Hz, 1H), 7.90-7.84 (m, 1H), 7.61 (d, J=8.4 Hz, 1H), 7.55-7.47 (m, 2H), 7.44 (t, J=7.6 Hz, 1H), 7.15 (d, J=7.2 Hz, 1H), 6.70-6.52 (m, 1H), 6.37 (dd, J=1.6, 16.8 Hz, 1H), 5.77 (br d, J=10.0 Hz, 1H), 4.66-4.31 (m, 3H), 4.27 (s, 2H), 4.14 (dd, J=6.8, 10.4 Hz, 1H), 4.02-3.73 (m, 2H), 3.64-3.25 (m, 4H), 3.24-2.99 (m, 2H), 2.86 (br s, 2H), 2.74-2.63 (m, 1H), 2.49 (s, 3H), 2.34-2.24 (m, 1H), 2.13-2.00 (m, 1H), 1.90-1.74 (m, 3H), 1.28 (br d, J=4.4 Hz, 3H).

Example 354

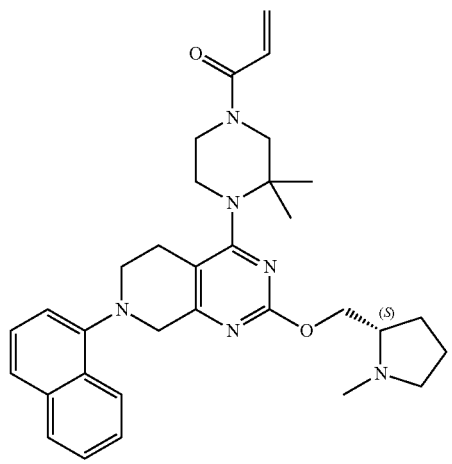

979

1-[3,3-dimethyl-4-[2-[[(2S)-1-methylpyrrolidin-2-yl] methoxy]-7-(1-naphthyl)-6,8-dihydro-5H-pyrido[3,4-d]pyrimidin-4-yl]piperazin-1-yl]prop-2-en-1-one

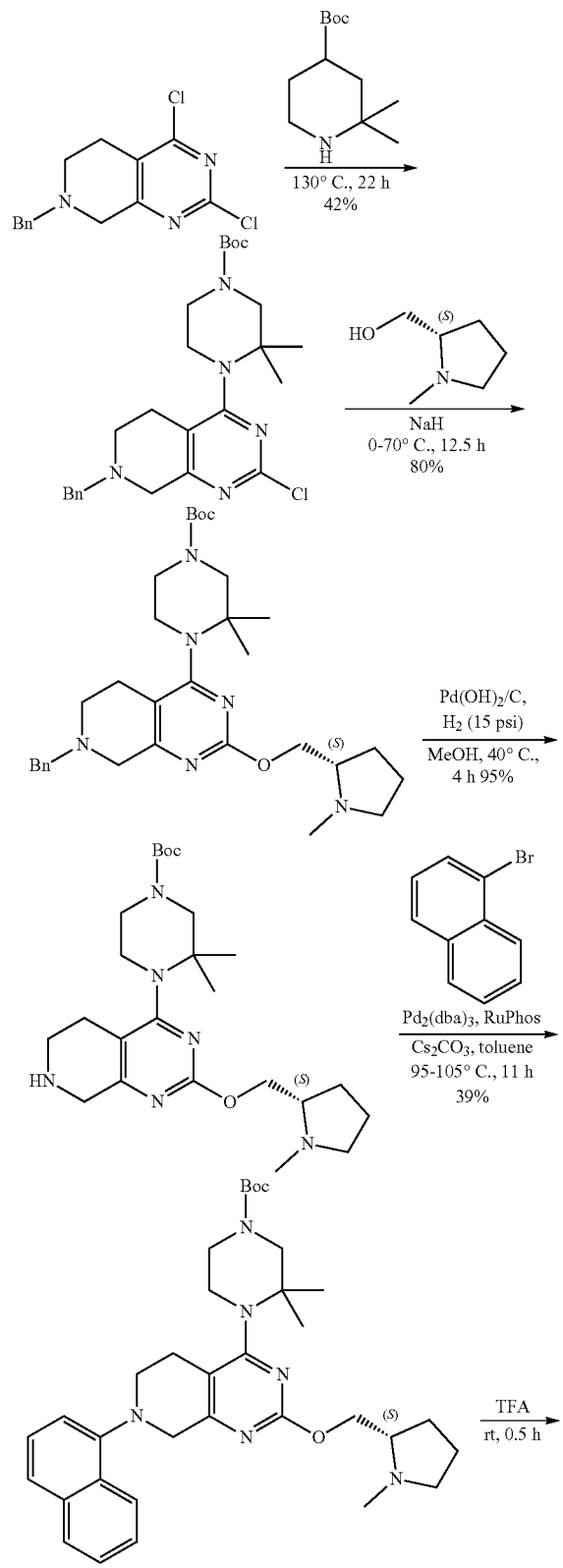

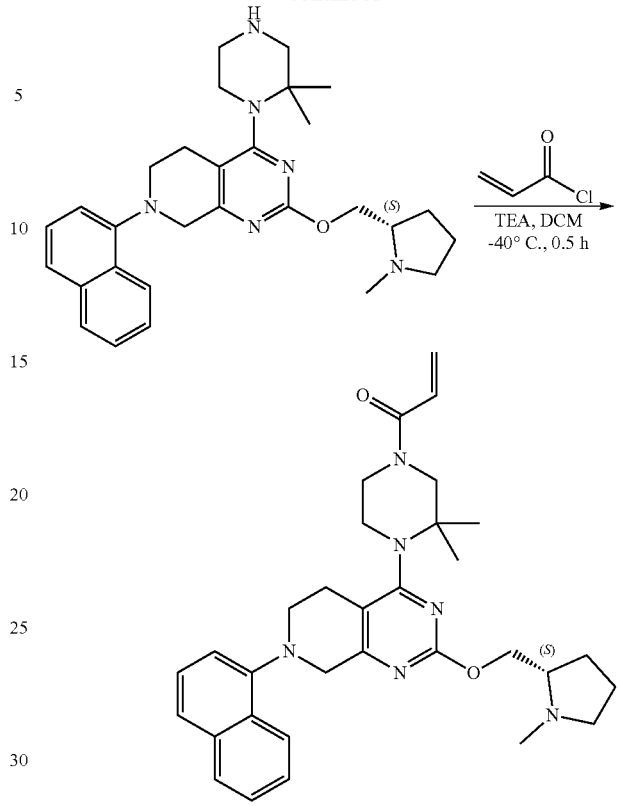

Step A: tert-butyl 4-(7-benzyl-2-chloro-6,8-dihydro-5H-pyrido[3,4-d]pyrimidin-4-yl)-3,3-dimethyl-piperazine-1-carboxylate The solution of 7-benzyl-2,4-dichloro-6,8-dihydro-5H-pyrido[3,4-d]pyrimidine (1.5 g, 5.10 mmol, 1 eq) and tert-butyl 3,3-dimethylpiperazine-1-carboxylate (4.37 g, 20.4 mmol, 4 eq) was stirred at 130° C. for 22 hours. The residue was used directly to purify. The residue was purified by silica gel chromatography (PE:EtOAc from 1:0 to 10:1). Then the residue was purified by prep-HPLC (column: Phenomenex Synergi Max-RP 250*80 mm*10 um; mobile phase: [water (0.225% FA)-ACN]; B %: 30%-60%, 35 min, 60% min) to give tert-butyl 4-(7-benzyl-2-chloro-6,8-dihydro-5H-pyrido[3,4-d]pyrimidin-4-yl)-3,3-dimethyl-piperazine-1-carboxylate (1 g, 2.12 mmol, 42% yield, 100% purity) as a yellow solid. LCMS [ESI, M+1]: 472.
$^1$H NMR (400 MHz, chloroform-d) δ=7.39-7.28 (m, 5H), 4.01 (t, J=5.6 Hz, 2H), 3.69 (s, 2H), 3.55-3.44 (m, 6H), 2.78-2.66 (m, 4H), 1.51 (s, 6H), 1.48 (s, 9H).

Step B: tert-butyl 4-[7-benzyl-2-[[(2S)-1-methylpyrrolidin-2-yl]methoxy]-6,8-dihydro-5H-pyrido[3,4-d]pyrimidin-4-yl]-3,3-dimethyl-piperazine-1-carboxylate To the solution of [(2S)-1-methylpyrrolidin-2-yl]methanol (610 mg, 5.30 mmol, 629 uL, 2.5 eq) in THF (20 mL) was added NaH (169 mg, 4.24 mmol, 60% purity, 2 eq) at 0° C. and stirred at 0° C. for 0.5 hour. Then tert-butyl 4-(7-benzyl-2-chloro-6,8-dihydro-5H-pyrido[3,4-d]pyrimidin-4-yl)-3,3-dimethyl-piperazine-1-carboxylate (1 g, 2.12 mmol, 1 eq) was added to the mixture. The reaction mixture was heated to 70° C. for 12 hours in a tube under N₂. The reaction mixture was quenched by Water (10 mL). The mixture was diluted with EtOAc (10 mL) and extracted with EtOAc (2×30 mL). The combined organic layers were dried over anhydrous Na₂SO₄, filtered and concentrated under vacuum. The residue was purified by prep-HPLC (column: Phenomenex luna C18 250*50 mm*10 um; mobile phase: [water (0.225% FA)-ACN]; B %: 25%-50%,30; 79% min) to give tert-butyl 4-[7-benzyl-2-[[(2S)-1-methylpyrrolidin-2-yl]methoxy]-6,8-dihydro-5H-pyrido[3,4-d]pyrimidin-4-yl]-3,3-dimethyl-piperazine-1-carboxylate (980 mg, 1.69 mmol, 80% yield, 95.0% purity) as a yellow oil. LCMS [ESI, M+1]: 551.

Step C: tert-butyl 3,3-dimethyl-4-[2-[[(2S)-1-methylpyrrolidin-2-yl]methoxy]-5,6,7,8-tetrahydropyrido[3,4-d]pyrimidin-4-yl]piperazine-1-carboxylate To the solution of tert-butyl 4-[7-benzyl-2-[[(2S)-1-methylpyrrolidin-2-yl]methoxy]-6,8-dihydro-5H-pyrido[3,4-d]pyrimidin-4-yl]-3,3-dimethyl-piperazine-1-carboxylate (980 mg, 1.78 mmol, 1 eq) in MeOH (20 mL) was added Pd(OH)₂/C (500 mg, 10% purity) under N₂. The suspension was degassed under vacuum and purged with H₂ several times. The mixture was stirred under H₂ (15 psi) at 40° C. for 4 hours. The mixture was filtered, the filter cake was washed with MeOH (3×10 mL). The filtrate was concentrated under vacuum to give tert-butyl 3,3-dimethyl-4-[2-[[(2S)-1-methylpyrrolidin-2-yl]methoxy]-5,6,7,8-tetrahydropyrido[3,4-d]pyrimidin-4-yl]piperazine-1-carboxylate (780 mg, 1.69 mmol, 95% yield, 100% purity) as a colorless oil which was used for next step without further purification. LCMS [ESI, M+1]: 461.

Step D: tert-butyl 3,3-dimethyl-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate To the solution of tert-butyl 3,3-dimethyl-4-[2-[[(2S)-1-methylpyrrolidin-2-yl]methoxy]-5,6,7,8-tetrahydropyrido[3,4-d]pyrimidin-4-yl]piperazine-1-carboxylate (400 mg, 868 umol, 1 eq), 1-bromonaphthalene (360 mg, 1.74 mmol, 241 uL, 2 eq), Cs₂CO₃ (849 mg, 2.61 mmol, 3 eq) and RuPhos (81.0 mg, 174 umol, 0.2 eq) in toluene (8 mL) was added Pd₂(dba)₃ (79.5 mg, 86.8 umol, 0.1 eq) under N₂. The suspension was degassed under vacuum and purged with N₂ several times. The mixture was stirred under N₂ at 95° C. for 8 hours. Water (10 mL) was added into the mixture. The mixture was diluted with EtOAc (10 mL) and extracted with EtOAc (2×20 mL). The combined organic layers were dried over anhydrous Na₂SO₄, filtered and concentrated under vacuum. The residue was purified by silica gel chromatography (PE:EtOAc=10:1~0:1). Then the residue was purified by reversed phase flash column (ACN/Water (0.1% FA)=52%) to give tert-butyl 3,3-dimethyl-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (210 mg, 340 umol, 39% yield, 95.0% purity) as a white solid. LCMS [ESI, M+1]: 587.

¹H NMR (400 MHz, chloroform-d) δ=8.22 (dd, J=3.2, 6.4 Hz, 1H), 7.87-7.82 (m, 1H), 7.58 (d, J=8.4 Hz, 1H), 7.51-7.45 (m, 2H), 7.42 (t, J=7.6 Hz, 1H), 7.15 (d, J=7.6 Hz, 1H), 4.39-4.27 (m, 2H), 4.12-4.05 (m, 3H), 3.60-3.26 (m, 6H), 3.14 (br t, J=7.6 Hz, 1H), 2.79 (br s, 2H), 2.74-2.65 (m, 1H), 2.53 (s, 3H), 2.39-2.28 (m, 1H), 2.05-2.00 (m, 1H), 1.92-1.70 (m, 4H), 1.58 (br d, J=4.0 Hz, 6H), 1.49 (s, 9H).

Step E: 4-(2,2-dimethylpiperazin-1-yl)-2-[[(2S)-1-methylpyrrolidin-2-yl]methoxy]-7-(1-naphthyl)-6,8-dihydro-5H-pyrido[3,4-d]pyrimidine The solution of tert-butyl 3,3-dimethyl-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (210 mg, 358 umol, 1 eq) and TFA (408 mg, 3.58 mmol, 265 uL, 10 eq) was stirred at 30° C. for 0.5 hour. The mixture was concentrated under vacuum to give 4-(2,2-dimethylpiperazin-1-yl)-2-[[(2S)-1-methylpyrrolidin-2-yl]methoxy]-7-(1-naphthyl)-6,8-dihydro-5H-pyrido[3,4-d]pyrimidine (210 mg, crude, TFA) as a brown oil which was used for next step without further purification.

Step F: 1-[3,3-dimethyl-4-[2-[[(2S)-1-methylpyrrolidin-2-yl]methoxy]-7-(1-naphthyl)-6,8-dihydro-5H-pyrido[3,4-d]pyrimidin-4-yl]piperazin-1-yl]prop-2-en-1-one To the solution of 4-(2,2-dimethylpiperazin-1-yl)-2-[[(2S)-1-methylpyrrolidin-2-yl]methoxy]-7-(1-naphthyl)-6,8-dihydro-5H-pyrido[3,4-d]pyrimidine (210 mg, crude, TFA) and TEA (531 mg, 5.24 mmol, 730 uL) in DCM (4 mL) was added prop-2-enoyl chloride (47.5 mg, 524 umol, 42.8 uL) at −40° C., the mixture was stirred at −40° C. for 0.5 hour. The mixture was quenched by water (2 mL). The mixture was diluted with EtOAc (5 mL) and extracted with EtOAc (10 mL). The organic layer was dried over anhydrous Na₂SO₄, filtered and concentrated under vacuum. The residue was purified by prep-HPLC (column: Gemini 150*25 5 u; mobile phase: [water (0.05% ammonia hydroxide v/v)-ACN]; B %: 73%-100%,12 min) to give title compound 1-[3,3-dimethyl-4-[2-[[(2S)-1-methylpyrrolidin-2-yl]methoxy]-7-(1-naphthyl)-6,8-dihydro-5H-pyrido[3,4-d]pyrimidin-4-yl]piperazin-1-yl]prop-2-en-1-one (EXAMPLE 354, 104 mg, 189 umol, 53% yield, 98.6% purity) as a white solid. LCMS [ESI, M+1]: 541.

¹H NMR (400 MHz, chloroform-d) δ=8.26-8.18 (m, 1H), 7.85 (dd, J=3.2, 6.4 Hz, 1H), 7.58 (d, J=8.0 Hz, 1H), 7.48 (dd, J=3.2, 6.4 Hz, 2H), 7.42 (t, J=7.6 Hz, 1H), 7.15 (br d, J=7.2 Hz, 1H), 6.65-6.52 (m, 1H), 6.48-6.33 (m, 1H), 5.79-5.70 (m, 1H), 4.37-4.26 (m, 2H), 4.21 (br t, J=5.6 Hz, 1H), 4.17-4.06 (m, 3H), 3.80 (s, 1H), 3.78-3.69 (m, 2H), 3.61 (s, 1H), 3.39 (br s, 2H), 3.13 (br t, J=7.6 Hz, 1H), 2.80 (br s, 2H), 2.73-2.65 (m, 1H), 2.52 (s, 3H), 2.37-2.28 (m, 1H), 2.09-1.99 (m, 1H), 1.94-1.68 (m, 3H), 1.62 (br s, 6H).

983
Example 355
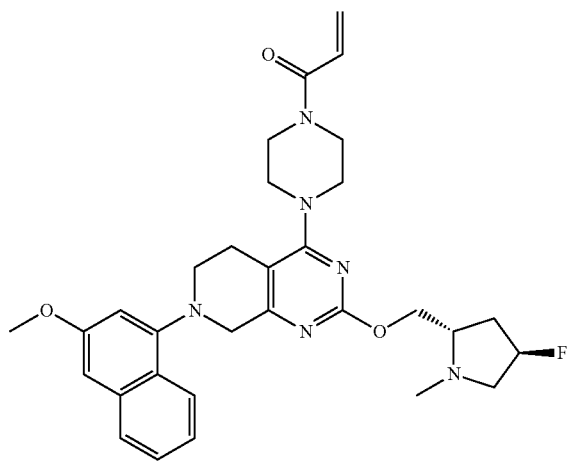 [SMILES: C=CC(=O)N1CCN(c2nc(OC[C@@H]3C[C@@H](F)CN3C)nc3c2CCN(c2cc(OC)cc4ccccc24)C3)CC1]
1-[4-[2-[[(2S,4R)-4-fluoro-1-methyl-pyrrolidin-2-yl]methoxy]-7-(3-methoxy-1-naphthyl)-6,8-dihydro-5H-pyrido[3,4-d]pyrimidin-4-yl]piperazin-1-yl]prop-2-en-1-one
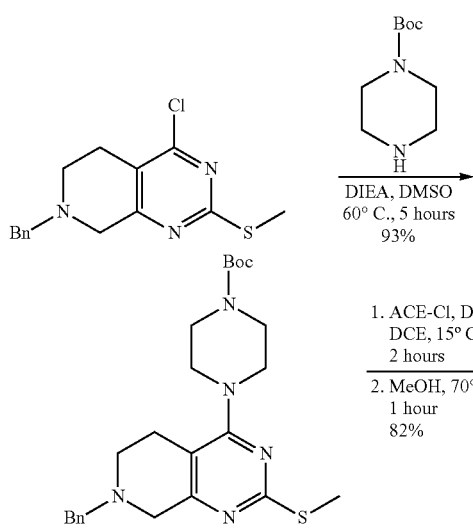
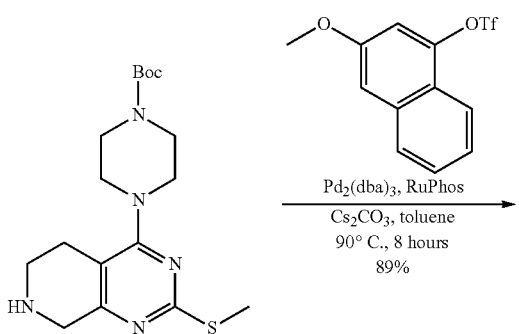
984
-continued
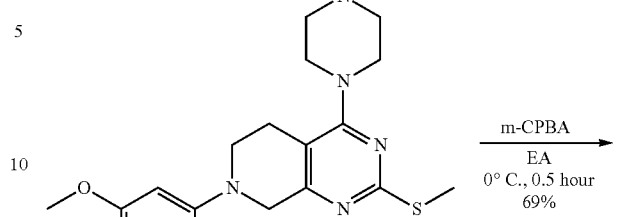
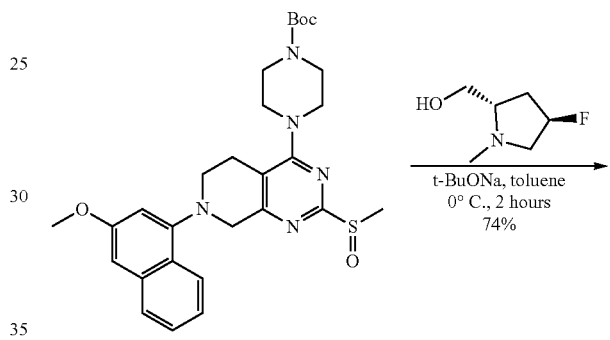
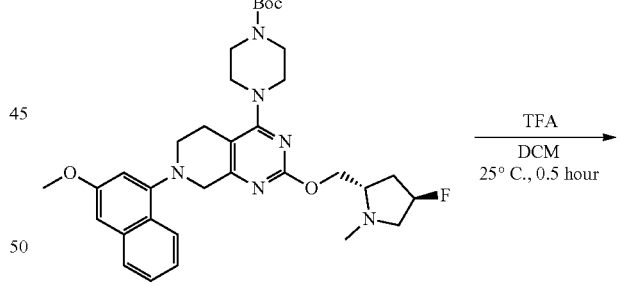
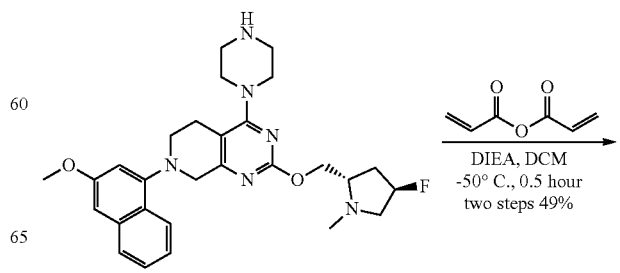

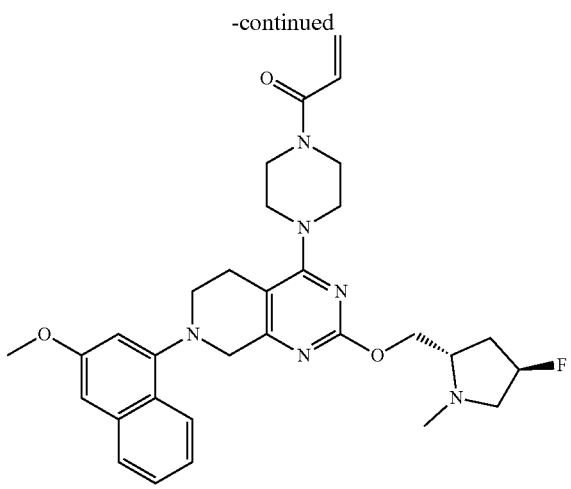

Step A: tert-butyl 4-(7-benzyl-2-methylsulfanyl-6,8-dihydro-5H-pyrido[3,4-d]pyrimidin-4-yl) piperazine-1-carboxylate. To a solution of 7-benzyl-4-chloro-2-methylsulfanyl-6,8-dihydro-5H-pyrido[3,4-d]pyrimidine (5.0 g, 16.4 mmol, 1.0 eq) and tert-butyl piperazine-1-carboxylate (4.57 g, 24.5 mmol, 1.50 eq) in DMSO (20.0 mL) was added DIEA (6.34 g, 49.1 mmol, 8.54 mL, 3.0 eq). The mixture was stirred at 60° C. for 5 hours. After completion, the mixture was added water (200 mL) and extracted with EA (200 mL×3). The organic layer was washed with brine (500 mL), dried over Na$_2$SO$_4$, filtered and concentrated. The obtained product was purified by column chromatography (SiO$_2$, PE:EA=50:1-5:1) to give tert-butyl 4-(7-benzyl-2-methylsulfanyl-6,8-dihydro-5H-pyrido[3,4-d]pyrimidin-4-yl) piperazine-1-carboxylate (7.0 g, 15.4 mmol, 93% yield). as light brown solid. LCMS [ESI, M+1]: 456.

$^1$H NMR (400 MHz, Chloroform-d) δ 7.40-7.27 (m, 5H), 3.68 (s, 2H), 3.58 (s, 2H), 3.54-3.48 (m, 4H), 3.47-3.38 (m, 4H), 2.65 (s, 4H), 1.48 (s, 9H).

Step B: tert-butyl 4-(2-methylsulfanyl-5,6,7,8-tetrahydropyrido[3,4-d]pyrimidin-4-yl)piperazine-1-carboxylate To a solution of tert-butyl 4-(7-benzyl-2-methylsulfanyl-6,8-dihydro-5H-pyrido[3,4-d]pyrimidin-4-yl)piperazine-1-carboxylate (7.0 g, 15.4 mmol, 1.0 eq) and DIEA (5.96 g, 46.1 mmol, 8.03 mL, 3.0 eq) in DCE (100 mL) was added 1-chloroethyl carbonochloridate (5.49 g, 38.4 mmol, 2.5 eq) at 0° C. The mixture was stirred at 15° C. for 2 hours. Then the mixture was concentrated. The residue was dissolved with MeOH (100 mL) and heated to 70° C., the reaction mixture was stirred at 70° C. for 1 hour. After completion, the mixture was concentrated under vacuum. The obtained product was purified by reversed phase flash column (C18, 0.1% FA in water, 0-50% MeCN) to give tert-butyl 4-(2-methylsulfanyl-5,6,7,8-tetrahydropyrido[3,4-d]pyrimidin-4-yl)piperazine-1-carboxylate (4.6 g, 12.6 mmol, 82% yield) as a yellow solid. LCMS [ESI, M+1]: 366.

Step C: To a solution of tert-butyl 4-(2-methylsulfanyl-5,6,7,8-tetrahydropyrido[3,4-d]pyrimidin-4-yl)piperazine-1-carboxylate (3.60 g, 9.85 mmol, 1.0 eq), (3-methoxy-1-naphthyl) trifluoromethanesulfonate (Intermediate 30, 7.54 g, 24.6 mmol, 2.50 eq) and RuPhos (919 mg, 1.97 mmol, 0.20 eq) and Cs$_2$CO$_3$ (9.63 g, 29.6 mmol, 3.0 eq) in toluene (30.0 mL) was added Pd$_2$(dba)$_3$ (1.35 g, 1.48 mmol, 0.15 eq). The mixture was degassed under vacuum and purged with N$_2$ 3 times. Then the mixture was stirred at 90° C. for 8 hours. After completion, the mixture was added water (50.0 mL) and extracted with EA (50.0 mL×3). The organic layer was dried over Na$_2$SO$_4$, filtered and concentrated. The obtained product was purified by column chromatography (SiO$_2$, PE:EA=20:1-EA:MeOH=10:1) to give tert-butyl 4-[7-(3-methoxy-1-naphthyl)-2-methylsulfanyl-6,8-dihydro-5H-pyrido[3,4-d]pyrimidin-4-yl]piperazine-1-carboxylate (4.60 g, 8.82 mmol, 89% yield) as yellow solid. LCMS [ESI, M+1]: 522.

Step D: tert-butyl 4-[7-(3-methoxy-1-naphthyl)-2-methylsulfinyl-6,8-dihydro-5H-pyrido[3,4-d]pyrimidin-4-yl]piperazine-1-carboxylate To a solution of tert-butyl 4-[7-(3-methoxy-1-naphthyl)-2-methylsulfanyl-6,8-dihydro-5H-pyrido[3,4-d]pyrimidin-4-yl]piperazine-1-carboxylate (3.80 g, 7.28 mmol, 1.0 eq) in EA (40.0 mL) was added m-CPBA (1.41 g, 6.56 mmol, 0.90 eq) at 0° C. The mixture was stirred at 0° C. for 0.5 hour. After completion, the mixture was quenched with saturated NaHSO$_3$ aqueous (30.0 mL) and extracted with EA (50.0 mL×3). The organic layer was dried over Na$_2$SO$_4$, filtered and concentrated. The obtained product was purified by reversed phase flash column (C18, 0.1% FA in water, 0-60% MeCN) to give tert-butyl 4-[7-(3-methoxy-1-naphthyl)-2-methylsulfinyl-6,8-dihydro-5H-pyrido[3,4-d]pyrimidin-4-yl]piperazine-1-carboxylate (2.70 g, 5.02 mmol, 69% yield) as yellow solid.

$^1$H NMR (400 MHz, Chloroform-d) δ 8.07 (d, J=8.4 Hz, 1H), 7.76 (d, J=8.0 Hz, 1H), 7.52-7.42 (m, 1H), 7.39-7.33 (m, 1H), 6.92 (d, J=2.0 Hz, 1H), 6.81 (d, J=2.0 Hz, 1H), 4.42 (br s, 2H), 3.93 (s, 3H), 3.61 (br d, J=4.0 Hz, 8H), 3.52-3.34 (m, 2H), 3.08-2.81 (m, 5H), 1.50 (s, 9H).

Step E: tert-butyl 4-[2-[[(2S,4R)-4-fluoro-1-methyl-pyrrolidin-2-yl]methoxy]-7-(3-methoxy-1-naphthyl)-6,8-dihydro-5H-pyrido[3,4-d]pyrimidin-4-yl]piperazine-1-carboxylate To a solution of tert-butyl 4-[7-(3-methoxy-1-naphthyl)-2-methylsulfinyl-6,8-dihydro-5H-pyrido[3,4-d]pyrimidin-4-yl]piperazine-1-carboxylate (800 mg, 1.49 mmol, 1.0 eq) and t-BuONa (286 mg, 2.98 mmol, 2.0 eq) in toluene (8.0 mL) was added [(2S,4R)-4-fluoro-1-methyl-pyrrolidin-2-yl] methanol (396 mg, 2.98 mmol, 2.0 eq). The mixture was stirred at 0° C. for 2 hours. After completion, the mixture was added water (10.0 mL) and extracted with EA (10.0 mL×3). The organic layer was dried over Na$_2$SO$_4$, filtered and concentrated. The obtained product was purified by reversed phase flash column (C18, 0.1% FA in water, 0-60% MeCN) to give tert-butyl 4-[2-[[(2S,4R)-4-fluoro-1-methyl-pyrrolidin-2-yl]methoxy]-7-(3-methoxy-1-naphthyl)-6,8-dihydro-5H-pyrido[3,4-d]pyrimidin-4-yl]piperazine-1-carboxylate (670 mg, 1.10 mmol, 74% yield) as yellow solid.

$^1$H NMR (400 MHz, Chloroform-d) δ=8.09 (d, J=8.4 Hz, 1H), 7.75 (d, J=8.0 Hz, 1H), 7.48-7.41 (m, 1H), 7.38-7.31 (m, 1H), 6.90 (d, J=2.0 Hz, 1H), 6.81 (d, J=2.4 Hz, 1H), 5.29-5.06 (m, 1H), 4.44 (dd, J=4.4, 10.8 Hz, 1H), 4.27-4.20 (m, 3H), 3.92 (s, 3H), 3.66-3.43 (m, 9H), 3.36 (br s, 2H), 3.11-2.99 (m, 1H), 2.85 (br s, 2H), 2.70-2.55 (m, 1H), 2.52 (s, 3H), 2.40-2.26 (m, 1H), 2.05-1.91 (m, 1H), 1.50 (s, 9H).

Step F. 2-[[(2S,4R)-4-fluoro-1-methyl-pyrrolidin-2-yl]methoxy]-7-(3-methoxy-1-naphthyl)-4-piperazin-1-yl-6,8-dihydro-5H-pyrido[3,4-d]pyrimidine To a solution of tert-butyl 4-[2-[[(2S,4R)-4-fluoro-1-methyl-pyrrolidin-2-yl]methoxy]-7-(3-methoxy-1-naphthyl)-6,8-dihydro-5H-pyrido[3,4-d]pyrimidin-4-yl]piperazine-1-carboxylate (650 mg, 1.07 mmol, 1.0 eq) in DCM (1.50 mL) was added TFA (2.39 g, 21.0 mmol, 1.55 mL, 19.6 eq). The mixture was stirred at 25° C. for 0.5 hour. After completion, the mixture was concentrated under vacuum. The product 2-[[(2S,4R)-4-fluoro-1-methyl-pyrrolidin-2-yl]methoxy]-7-(3-methoxy-1-naphthyl)-4-piperazin-1-yl-6,8-dihydro-5H-pyrido[3,4-d]pyrimidine (780 mg, crude, 2 TFA) as yellow oil. LCMS [ESI, M+1]: 507.

Step G: 1-[4-[2-[[(2S,4R)-4-fluoro-1-methyl-pyrrolidin-2-yl]methoxy]-7-(3-methoxy-1-naphthyl)-6,8-dihydro-5H-pyrido[3,4-d]pyrimidin-4-yl]piperazin-1-yl]prop-2-en-1-one To a solution of 2-[[(2S,4R)-4-fluoro-1-methyl-pyrrolidin-2-yl]methoxy]-7-(3-methoxy-1-naphthyl)-4-piperazin-1-yl-6,8-dihydro-5H-pyrido[3,4-d]pyrimidine (780 mg, 1.06 mmol, 1.0 eq, 2 TFA) and DIEA (1.65 g, 12.7 mmol, 2.22 mL, 12.0 eq) in DCM (8.0 mL) was added prop-2-enoyl prop-2-enoate (201 mg, 1.59 mmol, 1.50 eq) at −50° C. The mixture was stirred at −50° C. for 0.5 hour. After completion, the mixture was quenched with MeOH (1 mL), then concentrated under vacuum. The obtained product was purified by prep-HPLC (column: Gemini 150*25 5 u; mobile phase: [water (0.05% ammonia hydroxide v/v)-ACN]; B %: 46%-76%, 12 min) to give title compound 1-[4-[2-[[(2S,4R)-4-fluoro-1-methyl-pyrrolidin-2-yl]methoxy]-7-(3-methoxy-1-naphthyl)-6,8-dihydro-5H-pyrido[3,4-d]pyrimidin-4-yl]piperazin-1-yl]prop-2-en-1-one (EXAMPLE 355, 300 mg, 528 umol, two steps 49% yield, 98% purity) as white solid. LCMS [ESI, M+1]: 561.

¹H NMR (400 MHz, Chloroform-d) δ 8.10 (d, J=8.4 Hz, 1H), 7.75 (d, J=8.0 Hz, 1H), 7.49-7.42 (m, 1H), 7.40-7.32 (m, 1H), 6.91 (d, J=2.4 Hz, 1H), 6.81 (d, J=2.4 Hz, 1H), 6.61 (dd, J=10.8, 16.8 Hz, 1H), 6.36 (dd, J=2.0, 16.8 Hz, 1H), 5.77 (dd, J=1.6, 10.4 Hz, 1H), 5.28-5.07 (m, 1H), 4.44 (dd, J=4.8, 11.2 Hz, 1H), 4.30-4.19 (m, 3H), 3.93 (s, 3H), 3.84 (br s, 2H), 3.72 (br s, 2H), 3.65-3.50 (m, 5H), 3.37 (br s, 2H), 3.10-3.01 (m, 1H), 2.87 (br s, 2H), 2.70-2.55 (m, 1H), 2.52 (s, 3H), 2.42-2.26 (m, 1H), 2.07-1.90 (m, 1H).

Example 356

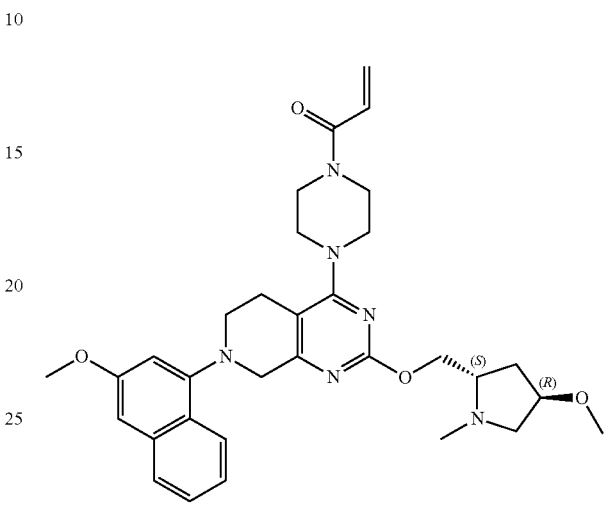

1-[4-[2-[[(2S,4R)-4-methoxy-1-methyl-pyrrolidin-2-yl]methoxy]-7-(3-methoxy-1-naphthyl)-6,8-dihydro-5H-pyrido[3,4-d]pyrimidin-4-yl]piperazin-1-yl]prop-2-en-1-one

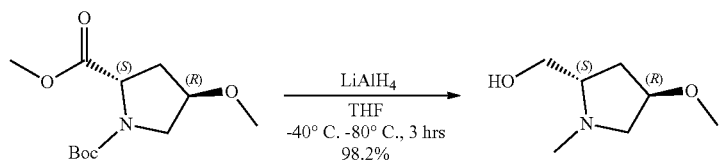

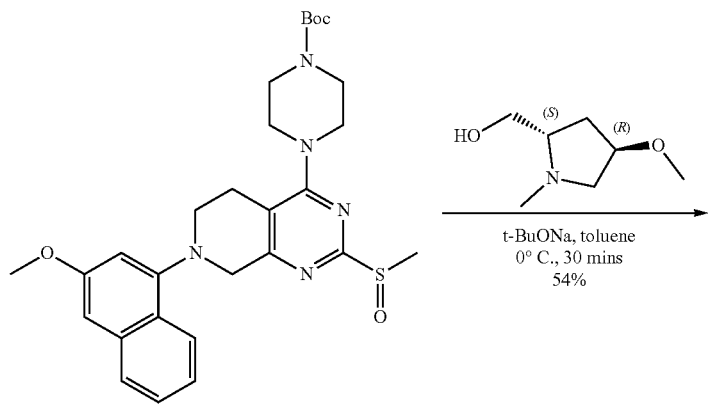

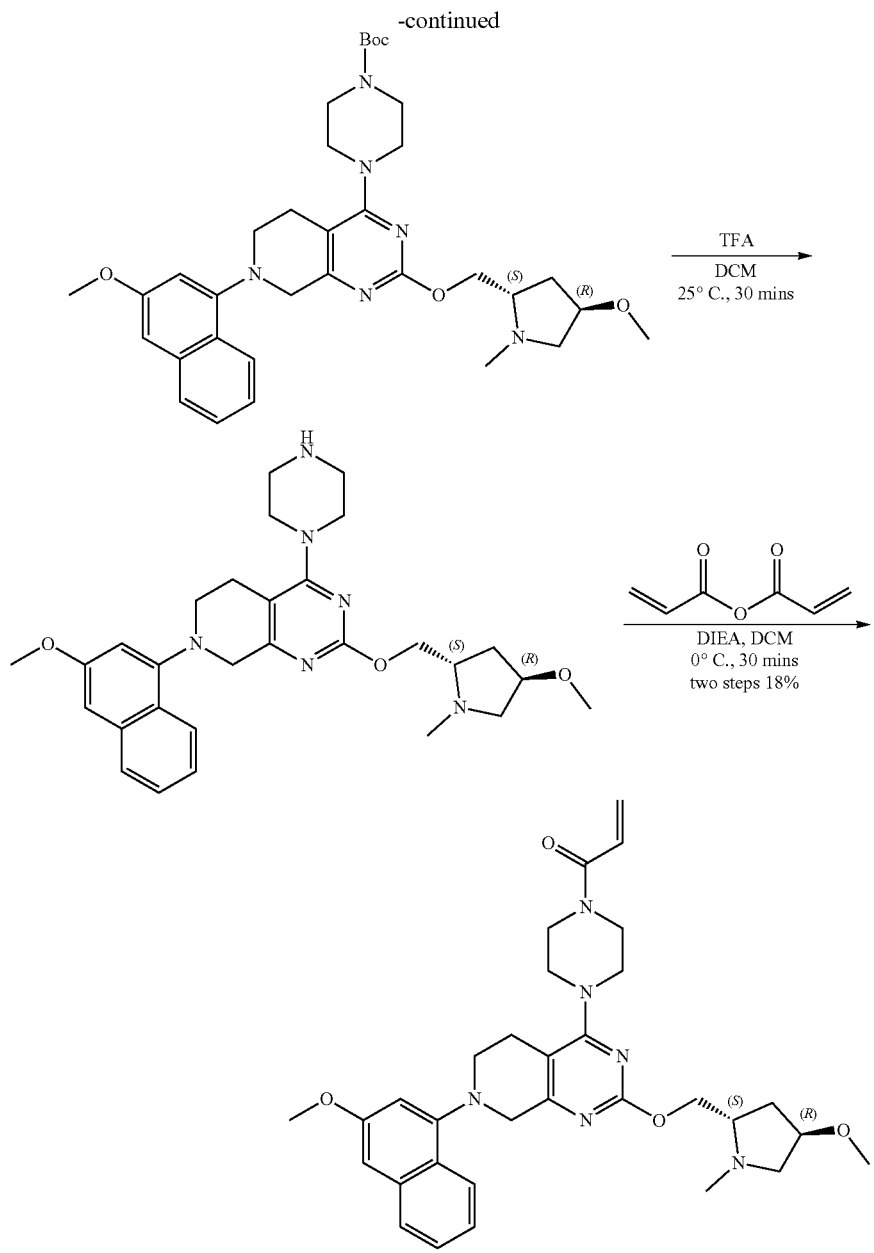

Step A: [(2S,4R)-4-methoxy-1-methyl-pyrrolidin-2-yl]methanol

To a solution of O1-tert-butyl O2-methyl (2S,4R)-4-methoxypyrrolidine-1,2-dicarboxylate (1.8 g, 6.94 mmol, 1.0 eq) in THF (30.0 mL) was added LiAlH$_4$ (790 mg, 20.8 mmol, 3.0 eq). The mixture was stirred at −40° C. for 1 hour. Then the mixture stirred 80° C. for 2 hours under N$_2$ atmosphere. The reaction mixture was quenched with saturated Na$_2$SO$_4$ aqueous solution (6.0 mL). Then the mixture was filtered and the filter was concentrated. Compound [(2S,4R)-4-methoxy-1-methyl-pyrrolidin-2-yl]methanol (1.1 g, 6.82 mmol, 98% yield, 90% purity) was obtained as a colorless oil and used to next step without further purification.

$^1$H NMR (400 MHz, Chloroform-d) δ 3.90-3.82 (m, 1H), 3.66 (dd, J=3.2 Hz, 10.8 Hz, 1H), 3.46-3.37 (m, 2H), 3.28 (s, 3H), 2.77-2.65 (m, 1H), 2.64-2.57 (m, 1H), 2.35-2.30 (m, 4H), 2.11-2.01 (m, 1H), 1.90-1.79 (m, 1H).

Step B: tert-butyl 4-[2-[[(2S,4R)-4-methoxy-1-methyl-pyrrolidin-2-yl]methoxy]-7-(3-methoxy-1-naphthyl)-6,8-dihydro-5H-pyrido[3,4-d]pyrimidin-4-yl]piperazine-1-carboxylate A mixture of tert-butyl 4-[7-(3-methoxy-1-naphthyl)-2-methylsulfinyl-6,8-dihydro-5H-pyrido[3,4-d]pyrimidin-4-yl]piperazine-1-carboxylate (800 mg, 1.49 mmol, 1.0 eq), [(2S,4R)-4-methoxy-1-methyl-pyrrolidin-2-yl]methanol (454 mg, 3.12 mmol, 2.1 eq), t-BuONa (286 mg, 2.98 mmol, 2.0 eq) in toluene (5.0 mL) was degassed and purged with N$_2$ for 3 times, and then the mixture was stirred at 0° C. for 30 mins under N$_2$ atmosphere. After completion, the reaction mixture was added water (15.0 mL), extracted with ethyl acetate (3×20.0 mL). Combine extracts were washed with brine (50.0 mL), dried with Na₂SO₄, the solvent was then removed under vacuum. The residue was purified by reversed phase flash HPLC [C18, 0.1% FA in water, 0-60% MeCN]. The obtained product was adjusted with saturated NaHCO₃ aqueous to pH ~8, then concentrated, the aqueous was extracted with EA (3×50.0 mL), the combined organic layer was dried over Na₂SO₄, filtered and concentrated. Compound tert-butyl 4-[2-[[(2S,4R)-4-methoxy-1-methyl-pyrrolidin-2-yl]methoxy]-7-(3-methoxy-1-naphthyl)-6,8-dihydro-5H-pyrido[3,4-d]pyrimidin-4-yl]piperazine-1-carboxylate (500 mg, 808 umol, 54% yield, 100% purity) was obtained as a yellow solid. LCMS [ESI, M+1]: 619.

Step C: 2-[[(2S,4R)-4-methoxy-1-methyl-pyrrolidin-2-yl]methoxy]-7-(3-methoxy-1-naphthyl)-4-piperazin-1-yl-6,8-dihydro-5H-pyrido[3,4-d]pyrimidine To a solution of tert-butyl 4-[2-[[(2S,4R)-4-methoxy-1-methyl-pyrrolidin-2-yl]methoxy]-7-(3-methoxy-1-naphthyl)-6,8-dihydro-5H-pyrido[3,4-d]pyrimidin-4-yl]piperazine-1-carboxylate (450 mg, 727 umol, 1.0 eq) in DCM (6.0 mL) was added TFA (6.93 g, 60.8 mmol, 4.50 mL, 83.6 eq). The mixture was stirred at 25° C. for 30 mins. After completion, the organic solvent was removed under vacuum to give 2-[[(2S,4R)-4-methoxy-1-methyl-pyrrolidin-2-yl]methoxy]-7-(3-methoxy-1-naphthyl)-4-piperazin-1-yl-6,8-dihydro-5H-pyrido[3,4-d]pyrimidine (540 mg, crude, 2TFA) as yellow oil. The crude product was used into the next step without further purification. LCMS [ESI, M+1]: 519.

Step D: 1-[4-[2-[[(2S,4R)-4-methoxy-1-methyl-pyrrolidin-2-yl] methoxy]-7-(3-methoxy-1-naphthyl)-6,8-dihydro-5H-pyrido[3,4-d]pyrimidin-4-yl] piperazin-1-yl]prop-2-en-1-one To a solution of 2-[[(2S,4R)-4-methoxy-1-methyl-pyrrolidin-2-yl]methoxy]-7-(3-methoxy-1-naphthyl)-4-piperazin-1-yl-6,8-dihydro-5H-pyrido[3,4-d]pyrimidine (540 mg, 2TFA) in DCM (6.0 mL) was dropwise added prop-2-enoyl prop-2-enoate (130 mg, 1.03 mmol) and DIEA (800 mg, 6.19 mmol, 1.08 mL) under N₂ atmosphere. The mixture was stirred at 0° C. for 30 min. After completion, the reaction was quenched with methanol (10.0 mL) and the mixture was removed under vacuum. The residue was purified by prep-HPLC (column: Phenomenex Gemini 150*25 mm*10 um; mobile phase: [water (0.05% ammonia hydroxide v/v)-ACN]; B %: 48%-78%, 12 min) and under lyophilization. Title compound 1-[4-[2-[[(2S,4R)-4-methoxy-1-methyl-pyrrolidin-2-yl] methoxy]-7-(3-methoxy-1-naphthyl)-6,8-dihydro-5H-pyrido[3,4-d]pyrimidin-4-yl]piperazin-1-yl]prop-2-en-1-one (EXAMPLE 356, 112 mg, 196 umol, 99% purity, 18% yield) was obtained as white solid. LCMS [ESI, M+1]: 573.

¹H NMR (400 MHz, Chloroform-d) δ 8.09 (d, J=8.4 Hz, 1H), 7.75 (d, J=8.0 Hz, 1H), 7.48-7.44 (m, 1H), 7.38-7.34 (m, 1H), 6.91 (d, J=2.4 Hz, 1H), 6.81 (d, J=2.4 Hz, 1H), 6.61 (dd, J=10.4 Hz, 16.8 Hz, 1H), 6.35 (dd, J=2.0 Hz, 16.8 Hz, 1H), 5.76 (dd, J=1.6 Hz, 9.6 Hz, 1H), 4.41 (dd, J=4.8 Hz, 10.8 Hz, 1H), 4.24 (s, 2H), 4.22-4.16 (m, 1H), 4.00-3.94 (m, 1H), 3.92 (s, 3H), 3.83-3.67 (m, 4H), 3.62-3.48 (m, 4H), 3.47-3.42 (m, 1H), 3.40-3.33 (m, 2H), 3.30 (s, 3H), 2.94-2.82 (m, 3H), 2.47 (s, 3H), 2.33 (dd, J=6.0 Hz, 10.0 Hz, 1H), 2.12-2.04 (m, 1H), 2.01-1.93 (m, 1H).

Example 357

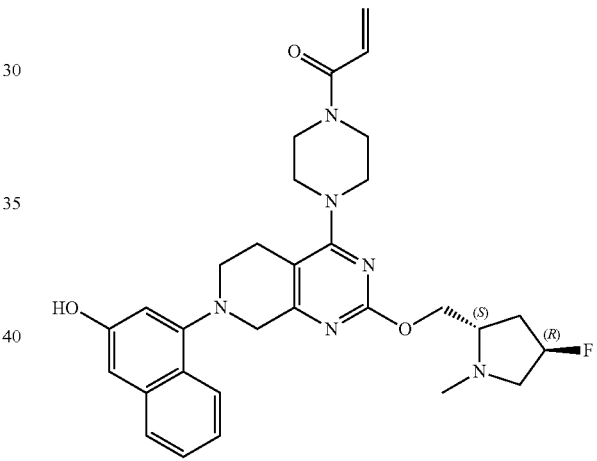

1-[4-[2-[[(2S,4R)-4-fluoro-1-methyl-pyrrolidin-2-yl] methoxy]-7-(3-hydroxy-1-naphthyl)-6,8-dihydro-5H-pyrido[3,4-d]pyrimidin-4-yl]piperazin-1-yl]prop-2-en-1-one

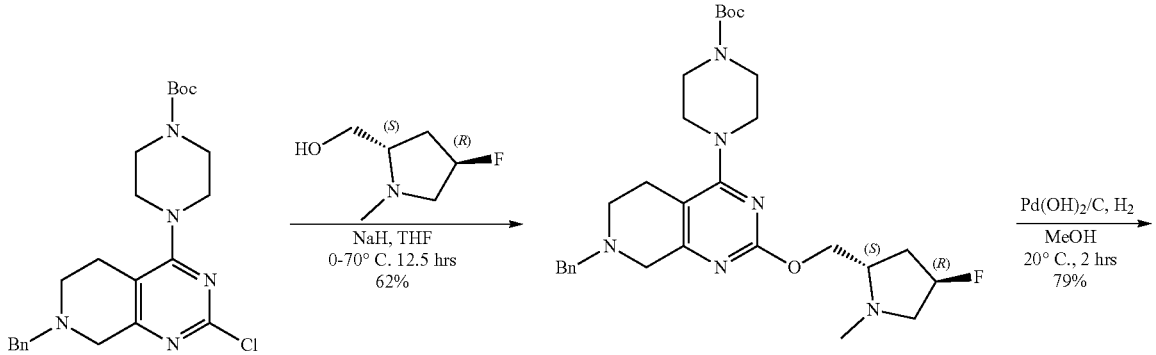

993 994
-continued
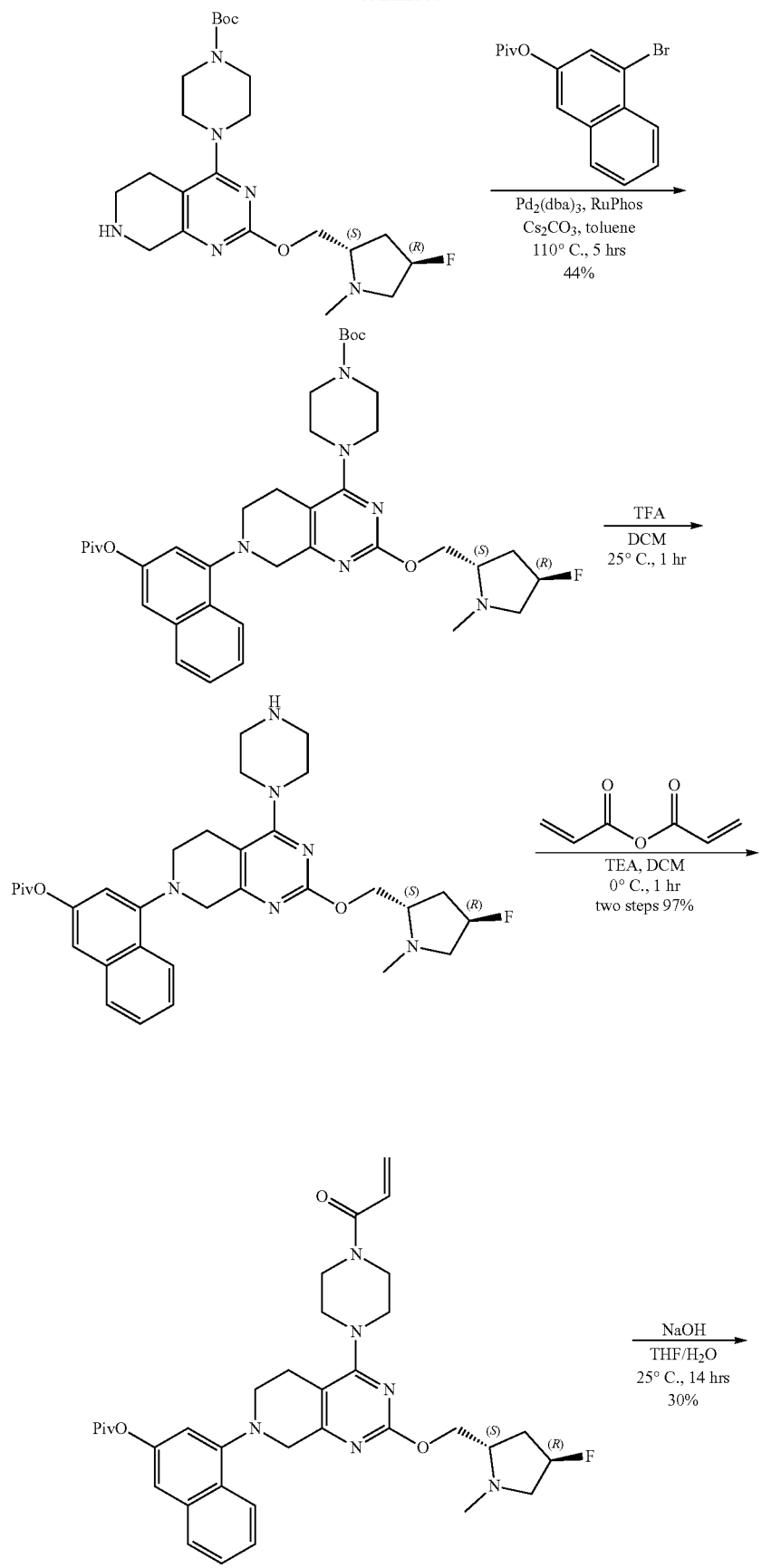

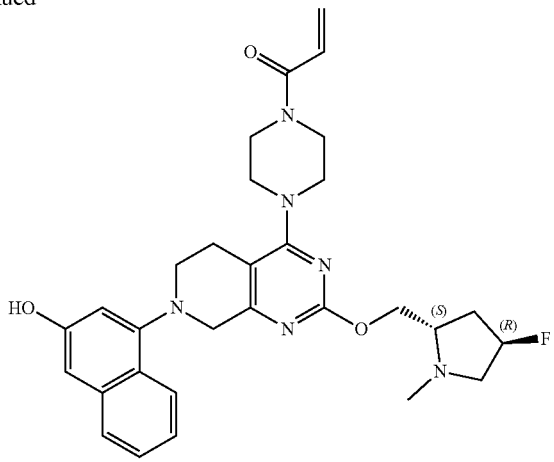

Step A: tert-butyl 4-[7-benzyl-2-[[(2S,4R)-4-fluoro-1-methyl-pyrrolidin-2-yl]methoxy]-6,8-dihydro-5H-pyrido[3,4-d]pyrimidin-4-yl]piperazine-1-carboxylate To a solution of [(2S,4R)-4-fluoro-1-methyl-pyrrolidin-2-yl]methanol (631 mg, 4.74 mmol, 3.76 eq) in THF (7.0 mL) was added NaH (126 mg, 3.16 mmol, 60% purity, 2.51 eq) at 0° C. Then the mixture was stirred at 0° C. for 0.5 hr. Then tert-butyl 4-(7-benzyl-2-chloro-6,8-dihydro-5H-pyrido[3,4-d]pyrimidin-4-yl)piperazine-1-carboxylate (700 mg, 1.26 mmol, 1.0 eq) was added to the above mixture. After addition, the mixture was stirred at 70° C. for 12 hrs. After completion, the mixture was quenched with saturated NH₄Cl aqueous (15.0 mL) and extracted with EA (3×20.0 mL). The organic layer was dried over Na₂SO₄, filtered and concentrated under reduced pressure to give a residue. The residue was purified by column chromatography (SiO₂, Dichloromethane:Methanol=20:1 to 10:1) to give tert-butyl 4-[7-benzyl-2-[[(2S,4R)-4-fluoro-1-methyl-pyrrolidin-2-yl]methoxy]-6,8-dihydro-5H-pyrido[3,4-d]pyrimidin-4-yl]piperazine-1-carboxylate (530 mg, 980 umol, 78% yield) as yellow oil. LCMS [ESI, M+1]: 541.

$^1$H NMR (400 MHz, Chloroform-d) δ 7.24-7.13 (m, 5H), 5.08-4.91 (m, 1H), 4.23 (dd, J=4.4 Hz, 10.8 Hz, 1H), 4.04 (dd, J=6.0 Hz, 10.8 Hz, 1H), 3.53 (s, 2H), 3.45-3.42 (m, 2H), 3.38-3.33 (m, 5H), 3.31-3.27 (m, 4H), 2.90-2.84 (m, 1H), 2.52-2.46 (m, 3H), 2.35 (s, 3H), 2.21-2.09 (m, 1H), 1.87-1.73 (m, 3H), 1.34 (s, 9H).

Step B: tert-butyl 4-[2-[[(2S,4R)-4-fluoro-1-methyl-pyrrolidin-2-yl]methoxy]-5,6,7,8-tetrahydropyrido[3,4-d]pyrimidin-4-yl]piperazine-1-carboxylate To a solution of tert-butyl 4-[7-benzyl-2-[[(2S,4R)-4-fluoro-1-methyl-pyrrolidin-2-yl]methoxy]-6,8-dihydro-5H-pyrido[3,4-d]pyrimidin-4-yl]piperazine-1-carboxylate (480 mg, 887 umol, 1 eq) in MeOH (6.0 mL) was added Pd(OH)₂/C (270 mg, 10% purity) under N₂. The suspension was degassed under vacuum and purged with H₂ several times. The mixture was stirred under H₂ (15 Psi) at 20° C. for 2 hours. After completion, the mixture was filtered and concentrated. The residue was purified by column chromatography (SiO₂, EA/MeOH=20:1 to 10:1). The product tert-butyl 4-[2-[[(2S,4R)-4-fluoro-1-methyl-pyrrolidin-2-yl]methoxy]-5,6,7,8-tetrahydropyrido[3,4-d]pyrimidin-4-yl]piperazine-1-carboxylate (350 mg, 706 umol, 79% yield, 91% purity) was obtained as yellow oil. LCMS [ESI, M+1]:451.

Step C: To a mixture of tert-butyl 4-[2-[[(2S,4R)-4-fluoro-1-methyl-pyrrolidin-2-yl]methoxy]-5,6,7,8-tetrahydropyrido[3,4-d]pyrimidin-4-yl]piperazine-1-carboxylate (280 mg, 621 umol, 1.0 eq), Pd₂(dba)₃ (85.3 mg, 93.2 umol, 0.15 eq), RuPhos (58.0 mg, 124.3 umol, 0.2 eq) and Cs₂CO₃ (404 mg, 1.24 mmol, 2.0 eq) in toluene (10.0 mL) was added (4-bromo-2-naphthyl) 2,2-dimethylpropanoate (Intermediate 54, 572 mg, 1.86 mmol, 3.0 eq). The mixture was stirred at 110° C. for 5 hrs under N₂. The mixture was quenched with water (15.0 mL) and extracted with EA (3×20.0 mL). The organic layer was dried over Na₂SO₄, filtered and concentrated under reduced pressure to give a residue. The residue was purified by reversed phase flash HPLC ($^{18}$C, 0.1% FA in water, 0-70% MeCN). The obtained product was adjusted with saturated NaHCO₃ aqueous to pH ~8, then concentrated, the aqueous was extracted with EA (3×40.0 mL), the combined organic layer was dried over Na₂SO₄, filtered and concentrated. Compound tert-butyl 4-[7-[3-(2,2-dimethylpropanoyloxy)-1-naphthyl]-2-[[(2S,4R)-4-fluoro-1-methyl-pyrrolidin-2-yl]methoxy]-6,8-dihydro-5H-pyrido[3,4-d]pyrimidin-4-yl]piperazine-1-carboxylate (190 mg, 272 umol, 44% yield, 97% purity) was obtained as a yellow oil. LCMS [ESI, M+1]: 677.

Step D: [4-[2-[[(2S,4R)-4-fluoro-1-methyl-pyrrolidin-2-yl]methoxy]-4-piperazin-1-yl-6,8-dihydro-5H-pyrido[3,4-d]pyrimidin-7-yl]-2-naphthyl]-2,2-dimethylpropanoate To a mixture of tert-butyl 4-[7-[3-(2,2-dimethyl propanoyloxy)-1-naphthyl]-2-[[(2S,4R)-4-fluoro-1-methyl-pyrrolidin-2-yl]methoxy]-6,8-dihydro-5H-pyrido[3,4-d]pyrimidin-4-yl]piperazine-1-carboxylate (110 mg, 162 umol, 1.0 eq) in DCM (1.5 mL) was added TFA (2.31 g, 20.2 mmol, 1.5 mL, 124 eq) in portions at 25° C. under N₂. The mixture was stirred at 25° C. for 1 hr. After completion, the reaction mixture was concentrated to give [4-[2-[[(2S,4R)-4-fluoro-1-methyl-pyrrolidin-2-yl]methoxy]-4-piperazin-1-yl-6,8-dihydro-5H-pyrido[3,4-d]pyrimidin-7-yl]-2-naphthyl]-2,2-dimethylpropanoate (200 mg, crude, 2TFA) as yellow solid, which was used into the next step without further purification. LCMS [ESI, M+1]: 577.

Step E: [4-[2-[[(2S,4R)-4-fluoro-1-methyl-pyrrolidin-2-yl]methoxy]-4-(4-prop-2-enoylpiperazin-1-yl)-6,8-dihydro-5H-pyrido[3,4-d]pyrimidin-7-yl]-2-naphthyl]-2,2-dimethylpropanoate To a mixture of [4-[2-[[(2S,4R)-4-fluoro-1-methyl-pyrrolidin-2-yl]methoxy]-4-piperazin-1-yl-6,8-dihydro-5H-pyrido[3,4-d]pyrimidin-7-yl]-2-naphthyl]-2,2-dimethylpropanoate (200 mg, 2TFA) and TEA (493 mg, 4.87 mmol, 678 uL) in DCM (2.0 mL) was added prop-2-enoyl prop-2-enoate (40.9 mg, 324 umol) in portions at 0° C. under $N_2$. The mixture was stirred at 0° C. for 1 hr. After completion, the reaction mixture was quenched by MeOH (3.0 mL) at 0° C., and then concentrated under reduced pressure to give a residue. The residue was purified by column chromatography ($SiO_2$, EA/MeOH=20:1 to 10:1). Compound [4-[2-[[(2S,4R)-4-fluoro-1-methyl-pyrrolidin-2-yl]methoxy]-4-(4-prop-2-enoylpiperazin-1-yl)-6,8-dihydro-5H-pyrido[3,4-d]pyrimidin-7-yl]-2-naphthyl]-2,2-dimethylpropanoate (100 mg, 153 umol, 97% purity) was obtained as a yellow oil. LCMS [ESI, M+1]:631.

Step F: 1-[4-[2-[[(2S,4R)-4-fluoro-1-methyl-pyrrolidin-2-yl]methoxy]-7-(3-hydroxy-1-naphthyl)-6,8-dihydro-5H-pyrido[3,4-d]pyrimidin-4-yl]piperazin-1-yl]prop-2-en-1-one A mixture of [4-[2-[[(2S,4R)-4-fluoro-1-methyl-pyrrolidin-2-yl]methoxy]-4-(4-prop-2-enoylpiperazin-1-yl)-6,8-dihydro-5H-pyrido[3,4-d]pyrimidin-7-yl]-2-naphthyl]-2,2-dimethylpropanoate (39.0 mg, 61.8 umol, 1.0 eq) and NaOH (61.8 mg, 1.55 mmol, 25.0 eq) in THF (1.5 mL) and $H_2O$ (1.5 mL) was stirred at 25° C. for 14 hours. After completion, the reaction mixture was quenched by water (10.0 mL) and then extracted with EA (3×15.0 mL). The organic layer was dried over $Na_2SO_4$, filtered and concentrated under reduced pressure to give a residue. The residue was purified by prep-HPLC (column: Phenomenex Gemini 150*25 mm*10 um; mobile phase: [water (0.05% ammonia hydroxide v/v)-ACN]; B: 38%-68%, 12 min) and lyophilization. Title compound 1-[4-[2-[[(2S,4R)-4-fluoro-1-methyl-pyrrolidin-2-yl]methoxy]-7-(3-hydroxy-1-naphthyl)-6,8-dihydro-5H-pyrido[3,4-d]pyrimidin-4-yl]piperazin-1-yl]prop-2-en-1-one (EXAMPLE 357, 10.1 mg, 18.4 umol, 30% yield, 99% purity) was obtained as a yellow solid. LCMS [ESI, M+1]: 547.

SFC Conditions: 100% ee.

$^1$H NMR (400 MHz, Chloroform-d) δ 8.04 (d, J=8.4 Hz, 1H), 7.65 (d, J=8.4 Hz, 1H), 7.42 (t, J=7.2 Hz, 1H), 7.30-7.34 (m, 1H), 6.88 (d, J=1.6 Hz, 1H), 6.72 (d, J=2.0 Hz, 1H), 6.60 (dd, J=10.4 Hz, 16.8 Hz, 1H), 6.37 (dd, J=1.6 Hz, 16.8 Hz, 1H), 5.79 (dd, J=2.0 Hz, 10.2 Hz, 1H), 5.28-5.14 (m, 1H), 4.46 (dd, J=4.8 Hz, 11.2 Hz, 1H), 4.32 (dd, J=5.2 Hz, 11.2 Hz, 1H), 4.18 (s, 2H), 3.82-3.68 (m, 2H), 3.66-3.55 (m, 4H), 3.52-3.42 (m 4H), 3.35-3.21 (m, 2H), 3.17-3.10 (m, 1H), 2.82-2.68 (m, 2H), 2.63-2.74 (m, 1H), 2.61 (s, 3H), 2.40-2.25 (m, 1H), 2.13-1.94 (m, 1H).

Example 358

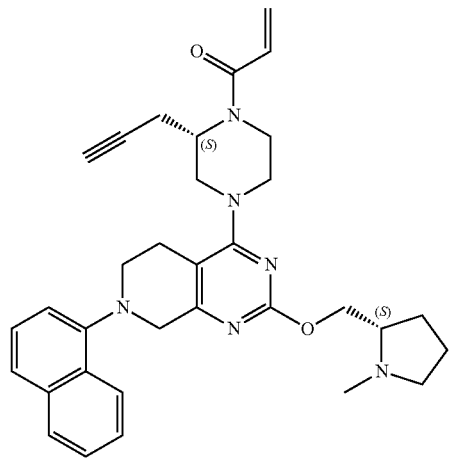

1-[(2S)-4-[2-[[(2S)-1-methylpyrrolidin-2-yl]methoxy]-7-(1-naphthyl)-6,8-dihydro-5H-pyrido[3,4-d]pyrimidin-4-yl]-2-prop-2-ynyl-piperazin-1-yl]prop-2-en-1-one

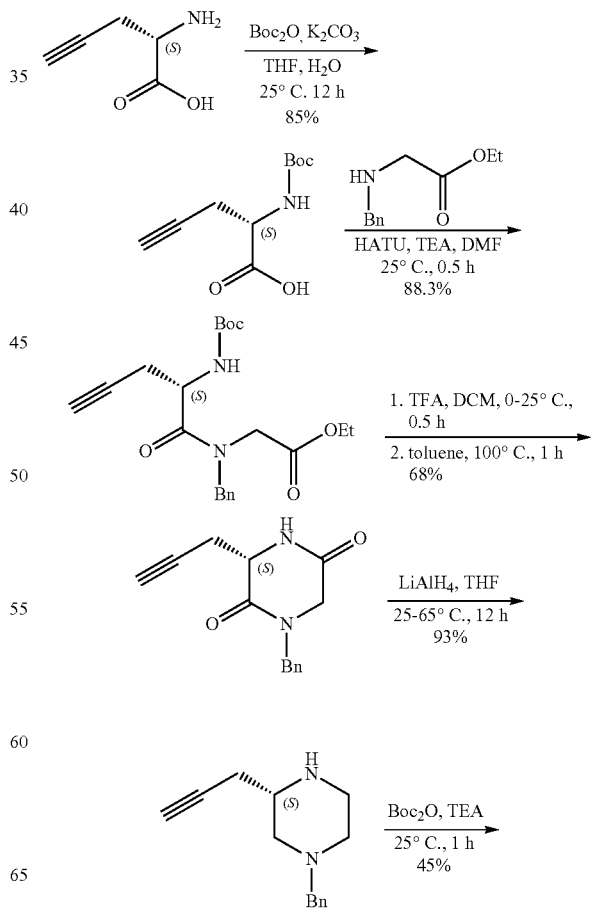

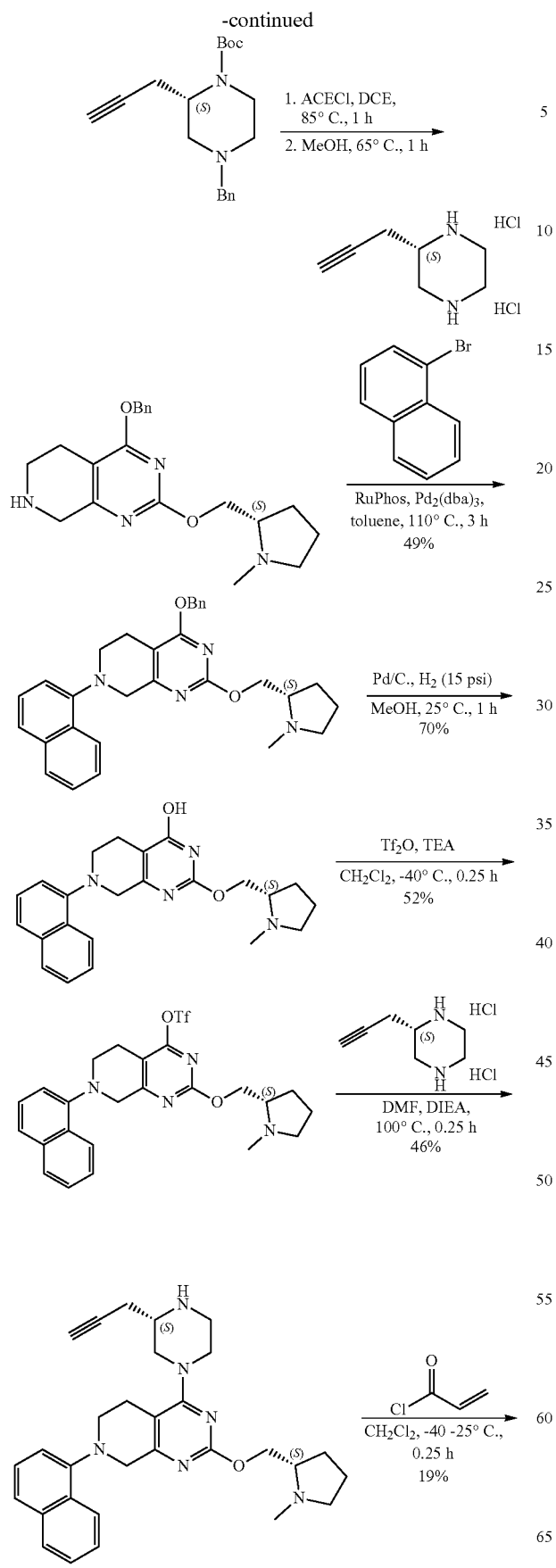

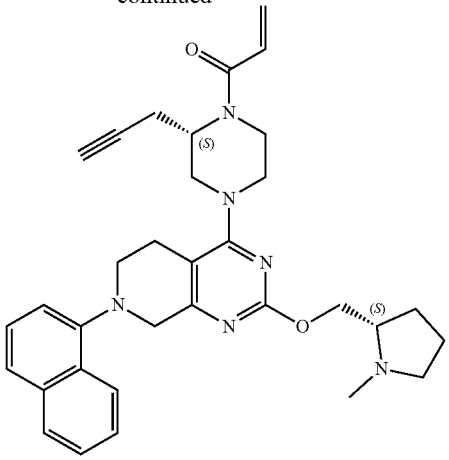

Step A:
(2S)-2-(tert-butoxycarbonylamino)pent-4-ynoic acid

To a suspension of (2S)-2-aminopent-4-ynoic acid (5 g, 44.2 mmol, 1 eq) in THF (15 mL) was added H₂O (15 mL), K₂CO₃ (18.3 g, 133 mmol, 3 eq) and Boc₂O (11.1 g, 50.8 mmol, 11.7 mL, 1.15 eq). Additional water was added to produce a solution which was stirred for 12 hours at 25° C. The organic solvent was then evaporated and the aqueous solution was washed with t-butyl methyl ether, then acidified to pH=3 with 1N HCl acid. The solution was extracted with ethyl acetate (2×100 mL). The solvent was evaporated to give (2S)-2-(tert-butoxycarbonylamino)pent-4-ynoic acid (8 g, 37.5 mmol, 85% yield) as a colorless oil used without further purification. LCMS [ESI, M+1]: 589.

$^1$H NMR (400 MHz, chloroform-d) δ=7.76 (br d, J=8.4 Hz, 1H), 7.62 (t, J=7.6 Hz, 1H), 7.53 (d, J=7.2 Hz, 1H), 7.45 (td, J=8.0, 13.2 Hz, 1H), 7.34 (t, J=7.6 Hz, 1H), 7.26-7.18 (m, 1H), 5.10 (br s, 1H), 4.49-4.33 (m, 2H), 4.21-4.01 (m, 3H), 3.96-3.79 (m, 2H), 3.60 (br d, J=6.8 Hz, 1H), 3.44 (br d, J=13.6 Hz, 1H), 3.32-2.97 (m, 5H), 2.88-2.53 (m, 4H), 2.48 (d, J=2.8 Hz, 3H), 2.29 (br d, J=8.8 Hz, 1H), 2.11-2.00 (m, 1H), 1.87-1.71 (m, 3H).

Step B: ethyl 2-[benzyl-[(2S)-2-(tert-butoxycarbonylamino)pent-4-ynoyl] amino] acetate To a solution of (2S)-2-(tert-butoxycarbonylamino)pent-4-ynoic acid (7.75 g, 36.4 mmol, 1 eq), ethyl 2-(benzylamino)acetate (7.02 g, 36.4 mmol, 1 eq) and HATU (16.6 g, 43.5 mmol, 1.20 eq) in DMF (50 mL) was added TEA (7.35 g, 72.7 mmol, 10.1 mL, 2.00 eq) at 25° C. The mixture was stirred at 25° C. for 0.5 h. The mixture was diluted with ethyl acetate (150 mL) and washed with water (3×200 mL) and brine (1×100 mL). The separated organic layer was washed with water (1×100 mL) and brine (1×100 mL), dried over sodium sulfate, filtered and concentrated under vacuum. The residue was used to next step without further purification. Compound ethyl 2-[benzyl-[(2S)-2-(tert-butoxycarbonylamino)pent-4-ynoyl]amino]acetate (13.7 g, 32.1 mmol, 88.3% yield, 91% purity) was obtained as red oil which become to red solid as standing at 25° C. for 16 hours. LCMS [ESI, M-99]: 289.

Step C: (3S)-1-benzyl-3-prop-2-ynyl-piperazine-2,5-dione

To a solution of ethyl 2-[benzyl-[(2S)-2-(tert-butoxycarbonylamino) pent-4-ynoyl]amino]acetate (11.7 g, 30.1 mmol, 1 eq) in DCM (40 mL) was added TFA (46.2 g, 405 mmol, 30 mL, 13.5 eq) at 0° C. and the mixture was stirred at 25° C. for 0.5 hour. The mixture was concentrated under vacuum and toluene (30 mL) was added. After stirred at 100° C. for 1 hour, the mixture was concentrated under vacuum. The residue was dissolved into ethyl acetate (200 mL) and basified with saturated aqueous sodium carbonate solution to pH=8. The separated organic layer was washed with water (1×200 mL) and brine (1×100 mL), dried over sodium sulfate, filtered and concentrated under vacuum. The residue was triturated with (ethyl acetate/petroleum ether 1/5, 100 mL) and the precipitate was filtered. The filter cake was dried under vacuum. Compound (3S)-1-benzyl-3-prop-2-ynyl-piperazine-2,5-dione (5 g, 20.5 mmol, 68% yield, 99.5% purity) was obtained as a white solid. LCMS [ESI, M+1]: 243.

$^1$H NMR (400 MHz, chloroform-d) δ=7.46-7.20 (m, 5H), 6.59 (br s, 1H), 4.76 (d, J=14.4 Hz, 1H), 4.50 (d, J=14.4 Hz, 1H), 4.20 (br d, J=4.4 Hz, 1H), 4.04-3.90 (m, 1H), 3.89-3.76 (m, 1H), 2.95-2.69 (m, 2H), 2.05 (t, J=2.8 Hz, 1H).

Step D: (3S)-1-benzyl-3-prop-2-ynyl-piperazine

To a mixture of (3S)-1-benzyl-3-prop-2-ynyl-piperazine-2,5-dione (5.00 g, 20.6 mmol, 1.00 eq) in THF (50.0 mL) was added LiAlH$_4$ (3.13 g, 82.6 mmol, 4.00 eq) at 25° C. After stirred at 65° C. for 12 hours, the mixture was filtered off and the filter cake was washed with ethyl acetate (100 mL). The filtrate was concentrated under vacuum to give (3S)-1-benzyl-3-prop-2-ynyl-piperazine (4.10 g, 19.1 mmol, 93% yield) as a yellow oil and used into next step without further purification.

$^1$H NMR (400 MHz, chloroform-d) δ=7.37-7.24 (m, 5H), 3.55-3.47 (m, 2H), 3.03-2.86 (m, 3H), 2.85-2.78 (m, 1H), 2.73 (br d, J=11.2 Hz, 1H), 2.33-2.20 (m, 2H), 2.13-2.04 (m, 1H), 2.02 (t, J=2.8 Hz, 1H), 1.90-1.83 (m, 1H).

Step E: tert-butyl (2S)-4-benzyl-2-prop-2-ynyl-piperazine-1-carboxylate

A mixture of (3S)-1-benzyl-3-prop-2-ynyl-piperazine (2.00 g, 9.33 mmol, 1.00 eq), TEA (2.83 g, 28.0 mmol, 3.90 mL, 3.00 eq) and (Boc)$_2$O (10.2 g, 46.7 mmol, 10.7 mL, 5.00 eq) in THF (20.0 mL) was stirred at 25° C. for 1 hour. The mixture was diluted with water (1×20.0 mL), extracted with ethyl acetate (3×20.0 mL). The combine organic layer was wash with brine (1×30.0 mL), dried over Na$_2$SO$_4$, filtered and concentrated under vacuum. The residue was purified by column chromatography (SiO$_2$, petroleum ether/ethyl acetate=5/1). The desired fractions were collected and concentrated under vacuum to give tert-butyl (2S)-4-benzyl-2-prop-2-ynyl-piperazine-1-carboxylate (1.50 g, 4.20 mmol, 45% yield, 88% purity) as a colorless oil. LCMS [ESI, M+1]: 315.

$^1$H NMR (400 MHz, chloroform-d) δ=7.38-7.27 (m, 5H), 4.26 (br s, 1H), 3.99-3.74 (m, 1H), 3.59-3.45 (m, 2H), 3.08-2.89 (m, 2H), 2.79-2.68 (m, 2H), 2.62-2.53 (m, 1H), 2.11 (dd, J=3.6, 11.2 Hz, 1H), 2.06-1.98 (m, 1H), 1.89 (t, J=2.8 Hz, 1H), 1.48-1.45 (m, 9H).

Step F: (2S)-2-prop-2-ynylpiperazine

A mixture of tert-butyl (2S)-4-benzyl-2-prop-2-ynyl-piperazine-1-carboxylate (1.40 g, 4.45 mmol, 1.00 eq), 1-chloro-1-(1-chlorovinyloxy)ethane (2.51 g, 17.8 mmol, 4.00 eq) in DCE (20.0 mL) was stirred at 85° C. for 1 hour. The mixture was concentrated under vacuum. The residue was dissolved in methanol (20.0 mL) and stirred at 65° C. for 1 hour. The mixture was concentrated under vacuum and triturated with petroleum ether (10.0 mL) to give (2S)-2-prop-2-ynylpiperazine (0.80 g, crude, 2 HCl) as a yellow solid and used into next step without further purification.

$^1$H NMR (400 MHz, methanol-d$_4$) δ=4.56-4.44 (m, 1H), 3.88-3.80 (m, 1H), 3.79-3.73 (m, 1H), 3.62-3.34 (m, 4H), 2.87-2.76 (m, 3H).

Step G: 4-benzyloxy-2-[[(2S)-1-methylpyrrolidin-2-yl]methoxy]-7-(1-naphthyl)-6,8-dihydro-5H-pyrido[3,4-d]pyrimidine A mixture of 4-benzyloxy-2-[[(2S)-1-methylpyrrolidin-2-yl]methoxy]-5,6,7,8-tetrahydropyrido[3,4-d]pyrimidine (2.00 g, 5.64 mmol, 1.00 eq), 1-bromonaphthalene (1.75 g, 8.46 mmol, 1.18 mL, 1.50 eq), Pd$_2$(dba)$_3$ (517 mg, 564 umol, 0.10 eq), RuPhos (527 mg, 1.13 mmol, 0.20 eq) and Cs$_2$CO$_3$ (3.68 g, 11.3 mmol, 2.00 eq) in toluene (20.0 mL) was stirred at 110° C. for 3 hours under N$_2$. The mixture was diluted with water (5.00 mL), extracted with ethyl acetate (3×5.00 mL). The organic layers were washed with brine (1×10.0 mL), dried over Na$_2$SO$_4$, filtered and concentrated under vacuum. The residue was purified by reversed phase flash [water (TFA, 0.10%)/acetonitrile]. The desired fraction was collected and adjusted pH >7 by saturated sodium bicarbonate (5.00 mL), and then extracted with ethyl acetate (3×20.0 mL). The combined organic layers were washed with brine (1×30.0 mL), dried over Na$_2$SO$_4$, filtered and concentrated under vacuum to give 4-benzyloxy-2-[[(2S)-1-methylpyrrolidin-2-yl]methoxy]-7-(1-naphthyl)-6,8-dihydro-5H-pyrido[3,4-d]pyrimidine (1.34 g, 2.78 mmol, 49% yield, 99.6% purity) as a yellow solid. LCMS [ESI, M+1]: 481.

$^1$H NMR (400 MHz, chloroform-d) δ=8.22-8.16 (m, 1H), 7.89-7.82 (m, 1H), 7.59 (d, J=8.0 Hz, 1H), 7.51-7.45 (m, 4H), 7.45-7.33 (m, 4H), 7.14 (dd, J=0.8, 7.2 Hz, 1H), 5.49 (s, 2H), 4.45 (dd, J=5.6, 10.4 Hz, 1H), 4.27-4.18 (m, 3H), 3.55-3.24 (m, 2H), 3.12 (br t, J=7.6 Hz, 1H), 2.89 (br s, 2H), 2.76-2.65 (m, 1H), 2.50 (s, 3H), 2.35-2.24 (m, 1H), 2.14-2.06 (m, 1H), 1.91-1.78 (m, 3H).

Step H: 2-[[(2S)-1-methylpyrrolidin-2-yl]methoxy]-7-(1-naphthyl)-6,8-dihydro-5H-pyrido[3,4-d]pyrimidin-4-ol A mixture of 4-benzyloxy-2-[[(2S)-1-methylpyrrolidin-2-yl]methoxy]-7-(1-naphthyl)-6,8-dihydro-5H-pyrido[3,4-d]pyrimidine (1.30 g, 2.70 mmol, 1.00 eq) and Pd/C (0.20 g, 10% purity) in methanol (200 mL) was stirred at 25° C. for 1 hour under H$_2$ at 15 psi. The catalyst was filtered off and the filtrate was concentrated under vacuum to give 2-[[(2S)-1-methylpyrrolidin-2-yl]methoxy]-7-(1-naphthyl)-6,8-dihydro-5H-pyrido[3,4-d]pyrimidin-4-ol (1.00 g, 1.90 mmol, 70% yield, 74% purity) as a yellow solid and used into next step without further purification. LCMS [ESI, M+1]: 391.

$^1$H NMR (400 MHz, chloroform-d) δ=8.24-8.16 (m, 1H), 7.90-7.81 (m, 1H), 7.59 (d, J=8.4 Hz, 1H), 7.54-7.47 (m, 2H), 7.42 (t, J=7.6 Hz, 1H), 7.14 (d, J=7.6 Hz, 1H), 4.43-4.31 (m, 2H), 4.05 (s, 2H), 3.38 (br s, 2H), 3.18-3.10 (m, 1H), 2.79 (br s, 2H), 2.70-2.54 (m, 2H), 2.47 (s, 3H), 2.32 (dt, J=7.2, 9.6 Hz, 1H), 2.02-1.96 (m, 1H), 1.91-1.75 (m, 3H).

Step I: [2-[[(2S)-1-methylpyrrolidin-2-yl]methoxy]-7-(1-naphthyl)-6,8-dihydro-5H-pyrido[3,4-d]pyrimidin-4-yl] trifluoromethanesulfonate To a solution of 2-[[(2S)-1-methylpyrrolidin-2-yl]methoxy]-7-(1-naphthyl)-6,8-dihydro-5H-pyrido[3,4-d]pyrimidin-4-ol (0.40 g, 1.02 mmol, 1.00 eq) and TEA (207 mg, 2.05 mmol, 285 uL, 2.00 eq) in dichloromethane (10.0 mL) was added Tf₂O (318 mg, 1.13 mmol, 186 uL, 1.10 eq) at −40° C. After stirred −40° C. for 0.25 hour, the mixture was diluted with water (3.00 mL) and then extracted with ethyl acetate (3×5.00 mL). The extracts were washed with brine (1×5.00 mL), dried over Na₂SO₄, filtered and concentrated under vacuum. The residue was purified by column chromatography (SiO₂, ethyl acetate/methanol=10/1). The desired fractions were collected and concentrated under vacuum to give [2-[[(2S)-1-methylpyrrolidin-2-yl]methoxy]-7-(1-naphthyl)-6,8-dihydro-5H-pyrido[3,4-d]pyrimidin-4-yl] trifluoromethanesulfonate (0.40 g, 528 umol, 52% yield, 69% purity) as a yellow solid. LCMS [ESI, M+1]: 523.

Step J: 2-[[(2S)-1-methylpyrrolidin-2-yl]methoxy]-7-(1-naphthyl)-4-[(3S)-3-prop-2-ynylpiperazin-1-yl]-6,8-dihydro-5H-pyrido[3,4-d]pyrimidine A mixture of [2-[[(2S)-1-methylpyrrolidin-2-yl]methoxy]-7-(1-naphthyl)-6,8-dihydro-5H-pyrido[3,4-d]pyrimidin-4-yl] trifluoromethanesulfonate (0.38 g, 727 umol, 1.00 eq), (2S)-2-prop-2-ynylpiperazine (350 mg, crude, 2 HCl) and DIEA (939 mg, 7.27 mmol, 1.27 mL, 10.0 eq) in DMF (4.00 mL) was stirred at 100° C. for 0.25 hour. The mixture was diluted with water (5.00 mL) and extracted with ethyl acetate (3×10.0 mL). The extracts were washed with brine (1×10.0 mL), dried over Na₂SO₄, filtered and concentrated under vacuum. The residue was purified by reversed phase flash [water (FA, 0.1%)/acetonitrile]. The desired fractions were collected and lyophilized to give 2-[[(2S)-1-methylpyrrolidin-2-yl]methoxy]-7-(1-naphthyl)-4-[(3S)-3-prop-2-ynylpiperazin-1-yl]-6,8-dihydro-5H-pyrido[3,4-d]pyrimidine (0.20 g, 336 umol, 46% yield, 99% purity, 2 FA) as a yellow oil. LCMS [ESI, M+1]: 497.

Step K: 1-[(2S)-4-[2-[[(2S)-1-methylpyrrolidin-2-yl]methoxy]-7-(1-naphthyl)-6,8-dihydro-5H-pyrido[3,4-d]pyrimidin-4-yl]-2-prop-2-ynyl-piperazin-1-yl]prop-2-en-1-one To a solution of 2-[[(2S)-1-methylpyrrolidin-2-yl]methoxy]-7-(1-naphthyl)-4-[(3S)-3-prop-2-ynylpiperazin-1-yl]-6,8-dihydro-5H-pyrido[3,4-d]pyrimidine (145 mg, 246 umol, 1.00 eq, 2 FA) and TEA (374 mg, 3.69 mmol, 514 uL, 15.0 eq) in dichloromethane (4.00 mL) was added prop-2-enoyl chloride (22.3 mg, 246 umol, 20.1 uL, 1.00 eq) at −40° C. After stirred at 25° C. for 0.25 h, the mixture was diluted with water (3.00 mL), and then extracted with dichloromethane (3×3.00 mL). The extracts were dried over Na₂SO₄, filtered and concentrated under vacuum. The residue was purified by prep-HPLC (column: Phenomenex Gemini 150*25 mm*10 um; mobile phase: [water (10 mM NH₄HCO₃)-ACN]; B %: 57%-87%, 12 min). The desired fractions were collected and lyophilized to give title compound 1-[(2S)-4-[2-[[(2S)-1-methylpyrrolidin-2-yl]methoxy]-7-(1-naphthyl)-6,8-dihydro-5H-pyrido[3,4-d]pyrimidin-4-yl]-2-prop-2-ynyl-piperazin-1-yl]prop-2-en-1-one (EXAMPLE 358, 25.6 mg, 46.3 umol, 19% yield, 99.5% purity) as a brown solid. LCMS [ESI, M+1]: 551.

SFC conditions: "OD-3S_3_40_3ML Column: Chiralcel OD-3 100×4.6 mm I.D., 3 um, Mobile phase: 40% methanol (0.05% DEA) in CO₂, Flow rate: 3 mL/min, Wavelength: 220 nm".

¹H NMR (400 MHz, chloroform-d) δ=8.21 (m, 1H), 7.91-7.81 (m, 1H), 7.60 (br d, J=8.0 Hz, 1H), 7.54-7.47 (m, 2H), 7.46-7.39 (m, 1H), 7.14 (d, J=7.2 Hz, 1H), 6.65 (br s, 1H), 6.36 (br d, J=16.8 Hz, 1H), 5.77 (dd, J=2.0, 10.8 Hz, 1H), 5.00-4.52 (m, 1H), 4.46-4.36 (m, 1H), 4.34-3.81 (m, 6H), 3.47 (m, 1H), 3.38-3.21 (m, 2H), 3.19-2.90 (m, 4H), 2.84 (br s, 1H), 2.73-2.52 (m, 3H), 2.48 (s, 3H), 2.34-2.24 (m, 1H), 2.10-2.03 (m, 1H), 1.90-1.70 (m, 4H).

Example 359

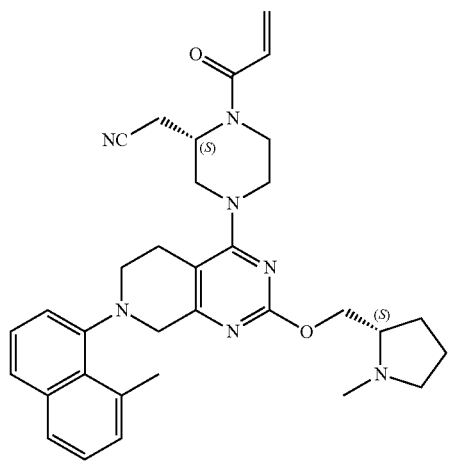

2-((S)-1-acryloyl-4-(7-(8-methylnaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile

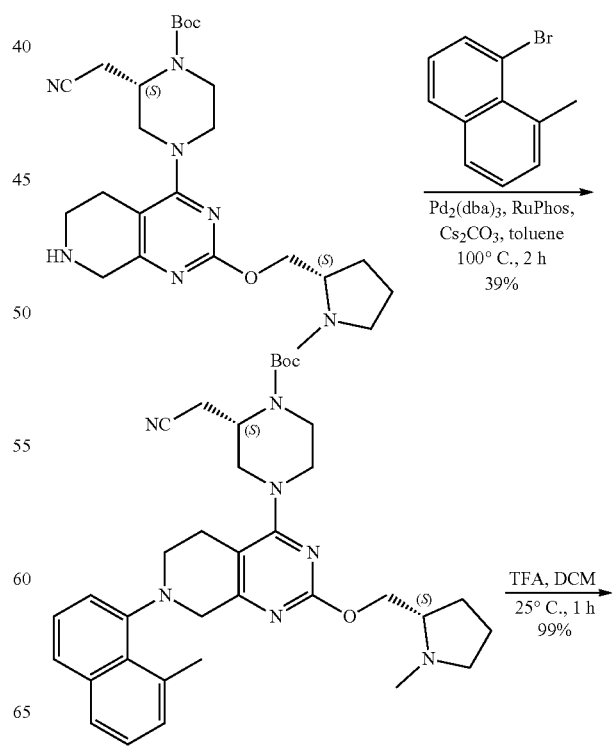

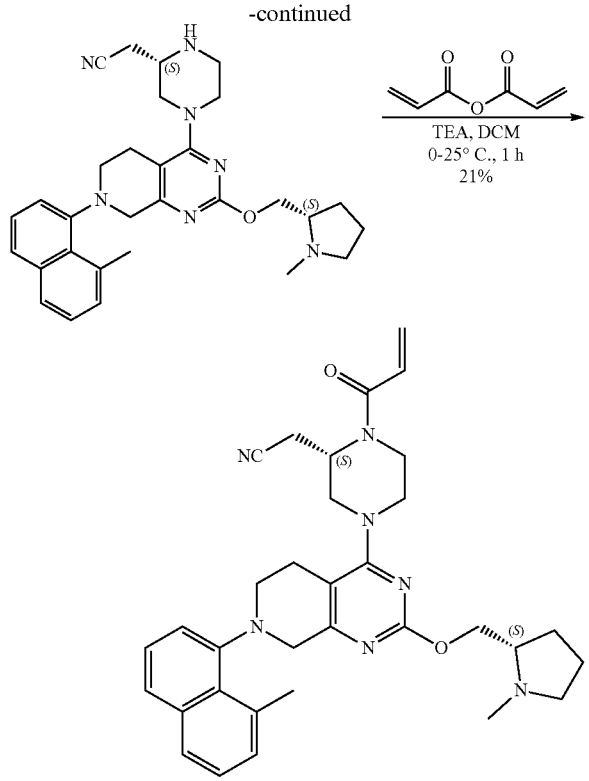

Step A: tert-Butyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate A mixture of 1-bromo-8-methyl-naphthalene (Intermediate 69, 507 mg, 1.65 mmol, 1.3 eq), tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 600 mg, 1.27 mmol, 1 eq), Cs₂CO₃ (1.04 g, 3.18 mmol, 2.5 eq), RuPhos (118 mg, 254 umol, 0.2 eq) and Pd₂(dba)₃ (233 mg, 254 umol, 0.2 eq) in toluene (10 mL) was degassed and purged with N₂ for 3 times, and then the mixture was stirred at 100° C. for 2 hours under N₂ atmosphere. The reaction mixture was diluted with water (30 mL) and extracted with ethyl acetate (20 mL×3). The combined organic layers were washed with brine (20 mL), dried over Na₂SO₄, filtered and concentrated under reduced pressure to give a residue. The residue was purified by reversed phase flash [water (0.1% formic acid)/acetonitrile)]. The mixture was adjusted pH ~7 with saturated NaHCO₃ aqueous solution and extracted with ethyl acetate (20 mL×3). The combined organic layers were washed with brine (20 mL), dried over Na₂SO₄, filtered and concentrated under reduced pressure to give the product. Compound tert-Butyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (310 mg, 501 umol, 39% yield, 99% purity) was obtained as a yellow solid. LCMS [ESI, M+1]: 612.

¹HNMR (400 MHz, chloroform-d) δ=7.74-7.60 (m, 2H), 7.46-7.37 (m, 1H), 7.34 (t, J=7.6 Hz, 1H), 7.27-7.16 (m, 2H), 4.61 (br s, 1H), 4.43-4.33 (m, 1H), 4.30-4.14 (m, 2H), 4.10-3.72 (m, 4H), 3.60-3.44 (m, 1H), 3.38 (br dd, J=3.6, 13.6 Hz, 1H), 3.24-3.04 (m, 4H), 3.03-2.84 (m, 5H), 2.82-2.53 (m, 4H), 2.52-2.42 (m, 3H), 2.29 (br s, 1H), 2.05-1.95 (m, 1H), 1.91-1.69 (m, 2H), 1.52 (s, 9H).

Step B: 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (310 mg, 506 umol, 1 eq) in DCM (500 uL) was added TFA (866 mg, 7.60 mmol, 562 uL, 15 eq). The mixture was stirred at 25° C. for 1 hour. The reaction mixture was concentrated under vacuum. Compound 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (317 mg, 506 umol, 99% yield, TFA) was obtained as a yellow oil and used to next step directly without purification. LCMS [ESI, M+1]: 512.

Step C: 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (317 mg, 506 umol, 1 eq, TFA) in DCM (5 mL) was added TEA (512 mg, 5.07 mmol, 705 uL, 10 eq) at 0° C. After addition, and prop-2-enoyl prop-2-enoate (51.1 mg, 405 umol, 0.8 eq) in DCM (1 mL) was added dropwise at 0° C. The resulting mixture was stirred at 25° C. for 1 hour. The reaction mixture was quenched with saturated NaHCO₃ aqueous solution (1 mL) and extracted with ethyl acetate (20 mL×3). The combined organic layers were washed with brine (20 mL), dried over Na₂SO₄, filtered and concentrated under reduced pressure to give a residue. The residue was purified by prep-HPLC (column: Phenomenex Gemini 150*25 mm*10 um; mobile phase: [water (0.05% ammonia hydroxide v/v)-ACN]; B %: 50%-80%, 12 min). Title compound 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 359, 60.2 mg, 105 umol, 21% yield, 99.5% purity) was obtained as a white solid. LCMS [ESI, M+1]: 566.

SFC condition: "OJ-3S_5_5_40_3ML Column: Chiralcel OJ-3 100×4.6 mm I.D., 3 um Mobile phase: ethanol (0.05% DEA) in CO₂ from 5% to 40% Flow rate: 3 mL/min Wavelength: 220 nm".

¹H NMR (400 MHz, chloroform-d) δ=7.75-7.60 (m, 2H), 7.46-7.38 (m, 1H), 7.34 (t, J=7.6 Hz, 1H), 7.27-7.17 (m, 2H), 6.57 (s, 1H), 6.46-6.33 (m, 1H), 5.83 (br d, J=10.4 Hz, 1H), 5.07 (br s, 1H), 4.64 (br s, 1H), 4.44-4.32 (m, 1H), 4.31-4.21 (m, 1H), 4.20-4.03 (m, 3H), 3.98-3.83 (m, 1H), 3.78-3.62 (m, 1H), 3.60-3.36 (m, 2H), 3.23-2.96 (m, 5H), 2.92 (s, 3H), 2.88-2.74 (m, 1H), 2.73-2.55 (m, 2H), 2.47 (d, J=4.4 Hz, 3H), 2.35-2.21 (m, 1H), 2.13-1.97 (m, 1H), 1.90-1.74 (m, 3H).

Alternatively, EXAMPLE 359 may be prepared as follows:

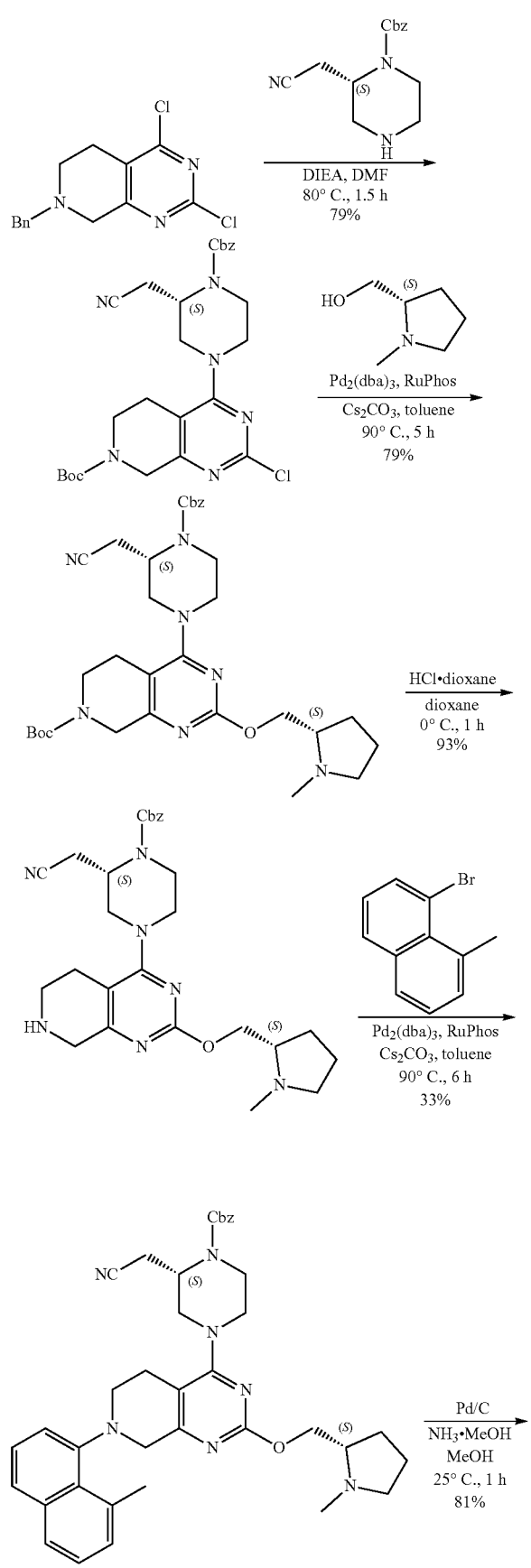

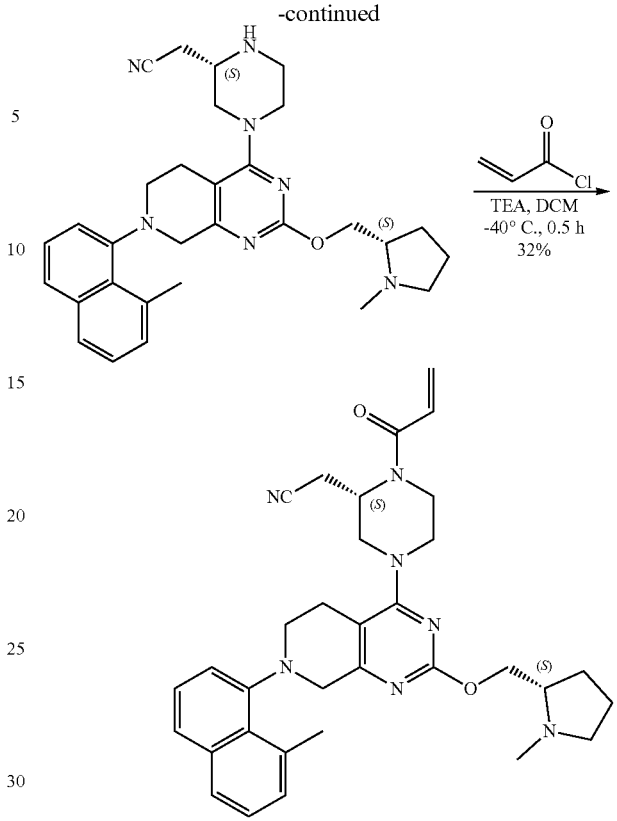

Step A: tert-Butyl 4-[(3S)-4-benzyloxycarbonyl-3-(cyanomethyl)piperazin-1-yl]-2-chloro-6,8-dihydro-5H-pyrido[3,4-d]pyrimidine-7-carboxylate To a solution of tert-butyl 2,4-dichloro-6,8-dihydro-5H-pyrido [3,4-d]pyrimidine-7-carboxylate (18.8 g, 61.7 mmol, 1 eq) in DMF (200 mL) was added DIEA (15.9 g, 123 mmol, 21.5 mL, 2 eq) and benzyl (2S)-2-(cyanomethyl)piperazine-1-carboxylate (Intermediate 63, 16.0 g, 61.7 mmol, 1 eq). After stirred at 80° C. for 1.5 hour, the reaction mixture was diluted with ethyl acetate (200 mL) and washed with water (200 mL×3). The combined organic layers were washed with brine (200 mL), dried over Na$_2$SO$_4$, filtered and concentrated under reduced pressure to give a residue. The residue was purified by column chromatography (SiO$_2$, Petroleum ether/Ethyl acetate=50/1 to 2/1). Compound tert-Butyl 4-[(3S)-4-benzyloxycarbonyl-3-(cyanomethyl)piperazin-1-yl]-2-chloro-6,8-dihydro-5H-pyrido[3,4-d]pyrimidine-7-carboxylate (26 g, 48.8 mmol, 79% yield, 99% purity) was obtained as a white solid. LCMS [ESI, M+1]: 527.

$^1$H NMR (400 MHz, chloroform-d) δ=7.43-7.34 (m, 5H), 5.20 (s, 2H), 4.73-4.60 (m, 2H), 4.45 (d, J=19.2 Hz, 1H), 4.13-4.02 (m, 2H), 3.94-3.75 (m, 2H), 3.45-3.25 (m, 3H), 3.11 (td, J=3.6, 12.4 Hz, 1H), 2.88-2.59 (m, 4H), 1.60 (s, 9H).

Step B: tert-Butyl 4-[(3S)-4-benzyloxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate A mixture of [(2S)-1-methylpyrrolidin-2-yl]methanol (10.5 g, 91.1 mmol, 10.8 mL, 2 eq), tert-butyl 4-[(3S)-4- benzyloxycarbonyl-3-(cyanomethyl) piperazin-1-yl]-2-chloro-6,8-dihydro-5H-pyrido[3,4-d]pyrimidine-7-carboxylate (24 g, 45.6 mmol, 1 eq), $Pd_2(dba)_3$ (6.18 g, 6.84 mmol, 0.15 eq), RuPhos (4.26 g, 9.12 mmol, 0.2 eq) and $Cs_2CO_3$ (37.1 g, 114 mmol, 2.5 eq) in toluene (450 mL) was degassed and purged with $N_2$ for 3 times, and then the mixture was stirred at 90° C. for 5 hours under $N_2$ atmosphere. The reaction mixture was diluted with water (200 mL) and extracted with ethyl acetate (500 mL×3). The combined organic layers were washed with brine (200 mL), dried over $Na_2SO_4$, filtered and concentrated under reduced pressure to give a residue. The residue was purified by column chromatography ($Al_2O_3$, ethyl acetate/methanol=1/0 to 10/1). Compound tert-Butyl 4-[(3S)-4-benzyloxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate (25 g, 35.9 mmol, 79% yield, 87% purity) was obtained as a yellow solid. LCMS [ESI, M+1]: 606.

Step C: benzyl (2S)-2-(cyanomethyl)-4-[2-[[(2S)-1-methylpyrrolidin-2-yl]methoxy]-5,6,7,8-tetrahydro-pyrido[3,4-d]pyrimidin-4-yl]piperazine-1-carboxylate To a solution of tert-butyl 4-[(3S)-4-benzyloxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate (16 g, 26.4 mmol, 1 eq) in dioxane (100 mL) was added HCl/dioxane (4 M, 99.1 mL, 15 eq). The mixture was stirred at 0° C. for 1 hour. The dioxane was decanted and the solid was collected. The solid residue was diluted with water (50 mL) and dichloromethane (200 mL), then adjusted pH=8 with saturated $Na_2CO_3$ aqueous solution and extracted with ethyl acetate (200 mL×3). The combined organic layers were washed with brine (100 mL), dried over $Na_2SO_4$, filtered and concentrated under reduced pressure to give benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 13.5 g, 24.5 mmol, 93% yield, 91.6% purity) as a yellow oil and used next step without purification. LCMS [ESI, M+1]: 506.

$^1$H NMR (400 MHz, chloroform-d) δ=7.45-7.31 (m, 5H), 5.19 (s, 2H), 4.65 (br s, 1H), 4.40-4.31 (m, 1H), 4.14-4.04 (m, 2H), 4.03-3.91 (m, 3H), 3.91-3.77 (m, 1H), 3.24 (d, J=13.2 Hz, 2H), 3.16-3.05 (m, 2H), 3.04-2.89 (m, 2H), 2.81 (br s, 1H), 2.75-2.51 (m, 4H), 2.47 (s, 3H), 2.35-2.22 (m, 1H), 2.08-2.00 (m, 1H), 1.92-1.76 (m, 3H).

Step D: benzyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate A mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (10 g, 19.8 mmol, 1 eq), 1-bromo-8-methyl-naphthalene (Intermediate 69, 5.68 g, 25.7 mmol, 1.3 eq), RuPhos (2.77 g, 5.93 mmol, 0.3 eq), $Cs_2CO_3$ (16.1 g, 49.5 mmol, 2.5 eq) and $Pd_2(dba)_3$ (3.62 g, 3.96 mmol, 0.2 eq) in toluene (100 mL) was degassed and purged with $N_2$ for 3 times, and then the mixture was stirred at 90° C. for 6 hours under $N_2$ atmosphere. The reaction mixture was diluted with water (100 mL) and extracted with ethyl acetate (200 mL×3). The combined organic layers were washed with brine (100 mL), dried over $Na_2SO_4$, filtered and concentrated under reduced pressure to give a residue. The residue was purified by reversed phase flash [water (0.1% formic acid)/acetonitrile)]. The mixture was adjusted pH=7 with saturated $NaHCO_3$ aqueous solution and extracted with ethyl acetate (500 mL×3). The combined organic layers were washed with brine (200 mL), dried over $Na_2SO_4$, filtered and concentrated under reduced pressure to give benzyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (9 g, 12.9 mmol, 33% yield, 93% purity) as a yellow solid. LCMS [ESI, M+1]: 646.

$^1$H NMR (400 MHz, $C_2D_2Cl_4$) δ=7.32 (d, J=8.0 Hz, 1H), 7.26 (t, J=8.0 Hz, 1H), 7.08-6.93 (m, 7H), 6.91-6.78 (m, 2H), 4.81 (s, 2H), 4.30 (s, 1H), 4.13-3.95 (m, 1H), 3.88-3.33 (m, 6H), 3.22-2.87 (m, 2H), 2.86-2.65 (m, 4H), 2.65-2.42 (m, 5H), 2.41-2.32 (m, 1H), 2.30-2.13 (m, 2H), 2.07 (d, J=7.2 Hz, 3H), 1.92 (br s, 1H), 1.72-1.45 (m, 4H).

Step E: 2-[(2S)-4-[7-(8-methyl-1-naphthyl)-2-[[(2S)-1-methyl pyrrolidin-2-yl]methoxy]-6,8-di-hydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (8 g, 12.4 mmol, 1 eq) in MeOH (100 mL) was added Pd/C (2 g, 10% purity) and $NH_3$·MeOH (50 mL, 15%) under $N_2$. The suspension was degassed under vacuum and purged with $H_2$ several times. The mixture was stirred under $H_2$ (15 psi) at 25° C. for 1 hour. The mixture was concentrated under vacuum. Compound 2-[(2S)-4-[7-(8-methyl-1-naphthyl)-2-[[(2S)-1-methyl pyrrolidin-2-yl]methoxy]-6,8-dihydro-5H-pyrido[3,4-d]pyrimidin-4-yl]piperazin-2-yl]acetonitrile (5.7 g, 10.0 mmol, 81% yield, 90% purity) was obtained as a yellow solid. LCMS [ESI, M+1]: 512.

$^1$H NMR (400 MHz, chloroform-d) δ=7.69 (d, J=8.0 Hz, 1H), 7.64 (dd, J=3.2, 7.6 Hz, 1H), 7.40 (td, J=4.4, 7.6 Hz, 1H), 7.34 (t, J=7.6 Hz, 1H), 7.26-7.19 (m, 2H), 4.46-4.34 (m, 1H), 4.25-4.03 (m, 2H), 3.97-3.69 (m, 3H), 3.49-3.44 (m, 1H), 3.39-3.07 (m, 5H), 3.06-2.83 (m, 6H), 2.76-2.63 (m, 1H), 2.62-2.51 (m, 3H), 2.48 (d, J=3.2 Hz, 3H), 2.35-2.22 (m, 1H), 2.13-1.98 (m, 1H), 1.83-1.69 (m, 3H).

Step F: 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (6.4 g, 12.5 mmol, 1 eq) in dichloromethane (120 mL) was added TEA (19 g, 187 mmol, 26 mL, 15 eq) at −40° C. After addition, a solution of prop-2-enoyl chloride (1.70 g, 18.8 mmol, 1.53 mL, 1.5 eq) in dichloromethane (2 mL) was added dropwise at −40° C. After stirred at −40° C. for 0.5 hour, the reaction mixture was quenched with saturated $NaHCO_3$ aqueous solution (10 mL), then diluted with water (50 mL) and extracted with dichloromethane (50 mL×3). The combined organic layers were washed with brine (20 mL), dried over $Na_2SO_4$, filtered and concentrated under reduced pressure to give a residue. The residue was purified by column chromatography ($SiO_2$, DCM/MeOH=100/1 to 10/1) and further purified by prep-HPLC (column: Kromasil 250*50 mm*10 um; mobile phase: [water (0.225% FA)-ACN]; B %: 20%-50%, 28 min). The mixture was adjusted pH=7 with saturated NaHCO₃ aqueous solution and extracted with dichloromethane (20 mL×3). The combined organic layers were washed with brine (20 mL), dried over Na₂SO₄, filtered and concentrated under reduced pressure to give title compound 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 359, 2.3 g, 4.03 mmol, 32% yield, 99% purity) as a yellow solid. LCMS [ESI, M+1]: 566.

¹H NMR (400 MHz, chloroform-d) δ=7.74-7.59 (m, 2H), 7.46-7.36 (m, 1H), 7.33 (t, J=7.6 Hz, 1H), 7.26-7.15 (m, 2H), 6.70-6.47 (s, 1H), 6.39 (d, J=16.4 Hz, 1H), 5.82 (d, J=10.4 Hz, 1H), 5.16-4.47 (m, 1H), 4.44-4.32 (m, 1H), 4.30-3.62 (m, 6H), 3.58-3.26 (m, 2H), 3.25-2.95 (m, 5H), 2.91 (s, 3H), 2.86-2.55 (m, 4H), 2.48 (d, J=5.2 Hz, 3H), 2.36-2.21 (m, 1H), 2.13-2.02 (m, 1H), 1.92-1.67 (m, 3H).

Example 360

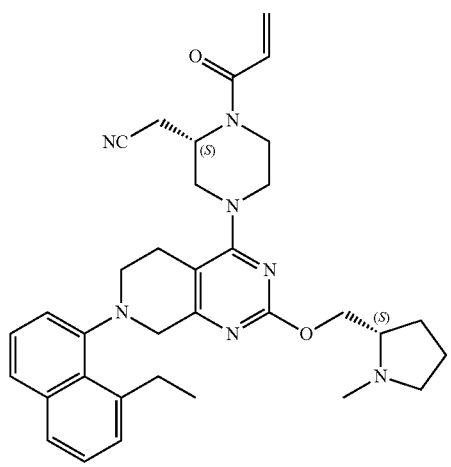

2-[(2S)-4-[7-(8-ethyl-1-naphthyl)-2-[[(2S)-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile

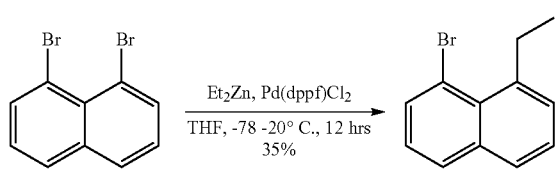

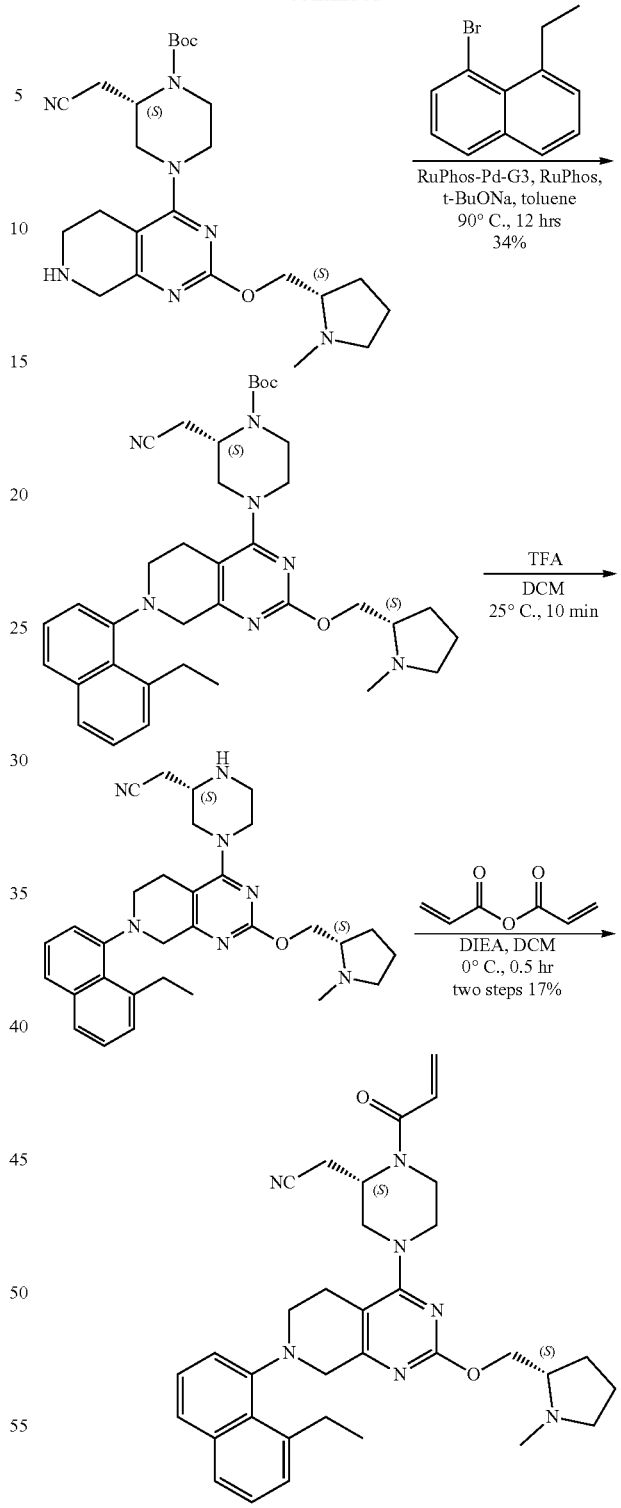

Insert: 1-bromo-8-ethyl-naphthalene

To a solution of 1,8-dibromonaphthalene (2.0 g, 6.99 mmol, 1.0 eq) and Pd(dppf)Cl₂ (367 mg, 501 umol, 7.16 e⁻² eq) in THF (15.0 mL) was added diethyl zinc (1.0 M in toluene, 3.50 mL, 0.50 eq) at −78° C. The mixture was stirred at −78-20° C. for 12 hours. After completion, the reaction mixture was added water (30.0 mL) and extracted with EA (30.0 mL×3). The organic layer was dried over Na₂SO₄, filtered and concentrated. The residue was triturated with PE (60.0 mL) and filtered. The filter cake was washed with PE (10.0 mL×2), the mother liquid was concentrated. The obtained product was purified by reversed phase flash column (C18, 0.1% FA in water, 0-100% MeCN) to give 1-bromo-8-ethyl-naphthalene (600 mg, 2.45 mmol, 35% yield, 96% purity) as yellow oil.

¹H NMR (400 MHz, Chloroform-d) δ 7.72-7.63 (m, 2H), 7.58 (dd, J=2.4, 7.2 Hz, 1H), 7.30-7.23 (m, 2H), 7.13-7.04 (m, 1H), 3.43 (q, J=7.6 Hz, 2H), 1.22 (t, J=7.6 Hz, 3H).

Step A: tert-butyl (2S)-2-(cyanomethyl)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a solution of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 300 mg, 636 umol, 1.0 eq), t-BuONa (183 mg, 1.91 mmol, 3.0 eq), RuPhos (59.4 mg, 127 umol, 0.2 eq) and RuPhos-Pd-G3 (106 mg, 127 umol, 0.20 eq) in toluene (5.0 mL) was added 1-bromo-8-ethyl-naphthalene (299 mg, 1.27 mmol, 2.0 eq). The mixture was stirred at 90° C. for 12 hours. After completion, the reaction mixture was added water (10.0 mL) and extracted with EA (10.0 mL×3). The organic layer was dried over Na₂SO₄, filtered and concentrated. The obtained product was purified by reversed phase flash column (C18, 0.1% FA in water, 0-60% MeCN) to give tert-butyl (2S)-2-(cyanomethyl)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (140 mg, 221 umol, 34% yield, 98% purity) as yellow oil. LCMS [ESI, M+1]: 626.

Step B: 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (130 mg, 208 umol, 1.0 eq) in DCM (1.0 mL) was added TFA (1.54 g, 13.5 mmol, 1.0 mL, 65.0 eq). The mixture was stirred at 25° C. for 10 min. After completion, the reaction mixture was concentrated under vacuum. The product 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, crude, 2TFA) was obtained as yellow oil. LCMS [ESI, M+1]: 526.

Step C: 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 199 umol, 1.0 eq, 2TFA) and DIEA (309 mg, 2.39 mmol, 416 uL, 12.0 eq) in DCM (2.0 mL) was added prop-2-enoyl prop-2-enoate (37.7 mg, 299 umol, 1.50 eq) at 0° C. The mixture was stirred at 0° C. for 0.5 hour. After completion, the mixture was quenched with MeOH (1.0 mL) and concentrated under vacuum. The obtained product was purified by prep-HPLC (column: Gemini 150*25 5 u; mobile phase: [water (0.05% ammonia hydroxide v/v)-ACN]; B %: 53%-83%, 12 min) to give title compound 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 360, 20.0 mg, 33.8 umol, 17% yield, 98% purity) as pink solid. LCMS [ESI, M+1]: 580.

¹H NMR (400 MHz, Chloroform-d) δ 7.74-7.64 (m, 2H), 7.46-7.35 (m, 2H), 7.27-7.20 (m, 2H), 6.64-6.60 (m, 1H), 6.46-6.36 (m, 1H), 5.83 (br d, J=10.4 Hz, 1H), 5.20-4.50 (m, 1H), 4.45-4.33 (m, 1H), 4.31-4.19 (m, 1H), 4.17-3.96 (m, 3H), 3.93-3.84 (m, 1H), 3.74 (br d, J=18.0 Hz, 1H), 3.65-3.39 (m, 3H), 3.37-2.92 (m, 7H), 2.88-2.76 (m, 1H), 2.71-2.57 (m, 2H), 2.47 (br d, J=4.8 Hz, 3H), 2.34-2.23 (m, 1H), 2.11-1.98 (m, 1H), 1.80-1.72 (m, 3H), 1.17 (t, J=7.4 Hz, 3H).

Example 361

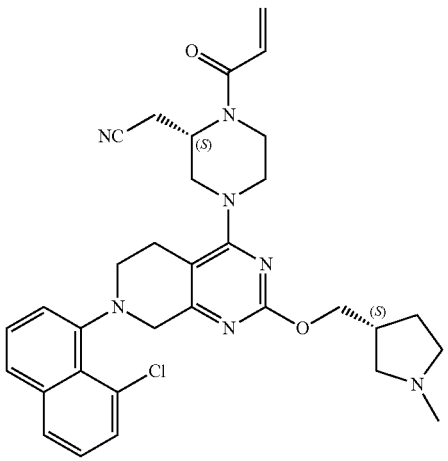

2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-1-prop-2-enoyl-piperazin-2-yl]acetonitrile

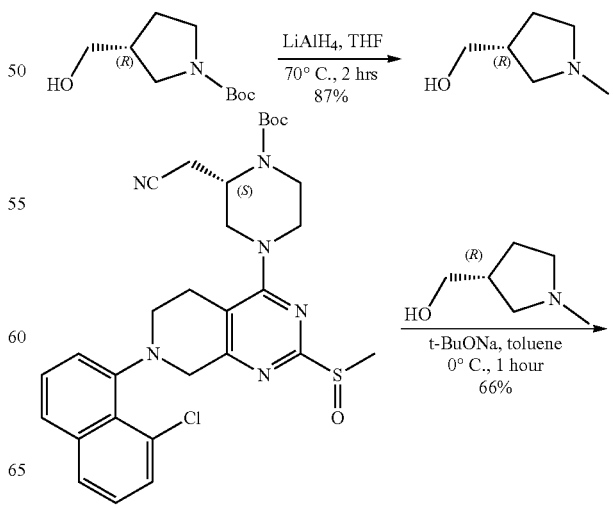

-continued

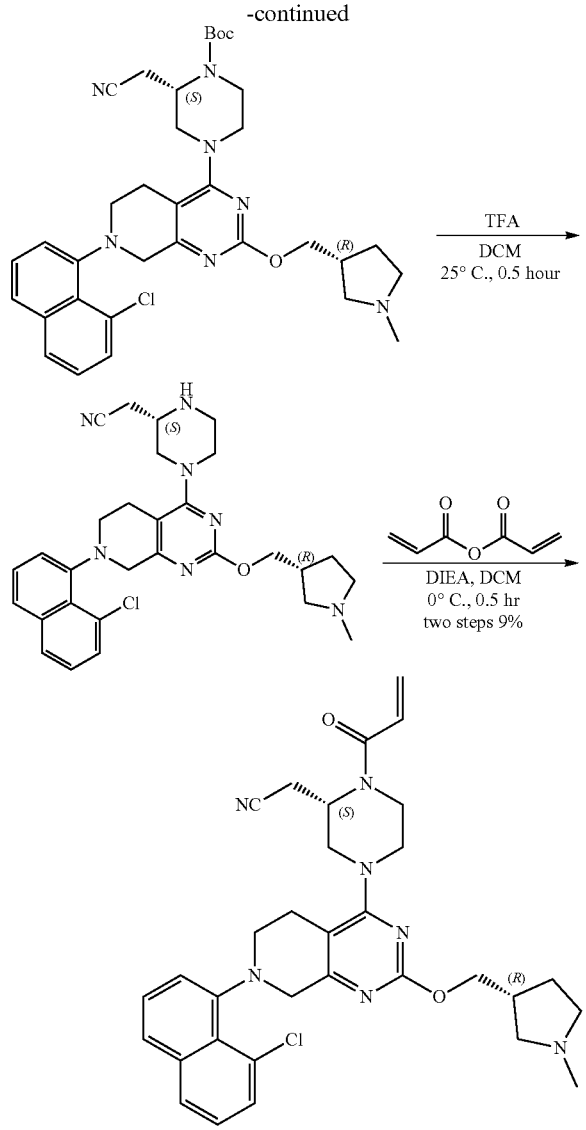

Insert: [(3R)-1-methylpyrrolidin-3-yl] methanol

To a solution of tert-butyl (3R)-3-(hydroxymethyl) pyrrolidine-1-carboxylate (1.0 g, 4.97 mmol, 1.0 eq) in THF (20.0 mL) was added LiAlH$_4$ (377 mg, 9.94 mmol, 2.0 eq). The mixture was stirred at 0° C. for 0.5 hour, then heated to 70° C. and stirred at 70° C. for 2 hours. After completion, the reaction mixture was quenched with saturated Na$_2$SO$_4$ aqueous (1.0 mL) and filtered. The filter cake was washed with THF (10.0 mL). Then the mother liquid was concentrated to give [(3R)-1-methylpyrrolidin-3-yl] methanol (500 mg, 4.34 mmol, 87% yield) as colorless oil.

$^1$H NMR (400 MHz, Chloroform-d) δ 3.65 (dd, J=4.8, 10.0 Hz, 1H), 3.52 (dd, J=5.6, 10.0 Hz, 1H), 3.05-2.69 (m, 2H), 2.63-2.53 (m, 1H), 2.51-2.44 (m, 1H), 2.40-2.25 (m, 5H), 2.04-1.94 (m, 1H), 1.72-1.59 (m, 1H).

Step A: tert-butyl(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-2-(cyanomethyl)piperazine-1-carboxylate To a solution of [(3R)-1-methylpyrrolidin-3-yl] methanol (178 mg, 1.55 mmol, 3.0 eq) in toluene (3.0 mL) was added t-BuONa (124 mg, 1.29 mmol, 2.50 eq). The mixture was stirred at 0° C. for 0.5 hour. Then tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (300 mg, 516 umol, 1.0 eq) was added to the above mixture. After addition, the mixture was stirred at 0° C. for 0.5 hour. After completion, the reaction mixture was added water (10.0 ml) and extracted with EA (10.0 mL×3). The organic layer was dried over Na$_2$SO$_4$, filtered and concentrated. The obtained product was purified by reversed phase flash (C18, 0.1% FA in water, 0-60% MeCN) to give tert-butyl(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-2-(cyanomethyl)piperazine-1-carboxylate (220 mg, 342 umol, 66% yield, 98% purity) as yellow solid. LCMS [ESI, M+1]: 632.

Step B: 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-2-(cyanomethyl)piperazine-1-carboxylate (360 mg, 569 umol, 1.0 eq) in DCM (1.50 mL) was added TFA (2.31 g, 20.3 mmol, 1.50 mL, 35.6 eq). The mixture was stirred at 25° C. for 0.5 hour. After completion, the mixture was concentrated to give 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (450 mg, crude, 2TFA) as yellow oil.

Step C: 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (450 mg, 592 umol, 1.0 eq, 2TFA) and DIEA (918 mg, 7.10 mmol, 1.24 mL, 12.0 eq) in DCM (4.0 mL) was added prop-2-enoyl prop-2-enoate (112 mg, 888 umol, 1.50 eq). The mixture was stirred at 0° C. for 0.5 hour. After completion, the mixture was quenched with MeOH (1.0 mL) and concentrated under vacuum. The obtained product was purified by prep-HPLC (column: Gemini 150*25 5 u; mobile phase: [water (0.04% NH$_3$.H$_2$O)-ACN]; B %: 70%-82%,10 min) to give title compound 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-1-prop-2-enoyl-piperazin-2-yl]acetonitrile (EXAMPLE 361, 32.6 mg, 53.8 umol, 9% yield, 97% purity) as gray solid. LCMS [ESI, M+1]: 586.

$^1$H NMR (400 MHz, Chloroform-d) δ 7.68 (br d, J=8.0 Hz, 1H), 7.54 (t, J=7.6 Hz, 1H), 7.45 (d, J=7.2 Hz, 1H), 7.41-7.32 (m, 1H), 7.26 (t, J=8.0 Hz, 1H), 7.18-7.11 (m, 1H), 6.60-6.43 (m, 1H), 6.32 (br d, J=16.4 Hz, 1H), 5.75 (br d, J=10.8 Hz, 1H), 5.15-4.50 (m, 1H), 4.41-4.28 (m, 1H), 4.18-4.10 (m, 2H), 4.09-3.88 (m, 2H), 3.87-3.68 (m, 2H), 3.57-3.45 (m, 1H), 3.42-3.26 (m, 1H), 3.25-2.87 (m, 5H), 2.86-2.74 (m, 1H), 2.73-2.57 (m, 3H), 2.56-2.47 (m, 2H), 2.46-2.37 (m, 2H), 2.28 (s, 3H), 2.07-1.90 (m, 1H). LCMS [ESI, M+1]: 586.

Example 362

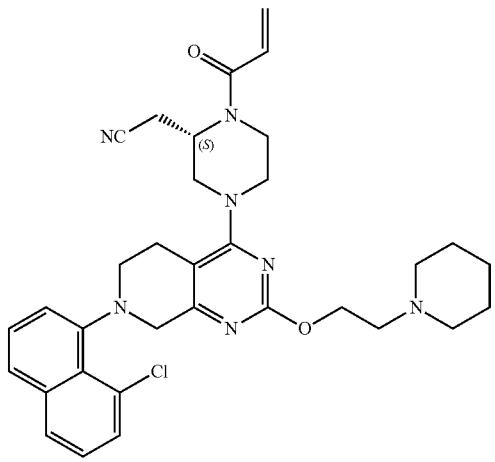

2-[(2S)-4-[7-(8-chloro-1-naphthyl)-2-[2-(1-piperidyl)ethoxy]-6,8-dihydro-5H-pyrido[3,4-d] pyrimidin-4-yl]-1-prop-2-enoyl-piperazin-2-yl]acetonitrile

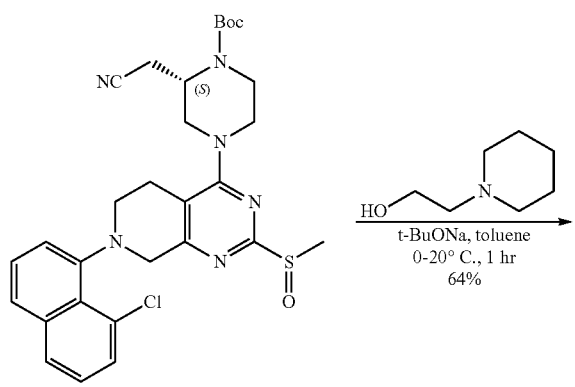

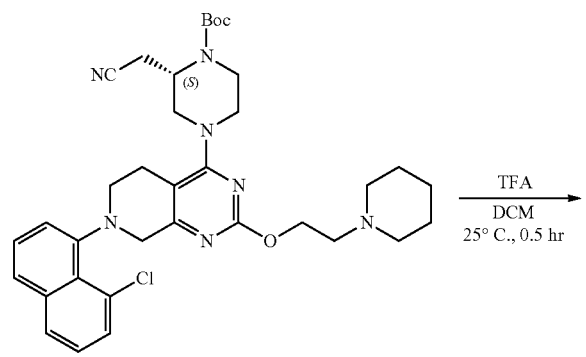

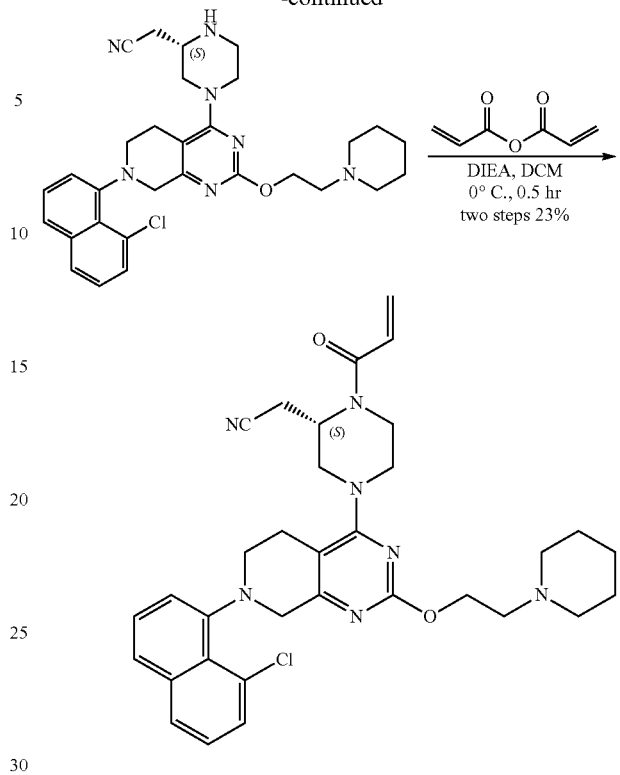

Step A: tert-butyl(2S)-4-[7-(8-chloro-1-naphthyl)-2-[2-(1-piperidyl)ethoxy]-6,8-dihydro-5H-pyrido[3,4-d]pyrimidin-4-yl]-2-(cyanomethyl)piperazine-1-carboxylate To a solution of 2-(1-piperidyl) ethanol (133 mg, 1.03 mmol, 137 uL, 3.0 eq) in toluene (2.0 mL) was added t-BuONa (66.2 mg, 688 umol, 2.0 eq) at 0° C. The mixture was stirred at 20° C. for 0.5 hour. Then tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (200 mg, 344 umol, 1.0 eq) was added to the above liquid at 0° C. After addition, the mixture was stirred at 0° C. for 0.5 hour. After completion, the reaction mixture was added water (5.0 mL) and extracted with EA (5.0 mL×3). The organic layer was dried over Na$_2$SO$_4$, filtered and concentrated. The obtained product was purified by column chromatography (SiO$_2$, PE:EA=3:1-EA:MeOH=10:1) to give tert-butyl(2S)-4-[7-(8-chloro-1-naphthyl)-2-[2-(1-piperidyl)ethoxy]-6,8-dihydro-5H-pyrido[3,4-d]pyrimidin-4-yl]-2-(cyanomethyl)piperazine-1-carboxylate (150 mg, 221 umol, 64% yield, 95% purity) as yellow oil. LCMS [ESI, M+1]: 646.

$^1$H NMR (400 MHz, Chloroform-d) δ 7.76 (d, J=8.0 Hz, 1H), 7.61 (t, J=7.8 Hz, 1H), 7.53 (d, J=7.6 Hz, 1H), 7.49-7.40 (m, 1H), 7.33 (t, J=7.8 Hz, 1H), 7.27-7.17 (m, 1H), 4.64-4.61 (m, 1H), 4.48-4.36 (m, 3H), 4.14-3.92 (m, 3H), 3.90-3.76 (m, 1H), 3.63-3.54 (m, 1H), 3.36 (br dd, J=3.6, 13.6 Hz, 1H), 3.26-3.06 (m, 3H), 3.01-2.86 (m, 1H), 2.82-2.76 (m, 2H), 2.71 (br d, J=6.8 Hz, 1H), 2.64-2.58 (m, 1H), 2.58-2.50 (m, 4H), 2.48-2.42 (m, 1H), 2.06 (d, J=6.4 Hz, 1H), 1.64-1.57 (m, 5H), 1.52 (s, 9H).

1019

Step B: 2-[(2S)-4-[7-(8-chloro-1-naphthyl)-2-[2-(1-piperidyl)ethoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[2-(1-piperidyl)ethoxy]-6,8-dihydro-5H-pyrido[3,4-d]pyrimidin-4-yl]-2-(cyanomethyl)piperazine-1-carboxylate (250 mg, 387 umol, 1.0 eq) in DCM (1.0 mL) was added TFA (1.54 g, 13.5 mmol, 1.0 mL, 34.9 eq). The mixture was stirred at 25° C. for 0.5 hour. After completion, the reaction mixture was concentrated under vacuum. The product 2-[(2S)-4-[7-(8-chloro-1-naphthyl)-2-[2-(1-piperidyl)ethoxy]-6,8-dihydro-5H-pyrido[3,4-d]pyrimidin-4-yl]piperazin-2-yl]acetonitrile (300 mg, crude, 2TFA) was obtained as yellow oil. LCMS [ESI, M+1]: 546.

Step C: 2-[(2S)-4-[7-(8-chloro-1-naphthyl)-2-[2-(1-piperidyl)ethoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-chloro-1-naphthyl)-2-[2-(1-piperidyl)ethoxy]-6,8-dihydro-5H-pyrido[3,4-d]pyrimidin-4-yl]piperazin-2-yl]acetonitrile (300 mg, 388 umol, 1.0 eq, 2TFA) and DIEA (601 mg, 4.65 mmol, 810 uL, 12.0 eq) in DCM (2.0 mL) was added prop-2-enoyl prop-2-enoate (73.3 mg, 581 umol, 1.5 eq). The mixture was stirred at 0° C. for 0.5 hour. After completion, the mixture was quenched with MeOH (1.0 mL) and concentrated under vacuum. The obtained product was purified by prep-HPLC (column: Gemini 150*25 5 u; mobile phase: [water (0.05% ammonia hydroxide v/v)-ACN]; B %: 55%-85%,12 min) to give title compound 2-[(2S)-4-[7-(8-chloro-1-naphthyl)-2-[2-(1-piperidyl)ethoxy]-6,8-dihydro-5H-pyrido[3,4-d]pyrimidin-4-yl]-1-prop-2-enoyl-piperazin-2-yl]acetonitrile (EXAMPLE 362, 54.0 mg, 88.1 umol, 23% yield, 98% purity) as colorless oil. LCMS [ESI, M+1]: 600.

$^1$H NMR (400 MHz, Chloroform-d) δ 7.76 (d, J=8.0 Hz, 1H), 7.62 (t, J=7.6 Hz, 1H), 7.53 (d, J=7.6 Hz, 1H), 7.49-7.39 (m, 1H), 7.34 (t, J=7.8 Hz, 1H), 7.27-7.18 (m, 1H), 6.58-6.62 (m, 1H), 6.44-6.36 (m, 1H), 5.83 (br d, J=10.8 Hz, 1H), 5.15-4.55 (m, 1H), 4.51-4.36 (m, 3H), 4.20-3.97 (m, 2H), 3.95-3.75 (m, 2H), 3.66-3.54 (m, 1H), 3.51-3.37 (m, 1H), 3.34-2.97 (m, 4H), 2.94-2.67 (m, 4H), 2.65-2.57 (m, 1H), 2.55-2.48 (m, 4H), 1.65-1.60 (m, 4H), 1.49-1.39 (m, 2H).

Example 363

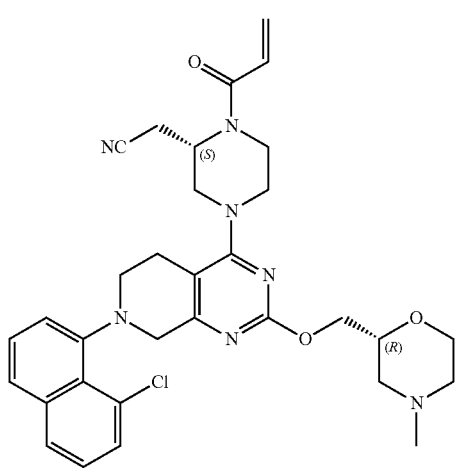

1020

2-[(2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]-1-prop-2-enoyl-piperazin-2-yl]acetonitrile

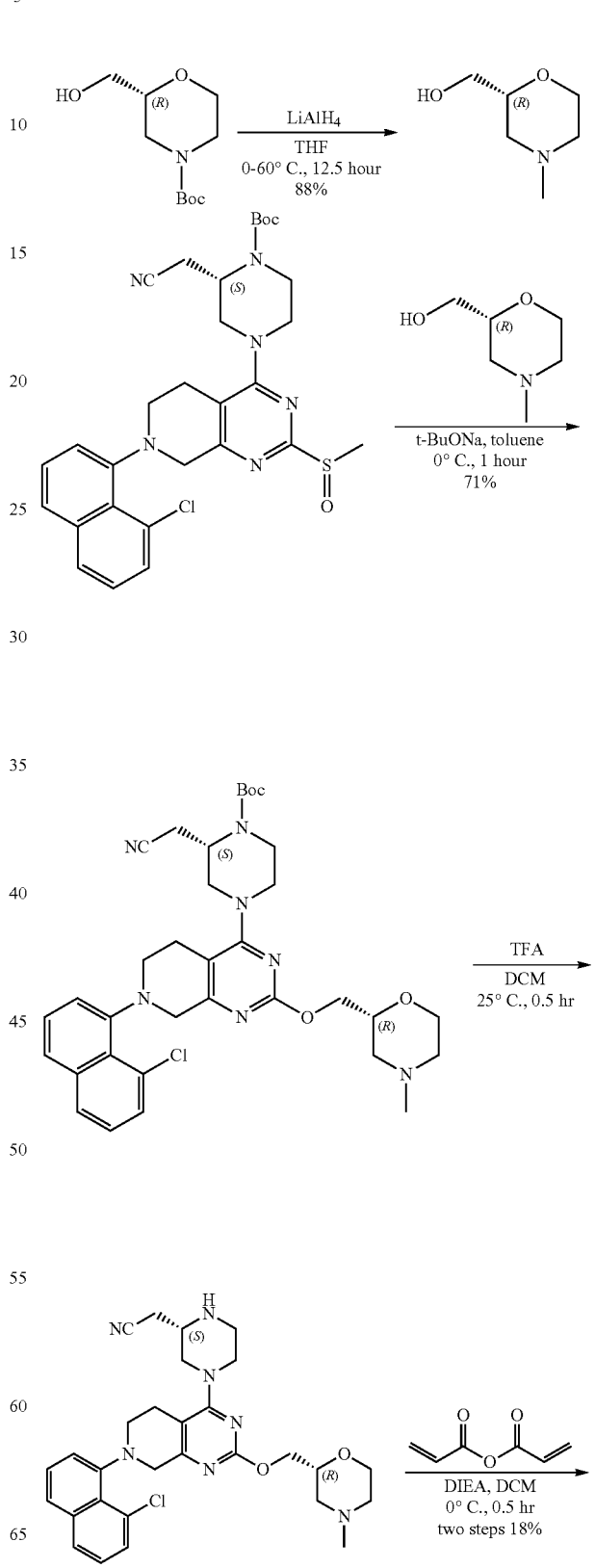

-continued

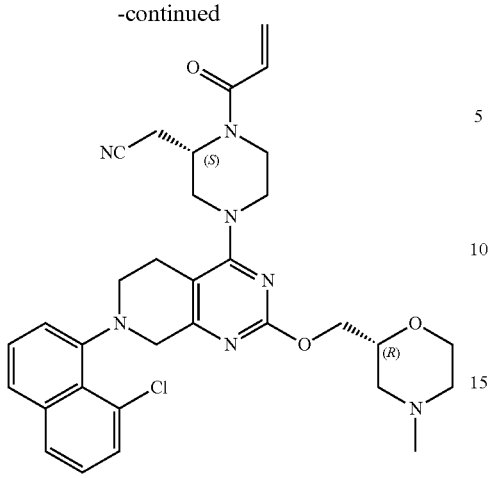

Insert: [(2R)-4-methylmorpholin-2-yl] methanol

To a solution of tert-butyl (2R)-2-(hydroxymethyl) morpholine-4-carboxylate (1.50 g, 6.90 mmol, 1.0 eq) in THF (20.0 mL) was added LiAlH$_4$ (524 mg, 13.8 mmol, 2.0 eq) in portions at 0° C. The mixture was stirred at 0° C. for 0.5 hour, then heated to 60° C. and stirred at 60° C. for 12 hours. After completion, the reaction mixture was quenched with saturated Na$_2$SO$_4$ aqueous (1.50 mL) and filtered. The cake was washed with THF (20.0 mL×2). Then the mother liquid was concentrated to give [(2R)-4-methylmorpholin-2-yl] methanol (800 mg, 6.10 mmol, 88% yield) as yellow oil.

$^1$H NMR (400 MHz, Chloroform-d) δ 3.92-3.86 (m, 1H), 3.73-3.52 (m, 4H), 2.84-2.56 (m, 3H), 2.27 (s, 3H), 2.11 (dt, J=3.6, 11.6 Hz, 1H), 1.93 (t, J=10.8 Hz, 1H).

Step A: tert-butyl (2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]-2-(cyanomethyl)piperazine-1-carboxylate To a solution of [(2R)-4-methylmorpholin-2-yl]methanol (203 mg, 1.55 mmol, 3.0 eq) in toluene (4.0 mL) was added t-BuONa (99.2 mg, 1.03 mmol, 2.0 eq). The mixture was stirred at 0° C. for 0.5 hour. Then tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (300 mg, 516 umol, 1.0 eq) was added to the above mixture. The mixture was stirred at 0° C. for 0.5 hour. After completion, the reaction mixture was added water (10.0 ml) and extracted with EA (10.0 mL×3). The organic layer was dried over Na$_2$SO$_4$, filtered and concentrated. The obtained product was purified by column chromatography (SiO$_2$, PE:EA=3:1-EA:MeOH=10:1) to give tert-butyl (2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]-2-(cyanomethyl)piperazine-1-carboxylate (250 mg, 366 umol, 71% yield, 95% purity) as yellow oil. LCMS [ESI, M+1]: 648.

$^1$H NMR (400 MHz, Chloroform-d) δ 7.75 (d, J=8.0 Hz, 1H), 7.61 (t, J=7.6 Hz, 1H), 7.52 (d, J=7.6 Hz, 1H), 7.49-7.39 (m, 1H), 7.33 (t, J=7.8 Hz, 1H), 7.26-7.17 (m, 1H), 4.68-4.53 (m, 1H), 4.48-4.31 (m, 2H), 4.29-4.19 (m, 1H), 4.16-4.01 (m, 3H), 4.00-3.82 (m, 4H), 3.79-3.69 (m, 1H), 3.63-3.53 (m, 1H), 3.36 (br dd, J=3.6, 13.6 Hz, 1H), 3.29-3.06 (m, 3H), 3.01-2.86 (m, 2H), 2.83-2.64 (m, 3H), 2.63-2.45 (m, 1H), 2.36-2.28 (m, 3H), 2.19 (dt, J=3.6, 11.6 Hz, 1H), 1.52 (s, 9H).

Step B: 2-[(2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]-2-(cyanomethyl)piperazine-1-carboxylate (240 mg, 370 umol, 1.0 eq) in DCM (1.0 mL) was added TFA (1.54 g, 13.5 mmol, 1.0 mL, 36.5 eq). The mixture was stirred at 25° C. for 0.5 hour. After completion, the reaction mixture was concentrated to give 2-[(2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]piperazin-2-yl]acetonitrile (300 mg, crude, 2TFA) as light red oil. LCMS [ESI, M+1]: 548.

Step C: 2-[(2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]piperazin-2-yl]acetonitrile (300 mg, 387 umol, 1.0 eq, 2TFA) and DIEA (599 mg, 4.64 mmol, 808 uL, 12.0 eq) in DCM (2.0 mL) was added prop-2-enoyl prop-2-enoate (73.1 mg, 580 umol, 1.50 eq). The mixture was stirred at 0° C. for 0.5 hour. After completion, the reaction mixture was quenched with MeOH (1.0 mL) and concentrated under vacuum. The obtained product was purified by prep-HPLC (column: Gemini 150*25 5 u; mobile phase: [water (0.04% NH$_3$.H$_2$O)-ACN]; B %: 45%-75%,10 min) to give title compound 2-[(2S)-4-[7-(8-chloro-1-naphthyl)-2-[[(2R)-4-methylmorpholin-2-yl]methoxy]-6,8-dihydro-5H-pyrido[3,4-d]pyrimidin-4-yl]-1-prop-2-enoyl-piperazin-2-yl]acetonitrile (EXAMPLE 363, 42.7 mg, 70.4 umol, 18% yield, 99% purity) as white solid. LCMS [ESI, M+1]: 602.

$^1$H NMR (400 MHz, Chloroform-d) δ 7.76 (d, J=8.0 Hz, 1H), 7.62 (t, J=7.2 Hz, 1H), 7.55-7.50 (m, 1H), 7.49-7.40 (m, 1H), 7.34 (t, J=7.8 Hz, 1H), 7.27-7.18 (m, 1H), 6.65-6.52 (m, 1H), 6.39 (br d, J=16.8 Hz, 1H), 5.83 (br d, J=10.8 Hz, 1H), 5.25-4.53 (m, 1H), 4.48-4.32 (m, 2H), 4.30-4.21 (m, 1H), 4.19-4.00 (m, 2H), 3.99-3.89 (m, 3H), 3.88-3.76 (m, 1H), 3.75-3.68 (m, 1H), 3.64-3.55 (m, 1H), 3.52-3.35 (m, 1H), 3.31-2.98 (m, 4H), 2.92-2.55 (m, 5H), 2.31 (s, 3H), 2.18 (dt, J=3.2, 11.4 Hz, 1H), 2.02 (dt, J=1.6, 10.8 Hz, 1H).

Example 364

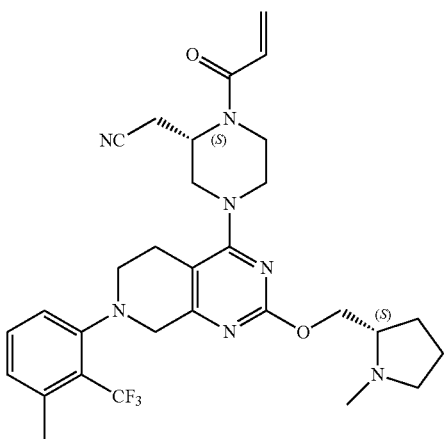

2-[(2S)-4-[2-[[(2S)-1-methylpyrrolidin-2-yl]methoxy]-7-[3-methyl-2-(trifluoromethyl)phenyl]-6,8-dihydro-5H-pyrido[3,4-d]pyrimidin-4-yl]-1-prop-2-enoyl-piperazin-2-yl]acetonitrile

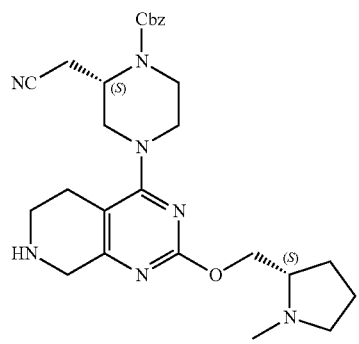
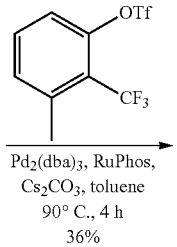
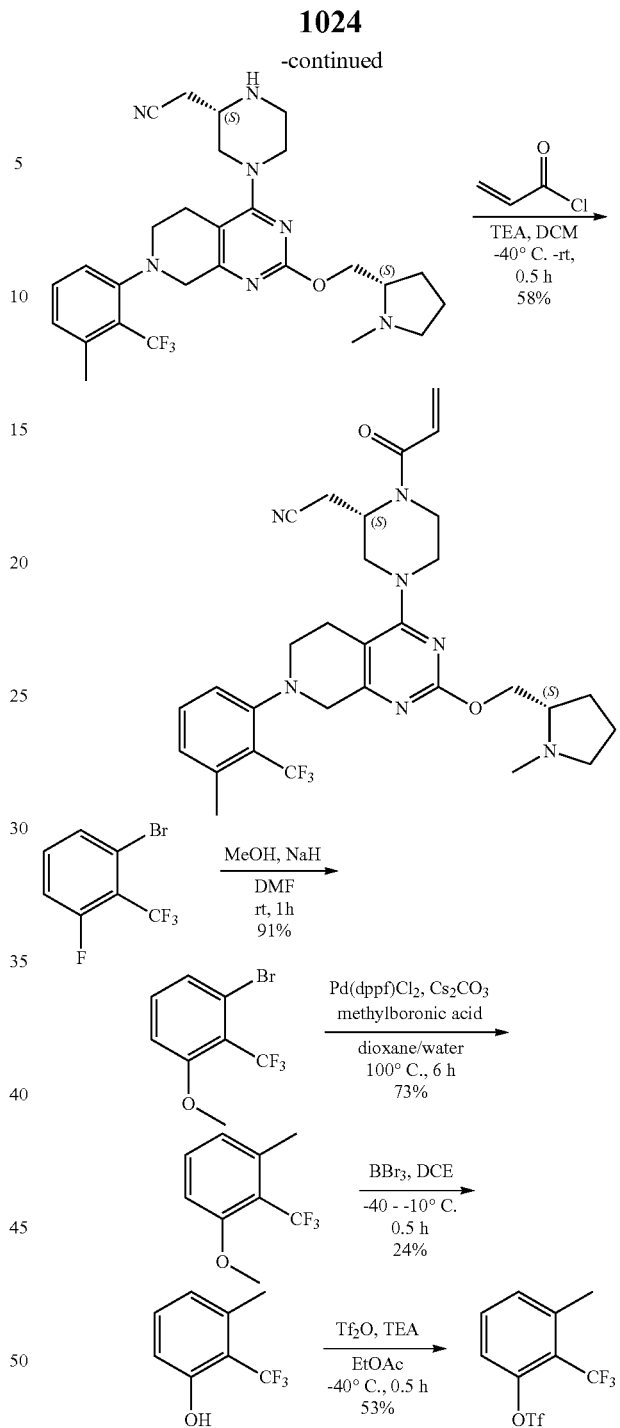

Step 1: 1-bromo-3-methoxy-2-(trifluoromethyl)benzene

To a solution of MeOH (1.32 g, 41.2 mmol, 1.67 mL, 2 eq) in DMF (125 mL) was added NaH (1.65 g, 41.2 mmol, 60.0% purity, 2 eq). The mixture was stirred at 25° C. for 0.5 hour. Then to the mixture was added 1-bromo-3-fluoro-2-(trifluoromethyl)benzene (5 g, 20.6 mmol, 1 eq) and stirred at 25° C. for 0.5 hour. The reaction mixture was quenched by ice water (20 mL). Water (300 mL) was added into the mixture and extracted with MTBE (3×100 mL). The combined organic layers were washed with water (50 mL) and brine (50 mL). The combined organic layers were dried over anhydrous $Na_2SO_4$, filtered and concentrated under vacuum. The residue was purified by silica gel chromatography (PE) to give 1-bromo-3-methoxy-2-(trifluoromethyl)benzene (5.28 g, 18.6 mmol, 91.0% yield, 90.0% purity) as a colorless oil.

$^1$H NMR (400 MHz, chloroform-d) δ=7.34-7.28 (m, 2H), 7.01-6.97 (m, 1H), 3.91 (s, 3H).

Step 2:
1-methoxy-3-methyl-2-(trifluoromethyl)benzene

To the solution of 1-bromo-3-methoxy-2-(trifluoromethyl)benzene (5.28 g, 20.7 mmol, 1 eq), $Cs_2CO_3$ (20.2 g, 62.1 mmol, 3 eq), methylboronic acid (6.20 g, 104 mmol, 5 eq) in dioxane (105 mL) and Water (21 mL) was added Pd(dppf)Cl$_2$ (2.27 g, 3.11 mmol, 0.15 eq) under $N_2$. The suspension was degassed under vacuum and purged with $N_2$ several times. The mixture was stirred under $N_2$ at 100° C. for 6 hours. Water (50 mL) was added into the mixture. The mixture was diluted with EtOAc (30 mL) and extracted with EtOAc (100 mL). The organic layer was dried over anhydrous $Na_2SO_4$, filtered and concentrated under vacuum. The residue was purified by silica gel chromatography (PE) to give 1-methoxy-3-methyl-2-(trifluoromethyl)benzene (3.2 g, 15.1 mmol, 73.1% yield, 90.0% purity) as a yellow oil.

$^1$H NMR (400 MHz, chloroform-d) δ=7.33 (t, J=8.0 Hz, 1H), 6.87 (br d, J=8.4 Hz, 1H), 6.83 (d, J=7.2 Hz, 1H), 3.88 (s, 3H), 2.49 (q, J=3.6 Hz, 3H).

Step 3: 3-methyl-2-(trifluoromethyl)phenol

To the solution of 1-methoxy-3-methyl-2-(trifluoromethyl)benzene (3.2 g, 16.8 mmol, 1 eq) in DCE (65 mL) was added BBr$_3$ (21.1 g, 84.1 mmol, 8.11 mL, 5 eq) at −40° C., the mixture was stirred at −40--10° C. for 0.5 hour. The reaction mixture was quenched by Water (100 mL). The mixture was diluted with EtOAc (20 mL) and extracted with EtOAc (2×50 mL). The combined organic layers were washed with brine (30 mL). The combined organic layers were dried over anhydrous $Na_2SO_4$, filtered and concentrated under vacuum. The residue was purified by silica gel chromatography (PE:EtOAc from 1:0 to 50:1) to give 3-methyl-2-(trifluoromethyl)phenol (740 mg, 4.08 mmol, 24.2% yield, 97.0% purity) as a yellow solid.

$^1$H NMR (400 MHz, chloroform-d) δ=7.29-7.24 (m, 1H), 6.87-6.77 (m, 2H), 5.95 (q, J=6.4 Hz, 1H), 2.46 (q, J=2.8 Hz, 3H).

Step 4: [3-methyl-2-(trifluoromethyl)phenyl] trifluoromethanesulfonate

To the solution of 3-methyl-2-(trifluoromethyl)phenol (600 mg, 3.41 mmol, 1 eq), TEA (1.38 g, 13.6 mmol, 1.90 mL, 4 eq) in EtOAc (12 mL) was added Tf$_2$O (1.44 g, 5.11 mmol, 843 uL, 1.5 eq) at −40° C., the mixture was stirred at −40° C. for 0.5 hour. The mixture was quenched by Water (10 mL). The mixture was diluted with EtOAc (10 mL) and extracted with EtOAc (30 mL). The organic layer was washed with brine (20 mL), dried over anhydrous $Na_2SO_4$, filtered and concentrated under vacuum. The residue was purified by silica gel chromatography (PE:EtOAc from 1:0 to 100:1) to give [3-methyl-2-(trifluoromethyl)phenyl] trifluoromethanesulfonate (590 mg, 1.82 mmol, 53.0% yield, 95.0% purity) as a colorless oil.

$^1$H NMR (400 MHz, chloroform-d) δ=7.53-7.47 (m, 1H), 7.33 (d, J=7.6 Hz, 1H), 7.29 (d, J=8.4 Hz, 1H), 2.57 (q, J=2.8 Hz, 3H).

Step A: benzyl (2S)-2-(cyanomethyl)-4-[2-[[(2S)-1-methylpyrrolidin-2-yl]methoxy]-7-[3-methyl-2-(trifluoromethyl)phenyl]-6,8-dihydro-5H-pyrido[3,4-d]pyrimidin-4-yl]piperazine-1-carboxylate To the solution of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 600 mg, 973 umol, 1 eq), [3-methyl-2-(trifluoromethyl)phenyl] trifluoromethanesulfonate (450 mg, 1.46 mmol, 1.5 eq), $Cs_2CO_3$ (951 mg, 2.92 mmol, 3 eq) and RuPhos (90.8 mg, 195 umol, 0.2 eq) in toluene (12 mL) was added Pd$_2$(dba)$_3$ (89.1 mg, 97.3 umol, 0.1 eq) under $N_2$. The suspension was degassed under vacuum and purged with $N_2$ several times. The mixture was stirred under $N_2$ at 90° C. for 4 hours. Water (15 mL) was added into the mixture. The mixture was diluted with EtOAc (10 mL) and extracted with EtOAc (30 mL). The organic layer was washed with brine (20 mL), dried over anhydrous $Na_2SO_4$, filtered and concentrated under vacuum. The residue was purified by silica gel chromatography (from PE:EtOAc=5:1~1:1 to EtOAc:MeOH=1:0~20:1). Then the residue was purified by reversed phase flash column (ACN/Water (0.1% FA)=50.0%) to give benzyl (2S)-2-(cyanomethyl)-4-[2-[[(2S)-1-methylpyrrolidin-2-yl]methoxy]-7-[3-methyl-2-(trifluoromethyl)phenyl]-6,8-dihydro-5H-pyrido[3,4-d]pyrimidin-4-yl]piperazine-1-carboxylate (240 mg, 354 umol, 36% yield, 98.0% purity) as a yellow oil. LCMS [ESI, M+1]: 664.

$^1$H NMR (400 MHz, chloroform-d) δ=7.41-7.35 (m, 6H), 7.18 (d, J=8.0 Hz, 1H), 7.07 (d, J=7.6 Hz, 1H), 7.10-7.04 (m, 1H), 5.20 (s, 2H), 4.69 (br s, 1H), 4.38 (dd, 10.8 Hz, 1H), 4.16 (t, J=3.2 Hz, 1H), 4.05 (s, 2H), 3.89 (br d, J=12.0 Hz, 1H), 3.30 (br s, 2H), 3.21-2.95 (m, 5H), 2.92-2.62 (m, 6H), 2.52 (q, J=3.6 Hz, 3H), 2.48 (s, 3H), 2.33-2.24 (m, 1H), 2.05-2.00 (m, 1H), 1.90-1.79 (m, 3H).

Step B: NH$_3$ was bubbled into MeOH (5 mL) for 5 minutes. To the solution was added benzyl (2S)-2-(cyanomethyl)-4-[2-[[(2S)-1-methylpyrrolidin-2-yl]methoxy]-7-[3-methyl-2-(trifluoromethyl)phenyl]-6,8-dihydro-5H-pyrido[3,4-d]pyrimidin-4-yl]piperazine-1-carboxylate (240 mg, 362 umol, 1 eq), Pd/C (50 mg, 10.0% purity) under $N_2$. The suspension was degassed under vacuum and purged with $H_2$ several times. The mixture was stirred under $H_2$ (15 psi) at 30° C. for 0.5 hour. The reaction mixture was filtered, the filtrate was concentrated under vacuum to give 2-[(2S)-4-[2-[[(2S)-1-methylpyrrolidin-2-yl]methoxy]-7-[3-methyl-2-(trifluoromethyl)phenyl]-6,8-dihydro-5H-pyrido[3,4-d]pyrimidin-4-yl]piperazin-2-yl]acetonitrile (180 mg, 336 umol, 93.0% yield, 99.0% purity) as a brown oil which was used for next step without further purification. LCMS [ESI, M+1]: 530.

Step C: 2-[(2S)-4-[2-[[(2S)-1-methylpyrrolidin-2-yl]methoxy]-7-[3-methyl-2-(trifluoromethyl)phenyl]-6,8-dihydro-5H-pyrido[3,4-d]pyrimidin-4-yl]-1-prop-2-enoyl-piperazin-2-yl]acetonitrile To the solution of 2-[(2S)-4-[2-[[(2S)-1-methylpyrrolidin-2-yl]methoxy]-7-[3-methyl-2-(trifluoromethyl)phenyl]-6,8-dihydro-5H-pyrido[3,4-d]pyrimidin-4-yl]piperazin-2-yl]acetonitrile (170 mg, 321 umol, 1 eq) and TEA (97.4 mg, 963 umol, 134 uL, 3 eq) in DCM (3.5 mL) was added prop-2- enoyl chloride (43.6 mg, 482 umol, 39.3 uL, 1.5 eq) at −40° C., the mixture was stirred at −40-30° C. for 0.5 hour. The reaction mixture was quenched by Water (2 mL) and separated. The aqueous phase was extracted with EtOAc (4 mL). The combined organic layers were dried over anhydrous Na₂SO₄, filtered and concentrated under vacuum. The residue was purified by prep-HPLC (column: Gemini 150*25 5 u; mobile phase: [water (0.05% ammonia hydroxide v/v)-ACN]; B %: 55%-85%,12 min) to give title compound 2-[(2S)-4-[2-[[(2S)-1-methylpyrrolidin-2-yl]methoxy]-7-[3-methyl-2-(trifluoromethyl)phenyl]-6,8-dihydro-5H-pyrido[3,4-d]pyrimidin-4-yl]-1-prop-2-enoyl-piperazin-2-yl]acetonitrile (EXAMPLE 364, 110 mg, 188 umol, 58.0% yield, 100% purity) as a white solid. LCMS [ESI, M+1]: 584.

¹H NMR (400 MHz, chloroform-d) δ=7.43-7.35 (m, 1H), 7.19 (d, J=8.4 Hz, 1H), 7.08 (d, J=7.6 Hz, 1H), 6.59 (br s, 1H), 6.40 (dd, J=1.6, 16.8 Hz, 1H), 5.83 (br d, J=10.4 Hz, 1H), 5.09 (br s, 1H), 4.64 (br s, 1H), 4.37 (dd, J=4.8, 10.4 Hz, 1H), 4.18-4.08 (m, 2H), 4.06 (s, 2H), 3.96 (br d, J=12.4 Hz, 1H), 3.60 (br s, 1H), 3.30 (br s, 1H), 3.22-3.01 (m, 4H), 2.98-2.62 (m, 5H), 2.52 (q, J=3.2 Hz, 3H), 2.48 (s, 3H), 2.33-2.23 (m, 1H), 2.11-1.99 (m, 1H), 1.90-1.68 (m, 3H).

Example 365

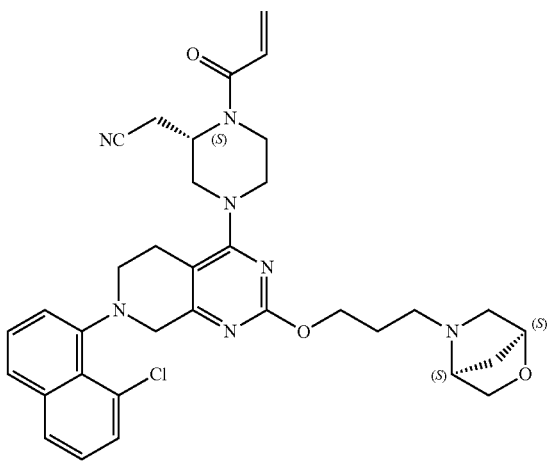

2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl]acetonitrile

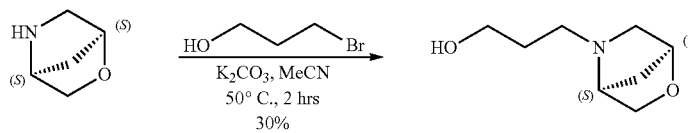

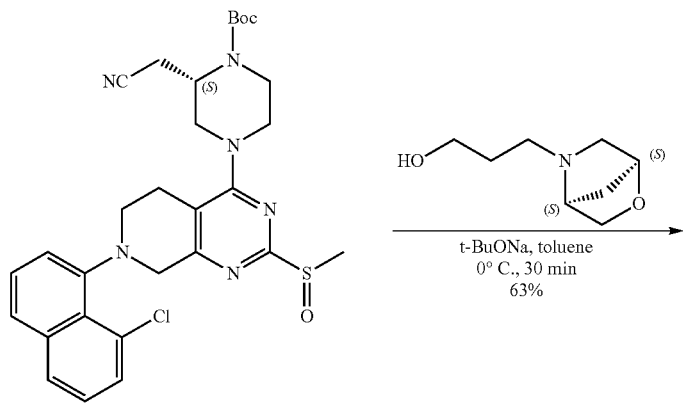

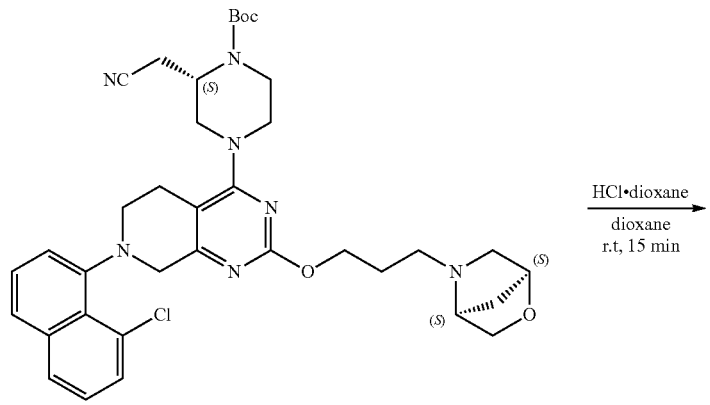

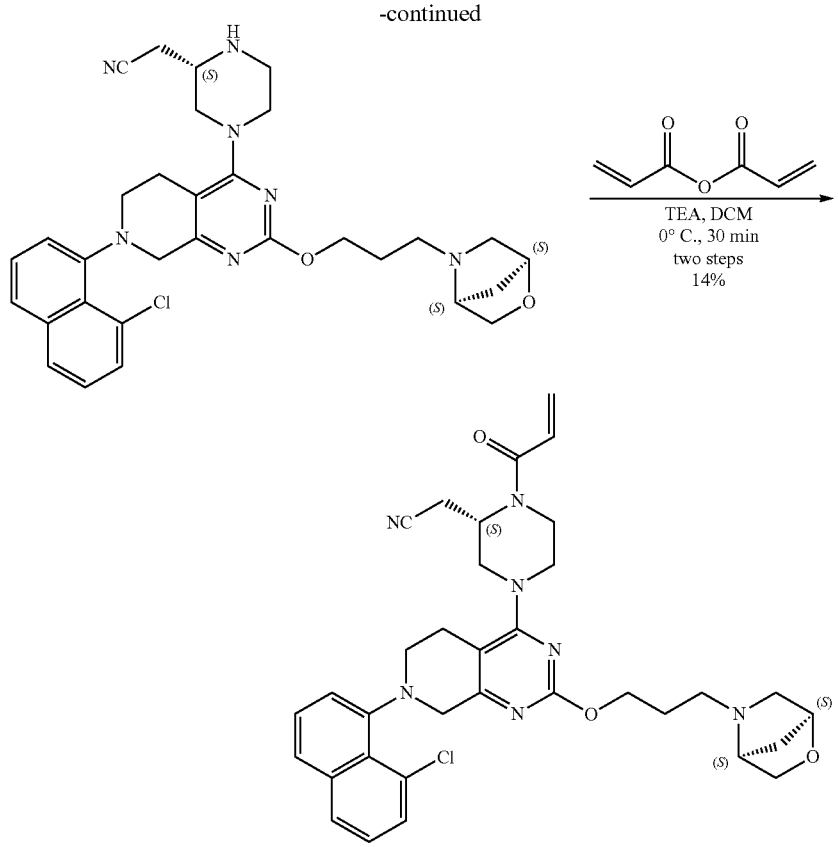

Insert: 3-[(1S,4S)-2-oxa-5-azabicyclo[2.2.1]heptan-5-yl]propan-1-ol

To a solution of (1S,4S)-2-oxa-5-azabicyclo[2.2.1]heptane (500 mg, 3.69 mmol, 1.0 eq, HCl), 3-bromopropan-1-ol (513 mg, 3.69 mmol, 333 uL, 1.0 eq) in $CH_3CN$ (6.0 mL) was added $K_2CO_3$ (1.53 g, 11.1 mmol, 3.0 eq). The mixture was stirred at 50° C. for 2 hours. After completion, the reaction mixture was filtered and the filtrate was evaporated. The residue was purified by column chromatography ($SiO_2$, Ethyl acetate:MeOH=50:1 to 20:1) to give 3-[(1S,4S)-2-oxa-5-azabicyclo[2.2.1]heptan-5-yl]propan-1-ol (195 mg, 1.12 mmol, 30% yield, 90% purity) as colorless oil.

$^1$H NMR (400 MHz, Chloroform-d) δ 4.42 (s, 1H), 3.99 (d, J=8.0 Hz, 1H), 3.82 (t, J=5.6 Hz, 2H), 3.65-3.61 (m, 1H), 3.53-3.45 (m, 2H), 2.99-2.92 (m, 2H), 2.84-2.77 (m, 1H), 2.67-2.61 (m, 1H), 1.86-1.80 (m, 1H), 1.79-1.58 (m, 3H).

Step A: tert-butyl (2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-2-(cyanomethyl)piperazine-1-carboxylate To a mixture of 3-[(1S,4S)-2-oxa-5-azabicyclo[2.2.1]heptan-5-yl]propan-1-ol (325 mg, 2.06 mmol, 3.0 eq), t-BuONa (198 mg, 2.06 mmol, 3.0 eq) in toluene (2.0 mL) was added a solution of tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (Intermediate 71, Step A, 400 mg, 688 umol, 1.0 eq) in toluene (2.0 mL) in portions, the mixture was stirred at 0° C. for 30 min under $N_2$ atmosphere. After completion, the organic solvent was added water (10.0 mL). The aqueous phase was extracted with ethyl acetate (3×10 mL). Combine extracts were washed with brine (20.0 mL), dried with $Na_2SO_4$, the solvent was then removed under vacuum. The residue was purified by column chromatography ($SiO_2$, Petroleum ether:Ethyl acetate=3:1 to Ethyl acetate:MeOH=20:1) to give tert-butyl (2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-2-(cyanomethyl)piperazine-1-carboxylate (320 mg, 432 umol, 62% yield, 91% purity) as yellow solid. LCMS [ESI, M+1]: 674.

Step B: 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-2-(cyanomethyl)piperazine-1-carboxylate (340 mg, 504 umol, 1.0 eq) in dioxane (3.0 mL) was added HCl.dioxane (4.0 M, 3.0 mL, 23.8 eq). The mixture was stirred at 25° C. for 15 min under $N_2$ atmosphere. After completion, the organic solvent was removed under vacuum. The obtained product was adjusted with saturated $NaHCO_3$ aqueous (10 mL), extracted with ethyl acetate (3×10 mL), the combined organic layer was dried over $Na_2SO_4$, filtered and concentrated. The crude product 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (270 mg, crude) was obtained as yellow solid and used into the next step without further purification. LCMS [ESI, M+1]: 574.

Step C: 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (270 mg, 470 umol, 1.0 eq) in DCM (4.0 mL) was added TEA (143 mg, 1.41 mmol, 196 uL, 3.0 eq) and prop-2-enoyl prop-2-enoate (178 mg, 1.41 mmol, 3.0 eq) at 0° C. The mixture was stirred at 0° C. for 30 min under $N_2$ atmosphere. After completion, the organic solvent was removed under vacuum. The residue was purified by column chromatography (Base $Al_2O_3$, Petroleum ether: Ethyl acetate=3:1 to 1:1), then the crude product was concentrated and repurified by prep-HPLC (column: Phenomenex Gemini 150*25 mm*10 um; mobile phase: [water (0.05% ammonia hydroxide v/v)-ACN]; B %: 45%-75%, 12 min) and under lyophilization. Title compound 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-prop-2-enoyl-piperazin-2-yl]acetonitrile (EXAMPLE 365, 43.1 mg, 67.7 umol, 14% yield, 98% purity) was obtained as off-white solid. LCMS [ESI, M+1]: 628.

$^1$H NMR (400 MHz, chloroform-d) δ 7.76 (d, J=9.6 Hz, 1H), 7.62 (t, J=7.6 Hz, 1H), 7.50 (d, J=6.4 Hz, 1H), 7.47-7.40 (m, 1H), 7.34 (t, J=8.0 Hz, 1H), 7.26-7.16 (m, 1H), 6.67-6.54 (m, 1H), 6.40 (d, J=16.8 Hz, 1H), 5.82 (d, J=10.8 Hz, 1H), 5.16-5.03 (m, 1H), 4.48-4.40 (m, 1H), 4.38-4.34 (m, 3H), 4.22-4.08 (m, 1H), 4.07-3.99 (m, 2H), 3.97-3.74 (m, 2H), 3.64-3.55 (m, 2H), 3.54-3.35 (m, 2H), 3.31-3.20 (m, 1H), 3.19-3.14 (m, 1H), 3.13-2.99 (m, 2H), 2.92 (d, J=10.4 Hz, 1H), 2.89-2.81 (m, 1H), 2.80-2.76 (m, 1H), 2.75-2.68 (m, 1H), 2.64-2.57 (m, 1H), 2.52 (d, J=10.0 Hz, 1H), 1.98-1.89 (m, 2H), 1.85 (d, J=9.2 Hz, 1H), 1.74-1.70 (m, 2H).

Example 366

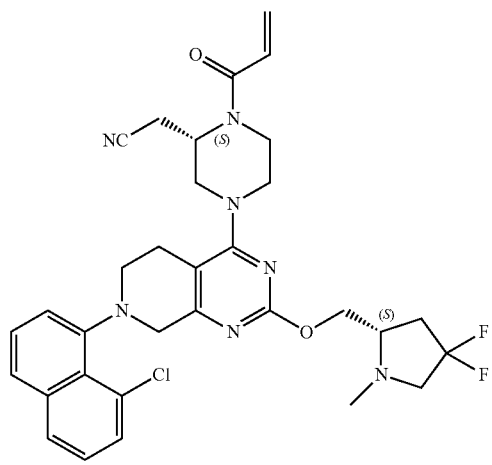

2-[(2S)-4-[7-(8-chloro-1-naphthyl)-2-[[(2S)-4,4-difluoro-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile

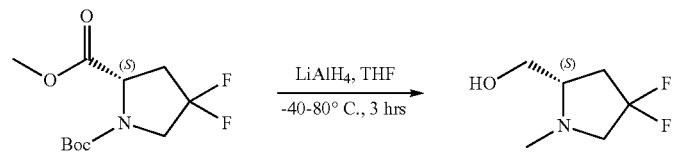

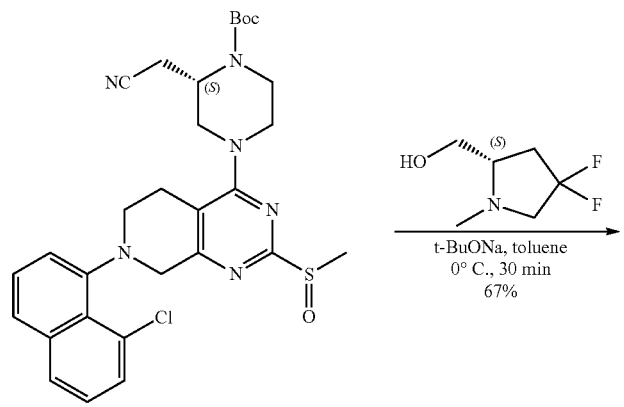

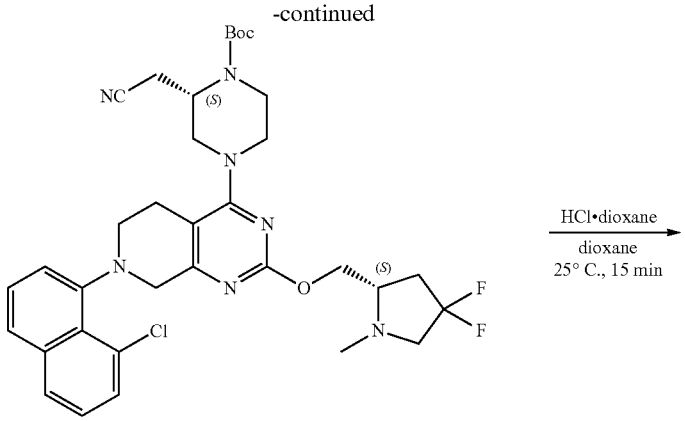

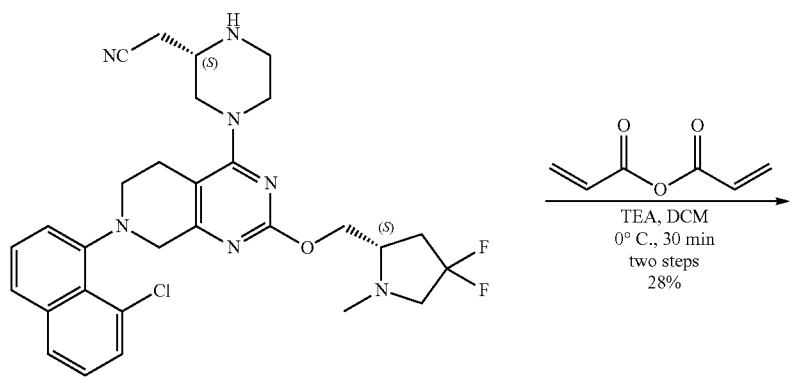

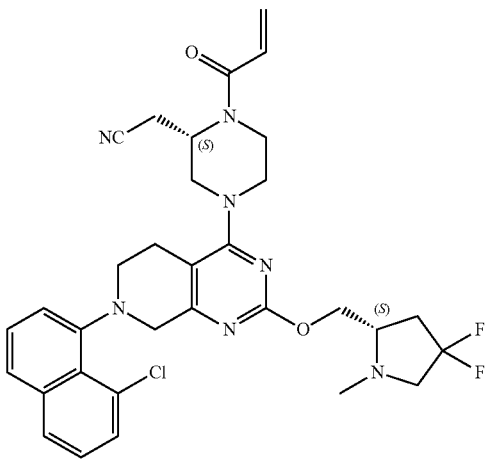

Insert: To a solution of O1-tert-butyl O2-methyl (2S)-4,4-difluoropyrrolidine-1,2-dicarboxylate (300 mg, 1.13 mmol, 1.0 eq) in THF (8.0 mL) was added LiAlH₄ (129 mg, 3.39 mmol, 3.0 eq). The mixture was stirred at −40° C. for 1 hour. Then the mixture was stirred at 80° C. for 2 hours under N₂ atmosphere. After completion, the reaction mixture was quenched with saturated Na₂SO₄ aqueous solution (6.0 mL), dried with Na₂SO₄. Then the mixture was filtered and the filtrate was concentrated. [(2S)-4,4-difluoro-1-methyl-pyrrolidin-2-yl] methanol (165 mg, crude) was obtained as colorless oil and used into the next step without further purification.

Step A: tert-butyl (2S)-4-[7-(8-chloro-1-naphthyl)-2-[[(2S)-4,4-difluoro-1-methyl-pyrrolidin-2-yl]methoxyl]-6,8-dihydro-5H-pyrido [3,4-d]pyrimidin-4-yl]-2-(cyanomethyl)piperazine-1-carboxylate To a solution of [(2S)-4,4-difluoro-1-methyl-pyrrolidin-2-yl]methanol (156 mg, 1.03 mmol, 3.0 eq) in toluene (2.0 mL) was added t-BuONa (99.2 mg, 1.03 mmol, 3.0 eq) at 0° C. and a solution of tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (200 mg, 344 umol, 1.0 eq) in toluene (1.0 mL) dropwise at 0° C. under N₂. The reaction mixture was stirred at 0° C. for 30 min. After completion, the organic solvent was added water (10.0 mL), extracted with ethyl acetate (3×10 mL). Combine extracts were washed with brine (20.0 mL), dried with Na₂SO₄, filtered and the filtrate was concentrated. The residue was purified by column chromatography (SiO₂, Petroleum ether: Ethyl acetate=5:1 to 1:1) to give tert-butyl (2S)-4-[7-(8-chloro-1-naphthyl)-2-[[(2S)-4,4-difluoro-1-methyl-pyrrolidin-2-yl]methoxy]-6,8-dihydro-5H-pyrido[3,4-d]pyrimidin-4-yl]-2-(cyanomethyl)piperazine-1-carboxylate (160 mg, 230 umol, 67% yield, 96% purity) as yellow solid. LCMS [ESI, M+1]: 668.

Step B: 2-[(2S)-4-[7-(8-chloro-1-naphthyl)-2-[[(2S)-4,4-difluoro-1-methyl-pyrrolidin-2-yl]methoxyl]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2S)-4,4-difluoro-1-methyl-pyrrolidin-2-yl]methoxy]-6,8-dihydro-5H-pyrido[3,4-d]pyrimidin-4-yl]-2-(cyanomethyl)piperazine-1-carboxylate (137 mg, 205 umol, 1.0 eq) in dioxane (1.0 mL) was added HCl.dioxane (4 M, 1.0 mL, 19.5 eq). The mixture was stirred at 25° C. for 15 min under N₂ atmosphere. After completion, the organic solvent was removed under vacuum. The obtained product was adjusted with saturated NaHCO₃ aqueous (10 mL), extracted with ethyl acetate (3×10 mL), dried over Na₂SO₄, filtered and concentrated. The crude product 2-[(2S)-4-[7-(8-chloro-1-naphthyl)-2-[[(2S)-4,4-difluoro-1-methyl-pyrrolidin-2-yl] methoxy]-6,8-dihydro-5H-pyrido[3,4-d]pyrimidin-4-yl]piperazin-2-yl]acetonitrile (110 mg, crude) was obtained as yellow solid and used into the next step without further purification. LCMS [ESI, M+1]: 568.

Step C: 2-[(2S)-4-[7-(8-chloro-1-naphthyl)-2-[[(2S)-4,4-difluoro-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-chloro-1-naphthyl)-2-[[(2S)-4,4-difluoro-1-methyl-pyrrolidin-2-yl]methoxy]-6,8-dihydro-5H-pyrido[3,4-d]pyrimidin-4-yl]piperazin-2-yl]acetonitrile (110 mg, 194 umol, 1.0 eq) in DCM (3.0 mL) was added TEA (196 mg, 1.94 mmol, 270 uL, 10.0 eq) and prop-2-enoyl prop-2-enoate (73.3 mg, 581 umol, 3.0 eq) at 0° C. The mixture was stirred at 0° C. for 30 min under N₂ atmosphere. After completion, the reaction mixture was quenched with methanol (6.0 mL) and the mixture was removed under vacuum. The residue was purified by prep-HPLC (column: Phenomenex Gemini 150×25 mm×10 um; mobile phase: [water (0.05% ammonia hydroxide v/v)-ACN]; B %: 55%-85%, 12 min) and under lyophilization. Title compound 2-[(2S)-4-[7-(8-chloro-1-naphthyl)-2-[[(2S)-4,4-difluoro-1-methyl-pyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 366, 34.1 mg, 54.5 umol, 28% yield, 99% purity) was obtained as off-white solid. LCMS [ESI, M+1]: 622.

¹H NMR (400 MHz, chloroform-d) δ 7.76 (d, J=8.0 Hz, 1H), 7.63 (t, J=7.2 Hz, 1H), 7.50 (d, J=7.6 Hz, 1H), 7.49-7.42 (m, 1H), 7.34 (t, J=8.0 Hz, 1H), 7.26-7.19 (m, 1H), 6.63-6.57 (m, 1H), 6.40 (d, J=16.8 Hz, 1H), 5.84 (d, J=10.4 Hz, 1H), 5.02-4.98 (m, 1H), 4.49-4.37 (m, 2H), 4.31-4.22 (m, 1H), 4.19-3.97 (m, 2H), 3.96-3.89 (m, 1H), 3.88-3.77 (m, 1H), 3.76-3.65 (m, 1H), 3.64-3.55 (m, 1H), 3.52-3.37 (m, 2H), 3.36-3.10 (m, 3H), 3.07-2.95 (m, 2H), 2.94-2.80 (m, 1H), 2.79-2.48 (m, 4H), 2.47-2.45 (m, 3H), 2.36-2.24 (m, 1H).

Example 367

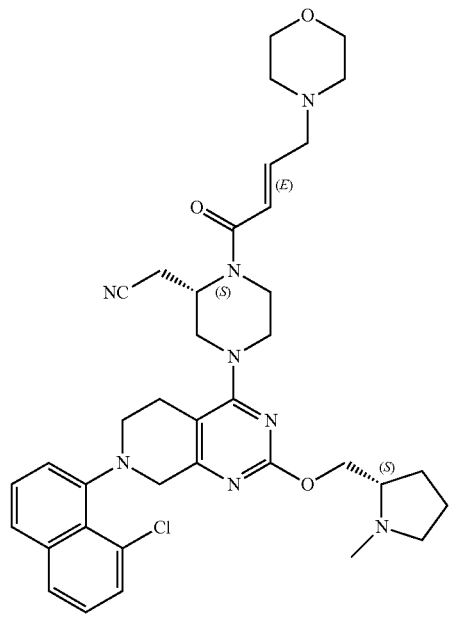

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-morpholinobut-2-enoyl]piperazin-2-yl]acetonitrile

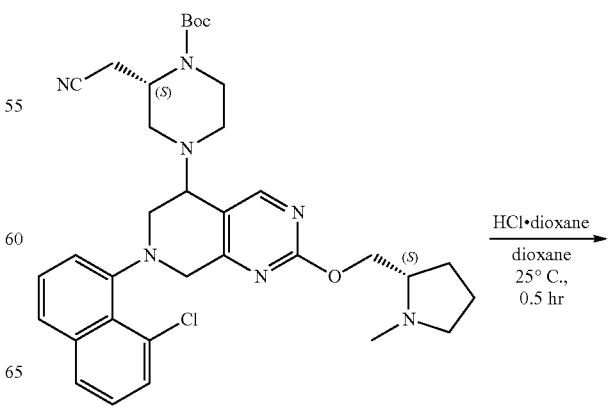

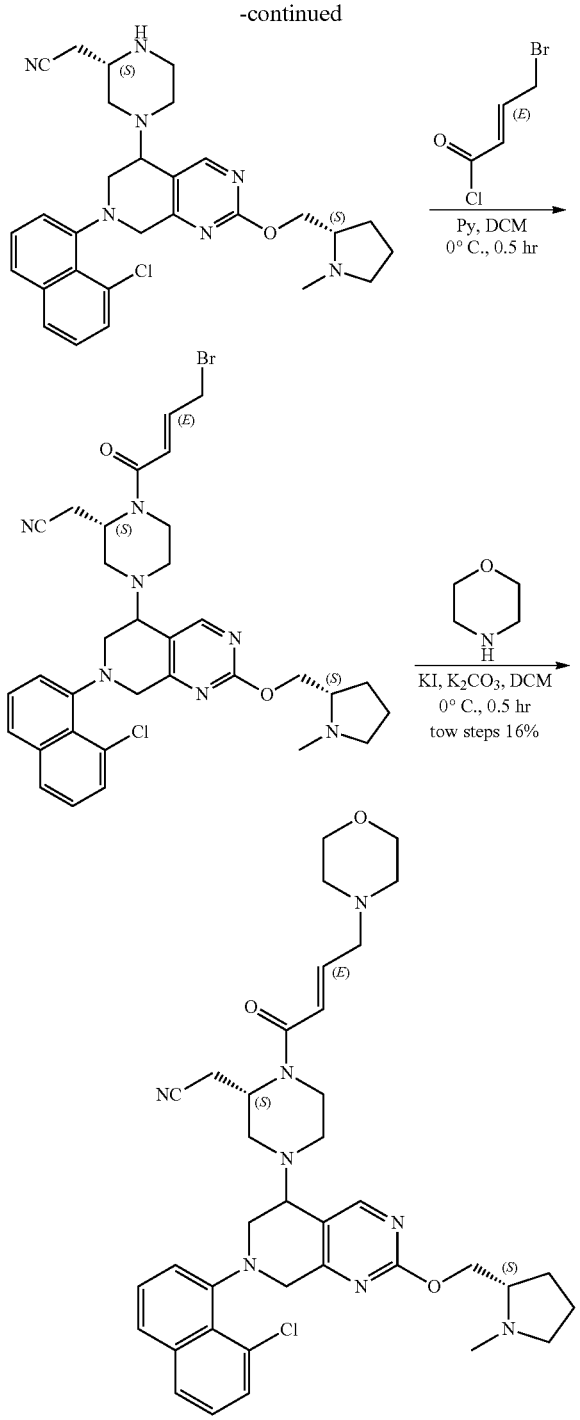

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (Intermediate 71, Step A, 200 mg, 316 umol, 1.0 eq) in dioxane (1.5 mL) was added HCl.dioxane (4 M, 1.5 mL, 19.0 eq). The mixture was stirred at 25° C. for 0.5 hour under N₂ atmosphere. After completion, the organic solvent was removed under vacuum. The obtained product was adjusted with saturated NaHCO₃ aqueous (10 mL), extracted with ethyl acetate (3×10 mL), dried over Na₂SO₄, filtered and the filtrate was concentrated. The crude product 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (130 mg, crude) was obtained as yellow solid and used into the next step without further purification. LCMS [ESI, M+1]: 532.

Step B: 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 282 umol, 1.0 eq) in DCM (3.0 mL) was added Pyridine (446 mg, 5.64 mmol, 455 uL, 20.0 eq) and (E)-4-bromobut-2-enoyl chloride (155 mg, 846 umol, 3.0 eq). The mixture was stirred at 0° C. for 0.5 hour. After completion, the mixture was concentrated. The crude product 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (190 mg, crude) was obtained as yellow solid and used into the next step without further purification. LCMS [ESI, M+1]: 680.

Step C: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-morpholinobut-2-enoyl]piperazin-2-yl]acetonitrile To a solution of 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido [3,4-d]pyrimidin-4-yl]piperazin-2-yl]acetonitrile (190 mg, 280 umol, 1.0 eq), KI (9.29 mg, 56.0 umol, 0.20 eq) and K₂CO₃ (387 mg, 2.80 mmol, 10.0 eq) in DCM (5.0 mL) was added morpholine (146 mg, 1.68 mmol, 148 uL, 6.0 eq). The mixture was stirred at 0° C. for 0.5 hour. After completion, the reaction mixture was quenched with methanol (10.0 mL) and the mixture was removed under vacuum. The residue was purified by prep-HPLC (column: Phenomenex Gemini 150*25 mm*10 um; mobile phase: [water (0.05% ammonia hydroxide v/v)-ACN]; B %: 60%-90%, 12 min) and then under lyophilization. The title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-morpholinobut-2-enoyl]piperazin-2-yl]acetonitrile (EXAMPLE 367, 31.6 mg, 45.2 umol, 16% yield, 98% purity) was obtained as yellow solid. LCMS [ESI, M+1]: 685.

¹H NMR (400 MHz, chloroform-d) δ 7.78-7.73 (m, 1H), 7.62 (t, J=7.6 Hz, 1H), 7.55-7.51 (m, 1H), 7.48-7.41 (m, 1H), 7.34 (t, J=7.8 Hz, 1H), 7.26-7.18 (m, 1H), 7.02-6.91 (m, 1H), 6.55-6.42 (m, 1H), 5.15-5.01 (m, 1H), 4.47-4.34 (m, 2H), 4.20-4.13 (m, 1H), 4.12-4.04 (m, 1H), 3.95-3.79 (m, 2H), 3.78-3.65 (m, 5H), 3.62-3.63 (m, 1H), 3.52-3.36 (m, 1H), 3.30-3.14 (m, 4H), 3.13-2.97 (m, 3H), 2.88-2.77 (m, 1H), 2.73-2.53 (m, 3H), 2.52-2.46 (m, 7H), 2.34-2.22 (m, 1H), 2.11-1.99 (m, 1H), 1.88-1.70 (m, 3H).

1039
Example 368
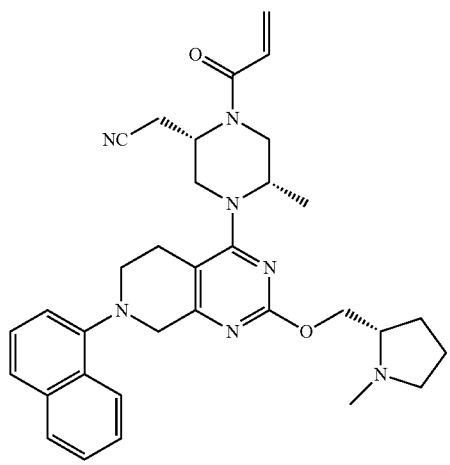 [SMILES: C=CC(=O)N1C[C@H](C)N(c2nc(OC[C@@H]3CCCN3C)nc3c2CCN(c2cccc4ccccc24)C3)C[C@@H]1CC#N]
2-((2S,5S)-1-acryloyl-5-methyl-4-(2-(((S)-1-methyl-pyrrolidin-2-yl)methoxy)-7-(naphthalen-1-yl)-5,6,7,8-tetrahydropyrido[3,4-d]pyrimidin-4-yl)piperazin-2-yl)acetonitrile
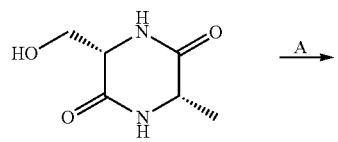 A→
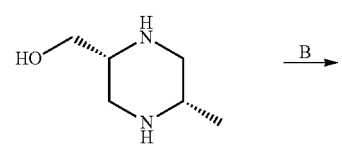 B→
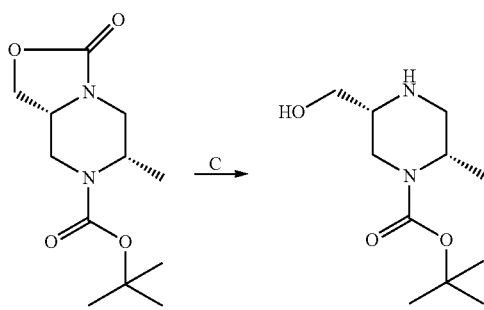
1040
-continued
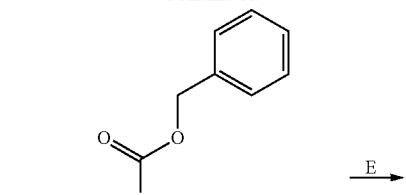 E→
 F→
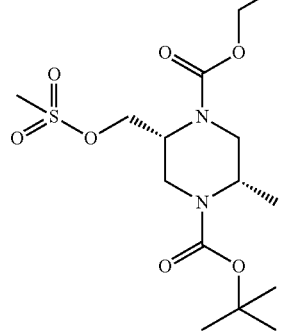 G→
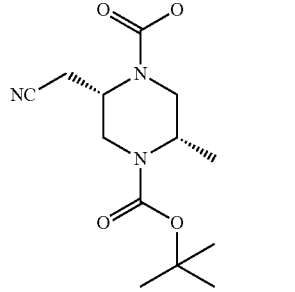 H→
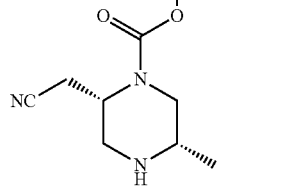

1041
-continued

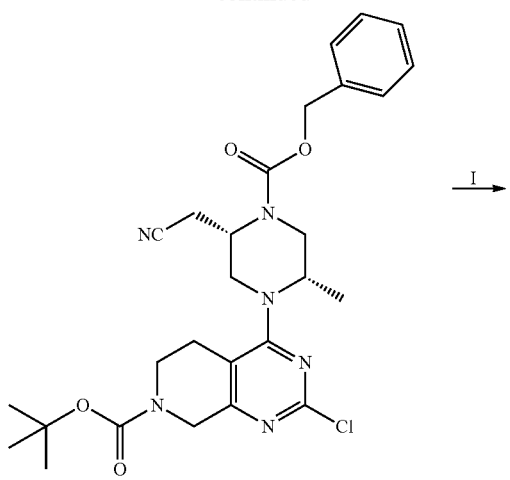

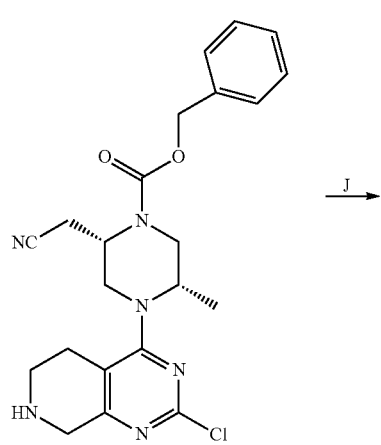

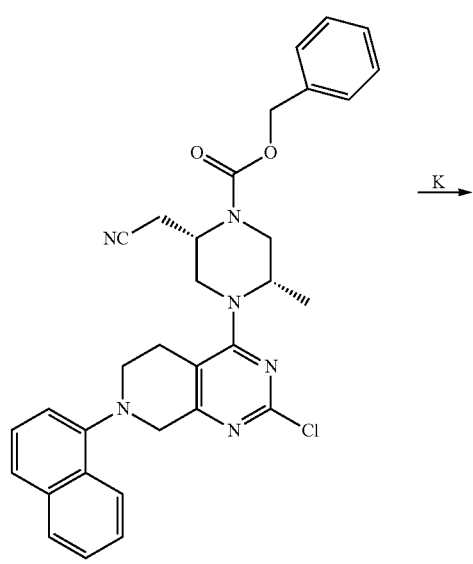

1042
-continued

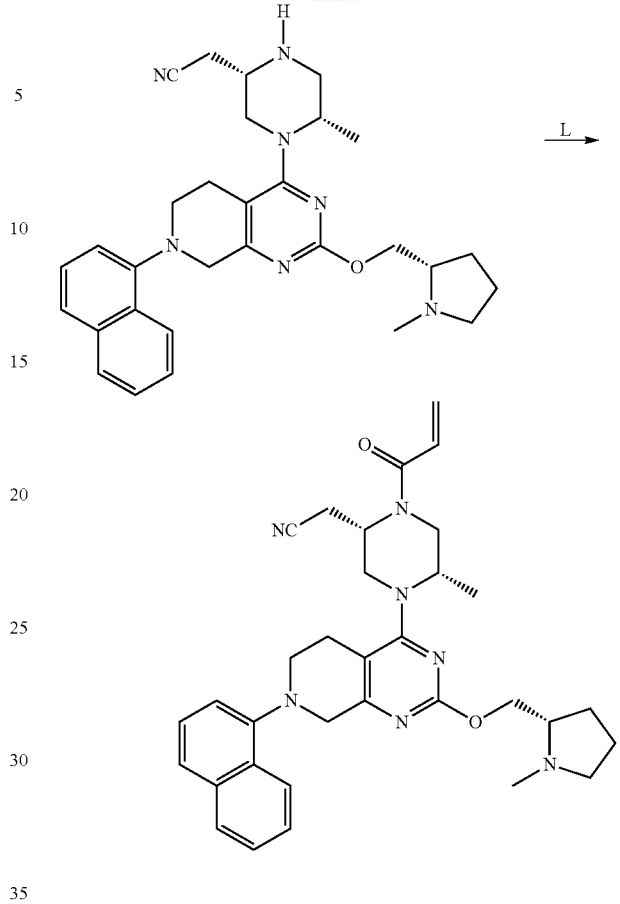

Step A: ((2R,5S)-5-methylpiperazin-2-yl)methanol

Cyclo(L-Ala-L-Ser) (400 mg, 2.53 mmol) was diluted with borane-tetrahydrofuran complex (18716 μl, 18.7 mmol), placed under nitrogen and heated to 70° C. After stirring for 12 hours, the reaction was allowed to cool. The reaction was cooled to 0° C. in an ice bath followed by the slow dropwise addition of MeOH (5116 μl, 126 mmol) followed by the addition of HCl (1096 μl, 6.58 mmol). After stirring for one hour, the reaction was concentrated to afford ((2R,5S)-5-methylpiperazin-2-yl)methanol (328 mg, 2.52 mmol, 99.6% yield).

Step B: tert-butyl (6S,8aR)-6-methyl-3-oxotetrahydro-3H-oxazolo[3,4-a]pyrazine-7(1H)-carboxylate ((2R,5S)-5-methylpiperazin-2-yl)methanol (500 mg, 3.84 mmol) was diluted with methanol (5 mL), placed under nitrogen and cooled to 0° C. TEA (2141 μl, 15.4 mmol) was added followed by BOC-Anhydride (2675 μl, 11.5 mmol) (in methanol 5 mL, over 15 minutes). The reaction was kept <10° C. for 1 hour and then the ice bath was removed. After 1 additional hour, the reaction was heated to 50° C. After stirring at 50° C. for 12 hours, the reaction was concentrated to afford tert-butyl (6S,8aR)-6-methyl-3-oxotetrahydro-3H-oxazolo[3,4-a]pyrazine-7(1H)-carboxylate (980 mg, 3.82 mmol, 99.6% yield).

Step C: tert-butyl (2S,5R)-5-(hydroxymethyl)-2-methylpiperazine-1-carboxylate

Tert-butyl (6S,8aR)-6-methyl-3-oxotetrahydro-3H-oxazolo[3,4-a]pyrazine-7(1H)-carboxylate (980 mg, 3.82 mmol) was diluted with ethanol (10047 µl, 172 mmol) followed by the addition of NaOH (9559 µl, 19.1 mmol). The reaction was placed under nitrogen, heated to 95° C. and stirred for 4 hours. TLC (methanol/DCM/NH$_4$OH, 10/89/1) staining with KMNO4 indicated the disappearance of a slightly higher rf spot. The reaction was allowed to cool, and then placed in an ice bath. The pH was adjusted to ~9 with 2N HCl and then extracted twice with DCM. The DCM was dried over MgSO$_4$, filtered and concentrated to afford tert-butyl (2S,5R)-5-(hydroxymethyl)-2-methylpiperazine-1-carboxylate (850 mg, 3.69 mmol, 96.5% yield).

Step D: 1-benzyl 4-(tert-butyl) (2R,5S)-2-(hydroxymethyl)-5-methylpiperazine-1,4-dicarboxylate Tert-butyl (2S,5R)-5-(hydroxymethyl)-2-methylpiperazine-1-carboxylate (350 mg, 1.52 mmol) was diluted with THF (4 mL), placed under nitrogen and cooled to 0° C. NaOH (1672 µl, 1.67 mmol) was added followed by the addition of benzyl chloroformate (228 µl, 1.52 mmol). After stirring for 2 hours, the reaction was diluted with ethyl acetate and water. The water was extracted two more times and the ethyl acetate was combined, dried over MgSO$_4$, filtered and concentrated. The material was purified on silica gel eluting with 10-80% ethyl acetate/hexanes to afford 1-benzyl 4-(tert-butyl) (2R,5S)-2-(hydroxymethyl)-5-methylpiperazine-1,4-dicarboxylate (300 mg, 0.823 mmol, 54.2% yield). ESI+APCI MS m/z 265.1 [M+H]$^+$ (minus boc).

Step E: 1-benzyl 4-(tert-butyl) (2R,5S)-5-methyl-2-(((methylsulfonyl)oxy)methyl)piperazine-1,4-dicarboxylate 1-benzyl 4-(tert-butyl) (2R,5S)-2-(hydroxymethyl)-5-methylpiperazine-1,4-dicarboxylate (300 mg, 0.823 mmol) was diluted with DCM (4 mL), placed under nitrogen and cooled to 0° C. DIEA (216 µl, 1.23 mmol) was added followed by the addition of methanesulfonyl chloride (70.1 µl, 0.905 mmol). After stirring for 2 hours at 0° C., the reaction was diluted with DCM and saturated sodium bicarbonate. The layers were separated and the ethyl acetate was dried over MgSO$_4$, filtered and concentrated. The material was purified on silica gel eluting with 10-50% ethyl acetate/hexanes to afford 1-benzyl 4-(tert-butyl) (2R,5S)-5-methyl-2-(((methylsulfonyl)oxy)methyl)piperazine-1,4-dicarboxylate (290 mg, 0.655 mmol, 79.6% yield).

Step F: 1-benzyl 4-(tert-butyl) (2S,5S)-2-(cyanomethyl)-5-methylpiperazine-1,4-dicarboxylate 1-benzyl 4-(tert-butyl) (2R,5S)-5-methyl-2-(((methylsulfonyl)oxy)methyl)piperazine-1,4-dicarboxylate (290 mg, 0.655 mmol) was diluted with DMA (4 mL) followed by the addition of NaCN (64.2 mg, 1.31 mmol). The reaction was heated to 55° C. and stirred for 12 hours. The reaction was allowed to cool, diluted with MTBE and washed with saturated sodium bicarbonate, water and brine. The MTBE was dried over MgSO$_4$, filtered and concentrated. The material was purified on silica gel eluting with 10-50% ethyl acetate/hexanes to afford 1-benzyl 4-(tert-butyl) (2S,5S)-2-(cyanomethyl)-5-methylpiperazine-1,4-dicarboxylate (200 mg, 0.536 mmol, 81.7% yield). ESI+APCI MS m/z 274.2 [M+H]$^+$ (minus boc).

Step G: benzyl (2S,5S)-2-(cyanomethyl)-5-methylpiperazine-1-carboxylate 1-benzyl 4-(tert-butyl) (2S,5S)-2-(cyanomethyl)-5-methylpiperazine-1,4-dicarboxylate (200 mg, 0.536 mmol) was diluted with DCM (2 mL) followed by the addition of HCl (669 µl, 2.68 mmol). After stirring for 3 hours, the reaction was concentrated to afford benzyl (2S,5S)-2-(cyanomethyl)-5-methylpiperazine-1-carboxylate (146 mg, 0.534 mmol, 99.7% yield). ESI+APCI MS m/z 274.1 [M+H]$^+$.

Step H: tert-butyl 4-((2S,5S)-4-((benzyloxy)carbonyl)-5-(cyanomethyl)-2-methylpiperazin-1-yl)-2-chloro-5,8-dihydropyrido[3,4-d]pyrimidine-7(6H)-carboxylate tert-Butyl 2,4-dichloro-5,6-dihydropyrido[3,4-d]pyrimidine-7(8H)-carboxylate (211 mg, 0.695 mmol) was diluted with DMA (4 mL) followed by the addition of benzyl (2S,5S)-2-(cyanomethyl)-5-methylpiperazine-1-carboxylate (190 mg, 0.695 mmol) and DIEA (364 µl, 2.09 mmol). The reaction was allowed to stir at ambient temperature for 12 hours. Very little product was detected so the reaction was heated to 75° C. for an additional 12 hours. The reaction was allowed to cool, diluted with ethyl acetate and water. The ethyl acetate was washed with water, brine, dried over MgSO$_4$, filtered and concentrated. The material was purified on silica gel eluting with 10-50% ethyl acetate/hexanes to afford tert-butyl 4-((2S,5S)-4-((benzyloxy)carbonyl)-5-(cyanomethyl)-2-methylpiperazin-1-yl)-2-chloro-5,8-dihydropyrido[3,4-d]pyrimidine-7(6H)-carboxylate (53 mg, 0.0980 mmol, 14.1% yield). ESI+APCI MS m/z 541.2 [M+H]$^+$.

Step I: benzyl (2S,5S)-4-(2-chloro-5,6,7,8-tetrahydropyrido[3,4-d]pyrimidin-4-yl)-2-(cyanomethyl)-5-methylpiperazine-1-carboxylate Tert-butyl 4-((2S,5S)-4-((benzyloxy)carbonyl)-5-(cyanomethyl)-2-methylpiperazin-1-yl)-2-chloro-5,8-dihydropyrido[3,4-d]pyrimidine-7(6H)-carboxylate (53 mg, 0.098 mmol) was diluted with DCM followed by the addition of HCl (122 µl, 0.49 mmol). After stirring for 4 hours, the reaction was concentrated to afford benzyl (2S,5S)-4-(2-chloro-5,6,7,8-tetrahydropyrido[3,4-d]pyrimidin-4-yl)-2-(cyanomethyl)-5-methylpiperazine-1-carboxylate (43 mg, 0.098 mmol, 100% yield). ESI+APCI MS m/z 441.1 [M+H]$^+$.

Step J: benzyl (2S,5S)-4-(2-chloro-7-(naphthalen-1-yl)-5,6,7,8-tetrahydropyrido[3,4-d]pyrimidin-4-yl)-2-(cyanomethyl)-5-methylpiperazine-1-carboxylate Benzyl (2S,5S)-4-(2-chloro-5,6,7,8-tetrahydropyrido[3,4-d]pyrimidin-4-yl)-2-(cyanomethyl)-5-methylpiperazine-1-carboxylate (43 mg, 0.0975 mmol), 1-iodonaphthalene (124 mg, 0.488 mmol), Cs$_2$CO$_3$ (95.3 mg, 0.293 mmol) and Methanesulfonato(2-dicyclohexylphosphino-2',6'-di-i-propoxy-1,1'-biphenyl)(2'-methylamino-1,1'-biphenyl-2-yl) palladium(II) (12.5 mg, 0.0146 mmol) were diluted with DMA (600 uL), purged with argon, sealed and heated to 92° C. After stirring for 12 hours, the reaction was allowed to cool, diluted with ethyl acetate and water. The layers were separated and the ethyl acetate was washed with brine, dried over MgSO₄, filtered and concentrated. The material was purified on silica gel eluting with 10-50% ethyl acetate/hexanes to afford benzyl (2S,5S)-4-(2-chloro-7-(naphthalen-1-yl)-5,6,7,8-tetrahydropyrido[3,4-d]pyrimidin-4-yl)-2-(cyanomethyl)-5-methylpiperazine-1-carboxylate (26.5 mg, 0.0467 mmol, 47.9% yield). ESI+APCI MS m/z 567.2 [M+H]⁺.

Step K: 2-((2S,5S)-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile benzyl (2S,5S)-4-(2-chloro-7-(naphthalen-1-yl)-5,6,7,8-tetrahydropyrido[3,4-d]pyrimidin-4-yl)-2-(cyanomethyl)-5-methylpiperazine-1-carboxylate (26.5 mg, 0.0467 mmol), (s)-(dicyclohexyl(2',6'-diisopropoxy-[1,1'-biphenyl]-2-yl)-15-phosphanyl)(2'-(methylamino)-[1,1'-biphenyl]-2-yl)palladium(III) methanesulfonate (7.96 mg, 0.00935 mmol) and Cs₂CO₃ (76.1 mg, 0.234 mmol) were diluted with DMA (300 uL) followed by the addition of N-Methyl-1-prolinol (21.5 mg, 0.187 mmol). The reaction was purged with argon, sealed and heated to 90° C. After stirring for 12 hours, the reaction was allowed to cool, diluted with ethyl acetate and water. The ethyl acetate was dried over MgSO₄, filtered and concentrated. The material was purified on silica gel eluting with 10% methanol/DCM (1% NH₄OH) to afford benzyl (2S,5S)-2-(cyanomethyl)-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (8 mg, 0.0124 mmol, 26.5% yield) and 2-((2S,5S)-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (10 mg, 0.0195 mmol, 41.8% yield). ESI+APCI MS m/z 512.3 [M+H]⁺.

Step L: 2-((2S,5S)-1-acryloyl-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile 2-((2S,5S)-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (10 mg, 0.020 mmol) was diluted with DCM (200 uL) followed by the addition of DIEA (6.8 μl, 0.039 mmol). The reaction was placed under nitrogen and cooled to 0° C. acryloyl chloride (1.8 μl, 0.021 mmol) was added and the reaction was stirred for 2 hours. The reaction was poured into a 10% sodium bicarbonate solution and extracted with DCM. The DCM was dried over MgSO₄, filtered and concentrated. The material was purified on silica gel eluting with 10% methanol/DCM (1% NH₄OH) to afford title compound 2-((2S,5S)-1-acryloyl-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (EXAMPLE 368, 6 mg, 0.011 mmol, 54% yield). ESI+APCI MS m/z 566.3 [M+H]⁺.

Example 369

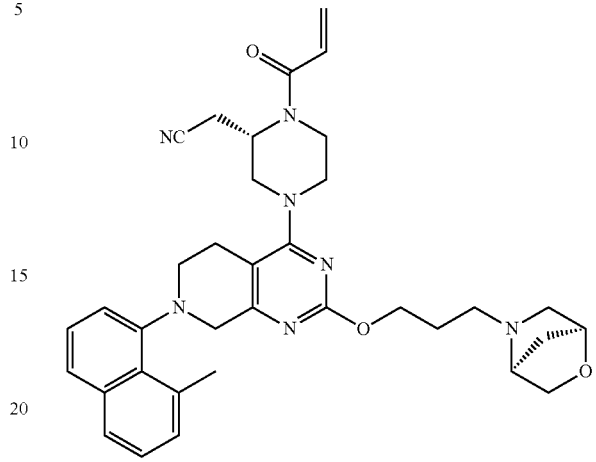

2-((S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)-1-acryloylpiperazin-2-yl)acetonitrile

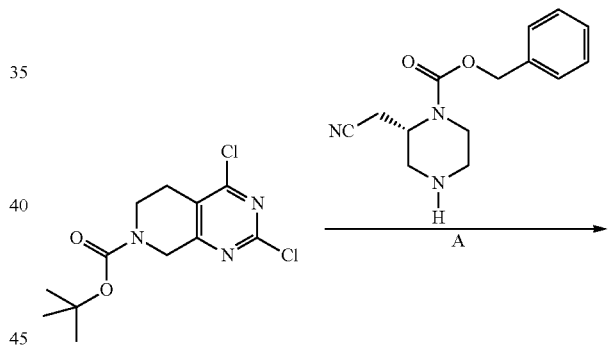

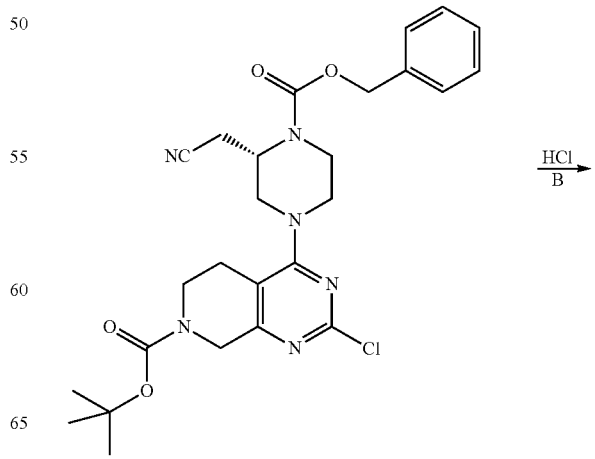

1047
-continued

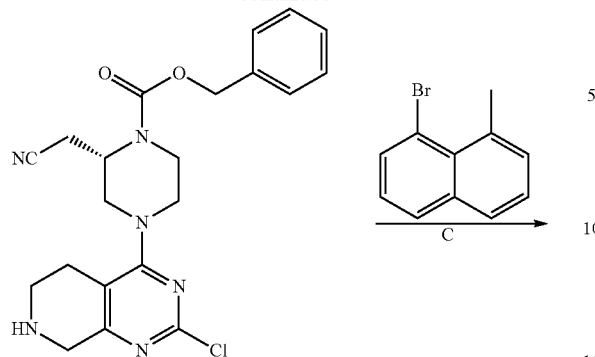

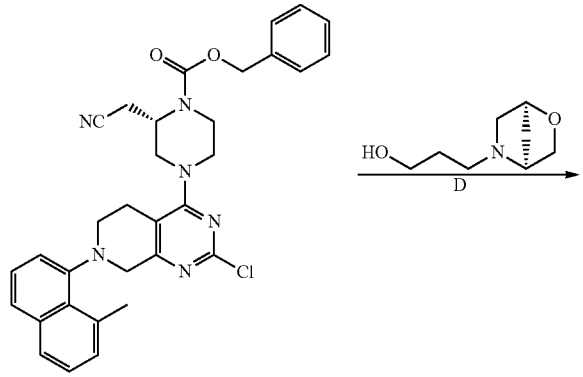

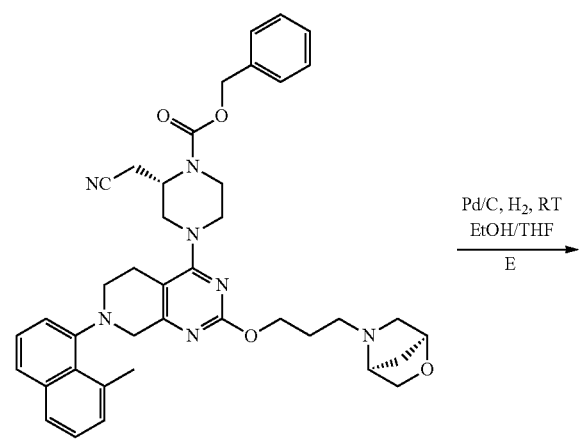

1048
-continued

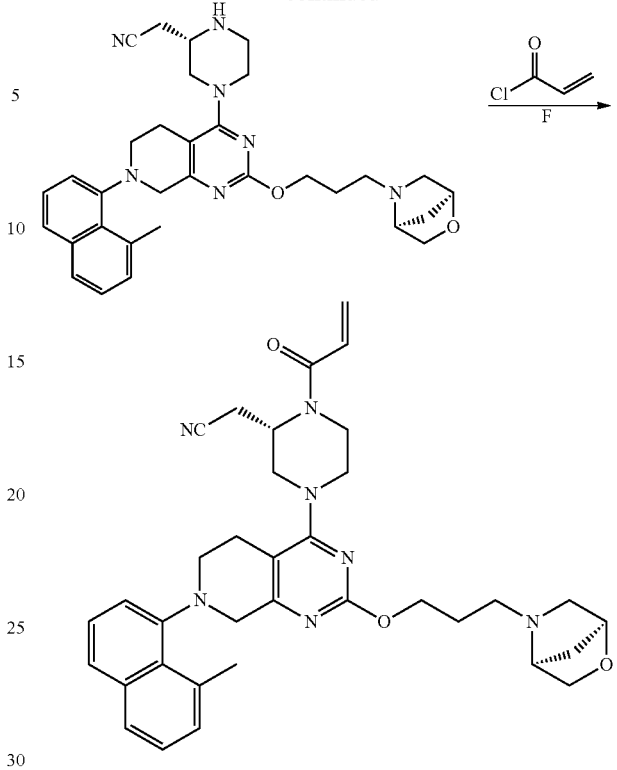

Step A: tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate Benzyl (S)-2-(cyanomethyl)piperazine-1-carboxylate hydrochloride (10 g, 34 mmol) was dissolved in DMA (68 ml, 34 mmol). To the solution was next added tert-butyl 2,4-dichloro-5,8-dihydropyrido[3,4-d]pyrimidine-7(6H)-carboxylate (9.3 g, 30 mmol) followed by Hunig's Base (24 ml, 135 mmol) and the reaction stirred at room temperature for 1 hour. The reaction was next poured into basic water and extracted with MTBE. The organics were washed with additional water, brine, dried over $Na_2SO_4$ and concentrated in vacuo. The material was chromatographed using 10% to 70% EtOAc:Hexane as eluent to give tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (12 g, 23 mmol, 67% yield). ESI+APCI MS m/z 527.2 $[M+H]^+$.

Step B: benzyl (S)-4-(2-chloro-5,6,7,8-tetrahydropyrido[3,4-d]pyrimidin-4-yl)-2-(cyanomethyl)piperazine-1-carboxylate Tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (1 g, 2 mmol) was dissolved in DCM (19 ml, 2 mmol) and treated with Hydrochloric Acid (4.0 M solution in 1,4-dioxane) (2 ml, 9 mmol). The reaction stirred at room temperature for 1 hour. The reaction was concentrated in vacuo and resuspended in DCM. The suspension was washed with 1M NaOH. The aqueous layer was extracted with DCM (2×). The combined organics were dried over $Na_2SO_4$, concentrated in vacuo and taken forward as crude benzyl (S)-4-(2-chloro-5,6,7,8-tetrahydropyrido[3, 4-d]pyrimidin-4-yl)-2-(cyanomethyl)piperazine-1-carboxylate (0.8 g, 2 mmol, 99% yield). ESI+APCI MS m/z 427.1 [M+H]⁺.

Step C: benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate Tris(dibenzylideneacetone)dipalladium(0) (343 mg, 0.375 mmol) and 2-(Dicyclohexylphosphino)-2',4',6'-tri-i-propyl-1,1'-biphenyl (357 mg, 0.750 mmol) were dissolved in 1,4-dioxane (18740 µl, 1.87 mmol) and purged under Argon for 5 minutes. The reaction stirred at 100° C. under argon for an additional 15 min. To the reaction was added benzyl (S)-4-(2-chloro-5,6,7,8-tetrahydropyrido[3,4-d]pyrimidin-4-yl)-2-(cyanomethyl)piperazine-1-carboxylate (800 mg, 1.87 mmol), 1-bromo-8-methylnaphthalene (1243 mg, 5.62 mmol), and cesium carbonate (1832 mg, 5.62 mmol) under Argon. The reaction was capped under Argon and stirred at 100° C. over night. The reaction was cooled to room temperature and filtered through GF/F paper. The filtrate was concentrated in vacuo and purified by normal phase chromatography on the CombiFlash eluting with 0%-15% DCM:MeOH (+2% NH₄OH modifier) to give benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate (378 mg, 0.667 mmol, 35.6% yield). ESI+APCI MS m/z 567.2 [M+H]⁺.

Step D: benzyl (S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)-2-(cyanomethyl)piperazine-1-carboxylate In a round bottom flask, a solution of benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate (0.3 g, 0.529 mmol) in dioxane (5.29 ml, 0.529 mmol) was sparged with Argon. 3-((1S,4S)-2-oxa-5-azabicyclo[2.2.1]heptan-5-yl)propan-1-ol (0.250 g, 1.59 mmol), Cs₂CO₃ (0.517 g, 1.59 mmol), Tris(dibenzylideneacetone)dipalladium (0) (0.0969 g, 0.106 mmol) and 9,9-Dimethyl-4,5-Bis(Dipheyl-Phosphino)Xanthene (0.122 g, 0.212 mmol) were sequentially added under Argon and sparged for an additional 5 minutes. The reaction mixture was capped and heated at 100° C. for 2 hours. The reaction was filtered through GF/F paper and concentrated in vacuo. The concentrate was purified by silica gel eluting with 0-12% MeOH in DCM with 2% NH₄OH to provide benzyl (S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)-2-(cyanomethyl)piperazine-1-carboxylate (0.155 g, 0.225 mmol, 42.6% yield). ESI+APCI MS m/z 688.3 [M+H]⁺.

Step E: 2-((S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)piperazin-2-yl)acetonitrile A solution of benzyl (S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)-2-(cyanomethyl)piperazine-1-carboxylate (155 mg, 0.225 mmol) in EtOH (2253 µl, 0.225 mmol) and THF (2253 µl, 0.225 mmol) and EtOH (2253 µl, 0.225 mmol) was purged with N₂ for 5 minutes. To this solution was added Palladium (60.0 mg, 0.0563 mmol) (Degussa Type, 10 wt %, 50% H₂O), and was immediately capped and purged with N₂ for an additional 5 minutes. The solution then stirred under an atmosphere of H₂. The mixture was then diluted with MeOH and filtered through packed celite. The filtrate was then concentrated in vacuo to provide 2-((S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)piperazin-2-yl)acetonitrile (98 mg, 0.177 mmol, 78.5% yield). This was taken forward as crude. ESI+APCI MS m/z 554.3 [M+H]⁺.

Step F: 2-((S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)-1-acryloylpiperazin-2-yl)acetonitrile To a suspension of 2-((S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)piperazin-2-yl)acetonitrile (98 mg, 0.177 mmol) in dichloromethane (1770 µl, 0.177 mmol) at ambient temperature was added Acyloyl Chloride (14.4 µl, 0.177 mmol) followed by Hunig's base (61.8 µl, 0.354 mmol). The reaction was then stirred at ambient temperature for 2 hours. The reaction mixture was concentrated in vacuo. The concentrate was resuspended in a 60:40 mixture of ACN: H₂O and purified on the Gilson (reverse prep HPLC), eluting with 5→95% ACN/0.1% TFA in water/0.1% TFA. Fractions containing product were combined and partitioned between saturated bicarb and DCM. The aqueous layer was extracted with DCM two more times. The organic layers were combined, dried over Na₂SO₄ and concentrated in vacuo to give title compound 2-((S)-4-(2-(3-((1S,4S)-2-oxa-5-azabicyclo[2.2.1]heptan-5-yl)propoxy)-7-(8-methylnaphthalen-1-yl)-5,6,7,8-tetrahydropyrido[3,4-d]pyrimidin-4-yl)-1-acryloylpiperazin-2-yl)acetonitrile (EXAMPLE 369, 63.5 mg, 0.104 mmol, 59.0% yield). ESI+APCI MS m/z 608.3 [M+H]⁺.

Example 370

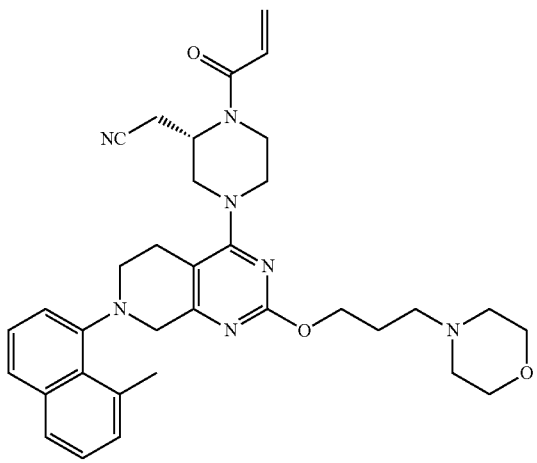 [SMILES: C=CC(=O)N1CCN(c2nc(OCCCN3CCOCC3)nc3c2CCN(c2cccc4cccc(C)c24)C3)C[C@@H]1CC#N]

(S)-2-(1-acryloyl-4-(7-(8-methylnaphthalen-1-yl)-2-(3-morpholinopropoxy)-5,6,7,8-tetrahydropyrido[3,4-d]pyrimidin-4-yl)piperazin-2-yl)acetonitrile (S)-2-(1-acryloyl-4-(7-(8-methylnaphthalen-1-yl)-2-(3-morpholinopropoxy)-5,6,7,8-tetrahydropyrido[3,4-d]pyrimidin-4-yl)piperazin-2-yl)acetonitrile The title compound was prepared following EXAMPLE 369 substituting N-Hydroxypropanylmorpholine for 3-((1S,4S)-2-oxa-5-azabicyclo[2.2.1]heptan-5-yl)propan-1-ol and also substituting Methanesulfonato(2-dicyclohexylphosphino-2',6'-di-i-propoxy-1,1'-biphenyl)(2'-methylamino-1,1'-biphenyl-2-yl)palladium(II) for Tris(dibenzylideneacetone)dipalladium (0) and 9,9-Dimethyl-4,5-Bis(Dipheyl-Phosphino)Xanthene in Step D. ESI+APCI MS m/z 596.3 [M+H]+.

Example 371

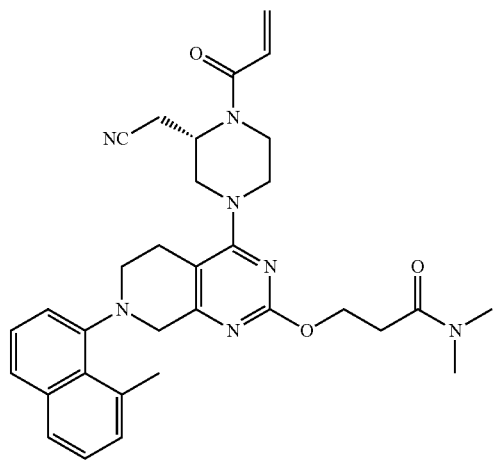 [SMILES: C=CC(=O)N1CCN(c2nc(OCCC(=O)N(C)C)nc3c2CCN(c2cccc4cccc(C)c24)C3)C[C@@H]1CC#N]

(S)-3-((4-(4-acryloyl-3-(cyanomethyl)piperazin-1-yl)-7-(8-methylnaphthalen-1-yl)-5,6,7,8-tetrahydropyrido[3,4-d]pyrimidin-2-yl)oxy)-N,N-dimethylpropanamide (S)-3-((4-(4-acryloyl-3-(cyanomethyl)piperazin-1-yl)-7-(8-methylnaphthalen-1-yl)-5,6,7,8-tetrahydropyrido[3,4-d]pyrimidin-2-yl)oxy)-N,N-dimethylpropanamide The title compound was prepared following EXAMPLE 369 substituting 3-Hydroxy-N,N-dimethylpropanamide for 3-((1S,4S)-2-oxa-5-azabicyclo[2.2.1]heptan-5-yl)propan-1-ol and also substituting Methanesulfonato(2-dicyclohexylphosphino-2',6'-di-i-propoxy-1,1'-biphenyl)(2'-methylamino-1,1'-biphenyl-2-yl)palladium(II) for Tris(dibenzylideneacetone)dipalladium (0) and 9,9-Dimethyl-4,5-Bis(Dipheyl-Phosphino)Xanthene in Step D. ESI+APCI MS m/z 568.3 [M+H]+.

Example 372

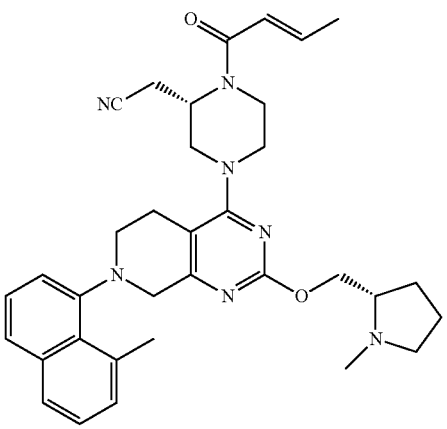 [SMILES: C/C=C/C(=O)N1CCN(c2nc(OC[C@@H]3CCCN3C)nc3c2CCN(c2cccc4cccc(C)c24)C3)C[C@@H]1CC#N]

2-((S)-1-((E)-but-2-enoyl)-4-(7-(8-methylnaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile

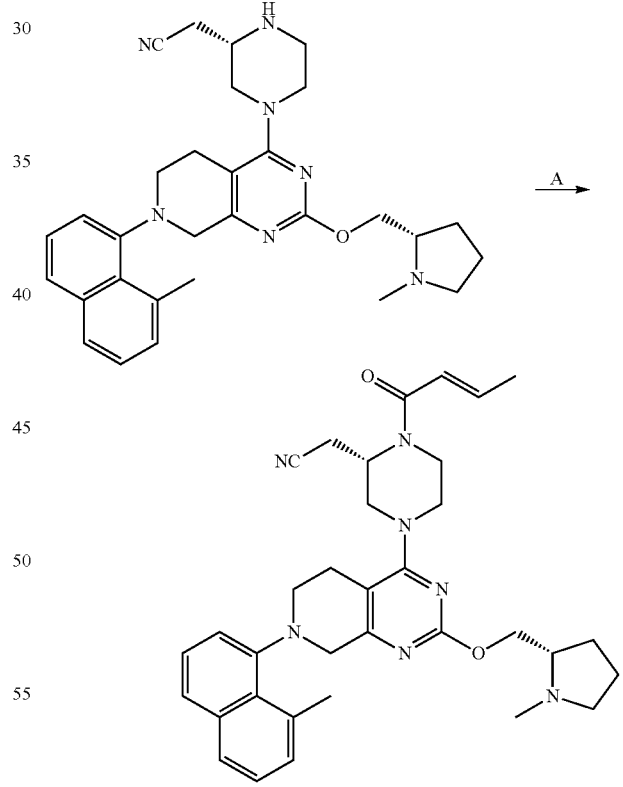

Step A: 2-((S)-1-((E)-but-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]

pyrimidin-4-yl)piperazin-2-yl)acetonitrile (30 mg, 0.05863 mmol) and 3-(E)-but-2-enoic acid (6.562 mg, 0.07622 mmol) were diluted with DMF (400 uL) followed by the addition of DIEA (20.48 µl, 0.1173 mmol) and 1-propane-phosphonic acid cyclic anhydride (52.35 µl, 0.08795 mmol). After stirring for 12 hours, the reaction was diluted with ethyl acetate and saturated sodium bicarbonate. The layers were separated and the ethyl acetate was dried over MgSO₄, filtered and concentrated. The material was purified on silica gel eluting with 10% methanol/DCM (1% NH₄OH) to afford title compound 2-((S)-1-((E)-but-2-enoyl)-4-(7-(8-methyl-naphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile (EXAMPLE 372, 10 mg, 0.01725 mmol, 29.42% yield). ESI+APCI MS m/z 580.3 [M+H]⁺.

Example 373

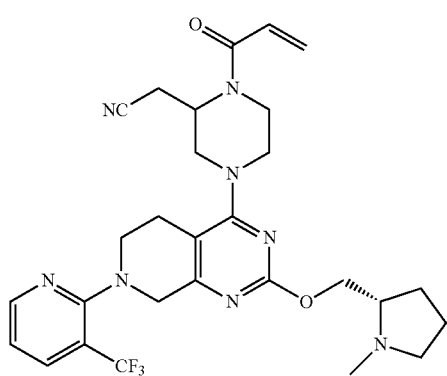 [SMILES: C=CC(=O)N1CCN(c2nc(OC[C@@H]3CCCN3C)nc3c2CCN(c2ncccc2C(F)(F)F)C3)CC1CC#N]

2-(1-acryloyl-4-(2-(((S)-1-methylpyrrolidin-2-yl)methoxy)-7-(3-(trifluoromethyl)pyridin-2-yl)-5,6,7,8-tetrahydropyrido[3,4-d]pyrimidin-4-yl)piperazin-2-yl)acetonitrile

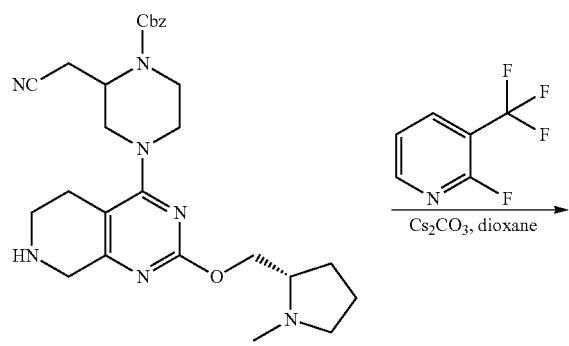

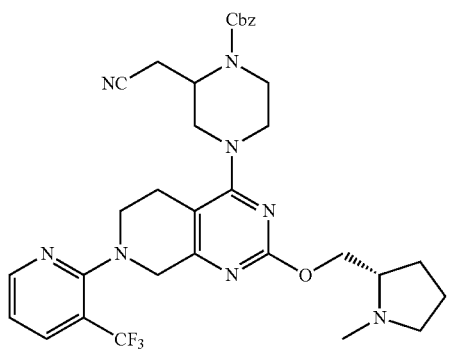

Step A: Benzyl 2-(cyanomethyl)-4-(2-(((S)-1-methylpyrrolidin-2-yl)methoxy)-7-(3-(trifluoromethyl)pyridin-2-yl)-5,6,7,8-tetrahydropyrido [3,4-d]pyrimidin-4-yl)piperazine-1-carboxylate In a microwave tube benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (100 mg, 0.198 mmol) was dissolved in dioxane (98.9 µl, 0.198 mmol) and treated with cesium carbonate (129 mg, 0.396 mmol), and 2-Fluoro-3-(trifluoromethyl)pyridine (163 mg, 0.989 mmol). The tube was then capped and heated to 90° C. for 12 hr. The reaction was cooled and filtered through GF/F paper and the filtrate was concentrated. The residue was purified by silica chromatography (0-12% MeOH in DCM with 0.25% NH₄OH) to provide benzyl 2-(cyanomethyl)-4-(2-(((S)-1-methylpyrrolidin-2-yl)methoxy)-7-(3-(trifluoromethyl)pyridin-2-yl)-5,6,7,8-tetrahydropyrido[3,4-d]pyrimidin-4-yl)piperazine-1-carboxylate (70 mg, 0.11 mmol, 54%).

Step B: 2-(1-acryloyl-4-(2-(((S)-1-methylpyrrolidin-2-yl)methoxy)-7-(3-(trifluoromethyl)pyridin-2-yl)-5,6,7,8-tetrahydropyrido[3,4-d]pyrimidin-4-yl)piperazin-2-yl)acetonitrile The title compound was prepared following EXAMPLE 375, Steps F-G substituting benzyl 2-(cyanomethyl)-4-(2-(((S)-1-methylpyrrolidin-2-yl)methoxy)-7-(3-(trifluoromethyl)pyridin-2-yl)-5,6,7,8-tetrahydropyrido[3,4-d]pyrimidin-4-yl)piperazine-1-carboxylate for benzyl 2-(cyanomethyl)-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazine-1-carboxylate in EXAMPLE 375 Step F. ESI+APCI MS m/z 571.3 [M+H]⁺.

Example 374

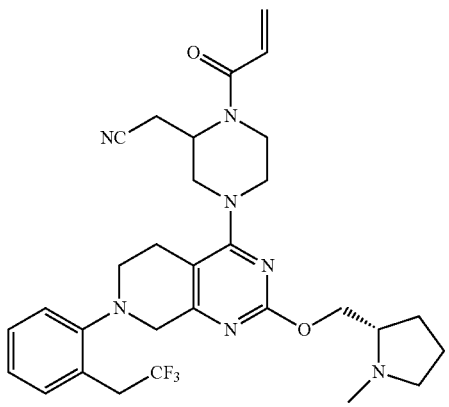 [SMILES: C=CC(=O)N1CCN(c2nc(OC[C@@H]3CCCN3C)nc3c2CCN(c2ccccc2CC(F)(F)F)C3)CC1CC#N]

2-(1-acryloyl-4-(2-(((S)-1-methylpyrrolidin-2-yl)
methoxy)-7-(2-(2,2,2-trifluoroethyl)phenyl)-5,6,7,8-
tetrahydropyrido[3,4-d]pyrimidin-4-yl)piperazin-2-
yl)acetonitrile 2-(1-acryloyl-4-(2-(((S)-1-methylpyrrolidin-2-yl)
methoxy)-7-(2-(2,2,2-trifluoroethyl)phenyl)-5,6,7,8-
tetrahydropyrido[3,4-d]pyrimidin-4-yl)piperazin-2-
yl)acetonitrile Was prepared following Example 375, Steps E-G, substituting 1-bromo-2-(2,2,2-trifluoroethyl)benzene for 4-Bromo-3-(trifluoromethyl)pyridine hydrobromide in Step E. ESI+APCI MS m/z 584.3 [M+H]+.

Example 375

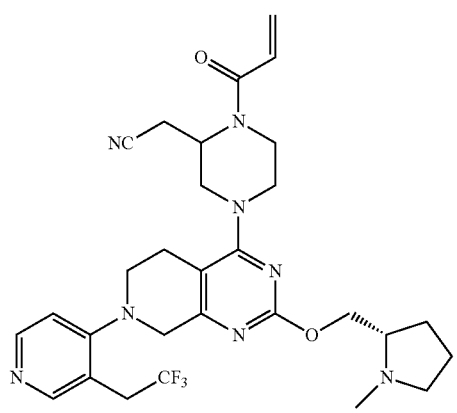 [SMILES: C=CC(=O)N1CCN(c2nc(OC[C@@H]3CCCN3C)nc3c2CCN(c2ccncc2CC(F)(F)F)C3)CC1CC#N]

2-(1-acryloyl-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazin-2-yl)acetonitrile

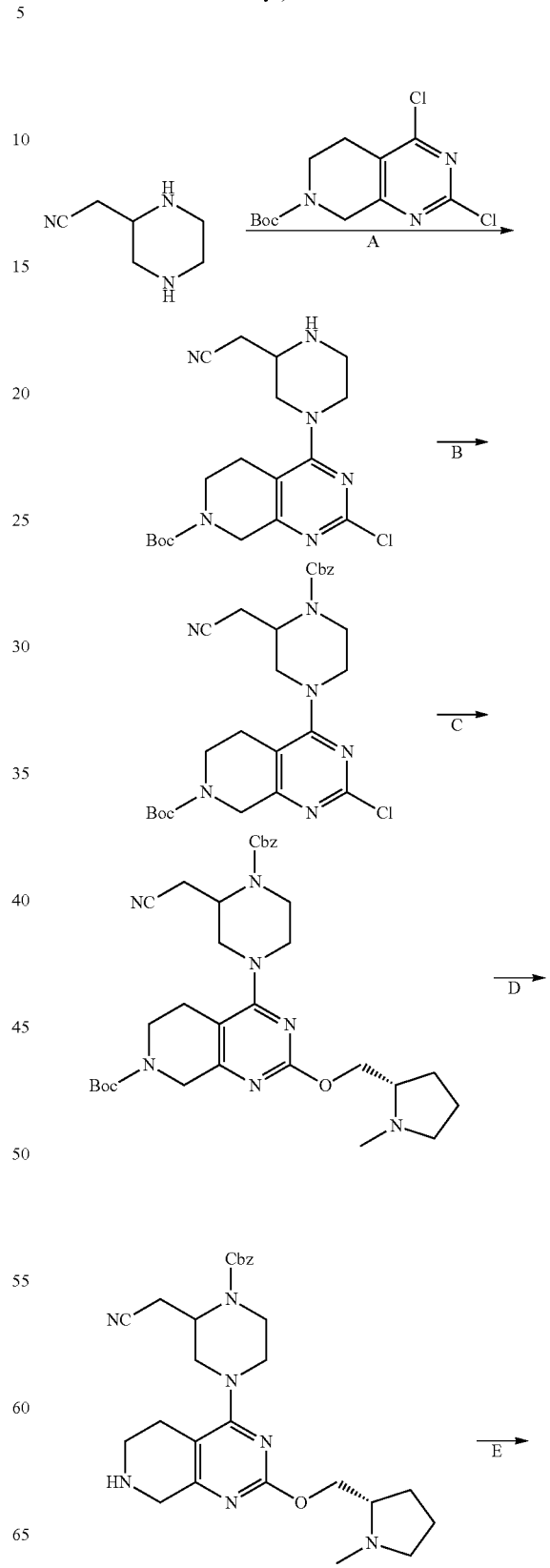

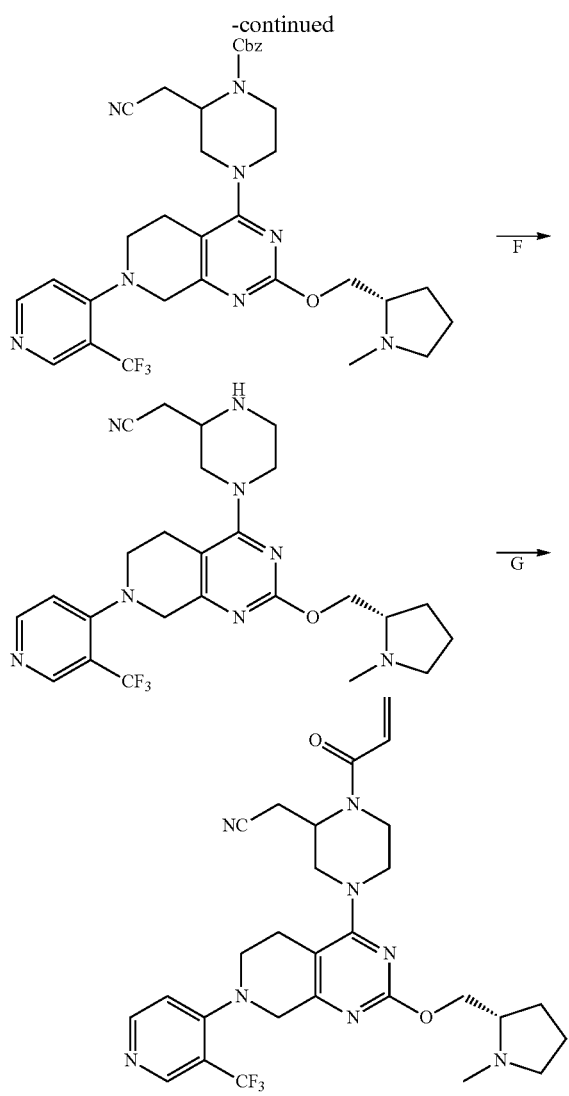

Step A: tert-butyl 2-chloro-4-(3-(cyanomethyl)piperazin-1-yl)-5,8-dihydropyrido[3,4-d]pyrimidine-7(6H)-carboxylate tert-butyl 2,4-dichloro-5,8-dihydropyrido[3,4-d]pyrimidine-7(6H)-carboxylate (8.0 g, 26.3 mmol), Hunig's base (22.9 ml, 132 mmol) and 2-(piperazin-2-yl)acetonitrile dihydrochloride (5.21 g, 26.3 mmol) were placed in DMA (75 mL) and stirred at rt for 20 min. Water was added and the mixture was extracted with EtOAc (3×100 mL). The extracts were combined and washed with water (3×50 mL) then was dried with sodium sulfate. The solids were filtered and the filtrate was concentrated to provide crude tert-butyl 2-chloro-4-(3-(cyanomethyl)piperazin-1-yl)-5,8-dihydropyrido[3,4-d]pyrimidine-7(6H)-carboxylate. ESI+APCI MS m/z 337.1 [M+H]$^+$.

Step B: tert-butyl 4-(4-((benzyloxy)carbonyl)-3-(cyanomethyl)piperazin-1-yl)-2-chloro-5,8-dihydropyrido[3,4-d]pyrimidine-7(6H)-carboxylate tert-butyl 2-chloro-4-(3-(cyanomethyl)piperazin-1-yl)-5,8-dihydropyrido[3,4-d]pyrimidine-7(6H)-carboxylate (10.50 g, 26.725 mmol) and TEA (5.5876 ml, 40.088 mmol) were placed in THF (100 mL) and was cooled to OC. Benzyl carbonochloridate (5.6518 ml, 40.088 mmol) was added and the reaction was stirred at OC for 30 min. Water was added and the mixture was extracted with DCM (3×50 mL). The extracts were combined and concentrated. The resulting residue was purified by silica gel (0-60% EtOAc in hex) to provide tert-butyl 4-(4-((benzyloxy)carbonyl)-3-(cyanomethyl)piperazin-1-yl)-2-chloro-5,8-dihydropyrido[3,4-d]pyrimidine-7(6H)-carboxylate (12.939 g, 24.551 mmol, 91.865% yield). ESI+APCI MS m/z 527.2 [M+H]$^+$.

Step C: tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate In a conical bottom vial, a solution of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (3.28 g, 6.22 mmol) in dioxane (62.2 ml, 6.22 mmol) was sparged with argon and (S)-(1-methylpyrrolidin-2-yl)methanol (2.15 g, 18.7 mmol), $Cs_2CO_3$ (6.08 g, 18.7 mmol), Methanesulfonato(2-dicyclohexylphosphino-2',6'-di-i-propoxy-1,1'-biphenyl)(2'-methylamino-1,1'-biphenyl-2-yl)palladium(II) (0.795 g, 0.934 mmol) were sequentially added under argon and sparged for an additional 5 min. The reaction mixture was capped and heated at 100° C. for 18 hr. The reaction was cooled and water was added. The mixture was extracted with DCM (3×15 mL) and the extracts were combined and concentrated. The resulting residue was purified by silica gel (0-12% MeOH in DCM with 0.25% $NH_4OH$) to provide tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (2.65 g, 4.37 mmol, 70.3% yield). ESI+APCI MS m/z 606.3 [M+H]$^+$.

Step D: benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate tert-butyl 4-(4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (0.6 g, 1.0 mmol) was dissolved in dichloromethane (10 ml, 1.0 mmol) and treated with hydrochloric acid (4.0 M solution in 1,4-dioxane (1 ml, 5 mmol) and the reaction was stirred at room temperature for 1 hour. The reaction was next concentrated in vacuo and the material partitioned between EtOAc and basic water and the layers separated. The organics were next washed with brine, dried over $Na_2SO_4$ and concentrated in vacuo to give benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (0.4 g, 0.8 mmol, 80% yield). ESI+APCI MS m/z 506.2 [M+H]$^+$.

Step E: benzyl 2-(cyanomethyl)-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazine-1-carboxylate To a vial was added Cesium carbonate (193 mg, 0.593 mmol), benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (60 mg, 0.119 mmol) and Rhuphos Pd G3 (9.92 mg, 0.0119 mmol), and 4-Bromo-3-

(trifluoromethyl)pyridine hydrobromide (93.4 mg, 0.356 mmol). the vial was sealed and the 1,4-dioxane (1187 µl, 0.119 mmol) added through a septum. Ar was bubbled through the mixture for 5 minutes and then the mixture was heated to 70° C. for 7 h. the reaction was cooled, filtered through qualitative paper and concentrated. The yellow solids were dissolved in minimal DCM and purified by silica chromatography (0-12% MeOH in DCM) to give benzyl 2-(cyanomethyl)-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazine-1-carboxylate (35 mg, 0.0541 mmol, 45.6%). ESI+APCI MS m/z 551.3 [M+H]⁺.

Step F: 2-(4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazin-2-yl)acetonitrile To a solution of benzyl 2-(cyanomethyl)-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazine-1-carboxylate (35.2 mg, 0.0541 mmol) in EtOH (541 µl, 0.0541 mmol) and THF (541 µl, 0.0541 mmol) was added Palladium (28.8 mg, 0.0135 mmol) (Degussa Type, 10 wt %, 50% H₂O) and then an atmosphere of H₂ was introduced via vacuum followed by balloon pressure. The mixture was then stirred at ambient temperature for 1 h. The mixture was then diluted with MeOH and filtered through GF/F paper. The filtrate was then concentrated to provide 2-(4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazin-2-yl)acetonitrile (26.4 mg, 0.0511 mmol, 94.5% yield).

Step G: 2-(1-acryloyl-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazin-2-yl)acetonitrile To a suspension of 2-(4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazin-2-yl)acetonitrile (26.4 mg, 0.0511 mmol) in CH₂Cl₂ (511 µl, 0.0511 mmol) at −78° C. was added acryloyl chloride (1022 µl, 0.102 mmol) (freshly prepared 0.1M solution in DCM) followed by Triethylamine (14.2 µl, 0.102 mmol). The reaction was then stirred at 0° C. for 45 minutes. LC-MS indicated product formation. Reaction concentrated and purified by prep HPLC to provide title compound 2-(1-acryloyl-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazin-2-yl)acetonitrile (EXAMPLE 375, 3 mg, 0.00526 mmol, 10.3% yield). ESI+APCI MS m/z 571.3 [M+H]⁺.

Example 376

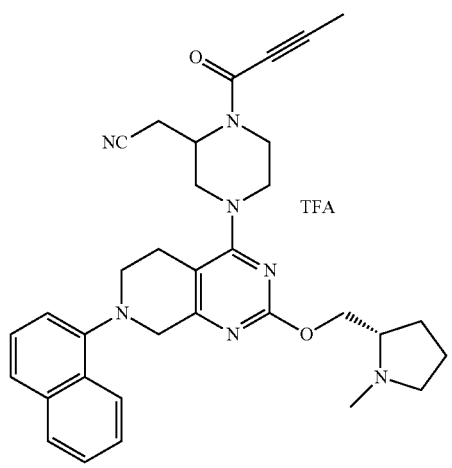 [SMILES: CC#CC(=O)N1CCN(c2nc(OC[C@@H]3CCCN3C)nc3c2CCN(c2cccc4ccccc24)C3)CC1CC#N]

2-(1-(but-2-ynoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile 2,2,2-trifluoroacetate

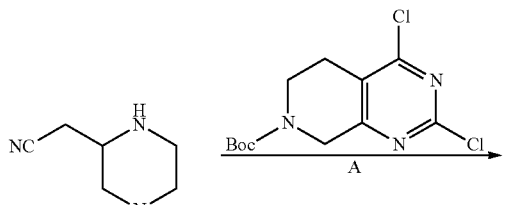

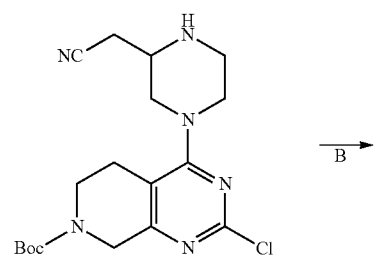

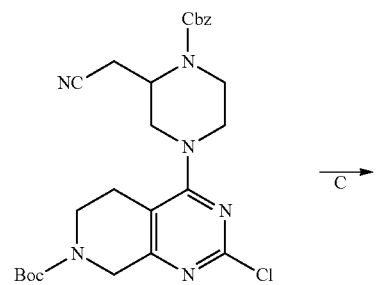

1061

-continued

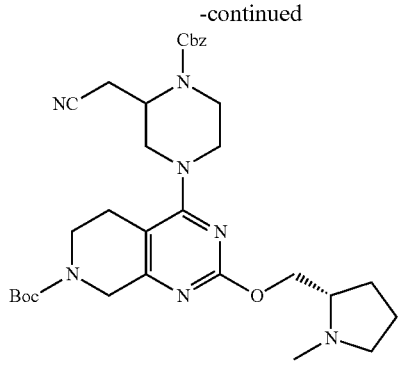

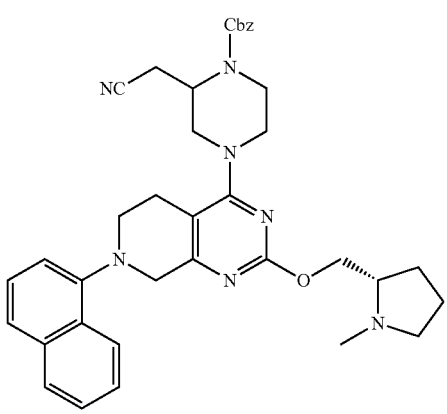

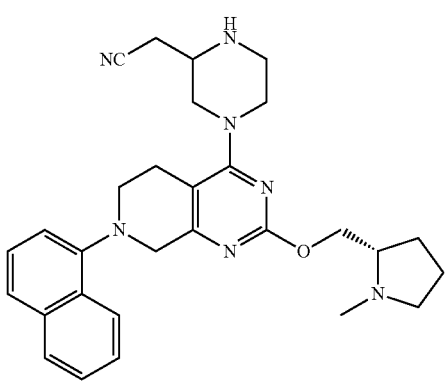

1062

-continued

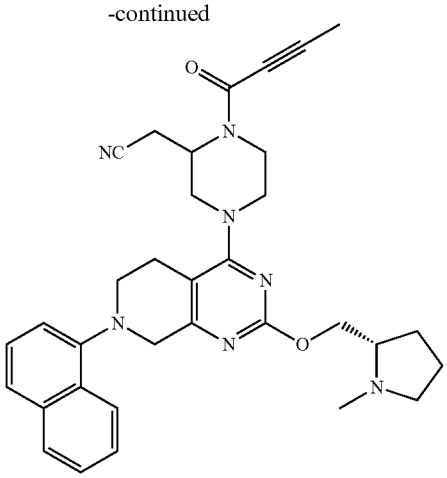

Step A: tert-butyl 2-chloro-4-(3-(cyanomethyl)piperazin-1-yl)-5,8-dihydropyrido[3,4-d]pyrimidine-7(6H)-carboxylate tert-butyl 2,4-dichloro-5,8-dihydropyrido[3,4-d]pyrimidine-7(6H)-carboxylate (8.0 g, 26.3 mmol), Hunig's base (22.9 ml, 132 mmol) and 2-(piperazin-2-yl)acetonitrile dihydrochloride (5.21 g, 26.3 mmol) were placed in DMA (75 mL) and stirred at rt for 20 min. Water was added and the mixture was extracted with EtOAc (3×100 mL). The extracts were combined and washed with water (3×50 mL) then was dried with sodium sulfate. The solids were filtered and the filtrate was concentrated to provide crude tert-butyl 2-chloro-4-(3-(cyanomethyl)piperazin-1-yl)-5,8-dihydropyrido[3,4-d]pyrimidine-7(6H)-carboxylate. ESI+APCI MS m/z 337.1 [M+H]⁺.

Step B: tert-butyl 4-(4-((benzyloxy)carbonyl)-3-(cyanomethyl)piperazin-1-yl)-2-chloro-5,8-dihydropyrido[3,4-d]pyrimidine-7(6H)-carboxylate tert-butyl 2-chloro-4-(3-(cyanomethyl)piperazin-1-yl)-5,8-dihydropyrido[3,4-d]pyrimidine-7(6H)-carboxylate (10.50 g, 26.73 mmol) and TEA (5.59 ml, 40.0 mmol) were placed in THF (100 mL) and was cooled to 0° C. Benzyl carbonochloridate (5.65 ml, 40.0 mmol) was added and the reaction was stirred at 0° C. for 30 min. Water was added and the mixture was extracted with DCM (3×50 mL). The extracts were combined and concentrated. The resulting residue was purified by silica gel (0-60% EtOAc in hex) to provide tert-butyl 4-(4-((benzyloxy)carbonyl)-3-(cyanomethyl)piperazin-1-yl)-2-chloro-5,8-dihydropyrido[3,4-d]pyrimidine-7(6H)-carboxylate (12.94 g, 24.6 mmol, 92% yield). ESI+APCI MS m/z 527.2 [M+H]⁺.

Step C: tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate In a conical bottom vial, a solution of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (3.28 g, 6.22 mmol) in dioxane (62.2 ml, 6.22 mmol) was sparged with argon and (S)-(1-methylpyrrolidin-2-yl)methanol (2.15 g, 18.7 mmol), Cs₂CO₃ (6.08 g, 18.7 mmol), methanesulfonato(2-dicyclohexylphosphino-2',6'-di-i-propoxy-1,1'-biphenyl)(2'-methylamino-1,1'-biphenyl-2-yl)palladium(II) (0.795 g, 0.934 mmol) were sequentially added under argon and sparged for an additional 5 min. The reaction mixture was capped and heated at 100° C. for 18 hr. The reaction was cooled and water was added. The mixture was extracted with DCM (3×15 mL) and the extracts were combined and concentrated. The resulting residue was purified by silica gel (0-12% MeOH in DCM with 0.25% $NH_4OH$) to provide tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (2.65 g, 4.37 mmol, 70% yield). ESI+ APCI MS m/z 606.3 [M+H]$^+$.

Step D: benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate tert-butyl 4-(4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (0.6 g, 1.0 mmol) was dissolved in dichloromethane (10 ml, 1.0 mmol) and treated with hydrochloric acid (4.0 M solution in 1,4-dioxane (1 ml, 5 mmol) and the reaction was stirred at room temperature for 1 hour. The reaction was concentrated in vacuo and the material partitioned between EtOAc and basic water and the layers were separated. The organics were washed with brine, dried over $Na_2SO_4$ and concentrated in vacuo to give benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (0.4 g, 0.8 mmol, 80% yield). ESI+APCI MS m/z 506.2 [M+H]$^+$.

Step E: benzyl 2-(cyanomethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate To a vial was added cesium carbonate (193 mg, 0.59 mmol), benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (60 mg, 0.12 mmol) and Rhuphos Pd G3 (9.92 mg, 0.012 mmol), and 1-bromonaphthalene (49.8 μl, 0.36 mmol). The vial was sealed and the 1,4-dioxane (1187 μl, 0.12 mmol) added through a septum. Ar was bubbled through the mixture for 5 minutes and then the mixture was heated to 70° C. for 7 h. The reaction was cooled, filtered through qualitative paper and concentrated. The yellow solids were dissolved in minimal DCM and purified by silica chromatography (0-12% MeOH in DCM) to provide benzyl 2-(cyanomethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (28 mg, 0.044 mmol, 37% yield). ESI+APCI MS m/z 632.4 [M+H]$^+$.

Step F: 2-(4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile To a solution of benzyl 2-(cyanomethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (45 mg, 0.071 mmol) in EtOH (712 μl, 0.071 mmol) and THF (712 μl, 0.071 mmol) was added palladium (38 mg, 0.018 mmol) (Degussa Type, 10 wt %, 50% $H_2O$) and then an atmosphere of $H_2$ was introduced via vacuum followed by balloon pressure. The mixture was then stirred at ambient temperature for 1 h. The mixture was then diluted with MeOH and filtered through GF/F paper. The filtrate was then concentrated to provide 2-(4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (30 mg, 0.060 mmol, 85% yield). ESI+APCI MS m/z 498.3 [M+H]$^+$.

Step G: 2-(1-(but-2-ynoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile 2,2,2-trifluoroacetate At 0° C., to a 25 mL RBF containing N,N-dimethylformamide (603 μl, 0.060 mmol) was added 2-(4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (30 mg, 0.060 mmol) and triethylamine (12.2 mg, 0.12 mmol). The reaction mixture was vigorously stirred while 2-butynoic acid (6.08 mg, 0.072 mmol) was added in one portion. 1-Propanephosphonic acid cyclic anhydride (26.9 μl, 0.090 mmol) was added slowly to the stirring mixture. The reaction was allowed to stir for 2 hr at 0° C. Water was added and the reaction extracted with EtOAc (2×25 mL). The organic layers were washed with saturated LiCl, NaCl, and water (10 mL each wash). Dried and concentrated to a solid that was purified by prep HPLC (5-95% ACN:H2O, TFA) which provided title compound 2-(1-(but-2-ynoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile 2,2,2-trifluoroacetate (EXAMPLE 376, 11.2 mg, 0.02 mmol, 33% yield) ESI+APCI MS m/z 564.3 [M+H]$^+$.

Example 377

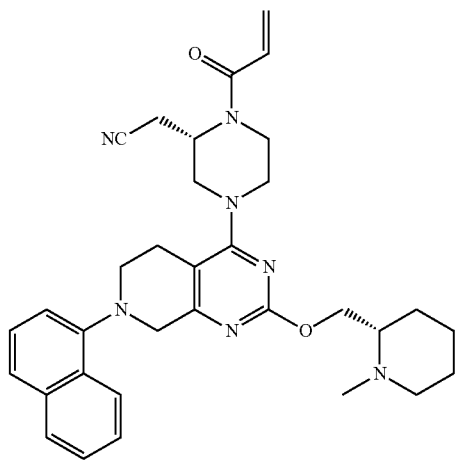 [SMILES: C=CC(=O)N1CCN(c2nc(OC[C@@H]3CCCCN3C)nc3c2CCN(c2cccc4ccccc24)C3)C[C@@H]1CC#N]

1065

2-((S)-1-acryloyl-4-(2-(((S)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile

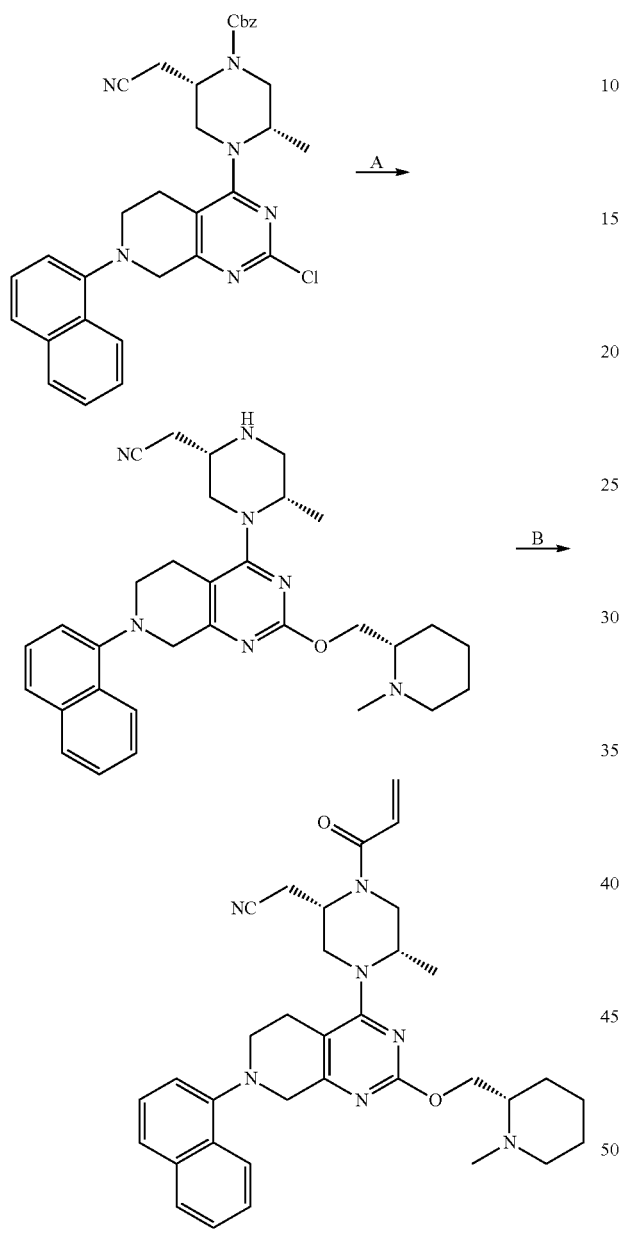

Step A: 2-((S)-4-(2-(((S)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile To a solution of benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (0.30 g, 0.54 mmol) in dioxanes was added (S)-(1-methylpiperidin-2-yl)methanol (0.49 g, 3.8 mmol) and Cs$_2$CO$_3$ (0.53 g, 1.6 mmol) and the reaction degassed with Argon for 15 minutes, followed by addition of Rhuphos Pd G3 (0.068 g, 0.081 mmol) and the reaction heated to 100° C. for overnight. The reaction was cooled and filtered through GFF paper and the filtrate concentrated in vacuo. The residue was next chromatographed using 1→15% MeOH/DCM with 2% Ammonium Hydroxide as eluent to give 2-((S)-4-(2-(((S)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile (0.23 g, 0.45 mmol, 83% yield). ESI+APCI MS m/z 512.3 [M+H]$^+$.

Step B: 2-((S)-1-acryloyl-4-(2-(((S)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile To a solution of 2-((S)-4-(2-(((S)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile (0.23 g, 0.45 mmol) in DCM (20 mL) cooled to 0° C. was added N-ethyl-N-isopropylpropan-2-amine (0.16 ml, 0.90 mmol) followed by addition of a solution of acryloyl chloride (0.037 ml, 0.45 mmol) (in 10 mL of DCM) and the reaction stirred at 0° C. for 10 minutes. To the reaction was next added 1 mL of methanol and the reaction concentrated in vacuo. The material was next chromatographed 2× using 1→10% MeOH/DCM with 2% NH$_4$OH as eluent to give a solid which was further purified by reverse prep HPLC using 5→95% ACN/water with 0.1% TFA as modifier to give title compound 2-((S)-1-acryloyl-4-(2-(((S)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile (EXAMPLE 377, 0.030 g, 0.053 mmol, 12% yield). ESI+APCI MS m/z 566.3 [M+H]$^+$.

Example 378

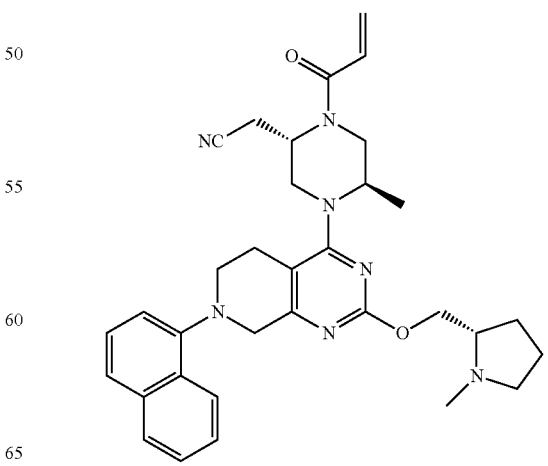

1067

2-((2S,5R)-1-acryloyl-5-methyl-4-(2-(((S)-1-methyl-pyrrolidin-2-yl)methoxy)-7-(naphthalen-1-yl)-5,6,7,8-tetrahydropyrido[3,4-d]pyrimidin-4-yl)piperazin-2-yl)acetonitrile

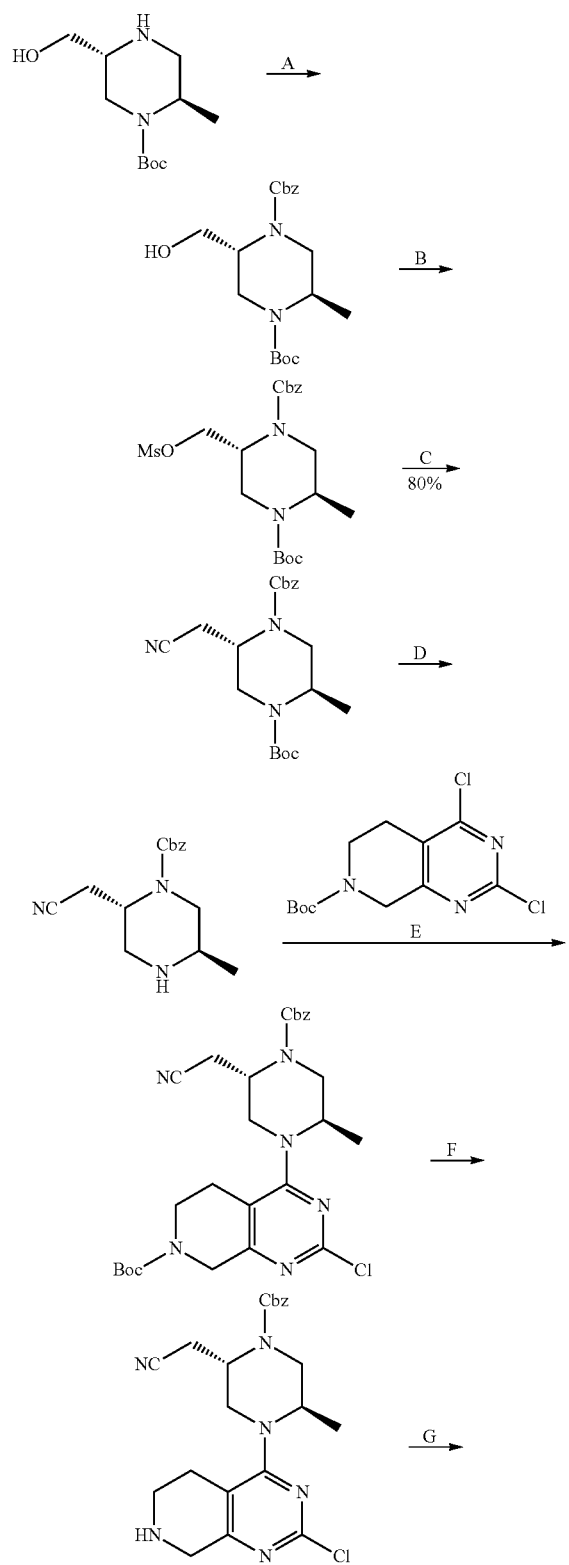

1068

-continued

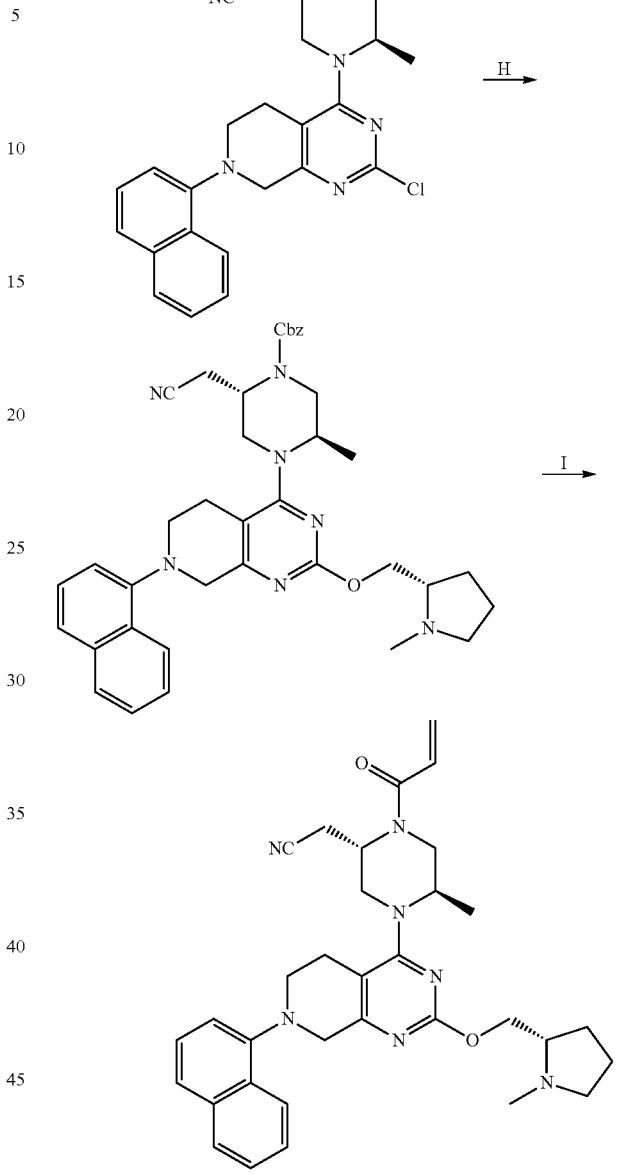

Step A: 1-benzyl 4-(tert-butyl) (2R,5R)-2-(hydroxymethyl)-5-methylpiperazine-1,4-dicarboxylate Tert-butyl (2R,5R)-5-(hydroxymethyl)-2-methylpiperazine-1-carboxylate (1.0 g, 4.34 mmol) was dissolved in water (50 mL) followed by addition of EtOAc (6.68 ml, 4.34 mmol) and sodium hydrogen carbonate (1.09 g, 13.0 mmol) and the reaction stirred 3 minutes. To the reaction was added benzyl carbonochloridate (0.648 ml, 4.56 mmol) in 1 bolus (internal temp from 19→25 C) and the reaction stirred overnight at room temperature. The layers were next separated and the organics washed with brine, dried over MgSO4 and concentrated in vacuo. The residue was chromatographed using 10→70% EtOAc/Hex as eluent to give 1-benzyl 4-(tert-butyl) (2R,5R)-2-(hydroxymethyl)-5-methylpiperazine-1,4-dicarboxylate (1.2 g, 3.29 mmol, 75.8% yield). ESI+APCI MS m/z 265.2 [M+H-boc]t Step B: 1-benzyl 4-(tert-butyl) (2R,5R)-5-methyl-2-(((methylsulfonyl)oxy)methyl)piperazine-1,4-dicarboxylate To a solution of 1-benzyl 4-(tert-butyl) (2R,5R)-2-(hydroxymethyl)-5-methylpiperazine-1,4-dicarboxylate (1.2 g, 3.3 mmol) in DCM cooled to OC was added N-ethyl-N-isopropylpropan-2-amine (0.64 g, 4.9 mmol) and methanesulfonyl chloride (0.30 ml, 3.6 mmol) and the reaction stirred at 0° C. for 2 hrs. The organics were next washed with brine, dried over MgSO$_4$ and concentrated in vacuo. The material was next chromatographed using 10→70% EtOAc/hex as eluent to give 1-benzyl 4-(tert-butyl) (2R,5R)-5-methyl-2-(((methylsulfonyl)oxy)methyl)piperazine-1,4-dicarboxylate (1.3 g, 2.9 mmol, 89% yield). ESI+APCI MS m/z 343.1 [M+H-boc]$^+$.

Step C: 1-benzyl 4-(tert-butyl) (2S,5R)-2-(cyanomethyl)-5-methylpiperazine-1,4-dicarboxylate To a solution of 1-benzyl 4-(tert-butyl) (2R,5R)-5-methyl-2-(((methylsulfonyl)oxy)methyl)piperazine-1,4-dicarboxylate (1.3 g, 2.9 mmol) in DMA (20 mL) was added cyanosodium (0.29 g, 5.9 mmol) and the reaction stirred 48 hrs at 55° C. The reaction was next diluted with basic water (220 mL) and the aq layer extracted with MTBE. The organics were next washed with water (2×50 mL), brine (50 mL), dried over MgSO$_4$ and concentrated in vacuo. The material was next chromatographed using 10450% EtOAc/hex as eluent to give 1-benzyl 4-(tert-butyl) (2S,5R)-2-(cyanomethyl)-5-methylpiperazine-1,4-dicarboxylate (0.90 g, 2.4 mmol, 82% yield). ESI+APCI MS m/z 274.1 [M+H-boc]$^+$.

Step D: benzyl (2S,5R)-2-(cyanomethyl)-5-methylpiperazine-1-carboxylate hydrochloride To a solution of 1-benzyl 4-(tert-butyl) (2S,5R)-2-(cyanomethyl)-5-methylpiperazine-1,4-dicarboxylate (0.90 g, 2.4 mmol) in DCM was added hydrogen chloride (3.0 ml, 12 mmol) and the reaction stirred for 2 hrs at rt (added 5 more eq of HCl at 1 hr). The reaction was next concentrated in vacuo and the material used crude in the next reaction. ESI+APCI MS m/z 274.2 [M+H]$^+$.

Step E: tert-butyl 4-((2R,5S)-4-((benzyloxy)carbonyl)-5-(cyanomethyl)-2-methylpiperazin-1-yl)-2-chloro-5,8-dihydropyrido[3,4-d]pyrimidine-7(6H)-carboxylate To the solid benzyl (2S,5R)-2-(cyanomethyl)-5-methylpiperazine-1-carboxylate hydrochloride (0.75 g, 2.4 mmol) and tert-butyl 2,4-dichloro-5,8-dihydropyrido[3,4-d]pyrimidine-7(6H)-carboxylate (0.74 g, 2.4 mmol) was added DMA (10 mL) followed by Hunig's Base (1.3 ml, 7.3 mmol) and the reaction stirred overnight at room temperature. The reaction was next poured into water and and the aqueous layer extracted with MTBE. The MTBE layer was washed with water, brine, dried over MgSO$_4$ and concentrated in vacuo. The material was purified by column chromatography using 10→70% etoac/hex as eluent to give tert-butyl 4-((2R,5S)-4-((benzyloxy)carbonyl)-5-(cyanomethyl)-2-methylpiperazin-1-yl)-2-chloro-5,8-dihydropyrido[3,4-d]pyrimidine-7(6H)-carboxylate (0.72 g, 1.3 mmol, 55% yield). ESI+APCI MS m/z 541.3 [M+H]$^+$.

Step F: benzyl (2S,5R)-4-(2-chloro-5,6,7,8-tetrahydropyrido[3,4-d]pyrimidin-4-yl)-2-(cyanomethyl)-5-methylpiperazine-1-carboxylate To a solution of tert-butyl 4-((2R,5S)-4-((benzyloxy)carbonyl)-5-(cyanomethyl)-2-methylpiperazin-1-yl)-2-chloro-5,8-dihydropyrido[3,4-d]pyrimidine-7(6H)-carboxylate (0.72 g, 1.3 mmol) in DCM (20 mL) was added hydrogen chloride (1.7 ml, 6.7 mmol) (4 M in dioxanes) and the reaction stirred for 1 hour at room temperature. The reaction was next concentrated in vacuo and the residue partitioned between EtOAc and basic water. The organics were separated and washed with brine, dried over MgSO$_4$ and concentrated in vacuo. The material was used crude in the next rxn. ESI+APCI MS m/z 441.2 [M+H]$^+$.

Step G: benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate To a solution of benzyl (2S,5R)-4-(2-chloro-5,6,7,8-tetrahydropyrido[3,4-d]pyrimidin-4-yl)-2-(cyanomethyl)-5-methylpiperazine-1-carboxylate (0.48 g, 1.1 mmol) in dioxanes (40 mL) was added 1-iodonaphthalene (1.4 g, 5.4 mmol) and Cs$_2$CO$_3$ (1.1 g, 3.3 mmol) and the reaction degassed with Ar for 15 minutes, followed by addition of Methanesulfonato(2-dicyclohexylphosphino-2',6'-di-i-propoxy-1,1'-biphenyl)(2'-methylamino-1,1'-biphenyl-2-yl)palladium(II) (0.14 g, 0.16 mmol) and the reaction heated to 100° C. for 5 hours. The reaction was next cooled and filtered through GFF paper and concentrated in vacuo. The material was next chromatographed using 10470 etoac/hex as eluent to give benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (2.8 g, 5.1 mmol, 64% yield). ESI+APCI MS m/z 567.2 [M+H]$^+$.

Step H: 2-((2S,5R)-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile To a solution of benzyl (2S,5R)-4-(2-chloro-7-(naphthalen-1-yl)-5,6,7,8-tetrahydropyrido[3,4-d]pyrimidin-4-yl)-2-(cyanomethyl)-5-methylpiperazine-1-carboxylate (0.48 g, 0.85 mmol) in dioxanes (40 mL) was added (S)-(1-methylpyrrolidin-2-yl)methanol (0.39 g, 3.4 mmol) and Cs$_2$CO$_3$ (1.4 g, 4.2 mmol) and the reaction degassed with Ar for 15 minutes followed by addition of Methanesulfonato(2-dicyclohexylphosphino-2',6'-di-i-propoxy-1,1'-biphenyl)(2'-methylamino-1,1'-biphenyl-2-yl)palladium(II) (0.11 g, 0.13 mmol) and the reaction heated to 100° C. for overnight. The reaction was next cooled and filtered through GFF paper and concentrated in vacuo. The material was next chromatographed using 1→15% (MeOH+2% NH$_4$OH)/DCM with to give benzyl (2S,5R)-2-(cyanomethyl)-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (0.20 g, 0.31 mmol, 37% yield) and 2-((2S,5R)-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (0.14 g, 0.27 mmol, 32% yield). ESI+APCI MS m/z 512.3 [M+H]$^+$.

Step I: 2-((2S,5R)-1-acryloyl-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile To a solution of 2-((2S,5R)-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (0.14 g, 0.274 mmol) cooled to 0° C. was added N-ethyl-N-isopropylpropan-2-amine (0.0982 ml, 0.547 mmol) followed by acryloyl chloride (0.0225 ml, 0.274 mmol) and the reaction stirred at 0° C. for 10 minutes. 1 mL of methanol was added to the reaction and the reaction concentrated in vacuo. The material was next purified by gilson reverse prep 2 HPLC 2 times eluting with 5→95% ACN/water with 0.1% TFA as modifier. The combined fractions were partitioned between EtOAc and basic water and the layers separated. The organics were next washed with brine, dried over MgSO₄ and concentrated in vacuo to give title compound 2-((2S,5R)-1-acryloyl-5-methyl-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (EXAMPLE 378, 0.0118 g, 0.0209 mmol, 7.62% yield). ESI+APCI MS m/z 566.3 [M+H]⁺.

Example 379

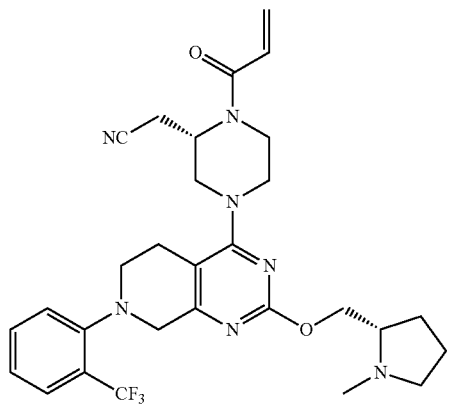 [SMILES: C=CC(=O)N1CCN(c2nc(OC[C@@H]3CCCN3C)nc3c2CCN(c2ccccc2C(F)(F)F)C3)C[C@@H]1CC#N]

2-((S)-1-acryloyl-4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazin-2-yl)acetonitrile 2-((S)-1-acryloyl-4-(2-(((S)-1-methylpyrrolidin-2-yl)methoxy)-7-(2-(trifluoromethyl)phenyl)-5,6,7,8-tetrahydropyrido[3,4-d]pyrimidin-4-yl)piperazin-2-yl)acetonitrile was prepared following Example 234, Steps H-J, substituting 1-bromo-2-(trifluoromethyl)benzene for 1-bromonaphthalene in Step H. ESI+APCI MS m/z 570.3 [M+H]⁺.

Example 380

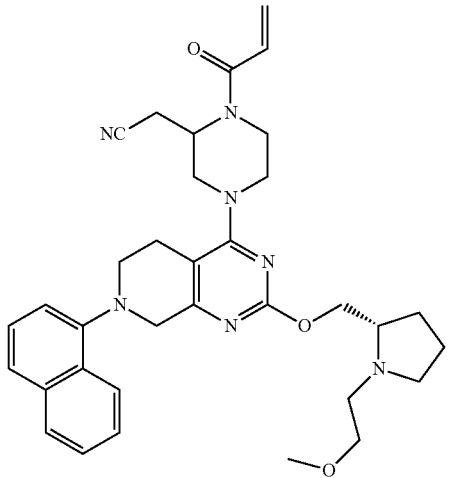 [SMILES: C=CC(=O)N1CCN(c2nc(OC[C@@H]3CCCN3CCOC)nc3c2CCN(c2cccc4ccccc24)C3)CC1CC#N]

2-(1-acryloyl-4-(2-(((S)-1-(2-methoxyethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile 2-(1-acryloyl-4-(2-(((S)-1-(2-methoxyethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile was prepared following Example 375, Steps C-G, substituting (S)-(1-(2-methoxyethyl)pyrrolidin-2-yl)methanol for (S)-(1-methylpyrrolidin-2-yl)methanol in Step C and 1-bromonaphthalene for 4-bromo-3-(trifluoromethyl)pyridine hydrobromide in Step E. ESI+APCI MS m/z 596.3 [M+H]⁺.

Example 381

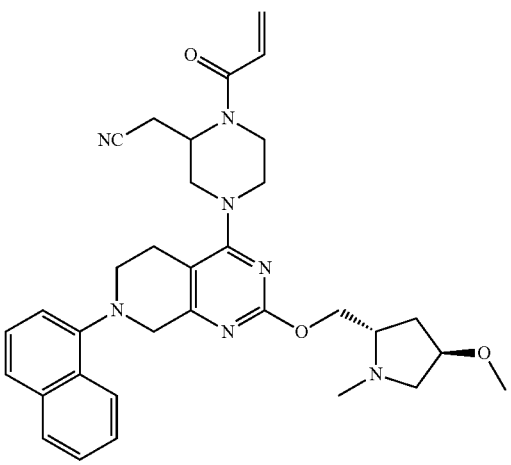 [SMILES: C=CC(=O)N1CCN(c2nc(OC[C@@H]3C[C@@H](OC)CN3C)nc3c2CCN(c2cccc4ccccc24)C3)CC1CC#N]

2-(1-acryloyl-4-(2-(((2S,4R)-4-methoxy-1-methyl-pyrrolidin-2-yl)methoxy)-7-(naphthalen-1-yl)-5,6,7,8-tetrahydropyrido[3,4-d]pyrimidin-4-yl)piperazin-2-yl)acetonitrile Step A: tert-butyl (2S,4R)-2-(((4-(4-acryloyl-3-(cyanomethyl)piperazin-1-yl)-7-(naphthalen-1-yl)-5,6,7,8-tetrahydropyrido [3,4-d]pyrimidin-2-yl)oxy)methyl)-4-methoxypyrrolidine-1-carboxylate was prepared following Example 375, Steps C-F, substituting tert-butyl (2S,4R)-2-(hydroxymethyl)-4-methoxypyrrolidine-1-carboxylate for (S)-(1-methylpyrrolidin-2-yl)methanol in Step C and 1-bromonaphthalene for 4-bromo-3-(trifluoromethyl)pyridine hydrobromide in Step E

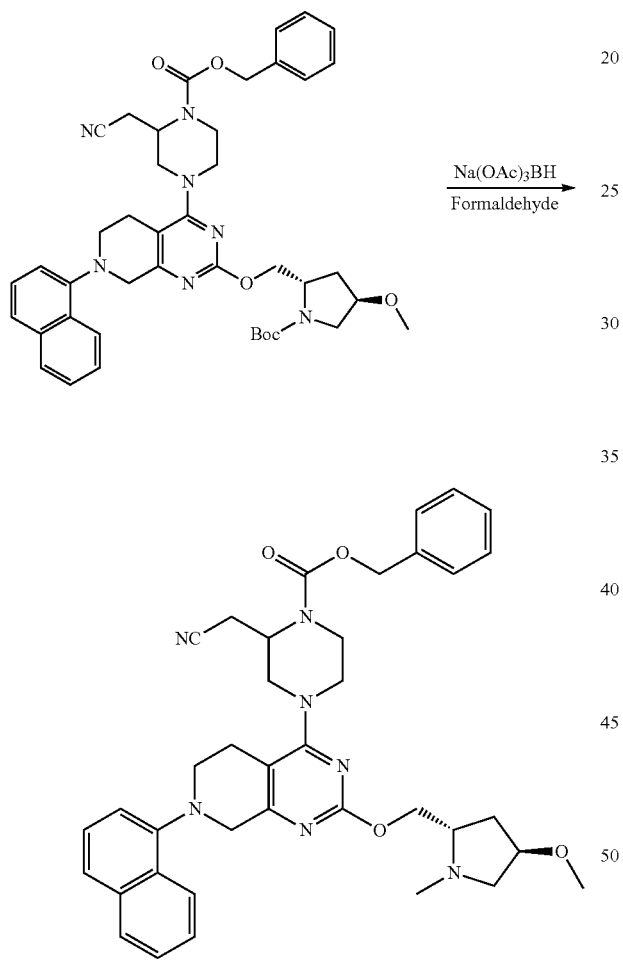

Step B: benzyl 2-(cyanomethyl)-4-(2-(((2S,4R)-4-methoxy-1-methylpyrrolidin-2-yl)methoxy)-7-(naphthalen-1-yl)-5,6,7,8-tetrahydropyrido[3,4-d]pyrimidin-4-yl)piperazine-1-carboxylate benzyl 4-(2-(((2S,4R)-1-(tert-butoxycarbonyl)-4-methoxypyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (27.0 mg, 0.04 mmol, formaldehyde (15.7 μl, 0.2 mmol), Na(OAc)3BH (17.7 mg, 0.08 mmol) were placed in THF (2 mL) and stirred for 2 hrs. Saturated bicarbonate was added and the mixture was extracted with 10% MeOH in DCM (3×15 mL). The extracts were combined, dried with sodium sulfate, and concentrated to provide crude material which was used as is.

Step C: 2-(1-acryloyl-4-(2-(((2S,4R)-4-methoxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile was prepared following Example 375 Step F and G, substituting benzyl 2-(cyanomethyl)-4-(2-(((2S,4R)-4-methoxy-1-methylpyrrolidin-2-yl)methoxy)-7-(naphthalen-1-yl)-5,6,7,8-tetrahydropyrido[3,4-d]pyrimidin-4-yl)piperazine-1-carboxylate for benzyl 2-(cyanomethyl)-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazine-1-carboxylate in Step F. ESI+APCI MS m/z 582.3 [M+H]+.

Example 382

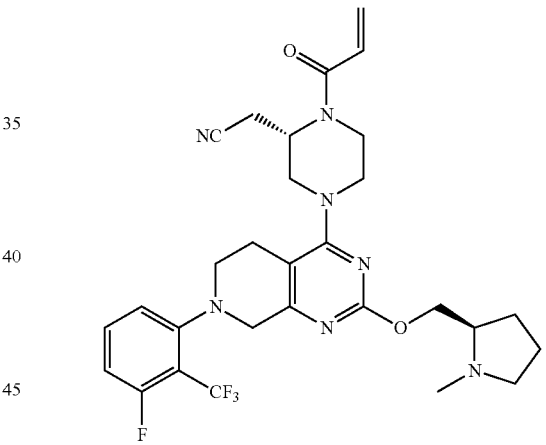

2-((S)-1-acryloyl-4-(7-(3-fluoro-2-(trifluoromethyl)phenyl)-2-(((R)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(3-fluoro-2-(trifluoromethyl)phenyl)-2-(((R)-1-methylpyrrolidin-2-yl)methoxy)-5,6,7,8-tetrahydropyrido[3,4-d]pyrimidin-4-yl)piperazin-2-yl)acetonitrile was prepared following Example 234, Steps F-J, substituting (R)-(1-methylpyrrolidin-2-yl)methanol for (S)-(1-methylpyrrolidin-2-yl)methanol in Step F and 1-bromo-3-fluoro-2-(trifluoromethyl)benzene for 1-bromonaphthalene in Step H. ESI+APCI MS m/z 588.3 [M+H]+.

Example 383

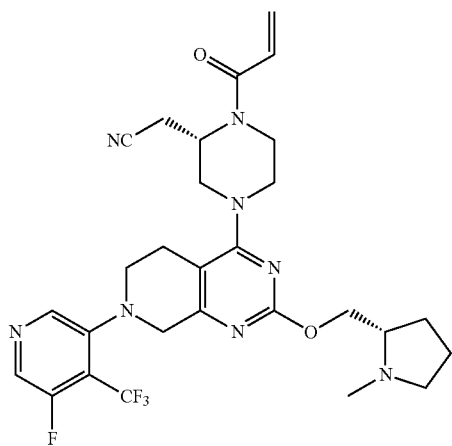 [SMILES: C=CC(=O)N1CCN(c2nc(OC[C@@H]3CCCN3C)nc3c2CCN(c2cncc(F)c2C(F)(F)F)C3)C[C@@H]1CC#N]

2-((S)-1-acryloyl-4-(7-(5-fluoro-4-(trifluoromethyl)pyridin-3-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(5-fluoro-4-(trifluoromethyl)pyridin-3-yl)-2-(((S)-1-methylpyrrolidin-2-yl)methoxy)-5,6,7,8-tetrahydropyrido[3,4-d]pyrimidin-4-yl)piperazin-2-yl)acetonitrile was prepared following Example 234, Steps H-J, substituting 3-bromo-5-fluoro-4-(trifluoromethyl)pyridine for 1-bromonaphthalene in Step H. ESI+APCI MS m/z 589.3 [M+H]⁺.

Example 384

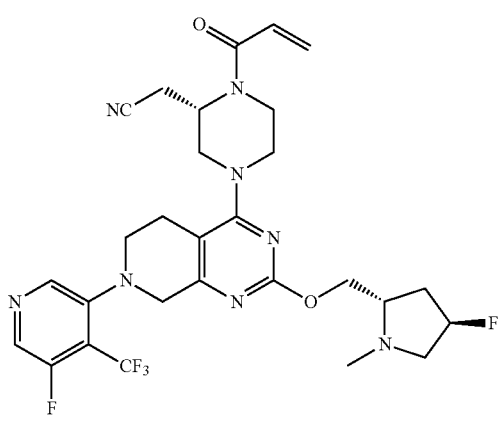 [SMILES: C=CC(=O)N1CCN(c2nc(OC[C@@H]3C[C@@H](F)CN3C)nc3c2CCN(c2cncc(F)c2C(F)(F)F)C3)C[C@@H]1CC#N]

Example 2-((S)-1-acryloyl-4-(2-(((2S,4R)-4-fluoro-1-methyl-pyrrolidin-2-yl)methoxy)-7-(5-fluoro-4-(trifluoromethyl)pyridin-3-yl)-5,6,7,8-tetrahydropyrido[3,4-d]pyrimidin-4-yl)piperazin-2-yl)acetonitrile

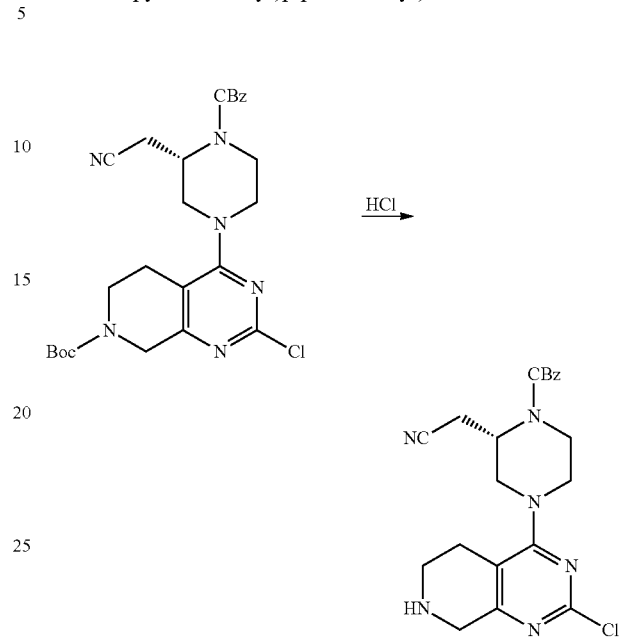

Step A: benzyl (S)-4-(2-chloro-5,6,7,8-tetrahydropyrido[3,4-d]pyrimidin-4-yl)-2-(cyanomethyl)piperazine-1-carboxylate Tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (5.37 g, 10.2 mmol) was placed in DCM (75 mL) and was cooled to 0° C. HCl (12.7 ml, 50.9 mmol) was added and the reaction was warmed to rt and was stirred for 2 hr. The reaction was concentrated and was brought up in DCM. Saturated bicarbonate was added and the mixture was extracted with DCM (3×50 mL). The organic layers were combined, dried, and concentrated to provide benzyl (S)-4-(2-chloro-5,6,7,8-tetrahydropyrido[3,4-d]pyrimidin-4-yl)-2-(cyanomethyl)piperazine-1-carboxylate (4.33 g, 10.1 mmol, 99% yield) which was used as is.

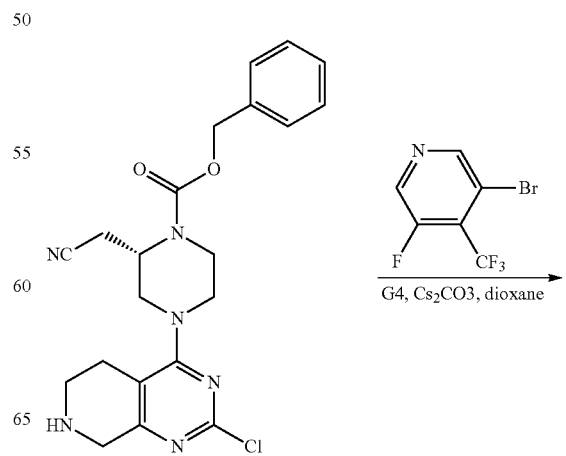

1077

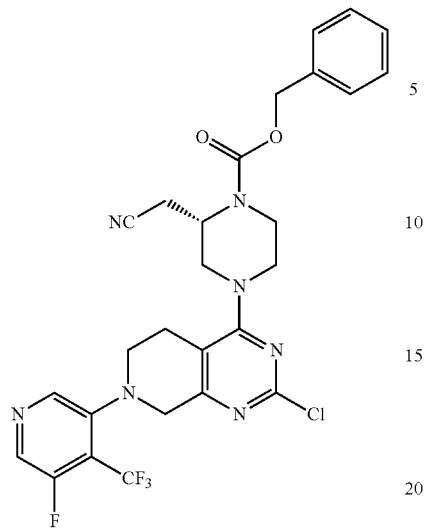

Step B: benzyl (S)-4-(2-chloro-7-(5-fluoro-4-(trifluoromethyl)pyridin-3-yl)-5,6,7,8-tetrahydropyrido[3,4-d]pyrimidin-4-yl)-2-(cyanomethyl)piperazine-1-carboxylate To a vial was added cesium carbonate (2.29 g, 7.0 mmol), benzyl (S)-4-(2-chloro-5,6,7,8-tetrahydropyrido[3,4-d]pyrimidin-4-yl)-2-(cyanomethyl)piperazine-1-carboxylate (1.00 g, 2.3 mmol), methanesulfonato(2-dicyclohexylphosphino-2',6'-di-i-propoxy-1,1'-biphenyl)(2'-methylamino-1,1'-biphenyl-2-yl)palladium(II) (0.30 g, 0.35 mmol), 3-bromo-5-fluoro-4-(trifluoromethyl)pyridine (1.29 g, 5.3 mmol) and 1,4-dioxane (15.6 ml, 2.3 mmol) the vial was degassed with Ar and sealed then heated to 90° C. for 24 hr. The reaction was cooled and water and saturated NH₄Cl was added and the mixture was extracted with DCM. The organic layers were combined and concentrated. The resulting residue was purified by silica gel (5-75% EtOAc in hexane) to provide benzyl (S)-4-(2-chloro-7-(5-fluoro-4-(trifluoromethyl)pyridin-3-yl)-5,6,7,8-tetrahydropyrido[3,4-d]pyrimidin-4-yl)-2-(cyanomethyl)piperazine-1-carboxylate (634 mg, 1.1 mmol, 46% yield).

1078

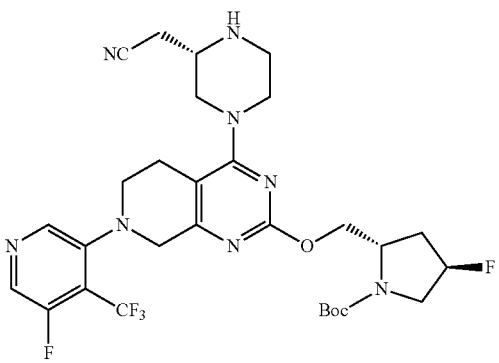

Step C: tert-butyl (2S,4R)-2-(((4-((S)-3-(cyanomethyl)piperazin-1-yl)-7-(5-fluoro-4-(trifluoromethyl)pyridin-3-yl)-5,6,7,8-tetrahydropyrido[3,4-d]pyrimidin-2-yl)oxy)methyl)-4-fluoropyrrolidine-1-carboxylate In a conical bottom vial, a solution of benzyl (S)-4-(2-chloro-7-(5-fluoro-4-(trifluoromethyl)pyridin-3-yl)-5,6,7,8-tetrahydropyrido[3,4-d]pyrimidin-4-yl)-2-(cyanomethyl)piperazine-1-carboxylate (634 mg, 1.07 mmol) in dioxane (10746 µl, 1.07 mmol) was sparged with argon. Tert-butyl (2S,4R)-4-fluoro-2-(hydroxymethyl)pyrrolidine-1-carboxylate (942 mg, 4.30 mmol), Cs₂CO₃ (1050 mg, 3.22 mmol), methanesulfonato(2-dicyclohexylphosphino-2',6'-di-i-propoxy-1,1'-biphenyl)(2'-methylamino-1,1'-biphenyl-2-yl)palladium(II) (137 mg, 0.161 mmol) were sequentially added under argon and sparged for an additional 5 min. The reaction mixture was capped and heated at 100° C. for 18 hr. The reaction was cooled and water was added. The mixture was extracted with DCM (3×20 mL) and the extracts were combined and concentrated. The resulting residue was purified by silica gel (0-10% MeOH) to provide tert-butyl (2S,4R)-2-(((4-((S)-3-(cyanomethyl)piperazin-1-yl)-7-(5-fluoro-4-(trifluoromethyl)pyridin-3-yl)-5,6,7,8-tetrahydropyrido[3,4-d]pyrimidin-2-yl)oxy)methyl)-4-fluoropyrrolidine-1-carboxylate (579 mg, 0.907 mmol, 84% yield).

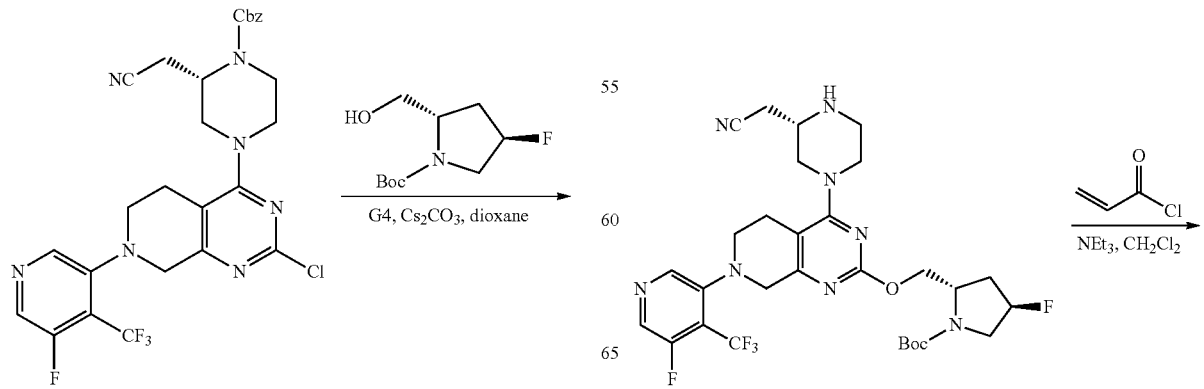

1079

-continued

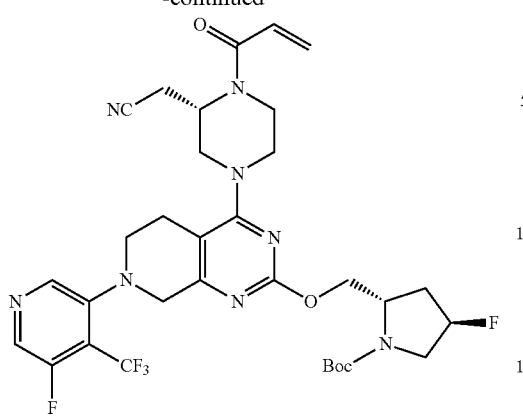

Step D: tert-butyl (2S,4R)-2-(((4-((S)-4-acryloyl-3-(cyanomethyl)piperazin-1-yl)-7-(5-fluoro-4-(trifluoromethyl)pyridin-3-yl)-5,6,7,8-tetrahydropyrido[3,4-d]pyrimidin-2-yl)oxy)methyl)-4-fluoropyrrolidine-1-carboxylate Tert-butyl (2S,4R)-2-(((4-((S)-3-(cyanomethyl)piperazin-1-yl)-7-(5-fluoro-4-(trifluoromethyl)pyridin-3-yl)-5,6,7,8-tetrahydropyrido[3,4-d]pyrimidin-2-yl)oxy)methyl)-4-fluoropyrrolidine-1-carboxylate (579 mg, 0.907 mmol), triethylamine (379 µl, 2.72 mmol) were placed in CH$_2$Cl$_2$ (9066 µl, 0.907 mmol) and cooled to 0° C. Acryloyl chloride (6044 µl, 1.81 mmol) was added (freshly prepared 0.3M solution in DCM) and the reaction was stirred for 45 min at 0° C. Water was added and the mixture was extracted with DCM (3×15 mL). The layers were combined and concentrated to provide crude material that was used as is.

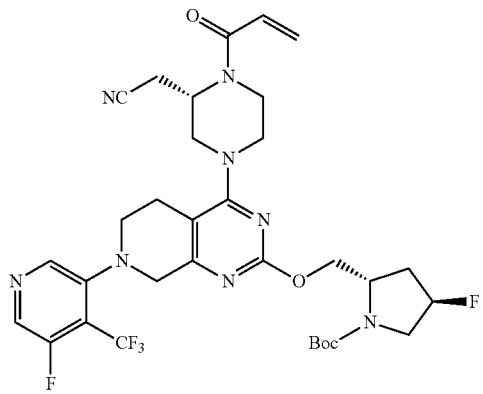

1080

-continued

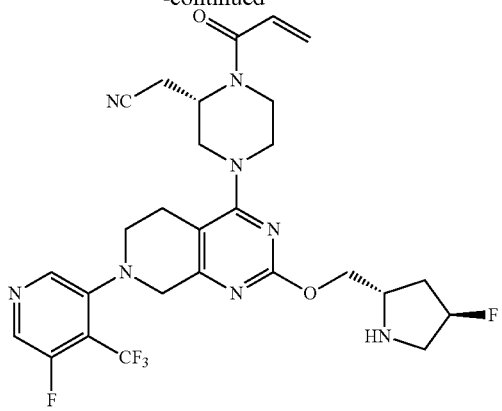

Step E: 2-((S)-1-acryloyl-4-(7-(5-fluoro-4-(trifluoromethyl)pyridin-3-yl)-2-(((2S,4R)-4-fluoropyrrolidin-2-yl)methoxy)-5,6,7,8-tetrahydropyrido[3,4-d]pyrimidin-4-yl)piperazin-2-yl)acetonitrile In a sealed vessel tert-butyl (2S,4R)-2-(((4-((S)-4-acryloyl-3-(cyanomethyl)piperazin-1-yl)-7-(5-fluoro-4-(trifluoromethyl)pyridin-3-yl)-5,6,7,8-tetrahydropyrido[3,4-d]pyrimidin-2-yl)oxy)methyl)-4-fluoropyrrolidine-1-carboxylate (628 mg, 0.91 mmol) was placed in MeOH (2 mL). HCl (756 µl, 4.53 mmol) (6M aqueous) was added and the mixture was stirred at rt for 5 hr. Saturated bicarbonate was added slowly to bring the pH ~9. The mixture was extracted with DCM (3×20 mL). The extracts were combined, dried, filtered and concentrated to provide crude material that was used as is.

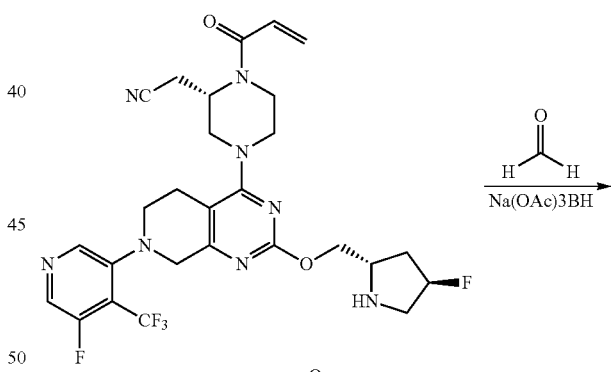

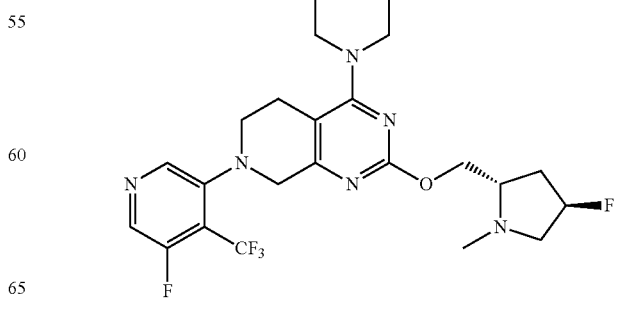

Step F: 2-((S)-1-acryloyl-4-(2-(((2S,4R)-4-fluoro-1-methylpyrrolidin-2-yl)methoxy)-7-(5-fluoro-4-(trifluoromethyl)pyridin-3-yl)-5,6,7,8-tetrahydropyrido[3,4-d]pyrimidin-4-yl)piperazin-2-yl)acetonitrile 2-((S)-1-acryloyl-4-(7-(5-fluoro-4-(trifluoromethyl)pyridin-3-yl)-2-(((2S,4R)-4-fluoropyrrolidin-2-yl)methoxy)-5,6,7,8-tetrahydropyrido[3,4-d]pyrimidin-4-yl)piperazin-2-yl)acetonitrile (175 mg, 0.30 mmol), formaldehyde (111 µl, 1.48 mmol), Na(OAc)3BH (125 mg, 0.59 mmol) and were placed in THF (2 mL) and stirred for 2 hrs. Saturated bicarbonate was added and the mixture was extracted with 10% MeOH in DCM (3×15 mL). The extracts were combined, dried with sodium sulfate, and concentrated. The resulting residue was purified by silica gel (4-13% MeOH in DCM with 0.25% NH₄OH) to provide 2-((S)-1-acryloyl-4-(2-(((2S,4R)-4-fluoro-1-methylpyrrolidin-2-yl)methoxy)-7-(5-fluoro-4-(trifluoromethyl)pyridin-3-yl)-5,6,7,8-tetrahydropyrido[3,4-d]pyrimidin-4-yl)piperazin-2-yl)acetonitrile (69.7 mg, 0.115 mmol, 39% yield). ESI+APCI MS m/z 607.2 [M+H]⁺.

Example 385

2-((S)-1-acryloyl-4-(7-(5-chloro-4-(trifluoromethyl)pyridin-3-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(5-chloro-4-(trifluoromethyl)pyridin-3-yl)-2-(((S)-1-methylpyrrolidin-2-yl)methoxy)-5,6,7,8-tetrahydropyrido[3,4-d]pyrimidin-4-yl)piperazin-2-yl)acetonitrile was prepared following Example 234, Steps H-J, substituting 3-bromo-5-chloro-4-(trifluoromethyl)pyridine for 1-bromonaphthalene in Step H and THF for MeOH in Step I. ESI+APCI MS m/z 605.3 [M+H]⁺.

Example 386

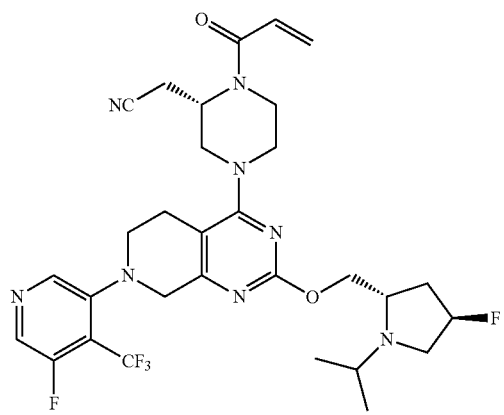 [SMILES: C=CC(=O)N1CCN(c2nc(OC[C@@H]3C[C@@H](F)CN3C(C)C)nc3c2CCN(c2cncc(F)c2C(F)(F)F)C3)C[C@@H]1CC#N]

2-((S)-1-acryloyl-4-(2-(((2S,4R)-4-fluoro-1-isopropylpyrrolidin-2-yl)methoxy)-7-(5-fluoro-4-(trifluoromethyl)pyridin-3-yl)-5,6,7,8-tetrahydropyrido[3,4-d] pyrimidin-4-yl)piperazin-2-yl)acetonitrile 2-((S)-1-acryloyl-4-(2-(((2S,4R)-4-fluoro-1-isopropylpyrrolidin-2-yl)methoxy)-7-(5-fluoro-4-(trifluoromethyl)pyridin-3-yl)-5,6,7,8-tetrahydropyrido[3,4-d]pyrimidin-4-yl)piperazin-2-yl)acetonitrile was prepared following the prep for Example 384, Step F, substituting propan-2-one for formaldehyde in step F. ESI+APCI MS m/z 635.3 [M+H]⁺.

Example 387

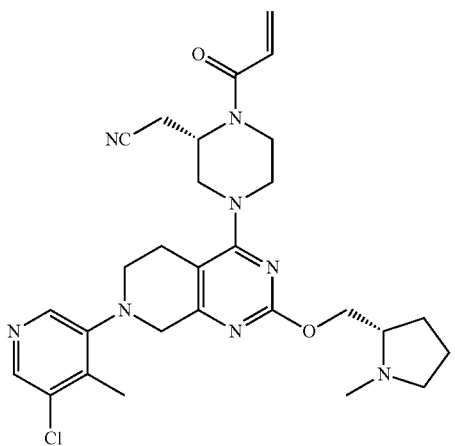 [SMILES: C=CC(=O)N1CCN(c2nc(OC[C@@H]3CCCN3C)nc3c2CCN(c2cncc(Cl)c2C)C3)C[C@@H]1CC#N]

2-((S)-1-acryloyl-4-(7-(5-chloro-4-methylpyridin-3-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(5-chloro-4-methylpyridin-3-yl)-2-(((S)-1-methylpyrrolidin-2-yl)methoxy)-5,6,7,8-tetrahydropyrido[3,4-d]pyrimidin-4-yl)piperazin-2-yl)acetonitrile was prepared following Example 234, Steps H-J, substituting 3-bromo-5-chloro-4-methylpyridine for 1-bromonaphthalene in Step H. ESI+APCI MS m/z 551.2 [M+H]+.

Example 388

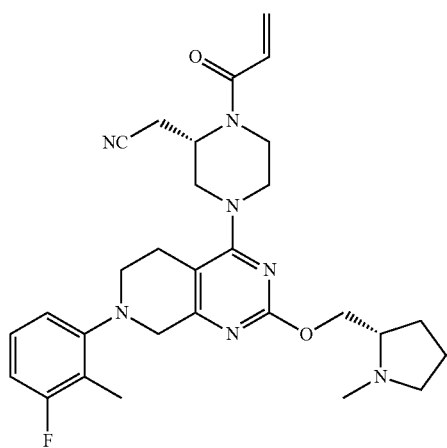 [SMILES: C=CC(=O)N1CCN(c2nc(OC[C@@H]3CCCN3C)nc3c2CCN(c2cccc(F)c2C)C3)C[C@@H]1CC#N]

2-((S)-1-acryloyl-4-(7-(3-fluoro-2-methylphenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(3-fluoro-2-methylphenyl)-2-(((S)-1-methylpyrrolidin-2-yl)methoxy)-5,6,7,8-tetrahydropyrido[3,4-d]pyrimidin-4-yl)piperazin-2-yl)acetonitrile was prepared following Example 234, Steps H-J, substituting 1-bromo-3-fluoro-2-methylbenzene for 1-bromonaphthalene in Step H. ESI+APCI MS m/z 534.3 [M+H]+.

Example 389

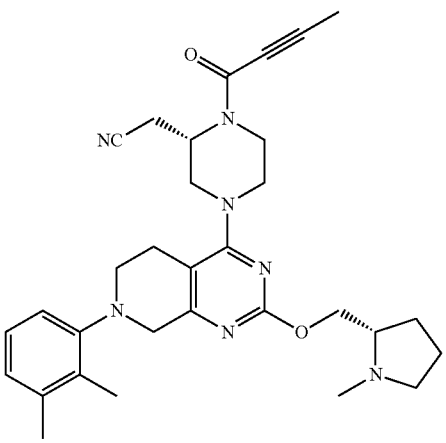 [SMILES: CC#CC(=O)N1CCN(c2nc(OC[C@@H]3CCCN3C)nc3c2CCN(c2cccc(C)c2C)C3)C[C@@H]1CC#N]

2-((S)-1-(but-2-ynoyl)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile

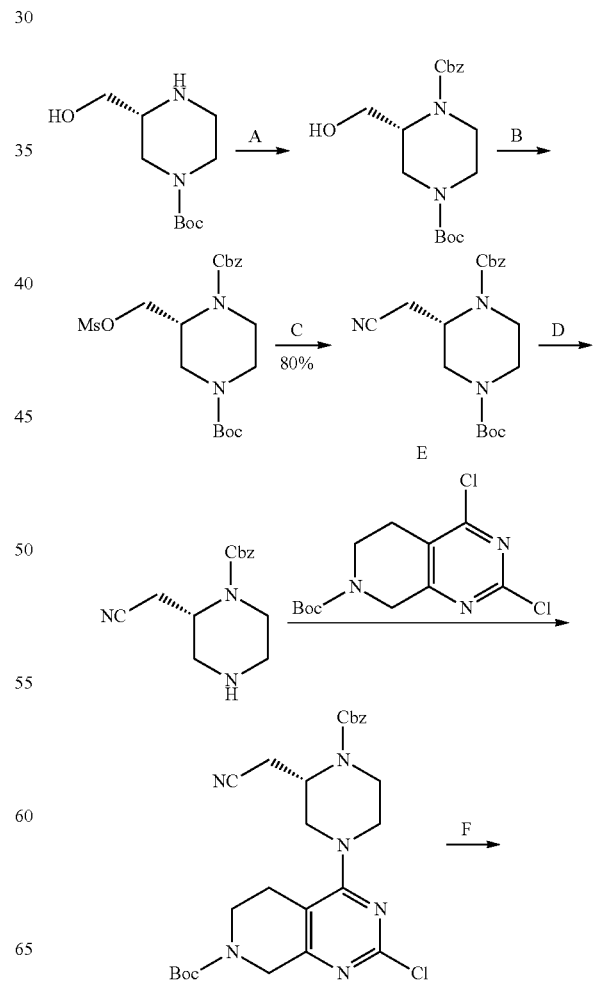

1085
-continued

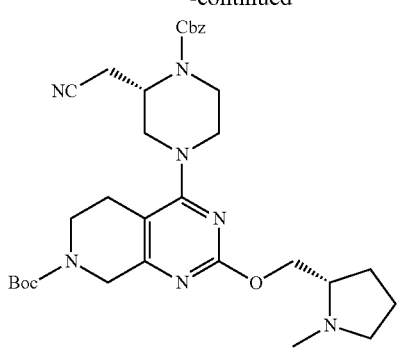

1086
-continued

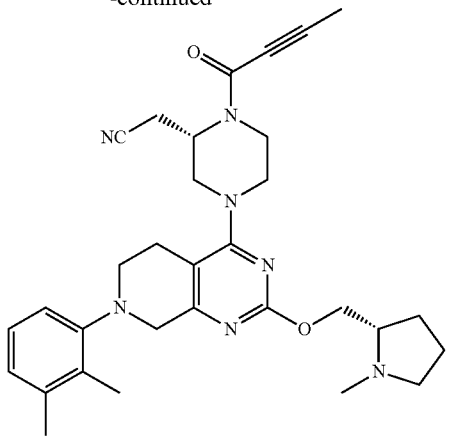

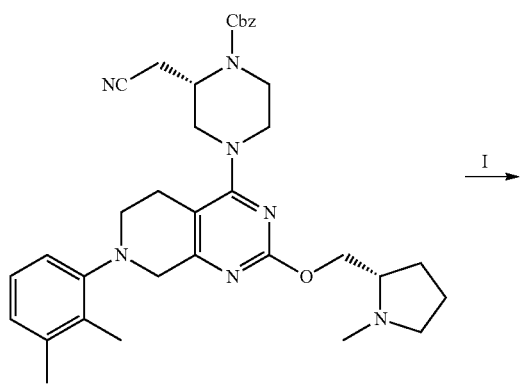

Step A: 1-benzyl 4-(tert-butyl) (R)-2-(hydroxymethyl)piperazine-1,4-dicarboxylate To tert-butyl (R)-3-(hydroxymethyl)piperazine-1-carboxylate (76.0 g, 351 mmol) in a 3 L flask was added water (500 mL) and the slurry was stirred until the material was completely dissolved. To this mixture was added EtOAc (541 ml, 351 mmol) followed by $NaHCO_3$ (88.6 g, 1.05 mol) and the resulting mixture was stirred for 3 min (internal temp=20° C.). To this mixture was added Cbz-Cl (52.5 ml, 369 mmol) over 3 minutes (internal temp from 20° C. to 25° C., off-gas seen at this point) and the reaction was stirred for 1 d at rt. The reaction mixture was transferred to a separatory funnel and the organic layer was washed with brine, dried ($MgSO_4$) and concentrated in vacuo. The residue was purified by flash chromatography eluting with 10-70% EtOAc/hex to afford 1-benzyl 4-(tert-butyl) (R)-2-(hydroxymethyl)piperazine-1,4-dicarboxylate (114.6 g, 327.0 mmol, 93% yield). ESI+APCI MS m/z 251.1 [M-Boc+H]$^+$.

Step B: 1-benzyl 4-(tert-butyl) (R)-2-(((methyl sulfonyl)oxy)methyl)piperazine-1,4-dicarboxylate To a solution of 1-benzyl 4-(tert-butyl) (R)-2-(hydroxymethyl)piperazine-1,4-dicarboxylate (32 g, 91.3 mmol) in $CH_2Cl_2$ (457 mL, 0.2 M) cooled to 0° C. was added DIEA (24.6 ml, 137 mmol) followed by methanesulfonyl chloride (7.77 ml, 100 mmol) over 1 minute and the mixture was stirred at 0° C. for 1 h. The reaction mixture was transferred to a separatory funnel and washed with 1:1 water/brine (500 mL). The organic layer was collected, dried ($MgSO_4$), and concentrated in vacuo. The residue was purified by flash chromatography eluting with 10-60% EtOAc/hex to afford 1-benzyl 4-(tert-butyl) (R)-2-(((methylsulfonyl)oxy)methyl)piperazine-1,4-dicarboxylate (33 g, 77.0 mmol, 84.3% yield). ESI+APCI MS m/z 329.1 [M-Boc+H]$^+$.

Step C: 1-benzyl 4-(tert-butyl) (S)-2-(cyanomethyl)piperazine-1,4-dicarboxylate To a solution of 1-benzyl 4-(tert-butyl) (R)-2-(((methylsulfonyl)oxy)methyl)piperazine-1,4-dicarboxylate (12.6 g, 29.4 mmol) in DMA (368 ml, 73.5 mmol) was sparged with argon. To the solution was added sodium cyanide (3.60 g, 73.5 mmol) and the reaction stirred at 55° C. for 1 d, monitoring by HPLC (long method) to determine reaction completion. The reaction mixture was transferred to a separatory funnel, diluted with 0.5M NaOH (800 mL) then extracted with MTBE (2×). The combined organic layers were next washed with basic water (2×200 mL), brine (100 mL), dried (MgSO$_4$) and concentrated in vacuo. The residue was purified by flash chromatography eluting with 10→60% EtOAc/hex as eluent to afford 1-benzyl 4-(tert-butyl) (S)-2-(cyanomethyl)piperazine-1,4-dicarboxylate (7.9 g, 22.0 mmol, 75% yield). ESI+APCI MS m/z 260.1 [M-Boc+H]$^+$.

Step D: benzyl (S)-2-(cyanomethyl)piperazine-1-carboxylate hydrochloride

To a solution of 1-benzyl 4-(tert-butyl) (S)-2-(cyanomethyl)piperazine-1,4-dicarboxylate (20.4 g, 56.8 mmol) in DCM (50 mL) was added hydrogen chloride (99.3 ml, 397 mmol) (4.0 M solution in dioxane) and the reaction stirred at rt for 1.5 hrs. The reaction mixture was concentrated in vacuo and dried under vacuum to give benzyl (S)-2-(cyanomethyl)piperazine-1-carboxylate hydrochloride (16.8 g, 56.8 mmol, 100% yield) as a foam. ESI+APCI MS m/z 260.1 [M+H]$^+$.

Step E: tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate To a solution of benzyl (S)-2-(cyanomethyl)piperazine-1-carboxylate hydrochloride (16.8 g, 56.8 mmol) in DMA (114 ml, 56.8 mmol) was added tert-butyl 2,4-dichloro-5,8-dihydropyrido[3,4-d]pyrimidine-7(6H)-carboxylate (15.5 g, 51.1 mmol) followed by DIEA (39.7 ml, 227 mmol) and the reaction mixture was stirred at RT for 1 hr. The reaction mixture was diluted with 1 L of water and extracted with MTBE (2×). The combined organics were washed with water (2×200 mL), brine, dried over MgSO$_4$ and concentrated in vacuo. The residue was purified by flash chromatography eluting with 10-60% EtOAc/hex as eluent to give tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (22.8 g, 43.3 mmol, 76% yield). ESI+APCI MS m/z 527.2 [M+H]$^+$.

Step F: tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate In 250 mL heavy-wall RBF with a PTFE screw cap, a solution of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (5.55 g, 10.5 mmol) in dioxane (60.2 ml, 10.5 mmol) was sparged with argon and (S)-(1-methylpyrrolidin-2-yl)methanol (3.64 g, 31.6 mmol), Cs$_2$CO$_3$ (10.3 g, 31.6 mmol), Ruphos Pd G3 (0.881 g, 1.05 mmol) were sequentially added and the resulting mixture was sparged with argon for an additional 5 min. The reaction mixture was capped and heated at 100° C. for 1 d. Upon consumption of starting material, the reaction mixture was cooled to ambient temperature and Cbz-Cl was added as necessary to convert Cbz-hydrolyzed product to title compound. The reaction mixture was then partitioned between EtOAc/10% brine. The aqueous layer was extracted with EtOAc (2×). The combined organic layers were dried (MgSO$_4$) and concentrated. The residue was purified by flash chromatography eluting with a gradient of 1.5% MeOH/0.15% NH$_4$OH/DCM to 11.25% MeOH/1.125% NH$_4$OH/DCM (Premix 15% MeOH/1.5% NH$_4$OH in DCM and ramp from 10-75% of this mixture in DCM) to afford the title compound (4.51 g, 7.45 mmol, 71%). ESI MS m/z 606.3 [M+H]$^+$.

Step G: benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate To a solution of tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (7.2 g, 12 mmol) in DCM (1.0 g, 12 mmol) was added HCl (4M in dioxane, 15 ml, 59 mmol). The mixture was stirred at RT for 2 h. The reaction mixture was concentrated to the bis HCl salt. The residue was partitioned between DCM/NaHCO$_3$ (sat) and the aqueous layer was extracted with DCM (3×). The combined organic layers were dried and concentrated to provide the title compound 4.72 g (0.009 mmol, 79%). ESI MS m/z 506.3 [M+H]$^+$.

Step H: benzyl (S)-2-(cyanomethyl)-4-(7-(2,3-dimethylphenyl)-2-((S)-1-methylpyrrolidin-2-yl)methoxy)-5,6,7,8-tetrahydropyrido[3,4-d]pyrimidin-4-yl)piperazine-1-carboxylate To a vial was added cesium carbonate (967 mg, 2.97 mmol), benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (500 mg, 0.989 mmol), Rhuphos Pd G3 (124 mg, 0.148 mmol), 1-bromo-2,3-dimethylbenzene (915 mg, 4.94 mmol) and 1,4-dioxane (9889 µl, 0.989 mmol) the vial was degassed with Ar and sealed then heated to 75° C. for 24 hr. Water and saturated NH$_4$Cl was added and the mixture was extracted with DCM. The organic layers were combined and concentrated. The resulting residue was purified by silica gel (0-12% MeOH in DCM w/0.25% NH$_4$OH) to provide benzyl (S)-2-(cyanomethyl)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazine-1-carboxylate (505 mg, 0.828 mmol, 83.7% yield). ESI MS m/z 610.4 [M+H]$^+$.

Step I: 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile To a solution of benzyl (S)-2-(cyanomethyl)-4-(7-(2,3-dimethylphenyl)-2-((S)-1-methylpyrrolidin-2-yl)methoxy)-5,6,7,8-tetrahydropyrido[3,4-d]pyrimidin-4-yl)piperazine-1-carboxylate (505 mg, 0.828 mmol) in EtOH (8282 µl, 0.828 mmol) and THF (8282 µl, 0.828 mmol) was added palladium (441 mg, 0.207 mmol) (Degussa Type, 10 wt %, 50% H$_2$O) and then an atmosphere of H$_2$ was introduced via vacuum followed by balloon pressure. The mixture was then stirred at ambient temperature for 2 hours. The mixture was then diluted with MeOH and THF 1:1 and filtered through GF/F paper. The filtrate was then concentrated to provide crude product which was used as is. ESI MS m/z 476.3 [M+H]$^+$.

Step J: 2-((S)-1-(but-2-ynoyl)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile At 0° C., to a 25 mL RBF containing N,N-dimethylformamide (4415 µl, 0.4415 mmol) was added 2-((S)-4-(7-(2, 3-dimethylphenyl)-2-((S)-1-methylpyrrolidin-2-yl)
methoxy)-5,6,7,8-tetrahydropyrido[3,4-d]pyrimidin-4-yl)
piperazin-2-yl)acetonitrile (210 mg, 0.44 mmol) and
triethylamine (122.7 μl, 0.88 mmol). The reaction mixture
was vigorously stirred while but-2-ynoic acid (44.54 mg,
0.53 mmol) was added in one portion. 1-Propanephosphonic
acid cyclic anhydride (197.1 μl, 0.66 mmol) was added
slowly to the stirring mixture. The reaction was allowed to
stir for 2 hr at 0° C. Water was added and the solids were
filtered. The solids were purified by silica gel (5-18% MeOH
in DCM with 0.25% NH$_4$OH) to provide title compound
2-((S)-1-(but-2-ynoyl)-4-(7-(2,3-dimethylphenyl)-2-(((S)-
1-methylpyrrolidin-2-yl)methoxy)-5,6,7,8-tetrahydropyrido
[3,4-d]pyrimidin-4-yl)piperazin-2-yl)acetonitrile (EX-
AMPLE 389, 144 mg, 0.27 mmol, 60%). ESI+APCI MS m/z
542.3 [M+H]$^+$.

Example 390

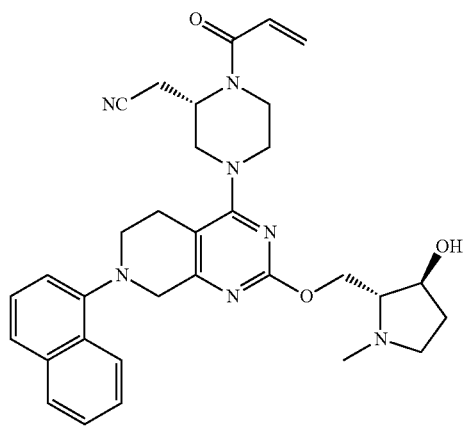 [SMILES: C=CC(=O)N1CCN(c2nc(OC[C@@H]3[C@@H](O)CCN3C)nc3c2CCN(c2cccc4ccccc24)C3)C[C@@H]1CC#N]

2-((S)-1-acryloyl-4-(2-(((2R,3S)-3-hydroxy-1-meth-
ylpyrrolidin-2-yl)methoxy)-7-(naphthalen-1-yl)-5,6,
7,8-tetrahydropyrido[3,4-d]pyrimidin-4-yl)piperazin-
2-yl)acetonitrile

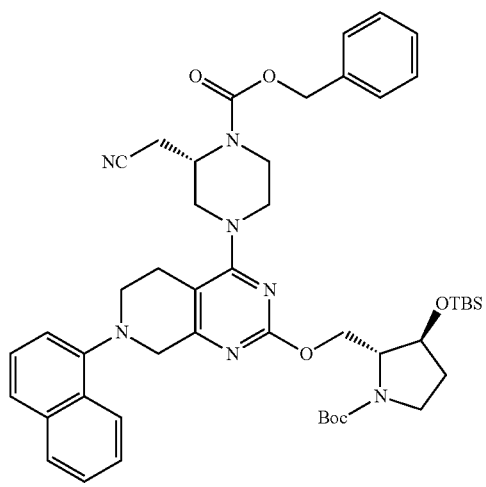 [SMILES: CC(C)(C)OC(=O)N1CC[C@H](O[Si](C)(C)C(C)(C)C)[C@H]1COc1nc2c(c(N3CCN(C(=O)OCc4ccccc4)[C@@H](CC#N)C3)n1)CCN(c1cccc3ccccc13)C2]

Step A: benzyl (S)-4-(2-(((2R,3S)-1-(tert-butoxycar-
bonyl)-3-((tert-butyldimethylsilyl)oxy)pyrrolidin-2-
yl)methoxy)-7-(naphthalen-1-yl)-5,6,7,8-tetrahydro-
pyrido[3,4-d]pyrimidin-4-yl)-2-(cyanomethyl)
piperazine-1-carboxylate was prepared according to Example 400, Step C-E substi-
tuting tert-butyl (2R,3S)-3-((tert-butyldimethylsilyl)oxy)-2-
(hydroxymethyl)pyrrolidine-1-carboxylate for (S)-(1-meth-
ylpyrrolidin-2-yl)methanol in Step C.

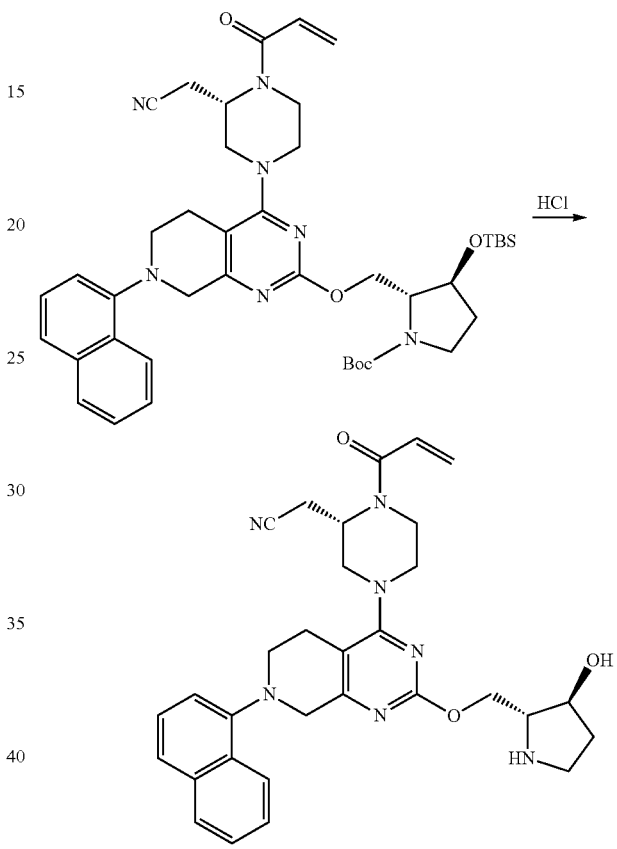

Step B: 2-((S)-1-acryloyl-4-(2-(((2R,3S)-3-hydroxy-
pyrrolidin-2-yl)methoxy)-7-(naphthalen-1-yl)-5,6,7,
8-tetrahydropyrido[3,4-d]pyrimidin-4-yl)piperazin-
2-yl)acetonitrile tert-butyl (2R,3S)-2-(((4-((S)-4-acryloyl-3-(cyanomethyl)
piperazin-1-yl)-7-(naphthalen-1-yl)-5,6,7,8-tetrahydro-
pyrido[3,4-d]pyrimidin-2-yl)oxy)methyl)-3-((tert-butyldim-
ethylsilyl)oxy)pyrrolidine-1-carboxylate (363 mg, 0.473
mmol) was placed in MeOH (10 mL). 6M aqueous HCl was
added and stirred at rt for 6 hr. The reaction was cooled to
0° C. and saturated bicarbonate was added slowly. The
mixture was extracted with DCM (3×20 ml). The extracts
were combined, dried, filtered and concentrated to provide
crude material that was used as is.

Step C: 2-((S)-1-acryloyl-4-(2-(((2R,3S)-3-hydroxy-
1-methylpyrrolidin-2-yl)methoxy)-7-(naphthalen-1-
yl)-5,6,7,8-tetrahydropyrido[3,4-d]pyrimidin-4-yl)
piperazin-2-yl)acetonitrile Was prepared according to EXAMPLE 384, Step F sub-
stituting 2-((S)-1-acryloyl-4-(2-(((2R,3S)-3-hydroxypyrrolidin-2-yl)methoxy)-7-(naphthalen-1-yl)-5,6,7,8-tetrahydro-pyrido[3,4-d]pyrimidin-4-yl)piperazin-2-yl)acetonitrile for 2-((S)-1-acryloyl-4-(7-(5-fluoro-4-(trifluoromethyl)pyridin-3-yl)-2-(((2S,4R)-4-fluoropyrrolidin-2-yl)methoxy)-5,6,7,8-tetrahydropyrido[3,4-d]pyrimidin-4-yl)piperazin-2-yl)acetonitrile. ESI+APCI MS m/z 568.3 [M+H]⁺.

Example 391

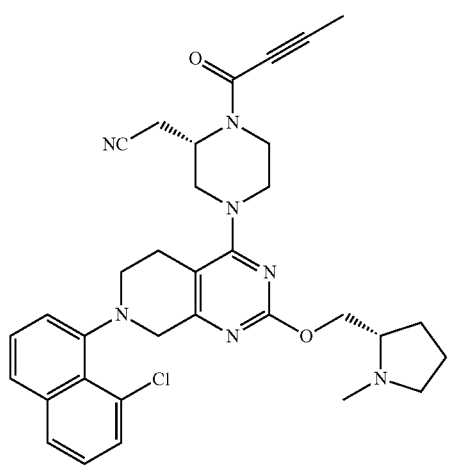 [SMILES: CC#CC(=O)N1CCN(c2nc(OC[C@@H]3CCCN3C)nc3c2CCN(c2cccc4cccc(Cl)c24)C3)C[C@@H]1CC#N]

2-((S)-1-(but-2-ynoyl)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-(but-2-ynoyl)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile Was prepared according to Example 389, Step H-J, substituting, 1-bromo-8-chloronaphthalene for 1-bromo-2,3-dimethylbenzene in Step H. ESI+APCI MS m/z 598.2 [M+H]⁺.

Example 392

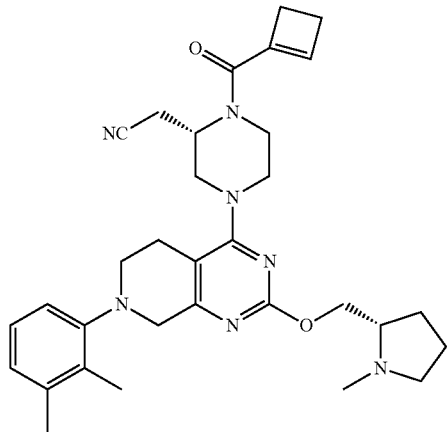 [SMILES: Cc1cccc(N2CCc3c(nc(OC[C@@H]4CCCN4C)nc3N3CCN(C(=O)C4=CCC4)[C@@H](CC#N)C3)C2)c1C]

2-((S)-1-(cyclobut-1-ene-1-carbonyl)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-(cyclobut-1-ene-1-carbonyl)-4-(7-(2,3-dimethylphenyl)-2-(((S)-1-methylpyrrolidin-2-yl)methoxy)-5,6,7,8-tetrahydropyrido [3,4-d]pyrimidin-4-yl)piperazin-2-yl)acetonitrile Was prepared following Example 389 Step J, substituting cyclobut-1-ene-1-carboxylic acid for but-2-ynoic acid. ESI+APCI MS m/z 556.3 [M+H]⁺.

Example 393

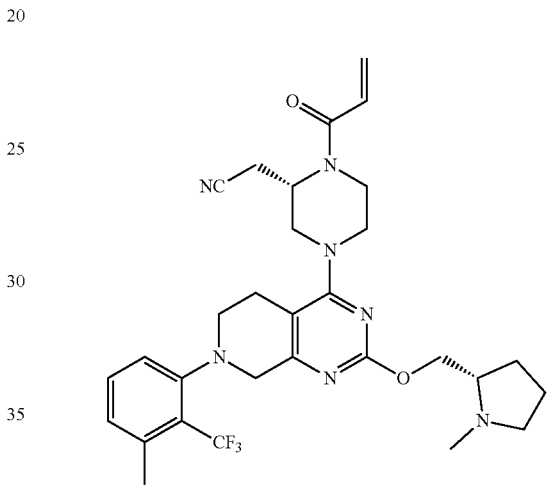

2-((S)-1-acryloyl-4-(7-(3-methyl-2-(trifluoromethyl)phenyl)-2-(((S)-1-methylpyrrolidin-2-yl)methoxy)-5,6,7,8-tetrahydropyrido[3,4-d]pyrimidin-4-yl)piperazin-2-yl)acetonitrile

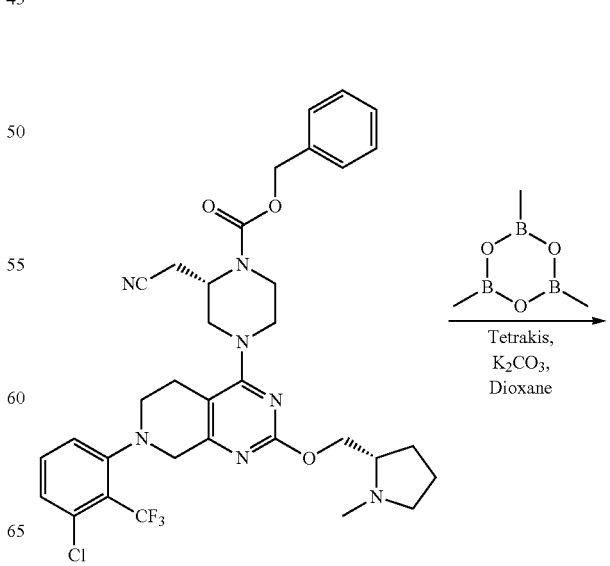

1093

-continued

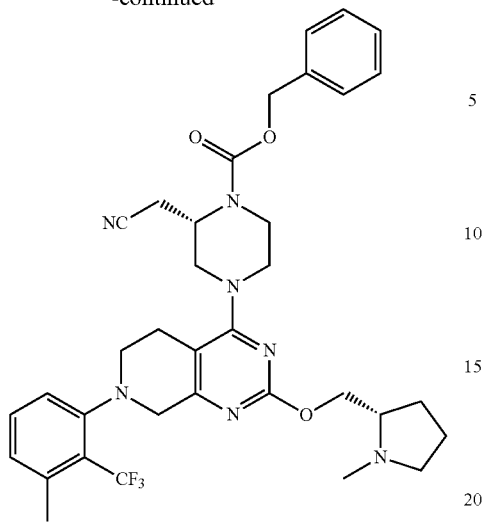

Step A: benzyl (S)-2-(cyanomethyl)-4-(7-(3-methyl-2-(trifluoromethyl)phenyl)-2-(((S)-1-methylpyrrolidin-2-yl)methoxy)-5,6,7,8-tetrahydropyrido[3,4-d]pyrimidin-4-yl)piperazine-1-carboxylate Benzyl (S)-4-(7-(3-chloro-2-(trifluoromethyl)phenyl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (150 mg, 0.22 mmol), K$_2$CO$_3$ (329 µl, 0.66 mmol), 2,4,6-trimethyl-1,3,5,2,4,6-trioxatriborinane (82.6 mg, 0.658 mmol) and Tetrakis (25.3 mg, 0.022 mmol) were placed in dioxane (731 µl, 0.22 mmol) and heated to 90° C. for 18 hr. Water was added and the mixture was extracted with 10% MeOH in DCM (3×15 mL). The extracts were combined and concentrated. The resulting residue was purified by silica gel (2-80% MeOH in DCM with 0.25% NH4OH) to provide benzyl (S)-2-(cyanomethyl)-4-(7-(3-methyl-2-(trifluoromethyl)phenyl)-2-((S)-1-methylpyrrolidin-2-yl)methoxy)-5,6,7,8-tetrahydropyrido[3,4-d]pyrimidin-4-yl)piperazine-1-carboxylate (75 mg, 0.11 mmol, 52% yield).

Step B: 2-((S)-1-acryloyl-4-(7-(3-methyl-2-(trifluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile Was prepared following Example 234, Step I and J substituting benzyl (S)-2-(cyanomethyl)-4-(7-(3-methyl-2-(trifluoromethyl)phenyl)-2-(((S)-1-methylpyrrolidin-2-yl)methoxy)-5,6,7,8-tetrahydropyrido[3,4-d]pyrimidin-4-yl)piperazine-1-carboxylate for benzyl (S)-2-(cyanomethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate in Step I. ESI+APCI MS m/z 584.3 [M+H]$^+$.

1094

Example 394

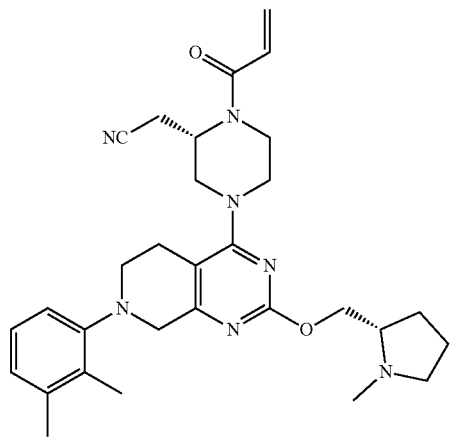 [SMILES: C=CC(=O)N1CCN(c2nc(OC[C@@H]3CCCN3C)nc3c2CCN(c2cccc(C)c2C)C3)C[C@@H]1CC#N]

2-((S)-1-acryloyl-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(2,3-dimethylphenyl)-2-((S)-1-methylpyrrolidin-2-yl)methoxy)-5,6,7,8-tetrahydropyrido[3,4-d]pyrimidin-4-yl)piperazin-2-yl)acetonitrile was prepared following Example 234, Steps H-J, substituting 1-bromo-2,3-dimethylbenzene for 1-bromonaphthalene in Step H. ESI+APCI MS m/z 530.3 [M+H]$^+$.

Example 395

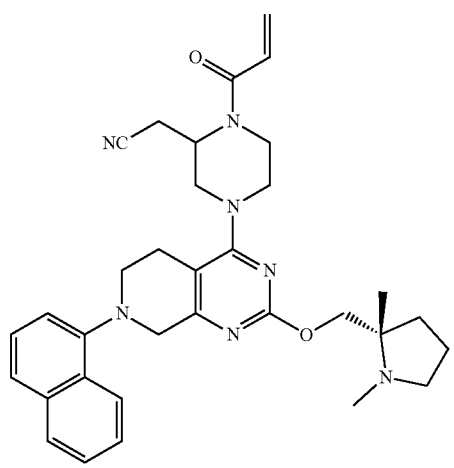 [SMILES: C=CC(=O)N1CCN(c2nc(OC[C@]3(C)CCCN3C)nc3c2CCN(c2cccc4ccccc24)C3)CC1CC#N]

1095

2-(1-acryloyl-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile

1096
-continued

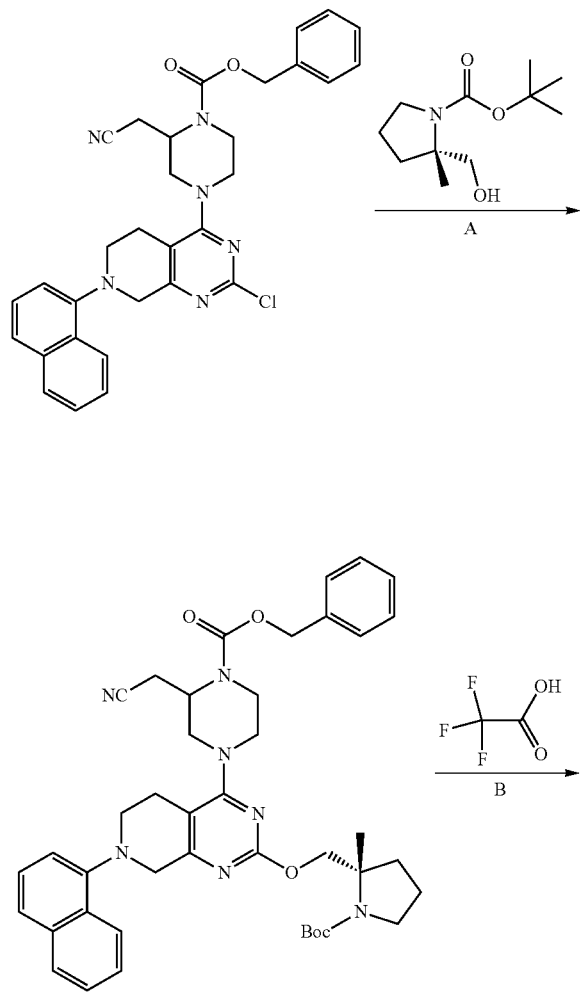
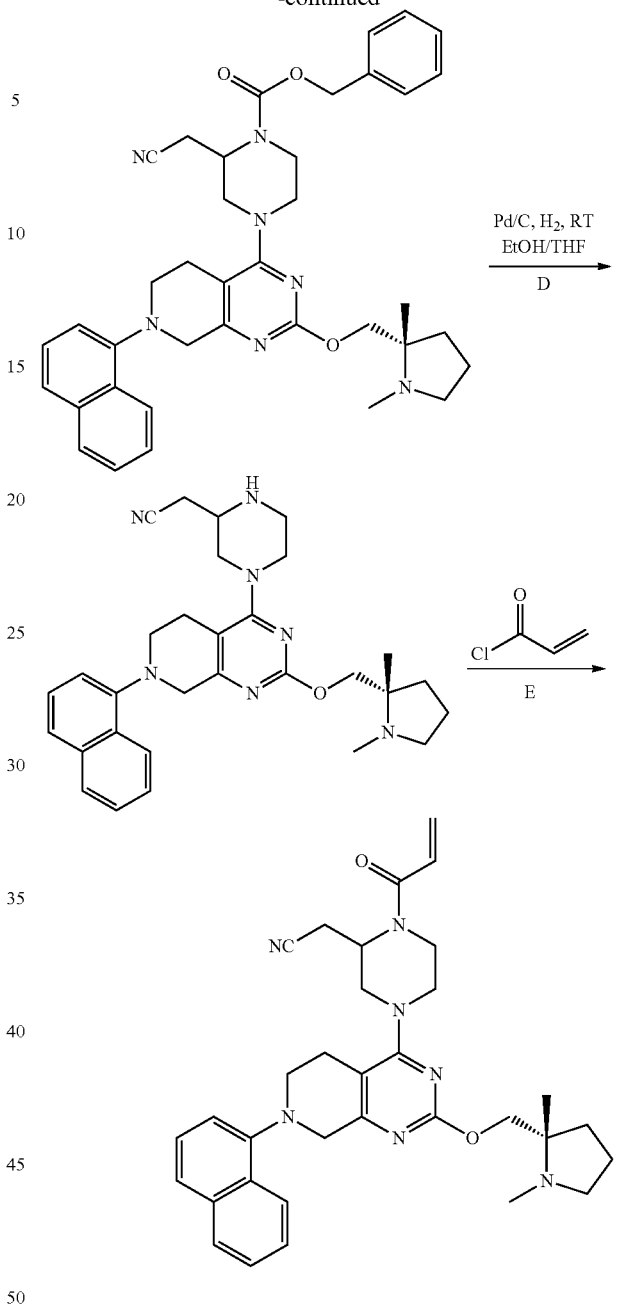

Step A: benzyl 4-(2-(((S)-1-(tert-butoxycarbonyl)-2-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate In a microwave tube benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (200 mg, 0.362 mmol) was dissolved in dioxane (181 μl, 0.362 mmol) and treated with cesium carbonate (236 mg, 0.723 mmol) and (S)-tert-butyl 2-(hydroxymethyl)-2-methylpyrrolidine-1-carboxylate (389 mg, 1.81 mmol). The tube was then capped and heated to 90° C. for 2 hours. The reaction was cooled to room temperature and filtered through GF/F paper. The filtrate was concentrated in vacuo and chromatographed on the CombiFlash eluting with 0%40% DCM:MeOH. All fractions containing clean product were combined and concentrated to give benzyl 4-(2-(((S)-1-(tert-butoxycarbonyl)-2-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (264 mg, 0.361 mmol, 99.7% yield). ESI+APCI MS m/z 732.4 [M+H]+.

Step B: benzyl 2-(cyanomethyl)-4-(2-(((S)-2-methylpyrrolidin-2-yl)methoxy)-7-(naphthalen-1-yl)-5,6,7,8-tetrahydropyrido[3,4-d]pyrimidin-4-yl)piperazine-1-carboxylate Benzyl 4-(2-(((S)-1-(tert-butoxycarbonyl)-2-methylpyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (264 mg, 0.361 mmol) was dissolved in dichloromethane (3607 µl, 0.361 mmol) and treated with TFA (556 µl, 7.21 mmol). The reaction stirred at room temperature for 1 hour. The reaction was concentrated in vacuo and treated with saturated bicarb. The aqueous was extracted with DCM (2×) and the combined organics dried over Na2SO4. The organics were concentrated in vacuo to give benzyl 2-(cyanomethyl)-4-(2-(((S)-2-methylpyrrolidin-2-yl)methoxy)-7-(naphthalen-1-yl)-5,6,7,8-tetrahydropyrido[3,4-d]pyrimidin-4-yl)piperazine-1-carboxylate (210 mg, 0.332 mmol, 92.2% yield). ESI+APCI MS m/z 632.3 [M+H]+.

Step C: benzyl 2-(cyanomethyl)-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazine-1-carboxylate Benzyl 2-(cyanomethyl)-4-(2-(((S)-2-methylpyrrolidin-2-yl)methoxy)-7-(naphthalen-1-yl)-5,6,7,8-tetrahydropyrido[3,4-d]pyrimidin-4-yl)piperazine-1-carboxylate (105 mg, 0.1662 mmol) was dissolved in formic acid (94.05 µl, 2.493 mmol) and treated with Formaldehyde (1868 µl, 24.93 mmol). The reaction mixture stirred at 85° C. for 1 hour. The reaction was cooled to room temperature and treated with saturated bicarb. The aqueous was extracted with DCM (2×). The combined organics were dried over Na2SO4, concentrated in vacuo and chromatographed on the CombiFlash eluting with 0%-10% DCM:MeOH. All fractions containing clean product were combined and concentrated in vacuo to give benzyl 2-(cyanomethyl)-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazine-1-carboxylate (75 mg, 0.1161 mmol, 69.88% yield). ESI+APCI MS m/z 646.3 [M+H]+.

Step D: 2-(4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile A solution of benzyl 2-(cyanomethyl)-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazine-1-carboxylate (117 mg, 0.181 mmol) in EtOH (1812 µl, 0.181 mmol) and THF (1812 µl, 0.181 mmol) was purged with N2 for 5 minutes. To this solution was added Palladium (96.4 mg, 0.0453 mmol) (Degussa Type, 10 wt %, 50% H2O), and was immediately capped and purged with N2 for an additional 5 min. The solution then stirred under an atmosphere of H2. The mixture was then diluted with MeOH and filtered through packed celite. The filtrate was then concentrated in vacuo to provide 2-(4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile (88 mg, 0.172 mmol, 94.9% yield). ESI+APCI MS m/z 512.3 [M+H]+.

Step E: 2-(1-acryloyl-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile To a suspension of 2-(4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile (88 mg, 0.17 mmol) in dichloromethane (1720 µl, 0.17 mmol) at ambient temperature was added Acryloyl Chloride (14 µl, 0.17 mmol) followed by Hunig's base (60 µl, 0.34 mmol). The reaction was then stirred at ambient temperature for 30 minutes. The reaction mixture was then concentrated in vacuo. The concentrate was suspended in a 60:40 mixture of ACN:H2O and purified on the Gilson (reverse prep HPLC), eluting with 5→95% ACN/0.1% TFA in water/0.1% TFA. Fractions containing product were combined and partitioned between saturated bicarb and DCM. The aqueous layer was extracted with DCM two more times. The organic layers were combined, dried over Na2SO4 and concentrated in vacuo to give 2-(1-acryloyl-4-(2-(((S)-1,2-dimethylpyrrolidin-2-yl)methoxy)-7-(naphthalen-1-yl)-5,6,7,8-tetrahydropyrido[3,4-d]pyrimidin-4-yl)piperazin-2-yl)acetonitrile (14 mg, 0.025 mmol, 14% yield). ESI+APCI MS m/z 566.3 [M+H]+.

Example 396

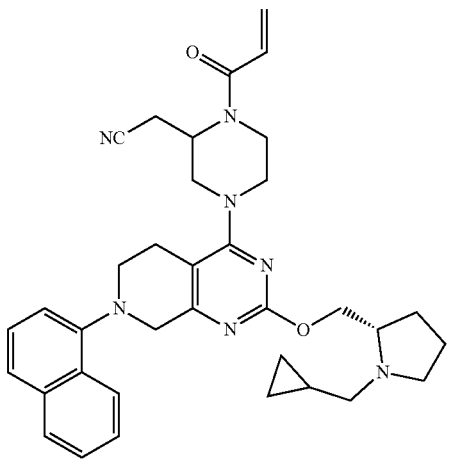 [SMILES: C=CC(=O)N1CCN(c2nc(OC[C@@H]3CCCN3CC3CC3)nc3c2CCN(c2cccc4ccccc24)C3)CC1CC#N]

1099

2-(1-acryloyl-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile

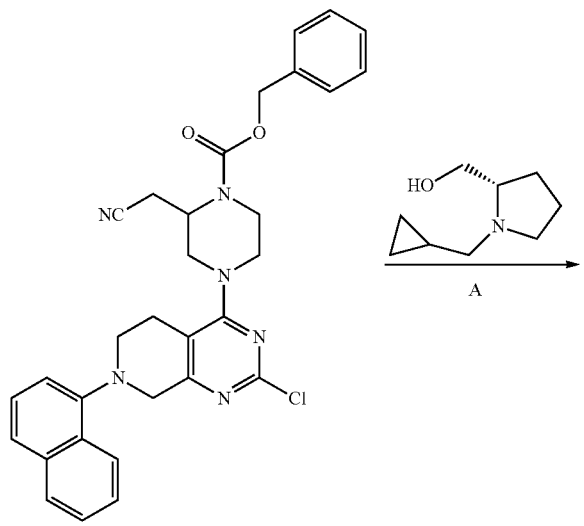

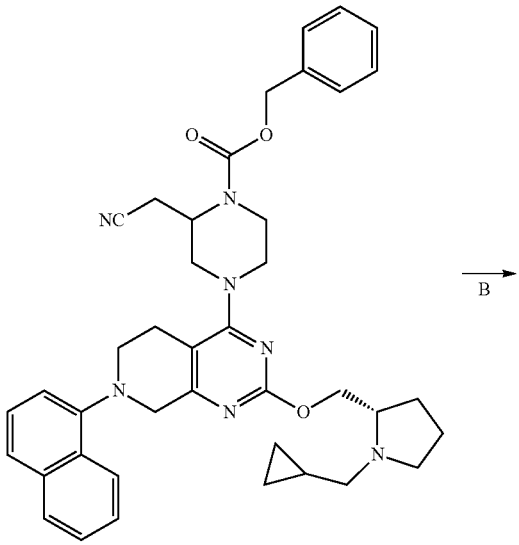

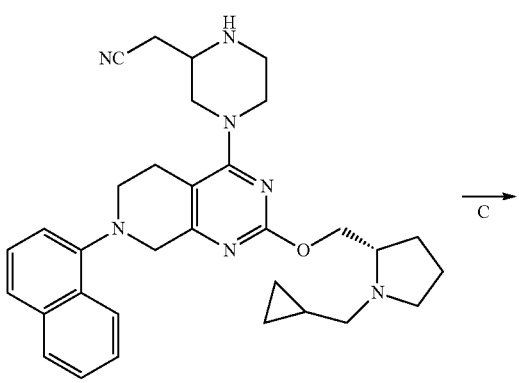

1100

-continued

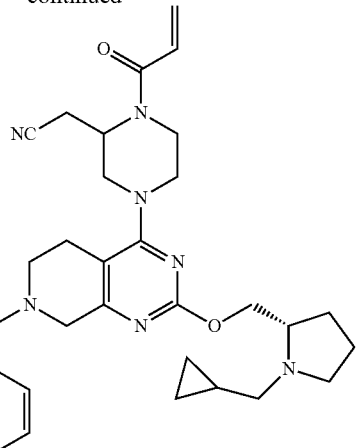

Step A: benzyl 2-(cyanomethyl)-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazine-1-carboxylate In a conical bottom vial, a solution of benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (200 mg, 0.362 mmol) in dioxane (3616 µl, 0.362 mmol) was sparged with Argon and (S)-(1-(cyclopropylmethyl)pyrrolidin-2-yl)methanol (168 mg, 1.08 mmol), Cs$_2$CO$_3$ (353 mg, 1.08 mmol), Rhuphos Pd G3 (30.2 mg, 0.0362 mmol) were sequentially added under argon and sparged for an additional 5 min. The reaction mixture was capped and heated at 100° C. for 1 hour. The reaction mixture was cooled to room temperature. EtOAc was added and washed with brine (2×). The combined organics were dried over Na$_2$SO$_4$ and concentrated in vacuo. The concentrate was purified by flash chromatography eluting with 0-20% DCM/MeOH+2% NH$_4$OH. All fractions containing clean desired product were combined and concentrated to give benzyl 2-(cyanomethyl)-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazine-1-carboxylate (90 mg, 0.134 mmol, 37.0% yield). ESI+APCI MS m/z 672.4 [M+H]$^+$.

Step B: 2-(4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile A solution of benzyl 2-(cyanomethyl)-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazine-1-carboxylate (90 mg, 0.13 mmol) in EtOH (1340 µl, 0.13 mmol) and THF (1340 µl, 0.13 mmol) was purged with N$_2$ for 5 min. To this solution was added Palladium (36 mg, 0.033 mmol) (Degussa Type, 10 wt %, 50% H$_2$O), and was immediately capped and purged with N$_2$ for an additional 5 min. The solution then stirred under an atmosphere of H$_2$. The mixture was diluted with MeOH and filtered through packed celite. The filtrate was concentrated in vacuo to provide crude 2-(4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile (71 mg, 0.13 mmol, 99% yield). ESI+APCI MS m/z 538.3 [M+H]$^+$.

Step C: 2-(1-acryloyl-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile To a suspension of 2-(4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile (71 mg, 0.132 mmol) in dichloromethane (1320 μl, 0.132 mmol) at ambient temperature was added Acryloyl Chloride (10.7 μl, 0.132 mmol) followed by Hunig's base (46.1 μl, 0.264 mmol). The reaction was stirred at ambient temperature for 1 hour. The reaction mixture was concentrated in vacuo. The concentrate was suspended in a 60:40 mixture of ACN: H₂O and purified on the Gilson (reverse prep HPLC), eluting with 5→95% ACN/0.1% TFA in water/0.1% TFA. Fractions containing product were combined and partitioned between saturated bicarb and DCM. The aqueous layer was extracted with DCM two more times. The organic layers were combined, dried over Na₂SO₄ and concentrated in vacuo to give title compound 2-(1-acryloyl-4-(2-(((S)-1-(cyclopropylmethyl)pyrrolidin-2-yl)methoxy)-7-(naphthalen-1-yl)-5,6,7,8-tetrahydropyrido[3,4-d]pyrimidin-4-yl)piperazin-2-yl)acetonitrile (EXAMPLE 396, 15.7 mg, 0.0265 mmol, 20.1% yield). ESI+APCI MS m/z 592.4 [M+H]⁺.

Example 397

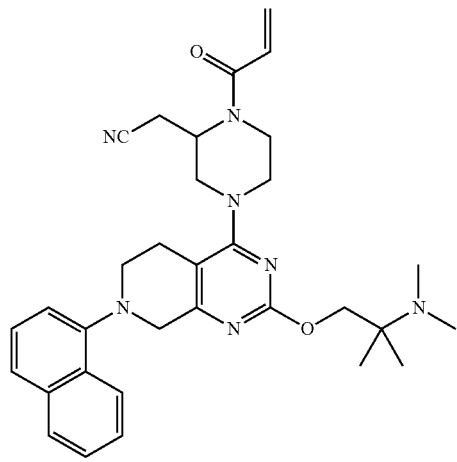 [SMILES: C=CC(=O)N1CCN(c2nc(OCC(C)(C)N(C)C)nc3c2CCN(c2cccc4ccccc24)C3)CC1CC#N]

2-(1-acryloyl-4-(2-(2-(dimethylamino)-2-methylpropoxy)-7-(naphthalen-1-yl)-5,6,7,8-tetrahydropyrido[3,4-d]pyrimidin-4-yl)piperazin-2-yl)acetonitrile 2-(1-acryloyl-4-(2-(2-(dimethylamino)-2-methylpropoxy)-7-(naphthalen-1-yl)-5,6,7,8-tetrahydropyrido[3,4-d]pyrimidin-4-yl)piperazin-2-yl)acetonitrile The title compound was prepared following Example 396 substituting 2-Dimethylamino-2-methyl-1-propanol for (S)-(1-(cyclopropylmethyl)pyrrolidin-2-yl)methanol in Step A. ESI+APCI MS m/z 554.4 [M+H]⁺.

Example 398

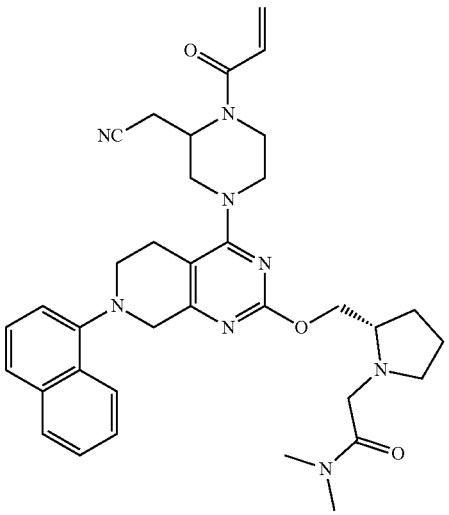 [SMILES: C=CC(=O)N1CCN(c2nc(OC[C@@H]3CCCN3CC(=O)N(C)C)nc3c2CCN(c2cccc4ccccc24)C3)CC1CC#N]

2-((2S)-2-(((4-(4-acryloyl-3-(cyanomethyl)piperazin-1-yl)-7-(naphthalen-1-yl)-5,6,7,8-tetrahydropyrido[3,4-d]pyrimidin-2-yl)oxy)methyl)pyrrolidin-1-yl)-N,N-dimethylacetamide

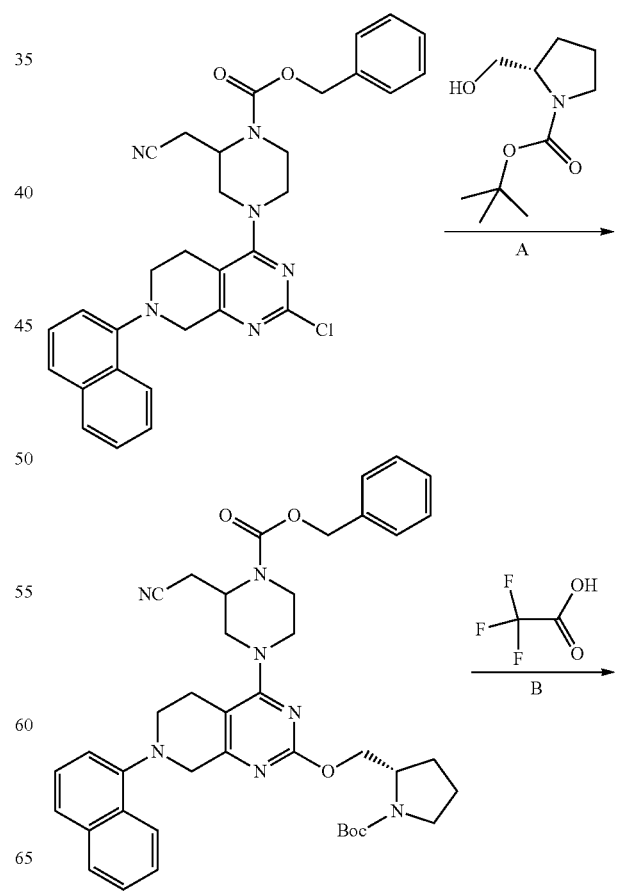

1103
-continued

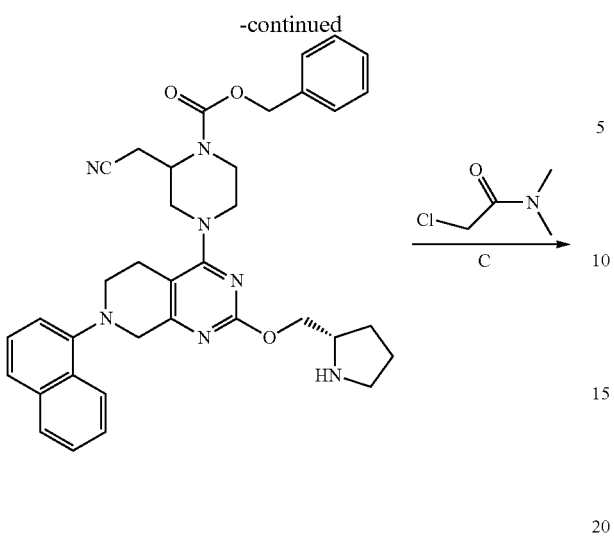

1104
-continued

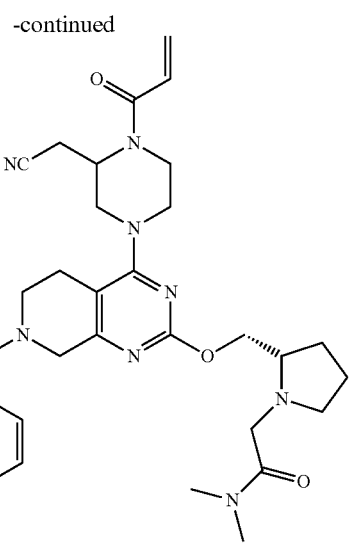

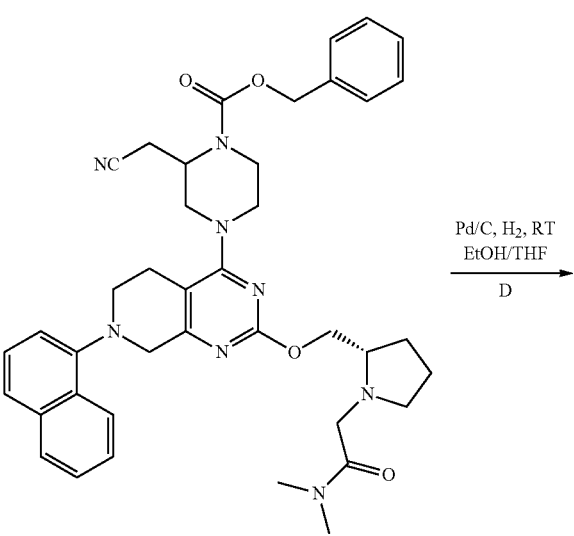

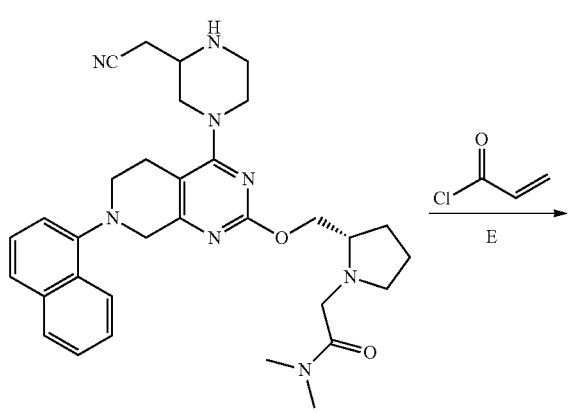

Step A: 2-benzyl 4-(2-(((S)-1-(tert-butoxycarbonyl)pyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate In a microwave tube benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (200 mg, 0.362 mmol) was dissolved in dioxane (181 µl, 0.362 mmol) and treated with cesium carbonate (236 mg, 0.723 mmol) and N-tert-Butoxycarbonyl-L-prolinol (364 mg, 1.81 mmol). The tube was then capped and heated to 90° C. overnight. The reaction mixture was cooled to room temperature and filtered through GF/F paper and concentrated in vacuo. The concentrate was chromatographed on the CombiFlash eluting with 0%-10% DCM:MeOH. All fractions containing clean product were combined and concentrated to give benzyl 4-(2-(((S)-1-(tert-butoxycarbonyl)pyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (225 mg, 0.313 mmol, 86.7% yield). ESI+APCI MS m/z 718.4 [M+H]+.

Step B: benzyl 2-(cyanomethyl)-4-(7-(naphthalen-1-yl)-2-((S)-pyrrolidin-2-yl)methoxy)-5,6,7,8-tetrahydropyrido[3,4-d]pyrimidin-4-yl)piperazine-1-carboxylate Benzyl 4-(2-(((S)-1-(tert-butoxycarbonyl)pyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (225 mg, 0.313 mmol) was dissolved in dichloromethane (3134 µl, 0.313 mmol) and treated with TFA (483 µl, 6.27 mmol). The reaction stirred at room temperature for 1 hour. The reaction was concentrated in vacuo and the organics washed with saturated bicarb. The organics were extracted with DCM (3×). The combined organics were dried over Na$_2$SO$_4$ and concentrated in vacuo to give benzyl 2-(cyanomethyl)-4-(7-(naphthalen-1-yl)-2-(((S)-pyrrolidin-2-yl)methoxy)-5,6,7,8-tetrahydropyrido[3,4-d]pyrimidin-4-yl)piperazine-1-carboxylate (111 mg, 0.180 mmol, 57.3% yield). ESI+APCI MS m/z 618.3 [M+H]+.

Step C: benzyl 2-(cyanomethyl)-4-(2-(((S)-1-(2-(dimethylamino)-2-oxoethyl)pyrrolidin-2-yl)methoxy)-7-(naphthalen-1-yl)-5,6,7,8-tetrahydropyrido[3,4-d]pyrimidin-4-yl)piperazine-1-carboxylate Benzyl 2-(cyanomethyl)-4-(7-(naphthalen-1-yl)-2-(((S)-pyrrolidin-2-yl)methoxy)-5,6,7,8-tetrahydropyrido[3,4-d]pyrimidin-4-yl)piperazine-1-carboxylate (111 mg, 0.1797 mmol) was dissolved in dichloromethane (1797 μl, 0.1797 mmol) and treated with N-ethyl-N-isopropylpropan-2-amine (156.9 μl, 0.8984 mmol) and Chloroacetyldimethylamine (46.20 μl, 0.4492 mmol). The reaction was stirred at room temperature for 30 minutes. 2 more equivalences of base were added and the reaction stirred for an additional 3 hours. The reaction was concentrated in vacuo and was chromatographed on the CombiFlash eluting with 0%-15% DCM/MeOH+0.5% NH$_4$OH modifier. All fractions containing clean desired product were combined and concentrated to give benzyl 2-(cyanomethyl)-4-(2-(((S)-1-(2-(dimethylamino)-2-oxoethyl)pyrrolidin-2-yl)methoxy)-7-(naphthalen-1-yl)-5,6,7,8-tetrahydropyrido[3,4-d]pyrimidin-4-yl)piperazine-1-carboxylate (73 mg, 0.1039 mmol, 57.80% yield). ESI+APCI MS m/z 703.3 [M+H]$^+$.

Step D: 2-((2S)-2-(((4-(3-(cyanomethyl)piperazin-1-yl)-7-(naphthalen-1-yl)-5,6,7,8-tetrahydropyrido[3,4-d]pyrimidin-2-yl)oxy)methyl)pyrrolidin-1-yl)-N,N-dimethylacetamide A solution of benzyl 2-(cyanomethyl)-4-(2-(((S)-1-(2-(dimethylamino)-2-oxoethyl)pyrrolidin-2-yl)methoxy)-7-(naphthalen-1-yl)-5,6,7,8-tetrahydropyrido[3,4-d]pyrimidin-4-yl)piperazine-1-carboxylate (73 mg, 0.10 mmol) in EtOH (1039 μl, 0.10 mmol) and THF (1039 μl, 0.10 mmol) was purged with N$_2$ for 5 minutes. To this solution was added Palladium (28 mg, 0.026 mmol) (Degussa Type, 10 wt %, 50% H$_2$O), and was immediately capped and purged with N$_2$ for an additional 5 minutes. The solution then stirred under an atmosphere of H$_2$. The mixture was then diluted with MeOH and filtered through packed celite. The filtrate was then concentrated in vacuo to provide 2-((2S)-2-(((4-(3-(cyanomethyl)piperazin-1-yl)-7-(naphthalen-1-yl)-5,6,7,8-tetrahydropyrido[3,4-d]pyrimidin-2-yl)oxy)methyl)pyrrolidin-1-yl)-N,N-dimethylacetamide (43 mg, 0.076 mmol, 73% yield). ESI+APCI MS m/z 569.3 [M+H]$^+$.

Step E: 2-((2S)-2-(((4-(4-acryloyl-3-(cyanomethyl)piperazin-1-yl)-7-(naphthalen-1-yl)-5,6,7,8-tetrahydropyrido[3,4-d]pyrimidin-2-yl)oxy)methyl)pyrrolidin-1-yl)-N,N-dimethylacetamide To a suspension of 2-((2S)-2-(((4-(3-(cyanomethyl)piperazin-1-yl)-7-(naphthalen-1-yl)-5,6,7,8-tetrahydropyrido[3,4-d]pyrimidin-2-yl)oxy)methyl)pyrrolidin-1-yl)-N,N-dimethylacetamide (43 mg, 0.0756 mmol) in dichloromethane (756 μl, 0.0756 mmol) at ambient temperature was added Acryloyl Chloride (6.14 μl, 0.0756 mmol) followed by Hunig's base (26.4 μl, 0.151 mmol). The reaction was then stirred at ambient temperature for 1 hour. The reaction mixture was concentrated in vacuo, resuspended in a 60:40 mixture of ACN: H$_2$O and purified on the Gilson (reverse prep HPLC), eluting with 5→95% ACN/0.1% TFA in water/0.1% TFA. Fractions containing product were combined and partitioned between saturated bicarb and DCM. The aqueous layer was extracted with DCM two more times. The organic layers were combined, dried over Na$_2$SO$_4$ and concentrated in vacuo to give 2-((2S)-2-(((4-(4-acryloyl-3-(cyanomethyl)piperazin-1-yl)-7-(naphthalen-1-yl)-5,6,7,8-tetrahydropyrido[3,4-d]pyrimidin-2-yl)oxy)methyl)pyrrolidin-1-yl)-N,N-dimethylacetamide (14.9 mg, 0.0239 mmol, 31.6% yield). ESI+APCI MS m/z 623.3 [M+H]$^+$.

Example 399

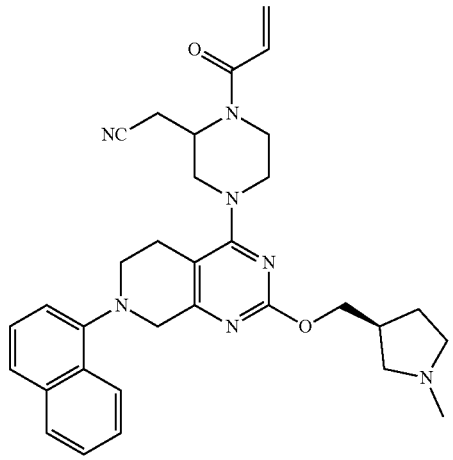 [SMILES: C=CC(=O)N1CCN(c2nc(OC[C@H]3CCN(C)C3)nc3c2CCN(c2cccc4ccccc24)C3)CC1CC#N]

2-(1-acryloyl-4-(2-(((S)-1-methylpyrrolidin-3-yl)methoxy)-7-(naphthalen-1-yl)-5,6,7,8-tetrahydropyrido[3,4-d]pyrimidin-4-yl)piperazin-2-yl)acetonitrile 2-(1-acryloyl-4-(2-(((S)-1-methylpyrrolidin-3-yl)methoxy)-7-(naphthalen-1-yl)-5,6,7,8-tetrahydropyrido[3,4-d]pyrimidin-4-yl)piperazin-2-yl)acetonitrile The title compound was prepared following Example 396 substituting (3R)-(1-Methyl-pyrrolidin-3-yl)-methanol for (S)-(1-(cyclopropylmethyl)pyrrolidin-2-yl)methanol in Step A. ESI+APCI MS m/z 552.3 [M+H]$^+$.

Example 400

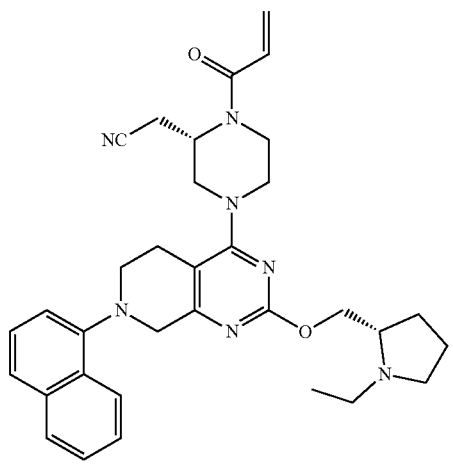 [SMILES: C=CC(=O)N1CCN(c2nc(OC[C@@H]3CCCN3CC)nc3c2CCN(c2cccc4ccccc24)C3)C[C@@H]1CC#N]

1107

2-((S)-1-acryloyl-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile

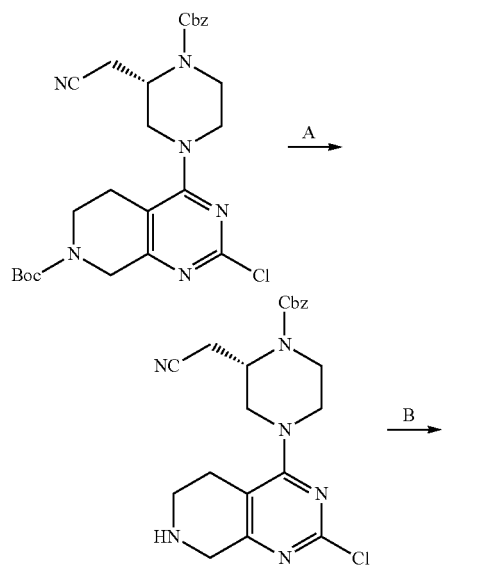

A →

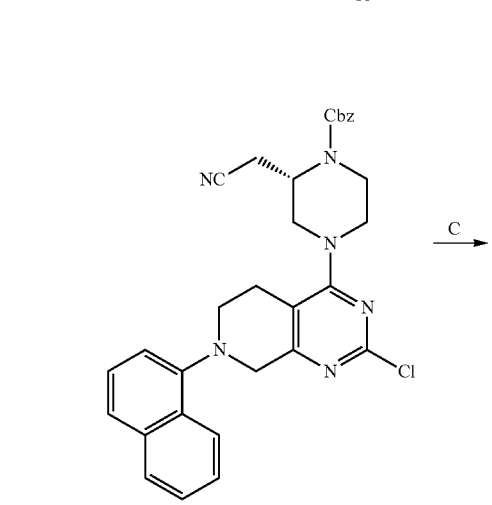

B →

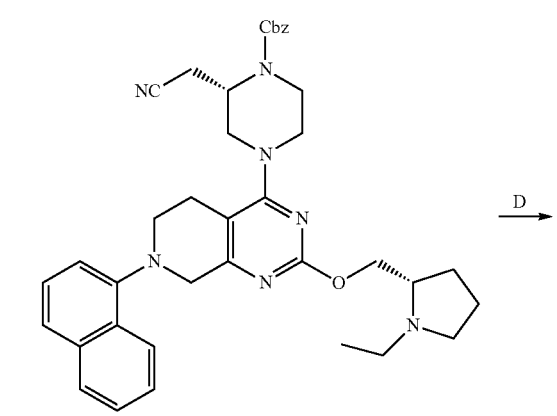

C →

D →

1108

-continued

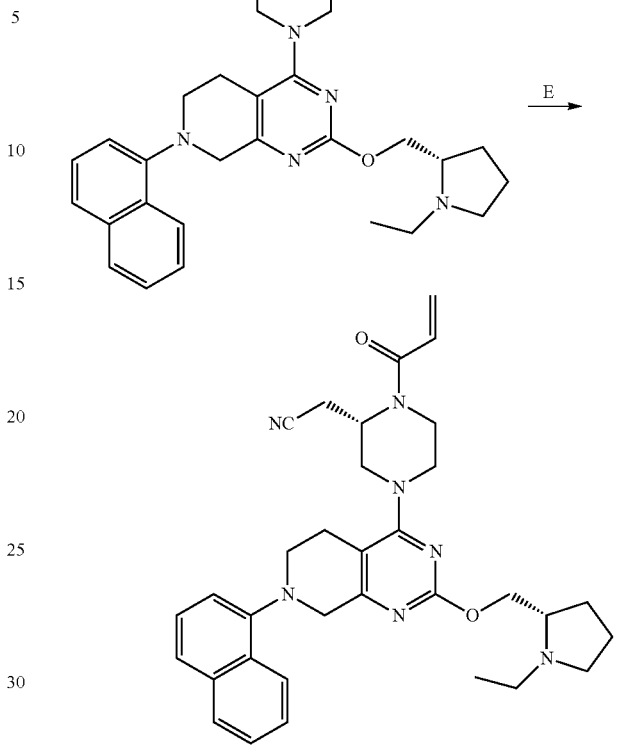

E →

Step A: benzyl (S)-4-(2-chloro-5,6,7,8-tetrahydropyrido[3,4-d]pyrimidin-4-yl)-2-(cyanomethyl)piperazine-1-carboxylate To a solution of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (5.0 g, 9.5 mmol) in DCM (50 mL) was added hydrogen chloride (12 ml, 47 mmol, 4 M solution in dioxanes) and the reaction stirred at room temperature for 1 hour. The reaction was next concentrated to a thick slurry and a mixture of EtOAc/water was added. The aqueous layer was basified with 1M NaOH and the aqueous layer extracted with EtOAc (2×). The combined organics were washed with brine, dried over $MgSO_4$ and concentrated in vacuo to give benzyl (S)-4-(2-chloro-5,6,7,8-tetrahydropyrido[3,4-d]pyrimidin-4-yl)-2-(cyanomethyl)piperazine-1-carboxylate (4.0 g, 9.4 mmol, 99% yield). ESI+APCI MS m/z 427.1 $[M+H]^+$.

Step B: benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate To a solution of benzyl (S)-4-(2-chloro-5,6,7,8-tetrahydropyrido[3,4-d]pyrimidin-4-yl)-2-(cyanomethyl)piperazine-1-carboxylate (3.4 g, 8.0 mmol) in dioxanes (40 mL) was added 1-iodonaphthalene (6.0 ml, 40 mmol) and cesium carbonate (5.2 g, 16 mmol) and the reaction degassed with Argon for 15 minutes followed by addition of Rhuphos Pd G3 (1.00 g, 1.2 mmol) and the reaction heated to 100° C. for overnight. The reaction was next filtered through GF/F paper and concentrated in vacuo. The material was next chromatographed using 10→70 EtOAc/Hexanes as eluent to give benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (2.8 g, 5.1 mmol, 64% yield). ESI+APCI MS m/z 553.2 [M+H]⁺.

Step C: benzyl (S)-2-(cyanomethyl)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazine-1-carboxylate In a conical bottom vial a solution of benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (250 mg, 0.452 mmol) in dioxane (4520 µl, 0.452 mmol) was sparged with Argon for 5 minutes. (3R)-(1-Ethylpyrrolidin-3-yl)-methanol (175 mg, 1.36 mmol), Cs₂CO₃ (442 mg, 1.36 mmol), Rhuphos Pd G3 (37.8 mg, 0.0452 mmol) were sequentially added under Argon and sparged for an additional 5 min. The reaction mixture was capped and heated at 100° C. for 1 hour. The reaction was cooled to room temperature and ethyl acetate was added. The organics were washed with brine (2×), dried over Na₂SO₄ and concentrate in vacuo. The concentrate was purified by flash chromatography eluting with 0-20% (MeOH+2% NH₄OH)/DCM. All fractions containing clean desired product were combined and concentrated to give benzyl (S)-2-(cyanomethyl)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazine-1-carboxylate (118 mg, 0.183 mmol, 40.4% yield). ESI+APCI MS m/z 646.3 [M+H]⁺.

Step D: 2-((S)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile A solution of benzyl (S)-2-(cyanomethyl)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazine-1-carboxylate (237 mg, 0.367 mmol) in EtOH (3670 µl, 0.367 mmol) and THF (3670 µl, 0.367 mmol) was purged with N₂ for 5 min. To this solution was added Palladium (97.6 mg, 0.0917 mmol) (Degussa Type, 10 wt %, 50% H₂O), and was immediately capped and purged with N₂ for an additional 5 min. The solution then stirred under an atmosphere of H₂. The mixture was then diluted with MeOH and filtered through packed celite. The filtrate was then concentrated in vacuo to provide 2-((S)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile (155 mg, 0.303 mmol, 82.5% yield). ESI+APCI MS m/z 512.3 [M+H]⁺.

Step E: 2-((S)-1-acryloyl-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile To a suspension of 2-((S)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile (226 mg, 0.442 mmol) in dichloromethane (4417 µl, 0.442 mmol) at ambient temperature was added Acyloyl Chloride (35.9 µl, 0.442 mmol) followed by Hunig's base (154 µl, 0.883 mmol). The reaction was stirred at ambient temperature for 2 hours. The reaction mixture was concentrated in vacuo and loaded onto a 12 g RediSep Gold column and chromatographed on the CombiFlash (0%-15% DCM:MeOH+1% NH₄OH modifier). All fractions containing product were combined and concentrated in vacuo. The concentrate was suspended in a 60:40 mixture of ACN:H₂O and purified on the Gilson (reverse prep HPLC), eluting with 5→95% ACN/0.1% TFA in water/0.1% TFA. Fractions containing product were combined and partitioned between saturated bicarb and DCM. The aqueous layer was extracted with DCM two more times. The organic layers were combined, dried over Na₂SO₄ and concentrated in vacuo to give title compound 2-((S)-1-acryloyl-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile (EXAMPLE 400, 136 mg, 0.240 mmol, 54.4% yield). ESI+APCI MS m/z 566.2 [M+H]⁺.

Example 401

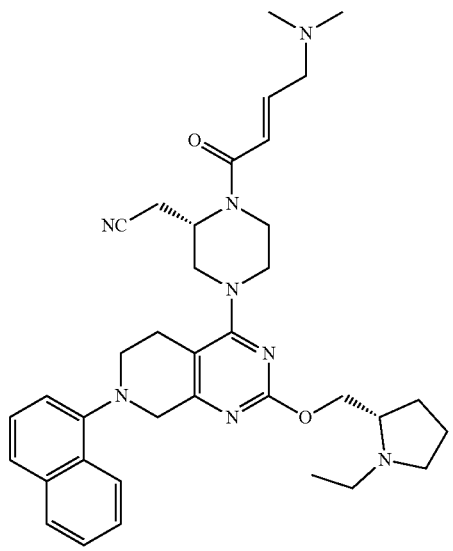 [SMILES: CCN1CCC[C@H]1COc1nc2c(c(N3CCN(C(=O)/C=C/CN(C)C)[C@@H](CC#N)C3)n1)CCN(c1cccc3ccccc13)C2]

2-((S)-1-((E)-4-(dimethylamino)but-2-enoyl)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile

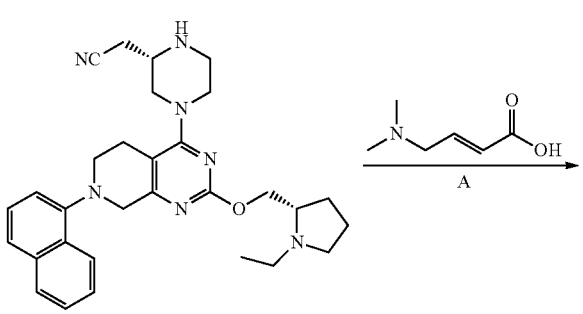

1111
-continued

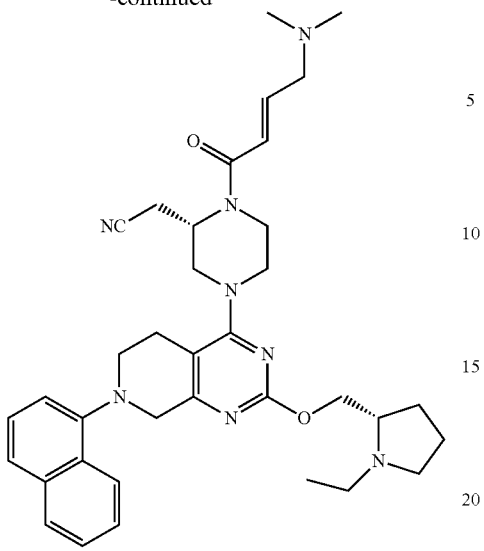

Step A: 2-((S)-1-((E)-4-(dimethylamino)but-2-enoyl)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile To a solution of 2-((S)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile (150 mg, 0.293 mmol), (2E)-4-(Dimethylamino)but-2-enoic acid (75.7 mg, 0.586 mmol), DIEA (256 µl, 1.47 mmol) in DCM (2932 µl, 0.293 mmol) was added HATU (167 mg, 0.440 mmol) and the resulting mixture was stirred at room temperature for 5 hours. The reaction mixture was partitioned between EtOAc and Brine. The aqueous was extracted with EtOAc (2×). The combined organics were dried over Na₂SO₄, and concentrated in vacuo. The concentrate was diluted in 60:40 ACN:H₂O and purified on the Gilson (reverse prep HPLC), eluting with 5→95% ACN/0.1% TFA in water/0.1% TFA. Fractions containing product were combined and partitioned between saturated bicarb and DCM. The aqueous layer was extracted with DCM two more times. The organic layers were combined, dried over Na₂SO₄ and concentrated in vacuo to give title compound 2-((S)-1-((E)-4-(dimethylamino)but-2-enoyl)-4-(2-(((S)-1-ethylpyrrolidin-2-yl)methoxy)-7-(naphthalen-1-yl)-5,6,7,8-tetrahydropyrido[3,4-d]pyrimidin-4-yl)piperazin-2-yl)acetonitrile (EXAMPLE 401, 27.6 mg, 0.0443 mmol, 15.1% yield). ESI+APCI MS m/z 623.4 [M+H]⁺.

1112
Example 402

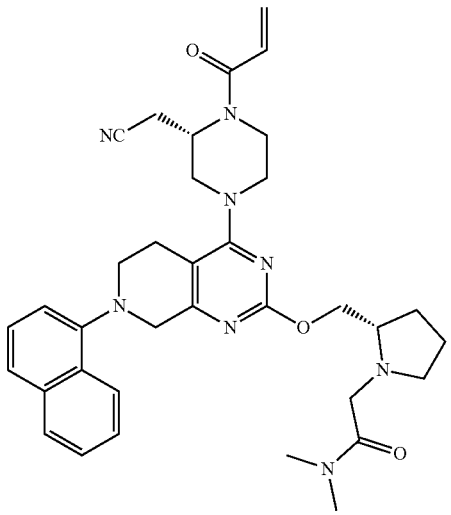 [SMILES: C=CC(=O)N1CCN(c2nc(OC[C@@H]3CCCN3CC(=O)N(C)C)nc3c2CCN(c2cccc4ccccc24)C3)C[C@@H]1CC#N]

2-((S)-2-(((4-((S)-4-acryloyl-3-(cyanomethyl)piper-azin-1-yl)-7-(naphthalen-1-yl)-5,6,7,8-tetrahydro-pyrido[3,4-d]pyrimidin-2-yl)oxy)methyl)pyrrolidin-1-yl)-N,N-dimethylacetamide 2-((S)-2-(((4-((S)-4-acryloyl-3-(cyanomethyl)piper-azin-1-yl)-7-(naphthalen-1-yl)-5,6,7,8-tetrahydro-pyrido[3,4-d]pyrimidin-2-yl)oxy)methyl)pyrrolidin-1-yl)-N,N-dimethylacetamide The title compound was prepared following Example 398 substituting benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate for benzyl 4-(2-chloro-7-(naphthalen-1-yl)-5,6,7,8-tetrahydropyrido[3,4-d]pyrimidin-4-yl)-2-(cyanomethyl)piperazine-1-carboxylate in Step A. ESI+APCI MS m/z 623.3 [M+H]⁺.

Example 403

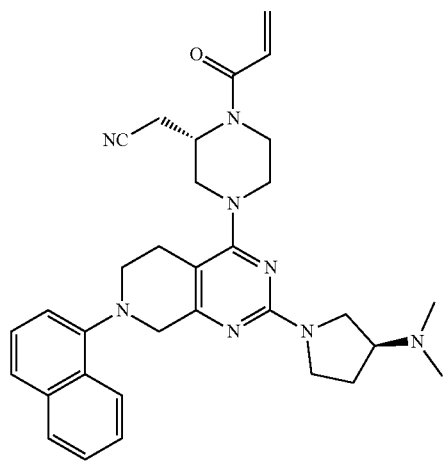 [SMILES: C=CC(=O)N1CCN(c2nc(N3CC[C@H](N(C)C)C3)nc3c2CCN(c2cccc4ccccc24)C3)C[C@@H]1CC#N]

1113 benzyl (S)-2-(cyanomethyl)-4-(2-(((S)-3-(dimethyl-amino)pyrrolidin-1-yl)-7-(naphthalen-1-yl)-5,6,7,8-tetrahydropyrido[3,4-d]pyrimidin-4-yl)piperazine-1-carboxylate benzyl (S)-2-(cyanomethyl)-4-(2-(((S)-3-(dimethyl-amino)pyrrolidin-1-yl)-7-(naphthalen-1-yl)-5,6,7,8-tetrahydropyrido[3,4-d]pyrimidin-4-yl)piperazine-1-carboxylate The title compound was prepared following Example 400 substituting (3S)-(−)-3-(Dimethylamino)Pyrrolidine for (3R)-(1-Ethyl-pyrrolidin-3-yl)-methanol in Step C. ESI+ APCI MS m/z 551.3 [M+H]+.

Example 404

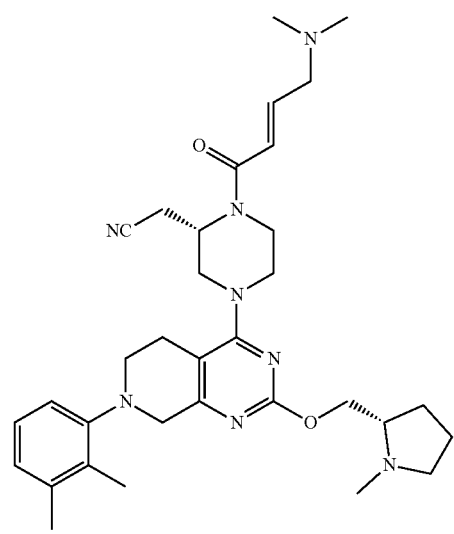 [SMILES: Cc1cccc(N2CCc3c(nc(OC[C@@H]4CCCN4C)nc3N3CCN(C(=O)/C=C/CN(C)C)[C@@H](CC#N)C3)C2)c1C]

2-((S)-1-((E)-4-(dimethylamino)but-2-enoyl)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile

1114

-continued

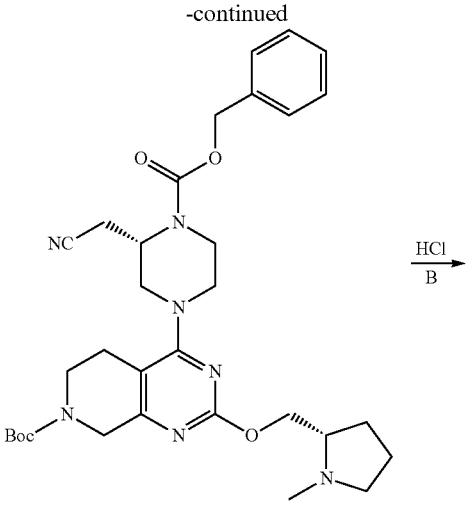

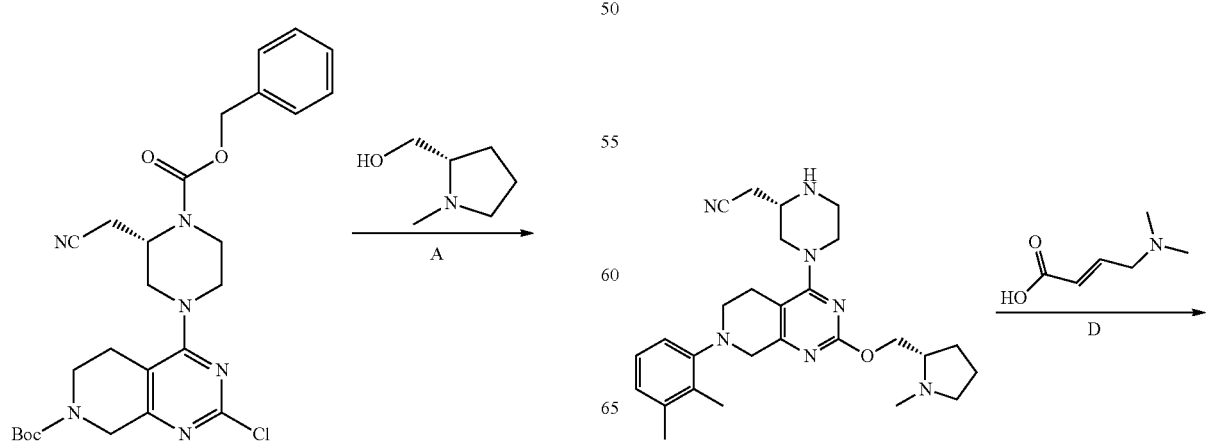

1115

-continued

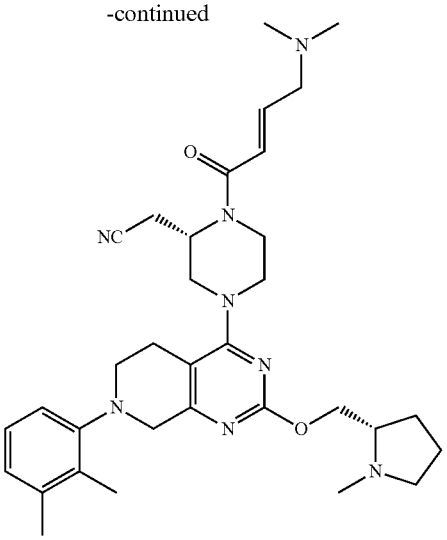

Step A: 2-tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate In a round bottom flask, a solution of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (5 g, 9.487 mmol) in dioxane (94.87 ml, 9.487 mmol) was sparged with argon and (S)-(1-methylpyrrolidin-2-yl)methanol (3.278 g, 28.46 mmol), $Cs_2CO_3$ (9.273 g, 28.46 mmol), Methanesulfonato(2-dicyclohexylphosphino-2',6'-di-i-propoxy-1,1'-biphenyl)(2'-methylamino-1,1'-biphenyl-2-yl)palladium(II) (0.8078 g, 0.9487 mmol) were sequentially added under Argon and sparged for an additional 5 minutes. The reaction mixture was capped and heated at 100° C. over night. The reaction was filtered through GF/F paper and concentrated in vacuo. The concentrate was purified on the Combi Flash (0-12% MeOH in DCM with 2% $NH_4OH$) to provide tert-butyl 4-((S)-4-((benzyloxy)carbonyl)-3-(cyanomethyl)piperazin-1-yl)-2-((S)-1-methylpyrrolidin-2-yl)methoxy)-5,8-dihydropyrido[3,4-d]pyrimidine-7(6H)-carboxylate (5.425 g, 8.508 mmol, 89.68% yield). ESI+APCI MS m/z 606.4 $[M+H]^+$.

Step B: benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (5.4 g, 8.915 mmol) was dissolved in dichloromethane (89.15 ml, 8.915 mmol) and treated with Hydrochloric Acid (4.0M solution in 1,4-dioxane) (11.14 ml, 44.57 mmol). The reaction stirred at room temperature for 1 hour. The reaction was next diluted with more DCM and 1M NaOH and the layers separated. The organics were next washed with brine, dried over $Na_2SO_4$ and concentrated in vacuo to give benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (4.364 g, 8.631 mmol, 96.82% yield). ESI+APCI MS m/z 506.3 $[M+H]^+$.

Step C: 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile In a round bottom flask, a solution of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (4.364 g, 8.631 mmol) in dioxane (43.15 ml, 8.631 mmol) was sparged with Argon for 5 minutes. 1-Bromo-2,3-dimethylbenzene (5.851 ml, 43.15 mmol), $Cs_2CO_3$ (14.06 g, 43.15 mmol), and Methanesulfonato(2-dicyclohexylphosphino-2',6'-di-i-propoxy-1,1'-biphenyl)(2'-methylamino-1,1'-biphenyl-2-yl)palladium(II) (0.7348 g, 0.8631 mmol) were sequentially added under Argon and sparged for an additional 5 min. The reaction mixture was capped and heated at 100° C. ON. The reaction was cooled to room temperature. Ethyl acetate was added and the reaction filtered through GF/F paper and concentrated in vacuo. The concentrate was purified twice via normal phase chromatography on the CombiFlash using 0-15% MeOH in DCM with 2% $NH_4OH$ as eluent. Fractions containing desired product were collected and concentrated in vacuo to give 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile (0.411 g, 0.8641 mmol, 100.1% yield). ESI+APCI MS m/z 476.3 $[M+H]^+$.

Step D: 2-((S)-1-((E)-4-(dimethylamino)but-2-enoyl)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile To a solution of 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile (95 mg, 0.200 mmol), (2E)-4-(Dimethylamino)but-2-enoic acid (51.6 mg, 0.399 mmol), DIEA (174 μl, 0.999 mmol) in DCM (1997 μl, 0.200 mmol) was added HATU (114 mg, 0.300 mmol) and the resulting mixture was stirred at room temperature for 5 hours. The reaction mixture was washed with Brine and the aqueous layer extracted with DCM (2×). The combined organic layers were dried over $Na_2SO_4$, concentrated, diluted in 60:40 ACN:$H_2O$ and purified on the Gilson (reverse prep HPLC), eluting with 5%-95% ACN/0.1% TFA in water/0.1% TFA. Fractions containing product were combined and free based with saturated bicarb and the organics extracted with DCM. The organics were dried over $Na_2SO_4$ and concentrated in vacuo to give 2-((S)-1-((E)-4-(dimethylamino)but-2-enoyl)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile (38 mg, 0.0648 mmol, 32.4% yield). ESI+APCI MS m/z 587.4 $[M+H]^+$.

Example 405

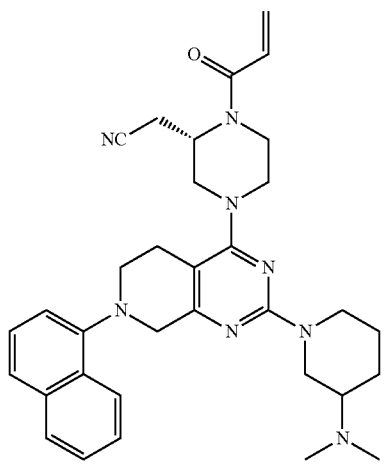 [SMILES: C=CC(=O)N1CCN(c2nc(N3CCCC(N(C)C)C3)nc3c2CCN(c2cccc4ccccc24)C3)C[C@@H]1CC#N]

2-((2S)-1-acryloyl-4-(2-(3-(dimethylamino)piperi-din-1-yl)-7-(naphthalen-1-yl)-5,6,7,8-tetrahydro-pyrido[3,4-d]pyrimidin-4-yl)piperazin-2-yl)acetoni-trile 2-((2S)-1-acryloyl-4-(2-(3-(dimethylamino)piperi-din-1-yl)-7-(naphthalen-1-yl)-5,6,7,8-tetrahydro-pyrido[3,4-d]pyrimidin-4-yl)piperazin-2-yl)acetoni-trile The title compound was prepared following Example 400 substituting N,N-Dimethylpiperidin-3-amine for (3R)-(1-Ethyl-pyrrolidin-3-yl)-methanol in Step C. ESI+APCI MS m/z 565.4 [M+H]⁺.

Example 406

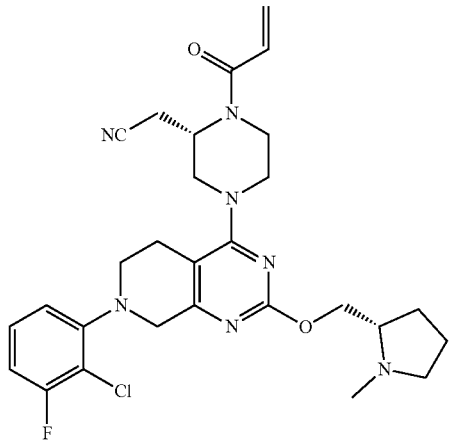 [SMILES: C=CC(=O)N1CCN(c2nc(OC[C@@H]3CCCN3C)nc3c2CCN(c2cccc(F)c2Cl)C3)C[C@@H]1CC#N]

2-((S)-1-acryloyl-4-(7-(2-chloro-3-fluorophenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(2-chloro-3-fluorophenyl)-2-(((S)-1-methylpyrrolidin-2-yl)methoxy)-5,6,7,8-tetrahydropyrido[3,4-d]pyrimidin-4-yl)piperazin-2-yl)acetonitrile The title compound was prepared following Example 234 substituting 1-Bromo-2-chloro-3-fluorobenzene for 1-bromonaphthalene in Step H. ESI+APCI MS m/z 554.2 [M+H]⁺.

Example 407

2-((S)-1-acryloyl-4-(7-(2,3-difluorophenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(2,3-difluorophenyl)-2-(((S)-1-methylpyrrolidin-2-yl)methoxy)-5,6,7,8-tetrahydropyrido[3,4-d]pyrimidin-4-yl)piperazin-2-yl)acetonitrile The title compound was prepared following Example 234 substituting 1-Bromo-2,3-difluorobenzene for 1-bromonaphthalene in Step H. ESI+APCI MS m/z 538.2 [M+H]⁺.

1119

Example 408

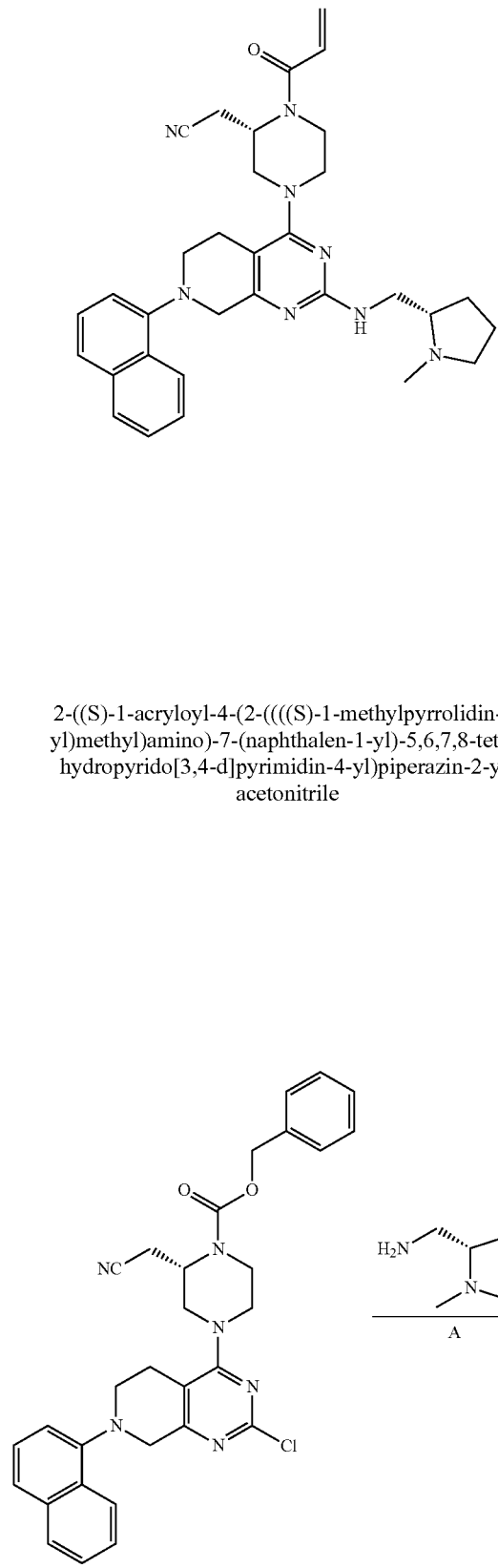

2-((S)-1-acryloyl-4-(2-((((S)-1-methylpyrrolidin-2-yl)methyl)amino)-7-(naphthalen-1-yl)-5,6,7,8-tetrahydropyrido[3,4-d]pyrimidin-4-yl)piperazin-2-yl)acetonitrile

1120

-continued

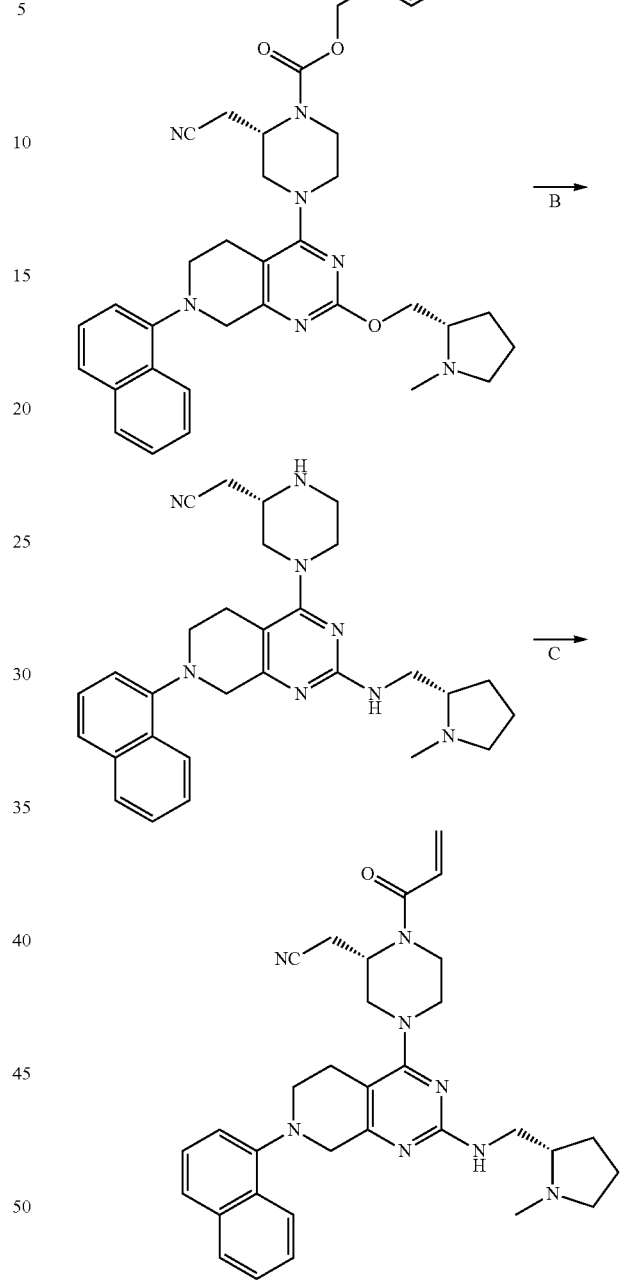

Step A: benzyl (S)-2-(cyanomethyl)-4-(2-((((S)-1-methylpyrrolidin-2-yl)methyl)amino)-7-(naphthalen-1-yl)-5,6,7,8-tetrahydropyrido[3,4-d]pyrimidin-4-yl)piperazine-1-carboxylate benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (300 mg, 0.542 mmol) was dissolved in Dioxane and treated with (S)-(1-methylpyrrolidin-2-yl)methanamine (356 μl, 2.71 mmol). The reaction was stirred at 80° C. for 3 hours. The reaction was cooled to room temperature and partitioned between water and EtOAc. The aqueous layer was extracted with EtOAc (2×). The combined organics were washed with water and brine then dried over Na$_2$SO$_4$ and filtered. The filtrate was concentrated in vacuo and chromatographed on the CombiFlash eluting with 0%-15% DCM:MeOH+2% NH$_4$OH to give benzyl (S)-2-(cyanomethyl)-4-(2-((((S)-1-methylpyrrolidin-2-yl)methyl) amino)-7-(naphthalen-1-yl)-5,6,7,8-tetrahydropyrido[3,4-d] pyrimidin-4-yl)piperazine-1-carboxylate acetonitrile (146 mg, 0.231 mmol, 42.7% yield). ESI+APCI MS m/z 631.3 [M+H]$^+$. The rest of the synthesis for the title compound was done by following Example 396 Steps B through C. ESI+APCI MS m/z 551.3 [M+H]$^+$.

Example 409

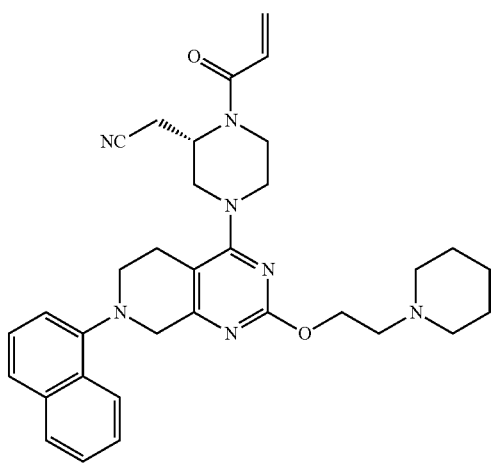

(S)-2-(1-acryloyl-4-(7-(naphthalen-1-yl)-2-(2-(piperidin-1-yl)ethoxy)-5,6,7,8-tetrahydropyrido[3,4-d]pyrimidin-4-yl)piperazin-2-yl)acetonitrile (S)-2-(1-acryloyl-4-(7-(naphthalen-1-yl)-2-(2-(piperidin-1-yl)ethoxy)-5,6,7,8-tetrahydropyrido[3,4-d] pyrimidin-4-yl)piperazin-2-yl)acetonitrile The title compound was prepared following Example 400 substituting 1-Piperidineethanol for (3R)-(1-Ethyl-pyrrolidin-3-yl)-methanol in Step C. ESI+APCI MS m/z 556.3 [M+H]$^+$.

Example 410

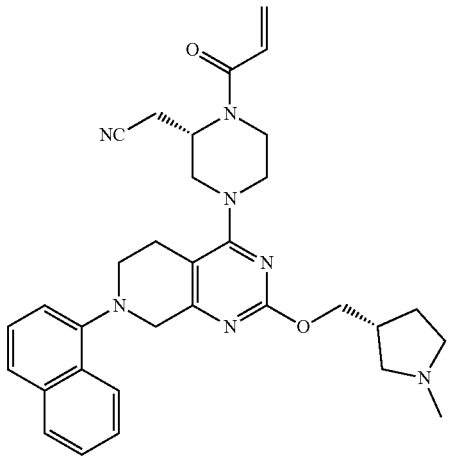 [SMILES: C=CC(=O)N1CCN(c2nc(OC[C@@H]3CCN(C)C3)nc3c2CCN(c2cccc4ccccc24)C3)C[C@@H]1CC#N]

2-((S)-1-acryloyl-4-(2-(((R)-1-methylpyrrolidin-3-yl)methoxy)-7-(naphthalen-1-yl)-5,6,7,8-tetrahydropyrido[3,4-d]pyrimidin-4-yl)piperazin-2-yl)acetonitrile 2-((S)-1-acryloyl-4-(2-(((R)-1-methylpyrrolidin-3-yl)methoxy)-7-(naphthalen-1-yl)-5,6,7,8-tetrahydropyrido[3,4-d]pyrimidin-4-yl)piperazin-2-yl)acetonitrile The title compound was prepared following Example 400 substituting (R)-3-(hydoxymethyl)-1-methylpyrrolidine for (3R)-(1-Ethyl-pyrrolidin-3-yl)-methanol in Step C. ESI+APCI MS m/z 552.3 [M+H]$^+$.

Example 411

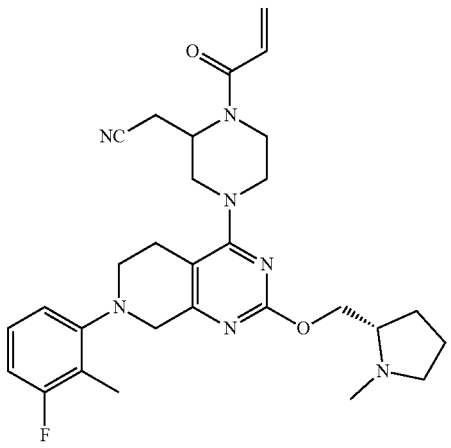 [SMILES: C=CC(=O)N1CCN(c2nc(OC[C@@H]3CCCN3C)nc3c2CCN(c2cccc(F)c2C)C3)CC1CC#N]

2-(1-acryloyl-4-(7-(3-fluoro-2-methylphenyl)-2-((S)-1-methylpyrrolidin-2-yl)methoxy)-5,6,7,8-tetrahydropyrido[3,4-d]pyrimidin-4-yl)piperazin-2-yl)acetonitrile 2-(1-acryloyl-4-(7-(3-fluoro-2-methylphenyl)-2-(((S)-1-methylpyrrolidin-2-yl)methoxy)-5,6,7,8-tetrahydropyrido[3,4-d]pyrimidin-4-yl)piperazin-2-yl)acetonitrile was prepared following Example 375, Steps E-G, substituting 1-bromo-3-fluoro-2-methylbenzene for 4-bromo-3-(trifluoromethyl)pyridine hydrobromide in Step E. ESI+APCI MS m/z 534.3 [M+H]⁺.

Example 412

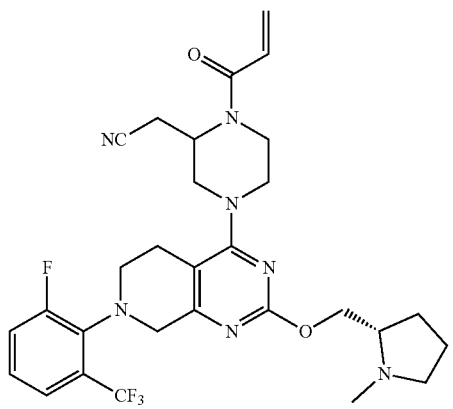 [SMILES: C=CC(=O)N1CCN(c2nc(OC[C@@H]3CCCN3C)nc3c2CCN(c2c(F)cccc2C(F)(F)F)C3)CC1CC#N]

2-(1-acryloyl-4-(7-(2-fluoro-6-(trifluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile 2-(1-acryloyl-4-(7-(2-fluoro-6-(trifluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile was prepared following Example 375 Steps E-G, substituting 2-bromo-1-fluoro-3-(trifluoromethyl)benzene for 4-bromo-3-(trifluoromethyl)pyridine hydrobromide in Step E. ESI+APCI MS m/z 588.3 [M+H]⁺.

Example 413

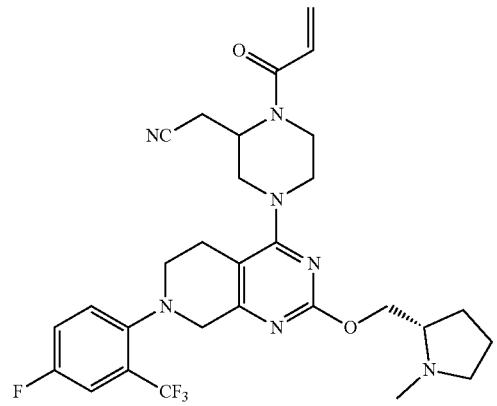 [SMILES: C=CC(=O)N1CCN(c2nc(OC[C@@H]3CCCN3C)nc3c2CCN(c2ccc(F)cc2C(F)(F)F)C3)CC1CC#N]

2-(1-acryloyl-4-(7-(4-fluoro-2-(trifluoromethyl)phenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-(1-acryloyl-4-(7-(4-fluoro-2-(trifluoromethyl)phenyl)-2-((S)-1-methylpyrrolidin-2-yl)methoxy)-5,6,7,8-tetrahydropyrido [3,4-d]pyrimidin-4-yl)piperazin-2-yl)acetonitrile was prepared following Example 375 Steps E-G, substituting 1-bromo-4-fluoro-2-(trifluoromethyl)benzene for 4-bromo-3-(trifluoromethyl)pyridine hydrobromide in Step E. ESI+APCI MS m/z 588.3 [M+H]⁺.

Example 414

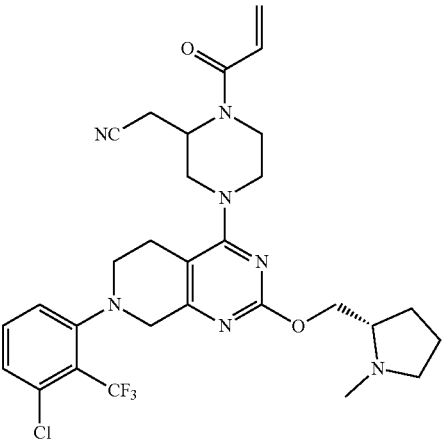 [SMILES: C=CC(=O)N1CCN(c2nc(OC[C@@H]3CCCN3C)nc3c2CCN(c2cccc(Cl)c2C(F)(F)F)C3)CC1CC#N]

1125

2-(1-acryloyl-4-(7-(3-chloro-2-(trifluoromethyl)phenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-(1-acryloyl-4-(7-(3-chloro-2-(trifluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile was prepared following Example 375 Steps E-G, substituting 1-bromo-3-chloro-2-(trifluoromethyl)benzene for 4-bromo-3-(trifluoromethyl)pyridine hydrobromide in Step E and THF for MeOH in Step F. ESI+APCI MS m/z 604.2 [M+H]⁺.

Example 415

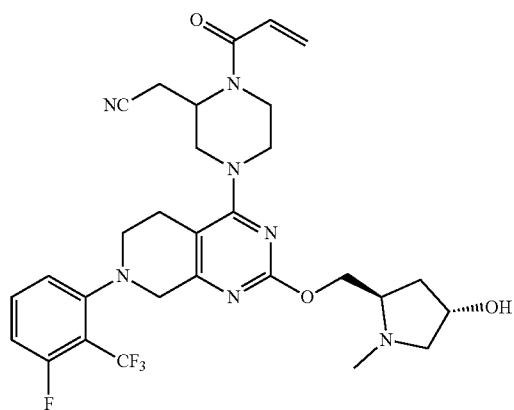 [SMILES: C=CC(=O)N1CCN(c2nc(OC[C@H]3C[C@H](O)CN3C)nc3c2CCN(c2cccc(F)c2C(F)(F)F)C3)CC1CC#N]

2-(1-acryloyl-4-(7-(3-fluoro-2-(trifluoromethyl)phenyl)-2-(((2R,4S)-4-hydroxy-1-methylpyrrolidin-2-yl)methoxy)-5,6,7,8-tetrahydropyrido[3,4-d]pyrimidin-4-yl)piperazin-2-yl)acetonitrile

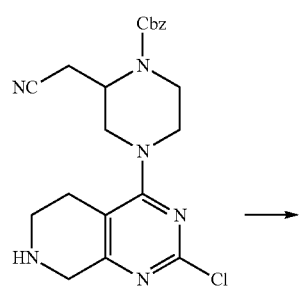

1126

-continued

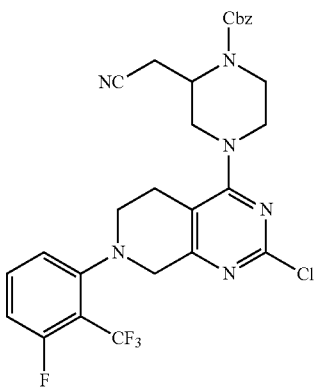

Step A: benzyl 4-(2-chloro-7-(3-fluoro-2-(trifluoromethyl)phenyl)-5,6,7,8-tetrahydropyrido[3,4-d]pyrimidin-4-yl)-2-(cyanomethyl)piperazine-1-carboxylate To a vial was added cesium carbonate (4.01 g, 12.3 mmol), benzyl 4-(2-chloro-5,6,7,8-tetrahydropyrido[3,4-d]pyrimidin-4-yl)-2-(cyanomethyl)piperazine-1-carboxylate (1.75 g, 4.10 mmol) and Rhuphos Pd G3 (0.343 g, 0.410 mmol), and 1-bromo-3-fluoro-2-(trifluoromethyl)benzene (4.98 g, 20.5 mmol). The vial was sealed and the 1,4-dioxane (41.0 ml, 4.10 mmol) added through a septum. Ar was bubbled through the mixture for 5 minutes and then the mixture was heated to 70° C. for 7 h. The reaction was cooled, filtered through qualitative paper and concentrated. The yellow solids were dissolved in minimal DCM and purified by silica chromatography (0-12% MeOH in DCM) which provided benzyl 4-(2-chloro-7-(3-fluoro-2-(trifluoromethyl)phenyl)-5,6,7,8-tetrahydropyrido[3,4-d]pyrimidin-4-yl)-2-(cyanomethyl)piperazine-1-carboxylate (1.3 g, 2.21 mmol, 54% yield.

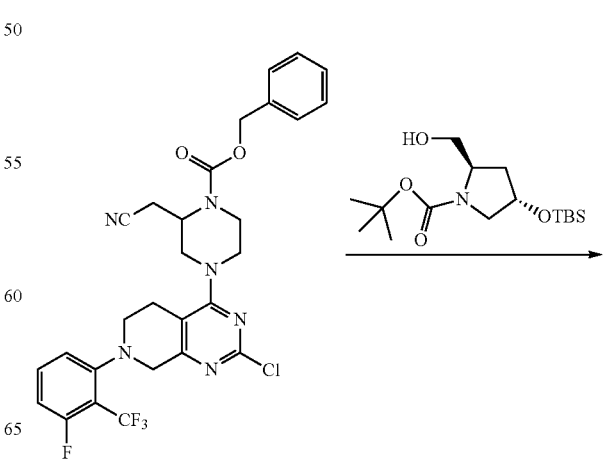

-continued

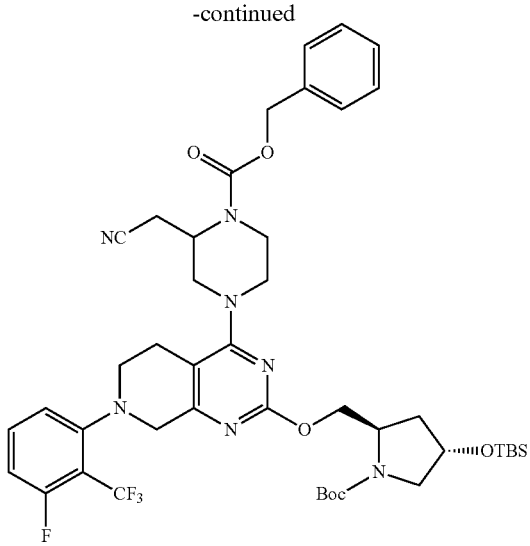

Step B: benzyl 4-(2-(((2R,4S)-1-(tert-butoxycarbo-
nyl)-4-((tert-butyldimethylsilyl)oxy)pyrrolidin-2-yl)
methoxy)-7-(3-fluoro-2-(trifluoromethyl)phenyl)-5,
6,7,8-tetrahydropyrido[3,4-d]pyrimidin-4-yl)-2-
(cyanomethyl)piperazine-1-carboxylate A solution of benzyl 4-(2-chloro-7-(3-fluoro-2-(trifluoromethyl)phenyl)-5,6,7,8-tetrahydropyrido[3,4-d]pyrimidin-4-yl)-2-(cyanomethyl)piperazine-1-carboxylate (150 mg, 0.255 mmol) in dioxane (2547 µl, 0.255 mmol) was sparged with argon and (2S,4R)-4-{[tert-Butyl(dimethyl) silyl]oxy}-2-(hydroxymethyl)pyrrolidine-1-carboxylate (211 mg, 0.637 mmol), $Cs_2CO_3$ (249 mg, 0.76 mmol), Rhuphos Pd G3 (21.3 mg, 0.026 mmol) were sequentially added under argon and sparged for an additional 5 min. The reaction mixture was capped and heated at 100° C. for 4 hr. The mixture was filtered through GF/F paper, concentrated and the residue was dissolved in DCM and washed with water, aqueous was separated and extracted with DCM (3×15 mL). The extracts were combined and concentrated and the resulting residue was purified by silica gel (0-50% EtOAc/hex 20CV, 50% EA/hex 2CV, 50-100% EA/hex 10CV) to provide benzyl 4-(2-(((2R,4S)-1-(tert-butoxycarbonyl)-4-((tert-butyldimethylsilyl)oxy)pyrrolidin-2-yl) methoxy)-7-(3-fluoro-2-(trifluoromethyl)phenyl)-5,6,7,8-tetrahydropyrido[3,4-d]pyrimidin-4-yl)-2-(cyanomethyl) piperazine-1-carboxylate (95 mg, 0.107 mmol, 42% yield).

Step C: tert-butyl (2R,4S)-2-(((4-(4-acryloyl-3-(cya-
nomethyl)piperazin-1-yl)-7-(3-fluoro-2-(trifluorom-
ethyl)phenyl)-5,6,7,8-tetrahydropyrido [3,4-d]py-
rimidin-2-yl)oxy)methyl)-4-((tert-butyldimethylsilyl)
oxy)pyrrolidine-1-carboxylate was prepared following the prep for EXAMPLE 375, Step F and G, substituting benzyl 4-(2-(((2R,4S)-1-(tert-butoxycarbonyl)-4-((tert-butyldimethyl silyl)oxy)pyrrolidin-2-yl) methoxy)-7-(3-fluoro-2-(trifluoromethyl)phenyl)-5,6,7,8-tetrahydropyrido[3,4-d]pyrimidin-4-yl)-2-(cyanomethyl) piperazine-1-carboxylate for benzyl 2-(cyanomethyl)-4-(2-(((S)-1-methylpyrrolidin-2-yl)methoxy)-7-(3-(trifluoromethyl)pyridin-4-yl)-5,6,7,8-tetrahydropyrido[3,4-d]pyrimidin-4-yl)piperazine-1-carboxylate in Step F.

Step D: 2-(1-acryloyl-4-(7-(3-fluoro-2-(trifluorom-
ethyl)phenyl)-2-(((2R,4S)-4-hydroxy-1-methylpyrro-
lidin-2-yl)methoxy)-5,6,7,8-tetrahydropyrido[3,4-d]
pyrimidin-4-yl)piperazin-2-yl)acetonitrile was prepared according to EXAMPLE 390, Step B and C, substituting tert-butyl (2R,4S)-2-(((4-(4-acryloyl-3-(cyanomethyl)piperazin-1-yl)-7-(3-fluoro-2-(trifluoromethyl) phenyl)-5,6,7,8-tetrahydropyrido[3,4-d]pyrimidin-2-yl)oxy) methyl)-4-((tert-butyldimethylsilyl)oxy)pyrrolidine-1-carboxylate for tert-butyl (2R,3S)-2-(((4-((S)-4-acryloyl-3-(cyanomethyl)piperazin-1-yl)-7-(naphthalen-1-yl)-5,6,7,8-tetrahydropyrido [3,4-d] pyrimidin-2-yl)oxy)methyl)-3-((tert-butyldimethylsilyl)oxy)pyrrolidine-1-carboxylate in Step B. ESI+APCI MS m/z 604.3 [M+H]+.

Example 416

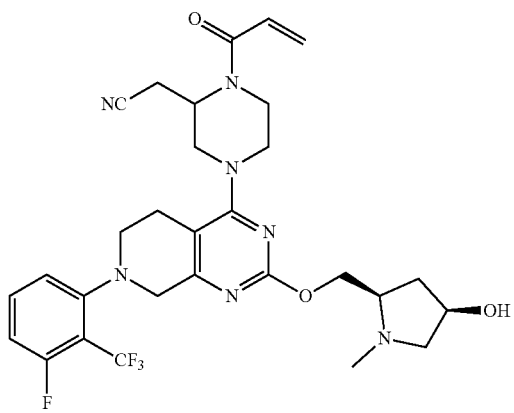 [SMILES: C=CC(=O)N1CCN(c2nc(OC[C@H]3C[C@@H](O)CN3C)nc3c2CCN(c2cccc(F)c2C(F)(F)F)C3)CC1CC#N]

2-(1-acryloyl-4-(7-(3-fluoro-2-(trifluoromethyl)phe-
nyl)-2-(((2R,4R)-4-hydroxy-1-methylpyrrolidin-2-
yl)methoxy)-5,6,7,8-tetrahydropyrido [3,4-d]pyrimi-
din-4-yl)piperazin-2-yl)acetonitrile 2-(1-acryloyl-4-(7-(3-fluoro-2-(trifluoromethyl)phe-
nyl)-2-(((2R,4R)-4-hydroxy-1-methylpyrrolidin-2-
yl)methoxy)-5,6,7,8-tetrahydropyrido[3,4-d]pyrimi-
din-4-yl)piperazin-2-yl)acetonitrile was prepared following Example 415, Steps B-D substituting tert-butyl (2R,4R)-4-((tert-butyldimethylsilyl)oxy)-2-(hydroxymethyl)pyrrolidine-1-carboxylate for (2S,4R)-4-{[tert-Butyl(dimethyl)silyl]oxy}-2-(hydroxymethyl)pyrrolidine-1-carboxylate in Step B. ESI+APCI MS m/z 604.3 [M+H]+.

Example 417

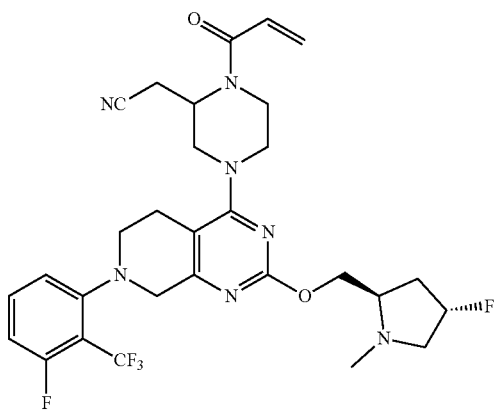 [SMILES: C=CC(=O)N1CCN(c2nc(OC[C@H]3C[C@H](F)CN3C)nc3c2CCN(c2cccc(F)c2C(F)(F)F)C3)CC1CC#N]

2-(1-acryloyl-4-(2-(((2R,4S)-4-fluoro-1-methylpyrrolidin-2-yl)methoxy)-7-(3-fluoro-2-(trifluoromethyl)phenyl)-5,6,7,8-tetrahydropyrido[3,4-d]pyrimidin-4-yl)piperazin-2-yl)acetonitrile 2-(1-acryloyl-4-(2-(((2R,4S)-4-fluoro-1-methylpyrrolidin-2-yl)methoxy)-7-(3-fluoro-2-(trifluoromethyl)phenyl)-5,6,7,8-tetrahydropyrido[3,4-d]pyrimidin-4-yl)piperazin-2-yl)acetonitrile was prepared following Example 415, Steps B-D substituting tert-butyl (2R,4S)-4-fluoro-2-(hydroxymethyl)pyrrolidine-1-carboxylate for (2S,4R)-4-{[tert-Butyl(dimethyl)silyl]oxy}-2-(hydroxymethyl)pyrrolidine-1-carboxylate in Step B. ESI+APCI MS m/z 606.2 [M+H]+.

Example 418

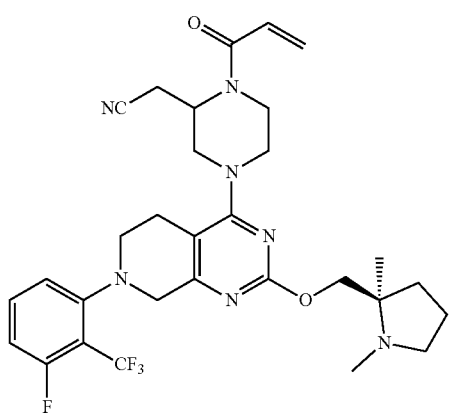 [SMILES: C=CC(=O)N1CCN(c2nc(OC[C@@]3(C)CCCN3C)nc3c2CCN(c2cccc(F)c2C(F)(F)F)C3)CC1CC#N]

2-(1-acryloyl-4-(2-(((R)-1,2-dimethylpyrrolidin-2-yl)methoxy)-7-(3-fluoro-2-(trifluoromethyl)phenyl)-5,6,7,8-tetrahydropyrido[3,4-d]pyrimidin-4-yl)piperazin-2-yl)acetonitrile 2-(1-acryloyl-4-(2-(((R)-1,2-dimethylpyrrolidin-2-yl)methoxy)-7-(3-fluoro-2-(trifluoromethyl)phenyl)-5,6,7,8-tetrahydropyrido[3,4-d]pyrimidin-4-yl)piperazin-2-yl)acetonitrile was prepared following Example 415, Steps B-D substituting tert-butyl (R)-2-(hydroxymethyl)-2-methylpyrrolidine-1-carboxylate for (2S,4R)-4-{[tert-Butyl(dimethyl)silyl]oxy}-2-(hydroxymethyl)pyrrolidine-1-carboxylate in Step B. ESI+APCI MS m/z 602.3 [M+H]+.

Example 419

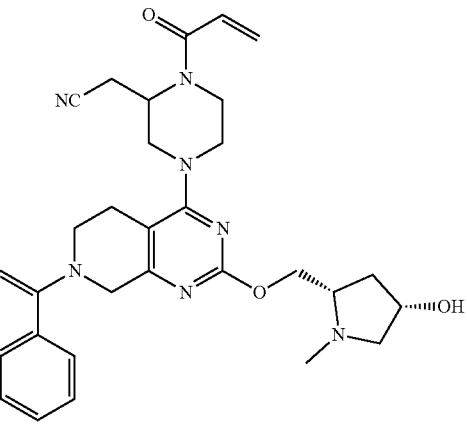

2-(1-acryloyl-4-(2-(((2S,4S)-4-hydroxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile 2-(1-acryloyl-4-(2-(((2S,4S)-4-hydroxy-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile was prepared following Example 415, Steps A-D substituting 1-bromonaphthalene for 1-bromo-3-fluoro-2-(trifluoromethyl)benzene in Step A tert-butyl (2S,4S)-4-((tert-butyldimethylsilyl)oxy)-2-(hydroxymethyl)pyrrolidine-1-carboxylate for (2S,4R)-4-{[tert-Butyl(dimethyl)silyl]oxy}-2-(hydroxymethyl)pyrrolidine-1-carboxylate in Step B. ESI+APCI MS m/z 568.3 [M+H]+.

Example 420

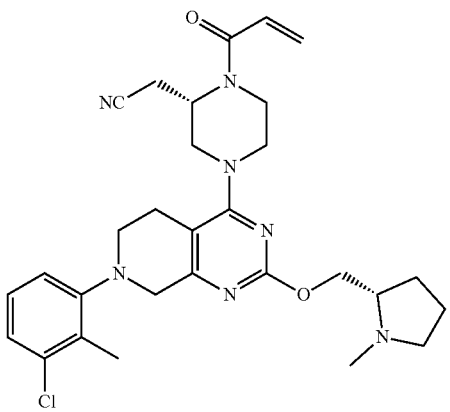 [SMILES: C=CC(=O)N1CCN(c2nc(OC[C@@H]3CCCN3C)nc3c2CCN(c2cccc(Cl)c2C)C3)C[C@@H]1CC#N]

2-((S)-1-acryloyl-4-(7-(3-chloro-2-methylphenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(3-chloro-2-methylphenyl)-2-(((S)-1-methylpyrrolidin-2-yl)methoxy)-5,6,7,8-tetrahydropyrido[3,4-d]pyrimidin-4-yl)piperazin-2-yl)acetonitrile Was prepared following Example 234, Step H-J substituting 1-bromo-3-chloro-2-methylbenzene for 1-bromonaphthalene in Step H and THF for MeOH in Step I. ESI+APCI MS m/z 550.3 [M+H]⁺.

Example 421

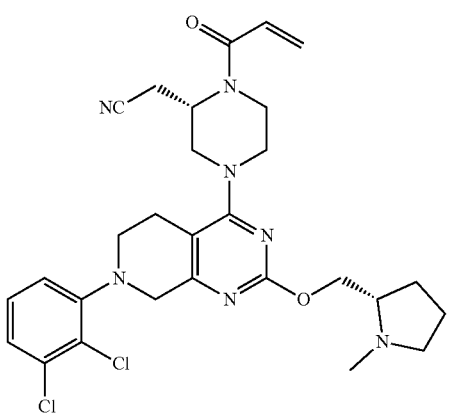

2-((S)-1-acryloyl-4-(7-(2,3-dichlorophenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(2,3-dichlorophenyl)-2-(((S)-1-methylpyrrolidin-2-yl)methoxy)-5,6,7,8-tetrahydropyrido[3,4-d]pyrimidin-4-yl)piperazin-2-yl)acetonitrile Was prepared following Example 234, Step H-J substituting 1-bromo-2,3-dichlorobenzene for 1-bromonaphthalene in Step H and THF for MeOH in Step I. ESI+APCI MS m/z 570.2 [M+H]⁺.

Example 422

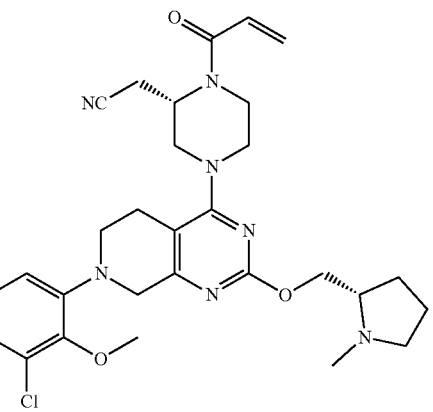

2-((S)-1-acryloyl-4-(7-(3-chloro-2-methoxyphenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(3-chloro-2-methoxyphenyl)-2-((S)-1-methylpyrrolidin-2-yl)methoxy)-5,6,7,8-tetrahydropyrido[3,4-d]pyrimidin-4-yl)piperazin-2-yl)acetonitrile Was prepared following Example 234, Step H-J substituting 1-bromo-3-chloro-2-methoxybenzene for 1-bromonaphthalene in Step H and THF for MeOH in Step I. ESI+APCI MS m/z 566.2 [M+H]⁺.

Example 423

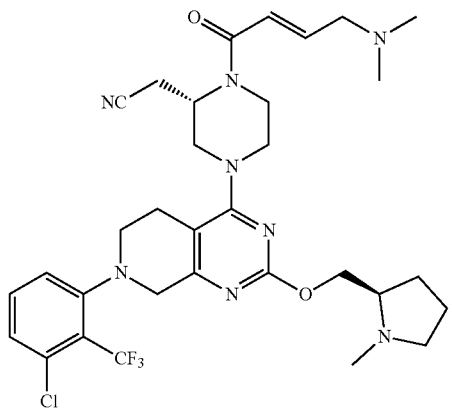 [SMILES: CN(C)C/C=C/C(=O)N1CCN(c2nc(OC[C@H]3CCCN3C)nc3c2CCN(c2cccc(Cl)c2C(F)(F)F)C3)C[C@@H]1CC#N]

2-((S)-4-(7-(3-chloro-2-(trifluoromethyl)phenyl)-2-(((R)-1-methylpyrrolidin-2-yl)methoxy)-5,6,7,8-tetrahydropyrido[3,4-d]pyrimidin-4-yl)-1-((E)-4-(dimethylamino)but-2-enoyl)piperazin-2-yl)acetonitrile Step A: 2-((S)-4-(7-(3-chloro-2-(trifluoromethyl)phenyl)-2-(((R)-1-methylpyrrolidin-2-yl)methoxy)-5,6,7,8-tetrahydropyrido[3,4-d]pyrimidin-4-yl)piperazin-2-yl)acetonitrile Example 234, Step F-I substituting (R)-(1-methylpyrrolidin-2-yl)methanol for (S)-(1-methylpyrrolidin-2-yl)methanol in Step F, 1-bromo-3-chloro-2-(trifluoromethyl)benzene for 1-bromonaphthalene in Step H and THF for MeOH in Step I.

Step B: 2-((S)-4-(7-(3-chloro-2-(trifluoromethyl)phenyl)-2-(((R)-1-methylpyrrolidin-2-yl)methoxy)-5,6,7,8-tetrahydropyrido[3,4-d]pyrimidin-4-yl)-1-((E)-4-(dimethylamino)but-2-enoyl)piperazin-2-yl)acetonitrile N,N'-Diisopropylethylamine (29.5 µl, 0.166 mmol) and O-(7-Azabenzotriazol-1-yl)-N,N,N',N'-tetramethyluronium PF6 HATU (25.2 mg, 0.066 mmol) were added to a solution of trans-4-dimethylaminocrotonic acid (6.42 mg, 0.05 mmol) and 2-((S)-4-(7-(3-chloro-2-(trifluoromethyl)phenyl)-2-(((R)-1-methylpyrrolidin-2-yl)methoxy)-5,6,7,8-tetrahydropyrido[3,4-d]pyrimidin-4-yl)piperazin-2-yl)acetonitrile 2,2,2-trifluoroacetate (22 mg, 0.033 mmol) in dichloromethane (331 µl, 0.033 mmol). The reaction was stirred at rt for 18 hr. The mixture was washed with brine, extracted with 30% iPrOH/CHCl3 (3×), combined extracts and concentrated. The resulting residue was purified by reverse phase chromatography (5-95% ACN/H$_2$O with 0.1% TFA) then free based using DCM and aqueous bicarb to give title compound 2-((S)-4-(7-(3-chloro-2-(trifluoromethyl)phenyl)-2-(((R)-1-methylpyrrolidin-2-yl)methoxy)-5,6,7,8-tetrahydropyrido [3,4-d]pyrimidin-4-yl)-1-((E)-4-(dimethylamino)but-2-enoyl)piperazin-2-yl)acetonitrile (EXAMPLE 423, 10 mg, 0.015 mmol, 46% yield). ESI+APCI MS m/z 661.3[M+H]$^+$.

Example 424

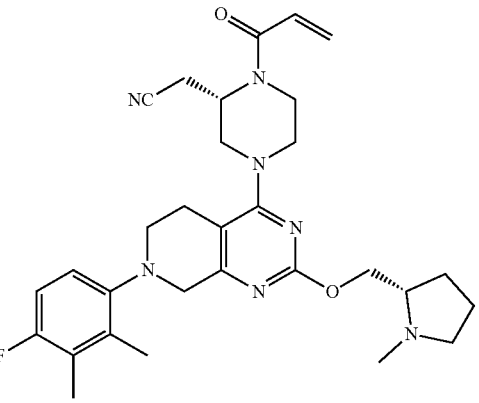

2-((S)-1-acryloyl-4-(7-(4-fluoro-2,3-dimethylphenyl)-2-((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(4-fluoro-2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile Was prepared following Example 234, Step H-J substituting 1-bromo-4-fluoro-2,3-dimethylbenzene for 1-bromonaphthalene in Step H. ESI+APCI MS m/z 548.3 [M+H]$^+$.

Example 425

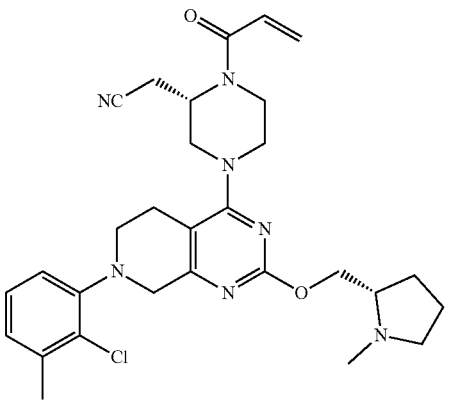 [SMILES: C=CC(=O)N1CCN(c2nc(OC[C@@H]3CCCN3C)nc3c2CCN(c2cccc(C)c2Cl)C3)C[C@@H]1CC#N]

2-((S)-1-acryloyl-4-(7-(2-chloro-3-methylphenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(2-chloro-3-methylphenyl)-2-(((S)-1-methylpyrrolidin-2-yl)methoxy)-5,6,7,8-tetrahydropyrido[3,4-d]pyrimidin-4-yl)piperazin-2-yl)acetonitrile Was prepared following Example 234, Step H-J substituting 1-bromo-2-chloro-3-methylbenzene for 1-bromonaphthalene in Step H and THF for MeOH in Step I. ESI+APCI MS m/z 550.2 [M+H]⁺.
Example 426
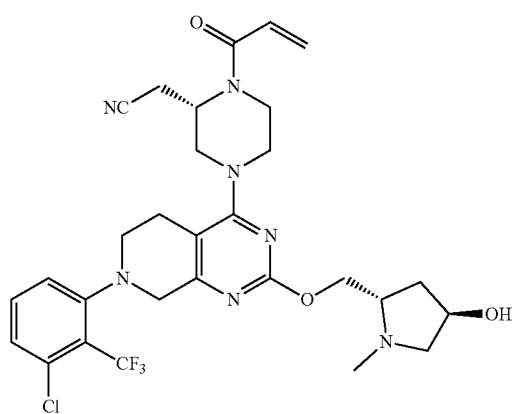 [SMILES: C=CC(=O)N1CCN(c2nc(OC[C@@H]3C[C@@H](O)CN3C)nc3c2CCN(c2cccc(Cl)c2C(F)(F)F)C3)C[C@@H]1CC#N]
2-((S)-1-acryloyl-4-(7-(3-chloro-2-(trifluoromethyl)phenyl)-2-(((2S,4R)-4-hydroxy-1-methylpyrrolidin-2-yl)methoxy)-5,6,7,8-tetrahydropyrido[3,4-d]pyrimidin-4-yl)piperazin-2-yl)acetonitrile
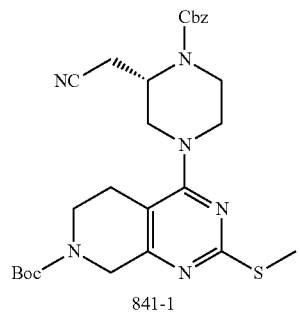
841-1
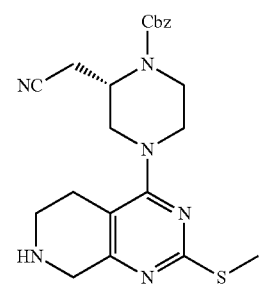
-continued
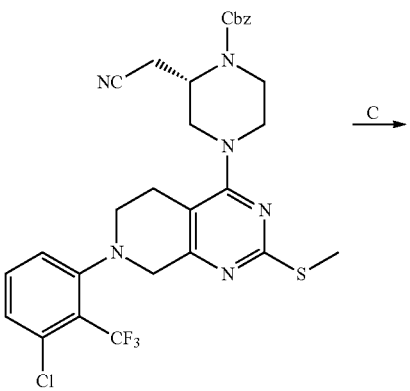
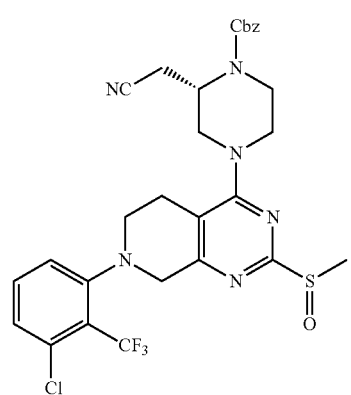
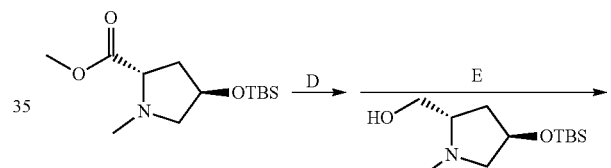
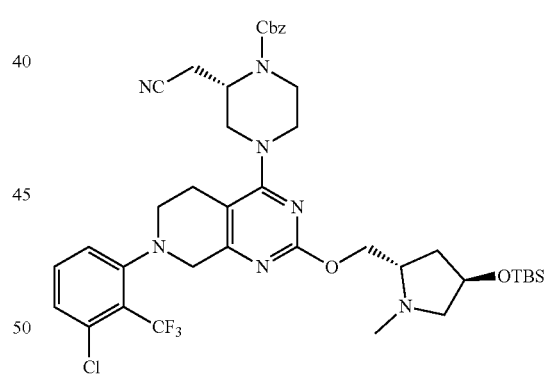
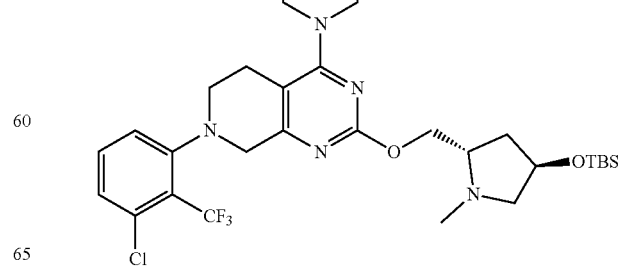

Step A: benzyl (S)-2-(cyanomethyl)-4-(2-(methylthio)-5,6,7,8-tetrahydropyrido[3,4-d]pyrimidin-4-yl)piperazine-1-carboxylate A mixture of tert-butyl (S)-4-(4-((benzyloxy)carbonyl)-3-(cyanomethyl)piperazin-1-yl)-2-(methylthio)-5,8-dihydropyrido[3,4-d]pyrimidine-7(6H)-carboxylate (741 mg, 1.38 mmol) in dichloromethane (9171 µl, 1.38 mmol) was treated with hydrochloric acid (1720 µl, 6.88 mmol) at 0° C. and stirred for 1 h after warming to rt. The mixture was quenched with saturated NaHCO₃, the aqueous phase was separated and extracted with DCM (3×). The combined extracts were dried, filtered and concentrated give benzyl (S)-2-(cyanomethyl)-4-(2-(methylthio)-5,6,7,8-tetrahydropyrido[3,4-d]pyrimidin-4-yl)piperazine-1-carboxylate (608 mg, 1.39 mmol, 100% yield). ESI+APCI MS m/z 439.2 [M+H]⁺.

Step B: benzyl (S)-4-(7-(3-chloro-2-(trifluoromethyl)phenyl)-2-(methylthio)-5,6,7,8-tetrahydropyrido[3,4-d]pyrimidin-4-yl)-2-(cyanomethyl)piperazine-1-carboxylate To a vial was added cesium carbonate (1.65 g, 5.06 mmol), benzyl (S)-2-(cyanomethyl)-4-(2-(methylthio)-5,6,7,8-tetrahydropyrido[3,4-d]pyrimidin-4-yl)piperazine-1-carboxylate (0.74 g, 1.69 mmol), and 1-bromo-3-chloro-2-(trifluoromethyl)benzene (0.876 g, 3.37 mmol) in 1,4-dioxane (11.2 ml, 1.69 mmol). The mixture was purged with Ar for 10 min and treated with methanesulfonato(2-dicyclohexylphosphino-2',6'-di-i-propoxy-1,1'-biphenyl)(2'-methylamino-1,1'-biphenyl-2-yl)palladium(II) RuPhos Pd G4 (0.215 g, 0.253 mmol). The mixture was purged with Ar for 10 min, the resulting mixture was heated to 100° C. for 4 hr. The reaction was concentrated, treated with water, extracted with 30% iPrOH/CHCl3 (3×), dried, filtered and concentrated and the resulting residue was purified by silica gel (2-16% MeOH in DCM with 0.25% NH₄OH) to provide benzyl (S)-4-(7-(3-chloro-2-(trifluoromethyl)phenyl)-2-(methylthio)-5,6,7,8-tetrahydropyrido[3,4-d]pyrimidin-4-yl)-2-(cyanomethyl)piperazine-1-carboxylate (388 mg, 0.63 mmol, 37% yield). ESI+APCI MS m/z 617.2 [M+H]⁺.

Step C: benzyl (2S)-4-(7-(3-chloro-2-(trifluoromethyl)phenyl)-2-(methylsulfinyl)-5,6,7,8-tetrahydropyrido[3,4-d]pyrimidin-4-yl)-2-(cyanomethyl)piperazine-1-carboxylate To a solution of benzyl (S)-4-(7-(3-chloro-2-(trifluoromethyl)phenyl)-2-(methylthio)-5,6,7,8-tetrahydropyrido[3,4-d]pyrimidin-4-yl)-2-(cyanomethyl)piperazine-1-carboxylate (388 mg, 0.566 mmol) in dichloromethane (5659 µl, 0.566 mmol) was added m-chloroperbenzoic acid (117.6 mg, 0.680 mmol) at 0° C. The mixture was stirred at this temp for 90 min. The mixture was quenched with saturated Na2S2O3, the aqueous layers were separated and extracted with EtOAc (3×). The extracts were combined dried, filtered and concentrated. The resulting residue was purified by silica gel (0-100% EA/hex) to give benzyl (2S)-4-(7-(3-chloro-2-(trifluoromethyl)phenyl)-2-(methylsulfinyl)-5,6,7,8-tetrahydropyrido[3,4-d]pyrimidin-4-yl)-2-(cyanomethyl)piperazine-1-carboxylate (282 mg, 0.445 mmol, 79% yield).

Step D: ((2S,4R)-4-((tert-butyldimethylsilyl)oxy)-1-methylpyrrolidin-2-yl)methanol To a suspension of methyl (2S,4R)-4-((tert-butyldimethylsilyl)oxy)-1-methylpyrrolidine-2-carboxylate (3.65 g, 13.3 mmol) in tetrahydrofuran (66.7 ml, 13.3 mmol), at 0° C. under nitrogen lithium borohydride (13.3 ml, 26.7 mmol) was added slowly. The reaction was allowed to warm to RT and the mixture stirred at rt for 18 h. The reaction mixture was slowly quenched with saturated NH4Cl, diluted with water and extracted twice with EtOAc (20 mL). The combined organic phases were dried, filtered and concentrated and purified by silica gel (0-80% EA/hex) to give ((2S,4R)-4-((tert-butyldimethylsilyl)oxy)-1-methylpyrrolidin-2-yl)methanol (1.8 g, 5.87 mmol, 44% yield).

Step E: benzyl (S)-4-(2-(((2S,4R)-4-((tert-butyldimethylsilyl)oxy)-1-methylpyrrolidin-2-yl)methoxy)-7-(3-chloro-2-(trifluoromethyl)phenyl)-5,6,7,8-tetrahydropyrido[3,4-d]pyrimidin-4-yl)-2-(cyanomethyl)piperazine-1-carboxylate To a solution of (2S,4R)-1-boc-4-(tert-butyldimethylsilyloxy)-2-(hydroxymethyl)pyrrolidine (144 mg, 0.587 mmol) and benzyl (2S)-4-(7-(3-chloro-2-(trifluoromethyl)phenyl)-2-(methylsulfinyl)-5,6,7,8-tetrahydropyrido[3,4-d]pyrimidin-4-yl)-2-(cyanomethyl)piperazine-1-carboxylate 2,2,2-trifluoroacetate (258 mg, 0.294 mmol) in toluene (2935 µl, 0.294 mmol) was added sodium-t-butoxide (42.3 mg, 0.440 mmol). The reaction was stirred at rt for 1 h. The mixture was washed with water, extracted with 30% iPrOH/CHCl3 (3×), combined extracts, dried, filtered and concentrated. The resulting residue was purified by silica gel (0-100% EA/hex 20 CV) to give benzyl (S)-4-(2-(((2S,4R)-4-((tert-butyldimethylsilyl)oxy)-1-methylpyrrolidin-2-yl)methoxy)-7-(3-chloro-2-(trifluoromethyl)phenyl)-5,6,7,8-tetrahydropyrido[3,4-d]pyrimidin-4-yl)-2-(cyanomethyl)piperazine-1-carboxylate (57 mg, 0.070 mmol, 23% yield).

Step F: 2-((S)-4-(2-(((2S,4R)-4-((tert-butyldimethylsilyl)oxy)-1-methylpyrrolidin-2-yl)methoxy)-7-(3-chloro-2-(trifluoromethyl)phenyl)-5,6,7,8-tetrahydropyrido[3,4-d]pyrimidin-4-yl)piperazin-2-yl)acetonitrile To a solution of benzyl (S)-4-(2-(((2S,4R)-4-((tert-butyldimethylsilyl)oxy)-1-methylpyrrolidin-2-yl)methoxy)-7-(3-chloro-2-(trifluoromethyl)phenyl)-5,6,7,8-tetrahydropyrido[3,4-d]pyrimidin-4-yl)-2-(cyanomethyl)piperazine-1-carboxylate (56 mg, 0.069 mmol) in THF (688 µl, 0.069 mmol) was added palladium (29 mg, 0.028 mmol) (Degussa Type, 10 wt %, 50% H₂O) and then an atmosphere of H₂ was introduced via vacuum followed by balloon pressure and was stirred for 6 hr. The mixture was then diluted with MeOH and filtered through GF/F paper. The filtrate was then concentrated to provide desired product which was used as is.

Step G: 2-((S)-1-acryloyl-4-(7-(3-chloro-2-(trifluoromethyl)phenyl)-2-(((2S,4R)-4-hydroxy-1-methylpyrrolidin-2-yl)methoxy)-5,6,7,8-tetrahydropyrido[3,4-d]pyrimidin-4-yl)piperazin-2-yl)acetonitrile was prepared according to EXAMPLE 384 Step D and E substituting 2-((S)-4-(2-(((2S,4R)-4-((tert-butyldimethylsilyl)oxy)-1-methylpyrrolidin-2-yl)methoxy)-7-(3-chloro-2-(trifluoromethyl)phenyl)-5,6,7,8-tetrahydropyrido[3,4-d]pyrimidin-4-yl)piperazin-2-yl)acetonitrile for Tert-butyl (2S,4R)-2-(((4-((S)-3-(cyanomethyl)piperazin-1-yl)-7-(5-fluoro-4-(trifluoromethyl)pyridin-3-yl)-5,6,7,8-tetrahydropyrido[3,4-d]pyrimidin-2-yl)oxy)methyl)-4-fluoropyrrolidine-1-carboxylate in Step D. ESI+APCI MS m/z 620.2 [M+H]⁺.

Example 427

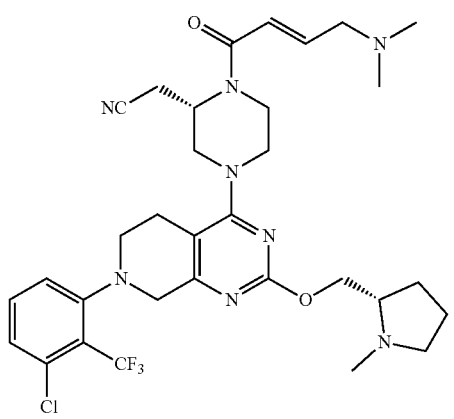 [SMILES: CN(C)C/C=C/C(=O)N1CCN(c2nc(OC[C@@H]3CCCN3C)nc3c2CCN(c2cccc(Cl)c2C(F)(F)F)C3)C[C@@H]1CC#N]

2-((S)-4-(7-(3-chloro-2-(trifluoromethyl)phenyl)-2-((S)-1-methylpyrrolidin-2-yl)methoxy)-5,6,7,8-tetrahydropyrido[3,4-d]pyrimidin-4-yl)-1-((E)-4-(dimethylamino)but-2-enoyl)piperazin-2-yl)acetonitrile 2-((S)-4-(7-(3-chloro-2-(trifluoromethyl)phenyl)-2-((S)-1-methylpyrrolidin-2-yl)methoxy)-5,6,7,8-tetrahydropyrido[3,4-d]pyrimidin-4-yl)-1-((E)-4-(dimethylamino)but-2-enoyl)piperazin-2-yl)acetonitrile was prepared according to Example 234, substituting (S)-(1-methylpyrrolidin-2-yl)methanol for (R)-(1-methylpyrrolidin-2-yl)methanol in Step A. ESI+APCI MS m/z 661.3 [M+H]⁺.

Example 428

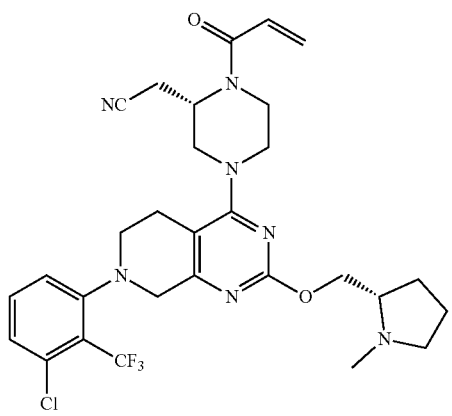 [SMILES: C=CC(=O)N1CCN(c2nc(OC[C@@H]3CCCN3C)nc3c2CCN(c2cccc(Cl)c2C(F)(F)F)C3)C[C@@H]1CC#N]

2-((S)-1-acryloyl-4-(7-(3-chloro-2-(trifluoromethyl)phenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(3-chloro-2-(trifluoromethyl)phenyl)-2-(((S)-1-methylpyrrolidin-2-yl)methoxy)-5,6,7,8-tetrahydropyrido [3,4-d]pyrimidin-4-yl)piperazin-2-yl)acetonitrile was prepared according to Example 234, Step H-J substituting 1-bromo-3-chloro-2-(trifluoromethyl)benzene for 1-bromonaphthalene in Step H and THF for MeOH in Step I. ESI+APCI MS m/z 604.2 [M+H]⁺.

Example 429

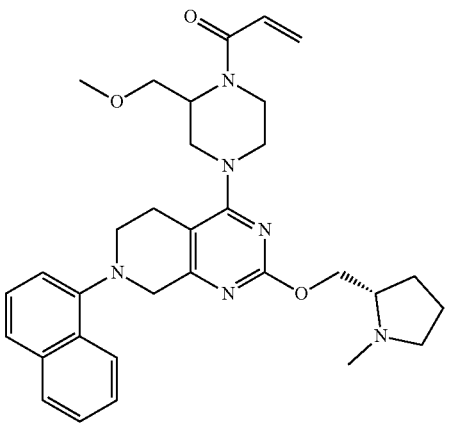 [SMILES: C=CC(=O)N1CCN(c2nc(OC[C@@H]3CCCN3C)nc3c2CCN(c2cccc4ccccc24)C3)CC1COC]

1-(2-(methoxymethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-1-yl)prop-2-en-1-one -continued

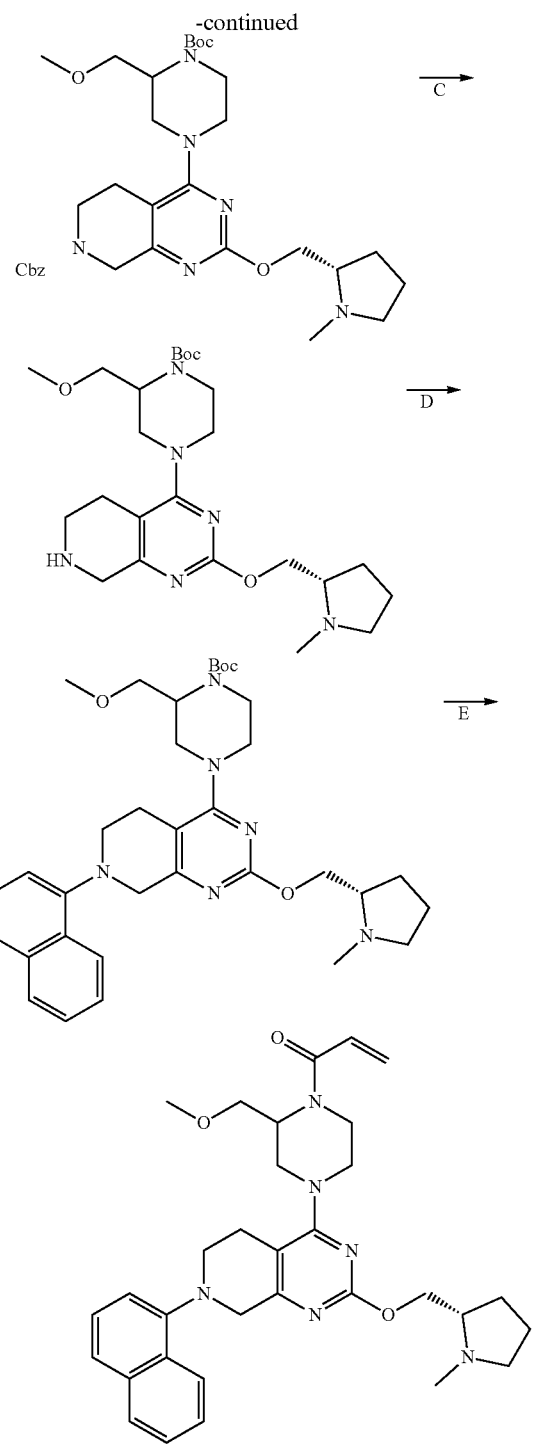

Step A: benzyl 4-(4-(tert-butoxycarbonyl)-3-(methoxymethyl)piperazin-1-yl)-2-chloro-5,8-dihydropyrido[3,4-d]pyrimidine-7(6H)-carboxylate A stirred solution of tert-butyl 2-(methoxymethyl)piperazine-1-carboxylate (0.715 g, 3.10 mmol) in N,N-dimethylacetamide (3 ml, 2.96 mmol) was cooled on an ice bath and then solid benzyl 2,4-dichloro-5,8-dihydropyrido[3,4-d]pyrimidine-7(6H)-carboxylate (1.00 g, 2.96 mmol) was added in small portions followed by addition of DIPEA (0.57 mL, 3.25 mmol). The resulting solution was warmed to r.t. and stirred for 1 hour. The reaction mixture was partitioned between water (15 mL) and MTBE (50 mL) and the layers separated. The organic layer was washed with water (2*10 mL), brine (10 mL), dried over $Na_2SO_4$ and evaporated in vacuo and used crude in the next reaction.

Step B: benzyl 4-(4-(tert-butoxycarbonyl)-3-(methoxymethyl)piperazin-1-yl)-2-(((S)-1-methylpyrrolidin-2-yl)methoxy)-5,8-dihydropyrido[3,4-d]pyrimidine-7(6H)-carboxylate A mixture of crude benzyl 4-(4-(tert-butoxycarbonyl)-3-(methoxymethyl)piperazin-1-yl)-2-chloro-5,8-dihydropyrido[3,4-d]pyrimidine-7(6H)-carboxylate (500 mg, 0.940 mmol), (S)-(1-methylpyrrolidin-2-yl)methanol (216 mg, 1.88 mmol), $Cs_2CO_3$ (612 mg, 1.88 mmol) and dioxane (0.5 mL) was flushed with nitrogen, the vial was capped and stirred at 100° C. for 2 hours and then at 120° C. overnight. The reaction mixture was cooled and partitioned between EtOAc (20 mL) and water (10 mL). The organic layer was separated and washed with water and brine (5 mL each), dried over $Na_2SO_4$ and evaporated in vacuo. The residue was chromatographed on silica gel using 4 to 10% MeOH/DCM+0.2% $NH_4OH$ as eluent to give product (197 mg, 34%). ESI+APCI MS m/z 611.4 [M+H]+.

Step C: tert-butyl 2-(methoxymethyl)-4-(2-(((S)-1-methylpyrrolidin-2-yl)methoxy)-5,6,7,8-tetrahydropyrido[3,4-d]pyrimidin-4-yl)piperazine-1-carboxylate A mixture of benzyl 4-(4-(tert-butoxycarbonyl)-3-(methoxymethyl)piperazin-1-yl)-2-(((S)-1-methylpyrrolidin-2-yl)methoxy)-5,8-dihydropyrido[3,4-d]pyrimidine-7(6H)-carboxylate (197 mg, 0.323 mmol), methanol (10 mL) and palladium on carbon (10 mg, 5%, Degussa type E101 NO/W) was degassed and stirred under hydrogen atmosphere for 1 hour. The mixture was filtered through Celite (2 mL) and the celite washed with MeOH (3×3 mL). The combined filtrates were evaporated in vacuo, azeotroped by evaporation with toluene, and dried under high vacuum to give product (150 mg, 98%). ESI+APCI MS m/z 477.2 [M+H]+.

Step D: tert-butyl 2-(methoxymethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate A mixture of tert-butyl 2-(methoxymethyl)-4-(2-(((S)-1-methylpyrrolidin-2-yl)methoxy)-5,6,7,8-tetrahydropyrido[3,4-d]pyrimidin-4-yl)piperazine-1-carboxylate (150 mg, 0.315 mmol), $Cs_2CO_3$ (308 mg, 0.944 mmol), dioxane (1 mL), 1-iodonaphthalene (0.0689 ml, 0.472 mmol) and methanesulfonato(2-dicyclohexylphosphino-2',6'-di-i-propoxy-1,1'-biphenyl)(2-amino-1,1'-biphenyl-2-yl)palladium(II) (RuPhos-Pd-G3, 0.1 eq., 26.3 mg, 0.0315 mmol) was purged with nitrogen, the flask was capped and the reaction stirred at 70° C. overnight. The reaction mixture was cooled, partitioned between EtOAc (15 mL) and water (5 mL) and the layers separated. The organic layer was washed with water and brine (5 mL each), dried over $Na_2SO_4$ and evaporated in vacuo. The residue was chromatographed on silica gel using 4 to 10% MeOH+0.5% $NH_4OH$ as eluent to give product (131 mg, 69%). ESI+APCI MS m/z 603.3 [M+H]+.

Step E: 1-(2-(methoxymethyl)-4-(2-(((S)-1-methyl-pyrrolidin-2-yl)methoxy)-7-(naphthalen-1-yl)-5,6,7,8-tetrahydropyrido[3,4-d]pyrimidin-4-yl)piperazin-1-yl)prop-2-en-1-one Tert-butyl 2-(methoxymethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (130 mg, 0.2157 mmol) was dissolved in 1M TFA/DCM and the solution stirred at r.t. for 1 hour. The solution was partitioned between 2M Na$_2$CO$_3$ (5 mL) and DCM (15 mL) and the layers separated and the organic layer concentrated in vacuo. The residue was dissolved in DCM (5 mL) and cooled to −30° C. with stirring and triethylamine (0.09018 ml, 0.6470 mmol) added followed by addition of acryloyl chloride (0.03504 ml, 0.4313 mmol). After 1 min at −30° C. the reaction mixture was quenched with NH$_4$OH (0.05 mL) and evaporated in vacuo and dried under high vacuum. The residue was dissolved in DCM (5 mL), filtered through a cotton plug and chromatographed on silica gel using 5 to 10% MeOH/DCM+0.25% NH$_4$OH as eluent to give title compound (EXAMPLE 429, 19.55 mg, 16%). ESI+APCI MS m/z 557.3 [M+H]$^+$.

Example 430

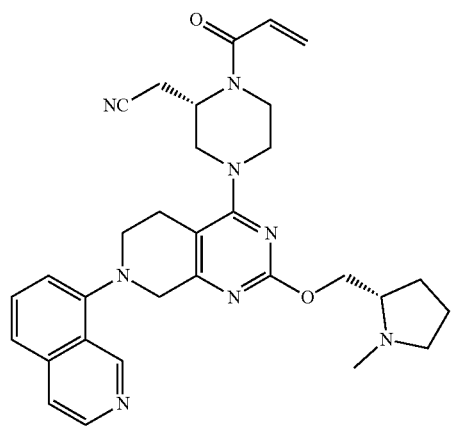 [SMILES: C=CC(=O)N1CCN(c2nc(OC[C@@H]3CCCN3C)nc3c2CCN(c2cccc4ccncc24)C3)C[C@@H]1CC#N]

2-((S)-1-acryloyl-4-(7-(isoquinolin-8-yl)-2-((S)-1-methylpyrrolidin-2-yl)methoxy)-5,6,7,8-tetrahydro-pyrido[3,4-d]pyrimidin-4-yl)piperazin-2-yl)acetonitrile

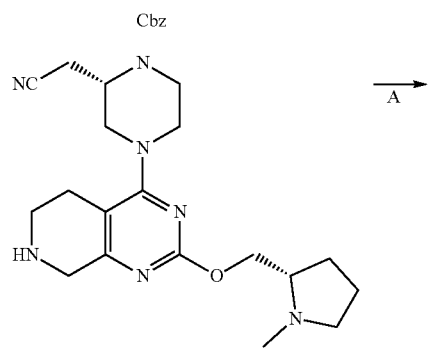

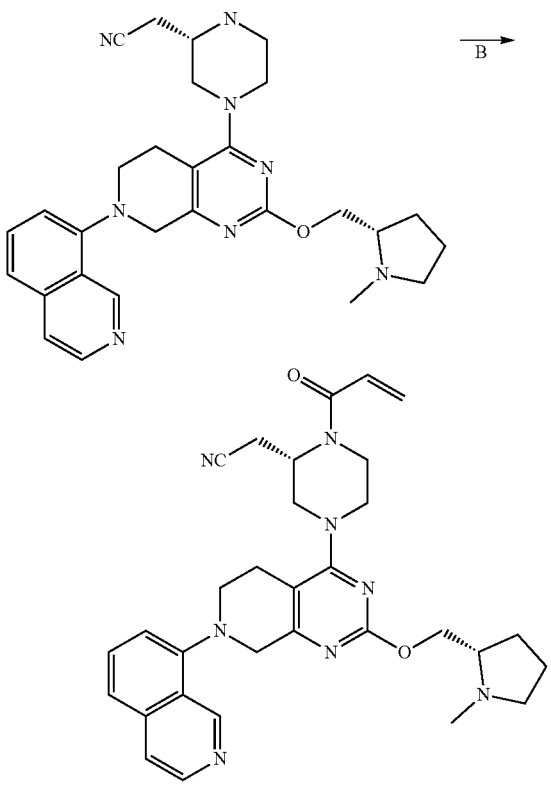

Step A: benzyl (S)-2-(cyanomethyl)-4-(7-(isoquinolin-8-yl)-2-(((S)-1-methylpyrrolidin-2-yl)methoxy)-5,6,7,8-tetrahydropyrido[3,4-d]pyrimidin-4-yl)piperazine-1-carboxylate A mixture of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (125 mg, 0.247 mmol), Cs$_2$CO$_3$ (242 mg, 0.742 mmol), 8-bromoisoquinoline (77.2 mg, 0.371 mmol) and methanesulfonato(2-dicyclohexylphosphino-2',6'-di-i-propoxy-1,1'-biphenyl)(2-amino-1,1'-biphenyl-2-yl)palladium(II) (RuPhos-Pd-G3, 0.1 eq., 20.7 mg, 0.0247 mmol) in 2 mL of dioxane was purged with nitrogen, the flask was capped and stirred at 80° C. for 2.5 hours. The reaction mixture was cooled, partitioned between EtOAc (20 mL) and water (10 mL) and the layers separated. The organic layer was washed with water and brine (5 mL each), dried over Na$_2$SO$_4$ and evaporated in vacuo. The residue was chromatographed on silica gel using 4% MeOH/DCM+0.4% NH$_4$OH as eluent to give product (100 mg, 64%). ESI+APCI MS m/z 633.3 [M+H]$^+$.

Step B: 2-((S)-1-acryloyl-4-(7-(isoquinolin-8-yl)-2-((S)-1-methylpyrrolidin-2-yl)methoxy)-5,6,7,8-tetrahydropyrido[3,4-d]pyrimidin-4-yl)piperazin-2-yl)acetonitrile To a solution of benzyl (S)-2-(cyanomethyl)-4-(7-(isoquinolin-8-yl)-2-((S)-1-methylpyrrolidin-2-yl)methoxy)-5,6,7,8-tetrahydropyrido[3,4-d]pyrimidin-4-yl)piperazine-1-carboxylate (100 mg, 0.1580 mmol) in MeOH-THF (1:1; 3 mL) was added palladium on carbon (30 mg, 5%, Degussa type E101 NO/W) and the mixture degassed under vacuum and backfilled with hydrogen and the reaction stirred under hydrogen atmosphere for 2 hours. The reaction was filtered through Celite (2 mL) and the celite washed with EtOH (3*2 mL). The combined organics were evaporated in vacuo The residue was dissolved in DCM (10 mL) and the solution cooled with stirring to −30° C. To the solution was added NEt$_3$ (0.14 mL) followed by acryloyl chloride (0.02568 ml, 0.3161 mmol) and the reaction mixture stirred at −30° C. for 1 minute. The reaction was quenched with addition of NH$_4$OH (0.05 mL) and concentrated in vacuo. The residue was dissolved in DCM (5 mL), filtered through a cotton plug and chromatographed on silica gel using 6 to 10% MeOH/DCM+0.6% NH$_4$OH as eluent to give title compound (EXAMPLE 430, 22.19 mg, 25%). ESI+APCI MS m/z 553.3 [M+H]$^+$.

Example 431

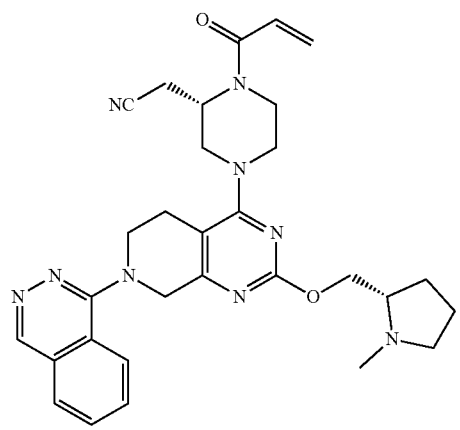 [SMILES: C=CC(=O)N1CCN(c2nc(OC[C@@H]3CCCN3C)nc3c2CCN(c2nncc4ccccc24)C3)C[C@@H]1CC#N]

2-((S)-1-acryloyl-4-(2-(((S)-1-methylpyrrolidin-2-yl)methoxy)-7-(phthalazin-1-yl)-5,6,7,8-tetrahydropyrido[3,4-d]pyrimidin-4-yl)piperazin-2-yl)acetonitrile

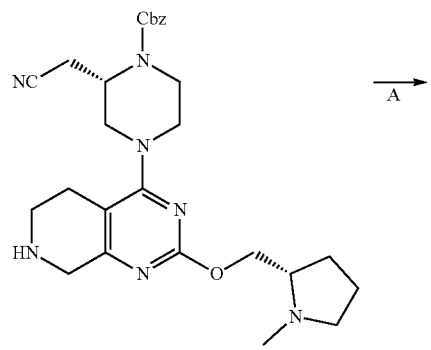

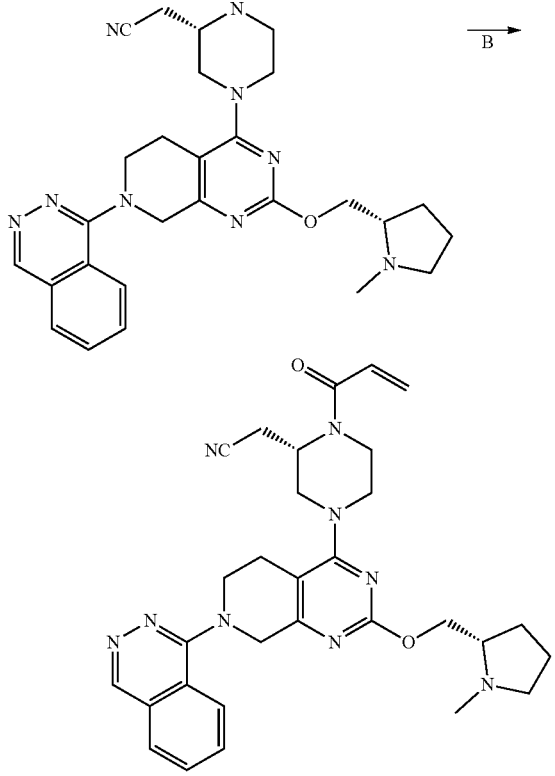

Step A: benzyl (S)-2-(cyanomethyl)-4-(2-(((S)-1-methylpyrrolidin-2-yl)methoxy)-7-(phthalazin-1-yl)-5,6,7,8-tetrahydropyrido[3,4-d]pyrimidin-4-yl)piperazine-1-carboxylate A mixture of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (101 mg, 0.200 mmol), 1-chlorophthalazine (65.8 mg, 0.400 mmol) and N-ethyl-N-isopropylpropan-2-amine (0.0696 ml, 0.400 mmol) in 1,4-dioxane (0.5 ml, 0.200 mmol) was purged with nitrogen, the reaction capped and stirred at 80° C. for 16 hours. The reaction mixture was cooled, partitioned between EtOAc (20 mL) and water (5 mL) and the layers separated. The organic layer was washed with water and brine (5 mL each), dried over Na$_2$SO$_4$ and concentrated in vacuo. The residue was chromatographed on silica gel using 6% MeOH/DCM+0.6% NH$_4$OH as eluent to give product (53 mg, 42%). ESI+APCI MS m/z 634.3 [M+H]$^+$.

Step B: 2-((S)-1-acryloyl-4-(2-(((S)-1-methylpyrrolidin-2-yl)methoxy)-7-(phthalazin-1-yl)-5,6,7,8-tetrahydropyrido[3,4-d]pyrimidin-4-yl)piperazin-2-yl)acetonitrile A mixture of benzyl (S)-2-(cyanomethyl)-4-(2-(((S)-1-methylpyrrolidin-2-yl)methoxy)-7-(phthalazin-1-yl)-5,6,7,8-tetrahydropyrido[3,4-d]pyrimidin-4-yl)piperazine-1-carboxylate (60 mg, 0.09467 mmol), methanol (2 ml) and palladium on carbon (20 mg, 5%, Degussa type E101 NO/W) was degassed under vacuum and backfilled with hydrogen and the reaction stirred under hydrogen atmosphere for 4 hours. The reaction was filtered through Celite (2 mL) and the celite washed with MeOH (3×3 mL). The combined organics were evaporated in vacuo. The residue was dissolved in DCM (5 mL) and cooled to −30° C. with stirring. To the solution was next added triethylamine (0.06598 ml, 0.4734 mmol) followed by acryloyl chloride (0.02308 ml, 0.2840 mmol) and the reaction stirred for 5 minutes at −30° C. The reaction was quenched by addition of sat. NaHCO$_3$ (1 mL). The mixture was warmed up to r.t., water was added (2 mL) and the layers were separated. The organics were dried over Na$_2$SO$_4$ and evaporated in vacuo and the residue chromatographed on silica gel using 4 to 10% MeOH+0.4% NH$_4$OH as eluent to give impure product, which was purified on the Gilson reverse prep HPCL eluting with 5 to 95% acetonitrile in water+0.1% TFA. Fractions containing product were partitioned between DCM and sat. Na$_2$CO$_3$ and the layers separated. The organics were next washed with brine, dried over Na$_2$SO$_4$ and concentrated in vacuo to give title compound (EXAMPLE 431, 1.1 mg, 2%). ESI+APCI MS m/z 554.2 [M+H]$^+$.

Example 432

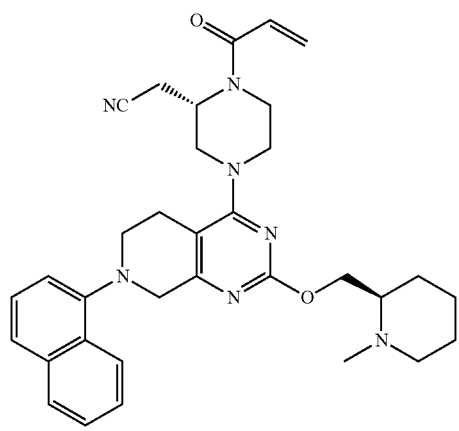 [SMILES: C=CC(=O)N1CCN(c2nc(OC[C@H]3CCCCN3C)nc3c2CCN(c2cccc4ccccc24)C3)C[C@@H]1CC#N]

2-((S)-1-acryloyl-4-(2-(((R)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile

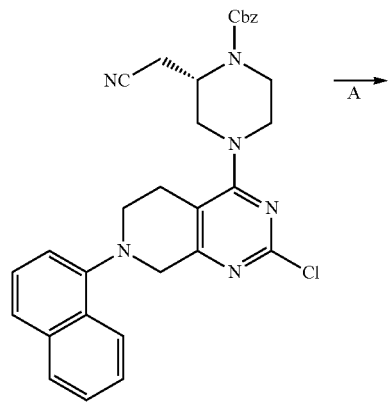

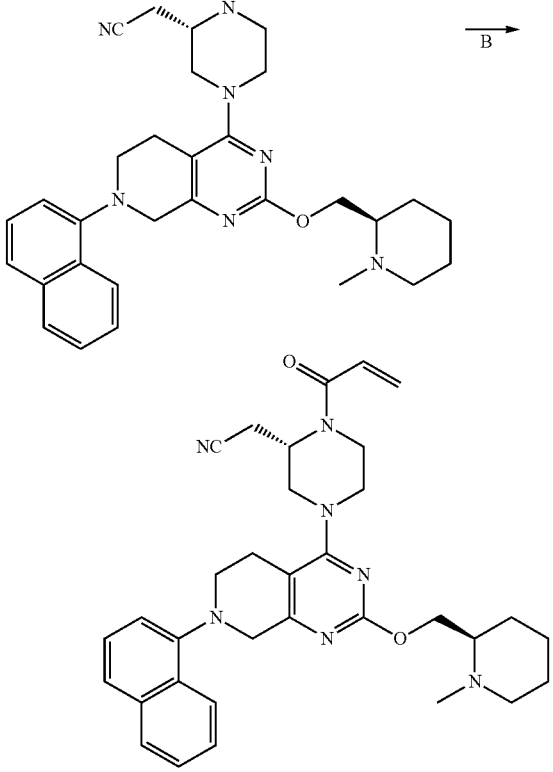

Step A: 2-((S)-4-(2-(((R)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile A mixture of benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (250 mg, 0.452 mmol), (R)-(1-methylpiperidin-2-yl)methanol (175 mg, 1.36 mmol) and Methanesulfonato(2-dicyclohexylphosphino-2',6'-di-i-propoxy-1,1'-biphenyl)(2'-methylamino-1,1'-biphenyl-2-yl)palladium(II) (19.2 mg, 0.0226 mmol) in 1,4-dioxane (2 mL) was purged with nitrogen and stirred at 80° C. overnight. The reaction mixture was cooled, partitioned between MTBE (20 mL) and water (5 mL) and the layers separated. The organic layer was washed with water and brine (5 mL each), dried over Na$_2$SO$_4$ and concentrated in vacuo. The residue was dissolved in MeOH (5 mL) followed by addition of palladium on carbon (70 mg, 5%, Degussa type E101 NO/W). The reaction mixture was degassed under vacuum and backfilled with hydrogen and the reaction stirred under H$_2$ atmosphere for 1.5 hours. The reaction was filtered through Celite (2 mL) and the Celite was washed with MeOH (3×3 mL) and concentrated in vacuo to give product, which was used crude in the next reaction. ESI+APCI MS m/z 512.3 [M+H]$^+$.

Step B: 2-((S)-1-acryloyl-4-(2-(((R)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile: Crude 2-((S)-4-(2-(((R)-1-methylpiperidin-2-yl)methoxy)-7-(naphthalen-1-yl)-5,6,7,8-tetrahydropyrido[3,4-d]pyrimidin-4-yl)piperazin-2-yl)acetonitrile (292 mg, 0.57068 mmol) was dissolved in DCM (10 mL) followed by addition of triethylamine (238.63 µl, 1.7120 mmol) and the solution cooled to −30° C. To the reaction was next added acryloyl chloride (92.728 µl, 1.1414 mmol) dropwise and the mixture stirred at −30° C. for 10 minutes. EtOH (0.1 mL) was next added and the reaction warmed to 0° C. The mixture was chromatographed directly on silica using 5% MeOH+0.5% NH₄OH/DCM as eluent followed by repurification of the material using the same eluent conditions to give title compound (EXAMPLE 432, 107.47 mg, 33%). ESI+APCI MS m/z 566.3 [M+H]⁺.

Example 433

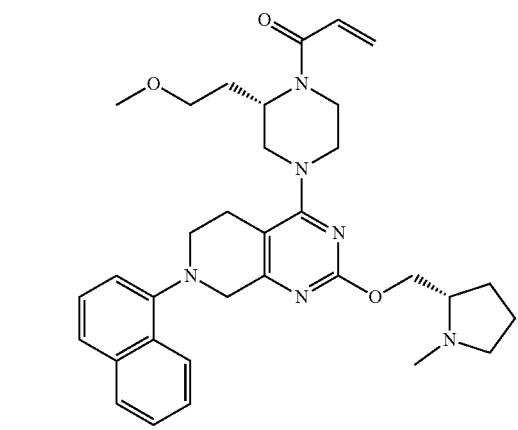 [SMILES: C=CC(=O)N1CCN(c2nc(OC[C@@H]3CCCN3C)nc3c2CCN(c2cccc4ccccc24)C3)C[C@@H]1CCOC]

1-((S)-2-(2-methoxyethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-1-yl)prop-2-en-1-one

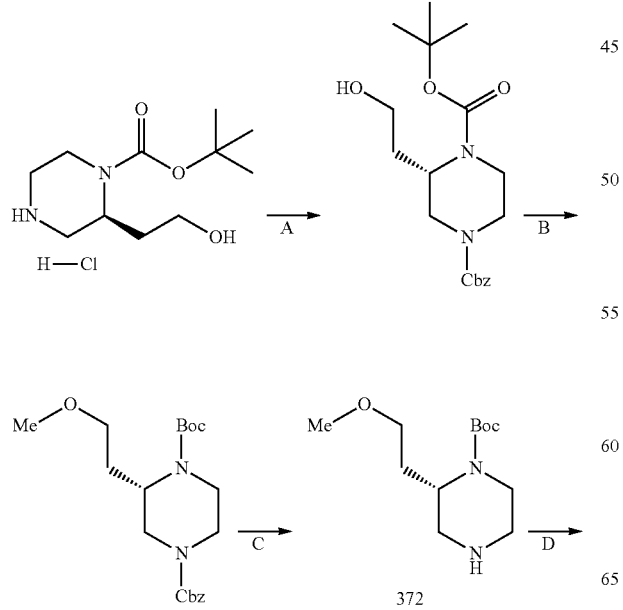

-continued

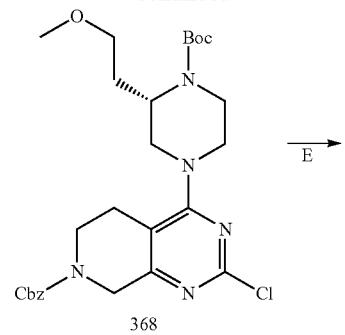

368

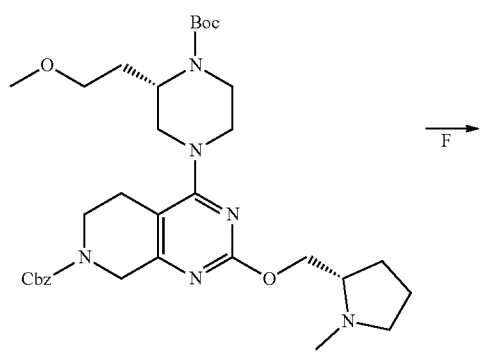

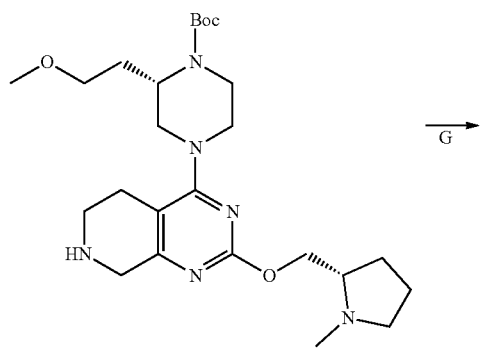

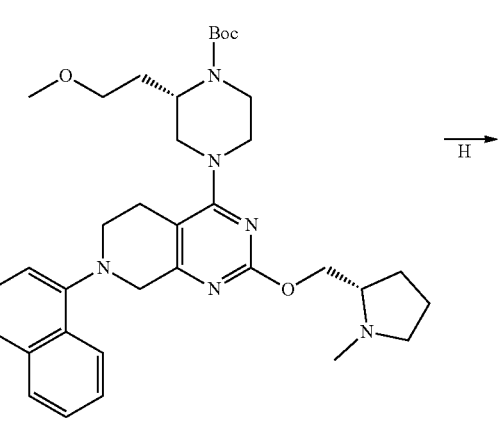

1151

-continued

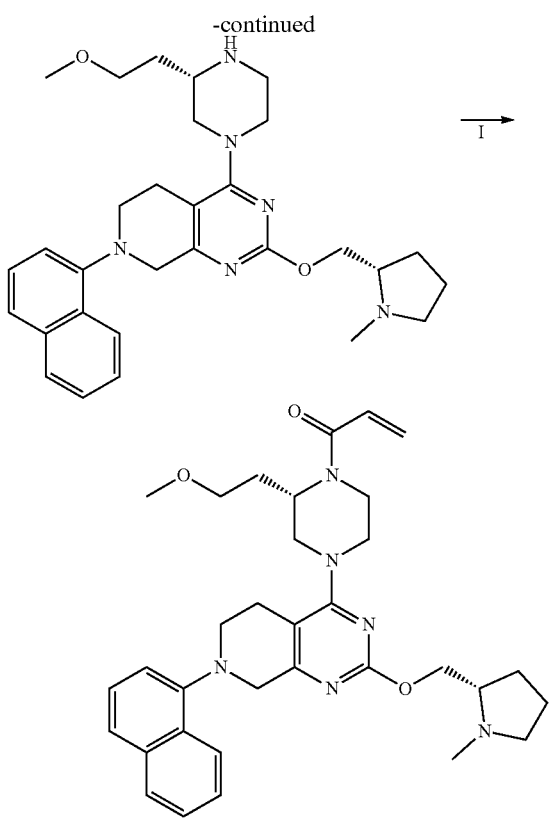

Step A: 4-benzyl 1-(tert-butyl) (S)-2-(2-hydroxy-ethyl)piperazine-1,4-dicarboxylate To a the solid (S)-tert-butyl-2-(2-hydroxyethyl)piperazine-1-carboxylate hydrochloride (500 mg, 1.874 mmol) and NaHCO₃ (629.8 mg, 7.497 mmol) were added EtOAc and water (10 mL each) and the mixture cooled to 0° C. followed by dropwise addition of benzyl carbonochloridate (0.4013 ml, 2.811 mmol) and the reaction mixture stirred overnight while warming to room temperature. The layers were next separated and the organic layer washed with water and brine (5 mL each), dried over Na₂SO₄ and concentrated in vacuo. The material was next chromatographed on silica gel using 20% to 40% EtOAc/hexane as eluent to give product (578 mg, 85%). ESI+APCI MS m/z 256.2 [M-Boc+H]⁺.

Step B: 4-benzyl 1-(tert-butyl) (S)-2-(2-methoxy-ethyl)piperazine-1,4-dicarboxylate A stirred solution of 4-benzyl 1-(tert-butyl) (S)-2-(2-hydroxyethyl)piperazine-1,4-dicarboxylate (270 mg, 0.741 mmol) in N,N-dimethylformamide (3 ml, 0.741 mmol) under N₂ was cooled to −20° C. followed by addition of sodium hydride (44.4 mg, 1.11 mmol) in one bolus. To the reaction was next added iodomethane (0.138 ml, 2.22 mmol) and the reaction mixture was warmed to r.t. over 1 hour and continued stirring for 1 hour at room temperature. The reaction was quenched by addition of ice (~5 g) and the mixture partitioned between MTBE (20 mL) and water (10 mL) and the layers separated. The organic layer was washed with water and brine (5 mL each), dried over Na₂SO₄ and concentrated in vacuo to give product which was used crude in the next reaction (252 mg, 90%). ESI+APCI MS m/z 279.1 [M-Boc+H]⁺.

1152

Step C: tert-butyl (S)-2-(2-methoxyethyl)piperazine-1-carboxylate

To a mixture of 4-benzyl 1-(tert-butyl) (S)-2-(2-methoxyethyl)piperazine-1,4-dicarboxylate (252 mg, 0.666 mmol) in methanol (5 ml) was added palladium on carbon (50 mg, 5%, Degussa type E101 NO/W) and the reaction degassed under vacuum and backfilled with hydrogen and the reaction stirred under hydrogen atmosphere for 3 hours. The slurry was filtered through Celite (2 mL) and the Celite washed with MeOH (3×3 mL). The combined organics were concentrated in vacuo and dried under high vacuum to give product (140 mg, 86%). ESI+APCI MS m/z 245.2 [M+H]⁺.

Step D: benzyl (S)-4-(4-(tert-butoxycarbonyl)-3-(2-methoxyethyl)piperazin-1-yl)-2-chloro-5,8-dihydro-pyrido[3,4-d]pyrimidine-7(6H)-carboxylate A solution of crude tert-butyl (S)-2-(2-methoxyethyl)piperazine-1-carboxylate (140 mg, 0.573 mmol) and N,N-dimethylacetamide (0.5 ml, 0.573 mmol) was cooled to 0° C. and benzyl 2,4-dichloro-5,6-dihydropyrido[3,4-d]pyrimidine-7(8H)-carboxylate (194 mg, 0.573 mmol) was added in one bolus. The reaction mixture was stirred overnight followed by addition of N-ethyl-N-isopropylpropan-2-amine (0.150 ml, 0.859 mmol) and the reaction stirred at room temperature for 1 hour. The reaction mixture was partitioned between MTBE (20 mL) and sat. NaHCO₃ (5 mL) and the layers separated. The organic layer was washed with water and brine (5 mL each), dried over Na₂SO₄ and concentrated in vacuo. The residue was chromatographed on silica gel using 2% MeOH/DCM as eluent to give product (190 mg, 61%).

Step E: benzyl 4-((S)-4-(tert-butoxycarbonyl)-3-(2-methoxyethyl)piperazin-1-yl)-2-(((S)-1-methylpyrrolidin-2-yl)methoxy)-5,8-dihydropyrido [3,4-d]pyrimidine-7(6H)-carboxylate A mixture of benzyl (S)-4-(4-(tert-butoxycarbonyl)-3-(2-methoxyethyl)piperazin-1-yl)-2-chloro-5,8-dihydropyrido [3,4-d]pyrimidine-7(6H)-carboxylate (190 mg, 0.348 mmol), (S)-(1-methylpyrrolidin-2-yl)methanol (120 mg, 1.04 mmol), Cs₂CO₃ (340 mg, 1.04 mmol) and 1,4-dioxane (0.5 ml) under N₂ atmosphere was heated to 120° C. for 20 hours. The reaction was cooled, diluted with EtOAc (3 mL), filtered through Celite and concentrated in vacuo. The residue was chromatographed on silica gel using 4 to 8% MeOH/DCM+0.4% NH₄OH as eluent to give product (77 mg, 35%). ESI+APCI MS m/z 625.3 [M+H]⁺.

Step F: tert-butyl (S)-2-(2-methoxyethyl)-4-(2-(((S)-1-methylpyrrolidin-2-yl)methoxy)-5,6,7,8-tetrahydropyrido[3,4-d]pyrimidin-4-yl)piperazine-1-carboxylate To a mixture of benzyl 4-((S)-4-(tert-butoxycarbonyl)-3-(2-methoxyethyl)piperazin-1-yl)-2-((S)-1-methylpyrrolidin-2-yl)methoxy)-5,8-dihydropyrido[3,4-d]pyrimidine-7(6H)-carboxylate (77 mg, 0.12 mmol) in methanol (5 ml) was added palladium on carbon (20 mg, 5%, Degussa type E101 NO/W) and the slurry degassed under vacuum and back filled with hydrogen and the reaction stirred under hydrogen atmosphere overnight. The slurry was filtered through Celite (2 mL) and the celite washed with MeOH (3×3 mL). The combined organics were concentrated in vacuo and azeotroped with toluene (2×2 mL) to give product which was used crude in the next reaction. ESI+APCI MS m/z 491.3 [M+H]⁺.

Step G: tert-butyl (S)-2-(2-methoxyethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate A mixture of crude tert-butyl (S)-2-(2-methoxyethyl)-4-(2-(((S)-1-methylpyrrolidin-2-yl)methoxy)-5,6,7,8-tetrahydropyrido[3,4-d]pyrimidin-4-yl)piperazine-1-carboxylate (60 mg, 0.122 mmol), $Cs_2CO_3$ (120 mg, 0.367 mmol), dioxane (2 mL), 1-iodonaphthalene (0.0268 ml, 0.183 mmol) (1.5 eq.) and methanesulfonato(2-dicyclohexylphosphino-2',6'-di-i-propoxy-1,1'-biphenyl)(2-amino-1,1'-biphenyl-2-yl)palladium(II) (RuPhos-Pd-G3, 0.1 eq., 10.2 mg, 0.0122 mmol) was purged with nitrogen and the reaction capped and stirred at 80° C. overnight. The reaction mixture was cooled, partitioned between EtOAc (20 mL) and water (10 mL) and the layers separated. The organic layer was washed with water and brine (5 mL each), dried over $Na_2SO_4$ and evaporated in vacuo. The residue was chromatographed on silica gel using 5% MeOH/DCM+0.5% $NH_4OH$ as eluent to give product (56 mg, 74%). ESI+APCI MS m/z 617.4 [M+H]⁺.

Step H: 4-((S)-3-(2-methoxyethyl)piperazin-1-yl)-2-((S)-1-methylpyrrolidin-2-yl)methoxy)-7-(naphthalen-1-yl)-5,6,7,8-tetrahydropyrido[3,4-d]pyrimidine To the solid tert-butyl (S)-2-(2-methoxyethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (56 mg, 0.091 mmol) was added hydrogen chloride (0.5 ml, 2.0 mmol) and the reaction stirred at 0° C. followed by warming to room temperature for 15 minutes, at which point a solid formed. The organics were decanted and the solids partitioned between DCM (12 mL) and 2M $Na_2CO_3$ (1 mL) and the layers separated. The organic layer was dried over $K_2CO_3$ and concentrated in vacuo to give crude product. ESI+APCI MS m/z 517.3 [M+H]⁺.

Step I: 1-((S)-2-(2-methoxyethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-1-yl)prop-2-en-1-one Crude 4-((S)-3-(2-methoxyethyl)piperazin-1-yl)-2-(((S)-1-methylpyrrolidin-2-yl)methoxy)-7-(naphthalen-1-yl)-5,6,7,8-tetrahydropyrido[3,4-d]pyrimidine (39 mg, 0.07548 mmol) was dissolved in DCM (10 mL) followed by addition of triethylamine (31.56 μl, 0.2264 mmol) and the solution cooled to −40° C. and stirred for 5 minutes followed by dropwise addition of acryloyl chloride (12.26 μl, 0.1510 mmol). The reaction mixture was stirred at −30° C. for 10 minutes followed by addition of MeOH (0.05 mL). The mixture was warmed up to 0° C. and the organics washed with 0.5M $Na_2CO_3$. The organic layer was evaporated in vacuo and chromatographed on silica gel using 5% MeOH+ 0.5% $NH_4OH$ in DCM as eluent to give title compound (EXAMPLE 433, 25.45 mg, 59%). ESI+APCI MS m/z 571.3 [M+H]⁺.

Example 434

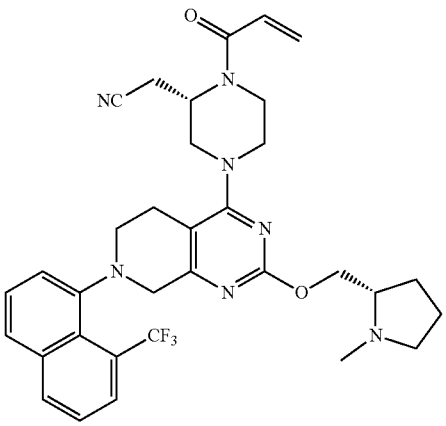 [SMILES: C=CC(=O)N1CCN(c2nc(OC[C@@H]3CCCN3C)nc3c2CCN(c2cccc4cccc(C(F)(F)F)c24)C3)C[C@@H]1CC#N]

2-((S)-1-acryloyl-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazin-2-yl)acetonitrile

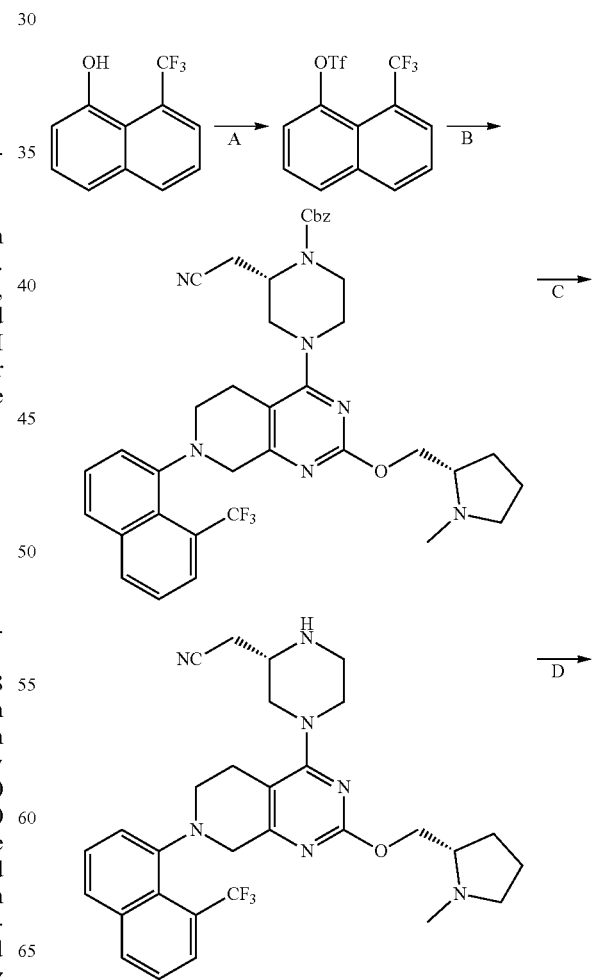

-continued

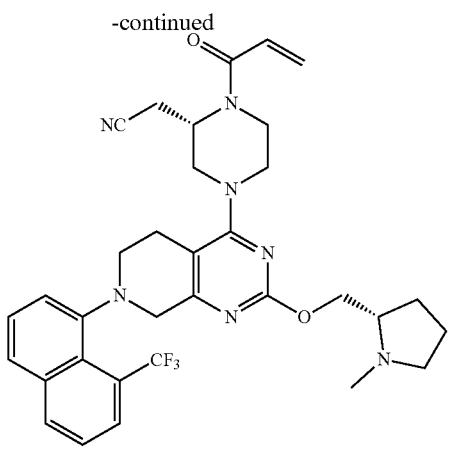

Step A: 8-(trifluoromethyl)naphthalen-1-yl trifluoromethanesulfonate

To a stirred solution of 8-(trifluoromethyl)naphthalen-1-ol (500 mg, 2.36 mmol) in DCM (10 mL) at 0° C. was added N-ethyl-N-isopropylpropan-2-amine (616 µl, 3.53 mmol) followed by dropwise addition of trifluoromethanesulfonic anhydride (475 µl, 2.83 mmol) and the reaction mixture stirred 1 hour while warming to room temperature. The reaction was next diluted with hexane (20 mL) and MTBE (5 mL) and the organics washed with sat. NaHCO$_3$, water and brine (5 mL each), dried over Na$_2$SO$_4$ and concentrated in vacuo. The residue was dissolved in 10% EtOAc/10% DCM in hexane and the material filtered through a silica gel plug. The organics were concentrated and chromatographed on silica gel using 5 to 10% EtOAc/hexane as eluent to give impure material. The solid was finally crystallized from hexane, and the solid washed with small amount of cold hexane to give product (482 mg, 59%).

Step B: benzyl (S)-2-(cyanomethyl)-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazine-1-carboxylate A mixture of crude benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (700 mg, 1.38 mmol), Cs$_2$CO$_3$ (1353 mg, 4.15 mmol), toluene (7 ml), methanesulfonato(2-dicyclohexylphosphino-2',6'-di-i-propoxy-1,1'-biphenyl)(2-amino-1,1'-biphenyl-2-yl)palladium(II) (RuPhos-Pd-G4, 0.1 eq., 116 mg, 0.138 mmol) and 8-(trifluoromethyl)naphthalen-1-yl trifluoromethanesulfonate (715 mg, 2.08 mmol) was purged with nitrogen and the reaction capped and stirred at 90° C. for 5 hours. The reaction mixture was cooled, partitioned between EtOAc (50 mL) and water (20 mL) and the layers separated. The organic layer was washed with water and brine (10 mL each), dried over Na$_2$SO$_4$ and evaporated in vacuo. The residue was chromatographed on silica gel using 4% MeOH/DCM+0.4% NH$_4$OH as eluent to give product (86 mg, 9%). ESI+APCI MS m/z 700.3 [M+H]$^+$.

Step C: 2-((S)-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazin-2-yl)acetonitrile A mixture of benzyl (S)-2-(cyanomethyl)-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazine-1-carboxylate (86 mg, 0.123 mmol), methanol (3 ml, 74.2 mmol) and palladium on carbon (30 mg, 5%, Degussa type E101 NO/W) was degassed under vacuum and backfilled with hydrogen and the reaction stirred under H$_2$ atmosphere for 1 hour. The reaction was next filtered through Celite (2 mL) and the Celite washed with MeOH (3×3 mL). The combined organics were concentrated in vacuo to give crude product (60 mg, 86%).

Step D: 2-((S)-1-acryloyl-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazin-2-yl)acetonitrile 2-((S)-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazin-2-yl)acetonitrile (50 mg, 0.08839 mmol) was dissolved in DCM (10 mL) followed by addition of triethylamine (36.96 µl, 0.2652 mmol) and the solution cooled to −40° C. and stirred for 5 minute followed by dropwise addition of acryloyl chloride (14.36 µl, 0.1768 mmol). The reaction mixture was stirred at −30° C. for 10 minutes followed by addition of 0.01 mL of acryloyl chloride. MeOH (0.05 mL) was next added to reaction and the mixture warmed to 0° C. The reaction was next washed with 0.5M Na$_2$CO$_3$ and the organics separated. The organics were evaporated in vacuo and chromatographed on silica gel using 5% MeOH+0.5% NH$_4$OH in DCM as eluent to give title compound (EXAMPLE 434, 39 mg, 71%).

Example 435

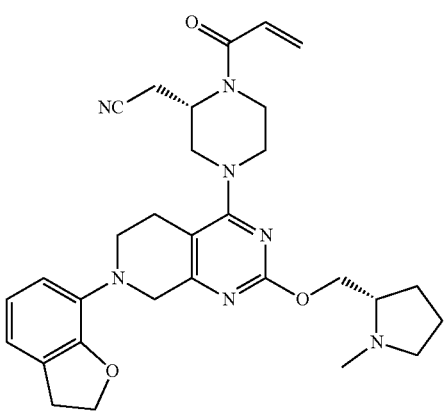 [SMILES: C=CC(=O)N1CCN(c2nc(OC[C@@H]3CCCN3C)nc3c2CCN(c2cccc4c2OCC4)C3)C[C@@H]1CC#N]

1157

2-((S)-1-acryloyl-4-(7-(2,3-dihydrobenzofuran-7-yl)-2-(((S)-1-methylpyrrolidin-2-yl)methoxy)-5,6,7,8-tetrahydropyrido[3,4-d]pyrimidin-4-yl)piperazin-2-yl)acetonitrile

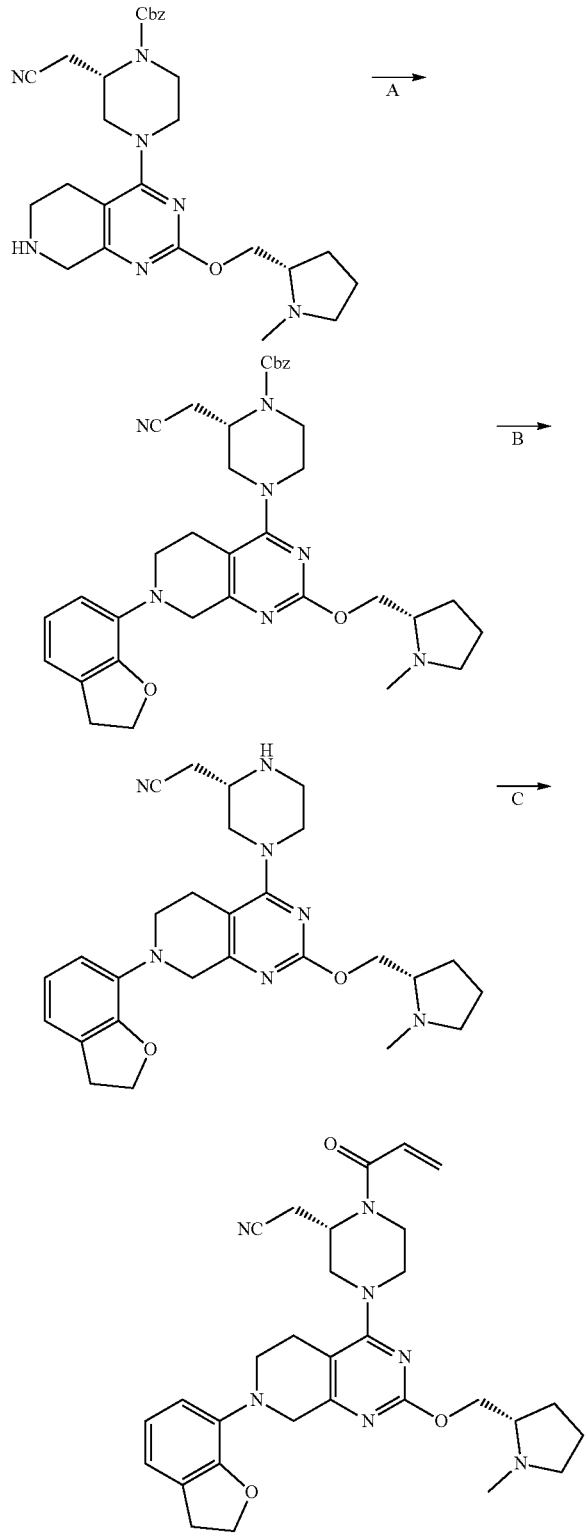

1158

Step A: benzyl (S)-2-(cyanomethyl)-4-(7-(2,3-dihydrobenzofuran-7-yl)-2-(((S)-1-methylpyrrolidin-2-yl)methoxy)-5,6,7,8-tetrahydropyrido[3,4-d]pyrimidin-4-yl)piperazine-1-carboxylate A mixture of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (200 mg, 0.396 mmol), $Cs_2CO_3$ (387 mg, 1.19 mmol), dioxane (0.5 mL), 7-bromo-2,3-dihydrobenzofuran (118 mg, 0.593 mmol, 1.5 eq.) and methanesulfonato(2-dicyclohexylphosphino-2',6'-di-i-propoxy-1,1'-biphenyl)(2'-methylamino-1,1'-biphenyl-2-yl)palladium(II) (RuPhos-Pd-G4, 0.1 eq., 33.7 mg, 0.0396 mmol) was purged with nitrogen, the reaction was capped and stirred at 80° C. overnight. The reaction mixture was cooled, partitioned between EtOAc (20 mL) and water (10 mL) and then the layers were separated. The organic layer was washed with water and brine (5 mL each), dried over $Na_2SO_4$ and evaporated in vacuo. The residue was chromatographed on silica gel using 4% MeOH/DCM+ 0.4% $NH_4OH$ as eluent to give product (97 mg, 39%). ESI+APCI MS m/z 624.3 [M+H]$^+$.

Step B: 2-((S)-4-(7-(2,3-dihydrobenzofuran-7-yl)-2-(((S)-1-methylpyrrolidin-2-yl)methoxy)-5,6,7,8-tetrahydropyrido[3,4-d]pyrimidin-4-yl)piperazin-2-yl)acetonitrile A mixture of benzyl (S)-2-(cyanomethyl)-4-(7-(2,3-dihydrobenzofuran-7-yl)-2-(((S)-1-methylpyrrolidin-2-yl)methoxy)-5,6,7,8-tetrahydropyrido[3,4-d]pyrimidin-4-yl)piperazine-1-carboxylate (97 mg, 0.16 mmol), methanol (4 ml), THF (4 mL) and palladium on carbon (30 mg, 5%, Degussa type E101 NO/W) was degassed under vacuum and backfilled with hydrogen and the reaction stirred under hydrogen atmosphere overnight. The residue was filtered through Celite (1 mL) and the celite was washed with MeOH (3×2 mL). The combined organics were evaporated in vacuo to give crude product. ESI+APCI MS m/z 490.3 [M+H]$^+$.

Step C: 2-((S)-1-acryloyl-4-(7-(2,3-dihydrobenzofuran-7-yl)-2-((S)-1-methylpyrrolidin-2-yl)methoxy)-5,6,7,8-tetrahydropyrido[3,4-d]pyrimidin-4-yl)piperazin-2-yl)acetonitrile A solution of 2-((S)-4-(7-(2,3-dihydrobenzofuran-7-yl)-2-(((S)-1-methylpyrrolidin-2-yl)methoxy)-5,6,7,8-tetrahydropyrido[3,4-d]pyrimidin-4-yl)piperazin-2-yl)acetonitrile (69 mg, 0.1409 mmol) in DCM (5 mL) was cooled to −30° C. with stirring. Triethylamine (58.93 μl, 0.4228 mmol) was added followed by addition of acryloyl chloride (22.90 μl, 0.2818 mmol) and the reaction stirred for 5 minutes at −30° C. The reaction was next quenched by addition of MeOH (0.05 mL) and the reaction warmed to room temperature. The organics were washed with 0.5M $Na_2CO_3$ (4 mL), dried over $K_2CO_3$ and evaporated in vacuo. The residue was chromatographed on silica gel in using 5% MeOH+0.5% $NH_4OH$ as eluent to give title compound (EXAMPLE 435, 45.85 mg, 60%). ESI+APCI MS m/z 544.3 [M+H]$^+$.

Example 436

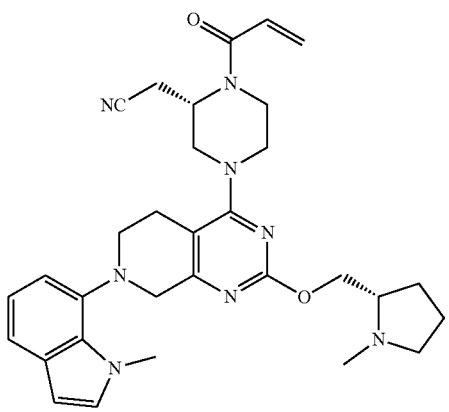 [SMILES: C=CC(=O)N1CCN(c2nc(OC[C@@H]3CCCN3C)nc3c2CCN(c2cccc4ccn(C)c24)C3)C[C@@H]1CC#N]

2-((S)-1-acryloyl-4-(7-(1-methyl-1H-indol-7-yl)-2-((S)-1-methylpyrrolidin-2-yl)methoxy)-5,6,7,8-tetrahydropyrido[3,4-d]pyrimidin-4-yl)piperazin-2-yl)acetonitrile

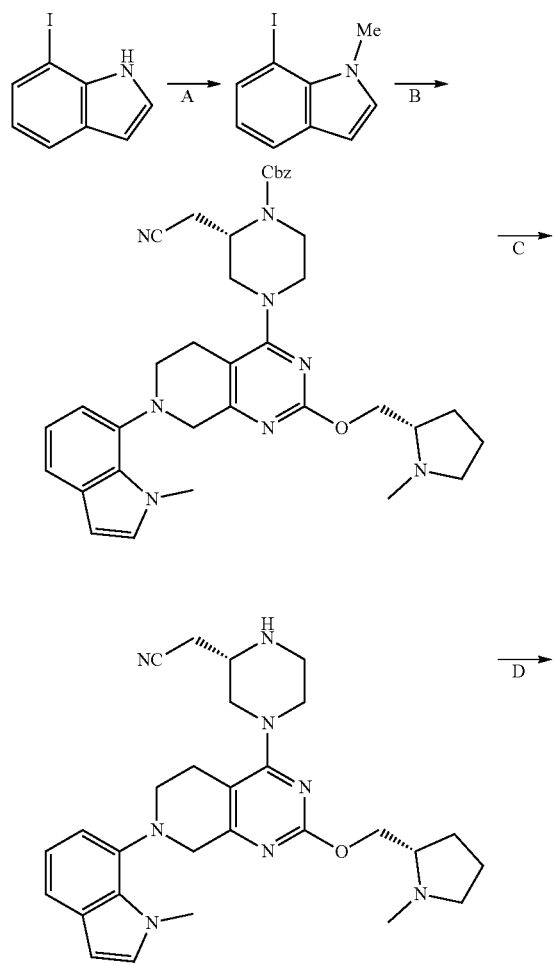

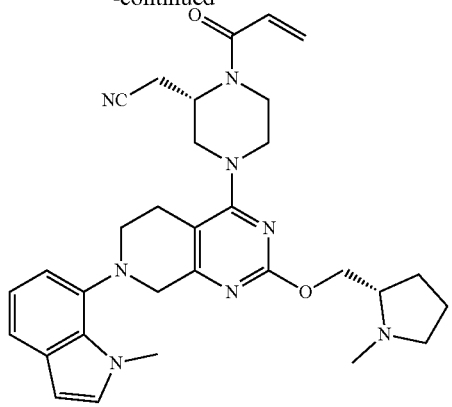

Step A: 7-iodo-1-methyl-1H-indole

A stirred solution of 7-iodo-1H-indole (4.11 ml, 2.06 mmol) in N,N-dimethylformamide (4 ml, 51.9 mmol) was cooled to −20° C. and sodium hydride (123 mg, 3.09 mmol) was added in small portions followed by addition of iodomethane (0.256 ml, 4.11 mmol) and the mixture was warmed to room temperature over a 2 hour period. The mixture was partitioned between MTBE (40 mL) and ice-water mixture (20 mL) and the layers separated. The organic layer was washed with water (2×20 mL), brine (10 mL), dried over $Na_2SO_4$ and evaporated in vacuo. The solid was washed with MTBE (1 mL). The solid was recrystallized from MTBE to give product (0.31 g, 59%).

Step B: benzyl (S)-2-(cyanomethyl)-4-(7-(1-methyl-1H-indol-7-yl)-2-(((S)-1-methylpyrrolidin-2-yl)methoxy)-5,6,7,8-tetrahydropyrido[3,4-d]pyrimidin-4-yl)piperazine-1-carboxylate A mixture of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (200 mg, 0.396 mmol), $Cs_2CO_3$ (387 mg, 1.19 mmol), dioxane (0.5 mL), 7-iodo-1-methyl-1H-indole (153 mg, 0.593 mmol) (1.5 eq.) and methanesulfonato (2-dicyclohexylphosphino-2',6'-di-i-propoxy-1,1'-biphenyl)(2'-methylamino-1,1'-biphenyl-2-yl)palladium(II) (RuPhos-Pd-G4, 0.1 eq., 33.7 mg, 0.0396 mmol) was purged with nitrogen and the reaction capped and stirred at 90° C. for 5 hours then overnight at 80° C. The reaction mixture was cooled, partitioned between EtOAc (20 mL) and water (10 mL) and the layers were separated. The organic layer was washed with water and brine (5 mL each), dried over $Na_2SO_4$ and evaporated in vacuo. The residue was chromatographed on silica gel using 4% MeOH/DCM+ 0.4% $NH_4OH$ as eluent to give product (65 mg, 26%). ESI+APCI MS m/z 635.3 $[M+H]^+$.

Step C: 2-((S)-4-(7-(1-methyl-1H-indol-7-yl)-2-(((S)-1-methylpyrrolidin-2-yl)methoxy)-5,6,7,8-tetrahydropyrido[3,4-d]pyrimidin-4-yl)piperazin-2-yl)acetonitrile A mixture of benzyl (S)-2-(cyanomethyl)-4-(7-(1-methyl-1H-indol-7-yl)-2-((S)-1-methylpyrrolidin-2-yl)methoxy)-5,6,7,8-tetrahydropyrido[3,4-d]pyrimidin-4-yl)piperazine-1-carboxylate (65 mg, 0.10 mmol), methanol (6 ml), and palladium on carbon (30 mg, 5%, Degussa type E101

NO/W) was degassed with vacuum and back filled with hydrogen and the mixture stirred under a hydrogen atmosphere overnight. The slurry was filtered through Celite (1 mL) and the Celite washed with MeOH (3×2 mL). The combined organics were evaporated in vacuo to give crude product. ESI+APCI MS m/z 501.3 [M+H]⁺.

Step D: 2-((S)-1-acryloyl-4-(7-(1-methyl-1H-indol-7-yl)-2-(((S)-1-methylpyrrolidin-2-yl)methoxy)-5,6,7,8-tetrahydropyrido[3,4-d]pyrimidin-4-yl)piperazin-2-yl)acetonitrile A solution of 2-((S)-4-(7-(1-methyl-1H-indol-7-yl)-2-((S)-1-methylpyrrolidin-2-yl)methoxy)-5,6,7,8-tetrahydropyrido[3,4-d]pyrimidin-4-yl)piperazin-2-yl)acetonitrile (51 mg, 0.1019 mmol) in DCM (5 mL) was cooled to −30° C. with stirring followed by addition of triethylamine (42.60 µl, 0.3056 mmol) and acryloyl chloride (16.55 µl, 0.2037 mmol). After stirring at 5 minutes at −30° C., the reaction mixture was quenched with MeOH (0.05 mL) and warmed to room temperature. The organics were washed with 0.5M Na₂CO₃ (4 mL), dried over K₂CO₃ and evaporated in vacuo. The residue was chromatographed on silica gel using 5% MeOH+0.5% NH₄OH as eluent to give title compound (EXAMPLE 436, 36 mg, 64%). ESI+APCI MS m/z 555.3 [M+H]⁺.

Example 437

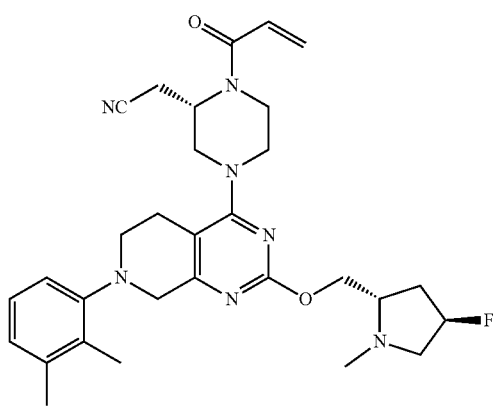 [SMILES: C=CC(=O)N1CCN(c2nc(OC[C@@H]3C[C@@H](F)CN3C)nc3c2CCN(c2cccc(C)c2C)C3)C[C@@H]1CC#N]

2-((S)-1-acryloyl-4-(7-(2,3-dimethylphenyl)-2-(((2S,4R)-4-fluoro-1-methylpyrrolidin-2-yl)methoxy)-5,6,7,8-tetrahydropyrido[3,4-d]pyrimidin-4-yl)piperazin-2-yl)acetonitrile

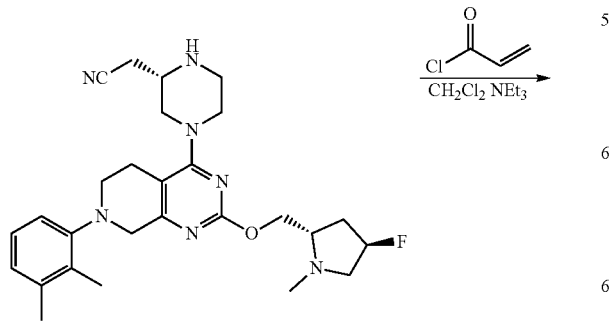

-continued

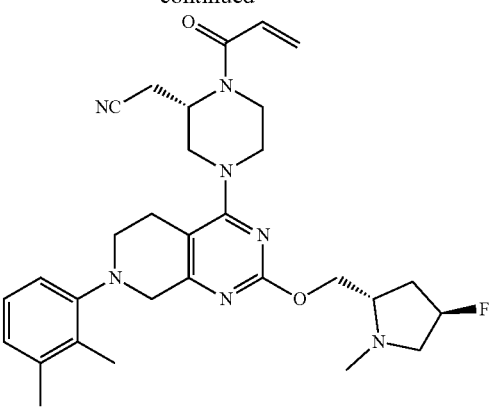

Step A: 2-((S)-1-acryloyl-4-(7-(2,3-dimethylphenyl)-2-(((2S,4R)-4-fluoro-1-methylpyrrolidin-2-yl)methoxy)-5,6,7,8-tetrahydropyrido[3,4-d]pyrimidin-4-yl)piperazin-2-yl)acetonitrile A solution of 2-((S)-4-(7-(2,3-dimethylphenyl)-2-(((2S,4R)-4-fluoro-1-methylpyrrolidin-2-yl)methoxy)-5,6,7,8-tetrahydropyrido[3,4-d]pyrimidin-4-yl)piperazin-2-yl)acetonitrile (50 mg, 0.1013 mmol) in DCM (5 mL) was cooled to −30° C. followed by addition of triethylamine (42.35 µl, 0.3039 mmol) and acryloyl chloride (16.46 µl, 0.2026 mmol). After stirring 5 minutes at −30° C. the reaction mixture was quenched with MeOH (0.05 mL) and warmed to room temperature. The organics were washed with 0.5M Na₂CO₃ (4 mL), dried over K₂CO₃ and evaporated in vacuo. The residue was chromatographed on silica gel using 4% MeOH+0.4% NH₄OH as eluent to give title compound (EXAMPLE 437, 34 mg, 61%). ESI+APCI MS m/z 548.3 [M+H]⁺.

Example 438

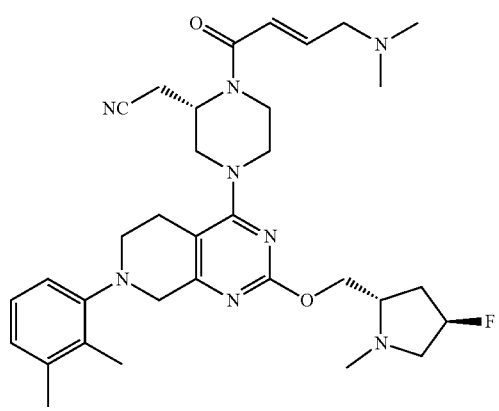 [SMILES: Cc1cccc(N2CCc3c(nc(OC[C@@H]4C[C@@H](F)CN4C)nc3N3CCN(C(=O)/C=C/CN(C)C)[C@@H](CC#N)C3)C2)c1C]

1163

2-((S)-1-((E)-4-(dimethylamino)but-2-enoyl)-4-(7-(2,3-dimethylphenyl)-2-(((2S,4R)-4-fluoro-1-methylpyrrolidin-2-yl)methoxy)-5,6,7,8-tetrahydropyrido[3,4-d]pyrimidin-4-yl)piperazin-2-yl)acetonitrile

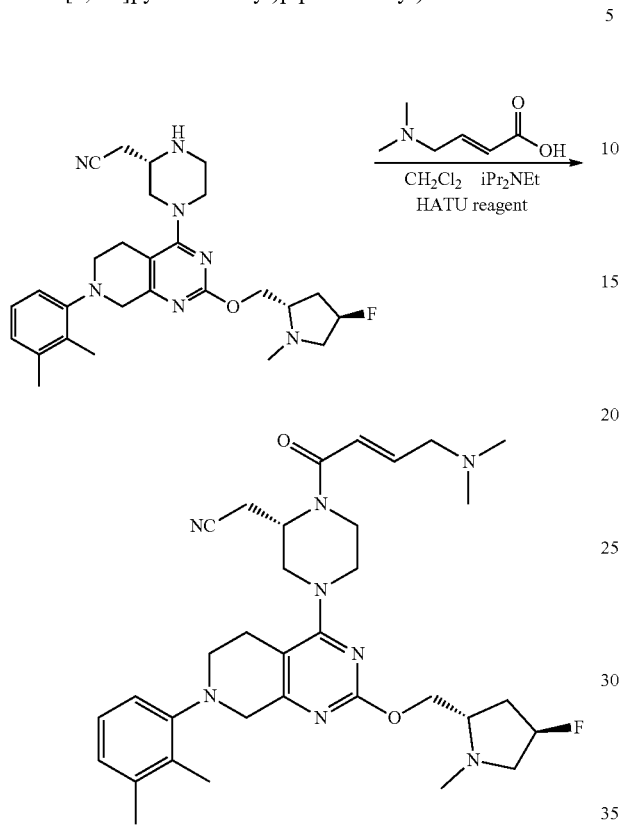

Step A: 2-((S)-1-((E)-4-(dimethylamino)but-2-enoyl)-4-(7-(2,3-dimethylphenyl)-2-(((2S,4R)-4-fluoro-1-methylpyrrolidin-2-yl)methoxy)-5,6,7,8-tetrahydropyrido[3,4-d]pyrimidin-4-yl)piperazin-2-yl)acetonitrile To a stirred solution of 2-((S)-4-(7-(2,3-dimethylphenyl)-2-(((2S,4R)-4-fluoro-1-methylpyrrolidin-2-yl)methoxy)-5,6,7,8-tetrahydropyrido[3,4-d]pyrimidin-4-yl)piperazin-2-yl)acetonitrile (50 mg, 0.1013 mmol) in DCM (1 mL) was added (2E)-4-(Dimethylamino)but-2-enoic acid (26.17 mg, 0.2026 mmol), N-ethyl-N-isopropylpropan-2-amine (0.03529 ml, 0.2026 mmol) and O-(7-azabenzotriazol-1-yl)-N,N,N',N'-tetramethyluronium hexafluorophosphate (57.77 mg, 0.1519 mmol) and the reaction mixture stirred at room temperature for 4 hours. Water (1 mL) was next added and the reaction mixture stirred for 5 minutes. The mixture was partitioned between EtOAc (10 mL) and sat. NaHCO₃ (5 mL) and the layers separated. The organic layer was washed with NaHCO₃, brine, dried over K₂CO₃ and evaporated in vacuo. The residue was chromatographed on silica gel using 5% MeOH+0.5% NH₄OH as eluent to give title compound (EXAMPLE 438, 45 mg, 74%). ESI+APCI MS m/z 605.3 [M+H]⁺.

1164

Example 439

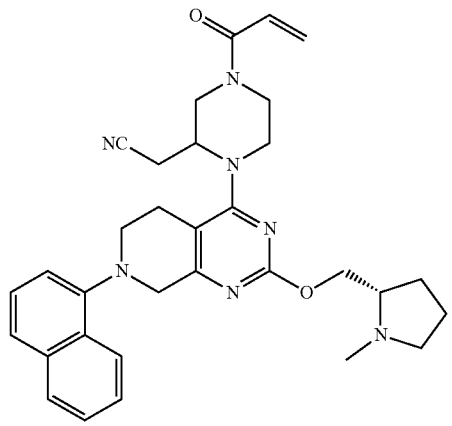 [SMILES: C=CC(=O)N1CCN(c2nc(OC[C@@H]3CCCN3C)nc3c2CCN(c2cccc4ccccc24)C3)C(CC#N)C1]

2-(4-acryloyl-1-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

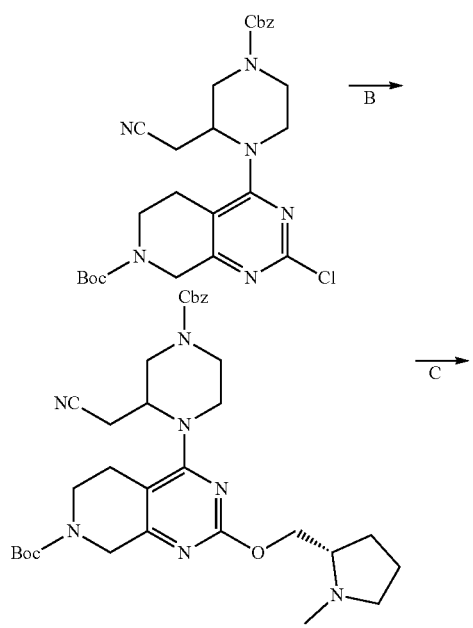

-continued

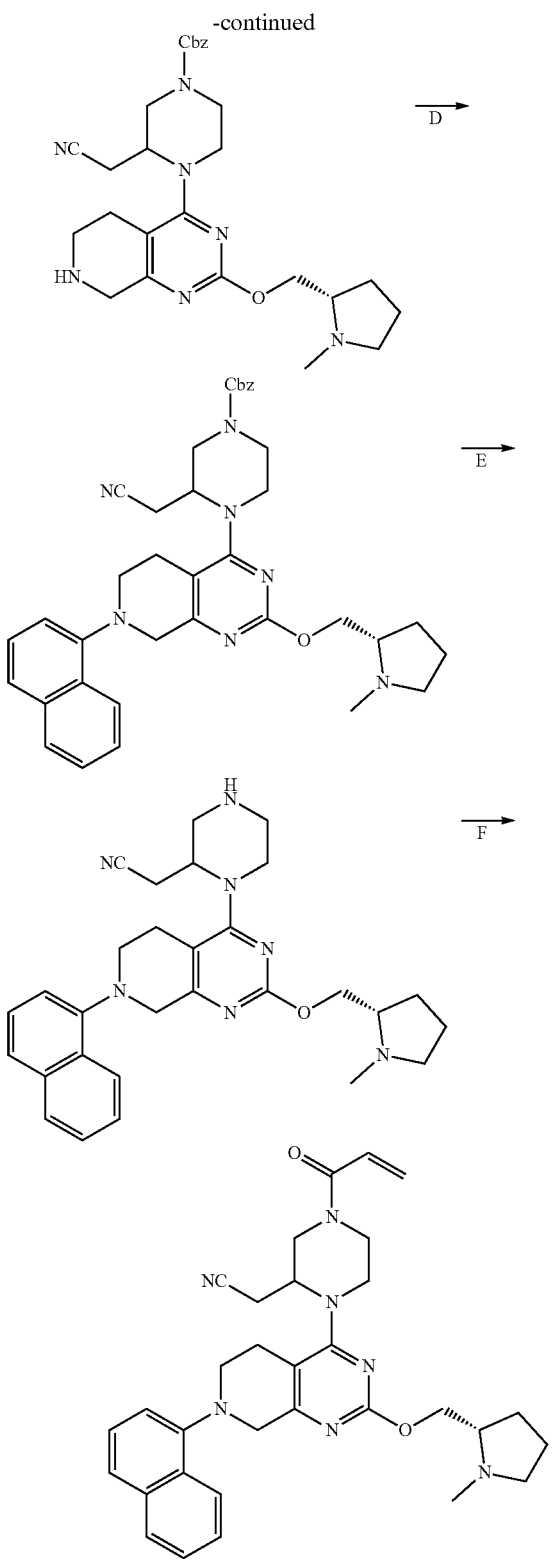

Step A: tert-butyl 4-(4-((benzyloxy)carbonyl)-2-(cyanomethyl)piperazin-1-yl)-2-chloro-5,8-dihydropyrido[3,4-d]pyrimidine-7(6H)-carboxylate A stirred solution of 2-(piperazin-2-yl)acetonitrile (0.2 g, 1.278 mmol) in a mixture of DCM (20 mL) and iPrOH (10 mL) was cooled to −30° C. and benzyl carbonochloridate (0.2190 ml, 1.534 mmol) was added dropwise and the reaction stirred for 1 hour while warming to room temperature. The organics were evaporated under the slow flow of $N_2$. The residue was dissolved in N,N-dimethylacetamide (1 ml, 1.278 mmol) followed by addition of N-ethyl-N-isopropylpropan-2-amine (0.3340 ml, 1.917 mmol) and tert-butyl 2,4-dichloro-5,8-dihydropyrido[3,4-d]pyrimidine-7(6H)-carboxylate (0.3888 g, 1.278 mmol). The reaction mixture was heated to 70° C. for 2 hours followed by stirring at room temperature for 4 days. The reaction was partitioned between water (5 mL) and MTBE (20 mL) and the layers were separated. The organics were washed with water and brine (5 mL each), dried over $Na_2SO_4$ and evaporated in vacuo. The residue was chromatographed on silica gel using 40 to 100% EtOAc/hexane as eluent to give product (134 mg, 20%). ESI+APCI MS m/z 527.2 [M+H]$^+$.

Step B: tert-butyl 4-(4-((benzyloxy)carbonyl)-2-(cyanomethyl)piperazin-1-yl)-2-(((S)-1-methylpyrrolidin-2-yl)methoxy)-5,8-dihydropyrido[3,4-d]pyrimidine-7(6H)-carboxylate A mixture of tert-butyl 4-(4-((benzyloxy)carbonyl)-2-(cyanomethyl)piperazin-1-yl)-2-chloro-5,8-dihydropyrido[3,4-d]pyrimidine-7(6H)-carboxylate (134 mg, 0.254 mmol), $Cs_2CO_3$ (249 mg, 0.763 mmol), methanesulfonato(2-dicyclohexylphosphino-2',6'-di-i-propoxy-1,1'-biphenyl)(2'-methylamino-1,1'-biphenyl-2-yl)palladium(II) (21.6 mg, 0.0254 mmol), (S)-(1-methylpyrrolidin-2-yl)methanol (146 mg, 1.27 mmol) and 1,4-dioxane (2 ml, 0.254 mmol) was purged with $N_2$, the reaction capped and stirred at 80° C. for 3 hours. The reaction mixture was cooled, partitioned between EtOAc (20 mL) and water (5 mL) and the layers were separated. The organics were washed with brine (5 mL), dried over $Na_2SO_4$ and evaporated in vacuo. The residue was chromatographed on silica gel using 4% MeOH+0.4% $NH_4OH$/DCM as eluent to give product (60 mg, 39%). ESI+APCI MS m/z 606.3 [M+H]$^+$.

Step C: benzyl 3-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate Neat (tert-butyl 4-(4-((benzyloxy)carbonyl)-2-(cyanomethyl)piperazin-1-yl)-2-(((S)-1-methylpyrrolidin-2-yl)methoxy)-5,8-dihydropyrido[3,4-d]pyrimidine-7(6H)-carboxylate (60 mg, 0.09905 mmol)) was diluted with DCM (0.2 mL). The reaction was cooled to 0° C. and 4M HCl in dioxane (0.50 mL, 20 eq) was added with stirring. The reaction mixture was warmed to room temperature and left in a fridge overnight, at which point a solid precipitated. The liquid phase was decanted and the solid partitioned between DCM (10 mL) and 2M $Na_2CO_3$ (0.5 mL) and the layers were separated. The organics were dried over $K_2CO_3$ and evaporated under $N_2$ flow. The product was used crude in the next reaction.

Step D: benzyl 3-(cyanomethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate A mixture of crude benzyl 3-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (50 mg, 0.0989 mmol), $Cs_2CO_3$ (96.7 mg, 0.297 mmol), dioxane (0.5 mL), 1-iodonaphthalene (37.7 mg, 0.148 mmol, 1.5 eq.) and methanesulfonato(2-dicyclohexylphosphino-2',6'-di-i-propoxy-1,1'-biphenyl)(2'-methylamino-1,1'-biphenyl-2-yl)palladium(II) (RuPhos-Pd-G4, 0.1 eq., 8.42 mg, 0.00989 mmol) was purged with nitrogen and the reaction capped and stirred at 80° C. for 2 hours. The reaction mixture was cooled and partitioned between EtOAc (20 mL) and water (5 mL) and the layers separated. The organics were washed with water and brine (5 mL each), dried over Na$_2$SO$_4$ and evaporated in vacuo. The residue was chromatographed on silica using 4% MeOH/DCM+0.4% NH$_4$OH as eluent to give impure product, which was purified by reversed prep HPLC chromatogaphy eluting with 5 to 95% MeCN/water+ 0.1% TFA (first eluted compound). The target fractions were diluted with 2M Na$_2$CO$_3$ and the aqueous later extracted with DCM (3×20 mL). The combined extracts were washed with brine (15 mL), dried over K$_2$CO$_3$ and evaporated in vacuo to afford product (26 mg, 42%). ESI+APCI MS m/z 632.3 [M+H]$^+$.

Step E: 2-(1-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile A mixture of benzyl 3-(cyanomethyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (26 mg, 0.041 mmol), methanol (2 ml), and palladium on carbon (10 mg, 5%, Degussa type E101 NO/W) was degassed under vacuum and backfilled with hydrogen and the reaction stirred under a hydrogen atmosphere for 1.5 hour. The reaction was filtered through Celite (2 mL) and the Celite washed with MeOH (3×3 mL). The combined organics were evaporated in vacuo to give product which was used crude in the next reaction. ESI+APCI MS m/z 498.3 [M+H]$^+$.

Step F: 2-(4-acryloyl-1-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile A solution of 2-(1-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (15 mg, 0.03014 mmol) in DCM (5 mL) was cooled to −30° C. with stirring followed by addition of triethylamine (12.60 µl, 0.09043 mmol) and acryloyl chloride (4.898 µl, 0.06028 mmol). After stirring 5 minutes at −30° C., the reaction mixture was quenched by addition of MeOH (0.05 mL) and warmed up to room temperature. The organics were washed with 0.5M Na$_2$CO$_3$ (4 mL), dried over Na$_2$CO$_3$ and evaporated in vacuo. The residue was chromatographed on silica gel using 4% MeOH+0.4% NH$_4$OH as eluent to give title compound (EXAMPLE 439, 8.43 mg, 51%). ESI+APCI MS m/z 552.2 [M+H]$^+$.

Example 440

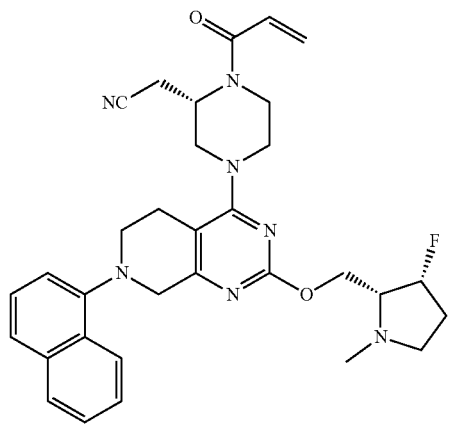 [SMILES: C=CC(=O)N1CCN(c2nc(OC[C@@H]3[C@H](F)CCN3C)nc3c2CCN(c2cccc4ccccc24)C3)C[C@@H]1CC#N]

2-((S)-1-acryloyl-4-(2-(((2R,3R)-3-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

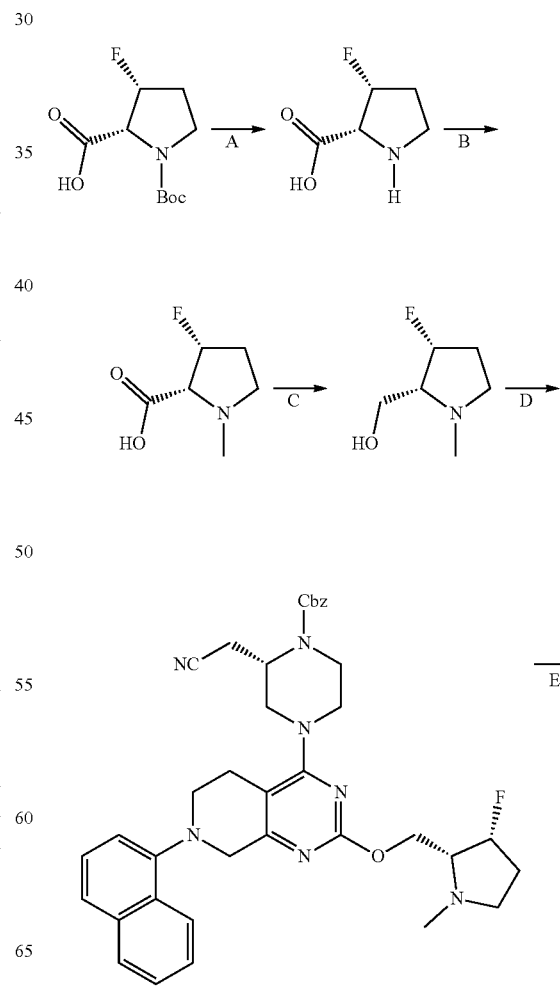

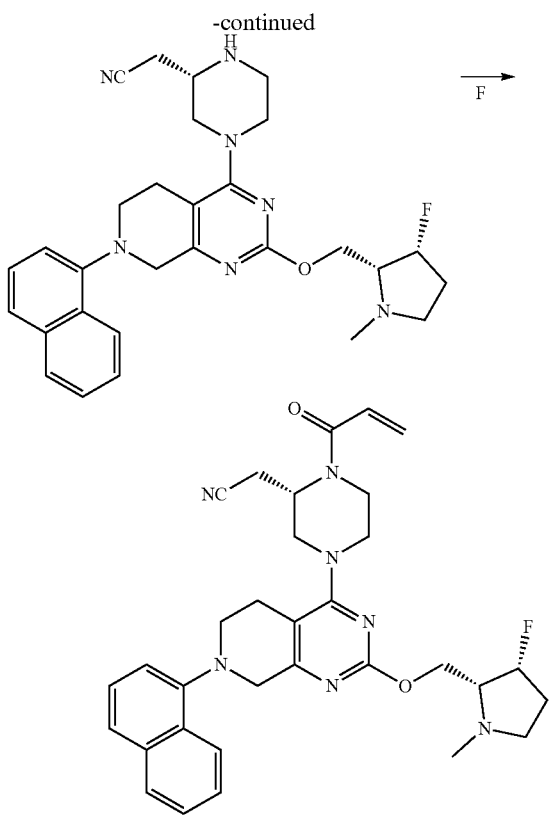

Step A: (2R,3R)-3-fluoropyrrolidine-2-carboxylic acid

To the solid (2R,3R)-1-Boc-3-fluoropyrrolidine-carboxylic acid (400 mg, 1.71 mmol) was added 4M hydrogen chloride (2144 μl, 8.57 mmol) dropwise and the reaction mixture stirred at room temperature for 1.5 hours. The reaction mixture was evaporated in vacuo followed by addition of solid NaHCO$_3$ (173 mg, 2.06 mmol) and methanol (1715 μl, 1.71 mmol) and the suspension stirred at room temperature overnight. To the mixture was added an additional portion of MeOH (10 mL) and the reaction mixture stirred for 30 minutes and was sonicated until full dispersion of semi-solids was achieved. This slurry was used crude in the next reaction.

Step B: (2R,3R)-3-fluoro-1-methylpyrrolidine-2-carboxylic acid

To a stirred suspension of crude (2R,3R)-3-fluoropyrrolidine-2-carboxylic acid (228 mg, 1.71 mmol) in MeOH (12 mL) was added palladium on carbon (30 mg, 5%, Degussa type E101 NO/W) followed by addition of aqueous formaldehyde (159 μl, 2.14 mmol) and the reaction mixture was degassed with hydrogen and stirred under hydrogen overnight. The reaction mixture was filtered through Celite and the Celite was washed with MeOH (3×2 mL). The combined organics were evaporated in vacuo. The semi-solid was taken up in dioxan and evaporated under N$_2$ over weekend. The product was used crude in the next reaction.

Step C: ((2R,3R)-3-fluoro-1-methylpyrrolidin-2-yl)methanol

A stirred suspension of crude 1-Boc-2-(S)-Pyrrolidinedicarboxylic acid, 3-(R)-fluoro-(252 mg, 1.71 mmol) in THF under nitrogen was cooled on to 0° C. followed by dropwise addition of 2.4M lithium aluminium hydride (0.999 ml, 2.40 mmol) and the reaction stirred for 30 minutes while warming to room temperature. The reaction was sonicated followed by addition of another portion of lithium aluminium hydride in THF (0.999 ml, 2.40 mmol) and the reaction mixture was stirred at room temperature. The slurry was cooled on to 0° C. and quenched with successive addition of water (0.18 mL), 15% NaOH (0.18 mL) and water (0.54 mL). The slurry was diluted with ether (20 mL) and the precipitate separated. The reaction mixture was filtered through Celite and the Celite washed with ether (3×3 mL). To the combined organics was added 4M HCl/dioxane (0.45 mL, 1.1 eq.). The mixture turned from a colorless suspension into a reddish precipitate. The supernatant solution was evaporated in vacuo. The residual red solid was extracted with a minimal amount of water, filtered through a cotton plug and the cotton plug was washed with a small amount of water. The combined water solution was saturated with KOH and extracted with ether (3×7 mL). The combined extracts were dried over NaOH and evaporated partially under nitrogen to give product as a solution in ether (340 mg as 40% solution in ether, 60%)

Step D: benzyl (S)-2-(cyanomethyl)-4-(2-(((2R,3R)-3-fluoro-1-methylpyrrolidin-2-yl)methoxy)-7-(naphthalen-1-yl)-5,6,7,8-tetrahydropyrido[3,4-d]pyrimidin-4-yl)piperazine-1-carboxylate A mixture of benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (150 mg, 0.2712 mmol), Cs$_2$CO$_3$ (265.1 mg, 0.8137 mmol), 1,4-dioxane (1 ml), methanesulfonato(2-dicyclohexylphosphino-2',6'-di-i-propoxy-1,1'-biphenyl)(2'-methylamino-1,1'-biphenyl-2-yl)palladium(II) (23.09 mg, 0.02712 mmol) and RuPhos (9.492 mg, 0.02034 mmol) was degassed with nitrogen and stirred at 70° C. for 1.5 hours. The reaction mixture was cooled and partitioned between EtOAc (20 mL) and water (5 mL) and the layers were separated. The organics were washed with water and brine (5 mL each), dried over Na$_2$SO$_4$ and evaporated in vacuo. The residue was chromatographed on silica gel using 3% MeOH+0.3% NH$_4$OH in DCM as eluent to give product (108 mg, 61%). ESI+APCI MS m/z 650.3 [M+H]$^+$.

Step E: 2-((S)-4-(2-(((2R,3R)-3-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile A mixture of benzyl (S)-2-(cyanomethyl)-4-(2-(((2R,3R)-3-fluoro-1-methylpyrrolidin-2-yl)methoxy)-7-(naphthalen-1-yl)-5,6,7,8-tetrahydropyrido[3,4-d]pyrimidin-4-yl)piperazine-1-carboxylate (108 mg, 0.166 mmol), methanol (5 ml), and palladium on carbon (35 mg, 5%, Degussa type E101 NO/W) was degassed under vacuum and backfilled with hydrogen and the reaction stirred under hydrogen atmosphere for 1.5 hours. The reaction mixture was filtered through Celite (2 mL) and the celite was washed with MeOH (3×3 mL). The combined organics were evaporated in vacuo to give the crude product which was used in the next reaction.

Step F: 2-((S)-1-acryloyl-4-(2-(((2R,3R)-3-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile A solution of 2-((S)-4-(2-(((2R,3R)-3-fluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (78 mg, 0.1513 mmol) in DCM (5 mL) was cooled to −30° C. followed by addition of triethylamine (63.25 µl, 0.4538 mmol) and acryloyl chloride (24.58 µl, 0.3025 mmol). After stirring 5 minutes at −30° C., the reaction mixture was quenched with MeOH (0.05 mL) and warmed to room temperature. The mixture was washed with 0.5M Na₂CO₃ (4 mL), dried over Na₂CO₃ and evaporated in vacuo. The residue was chromatographed on silica gel using 4% to 10% MeOH eluent to give title compound (EXAMPLE 440, 63 mg, 73%). ESI+APCI MS m/z 570.3 [M+H]⁺.

Example 441

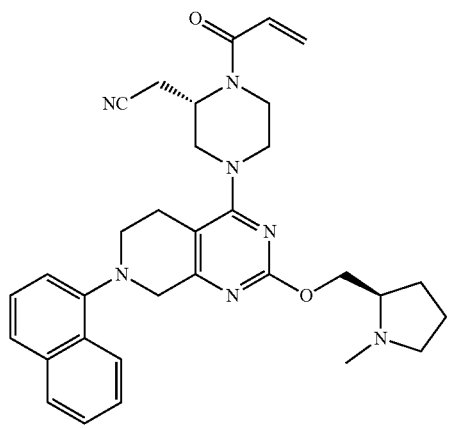 [SMILES: C=CC(=O)N1CCN(c2nc(OC[C@H]3CCCN3C)nc3c2CCN(c2cccc4ccccc24)C3)C[C@@H]1CC#N]

2-((S)-1-acryloyl-4-(2-(((R)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

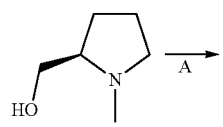

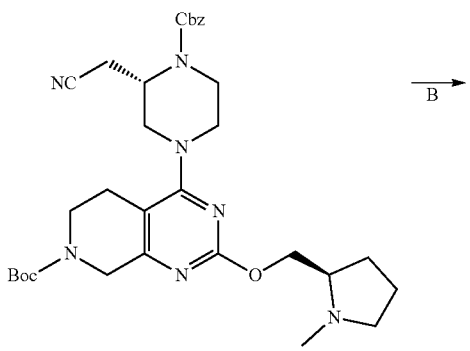

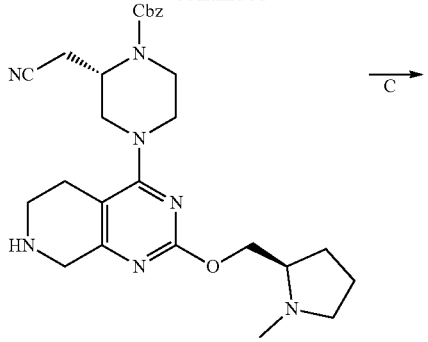

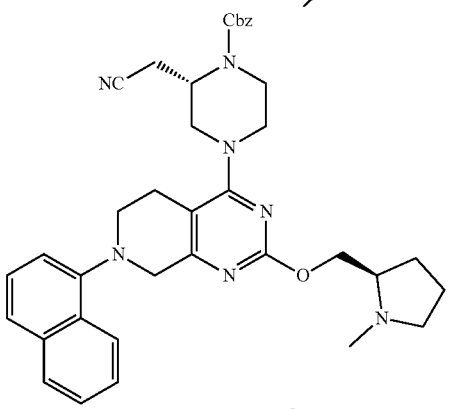

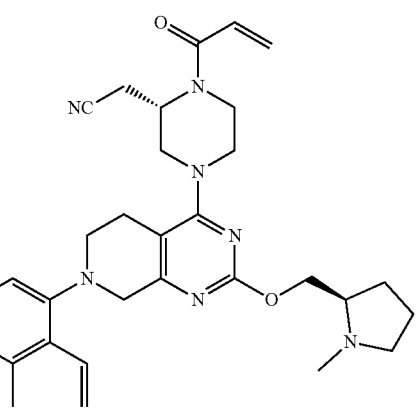

Step A: tert-butyl 4-((S)-4-((benzyloxy)carbonyl)-3-(cyanomethyl)piperazin-1-yl)-2-(((R)-1-methylpyrrolidin-2-yl)methoxy)-5,8-dihydropyrido[3,4-d]pyrimidine-7(6H)-carboxylate A mixture of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (500 mg, 0.949 mmol), (D)-(R)-(1-methylpyrrolidin-2-yl)methanol (328 mg, 2.85 mmol)(3 eq.), Cs₂CO₃ (927 mg, 2.85 mmol), dioxane (1 mL) and methanesulfonato(2-dicyclohexylphosphino-2',6'-di-i-propoxy-1,1'-biphenyl)(2-amino-1,1'-biphenyl-2-yl)palladium(II) (RuPhos-Pd-G3, 0.1 eq., 79.3 mg, 0.0949 mmol) was purged with nitrogen and the reaction was capped and stirred at 70° C. for 5 hours. The reaction mixture was cooled, partitioned between EtOAc (20 mL) and water (10 mL) and the layers were separated. The organics were washed with water and brine (5 mL each), dried over Na₂SO₄ and evaporated in vacuo. The residue was chromatographed on silica gel using 4 to 10% MeOH+

0.5% NH₄OH as eluent to give product (150 mg, 26%). ESI+APCI MS m/z 606.3 [M+H]⁺.

Step B: benzyl (S)-2-(cyanomethyl)-4-(2-(((R)-1-methylpyrrolidin-2-yl)methoxy)-5,6,7,8-tetrahydropyrido[3,4-d]pyrimidin-4-yl)piperazine-1-carboxylate A solution of tert-butyl 4-((S)-4-((benzyloxy)carbonyl)-3-(cyanomethyl)piperazin-1-yl)-2-(((R)-1-methylpyrrolidin-2-yl)methoxy)-5,8-dihydropyrido[3,4-d]pyrimidine-7(6H)-carboxylate (296 mg, 0.489 mmol) in DCM (2.5 mL) was cooled on dry ice followed by addition of 4M HCl in dioxane (1.2 mL) and the reaction stirred for 3 hours while warming to room temperature, at which point a precipitate formed. The liquid layer was decanted and the precipitate was washed with DCM (2 mL). The solid was then stirred with a mixture of DCM (20 mL) and 2M Na₂CO₃ (3 mL) for 1 hour. The layers were separated and the organics was dried over Na₂CO₃, filtered and evaporated in vacuo. The material was used crude in the next reaction. ESI+APCI MS m/z 506.3 [M+H]⁺.

Step C: benzyl (S)-2-(cyanomethyl)-4-(2-(((R)-1-methylpyrrolidin-2-yl)methoxy)-7-(naphthalen-1-yl)-5,6,7,8-tetrahydropyrido[3,4-d]pyrimidin-4-yl)piperazine-1-carboxylate A mixture of crude benzyl (S)-2-(cyanomethyl)-4-(2-(((R)-1-methylpyrrolidin-2-yl)methoxy)-5,6,7,8-tetrahydropyrido[3,4-d]pyrimidin-4-yl)piperazine-1-carboxylate (247 mg, 0.489 mmol), Cs₂CO₃ (477 mg, 1.47 mmol), dioxane (2 mL), 1-iodonaphthalene (107 µl, 0.733 mmol, 1.5 eq.) and methanesulfonato(2-dicyclohexylphosphino-2',6'-di-i-propoxy-1,1'-biphenyl)(2-amino-1,1'-biphenyl-2-yl)palladium(II) (RuPhos-Pd-G3, 0.1 eq., 40.9 mg, 0.0489 mmol) was purged with nitrogen and the reaction was capped and stirred at 80° C. overnight. The reaction mixture was cooled, partitioned between EtOAc (20 mL) and water (10 mL) and the layers separated. The organics were washed with water and brine (5 mL each), dried over Na₂SO₄ and evaporated in vacuo. The residue was chromatographed on silica gel using 5% MeOH/DCM+0.25% NH₄OH as eluent to give product (216 mg, 70%). ESI+APCI MS m/z 632.3 [M+H]⁺.

Step D: 2-((S)-1-acryloyl-4-(2-(((R)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile To a stirred solution of benzyl (S)-2-(cyanomethyl)-4-(2-(((R)-1-methylpyrrolidin-2-yl)methoxy)-7-(naphthalen-1-yl)-5,6,7,8-tetrahydropyrido[3,4-d]pyrimidin-4-yl)piperazine-1-carboxylate (216 mg, 0.3419 mmol) in MeOH-THF (1:1, 3 mL) was added palladium on carbon (50 mg, 5%, Degussa type E101 NO/W) and the mixture was degassed under vacuum, backfilled with hydrogen and the reaction stirred under hydrogen atmosphere for 4 hours. The reaction mixture was filtered through Celite (2 mL) and the celite washed with EtOH (3×2 mL). The combined organics were evaporated in vacuo and the residue dissolved in DCM (10 mL). The solution was cooled with stirring to −30° C. followed by addition of NEt₃ (0.28 mL, 1.71 mmol) acryloyl chloride (0.08333 ml, 1.026 mmol) and the reaction stirred at −30° C. for 1 minute. The reaction was quenched with addition of NH₄OH (0.05 mL) and warmed to room temperature. The solution was evaporated in vacuo. The residue was dissolved in DCM (10 mL), filtered through a cotton plug and chromatographed on silica gel using 5 to 10% MeOH+0.25% NH₄OH in DCM as eluent to give title compound (EXAMPLE 441, 109 mg, 58%). ESI+APCI MS m/z 552.3 [M+H]⁺.

Example 442

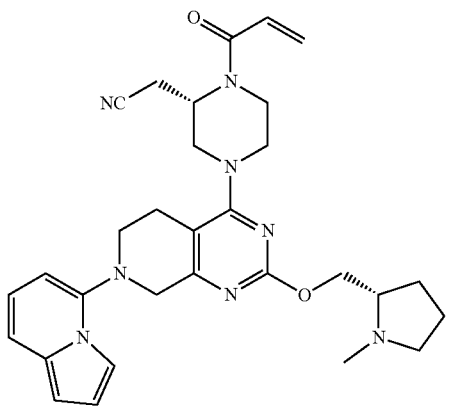 [SMILES: C=CC(=O)N1CCN(c2nc(OC[C@@H]3CCCN3C)nc3c2CCN(c2cccc4cccn24)C3)C[C@@H]1CC#N]

2-((S)-1-acryloyl-4-(7-(indolizin-5-yl)-2-(((S)-1-methylpyrrolidin-2-yl)methoxy)-5,6,7,8-tetrahydropyrido[3,4-d]pyrimidin-4-yl)piperazin-2-yl)acetonitrile

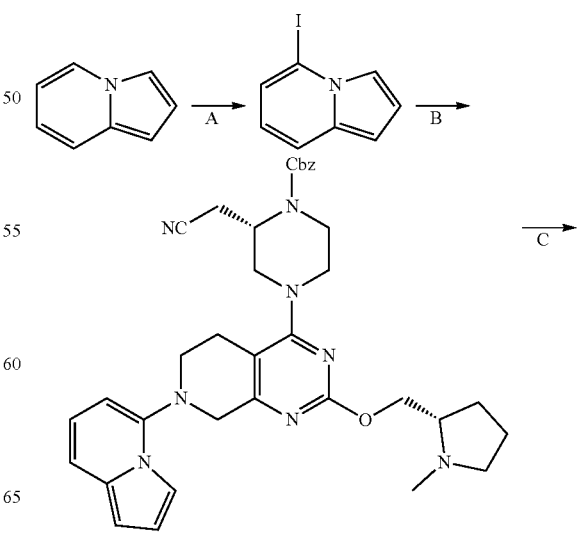

-continued

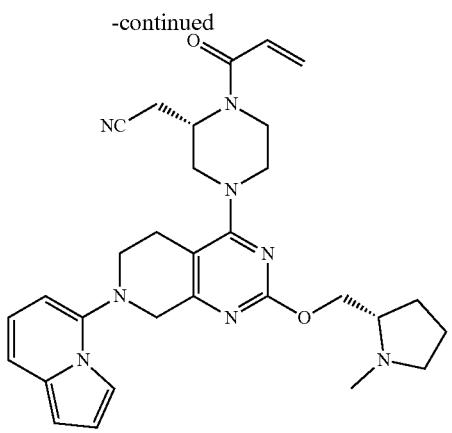

Step A: 5-iodoindolizine

To a stirred solution of indolizine (5.69 ml, 1.71 mmol) and N1,N1,N2,N2-tetramethylethane-1,2-diamine (0.282 ml, 1.88 mmol) in anhydrous tetrahydrofuran (5.7 ml, 1.71 mmol) cooled to −80° C. was added a solution of butyllithium (120 mg, 1.88 mmol) dropwise. The reaction mixture was warmed to −20° C. and kept at −20° C. for 2 hours. The mixture was cooled to −80° C. and a solution of iodine (433 mg, 1.71 mmol) in dry THF (3 mL) was added. The reaction mixture was warmed to room temperature and treated with a saturated solution of ammonium chloride. The organic layer was separated and the aqueous layer was extracted with hexane. The combined organics were dried over anhydrous $Na_2SO_4$ and concentrated in vacuo. The crude product was purified by column chromatography on silica gel using hexane as eluent to give product (216 mg).

Step B: benzyl (S)-2-(cyanomethyl)-4-(7-(indolizin-5-yl)-2-(((S)-1-methylpyrrolidin-2-yl)methoxy)-5,6,7,8-tetrahydropyrido[3,4-d]pyrimidin-4-yl)piperazine-1-carboxylate A mixture of crude benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (100 mg, 0.198 mmol), $Cs_2CO_3$ (193 mg, 0.593 mmol), dioxane (0.5 mL), 5-iodoindolizine (72.1 mg, 0.297 mmol) (1.5 eq.) and methanesulfonato(2-dicyclohexylphosphino-2',6'-di-i-propoxy-1,1'-biphenyl)(2'-methylamino-1,1'-biphenyl-2-yl)palladium(II) (RuPhos-Pd-G4, 0.1 eq., 16.8 mg, 0.0198 mmol) was purged with nitrogen and the reaction was capped and stirred at 80° C. for 4 hours. The reaction mixture was cooled, partitioned between EtOAc (20 mL) and water (10 mL) and the layers were separated. The organics were washed with water and brine (5 mL each), dried over $Na_2SO_4$ and evaporated in vacuo. The residue was chromatographed on silica gel using 4% MeOH/DCM+ 0.4% $NH_4OH$ as eluent to give product (74 mg, 60%). ESI+APCI MS m/z 621.3 $[M+H]^+$.

Step C: 2-((S)-4-(7-(indolizin-5-yl)-2-(((S)-1-methylpyrrolidin-2-yl)methoxy)-5,6,7,8-tetrahydropyrido[3,4-d]pyrimidin-4-yl)piperazin-2-yl)acetonitrile A mixture of benzyl (S)-2-(cyanomethyl)-4-(7-(indolizin-5-yl)-2-(((S)-1-methylpyrrolidin-2-yl)methoxy)-5,6,7,8-tetrahydropyrido[3,4-d]pyrimidin-4-yl)piperazine-1-carboxylate (74 mg, 0.12 mmol), methanol (5 ml) and palladium on carbon (20 mg, 5%, Degussa type E101 NO/W) was degassed under vacuum and backfilled with hydrogen and the reaction was stirred under a hydrogen atmosphere for 2 hours. The slurry was filtered through Celite (1 mL) and the Celite was washed with MeOH (3×2 mL). The combined organics were evaporated in vacuo to give product which was used crude in the next reaction. ESI+APCI MS m/z 487.3 $[M+H]^+$.

Step D: 2-((S)-1-acryloyl-4-(7-(indolizin-5-yl)-2-((S)-1-methylpyrrolidin-2-yl)methoxy)-5,6,7,8-tetrahydropyrido[3,4-d]pyrimidin-4-yl)piperazin-2-yl)acetonitrile A solution of 2-((S)-4-(7-(indolizin-5-yl)-2-(((S)-1-methylpyrrolidin-2-yl)methoxy)-5,6,7,8-tetrahydropyrido[3,4-d]pyrimidin-4-yl)piperazin-2-yl)acetonitrile (50 mg, 0.1027 mmol) in DCM (5 mL) was cooled to −30° C. followed by addition of triethylamine (42.96 µl, 0.3082 mmol) and acryloyl chloride (16.70 µl, 0.2055 mmol). After stirring 5 minutes at −30° C. the reaction mixture was quenched with sat. $NaHCO_3$ (1 mL) and warmed to room temperature followed by addition of water (2 mL). The layers were separated and the organics were dried over $Na_2SO_4$ and evaporated in vacuo. The residue was chromatographed on silica gel using 4% MeOH+0.4% $NH_4OH$ as eluent to give title compound (EXAMPLE 442, 33 mg, 59%). ESI+APCI MS m/z 571.3 $[M+H]^+$.

Example 443

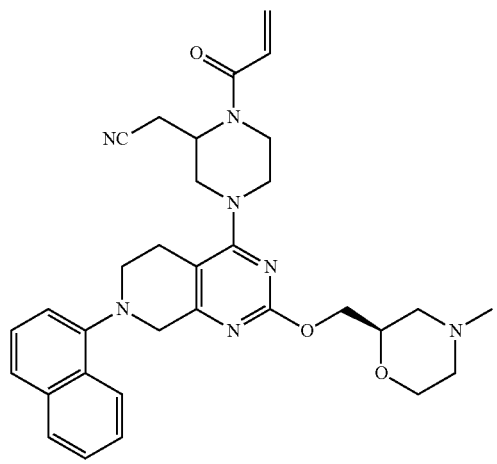 [SMILES: C=CC(=O)N1CCN(c2nc(OC[C@H]3CN(C)CCO3)nc3c2CCN(c2cccc4ccccc24)C3)CC1CC#N]

1177

2-(1-Acryloyl-4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile

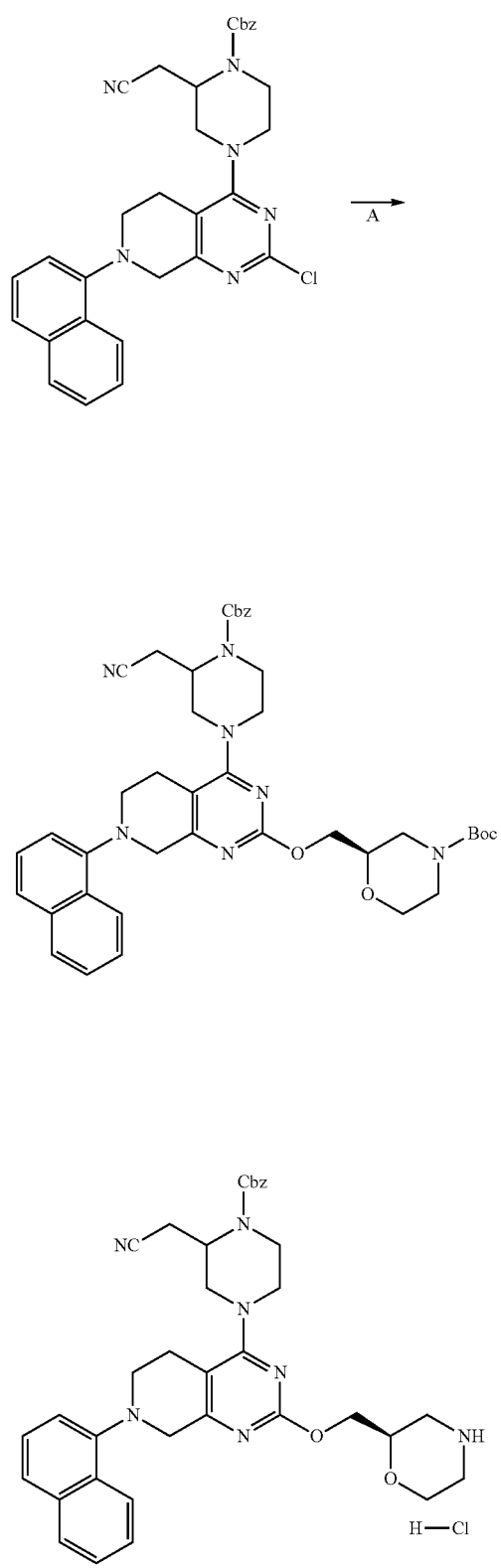

1178

-continued

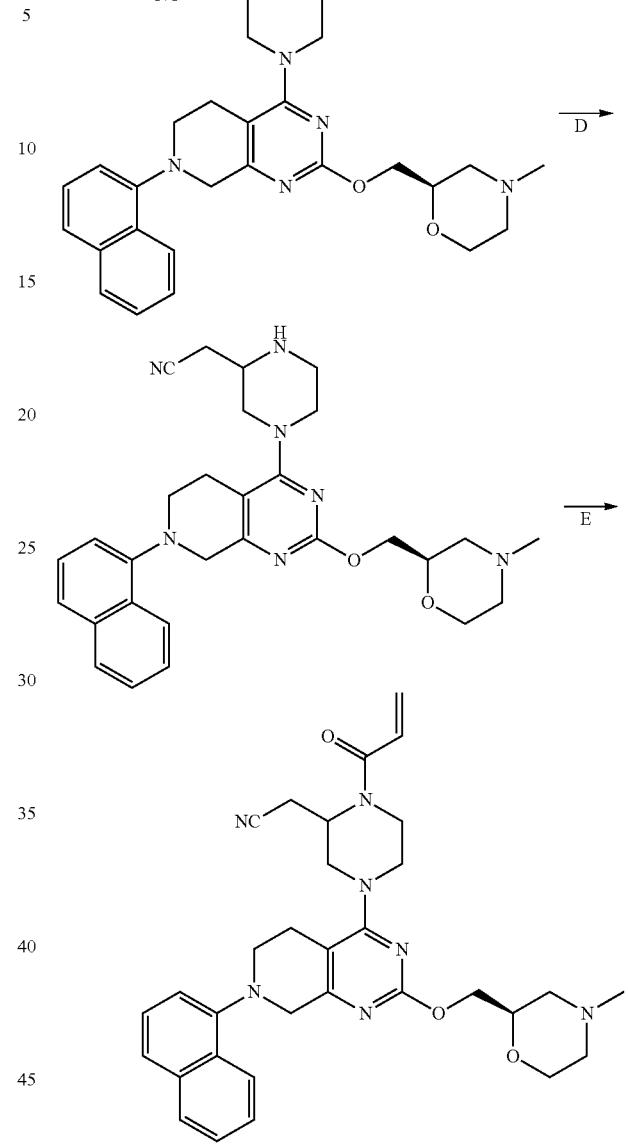

Step A: tert-Butyl (2R)-2-(((4-(4-((benzyloxy)carbonyl)-3-(cyanomethyl)piperazin-1-yl)-7-(naphthalen-1-yl)-5,6,7,8-tetrahydropyrido [3,4-d]pyrimidin-2-yl)oxy)methyl)morpholine-4-carboxylate Prepared according to the procedure of Example 375 Step C, substituting benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (65 mg, 0.118 mmol) and (R)—N-Boc-2-hydroxymethylmorpholine (76.6 mg, 0.353 mmol), purifying by flash chromatography eluting with 25-100% hex/EtOAc to afford tert-butyl (2R)-2-(((4-(4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (49 mg, 0.0668 mmol, 56.8% yield). ESI+MS m/z 734.3 (100%) [M+H]⁺.

Step B: Benzyl 2-(cyanomethyl)-4-(2-(((R)-morpholin-2-yl)methoxy)-7-(naphthalen-1-yl)-5,6,7,8-tetrahydropyrido [3,4-d]pyrimidin-4-yl)piperazine-1-carboxylate hydrochloride Prepared according to the procedure of Example 375 Step D, substituting tert-butyl (2R)-2-(((4-(4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (49 mg, 0.067 mmol) to afford benzyl 2-(cyanomethyl)-4-(2-(((R)-morpholin-2-yl)methoxy)-7-(naphthalen-1-yl)-5,6,7,8-tetrahydropyrido[3,4-d]pyrimidin-4-yl)piperazine-1-carboxylate hydrochloride (45 mg, 0.067 mmol, 100%). ESI+MS m/z 634.3 (100%) [M+H]+.

Step C: Benzyl 2-(cyanomethyl)-4-(2-(((R)-4-methylmorpholin-2-yl)methoxy)-7-(naphthalen-1-yl)-5,6,7,8-tetrahydropyrido[3,4-d]pyrimidin-4-yl)piperazine-1-carboxylate To a solution of benzyl 2-(cyanomethyl)-4-(2-(((R)-morpholin-2-yl)methoxy)-7-(naphthalen-1-yl)-5,6,7,8-tetrahydropyrido[3,4-d]pyrimidin-4-yl)piperazine-1-carboxylate hydrochloride (45 mg, 0.067 mmol), formaldehyde (54 mg, 0.67 mmol) (37 wt % in MeOH/water) in DCM (671 µl, 0.067 mmol) and THF (671 µl, 0.067 mmol) was added NaBH(OAc)₃ (142 mg, 0.67 mmol) and the resulting mixture was stirred at RT for 15 m. The reaction mixture was partitioned between ethyl acetate and 1N NaOH. The aqueous layer was extracted with ethyl acetate (1×). The combined organic layers were dried (MgSO₄) and concentrated to give a residue that was purified by flash eluting with a gradient of 25-50% of a 10% MeOH/1% NH₄OH/DCM mixture in DCM. The product-containing fractions were concentrated to afford benzyl 2-(cyanomethyl)-4-(2-(((R)-4-methylmorpholin-2-yl)methoxy)-7-(naphthalen-1-yl)-5,6,7,8-tetrahydropyrido[3,4-d]pyrimidin-4-yl)piperazine-1-carboxylate (22 mg, 0.034 mmol, 51%). ESI+MS m/z 648.3 (100%) [M+H]+.

Step D: 2-(4-(2-(((R)-4-Methylmorpholin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl 2-(cyanomethyl)-4-(2-(((R)-4-methylmorpholin-2-yl)methoxy)-7-(naphthalen-1-yl)-5,6,7,8-tetrahydropyrido[3,4-d]pyrimidin-4-yl)piperazine-1-carboxylate (22 mg, 0.034 mmol) to afford 2-(4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile (15.9 mg, 0.031 mmol, 91%). ESI+MS m/z 514.3 (100%) [M+H]+.

Step E: 2-(1-Acryloyl-4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step G, substituting 2-(4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile (16 mg, 0.031 mmol) to afford title compound 2-(1-acryloyl-4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile (EXAMPLE 443, 8.0 mg, 0.014 mmol, 46%). ESI+MS m/z 568.3 (100%) [M+H]+.

Example 444

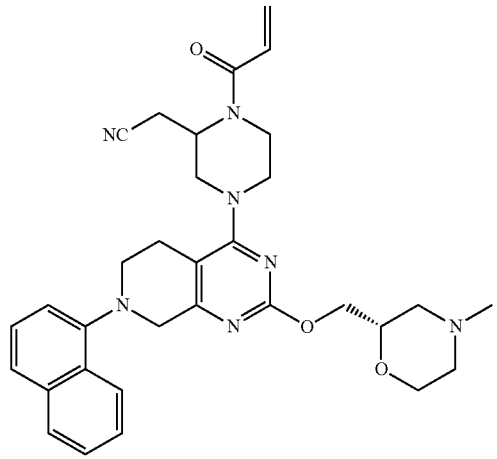 [SMILES: C=CC(=O)N1CCN(c2nc(OC[C@@H]3CN(C)CCO3)nc3c2CCN(c2cccc4ccccc24)C3)CC1CC#N]

2-(1-Acryloyl-4-(2-(((S)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile

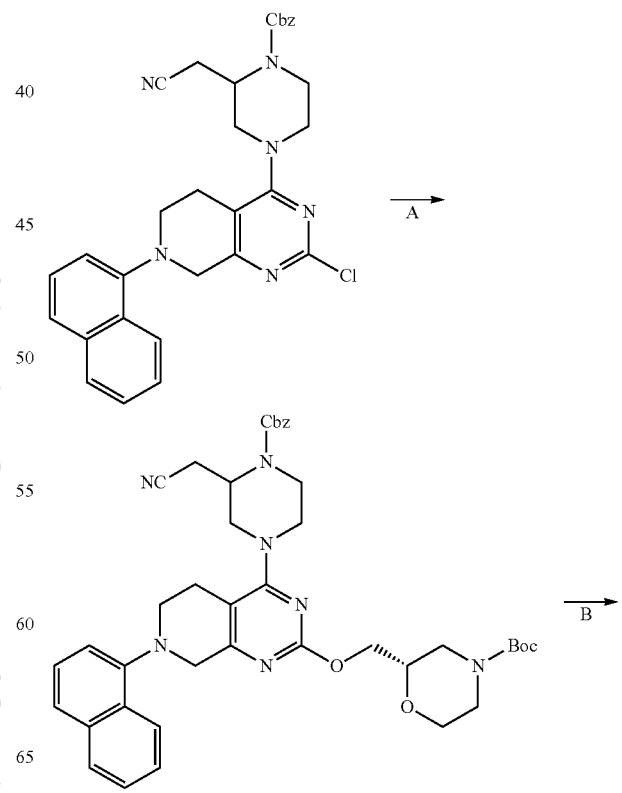

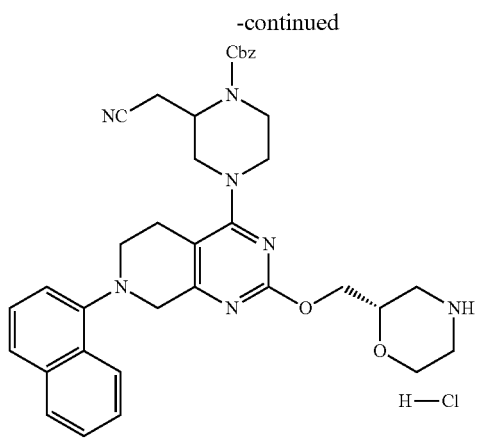

Step A: tert-Butyl (2S)-2-(((4-(4-((benzyloxy)carbo-nyl)-3-(cyanomethyl)piperazin-1-yl)-7-(naphthalen-1-yl)-5,6,7,8-tetrahydropyrido [3,4-d]pyrimidin-2-yl)oxy)methyl)morpholine-4-carboxylate Prepared according to the procedure of Example 375 Step C, substituting benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (65 mg, 0.118 mmol) and tert-butyl (S)-2-(hydroxymethyl)morpholine-4-carboxylate (76.6 mg, 0.353 mmol), purifying by flash chromatography eluting with 25-100% hex/EtOAc to afford tert-butyl (2S)-2-(((4-(4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (43 mg, 0.059 mmol, 49.9% yield). ESI+MS m/z 734.3 (100%) [M+H]$^+$.

Step B: Benzyl 2-(cyanomethyl)-4-(2-(((S)-morpholin-2-yl)methoxy)-7-(naphthalen-1-yl)-5,6,7,8-tetrahydropyrido [3,4-d]pyrimidin-4-yl)piperazine-1-carboxylate hydrochloride Prepared according to the procedure of Example 375 Step D, substituting tert-butyl (2S)-2-(((4-(4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (43 mg, 0.059 mmol) to afford benzyl 2-(cyanomethyl)-4-(2-(((S)-morpholin-2-yl)methoxy)-7-(naphthalen-1-yl)-5,6,7,8-tetrahydropyrido[3,4-d]pyrimidin-4-yl)piperazine-1-carboxylate hydrochloride (39 mg, 0.058 mmol, 100%). ESI+MS m/z 634.3 (100%) [M+H]$^+$.

Step C: Benzyl 2-(cyanomethyl)-4-(2-(((S)-4-methylmorpholin-2-yl)methoxy)-7-(naphthalen-1-yl)-5,6,7,8-tetrahydropyrido[3,4-d]pyrimidin-4-yl)piperazine-1-carboxylate Prepared according to the procedure from Example 443 step C, substituting benzyl 2-(cyanomethyl)-4-(2-(((S)-morpholin-2-yl)methoxy)-7-(naphthalen-1-yl)-5,6,7,8-tetrahydropyrido[3,4-d]pyrimidin-4-yl)piperazine-1-carboxylate hydrochloride (39 mg, 0.067 mmol), to afford benzyl 2-(cyanomethyl)-4-(2-(((S)-4-methylmorpholin-2-yl)methoxy)-7-(naphthalen-1-yl)-5,6,7,8-tetrahydropyrido[3,4-d]pyrimidin-4-yl)piperazine-1-carboxylate (17 mg, 0.026 mmol, 45%). ESI+MS m/z 648.3 (100%) [M+H]$^+$.

Step D: 2-(4-(2-(((S)-4-Methylmorpholin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl 2-(cyanomethyl)-4-(2-(((S)-4-methylmorpholin-2-yl)methoxy)-7-(naphthalen-1-yl)-5,6,7,8-tetrahydropyrido[3,4-d]pyrimidin-4-yl)piperazine-1-carboxylate (17 mg, 0.026 mmol) to afford 2-(4-(2-(((S)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile (13.5 mg, 0.026 mmol, 100%). ESI+MS m/z 514.3 (100%) [M+H]$^+$.

Step E: 2-(1-Acryloyl-4-(2-(((S)-4-methylmorpholin-2-yl)methoxy)-7-(naphthalen-1-yl)-5,6,7,8-tetrahydropyrido[3,4-d]pyrimidin-4-yl)piperazin-2-yl) acetonitrile Prepared according to the procedure of Example 375 Step G, substituting 2-(4-(2-(((S)-4-methylmorpholin-2-yl)

methoxy)-7-(naphthalen-1-yl)-5,6,7,8-tetrahydropyrido[3,4-d]pyrimidin-4-yl)piperazin-2-yl)acetonitrile (13.5 mg, 0.026 mmol) to afford title compound 2-(1-acryloyl-4-(2-(((S)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile (EXAMPLE 444, 9.5 mg, 0.017 mmol, 65%). ESI+MS m/z 568.3 (100%) [M+H]⁺.

Example 445

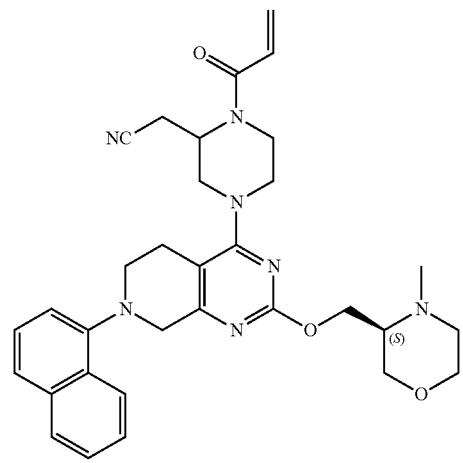

2-(1-Acryloyl-4-(2-(((S)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile

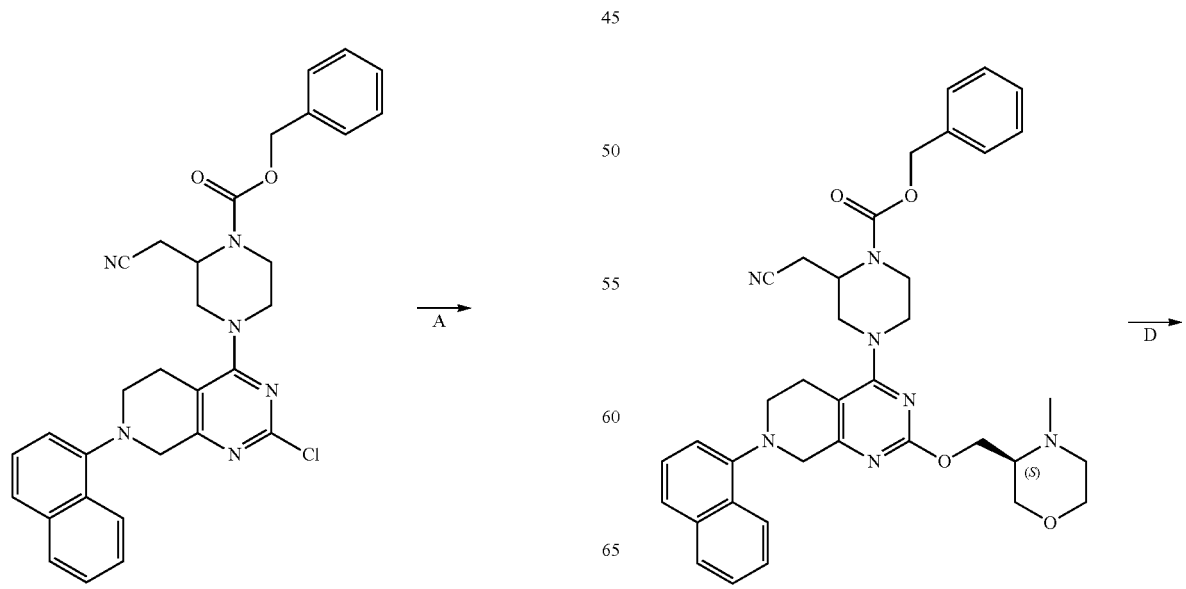

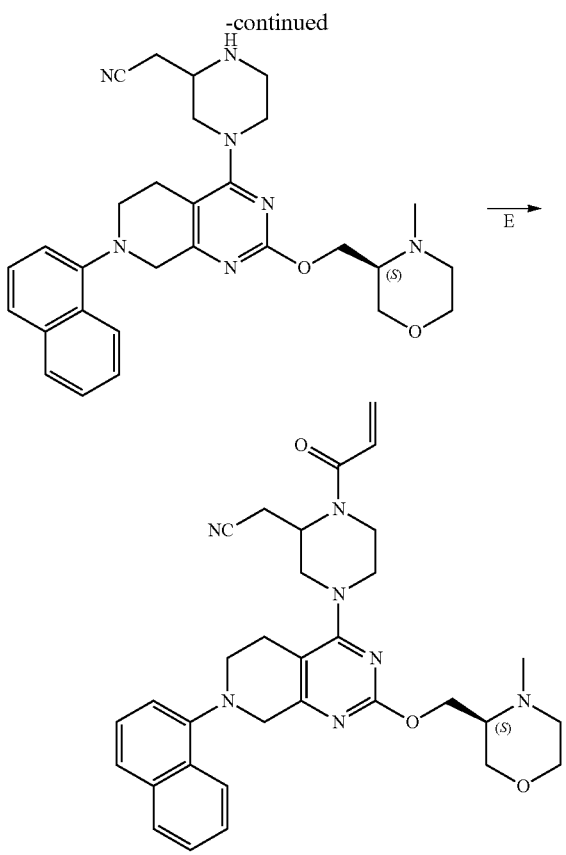

Step A: tert-Butyl (3S)-3-(((4-(4-((benzyloxy)carbonyl)-3-(cyanomethyl)piperazin-1-yl)-7-(naphthalen-1-yl)-5,6,7,8-tetrahydropyrido [3,4-d]pyrimidin-2-yl)oxy)methyl)morpholine-4-carboxylate Prepared according to the procedure of Example 375 Step C, substituting benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (65 mg, 0.118 mmol) and tert-butyl (R)-3-(hydroxymethyl)morpholine-4-carboxylate (76.6 mg, 0.353 mmol), purifying by flash chromatography eluting with 25-100% hex/EtOAc to afford tert-butyl (3S)-3-(((4-(4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (80 mg, 0.109 mmol, 92.8% yield). ESI+MS m/z 734.3 (100%) [M+H]⁺.

Step B: Benzyl 2-(cyanomethyl)-4-(2-(((S)-morpholin-3-yl)methoxy)-7-(naphthalen-1-yl)-5,6,7,8-tetrahydropyrido [3,4-d]pyrimidin-4-yl)piperazine-1-carboxylate hydrochloride Prepared according to the procedure of Example 375 Step D, substituting tert-butyl (3S)-3-(((4-(4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (80 mg, 0.11 mmol) to afford benzyl 2-(cyanomethyl)-4-(2-(((S)-morpholin-3-yl)methoxy)-7-(naphthalen-1-yl)-5,6,7,8-tetrahydropyrido[3,4-d]pyrimidin-4-yl)piperazine-1-carboxylate hydrochloride (73 mg, 0.11 mmol, 100%). ESI+MS m/z 634.3 (100%) [M+H]⁺.

Step C: Benzyl 2-(cyanomethyl)-4-(2-(((S)-4-methylmorpholin-3-yl)methoxy)-7-(naphthalen-1-yl)-5,6,7,8-tetrahydropyrido [3,4-d]pyrimidin-4-yl)piperazine-1-carboxylate Prepared according to the procedure from Example 443 step C, substituting benzyl 2-(cyanomethyl)-4-(2-(((S)-morpholin-3-yl)methoxy)-7-(naphthalen-1-yl)-5,6,7,8-tetrahydropyrido[3,4-d]pyrimidin-4-yl)piperazine-1-carboxylate hydrochloride (73 mg, 0.109 mmol), to afford benzyl 2-(cyanomethyl)-4-(2-(((S)-4-methylmorpholin-3-yl)methoxy)-7-(naphthalen-1-yl)-5,6,7,8-tetrahydropyrido[3,4-d]pyrimidin-4-yl)piperazine-1-carboxylate (27.6 mg, 0.042 mmol, 39%). ESI+MS m/z 648.3 (100%) [M+H]⁺.

Step D: 2-(4-(2-(((S)-4-Methylmorpholin-3-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl 2-(cyanomethyl)-4-(2-(((S)-4-methylmorpholin-2-yl)methoxy)-7-(naphthalen-1-yl)-5,6,7,8-tetrahydropyrido[3,4-d]pyrimidin-4-yl)piperazine-1-carboxylate (27.6 mg, 0.042 mmol) to afford 2-(4-(2-(((S)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile (20.2 mg, 0.039 mmol, 100%). ESI+MS m/z 514.3 (100%) [M+H]⁺.

Step E: 2-(1-Acryloyl-4-(2-(((S)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step G, substituting 2-(4-(2-(((S)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile (20.2 mg, 0.0393 mmol) to afford title compound 2-(1-acryloyl-4-(2-(((S)-4-methylmorpholin-3-yl)methoxy)-7-(naphthalen-1-yl)-5,6,7,8-tetrahydropyrido [3,4-d]pyrimidin-4-yl)piperazin-2-yl)acetonitrile (EXAMPLE 445, 15 mg, 0.026 mmol, 67%). ESI+MS m/z 568.3 (100%) [M+H]⁺.

Example 446

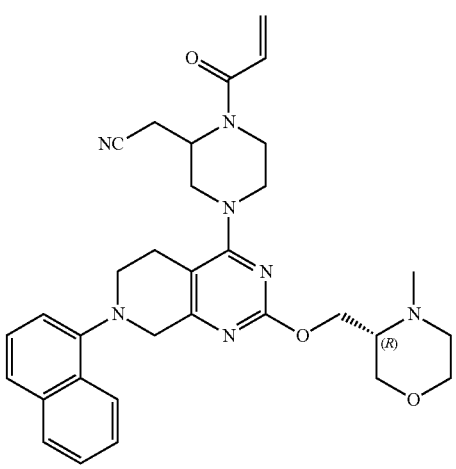

1187
2-(1-Acryloyl-4-(2-(((R)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile
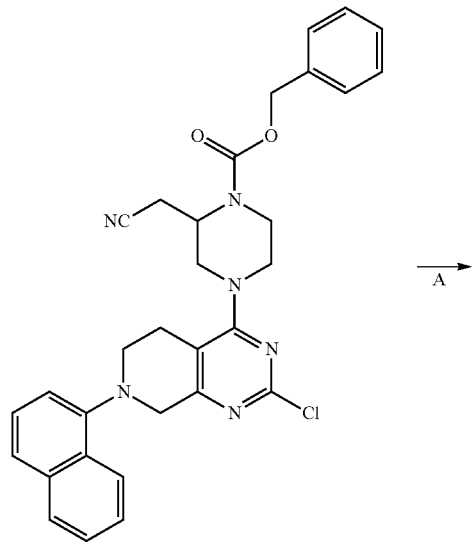
1188
-continued
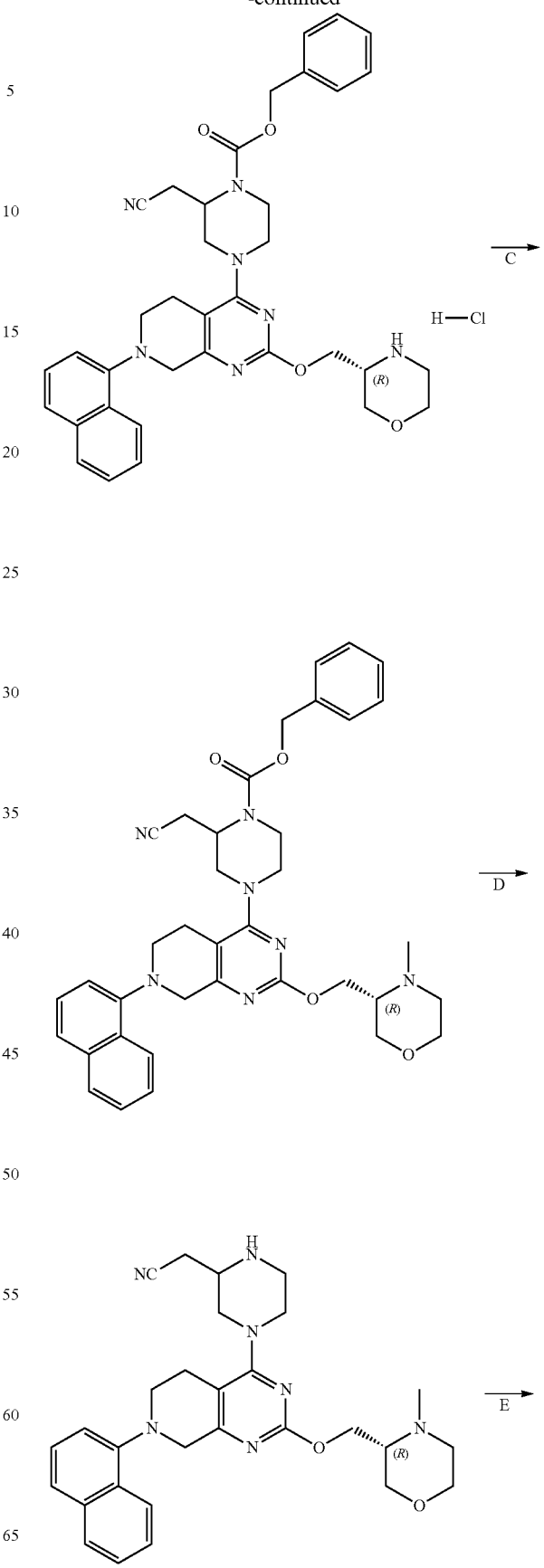

-continued

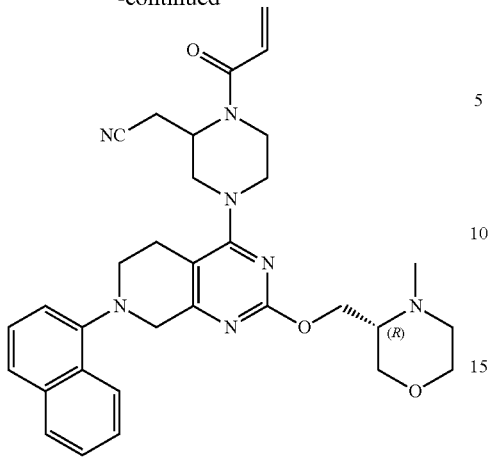

Step A: tert-Butyl (3R)-3-(((4-(4-((benzyloxy)carbonyl)-3-(cyanomethyl)piperazin-1-yl)-7-(naphthalen-1-yl)-5,6,7,8-tetrahydropyrido [3,4-d] pyrimidin-2-yl)oxy)methyl)morpholine-4-carboxylate Prepared according to the procedure of Example 375 Step C, substituting benzyl 4-(2-chloro-7-(naphthalen-1-yl)-5,6,7,8-tetrahydropyrido[3,4-d]pyrimidin-4-yl)-2-(cyanomethyl)piperazine-1-carboxylate (65 mg, 0.118 mmol) and tert-butyl (S)-3-(hydroxymethyl)morpholine-4-carboxylate (76.6 mg, 0.353 mmol), purifying by flash chromatography eluting with 25-100% hex/EtOAc to afford tert-butyl (3R)-3-(((4-(4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (50 mg, 0.068 mmol, 58.0% yield). ESI+MS m/z 734.3 (100%) [M+H]+.

Step B: Benzyl 2-(cyanomethyl)-4-(2-(((R)-morpholin-3-yl)methoxy)-7-(naphthalen-1-yl)-5,6,7,8-tetrahydropyrido [3,4-d]pyrimidin-4-yl)piperazine-1-carboxylate hydrochloride Prepared according to the procedure of Example 375 Step D, substituting tert-butyl (3R)-3-(((4-(4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (50 mg, 0.068 mmol) to afford benzyl 2-(cyanomethyl)-4-(2-(((R)-morpholin-3-yl)methoxy)-7-(naphthalen-1-yl)-5,6,7,8-tetrahydropyrido[3,4-d]pyrimidin-4-yl)piperazine-1-carboxylate hydrochloride (46 mg, 0.068 mmol, 100%). ESI+MS m/z 634.3 (100%) [M+H]+.

Step C: Benzyl 2-(cyanomethyl)-4-(2-(((R)-4-methylmorpholin-3-yl)methoxy)-7-(naphthalen-1-yl)-5,6,7,8-tetrahydropyrido [3,4-d]pyrimidin-4-yl)piperazine-1-carboxylate Prepared according to the procedure from Example 443 step C, substituting benzyl 2-(cyanomethyl)-4-(2-(((R)-morpholin-3-yl)methoxy)-7-(naphthalen-1-yl)-5,6,7,8-tetrahydropyrido[3,4-d]pyrimidin-4-yl)piperazine-1-carboxylate hydrochloride (73 mg, 0.109 mmol), to afford benzyl 2-(cyanomethyl)-4-(2-(((R)-4-methylmorpholin-3-yl)methoxy)-7-(naphthalen-1-yl)-5,6,7,8-tetrahydropyrido[3,4-d]pyrimidin-4-yl)piperazine-1-carboxylate (23.0 mg, 0.036 mmol, 52%). ESI+MS m/z 648.3 (100%) [M+H]+.

Step D: 2-(4-(2-(((R)-4-Methylmorpholin-3-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl 2-(cyanomethyl)-4-(2-(((R)-4-methylmorpholin-2-yl)methoxy)-7-(naphthalen-1-yl)-5,6,7,8-tetrahydropyrido[3,4-d]pyrimidin-4-yl)piperazine-1-carboxylate (23.0 mg, 0.036 mmol) to afford 2-(4-(2-(((R)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile (18.2 mg, 0.036 mmol, 100%). ESI+MS m/z 514.3 (100%) [M+H]+.

Step E: 2-(1-Acryloyl-4-(2-(((R)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step G, substituting 2-(4-(2-(((R)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile (18.2 mg, 0.036 mmol) to afford title compound 2-(1-acryloyl-4-(2-(((R)-4-methylmorpholin-3-yl)methoxy)-7-(naphthalen-1-yl)-5,6,7,8-tetrahydropyrido[3,4-d]pyrimidin-4-yl)piperazin-2-yl)acetonitrile (EXAMPLE 446, 14 mg, 0.025 mmol, 69%). ESI+MS m/z 568.3 (100%) [M+H]+.

Example 447

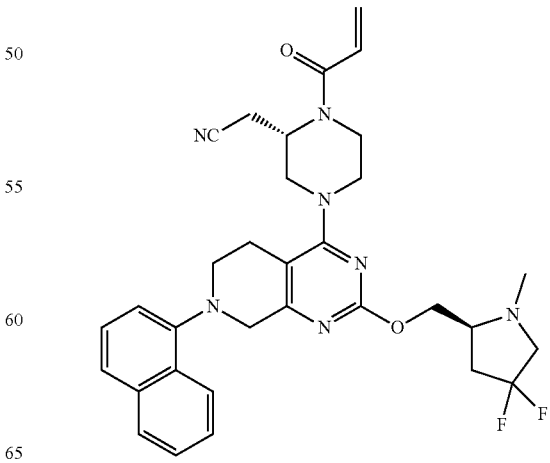

1191

2-((S)-1-Acryloyl-4-(2-(((S)-4,4-difluoro-1-methyl-pyrrolidin-2-yl)methoxy)-7-(naphthalen-1-yl)-5,6,7,8-tetrahydropyrido[3,4-d]pyrimidin-4-yl)piperazin-2-yl)acetonitrile

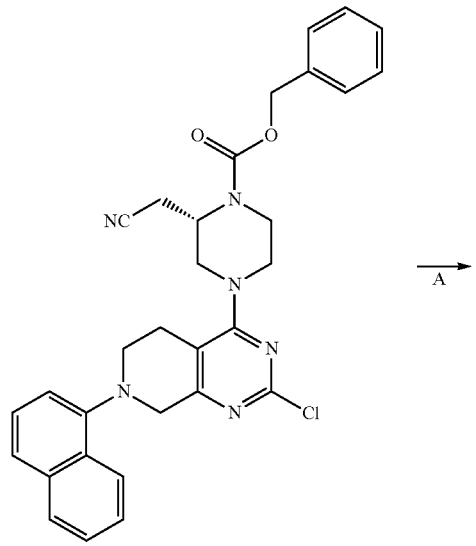

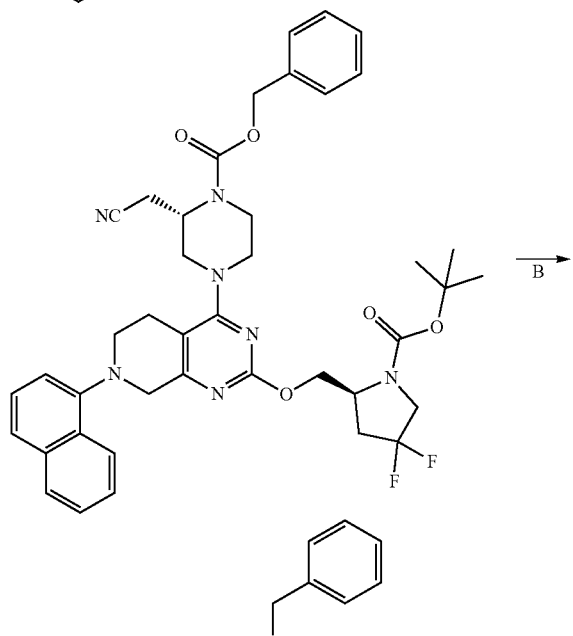

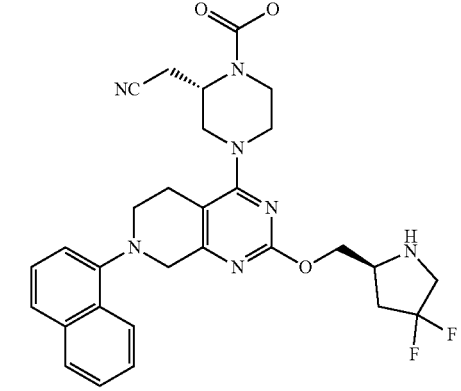

1192

-continued

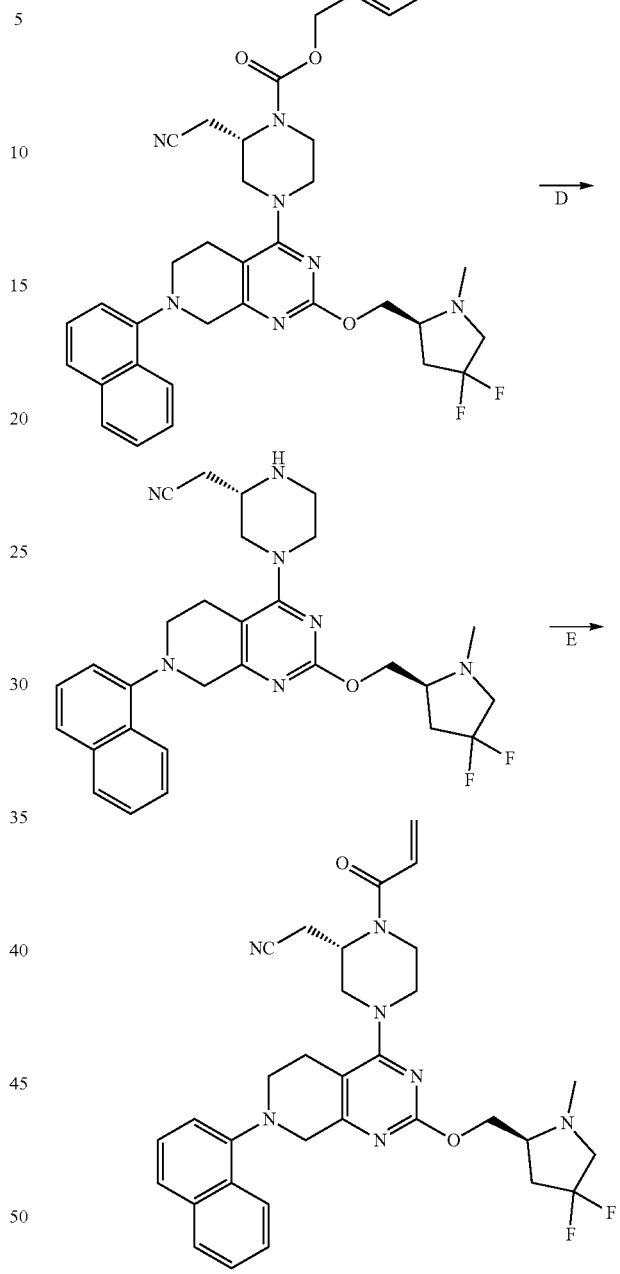

Step A: Benzyl (S)-4-(2-(((S)-1-(tert-butoxycarbonyl)-4,4-difluoropyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate Prepared according to the procedure of Example 375 Step C, substituting benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (50 mg, 0.090 mmol) and tert-butyl (S)-4,4-difluoro-2-(hydroxymethyl)pyrrolidine-1-carboxylate (64.3 mg, 0.271 mmol), purifying by flash chromatography eluting with 25-100% hex/EtOAc to afford benzyl (S)-4-(2-(((S)-1-(tert-butoxycarbonyl)-4,4-difluoropyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (15 mg, 0.020 mmol, 22.0% yield). ESI+ MS m/z 754.3 (100%) [M+H]+.

Step B: Benzyl (S)-2-(cyanomethyl)-4-(2-(((S)-4,4-difluoropyrrolidin-2-yl)methoxy)-7-(naphthalen-1-yl)-5,6,7,8-tetrahydropyrido[3,4-d]pyrimidin-4-yl)piperazine-1-carboxylate hydrochloride Prepared according to the procedure of Example 375 Step D, substituting benzyl (S)-4-(2-(((S)-1-(tert-butoxycarbonyl)-4,4-difluoropyrrolidin-2-yl)methoxy)-7-(naphthalen-1-yl)-5,6,7,8-tetrahydropyrido[3,4-d]pyrimidin-4-yl)-2-(cyanomethyl)piperazine-1-carboxylate (18 mg, 0.024 mmol) to afford benzyl (S)-2-(cyanomethyl)-4-(2-(((S)-4,4-difluoropyrrolidin-2-yl)methoxy)-7-(naphthalen-1-yl)-5,6,7,8-tetrahydropyrido[3,4-d]pyrimidin-4-yl)piperazine-1-carboxylate hydrochloride (16 mg, 0.023 mmol, 100%). ESI+MS m/z 654.3 (100%) [M+H]+.

Step C: Benzyl (S)-2-(cyanomethyl)-4-(2-(((S)-4,4-difluoro-1-methylpyrrolidin-2-yl)methoxy)-7-(naphthalen-1-yl)-5,6,7,8-tetrahydropyrido[3,4-d]pyrimidin-4-yl)piperazine-1-carboxylate Prepared according to the procedure from Example 443 step C, substituting benzyl (S)-2-(cyanomethyl)-4-(2-(((S)-4,4-difluoropyrrolidin-2-yl)methoxy)-7-(naphthalen-1-yl)-5,6,7,8-tetrahydropyrido[3,4-d]pyrimidin-4-yl)piperazine-1-carboxylate (16 mg, 0.023 mmol), to afford benzyl (S)-2-(cyanomethyl)-4-(2-(((S)-4,4-difluoro-1-methylpyrrolidin-2-yl)methoxy)-7-(naphthalen-1-yl)-5,6,7,8-tetrahydropyrido [3,4-d]pyrimidin-4-yl)piperazine-1-carboxylate (16.0 mg, 0.024 mmol, 52%). ESI+MS m/z 668.3 (100%) [M+H]+.

Step D: 2-((S)-4-(2-(((S)-4,4-Difluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl (S)-2-(cyanomethyl)-4-(2-(((S)-4,4-difluoro-1-methylpyrrolidin-2-yl)methoxy)-7-(naphthalen-1-yl)-5,6,7,8-tetrahydropyrido[3,4-d]pyrimidin-4-yl)piperazine-1-carboxylate (16.0 mg, 0.024 mmol) to afford 2-((S)-4-(2-(((S)-4,4-difluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (8.0 mg, 0.015 mmol, 63%). ESI+MS m/z 534.3 (100%) [M+H]+.

Step E: 2-((S)-1-Acryloyl-4-(2-(((S)-4,4-difluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step G, substituting 2-((S)-4-(2-(((S)-4,4-difluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (8.0 mg, 0.015 mmol) to afford title compound 2-((S)-1-acryloyl-4-(2-(((S)-4,4-difluoro-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile (EXAMPLE 447, 4 mg, 0.007 mmol, 45%). ESI+MS m/z 588.3 (100%) [M+H]+.

Example 448

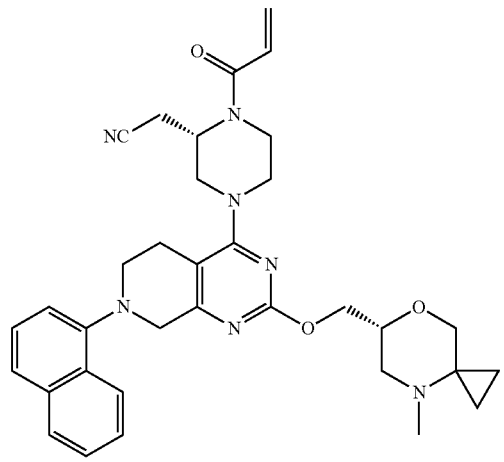 [SMILES: C=CC(=O)N1CCN(c2nc(OC[C@H]3CN(C)C4(CC4)CO3)nc3c2CCN(c2cccc4ccccc24)C3)C[C@@H]1CC#N]

2-((S)-1-Acryloyl-4-(2-(((R)-4-methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazin-2-yl)acetonitrile

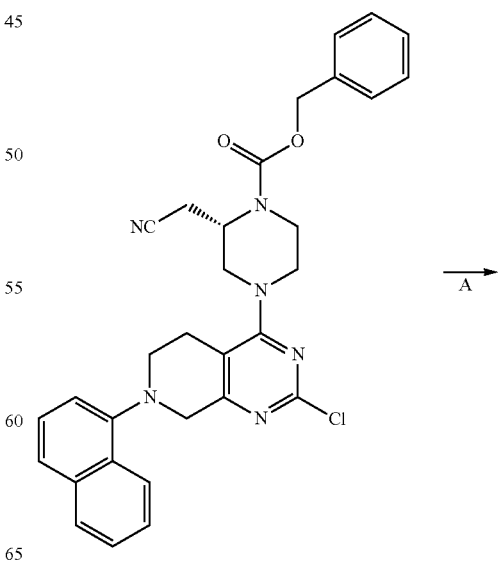

1195
-continued

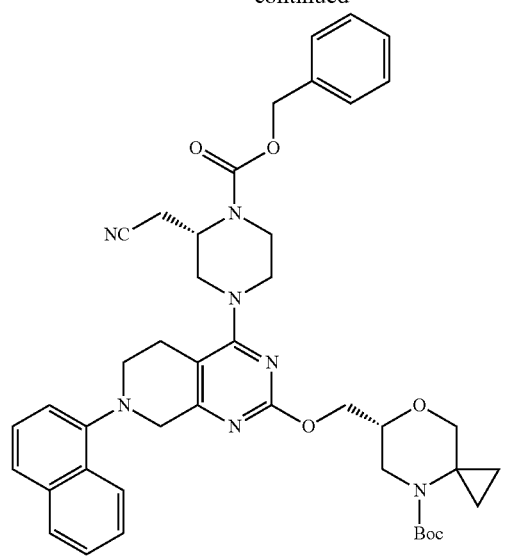

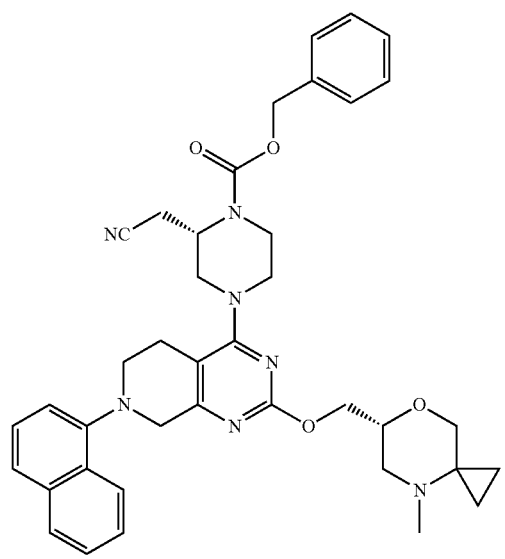

1196
-continued

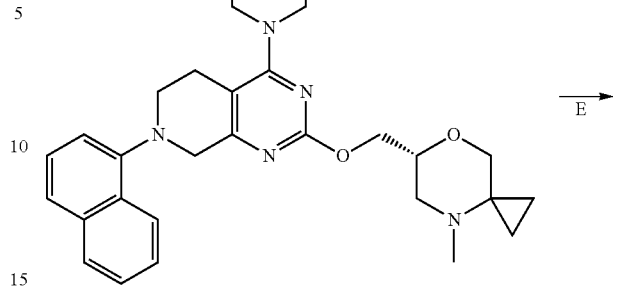

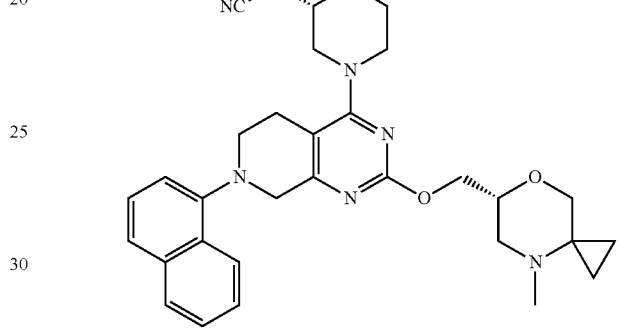

Step A: tert-Butyl (R)-6-(((4-((S)-4-((benzyloxy)carbonyl)-3-(cyanomethyl)piperazin-1-yl)-7-(naphthalen-1-yl)-5,6,7,8-tetrahydropyrido [3,4-d]pyrimidin-2-yl)oxy)methyl)-7-oxa-4-azaspiro[2.5]octane-4-carboxylate Prepared according to the procedure of Example 375 Step C, substituting benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (25 mg, 0.045 mmol) and tert-butyl (R)-6-(hydroxymethyl)-7-oxa-4-azaspiro[2.5]octane-4-carboxylate (33.0 mg, 0.136 mmol), purifying by flash chromatography eluting with 25-100% hex/EtOAc to afford tert-butyl (R)-6-(((4-((S)-4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)-7-oxa-4-azaspiro[2.5]octane-4-carboxylate (35 mg, 0.0461 mmol, 100% yield). ESI+MS m/z 760.3 (100%) [M+H]$^+$.

Step B: Benzyl (S)-4-(2-(((R)-7-oxa-4-azaspiro[2.5]octan-6-yl)methoxy)-7-(naphthalen-1-yl)-5,6,7,8-tetrahydropyrido[3,4-d]pyrimidin-4-yl)-2-(cyanomethyl)piperazine-1-carboxylate hydrochloride Prepared according to the procedure of Example 375 Step D, substituting tert-butyl (R)-6-(((4-((S)-4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)-7-oxa-4-azaspiro[2.5]octane-4-carboxylate (35 mg, 0.046 mmol) to afford benzyl (S)-4-(2-(((R)-7-oxa-4-azaspiro[2.5]octan-6-yl)methoxy)-7-(naphthalen-1-yl)-5,6,7,8-tetrahydropyrido[3,4-d]pyrimidin-4-yl)-2-(cyanomethyl)piperazine-1-carboxylate hydrochloride (32 mg, 0.046 mmol, 100%). ESI+MS m/z 660.3 (100%) [M+H]+.

Step C: Benzyl (S)-2-(cyanomethyl)-4-(2-(((R)-4-methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazine-1-carboxylate Prepared according to the procedure from Example 443 step C, substituting benzyl (S)-4-(2-(((R)-7-oxa-4-azaspiro[2.5]octan-6-yl)methoxy)-7-(naphthalen-1-yl)-5,6,7,8-tetrahydropyrido[3,4-d]pyrimidin-4-yl)-2-(cyanomethyl)piperazine-1-carboxylate hydrochloride (32 mg, 0.046 mmol), to afford benzyl (S)-2-(cyanomethyl)-4-(2-(((R)-4-methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazine-1-carboxylate (31 mg, 0.046 mmol, 100%). ESI+MS m/z 674.3 (100%) [M+H]+.

Step D: 2-((S)-4-(2-(((R)-4-Methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl (S)-2-(cyanomethyl)-4-(2-(((R)-4-methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazine-1-carboxylate (31.0 mg, 0.046 mmol) to afford 2-((S)-4-(2-(((R)-4-methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazin-2-yl)acetonitrile (18.0 mg, 0.033 mmol, 72%). ESI+MS m/z 540.3 (100%) [M+H]+.

Step E: 2-((S)-1-Acryloyl-4-(2-(((R)-4-methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step G, substituting 2-((S)-4-(2-(((R)-4-methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazin-2-yl)acetonitrile (18.0 mg, 0.033 mmol) to afford title compound 2-((S)-1-acryloyl-4-(2-(((R)-4-methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazin-2-yl)acetonitrile (EXAMPLE 448, 5.8 mg, 0.010 mmol, 29%). ESI+MS m/z 594.3 (100%) [M+H]+.

Example 449

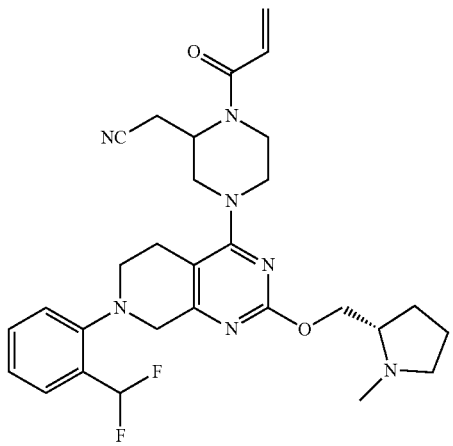 [SMILES: C=CC(=O)N1CCN(c2nc(OC[C@@H]3CCCN3C)nc3c2CCN(c2ccccc2C(F)F)C3)CC1CC#N]

2-(1-Acryloyl-4-(7-(2-(difluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile

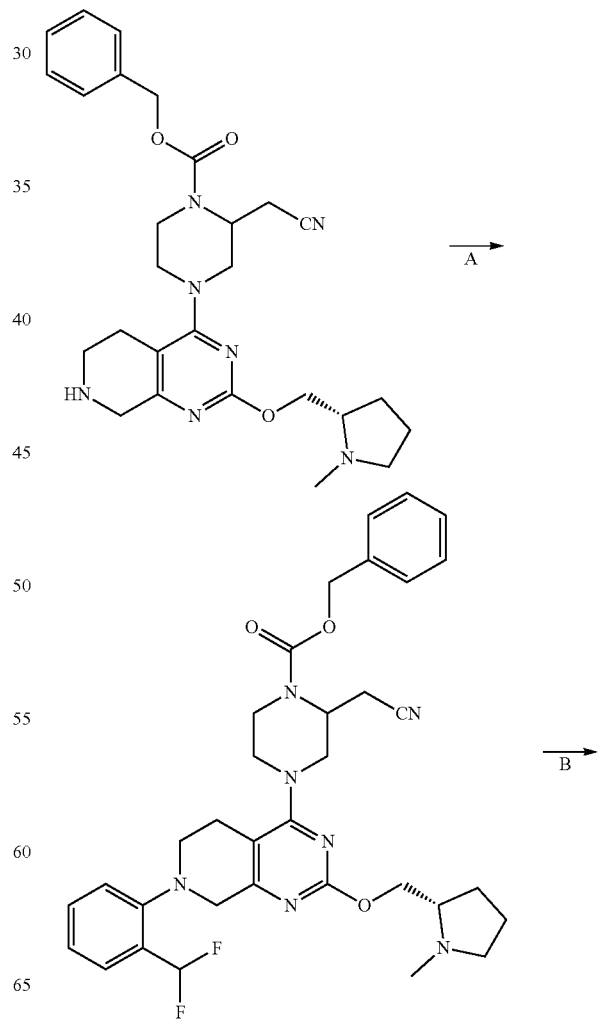

-continued

[Structure]

Step A. Benzyl 2-(cyanomethyl)-4-(7-(2-(difluoromethyl)phenyl)-2-((S)-1-methylpyrrolidin-2-yl)methoxy)-5,6,7,8-tetrahydropyrido[3,4-d]pyrimidin-4-yl)piperazine-1-carboxylate A mixture of benzyl 2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (30 mg, 0.0593 mmol), 1-Bromo-2-difluoromethylbenzene (36.8 mg, 0.178 mmol), BINAP Palladacycle Gen. 3 (5.9 mg, 0.006 mmol), $Cs_2CO_3$ (77.3 mg, 0.237 mmol) in dioxane (593 µl, 0.0593 mmol) was sparged with Ar for 5 m then sealed and heated at 100° C. for 1 d. The reaction mixture was loaded onto a silica gel samplet and purified by flash chromatography eluting with a 1-10% MeOH/DCM (1% $NH_4OH$) gradient to afford benzyl 2-(cyanomethyl)-4-(7-(2-(difluoromethyl)phenyl)-2-((S)-1-methylpyrrolidin-2-yl)methoxy)-5,6,7,8-tetrahydropyrido[3,4-d]pyrimidin-4-yl)piperazine-1-carboxylate (12 mg, 0.019 mmol, 32%). ESI+MS m/z 632.3 (100%) [M+H]+.

Step B: 2-((S)-4-(2-(((R)-4-Methyl-7-oxa-4-azaspiro[2.5]octan-6-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl 2-(cyanomethyl)-4-(7-(2-(difluoromethyl)phenyl)-2-((S)-1-methylpyrrolidin-2-yl)methoxy)-5,6,7,8-tetrahydropyrido[3,4-d]pyrimidin-4-yl)piperazine-1-carboxylate (12.0 mg, 0.019 mmol) to afford 2-(4-(7-(2-(difluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile (9.5 mg, 0.019 mmol, 100%). ESI+MS m/z 498.3 (100%) [M+H]+.

Step C: 2-(1-Acryloyl-4-(7-(2-(difluoromethyl)phenyl)-2-(((S)-1-methylpyrrolidin-2-yl)methoxy)-5,6,7,8-tetrahydropyrido[3,4-d]pyrimidin-4-yl)piperazin-2-yl)acetonitrile Prepared according to the procedure of Example 375 Step G, substituting 2-(4-(7-(2-(difluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile (9.5 mg, 0.019 mmol) to afford title compound 2-(1-acryloyl-4-(7-(2-(difluoromethyl)phenyl)-2-((S)-1-methylpyrrolidin-2-yl)methoxy)-5,6,7,8-tetrahydropyrido[3,4-d]pyrimidin-4-yl)piperazin-2-yl)acetonitrile (EXAMPLE 449, 4.2 mg, 0.008 mmol, 40%). ESI+MS m/z 552.3 (100%) [M+H]+.

Example 450

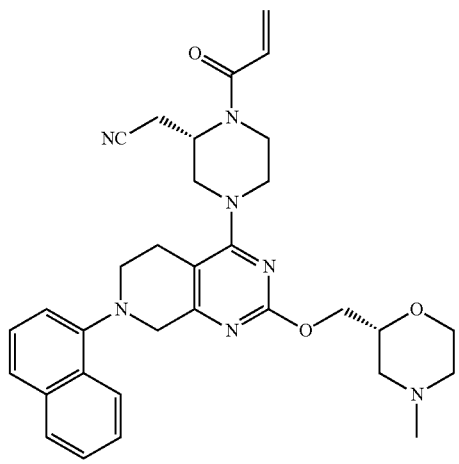 [SMILES: C=CC(=O)N1CCN(c2nc(OC[C@H]3CN(C)CCO3)nc3c2CCN(c2cccc4ccccc24)C3)C[C@@H]1CC#N]

2-((S)-1-Acryloyl-4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile

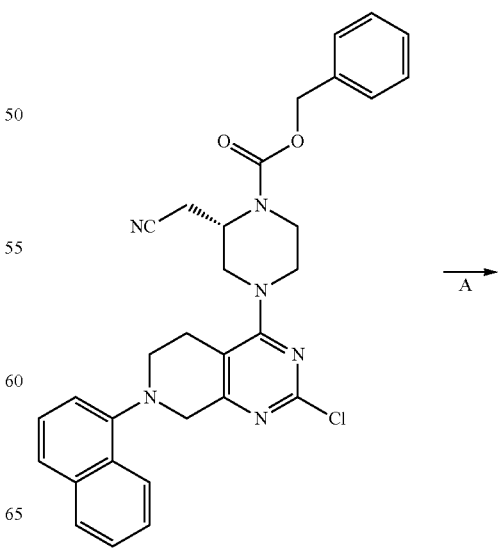

1201

-continued

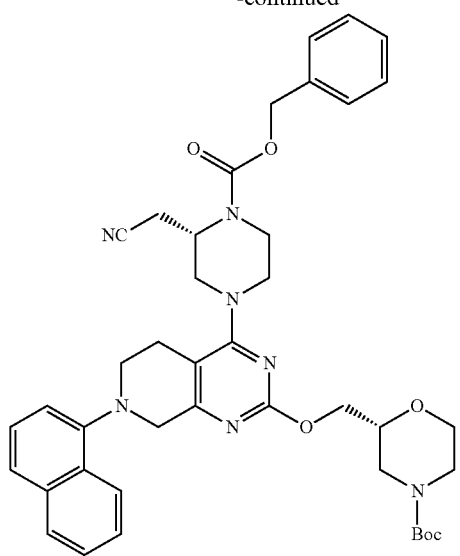


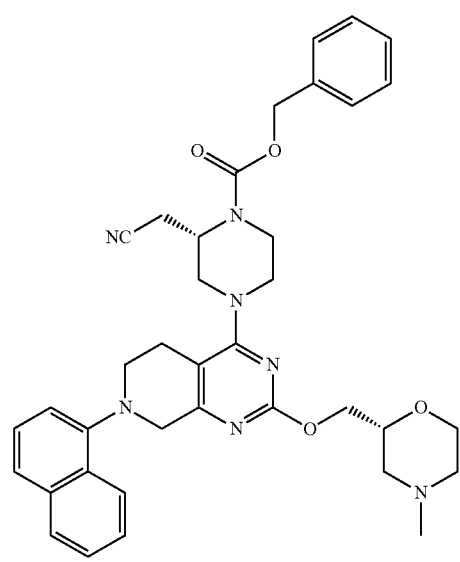

1202

-continued

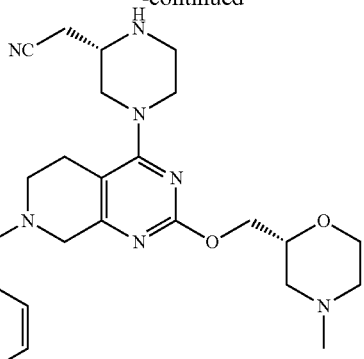

Step A: tert-Butyl (R)-2-(((4-((S)-4-((benzyloxy) carbonyl)-3-(cyanomethyl)piperazin-1-yl)-7-(naphthalen-1-yl)-5,6,7,8-tetrahydropyrido [3,4-d]pyrimidin-2-yl)oxy)methyl)morpholine-4-carboxylate Prepared according to the procedure of Example 443 Step A, substituting benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (95 mg, 0.172 mmol) and (R)—N-Boc-2-hydroxymethylmorpholine (112 mg, 0.515 mmol), purifying by flash chromatography eluting with 25-100% hex/EtOAc to afford tert-butyl (R)-2-(((4-((S)-4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (126 mg, 0.172 mmol, 100% yield). ESI+MS m/z 734.3 (100%) [M+H]+.

Step B: Benzyl (S)-2-(cyanomethyl)-4-(2-((R)-morpholin-2-yl)methoxy)-7-(naphthalen-1-yl)-5,6,7,8-tetrahydropyrido [3,4-d]pyrimidin-4-yl)piperazine-1-carboxylate hydrochloride Prepared according to the procedure of Example 375 Step D, substituting tert-butyl (R)-2-(((4-((S)-4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)morpholine-4-carboxylate (126 mg, 0.172 mmol) to afford benzyl (S)-2-(cyanomethyl)-4-(2-(((R)-morpholin-2-yl)methoxy)-7-(naphthalen-1-yl)-5,6,7,8-tetrahydropyrido [3,4-d]pyrimidin-4-yl)piperazine-1-carboxylate hydrochloride (109 mg, 0.172 mmol, 100%). ESI+MS m/z 634.3 (100%) [M+H]+.

Step C: Benzyl (S)-2-(cyanomethyl)-4-(2-(((R)-4-methylmorpholin-2-yl)methoxy)-7-(naphthalen-1-yl)-5,6,7,8-tetrahydropyrido[3,4-d]pyrimidin-4-yl)piperazine-1-carboxylate Prepared according to the procedure of Example 443 Step C, substituting benzyl (S)-2-(cyanomethyl)-4-(2-(((R)-4-methylmorpholin-2-yl)methoxy)-7-(naphthalen-1-yl)-5,6,7,8-tetrahydropyrido[3,4-d]pyrimidin-4-yl)piperazine-1-carboxylate (109 mg, 0.172 mmol) to afford benzyl (S)-2-(cyanomethyl)-4-(2-(((R)-4-methylmorpholin-2-yl)methoxy)-7-(naphthalen-1-yl)-5,6,7,8-tetrahydropyrido[3,4-d]pyrimidin-4-yl)piperazine-1-carboxylate (76 mg, 0.117 mmol, 68%). ESI+MS m/z 648.3 (100%) [M+H]+.

Step D: 2-((S)-4-(2-(((R)-4-Methylmorpholin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl (S)-2-(cyanomethyl)-4-(2-(((R)-4-methylmorpholin-2-yl)methoxy)-7-(naphthalen-1-yl)-5,6,7,8-tetrahydropyrido[3,4-d]pyrimidin-4-yl)piperazine-1-carboxylate (76 mg, 0.117 mmol) to afford 2-((S)-4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile (57.1 mg, 0.111 mmol, 95%). ESI+MS m/z 514.3 (100%) [M+H]+.

Step E: 2-(1-Acryloyl-4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step G, substituting 2-((S)-4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile (56 mg, 0.11 mmol) to afford title compound 2-((S)-1-acryloyl-4-(2-(((R)-4-methylmorpholin-2-yl)methoxy)-7-(naphthalen-1-yl)-5,6,7,8-tetrahydropyrido[3,4-d]pyrimidin-4-yl)piperazin-2-yl)acetonitrile (EXAMPLE 450, 50 mg, 0.088 mmol, 81%). ESI+MS m/z 568.3 (100%) [M+H]+.

Example 451

2-((S)-1-Acryloyl-4-(2-(((2R,5R)-4,5-dimethylmorpholin-2-yl)methoxy)-7-(naphthalen-1-yl)-5,6,7,8-tetrahydropyrido[3,4-d]pyrimidin-4-yl)piperazin-2-yl)acetonitrile

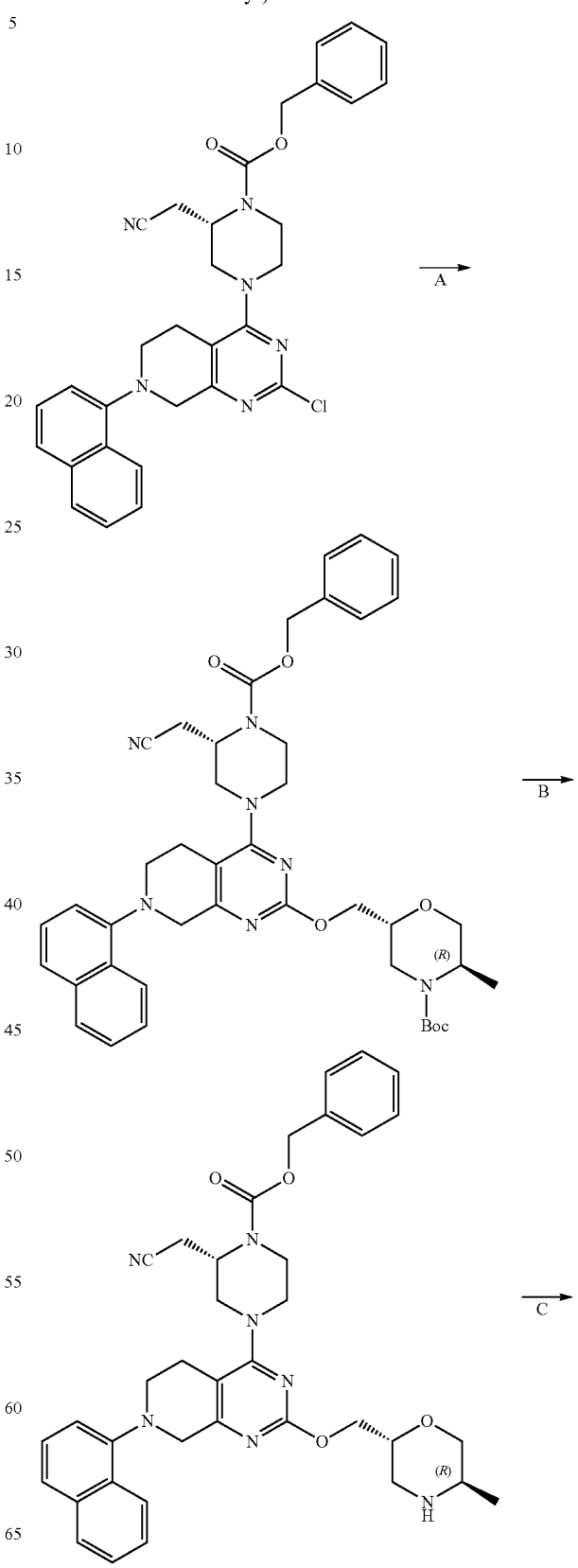

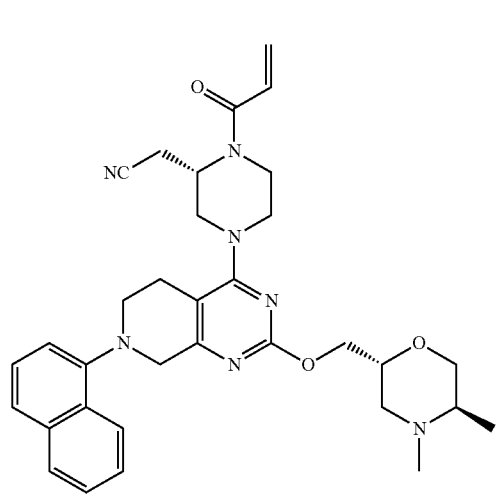 [SMILES: C=CC(=O)N1CCN(c2nc(OC[C@H]3CN(C)[C@H](C)CO3)nc3c2CCN(c2cccc4ccccc24)C3)C[C@@H]1CC#N]

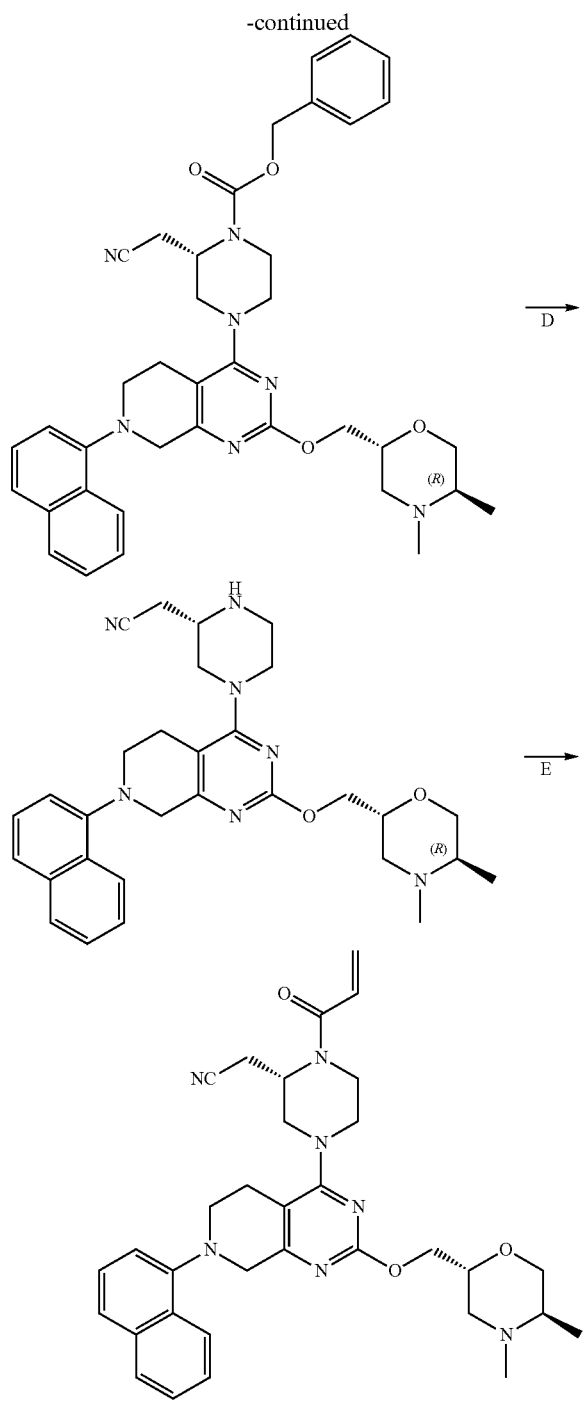

Step A: tert-Butyl (2R,5R)-2-(((4-((S)-4-((benzyloxy)carbonyl)-3-(cyanomethyl)piperazin-1-yl)-7-(naphthalen-1-yl)-5,6,7,8-tetrahydropyrido [3,4-d] pyrimidin-2-yl)oxy)methyl)-5-methylmorpholine-4-carboxylate Prepared according to the procedure of Example 375 Step C, substituting benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (95 mg, 0.172 mmol) and tert-butyl (2R,5R)-2-(hydroxymethyl)-5-methylmorpholine-4-carboxylate (119 mg, 0.515 mmol), purifying by flash chromatography eluting with 25-100% hex/EtOAc to afford tert-butyl (2R,5R)-2-(((4-((S)-4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)-5-methylmorpholine-4-carboxylate (128 mg, 0.171 mmol, 100% yield). ESI+MS m/z 748.3 (100%) [M+H]$^+$.

Step B: Benzyl (S)-2-(cyanomethyl)-4-(2-(((2R,5R)-5-methylmorpholin-2-yl)methoxy)-7-(naphthalen-1-yl)-5,6,7,8-tetrahydropyrido[3,4-d]pyrimidin-4-yl)piperazine-1-carboxylate Prepared according to the procedure of Example 375 Step D, substituting tert-butyl (2R,5R)-2-(((4-((S)-4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)-5-methylmorpholine-4-carboxylate (128 mg, 0.171 mmol) to afford benzyl (S)-2-(cyanomethyl)-4-(2-(((2R,5R)-5-methylmorpholin-2-yl)methoxy)-7-(naphthalen-1-yl)-5,6,7,8-tetrahydropyrido[3,4-d]pyrimidin-4-yl)piperazine-1-carboxylate (111 mg, 0.171 mmol, 100%). ESI+MS m/z 648.3 (100%) [M+H]$^+$.

Step C: Benzyl (S)-2-(cyanomethyl)-4-(2-(((2R,5R)-4,5-dimethylmorpholin-2-yl)methoxy)-7-(naphthalen-1-yl)-5,6,7,8-tetrahydropyrido[3,4-d]pyrimidin-4-yl)piperazine-1-carboxylate Prepared according to the procedure from Example 443 step C, substituting benzyl (S)-2-(cyanomethyl)-4-(2-(((2R,5R)-5-methylmorpholin-2-yl)methoxy)-7-(naphthalen-1-yl)-5,6,7,8-tetrahydropyrido[3,4-d]pyrimidin-4-yl)piperazine-1-carboxylate (111 mg, 0.171 mmol), to afford benzyl (S)-2-(cyanomethyl)-4-(2-(((2R,5R)-4,5-dimethylmorpholin-2-yl)methoxy)-7-(naphthalen-1-yl)-5,6,7,8-tetrahydropyrido [3,4-d]pyrimidin-4-yl)piperazine-1-carboxylate (56 mg, 0.085 mmol, 49%). ESI+MS m/z 662.3 (100%) [M+H]$^+$.

Step D: 2-((S)-4-(2-(((2R,5R)-4,5-Dimethylmorpholin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step F, substituting benzyl (S)-2-(cyanomethyl)-4-(2-(((2R,5R)-4,5-dimethylmorpholin-2-yl)methoxy)-7-(naphthalen-1-yl)-5,6,7,8-tetrahydropyrido[3,4-d]pyrimidin-4-yl)piperazine-1-carboxylate (56 mg, 0.085 mmol) to afford 2-((S)-4-(2-(((2R,5R)-4,5-dimethylmorpholin-2-yl)methoxy)-7-(naphthalen-1-yl)-5,6,7,8-tetrahydropyrido[3,4-d]pyrimidin-4-yl)piperazin-2-yl)acetonitrile (44.3 mg, 0.084 mmol, 99%). ESI+MS m/z 528.3 (100%) [M+H]$^+$.

Step E: 2-((S)-1-Acryloyl-4-(2-(((2R,5R)-4,5-dimethylmorpholin-2-yl)methoxy)-7-(naphthalen-1-yl)-5,6,7,8-tetrahydropyrido[3,4-d]pyrimidin-4-yl)piperazin-2-yl)acetonitrile Prepared according to the procedure of Example 375 Step G, substituting 2-((S)-4-(2-(((2R,5R)-4,5-dimethylmorpholin-2-yl)methoxy)-7-(naphthalen-1-yl)-5,6,7,8-tetrahydropyrido[3,4-d]pyrimidin-4-yl)piperazin-2-yl)acetonitrile (43 mg, 0.081 mmol) to afford title compound 2-((S)-1-acryloyl-4-(2-(((2R,5R)-4,5-dimethylmorpholin-2-yl)methoxy)-7-(naphthalen-1-yl)-5,6,7,8-tetrahydropyrido [3,4-d] pyrimidin-4-yl)piperazin-2-yl)acetonitrile (EXAMPLE 451, 32 mg, 0.055 mmol, 68%). ESI+MS m/z 582.3 (100%) [M+H]$^+$.
Example 452
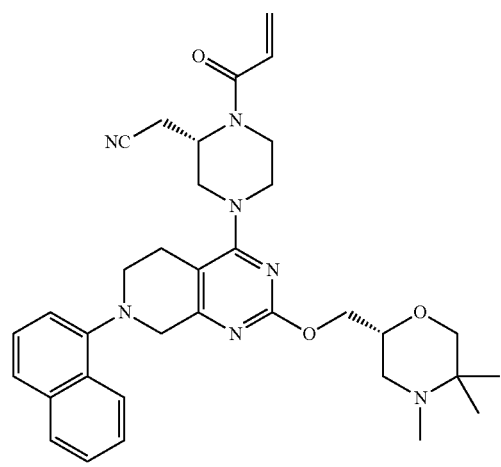
2-((S)-1-Acryloyl-4-(7-(naphthalen-1-yl)-2-(((R)-4,5,5-trimethylmorpholin-2-yl)methoxy)-5,6,7,8-tetrahydropyrido[3,4-d]pyrimidin-4-yl)piperazin-2-yl)acetonitrile
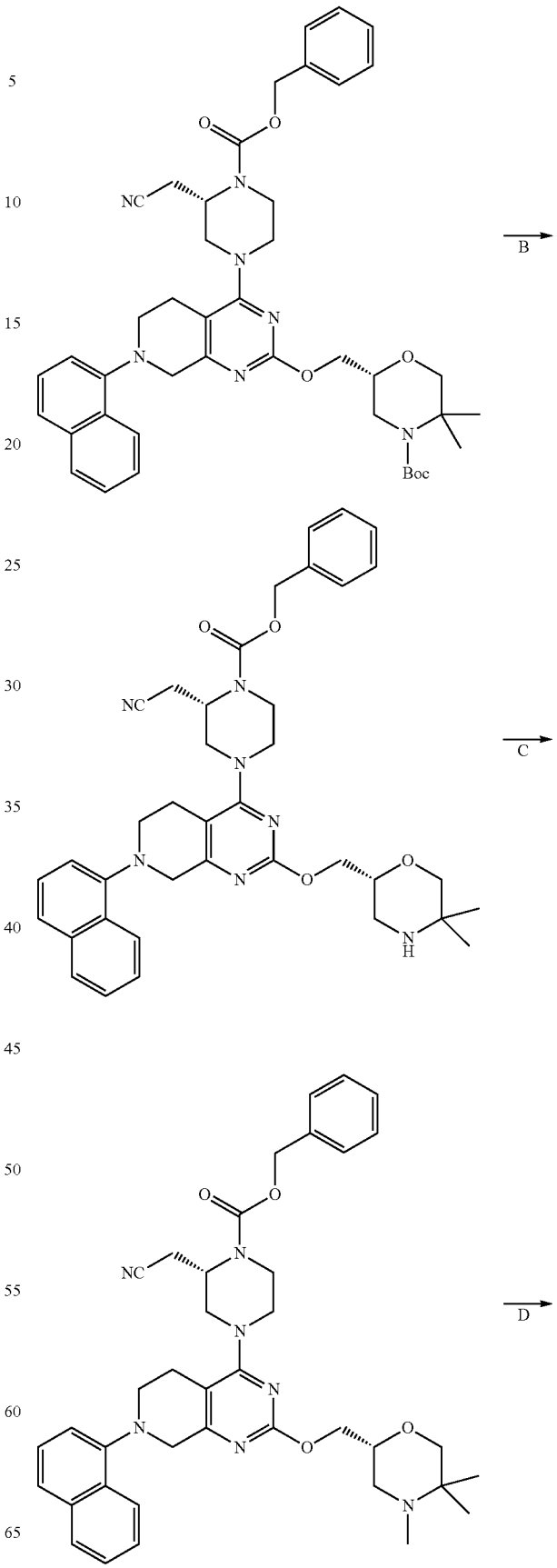

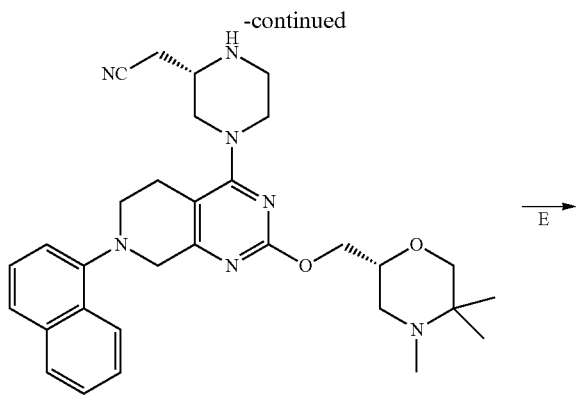

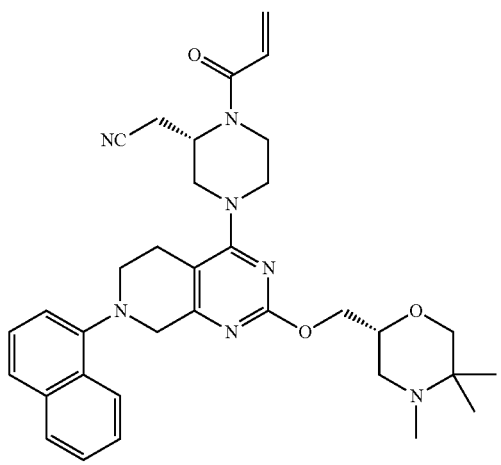 [SMILES: C=CC(=O)N1CCN(c2nc(OC[C@H]3CN(C)C(C)(C)CO3)nc3c2CCN(c2cccc4ccccc24)C3)C[C@@H]1CC#N]

Step A: tert-Butyl (R)-2-(((4-((S)-4-((benzyloxy) carbonyl)-3-(cyanomethyl)piperazin-1-yl)-7-(naphthalen-1-yl)-5,6,7,8-tetrahydropyrido [3,4-d]pyrimidin-2-yl)oxy)methyl)-5,5-dimethylmorpholine-4-carboxylate Prepared according to the procedure of Example 375 Step C, substituting benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate (95 mg, 0.172 mmol) and tert-butyl (R)-2-(hydroxymethyl)-5,5-dimethylmorpholine-4-carboxylate (126 mg, 0.515 mmol), purifying by flash chromatography eluting with 25-100% hex/EtOAc to afford tert-butyl (R)-2-(((4-((S)-4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)-5,5-dimethylmorpholine-4-carboxylate (131 mg, 0.172 mmol, 100% yield). ESI+MS m/z 762.3 (100%) [M+H]+.

Step B: Benzyl (S)-2-(cyanomethyl)-4-(2-(((R)-5,5-dimethylmorpholin-2-yl)methoxy)-7-(naphthalen-1-yl)-5,6,7,8-tetrahydropyrido[3,4-d]pyrimidin-4-yl)piperazine-1-carboxylate Prepared according to the procedure of Example 375 Step D, substituting tert-butyl (R)-2-(((4-((S)-4-((benzyloxy)carbonyl)-3-(cyanomethyl)piperazin-1-yl)-7-(naphthalen-1-yl)-5,6,7,8-tetrahydropyrido[3,4-d]pyrimidin-2-yl)oxy)methyl)-5,5-dimethylmorpholine-4-carboxylate (131 mg, 0.172 mmol) to afford benzyl (S)-2-(cyanomethyl)-4-(2-(((R)-5,5-dimethylmorpholin-2-yl)methoxy)-7-(naphthalen-1-yl)-5,6,7,8-tetrahydropyrido[3,4-d]pyrimidin-4-yl)piperazine-1-carboxylate (114 mg, 0.172 mmol, 100%). ESI+MS m/z 662.3 (100%) [M+H]+.

Step C: Benzyl (S)-2-(cyanomethyl)-4-(7-(naphthalen-1-yl)-2-(((R)-4,5,5-trimethylmorpholin-2-yl)methoxy)-5,6,7,8-tetrahydropyrido[3,4-d]pyrimidin-4-yl)piperazine-1-carboxylate Prepared according to the procedure from Example 443 step C, substituting benzyl (S)-2-(cyanomethyl)-4-(2-(((R)-5,5-dimethylmorpholin-2-yl)methoxy)-7-(naphthalen-1-yl)-5,6,7,8-tetrahydropyrido[3,4-d]pyrimidin-4-yl)piperazine-1-carboxylate (114 mg, 0.172 mmol), to afford benzyl (S)-2-(cyanomethyl)-4-(7-(naphthalen-1-yl)-2-(((R)-4,5,5-trimethylmorpholin-2-yl)methoxy)-5,6,7,8-tetrahydropyrido[3,4-d]pyrimidin-4-yl)piperazine-1-carboxylate (77 mg, 0.114 mmol, 66%). ESI+MS m/z 676.3 (100%) [M+H]+.

Step D: 2-((S)-4-(7-(Naphthalen-1-yl)-2-(((R)-4,5,5-trimethylmorpholin-2-yl)methoxy)-5,6,7,8-tetrahydropyrido[3,4-d]pyrimidin-4-yl)piperazin-2-yl)acetonitrile Prepared according to the procedure of Example 375 Step F, substituting benzyl (S)-2-(cyanomethyl)-4-(7-(naphthalen-1-yl)-2-(((R)-4,5,5-trimethylmorpholin-2-yl)methoxy)-5,6,7,8-tetrahydropyrido[3,4-d]pyrimidin-4-yl)piperazine-1-carboxylate (77 mg, 0.114 mmol) to afford 2-((S)-4-(7-(naphthalen-1-yl)-2-(((R)-4,5,5-trimethylmorpholin-2-yl)methoxy)-5,6,7,8-tetrahydropyrido[3,4-d]pyrimidin-4-yl)piperazin-2-yl)acetonitrile (47 mg, 0.087 mmol, 77%). ESI+MS m/z 542.3 (100%) [M+H]+.

Step E: 2-((S)-1-Acryloyl-4-(7-(naphthalen-1-yl)-2-(((R)-4,5,5-trimethylmorpholin-2-yl)methoxy)-5,6,7,8-tetrahydropyrido[3,4-d]pyrimidin-4-yl)piperazin-2-yl)acetonitrile Prepared according to the procedure of Example 1 Step G, substituting 2-((S)-4-(7-(naphthalen-1-yl)-2-(((R)-4,5,5-trimethylmorpholin-2-yl)methoxy)-5,6,7,8-tetrahydropyrido[3,4-d]pyrimidin-4-yl)piperazin-2-yl)acetonitrile (46 mg, 0.085 mmol) to afford title compound 2-((S)-1-acryloyl-4-(7-(naphthalen-1-yl)-2-(((R)-4,5,5-trimethylmorpholin-2-yl)methoxy)-5,6,7,8-tetrahydropyrido[3,4-d]pyrimidin-4-yl)piperazin-2-yl)acetonitrile (EXAMPLE 452, 36 mg, 0.060 mmol, 71%). ESI+MS m/z 582.3 (100%) [M+H]+.

Example 453

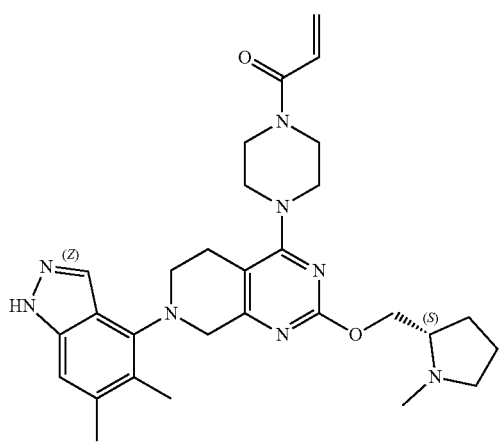

1-[4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one

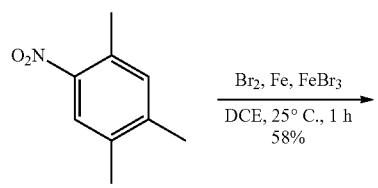

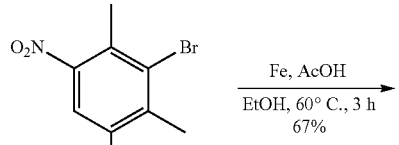

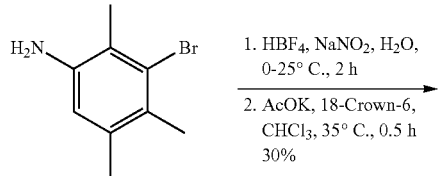

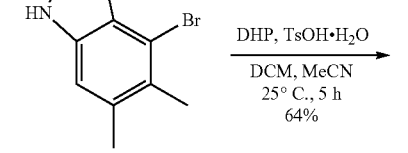

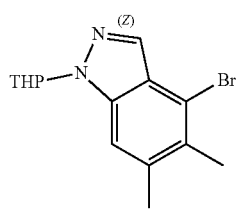

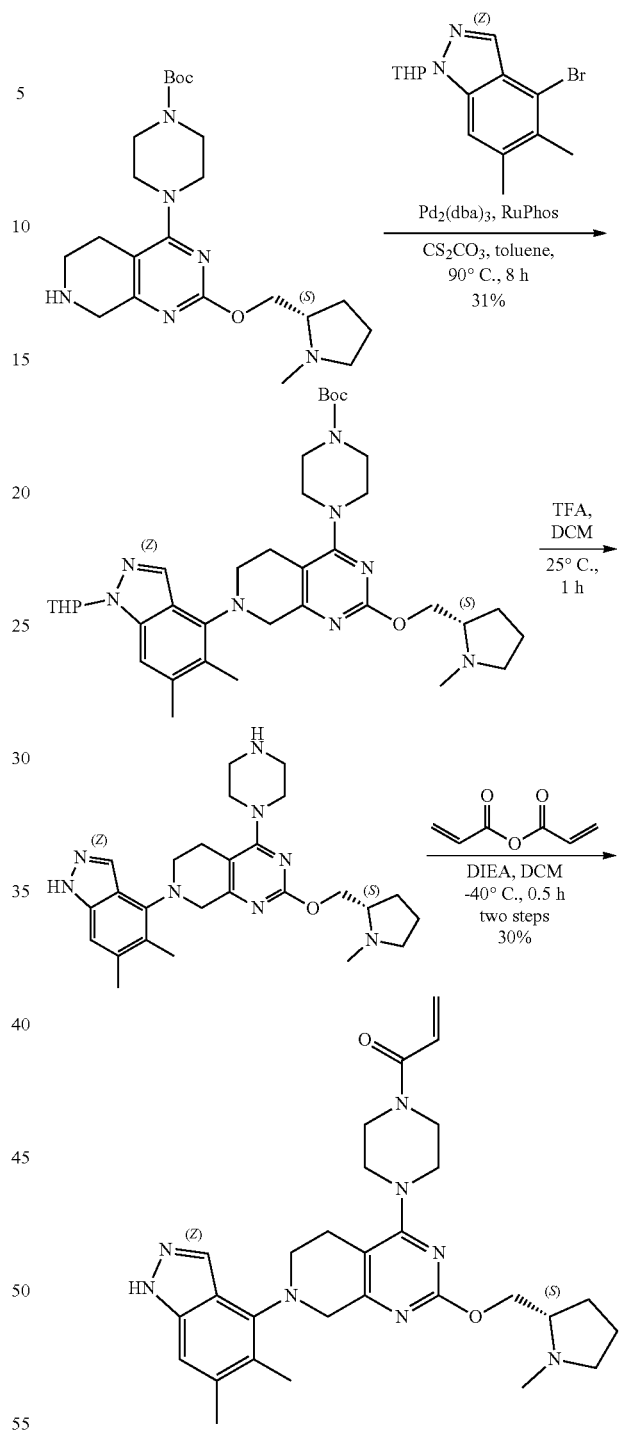

Step 1: 3-bromo-1,2,4-trimethyl-5-nitro-benzene

To a solution of 1,2,4-trimethyl-5-nitro-benzene (10 g, 60 mmol, 1 eq) in DCE (200 mL) was added FeBr$_3$ (358 mg, 1.21 mmol, 0.02 eq), Fe (879 mg, 15.7 mmol, 0.26 eq) following by Br$_2$ (11.6 g, 72.6 mmol, 3.74 mL, 1.2 eq) dropwise. After stirred at 25° C. for 1 hour, the reaction mixture was diluted with water (20 mL) and extracted with ethyl acetate (20 mL×3). The combined organic layers were washed with brine (20 mL), dried over Na$_2$SO$_4$, filtered and concentrated under reduced pressure to give a residue. The crude product was slurried in water and collected by filtration. 3-bromo-1,2,4-trimethyl-5-nitro-benzene (8.6 g, 34.9 mmol, 58% yield, 99% purity) was obtained as a white solid.

Step 2: 3-bromo-2,4,5-trimethyl-aniline

To a solution of 3-bromo-1,2,4-trimethyl-5-nitro-benzene (5.2 g, 21.3 mmol, 1 eq) in EtOH (100 mL) was added Fe (5.95 g, 107 mmol, 5 eq) and AcOH (12.8 g, 213 mmol, 12.2 mL, 10 eq). The mixture was stirred at 60° C. for 3 hours. Upon completion, the reaction mixture was filtered and the filtrate was concentrated. The residue was purified by reversed phase flash [water (0.1% formic acid)/acetonitrile)]. The desired fractions were collected and neutralized with saturated aqueous NaHCO$_3$, and then concentrated under vacuum to remove MeCN and extracted with EtOAc (2×100 mL). The organic layers were dried over Na$_2$SO$_4$ and concentrated under vacuum to give 3-bromo-2,4,5-trimethyl-aniline (3.4 g, 14.3 mmol, 67% yield, 90% purity) as a yellow solid.

$^1$H NMR (400 MHz, chloroform-d) δ=6.51 (s, 1H), 3.56 (br s, 2H), 2.32 (s, 3H), 2.31 (s, 3H), 2.26 (s, 3H).

Step 3: 4-bromo-5,6-dimethyl-1H-indazole 3-bromo-2,4,5-trimethyl-aniline (200 mg, 934.14 umol, 1 eq) was dissolved in trifluoroborane; hydrofluoride (1.69 g, 7.71 mmol, 1.20 mL, 8.25 eq, 40% in water) dropwise at 0° C. A cooled aqueous solution of NaNO$_2$ (96.7 mg, 1.40 mmol, 1.5 eq) (in the minimum of water to saturated aqueous). After addition, the mixture was stirred at 0° C. for 1 hour and 25° C. for 0.5 hour. NaNO$_2$ (64 mg, in the minimum of water to saturated aqueous) was added at 0° C. and the mixture was stirred at 0° C. for 0.5 hour. Then, the resulting precipitate was filtered, washed with (i-Pr)$_2$O (40 mL) and concentrated under vacuum which was directly added in one portion under N$_2$ to a stirred mixture of KOAc (183 mg, 1.87 mmol, 2 eq) and 18-CROWN-6 (12.4 mg, 46.7 umol, 0.05 eq) in CHCl$_3$ (8 mL). The mixture was stirred at 35° C. for 0.5 hour. Upon completion, the mixture was filtered and the filtrate was concentrated under vacuum. The residue was purified by silica gel chromatography (PE/EtOAc 100/1 to 5/1) to give 4-bromo-5,6-dimethyl-1H-indazole (70 mg, 280 umol, 30% yield, 90% purity) as a yellow solid.

Step 4: 4-bromo-5,6-dimethyl-1-tetrahydropyran-2-yl-indazole

To a solution of 4-bromo-5,6-dimethyl-1H-indazole (290 mg, 1.29 mmol, 1 eq) in DCM (6 mL) was added TsOH.H$_2$O (24.5 mg, 129 umol, 0.1 eq), followed by DHP (217 mg, 2.58 mmol, 236 uL, 2 eq) and MeCN (1 mL). The mixture was stirred at 25° C. for 5 hours. Upon completion, the mixture was quenched with saturated aqueous NaHCO$_3$ solution (5 mL), diluted with water (20 mL). layers were separated and the aqueous phase was extracted with EtOAc (2×200 mL). Combined organic layers were dried over Na$_2$SO$_4$, filtered and concentrated under vacuum. The residue was purified by silica gel chromatography (PE/EtOAc 100/1 to 25/1) to give 4-bromo-5,6-dimethyl-1-tetrahydropyran-2-yl-indazole (320 mg, 828 umol, 64% yield, 80% purity) as a yellow oil. LCMS [ESI, M+1]: 309.

$^1$H NMR (400 MHz, chloroform-d) δ=7.94 (s, 1H), 7.33 (s, 1H), 5.66 (dd, J=2.8, 9.2 Hz, 1H), 4.06-3.97 (m, 1H), 3.79-3.67 (m, 1H), 2.47 (s, 3H), 2.44 (s, 3H), 2.16 (qd, J=4.4, 7.6 Hz, 1H), 2.06 (qd, J=3.2, 13.2 Hz, 1H), 1.83-1.64 (m, 4H).

Step A: tert-butyl 4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate (385 mg, 890 umol, 1 eq), 4-bromo-5,6-dimethyl-1-tetrahydropyran-2-yl-indazole (303 mg, 979 umol, 1.10 eq), Pd$_2$(dba)$_3$ (163 mg, 178 umol, 0.2 eq), RuPhos (166 mg, 356 umol, 0.4 eq) and Cs$_2$CO$_3$ (725 mg, 2.23 mmol, 2.5 eq) in toluene (30 mL) was de-gassed and then heated to 90° C. for 8 hours under N$_2$. Upon completion, the mixture was filtered and the filtrate was concentrated under vacuum. The residue was purified by silica gel chromatography (EtOAc/MeOH 100/1 to 5/1) to give tert-butyl 4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (200 mg, 275 umol, 31% yield, 91% purity) as a yellow solid. LCMS [ESI, M+1]: 661.

Step B: 7-(5,6-dimethyl-1H-indazol-4-yl)-2-[[(2S)-1-methylpyrrolidin-2-yl]methoxy]-4-piperazin-1-yl-6,8-dihydro-5H-pyrido[3,4-d]pyrimidine To a solution of tert-butyl 4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (190 mg, 288 umol, 1 eq) in DCM (0.4 mL) was added TFA (924 mg, 8.10 mmol, 0.6 mL, 28.2 eq). The mixture was stirred at 25° C. for 1 hour. Upon completion, the mixture was concentrated under vacuum to give 7-(5,6-dimethyl-1H-indazol-4-yl)-2-[[(2S)-1-methylpyrrolidin-2-yl]methoxy]-4-piperazin-1-yl-6,8-dihydro-5H-pyrido[3,4-d]pyrimidine (220 mg, crude, 2TFA) as a yellow oil which was used directly into the next step without further purification.

Step C: 1-[4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one To a solution of 7-(5,6-dimethyl-1H-indazol-4-yl)-2-[[(2S)-1-methylpyrrolidin-2-yl]methoxy]-4-piperazin-1-yl-6,8-dihydro-5H-pyrido[3,4-d]pyrimidine (200 mg, 284 umol, 1 eq, 2 TFA) and TEA (574 mg, 5.68 mmol, 790 uL, 20 eq) in DCM (4 mL) was added prop-2-enoyl prop-2-enoate (35.8 mg, 284 umol, 1 eq) dropwise at −40° C. The mixture was stirred at −40° C. for 30 minutes. Upon completion, the mixture was quenched with MeOH (0.5 mL), diluted with water (5 mL) and then extracted with DCM (2×10 mL). The extracts were dried over Na$_2$SO$_4$, filtered and concentrated under vacuum. The residue was purified by chromatography (Al$_2$O$_3$, EtOAc/MeOH 100/1 to 10/1) and prep-HPLC (column: Gemini 150*25 5 u; mobile phase: [water (0.05% ammonia hydroxide v/v)-ACN]; B %: 35%-65%, 12 min). The desired fractions were collected and lyophilized to give title compound 1-[4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one (EXAMPLE 453, 45.3 mg, 85.2 umol, two steps 30% yield, 99.7% purity) as a white solid. LCMS [ESI, M+1]:531.

SFC condition: Column: Chiralcel OJ-3 100×4.6 mm I.D., 3 um, Mobile phase: methanol (0.05% DEA) in CO$_2$ from 5% to 40%, Flow rate: 3 mL/min, Wavelength: 220 nm.

$^1$H NMR (400 MHz, chloroform-d) δ=10.84 (br s, 1H), 8.02 (s, 1H), 7.13 (s, 1H), 6.59 (dd, J=10.4, 16.8 Hz, 1H), 6.34 (dd, J=1.2, 16.8 Hz, 1H), 5.79-5.68 (m, 1H), 4.40 (dd, J=4.8, 10.4 Hz, 1H), 4.26 (s, 2H), 4.17 (dd, J=6.8, 10.4 Hz, 1H), 3.90-3.39 (m, 10H), 3.09 (br t, J=7.6 Hz, 1H), 2.89-2.62 (m, 3H), 2.47 (s, 3H), 2.39 (s, 3H), 2.33 (s, 3H), 2.30-2.23 (m, 1H), 2.09-1.97 (m, 1H), 1.91-1.69 (m, 3H).

Example 454

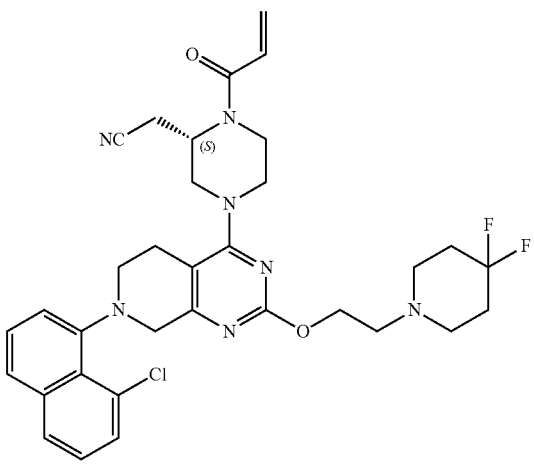

2-[(2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]-1-prop-2-enoyl-piperazin-2-yl]acetonitrile

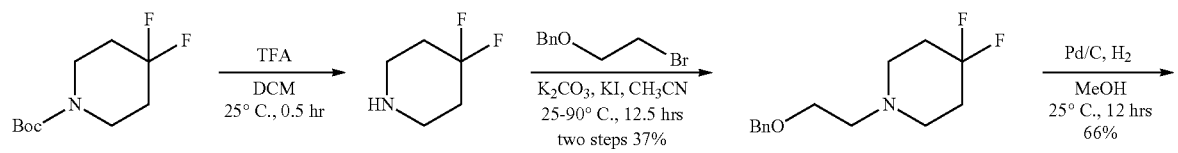

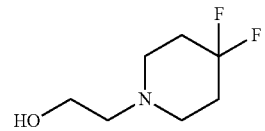

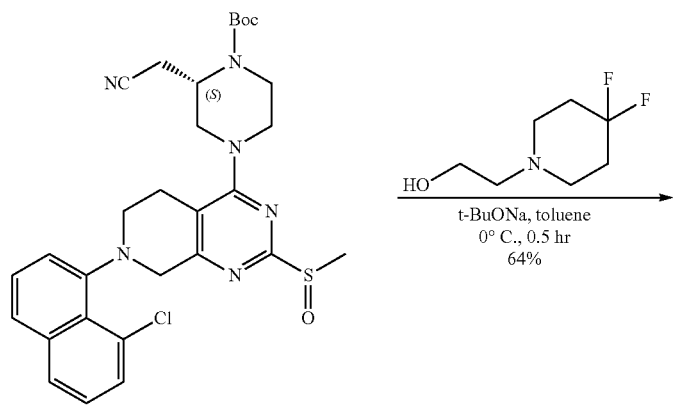

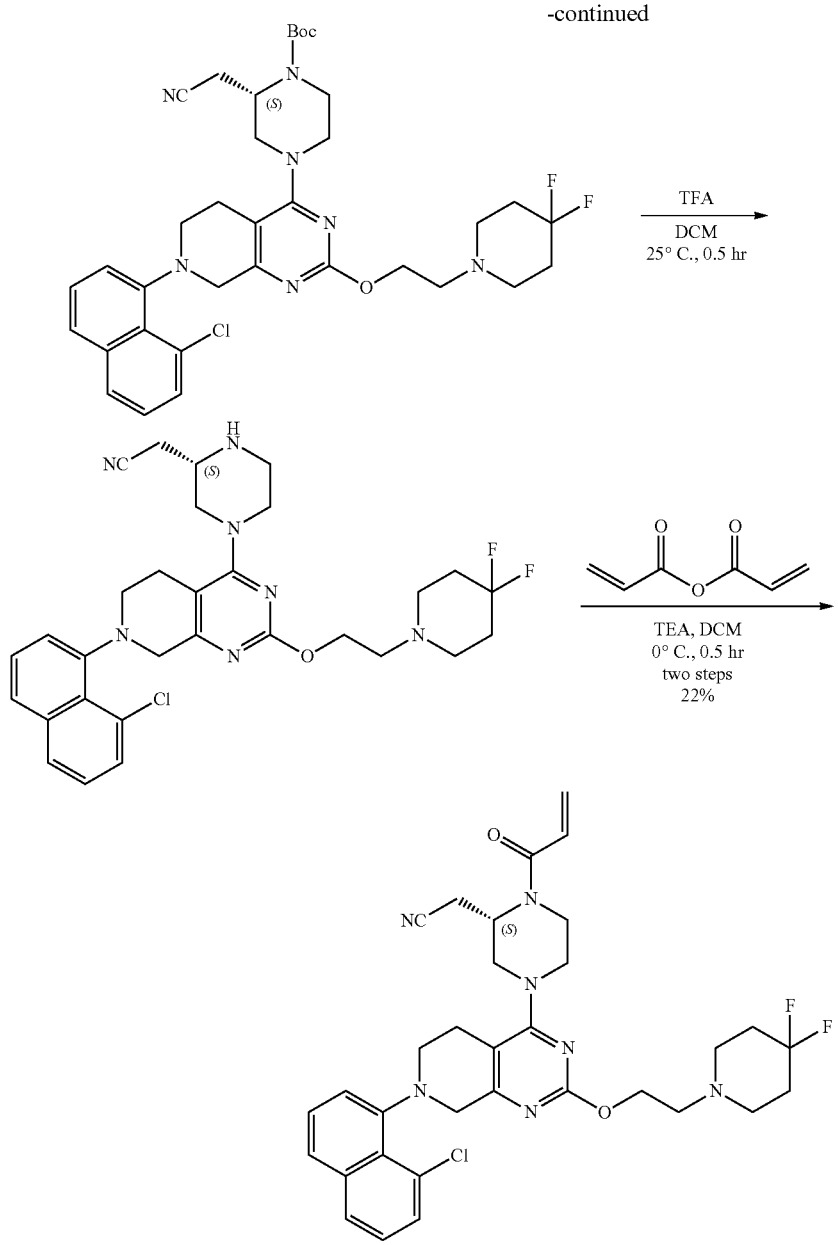

Step 1: 4,4-difluoropiperidine

To a solution of tert-butyl 4,4-difluoropiperidine-1-carboxylate (2.0 g, 9.04 mmol, 1.0 eq) in DCM (0.50 mL) was added TFA (770 mg, 6.75 mmol, 0.50 mL, 7.47 e$^{-1}$ eq). The mixture was stirred at 25° C. for 0.5 hour. After completion, the reaction mixture was concentrated under vacuum to give the product 4,4-difluoropiperidine (1.50 g, crude, TFA) as yellow oil which was used for the next step without further purification.

Step 2: 1-(2-benzyloxyethyl)-4,4-difluoro-piperidine

To a solution of 4,4-difluoropiperidine (1.50 g, 6.38 mmol, 1.0 eq, TFA) in MeCN (20.0 mL) was added NaOH (765 mg, 19.1 mmol, 3.0 eq). The mixture was stirred at 25° C. for 0.5 hour. Then 2-bromoethoxymethylbenzene (1.65 g, 7.65 mmol, 1.21 mL, 1.20 eq) and KI (212 mg, 1.28 mmol, 0.20 eq) was added to the above liquid, the mixture was stirred at 90° C. for 12 hours. After completion, the reaction mixture was added water (20.0 mL), and then extracted with EA (3×20.0 mL). The combined organic layers were dried over by Na$_2$SO$_4$, filtered and concentrated. The residue was purified by column chromatography (SiO$_2$, Petroleum ether: Ethyl acetate=10:1 to 0:1) to give 1-(2-benzyloxyethyl)-4,4-difluoro-piperidine (600 mg, 2.35 mmol, two steps 37% yield) as yellow oil.

$^1$H NMR (400 MHz, Chloroform-d) δ 7.41-7.29 (m, 5H), 4.54 (s, 2H), 3.82-3.72 (m, 2H), 3.33-2.94 (m, 6H), 2.37-2.15 (m, 4H).

Step 3: 2-((4,4-difluoro-1-piperidyl)ethanol

A solution of 1-(2-benzyloxyethyl)-4,4-difluoro-piperidine (400 mg, 1.57 mmol, 1.0 eq) and Pd/C (200 mg, 10% purity) in EtOH (5.0 mL) was stirred under H$_2$ (15 Psi)

atmosphere at 25° C. for 12 hours. After completion, the reaction mixture was filtered through Celite, the filter cake was washed with THF (10.0 mL). The filtrate was collected and concentrated to give the product 2-((4,4-difluoro-1-piperidyl)ethanol (170 mg, 1.03 mmol, 66% yield) as colorless oil. The product was used for the next step without further purification.

$^1$H NMR (400 MHz, Chloroform-d) δ 3.84-3.70 (m, 2H), 2.98-2.89 (m, 4H), 2.86-2.80 (m, 3H), 2.24-2.11 (m, 4H).

Step A: tert-butyl (2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]-2-(cyanomethyl)piperazine-1-carboxylate To a solution of 2-((4,4-difluoro-1-piperidyl)ethanol (102 mg, 619 umol, 3.0 eq) in toluene (3.0 mL) and tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (120 mg, 206 umol, 1.0 eq) was added t-BuONa (39.7 mg, 413 umol, 2.0 eq), the mixture was stirred at 0° C. for 0.5 hour. After completion, the reaction mixture was added water (10.0 mL) and extracted with EA (3×10.0 mL). The organic layer was dried over Na$_2$SO$_4$, filtered and concentrated under vacuum. The residue was purified by reversed phase flash (C18, 0.1% NH$_3$.H$_2$O, 0-60% MeCN) to give the product tert-butyl (2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]-2-(cyanomethyl)piperazine-1-carboxylate (90.0 mg, 132 umol, 64% yield) as yellow oil. LCMS [ESI, M+1]: 682.

Step B: 2-[(2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]-2-(cyanomethyl)piperazine-1-carboxylate (30.0 mg, 44.0 umol, 1.0 eq) in DCM (0.5 mL) was added TFA (770 mg, 6.75 mmol, 0.50 mL, 154 eq). The mixture was stirred at 25° C. for 0.5 hour. After completion, the mixture was concentrated. The residue was adjusted with saturated NaHCO$_3$ aqueous to pH ~7, then extracted with EA (3×5.0 mL). The organic layer was dried over Na$_2$SO$_4$, filtered and concentrated to give the product 2-[(2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]piperazin-2-yl]acetonitrile (26.0 mg, crude) as yellow oil which was used for the next step without further purification. LCMS [ESI, M+1]: 582.

Step C: 2-[(2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]-1-prop-2-enoyl-piperazin-2-yl]acetonitrile To a solution of 2-[(2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]piperazin-2-yl]acetonitrile (26.0 mg, 44.7 umol, 1.0 eq) and DIEA (69.3 mg, 536 umol, 93.4 uL, 12.0 eq) in DCM (1.0 mL) was added prop-2-enoyl prop-2-enoate (8.45 mg, 67.0 umol, 1.50 eq). The mixture was stirred at 0° C. for 0.5 hour. After completion, the mixture was quenched by addition MeOH (1.0 mL), and then concentrated to give a residue. Then the residue was purified by prep-HPLC (column: Gemini 150*25 5 u; mobile phase: [water (0.05% ammonia hydroxide v/v)-ACN]; B %: 47%-77%, 12 min) to give title compound 2-[(2S)-4-[7-(8-chloro-1-naphthyl)-2-[2-((4,4-difluoro-1-piperidyl)ethoxy]-6,8-dihydro-5H-pyrido[3,4-d]pyrimidin-4-yl]-1-prop-2-enoyl-piperazin-2-yl]acetonitrile (EXAMPLE 454, 6.35 mg, 9.82 umol, two steps 22% yield, 98% purity) as white solid. LCMS [ESI, M+1]: 636.

$^1$H NMR (400 MHz, Chloroform-d) δ 7.76 (br d, J=8.0 Hz, 1H), 7.63 (t, J=7.2 Hz, 1H), 7.53 (d, J=7.2 Hz, 1H), 7.49-7.40 (m, 1H), 7.34 (t, J=7.8 Hz, 1H), 7.27-7.17 (m, 1H), 6.67-6.54 (m, 1H), 6.40 (br d, J=16.4 Hz, 1H), 5.83 (br d, J=11.2 Hz, 1H), 5.20-4.56 (m, 1H), 4.50-4.35 (m, 3H), 4.22-4.01 (m, 2H), 3.98-3.75 (m, 2H), 3.66-3.57 (m, 1H), 3.53-3.36 (m, 1H), 3.31-2.98 (m, 4H), 2.91-2.80 (m, 3H), 2.79-2.49 (m, 6H), 2.09-1.94 (m, 4H).

Example 455

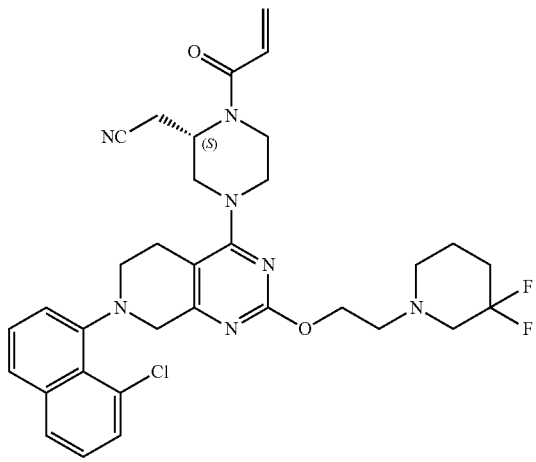

2-[(2S)-4-[7-(8-chloro-1-naphthyl)-2-[2-(3,3-difluoro-1-piperidyl)ethoxy]-6,8-dihydro-5H-pyrido[3,4-d]pyrimidin-4-yl]-1-prop-2-enoyl-piperazin-2-yl]acetonitrile

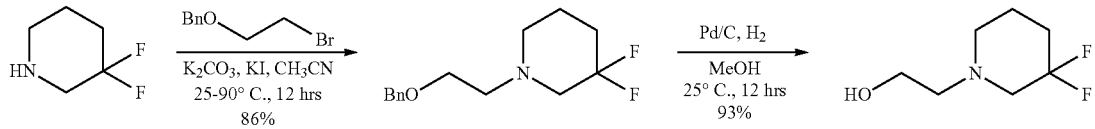

1221                                    -continued                                    1222
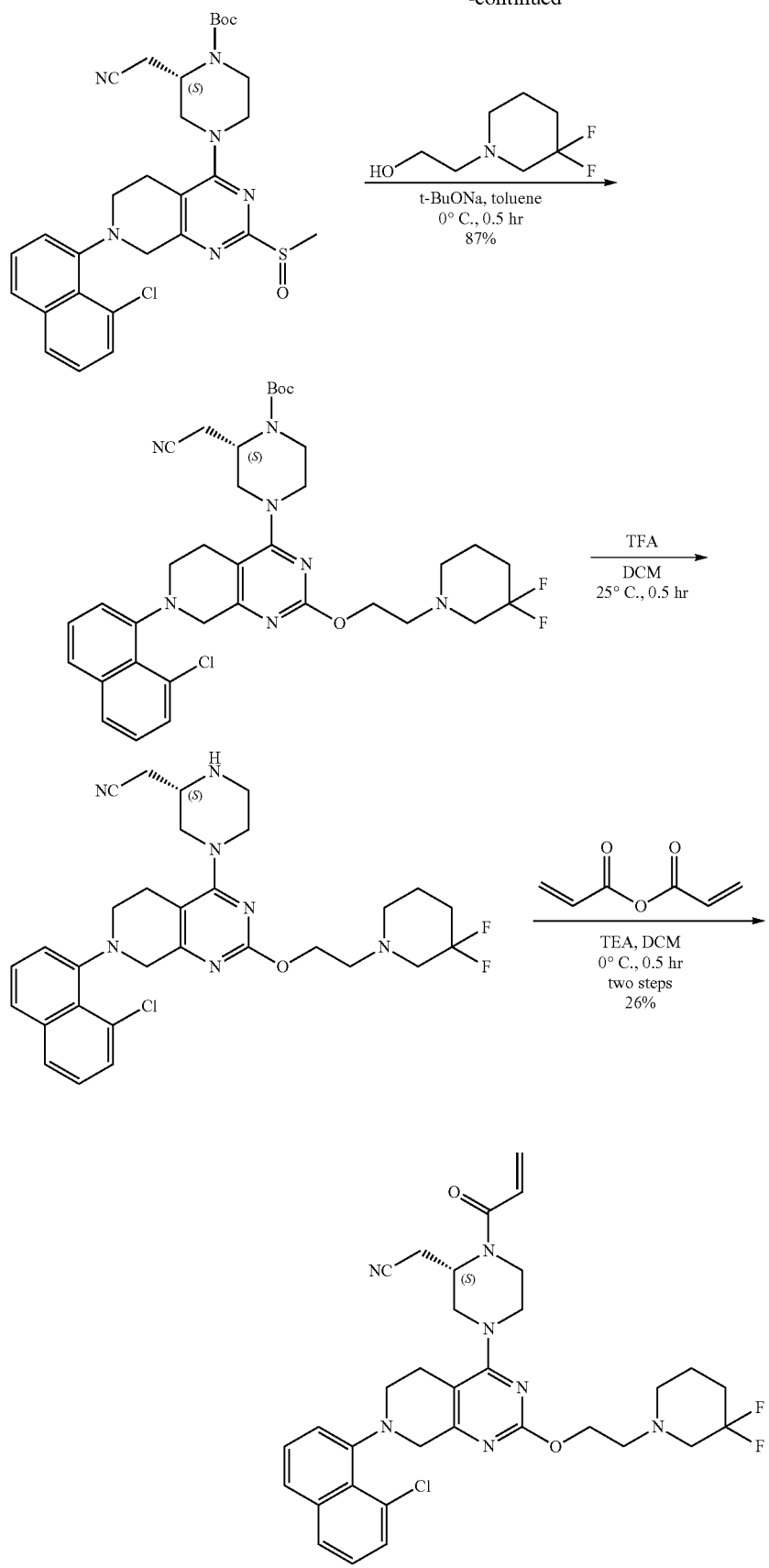

Step 1: 1-(2-benzyloxyethyl)-3,3-difluoro-piperidine

To a solution of 3,3-difluoropiperidine (1.0 g, 6.35 mmol, 1.0 eq, HCl) in MeCN (6.0 mL) was added NaOH (761 mg, 19.0 mmol, 3.0 eq) in one portion at 25° C. The mixture was stirred at 25° C. for 5 minutes, then 2-bromoethoxymethylbenzene (1.64 g, 7.61 mmol, 1.20 mL, 1.20 eq) and KI (211 mg, 1.27 mmol, 0.20 eq) was added. The mixture was stirred at 90° C. for 12 hours. After completion, the reaction mixture was added H$_2$O (15.0 mL), and then extracted with EA (3×20.0 mL). The combined organic layers were dried over by Na$_2$SO$_4$, filtered and concentrated to give a residue. The residue was purified by column chromatography (SiO$_2$, Petroleum ether/Ethyl acetate=10:1 to 5:1) to give 1-(2-benzyloxyethyl)-3,3-difluoro-piperidine (1.40 g, 5.48 mmol, 86% yield) as colorless oil.

$^1$H NMR (400 MHz, Chloroform-d) δ 7.38-7.31 (m, 5H), 4.56 (s, 2H), 3.64 (t, J=5.8 Hz, 2H), 2.79-2.73 (m, 4H), 2.55 (t, J=5.4 Hz, 2H), 1.85-1.85 (m, 2H), 1.82-1.76 (m, 2H).

Step 2: 2-(3,3-difluoro-1-piperidyl)ethanol

To a solution of 1-(2-benzyloxyethyl)-3,3-difluoro-piperidine (400 mg, 1.57 mmol, 1.0 eq) in MeOH (5.0 mL) was added Pd/C (200 mg, 10% purity) under N$_2$. The suspension was degassed under vacuum and purged with H$_2$ several times. The mixture was stirred under H$_2$ (15 psi) at 40° C. for 12 hours. After completion, the reaction mixture was filtered and concentrated to give 2-(3,3-difluoro-1-piperidyl)ethanol (240 mg, 1.45 mmol, 93% yield) as colorless oil. The product was used for the next step without further purification.

$^1$H NMR (400 MHz, Chloroform-d) δ 3.64 (t, J=5.4 Hz, 2H), 2.73 (t, J=11.2 Hz, 2H), 2.63 (t, J=5.4 Hz, 2H), 2.54 (t, J=5.2 Hz, 2H), 1.97-1.87 (m, 2H), 1.82-1.76 (m, 2H).

Step A: tert-butyl (2S)-4-[7-(8-chloro-1-naphthyl)-2-[2-(3,3-difluoro-1-piperidyl)ethoxy]-6,8-dihydro-5H-pyrido[3,4-d]pyrimidin-4-yl]-2-(cyanomethyl)piperazine-1-carboxylate A mixture of tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (230 mg, 396 umol, 1.0 eq), 2-(3,3-difluoro-1-piperidyl)ethanol (196 mg, 1.19 mmol, 3.0 eq), t-BuONa (114 mg, 1.19 mmol, 3.0 eq) in toluene (5.0 mL) was degassed and purged with N$_2$ for 3 times, and then the mixture was stirred at 0° C. for 0.5 hour under N$_2$ atmosphere. After completion, the reaction mixture was quenched by H$_2$O (5.0 mL) and extracted with EA (3×10.0 mL). The combined organic layer was washed with saturated NaCl aqueous solution (20.0 mL), dried over Na$_2$SO$_4$, filtered and concentrated to give a residue. The residue was purified by column chromatography (SiO$_2$, Petroleum ether/Ethyl acetate=3:1 to 0:1) to give tert-butyl (2S)-4-[7-(8-chloro-1-naphthyl)-2-[2-(3,3-difluoro-1-piperidyl)ethoxy]-6,8-dihydro-5H-pyrido[3,4-d]pyrimidin-4-yl]-2-(cyanomethyl)piperazine-1-carboxylate (250 mg, 344 umol, 87% yield, 94% purity) as yellow oil.

$^1$H NMR (400 MHz, Chloroform-d) δ 7.77 (d, J=8.0 Hz, 1H), 7.63 (t, J=8.0 Hz, 1H), 7.54 (d, J=7.2 Hz, 1H), 7.50-7.42 (m, 1H), 7.37-7.33 (m, 1H), 7.27-7.20 (m, 1H), 4.67-4.64 (m, 1H), 4.48-4.39 (m, 3H), 4.06 (d, J=12.8 Hz, 1H), 4.01-3.80 (m, 3H), 3.60 (d, J=4.0 Hz, 1H), 3.37 (dd, J=3.6, 13.6 Hz, 1H), 3.27-3.10 (m, 3H), 2.97-2.90 (m, 3H), 2.84-2.78 (m, 3H), 2.61-2.57 (m, 2H), 1.89-1.85 (m, 3H), 1.72-1.54 (m, 3H), 1.53 (s, 9H).

Step B: 2-[(2S)-4-[7-(8-chloro-1-naphthyl)-2-[2-(3,3-difluoro-1-piperidyl)ethoxy]-6,8-dihydro-5H-pyrido[3,4-d]pyrimidin-4-yl]piperazin-2-yl]acetonitrile To a mixture of tert-butyl (2S)-4-[7-(8-chloro-1-naphthyl)-2-[2-(3,3-difluoro-1-piperidyl)ethoxy]-6,8-dihydro-5H-pyrido[3,4-d]pyrimidin-4-yl]-2-(cyanomethyl)piperazine-1-carboxylate (200 mg, 293 umol, 1.0 eq) in DCM (1.50 mL) was added TFA (2.31 g, 20.3 mmol, 1.50 mL, 69.0 eq) in one portion at 25° C. under N$_2$. The mixture was stirred at 25° C. for 0.5 hour. After completion, the mixture was concentrated to give 2-[(2S)-4-[7-(8-chloro-1-naphthyl)-2-[2-(3,3-difluoro-1-piperidyl)ethoxy]-6,8-dihydro-5H-pyrido[3,4-d]pyrimidin-4-yl]piperazin-2-yl]acetonitrile (400 mg, crude, 2TFA) as yellow solid. The product was used for the next step without further purification. LCMS [ESI, M+1]: 582.

Step C: 2-[(2S)-4-[7-(8-chloro-1-naphthyl)-2-[2-(3,3-difluoro-1-piperidyl)ethoxyl]-6,8-dihydro-5H-pyrido[3,4-d]pyrimidin-4-yl]-1-prop-2-enoyl-piperazin-2-yl]acetonitrile To a mixture of 2-[(2S)-4-[7-(8-chloro-1-naphthyl)-2-[2-(3,3-difluoro-1-piperidyl)ethoxy]-6,8-dihydro-5H-pyrido[3,4-d]pyrimidin-4-yl]piperazin-2-yl]acetonitrile (400 mg, 494 umol, crude, 2TFA) and TEA (727 mg, 7.18 mmol, 1.0 mL) in DCM (2.0 mL) was added prop-2-enoyl prop-2-enoate (100 mg, 793 umol) in one portion at 0° C. under N$_2$. The mixture was stirred at 0° C. for 0.5 hour. After completion, the mixture was quenched by addition MeOH (3.0 mL) at 0° C., and then concentrated to give a residue. Then the residue was purified by prep-HPLC (column: Phenomenex Gemini 150*25 mm*10 um; mobile phase: [water (10.0 mM NH$_4$HCO$_3$)-ACN]; B %: 57%-87%, 10 min.) and lyophilized to give title compound 2-[(2S)-4-[7-(8-chloro-1-naphthyl)-2-[2-(3,3-difluoro-1-piperidyl)ethoxy]-6,8-dihydro-5H-pyrido[3,4-d]pyrimidin-4-yl]-1-prop-2-enoyl-piperazin-2-yl]acetonitrile (EXAMPLE 455, 48.4 mg, 75.8 umol, 26% yield, 99% purity) as white solid.

SFC condition: 100%. e.e.

$^1$H NMR (400 MHz, Chloroform-d) δ 7.78 (d, J=8.0 Hz, 1H), 7.64 (t, J=7.4 Hz, 1H), 7.54 (d, J=7.6 Hz, 1H), 7.50-7.43 (m, 1H), 7.36 (t, J=7.8 Hz, 1H), 7.27-7.21 (m, 1H), 6.60-6.58 (m, 1H), 6.44-6.39 (m, 1H), 5.85 (d, J=10.4 Hz, 1H), 5.10-4.66 (m, 1H), 4.49-4.40 (m, 3H), 4.18-4.08 (m, 2H), 3.94-3.89 (m, 1H), 3.85-3.73 (m, 1H), 3.63-3.60 (m, 1H), 3.50-3.41 (m, 1H), 3.33-3.02 (m, 4H), 2.94-2.76 (m, 6H), 2.64-2.61 (m, 3H), 1.95-1.85 (m, 2H), 1.80-1.78 (m, 2H). LCMS [ESI, M+1]: 636.

Example 456
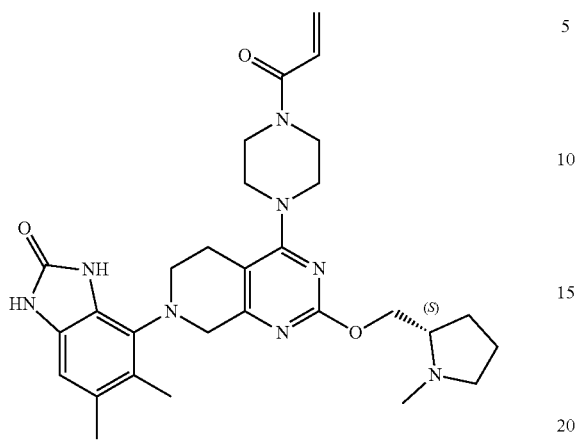
5,6-dimethyl-4-[2-[[(2S)-1-methylpyrrolidin-2-yl]
methoxy]-4-(4-prop-2-enoylpiperazin-1-yl)-6,8-di-
hydro-5H-pyrido[3,4-d]pyrimidin-7-yl]-1,3-dihyd-
robenzimidazol-2-one
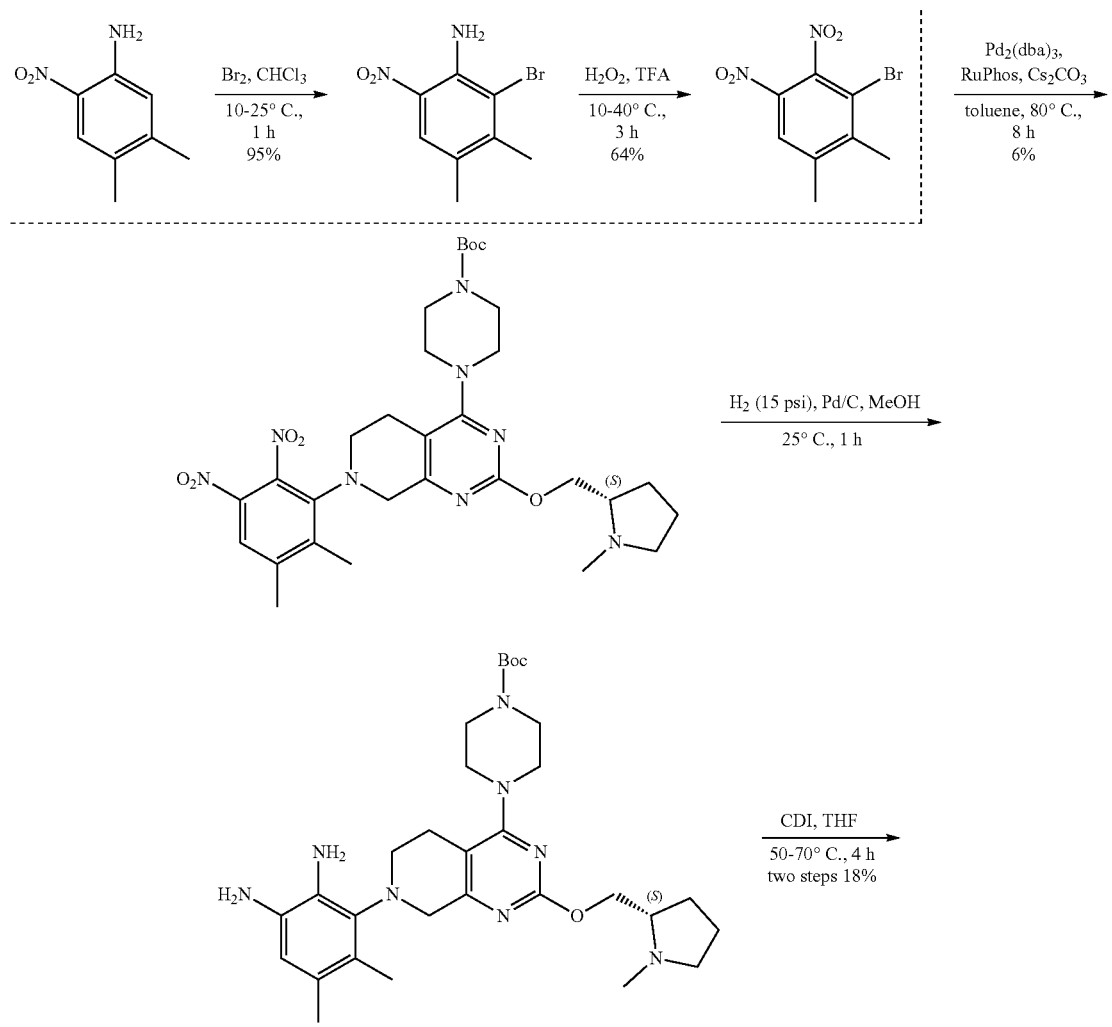

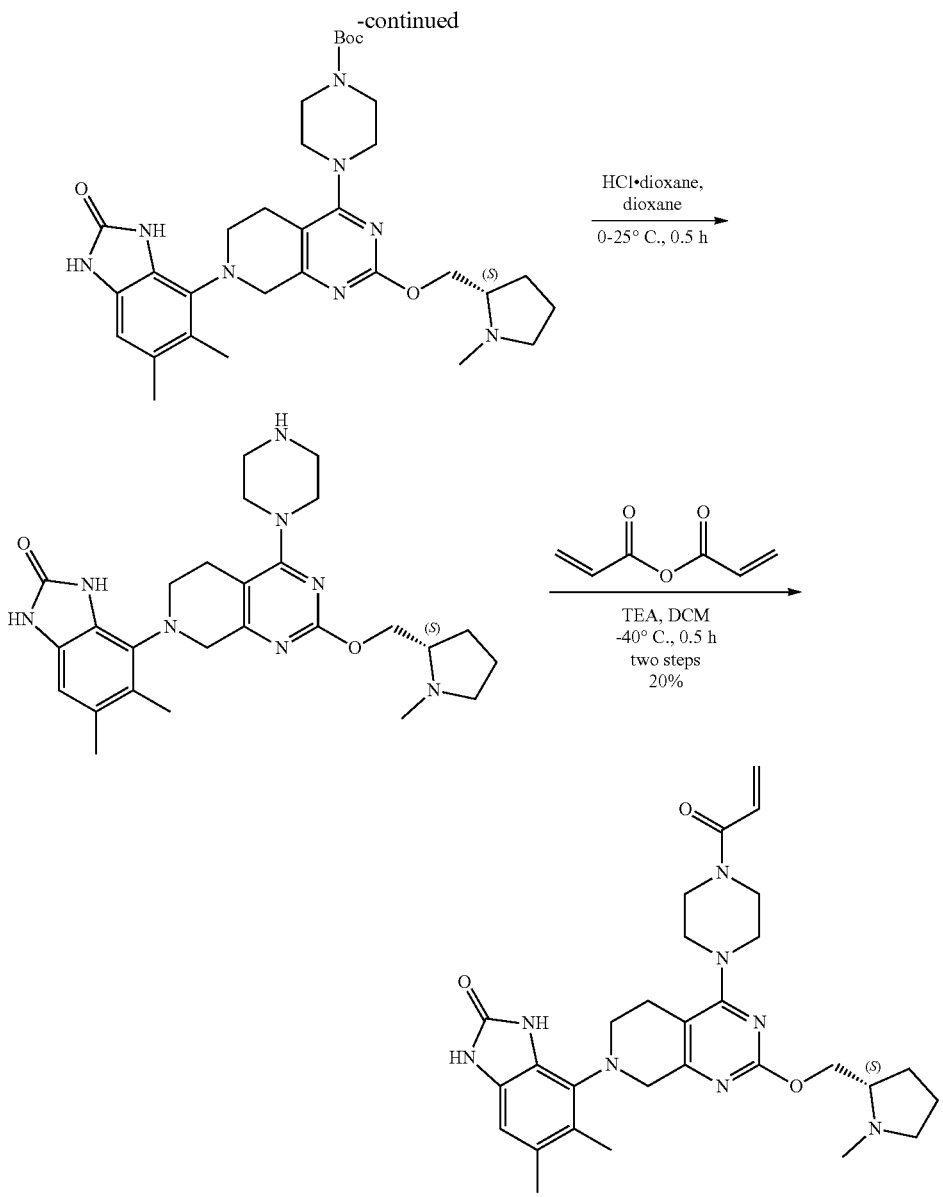

Insert Step 1: 2-bromo-3,4-dimethyl-6-nitro-aniline

To a solution of 4,5-dimethyl-2-nitro-aniline (5 g, 30.1 mmol, 1 eq) in CHCl$_3$ (100 mL) was added Br$_2$ (7.21 g, 45.1 mmol, 2.33 mL, 1.5 eq) dropwise at 10° C. The reaction mixture was stirred at 10° C. for 30 mins and 25° C. for 30 mins. After completion, the reaction mixture was washed with saturated with NaHCO$_3$ aqueous (80 mL). The aqueous was extracted with CHCl$_3$ (30 mL). The combined organic phase was dried over Na$_2$SO$_4$, filtered through a pad of silica gel, and then concentrated to dryness. 2-bromo-3,4-dimethyl-6-nitro-aniline (7 g, 28.5 mmol, 95% yield, 99.7% purity) was obtained as yellow solid. LCMS [ESI, M+3]: 247

Step 2: 3-bromo-1,2-dimethyl-4,5-dinitro-benzene

To a solution of 2-bromo-3,4-dimethyl-6-nitro-aniline (7 g, 28.6 mmol, 1 eq) in TFA (50 mL) was added hydrogen peroxide (25.9 g, 229 mmol, 22.0 mL, 30% purity, 8.0 eq) dropwise at 10° C. The reaction mixture was stirred at 10° C. for 30 mins and 25° C. for 30 mins, and then at 40° C. for another 2 hrs. The reaction mixture was cooled to 5-10° C. and then was filtered. The filter cake was washed with PE (3×20 mL). The solid was then dried under reduced pressure at 50° C. 3-bromo-1,2-dimethyl-4,5-dinitro-benzene (5 g, 18.2 mmol, 64% yield) was obtained as yellow solid.

Step A: tert-butyl 4-[7-(2,3-dimethyl-5,6-dinitro-phenyl)-2-[[(2S)-1-methylpyrrolidin-2-yl]methoxy]-6,8-dihydro-5H-pyrido[3,4-d]pyrimidin-4-yl]piperazine-1-carboxylate To a mixture of tert-butyl 4-[2-[[(2S)-1-methylpyrrolidin-2-yl] methoxy]-5,6,7,8-tetrahydropyrido[3,4-d]pyrimidin-4-yl]piperazine-1-carboxylate (250 mg, 578 umol, 1 eq), 3-bromo-1,2-dimethyl-4,5-dinitro-benzene (318 mg, 1.16 mmol, 2 eq), Pd$_2$(dba)$_3$ (52.9 mg, 57.8 umol, 0.1 eq), RuPhos (40.5 mg, 86.7 umol, 0.15 eq) and Cs$_2$CO$_3$ (377 mg, 1.16 mmol, 2 eq) in toluene (25 mL) was degassed and purged with N₂ for 3 times, and then the mixture was stirred at 90° C. for 8 hours under N₂ atmosphere. The reaction mixture was diluted with H₂O (100 mL×1) and ethyl acetate (100 mL×2). The separated organic phase was washed with brine (100 mL×1), dried over sodium sulfate, filtered and concentrated under reduced pressure to give a residue. The residue was purified by silica gel chromatography (SiO₂, Ethyl acetate/MeOH=50/1 to 3/1) and reversed phase flash [water (0.1% FA)/acetonitrile]. The desired fractions were collected and neutralized with saturated NaHCO₃ solution and extracted with ethyl acetate (1×100 mL). The separated organic layer was dried over sodium sulfate, filtered and concentrated under vacuum. tert-butyl 4-[7-(2,3-dimethyl-5,6-dinitro-phenyl)-2-[[(2S)-1-methylpyrrolidin-2-yl]methoxy]-6,8-dihydro-5H-pyrido[3,4-d]pyrimidin-4-yl]piperazine-1-carboxylate (22.0 mg, 140 umol, 6% yield, 99.7% purity) was obtained as a yellow solid. LCMS [ESI, M+1]: 627.

Step B: tert-butyl 4-[7-(2,3-diamino-5,6-dimethyl-phenyl)-2-[[(2S)-1-methylpyrrolidin-2-yl]methoxy]-6,8-dihydro-5H-pyrido[3,4-d]pyrimidin-4-yl]piperazine-1-carboxylate To a solution of tert-butyl 4-[7-(2,3-dimethyl-5,6-dinitro-phenyl)-2-[[(2S)-1-methylpyrrolidin-2-yl]methoxy]-6,8-dihydro-5H-pyrido[3,4-d]pyrimidin-4-yl]piperazine-1-carboxylate (120 mg, 191 umol, 1 eq) in MeOH (10 mL) was added Pd/C (24.0 mg, 10% purity) under N₂. The suspension was degassed under vacuum and purged with H₂ for several times. The mixture was stirred under H₂ (15 psi) at 25° C. for 1 hour. The catalyst was filtered off and the filtrate was concentrated under vacuum. tert-butyl 4-[7-(2,3-diamino-5,6-dimethyl-phenyl)-2-[[(2S)-1-methylpyrrolidin-2-yl]methoxy]-6,8-dihydro-5H-pyrido[3,4-d]pyrimidin-4-yl]piperazine-1-carboxylate (100 mg, crude) was obtained as a yellow solid and used into next step without further purification. LCMS [ESI, M+1]: 567.

Step C: tert-butyl 4-[7-(5,6-dimethyl-2-oxo-1,3-dihydrobenzimidazol-4-yl)-2-[[(2S)-1-methylpyrrolidin-2-yl]methoxy]-6,8-dihydro-5H-pyrido[3,4-d]pyrimidin-4-yl]piperazine-1-carboxylate To a solution of tert-butyl 4-[7-(2,3-diamino-5,6-dimethyl-phenyl)-2-[[(2S)-1-methylpyrrolidin-2-yl]methoxy]-6,8-dihydro-5H-pyrido[3,4-d]pyrimidin-4-yl]piperazine-1-carboxylate (100 mg, 176 umol, 1 eq) in THF (10 mL) was added CDI (57.2 mg, 353 umol, 2 eq). After stirred at 50° C. for 1 h, CDI (171 mg) was added and the mixture was stirred at 70° C. for further 3 hours. The reaction mixture was quenched with H₂O (3 mL×1), and then extracted with ethyl acetate (2×20 mL). The combined organic layers were washed with brine (1×10 mL), dried over sodium sulfate, filtered and concentrated under vacuum. The residue was purified by prep-HPLC (column: Luna C18 150*25 5 u; mobile phase: [water (0.225% FA)-ACN]; B %: 17%-47%, 10 min). The desired fractions were collected and neutralized with saturated NaHCO₃ solution and extracted with ethyl acetate (1×30 mL). The separated organic layer was dried over sodium sulfate, filtered and concentrated under vacuum. tert-butyl 4-[7-(5,6-dimethyl-2-oxo-1,3-dihydrobenzimidazol-4-yl)-2-[[(2S)-1-methylpyrrolidin-2-yl]methoxy]-6,8-dihydro-5H-pyrido[3,4-d]pyrimidin-4-yl]piperazine-1-carboxylate (20.0 mg, 33.7 umol, two steps 19% yield, 100% purity) was obtained as a yellow solid. LCMS [ESI, M+1]: 593.

Step D: 5,6-dimethyl-4-[2-[[(2S)-1-methylpyrrolidin-2-yl]methoxy]-4-piperazin-1-yl-6,8-dihydro-5H-pyrido[3,4-d]pyrimidin-7-yl]-1,3-dihydrobenzimidazol-2-one To a solution of tert-butyl 4-[7-(5,6-dimethyl-2-oxo-1,3-dihydrobenzimidazol-4-yl)-2-[[(2S)-1-methylpyrrolidin-2-yl]methoxy]-6,8-dihydro-5H-pyrido[3,4-d]pyrimidin-4-yl]piperazine-1-carboxylate (16.0 mg, 27.0 umol, 1 eq) in dioxane (2 mL) was added HCl/dioxane (4 M, 101 uL, 15 eq) at 0° C. After stirred at 25° C. for 0.5 h, the mixture was concentrated under vacuum. 5,6-dimethyl-4-[2-[[(2S)-1-methylpyrrolidin-2-yl]methoxy]-4-piperazin-1-yl-6,8-dihydro-5H-pyrido[3,4-d]pyrimidin-7-yl]-1,3-dihydrobenzimidazol-2-one (20.0 mg, crude, HCl) was obtained as a yellow oil and used into next step without further purification. LCMS [ESI, M+1]: 493.

Step E: 5,6-dimethyl-4-[2-[[(2S)-1-methylpyrrolidin-2-yl]methoxy]-4-(4-prop-2-enoylpiperazin-1-yl)-6,8-dihydro-5H-pyrido[3,4-d]pyrimidin-7-yl]-1,3-dihydrobenzimidazol-2-one To a mixture of 5,6-dimethyl-4-[2-[[(2S)-1-methylpyrrolidin-2-yl]methoxy]-4-piperazin-1-yl-6,8-dihydro-5H-pyrido[3,4-d]pyrimidin-7-yl]-1,3-dihydrobenzimidazol-2-one (20.0 mg, 37.8 umol, 1 eq, HCl) and TEA (38.3 mg, 378 umol, 52.6 uL, 10 eq) in DCM (2 mL) was added prop-2-enoyl prop-2-enoate (4.77 mg, 37.8 umol, 1 eq) in portion at −40° C. After stirred at −40° C. for 30 mins, the reaction mixture was quenched with saturated NaHCO₃ solution (0.5 mL) at 0° C., and then extracted with CH₂Cl₂ (2×10 mL). The combined organic layers were washed with brine (1×10 mL), dried over sodium sulfate, filtered and concentrated under vacuum to give a residue. The residue was purified by prep-HPLC (column: Phenomenex Synergi C18 150*25*10 um; mobile phase: [water (0.225% FA)-ACN]; B %: 10%-37%, 9 min). The desired fractions were collected and concentrated under reduced pressure to remove ACN, and then lyophlizated. Title compound 5,6-dimethyl-4-[2-[[(2S)-1-methylpyrrolidin-2-yl]methoxy]-4-(4-prop-2-enoylpiperazin-1-yl)-6,8-dihydro-5H-pyrido[3,4-d]pyrimidin-7-yl]-1,3-dihydrobenzimidazol-2-one (EXAMPLE 456, 3.15 mg, 5.25 umol, two steps 14% yield, 98.8% purity, HCOOH) was obtained as a brown solid. LCMS [ESI, M+1]: 547.

¹H NMR (400 MHz, methanol-d₄) 6.90-6.81 (m, 1H), 6.80-6.72 (m, 1H), 6.28 (br d, J=16.8 Hz, 1H), 5.82 (br d, J=10.4 Hz, 1H), 4.72-4.46 (m, 2H), 4.32-4.01 (m, 2H), 3.93-3.53 (m, 10H), 3.53-3.38 (m, 1H), 3.21-3.02 (m, 2H), 2.98 (s, 3H), 2.95-2.58 (m, 2H), 2.48-2.32 (m, 1H), 2.31 (br s, 3H), 2.29 (br s, 3H), 2.19-1.94 (m, 3H).

Example 457
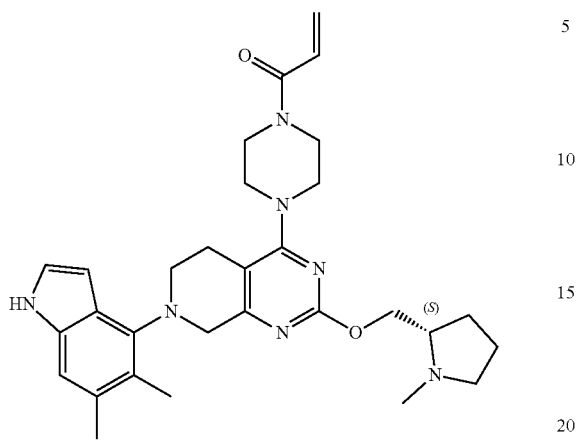
1-[4-[7-(5,6-dimethyl-1H-indol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one
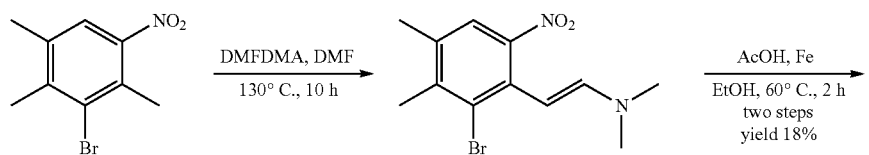
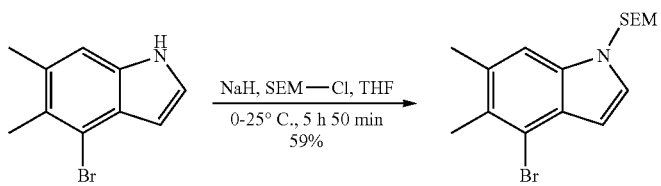
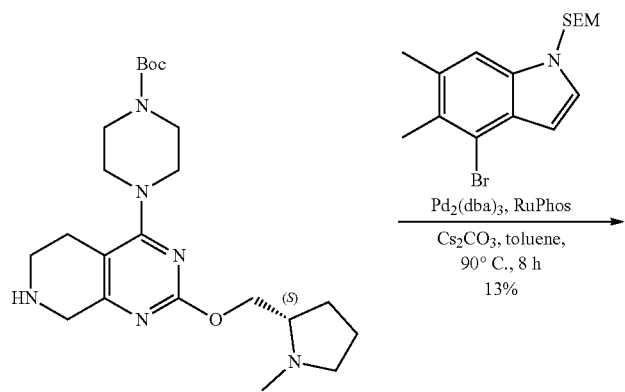

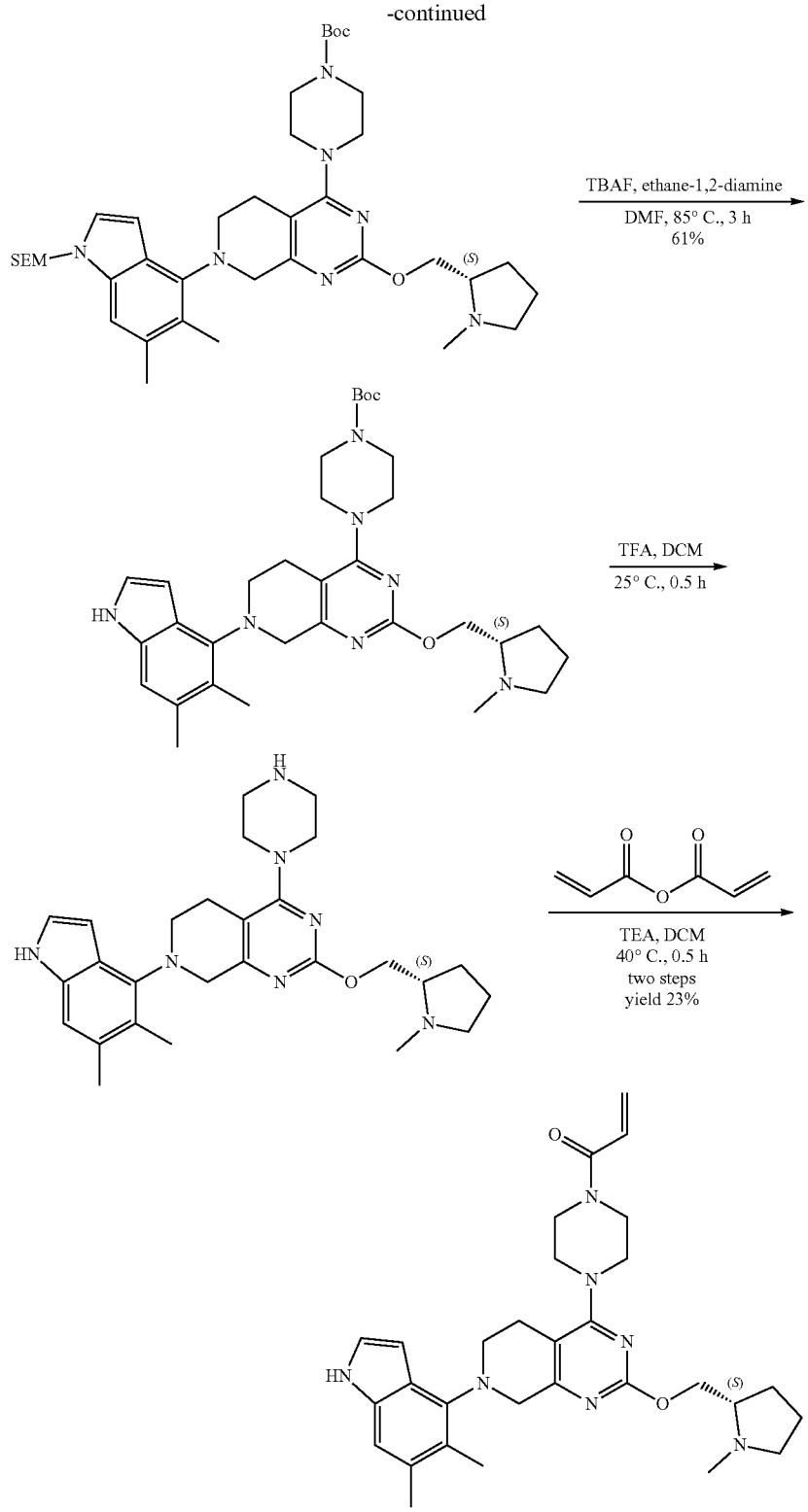

Step 1: (E)-2-(2-bromo-3,4-dimethyl-6-nitro-phenyl)-N,N-dimethyl-ethenamine

To a solution of 3-bromo-1,2,4-trimethyl-5-nitro-benzene (2 g, 8.19 mmol, 1 eq) in DMF (20 mL) was added DMFDMA (5.86 g, 49.2 mmol, 6.53 mL, 6 eq). The mixture was stirred at 130° C. for 10 hours. Upon completion, the mixture was concentrated under vacuum to give (E)-2-(2-bromo-3,4-dimethyl-6-nitro-phenyl)-N,N-dimethyl-ethenamine (2.5 g, crude) as a brown oil which was used directly into the next step without further purification.

Step 2: 4-bromo-5,6-dimethyl-1H-indole

To a solution of (E)-2-(2-bromo-3,4-dimethyl-6-nitrophenyl)-N,N-dimethyl-ethenamine (2.5 g, 8.36 mmol, 1 eq) in EtOH (50 mL) was added Fe (2.33 g, 41.8 mmol, 5 eq) and AcOH (5.02 g, 83.6 mmol, 4.78 mL, 10 eq). The mixture was stirred at 60° C. for 2 hours. Upon completion, the mixture was filtered and the filtrate was concentrated. The mixture was adjusted pH=7 with saturated NaHCO₃ aqueous solution and extracted with ethyl acetate (50 mL×2). The combined organic layers were washed with brine (50 mL), dried over Na₂SO₄ and concentrated under vacuum. The residue was purified by silica gel chromatography (PE/EtOAc 1/0 to 50/1) to give 4-bromo-5,6-dimethyl-1H-indole (380 mg, 1.46 mmol, two steps yield 18%, 86% purity) as a yellow oil.

$^1$H NMR (400 MHz, chloroform-d) δ=8.12 (br s, 1H), 7.20-7.10 (m, 2H), 6.59-6.52 (m, 1H), 2.47 (s, 3H), 2.43 (s, 3H).

Step 3: 2-[(4-bromo-5,6-dimethyl-indol-1-yl)methoxy]ethyl-trimethyl-silane

To a solution of 4-bromo-5,6-dimethyl-1H-indole (450 mg, 2.01 mmol, 1 eq) in THF (9 mL) was added NaH (161 mg, 4.02 mmol, 60% purity, 2 eq) at 0° C. The reaction was stirred at 0° C. for 15 minutes under N₂. The reaction was allowed to warm to 25° C. and stirred for 0.5 hour. The reaction was chilled again to 0° C. And SEM-Cl (502 mg, 3.01 mmol, 533 uL, 1.5 eq) in THF (100 uL) was added drop-wise at 0° C. After stirring for 5 minutes, the mixture was allowed to warm to room temperature (25° C.) and stirred for another 5 hours. Upon completion, the mixture was quenched with saturated aqueous ammonium chloride solution (20 mL), diluted with water (10 mL), and then extracted with ethyl acetate (2×30 mL). The extracts were dried over Na₂SO₄, filtered and concentrated under vacuum. The residue was purified by silica gel chromatography (PE/EtOAc 1/0 to 50/1) to give 2-[(4-bromo-5,6-dimethyl-indol-1-yl)methoxy]ethyl-trimethyl-silane (440 mg, 1.18 mmol, 59% yield, 95% purity) as a yellow oil.

$^1$H NMR (400 MHz, chloroform-d) δ=7.25 (s, 1H), 7.11 (d, J=3.2 Hz, 1H), 6.51 (d, J=2.8 Hz, 1H), 5.43 (s, 2H), 3.52-3.40 (m, 2H), 2.47 (s, 3H), 2.46 (s, 3H), 0.92-0.87 (m, 2H), −0.01--0.08 (m, 9H).

Step A: tert-butyl 4-[7-[5,6-dimethyl-1-(2-trimethylsilylethoxymethyl)indol-4-yl]-2-[[(2S)-1-methylpyrrolidin-2-yl]methoxy]-6,8-dihydro-5H-pyrido[3,4-d]pyrimidin-4-yl]piperazine-1-carboxylate tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 66, 450 mg, 1.04 mmol, 1 eq), 2-[(4-bromo-5,6-dimethyl-indol-1-yl)methoxy]ethyl-trimethyl-silane (406 mg, 1.14 mmol, 1.1 eq), Pd₂(dba)₃ (191 mg, 208 umol, 0.2 eq), RuPhos (194 mg, 416 umol, 0.4 eq) and Cs₂CO₃ (847 mg, 2.60 mmol, 2.5 eq) in toluene (30 mL) was de-gassed and then heated to 90° C. for 8 hours under N₂. Upon completion, the mixture was filtered and the filtrate was concentrated under vacuum. The residue was purified by silica gel chromatography (EtOAc/MeOH 50/1 to 10/1) to give tert-butyl 4-[7-[5,6-dimethyl-1-(2-trimethylsilylethoxymethyl)indol-4-yl]-2-[[(2S)-1-methylpyrrolidin-2-yl]methoxy]-6,8-dihydro-5H-pyrido[3,4-d]pyrimidin-4-yl]piperazine-1-carboxylate (106 mg, 135 umol, 13% yield, 90% purity) as a yellow solid. LCMS [ESI, M+1]: 706.

Step B: tert-butyl 4-[7-(5,6-dimethyl-1H-indol-4-yl)-2-[[(2S)-1-methylpyrrolidin-2-yl]methoxy]-6,8-dihydro-5H-pyrido[3,4-d]pyrimidin-4-yl]piperazine-1-carboxylate To a solution of tert-butyl 4-[7-[5,6-dimethyl-1-(2-trimethylsilylethoxymethyl)indol-4-yl]-2-[[(2S)-1-methylpyrrolidin-2-yl]methoxy]-6,8-dihydro-5H-pyrido[3,4-d]pyrimidin-4-yl]piperazine-1-carboxylate (70 mg, 99.2 umol, 1 eq) in DMF (0.35 mL) was added TBAF (1 M in THF, 496 uL, 5 eq) followed by ethane-1,2-diamine (8.94 mg, 149 umol, 9.95 uL, 1.5 eq). The mixture was stirred at 85° C. for 3 hours. Upon completion, the mixture was diluted with EtOAc (3 mL) and water (2 mL). The separated organic layer was dried over Na₂SO₄ and concentrated under vacuum. The residue was purified by prep-TLC (DCM/MeOH 10/1) to give tert-butyl 4-[7-(5,6-dimethyl-1H-indol-4-yl)-2-[[(2S)-1-methylpyrrolidin-2-yl]methoxy]-6,8-dihydro-5H-pyrido[3,4-d]pyrimidin-4-yl]piperazine-1-carboxylate (50 mg, 60.8 umol, 61% yield, 70% purity) as a yellow oil. LCMS [ESI, M+1]: 576.

Step C: 7-(5,6-dimethyl-1H-indol-4-yl)-2-[[(2S)-1-methylpyrrolidin-2-yl]methoxy]-4-piperazin-1-yl-6,8-dihydro-5H-pyrido[3,4-d]pyrimidine To a solution of tert-butyl 4-[7-(5,6-dimethyl-1H-indol-4-yl)-2-[[(2S)-1-methylpyrrolidin-2-yl]methoxy]-6,8-dihydro-5H-pyrido[3,4-d]pyrimidin-4-yl]piperazine-1-carboxylate (45 mg, 78.2 umol, 1 eq) in DCM (70 uL) was added TFA (89.1 mg, 782 umol, 57.9 uL, 10 eq). The mixture was stirred at 25° C. for 0.5 hour. Upon completion, the mixture was concentrated under vacuum to give 7-(5,6-dimethyl-1H-indol-4-yl)-2-[[(2S)-1-methylpyrrolidin-2-yl]methoxy]-4-piperazin-1-yl-6,8-dihydro-5H-pyrido[3,4-d]pyrimidine (60 mg, crude, 2 TFA) as a yellow oil which was used directly into the next step without further purification.

Step D: 1-[4-[7-(5,6-dimethyl-1H-indol-4-yl)-2-[[(2S)-1-methylpyrrolidin-2-yl]methoxy]-6,8-dihydro-5H-pyrido[3,4-d]pyrimidin-4-yl]piperazin-1-yl]prop-2-en-1-one To a solution of 7-(5,6-dimethyl-1H-indol-4-yl)-2-[[(2S)-1-methyl pyrrolidin-2-yl]methoxy]-4-piperazin-1-yl-6,8-dihydro-5H-pyrido[3,4-d]pyrimidine (55 mg, 78.2 umol, 1 eq, 2 TFA) and TEA (158 mg, 1.56 mmol, 218 uL, 20 eq) in DCM (1 mL) was added prop-2-enoyl prop-2-enoate (9.86 mg, 78.2 umol, 1 eq) dropwise at −40° C. The mixture was stirred at −40° C. for 30 minutes. Upon completion, the mixture was quenched with MeOH (0.5 mL), diluted with water (5 mL) and then extracted with DCM (2×10 mL). The organic layers were dried over Na₂SO₄, filtered and concentrated under vacuum. The residue was purified by chromatography (Al₂O₃, EtOAc/MeOH 100/1 to 10/1) and prep-HPLC (column: Phenomenex Synergi C18 150*25*10 um; mobile phase: [water (0.1% TFA)-ACN]; B %: 16%-43%, 12 min). The desired fractions were collected and neutralized with saturated aqueous NaHCO₃, extracted with DCM (2×15 mL). The organic layers were dried over Na₂SO₄ and concentrated under vacuum to give title compound 1-[4-[7-(5,6-dimethyl-1H-indol-4-yl)-2-[[(2S)-1-methylpyrrolidin-2-yl]methoxy]-6,8-dihydro-5H-pyrido[3,4-d]pyrimidin-4- yl]piperazin-1-yl]prop-2-en-1-one (EXAMPLE 457, 9.81 mg, 18.3 umol, two steps 23% yield, 98.8% purity) as a brown solid. LCMS [ESI, M+1]: 530.

SFC condition: OJ-3S_3_5_40_3ML Column: Chiralcel OJ-3 100×4.6 mm I.D., 3 um Mobile phase: methanol (0.05% DEA) in $CO_2$ from 5% to 40% Flow rate: 3 mL/min Wavelength: 220 nm.

$^1$H NMR (400 MHz, chloroform-d) δ=8.22 (br s, 1H), 7.09 (s, 1H), 7.07-7.03 (m, 1H), 6.60 (dd, J=10.8, 16.8 Hz, 1H), 6.53-6.48 (m, 1H), 6.34 (dd, J=2.0, 16.9 Hz, 1H), 5.76 (dd, J=2.0, 10.4 Hz, 1H), 4.49-4.10 (m, 4H), 3.81 (br s, 2H), 3.76-3.38 (m, 8H), 3.13 (br t, J=7.2 Hz, 1H), 3.02-2.56 (m, 3H), 2.50 (s, 3H), 2.39 (s, 3H), 2.36 (s, 3H), 2.34-2.25 (m, 1H), 2.13-2.06 (m, 1H), 1.84-1.71 (m, 3H).

Example 458

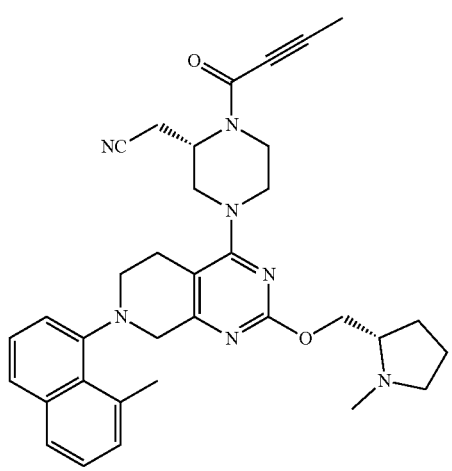 [SMILES: CC#CC(=O)N1CCN(c2nc(OC[C@@H]3CCCN3C)nc3c2CCN(c2cccc4cccc(C)c24)C3)C[C@@H]1CC#N]

2-((S)-1-(but-2-ynoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

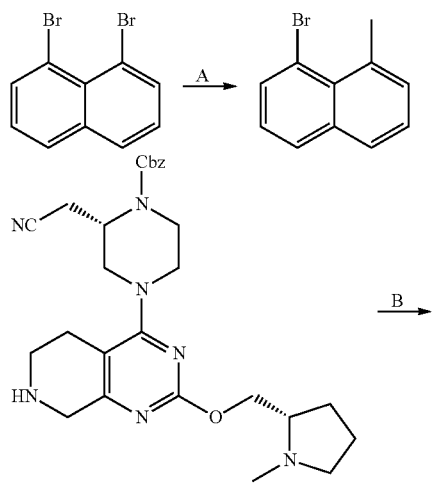

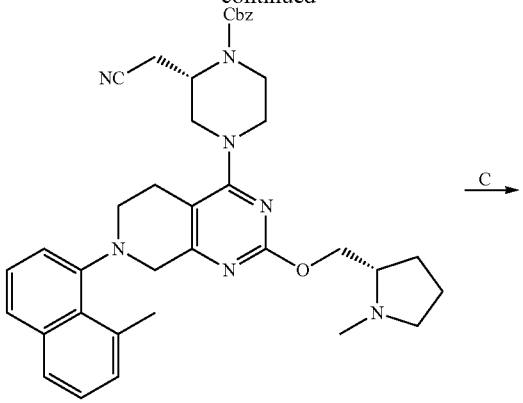

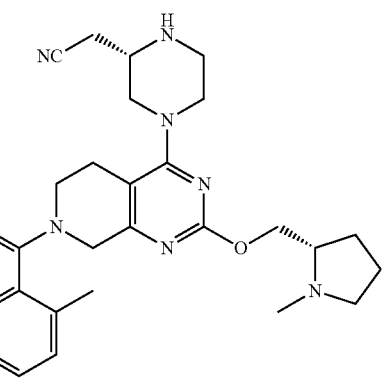

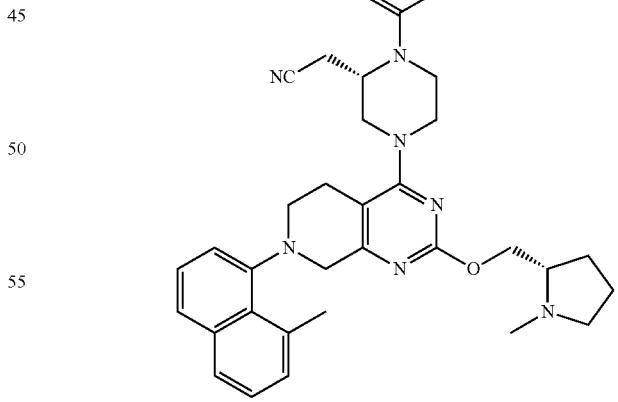

Step A: 1-bromo-8-methylnaphthalene

To a solution of 1,8-dibromonaphthalene (33.8 g, 118 mmol) in THF (200 mL) cooled to −78° C. was added butyllithium (49.6 ml, 124 mmol) at such a rate that the internal temperature did not exceed −69° C. After complete addition, the reaction was cooled to −78° C., and methyl iodide (14.8 ml, 236 mmol) was added in a bolus such that the internal temp increased to −40° C. After methyl iodide addition, the dry ice/acetone bath was removed and the reaction warmed to room temperature. The reaction was next poured into brine and the aqueous layer extracted with EtOAc (300 mL) and the organics separated. The organics were next dried over MgSO$_4$ and concentrated in vacuo and the residue chromatographed using hexanes as eluent to give a white solid (24 g). The solid was next slurried in IPA (ca. 60 mL) and the slurry heated to 60° C. at which point the solids dissolved. The solution was removed from heating and cooled to room temperature over 2 hrs. The resulting slurry was filtered and the solids dried in vacuo to give 1-bromo-8-methylnaphthalene (16 g, 72.4 mmol, 61% yield) >95% purity.

Step B: benzyl (S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazine-1-carboxylate A solution of xantphos (4.5 g, 7.8 mmol) and Pd$_2$(dba)$_3$ (3.5 g, 3.9 mmol) in dioxane (100 mL) was degassed with Argon for 15 minutes, followed by heating the solution for 20 minutes at 100° C. The solution was cooled to room temperature and benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (9.8 g, 19 mmol), 1-bromo-8-methylnaphthalene (13 g, 58 mmol) and Cs2CO3 (32 g, 97 mmol), Pd2(dba)3 (3.5 g, 3.9 mmol) were added to the solution and the mixture was degassed for an additional 20 minutes with Argon and the reaction heated to 100° C. overnight. The reaction was next cooled to room temperature and filtered through GFF paper and the filtrate was concentrated in vacuo. The residue was next chromatographed 3 times using 1→10% (MeOH+2% NH$_4$OH)/DCM to give benzyl (S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazine-1-carboxylate (7.8 g, 12 mmol, 62% yield). ESI+APCI MS m/z 646.3 [M+H]$^+$.

Step C: 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile A solution of benzyl (S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazine-1-carboxylate (7.8 g, 12 mmol) in 1:1 EtOH/THF (100 mL) was degassed with N2 for 5 minutes followed by addition of Pd/C (2.6 g, 2.4 mmol). The slurry was next degassed under vacuum and backfilled with H$_2$ (3×). On the third back fill the mixture was stirred under a balloon of hydrogen for overnight. The slurry was again degassed with N2 and the slurry filtered through celite. The combined filtrate was concentrated in vacuo and the solids chromatographed using 1→10% (MeOH+2% NH$_4$OH)/DCM as eluent to give 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (5.0 g, 9.8 mmol, 81% yield).

Step D: 2-((S)-1-(but-2-ynoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile At 0° C., to a 25 mL RBF containing N,N-dimethylformamide (1954 μl, 0.391 mmol) was added 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (200 mg, 0.391 mmol) and triethylamine (136 μl, 0.977 mmol). The reaction mixture was vigorously stirred while but-2-ynoic acid (49.3 mg, 0.586 mmol) was added in one portion. 1-Propanephosphonic acid cyclic anhydride (175 μl, 0.293 mmol) was added slowly to the stirring mixture. The reaction was allowed to stir at rt for 18 hr. Water was added and the solids were filtered. The solids were purified by silica gel (5-18% MeOH in DCM with 0.25% NH$_4$OH) to provide title compound 2-((S)-1-(but-2-ynoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (EXAMPLE 458, 110 mg, 0.190 mmol, 49% yield). ESI+APCI MS m/z 578.3 [M+H]$^+$.

Example 459

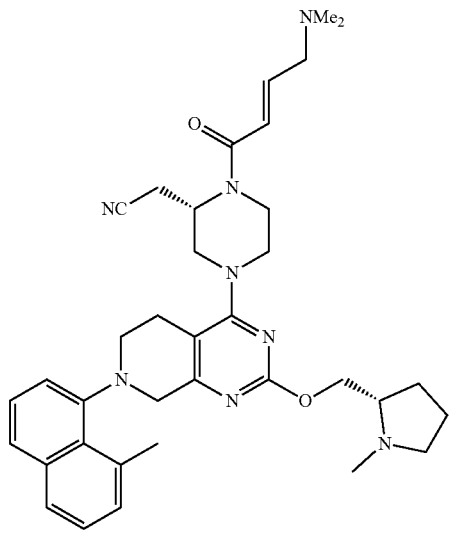 [SMILES: Cc1cccc2cccc(N3CCc4c(nc(OC[C@@H]5CCCN5C)nc4N4CCN(C(=O)/C=C/CN(C)C)[C@@H](CC#N)C4)C3)c12]

2-((S)-1-((E)-4-(dimethylamino)but-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

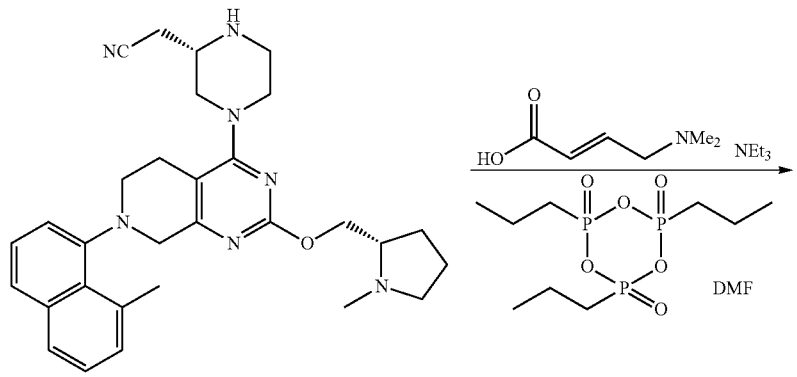

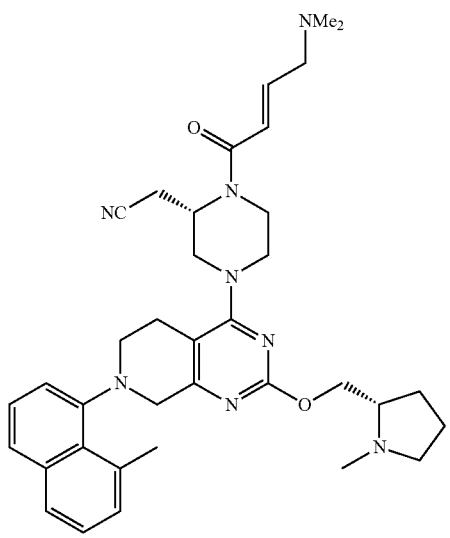

Step A: 2-((S)-1-((E)-4-(dimethylamino)but-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile A stirred mixture of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (100 mg, 0.1954 mmol), (E)-4-(dimethylamino)but-2-enoic acid (37.86 mg, 0.2932 mmol) and N,N-dimethylformamide (2 mL, 25.58 mmol) was cooled on ice-salt bath and triethylamine (0.02724 mL, 0.1954 mmol) was added at once, followed by 2,4,6-tripropyl-1,3,5,2,4,6-trioxatriphosphinane 2,4,6-trioxide, 50% in EtOAc (0.1745 mL, 0.2932 mmol). The reaction mixture was allowed to warm to r.t. over 5 min, then stirred at r.t. for 3 h. The reaction mixture was partitioned between EtOAc (50 mL) and 0.5 M $Na_2CO_3$ (20 mL), the organics were separated, the organic layer was washed with water and brine (10 mL each), dried over $Na_2SO_4$ and evaporated in vacuo. Chromatography on silica gel in 5 to 10% MeOH+0.5% $NH_4OH$ in DCM afforded crude product that was purified on the reverse phase, Gilson, 5 to 95% MeCN+0.1% TFA in water. The target fractions were combined, basified with 2M $Na_2CO_3$ and extracted with DCM (3*20 mL). The combined extracts were washed with brine (10 mL), dried over $Na_2SO_4$ and evaporated in vacuo. The solid residue was dissolved in DCM (3 mL), filtered and evaporated to yield the desired title compound as colorless solid (EXAMPLE 459, 40 mg, 33%). ESI+APCI MS m/z 623.3 [M+H]$^+$.

1243

Example 460

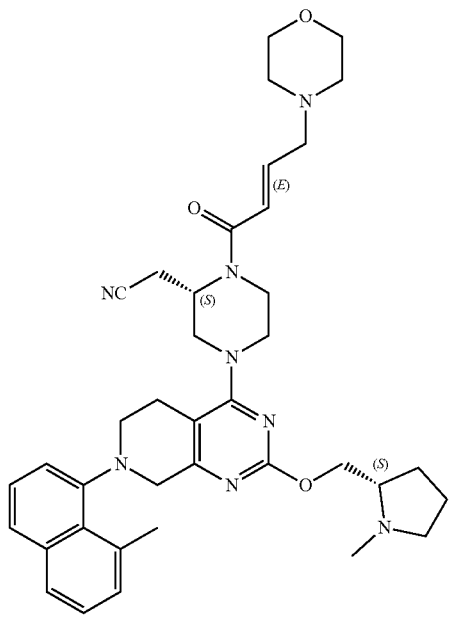

2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-[(E)-4-morpholinobut-2-enoyl]piperazin-2-yl]acetonitrile

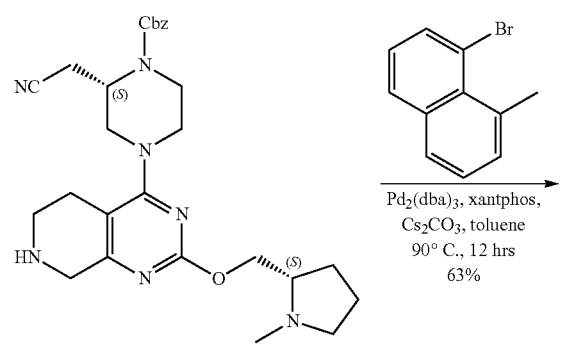

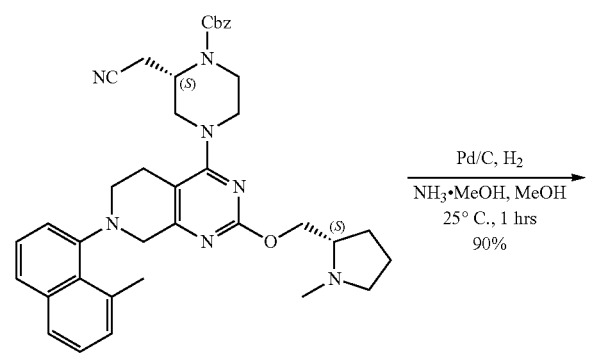

1244

-continued

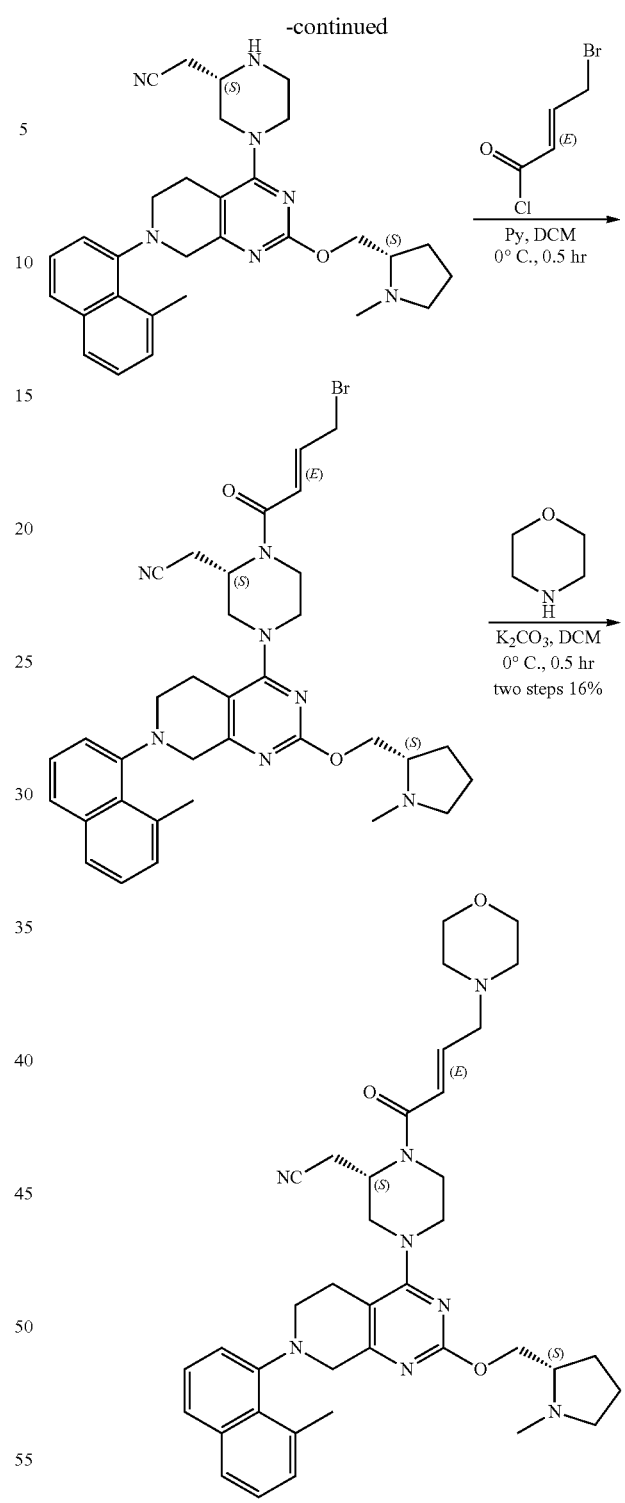

Step A: benzyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a solution of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 500 mg, 989 umol, 1.0 eq), Pd$_2$(dba)$_3$ (181 mg, 198 umol, 0.20 eq), Xantphos (172 mg, 297 umol, 0.30 eq) and Cs$_2$CO$_3$ (967 mg, 2.97 mmol, 3.0 eq) in toluene (5.0 mL) was added 1-bromo-8-methyl-naphthalene (Intermediate 69, 284 mg, 1.29 mmol, 1.30 eq). The mixture was stirred at 90° C. for 12 hours. After completion, the reaction mixture was added water (10.0 mL) and extracted with ethyl acetate (10.0 mL×4). The organic layer was dried over Na$_2$SO$_4$, filtered and concentrated under vacuum. The residue was purified by reversed phase flash column (C18, 0.1% in formic acid, 0-70% acetonitrile) to give the product benzyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (400 mg, 619 umol, 63% yield) as yellow oil. LCMS [ESI, M+1]: 646.

Step B: 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (700 mg, 1.08 mmol, 1.0 eq) and NH$_3$.MeOH (20.0 mL, 30% purity) in methanol (20.0 mL) was added Pd/C (200 mg, 10% purity). The mixture was purged by nitrogen for 3 times. Then the mixture was stirred under hydrogen atmosphere (15 Psi) at 25° C. for 1 hour. After completion, the reaction mixture was filtered through celite, the filter cake was washed with tetrahydrofuran (20.0 mL). The mother liquor was collected and concentrated under vacuum to give the product 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (500 mg, 977 umol, 90% yield) as yellow oil.

$^1$H NMR (400 MHz, Chloroform-d) δ 7.70 (d, J=8.0 Hz, 1H), 7.64 (dd, J=3.2, 7.2 Hz, 1H), 7.43-7.37 (m, 1H), 7.34 (t, J=7.6 Hz, 1H), 7.26-7.19 (m, 2H), 4.43-4.33 (m, 1H), 4.22 (dd, J=6.8, 18.0 Hz, 1H), 4.17-4.08 (m, 1H), 4.07-3.89 (m, 1H), 3.89-3.70 (m, 2H), 3.52-3.45 (m, 2H), 3.38-3.20 (m, 1H), 3.19-3.04 (m, 4H), 3.03-2.94 (m, 2H), 2.93-2.82 (m, 4H), 2.70-2.60 (m, 1H), 2.60-2.49 (m, 3H), 2.47 (d, J=2.4 Hz, 3H), 2.31-2.22 (m, 1H), 2.11-2.00 (m, 1H), 1.88-1.76 (m, 3H).

Step C: 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (250 mg, 489 umol, 1.0 eq) and pyridine (309 mg, 3.91 mmol, 316 uL, 8.0 eq) in dichloromethane (4.0 mL) was added (E)-4-bromobut-2-enoyl chloride (359 mg, 1.95 mmol, 4.0 eq). The mixture was stirred at 0° C. for 0.5 hour. After completion, the reaction mixture was concentrated to give the product 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (330 mg, crude) as yellow oil. The product was used for the next step without further purification. LCMS [ESI, M+1]: 658.

Step D: 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-[(E)-4-morpholinobut-2-enoyl]piperazin-2-yl]acetonitrile To a solution of 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, crude) and K$_2$CO$_3$ (630 mg, 4.55 mmol, 10.0 eq) in dichloromethane (2.0 mL) was added morpholine (238 mg, 2.73 mmol, 241 uL, 6.0 eq). The mixture was stirred at 0° C. for 12 hours. After completion, the reaction mixture was added water (10.0 mL) and extracted with ethyl acetate (10.0 mL×3). The organic layer was dried over Na$_2$SO$_4$, filtered and concentrated under vacuum. The residue was purified by prep-HPLC (column: Gemini 150*25 5 u; mobile phase: [water (0.05% ammonia hydroxide v/v)-ACN]; B %: 50%-80%, 12 min) to give the title compound 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-[(E)-4-morpholinobut-2-enoyl]piperazin-2-yl]acetonitrile (EXAMPLE 460, 48.2 mg, 72.5 umol, 16% yield) as white solid. LCMS [ESI, M+1]: 665.

$^1$H NMR (400 MHz, Chloroform-d) δ 7.70 (br d, J=8.4 Hz, 1H), 7.65 (t, J=8.4 Hz, 1H), 7.41 (dd, J=7.6, 15.2 Hz 1H), 7.35 (t, J=7.6 Hz, 1H), 7.27-7.17 (m, 2H), 7.02-6.91 (m, 1H), 6.55-6.39 (m, 1H), 5.23-4.47 (m, 1H), 4.40-4.33 (m, 1H), 4.31-4.19 (m, 1H), 4.19-4.09 (m, 2H), 4.07-3.83 (m, 2H), 3.81-3.64 (m, 5H), 3.59-3.40 (m, 2H), 3.24-3.13 (m, 4H), 3.12-2.94 (m, 3H), 2.92 (s, 3H), 2.86-2.76 (m, 1H), 2.75-2.54 (m, 3H), 2.50 (br s, 4H), 2.48-2.45 (m, 3H), 2.33-2.22 (m, 1H), 2.10-2.00 (m, 1H), 1.87-1.71 (m, 3H).

Example 461

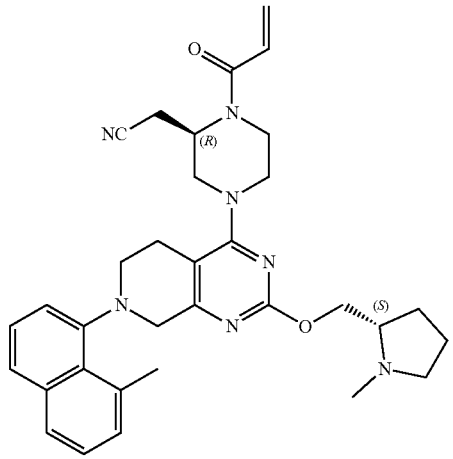

1247

2-[(2R)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

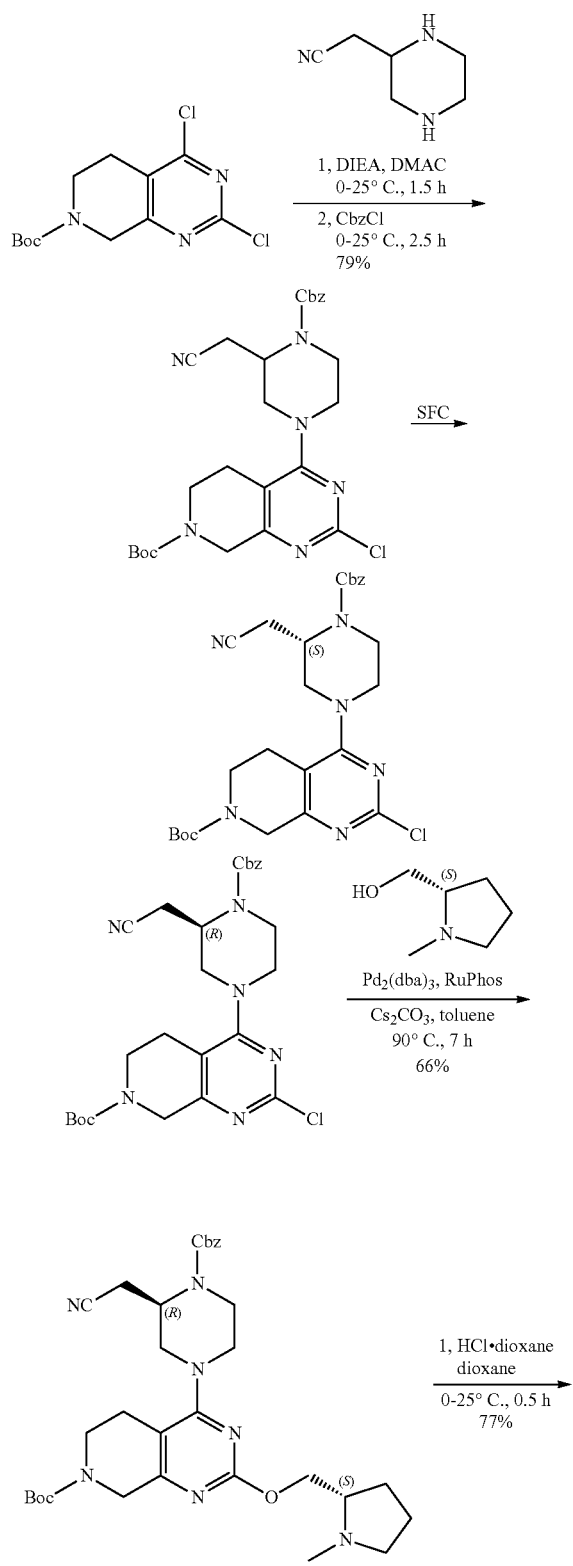

1248

-continued

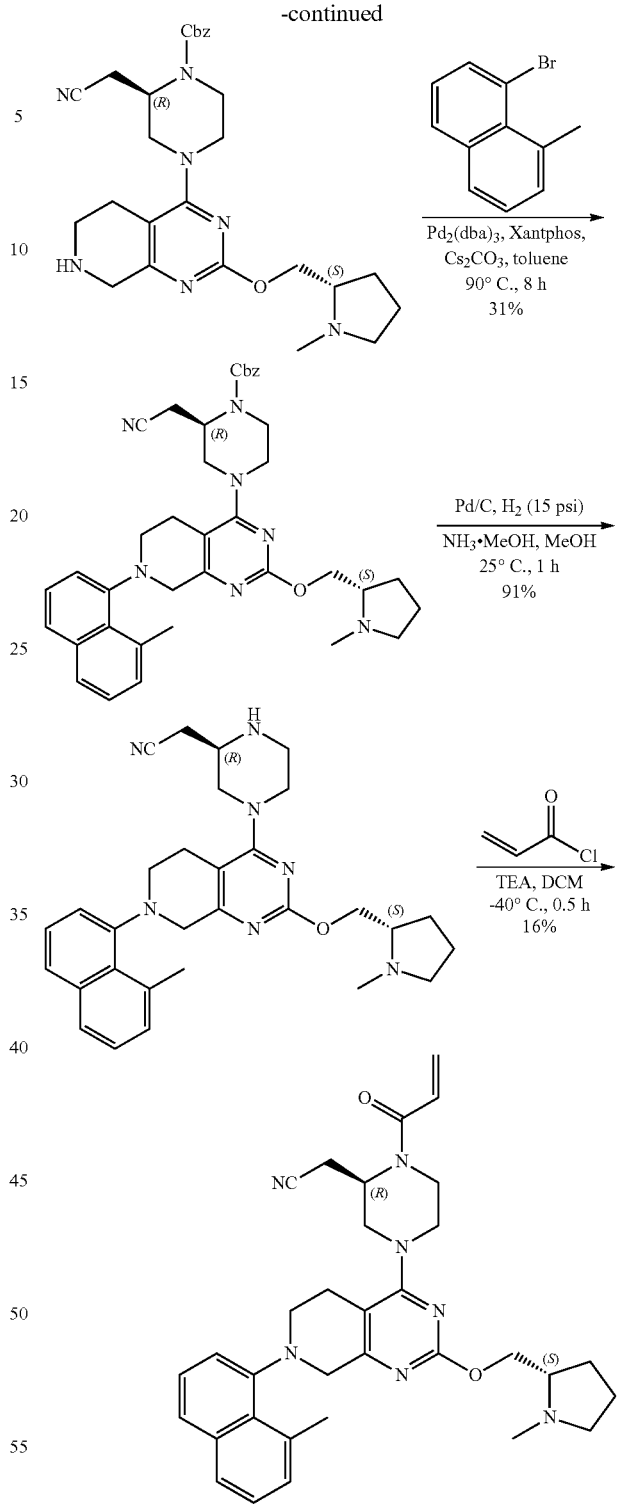

Step A: tert-butyl 4-[4-benzyloxycarbonyl-3-(cyanomethyl)piperazin-1-yl]-2-chloro-6,8-dihydro-5H-pyrido[3,4-d]pyrimidine-7-carboxylate To a solution of tert-butyl 2,4-dichloro-6,8-dihydro-5H-pyrido[3,4-d] pyrimidine-7-carboxylate (3 g, 9.86 mmol, 1 eq) in DMAc (60 mL) was added DIEA (3.82 g, 29.6 mmol, 5.15 mL, 3 eq) and 2-piperazin-2-ylacetonitrile (Intermediate 62, 2.15 g, 10.9 mmol, 1.1 eq, 2HCl) at 0° C. The mixture was stirred at 25° C. for 1.5 hrs. Then to the solution was added DIEA (2.55 g, 19.7 mmol, 3.43 mL, 2 eq) and benzyl chloroformate (2.52 g, 14.8 mmol, 2.10 mL, 1.5 eq) at 0° C. The mixture was stirred at 25° C. for another 2.5 hrs. To the reaction mixture was added $H_2O$ (40 mL) and ethyl acetate (100 mL). The separated organic phase was washed with 5% of aqueous citric acid solution (40 mL×1), aqueous saturated $Na_2CO_3$ solution (40 mL×1) and brine (40 mL×1), dried over sodium sulfate and filtered. The filtrate was concentrated under reduced pressure to give a residue. The residue was triturated with methyl tert-butyl ether (25 mL) to give a pure product. tert-butyl 4-[4-benzyloxycarbonyl-3-(cyanomethyl)piperazin-1-yl]-2-chloro-6,8-dihydro-5H-pyrido[3,4-d]pyrimidine-7-carboxylate (4.10 g, 7.62 mmol, 79% yield, 98% purity) was obtained as a white solid. LCMS [ESI, M+1]: 527.

$^1$H NMR (400 MHz, chloroform-d) δ=7.43-7.29 (m, 5H), 5.17 (s, 2H), 4.71-4.55 (m, 2H), 4.48-4.37 (m, 1H), 4.21-3.97 (m, 2H), 3.92-3.67 (m, 2H), 3.40-3.20 (m, 3H), 3.09 (dt, J=3.6, 12.4 Hz, 1H), 2.88-2.57 (m, 4H), 1.47 (s, 9H).

SFC condition (40935): Column: Chiralcel OD-3 50×4.6 mm I.D., 3 um Mobile phase: methanol (0.05% DEA) in $CO_2$ from 5% to 40%, Flow rate: 3 mL/min, Wavelength: 220 nm.

Step B: tert-butyl 4-[(3R)-4-benzyloxycarbonyl-3-(cyanomethyl) piperazin-1-yl]-2-chloro-6,8-dihydro-5H-pyrido[3,4-d]pyrimidine-7-carboxylate tert-Butyl 4-[4-benzyloxycarbonyl-3-(cyanomethyl)piperazin-1-yl]-2-chloro-6,8-dihydro-5H-pyrido[3,4-d]pyrimidine-7-carboxylate (2.20 g, 4.17 mmol, 1 eq) was separated by SFC (column: OD (250 mm*30 mm, 10 um); mobile phase: [0.1% $NH_3H_2O$ MeOH]; B %: 40%-40%, 3.1 min: 180 min). The desired fractions were collected and concentrated under vacuum to give tert-butyl 4-[(3R)-4-benzyloxycarbonyl-3-(cyanomethyl) piperazin-1-yl]-2-chloro-6,8-dihydro-5H-pyrido[3,4-d]pyrimidine-7-carboxylate (940 mg, 1.78 mmol, 43% yield, 99.7% purity) as a white solid. LCMS [ESI, M+1]: 527.

SFC condition: Column: Chiralcel OD-3 50×4.6 mm I.D., 3 um, Mobile phase: methanol (0.05% DEA) in $CO_2$ from 5% to 40%, Flow rate: 3 mL/min, Wavelength: 220 nm.

Step C: tert-Butyl 4-[(3R)-4-benzyloxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate To a mixture of tert-butyl 4-[(3R)-4-benzyloxycarbonyl-3-(cyanomethyl)piperazin-1-yl]-2-chloro-6,8-dihydro-5H-pyrido[3,4-d]pyrimidine-7-carboxylate (290 mg, 550 umol, 1 eq), [(2S)-1-methylpyrrolidin-2-yl]methanol (127 mg, 1.10 mmol, 131 uL, 2 eq), $Pd_2(dba)_3$ (60.5 mg, 66.0 umol, 0.12 eq), RuPhos (51.4 mg, 110 umol, 0.2 eq) and $Cs_2CO_3$ (448 mg, 1.38 mmol, 2.5 eq) in toluene (20 mL) was degassed and purged with $N_2$ for 3 times, and then the mixture was stirred at 90° C. for 7 hours under $N_2$ atmosphere. To the reaction mixture was added $H_2O$ (25 mL×1) and ethyl acetate (25 mL×2). The separated organic phase was washed with brine (100 mL×1), dried over sodium sulfate and then filtered. The filtrate was concentrated under reduced pressure. The residue was diluted with ethyl acetate (50 mL) and acidified with aqueous HCl solution (1 mol/L) to pH=3-4. To the separated water layer was added ethyl acetate (60 mL) and basified with saturated aqueous $Na_2CO_3$ solution to pH=8~9. The organic phase was separated, dried over sodium sulfate, filtered and concentrated under reduced pressure to give a residue. tert-Butyl 4-[(3R)-4-benzyloxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate (225 mg, 0.36 mmol, 66% yield, 97.7% purity) was obtained as a yellow solid. LCMS [ESI, M+1]: 606.

$^1$H NMR (400 MHz, chloroform-d) δ=7.47-7.30 (m, 5H), 5.19 (s, 2H), 4.73-4.52 (m, 2H), 4.44-4.26 (m, 2H), 4.22-4.14 (m, 1H), 4.03-3.74 (m, 3H), 3.41-3.21 (m, 3H), 3.08 (br t, J=7.6 Hz, 1H), 2.97 (dt, J=3.6, 12.4 Hz, 1H), 2.89-2.53 (m, 5H), 2.46 (s, 3H), 2.38-2.10 (m, 2H), 2.08-2.03 (m, 1H), 1.89-1.65 (m, 3H), 1.48 (s, 9H).

SFC condition: Column: Chiralpak AD-3 50×4.6 mm I.D., 3 um, Mobile phase: methanol (0.05% DEA) in $CO_2$ from 5% to 40%, Flow rate: 3 mL/min, Wavelength: 220 nm.

Step D: benzyl (2R)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate To a solution of tert-butyl 4-[(3R)-4-benzyloxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate (620 mg, 1.02 mmol, 1 eq) in dioxane (12 mL) was added HCl/dioxane (4 M, 12.4 mL, 48.5 eq) at 0° C. The mixture was stirred at 25° C. for 0.5 h. The liquid was decanted and the residue was concentrated under vacuum. Benzyl (2R)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (470 mg, crude, HCl) was obtained as a yellow oil which was dissolved into DCM (10 mL). The mixture basified with saturated aqueous sodium carbonate solution to pH=9. The organic phase was separated, washed with brine (5 mL×1), filtered and concentrated under reduced pressure to give a residue which was pure enough without further purification. Benzyl (2R)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (400 mg, 718 umol, 77% yield, 90.8% purity) was obtained as a yellow solid. LCMS [ESI, M+1]: 506.

Step E: benzyl (2R)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a mixture of benzyl (2R)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (210 mg, 415 umol, 1 eq), 1-bromo-8-methyl-naphthalene (Intermediate 69, 119 mg, 540 umol, 1.3 eq) $Pd_2(dba)_3$ (76.1 mg, 83.1 umol, 0.2 eq), $Cs_2CO_3$ (406 mg, 1.25 mmol, 3 eq) and Xantphos (72.1 mg, 125 umol, 0.3 eq) in toluene (7 mL) was degassed and purged with $N_2$ for 3 times, and then the mixture was stirred at 90° C. for 8 hours under $N_2$ atmosphere. To the reaction mixture was added $H_2O$ (20 mL×1) and the mixture was extracted with ethyl acetate (20 mL×2). The extracts were dried over sodium sulfate, filtered and concentrated under reduced pressure. The residue was diluted with ethyl acetate (50 mL) and acidified to pH=3~4 with aqueous HCl solution (1 mol/L). To the water layer was added ethyl acetate (60 mL) and basified to pH=8~9 with saturated $Na_2CO_3$ solution. The organic phase was separated, dried over sodium sulfate, filtered and the filtrate was concentrated under reduced pressure. The residue was purified by column chromatography (SiO$_2$, ethyl acetate/methanol 50/1 to 5/1). Benzyl (2R)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (86 mg, 0.128 mmol, 31% yield, 96.0 purity) was obtained as a yellow solid. LCMS [ESI, M+1]: 646.

Step E: 2-[(2R)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2R)-2-(cyanomethyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (130 mg, 201 umol, 1 eq) in MeOH (15 mL) was added Pd/C (25 mg, 15.5 umol, 10% purity) and NH$_3$.MeOH (15.5 umol, 15 mL, 20% purity) under N$_2$. The suspension was degassed under vacuum and purged with H$_2$ for several times. The mixture was stirred under H$_2$ (15 psi) at 25° C. for 1 hour. The catalyst was filtered off through a pad of celite. The filtrate was concentrated under vacuum. 2-[(2R)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (100 mg, 0.183 mmol, 91% yield, 93.5% purity) was obtained as a yellow solid and used into next step without further purification. LCMS [ESI, M+1]: 512.

Step F: 2-[(2R)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a mixture of 2-[(2R)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (100 mg, 195 umol, 1 eq) and TEA (198 mg, 1.95 mmol, 272 uL, 10 eq) in DCM (10 mL) was added prop-2-enoyl chloride (17.7 mg, 195 umol, 15.9 uL, 1 eq) in portion. After stirring at −40° C. for 30 min, the mixture was quenched with MeOH (2 mL) and concentrated under vacuum. The residue was purified by column chromatography (Al$_2$O$_3$, Dichloromethane/Methanol=10/1 to 10/1). The residue was purified by prep-HPLC (column: Luna C18 150*25 5 u; mobile phase: [water (0.225% FA)-ACN]; B %: 25%-45%, 7.8 min) and (column: Gemini 150*25 5 u; mobile phase: [water (0.05% ammonia hydroxide v/v)-ACN]; B %: 57%-87%, 12 min). The desired fractions were concentrated under reduced pressure to remove acetonitrile, and then lyophlizated. Title compound 2-[(2R)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 461, 17.6 mg, 31.0 umol, 16% yield, 100% purity) was obtained as a white solid. LCMS [ESI, M+1]: 566.

SFC condition: Column: Chiralcel OJ-3 50×4.6 mm I.D., 3 um, Mobile phase: methanol (0.05% DEA) in CO$_2$ from 5% to 40%, Flow rate: 3 mL/min, Wavelength: 220 nm.

$^1$H NMR (400M Hz, chloroform-d) δ=7.77-7.63 (m, 2H), 7.48-7.32 (m, 2H), 7.31-7.18 (m, 2H), 6.61 (br s, 1H), 6.48-6.37 (m, 1H), 5.85 (br d, J=10.0 Hz, 1H), 5.27-4.49 (m, 1H), 4.45-4.33 (m, 1H), 4.33-4.06 (m, 4H), 4.05-3.62 (m, 3H), 3.61-3.34 (m, 2H), 3.33-2.99 (m, 5H), 2.94 (s, 3H), 2.88-2.77 (m, 1H), 2.75-2.57 (m, 2H), 2.54-2.44 (m, 3H), 2.30 (br d, J=7.2 Hz, 1H), 2.15-1.95 (m, 1H), 1.95-1.79 (m, 3H).

Example 462

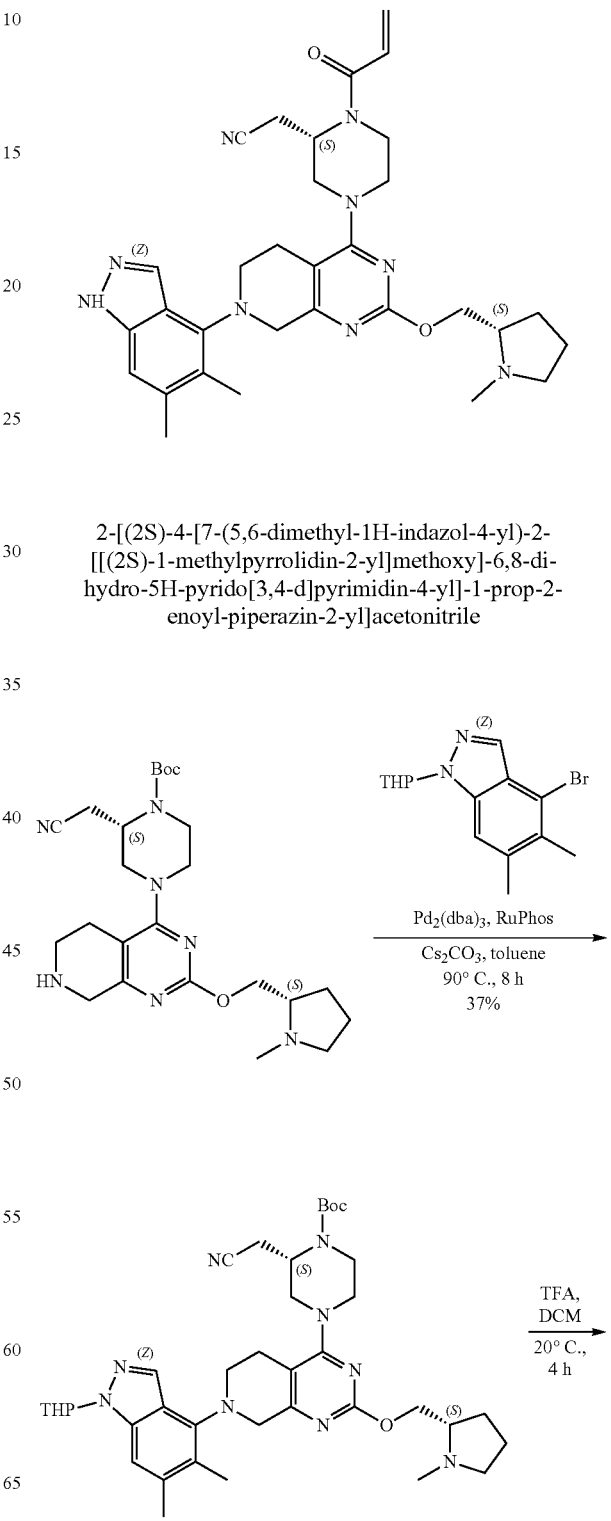

2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile

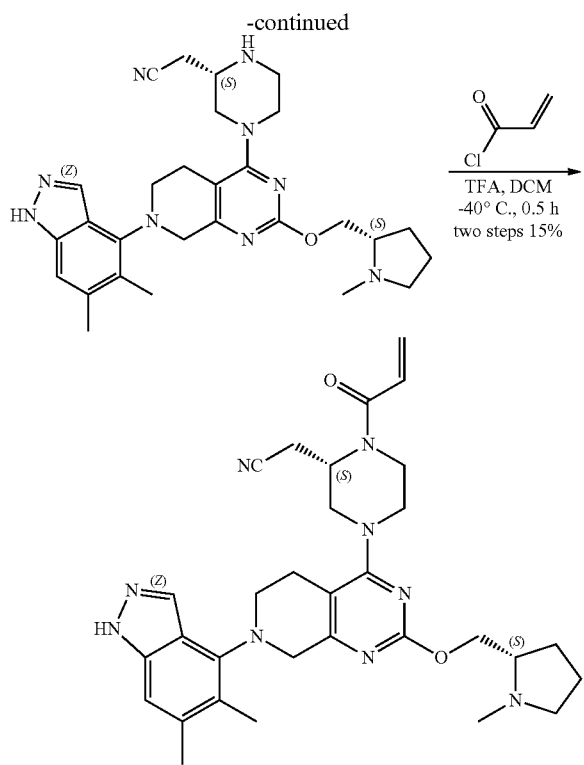

Step A: tert-butyl (2S)-2-(cyanomethyl)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (600 mg, 1.27 mmol, 1 eq), 4-bromo-5,6-dimethyl-1-tetrahydropyran-2-yl-indazole (511 mg, 1.65 mmol, 1.3 eq), RuPhos (237 mg, 509 umol, 0.4 eq), Cs$_2$CO$_3$ (1.04 g, 3.18 mmol, 2.5 eq) and Pd$_2$(dba)$_3$ (233 mg, 254 umol, 0.2 eq) in toluene (20 mL) was de-gassed and then heated to 90° C. for 8 hours under N$_2$. Upon completion, the mixture was filtered and the filtrate was concentrated under vacuum. The residue was purified by reversed phase flash [water (0.1% FA)/acetonitrile]. The desired fractions were collected and neutralized with saturated aqueous NaHCO$_3$. The mixture was concentrated under vacuum to remove MeCN and extracted with EtOAc (2×50 mL). The organic layers were washed with brine (50 mL), dried over Na$_2$SO$_4$, filtered and concentrated under vacuum to give tert-butyl (2S)-2-(cyanomethyl)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (365 mg, 469 umol, 37% yield, 90% purity) as a yellow solid. LCMS [ESI, M+1]: 700.

$^1$H NMR (400 MHz, chloroform-d) δ=7.99 (s, 1H), 7.22 (s, 1H), 5.66 (dd, J=2.8, 9.6 Hz, 1H), 4.61 (br s, 1H), 4.40 (br dd, J=4.8, 10.4 Hz, 1H), 4.26 (br s, 2H), 4.09-3.97 (m, 3H), 3.90 (br d, J=11.6 Hz, 1H), 3.80-3.71 (m, 1H), 3.50 (br t, J=4.8 Hz, 2H), 3.25 (br s, 2H), 3.09 (br t, J=7.6 Hz, 1H), 2.99 (br t, J=11.2 Hz, 1H), 2.83-2.51 (m, 6H), 2.48 (s, 3H), 2.43 (s, 3H), 2.33 (s, 3H), 2.31-2.24 (m, 1H), 2.21-2.13 (m, 1H), 2.11-2.06 (m, 1H), 1.90-1.69 (m, 8H), 1.52 (s, 9H).

Step B: 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (720 mg, 1.03 mmol, 1 eq) in DCM (1 mL) was added TFA (4.62 g, 40.5 mmol, 3 mL, 39.4 eq). The mixture was stirred at 20° C. for 4 hours. Upon completion, the mixture was diluted with DCM (10 mL) and neutralized with saturated aqueous NaHCO$_3$. Then the aqueous phase was extracted with EtOAc (2×30 mL). The organic layers were combined, dried over Na$_2$SO$_4$, filtered and concentrated under vacuum to give 2-[(2S)-4-[7-(5,6-dimethyl-1H-indazol-4-yl)-2-[[(2S)-1-methylpyrrolidin-2-yl] methoxy]-6,8-dihydro-5H-pyrido[3,4-d]pyrimidin-4-yl]piperazin-2-yl]acetonitrile (880 mg, crude) as a yellow solid which was used directly in the next step without further purification. LCMS [ESI, M+1]: 516.

Step C: (2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile To a solution of 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, crude) and TEA (177 mg, 1.75 mmol, 243 uL) in DCM (4 mL) was added prop-2-enoyl chloride (13.2 mg, 145 umol, 11.9 uL) dropwise at −40° C. After stirring at −40° C. for 30 minutes, the mixture was quenched with saturated aqueous NaHCO$_3$ (1 mL) and extracted with DCM (2×10 mL). The organic layers were dried over Na$_2$SO$_4$, filtered and concentrated under vacuum. The residue was purified by chromatography (Al$_2$O$_3$, EtOAc/MeOH 1/0 to 10/1) followed by prep-HPLC (column: Gemini 200*30 10μ; mobile phase: [water (10 mM NH$_4$HCO$_3$)-ACN]; B %: 40%-70%, 6.0 min). The desired fractions were collected and lyophilized to give title compound (2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-prop-2-enoyl-piperazin-2-yl]acetonitrile (EXAMPLE 462, 15.6 mg, 27.2 umol, two steps 15% yield, 99.6% purity) as a white solid. LCMS [ESI, M+1]:570.

SFC condition: Column: Chiralcel OJ-3 100×4.6 mm I.D., 3 um, Mobile phase: methanol (0.05% DEA) in CO$_2$ from 5% to 40%, Flow rate: 3 mL/min, Wavelength: 220 nm.

$^1$H NMR (400 MHz, chloroform-d) δ=10.26 (br s, 1H), 8.03 (s, 1H), 7.14 (s, 1H), 6.57 (br d, J=9.6 Hz, 1H), 6.39 (dd, J=1.2, 16.4 Hz, 1H), 5.83 (br d, J=10.4 Hz, 1H), 5.12-4.38 (m, 2H), 4.28 (s, 2H), 4.23-3.84 (m, 4H), 3.73-3.40 (m, 3H), 3.32 (br s, 1H), 3.10 (br t, J=7.6 Hz, 2H), 2.98-2.61 (m, 5H), 2.48 (s, 3H), 2.41 (s, 3H), 2.34 (s, 3H), 2.32-2.24 (m, 1H), 2.11-1.99 (m, 1H), 1.91-1.78 (m, 3H).

1255
Example 463
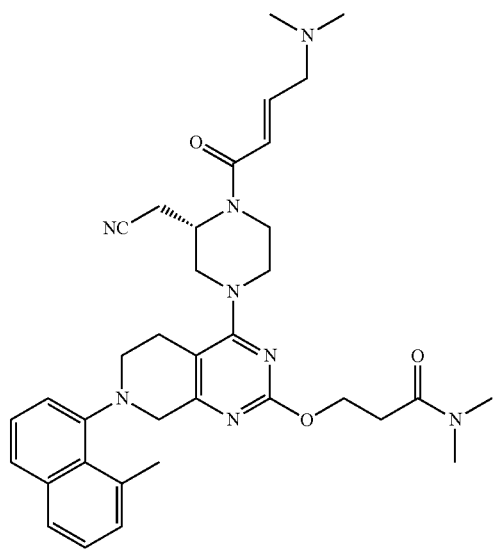 [SMILES: Cc1cccc2cccc(N3CCc4c(nc(OCCC(=O)N(C)C)nc4N4CCN(C(=O)/C=C/CN(C)C)[C@@H](CC#N)C4)C3)c12]
(S,E)-3-((4-(3-(cyanomethyl)-4-(4-(dimethylamino)but-2-enoyl)piperazin-1-yl)-7-(8-methylnaphthalen-1-yl)-5,6,7,8-tetrahydropyrido[3,4-d]pyrimidin-2-yl)oxy)-N,N-dimethylpropanamide
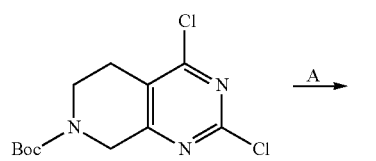 A →
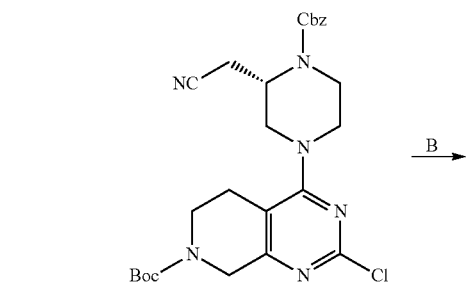 B →
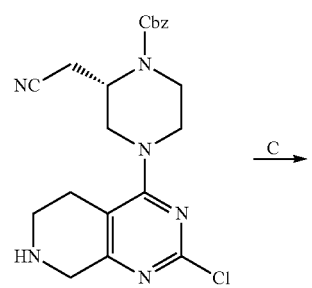 C →
1256
-continued
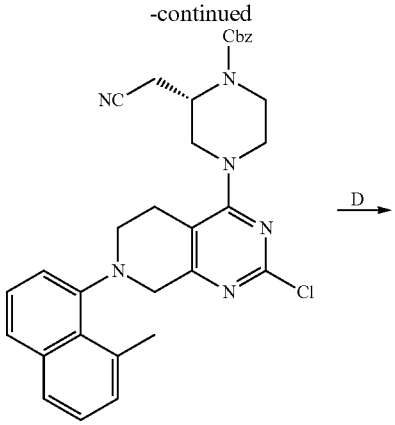 D →
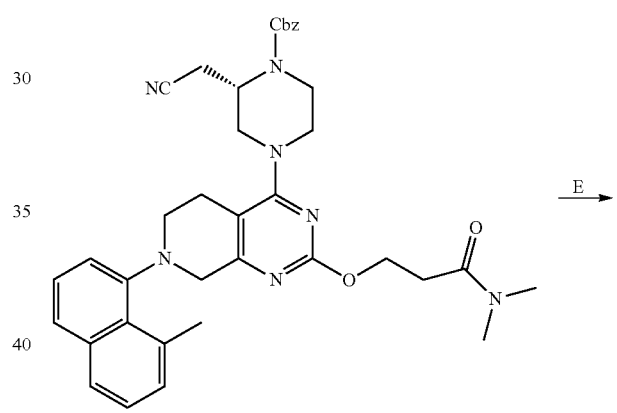 E →
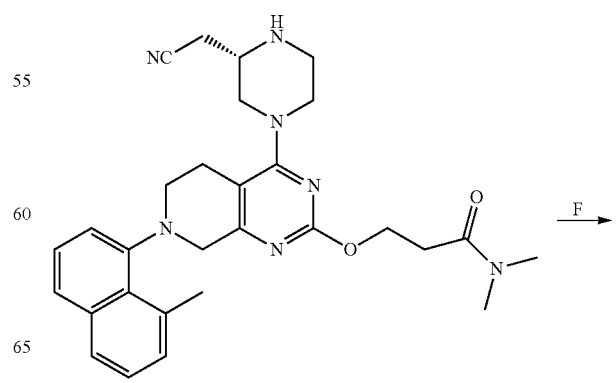 F →

-continued

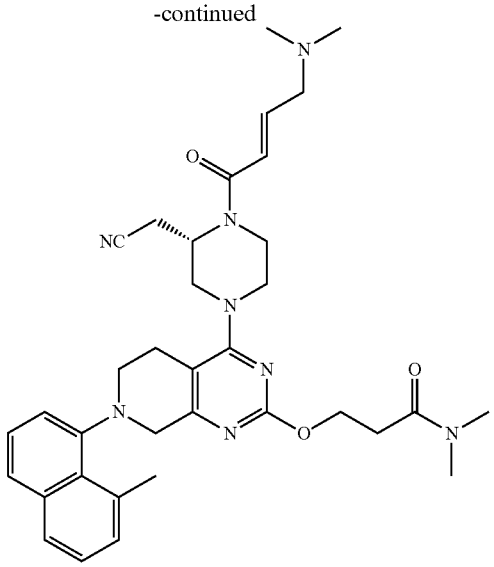

Step A: tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate Benzyl (S)-2-(cyanomethyl)piperazine-1-carboxylate hydrochloride (10 g, 34 mmol) was dissolved in DMA (68 ml, 34 mmol). To the solution was next added tert-butyl 2,4-dichloro-5,8-dihydropyrido[3,4-d]pyrimidine-7(6H)-carboxylate (9.3 g, 30 mmol) followed by Hunig's Base (24 ml, 135 mmol) and the reaction stirred at room temperature for 1 hour. The reaction was next poured into basic water and extracted with MTBE. The organics were washed with additional water, brine, dried over Na$_2$SO$_4$ and concentrated in vacuo. The concentrate was then chromatographed using 10→70% EtOAc/Hexane as eluent to give tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (12 g, 67% yield). ESI+APCI MS m/z 580.3 [M+H]$^+$.

Step B: benzyl (S)-4-(2-chloro-5,6,7,8-tetrahydropyrido[3,4-d]pyrimidin-4-yl)-2-(cyanomethyl)piperazine-1-carboxylate Tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (1.5 g, 2.8 mmol) was dissolved in DCM (28 ml, 2.8 mmol) and treated with Hydrochloric Acid Solution (4.0 M in 1,4-dioxane) (3.6 ml, 14 mmol). The reaction was stirred at room temperature for 1 hour. The organics were washed with 1M NaOH. The aqueous layer was extracted with DCM (2×). The combined organics were dried over Na$_2$SO$_4$, concentrated in vacuo and taken forward as crude benzyl (S)-4-(2-chloro-5,6,7,8-tetrahydropyrido[3,4-d]pyrimidin-4-yl)-2-(cyanomethyl)piperazine-1-carboxylate (1.2 g, 99% yield). ESI+APCI MS m/z 427.2 [M+H]$^+$.

Step C: benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate Tris(dibenzylideneacetone)dipalladium(0) (0.51 g, 0.56 mmol) and Xantphos (0.54 g, 1.1 mmol) were dissolved in 1,4-dioxane (28 ml, 2.8 mmol) and purged under Argon for 5 minutes followed by stirring at 100° C. under Argon for 15 minutes. The reaction was next cooled to room temperature. To the reaction was added benzyl (S)-4-(2-chloro-5,6,7,8-tetrahydropyrido[3,4-d]pyrimidin-4-yl)-2-(cyanomethyl)piperazine-1-carboxylate (1.2 g, 2.8 mmol), 1-bromo-8-methylnaphthalene (1.9 g, 8.4 mmol), and Cesium Carbonate (2.7 g, 8.4 mmol) under Argon. The reaction was capped under Argon and stirred at 100° C. over night. The reaction was cooled to room temperature and was filtered through GF/F paper. The filtrate was concentrated in vacuo and purified by normal phase chromatography on the CombiFlash using 0% 475% Hexanes/EtOAc as the eluent to give benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate (0.45 g, 28% yield). ESI+APCI MS m/z 567.2 [M+H]$^+$.

Step D: benzyl (S)-2-(cyanomethyl)-4-(2-(3-(dimethylamino)-3-oxopropoxy)-7-(8-methylnaphthalen-1-yl)-5,6,7,8-tetrahydropyrido[3,4-d]pyrimidin-4-yl)-3,4-dihydropyrazine-1(2H)-carboxylate In a microwave tube a solution of benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate (250 mg, 0.441 mmol) in dioxane (4408 µl, 0.441 mmol) was sparged with Argon for 5 minutes. 3-Hydroxy-N,N-dimethylpropanamide (155 mg, 1.32 mmol), Cesium Carbonate (431 mg, 1.32 mmol), Methanesulfonato(2-dicyclohexylphosphino-2',6'-di-i-propoxy-1,1'-biphenyl)(2'-methylamino-1,1'-biphenyl-2-yl)palladium(II) (37.5 mg, 0.0441 mmol) were sequentially added under Argon and the reaction sparged for an additional 5 minutes with Argon. The reaction mixture was capped and heated at 100° C. for 1 hour. The reaction was cooled to room temperature and Ethyl Acetate was added. The reaction was filtered through GF/F paper and the filtrated concentrated in vacuo. The residue was purified by flash chromatography eluting with 0→20% MeOH+2% NH$_4$OH/DCM. All fractions containing clean desired product were combined and concentrated to give benzyl (S)-2-(cyanomethyl)-4-(2-(3-(dimethylamino)-3-oxopropoxy)-7-(8-methylnaphthalen-1-yl)-5,6,7,8-tetrahydropyrido[3,4-d]pyrimidin-4-yl)-3,4-dihydropyrazine-1(2H)-carboxylate (140 mg, 49.2% yield). ESI+APCI MS m/z 648.3 [M+H]$^+$.

Step E: (S)-3-((4-(3-(cyanomethyl)piperazin-1-yl)-7-(8-methylnaphthalen-1-yl)-5,6,7,8-tetrahydropyrido[3,4-d]pyrimidin-2-yl)oxy)-N,N-dimethylpropanamide A solution of benzyl (S)-2-(cyanomethyl)-4-(2-(3-(dimethylamino)-3-oxopropoxy)-7-(8-methylnaphthalen-1-yl)-5,6,7,8-tetrahydropyrido[3,4-d]pyrimidin-4-yl)piperazine-1-carboxylate (140 mg, 0.216 mmol) in EtOH (2161 µl, 0.216 mmol) and THF (2161 µl, 0.216 mmol) was purged with N$_2$ for 5 minutes. To this solution was added Palladium (57.5 mg, 0.0540 mmol) (Degussa Type, 10 wt %, 50% H$_2$O) and the reaction capped and purged with N$_2$ for an additional 5 minutes. The solution was stirred under one atmosphere of H₂ overnight. The mixture was diluted with MeOH and filtered through packed celite. The filtrate was then concentrated in vacuo to provide crude (S)-3-((4-(3-(cyanomethyl)piperazin-1-yl)-7-(8-methylnaphthalen-1-yl)-5,6,7,8-tetrahydropyrido[3,4-d]pyrimidin-2-yl)oxy)-N,N-dimethylpropanamide (111 mg, 100.0% yield). ESI+APCI MS m/z 514.3 [M+H]⁺.

Step F: (S,E)-3-((4-(3-(cyanomethyl)-4-(4-(dimethylamino)but-2-enoyl)piperazin-1-yl)-7-(8-methylnaphthalen-1-yl)-5,6,7,8-tetrahydropyrido[3,4-d]pyrimidin-2-yl)oxy)-N,N-dimethylpropanamide To a 25 mL round bottom flask containing dichloromethane (2161 μl, 0.216 mmol) cooled to 0° C. was added (S)-3-((4-(3-(cyanomethyl)piperazin-1-yl)-7-(8-methylnaphthalen-1-yl)-5,6,7,8-tetrahydropyrido[3,4-d]pyrimidin-2-yl)oxy)-N,N-dimethylpropanamide (111 mg, 0.216 mmol) and Hunig's base (226 μl, 1.30 mmol). The reaction mixture was vigorously stirred while (E)-4-(dimethylamino)but-2-enoic acid (167 mg, 1.30 mmol) was added in one portion. Next, 1-Propanephosphonic acid cyclic anhydride (772 μl, 1.30 mmol) was added slowly to the stirring mixture. The reaction was stirred for 2 hours at 0° C. The reaction was treated with basic water and the aqueous layer extracted with EtOAc (3×). The combined organics were concentrated in vacuo and purified on the Gilson (prep HPLC) eluting with 5→95% ACN+0.1% TFA/water+0.1% TFA. Fractions containing product were combined, diluted with 1M NaOH and the aqueous layer extracted with DCM. The organics were dried over Na₂SO₄ and concentrated in vacuo to give title compound (S,E)-3-((4-(3-(cyanomethyl)-4-(4-(dimethylamino)but-2-enoyl)piperazin-1-yl)-7-(8-methylnaphthalen-1-yl)-5,6,7,8-tetrahydropyrido[3,4-d]pyrimidin-2-yl)oxy)-N,N-dimethylpropanamide (17.6 mg, 13.0% yield). ESI+APCI MS m/z 625.4 [M+H]⁺.

Example 464

2-((S)-1-acryloyl-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

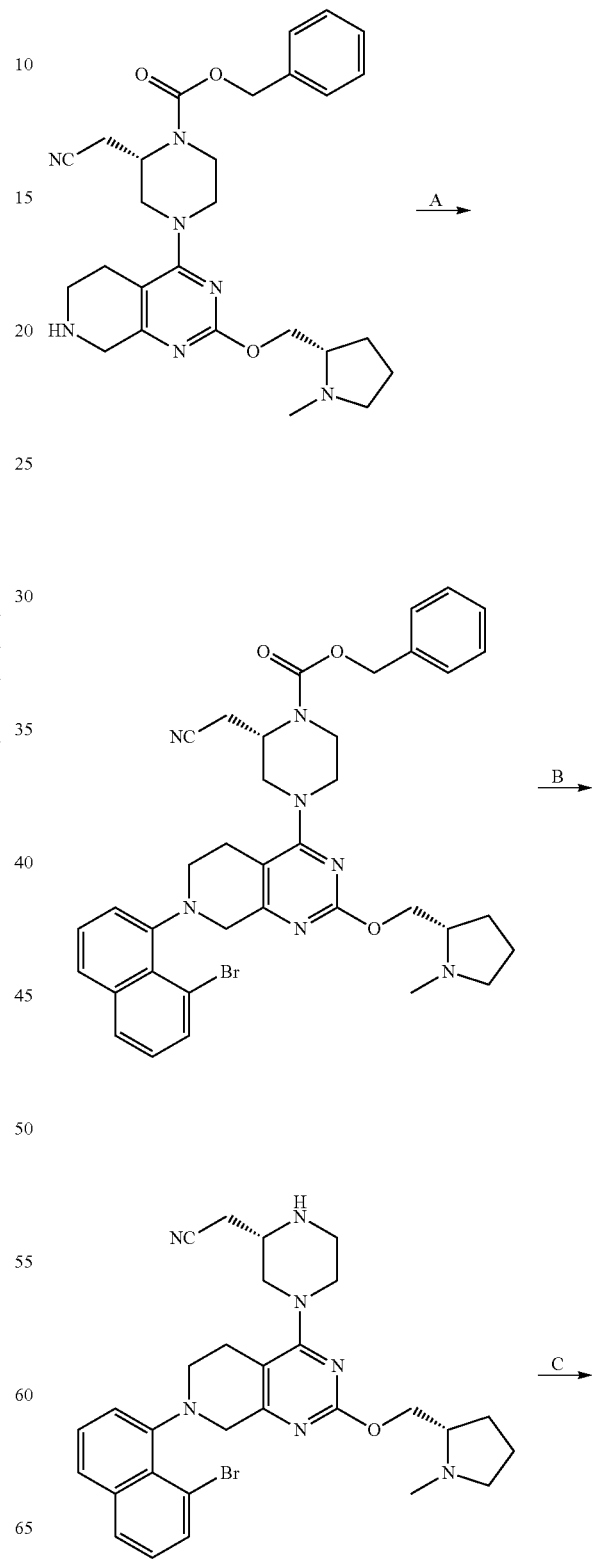

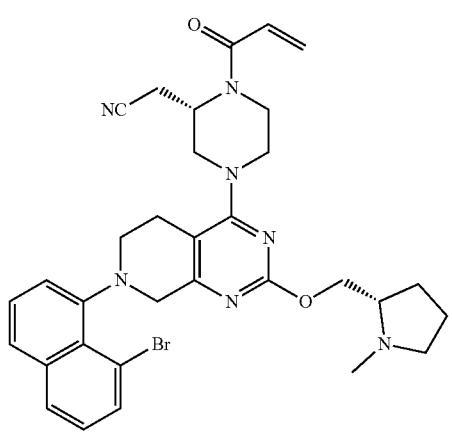 [SMILES: C=CC(=O)N1CCN(c2nc(OC[C@@H]3CCCN3C)nc3c2CCN(c2cccc4cccc(Br)c24)C3)C[C@@H]1CC#N]

-continued

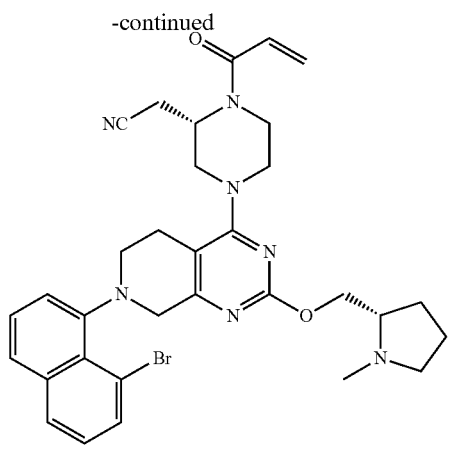

Step A: Benzyl (S)-4-(7-(8-bromonaphthalen-1-yl)-2-((S)-1-methylpyrrolidin-2-yl)methoxy)-5,6,7,8-tetrahydropyrido[3,4-d]pyrimidin-4-yl)-2-(cyanomethyl)piperazine-1-carboxylate Benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (200 mg, 0.396 mmol), Cs$_2$CO$_3$ (644 mg, 1.98 mmol), 1,8-dibromonaphthalene (339 mg, 1.19 mmol), Pd$_2$(dba)$_3$ (72.4 mg, 0.0791 mmol) and XANTPHOS (91.6 mg, 0.158 mmol) were diluted with toluene (1582 µl, 0.396 mmol). The reaction was purged with argon, sealed and heated to 100° C. After stirring for 23 hours, the reaction was cooled and diluted with ethyl acetate and saturated sodium bicarbonate. The layers were separated and the ethyl acetate was dried over MgSO$_4$, filtered and concentrated. The material was purified on silica gel eluting with 1-10% methanol/DCM (1% NH$_4$OH as additive) to afford benzyl (S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (68 mg, 24.2% yield). ESI+APCI MS m/z 712.2 [M+H]$^+$.

Step B: 2-((S)-4-(7-(8-bromonaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile Benzyl (S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (25 mg, 0.035 mmol) was diluted with TFA (2 mL), placed under nitrogen and heated to 90° C. After stirring for 2 hours, the reaction was cooled and concentrated. The material was diluted with DCM and washed with saturated sodium bicarbonate. The DCM was dried over MgSO$_4$, filtered and concentrated. The material was purified on silica gel eluting with 10% methanol/DCM (1% NH4OH as additive) to afford 2-((S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (8 mg, 39% yield). ESI-APCI MS m/z 578.2 [M+H]$^+$.

Step C: 2-((S)-1-acryloyl-4-(7-(8-bromonaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile 2-((S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (8 mg, 0.014 mmol) was diluted with DCM (200 uL) followed by the addition of acryloyl chloride (1.4 mg, 0.015 mmol) and DIEA (4.8 µl, 0.028 mmol). After stirring for 12 hours, the reaction was diluted with saturated sodium carbonate and extracted twice with DCM. The DCM was dried over MgSO$_4$, filtered and concentrated. The material was purified on silica gel eluting with 10% methanol/DCM (1% NH$_4$OH as additive) to afford title compound 2-((S)-1-acryloyl-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (EXAMPLE 464, 6 mg, 69% yield). ESI+APCI MS m/z 632.2 [M+H]$^+$.

Example 465

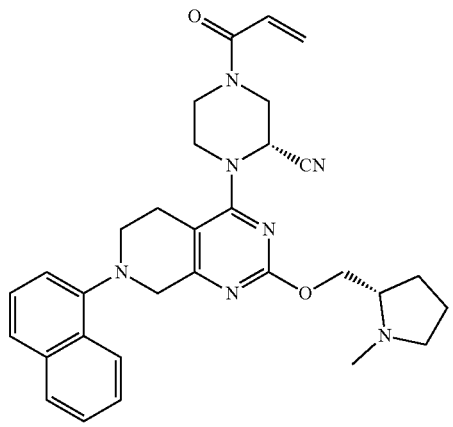 [SMILES: C=CC(=O)N1CCN(c2nc(OC[C@@H]3CCCN3C)nc3c2CCN(c2cccc4ccccc24)C3)[C@@H](C#N)C1]

(R)-4-acryloyl-1-(2-(((S)-1-methylpyrrolidin-2-yl)methoxy)-7-(naphthalen-1-yl)-5,6,7,8-tetrahydropyrido[3,4-d]pyrimidin-4-yl)piperazine-2-carbonitrile

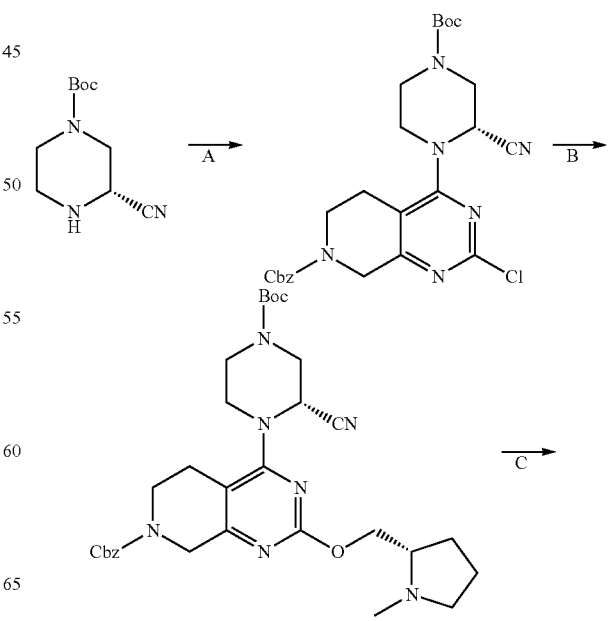

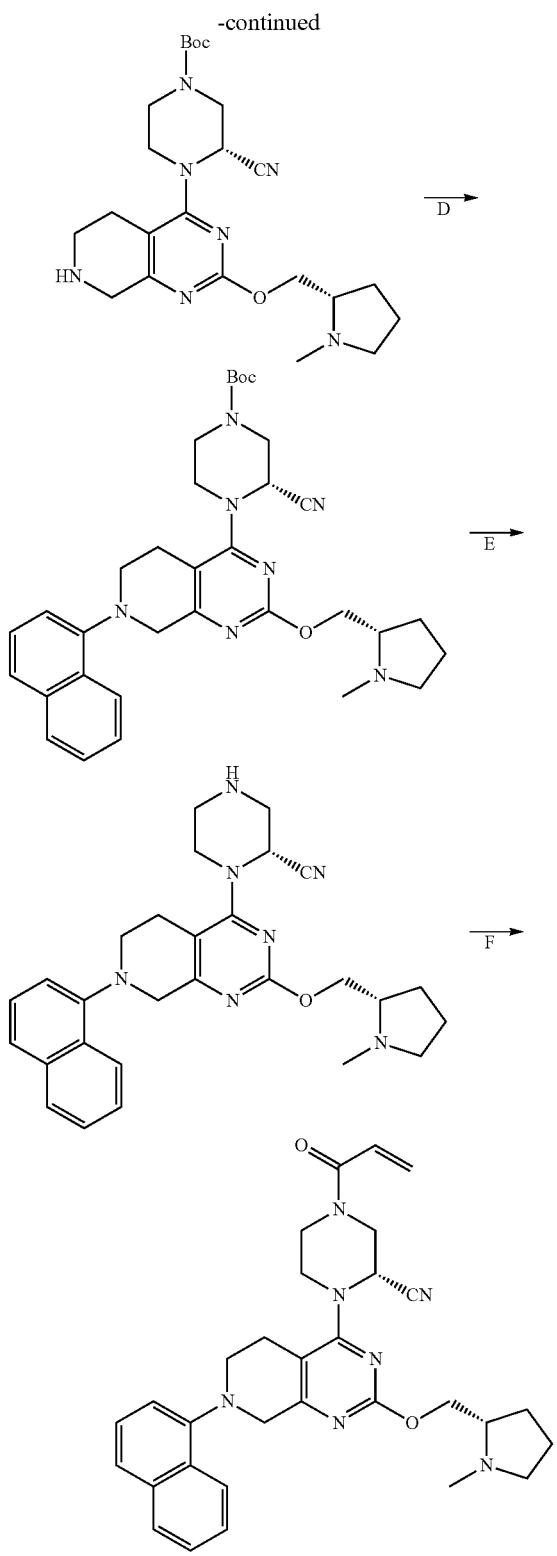

Step A: benzyl (R)-4-(4-(tert-butoxycarbonyl)-2-cyanopiperazin-1-yl)-2-chloro-5,8-dihydropyrido[3,4-d]pyrimidine-7(6H)-carboxylate A mixture of benzyl 2,4-dichloro-5,6-dihydropyrido[3,4-d]pyrimidine-7(8H)-carboxylate (700 mg, 2.07 mmol), R-1-N-Boc-3-cyanopiperazine (656 mg, 3.10 mmol), N,N-dimethylacetamide (1 ml) and N-ethyl-N-isopropylpropan-2-amine (0.433 ml, 2.48 mmol) was stirred at 60° C. under nitrogen atmosphere for 48 hours. The reaction mixture was cooled, partitioned between MTBE (50 mL) and 0.2M $Na_2CO_3$ (15 mL) and the layers separated. The organic layer was washed with water and brine (10 mL each), dried over $Na_2SO_4$ and evaporated in vacuo. The material crystallized upon dilution with MTBE (5 mL). The mother liquor was decanted and the solid was washed with MTBE (2*1 mL) followed by purification on silica gel using in 40 to 60% EtOAc/hexane as eluent to give product (308 mg, 29%). ESI+APCI MS m/z 513.2 [M+H]+.

Step B: benzyl 4-((R)-4-(tert-butoxycarbonyl)-2-cyanopiperazin-1-yl)-2-(((S)-1-methylpyrrolidin-2-yl)methoxy)-5,8-dihydropyrido[3,4-d]pyrimidine-7(6H)-carboxylate A mixture of benzyl (R)-4-(4-(tert-butoxycarbonyl)-2-cyanopiperazin-1-yl)-2-chloro-5,8-dihydropyrido[3,4-d]pyrimidine-7(6H)-carboxylate (308 mg, 0.600 mmol), $Cs_2CO_3$ (587 mg, 1.80 mmol), methanesulfonato(2-dicyclohexylphosphino-2',6'-di-i-propoxy-1,1'-biphenyl)(2'-methylamino-1,1'-biphenyl-2-yl)palladium(II) (RuPhos-Pd-G4, 51.1 mg, 0.0600 mmol), (S)-(1-methylpyrrolidin-2-yl)methanol (346 mg, 3.00 mmol) and 1,4-dioxane (4 ml) was purged with $N_2$ and the vial was capped and reaction stirred at 70° C. for 2 hours. The reaction mixture was partitioned between water (5 mL) and EtOAc (20 mL) and the organic layer separated. The organics were washed with water and brine (3 mL each), dried over $Na_2SO_4$ and evaporated in vacuo. The residue was chromatographed on silica gel using 4% MeOH+0.4% $NH_4OH$/DCM as eluent to give product as a mixture of isomers (214 mg of ~60% purity, 36%). ESI+APCI MS m/z 592.3 [M+H]+.

Step C: tert-butyl (R)-3-cyano-4-(2-(((S)-1-methyl-pyrrolidin-2-yl)methoxy)-5,6,7,8-tetrahydropyrido[3,4-d]pyrimidin-4-yl)piperazine-1-carboxylate A mixture of crude benzyl 4-((R)-4-(tert-butoxycarbonyl)-2-cyanopiperazin-1-yl)-2-(((S)-1-methylpyrrolidin-2-yl)methoxy)-5,8-dihydropyrido[3,4-d]pyrimidine-7(6H)-carboxylate (214 mg, 0.362 mmol), methanol (7 ml, 0.362 mmol), and palladium on carbon (20 mg, 5%, Degussa type E101 NO/W) was degassed and stirred under hydrogen atmosphere for 1.5 hours. The reaction mixture was filtered through Celite (2 mL), the celite washed with MeOH (3*3 mL) and the combined organics evaporated in vacuo to give product which was used crude in the next reaction. ESI+APCI MS m/z 458.3 [M+H]+.

Step D: tert-butyl (R)-3-cyano-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate A mixture of tert-butyl (R)-3-cyano-4-(2-(((S)-1-methyl-pyrrolidin-2-yl)methoxy)-5,6,7,8-tetrahydropyrido[3,4-d]pyrimidin-4-yl)piperazine-1-carboxylate (165 mg, 0.361 mmol), $Cs_2CO_3$ (352 mg, 1.08 mmol), dioxane (0.5 mL), 1-iodonaphthalene (0.0790 ml, 0.541 mmol) and methanesulfonato(2-dicyclohexylphosphino-2',6'-di-i-propoxy-1,1'-biphenyl)(2'-methylamino-1,1'-biphenyl-2-yl)palladium(II) (RuPhos-Pd-G4, 0.1 eq., 30.7 mg, 0.0361 mmol) was purged with nitrogen, the flask capped and stirred at 70° C. for 1.5 hours. The reaction mixture was cooled and partitioned between EtOAc (20 mL) and water (5 mL) and the layers separated. The organic layer was washed with water and brine (5 mL each), dried over Na$_2$SO$_4$ and evaporated in vacuo. The residue was chromatographed on silica gel using 4% MeOH+0.4% NH$_4$OH/DCM as eluent to give product (120 mg, 57%). ESI+APCI MS m/z 584.3 [M+H]$^+$.

Step E: (R)-1-(2-(((S)-1-methylpyrrolidin-2-yl)methoxy)-7-(naphthalen-1-yl)-5,6,7,8-tetrahydro-pyrido[3,4-d]pyrimidin-4-yl)piperazine-2-carbonitrile The (tert-butyl (R)-3-cyano-4-(2-(((S)-1-methylpyrrolidin-2-yl)methoxy)-7-(naphthalen-1-yl)-5,6,7,8-tetrahydropyrido[3,4-d]pyrimidin-4-yl)piperazine-1-carboxylate (120 mg, 0.206 mmol) was dissolved in dichloromethane (0.5 ml) and cooled to 0° C. followed by addition of 4M hydrogen chloride (1.03 ml, 4.11 mmol) and the reaction stirred for 1 hr while warming to room temperature. The mixture was evaporated in vacuo and the residue was partitioned between DCM (10 mL) and 2M Na$_2$CO$_3$ (0.5 mL) and the layers separated. The organics were dried over Na$_2$CO$_3$, filtered and evaporated in vacuo. The material was used crude in the next reaction. ESI+APCI MS m/z 484.2 [M+H]$^+$.

Step F: (R)-4-acryloyl-1-(2-(((S)-1-methylpyrrolidin-2-yl)methoxy)-7-(naphthalen-1-yl)-5,6,7,8-tetrahydropyrido[3,4-d]pyrimidin-4-yl)piperazine-2-carbonitrile A solution of (R)-1-(2-(((S)-1-methylpyrrolidin-2-yl)methoxy)-7-(naphthalen-1-yl)-5,6,7,8-tetrahydropyrido[3,4-d]pyrimidin-4-yl)piperazine-2-carbonitrile (79 mg, 0.1634 mmol) in DCM (5 mL) was cooled to −30° C. with stirring followed by addition of triethylamine (68.31 µl, 0.4901 mmol) and acryloyl chloride (26.54 µl, 0.3267 mmol). After 5 minutes at −30° C., the reaction was quenched by addition of MeOH (0.05 mL) and the reaction warmed to room temperature. The organics were next separated and washed with 0.5M Na$_2$CO$_3$ (4 mL), dried over Na$_2$CO$_3$ and evaporated in vacuo. The residue was chromatographed on silica gel using 4% MeOH+0.4% NH$_4$OH/DCM as eluent to give title compound (EXAMPLE 465, 17 mg, 19%). ESI+APCI MS m/z 538.3 [M+H]$^+$.

Example 466

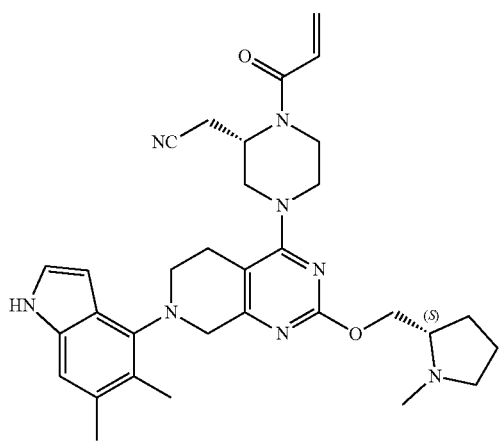

2-((S)-1-acryloyl-4-(7-(5,6-dimethyl-1H-indol-4-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-acryloyl-4-(7-(5,6-dimethyl-1H-indol-4-yl)-2-(((S)-1-methylpyrrolidin-2-yl)methoxy)-5,6,7,8-tetrahydropyrido[3,4-d]pyrimidin-4-yl)piperazin-2-yl)acetonitrile The title compound is prepared following Example 454 substituting Intermediate 66 for tert-butyl 4-[2-[[(2S)-1-methylpyrrolidin-2-yl]methoxy]-5,6,7,8-tetrahydropyrido[3,4-d]pyrimidin-4-yl]piperazine-1-carboxylate in Step A.

Example 467

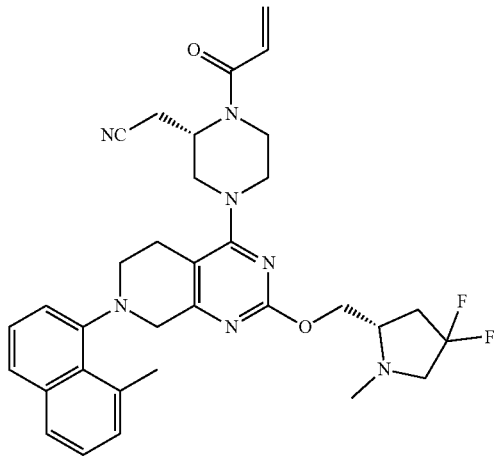 [SMILES: C=CC(=O)N1CCN(c2nc(OC[C@@H]3CC(F)(F)CN3C)nc3c2CCN(c2cccc4cccc(C)c24)C3)C[C@@H]1CC#N]

2-((S)-1-acryloyl-4-(2-(((S)-4,4-difluoro-1-methyl-pyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile 2-((S)-1-acryloyl-4-(2-(((S)-4,4-difluoro-1-methyl-pyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile The title compound is prepared following Example 447 substituting benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate in Example 447, Step A for benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate in Example 447, Step A.

Example 468

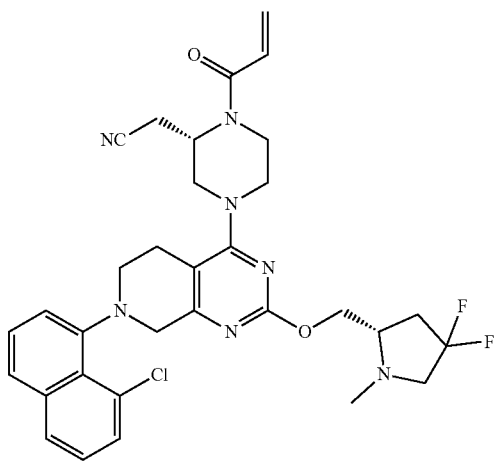 [SMILES: C=CC(=O)N1CCN(c2nc(OC[C@@H]3CC(F)(F)CN3C)nc3c2CCN(c2cccc4cccc(Cl)c24)C3)C[C@@H]1CC#N]

2-((S)-1-acryloyl-4-(7-(8-chloronaphthalen-1-yl)-2-
(((S)-4,4-difluoro-1-methylpyrrolidin-2-yl)
methoxy)-5,6,7,8-tetrahydropyrido[3,4-d]pyrimidin-
4-yl)piperazin-2-yl)acetonitrile 2-((S)-1-acryloyl-4-(7-(8-chloronaphthalen-1-yl)-2-
((S)-4,4-difluoro-1-methylpyrrolidin-2-yl)methoxy)-
5,6,7,8-tetrahydropyrido[3,4-d]pyrimidin-4-yl)piper-
azin-2-yl)acetonitrile The title compound is prepared following Example 447 substituting benzyl (S)-4-(2-chloro-7-(8-chloronaphthalen-1-yl)-5,6,7,8-tetrahydropyrido[3,4-d]pyrimidin-4-yl)-2-(cyanomethyl)piperazine-1-carboxylate in Example 447, Step A for benzyl (S)-4-(2-chloro-7-(naphthalen-1-yl)-5,6,7,8-tetrahydropyrido[3,4-d]pyrimidin-4-yl)-2-(cyanomethyl)piperazine-1-carboxylate in Example 447, Step A.

Example 469

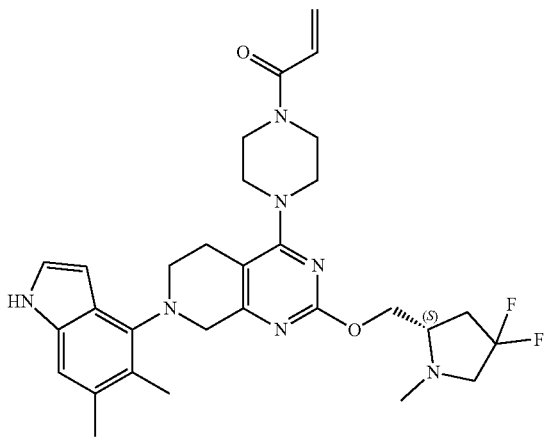

(S)-1-(4-(2-((4,4-difluoro-1-methylpyrrolidin-2-yl)
methoxy)-7-(5,6-dimethyl-1H-indol-4-yl)-5,6,7,8-
tetrahydropyrido[3,4-d]pyrimidin-4-yl)piperazin-1-
yl)prop-2-en-1-one (S)-1-(4-(2-((4,4-difluoro-1-methylpyrrolidin-2-yl)
methoxy)-7-(5,6-dimethyl-1H-indol-4-yl)-5,6,7,8-
tetrahydropyrido[3,4-d]pyrimidin-4-yl)piperazin-1-
yl)prop-2-en-1-one The title compound is prepared following EXAMPLE 457 substituting EXAMPLE 139, Step B product 2-(3,3-difluoropyrrolidin-1-yl)ethanol for [(2S)-1-methylpyrrolidin-2-yl]methanol in preparation of Intermediate 66, Step E and then following EXAMPLE 457 Steps B-D.

Example 470

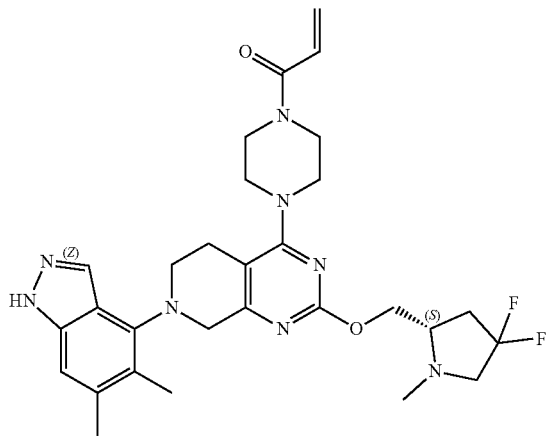

(S)-1-(4-(2-((4,4-difluoro-1-methylpyrrolidin-2-yl)
methoxy)-7-(5,6-dimethyl-1H-indazol-4-yl)-5,6,7,8-
tetrahydropyrido[3,4-d]pyrimidin-4-yl)piperazin-1-
yl)prop-2-en-1-one (S)-1-(4-(2-((4,4-difluoro-1-methylpyrrolidin-2-yl)
methoxy)-7-(5,6-dimethyl-1H-indazol-4-yl)-5,6,7,8-
tetrahydropyrido[3,4-d]pyrimidin-4-yl)piperazin-1-
yl)prop-2-en-1-one The title compound is prepared following Example 453 substituting Example 139, Step B product 2-(3,3-difluoropyrrolidin-1-yl)ethanol for [(2S)-1-methylpyrrolidin-2-yl]methanol in preparation of Intermediate 66, Step E and then following Example 453 Steps B-C.

Example 471

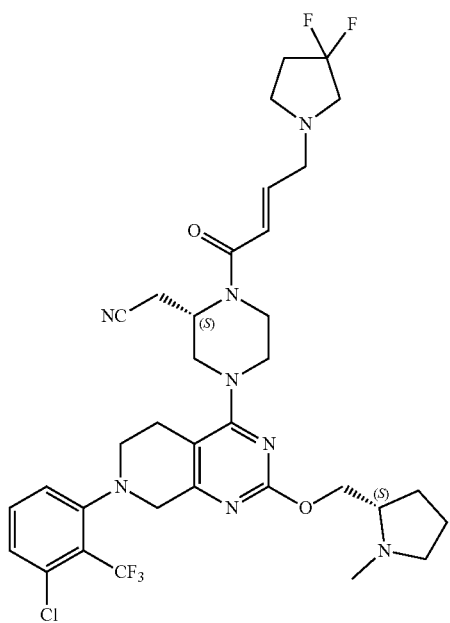

2-[(2S)-4-[7-[3-chloro-2-(trifluoromethyl)phenyl]-2-
[[(2S)-1-methylpyrrolidin-2-yl]methoxy]-6,8-di-
hydro-5H-pyrido[3,4-d]pyrimidin-4-yl]-1-[(E)-4-(3,
3-difluoropyrrolidin-1-yl)but-2-enoyl]piperazin-2-yl]
acetonitrile

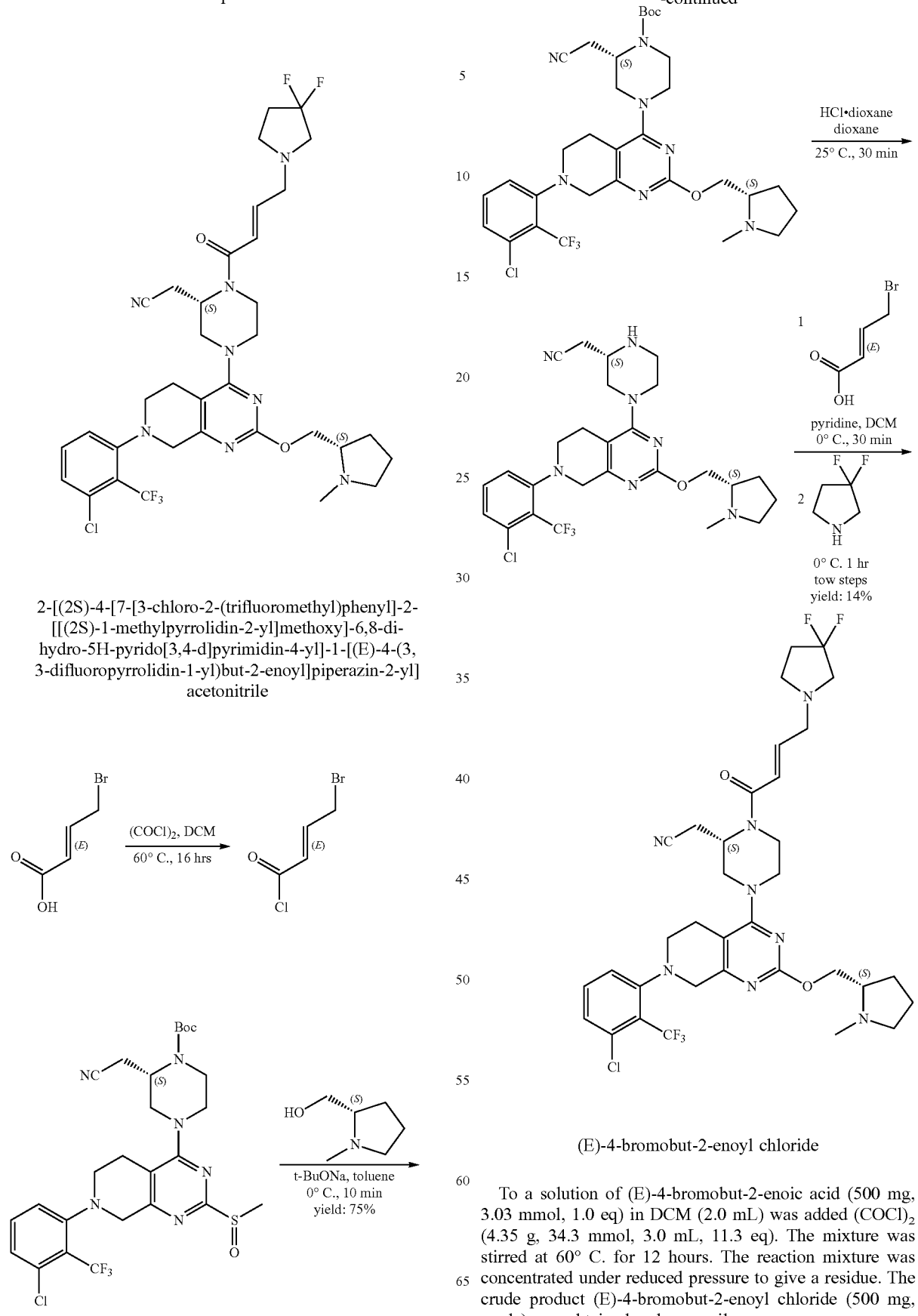

(E)-4-bromobut-2-enoyl chloride

To a solution of (E)-4-bromobut-2-enoic acid (500 mg, 3.03 mmol, 1.0 eq) in DCM (2.0 mL) was added (COCl)₂ (4.35 g, 34.3 mmol, 3.0 mL, 11.3 eq). The mixture was stirred at 60° C. for 12 hours. The reaction mixture was concentrated under reduced pressure to give a residue. The crude product (E)-4-bromobut-2-enoyl chloride (500 mg, crude) was obtained as brown oil.

Step A: tert-butyl (2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate To a solution of tert-butyl (2S)-4-[7-[3-chloro-2-(trifluoromethyl)phenyl]-2-methylsulfinyl-6,8-dihydro-5H-pyrido[3,4-d]pyrimidin-4-yl]-2-(cyanomethyl)piperazine-1-carboxylate (1.30 g, 2.17 mmol, 1.0 eq) and [(2S)-1-methylpyrrolidin-2-yl]methanol (500 mg, 4.34 mmol, 515 uL, 2.0 eq) in toluene (20.0 mL) was added t-BuONa (417 mg, 4.34 mmol, 2.0 eq). The mixture was stirred at 0° C. for 10 min. The reaction mixture was quenched by addition saturated brine (30.0 mL) at 20° C., and extracted with EA (3×30.0 mL). The combined organic layers were washed with saturated brine (30.0 mL), dried over Na$_2$SO$_4$, filtered and concentrated under reduced pressure to give a residue. The residue was purified by column chromatography (SiO$_2$, Petroleum ether/Ethyl acetate=3/1 to EA/MeOH=10/1). The product tert-butyl (2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (1.1 g, 1.62 mmol, 75% yield, 96% purity) was obtained as a yellow solid. LCMS [ESI, M+1]: 650.

Step B: 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (100 mg, 154 umol, 1.00 eq) in dioxane (0.5 mL) was added HCl.dioxane (4 M, 1.00 mL, 26.0 eq). The mixture was stirred at 0° C. for 10 min. The reaction mixture was concentrated under reduced pressure to remove dioxane. The residue was diluted with saturated NaHCO$_3$ aqueous (10.0 mL) and extracted with EA (10 mL×3). The combined organic layers were washed with saturated brine (20.0 mL), dried over Na$_2$SO$_4$, filtered and concentrated under reduced pressure to give a residue. The crude product 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (90.0 mg, crude) was obtained as a white solid. LCMS [ESI, M+1]:550.

Step C: 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-[(E)-4-(3,3-difluoropyrrolidin-1-yl)but-2-enoyl]piperazin-2-yl]acetonitrile To a solution of 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]piperazin-2-yl]acetonitrile (80.0 mg, 145 umol, 1.0 eq) in DCM (3.0 mL) was added Py (115 mg, 1.45 mmol, 117 uL, 10.0 eq) and (E)-4-bromobut-2-enoyl chloride (107 mg, 582 umol, 4.0 eq) in DCM (3.0 mL). The mixture was stirred at 0° C. for 1 hour. After the starting material was consumed, then to a solution of 3,3-difluoropyrrolidine (156 mg, 1.45 mmol, 10.0 eq) in DCM (6.0 mL) was added the reaction mixture. The mixture was stirred at 0° C. at 2 hours. The reaction mixture was concentrated under reduced pressure to give a residue. The residue was purified by prep-HPLC (column: Phenomenex Gemini 150*25 mm*10 um; mobile phase: [water (0.05% ammonia hydroxide v/v)-ACN]; B %: 62%-92%,12 min). And the residue was concentrated under reduced pressure to remove ACN, and then lyophilization. Title compound 2-[(2S)-4-[7-[3-chloro-2-(trifluoromethyl)phenyl]-2-[[(2S)-1-methylpyrrolidin-2-yl]methoxy]-6,8-dihydro-5H-pyrido[3,4-d]pyrimidin-4-yl]-1-[(E)-4-(3,3-difluoropyrrolidin-1-yl)but-2-enoyl]piperazin-2-yl]acetonitrile (EXAMPLE 471, 15.4 mg, 20.8 umol, 14% yield, 97.7% purity) was obtained as a white solid. LCMS [ESI, M+1]: 723.

$^1$H NMR (400 MHz, CHLOROFORM-d) δ=7.40 (t, J=8.2 Hz, 1H), 7.30-7.26 (m, 1H), 7.19 (d, J=8.0 Hz, 1H), 7.05-6.90 (m, 1H), 6.60-6.40 (m, 1H), 5.08 (br s, 1H), 4.39 (br dd, J=5.2, 10.8 Hz, 1H), 4.17 (br dd, J=6.8, 10.8 Hz, 1H), 4.1 (br s, 2H), 4.12-4.05 (m, 1H), 3.97 (br d, J=10.8 Hz, 2H), 3.70-3.53 (m, 1H), 3.35-3.25 (m, 3H), 3.17-3.07 (m, 2H), 2.96 (br t, J=13.2 Hz, 3H), 2.90-2.85 (m, 1H), 2.81 (br t, J=6.8 Hz, 3H), 2.75-2.65 (m, 2H), 2.50 (s, 3H), 2.40-2.27 (m, 3H), 2.15-1.95 (m, 1H), 1.95-1.72 (m, 5H).

Example 472

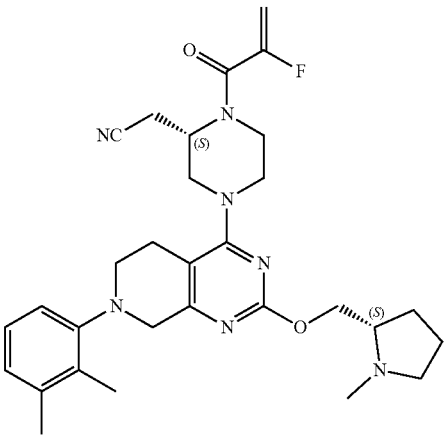

2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

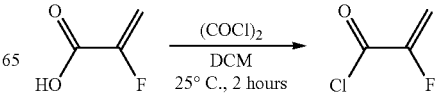

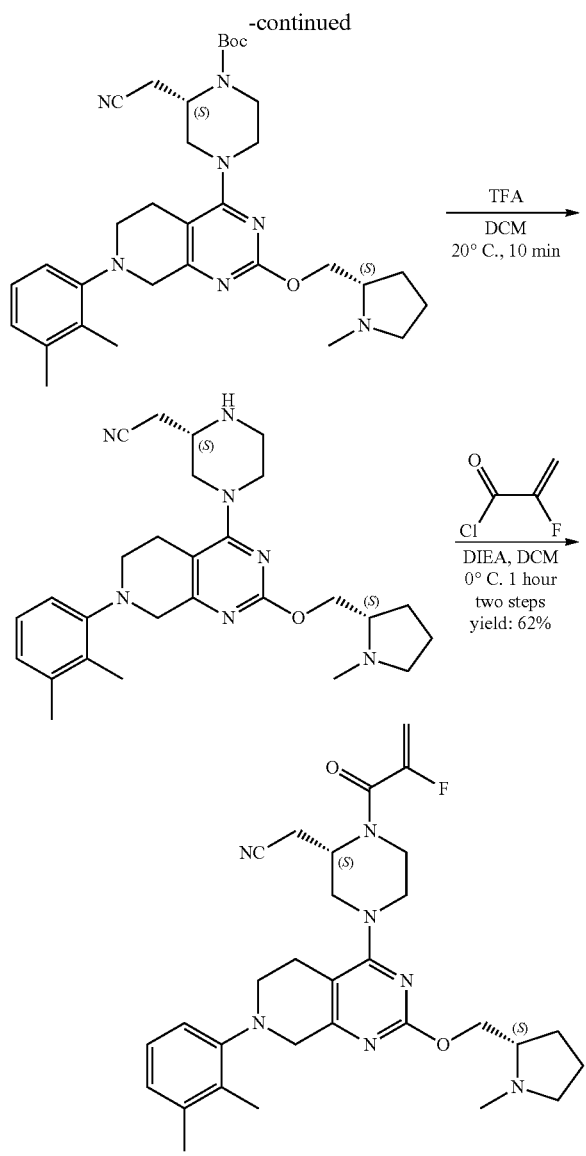

2-chloroprop-2-enoyl chloride

To a solution of 2-fluoroprop-2-enoic acid (400 mg, 4.44 mmol, 1.0 eq) in DCM (1.50 mL) was added (COCl)₂ (846 mg, 6.66 mmol, 583 uL, 1.50 eq) and DMF (32.5 mg, 444 umol, 34.2 uL, 0.10 eq). The mixture was stirred at 25° C. for 2 hours. 2-chloroprop-2-enoyl chloride (400 mg, crude) was used for the next step directly.

Step A: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (200 mg, 347 umol, 1.0 eq) in DCM (2.0 mL) was added TFA (3.08 g, 27.0 mmol, 2.0 mL, 77.8 eq). The mixture was stirred at 20° C. for 10 min. The reaction mixture was concentrated under reduced pressure to give a residue. The product 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, crude, TFA) was obtained as a yellow solid and used into the next step without further purification.

Step B: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 339 umol, 1.0 eq, TFA) in DCM (2.0 mL) was added DIEA (1.11 g, 8.61 mmol, 1.50 mL, 25.4 eq) and 2-fluoroprop-2-enoyl chloride (200 mg, 1.84 mmol, 5.43 eq) in DCM (2.0 mL). The mixture was stirred at 0° C. for 1 hour. The reaction mixture was concentrated under reduced pressure to give a residue. The residue was purified by prep-HPLC (column: Phenomenex Gemini 150*25 mm*10 um; mobile phase: [water (0.05% ammonia hydroxide v/v)-ACN]; B %: 55%-83%, 12 min). Title compound 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (EXAMPLE 472, 120 mg, 217 umol, two steps 62% yield, 98.9% purity) was obtained as a yellow solid. LCMS [ESI, M+1]: 548.

¹H NMR (400 MHz, CHLOROFORM-d) δ=7.11 (t, J=7.8 Hz, 1H), 7.01-6.91 (m, 2H), 5.52-5.32 (m, 1H), 5.26 (dd, J=3.2, 16.8 Hz, 1H), 5.08-4.70 (br s, 1H), 4.39 (dd, J=5.2, 10.4 Hz, 1H), 4.25-4.02 (m, 5H), 3.97 (d, J=12.8 Hz, 1H), 3.43-3.73 (br s, 1H) 3.32 (d, J=13.2 Hz, 1H), 3.25-3.16 (m, 1H), 3.15-3.02 (m, 3H), 3.01-2.91 (m, 1H), 2.90-2.80 (m, 2H) 2.79-2.60 (m, 2H), 2.49 (s, 3H), 2.31-2.28 (m, 7H), 2.13-1.97 (m, 1H), 1.90-1.70 (m, 3H).

Example 473

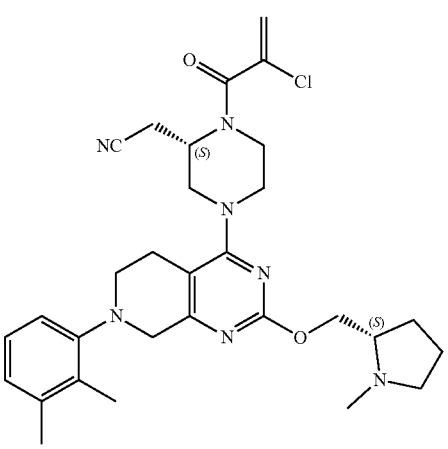

1275

2-[(2S)-1-(2-chloroprop-2-enoyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile

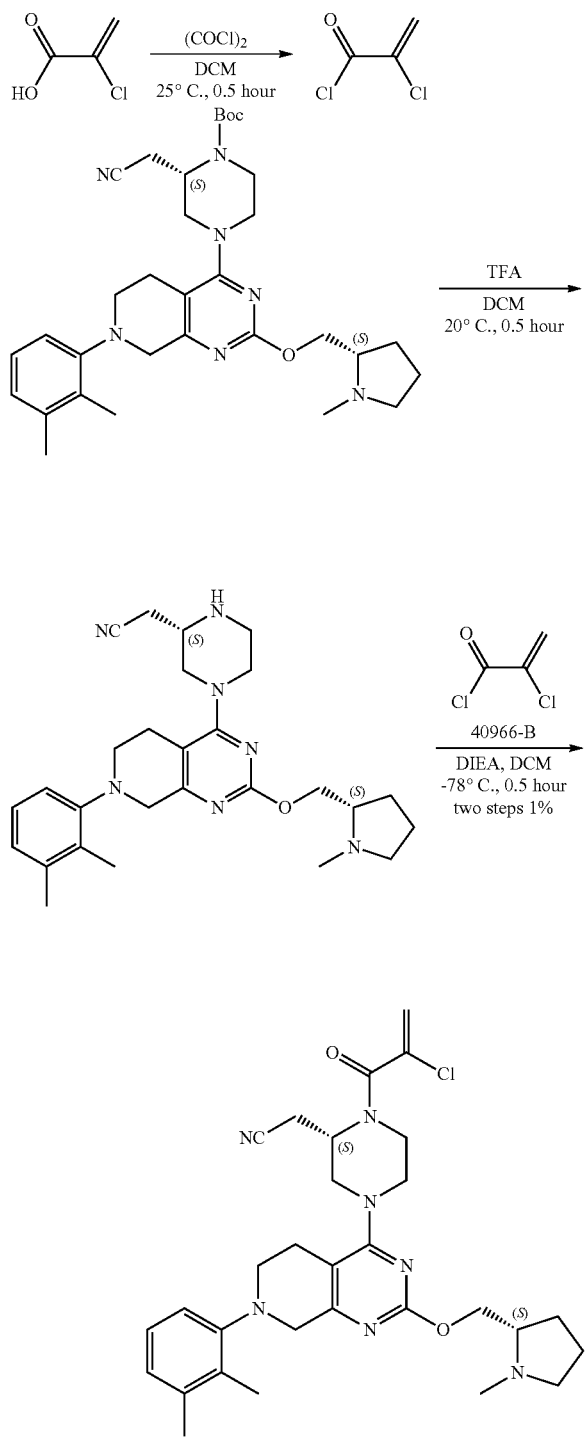

2-chloroacryloyl chloride

A solution of 2-chloroprop-2-enoic acid (400 mg, 3.76 mmol, 1.0 eq) and (COCl)₂ (715 mg, 5.63 mmol, 493 uL, 1.50 eq) in DCM (1.0 mL) was stirred at 25° C. for 0.5 hour. After completion, the reaction mixture was not work-up, and used for the next step directly.

Step A: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (Intermediate 73, 400 mg, 695 umol, 1.0 eq) in DCM (0.50 mL) was added TFA (3.08 g, 27.0 mmol, 2.0 mL, 38.9 eq). The mixture was stirred at 20° C. for 0.5 hour. After completion, the mixture was concentrated and adjusts with saturated NaHCO₃ aqueous to pH ~7, then extracted with DCM (5.0 mL×3). The organic layer was dried over Na₂SO₄, filtered and concentrated. The product 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (400 mg, crude) was obtained as yellow oil and used to the next step without further purification.

Step B: 2-[(2S)-1-(2-chloroprop-2-enoyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, 631 umol, 1.0 eq) and DIEA (245 mg, 1.89 mmol, 330 uL, 3.0 eq) in DCM (1.0 mL) was added 2-chloroprop-2-enoyl chloride (236 mg, 1.89 mmol, 3.0 eq) at −78° C. The mixture was stirred at −78° C. for 0.5 hour. After completion, the mixture was added saturated NaHCO₃ aqueous (2.0 mL) and extracted with EA (10.0 mL×3). The obtained product was purified by prep-HPLC (column: Gemini 150*25 5 u; mobile phase: [water (0.05% ammonia hydroxide v/v)-ACN]; B %: 53%-83%,12 min) to give title compound 2-[(2S)-1-(2-chloroprop-2-enoyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (EXAMPLE 473, 4.72 mg, 8.35 umol, two steps 1% yield, 99.8% purity) as white solid. LCMS [ESI, M+1]: 564.

¹H NMR (400 MHz, Chloroform-d) δ 7.11 (t, J=7.8 Hz, 1H), 6.98-6.94 (m, 2H), 5.86-5.78 (m, 1H), 5.77-5.72 (m, 1H), 5.15-4.78 (m, 1H), 4.45-4.30 (m, 1H), 4.21-4.12 (m, 1H), 4.10-4.03 (m, 3H), 3.96 (br d, J=12.4 Hz, 2H), 3.30 (br dd, J=3.2, 13.6 Hz, 1H), 3.23-3.04 (m, 4H), 3.04-2.54 (m, 6H), 2.50 (br s, 3H), 2.34-2.23 (m, 7H), 2.12-2.02 (m, 1H), 1.91-1.66 (m, 3H).

Example 474

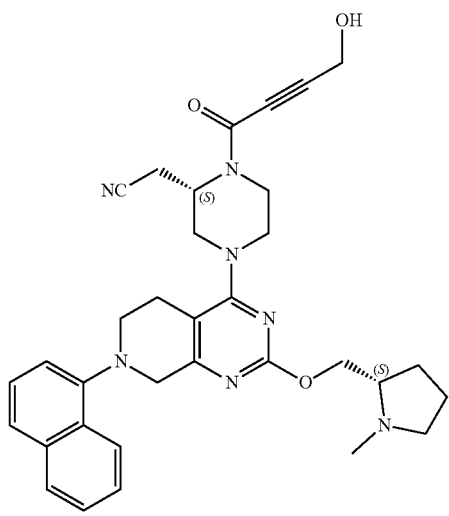

2-((S)-1-(4-hydroxybut-2-ynoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

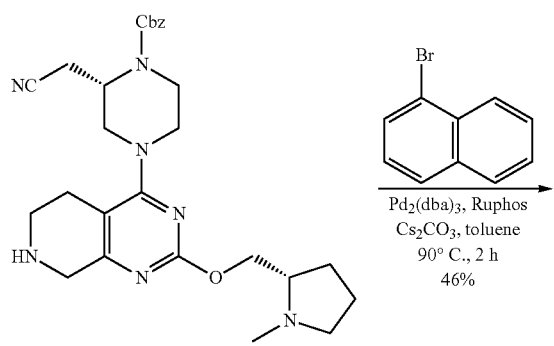

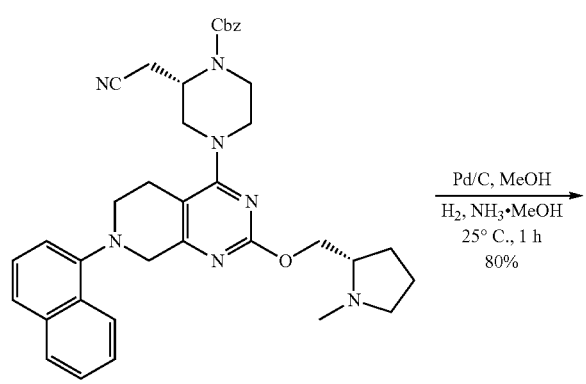

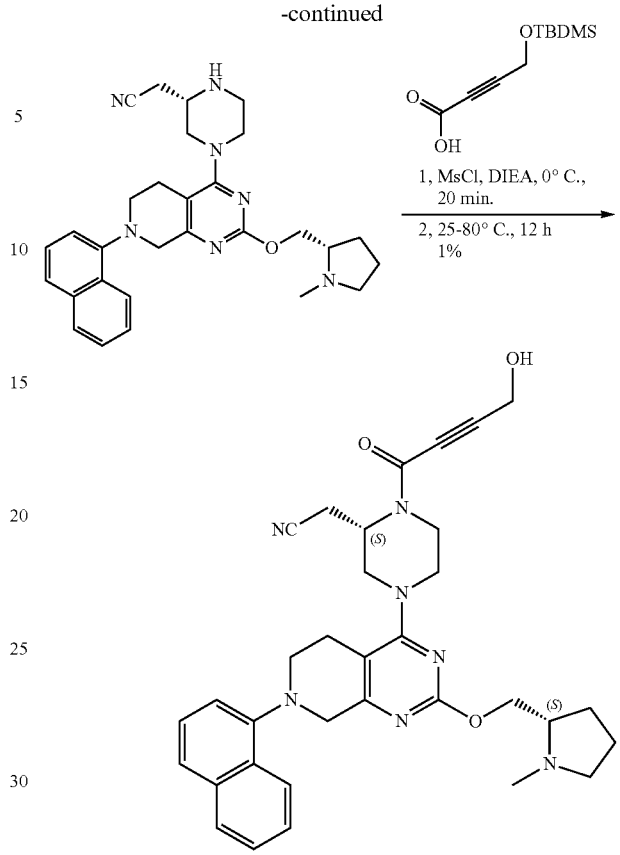

Step A: benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate To a mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 1 g, 1.58 mmol, 1 eq) and 1-bromonaphthalene (655 mg, 3.16 mmol, 440 uL, 2 eq) in toluene (20 mL) was added $Pd_2(dba)_3$ (145 mg, 158 umol, 0.1 eq), RuPhos (148 mg, 316 umol, 0.2 eq), $Cs_2CO_3$ (1.55 g, 4.75 mmol, 3 eq) in one portion. The mixture was degassed and purged with $N_2$ for 3 times, then heated to 90° C. and stirred for 2 hours. The reaction mixture was diluted with water (15 mL) and extracted with ethyl acetate (50 mL×3). The combined organic layers were washed with water (50 mL×1), dried over $Na_2SO_4$, filtered and concentrated under reduced pressure to give a residue. The residue was purified by reversed phase flash [water (0.1% TFA)/acetonitrile]. The desired fractions were collected and neutralized with saturated $NaHCO_3$ solution (6 mL) and extracted with ethyl acetate (100 mL×2). The separated organic layers were dried over sodium sulfate, filtered and concentrated under vacuum. Compound benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (515 mg, 726 umol, 45.9% yield, 89.1% purity) was obtained as a yellow solid. LCMS [ESI, M+1]: 632.

Step B: 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile. To a solution of benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (1 g, 1.58 mmol, 1 eq) in MeOH (60 mL) was added Pd/C (500 mg, 10% purity) and NH$_3$.MeOH (20%, 50 mL) under N$_2$. The suspension was degassed under vacuum and purged with H$_2$ three times. The mixture was stirred under H$_2$ (15 psi) at 25° C. for 1 hour. The reaction mixture was concentrated under reduced pressure. Compound 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (680 mg, 1.26 mmol, 80% yield, 92.3% purity) was obtained as a yellow solid which was used directly into the next step without further purification. LCMS [ESI, M+1]: 498.

$^1$H NMR (400 MHz, chloroform-d) δ=8.26-8.19 (m, 1H), 7.89-7.83 (m, 1H), 7.60 (d, J=8.4 Hz, 1H), 7.53-7.47 (m, 2H), 7.43 (t, J=7.6 Hz, 1H), 7.16-7.12 (m, 1H), 4.41 (dd, J=5.2, 10.8 Hz, 1H), 4.26 (s, 2H), 4.16 (dd, J=7.2, 10.8 Hz, 1H), 4.01 (br d, J=12.4 Hz, 1H), 3.95-3.82 (m, 1H), 3.44-3.21 (m, 3H), 3.18-2.97 (m, 4H), 2.95-2.76 (m, 3H), 2.74-2.63 (m, 1H), 2.55 (dd, J=1.2, 5.6 Hz, 2H), 2.51-2.46 (m, 3H), 2.33-2.22 (m, 1H), 2.12-1.99 (m, 1H), 1.88-1.80 (m, 3H).

Step C: 2-[(2S)-1-(4-hydroxybut-2-ynoyl)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile To a solution of 4-[tert-butyl(dimethyl)silyl]oxybut-2-ynoic acid (172 mg, 803 umol, 2 eq) and DIEA (155 mg, 1.21 mmol, 210 uL, 3 eq) in MeCN (5 mL) was added MsCl (92.1 mg, 803 umol, 62.2 uL, 2 eq) at 0° C. After stirring at 0° C. for 20 minutes, to the mixture was added 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (200 mg, 402 umol, 1 eq) and the mixture was stirred at 25° C. for 2 hours. Then the reaction mixture was heated to 80° C. and stirred for 10 hours. The reaction mixture was diluted with water (20 mL) and extracted with ethyl acetate (20 mL×3). The combined organic layers were washed with brine (20 mL), dried over Na$_2$SO$_4$, filtered and concentrated under reduced pressure to give a residue. The residue was purified by prep-HPLC (column: Boston Green ODS 150*30 5 u; mobile phase: [water (0.225% FA)-ACN]; B %: 25%-45%, 10 min) and further purified by prep-HPLC (column: Phenomenex Gemini 150*25 mm*10 um; mobile phase: [water (0.05% ammonia hydroxide v/v)-ACN]; B %: 45%-75%, 12 min). Title compound 2-[(2S)-1-(4-hydroxybut-2-ynoyl)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (EXAMPLE 474, 1.43 mg, 2.39 umol, 1% yield, 96.7% purity) was obtained as a white solid. LCMS [ESI, M+1]: 580.

$^1$H NMR (400 MHz, chloroform-d) δ=8.22 (d, J=6.8 Hz, 1H), 7.90-7.82 (m, 1H), 7.61 (d, J=8.4 Hz, 1H), 7.55-7.47 (m, 2H), 7.44 (t, J=7.6 Hz, 1H), 7.15 (d, J=7.2 Hz, 1H), 5.26-4.89 (m, 1H), 4.60-4.34 (m, 4H), 4.33-4.16 (m, 3H), 4.14-3.96 (m, 1H), 3.95-3.80 (m, 1H), 3.78-3.50 (m, 2H), 3.50-3.28 (m, 2H), 3.27-3.07 (m, 3H), 3.06-2.82 (m, 3H), 2.80-2.64 (m, 2H), 2.51 (d, J=12.4 Hz, 3H), 2.38-2.24 (m, 1H), 2.14-2.00 (m, 1H), 1.97-1.85 (m, 2H).

Example 475

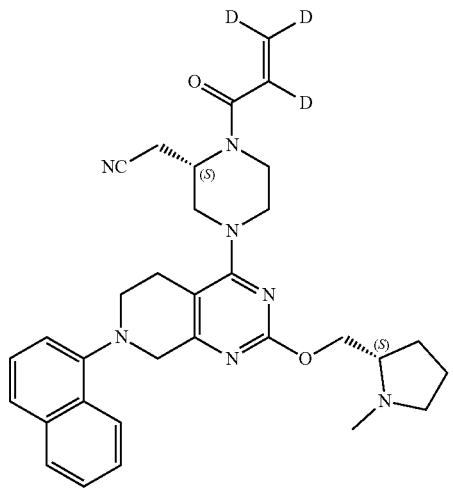

2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]-1-(2,3,3-trideuterioprop-2-enoyl)piperazin-2-yl]acetonitrile

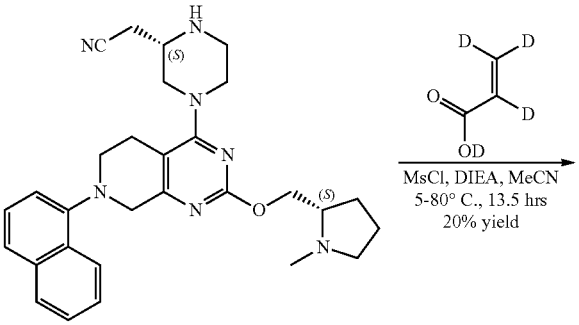

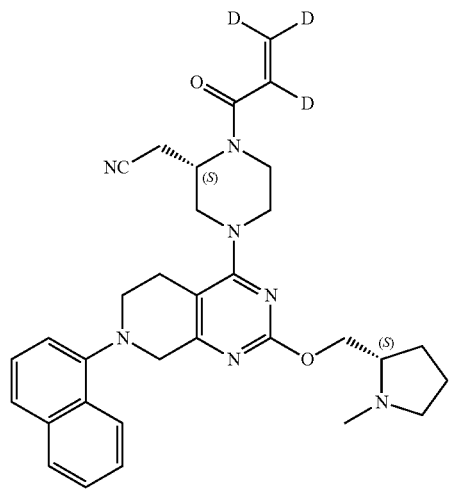

1281

Step A: 2-[(2S)-4-[2-[[(2S)-1-methylpyrrolidin-2-yl] methoxy]-7-(1-naphthyl)-6,8-dihydro-5H-pyrido[3, 4-d]pyrimidin-4-yl]-1-(2,3,3-trideuterioprop-2-enoyl)piperazin-2-yl]acetonitrile To a solution of deuterio 2,3,3-trideuterioprop-2-enoate (68.8 mg, 904 umol, 3 eq) and DIEA (234 mg, 1.81 mmol, 315 uL, 6 eq) in MeCN (3 mL) was added MsCl (69.1 mg, 603 umol, 46.7 uL, 2 eq) at 5° C. for 0.5 hour. To the resulting reaction was added 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (150 mg, 301 umol, 1 eq). The reaction mixture was stirred at 5° C. for 1 hour. Then the reaction mixture was heated to 80° C. for 12 hrs. Upon completion, the reaction mixture was quenched by water (0.5 mL). The residue mixture was purified by prep-HPLC (column: Phenomenex Gemini 150*25 mm*10 um; mobile phase: [water (0.05% ammonia hydroxide v/v)-ACN]; B %: 50%-80%,12 min) to give title compound 2-[(2S)-4-[2-[[(2S)-1-methylpyrrolidin-2-yl] methoxy]-7-(1-naphthyl)-6,8-dihydro-5H-pyrido[3,4-d]pyrimidin-4-yl]-1-(2,3,3-trideuterioprop-2-enoyl)piperazin-2-yl]acetonitrile (EXAMPLE 475, 34.2 mg, 60.2 umol, 20% yield, 97.7% purity) as a white solid. LCMS [ESI, M+1]: 555.

$^1$H NMR (400 MHz, CHLOROFORM-d) δ=8.28-8.16 (m, 1H), 7.91-7.83 (m, 1H), 7.63 (d, J=8.0 Hz, 1H), 7.56-7.48 (m, 2H), 7.45 (t, J=7.6 Hz, 1H), 7.16 (d, J=7.2 Hz, 1H), 5.28-4.94 (m, 1H), 4.41 (dd, J=5.2, 10.8 Hz, 1H), 4.36-4.24 (m, 2H), 4.23-4.11 (m, 2H), 4.04 (br d, J=11.6 Hz, 2H), 3.73-3.25 (m, 3H), 3.22-2.74 (m, 7H), 2.69 (td, J=6.4, 13.2 Hz, 1H), 2.50 (s, 3H), 2.36-2.24 (m, 1H), 2.15-2.02 (m, 1H), 1.83-1.77 (m, 3H).

Example 476

1282

2-[(2S)-4-[7-(2,3-dimethylphenyl)-2-[[(2S)-1-methylpyrrolidin-2-yl]methoxy]-6,8-dihydro-5H-pyrido [3,4-d]pyrimidin-4-yl]-1-[(E)-4-(3-fluoropyrrolidin-1-yl)but-2-enoyl]piperazin-2-yl]acetonitrile

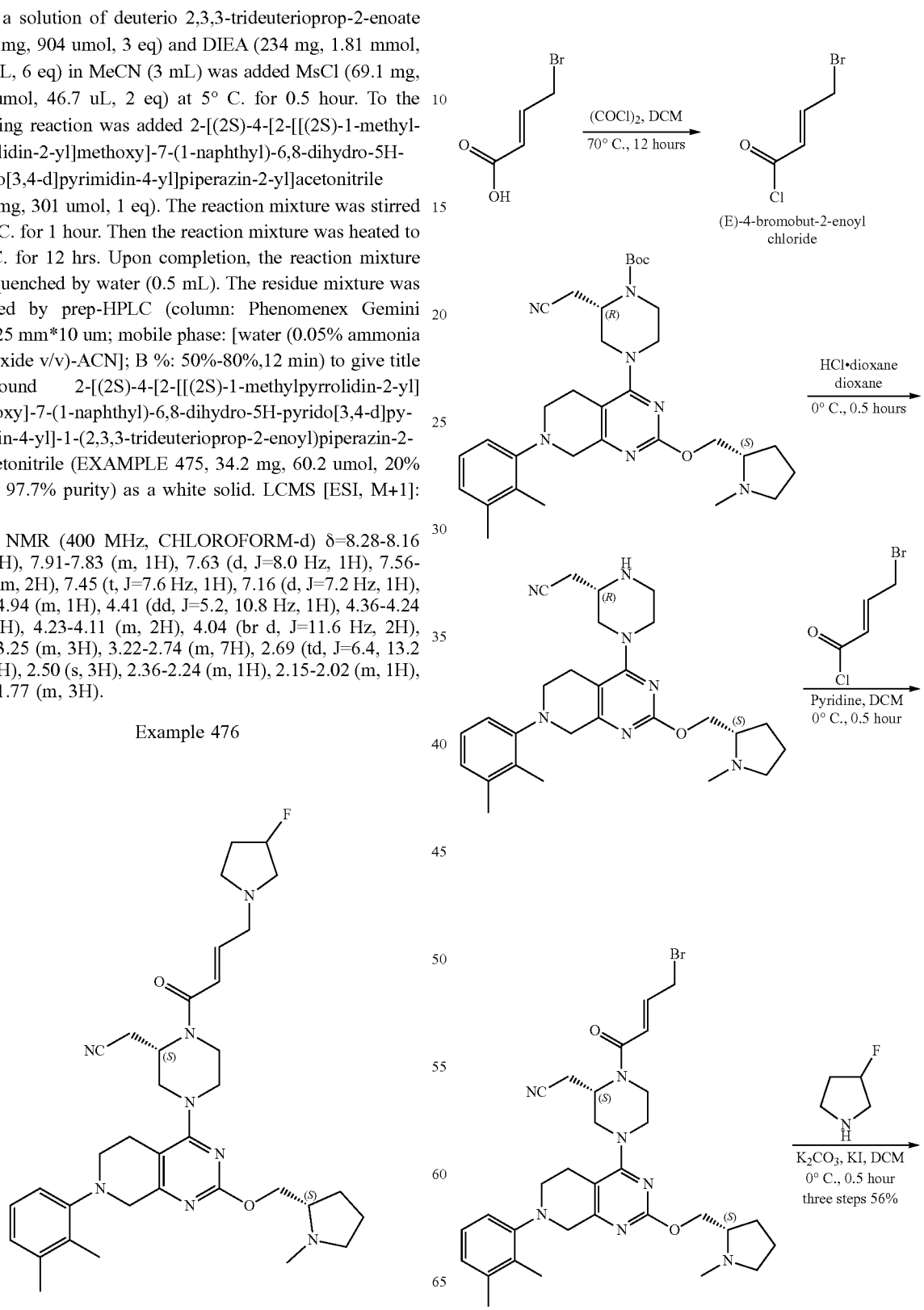

-continued

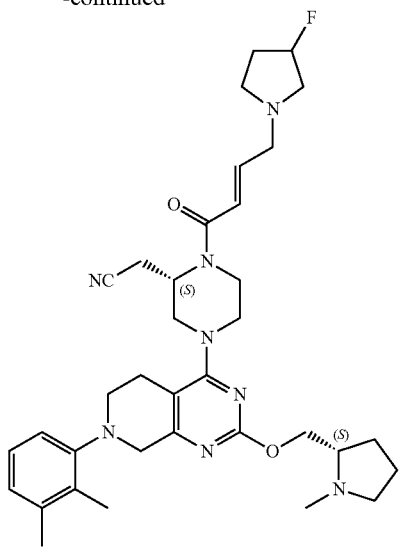

Insert: (E)-4-bromobut-2-enoyl chloride

A solution of (E)-4-bromobut-2-enoic acid (1.0 g, 6.06 mmol, 1.0 eq) in (COCl)$_2$ (14.5 g, 114 mmol, 10.0 mL, 18.9 eq) and DCM (10.0 mL) was stirred at 70° C. for 2 hours. After completion, the mixture was concentrated under vacuum. The product (E)-4-bromobut-2-enoyl chloride (1.0 g, crude) was obtained as yellow oil. The crude compound was used directly to the next step without further purification.

Step A: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (Intermediate 73, 200 mg, 347 umol, 1.0 eq) in dioxane (2.0 mL) was added HCl.dioxane (4.0 M, 2.0 mL, 23.0 eq). The mixture was stirred at 25° C. for 0.5 hour. After completion, the reaction mixture was concentrated under reduced pressure to give a residue. The residue was adjusted pH=7 with saturated of NaHCO$_3$ aqueous solution and extracted with EA (5.0 mL×3). The combined organic layers were washed with brine (10.0 mL), dried over Na$_2$SO$_4$, filtered and concentrated under reduced pressure to give the residue. The product 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (160 mg, crude) was obtained as a yellow solid and used into the next step without further purification.

Step B: 2-[(2S)-1-[(E)-4-bromobut-2-enoyl]-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (160 mg, 336 umol, 1.0 eq) in DCM (6.0 mL) was added Py (532 mg, 6.73 mmol, 543 uL, 20.0 eq) and (E)-4-bromobut-2-enoyl chloride (246 mg, 1.35 mmol, 4.0 eq) in DCM (2.0 mL). The mixture was stirred at 0° C. for 1 hour. After completion, the reaction mixture was quenched by addition MeOH (5.0 mL) at 0° C., and then concentrated under reduced pressure to give a residue. The product 2-[(2S)-1-[(E)-4-bromobut-2-enoyl]-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, crude) was obtained as a yellow oil and used into the next step without further purification. LCMS [ESI, M+1]: 622.

Step C: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile To a solution of 2-[(2S)-1-[(E)-4-bromobut-2-enoyl]-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 321 umol, 1.0 eq) in DCM (3.0 mL) was added K$_2$CO$_3$ (88.8 mg, 642 umol, 2.0 eq), KI (2.67 mg, 16.1 umol, 0.05 eq) and 3-fluoropyrrolidine (403 mg, 3.21 mmol, 10.0 eq, HCl salt). The mixture was stirred at 0° C. for 1 hour. After completion, the reaction mixture was concentrated under reduced pressure to give a residue. The residue was adjusted pH=7 with saturated of NaHCO$_3$ aqueous solution and extracted with EA (10.0 mL×3). The combined organic layers were washed with brine (20.0 mL), dried over Na$_2$SO$_4$, filtered and concentrated under reduced pressure to give the residue. The residue was purified by prep-HPLC (column: Gemini 150*25 5 u; mobile phase: [water (0.04% NH3H2O)-ACN]; B %: 60%-84%,10 min). The residue was concentrated under reduced pressure and then lyophilization to give title compound 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile (EXAMPLE 476, 123 mg, 193 umol, 56% yield in three steps, 99.2% purity) was obtained as a yellow solid. LCMS [ESI, M+1]: 631.

$^1$H NMR (400 MHz, Chloroform-d) δ 7.16-7.07 (m, 1H), 7.02-6.92 (m, 3H), 6.59-6.41 (m, 1H), 5.31-5.10 (m, 1H), 5.09-4.46 (m, 1H), 4.38 (dd, J=4.8, 10.4 Hz, 1H), 4.26-3.83 (m, 6H), 3.80-3.45 (m, 1H), 3.42-3.24 (m, 3H), 3.23-3.15 (m, 1H), 3.14-3.03 (m, 3H), 3.02-2.83 (m, 4H), 2.82-2.62 (m, 4H), 2.54-2.49 (m, 1H), 2.47 (s, 3H), 2.32-2.26 (m, 6H), 2.25-2.17 (m, 1H), 2.16-2.09 (m, 1H), 2.08-2.02 (m, 1H), 1.92-1.78 (m, 4H).

Example 477

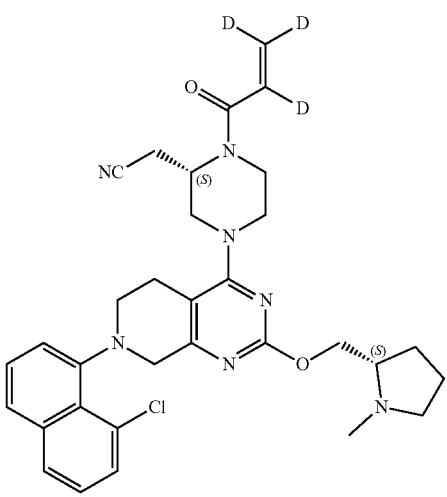

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2,3,3-trideuterioprop-2-enoyl)piperazin-2-yl]acetonitrile

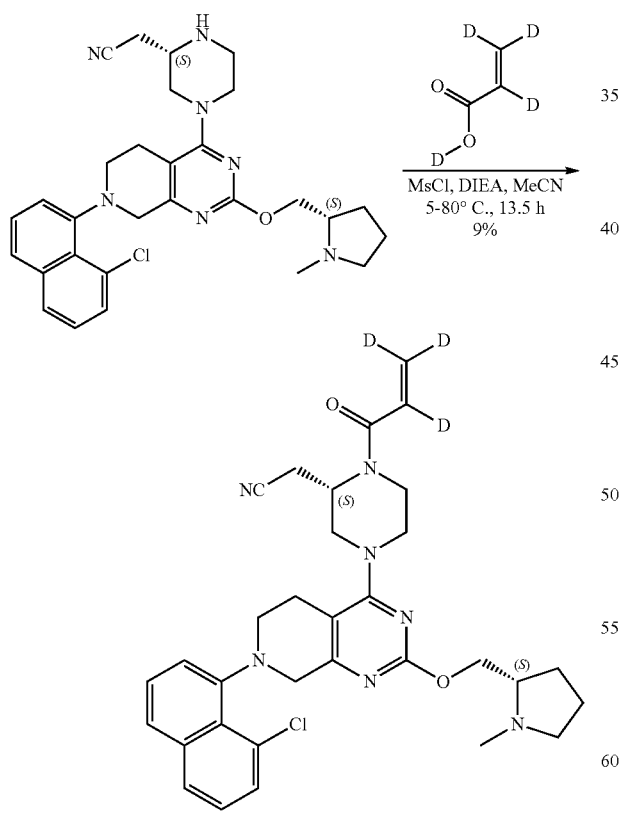

Step A: 2-[(2S)-4-[7-(8-chloro-1-naphthyl)-2-[[(2S)-1-methylpyrrolidin-2-yl] methoxy]-6,8-dihydro-5H-pyrido[3,4-d] pyrimidin-4-yl]-1-(2,3,3-trideuterioprop-2-enoyl)piperazin-2-yl]acetonitrile. To the solution of deuterio 2,3,3-trideuterioprop-2-enoate (56.6 mg, 744 umol, 3 eq) and DIEA (481 mg, 3.72 mmol, 648 uL, 15 eq) in ACN (3 mL) was added MsCl (56.8 mg, 496 umol, 38.4 uL, 2 eq) at 5° C., the mixture was stirred at 5° C. for 0.5 hour. Then to the mixture was added 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 150 mg, 248 umol, 1 eq, 2 HCl), the resulting mixture was stirred at 5° C. for 1 hour. Then the mixture was heated to 80° C. and stirred at 80° C. for 12 hours. The mixture was quenched by Water (0.5 mL). The reaction mixture was purified by prep-HPLC (column: Phenomenex Gemini 150*25 mm*10 um; mobile phase: [water (0.05% ammonia hydroxide v/v)-ACN]; B %: 50-80%,10 min) to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2,3,3-trideuterioprop-2-enoyl)piperazin-2-yl]acetonitrile (EXAMPLE 477, 13.0 mg, 21.6 umol, 9% yield, 98.2% purity) as a off-white solid. LCMS [ESI, M+1]: 589.

$^1$H NMR (400 MHz, chloroform-d) δ=7.76 (br d, J=8.4 Hz, 1H), 7.62 (t, J=7.6 Hz, 1H), 7.53 (d, J=7.2 Hz, 1H), 7.45 (td, J=8.0, 13.2 Hz, 1H), 7.34 (t, J=7.6 Hz, 1H), 7.26-7.18 (m, 1H), 5.10 (br s, 1H), 4.49-4.33 (m, 2H), 4.21-4.01 (m, 3H), 3.96-3.79 (m, 2H), 3.60 (br d, J=6.8 Hz, 1H), 3.44 (br d, J=13.6 Hz, 1H), 3.32-2.97 (m, 5H), 2.88-2.53 (m, 4H), 2.48 (d, J=2.8 Hz, 3H), 2.29 (br d, J=8.8 Hz, 1H), 2.11-2.00 (m, 1H), 1.87-1.71 (m, 3H).

Example 478

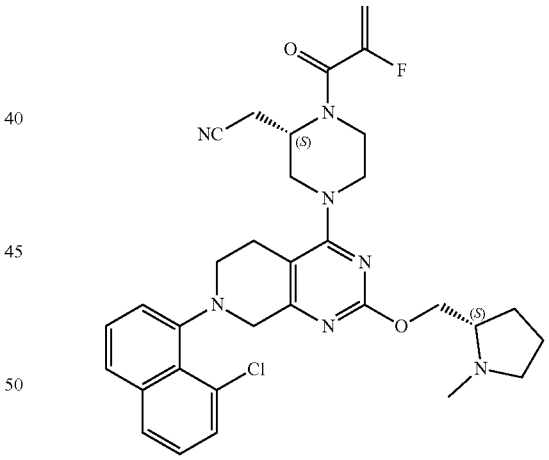

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl] acetonitrile

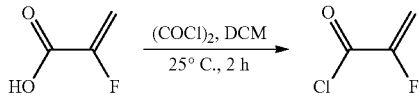

-continued

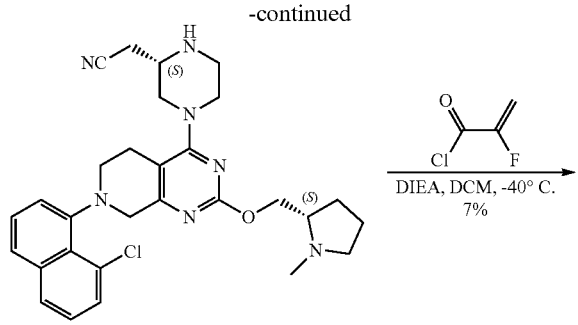

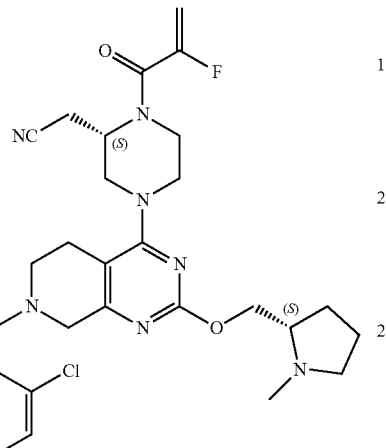

2-fluoroprop-2-enoyl chloride

To a solution of 2-fluoroprop-2-enoic acid (400 mg, 4.44 mmol, 1 eq) in DCM (4 mL) was added (COCl)₂ (846 mg, 6.66 mmol, 583 uL, 1.5 eq) and DMF (32.5 mg, 444 umol, 34.2 uL, 0.1 eq). The mixture was stirred at 25° C. for 2 hrs. The reaction mixture was concentrated under reduced pressure to remove a part of solvent and give a residue in DCM. Compound 2-fluoroprop-2-enoyl chloride (400 mg, crude) was obtained as a yellow liquid and used into the next step without further purification.

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, 528 umol, 1 eq, HCl) in DCM (5 mL) was added DIEA (1.73 g, 13.4 mmol, 2.33 mL, 25.4 eq) and 2-fluoroprop-2-enoyl chloride (286 mg, 2.64 mmol, 5 eq) in DCM (5 mL). The mixture was stirred at 0° C. for 1 hour. The reaction mixture was concentrated under reduced pressure to give a residue. The residue was purified by column chromatography (Al₂O₃, Dichloromethane/Methanol=10/1 to 10/1). The residue was purified by prep-HPLC (column: Gemini 150*25 5 u; mobile phase: [water (0.05% ammonia hydroxide v/v)-ACN]; B %: 55%-85%, 12 min). The residue was purified by prep-HPLC (column: Phenomenex Synergi C18 150*30 mm*4 um; mobile phase: [water (0.225% FA)-ACN]; B %: 20%-50%, 10.5 min). The residue was concentrated under reduced pressure to remove ACN, and then lyophlization. Title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (EXAMPLE 478, 24.1 mg, 36.7 umol, 7% yield, 99.1% purity, FA) was obtained as a brown solid.

SFC condition: "AD-3S_3_5_40_3ML Column: Chiralpak AD-3 100×4.6 mm I.D., 3 um Mobile phase: methanol (0.05% DEA) in CO₂ from 5% to 40% Flow rate: 3 mL/min Wavelength: 220 nm".

¹H NMR (400 MHz, Acetic) δ=7.82 (d, J=8.0 Hz, 1H), 7.69 (d, J=8.0 Hz, 1H), 7.56 (d, J=7.6 Hz, 1H), 7.49 (t, J=7.6 Hz, 1H), 7.41-7.30 (m, 2H), 5.58-5.25 (m, 2H), 5.17-4.59 (m, 4H), 4.57-4.28 (m, 3H), 4.24-3.78 (m, 4H), 3.67-3.13 (m, 7H), 3.08 (br d, J=2.4 Hz, 3H), 2.98 (br d, J=6.4 Hz, 1H), 2.83-2.61 (m, 1H), 2.45-2.29 (m, 1H), 2.24-2.08 (m, 3H).

Example 479

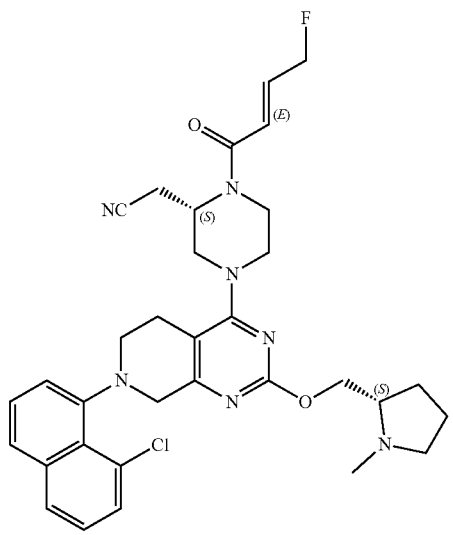

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile

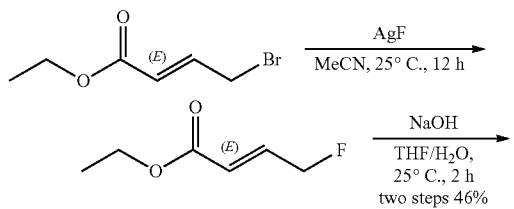

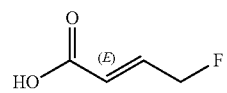

-continued

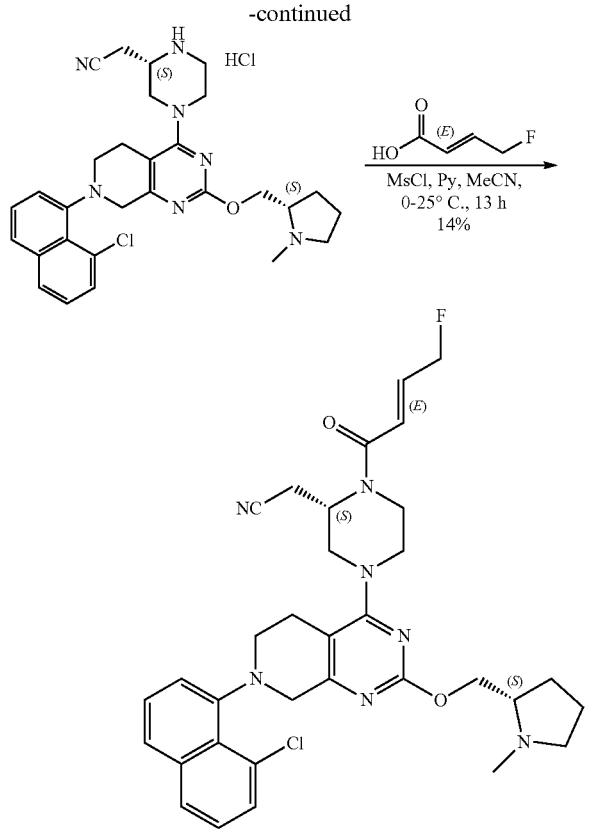

Step A: ethyl (E)-4-fluorobut-2-enoate

A mixture of ethyl (E)-4-bromobut-2-enoate (2.00 g, 10.4 mmol, 1.43 mL, 1.00 eq) and AgF (3.94 g, 31.1 mmol, 674 uL, 3.00 eq) in acetonitrile (20.0 mL) was stirred at 25° C. for 12 hours. The mixture was filtered and washed with THF (10.0 mL), then concentrated under vacuum to give ethyl (E)-4-fluorobut-2-enoate (2.50 g, crude) as a yellow oil and used into next step without further purification.

$^1$H NMR (400 MHz, chloroform-d) δ=7.04-6.89 (m, 1H), 6.12 (qd, J=2.0, 16.0 Hz, 1H), 5.14-4.94 (m, 2H), 4.22 (q, J=6.8 Hz, 2H), 1.30 (t, J=6.8 Hz, 3H).

Step B: (E)-4-fluorobut-2-enoic acid

A mixture of ethyl (E)-4-fluorobut-2-enoate (0.10 g, crude) and NaOH (121 mg, 3.03 mmol) in THF (1.00 mL) and H$_2$O (1.00 mL) was stirred at 25° C. for 2 hours. The pH value was adjusted to 1-3 by HCl (1N, 5.00 mL), extracted with ethyl acetate (3×10.0 mL), the organic layer was dried over Na$_2$SO$_4$, filtered and concentrated under vacuum to give (E)-4-fluorobut-2-enoic acid (0.02 g, 192 mmol, two steps 46%) as a yellow oil and used into next step without further purification.

$^1$H NMR (400 MHz, chloroform-d) δ=8.37-7.31 (m, 1H), 7.15-7.01 (m, 1H), 6.15 (dd, J=1.6, 16.0 Hz, 1H), 5.22-4.96 (m, 2H).

Step C: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile To a solution of (E)-4-fluorobut-2-enoic acid (7.32 mg, 70.4 umol, 2 eq) and Py (8.35 mg, 106 umol, 8.52 uL, 3.00 eq) in acetonitrile (1.00 mL) was added MsCl (8.06 mg, 70.4 umol, 5.45 uL, 2.00 eq) at 0° C. After stirred at 0° C. for 1 hour, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (0.02 g, 35.2 umol, 1.00 eq, HCl) was added into the mixture. The mixture was stirred at 25° C. for 12 h. The mixture was diluted with water (5.00 mL), extracted with ethyl acetate (3×5.00 mL), the organic layer was dried over Na$_2$SO$_4$, filtered and concentrated under vacuum. The residue was purified by prep-HPLC (column: Gemini 150*25 5 u; mobile phase: [water (0.05% ammonia hydroxide v/v)-ACN]; B %: 50%-80%, 12 min). The desired fraction was collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile (EXAMPLE 479, 3.01 mg, 4.82 umol, 14% yield, 98.9% purity) as a brown solid. LCMS [ESI, M+1]: 618.

$^1$H NMR (400 MHz, CHLOROFORM-d) δ=7.76 (br d, J=8.0 Hz, 1H), 7.62 (t, J=7.2 Hz, 1H), 7.53 (d, J=7.2 Hz, 1H), 7.45 (td, J=7.6, 12.8 Hz, 1H), 7.34 (t, J=7.6 Hz, 1H), 7.26-7.17 (m, 1H), 7.09-6.91 (m, 1H), 6.59 (br d, J=15.6 Hz, 1H), 5.19-5.05 (m, 2H), 4.49-4.36 (m, 2H), 4.22-3.79 (m, 5H), 3.76-2.96 (m, 8H), 2.92-2.55 (m, 4H), 2.48 (d, J=2.4 Hz, 3H), 2.29 (br d, J=9.6 Hz, 1H), 2.06 (br d, J=10.0 Hz, 1H), 1.83-1.71 (m, 3H).

Example 480

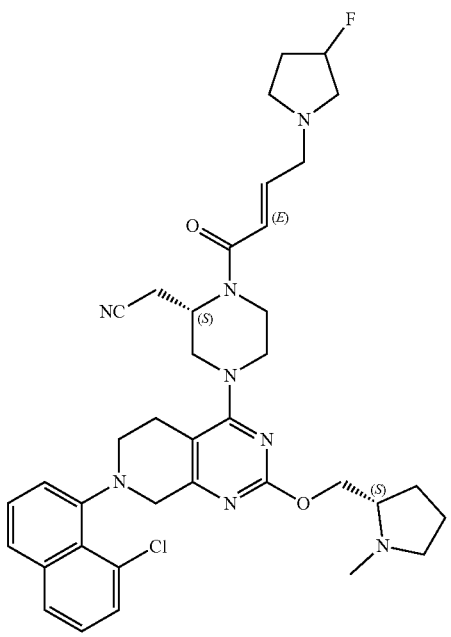

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile

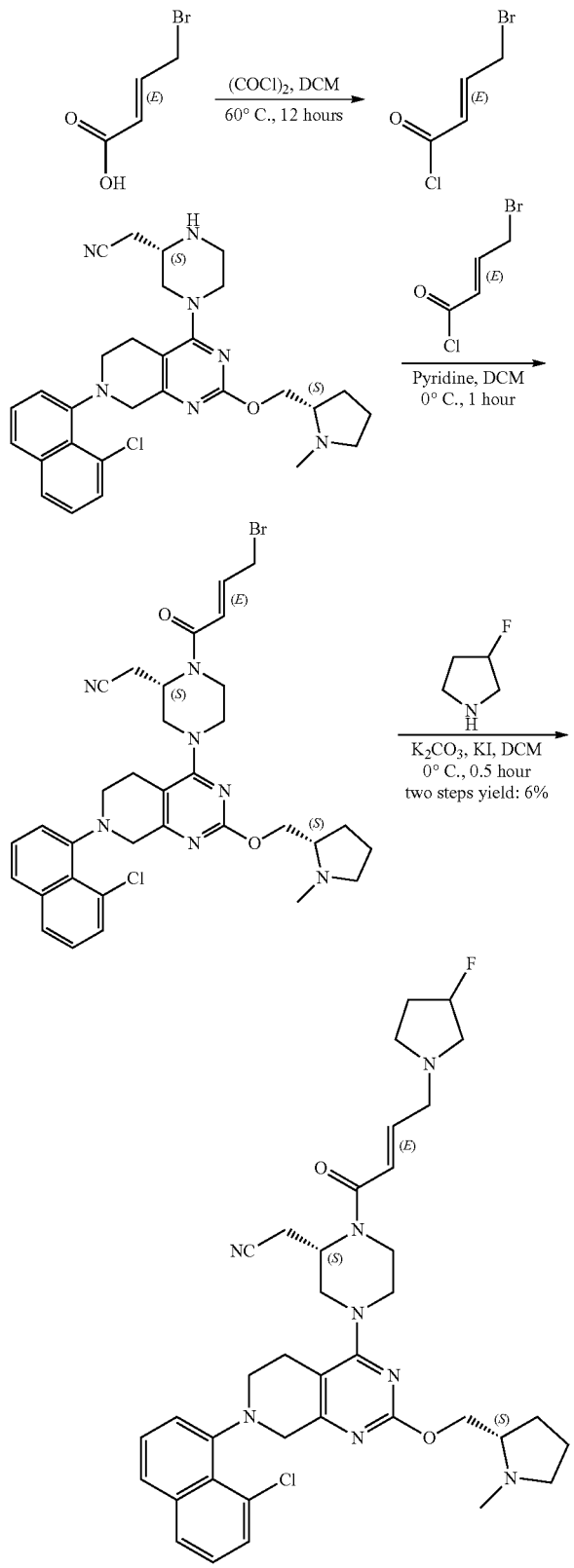

Insert: (E)-4-bromobut-2-enoyl chloride

To a solution of (E)-4-bromobut-2-enoic acid (930 mg, 5.64 mmol, 1.0 eq) in DCM (2.0 mL) was added (COCl)$_2$ (2.90 g, 22.9 mmol, 2.0 mL, 4.05 eq). The mixture was stirred at 60° C. for 12 hours. After completion, the mixture was concentrated under vacuum. The product (E)-4-bromobut-2-enoyl chloride (650 mg, crude) was obtained as yellow oil and used directly to the next step without further purification.

Step A: 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 150 mg, 282 umol, 1.0 eq) in DCM (3.0 mL) was added Py (446 mg, 5.64 mmol, 455 uL, 20.0 eq) and (E)-4-bromobut-2-enoyl chloride (207 mg, 1.13 mmol, 4.0 eq) in DCM (1.0 mL). The mixture was stirred at 0° C. for 1 hour. After completion, the reaction mixture was concentrated under reduced pressure to give a residue. The product 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, crude) was obtained as brown oil and used into the next step without further purification. LCMS [ESI, M+1]: 680.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile To a solution of 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido [3,4-d]pyrimidin-4-yl]piperazin-2-yl]acetonitrile (150 mg, 221 umol, 1.0 eq) in DCM (10.0 mL) was added K$_2$CO$_3$ (366 mg, 2.65 mmol, 12.0 eq), KI (1.83 mg, 11.0 umol, 0.05 eq) and 3-fluoropyrrolidine (277 mg, 2.21 mmol, 10.0 eq, HCl). The mixture was stirred at 0° C. for 0.5 hour. After completion, the reaction mixture was concentrated under reduced pressure to give a residue. The residue was adjusted pH ~7 with saturated NaHCO$_3$ aqueous solution and extracted with EA (3×10 mL). The combined organic layers were washed with brine (20 mL), dried over Na$_2$SO$_4$, filtered and concentrated under reduced pressure to give the residue. The residue was purified by prep-HPLC (column: Gemini 150*25 5 u; mobile phase: [water (0.04% NH$_3$.H$_2$O)-ACN]; B %: 60%-84%, 10 min). The residue was concentrated under reduced pressure and then lyophilization. Title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile (EXAMPLE 480, 9.67 mg, 14.0 umol, 6% yield, 99.2% purity) was obtained as yellow solid. LCMS [ESI, M+1]: 687.

$^1$H NMR (400 MHz, Chloroform-d) δ 7.76 (br d, J=8.0 Hz, 1H), 7.62 (t, J=7.8 Hz, 1H), 7.26 (br d, J=7.2 Hz, 1H), 7.49-7.40 (m, 1H), 7.34 (t, J=7.8 Hz, 1H), 7.27-7.17 (m, 1H), 7.05-6.92 (m, 1H), 6.57-6.42 (m, 1H), 5.32-5.11 (m, 1H), 5.10-4.50 (m, 1H), 4.47-4.35 (m, 2H), 4.19-4.00 (m, 2H), 3.95-3.75 (m, 2H), 3.65-3.55 (m, 1H), 3.47-3.28 (m, 3H), 3.24-3.05 (m, 4H), 3.04-2.86 (m, 4H), 2.85-2.71 (m, 2H), 2.70-2.50 (m, 3H), 2.47-2.45 (m, 3H), 2.32-2.15 (m, 2H), 2.14-2.02 (m, 2H), 1.87-1.67 (m, 4H).

Example 481

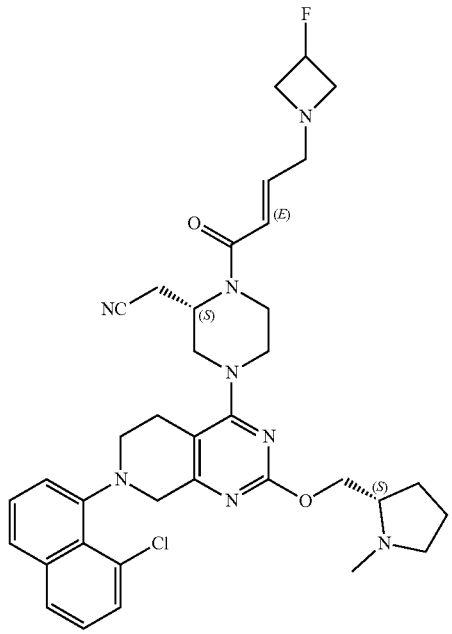

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoroazetidin-1-yl)but-2-enoyl]piperazin-2-yl]acetonitrile

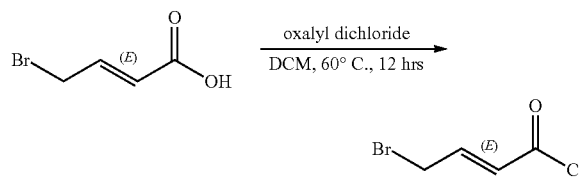

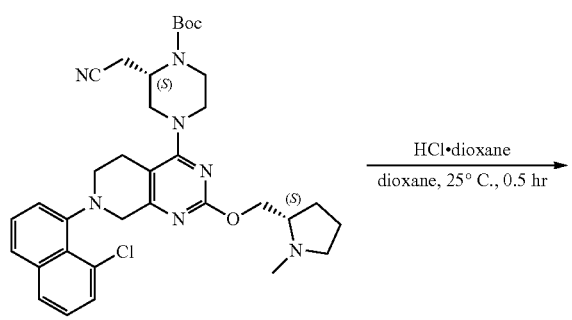

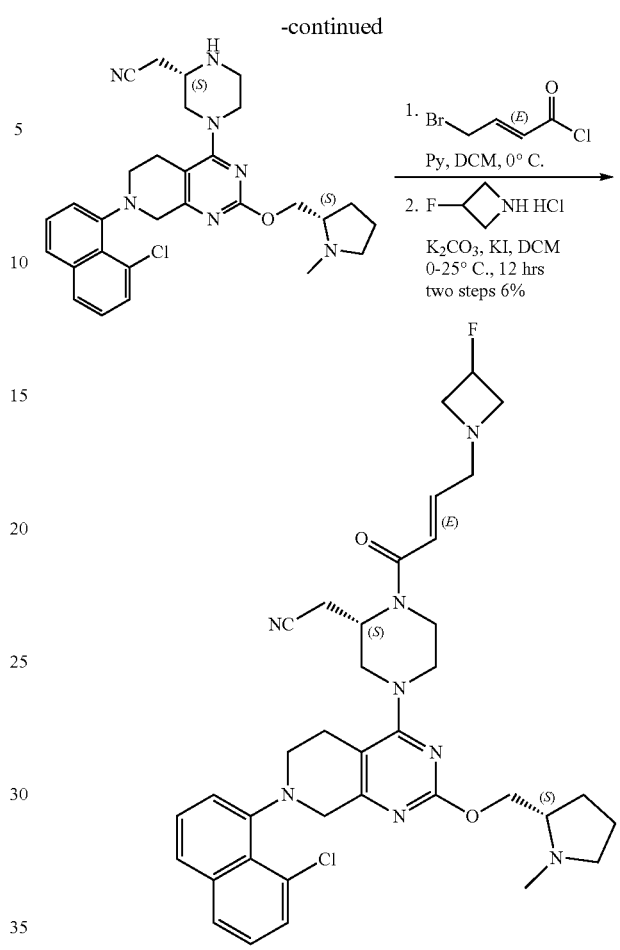

Insert: (E)-4-bromobut-2-enoyl chloride

To a solution of (E)-4-bromobut-2-enoic acid (1 g, 6.06 mmol, 1.0 eq) in DCM (5.0 mL) was added oxalyl dichloride (7.25 g, 57.1 mmol, 5.0 mL, 9.4 eq). The mixture was stirred at 60° C. for 12 hours. After completion, the reaction mixture was concentrated under reduced pressure to give (E)-4-bromobut-2-enoyl chloride (850 mg, crude) as yellow oil which was used for the next step without further purification.

Step A: Intermediate 71, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (310 mg, 414 umol, 1.0 eq) in dioxane (4.0 mL) was added HCl/dioxane (4.0 M, 4.0 mL, 39.0 eq) at 25° C. The mixture was stirred at 25° C. for 0.5 hour. After completion, the reaction mixture was quenched by saturated NaHCO₃ aqueous solution (20.0 mL), and then extracted with EA (3×40.0 mL). The combined organic layers were washed with saturated NaCl aqueous solution (100.0 mL), dried over Na₂SO₄, filtered and concentrated to give a residue 2-[(2S)-4-[7-(8-chloro-1-naphthyl)-2-[[(2S)-1-methylpyrrolidin-2-yl]methoxy]-6,8-dihydro-5H-pyrido

[3,4-d]pyrimidin-4-yl]piperazin-2-yl]acetonitrile (250 mg, crude) as yellow solid. The crude product was used into the next step without further purification. LCMS [ESI, M+1]: 532.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoroazetidin-1-yl)but-2-enoyl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 150 mg, 282 umol, 1.0 eq, crude) in DCM (6.0 mL) was added Py (446 mg, 5.6 mmol, 455 uL, 20.0 eq) and (E)-4-bromobut-2-enoyl chloride (207 mg, 1.2 mmol, 4.0 eq, crude) in DCM (1.0 mL). The mixture was stirred at 0° C. for 1 hour. Then $K_2CO_3$ (779 mg, 5.6 mmol, 20.0 eq), KI (4.6 mg, 28.2 umol, 0.1 eq) and 3-fluoroazetidine (472 mg, 4.2 mmol, 15.0 eq, HCl) was added at 0° C. Then the mixture was stirred at 25° C. for 12 hours. After completion, the mixture was filtered and concentrated under reduced pressure. The residue was purified by prep-HPLC (column: Phenomenex Gemini 150*25 mm*10 um; mobile phase: [water (10.0 mM $NH_4HCO_3$)-ACN]; B %: 55%-85%, 10 min.) and lyophilization to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoroazetidin-1-yl)but-2-enoyl]piperazin-2-yl]acetonitrile (EXAMPLE 481, 10.8 mg, 15.7 umol, 6% yield, 98% purity) as yellow solid. LCMS [ESI, M+1]: 673.

SFC Conditions: 100%. e.e.

$^1$H NMR (400 MHz, Chloroform-d) δ 7.77 (d, J=8.0 Hz, 1H), 7.63 (t, J=7.8 Hz, 1H), 7.54 (d, J=7.2 Hz, 1H), 7.50-7.43 (m, 1H), 7.35 (t, J=7.8 Hz, 1H), 7.26-7.21 (m, 1H), 6.89 (d, J=15.2 Hz, 1H), 6.42 (d, J=14.8 Hz, 1H), 5.26-4.62 (m, 1H), 5.11 (t, J=5.2 Hz, 1H), 4.80-4.37 (m, 2H), 4.20-4.08 (m, 2H), 3.92 (br d, J=17.6 Hz, 1H), 3.86-3.71 (m, 3H), 3.60 (s, 1H), 3.52-3.47 (m, 1H), 3.45-3.33 (m, 1H), 3.28-3.21 (m, 3H), 3.16-3.11 (m, 3H), 3.03 (dd, J=8.4, 16.8 Hz, 1H), 2.82-2.60 (m, 4H), 2.49 (d, J=2.8 Hz, 3H), 2.37-2.25 (m, 1H), 2.09-2.03 (m, 1H), 1.86-1.83 (m, 1H), 1.78-1.76 (m, 3H).

Example 482

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-[methyl(2,2,2-trifluoroethyl)amino]but-2-enoyl]piperazin-2-yl]acetonitrile

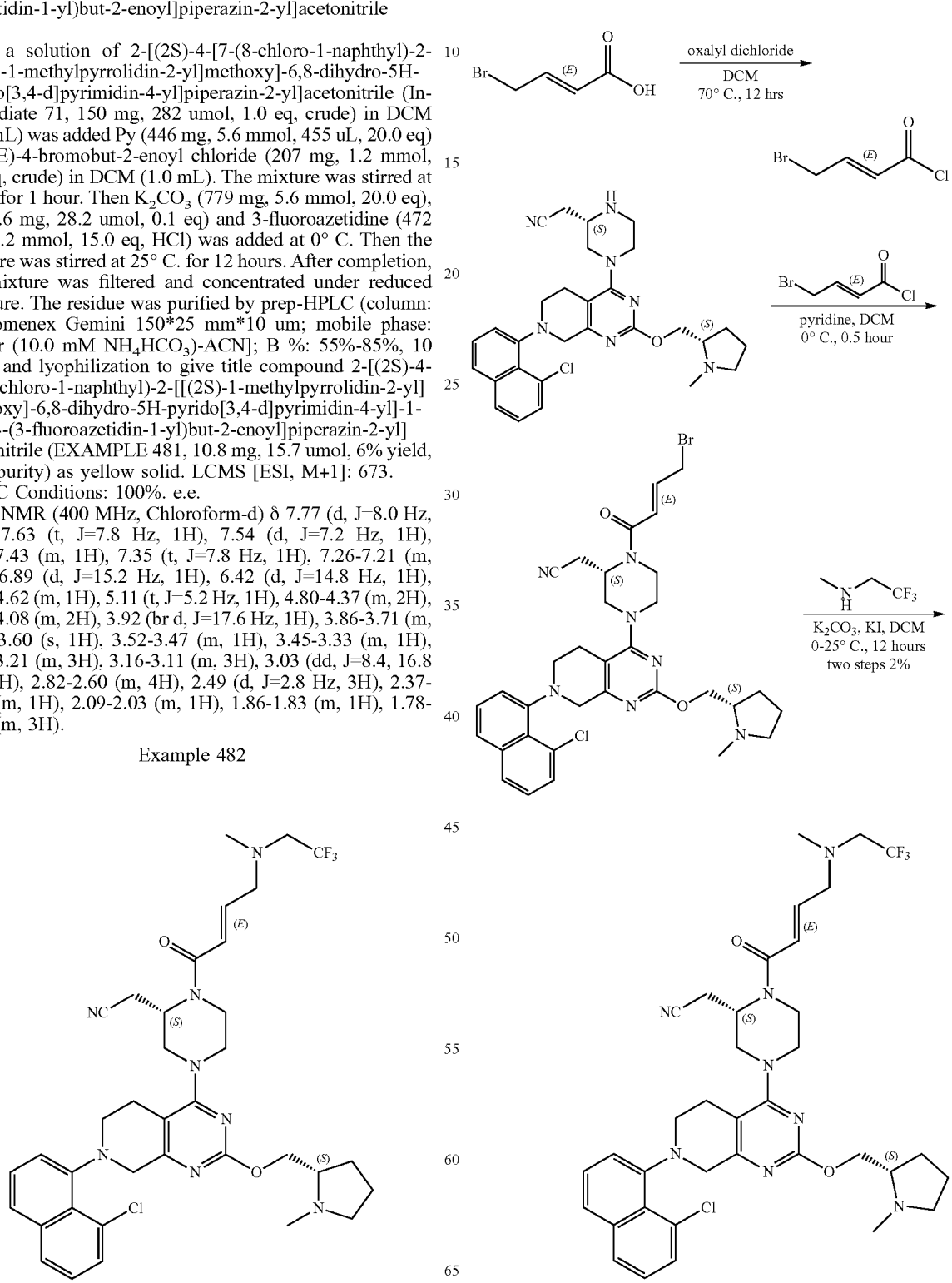

Insert: (E)-4-bromobut-2-enoyl chloride

A solution of (E)-4-bromobut-2-enoic acid (600 mg, 3.64 mmol, 1.0 eq) in (COCl)$_2$ (10.2 g, 80.0 mmol, 7.0 mL, 22.0 eq) and DCM (7.0 mL) was stirred at 70° C. for 12 hours. After completion, the reaction mixture was concentrated to give (E)-4-bromobut-2-enoyl chloride (500 mg, crude) as yellow oil. The crude product was used for the next step without further purification.

Step A: 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (100 mg, 188 umol, 1.0 eq) and pyridine (119 mg, 1.50 mmol, 121 uL, 8.0 eq) in DCM (2.0 mL) was added (E)-4-bromobut-2-enoyl chloride (138 mg, 752 umol, 4.0 eq). The mixture was stirred at 0° C. for 0.5 hour. After completion, the reaction mixture was concentrated to give 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (130 mg, crude) as yellow oil. LCMS [ESI, M+1]: 678, 680.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-[methyl(2,2,2-trifluoroethyl)amino]but-2-enoyl]piperazin-2-yl]acetonitrile To a solution of 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (128 mg, 189 umol, 1.0 eq), K$_2$CO$_3$ (130 mg, 943 umol, 5.0 eq) and KI (9.39 mg, 56.6 umol, 0.30 eq) in DCM (3.0 mL) was added 2,2,2-trifluoro-N-methyl-ethanamine (213 mg, 1.88 mmol, 10.0 eq) in portions. The mixture was stirred at 0-25° C. for 12 hours. After completion, the mixture was concentrated under vacuum. The obtained product was purified by prep-HPLC (column: Gemini 150*25 5 u; mobile phase: [water (0.04% NH$_3$.H$_2$O)-ACN]; B %: 70%-100%, 10 min) to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-[methyl(2,2,2-trifluoroethyl)amino]but-2-enoyl]piperazin-2-yl]acetonitrile (EXAMPLE 482, 2.87 mg, 3.84 umol, 2% yield, 95% purity) as white solid. LCMS [ESI, M+1]: 711.

$^1$H NMR (400 MHz, Chloroform-d) δ 7.76 (br d, J=7.6 Hz, 1H), 7.62 (t, J=7.6 Hz, 1H), 7.53 (d, J=7.2 Hz, 1H), 7.49-7.40 (m, 1H), 7.34 (t, J=7.8 Hz, 1H), 7.27-7.18 (m, 1H), 6.95-6.79 (m, 1H), 6.54-6.38 (m, 1H), 5.12-4.50 (m, 1H), 4.48-4.35 (m, 2H), 4.24-3.99 (m, 3H), 3.96-3.78 (m, 2H), 3.77-3.64 (m, 1H), 3.61-3.53 (m, 1H), 3.52-3.34 (m, 3H), 3.33-2.97 (m, 7H), 2.92-2.76 (m, 1H), 2.75-2.65 (m, 1H), 2.63-2.55 (m, 1H), 2.51 (s, 3H), 2.49 (br d, J=3.2 Hz, 3H), 2.35-2.25 (m, 1H), 2.13-1.99 (m, 1H), 1.89-1.67 (m, 3H).

Example 483

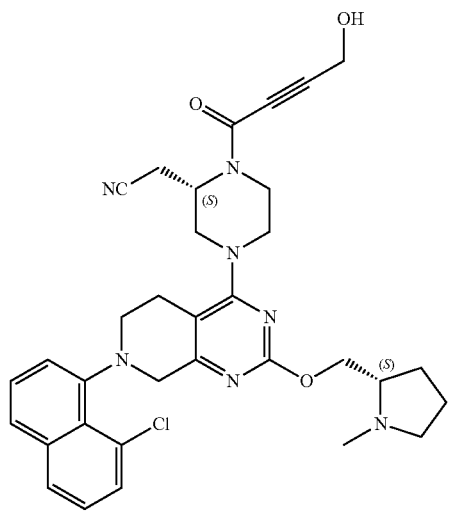

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(4-hydroxybut-2-ynoyl)piperazin-2-yl] acetonitrile

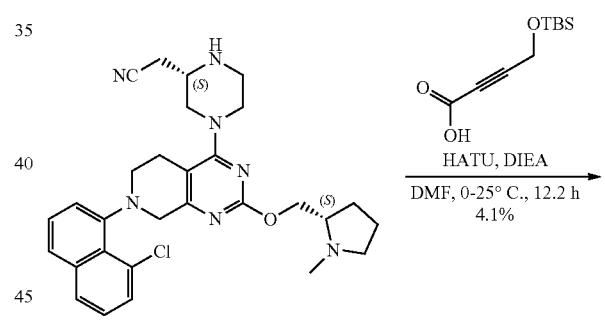

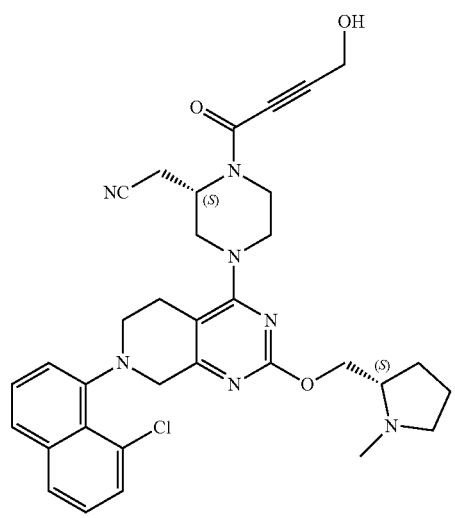

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(4-hydroxybut-2-ynoyl)piperazin-2-yl]acetonitrile To a solution of 4-[tert-butyl(dimethyl)silyl]oxybut-2-ynoic acid (129 mg, 564 umol, 1.50 eq) and DIEA (194 mg, 1.50 mmol, 262 uL, 4.00 eq) in DMF (2.00 mL) was added HATU (214 mg, 564 umol, 1.50 eq) at 0° C. After stirred at 0° C. for 10 mins, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (0.20 g, 376 umol, 1.00 eq) was added into the mixture. After stirred at 25° C. for 12 hours, the mixture was diluted with ethyl acetate (10.0 mL), washed with brine (3×10.0 mL), dried over Na₂SO₄, filtered and concentrated under vacuum. The residue was purified by reversed phase flash [water (FA, 0.10%)/acetonitrile]. The desired fractions were collected, neutralized with saturated sodium bicarbonate (5.00 mL) to pH >7 and extracted with ethyl acetate (3×20.0 mL). The organic layers were washed with brine (1×30.0 mL), dried over Na₂SO₄, filtered and concentrated under vacuum. The residue was purified by prep-HPLC column: Phenomenex Synergi C18 150*25*10 um; mobile phase: [water (0.225%, FA)-ACN]; B %: 10%-40%, 10 min. The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(4-hydroxybut-2-ynoyl)piperazin-2-yl]acetonitrile (EXAMPLE 483, 10.1 mg, 15.3 umol, 4.1% yield, 99.6% purity, FA) as a yellow solid. LCMS [ESI, M+1]: 614.

$^1$H NMR (400 MHz, Acetic acid-d4) δ=7.82 (d, J=8.4 Hz, 1H), 7.69 (d, J=8.4 Hz, 1H), 7.56 (d, J=7.6 Hz, 1H), 7.49 (t, J=7.6 Hz, 1H), 7.42-7.31 (m, 2H), 5.14-4.73 (m, 4H), 4.70-4.23 (m, 5H), 4.01-3.81 (m, 3H), 3.80-3.51 (m, 3H), 3.49-3.17 (m, 4H), 3.09 (m, 5H), 2.81-2.63 (m, 1H), 2.45-2.34 (m, 1H), 2.22-2.08 (m, 3H).

Example 484

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4,4-difluorobut-2-enoyl]piperazin-2-yl]acetonitrile

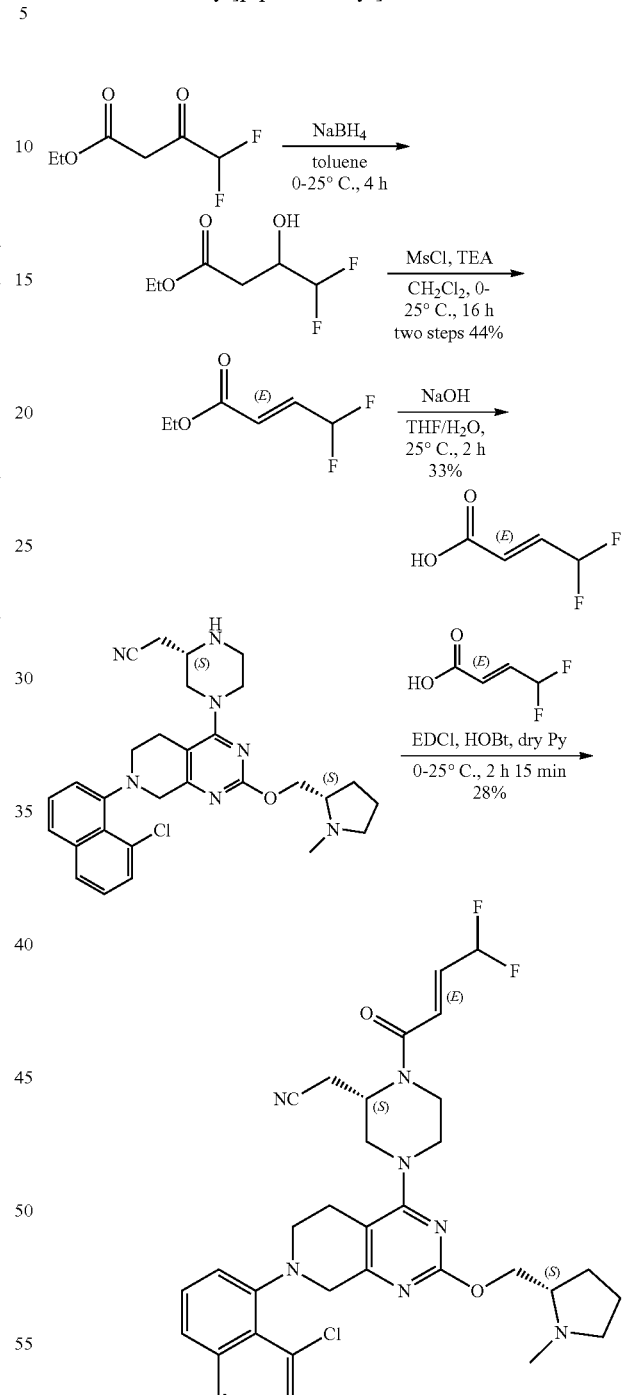

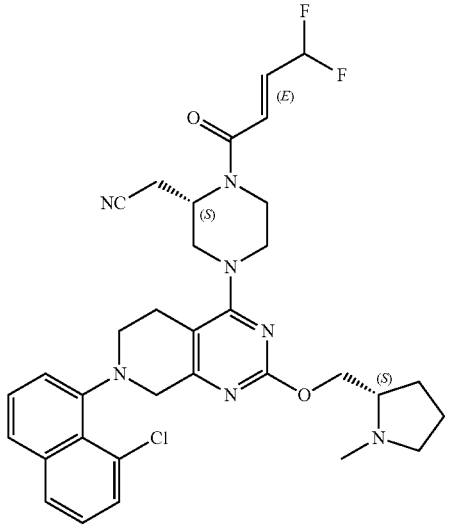

Step 1: 4,4-difluoro-3-hydroxy-butanoate

To a solution of ethyl 4,4-difluoro-3-oxo-butanoate (5.00 g, 30.1 mmol, 1.00 eq) in toluene (150 mL) was added NaBH₄ (1.20 g, 31.7 mmol, 1.05 eq) at 0° C. After stirred at 25° C. for 4 hours, the mixture was diluted with water (50.0 mL) at 0° C. and extracted with ethyl acetate (3×100 mL).

The extracts were washed with brine (1×100 mL), dried over Na$_2$SO$_4$, filtered and concentrated under vacuum to give ethyl 4,4-difluoro-3-hydroxy-butanoate (4.30 g, crude) as a yellow oil and used into next step without further purification.

$^1$H NMR (400 MHz, DMSO-d$_6$) δ=6.05-5.87 (m, 1H), 5.86-5.72 (m, 1H), 4.11-4.01 (m, 2H), 2.57 (dd, J=4.0, 15.6 Hz, 1H), 2.38 (dd, J=9.2, 15.6 Hz, 1H), 1.21-1.17 (m, 3H).

Step 2: ethyl (E)-4,4-difluorobut-2-enoate

To a solution of ethyl 4,4-difluoro-3-hydroxy-butanoate (3.00 g, crude) in dichloromethane (20.0 mL) was added TEA (1.81 g, 17.8 mmol, 2.48 mL) and MsCl (3.68 g, 32.1 mmol, 2.49 mL) at 0° C. After stirred for 4 hours, to the mixture was added TEA (3.61 g, 35.68 mmol, 4.97 mL, 2 eq) 0° C. After warmed up to 25° C. and stirred for 12 hours, the mixture was diluted with water (10.0 mL), washed with HCl (1N, 1×20.0 mL) and brine (1×20.0 mL), dried over Na$_2$SO$_4$, filtered and concentrated under vacuum to give ethyl (E)-4,4-difluorobut-2-enoate (1.40 g, 9.33 mmol, two steps 44% yield) as a colourless oil and used into next step with further purification.

$^1$H NMR (400 MHz, chloroform-d) δ=6.81 (m, 1H), 6.29 (dt, J=2.8, 1.6 Hz, 1H), 6.23 (dd, J=4.0, 55.2 Hz, 1H), 4.25 (q, J=7.2 Hz, 2H), 1.31 (t, J=7.2 Hz, 3H).

Step 3: (E)-4,4-difluorobut-2-enoic acid

A mixture of ethyl (E)-4,4-difluorobut-2-enoate (1.30 g, 8.66 mmol, 1.00 eq) and NaOH (1.39 g, 34.6 mmol, 4.00 eq) in THF (5.00 mL) and H$_2$O (5.00 mL) was stirred at 25° C. for 2 hours. The mixture was acidified with HCl (2N, 20.0 mL) to pH=1-3 and extracted with ethyl acetate (3×20.0 mL). The organic layers were dried over Na$_2$SO$_4$, filtered and concentrated under vacuum to give (E)-4,4-difluorobut-2-enoic acid (0.35 g, 2.87 mmol, 33% yield) as a yellow solid and used into next step without further purification.

$^1$H NMR (400 MHz, chloroform-d) δ=6.92 (m, 1H), 6.32 (dtd, J=0.8, 2.8, 16.8 Hz, 1H), 6.27 (dtd, J=1.2, 54.8 Hz, 4.0, 1H).

Step A: 2-[(2)-4-[7-(8-chloro-1-naphthyl)-2-[[(2$_S$)-1-methylpyrrolidin-2-yl]methoxy]-6,8-dihydro-5H-pyrido[3,4-d]pyrimidin-4-yl]-1-[(E)-4,4-difluorobut-2-enoyl]piperazin-2-yl]acetonitrile A mixture of (E)-4,4-difluorobut-2-enoic acid (68.8 mg, 564 umol, 1.50 eq), EDCI (108 mg, 564 umol, 1.50 eq) and HOBt (50.8 mg, 376 umol, 1.00 eq) in Py (3 mL) was stirred at 0° C. for 15 min, then 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 0.20 g, 376 umol, 1.00 eq) was added into the mixture. After stirred at 0° C. for 1 hour and 25° C. for 1 hour, the mixture was diluted with water (10.0 mL), extracted with ethyl acetate (1×10.0 mL). The extracts were washed with brine (1×10.0 mL), dried over Na$_2$SO$_4$, filtered and concentrated under vacuum. The residue was purified by reversed phase flash [water (FA, 0.10%)/acetonitrile]. The desired fractions were collected and the mixture was neutralized with saturated sodium bicarbonate (5.00 mL), extracted with ethyl acetate (3×20.0 mL). The organic layers were washed with brine (1×30.0 mL), dried over Na$_2$SO$_4$, filtered and concentrated under vacuum. The residue was purified by prep-HPLC (column: Gemini 150*25 5 u; mobile phase: [water (0.05% ammonia hydroxide v/v)-ACN]; B %: 55%-85%, 12 min). The desired fractions were collected and lyophilized to give title compound 2-[(2s)-4-[7-(8-chloro-1-naphthyl)-2-[[(2s)-1-methylpyrrolidin-2-yl]methoxy]-6,8-dihydro-5H-pyrido[3,4-d]pyrimidin-4-yl]-1-[(E)-4,4-difluorobut-2-enoyl]piperazin-2-yl]acetonitrile (EXAMPLE 484, 66.9 mg, 104 umol, 28% yield, 98.7% purity) as a yellow solid. LCMS [ESI, M+1]: 636.

$^1$H NMR (400 MHz, chloroform-d) δ=7.76 (d, J=8.0 Hz, 1H), 7.62 (t, J=7.2 Hz, 1H), 7.52 (d, J=7.2 Hz, 1H), 7.45 (td, J=7.6, 12.8 Hz, 1H), 7.37-7.31 (m, 1H), 7.27-7.18 (m, 1H), 6.88-6.71 (m, 2H), 6.45-6.12 (m, 1H), 5.17-4.59 (m, 1H), 4.55-4.41 (m, 1H), 4.40-4.33 (m, 1H), 4.21-3.69 (m, 5H), 3.64-3.32 (m, 2H), 3.31-2.97 (m, 5H), 2.96-2.52 (m, 4H), 2.47 (d, J=1.6 Hz, 3H), 2.33-2.23 (m, 1H), 2.11-2.00 (m, 1H), 1.90-1.77 (m, 3H).

Example 485

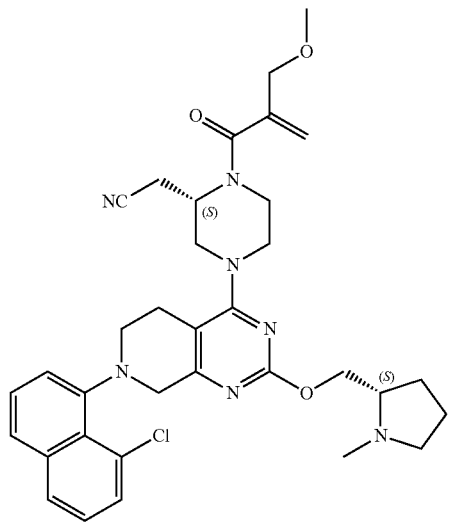

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(methoxymethyl)prop-2-enoyl]piperazin-2-yl]acetonitrile

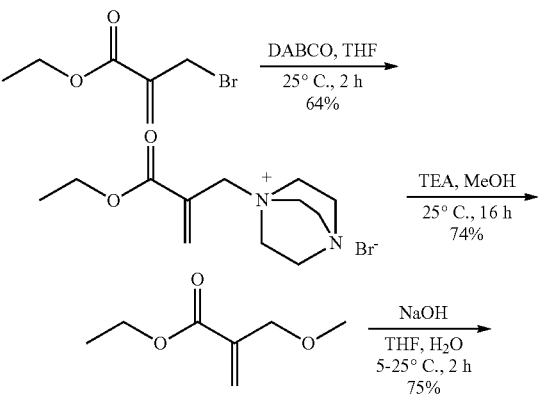

-continued

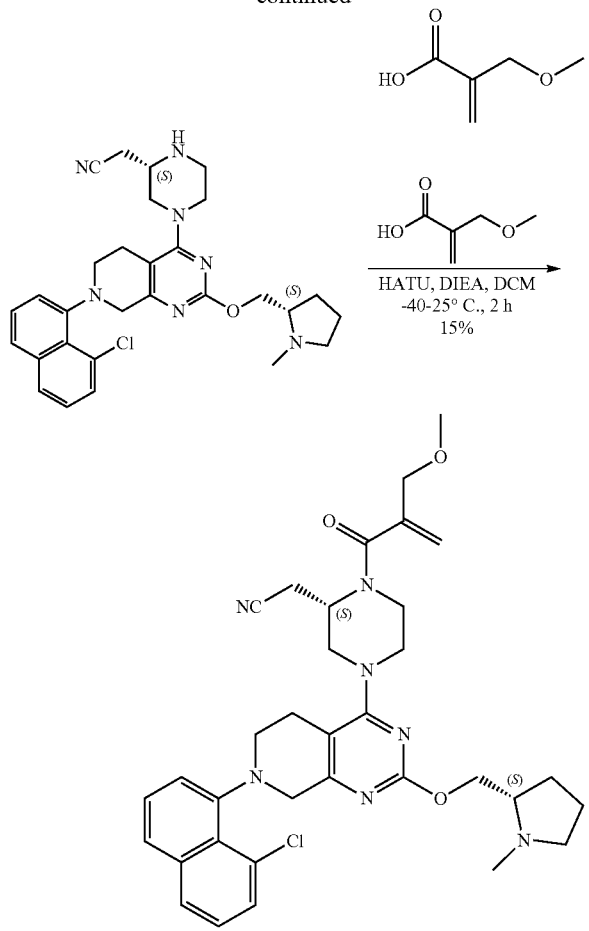

Step 1: 1-(2-(ethoxycarbonyl)allyl)-1,4-diazabicyclo[2.2.2] octan-1-ium bromide

To ethyl 2-(bromomethyl)prop-2-enoate (15 g, 77.7 mmol, 1 eq) in THF (5 mL) was added DABCO (10.5 g, 93.6 mmol, 10.3 mL, 1.20 eq) and the resulting mixture was stirred at 25° C. for 2 hours. The precipitate was formed and filtered under nitrogen atmosphere. The filter cake was collected to give 1-(2-(ethoxycarbonyl)allyl)-1,4-diazabicyclo[2.2.2]octan-1-ium bromide (15 g, 49.6 mmol, 64% yield) as a light yellow solid which was used directly in the next step without further purification.

Step 2: ethyl 2-(methoxymethyl)prop-2-enoate

A mixture of 1-(2-(ethoxycarbonyl)allyl)-1,4-diazabicyclo[2.2.2] octan-1-ium bromide (15 g, 49.6 mmol, 1 eq) and TEA (10.5 g, 104 mmol, 14.5 mL, 2.09 eq) in MeOH (150 mL) was stirred at 25° C. for 16 hours. The solvent was evaporated under vacuum (25° C.). The residue was dissolved into DCM (40 ml) and then washed with 5% aqueous citric acid solution (1×40 mL) and saturated sodium bicarbonate aqueous solution (1×40 mL). The organic layer was dried over sodium sulfate, filtered and concentrated under vacuum at 25° C. to give ethyl 2-(methoxymethyl)prop-2-enoate (5.3 g, 36.8 mmol, 74% yield) as a yellow liquid which was used directly in the next step without further purification.

Step 3: 2-(methoxymethyl)prop-2-enoic acid

To a solution of ethyl 2-(methoxymethyl)prop-2-enoate (5.1 g, 35.4 mmol, 1 eq) in THF (71 mL) was added a solution of NaOH (5.66 g, 142 mmol, 4 eq) in $H_2O$ (71 mL) at 5° C. The mixture was stirred at 25° C. for 2 hours. Upon completion, the THF was evaporated under vacuum. The pH of the mixture was adjusted to 3 with 1 M HCl and extracted with EtOAc (3×70 mL). The organic layers were dried over $Na_2SO_4$ and concentrated under vacuum to give 2-(methoxymethyl)prop-2-enoic acid (3.4 g, 26.4 mmol, 75% yield, 90% purity) as a light yellow liquid which was used directly in the next step without further purification.

$^1$H NMR (400 MHz, chloroform-d) δ=6.45 (d, J=1.2 Hz, 1H), 5.98 (q, J=1.6 Hz, 1H), 4.16 (t, J=1.2 Hz, 2H), 3.42 (s, 3H).

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(methoxymethyl)prop-2-enoyl]piperazin-2-yl]acetonitrile To a solution of 2-(methoxymethyl)prop-2-enoic acid (175 mg, 1.50 mmol, 2 eq) and DIEA (389 mg, 3.01 mmol, 524 uL, 4 eq) in DCM (8 mL) was added HATU (429 mg, 1.13 mmol, 1.5 eq) at −40° C. After stirred at −40° C. for 10 minutes, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 400 mg, 752 umol, 1 eq) was added into the mixture. The mixture was stirred at −40° C. for 20 minutes, 0° C. for 0.5 hour and 25° C. for 1 hour. Upon completion, to the mixture was added water (10 mL) and extracted with DCM (2×20 mL). The combined organic layers were dried over $Na_2SO_4$, filtered and concentrated under vacuum. The residue was purified by chromatography ($Al_2O_3$, EtOAc/MeOH 100/1 to 40/1) and purified by prep-HPLC (column: Gemini 150*25 5 u; mobile phase: [water (0.05% ammonia hydroxide v/v)-ACN]; B %: 50%-80%, 12 min). The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(methoxymethyl)prop-2-enoyl]piperazin-2-yl]acetonitrile (EXAMPLE 485, 73.0 mg, 116 umol, 15% yield, 98.9% purity) as a off-white solid. LCMS [ESI, M+1]:630.

SFC condition: Column: Chiralpak AS-3 100×4.6 mm I.D., 3 um Mobile phase: methanol (0.05% DEA) in $CO_2$ from 5% to 40% Flow rate: 3 mL/min Wavelength: 220 nm.

$^1$H NMR (400 MHz, chloroform-d) δ=7.76 (br d, J=8 Hz, 1H), 7.62 (t, J=7.6 Hz, 1H), 7.52 (d, J=7.6 Hz, 1H), 7.45 (td, J=7.6, 13.2 Hz, 1H), 7.37-7.30 (m, 1H), 7.26-7.17 (m, 1H), 5.51 (s, 1H), 5.32 (br s, 1H), 5.19-4.58 (m, 1H), 4.48-4.34 (m, 2H), 4.23-4.07 (m, 4H), 4.06-3.78 (m, 3H), 3.64-3.55 (m, 1H), 3.39 (s, 3H), 3.36-2.72 (m, 8H), 2.71-2.53 (m, 2H), 2.47 (s, 3H), 2.35-2.22 (m, 1H), 2.14-1.98 (m, 1H), 1.90-1.73 (m, 3H).

1305

Example 486

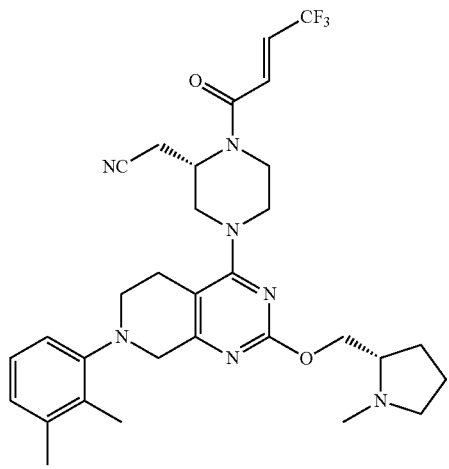 [SMILES: Cc1cccc(N2CCc3c(nc(OC[C@@H]4CCCN4C)nc3N3CCN(C(=O)/C=C/C(F)(F)F)[C@@H](CC#N)C3)C2)c1C]

2-((S)-4-(7-(2,3-dimethylphenyl)-2-((S)-1-methyl-pyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile

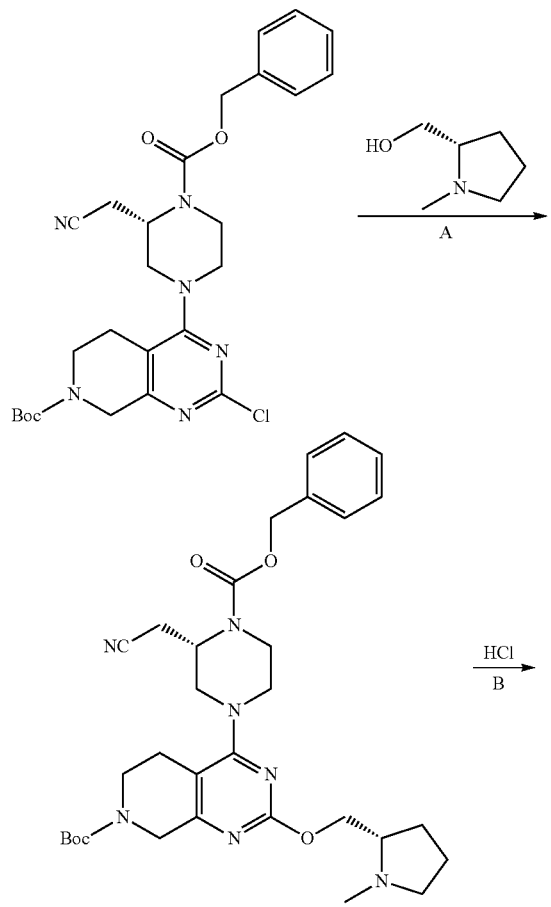

1306

-continued

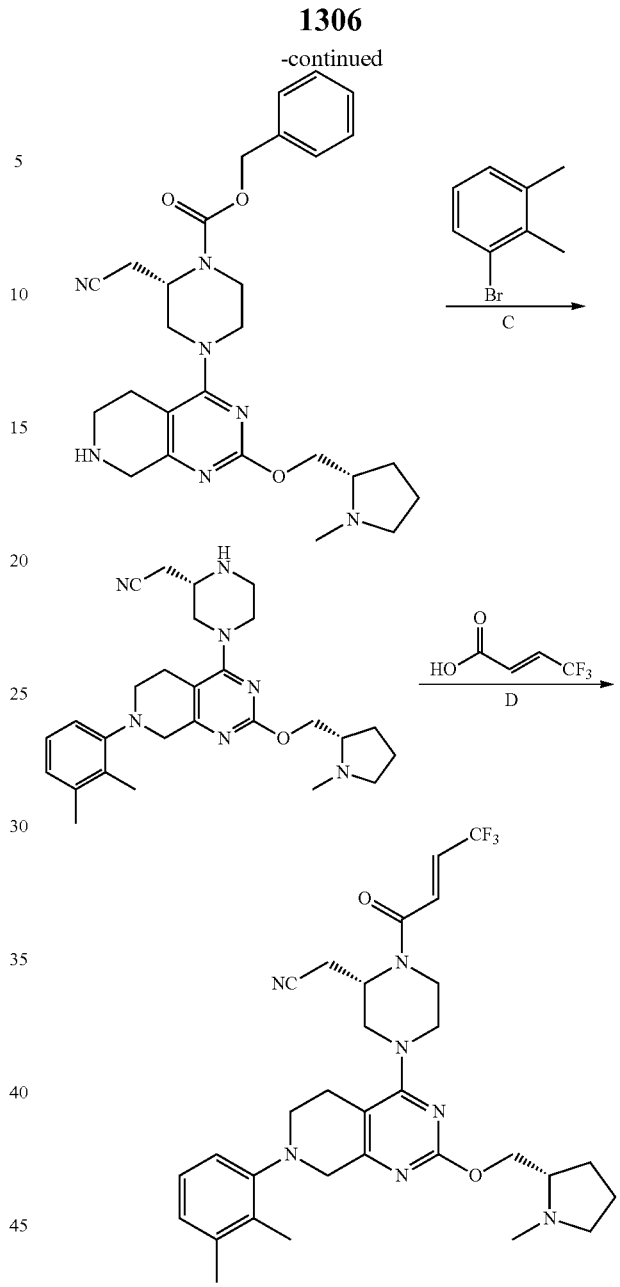

Step A: 2-tert-butyl 4-((S)-4-((benzyloxy)carbonyl)-3-(cyanomethyl)piperazin-1-yl)-2-((S)-1-methylpyr-rolidin-2-yl)methoxy)-5,8-dihydropyrido[3,4-d]py-rimidine-7(6H)-carboxylate In a round bottom flask, a solution of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (5 g, 9.487 mmol) in dioxane (94.87 ml, 9.487 mmol) was sparged with argon and (S)-(1-methylpyrrolidin-2-yl)methanol (3.278 g, 28.46 mmol), Cs$_2$CO$_3$ (9.273 g, 28.46 mmol), Methanesulfonato(2-dicyclohexylphosphino-2',6'-di-i-propoxy-1,1'-biphenyl)(2'-methylamino-1,1'-biphenyl-2-yl)palladium(II) (0.8078 g, 0.9487 mmol) were sequentially added under Argon and sparged for an additional 5 minutes. The reaction mixture was capped and heated at 100° C. overnight. The reaction was filtered through GF/F paper and concentrated in vacuo. The concentrate was purified on the Combi Flash (0-12% MeOH in DCM with 2% NH₄OH) to provide tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (5.425 g, 8.508 mmol, 89.68% yield). ESI+APCI MS m/z 606.4 [M+H]⁺.

Step B: benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (5.4 g, 8.915 mmol) was dissolved in dichloromethane (89.15 ml, 8.915 mmol) and treated with Hydrochloric Acid (4.0M solution in 1,4-dioxane) (11.14 ml, 44.57 mmol). The reaction stirred at room temperature for 1 hour. The reaction was diluted with more DCM and 1M NaOH and the layers separated. The organics were next washed with brine, dried over Na₂SO₄ and concentrated in vacuo to give benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (4.364 g, 8.631 mmol, 96.82% yield). ESI+APCI MS m/z 506.3 [M+H]⁺.

Step C: 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile In a round bottom flask, a solution of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (4.364 g, 8.631 mmol) in dioxane (43.15 ml, 8.631 mmol) was sparged with Argon for 5 minutes. 1-Bromo-2,3-dimethylbenzene (5.851 ml, 43.15 mmol), Cs₂CO₃ (14.06 g, 43.15 mmol), and Methanesulfonato(2-dicyclohexylphosphino-2',6'-di-i-propoxy-1,1'-biphenyl)(2'-methylamino-1,1'-biphenyl-2-yl)palladium(II) (0.7348 g, 0.8631 mmol) were sequentially added under Argon and sparged for an additional 5 min. The reaction mixture was capped and heated at 100° C. ON. The reaction was cooled to room temperature. Ethyl acetate was added and the reaction filtered through GF/F paper and concentrated in vacuo. The concentrate was purified twice via normal phase chromatography on the CombiFlash using 0-15% MeOH in DCM with 2% NH₄OH as eluent. Fractions containing desired product were collected and concentrated in vacuo to give 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile (0.411 g, 0.8641 mmol, 100.1% yield). ESI+APCI MS m/z 476.3 [M+H]⁺.

Step D: 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile To a solution of 2-((S)-4-(7-(2,3-dimethylphenyl)-2-((S)-1-methylpyrrolidin-2-yl)methoxy)-5,6,7,8-tetrahydropyrido[3,4-d]pyrimidin-4-yl)piperazin-2-yl)acetonitrile (200 mg, 0.420 mmol), 4,4,4-Trifluorocrotonic Acid (118 mg, 0.841 mmol), DIEA (367 µl, 2.10 mmol) in DCM (4205 µl, 0.420 mmol) was added HATU (240 mg, 0.631 mmol) and the resulting mixture was stirred at room temperature for 5 hours. The reaction mixture was washed with Brine and the aqueous layer extracted with DCM (2×). The combined organic layers were dried over Na₂SO₄, concentrated, diluted in 60:40 ACN:H₂O and purified on the Gilson (reverse prep HPLC), eluting with 5→95% ACN/0.1% TFA in water/0.1% TFA. Fractions containing product were combined and free based with saturated bicarb and the organics extracted with DCM. The organics were dried over Na₂SO₄ and concentrated in vacuo to give title compound 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile (EXAMPLE 486, 28 mg, 0.0468 mmol, 11.1% yield). ESI+APCI MS m/z 598.3 [M+H]⁺.

Example 487

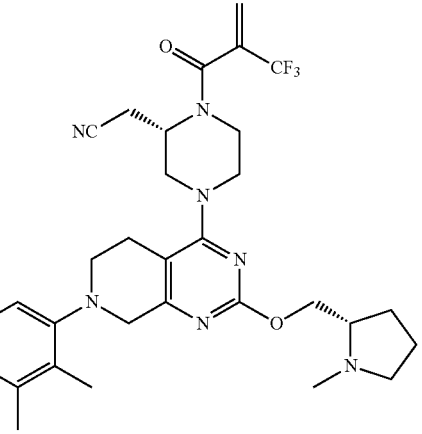

2-((S)-4-(7-(2,3-dimethylphenyl)-2-((S)-1-methylpyrrolidin-2-yl)methoxy)-5,6,7,8-tetrahydropyrido[3,4-d]pyrimidin-4-yl)-1-(2-(trifluoromethyl)acryloyl)piperazin-2-yl)acetonitrile 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-(2-(trifluoromethyl)acryloyl)piperazin-2-yl)acetonitrile The title compound was prepared following Example 486 substituting 2-(Trifluoromethyl)propenoic acid for 4,4,4-Trifluorocrotonic Acid in Step D. ESI+APCI MS m/z 598.3 [M+H]⁺.

1309

Example 488

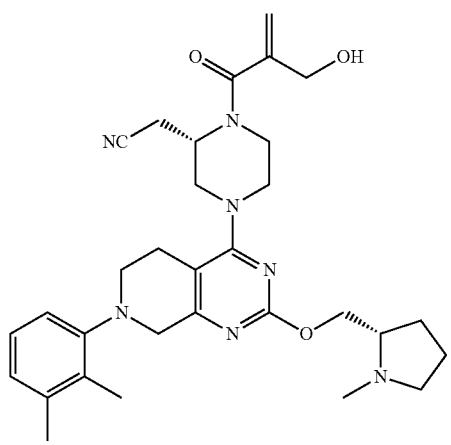 [SMILES: C=C(CO)C(=O)N1CCN(c2nc(OC[C@@H]3CCCN3C)nc3c2CCN(c2cccc(C)c2C)C3)C[C@@H]1CC#N]

2-((S)-4-(7-(2,3-dimethylphenyl)-2-(((S)-1-methyl-
pyrrolidin-2-yl)methoxy)-5,6,7,8-tetrahydropyrido[3,
4-d]pyrimidin-4-yl)-1-(2-(hydroxymethyl)acryloyl)
piperazin-2-yl)acetonitrile 2-((S)-4-(7-(2,3-dimethylphenyl)-2-((S)-1-methyl-
pyrrolidin-2-yl)methoxy)-5,6,7,8-tetrahydropyrido[3,
4-d]pyrimidin-4-yl)-1-(2-(hydroxymethyl)acryloyl)
piperazin-2-yl)acetonitrile The title compound was prepared following Example 486 substituting 2-(hydroxymethyl)prop-2-enoic acid for 4,4,4-Trifluorocrotonic Acid in Step D. ESI+APCI MS m/z 560.3 [M+H]+.

Example 489

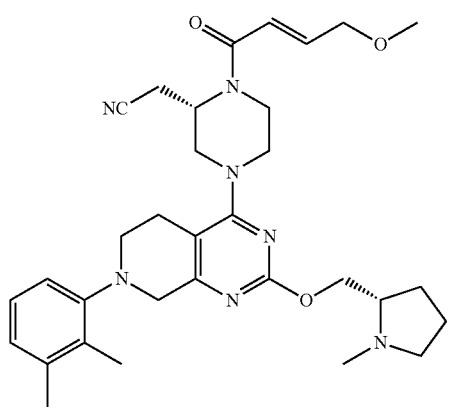 [SMILES: COC/C=C/C(=O)N1CCN(c2nc(OC[C@@H]3CCCN3C)nc3c2CCN(c2cccc(C)c2C)C3)C[C@@H]1CC#N]

1310

2-((S)-4-(7-(2,3-dimethylphenyl)-2-(((S)-1-methyl-
pyrrolidin-2-yl)methoxy)-5,6,7,8-tetrahydropyrido[3,
4-d]pyrimidin-4-yl)-1-((E)-4-methoxybut-2-enoyl)
piperazin-2-yl)acetonitrile

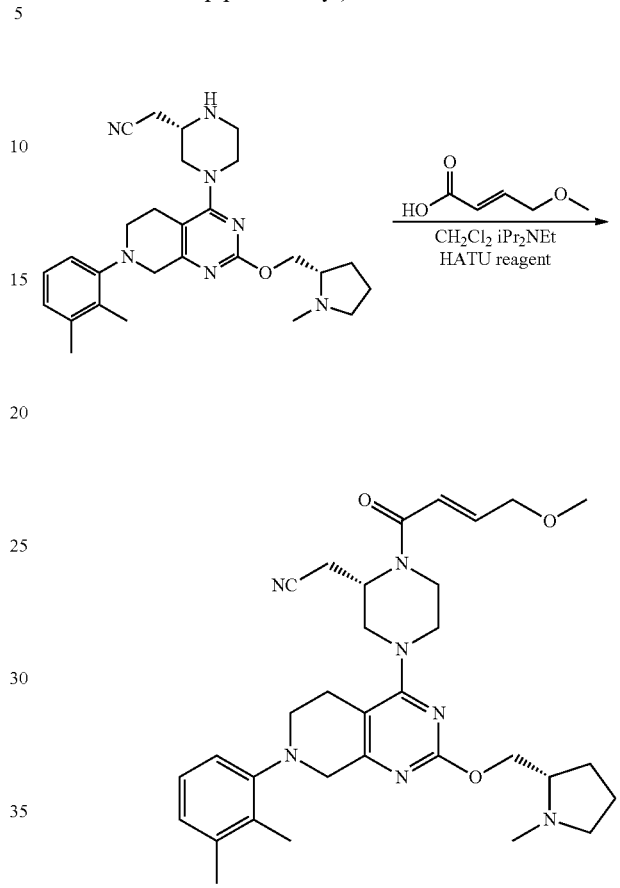

Step A: 2-((S)-4-(7-(2,3-dimethylphenyl)-2-(((S)-1-
methylpyrrolidin-2-yl)methoxy)-5,6,7,8-tetrahydro-
pyrido[3,4-d]pyrimidin-4-yl)-1-((E)-4-methoxybut-
2-enoyl)piperazin-2-yl)acetonitrile To a solution of 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile (50 mg, 0.1051 mmol) in DCM (1 mL) was added (E)-4-methoxybut-2-enoic acid (24.41 mg, 0.2102 mmol), N-ethyl-N-isopropylpropan-2-amine (0.03662 ml, 0.2102 mmol) and O-(7-azabenzotriazol-1-yl)-N,N,N',N'-tetramethyluronium $PF_6$ (59.96 mg, 0.1577 mmol) and the reaction mixture stirred at room temperature for 4 hours. Water (1 mL) was next added and the reaction mixture stirred for 5 minutes. The mixture was divided between EtOAc (10 mL) and 0.5M $NaHCO_3$ (5 mL) and the layers separated. The organics were washed with brine (3 mL), dried over $Na_2SO_4$ and evaporated in vacuo. The residue was chromatographed on silica gel using 3% MeOH+0.3% $NH_4OH$ to 4% MeOH+0.4% $NH_4OH$ as eluent to give title compound (EXAMPLE 489, 26 mg, 43%). ESI+APCI MS m/z 574.4 [M+H]+.

1311
Example 490

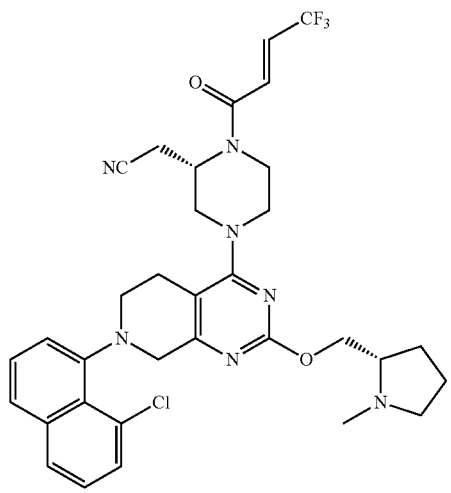 [SMILES: CN1CCC[C@H]1COc1nc2c(c(N3CCN(C(=O)/C=C/C(F)(F)F)[C@@H](CC#N)C3)n1)CCN(c1cccc3cccc(Cl)c13)C2]

2-((S)-4-(7-(8-chloronaphthalen-1-yl)-2-(((S)-1-methylpyrrolidin-2-yl)methoxy)-5,6,7,8-tetrahydropyrido [3,4-d]pyrimidin-4-yl)-1-((E)-4,4,4-trifluorobut-2-enoyl)piperazin-2-yl)acetonitrile

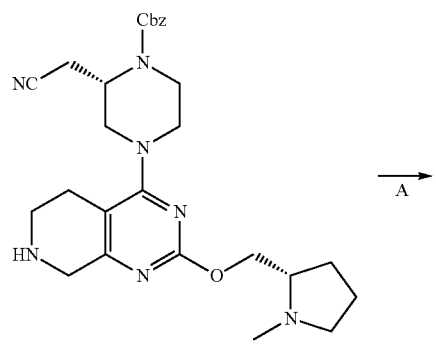

A →

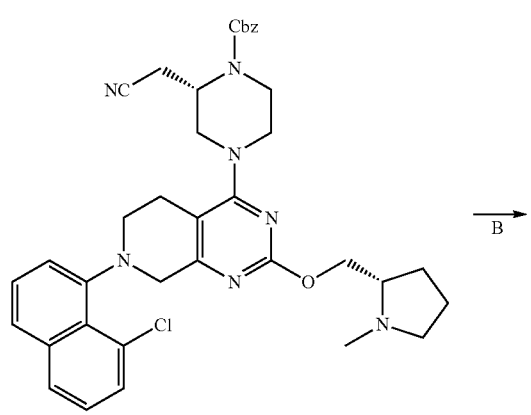

B →

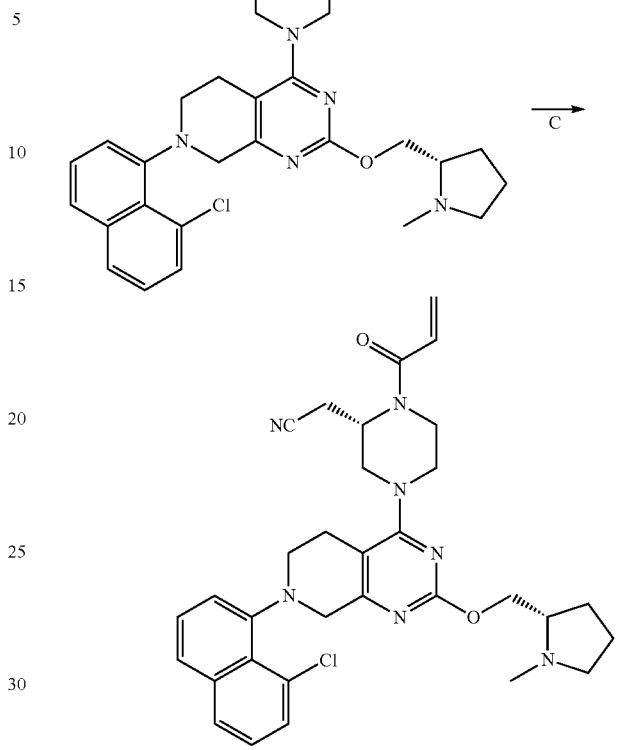

C →

Step A: benzyl (S)-4-(7-(8-chloronaphthalen-1-yl)-2-((S)-1-methylpyrrolidin-2-yl)methoxy)-5,6,7,8-tetrahydropyrido[3,4-d]pyrimidin-4-yl)-2-(cyanomethyl)piperazine-1-carboxylate To a solution of benzyl (S)-2-(cyanomethyl)-4-(2-(((S)-1-methylpyrrolidin-2-yl)methoxy)-5,6,7,8-tetrahydropyrido [3,4-d]pyrimidin-4-yl)piperazine-1-carboxylate (0.6 g, 1.2 mmol) in dioxanes (10 mL) was added 1-bromo-8-chloronaphthalene (0.37 g, 1.5 mmol) and the reaction degassed with Ar for 15 minutes followed by addition of $Cs_2CO_3$ (1.2 g, 3.6 mmol), $Pd_2(dba)_3$ (0.22 g, 0.24 mmol) and 2-Dicyclohexylphosphino-2',6'-di-i-propoxy-1,1'-biphenyl (0.11 g, 0.24 mmol) and the reaction heated to 100° C. for overnight. The reaction was next filtered through GFF paper and the filtrated concentrated in vacuo. The residue was next chromatographed using 1410% (MeOH+2% $NH_4OH$)/DCM to give benzyl (S)-4-(7-(8-chloronaphthalen-1-yl)-2-(((S)-1-methylpyrrolidin-2-yl)methoxy)-5,6,7,8-tetrahydropyrido [3,4-d]pyrimidin-4-yl)-2-(cyanomethyl)piperazine-1-carboxylate (0.20 g, 0.30 mmol, 25% yield). ESI+APCI MS m/z 666.2 [M+H]$^+$.

Step B: 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile A solution of benzyl (S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (0.17 g, 0.255 mmol) in THF (30 mL)

1313 was purged with N$_2$ followed by addition of Pd/C (0.0272 g, 0.255 mmol). The reaction was evacuated by vacuum and backfilled with H$_2$ 3× and the mixture was stirred for 3 days at room temperature. The reaction was again purged with N$_2$ followed by filtering through celite and the filtrate concentrated in vacuo. The material used crude in the next reaction. ESI+APCI MS m/z 532.2 [M+H]$^+$.

Step C: 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile To a solution of 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (0.055 g, 0.10 mmol) in DCM (20 mL) was added N-ethyl-N-isopropylpropan-2-amine (0.040 g, 0.31 mmol), (E)-4,4,4-trifluorobut-2-enoic acid (0.017 g, 0.12 mmol) and 1-Propanephosphonic acid cyclic anhydride (0.033 g, 0.10 mmol) and the reaction stirred at room temperature for 30 minutes. Next additional TEP3 and acid (0.24 mmol) were added and the reaction an addition 1 hour. The organics were next washed with 1 N NaOH, brine, dried over MgSO$_4$ and concentrated in vacuo. The material was chromatographed 2× on normal phase silica (1→10% (MeOH+2% NH$_4$OH)/DCM) followed by purification by gilson reverse prep HPLC using 5→95% ACN/water with 0.1% TFA as additive. The PURE fractions were poured into basic water and extracted into EtOAc. The organics were washed with brine, dried over MgSO$_4$ and concentrated in vacuo to give title compound 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile (EXAMPLE 490, 0.0094 g, 0.014 mmol, 14% yield). ESI+APCI MS m/z 654.2 [M+H]$^+$.

Example 491

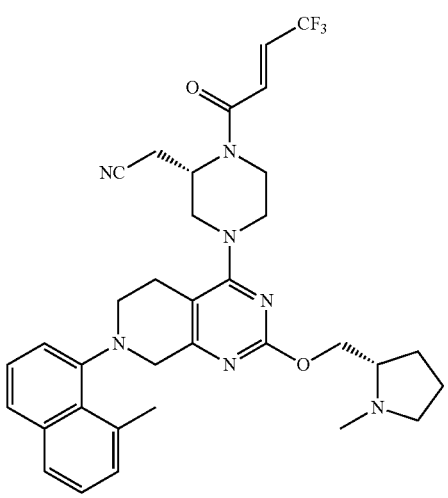 [SMILES: Cc1cccc2cccc(N3CCc4c(nc(OC[C@@H]5CCCN5C)nc4N4CCN(C(=O)/C=C/C(F)(F)F)[C@@H](CC#N)C4)C3)c12]

1314

2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile

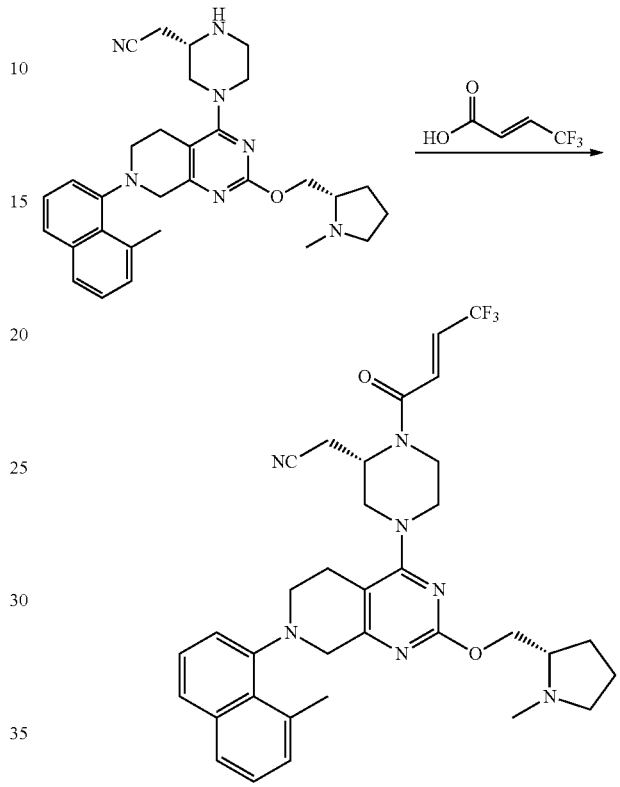

Step A: 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile At 0° C., to a 25 mL RBF containing N,N-dimethylformamide (2932 µl, 0.293 mmol) was added 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (150 mg, 0.293 mmol) and Hunig's base (102 µl, 0.586 mmol). The reaction mixture was vigorously stirred while (E)-4,4,4-trifluorobut-2-enoic acid (49.3 mg, 0.352 mmol) was added in one portion. Next, 1-Propanephosphonic acid cyclic anhydride (262 µl, 0.440 mmol) was added slowly to the stirring mixture. The reaction was stirred for 2 hours at 0° C. The reaction was treated with basic water and the aqueous layer extracted with EtOAc (3×). The combined organics were concentrated in vacuo and resuspended in a 60:40 mixture of ACN:H$_2$O and purified on the Gilson (reverse prep HPLC), eluting with 5→95% ACN/0.1% TFA in water/0.1% TFA. Fractions containing product were combined and partitioned between saturated bicarb and DCM. The aqueous layer was extracted with DCM two more times. The organic layers were combined, dried over Na$_2$SO$_4$ and concentrated in vacuo to give title compound 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2- enoyl)piperazin-2-yl)acetonitrile (EXAMPLE 491, 74.5 mg, 0.118 mmol, 40.1% yield). ESI+APCI MS m/z 634.3 [M+H]+.

Example 492

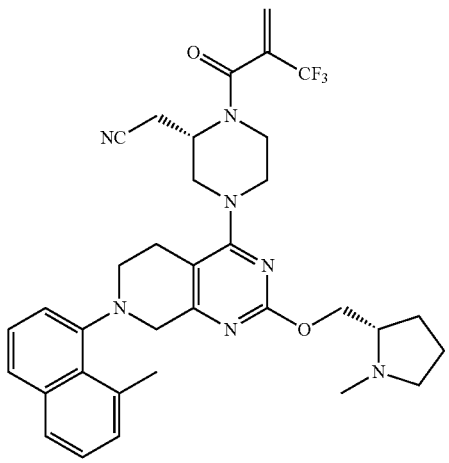 [SMILES: C=C(C(=O)N1CCN(c2nc(OC[C@@H]3CCCN3C)nc3c2CCN(c2cccc4cccc(C)c24)C3)C[C@@H]1CC#N)C(F)(F)F]

2-((S)-4-(7-(8-methylnaphthalen-1-yl)-2-(((S)-1-methylpyrrolidin-2-yl)methoxy)-5,6,7,8-tetrahydro-pyrido[3,4-d]pyrimidin-4-yl)-1-(2-(trifluoromethyl)acryloyl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydro-pyrido[3,4-d]pyrimidin-4-yl)-1-(2-(trifluoromethyl)acryloyl)piperazin-2-yl)acetonitrile The title compound was prepared following Example 491 substituting 2-(trifluoromethyl)acrylic acid for (E)-4,4,4-trifluorobut-2-enoic acid in Step A. ESI+APCI MS m/z 634.2 [M+H]+.

Example 493

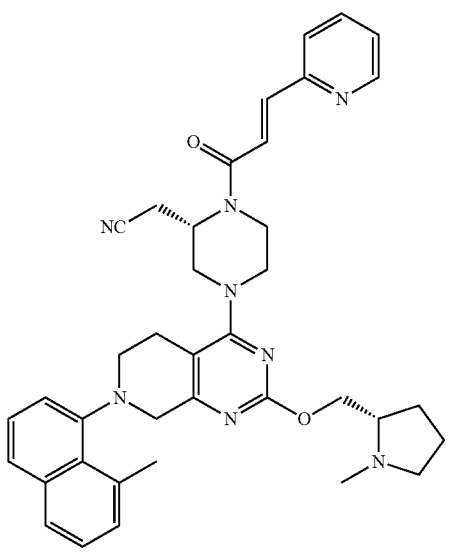 [SMILES: Cc1cccc2cccc(N3CCc4c(nc(OC[C@@H]5CCCN5C)nc4N4CCN(C(=O)/C=C/c5ccccn5)[C@@H](CC#N)C4)C3)c12]

2-((S)-4-(7-(8-methylnaphthalen-1-yl)-2-(((S)-1-methylpyrrolidin-2-yl)methoxy)-5,6,7,8-tetrahydro-pyrido[3,4-d]pyrimidin-4-yl)-1-((E)-3-(pyridin-2-yl)acryloyl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydro-pyrido[3,4-d]pyrimidin-4-yl)-1-((E)-3-(pyridin-2-yl)acryloyl)piperazin-2-yl)acetonitrile The title compound was prepared following Example 491 substituting 3-(Pyridin-2-yl)acrylic acid for (E)-4,4,4-trifluorobut-2-enoic acid in Step A. ESI+APCI MS m/z 643.3 [M+H]+.

Example 494

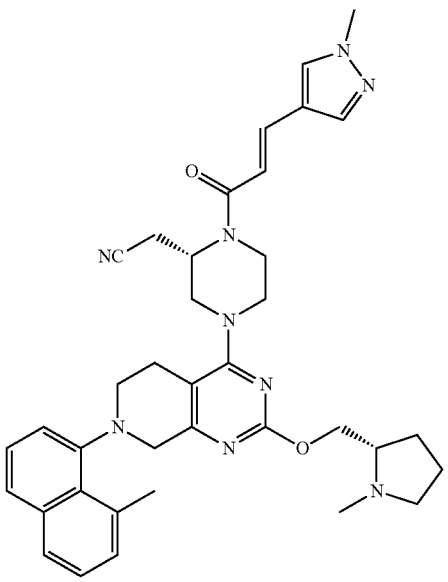 [SMILES: Cc1cccc2cccc(N3CCc4c(nc(OC[C@@H]5CCCN5C)nc4N4CCN(C(=O)/C=C/c5cnn(C)c5)[C@@H](CC#N)C4)C3)c12]

2-((S)-1-((E)-3-(1-methyl-1H-pyrazol-4-yl)acryloyl)-4-(7-(8-methylnaphthalen-1-yl)-2-(((S)-1-methylpyrrolidin-2-yl)methoxy)-5,6,7,8-tetrahydro-pyrido[3,4-d]pyrimidin-4-yl)piperazin-2-yl)acetonitrile 2-((S)-1-((E)-3-(1-methyl-1H-pyrazol-4-yl)acryloyl)-4-(7-(8-methylnaphthalen-1-yl)-2-(((S)-1-methylpyrrolidin-2-yl)methoxy)-5,6,7,8-tetrahydro-pyrido[3,4-d]pyrimidin-4-yl)piperazin-2-yl)acetonitrile The title compound was prepared following Example 491 substituting (2E)-3-(1-Methyl-1H-pyrazol-4-yl)acrylic acid for (E)-4,4,4-trifluorobut-2-enoic acid in Step A. ESI+APCI MS m/z 646.4 [M+H]+.

Example 495

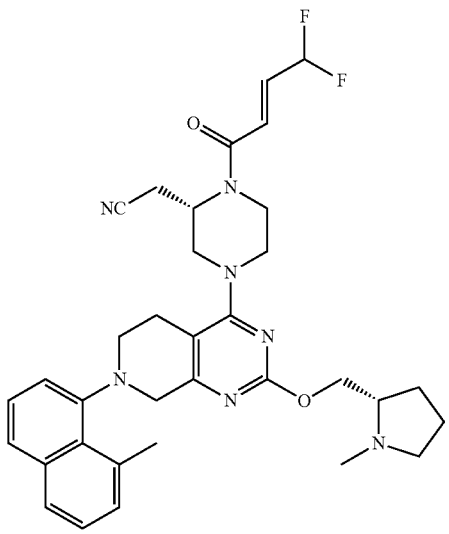 [SMILES: Cc1cccc2cccc(N3CCc4c(nc(OC[C@@H]5CCCN5C)nc4N4CCN(C(=O)/C=C/C(F)F)[C@@H](CC#N)C4)C3)c12]

2-((S)-1-((E)-4,4-difluorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-((E)-4,4-difluorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile The title compound was prepared following Example 491 substituting 4,4-Difluorobut-2-enoic acid for (E)-4,4-trifluorobut-2-enoic acid in Step A. ESI+APCI MS m/z 616.3 [M+H]⁺.

Example 496

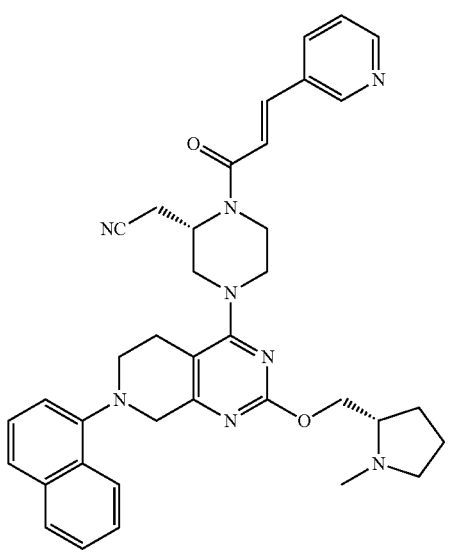 [SMILES: CN1CCC[C@H]1COc1nc2c(c(N3CCN(C(=O)/C=C/c4cccnc4)[C@@H](CC#N)C3)n1)CCN(c1cccc3ccccc13)C2]

2-((S)-4-(2-(((S)-1-methylpiperidin-2-yl)methoxy)-7-(naphthalen-1-yl)-5,6,7,8-tetrahydropyrido[3,4-d]pyrimidin-4-yl)-1-((E)-3-(pyridin-3-yl)acryloyl)piperazin-2-yl)acetonitrile

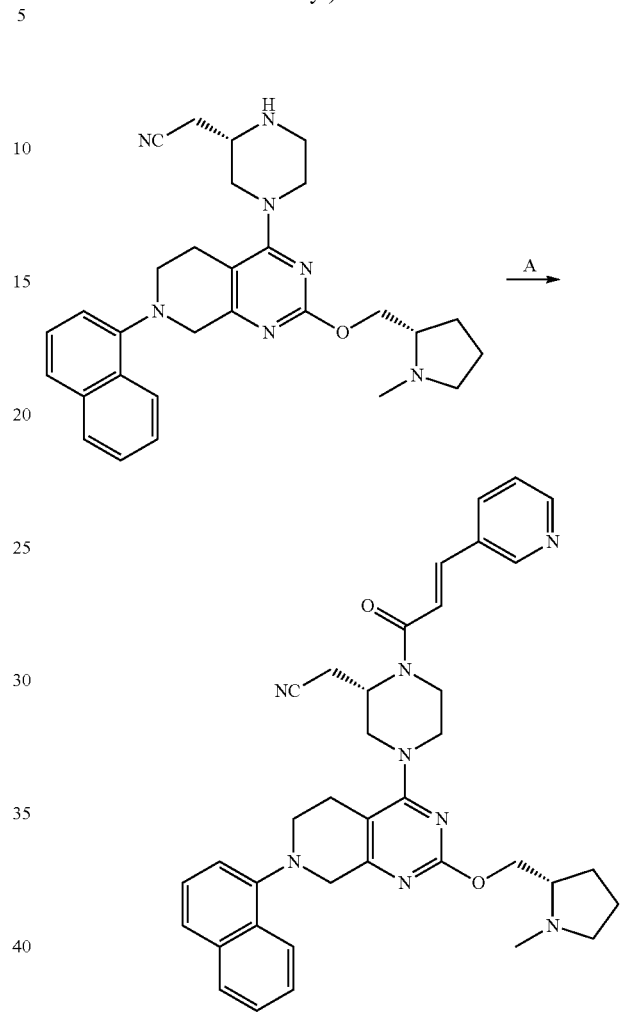

Step A: To a solution of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (0.12 g, 0.23 mmol) in DCM (10 mL) N-ethyl-N-isopropylpropan-2-amine (0.13 ml, 0.70 mmol), (E)-3-(pyridin-3-yl)acrylic acid (0.070 g, 0.47 mmol) and 2,4,6-tripropyl-1,3,5,2,4,6-trioxatriphosphinane 2,4,6-trioxide (0.30 g, 0.47 mmol) and the reaction stirred at room temperature for 3 hours. The reaction was next poured into 1N NaOH and the layers separated. The organics were next washed with brine, dried over MgSO₄ and concentrated in vacuo. The material was next purified by Gilson reverse prep HPLC eluting with 5→95 ACN/water with 0.1% TFA as modifier. Fractions containing product were poured into 1N NaOH and the aqueous layer extracted with EtOAc (3×). The combined organics were washed with brine, dried over MgSO₄ and concentrated in vacuo to give title compound 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-3-(pyridin-3-yl)acryloyl)piperazin-2-yl)acetonitrile (EXAMPLE 496, 0.040 g, 0.062 mmol, 27% yield). ESI+APCI MS m/z 643.3 [M+H]⁺.

Example 497

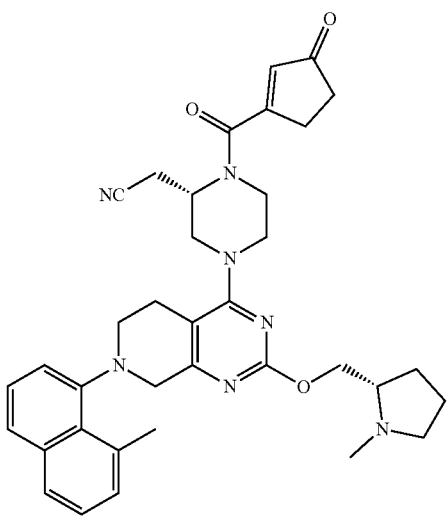 [SMILES: Cc1cccc2cccc(N3CCc4c(nc(OC[C@@H]5CCCN5C)nc4N4CCN(C(=O)C5=CC(=O)CC5)[C@@H](CC#N)C4)C3)c12]

2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-(3-oxocyclopent-1-ene-1-carbonyl)piperazin-2-yl)acetonitrile

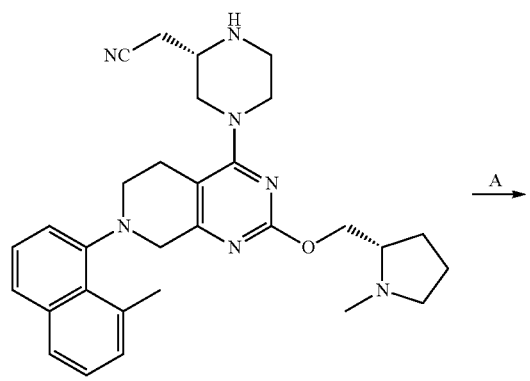

A →

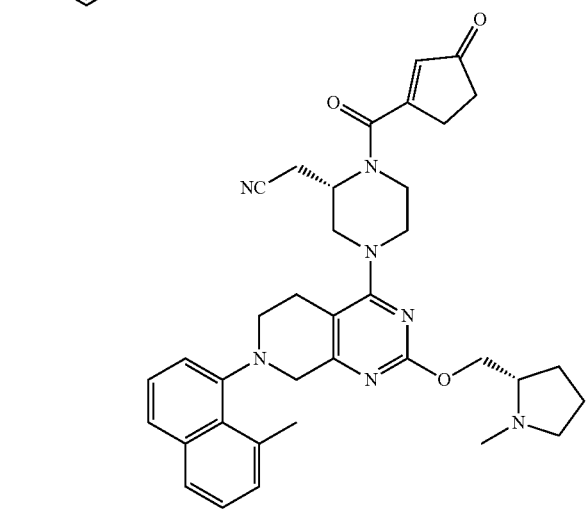

Step A: 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-(3-oxocyclopent-1-ene-1-carbonyl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (30 mg, 0.05863 mmol) and 3-oxocyclopent-1-enecarboxylic acid (9.612 mg, 0.07622 mmol) were diluted with DMF (400 uL) followed by the addition of DIEA (20.48 µl, 0.1173 mmol) and 1-propanephosphonic acid cyclic anhydride (52.35 µl, 0.08795 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silica gel eluting with 10% methanol/DCM (1% NH$_4$OH) to afford title compound 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-(3-oxocyclopent-1-ene-1-carbonyl)piperazin-2-yl)acetonitrile (EXAMPLE 497, 2.3 mg, 0.003711 mmol, 6.329% yield). ESI+APCI MS m/z 620.3 [M+H]$^+$.

Example 498

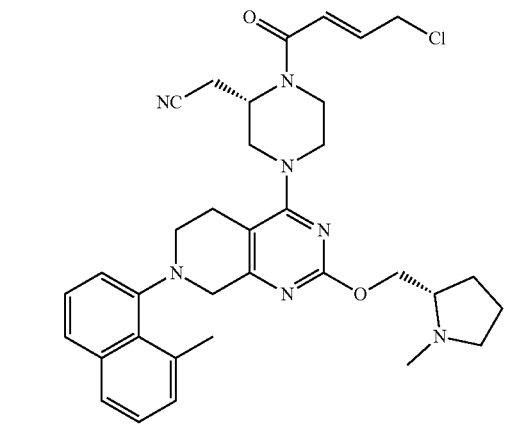

2-((S)-1-((E)-4-chlorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

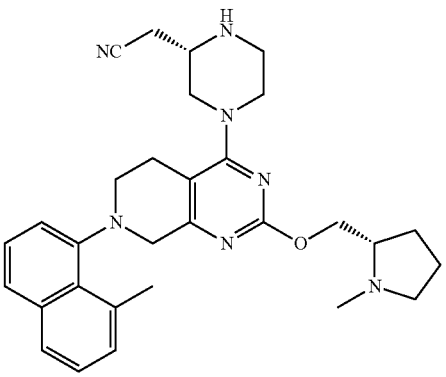

A →

1321

-continued

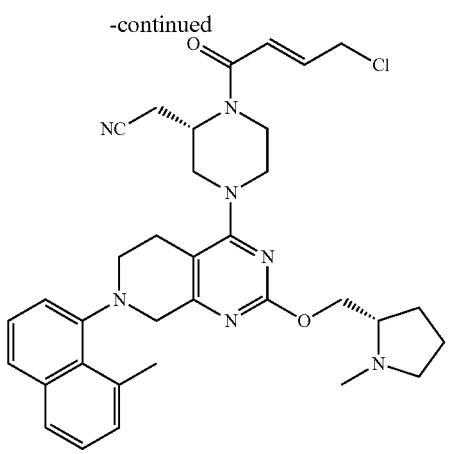

Step A: 2-((S)-1-((E)-4-chlorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (30 mg, 0.05863 mmol) and gamma-chlorocrotonic acid (10.60 mg, 0.08795 mmol) were diluted with DMF (400 uL) followed by the addition of DIEA (20.48 µl, 0.1173 mmol) and 1-propanephosphonic acid cyclic anhydride (55.84 µl, 0.09381 mmol). After stirring for 12 hours, the reaction was diluted with ethyl acetate and saturated sodium bicarbonate. The layers were separated and the ethyl acetate was dried over MgSO₄, filtered and concentrated. The material was purified on silica gel eluting with 10% methanol/DCM (1% NH₄OH) to afford title compound 2-((S)-1-((E)-4-chlorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (EXAMPLE 498, 4.5 mg, 0.007327 mmol, 12.50% yield). ESI+APCI MS m/z 614.3 [M+H]⁺.

Example 499

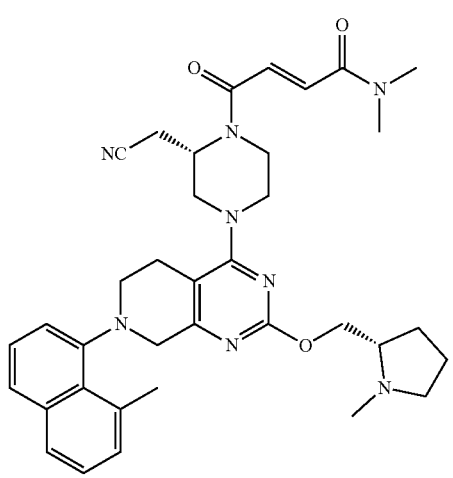 [SMILES: Cc1cccc2cccc(N3CCc4c(nc(OC[C@@H]5CCCN5C)nc4N4CCN(C(=O)/C=C/C(=O)N(C)C)[C@@H](CC#N)C4)C3)c12]

1322

(E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-N,N-dimethyl-4-oxobut-2-enamide

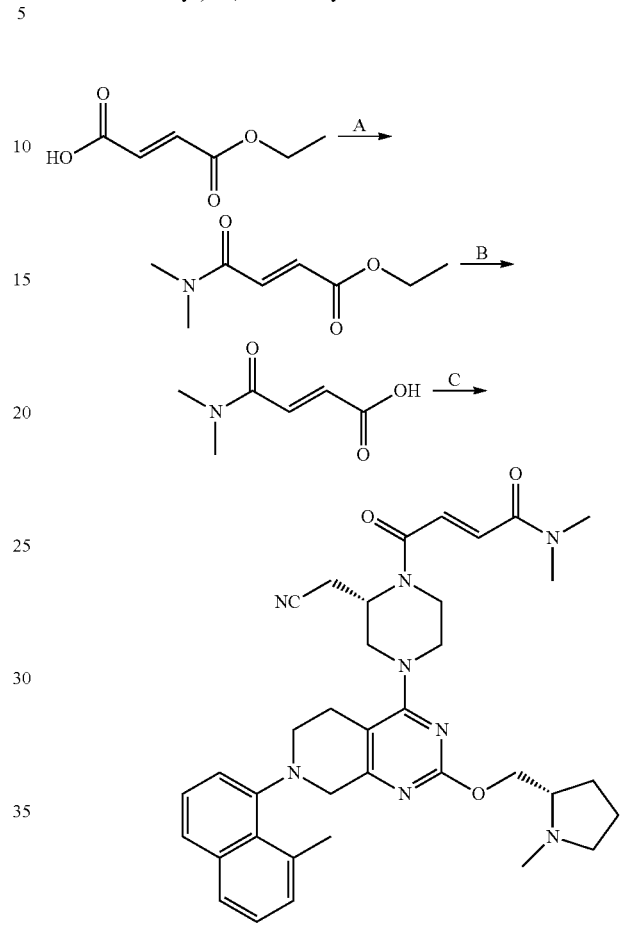

Step A: Ethyl (E)-4-(dimethylamino)-4-oxobut-2-enoate

Fumaric acid monoethyl ester (442 mg, 3.07 mmol) was diluted with DCM (5 mL) followed by the addition of oxalyl chloride (1533 µl, 3.07 mmol) and 1 drop of DMF. After stirring for 15 minutes, dimethylamine (4600 µl, 9.20 mmol) was added and the reaction was stirred for 3 hours. The reaction was diluted with ethyl acetate and water. The layers were separated and the ethyl acetate was dried over MgSO₄, filtered and concentrated. The material was purified on silica gel eluting with 10-70% ethyl acetate/hexanes to afford ethyl (E)-4-(dimethylamino)-4-oxobut-2-enoate (382 mg, 2.23 mmol, 72.8% yield). ESI+APCI MS m/z 172.1 [M+H]⁺.

Step B: (E)-4-(dimethylamino)-4-oxobut-2-enoic acid

Ethyl (E)-4-(dimethylamino)-4-oxobut-2-enoate (382 mg, 2.23 mmol) was diluted with methanol (8 mL) followed by the addition of NaOH (4463 µl, 8.93 mmol). After stirring for 4 hours, the reaction was diluted with 2N HCl (4.5 mL) and extracted with ethyl acetate. The ethyl acetate was dried over MgSO₄, filtered and concentrated to afford (E)-4-(dimethylamino)-4-oxobut-2-enoic acid.

Step C: (E)-4-((S)-2-(cyanomethyl)-4-(7-(8-methyl-naphthalen-1-yl)-2-(((S)-1-methylpyrrolidin-2-yl)methoxy)-5,6,7,8-tetrahydropyrido[3,4-d]pyrimidin-4-yl)piperazin-1-yl)-N,N-dimethyl-4-oxobut-2-enamide 2-((S)-4-(7-(8-methylnaphthalen-1-yl)-2-(((S)-1-methyl-pyrrolidin-2-yl)methoxy)-5,6,7,8-tetrahydropyrido[3,4-d]pyrimidin-4-yl)piperazin-2-yl)acetonitrile (30 mg, 0.05863 mmol) was diluted with DMF followed by the addition of (E)-4-(dimethylamino)-4-oxobut-2-enoic acid (10.07 mg, 0.07036 mmol), DIEA (20.48 µl, 0.1173 mmol) and 1-pro-panephosphonic acid cyclic anhydride (52.35 µl, 0.08795 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silica gel eluting with 10% methanol/DCM (1% NH$_4$OH) to afford title compound (E)-4-((S)-2-(cyanomethyl)-4-(7-(8-methylnaphthalen-1-yl)-2-((S)-1-methylpyrrolidin-2-yl)methoxy)-5,6,7,8-tetrahydropyrido[3,4-d]pyrimidin-4-yl)piperazin-1-yl)-N,N-dimethyl-4-oxobut-2-enamide (EXAMPLE 499, 3.7 mg, 0.005810 mmol, 9.910% yield). ESI+APCI MS m/z 637.3 [M+H]$^+$.

Example 500

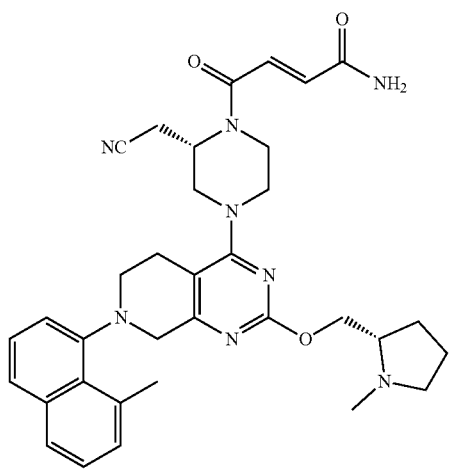 [SMILES: Cc1cccc2cccc(N3CCc4c(nc(OC[C@@H]5CCCN5C)nc4N4CCN(C(=O)/C=C/C(N)=O)[C@@H](CC#N)C4)C3)c12]

(E)-4-((S)-2-(cyanomethyl)-4-(7-(8-methylnaphtha-len-1-yl)-2-(((S)-1-methylpyrrolidin-2-yl)methoxy)-5,6,7,8-tetrahydropyrido[3,4-d]pyrimidin-4-yl)piper-azin-1-yl)-4-oxobut-2-enamide

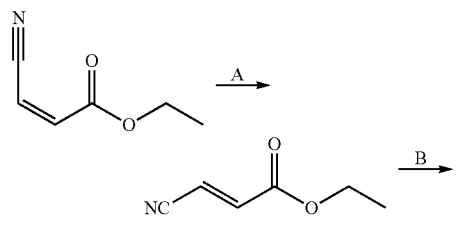

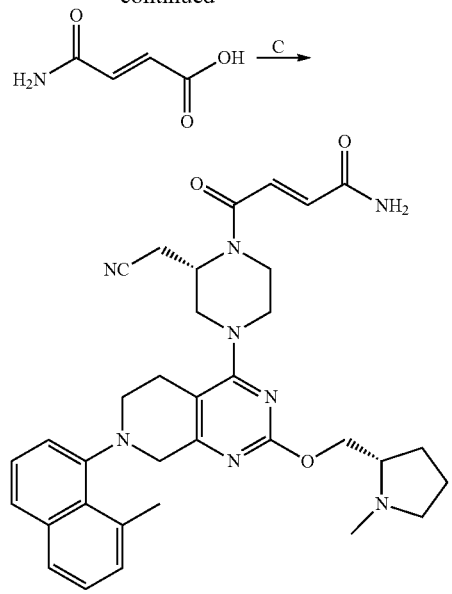

Step A: Ethyl (E)-3-cyanoacrylate

Ethyl cis-(beta-cyano)acrylate (1.0 g, 7.99 mmol) was diluted with ACN (30 mL), placed under nitrogen and heated to reflux for 3 days. The reaction was allowed to cool and then concentrated. The material was purified on silica gel eluting with hexanes to afford ethyl (E)-3-cyanoacrylate (300 mg, 2.40 mmol, 30.0% yield).

Step B: (E)-4-amino-4-oxobut-2-enoic acid

Ethyl (E)-3-cyanoacrylate (300 mg, 2.40 mmol) was diluted with HCl (3996 µl, 24.0 mmol). The reaction was placed under nitrogen and heated to 100° C. for 4 hours. The reaction was allowed to cool and then concentrated to afford (E)-4-amino-4-oxobut-2-enoic acid (214 mg, 1.86 mmol, 77.6% yield).

Step C: (E)-4-((S)-2-(cyanomethyl)-4-(7-(8-methyl-naphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enamide 2-((S)-4-(7-(8-methylnaphthalen-1-yl)-2-(((S)-1-methyl-pyrrolidin-2-yl)methoxy)-5,6,7,8-tetrahydropyrido[3,4-d]pyrimidin-4-yl)piperazin-2-yl)acetonitrile (20 mg, 0.039 mmol), HATU (30 mg, 0.078 mmol) and (E)-4-amino-4-oxobut-2-enoic acid (9.0 mg, 0.078 mmol) were diluted with DMF (400 uL) followed by the addition of DIEA (14 µl, 0.078 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silica gel eluting with 10% methanol/DCM (1% NH$_4$OH) to afford title compound (E)-4-((S)-2-(cyanom-ethyl)-4-(7-(8-methylnaphthalen-1-yl)-2-(((S)-1-methylpyr-rolidin-2-yl)methoxy)-5,6,7,8-tetrahydropyrido[3,4-d]py-rimidin-4-yl)piperazin-1-yl)-4-oxobut-2-enamide (EXAMPLE 500, 2.9 mg, 0.0048 mmol, 12% yield). ESI+APCI MS m/z 609.3 [M+H]$^+$.

Example 501

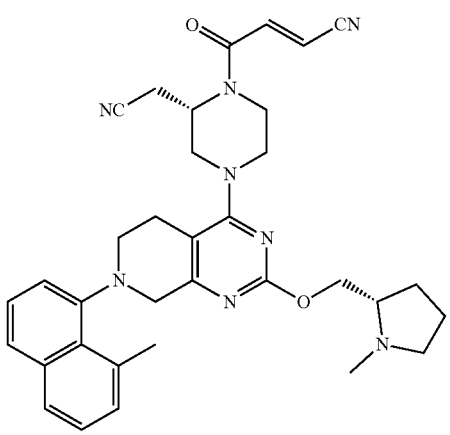 [SMILES: Cc1cccc2cccc(N3CCc4c(nc(OC[C@@H]5CCCN5C)nc4N4CCN(C(=O)/C=C/C#N)[C@@H](CC#N)C4)C3)c12]

(E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile

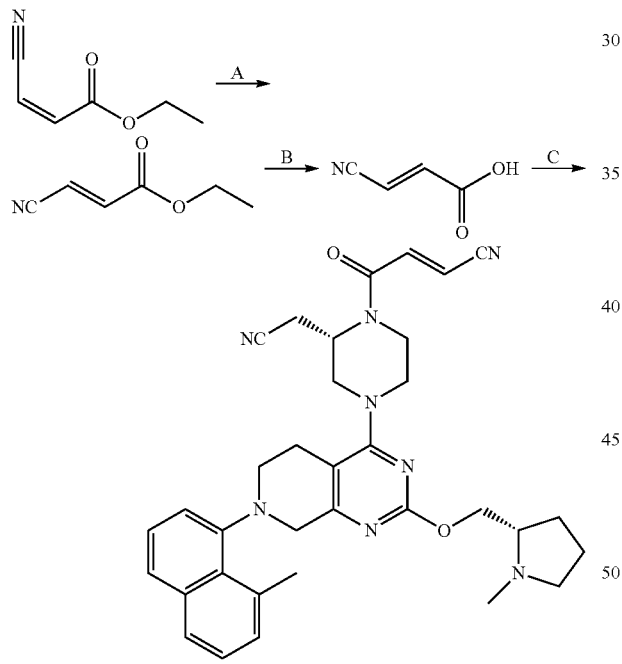

Step A: Ethyl (E)-3-cyanoacrylate

Ethyl cis-(beta-cyano)acrylate (1.0 g, 7.99 mmol) was diluted with ACN (30 mL), placed under nitrogen and heated to reflux for 3 days. The reaction was allowed to cool and then concentrated. The material was purified on silica gel eluting with hexanes to afford ethyl (E)-3-cyanoacrylate (300 mg, 2.40 mmol, 30.0% yield).

Step B: (E)-3-cyanoacrylic acid

Ethyl (E)-3-cyanoacrylate (10 mg, 0.080 mmol) was diluted with HCl (133 μl, 0.80 mmol), placed under nitrogen and heated to 100° C. After stirring for 15 minutes the reaction was concentrated to afford (E)-3-cyanoacrylic acid (7.5 mg, 0.077 mmol, 97% yield).

Step C: (E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile 2-((S)-4-(7-(8-methylnaphthalen-1-yl)-2-(((S)-1-methyl-pyrrolidin-2-yl)methoxy)-5,6,7,8-tetrahydropyrido[3,4-d]pyrimidin-4-yl)piperazin-2-yl)acetonitrile (20 mg, 0.03909 mmol) and (E)-3-cyanoacrylic acid (5.312 mg, 0.05472 mmol) were diluted with DMF (400 uL) followed by the addition of DIEA (13.65 μl, 0.07817 mmol) and 1-propanephosphonic acid cyclic anhydride (34.90 μl, 0.05863 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silica gel eluting with 10% methanol/DCM (1% NH$_4$OH) to afford title compound (E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile (EXAMPLE 501, 3.5 mg, 0.005925 mmol, 15.16% yield). ESI+APCI MS m/z 591.3 [M+H]$^+$.

Example 502

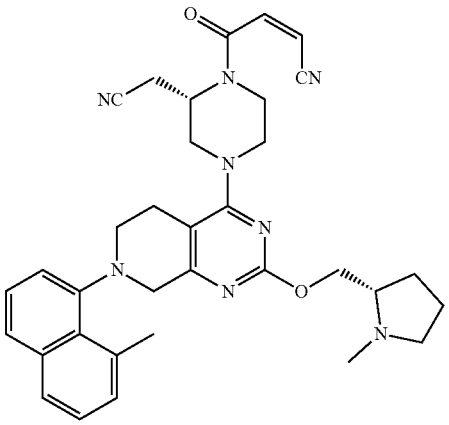 [SMILES: Cc1cccc2cccc(N3CCc4c(nc(OC[C@@H]5CCCN5C)nc4N4CCN(C(=O)/C=C\C#N)[C@@H](CC#N)C4)C3)c12]

(Z)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile

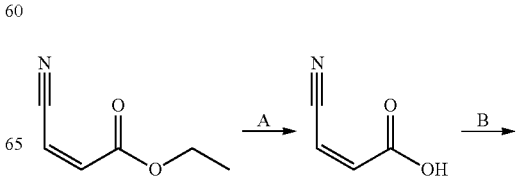

1327

-continued

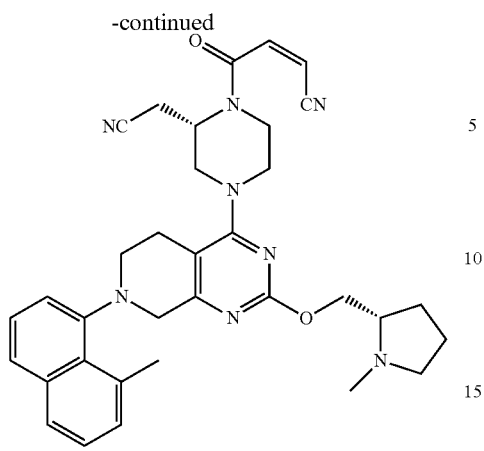

Step A: (Z)-3-cyanoacrylic acid

Ethyl cis-(beta-cyano)acrylate (50 mg, 0.40 mmol) was diluted with HCl (200 µl, 1.2 mmol), placed under nitrogen and heated to 100° C. After stirring for 1 minute the reaction was cooled and concentrated to afford (Z)-3-cyanoacrylic acid (35 mg, 0.36 mmol, 90% yield).

Step B: (Z)-4-((S)-2-(cyanomethyl)-4-(7-(8-methyl-naphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile 2-((S)-4-(7-(8-methylnaphthalen-1-yl)-2-(((S)-1-methyl-pyrrolidin-2-yl)methoxy)-5,6,7,8-tetrahydropyrido[3,4-d]pyrimidin-4-yl)piperazin-2-yl)acetonitrile (20 mg, 0.03909 mmol) and (Z)-3-cyanoacrylic acid (6.071 mg, 0.06254 mmol) were diluted with DMF (400 uL) followed by the addition of DIEA (13.65 µl, 0.07817 mmol) and 1-propanephosphonic acid cyclic anhydride (39.56 µl, 0.06645 mmol). After stirring for 12 hours, the reaction was diluted with ethyl acetate and saturated sodium bicarbonate. The layers were separated and the ethyl acetate was dried over MgSO₄, filtered and concentrated. The material was purified on silica gel eluting with 10% methanol/DCM (1% NH₄OH) to afford title compound (Z)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile (EXAMPLE 502, 2.1 mg, 0.003555 mmol, 9.095% yield). ESI+APCI MS m/z 591.3 [M+H]⁺.

1328

Example 503

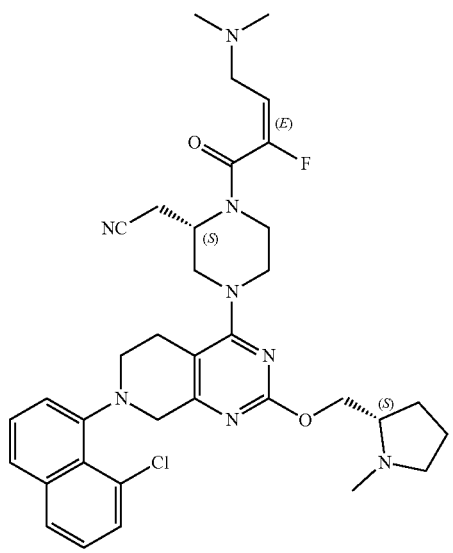

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(dimethylamino)-2-fluoro-but-2-enoyl]piperazin-2-yl]acetonitrile

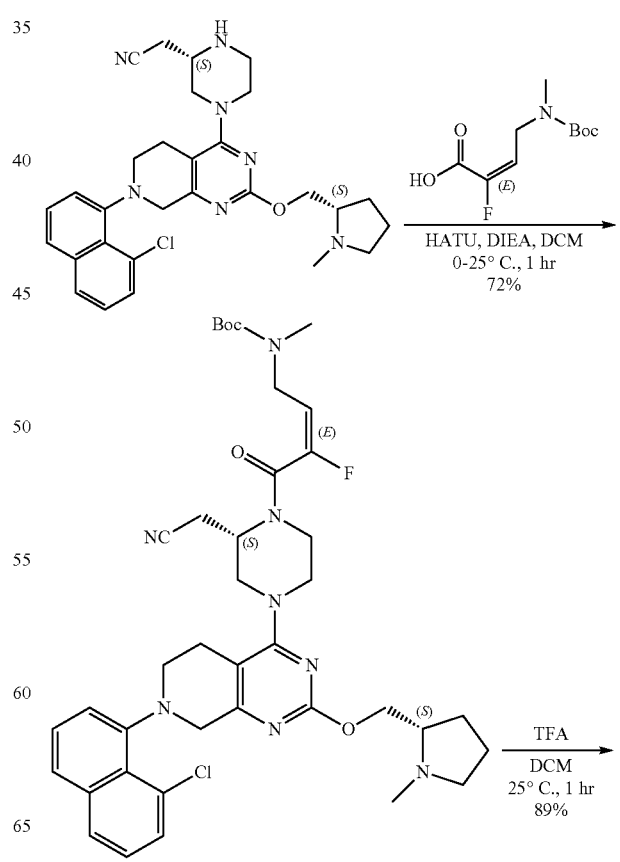

-continued

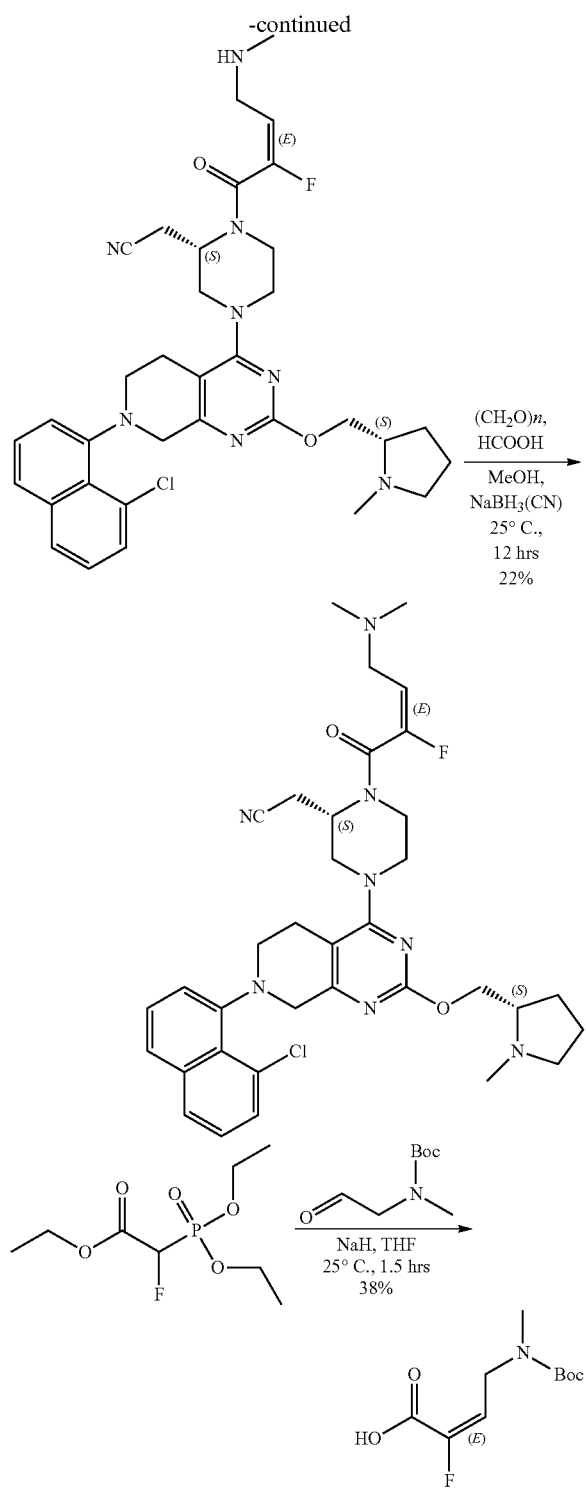

Step 1: (E)-4-[tert-butoxycarbonyl(methyl)amino]-2-fluoro-but-2-enoic acid

To the solution of ethyl 2-diethoxyphosphoryl-2-fluoroacetate (2 g, 8.26 mmol, 1.68 mL, 1 eq) and tert-butyl N-methyl-N-(2-oxoethyl)carbamate (2.15 g, 12.4 mmol, 1.5 eq) in THF (40 mL) was added NaH (661 mg, 16.5 mmol, 60% purity, 2 eq). The mixture was stirred at 25° C. for 1.5 hour. Upon completion, the reaction mixture was quenched by saturated NH₄Cl (8 mL) and concentrated under vacuum. The residue was purified by prep-HPLC (column: Phenomenex Synergi Max-RP 250*50 mm*10 um; mobile phase: [water (0.225% FA)-ACN]; B %: 20ACN %-50ACN %,30 min; 50% min) to give (E)-4-[tert-butoxycarbonyl(methyl)amino]-2-fluoro-but-2-enoic acid (820 mg, 3.16 mmol, 38.3% yield, 90% purity) as a brown oil.

Step A: tert-butyl N-[(E)-4-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazin-1-yl]-3-fluoro-4-oxo-but-2-enyl]-N-methyl-carbamate To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 300 mg, 564 umol, 1 eq), (E)-4-[tert-butoxycarbonyl(methyl)amino]-2-fluoro-but-2-enoic acid (600 mg, 2.57 mmol, 4.56 eq) and DIEA (729 mg, 5.64 mmol, 982 uL, 10 eq) in DCM (10 mL) was added HATU (643 mg, 1.69 mmol, 3 eq) at 0° C. The reaction mixture was stirred at 25° C. for 1 hour. Upon completion, the reaction mixture was quenched by water (3 mL) and extracted with DCM (3×8 mL). The combined organic layers were dried over Na₂SO₄ and concentrated under vacuum. The residue was purified by reversed flash chromatography (FA condition: 60% MeCN in water (0.1% FA)) to give tert-butyl N-[(E)-4-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazin-1-yl]-3-fluoro-4-oxo-but-2-enyl]-N-methyl-carbamate (330 mg, 404 umol, 72% yield, 91.5% purity) as a brown solid. LCMS [ESI, M+1]: 747.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-2-fluoro-4-(methylamino)but-2-enoyl]piperazin-2-yl]acetonitrile To a solution of tert-butyl N-[(E)-4-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazin-1-yl]-3-fluoro-4-oxo-but-2-enyl]-N-methyl-carbamate (300 mg, 401 umol, 1 eq) in DCM (1 mL) was added TFA (915 mg, 8.03 mmol, 594 uL, 20 eq). The reaction mixture was stirred at 25° C. for 1 hour. Upon completion, the reaction mixture was diluted by DCM (10 mL) and basified by saturated NaHCO₃ (8 mL). The mixture was extracted with DCM (3×10 mL). The combined organic layer was dried over Na₂SO₄ and concentrated under vacuum to give 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-2-fluoro-4-(methylamino)but-2-enoyl]piperazin-2-yl]acetonitrile (240 mg, 356 umol, 89% yield, 95.9% purity) as a brown solid which was used for next step without further purification. LCMS [ESI, M+1]: 647.

Step C: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(dimethylamino)-2-fluoro-but-2-enoyl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H- pyrido[3,4-d]pyrimidin-4-yl]-1-[(E)-2-fluoro-4-(methyl-amino)but-2-enoyl]piperazin-2-yl]acetonitrile (120 mg, 185 umol, 1 eq) and paraformaldehyde (83.5 mg, 927 umol, 5 eq), HCOOH (26.7 mg, 556 umol, 3 eq) in MeOH (5 mL) was added NaBH$_3$CN (35.0 mg, 556 umol, 3 eq). The reaction mixture was stirred at 25° C. for 12 hours. Upon completion, the reaction mixture was quenched by water (0.5 mL) and filtered. The residue was purified by silica gel chromatography (EA:MeOH:NH$_3$.H$_2$O=50:1:0 to 10:1:0.1), then prep-HPLC (column: Phenomenex Gemini 150*25 mm*10 um; mobile phase: [water (10 mM NH$_4$HCO$_3$)-ACN]; B %:50%-100%,10 min) to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(dimethylamino)-2-fluoro-but-2-enoyl]piperazin-2-yl]acetonitrile (EXAMPLE 503, 26.7 mg, 40.2 umol, 22% yield, 99.5% purity) as a yellow solid. LCMS [ESI, M+1]: 661.

$^1$H NMR (400 MHz, chloroform-d) δ=7.68 (d, J=8.0 Hz, 1H), 7.54 (t, J=7.2 Hz, 1H), 7.45 (d, J=7.2 Hz, 1H), 7.37 (td, J=7.6, 12.8 Hz, 1H), 7.26 (t, J=8.0 Hz, 1H), 7.19-7.08 (m, 1H), 5.81-5.60 (m, 1H), 5.04-4.41 (m, 1H), 4.40-4.25 (m, 2H), 4.16-3.91 (m, 3H), 3.88-3.71 (m, 2H), 3.66-3.46 (m, 2H), 3.36 (br d, J=10.8 Hz, 1H), 3.27-2.69 (m, 9H), 2.64-2.56 (m, 1H), 2.55-2.46 (m, 1H), 2.40 (d, J=2.4 Hz, 3H), 2.27-2.15 (m, 7H), 2.06-1.90 (m, 1H), 1.85-1.72 (m, 3H).

Example 504

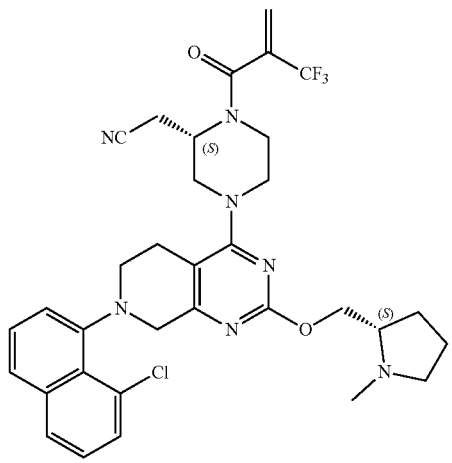

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(trifluoromethyl)prop-2-enoyl]piperazin-2-yl]acetonitrile

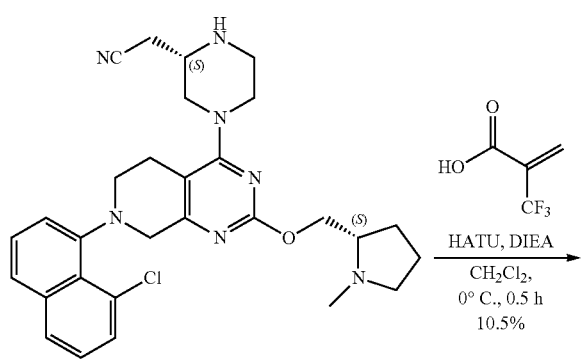

-continued

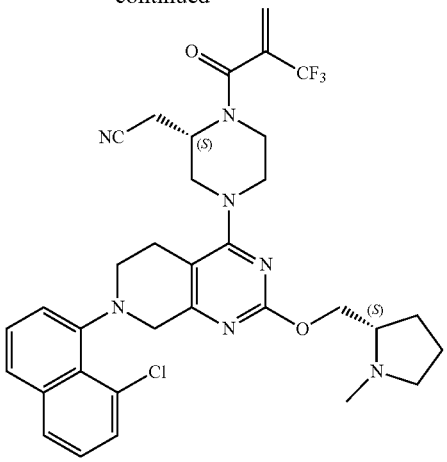

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(trifluoromethyl)prop-2-enoyl]piperazin-2-yl]acetonitrile To a solution of 2-(trifluoromethyl)prop-2-enoic acid (39.5 mg, 282 umol, 1.50 eq), 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 0.10 g, 188 umol, 1.00 eq) and DIEA (48.6 mg, 376 umol, 65.5 uL, 2.00 eq) in dichloromethane (0.20 mL) was added HATU (107 mg, 282 umol, 1.50 eq) at 0° C. After stirred at 0° C. for 0.5 h, the mixture diluted with water and the layer was separated. The organic layer was dried over Na$_2$SO$_4$, filtered and concentrated under vacuum. The residue was purified by reverse phase flash [water (FA, 0.1%)/acetonitrile] and prep HPLC (column: Gemini 150*25 5 u; mobile phase: [water (0.05% ammonia hydroxide v/v)-ACN]; B %: 56%-86%, 12 min). The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(trifluoromethyl)prop-2-enoyl]piperazin-2-yl]acetonitrile (EXAMPLE 504, 13.1 mg, 19.6 umol, 10.5% yield, 97.9% purity) as a white solid. LCMS [ESI, M+1]: 654.

SFC condition: Column: Chiralcel OJ-3 50×4.6 mm I.D., 3 um, Mobile phase: methanol (0.05% DEA) in CO$_2$ from 5% to 40%, Flow rate: 3 mL/min, Wavelength: 220 nm.

$^1$H NMR (400 MHz, chloroform-d) δ=7.76 (d, J=8.4 Hz, 1H), 7.65-7.59 (m, 1H), 7.55-7.50 (m, 1H), 7.45 (td, J=7.6, 10.0 Hz, 1H), 7.34 (t, J=7.6 Hz, 1H), 7.26-7.18 (m, 1H), 6.18 (br s, 1H), 5.86 (br s, 1H), 5.11 (br s, 1H), 4.57-4.36 (m, 2H), 4.33-4.10 (m, 2H), 4.04 (br d, J=12.8 Hz, 1H), 3.97-3.79 (m, 2H), 3.66-3.54 (m, 1H), 3.50-3.33 (m, 1H), 3.29-3.07 (m, 4H), 3.04-2.72 (m, 4H), 2.63-2.50 (m, 4H), 2.45-2.32 (m, 1H), 2.15-2.04 (m, 1H), 1.90 (br s, 3H).

Example 505

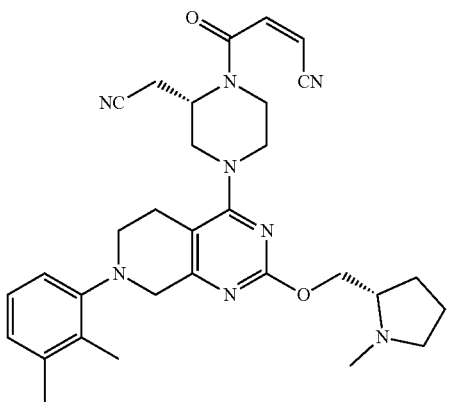 [SMILES: Cc1cccc(N2CCc3c(nc(OC[C@@H]4CCCN4C)nc3N3CCN(C(=O)/C=C\C#N)[C@@H](CC#N)C3)C2)c1C]

2-((S)-1-((Z)-3-chloroacryloyl)-4-(7-(2,3-dimethyl-phenyl)-2-(((S)-1-methylpyrrolidin-2-yl)methoxy)-5,6,7,8-tetrahydropyrido[3,4-d]pyrimidin-4-yl)piper-azin-2-yl)acetonitrile 2-((S)-1-((Z)-3-chloroacryloyl)-4-(7-(2,3-dimethyl-phenyl)-2-(((S)-1-methylpyrrolidin-2-yl)methoxy)-5,6,7,8-tetrahydropyrido[3,4-d]pyrimidin-4-yl)piper-azin-2-yl)acetonitrile Was prepared following Example 389 Step J, substituting (Z)-3-chloroacrylic acid for but-2-ynoic acid. ESI+APCI MS m/z 564.3 [M+H]+.

Example 506

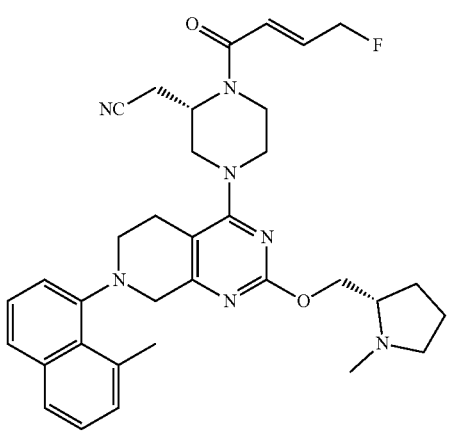 [SMILES: Cc1cccc2cccc(N3CCc4c(nc(OC[C@@H]5CCCN5C)nc4N4CCN(C(=O)/C=C/CF)[C@@H](CC#N)C4)C3)c12]

2-((S)-1-((E)-4-fluorobut-2-enoyl)-4-(7-(8-methyl-naphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

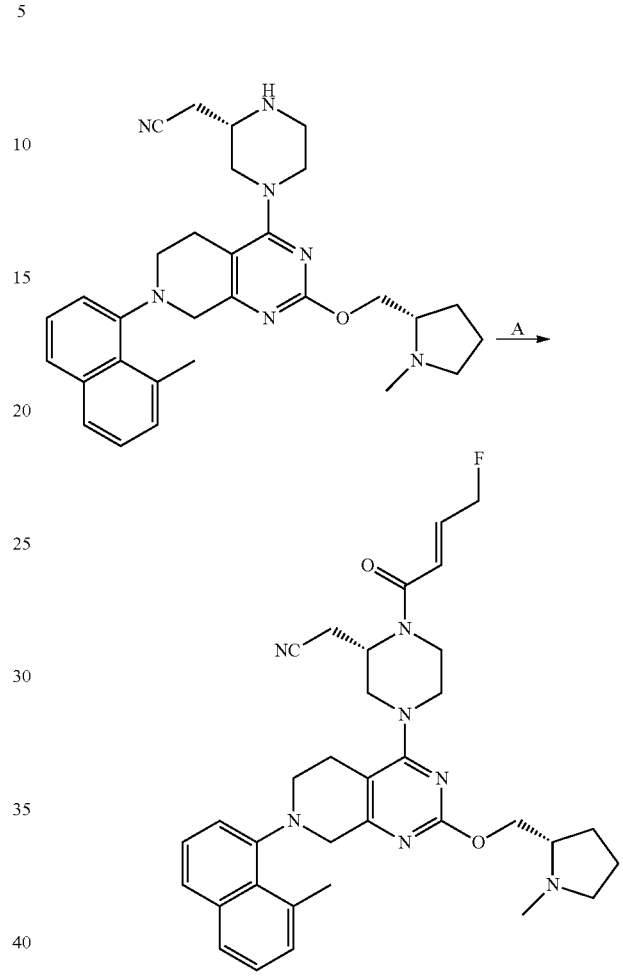

Step A: 2-((S)-1-((E)-4-fluorobut-2-enoyl)-4-(7-(8-methylnaphthalen-1-yl)-2-(((S)-1-methylpyrrolidin-2-yl)methoxy)-5,6,7,8-tetrahydropyrido[3,4-d]py-rimidin-4-yl)piperazin-2-yl)acetonitrile At 0° C., to a 25 mL RBF containing N,N-dimethylfor-mamide (3909 µl, 0.39 mmol) was added 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (200 mg, 0.391 mmol) and triethylamine (136 µl, 0.98 mmol). The reaction mixture was vigorously stirred while (E)-4-fluorobut-2-enoic acid (61.0 mg, 0.59 mmol) was added in one portion. Next, 1-propa-nephosphonic acid cyclic anhydride (175 µl, 0.59 mmol) was added slowly to the stirring mixture. The reaction was stirred at room temperature for 18 hr. Water was added and the mixture was extracted with EtOAc (3×15 mL). The extracts were combined and washed with water (1×10 mL) and concentrated. The residue was purified by silica gel (5-18% MeOH in DCM with 0.25% NH$_4$OH) to provide title compound 2-((S)-1-((E)-4-fluorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)

piperazin-2-yl)acetonitrile (EXAMPLE 506, 89.3 mg, 0.15 mmol, 38% yield). ESI+APCI MS m/z 598.3 [M+H]+.

Example 507

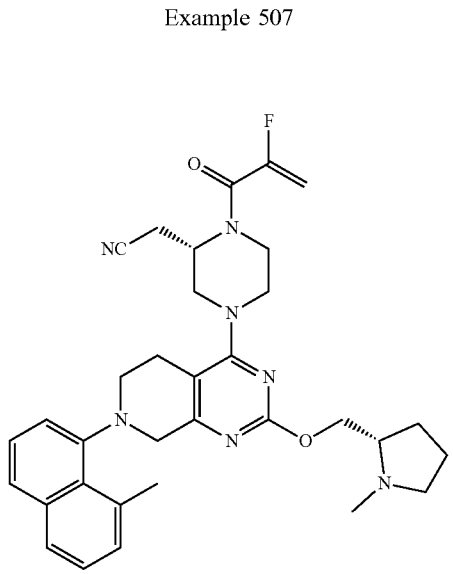

2-((S)-1-(2-fluoroacryloyl)-4-(7-(8-methylnaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile Step A: 2-((S)-1-(2-fluoroacryloyl)-4-(7-(8-methylnaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (8 g, 15.63 mmol) was diluted with DMF (78.17 ml, 15.63 mmol), placed under nitrogen and cooled to 0° C. DIEA (6.827 ml, 39.09 mmol) was added followed by the addition of 2-Fluoroacrylic acid (2.112 g, 23.45 mmol) and the dropwise addition of 1-Propanephosphonic acid cyclic anhydride (9.307 ml, 15.63 mmol). The reaction was stirred at 0° C. for 6 hours and left to stir for an additional 10 hours warming to ambient temperature. The reaction was poured into a 5% sodium bicarbonate solution and extracted twice with ethyl acetate. The ethyl acetate was washed with water, brine, dried over MgSO4, filtered and concentrated. The material was purified on silica gel eluting with 1-10% methanol/ DCM (1% NH4OH as additive) to afford title compound 2-((S)-1-(2-fluoroacryloyl)-4-(7-(8-methylnaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile (EXAMPLE 507, 6.6 g, 11.31 mmol, 72.32% yield). ESI+APCI MS m/z 584.3 [M+H]+.

Example 508

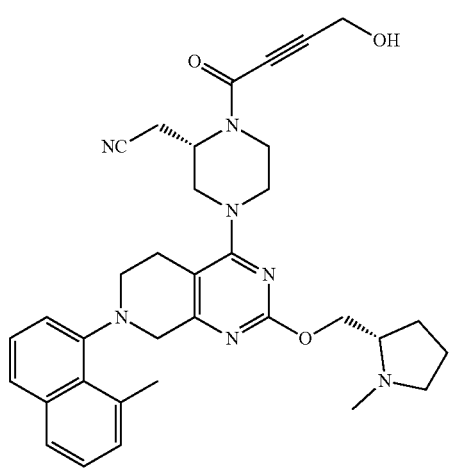 [SMILES: Cc1cccc2cccc(N3CCc4c(nc(OC[C@@H]5CCCN5C)nc4N4CCN(C(=O)C#CCO)[C@@H](CC#N)C4)C3)c12]

2-((S)-1-(4-hydroxybut-2-ynoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-(4-hydroxybut-2-ynoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile was prepared according to Example 458, Step D, substituting 4-((tert-butyldimethylsilyl)oxy)but-2-ynoic acid for but-2-ynoic acid. ESI+APCI MS m/z 594.3 [M+H]+.

Example 509

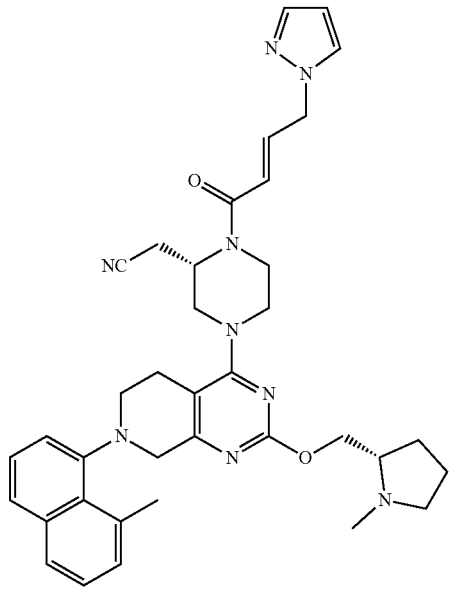 [SMILES: Cc1cccc2cccc(N3CCc4c(nc(OC[C@@H]5CCCN5C)nc4N4CCN(C(=O)/C=C/Cn5cccn5)[C@@H](CC#N)C4)C3)c12]

1337

2-((S)-1-((E)-4-(1H-pyrazol-1-yl)but-2-enoyl)-4-(7-(8-methylnaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile

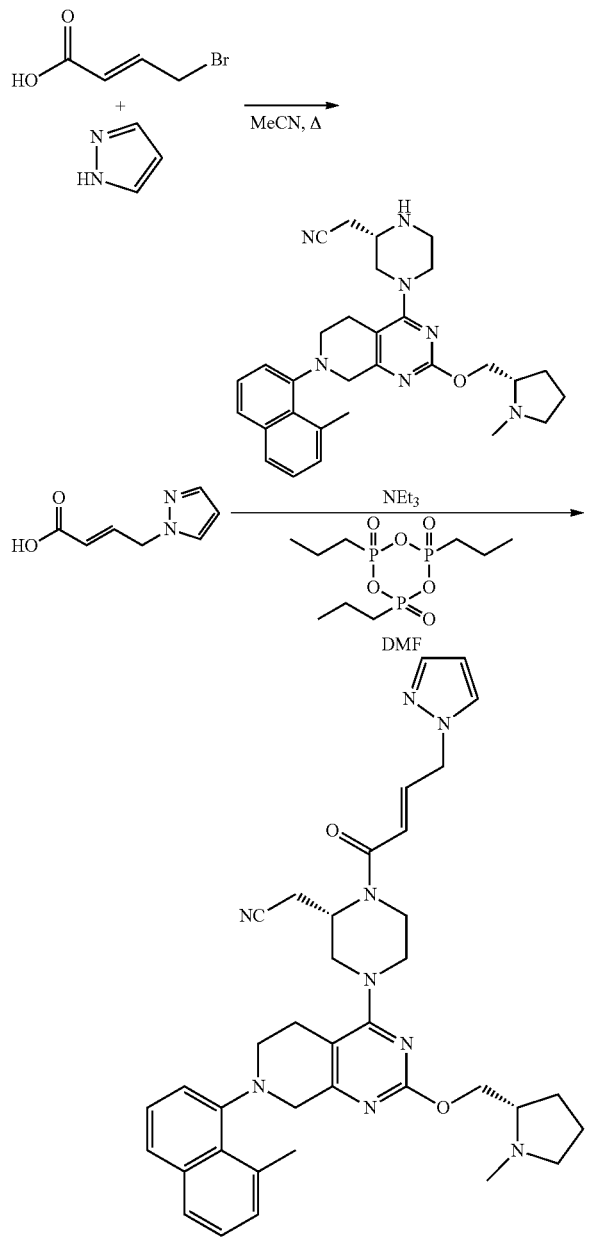

Step A: (E)-4-(1H-pyrazol-1-yl)but-2-enoic acid

A solution of 4-bromocrotonic acid (100 mg, 0.606 mmol) and pyrazole (37.1 mg, 0.546 mmol) in acetonitrile (1 ml, 19.1 mmol) was heated in a closed vial for 48 h to 60° C. with stirring. The resulted light-green solution was divided between water (5 mL) and EtOAc (15 mL), the organics were separated, the organic layer was washed with brine, dried over Na₂SO₄ and evaporated in vacuo. The material was chromatographed on silica gel in 2 to 5% MeOH/DCM+ 0.2% TFA. The resulting solid was dissolved in minimal amount of 6M HCl and evaporated under slow N₂ flow. This material was used in the next step without further purification.

Step B: 2-((S)-1-((E)-4-(1H-pyrazol-1-yl)but-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile A stirred mixture of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (42.37 mg, 0.08281 mmol), (E)-4-(1H-pyrazol-1-yl) but-2-enoic acid (12.6 mg, 0.08281 mmol) and N,N-dimethylformamide (1 mL, 12.79 mmol) was cooled on ice-salt bath with stirring, and triethylamine (0.03463 mL, 0.2484 mmol) was added at once, followed by 2,4,6-tripropyl-1,3,5,2,4,6-trioxatriphosphinane 2,4,6-trioxide, 50% in EtOAc (0.07395 mL, 0.1242 mmol). The reaction mixture was allowed to warm up to r.t. over 5 min and was stirred at r.t. overnight. The reaction mixture was divided between 0.5M Na₂CO₃ (5 mL) and EtOAc (10 mL), the organics were separated, the organic layer was washed with water and brine (5 mL each), dried over Na₂SO₄ and evaporated in vacuo. The product was purified by silicia gel chromatography using 5% MeOH+0.5% NH₄OH in DCM to give title compound as a colorless solid (EXAMPLE 509, 11.46 mg, 23%). ESI+APCI MS m/z 646.3 [M+H]⁺.

Example 510

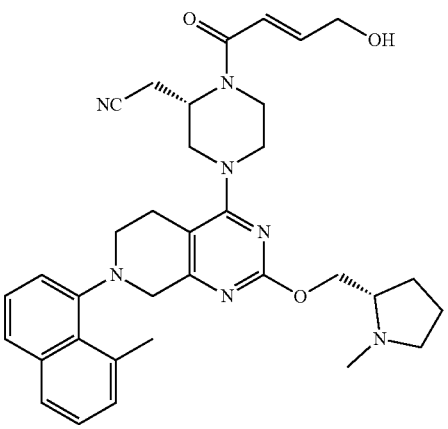 [SMILES: Cc1cccc2cccc(N3CCc4c(nc(OC[C@@H]5CCCN5C)nc4N4CCN(C(=O)/C=C/CO)[C@@H](CC#N)C4)C3)c12]

2-((S)-1-((E)-4-hydroxybut-2-enoyl)-4-(7-(8-methylnaphthalen-1-yl)-2-(((S)-1-methylpyrrolidin-2-yl) methoxy)-5,6,7,8-tetrahydropyrido[3,4-d]pyrimidin-4-yl)piperazin-2-yl)acetonitrile

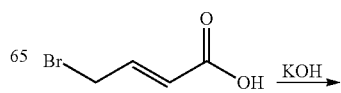

-continued

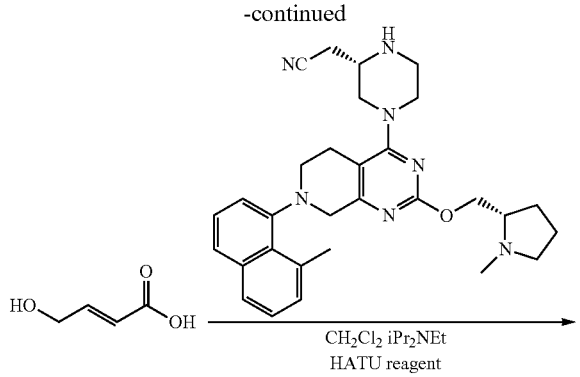

Step A: (E)-4-hydroxybut-2-enoic acid

To a stirred suspension of 4-bromocrotonic acid (4824 mg, 29.24 mmol) in water (48 mL) a 2M solution of potassium hydroxide (4.921 g, 87.72 mmol) was added dropwise and the resulted solution was heated to reflux for 5 min. The reaction mixture was left under a $N_2$ stream to cool and concentrate. The residue was cooled on ice bath, acidified with 4M $H_2SO_4$ to pH 1-2, the resulted suspension was evaporated in vacuo by half and then extracted with EtOAc (3*60 mL). The combined extracts were dried over $Na_2SO_4$ and evaporated in vacuo. The material was purified by chromatography using 2 to 5% MeOH+0.2% TFA to afford the target acid as colorless crystals (2.165 g, 73%).

Step B: 2-((S)-1-((E)-4-hydroxybut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile To a stirred solution of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (100 mg, 0.1954 mmol), (2E)-4-hydroxybut-2-enoic acid (39.90 mg, 0.3909 mmol) and N-ethyl-N-isopropylpropan-2-amine (0.06809 ml, 0.3909 mmol) in DCM (5 mL), O-(7-Azabenzotriazol-1-yl)-N,N,N',N'-Tetramethyluronium hexafluorophosphate (111.5 mg, 0.2932 mmol) was added at once and the reaction mixture was stirred at r.t for 4 h. Water (1 mL) was added, the reaction mixture was stirred for 5 min and divided between EtOAc (10 mL) and sat. $NaHCO_3$ (5 mL). The organic layer was separated, washed with $NaHCO_3$, brine (5 mL each), dried over $K_2CO_3$ and evaporated in vacuo. The residue was chromatographed on silica gel with 5% MeOH+0.5% $NH_4OH$. Title compound as a colorless solid (EXAMPLE 510, 29 mg, 25%). ESI+APCI MS m/z 596.3 $[M+H]^+$.

Example 511

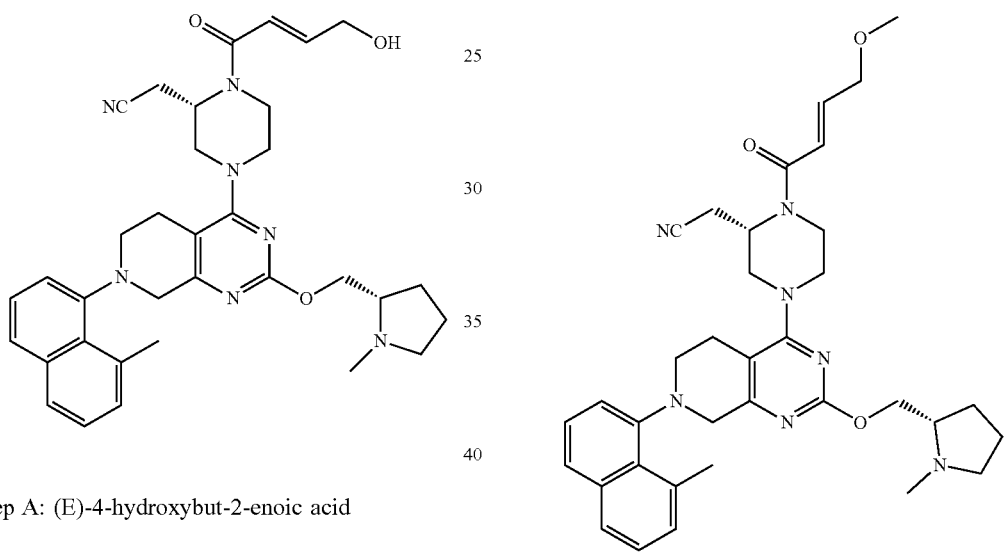

2-((S)-1-((E)-4-methoxybut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

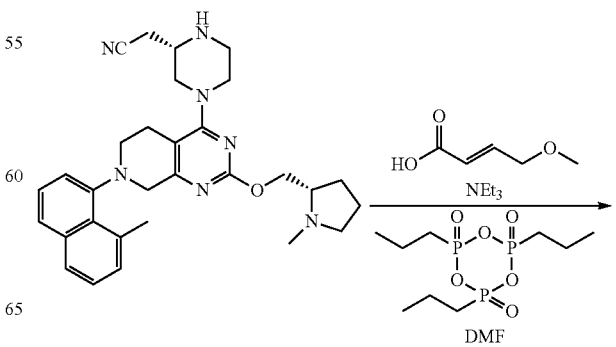

1341
-continued

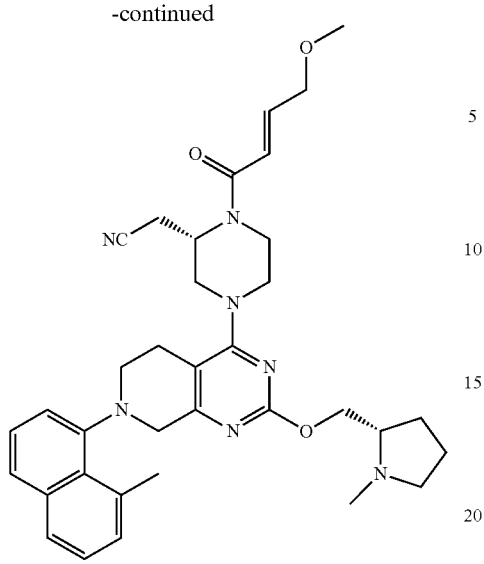

Step A: 2-((S)-1-((E)-4-methoxybut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile A stirred mixture of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (250 mg, 0.4886 mmol), (E)-4-methoxybut-2-enoic acid (85.10 mg, 0.7329 mmol) and N,N-dimethylformamide (2 mL, 25.58 mmol) was cooled on an ice-salt bath and triethylamine (0.2043 mL, 1.466 mmol) was added at once, followed by 2,4,6-tripropyl-1,3,5,2,4,6-trioxatriphosphinane 2,4,6-trioxide, 50% in EtOAc (0.4363 mL, 0.7329 mmol). The reaction mixture was allowed to warm to r.t. over 5 min, and stirred at r.t. for 2 h. The resulted solution was divided between 0.5M $Na_2CO_3$ (10 mL) and EtOAc (30 mL), the organic layer was separated, washed with water and brine (10 mL each), dried over $Na_2SO_4$ and evaporated in vacuo. The material was purified by silica gel chromatography using 5% MeOH+0.5% $NH_4OH$ in DCM. The material was further purified by the reverse phase chromatography, Gilson, 25 to 75% $MeCN/H_2O$+0.1% TFA. Target fractions were basified with excess of 2M $Na_2CO_3$ and extracted with DCM (3*50 mL). The combined organic extracts were washed with brine, dried over $Na_2SO_4$ and evaporated in vacuo. Title compound as a light-yellow solid (EXAMPLE 511, 123 mg, 41%). ESI+APCI MS m/z 610.3 $[M+H]^+$.

1342
Example 512

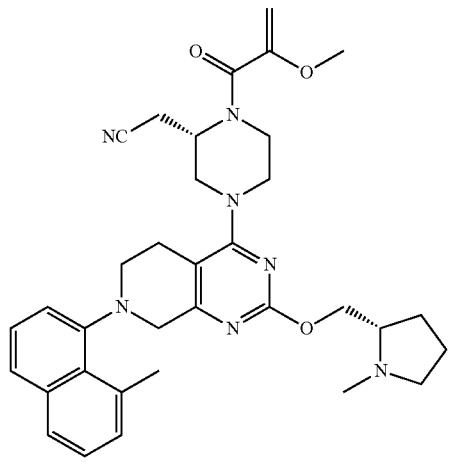 [SMILES: C=C(OC)C(=O)N1CCN(c2nc(OC[C@@H]3CCCN3C)nc3c2CCN(c2cccc4cccc(C)c24)C3)C[C@@H]1CC#N]

2-[(2S)-1-(2-methoxyprop-2-enoyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile

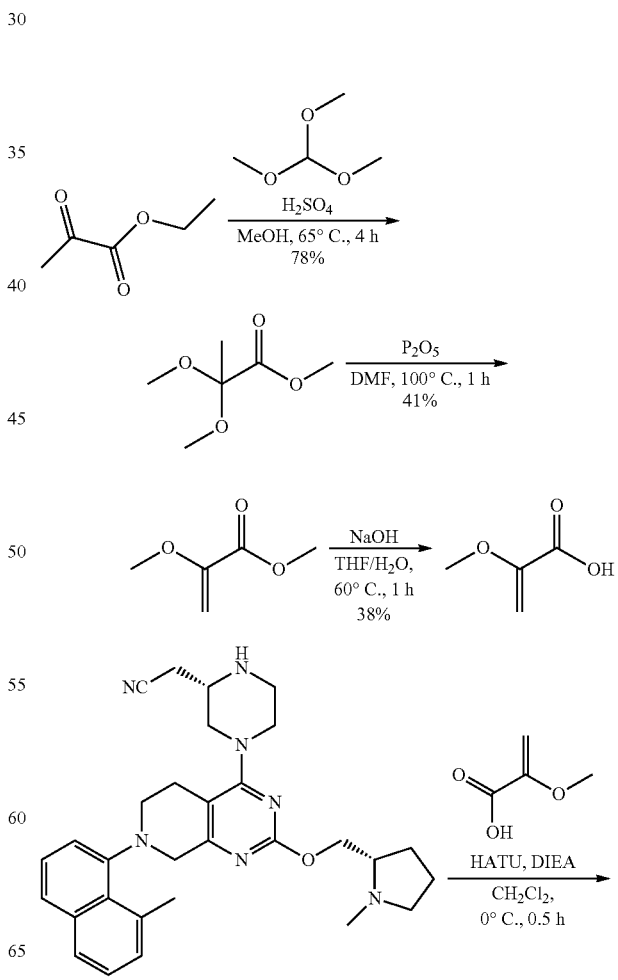

-continued

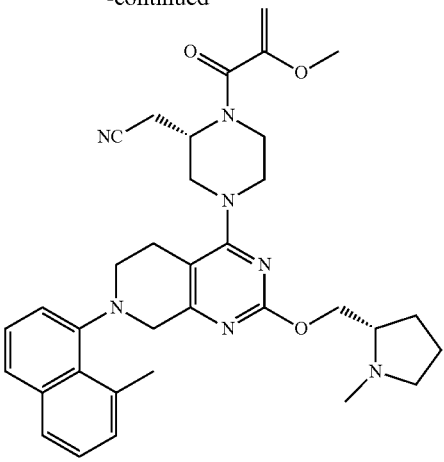

Step A: methyl 2,2-dimethoxypropanoate

To a solution of ethyl 2-oxopropanoate (4.00 g, 34.5 mmol, 3.81 mL, 1.00 eq) and trimethoxymethane (4.75 g, 44.8 mmol, 4.91 mL, 1.30 eq) in methanol (10.0 mL) was added $H_2SO_4$ (33.8 mg, 344 umol, 18.4 uL, 0.01 eq). After stirred at 65° C. for 4 hours, the pH value was adjusted >7 by KOH (120 mg in 20.0 mL water) and extracted with ethyl acetate (3×20.0 mL). The organic layer was washed with brine (1×30.0 mL), dried over $Na_2SO_4$, filtered and concentrated under vacuum. The residue was distilled at 60° C. under oil pump to give methyl 2,2-dimethoxypropanoate (4.00 g, 27.0 mmol, 78% yield) as a colourless oil and used into next step without further purification.

$^1$H NMR (400 MHz, chloroform-d) δ=3.81 (s, 3H), 3.28 (s, 6H), 1.52 (s, 3H).

Step B: methyl 2-methoxyprop-2-enoate

To a solution of methyl 2,2-dimethoxypropanoate (2.00 g, 13.5 mmol, 1.00 eq) in DMF (20.0 mL) was added $P_2O_5$ (1.05 g, 7.42 mmol, 458 uL, 0.55 eq) in portions. After heated to 100° C. for 1 hour, the mixture was diluted with saturated sodium bicarbonate (20.0 mL), extracted with isopropyl ether (3×30.0 mL), washed with brine (3×40.0 mL), dried over $Na_2SO_4$, filtered and concentrated under vacuum. The residue was distilled under oil pump to give methyl 2-methoxyprop-2-enoate (0.65 g, 5.60 mmol, 41% yield) as a colorless oil and used into next step without further purification.

Step C: 2-methoxyprop-2-enoic acid

A mixture of methyl 2-methoxyprop-2-enoate (0.60 g, 5.17 mmol, 1.00 eq) and NaOH (827 mg, 20.7 mmol, 4.00 eq) in $H_2O$ (5.00 mL) and THF (5.00 mL) was stirred at 60° C. for 1 hour. The mixture was adjusted to pH <3 by concentrated HCl (10.0 mL) and extracted with ethyl acetate (3×20.0 mL). The organic layer was dried over $Na_2SO_4$, filtered and concentrated under vacuum to give 2-methoxyprop-2-enoic acid (0.40 g, 1.96 mmol, 38% yield, 50% purity) as a pink oil and used into next step without further purification.

$^1$H NMR (400 MHz, chloroform-d) δ=8.63 (br s, 1H), 5.52 (d, J=2.8 Hz, 1H), 4.75 (d, J=2.8 Hz, 1H), 3.70 (s, 3H).

Step D: 2-[(2S)-1-(2-methoxyprop-2-enoyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (0.14 g, 274 umol, 1.00 eq), 2-methoxyprop-2-enoic acid (112 mg, 1.09 mmol, 4.00 eq) and DIEA (141 mg, 1.09 mmol, 191 uL, 4.00 eq) in dichloromethane (5.00 mL) was added HATU (208 mg, 547 umol, 2.00 eq) at 0° C. After stirred at 0° C. for 0.5 h, the mixture was diluted with water (3.00 mL). The organic layer was dried over $Na_2SO_4$, filtered and concentrated under vacuum. The residue was purified by reverse phase flash [water (FA, 0.10%)/acetonitrile] and prep-HPLC (column: Gemini 150*25 5 u; mobile phase: [water (0.05% ammonia hydroxide v/v)-ACN]; B %: 60%-90%, 12 min). The desired fraction was collected and lyophilized to give title compound 2-[(2S)-1-(2-methoxyprop-2-enoyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (EXAMPLE 512, 10.27 mg, 17.22 umol, 6.3% yield, 99.9% purity) as a off-white solid. LCMS [ESI, M+1]: 596.

SFC condition: "IC-3S_3_40_3ML Column: Chiralpak IC-3 100×4.6 mm I.D., 3 um, Mobile phase: 40% methanol (0.05% DEA) in $CO_2$, Flow rate: 3 mL/min, Wavelength: 220 nm".

$^1$H NMR (400 MHz, chloroform-d) δ=7.72-7.61 (m, 2H), 7.45-7.31 (m, 2H), 7.27-7.17 (m, 2H), 5.05-4.61 (m, 1H), 4.48 (br s, 1H), 4.37 (td, J=4.4, 10.0 Hz, 1H), 4.30-3.98 (m, 4H), 3.96-3.74 (m, 2H), 3.69 (br s, 3H), 3.59-3.28 (m, 2H), 3.27-2.93 (m, 6H), 2.92 (s, 3H), 2.88-2.51 (m, 4H), 2.47 (d, J=3.2 Hz, 3H), 2.33-2.23 (m, 1H), 2.11-1.98 (m, 1H), 1.89-1.74 (m, 3H).

Example 513

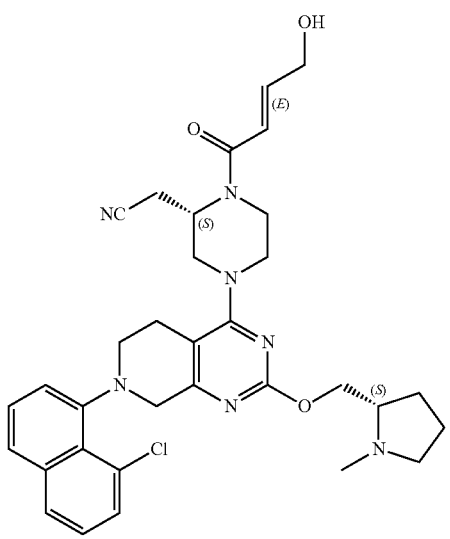

1345

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-hydroxybut-2-enoyl]piperazin-2-yl]acetonitrile

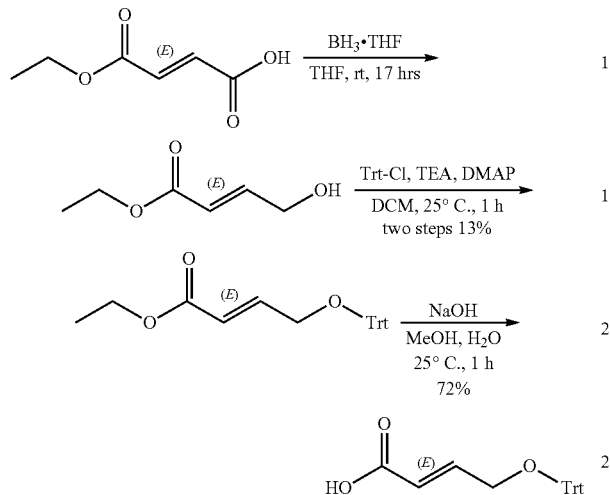

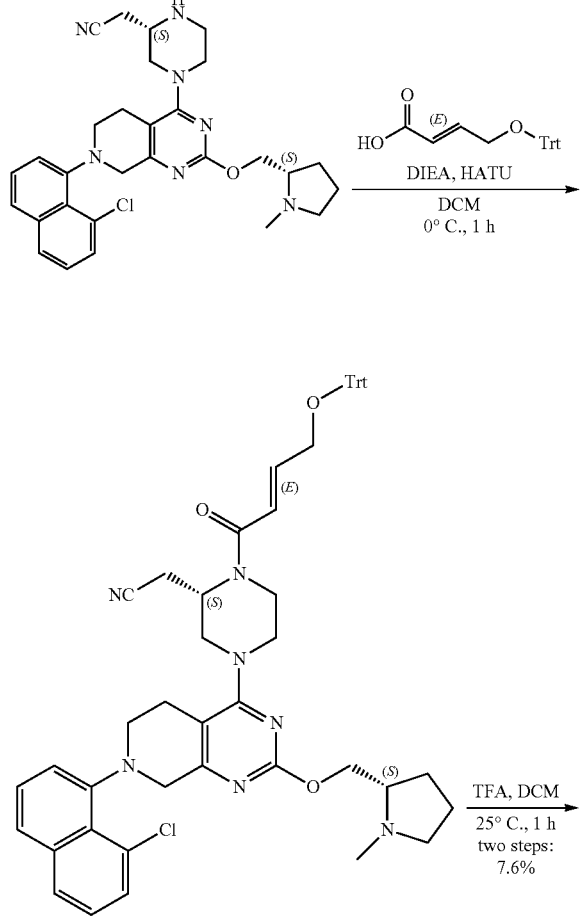

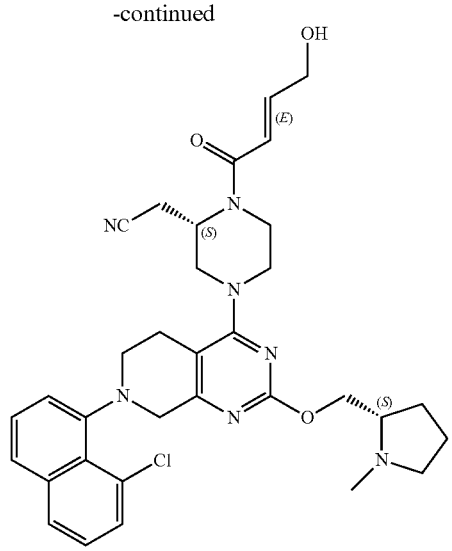

Step 1: ethyl (E)-4-hydroxybut-2-enoate

To a solution of (E)-4-ethoxy-4-oxo-but-2-enoic acid (1.0 g, 7.29 mmol, 1.0 eq) in THF (6.0 mL) was added a solution of BH$_3$-Me$_2$S (10.0 M, 692 uL, 0.95 eq) in THF (8.0 mL) dropwise over 1 hour at −10° C. The reaction mixture was gradually warmed to 25° C. and stirred for 17 hours. After completion, the reaction mixture was quenched by addition water (30.0 mL) and extracted with Ethyl acetate (30.0 mL×3). The combined organic layers were washed with brine (30.0 mL×2), dried over Na$_2$SO$_4$, filtered and concentrated under reduced pressure to give a residue. Compound ethyl (E)-4-hydroxybut-2-enoate (900 mg, crude) was obtained as colorless oil. The crude product was used directly in the next step without further purification.

Step 2: (E)-4-trityloxybut-2-enoate

A mixture of ethyl (E)-4-hydroxybut-2-enoate (900 mg, crude), [chloro(diphenyl)methyl]benzene (2.89 g, 10.4 mmol), DMAP (84.5 mg, 692 umol), TEA (1.4 g, 13.8 mmol, 1.9 mL) in DCM (5.0 mL) was degassed and purged with N$_2$ for 3 times, and then the mixture was stirred at 25° C. for 1 hour under N$_2$ atmosphere. After completion, the reaction mixture was quenched by addition H$_2$O (10.0 mL) and extracted with Ethyl acetate (10.0 mL×3). The combined organic layers were dried over Na$_2$SO$_4$, filtered and concentrated under reduced pressure to give a residue. The residue was purified by column chromatography (SiO$_2$, Petroleum ether/Ethyl acetate=20:1 to 15:1). Compound ethyl (E)-4-trityloxybut-2-enoate (340 mg, 913 umol, 13% yield) was obtained as colorless oil.

$^1$H NMR (400 MHz, Chloroform-d) δ 7.38-7.35 (m, 6H), 7.26-7.22 (m, 6H), 7.18-7.15 (m, 3H), 6.88 (dt, J=15.6, 3.6 Hz, 1H), 6.29 (dt, J=15.6, 2.2 Hz, 1H), 4.16 (q, J=7.1 Hz, 2H), 3.72 (dd, J=2.4, 2.0 Hz, 2H), 1.25 (t, J=7.0 Hz, 3H).

Step 3: (E)-4-trityloxybut-2-enoic acid

To a solution of ethyl (E)-4-trityloxybut-2-enoate (170 mg, 456 umol, 1.0 eq) in MeOH (1.0 mL) was added solution of NaOH (54.5 mg, 1.37 mmol, 3.0 eq) in H$_2$O (0.5 mL) and then the mixture was stirred at 40° C. for 1 hour under N$_2$ atmosphere. After completion, the reaction mixture was quenched by addition 1M HCl at 0° C. until pH=5, and then extracted with Ethyl acetate (8.0 mL×3). The combined organic layers were dried over $Na_2SO_4$, filtered and concentrated under reduced pressure to give a residue. The residue was purified by column chromatography ($SiO_2$, Petroleum ether/Ethyl acetate=3:1 to 1:1). Compound (E)-4-trityloxybut-2-enoic acid (113 mg, 328 umol, 72% yield) was obtained as a white solid.

$^1$H NMR (400 MHz, Chloroform-d) δ 7.38-7.36 (m, 6H), 7.26-7.24 (m, 5H), 7.20-7.16 (m, 4H), 7.0 (dt, J=15.6, 3.6 Hz, 1H), 6.32 (dt, J=15.6, 2.0 Hz, 1H), 3.76 (dd, J=3.2, 2.4 Hz, 2H).

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 60.0 mg, 113 umol, 1.0 eq), (E)-4-trityloxybut-2-enoic acid (77.8 mg, 226 umol, 2.0 eq) and DIEA (73.0 mg, 564 umol, 98 uL, 5.0 eq) in DCM (2.0 mL) was added HATU (64 mg, 169 umol, 1.5 eq) in one portion at 0° C. under $N_2$. The mixture was stirred at 25° C. for 1 hour. After completion, the reaction mixture was quenched by addition $H_2O$ (8.0 mL) and then extracted with Ethyl acetate (10.0 mL×3). The combined organic layers were dried over $Na_2SO_4$, filtered and concentrated under reduced pressure to give a residue. Compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile (150 mg, crude) was obtained as a yellow solid, and the crude product was used directly in the next step without further purification. LCMS [ESI, M+1]: 858.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-hydroxybut-2-enoyl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile (150 mg, crude) in DCM (1.0 mL) was added TFA (1.0 ml, 13.5 mmol). The mixture was stirred at 25° C. for 1 hour. After completion, the reaction mixture was quenched by addition $NaHCO_3$ aqueous solution at 0° C. until pH=8, and then extracted with Ethyl acetate (10.0 mL×3). The combined organic layers were dried over $Na_2SO_4$, filtered and concentrated under reduced pressure to give a residue. The residue was purified by prep-HPLC (column: Phenomenex Gemini 150*25 mm*10 um; mobile phase: [water (0.04% $NH_3H_2O$+10 mM $NH_4HCO_3$)-ACN]; B %: 48%-72%, 10 min.) and lyophilization. Title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-hydroxybut-2-enoyl]piperazin-2-yl]acetonitrile (EXAMPLE 513, 8.21 mg, 13.3 umol, 7.6% yield, 99.8% purity) was obtained as a white solid. LCMS [ESI, M+1]: 616.

SFC condition: 100% e.e.

$^1$H NMR (400 MHz, Chloroform-d) δ 7.68 (d, J=8.0 Hz, 1H), 7.70-7.33 (m, 1H), 7.49 (dd, J=6.8, 0.8 Hz, 1H), 7.37 (dt, J=11.98, 7.82 Hz, 1H), 7.26 (t, J=11.8 Hz, 1H), 7.19-7.11 (m, 1H), 6.99 (dt, J=14.8, 3.4 Hz, 1H), 6.56 (br s, 1H), 5.02-4.57 (m, 1H), 4.39-4.29 (m, 4H), 4.12-4.06 (m, 1H), 4.03-3.99 (m, 2H), 3.85-3.72 (m, 2H), 3.67-3.36 (m, 3H), 3.24-3.09 (m, 2H), 3.03-2.89 (m, 3H), 2.73 (br s, 1H), 2.63-2.61 (m, 1H), 2.50 (br s, 1H), 2.41 (s, 3H), 2.25-2.19 (m, 1H), 2.03-1.92 (m, 1H), 1.70-1.60 (m, 3H).

Example 514

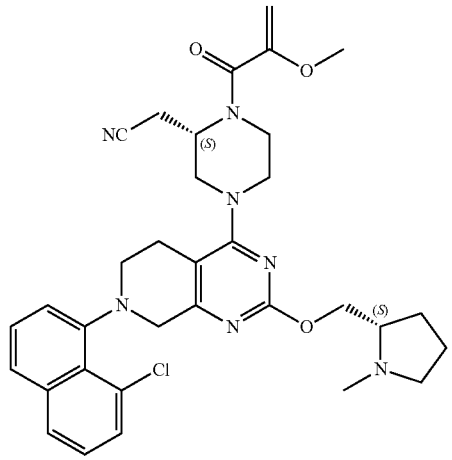

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-methoxyprop-2-enoyl)piperazin-2-yl] acetonitrile

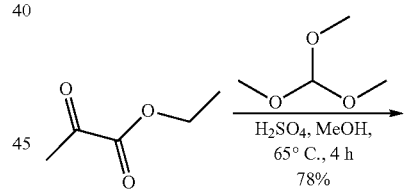

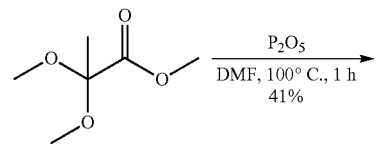

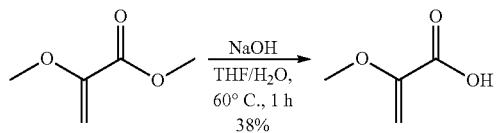

-continued

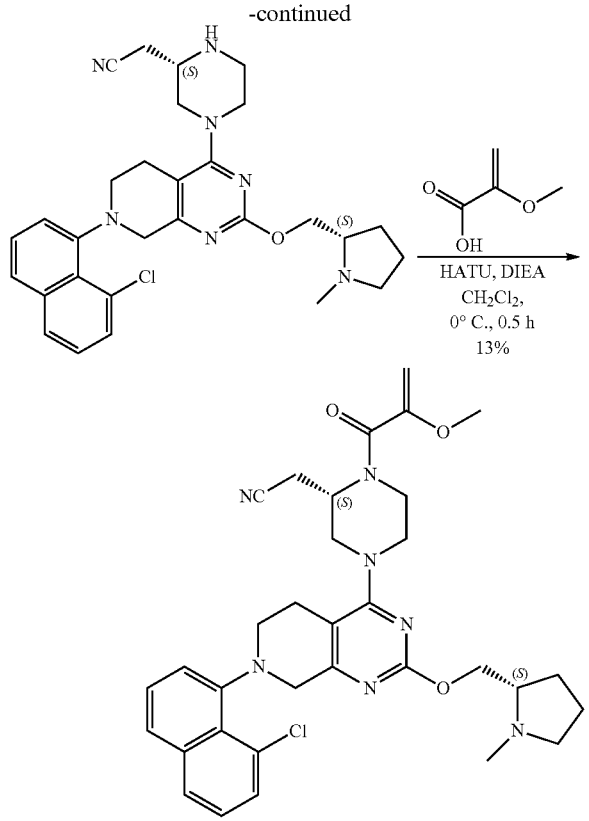

Step 1: methyl 2,2-dimethoxypropanoate

To a solution of ethyl 2-oxopropanoate (4.00 g, 34.5 mmol, 3.81 mL, 1.00 eq) and trimethoxymethane (4.75 g, 44.8 mmol, 4.91 mL, 1.30 eq) in methanol (10.0 mL) was added $H_2SO_4$ (33.8 mg, 344 umol, 18.4 uL, 0.01 eq). After stirring at 65° C. for 4 hours, the reaction mixture was adjusted to pH value was adjusted >7 by KOH aqueous (120 mg in 20.0 mL water) and extracted with ethyl acetate (3×20.0 mL). The organic layers were washed with brine (1×30.0 mL), dried over $Na_2SO_4$, filtered and concentrated under vacuum. The residue was distilled at 60° C. under vacuum to give methyl 2,2-dimethoxypropanoate (4.00 g, 27.0 mmol, 78% yield) as a colorless oil.

$^1$H NMR (400 MHz, chloroform-d) δ=3.81 (s, 3H), 3.28 (s, 6H), 1.52 (s, 3H).

Step 2: methyl 2-methoxyprop-2-enoate

To a solution of methyl 2,2-dimethoxypropanoate (2.00 g, 13.5 mmol, 1.00 eq) in DMF (20.0 mL) was added $P_2O_5$ (1.05 g, 7.42 mmol, 458 uL, 0.55 eq) in portions. After stirring at 100° C. for 1 hour, the mixture was diluted with saturated sodium bicarbonate (20.0 mL), extracted with isopropyl ether (3×30.0 mL). The extracts were washed with brine (3×40.0 mL), dried over $Na_2SO_4$, filtered and concentrated under vacuum. The residue was distilled under vacuum to give methyl 2-methoxyprop-2-enoate (0.65 g, 5.60 mmol, 41% yield) as a colorless oil which was used to next step without further purification.

$^1$H NMR (400 MHz, chloroform-d) δ=5.36 (d, J=2.8 Hz, 1H), 4.63 (d, J=2.8 Hz, 1H), 3.81 (s, 3H), 3.66 (s, 3H).

Step 3: 2-methoxyprop-2-enoic acid

A mixture of methyl 2-methoxyprop-2-enoate (0.60 g, 5.17 mmol, 1.00 eq) and NaOH (827 mg, 20.7 mmol, 4.00 eq) in $H_2O$ (5.00 mL) and THF (5.00 mL) was stirred at 60° C. for 1 hour. The mixture was adjusted to pH <3 by concentrated HCl (10.0 mL) and extracted with ethyl acetate (3×20.0 mL). The organic layer was dried over $Na_2SO_4$, filtered and concentrated under vacuum to give 2-methoxyprop-2-enoic acid (0.40 g, 1.96 mmol, 38% yield, 50% purity) as a pink oil and used into next step without further purification.

$^1$H NMR (400 MHz, chloroform-d) δ=8.63 (br s, 1H), 5.52 (d, J=2.8 Hz, 1H), 4.75 (d, J=2.8 Hz, 1H), 3.70 (s, 3H).

Step A: 2-[(2S)-4-[7-(8-chloro-1-naphthyl)-2-[[(2S)-1-methyl pyrrolidin-2-yl]methoxy]-6,8-dihydro-5H-pyrido[3,4-d]pyrimidin-4-yl]-1-(2-methoxyprop-2-enoyl)piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (0.20 g, 376 umol, 1.00 eq), 2-methoxyprop-2-enoic acid (153 mg, 1.50 mmol, 4.00 eq) and DIEA (194 mg, 1.50 mmol, 262 uL, 4.00 eq) in dichloromethane (5.00 mL) was added HATU (286 mg, 752 umol, 2.00 eq) at 0° C. After stirred at 0° C. for 0.5 h, the reaction was purified by reversed phase flash [water (FA, 0.1%)/acetonitrile], prep-HPLC (column: Luna C18 150*25 5 u; mobile phase: [water (0.225% FA)-ACN]; B %: 25%-45%, 7.8 min) and further prep-HPLC (column: Waters Xbridge 150*25 5 u; mobile phase: [water (0.05% ammonia hydroxide v/v)-ACN]; B %: 55%-79%, 10 min). The desired fractions were collected and lyophilized to give title compound 2-[(2S)-4-[7-(8-chloro-1-naphthyl)-2-[[(2S)-1-methyl pyrrolidin-2-yl]methoxy]-6,8-dihydro-5H-pyrido[3,4-d]pyrimidin-4-yl]-1-(2-methoxyprop-2-enoyl)piperazin-2-yl]acetonitrile (EXAMPLE 514, 30.1 mg, 48.9 umol, 13% yield, 100% purity) as a yellow solid. LCMS [ESI, M+1]: 616.

SFC condition: "AS-3_MeOH (DEA)_5_40_3 mL-35T Column: Chiralpak AS-3 50×4.6 mm I.D., 3 um, Mobile phase: methanol (0.05% DEA) in $CO_2$ from 5% to 40%, Flow rate: 3 mL/min, Wavelength: 220 nm".

$^1$H NMR (400 MHz, chloroform-d) δ=7.76 (br d, J=8.0 Hz, 1H), 7.62 (t, J=7.6 Hz, 1H), 7.52 (d, J=7.2 Hz, 1H), 7.44 (td, J=7.6, 13.6 Hz, 1H), 7.34 (t, J=8.0 Hz, 1H), 7.27-7.18 (m, 1H), 5.07-4.63 (m, 1H), 4.57-4.29 (m, 4H), 4.21-3.96 (m, 3H), 3.95-3.77 (m, 2H), 3.69 (br s, 3H), 3.59 (br d, J=11.2 Hz, 1H), 3.51-3.32 (m, 1H), 3.30-3.02 (m, 5H), 2.89-2.50 (m, 4H), 2.47 (d, J=2.0 Hz, 3H), 2.32-2.23 (m, 1H), 2.11-2.00 (m, 1H), 1.89-1.72 (m, 3H).

Example 515

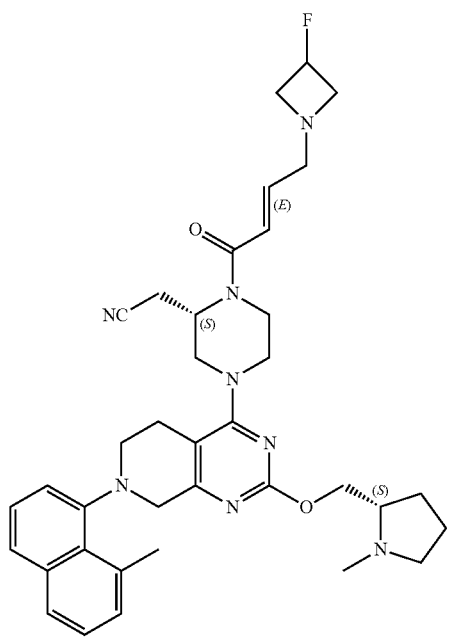

2-[(2S)-1-[(E)-4-(3-fluoroazetidin-1-yl)but-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile

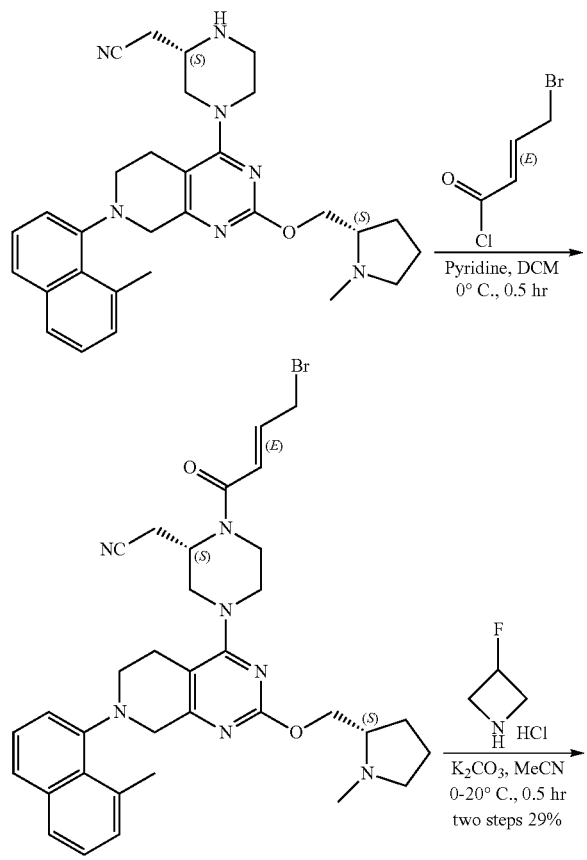

Step A: 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile

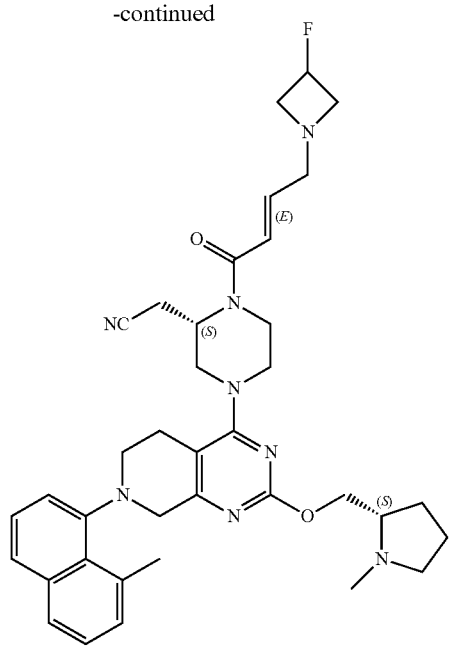

To a solution of 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 293 umol, 1.0 eq) and pyridine (186 mg, 2.35 mmol, 189 uL, 8.0 eq) in dichloromethane (4.0 mL) was added (E)-4-bromobut-2-enoyl chloride (215 mg, 1.17 mmol, 4.0 eq). The mixture was stirred at 0° C. for 0.5 hour. After completion, the reaction mixture was concentrated to give the product 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, crude) as yellow oil. The product was used for the next step without further purification. LCMS [ESI, M+1]: 658.

Step B: 2-[(2S)-1-[(E)-4-(3-fluoroazetidin-1-yl)but-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 228 umol, 1.0 eq) and $K_2CO_3$ (315 mg, 2.28 mmol, 10.0 eq) in acetonitrile (2.0 mL) was added 3-fluoroazetidine (152 mg, 1.37 mmol, 6.0 eq, HCl). The mixture was stirred at 0° C. for 0.5 hour. After completion, the reaction mixture was added water (5.0 mL) and extracted with ethyl acetate (5.0 mL×4). The organic layer was dried over $Na_2SO_4$, filtered and concentrated under vacuum. The residue was purified by prep-HPLC (column: Gemini 150*25 5 u; mobile phase: [water (0.05% ammonia hydroxide v/v)-ACN]; B %: 60%-90%,12 min) to give the title compound 2-[(2S)-1-[(E)-4-(3-fluoroazetidin- 1-yl)but-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (EXAMPLE 515, 45.0 mg, 66 umol, 29% yield, 96% purity) as white solid. LCMS [ESI, M+1]: 653.

¹H NMR (400 MHz, Chloroform-d) δ 7.70 (br d, J=8.0 Hz, 1H), 7.65 (t, J=8.4 Hz, 1H), 7.41 (dd, J=7.6, 15.2 Hz, 1H), 7.34 (t, J=7.6 Hz, 1H), 7.27-7.18 (m, 2H), 6.92-6.82 (m, 1H), 6.52-6.31 (m, 1H), 5.28-5.08 (m, 1H), 5.07-4.46 (m, 1H), 4.41-4.33 (m, 1H), 4.32-4.01 (m, 4H), 4.01-3.79 (m, 2H), 3.79-3.56 (m, 3H), 3.55-3.37 (m, 2H), 3.36-3.31 (m, 2H), 3.30-3.24 (m, 1H), 3.23-3.18 (m, 2H), 3.17-3.15 (m, 1H), 3.14-3.06 (m, 2H), 3.05-2.95 (m, 1H), 2.92 (s, 3H), 2.86-2.75 (m, 1H), 2.71-2.57 (m, 2H), 2.47 (d, J=4.0 Hz, 3H), 2.33-2.22 (m, 1H), 2.11-1.99 (m, 1H), 1.88-1.67 (m, 3H).

Example 516

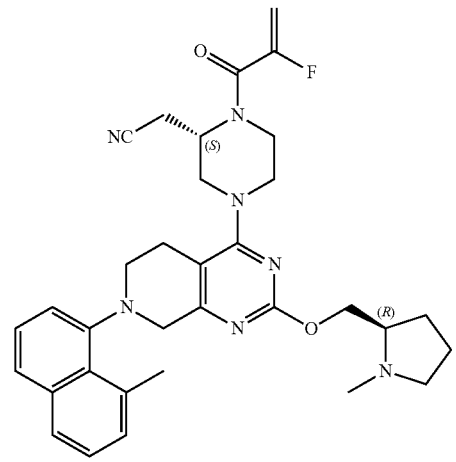

2-((S)-1-(2-fluoroacryloyl)-4-(7-(8-methylnaphthalen-1-yl)-2-(((R)-1-methylpyrrolidin-2-yl)methoxy)-5,6,7,8-tetrahydropyrido[3,4-d] pyrimidin-4-yl)piperazin-2-yl)acetonitrile

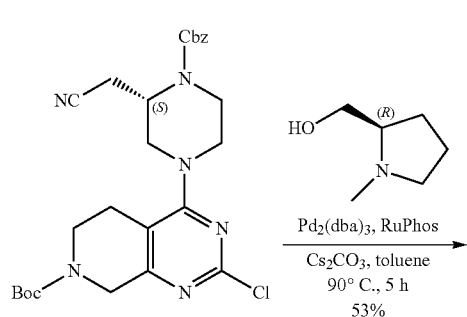

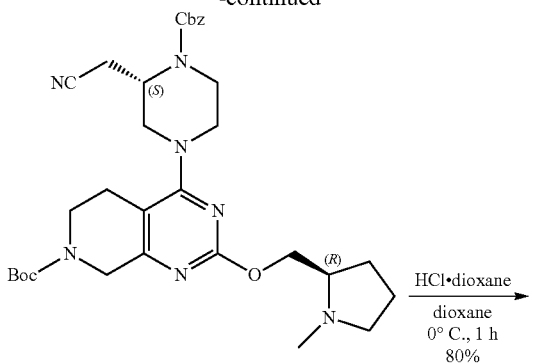

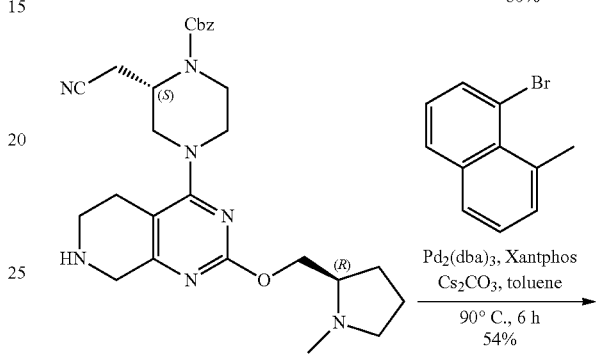

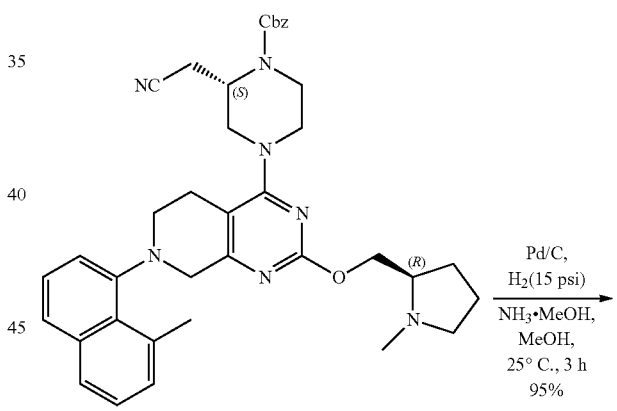

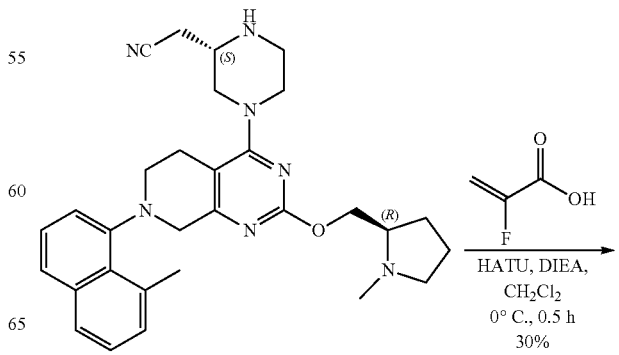

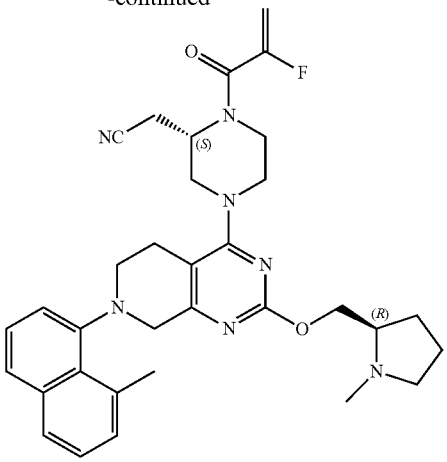

Step A: tert-Butyl 4-[(3S)-4-benzyloxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate A mixture of tert-butyl 4-[(3S)-4-benzyloxycarbonyl-3-(cyanomethyl)piperazin-1-yl]-2-chloro-6,8-dihydro-5H-pyrido[3,4-d]pyrimidine-7-carboxylate (5.5 g, 10.4 mmol, 1 eq), [(2R)-1-methylpyrrolidin-2-yl]methanol (2.40 g, 20.9 mmol, 2.25 mL, 2 eq), Pd$_2$(dba)$_3$ (1.91 g, 2.09 mmol, 0.2 eq), RuPhos (1.95 g, 4.17 mmol, 0.4 eq) and Cs$_2$CO$_3$ (8.50 g, 26.1 mmol, 2.5 eq) in toluene (100 mL) was degassed and purged with N$_2$ for 3 times, and then the mixture was stirred at 90° C. for 5 hours under N$_2$ atmosphere. The reaction mixture was concentrated under reduced pressure to give a residue. The residue was diluted with ethyl acetate (100 mL) and water (50 mL). Then the mixture was acidified to PH ~4 with 1 M HCl aqueous solution. The water phase was separated and basified to PH ~8 with saturated Na$_2$CO$_3$ aqueous solution, then the mixture was extracted with ethyl acetate (50 mL×2). The combined organic layers were washed with brine (30 mL), dried over Na$_2$SO$_4$, filtered and concentrated under reduced pressure. tert-Butyl 4-[(3S)-4-benzyloxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (4 g, 5.55 mmol, 53% yield, 84% purity) was obtained as a yellow solid and used to next step without purification.

$^1$H NMR (400 MHz, chloroform-d) δ=7.46-7.31 (m, 5H), 5.23 (s, 2H), 4.74-4.49 (m, 2H), 4.43-4.27 (m, 2H), 4.21-3.70 (m, 5H), 3.42-3.17 (m, 3H), 3.09 (t, J=7.6 Hz, 1H), 2.98 (td, J=3.6, 12.4 Hz, 1H), 2.86-2.74 (m, 1H), 2.74-2.54 (m, 4H), 2.47 (s, 3H), 2.35-2.21 (m, 1H), 2.05-1.97 (m, 1H), 1.90-1.74 (m, 3H), 1.49 (s, 9H).

Step B: benzyl (2S)-2-(cyanomethyl)-4-[2-[[(2R)-1-methylpyrrolidin-2-yl]methoxy]-5,6,7,8-tetrahydro-pyrido[3,4-d]pyrimidin-4-yl]piperazine-1-carboxylate To a solution of tert-butyl 4-[(3S)-4-benzyloxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (3.7 g, 6.11 mmol, 1 eq) in dioxane (20 mL) was added HCl/dioxane (4 M, 22.9 mL, 15 eq). The mixture was stirred at 0° C. for 1 hour. The liquid was decanted and the solid was collected. The solid residue was diluted with water (50 mL) and dichloromethane (100 mL), then the mixture was basified to pH ~8 with saturated Na$_2$CO$_3$ aqueous solution and extracted with dichloromethane (100 mL×3). The combined organic layers were washed with brine (50 m L), dried over Na$_2$SO$_4$, filtered and concentrated under reduced pressure. Benzyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (2.6 g, 4.89 mmol, 80% yield, 95% purity) was obtained as a yellow solid and used next step without purification. LCMS [ESI, M+1]: 506.

Step C: benzyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate A mixture of benzyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (2.3 g, 4.55 mmol, 1 eq), 1-bromo-8-methyl-naphthalene (Intermediate 69, 1.31 g, 5.91 mmol, 1.3 eq), Cs$_2$CO$_3$ (3.71 g, 11.4 mmol, 2.5 eq), Pd$_2$(dba)$_3$ (833 mg, 909 umol, 0.2 eq) and Xantphos (1.05 g, 1.82 mmol, 0.4 eq) in toluene (50 mL) was degassed and purged with N$_2$ for 3 times, and then the mixture was stirred at 90° C. for 6 hours under N$_2$ atmosphere. The reaction mixture was diluted with water (100 mL) and extracted with ethyl acetate (200 mL×3). The combined organic layers were washed with brine (100 mL), dried over Na$_2$SO$_4$, filtered and concentrated under reduced pressure to give a residue. The residue was purified by column chromatography (SiO$_2$, Ethyl acetate/Methanol=100/1 to 10/1). Benzyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (1.6 g, 2.48 mmol, 54% yield) was obtained as a yellow solid.

Step D: 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile A mixture of benzyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (1.60 g, 2.48 mmol, 1.00 eq) in MeOH (20.0 mL) and NH$_3$ (20% w/w in MeOH, 7 mL) was hydrogenated with Pd/C (100 mg, 2.48 mmol, 10% purity, 1.00 eq) as a catalyst under H$_2$ (4.99 mg, 2.48 mmol, 1.00 eq, 15 psi) at 25° C. for 3 hours. The catalyst was filtered off through a pad of celite and the filtrate was concentrated under vacuum. The crude product was used to next step directly without further purification. 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (1.20 g, 2.35 mmol, 95% yield) was obtained as a light yellow solid. LCMS [ESI, M+1]: 512.

Step E: 2-[(2S)-1-(2-fluoroprop-2-enoyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a mixture of 2-[(2S)-4-[7-(8-methyl-1-naphthyl)-2-[[(2R)-1-methylpyrrolidin-2-yl]methoxy]-6,8-dihydro-5H- pyrido[3,4-d]pyrimidin-4-yl]piperazin-2-yl]acetonitrile (140 mg, 274 umol, 1.00 eq) and 2-fluoroprop-2-enoic acid (73.9 mg, 821 umol, 3.00 eq) in dichloromethane (3.00 mL) was added DIEA (212 mg, 1.64 mmol, 286 uL, 6.00 eq), HATU (312 mg, 821 umol, 3.00 eq) in one portion at 0° C. under N$_2$. After stirring at 0° C. for 30 min, the reaction mixture was diluted with water (10.0 mL) and extracted with dichloromethane (2×10.0 mL). The combined organic layers were washed with water (1×10.0 mL), dried over sodium sulfate, filtered and concentrated under reduced pressure to give a residue. The residue was purified by prep-HPLC (column: Phenomenex Gemini 150*25 mm*10 um; mobile phase: [water (0.04% NH$_3$H$_2$O+10 mM NH$_4$HCO$_3$)-ACN]; B %: 55%-85%, 10 min). Title compound 2-[(2S)-1-(2-fluoroprop-2-enoyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (EXAMPLE 516, 48.7 mg, 82.1 umol, 30% yield, 98.4% purity) was obtained as a white solid.

SFC condition: "Column: Chiralcel OJ-3 50×4.6 mm I.D., 3 um, Mobile phase: methanol (0.05% DEA) in CO$_2$ from 5% to 40%, Flow rate: 3 mL/min, Wavelength: 220 nm".

$^1$H NMR (400 MHz, chloroform-d) δ=7.73-7.62 (m, 2H), 7.45-7.31 (m, 2H), 7.27-7.17 (m, 2H), 5.53-5.34 (m, 1H), 5.26 (dd, J=3.6, 17.2 Hz, 1H), 4.88 (br s, 1H), 4.41-4.32 (m, 1H), 4.31-4.22 (m, 1H), 4.21-4.10 (m, 2H), 4.10-4.02 (m, 1H), 3.89 (br d, J=18.0 Hz, 1H), 3.78 (d, J=18.4 Hz, 1H), 3.59-3.40 (m, 2H), 3.27-3.15 (m, 2H), 3.14-3.04 (m, 2H), 3.03-2.90 (m, 4H), 2.90-2.73 (m, 2H), 2.72-2.56 (m, 2H), 2.47 (d, J=4.8 Hz, 3H), 2.33-2.23 (m, 1H), 2.11-1.98 (m, 1H), 1.90-1.74 (m, 3H).

Example 517

2-((S)-1-((E)-4-hydroxybut-2-enoyl)-4-(7-(8-methyl-naphthalen-1-yl)-2-(((R)-1-methylpyrrolidin-2-yl)methoxy)-5,6,7,8-tetrahydropyrido[3,4-d]pyrimidin-4-yl)piperazin-2-yl)acetonitrile

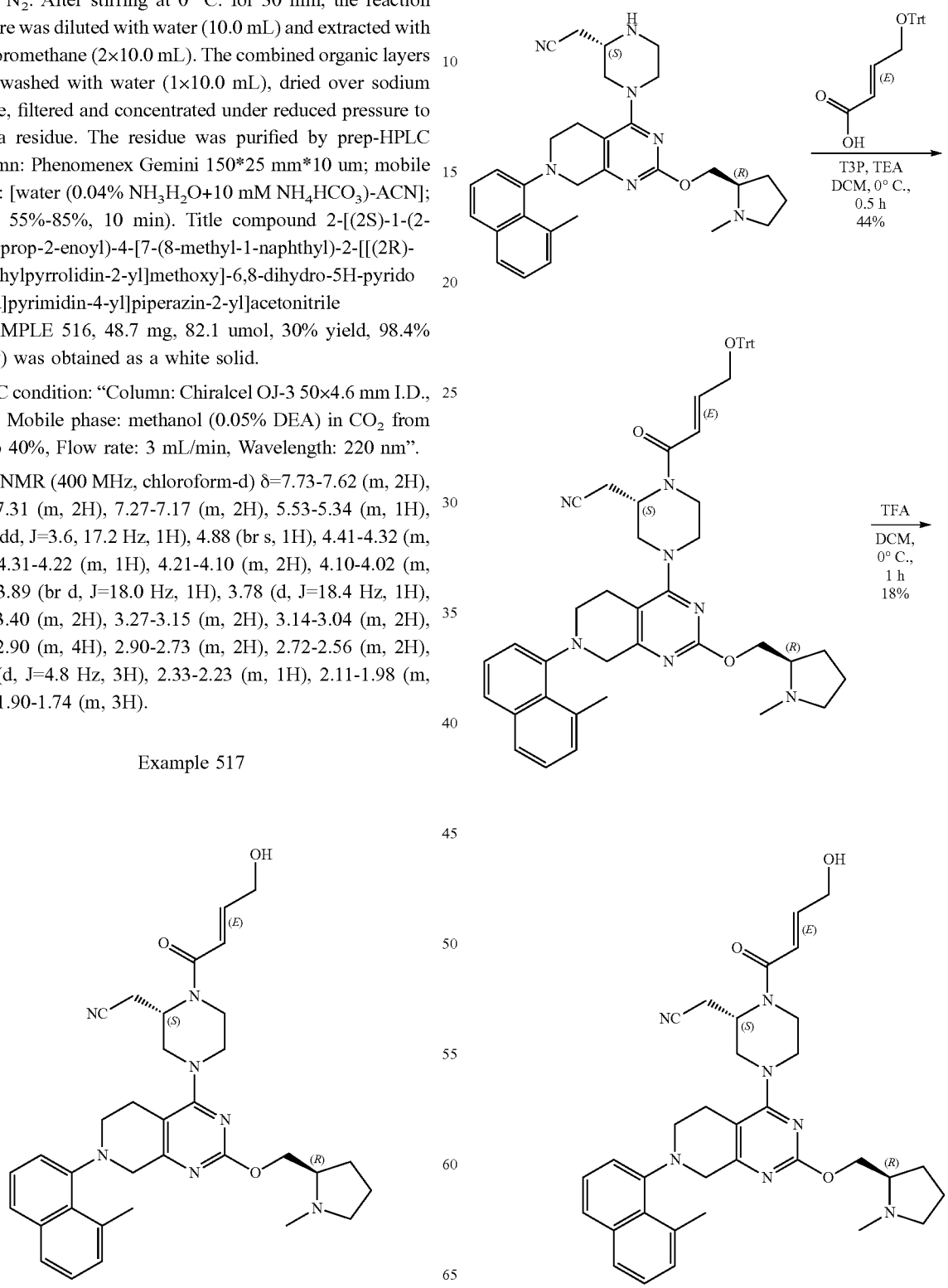

Step A: 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (120 mg, 234 umol, 1 eq), TEA (142 mg, 1.41 mmol, 195 uL, 6 eq) and (E)-4-trityloxybut-2-enoic acid (96.9 mg, 281 umol, 1.2 eq) in ethyl acetate (2 mL) was added T3P (448 mg, 703 umol, 418 uL, 50% purity in EtOAc, 3 eq) at 0° C. The mixture was stirred at 0° C. for 0.5 hour. The reaction mixture was diluted with water (5 mL) and extracted with ethyl acetate (10 mL×3). The combined organic layers were washed with brine (10 mL), dried over Na₂SO₄, filtered and concentrated under reduced pressure to give a residue. The residue was purified by column chromatography (SiO₂, Ethyl acetate/Methanol=200/1 to 10/1). 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile (90 mg, 103 umol, 44% yield, 96% purity) was obtained as a yellow oil. LCMS [ESI, M+1]: 838.

Step B: 2-[(2S)-1-[(E)-4-hydroxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile (80 mg, 95.5 umol, 1 eq) in dichloromethane (200 uL) was added TFA (218 mg, 1.91 mmol, 141 uL, 20 eq). The mixture was stirred at 0° C. for 1 hour. The reaction mixture was diluted with water (5 mL) and basified to pH ~8 with NaHCO₃ aqueous solution (2 mL). The mixture was extracted with dichloromethane (5 mL×3). The combined organic layers were washed with brine (3 mL), dried over Na₂SO₄, filtered and concentrated under reduced pressure to give a residue. The residue was purified by prep-HPLC (column: Gemini 150*25 5 u; mobile phase: [water (0.05% ammonia hydroxide v/v)-ACN]; B %: 50%-80%, 12 min). The mixture was collected and lyophlizated. Title compound 2-[(2S)-1-[(E)-4-hydroxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (EXAMPLE 517, 10.2 mg, 16.8 umol, 18% yield, 98.5% purity) was obtained as a off-white solid. LCMS [ESI, M+1]: 596.

SFC condition: Column: Chiralcel OD-3 50×4.6 mm I.D., 3 um, Mobile phase: 40% methanol (0.05% DEA) in CO₂, Flow rate: 3 mL/min, Wavelength: 220 nm.

¹H NMR (400 MHz, chloroform-d) δ=7.73-7.61 (m, 2H), 7.46-7.30 (m, 2H), 7.27-7.16 (m, 2H), 7.06 (d, J=14.8 Hz, 1H), 6.62 (br d, J=13.6 Hz, 1H), 5.25-4.53 (m, 1H), 4.48-4.32 (m, 3H), 4.30-3.95 (m, 4H), 3.93-3.82 (m, 3H), 3.81-3.61 (m, 1H), 3.59-3.39 (m, 2H), 3.30-2.96 (m, 5H), 2.92 (s, 3H), 2.87-2.53 (m, 4H), 2.47 (d, J=4.0 Hz, 3H), 2.34-2.21 (m, 1H), 2.13-1.99 (m, 1H), 1.98-1.82 (m, 3H).

Example 518

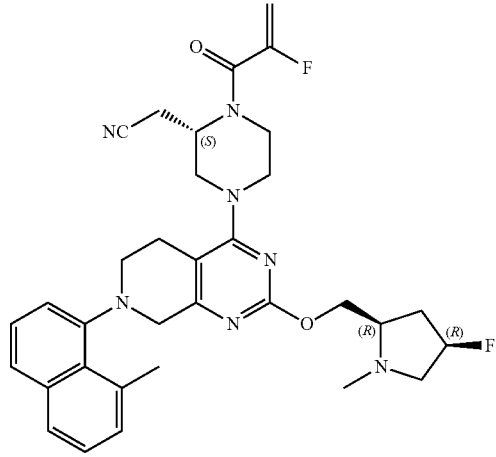

2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile

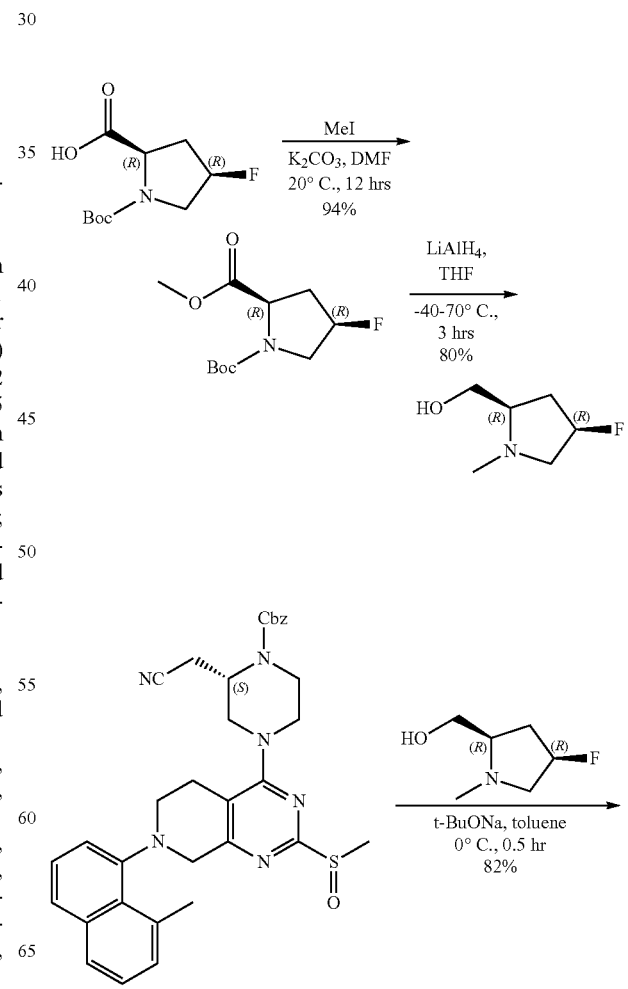

-continued

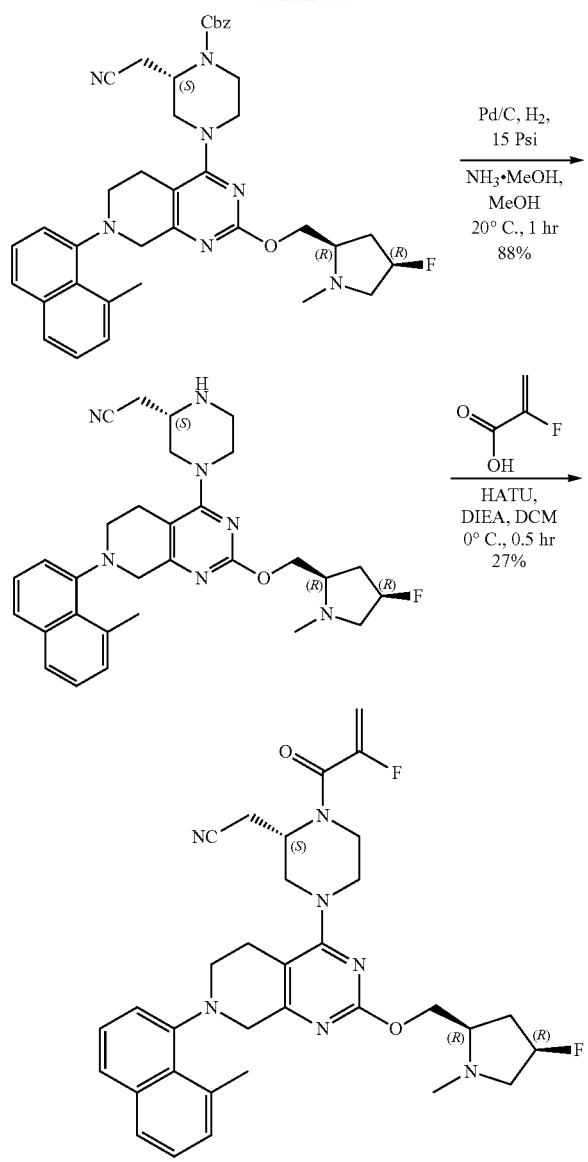

Step 1: O1-tert-butyl O2-methyl
(2R,4R)-4-fluoropyrrolidine-1,2-dicarboxylate

To a solution of (2R,4R)-1-tert-butoxycarbonyl-4-fluoropyrrolidine-2-carboxylic acid (300 mg, 1.29 mmol, 1.0 eq) and K$_2$CO$_3$ (533 mg, 3.86 mmol, 3.0 eq) in DMF (2.0 mL) was added MeI (4.80 g, 33.8 mmol, 2.11 mL, 26.3 eq). The mixture was stirred at 20° C. for 12 hours. After completion, the reaction mixture was added water (5.0 mL) and extracted with ethyl acetate (10.0 ml×2). The organic layer was dried over Na$_2$SO$_4$, filtered and concentrated. The residue was purified by column chromatography (SiO$_2$, Petroleum ether: Ethyl acetate=10:1-1:1) to give the product O1-tert-butyl O2-methyl (2R,4R)-4-fluoropyrrolidine-1,2-dicarboxylate (300 mg, 1.21 mmol, 94% yield) as yellow oil.

$^1$H NMR (400 MHz, Chloroform-d) δ 5.30-5.10 (m, 1H), 4.58-4.37 (m, 1H), 3.94-3.76 (m, 1H), 3.75 (s, 3H), 3.72-3.55 (m, 1H), 2.54-2.23 (m, 2H), 1.52-1.40 (m, 9H).

Step 2: [(2R,4R)-4-fluoro-1-methyl-pyrrolidin-2-yl]
methanol To a solution of O1-tert-butyl O2-methyl
(2R,4R)-4-fluoropyrrolidine-1,2-dicarboxylate (300 mg, 1.21 mmol, 1.0 eq) in THF (3.0 mL) was added LiAlH$_4$ (138 mg, 3.64 mmol, 3.0 eq) at −40° C. The mixture was stirred at this temperature for 1 hour, then heated to 70° C. and stirred at 70° C. for 2 hours. After completion, the reaction mixture was quenched with saturated Na$_2$SO$_4$ aqueous (0.30 mL), then filtered. The mother liquor was collected and concentrated under vacuum to give the product [(2R,4R)-4-fluoro-1-methyl-pyrrolidin-2-yl]methanol (130 mg, 976 umol, 80% yield) as yellow oil.

$^1$H NMR (400 MHz, Chloroform-d) δ 5.18-4.98 (m, 1H), 3.76-3.70 (m, 1H), 3.54-3.43 (m, 1H), 3.38-3.28 (m, 1H), 2.51-2.44 (m, 1H), 2.42-2.37 (m, 1H), 2.35 (s, 3H), 2.34-2.26 (m, 1H), 2.21-2.09 (m, 1H).

Step A: benzyl(2S)-2-(cyanomethyl)-4-[2-[[(2R, 4R)-4-fluoro-1-methyl-pyrrolidin-2-yl]methoxy]-7-(8-methyl-1-naphthyl)-6,8-dihydro-5H-pyrido[3,4-d]
pyrimidin-4-yl]piperazine-1-carboxylate To a solution of [(2R,4R)-4-fluoro-1-methyl-pyrrolidin-2-yl] methanol (103 mg, 773 umol, 2.0 eq) and t-BuONa (55.8 mg, 580 umol, 1.50 eq) in toluene (2.0 mL) was added benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (230 mg, 387 umol, 1.0 eq). The mixture was stirred at 0° C. for 0.5 hour. After completion, the reaction mixture was added water (10.0 mL) and extracted with ethyl acetate (10.0 ml×3). The organic layer was dried over Na$_2$SO$_4$, filtered and concentrated. The residue was purified by reversed phase flash HPLC (C18, 0.1% FA in water, 0-60% MeCN) to give the product benzyl(2S)-2-(cyanomethyl)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (210 mg, 316 umol, 82% yield) as yellow solid. LCMS [ESI, M+1]:664.

$^1$H NMR (400 MHz, Chloroform-d) δ 7.70 (br d, J=8.4 Hz, 1H), 7.65 (t, J=8.6 Hz, 1H), 7.45-7.32 (m, 7H), 7.26-7.17 (m, 2H), 5.24-5.02 (m, 3H), 4.73-4.61 (m, 1H), 4.53-4.42 (m, 1H), 4.30-4.18 (m, 2H), 4.11-3.96 (m, 2H), 3.94-3.81 (m, 1H), 3.81-3.67 (m, 1H), 3.58-3.47 (m, 1H), 3.46-3.29 (m, 2H), 3.24-3.06 (m, 3H), 3.05-2.96 (m, 1H), 2.92 (s, 3H), 2.82-2.71 (m, 2H), 2.70-2.51 (m, 2H), 2.50-2.47 (m, 4H), 2.45-2.35 (m, 1H), 2.12-2.05 (m, 1H).

Step B: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-[[(2R,4R)-4-fluoro-1-methyl-pyrrolidin-2-yl]methoxy]-7-(8-methyl-1-naphthyl)-6,8-dihydro-5H-pyrimidin-4-yl]piperazine-1-carboxylate (200 mg, 301 umol, 1.0 eq) and NH$_3$.MeOH (2.0 mL, 20% purity) in methanol (4.0 mL) was added Pd/C (80 mg, 10% purity). The mixture was purged by N$_2$ for 3 times, and then stirred under H$_2$ atmosphere (15 Psi) at 25° C. for 1 hour. After completion, the reaction mixture was filtered through Celite. The mother liquor was concentrated under vacuum to give the product 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (140 mg,

1363

264 umol, 88% yield) as yellow oil. The product was used for the next step directly without further purification. LCMS [ESI, M+1]:664.

Step C: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile To a solution of 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (120 mg, 226 umol, 1.0 eq), 2-fluoroprop-2-enoic acid (61.2 mg, 680 umol, 3.0 eq) and DIEA (176 mg, 1.36 mmol, 238 uL, 6.0 eq) in DCM (3.0 mL) was added HATU (258.44 mg, 679.69 umol, 3 eq). The mixture was stirred at 0° C. for 0.5 hour. After completion, the reaction mixture was added water (5.0 mL) and extracted with ethyl acetate (5.0 mL×3). The organic layer was dried over $Na_2SO_4$, filtered and concentrated under vacuum. The residue was purified by prep-HPLC (column: Gemini 150*25 5 u; mobile phase: [water (0.05% ammonia hydroxide v/v)-ACN]; B %: 50%-80%,12 min) to give the title compound 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile (EXAMPLE 518, 37.9 mg, 60.1 umol, 27% yield, 96% purity) as white solid. LCMS [ESI, M+1]: 602.

$^1$H NMR (400 MHz, Chloroform-d) δ 7.70 (br d, J=8.0 Hz, 1H), 7.65 (t, J=8.2 Hz, 1H), 7.45-7.37 (m, 1H), 7.34 (t, J=7.6 Hz, 1H), 7.27-7.18 (m, 2H), 5.53-5.32 (m, 1H), 5.30-5.22 (m, 1H), 5.21-5.03 (m, 1H), 4.97-4.68 (m, 1H), 4.52-4.42 (m, 1H), 4.29-4.20 (m, 2H), 4.18-4.03 (m, 2H), 3.95-3.68 (m, 2H), 3.60-3.41 (m, 2H), 3.39-3.30 (m, 1H), 3.26-3.15 (m, 2H), 3.15-2.95 (m, 2H), 2.92 (s, 3H), 2.90-2.54 (m, 4H), 2.53-2.46 (m, 4H), 2.45-2.35 (m, 1H), 2.13-1.97 (m, 1H).

Example 519

1364

2-[(2S)-1-(2-fluoroprop-2-enoyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile

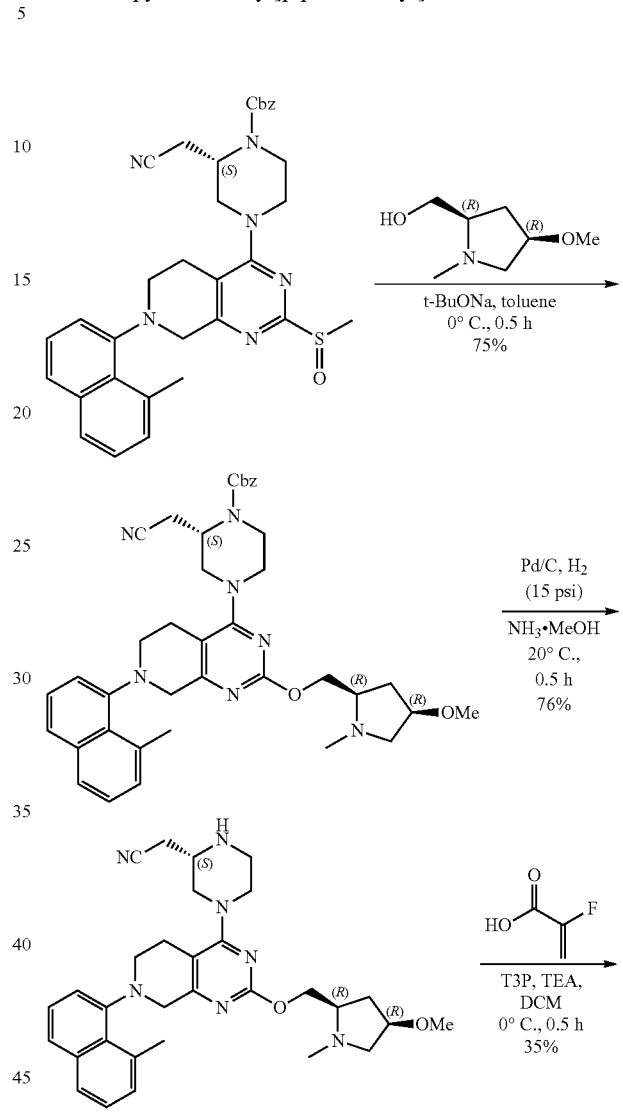

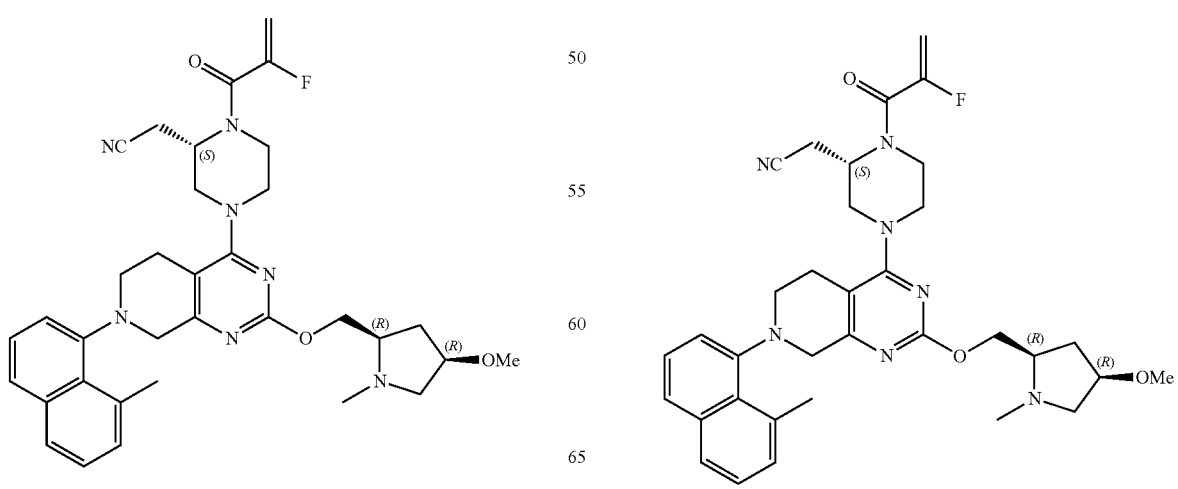

-continued

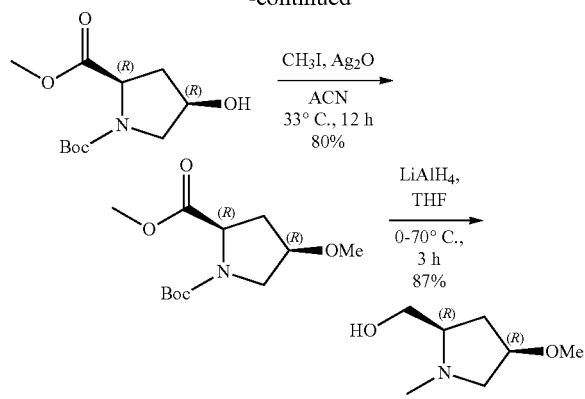

Step 1: O1-tert-butyl O2-methyl (2R,4R)-4-methoxypyrrolidine-1,2-dicarboxylate To a solution of O1-tert-butyl O2-methyl (2R,4R)-4-hydroxypyrrolidine-1,2-dicarboxylate (2.1 g, 8.56 mmol, 1 eq) in MeCN (42 mL) was added $Ag_2O$ (5.95 g, 25.7 mmol, 3 eq) and $CH_3I$ (7.75 g, 54.6 mmol, 3.40 mL, 6.38 eq). The reaction mixture was stirred at 33° C. for 12 hours. The reaction mixture was filtered and the filtrate was concentrated under vacuum. The residue was purified by column chromatography ($SiO_2$, Petroleum ether/Ethyl acetate=8/1 to 5/1) to give O1-tert-butyl O2-methyl (2R,4R)-4-methoxy-pyrrolidine-1,2-dicarboxylate (1.88 g, 6.89 mmol, 80% yield, 95.0% purity) as a colorless oil.

$^1$H NMR (400 MHz, chloroform-d) δ=4.45-4.26 (m, 1H), 3.96-3.89 (m, 1H), 3.72 (s, 3H), 3.68-3.55 (m, 1H), 3.54-3.43 (m, 1H), 3.27 (s, 3H), 2.38-2.17 (m, 2H), 1.51-1.37 (m, 9H).

Step 2: [(2R,4R)-4-methoxy-1-methyl-pyrrolidin-2-yl]methanol

To the solution of O1-tert-butyl O2-methyl (2R,4R)-4-methoxypyrrolidine-1,2-dicarboxylate (2.98 g, 11.5 mmol, 1 eq) in THF (60 mL) was added $LiAlH_4$ (872 mg, 23.0 mmol, 2 eq) at 0° C., the mixture was stirred at 0° C. for 1 hour. Then the reaction mixture was heated to 80° C. and stirred for 2 hours. The reaction was quenched with saturated $Na_2SO_4$ aqueous (3 mL), then filtered and the filter cake was washed with THF (3×20 mL). The filtrate was concentrated under vacuum to give [(2R,4R)-4-methoxy-1-methyl-pyrrolidin-2-yl]methanol (1.53 g, 10.0 mmol, 87% yield, 95.0% purity) as a brown oil which was used for next step without further purification.

$^1$H NMR (400 MHz, chloroform-d) δ=3.82-3.76 (m, 1H), 3.69 (dd, J=3.2, 11.2 Hz, 1H), 3.45 (dd, J=1.6, 10.8 Hz, 1H), 3.29 (s, 3H), 3.18 (d, J=10.4 Hz, 1H), 2.62 (br s, 1H), 2.42 (tdd, J=2.8, 6.4, 9.2 Hz, 1H), 2.38-2.33 (m, 1H), 2.32 (s, 3H), 2.16 (ddd, J=6.8, 8.8, 14.0 Hz, 1H), 1.92 (tdd, J=1.6, 6.8, 14.0 Hz, 1H).

Step A: (benzyl (2S)-2-(cyanomethyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate To the solution of [(2R,4R)-4-methoxy-1-methyl-pyrrolidin-2-yl]methanol (1.37 g, 9.42 mmol, 2.8 eq) in toluene (40 mL) was added t-BuONa (970 mg, 10.1 mmol, 3 eq) at 0° C., then benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (2 g, 3.36 mmol, 1 eq) was added at 0° C., the reaction mixture was stirred at 0° C. for 0.5 hour. Water (20 mL) was added into the mixture. The mixture was diluted with EtOAc (10 mL) and extracted with EtOAc (2×20 mL). The combined organic layers were washed with brine (20 mL). The combined organic layers were dried over anhydrous $Na_2SO_4$, filtered and concentrated under vacuum. The residue was purified by reversed phase flash column (ACN/Water (0.1% FA)=57%) to give (benzyl (2S)-2-(cyanomethyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl] piperazine-1-carboxylate (1.8 g, 2.53 mmol, 75% yield, 95.0% purity)) as a yellow solid. LCMS [ESI, M+1]: 676.

$^1$H NMR (400 MHz, chloroform-d) δ=7.73-7.60 (m, 2H), 7.47-7.31 (m, 7H), 7.27-7.16 (m, 2H), 5.21 (s, 2H), 4.67 (br s, 1H), 4.45 (br dd, J=4.4, 10.0 Hz, 1H), 4.24-4.16 (m, 2H), 4.10-3.96 (m, 2H), 3.96-3.65 (m, 3H), 3.59-3.40 (m, 2H), 3.29 (d, J=1.6 Hz, 3H), 3.25-3.06 (m, 4H), 3.00 (dt, J=3.6, 12.4 Hz, 1H), 2.91 (s, 3H), 2.81-2.55 (m, 4H), 2.45 (d, J=6.0 Hz, 3H), 2.42-2.29 (m, 2H), 1.88-1.68 (m, 2H).

Step B: 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To the solution of benzyl (2S)-2-(cyanomethyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (2 g, 2.96 mmol, 1 eq) and $NH_3$.MeOH (20 mL, 20% purity) in MeOH (40 mL) was added Pd/C (1 g, 10% purity) under $N_2$. The suspension was degassed under vacuum and purged with $H_2$ several times. The mixture was stirred under $H_2$ (15 psi) at 20° C. for 0.5 hour. The reaction mixture was filtered, the filtrate was concentrated under vacuum to give 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (1.29 g, 2.26 mmol, 76% yield, 95% purity) as a yellow solid which was used for next step without further purification. LCMS [ESI, M+1]: 542.

Step C: 2-[(2S)-1-(2-fluoroprop-2-enoyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To the solution of 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (150 mg, 277 umol, 1 eq), 2-fluoroprop-2-enoic acid (74.8 mg, 831 umol, 3 eq) and TEA (336 mg, 1.66 mmol, 462 uL, 50% purity, 6 eq) in EtOAc (3 mL) was added T3P (264 mg, 831 umol, 247 uL, 3 eq) at 0° C., the mixture was stirred at 0° C. for 0.5 hour. Water (4 mL) was added into the mixture. The mixture was extracted with EtOAc (3×8 mL). The combined organic layers were dried over anhydrous $Na_2SO_4$, filtered and concentrated under vacuum. The residue was purified by reversed phase flash column (ACN/Water (0.1% FA)=32%). Then the residue was purified by prep-HPLC (column: Gemini 150*25 5 u; mobile phase: [water (0.05% ammonia hydroxide v/v)-

ACN]; B %: 55%-85%,12 min) to give title compound 2-[(2S)-1-(2-fluoroprop-2-enoyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (EXAMPLE 519, 59.5 mg, 97.0 umol, 35% yield, 100% purity) as a white solid. LCMS [ESI, M+1]: 614.

$^1$H NMR (400 MHz, chloroform-d) δ=7.70 (br d, J=8.4 Hz, 1H), 7.65 (t, J=8.0 Hz, 1H), 7.45-7.38 (m, 1H), 7.34 (t, J=7.6 Hz, 1H), 7.27-7.17 (m, 2H), 5.53-5.33 (m, 1H), 5.26 (dd, J=3.6, 16.8 Hz, 1H), 4.88 (br s, 1H), 4.50-4.41 (m, 1H), 4.30-3.99 (m, 4H), 3.96-3.71 (m, 3H), 3.59-3.40 (m, 2H), 3.30 (s, 3H), 3.25-3.15 (m, 3H), 3.14-2.94 (m, 2H), 2.92 (s, 3H), 2.90-2.74 (m, 2H), 2.73-2.55 (m, 2H), 2.45 (d, J=5.6 Hz, 3H), 2.42-2.29 (m, 2H), 1.81 (br dd, J=7.2, 14.4 Hz, 1H).

Example 520

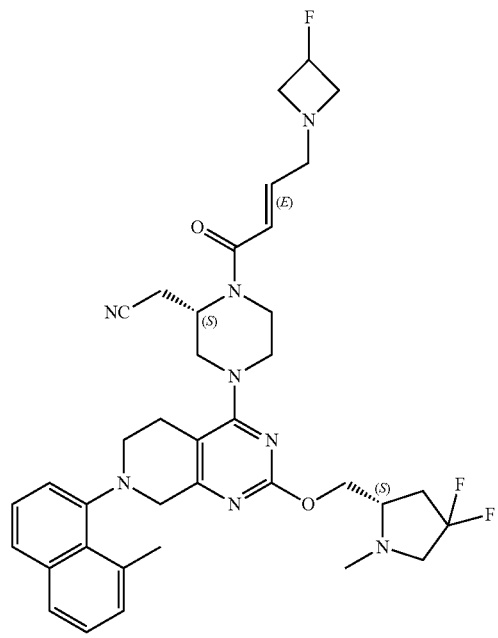

2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-(3-fluoroazetidin-1-yl)but-2-enoyl]piperazin-2-yl]acetonitrile

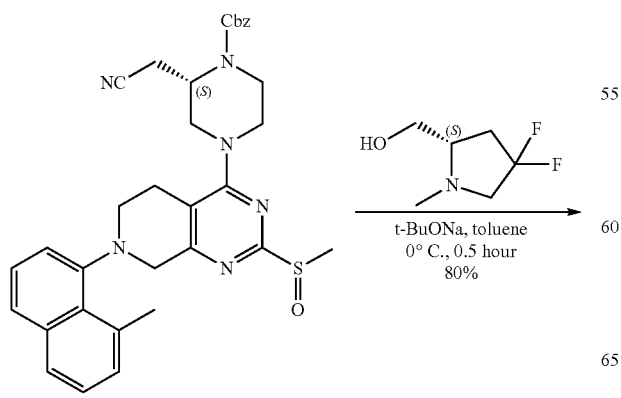

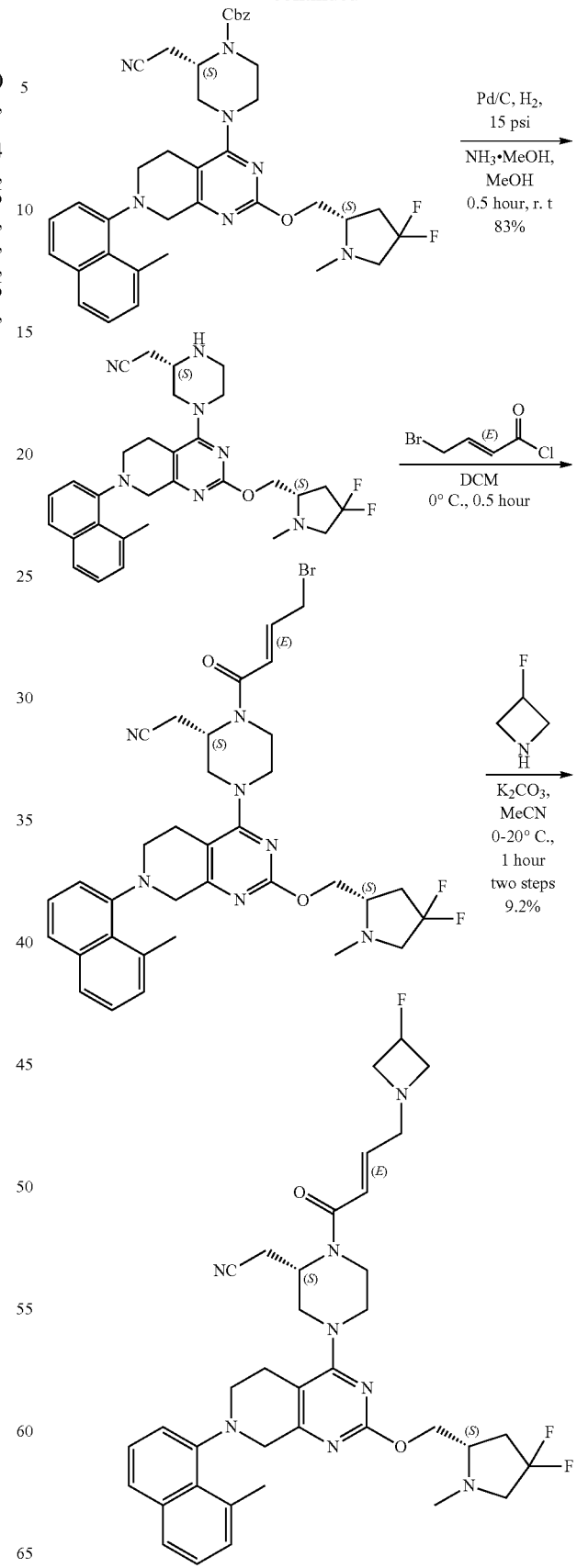

Step A: benzyl(2S)-2-(cyanomethyl)-4-[2-[[(2S)-4,4-difluoro-1-methyl-pyrrolidin-2-yl]methoxyl]-7-(8-methyl-1-naphthyl)-6,8-dihydro-5H-pyrido[3,4-d]pyrimidin-4-yl]piperazine-1-carboxylate To a solution of [(2S)-4,4-difluoro-1-methyl-pyrrolidin-2-yl]methanol (609.98 mg, 4.04 mmol, 3.0 eq) and t-BuONa (388 mg, 4.04 mmol, 3.0 eq) in toluene (2.0 mL) was dropwise added a solution of benzyl(2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (800 mg, 1.35 mmol, 1.0 eq) in toluene (4.0 mL) at 0° C. The reaction mixture was stirred at 0° C. for 0.5 hour. After completion, the reaction mixture was washed with water (15.0 mL) and extracted with ethyl acetate (3×20.0 mL). The Combine extracts were washed with brine (50.0 mL), dried with $Na_2SO_4$, filtrated and the solvent was removed under vacuum. The residue was purified by reversed phase flash HPLC [C18, 0.1% FA in water, 0-80% MeCN]. The obtained product was then concentrated, the aqueous was extracted with Ethyl acetate (3×50.0 mL), the combined organic layer was dried over $Na_2SO_4$, filtered and concentrated. Compound benzyl(2S)-2-(cyanomethyl)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (750 mg, 1.08 mmol, 80.1% yield, 98% purity) was obtained as yellow solid. LCMS [ESI, M+1]: 682.

Step B: 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile benzyl (2S)-2-(cyanomethyl)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (650 mg, 953 umol, 1.0 eq) and Pd/C (200 mg, 10% purity) was added in MeOH (8.0 mL) and $NH_3$.MeOH (8.0 mL, 20% purity) then the mixture was degassed and purged with $H_2$ for 3 times, and then the mixture was stirred at 20° C. for 0.5 hour under $H_2$ (15 psi) atmosphere. After completion, the crude mixture was filtered through a pad of celite. The cake was washed with MeOH (50.0 mL) and the filtrate dried under high vacuum. Compound 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (420 mg, 736 umol, 77.2% yield, 96% purity) was obtained as yellow solid. LCMS [ESI, M+1]: 548.

Step C: 2-[(2S)-1-[(E)-4-bromobut-2-enoyl]-4-[2-[[(2S)-4,4-difluoro-1-methyl-pyrrolidin-2-yl]methoxyl]-7-(8-methyl-1-naphthyl)-6,8-dihydro-5H-pyrido[3,4-d]pyrimidin-4-yl]piperazin-2-yl]acetonitrile To a solution of 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (420 mg, 822 umol, 1.0 eq) and pyridine (520 mg, 6.57 mmol, 531 uL, 8.0 eq) in DCM (6.0 mL) was added (E)-4-bromobut-2-enoyl chloride (603 mg, 3.29 mmol, 4.0 eq). The mixture was stirred at 0° C. for 0.5 hour. After completion, the mixture was concentrated under vacuum. The product 2-[(2S)-1-[(E)-4-bromobut-2-enoyl]-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (500 mg, crude) was obtained as yellow oil. The crude product was used directly to the next step without further purification. LCMS [ESI, M+1]: 695.

Step D: 2-[(2S)-4-[2-[[(2S)-4,4-difluoro-1-methyl-pyrrolidin-2-yl] methoxy]-7-(8-methyl-1-naphthyl)-6,8-dihydro-5H-pyrido[3,4-d]pyrimidin-4-yl]-1-[(E)-4-(3-fluoroazetidin-1-yl)but-2-enoyl]piperazin-2-yl] acetonitrile To a solution of 2-[(2S)-1-[(E)-4-bromobut-2-enoyl]-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (500 mg, 720 umol, 1.0 eq) and $K_2CO_3$ (995 mg, 7.20 mmol, 10.0 eq) in MeCN (12.0 mL) was added 3-fluoroazetidine (482 mg, 4.32 mmol, 6.0 eq, HCl) at 0° C. The mixture was stirred at 20° C. for 1 hour. After completion, the organic solvent was washed with water (10.0 mL). The aqueous phase was extracted with ethyl acetate (3×10 mL). Combine extracts were washed with brine (20.0 mL), dried with $Na_2SO_4$ the solvent was then removed under vacuum. The residue was purified by column chromatography (Base $Al_2O_3$, Petroleum ether:Ethyl acetate=3:1 to Ethyl acetate:Methanol=100:1), then the crude product was concentrated and purified by prep-HPLC (column: Waters Xbridge 150×25 5 u; mobile phase: [water (0.05% ammonia hydroxide v/v)-ACN]; B %: 55%-79%,10 min]; B %: 45%-75%,12 min) and lyophilization. Title compound 2-[(2S)-4-[2-[[(2S)-4,4-difluoro-1-methyl-pyrrolidin-2-yl] methoxy]-7-(8-methyl-1-naphthyl)-6,8-dihydro-5H-pyrido[3,4-d]pyrimidin-4-yl]-1-[(E)-4-(3-fluoroazetidin-1-yl)but-2-enoyl]piperazin-2-yl]acetonitrile (EXAMPLE 520, 45.8 mg, 66.5 umol, 9.24% yield, 100% purity) was obtained as yellow solid. LCMS [ESI, M+1]: 689.

$^1$H NMR (400 MHz, chloroform-d) δ=7.74-7.63 (m, 2H), 7.47-7.32 (m, 2H), 7.27-7.18 (m, 2H), 6.88 (br d, J=15.3 Hz, 1H), 6.42 (br d, J=15.4 Hz, 1H), 5.27-5.05 (m, 1H), 4.64 (br s, 1H), 4.48-4.41 (m, 1H), 4.31-4.18 (m, 2H), 4.16-3.95 (m, 2H), 3.94-3.84 (m, 1H), 3.82-3.66 (m, 3H), 3.54 (br d, J=7.6 Hz, 1H), 3.50-3.36 (m, 2H), 3.34 (br d, J=3.8 Hz, 2H), 3.30-3.24 (m, 1H), 3.24-3.08 (m, 4H), 3.07-2.95 (m, 2H), 2.92 (s, 3H), 2.86-2.76 (m, 1H), 2.76-2.57 (m, 3H), 2.57-2.47 (m, 1H), 2.46 (d, J=4.5 Hz, 3H), 2.34-2.17 (m, 1H).

Example 521

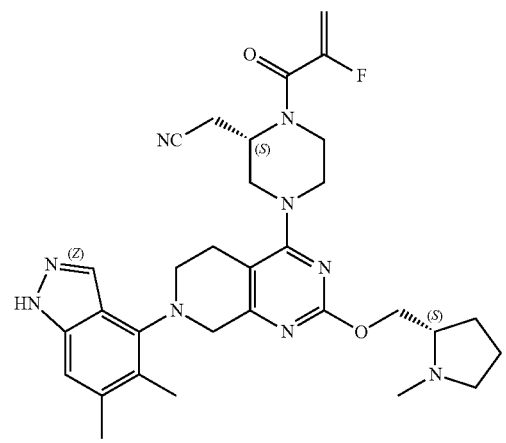

2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

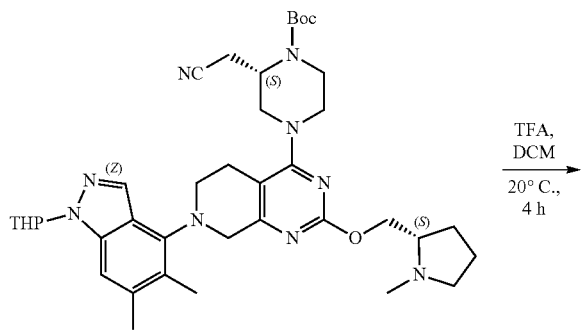

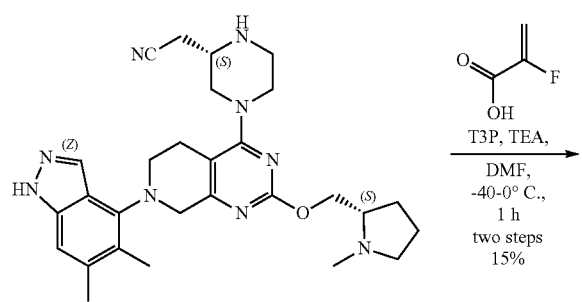

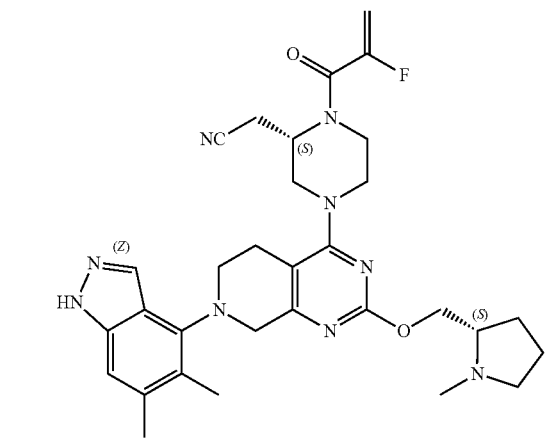

Step A: 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (720 mg, 1.03 mmol, 1 eq) in DCM (1 mL) was added TFA (4.62 g, 40.5 mmol, 3 mL, 39.4 eq). The mixture was stirred at 20° C. for 4 hours. Upon completion, the mixture was diluted with DCM (10 mL) and neutralized with saturated aqueous NaHCO$_3$. Then the aqueous phase was extracted with EtOAc (2×30 mL). The combined organic layers were dried over Na$_2$SO$_4$ and concentrated under vacuum to give 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile (880 mg, crude) as a yellow solid which was used directly into the next step without further purification.

Step B: 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile (500 mg, crude), 2-fluoroprop-2-enoic acid (61.1 mg, 679 umol) and TEA (294 mg, 2.91 mmol, 405 uL) in DMF (10 mL) was added T3P (926 mg, 1.45 mmol, 865 uL, 50% purity in EtOAc) at −40° C. Then the mixture was stirred at −40° C. for 0.5 hour and 0° C. for another 0.5 hour. Upon completion, the mixture was diluted with water (20 mL) and extracted with EtOAc (2×40 mL). The organic layers were washed with brine (50 mL), dried over Na$_2$SO$_4$ and concentrated under vacuum. The residue was purified by reversed phase flash [water (0.1% FA)/acetonitrile]. The desired fractions were collected and neutralized with saturated aqueous NaHCO$_3$ and extracted with EtOAc (2×70 mL). The organic layers were dried over Na$_2$SO$_4$ and concentrated under vacuum. The residue was purified by prep-HPLC (column: Phenomenex Synergi C18 150*30 mm*4 um; mobile phase: [water (0.225% FA)-ACN]; B %: 10%-40%, 12 min). The desired fractions were collected and lyophilized to give title compound 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (EXAMPLE 521, 52.5 mg, 79.8 umol, two steps 15% yield, 96.4% purity, FA) as a white solid. LCMS [ESI, M+1]:588.

SFC condition: Column: Chiralcel OJ-3 100×4.6 mm I.D., 3 um, Mobile phase: methanol (0.05% DEA) in CO$_2$ from 5% to 40%, Flow rate: 3 mL/min, Wavelength: 220 nm.

$^1$H NMR (400 MHz, chloroform-d) δ=8.03 (s, 1H), 7.15 (s, 1H), 5.53-5.34 (m, 1H), 5.25 (br dd, J=3.2, 16.8 Hz, 1H), 5.02-4.61 (m, 3H), 4.43 (dd, J=4.8, 11.6 Hz, 1H), 4.27 (s, 2H), 4.19 (br d, J=13.2 Hz, 1H), 4.01 (br d, J=12.4 Hz, 1H), 3.68-3.56 (m, 1H), 3.55-3.50 (m, 2H), 3.49-3.21 (m, 3H), 3.14 (br s, 1H), 2.98 (br s, 1H), 2.91-2.61 (m, 7H), 2.41 (s, 3H), 2.34 (s, 3H), 2.23 (qd, J=8.4, 12.4 Hz, 1H), 2.14-1.95 (m, 3H).

1373

Example 522

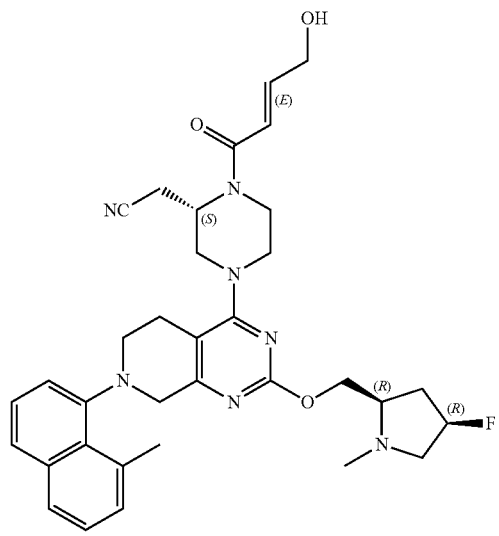

2-((S)-4-(2-(((2R,4R)-4-fluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-hydroxybut-2-enoyl)piperazin-2-yl)acetonitrile

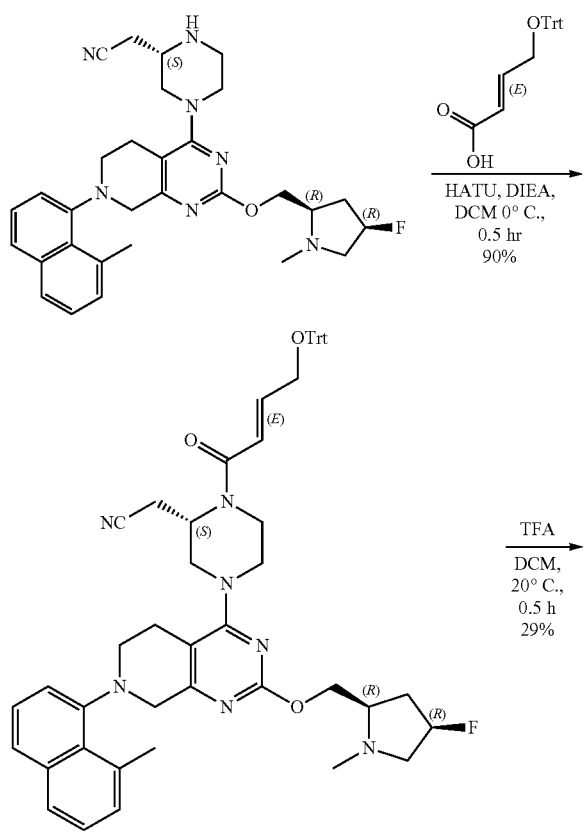

1374

-continued

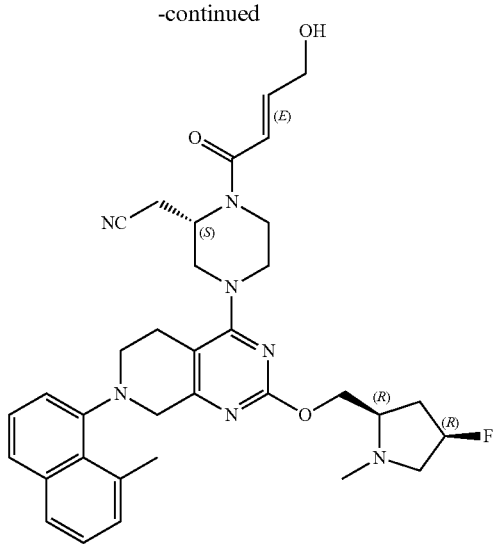

Step A: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile To a solution of 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (200 mg, 378 umol, 1.0 eq), (E)-4-trityloxybut-2-enoic acid (169 mg, 491 umol, 1.3 eq) and DIEA (293 mg, 2.27 mmol, 395 uL, 6.0 eq) in DCM (3.0 mL) was added HATU (431 mg, 1.13 mmol, 3.0 eq). The mixture was stirred at 0° C. for 0.5 hour. After completion, the mixture was added water (10 mL) and extracted with ethyl acetate (2×10.0 mL). The organic layer was dried over Na$_2$SO$_4$, filtered and concentrated. The residue was purified by column chromatography (SiO$_2$, Petroleum ether/Ethyl acetate=3/1 to Ethyl acetate:Methanol=20:1). The product 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile (290 mg, 339 umol, 90% yield) was obtained as yellow solid.

Step B: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-hydroxybut-2-enoyl]piperazin-2-yl]acetonitrile To a solution of 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile (290 mg, 339 umol, 1.0 eq) in dichloromethane (1.5 mL) was added TFA (2.31 g, 20.3 mmol, 1.5 mL, 59.8 eq), the mixture was stirred at 20° C. for 0.5 hour. After completion, the reaction mixture was concentrated, then added dichloromethane (10.0 mL), the organic layer was washed with saturated NaHCO$_3$ aqueous (2×10.0 mL), the organic layer was dried over Na$_2$SO$_4$, filtered and concentrated. The residue was purified by column chromatography (Base Al$_2$O$_3$, Petroleum ether/Ethyl acetate=3/1 to Ethyl acetate:Methanol=20:1). The crude product was then repurified by prep-HPLC (column: Gemini 150*25 5 u; mobile phase: [water (0.05% ammonia hydroxide v/v)-ACN]; B %: 45%-75%,12 min), the obtained product was concentrated and under lyophilization. Title compound 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-hydroxybut-2-enoyl]piperazin-2-yl]acetonitrile (EXAMPLE 522, 61.3 mg, 99.9 umol, 29% yield, 99% purity) was obtained as white solid. LCMS [ESI, M+1]: 614.

¹H NMR (400 MHz, chloroform-d) δ 7.73-7.61 (m, 2H), 7.46-7.31 (m, 2H), 7.27-7.18 (m, 2H), 7.06 (br d, J=14.8 Hz, 1H), 6.62 (br d, J=14.8 Hz, 1H), 5.27-4.97 (m, 1H), 4.74-4.55 (m, 1H), 4.52-4.34 (m, 3H), 4.31-4.16 (m, 2H), 4.15-3.96 (m, 2H), 3.94-3.58 (m, 3H), 3.56-3.48 (m, 1H), 3.46-3.41 (m, 1H), 3.36-3.29 (m, 1H), 3.26-3.07 (m, 3H), 3.04-2.97 (m, 1H), 2.92 (s, 3H), 2.85-2.57 (m, 4H), 2.49 (d, J=4.8 Hz, 3H), 2.45-2.34 (m, 1H), 2.29-1.91 (m, 2H).

Example 523

2-[(2S)-1-[(E)-4-hydroxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile

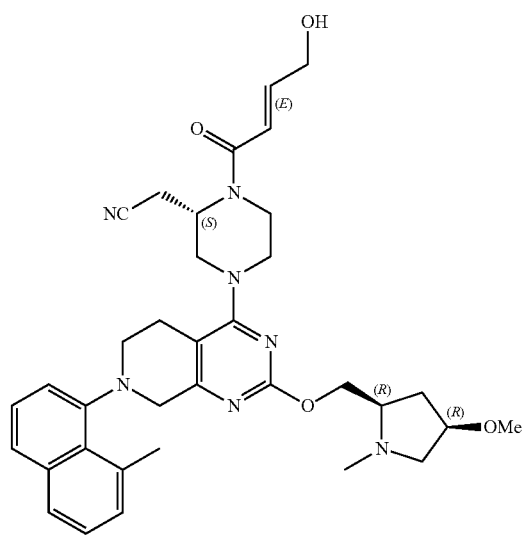

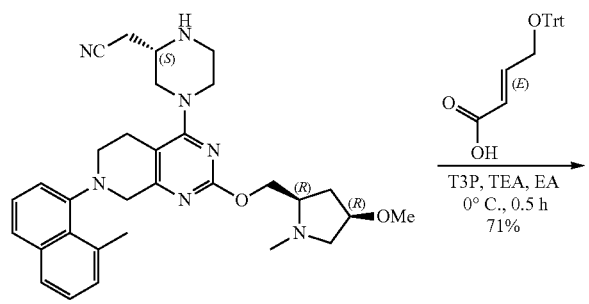

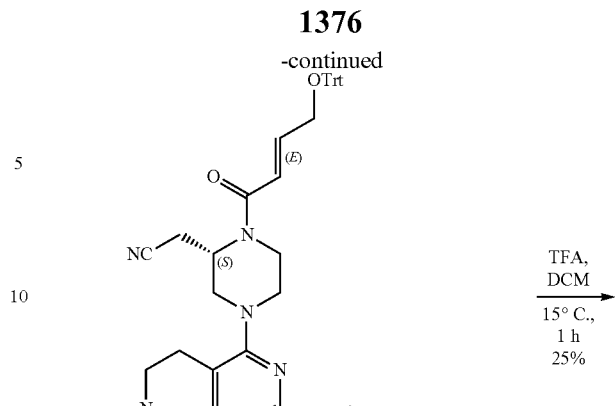

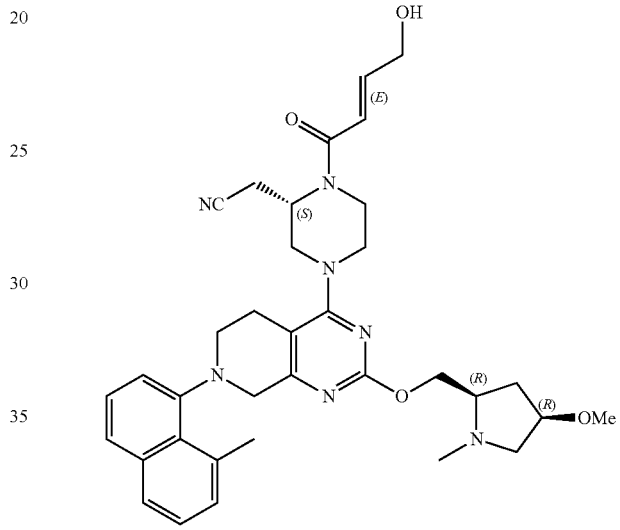

Step A: 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido [3,4-d]pyrimidin-4-yl]-1-[(E)-4-trityloxybut-2-enoyl]piperazin-2-yl]acetonitrile To the solution of 2-[(2S)-4-[2-[[(2R,4R)-4-methoxy-1-methyl-pyrrolidin-2-yl]methoxy]-7-(8-methyl-1-naphthyl)-6, 8-dihydro-5H-pyrido [3,4-d]pyrimidin-4-yl]piperazin-2-yl]acetonitrile (200 mg, 369 umol, 1 eq), (E)-4-trityloxybut-2-enoic acid (254 mg, 738 umol, 2 eq) and TEA (374 mg, 3.69 mmol, 514 uL, 10 eq) in EtOAc (4 mL) was added T3P (705 mg, 1.11 mmol, 659 uL, 50% purity, 3 eq) at 0° C., the mixture was stirred at 0° C. for 0.5 hour. Water (10 mL) was added into the mixture. The mixture was diluted with EtOAc (5 mL) and extracted with EtOAc (15 mL). The organic layer was washed with brine (10 mL), dried over anhydrous Na₂SO₄, filtered and concentrated under vacuum. The residue was purified by reversed phase flash column (ACN/Water (0.1% FA)=70%) to give 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile (230 mg, 262 umol, 71% yield, 99% purity) as a yellow solid.

Step B: 2-[(2S)-1-[(E)-4-hydroxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To the solution of 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile (230 mg, 265 umol, 1 eq) in DCM (2.3 mL) was added TFA (3.54 g, 31.1 mmol, 2.3 mL, 117 eq), the mixture was stirred at 15° C. for 1 hour. The reaction mixture was basified with saturated NaHCO₃ (30 mL) to PH=7~8, then extracted with DCM (2×15 mL). The combined organic layers were dried over anhydrous Na₂SO₄, filtered and concentrated under vacuum. The residue was purified by reversed phase flash column (ACN/Water (0.1% FA)=32%). Then the residue was purified by prep-HPLC (column: Gemini 150*25 5 u; mobile phase: [water (0.05% ammonia hydroxide v/v)-ACN]; B %: 37%-67%,12 min) to give title compound 2-[(2S)-1-[(E)-4-hydroxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (EXAMPLE 523, 41.7 mg, 66.6 umol, 25% yield, 100% purity) as a white solid. LCMS [ESI, M+1]: 626.

¹H NMR (400 MHz, chloroform-d) δ=7.70 (br d, J=8.4 Hz, 1H), 7.65 (t, J=8.0 Hz, 1H), 7.45-7.38 (m, 1H), 7.37-7.31 (m, 1H), 7.27-7.17 (m, 2H), 7.07 (br d, J=14.8 Hz, 1H), 6.62 (br d, J=14.0 Hz, 1H), 5.07 (br s, 1H), 4.85-4.55 (m, 1H), 4.51-4.37 (m, 3H), 4.30-3.97 (m, 4H), 3.94-3.65 (m, 2H), 3.58-3.40 (m, 2H), 3.29 (d, J=1.6 Hz, 3H), 3.25-2.96 (m, 5H), 2.92 (s, 3H), 2.86-2.54 (m, 4H), 2.45 (d, J=4.8 Hz, 3H), 2.42-2.28 (m, 2H), 1.81 (br dd, J=8.9, 13.6 Hz, 1H).

Example 524

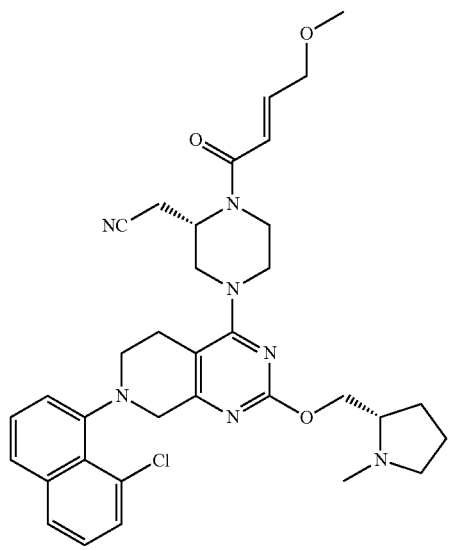 [SMILES: COC/C=C/C(=O)N1CCN(c2nc(OC[C@@H]3CCCN3C)nc3c2CCN(c2cccc4cccc(Cl)c24)C3)C[C@@H]1CC#N]

2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile

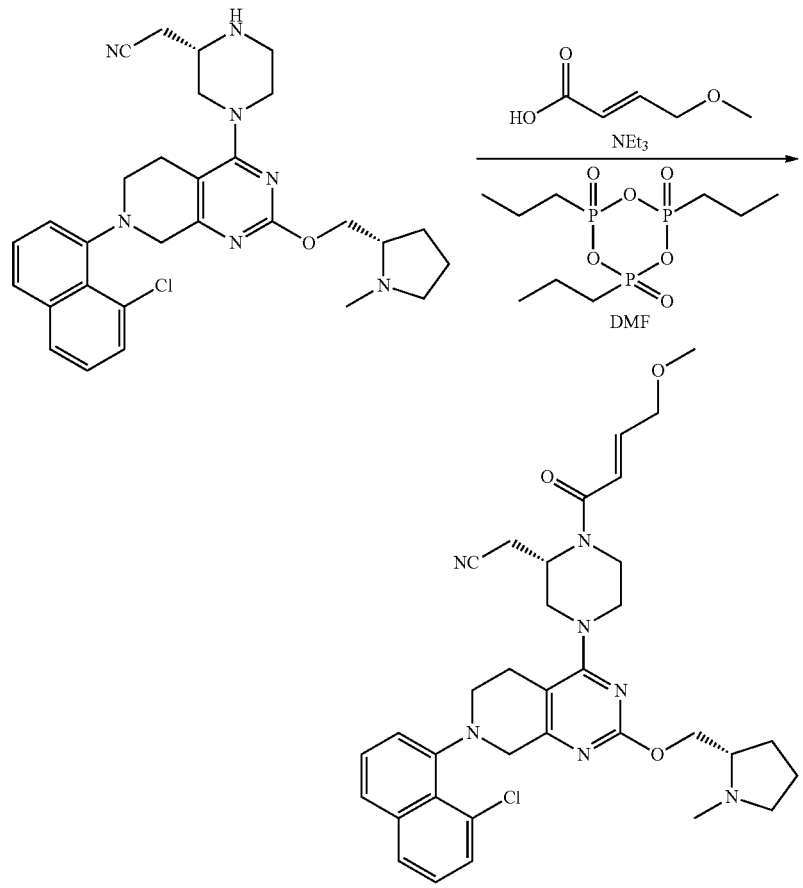

1379

Step A: 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile A stirred mixture of 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (100 mg, 0.1879 mmol), (E)-4-methoxybut-2-enoic acid (32.73 mg, 0.2819 mmol) and N,N-dimethylformamide (1 mL, 12.79 mmol) was cooled to 0° C. followed by addition of triethylamine (0.07859 mL, 0.5638 mmol) and 2,4,6-tripropyl-1,3,5,2,4,6-trioxatriphosphinane 2,4,6-trioxide, 50% in EtOAc (0.1678 mL, 0.2819 mmol). The reaction mixture was stirred for 2 hours while warming to room temperature. The mixture was partitioned between 0.5M Na$_2$CO$_3$ (5 mL) and EtOAc (15 mL) and the organics separated. The organics were next washed with water and brine (5 mL each), dried over Na$_2$SO$_4$ and evaporated in vacuo. The residue was next chromatographed on silica gel using 4% MeOH+0.4% NH$_4$OH/DCM as eluent to give impure material which was further purified by Gilson reverse prep HPLC eluting with 5 to 75% ACN+0.1% TFA/H$_2$O+0.1% TFA. Fractions containing pure product were combined and partitioned between DCM and a saturated solution of Na$_2$CO$_3$ and the layers separated. The organics were next washed with brine, dried over MgSO$_4$ and concentrated in vacuo to give pure title compound (EXAMPLE 524, 33 mg, 28%). ESI+APCI MS m/z 630.3 [M$^+$].

Example 525

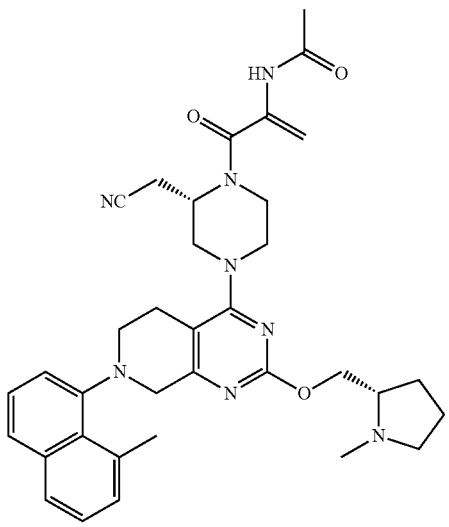 [SMILES: C=C(NC(C)=O)C(=O)N1CCN(c2nc(OC[C@@H]3CCCN3C)nc3c2CCN(c2cccc4cccc(C)c24)C3)C[C@@H]1CC#N]

1380

N-(3-((S)-2-(cyanomethyl)-4-(7-(8-methylnaphthalen-1-yl)-2-(((S)-1-methylpyrrolidin-2-yl)methoxy)-5,6,7,8-tetrahydropyrido [3,4-d]pyrimidin-4-yl)piperazin-1-yl)-3-oxoprop-1-en-2-yl)acetamide

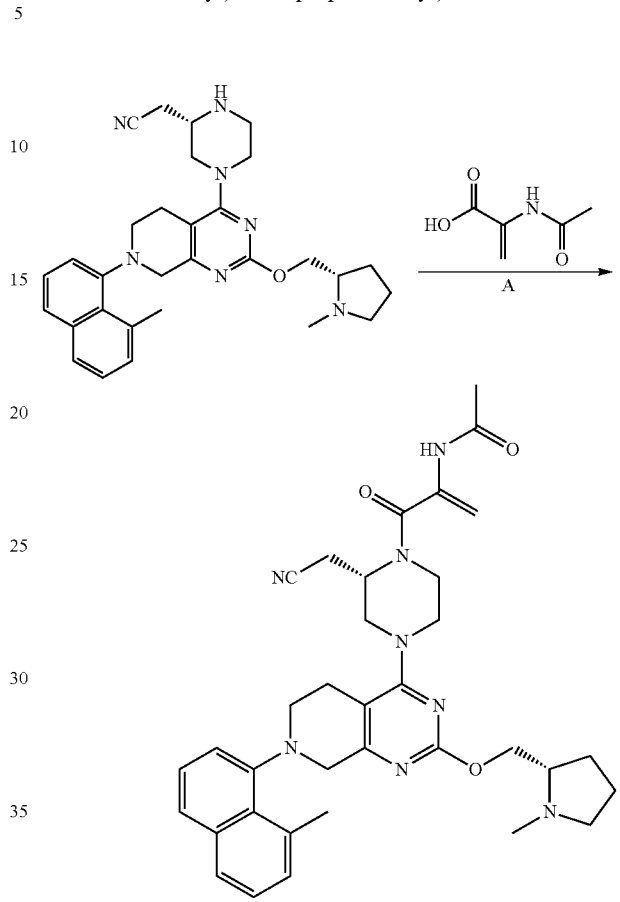

Step A: N-(3-((S)-2-(cyanomethyl)-4-(7-(8-methylnaphthalen-1-yl)-2-((S)-1-methylpyrrolidin-2-yl)methoxy)-5,6,7,8-tetrahydropyrido [3,4-d]pyrimidin-4-yl)piperazin-1-yl)-3-oxoprop-1-en-2-yl)acetamide To a 25 mL round bottom flask containing dichloromethane (2932 µl, 0.2932 mmol) cooled to 0° C. was added 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (150 mg, 0.2932 mmol) and Hunig's base (307.2 µl, 1.759 mmol). The reaction mixture was vigorously stirred while 2-Acetamidoacrylic acid (227.1 mg, 1.759 mmol) was added in one portion. Next, 1-Propanephosphonic acid cyclic anhydride (1047 µl, 1.759 mmol) was added slowly to the stirring mixture. The reaction was stirred for 2 hours at 0° C. The reaction was treated with basic water and the aqueous layer extracted with EtOAc (3×). The combined organics were concentrated in vacuo and purified on the Gilson (prep HPLC) eluting with 5→95% ACN+0.1% TFA/water+0.1% TFA. Fractions containing product were combined and basified with 1M NaOH and the aqueous layer extracted with DCM (2×). The organics were dried over Na$_2$SO$_4$ and concentrated in vacuo to give title compound N-(3-((S)-2-(cyanomethyl)-4-(7-(8-methylnaphthalen-1-yl)-2-((S)-1-methylpyrrolidin-2-yl)methoxy)-5,6,7,8-tetrahydropyrido

[3,4-d]pyrimidin-4-yl)piperazin-1-yl)-3-oxoprop-1-en-2-yl)
acetamide (EXAMPLE 525, 124.2 mg, 68.03% yield). ESI+
APCI MS m/z 623.3 [M+H]⁺.

Example 526

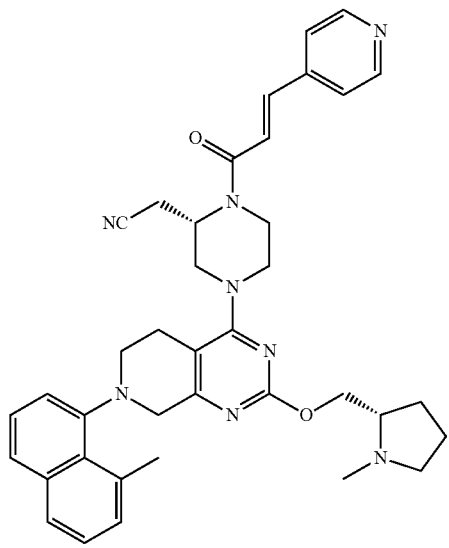 [SMILES: Cc1cccc2cccc(N3CCc4c(nc(OC[C@@H]5CCCN5C)nc4N4CCN(C(=O)/C=C/c5ccncc5)[C@@H](CC#N)C4)C3)c12]

2-((S)-4-(7-(8-methylnaphthalen-1-yl)-2-(((S)-1-
methylpyrrolidin-2-yl)methoxy)-5,6,7,8-tetrahydro-
pyrido[3,4-d]pyrimidin-4-yl)-1-((E)-3-(pyridin-4-yl)
acryloyl)piperazin-2-yl)acetonitrile 2-((S)-4-(7-(8-methylnaphthalen-1-yl)-2-(((S)-1-
methylpyrrolidin-2-yl)methoxy)-5,6,7,8-tetrahydro-
pyrido[3,4-d]pyrimidin-4-yl)-1-((E)-3-(pyridin-4-yl)
acryloyl)piperazin-2-yl)acetonitrile The title compound was prepared following Example 525
substituting Trans-3-(4-Pyridyl) Acrylic Acid for 2-Acet-
amidoacrylic acid in Step A. ESI+APCI MS m/z 643.3
[M+H]⁺.

Example 527

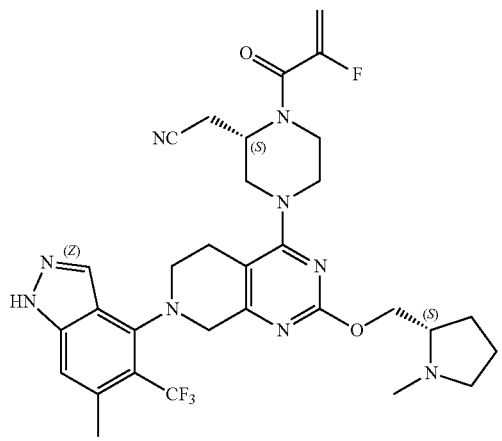

2-((S)-1-(2-fluoroacryloyl)-4-(7-(6-methyl-5-(trif-
luoromethyl)-1H-indazol-4-yl)-2-((S)-1-methylpyr-
rolidin-2-yl)methoxy)-5,6,7,8-tetrahydropyrido[3,4-
d]pyrimidin-4-yl)piperazin-2-yl)acetonitrile

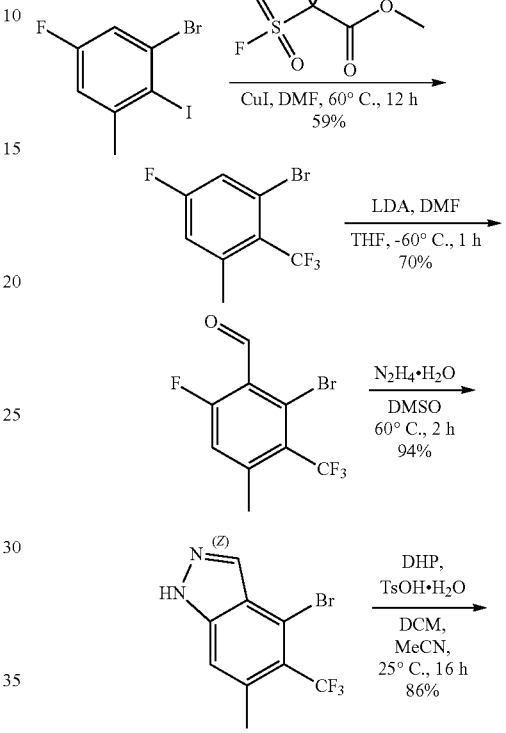

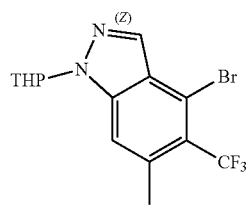

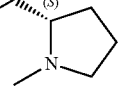

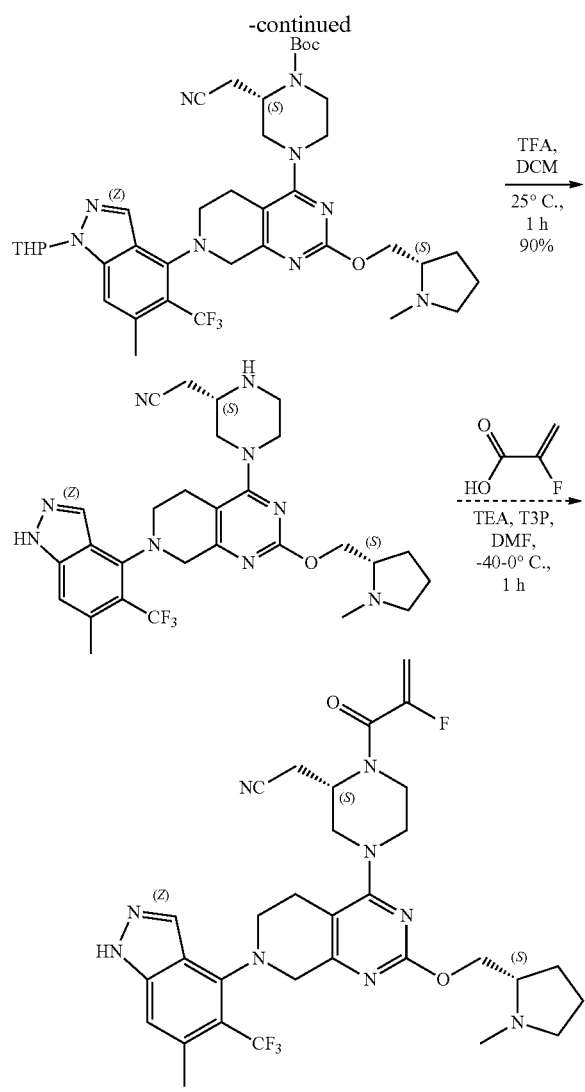

1-bromo-5-fluoro-3-methyl-2-(trifluoromethyl)benzene

To a solution of 1-bromo-5-fluoro-2-iodo-3-methyl-benzene (2 g, 6.35 mmol, 1 eq) in DMF (40 mL) was added CuI (7.26 g, 38.1 mmol, 6 eq) and methyl 2,2-difluoro-2-fluorosulfonyl-acetate (7.32 g, 38.1 mmol, 4.85 mL, 6 eq). The mixture was stirred at 60° C. for 12 hours. The reaction mixture was diluted with ethyl acetate (20 mL) and washed with water (20 mL×3). The organic layer was washed with brine (20 mL), dried over Na$_2$SO$_4$, filtered and concentrated under reduced pressure to give a residue. The residue was purified by column chromatography (SiO$_2$, Petroleum ether/ Ethyl acetate=1/0 to 10/1). 1-bromo-5-fluoro-3-methyl-2-(trifluoromethyl)benzene (1.3 g, 3.74 mmol, 59% yield, 74% purity) was obtained as a yellow oil.

$^1$H NMR (400 MHz, chloroform-d) δ=7.33 (dd, J=2.4, 7.6 Hz, 1H), 6.95 (dd, J=2.0, 8.8 Hz, 1H), 2.54 (q, J=3.6 Hz, 3H).

2-bromo-6-fluoro-4-methyl-3-(trifluoromethyl)benzaldehyde

To a mixture of 1-bromo-5-fluoro-3-methyl-2-(trifluoromethyl)benzene (900 mg, 3.50 mmol, 1 eq) in THF (20 mL) was added LDA (2 M in THF, 3.50 mL, 2 eq) at −60° C. under nitrogen atmosphere. After stirring for 0.5 hour, to the mixture was added DMF (768 mg, 10.5 mmol, 808 uL, 3 eq). The mixture was stirred at −60° C. for 1 hour. The reaction was quenched with saturated NH$_4$Cl aqueous solution (10 mL) and then extracted with ethyl acetate (50 mL×3). The combined organic phase was washed with brine (10 mL), dried over anhydrous Na$_2$SO$_4$, filtered and concentrated in vacuo. The residue was purified by column chromatography (SiO$_2$, Petroleum ether/Ethyl acetate=200/1 to 5/1). 2-bromo-6-fluoro-4-methyl-3-(trifluoromethyl)benzaldehyde (700 mg, 2.46 mmol, 70% yield) was obtained as a yellow oil.

$^1$H NMR (400 MHz, chloroform-d) δ=10.35 (s, 1H), 7.08 (d, J=10.4 Hz, 1H), 2.66-2.58 (m, 3H).

4-bromo-6-methyl-5-(trifluoromethyl)-1H-indazole

A solution of 2-bromo-6-fluoro-4-methyl-3-(trifluoromethyl)benzaldehyde (600 mg, 2.11 mmol, 1 eq) and hydrazine monohydrate (2.11 g, 42.1 mmol, 2.05 mL, 20 eq) in DMSO (8 mL) was stirred at 60° C. for 2 hours. The mixture was diluted with ethyl acetate (50 mL) and washed with water (3×50 mL) and brine (1×50 mL). The separated organic layer was dried over sodium sulfate, filtered and concentrated under vacuum. The residue was used to next step without further purification. 4-bromo-6-methyl-5-(trifluoromethyl)-1H-indazole (550 mg, 1.97 mmol, 94% yield) was obtained as a white solid.

4-bromo-6-methyl-1-tetrahydropyran-2-yl-5-(trifluoromethyl)indazole

To a solution of 4-bromo-6-methyl-5-(trifluoromethyl)-1H-indazole (500 mg, 1.79 mmol, 1 eq) in DCM (10 mL) was added 4-methylbenzenesulfonic acid hydrate (34.1 mg, 1791 umol, 0.1 eq) 1 followed by a solution of DHP (603 mg, 7.17 mmol, 655 uL, 4 eq) in CH$_3$CN (2 mL). The mixture was stirred at 25° C. for 16 hours. The mixture was diluted with ethyl acetate (100 mL) and washed with water (2×100 mL) and brine (1×50 mL). The organic layer was dried over sodium sulfate, filtered and concentrated under vacuum. The residue was purified by column chromatography over silica gel (petroleum ether/ethyl acetate 20/1 to 3/1). The desired fractions were collected and concentrated under vacuum to give 4-bromo-6-methyl-1-tetrahydropyran-2-yl-5-(trifluoromethyl)indazole (600 mg, 1.54 mmol, 86% yield, 93% purity) as a light yellow gum. LCMS [MSI, M+1]: 363.

Step A: tert-Butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl)indazol-4-yl]-6,8-dihydro-5H-pyrido[3,4-d]pyrimidin-4-yl]piperazine-1-carboxylate To a mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (400 mg, 848 umol, 1 eq), 4-bromo-6-methyl-1-tetrahydropyran-2-yl-5-(trifluoromethyl)indazole (431 mg, 1.19 mmol, 1.4 eq) Pd$_2$(dba)$_3$ (155 mg, 170 umol, 0.2 eq), RuPhos (158 mg, 339 umol, 0.4 eq) and Cs$_2$CO$_3$ (691 mg, 2.12 mmol, 2.5 eq) in toluene (20 mL) was degassed and purged with N$_2$ for 3 times, and then the mixture was stirred at 100° C. for 16 hours under N$_2$ atmosphere. To the mixture was added H$_2$O (20 mL×1) and Ethyl acetate (20 mL×1). The organic phase was separated, filtered and concentrated under reduced pressure to give a residue. The residue was purified by silica gel chromatography (Ethyl acetate/Methanol=50/1 to 2/1). tert-Butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl)indazol-4-yl]-6,8-dihydro-5H-pyrido[3,4-d]pyrimidin-4-yl]piperazine-1-carboxylate (500 mg, 535 umol, 32% yield, 80.7% purity) was obtained as a yellow solid. LCMS [MSI, M+1]: 754.

Step B: 2-[(2S)-4-[2-[[(2S)-1-methylpyrrolidin-2-yl]methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile To a solution of tert-butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl)indazol-4-yl]-6,8-dihydro-5H-pyrido[3,4-d]pyrimidin-4-yl]piperazine-1-carboxylate (470 mg, 503 umol, 1 eq) in DCM (1 mL) was added TFA (2.29 g, 20.1 mmol, 1.49 mL, 40 eq). The mixture was stirred at 25° C. for 1 h. To the mixture was added dichloromethane (5 mL) and basified with saturated aqueous NaHCO$_3$ solution to pH=8~9. The organic phase was separated, dried over sodium sulfate, filtered and concentrated under reduced pressure to give 2-[(2S)-4-[2-[[(2S)-1-methylpyrrolidin-2-yl]methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile (420 mg, 453 umol, 90% yield, 61.4% purity) was obtained as a yellow solid and used into next step without further purification. LCMS [MSI, M+1]: 570.

Step C: 2-((S)-1-(2-fluoroacryloyl)-4-(7-(6-methyl-5-(trifluoromethyl)-1H-indazol-4-yl)-2-(((S)-1-methylpyrrolidin-2-yl)methoxy)-5,6,7,8-tetrahydropyrido[3,4-d]pyrimidin-4-yl)piperazin-2-yl)acetonitrile To a solution of 2-[(2S)-4-[2-[[(2S)-1-methylpyrrolidin-2-yl]methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile (380 mg, 410 umol, 1 eq), 2-fluoroprop-2-enoic acid (18.4 mg, 205 umol, 0.5 eq) and TEA (124 mg, 1.23 mmol, 171 uL, 3 eq) in DMF (8 mL) was added T3P (391 mg, 614 umol, 365 uL, 50% purity in DMF, 1.5 eq) at −40° C. Then the mixture was stirred at −40° C. for 0.5 hour and 0° C. for another 0.5 hour. 2-fluoroprop-2-enoic acid (11 mg) and T3P (100 uL) was added and the mixture was stirred at −40° C. for further 0.5 hour. The mixture was diluted with water (15 mL) and extracted with EtOAc (2×40 mL). The organic layers were washed with brine (50 mL), dried over Na$_2$SO$_4$ and concentrated under vacuum. The residue was purified by prep-HPLC (column: Luna C18 150*25 5 u; mobile phase: [water (0.225% FA)-ACN]; B %: 22%-42%, 7.8 min) and (column: Phenomenex Gemini 150*25 mm*10 um; mobile phase: [water (0.04% NH$_3$H$_2$O+10 mM NH$_4$HCO$_3$)-ACN]; B %: 50%-68%, 12 min). The desired fractions were collected and lyophilize to give title compound 2-((S)-1-(2-fluoroacryloyl)-4-(7-(6-methyl-5-(trifluoromethyl)-1H-indazol-4-yl)-2-(((S)-1-methylpyrrolidin-2-yl)methoxy)-5,6,7,8-tetrahydropyrido[3,4-d]pyrimidin-4-yl)piperazin-2-yl)acetonitrile (EXAMPLE 527) as white solid.

Example 528

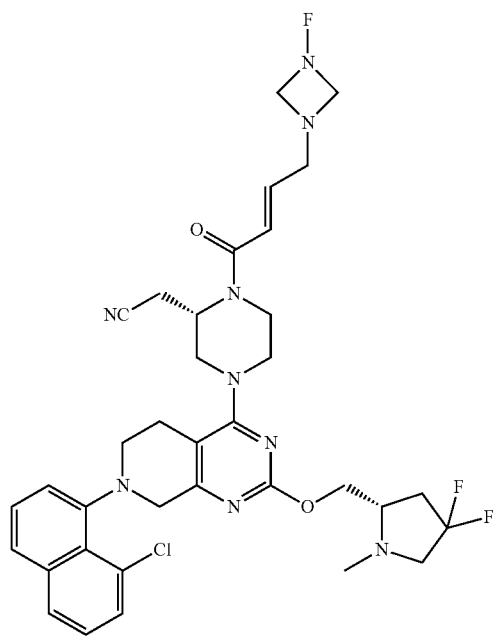 [SMILES: CN1CC(F)(F)C[C@H]1COc1nc2c(c(N3CCN(C(=O)/C=C/CN4CN(F)C4)[C@@H](CC#N)C3)n1)CCN(c1cccc3cccc(Cl)c13)C2]

2-((S)-4-(7-(8-chloronaphthalen-1-yl)-2-(((S)-4,4-difluoro-1-methylpyrrolidin-2-yl)methoxy)-5,6,7,8-tetrahydropyrido[3,4-d]pyrimidin-4-yl)-1-((E)-4-(3-fluoroazetidin-1-yl)but-2-enoyl)piperazin-2-yl)acetonitrile The title compound is prepared following Example 520 by modifying Intermediate 66 by substituting (S)-(4,4-difluoro-1-methylpyrrolidin-2-yl)methanol for (1-methylpyrrolidin-2-yl)methanol in Intermediate 66, Step E, modified Intermediate 66 is deprotected using the conditions in Intermediate 71, Step A, then substituted for Intermediate 66 in Example 520, Step A.

Example 529

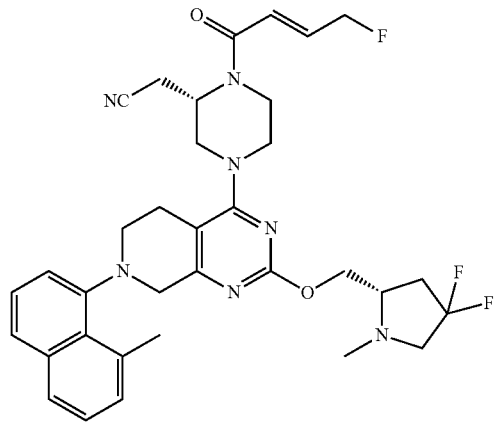 [SMILES: Cc1cccc2cccc(N3CCc4c(nc(OC[C@@H]5CC(F)(F)CN5C)nc4N4CCN(C(=O)/C=C/CF)[C@@H](CC#N)C4)C3)c12]

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-fluorobut-2-enoyl)piperazin-2-yl)acetonitrile The title compound was prepared following Example 467 substituting (E)-4-fluorobut-2-enoic acid for acryloyl chloride using the conditions of Example 479, Step C. LCMS [ESI, M+1]: 634.

¹H NMR (400 MHz, chloroform-d) δ=7.70 (br d, J=8.0 Hz, 1H), 7.66 (t, J=8.0 Hz, 1H), 7.45-7.38 (m, 1H), 7.38-7.32 (m, 1H), 7.27-7.18 (m, 2H), 7.09-6.93 (m, 1H), 6.60 (br d, J=14.8 Hz, 1H), 5.32-4.93 (m, 3H), 4.64 (br s, 1H), 4.45 (td, J=5.2, 11.2 Hz, 1H), 4.32-3.63 (m, 6H), 3.58-3.36 (m, 3H), 3.25-2.96 (m, 5H), 2.93 (s, 3H), 2.88-2.77 (m, 1H), 2.75-2.50 (m, 3H), 2.46 (d, J=4.4 Hz, 3H), 2.34-2.15 (m, 1H).

SFC condition: Column: Chiralcel OJ-3 50×4.6 mm I.D., 3 um, Mobile phase: methanol (0.05% DEA) in CO₂ from 5% to 40%, Flow rate: 3 mL/min, Wavelength: 220 nm.

Example 530

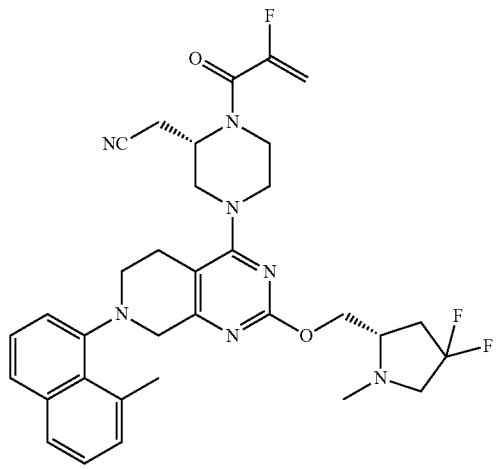 [SMILES: C=C(F)C(=O)N1CCN(c2nc(OC[C@@H]3CC(F)(F)CN3C)nc3c2CCN(c2cccc4cccc(C)c24)C3)C[C@@H]1CC#N]

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile The title compound was prepared following Example 467 substituting 2-fluoroprop-2-enoyl chloride for acryloyl chloride using the conditions of Example 478, Step A. LCMS [ESI, M+1]:620.

¹H NMR (400 MHz, chloroform-d) δ=7.73-7.63 (m, 2H), 7.46-7.33 (m, 2H), 7.27-7.18 (m, 2H), 5.54-5.33 (d, J=47.6 Hz, 1H), 5.26 (dd, J=3.6, 16.8 Hz, 1H), 5.05-4.62 (m, 1H), 4.58-4.37 (m, 1H), 4.31-4.13 (m, 3H), 4.12-4.05 (m, 1H), 3.97-3.73 (m, 1H), 3.59-3.36 (m, 3H), 3.27-2.95 (m, 6H), 2.92 (s, 3H), 2.89-2.49 (m, 5H), 2.46 (d, J=4.4 Hz, 3H), 2.34-2.17 (m, 1H).

SFC: "Column: Chiralcel OJ-3 50×4.6 mm I.D., 3 um Mobile phase: methanol (0.05% DEA) in CO₂ from 5% to 40% Flow rate: 3 mL/min Wavelength: 220 nm".

Example 531

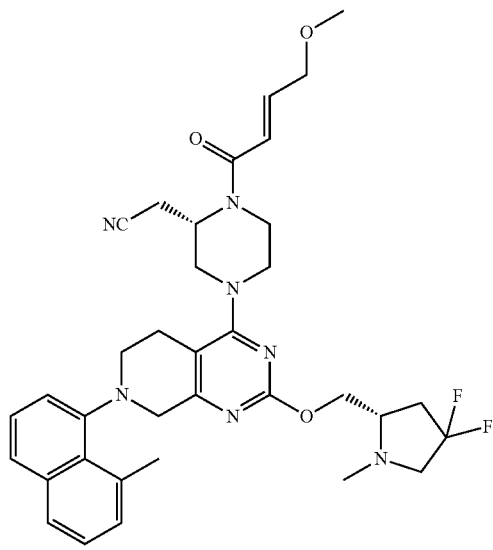 [SMILES: COC/C=C/C(=O)N1CCN(c2nc(OC[C@@H]3CC(F)(F)CN3C)nc3c2CCN(c2cccc4cccc(C)c24)C3)C[C@@H]1CC#N]

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-methoxybut-2-enoyl)piperazin-2-yl)acetonitrile The title compound is prepared following Example 467 substituting (methoxymethyl)prop-2-enoic acid for acryloyl chloride using the conditions of Example 489, Step A.

Example 532

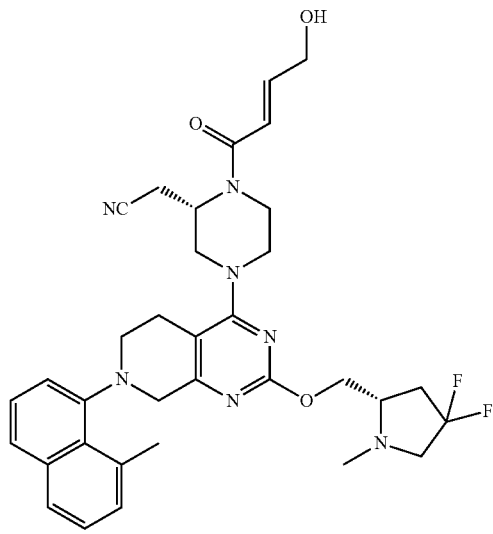 [SMILES: Cc1cccc2cccc(N3CCc4c(nc(OC[C@@H]5CC(F)(F)CN5C)nc4N4CCN(C(=O)/C=C/CO)[C@@H](CC#N)C4)C3)c12]

1389

2-((S)-4-(2-(((S)-4,4-difluoro-1-methylpyrrolidin-2-yl)methoxy)-7-(8-methylnaphthalen-1-yl)-5,6,7,8-tetrahydropyrido [3,4-d] pyrimidin-4-yl)-1-((E)-4-hydroxybut-2-enoyl)piperazin-2-yl)acetonitrile The title compound is prepared following Example 467 substituting 4-[tert-butyl(dimethyl)silyl]oxybut-2-ynoic acid for acryloyl chloride using the conditions of Example 483, Step A.

Example 533

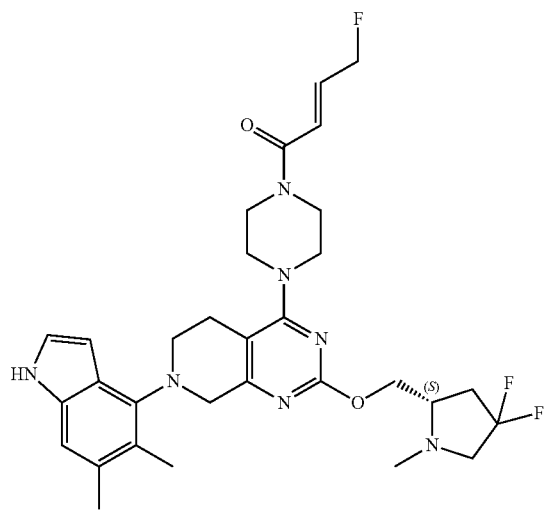

(S,E)-1-(4-(2-((4,4-difluoro-1-methylpyrrolidin-2-yl)methoxy)-7-(5,6-dimethyl-1H-indol-4-yl)-5,6,7,8-tetrahydropyrido[3,4-d]pyrimidin-4-yl)piperazin-1-yl)-4-fluorobut-2-en-1-one The title compound is prepared following Example 469 substituting (E)-4-fluorobut-2-enoic acid for prop-2-enoyl prop-2-enoate in Example 479, Step C.

Example 534

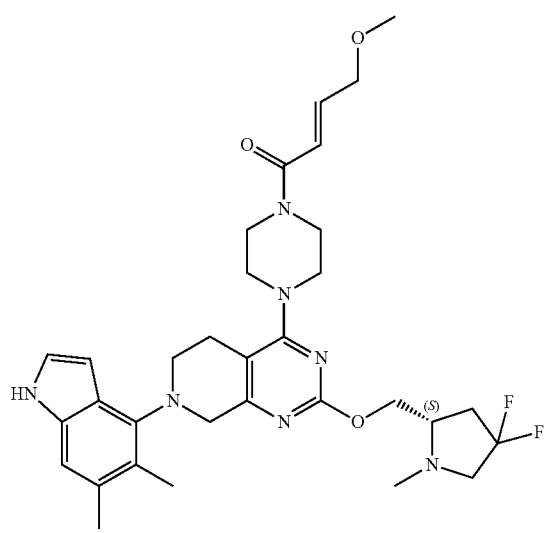

1390

(S,E)-1-(4-(2-((4,4-difluoro-1-methylpyrrolidin-2-yl)methoxy)-7-(5,6-dimethyl-1H-indol-4-yl)-5,6,7,8-tetrahydropyrido[3,4-d]pyrimidin-4-yl)piperazin-1-yl)-4-methoxybut-2-en-1-one The title compound is prepared following Example 469 substituting 2-(methoxymethyl)prop-2-enoic acid for prop-2-enoyl prop-2-enoate in Example 489, Step A.

Example 535

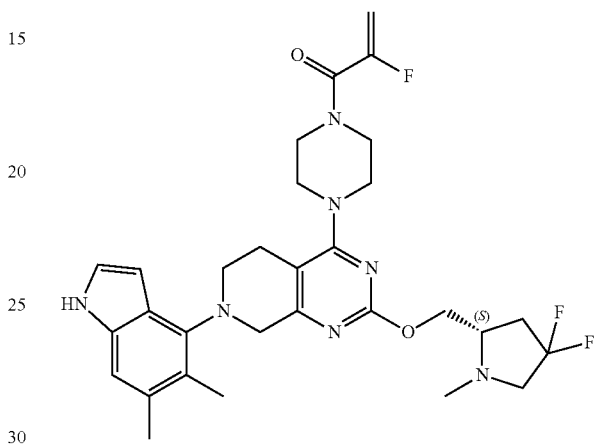

(S)-1-(4-(2-((4,4-difluoro-1-methylpyrrolidin-2-yl)methoxy)-7-(5,6-dimethyl-1H-indol-4-yl)-5,6,7,8-tetrahydropyrido[3,4-d]pyrimidin-4-yl)piperazin-1-yl)-2-fluoroprop-2-en-1-one The title compound is prepared following Example 469 substituting 2-fluoroacrylic acid for prop-2-enoyl prop-2-enoate in Example 478, Step A.

Example 536

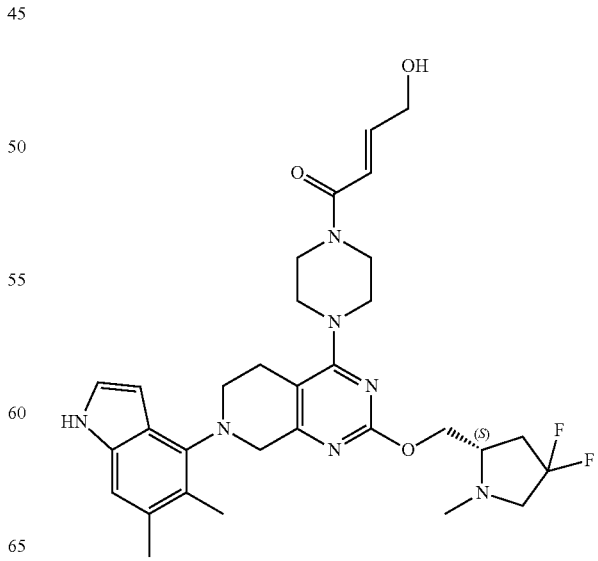

1391

(S,E)-1-(4-(2-((4,4-difluoro-1-methylpyrrolidin-2-yl)methoxy)-7-(5,6-dimethyl-1H-indol-4-yl)-5,6,7,8-tetrahydropyrido[3,4-d]pyrimidin-4-yl)piperazin-1-yl)-4-hydroxybut-2-en-1-one The title compound is prepared following Example 469 substituting 4-[tert-butyl(dimethyl)silyl]oxybut-2-ynoic acid for prop-2-enoyl prop-2-enoate in Example 469, Step D, and following the procedures of Example 483, Step A.

Example 537

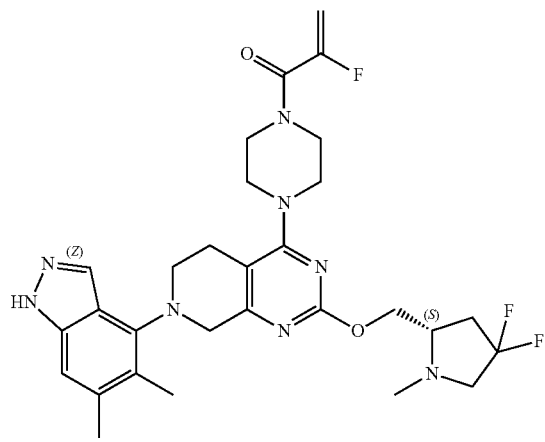

(S)-1-(4-(2-((4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)piperazin-1-yl)-2-fluoroprop-2-en-1-one The title compound is prepared following Example 470 substituting (E)-4-fluorobut-2-enoic acid for prop-2-enoyl prop-2-enoate in Example 478, Step A.

Example 538

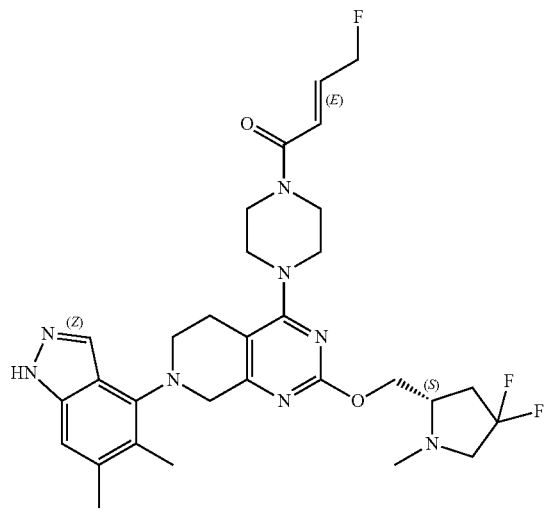

1392

(S,E)-1-(4-(2-((4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)piperazin-1-yl)-4-fluorobut-2-en-1-one The title compound is prepared following Example 470 substituting (E)-4-fluorobut-2-enoic acid for prop-2-enoyl prop-2-enoate in Example 479, Step C.

Example 539

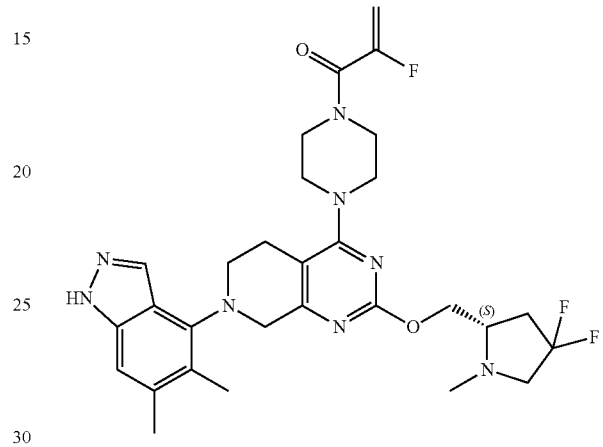

(S)-1-(4-(2-((4,4-difluoro-1-methylpyrrolidin-2-yl)methoxy)-7-(5,6-dimethyl-1H-indol-4-yl)-5,6,7,8-tetrahydropyrido[3,4-d]pyrimidin-4-yl)piperazin-1-yl)-2-fluoroprop-2-en-1-one The title compound is prepared following Example 470 substituting 2-fluoroacrylic acid for prop-2-enoyl prop-2-enoate in Example 478, Step A.

Example 540

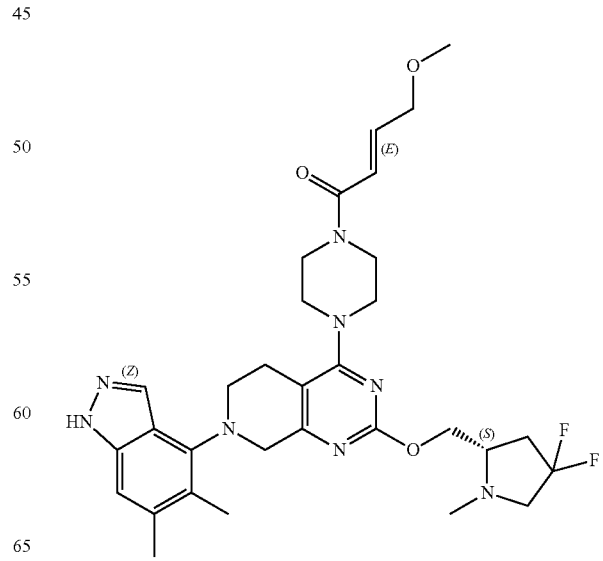

1393

(S,E)-1-(4-(2-((4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)piperazin-1-yl)-4-methoxybut-2-en-1-one The title compound is prepared following Example 470 substituting 2-(methoxymethyl)prop-2-enoic acid for prop-2-enoyl prop-2-enoate in Example 489, Step A.

Example 541

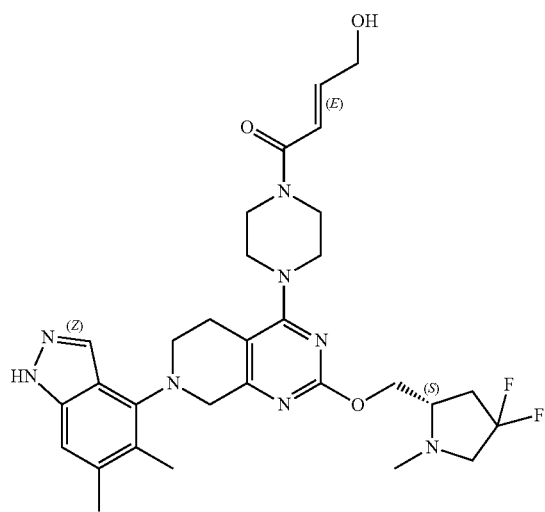

(S,E)-1-(4-(2-((4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)piperazin-1-yl)-4-hydroxybut-2-en-1-one The title compound is prepared following Example 470 substituting 4-[tert-butyl(dimethyl)silyl]oxybut-2-ynoic acid for prop-2-enoyl prop-2-enoate in Example 470, Step C and following the procedures of Example 483, Step A.

Example 542

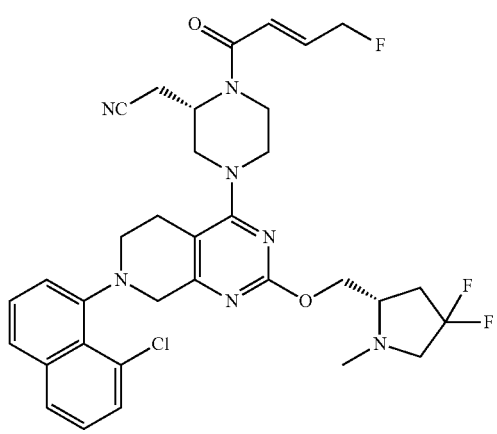 [SMILES: CN1CC(F)(F)C[C@H]1COc1nc2c(c(N3CCN(C(=O)/C=C/CF)[C@@H](CC#N)C3)n1)CCN(c1cccc3cccc(Cl)c13)C2]

1394

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-fluorobut-2-enoyl)piperazin-2-yl)acetonitrile The title compound was prepared following Example 468 substituting 2-fluoroprop-2-enoyl chloride for acryloyl chloride using the conditions of Example 479, Step C. LCMS [ESI, M+1]: 655.

¹H NMR (400 MHz, Chloroform-d) δ 7.76 (d, J=8.0 Hz, 1H), 7.63 (t, J=7.2 Hz, 1H), 7.53 (d, J=7.2 Hz, 1H), 7.50-7.40 (m, 1H), 7.34 (t, J=7.8 Hz, 1H), 7.26-7.18 (m, 1H), 7.08-6.94 (m, 1H), 6.60 (br d, J=14.8 Hz, 1H), 5.26-5.03 (m, 2H), 4.90-4.58 (m, 1H), 4.52-4.38 (m, 2H), 4.31-4.21 (m, 1H), 4.19-3.98 (m, 2H), 3.97-3.72 (m, 2H), 3.66-7.56 (m, 1H), 3.53-3.37 (m, 2H), 3.34-3.11 (m, 3H), 3.07-2.92 (m, 2H), 2.89-2.79 (m, 1H), 2.77-2.48 (m, 4H), 2.47 (d, J=2.4 Hz, 3H), 2.35-2.18 (m, 1H).

Example 543

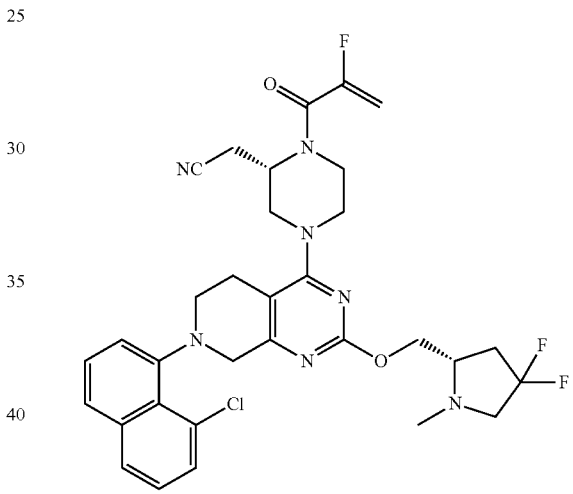

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile The title compound was prepared following Example 468 substituting 2-fluoroprop-2-enoyl chloride for acryloyl chloride using the conditions of Example 478, Step A. LCMS [ESI, M+1]: 640.

¹H NMR (400 MHz, chloroform-d) δ=7.76 (d, J=8.0 Hz, 1H), 7.63 (t, J=7.2 Hz, 1H), 7.53 (d, J=7.6 Hz, 1H), 7.45 (td, J=7.6, 12.4 Hz, 1H), 7.34 (t, J=7.6 Hz, 1H), 7.27-7.19 (m, 1H), 5.54-5.33 (dd, J=2.8, 47.6 Hz, 1H), 5.26 (dd, J=3.6, 16.8 Hz, 1H), 4.85 (br s, 1H), 4.51-4.38 (m, 2H), 4.31-3.77 (m, 4H), 3.69-3.54 (m, 1H), 3.41 (m, 2H), 3.35-2.48 (m, 11H), 2.47 (d, J=2.4 Hz, 3H), 2.35-2.16 (m, 1H).

SFC: "Column: Cellucoat 50×4.6 mm I.D., 3 um Mobile phase: methanol (0.05% DEA) in CO₂ from 5% to 40% Flow rate: 3 mL/min Wavelength: 220 nm".

Example 544

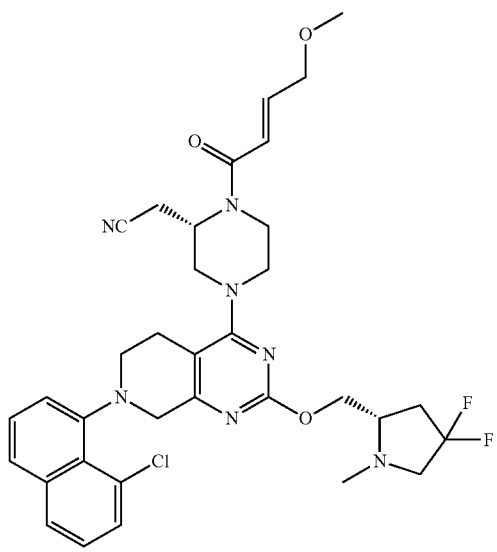 [SMILES: COC/C=C/C(=O)N1CCN(c2nc(OC[C@@H]3CC(F)(F)CN3C)nc3c2CCN(c2cccc4cccc(Cl)c24)C3)C[C@@H]1CC#N]

2-((S)-4-(7-(8-chloronaphthalen-1-yl)-2-(((S)-4,4-difluoro-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile The title compound is prepared following Example 468 substituting (methoxymethyl)prop-2-enoic acid for acryloyl chloride using the conditions of Example 489, Step A.

Example 545

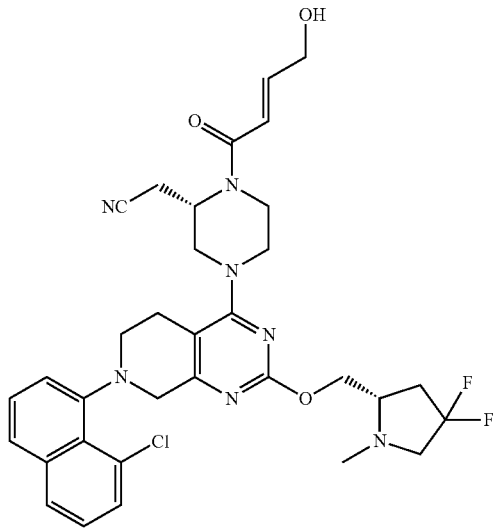 [SMILES: CN1CC(F)(F)C[C@H]1COc1nc2c(c(N3CCN(C(=O)/C=C/CO)[C@@H](CC#N)C3)n1)CCN(c1cccc3cccc(Cl)c13)C2]

2-((S)-4-(2-(((S)-4,4-difluoro-1-methylpyrrolidin-2-yl)methoxy)-7-(8-chloronaphthalen-1-yl)-5,6,7,8-tetrahydropyrido[3,4-d]pyrimidin-4-yl)-1-((E)-4-hydroxybut-2-enoyl)piperazin-2-yl)acetonitrile The title compound is prepared following Example 468 substituting 4-[tert-butyl(dimethyl)silyl]oxybut-2-ynoic acid for acryloyl chloride using the conditions of Example 483, Step A.

Example 546

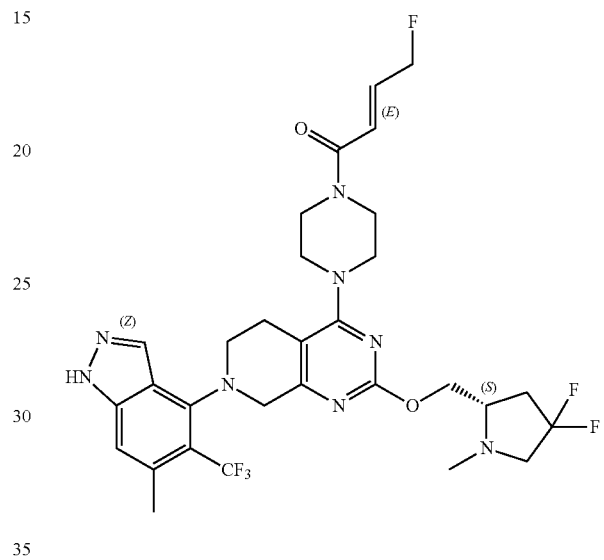

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-fluorobut-2-enoyl)piperazin-2-yl)acetonitrile The title compound is prepared following Example 527 substituting 2-fluoroprop-2-enoyl chloride for acryloyl chloride using the conditions of Example 479, Step C.

Example 547

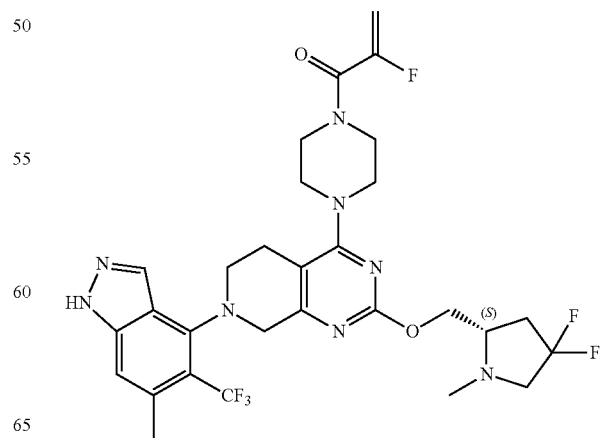

1397

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-(2-fluoro-acryloyl)piperazin-2-yl)acetonitrile The title compound is prepared following Example 527 substituting 2-fluoroprop-2-enoyl chloride for acryloyl chloride using the conditions of Example 478, Step A.

Example 548

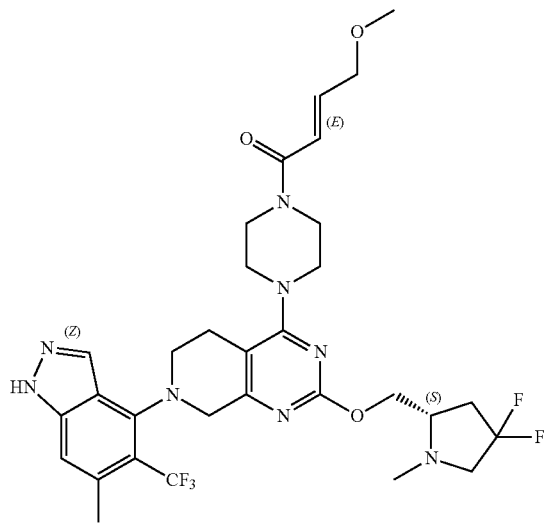

2-((S)-4-(7-(8-chloronaphthalen-1-yl)-2-(((S)-4,4-difluoro-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile The title compound is prepared following Example 527 substituting (methoxymethyl)prop-2-enoic acid for acryloyl chloride using the conditions of Example 489, Step A.

Example 549

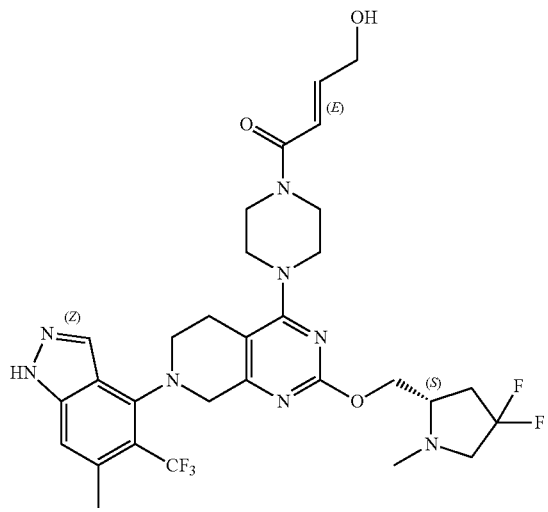

1398

2-((S)-4-(2-(((S)-4,4-difluoro-1-methylpyrrolidin-2-yl)methoxy)-7-(8-chloronaphthalen-1-yl)-5,6,7,8-tetrahydropyrido[3,4-d]pyrimidin-4-yl)-1-((E)-4-hydroxybut-2-enoyl)piperazin-2-yl)acetonitrile The title compound is prepared following Example 527 substituting 4-[tert-butyl(dimethyl)silyl]oxybut-2-ynoic acid for acryloyl chloride using the conditions of Example 483, Step A.

Example 550

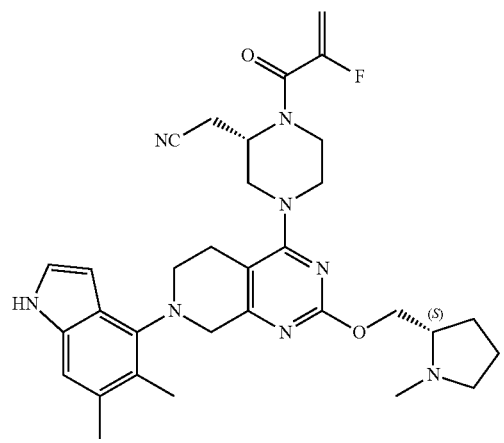

2-((S)-4-(7-(5,6-dimethyl-1H-indol-4-yl)-2-((S)-1-methylpyrrolidin-2-yl)methoxy)-5,6,7,8-tetrahydro-pyrido[3,4-d]pyrimidin-4-yl)-1-(2-fluoroacryloyl)piperazin-2-yl)acetonitrile 2-((S)-1-acryloyl-4-(7-(5,6-dimethyl-1H-indol-4-yl)-2-(((S)-1-methylpyrrolidin-2-yl)methoxy)-5,6,7,8-tetrahydropyrido[3,4-d]pyrimidin-4-yl)piperazin-2-yl)acetonitrile The title compound is prepared following Example 466 substituting 2-fluoroacrylic acid for prop-2-enoyl prop-2-enoate as described in Example 478, Step A.

Example 551

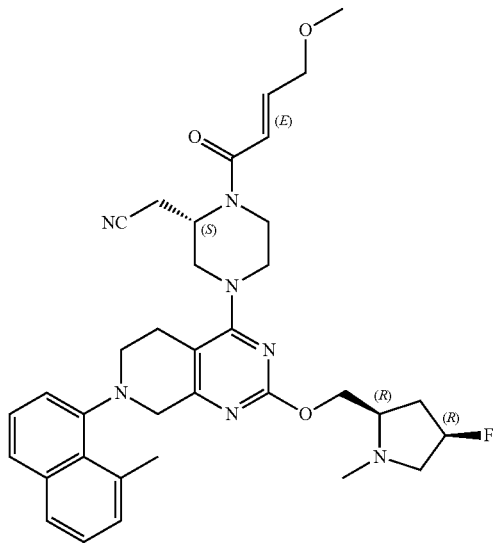

2-[(2S)-4-[2-[[(2R,4R)-4-fluoro-1-methyl-pyrrolidin-2-yl]methoxy]-7-(8-methyl-1-naphthyl)-6, 8-dihydro-5H-pyrido[3,4-d]pyrimidin-4-yl]-1-[(E)-4-methoxybut-2-enoyl]piperazin-2-yl]acetonitrile

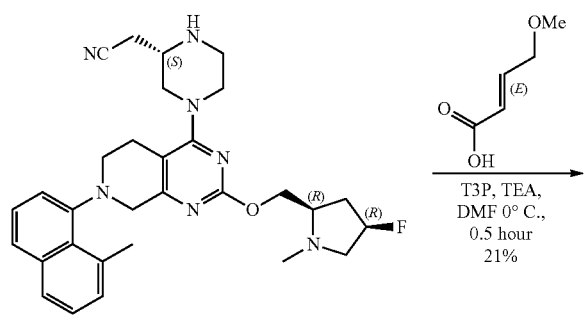

Step A: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-methoxybut-2-enoyl]piperazin-2-yl]acetonitrile To a solution of 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (200 mg, 378 umol, 1.0 eq), (E)-4-methoxybut-2-enoic acid (110 mg, 944 umol, 2.5 eq) in DMF (3.0 mL) was added TEA (382 mg, 3.78 mmol, 526 uL, 10.0 eq) and T3P (721 mg, 1.13 mmol, 674 uL, 50% purity, 3.0 eq). The mixture was stirred at 0° C. for 0.5 hour. After completion, the organic solvent was washed with water (10.0 mL). The aqueous phase was extracted with ethyl acetate (3×10.0 mL). Combine extracts were washed with brine (20.0 mL), dried with $Na_2SO_4$ and filtrated. The solvent was then removed under vacuum. The residue was purified by column chromatography (Base $Al_2O_3$, Petroleum ether: Ethyl acetate=10:1 to 1:1), then the crude product was concentrated and repurified by prep-HPLC (column: Phenomenex Gemini 150×25 mm×10 um; mobile phase: [water (0.05% ammonia hydroxide v/v)-ACN]; B %: 48%-78%,9-10 min) and lyophilization to give title compound 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-methoxybut-2-enoyl]piperazin-2-yl]acetonitrile (EXAMPLE 551, 50 mg, 79.6 umol, 21% yield, 99.9% purity) was obtained as yellow solid. LCMS [ESI, M+1]: 628.

$^1$H NMR (400 MHz, Chloroform-d) δ=7.73-7.62 (m, 2H), 7.45-7.31 (m, 2H), 7.27-7.18 (m, 2H), 7.05-6.94 (m, 1H), 6.55 (br d, J=15.0 Hz, 1H), 5.23-5.03 (m, 1H), 4.66 (br s, 1H), 4.52-4.42 (m, 1H), 4.30-4.18 (m, 2H), 4.18-3.94 (m, 4H), 3.93-3.84 (m, 1H), 3.83-3.65 (m, 1H), 3.54 (br d, J=6.7 Hz, 1H), 3.44 (s, 3H), 3.42-3.26 (m, 2H), 3.25-3.15 (m, 2H), 3.05 (br dd, J=8.5, 16.4 Hz, 2H), 2.92 (s, 3H), 2.88-2.58 (m, 4H), 2.57-2.35 (m, 5H), 2.14-1.96 (m, 1H).

Example 552

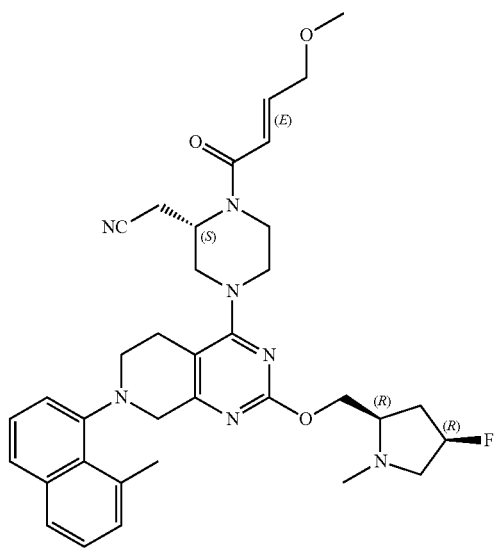

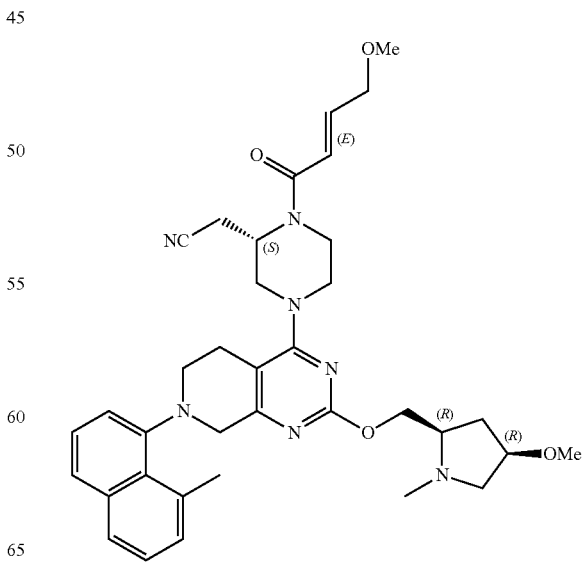

1401

2-[(2S)-1-[(E)-4-methoxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile

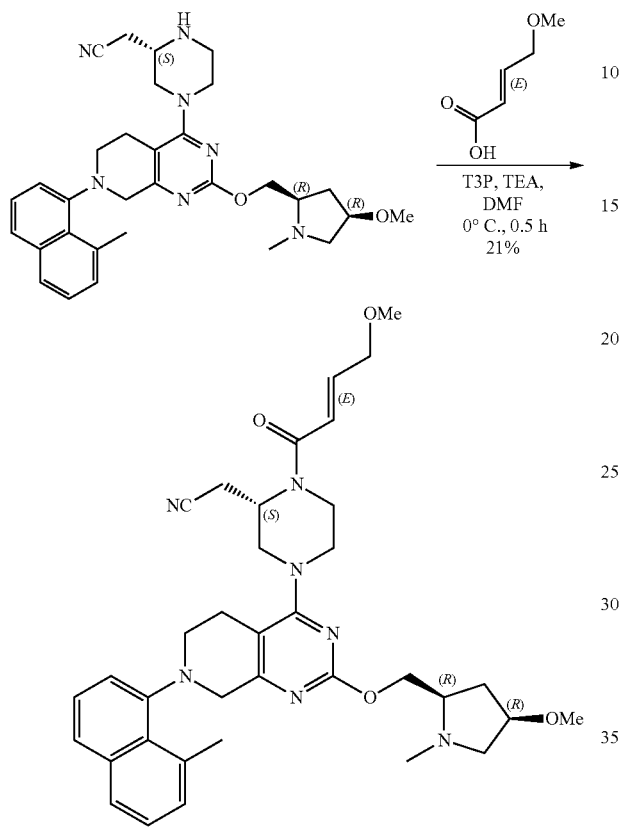

Step A: 2-[(2S)-1-[(E)-4-methoxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To the solution of 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (150 mg, 277 umol, 1 eq), (E)-4-methoxybut-2-enoic acid (64.3 mg, 554 umol, 2 eq) and TEA (280 mg, 2.77 mmol, 385 uL, 10 eq) in DMF (3 mL) was added T3P (529 mg, 831 umol, 494 uL, 50% purity, 3 eq) at 0° C., the mixture was stirred at 0° C. for 0.5 hour. Water (10 mL) was added into the mixture. The mixture was diluted with EtOAc (5 mL) and extracted with EtOAc (2×10 mL). The combined organic layers were washed with brine (10 mL), dried over anhydrous Na₂SO₄, filtered and concentrated under vacuum. The residue was purified by reversed phase flash column (ACN/Water (0.1% FA)=35%). Then the residue was purified by prep-HPLC (column: Waters Xbridge 150*25 5 u; mobile phase: [water (0.05% ammonia hydroxide v/v)-ACN]; B %: 50%-74%,10 min) to give title compound 2-[(2S)-1-[(E)-4-methoxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (EXAMPLE 552, 37.1 mg, 57.2 umol, 21% yield, 98.7% purity) as a white solid. LCMS [ESI, M+1]: 640.

¹H NMR (400 MHz, chloroform-d) δ=7.72-7.61 (m, 2H), 7.45-7.31 (m, 2H), 7.27-7.17 (m, 2H), 6.99 (br d, J=14.8 Hz, 1H), 6.55 (br d, J=15.2 Hz, 1H), 5.07 (br s, 1H), 4.51-4.40 (m, 1H), 4.31-4.04 (m, 5H), 3.95-3.68 (m, 3H), 3.63-3.47 (m, 2H), 3.44 (s, 3H), 3.42-3.35 (m, 1H), 3.30 (d, J=1.2 Hz, 3H), 3.24-2.96 (m, 5H), 2.92 (s, 3H), 2.76 (br dd, J=8.0, 16.8 Hz, 1H), 2.72-2.52 (m, 3H), 2.45 (d, J=5.2 Hz, 3H), 2.41-2.27 (m, 2H), 1.81 (br dd, J=7.2, 14.0 Hz, 1H).

Example 553

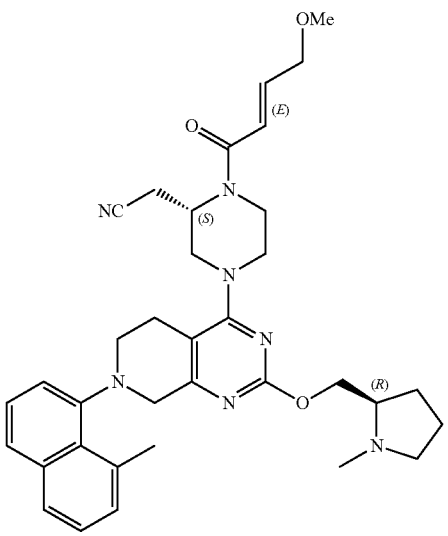

2-((S)-1-((E)-4-methoxybut-2-enoyl)-4-(7-(8-methylnaphthalen-1-yl)-2-(((R)-1-methylpyrrolidin-2-yl)methoxy)-5,6,7,8-tetrahydropyrido[3,4-d]pyrimidin-4-yl)piperazin-2-yl)acetonitrile

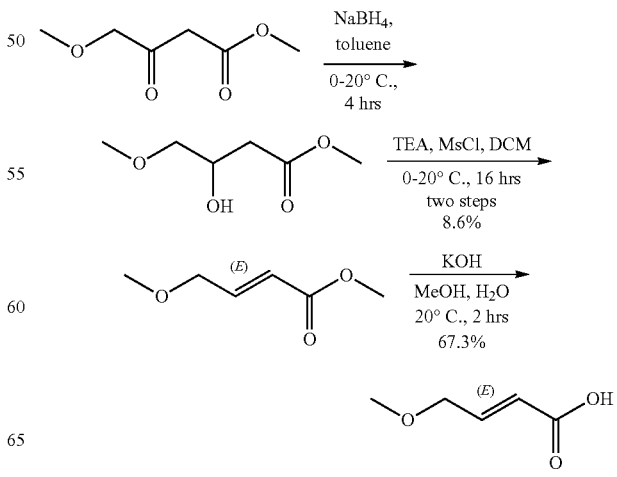

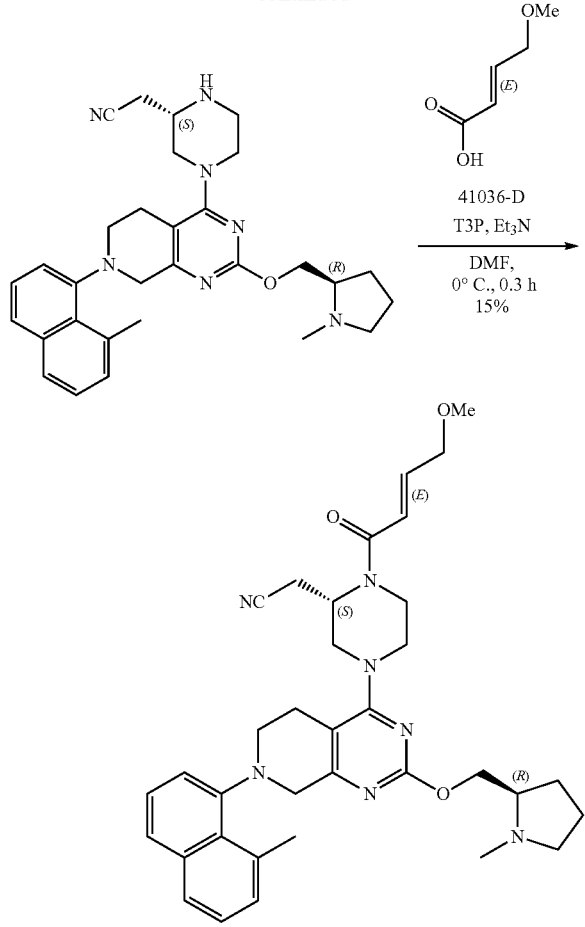

Step A: methyl 3-hydroxy-4-methoxy-butanoate

To a solution of methyl 4-methoxy-3-oxo-butanoate (20 g, 137 mmol, 1.0 eq) in toluene (300 mL) was added NaBH$_4$ (5.44 g, 144 mmol, 1.05 eq) at 0° C. Then the mixture was stirred at 20° C. for 4 hours. After completion, the mixture was diluted with water (100 mL) at 0° C. and extracted with ethyl acetate (3×100 mL). The extracts were washed with brine (200 mL), dried over Na$_2$SO$_4$, filtered and concentrated under vacuum to give methyl 3-hydroxy-4-methoxy-butanoate (7.5 g, crude) as yellow oil and used into next step without further purification.

$^1$H NMR (400 MHz, chloroform-d) δ=4.23-4.15 (m, 1H), 3.70 (s, 3H), 3.44-3.38 (m, 2H), 3.37 (s, 3H), 3.04 (br s, 1H), 2.51 (d, J=6.4 Hz, 2H).

Step B: methyl (E)-4-methoxybut-2-enoate

To a solution of methyl 3-hydroxy-4-methoxy-butanoate (7.5 g, crude) in DCM (50.0 mL) was added TEA (5.12 g, 50.6 mmol, 7.05 mL) and MsCl (8.70 g, 75.9 mmol, 5.88 mL) at 0° C. After stirred for 4 hours, to the mixture was added TEA (10.2 g, 101 mmol, 14.1 mL) 0° C. The mixture was warmed up to 20° C. and stirred for 12 hours. After completion, the mixture was diluted with water (50.0 mL), washed with HCl (1N, 15.0 mL) and brine (20.0 mL), dried over Na$_2$SO$_4$, filtered and concentrated under vacuum. The residue was purified by column chromatography (SiO$_2$, Petroleum ether/Ethyl acetate=1/0 to 50:1) to give methyl (E)-4-methoxybut-2-enoate (1.7 g, 11.8 mmol, two steps 8.6% yield, 90% purity) as yellow oil.

$^1$H NMR (400 MHz, chloroform-d) δ=6.93 (td, J=4.3, 15.8 Hz, 1H), 6.04 (td, J=2.0, 15.8 Hz, 1H), 4.06 (dd, J=2.0, 4.3 Hz, 2H), 3.72 (s, 3H), 3.36 (s, 3H).

Step C: (E)-4-methoxybut-2-enoic acid

A mixture of methyl (E)-4-methoxybut-2-enoate (300 mg, 2.31 mmol, 1.0 eq) and KOH (517 mg, 9.22 mmol, 4.0 eq) in MeOH (2.0 mL) and H$_2$O (2.0 mL) was stirred at 20° C. for 2 hours. After completion, the mixture was acidified with HCl (2N, 5.0 mL) to pH=1-3 and extracted with ethyl acetate (2×20 mL). The organic layers were dried over Na$_2$SO$_4$, filtered and concentrated under vacuum to give (E)-4-methoxybut-2-enoic acid (200 mg, 1.55 mmol, 67.3% yield, 90% purity) as yellow solid.

$^1$H NMR (400 MHz, chloroform-d) δ=11.13 (br s, 1H), 7.06 (td, J=4.1, 15.7 Hz, 1H), 6.08 (td, J=2.0, 15.7 Hz, 1H), 4.12 (dd, J=2.0, 4.1 Hz, 2H), 3.40 (s, 3H).

Step D: 2-[(2S)-1-[(E)-4-methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (200 mg, 391 umol, 1 eq), (E)-4-methoxybut-2-enoic acid (113 mg, 977 umol, 2.5 eq), TEA (395 mg, 3.91 mmol, 544 uL, 10 eq) in DMF (4 mL) was added T3P (746 mg, 1.17 mmol, 697 uL, 50% purity, 3 eq) at 0° C. The mixture was stirred at 0° C. for 0.3 hour. The reaction mixture was diluted with ethyl acetate (20 mL) and washed with water (10 mL×3). The organic layers were washed with brine (10 mL), dried over Na$_2$SO$_4$, filtered and concentrated under reduced pressure to give a residue. The residue was purified by column chromatography (SiO$_2$, Ethyl acetate/MeOH=100/1 to 10:1) and further purified by prep-HPLC (column: Boston pH-lex 150*25 10 um; mobile phase: [water (0.1% TFA)-ACN]; B %: 35%-59%, 8 min). The mixture was collected and lyophilized. Title compound 2-[(2S)-1-[(E)-4-methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (EXAMPLE 553, 37.5 mg, 60.4 umol, 15% yield, 98.2% purity) was obtained as a white solid. LCMS [ESI, M+1]: 610.

$^1$H NMR (400 MHz, chloroform-d) δ=7.77-7.57 (m, 2H), 7.46-7.37 (m, 1H), 7.34 (t, J=7.6 Hz, 1H), 7.27-7.17 (m, 2H), 6.99 (br d, J=14.4 Hz, 1H), 6.55 (br d, J=14.8 Hz, 1H), 5.24-4.49 (m, 1H), 4.46-4.32 (m, 1H), 4.32-3.74 (m, 7H), 3.73-3.25 (m, 6H), 3.25-2.94 (m, 5H), 2.92 (s, 3H), 2.86-2.54 (m, 4H), 2.49 (d, J=5.6 Hz, 3H), 2.38-2.23 (m, 1H), 2.11-2.00 (m, 1H), 1.93-1.65 (m, 3H).

Example 554

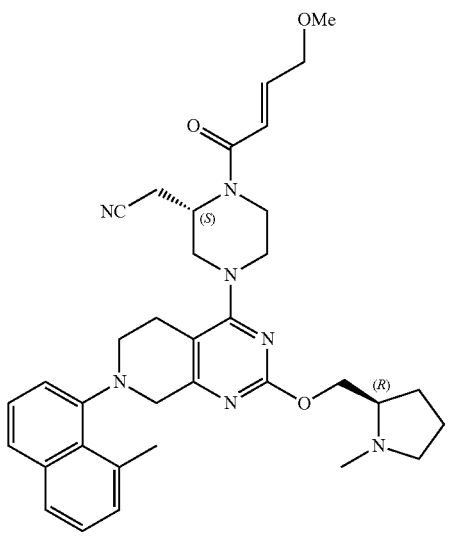

2-[(2S)-1-[(E)-4-Methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl] acetonitrile

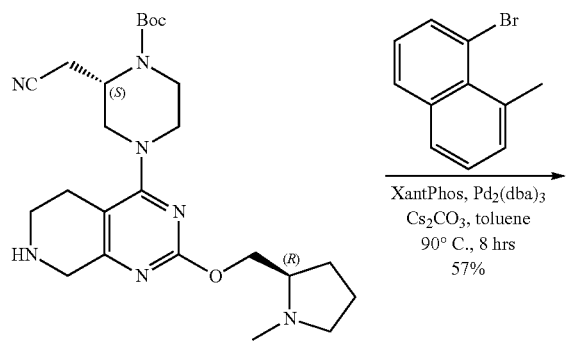

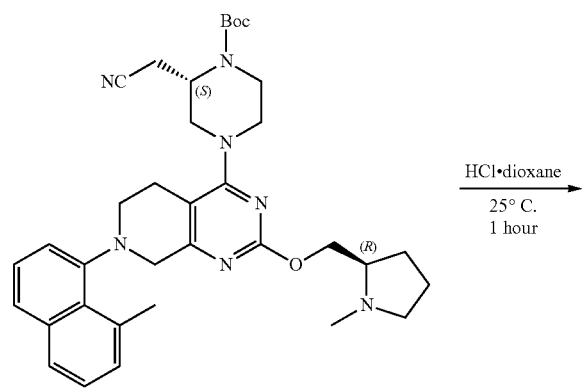

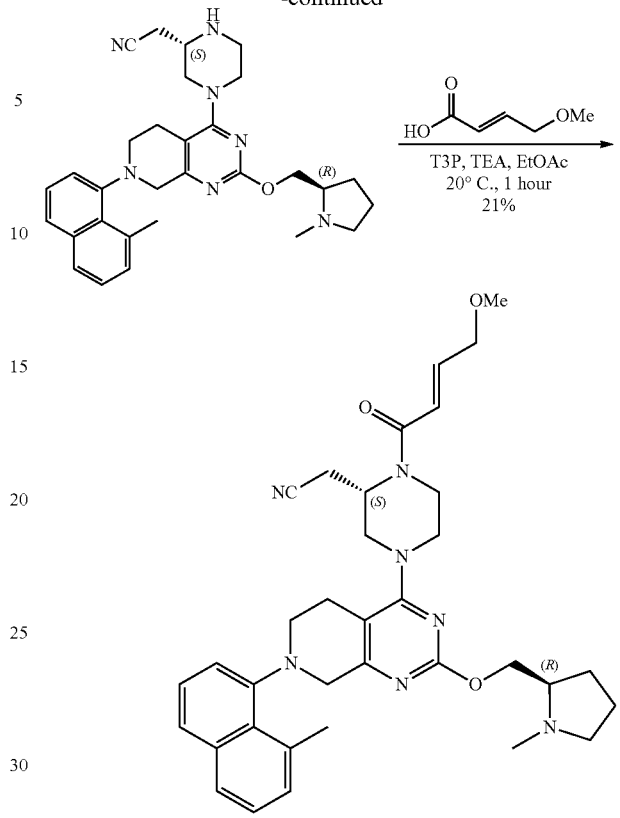

Step A: tert-butyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate A mixture of tert-butyl(2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (850 mg, 1.80 mmol, 1.0 eq), 1-bromo-8-methyl-naphthalene (1.20 g, 5.41 mmol, 3.0 eq), Pd$_2$(dba)$_3$ (330 mg, 360 µmol, 0.20 eq), Xantphos (417 mg, 721 µmol, 0.40 eq) and Cs$_2$CO$_3$ (1.76 g, 5.41 mmol, 3.0 eq) in toluene (10.0 mL) was degassed and purged with N$_2$ for 3 times, and then the mixture was stirred at 90° C. for 8 hours under N$_2$. After completion, the reaction was washed with 2 N HCl (2×15.0 mL). The aqueous phase was basified with solid NaHCO$_3$ to pH ~7 and extracted with ethyl acetate (2×50.0 mL). The organic layers were dried over Na$_2$SO$_4$, filtered and concentrated under vacuum. The residue was purified by reverse phase flash HPLC [C18, 0.1% FA in water, 0-65% MeCN] and was adjusted with solid NaHCO$_3$ to pH ~7 and extracted with ethyl acetate (2×150 mL). The organic layers were dried over Na$_2$SO$_4$, filtered and concentrated under vacuum. Compound tert-butyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (650 mg, 1.03 mmol, 57% yield, 97% purity) was obtained as white solid. LCMS [ESI, M+1]: 612.

$^1$H NMR (400 MHz, chloroform-d) δ 7.72-7.61 (m, 2H), 7.44-7.37 (m, 1H), 7.36-7.30 (m, 1H), 7.27-7.16 (m, 2H), 4.63-4.52 (m, 1H), 4.46-4.36 (m, 1H), 4.30-4.15 (m, 2H), 4.09-3.95 (m, 2H), 3.93-3.73 (m, 2H), 3.57-3.47 (m, 1H), 3.42-3.27 (m, 1H), 3.22-3.04 (m, 4H), 3.02-2.94 (m, 1H), 2.92 (s, 3H), 2.81-2.54 (m, 4H), 2.53-2.47 (m, 3H), 2.40-2.26 (m, 1H), 2.12-2.05 (m, 1H), 1.92-1.71 (m, 3H), 1.52 (s, 9H).

Step B: 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (600 mg, 981 µmol, 1.0 eq) in dioxane (3.0 mL) was added HCl/dioxane (4 M, 3.0 mL, 12.2 eq) at 25° C., and the mixture was stirred at 25° C. for 1 hour. After completion, the reaction mixture was quenched by saturated aqueous NaHCO₃ (8.0 mL) at 0° C., and then diluted with H₂O (5.0 mL) and extracted with ethyl acetate (3×15.0 mL). The combined organic layers were dried over Na₂SO₄, filtered and concentrated under reduced pressure to give 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (410 mg, crude) as yellow solid which was used into the next step without further purification.

Step C: 2-[(2S)-1-[(E)-4-methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl] acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (150 mg, 293 µmol, 1.0 eq), (E)-4-methoxybut-2-enoic acid (102 mg, 880 µmol, 3.0 eq) in ethyl acetate (3.0 mL) was added TEA (237 mg, 2.35 mmol, 326 µL, 8.0 eq) and T3P (560 mg, 880 µmol, 523 µL, 50% purity, 3.0 eq) at 0° C. The mixture was stirred at 20° C. for 1 hour. After completion, water was added (5.0 mL). The organic layer was separated, and the aqueous phase was extracted with ethyl acetate (3×10 mL). Combined extracts were washed with brine (20.0 mL), dried with Na₂SO₄, filtered and concentrated under vacuum. The residue was purified by column chromatography (basic Al₂O₃, petroleum ether: ethyl acetate=3:1 to ethyl acetate:methanol=50:1), then the crude product repurified by prep-HPLC (column: Waters Xbridge 150*25 5 u; mobile phase: [water (0.05% ammonium hydroxide v/v)-MeCN]; B %: 50%-77%,10 min) and lyophilization. Compound 2-[(2S)-1-[(E)-4-methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl] acetonitrile (38.6 mg, 62.4 µmol, 21% yield, 98% purity) was obtained as white solid. LCMS [ESI, M+1]: 512.

Step D: 2-[(2S)-1-[(E)-4-methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl] acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (150 mg, 293 µmol, 1.0 eq), (E)-4-methoxybut-2-enoic acid (102 mg, 880 µmol, 3.0 eq) in ethyl acetate (3.0 mL) was added TEA (237 mg, 2.35 mmol, 326 µL, 8.0 eq) and T3P (560 mg, 880 µmol, 523 µL, 50% purity, 3.0 eq) at 0° C. The mixture was stirred at 20° C. for 1 hour. After completion, water was added (5.0 mL). The organic layer was separated, and the aqueous phase was extracted with ethyl acetate (3×10 mL). Combined extracts were washed with brine (20.0 mL), dried with Na₂SO₄, filtered and concentrated under vacuum. The residue was purified by column chromatography (basic Al₂O₃, petroleum ether: ethyl acetate=3:1 to ethyl acetate:methanol=50:1), then the crude product repurified by prep-HPLC (column: Waters Xbridge 150*25 5 u; mobile phase: [water (0.05% ammonium hydroxide v/v)-MeCN]; B %: 50%-77%,10 min) and lyophilization. Compound 2-[(2S)-1-[(E)-4-methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl] acetonitrile (38.6 mg, 62.4 µmol, 21% yield, 98% purity) was obtained as white solid. LCMS [ESI, M+1]: 610.

¹H NMR (400 MHz, chloroform-d) δ 7.73-7.62 (m, 2H), 7.45-7.31 (m, 2H), 7.26-7.17 (m, 2H), 6.99 (br d, J=15.2 Hz, 1H), 6.55 (br d, J=15.6 Hz, 1H), 5.20-4.50 (m, 1H) 4.43-4.33 (m, 1H), 4.29-3.96 (m, 6H), 3.94-3.83 (m, 1H), 3.81-3.63 (m, 1H), 3.58-3.37 (m, 5H), 3.23-2.96 (m, 5H), 2.92 (s, 3H), 2.87-2.54 (m, 4H), 2.52-2.43 (m, 3H), 2.33-2.24 (m, 1H), 2.13-2.01 (m, 1H), 1.87-1.72 (m, 3H).

Example 555

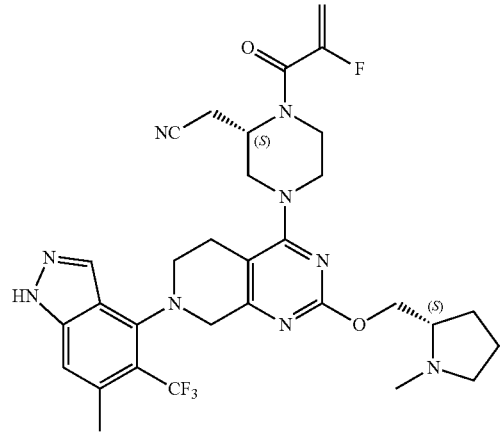

2-((S)-1-(2-Fluoroacryloyl)-4-(7-(6-methyl-5-(trifluoromethyl)-1H-indazol-4-yl)-2-(((S)-1-methylpyrrolidin-2-yl)methoxy)-5,6,7,8-tetrahydropyrido [3,4-d]pyrimidin-4-yl)piperazin-2-yl)acetonitrile

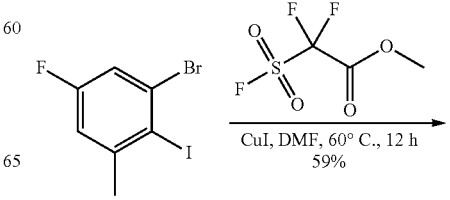

-continued

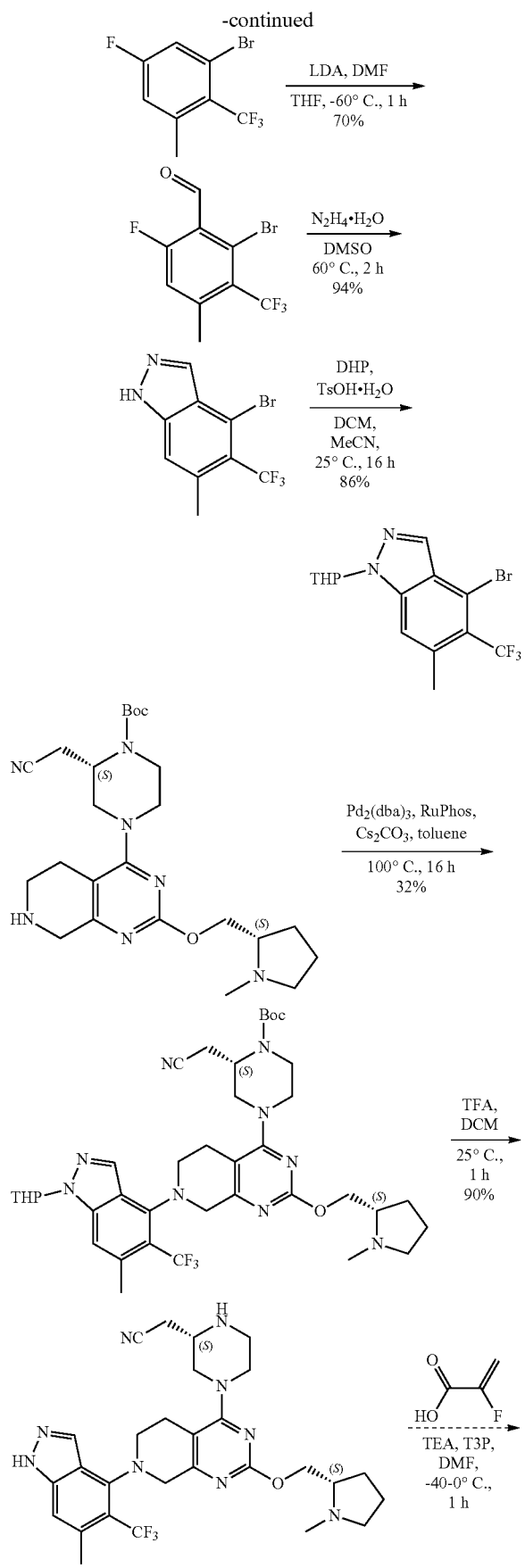

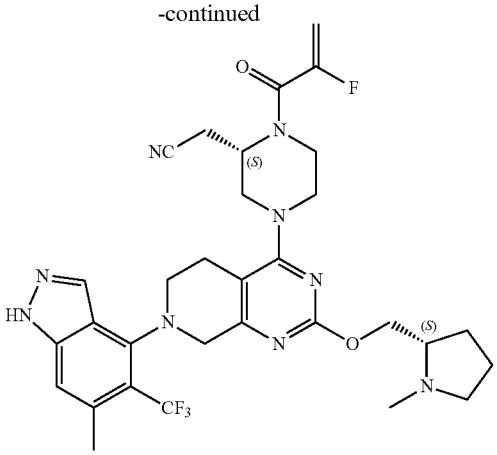

1-Bromo-5-fluoro-3-methyl-2-(trifluoromethyl)benzene

To a solution of 1-bromo-5-fluoro-2-iodo-3-methyl-benzene (2 g, 6.35 mmol, 1 eq) in DMF (40 mL) was added CuI (7.26 g, 38.1 mmol, 6 eq) and methyl 2,2-difluoro-2-fluorosulfonyl-acetate (7.32 g, 38.1 mmol, 4.85 mL, 6 eq). The mixture was stirred at 60° C. for 12 hours. The reaction mixture was diluted with ethyl acetate (20 mL) and washed with water (20 mL×3). The organic layer was washed with brine (20 mL), dried over $Na_2SO_4$, filtered and concentrated under reduced pressure to give a residue. The residue was purified by column chromatography ($SiO_2$, petroleum ether/ethyl acetate=1/0 to 10/1). 1-bromo-5-fluoro-3-methyl-2-(trifluoromethyl)benzene (1.3 g, 3.74 mmol, 59% yield, 74% purity) was obtained as a yellow oil.
$^1$H NMR (400 MHz, chloroform-d) δ=7.33 (dd, J=2.4, 7.6 Hz, 1H), 6.95 (dd, J=2.0, 8.8 Hz, 1H), 2.54 (q, J=3.6 Hz, 3H).

2-Bromo-6-fluoro-4-methyl-3-(trifluoromethyl)benzaldehyde

To a mixture of 1-bromo-5-fluoro-3-methyl-2-(trifluoromethyl)benzene (900 mg, 3.50 mmol, 1 eq) in THF (20 mL) was added LDA (2 M in THF, 3.50 mL, 2 eq) at −60° C. under nitrogen. After stirring for 0.5 hour, to the mixture was added DMF (768 mg, 10.5 mmol, 808 μL, 3 eq). The mixture was stirred at −60° C. for 1 hour. The reaction was quenched with saturated aqueous $NH_4Cl$ (10 mL) and then extracted with ethyl acetate (50 mL×3). The combined organic phase was washed with brine (10 mL), dried over anhydrous $Na_2SO_4$, filtered and concentrated in vacuo. The residue was purified by column chromatography ($SiO_2$, petroleum ether/ethyl acetate=200/1 to 5/1). 2-bromo-6-fluoro-4-methyl-3-(trifluoromethyl)benzaldehyde (700 mg, 2.46 mmol, 70% yield) was obtained as a yellow oil.
$^1$H NMR (400 MHz, chloroform-d) δ=10.35 (s, 1H), 7.08 (d, J=10.4 Hz, 1H), 2.66-2.58 (m, 3H).

4-Bromo-6-methyl-5-(trifluoromethyl)-1H-indazole

A solution of 2-bromo-6-fluoro-4-methyl-3-(trifluoromethyl)benzaldehyde (600 mg, 2.11 mmol, 1 eq) and hydrazine monohydrate (2.11 g, 42.1 mmol, 2.05 mL, 20 eq) in DMSO (8 mL) was stirred at 60° C. for 2 hours. The mixture was diluted with ethyl acetate (50 mL) and washed with water (3×50 mL) and brine (1×50 mL). The separated organic layer was dried over sodium sulfate, filtered and concentrated under vacuum. The residue was used in the next step without further purification. 4-Bromo-6-methyl-5-(trifluoromethyl)-1H-indazole (550 mg, 1.97 mmol, 94% yield) was obtained as a white solid.

4-Bromo-6-methyl-1-tetrahydropyran-2-yl-5-(trifluoromethyl)indazole

To a solution of 4-bromo-6-methyl-5-(trifluoromethyl)-1H-indazole (500 mg, 1.79 mmol, 1 eq) in DCM (10 mL) was added 4-methylbenzenesulfonic acid hydrate (34.1 mg, 1791 µmol, 0.1 eq) followed by a solution of DHP (603 mg, 7.17 mmol, 655 µL, 4 eq) in CH$_3$CN (2 mL). The mixture was stirred at 25° C. for 16 hours. The mixture was diluted with ethyl acetate (100 mL) and washed with water (2×100 mL) and brine (1×50 mL). The organic layer was dried over sodium sulfate, filtered and concentrated under vacuum. The residue was purified by column chromatography over silica gel (petroleum ether/ethyl acetate 20/1 to 3/1). The desired fractions were collected and concentrated under vacuum to give 4-bromo-6-methyl-1-tetrahydropyran-2-yl-5-(trifluoromethyl)indazole (600 mg, 1.54 mmol, 86% yield, 93% purity) as a light yellow gum. LCMS [MSI, M+1]: 363.

Step A: tert-Butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl)indazol-4-yl]-6,8-dihydro-5H-pyrido[3,4-d]pyrimidin-4-yl]piperazine-1-carboxylate A mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (400 mg, 848 µmol, 1 eq), 4-bromo-6-methyl-1-tetrahydropyran-2-yl-5-(trifluoromethyl)indazole (431 mg, 1.19 mmol, 1.4 eq) Pd$_2$(dba)$_3$ (155 mg, 170 µmol, 0.2 eq), RuPhos (158 mg, 339 µmol, 0.4 eq) and Cs$_2$CO$_3$ (691 mg, 2.12 mmol, 2.5 eq) in toluene (20 mL) was degassed and purged with N$_2$ for 3 times, and stirred at 100° C. for 16 hours under N$_2$. To the mixture was added H$_2$O (20 mL×1) and ethyl acetate (20 mL×1). The organic phase was separated, filtered and concentrated under reduced pressure to give a residue. The residue was purified by silica gel chromatography (ethyl acetate/methanol=50/1 to 2/1). tert-Butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl)indazol-4-yl]-6,8-dihydro-5H-pyrido[3,4-d]pyrimidin-4-yl]piperazine-1-carboxylate (500 mg, 535 µmol, 32% yield, 80.7% purity) was obtained as a yellow solid. LCMS [MSI, M+1]: 754.

Step B: 2-[(2S)-4-[2-[[(2S)-1-Methylpyrrolidin-2-yl]methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile To a solution of tert-butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl)indazol-4-yl]-6,8-dihydro-5H-pyrido[3,4-d]pyrimidin-4-yl]piperazine-1-carboxylate (470 mg, 503 µmol, 1 eq) in DCM (1 mL) was added TFA (2.29 g, 20.1 mmol, 1.49 mL, 40 eq). The mixture was stirred at 25° C. for 1 h. To the mixture was added dichloromethane (5 mL) and basified with saturated aqueous NaHCO$_3$ to pH=8~9. The organic phase was separated, dried over sodium sulfate, filtered and concentrated under reduced pressure to give 2-[(2S)-4-[2-[[(2S)-1-methylpyrrolidin-2-yl]methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile (420 mg, 453 µmol, 90% yield, 61.4% purity) as a yellow solid that was used into next step without further purification. LCMS [MSI, M+1]: 570.

Step C: 2-((S)-1-(2-Fluoroacryloyl)-4-(7-(6-methyl-5-(trifluoromethyl)-1H-indazol-4-yl)-2-(((S)-1-methylpyrrolidin-2-yl)methoxy)-5,6,7,8-tetrahydropyrido[3,4-d]pyrimidin-4-yl)piperazin-2-yl)acetonitrile To a solution of 2-[(2S)-4-[2-[[(2S)-1-methylpyrrolidin-2-yl] methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile (380 mg, 410 µmol, 1 eq), 2-fluoroprop-2-enoic acid (18.4 mg, 205 µmol, 0.5 eq) and TEA (124 mg, 1.23 mmol, 171 µL, 3 eq) in DMF (8 mL) was added T3P (391 mg, 614 µmol, 365 µL, 50% purity in DMF, 1.5 eq) at −40° C. Then the mixture was stirred at −40° C. for 0.5 hour and 0° C. for another 0.5 hour. 2-Fluoroprop-2-enoic acid (11 mg) and T3P (100 µL) were added and the mixture was stirred at −40° C. for further 0.5 hour. The mixture was diluted with water (15 mL) and extracted with EtOAc (2×40 mL). The organic layers were washed with brine (50 mL), dried over Na$_2$SO$_4$ and concentrated under vacuum. The residue was purified by prep-HPLC (column: Luna C18 150*25 5 u; mobile phase: [water (0.225% FA)-MeCN]; B %: 22%-42%, 7.8 min) and (column: Phenomenex Gemini 150*25 mm*10 µm; mobile phase: [water (0.04% NH$_3$H$_2$O+10 mM NH$_4$HCO$_3$)-MeCN]; B %: 50%-68%, 12 min). The desired fractions were collected and lyophilized to give title compound 2-((S)-1-(2-fluoroacryloyl)-4-(7-(6-methyl-5-(trifluoromethyl)-1H-indazol-4-yl)-2-((S)-1-methylpyrrolidin-2-yl)methoxy)-5,6,7,8-tetrahydropyrido[3,4-d]pyrimidin-4-yl)piperazin-2-yl)acetonitrile as white solid. LCMS [ESI, M+1]: 642.

Example 556

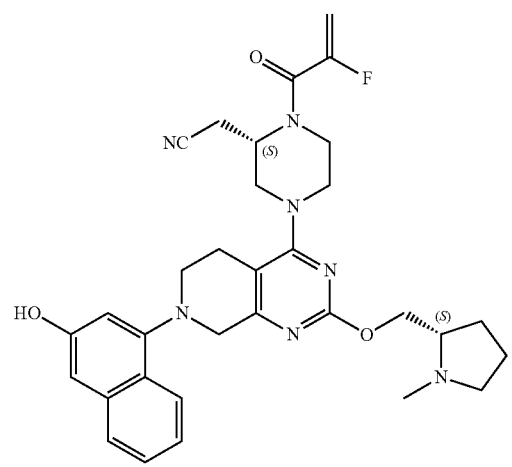

1413

2-[(2S)-1-(2-Fluoroprop-2-enoyl)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile

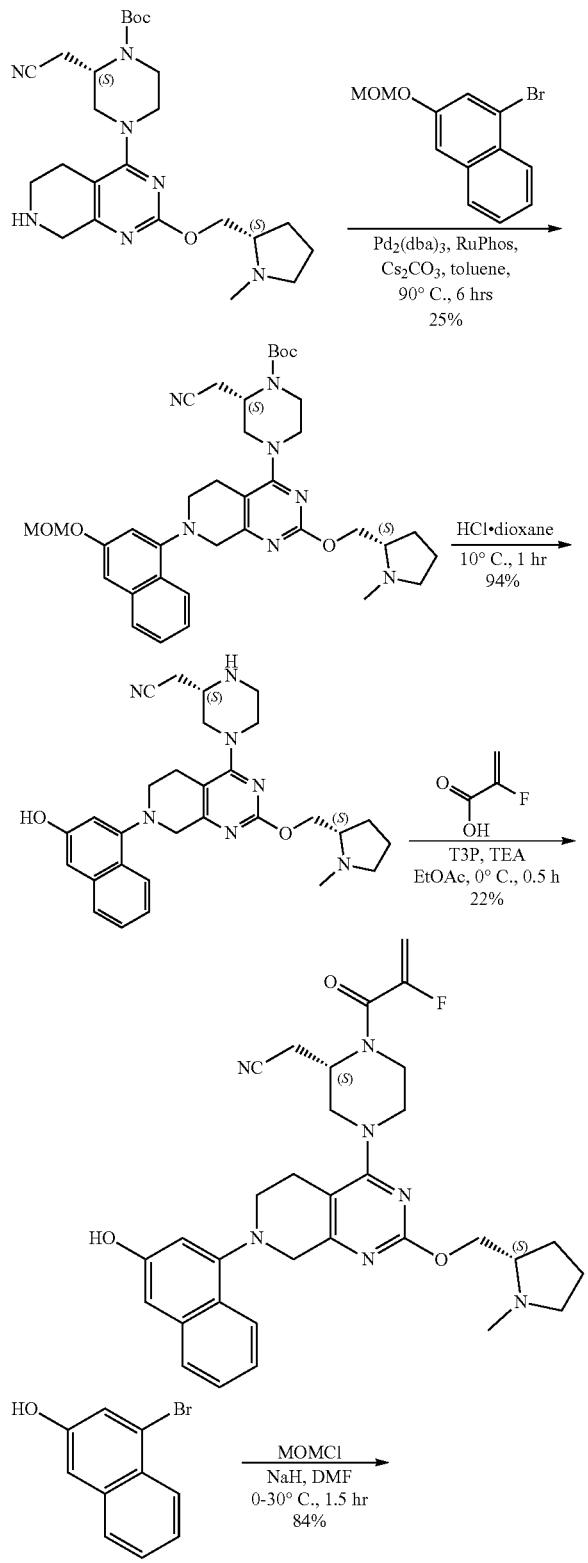

1414

3-Bromo-1-(methoxymethoxy)naphthalene

To a solution of 4-bromonaphthalen-2-ol (3.50 g, 15.7 mmol, 1.0 eq) in DMF (35.0 mL) was added NaH (941 mg, 23.5 mmol, 60% purity, 1.50 eq). After addition, the mixture was stirred at this temperature for 0.5 hour, and then chloro(methoxy)methane (5.90 g, 73.3 mmol, 5.57 mL, 4.67 eq) was added dropwise at 0° C. The mixture was warmed to 30° C. and stirred for further 1 hour. After completion, the combined reaction mixture was diluted with water (100 mL) and extracted with EtOAc (3×50.0 mL). The combined organic layers were washed with saturated brine (200 mL), dried over $Na_2SO_4$, filtered and concentrated under reduced pressure to give a residue. The residue was purified by column chromatography ($SiO_2$, petroleum ether/ethyl acetate=1/0 to 100/1). Compound 3-bromo-1-(methoxymethoxy)naphthalene (3.50 g, 13.1 mmol, 84% yield) was obtained as a red oil.

$^1$H NMR (400 MHz, chloroform-d) δ 8.19-8.12 (m, 1H), 7.78-7.71 (m, 1H), 7.61-7.57 (m, 1H), 7.52-7.44 (m, 2H), 7.40 (d, J=2.0 Hz, 1H), 5.29 (s, 2H), 3.53 (s, 3H).

Step A: tert-Butyl (2S)-2-(cyanomethyl)-4-[7-[3-(methoxymethoxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate To a solution of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (800 mg, 1.70 mmol, 1.0 eq) and 1-bromo-3-(methoxymethoxy)naphthalene (680 mg, 2.54 mmol, 1.50 eq) in toluene (10.0 mL) was added $Cs_2CO_3$ (2.21 g, 6.79 mmol, 4.00 eq), RuPhos (158 mg, 339 μmol, 0.20 eq) and $Pd_2(dba)_3$ (233 mg, 254 μmol, 0.15 eq). The mixture was stirred at 90° C. for 6 hours. The reaction mixture was diluted with $H_2O$ 100 mL and extracted with ethyl acetate (3×100 mL). The combined organic layers were concentrated under reduced pressure to give a residue. The residue was further purified by reverse phase flash [water (0.1% formic acid)/acetonitrile)]. The mixture was adjusted pH=7 with $NaHCO_3$ aqueous solution and extracted with ethyl acetate (3×50.0 mL). The combined organic layers were washed with saturated brine (100 mL), dried over $Na_2SO_4$, filtered and concentrated under reduced pressure to give the product. Compound tert-butyl (2S)-2-(cyanomethyl)-4-[7-[3-(methoxymethoxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate (280 mg, 426 μmol, 25% yield) was obtained as a yellow solid. LCMS [ESI, M+1]: 658.

$^1$H NMR (400 MHz, chloroform-d) δ 8.09 (d, J=8.0 Hz, 1H), 7.75 (d, J=8.2 Hz, 1H), 7.45 (t, J=7.0 Hz, 1H), 7.40-7.34 (m, 1H), 7.16 (d, J=2.0 Hz, 1H), 6.87 (d, J=2.4 Hz, 1H), 5.30 (s, 2H), 4.63 (br s, 1H), 4.40 (dd, J=4.8, 10.4 Hz, 1H), 4.33-4.22 (m, 2H), 4.21-4.16 (m, 1H), 4.09-3.86 (m, 3H), 3.54 (s, 3H), 3.51-3.40 (m, 1H), 3.37-3.17 (m, 3H), 3.15-2.96 (m, 3H), 2.89-2.73 (m, 3H), 2.72-2.64 (m, 1H), 2.49 (s, 3H), 2.33-2.25 (m, 1H), 2.13-2.05 (m, 1H), 1.91-1.78 (m, 3H), 1.52 (s, 9H).

Step B: 2-[(2S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-[3-(methoxymethoxy)-1-naphthyl]-2-[[(2S)-1-methylpyrrolidin-2-yl]methoxy]-6,8-dihydro-5H-pyrido[3,4-d]pyrimidin-4-yl]piperazine-1-carboxylate (260 mg, 395 μmol, 1.0 eq) in dioxane (2.0 mL) was added HCl.dioxane (4 M, 98.8 μL, 1.0 eq). The mixture was stirred at 20° C. for 1 hour. After completion, the reaction mixture was concentrated under reduced pressure to give a residue. The residue was adjusted pH=7 with saturated of NaHCO$_3$ aqueous solution and extracted with ethyl acetate (3×20.0 mL). The combined organic layers were washed with saturated brine (30.0 mL), dried over Na$_2$SO$_4$, filtered and concentrated under reduced pressure to give the residue. Compound 2-[(2S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 373 μmol, 94% yield, 96% purity) was obtained as a yellow solid. LCMS [ESI, M+1]: 514.

Step C: 2-[(2S)-1-(2-fluoroprop-2-enoyl)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 389 μmol, 1.0 eq) and 2-fluoroprop-2-enoic acid (105 mg, 1.17 mmol, 3.0 eq) in DMF (4.00 mL) was added TEA (158 mg, 1.56 mmol, 217 μL, 4.0 eq) and T3P (743 mg, 1.17 mmol, 695 μL, 50% purity, 3.0 eq) at 0° C. The mixture was stirred at 0° C. for 0.5 hour. After completion, the reaction mixture was diluted with H$_2$O (10.0 mL) and extracted with DCM (3×10.0 mL). The combined organic layers were washed with saturated brine (20.0 mL), dried over Na$_2$SO$_4$, filtered and concentrated under reduced pressure to give a residue. The residue was purified by column chromatography (Al$_2$O$_3$, petroleum ether/ethyl acetate=10/1 to DCM/MeOH=5/1), and the residue was purified by prep-HPLC (column: Phenomenex Gemini 150*25 mm*10 μm; mobile phase: [water (0.04% NH3H2O+10 mM NH4HCO3)-MeCN]; B %: 45%-75%,12 min). Title compound 2-[(2S)-1-(2-fluoroprop-2-enoyl)-4-[7-(3-hydroxy-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (50.0 mg, 85.0 μmol, 22% yield, 99.6% purity) was obtained as a yellow solid. LCMS [ESI, M+1]: 586.

$^1$H NMR (400 MHz, chloroform-d) δ 7.94 (br d, J=8.4 Hz, 1H), 7.62 (d, J=8.0 Hz, 1H), 7.40 (t, J=7.2 Hz, 1H), 7.31-7.26 (m, 1H), 6.86 (s, 1H), 6.52 (br s, 1H), 5.51-5.29 (m, 1H), 5.25 (dd, J=3.6, 16.8 Hz, 1H), 4.95-4.35 (m, 2H), 4.24 (dd, J=4.4, 11.2 Hz, 1H), 4.15-3.93 (m, 3H), 3.85-3.69 (m, 1H), 3.45-3.26 (m, 1H), 3.25-3.18 (m, 2H), 3.17-2.95 (m, 2H), 2.94-2.73 (m, 3H), 2.72-2.62 (m, 5H), 2.60-2.50 (m, 1H), 2.45-2.35 (m, 1H), 2.15-2.06 (m, 1H), 2.01-1.93 (m, 1H), 1.88-1.74 (m, 3H).

Example 557

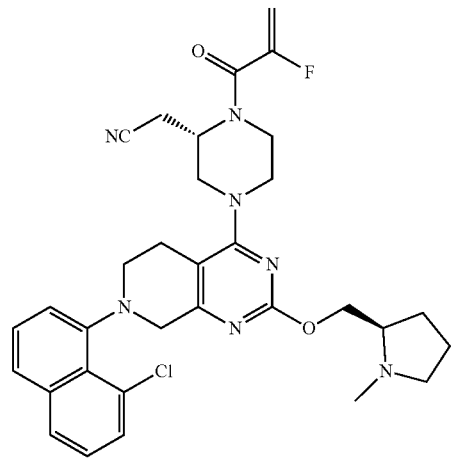 [SMILES: C=C(F)C(=O)N1CCN(c2nc(OC[C@H]3CCCN3C)nc3c2CCN(c2cccc4cccc(Cl)c24)C3)C[C@@H]1CC#N]

2-[(2S)-4-[7-(8-Chloro-1-naphthyl)-2-[[(2R)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

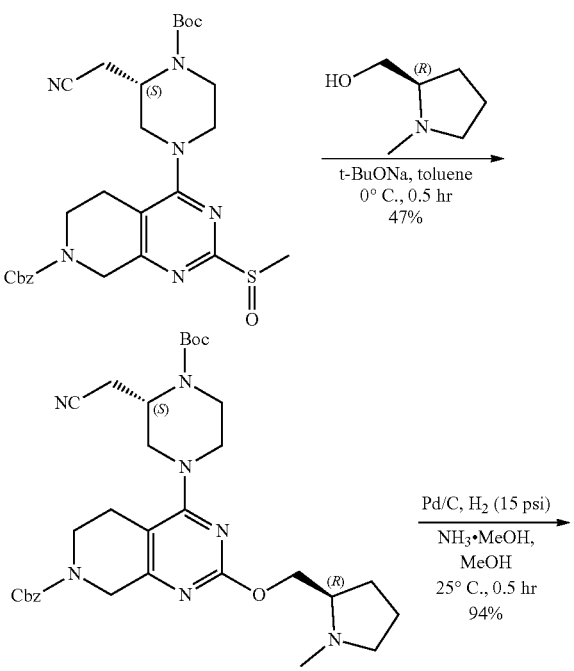

1417

-continued

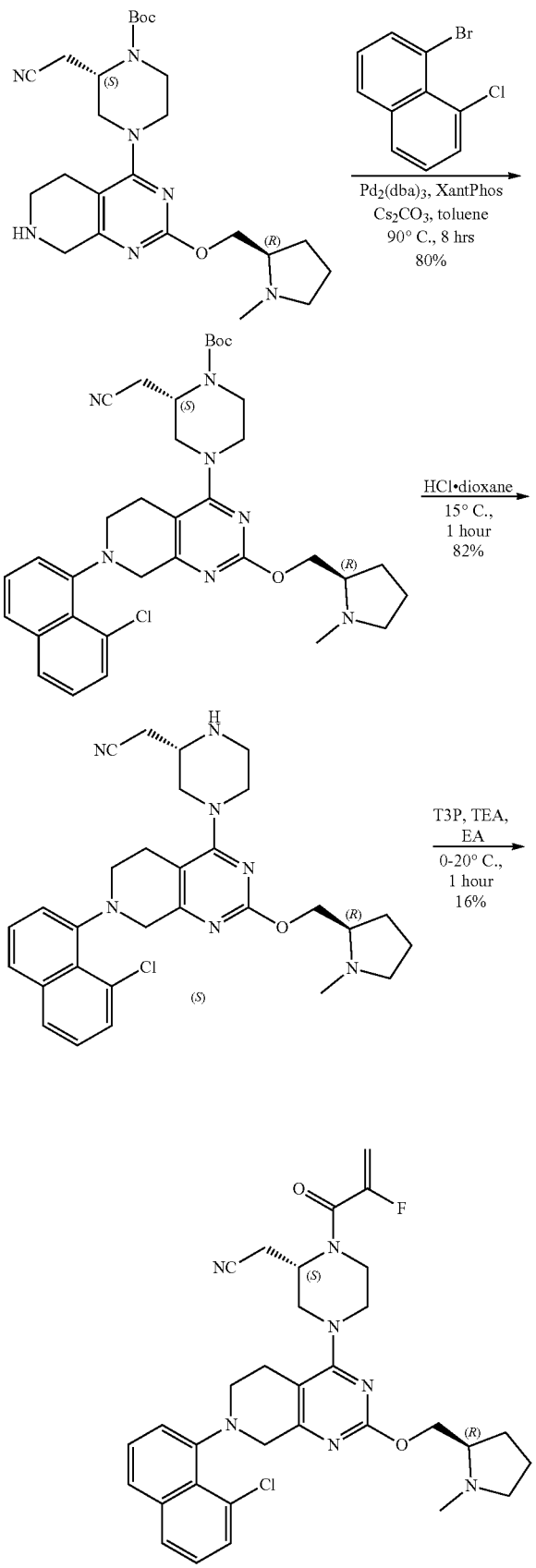

1418

Step A: Benzyl 4-[(3S)-4-tert-butoxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate To a solution of [(2R)-1-methylpyrrolidin-2-yl]methanol (934 mg, 8.11 mmol, 3.0 eq) and t-BuONa (780 mg, 8.11 mmol, 3.0 eq) in toluene (15.0 mL) was added a solution of benzyl 4-[(3S)-4-tert-butoxycarbonyl-3-(cyanomethyl)piperazin-1-yl]-2-methylsulfinyl-6,8-dihydro-5H-pyrido[3,4-d]pyrimidine-7-carboxylate (1.5 g, 2.70 mmol, 1.0 eq) in toluene (10.0 mL) dropwise at 0° C. The reaction mixture was stirred at 0° C. for another 0.5 hr. After completion, the reaction was quenched with water (30.0 mL). The crude mixture was extracted with ethyl acetate (2×50.0 mL). Combine extracts were washed with brine (100 mL), dried with $Na_2SO_4$, the solvent was then removed under vacuum. The residue was purified by reverse phase flash HPLC [C18, 0.1% FA in water, 0-65% MeCN] and was acidified with $NaHCO_3$ to pH=8 and extracted with ethyl acetate (2×150 mL). The organic layers were dried over $Na_2SO_4$, filtered and concentrated under vacuum. Compound benzyl 4-[(3S)-4-tert-butoxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (820 mg, 1.26 mmol, 47% yield, 93% purity) was obtained as white solid. LCMS [ESI, M+1]: 606.

$^1$H NMR (400 MHz, chloroform-d) δ 7.42-7.29 (m, 5H), 5.18 (s, 2H), 4.69 (br d, J=18.6 Hz, 1H), 4.59 (br s, 1H), 4.44 (d, J=18.8 Hz, 1H), 4.34 (br s, 1H), 4.05-3.69 (m, 4H), 3.42 (br s, 1H), 3.24 (br d, J=13.0 Hz, 2H), 3.09 (br t, J=7.6 Hz, 1H), 3.02-2.90 (m, 1H), 2.81-2.56 (m, 5H), 2.47 (s, 3H), 2.28 (dt, J=7.2, 9.4 Hz, 1H), 2.05-1.99 (m, 1H), 1.89-1.67 (m, 4H), 1.51 (s, 9H).

Step B: tert-Butyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate $NH_3$ was bubbled into MeOH (10.0 mL) of at −70° C. for 0.5 hr. Benzyl 4-[(3S)-4-tert-butoxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (820 mg, 1.35 mmol, 1.0 eq) and Pd/C (250 mg, 10% purity) was added to the above mixture and MeOH (10.0 mL), then the mixture was degassed and purged with $H_2$ 3 times, and then the mixture was stirred at 20° C. for 0.5 hr under $H_2$ (15 psi). After completion, the crude mixture was filtered through a pad of celite. The cake was washed with MeOH (50.0 mL) and the filtrate dried under high vacuum. Compound tert-butyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (600 mg, 1.27 mmol, 94% yield, 100% purity) was obtained as white solid and used into the next step without further purification. LCMS [ESI, M+1]: 472.

Step C: tert-Butyl(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate A mixture of tert-butyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (550 mg, 1.17 mmol, 1.0 eq), 1-bromo-8-chloro-naphthalene (845 mg, 3.50 mmol, 3.0 eq), Pd$_2$(dba)$_3$ (160 mg, 175 μmol, 0.15 eq), Xantphos (135 mg, 233 μmol, 0.20 eq) and Cs$_2$CO$_3$ (1.14 g, 3.50 mmol, 3.0 eq) in toluene (10.0 mL) was degassed and purged with N$_2$ 3 times, and then the mixture was stirred at 90° C. for 8 hrs under N$_2$. After completion, the reaction was washed with HCl (2N 2×15 mL) aqueous solution. The aqueous phase was basified with NaHCO$_3$ to pH 8 and extracted with ethyl acetate (2×50 mL). The organic layers were dried over Na$_2$SO$_4$, filtered and concentrated under vacuum. The residue was purified by reverse phase flash HPLC [C18, 0.1% FA in water, 0-65% MeCN] and was acidified with NaHCO$_3$ to pH=8 and extracted with ethyl acetate (2×150 mL). The organic layers were dried over Na$_2$SO$_4$, filtered and concentrated under vacuum. Compound tert-butyl(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate (600 mg, 930 μmol, 80% yield, 98% purity) was obtained as white solid. LCMS [ESI, M+1]: 632.

$^1$H NMR (400 MHz, chloroform-d) δ 7.75 (br d, J=8.2 Hz, 1H), 7.61 (t, J=8.0 Hz, 1H), 7.52 (d, J=7.5 Hz, 1H), 7.44 (td, J=7.8, 15.2 Hz, 1H), 7.33 (t, J=7.8 Hz, 1H), 7.27-7.17 (m, 1H), 4.61 (br s, 1H), 4.48-4.34 (m, 2H), 4.10-3.91 (m, 3H), 3.90-3.78 (m, 1H), 3.63-3.53 (m, 1H), 3.34 (br dd, J=3.6, 13.8 Hz, 1H), 3.30-3.01 (m, 5H), 2.95 (dt, J=3.5, 12.3 Hz, 1H), 2.89-2.75 (m, 1H), 2.70 (br s, 2H), 2.57 (br d, J=14.2 Hz, 1H), 2.53-2.46 (m, 3H), 2.35-2.25 (m, 1H), 2.13-2.06 (m, 1H), 1.93-1.66 (m, 3H), 1.52 (s, 9H).

Step D: 2-[(2S)-4-[7-(8-Chloro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate (200 mg, 316 μmol, 1.0 eq) in dioxane (2.0 mL) was added HCl/dioxane (4 M, 2.0 mL, 25.3 eq). The mixture was stirred at 20° C. for 0.5 hour under N$_2$. After completion, the organic solvent was removed under vacuum. The obtained product was adjusted with saturated aqueous NaHCO$_3$ to Ph=8, then concentrated. The aqueous phase was extracted with ethyl acetate (3×10.0 mL), the combined organic layer was dried over Na$_2$SO$_4$, filtered and concentrated. The crude product 2-[(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (145 mg, 259 μmol, 82% yield, 95% purity) was obtained as yellow solid and used into the next step without further purification. LCMS [ESI, M+1]: 532

Step E: 2-[(2S)-4-[7-(8-Chloro-1-naphthyl)-2-[[(2R)-1-methylpyrrolidin-2-yl]methoxy]-6,8-dihydro-5H-pyrido[3,4-d]pyrimidin-4-yl]-1-(2-fluoro-prop-2-enoyl)piperazin-2-yl]acetonitrile To a solution of 2-[(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (125 mg, 235 μmol, 1.0 eq), 2-fluoroprop-2-enoic acid (42.3 mg, 470 μmol, 2.0 eq) in ethyl acetate (2.0 mL) was added TEA (190 mg, 1.88 mmol, 262 μL, 8.0 eq) and T3P (449 mg, 705 μmol, 419 μL, 50% purity, 3.0 eq) at 0° C. The mixture was stirred at 20° C. for 1 hour. After completion, the organic solvent was washed with water (5.0 mL). The aqueous phase was extracted with ethyl acetate (3×10 mL). The combined organic extracts were washed with brine (20.0 mL), dried with Na$_2$SO$_4$ the solvent was then removed under vacuum. The residue was purified by column chromatography (basic Al$_2$O$_3$, petroleum ether: ethyl acetate=3:1 to ethyl acetate:methanol=50:1), then the crude product was concentrated and re-purified by prep-HPLC (column: Phenomenex Gemini 150×25 mm×10 μm; mobile phase: [water (0.05% ammonium hydroxide v/v)-MeCN]; B %: 55%-85%,11.5 min) and lyophilization. Title compound 2-[(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (22.5 mg, 37.1 μmol, 16% yield, 99% purity) was obtained as white solid. LCMS [ESI, M+1]: 605.

$^1$H NMR (400 MHz, chloroform-d) δ 7.76 (br d, J=8.4 Hz, 1H), 7.62 (t, J=7.6 Hz, 1H), 7.53 (d, J=7.2 Hz, 1H), 7.49-7.40 (m, 1H), 7.34 (t, J=7.8 Hz, 1H), 7.26-7.18 (m, 1H), 5.51-5.32 (m, 1H), 5.26 (br dd, J=3.2, 16.8 Hz, 1H), 4.90 (br s, 1H), 4.49-4.34 (m, 2H), 4.24-4.01 (m, 3H), 3.97-3.78 (m, 2H), 3.64-3.55 (m, 1H), 3.44 (br s, 1H), 3.32-2.95 (m, 5H), 2.94-2.43 (m, 7H), 2.38-2.20 (m, 1H), 2.14-1.99 (m, 1H) 1.91-1.71 (m, 3H).

Example 558

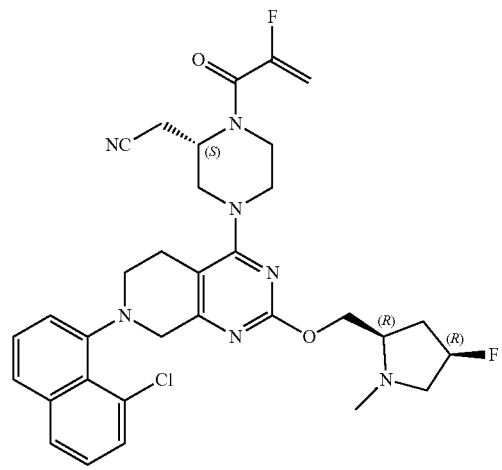

2-((S)-4-(7-(8-Chloronaphthalen-1-yl)-2-(((2R,4R)-4-fluoro-1-methylpyrrolidin-2-yl)methoxy)-5,6,7,8-tetrahydropyrido[3,4-d]pyrimidin-4-yl)-1-(2-fluoro-acryloyl)piperazin-2-yl)acetonitrile

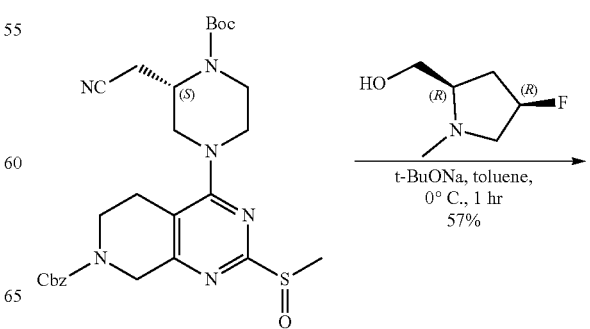

1421
-continued

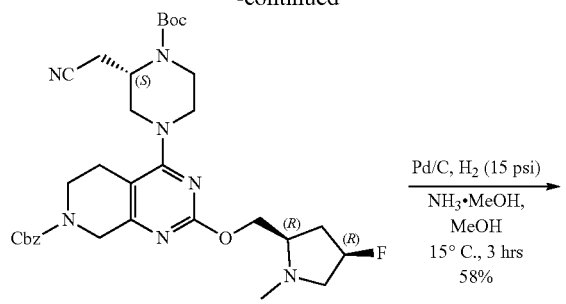

Pd/C, H₂ (15 psi)
NH₃·MeOH,
MeOH
15° C., 3 hrs
58%

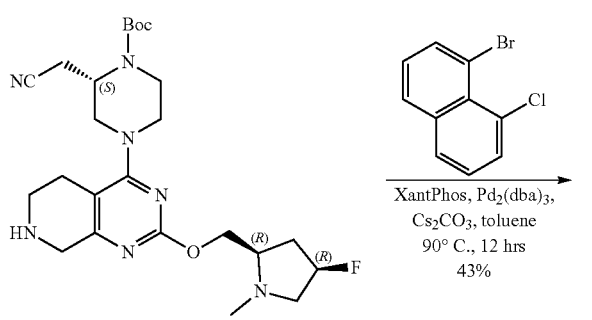

XantPhos, Pd₂(dba)₃,
Cs₂CO₃, toluene
90° C., 12 hrs
43%

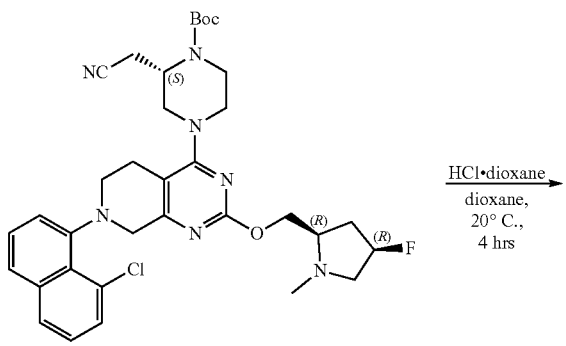

HCl·dioxane
dioxane,
20° C.,
4 hrs

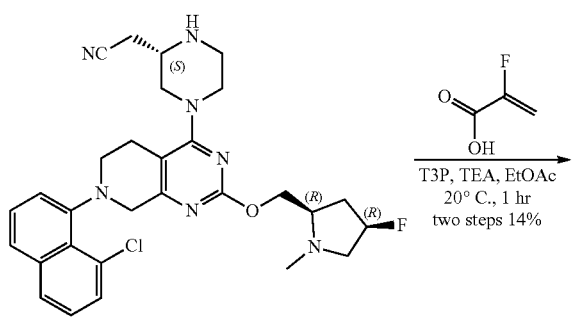

T3P, TEA, EtOAc
20° C., 1 hr
two steps 14%

1422
-continued

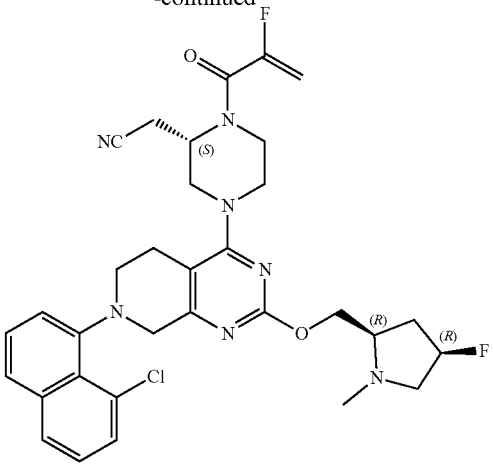

Step A: Benzyl 4-[(3S)-4-tert-butoxycarbonyl-3-(cyanomethyl)piperazin-1-yl]-2-[[(2R,4R)-4-fluoro-1-methyl-pyrrolidin-2-yl]methoxy]-6,8-dihydro-5H-pyrido[3,4-d]pyrimidine-7-carboxylate To a solution of [(2R,4R)-4-fluoro-1-methyl-pyrrolidin-2-yl]methanol (169 mg, 1.27 mmol, 1.5 eq) in toluene (4.0 mL) was added t-BuONa (163 mg, 1.69 mmol, 2.0 eq) at 0° C., after the reaction mixture was stirred at 0° C. for 0.5 hour, benzyl 4-[(3S)-4-tert-butoxycarbonyl-3-(cyanomethyl)piperazin-1-yl]-2-methyl sulfinyl-6,8-dihydro-5H-pyrido[3,4-d]pyrimidine-7-carboxylate (470 mg, 847 µmol, 1.0 eq) was added to the mixture, the reaction mixture was stirred at 0° C. for 0.5 hour. After completion, the reaction mixture was added to water (10 mL), then extracted with ethyl acetate (2×10.0 mL), the organic layer was dried over Na₂SO₄, filtered and concentrated. The residue was purified by column chromatography (SiO₂, petroleum ether/ethyl acetate=3/1 to ethyl acetate/methanol=20/1) to give benzyl 4-[(3S)-4-tert-butoxycarbonyl-3-(cyanomethyl)piperazin-1-yl]-2-[[(2R,4R)-4-fluoro-1-methyl-pyrrolidin-2-yl]methoxy]-6,8-dihydro-5H-pyrido[3,4-d]pyrimidine-7-carboxylate (330 mg, 484 µmol, 57% yield, 92% purity) as white solid. LCMS [ESI, M+1]: 624.

¹H NMR (400 MHz, chloroform-d) δ 7.40-7.30 (m, 5H), 5.24-5.03 (m, 3H), 4.69 (d, J=18.8 Hz, 1H), 4.61-4.53 (m, 1H), 4.51-4.38 (m, 2H), 4.23 (dd, J=7.6, 10.4 Hz, 1H), 4.08-3.73 (m, 4H), 3.52-3.11 (m, 4H), 3.04-2.91 (m, 1H), 2.81-2.57 (m, 5H), 2.55-2.36 (m, 5H), 2.11-1.99 (m, 1H), 1.51 (s, 9H).

Step B: tert-Butyl (2S)-2-(cyanomethyl)-4-[2-[[(2R,4R)-4-fluoro-1-methyl-pyrrolidin-2-yl]methoxy]-5,6,7,8-tetrahydropyrido[3,4-d]pyrimidin-4-yl]piperazine-1-carboxylate To a solution of benzyl 4-[(3S)-4-tert-butoxycarbonyl-3-(cyanomethyl)piperazin-1-yl]-2-[[(2R,4R)-4-fluoro-1-methyl-pyrrolidin-2-yl]methoxy]-6,8-dihydro-5H-pyrido[3,4-d]pyrimidine-7-carboxylate (330 mg, 529 µmol, 1.0 eq) in methanol (3.0 mL) and NH₃·MeOH (529 µmol, 3 mL, 20% purity, 1.0 eq) was added Pd/C (50 mg, 529 µmol, 10% purity) under N₂. The suspension was degassed under vacuum and purged with H₂ several times. The mixture was stirred under H₂ (15 psi) at 15° C. for 3 hours. After completion, the mixture was filtered, and the filter cake was washed with THF (2×3.0 mL), the filtrate was concentrated. The residue was purified by reverse phase flash chromatography (0.1% FA in MeCN). The mixture was adjusted with NaHCO$_3$ solid to pH ~8, then concentrated. The aqueous layer (20.0 mL) was extracted with ethyl acetate (2×15.0 mL), the organic layer was dried over Na$_2$SO$_4$, filtered and concentrated to give tert-butyl (2S)-2-(cyanomethyl)-4-[2-[[(2R,4R)-4-fluoro-1-methyl-pyrrolidin-2-yl]methoxy]-5,6,7,8-tetrahydropyrido[3,4-d]pyrimidin-4-yl]piperazine-1-carboxylate (150 mg, 299 μmol, 58% yield, 98% purity) as white solid. LCMS [ESI, M+1]: 490.

Step C: tert-Butyl(2S)-4-[7-(8-chloro-1-naphthyl)-2-[[(2R,4R)-4-fluoro-1-methyl-pyrrolidin-2-yl]methoxy]-6,8-dihydro-5H-pyrido[3,4-d]pyrimidin-4-yl]-2-(cyanomethyl)piperazine-1-carboxylate To a solution of tert-butyl (2S)-2-(cyanomethyl)-4-[2-[[(2R,4R)-4-fluoro-1-methyl-pyrrolidin-2-yl]methoxy]-5,6,7,8-tetrahydropyrido[3,4-d]pyrimidin-4-yl]piperazine-1-carboxylate (150 mg, 306 μmol, 1.0 eq) and 1-bromo-8-chloro-naphthalene (148 mg, 618 μmol, 2.0 eq) in toluene (3.0 mL) was added XantPhos (35.5 mg, 61.3 μmol, 0.2 eq), Pd$_2$(dba)$_3$ (42.1 mg, 45.9 μmol, 0.15 eq), and Cs$_2$CO$_3$ (399 mg, 1.23 mmol, 4.0 eq), the reaction mixture was stirred at 90° C. for 12 hours under N$_2$. After completion, the reaction mixture was filtered through celite, and the filtrate was washed with 1N aqueous HCl (2×10.0 mL), the aqueous layer was adjusted to pH ~8 with solid Na$_2$CO$_3$, then extracted with ethyl acetate (2×15.0 mL), the organic layer was dried over Na$_2$SO$_4$, filtered and concentrated. The residue was purified by reverse phase flash chromatography (0.1% FA in MeCN). The obtained product was adjusted with solid NaHCO$_3$ to pH ~8, and concentrated. The aqueous layer (20 mL) was extracted with ethyl acetate (2×15.0 mL), the organic layer was dried over Na$_2$SO$_4$, filtered and concentrated. The product tert-butyl(2S)-4-[7-(8-chloro-1-naphthyl)-2-[[(2R,4R)-4-fluoro-1-methyl-pyrrolidin-2-yl]methoxy]-6,8-dihydro-5H-pyrido[3,4-d]pyrimidin-4-yl]-2-(cyanomethyl)piperazine-1-carboxylate (85 mg, 129 μmol, 43% yield, 98% purity) was obtained as white solid. LCMS [ESI, M+1, M+23]: 650, 672.

$^1$H NMR (400 MHz, chloroform-d) δ 7.76 (br d, J=8.0 Hz, 1H), 7.62 (t, J=8.0 Hz, 1H), 7.52 (d, J=7.6 Hz, 1H), 7.49-7.40 (m, 1H), 7.34 (t, J=7.8 Hz, 1H), 7.26-7.17 (m, 1H), 5.24-5.03 (m, 1H), 4.67-4.55 (m, 1H), 4.52-4.36 (m, 2H), 4.23 (dd, J=7.6, 10.4 Hz, 1H), 4.13-3.77 (m, 4H), 3.65-3.52 (m, 1H), 3.43-2.86 (m, 7H), 2.84-2.64 (m, 3H), 2.62-2.38 (m, 5H), 2.16-1.98 (m, 1H), 1.52 (s, 9H).

Step D: 2-[(2S)-4-[7-(8-Chloro-1-naphthyl)-2-[[(2R,4R)-4-fluoro-1-methyl-pyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2R,4R)-4-fluoro-1-methyl-pyrrolidin-2-yl]methoxy]-6,8-dihydro-5H-pyrido[3,4-d]pyrimidin-4-yl]-2-(cyanomethyl)piperazine-1-carboxylate (85.0 mg, 131 μmol, 1.0 eq) in dioxane (1.0 mL) was added 4 M HCl/dioxane (1.0 mL), the reaction mixture was stirred at 20° C. for 4 hours. After completion, the reaction mixture was concentrated, the mixture was added dichloromethane (10 mL), then adjusted with saturated aqueous Na$_2$CO$_3$ to pH ~8, the organic layer was separated, then dried over Na$_2$SO$_4$, filtered and concentrated. The product 2-[(2S)-4-[7-(8-chloro-1-naphthyl)-2-[[(2R,4R)-4-fluoro-1-methyl-pyrrolidin-2-yl]methoxy]-6,8-dihydro-5H-pyrido[3,4-d]pyrimidin-4-yl]piperazin-2-yl]acetonitrile (90 mg, crude) was obtained as brown solid. LCMS [ESI, M+1]: 550.

Step E: 2-((S)-4-(7-(8-Chloronaphthalen-1-yl)-2-(((2R,4R)-4-fluoro-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile To a solution of 2-[(2S)-4-[7-(8-chloro-1-naphthyl)-2-[[(2R,4R)-4-fluoro-1-methyl-pyrrolidin-2-yl]methoxy]-6,8-dihydro-5H-pyrido[3,4-d]pyrimidin-4-yl]piperazin-2-yl]acetonitrile (90.0 mg, 120 μmol, 73% purity, 1.0 eq) and 2-fluoroprop-2-enoic acid (21.7 mg, 241 μmol, 2.0 eq) in ethyl acetate (2.0 mL) was added T3P (230 mg, 361 μmol, 215 μL, 50% purity, 3.0 eq) and TEA (97.6 mg, 962 μmol, 134 μL, 8.0 eq), the reaction mixture was stirred at 20° C. for 1 hour. After completion, water was added (10.0 mL), then the organic layer was separated, the aqueous layer was extracted with ethyl acetate (2×10.0 mL). The combined organic layer was dried over Na$_2$SO$_4$, filtered and concentrated. The residue was purified by column chromatography (SiO$_2$, petroleum ether/ethyl acetate=3/1 to ethyl acetate: methanol=10:1). The crude product was re-purified by prep-HPLC (column: Phenomenex Gemini 150*25 mm*10 μm; mobile phase: [water (0.04% NH$_3$H$_2$O+10 mM NH$_4$HCO$_3$)-MeCN]; B %: 48%-78%, 12 min), the obtained product was concentrated, and then lyophilized. The product title compound 2-((S)-4-(7-(8-chloronaphthalen-1-yl)-2-(((2R,4R)-4-fluoro-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile (10.9 mg, 17.3 μmol, 14% yield, 99% purity) was obtained as white solid. LCMS [ESI, M+1]: 622.

$^1$H NMR (400 MHz, Chloroform-d) δ 7.76 (d, J=8.0 Hz, 1H), 7.63 (t, J=7.6 Hz, 1H), 7.53 (d, J=7.2 Hz, 1H), 7.49-7.41 (m, 1H), 7.34 (t, J=7.8 Hz, 1H), 7.27-7.18 (m, 1H), 5.50-5.34 (m, 1H), 5.26 (dd, J=3.6, 16.8 Hz, 1H), 5.22-5.04 (m, 1H), 4.98-4.72 (m, 1H), 4.54-4.37 (m, 2H), 4.30-4.02 (m, 3H), 3.96-3.75 (m, 2H), 3.66-3.54 (m, 1H), 3.51-2.99 (m, 6H), 2.98-2.67 (m, 3H), 2.64-2.36 (m, 6H), 2.14-1.97 (m, 1H).

Example 559

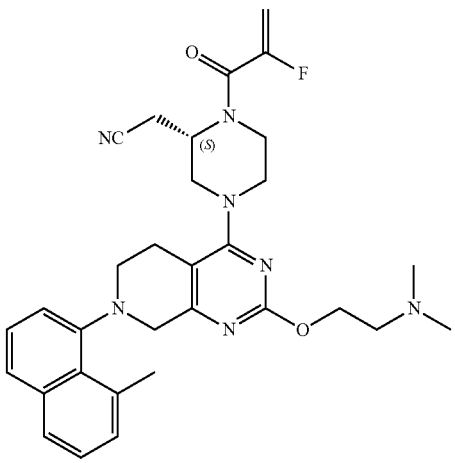

1425

2-[(2S)-4-[2-[2-(Dimethylamino)ethoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile

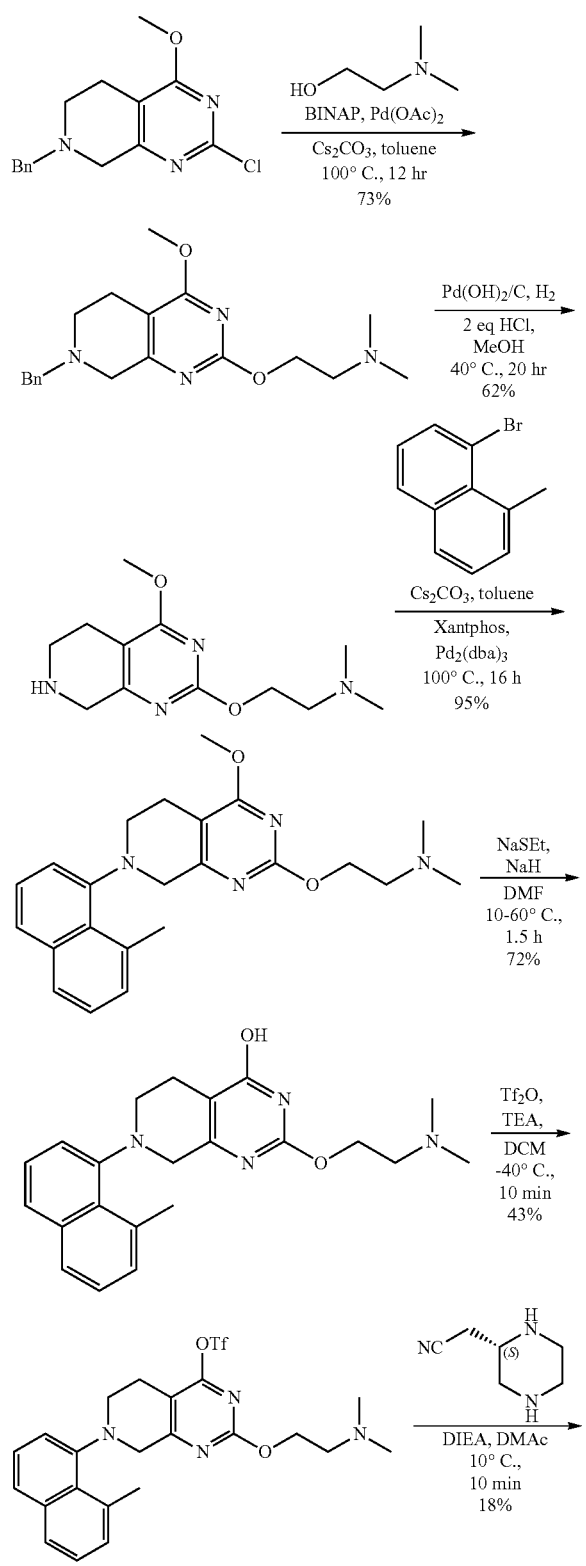

1426

-continued

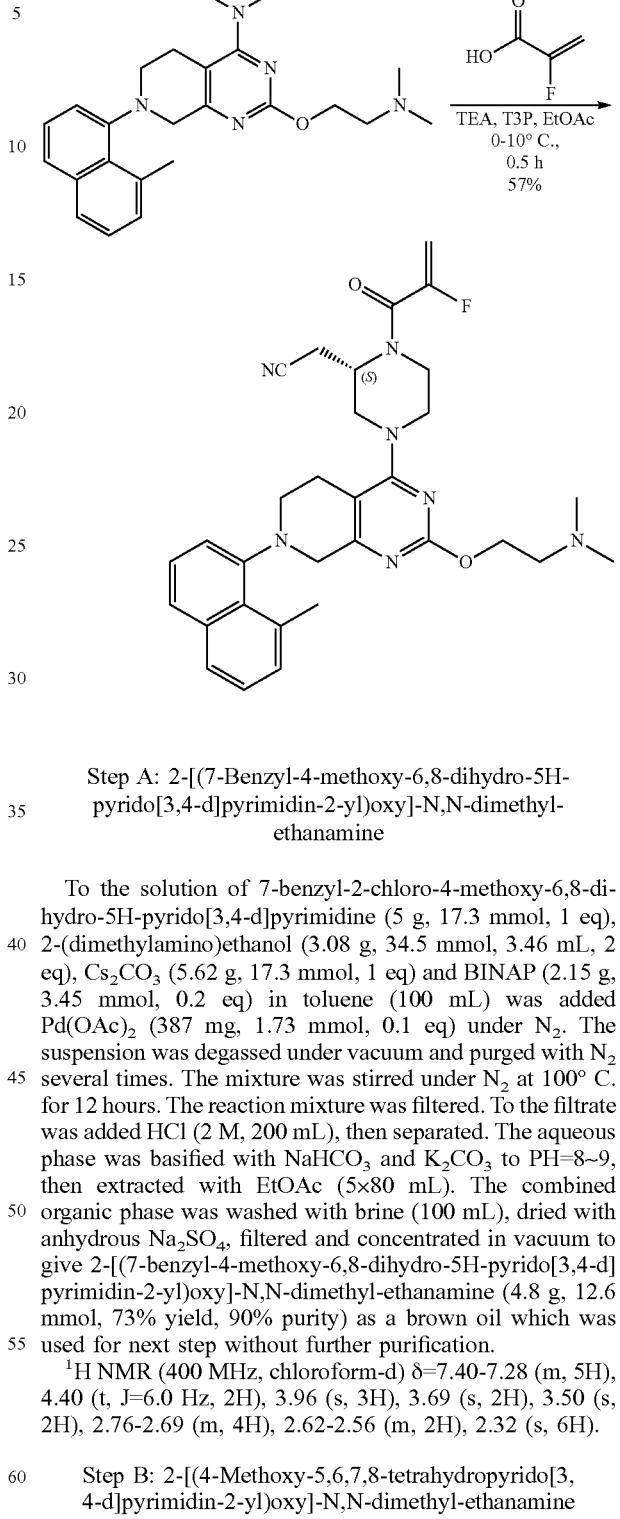

Step A: 2-[(7-Benzyl-4-methoxy-6,8-dihydro-5H-pyrido[3,4-d]pyrimidin-2-yl)oxy]-N,N-dimethyl-ethanamine To the solution of 7-benzyl-2-chloro-4-methoxy-6,8-dihydro-5H-pyrido[3,4-d]pyrimidine (5 g, 17.3 mmol, 1 eq), 2-(dimethylamino)ethanol (3.08 g, 34.5 mmol, 3.46 mL, 2 eq), $Cs_2CO_3$ (5.62 g, 17.3 mmol, 1 eq) and BINAP (2.15 g, 3.45 mmol, 0.2 eq) in toluene (100 mL) was added $Pd(OAc)_2$ (387 mg, 1.73 mmol, 0.1 eq) under $N_2$. The suspension was degassed under vacuum and purged with $N_2$ several times. The mixture was stirred under $N_2$ at 100° C. for 12 hours. The reaction mixture was filtered. To the filtrate was added HCl (2 M, 200 mL), then separated. The aqueous phase was basified with $NaHCO_3$ and $K_2CO_3$ to PH=8~9, then extracted with EtOAc (5×80 mL). The combined organic phase was washed with brine (100 mL), dried with anhydrous $Na_2SO_4$, filtered and concentrated in vacuum to give 2-[(7-benzyl-4-methoxy-6,8-dihydro-5H-pyrido[3,4-d]pyrimidin-2-yl)oxy]-N,N-dimethyl-ethanamine (4.8 g, 12.6 mmol, 73% yield, 90% purity) as a brown oil which was used for next step without further purification.

$^1$H NMR (400 MHz, chloroform-d) δ=7.40-7.28 (m, 5H), 4.40 (t, J=6.0 Hz, 2H), 3.96 (s, 3H), 3.69 (s, 2H), 3.50 (s, 2H), 2.76-2.69 (m, 4H), 2.62-2.56 (m, 2H), 2.32 (s, 6H).

Step B: 2-[(4-Methoxy-5,6,7,8-tetrahydropyrido[3,4-d]pyrimidin-2-yl)oxy]-N,N-dimethyl-ethanamine To the solution of 2-[(7-benzyl-4-methoxy-6,8-dihydro-5H-pyrido[3,4-d]pyrimidin-2-yl)oxy]-N,N-dimethyl-ethanamine (4.8 g, 14.0 mmol, 1 eq) in MeOH (100 mL) was added $Pd(OH)_2$/C (2 g, 10% purity) under $N_2$. The suspension was degassed under vacuum and purged with $H_2$ several times. The mixture was stirred under H$_2$ (15 psi) at 40° C. for 18 hours. To the mixture was added HCl/MeOH (4 M, 7.01 mL, 2 eq). The suspension was degassed under vacuum and purged with H$_2$ several times. The mixture was stirred under H$_2$ (15 psi) at 40° C. for 2 hours. The mixture was filtered, the filter cake was washed with NH$_3$.MeOH (10%, 3×30 mL). The filtrate was concentrated under vacuum. The residue was dissolved with water (10 mL) and EtOAc (10 mL), then the mixture was basified with K$_2$CO$_3$ to pH=11. The mixture was extracted with EtOAc (8×20 mL). The combined organic layers were dried over anhydrous Na$_2$SO$_4$, filtered and concentrated under vacuum to give 2-[(4-methoxy-5,6,7,8-tetrahydropyrido[3,4-d]pyrimidin-2-yl)oxy]-N,N-dimethyl-ethanamine (2.58 g, 8.69 mmol, 62% yield, 85% purity) as a brown oil which was used for next step without further purification. LCMS [ESI, M+1]: 253.

Step C: 2-[[4-Methoxy-7-(8-methyl-1-naphthyl)-6,8-dihydro-5H-pyrido[3,4-d]pyrimidin-2-yl]oxy]-N,N-dimethyl-ethanamine To the solution of 2-[(4-methoxy-5,6,7,8-tetrahydro-pyrido[3,4-d]pyrimidin-2-yl)oxy]-N,N-dimethyl-ethanamine (2.28 g, 7.68 mmol, 1 eq), 1-bromo-8-methyl-naphthalene (2.55 g, 11.5 mmol, 1.5 eq), Cs$_2$CO$_3$ (7.51 g, 23.0 mmol, 3 eq) and Xantphos (889 mg, 1.54 mmol, 0.2 eq) in toluene (70 mL) was added Pd$_2$(dba)$_3$ (703 mg, 768 μmol, 0.1 eq) under N$_2$. The suspension was degassed under vacuum and purged with N$_2$ several times. The mixture was stirred under N$_2$ at 100° C. for 16 hours. The reaction mixture was filtered, the filtrate was concentrated under vacuum. The residue was purified by silica gel chromatography (PE:EtOAc=10:1~0:1 to EtOAc:MeOH=1:0~10:1) to give 2-[[4-methoxy-7-(8-methyl-1-naphthyl)-6,8-dihydro-5H-pyrido[3,4-d]pyrimidin-2-yl]oxy]-N,N-dimethyl-ethanamine (3.2 g, 7.34 mmol, 95% yield, 90% purity) as a brown solid. LCMS [ESI, M+1]: 393.

$^1$H NMR (400 MHz, chloroform-d) δ=7.69 (d, J=8.0 Hz, 1H), 7.64 (d, J=7.6 Hz, 1H), 7.40 (t, J=7.6 Hz, 1H), 7.33 (t, J=7.6 Hz, 1H), 7.27-7.22 (m, 2H), 4.44 (t, J=6.4 Hz, 2H), 4.17-4.05 (m, 1H), 4.03 (s, 3H), 3.81 (d, J=17.6 Hz, 1H), 3.57-3.48 (m, 1H), 3.20 (dt, J=4.0, 11.2 Hz, 1H), 2.94-2.82 (m, 4H), 2.75 (t, J=6.4 Hz, 2H), 2.67 (br d, J=16.4 Hz, 1H), 2.34 (s, 6H).

Step D: 2-[2-(Dimethylamino)ethoxy]-7-(8-methyl-1-naphthyl)-6,8-dihydro-5H-pyrido[3,4-d]pyrimidin-4-ol To the solution of EtSH (1.96 g, 31.5 mmol, 2.33 mL, 3.64 eq) in DMF (60 mL) was added NaH (693 mg, 17.3 mmol, 60% purity, 2 eq), the mixture was stirred at 10° C. for 0.5 hour. Then 2-[[4-methoxy-7-(8-methyl-1-naphthyl)-6,8-dihydro-5H-pyrido[3,4-d]pyrimidin-2-yl]oxy]-N,N-dimethyl-ethanamine (3.4 g, 8.66 mmol, 1 eq) in DMF (10 mL) was added, the mixture was heated to 60° C. and stirred for 1 hour. The mixture was poured into ice water (200 mL) and extracted with EtOAc (30 mL). The aqueous phase was acidified with HCl (2 M) to PH=7~8, then extracted with EtOAc (6×80 mL). The combined organic layers were dried over anhydrous Na$_2$SO$_4$, filtered and concentrated under vacuum. The residue was triturated with PE:EtOAc=5:1 to give 2-[2-(dimethylamino)ethoxy]-7-(8-methyl-1-naphthyl)-6,8-dihydro-5H-pyrido[3,4-d]pyrimidin-4-ol (2.4 g, 6.28 mmol, 72% yield, 99% purity) as a white solid. LCMS [ESI, M+1]: 379.

Step E: [2-[2-(Dimethylamino)ethoxy]-7-(8-methyl-1-naphthyl)-6,8-dihydro-5H-pyrido[3,4-d]pyrimidin-4-yl] trifluoromethanesμLfonate To the solution of 2-[2-(dimethylamino)ethoxy]-7-(8-methyl-1-naphthyl)-6,8-dihydro-5H-pyrido[3,4-d]pyrimidin-4-ol (1 g, 2.64 mmol, 1 eq) and TEA (668 mg, 6.61 mmol, 919 μL, 2.5 eq) in DCM (20 mL) was added Tf$_2$O (1.12 g, 3.96 mmol, 654 μL, 1.5 eq) at −40° C., the mixture was stirred at −40° C. for 10 min. To the mixture was added water (10 mL), then separated. The aqueous phase was extracted with EtOAc (20 mL). The combined organic layers were dried over anhydrous Na$_2$SO$_4$, filtered and concentrated under vacuum. The residue was purified by silica gel chromatography (PE:EtOAc=5:1~0:1) to give [2-[2-(dimethylamino)ethoxy]-7-(8-methyl-1-naphthyl)-6,8-dihydro-5H-pyrido[3,4-d]pyrimidin-4-yl] trifluoromethanesμLfonate (650 mg, 1.15 mmol, 43% yield, 90% purity) as a brown oil.

Step F: 2-[(2S)-4-[2-[2-(Dimethylamino)ethoxy]-7-(8-methyl-1-naphthyl)-6,8-dihydro-5H-pyrido[3,4-d]pyrimidin-4-yl]piperazin-2-yl]acetonitrile To the solution of [2-[2-(dimethylamino)ethoxy]-7-(8-methyl-1-naphthyl)-6,8-dihydro-5H-pyrido[3,4-d]pyrimidin-4-yl] trifluoromethanesμLfonate (350 mg, 685 μmol, 1 eq) and 2-[(2S)-piperazin-2-yl]acetonitrile (111 mg, 754 μmol, 1.1 eq) in DMAC (4 mL) was added DIEA (177 mg, 1.37 mmol, 239 μL, 2 eq), the mixture was stirred at 10° C. for 10 min. The mixture was purified by reversed phase flash column (MeCN/Water (0.1% FA)=40%) to give 2-[(2S)-4-[2-[2-(dimethylamino)ethoxy]-7-(8-methyl-1-naphthyl)-6,8-dihydro-5H-pyrido[3,4-d]pyrimidin-4-yl]piperazin-2-yl]acetonitrile (60 mg, 121 μmol, 18% yield, 98% purity) as a brown oil. LCMS [ESI, M+1]: 486.

Step F: 2-[(2S)-4-[2-[2-(Dimethylamino)ethoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile To the solution of 2-[(2S)-4-[2-[2-(dimethylamino)ethoxy]-7-(8-methyl-1-naphthyl)-6,8-dihydro-5H-pyrido[3,4-d]pyrimidin-4-yl]piperazin-2-yl]acetonitrile (60 mg, 123 μmol, 1 eq), 2-fluoroprop-2-enoic acid (22.2 mg, 247 μmol, 2 eq) and TEA (100 mg, 988 μmol, 138 μL, 8 eq) in EtOAc (1.2 mL) was added T3P (236 mg, 370 μmol, 220 μL, 50% purity, 3 eq) at 0° C., the mixture was stirred at 10° C. for 0.5 hour. Water (5 mL) was added into the mixture. The mixture was extracted with EtOAc (2×8 mL). The combined organic layers were dried over anhydrous Na$_2$SO$_4$, filtered and concentrated under vacuum. The residue was purified by Al$_2$O$_3$ chromatography (EtOAc:MeOH=1:0~20:1). Then the residue was purified by prep-HPLC (column: Gemini 150*25 5μ; mobile phase: [water (0.05% ammonium hydroxide v/v)-MeCN]; B %: 53-83%, 12 min) to give title compound 2-[(2S)-4-[2-[2-(dimethylamino)ethoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile (39.5 mg, 70.4 μmol, 57% yield, 99.4% purity) as a gray solid. LCMS [ESI, M+1]: 558.

$^1$H NMR (400 MHz, chloroform-d) δ=7.70 (br d, J=8.4 Hz, 1H), 7.65 (t, J=8.0 Hz, 1H), 7.46-7.38 (m, 1H), 7.35 (t, J=7.6 Hz, 1H), 7.27-7.18 (m, 2H), 5.52-5.33 (m, 1H), 5.26 (dd, J=3.6, 16.8 Hz, 1H), 4.88 (br s, 1H), 4.47-4.37 (m, 2H), 4.31-4.18 (m, 1H), 4.17-4.01 (m, 2H), 3.94-3.84 (m, 1H), 3.77 (d, J=18.0 Hz, 1H), 3.58-3.41 (m, 2H), 3.25-2.95 (m, 4H), 2.92 (s, 3H), 2.90-2.77 (m, 2H), 2.77-2.70 (m, 2H), 2.68-2.56 (m, 1H), 2.34 (d, J=3.6 Hz, 6H).
Example 560
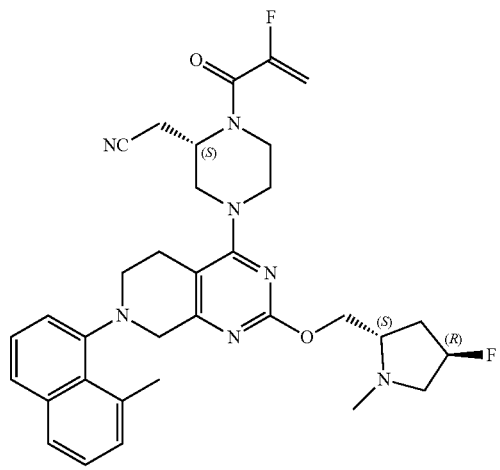
2-[(2S)-4-[2-[[(2S,4R)-4-Fluoro-1-methyl-pyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile
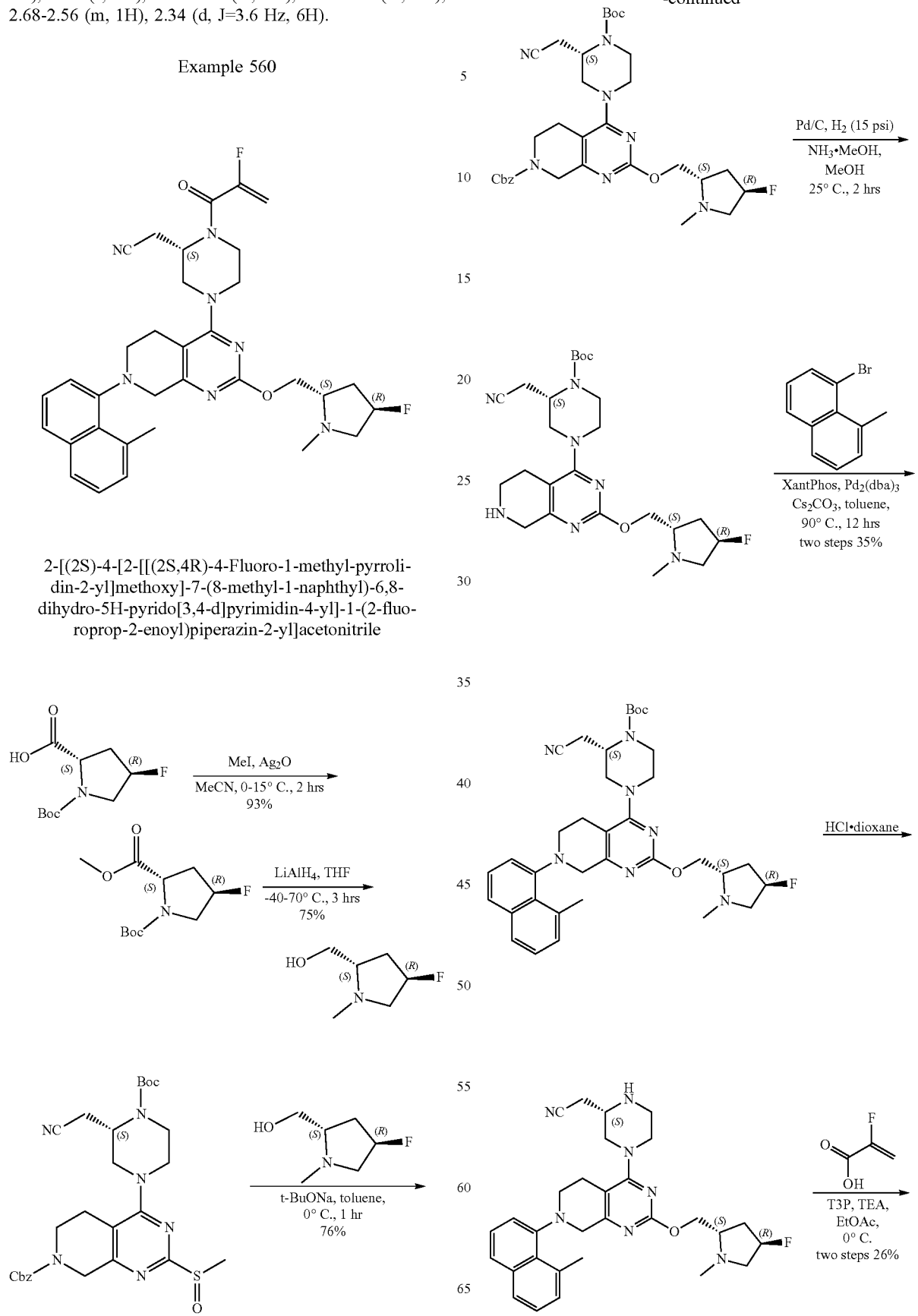

-continued

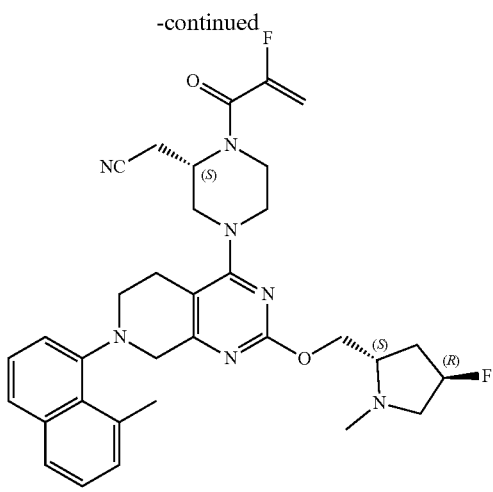

1-tert-Butyl-2-methyl
(2S,4R)-4-fluoropyrrolidine-1,2-dicarboxylate

To a solution of (2S,4R)-1-tert-butoxycarbonyl-4-fluoropyrrolidine-2-carboxylic acid (2.0 g, 8.58 mmol, 1.0 eq) and $Ag_2O$ (3.97 g, 17.2 mmol, 2.0 eq) in $CH_3CN$ (20.0 mL) was added MeI (2.43 g, 17.2 mmol, 1.07 mL, 2.0 eq) at 0° C. in portions, the reaction mixture was stirred at 15° C. for 12 hours. After completion, the reaction mixture was added to water (30.0 mL), then the organic layer was separated, the aqueous phase was extracted with ethyl acetate (30.0 mL×2), the combined organic layer was dried over $Na_2SO_4$, filtered and concentrated. The residue was purified by column chromatography ($SiO_2$, petroleum ether: ethyl acetate=3:1 to ethyl acetate:methanol=10:1). The product 1-tert-butyl-2-methyl (2S,4R)-4-fluoropyrrolidine-1,2-dicarboxylate (1.98 g, 8.01 mmol, 93% yield) was obtained as colorless oil.

$^1$H NMR (400 MHz, Chloroform-d) δ 5.29-5.15 (m, 1H), 4.49-4.38 (m, 1H), 3.92-3.74 (m, 1H), 3.68 (s, 3H), 3.60-3.56 (m, 1H), 2.63-2.54 (m, 1H), 2.17-2.05 (m, 1H), 1.44 (d, J=18.0 Hz, 9H).

[(2S,4R)-4-Fluoro-1-methyl-pyrrolidin-2-yl]methanol

To a solution of 1-tert-butyl-2-methyl (2S,4R)-4-fluoropyrrolidine-1,2-dicarboxylate (1.98 g, 8.0 mmol, 1.0 eq) in THF (20.0 mL) was added $LiAlH_4$ (912 mg, 24.0 mmol, 3.0 eq) slowly at −40° C., after completion the mixture was stirred at −40° C. for 0.5 hour, then the mixture was warmed to 70° C. and stirred at this temperature for 3 hours. After completion, the reaction mixture was quenched by addition a solution of $Na_2SO_4$ (6.0 mL) at 0° C., and then diluted with THF (10.0 mL), then filtered and the solid was washed with ethyl acetate (30.0 mL). The combined organic layers were dried over $Na_2SO_4$, filtered and concentrated under reduced pressure to give [(2S,4R)-4-fluoro-1-methyl-pyrrolidin-2-yl]methanol (800 mg, 6.01 mmol, 75% yield) as yellow oil.

$^1$H NMR (400 MHz, Chloroform-d) δ 5.13-4.97 (m, 1H), 3.67-3.63 (m, 1H), 3.51-3.37 (m, 2H), 2.95 (s, 1H), 2.74-2.68 (m, 1H), 2.63-2.51 (m, 1H), 2.33 (s, 3H), 2.07-2.02 (m, 1H), 1.99-1.95 (m, 1H).

Step A: Benzyl 4-[(3S)-4-tert-butoxycarbonyl-3-(cyanomethyl)piperazin-1-yl]-2-[[(2S,4R)-4-fluoro-1-methyl-pyrrolidin-2-yl]methoxy]-6,8-dihydro-5H-pyrido[3,4-d]pyrimidine-7-carboxylate A mixture of [(2S,4R)-4-fluoro-1-methyl-pyrrolidin-2-yl]methanol (480 mg, 3.6 mmol, 2.0 eq) and t-BuONa (295 mg, 3.1 mmol, 1.7 eq) in toluene (8.0 mL) was degassed and purged with $N_2$ for 3 times and the mixture was stirred at 0° C., then benzyl 4-[(3S)-4-tert-butoxycarbonyl-3-(cyanomethyl)piperazin-1-yl]-2-methylsulfinyl-6,8-dihydro-5H-pyrido[3,4-d]pyrimidine-7-carboxylate (1 g, 1.8 mmol, 1.0 eq) in toluene (8.0 mL) was added. The mixture was stirred at 0° C. for 0.5 hour under $N_2$. After completion, the mixture was quenched by addition $H_2O$ (25.0 mL), and then extracted with ethyl acetate (30.0 mL×3). The combined organic layers were dried over $Na_2SO_4$, filtered and concentrated under reduced pressure to give a residue. The residue was purified by reverse phase flash HPLC ($^{18}C$, 0.1% FA in water, 0-60% MeCN). The obtained product was adjusted with saturated aqueous $NaHCO_3$ to pH ~8, then concentrated, the aqueous layer was extracted with ethyl acetate (100.0 mL×3), the combined organic layer was dried over $Na_2SO_4$, filtered and concentrated to give benzyl 4-[(3S)-4-tert-butoxycarbonyl-3-(cyanomethyl)piperazin-1-yl]-2-[[(2S,4R)-4-fluoro-1-methyl-pyrrolidin-2-yl]methoxy]-6,8-dihydro-5H-pyrido[3,4-d]pyrimidine-7-carboxylate (860 mg, 1.38 mmol, 76% yield, 100% purity) as a white solid. LCMS [ESI, M+1]: 624.

$^1$H NMR (400 MHz, Chloroform-d) δ 7.31-7.25 (m, 5H), 5.15-5.02 (m, 3H), 4.63-4.58 (m, 1H), 4.51 (br s, 1H), 4.39-4.31 (m, 2H), 4.16-4.12 (m, 1H), 3.99-3.88 (m, 3H), 3.71 (br d, J=11.2 Hz, 1H), 3.52-3.41 (m, 1H), 3.36 (br s, 1H), 3.19-3.16 (m, 2H), 2.99-2.86 (m, 2H), 2.71-2.48 (m, 5H), 2.43 (s, 3H), 2.76-2.17 (m, 1H), 1.96-1.80 (m, 1H), 1.74 (br s, 1H), 1.43 (s, 9H).

Step B: tert-Butyl-(2S)-2-(cyanomethyl)-4-[2-[[(2S,4R)-4-fluoro-1-methyl-pyrrolidin-2-yl]methoxy]-5,6,7,8-tetrahydropyrido[3,4-d]pyrimidin-4-yl]piperazine-1-carboxylate To a solution of benzyl 4-[(3S)-4-tert-butoxycarbonyl-3-(cyanomethyl)piperazin-1-yl]-2-[[(2S,4R)-4-fluoro-1-methyl-pyrrolidin-2-yl]methoxy]-6,8-dihydro-5H-pyrido[3,4-d]pyrimidine-7-carboxylate (860 mg, 1.4 mmol, 1.0 eq) in MeOH (20.0 mL) and $NH_3.MeOH$ (10.0 mL, 50% w/w) was added Pd/C (200 mg, 10% purity, 1.0 eq) under $N_2$. The suspension was degassed under vacuum and purged with $H_2$ several times. The mixture was stirred under $H_2$ (15 psi) at 25° C. for 1 hour. After completion, the reaction mixture was filtered and concentrated under reduced pressure to give tert-butyl-(2S)-2-(cyanomethyl)-4-[2-[[(2S,4R)-4-fluoro-1-methyl-pyrrolidin-2-yl]methoxy]-5,6,7,8-tetrahydropyrido[3,4-d]pyrimidin-4-yl]piperazine-1-carboxylate (620 mg, crude) as a white solid. The crude product was used into the next step without further purification. LCMS [ESI, M+1]: 490.

$^1$H NMR (400 MHz, Chloroform-d) δ 5.16-5.02 (m, 1H), 4.51 (br s, 1H), 4.31 (dd, J=4.8, 11.2 Hz, 1H), 4.13 (dd, J=6.0, 11.2 Hz, 1H), 3.87 (s, 2H), 3.76 (d, J=12.4 Hz, 1H), 3.52-3.41 (m, 1H), 3.14 (dd, J=3.6, 13.6 Hz, 2H), 3.06-3.03 (m, 1H), 2.99-2.88 (m, 3H), 2.74-2.48 (m, 6H), 2.43 (s, 3H), 2.29-2.18 (m, 1H), 1.96-1.80 (m, 1H), 1.68-1.59 (m, 2H), 1.44 (s, 9H).

Step C: tert-Butyl-(2S)-2-(cyanomethyl)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate A mixture of tert-butyl-(2S)-2-(cyanomethyl)-4-[2-[[(2S,4R)-4-fluoro-1-methyl-pyrrolidin-2-yl]methoxy]-5,6,7,8-tetrahydropyrido[3,4-d]pyrimidin-4-yl]piperazine-1-carboxylate (600 mg, 1.2 mol, 1.0 eq), 1-bromo-8-methyl-naphthalene (812 mg, 3.7 mmol, 3.0 eq), Pd$_2$(dba)$_3$ (168 mg, 184 μmol, 0.15 eq), Cs$_2$CO$_3$ (1.2 g, 3.7 mmol, 3.0 eq) and Xantphos (142 mg, 246 μmol, 0.2 eq) in toluene (5.0 mL) was degassed and purged with N$_2$ for 3 times, and then the mixture was stirred at 90° C. for 12 hours under N$_2$. After completion, the reaction mixture was filtered and concentrated under reduced pressure to give a residue, and then the residue was dissolved with EA 15.0 mL, then was adjusted with 0.5 M HCl to pH ~2. The organic layer was washed with H$_2$O (15.0 mL×3), then the solid NaHCO$_3$ was added to the combined aqueous phase until pH was reached to 8, after that, the aqueous phase was extracted with ethyl acetate (50.0 mL×3), the combined organic layer was dried over Na$_2$SO$_4$, filtered and concentrated. The residue was purified by reverse phase flash HPLC ($^{18}$C, 0.1% TFA in water, 0-50% MeCN). The obtained product was adjusted with saturated aqueous NaHCO$_3$ to pH ~8, then concentrated, the aqueous layer was extracted with EA (100.0 mL×3), the combined organic layer was dried over Na$_2$SO$_4$, filtered and concentrated to give tert-butyl-(2S)-2-(cyanomethyl)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (300 mg, 467 μmol, 35% yield, 99% purity) as yellow oil. LCMS [ESI, M+1]: 630.

Step D: 2-[(2S)-4-[2-[[(2S,4R)-4-Fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To a solution of tert-butyl-(2S)-2-(cyanomethyl)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (200 mg, 318 μmol, 1.0 eq) in dioxane (1.5 mL) was added HCl/dioxane (4 M, 2.0 mL, 25.0 eq) at 25° C. The mixture was stirred at 25° C. for 1 hour. After completion, the reaction mixture was quenched by addition saturated aqueous NaHCO$_3$ (6.0 mL) at 0° C., and then diluted with H$_2$O 10.0 mL and extracted with EA (15.0 mL×3). The combined organic layers were dried over Na$_2$SO$_4$, filtered and concentrated under reduced pressure to give 2-[(2S)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (150 mg, crude) as yellow oil. The product was used into the next step without further purification. LCMS [ESI, M+1]: 530.

Step E: 2-[(2S)-4-[2-[[(2S,4R)-4-Fluoro-1-methyl-pyrrolidin-2-yl]methoxy]-7-(8-methyl-1-naphthyl)-6,8-dihydro-5H-pyrido [3,4-d]pyrimidin-4-yl]-1-(2-fluoroprop-2-enoyl)piperazin-2-yl]acetonitrile To a solution of 2-[(2S)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (150 mg, 283 μmol, 1.0 eq) in ethyl acetate (1.0 mL) was added a solution of 2-fluoroprop-2-enoic acid (42.9 mg, 476 μmol, 1.68 eq) in ethyl acetate (0.5 mL), then was added TEA (1.93 g, 19 mmol, 2.65 mL, 67.0 eq) and T3P (455 mg, 715 μmol, 425 μL, 50% purity, 2.5 eq) and the mixture was stirred at 0° C., after that the reaction mixture was warmed to 20° C. and stirred for 1 hours. After completion, the reaction mixture was quenched by addition H$_2$O 10.0 mL, and then extracted with ethyl acetate (15.0 mL×3). The combined organic layers were dried over Na$_2$SO$_4$, filtered and concentrated under reduced pressure to give a residue. The residue was purified by prep-HPLC (column: Phenomenex Gemini 150*25 mm*10 μm; mobile phase: [water (0.05% ammonium hydroxide v/v)-MeCN]; B %: 58%-88%, 11.5 min) and lyophilization to give title compound 2-[(2S)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile (50.1 mg, 82.9 two steps 26% yield, 99.5% purity) as a white solid. LCMS [ESI, M+1]: 602.

$^1$H NMR (400 MHz, Chloroform-d) δ 7.72 (d, J=8.4 Hz, 1H), 7.67 (t, J=8.0 Hz, 1H), 7.46-7.43 (m, 2H), 7.26-7.21 (m, 2H), 5.50-5.38 (m, 1H), 5.30-5.11 (m, 2H), 4.89 (br s, 1H), 4.45-4.40 (m, 1H), 4.30-4.20 (m, 2H), 4.19-4.13 (m, 1H), 4.10-4.05 (m, 1H), 3.92-3.88 (m, 1H), 3.82-3.77 (m, 1H), 3.62-3.46 (m, 3H), 3.25-3.18 (m, 2H), 3.15-3.09 (m, 1H), 3.08-2.98 (m, 2H), 2.94 (s, 3H), 2.90-2.77 (m, 2H), 2.67-2.56 (m, 2H), 2.51 (d, J=4.8 Hz, 3H), 2.38-2.27 (m, 1H), 2.07-1.89 (m, 1H).

Example 561

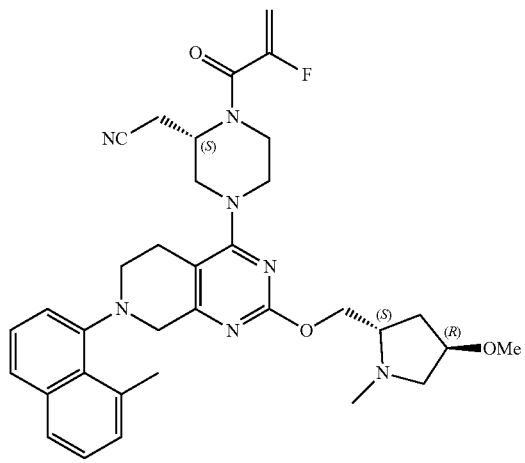

1435

2-[(2S)-1-(2-Fluoroprop-2-enoyl)-4-[2-[[(2S,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile

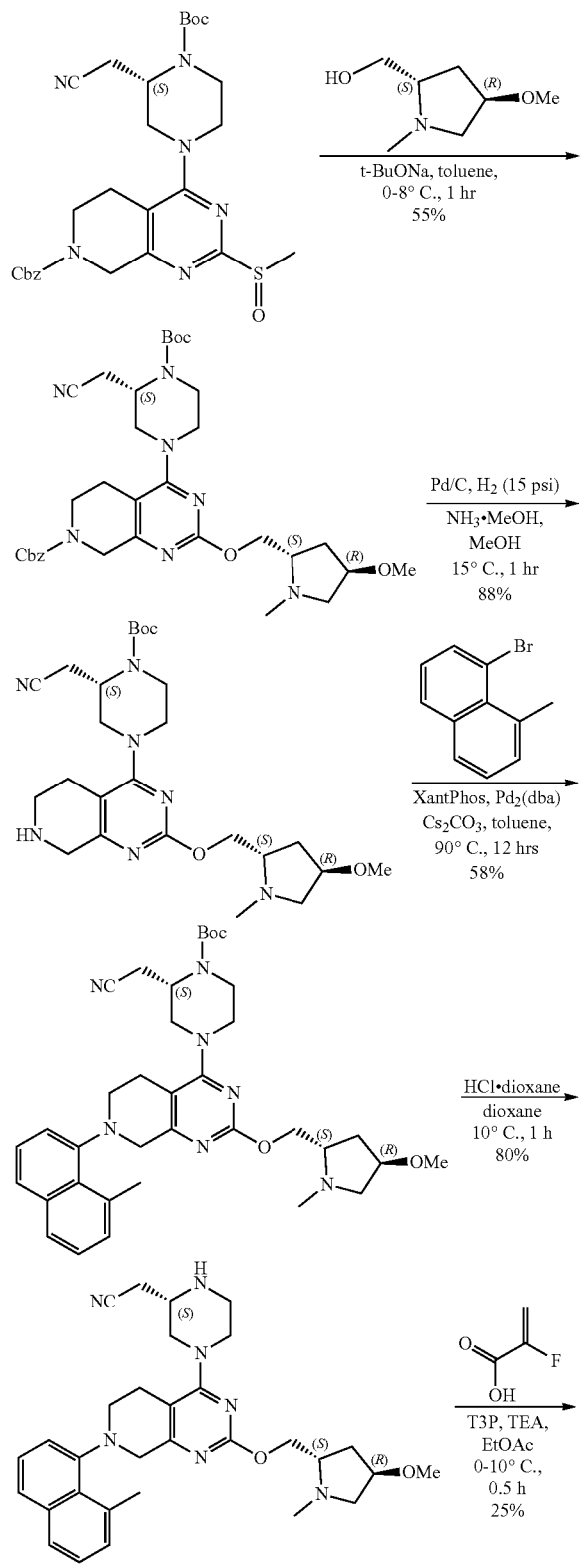

1436

-continued

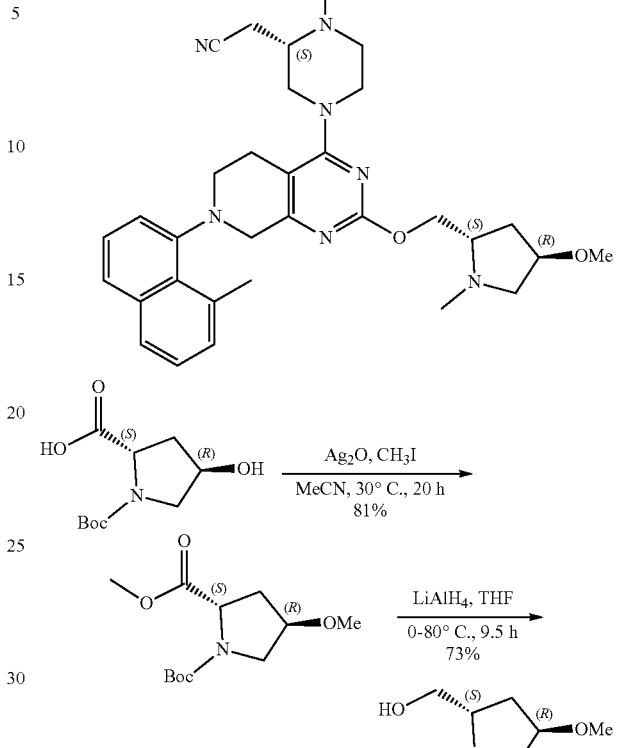

1-tert-Butyl-2-methyl (2S,4R)-4-methoxypyrrolidine-1,2-dicarboxylate

To the solution of (2S,4R)-1-tert-butoxycarbonyl-4-hydroxy-pyrrolidine-2-carboxylic acid (2 g, 8.65 mmol, 1 eq) and $Ag_2O$ (6.01 g, 26.0 mmol, 3 eq) in MeCN (40 mL) was added $CH_3I$ (10.0 g, 70.8 mmol, 4.41 mL, 8.19 eq), the mixture was stirred at 30° C. for 14 hours. To the mixture was added $CH_3I$ (13.2 g, 93.1 mmol, 5.80 mL, 10.8 eq), the mixture was stirred at 30° C. for 6 hours. The reaction mixture was filtered, the filtrate was concentrated under vacuum. The residue was purified by silica gel chromatography (PE:EtOAc=20:1~10:1) to give 1-tert-butyl-2-methyl (2S,4R)-4-methoxypyrrolidine-1,2-dicarboxylate (1.85 g, 6.99 mmol, 81% yield, 98% purity) as a yellow oil.

[(2S,4R)-4-Methoxy-1-methyl-pyrrolidin-2-yl]methanol

To the solution of O1-tert-butyl O2-methyl (2S,4R)-4-methoxypyrrolidine-1,2-dicarboxylate (1.85 g, 7.13 mmol, 1 eq) in THF (50 mL) was added $LiAlH_4$ (542 mg, 14.3 mmol, 2 eq) at 0° C., the mixture was stirred at 0° C. for 0.5 hour. Then the mixture was heated to 70° C. and stirred for 3 hours. Then $LiAlH_4$ (542 mg, 14.27 mmol, 2 eq) was added at 10° C., the mixture was heated to 80° C. and stirred for 6 hours. The reaction mixture was quenched by saturated $Na_2SO_4$ (5 mL), then filtered. The filter cake was washed with THF (3×30 mL). The filtrate was concentrated under vacuum to give [(2S,4R)-4-methoxy-1-methyl-pyrrolidin-2- yl]methanol (840 mg, 5.21 mmol, 73% yield, 90% purity) as a yellow oil which was used for next step without further purification.

¹H NMR (400 MHz, chloroform-d) δ=3.93-3.83 (m, 1H), 3.68 (dd, J=3.2, 11.2 Hz, 1H), 3.48-3.36 (m, 2H), 3.30 (s, 3H), 2.67-2.58 (m, 1H), 2.40-2.30 (m, 4H), 2.08 (td, J=8.0, 13.2 Hz, 1H), 1.90-1.79 (m, 1H).

Step A: Benzyl 4-[(3S)-4-tert-butoxycarbonyl-3-(cyanomethyl)piperazin-1-yl]-2-[[(2S,4R)-4-methoxy-1-methyl-pyrrolidin-2-yl]methoxy]-6, 8-dihydro-5H-pyrido [3,4-d]pyrimidine-7-carboxylate To the solution of [(2S,4R)-4-methoxy-1-methyl-pyrrolidin-2-yl]methanol (367 mg, 2.52 mmol, 2 eq) in toluene (18 mL) was added t-BuONa (364 mg, 3.79 mmol, 3 eq) at 0° C., then benzyl 4-[(3S)-4-tert-butoxycarbonyl-3-(cyanomethyl)piperazin-1-yl]-2-methylsulfinyl-6,8-dihydro-5H-pyrido[3,4-d]pyrimidine-7-carboxylate (700 mg, 1.26 mmol, 1 eq) was added at 0° C., the reaction mixture was stirred at 8° C. for 1 hour. Water (30 mL) was added into the mixture. The mixture was diluted with EtOAc (10 mL) and extracted with EtOAc (2×30 mL). The combined organic layers were washed with brine (20 mL). The combined organic layers were dried over anhydrous Na₂SO₄, filtered and concentrated under vacuum. The residue was purified by reverse phase flash column (MeCN/Water (0.1% FA)=30%) to give benzyl 4-[(3S)-4-tert-butoxycarbonyl-3-(cyanomethyl)piperazin-1-yl]-2-[[(2S,4R)-4-methoxy-1-methyl-pyrrolidin-2-yl]methoxy]-6, 8-dihydro-5H-pyrido[3,4-d]pyrimidine-7-carboxylate (450 mg, 694 μmol, 55% yield, 98% purity) as a yellow solid. LCMS [ESI, M+1]: 636.

Step B: tert-Butyl-(2S)-2-(cyanomethyl)-4-[2-[[(2S,4R)-4-methoxy-1-methyl-pyrrolidin-2-yl]methoxyl]-5,6,7,8-tetrahydropyrido[3,4-d]pyrimidin-4-yl]piperazine-1-carboxylate To the solution of benzyl 4-[(3S)-4-tert-butoxycarbonyl-3-(cyanomethyl)piperazin-1-yl]-2-[[(2S,4R)-4-methoxy-1-methyl-pyrrolidin-2-yl]methoxy]-6,8-dihydro-5H-pyrido[3,4-d]pyrimidine-7-carboxylate (490 mg, 771 μmol, 1 eq) and NH₃.MeOH (5 mL, 25% purity) in MeOH (5 mL) was added Pd/C (100 mg, 10% purity) under N₂. The suspension was degassed under vacuum and purged with H₂ several times. The mixture was stirred under H₂ (15 psi) at 15° C. for 1 hour. The reaction mixture was filtered, the filter cake was washed with MeOH (3×5 mL). The filtrate was concentrated under vacuum to give tert-butyl(2S)-2-(cyanomethyl)-4-[2-[[(2S,4R)-4-methoxy-1-methyl-pyrrolidin-2-yl]methoxy]-5,6,7,8-tetrahydropyrido[3,4-d]pyrimidin-4-yl]piperazine-1-carboxylate (360 mg, 682 μmol, 88% yield, 95% purity) as a yellow solid which was used for next step without further purification.

Step C: tert-Butyl(2S)-2-(cyanomethyl)-4-[2-[[(2S,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate To the solution of tert-butyl (2S)-2-(cyanomethyl)-4-[2-[[(2S,4R)-4-methoxy-1-methyl-pyrrolidin-2-yl]methoxy]-5,6,7,8-tetrahydropyrido[3,4-d]pyrimidin-4-yl]piperazine-1-carboxylate (360 mg, 718 μmol, 1 eq), 1-bromo-8-methyl-naphthalene (238 mg, 1.08 mmol, 1.5 eq), Cs₂CO₃ (701 mg, 2.15 mmol, 3 eq) and Xantphos (83.0 mg, 143 μmol, 0.2 eq) in toluene (8 mL) was added Pd₂(dba)₃ (65.7 mg, 71.8 μmol, 0.1 eq) under N₂. The suspension was degassed under vacuum and purged with N₂ several times. The mixture was stirred under N₂ at 90° C. for 12 hours. The reaction mixture was filtered, the filtrate was concentrated under vacuum. The residue was purified by silica gel chromatography (from PE:EtOAc=5:1~1:1 to EtOAc:MeOH=1:0~20:1). Then the residue was purified by reverse phase flash column (ACN/Water (0.1% FA)=45%) to give tert-butyl(2S)-2-(cyanomethyl)-4-[2-[[(2S,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (280 mg, 414 μmol, 58% yield, 95% purity) as a brown solid. LCMS [ESI, M+1]: 642.

¹H NMR (400 MHz, chloroform-d) δ=7.74-7.60 (m, 2H), 7.45-7.37 (m, 1H), 7.34 (t, J=7.6 Hz, 1H), 7.27-7.17 (m, 2H), 4.61 (br s, 1H), 4.39 (ddd, J=4.8, 6.8, 11.2 Hz, 1H), 4.30-4.20 (m, 1H), 4.16-4.11 (m, 1H), 4.11-3.89 (m, 4H), 3.88-3.68 (m, 1H), 3.56-3.47 (m, 1H), 3.46-3.32 (m, 2H), 3.30 (d, J=2.4 Hz, 3H), 3.21-3.05 (m, 3H), 3.01-2.85 (m, 5H), 2.81-2.67 (m, 2H), 2.65-2.54 (m, 1H), 2.46 (d, J=4.0 Hz, 3H), 2.35-2.26 (m, 1H), 2.11-2.05 (m, 1H), 2.00-1.88 (m, 1H), 1.52 (s, 9H).

Step D: 2-[(2S)-4-[2-[[(2S,4R)-4-Methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl] acetonitrile To the solution of tert-butyl (2S)-2-(cyanomethyl)-4-[2-[[(2S,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (280 mg, 436 μmol, 1 eq) in dioxane (1 mL) was added HCl/dioxane (4 M, 1.64 mL, 15 eq) was stirred at 10° C. for 1 hour. The reaction mixture was concentrated under vacuum. The mixture was basified with saturated NaHCO₃ to PH=8~9 and extracted with EtOAc (3×15 mL). The combined organic layers were dried over anhydrous Na₂SO₄, filtered and concentrated under vacuum to give 2-[(2S)-4-[2-[[(2S,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (210 mg, 349 μmol, 80% yield, 90% purity) as a yellow solid which was used for next step without further purification. LCMS [ESI, M+1]: 542.

Step E: 2-[(2S)-1-(2-Fluoroprop-2-enoyl)-4-[2-[[(2S,4R)-4-methoxy-1-methyl-pyrrolidin-2-yl]methoxyl]-7-(8-methyl-1-naphthyl)-6,8-dihydro-5H-pyrido[3,4-d]pyrimidin-4-yl]piperazin-2-yl] acetonitrile To the solution of 2-[(2S)-4-[2-[[(2S,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (100 mg, 185 μmol, 1 eq), 2-fluoroprop-2-enoic acid (33.2 mg, 369 μmol, 2 eq) and TEA (149 mg, 1.48 mmol, 206 μL, 8 eq) in EtOAc (2 mL) was added T3P (352 mg, 554 μmol, 329 μL, 50% purity, 3 eq) at 0° C., the mixture was stirred at 10° C. for 0.5 hour. Water (3 mL) was added into the mixture. The mixture was extracted with EtOAc (2×3 mL). The combined organic layers were dried over anhydrous Na₂SO₄, filtered and concentrated under vacuum. The residue was purified by prep-HPLC (column: Xtimate C18 150*25 mm*5 μm; mobile phase: [water (0.05% ammonium hydroxide v/v)-ACN]; B %: 52%-82%, 12 min) to give title compound 2-[(2S)-1-(2-fluoroprop-2-enoyl)-4-[2-[[(2S,4R)-4-methoxy-1-methyl-pyrrolidin-2-yl]

methoxy]-7-(8-methyl-1-naphthyl)-6,8-dihydro-5H-pyrido[3,4-d]pyrimidin-4-yl]piperazin-2-yl]acetonitrile (28.1 mg, 45.5 µmol, 25% yield, 99.4% purity) as a white solid. LCMS [ESI, M+1]: 614.

¹H NMR (400 MHz, chloroform-d) δ=7.65-7.54 (m, 2H), 7.38-7.30 (m, 1H), 7.27 (t, J=7.6 Hz, 1H), 7.19-7.10 (m, 2H), 5.46-5.26 (m, 1H), 5.18 (br dd, J=3.6, 16.8 Hz, 1H), 4.83 (br s, 1H), 4.37-4.27 (m, 1H), 4.23-3.94 (m, 4H), 3.92-3.85 (m, 1H), 3.84-3.76 (m, 1H), 3.70 (br d, J=18.0 Hz, 1H), 3.46 (br d, J=8.8 Hz, 1H), 3.42-3.31 (m, 2H), 3.22 (d, J=2.0 Hz, 3H), 3.18-3.07 (m, 2H), 3.06-2.87 (m, 2H), 2.87-2.64 (m, 6H), 2.59-2.49 (m, 1H), 2.38 (d, J=4.4 Hz, 3H), 2.24 (ddd, J=3.2, 6.0, 9.6 Hz, 1H), 2.04-1.94 (m, 1H), 1.93-1.81 (m, 1H).

Example 562

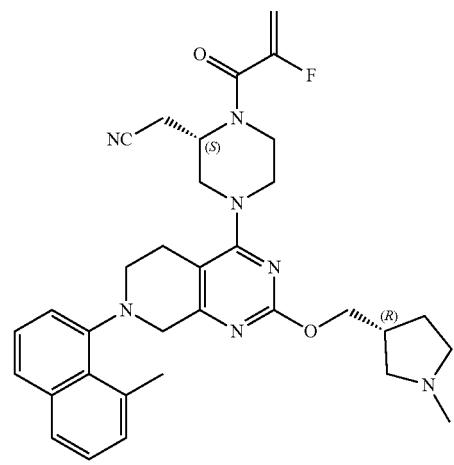

2-[(2S)-1-(2-Fluoroprop-2-enoyl)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile

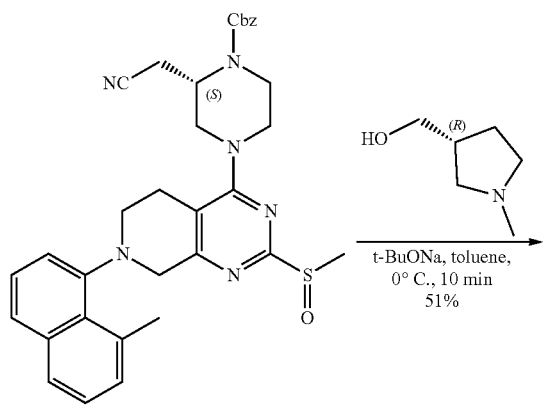

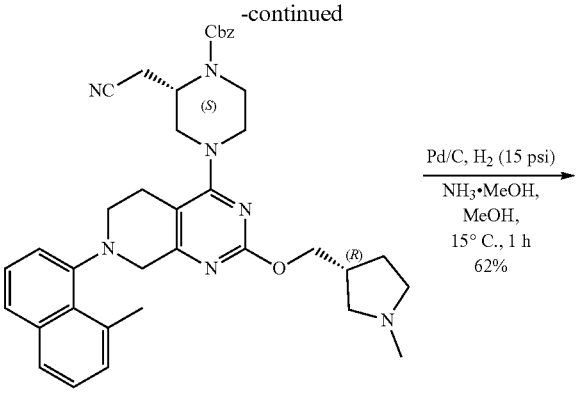

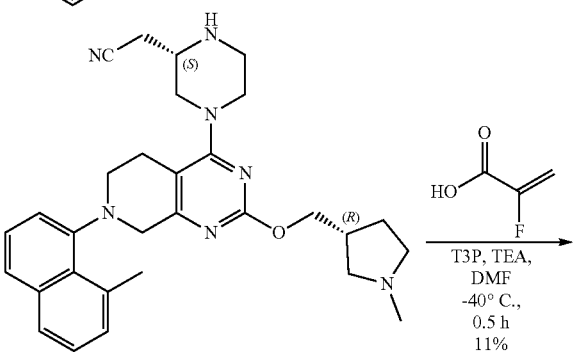

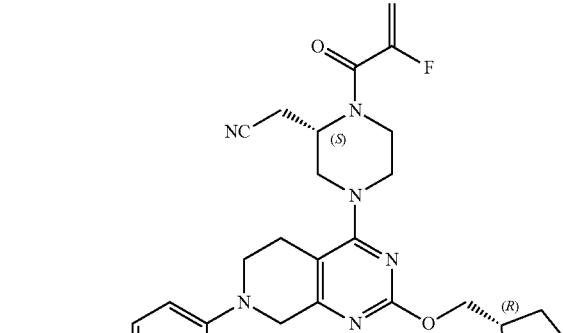

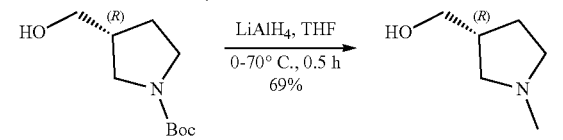
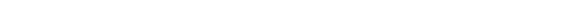

[(3R)-1-Methylpyrrolidin-3-yl]methanol

To the solution of tert-butyl (3R)-3-(hydroxymethyl)pyrrolidine-1-carboxylate (0.5 g, 2.48 mmol, 1 eq) in THF (20 mL) was added LiAlH₄ (189 mg, 4.97 mmol, 2 eq) at 0° C., then the mixture was warmed to 70° C. and stirred at 70° C. for 0.5 hour. Upon completion, the reaction mixture was quenched with saturated Na₂SO₄ (1 mL). The precipitate was filtered off and the filter cake was washed with THF (3×20 mL). The combined organic layers were dried over Na₂SO₄ and concentrated under vacuum to give [(3R)-1-methylpyrrolidin-3-yl]methanol (220 mg, 1.72 mmol, 69% yield, 90% purity) as a colorless oil which was used directly in the next step without further purification.

1H NMR (400 MHz, chloroform-d) δ=3.67-3.57 (m, 1H), 3.50 (dd, J=6.0, 10.0 Hz, 1H), 3.45-3.18 (m, 1H), 2.70 (dt, J=4.8, 8.8 Hz, 1H), 2.56-2.44 (m, 2H), 2.42-2.24 (m, 5H), 2.04-1.90 (m, 1H), 1.68-1.54 (m, 1H).

Step A: Benzyl (2S)-2-(cyanomethyl)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazine-1-carboxylate To a solution of benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (500 mg, 841 μmol, 1 eq) and [(3R)-1-methylpyrrolidin-3-yl]methanol (194 mg, 1.68 mmol, 2 eq) in toluene (10 mL) was added t-BuONa (162 mg, 1.68 mmol, 2 eq). The mixture was stirred at 0° C. for 10 minutes. Upon completion, the mixture was diluted with water (10 mL) and extracted with EtOAc (2×40 mL). The organic layers were dried over Na$_2$SO$_4$ and concentrated under vacuum. The residue was purified by silica gel chromatography (EtOAc/MeOH 50/1 to 3/1) to give benzyl (2S)-2-(cyanomethyl)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazine-1-carboxylate (290 mg, 427 μmol, 51% yield, 95% purity) as a yellow solid. LCMS [ESI, M+1]: 646.
$^1$H NMR (400 MHz, chloroform-d) δ=7.72-7.61 (m, 2H), 7.45-7.37 (m, 5H), 7.37-7.30 (m, 2H), 7.27-7.16 (m, 2H), 5.28-5.15 (m, 2H), 4.68 (br s, 1H), 4.30-4.01 (m, 6H), 4.00-3.73 (m, 2H), 3.56-3.31 (m, 2H), 3.26-3.06 (m, 3H), 3.05-2.94 (m, 2H), 2.91 (s, 3H), 2.82-2.70 (m, 4H), 2.70-2.57 (m, 2H), 2.47 (d, J=4.4 Hz, 3H), 2.20-2.07 (m, 1H), 1.80-1.67 (m, 1H).

Step B: 2-[(2S)-4-[7-(8-Methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazine-1-carboxylate (290 mg, 449 μmol, 1 eq) in MeOH (4 mL) was added NH$_3$.MeOH (2 mL, 15% purity), Pd/C (100 mg, 449 μmol, 10% purity, 1 eq) under N$_2$. The suspension was degassed under vacuum and purged with H$_2$ several times. The mixture was stirred under H$_2$ (15 psi) at 15° C. for 1 hour. Upon completion, the mixture was filtered and the filtrate was concentrated under vacuum to give 2-[(2S)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (150 mg, 279 μmol, 62% yield, 95% purity) as a yellow solid which was used directly in the next step without further purification. LCMS [ESI, M+1]: 512.

Step C: 2-[(2S)-1-(2-Fluoroprop-2-enoyl)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (120 mg, 235 μmol, 1 eq), 2-fluoroprop-2-enoic acid (42.2 mg, 469 μmol, 2 eq) and TEA (71.2 mg, 704 μmol, 97.9 μL, 3 eq) in DMF (2 mL) was added T3P (224 mg, 352 μmol, 209 μL, 50% purity in EtOAc, 1.5 eq) at −40° C. Then the mixture was stirred at −40° C. for 0.5 hour. Upon completion, the mixture was diluted with water (2 mL) and extracted with the mixed solvent (EtOAc/MeOH 10/1, 5×5 mL). The organic layers were dried over Na$_2$SO$_4$ and concentrated under vacuum. The residue was purified by chromatography (Al$_2$O$_3$, EtOAc/MeOH 50/1 to 20/1) followed by prep-HPLC (column: Phenomenex Gemini 150*25 mm*10 μm; mobile phase: [water (10 mM NH$_4$HCO$_3$)-ACN]; B %: 50%-100%, 10 min). The desired fractions were collected and lyophilized to give title compound 2-[(2S)-1-(2-fluoroprop-2-enoyl)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (16.0 mg, 26.5 μmol, 11% yield, 96.5% purity) as off-white solid. LCMS [ESI, M+1]: 584.
$^1$H NMR (400 MHz, chloroform-d) δ=7.74-7.61 (m, 2H), 7.45-7.38 (m, 1H), 7.35 (t, J=7.6 Hz, 1H), 7.27-7.17 (m, 2H), 5.55-5.32 (m, 1H), 5.26 (dd, J=3.6, 16.8 Hz, 1H), 4.88 (br s, 1H), 4.33-4.02 (m, 5H), 4.01-3.65 (m, 2H), 3.61-3.36 (m, 2H), 3.27-2.97 (m, 4H), 2.92 (s, 3H), 2.90-2.74 (m, 2H), 2.74-2.56 (m, 4H), 2.55-2.42 (m, 2H), 2.36 (d, J=2.4 Hz, 3H), 2.14-1.99 (m, 1H), 1.66-1.52 (m, 1H).

Example 563

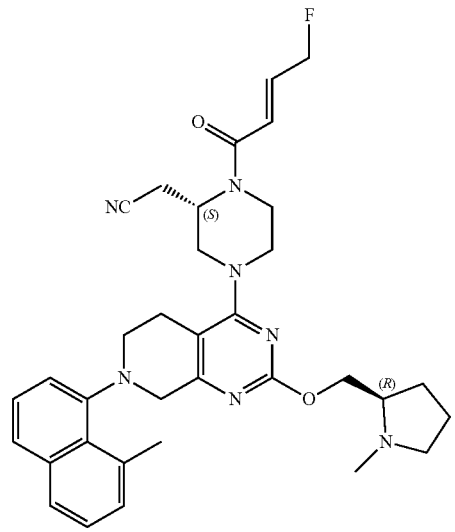

2-[(2S)-1-[(E)-4-Fluorobut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile

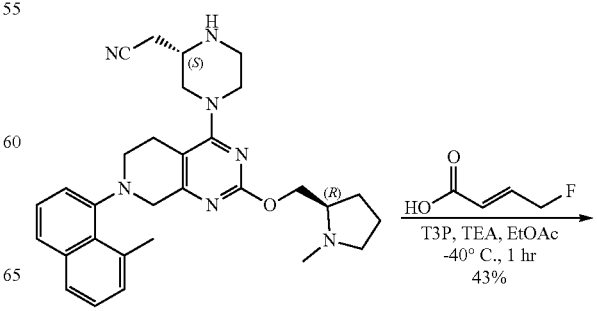

1443

-continued

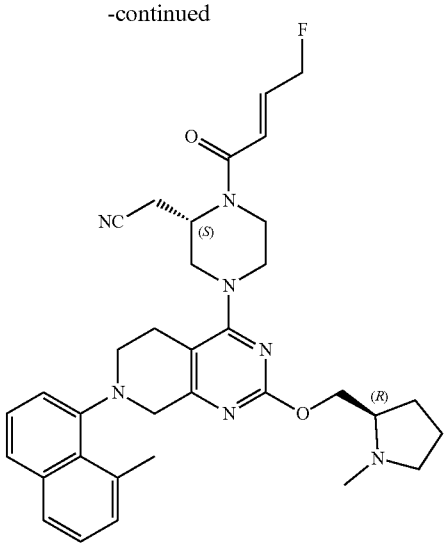

2-[(2S)-1-[(E)-4-Fluorobut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (260 mg, 508 μmol, 1.0 eq) in ethyl acetate (1.5 mL) was added a solution of (E)-4-fluorobut-2-enoic acid (106 mg, 1.02 mmol, 2.0 eq) in ethyl acetate (0.5 mL), TEA (206 mg, 2.03 mmol, 283 μL, 4.0 eq) and T3P (647 mg, 1.02 mmol, 605 μL, 50% purity, 2.0 eq), and the mixture was stirred at −40° C. and stirred for 1 hour. After completion, the reaction mixture was quenched by H$_2$O (10.0 mL), and extracted with ethyl acetate (3×15.0 mL). The combined organic layers were dried over Na$_2$SO$_4$, filtered and concentrated under reduced pressure to give a residue. The residue was purified by prep-HPLC (column: Luna C18 150*25 5 u; mobile phase: [water (0.225% FA)-ACN]; B %: 25%-45%, 7.8 min). The obtained product was adjusted to pH ~8 with saturated aqueous NaHCO$_3$, then concentrated, the aqueous layer was extracted with ethyl acetate (3×20.0 mL), the combined organic layer was dried over Na$_2$SO$_4$, filtered and concentrated to give title compound 2-[(2S)-1-[(E)-4-fluorobut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (132 mg, 220 μmol, 43% yield, 99% purity) as a white solid. LCMS [ESI, M+1]: 598.

$^1$H NMR (400 MHz, Chloroform-d) δ 7.70-7.62 (m, 2H), 7.43-7.38 (m, 1H), 7.36-7.31 (m, 1H), 7.26-7.19 (m, 2H), 7.04-6.94 (m, 1H), 6.59 (d, J=14.4 Hz, 1H), 5.17-4.60 (m, 3H), 4.41-4.35 (m, 1H), 4.28-3.44 (m, 9H), 3.20-3.08 (m, 4H), 3.05-2.99 (m, 1H), 2.92 (s, 3H), 2.83-2.77 (m, 1H), 2.72-2.62 (m, 2H), 2.47 (d, J=4.8 Hz, 3H), 2.32-2.25 (m, 1H), 2.09-2.01 (m, 1H), 1.88-1.70 (m, 3H).

1444

Example 564

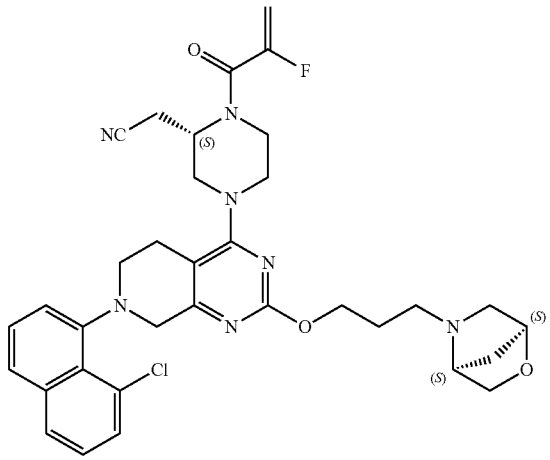

2-[(2S)-4-[7-(8-Chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-(2-fluoroprop-2-enoyl)piperazin-2-yl]acetonitrile

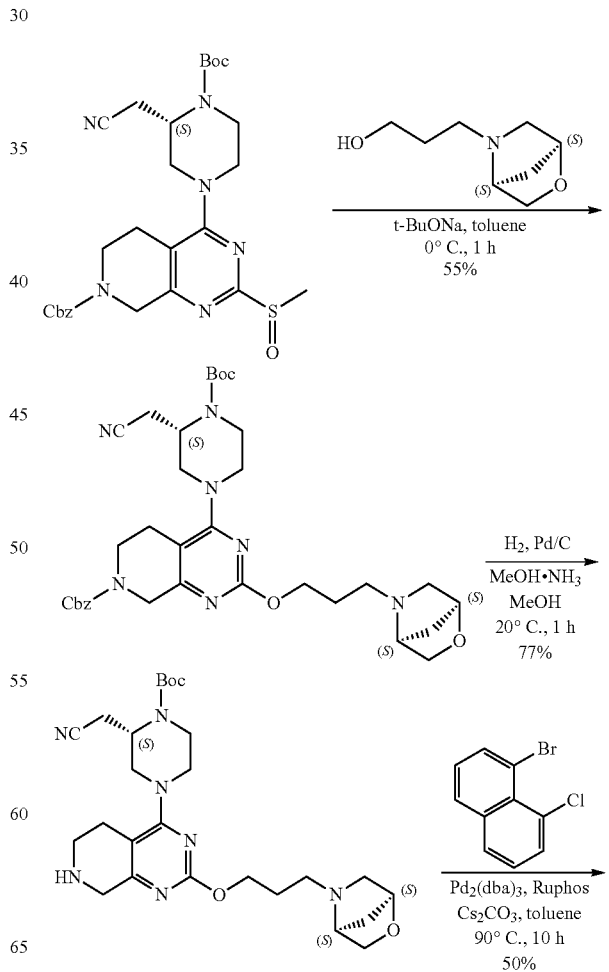

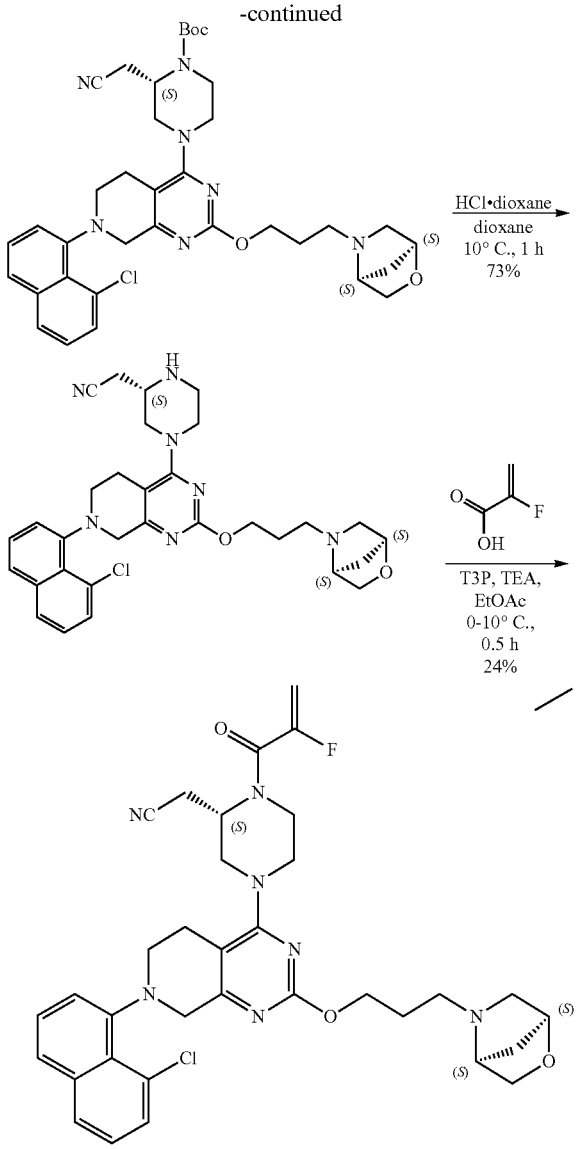

Step A: Benzyl 4-[(3S)-4-tert-butoxycarbonyl-3-(cyanomethyl)piperazin-1-yl]-2-[3-[(1S,4S)-2-oxa-5-azabicyclo[2.2.1]heptan-5-yl]propoxy]-6,8-dihydro-5H-pyrido[3,4-d]pyrimidine-7-carboxylate To a solution of benzyl 4-[(3S)-4-tert-butoxycarbonyl-3-(cyanomethyl)piperazin-1-yl]-2-methylsulfinyl-6,8-dihydro-5H-pyrido[3,4-d]pyrimidine-7-carboxylate (800 mg, 1.44 mmol, 1 eq) in toluene (20 mL) was added t-BuONa (277 mg, 2.88 mmol, 2 eq) and 3-[(1S,4S)-2-oxa-5-azabicyclo[2.2.1]heptan-5-yl]propan-1-ol (340 mg, 2.16 mmol, 1.5 eq) at 0° C. The mixture was stirred at 0° C. for 0.5 hour. The reaction mixture was diluted with water (30 mL) and extracted with ethyl acetate (30 mL×3). The combined organic layers were washed with brine (20 mL), dried over $Na_2SO_4$, filtered and concentrated under reduced pressure to give a residue. The residue was purified by reverse phase flash [water (0.1% formic acid)/acetonitrile)]. The mixture was adjusted pH=7 with saturated aqueous $NaHCO_3$ and extracted with ethyl acetate (20 mL×3). The combined organic layers were washed with brine (20 mL), dried over $Na_2SO_4$, filtered and concentrated under reduced pressure to give the product. Benzyl 4-[(3S)-4-tert-butoxycarbonyl-3-(cyanomethyl)piperazin-1-yl]-2-[3-[(1S,4S)-2-oxa-5-azabicyclo[2.2.1]heptan-5-yl]propoxy]-6,8-dihydro-5H-pyrido[3,4-d]pyrimidine-7-carboxylate (500 mg, 725 μmol, 50% yield, 94% purity) was obtained as a yellow solid. LCMS [ESI, M+1]: 648.

$^1$H NMR (400 MHz, chloroform-d) δ=7.44-7.30 (m, 5H), 5.19 (s, 2H), 4.79-4.53 (m, 2H), 4.51-4.30 (m, 4H), 4.09-3.71 (m, 5H), 3.67-3.58 (m, 1H), 3.54-3.36 (m, 2H), 3.32-3.12 (m, 2H), 3.04-2.87 (m, 2H), 2.85-2.46 (m, 7H), 2.00-1.89 (m, 2H), 1.85 (d, J=9.2 Hz, 1H), 1.72 (d, J=9.2 Hz, 1H), 1.51 (s, 9H).

Step B: tert-Butyl (2S)-2-(cyanomethyl)-4-[2-[3-[(1S,4S)-2-oxa-5-azabicyclo[2.2.1]heptan-5-yl]propoxy]-5,6,7,8-tetrahydropyrido[3,4-d]pyrimidin-4-yl]piperazine-1-carboxylate To a solution of benzyl 4-[(3S)-4-tert-butoxycarbonyl-3-(cyanomethyl)piperazin-1-yl]-2-[3-[(1S,4S)-2-oxa-5-azabicyclo[2.2.1]heptan-5-yl]propoxy]-6,8-dihydro-5H-pyrido[3,4-d]pyrimidine-7-carboxylate (900 mg, 1.39 mmol, 1 eq) in MeOH (30 mL) was added Pd/C (100 mg, 10% purity) and $NH_3$.MeOH (20 mL, 25% purity) under $N_2$. The suspension was degassed under vacuum and purged with $H_2$ several times. The mixture was stirred under $H_2$ (15 psi) at 20° C. for 1 hour. The catalyst was filtered off and the filtrate was concentrated under vacuum. tert-butyl (2S)-2-(cyanomethyl)-4-[2-[3-[(1S,4S)-2-oxa-5-azabicyclo[2.2.1]heptan-5-yl]propoxy]-5,6,7,8-tetrahydropyrido[3,4-d]pyrimidin-4-yl]piperazine-1-carboxylate (650 mg, 1.06 mmol, 77% yield, 84% purity) was obtained as a yellow solid and used to next step without purification. LCMS [ESI, M+1]: 514.

Step C: tert-Butyl (2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-2-(cyanomethyl)piperazine-1-carboxylate To the solution of tert-butyl (2S)-2-(cyanomethyl)-4-[2-[3-[(1S,4S)-2-oxa-5-azabicyclo[2.2.1]heptan-5-yl]propoxy]-5,6,7,8-tetrahydropyrido[3,4-d]pyrimidin-4-yl]piperazine-1-carboxylate (180 mg, 350 μmol, 1 eq), 1-bromo-8-chloro-naphthalene (127 mg, 526 μmol, 1.5 eq), $Cs_2CO_3$ (342 mg, 1.05 mmol, 3 eq) and RuPhos (65.4 mg, 140 μmol, 0.4 eq) in toluene (6 mL) was added $Pd_2(dba)_3$ (64.2 mg, 70.1 μmol, 0.2 eq) under $N_2$. The suspension was degassed under vacuum and purged with $N_2$ several times. The mixture was stirred under $N_2$ at 90° C. for 10 hours. The reaction mixture was filtered, and the filtrate was concentrated under vacuum. The residue was purified by silica gel chromatography (from PE:EtOAc=5:1~1:1 to EtOAc:MeOH=1:0-20:1) to give tert-butyl (2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-2-(cyanomethyl)piperazine-1-carboxylate (130 mg, 173 μmol, 50% yield, 90% purity) as a brown solid. LCMS [ESI, M+1]: 674.

Step D: 2-[(2S)-4-[7-(8-Chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile To the solution of tert-butyl (2S)-4-[7-(8-chloro-1-naphthyl)-2-[3-[(1S,4S)-2-oxa-5-azabicyclo[2.2.1]heptan-5-yl]

propoxy]-6,8-dihydro-5H-pyrido[3,4-d]pyrimidin-4-yl]-2-(cyanomethyl)piperazine-1-carboxylate (150 mg, 222 µmol, 1 eq) in dioxane (0.6 mL) was added HCl/dioxane (4 M, 556 µL, 10 eq), the mixture was stirred at 10° C. for 1 hour. The reaction mixture was concentrated under vacuum. The residue was dissolved with water (15 mL) and EtOAc (10 mL), then separated. The aqueous phase was basified by NaHCO₃ solid to PH=8~9 and extracted with EtOAc (2×15 mL). The combined organic layers were washed with brine (20 mL). The combined organic layers were dried over anhydrous Na₂SO₄, filtered and concentrated under vacuum to give 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (100 mg, 162 µmol, 73% yield, 93% purity) as a brown solid which was used for next step without further purification. LCMS [ESI, M+1]: 574.

Step E: 2-[(2S)-4-[7-(8-Chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-(2-fluoroprop-2-enoyl)piperazin-2-yl]acetonitrile To the solution of 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (100 mg, 174 µmol, 1 eq), 2-fluoroprop-2-enoic acid (31.4 mg, 348 µmol, 2 eq) and TEA (141 mg, 1.39 mmol, 194 µL, 8 eq) in EtOAc (2 mL) was added T3P (332 mg, 522 µmol, 311 µL, 50% purity, 3 eq) at 0° C., the mixture was stirred at 10° C. for 0.5 hour. Water (3 mL) was added into the mixture. The mixture was extracted with EtOAc (2×3 mL). The combined organic layers were dried over anhydrous Na₂SO₄, filtered and concentrated under vacuum. The residue was purified by prep-HPLC (column: Xtimate C18 10µ 250 mm*50 mm; mobile phase: [water (0.05% ammonium hydroxide v/v)-ACN]; B %: 45%-75%,12 min) to give title compound 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-1-(2-fluoroprop-2-enoyl)piperazin-2-yl]acetonitrile (26.5 mg, 41 µmol, 24% yield, 99.9% purity) as a white solid. LCMS [ESI, M+1]: 646.

¹H NMR (400 MHz, chloroform-d) δ=7.76 (d, J=8.4 Hz, 1H), 7.62 (t, J=7.2 Hz, 1H), 7.53 (d, J=7.2 Hz, 1H), 7.45 (td, J=7.6, 12.4 Hz, 1H), 7.34 (t, J=7.6 Hz, 1H), 7.26-7.18 (m, 1H), 5.53-5.32 (m, 1H), 5.25 (dd, J=3.6, 16.8 Hz, 1H), 5.12-4.64 (m, 1H), 4.49-4.31 (m, 4H), 4.21-3.98 (m, 3H), 3.95-3.76 (m, 2H), 3.68-3.55 (m, 2H), 3.52-3.36 (m, 2H), 3.33-2.97 (m, 4H), 2.95-2.66 (m, 5H), 2.64-2.49 (m, 2H), 1.93 (m, 2H), 1.84 (br d, J=8.4 Hz, 1H), 1.71 (br d, J=10.0 Hz, 1H).

Example 565

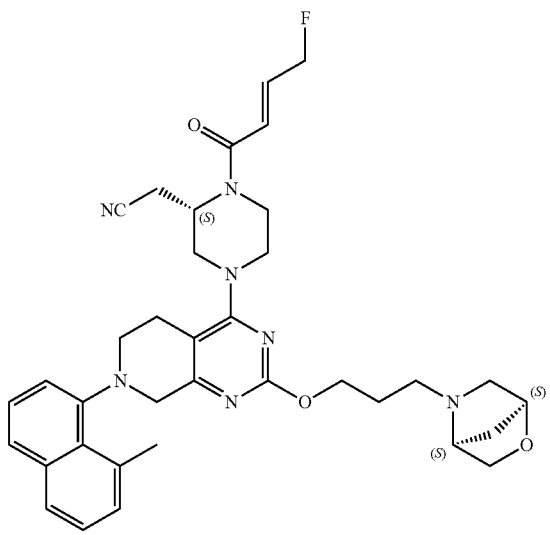

2-[(2S)-1-[(E)-4-Fluorobut-2-enoyl]-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile

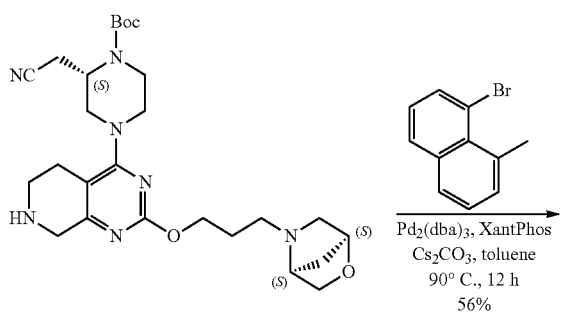

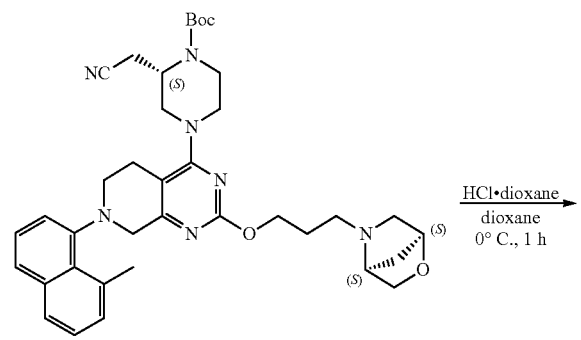

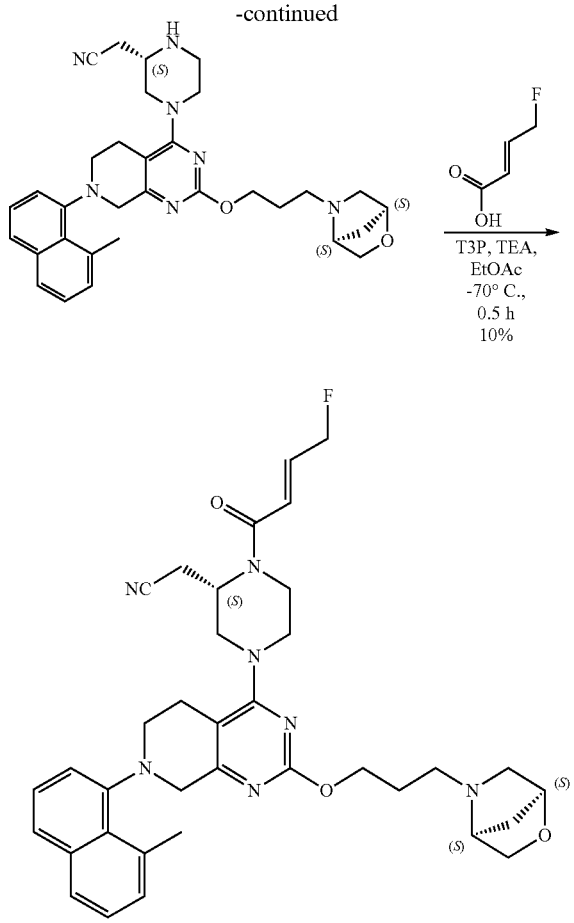

2H), 4.62 (br s, 1H), 4.45-4.31 (m, 3H), 4.30-4.16 (m, 1H), 4.10-3.70 (m, 5H), 3.61 (br d, J=7.6 Hz, 1H), 3.57-3.44 (m, 2H), 3.43-3.25 (m, 1H), 3.24-3.05 (m, 3H), 3.03-2.86 (m, 5H), 2.84-2.67 (m, 4H), 2.66-2.48 (m, 2H), 2.00-1.88 (m, 2H), 1.84 (d, J=9.6 Hz, 1H), 1.72 (d, J=9.6 Hz, 1H), 1.52 (s, 9H).

Step B: 2-[(2S)-4-[7-(8-Methyl-1-naphthyl)-2-[3-[(1S,4S)-2-oxa-5-azabicyclo[2.2.1] heptan-5-yl] propoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazine-1-carboxylate (250 mg, 382 µmol, 1 eq) in dioxane (2 mL) was added HCl/dioxane (4 M, 1.91 mL, 1.00 eq) at 0° C. The mixture was stirred at 0° C. for 1 hour. The reaction mixture was concentrated under vacuum. The residue was diluted with water (20 mL), and then the mixture was adjusted pH=7 with saturated NaHCO₃ aqueous solution and extracted with ethyl acetate (20 mL×3). The combined organic layers were washed with brine (20 mL), dried over Na₂SO₄, filtered and concentrated under reduced pressure to give the product. 2-[(2S)-4-[7-(8-methyl-1-naphthyl)-2-[3-[(1S,4S)-2-oxa-5-azabicyclo[2.2.1] heptan-5-yl]propoxy]-6,8-dihydro-5H-pyrido[3,4-d]pyrimidin-4-yl]piperazin-2-yl]acetonitrile (260 mg, crude) was obtained as a yellow oil and used to next step without purification. LCMS [ESI, M+1]: 554.

Step C: 2-[(2S)-1-[(E)-4-Fluorobut-2-enoyl]-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl] acetonitrile Step A: tert-Butyl (2S)-2-(cyanomethyl)-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazine-1-carboxylate A mixture of tert-butyl (2S)-2-(cyanomethyl)-4-[2-[3-[(1S,4S)-2-oxa-5-azabicyclo[2.2.1]heptan-5-yl]propoxy]-5,6,7,8-tetrahydropyrido[3,4-d]pyrimidin-4-yl]piperazine-1-carboxylate (350 mg, 681 µmol, 1 eq), 1-bromo-8-methyl-naphthalene (226 mg, 1.02 mmol, 1.5 eq), Xantphos (78.9 mg, 136 µmol, 0.2 eq), Pd₂(dba)₃ (62.4 mg, 68.1 µmol, 0.1 eq) and Cs₂CO₃ (555 mg, 1.70 mmol, 2.5 eq) in toluene (10 mL) was degassed and purged with N₂ for 3 times, and then the mixture was stirred at 90° C. for 12 hours under N₂. The reaction mixture was diluted with water (20 mL) and extracted with ethyl acetate (20 mL×3). The combined organic layers were washed with brine (20 mL), dried over Na₂SO₄, filtered and concentrated under reduced pressure to give a residue. The residue was purified by column chromatography (SiO₂, ethyl acetate/methanol=300/1 to 10/1). tert-butyl (2S)-2-(cyanomethyl)-4-[7-(8-methyl-1-naphthyl)-2-[3-[(1S,4S)-2-oxa-5-azabicyclo[2.2.1]heptan-5-yl] propoxy]-6,8-dihydro-5H-pyrido[3,4-d]pyrimidin-4-yl]piperazine-1-carboxylate (270 mg, 379 µmol, 56% yield, 92% purity) was obtained as a yellow solid. LCMS [ESI, M+1]: 654.

¹H NMR (400 MHz, chloroform-d) δ=7.75-7.61 (m, 2H), 7.45-7.37 (m, 1H), 7.34 (t, J=7.2 Hz, 1H), 7.26-7.15 (m, To a solution of 2-[(2S)-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl] acetonitrile (120 mg, 216 µmol, 1 eq), TEA (87.7 mg, 866 µmol, 121 µL, 4 eq) and (E)-4-fluorobut-2-enoic acid (45.1 mg, 433 µmol, 2 eq) in ethyl acetate (2 mL) was added T3P (276 mg, 433 µmol, 258 µL, 50% purity, 2 eq) at −70° C. The mixture was stirred at −70° C. for 0.5 hour. The reaction mixture was quenched with diluted with HCl (1 N, 1 mL) and then diluted with water (20 mL). The mixture was extracted with ethyl acetate (20 mL×3). The combined organic layers were washed with brine (10 mL), dried over Na₂SO₄, filtered and concentrated under reduced pressure to give a residue. The residue was purified by prep-HPLC (column: Waters Xbridge 150*25 5µ; mobile phase: [water (0.05% ammonium hydroxide v/v)-ACN]; B %: 40%-70%, 10 min). The desired fractions were collected and lyophilized. Title compound 2-[(2S)-1-[(E)-4-fluorobut-2-enoyl]-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (14.5 mg, 22.5 µmol, 10% yield, 99.3% purity) was obtained as a white solid. LCMS [ESI, M+1]: 640.

¹H NMR (400 MHz, chloroform-d) δ=7.70 (d, J=8.4 Hz, 1H), 7.65 (t, J=8.0 Hz, 1H), 7.45-7.30 (m, 2H), 7.27-7.16 (m, 2H), 7.09-6.91 (m, 1H), 6.59 (d, J=15.2 Hz, 1H), 5.29-4.48 (m, 3H), 4.44-4.31 (m, 3H), 4.29-3.72 (m, 6H), 3.71-3.40 (m, 4H), 3.28-2.96 (m, 4H), 2.95-2.88 (m, 4H), 2.87-2.56 (m, 5H), 2.52 (d, J=10.0 Hz, 1H), 1.99-1.87 (m, 2H), 1.84 (d, J=9.6 Hz, 1H), 1.71 (d, J=9.6 Hz, 1H).

Example 566

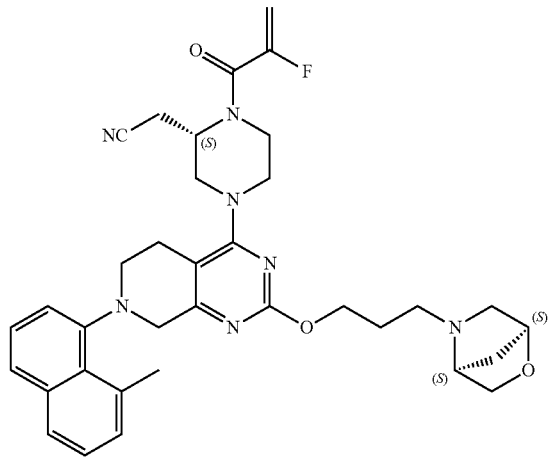

2-[(2S)-1-(2-Fluoroprop-2-enoyl)-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile

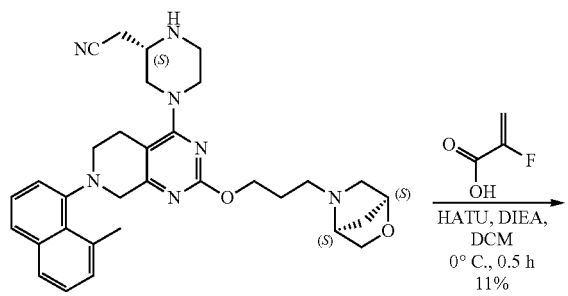

1452

2-[(2S)-1-(2-Fluoroprop-2-enoyl)-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (100 mg, 181 µmol, 1 eq) and 2-fluoroprop-2-enoic acid (32.5 mg, 361 µmol, 2 eq) in DCM (1 mL) was added HATU (137 mg, 361 µmol, 2 eq) and DIEA (93.4 mg, 722 µmol, 126 µL, 4 eq). After stirred at 0° C. for 0.5 hour, the reaction mixture was diluted with water (10 mL) and extracted with ethyl acetate (10 mL×3). The combined organic layers were washed with brine (10 mL), dried over Na₂SO₄, filtered and concentrated under reduced pressure to give a residue. The residue was purified by TLC (DCM/MeOH=10/1) and further purified by prep-HPLC (column: Xtimate C18 10µ 250 mm*50 mm; mobile phase: [water (0.05% ammonium hydroxide v/v)-ACN]; B %: 45%-75%, 12 min). The desired fraction was collected and lyophilized. Title compound 2-[(2S)-1-(2-fluoroprop-2-enoyl)-4-[7-(8-methyl-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (12 mg, 19.1 µmol, 11% yield, 99.6% purity) was obtained as a white solid. LCMS [ESI, M+1]: 626.

¹H NMR (400 MHz, chloroform-d) δ=7.63 (d, J=8.0 Hz, 1H), 7.58 (t, J=8.4 Hz, 1H), 7.39-7.23 (m, 2H), 7.19-7.09 (m, 2H), 5.35 (d, J=48.8 Hz, 1H), 5.18 (dd, J=3.6, 16.8 Hz, 1H), 5.04-4.40 (m, 1H), 4.37-3.89 (m, 7H), 3.86-3.61 (m, 2H), 3.59-3.32 (m, 4H), 3.20-2.40 (m, 14H), 1.95-1.81 (m, 2H), 1.78 (d, J=9.6 Hz, 1H), 1.65 (d, J=9.6 Hz, 1H).

Example 567

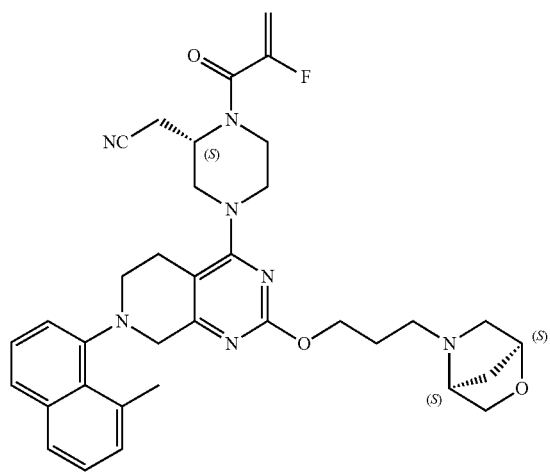

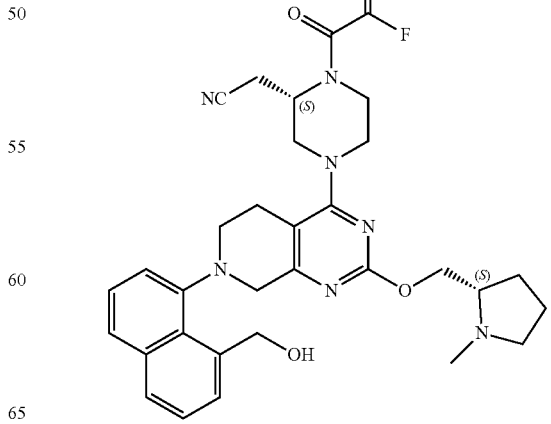

1453

2-[(2S)-1-(2-Fluoroprop-2-enoyl)-4-[7-[8-(hydroxymethyl)-1-naphthyl]-2-[[(2S)-1-methylpyrrolidin-2-yl]methoxy]-6,8-dihydro-5H-pyrido[3,4-d]pyrimidin-4-yl]piperazin-2-yl]acetonitrile

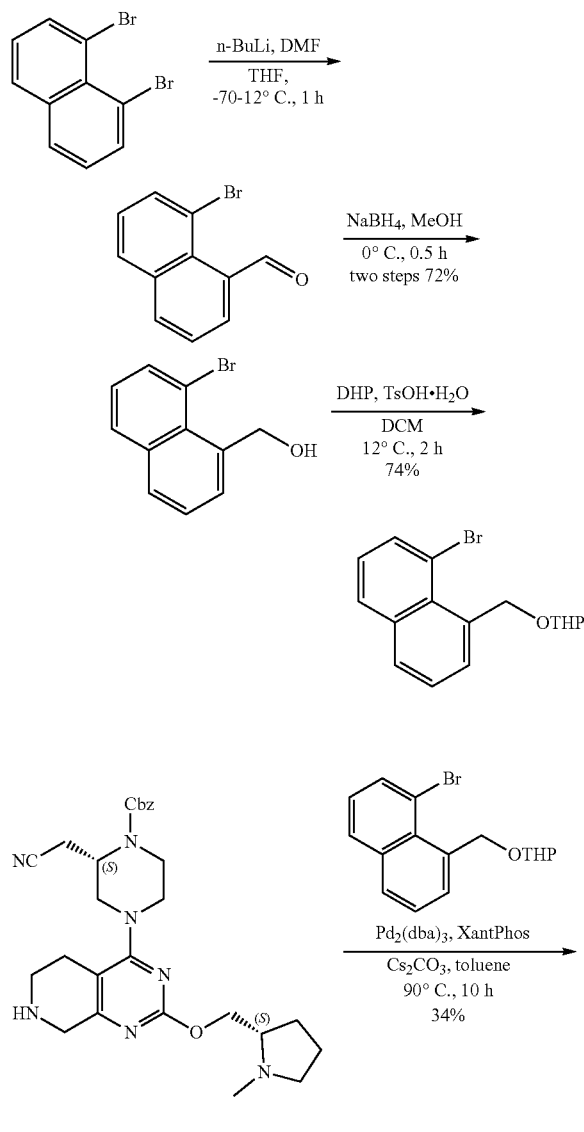

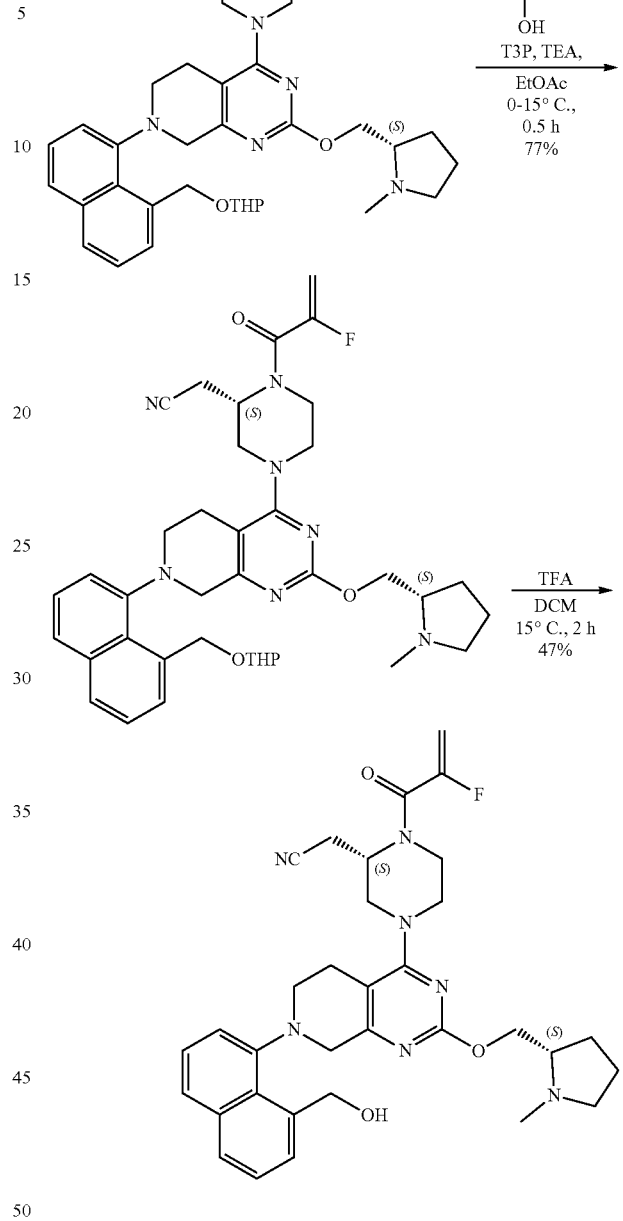

8-Bromonaphthalene-1-carbaldehyde

To a solution of 1,8-dibromonaphthalene (5 g, 17.5 mmol, 1 eq) in THF (100 mL) was added n-BuLi (2.5 M, 9.09 mL, 1.3 eq) at −70° C. dropwise. After stirring for 30 minutes at −70° C., DMF (12.8 g, 175 mmol, 13.5 mL, 10 eq) was added dropwise. The mixture was warmed up to 12° C. and stirred for another 0.5 hour. Upon completion, the mixture was quenched with saturated aqueous NH$_4$Cl (20 mL). The separated aqueous phase was extracted with EtOAc (2×50 mL). The combined organic layers were dried over Na$_2$SO$_4$, filtered and concentrated under vacuum to give 8-bromonaphthalene-1-carbaldehyde (4.5 g, crude) as a yellow solid which was used directly in the next step without further purification.

¹H NMR (400 MHz, chloroform-d) δ=11.4 (s, 1H), 8.04-7.92 (m, 2H), 7.90 (d, J=8.0 Hz, 2H), 7.60-7.55 (m, 1H), 7.39 (t, J=8.0 Hz, 1H).

(8-Bromo-1-naphthyl)methanol

To a mixture of 8-bromonaphthalene-1-carbaldehyde (4.5 g, 19.1 mmol) in MeOH (80 mL) was added NaBH₄ (2.90 g, 76.6 mmol) in one portion at 0° C. The mixture was stirred at 0° C. for 30 minutes. Upon completion, to the mixture was added water (1 mL) and the mixture was concentrated under vacuum. The residue was diluted with water (10 mL) and extracted with EtOAc (2×40 mL). The organic layers were dried over Na₂SO₄ and concentrated under vacuum. The residue was purified by silica gel chromatography (PE/EtOAc 30/1 to 3/1) to give (8-bromo-1-naphthyl)methanol (3.3 g, 12.5 mmol, two steps 72% yield, 90% purity) as a yellow solid.

¹H NMR (400 MHz, chloroform-d) δ=7.92-7.82 (m, 3H), 7.71 (d, J=6.8 Hz, 1H), 7.49 (t, J=7.6 Hz, 1H), 7.32-7.27 (m, 1H), 5.48 (br s, 2H).

2-[(8-Bromo-1-naphthyl)methoxy]tetrahydropyran

To a solution of (8-bromo-1-naphthyl)methanol (0.5 g, 2.11 mmol, 1 eq) in DCM (10 mL) was added DHP (355 mg, 4.22 mmol, 386 µL, 2 eq), followed by TsOH.H₂O (40.1 mg, 211 µmol, 0.1 eq) at 12° C. The mixture was stirred at 12° C. for 2 hours. Upon completion, the mixture was quenched with saturated aqueous NaHCO₃ solution (2 mL) and diluted with water (5 mL). The separated aqueous phase was extracted with EtOAc (10 mL). The combined organic layers were dried over Na₂SO₄, filtered and concentrated under vacuum. The residue was purified by silica gel chromatography (PE/EtOAc 500/1 to 100/1) to give 2-[(8-bromo-1-naphthyl)methoxy]tetrahydropyran (560 mg, 1.57 mmol, 74% yield, 90% purity) as a colorless oil.

¹H NMR (400 MHz, chloroform-d) δ=7.94-7.88 (m, 2H), 7.85 (t, J=8.4 Hz, 2H), 7.56-7.50 (m, 1H), 7.36-7.28 (m, 1H), 5.63 (s, 2H), 4.92 (t, J=3.6 Hz, 1H), 4.07-3.97 (m, 1H), 3.69-3.61 (m, 1H), 2.08-1.76 (m, 4H), 1.75-1.65 (m, 2H).

Step A: Benzyl (2S)-2-(cyanomethyl)-4-[2-[[(2S)-1-methylpyrrolidin-2-yl]methoxy]-7-[8-(tetrahydropyran-2-yloxymethyl)-1-naphthyl]-6,8-dihydro-5H-pyrido[3,4-d]pyrimidin-4-yl]piperazine-1-carboxylate 2-[(8-bromo-1-naphthyl)methoxy]tetrahydropyran (476 mg, 1.48 mmol, 1.5 eq), benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (500 mg, 989 µmol, 1 eq), Cs2CO3 (806 mg, 2.47 mmol, 2.5 eq), (5-diphenylphosphanyl-9,9-dimethyl-xanthen-4-yl)-diphenyl-phosphane (229 mg, 396 µmol, 0.4 eq) and Pd₂(dba)₃ (181 mg, 198 µmol, 0.2 eq) in toluene (20 mL) was de-gassed and then heated to 90° C. for 10 hours under N2. Upon completion, the mixture was filtered through a pad of celite and the filtrate was concentrated under vacuum. The residue was purified by reverse phase flash [water (0.1% FA)/acetonitrile]. The desired fractions were collected, neutralized with saturated aqueous NaHCO₃, concentrated under vacuum to remove MeCN and extracted with EtOAc (2×30 mL). The organic layers were dried over Na₂SO₄ and concentrated under vacuum to give benzyl (2S)-2-(cyanomethyl)-4-[2-[[(2S)-1-methylpyrrolidin-2-yl]methoxy]-7-[8-(tetrahydropyran-2-yloxymethyl)-1-naphthyl]-6,8-dihydro-5H-pyrido[3,4-d]pyrimidin-4-yl]piperazine-1-carboxylate (280 mg, 338 µmol, 34% yield, 90% purity) as a yellow solid. LCMS [ESI, M+1]: 746.

Step B: 2-[(2S)-4-[2-[[(2S)-1-Methylpyrrolidin-2-yl]methoxy]-7-[8-(tetrahydropyran-2-yloxymethyl)-1-naphthyl]-6,8-dihydro-5H-pyrido[3,4-d]pyrimidin-4-yl]piperazin-2-yl]acetonitrile To a solution of benzyl (2S)-2-(cyanomethyl)-4-[2-[[(2S)-1-methylpyrrolidin-2-yl]methoxy]-7-[8-(tetrahydropyran-2-yloxymethyl)-1-naphthyl]-6,8-dihydro-5H-pyrido[3,4-d]pyrimidin-4-yl]piperazine-1-carboxylate (280 mg, 375 µmol, 1 eq) in MeOH (6 mL) was added NH₃/MeOH (4 mL, 20% purity), Pd/C (120 mg, 10% purity) under N₂. The suspension was degassed under vacuum and purged with H₂ for several times. The mixture was stirred under H₂ (15 psi) at 15° C. for 1 hour. Upon completion, the mixture was filtered through a pad of celite and the filtrate was concentrated under vacuum to give 2-[(2S)-4-[2-[[(2S)-1-methylpyrrolidin-2-yl]methoxy]-7-[8-(tetrahydropyran-2-yloxymethyl)-1-naphthyl]-6,8-dihydro-5H-pyrido[3,4-d]pyrimidin-4-yl]piperazin-2-yl]acetonitrile (200 mg, 294 µmol, 78% yield, 90% purity) as a yellow solid which was used directly in the next step without further purification. LCMS [ESI, M+1]: 612.

Step C: 2-[(2S)-1-(2-Fluoroprop-2-enoyl)-4-[2-[[(2S)-1-methylpyrrolidin-2-yl]methoxy]-7-[8-(tetrahydropyran-2-yloxymethyl)-1-naphthyl]-6,8-dihydro-5H-pyrido [3,4-d]pyrimidin-4-yl]piperazin-2-yl]acetonitrile To a solution of 2-[(2S)-4-[2-[[(2S)-1-methylpyrrolidin-2-yl]methoxy]-7-[8-(tetrahydropyran-2-yloxymethyl)-1-naphthyl]-6,8-dihydro-5H-pyrido[3,4-d]pyrimidin-4-yl]piperazin-2-yl]acetonitrile (180 mg, 294 µmol, 1 eq), T3P (562 mg, 883 µmol, 525 µL, 50% purity in EtOAc, 3 eq) and TEA (238 mg, 2.35 mmol, 328 µL, 8 eq) in EtOAc (4 mL) was added 2-fluoroprop-2-enoic acid (53.0 mg, 588 µmol, 2 eq) at 0° C. The mixture was stirred at 15° C. for 0.5 hour. Upon completion, the mixture was diluted with water (4 mL) and extracted with EtOAc (3×10 mL). The organic layers were dried over Na₂SO₄ and concentrated under vacuum. The residue was purified by reverse phase flash [water (0.1% FA)/acetonitrile]. The desired fractions were collected and neutralized with NaHCO₃, concentrated under vacuum to remove MeCN and extracted with EtOAc (2×100 mL). The organic layers were dried over Na₂SO₄ and concentrated under vacuum to give 2-[(2S)-1-(2-fluoroprop-2-enoyl)-4-[2-[[(2S)-1-methylpyrrolidin-2-yl]methoxy]-7-[8-(tetrahydropyran-2-yloxymethyl)-1-naphthyl]-6,8-dihydro-5H-pyrido[3,4-d]pyrimidin-4-yl]piperazin-2-yl]acetonitrile (160 mg, 227 µmol, 77% yield, 97% purity) as a yellow solid. LCMS [ESI, M+1]: 684.

Step D: 2-[(2S)-1-(2-Fluoroprop-2-enoyl)-4-[7-[8-(hydroxymethyl)-1-naphthyl]-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-1-(2-fluoroprop-2-enoyl)-4-[2-[[(2S)-1-methylpyrrolidin-2-yl]methoxy]-7-[8-(tetrahydropyran-2-yloxymethyl)-1-naphthyl]-6,8-dihydro-5H-pyrido [3,4-d]pyrimidin-4-yl]piperazin-2-yl]acetonitrile (150 mg, 219 µmol, 1 eq) in DCM (160 µL) was added TFA (250 mg, 2.19 mmol, 162 µL, 10 eq). The mixture was stirred at 15°

C. for 2 hours. Upon completion, the mixture was diluted with dichloromethane (3 mL) and adjusted pH=9 with saturated Na$_2$CO$_3$ aqueous solution. The separated aqueous phase was extracted with DCM (5 mL). The combined organic layers were dried over Na$_2$SO$_4$, filtered and concentrated under vacuum. The residue was purified by prep-HPLC (column: Xtimate C18 150*25 mm*5 μm; mobile phase: [water (0.05% ammonium hydroxide v/v)-ACN]; B %: 42%-72%, 8 min). The desired fractions were collected and lyophilized to give title compound 2-[(2S)-1-(2-fluoro-prop-2-enoyl)-4-[7-[8-(hydroxymethyl)-1-naphthyl]-2-[[(2S)-1-methylpyrrolidin-2-yl]methoxy]-6, 8-dihydro-5H-pyrido[3,4-d]pyrimidin-4-yl]piperazin-2-yl]acetonitrile (62.0 mg, 103 μmol, 47% yield, 100% purity) as a white solid. LCMS [ESI, M+1]: 600.

$^1$H NMR (400 MHz, chloroform-d) δ=7.84 (d, J=8.0 Hz, 1H), 7.79 (dd, J=3.2, 7.2 Hz, 1H), 7.55-7.44 (m, 3H), 7.44-7.38 (m, 1H), 5.55-5.32 (m, 1H), 5.26 (dd, J=3.6, 16.8 Hz, 1H), 5.21-4.94 (m, 2H), 4.89 (br t, J=13.2 Hz, 1H), 4.41-3.90 (m, 7H), 3.66-3.39 (m, 2H), 3.37-3.00 (m, 5H), 3.00-2.58 (m, 4H), 2.50-2.43 (m, 3H), 2.33-2.22 (m, 1H), 2.11-1.98 (m, 1H), 1.90-1.73 (m, 3H).

Example 568

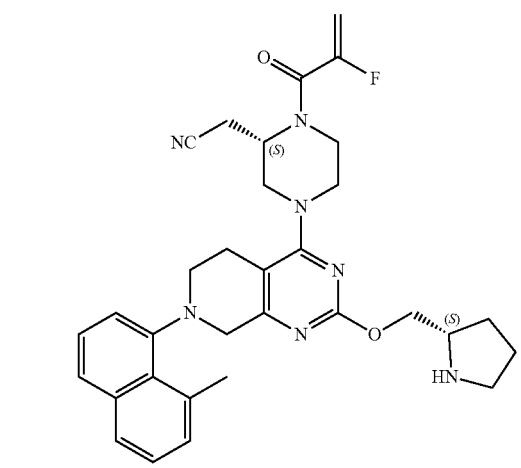

2-[(2S)-1-(2-Fluoroprop-2-enoyl)-4-[7-(8-methyl-1-naphthyl)-2-[[(2S)-pyrrolidin-2-yl]methoxy]-6,8-dihydro-5H-pyrido[3,4-d]pyrimidin-4-yl]piperazin-2-yl]acetonitrile

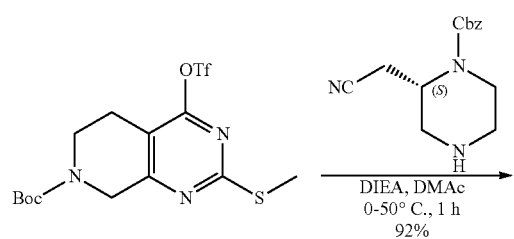

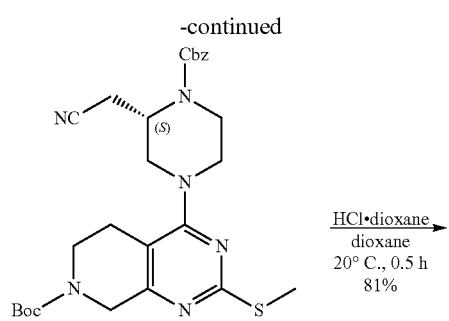

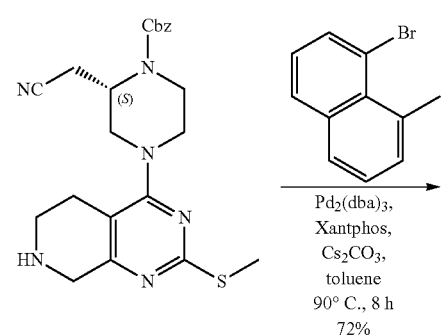

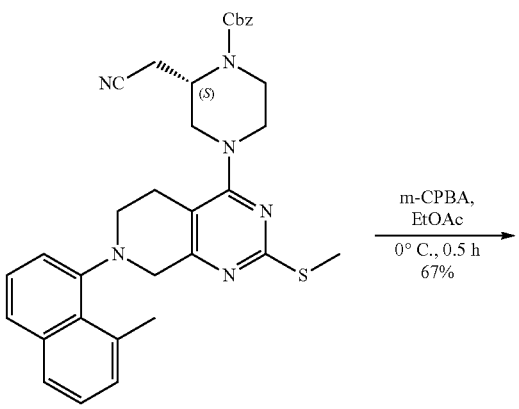

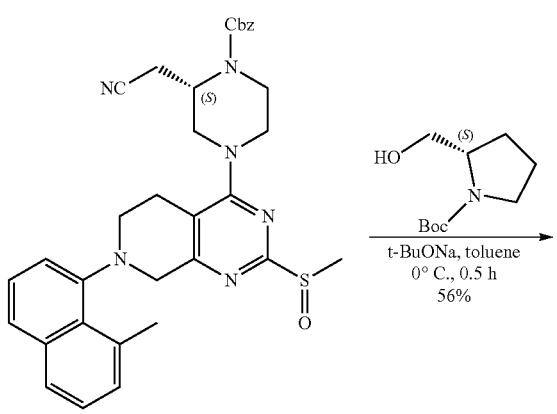

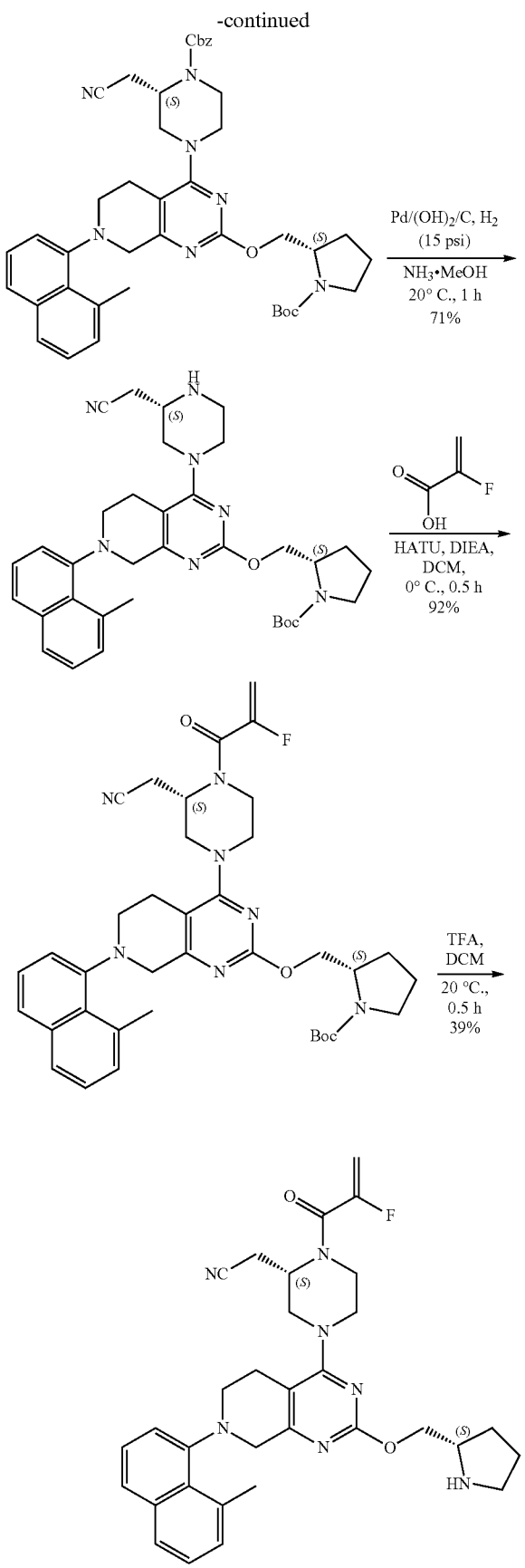

Step A: tert-Butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate To a mixture of tert-butyl 2-methylsulfanyl-4-(trifluoromethylsulfonyloxy)-6,8-dihydro-5H-pyrido[3,4-d]pyrimidine-7-carboxylate (20.0 g, 46.6 mmol, 1.00 eq) and benzyl (2S)-2-(cyanomethyl)piperazine-1-carboxylate (13.3 g, 51.2 mmol, 1.10 eq) in DMAc (250 mL) was added DIEA (18.1 g, 140 mmol, 24.3 mL, 3 eq) in portion at 0° C. under $N_2$. The mixture was heated to 50° C. and stirred for 1 hour. The reaction mixture was diluted with water (100 mL) and extracted with ethyl acetate (3×300 mL). The combined organic layers were washed with water (3×500 mL), dried over sodium sulfate, filtered and concentrated under reduced pressure to give a residue. The residue was purified by column chromatography ($SiO_2$, petroleum ether/ethyl acetate=50/1 to 1/1). Compound tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (23.0 g, 42.7 mmol, 92% yield, 100% purity) was obtained as a yellow solid. LCMS [ESI, M+1]: 539.

Step B: Benzyl (2S)-2-(cyanomethyl)-4-(2-methylsulfanyl-5,6,7,8-tetrahydropyrido [3,4-d]pyrimidin-4-yl)piperazine-1-carboxylate To a mixture of tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (23.0 g, 42.7 mmol, 1.00 eq) in dioxane (200 mL) was added HCl/dioxane (4 M, 192 mL, 18.0 eq). After stirred at 20° C. and for 0.5 hour, the reaction mixture was filtered and the filter cake was dissolved in ethyl acetate (200 mL). The pH was adjusted to 8-9 with saturated $Na_2CO_3$ solution and then diluted with water (20.0 mL). The separated water layer was extracted with ethyl acetate (2×50 mL). The combined organic layers were dried over sodium sulfate, filtered and concentrated under reduced pressure to give a residue. The residue was used into the next step directly without further purification. Compound benzyl (2S)-2-(cyanomethyl)-4-(2-methylsulfanyl-5,6,7,8-tetrahydropyrido [3,4-d]pyrimidin-4-yl)piperazine-1-carboxylate (16.1 g, 34.5 mmol, 81% yield, 94% purity) was obtained as a yellow solid.

$^1$H NMR (400 MHz, chloroform-d) δ=7.42-7.33 (m, 5H), 5.25-5.12 (m, 2H), 4.66 (br s, 1H), 4.11-4.04 (m, 1H), 4.03-3.90 (m, 3H), 3.84 (br d, J=13.6 Hz, 1H), 3.34-3.17 (m, 2H), 3.11 (td, J=5.2, 10.4 Hz, 1H), 3.04-2.93 (m, 2H), 2.88-2.76 (m, 1H), 2.75-2.56 (m, 3H), 2.50 (s, 3H).

Step C: Benzyl (2S)-2-(cyanomethyl)-4-[7-(8-methyl-1-naphthyl)-2-methylsulfanyl-6,8-dihydro-5H-pyrido[3,4-d]pyrimidin-4-yl]piperazine-1-carboxylate To a mixture of benzyl (2S)-2-(cyanomethyl)-4-(2-methylsulfanyl-5,6,7,8-tetrahydropyrido[3,4-d]pyrimidin-4-yl) piperazine-1-carboxylate (16.1 g, 36.7 mmol, 1.00 eq) and 1-bromo-8-methyl-naphthalene (10.6 g, 47.7 mmol, 1.30 eq) in toluene (350 mL) was added $Pd_2(dba)_3$ (6.72 g, 7.34 mmol, 0.20 eq), Xantphos (8.50 g, 14.7 mmol, 0.40 eq) and $Cs_2CO_3$ (35.9 g, 110 mmol, 3.00 eq). The mixture was degassed and purged with $N_2$ for 3 times. After stirred at 90° C. for 8 hours, the reaction mixture was diluted with water (1×100 mL) and extracted with ethyl acetate (3×150 mL). The combined organic layers were washed with water (1×300 mL) and brine (1×300 mL), dried over sodium sulfate, filtered and concentrated under reduced pressure to give a residue. The residue was purified by column chromatography (SiO$_2$, petroleum ether/ethyl acetate=100/1 to 2/1) and concentrated under reduced pressure to give a residue. Compound benzyl (2S)-2-(cyanomethyl)-4-[7-(8-methyl-1-naphthyl)-2-methylsulfanyl-6,8-dihydro-5H-pyrido[3,4-d]pyrimidin-4-yl]piperazine-1-carboxylate (15.3 g, 26.5 mmol, 72% yield) was obtained as a yellow solid.

$^1$H NMR (400 MHz, chloroform-d) δ=7.68-7.55 (m, 2H), 7.40-7.28 (m, 7H), 7.22 (s, 2H), 5.22-5.09 (m, 2H), 4.64 (br s, 1H), 4.27-4.14 (m, 1H), 4.05-3.84 (m, 2H), 3.83-3.68 (m, 1H), 3.55-3.30 (m, 2H), 3.18-3.03 (m, 3H), 3.01-2.79 (m, 5H), 2.78-2.50 (m, 3H), 2.45 (d, J=4.8 Hz, 3H).

Step D: Benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate To a mixture of benzyl (2S)-2-(cyanomethyl)-4-[7-(8-methyl-1-naphthyl)-2-methylsulfanyl-6,8-dihydro-5H-pyrido[3,4-d]pyrimidin-4-yl]piperazine-1-carboxylate (13.3 g, 23.0 mmol, 1.00 eq) in EtOAc (200 mL) was added m-CPBA (4.67 g, 23.0 mmol, 85% purity, 1.00 eq) at 0° C. under N$_2$. After stirring at 0° C. for 30 min, the reaction mixture was quenched with saturated Na$_2$S$_2$O$_3$ (100 mL) at 0° C. The separated organic layer was diluted with water (1×100 mL) and extracted with ethyl acetate (3×100 mL). The combined organic layers were dried over anhydrous Na$_2$SO$_4$, filtered and concentrated under reduced pressure to give a residue. The residue was purified by column chromatography (SiO$_2$, petroleum ether/ethyl acetate=50/1 to 0/1). Compound benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (9.60 g, 15.3 mmol, 67% yield, 95% purity) was obtained as a yellow solid. LCMS [ESI, M+1]: 595.

$^1$H NMR (400 MHz, chloroform-d) δ=7.74-7.63 (m, 2H), 7.47-7.31 (m, 7H), 7.27-7.17 (m, 2H), 5.25-5.17 (m, 2H), 4.67 (br s, 1H), 4.48-4.21 (m, 2H), 4.10-3.88 (m, 2H), 3.66-3.46 (m, 2H), 3.42-3.04 (m, 4H), 3.02-2.83 (m, 6H), 2.81-2.60 (m, 1H), 2.81-2.60 (m, 3H).

Step E: tert-Butyl (2S)-4-[2-[[(2S)-1-tert-butoxycarbonylpyrrolidin-2-yl]methoxy]-7-(8-methyl-1-naphthyl)-6,8-dihydro-5H-pyrido[3,4-d]pyrimidin-4-yl]-2-(cyanomethyl)piperazine-1-carboxylate To a mixture of benzyl (2S)-2-(cyanomethyl)-4-[7-(8-methyl-1-naphthyl)-2-methyl sulfinyl-6,8-dihydro-5H-pyrido[3,4-d]pyrimidin-4-yl]piperazine-1-carboxylate (500 mg, 841 µmol, 1.00 eq) and tert-butyl (2S)-2-(hydroxymethyl)pyrrolidine-1-carboxylate (338 mg, 1.68 mmol, 2.00 eq) in toluene (10.0 mL) was added t-BuONa (242 mg, 2.52 mmol, 3.00 eq) in portion at 0° C. under N$_2$. After stirring at 0° C. for 30 min, the reaction mixture was quenched by adding hydrochloric acid (1 M) 2 mL at 0° C., and water (10 mL). The mixture was extracted with ethyl acetate (20 mL×3). The combined organic layers were washed with water (30 mL×1) and brine (30 mL×1), dried over sodium sulfate, filtered and concentrated under reduced pressure to give a residue. The residue was purified by column chromatography (SiO$_2$, petroleum ether/ethyl acetate=50/1 to 0/1). Compound tert-butyl (2S)-4-[2-[[(2S)-1-tert-butoxycarbonylpyrrolidin-2-yl]methoxy]-7-(8-methyl-1-naphthyl)-6,8-dihydro-5H-pyrido[3,4-d]pyrimidin-4-yl]-2-(cyanomethyl)piperazine-1-carboxylate (330 mg, 473 µmol, 56% yield) was obtained as a yellow solid.

$^1$H NMR (400 MHz, chloroform-d) δ=7.73-7.61 (m, 2H), 7.47-7.31 (m, 7H), 7.26-7.15 (m, 2H), 5.27-5.14 (m, 2H), 4.68 (br s, 1H), 4.42-4.17 (m, 3H), 4.07-3.73 (m, 3H), 3.58-3.29 (m, 5H), 3.25-2.88 (m, 8H), 2.86-2.51 (m, 3H), 2.03-1.76 (m, 4H), 1.44 (d, J=4.8 Hz, 9H).

Step F: tert-Butyl (2S)-2-[[4-[(3S)-3-(cyanomethyl)piperazin-1-yl]-7-(8-methyl-1-naphthyl)-6,8-dihydro-5H-pyrido[3,4-d]pyrimidin-2-yl]oxymethyl]pyrrolidine-1-carboxylate To a mixture of tert-butyl (2S)-4-[2-[[(2S)-1-tert-butoxycarbonylpyrrolidin-2-yl]methoxy]-7-(8-methyl-1-naphthyl)-6,8-dihydro-5H-pyrido[3,4-d]pyrimidin-4-yl]-2-(cyanomethyl)piperazine-1-carboxylate (330 mg, 473 µmol, 1.00 eq) in MeOH (15 mL) was added NH$_3$.MeOH (15 mL, 20% purity), Pd(OH)$_2$/C (80 mg, 20% purity) in one portion under N$_2$. The suspension was degassed under vacuum and purged with H$_2$ for three times. The mixture was stirred under H$_2$ (15 psi) at 20° C. for 1 hour. The catalyst was filtered off and the filtrate was concentrated under reduced pressure to give a residue. The crude product was used into the next step directly without further purification. Compound tert-butyl (2S)-2-[[4-[(3S)-3-(cyanomethyl)piperazin-1-yl]-7-(8-methyl-1-naphthyl)-6,8-dihydro-5H-pyrido[3,4-d]pyrimidin-2-yl]oxymethyl]pyrrolidine-1-carboxylate (200 mg, 335 µmol, 71% yield) was obtained as a yellow solid. LCMS [ESI, M+1]: 598.

Step G: tert-Butyl (2S)-2-[[4-[(3S)-3-(cyanomethyl)-4-(2-fluoroprop-2-enoyl)piperazin-1-yl]-7-(8-methyl-1-naphthyl)-6,8-dihydro-5H-pyrido[3,4-d]pyrimidin-2-yl]oxymethyl]pyrrolidine-1-carboxylate To a mixture of tert-butyl (2S)-2-[[4-[(3S)-3-(cyanomethyl)piperazin-1-yl]-7-(8-methyl-1-naphthyl)-6,8-dihydro-5H-pyrido[3,4-d]pyrimidin-2-yl]oxymethyl]pyrrolidine-1-carboxylate (190 mg, 318 µmol, 1.00 eq) and 2-fluoroprop-2-enoic acid (42.9 mg, 477 µmol, 1.50 eq) in DCM (15.0 mL) was added DIEA (123 mg, 954 µmol, 166 uL, 3.00 eq) and HATU (181 mg, 477 µmol, 1.50 eq) in one portion at 0° C. under N$_2$. After stirring at 0° C. for 30 min, the reaction mixture was diluted with water (10 mL). The separated organic layer was washed with brine (1×10 mL), dried over Na$_2$SO$_4$, filtered and concentrated under vacuum. The residue was purified by column chromatography (SiO$_2$, DCM: MeOH=50:1 to 5:1). Compound tert-butyl (2S)-2-[[4-[(3S)-3-(cyanomethyl)-4-(2-fluoroprop-2-enoyl)piperazin-1-yl]-7-(8-methyl-1-naphthyl)-6,8-dihydro-5H-pyrido[3,4-d]pyrimidin-2-yl]oxymethyl]pyrrolidine-1-carboxylate (210 mg, 292 µmol, 92% yield, 93% purity) was obtained as a yellow solid. LCMS [ESI, M+1]: 670.

Step H: 2-[(2S)-1-(2-Fluoroprop-2-enoyl)-4-[7-(8-methyl-1-naphthyl)-2-[[(2S)-pyrrolidin-2-yl]methoxy]-6,8-dihydro-5H-pyrido[3,4-d]pyrimidin-4-yl]piperazin-2-yl]acetonitrile To a mixture of tert-butyl (2S)-2-[[4-[(3S)-3-(cyanomethyl)-4-(2-fluoroprop-2-enoyl)piperazin-1-yl]-7-(8-methyl-1-naphthyl)-6,8-dihydro-5H-pyrido[3,4-d]pyrimidin-2-yl]oxymethyl]pyrrolidine-1-carboxylate (210 mg, 314 µmol, 1.00 eq) in DCM (5.00 mL) was added TFA (1.07 g, 9.41 mmol, 696 µL, 30.0 eq) in one portion at 20° C. under N$_2$. After stirred at 20° C. for 30 min, the reaction mixture was concentrated under reduced pressure to give a residue. The residue was purified by prep-HPLC (column: Phenomenex Synergi C18 150×30 mm×4 μm; mobile phase: [water (0.225% FA)-ACN]; B %: 20%-50%,5 min). Title compound 2-[(2S)-1-(2-fluoroprop-2-enoyl)-4-[7-(8-methyl-1-naphthyl)-2-[[(2S)-pyrrolidin-2-yl]methoxy]-6,8-dihydro-5H-pyrido[3,4-d]pyrimidin-4-yl]piperazin-2-yl]acetonitrile (75.5 mg, 122 μmol, 39% yield, 99.8% purity, FA) was obtained as a off-white solid. LCMS [ESI, M+1]: 570.

$^1$H NMR (400 MHz, chloroform-d) δ=7.72-7.61 (m, 2H), 7.44-7.30 (m, 2H), 7.27-7.14 (m, 2H), 6.49-5.98 (m, 1H), 5.55-5.32 (m, 1H), 5.25 (dd, J=3.6, 16.8 Hz, 1H), 4.58-4.42 (m, 2H), 4.36-3.87 (m, 5H), 3.86-3.67 (m, 1H), 3.64-3.37 (m, 2H), 3.35-3.26 (m, 2H), 3.25-2.94 (m, 4H), 2.92-2.70 (m, 5H), 2.66-2.51 (m, 1H), 2.18-1.81 (m, 4H).

Example 569

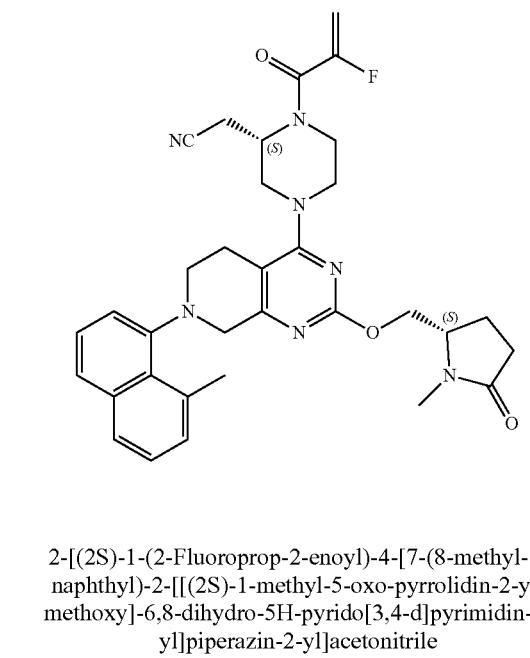

2-[(2S)-1-(2-Fluoroprop-2-enoyl)-4-[7-(8-methyl-1-naphthyl)-2-[[(2S)-1-methyl-5-oxo-pyrrolidin-2-yl]methoxy]-6,8-dihydro-5H-pyrido[3,4-d]pyrimidin-4-yl]piperazin-2-yl]acetonitrile

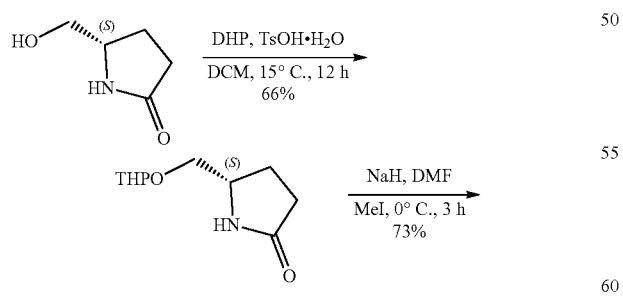

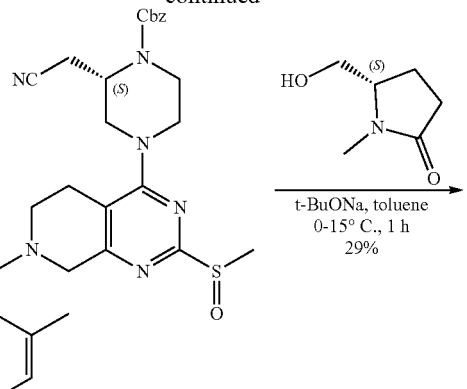

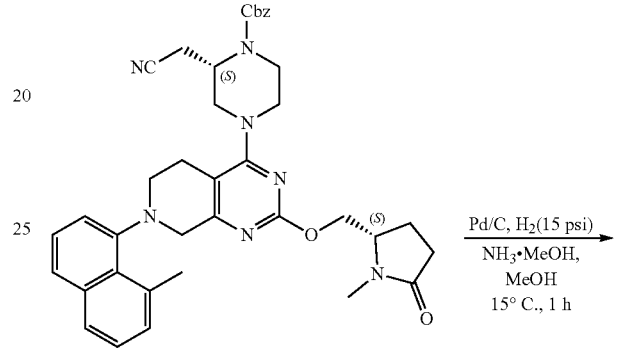

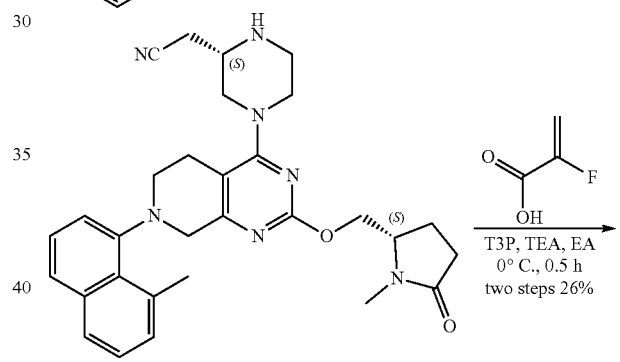

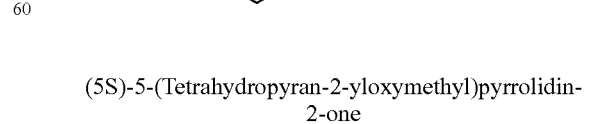

(5S)-5-(Tetrahydropyran-2-yloxymethyl)pyrrolidin-2-one

To a mixture of (5S)-5-(hydroxymethyl)pyrrolidin-2-one (5.00 g, 43.4 mmol, 1.00 eq) and DHP (3.65 g, 43.4 mmol, 3.97 mL, 1.00 eq) in DCM (80.0 mL) was added TsOH.H₂O (826 mg, 4.34 mmol, 0.10 eq). The mixture was stirred at 15° C. for 12 hours. The reaction mixture was washed with brine (30.0 mL×1), dried over sodium sulfate, filtered and concentrated under reduced pressure to give a residue. The residue was purified by column chromatography (SiO₂, petroleum ether/ethyl acetate=20/1 to 0:1). Compound (5S)-5-(tetrahydropyran-2-yloxymethyl)pyrrolidin-2-one (5.70 g, 28.6 mmol, 66% yield) was obtained as a yellow oil.

¹H NMR (400 MHz, chloroform-d) δ=6.36-6.01 (m, 1H), 4.66-4.47 (m, 1H), 3.92-3.71 (m, 2.5H), 3.64-3.43 (m, 2H), 3.24 (dd, J=8.0, 9.6 Hz, 0.5H), 2.42-2.10 (m, 3H), 1.86-1.64 (m, 3H), 1.62-1.48 (m, 4H).

(5S)-1-Methyl-5-(tetrahydropyran-2-yloxymethyl)pyrrolidin-2-one

To a mixture of (5S)-5-(tetrahydropyran-2-yloxymethyl)pyrrolidin-2-one (5.60 g, 28.1 mmol, 1.00 eq) in DMF (60.0 mL) was added NaH (1.35 g, 33.7 mmol, 60% purity, 1.20 eq) in portion at −40° C. under N₂. The mixture was stirred at −40° C. for 30 min, then CH₃I (6.58 g, 46.4 mmol, 2.89 mL, 1.65 eq) was added and stirred at 0° C. for 2.5 hours. The reaction mixture was quenched by adding saturated NaHSO₃ aqueous solution (30.0 mL) and extracted with EA (3×50.0 mL). The combined organic phase was dried over Na₂SO₄ and concentrated to dryness. The residue was purified by column chromatography (SiO₂, petroleum ether/ethyl acetate=10/1 to 0/1). Compound (5S)-1-methyl-5-(tetrahydropyran-2-yloxymethyl)pyrrolidin-2-one (4.40 g, 20.6 mmol, 73% yield) was obtained as a yellow oil.

¹H NMR (400 MHz, chloroform-d) δ=4.59 (td, J=3.2, 13.6 Hz, 1H), 3.93-3.73 (m, 2H), 3.63-371 (m, 1H), 3.57-3.44 (m, 2H), 2.88 (d, J=4.4 Hz, 3H), 2.54-2.40 (m, 1H), 2.38-2.24 (m, 1H), 2.07-2.20 (m, 1H), 1.93-1.53 (m, 7H).

(5S)-5-(Hydroxymethyl)-1-methyl-pyrrolidin-2-one

To a mixture of (5S)-1-methyl-5-(tetrahydropyran-2-yloxymethyl)pyrrolidin-2-one (2.20 g, 10.3 mmol, 1.00 eq) in DCM (20.0 mL) was added TFA (23.5 g, 206 mmol, 15.3 mL, 20.0 eq). The mixture was stirred at 15° C. for 30 min. The reaction mixture was concentrated under reduced pressure to give a residue. The crude product was used in the next step directly without further purification. Compound (5S)-5-(hydroxymethyl)-1-methyl-pyrrolidin-2-one (2.60 g, crude) was obtained as a red oil.

Step A: Benzyl (2S)-2-(cyanomethyl)-4-[7-(8-methyl-1-naphthyl)-2-[[(2S)-1-methyl-5-oxo-pyrrolidin-2-yl]methoxy]-6,8-dihydro-5H-pyrido[3,4-d]pyrimidin-4-yl]piperazine-1-carboxylate To a mixture of (5S)-5-(hydroxymethyl)-1-methyl-pyrrolidin-2-one (543 mg, 4.20 mmol, 5.00 eq) in THF (30.0 mL) was added t-BuONa (808 mg, 8.41 mmol, 10.0 eq) in portion at 0° C. under N₂. The mixture was stirred at 0° C. for 30 min, then benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (500 mg, 841 μmol, 1.00 eq) was added and warmed to 15° C. and stirred for 0.5 hour. The reaction mixture was diluted with water (20 mL) and extracted with ethyl acetate (30 mL×3). The combined organic layers were washed with water (50 mL×1), dried over sodium sulfate, filtered and concentrated under reduced pressure to give a residue. The residue was purified by reverse phase flash [water (0.1% TFA)/acetonitrile]. The desired fractions were collected and neutralized with saturated NaHCO₃ solution (10.0 mL) and extracted with ethyl acetate (50.0 mL×2). The separated organic layer was dried over sodium sulfate, filtered and concentrated under vacuum. Compound benzyl (2S)-2-(cyanomethyl)-4-[7-(8-methyl-1-naphthyl)-2-[[(2S)-1-methyl-5-oxo-pyrrolidin-2-yl]methoxy]-6,8-dihydro-5H-pyrido[3,4-d]pyrimidin-4-yl]piperazine-1-carboxylate (162 mg, 243 μmol, 29% yield, 99% purity) was obtained as a yellow solid. LCMS [ESI, M+1]: 660.

Step B: 2-[(2S)-4-[7-(8-Methyl-1-naphthyl)-2-[[(2S)-1-methyl-5-oxo-pyrrolidin-2-yl]methoxy]-6,8-dihydro-5H-pyrido[3,4-d]pyrimidin-4-yl]piperazin-2-yl]acetonitrile To a mixture of benzyl (2S)-2-(cyanomethyl)-4-[7-(8-methyl-1-naphthyl)-2-[[(2S)-1-methyl-5-oxo-pyrrolidin-2-yl]methoxy]-6,8-dihydro-5H-pyrido[3,4-d]pyrimidin-4-yl]piperazine-1-carboxylate (130 mg, 197 μmol, 1.00 eq) in MeOH (2.00 mL) was added NH₃.MeOH (1.00 mL, 20% purity) and Pd/C (35.0 mg, 10% purity). The suspension was degassed under vacuum and purged with H₂ several times. The mixture was stirred under H₂ (15 psi) at 15° C. for 1 hour. The reaction mixture was filtered and concentrated under reduced pressure to give a residue. The crude product was used in the next step directly without further purification. Compound 2-[(2S)-4-[7-(8-methyl-1-naphthyl)-2-[[(2S)-1-methyl-5-oxo-pyrrolidin-2-yl]methoxy]-6,8-dihydro-5H-pyrido[3,4-d]pyrimidin-4-yl]piperazin-2-yl]acetonitrile (70.0 mg, crude) was obtained as a brown solid. LCMS [ESI, M+1]: 526.

Step C: 2-[(2S)-1-(2-Fluoroprop-2-enoyl)-4-[7-(8-methyl-1-naphthyl)-2-[[(2S)-1-methyl-5-oxo-pyrrolidin-2-yl]methoxy]-6,8-dihydro-5H-pyrido[3,4-d]pyrimidin-4-yl]piperazin-2-yl]acetonitrile To a mixture of 2-[(2S)-4-[7-(8-methyl-1-naphthyl)-2-[[(2S)-1-methyl-5-oxo-pyrrolidin-2-yl]methoxy]-6,8-dihydro-5H-pyrido[3,4-d]pyrimidin-4-yl]piperazin-2-yl]acetonitrile (60.0 mg, 114 μmol, 1.00 eq) and 2-fluoroprop-2-enoic acid (20.6 mg, 228 μmol, 2.00 eq) in EA (1.00 mL) was added TEA (92.4 mg, 913 μmol, 127 uL, 8.00 eq), T3P (218 mg, 342 μmol, 204 uL, 50% purity, 3.00 eq) in portion at 0° C. under N₂. The mixture was stirred at 0° C. for 30 min. The reaction mixture was diluted with water (5.00 mL) and extracted with ethyl acetate (10.0 mL×3). The combined organic layers were washed with water (10.0 mL×1) and brine (10.0 mL×1), dried over sodium sulfate, filtered and concentrated under reduced pressure to give a residue. The residue was purified by prep-HPLC (column: Xtimate C18 150×25 mm×5 um; mobile phase: [water (0.05% ammonium hydroxide v/v)-ACN]; B %: 42%-72%,10 min). Title compound 2-[(2S)-1-(2-fluoroprop-2-enoyl)-4-[7-(8-methyl-1-naphthyl)-2-[[(2S)-1-methyl-5-oxo-pyrrolidin-2-yl]methoxy]-6, 8-dihydro-5H-pyrido [3,4-d]pyrimidin-4-yl]piperazin-2-yl]acetonitrile (26.8 mg, 43.9 μmol, two steps 26% yield, 98% purity) was obtained as a white solid. LCMS [ESI, M+1]: 598.

¹H NMR (400 MHz, chloroform-d) δ=7.73-7.62 (m, 2H), 7.46-7.38 (m, 1H), 7.38-7.32 (m, 1H), 7.27-7.17 (m, 2H), 5.55-5.32 (m, 1H), 5.26 (dd, J=3.6, 16.8 Hz, 1H), 5.08-4.63 (m, 1H), 4.53-4.39 (m, 1H), 4.37-4.26 (m, 1H), 4.25-4.00 (m, 3H), 3.97-3.71 (m, 3H), 3.59-3.35 (m, 2H), 3.29-2.98

(m, 4H), 2.91 (d, J=5.6 Hz, 8H), 2.69-2.58 (m, 1H), 2.57-2.45 (m, 1H), 2.42-2.29 (m, 1H), 2.28-2.14 (m, 1H), 2.06-1.91 (m, 1H).
Example 570
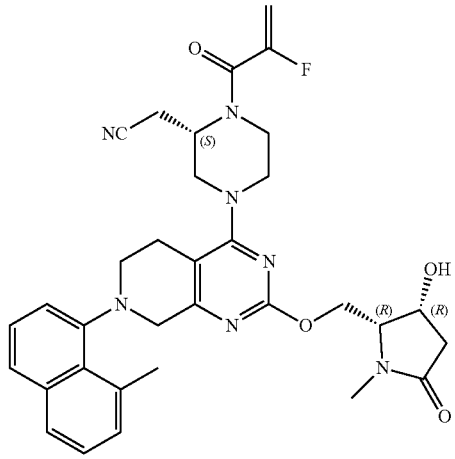
2-[(2S)-1-(2-Fluoroprop-2-enoyl)-4-[2-[[(2R,3R)-3-hydroxy-1-methyl-5-oxo-pyrrolidin-2-yl]methoxy]-7-(8-methyl-1-naphthyl)-6,8-dihydro-5H-pyrido[3,4-d]pyrimidin-4-yl]piperazin-2-yl]acetonitrile
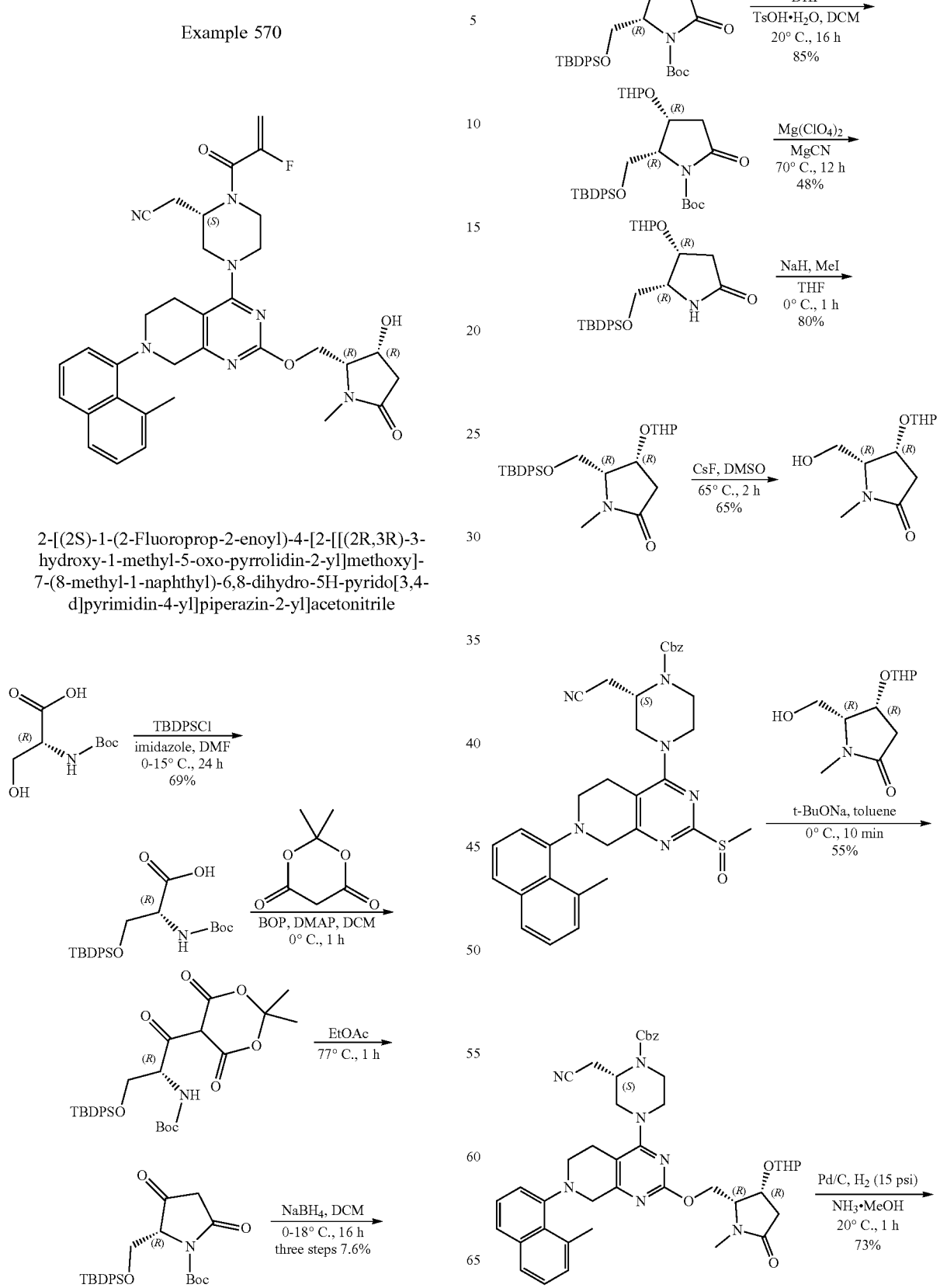

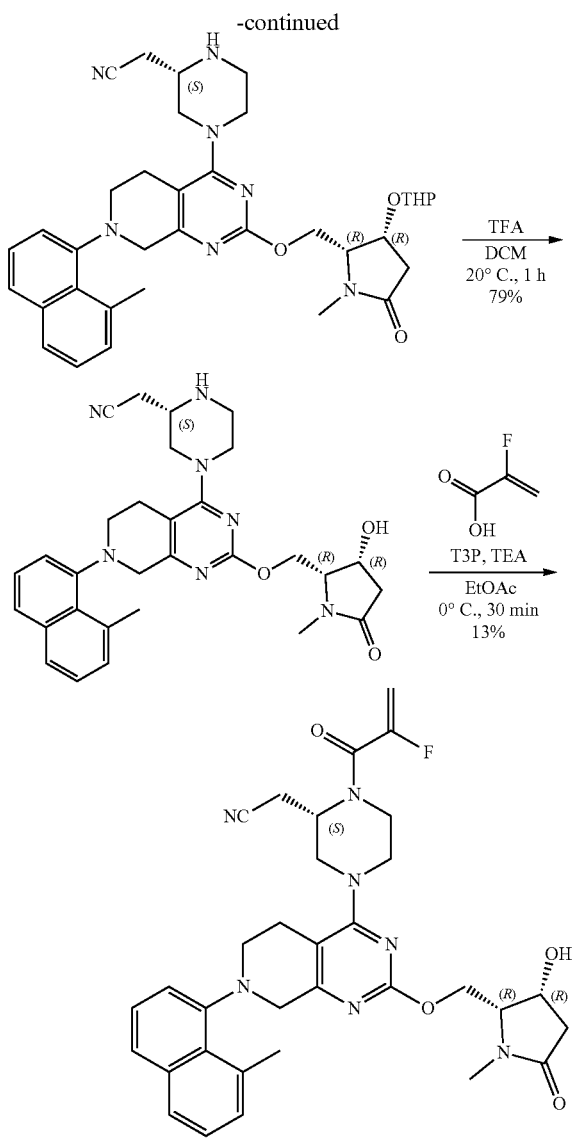

(2R)-2-(tert-Butoxycarbonylamino)-3-[tert-butyl (diphenyl)silyl] oxy-propanoic acid To a solution of (2R)-2-(tert-butoxycarbonylamino)-3-hydroxy-propanoic acid (27 g, 132 mmol, 1 eq) in DMF (270 mL) was added imidazole (45.4 g, 667 mmol, 5.07 eq) at 0° C. under nitrogen. After the solution became clear, TBDPSCl (90.4 g, 329 mmol, 84.5 mL, 2.5 eq) was added. The reaction was warmed to 15° C. After stirring at 15° C. for 24 h, the reaction mixture was concentrated under vacuum, diluted with ether (250 ml) and poured into saturated NaCl (100 mL). The separated organic layer was washed with a mixture of 10% HCl (25 mL) and saturated NaCl (50 mL), dried over Na$_2$SO$_4$ and concentrated under reduced pressure. The residue was diluted with acetonitrile and then white precipitate was formed. The precipitate was filtered and the filter cake was dried under vacuum to give (2R)-2-(tert-butoxycarbonylamino)-3-[tert-butyl(diphenyl) silyl]oxy-propanoic acid (45 g, 90 mmol, 69% yield, 89% purity) as a white solid.

tert-Butyl N-[(1R)-1-[[tert-butyl(diphenyl)silyl] oxymethyl]-2-(2,2-dimethyl-4,6-dioxo-1,3-dioxan-5-yl)-2-oxo-ethyl]carbamate To a stirred solution of (2R)-2-(tert-butoxycarbonylamino)-3-[tert-butyl(diphenyl)silyl]oxy-propanoic acid (24 g, 54.1 mmol, 1 eq) in DCM (400 mL) at 0° C. was added 2,2-dimethyl-1,3-dioxane-4,6-dione (8.19 g, 56.8 mmol, 1.05 eq) and DMAP (16.0 g, 131 mmol, 2.42 eq), followed by BOP (25.1 g, 56.8 mmol, 1.05 eq) in small portions. The mixture was stirred for 1 hour at 0° C. Upon completion, the mixture was washed with 1N KHSO$_4$ (2×360 mL). The organic layers were dried over Na$_2$SO$_4$ and concentrated under vacuum at room temperature to give tert-butyl N-[(1R)-1-[[tert-butyl(diphenyl)silyl] oxymethyl]-2-(2,2-dimethyl-4,6-dioxo-1,3-dioxan-5-yl)-2-oxo-ethyl]carbamate (35 g, crude) as a yellow oil which as used directly into the next step without further purification.

tert-Butyl (2R)-2-[[tert-butyl(diphenyl)silyl]oxymethyl]-3,5-dioxo-pyrrolidine-1-carboxylate tert-butyl N-[(1R)-1-[[tert-butyl(diphenyl)silyl]oxymethyl]-2-(2,2-dimethyl-4,6-dioxo-1,3-dioxan-5-yl)-2-oxo-ethyl]carbamate (35 g, 61.43 mmol, 1 eq) was refluxed in EtOAc (600 mL) at 77° C. for 1 hour. Upon completion, the mixture was concentrated under vacuum to give tert-butyl (2R)-2-[[tert-butyl(diphenyl)silyl]oxymethyl]-3,5-dioxo-pyrrolidine-1-carboxylate (30 g, crude) as a yellow oil which used directly in the next step without further purification.

tert-Butyl (2R,3R)-2-[[tert-butyl(diphenyl)silyl] oxymethyl]-3-hydroxy-5-oxo-pyrrolidine-1-carboxylate tert-butyl (2R)-2-[[tert-butyl(diphenyl)silyl]oxymethyl]-3,5-dioxo-pyrrolidine-1-carboxylate (30 g, 64.2 mmol, 1 eq) was dissolved in DCM (480 mL) at 0° C., followed by NaBH$_4$ (3.78 g, 99.9 mmol, 1.56 eq) in small portions. The suspension was stirred at 18° C. for 16 hours. Upon completion, the reaction mixture was poured into water (300 ml) and stirred until no solid remained. The separated organic layer was washed with water (150 mL), dried over Na$_2$SO$_4$ filtered and concentrated under vacuum. The residue was purified by silica gel chromatography (PE/EtOAc 10/1 to 2/1) followed by reverse phase flash [water (0.1% FA)/acetonitrile]. The desired fractions were collected and neutralized with NaHCO$_3$, concentrated under vacuum to remove MeCN, and then extracted with DCM (2×50 mL). The organic layers were dried over Na$_2$SO$_4$ and concentrated under vacuum to give tert-butyl (2R,3R)-2-[[tert-butyl (diphenyl)silyl]oxymethyl]-3-hydroxy-5-oxo-pyrrolidine-1-carboxylate (2.13 g, 3.99 mmol, three steps 7.6% yield, 88% purity) as a yellow solid.

$^1$H NMR (400 MHz, DMSO-d$_6$) δ=7.72 (dd, J=1.6, 8.0 Hz, 2H), 7.59 (dd, J=1.2, 8.0 Hz, 2H), 7.47-7.39 (m, 6H), 5.67 (d, J=4.0 Hz, 1H), 4.57-4.46 (m, 1H), 4.09-3.97 (m, 2H), 3.83 (dd, J=2.8, 10.0 Hz, 1H), 2.75-2.65 (m, 1H), 2.62-2.53 (m, 1H), 1.38 (s, 9H), 0.93 (s, 9H).

tert-Butyl (2R,3R)-2-[[tert-butyl (diphenyl)silyl] oxymethyl]-5-oxo-3-tetrahydropyran-2-yloxy-pyrrolidine-1-carboxylate To a solution of tert-butyl (2R,3R)-2-[[tert-butyl(diphenyl)silyl] oxymethyl]-3-hydroxy-5-oxo-pyrrolidine-1-carboxylate (2.55 g, 5.43 mmol, 1 eq) in DCM (50 mL) was added DHP (913 mg, 10.9 mmol, 993 µL, 2 eq), followed by TsOH.H$_2$O (103 mg, 543 µmol, 0.1 eq) at 20° C. The mixture was stirred at 20° C. for 16 hours. Upon completion, the mixture was quenched with saturated aqueous NaHCO$_3$ solution (10 mL), diluted with water (5 mL) and extracted with DCM (2×40 mL). The combined organic layers were dried over Na$_2$SO$_4$, filtered and concentrated under vacuum. The residue was purified by silica gel chromatography (PE/EtOAc 15/1 to 7/1) to give tert-butyl (2R,3R)-2-[[tert-butyl (diphenyl)silyl] oxymethyl]-5-oxo-3-tetrahydropyran-2-yloxy-pyrrolidine-1-carboxylate (2.62 g, 4.64 mmol, 85% yield, 98% purity) as a yellow solid.

$^1$H NMR (400 MHz, chloroform-d) δ=7.75 (td, J=1.2, 7.6 Hz, 2H), 7.66 (td, J=1.6, 8.0 Hz, 2H), 7.47-7.34 (m, 6H), 4.75-4.68 (m, 1H), 4.63-4.51 (m, 1H), 4.20-4.17 (m, 1H), 3.99-3.88 (m, 2H), 3.87-3.74 (m, 1H), 3.60-3.50 (m, 1H), 3.23-3.01 (m, 1H), 2.76 (ddd, J=8.8, 10.4, 16.8 Hz, 1H), 2.01-1.80 (m, 2H), 1.79-1.62 (m, 4H), 1.45 (s, 9H), 1.02 (d, J=8.0 Hz, 9H).

(4R,5R)-5-[[tert-Butyl(diphenyl) silyl]oxymethyl]-4-tetrahydropyran-2-yloxy-pyrrolidin-2-one To a solution of tert-butyl (2R,3R)-2-[[tert-butyl(diphenyl)silyl] oxymethyl]-5-oxo-3-tetrahydropyran-2-yloxy-pyrrolidine-1-carboxylate (2.62 g, 4.73 mmol, 1 eq) in MeCN (50 mL) was added Mg(ClO$_4$)$_2$ (211 mg, 946 µmol, 95.6 µL, 0.2 eq). The reaction mixture was stirred at 70° C. for 12 hours. Upon completion, the mixture was filtered and the filtrate was concentrated under vacuum. The residue was purified by reverse phase flash [water (0.1% FA)/acetonitrile]. The desired fractions were collected and concentrated under vacuum to give (4R,5R)-5-[[tert-butyl(diphenyl) silyl] oxymethyl]-4-tetrahydropyran-2-yloxy-pyrrolidin-2-one (1.14 g, 2.29 mmol, 48% yield, 91% purity) as a yellow oil. LCMS [ESI, M+1]: 454.

(4R,5R)-5-[[tert-Butyl(diphenyl)silyl]oxymethyl]-1-methyl-4-tetrahydropyran-2-yloxy-pyrrolidin-2-one To a solution of (4R,5R)-5-[[tert-butyl(diphenyl)silyl] oxymethyl]-4-tetrahydropyran-2-yloxy-pyrrolidin-2-one (0.95 g, 2.09 mmol, 1 eq) in THF (20 mL) was added NaH (168 mg, 4.19 mmol, 60% purity in mineral oil, 2 eq) in portion at 0° C. under N$_2$. The mixture was stirred at 0° C. for 30 minutes, then CH$_3$I (594 mg, 4.19 mmol, 261 uL, 2 eq) was added. After stirred at 0° C. for another 0.5 hour, the mixture was quenched with water (10 mL) and extracted with EtOAc (2×30 mL). The organic layers were dried over Na$_2$SO$_4$ and concentrated under vacuum. The residue was purified by reverse phase flash [water (0.1% FA)/acetonitrile]. The desired fractions were collected and concentrated under vacuum to give (4R,5R)-5-[[tert-butyl(diphenyl)silyl] oxymethyl]-1-methyl-4-tetrahydropyran-2-yloxy-pyrrolidin-2-one (820 mg, 1.67 mmol, 80% yield, 95% purity) as a brown oil.

$^1$H NMR (400 MHz, chloroform-d) δ=7.75-7.70 (m, 2H), 7.70-7.65 (m, 2H), 7.48-7.36 (m, 6H), 4.68-4.60 (m, 1H), 4.59-4.48 (m, 1H), 4.07-3.77 (m, 2H), 3.77-3.66 (m, 1H), 3.65-3.56 (m, 1H), 3.55-3.40 (m, 1H), 2.89-2.79 (m, 3H), 2.79-2.53 (m, 2H), 1.90-1.69 (m, 2H), 1.68-1.53 (m, 4H), 1.09-1.03 (m, 9H).

(4R,5R)-5-(Hydroxymethyl)-1-methyl-4-tetrahydropyran-2-yloxy-pyrrolidin-2-one

To a mixture of (4R,5R)-5-[[tert-butyl(diphenyl)silyl] oxymethyl]-1-methyl-4-tetrahydropyran-2-yloxy-pyrrolidin-2-one (1.07 g, 2.29 mmol, 1 eq) in DMSO (10 mL) was added CsF (1.04 g, 6.86 mmol, 253 µL, 3 eq). The mixture was stirred at 65° C. for 2 hours. Upon completion, the mixture was concentrated under vacuum. The residue was purified by chromatography (Al$_2$O$_3$, EtOAc/MeOH 50/1 to 5/1) to give (4R,5R)-5-(hydroxymethyl)-1-methyl-4-tetrahydropyran-2-yloxy-pyrrolidin-2-one (380 mg, 1.49 mmol, 65% yield, 90% purity) as a yellow oil.

$^1$H NMR (400 MHz, chloroform-d) δ=4.80-4.52 (m, 2H), 3.98-3.81 (m, 3H), 3.72-3.61 (m, 1H), 3.60-3.48 (m, 1H), 2.87 (d, J=9.6 Hz, 3H), 2.67 (d, J=7.2 Hz, 1H), 2.60-2.46 (m, 1H), 1.86-1.74 (m, 2H), 1.67-1.51 (m, 4H).

Step A: Benzyl (2S)-2-(cyanomethyl)-4-[7-(8-methyl-1-naphthyl)-2-[[(2R,3R)-1-methyl-5-oxo-3-tetrahydropyran-2-yloxy-pyrrolidin-2-yl]methoxy]-6,8-dihydro-5H-pyrido[3,4-d]pyrimidin-4-yl] piperazine-1-carboxylate To a solution of benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (280 mg, 471 µmol, 1 eq) and (4R,5R)-5-(hydroxymethyl)-1-methyl-4-tetrahydropyran-2-yloxy-pyrrolidin-2-one (140 mg, 612 µmol, 1.3 eq) in toluene (6 mL) was added t-BuONa (90.5 mg, 942 µmol, 2 eq) at 0° C. After stirred at 0° C. for 10 minutes, the mixture was diluted with water (5 mL) and extracted with EtOAc (2×10 mL). The organic layers were dried over Na$_2$SO$_4$ and concentrated under vacuum. The residue was purified by reverse phase flash [water (0.1% FA)/acetonitrile]. The desired fractions were collected and neutralized with NaHCO$_3$, concentrated under vacuum to remove MeCN and extracted with EtOAc (2×20 mL). The organic layers were dried over Na$_2$SO$_4$ and concentrated under vacuum to give benzyl (2S)-2-(cyanomethyl)-4-[7-(8-methyl-1-naphthyl)-2-[[(2R,3R)-1-methyl-5-oxo-3-tetrahydropyran-2-yloxy-pyrrolidin-2-yl]methoxy]-6,8-dihydro-5H-pyrido[3,4-d]pyrimidin-4-yl]piperazine-1-carboxylate (200 mg, 258 µmol, 55% yield, 98% purity) as a yellow solid. LCMS [ESI, M+1]: 760.

$^1$H NMR (400 MHz, chloroform-d) δ=7.74-7.63 (m, 2H), 7.47-7.31 (m, 7H), 7.27-7.17 (m, 2H), 5.21 (s, 2H), 4.84-4.43 (m, 5H), 4.30-3.70 (m, 8H), 3.59-3.34 (m, 3H), 3.25-2.98 (m, 4H), 2.96-2.90 (m, 6H), 2.81-2.56 (m, 4H), 1.83-1.63 (m, 2H), 1.60-1.47 (m, 4H).

Step B: 2-[(2S)-4-[7-(8-Methyl-1-naphthyl)-2-[[(2R, 3R)-1-methyl-5-oxo-3-tetrahydropyran-2-yloxy-pyrrolidin-2-yl]methoxy]-6,8-dihydro-5H-pyrido[3, 4-d]pyrimidin-4-yl]piperazin-2-yl]acetonitrile To a solution of benzyl (2S)-2-(cyanomethyl)-4-[7-(8-methyl-1-naphthyl)-2-[[(2R,3R)-1-methyl-5-oxo-3-tetrahydropyran-2-yloxy-pyrrolidin-2-yl]methoxy]-6,8-dihydro-5H-pyrido[3,4-d]pyrimidin-4-yl]piperazine-1-carboxylate (150 mg, 197 µmol, 1 eq) in MeOH (3 mL) was added NH$_3$/MeOH (3 mL, 20% purity), Pd/C (75 mg, 10% purity) under N$_2$. The suspension was degassed under vacuum and purged with H$_2$ several times. The mixture was stirred under H$_2$ (15 psi) at 20° C. for 1 hour. Upon completion, the mixture was filtered and the filtrate was concentrated under vacuum to give 2-[(2S)-4-[7-(8-methyl-1-naphthyl)-2-[[(2R,3R)-1-methyl-5-oxo-3-tetrahydropyran-2-yloxy-pyrrolidin-2-yl]methoxy]-6,8-dihydro-5H-pyrido[3,4-d]pyrimidin-4-yl]piperazin-2-yl]acetonitrile (100 mg, 144 µmol, 73% yield, 90% purity) as a yellow solid which was used directly in the next step without further purification. LCMS [ESI, M+1]: 626.

Step C: 2-[(2S)-4-[2-[[(2R,3R)-3-Hydroxy-1-methyl-5-oxo-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2R,3R)-1-methyl-5-oxo-3-tetrahydropyran-2-yloxy-pyrrolidin-2-yl]methoxy]-6,8-dihydro-5H-pyrido[3,4-d]pyrimidin-4-yl]piperazin-2-yl]acetonitrile (100 mg, 160 µmol, 1 eq) in DCM (100 µL) was added TFA (273 mg, 2.40 mmol, 177 µL, 15 eq). The mixture was stirred at 20° C. for 1 hour. Upon completion, the mixture was diluted with DCM (5 mL) and basified with saturated sodium bicarbonate aqueous solution to pH=8. The separated aqueous layer was extracted with EtOAc (3×5 mL). Combined organic layers were dried over MgSO$_4$, filtered and concentrated under vacuum to give 2-[(2S)-4-[2-[[(2R,3R)-3-hydroxy-1-methyl-5-oxo-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (80 mg, 126 µmol, 79% yield, 85% purity) as a yellow oil which was used directly in the next step without further purification.

Step D: 2-[(2S)-1-(2-Fluoroprop-2-enoyl)-4-[2-[[(2R,3R)-3-hydroxy-1-methyl-5-oxo-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To a solution of 2-[(2S)-4-[2-[[(2R,3R)-3-hydroxy-1-methyl-5-oxo-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (80 mg, 148 µmol, 1 eq), TEA (44.8 mg, 443 µmol, 61.7 µL, 3 eq) and 2-fluoroprop-2-enoic acid (26.6 mg, 295 µmol, 2 eq) in EA (3 mL) was added T3P (141 mg, 222 µmol, 132 uL, 50% purity in EtOAc, 1.5 eq) at 0° C. The mixture was stirred at 0° C. for 0.5 hour. Upon completion, the mixture was quenched with saturated NaHCO$_3$ aqueous solution (5 mL) and extracted with EtOAc (2×10 mL). The organic layers were dried over Na$_2$SO$_4$ and concentrated under vacuum. The residue was purified by chromatography (Al$_2$O$_3$, EtOAc/MeOH 1/0 to 10/1) followed by prep-HPLC (column: Xtimate C18 150*25 mm*5 um; mobile phase: [water (0.05% ammonium hydroxide v/v)-ACN]; B %: 34%-64%, 10 min). The desired fractions were collected and lyophilized to give title compound 2-[(2S)-1-(2-fluoroprop-2-enoyl)-4-[2-[[(2R,3R)-3-hydroxy-1-methyl-5-oxo-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (11.8 mg, 19.1 µmol, 13% yield, 99.3% purity) as a off-white solid. LCMS [ESI, M+1]: 614.

$^1$H NMR (400 MHz, chloroform-d) δ=7.71 (d, J=8.0 Hz, 1H), 7.69-7.63 (m, 1H), 7.41 (q, J=7.6 Hz, 1H), 7.35 (t, J=7.6 Hz, 1H), 7.27-7.19 (m, 2H), 5.55-5.33 (m, 1H), 5.27 (dd, J=3.6, 16.8 Hz, 1H), 4.86 (dd, J=5.6, 12.0 Hz, 1H), 4.79 (dd, J=5.6, 12.0 Hz, 1H), 4.63-4.49 (m, 2H), 4.39-3.94 (m, 3H), 3.89-3.77 (m, 2H), 3.76-3.63 (m, 1H), 3.61-3.44 (m, 2H), 3.38-2.99 (m, 4H), 2.91 (d, J=7.2 Hz, 6H), 2.89-2.70 (m, 2H), 2.70-2.55 (m, 2H), 2.46 (dt, J=5.2, 16.0 Hz, 1H).

Example 571

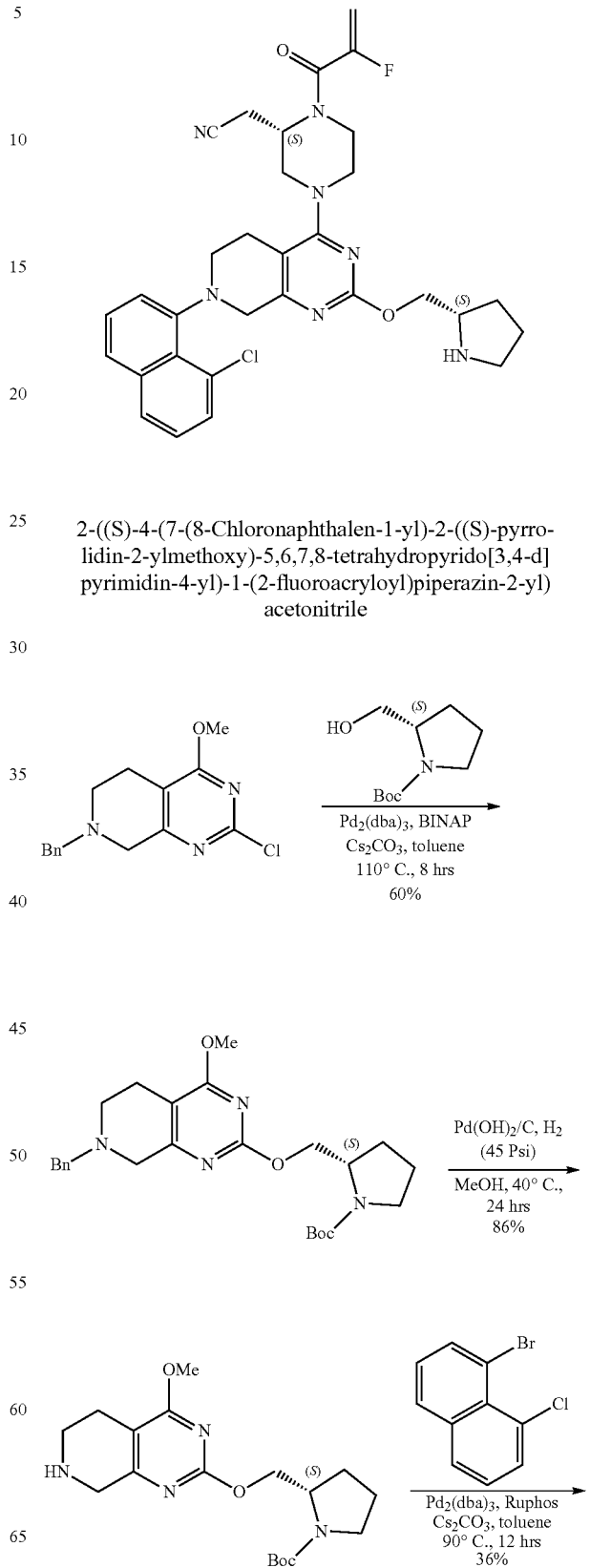

2-((S)-4-(7-(8-Chloronaphthalen-1-yl)-2-((S)-pyrrolidin-2-ylmethoxy)-5,6,7,8-tetrahydropyrido[3,4-d]pyrimidin-4-yl)-1-(2-fluoroacryloyl)piperazin-2-yl)acetonitrile -continued

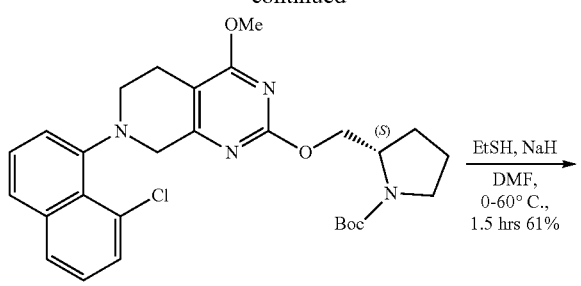

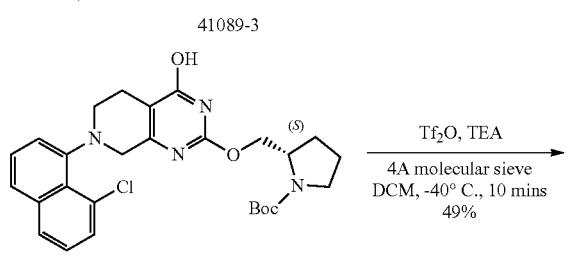

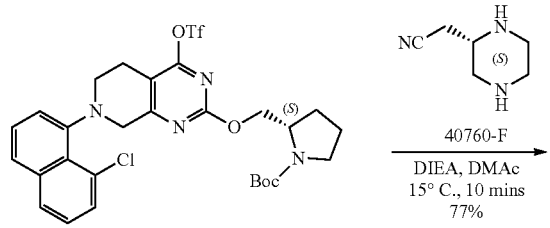

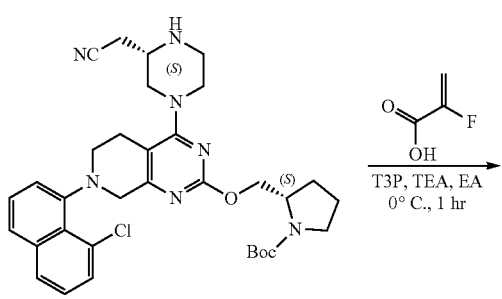

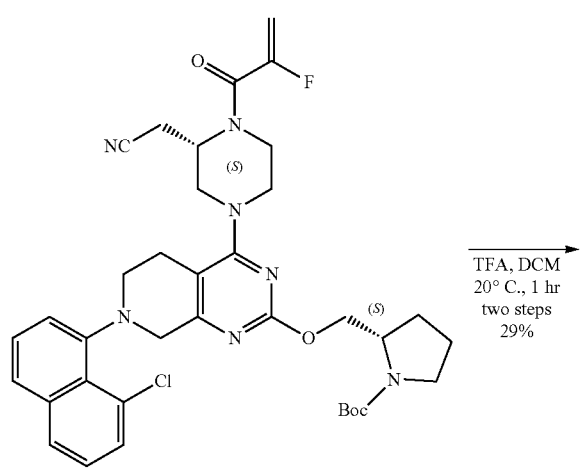

-continued

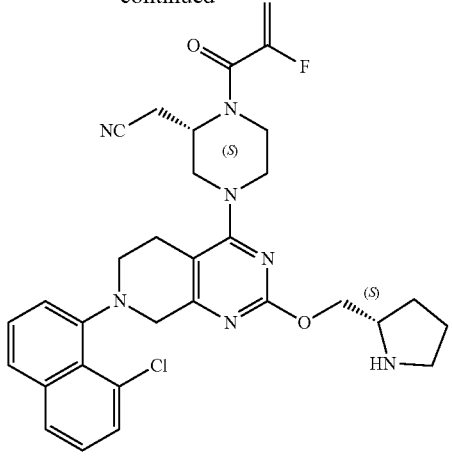

Step A: tert-Butyl (2S)-2-[(7-benzyl-4-methoxy-6,8-dihydro-5H-pyrido[3,4-d]pyrimidin-2-yl) oxymethyl]pyrrolidine-1-carboxylate To a solution of 7-benzyl-2-chloro-4-methoxy-6,8-dihydro-5H-pyrido[3,4-d]pyrimidine (4.00 g, 13.8 mmol, 1.00 eq) and tert-butyl (2S)-2-(hydroxymethyl)pyrrolidine-1-carboxylate (5.56 g, 27.6 mmol, 2.00 eq) in toluene (80.0 mL) was added BINAP (1.72 g, 2.76 mmol, 0.20 eq), Pd(OAc)$_2$ (310 mg, 1.38 mmol, 0.10 eq) and Cs$_2$CO$_3$ (13.5 g, 41 mmol, 3.00 eq). The mixture was stirred at 110° C. for 8 hours. After completion, the reaction mixture was filtered and concentrated under reduced pressure to give a residue. The residue was diluted with H$_2$O (200 mL) and ethyl acetate (200 mL). The mixture was acidified to pH ~3 with aqueous HCl (2N). The aqueous phase was separated and extracted with ethyl acetate (3×200 mL). The combined organic layers were dried over Na$_2$SO$_4$, filtered and concentrated under reduced pressure to give a residue. The residue was purified by column chromatography (SiO$_2$, petroleum ether/ethyl acetate=20/1 to 1/1) to give tert-butyl (2S)-2-[(7-benzyl-4-methoxy-6,8-dihydro-5H-pyrido[3,4-d]pyrimidin-2-yl) oxymethyl]pyrrolidine-1-carboxylate (3.80 g, 8.26 mmol, 60% yield, 99% purity) as yellow oil. LCMS [ESI, M+1]: 455.

$^1$H NMR (400 MHz, chloroform-d) δ 7.37-7.27 (m, 5H), 4.50-4.35 (m, 1H), 4.25-4.16 (m, 1H), 3.98 (s, 3H), 3.69 (s, 2H), 3.50 (s, 2H), 3.43-3.33 (m, 2H), 2.76-2.72 (m, 2H), 2.62-2.57 (m, 2H), 2.04-1.90 (m, 3H), 1.85-1.76 (m, 1H), 1.61-1.54 (m, 1H), 1.45 (s, 9H).

Step B: tert-Butyl (2S)-2-[(4-methoxy-5,6,7,8-tetrahydropyrido[3,4-d] pyrimidin-2-yl)oxymethyl]pyrrolidine-1-carboxylate To a solution of tert-butyl (2S)-2-[(7-benzyl-4-methoxy-6,8-dihydro-5H-pyrido[3,4-d]pyrimidin-2-yl)oxymethyl]pyrrolidine-1-carboxylate (3.80 g, 8.36 mmol, 1.00 eq) in methanol (100 mL) was added Pd(OH)$_2$/C (1.00 g, 10.3 mmol, 20% purity) under N$_2$. The suspension was degassed under vacuum and purged with H$_2$ three times. The mixture was stirred under H$_2$ (45 psi) at 40° C. for 24 hours. After completion, the reaction mixture was concentrated under reduced pressure to give a residue. Compound tert-butyl (2S)-2-[(4-methoxy-5,6,7,8-tetrahydropyrido[3,4-d] pyrimidin-2-yl)oxymethyl]pyrrolidine-1-carboxylate (2.70 g, 7.17 mmol, 86% yield, 97% purity) was obtained as yellow oil and used into the next step without further purification. LCMS [ESI, M+1]: 365.

$^1$H NMR (400 MHz, chloroform-d) δ 4.54-4.35 (m, 1H), 4.25-4.10 (m, 2H), 3.98 (s, 3H), 3.86 (s, 2H), 3.48 (s, 1H), 3.43-3.33 (m, 2H), 3.13-3.04 (m, 2H), 2.56-2.46 (m, 2H), 2.10-1.93 (m, 3H), 1.87-1.82 (m, 1H), 1.45 (s, 9H).

Step C: tert-Butyl (2S)-2-[[7-(8-chloro-1-naphthyl)-4-methoxy-6,8-dihydro-5H-pyrido[3,4-d]pyrimidin-2-yl]oxymethyl]pyrrolidine-1-carboxylate To a solution of tert-butyl (2S)-2-[(4-methoxy-5,6,7,8-tetrahydropyrido[3,4-d]pyrimidin-2-yl)oxymethyl]pyrrolidine-1-carboxylate (2.5 g, 6.86 mmol, 1.0 eq) and 1-bromo-8-chloro-naphthalene (3.31 g, 13.7 mmol, 2.0 eq) in toluene (50 mL) was added Pd$_2$(dba)$_3$ (1.26 g, 1.37 mmol, 0.2 eq), Cs$_2$CO$_3$ (5.59 g, 17.2 mmol, 2.5 eq), and RuPhos (1.28 g, 2.74 mmol, 0.4 eq), the reaction mixture was stirred at 90° C. for 12 hours under N$_2$. After completion, the reaction mixture was filtered through celite, and the filtrate was washed with saturated brine (1×80 mL), the organic layer was dried over Na$_2$SO$_4$, filtered and concentrated. The residue was purified by column chromatography (SiO$_2$, petroleum ether/ethyl acetate=10/1 to 3/1). The product tert-butyl (2S)-2-[[7-(8-chloro-1-naphthyl)-4-methoxy-6,8-dihydro-5H-pyrido[3,4-d]pyrimidin-2-yl]oxymethyl]pyrrolidine-1-carboxylate (1.3 g, 2.46 mmol, 36% yield, 99% purity) as light yellow solid. LCMS [ESI, M+1]: 525.

$^1$H NMR (400 MHz, chloroform-d) δ 7.74 (d, J=8.4 Hz, 1H), 7.60 (br d, J=8.0 Hz, 1H), 7.51 (d, J=7.6 Hz, 1H), 7.43 (t, J=7.8 Hz, 1H), 7.33 (t, J=7.8 Hz, 1H), 7.23 (br d, J=7.6 Hz, 1H), 4.60-4.37 (m, 1H), 4.34-4.16 (m, 3H), 4.03 (s, 3H), 3.87 (br d, J=17.2 Hz, 1H), 3.63-3.57 (m, 1H), 3.45-3.30 (m, 2H), 3.21-3.10 (m, 1H), 2.99 (br s, 1H), 2.62 (br d, J=16.8 Hz, 1H), 2.07-1.79 (m, 4H), 1.45 (s, 9H).

Step D: tert-Butyl (2S)-2-[[7-(8-chloro-1-naphthyl)-4-hydroxy-6,8-dihydro-5H-pyrido[3,4-d]pyrimidin-2-yl]oxymethyl]pyrrolidine-1-carboxylate To a solution of NaH (168 mg, 4.19 mmol, 60% purity, 2.0 eq) in DMF (15 mL) was added EtSH (391 mg, 6.29 mmol, 465 μL, 3.0 eq) in portions at 15° C. After stirring for 0.5 hour, a solution of tert-butyl(2S)-2-[[7-(8-chloro-1-naphthyl)-4-methoxy-6,8-dihydro-5H-pyrido[3,4-d]pyrimidin-2-yl]oxymethyl]pyrrolidine-1-carboxylate (1.1 g, 2.10 mmol, 1.0 eq) in DMF (7.0 mL) was added to the mixture, then the reaction mixture was stirred at 60° C. for 1 hour. After completion, the reaction mixture was poured into ice water (10 mL), then the mixture was adjusted with 1N HCl aqueous to pH 7~8, the mixture was filtered, the filter cake was dissolved with dichloromethane (10 mL), washed with saturated brine (2×15 mL), dried over Na$_2$SO$_4$, filtered and concentrated. The residue was purified by column chromatography (SiO$_2$, petroleum ether/ethyl acetate=3/1 to ethyl acetate:methanol=10:1) to give tert-butyl (2S)-2-[[7-(8-chloro-1-naphthyl)-4-hydroxy-6,8-dihydro-5H-pyrido[3,4-d]pyrimidin-2-yl]oxymethyl]pyrrolidine-1-carboxylate (670 mg, 1.28 mmol, 61% yield, 98% purity) as yellow solid. LCMS [ESI, M+1]: 511.

Step E: tert-Butyl(2S)-2-[[7-(8-chloro-1-naphthyl)-4-(trifluoromethylsulfonyloxy)-6,8-dihydro-5H-pyrido[3,4-d]pyrimidin-2-yl]oxymethyl]pyrrolidine-1-carboxylate To a solution of tert-butyl (2S)-2-[[7-(8-chloro-1-naphthyl)-4-hydroxy-6,8-dihydro-5H-pyrido[3,4-d]pyrimidin-2-yl]oxymethyl]pyrrolidine-1-carboxylate (640 mg, 1.25 mmol, 1.0 eq) in DCM (10 mL) was added TEA (380 mg, 3.76 mmol, 523 μL, 3.0 eq), 4 A molecular sieves (500 mg), and Tf$_2$O (530 mg, 1.88 mmol, 310 μL, 1.5 eq) at −40° C., and the reaction mixture was stirred at −40° C. for 10 mins. After completion, water was added (10 mL) in portions at −40° C., then the reaction mixture was warmed to 15° C. and the organic layer was separated and washed with saturated brine (1×10 mL), the organic layer was dried over Na$_2$SO$_4$, filtered and concentrated. The residue was purified by column chromatography (SiO$_2$, petroleum ether/ethyl acetate=10/1 to 3/1). The product tert-butyl(2S)-2-[[7-(8-chloro-1-naphthyl)-4-(trifluoromethylsulfonyloxy)-6,8-dihydro-5H-pyrido[3,4-d]pyrimidin-2-yl]oxymethyl]pyrrolidine-1-carboxylate (400 mg, 616 μmol, 49% yield, 99% purity) was obtained as light yellow solid. LCMS [ESI, M+1]: 643.

Step F: tert-Butyl (2S)-2-[[7-(8-chloro-1-naphthyl)-4-[(3S)-3-(cyanomethyl)piperazin-1-yl]-6,8-dihydro-5H-pyrido[3,4-d]pyrimidin-2-yl]oxymethyl]pyrrolidine-1-carboxylate To a solution of tert-butyl (2S)-2-[[7-(8-chloro-1-naphthyl)-4-(trifluoromethylsulfonyloxy)-6,8-dihydro-5H-pyrido[3,4-d]pyrimidin-2-yl]oxymethyl]pyrrolidine-1-carboxylate (400 mg, 622 μmol, 1.0 eq) in DMAC (4.0 mL) was added 2-[(2S)-piperazin-2-yl]acetonitrile (86.5 mg, 622 μmol, 1.0 eq) and DIEA (161 mg, 1.24 mmol, 217 μL, 2.0 eq), the reaction mixture was stirred at 15° C. for 10 mins. After completion, the reaction mixture was poured into ice water (10 mL), the precipitated solid was filtered, dissolved with ethyl acetate (15 mL), the organic layer was washed with saturated brine (2×15 mL), dried over Na$_2$SO$_4$, filtered and concentrated. The residue was purified by reverse phase flash (0.1% FA condition, 20%-30% MeCN in water), the obtained product was adjusted with NaHCO$_3$ solid to pH ~8, then concentrated, the aqueous was extracted with ethyl acetate (2×15 mL), the organic layer was washed with saturated brine (1×20 mL), dried over Na$_2$SO$_4$, filtered and concentrated. The product tert-butyl (2S)-2-[[7-(8-chloro-1-naphthyl)-4-[(3S)-3-(cyanomethyl)piperazin-1-yl]-6,8-dihydro-5H-pyrido[3,4-d]pyrimidin-2-yl]oxymethyl]pyrrolidine-1-carboxylate (300 mg, 480 μmol, 77% yield, 99% purity) was obtained as light yellow solid. LCMS [ESI, M+1]: 618.

$^1$H NMR (400 MHz, chloroform-d) δ 7.75 (d, J=8.0 Hz, 1H), 7.61 (br d, J=8.0 Hz, 1H), 7.52 (d, J=6.8 Hz, 1H), 7.47-7.42 (m, 1H), 7.33 (t, J=7.8 Hz, 1H), 7.23 (br t, J=6.2 Hz, 1H), 4.71-4.31 (m, 2H), 4.29-4.06 (m, 3H), 3.95-3.69 (m, 2H), 3.63-3.28 (m, 4H), 3.26-2.82 (m, 7H), 2.72-2.46 (m, 3H), 2.02-1.79 (m, 4H), 1.45 (s, 9H).

Step G: tert-Butyl(2S)-2-[[7-(8-chloro-1-naphthyl)-4-[(3S)-3-(cyanomethyl)-4-(2-fluoroprop-2-enoyl)piperazin-1-yl]-6,8-dihydro-5H-pyrido[3,4-d]pyrimidin-2-yl]oxymethyl]pyrrolidine-1-carboxylate To a solution of tert-butyl (2S)-2-[[7-(8-chloro-1-naphthyl)-4-[(3S)-3-(cyanomethyl)piperazin-1-yl]-6,8-dihydro-5H-pyrido[3,4-d]pyrimidin-2-yl]oxymethyl]pyrrolidine-1-carboxylate (100 mg, 162 μmol, 1.0 eq) and 2-fluoroprop-2-enoic acid (29.1 mg, 324 μmol, 2.0 eq) in ethyl acetate (1.5 mL) was added TEA (131 mg, 1.29 mmol, 180 μL, 8.0 eq) and T3P (309 mg, 485 μmol, 289 μL, 50% purity, 3.0 eq) in portions at 0° C., the reaction mixture was stirred at 0° C. for 1 hour. After completion, water was added (10 ml), then the organic layer was separated, the aqueous phase was extracted with ethyl acetate (2×10 mL), the combined organic layer was dried over $Na_2SO_4$, filtered and concentrated. The residue was purified column chromatography (basic $Al_2O_3$, petroleum ether/ethyl acetate=3/1 to 1/1). The product tert-butyl(2S)-2-[[7-(8-chloro-1-naphthyl)-4-[(3S)-3-(cyanomethyl)-4-(2-fluoroprop-2-enoyl)piperazin-1-yl]-6,8-dihydro-5H-pyrido[3,4-d]pyrimidin-2-yl]oxymethyl]pyrrolidine-1-carboxylate (110 mg, crude) was obtained as light yellow solid. LCMS [ESI, M+1]: 690.

Step H: 2-((S)-4-(7-(8-Chloronaphthalen-1-yl)-2-((S)-pyrrolidin-2-ylmethoxy)-5,6,7,8-tetrahydro-pyrido[3,4-d]pyrimidin-4-yl)-1-(2-fluoroacryloyl)piperazin-2-yl)acetonitrile To a solution of tert-butyl (2S)-2-[[7-(8-chloro-1-naphthyl)-4-[(3S)-3-(cyanomethyl)-4-(2-fluoroprop-2-enoyl)piperazin-1-yl]-6,8-dihydro-5H-pyrido[3,4-d]pyrimidin-2-yl]oxymethyl]pyrrolidine-1-carboxylate (90.0 mg, 130.40 µmol, 1.0 eq) in dichloromethane (0.5 mL) was added TFA (770 mg, 6.75 mmol, 0.5 mL, 51.8 eq), and the reaction mixture was stirred at 20° C. for 1 hour. After completion, the reaction mixture was concentrated, then dissolved with ethyl acetate (10 mL), washed with saturated aqueous $Na_2CO_3$ (1×10 mL), the organic layer was dried over $Na_2SO_4$, filtered and concentrated. The residue was purified by column chromatography ($SiO_2$, petroleum ether/ethyl acetate=3/1 to ethyl acetate:methanol=10:1), then purified by prep-HPLC (column: Phenomenex Synergi C18 150*25*10 µm; mobile phase: [water (0.225% FA)-ACN]; B %: 20%-50%, 10 min), the obtained product was concentrated and lyophilized. Title compound 2-((S)-4-(7-(8-chloronaphthalen-1-yl)-2-((S)-pyrrolidin-2-ylmethoxy)-5,6,7,8-tetrahydropyrido[3,4-d]pyrimidin-4-yl)-1-(2-fluoroacryloyl)piperazin-2-yl)acetonitrile (24.7 mg, 38.1 µmol, 29% yield, 98% purity, FA) was obtained as off-white solid. LCMS [ESI, M+1]: 590.

$^1H$ NMR (400 MHz, chloroform-d) δ 7.76 (d, J=8.0 Hz, 1H), 7.62 (t, J=7.0 Hz, 1H), 7.56-7.49 (m, 1H), 7.54-7.50 (m, 1H), 7.34 (t, J=7.8 Hz, 1H), 7.26-7.17 (m, 1H), 5.53-5.32 (m, 1H), 5.25 (dd, J=3.6, 16.8 Hz, 1H), 4.89-4.52 (m, 1H), 4.64-4.45 (m, 2H), 4.42-4.23 (m, 2H), 4.17-3.92 (m, 4H), 3.89-3.78 (m, 2H), 3.51-3.42 (m, 1H), 3.35-3.05 (m, 5H), 2.95-2.73 (m, 2H), 2.62-2.51 (m, 1H), 2.21-1.84 (m, 4H).

Example 572

2-[(2S)-4-[7-(8-Chloro-1-naphthyl)-2-[[(2S)-1-methyl-5-oxo-pyrrolidin-2-yl]methoxy]-6, 8-dihydro-5H-pyrido [3,4-d]pyrimidin-4-yl]-1-(2-fluoro-prop-2-enoyl)piperazin-2-yl] acetonitrile

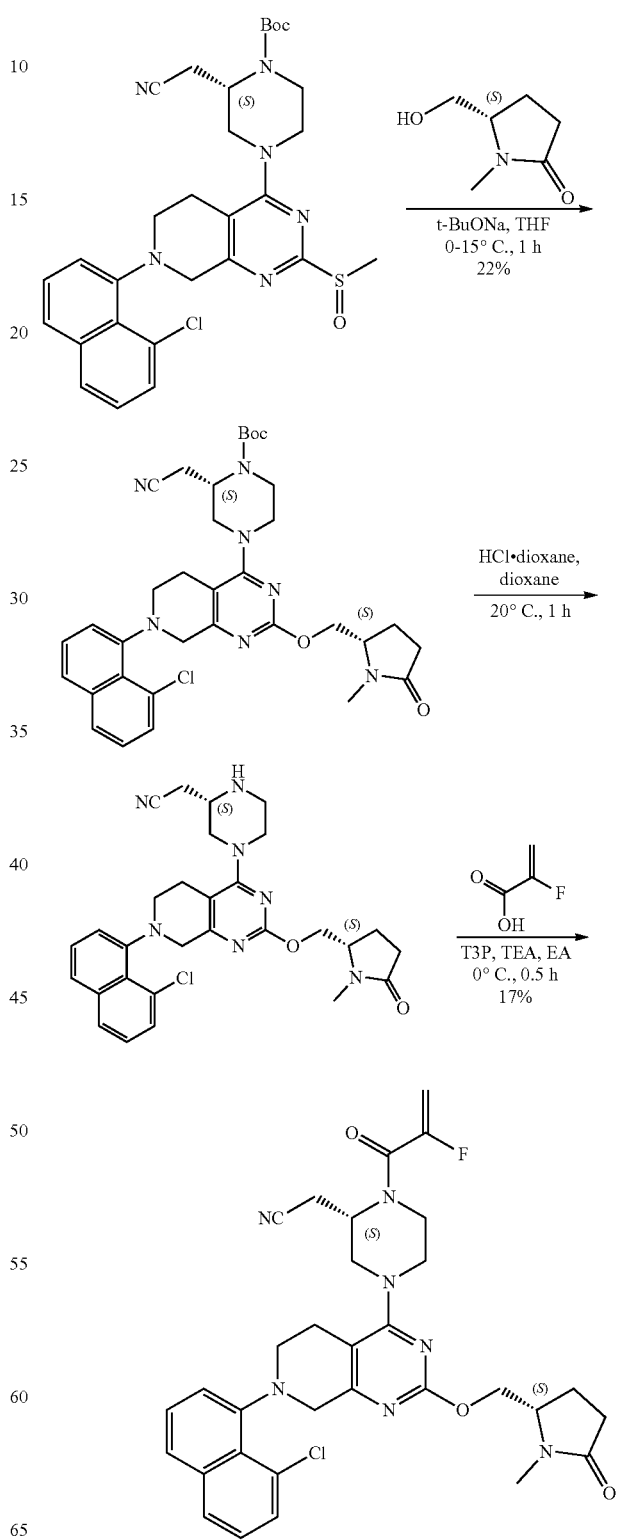

Step A: tert-Butyl (2S)-4-[7-(8-chloro-1-naphthyl)-2-[[(2S)-1-methyl-5-oxo-pyrrolidin-2-yl]methoxy]-6,8-dihydro-5H-pyrido[3,4-d]pyrimidin-4-yl]-2-(cyanomethyl)piperazine-1-carboxylate To a mixture of (5S)-5-(hydroxymethyl)-1-methyl-pyrrolidin-2-one (556 mg, 4.30 mmol, 5.00 eq) in THF (20.0 mL) was added t-BuONa (827 mg, 8.60 mmol, 10.0 eq) in portion at 0° C. under $N_2$. The mixture was stirred at 0° C. for 30 min, followed by adding tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (500 mg, 860 μmol, 1.00 eq). The mixture was warmed to 15° C. and stirred for 0.5 hour. The reaction mixture was diluted with ethyl acetate (50.0 mL) and washed with water (30 mL×2), dried over sodium sulfate, filtered and concentrated under reduced pressure to give a residue. The residue was purified by reverse phase flash [water (0.1% TFA)/acetonitrile]. The desired fractions were collected and neutralized with saturated $NaHCO_3$ solution (10.0 mL) and extracted with ethyl acetate (50.0 mL×3). The separated organic layer was dried over sodium sulfate, filtered and concentrated under vacuum. Compound tert-butyl (2S)-4-[7-(8-chloro-1-naphthyl)-2-[[(2S)-1-methyl-5-oxo-pyrrolidin-2-yl]methoxy]-6,8-dihydro-5H-pyrido[3,4-d]pyrimidin-4-yl]-2-(cyanomethyl)piperazine-1-carboxylate (125 mg, 193 μmol, 22% yield) was obtained as a yellow solid.

$^1$H NMR (400 MHz, chloroform-d) δ=7.75 (d, J=8.0 Hz, 1H), 7.61 (dd, J=4.8, 8.0 Hz, 1H), 7.52 (dd, J=0.8, 7.2 Hz, 1H), 7.45 (q, J=8.0 Hz, 1H), 7.37-7.28 (m, 1H), 7.23 (br d, J=7.6 Hz, 1H), 4.70-4.31 (m, 3H), 4.10-3.82 (m, 4H), 3.65-3.51 (m, 1H), 3.46-2.99 (m, 5H), 2.98-2.82 (m, 3H), 2.79-2.37 (m, 5H), 2.22 (br d, J=8.0 Hz, 1H), 1.93-1.59 (m, 3H), 1.52 (s, 9H).

Step B: 2-[(2S)-4-[7-(8-Chloro-1-naphthyl)-2-[[(2S)-1-methyl-5-oxo-pyrrolidin-2-yl]methoxy]-6,8-dihydro-5H-pyrido[3,4-d]pyrimidin-4-yl]piperazin-2-yl]acetonitrile To a mixture of tert-butyl (2S)-4-[7-(8-chloro-1-naphthyl)-2-[[(2S)-1-methyl-5-oxo-pyrrolidin-2-yl]methoxy]-6,8-dihydro-5H-pyrido[3,4-d]pyrimidin-4-yl]-2-(cyanomethyl)piperazine-1-carboxylate (100 mg, 155 μmol, 1.00 eq) in dioxane (1.50 mL) was added HCl/dioxane (4 M, 967 μL, 25.0 eq). The mixture was stirred at 20° C. for 1 h. The reaction mixture was concentrated under reduced pressure to give a residue. The residue was dissolved with ethyl acetate (10.0 mL) and basified to pH=8 with saturated $NaHCO_3$ solution (3.00 mL), and extracted with ethyl acetate (5.00 mL×3). The combined organic layers were washed with brine (10.0 mL×1), dried over sodium sulfate, filtered and concentrated under reduced pressure to give a residue. The crude product was used in the next step directly without further purification. Compound 2-[(2S)-4-[7-(8-chloro-1-naphthyl)-2-[[(2S)-1-methyl-5-oxo-pyrrolidin-2-yl]methoxy]-6,8-dihydro-5H-pyrido[3,4-d]pyrimidin-4-yl]piperazin-2-yl]acetonitrile (80.0 mg, crude) was obtained as a yellow solid. LCMS [ESI, M+1]: 546.

Step C: 2-[(2S)-4-[7-(8-Chloro-1-naphthyl)-2-[[(2S)-1-methyl-5-oxo-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a mixture of 2-[(2S)-4-[7-(8-chloro-1-naphthyl)-2-[[(2S)-1-methyl-5-oxo-pyrrolidin-2-yl]methoxy]-6,8-dihydro-5H-pyrido[3,4-d]pyrimidin-4-yl]piperazin-2-yl]acetonitrile (60.0 mg, 110 μmol, 1.00 eq) and 2-fluoroprop-2-enoic acid (19.8 mg, 220 μmol, 2.00 eq) in EA (1 mL) was added TEA (89.0 mg, 879 μmol, 122 μL, 8.00 eq), T3P (210 mg, 330 μmol, 196 μL, 50% purity in ethyl acetate, 3.00 eq) in portion at 0° C. under $N_2$. The mixture was stirred at 0° C. for 30 min. The reaction mixture was diluted with water (5 mL) and extracted with ethyl acetate (10 mL×3). The combined organic layers were washed with water (10 mL×1) and brine (10 mL×1), dried over sodium sulfate, filtered and concentrated under reduced pressure to give a residue. The residue was purified by prep-HPLC (column: Xtimate C18 150×25 mm×5 μm; mobile phase: [water (0.05% ammonium hydroxide v/v)-ACN]; B %: 35%-65%, 10 min). Title compound 2-[(2S)-4-[7-(8-chloro-1-naphthyl)-2-[[(2S)-1-methyl-5-oxo-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (11.3 mg, 18.2 umol, 17% yield, 99% purity) was obtained as a white solid LCMS [ESI, M+1]: 618.

$^1$H NMR (400 MHz, chloroform-d) δ=7.77 (d, J=8.0 Hz, 1H), 7.63 (t, J=7.6 Hz, 1H), 7.53 (d, J=6.8 Hz, 1H), 7.46 (td, J=8.0, 10.4 Hz, 1H), 7.35 (t, J=7.6 Hz, 1H), 7.27-7.20 (m, 1H), 5.52-5.34 (m, 1H), 5.26 (dd, J=3.6, 16.8 Hz, 1H), 4.92 (br s, 1H), 4.52-4.31 (m, 3H), 4.27-3.77 (m, 5H), 3.61 (br d, J=10.8 Hz, 1H), 3.46 (br d, J=12.0 Hz, 1H), 3.36-2.94 (m, 5H), 2.92 (s, 3H), 2.90-2.79 (m, 1H), 2.64-2.48 (m, 2H), 2.41-2.31 (m, 1H), 2.28-2.17 (m, 1H), 2.05-1.95 (m, 1H).

Example 573

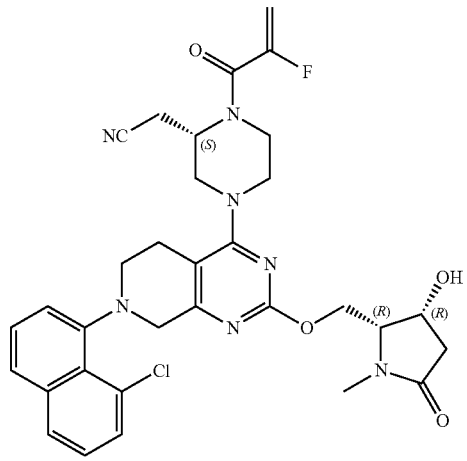

1483

2-[(2S)-4-[7-(8-Chloro-1-naphthyl)-2-[[(2R,3R)-3-hydroxy-1-methyl-5-oxo-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

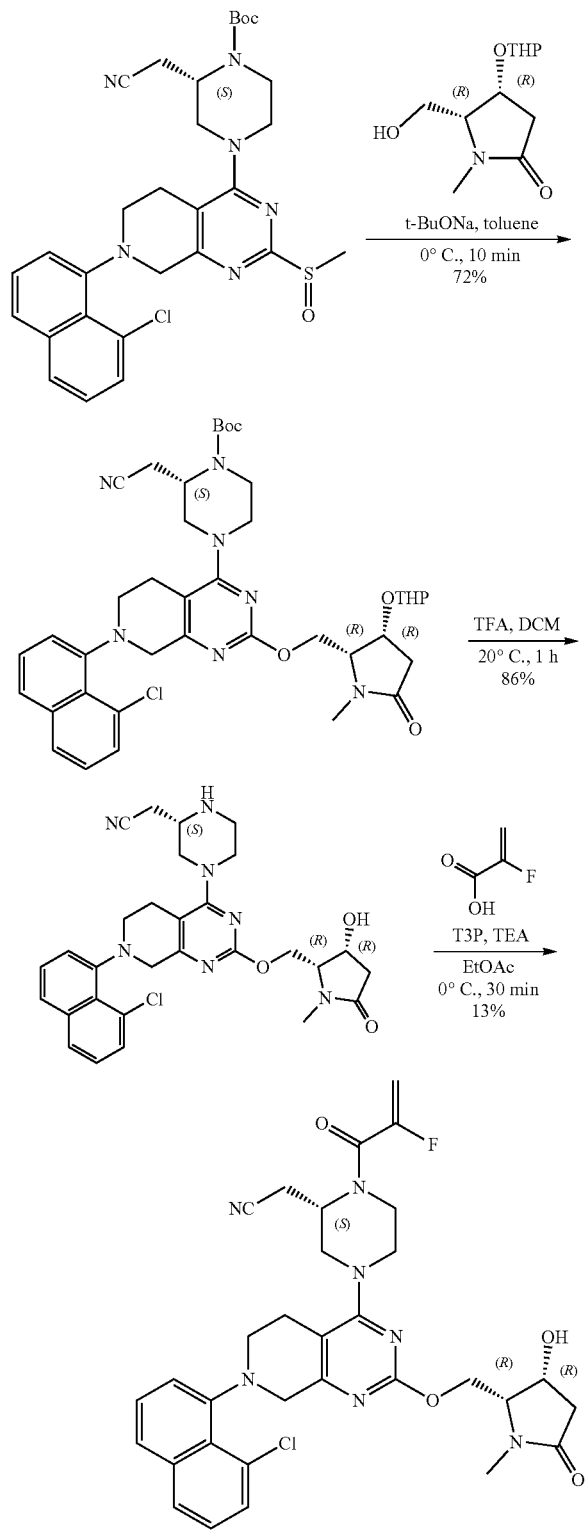

1484

Step A: tert-Butyl (2S)-4-[7-(8-chloro-1-naphthyl)-2-[[(2R,3R)-1-methyl-5-oxo-3-tetrahydropyran-2-yloxy-pyrrolidin-2-yl]methoxy]-6,8-dihydro-5H-pyrido[3,4-d]pyrimidin-4-yl]-2-(cyanomethyl) piperazine-1-carboxylate To a solution of tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (280 mg, 482 μmol, 1 eq) and (4R,5R)-5-(hydroxymethyl)-1-methyl-4-tetrahydropyran-2-yloxy-pyrrolidin-2-one (144 mg, 626 μmol, 1.3 eq) in toluene (6 mL) was added t-BuONa (92.6 mg, 964 μmol, 2 eq). The mixture was stirred at 0° C. for 10 minutes. Upon completion, the mixture was diluted with water (5 mL) and extracted with EtOAc (2×10 mL). The organic layers were dried over Na$_2$SO$_4$ and concentrated under vacuum. The residue was purified by reverse phase flash [water (0.1% FA)/acetonitrile]. The desired fractions were collected and neutralized with NaHCO$_3$, concentrated under vacuum to remove MeCN and extracted with EtOAc (2×20 mL). The organic layers were dried over Na$_2$SO$_4$ and concentrated under vacuum to give tert-butyl (2S)-4-[7-(8-chloro-1-naphthyl)-2-[[(2R,3R)-1-methyl-5-oxo-3-tetrahydropyran-2-yloxy-pyrrolidin-2-yl]methoxy]-6,8-dihydro-5H-pyrido[3,4-d]pyrimidin-4-yl]-2-(cyanomethyl)piperazine-1-carboxylate (280 mg, 345 μmol, 72% yield, 92% purity) as a yellow solid. LCMS [ESI, M+1]: 746.

$^1$H NMR (400 MHz, chloroform-d) δ=7.76 (br d, J=8.0 Hz, 1H), 7.66-7.57 (m, 1H), 7.53 (d, J=7.2 Hz, 1H), 7.50-7.41 (m, 1H), 7.37-7.31 (m, 1H), 7.27-7.18 (m, 1H), 4.88-4.69 (m, 1H), 4.68-4.47 (m, 4H), 4.46-4.35 (m, 1H), 4.11-3.74 (m, 6H), 3.65-3.48 (m, 2H), 3.44-2.99 (m, 5H), 2.96 (dd, J=2.8, 8.4 Hz, 3H), 2.91-2.51 (m, 5H), 1.81-1.64 (m, 2H), 1.52 (s, 13H).

Step B: 2-[(2S)-4-[7-(8-Chloro-1-naphthyl)-2-[[(2R,3R)-3-hydroxy-1-methyl-5-oxo-pyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2R,3R)-1-methyl-5-oxo-3-tetrahydropyran-2-yloxy-pyrrolidin-2-yl]methoxy]-6,8-dihydro-5H-pyrido[3,4-d]pyrimidin-4-yl]-2-(cyanomethyl)piperazine-1-carboxylate (200 mg, 268 μmol, 1 eq) in DCM (0.15 mL) was added TFA (458 mg, 4.02 mmol, 298 μL, 15 eq). The mixture was stirred at 20° C. for 1 hour. Upon completion, the mixture was diluted with DCM (5 mL) and basified with saturated sodium bicarbonate aqueous solution to pH=8. The separated aqueous layer was extracted with EtOAc (5×5 mL). Combined organic layers were dried over MgSO$_4$, filtered and concentrated under vacuum to give 2-[(2S)-4-[7-(8-chloro-1-naphthyl)-2-[[(2R,3R)-3-hydroxy-1-methyl-5-oxo-pyrrolidin-2-yl]methoxy]-6,8-dihydro-5H-pyrido[3,4-d]pyrimidin-4-yl]piperazin-2-yl]acetonitrile (150 mg, 230

µmol, 86% yield, 86% purity) as a yellow solid which was used directly in the next step without further purification. LCMS [ESI, M+1]: 562.

Step C: 2-[(2S)-4-[7-(8-Chloro-1-naphthyl)-2-[[(2R,3R)-3-hydroxy-1-methyl-5-oxo-pyrrolidin-2-yl]methoxy]-6,8-dihydro-5H-pyrido[3,4-d]pyrimidin-4-yl]-1-(2-fluoroprop-2-enoyl)piperazin-2-yl] acetonitrile To a solution of 2-[(2S)-4-[7-(8-chloro-1-naphthyl)-2-[[(2R,3R)-3-hydroxy-1-methyl-5-oxo-pyrrolidin-2-yl]methoxy]-6,8-dihydro-5H-pyrido[3,4-d]pyrimidin-4-yl]piperazin-2-yl]acetonitrile (150 mg, 267 umol, 1 eq), TEA (81.0 mg, 801 umol, 111 uL, 3 eq) and 2-fluoroprop-2-enoic acid (48.1 mg, 534 umol, 2 eq) in EtOAc (4 mL) was added T3P (255 mg, 400 umol, 238 uL, 50% purity in EtOAc, 1.5 eq) at 0° C. The mixture was stirred at 0° C. for 0.5 hour. Upon completion, the mixture was quenched with saturated NaHCO₃ aqueous solution (5 mL) and extracted with EtOAc (2×10 mL). The organic layers were dried over Na₂SO₄ and concentrated under vacuum. The residue was purified by chromatography (Al₂O₃, EtOAc/MeOH 1/0 to 20/1) followed by prep-HPLC (column: Xtimate C18 150*25 mm*5 µm; mobile phase: [water (0.05% ammonium hydroxide v/v)-ACN]; B %: 33%-63%, 10 min). The desired fractions were collected and lyophilized to give title compound 2-[(2S)-4-[7-(8-chloro-1-naphthyl)-2-[[(2R,3R)-3-hydroxy-1-methyl-5-oxo-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (22.0 mg, 34.5 umol, 13% yield, 99.6% purity) as a white solid. LCMS [ESI, M+1]: 634.

¹H NMR (400 MHz, chloroform-d) δ=7.77 (d, J=8.4 Hz, 1H), 7.64 (dd, J=4.4, 8.0 Hz, 1H), 7.54 (d, J=7.6 Hz, 1H), 7.46 (dt, J=6.0, 8.0 Hz, 1H), 7.35 (t, J=7.6 Hz, 1H), 7.27-7.21 (m, 1H), 5.54-5.33 (m, 1H), 5.27 (dd, J=2.8, 17.2 Hz, 1H), 4.88 (dd, J=1.6, 12.0 Hz, 1H), 4.80 (dd, J=6.0, 12.0 Hz, 1H), 4.64-4.48 (m, 2H), 4.47-3.94 (m, 4H), 3.91-3.65 (m, 3H), 3.64-3.43 (m, 2H), 3.37-2.98 (m, 4H), 2.91 (d, J=7.6 Hz, 3H), 2.89-2.76 (m, 1H), 2.70-2.53 (m, 2H), 2.46 (dt, J=5.2, 16.4 Hz, 1H).

Example 574

2-[(2S)-4-[7-(8-Chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl] acetonitrile Step A: tert-Butyl (2S)-4-[7-(8-chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]-2-(cyanomethyl)piperazine-1-carboxylate To a mixture of [(2S,4R)-4-fluoro-1-methyl-pyrrolidin-2-yl]methanol (275 mg, 2.06 mmol, 2.0 eq) in toluene (12.0 mL) was added t-BuONa (198 mg, 2.06 mmol, 2.0 eq) in portions at 0° C., after stirring at 0° C. for 0.5 hour, tert-butyl (2S)-4-[7-(8-chloro-1-naphthyl)-2-methylsulfinyl-6,8-dihydro-5H-pyrido [3,4-d]pyrimidin-4-yl]-2-(cyanomethyl) piperazine-1-carboxylate (600 mg, 1.03 mmol, 1.0 eq) was added, and stirred at 0° C. for 0.5 hour. After completion, water was added (15.0 mL), the resulting mixture was extracted with ethyl acetate (2×10 mL), the combined organic layer was dried over Na$_2$SO$_4$, filtered and concentrated. The residue was purified by reverse phase flash (C18, 0.1% TFA in water, 30%-50% MeCN), the obtained product was adjusted with NaHCO$_3$ solid to pH=8, then concentrated, the aqueous phase was extracted with ethyl acetate (2×15 mL), the organic layer was washed with saturated brine (20.0 mL), then dried over Na$_2$SO$_4$, filtered and concentrated. The product tert-butyl (2S)-4-[7-(8-chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]-2-(cyanomethyl)piperazine-1-carboxylate (510 mg, 769 μmol, 75% yield, 98% purity) was obtained as light yellow solid. LCMS [ESI, M+1]: 650.

$^1$H NMR (400 MHz, chloroform-d) δ 7.80-7.72 (m, 1H), 7.62 (t, J=7.8 Hz, 1H), 7.56-7.50 (m, 1H), 7.46-7.40 (m, 1H), 7.37-7.31 (m, 1H), 7.26-7.17 (m, 1H), 5.29-5.07 (m, 1H), 4.65-4.57 (m, 1H), 4.50-4.34 (m, 2H), 4.30-4.17 (m, 1H), 4.06-3.76 (m, 3H), 3.65-3.47 (m, 2H), 3.41-2.86 (m, 7H), 2.84-2.45 (m, 7H), 2.40-2.24 (m, 1H), 2.04-1.86 (m, 1H), 1.52 (s, 9H).

Step B: 2-[(2S)-4-[7-(8-Chloro-1-naphthyl)-2-[[(2S,4R)-4-fluoro-1-methyl-pyrrolidin-2-yl]methoxyl]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]-2-(cyanomethyl)piperazine-1-carboxylate (500 mg, 769 μmol, 1.0 eq) in dioxane (5.0 mL) was added 4N HCl.dioxane (5.0 mL), the reaction mixture was stirred at 15° C. for 1 hour. After completion, the reaction mixture was filtered, and the solid was dissolved with dichloromethane (15.0 mL), the organic layer was washed with saturated brine (1×15 mL), dried over Na$_2$SO$_4$, filtered and concentrated to give 2-[(2S)-4-[7-(8-chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile (360 mg, 635 μmol, 85% yield, 97% purity) as light yellow solid. LCMS [ESI, M+1]: 550.

Step C: 2-[(2S)-4-[7-(8-Chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(8-chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile (120 mg, 218 μmol, 1.0 eq) and 2-fluoroprop-2-enoic acid (39.3 mg, 436 μmol, 2.0 eq) in ethyl acetate (1.2 mL) was added TEA (177 mg, 1.75 mmol, 243 μL, 8.0 eq) and T3P (416 mg, 654 μmol, 389 μL, 50% purity, 3.0 eq) at 0° C., the reaction mixture was stirred at 0° C. for 1 hour. After completion, the reaction mixture was added saturated brine (10.0 mL), then extracted with ethyl acetate (2×10 mL), the organic layer was dried over Na$_2$SO$_4$, filtered and concentrated. The residue was purified by column chromatography (basic Al$_2$O$_3$, petroleum ether/ethyl acetate=3/1 to ethyl acetate/methanol=20/1), the crude product was re-purified by prep-HPLC (column: Waters Xbridge 150*25 5μ; mobile phase: [water (0.05% ammonium hydroxide v/v)-ACN]; B %: 45%-75%, 10 min]; B %: 45%-75%, 10 min), the obtained product was concentrated, and lyophilized. Title compound 2-[(2S)-4-[7-(8-chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (50.9 mg, 81.0 μmol, 37% yield, 99% purity) was obtained as white solid. LCMS [ESI, M+1]: 622.

$^1$H NMR (400 MHz, chloroform-d) δ 7.76 (d, J=8.0 Hz, 1H), 7.62 (t, J=7.4 Hz, 1H), 7.53 (d, J=7.2 Hz, 1H), 7.49-7.41 (m, 1H), 7.34 (t, J=7.8 Hz, 1H), 7.26-7.18 (m, 1H), 5.55-5.33 (m, 1H), 5.30-5.07 (m, 2H), 5.01-4.66 (m, 1H), 4.53-4.35 (m, 2H), 4.29-3.98 (m, 3H), 3.96-3.78 (m, 2H), 3.73-3.33 (m, 3H), 3.32-2.98 (m, 5H), 2.94-2.71 (m, 2H), 2.68-2.53 (m, 2H), 2.51 (d, J=2.8 Hz, 3H), 2.39-2.23 (m, 1H), 2.08-1.87 (m, 1H).

Example 575

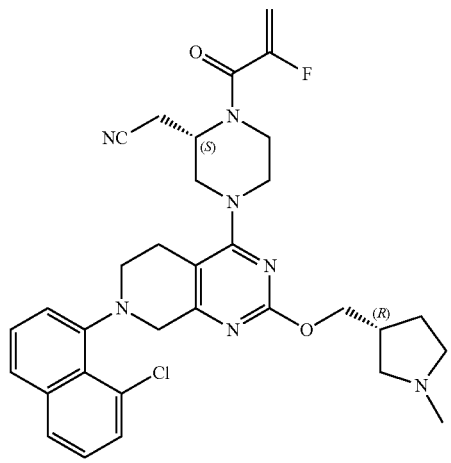

1489

2-[(2S)-4-[7-(8-Chloro-1-naphthyl)-2-[[(3R)-1-methylpyrrolidin-3-yl]methoxy]-6,8-dihydro-5H-pyrido[3,4-d]pyrimidin-4-yl]-1-(2-fluoroprop-2-enoyl)piperazin-2-yl]acetonitrile

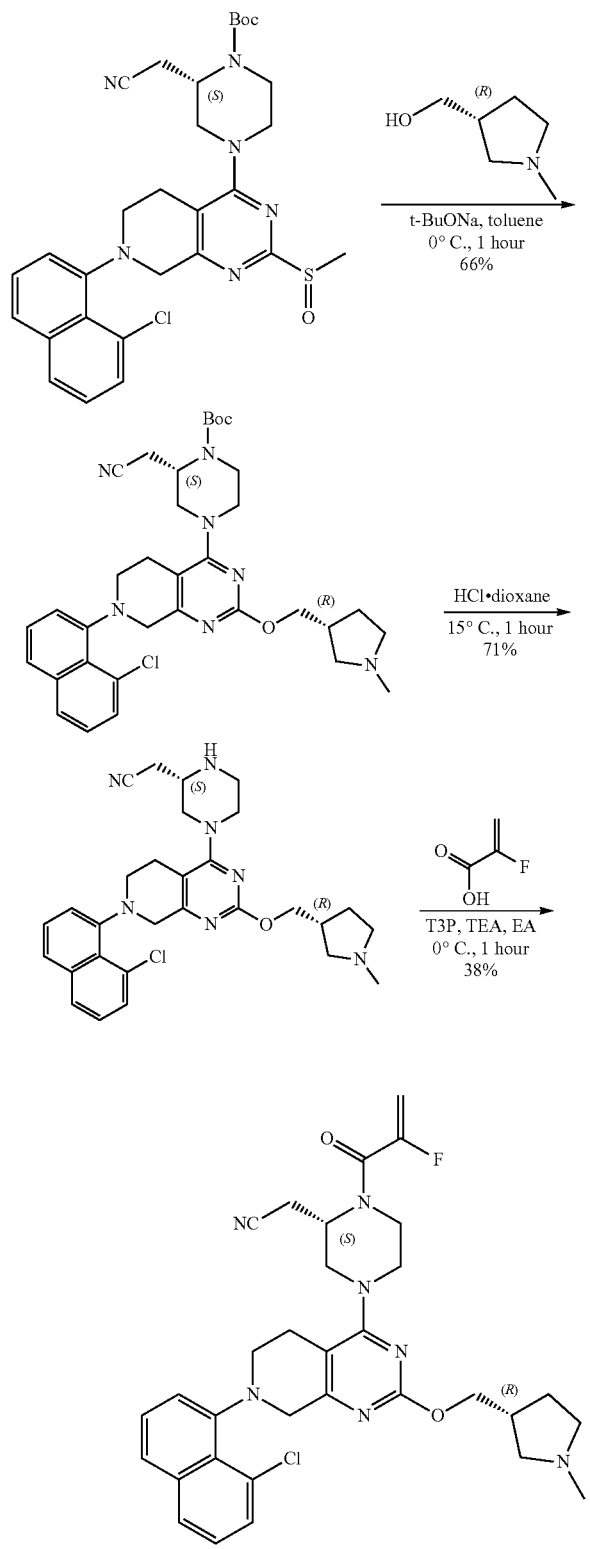

1490

Step A: tert-Butyl (2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-2-(cyanomethyl)piperazine-1-carboxylate To a solution of [(3R)-1-methylpyrrolidin-3-yl]methanol (297 mg, 2.58 mmol, 2.50 eq) in toluene (6.0 mL) was added t-BuONa (198 mg, 2.06 mmol, 2.0 eq). The mixture was stirred at 0° C. for 0.5 hour. Then tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (600 mg, 1.03 mmol, 1.0 eq) was added to the above liquid. After addition, the mixture was stirred at 0° C. for another 0.5 hour. After completion, water was added (20.0 mL) and the resulting mixture extracted with ethyl acetate (3×10.0 mL). The organic layer was dried over $Na_2SO_4$, filtered and concentrated. The residue was purified by reverse phase flash (C18, 0.1% FA in water, 0-60% MeCN) to give the compound tert-butyl (2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-2-(cyanomethyl)piperazine-1-carboxylate (430 mg, 680 µmol, 66% yield) as yellow solid. LCMS [ESI, M+1]: 632.

$^1$H NMR (400 MHz, Chloroform-d) δ 7.75 (d, J=8.0 Hz, 1H), 7.61 (t, J=7.6 Hz, 1H), 7.52 (d, J=7.2 Hz, 1H), 7.48-7.39 (m, 1H), 7.33 (t, J=7.6 Hz, 1H), 7.26-7.15 (m, 1H), 4.67-4.55 (m, 1H), 4.50-4.35 (m, 1H), 4.27-4.17 (m, 2H), 4.08-3.75 (m, 4H), 3.65-3.50 (m, 1H), 3.39-3.02 (m, 5H), 3.00-2.86 (m, 1H), 2.81-2.64 (m, 4H), 2.62-2.46 (m, 4H), 2.35 (s, 3H), 2.15-2.05 (m, 1H), 1.52 (s, 9H).

Step B: 2-[(2S)-4-[7-(8-Chloro-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-2-(cyanomethyl)piperazine-1-carboxylate (400 mg, 632 µmol, 1.0 eq) in dioxane (2.0 mL) was added HCl.dioxane (4.0 M, 2.0 mL, 12.6 eq). The mixture was stirred at 15° C. for 1 hour. After completion, the reaction mixture was concentrated. The residue was adjusted with saturated aqueous $NaHCO_3$ (10.0 mL) to pH ~7, and then extracted with ethyl acetate (3×10.0 mL). The organic layer was dried over $Na_2SO_4$, filtered and concentrated to give the compound 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (240 mg, 451 µmol, 71% yield) as yellow solid which was used for the next step without further purification. LCMS [ESI, M+1]: 532.

Step C: 2-[(2S)-4-[7-(8-Chloro-1-naphthyl)-2-[[(3R)-1-methylpyrrolidin-3-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(8-chloro-1-naphthyl)-2-[[(3R)-1-methylpyrrolidin-3-yl]methoxy]-6,8-dihydro-5H- pyrido[3,4-d]pyrimidin-4-yl]piperazin-2-yl]acetonitrile (80.0 mg, 150 μmol, 1.0 eq), 2-fluoroprop-2-enoic acid (27.1 mg, 301 μmol, 2.0 eq) and TEA (122 mg, 1.20 mmol, 167 μL, 8.0 eq) in ethyl acetate (2.0 mL) was added T3P (287 mg, 451 umol, 268 μL, 50% purity in ethyl acetate, 3.0 eq). The mixture was stirred at 0° C. for 0.5 hour. After completion, the reaction mixture was quenched with HCl (12.0 M, 60.0 uL in 2.0 mL of water). The mixture was adjusted to pH ~8 with saturated aqueous NaHCO₃ and extracted with ethyl acetate (3×10.0 mL). The combined organic layers were washed with brine (30.0 mL), dried over Na₂SO₄, filtered and concentrated. The residue was purified by prep-HPLC (column: Phenomenex Synergi C18 150*25*10 μm; mobile phase: [water (0.225% FA)-ACN]; B %: 25%-45%, 8 min), then concentrated. The aqueous layer was adjusted with saturated aqueous NaHCO₃ to pH ~8 and extracted with ethyl acetate (3×10.0 mL). The organic layer was dried over Na₂SO₄, filtered and concentrated under reduced pressure to give the title compound 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-1-(2-fluoroprop-2-enoyl)piperazin-2-yl]acetonitrile (35.9 mg, 57.5 μmol, 38% yield, 96.8% purity) as white solid. LCMS [ESI, M+1]: 604.

¹H NMR (400 MHz, Chloroform-d) δ 7.78-7.73 (d, J=8.4 Hz, 1H), 7.62 (t, J=7.2 Hz, 1H), 7.52 (d, J=7.2 Hz, 1H), 7.49-7.40 (m, 1H), 7.34 (t, J=8.0 Hz, 1H), 7.27-7.18 (m, 1H), 5.54-5.32 (m, 1H), 5.30-5.21 (m, 1H), 5.04-4.75 (m, 1H), 4.48-4.36 (m, 1H), 4.27-4.17 (m, 2H), 4.16-3.96 (m, 2H), 3.89-3.75 (m, 1H), 3.64-3.55 (m, 1H), 3.51-3.32 (m, 1H), 3.30-2.98 (m, 4H), 2.96-2.67 (m, 4H), 2.66-2.46 (m, 4H), 2.37 (d, J=2.0 Hz, 3H), 2.14-2.06 (m, 1H), 1.70-1.57 (m, 1H).

Example 576

2-[(2S)-4-[7-(8-Chloro-1-naphthyl)-2-[[(2R,4R)-4-methoxy-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

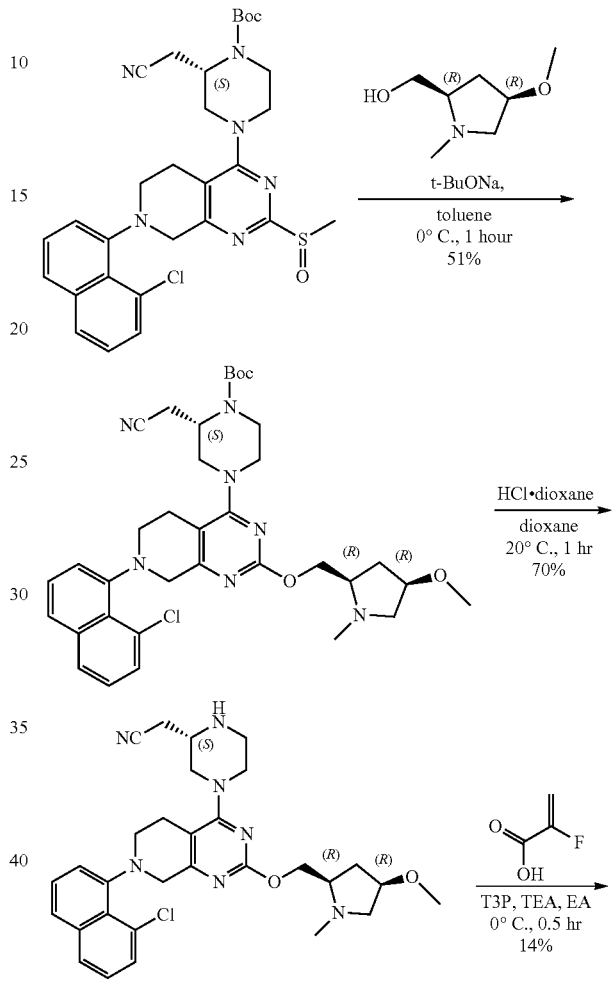

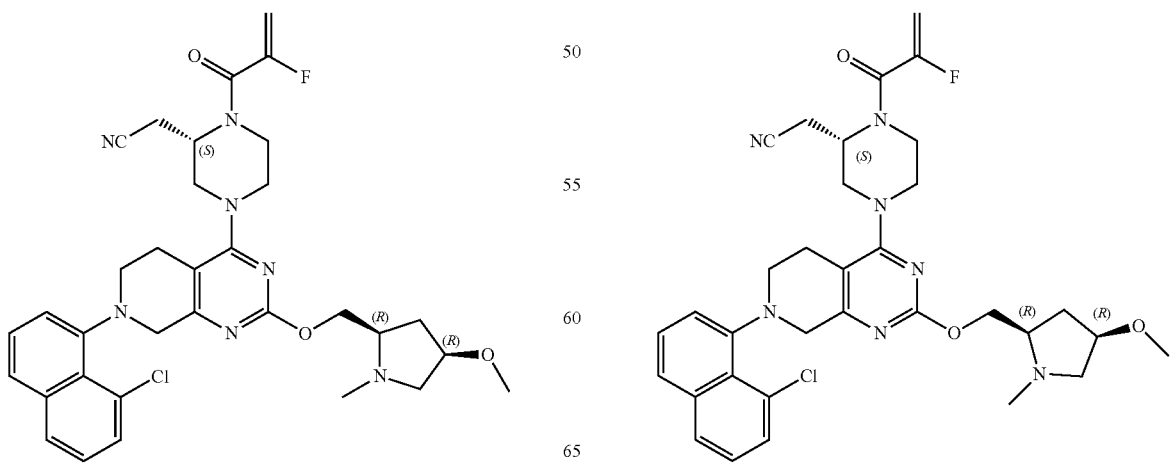

Step A: tert-Butyl (2S)-4-[7-(8-chloro-1-naphthyl)-2-[[(2R,4R)-4-methoxy-1-methyl-pyrrolidin-2-yl]methoxy]-6,8-dihydro-5H-pyrido[3,4-d]pyrimidin-4-yl]-2-(cyanomethyl)piperazine-1-carboxylate To a solution of tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (300 mg, 516 µmol, 1 eq) in toluene (5.00 mL) was added t-BuONa (124 mg, 1.29 mmol, 2.5 eq) and [(2R,4R)-4-methoxy-1-methyl-pyrrolidin-2-yl]methanol (149 mg, 1.03 mmol, 2 eq). The mixture was stirred at 0° C. for 1 hour. The reaction mixture was diluted with water (20 mL) and extracted with ethyl acetate (50 mL×3). The combined organic layers were washed with brine (20 mL), dried over Na₂SO₄, filtered and concentrated under reduced pressure to give a residue. The residue was purified by column chromatography (SiO₂, ethyl acetate/methanol=100/1 to 10:1). tert-butyl (2S)-4-[7-(8-chloro-1-naphthyl)-2-[[(2R,4R)-4-methoxy-1-methyl-pyrrolidin-2-yl]methoxy]-6,8-dihydro-5H-pyrido[3,4-d]pyrimidin-4-yl]-2-(cyanomethyl)piperazine-1-carboxylate (200 mg, 265 µmol, 51% yield, 88% purity) was obtained as a yellow solid. LCMS [ESI, M+1]: 662.

Step B: 2-[(2S)-4-[7-(8-Chloro-1-naphthyl)-2-[[(2R,4R)-4-methoxy-1-methyl-pyrrolidin-2-yl]methoxyl]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2R,4R)-4-methoxy-1-methyl-pyrrolidin-2-yl]methoxy]-6,8-dihydro-5H-pyrido[3,4-d]pyrimidin-4-yl]-2-(cyanomethyl)piperazine-1-carboxylate (200 mg, 302 µmol, 1 eq) in dioxane (1.00 mL) was added HCl/dioxane (4 M, 1.13 mL, 1.00 eq). The mixture was stirred at 20° C. for 1 hour. The reaction mixture was concentrated under vacuum and diluted with water (20 mL). The mixture was adjusted to pH=8 with saturated NaHCO₃ aqueous solution and extracted with ethyl acetate (30 mL×3). The combined organic layers were washed with brine (20 mL), dried over Na₂SO₄, filtered and concentrated under reduced pressure to give the residue. 2-[(2S)-4-[7-(8-chloro-1-naphthyl)-2-[[(2R,4R)-4-methoxy-1-methyl-pyrrolidin-2-yl]methoxy]-6,8-dihydro-5H-pyrido[3,4-d]pyrimidin-4-yl]piperazin-2-yl]acetonitrile (110 mg, 154.60 µmol, 70% yield, 79% purity) was obtained as a yellow solid and used next step without purification. LCMS [ESI, M+1]: 562.

Step C: 2-[(2S)-4-[7-(8-Chloro-1-naphthyl)-2-[[(2R,4R)-4-methoxy-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(8-chloro-1-naphthyl)-2-[[(2R,4R)-4-methoxy-1-methyl-pyrrolidin-2-yl]methoxy]-6,8-dihydro-5H-pyrido[3,4-d]pyrimidin-4-yl]piperazin-2-yl]acetonitrile (110 mg, 195 µmol, 1 eq) in ethyl acetate (1.00 mL) was added 2-fluoroprop-2-enoic acid (35.3 mg, 391 µmol, 2 eq), T3P (374 mg, 587 µmol, 349 µL, 50% purity, 3 eq) and TEA (158 mg, 1.57 mmol, 218 µL, 8 eq). The mixture was stirred at 0° C. for 0.5 hour. The reaction mixture was diluted with water (20 mL) and extracted with ethyl acetate (30 mL×3). The combined organic layers were washed with brine (20 mL), dried over Na₂SO₄, filtered and concentrated under reduced pressure to give a residue. The residue was purified by column chromatography (SiO₂, ethyl acetate/methanol=100/1 to 10/1) and further by prep-HPLC (column: Waters Xbridge 150*25 5µ; mobile phase: [water (0.05% ammonium hydroxide v/v)-ACN]; B %: 45%-75%, 10 min). The desired fractions were collected and lyophilized. Title compound 2-[(2S)-4-[7-(8-chloro-1-naphthyl)-2-[[(2R,4R)-4-methoxy-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (17 mg, 26.7 µmol, 14% yield, 99.8% purity) was obtained as a white gum. LCMS [ESI, M+1]: 634.

¹H NMR (400 MHz, chloroform-d) δ=7.76 (d, J=8.4 Hz, 1H), 7.62 (t, J=7.6 Hz, 1H), 7.53 (d, J=7.2 Hz, 1H), 7.49-7.40 (m, 1H), 7.34 (t, J=7.6 Hz, 1H), 7.27-7.18 (m, 1H), 5.42 (d, J=49.2 Hz, 1H), 5.26 (dd, J=3.6, 16.8 Hz, 1H), 4.91 (br s, 1H), 4.54-4.34 (m, 2H), 4.27-4.00 (m, 3H), 3.96-3.77 (m, 2H), 3.67-3.54 (m, 1H), 3.51-3.37 (m, 1H), 3.37-2.96 (m, 9H), 2.95-2.64 (m, 3H), 2.63-2.53 (m, 1H), 2.52-2.27 (m, 5H), 1.91-1.74 (m, 1H).

Example 577

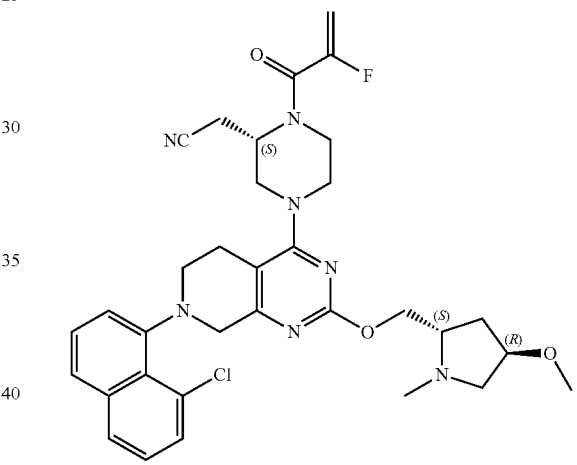

2-[(2S)-4-[7-(8-Chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl] acetonitrile

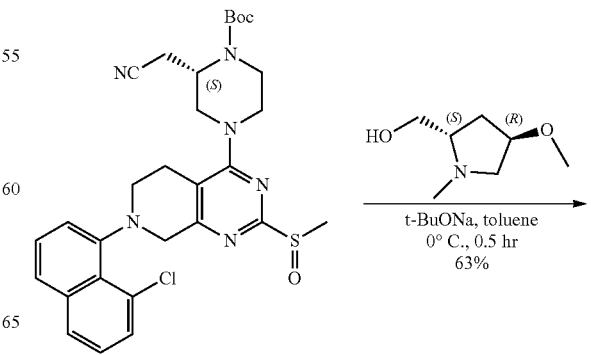

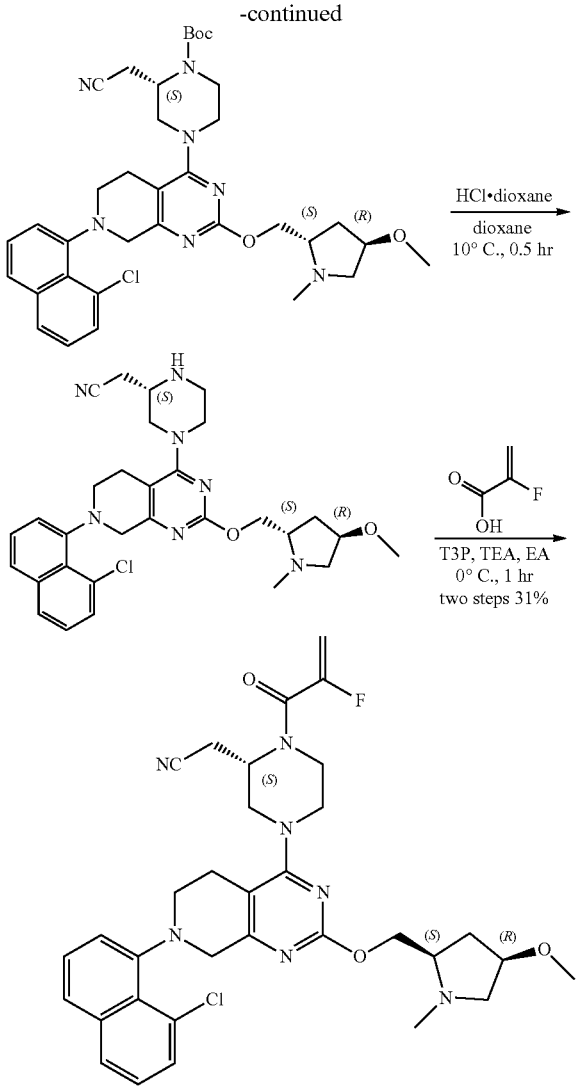

Step A: tert-Butyl (2S)-4-[7-(8-chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]-2-(cyanomethyl)piperazine-1-carboxylate To a solution of [(2S,4R)-4-methoxy-1-methyl-pyrrolidin-2-yl]methanol (300 mg, 2.06 mmol, 2.0 eq) and t-BuONa (149 mg, 1.55 mmol, 1.50 eq) in toluene (7.0 mL) was added tert-butyl(2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (600 mg, 1.03 mmol, 1.0 eq). The mixture was stirred at 0° C. for 0.5 hour. After completion, water was added (20.0 mL) and the resulting mixture extracted with ethyl acetate (3×10.0 mL). The organic layer was dried over Na₂SO₄, filtered and concentrated. The residue was purified by reverse phase flash (C18, 0.1% FA in water, 0-60% MeCN) to give the compound tert-butyl (2S)-4-[7-(8-chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]-2-(cyanomethyl)piperazine-1-carboxylate (450 mg, 652 μmol, 63% yield, 96% purity) as yellow solid. LCMS [ESI, M+1]: 662.

¹H NMR (400 MHz, Chloroform-d) δ 7.76 (br d, J=8.4 Hz, 1H), 7.61 (t, J=7.8 Hz, 1H), 7.52 (d, J=7.6 Hz, 1H), 7.48-7.40 (m, 1H), 7.35 (t, J=7.8 Hz, 1H), 7.27-7.16 (m, 1H), 4.63-4.56 (m, 1H), 4.50-4.35 (m, 2H), 4.23-4.15 (m, 1H), 4.12-3.91 (m, 4H), 3.90-3.75 (m, 1H), 3.65-3.53 (m, 1H), 3.50-3.39 (m, 1H), 3.38-3.32 (m, 1H), 3.30 (d, J=2.0 Hz, 3H), 3.28-3.06 (m, 3H), 3.02-2.85 (m, 2H), 2.83-2.64 (m, 2H), 2.62-2.52 (m, 1H), 2.47 (d, J=2.8 Hz, 3H), 2.35-2.29 (m, 1H), 2.11-2.06 (m, 1H), 2.03-1.91 (m, 1H), 1.52 (s, 9H).

Step B: 2-[(2S)-4-[7-(8-Chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]-2-(cyanomethyl)piperazine-1-carboxylate (450 mg, 680 μmol, 1.0 eq) in dioxane (4.0 mL) was added HCl.dioxane (4 M, 4.0 mL, 23.6 eq). The mixture was stirred at 15° C. for 0.5 hour. After completion, the reaction mixture was concentrated. The residue was adjusted with saturated aqueous NaHCO₃ (10.0 mL) to pH ~7, and then extracted with ethyl acetate (3×10.0 mL). The organic layer was dried over Na₂SO₄, filtered and concentrated to give 2-[(2S)-4-[7-(8-chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]piperazin-2-yl]acetonitrile (300 mg, crude) as yellow solid which was used for the next step without further purification. LCMS [ESI, M+1]: 562.

Step C: 2-[(2S)-4-[7-(8-Chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(8-chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]piperazin-2-yl]acetonitrile (90.0 mg, 160 μmol, 1.0 eq), 2-fluoroprop-2-enoic acid (28.8 mg, 320 μmol, 2.0 eq) and TEA (130 mg, 1.28 mmol, 178 μL, 8.0 eq) in EA (3.0 mL) was added T3P (306 mg, 480 μmol, 286 μL, 50% purity, 3.0 eq). The mixture was stirred at 0° C. for 1 hour. After completion, water was added (10.0 mL) and the resulting mixture extracted with ethyl acetate (3×10.0 mL). The organic layer was dried over Na₂SO₄, filtered and concentrated under vacuum. The residue was purified by prep-HPLC (column: Waters Xbridge 150*25 5μ; mobile phase: [water (0.05% ammonium hydroxide v/v)-ACN]; B %: 50%-80%,10 min) to give title compound 2-[(2S)-4-[7-(8-chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (32.0 mg, 50.3 μmol, 31% yield, 99% purity) as white solid. LCMS [ESI, M+1]: 635.

¹H NMR (400 MHz, Chloroform-d) δ 7.76 (d, J=8.4 Hz, 1H), 7.62 (t, J=7.6 Hz, 1H), 7.53 (d, J=7.6 Hz, 1H), 7.49-7.40 (m, 1H), 7.34 (t, J=7.8 Hz, 1H), 7.26-7.17 (m, 1H), 5.54-5.32 (m, 1H), 5.26 (dd, J=3.6, 16.8 Hz, 1H), 5.10-4.70 (m, 1H), 4.52-4.34 (m, 2H), 4.27-3.80 (m, 6H), 3.69-3.54 (m, 1H), 3.50-3.37 (m, 2H), 3.30 (d, J=1.6 Hz, 3H), 3.28-3.02 (m, 4H), 2.98-2.68 (m, 3H), 2.65-2.53 (m, 1H), 2.47 (d, J=2.4 Hz, 3H), 2.37-2.28 (m, 1H), 2.13-2.03 (m, 1H), 2.02-1.90 (m, 1H).

Example 578

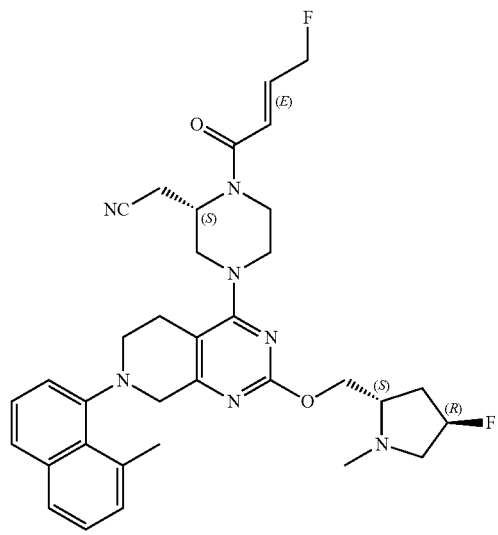

2-[(2S)-1-[(E)-4-Fluorobut-2-enoyl]-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl] acetonitrile

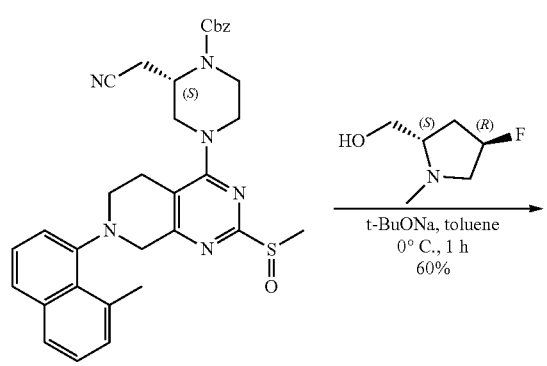

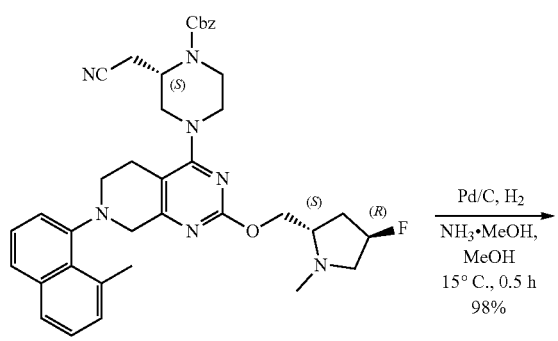

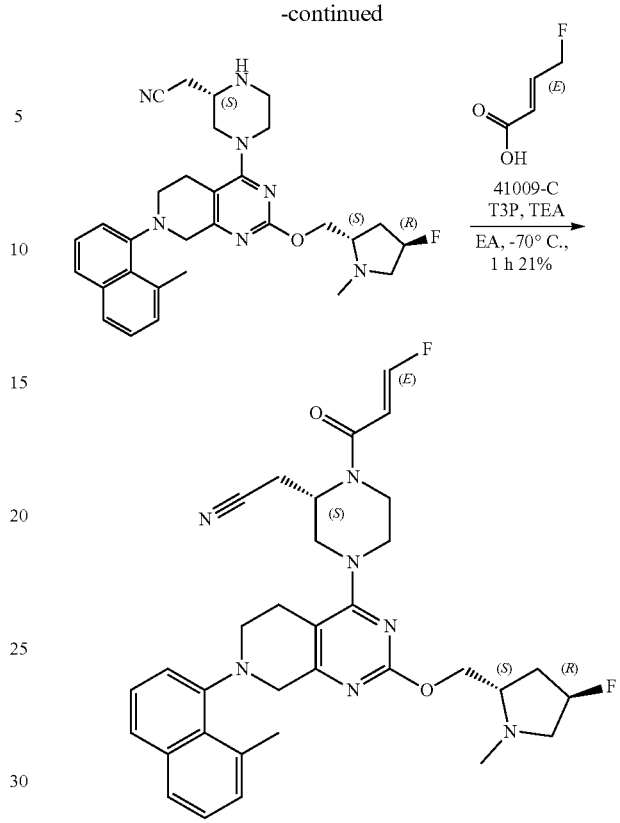

Step A: Benzyl (2S)-2-(cyanomethyl)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate To a solution of benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (500 mg, 840 µmol, 1.00 eq) in toluene (10.0 mL) was added t-BuONa (202 mg, 2.10 mmol, 2.50 eq) and [(2S,4R)-4-fluoro-1-methyl-pyrrolidin-2-yl]methanol (224 mg, 1.68 mmol, 2.00 eq). After stirred at 0° C. for 1 hour, the reaction mixture was diluted with water (20 mL) and extracted with ethyl acetate (50 mL×3). The combined organic layers were washed with brine (20 mL), dried over Na$_2$SO$_4$, filtered and concentrated under reduced pressure to give a residue. The residue was purified by column chromatography (SiO$_2$, ethyl acetate/methanol=100/1 to 10/1). Benzyl (2S)-2-(cyanomethyl)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (340 mg, 502 µmol, 60% yield, 98% purity) was obtained as a yellow solid. LCMS [ESI, M+1]: 664.

Step B: 2-[(2S)-4-[2-[[(2S,4R)-4-fluoro-1-methyl-pyrrolidin-2-yl] methoxy]-7-(8-methyl-1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (200 mg, 301 µmol, 1.00 eq) in MeOH (15.0 mL) was added Pd/C (30.0 mg, 10% purity) and NH₃/MeOH (5.00 mL, 20% purity) under N₂. The suspension was degassed under vacuum and purged with H₂ several times. The mixture was stirred under H₂ (15 psi) at 15° C. for 0.5 hour. The catalyst was filtered off. The filtrate was concentrated under vacuum. 2-[(2S)-4-[2-[[(2S,4R)-4-fluoro-1-methyl-pyrrolidin-2-yl] methoxy]-7-(8-methyl-1-naphthyl)-6,8-dihydro-5H-pyrido[3,4-d]pyrimidin-4-yl]piperazin-2-yl]acetonitrile (159 mg, 294 µmol, 98% yield, 98% purity) was obtained as a yellow solid and used next step directly without purification. LCMS [ESI, M+1]: 530.

Step C: 2-[(2S)-1-[(E)-4-Fluorobut-2-enoyl]-4-[2-[[(2S,4R)-4-fluoro-1-methyl-pyrrolidin-2-yl] methoxy]-7-(8-methyl-1-naphthyl)-6, 8-dihydro-5H-pyrido[3,4-d]pyrimidin-4-yl]piperazin-2-yl] acetonitrile To a solution of 2-[(2S)-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (140 mg, 264 µmol, 1.00 eq) and (E)-4-fluorobut-2-enoic acid (82.5 mg, 793 µmol, 3.00 eq) in ethyl acetate (2.00 mL) was added TEA (160 mg, 1.59 mmol, 220 µL, 6.00 eq) and T3P (505 mg, 793 µmol, 472 µL, 50% purity, 3.00 eq) at −70° C. The mixture was stirred at −70° C. for 1 hour. The reaction mixture was quenched with HCl (12 N, 130 µL in 2 mL of water) at −70° C. The mixture was warmed to 0° C. and basified with saturated NaHCO₃ aqueous solution to pH=8 and extracted with ethyl acetate (20 mL×3). The combined organic layers were washed with brine (10 mL), dried over Na₂SO₄, filtered and concentrated under reduced pressure to give the residue. The residue was purified by prep-HPLC (column: Waters Xbridge 150*25 5µ; mobile phase: [water (0.05% ammonium hydroxide v/v)-ACN]; B %: 45%-75%, 10 min). The desired fractions were collected and lyophilized. Title compound 2-[(2S)-1-[(E)-4-fluorobut-2-enoyl]-4-[2-[[(2S,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (34.5 mg, 55.8 umol, 21% yield, 99.7% purity) was obtained as a white solid. LCMS [ESI, M+1]: 616.

¹H NMR (400 MHz, chloroform-d) δ=7.74-7.62 (m, 2H), 7.46-7.31 (m, 2H), 7.27-7.17 (m, 2H), 7.09-6.93 (m, 1H), 6.59 (d, J=15.2 Hz, 1H), 5.30-4.51 (m, 4H), 4.48-4.35 (m, 1H), 4.30-3.66 (m, 6H), 3.63-3.34 (m, 3H), 3.24-2.96 (m, 5H), 2.92 (s, 3H), 2.87-2.53 (m, 4H), 2.50 (d, J=4.4 Hz, 3H), 2.40-2.22 (m, 1H), 2.10-1.86 (m, 1H) (m, 3H).

Example 579

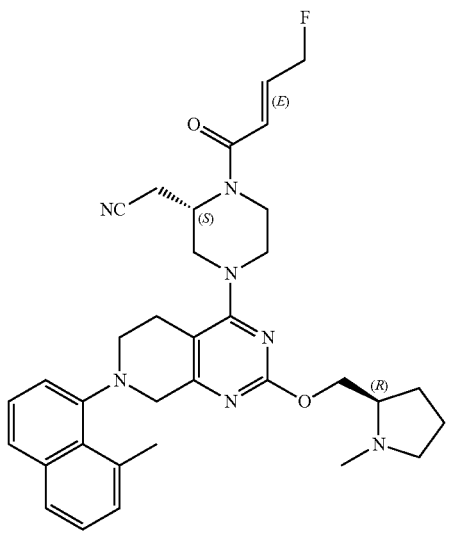

2-[(2S)-1-[(E)-4-Fluorobut-2-enoyl]-4-[7-(8-methyl-1-naphthyl)-2-[[(2R)-1-methylpyrrolidin-2-yl] methoxy]-6,8-dihydro-5H-pyrido[3,4-d]pyrimidin-4-yl]piperazin-2-yl]acetonitrile

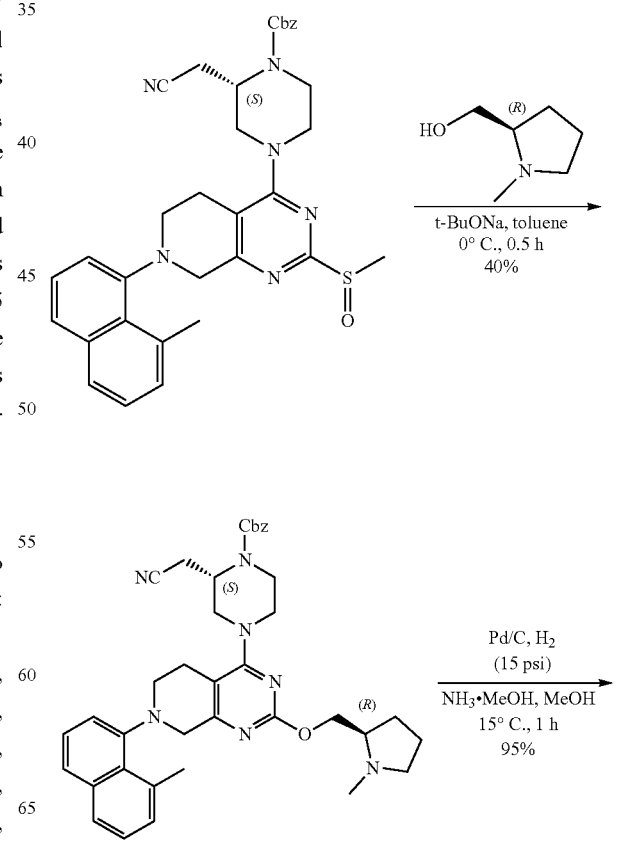

-continued

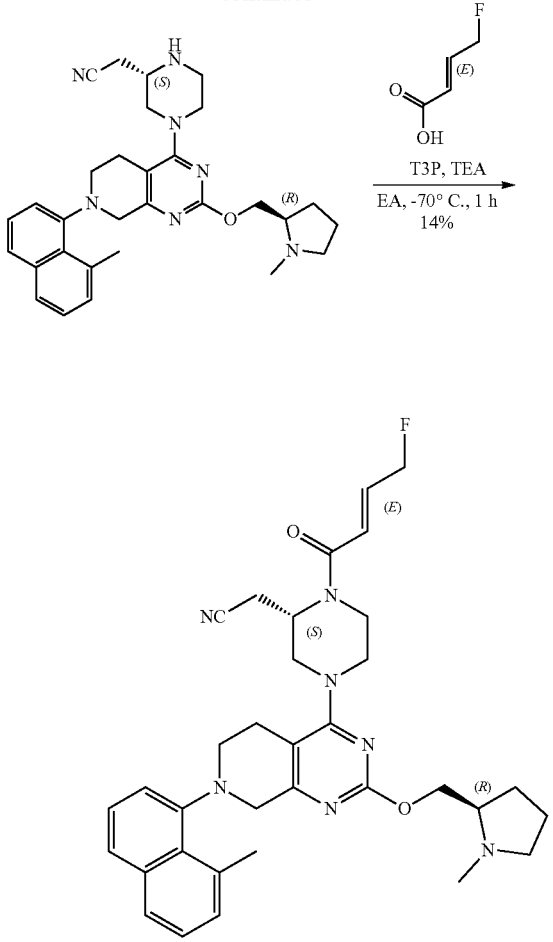

Step A: Benzyl (2S)-2-(cyanomethyl)-4-[7-(8-methyl-1-naphthyl)-2-[[(2R)-1-methyl pyrrolidin-2-yl]methoxy]-6,8-dihydro-5H-pyrido[3,4-d]pyrimidin-4-yl]piperazine-1-carboxylate To a solution of benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (500 mg, 841 μmol, 1 eq) in toluene (10 mL) was added t-BuONa (242 mg, 2.52 mmol, 3 eq) and [(2R)-1-methylpyrrolidin-2-yl]methanol (194 mg, 1.68 mmol, 2 eq) at 0° C. The mixture was stirred at 0° C. for 0.5 hour. The reaction mixture was diluted with water (20 mL) and extracted with ethyl acetate (20 mL×3). The combined organic layers were washed with brine (20 mL), dried over Na$_2$SO$_4$, filtered and concentrated under reduced pressure to give a residue. The residue was purified by column chromatography (SiO$_2$, Ethyl acetate/MeOH=100/1 to 10/1). benzyl (2S)-2-(cyanomethyl)-4-[7-(8-methyl-1-naphthyl)-2-[[(2R)-1-methyl pyrrolidin-2-yl]methoxy]-6,8-dihydro-5H-pyrido[3,4-d]pyrimidin-4-yl]piperazine-1-carboxylate (240 mg, 338 μmol, 40% yield, 91% purity) was obtained as a yellow solid. LCMS [ESI, M+1]: 646.

Step B: 2-[(2S)-4-[7-(8-Methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (240 mg, 372 μmol, 1 eq) in MeOH (15 mL) was added Pd/C (30 mg, 10% purity) and NH$_3$.MeOH (5 mL, 20% purity) under N$_2$. The suspension was degassed under vacuum and purged with H$_2$ several times. The mixture was stirred under H$_2$ (15 psi) at 15° C. for 1 hour. The catalyst was filtered off. The filtrate was concentrated under vacuum. 2-[(2S)-4-[7-(8-methyl-1-naphthyl)-2-[[(2R)-1-methylpyrrolidin-2-yl]methoxy]-6, 8-dihydro-5H-pyrido [3,4-d]pyrimidin-4-yl]piperazin-2-yl]acetonitrile (180 mg, 352 μmol, 95% yield) was obtained as a yellow solid and used next step directly without purification. LCMS [ESI, M+1]: 512.

Step C: 2-[(2S)-1-[(E)-4-Fluorobut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (100 mg, 195 umol, 1 eq) and (E)-4-fluorobut-2-enoic acid (40.7 mg, 391 umol, 2 eq) in EtOAc (2 mL) was added TEA (79.1 mg, 782 umol, 109 uL, 4 eq) and T3P (249 mg, 391 umol, 232 uL, 50% purity in EtOAc, 2 eq) at −70° C. The mixture was stirred at −70° C. for 1 hour. The reaction mixture was quenched with HCl (60 uL (12 M) in 2 mL of water). The mixture was adjusted pH=8 with saturated NaHCO$_3$ aqueous solution and extracted with ethyl acetate (20 mL×3). The combined organic layers were washed with brine (10 mL), dried over Na$_2$SO$_4$, filtered and concentrated under reduced pressure to give the residue. The residue was purified by prep-HPLC (column: Luna C18 150*25 5 u; mobile phase: [water (0.225% FA)-ACN]; B %: 25%-45%, 7.8 min) and further purified by prep-HPLC (column: Waters Xbridge 150*25 5 u; mobile phase: [water (0.05% ammonia hydroxide v/v)-ACN]; B %: 52%-79%, 10 min). The desired fractions were collected and lyophilized. Title compound 2-[(2S)-1-[(E)-4-fluorobut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (16.6 mg, 27.7 umol, 14% yield, 99.6% purity) was obtained as a yellow gum. LCMS [ESI, M+1]: 598.

$^1$H NMR (400 MHz, chloroform-d) δ=7.72-7.62 (m, 2H), 7.45-7.32 (m, 2H), 7.27-7.16 (m, 2H), 7.07-6.93 (m, 1H), 6.60 (d, J=15.6 Hz, 1H), 5.26-4.51 (m, 3H), 4.39 (s, 1H), 4.31-3.33 (m, 9H), 3.27-2.97 (m, 5H), 2.92 (s, 3H), 2.87-2.76 (m, 1H), 2.65 (m, 2H), 2.49 (br d, J=4.6 Hz, 3H), 2.29 (m, 1H), 2.15-1.96 (m, 1H), 1.92-1.67 (m, 3H).

Example 580

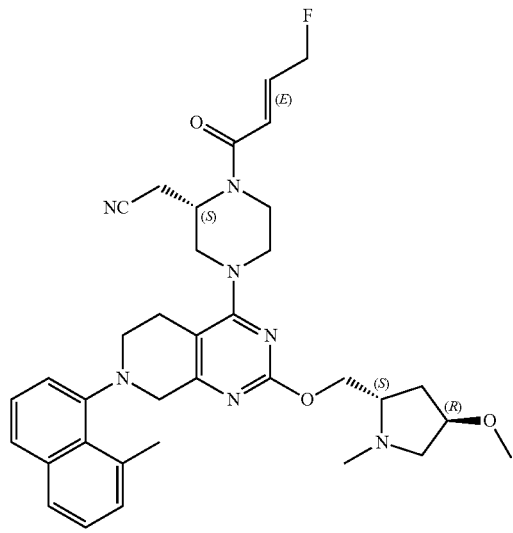

2-[(2S)-1-[(E)-4-fluorobut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile

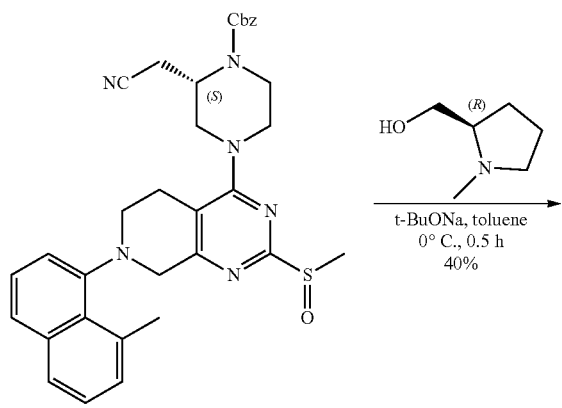

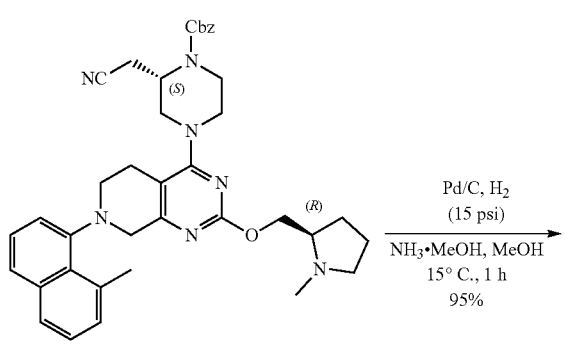

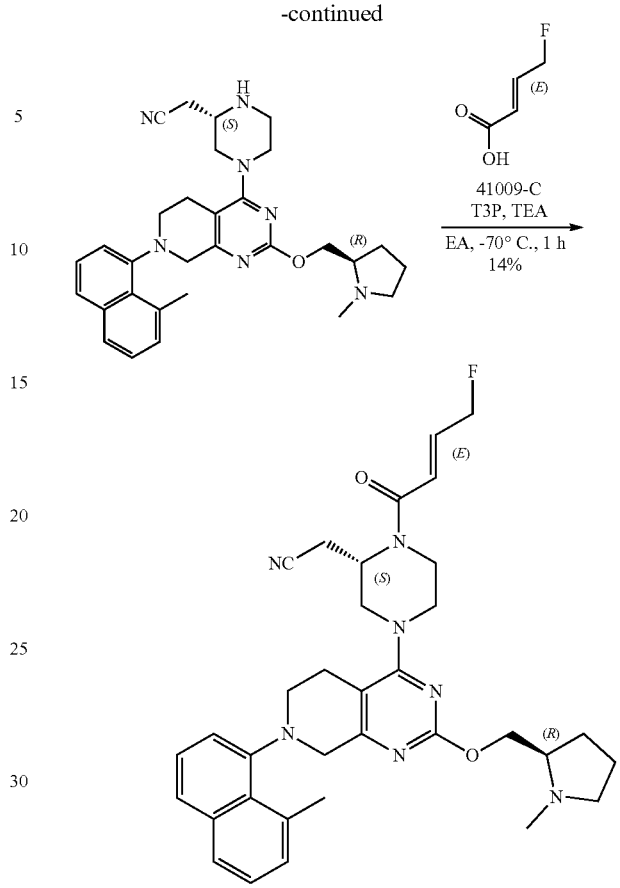

Step A: Benzyl (2S)-2-(cyanomethyl)-4-[7-(8-methyl-1-naphthyl)-2-[[(2R)-1-methyl pyrrolidin-2-yl]methoxy]-6,8-dihydro-5H-pyrido[3,4-d]pyrimidin-4-yl]piperazine-1-carboxylate To a solution of benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (500 mg, 841 μmol, 1 eq) in toluene (10 mL) was added t-BuONa (242 mg, 2.52 mmol, 3 eq) and [(2R)-1-methylpyrrolidin-2-yl]methanol (194 mg, 1.68 mmol, 2 eq) at 0° C. The mixture was stirred at 0° C. for 0.5 hour. The reaction mixture was diluted with water (20 mL) and extracted with ethyl acetate (20 mL×3). The combined organic layers were washed with brine (20 mL), dried over Na$_2$SO$_4$, filtered and concentrated under reduced pressure to give a residue. The residue was purified by column chromatography (SiO$_2$, ethyl acetate/MeOH=100/1 to 10/1). Benzyl (2S)-2-(cyanomethyl)-4-[7-(8-methyl-1-naphthyl)-2-[[(2R)-1-methyl pyrrolidin-2-yl]methoxy]-6,8-dihydro-5H-pyrido[3,4-d]pyrimidin-4-yl]piperazine-1-carboxylate (240 mg, 338 μmol, 40% yield, 91% purity) was obtained as a yellow solid. LCMS [ESI, M+1]: 646.

Step B: 2-[(2S)-4-[7-(8-Methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-2-[[(2R)-1-methylpyrrolidin-2-yl]

methoxy]-6,8-dihydro-5H-pyrido[3,4-d]pyrimidin-4-yl]piperazine-1-carboxylate (240 mg, 372 µmol, 1 eq) in MeOH (15 mL) was added Pd/C (30 mg, 10% purity) and NH$_3$·MeOH (5 mL, 20% purity) under N$_2$. The suspension was degassed under vacuum and purged with H$_2$ several times. The mixture was stirred under H$_2$ (15 psi) at 15° C. for 1 hour. The catalyst was filtered off. The filtrate was concentrated under vacuum. 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (180 mg, 352 µmol, 95% yield) was obtained as a yellow solid and used next step directly without purification. LCMS [ESI, M+1]: 512.

Step C: 2-[(2S)-1-[(E)-4-Fluorobut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (100 mg, 195 µmol, 1 eq) and (E)-4-fluorobut-2-enoic acid (40.7 mg, 391 umol, 2 eq) in EtOAc (2 mL) was added TEA (79.1 mg, 782 µmol, 109 µL, 4 eq) and T3P (249 mg, 391 µmol, 232 µL, 50% purity in EtOAc, 2 eq) at −70° C. The mixture was stirred at −70° C. for 1 hour. The reaction mixture was quenched with HCl (60 µL (12 M) in 2 mL of water). The mixture was adjusted pH=8 with saturated NaHCO$_3$ aqueous solution and extracted with ethyl acetate (20 mL×3). The combined organic layers were washed with brine (10 mL), dried over Na$_2$SO$_4$, filtered and concentrated under reduced pressure to give the residue. The residue was purified by prep-HPLC (column: Luna C18 150*25 5µ; mobile phase: [water (0.225% FA)-MeCN]; B %: 25%-45%, 7.8 min) and further purified by prep-HPLC (column: Waters Xbridge 150*25 5µ; mobile phase: [water (0.05% ammonium hydroxide v/v)-MeCN]; B %: 52%-79%, 10 min). The desired fractions were collected and lyophilized. Title compound 2-[(2S)-1-[(E)-4-fluorobut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (16.6 mg, 27.7 µmol, 14% yield, 99.6% purity) was obtained as a yellow gum. LCMS [ESI, M+1]: 628.

$^1$H NMR (400 MHz, chloroform-d) δ=7.73-7.62 (m, 2H), 7.45-7.32 (m, 2H), 7.27-7.17 (m, 2H), 7.08-6.93 (m, 1H), 6.60 (br d, J=16.0 Hz, 1H), 5.26-4.54 (m, 3H), 4.40 (m, 1H), 4.31-3.69 (m, 7H), 3.61-3.36 (m, 3H), 3.30 (d, J=2.0 Hz, 3H), 3.24-2.96 (m, 4H), 2.92 (s, 3H), 2.91-2.55 (m, 4H), 2.47 (d, J=4.8 Hz, 3H), 2.37-2.26 (m, 1H), 2.13-2.03 (m, 1H), 2.01-1.89 (m, 1H).

Example 581

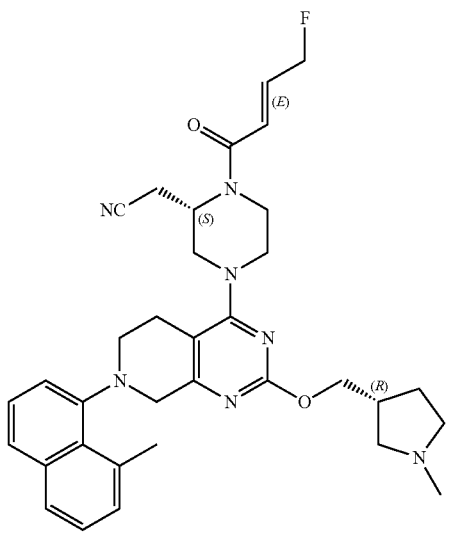

2-[(2S)-1-[(E)-4-fluorobut-2-enoyl]-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile

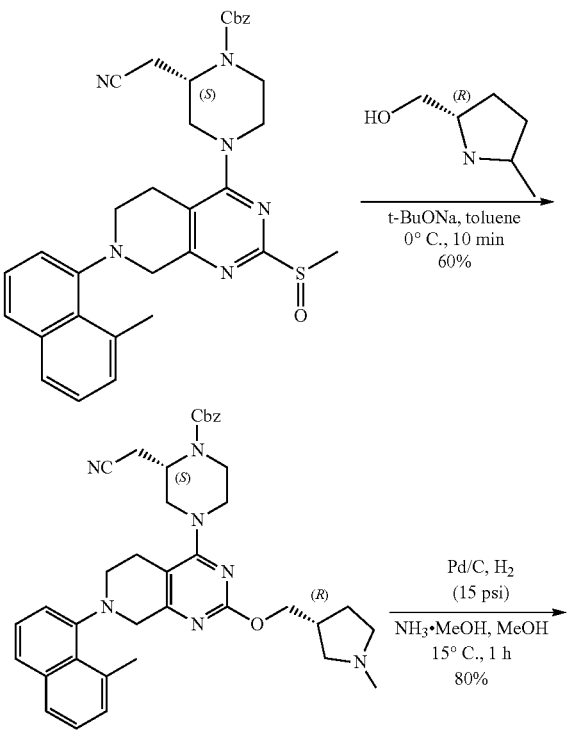

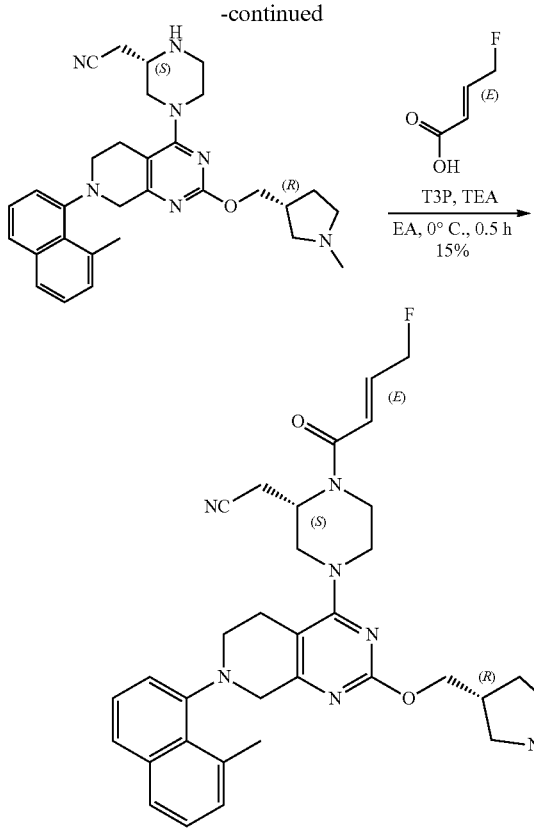

Step A: Benzyl (2S)-2-(cyanomethyl)-4-[7-(8-methyl-1-naphthyl)-2-[[(3R)-1-methylpyrrolidin-3-yl] methoxy]-6,8-dihydro-5H-pyrido[3,4-d]pyrimidin-4-yl]piperazine-1-carboxylate To a solution of benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (450 mg, 757 umol, 1 eq) and [(3R)-1-methylpyrrolidin-3-yl]methanol (131 mg, 1.13 mmol, 1.5 eq) in toluene (9 mL) was added t-BuONa (145 mg, 1.51 mmol, 2 eq). The mixture was stirred at 0° C. for 10 minutes. Upon completion, water was added (15 mL) and the resulting mixture extracted with ethyl acetate (30 mL×2). The organic layers were dried over $Na_2SO_4$, filtered and concentrated under vacuum. The residue was purified by reverse phase flash [water (0.1% FA)/acetonitrile]. The desired fractions were collected and neutralized with $NaHCO_3$, concentrated under vacuum to remove MeCN and extracted with EtOAc (2×50 mL). The organic layers were dried over $Na_2SO_4$ and concentrated under vacuum to give benzyl (2S)-2-(cyanomethyl)-4-[7-(8-methyl-1-naphthyl)-2-[[(3R)-1-methylpyrrolidin-3-yl] methoxy]-6, 8-dihydro-5H-pyrido[3,4-d]pyrimidin-4-yl] piperazine-1-carboxylate (300 mg, 455 μmol, 60% yield, 98% purity) as a pink solid.

$^1$H NMR (400 MHz, chloroform-d) δ=7.73-7.60 (m, 2H), 7.45-7.37 (m, 5H), 7.37-7.30 (m, 2H), 7.26-7.16 (m, 2H), 5.21 (s, 2H), 4.68 (br s, 1H), 4.30-3.78 (m, 7H), 3.59-3.29 (m, 2H), 3.25-2.94 (m, 4H), 2.91 (s, 3H), 2.82-2.62 (m, 4H), 2.62-2.53 (m, 2H), 2.53-2.42 (m, 2H), 2.35 (s, 3H), 2.05 (s, 1H), 1.66-1.51 (m, 1H).

Step B: 2-[(2S)-4-[7-(8-Methyl-1-naphthyl)-2-[[(3R)-1-methyl pyrrolidin-3-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazine-1-carboxylate (300 mg, 465 μmol, 1 eq) in MeOH (4 mL) was added Pd/C (150 mg, 10% purity), $NH_3$/MeOH (4 mL, 20% purity) under $N_2$. The suspension was degassed under vacuum and purged with $H_2$ several times. The mixture was stirred under $H_2$ (15 psi) at 15° C. for 1 hour. Upon completion, the mixture was filtered and the filtrate was concentrated under vacuum to give 2-[(2S)-4-[7-(8-methyl-1-naphthyl)-2-[[(3R)-1-methyl pyrrolidin-3-yl]methoxy]-6,8-dihydro-5H-pyrido[3,4-d]pyrimidin-4-yl]piperazin-2-yl] acetonitrile (210 mg, 369 μmol, 80% yield, 90% purity) as a pink solid which was used directly in the next step without further purification. LCMS [ESI, M+1]: 512.

Step C: 2-[(2S)-1-[(E)-4-Fluorobut-2-enoyl]-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (70 mg, 137 μmol, 1 eq), TEA (41.5 mg, 410 μmol, 57.1 μL, 3 eq) and (E)-4-fluorobut-2-enoic acid (28.5 mg, 274 μmol, 2 eq) in EtOAc (2 mL) was added T3P (131 mg, 205 μmol, 122 μL, 50% purity in EtOAc, 1.5 eq) at 0° C. The mixture was stirred at 0° C. for 0.5 hour. Upon completion, the reaction mixture was quenched with 1 M HCl (0.4 mL) at −40° C. and stirred until no ice remained. The separated aqueous layer was concentrated under vacuum. The residue was purified by prep-HPLC (column: Phenomenex Synergi C18 150*30 mm*4 μm; mobile phase: [water (0.225% FA)-MeCN]; B %: 20%-50%, 10 min). The desired fractions were collected and lyophilized to give title compound 2-[(2S)-1-[(E)-4-fluorobut-2-enoyl]-4-[7-(8-methyl-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (13.7 mg, 20.8 μmol, 15% yield, 97.7% purity, FA) as a gray solid. LCMS [ESI, M+1]: 598.

$^1$H NMR (400 MHz, chloroform-d) δ=7.66-7.59 (m, 1H), 7.59-7.51 (m, 1H), 7.32 (td, J=7.6, 11.6 Hz, 1H), 7.26 (t, J=7.6 Hz, 1H), 7.19-7.07 (m, 2H), 7.00-6.83 (m, 1H), 6.52 (br d, J=14.8 Hz, 1H), 5.21-4.31 (m, 3H), 4.29-3.96 (m, 3H), 3.94-3.53 (m, 7H), 3.45 (br d, J=6.8 Hz, 4H), 3.15-2.88 (m, 7H), 2.84 (s, 3H), 2.81-2.74 (m, 1H), 2.61-2.47 (m, 2H), 2.18 (br s, 1H), 1.85 (br s, 1H).

Example 582

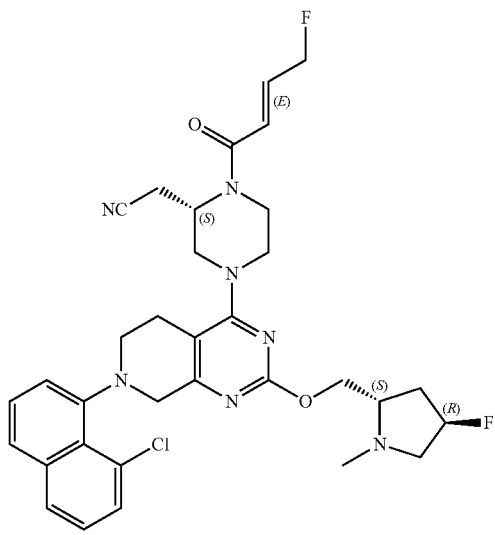

2-((S)-4-(7-(8-Chloronaphthalen-1-yl)-2-(((2S,4R)-4-fluoro-1-methylpyrrolidin-2-yl)methoxy)-5,6,7,8-tetrahydropyrido[3,4-d]pyrimidin-4-yl)-1-((E)-4-fluorobut-2-enoyl)piperazin-2-yl)acetonitrile

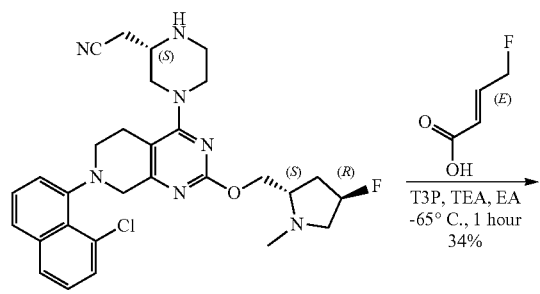

2-((S)-4-(7-(8-Chloronaphthalen-1-yl)-2-(((2S,4R)-4-fluoro-1-methylpyrrolidin-2-yl)methoxy)-5,6,7,8-tetrahydropyrido[3,4-d]pyrimidin-4-yl)-1-((E)-4-fluorobut-2-enoyl)piperazin-2-yl)acetonitrile To a solution of 2-[(2S)-4-[7-(8-chloro-1-naphthyl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile (180 mg, 327 µmol, 1.0 eq) and (E)-4-fluorobut-2-enoic acid (102 mg, 982 µmol, 3.0 eq) was added TEA (265 mg, 2.62 mmol, 364 µL, 8.0 eq) and T3P (833 mg, 1.31 mmol, 778 µL, 50% purity, 4.0 eq), the reaction mixture was stirred at −65° C. for 1 hour. After completion, the reaction mixture was quenched with 2 N HCl to pH ~7 at −65° C., then the organic layer was separated, the aqueous phase was extracted with ethyl acetate (2×10 mL), the combined organic layer was dried over Na$_2$SO$_4$, filtered and concentrated. The residue was purified column chromatography (basic Al$_2$O$_3$, petroleum ether/ethyl acetate=3/1 to ethyl acetate/methanol=20/1), the crude product was re-purified by prep-HPLC (column: Xtimate C18 150*25 mm*5 µm; mobile phase: [water (0.05% ammonium hydroxide v/v)-MeCN]; B %: 50%-80%, 8 min), the obtained product was concentrated, and lyophilized. Title compound 2-((S)-4-(7-(8-chloronaphthalen-1-yl)-2-(((2S,4R)-4-fluoro-1-methyl-pyrrolidin-2-yl)methoxy)-5,6,7,8-tetrahydropyrido[3,4-d]pyrimidin-4-yl)-1-((E)-4-fluorobut-2-enoyl)piperazin-2-yl) acetonitrile (72.2 mg, 113 µmol, 34% yield, 99% purity) was obtained as white solid. LCMS [ESI, M+1]: 637.

$^1$H NMR (400 MHz, chloroform-d) δ 7.79-7.73 (m, 1H), 7.62 (t, J=7.0 Hz, 1H), 7.53 (d, J=7.2 Hz, 1H), 7.49-7.41 (m, 1H), 7.34 (t, J=7.6 Hz, 1H), 7.27-7.18 (m, 1H), 7.08-6.93 (m, 1H), 6.59 (br d, J=14.8 Hz, 1H), 5.29-5.03 (m, 3H), 4.54-4.52 (m, 1H), 4.50-4.35 (m, 2H), 4.30-3.78 (m, 5H), 3.76-3.35 (m, 3H), 3.32-2.96 (m, 5H), 2.91-2.54 (m, 4H), 2.51 (d, J=3.2 Hz, 3H), 2.39-2.23 (m, 1H), 2.08-1.86 (m, 1H).

Example 583

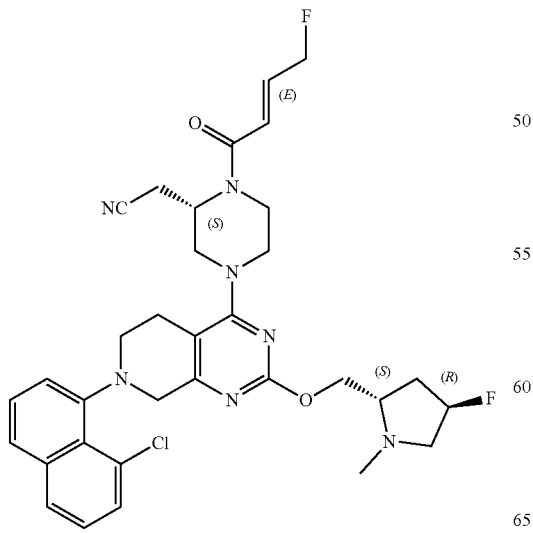

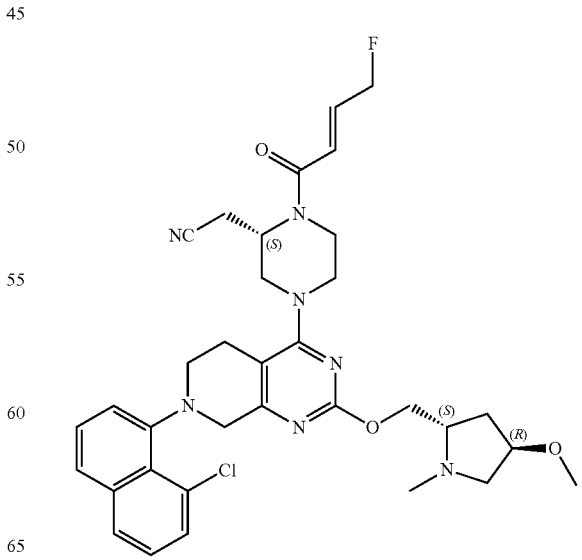

1511

2-[(2S)-4-[7-(8-chloro-1-naphthyl)-2-[[(2S,4R)-4-methoxy-1-methyl-pyrrolidin-2-yl] methoxy]-6,8-dihydro-5H-pyrido[3,4-d]pyrimidin-4-yl]-1-[(E)-4-fluorobut-2-enoyl]piperazin-2-yl]acetonitrile

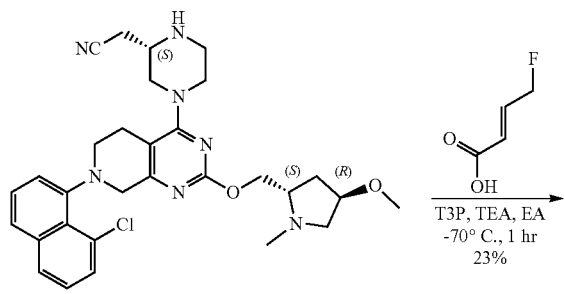

2-[(2S)-4-[7-(8-Chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile To a solution of 2-[(2S)-4-[7-(8-chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]piperazin-2-yl]acetonitrile (150 mg, 267 μmol, 1.0 eq), (E)-4-fluorobut-2-enoic acid (55.6 mg, 534 μmol, 2.0 eq) and TEA (108 mg, 1.07 mmol, 149 μL, 4.0 eq) in ethyl acetate (4.0 mL) was added T3P (340 mg, 534 μmol, 317 μL, 50% purity, 2.0 eq). The mixture was stirred at −70° C. for 1 hour. After completion, the reaction mixture was quenched with HCl (12 M, 60.0 μL in 2.0 mL of water). The mixture was adjusted to pH ~8 with saturated NaHCO3 aqueous solution and extracted with ethyl acetate (3×20.0 mL). The combined organic layers were washed with saturated brine (60.0 mL), dried over Na2SO4, filtered and concentrated. The residue was purified by prep-HPLC (column: Xtimate C18 150*25 mm*5 um; mobile phase: [water (0.05% ammonium hydroxide v/v)-MeCN]; B %: 50%-80%, 8 min) to give title compound 2-[(2S)-4-[7-(8-chloro-1-naphthyl)-2-[[(2S,4R)-4-methoxy-1-methyl-pyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile (39.6 mg, 60.9 μmol, 23% yield, 99% purity) as white solid. LCMS [ESI, M+1]: 619.

$^1$H NMR (400 MHz, Chloroform-d) δ 7.76 (br d, J=8.0 Hz, 1H), 7.62 (t, J=7.6 Hz, 1H), 7.53 (d, J=7.6 Hz, 1H), 7.49-7.40 (m, 1H), 7.34 (t, J=8.0 Hz, 1H), 7.27-7.17 (m, 1H), 7.08-6.94 (m, 1H), 6.67-6.54 (m, 1H), 5.25-5.03 (m, 2H), 4.80-4.60 (m, 1H), 4.48-4.34 (m, 2H), 4.21-3.77 (m, 5H), 3.65-3.55 (m, 1H), 3.51-3.37 (m, 1H), 3.31-2.97 (m, 5H), 2.88-2.54 (m, 4H), 2.48 (d, J=3.6 Hz, 3H), 2.34-2.24 (m, 1H), 2.11-2.01 (m, 1H), 1.90-1.69 (m, 3H).

Example 584

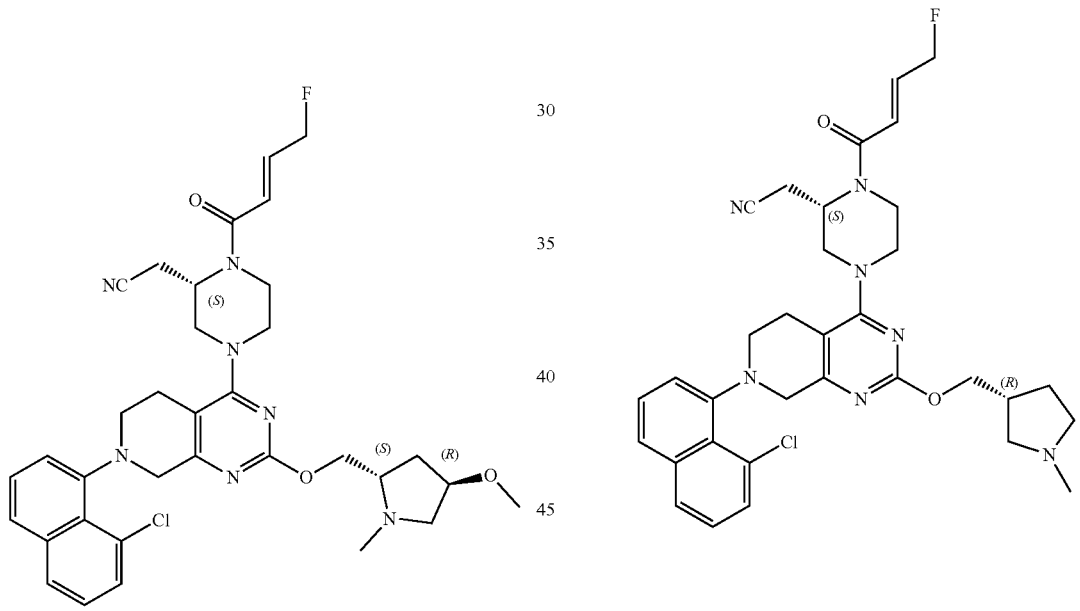

2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-1-[(E)-4-fluorobut-2-enoyl]piperazin-2-yl]acetonitrile

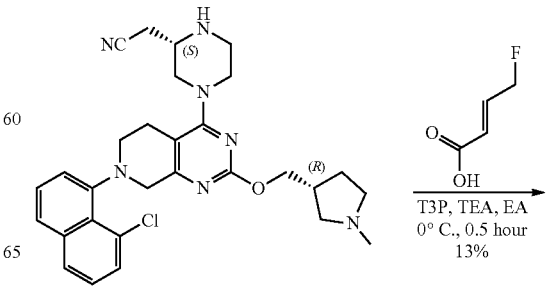

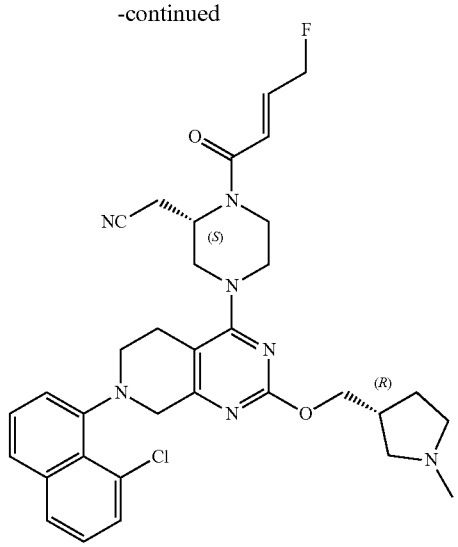

2-[(2S)-4-[7-(8-Chloro-1-naphthyl)-2-[[(3R)-1-methylpyrrolidin-3-yl]methoxy]-6,8-dihydro-5H-pyrido[3,4-d]pyrimidin-4-yl]-1-[(E)-4-fluorobut-2-enoyl]piperazin-2-yl]acetonitrile To a solution of 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]piperazin-2-yl]acetonitrile (100 mg, 188 μmol, 1.0 eq), (E)-4-fluorobut-2-enoic acid (39.1 mg, 376 μmol, 2.0 eq) and TEA (95.1 mg, 940 μmol, 131 μL, 5.0 eq) in ethyl acetate (3.0 mL) was added T3P (179 mg, 282 μmol, 168 μL, 50% purity, 1.50 eq). The mixture was stirred at 0° C. for 0.5 hour. After completion, the reaction mixture was quenched with HCl (12 M, 5.0 eq) at −40° C. The mixture was adjusted to pH ~8 with saturated aqueous NaHCO₃ and extracted with ethyl acetate (3×10.0 mL). The combined organic layers were washed with brine (30.0 mL), dried over Na₂SO₄, filtered and concentrated. The residue was purified by prep-HPLC (column: Phenomenex Synergi C18 150*25*10 μm; mobile phase: [water (0.225% FA)-MeCN]; B %: 30%-50%, 8 min) to give the title compound 2-[(2S)-4-[7-(8-chloro-1-naphthyl)-2-[[(3R)-1-methylpyrrolidin-3-yl]methoxy]-6,8-dihydro-5H-pyrido[3,4-d]pyrimidin-4-yl]-1-[(E)-4-fluorobut-2-enoyl]piperazin-2-yl]acetonitrile (15.7 mg, 24.9 μmol, 13% yield, 98% purity) as a yellow solid. LCMS [ESI, M+1]: 619.

¹H NMR (400 MHz, Chloroform-d) δ 7.76 (d, J=8.4 Hz, 1H), 7.65-7.59 (m, 1H), 7.56-7.49 (m, 1H), 7.48-7.40 (m, 1H), 7.34 (t, J=7.6 Hz, 1H), 7.26-7.18 (m, 1H), 7.08-6.92 (m, 1H), 6.74-6.46 (m, 1H), 5.25-4.95 (m, 3H), 4.75-4.55 (m, 1H), 4.47-4.36 (m, 1H), 4.35-4.26 (m, 2H), 4.14-3.92 (m, 2H), 3.91-3.76 (m, 1H), 3.64-3.55 (m, 1H), 3.53-3.35 (m, 1H), 3.33-3.04 (m, 7H), 3.03-2.72 (m, 4H), 2.67 (d, J=4.0 Hz, 3H), 2.64-2.51 (m, 1H), 2.31-2.19 (m, 1H), 1.98-1.85 (m, 1H).

Example 585

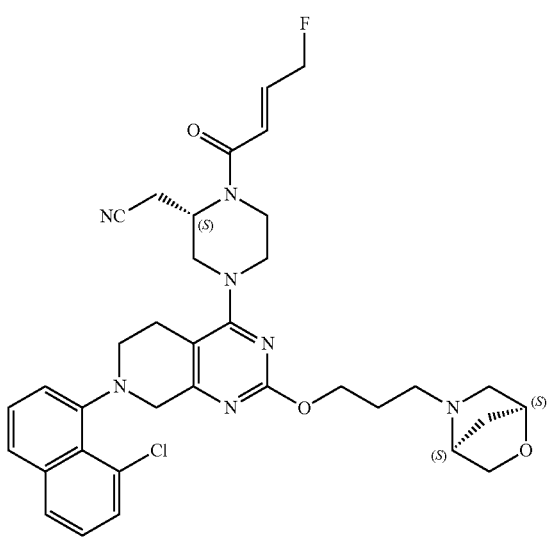

2-((S)-4-(2-(3-(((1S,4S)-2-oxa-5-azabicyclo[2.2.1]heptan-5-yl)propoxy)-7-(8-chloronaphthalen-1-yl)-5,6,7,8-tetrahydropyrido[3,4-d]pyrimidin-4-yl)-1-((E)-4-fluorobut-2-enoyl)piperazin-2-yl)acetonitrile

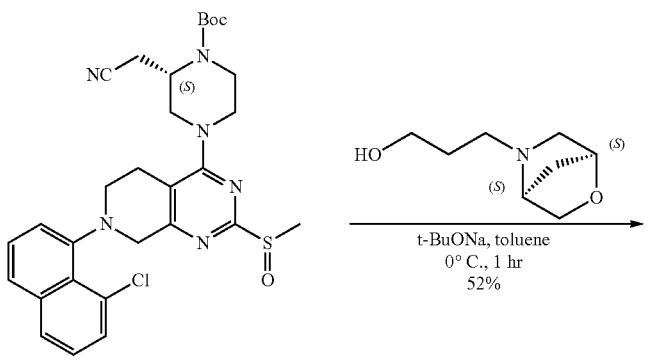

-continued

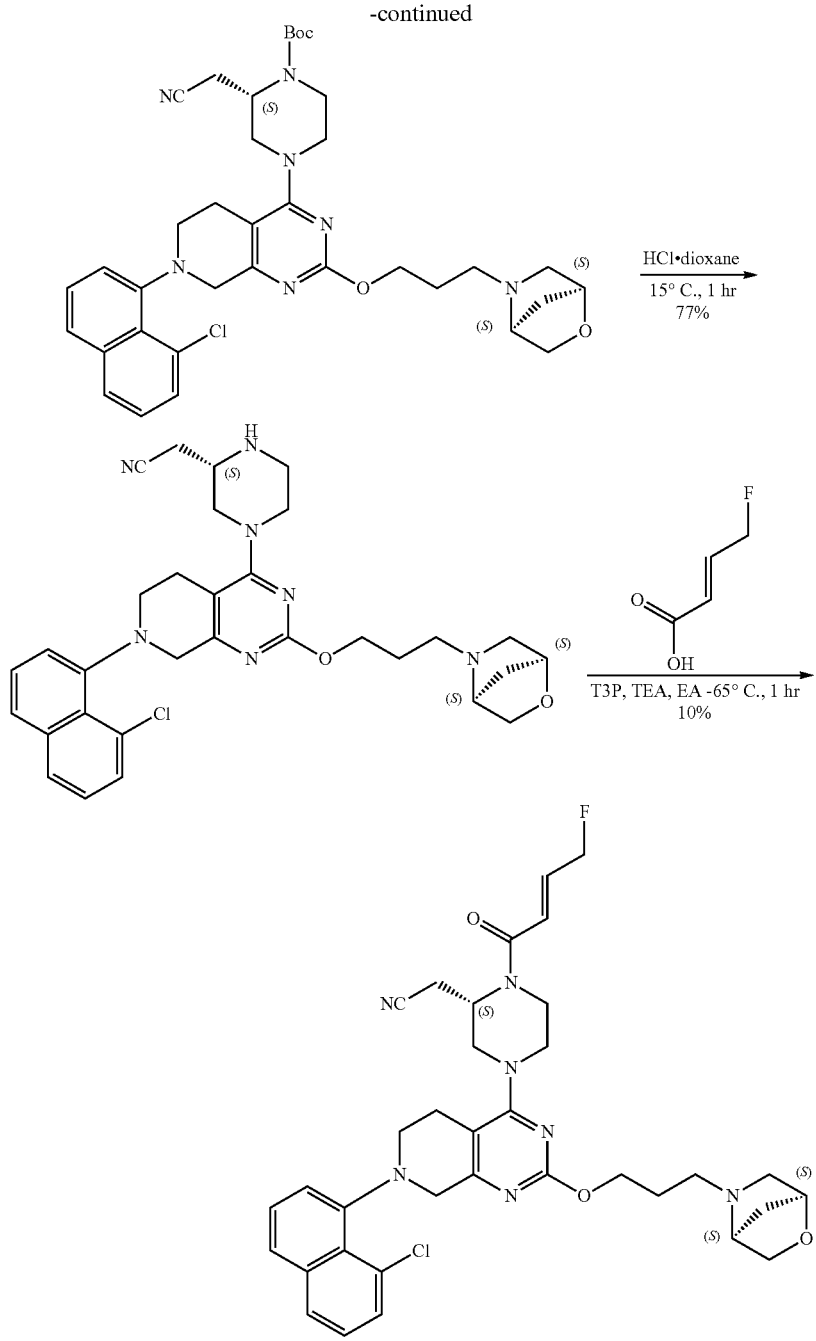

Step A: tert-Butyl (2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-2-(cyanomethyl)piperazine-1-carboxylate To a mixture of 3-[(1S,4S)-2-oxa-5-azabicyclo[2.2.1]heptan-5-yl]propan-1-ol (150 mg, 954 µmol, 1.85 eq) in toluene (3.0 mL) was added t-BuONa (99.2 mg, 1.03 mmol, 2.0 eq) in portions at 0° C., after stirring at 0° C. for 0.5 hour, tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (300 mg, 516 µmol, 1.0 eq) was added to the mixture, and stirred at 0° C. for 0.5 hour. After completion, water was added (15 mL), and the resulting mixture extracted with ethyl acetate (2×10 mL), the combined organic layer was dried over $Na_2SO_4$, filtered and concentrated. The residue was purified by reverse phase flash (C18, 0.1% TFA in water, 30%-50% MeCN), the obtained product was adjusted with $NaHCO_3$ solid to pH ~8, then concentrated, the aqueous phase was extracted with ethyl acetate (2×15 mL), the organic layer was washed with saturated brine (1×20 mL), dried over $Na_2SO_4$, filtered and concentrated. The product tert-butyl (2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-2-(cyanomethyl)piperazine-1-carboxylate (180 mg, 267 µmol, 52% yield, 100% purity) was obtained as light yellow solid. LCMS [ESI, M+1]: 674.

¹H NMR (400 MHz, chloroform-d) δ 7.76 (br d, J=8.4 Hz, 1H), 7.61 (t, J=7.6 Hz, 1H), 7.52 (d, J=7.2 Hz, 1H), 7.48-7.40 (m, 1H), 7.34 (t, J=7.8 Hz, 1H), 7.26-7.17 (m, 1H), 4.66-4.54 (m, 1H), 4.50-4.29 (m, 4H), 4.08-3.77 (m, 5H), 3.65-3.54 (m, 2H), 3.51-3.44 (m, 1H), 3.39-3.31 (m, 1H), 3.29-3.02 (m, 4H), 3.00-2.87 (m, 2H), 2.84-2.46 (m, 6H), 1.99-1.82 (m, 3H), 1.52 (s, 9H).

Step B: 2-[(2S)-4-[7-(8-Chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]-2-(cyanomethyl)piperazine-1-carboxylate (150 mg, 222 μmol, 1.0 eq) in dioxane (1.0 mL) was added 4 N HCl.dioxane (1.0 mL), the reaction mixture was stirred at 15° C. for 1 hour. After completion, the reaction mixture was concentrated, added dichloromethane (10 mL), then washed with saturated aqueous Na₂CO₃ (1×10 mL), the organic layer was dried over Na₂SO₄, filtered and concentrated. The product 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (100 mg, 172 μmol, 77% yield, 98% purity) was obtained as brown oil. LCMS [ESI, M+1]: 574.

Step C: 2-((S)-4-(2-(3-((1S,4S)-2-Oxa-5-azabicyclo[2.2.1]heptan-5-yl)propoxy)-7-(8-chloronaphthalen-1-yl)-5,6,7,8-tetrahydropyrido[3,4-d]pyrimidin-4-yl)-1-((E)-4-fluorobut-2-enoyl)piperazin-2-yl)acetonitrile To a solution of 2-[(2S)-4-[7-(8-chloro-1-naphthyl)-2-[3-[(1S,4S)-2-oxa-5-azabicyclo[2.2.1]heptan-5-yl]propoxy]-6,8-dihydro-5H-pyrido[3,4-d]pyrimidin-4-yl]piperazin-2-yl]acetonitrile (90.0 mg, 157 μmol, 1.0 eq) and (E)-4-fluorobut-2-enoic acid (48.9 mg, 470 μmol, 3.0 eq) in ethyl acetate (1.0 mL) was added TEA (127 mg, 1.25 mmol, 175 μL, 8.0 eq) and T3P (399 mg, 627 μmol, 373 μL, 50% purity, 4.0 eq) in portions at −65° C., the reaction mixture was stirred at −65° C. for 1 hour. After completion, the reaction mixture was quenched with 2 N HCl to pH ~7 at −65° C., then the organic layer was separated, the aqueous phase was extracted with ethyl acetate (2×10 mL), the combined organic layer was dried over Na₂SO₄, filtered and concentrated. The residue was purified column chromatography (basic Al₂O₃, petroleum ether/ethyl acetate=3/1 to ethyl acetate/methanol=20/1), the crude product was re-purified by prep-HPLC (column: Xtimate C18 150*25 mm*5 μm; mobile phase: [water (0.05% ammonium hydroxide v/v)-MeCN]; B %: 44%-74%, 8 min), the obtained product was concentrated, and lyophilized. Title compound 2-((S)-4-(2-(3-((1S,4S)-2-oxa-5-azabicyclo[2.2.1]heptan-5-yl)propoxy)-7-(8-chloronaphthalen-1-yl)-5,6,7,8-tetrahydropyrido[3,4-d]pyrimidin-4-yl)-1-((E)-4-fluorobut-2-enoyl)piperazin-2-yl)acetonitrile (10.6 mg, 16.0 μmol, 10% yield, 99% purity) was obtained as white solid. LCMS [ESI, M+1]: 660.

¹H NMR (400 MHz, chloroform-d) δ 7.76 (br d, J=8.4 Hz, 1H), 7.62 (t, J=7.4 Hz, 1H), 7.53 (d, J=7.2 Hz, 1H), 7.49-7.41 (m, 1H), 7.34 (t, J=7.8 Hz, 1H), 7.26-7.18 (m, 1H), 7.09-6.93 (m, 1H), 6.60 (br d, J=14.0 Hz, 1H), 5.26-5.01 (m, 2H), 4.76-7.54 (m, 1H), 4.52-4.29 (m, 4H), 4.19-3.97 (m, 3H), 3.95-3.69 (m, 2H), 3.66-3.37 (m, 4H), 3.33-2.99 (m, 4H), 2.97-2.67 (m, 5H), 2.65-2.48 (m, 2H), 2.01-1.90 (m, 2H), 1.90-1.82 (m, 1H), 1.76-1.69 (m, 1H).

Example 586

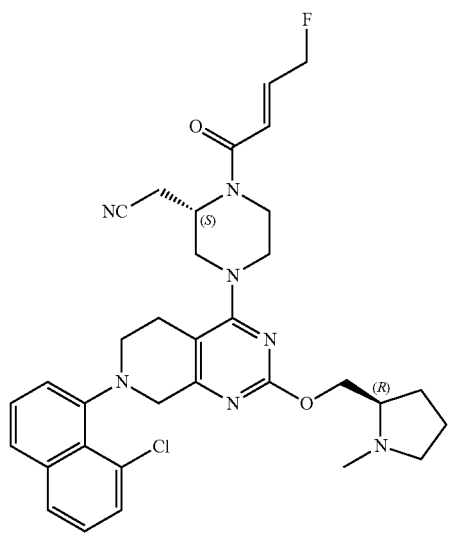

2-[(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile

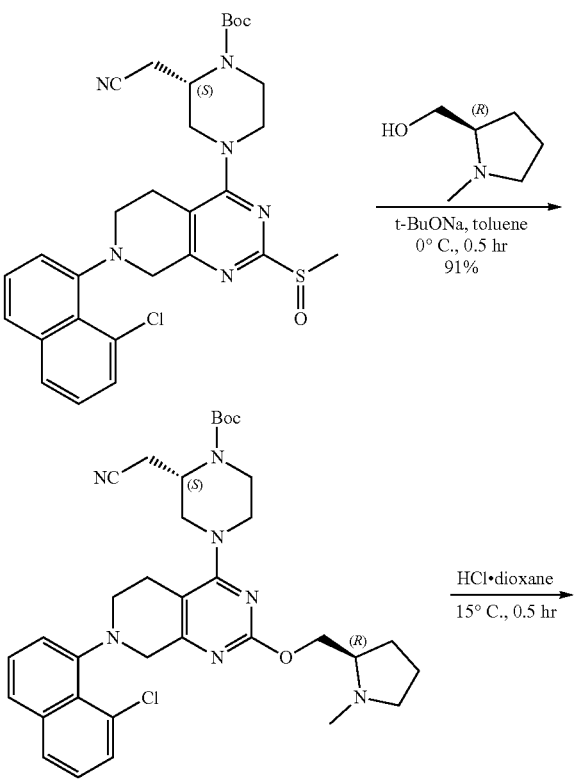

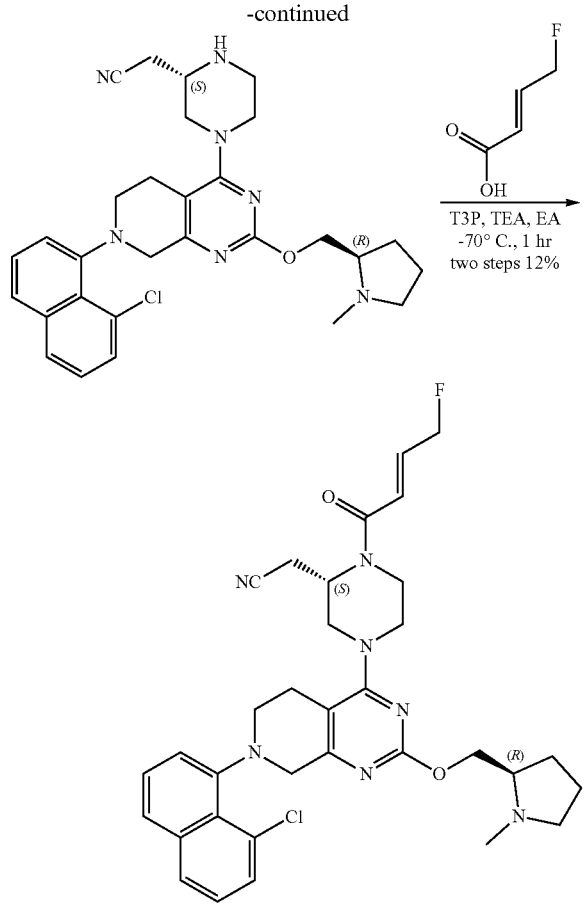

Step A: tert-Butyl (2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate To a solution of [(2R)-1-methylpyrrolidin-2-yl]methanol (99.1 mg, 860 μmol, 2.50 eq) in toluene (5.0 mL) was added t-BuONa (66.2 mg, 688 μmol, 2.0 eq) and tert-butyl (2S)-4-[7-(8-chloro-1-naphthyl)-2-methylsulfinyl-6,8-dihydro-5H-pyrido[3,4-d]pyrimidin-4-yl]-2-(cyanomethyl)piperazine-1-carboxylate (200 mg, 344 μmol, 1.0 eq) in portions. The mixture was stirred at 0° C. for 0.5 hour. After completion, water was added (20.0 mL) and the resulting mixture extracted with ethyl acetate (3×10.0 mL). The organic layer was dried over Na$_2$SO$_4$, filtered and concentrated. The residue was purified by reverse phase flash (C18, 0.1% FA in water, 0-60% MeCN) to give the compound tert-butyl (2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate (200 mg, 313 μmol, 91% yield, 99% purity) as yellow solid. LCMS [ESI, M+1]: 632.

$^1$H NMR (400 MHz, Chloroform-d) δ 7.77-7.73 (m, 1H), 7.61 (t, J=7.6 Hz, 1H), 7.54-7.50 (m, 1H), 7.49-7.39 (m, 1H), 7.33 (t, J=7.6 Hz, 1H), 7.27-7.16 (m, 1H), 4.67-4.56 (m, 1H), 4.47-4.35 (m, 2H), 4.23-4.15 (m, 1H), 4.09-3.89 (m, 3H), 3.88-3.77 (m, 1H), 3.63-3.53 (m, 1H), 3.41-3.30 (m, 1H), 3.22-3.03 (m, 4H), 3.01-2.85 (m, 1H), 2.74-2.67 (m, 2H), 2.63-2.51 (m, 2H), 2.49 (d, J=4.4 Hz, 3H), 2.36-2.25 (m, 1H), 2.11-2.05 (m, 1H), 1.90-1.74 (m, 3H), 1.52 (s, 9H).

Step B: 2-[(2S)-4-[7-(8-Chloro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-2-(cyanomethyl)piperazine-1-carboxylate (200 mg, 316 μmol, 1.0 eq) in dioxane (3.0 mL) was added HCl.dioxane (4.0 M, 3.0 mL, 37.9 eq). The mixture was stirred at 15° C. for 0.5 hour. After completion, the reaction mixture was concentrated. The residue was adjusted with saturated aqueous NaHCO$_3$ (10.0 mL) to pH ~7, and then extracted with ethyl acetate (3×10.0 mL). The organic layer was dried over Na$_2$SO$_4$, filtered and concentrated to give the compound 2-[(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (150 mg, crude) as yellow solid. The product was used for the next step without further purification. LCMS [ESI, M+1]: 532.

Step C: 2-[(2S)-4-[7-(8-Chloro-1-naphthyl)-2-[[(2R)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile To a solution of 2-[(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (100 mg, 188 μmol, 1.0 eq) and (E)-4-fluorobut-2-enoic acid (39.1 mg, 376 μmol, 2.0 eq) in ethyl acetate (2.0 mL) was added TEA (76.1 mg, 752 μmol, 105 μL, 4.0 eq) and T3P (239 mg, 376 μmol, 224 μL, 50% purity, 2.0 eq) at −70° C. The mixture was stirred at −70° C. for 1 hour. After completion, the reaction mixture was quenched with HCl (12.0 M, 60.0 in 2.0 mL of water). The mixture was adjusted to pH=8 with saturated aqueous NaHCO$_3$ and extracted with ethyl acetate (3×10.0 mL). The combined organic layers were washed with brine (30.0 mL), dried over Na$_2$SO$_4$, filtered and concentrated under reduced pressure to give the residue. The residue was purified by prep-HPLC (column: Xtimate C18 150*25 mm*5 μm; mobile phase: [water (0.05% ammonium hydroxide v/v)-MeCN]; B %: 598%-89%, 8 min) to give the title compound 2-[(2S)-4-[7-(8-chloro-1-naphthyl)-2-[[(2R)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile (13.97 mg, 22.2 μmol, 12% yield, 98.4% purity) as white solid. LCMS [ESI, M+1]: 619.

$^1$H NMR (400 MHz, Chloroform-d) δ 7.76 (br d, J=8.0 Hz, 1H), 7.62 (t, J=7.6 Hz, 1H), 7.53 (d, J=7.6 Hz, 1H), 7.49-7.40 (m, 1H), 7.34 (t, J=8.0 Hz, 1H), 7.27-7.17 (m, 1H), 7.08-6.94 (m, 1H), 6.67-6.54 (m, 1H), 5.25-5.03 (m, 2H), 4.80-4.60 (m, 1H), 4.48-4.34 (m, 2H), 4.21-3.77 (m, 5H), 3.65-3.55 (m, 1H), 3.51-3.37 (m, 1H), 3.31-2.97 (m, 5H), 2.88-2.54 (m, 4H), 2.48 (d, J=3.6 Hz, 3H), 2.34-2.24 (m, 1H), 2.11-2.01 (m, 1H), 1.90-1.69 (m, 3H).

Example 587

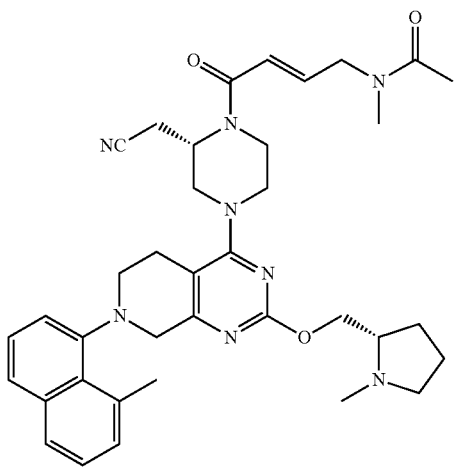 [SMILES: CC(=O)N(C)C/C=C/C(=O)N1CCN(c2nc(OC[C@@H]3CCCN3C)nc3c2CCN(c2cccc4cccc(C)c24)C3)C[C@@H]1CC#N]

N-((E)-4-((S)-2-(Cyanomethyl)-4-(7-(8-methylnaph-thalen-1-yl)-2-((S)-1-methylpyrrolidin-2-yl)methoxy)-5,6,7,8-tetrahydropyrido[3,4-d]pyrimidin-4-yl)piperazin-1-yl)-4-oxobut-2-en-1-yl)-N-methylacetamide

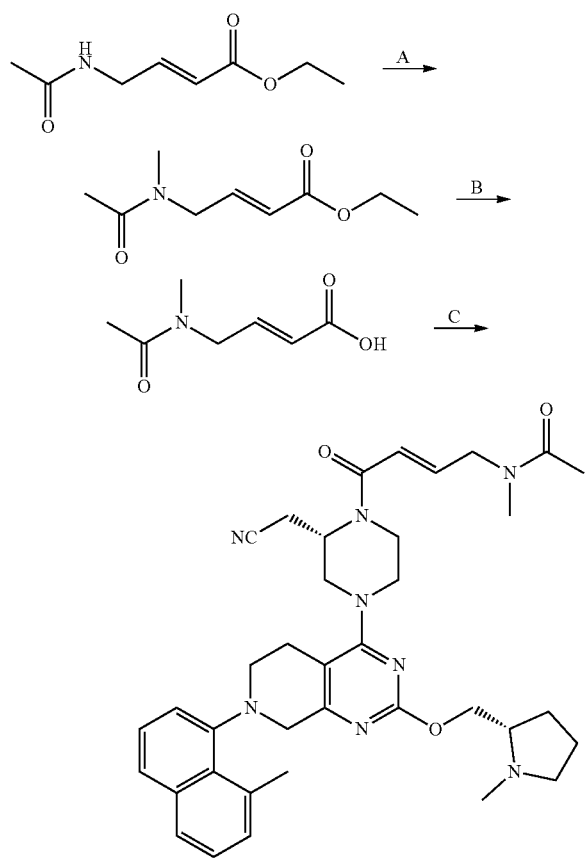

Step A: Ethyl (E)-4-(N-methylacetamido)but-2-enoate

Ethyl (E)-4-acetamidobut-2-enoate (140 mg, 0.818 mmol) was diluted with DMF (4 mL) followed by the addition of NaH (21.6 mg, 0.900 mmol) and MeI (56.2 µl, 0.900 mmol). After stirring for 12 hours, the reaction was diluted with ethyl acetate and saturated sodium bicarbonate. The layers were separated and the organic layer was dried over MgSO$_4$, filtered and concentrated. The material was purified on silica gel eluting with 10-70% ethyl acetate/hexanes to afford ethyl (E)-4-(N-methylacetamido)but-2-enoate (120 mg, 0.648 mmol, 79.2% yield).

Step B: (E)-4-(N-methylacetamido)but-2-enoic acid

Ethyl (E)-4-(N-methylacetamido)but-2-enoate (20 mg, 0.11 mmol) was diluted with methanol (1 mL) followed by the addition of NaOH (270 µl, 0.54 mmol). After stirring for 4 hours, the reaction was diluted with 2N HCl to pH ~4 and the aqueous layer extracted with ethyl acetate. The ethyl acetate was dried over MgSO$_4$, filtered and concentrated to afford (E)-4-(N-methylacetamido)but-2-enoic acid (15 mg, 0.095 mmol, 88% yield).

Step C: N-((E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-en-1-yl)-N-methylacetamide 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (20 mg, 0.039 mmol) was diluted with DMF followed by the addition of DIEA (13.65 µl, 0.07817 mmol). (E)-4-(N-methylacetamido)but-2-enoic acid (9.83 mg, 0.0625 mmol) was added followed by the addition of 1-Propanephosphonic acid cyclic anhydride (39.6 µl, 0.0664 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silica gel eluting with 10% methanol/DCM (1% NH$_4$OH) to afford N-((E)-4-((S)-2-(cyanomethyl)-4-(7-(8-methylnaphthalen-1-yl)-2-((S)-1-methylpyrrolidin-2-yl)methoxy)-5,6,7,8-tetrahydropyrido[3,4-d]pyrimidin-4-yl)piperazin-1-yl)-4-oxobut-2-en-1-yl)-N-methylacetamide (2.1 mg, 0.0032 mmol, 8.2% yield). ESI+APCI MS m/z 651.4 [M+H]$^+$.

Example 588

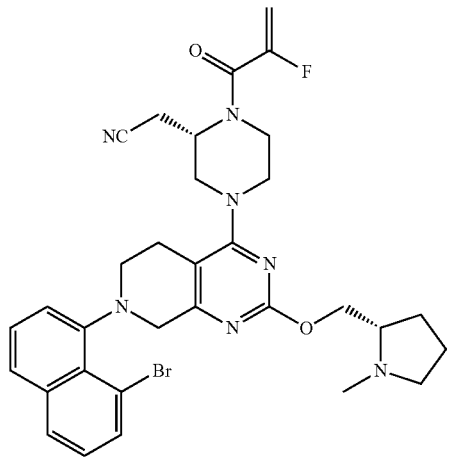 [SMILES: C=C(F)C(=O)N1CCN(c2nc(OC[C@@H]3CCCN3C)nc3c2CCN(c2cccc4cccc(Br)c24)C3)C[C@@H]1CC#N]

2-((S)-4-(7-(8-Bromonaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile

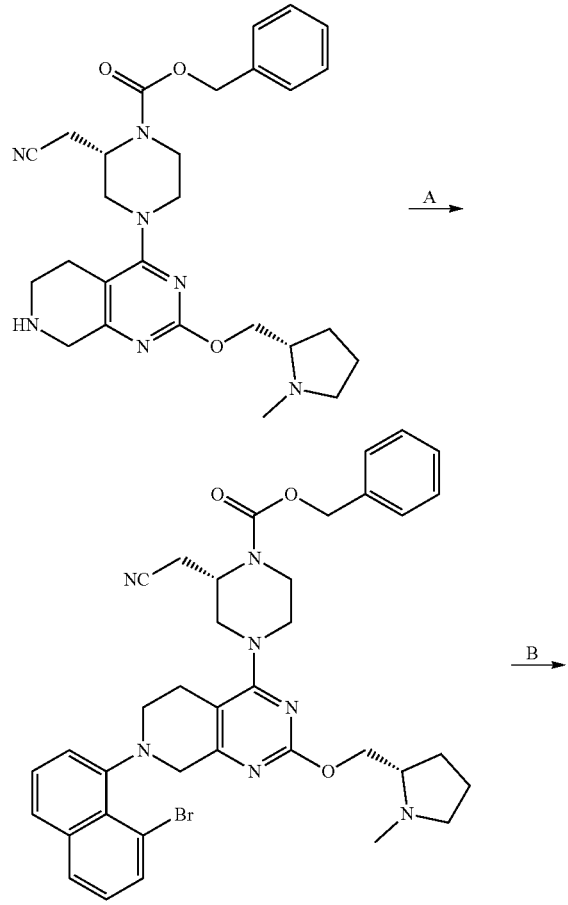

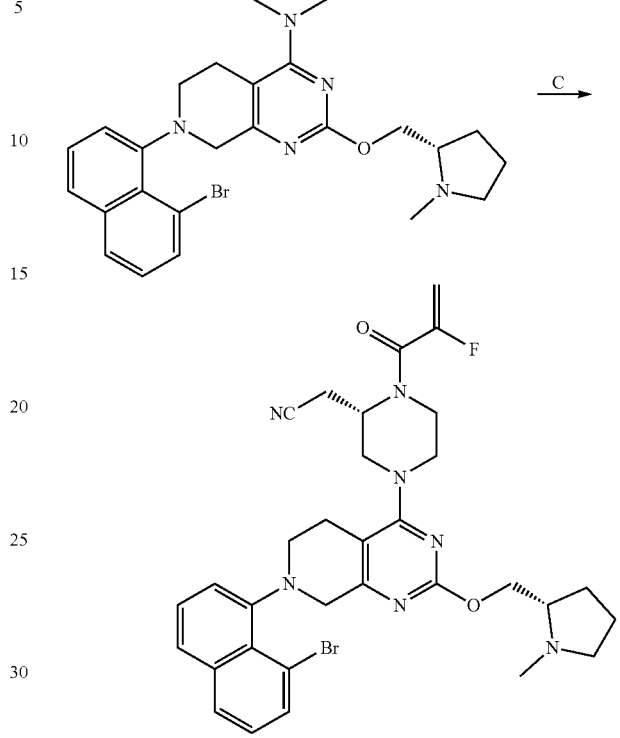

Step A: Benzyl (S)-4-(7-(8-bromonaphthalen-1-yl)-2-((S)-1-methylpyrrolidin-2-yl)methoxy)-5,6,7,8-tetrahydropyrido[3,4-d]pyrimidin-4-yl)-2-(cyanomethyl)piperazine-1-carboxylate Benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (140 mg, 0.277 mmol), 1,8-dibromonaphthalene (238 mg, 0.831 mmol), $Pd_2(dba)_3$ (25.4 mg, 0.0277 mmol), $Cs_2CO_3$ (451 mg, 1.38 mmol) and XANTPHOS (32.0 mg, 0.0554 mmol) were diluted with toluene (111 µl, 0.277 mmol). The reaction was purged with argon, sealed and heated to 110° C. while stirring for 12 hours. The reaction was allowed to cool and diluted with ethyl acetate and water. The layers were separated and the ethyl acetate was dried over $MgSO_4$, filtered and concentrated. The material was purified on silica gel eluting with 1-10% methanol/DCM (1% $NH_4OH$) to afford benzyl (S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (80 mg, 0.113 mmol, 40.7% yield).

Step B: 2-((S)-4-(7-(8-Bromonaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile Benzyl (S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (80 mg, 0.11 mmol) was diluted with TFA (2 mL),

1525 placed under nitrogen and heated to 90° C. After stirring for 2 hours, the reaction was cooled and concentrated. The material was diluted with DCM and washed with saturated sodium bicarbonate. The DCM was dried over $MgSO_4$, filtered and concentrated. The material was purified on silica gel eluting with 10% methanol/DCM (1% $NH_4OH$) to afford 2-((S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (23 mg, 0.040 mmol, 35% yield).

Step C: 2-((S)-4-(7-(8-Bromonaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile 2-((S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (23 mg, 0.040 mmol) was diluted with DMF (350 μL) followed by the addition of DIEA (22 μl, 0.13 mmol) and 2-fluoroacrylic acid (5.4 mg, 0.060 mmol). 2,4,6-tripropyl-1,3,5,2,4,6-trioxatriphosphinane 2,4,6-trioxide (25 mg, 0.040 mmol) was added and the reaction was stirred for 12 hours at room temperature. The reaction was diluted with ethyl acetate and saturated sodium bicarbonate. The layers were separated and the ethyl acetate was dried over $MgSO_4$, filtered and concentrated. The material was purified on silica gel eluting with 10% methanol/DCM (1% $NH_4OH$) to afford 2-((S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile (9 mg, 0.014 mmol, 35% yield). ESI+APCI MS m/z 650.2 $[M+H]^+$.

Example 589

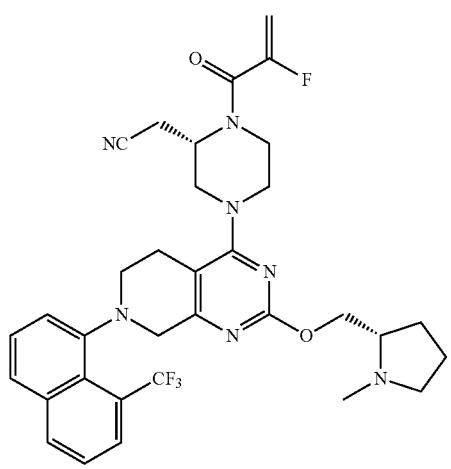 [SMILES: C=C(F)C(=O)N1CCN(c2nc(OC[C@@H]3CCCN3C)nc3c2CCN(c2cccc4cccc(C(F)(F)F)c24)C3)C[C@@H]1CC#N]

1526

2-((S)-1-(2-Fluoroacryloyl)-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazin-2-yl)acetonitrile

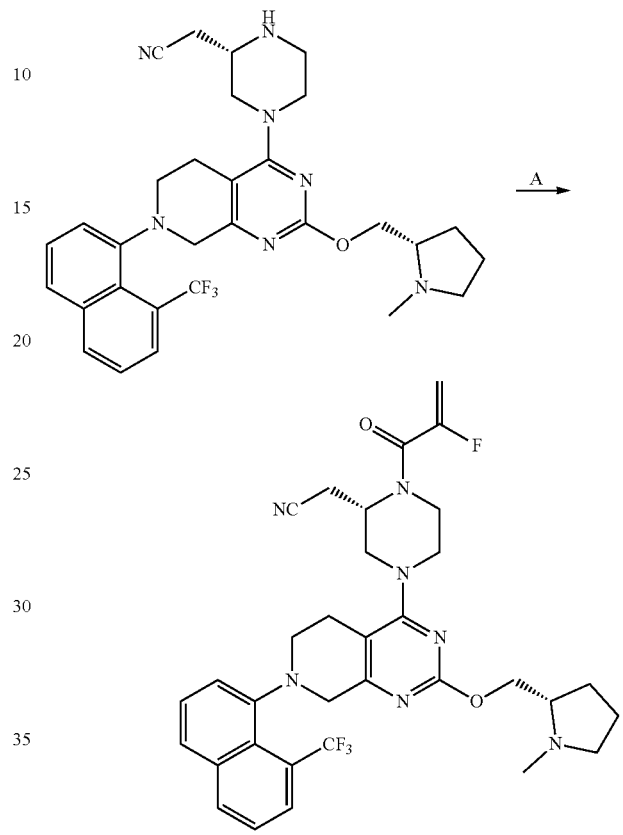

Step A: 2-((S)-1-(2-Fluoroacryloyl)-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazin-2-yl)acetonitrile 2-((S)-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazin-2-yl)acetonitrile (24 mg, 0.042 mmol) was diluted with DMF (400 DIEA (19 μl, 0.11 mmol) was added followed by the addition of 2-fluoroacrylic acid (6.1 mg, 0.068 mmol) and the addition of 2,4,6-tripropyl-1,3,5,2,4,6-trioxatriphosphinane 2,4,6-trioxide (30 μl, 0.047 mmol). The reaction was stirred at ambient temperature for 10 hours. The reaction was poured into a 5% sodium bicarbonate solution and extracted twice with ethyl acetate. The ethyl acetate was washed with water, brine, dried over $MgSO_4$, filtered and concentrated. The material was purified on silica gel eluting with 1-10% methanol/DCM (1% $NH_4OH$) to afford 2-((S)-1-(2-fluoroacryloyl)-4-(2-(((S)-1-methylpyrrolidin-2-yl)methoxy)-7-(8-(trifluoromethyl)naphthalen-1-yl)-5,6,7,8-tetrahydropyrido[3,4-d]pyrimidin-4-yl)piperazin-2-yl)acetonitrile (5 mg, 0.0078 mmol, 18% yield). ESI+APCI MS m/z 638.3 $[M+H]^+$.

Example 590

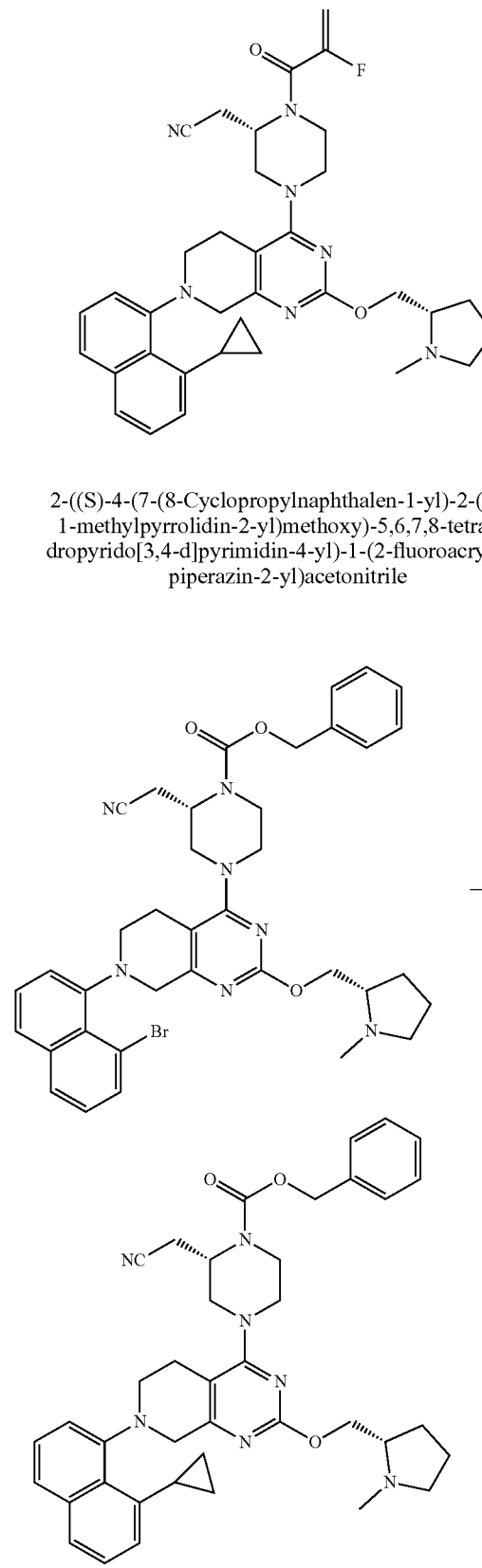

2-(((S)-4-(7-(8-Cyclopropylnaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile

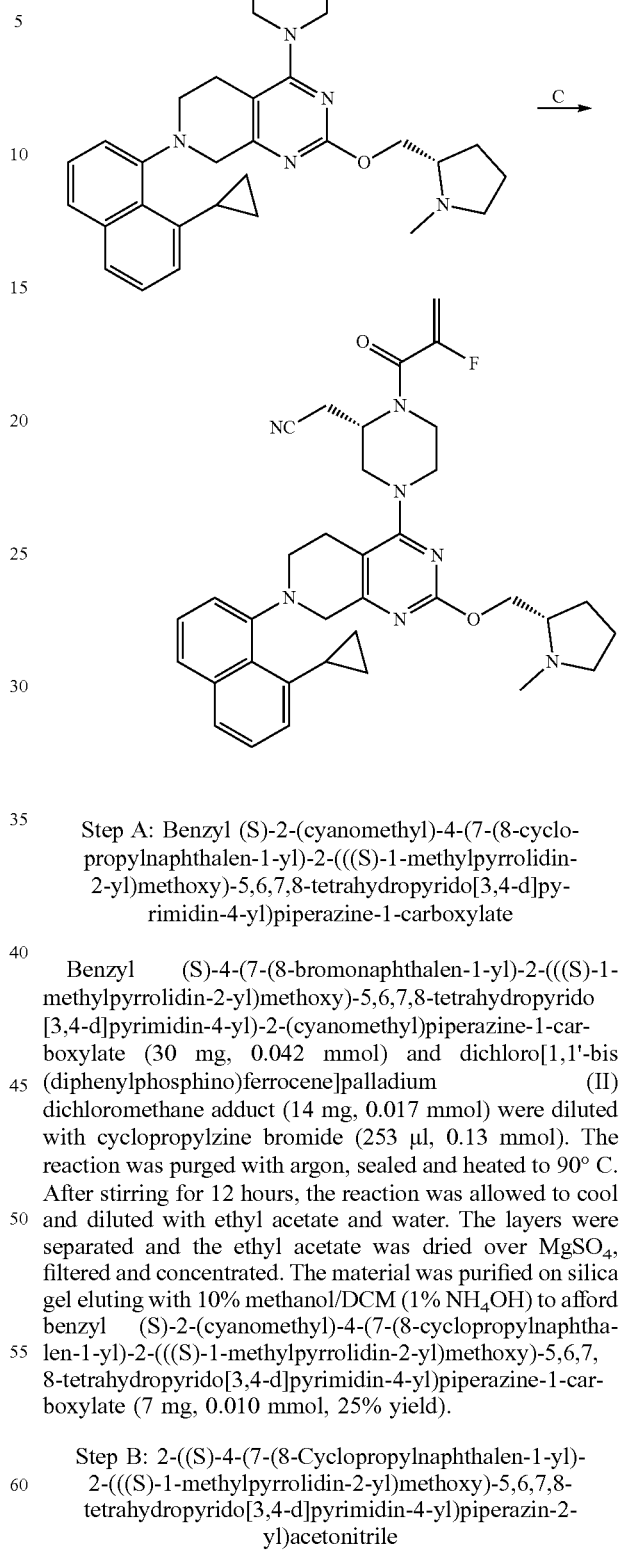

Step A: Benzyl (S)-2-(cyanomethyl)-4-(7-(8-cyclopropylnaphthalen-1-yl)-2-(((S)-1-methylpyrrolidin-2-yl)methoxy)-5,6,7,8-tetrahydropyrido[3,4-d]pyrimidin-4-yl)piperazine-1-carboxylate Benzyl (S)-4-(7-(8-bromonaphthalen-1-yl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (30 mg, 0.042 mmol) and dichloro[1,1'-bis(diphenylphosphino)ferrocene]palladium (II) dichloromethane adduct (14 mg, 0.017 mmol) were diluted with cyclopropylzine bromide (253 μl, 0.13 mmol). The reaction was purged with argon, sealed and heated to 90° C. After stirring for 12 hours, the reaction was allowed to cool and diluted with ethyl acetate and water. The layers were separated and the ethyl acetate was dried over $MgSO_4$, filtered and concentrated. The material was purified on silica gel eluting with 10% methanol/DCM (1% $NH_4OH$) to afford benzyl (S)-2-(cyanomethyl)-4-(7-(8-cyclopropylnaphthalen-1-yl)-2-(((S)-1-methylpyrrolidin-2-yl)methoxy)-5,6,7,8-tetrahydropyrido[3,4-d]pyrimidin-4-yl)piperazine-1-carboxylate (7 mg, 0.010 mmol, 25% yield).

Step B: 2-((S)-4-(7-(8-Cyclopropylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile Benzyl (S)-2-(cyanomethyl)-4-(7-(8-cyclopropylnaphthalen-1-yl)-2-(((S)-1-methylpyrrolidin-2-yl)methoxy)-5,6,7,8-tetrahydropyrido[3,4-d]pyrimidin-4-yl)piperazine-1-carboxylate (9 mg, 0.01 mmol) was diluted with methanol (1 mL) followed by the addition of Pd—C (1 mg, 0.01 mmol). The reaction was equipped with a hydrogen balloon and purged three times followed by stirring under an atmosphere of hydrogen for 4 hours. The solids were collected by filtration, rinsed with methanol and the combined organic phase was concentrated to afford 2-((S)-4-(7-(8-cyclopropylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (7 mg, 0.01 mmol, 97% yield).

Step C: 2-((S)-4-(7-(8-Cyclopropylnaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile 2-((S)-4-(7-(8-cyclopropylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (10 mg, 0.019 mmol) was diluted with DMF (500 µL) followed by the addition of DIEA (11 µl, 0.065 mmol), 2-fluoroacrylic acid (2.5 mg, 0.028 mmol) and 2,4,6-tripropyl-1,3,5,2,4,6-trioxatriphosphinane 2,4,6-trioxide (13 µl, 0.020 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silca gel eluting with 10% methanol/DCM (1% NH$_4$OH) to afford 2-((S)-4-(7-(8-cyclopropylnaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile (0.9 mg, 0.0015 mmol, 7.9% yield). ESI+APCI MS m/z 610.3 [M+H]$^+$.

Example 591

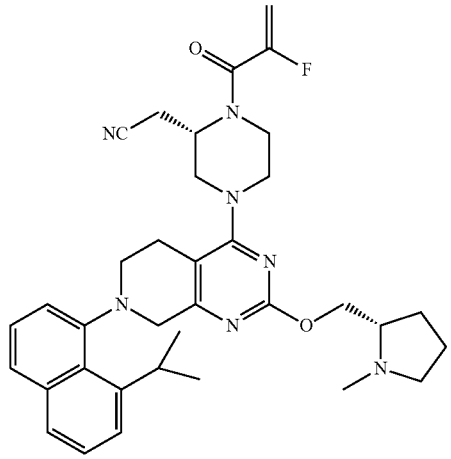 [SMILES: C=C(F)C(=O)N1CCN(c2nc(OC[C@@H]3CCCN3C)nc3c2CCN(c2cccc4cccc(C(C)C)c24)C3)C[C@@H]1CC#N]

2-((S)-1-(2-Fluoroacryloyl)-4-(7-(8-isopropylnaphthalen-1-yl)-2-((S)-1-methylpyrrolidin-2-yl)methoxy)-5,6,7,8-tetrahydropyrido[3,4-d]pyrimidin-4-yl)piperazin-2-yl)acetonitrile Synthesized in the same fashion as Example 590 substituting isopropyl zinc bromide for cyclopropyl zinc bromide in step A. ESI+APCI MS m/z 612.3 [M+H]$^+$.

Example 592

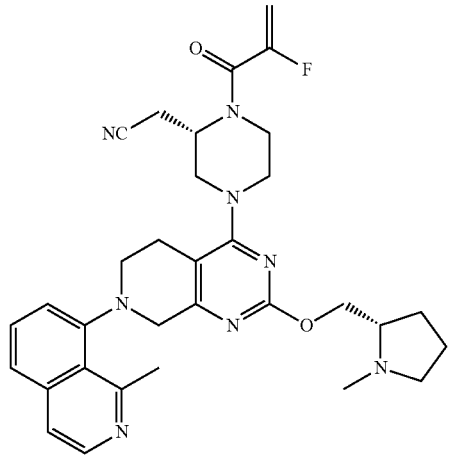 [SMILES: C=C(F)C(=O)N1CCN(c2nc(OC[C@@H]3CCCN3C)nc3c2CCN(c2cccc4ccnc(C)c24)C3)C[C@@H]1CC#N]

2-((S)-1-(2-Fluoroacryloyl)-4-(7-(1-methylisoquinolin-8-yl)-2-((S)-1-methylpyrrolidin-2-yl)methoxy)-5,6,7,8-tetrahydropyrido[3,4-d]pyrimidin-4-yl)piperazin-2-yl)acetonitrile Synthesized in the same fashion as Example 588 substituting 8-bromo-1-methylisoquinoline for 1,8-dibromonaphthalene in step A. ESI+APCI MS m/z 585.3 [M+H]$^+$.

Example 593

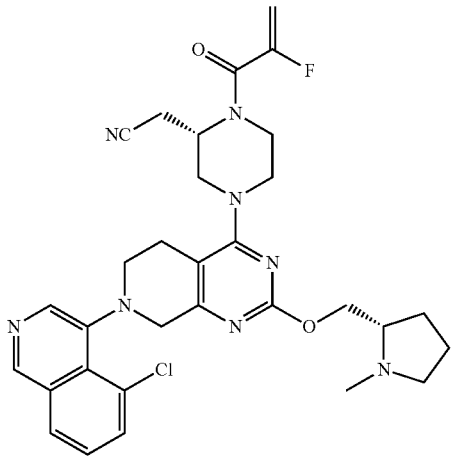 [SMILES: C=C(F)C(=O)N1CCN(c2nc(OC[C@@H]3CCCN3C)nc3c2CCN(c2cncc4cccc(Cl)c24)C3)C[C@@H]1CC#N]

2-((S)-4-(7-(5-Chloroisoquinolin-4-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile Synthesized in the same fashion as Example 588 substituting 4-bromo-5-chloroisoquinoline for 1,8-dibromonaphthalene in step A. ESI+APCI MS m/z 605.2 [M+H]$^+$.

Example 594

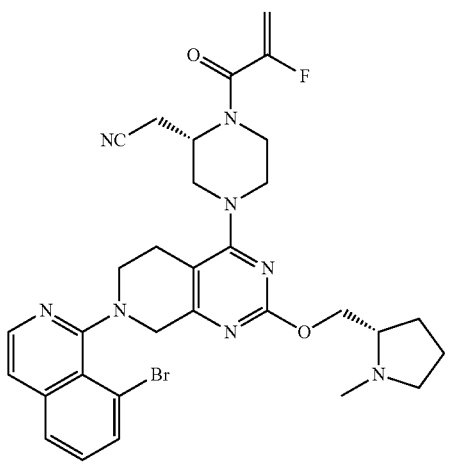 [SMILES: C=C(F)C(=O)N1CCN(c2nc(OC[C@@H]3CCCN3C)nc3c2CCN(c2nccc4cccc(Br)c24)C3)C[C@@H]1CC#N]

2-((S)-4-(7-(8-Bromoisoquinolin-1-yl)-2-(((S)-1-methylpyrrolidin-2-yl)methoxy)-5,6,7,8-tetrahydro-pyrido[3,4-d]pyrimidin-4-yl)-1-(2-fluoroacryloyl)piperazin-2-yl)acetonitrile Synthesized in the same fashion as Example 588 substituting 8-bromo-1-chloroisoquinoline for 1,8-dibromonaphthalene in step A. ESI+APCI MS m/z 651.2 [M+H]⁺.

Example 595

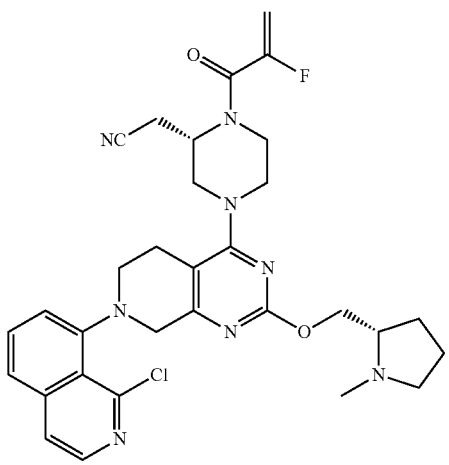 [SMILES: C=C(F)C(=O)N1CCN(c2nc(OC[C@@H]3CCCN3C)nc3c2CCN(c2cccc4ccnc(Cl)c24)C3)C[C@@H]1CC#N]

2-((S)-4-(7-(1-chloroisoquinolin-8-yl)-2-(((S)-1-methylpyrrolidin-2-yl)methoxy)-5,6,7,8-tetrahydro-pyrido[3,4-d]pyrimidin-4-yl)-1-(2-fluoroacryloyl)piperazin-2-yl)acetonitrile Synthesized in the same fashion as Example 589 substituting 8-bromo-1-chloroisoquinoline for 1,8-dibromonaphthalene in step A. ESI+APCI MS m/z 605.3 [M+H]⁺.

Example 596

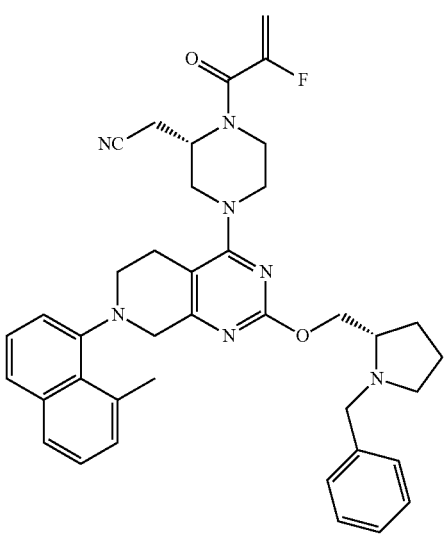 [SMILES: C=C(F)C(=O)N1CCN(c2nc(OC[C@@H]3CCCN3Cc3ccccc3)nc3c2CCN(c2cccc4cccc(C)c24)C3)C[C@@H]1CC#N]

2-((S)-4-(2-(((S)-1-Benzylpyrrolidin-2-yl)methoxy)-7-(8-methylnaphthalen-1-yl)-5,6,7,8-tetrahydro-pyrido[3,4-d]pyrimidin-4-yl)-1-(2-fluoroacryloyl)piperazin-2-yl)acetonitrile

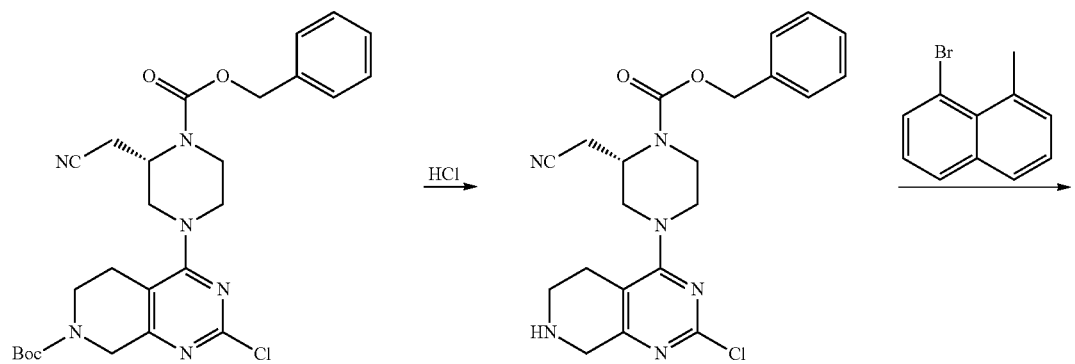

1533
1534
-continued
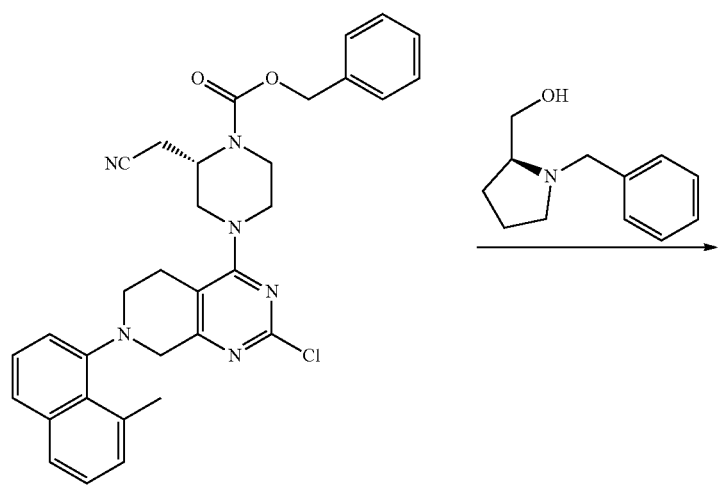
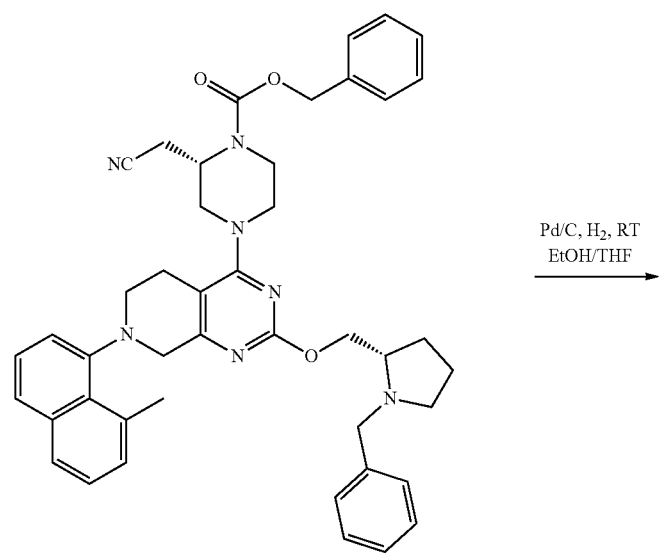
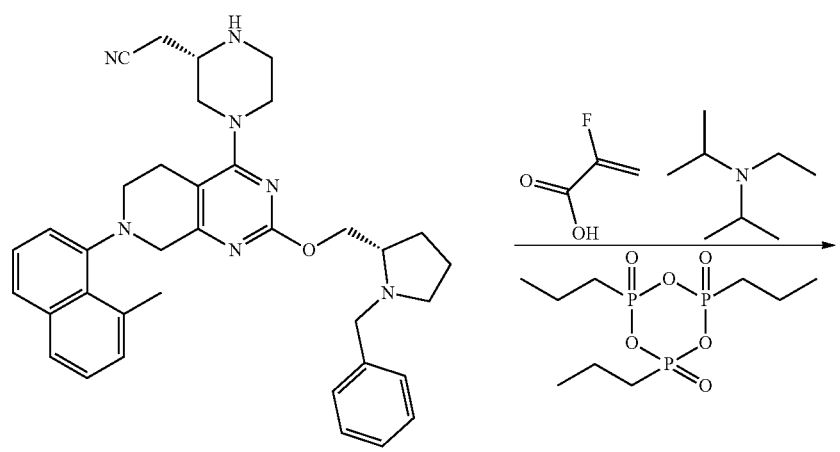

-continued

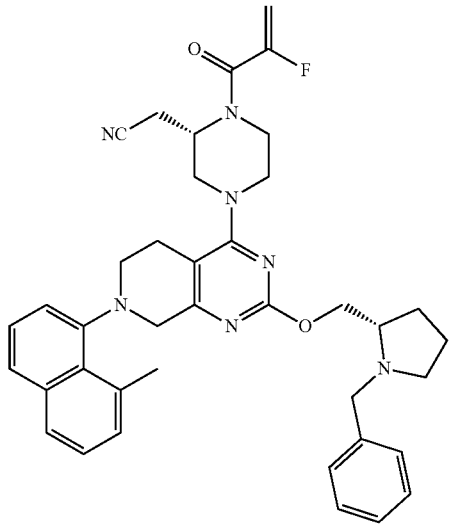 [SMILES: C=C(F)C(=O)N1CCN(c2nc(OC[C@@H]3CCCN3Cc3ccccc3)nc3c2CCN(c2cccc4cccc(C)c24)C3)C[C@@H]1CC#N]

Step A: Benzyl (S)-4-(2-chloro-5,6,7,8-tetrahydropyrido[3,4-d]pyrimidin-4-yl)-2-(cyanomethyl)piperazine-1-carboxylate Tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (3 g, 5.7 mmol) was dissolved in DCM (57 ml, 5.7 mmol) and treated with hydrochloric acid solution (4.0M in 1,4-dioxane) (7.1 ml, 28 mmol). The reaction was stirred at room temperature for 1 hour. The reaction was washed with 1M NaOH. The aqueous phase was extracted with additional DCM (2×), the combined organic phase was dried over MgSO$_4$ and concentrated in vacuo to give benzyl (S)-4-(2-chloro-5,6,7,8-tetrahydropyrido[3,4-d]pyrimidin-4-yl)-2-(cyanomethyl)piperazine-1-carboxylate (2.4 g, 5.6 mmol, 99% yield). ESI+APCI MS m/z 427.2 [M+H]$^+$.

Step B: Benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate Tris(dibenzylideneacetone)dipalladium(0) (1.030 g, 1.124 mmol) and 9,9-dimethyl-4,5-bis(diphenylphosphino)xanthene (1.301 g, 2.249 mmol) were dissolved in 1,4-dioxane (56.22 ml, 5.622 mmol) and purged under argon for 5 minutes. The reaction was stirred at 100° C. under argon for 15 minutes and the reaction cooled to room temperature. To the reaction was added benzyl (S)-4-(2-chloro-5,6,7,8-tetrahydropyrido[3,4-d]pyrimidin-4-yl)-2-(cyanomethyl)piperazine-1-carboxylate (2.4 g, 5.622 mmol), 1-bromo-8-methylnaphthalene (3.729 g, 16.87 mmol), and cesium carbonate (5.495 g, 16.87 mmol) under argon. The reaction was capped under argon and stirred at 100° C. over night. The reaction was cooled to room temperature and the solids were removed by filtration. The filtrate was concentrated in vacuo and purified by normal phase chromatography (2×) on the CombiFlash using 0475% Hexanes/EtOAc as the eluent to give benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate (2.532 g, 4.465 mmol, 79.42% yield). ESI+APCI MS m/z 567.2 [M+H]$^+$.

Step C: 2-((S)-4-(2-(((S)-1-Benzylpyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile In a microwave tube a solution of benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate (250 mg, 0.441 mmol) in dioxane (2204 µl, 0.441 mmol) was sparged with argon for 5 minutes. (S)-(−)-1-benzyl-2-pyrrolidinemethanol (169 mg, 0.882 mmol), Cs$_2$CO$_3$ (431 mg, 1.32 mmol), methanesulfonato(2-dicyclohexylphosphino-2',6'-di-i-propoxy-1,1'-biphenyl)(2'-methylamino-1,1'-biphenyl-2-yl)palladium(II) (37.5 mg, 0.0441 mmol) were sequentially added under argon and the reaction sparged with Ar for an additional 5 minutes. The reaction mixture was capped and heated at 100° C. for 2 hours. The reaction was cooled to room temperature and ethyl acetate was added. The solids were removed by filtration, and the filtrate was concentrated and purified by flash chromatography eluting with 0420% DCM/MeOH+2% NH$_4$OH. All fractions containing desired product were combined and concentrated to give 2-((S)-4-(2-(((S)-1-benzylpyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile (120 mg, 0.204 mmol, 77.2% yield). ESI+APCI MS m/z 722.4 [M+H]$^+$.

Step D: 2-((S)-4-(2-(((S)-1-Benzylpyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile A solution of benzyl (S)-4-(2-(((S)-1-benzylpyrrolidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate (200 mg, 0.277 mmol) in EtOH (2770 µl, 0.277 mmol) and THF (2770 µl, 0.277 mmol) was purged with N$_2$ for 5 minutes. To this solution was added palladium (73.7 mg, 0.0693 mmol) (Degussa Type, 10 wt %, 50% H$_2$O), and was immediately capped and purged with N$_2$ for an additional 5 minutes. The solution was then stirred under one atmosphere of H$_2$ for 1 hour. The mixture was diluted with MeOH and filtered through packed celite. The filtrate was then concentrated in vacuo to provide crude 2-((S)-4-(2-(((S)-1-benzylpyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile (160 mg, 0.272 mmol, 98.3% yield). ESI+APCI MS m/z 588.4 [M+H]+.

Step E: 2-((S)-4-(2-(((S)-1-Benzylpyrrolidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile To a 25 mL RBF containing dichloromethane (2722 µl, 0.272 mmol) at 0° C. was added 2-((S)-4-(2-(((S)-1-benzylpyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile (160 mg, 0.272 mmol) and Hunig's base (95.1 µl, 0.544 mmol). The reaction mixture was vigorously stirred while 2-fluoroacrylic acid (98.1 mg, 1.09 mmol) was added in one portion. Next, 1-propanephosphonic acid cyclic anhydride (243 µl, 0.408 mmol) was added slowly to the stirring mixture. The reaction was stirred for 2 hours at 0° C. The reaction was treated with basic water and the aqueous layer extracted with DCM (3×). The combined organic phase was concentrated in vacuo and the residue resuspended in a 60:40 mixture of MeCN:H2O and purified (prep HPLC), eluting with 5→95% MeCN/0.1% TFA in water/0.1% TFA to give product. Pure fractions were pooled and diluted with EtOAc and 1N NaOH and the layers separated. The combined organic phase was washed with brine, dried over MgSO4 and concentrated in vacuo to give 2-((S)-4-(2-(((S)-1-benzylpyrrolidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile (8 mg, 0.0121 mmol, 4.45% yield). ESI+APCI MS m/z 660.4 [M+H]+.

Example 597

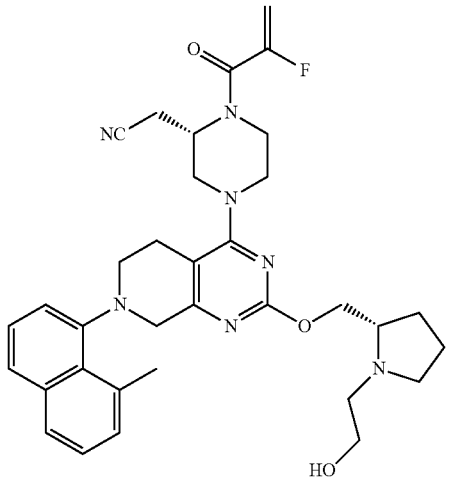 [SMILES: C=C(F)C(=O)N1CCN(c2nc(OC[C@@H]3CCCN3CCO)nc3c2CCN(c2cccc4cccc(C)c24)C3)C[C@@H]1CC#N]

2-((S)-4-(7-(8-Chloronaphthalen-1-yl)-2-(((S)-1-(2-fluoroethyl)pyrrolidin-2-yl)methoxy)-5,6,7,8-tetrahydropyrido[3,4-d]pyrimidin-4-yl)-1-(2-fluoroacryloyl)piperazin-2-yl)acetonitrile

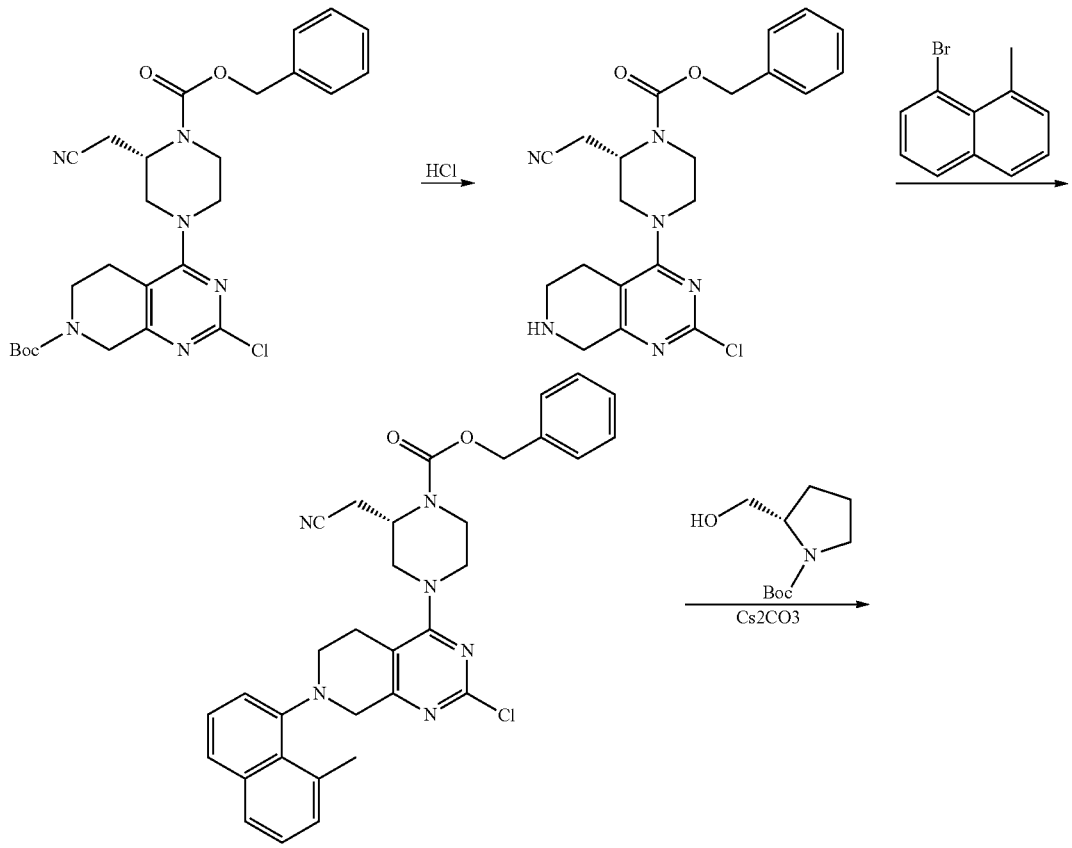

1539 -continued 1540
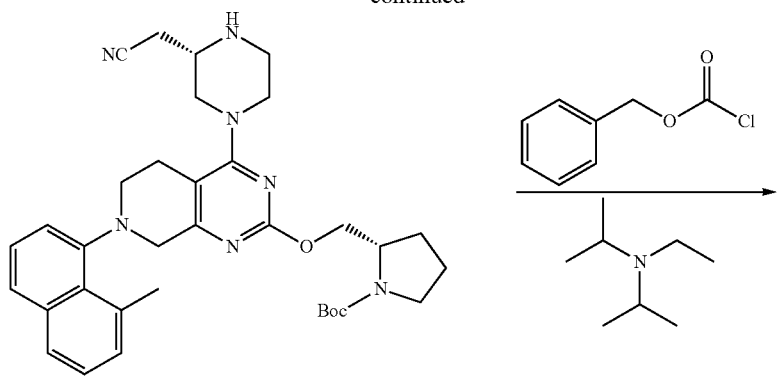
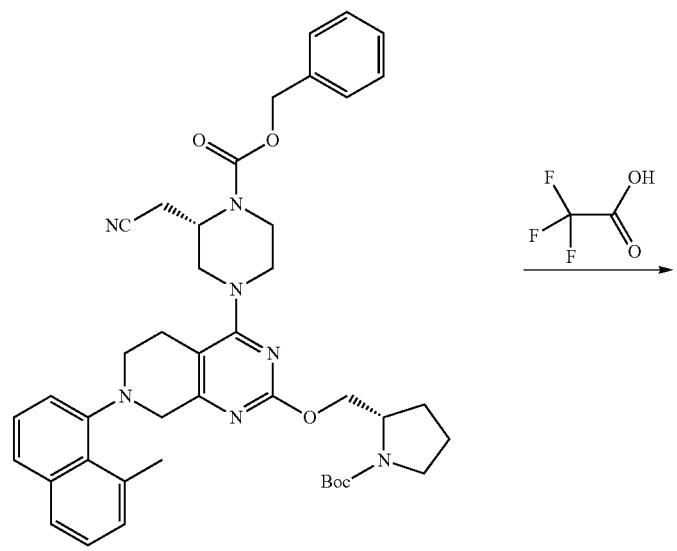
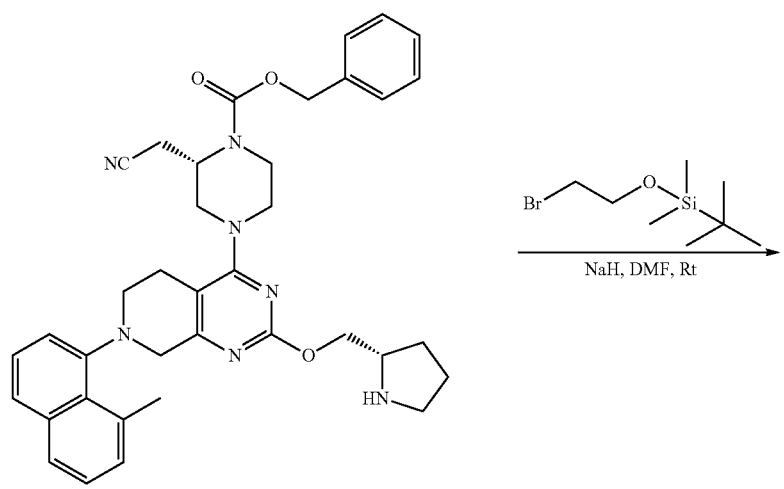

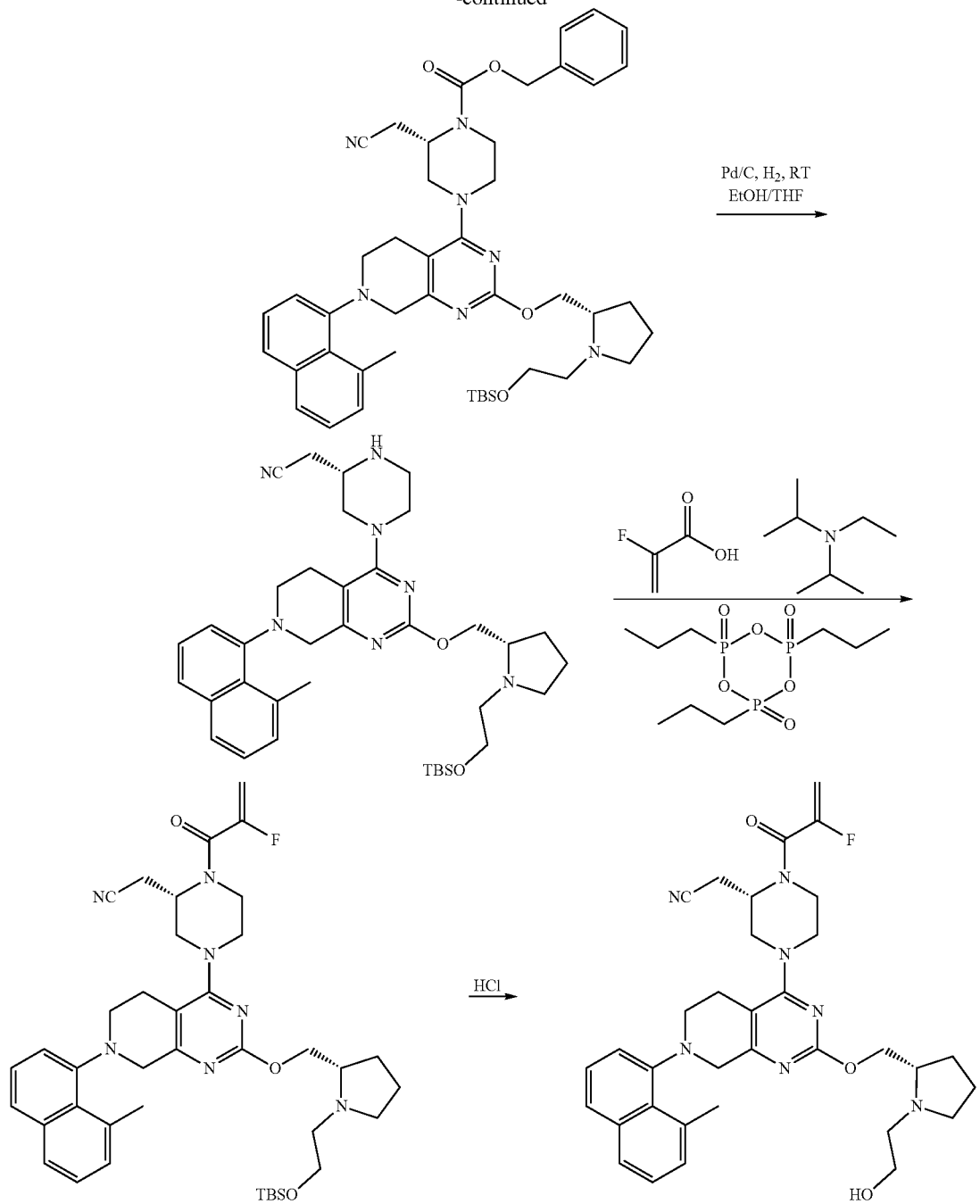

Step A: Benzyl (S)-4-(2-chloro-5,6,7,8-tetrahydropyrido[3,4-d]pyrimidin-4-yl)-2-(cyanomethyl)piperazine-1-carboxylate tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (2 g, 3.795 mmol) was dissolved in DCM (37.95 ml, 3.795 mmol) and treated with hydrochloric acid solution (4.0 M in 1,4-dioxane) (4.744 ml, 18.97 mmol). The reaction was stirred at room temperature for 1 hour. The reaction was washed with 1M NaOH and the aqueous layer extracted with DCM (2×). The organic phase was combined, dried over $Na_2SO_4$ and concentrated to give benzyl (S)-4-(2-chloro-5,6,7,8-tetrahydropyrido[3,4-d]pyrimidin-4-yl)-2-(cyanomethyl)piperazine-1-carboxylate (1.619 g, 3.792 mmol, 99.93% yield). ESI+APCI MS m/z 427.2 [M+H]$^+$.

Step B: Benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate Tris(dibenzylideneacetone)dipalladium(0) (0.6946 g, 0.7585 mmol) and 9,9-dimethyl-4,5-bis(diphenylphosphino)xanthene (0.8778 g, 1.517 mmol) were dissolved in 1,4-dioxane (37.92 ml, 3.792 mmol), purged under argon for 5 minutes and stirred at 100° C. under argon for 15 minutes and the reaction cooled to room temperature. To the mixture was added benzyl (S)-4-(2-chloro-5,6,7,8-tetrahydropyrido[3,4-d]pyrimidin-4-yl)-2-(cyanomethyl)piperazine-1-carboxylate (1.619 g, 3.792 mmol), 1-bromo-8-methylnaphthalene (2.515 g, 11.38 mmol), and cesium carbonate (3.707 g, 11.38 mmol) under argon. The reaction was capped under argon and stirred at 100° C. over night. The reaction was cooled to room temperature and the solids removed by filtration. The filtrate was concentrated in vacuo and purified by normal phase chromatography (2×) using 0→75% hexanes/EtOAc as the eluent to give benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate (958 mg, 1.689 mmol, 44.54% yield). ESI+APCI MS m/z 567.2 [M+H]$^+$.

Step C: tert-Butyl (S)-2-(((4-((S)-3-(cyanomethyl)piperazin-1-yl)-7-(8-methylnaphthalen-1-yl)-5,6,7,8-tetrahydropyrido[3,4-d]pyrimidin-2-yl)oxy)methyl)pyrrolidine-1-carboxylate In a microwave tube, a solution of benzyl (S)-4-(2-chloro-7-(8-methylnaphthalen-1-yl)-5,6,7,8-tetrahydropyrido[3,4-d]pyrimidin-4-yl)-2-(cyanomethyl)piperazine-1-carboxylate (250 mg, 0.441 mmol) in dioxane (2204 µl, 0.441 mmol) was sparged with argon for 5 minutes. (S)-(−)-1-(tert-Butoxycarbonyl)-2-pyrrolidinemethanol (222 mg, 1.10 mmol), $Cs_2CO_3$ (431 mg, 1.32 mmol) and methanesulfonato(2-dicyclohexylphosphino-2',6'-di-i-propoxy-1,1'-biphenyl)(2'-methylamino-1,1'-biphenyl-2-yl)palladium(II) (37.5 mg, 0.0441 mmol) were sequentially added under argon and the reaction sparged with Ar for an additional 5 minutes. The reaction mixture was capped and heated at 100° C. for 2 hours. The reaction was cooled to room temperature and ethyl acetate was added. The solids were removed by filtration, the filtrate was concentrated and purified by flash chromatography eluting with 0→20% DCM/MeOH+2% $NH_4OH$. All fractions containing desired product were combined and concentrated to give benzyl (S)-4-(2-(((S)-1-(tert-butoxycarbonyl)pyrrolidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate (306 mg, 0.418 mmol, 94.8% yield). ESI+APCI MS m/z 598.3 [M+H]+.

Step D: Benzyl (S)-4-(2-(((S)-1-(tert-butoxycarbonyl)pyrrolidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate tert-Butyl (S)-2-(((4-((S)-3-(cyanomethyl)piperazin-1-yl)-7-(8-methylnaphthalen-1-yl)-5,6,7,8-tetrahydropyrido[3,4-d]pyrimidin-2-yl)oxy)methyl)pyrrolidine-1-carboxylate (93 mg, 0.1556 mmol) was dissolved in dichloromethane (1556 µl, 0.1556 mmol) and treated with Hunig's base (135.9 µl, 0.7779 mmol) and benzyl carbonochloridate (33.31 µl, 0.2334 mmol). The reaction was stirred at room temperature for 2 hours. The reaction was partitioned between DCM and water and the layers separated. The aqueous layer was extracted with DCM (2×). The combined organic phase was dried over $Na_2SO_4$, concentrated in vacuo and the residue purified by chromatography using 0→15% DCM/MeOH+2% $NH_4OH$ as eluent. All fractions containing product were combined and concentrated to give benzyl (S)-4-(2-(((S)-1-(tert-butoxycarbonyl)pyrrolidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate (367 mg, 0.5014 mmol, 322.3% yield). ESI+APCI MS m/z 732.4 [M+H]$^+$.

Step E: Benzyl (S)-2-(cyanomethyl)-4-(7-(8-methylnaphthalen-1-yl)-2-((S)-pyrrolidin-2-yl)methoxy)-5,6,7,8-tetrahydropyrido[3,4-d]pyrimidin-4-yl)piperazine-1-carboxylate Benzyl (S)-4-(2-(((S)-1-(tert-butoxycarbonyl)pyrrolidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate (367 mg, 0.501 mmol) was dissolved in DCM (5014 µl, 0.501 mmol) and treated with TFA (193 µl, 2.51 mmol) and the reaction stirred at room temperature for 1 hour. No reaction was observed. The mixture was concentrated in vacuo and resuspended in DCM. To this was added HCl (4M in Dioxane, 500 µL) and the reaction stirred at room temperature for 1 hour. The reaction was concentrated in vacuo and the residue partitioned between 1M NaOH and DCM. The combined organic phase was concentrated in vacuo to give crude benzyl (S)-2-(cyanomethyl)-4-(7-(8-methylnaphthalen-1-yl)-2-(((S)-pyrrolidin-2-yl)methoxy)-5,6,7,8-tetrahydropyrido[3,4-d]pyrimidin-4-yl)piperazine-1-carboxylate (192 mg, 0.304 mmol, 60.6% yield). ESI+APCI MS m/z 632.3 [M+H]$^+$.

Step F: Benzyl (S)-4-(2-(((S)-1-(2-((tert-butyldimethylsilyl)oxy)ethyl)pyrrolidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate To a stirred solution of benzyl (S)-2-(cyanomethyl)-4-(7-(8-methylnaphthalen-1-yl)-2-(((S)-pyrrolidin-2-yl)methoxy)-5,6,7,8-tetrahydropyrido[3,4-d]pyrimidin-4-yl)piperazine-1-carboxylate (150 mg, 0.23742 mmol) in 2.5 mL of DMF was added sodium hydride (60% dispersion in mineral oil (8.5465 mg, 0.35614 mmol)). After 15 minutes (2-bromoethoxy)(tert-butyl)dimethylsilane (142.00 mg, 0.59356 mmol) was added and the reaction heated to 75° C. for 3.5 hours. The reaction was cooled to room temperature and partitioned between water and EtOAc and the layers separated. The aqueous layer was extracted with EtOAc and the combined organic phase washed with more water and brine, dried over $Na_2SO_4$ and concentrated in vacuo to give crude benzyl (S)-4-(2-(((S)-1-(2-((tert-butyldimethylsilyl)oxy)ethyl)pyrrolidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate (187 mg, 0.237 mmol, 99.7% yield). ESI+APCI MS m/z 790.4 [M+H]$^+$.

Step G: 2-((S)-4-(2-(((S)-1-(2-((tert-Butyldimethylsilyl)oxy)ethyl)pyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile A solution of benzyl (S)-4-(2-(((S)-1-(2-((tert-butyldimethylsilyl)oxy)ethyl)pyrrolidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate (187 mg, 0.237 mmol) in EtOH (2367 µl, 0.237 mmol) and THF (2367 µl, 0.237 mmol) was purged with $N_2$ for 5 minutes. To this solution was added palladium (63.0 mg, 0.0592 mmol) (Degussa Type, 10 wt %, 50% $H_2O$), and was immediately capped and purged with $N_2$ for an additional 5 minutes. The solution was then stirred under one atmosphere of $H_2$ overnight. The mixture was diluted with MeOH and filtered through packed celite. The filtrate was then concentrated in vacuo to provide crude 2-((S)-4-(2-(((S)-1-(2-((tert-butyldimethylsilyl)oxy)ethyl)pyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile (134 mg, 0.204 mmol, 86.3% yield). ESI+APCI MS m/z 656.4 [M+H]+.

Step H: 2-((S)-4-(2-(((S)-1-(2-((tert-Butyldimethylsilyl)oxy)ethyl)pyrrolidin-2-yl)methoxy)-7-(8-methylnaphthalen-1-yl)-5,6,7,8-tetrahydropyrido [3,4-d] pyrimidin-4-yl)-1-(2-fluoroacryloyl)piperazin-2-yl) acetonitrile At 0° C., to a 25 mL RBF containing N,N-dimethylformamide (2043 µl, 0.204 mmol) was added 2-((S)-4-(2-(((S)-1-(2-((tert-butyldimethyl silyl)oxy)ethyl)pyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile (134 mg, 0.204 mmol) and Hunig's base (71.4 µl, 0.409 mmol). The reaction mixture was vigorously stirred while 2-fluoroacrylic acid (22.1 mg, 0.245 mmol) was added in one portion. Next, 1-propanephosphonic acid cyclic anhydride (182 µl, 0.306 mmol) was added slowly to the stirring mixture. The reaction was stirred for 1 hour at 0° C. The reaction was treated with aqueous NaOH and the aqueous layer extracted with EtOAc (3×). The combined organic phase was concentrated in vacuo to give crude 2-((S)-4-(2-(((S)-1-(2-((tert-butyldimethylsilyl)oxy)ethyl)pyrrolidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile (120 mg, 0.165 mmol, 80.7% yield). ESI+APCI MS m/z 728.4 [M+H]+.

Step I: 2-((S)-1-(2-Fluoroacryloyl)-4-(2-(((S)-1-(2-hydroxyethyl)pyrrolidin-2-yl)methoxy)-7-(8-methylnaphthalen-1-yl)-5,6,7,8-tetrahydropyrido[3,4-d] pyrimidin-4-yl)piperazin-2-yl)acetonitrile 2-((S)-4-(2-(((S)-1-(2-((tert-butyldimethylsilyl)oxy) ethyl)pyrrolidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile (50 mg, 0.069 mmol) was dissolved in dichloromethane (687 µl, 0.069 mmol) and treated with hydrogen chloride (52 µl, 0.21 mmol) (4M in dioxane). The reaction stirred at room temperature for 1 hour. The reaction was then concentrated in vacuo and resuspended in a 60:40 mixture of MeCN:H2O and purified (prep HPLC) eluting with 5→95% MeCN/0.1% TFA in water/0.1% TFA. Fractions containing product were combined and partitioned between 1M NaOH and DCM and the layers separated and the aqueous layer extracted with additional DCM. The combined organic phase was dried over Na2SO4 and concentrated in vacuo to give 2-((S)-1-(2-fluoroacryloyl)-4-(2-(((S)-1-(2-hydroxyethyl)pyrrolidin-2-yl)methoxy)-7-(8-methylnaphthalen-1-yl)-5,6,7,8-tetrahydropyrido[3,4-d]pyrimidin-4-yl)piperazin-2-yl)acetonitrile (2.7 mg, 0.0044 mmol, 6.4% yield). ESI+APCI MS m/z 614.3 [M+H]+.

Example 598

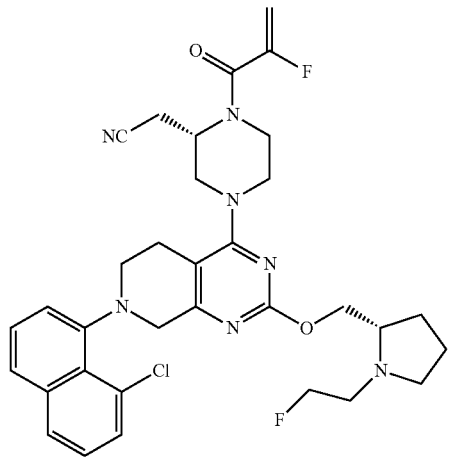 [SMILES: C=C(F)C(=O)N1CCN(c2nc(OC[C@@H]3CCCN3CCF)nc3c2CCN(c2cccc4cccc(Cl)c24)C3)C[C@@H]1CC#N]

2-((S)-4-(7-(8-Chloronaphthalen-1-yl)-2-(((S)-1-(2-fluoroethyl)pyrrolidin-2-yl)methoxy)-5,6,7,8-tetrahydropyrido[3,4-d]pyrimidin-4-yl)-1-(2-fluoroacryloyl)piperazin-2-yl)acetonitrile

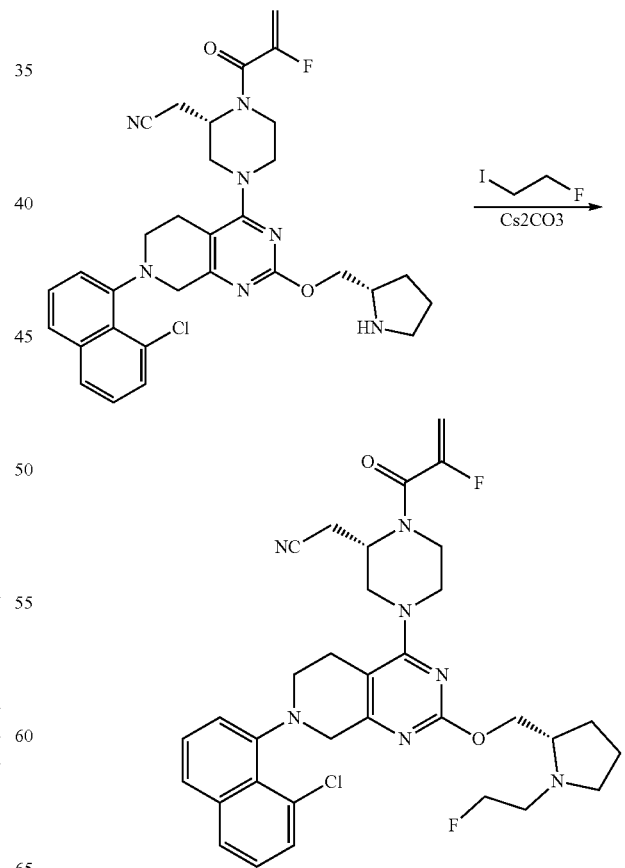

1547

Step A: 2-((S)-4-(7-(8-Chloronaphthalen-1-yl)-2-(((S)-1-(2-fluoroethyl)pyrrolidin-2-yl)methoxy)-5,6,7,8-tetrahydropyrido[3,4-d]pyrimidin-4-yl)-1-(2-fluoroacryloyl)piperazin-2-yl)acetonitrile 2-((S)-4-(7-(8-chloronaphthalen-1-yl)-2-(((S)-pyrrolidin-2-yl)methoxy)-5,6,7,8-tetrahydropyrido[3,4-d]pyrimidin-4-yl)-1-(2-fluoroacryloyl)piperazin-2-yl)acetonitrile (30 mg, 0.0508 mmol) was dissolved in acetonitrile (508 µl, 0.0508 mmol) and cesium carbonate (19.9 mg, 0.0610 mmol) was added in one portion. To this mixture was then added 1-fluoro-2-iodoethane (3.72 µl, 0.0458 mmol) and the reaction stirred at 60° C. over night. The reaction was cooled to room temperature, the solids were removed by filtration, and the filtrate was concentrated in vacuo. The residue was resuspended in 60:40 MeCN:water and purified (prep HPLC), eluting with 5→95% MeCN/0.1% TFA in water/0.1% TFA. Fractions containing desired product were combined and partitioned between EtOAc and 1M NaOH and the layers separated. The aqueous layer was extracted with additional EtOAc (2×). The combined organic phase was dried over $Na_2SO_4$ and concentrated in vacuo to give 2-((S)-4-(7-(8-chloronaphthalen-1-yl)-2-(((S)-1-(2-fluoroethyl)pyrrolidin-2-yl)methoxy)-5,6,7,8-tetrahydropyrido[3,4-d]pyrimidin-4-yl)-1-(2-fluoroacryloyl)piperazin-2-yl)acetonitrile (4.8 mg, 0.00755 mmol, 14.8% yield). ESI+ APCI MS m/z 636.3 [M+H]+.

Example 599

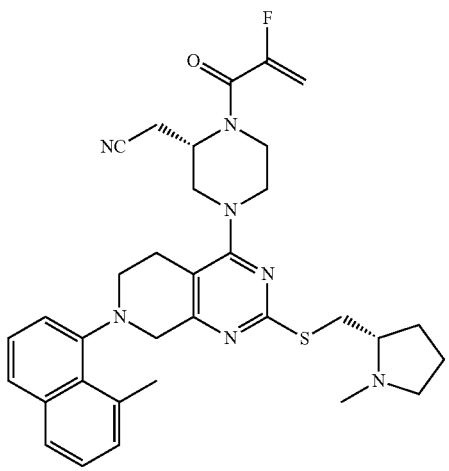 [SMILES: C=C(F)C(=O)N1CCN(c2nc(SC[C@@H]3CCCN3C)nc3c2CCN(c2cccc4cccc(C)c24)C3)C[C@@H]1CC#N]

2-((S)-1-(2-Fluoroacryloyl)-4-(7-(8-methylnaphthalen-1-yl)-2-((((S)-1-methylpyrrolidin-2-yl)methyl)thio)-5,6,7,8-tetrahydropyrido [3,4-d]pyrimidin-4-yl) piperazin-2-yl)acetonitrile

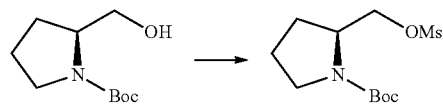

1548

Step A: tert-Butyl (S)-2-(((methylsulfonyl)oxy)methyl)pyrrolidine-1-carboxylate To a solution of tert-butyl (S)-2-(hydroxymethyl)pyrrolidine-1-carboxylate (3.0 g, 14.91 mmol) in DCM (74.53 ml, 14.91 mmol) cooled to 0° C. was added N-ethyl-N-isopropylpropan-2-amine (4.01 ml, 22.36 mmol) followed by addition of methanesulfonyl chloride (1.38 ml, 17.89 mmol) over the course of 1 minute and the reaction stirred at 0° C. for 1 hr. The reaction was next washed with 1:1 water/brine (10 mL) and the layers separated. The combined organic phase was next dried over $MgSO_4$, filtered and concentrated in vacuo. The material was next purified by chromatography using 0-10% MeOH in DCM as eluent to give tert-butyl (S)-2-(((methylsulfonyl)oxy)methyl)pyrrolidine-1-carboxylate (3.786 g, 13.55 mmol, 90.9% yield).

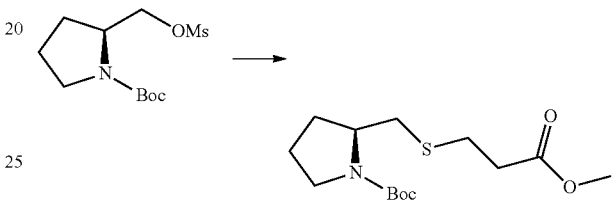

Step B: tert-Butyl (S)-2-(((3-methoxy-3-oxopropyl)thio)methyl)pyrrolidine-1-carboxylate tert-Butyl (S)-2-(((methylsulfonyl)oxy)methyl)pyrrolidine-1-carboxylate (2.00 g, 7.16 mmol) and $Cs_2CO_3$ (4.665 g, 14.32 mmol) were placed in dioxane (10 mL) and stirred for 3 hours at room temperature. NaOH (0.5M) was added and the mixture was extracted with DCM. The combined organic phase was concentrated and the residue purified by silica gel (0-12% MeOH in DCM with 0.25% $NH_4OH$) to provide tert-butyl (S)-2-(((3-methoxy-3-oxopropyl)thio)methyl)pyrrolidine-1-carboxylate (2.172 g, 7.16 mmol, 99% yield).

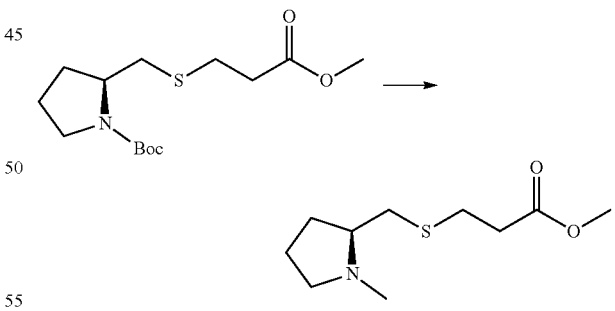

Step C: Methyl (S)-3-(((1-methylpyrrolidin-2-yl)methyl)thio)propanoate

To a vial was added tert-butyl (S)-2-(((3-methoxy-3-oxopropyl)thio)methyl)pyrrolidine-1-carboxylate (2.172 g, 7.16 mmol) in formic acid (6.751 ml, 179.0 mmol) followed by addition of formaldehyde (10.76 ml, 143.2 mmol) (37% aqueous). The mixture was then heated to 65° C. and stirred for 18 hours. The reaction was cooled and saturated bicarbonate was added slowly and the mixture was extracted with 10% MeOH in DCM (3×20 mL). The extracts were combined, dried over MgSO₄ and concentrated. The residue was purified by silica gel (5-20% MeOH in DCM with 0.25% NH₄OH) to provide methyl (S)-3-(((1-methylpyrrolidin-2-yl)methyl)thio)propanoate (186 mg, 0.86 mmol, 12% yield).

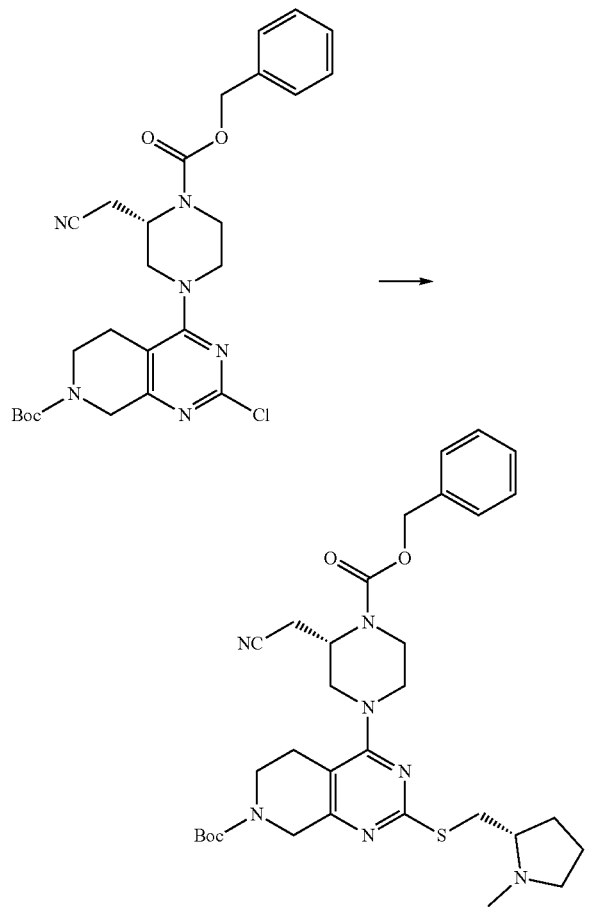

Step D: tert-Butyl 4-((S)-4-((benzyloxy)carbonyl)-3-(cyanomethyl)piperazin-1-yl)-2-((((S)-1-methyl-pyrrolidin-2-yl)methyl)thio)-5,8-dihydropyrido[3,4-d]pyrimidine-7(6H)-carboxylate Methyl (S)-3-(((1-methylpyrrolidin-2-yl)methyl)thio)propanoate (186 mg, 0.854 mmol) was placed in dioxane (5 mL). KOtBu (1708 µl, 1.71 mmol) was added and the mixture was stirred for 30 minutes. tert-Butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (300 mg, 0.569 mmol) was added and the mixture was heated to 80° C. for 24 hours. The mixture was cooled, diluted with water and extracted with DCM (3×15 mL). The extracts were combined and concentrated. The residue was purified by silica gel (0-15% MeOH in DCM with 0.25% NH₄OH) to provide tert-butyl 4-((S)-4-((benzyloxy)carbonyl)-3-(cyanomethyl)piperazin-1-yl)-2-((((S)-1-methylpyrrolidin-2-yl)methyl)thio)-5,8-dihydropyrido[3,4-d]pyrimidine-7(6H)-carboxylate (72 mg, 0.116 mmol, 20.3% yield).

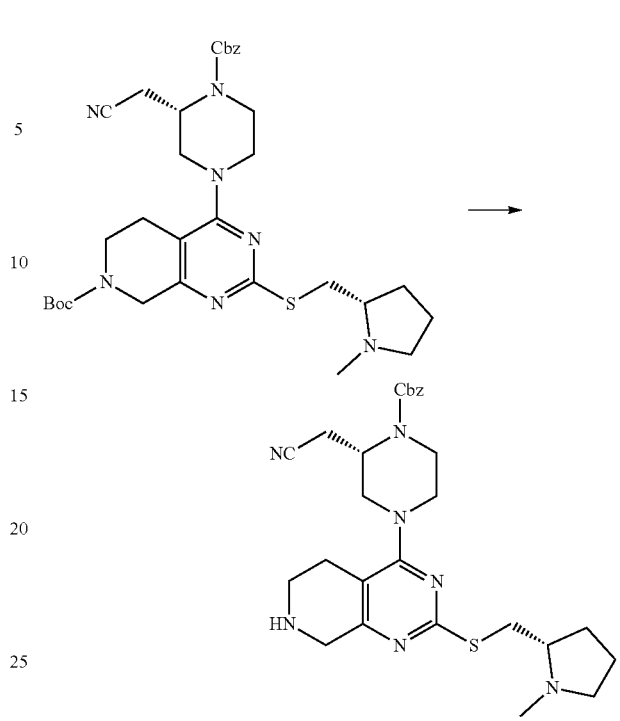

Step E: Benzyl (S)-2-(cyanomethyl)-4-(2-((((S)-1-methylpyrrolidin-2-yl)methyl)thio)-5,6,7,8-tetrahydropyrido[3,4-d]pyrimidin-4-yl)piperazine-1-carboxylate tert-Butyl 4-((S)-4-((benzyloxy)carbonyl)-3-(cyanomethyl)piperazin-1-yl)-2-((((S)-1-methylpyrrolidin-2-yl)methyl)thio)-5,8-dihydropyrido[3,4-d]pyrimidine-7(6H)-carboxylate (72 mg, 0.12 mmol) was placed in DCM (5 mL) and cooled to 0° C. HCl (145 µl, 0.58 mmol) was added and the reaction warmed to room temperature and stirred for 18 hours. The reaction was concentrated and was brought up in DCM. Saturated bicarbonate was added and the mixture was extracted with DCM (3×20 mL). The organic layers were combined, dried over MgSO₄ and concentrated to provide benzyl (S)-2-(cyanomethyl)-4-(2-((((S)-1-methylpyrrolidin-2-yl)methyl)thio)-5,6,7,8-tetrahydropyrido[3,4-d]pyrimidin-4-yl)piperazine-1-carboxylate (61 mg, 0.12 mmol).

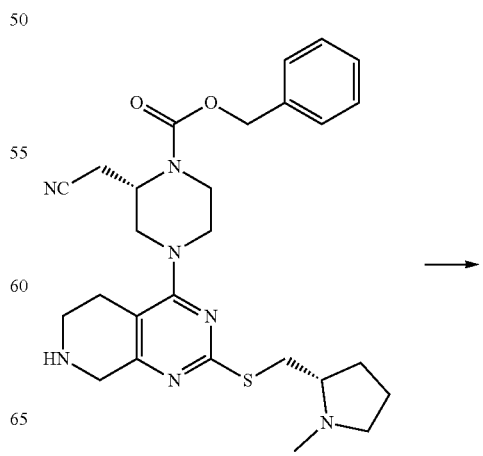

-continued

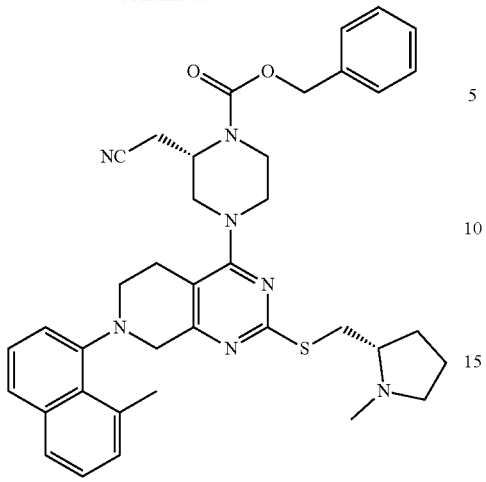

Step F: Benzyl (S)-2-(cyanomethyl)-4-(7-(8-methyl-naphthalen-1-yl)-2-((((S)-1-methylpyrrolidin-2-yl)methyl)thio)-5,6,7,8-tetrahydropyrido[3,4-d]pyrimidin-4-yl)piperazine-1-carboxylate To a solution of benzyl (S)-2-(cyanomethyl)-4-(2-((((S)-1-methylpyrrolidin-2-yl)methyl)thio)-5,6,7,8-tetrahydropyrido[3,4-d]pyrimidin-4-yl)piperazine-1-carboxylate (61 mg, 0.12 mmol) in toluene (2 mL) was added 1-bromo-8-methylnaphthalene (78 mg, 0.35 mmol) and the reaction degassed with argon for 15 minutes followed by addition of $Cs_2CO_3$ (190 mg, 0.58 mmol), $Pd_2(dba)_3$ (21 mg, 0.023 mmol) and Xantphos (27 mg, 0.047 mmol) and the reaction heated to 100° C. for 18 hr. The solids were removed by filtration, and the filtrate was concentrated in vacuo. The residue was next purified by chromatography using 1→12% MeOH/DCM with 2% $NH_4OH$ as additive to give benzyl (S)-2-(cyanomethyl)-4-(7-(8-methylnaphthalen-1-yl)-2-((((S)-1-methylpyrrolidin-2-yl)methyl)thio)-5,6,7,8-tetrahydropyrido[3,4-d]pyrimidin-4-yl)piperazine-1-carboxylate (54 mg, 0.082 mmol, 70% yield).

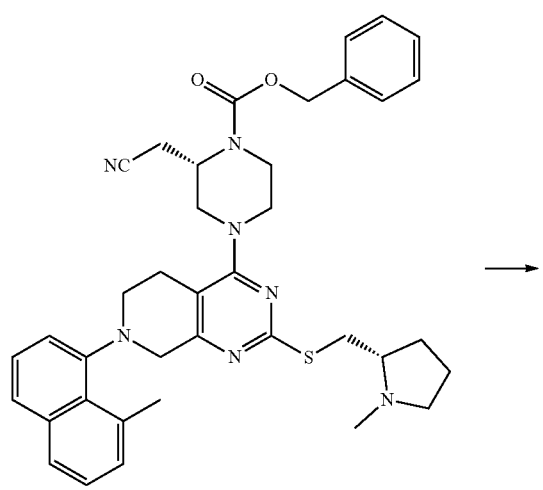

→

-continued

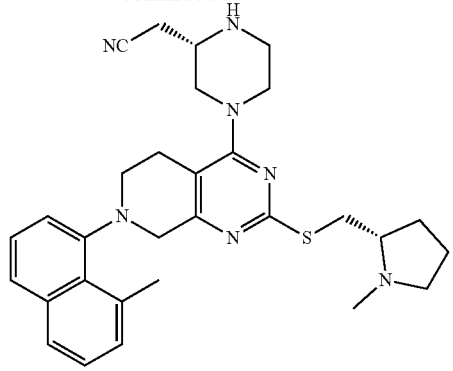

Step G: 2-((S)-4-(7-(8-Methylnaphthalen-1-yl)-2-((((S)-1-methylpyrrolidin-2-yl)methyl)thio)-5,6,7,8-tetrahydropyrido[3,4-d]pyrimidin-4-yl)piperazin-2-yl)acetonitrile Benzyl (S)-2-(cyanomethyl)-4-(7-(8-methylnaphthalen-1-yl)-2-((((S)-1-methylpyrrolidin-2-yl)methyl)thio)-5,6,7,8-tetrahydropyrido[3,4-d]pyrimidin-4-yl)piperazine-1-carboxylate (54 mg, 0.082 mmol) was placed in DCM (10 mL) and the reaction cooled to 0° C. AcOH (14.01 µl, 0.244 mmol) and TMS-I (69.67 µl, 0.490 mmol) were added and the reaction slowly warmed to room temperature and stirred for 1 hour. Saturated bicarbonate was added and the mixture was extracted with DCM. The extracts were concentrated and the residue purified by reverse phase chromatography (5-95% MeCN in water with 0.1% TFA). The isolated product was then free based by bring up in DCM and adding saturated bicarbonate. The organic layer was separated, dried over $MgSO_4$ and concentrated to provide 2-((S)-4-(7-(8-methylnaphthalen-1-yl)-2-((((S)-1-methylpyrrolidin-2-yl)methyl)thio)-5,6,7,8-tetrahydropyrido[3,4-d]pyrimidin-4-yl)piperazin-2-yl)acetonitrile (8 mg, 0.15 mmol, 19%).

Step H: 2-((S)-1-(2-Fluoroacryloyl)-4-(7-(8-methyl-naphthalen-1-yl)-2-((((S)-1-methylpyrrolidin-2-yl)methyl)thio)-5,6,7,8-tetrahydropyrido[3,4-d]pyrimidin-4-yl)piperazin-2-yl)acetonitrile To a 0° C. solution of N,N-dimethylformamide (152 µl, 0.015 mmol) was added 2-((S)-4-(7-(8-methylnaphthalen-1-yl)-2-((((S)-1-methylpyrrolidin-2-yl)methyl)thio)-5,6,7,8-tetrahydropyrido[3,4-d]pyrimidin-4-yl)piperazin-2-yl)acetonitrile (8.0 mg, 0.015 mmol) and triethylamine (7.37 µl, 0.053 mmol). The reaction mixture was vigorously stirred while 2-fluoroacrylic acid (4.10 mg, 0.046 mmol) was added in one portion. Next, 1-propanephosphonic acid cyclic anhydride (13.5 µl, 0.023 mmol) was added slowly to the stirring mixture. The reaction was stirred at room temperature for 20 minutes. Water was added and the mixture was extracted with DCM and the extracts were concentrated. The residue was purified by silica gel (0-12% MeOH in DCM with 0.25% $NH_4OH$) to provide 2-((S)-1-(2-fluoroacryloyl)-4-(7-(8-methylnaphthalen-1-yl)-2-((((S)-1-methylpyrrolidin-2-yl)methyl)thio)-5,6,7,8-tetrahydropyrido[3,4-d]pyrimidin-4-yl)piperazin-2-yl)acetonitrile (2.3 mg, 0.0038 mmol, 25.3% yield). ES+APCI MS m/z 600.3 [M+H]+.

Example 600

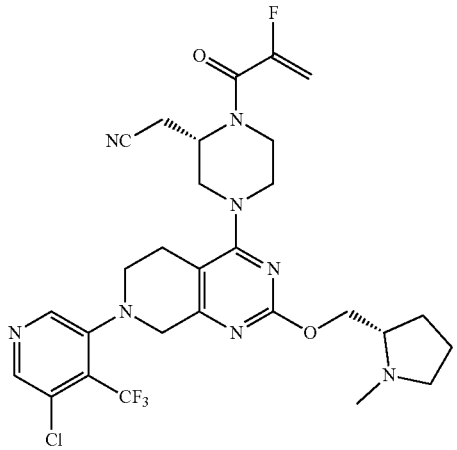 [SMILES: C=C(F)C(=O)N1CCN(c2nc(OC[C@@H]3CCCN3C)nc3c2CCN(c2cncc(Cl)c2C(F)(F)F)C3)C[C@@H]1CC#N]

2-((S)-4-(7-(5-Chloro-4-(trifluoromethyl)pyridin-3-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile 2-((S)-4-(7-(5-Chloro-4-(trifluoromethyl)pyridin-3-yl)-2-((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile was prepared according to Example 359 substituting 3,5-dichloro-4-(trifluoromethyl)pyridine for 1-bromo-8-methyl-naphthalene in step A. ES+APCI MS m/z 623.2 [M+H]+.

Example 601

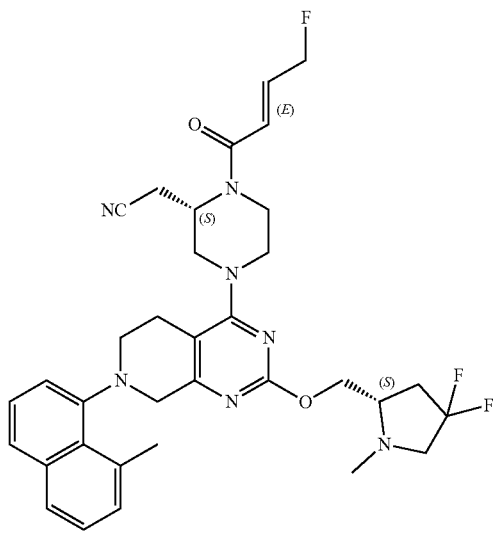

2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-fluorobut-2-enoyl]piperazin-2-yl]acetonitrile

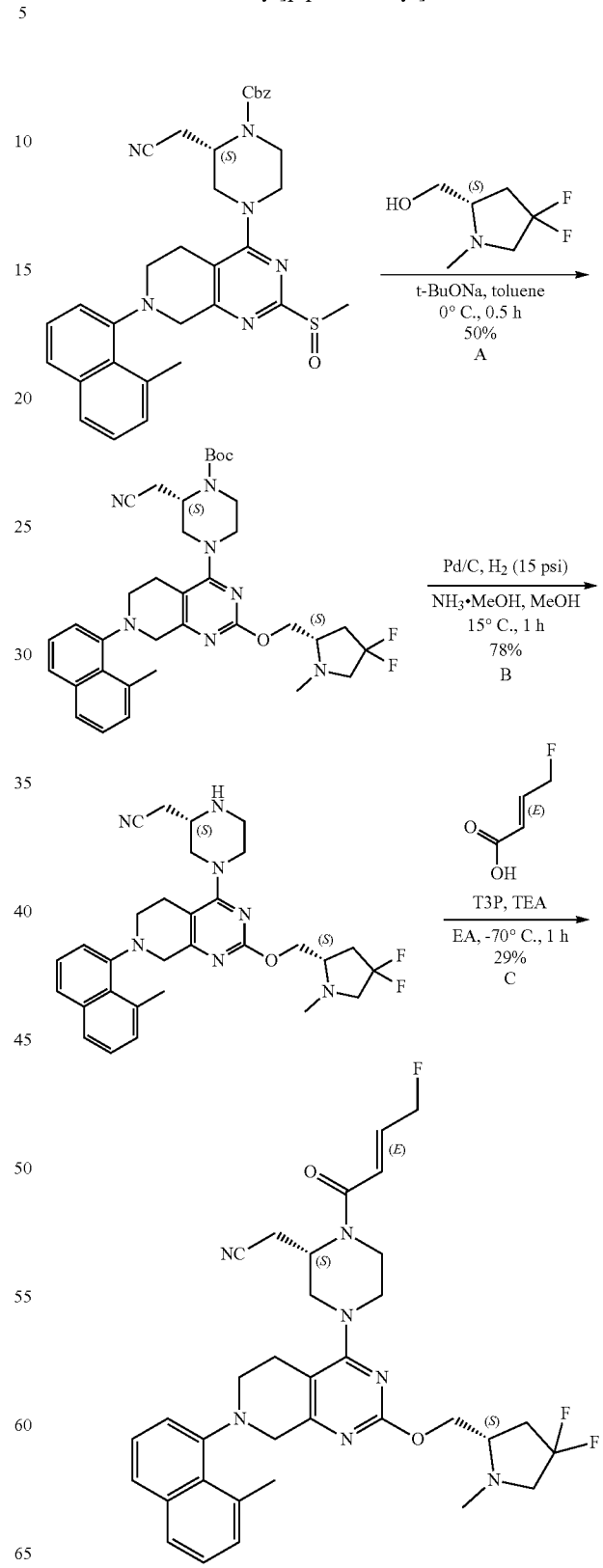

Step A: benzyl (2S)-2-(cyanomethyl)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate To a solution of benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (500 mg, 841 µmol, 1 eq) and [(2S)-4,4-difluoro-1-methyl-pyrrolidin-2-yl]methanol (191 mg, 1.26 mmol, 1.5 eq) in toluene (10 mL) was added t-BuONa (162 mg, 1.68 mmol, 2 eq). The mixture was stirred at 0° C. for 30 minutes. Upon completion, the mixture was diluted with water (10 mL) and extracted with EtOAc (2×40 mL). The organic layers were dried over Na₂SO₄ and concentrated under vacuum. The residue was purified by reversed phase flash [water (0.1% FA)/acetonitrile]. The desired fractions were collected and neutralized with NaHCO₃, concentrated under vacuum to remove MeCN and extracted with EtOAc (2×100 mL). The organic layers were dried over Na₂SO₄ and concentrated under vacuum to give benzyl (2S)-2-(cyanomethyl)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (300 mg, 418 µmol, 50% yield, 95% purity) as a yellow solid. LCMS [ESI, M+1]: 682.

Step B: 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (260 mg, 381 µmol, 1 eq) in MeOH (4 mL) was added Pd/C (120 mg, 10% purity), NH₃/MeOH (3 mL, 20% purity) under N₂. The suspension was degassed under vacuum and purged with H₂ several times. The mixture was stirred under H₂ (15 psi) at 15° C. for 1 hour. Upon completion, the mixture was filtered and the filtrate was concentrated under vacuum to give 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (180 mg, 296 µmol, 78% yield, 90% purity) as a yellow solid used directly into the next step without further purification. LCMS [ESI, M+1]: 548.

Step C: 2-[(2S)-4-[2-[[(2S)-4,4-difluoro-1-methyl-pyrrolidin-2-yl] methoxy]-7-(8-methyl-1-naphthyl)-6,8-dihydro-5H-pyrido[3,4-d]pyrimidin-4-yl]-1-[(E)-4-fluorobut-2-enoyl]piperazin-2-yl]acetonitrile To a solution of 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (150 mg, 274 umol, 1 eq), TEA (222 mg, 2.19 mmol, 305 uL, 8 eq) and (E)-4-fluorobut-2-enoic acid (57.0 mg, 548 µmol, 2 eq) in EA (3 mL) was added T3P (523 mg, 822 µmol, 489 µL, 50% purity in EA, 3 eq) at −70° C. The mixture was stirred at −70° C. for 1 hour. Upon completion, the reaction mixture was quenched with 1 M HCl (2.2 mL) at −70° C., stirred until no ice remained. Layers were separated. The organic layer was basified with saturated NaHCO₃ aqueous solution to pH=8 and extracted with ethyl acetate (15 mL×3). The combined organic layers were dried over Na₂SO₄, filtered and concentrated under vacuum. The residue was purified by chromatography (Al₂O₃, EtOAc/MeOH 1/0 to 20/1) followed by prep-HPLC (column: Waters Xbridge 150*25 5 u; mobile phase: [water (0.05% ammonia hydroxide v/v)-ACN]; B %: 55%-85%, 10 min). The desired fractions were collected and lyophilized to give 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-fluorobut-2-enoyl]piperazin-2-yl]acetonitrile (50.6 mg, 78 µmol, 29% yield, 98% purity) as a white solid. LCMS [ESI, M+1]: 634.

¹H NMR (400 MHz, chloroform-d) δ=7.70 (br d, J=8.0 Hz, 1H), 7.66 (t, J=8.0 Hz, 1H), 7.45-7.38 (m, 1H), 7.38-7.32 (m, 1H), 7.27-7.18 (m, 2H), 7.09-6.93 (m, 1H), 6.60 (br d, J=14.8 Hz, 1H), 5.32-4.93 (m, 3H), 4.64 (br s, 1H), 4.45 (td, J=5.2, 11.2 Hz, 1H), 4.32-3.63 (m, 6H), 3.58-3.36 (m, 3H), 3.25-2.96 (m, 5H), 2.93 (s, 3H), 2.88-2.77 (m, 1H), 2.75-2.50 (m, 3H), 2.46 (d, J=4.4 Hz, 3H), 2.34-2.15 (m, 1H).

Example 602

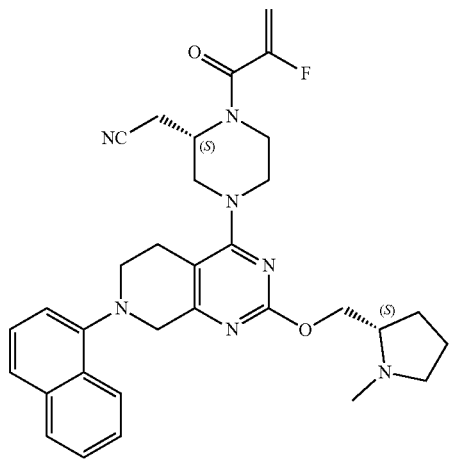

2-[(2S)-1-(2-fluoroprop-2-enoyl)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile

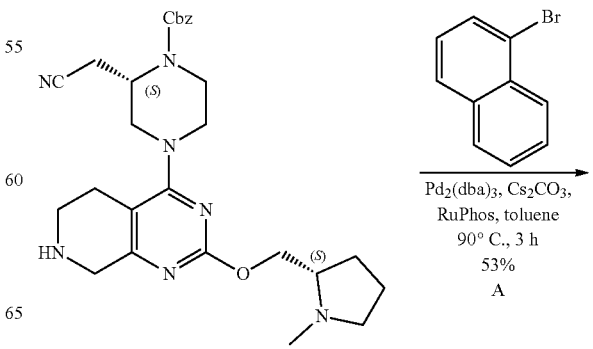

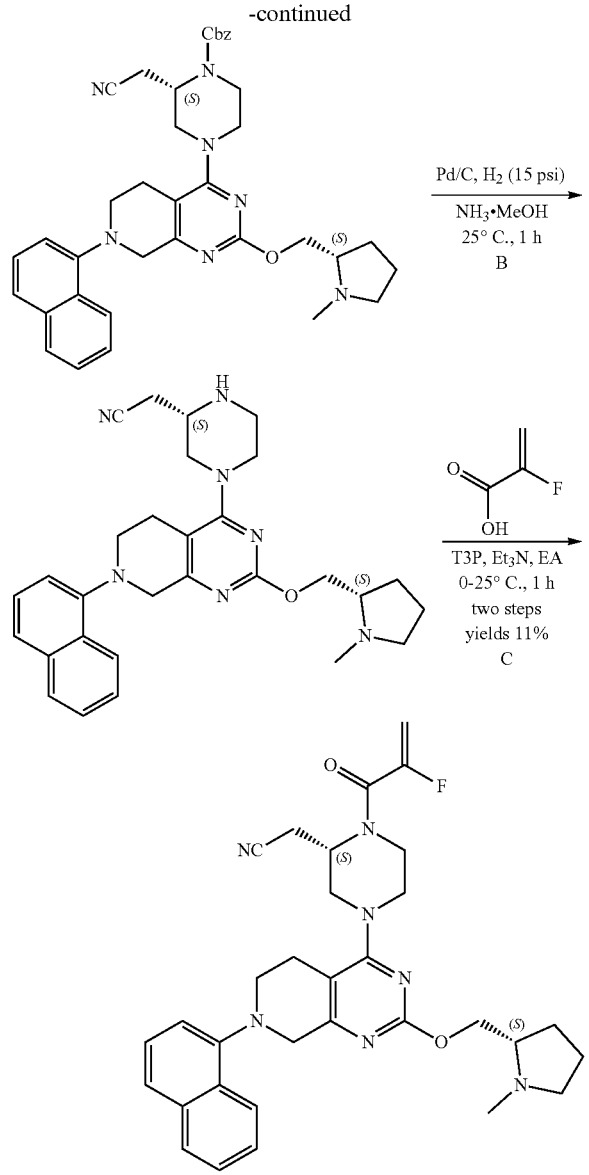

Step A: benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate To a mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (300 mg, 593 umol, 1.0 eq), 1-bromonaphthalene (184 mg, 890 μmol, 124 μL, 1.5 eq), Pd$_2$(dba)$_3$ (54.3 mg, 59.3 μmol, 0.1 eq), Cs$_2$CO$_3$ (483 mg, 1.48 mmol, 2.5 eq) and RuPhos (55.4 mg, 119 umol, 0.2 eq) in toluene (10 mL) was degassed and purged with N$_2$ for 3 times, and then the mixture was stirred at 90° C. for 3 hours under N$_2$ atmosphere. Upon completion, the mixture was diluted with water (10 mL) and extracted with ethyl acetate (1×50 mL) and the organic layer was separated, dried over sodium sulfate, filtered and concentrated under vacuum. The residue was purified by reverse phase HPLC (0.1% FA condition). The residue was basified with saturated aqueous NaHCO$_3$ solution to pH ~8, and then extracted with ethyl acetate (2×25 mL). The organic phase was separated, dried over sodium sulfate, filtered and concentrated under vacuum. Benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (200 mg, 317 μmol, 53% yield, 100% purity) was obtained as a yellow solid. LCMS [ESI, M+1]: 632.

Step B: 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (100 mg, 158 μmol, 1.0 eq) in MeOH (10 mL) was added Pd/C (20 mg, 10% purity) and NH$_3$.MeOH (8 mL, 20% purity) under N$_2$. The suspension was degassed under vacuum and purged with H$_2$ several times. The mixture was stirred under H$_2$ (15 psi) at 25° C. for 1 hour. Upon completion, the mixture was concentrated under vacuum. 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (70 mg, crude) was obtained as a yellow oil and used into next steps without further purification. LCMS [ESI, M+1]: 498.

Step C: 2-[(2S)-1-(2-fluoroprop-2-enoyl)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile To a solution of 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (60 mg, 121 umol, 1.0 eq), 2-fluoroprop-2-enoic acid (21.7 mg, 241 μmol, 2.0 eq) and Et$_3$N (97.6 mg, 965 umol, 134 uL, 8.0 eq) in ethyl acetate (6 mL) was added T3P (230 mg, 362 μmol, 215 μL, 50% purity, 3.0 eq) at 0° C. The mixture was stirred at 0-25° C. for 1 hour. Upon completion, the mixture was diluted with water (6 mL). The organic layer was separated, washed with brine (1×10 mL), dried over sodium sulfate, filtered and concentrated under vacuum. The mixture was purified by column chromatography (SiO$_2$, ethyl acetate/methanol=20/1 to 5/1). The residue was purified by prep-HPLC (column: Waters Xbridge 150*25 5 u; mobile phase: [water (0.05% ammonia hydroxide v/v)-ACN]; B %: 60%-78%, 10 min). The residue was concentrated under reduced pressure to remove ACN, and then lyophilized. 2-[(2S)-1-(2-fluoroprop-2-enoyl)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (7.23 mg, 12.7 μmol, 11% yield, 100% purity) was obtained as a white solid. LCMS [ESI, M+1]: 571.

1H NMR (400 MHz, chloroform-d) δ=8.27-8.16 (m, 1H), 7.91-7.81 (m, 1H), 7.61 (d, J=8.4 Hz, 1H), 7.55-7.47 (m, 2H), 7.43 (t, J=7.6 Hz, 1H), 7.15 (d, J=7.2 Hz, 1H), 5.56-5.33 (m, 1H), 5.26 (dd, J=3.2, 16.8 Hz, 1H), 4.85 (br s, 1H), 4.41 (dd, J=5.2, 10.8 Hz, 1H), 4.34-4.24 (m, 2H), 4.22-3.96 (m, 4H), 3.75-3.21 (m, 4H), 3.12 (br t, J=6.8 Hz, 2H), 3.04-2.92 (m, 2H), 2.87 (m, 2H), 2.70 (m, 1H), 2.50 (s, 3H), 2.38-2.23 (m, 1H), 2.15-1.99 (m, 1H), 1.94-1.73 (m, 3H).

Example 603

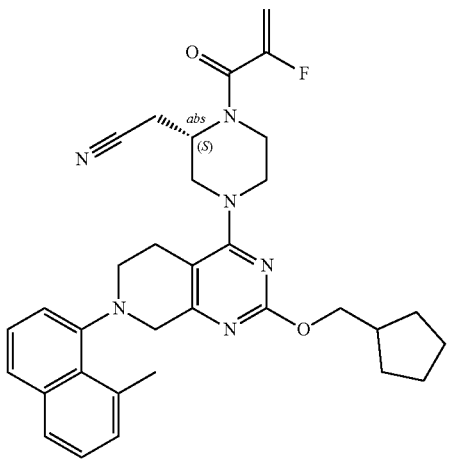

2-[(2S)-4-[2-(cyclopentylmethoxy)-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile

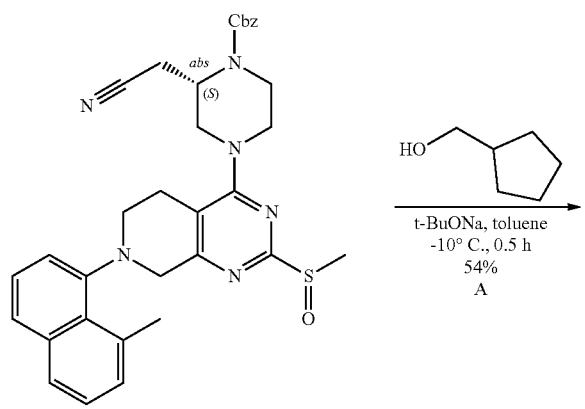

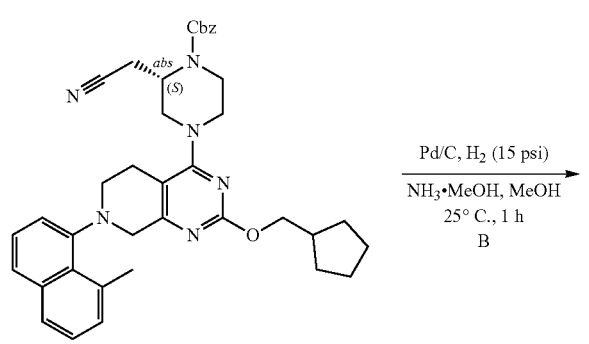

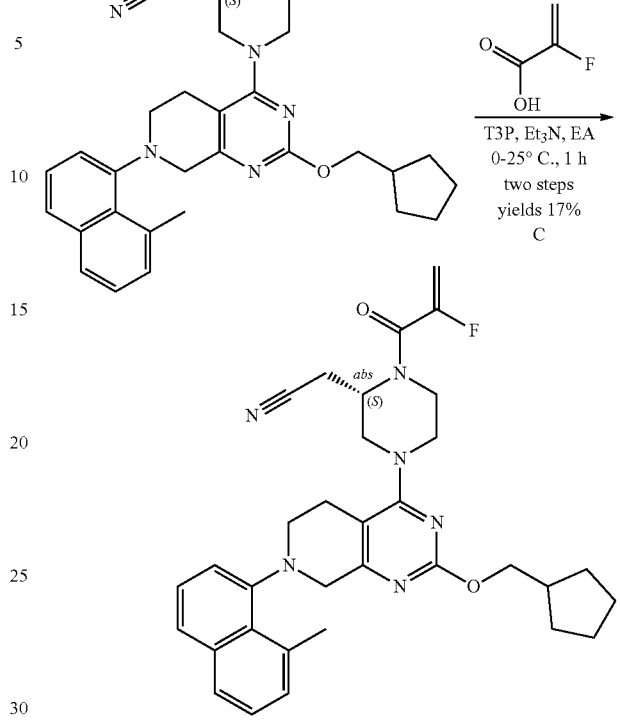

Step A: benzyl (2S)-2-(cyanomethyl)-4-[2-(cyclopentylmethoxy)-7-(8-methyl-1-naphthyl)-6,8-dihydro-5H-pyrido[3,4-d]pyrimidin-4-yl]piperazine-1-carboxylate To a solution of cyclopentylmethanol (50.5 mg, 504 μmol, 54.6 μL, 3.0 eq) and benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (100 mg, 168 μmol, 1.0 eq) in toluene (5 mL) was added t-BuONa (48.5 mg, 504 umol, 3.0 eq) at −10° C. The mixture was stirred at −10° C. for 0.5 hour. Upon completion, the reaction mixture was quenched with water (5 mL) at −10° C., and then extracted with ethyl acetate (2×20 mL). The combined organic layers were washed with brine (1×20 mL), dried over $Na_2SO_4$, filtered and concentrated under vacuum. The residue was purified by column chromatography ($SiO_2$, petroleum ether/ethyl acetate=50/1 to 3/1). The compound benzyl (2S)-2-(cyanomethyl)-4-[2-(cyclopentylmethoxy)-7-(8-methyl-1-naphthyl)-6,8-dihydro-5H-pyrimidin-4-yl]piperazine-1-carboxylate (58 mg, 91.6 μmol, 54% yield, 99.6% purity) was obtained as a white solid. LCMS [ESI, M+1]: 631.

$^1$H NMR (400 MHz, chloroform-d) δ=7.72-7.61 (m, 2H), 7.46-7.30 (m, 7H), 7.26-7.16 (m, 2H), 5.27-5.15 (m, 2H), 4.69 (br s, 1H), 4.32-3.72 (m, 7H), 3.59-3.30 (m, 2H), 3.24-2.87 (m, 7H), 2.87-2.30 (m, 4H), 1.90-1.76 (m, 2H), 1.64 (m, 2H), 1.57-1.51 (m, 1H), 1.42-1.21 (m, 3H).

Step B: 2-[(2S)-4-[2-(cyclopentylmethoxy)-7-(8-methyl-1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-(cyclopentylmethoxy)-7-(8-methyl-1-naphthyl)-6,8-dihydro-5H-pyrido[3,4-d]pyrimidin-4-yl]piperazine-1-carboxylate (58 mg, 92.0 μmol, 1.0 eq) in MeOH (3 mL) was added Pd/C (20 mg, 10% purity) and NH₃.MeOH (2 mL, 20% purity) under N₂. The suspension was degassed under vacuum and purged with H₂ several times. The mixture was stirred under H₂ (15 psi) at 25° C. for 1 hour. Upon completion, the mixture was concentrated under vacuum. 2-[(2S)-4-[2-(cyclopentylmethoxy)-7-(8-methyl-1-naphthyl)-6,8-dihydro-5H-pyrido[3,4-d]pyrimidin-4-yl]piperazin-2-yl]acetonitrile (34 mg, crude) was obtained as a yellow oil and used into next steps without further purification. LCMS [ESI, M+1]: 497.

Step C: 2-[(2S)-4-[2-(cyclopentylmethoxy)-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile To a solution of 2-[(2S)-4-[2-(cyclopentylmethoxy)-7-(8-methyl-1-naphthyl)-6,8-dihydro-5H-pyrido[3,4-d]pyrimidin-4-yl]piperazin-2-yl]acetonitrile (30 mg, 60.4 μmol, 1.0 eq), 2-fluoroprop-2-enoic acid (16.3 mg, 181 umol, 3.0 eq) and Et₃N (55.0 mg, 544 μmol, 75.7 μL, 9.0 eq) in EA (2.0 mL) was added T3P (154 mg, 242 umol, 144 uL, 50% purity, 4.0 eq) at 0° C. The mixture was stirred at 25° C. for 1 hour. Upon completion, the mixture was diluted with water (6 mL). The organic layer was separated, washed with brine (1×10 mL), dried over sodium sulfate, filtered and concentrated under vacuum. The mixture was purified by column chromatography (SiO₂, petroleum ether/ethyl acetate=20/1 to 1/1). The residue was purified by prep-HPLC (column: Waters Xbridge 150*25 5 u; mobile phase: [water (0.05% ammonia hydroxide v/v)-ACN]; B %: 65%-95%, 10 min). The residue was concentrated under reduced pressure to remove ACN, and then lyophilized. 2-[(2S)-4-[2-(cyclopentylmethoxy)-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile (8.85 mg, 15.3 μmol, two steps 17% yield, 98.2% purity) was obtained as a yellow solid. LCMS [ESI, M+1]: 569.

¹H NMR (400 MHz, chloroform-d) δ=7.70 (br d, J=8.0 Hz, 1H), 7.67-7.61 (m, 1H), 7.46-7.36 (m, 1H), 7.36-7.31 (m, 1H), 7.27-7.17 (m, 2H), 5.56-5.32 (m, 1H), 5.25 (dd, J=3.6, 16.8 Hz, 1H), 4.89 (br s, 1H), 4.33-3.98 (m, 5H), 3.95-3.72 (m, 2H), 3.60-3.39 (m, 2H), 3.30-2.96 (m, 4H), 2.92 (s, 3H), 2.91-2.73 (m, 2H), 2.69-2.54 (m, 1H), 2.45-2.29 (m, 1H), 1.93-1.74 (m, 2H), 1.69-1.62 (m, 2H), 1.60-1.53 (m, 2H), 1.45-1.25 (m, 2H).

Example 604

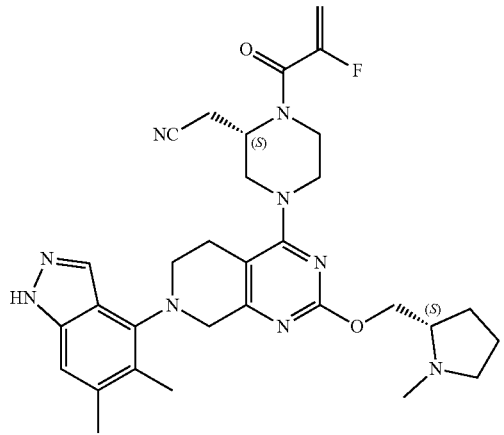

2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

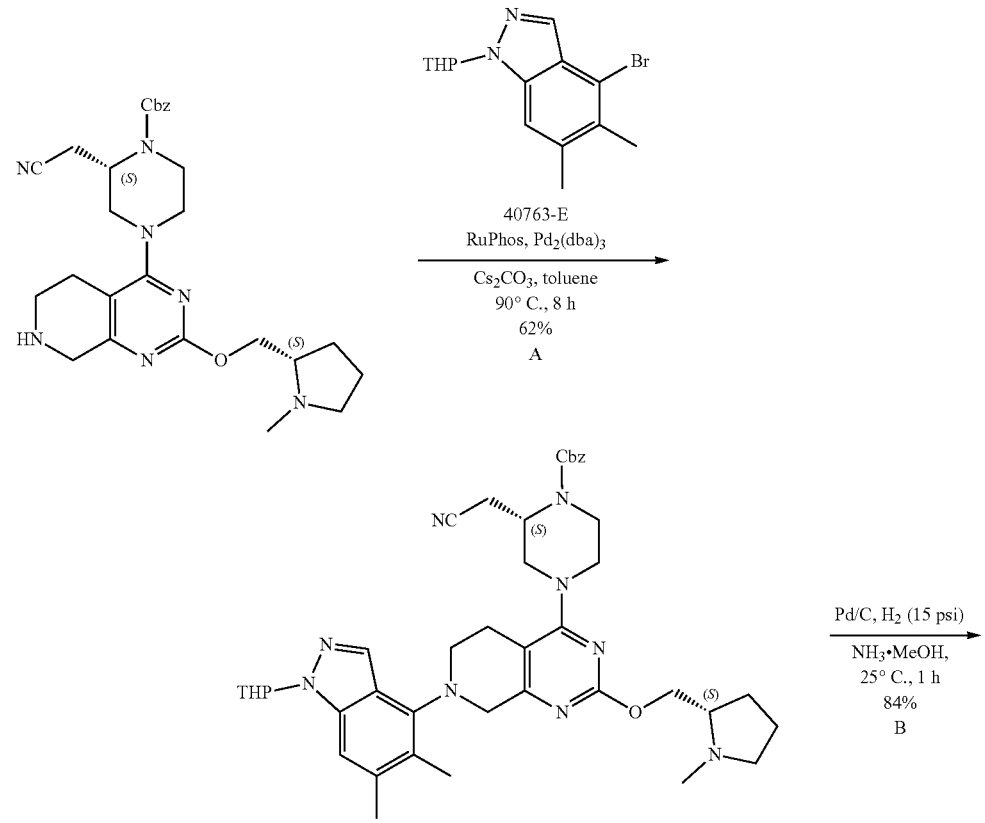

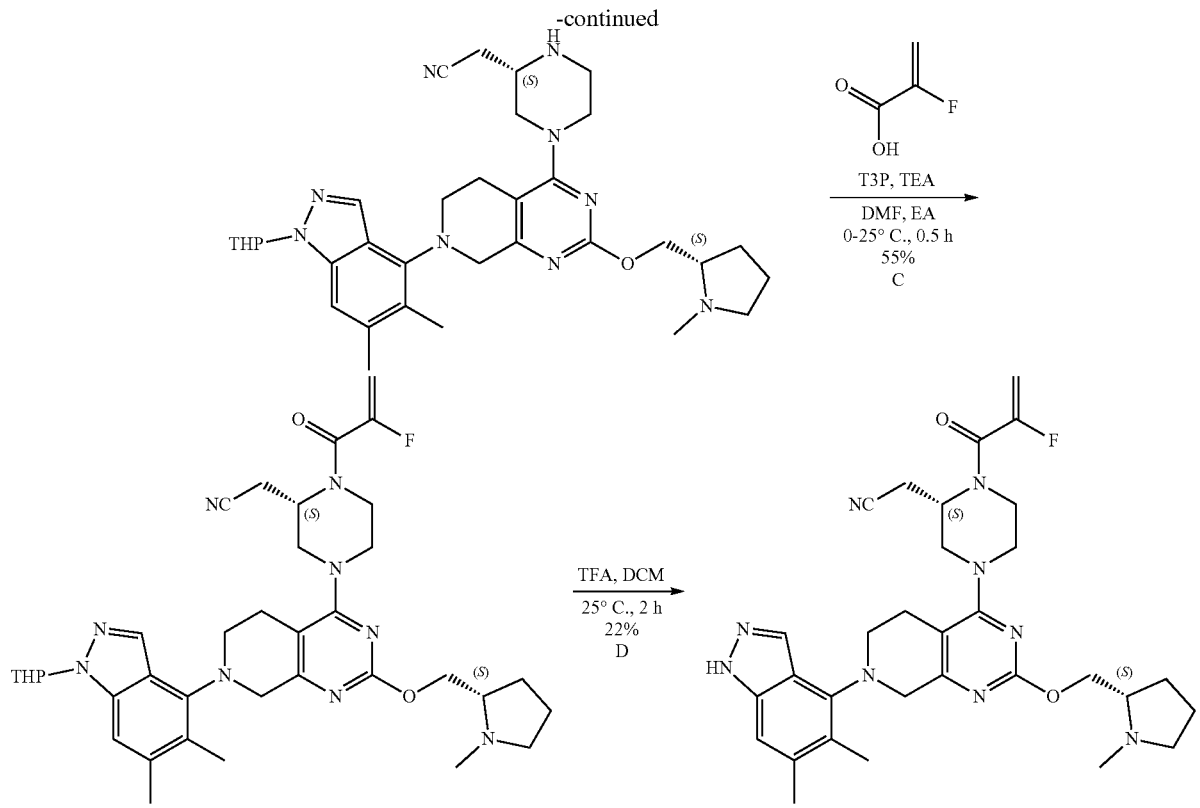

Step A: benzyl (2S)-2-(cyanomethyl)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate A mixture of benzyl (2S)-2-(cyanomethyl)-4-[2-[[(2S)-1-methyl pyrrolidin-2-yl]methoxy]-5,6,7,8-tetrahydropyrido[3,4-d]pyrimidin-4-yl]piperazine-1-carboxylate (1 g, 1.98 mmol, 1 eq), 4-bromo-5,6-dimethyl-1-tetrahydropyran-2-yl-indazole (795 mg, 2.57 mmol, 1.3 eq), RuPhos (369 mg, 791 umol, 0.4 eq), Cs$_2$CO$_3$ (1.61 g, 4.94 mmol, 2.5 eq) and Pd$_2$(dba)$_3$ (362 mg, 396 umol, 0.2 eq) in toluene (20 mL) was de-gassed and then heated to 90° C. for 8 hours under N$_2$. Upon completion, the mixture was filtered and the filtrate was concentrated under vacuum. The residue was purified by reverse phase flash [water (0.1% FA)/acetonitrile]. The desired fractions were collected and neutralized with solid NaHCO$_3$, concentrated under vacuum to remove MeCN and extracted with EtOAc (2×40 mL). The organic layers were dried over Na$_2$SO$_4$ and concentrated under vacuum to give benzyl (2S)-2-(cyanomethyl)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (900 mg, 1.23 mmol, 62% yield, 100% purity) as a brown solid.

$^1$H NMR (400 MHz, chloroform-d) δ=7.98 (s, 1H), 7.43-7.33 (m, 5H), 7.22 (s, 1H), 5.66 (dd, J=2.8, 9.6 Hz, 1H), 5.20 (s, 2H), 4.68 (br s, 1H), 4.39 (dd, J=4.8, 10.0 Hz, 1H), 4.25 (s, 2H), 4.18-4.14 (m, 1H), 4.04 (br d, J=12.0 Hz, 2H), 3.95-3.84 (m, 1H), 3.75 (dt, J=2.8, 10.8 Hz, 1H), 3.50 (br t, J=5.2 Hz, 2H), 3.30 (br s, 2H), 3.13-2.98 (m, 2H), 2.95-2.52 (m, 6H), 2.47 (s, 3H), 2.43 (s, 3H), 2.32 (s, 3H), 2.30-2.23 (m, 1H), 2.22-2.11 (m, 1H), 2.07 (br d, J=3.2 Hz, 1H), 1.89-1.63 (m, 8H).

Step B: 2-[(2S)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (0.9 g, 1.23 mmol, 1 eq) in MeOH (20 mL) was added NH$_3$.MeOH (20 mL, 20% purity), Pd/C (0.45 g, 10% purity) under N$_2$. The suspension was degassed under vacuum and purged with H$_2$ several times. The mixture was stirred under H$_2$ (15 psi) at 25° C. for 1 hour. Upon completion, the catalyst was removed by filtering through a plug of celite. The solvent was removed under reduced pressure. 2-[(2S)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile (620 mg, 1.03 mmol, 84% yield, 100% purity) was obtained as a yellow solid which was used directly in the next step without further purification. LCMS [ESI, M+1]: 600.

Step C: 2-[(2S)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(5,6-dimethyl-1-tetrahydropyran-2-yl-indazol-4-yl)-2-[[(2S)-1-methylpyrrolidin-2-yl]

methoxy]-6,8-dihydro-5H-pyrido[3,4-d]pyrimidin-4-yl]piperazin-2-yl]acetonitrile (600 mg, 1.00 mmol, 1 eq) in DMF (8 mL) was added 2-fluoroprop-2-enoic acid (180 mg, 2.00 mmol, 2 eq) in EA (4 mL) and TEA (304 mg, 3.00 mmol, 414 μL, 3 eq) followed by T3P (955 mg, 1.50 mmol, 892 μL, 50% purity in EtOAc, 1.5 eq) at 0° C. The mixture was stirred at 25° C. for 0.5 hour. Upon completion, the mixture was diluted with water (20 mL) and extracted with EtOAc (3×20 mL). The organic layers were dried over Na$_2$SO$_4$ and concentrated under vacuum. The residue was purified by reverse phase flash [water (0.1% FA)/acetonitrile]. The desired fractions were collected and neutralized with solid NaHCO$_3$, concentrated under vacuum to remove MeCN and extracted with EtOAc (3×100 mL). The organic layers were dried over Na$_2$SO$_4$ and concentrated under vacuum to give 2-[(2S)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (380 mg, 554 μmol, 55% yield, 98% purity) as a yellow solid. LCMS [ESI, M+1]: 672.

$^1$H NMR (400 MHz, chloroform-d) δ=7.98 (s, 1H), 7.22 (s, 1H), 5.66 (dd, J=2.4, 9.2 Hz, 1H), 5.51-5.32 (m, 1H), 5.25 (br dd, J=3.6, 16.8 Hz, 1H), 5.09-4.59 (m, 1H), 4.44-4.33 (m, 1H), 4.26 (br s, 2H), 4.19-4.14 (m, 1H), 4.05 (br d, J=14.4 Hz, 2H), 4.00-3.91 (m, 1H), 3.76 (dt, J=2.4, 11.2 Hz, 1H), 3.59-3.39 (m, 3H), 3.37-3.21 (m, 1H), 3.14-3.02 (m, 2H), 2.90-2.52 (m, 6H), 2.48 (s, 3H), 2.43 (s, 3H), 2.33 (s, 3H), 2.29-2.23 (m, 1H), 2.22-2.08 (m, 2H), 1.90-1.69 (m, 8H).

Step D: 2-[(2S)-4-[7-(5,6-dimethyl-1H-indazol-4-yl)-2-[[(2S)-1-methyl pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (360 mg, 536 μmol, 1 eq) in DCM (0.4 mL) was added TFA (1.22 g, 10.7 mmol, 794 μL, 20 eq). The mixture was stirred at 25° C. for 2 hours. Upon completion, the mixture was diluted with DCM (10 mL) and neutralized with saturated NaHCO$_3$ solution. The separated aqueous layer was extracted with DCM (2×10 mL). Combined organic layers were dried over Na$_2$SO$_4$ and concentrated under vacuum. The residue was purified by reverse phase flash [water (0.1% FA)/acetonitrile]. The desired fractions were collected and neutralized with solid NaHCO$_3$, concentrated under vacuum to remove MeCN and extracted with EtOAc (2×15 mL). The organic layers were dried over Na$_2$SO$_4$ and concentrated under vacuum. The residue was purified by prep-HPLC (column: Xtimate C18 150*25 mm*5 um; mobile phase: [water (0.05% ammonia hydroxide v/v)-ACN]; B %: 40%-70%, 10 min). The desired fractions were collected and lyophilized to give 2-[(2S)-4-[7-(5,6-dimethyl-1H-indazol-4-yl)-2-[[(2S)-1-methyl pyrrolidin-2-yl]methoxy]-6,8-dihydro-5H-pyrido [3,4-d]pyrimidin-4-yl]-1-(2-fluoroprop-2-enoyl)piperazin-2-yl]acetonitrile (73.3 mg, 120 μmol, 22% yield, 96.6% purity) as a white solid. LCMS [ESI, M+1]: 588.

$^1$H NMR (400 MHz, chloroform-d) δ=9.97 (br s, 1H), 8.04 (s, 1H), 7.15 (s, 1H), 5.55-5.31 (m, 1H), 5.26 (dd, J=3.6, 16.8 Hz, 1H), 5.08-4.50 (m, 1H), 4.39 (dd, J=4.8, 10.8 Hz, 1H), 4.29 (s, 2H), 4.20-3.68 (m, 4H), 3.65-3.27 (m, 4H), 3.10 (br t, J=7.8 Hz, 2H), 3.02-2.72 (m, 4H), 2.71-2.60 (m, 1H), 2.48 (s, 3H), 2.42 (s, 3H), 2.34 (s, 3H), 2.31-2.24 (m, 1H), 2.12-2.01 (m, 1H), 1.93-1.73 (m, 3H).

Example 605

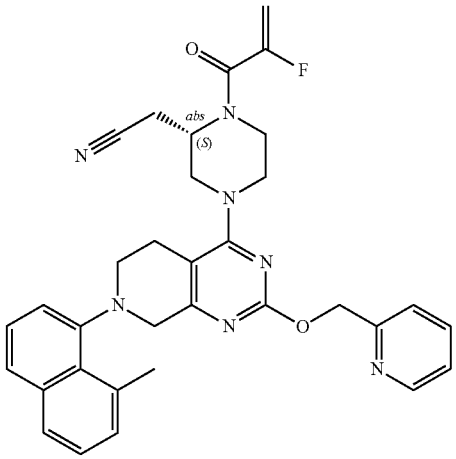

2-[(2S)-1-(2-fluoroprop-2-enoyl)-4-[7-(8-methyl-1-naphthyl)-2-(2-pyridylmethoxy)-6,8-dihydro-5H-pyrido[3,4-d]pyrimidin-4-yl]piperazin-2-yl]acetonitrile

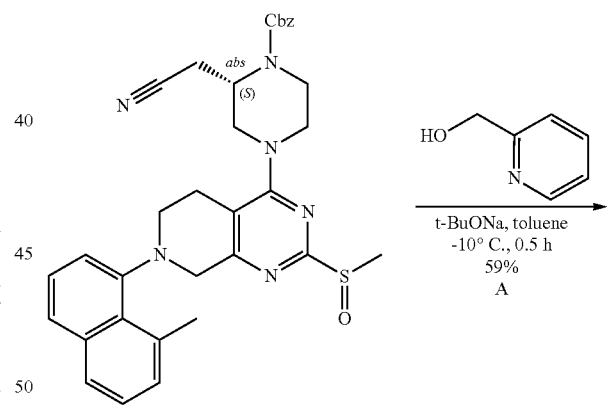

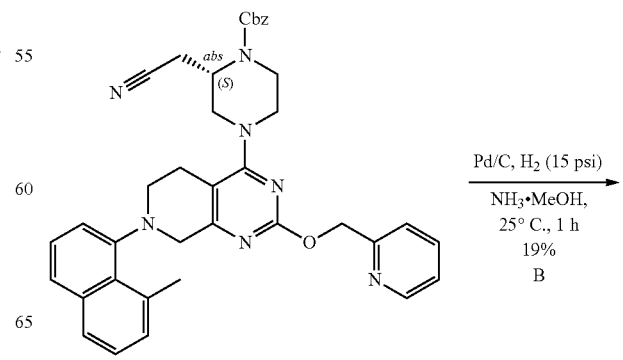

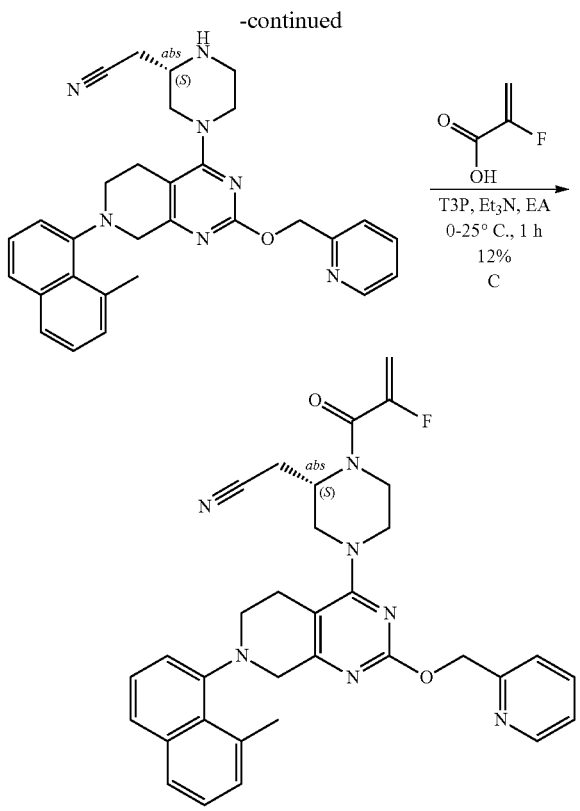

Step A: benzyl (2S)-2-(cyanomethyl)-4-[7-(8-methyl-1-naphthyl)-2-(2-pyridylmethoxy)-6,8-dihydro-5H-pyrido[3,4-d]pyrimidin-4-yl]piperazine-1-carboxylate To a solution of 2-pyridylmethanol (55.1 mg, 504 µmol, 48.7 µL, 3.0 eq) and benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (100 mg, 168 µmol, 1.0 eq) in toluene (5.00 mL) was added t-BuONa (48.5 mg, 504 µmol, 3.0 eq) at −10° C. The mixture was stirred at −10° C. for 0.5 hour. Upon completion, the mixture was quenched with water (5.00 mL) and extracted with ethyl acetate (2×10 mL). The combined organic layers were washed with brine (1×10 mL), dried over Na$_2$SO$_4$, filtered and concentrated under vacuum. The residue was purified by column chromatography (SiO$_2$, petroleum ether/ethyl acetate=50/1 to 1/1). Benzyl (2S)-2-(cyanomethyl)-4-[7-(8-methyl-1-naphthyl)-2-(2-pyridylmethoxy)-6,8-dihydro-5H-pyrido[3,4-d]pyrimidin-4-yl]piperazine-1-carboxylate (64.0 mg, 98.8 µmol, 59% yield, 98.8% purity) was obtained as a yellow solid. LCMS [ESI, M+1]: 641.

Step B: 2-[(2S)-4-[7-(8-methyl-1-naphthyl)-2-(2-pyridylmethoxy)-6,8-dihydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-2-(2-pyridylmethoxy)-6,8-dihydro-5H-pyrido[3,4-d]pyrimidin-4-yl]piperazine-1-carboxylate (64.0 mg, 100 µmol, 1.0 eq) in MeOH (3.00 mL) was added Pd/C (20.0 mg, 10% purity) and NH$_3$.MeOH (2.00 mL, 20% purity) under N$_2$. The suspension was degassed under vacuum and purged with H$_2$ several times. The mixture was stirred under H$_2$ (15 psi) at 25° C. for 1 hour. Upon completion, the mixture was concentrated under vacuum. The residue was purified by column chromatography (SiO$_2$, dichloromethane/methanol=100/1 to 8/1). 2-[(2S)-4-[7-(8-methyl-1-naphthyl)-2-(2-pyridylmethoxy)-6,8-dihydro-5H-pyrido[3,4-d]pyrimidin-4-yl]piperazin-2-yl]acetonitrile (15.0 mg, 19.3 µmol, 19% yield, 64.9% purity) was obtained as a yellow oil. LCMS [ESI, M+1]: 506.

Step C: 2-[(2S)-1-(2-fluoroprop-2-enoyl)-4-[7-(8-methyl-1-naphthyl)-2-(2-pyridylmethoxy)-6,8-dihydro-5H-pyrido[3,4-d]pyrimidin-4-yl]piperazin-2-yl]acetonitrile To a solution of 2-[(2S)-4-[7-(8-methyl-1-naphthyl)-2-(2-pyridylmethoxy)-6,8-dihydro-5H-pyrido[3,4-d]pyrimidin-4-yl]piperazin-2-yl]acetonitrile (10.0 mg, 19.8 µmol, 1.0 eq), 2-fluoroprop-2-enoic acid (5.34 mg, 59.3 µmol, 3.0 eq) and Et$_3$N (18.0 mg, 178 µmol, 24.8 µL, 9.0 eq) in EtOAc (2.00 mL) was added T3P (50.3 mg, 79.1 µmol, 47.1 µL, 50% purity in ethyl acetate, 4.0 eq) at 0° C. The mixture was stirred at 25° C. for 1 hour. Upon completion, the mixture was diluted with water (3.00 mL). The organic layer was separated, washed with brine (1×10 mL), dried over sodium sulfate, filtered and concentrated under vacuum. The mixture was purified by column chromatography (SiO$_2$, ethyl acetate/methanol=50/1 to 10/1). The residue was purified by prep-HPLC (column: Xtimate C18 150*25 mm*5 um; mobile phase: [water (0.05% ammonia hydroxide v/v)-ACN]; B %: 50%-80%, 10 min). The residue was concentrated under reduced pressure to remove ACN, and then lyophilized. 2-[(2S)-1-(2-fluoroprop-2-enoyl)-4-[7-(8-methyl-1-naphthyl)-2-(2-pyridylmethoxy)-6,8-dihydro-5H-pyrido[3,4-d]pyrimidin-4-yl]piperazin-2-yl]acetonitrile (1.41 mg, 2.44 umol, 12% yield, 99.8% purity) was obtained as a yellow solid. LCMS [ESI, M+1]: 579.

$^1$H NMR (400 MHz, chloroform-d) δ=8.61-8.55 (m, 1H), 7.74-7.62 (m, 3H), 7.55-7.48 (m, 1H), 7.45-7.32 (m, 2H), 7.26-7.17 (m, 3H), 5.52-5.48 (m, 2H), 5.47-5.33 (m, 1H), 5.25 (dd, J=3.6, 17.2 Hz, 1H), 4.79 (br s, 1H), 4.38-3.73 (m, 6H), 3.61-3.41 (m, 2H), 3.26-3.12 (m, 2H), 3.09-2.95 (m, 2H), 2.92 (s, 3H), 2.85-2.56 (m, 2H).

Example 606

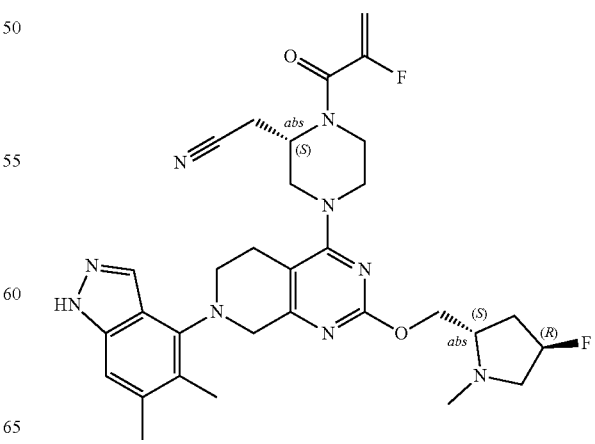

2-((S)-4-(7-(5,6-dimethyl-1H-indazol-4-yl)-2-(((2S,4R)-4-fluoro-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile
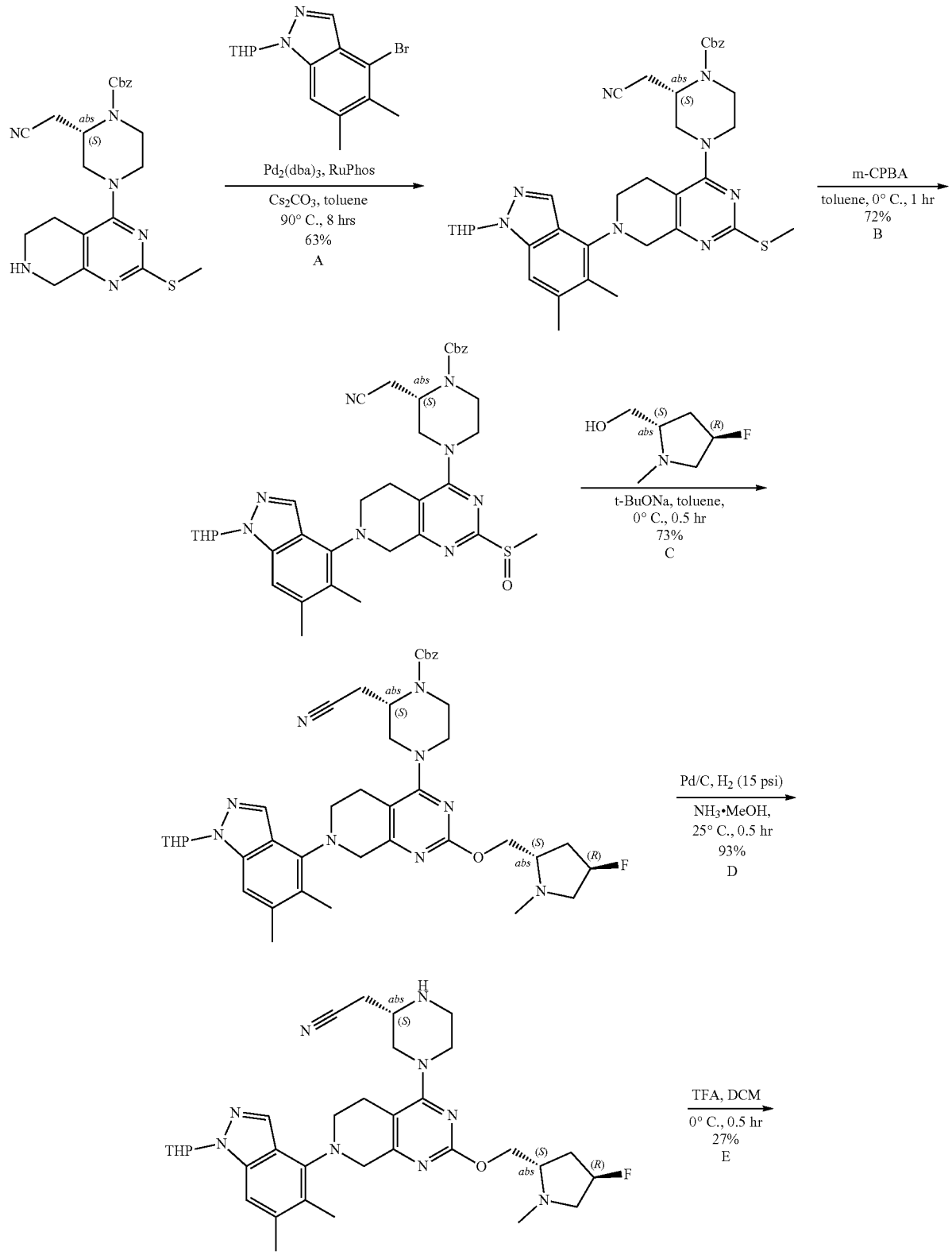

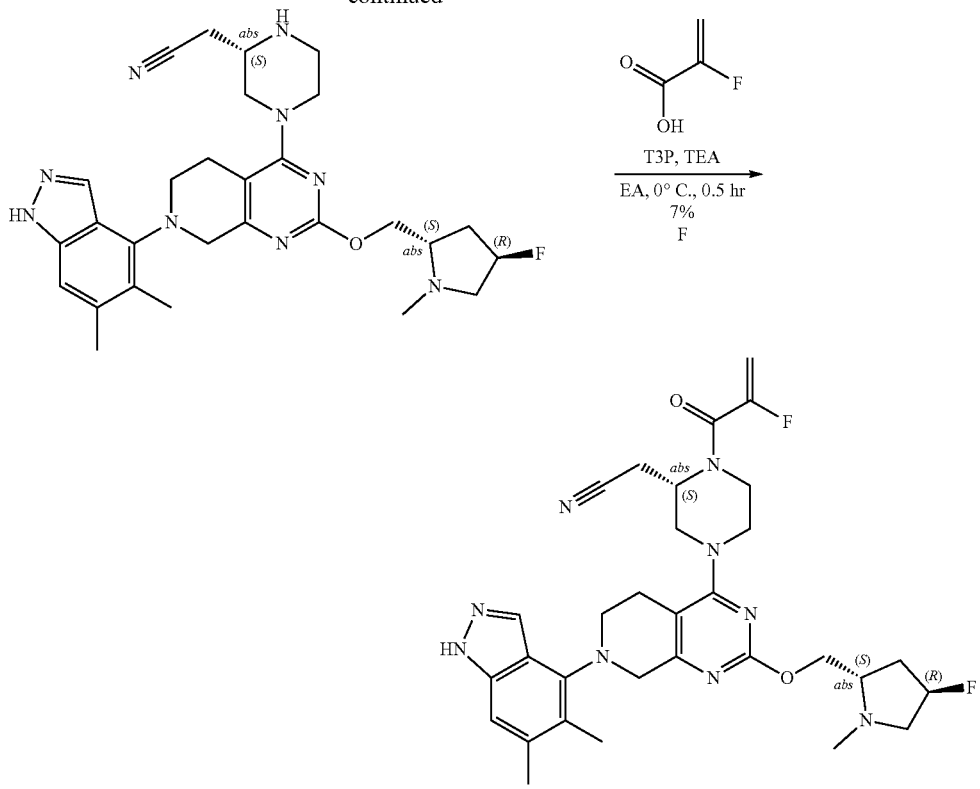

Step A: benzyl (2S)-2-(cyanomethyl)-4-[7-(5,6-dimethyl-1-tetrahydropyran-2-yl-indazol-4-yl)-2-methylsulfanyl-6,8-dihydro-5H-pyrido[3,4-d]pyrimidin-4-yl]piperazine-1-carboxylate A mixture of benzyl (2S)-2-(cyanomethyl)-4-(2-methylsulfanyl-5,6,7,8-tetrahydropyrido[3,4-d]pyrimidin-4-yl)piperazine-1-carboxylate (5.0 g, 11.4 mmol, 1.0 eq), 4-bromo-5,6-dimethyl-1-tetrahydropyran-2-yl-indazole (7.05 g, 22.8 mmol, 2.0 eq), Pd$_2$(dba)$_3$ (2.09 g, 2.28 mmol, 0.2 eq), RuPhos (2.13 g, 4.56 mmol, 0.4 eq) and Cs$_2$CO$_3$ (9.29 g, 28.5 mmol, 2.5 eq) in toluene (100 mL) was degassed and purged with N$_2$ 3 times, and then the mixture was stirred at 90° C. for 8 hours under N$_2$ atmosphere. The reaction mixture was diluted with water (100 mL) and extracted with ethyl acetate (3×200 mL). The combined organic layers were washed with brine (100 mL), dried over Na$_2$SO$_4$, filtered and concentrated under reduced pressure to give a residue. The residue was purified by column chromatography (SiO$_2$, Petroleum ether/Ethyl acetate=20/1 to 2/1) and further purified by reverse phase flash [water (0.1% formic acid)/acetonitrile)]. The mixture was adjusted pH ~7 with saturated NaHCO$_3$ aqueous solution and extracted with ethyl acetate (3×100 mL). The combined organic layers were washed with brine (50 mL), dried over Na$_2$SO$_4$, filtered and concentrated under reduced pressure to give the product. Benzyl (2S)-2-(cyanomethyl)-4-[7-(5,6-dimethyl-1-tetrahydropyran-2-yl-indazol-4-yl)-2-methylsulfanyl-6,8-dihydro-5H-pyrido[3,4-d]pyrimidin-4-yl]piperazine-1-carboxylate (4.90 g, 7.20 mmol, 63% yield, 98% purity) was obtained as a yellow solid. LCMS [ESI, M+1]: 667.

$^1$H NMR (400 MHz, chloroform-d) δ=7.98 (s, 1H), 7.50-7.31 (m, 5H), 7.22 (s, 1H), 5.66 (dd, J=2.4, 9.6 Hz, 1H), 5.27-5.13 (m, 2H), 4.69 (br s, 1H), 4.27 (s, 2H), 4.13-3.97 (m, 3H), 3.89 (d, J=11.6 Hz, 1H), 3.81-3.68 (m, 1H), 3.51 (t, J=5.2 Hz, 2H), 3.30 (br s, 2H), 3.04 (t, J=11.6 Hz, 1H), 2.93-2.66 (m, 4H), 2.62-2.48 (m, 4H), 2.43 (s, 3H), 2.32 (s, 3H), 2.23-2.12 (m, 1H), 2.11-2.05 (m, 1H), 1.85-1.67 (m, 3H).

Step B: benzyl (2S)-2-(cyanomethyl)-4-[7-(5,6-dimethyl-1-tetrahydropyran-2-yl-indazol-4-yl)-2-methylsulfinyl-6,8-dihydro-5H-pyrido[3,4-d]pyrimidin-4-yl]piperazine-1-carboxylate To a solution of benzyl (2S)-2-(cyanomethyl)-4-[7-(5,6-dimethyl-1-tetrahydropyran-2-yl-indazol-4-yl)-2-methylsulfanyl-6,8-dihydro-5H-pyrido[3,4-d]pyrimidin-4-yl]piperazine-1-carboxylate (500 mg, 749 μmol, 1.0 eq) in toluene (10 mL) was added m-CPBA (152 mg, 749 μmol, 85% purity, 1.0 eq). The mixture was stirred at 0° C. for 1 hour. The mixture was diluted with water (10 mL) and adjusted pH ~7 with saturated NaHCO$_3$ aqueous solution. Then the mixture was extracted with ethyl acetate (3×20 mL). The combined organic layers were washed with brine (20 mL), dried over Na$_2$SO$_4$, filtered and concentrated under reduced pressure to give the product. Benzyl (2S)-2-(cyanomethyl)-4-[7-(5,6-dimethyl-1-tetrahydropyran-2-yl-indazol-4-yl)-2-methylsulfinyl-6,8-dihydro-5H-pyrido[3,4-d]pyrimidin-4-yl]piperazine-1-carboxylate (400 mg, 539 μmol, 72% yield, 92% purity) was obtained as a yellow solid and used next step directly without purification. LCMS [ESI, M+1]: 683.

Step C: benzyl (2S)-2-(cyanomethyl)-4-[7-(5,6-dimethyl-1-tetrahydropyran-2-yl-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazine-1-carboxylate To a solution of benzyl (2S)-2-(cyanomethyl)-4-[7-(5,6-dimethyl-1-tetrahydropyran-2-yl-indazol-4-yl)-2-methylsulfinyl-6,8-dihydro-5H-pyrido[3,4-d]pyrimidin-4-yl]piperazine-1-carboxylate (350 mg, 512 µmol, 1.0 eq) in toluene (10 mL) was added t-BuONa (148 mg, 1.54 mmol, 3.0 eq) and [(2S,4R)-4-fluoro-1-methyl-pyrrolidin-2-yl]methanol (136 mg, 1.03 mmol, 2.0 eq). The mixture was stirred at 0° C. for 0.5 hour. The reaction mixture was diluted with water (20 mL) and extracted with ethyl acetate (3×30 mL). The combined organic layers were washed with brine (20 mL), dried over $Na_2SO_4$, filtered and concentrated under reduced pressure to give a residue. The residue was purified by reverse phase flash [water (0.1% formic acid)/acetonitrile)]. The mixture was adjusted pH ~7 with saturated $NaHCO_3$ aqueous solution and extracted with ethyl acetate (3×50 mL). The combined organic layers were washed with brine (20 mL), dried over $Na_2SO_4$, filtered and concentrated under reduced pressure to give the product. Benzyl (2S)-2-(cyanomethyl)-4-[7-(5,6-dimethyl-1-tetrahydropyran-2-yl-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazine-1-carboxylate (280 mg, 372 µmol, 73% yield, 100% purity) was obtained as a yellow solid. LCMS [ESI, M+1]: 752.

Step C: 2-[(2S)-4-[7-(5,6-dimethyl-1-tetrahydropyran-2-yl-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(5,6-dimethyl-1-tetrahydropyran-2-yl-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazine-1-carboxylate (230 mg, 306 umol, 1.0 eq) in methanol (2.0 mL) was added dry Pd/C (50.0 mg, 10% purity) and $NH_3$/methanol (1.00 mL, 20% purity) under $N_2$. The suspension was degassed under vacuum and purged with $H_2$ several times. The mixture was stirred under $H_2$ (15 psi) at 25° C. for 0.5 hour. The mixture was concentrated under vacuum. 2-[(2S)-4-[7-(5,6-dimethyl-1-tetrahydropyran-2-yl-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile (180 mg, 285 µmol, 93% yield, 98% purity) was obtained as a yellow solid and used next step without purification. LCMS [ESI, M+1]: 618.

Step D: 2-[(2S)-4-[7-(5,6-dimethyl-1H-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile To a solution of 2-[(2S)-4-[7-(5,6-dimethyl-1-tetrahydropyran-2-yl-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile (30 mg, 48.6 µmol, 1.0 eq) in dichloromethane (300 uL) was added TFA (221 mg, 1.94 mmol, 144 µL, 40 eq). The mixture was stirred at 0° C. for 0.5 hour. The mixture was concentrated under vacuum and diluted with water (10 mL). The mixture was adjusted pH ~8 with saturated $NaHCO_3$ aqueous solution and extracted with dichloromethane (3×20 mL). The combined organic layers were washed with brine (20 mL), dried over $Na_2SO_4$, filtered and concentrated under reduced pressure to give the product. The residue was purified by prep-HPLC (column: Xtimate C18 150*25 mm*5 um; mobile phase: [water (0.05% ammonia hydroxide v/v)-ACN]; B %: 26%-56%, 1 min). The desired fraction was collected and lyophilized. 2-[(2S)-4-[7-(5,6-dimethyl-1H-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile (7.08 mg, 13.1 µmol, 27% yield, 98.5% purity) was obtained as a yellow solid. LCMS [ESI, M+1]: 534.

$^1$H NMR (400 MHz, chloroform-d) δ=10.14 (br s, 1H), 8.04 (d, J=0.8 Hz, 1H), 7.14 (s, 1H), 5.32-5.03 (m, 1H), 4.44 (dd, J=4.4, 11.2 Hz, 1H), 4.33-4.19 (m, 3H), 4.00 (br d, J=12.8 Hz, 1H), 3.82 (br d, J=12.0 Hz, 1H), 3.65-3.41 (m, 3H), 3.27 (br d, J=6.4 Hz, 1H), 3.17-2.95 (m, 4H), 2.90 (br dd, J=10.0, 12.4 Hz, 1H), 2.83-2.47 (m, 8H), 2.41 (s, 3H), 2.38-2.23 (m, 4H), 2.09-1.90 (m, 1H).

Step E: 2-[(2S)-4-[7-(5,6-dimethyl-1H-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(5,6-dimethyl-1H-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]piperazin-2-yl]acetonitrile (100 mg, 187 µmol, 1.0 eq) and 2-fluoroprop-2-enoic acid (25.3 mg, 281 µmol, 1.5 eq) in ethyl acetate (2.0 mL) was added T3P (477 mg, 749 µmol, 446 µL, 50% purity in ethyl acetate, 4.0 eq) and TEA (114 mg, 1.12 mmol, 156 µL, 6.0 eq) at 0° C. The mixture was stirred at 0° C. for 0.5 hour. The reaction mixture was diluted with water (20 mL) and extracted with ethyl acetate (3×30 mL). The combined organic layers were washed with brine (20 mL), dried over $Na_2SO_4$, filtered and concentrated under reduced pressure to give a residue. The residue was purified by column chromatography ($SiO_2$, Ethyl acetate/Methanol=100/1 to 10/1) and further purification by prep-HPLC (column: Waters Xbridge 150*25 5 u; mobile phase: [water (0.05% ammonia hydroxide v/v)-ACN]; B %: 38%-68%, 10 min). The desired fraction was collected and lyophilized. 2-[(2S)-4-[7-(5,6-dimethyl-1H-indazol-4-yl)-2-[[(2S,4R)-4-fluoro-1-methyl-pyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (8 mg, 12.8 umol, 7% yield, 96.9% purity) was obtained as a white solid. LCMS [ESI, M+1]: 606.

$^1$H NMR (400 MHz, chloroform-d) δ=10.03 (br s, 1H), 8.04 (s, 1H), 7.15 (s, 1H), 5.42 (dd, J=6.4 Hz, J=47.2 Hz 1H), 5.31-5.05 (m, 2H), 5.04-3.76 (m, 9H), 3.65-3.47 (m, 3H), 3.42-3.25 (m, 1H), 3.20-2.70 (m, 6H) 2.70-2.55 (m, 1H), 2.51 (s, 3H), 2.42 (s, 3H), 2.38-2.25 (m, 4H), 2.10-1.87 (m, 1H).

Example 607

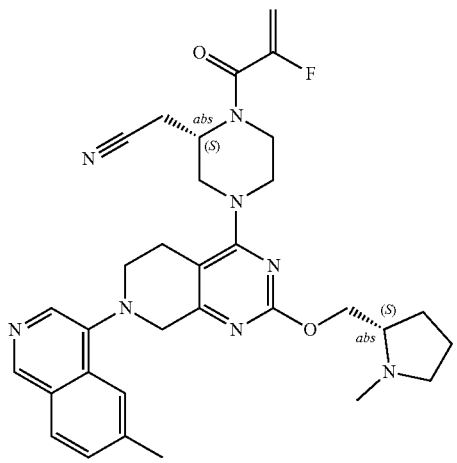

2-((S)-1-(2-fluoroacryloyl)-4-(7-(6-methylisoquino-lin-4-yl)-2-(((S)-1-methylpyrrolidin-2-yl)methoxy)-5,6,7,8-tetrahydropyrido[3,4-d]pyrimidin-4-yl)piper-azin-2-yl)acetonitrile

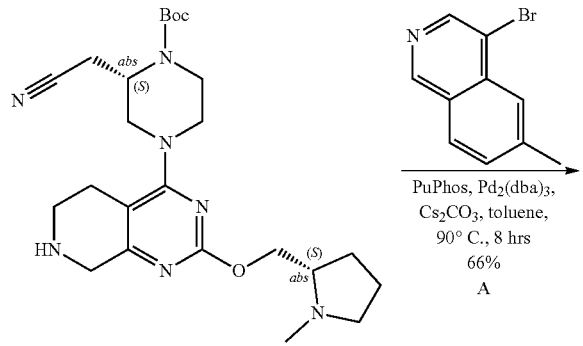

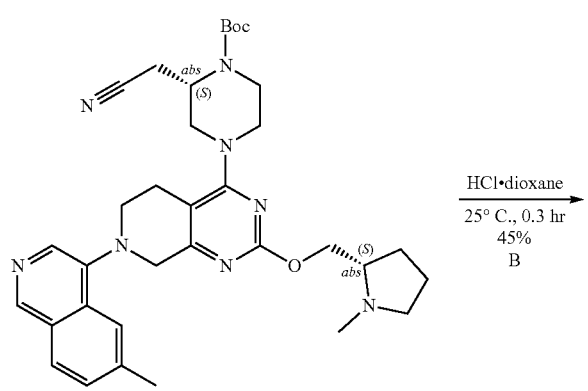

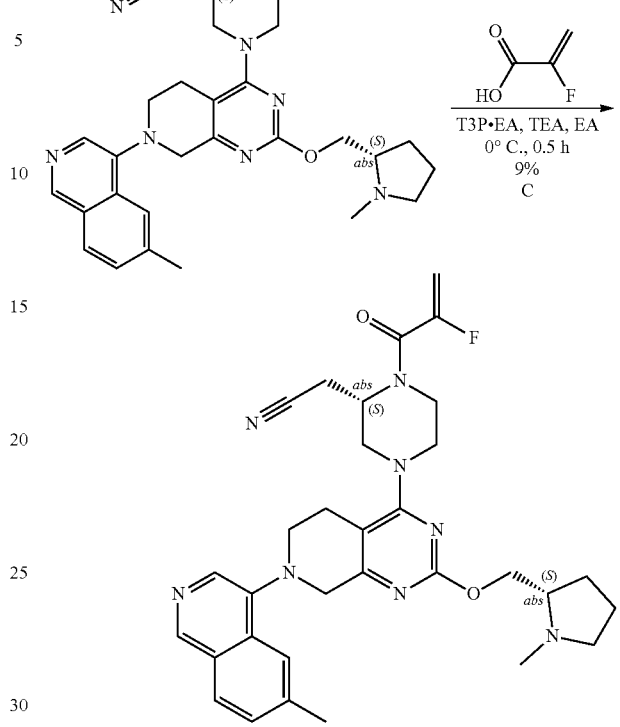

Step A: tert-butyl (2S)-2-(cyanomethyl)-4-[7-(6-methyl-4-isoquinolyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (250 mg, 530 μmol, 1.0 eq), 4-bromo-6-methyl-isoquinoline (235 mg, 1.06 mmol, 2.0 eq), RuPhos (98.9 mg, 212 μmol, 0.4 eq), Pd$_2$(dba)$_3$ (97.1 mg, 106 umol, 0.2 eq) and Cs$_2$CO$_3$ (432 mg, 1.33 mmol, 2.5 eq) in toluene (5 mL) was degassed and purged with N$_2$ 3 times, and then the mixture was stirred at 90° C. for 8 hours under N$_2$ atmosphere. The reaction mixture was diluted with water (20 mL) and extracted with ethyl acetate (3×30 mL). The combined organic layers were washed with brine (20 mL), dried over Na$_2$SO$_4$, filtered and concentrated under reduced pressure to give a residue. The residue was purified by reverse phase flash [water (0.1% formic acid)/acetonitrile)]. The mixture was adjusted pH ~7 with saturated NaHCO$_3$ aqueous solution and extracted with ethyl acetate (3×30 mL). The combined organic layers were washed with brine (20 mL), dried over Na$_2$SO$_4$, filtered and concentrated under reduced pressure to give the product. tert-butyl (2S)-2-(cyanomethyl)-4-[7-(6-methyl-4-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (230 mg, 349 μmol, 66% yield, 93% purity) was obtained as a yellow solid. LCMS [ESI, M+1]: 613.

Step B: 2-[(2S)-4-[7-(6-methyl-4-isoquinolyl)-2-[[(2S)-1-methylpyrrolidin-2-yl]methoxy]-6,8-di-hydro-5H-pyrido[3,4-d]pyrimidin-4-yl]piperazin-2-yl]acetonitrile To a solution of tert-butyl (2S)-2-(cyanomethyl)-4-[7-(6-methyl-4-isoquinolyl)-2-[[(2S)-1-methylpyrrolidin-2-yl]

methoxy]-6,8-dihydro-5H-pyrido[3,4-d]pyrimidin-4-yl]piperazine-1-carboxylate (50 mg, 81.6 μmol, 1.0 eq) in dioxane (400 μL) was added HCl/dioxane (4 M, 408 uL). The mixture was stirred at 25° C. for 0.3 hour. The mixture was concentrated under vacuum and diluted with water (10 mL). The mixture was adjusted pH ~8 with saturated NaHCO₃ aqueous solution and extracted with dichloromethane (3×20 mL). The combined organic layers were washed with brine (20 mL), dried over Na₂SO₄, filtered and concentrated under reduced pressure to give the residue. The residue was purified prep-HPLC (column: Xtimate C18 150*25 mm*5 um; mobile phase: [water (0.05% ammonia hydroxide v/v)-ACN]; B %: 28%-58%, 1 min). The desired fraction was collected and lyophilized. 2-[(2S)-4-[7-(6-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (19 mg, 37 μmol, 45% yield, 99.9% purity) was obtained as a yellow solid. LCMS [ESI, M+1]: 513.

¹H NMR (400 MHz, chloroform-d) δ=8.94 (s, 1H), 8.20 (s, 1H), 7.92-7.83 (m, 2H), 7.45 (dd, J=1.2, 8.4 Hz, 1H), 4.40 (dd, J=4.8, 10.8 Hz, 1H), 4.29 (s, 2H), 4.17 (dd, 10.8 Hz, 1H), 4.03 (br d, J=12.8 Hz, 1H), 3.86 (br d, J=12.4 Hz, 1H), 3.42 (br t, J=5.2 Hz, 2H), 3.33-3.22 (m, 1H), 3.17-2.80 (m, 7H), 2.72-2.63 (m, 1H), 2.61-2.52 (m, 5H), 2.47 (s, 3H), 2.33-2.23 (m, 1H), 2.11-2.06 (m, 1H), 1.89-1.68 (m, 3H).

Step C: 2-[(2S)-1-(2-fluoroprop-2-enoyl)-4-[7-(6-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(6-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (100 mg, 195 μmol, 1.0 eq) and 2-fluoroprop-2-enoic acid (35.1 mg, 390 umol, 2.0 eq) in ethyl acetate (2 mL) was added T3P (372 mg, 585 μmol, 348 μL, 50% purity in ethyl acetate, 3.0 eq) and TEA (158 mg, 1.56 mmol, 217 μL, 8.0 eq) at 0° C. The mixture was stirred at 0° C. for 0.5 hour. The reaction mixture was diluted with water (20 mL) and extracted with ethyl acetate (3×30 mL). The combined organic layers were washed with brine (20 mL), dried over Na₂SO₄, filtered and concentrated under reduced pressure to give a residue. The residue was purified by column chromatography (SiO₂, Ethyl acetate/Methanol=100/1 to 10/1) and further purification by prep-HPLC (column: Waters Xbridge 150*25 5 u; mobile phase: [water (0.05% ammonia hydroxide v/v)-ACN]; B %: 38%-62%, 10 min). The desired fraction was collected and lyophilized. 2-[(2S)-1-(2-fluoroprop-2-enoyl)-4-[7-(6-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (11 mg, 18.6 μmol, 9% yield, 98.9% purity) was obtained as a white solid. LCMS [ESI, M+1]: 585.

¹H NMR (400 MHz, chloroform-d) δ=8.96 (s, 1H), 8.22 (s, 1H), 7.93-7.85 (m, 2H), 7.46 (dd, J=1.2, 8.4 Hz, 1H), 5.49-5.36 (m, 1H), 5.26 (dd, J=3.6, 16.8 Hz, 1H), 4.88 (br s, 1H), 4.50-4.29 (m, 3H), 4.27-3.96 (m, 4H), 3.61-3.30 (m, 4H), 3.22-3.06 (m, 2H), 3.04-2.77 (m, 4H), 2.75-2.65 (m, 1H), 2.59 (s, 3H), 2.49 (s, 3H), 2.31-2.29 (m, 1H), 2.15-1.97 (m, 1H), 1.80-1.77 (m, 3H).

Example 608

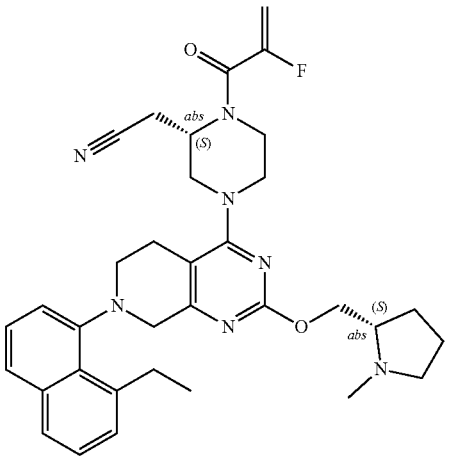

2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

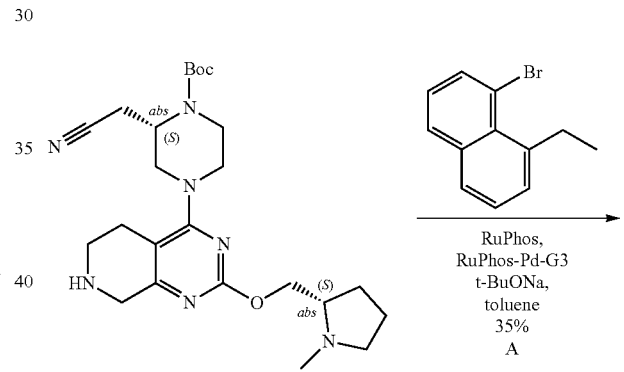

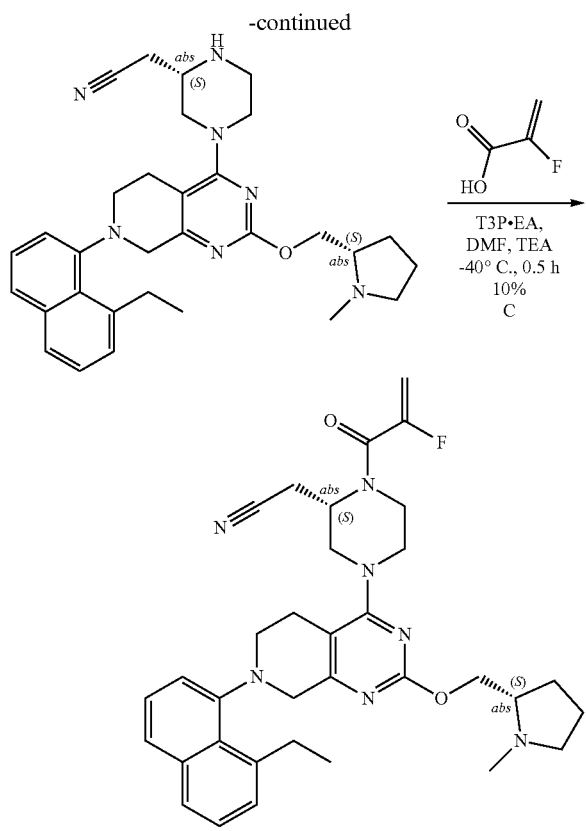

Step A: tert-butyl (2S)-2-(cyanomethyl)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate To a solution of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (240 mg, 508.91 µmol, 1 eq), t-BuONa (146.72 mg, 1.53 mmol, 3 eq), RuPhos (47.50 mg, 101.78 umol, 0.2 eq) and RuPhos Pd G3 (85.13 mg, 101.78 µmol, 0.2 eq) in toluene (5 mL) was added 1-bromo-8-ethyl-naphthalene (239.31 mg, 1.02 mmol, 2 eq). The mixture was stirred at 90° C. for 12 hrs. The mixture was added water (10 mL) and extracted with ethyl acetate (10 mL×3). The organic layers was dried over Na₂SO₄, filtered and concentrated. The residue was purified by reverse phase flash HPLC (C18, 0.1% FA in water, 0-45% MeCN). The product of tert-butyl (2S)-2-(cyanomethyl)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazine-1-carboxylate (113 mg, 180.57 µmol, 35.48% yield, 100% purity) was obtained as yellow solid. LCMS [ESI, M+1]:626.

Step B: 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(8-ethyl-1-naphthyl)-2-[[(2S)-1-methylpyrrolidin-2-yl] methoxy]-6,8-dihydro-5H-pyrido[3,4-d]pyrimidin-4-yl]piperazine-1-carboxylate (103 mg, 164.59 µmol, 1 eq) in DCM (2 mL) was added TFA (2 mL) at 25° C. The reaction mixture was stirred at 25° C. for 0.5 hr. The reaction mixture was quenched by addition saturated NaHCO₃ aqueous (20 mL) at 25° C. until pH=8, and then extracted with ethyl acetate (3×10 mL). The combined organic layers were dried over Na₂SO₄, filtered and concentrated under reduced pressure. 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (81 mg, crude) was obtained as white solid. LCMS [ESI, M+1]: 526.

1H NMR (400 MHz, chloroform-d) δ=7.66-7.55 (m, 2H), 7.37-7.25 (m, 2H), 7.25-7.20 (m, 1H), 7.19-7.14 (m, 1H), 4.36-4.26 (m, 1H), 4.21-4.02 (m, 2H), 4.00-3.62 (m, 3H), 3.56-2.73 (m, 11H), 2.65-2.34 (m, 7H), 2.26-2.14 (m, 1H), 2.02-1.88 (m, 1H), 1.82-1.62 (m, 4H), 1.13-1.02 (m, 3H).

Step C: 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(8-ethyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (61 mg, 116.04 µmol, 1 eq) and 2-fluoroprop-2-enoic acid (20.90 mg, 232.08 µmol, 2 eq) in DMF (10 mL) were added TEA (281.81 mg, 2.78 mmol, 387.63 µL, 24 eq) and T3P (332.29 mg, 1.04 mmol, 310.55 uL, 9 eq) at −40° C. After addition, the mixture was stirred at 0° C. for 2 hrs. The mixture was diluted with water (3×20 mL) and diluted with ethyl acetate (3×20 mL). The organic layer was washed with brine (1×20 mL), dried over Na₂SO₄, filtered and concentrated under vacuum. The residue was purified by prep-HPLC (column: Waters Xbridge 150*25 5 u; mobile phase: [water (0.05% ammonia hydroxide v/v)-ACN]; B %: 55%-85%, 10 min). The mixture was diluted with water (3×20 mL) and diluted with ethyl acetate (3×20 mL). The organic layer was washed with brine (1×20 mL), dried over Na₂SO₄, filtered and concentrated under vacuum to give 2-[(2S)-4-[7-(8-ethyl-1-naphthyl)-2-[[(2S)-1-methylpyrrolidin-2-yl] methoxy]-6,8-dihydro-5H-pyrido[3,4-d]pyrimidin-4-yl]-1-(2-fluoroprop-2-enoyl)piperazin-2-yl]acetonitrile (7 mg, 11.63 µmol, 10.02% yield, 99.3% purity) was obtained as yellow solid. LCMS [ESI, M+1]:598.

1H NMR (400 MHz, chloroform-d) δ=7.67-7.54 (m, 2H), 7.39-7.26 (m, 2H), 7.25-7.20 (m, 1H), 7.15 (s, 1H), 5.45-5.24 (m, 1H), 5.23-5.12 (m, 1H), 4.95-4.58 (m, 1H), 4.33-4.25 (m, 1H), 4.25-3.63 (m, 6H), 3.57-3.33 (m, 3H), 3.21-2.49 (m, 10H), 2.44-2.35 (m, 3H), 2.27-2.15 (m, 1H), 2.03-1.90 (m, 1H), 1.82-1.66 (m, 3H), 1.13-1.04 (m, 3H).

Example 609

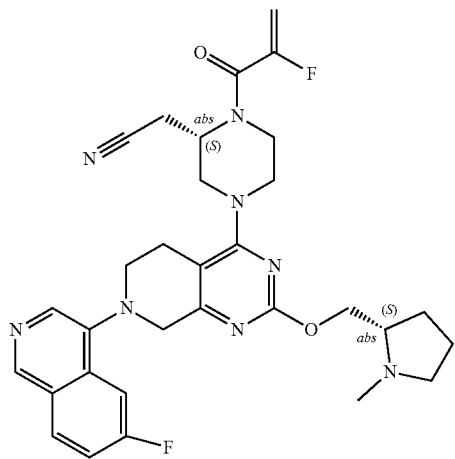

2-[(2S)-4-[7-(6-fluoro-4-isoquinolyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

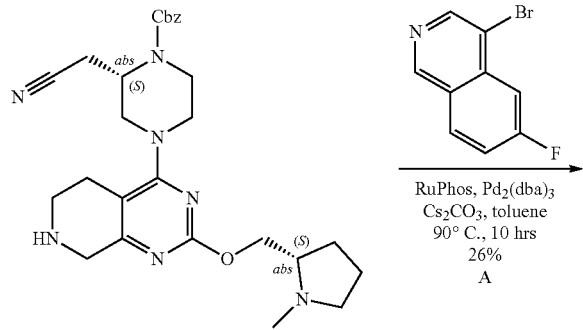

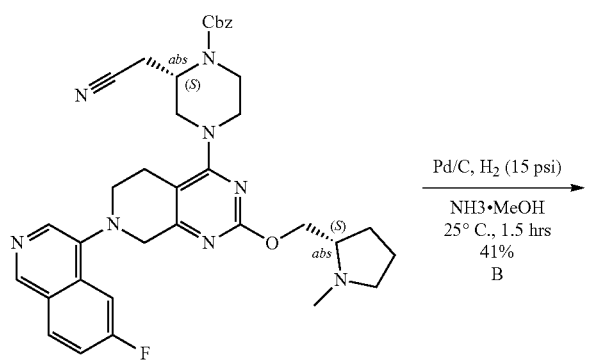

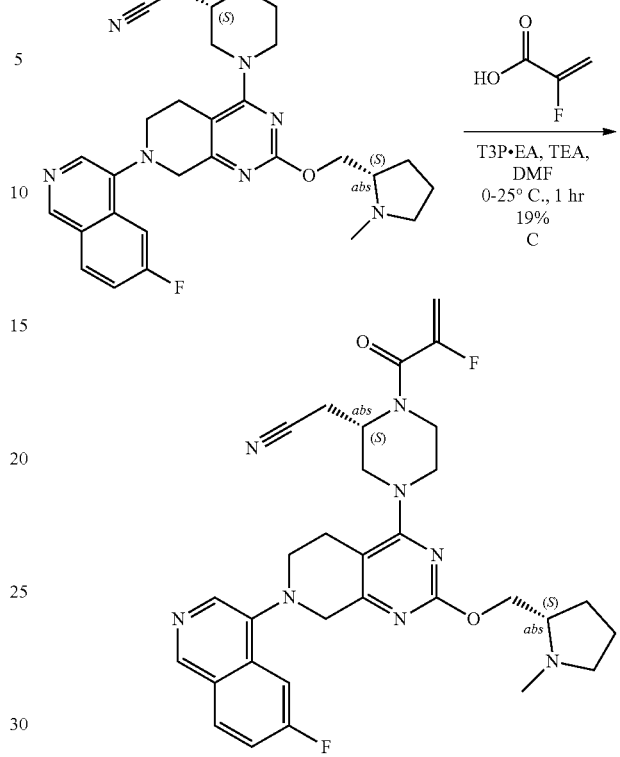

Step A: benzyl (2S)-2-(cyanomethyl)-4-[7-(6-fluoro-4-isoquinolyl)-2-[[(2S)-1-methylpyrrolidin-2-yl]methoxy]-6,8-dihydro-5H-pyrido[3,4-d]pyrimidin-4-yl]piperazine-1-carboxylate To the mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (400 mg, 791 μmol, 1.0 eq), 4-bromo-6-fluoro-isoquinoline (215 mg, 949 μmol, 1.2 eq), $Cs_2CO_3$ (773 mg, 2.37 mmol, 3.0 eq) and RuPhos (148 mg, 316 μmol, 0.4 eq) in toluene (10 mL) was added $Pd_2(dba)_3$ (145 mg, 158 μmol, 0.2 eq) under $N_2$. The suspension was degassed under vacuum and purged with $N_2$ several times. The mixture was stirred under $N_2$ at 90° C. for 10 hours. The reaction mixture filtered and the filtrate was concentrated under vacuum. The residue was purified by reverse phase flash [water (0.1% FA)/acetonitrile]. The desired fractions were collected and basified with solid $NaHCO_3$, concentrated under vacuum to remove MeCN and extracted with ethyl acetate (2×40 mL). The organic layers were dried over $Na_2SO_4$ and concentrated under vacuum to give benzyl (2S)-2-(cyanomethyl)-4-[7-(6-fluoro-4-isoquinolyl)-2-[[(2S)-1-methylpyrrolidin-2-yl]methoxy]-6,8-dihydro-5H-pyrido[3,4-d]pyrimidin-4-yl]piperazine-1-carboxylate (140 mg, 204 μmol, 26% yield, 95% purity) as a yellow solid.

Step B: 2-[(2S)-4-[7-(6-fluoro-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile To the mixture of benzyl (2S)-2-(cyanomethyl)-4-[7-(6-fluoro-4-isoquinolyl)-2-[[(2S)-1-methylpyrrolidin-2-yl]

methoxy]-6,8-dihydro-5H-pyrido[3,4-d]pyrimidin-4-yl]piperazine-1-carboxylate (30 mg, 46.1 µmol, 1.0 eq) and NH$_3$.MeOH (0.3 mL, 20% purity) in MeOH (0.3 mL) was added Pd/C (10 mg, 10% purity) under N$_2$. The suspension was degassed under vacuum and purged with H$_2$ several times. The mixture was stirred under H$_2$ (15 psi) at 25° C. for 1.5 hours. The reaction mixture was filtered and the filtrate was concentrated under vacuum. The residue was purified by prep-HPLC (column: Xtimate C18 150*25 mm*5 um; mobile phase: [water (0.05% ammonia hydroxide v/v)-ACN]; B %: 30%-60%,1 min). The desired fractions were collected and lyophilized to give 2-[(2S)-4-[7-(6-fluoro-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (9.78 mg, 18.9 µmol, 41% yield, 99.9% purity) as a white solid. LCMS [ESI, M+1]: 517.

$^1$H NMR (400 MHz, chloroform-d) δ=9.00 (s, 1H), 8.27 (s, 1H), 8.02 (dd, 9.2 Hz, 1H), 7.74 (dd, J=2.4, 10.4 Hz, 1H), 7.39 (dt, J=2.4, 8.8 Hz, 1H), 4.41 (dd, J=4.8, 10.4 Hz, 1H), 4.28 (s, 2H), 4.18 (dd, J=6.8, 10.4 Hz, 1H), 4.02 (br d, J=12.4 Hz, 1H), 3.91-3.82 (m, 1H), 3.47-3.35 (m, 2H), 3.33-3.24 (m, 1H), 3.18-3.07 (m, 3H), 3.07-2.97 (m, 1H), 2.93 (dd, J=9.6, 12.8 Hz, 1H), 2.85 (br s, 2H), 2.73-2.64 (m, 1H), 2.56 (dd, J=2.4, 6.4 Hz, 2H), 2.49 (s, 3H), 2.34-2.24 (m, 1H), 2.13-2.00 (m, 1H), 1.91-1.76 (m, 3H).

Step C: 2-[(2S)-4-[7-(6-fluoro-4-isoquinolyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To the mixture of 2-[(2S)-4-[7-(6-fluoro-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (80 mg, 155 µmol, 1.0 eq), 2-fluoroprop-2-enoic acid (41.8 mg, 464 µmol, 3.0 eq) and TEA (235 mg, 2.32 mmol, 323 uL, 15 eq) in ethyl acetate (1.5 mL) and DMF (1 mL) was added T3P (493 mg, 774 µmol, 460 uL, 50% purity, 5.0 eq) at 0° C., the mixture was stirred at 25° C. for 1 hour. Water (10 mL) was added into the mixture. The mixture was diluted with ethyl acetate (30 mL) and extracted with ethyl acetate (2×5 mL). The combined organic layers were dried over anhydrous Na$_2$SO$_4$, filtered and concentrated under vacuum. The residue was purified by prep-HPLC (column: Xtimate C18 150*25 mm*5 um; mobile phase: [water (0.05% ammonia hydroxide v/v)-ACN]; B %: 40%-70%, 1 min). The desired fractions were collected and lyophilized to give 2-[(2S)-4-[7-(6-fluoro-4-isoquinolyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (17.4 mg, 29.3 µmol, 19% yield, 99.2% purity) as a white solid. LCMS [ESI, M+1]: 589.

$^1$H NMR (400 MHz, chloroform-d) δ=9.01 (s, 1H), 8.28 (s, 1H), 8.03 (dd, 8.8 Hz, 1H), 7.73 (dd, J=2.4, 10.4 Hz, 1H), 7.40 (dt, J=2.4, 8.8 Hz, 1H), 5.52-5.35 (m, 1H), 5.27 (dd, J=3.6, 17.2 Hz, 1H), 5.02-4.62 (m, 1H), 4.46-4.38 (m, 1H), 4.36-4.25 (m, 2H), 4.24-4.07 (m, 3H), 4.02 (br d, J=13.2 Hz, 1H), 3.62-3.29 (m, 4H), 3.13 (br s, 2H), 3.03-2.93 (m, 2H), 2.91-2.77 (m, 2H), 2.72 (br s, 1H), 2.51 (s, 3H), 2.32 (br d, J=8.4 Hz, 1H), 2.13-2.02 (m, 1H), 1.92-1.70 (m, 3H).

Example 610

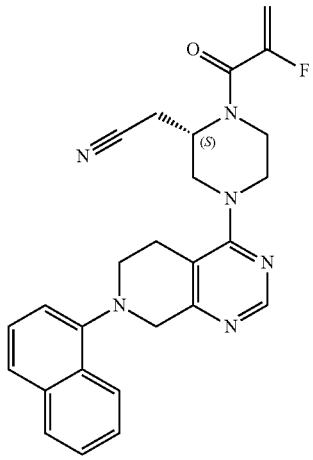

(S)-2-(1-(2-fluoroacryloyl)-4-(7-(naphthalen-1-yl)-5,6,7,8-tetrahydropyrido[3,4-d]pyrimidin-4-yl)piperazin-2-yl)acetonitrile

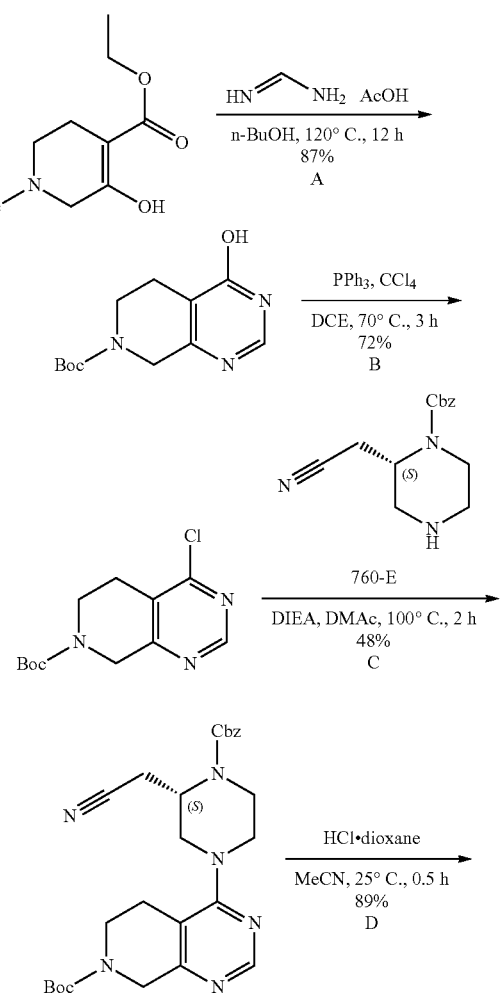

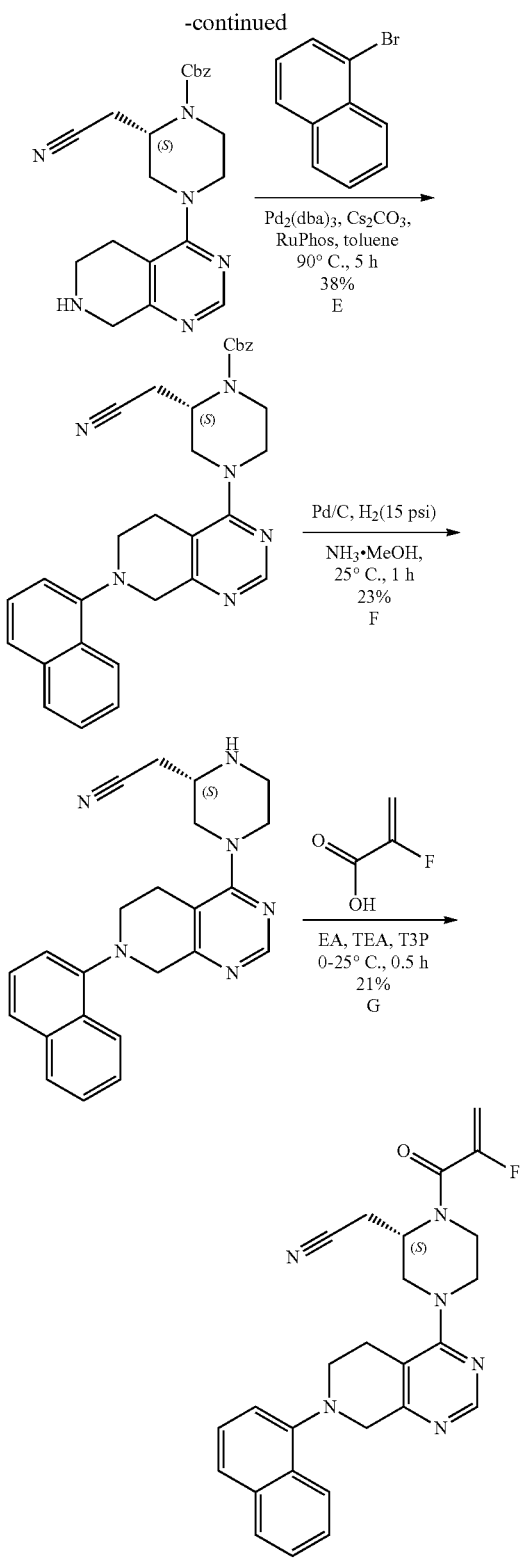

Step A: tert-butyl 4-hydroxy-6,8-dihydro-5H-pyrido [3,4-d]pyrimidine-7-carboxylate To a mixture of O1-tert-butyl O4-ethyl 3-oxopiperidine-1,4-dicarboxylate (5.00 g, 18.4 mmol, 1.00 eq) in n-BuOH (30.0 mL) was added acetic acid; methanimidamide (9.59 g, 92.2 mmol, 5.00 eq) in portion. The mixture was stirred at 120° C. for 12 hours. The mixture was concentrated to remove the solvent. The residue was added water (30.0 mL) and filtered. The precipitate was washed with water (30.0 mL) and concentrated. The crude product was used in the next step directly without further purification. Compound tert-butyl 4-hydroxy-6,8-dihydro-5H-pyrido[3,4-d]pyrimidine-7-carboxylate (4.10 g, 16.1 mmol, 87% yield, 98.4% purity) was obtained as a brown solid. LCMS [ESI, M+1]: 196.

Step B: tert-butyl 4-chloro-6,8-dihydro-5H-pyrido [3,4-d]pyrimidine-7-carboxylate To a mixture of tert-butyl 4-hydroxy-6,8-dihydro-5H-pyrido[3,4-d]pyrimidine-7-carboxylate (3.30 g, 13.1 mmol, 1.00 eq) in DCE (60.0 mL) was added PPh$_3$ (6.89 g, 26.3 mmol, 2.00 eq), CCl$_4$ (6.06 g, 39.4 mmol, 3.79 mL, 3.00 eq) in portion under N$_2$. The mixture was stirred at 70° C. for 3 hours. The reaction mixture was filtered and concentrated under reduced pressure to give a residue. The residue was purified by column chromatography (SiO$_2$, Petroleum ether/Ethyl acetate=20/1 to 1/1). Compound tert-butyl 4-chloro-6,8-dihydro-5H-pyrido[3,4-d]pyrimidine-7-carboxylate (2.54 g, 9.42 mmol, 72% yield, 100% purity) was obtained as a yellow solid. LCMS [ESI, M+1]: 214.

Step C: tert-butyl 4-[(3S)-4-benzyloxycarbonyl-3-(cyanomethyl)piperazin-1-yl]-6,8-dihydro-5H-pyrido[3,4-d]pyrimidine-7-carboxylate To a mixture of tert-butyl 4-chloro-6,8-dihydro-5H-pyrido[3,4-d]pyrimidine-7-carboxylate (1.30 g, 4.82 mmol, 1.00 eq) and benzyl (2S)-2-(cyanomethyl)piperazine-1-carboxylate (1.00 g, 3.86 mmol, 0.80 eq) in DMAc (30.0 mL) was added DIEA (3.11 g, 24.1 mmol, 4.20 mL, 5.00 eq) under N$_2$. The mixture was stirred at 100° C. for 2 hours. The reaction mixture was diluted with ethyl acetate (100 mL). The organic layers were washed with water (30 mL×2) and brine (30 mL×1), dried over sodium sulfate, filtered and concentrated under reduced pressure to give a residue. The residue was purified by column chromatography (SiO$_2$, Petroleum ether/Ethyl acetate=20/1 to 0/1). Compound tert-butyl 4-[(3S)-4-benzyloxycarbonyl-3-(cyanomethyl)piperazin-1-yl]-6,8-dihydro-5H-pyrido[3,4-d]pyrimidine-7-carboxylate (1.18 g, 2.30 mmol, 48% yield, 96% purity) was obtained as a white solid. LCMS [ESI, M+1]: 493.

Step D: benzyl (2S)-2-(cyanomethyl)-4-(5,6,7,8-tetrahydropyrido[3,4-d]pyrimidin-4-yl) piperazine-1-carboxylate To a mixture of tert-butyl 4-[(3S)-4-benzyloxycarbonyl-3-(cyanomethyl)piperazin-1-yl]-6,8-dihydro-5H-pyrido[3,4-d]pyrimidine-7-carboxylate (1.20 g, 2.44 mmol, 1.00 eq) in acetonitrile (10.0 mL) was added HCl/dioxane (4.00 M, 12.2 mL, 20.0 eq) in portion at 25° C. under N$_2$. The mixture was stirred at 25° C. for 30 min. The reaction mixture was concentrated under reduced pressure to give a residue. The crude product was used in the next step directly without further purification. Compound benzyl (2S)-2-(cyanomethyl)-4-(5,6,7,8-tetrahydropyrido[3,4-d]pyrimidin-4-yl) piperazine-1-carboxylate (883 mg, 2.16 mmol, 89% yield, 96% purity) was obtained as a yellow solid. LCMS [ESI, M+1]: 393.

Step E: benzyl (2S)-2-(cyanomethyl)-4-[7-(1-naphthyl)-6,8-dihydro-5H-pyrido[3,4-d]pyrimidin-4-yl]piperazine-1-carboxylate To a mixture of benzyl (2S)-2-(cyanomethyl)-4-(5,6,7,8-tetrahydropyrido[3,4-d]pyrimidin-4-yl)piperazine-1-carboxylate (300 mg, 764 µmol, 1.00 eq) and 1-bromonaphthalene (317 mg, 1.53 mmol, 212 uL, 2.00 eq) in toluene (15.0 mL) was added $Pd_2(dba)_3$ (140 mg, 153 µmol, 0.20 eq), RuPhos (143 mg, 306 µmol, 0.40 eq) $Cs_2CO_3$ (747 mg, 2.29 mmol, 3.00 eq) in one portion under $N_2$. The mixture was stirred at 90° C. for 5 hours. The reaction mixture was diluted with water (10.0 mL) and extracted with ethyl acetate (20.0 mL×3). The combined organic layers were washed with brine (20.0 mL×1), dried over sodium sulfate, filtered and concentrated under reduced pressure to give a residue. The residue was purified by reversed phase flash [water (0.1% FA)/acetonitrile]. The desired fractions were collected and neutralized with saturated $NaHCO_3$ solution (5.00 mL) and extracted with ethyl acetate (50.0 mL×2). The separated organic layer was dried over sodium sulfate, filtered and concentrated under vacuum. Compound benzyl (2S)-2-(cyanomethyl)-4-[7-(1-naphthyl)-6,8-dihydro-5H-pyrido[3,4-d]pyrimidin-4-yl]piperazine-1-carboxylate (150 mg, 289 µmol, 38% yield) was obtained as a yellow solid.

Step F: 2-[(2S)-4-[7-(1-naphthyl)-6,8-dihydro-5H-pyrido[3,4-d]pyrimidin-4-yl]piperazin-2-yl]acetonitrile To a solution of benzyl (2S)-2-(cyanomethyl)-4-[7-(1-naphthyl)-6,8-dihydro-5H-pyrido[3,4-d]pyrimidin-4-yl]piperazine-1-carboxylate (50.0 mg, 96.4 µmol, 1.00 eq) in MeOH (3.00 mL) was added Pd/C (30.0 mg, 10% purity), $NH_3$.MeOH (0.50 mL, 20% purity) under $N_2$. The suspension was degassed under vacuum and purged with $H_2$ several times. The mixture was stirred under $H_2$ (15 psi) at 25° C. for 1 hour. The reaction mixture was filtered and concentrated under reduced pressure to give a residue. The residue was purified by prep-HPLC (column: Waters Xbridge 150×25 5 u; mobile phase: [water (0.05% ammonia hydroxide v/v)-ACN]; B %: 35%-59%, 10 min). Compound 2-[(2S)-4-[7-(1-naphthyl)-6,8-dihydro-5H-pyrido[3,4-d]pyrimidin-4-yl]piperazin-2-yl]acetonitrile (8.63 mg, 22.4 µmol, 23% yield, 99.8% purity) was obtained as a off-white solid. LCMS [ESI, M+1]: 385.

$^1$H NMR (400 MHz, chloroform-d) δ=8.63 (s, 1H), 8.26-8.19 (m, 1H), 7.91-7.84 (m, 1H), 7.62 (d, J=8.0 Hz, 1H), 7.54-7.48 (m, 2H), 7.45 (t, J=7.6 Hz, 1H), 7.17 (d, J=7.2 Hz, 1H), 4.35 (s, 2H), 3.99 (br d, J=12.8 Hz, 1H), 3.83 (br d, J=12.8 Hz, 1H), 3.53-3.23 (m, 3H), 3.20-3.07 (m, 2H), 3.07-2.90 (m, 4H), 2.63-2.49 (m, 2H).

Step G

To a mixture of 2-[(2S)-4-[7-(1-naphthyl)-6,8-dihydro-5H-yrido[3,4-d]pyrimidin-4-yl]piperazin-2-yl]acetonitrile (60.0 mg, 156 µmol, 1.00 eq) in ethyl acetate (0.60 mL) was added 2-fluoroprop-2-enoic acid (56.2 mg, 624 µmol, 4.00 eq), TEA (253 mg, 2.50 mmol, 348 uL, 16.0 eq) and T3P (596 mg, 936 µmol, 557 uL, 50% purity, 6.00 eq) in portion at 0° C. under $N_2$. The mixture was stirred at 25° C. for 30 min. The reaction mixture was quenched by addition water (1.00 mL) at 0° C., and then extracted with ethyl acetate (10.0 mL×3). The combined organic layers were washed with brine (5.00 mL×1), dried over sodium sulfate, filtered and concentrated under reduced pressure to give a residue. The residue was purified by prep-HPLC (column: Waters Xbridge 150×25 5 u; mobile phase: [water (0.05% ammonia hydroxide v/v)-ACN]; B %: 40%-70%, 10 min). Compound 2-[(2S)-1-(2-luoroprop-2-enoyl)-4-[7-(1-naphthyl)-6,8-dihydro-5H-pyrido[3,4-d]pyrimidin-4-yl]piperazin-2-yl]acetonitrile (15.2 mg, 32.8 µmol, 21% yield, 98.9% purity) was obtained as a white solid. LCMS [ESI, M+1]: 457.

$^1$H NMR (400 MHz, chloroform-d) δ=8.67 (s, 1H), 8.26-8.18 (m, 1H), 7.91-7.84 (m, 1H), 7.63 (d, J=8.0 Hz, 1H), 7.56-7.49 (m, 2H), 7.45 (t, J=7.6 Hz, 1H), 7.18 (d, J=6.8 Hz, 1H), 5.54-5.34 (m, 1H), 5.27 (dd, J=4.0, 17.2 Hz, 1H), 4.91 (br s, 1H), 4.46-4.29 (m, 2H), 4.14 (br d, J=13.6 Hz, 1H), 3.99 (br d, J=13.2 Hz, 1H), 3.63-3.32 (m, 4H), 3.16 (br t, J=11.2 Hz, 2H), 2.99 (br dd, J=8.0, 16.4 Hz, 3H), 2.90-2.77 (m, 1H).

Example 611

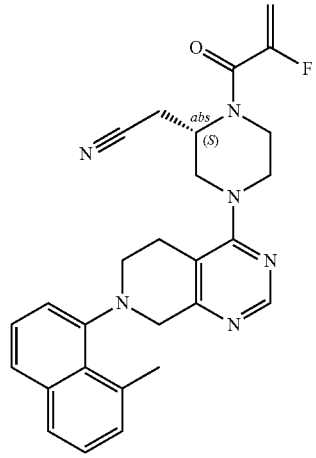

(S)-2-(1-(2-fluoroacryloyl)-4-(7-(8-methylnaphthalen-1-yl)-5,6,7,8-tetrahydropyrido[3,4-d]pyrimidin-4-yl)piperazin-2-yl)acetonitrile

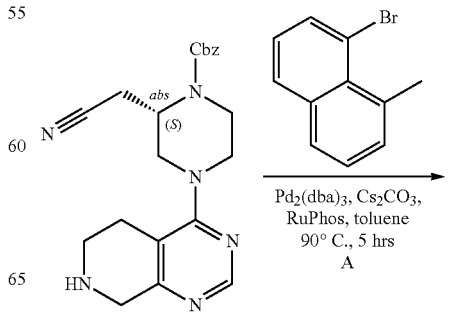

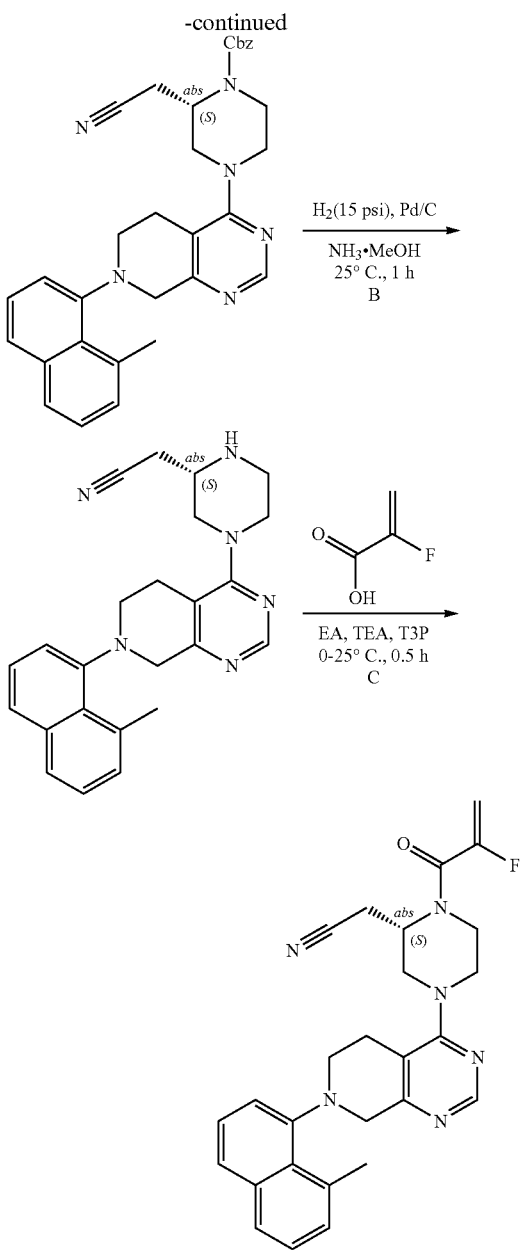

Step A: benzyl (2S)-2-(cyanomethyl)-4-[7-(8-methyl-1-naphthyl)-6,8-dihydro-5H-pyrido[3,4-d]pyrimidin-4-yl]piperazine-1-carboxylate To a mixture of benzyl (2S)-2-(cyanomethyl)-4-(5,6,7,8-tetrahydropyrido[3,4-d]pyrimidin-4-yl)piperazine-1-carboxylate (100 mg, 255 μmol, 1.00 eq) and 1-bromo-8-methyl-naphthalene (113 mg, 510 μmol, 10.6 uL, 2.00 eq) in toluene (8.00 mL) was added Pd$_2$(dba)$_3$ (46.7 mg, 51.0 μmol, 0.20 eq), RuPhos (47.6 mg, 102 μmol, 0.40 eq) Cs$_2$CO$_3$ (249 mg, 764 μmol, 3.00 eq) in one portion under N$_2$. The mixture was stirred at 90° C. for 5 hours. The reaction mixture was diluted with water (10.0 mL) and extracted with ethyl acetate (20.0 mL×3). The combined organic layers were washed with brine (20.0 mL×1), dried over sodium sulfate, filtered and concentrated under reduced pressure to give a residue. The residue was purified by reversed phase flash [water (0.1% FA)/acetonitrile]. The desired fractions were collected and neutralized with saturated NaHCO$_3$ solution (5.00 mL) and extracted with ethyl acetate (50.0 mL×2). The separated organic layer was dried over sodium sulfate, filtered and concentrated under vacuum. Compound benzyl (2S)-2-(cyanomethyl)-4-[7-(8-methyl-1-naphthyl)-6,8-dihydro-5H-pyrido[3,4-d]pyrimidin-4-yl]piperazine-1-carboxylate (150 mg, crude) was obtained as a yellow solid.

Step B: 2-[(2S)-4-[7-(8-methyl-1-naphthyl)-6,8-dihydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-6,8-dihydro-5H-pyrido[3,4-d]pyrimidin-4-yl]piperazine-1-carboxylate (50.0 mg, 93.9 μmol, 1.00 eq) in methanol (1.00 mL) was added NH$_3$.MeOH (93.9 μmol, 0.2 mL, 20% purity, 1.00 eq), Pd/C (15.0 mg, 10% purity) under N$_2$. The suspension was degassed under vacuum and purged with H$_2$ several times. The mixture was stirred under H$_2$ (15 psi) at 25° C. for 1 hour. The reaction mixture was filtered and concentrated under reduced pressure to give a residue. The residue was purified by prep-HPLC (column: Waters Xbridge 150*25 5 u; mobile phase: [water (0.05% ammonia hydroxide v/v)-ACN]; B %: 38%-62%, 10 min). Compound 2-[(2S)-4-[7-(8-methyl-1-naphthyl)-6,8-dihydro-5H-pyrido[3,4-d]pyrimidin-4-yl]piperazin-2-yl]acetonitrile (6.13 mg, 15.3 μmol, 16% yield, 99.5% purity) was obtained as a white solid. LCMS [ESI, M+1]: 399.

$^1$H NMR (400 MHz, chloroform-d) δ=8.61 (d, J=4.8 Hz, 1H), 7.74-7.63 (m, 2H), 7.41 (dt, J=2.8, 7.6 Hz, 1H), 7.37-7.31 (m, 1H), 7.27-7.22 (m, 2H), 4.32 (br d, J=18.0 Hz, 1H), 4.07-3.92 (m, 1H), 3.92-3.86 (m, 1H), 3.86-3.67 (m, 1H), 3.56-3.48 (m, 1H), 3.30-3.24 (m, 1H), 3.24-3.18 (m, 1H), 3.18-2.96 (m, 4H), 2.94 (d, J=2.4 Hz, 3H), 2.92 (br s, 1H), 2.92-2.83 (m, 1H), 2.69-2.59 (m, 1H), 2.57-2.53 (m, 2H).

Step C: 2-[(2S)-1-(2-fluoroprop-2-enoyl)-4-[7-(8-methyl-1-naphthyl)-6,8-dihydro-5H-pyrido[3,4-d]pyrimidin-4-yl]piperazin-2-yl]acetonitrile To a mixture of 2-[(2S)-4-[7-(8-methyl-1-naphthyl)-6,8-dihydro-5H-pyrido[3,4-d]pyrimidin-4-yl]piperazin-2-yl]acetonitrile (60.0 mg, 151 μmol, 1.00 eq) in ethyl acetate (1.00 mL) was added 2-fluoroprop-2-enoic acid (54.2 mg, 602 μmol, 4.00 eq), TEA (244 mg, 2.41 mmol, 335 uL, 16.0 eq) and T3P (575 mg, 903 μmol, 537 uL, 50% purity, 6.00 eq) in portion at 0° C. under N$_2$. The mixture was stirred at 25° C. for 30 min. The reaction mixture was quenched by addition water (1.00 mL) at 0° C., and then extracted with ethyl acetate (10 mL×3). The combined organic layers were washed with brine (5 mL×1), dried over sodium sulfate, filtered and concentrated under reduced pressure to give a residue. The residue was purified by prep-HPLC (column: Waters Xbridge 150×25 5 u; mobile phase: [water (0.05% ammonia hydroxide v/v)-ACN]; B %: 40%-70%, 10 min). Compound 2-[(2S)-1-(2-fluoroprop-2-enoyl)-4-[7-(8-methyl-1-naphthyl)-6,8-dihydro-5H-pyrido[3,4-d]pyrimidin-4-yl]piperazin-2-yl]acetonitrile (8.97 mg, 18.7 μmol, 12% yield, 98.2% purity) was obtained as a yellow solid. LCMS [ESI, M+1]: 492.

$^1$H NMR (400 MHz, chloroform-d) δ=8.64 (d, J=7.2 Hz, 1H), 7.74-7.64 (m, 2H), 7.47-7.39 (m, 1H), 7.39-7.32 (m, 1H), 7.29 (br d, J=1.2 Hz, 1H), 7.26-7.19 (m, 1H), 5.53-5.33

(m, 1H), 5.26 (dd, J=3.6, 17.2 Hz, 1H), 4.87 (br s, 1H), 4.33 (br dd, J=14.8, 18.0 Hz, 1H), 4.19 (br d, J=13.6 Hz, 1H), 4.12-3.97 (m, 2H), 3.95-3.84 (m, 1H), 3.61-3.42 (m, 2H), 3.27-3.04 (m, 4H), 2.92 (d, J=2.4 Hz, 3H), 2.89-2.62 (m, 3H).

Example 612

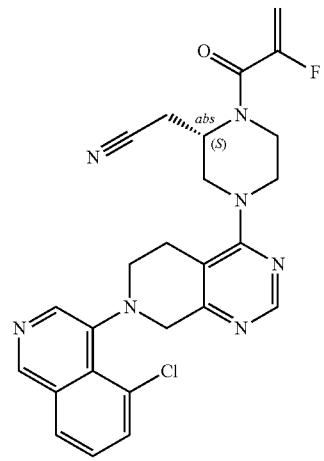

(S)-2-(4-(7-(5-chloroisoquinolin-4-yl)-5,6,7,8-tetrahydropyrido[3,4-d]pyrimidin-4-yl)-1-(2-fluoroacryloyl)piperazin-2-yl)acetonitrile

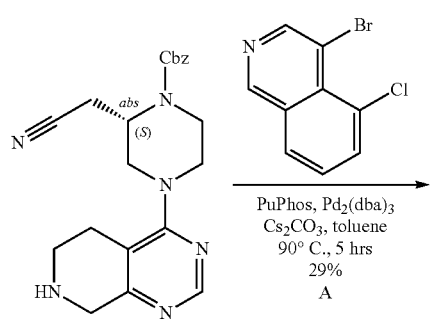

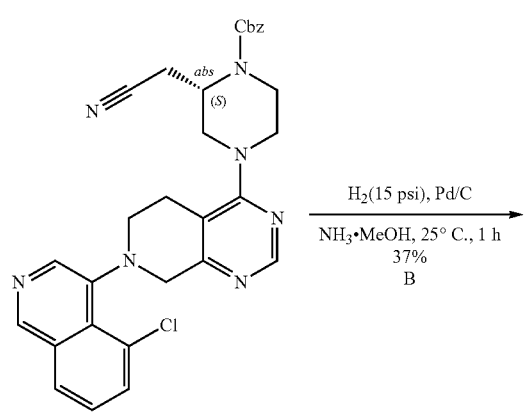

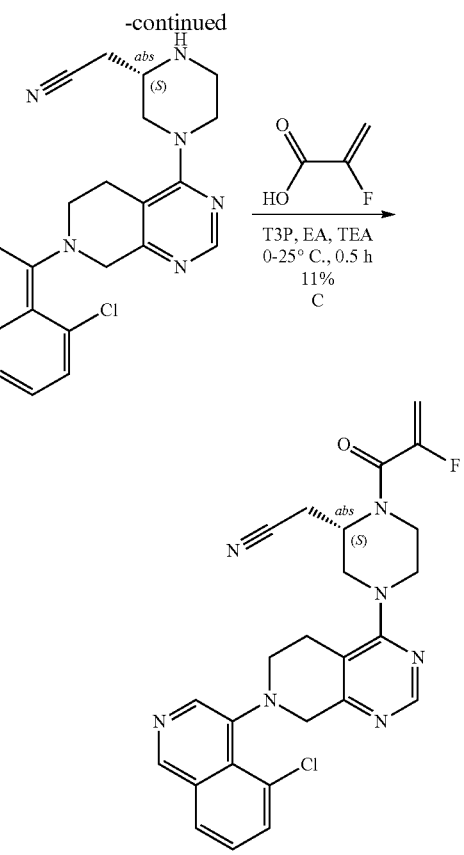

Step A: benzyl (2S)-4-[7-(5-chloro-4-isoquinolyl)-6,8-dihydro-5H-pyrido [3,4-d]pyrimidin-4-yl]-2-(cyanomethyl)piperazine-1-carboxylate To a mixture of benzyl (2S)-2-(cyanomethyl)-4-(5,6,7,8-tetrahydropyrido[3,4-d]pyrimidin-4-yl)piperazine-1-carboxylate (300 mg, 764 μmol, 1.00 eq) and 4-bromo-5-chloro-isoquinoline (371 mg, 1.53 mmol, 10.6 μL, 2.00 eq) in toluene (15.0 mL) was added Pd₂(dba)₃ (140 mg, 153 μmol, 0.20 eq), RuPhos (143 mg, 306 μmol, 0.40 eq), Cs₂CO₃ (747 mg, 2.29 mmol, 3.00 eq) in one portion under N₂. The mixture was degassed and purged with N₂ 3 times and stirred at 90° C. for 5 hours. The reaction mixture was diluted with water (10.0 mL) and extracted with ethyl acetate (20.0 mL×3). The combined organic layers were washed with brine (20.0 mL×1), dried over sodium sulfate, filtered and concentrated under reduced pressure to give a residue. The residue was purified by reversed phase flash [water (0.1% FA)/acetonitrile]. The desired fractions were collected and neutralized with saturated NaHCO₃ solution (5 mL) and extracted with ethyl acetate (50 mL×2). The separated organic layer was dried over sodium sulfate, filtered and concentrated under vacuum. Compound benzyl (2S)-4-[7-(5-chloro-4-isoquinolyl)-6,8-dihydro-5H-pyrido [3,4-d]pyrimidin-4-yl]-2-(cyanomethyl)piperazine-1-carboxylate (130 mg, 223 μmol, 29% yield, 95% purity) was obtained as a yellow solid. LCMS [ESI, M+1]: 554.

Step B: 2-[(2S)-4-[7-(5-chloro-4-isoquinolyl)-6,8-dihydro-5H-pyrido[3,4-d]pyrimidin-4-yl]piperazin-2-yl]acetonitrile To a solution of benzyl (2S)-4-[7-(5-chloro-4-isoquinolyl)-6,8-dihydro-5H-pyrido[3,4-d]pyrimidin-4-yl]-2-

(cyanomethyl)piperazine-1-carboxylate (30.0 mg, 54.2 µmol, 1.00 eq) in methanol (3.00 mL) was added NH$_3$.MeOH (0.50 mL, 20% purity), Pd/C (35.0 mg, 10% purity) under N$_2$. The suspension was degassed under vacuum and purged with H$_2$ several times. The mixture was stirred under H$_2$ (15 psi) at 25° C. for 1 hour. The reaction mixture was filtered and concentrated under reduced pressure to give a residue. The residue was purified by prep-HPLC (column: Waters Xbridge 150×25 5 u; mobile phase: [water (0.05% ammonia hydroxide v/v)-ACN]; B %: 22%-46%, 10 min). Compound 2-[(2S)-4-[7-(5-chloro-4-isoquinolyl)-6,8-dihydro-5H-pyrido[3,4-d]pyrimidin-4-yl]piperazin-2-yl]acetonitrile (8.51 mg, 20.1 µmol, 37% yield, 99.4% purity) was obtained as a white solid. LCMS [ESI, M+1]: 420.

$^1$H NMR (400 MHz, chloroform-d) δ=9.02 (s, 1H), 8.60 (d, J=4.4 Hz, 1H), 8.35 (d, J=1.6 Hz, 1H), 7.91 (dd, J=1.2, 8.4 Hz, 1H), 7.75 (dd, J=1.2, 7.2 Hz, 1H), 7.50 (t, J=7.6 Hz, 1H), 4.54 (br d, J=17.2 Hz, 1H), 4.06-3.61 (m, 4H), 3.41-3.08 (m, 5H), 3.07-2.85 (m, 2H), 2.72-2.59 (m, 1H), 2.58-2.49 (m, 2H).

Step C: 2-[(2S)-4-[7-(5-chloro-4-isoquinolyl)-6,8-dihydro-5H-pyrido[3,4-d]pyrimidin-4-yl]-1-(2-fluoroprop-2-enoyl)piperazin-2-yl]acetonitrile To a mixture of 2-[(2S)-4-[7-(5-chloro-4-isoquinolyl)-6,8-dihydro-5H-pyrido[3,4-d]pyrimidin-4-yl]piperazin-2-yl]acetonitrile (60.0 mg, 143 µmol, 1.00 eq) in ethyl acetate (0.80 mL) was added 2-fluoroprop-2-enoic acid (25.7 mg, 286 µmol, 2.00 eq), TEA (86.8 mg, 857 µmol, 119 uL, 6.00 eq) and T3P (273 mg, 429 µmol, 255 uL, 50% purity, 3.00 eq) in portion at 0° C. under N$_2$. The mixture was stirred at 25° C. for 30 min. The reaction mixture was quenched by addition water (1.00 mL) at 0° C., and then extracted with ethyl acetate (10.0 mL×3). The combined organic layers were washed with brine (5.00 mL×1), dried over sodium sulfate, filtered and concentrated under reduced pressure to give a residue. The residue was purified by prep-HPLC (column: Waters Xbridge 150×25 5 u; mobile phase: [water (0.05% ammonia hydroxide v/v)-ACN]; B %: 22%-52%, 10 min). Compound 2-[(2S)-4-[7-(5-chloro-4-isoquinolyl)-6,8-dihydro-5H-pyrido[3,4-d]pyrimidin-4-yl]-1-(2-fluoroprop-2-enoyl)piperazin-2-yl]acetonitrile (7.88 mg, 16.0 µmol, 11% yield, 100% purity) was obtained as a yellow solid. LCMS [ESI, M+1]: 492.

$^1$H NMR (400 MHz, chloroform-d) δ=9.04 (d, J=3.6 Hz, 1H), 8.65 (d, J=6.4 Hz, 1H), 8.35 (d, J=11.6 Hz, 1H), 7.96-7.88 (m, 1H), 7.76 (dd, J=1.2, 7.2 Hz, 1H), 7.56-7.47 (m, 1H), 5.55-5.33 (m, 1H), 5.26 (dd, J=3.2, 16.8 Hz, 1H), 5.03-4.70 (m, 1H), 4.55 (br dd, J=6.4, 18.0 Hz, 1H), 4.23-3.84 (m, 4H), 3.69 (br d, J=6.4 Hz, 1H), 3.50 (br d, J=13.6 Hz, 1H), 3.35-3.19 (m, 3H), 3.16-3.00 (m, 1H), 2.97-2.61 (m, 3H).

Example 613

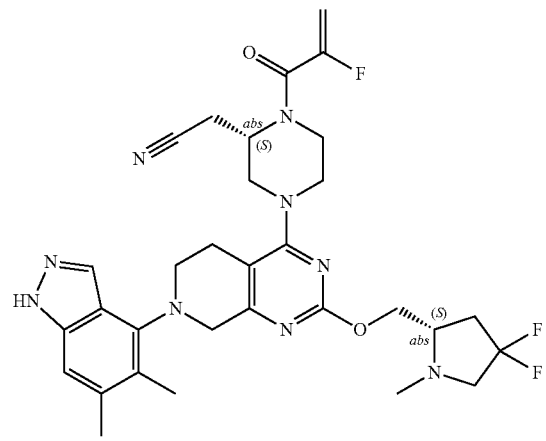

2-((S)-4-(2-(((S)-4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)-1-(2-fluoroacryloyl)piperazin-2-yl)acetonitrile

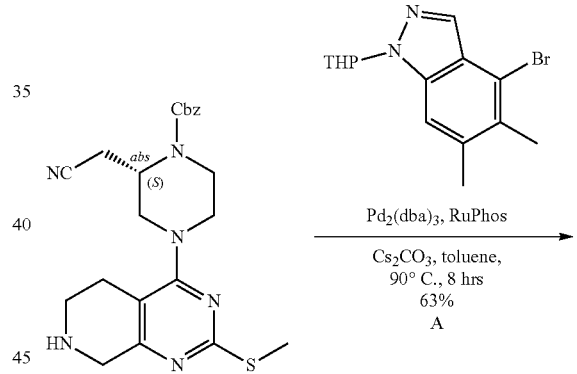

Pd$_2$(dba)$_3$, RuPhos
Cs$_2$CO$_3$, toluene,
90° C., 8 hrs
63%
A

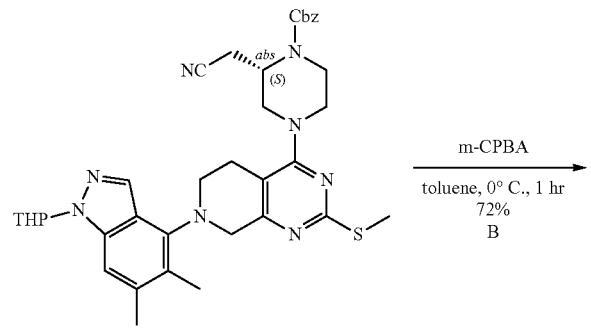

m-CPBA
toluene, 0° C., 1 hr
72%
B

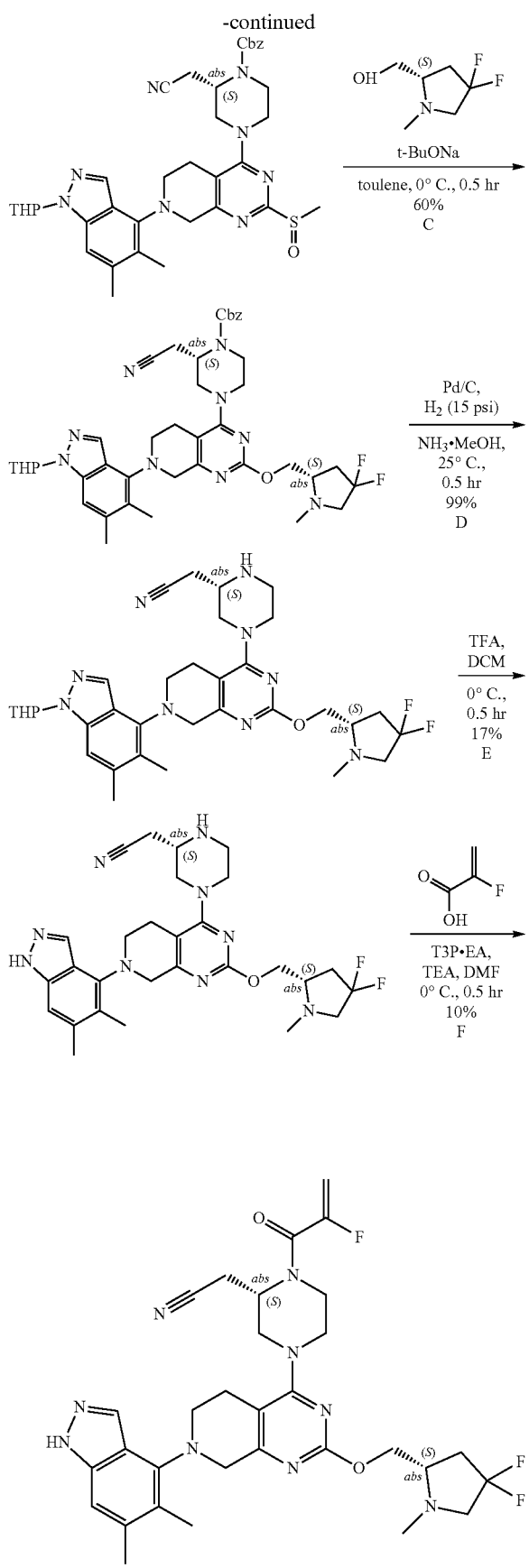

Step A: benzyl (2S)-2-(cyanomethyl)-4-[7-(5,6-dimethyl-1-tetrahydropyran-2-yl-indazol-4-yl)-2-methylsulfanyl-6,8-dihydro-5H-pyrido[3,4-d]pyrimidin-4-yl]piperazine-1-carboxylate A mixture of benzyl (2S)-2-(cyanomethyl)-4-(2-methylsulfanyl-5,6,7,8-tetrahydropyrido[3,4-d]pyrimidin-4-yl)piperazine-1-carboxylate (5.0 g, 11.4 mmol, 1.0 eq), 4-bromo-5,6-dimethyl-1-tetrahydropyran-2-yl-indazole (7.05 g, 22.8 mmol, 2.0 eq), $Pd_2(dba)_3$ (2.09 g, 2.28 mmol, 0.2 eq), RuPhos (2.13 g, 4.56 mmol, 0.4 eq) and $Cs_2CO_3$ (9.29 g, 28.5 mmol, 2.5 eq) in toluene (100 mL) was degassed and purged with $N_2$ for 3 times, and then the mixture was stirred at 90° C. for 8 hours under $N_2$ atmosphere. The reaction mixture was diluted with water (100 mL) and extracted with ethyl acetate (3×200 mL). The combined organic layers were washed with brine (100 mL), dried over $Na_2SO_4$, filtered and concentrated under reduced pressure to give a residue. The residue was purified by column chromatography ($SiO_2$, Petroleum ether/Ethyl acetate=20/1 to 2/1) and further purified by reverse phase flash [water (0.1% formic acid)/acetonitrile]. The mixture was adjusted pH ~7 with saturated $NaHCO_3$ aqueous solution and extracted with ethyl acetate (3×100 mL). The combined organic layers were washed with brine (50 mL), dried over $Na_2SO_4$, filtered and concentrated under reduced pressure to give the product. benzyl (2S)-2-(cyanomethyl)-4-[7-(5,6-dimethyl-1-tetrahydropyran-2-yl-indazol-4-yl)-2-methylsulfanyl-6,8-dihydro-5H-pyrido[3,4-d]pyrimidin-4-yl]piperazine-1-carboxylate (4.90 g, 7.20 mmol, 63% yield, 98% purity) was obtained as a yellow solid. LCMS [ESI, M+1]: 667.

$^1$H NMR (400 MHz, chloroform-d) δ=7.98 (s, 1H), 7.50-7.31 (m, 5H), 7.22 (s, 1H), 5.66 (dd, J=2.4, 9.6 Hz, 1H), 5.27-5.13 (m, 2H), 4.69 (br s, 1H), 4.27 (s, 2H), 4.13-3.97 (m, 3H), 3.89 (d, J=11.6 Hz, 1H), 3.81-3.68 (m, 1H), 3.51 (t, J=5.2 Hz, 2H), 3.30 (br s, 2H), 3.04 (t, J=11.6 Hz, 1H), 2.93-2.66 (m, 4H), 2.62-2.48 (m, 4H), 2.43 (s, 3H), 2.32 (s, 3H), 2.23-2.12 (m, 1H), 2.11-2.05 (m, 1H), 1.85-1.67 (m, 3H).

Step B: benzyl (2S)-2-(cyanomethyl)-4-[7-(5,6-dimethyl-1-tetrahydropyran-2-yl-indazol-4-yl)-2-methylsulfinyl-6,8-dihydro-5H-pyrido[3,4-d]pyrimidin-4-yl]piperazine-1-carboxylate To a solution of benzyl (2S)-2-(cyanomethyl)-4-[7-(5,6-dimethyl-1-tetrahydropyran-2-yl-indazol-4-yl)-2-methylsulfanyl-6,8-dihydro-5H-pyrido[3,4-d]pyrimidin-4-yl]piperazine-1-carboxylate (500 mg, 749 μmol, 1.0 eq) in toluene (10 mL) was added m-CPBA (152 mg, 749 μmol, 85% purity, 1.0 eq). The mixture was stirred at 0° C. for 1 hour. The mixture was diluted with water (10 mL) and adjusted pH ~7 with saturated $NaHCO_3$ aqueous solution. Then the mixture was extracted with ethyl acetate (3×20 mL). The combined organic layers were washed with brine (20 mL), dried over $Na_2SO_4$, filtered and concentrated under reduced pressure to give the product. Benzyl (2S)-2-(cyanomethyl)-4-[7-(5,6-dimethyl-1-tetrahydropyran-2-yl-indazol-4-yl)-2-methylsulfinyl-6,8-dihydro-5H-pyrido[3,4-d]pyrimidin-4-yl]piperazine-1-carboxylate (400 mg, 539 μmol, 72% yield, 92% purity) was obtained as a yellow solid and used next step directly without purification. LCMS [ESI, M+1]: 683.

Step C: benzyl (2S)-2-(cyanomethyl)-4-[2-[[(2S)-4,4-difluoro-1-methyl-pyrrolidin-2-yl]methoxyl]-7-(5,6-dimethyl-1-tetrahydropyran-2-yl-indazol-4-yl)-6,8-dihydro-5H-pyrido[3,4-d]pyrimidin-4-yl]piperazine-1-carboxylate To a solution of benzyl (2S)-2-(cyanomethyl)-4-[7-(5,6-dimethyl-1-tetrahydropyran-2-yl-indazol-4-yl)-2-methylsulfinyl-6,8-dihydro-5H-pyrido[3,4-d]pyrimidin-4-yl]piperazine-1-carboxylate (900 mg, 1.32 mmol, 1.0 eq) in toluene (20 mL) was added t-BuONa (379 mg, 3.95 mmol, 3.0 eq) and [(2S)-4,4-difluoro-1-methyl-pyrrolidin-2-yl] methanol (398 mg, 2.64 mmol, 2.0 eq). The mixture was stirred at 0° C. for 0.5 hour. The reaction mixture was diluted with water (30 mL) and extracted with ethyl acetate (3×50 mL). The combined organic layers were washed with brine (20 mL), dried over $Na_2SO_4$, filtered and concentrated under reduced pressure to give a residue. The residue was purified by column chromatography ($SiO_2$, Ethyl acetate/Methanol=100/1 to 10/1). Benzyl (2S)-2-(cyanomethyl)-4-[2-[[(2S)-4,4-difluoro-1-methyl-pyrrolidin-2-yl]methoxy]-7-(5,6-dimethyl-1-tetrahydropyran-2-yl-indazol-4-yl)-6,8-dihydro-5H-pyrido[3,4-d]pyrimidin-4-yl]piperazine-1-carboxylate (630 mg, 793 μmol, 60% yield, 97% purity) was obtained as a yellow solid. LCMS [ESI, M+1]: 770.

Step D: 2-[(2S)-4-[2-[[(2S)-4,4-difluoro-1-methyl-pyrrolidin-2-yl]methoxy]-7-(5,6-dimethyl-1-tetrahydropyran-2-yl-indazol-4-yl)-6,8-dihydro-5H-pyrido[3,4-d]pyrimidin-4-yl]piperazin-2-yl]acetonitrile To a solution of benzyl (2S)-2-(cyanomethyl)-4-[2-[[(2S)-4,4-difluoro-1-methyl-pyrrolidin-2-yl]methoxy]-7-(5,6-dimethyl-1-tetrahydropyran-2-yl-indazol-4-yl)-6,8-dihydro-5H-pyrido[3,4-d]pyrimidin-4-yl]piperazine-1-carboxylate (400 mg, 519 μmol, 1.0 eq) in methanol (2 mL) was added dry Pd/C (50 mg, 10% purity) and $NH_3$/methanol (1 mL, 20% purity) under $N_2$. The suspension was degassed under vacuum and purged with $H_2$ several times. The mixture was stirred under $H_2$ (15 psi) at 25° C. for 0.5 hour. The mixture was concentrated under vacuum. 2-[(2S)-4-[2-[[(2S)-4,4-difluoro-1-methyl-pyrrolidin-2-yl]methoxy]-dimethyl-1-tetrahydropyran-2-yl-indazol-4-yl)-6,8-dihydro-5H-pyrido[3,4-d]pyrimidin-4-yl]piperazin-2-yl]acetonitrile (330 mg, 519 μmol, 99% yield) was obtained as a yellow solid and used next step directly without purification. LCMS [ESI, M+1]: 636.

Step E: 2-[(2S)-4-[2-[[(2S)-4,4-difluoro-1-methyl-pyrrolidin-2-yl]methoxy]-7-(5,6-dimethyl-1H-indazol-4-yl)-6,8-dihydro-5H-pyrido[3,4-d]pyrimidin-4-yl]piperazin-2-yl]acetonitrile To a solution of 2-[(2S)-4-[2-[[(2S)-4,4-difluoro-1-methyl-pyrrolidin-2-yl]methoxy]-7-(5,6-dimethyl-1-tetrahydropyran-2-yl-indazol-4-yl)-6,8-dihydro-5H-pyrido[3,4-d]pyrimidin-4-yl]piperazin-2-yl]acetonitrile (50 mg, 78.6 μmol, 1.0 eq) in dichloromethane (50 uL) was added TFA (359 mg, 3.15 mmol, 233 μL, 40 eq). The mixture was stirred at 0° C. for 0.5 hour. The mixture was concentrated under vacuum and diluted with water (10 mL). The mixture was adjusted pH ~8 with saturated $NaHCO_3$ aqueous solution and extracted with dichloromethane (3×20 mL). The combined organic layers were washed with brine (20 mL), dried over $Na_2SO_4$, filtered and concentrated under reduced pressure to give the product. The residue was purified by column chromatography ($SiO_2$, Ethyl acetate/Methanol=100/1 to 10/1) and further purification by prep-HPLC (column: Waters Xbridge 150*25 5 u; mobile phase: [water (0.05% ammonia hydroxide v/v)-ACN]; B %: 30%-60%, 10 min). The desired fraction was collected and lyophilized. 2-[(2S)-4-[2-[[(2S)-4,4-difluoro-1-methyl-pyrrolidin-2-yl]methoxy]-7-(5,6-dimethyl-1H-indazol-4-yl)-6,8-dihydro-5H-pyrido[3,4-d]pyrimidin-4-yl]piperazin-2-yl]acetonitrile (7.29 mg, 13.2 μmol, 17% yield, 99.7% purity) was obtained as a white solid. LCMS [ESI, M+1]: 552.

$^1$H NMR (400 MHz, chloroform-d) δ=9.95 (br s, 1H), 8.04 (s, 1H), 7.15 (s, 1H), 4.48 (dd, J=4.4, 10.8 Hz, 1H), 4.33-4.19 (m, 3H), 4.00 (br d, J=11.6 Hz, 1H), 3.83 (br d, J=11.6 Hz, 1H), 3.51 (t, J=5.2 Hz, 2H), 3.42 (dt, J=5.6, 11.7 Hz, 1H), 3.26 (br s, 1H), 3.17-2.95 (m, 4H), 2.94-2.85 (m, 1H), 2.84-2.62 (m, 3H), 2.61-2.49 (m, 3H), 2.47 (s, 3H), 2.42 (s, 3H), 2.35 (s, 3H), 2.32-2.18 (m, 1H).

Step F: 2-[(2S)-4-[2-[[(2S)-4,4-difluoro-1-methyl-pyrrolidin-2-yl]methoxy]-7-(5,6-dimethyl-1H-indazol-4-yl)-6,8-dihydro-5H-pyrido[3,4-d]pyrimidin-4-yl]-1-(2-fluoroprop-2-enoyl)piperazin-2-yl] acetonitrile To a solution of 2-[(2S)-4-[2-[[(2S)-4,4-difluoro-1-methyl-pyrrolidin-2-yl]methoxy]-7-(5,6-dimethyl-1H-indazol-4-yl)-6,8-dihydro-5H-pyrido[3,4-d]pyrimidin-4-yl]piperazin-2-yl]acetonitrile (100 mg, 181 μmol, 1.0 eq) and 2-fluoroprop-2-enoic acid (24.5 mg, 272 μmol, 1.5 eq) in DMF (2 mL) was added T3P (461 mg, 725 μmol, 431 μL, 50% purity in ethyl acetate, 4.0 eq) and TEA (147 mg, 1.45 mmol, 202 uL, 8.0 eq) at 0° C. The mixture was stirred at 0° C. for 0.5 hour. The reaction mixture was diluted with water (20 mL) and extracted with ethyl acetate (3×30 mL). The combined organic layers were washed with brine (20 mL), dried over $Na_2SO_4$, filtered and concentrated under reduced pressure to give a residue. The residue was purified by column chromatography ($SiO_2$, Ethyl acetate/Methanol=100/1 to 10/1) and further purification by prep-HPLC (column: Waters Xbridge 150*25 5 u; mobile phase: [water (0.05% ammonia hydroxide v/v)-ACN]; B %: 38%-68%, 10 min). The desired fraction was collected and lyophilized. 2-[(2S)-4-[2-[[(2S)-4,4-difluoro-1-methyl-pyrrolidin-2-yl]methoxy]-7-(5,6-dimethyl-1H-indazol-4-yl)-6,8-dihydro-5H-pyrido[3,4-d]pyrimidin-4-yl]-1-(2-fluoroprop-2-enoyl)piperazin-2-yl]acetonitrile (11 mg, 17.5 μmol, 10% yield, 99.2% purity, 100% ee) was obtained as a off-white solid. LCMS [ESI, M+1]: 624.

$^1$H NMR (400 MHz, chloroform-d) δ=10.27-9.49 (s, 1H), 8.04 (s, 1H), 7.16 (s, 1H), 5.55-5.34 (m, 1H), 5.26 (dd, J=3.6, 16.8 Hz, 1H), 4.86 (br s, 1H), 4.46 (dd, J=4.8, 10.8 Hz, 1H), 4.34-3.88 (m, 6H), 3.66-3.25 (m, 5H), 3.19-2.62 (m, 7H), 2.60-2.45 (m, 4H), 2.42 (s, 3H), 2.35 (s, 3H), 2.32-2.19 (m, 1H).

Example 614

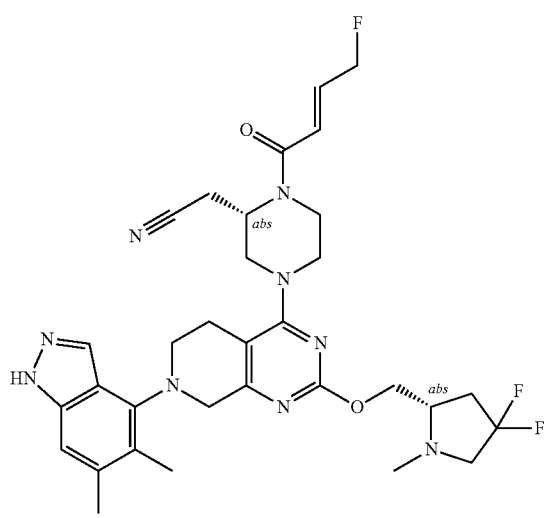 [SMILES: Cc1cc2[nH]ncc2c(N2CCc3c(nc(OC[C@@H]4CC(F)(F)CN4C)nc3N3CCN(C(=O)/C=C/CF)[C@@H](CC#N)C3)C2)c1C]

2-((S)-4-(2-(((S)-4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)-1-((E)-4-fluorobut-2-enoyl)piperazin-2-yl)acetonitrile Step A: 2-[(2S)-4-[2-[[(2S)-4,4-difluoro-1-methyl-pyrrolidin-2-yl]methoxy]-7-(5,6-dimethyl-1H-indazol-4-yl)-6,8-dihydro-5H-pyrido[3,4-d]pyrimidin-4-yl]-1-[(E)-4-fluorobut-2-enoyl]piperazin-2-yl] acetonitrile To a solution of 2-[(2S)-4-[2-[[(2S)-4,4-difluoro-1-methyl-pyrrolidin-2-yl]methoxy]-7-(5,6-dimethyl-1H-indazol-4-yl)-6,8-dihydro-5H-pyrido[3,4-d]pyrimidin-4-yl]piperazin-2-yl]acetonitrile (100 mg, 181 μmol, 1.0 eq) and (E)-4-fluorobut-2-enoic acid (28.3 mg, 272 μmol, 1.5 eq) in DMF (2 mL) was added T3P (461 mg, 725 μmol, 431 uL, 50% purity in ethyl acetate, 4.0 eq) and TEA (147 mg, 1.45 mmol, 202 uL, 8.0 eq) at 0° C. The mixture was stirred at 0° C. for 0.5 hour. The reaction mixture was diluted with water (20 mL) and extracted with ethyl acetate (3×30 mL). The combined organic layers were washed with brine (20 mL), dried over Na$_2$SO$_4$, filtered and concentrated under reduced pressure to give a residue. The residue was purified by column chromatography (SiO$_2$, Ethyl acetate/Methanol=100/1 to 10/1) and further purification by prep-HPLC (column: Xtimate C18 150*25 mm*5 um; mobile phase: [water (0.05% ammonia hydroxide v/v)-ACN]; B %: 40%-70%, 10 min). The desired fraction was collected and lyophilized. 2-[(2S)-4-[2-[[(2S)-4,4-difluoro-1-methyl-pyrrolidin-2-yl]methoxy]-7-(5,6-dimethyl-1H-indazol-4-yl)-6,8-dihydro-5H-pyrido[3,4-d]pyrimidin-4-yl]-1-[(E)-4-fluorobut-2-enoyl]piperazin-2-yl]acetonitrile (12 mg, 18.3 μmol, 10% yield, 97.3% purity, 95% ee) was obtained as a white solid. LCMS [ESI, M+1]: 638.

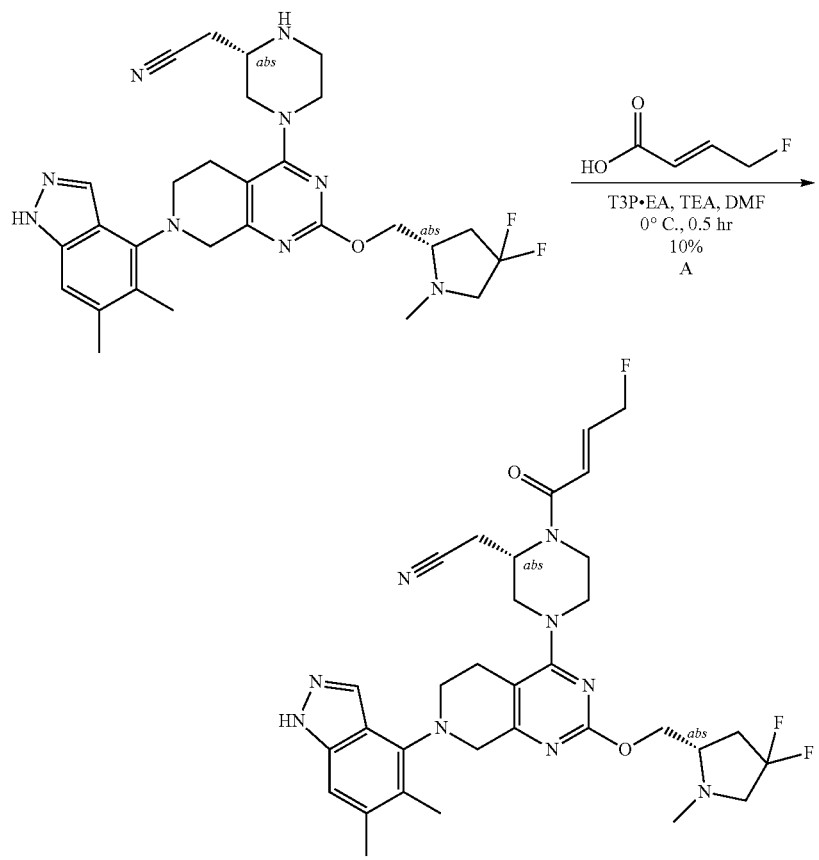

¹H NMR (400 MHz, chloroform-d) δ=10.06 (br s, 1H), 8.05 (s, 1H), 7.17 (s, 1H), 7.07-6.97 (m, 1H), 6.61 (br d, J=14.8 Hz, 1H), 5.20-5.07 (m, 3H), 4.48 (dd, J=4.8, 11.2 Hz, 1H), 4.31-4.27 (m, 3H), 4.20-3.80 (m, 3H), 3.55 (br t, J=5.2 Hz, 3H), 3.49-3.27 (m, 2H), 3.13 (br s, 1H), 3.05-2.63 (m, 6H), 2.62-2.46 (m, 4H), 2.43 (s, 3H), 2.36 (s, 3H), 2.33-2.21 (m, 1H).

Example 615

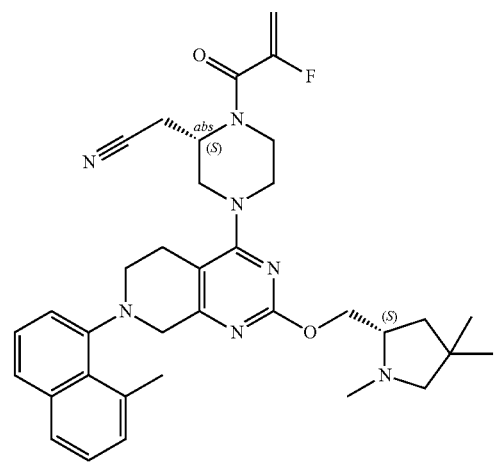

2-[(2S)-1-(2-fluoroprop-2-enoyl)-4-[7-(8-methyl-1-naphthyl)-2-[[(2S)-1,4,4-trimethylpyrrolidin-2-yl]methoxy]-6,8-dihydro-5H-pyrido[3,4-d]pyrimidin-4-yl]piperazin-2-yl]acetonitrile

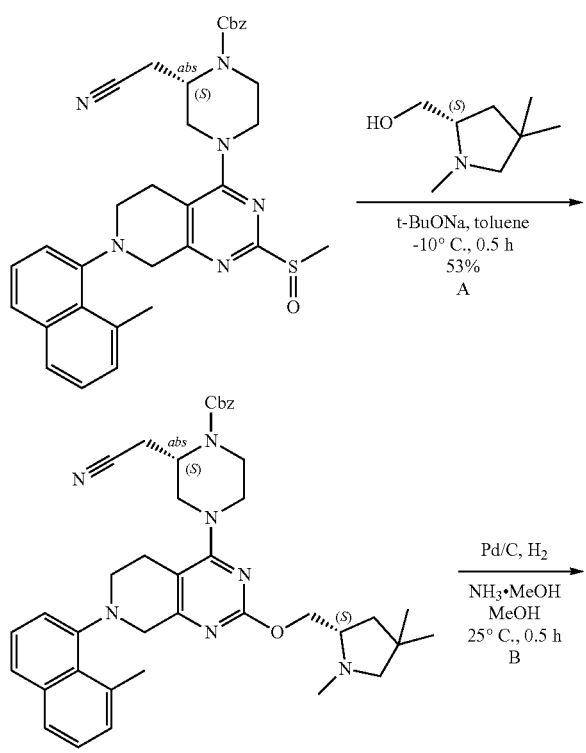

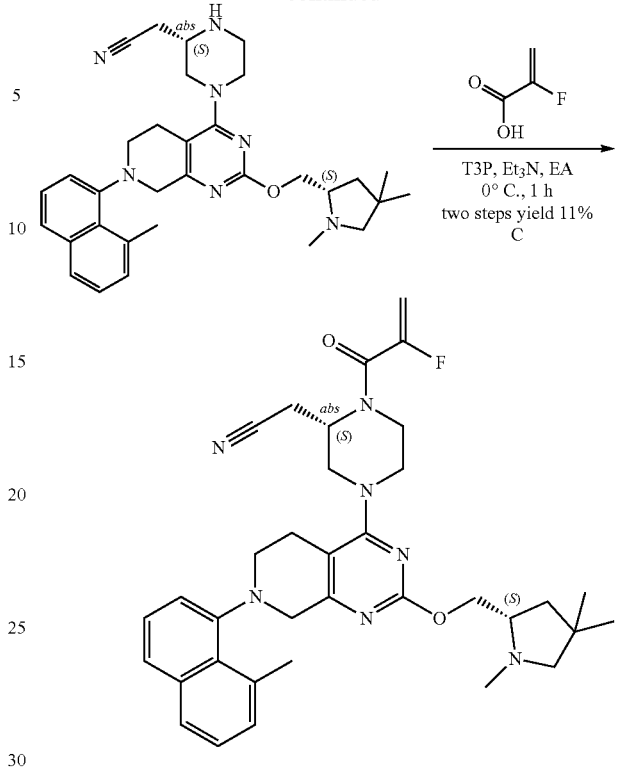

Step A: benzyl (2S)-2-(cyanomethyl)-4-[7-(8-methyl-1-naphthyl)-2-[[(2S)-1,4,4-trimethylpyrrolidin-2-yl]methoxy]-6,8-dihydro-5H-pyrido[3,4-d]pyrimidin-4-yl]piperazine-1-carboxylate To a solution of [(2S)-1,4,4-trimethylpyrrolidin-2-yl]methanol (217 mg, 1.51 mmol, 68.2 μL, 3 eq) and benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (300 mg, 504 μmol, 1 eq) in toluene (15 mL) was added t-BuONa (145 mg, 1.51 mmol, 3 eq) at 0° C. The mixture was stirred at 0° C. for 0.5 hour. Upon completion, the mixture was quenched with water (10 mL) and extracted with ethyl acetate (2×50 mL). The combined organic layers were washed with brine (1×50 mL), dried over Na$_2$SO$_4$, filtered and concentrated under vacuum. The residue was purified by reverse phase flash [water (0.1% FA)/acetonitrile]. The desired fractions were collected and neutralized with saturated Na$_2$CO$_3$ solution (10 mL) and extracted with ethyl acetate (3×50 mL). The separated organic layers were dried over sodium sulfate, filtered and concentrated under vacuum. Benzyl (2S)-2-(cyanomethyl)-4-[7-(8-methyl-1-naphthyl)-2-[[(2S)-1,4,4-trimethylpyrrolidin-2-yl]methoxy]-6,8-dihydro-5H-pyrido[3,4-d]pyrimidin-4-yl]piperazine-1-carboxylate (180 mg, 267 μmol, 53% yield, 99.8% purity) was obtained as a yellow solid. LCMS [ESI, M+1]: 675.

¹H NMR (400 MHz, chloroform-d) δ=7.73-7.60 (m, 2H), 7.27 (s, 9H), 5.21 (s, 2H), 4.68 (br s, 1H), 4.47-4.34 (m, 1H), 4.30-4.15 (m, 2H), 4.13-4.04 (m, 1H), 3.95-3.69 (m, 2H), 3.56-3.34 (m, 2H), 3.28-2.48 (m, 13H), 2.47-2.33 (m, 3H), 2.22-2.11 (m, 1H), 1.88 (br dd, J=8.4, 12.6 Hz, 1H), 1.56 (ddd, J=4.6, 7.8, 12.6 Hz, 1H), 1.16 (d, J=4.0 Hz, 3H), 1.10-0.98 (m, 3H).

Step B: 2-[(2S)-4-[7-(8-methyl-1-naphthyl)-2-[[(2S)-1,4,4-trimethyl pyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(8-methyl-1-naphthyl)-2-[[(2S)-1,4,4-trimethylpyrrolidin-2-yl]methoxy]-6,8-dihydro-5H-pyrido[3,4-d]pyrimidin-4-yl]piperazine-1-carboxylate (130 mg, 193 μmol, 1 eq) in MeOH (4 mL) was added $NH_3$.MeOH (2 mL, 15% purity) and Pd/C (26 mg, 10% purity) under $N_2$. The suspension was degassed under vacuum and purged with $H_2$ several times. The mixture was stirred under $H_2$ (15 psi) at 25° C. for 0.5 hour. Upon completion, the mixture was filtered and the filtrate was concentrated under vacuum. 2-[(2S)-4-[7-(8-methyl-1-naphthyl)-2-[[(2S)-1,4,4-trimethyl pyrrolidin-2-yl]methoxy]-6,8-dihydro-5H-pyrido[3,4-d]pyrimidin-4-yl]piperazin-2-yl]acetonitrile (100 mg, 159 μmol, 85.9% purity) was obtained as a yellow solid which was used into next step without further purification. LCMS [ESI, M+1]: 540.

Step C: 2-[(2S)-1-(2-fluoroprop-2-enoyl)-4-[7-(8-methyl-1-naphthyl)-2-[[(2S)-1,4,4-trimethylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2S)-1,4,4-trimethylpyrrolidin-2-yl]methoxy]-6,8-dihydro-5H-pyrido[3,4-d]pyrimidin-4-yl]piperazin-2-yl]acetonitrile (90 mg, 143 μmol, 1 eq), 2-fluoroprop-2-enoic acid (38.7 mg, 430 μmol, 3 eq) and $Et_3N$ (130 mg, 1.29 mmol, 179 uL, 9 eq) in ethyl acetate (15 mL) was added T3P (365 mg, 573 μmol, 341 uL, 50% purity in ethyl acetate, 4 eq) at 0° C. The mixture was stirred at 0° C. for 1 hour. Upon completion, the mixture was diluted with water (3 mL). The organic layer was separated, washed with brine (1×10 mL), dried over sodium sulfate, filtered and concentrated under vacuum. The mixture was purified by column chromatography ($SiO_2$, ethyl acetate/methanol=20/1 to 10/1). The residue was purified by prep-HPLC (column: Waters Xbridge 150*25 5 u; mobile phase: [water (0.05% ammonia hydroxide v/v)-ACN]; B %: 62%-89%, 10 min). The residue was concentrated under reduced pressure to remove ACN, and then lyophilization. 2-[(2S)-1-(2-fluoroprop-2-enoyl)-4-[7-(8-methyl-1-naphthyl)-2-[[(2S)-1,4,4-trimethylpyrrolidin-2-yl]methoxy]-6,8-dihydro-5H-pyrido[3,4-d]pyrimidin-4-yl]piperazin-2-yl]acetonitrile (12.7 mg, 20.6 μmol, 99.7% purity) was obtained as a white solid. LCMS [ESI, M+1]: 612.

$^1$H NMR (400 MHz, chloroform-d) δ=7.79-7.56 (m, 2H), 7.51-7.31 (m, 2H), 7.27-7.08 (m, 2H), 5.65-5.08 (m, 2H), 4.85 (br s, 1H), 4.49-4.32 (m, 1H), 4.30-3.96 (m, 4H), 3.95-3.71 (m, 1H), 3.59-3.35 (m, 2H), 3.28-2.54 (m, 13H), 2.42 (br s, 3H), 2.16 (br d, J=8.8 Hz, 1H), 1.96-1.81 (m, 1H), 1.63-1.45 (m, 1H), 1.15 (br s, 3H), 1.06 (br s, 3H).

Example 616

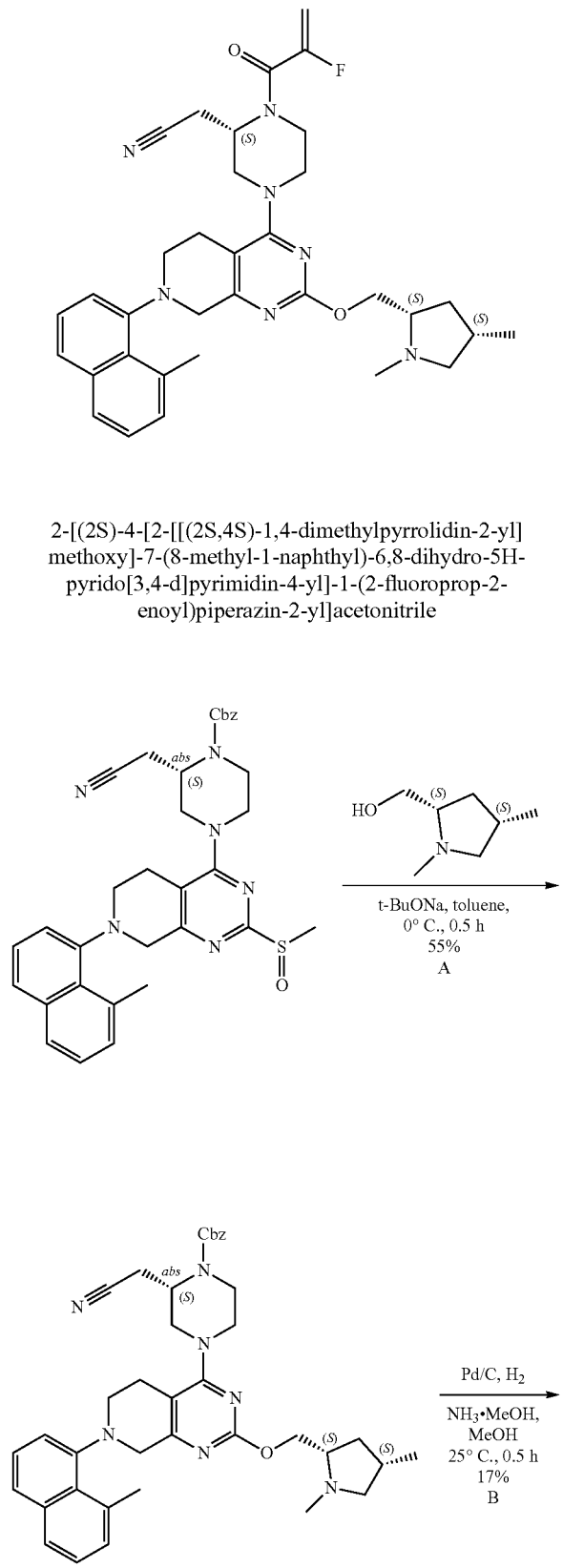

2-[(2S)-4-[2-[[(2S,4S)-1,4-dimethylpyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile

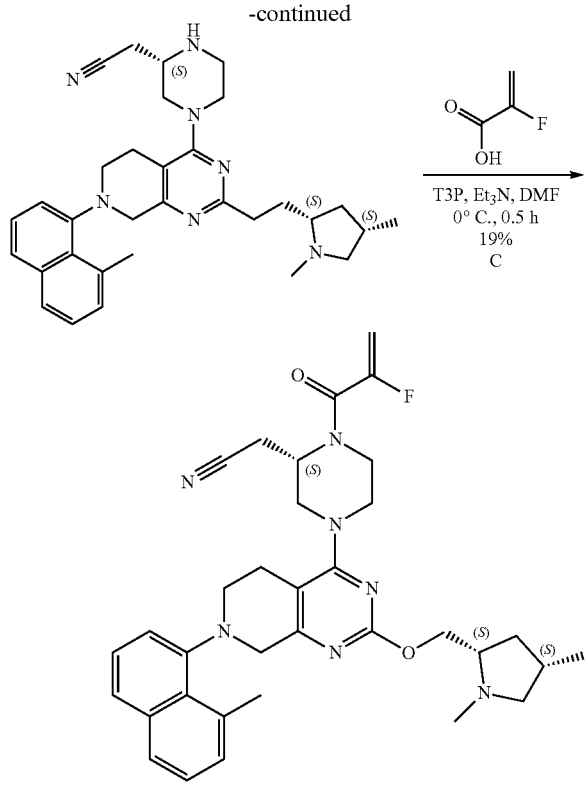

Step A: benzyl (2S)-2-(cyanomethyl)-4-[2-[[(2S,4S)-1,4-dimethylpyrrolidin-2-yl]methoxy]-7-(8-methyl-1-naphthyl)-6,8-dihydro-5H-pyrido[3,4-d]pyrimidin-4-yl]piperazine-1-carboxylate To a solution of [(2S,4S)-1,4-dimethylpyrrolidin-2-yl]methanol (326 mg, 2.52 mmol, 68.2 uL, 3 eq) and benzyl (2S)-2-(cyanomethyl)-4-[7-(8-methyl-1-naphthyl)-2-methyl sulfinyl-6, 8-dihydro-5H-pyrido [3,4-d]pyrimidin-4-yl]piperazine-1-carboxylate (500 mg, 841 μmol, 1 eq) in toluene (20 mL) was added t-BuONa (242 mg, 2.52 mmol, 3 eq) at 0° C. The mixture was stirred at 0° C. for 0.5 hour. Upon completion, the mixture was quenched with water (10 mL) and extracted with ethyl acetate (2×20 mL). The combined organic layers were washed with brine (1×20 mL), dried over Na$_2$SO$_4$, filtered and concentrated under vacuum. The residue was purified by reverse phase HPLC (0.1% FA condition). The residue was basified with saturated aqueous NaHCO$_3$ solution to pH=8 and extracted with ethyl acetate (3×50 mL). The organic phase was separated, dried over sodium sulfate, filtered and concentrated under vacuum. benzyl (2S)-2-(cyanomethyl)-4-[2-[[(2S,4S)-1,4-dimethylpyrrolidin-2-yl]methoxy]-7-(8-methyl-1-naphthyl)-6,8-dihydro-5H-pyrido [3,4-d]pyrimidin-4-yl]piperazine-1-carboxylate (328 mg, 461 μmol, 55% yield, 92.7% purity) was obtained as a yellow solid. LCMS [ESI, M+1]: 661.

Step B: 2-[(2S)-4-[2-[[(2S,4S)-1,4-dimethylpyrrolidin-2-yl]methoxy]-7-(8-methyl-1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-[[(2S,4S)-1,4-dimethylpyrrolidin-2-yl]methoxy]-7-(8-methyl-1-naphthyl)-6,8-dihydro-5H-pyrido[3,4-d]pyrimidin-4-yl]piperazine-1-carboxylate (100 mg, 151 μmol, 1 eq) in MeOH (4 mL) was added NH$_3$.MeOH (2 mL, 20% purity) and Pd/C (20 mg, 10% purity) under N$_2$. The suspension was degassed under vacuum and purged with H$_2$ several times. The mixture was stirred under H$_2$ (15 psi) at 25° C. for 0.5 hour. Upon completion, the mixture was filtered and the filtrate was concentrated under vacuum. The residue was purified by prep-HPLC (column: Phenomenex Synergi C18 150*30 mm*4 um; mobile phase: [water (0.225% FA)-ACN]; B %: 13%-43%, 10 min). After that, the residue was purified by prep-HPLC (column: Waters Xbridge 150*25 5 u; mobile phase: [water (0.05% ammonia hydroxide v/v)-ACN]; B %: 55%-85%, 10 min). The residue was concentrated under reduced pressure to remove ACN, and then lyophilization. 2-[(2S)-4-[2-[[(2S,4S)-1,4-dimethylpyrrolidin-2-yl]methoxy]-7-(8-methyl-1-naphthyl)-6,8-dihydro-5H-pyrido[3,4-d]pyrimidin-4-yl]piperazin-2-yl]acetonitrile (13.9 mg, 26.4 μmol, 17% yield, 100% purity) was obtained as a white solid. LCMS [ESI, M+1]: 526.

$^1$H NMR (400 MHz, chloroform-d) δ=7.69 (d, J=8.2 Hz, 1H), 7.64 (dd, 7.6 Hz, 1H), 7.40 (dt, J=4.0, 7.8 Hz, 1H), 7.36-7.31 (m, 1H), 7.26-7.19 (m, 2H), 4.43 (dt, J=4.8, 10.2 Hz, 1H), 4.28-4.11 (m, 2H), 4.07-3.70 (m, 3H), 3.48 (br d, J=11.8 Hz, 1H), 3.38-2.82 (m, 11H), 2.80-2.64 (m, 2H), 2.61-2.53 (m, 3H), 2.49 (t, J=8.6 Hz, 1H), 2.42 (d, J=2.4 Hz, 3H), 2.35-2.15 (m, 2H), 1.39-1.25 (m, 1H), 1.08 (d, J=6.8 Hz, 3H).

Step C: 2-[(2S)-4-[2-[[(2S,4S)-1,4-dimethylpyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile To a solution of 2-[(2S)-4-[2-[[(2S,4S)-1,4-dimethylpyrrolidin-2-yl] methoxy]-7-(8-methyl-1-naphthyl)-6,8-dihydro-5H-pyrido[3,4-d]pyrimidin-4-yl]piperazin-2-yl]acetonitrile (100 mg, 190 μmol, 1 eq), 2-fluoroprop-2-enoic acid (51.4 mg, 571 μmol, 3 eq) and Et$_3$N (173 mg, 1.71 mmol, 238 uL, 9 eq) in DMF (10 mL) was added T3P (484 mg, 761 μmol, 452 uL, 50% purity, 4 eq) at 0° C. The mixture was stirred at 0° C. for 0.5 hour. Upon completion, the residue was diluted with water (10 mL) and extracted with ethyl acetate (2×20 mL). The combined organic layers were washed with brine (1×20 mL), dried over sodium sulfate, filtered and concentrated under vacuum. The mixture was purified by column chromatography (SiO$_2$, Dichloromethane/Methanol=10/1). After that, the residue was purified by prep-HPLC (column: Xtimate C18 150*25 mm*5 um; mobile phase: [water (0.05% ammonia hydroxide v/v)-ACN]; B %: 60%-90%, 10 min). The residue was concentrated under reduced pressure to remove ACN, and then lyophilization. 2-[(2S)-4-[2-[[(2S,4S)-1,4-dimethylpyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile (22.2 mg, 37.1 μmol, 19% yield, 99.8% purity) was obtained as a white solid. LCMS [ESI, M+1]: 598.

$^1$H NMR (400 MHz, chloroform-d) δ=7.72-7.61 (m, 2H), 7.45-7.37 (m, 1H), 7.37-7.31 (m, 1H), 7.26-7.17 (m, 2H), 5.53-5.32 (m, 1H), 5.26 (dd, J=3.6, 16.8 Hz, 1H), 4.86 (br s, 1H), 4.48-4.35 (m, 1H), 4.30-3.99 (m, 4H), 3.95-3.73 (m, 1H), 3.60-3.39 (m, 2H), 3.29-2.94 (m, 5H), 2.93-2.67 (m, 7H), 2.66-2.56 (m, 1H), 2.55-2.47 (m, 1H), 2.43 (d, J=4.6 Hz, 3H), 2.35-2.13 (m, 2H), 1.36-1.25 (m, 1H), 1.09 (dd, J=3.0, 6.8 Hz, 3H).

Example 617

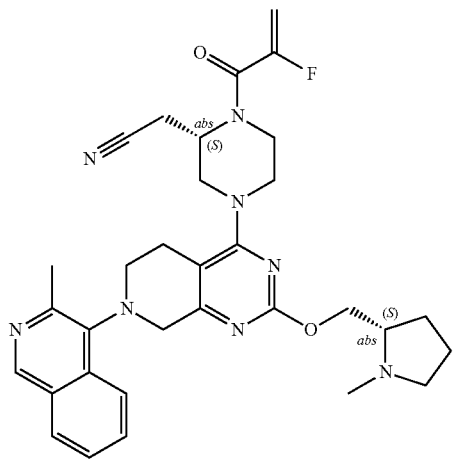

2-(((S)-1-(2-fluoroacryloyl)-4-(7-(3-methylisoquino-lin-4-yl)-2-(((S)-1-methylpyrrolidin-2-yl)methoxy)-5,6,7,8-tetrahydropyrido[3,4-d]pyrimidin-4-yl)piper-azin-2-yl)acetonitrile

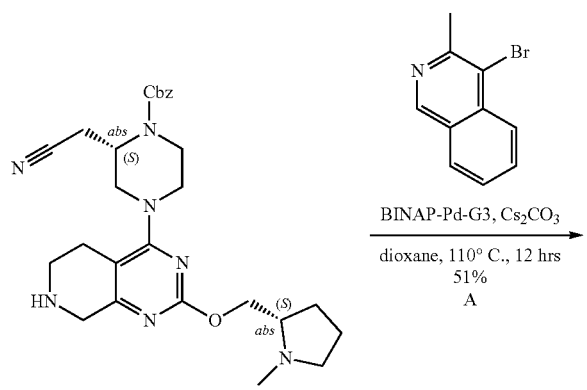

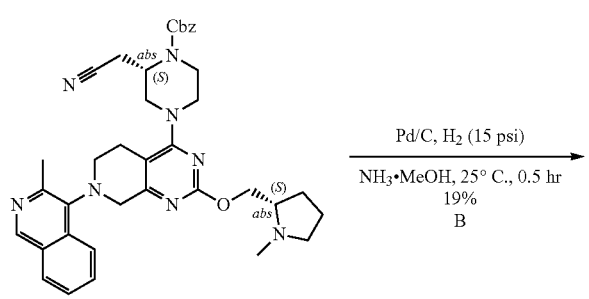

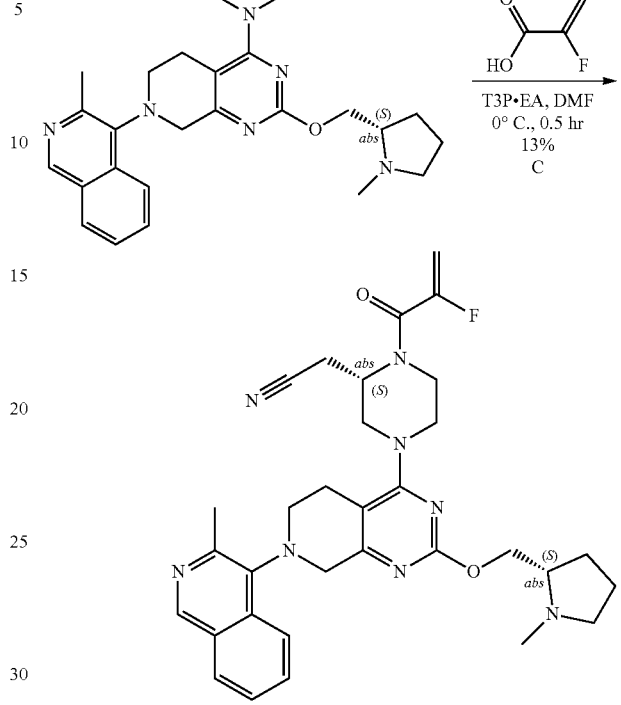

Step A: benzyl (2S)-2-(cyanomethyl)-4-[7-(3-methyl-4-isoquinolyl)-2-[[(2S)-1-methylpyrrolidin-2-yl]methoxy]-6,8-dihydro-5H-pyrido[3,4-d]pyrimidin-4-yl]piperazine-1-carboxylate A mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (300 mg, 593 µmol, 1.0 eq), 4-bromo-3-methyl-isoquinoline (198 mg, 890 µmol, 1.5 eq), Cs₂CO₃ (483 mg, 1.48 mmol, 2.5 eq), BINAP-Pd-G3 (118 mg, 119 µmol, 0.2 eq) in dioxane (6 mL) was degassed and purged with N₂ 3 times. The mixture was heated at 110° C. for 12 hours. The reaction mixture was diluted with water (20 mL) and extracted with ethyl acetate (3×30 mL). The combined organic layers were washed with brine (20 mL), dried over Na₂SO₄, filtered and concentrated under reduced pressure to give a residue. The residue was purified by column chromatography (SiO₂, Ethyl acetate/ Methanol=100/1 to 10:1). benzyl (2S)-2-(cyanomethyl)-4-[7-(3-methyl-4-isoquinolyl)-2-[[(2S)-1-methylpyrrolidin-2-yl]methoxy]-6,8-dihydro-5H-pyrido[3,4-d]pyrimidin-4-yl] piperazine-1-carboxylate (200 mg, 303 µmol, 51% yield, 98% purity) was obtained as a yellow solid. LCMS [ESI, M+1]: 647.

Step B: 2-[(2S)-4-[7-(3-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-2-(cyanomethyl)-4-[7-(3-methyl-4-isoquinolyl)-2-[[(2S)-1-methylpyrrolidin-2-yl] methoxy]-6,8-dihydro-5H-pyrido[3,4-d]pyrimidin-4-yl]piperazine-1-carboxylate (50 mg, 77.3 µmol, 1.0 eq) in methanol (2 mL) was added dry Pd/C (10 mg, 10% purity) and NH₃/MeOH (1 mL, 20% purity) under N₂. The suspension was degassed under vacuum and purged with H₂ several times. The mixture was stirred under H₂ (15 psi) at 25° C. for 0.5 hour. The mixture was concentrated under vacuum. The residue was purified by prep-HPLC (column: Waters Xbridge 150*25 5 u; mobile phase: [water (0.05% ammonia hydroxide v/v)-ACN]; B %: 30%-60%, 10 min). The desired fraction was collected and lyophilized. 2-[(2S)-4-[7-(3-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (7.81 mg, 14.9 μmol, 19% yield, 98.3% purity) was obtained as a yellow solid. LCMS [ESI, M+1]: 513.

¹H NMR (400 MHz, chloroform-d) δ=9.07 (s, 1H), 8.14 (d, J=8.4 Hz, 1H), 7.97 (d, J=8.0 Hz, 1H), 7.65 (dt, J=1.2, 7.6 Hz, 1H), 7.58-7.47 (m, 1H), 4.41 (br dd, J=4.8, 10.4 Hz, 1H), 4.3 (s, 2H), 4.16 (dd, J=6.8, 10.8 Hz, 1H), 4.10-3.93 (m, 1H), 3.91-3.77 (m, 1H), 3.57-3.37 (m, 2H), 3.36-3.21 (m, 1H), 3.18-2.85 (m, 6H), 2.75-2.61 (m, 5H), 2.56 (br d, J=6.8 Hz, 2H), 2.48 (s, 3H), 2.33-2.22 (m, 1H), 2.12-1.98 (m, 1H), 1.94-1.80 (m, 3H).

Step C: 2-[(2S)-1-(2-fluoroprop-2-enoyl)-4-[7-(3-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(3-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (80 mg, 156 μmol, 1.0 eq) and 2-fluoroprop-2-enoic acid (28.1 mg, 312 μmol, 2.0 eq) in DMF (2 mL) was added T3P (297 mg, 468 μmol, 278 μL, 50% purity in ethyl acetate, 3.0 eq) and TEA (126 mg, 1.25 mmol, 173 μL, 8.0 eq) at 0° C. The mixture was stirred at 0° C. for 0.5 hour. The reaction mixture was diluted with ethyl acetate (20 mL) and washed with water (3×20 mL). The combined organic layers were washed with brine (20 mL), dried over Na₂SO₄, filtered and concentrated under reduced pressure to give a residue. The residue was purified by column chromatography (SiO₂, Ethyl acetate/Methanol=100/1 to 10/1) and further purification by prep-HPLC (column: Waters Xbridge 150*25 5 u; mobile phase: [water (0.05% ammonia hydroxide v/v)-ACN]; B %: 35%-65%, 10 min). The desired fraction was collected and lyophilized. 2-[(2S)-1-(2-fluoroprop-2-enoyl)-4-[7-(3-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (12 mg, 19.9 μmol, 13% yield, 97.4% purity, 100% ee) was obtained as a yellow solid. LCMS [ESI, M+1]: 585.

¹H NMR (400 MHz, chloroform-d) δ=9.08 (s, 1H), 8.26-8.04 (m, 1H), 7.97 (br d, J=7.6 Hz, 1H), 7.73-7.60 (m, 1H), 7.58-7.49 (m, 1H), 5.42 (d, J=47.6 Hz, 1H), 5.27 (dd, J=3.6, 16.8 Hz, 1H), 4.85 (br s, 1H), 4.45-3.92 (m, 7H), 3.83-3.25 (m, 4H), 3.22-2.59 (m, 10H), 2.49 (s, 3H), 2.36-2.24 (m, 1H), 2.13-1.99 (m, 1H), 1.92-1.76 (m, 3H).

Example 618

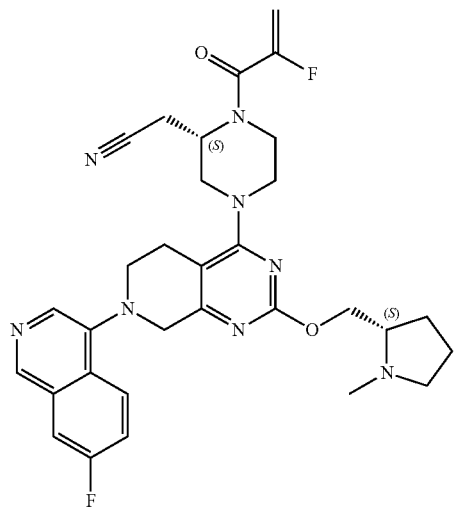

(S)-benzyl-2-(cyanomethyl)-4-(7-(7-fluoroisoquinolin-4-yl)-2-((S)-1-methylpyrrolidin-2-yl)methoxy)-5,6,7,8-tetrahydropyrido[3,4-d]pyrimidin-4-yl)piperazine-1-carboxylate

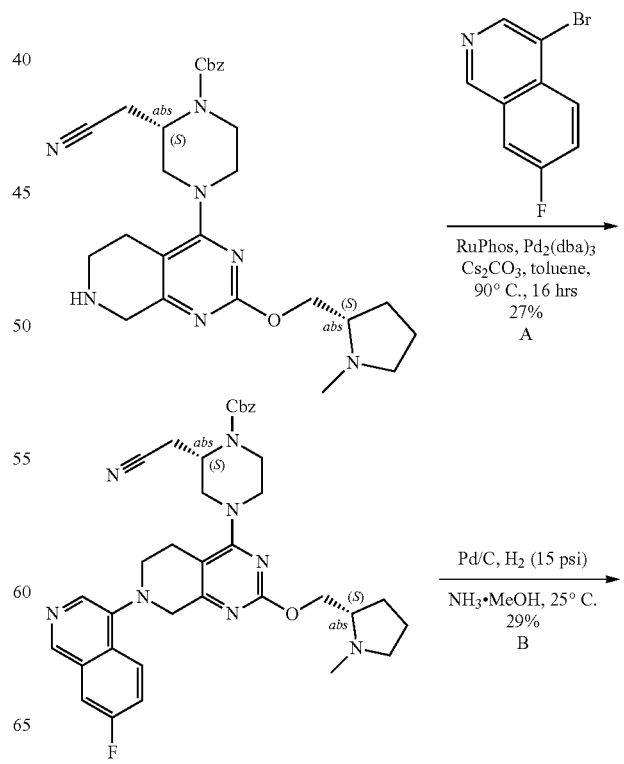

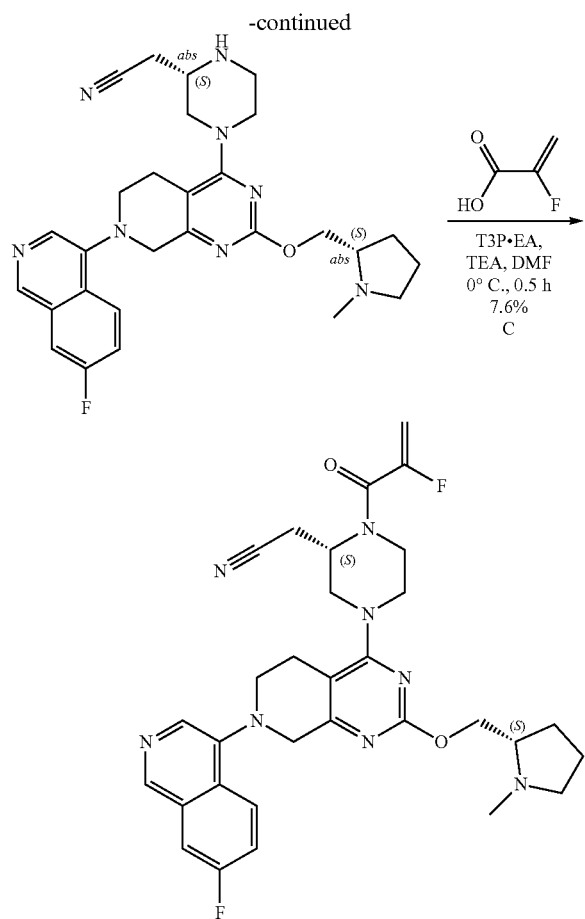

Step A: (S)-benzyl-2-(cyanomethyl)-4-(7-(7-fluoroisoquinolin-4-yl)-2-(((S)-1-methylpyrrolidin-2-yl)methoxy)-5,6,7,8-tetrahydropyrido[3,4-d]pyrimidin-4-yl)piperazine-1-carboxylate To a solution of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (300 mg, 0.59 mmol, 1.0 eq) in toluene (10.0 mL) was added 4-bromo-7-fluoro-isoquinoline (268 mg, 1.19 mmol, 2.0 eq), RuPhos (111 mg, 237 μmol, 0.40 eq), Cs₂CO₃ (483 mg, 1.48 mmol, 2.5 eq) and Pd₂(dba)₃ (109 mg, 118 μmol, 0.20 eq) at 25° C., the mixture was stirred at 90° C. for 16 hours. The reaction mixture was diluted with water (5.0 mL) and extracted with ethyl acetate (3×5.0 mL). The combined organic layers were washed with brine (3×5.0 mL), dried over Na₂SO₄, filtered and the filtrate was concentrated under reduced pressure to give a residue. The residue was purified by column chromatography (SiO₂, Petroleum ether/Ethyl acetate=1/1 to Petroleum ether/Ethyl acetate/EtOH (2% NH₃H₂O)=4/3/1). Then the crude product was purified by reversed-phase HPLC (0.1% FA condition). The desired fractions were collected and concentrated under vacuum to give (S)-benzyl-2-(cyanomethyl)-4-(7-(7-fluoroisoquinolin-4-yl)-2-((S)-1-methylpyrrolidin-2-yl)methoxy)-5,6,7,8-tetrahydropyrido[3,4-d]pyrimidin-4-yl)piperazine-1-carboxylate (105 mg, 160 μmol, 27% yield, 99% purity) as a yellow solid. LCMS [M+1]: 651.

¹H NMR (400 MHz, chloroform-d) δ=2.04-2.08 (m, 4H), 2.69 (d, J=5.64 Hz, 1H), 2.73 (d, J=5.52 Hz, 1H), 2.81-2.85 (m, 3H), 2.87-3.02 (m, 3H), 3.09-3.19 (m, 1H), 3.32-3.45 (m, 3H), 3.45-3.55 (m, 1H), 3.57-3.68 (m, 1H), 3.99 (br d, J=12.52 Hz, 1H), 4.09-4.17 (m, 1H), 4.28-4.34 (m, 1H), 4.31 (m, 1H), 4.46 (dd, J=11.84, 4.31 Hz, 1H), 4.63-4.74 (m, 1H), 4.80 (br dd, J=11.32, 6.82 Hz, 1H), 5.20-5.23 (m, 2H), 5.30-5.32 (m, 2H), 7.35-7.42 (m, 5H), 7.47-7.53 (m, 1H), 7.60 (dd, J=8.68, 2.56 Hz, 1H), 8.16 (dd, J=9.24, 5.25 Hz, 1H), 8.22-8.25 (m, 1H), 8.95-9.00 (m, 1H).

Step B: 2-((S)-4-(7-(7-fluoroisoquinolin-4-yl)-2-(((S)-1-methylpyrrolidin-2-yl)methoxy)-5,6,7,8-tetrahydropyrido[3,4-d]pyrimidin-4-yl)piperazin-2-yl)acetonitrile To a solution of (S)-benzyl 2-(cyanomethyl)-4-(7-(7-fluoroisoquinolin-4-yl)-2-((S)-1-methylpyrrolidin-2-yl)methoxy)-5,6,7,8-tetrahydropyrido[3,4-d]pyrimidin-4-yl)piperazine-1-carboxylate (30.0 mg, 46.1 μmol, 1.0 eq) in MeOH (1.0 mL) was added NH₃/MeOH (46.1 μmol, 1.5 mL, 15% purity, 1.0 eq) and Pd/C (20.0 mg, 46.1 μmol, 10% purity, 1.0 eq) under N₂. The suspension was degassed under vacuum and purged with H₂ (93.1 ug, 46.1 μmol, 1.0 eq) several times. The mixture was stirred under H₂ (15 psi) at 25° C. for 1 hour. The reaction mixture was filtered through a celite and washed with MeOH (20 mL). The filtrate was concentrated under reduced pressure at 45° C. to give a residue. The residue was purified by prep-HPLC (basic condition) (column: Xtimate C18 150*25 mm*5 um; mobile phase: [water (0.05% ammonia hydroxide v/v)-ACN]; B %: 43%-73%, 10 min). The desired fraction was collected and lyophilized. 2-((S)-4-(7-(7-fluoroisoquinolin-4-yl)-2-(((S)-1-methylpyrrolidin-2-yl)methoxy)-5,6,7,8-tetrahydropyrido[3,4-d]pyrimidin-4-yl)piperazin-2-yl)acetonitrile (7 mg, 13.3 μmol, 28.8% yield, 98% purity) was obtained as a yellow solid. LCMS [M+1]: 517.

¹H NMR (400 MHz, chloroform-d) δ=1.75-1.90 (m, 3H), 1.99-2.13 (m, 1H), 2.24-2.34 (m, 1H), 2.45-2.51 (m, 3H), 2.53-2.58 (m, 2H), 2.64-2.74 (m, 1H), 2.80-2.88 (m, 2H), 2.89-2.96 (m, 1H), 2.97-3.06 (m, 1H), 3.07-3.18 (m, 3H), 3.22-3.33 (m, 1H), 3.38-3.48 (m, 2H), 3.82-3.89 (m, 1H), 4.03 (br d, J=12.36 Hz, 1H), 4.18 (dd, J=10.56, 6.69 Hz, 1H), 4.30 (s, 2H), 4.40 (dd, J=10.64, 4.75 Hz, 1H), 7.49 (ddd, J=9.16, 8.35, 2.63 Hz, 1H), 7.60 (dd, J=8.76, 2.50 Hz, 1H), 8.17 (dd, J=9.24, 5.38 Hz, 1H), 8.24 (s, 1H), 8.96 (s, 1H).

Step C: 2-[(2S)-4-[7-(7-fluoro-4-isoquinolyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(7-fluoro-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (90.7 mg, 175 μmol, 1.0 eq) and 2-fluoroprop-2-enoic acid (31.6 mg, 351 μmol, 2.0 eq) in DMF (2 mL) was added T3P (335 mg, 526 μmol, 313 μL, 50% purity in ethyl acetate, 3.0 eq) and TEA (142 mg, 1.40 mmol, 195 μL, 8.0 eq) at 0° C. The mixture was stirred at 0° C. for 0.5 hour. The reaction mixture was diluted with ethyl acetate (20 mL) and washed with water (3×20 mL). The combined organic layers were washed with brine (20 mL), dried over Na₂SO₄, filtered and the filtrate was concentrated under reduced pressure to give a residue. The residue was purified by column chromatography (SiO₂, Ethyl acetate/Methanol=100/1 to 10/1) and further purification by prep-HPLC (column: Waters Xbridge 150*25 mm*5 um; mobile phase: [water (0.05% ammonia hydroxide v/v)-ACN]; B %: 32%-59%, 10 min). The desired fraction was collected and lyophilized. 2-[(2S)-4-[7-(7-fluoro-4-isoquinolyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (8 mg, 13.4 μmol, 7.6% yield, 98.3% purity, 100% ee) was obtained as a white solid. LCMS [M+1]: 589.

¹H NMR (400 MHz, chloroform-d) δ=8.97 (s, 1H), 8.24 (s, 1H), 8.16 (dd, 9.2 Hz, 1H), 7.60 (dd, J=2.4, 8.8 Hz, 1H), 7.54-7.40 (m, 1H), 5.55-5.33 (m, 1H), 5.27 (dd, J=3.6, 16.8 Hz, 1H), 4.87 (br s, 1H), 4.44-3.94 (m, 7H), 3.72-3.28 (m, 4H), 3.22-3.06 (m, 2H), 3.04-2.93 (m, 2H), 2.93-2.74 (m, 2H), 2.72-2.66 (m, 1H), 2.49 (s, 3H), 2.36-2.24 (m, 1H), 2.13-2.03 (m, 1H), 1.92-1.76 (m, 3H).

Example 619

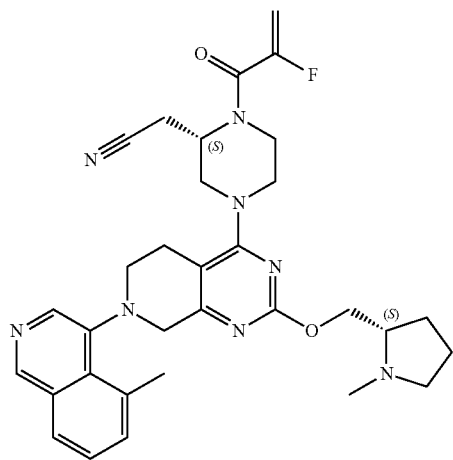

2-[(2S)-1-(2-fluoroprop-2-enoyl)-4-[7-(5-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile

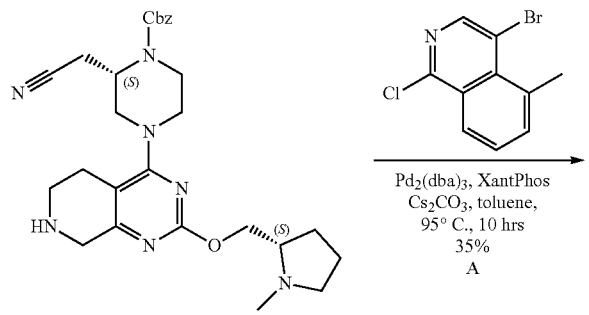

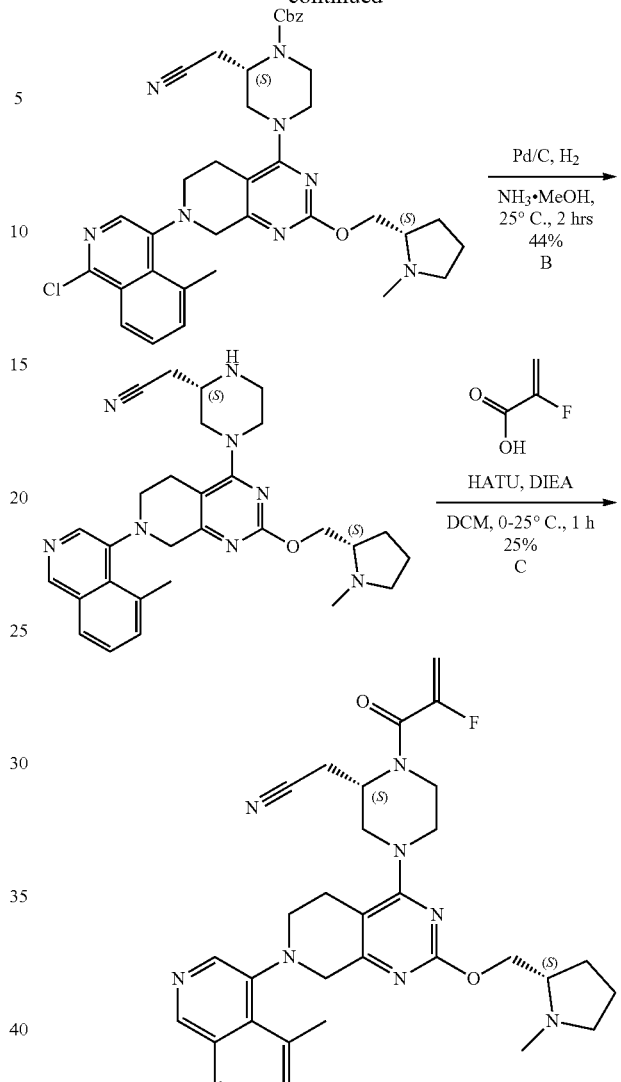

Step A: benzyl (2S)-4-[7-(1-chloro-5-methyl-4-isoquinolyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate Benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (300 mg, 593 μmol, 1.0 eq), 4-bromo-1-chloro-5-methyl-isoquinoline (198 mg, 771 μmol, 1.3 eq), Pd₂(dba)₃ (109 mg, 119 μmol, 0.2 eq) and Cs₂CO₃ (483 mg, 1.48 mmol, 2.5 eq), XantPhos (137 mg, 237 μmol, 0.4 eq) in toluene (10 mL) was de-gassed and then heated to 95° C. for 10 hours under N₂. Upon completion, the mixture was filtered and the filtrate was concentrated under vacuum. The residue was purified by chromatography (Al₂O₃, petroleum ether/ethyl acetate 2/1 to 0/1) followed by reversed phase flash [water (0.1% FA)/acetonitrile]. The desired fractions were collected and neutralized with solid NaHCO₃, concentrated under vacuum to remove MeCN and extracted with ethyl acetate (2×15 mL). The organic layers were dried over Na₂SO₄ and concentrated under vacuum to give benzyl (2S)-4-[7-(1-chloro-5-methyl-4-isoquinolyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (150 mg, 209 µmol, 35% yield, 95% purity) as a yellow solid. LCMS [ESI, M+1]: 681.

1H NMR (400 MHz, chloroform-d) δ=8.27 (d, J=8.0 Hz, 1H), 8.08-7.99 (m, 1H), 7.60-7.51 (m, 2H), 7.44-7.36 (m, 5H), 5.25-5.17 (m, 2H), 4.74-4.60 (m, 1H), 4.41-4.32 (m, 1H), 4.28-4.14 (m, 2H), 4.08-3.88 (m, 2H), 3.83 (br d, J=17.6 Hz, 1H), 3.61-3.51 (m, 1H), 3.50-3.36 (m, 1H), 3.31-2.94 (m, 6H), 2.91 (d, J=2.4 Hz, 3H), 2.81-2.59 (m, 4H), 2.46 (d, J=4.0 Hz, 3H), 2.33-2.21 (m, 1H), 2.06-1.97 (m, 1H), 1.92-1.72 (m, 3H).

Step B: 2-[(2S)-4-[7-(5-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of benzyl (2S)-4-[7-(1-chloro-5-methyl-4-isoquinolyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (130 mg, 191 µmol, 1 eq) in MeOH (3 mL) was added NH$_3$.MeOH (2 mL, 20% purity), Pd/C (65 mg, 10% purity) under N$_2$. The suspension was degassed under vacuum and purged with H$_2$ several times. The mixture was stirred at 25° C. for 2 hours. Upon completion, the catalyst was removed by filtering through a plug of celite. The solvent was removed under reduced pressure to give 80 mg of crude product. Taking 20 mg of the crude product was purified by prep-HPLC (column: Waters Xbridge 150*25 5 u; mobile phase: [water (0.05% ammonia hydroxide v/v)-ACN]; B %: 28%-58%, 10 min). The desired fractions were collected and lyophilized to give 2-[(2S)-4-[7-(5-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (10.8 mg, 21.0 µmol, 44% yield, 99.9% purity) as a yellow solid. LCMS [ESI, M+1]: 513.

Step C: 2-[(2S)-1-(2-fluoroprop-2-enoyl)-4-[7-(5-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-fluoroprop-2-enoic acid (24.6 mg, 273 µmol, 2.0 eq) and DIEA (70.6 mg, 546 µmol, 95.1 µL, 4.0 eq) in DCM (1.4 mL) was added HATU (77.9 mg, 205 µmol, 1.5 eq) at 0° C. After stirring at 0° C. for 20 minutes, 2-[(2S)-4-[7-(5-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (70 mg, 137 µmol, 1.0 eq) was added into the mixture. The mixture was stirred at 25° C. for 40 minutes. Upon completion, the mixture was diluted with water (2 mL) and extracted with dichloromethane (6×5 mL). The organic layers were dried over Na$_2$SO$_4$ and concentrated under vacuum. The residue was purified by chromatography (Al$_2$O$_3$, petroleum ether/ethyl acetate 1/1 to ethyl acetate/methanol 10/1) followed by prep-HPLC (column: Waters Xbridge 150*25 5 u; mobile phase: [water (0.05% ammonia hydroxide v/v)-ACN]; B %: 35%-65%, 10 min). The desired fractions were collected and lyophilized to give 2-[(2S)-1-(2-fluoroprop-2-enoyl)-4-[7-(5-methyl-4-isoquinolyl)-2-[[(2S)-1-methylpyrrolidin-2-yl]methoxy]-6,8-dihydro-5H-pyrido[3,4-d]pyrimidin-4-yl]piperazin-2-yl]acetonitrile (20.6 mg, 34.3 µmol, 25% yield, 97.3% purity) as a white solid. LCMS [ESI, M+1]: 585.

1H NMR (400 MHz, chloroform-d) δ=9.03 (d, J=6.0 Hz, 1H), 8.30 (d, J=16.8 Hz, 1H), 7.83 (br d, J=7.6 Hz, 1H), 7.55-7.44 (m, 2H), 5.54-5.32 (m, 1H), 5.31-5.18 (m, 1H), 5.09-4.48 (m, 1H), 4.43-4.34 (m, 1H), 4.32-4.07 (m, 4H), 4.06-3.81 (m, 2H), 3.64-3.42 (m, 2H), 3.35-3.26 (m, 1H), 3.25-2.96 (m, 4H), 2.92 (d, J=2.8 Hz, 3H), 2.90-2.73 (m, 2H), 2.72-2.61 (m, 2H), 2.51-2.42 (m, 3H), 2.34-2.23 (m, 1H), 2.13-1.99 (m, 1H), 1.92-1.73 (m, 3H).

Example 620

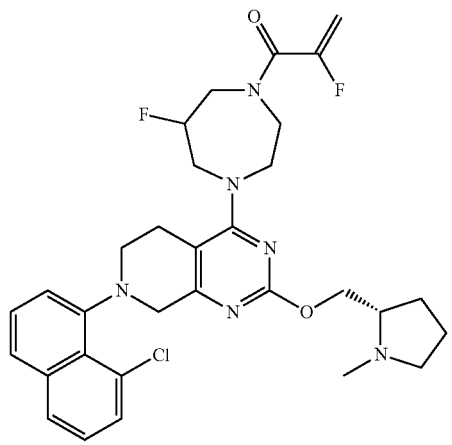 [SMILES: C=C(F)C(=O)N1CCN(c2nc(OC[C@@H]3CCCN3C)nc3c2CCN(c2cccc4cccc(Cl)c24)C3)CC(F)C1]

1-[4-[7-(8-chloro-1-naphthyl)-2-[[(2S)-1-methylpyrrolidin-2-yl] methoxy]-6,8-dihydro-5H-pyrido[3,4-d]pyrimidin-4-yl]-6-fluoro-1,4-diazepan-1-yl]-2-fluoro-prop-2-en-1-one

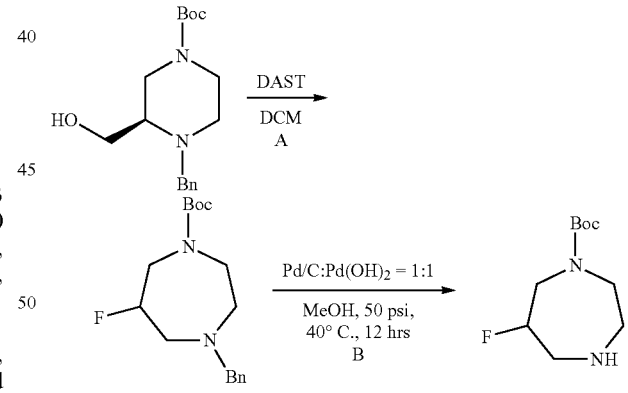

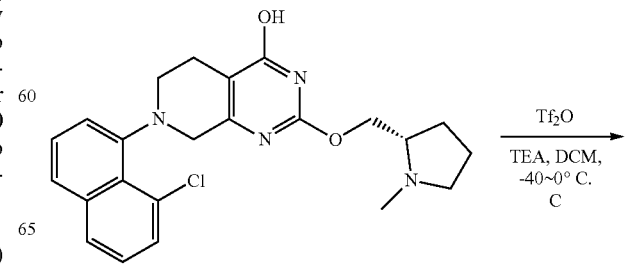

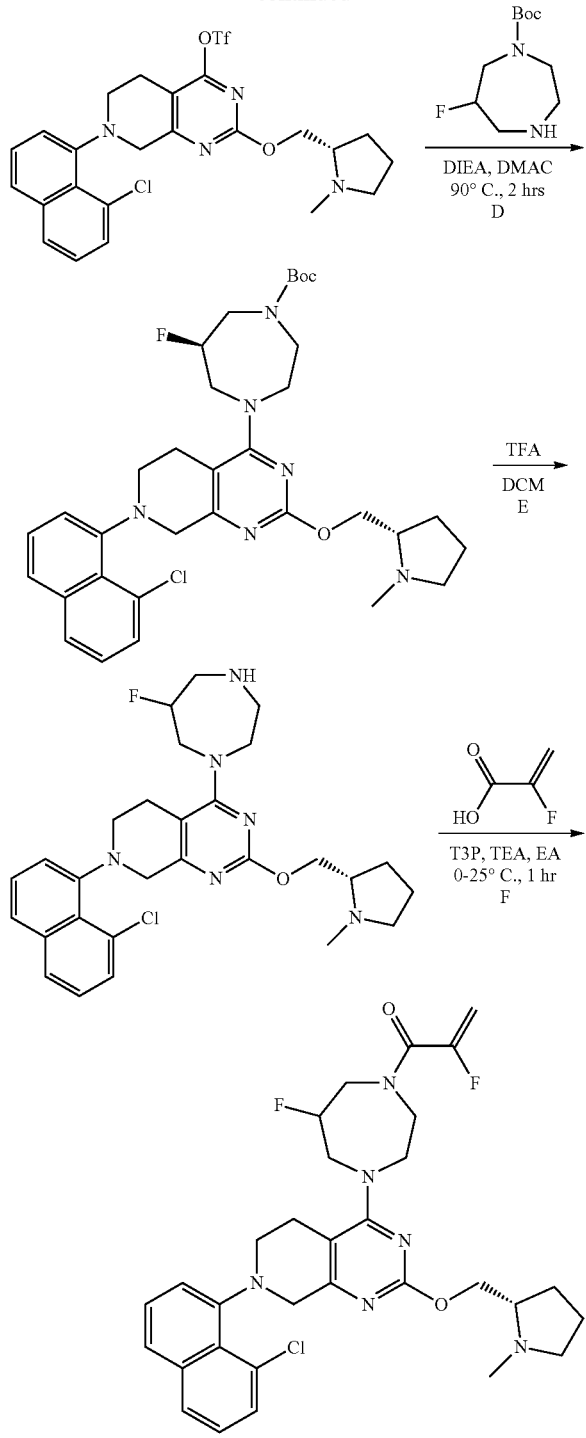

Step A: tert-butyl 4-benzyl-6-fluoro-1,4-diazepane-1-carboxylate. tert-butyl 4-benzyl-6-fluoro-1,4-diazepane-1-carboxylate To a solution of tert-butyl (3R)-4-benzyl-3-(hydroxymethyl) piperazine-1-carboxylate (1.5 g, 4.90 mmol, 1 eq) in DCM (40 mL) was added DAST (3.95 g, 24.48 mmol, 3.23 mL, 5 eq) drop-wise at 0° C., and the mixture was stirred at 20° C. for 5 hrs. The mixture was added sat, NaHCO$_3$ (30 mL) and extracted with ethyl acetate (30 mL×2). The organic layer was dried over Na$_2$SO$_4$, filtered, concentrated. The residue was purified by silica gel column chromatography (PE:EA=20~5:1) to give tert-butyl 4-benzyl-6-fluoro-1,4-diazepane-1-carboxylate (980 mg, 3.18 mmol, 64.91% yield) as yellow oil. LCMS [ESI, M+1]: 309.

Step B: tert-butyl 6-fluoro-1,4-diazepane-1-carboxylate

To a solution of tert-butyl 4-benzyl-6-fluoro-1,4-diazepane-1-carboxylate (900.00 mg, 2.92 mmol, 1 eq) and Pd/C (200 mg, 2.92 mmol, 10% purity, 1 eq) and Pd(OH)$_2$ (179.92 mg, 1.28 mmol, 4.39e-1 eq) in MeOH (20 mL) and the mixture was stirred at 40° C. for 12 hrs under H$_2$ (50 psi). The mixture was filtered, concentrated to give tert-butyl 6-fluoro-1,4-diazepane-1-carboxylate (630 mg, 2.89 mmol, 98.90% yield) as colorless oil.

Step C: [7-(8-chloro-1-naphthyl)-2-[[(2S)-1-methyl-pyrrolidin-2-yl]methoxy]-6,8-dihydro-5H-pyrido[3,4-d]pyrimidin-4-yl] trifluoromethanesulfonate To a solution of 7-(8-chloro-1-naphthyl)-2-[[(2S)-1-methylpyrrolidin-2-yl]methoxy]-6,8-dihydro-5H-pyrido[3,4-d]pyrimidin-4-ol (700 mg, 1.65 mmol, 1 eq) and TEA (500.09 mg, 4.94 mmol, 687.88 μL, 3 eq), 4 A molecular sieves (500 mg) in DCM (7 mL) was added Tf$_2$O (697.18 mg, 2.47 mmol, 407.71 μL, 1.5 eq) at −40° C., and stirred at 0° C. for 30 min. The mixture was added water (2 mL) and extracted with DCM (5 mL). The organic layer was dried over Na$_2$SO$_4$, filtered, concentrated. The residue was purified by silica gel column chromatography (PE:EA=10~1:1) to give [7-(8-chloro-1-naphthyl)-2-[[(2S)-1-methylpyrrolidin-2-yl]methoxy]-6,8-dihydro-5H-pyrido [3,4-d]pyrimidin-4-yl] trifluoromethanesulfonate (470 mg, 843.83 μmol, 51.22% yield) as red oil. LCMS [ESI, M+1]: 557.

Step D: tert-butyl 4-[7-(8-chloro-1-naphthyl)-2-[[(2S)-1-methylpyrrolidin-2-yl] methoxy]-6,8-dihydro-5H-pyrido[3,4-d]pyrimidin-4-yl]-6-fluoro-1,4-diazepane-1-carboxylate To solution of [7-(8-chloro-1-naphthyl)-2-[[(2S)-1-methylpyrrolidin-2-yl] methoxy]-6,8-dihydro-5H-pyrido[3,4-d]pyrimidin-4-yl], trifluoromethanesulfonate (440 mg, 789.97 μmol, 1 eq) and tert-butyl-6-fluoro-1,4-diazepane-1-carboxylate (258.64 mg, 1.18 mmol, 1.5 eq) in DMAC (5 mL) was added DIEA (306.29 mg, 2.37 mmol, 412.79 μL, 3 eq), and the mixture was stirred at 25° C. for 30 min. The mixture was purified by reverse silica gel column chromatography column (0.001 FA) to give tert-butyl 4-[7-(8-chloro-1-naphthyl)-2-[[(2S)-1-methylpyrrolidin-2-yl] methoxy]-6,8-dihydro-5H-pyrido[3,4-d]pyrimidin-4-yl]-6-fluoro-1,4-diazepane-1-carboxylate (260 mg, 415.88 μmol, 52.65% yield) as yellow solid. LCMS [ESI, M+1]: 625.

Step E: 7-(8-chloro-1-naphthyl)-4-(6-fluoro-1,4-diazepan-1-yl)-2-[[(2S)-1-methylpyrrolidin-2-yl]methoxy]-6,8-dihydro-5H-pyrido[3,4-d]pyrimidine To a solution of tert-butyl 4-[7-(8-chloro-1-naphthyl)-2-[[(2S)-1-methylpyrrolidin-2-yl]methoxy]-6,8-dihydro-5H-pyrido[3,4-d]pyrimidin-4-yl]-6-fluoro-1,4-diazepane-1-carboxylate (240.00 mg, 383.89 μmol, 1 eq) in DCM (3 mL) was added TFA (12.32 g, 108.05 mmol, 8.00 mL, 281.45 eq), and the mixture was stirred at 20° C. for 30 min. The mixture was concentrated, and added DCM (10 mL), washed with sat.Na$_2$CO$_3$ (5 mL). The organic layer was dried over Na$_2$SO$_4$, filtered, concentrated to give 7-(8-chloro-1-naphthyl)-4-(6-fluoro-1,4-diazepan-1-yl)-2-[[(2S)-1-methylpyrrolidin-2-yl]methoxy]-6,8-dihydro-5Hpyrido[3,4-d] pyrimidine (200 mg, crude) as yellow solid. Some of this material (160 mg, 304.73 μmol) was used directly in the next step. 40 mg of crude product was purified by prep-HPLC (purified by prep-HPLC (column: Shim-pack C18 150*25*10 um; mobile phase: [water (0.225% FA)-ACN]; B %: 4%-34%,10 min), then residue was prep-HPLC (column: Xtimate C18 150*25 mm*5 um; mobile phase: [water (0.05% ammonia hydroxide v/v)-ACN]; B %: 60%-90%,10 min) to give 7-(8-chloro-1-naphthyl)-4-(6-fluoro-1,4-diazepan-1-yl)-2-[[(2S)-1-methylpyrrolidin-2-yl]methoxy]-6,8-dihydro-5H-pyrido[3,4-d]pyrimidine (9 mg, 16.99 μmol). LCMS [ESI, M+1]: 523.

$^1$H NMR (400 MHz, chloroform-d) δ=7.76 (d, J=8.07 Hz, 1H) 7.61 (t, J=8.38 Hz, 1H) 7.52 (br d, J=7.46 Hz, 1H) 7.44 (dt, J=15.86, 7.90 Hz, 1H) 7.34 (t, J=7.76 Hz, 1H) 7.25-7.18 (dd, J=7.46 Hz, 1H) 4.80-5.24 (m, 1H) 4.31-4.46 (m, 2H) 4.08-4.30 (m, 2H) 3.71-4.04 (m, 3H) 3.50-3.68 (m, 2H) 2.81-3.37 (m, 7H) 2.46-2.73 (m, 5H) 2.25-2.35 (m, 1H) 2.01-2.14 (m, 1H) 1.82-1.91 (m, 3H).

Step F: 1-[4-[7-(8-chloro-1-naphthyl)-2-[[(2S)-1-methylpyrrolidin-2-yl] methoxy]-6,8-dihydro-5H-pyrido[3,4-d]pyrimidin-4-yl]-6-fluoro-1,4-diazepan-1-yl]-2-fluoro-prop-2-en-1-one To a solution of 7-(8-chloro-1-naphthyl)-4-(6-fluoro-1,4-diazepan-1-yl)-2-[[(2S)-1-methylpyrrolidin-2-yl]methoxy]-6,8-dihydro-5H-pyrido [3,4-d] pyrimidine (150.00 mg, 285.68 μmol, 1 eq) and 2-fluoroprop-2-enoic acid (51.45 mg, 571.36 μmol, 2 eq) in EA (2 mL) was added T3P (50 M, 17.14 μL, 3 eq) and TEA (231.27 mg, 2.29 mmol, 318.11 μL, 8 eq) at −40° C., and the mixture was stirred at −40° C. for 30 min. The mixture was diluted with water (2 mL) and extracted with ethyl acetate (2 mL×2). The organic layer was dried over Na$_2$SO$_4$, filtered, concentrated. The residue was purified by prep-HPLC (column: Shim-pack C18 150*25*10 um; mobile phase: [water (0.225% FA)-ACN]; B %: 18%-48%, 10 min) to give 1-[4-[7-(8-chloro-1-naphthyl)-2-[[(2S)-1-methylpyrrolidin-2-yl] methoxy]-6,8-dihydro-5H-pyrido[3,4-d]pyrimidin-4-yl]-6-fluoro-1,4-diazepan-1-yl]-2-fluoro-prop-2-en-1-one (90 mg, 140.78 μmol, 49.28% yield, 93.4% purity) as yellow solid. LCMS [ESI, M+1]: 597.

$^1$H NMR (400 MHz, chloroform-d) δ=7.76 (d, J=8.19 Hz, 1H) 7.58-7.66 (m, 1H) 7.50-7.56 (m, 1H) 7.38-7.50 (m, 1H) 7.31-7.37 (m, 1H) 7.24-7.16 (m, 1H) 4.90-5.55 (m, 3H) 4.32-4.48 (m, 2H) 3.48-4.27 (m, 11H) 3.21-3.43 (m, 1H) 2.80-3.16 (m, 2H) 2.44-2.73 (m, 5H) 2.25-2.36 (m, 1H) 2.00-2.14 (m, 1H) 1.77-1.91 (m, 3H).

Example 621

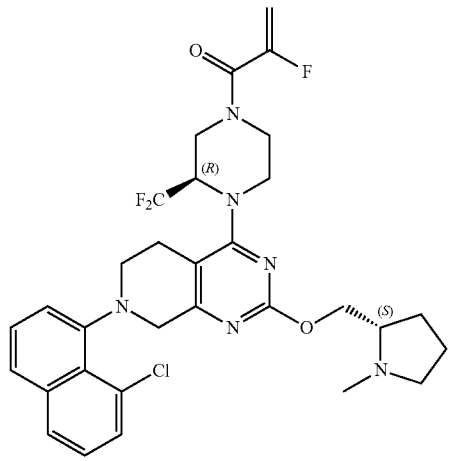

1-[(3R)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-3-(difluoromethyl)piperazin-1-yl]-2-fluoro-prop-2-en-1-one

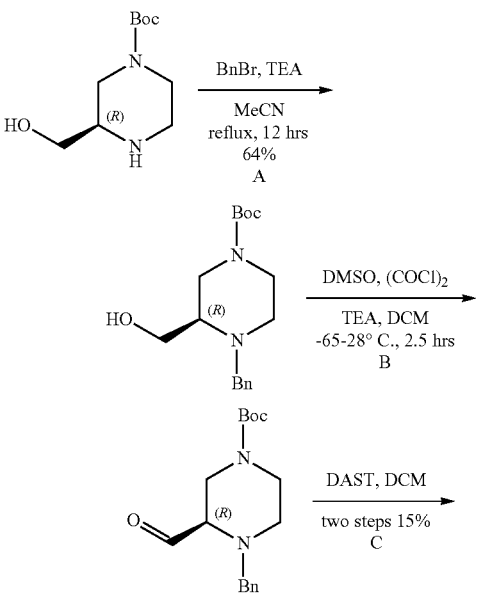

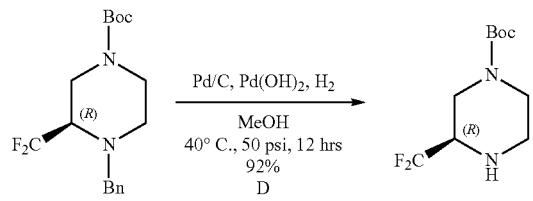

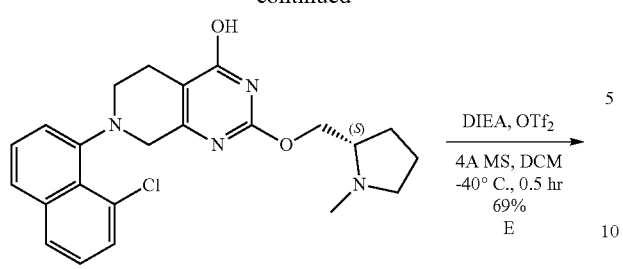

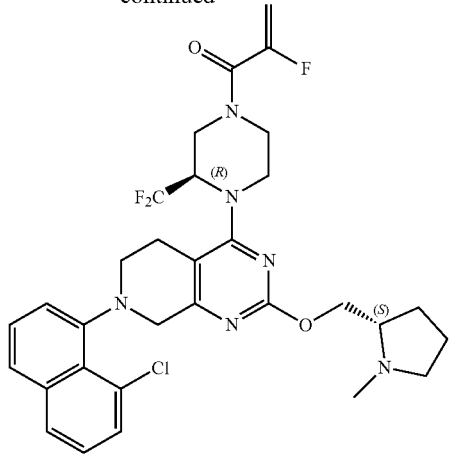

Step A: tert-butyl (3R)-4-benzyl-3-(hydroxymethyl)piperazine-1-carboxylate

A reaction mixture of tert-butyl (3R)-3-(hydroxymethyl)piperazine-1-carboxylate (10 g, 46.2 mmol, 1 eq), BnBr (8.70 g, 50.9 mmol, 6.04 mL, 1.1 eq) and TEA (7.02 g, 69.36 mmol, 9.65 mL, 1.5 eq) in MeCN (100 mL) was heated to 80° C. for 12 hours. Upon completion, the reaction mixture was concentrated under vacuum. The residue was dissolved into water (30 mL) and ethyl acetate (50 mL). The mixture was extracted with ethyl acetate (3×50 mL). The combined organic layers were washed with brine (30 mL), dried over $Na_2SO_4$, and concentrated under vacuum. The residue was purified by silica gel chromatography (petroleum ether: ethyl acetate=5:1 to 3:1). tert-butyl (3R)-4-benzyl-3-(hydroxymethyl)piperazine-1-carboxylate (9 g, 29.4 mmol, 64% yield, 100% purity) was obtained as a white solid. LCMS [ESI, M+1]: 307.
$^1$H NMR (400 MHz, chloroform-d) δ=7.28-7.20 (m, 5H), 3.95 (br d, J=13.2 Hz, 1H), 3.79 (dd, J=5.6, 11.6 Hz, 1H), 3.61 (br dd, J=3.2, 13.6 Hz, 1H), 3.52 (br dd, J=4.0, 11.2 Hz, 2H), 3.35 (br d, J=13.3 Hz, 2H), 3.09 (br s, 1H), 2.77-2.65 (m, 1H), 2.51 (br s, 1H), 2.20 (ddd, J=3.2, 8.4, 12.0 Hz, 1H), 1.38 (s, 9H).

Step B: tert-butyl (3R)-4-benzyl-3-formyl-piperazine-1-carboxylate

DMSO (13.8 g, 176 mmol, 13.8 mL, 6.0 eq) was added to a to −65° C. solution of $(COCl)_2$ (11.2 g, 88.1 mmol, 7.71 mL, 3.0 eq) in dichloromethane (90 mL). After 10 min, a solution of tert-butyl (3R)-4-benzyl-3-(hydroxymethyl)piperazine-1-carboxylate (9 g, 29.4 mmol, 1 eq) in dichloromethane (40 mL) was slowly introduced over 15 minutes. After stirring at −65° C. for 1 hour, TEA (29.7 g, 294 mmol, 40.9 mL, 10.0 eq) was added. The mixture was warmed to 28° C. over 30 min and then stirred for another 30 min at that temperature. Upon completion, the reaction mixture was quenched with water (5 mL) and separated. The organic layer was dried over $Na_2SO_4$ and concentrated under vacuum. tert-butyl (3R)-4-benzyl-3-formyl-piperazine-1-carboxylate (8.9 g, 29 mmol) was obtained as a yellow oil which was used for next step without further purification.

Step C: tert-butyl (3R)-4-benzyl-3-(difluoromethyl)piperazine-1-carboxylate

To a solution of tert-butyl (3R)-4-benzyl-3-formyl-piperazine-1-carboxylate (8.9 g, 29.2 mmol, 1.0 eq) in dichloromethane (180 mL) was added DAST (9.43 g, 58.5 mmol, 7.73 mL, 2 eq) at 0° C. The reaction mixture was stirred at 0° C. for 2 hours. Upon completion, the reaction mixture was quenched by saturated NaHCO$_3$ (150 mL) and extracted with ethyl acetate (3×150 mL). The combined organic layers were washed with brine (60 mL) and concentrated under vacuum. The residue (Petroleum ether: Ethyl acetate=5:1) was purified by silica gel chromatography (Petroleum ether: Ethyl acetate=1:0 to 10:1). tert-butyl (3R)-4-benzyl-3-(difluoromethyl)piperazine-1-carboxylate (1.5 g, 4.48 mmol, two steps 15% yield, 97.5% purity) was obtained as a yellow oil. LCMS [ESI, M+1]:327.

Step D: tert-butyl (3R)-3-(difluoromethyl)piperazine-1-carboxylate

To a solution of tert-butyl (3R)-4-benzyl-3-(difluoromethyl)piperazine-1-carboxylate (1.5 g, 4.60 mmol, 1.0 eq) in MeOH (10 mL) was added Pd/C (150 mg, 10% purity), Pd(OH)$_2$/C (150 mg, 20% purity) under N$_2$. The suspension was degassed under vacuum and purged with H$_2$ several times. The mixture was stirred under H$_2$ (50 psi) at 40° C. for 12 hours. Upon completion, the mixture was filtered and the filtrate was concentrated under vacuum. tert-butyl (3R)-3-(difluoromethyl)piperazine-1-carboxylate (1.0 g, 4.23 mmol, 92% yield) was obtained as a yellow oil which was used for next step without further purification.

1H NMR (400 MHz, chloroform-d) δ=5.91-5.43 (m, 1H), 4.17-3.78 (m, 2H), 3.13-2.66 (m, 5H), 1.48 (s, 9H).

Step E: [7-(8-chloro-1-naphthyl)-2-[[(2S)-1-methylpyrrolidin-2-yl]methoxy]-6,8-dihydro-5H-pyrido[3,4-d]pyrimidin-4-yl] trifluoromethanesulfonate To a solution of 7-(8-chloro-1-naphthyl)-2-[[(2S)-1-methylpyrrolidin-2-yl]methoxy]-6,8-dihydro-5H-pyrido[3,4-d]pyrimidin-4-ol (1.0 g, 2.35 mmol, 1 eq), 4 A molecular sieve (1.0 g) and TEA (953 mg, 9.41 mmol, 1.31 mL, 4.0 eq) in dichloromethane (20 mL) was added Tf$_2$O (996 mg, 3.53 mmol, 582 uL, 1.5 eq) at −40° C. and stirred for 0.5 hours. Upon completion, the reaction mixture was quenched by water (15 mL). The mixture was filtered through a pad of celite. The filtrate separated and the aqueous layers were extracted with dichloromethane (30 mL). The organic layers were washed with brine (10 mL), dried over Na$_2$SO$_4$ and concentrated under vacuum. The mixture was purified by silica gel chromatography (SiO$_2$, Petroleum ether: Ethyl acetate=5:1 to 0:1) to give [7-(8-chloro-1-naphthyl)-2-[[(2S)-1-methylpyrrolidin-2-yl]methoxy]-6,8-dihydro-5H-pyrido[3,4-d]pyrimidin-4-yl] trifluoromethanesulfonate (1.0 g, 1.63 mmol, 69% yield, 91% purity) as a brown oil. LCMS [ESI, M+1]:557.

Step F: tert-butyl (3R)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-3-(difluoromethyl)piperazine-1-carboxylate A reaction mixture of [7-(8-chloro-1-naphthyl)-2-[[(2S)-1-methylpyrrolidin-2-yl]methoxy]-6,8-dihydro-5H-pyrido[3,4-d]pyrimidin-4-yl] trifluoromethanesulfonate (1.0 g, 1.80 mmol, 1.0 eq) and tert-butyl (3R)-3-(difluoromethyl)piperazine-1-carboxylate (780 mg, 3.30 mmol, 1.84 eq) was stirred at 90° C. for 5 hours. Upon completion, the reaction mixture was dissolved in MeCN (5 mL). The reaction mixture was purified by reversed-phase flash [water (0.1% FA)/acetonitrile]. The fractions were basidified by solid NaHCO$_3$ to pH >7 and concentrated under vacuum. The aqueous layer was extracted with Ethyl acetate (3×20 mL) and concentrated under vacuum. The residue was purified by prep-TLC (dichloromethane:MeOH=7:1) to give tert-butyl (3R)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-3-(difluoromethyl)piperazine-1-carboxylate (80 mg, 122 μmol, 7% yield, 98% purity) as a brown oil. LCMS [ESI, M+1]: 643.

Step G: 7-(8-chloro-1-naphthyl)-4-[(2R)-2-(difluoromethyl)piperazin-1-yl]-2-[[(2S)-1-methylpyrrolidin-2-yl]methoxy]-6,8-dihydro-5H-pyrido[3,4-d] pyrimidine To a solution of tert-butyl (3R)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-3-(difluoromethyl)piperazine-1-carboxylate (20 mg, 31.1 μmol, 1 eq) in dichloromethane (0.05 mL) was added TFA (70.9 mg, 622 μmol, 46.0 μL, 20 eq). The reaction mixture was stirred at 25° C. for 1 hour. Upon completion, the reaction mixture was quenched by saturated Na$_2$CO$_3$ (4 mL) and extracted with dichloromethane: MeOH (10:1, 3×8 mL). The combined organic layers were dried over Na$_2$SO$_4$ and concentrated under vacuum. The residue was purified by Prep-HPLC (column: Waters Xbridge 150*25 5 u; mobile phase: [water (10 mM NH4HCO3)-ACN]; B %: 43%-73%,10 min). The fractions were concentrated and lyophilized. 7-(8-chloro-1-naphthyl)-4-[(2R)-2-(difluoromethyl)piperazin-1-yl]-2-[[(2S)-1-methylpyrrolidin-2-yl]methoxy]-6,8-dihydro-5H-pyrido[3,4-d]pyrimidine (4.22 mg, 7.77 μmol, 25% yield, 100% purity) was obtained as a white solid. LCMS [ESI, M+1]:543.

1H NMR (400 MHz, chloroform-d) δ=7.81-7.74 (m, 1H), 7.66-7.59 (m, 1H), 7.56-7.52 (m, 1H), 7.50-7.40 (m, 1H), 7.35 (t, J=7.6 Hz, 1H), 7.28-7.16 (m, 1H), 6.69-6.09 (m, 1H), 4.68-4.54 (m, 1H), 4.51-4.34 (m, 2H), 4.30-4.11 (m, 1H), 4.07-3.68 (m, 2H), 3.63-3.46 (m, 2H), 3.44-3.31 (m, 2H), 3.30-3.21 (m, 1H), 3.20-2.97 (m, 4H), 2.92-2.83 (m, 1H), 2.78-2.67 (m, 1H), 2.58-2.49 (m, 3H), 2.38-2.26 (m, 1H), 2.15-2.02 (m, 1H), 1.94-1.73 (m, 3H).

Step H: 1-[(3R)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-3-(difluoromethyl)piperazin-1-yl]-2-fluoro-prop-2-en-1-one To a solution of 7-(8-chloro-1-naphthyl)-4-[(2R)-2-(difluoromethyl)piperazin-1-yl]-2-[[(2S)-1-methylpyrrolidin-2-yl]methoxy]-6, 8-dihydro-5H-pyrido[3,4-d]pyrimidine (45 mg, 82.9 μmol, 1.0 eq), 2-fluoroprop-2-enoic acid (22.4 mg, 249 μmol, 3.0 eq) in Ethyl acetate (1 mL) was added 4 A molecular sieve (100 mg). After stirring at 25° C. for 0.5 hour, TEA (126 mg, 1.24 mmol, 173 μL, 15 eq) and T3P (211 mg, 331 μmol, 197 μL, 50% purity, 4 eq) was added at 0° C. The mixture was stirred at 25° C. for 0.5 hour. Upon completion, the reaction mixture was quenched by water (1 mL) and extracted with Ethyl acetate (3×5 mL). The combined organic layers were dried over Na$_2$SO$_4$ and concentrated under vacuum. The residue was purified by column (Al$_2$O$_3$, Petroleum ether:Ethyl acetate=3:1 to 0:1), followed by prep-HPLC (column: Waters Xbridge 150*25 5 u; mobile phase: [water (0.05% ammonia hydroxide v/v)-ACN]; B %: 55%-85%,10 min) to give 1-[(3R)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-3-(difluoromethyl)

piperazin-1-yl]-2-fluoro-prop-2-en-1-one (5.98 mg, 9.72 μmol, 11% yield, 99.4% purity) as a white solid. LCMS [ESI, M+1]: 615.

1H NMR (400 MHz, chloroform-d) δ=7.81-7.75 (m, 1H), 7.67-7.61 (m, 1H), 7.55 (td, J=1.2, 7.6 Hz, 1H), 7.51-7.41 (m, 1H), 7.36 (t, J=7.6 Hz, 1H), 7.28-7.17 (m, 1H), 6.48-5.83 (m, 1H), 5.47-5.31 (m, 1H), 5.27-5.19 (m, 1H), 4.88-4.65 (m, 1H), 4.59-4.31 (m, 4H), 4.21-4.10 (m, 1H), 4.04-3.76 (m, 2H), 3.69-3.44 (m, 3H), 3.33-2.92 (m, 4H), 2.75-2.64 (m, 1H), 2.61-2.52 (m, 1H), 2.49-2.48 (m, 3H), 2.36-2.25 (m, 1H), 2.13-2.02 (m, 1H), 1.88-1.72 (m, 3H).

EXAMPLES 622-678 listed in Table 1 are prepared using commercially available intermediates and/or those intermediates disclosed herein following the methods outlined in the general reactions schemes and the teachings of the exemplified Examples.

TABLE 1

EXAMPLES 622-678

| Example No. | Structure |
|---|---|
| 622 | 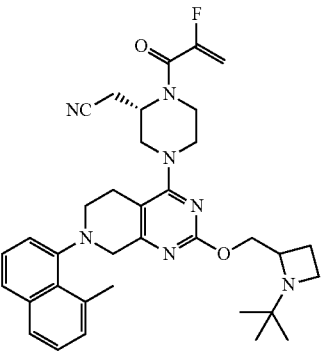 [SMILES: C=C(F)C(=O)N1CCN(c2nc(OCC3CCN3C(C)(C)C)nc3c2CCN(c2cccc4cccc(C)c24)C3)C[C@@H]1CC#N] |
| 623 | 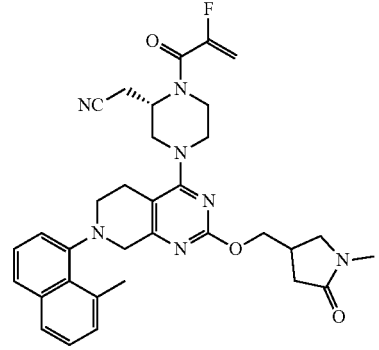 [SMILES: C=C(F)C(=O)N1CCN(c2nc(OCC3CC(=O)N(C)C3)nc3c2CCN(c2cccc4cccc(C)c24)C3)C[C@@H]1CC#N] |
| 624 | 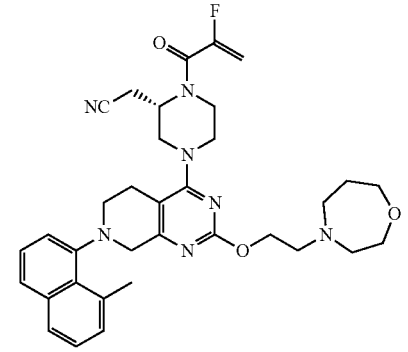 [SMILES: C=C(F)C(=O)N1CCN(c2nc(OCCN3CCCOCC3)nc3c2CCN(c2cccc4cccc(C)c24)C3)C[C@@H]1CC#N] |
| 625 | 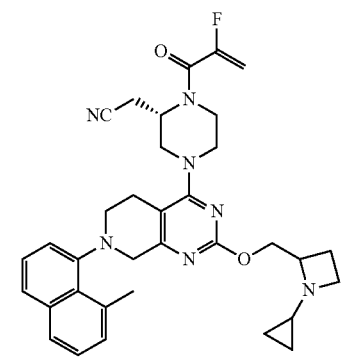 [SMILES: C=C(F)C(=O)N1CCN(c2nc(OCC3CCN3C3CC3)nc3c2CCN(c2cccc4cccc(C)c24)C3)C[C@@H]1CC#N] |
| 626 | 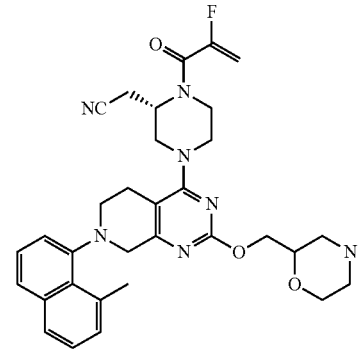 |
| 627 | 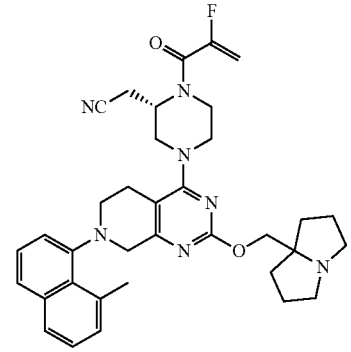 [SMILES: C=C(F)C(=O)N1CCN(c2nc(OCC34CCCN3CCC4)nc3c2CCN(c2cccc4cccc(C)c24)C3)C[C@@H]1CC#N] |
| 628 | 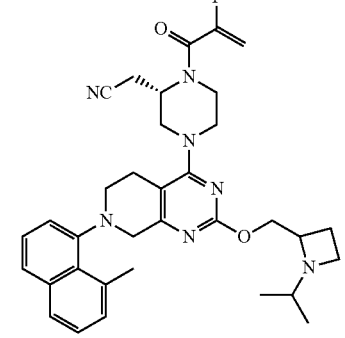 |

TABLE 1-continued
EXAMPLES 622-678
| Example No. | Structure |
|---|---|
| 629 | 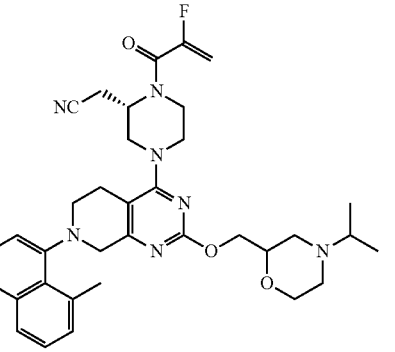 |
| 630 | 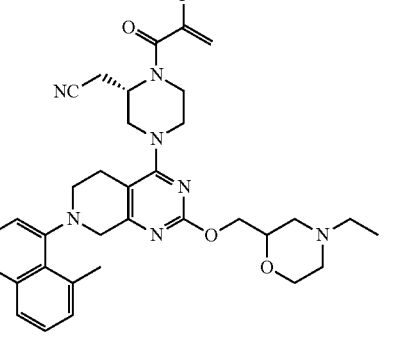 |
| 631 | 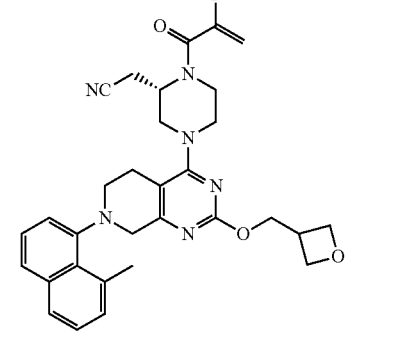 |
| 632 | 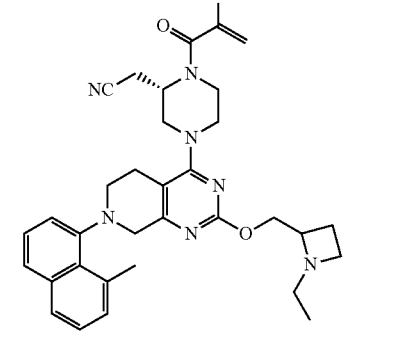 |
| 633 | 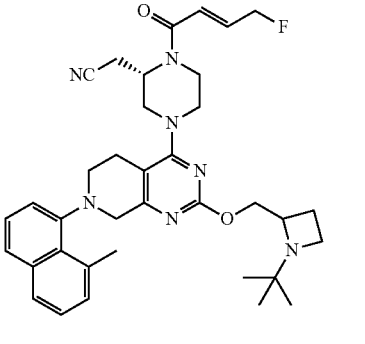 [SMILES: Cc1cccc2cccc(N3CCc4c(nc(OCC5CCN5C(C)(C)C)nc4N4CCN(C(=O)/C=C/CF)[C@@H](CC#N)C4)C3)c12] |
| 634 | 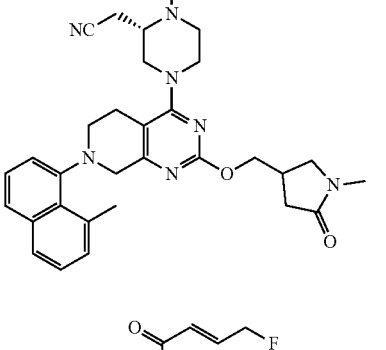 |
| 635 | 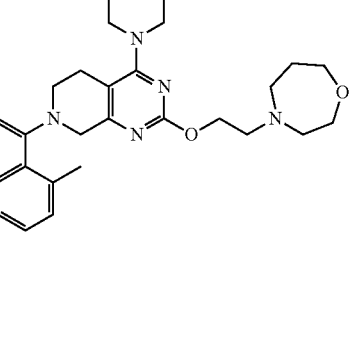 |
| 636 | 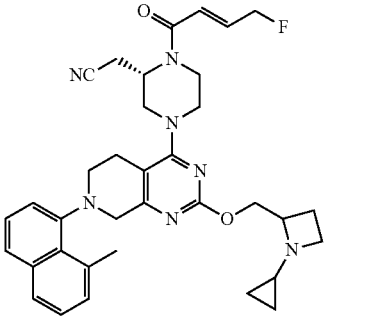 [SMILES: Cc1cccc2cccc(N3CCc4c(nc(OCC5CCN5C5CC5)nc4N4CCN(C(=O)/C=C/CF)[C@@H](CC#N)C4)C3)c12] |

TABLE 1-continued

EXAMPLES 622-678

| Example No. | Structure |
|---|---|
| 637 | 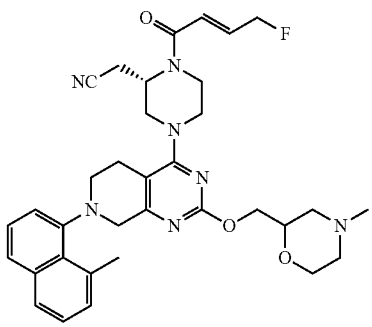 [SMILES: Cc1cccc2cccc(N3CCc4c(nc(OCC5CN(C)CCO5)nc4N4CCN(C(=O)/C=C/CF)[C@@H](CC#N)C4)C3)c12] |
| 638 | 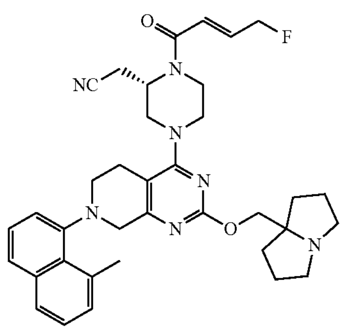 [SMILES: Cc1cccc2cccc(N3CCc4c(nc(OCC56CCCN5CCC6)nc4N4CCN(C(=O)/C=C/CF)[C@@H](CC#N)C4)C3)c12] |
| 639 | 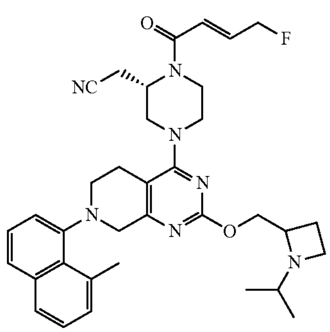 [SMILES: Cc1cccc2cccc(N3CCc4c(nc(OCC5CCN5C(C)C)nc4N4CCN(C(=O)/C=C/CF)[C@@H](CC#N)C4)C3)c12] |
| 640 | 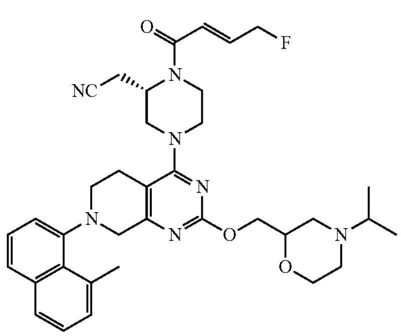 [SMILES: Cc1cccc2cccc(N3CCc4c(nc(OCC5CN(C(C)C)CCO5)nc4N4CCN(C(=O)/C=C/CF)[C@@H](CC#N)C4)C3)c12] |
| 641 | |
| 642 | |
| 643 | |
| 644 | |

TABLE 1-continued

EXAMPLES 622-678

| Example No. | Structure |
|---|---|
| 645 | 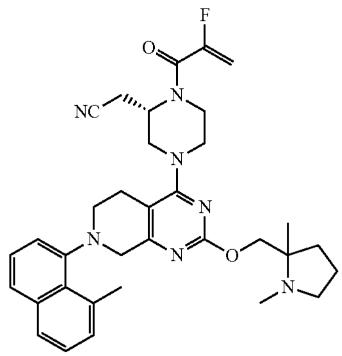 [SMILES: C=C(F)C(=O)N1CCN(c2nc(OCC3(C)CCCN3C)nc3c2CCN(c2cccc4cccc(C)c24)C3)C[C@@H]1CC#N] |
| 646 | 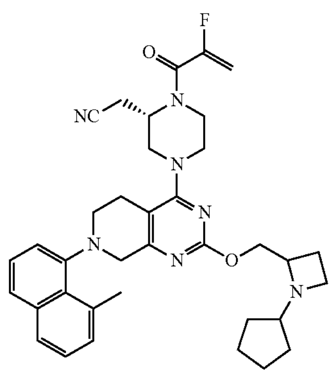 [SMILES: C=C(F)C(=O)N1CCN(c2nc(OCC3CCN3C3CCCC3)nc3c2CCN(c2cccc4cccc(C)c24)C3)C[C@@H]1CC#N] |
| 647 | 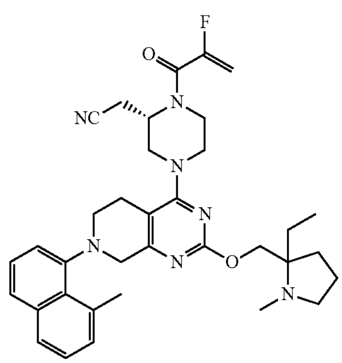 [SMILES: C=C(F)C(=O)N1CCN(c2nc(OCC3(CC)CCCN3C)nc3c2CCN(c2cccc4cccc(C)c24)C3)C[C@@H]1CC#N] |
| 648 | 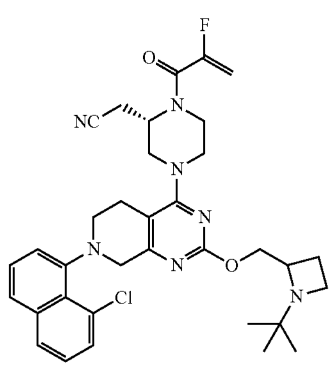 |
| 649 | |
| 650 | |
| 651 | |
| 652 | |

TABLE 1-continued

EXAMPLES 622-678

| Example No. | Structure |
|---|---|
| 653 | 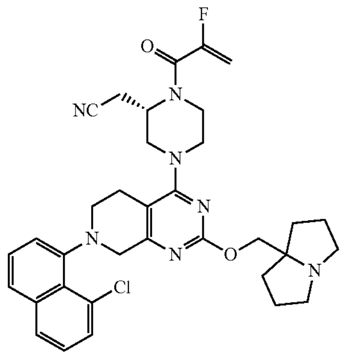 [SMILES: C=C(F)C(=O)N1CCN(c2nc(OCC34CCCN3CCC4)nc3c2CCN(c2cccc4cccc(Cl)c24)C3)C[C@@H]1CC#N] |
| 654 | 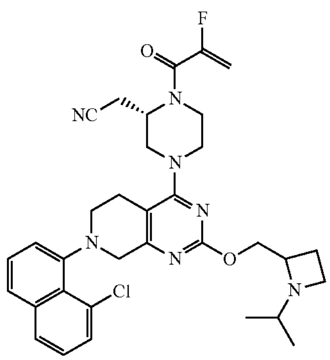 [SMILES: C=C(F)C(=O)N1CCN(c2nc(OCC3CCN3C(C)C)nc3c2CCN(c2cccc4cccc(Cl)c24)C3)C[C@@H]1CC#N] |
| 655 | 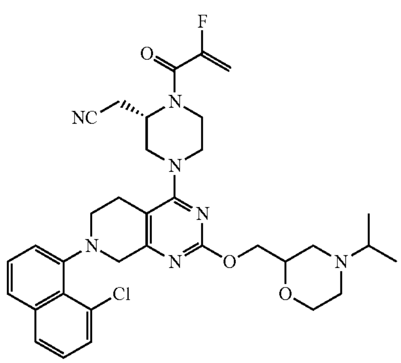 [SMILES: C=C(F)C(=O)N1CCN(c2nc(OCC3CN(C(C)C)CCO3)nc3c2CCN(c2cccc4cccc(Cl)c24)C3)C[C@@H]1CC#N] |
| 656 | 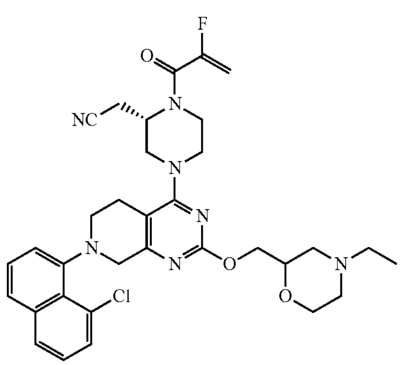 [SMILES: C=C(F)C(=O)N1CCN(c2nc(OCC3CN(CC)CCO3)nc3c2CCN(c2cccc4cccc(Cl)c24)C3)C[C@@H]1CC#N] |
| 657 | 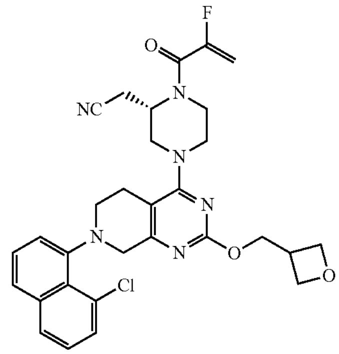 [SMILES: C=C(F)C(=O)N1CCN(c2nc(OCC3COC3)nc3c2CCN(c2cccc4cccc(Cl)c24)C3)C[C@@H]1CC#N] |
| 658 | 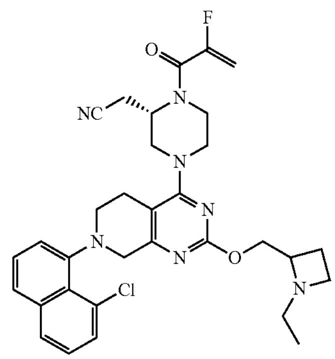 [SMILES: C=C(F)C(=O)N1CCN(c2nc(OCC3CCN3CC)nc3c2CCN(c2cccc4cccc(Cl)c24)C3)C[C@@H]1CC#N] |
| 659 | 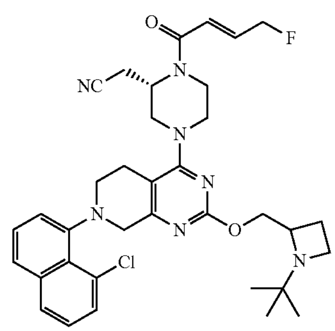 [SMILES: CC(C)(C)N1CCC1COc1nc2c(c(N3CCN(C(=O)/C=C/CF)[C@@H](CC#N)C3)n1)CCN(c1cccc3cccc(Cl)c13)C2] |
| 660 | 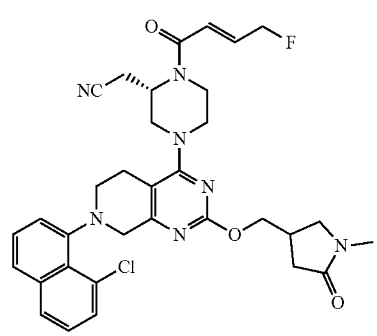 [SMILES: CN1CC(COc2nc3c(c(N4CCN(C(=O)/C=C/CF)[C@@H](CC#N)C4)n2)CCN(c2cccc4cccc(Cl)c24)C3)CC1=O] |

TABLE 1-continued

EXAMPLES 622-678

| Example No. | Structure |
|---|---|
| 661 | 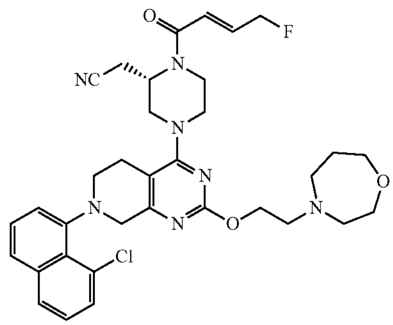 [SMILES: N#CC[C@H]1CN(c2nc(OCCN3CCCOCC3)nc3c2CCN(c2cccc4cccc(Cl)c24)C3)CCN1C(=O)/C=C/CF] |
| 662 | 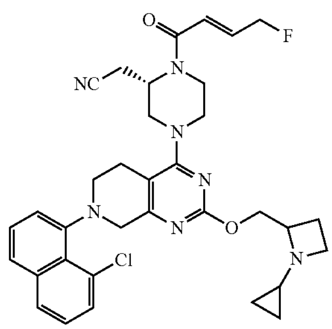 [SMILES: N#CC[C@H]1CN(c2nc(OCC3CCN3C3CC3)nc3c2CCN(c2cccc4cccc(Cl)c24)C3)CCN1C(=O)/C=C/CF] |
| 663 | 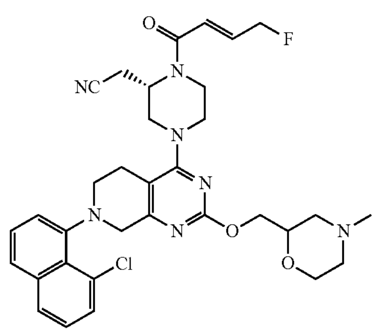 [SMILES: CN1CCOC(COc2nc3c(c(N4CCN(C(=O)/C=C/CF)[C@@H](CC#N)C4)n2)CCN(c2cccc4cccc(Cl)c24)C3)C1] |
| 664 | 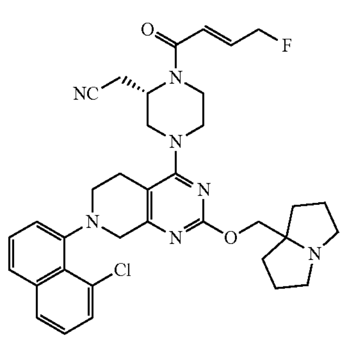 [SMILES: N#CC[C@H]1CN(c2nc(OCC34CCCN3CCC4)nc3c2CCN(c2cccc4cccc(Cl)c24)C3)CCN1C(=O)/C=C/CF] |
| 665 | |
| 666 | |
| 667 | |
| 668 | |

TABLE 1-continued

EXAMPLES 622-678

| Example No. | Structure |
|---|---|
| 669 | 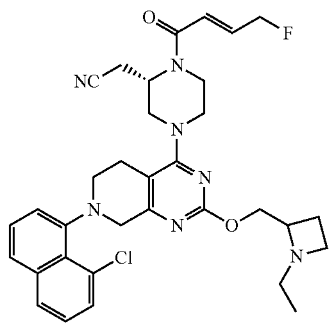 [SMILES: CCN1CCC1COc1nc2c(c(N3CCN(C(=O)/C=C/CF)[C@@H](CC#N)C3)n1)CCN(c1cccc3cccc(Cl)c13)C2] |
| 670 | 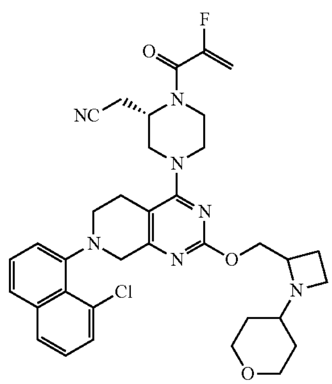 [SMILES: C=C(F)C(=O)N1CCN(c2nc(OCC3CCN3C3CCOCC3)nc3c2CCN(c2cccc4cccc(Cl)c24)C3)C[C@@H]1CC#N] |
| 671 | 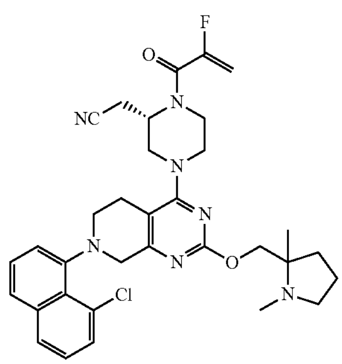 [SMILES: C=C(F)C(=O)N1CCN(c2nc(OCC3(C)CCCN3C)nc3c2CCN(c2cccc4cccc(Cl)c24)C3)C[C@@H]1CC#N] |
| 672 | 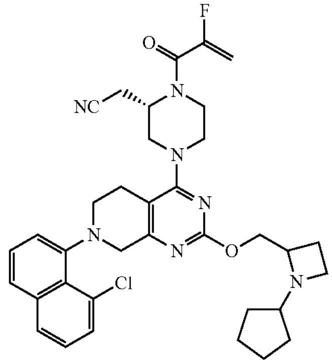 [SMILES: C=C(F)C(=O)N1CCN(c2nc(OCC3CCN3C3CCCC3)nc3c2CCN(c2cccc4cccc(Cl)c24)C3)C[C@@H]1CC#N] |
| 673 | |
| 674 | |
| 675 | |
| 676 | |

TABLE 1-continued

EXAMPLES 622-678

| Example No. | Structure |
|---|---|
| 677 | (structure) |
| 678 | (structure) |

Example A

KRas G12C Modification Assay

This Example illustrates that exemplary compounds of the present invention covalently bind to KRas G12C using a LCMS assay to detect a covalent adduct of the exemplary compound and KRAS G12C.

The protein concentration of GDP-loaded K-Ras (1-169) G12C, C51S, C80L, C118S and GTP-loaded K-Ras (1-169) G12C, C51S, C80L, C118S, Q61H was adjusted to 2 μM in K-Ras Assay Buffer (25 mM HEPES, 150 mM NaCl, 5 mM MgCl$_2$, and 10 mM Octyl β-glucopyranoside at pH 7.5). A 10 μL aliquot of each protein solution was then transferred to a 384 well microtiter plate. Initial compound stocks were generated at fifty times their desired final assay concentration in DMSO.

Exemplary compounds of Formula (I) were diluted 25-fold into K-Ras Assay Buffer to a final of two times their final concentration. A 10 μL aliquot of each diluted compound solution was then added to each of the protein solutions in the microtiter plate to initiate reaction. Typical final compound concentrations were 3.0, 5.0 and 25.0 μM. At each time point, the reactions were quenched with 20 μL of a 25 mM acetic acid solution. Usual assay endpoints were 15, 180 and 1440 minutes. Once all reactions were quenched, the plates were heat sealed and the samples were injected into a LC/MS system for data acquisition.

Data collection took place on an Agilent 6520 Q-TOF Accurate Mass Spectrometer. Samples were injected in their liquid phase onto a C-3 reverse phase column to remove assay buffer and prepare the samples for mass spectrometer. The proteins were eluted from the column using an acetonitrile gradient and fed directly into the mass analyzer. Initial raw data analysis took place in Agilent MassHunter software immediately post data acquisition.

Raw data analysis of the intact protein was exclusively a deconvolution of the multiple charge states of each protein in solution using a maximum entropy deconvolution provided in Mass Hunter. To minimize complexity, only the data over limited mass ranges were considered for analysis, with a minimum of one Dalton mass step intervals. The heights of all masses identified during raw data analysis were exported to be further analyzed in Spotfire® data analysis software.

Final data analysis was a multistep process in the Spotfire® data analysis software package. Briefly, each protein mass was calculated as a percent of the total signal of that sample, that percentage was then normalized to the percentage of signal of the protein in the absence of reactive compounds. Those normalized signals were reported as normalized percent of control (POC). An increased POC value indicates a compound that displays a higher degree of modification at a given condition compared to other compounds under the same conditions. The results for exemplary compounds of Formula (I) and Formula (II) tested at 5 μM concentration for 3 hours are shown in Table 2. Key: "A"≤25% POC; "B">25% POC-≤50% POC; "C">50% POC and ND=not determined.

TABLE 2

Inhibition of KRas G12C Activity by Exemplary Compounds

| Example No. | POC |
|---|---|
| 1 | B |
| 2 | A |
| 3 | A |
| 4 | A |
| 5 | A |
| 6 | B |
| 7 | A |
| 8 | B |
| 9 | C |
| 10 | C |
| 11 | C |
| 12 | C |
| 13 | C |
| 14 | C |
| 15 | C |
| 16 | C |
| 17 | B |
| 18 | C |
| 19 | C |
| 20 | C |
| 21 | C |
| 22 | C |
| 23 | C |
| 24 | A |
| 25 | A |
| 26 | C |
| 27 | C |
| 28 | C |
| 29 | C |
| 30 | A |
| 31 | B |
| 32 | C |
| 33 | B |
| 34 | A |
| 35 | C |
| 36 | C |
| 37 | C |
| 38 | C |
| 39 | C |
| 40 | C |
| 41 | A |
| 42 | A |
| 43 | C |

TABLE 2-continued

Inhibition of KRas G12C Activity by Exemplary Compounds

| Example No. | POC |
|---|---|
| 44 | C |
| 45 | A |
| 46 | A |
| 47 | C |
| 48 | C |
| 49 | B |
| 50 | C |
| 51 | A |
| 52 | C |
| 53 | C |
| 54 | A |
| 55 | C |
| 56 | C |
| 57 | C |
| 58 | C |
| 59 | C |
| 60 | C |
| 61 | C |
| 62 | C |
| 63 | C |
| 64 | C |
| 65 | C |
| 66 | C |
| 67 | C |
| 68 | A |
| 69 | A |
| 70 | C |
| 71 | A |
| 72 | C |
| 73 | C |
| 74 | C |
| 75 | C |
| 76 | C |
| 77 | C |
| 78 | C |
| 79 | A |
| 80 | C |
| 81 | C |
| 82 | C |
| 83 | C |
| 84 | A |
| 85 | C |
| 86 | A |
| 87 | A |
| 88 | C |
| 89 | C |
| 90 | C |
| 91 | A |
| 92 | C |
| 93 | C |
| 94 | A |
| 95 | A |
| 96 | A |
| 97 | C |
| 98 | C |
| 99 | C |
| 100 | C |
| 101 | C |
| 102 | C |
| 103 | C |
| 104 | C |
| 105 | B |
| 106 | A |
| 107 | C |
| 108 | C |
| 109 | C |
| 110 | C |
| 111 | C |
| 112 | A |
| 113 | C |
| 114 | B |
| 115 | C |
| 116 | C |
| 117 | C |
| 118 | A |
| 119 | B |
| 120 | C |
| 121 | C |
| 122 | C |
| 123 | A |
| 124 | C |
| 125 | A |
| 126 | C |
| 127 | C |
| 128 | C |
| 129 | C |
| 130 | C |
| 131 | C |
| 132 | C |
| 133 | C |
| 134 | C |
| 135 | C |
| 136 | C |
| 137 | C |
| 138 | C |
| 139 | C |
| 140 | C |
| 141 | C |
| 142 | C |
| 143 | C |
| 144 | C |
| 145 | C |
| 146 | B |
| 147 | C |
| 148 | C |
| 149 | B |
| 150 | C |
| 151 | B |
| 152 | C |
| 153 | C |
| 154 | C |
| 155 | C |
| 156 | C |
| 157 | C |
| 158 | C |
| 159 | C |
| 160 | C |
| 161 | C |
| 162 | B |
| 163 | C |
| 164 | C |
| 165 | C |
| 166 | B |
| 167 | B |
| 168 | C |
| 169 | C |
| 170 | C |
| 171 | C |
| 172 | C |
| 173 | C |
| 174 | C |
| 175 | C |
| 176 | C |
| 177 | C |
| 178 | C |
| 179 | C |
| 180 | C |
| 181 | C |
| 182 | C |
| 183 | C |
| 184 | C |
| 185 | C |
| 186 | B |
| 187 | C |
| 188 | C |
| 189 | C |
| 190 | C |
| 191 | C |
| 192 | C |
| 193 | C |
| 194 | C |
| 195 | C |

TABLE 2-continued

Inhibition of KRas G12C Activity by Exemplary Compounds

| Example No. | POC |
| --- | --- |
| 196 | C |
| 197 | C |
| 198 | C |
| 199 | C |
| 200 | C |
| 201 | B |
| 202 | C |
| 203 | C |
| 204 | C |
| 205 | C |
| 206 | C |
| 207 | C |
| 208 | C |
| 209 | C |
| 210 | C |
| 211 | C |
| 212 | C |
| 213 | C |
| 214 | C |
| 215 | C |
| 216 | C |
| 217 | C |
| 218 | C |
| 219 | C |
| 220 | C |
| 221 | C |
| 222 | C |
| 223 | C |
| 224 | C |
| 225 | C |
| 226 | C |
| 227 | A |
| 228 | C |
| 229 | C |
| 230 | C |
| 231 | C |
| 232 | C |
| 233 | C |
| 234 | C |
| 235 | C |
| 236 | C |
| 237 | C |
| 238 | C |
| 239 | C |
| 240 | C |
| 241 | C |
| 242 | C |
| 243 | C |
| 244 | C |
| 245 | C |
| 246 | C |
| 247 | C |
| 248 | C |
| 249 | C |
| 250 | C |
| 251 | C |
| 252 | C |
| 253 | C |
| 254 | C |
| 255 | A |
| 256 | C |
| 257 | C |
| 258 | C |
| 259 | C |
| 260 | C |
| 261 | A |
| 262 | A |
| 263 | C |
| 264 | C |
| 265 | C |
| 266 | C |
| 267 | C |
| 268 | C |
| 269 | C |
| 270 | C |
| 271 | C |
| 272 | C |
| 273 | C |
| 274 | C |
| 275 | C |
| 276 | C |
| 277 | C |
| 278 | C |
| 279 | C |
| 280 | C |
| 281 | C |
| 282 | A |
| 283 | C |
| 284 | C |
| 285 | C |
| 286 | C |
| 287 | C |
| 288 | A |
| 289 | C |
| 290 | C |
| 291 | C |
| 292 | A |
| 293 | C |
| 294 | C |
| 295 | A |
| 296 | C |
| 297 | C |
| 298 | C |
| 299 | C |
| 300 | C |
| 301 | C |
| 302 | C |
| 303 | C |
| 304 | C |
| 305 | C |
| 306 | C |
| 307 | C |
| 308 | C |
| 309 | C |
| 310 | C |
| 311 | C |
| 312 | C |
| 313 | C |
| 314 | C |
| 315 | C |
| 316 | C |
| 317 | C |
| 318 | C |
| 319 | C |
| 320 | C |
| 321 | B |
| 322 | C |
| 323 | C |
| 324 | C |
| 325 | C |
| 326 | C |
| 327 | C |
| 328 | C |
| 329 | C |
| 330 | C |
| 331 | C |
| 332 | C |
| 333 | C |
| 334 | C |
| 335 | C |
| 336 | C |
| 337 | C |
| 338 | C |
| 339 | C |
| 340 | C |
| 341 | C |
| 342 | C |
| 343 | C |
| 344 | C |
| 345 | C |
| 346 | C |
| 347 | C |

TABLE 2-continued

Inhibition of KRas G12C Activity by Exemplary Compounds

| Example No. | POC |
|---|---|
| 348 | C |
| 349 | C |
| 350 | C |
| 351 | C |
| 352 | C |
| 353 | C |
| 354 | C |
| 355 | A |
| 356 | C |
| 357 | A |
| 358 | C |
| 359 | C |
| 360 | C |
| 361 | C |
| 362 | C |
| 363 | C |
| 364 | C |
| 365 | C |
| 366 | C |
| 367 | C |
| 368 | C |
| 369 | C |
| 370 | C |
| 371 | C |
| 372 | C |
| 373 | C |
| 374 | C |
| 375 | C |
| 376 | C |
| 377 | C |
| 378 | C |
| 379 | C |
| 380 | C |
| 381 | C |
| 382 | C |
| 383 | C |
| 384 | C |
| 385 | C |
| 386 | C |
| 387 | C |
| 388 | C |
| 389 | C |
| 390 | C |
| 391 | C |
| 392 | C |
| 393 | C |
| 394 | C |
| 395 | C |
| 396 | C |
| 397 | C |
| 398 | C |
| 399 | C |
| 400 | C |
| 401 | C |
| 402 | C |
| 403 | C |
| 404 | C |
| 405 | C |
| 406 | C |
| 407 | C |
| 408 | C |
| 409 | C |
| 410 | C |
| 411 | C |
| 412 | C |
| 413 | C |
| 414 | C |
| 415 | C |
| 416 | C |
| 417 | C |
| 418 | C |
| 419 | C |
| 420 | C |
| 421 | C |
| 422 | C |
| 423 | C |
| 424 | C |
| 425 | C |
| 426 | C |
| 427 | C |
| 428 | C |
| 429 | C |
| 430 | C |
| 431 | C |
| 432 | C |
| 433 | C |
| 434 | C |
| 435 | C |
| 436 | C |
| 437 | C |
| 438 | C |
| 439 | C |
| 440 | C |
| 441 | C |
| 442 | C |
| 443 | C |
| 444 | C |
| 445 | C |
| 446 | C |
| 447 | C |
| 448 | C |
| 449 | C |
| 450 | C |
| 451 | C |
| 452 | C |
| 453 | C |
| 454 | C |
| 455 | C |
| 456 | C |
| 457 | C |
| 458 | C |
| 459 | C |
| 460 | C |
| 461 | C |
| 462 | C |
| 463 | C |
| 464 | C |
| 465 | C |
| 466 | C |
| 467 | N.D. |
| 468 | N.D. |
| 469 | N.D. |
| 470 | N.D. |
| 471 | C |
| 472 | C |
| 473 | C |
| 474 | C |
| 475 | C |
| 476 | C |
| 477 | C |
| 478 | C |
| 479 | C |
| 480 | C |
| 481 | C |
| 482 | C |
| 483 | C |
| 484 | C |
| 485 | A |
| 486 | C |
| 487 | A |
| 488 | B |
| 489 | C |
| 490 | C |
| 491 | C |
| 492 | A |
| 493 | C |
| 494 | C |
| 495 | C |
| 496 | C |
| 497 | C |
| 498 | C |
| 499 | C |

TABLE 2-continued

Inhibition of KRas G12C Activity by Exemplary Compounds

| Example No. | POC |
|---|---|
| 500 | C |
| 501 | C |
| 502 | C |
| 503 | C |
| 504 | C |
| 505 | C |
| 506 | C |
| 507 | C |
| 508 | C |
| 509 | C |
| 510 | C |
| 511 | C |
| 512 | A |
| 513 | C |
| 514 | A |
| 515 | N.D. |
| 516 | N.D. |
| 517 | N.D. |
| 518 | N.D. |
| 519 | N.D. |
| 520 | N.D. |
| 521 | N.D. |
| 522 | N.D. |
| 523 | N.D. |
| 524 | C |
| 525 | B |
| 526 | C |
| 527 | N.D. |
| 529 | C |
| 530 | C |
| 542 | C |
| 543 | C |
| 554 | C |
| 555 | C |
| 556 | C |
| 557 | C |
| 558 | C |
| 559 | C |
| 560 | C |
| 561 | C |
| 562 | C |
| 563 | C |
| 564 | C |
| 565 | C |
| 566 | C |
| 567 | C |
| 568 | C |
| 569 | N.D. |
| 570 | N.D. |
| 571 | C |
| 572 | C |
| 573 | N.D. |
| 574 | C |
| 575 | C |
| 576 | C |
| 577 | C |
| 578 | C |
| 579 | C |
| 580 | C |
| 581 | C |
| 582 | C |
| 583 | C |
| 584 | N.D. |
| 585 | C |
| 586 | C |
| 587 | A |
| 588 | C |
| 589 | C |
| 590 | B |
| 591 | B |
| 592 | C |
| 593 | C |
| 594 | A |
| 595 | C |
| 596 | C |
| 597 | C |
| 598 | C |
| 599 | C |
| 600 | C |

Example B

Inhibition of KRas G12C-Dependent Cell Growth

This Example illustrates that exemplary compounds of the present invention inhibit the growth of tumor cell lines that express KRas G12C.

The cellular inhibition of KRAs G12C by exemplary compounds of the present invention was determined by measuring the amount of a downstream marker of KRas activity, phosphorylated ERK ("Phospho-ERK").

NCI-H358 cells (ATCC CRL-5807) express KRas G12C and were grown in RPMI medium supplemented with 10% fetal bovine serum, penicillin/streptomycin and 10 mM HEPES. Cells were plated in poly-D-Lysine coated 96-well plates at a concentration of 50,000 cells/well and allowed to attach for 8-12 hours. Diluted compounds were then added at a final concentration of 0.5% DMSO. After 3 hours, the medium was removed, 150 µL of 4% formaldehyde was added and the plates were incubated for 20 minutes. The plates were washed with PBS, and permeabilized using 150 µL of ice cold 100% methanol for 10 minutes. Non-specific antibody binding to the plates was blocked using 100 µL Licor Blocking Buffer (Li-Cor Biotechnology, Lincoln Nebr.) for 1 hour at room temperature. Positive control samples and samples lacking cells were parallel processed with test samples as standards.

The amount Phospho-ERK was determined using an antibody specific for the phosphorylated form of ERK and compared to the amount of GAPDH. Primary antibodies used for detection were added as follows: Phospho-ERK (Cell Signaling cs9101) diluted 1:500 and GAPDH (Millipore MAB374) diluted 1:5000 in Licor block+0.05% Tween 20. The plates were incubated for 2 hours at room temperature. The plates were washed with PBS+0.05% Tween 20.

Secondary antibodies used to visualize primary antibodies were added as follows: Anti-rabbit-680 diluted 1:1000 and Anti-mouse-800 diluted 1:1000 in Licor Block+0.05% Tween 20 and incubated for 1 hour at room temperature. The plates were washed with PBS+0.05% Tween 20. A 100 µL aliquot of PBS was added to each well and the plates were read on a LICOR AERIUS plate reader.

The pERK(Thr202/Tyr204) signal was normalized with the GAPDH signal and percent of DMSO control values were calculated. $IC_{50}$ values were generated using a 4 parameter fit of the dose response curve. The results for exemplary compounds of Formula (I) Formula (II) are shown in Table 3. Key: "A"≥0.0001-≤1 µM; "B">1 µM and ND=not determined.

TABLE 3

Inhibition of KRas G12C-mediated Cell Proliferation by Exemplary Compounds

| Example No. | IC$_{50}$ |
|---|---|
| 1 | B |
| 2 | B |
| 3 | B |
| 4 | B |
| 5 | B |
| 6 | B |
| 7 | B |
| 8 | B |
| 9 | B |
| 10 | B |
| 11 | A |
| 12 | B |
| 13 | B |
| 14 | B |
| 15 | B |
| 16 | B |
| 17 | B |
| 18 | B |
| 19 | A |
| 20 | B |
| 21 | A |
| 22 | B |
| 23 | B |
| 24 | B |
| 25 | B |
| 26 | B |
| 27 | A |
| 28 | A |
| 29 | B |
| 30 | B |
| 31 | B |
| 32 | A |
| 33 | B |
| 34 | B |
| 35 | B |
| 36 | B |
| 37 | B |
| 38 | A |
| 39 | A |
| 40 | A |
| 41 | B |
| 42 | B |
| 43 | B |
| 44 | B |
| 45 | B |
| 46 | B |
| 47 | B |
| 48 | B |
| 49 | B |
| 50 | B |
| 51 | B |
| 52 | A |
| 53 | B |
| 54 | B |
| 55 | A |
| 56 | A |
| 57 | B |
| 58 | B |
| 59 | B |
| 60 | B |
| 61 | B |
| 62 | B |
| 63 | B |
| 64 | A |
| 65 | B |
| 66 | B |
| 67 | A |
| 68 | B |
| 69 | B |
| 70 | B |
| 71 | B |
| 72 | A |
| 73 | B |
| 74 | A |
| 75 | A |
| 76 | B |
| 77 | A |
| 78 | B |
| 79 | B |
| 80 | B |
| 81 | B |
| 82 | A |
| 83 | B |
| 84 | B |
| 85 | B |
| 86 | B |
| 87 | B |
| 88 | A |
| 89 | A |
| 90 | A |
| 91 | B |
| 92 | A |
| 93 | B |
| 94 | B |
| 95 | B |
| 96 | B |
| 97 | A |
| 98 | B |
| 99 | B |
| 100 | B |
| 101 | A |
| 102 | A |
| 103 | A |
| 104 | A |
| 105 | B |
| 106 | B |
| 107 | B |
| 108 | A |
| 109 | B |
| 110 | A |
| 111 | A |
| 112 | B |
| 113 | B |
| 114 | B |
| 115 | A |
| 116 | A |
| 117 | B |
| 118 | B |
| 119 | B |
| 120 | A |
| 121 | B |
| 122 | B |
| 123 | B |
| 124 | B |
| 125 | B |
| 126 | B |
| 127 | A |
| 128 | B |
| 129 | A |
| 130 | A |
| 131 | A |
| 132 | A |
| 133 | B |
| 134 | B |
| 135 | A |
| 136 | B |
| 137 | B |
| 138 | B |
| 139 | B |
| 140 | B |
| 141 | B |
| 142 | B |
| 143 | B |
| 144 | A |
| 145 | A |
| 146 | B |
| 147 | A |
| 148 | A |
| 149 | A |
| 150 | A |

TABLE 3-continued

Inhibition of KRas G12C-mediated Cell Proliferation by Exemplary Compounds

| Example No. | IC$_{50}$ |
|---|---|
| 151 | B |
| 152 | A |
| 153 | A |
| 154 | A |
| 155 | A |
| 156 | A |
| 157 | B |
| 158 | B |
| 159 | B |
| 160 | B |
| 161 | B |
| 162 | B |
| 163 | B |
| 164 | B |
| 165 | B |
| 166 | B |
| 167 | B |
| 168 | B |
| 169 | A |
| 170 | A |
| 171 | B |
| 172 | B |
| 173 | B |
| 174 | B |
| 175 | A |
| 176 | A |
| 177 | A |
| 178 | A |
| 179 | A |
| 180 | A |
| 181 | B |
| 182 | A |
| 183 | A |
| 184 | B |
| 185 | A |
| 186 | B |
| 187 | A |
| 188 | A |
| 189 | B |
| 190 | A |
| 191 | B |
| 192 | A |
| 193 | A |
| 194 | B |
| 195 | B |
| 196 | A |
| 197 | A |
| 198 | B |
| 199 | B |
| 200 | B |
| 201 | B |
| 202 | A |
| 203 | A |
| 204 | B |
| 205 | B |
| 206 | A |
| 207 | B |
| 208 | B |
| 209 | B |
| 210 | A |
| 211 | A |
| 212 | A |
| 213 | B |
| 214 | B |
| 215 | B |
| 216 | B |
| 217 | B |
| 218 | A |
| 219 | B |
| 220 | A |
| 221 | A |
| 222 | A |
| 223 | A |
| 224 | A |
| 225 | A |
| 226 | A |
| 227 | A |
| 228 | A |
| 229 | A |
| 230 | A |
| 231 | A |
| 232 | B |
| 233 | A |
| 234 | A |
| 235 | A |
| 236 | A |
| 237 | A |
| 238 | A |
| 239 | B |
| 240 | B |
| 241 | B |
| 242 | A |
| 243 | A |
| 244 | A |
| 245 | A |
| 246 | A |
| 247 | B |
| 248 | B |
| 249 | A |
| 250 | B |
| 251 | A |
| 252 | A |
| 253 | A |
| 254 | A |
| 255 | B |
| 256 | B |
| 257 | A |
| 258 | B |
| 259 | A |
| 260 | A |
| 261 | B |
| 262 | B |
| 263 | A |
| 264 | B |
| 265 | A |
| 266 | A |
| 267 | A |
| 268 | A |
| 269 | A |
| 270 | A |
| 271 | A |
| 272 | A |
| 273 | B |
| 274 | A |
| 275 | A |
| 276 | A |
| 277 | A |
| 278 | A |
| 279 | A |
| 280 | A |
| 281 | A |
| 282 | B |
| 283 | A |
| 284 | A |
| 285 | A |
| 286 | A |
| 287 | A |
| 288 | B |
| 289 | B |
| 290 | A |
| 291 | A |
| 292 | B |
| 293 | A |
| 294 | B |
| 295 | B |
| 296 | A |
| 297 | A |
| 298 | A |
| 299 | A |
| 300 | A |

TABLE 3-continued

Inhibition of KRas G12C-mediated Cell Proliferation by Exemplary Compounds

| Example No. | IC$_{50}$ |
|---|---|
| 301 | A |
| 302 | A |
| 303 | A |
| 304 | A |
| 305 | B |
| 306 | A |
| 307 | B |
| 308 | A |
| 309 | A |
| 310 | A |
| 311 | A |
| 312 | A |
| 313 | A |
| 314 | A |
| 315 | A |
| 316 | A |
| 317 | A |
| 318 | A |
| 319 | A |
| 320 | A |
| 321 | B |
| 322 | A |
| 323 | A |
| 324 | A |
| 325 | B |
| 326 | A |
| 327 | A |
| 328 | A |
| 329 | A |
| 330 | A |
| 331 | A |
| 332 | A |
| 333 | A |
| 334 | A |
| 335 | A |
| 336 | A |
| 337 | A |
| 338 | A |
| 339 | A |
| 340 | B |
| 341 | A |
| 342 | A |
| 343 | B |
| 344 | A |
| 345 | B |
| 346 | A |
| 347 | A |
| 348 | A |
| 349 | A |
| 350 | A |
| 351 | A |
| 352 | A |
| 353 | B |
| 354 | B |
| 355 | B |
| 356 | B |
| 357 | A |
| 358 | A |
| 359 | A |
| 360 | A |
| 361 | A |
| 362 | A |
| 363 | A |
| 364 | A |
| 365 | A |
| 366 | A |
| 367 | A |
| 368 | B |
| 369 | A |
| 370 | A |
| 371 | A |
| 372 | A |
| 373 | B |
| 374 | B |
| 375 | B |
| 376 | A |
| 377 | A |
| 378 | A |
| 379 | A |
| 380 | A |
| 381 | A |
| 382 | A |
| 383 | A |
| 384 | A |
| 385 | A |
| 386 | A |
| 387 | A |
| 388 | A |
| 389 | B |
| 390 | A |
| 391 | A |
| 392 | B |
| 393 | A |
| 394 | A |
| 395 | A |
| 396 | A |
| 397 | A |
| 398 | A |
| 399 | A |
| 400 | A |
| 401 | A |
| 402 | A |
| 403 | A |
| 404 | A |
| 405 | A |
| 406 | A |
| 407 | B |
| 408 | B |
| 409 | A |
| 410 | A |
| 411 | A |
| 412 | A |
| 413 | A |
| 414 | A |
| 415 | A |
| 416 | A |
| 417 | A |
| 418 | A |
| 419 | A |
| 420 | A |
| 421 | A |
| 422 | A |
| 423 | A |
| 424 | A |
| 425 | A |
| 426 | A |
| 427 | A |
| 428 | A |
| 429 | B |
| 430 | A |
| 431 | B |
| 432 | A |
| 433 | B |
| 434 | A |
| 435 | A |
| 436 | A |
| 437 | A |
| 438 | A |
| 439 | B |
| 440 | A |
| 441 | A |
| 442 | A |
| 443 | A |
| 444 | A |
| 445 | A |
| 446 | B |
| 447 | A |
| 448 | A |
| 449 | A |
| 450 | A |

TABLE 3-continued

Inhibition of KRas G12C-mediated Cell Proliferation by Exemplary Compounds

| Example No. | IC$_{50}$ |
|---|---|
| 451 | A |
| 452 | A |
| 453 | A |
| 454 | A |
| 455 | A |
| 456 | B |
| 457 | A |
| 458 | A |
| 459 | A |
| 460 | A |
| 461 | A |
| 462 | A |
| 463 | A |
| 464 | A |
| 465 | B |
| 466 | A |
| 467 | N.D. |
| 468 | N.D. |
| 469 | N.D. |
| 470 | N.D. |
| 471 | B |
| 472 | A |
| 473 | A |
| 474 | A |
| 475 | A |
| 476 | A |
| 477 | A |
| 478 | A |
| 479 | A |
| 480 | A |
| 481 | A |
| 482 | A |
| 483 | A |
| 484 | A |
| 485 | A |
| 486 | A |
| 487 | A |
| 488 | B |
| 489 | A |
| 490 | A |
| 491 | A |
| 492 | A |
| 493 | A |
| 494 | B |
| 495 | A |
| 496 | A |
| 497 | A |
| 498 | A |
| 499 | A |
| 500 | A |
| 501 | A |
| 502 | A |
| 503 | B |
| 504 | A |
| 505 | B |
| 506 | A |
| 507 | A |
| 508 | A |
| 509 | A |
| 510 | A |
| 511 | A |
| 512 | B |
| 513 | A |
| 514 | B |
| 515 | N.D. |
| 516 | A |
| 517 | A |
| 518 | A |
| 519 | A |
| 520 | A |
| 521 | A |
| 522 | A |
| 523 | A |
| 524 | A |
| 525 | A |
| 526 | A |
| 527 | A |
| 528 | B |
| 529 | A |
| 530 | A |
| 542 | A |
| 543 | A |
| 554 | A |
| 555 | A |
| 556 | A |
| 557 | A |
| 558 | A |
| 559 | A |
| 560 | A |
| 561 | A |
| 562 | A |
| 563 | A |
| 564 | A |
| 565 | A |
| 566 | A |
| 567 | B |
| 568 | A |
| 569 | B |
| 570 | B |
| 571 | A |
| 572 | B |
| 573 | B |
| 574 | A |
| 575 | A |
| 576 | A |
| 577 | A |
| 578 | A |
| 579 | A |
| 580 | A |
| 581 | A |
| 582 | A |
| 583 | A |
| 584 | A |
| 585 | A |
| 586 | A |
| 587 | B |
| 588 | A |
| 589 | A |
| 590 | B |
| 591 | B |
| 592 | B |
| 593 | A |
| 594 | B |
| 595 | A |
| 596 | A |
| 597 | A |
| 598 | A |
| 599 | B |
| 600 | A |
| 601 | A |
| 602 | A |
| 603 | B |
| 604 | A |
| 605 | B |
| 606 | A |
| 607 | A |
| 608 | A |
| 609 | A |
| 610 | B |
| 611 | B |
| 612 | B |
| 613 | A |
| 614 | A |
| 615 | A |
| 616 | A |
| 617 | B |
| 618 | B |
| 619 | A |

TABLE 3-continued

Inhibition of KRas G12C-mediated Cell
Proliferation by Exemplary Compounds

| Example No. | IC$_{50}$ |
|---|---|
| 620 | N.D. |
| 621 | B |

Example C

Improved In Vitro Stability of Compounds Having Substitutions at R$^A$ or R$^B$ in Whole Blood This Example illustrates that exemplary compounds of the present invention comprising substitutions at R$^A$ or at least one R$^B$ exhibit improved whole blood stability compared to compounds in which R$^A$ and both R$^B$ substituents are hydrogen.

Materials: The following reagents were used as received: acetonitrile (HPLC grade, Burdick & Jackson, Madison, Wis.), phosphate buffered saline (PBS), pH 7.4 (Sigma-Aldrich, Co., St. Louis, Mo.), water (HPLC grade, JT Baker, Phillipsburg, N.J.), DMSO (EM Science, Merck KGaA, Darmstadt, Germany) and isopropanol (IPA, reagent grade, EMD Chemicals, Gibbstown, N.J.). Propantheline and esmolol (Sigma-Aldrich) were used as the positive control compounds in the assay. Diazepam (Sigma-Aldrich) was used as an internal standard for quantitation. Human whole blood was obtained from BioIVT (Westbury, N.Y.) and was of the male gender. All other reagents and solvents were of the highest analytical grade supplied by Sigma (St. Louis, Mo.) and were used as received.

Blood Incubations: The in vitro stability of representative KRas G12C inhibitor compounds of the present invention in the presence whole blood was conducted in the following manner. Esmolol or propantheline, which are known to undergo ester hydrolysis by esterases in blood and plasma, were used as the positive controls in the assays. A 10 mM stock solution of propantheline, esmolol, or a compound of the present invention in DMSO was diluted to 500 μM with DMSO. Aliquots of whole blood (600 μL), in triplicate, were placed in the appropriate wells of a polypropylene 96-deep well plate (Axygen Scientific, Union City, Calif.). The blood was diluted to 50% using PBS, pH 7.4 (600 μL). The diluted blood was pre-incubated for 15 minutes at 37° C. Each well was dosed with 12 μL of the 500 μM DMSO stock simultaneously for a final test concentration of 5 μM. The plates were mixed at 600 rpm for 10 seconds on a plate shaker (IKA MTS 2/4 Digital Microtiter Shaker, VWR). Aliquots of 100 μL from each well of whole blood were transferred to three separate 96-deep well plates labeled 0, 60, or 240 minutes. At the end of each designated time point, the red blood cells were lysed with 100 μL of water, mixed at 600 rpm for one minute, and stopped with 800 μL of acetonitrile containing IS (0.625 μM diazepam). The plates were mixed on the plate shaker at 600 rpm for one minute and spun in a centrifuge at 2095×g for 7 minutes at room temperature using an Allegra benchtop centrifuge (Beckman Coulter, Fullerton, Calif.). Supernatant (100 μL) was transferred to a shallow 96-well plate (Costar) using a liquid sample handling system (Apricot, Perkin-Elmer, Boston, Mass.). The addition of 100 μL of water was added to each sample of supernatant for a final volume of 200 μL. The plates were sealed and the contents of each well were analyzed by LC-MS/MS.

Analytical quantitation: The LC-MS/MS system was comprised of an HTS-PAL autosampler (Leap Technologies, Carrboro, N.C.), an HP1200 HPLC (Agilent, Palo Alto, Calif.), and an API4000 triple quadrupole mass spectrometer (PE Sciex, a division of Applied Biosystems, Foster City, Calif.). Chromatographic separation of the analyte and internal standard was achieved at room temperature using a C18 column (Kinetex®, 30×3.0 mm, 2.6 μm particle size, Phenomenex, Torrance, Calif.) in conjunction with gradient conditions using mobile phases A (aqueous 0.1% formic acid with 1% isopropyl alcohol) and B (0.1% formic acid in acetonitrile). The total run time, including re-equilibration, for a single injection was 2 minutes. Mass spectrometric detection of the analytes was accomplished using the ESI ionization mode. Ion current was optimized during infusion of a stock solution of propantheline, esmolol, or the representative test compound. Analyte responses, including the IS were measured by multiple reaction monitoring (MRM) of transitions unique to each compound.

Calculations: Data were acquired and peak areas were calculated for test compounds and the internal standard using Analyst 1.6.2 software (Sciex). The mean peak area ratios were calculated by averaging the peak area ratios (n=3) of each test compound and the IS for each sample.

Peak area tables were exported to BioAssay Enterprise (CambridgeSoft, Cambridge, Mass.), where the average analyte-to-internal standard peak area ratios were used to calculate percent remaining (% REM) and half-life ($t_{1/2}$). Percent remaining (f) was calculated by determining the ratio of the peak area ratio at each time point to the peak area ratio of the time-zero samples. The $t_{1/2}$ was determined dividing ln(2) by $k_m$. The rate of loss of test compound ($k_m$) was determined by linear regression of −ln(f(t)) versus time. The regression used the form "y=mx", therefore the model forced an intercept of 100% remaining and assumed that the metabolism followed first order kinetics.

The positive control compounds, propantheline or esmolol, and representative KRas G12C inhibitor compounds of the present invention were incubated in the presence of human whole blood at 37° C. over a 240-minute incubation period. The half-life of propantheline, esmolol, and each test compound after 240 minutes of incubation at 37° C. is shown in Table 4. Key: A≤200 min; B >200 min-≤1000 min; C >1000 min-≤2000 min; and D >2000 min

TABLE 4

In Vitro Stability of Exemplary KRas
G12C inhibitors in Human Whole Blood

| Example No. | Compound Half-life |
|---|---|
| propantheline | A |
| 235 | D |
| 236 | B |
| 331 | B |
| 359 | B |
| 367 | C |
| 372 | D |
| 478 | D |
| 479 | D |
| 480 | D |
| 481 | D |
| 482 | D |
| 484 | A |
| 485 | D |
| 490 | A |
| 491 | A |
| 495 | B |
| 498 | D |
| 501 | A |

TABLE 4-continued

In Vitro Stability of Exemplary KRas
G12C inhibitors in Human Whole Blood

| Example No. | Compound Half-life |
|---|---|
| 502 | B |
| 504 | A |
| 506 | C |
| 507 | D |
| 509 | D |
| 510 | C |
| 511 | D |
| 512 | D |
| 513 | C |
| 514 | D |
| 515 | D |
| 516 | D |
| 517 | C |
| 524 | D |
| 552 | D |
| 557 | D |
| 579 | C |

Results: As expected, positive control propantheline displayed a short half life of 98 min. In comparison, the half life of exemplary KRas G12C inhibitor compounds comprising substitutions at $R^A$ or $R^B$ in human whole blood was, in some instances, increased by greater than 3-fold or greater than 4-fold compared to unsubstituted compounds, e.g., Examples 331 and 359, resulting in greatly improved pharmacodynamic and pharmacokinetic properties of these compounds resulting in greater in vivo stability and increased bioavailability.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:
1. A compound of formula (II):

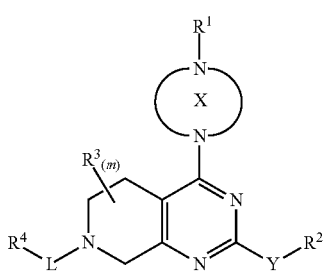

Formula (II)

or a pharmaceutically acceptable salt thereof:
wherein:
X is selected from the group consisting of a piperazine, a bridged piperazine, a 7-membered spirocyclic ring and a diazepane, wherein X is optionally substituted with one or more $R^8$;
Y is a bond, O, S or $NR^5$;
$R^1$ is —C(O)C($R^A$)═══C($R^B$)$_p$ or —SO$_2$C($R^A$)═══C($R^B$)$_p$;
$R^2$ is hydrogen, alkyl, hydroxyalkyl, dihydroxyalkyl, alkylaminylalkyl, dialkylaminylalkyl, —Z—$NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;
each Z is C1-C4 alkylene;
each $R^3$ is independently C1-C3 alkyl, oxo, haloalkyl, hydroxyl or halogen;
L is a bond, —C(O)—, or C1-C3 alkylene;
$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$, $R^7$ or $R^8$;
each $R^5$ is independently hydrogen or C1-C3 alkyl;
$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;
each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;
$R^8$ is oxo, C1-C3 alkyl, C2-C4 alkynyl, heteroalkyl, cyano, —C(O)$OR^5$, —C(O)N($R^5$)$_2$, —N($R^5$)$_2$, wherein the C1-C3 alkyl may be optionally substituted with cyano, halogen, —$OR^5$, —N($R^5$)$_2$, or heteroaryl;
each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;
each $R^{10}$ is independently hydrogen, acyl, C1-C3 alkyl, heteroalkyl or hydroxyalkyl;
$R^{11}$ is haloalkyl;
$R^A$ is absent, hydrogen, deuterium, cyano, halogen, C1-C-3 alkyl, haloalkyl, heteroalkyl, —C(O)N($R^5$)$_2$, or hydroxyalkyl;
each $R^B$ is independently hydrogen, deuterium, cyano, C1-C3 alkyl, hydroxyalkyl, heteroalkyl, C1-C3 alkoxy, halogen, haloalkyl, —ZNR$^5$R$^{11}$, —C(O)N($R^5$)$_2$, —NHC(O)C1-C3 alkyl, —CH$_2$NHC(O)C1-C3 alkyl, -CH$_2$N(CH$_3$)C(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;

or when ═══ is a double bond and p is two, one $R^B$ is hydrogen and $R^A$ and one $R^B$ and the carbon atoms to which they are attached form a 4-8 membered partially saturated cycloalkyl substituted with oxo;
m is zero or an integer between 1 and 2;
p is one or two; and wherein, when ═══ is a triple bond then $R^A$ is absent, p equals one and $R^B$ is hydroxyalkyl, or when ═══ is a double bond then $R^A$ is present, $R^B$ is present and p equals two, wherein when $R^A$ is hydrogen or C1-C3 alkyl, at least one $R^B$ is deuterium, cyano, halogen, haloalkyl, hydroxyalkyl, heteroalkyl, heteroaryl, heteroarylalkyl, —ZNR$^5$R$^{11}$, —C(O)N($R^5$)$_2$, —NHC(O)C1-C3 alkyl, -CH$_2$NHC(O)C1-C3 alkyl, —NHC(O)C1-C3 alkyl or heterocyclylalkyl, wherein the heterocyclyl portion is substituted with one or more substituents independently selected from halogen, hydroxyl, alkoxy and C1-C3 alkyl; or when each $R^B$ is hydrogen, then $R^A$ is deuterium, cyano, halogen, haloalkyl, —C(O)N($R^5$)$_2$, hydroxyalkyl or heteroalkyl.

2. The compound of claim 1, wherein $R^1$—X is:

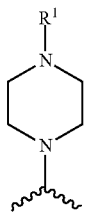

wherein the piperazinyl ring is optionally substituted with $R^8$.

3. The compound of claim 2, wherein $R^1$ is —C(O)C($R^A$)$=\!=\!=$C($R^B$)$_p$.

4. The compound of claim 3, wherein $=\!=\!=$ is a triple bond and $R^A$ is absent, p is one and $R^B$ is hydroxyalkyl or C1-C3 alkoxy.

5. The compound of claim 3, wherein $=\!=\!=$ is a double bond and $R^A$ is hydrogen, p is two and at least one $R^B$ is independently deuterium, cyano, halogen, haloalkyl, hydroxyalkyl, heteroalkyl, heteroaryl, heteroarylalkyl, —ZNR$^5$R$^{11}$, —C(O)N(R$^5$)$_2$, —NHC(O)C1-C3 alkyl, —NHC(O)C1-C3 alkyl or heterocyclylalkyl wherein the heterocyclyl portion is substituted with one or more substituents independently selected from halogen, hydroxyl, alkoxy or C1-C3 alkyl.

6. The compound of claim 5, wherein the at least one $R^B$ is halogen.

7. The compound of claim 5, wherein the at least one $R^B$ is haloalkyl.

8. The compound of claim 5, wherein the at least one $R^B$ is —ZNR$^5$R$^{11}$.

9. The compound of claim 5, wherein the at least one $R^B$ is cyano.

10. The compound of claim 5, wherein the at least one $R^B$ is hydroxyalkyl.

11. The compound of claim 5, wherein the at least one $R^B$ is heteroalkyl.

12. The compound of claim 5, wherein the at least one $R^B$ is —C(O)N(R$^5$)$_2$, wherein each $R^5$ is hydrogen.

13. The compound of claim 5, wherein the at least one $R^B$ is —C(O)N(R$^5$)$_2$, wherein each $R^5$ is C1-C3 alkyl.

14. The compound of claim 5, wherein the at least one $R^B$ is heteroaryl optionally substituted with one or more $R^7$.

15. The compound of claim 5, wherein the at least one $R^B$ is heteroarylalkyl optionally substituted with one or more $R^7$.

16. The compound of claim 5, wherein the at least one $R^B$ is heterocyclylalkyl substituted with one or more $R^7$.

17. The compound of claim 3, wherein $=\!=\!=$ is a double bond and p is two, each $R^B$ is hydrogen, and $R^A$ is deuterium, cyano, halogen, haloalkyl, heteroalkyl, —C(O)N(R$^5$)$_2$, or hydroxyalkyl.

18. The compound of claim 17, wherein $R^A$ is halogen.

19. The compound of claim 17, wherein $R^A$ is haloalkyl.

20. The compound of claim 17, wherein $R^A$ is cyano.

21. The compound of claim 17, wherein $R^A$ is heteroalkyl.

22. The compound of claim 17, wherein $R^A$ is —C(O)N(R$^5$)$_2$, wherein each $R^5$ is hydrogen.

23. The compound of claim 17, wherein $R^A$ is hydroxyalkyl.

24. The compound of claim 2, wherein $=\!=\!=$ is a double bond and p is two, one $R^B$ is hydrogen, the second $R^B$ is dialkylaminylalkyl, and $R^A$ is halogen.

25. The compound of claim 2, wherein $=\!=\!=$ is a double bond and p is two, each $R^B$ is deuterium, and $R^A$ is deuterium.

26. The compound of claim 2, wherein Y is O.

27. The compound of claim 2, wherein $R^2$ is selected from the group consisting of hydroxyalkyl, alkylaminylalkyl, dialkylaminylalkyl, —ZNR$^5$R$^{10}$, heterocyclyl and heterocyclylalkyl, wherein each of the Z, heterocyclyl or heterocyclylalkyl are independently optionally substituted with $R^9$.

28. The compound of claim 27, wherein $R^2$ is heterocyclylalkyl optionally substituted with one or more $R^9$.

29. The compound of claim 28, wherein the heterocyclyl of the heterocyclylalkyl is independently azetidinyl, methylazetidinyl, N-ethylazetidinyl, N-isopropylazetidinyl, N-tert-butylazetidinyl, fluoroazetidinyl, difluoroazetidinyl, cyclopropylazetidinyl, cyclopentylazetidinyl, tetrahydropyranylazetidinyl, tetrahydropyranyl, pyrrolidinyl, methylpyrrolidinyl, dimethylpyrrolidinyl, (N-methyl)-2-methylpyrrolidinyl, (N-methyl)-2-ethylpyrrolidinyl, (N-methyl)-3,3-dimethylpyrrolidinyl, isopropylpyrrolidinyl, N-tert-butylpyrrolidinyl, cycloalkylalkylpyrrolidinyl, hydroxypyrrolindinyl, hydroxyethylpyrrolidinyl, fluoropyrrolidinyl, difluoropyrrolidinyl, (N-methyl)fluoropyrrolidinyl, (N-methyl)difluoropyrrolidinyl, fluoroethylpyrrolidinyl, methoxyethylpyrrolidinyl, (N-methyl)methoxypyrrolidinyl, piperazinyl, dimethylaminylpyrrolidinyl, morpholinyl, methylmorpholinyl, N-ethylmorpholinyl, N-isopropylmorpholinyl, oxetanyl, 1,4-oxazepanyl, piperdinyl, methylpiperidinyl acylpiperdinyl, cyanopiperdinyl, cycloalkylpiperdinyl, halopiperdinyl, dihalopiperdinyl, fluoropiperdinyl, difluoropiperdinyl, alkoxypiperdinyl, pyrrolidonyl, methylpyrrolidonyl, (N-methyl)-2-pyrrolidin-2-one, (N-ethyl)-2-pyrrolidonyl, (N-benzyl)-2-pyrrolidonyl, hydroxy-substituted-(N-methyl)pyrrolidonyl, piperidinonyl, hexahydropyrrolizinyl, thiomorpholinyl-1,1-dioxide, 3-azabicyclo[3.1.0]hexanyl, oxa-5-azabicyclo[2.2.1]heptan-5-yl, or azabicyclo[2.2.1]heptan-2-yl.

30. The compound of claim 29, wherein the (N-methyl)difluoropyrrolidinyl is 3,3-difluoro-1-methylpyrrolidinyl.

31. The compound of claim 29, wherein the heterocyclyl is N-methylpyrrolidinyl.

32. The compound of claim 27, wherein $R^2$ is dialkylaminylalkyl optionally substituted with one or more $R^9$.

33. The compound of claim 2, wherein $R^4$ is aryl optionally substituted with one or more $R^7$.

34. The compound of claim 33, wherein the aryl is selected from the group consisting of phenyl and naphthyl optionally substituted with one or more $R^7$.

35. The compound of claim 34, wherein the phenyl and the naphthyl are each optionally substituted with one or more $R^7$ selected from the group consisting of cyano, halogen, hydroxyl, C1-C6 alkyl, hydroxyalkyl, Q-haloalkyl, cycloalkyl, and alkoxy.

36. The compound of claim 35, wherein $R^7$ is selected from the group consisting of chloro, fluoro, bromo, hydroxymethyl, methyl, ethyl, isopropyl, methoxy, trifluoromethyl, hydroxyl, cyclopropyl and cyano.

37. The compound of claim 2, wherein $R^4$ is heteroaryl.

38. The compound of claim 2, wherein $R^4$ is aralkyl optionally substituted with one or more $R^7$.

39. The compound of claim 2, wherein m is zero.

40. The compound of claim 2, wherein L is a bond.

41. The compound of claim 2, wherein $R^8$ is heteroalkyl, C2-C4 alkynyl, or C1-C3alkyl optionally substituted with halogen, —$OR^5$, cyano or heteroaryl.

42. The compound of claim 41, wherein $R^8$ is C1-C3 alkyl optionally substituted with cyano.

43. The compound of claim 41, wherein $R^8$ is cyanomethyl.

44. The compound of claim 41, wherein X is substituted with one $R^8$.

45. The compound of claim 1, wherein the compound is:

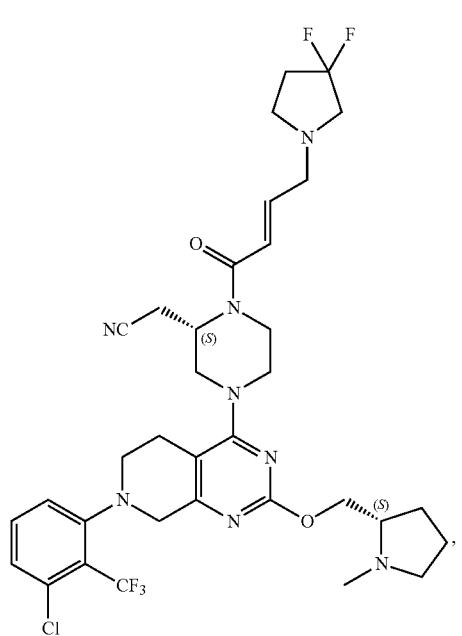

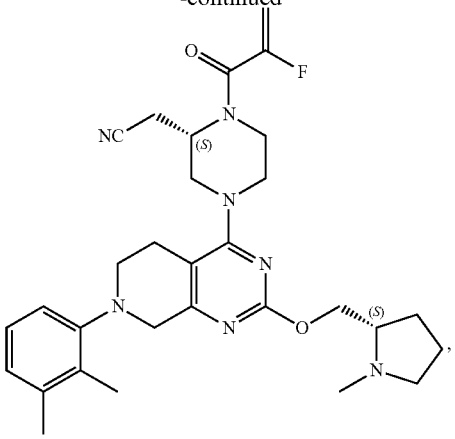

-continued

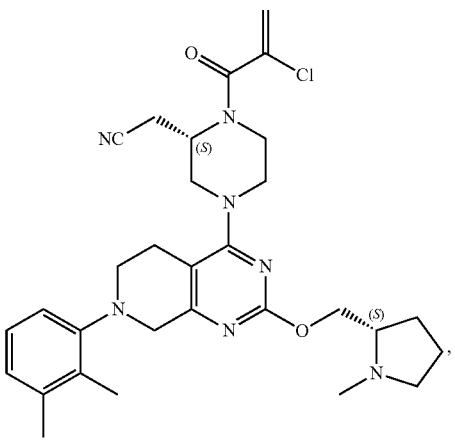

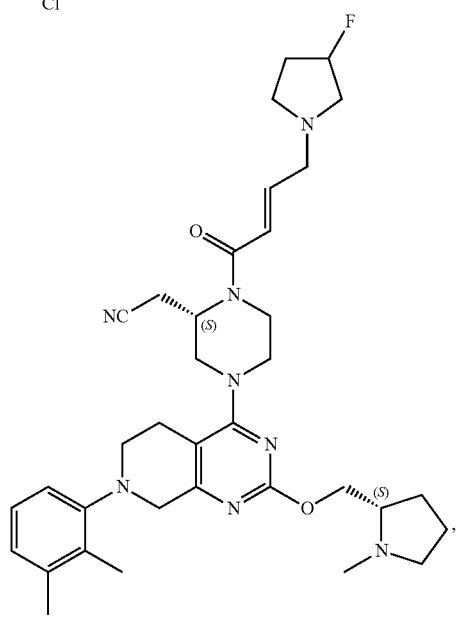

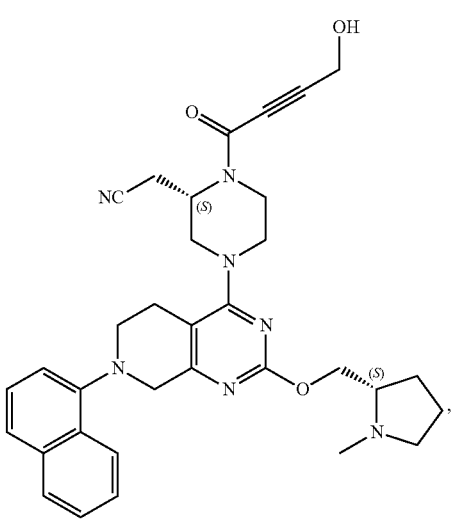

1665
-continued
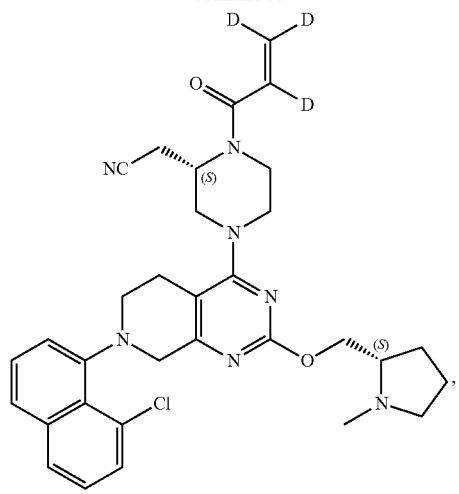
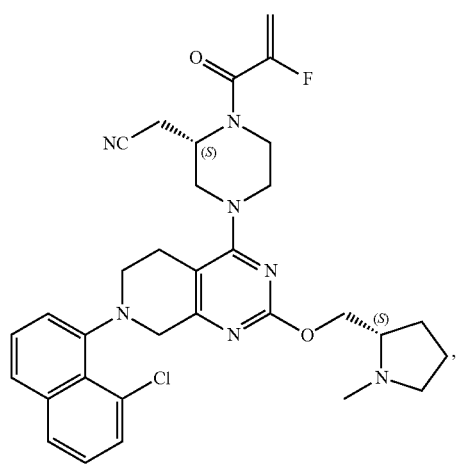
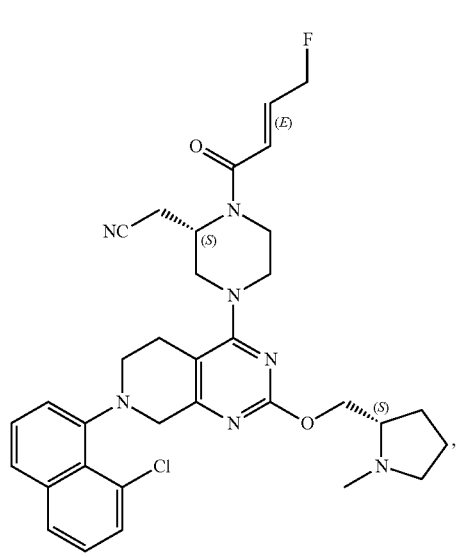
1666
-continued
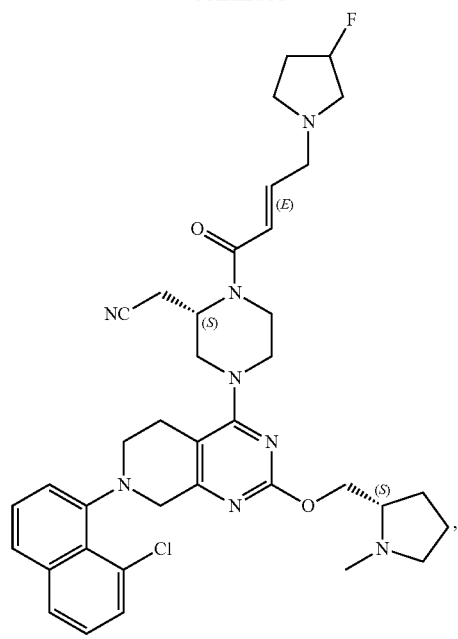
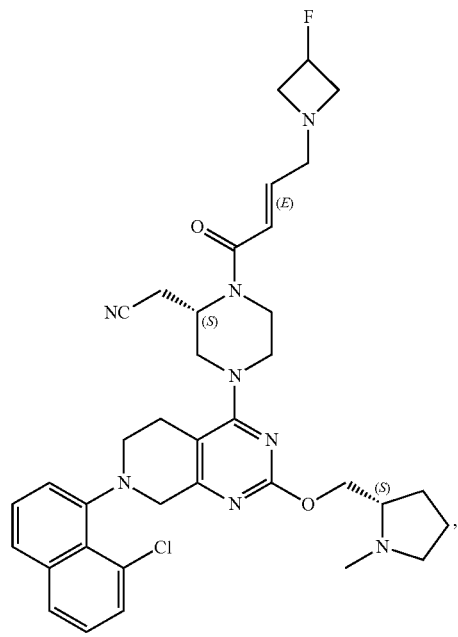

1667
-continued
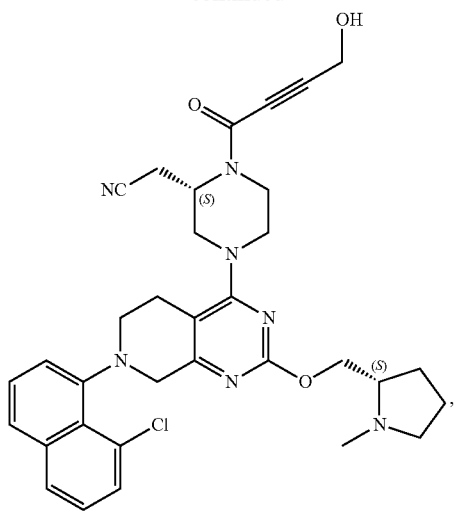
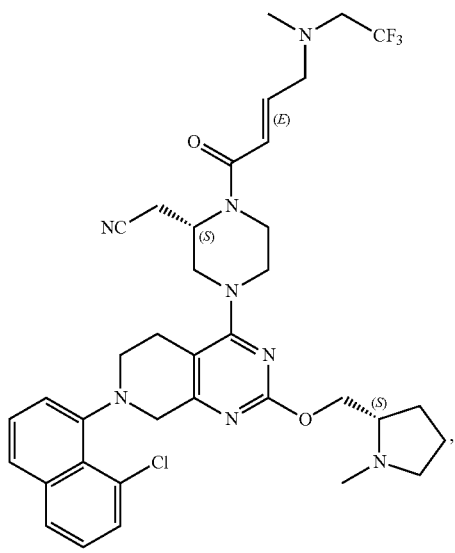
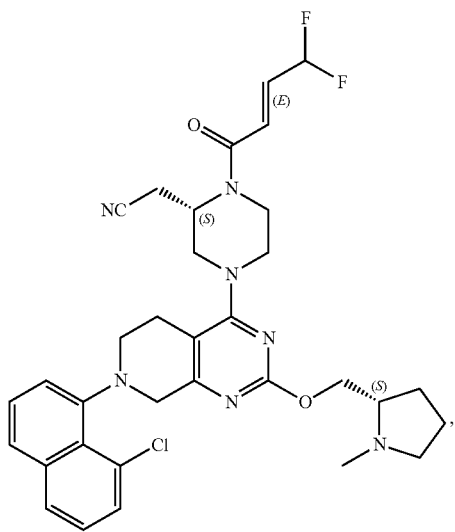
1668
-continued
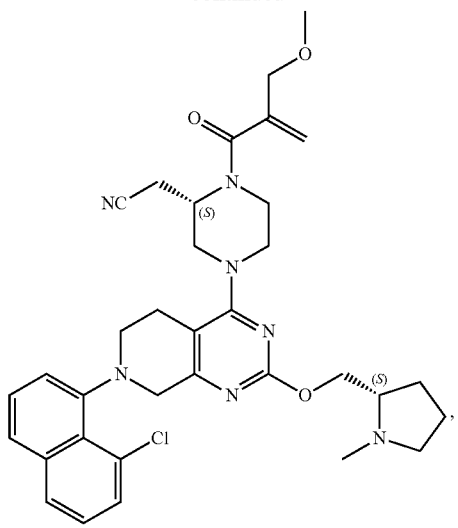
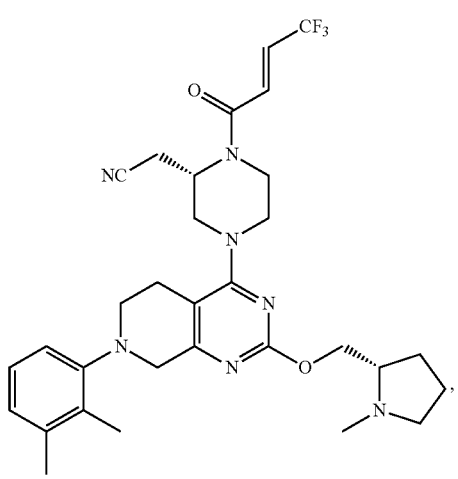
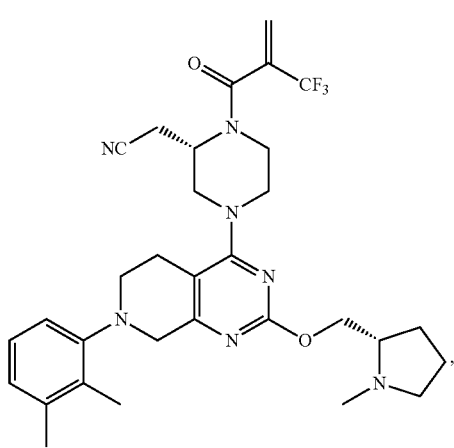

1669
-continued
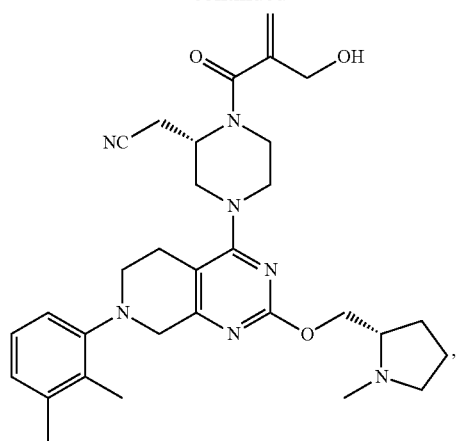
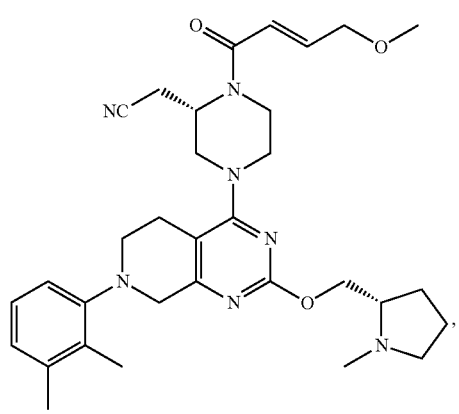
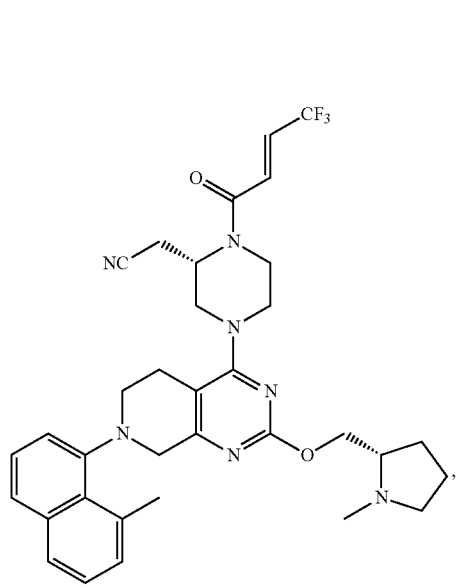
1670
-continued
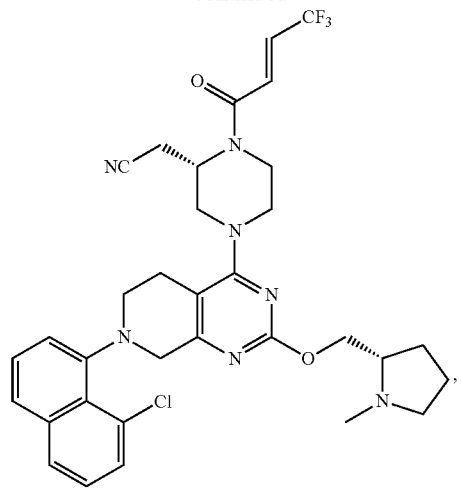
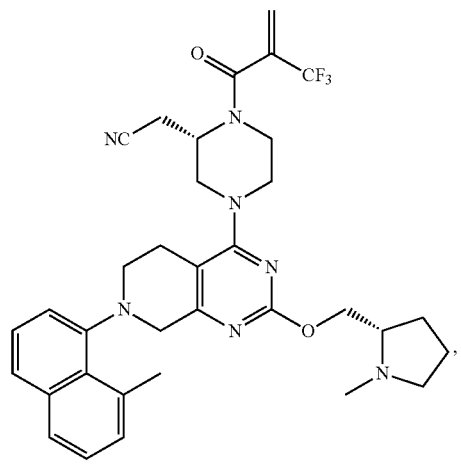
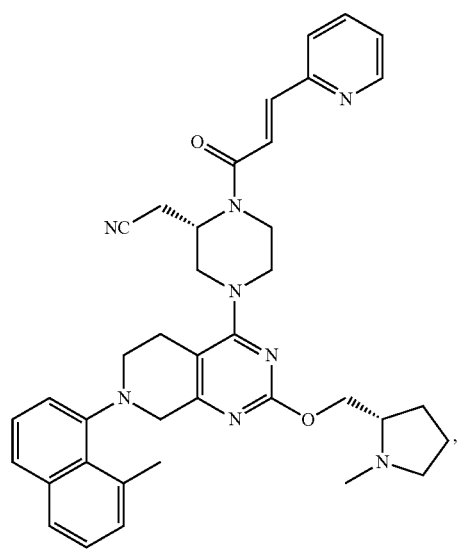

1671
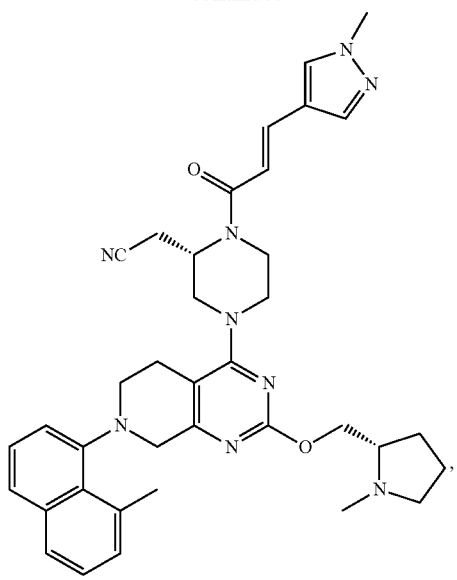
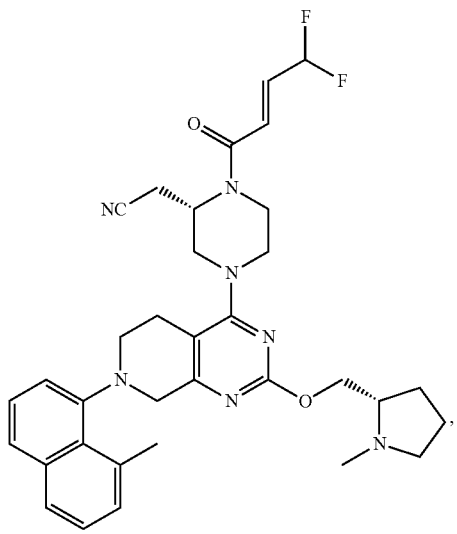
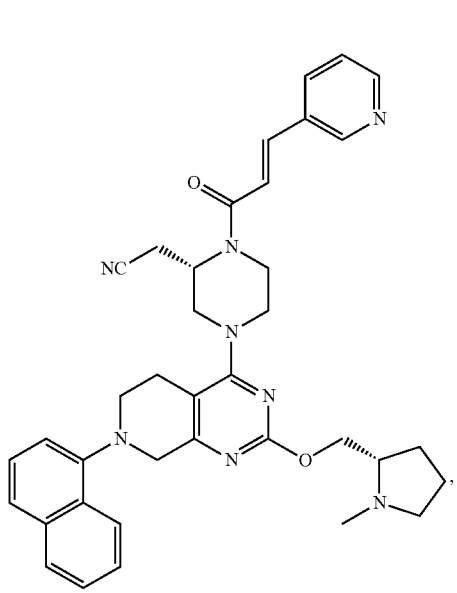
1672
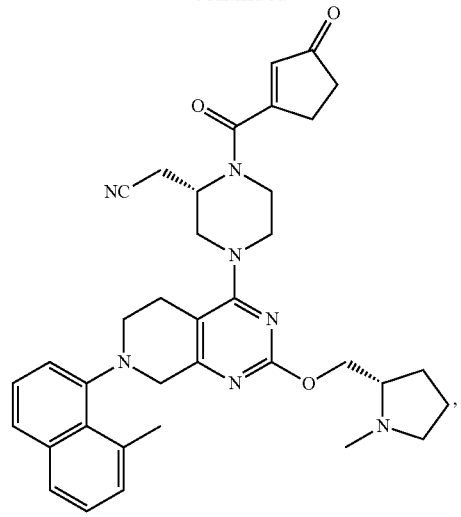
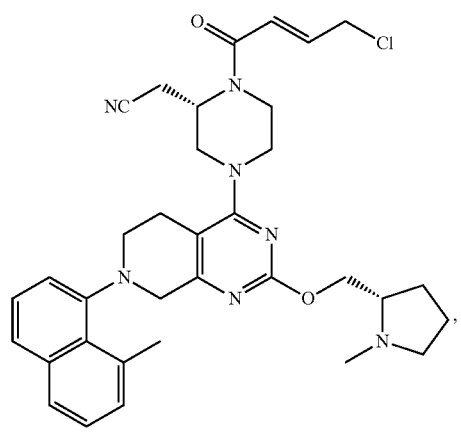
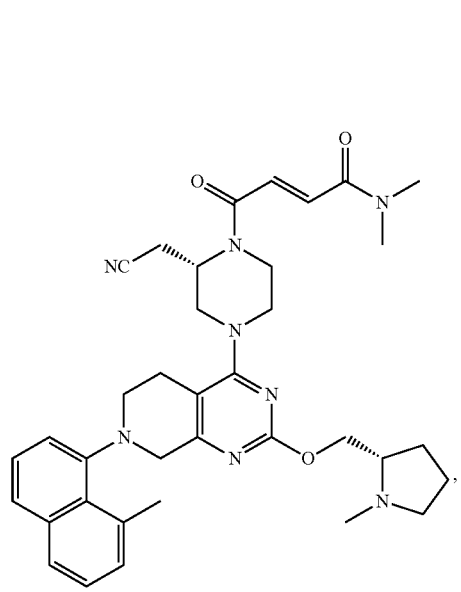

1673
-continued
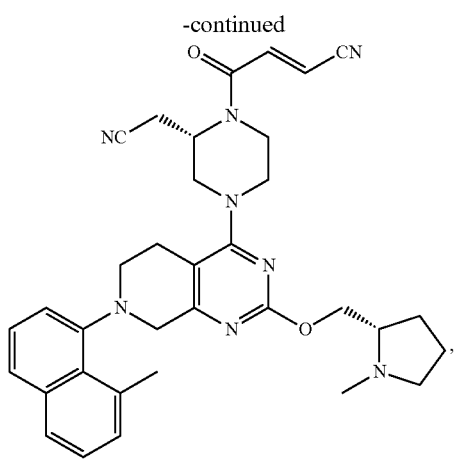
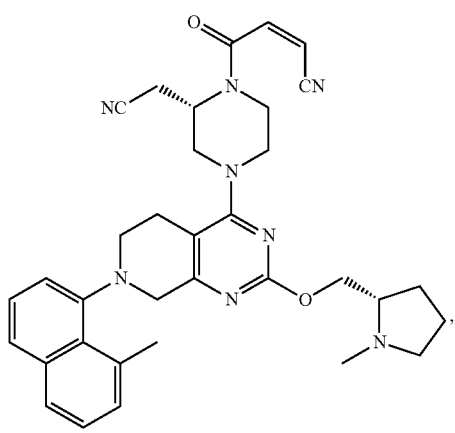
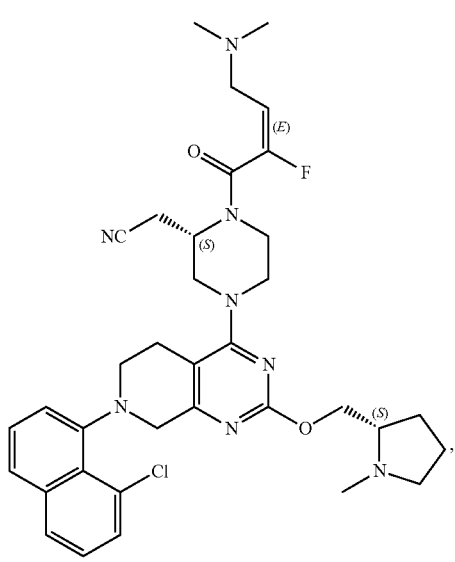
1674
-continued
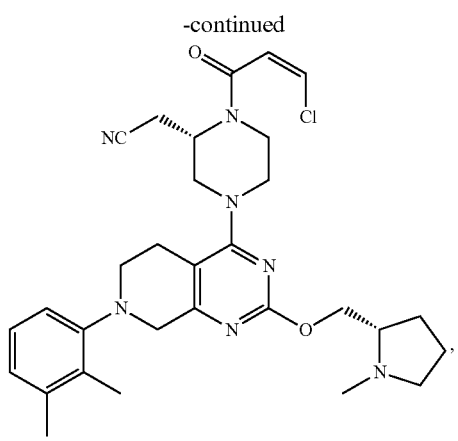
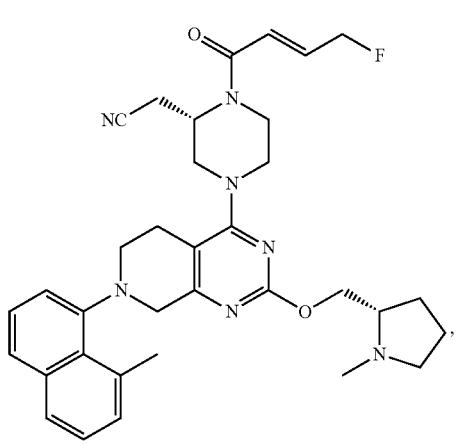
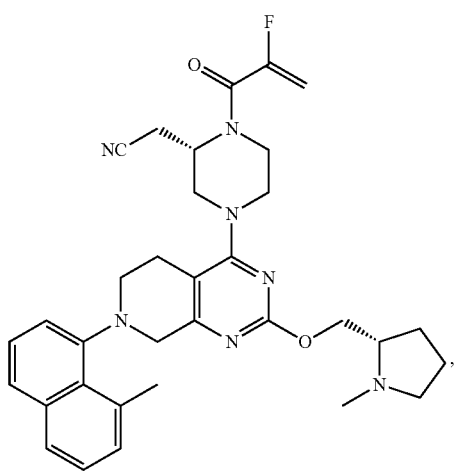

1675
-continued
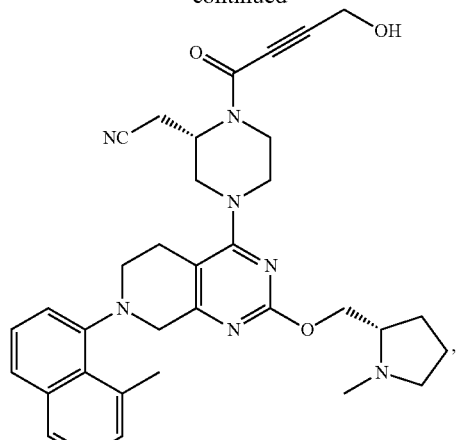
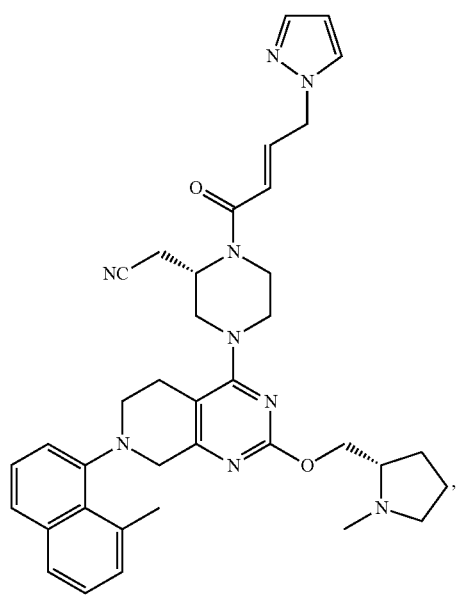
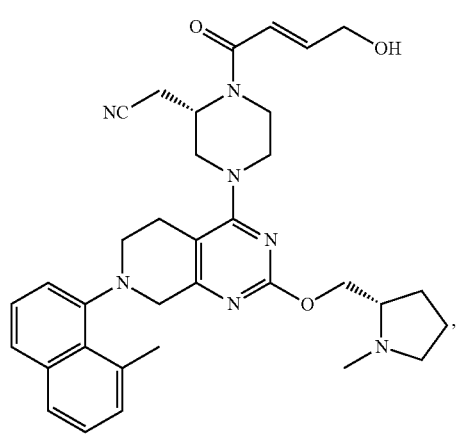
1676
-continued
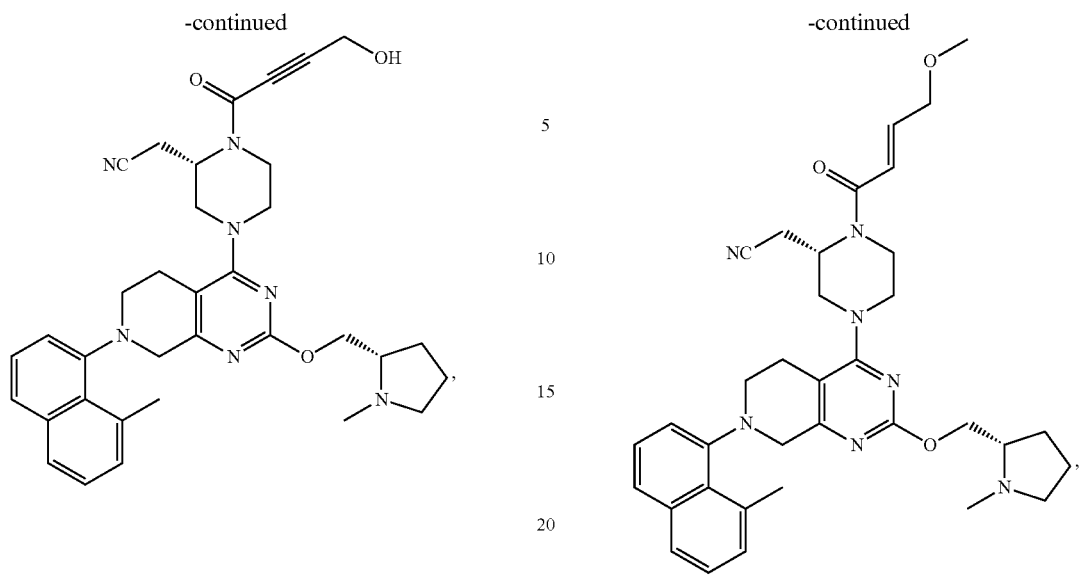
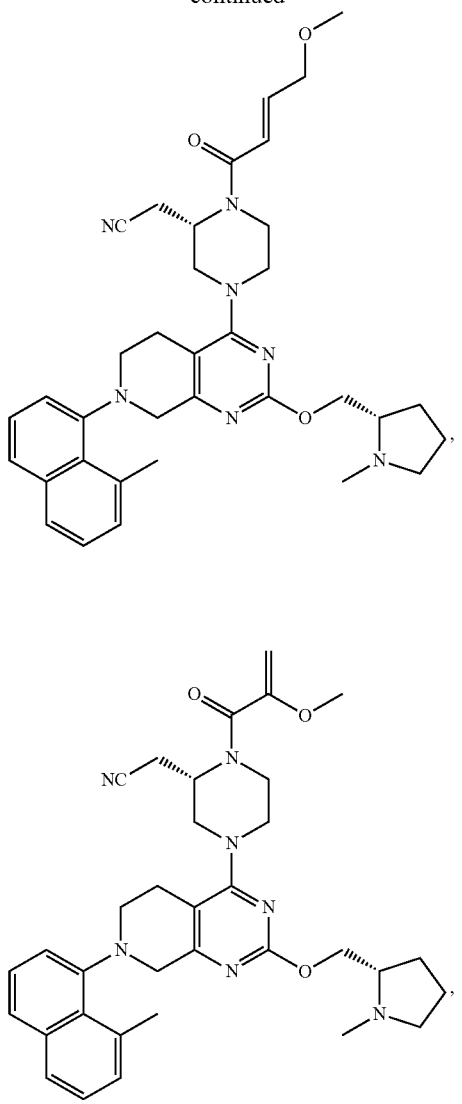
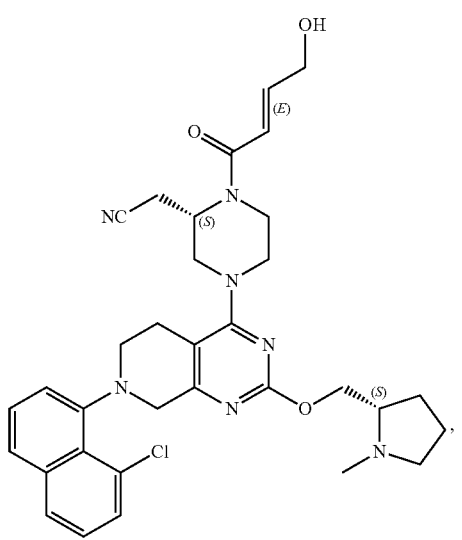

1677
-continued
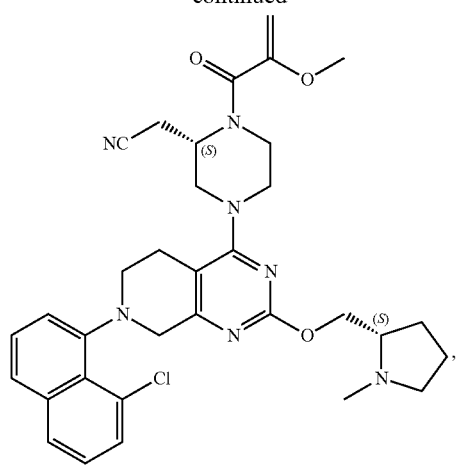
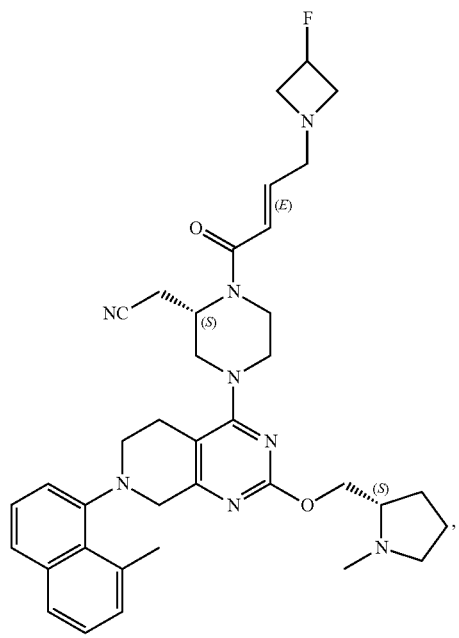
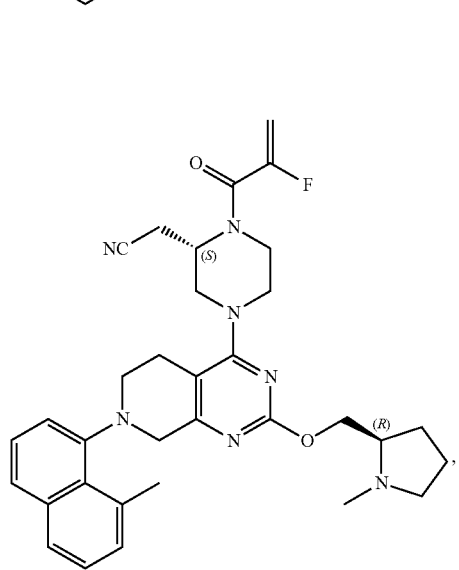
1678
-continued
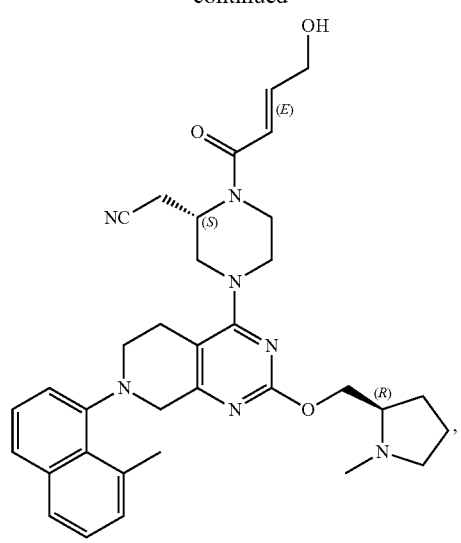
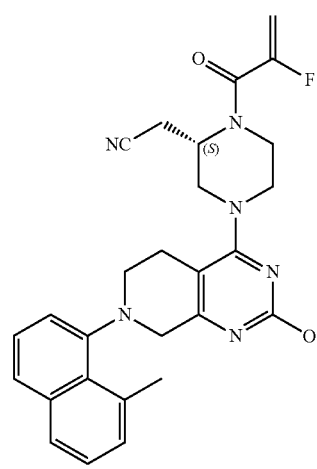
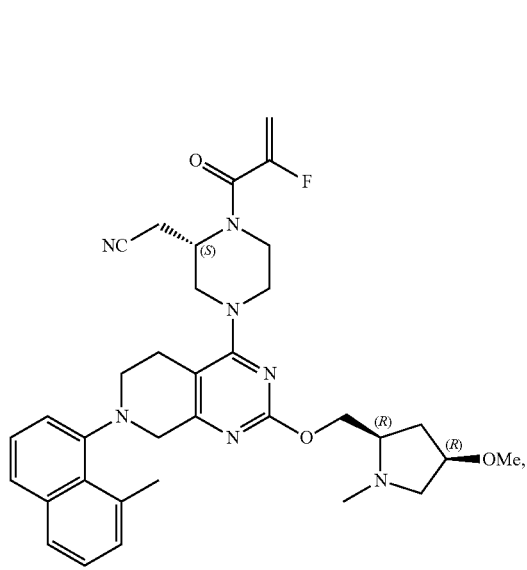

1679
-continued
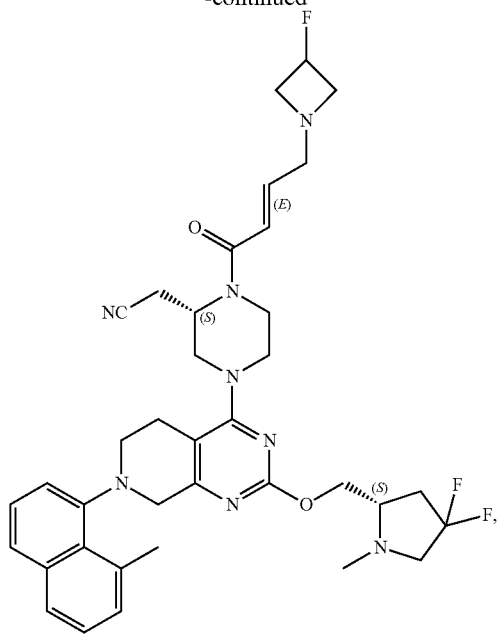
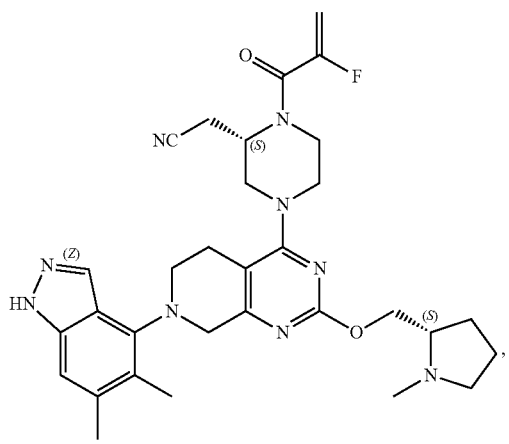
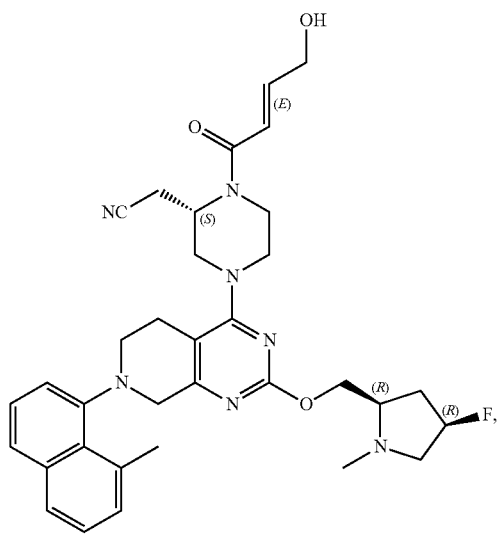
1680
-continued
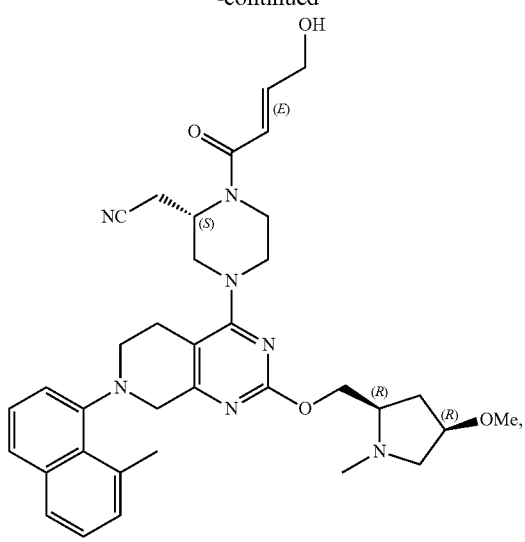
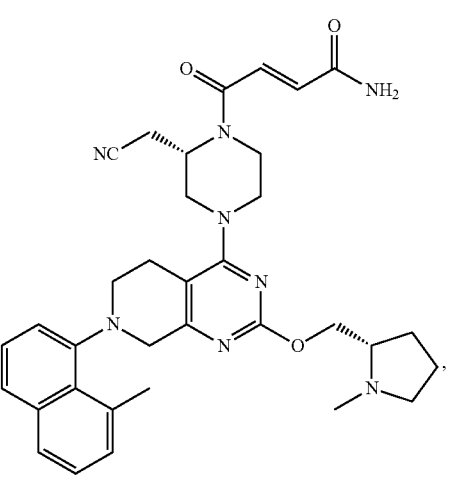
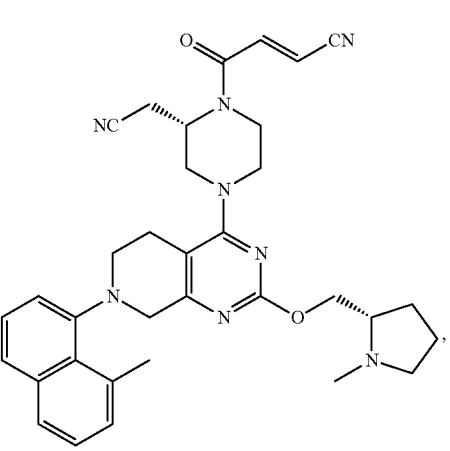

1681
-continued
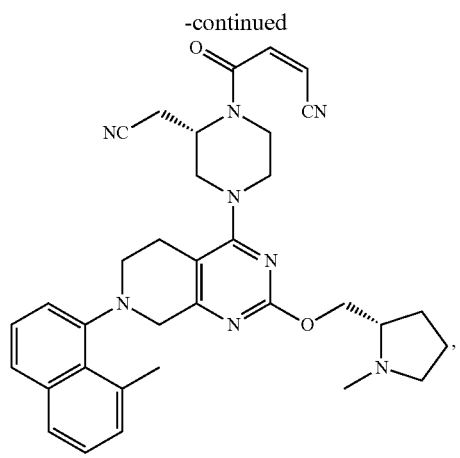
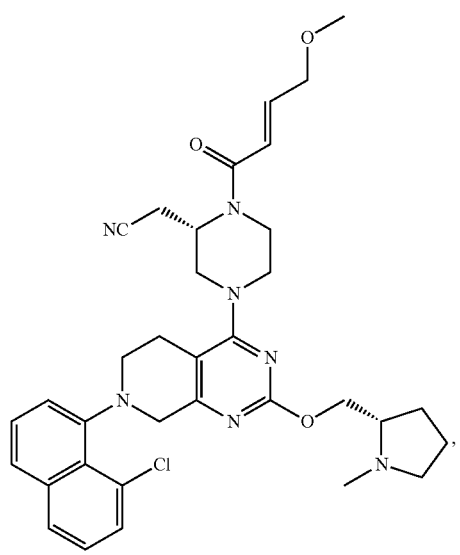
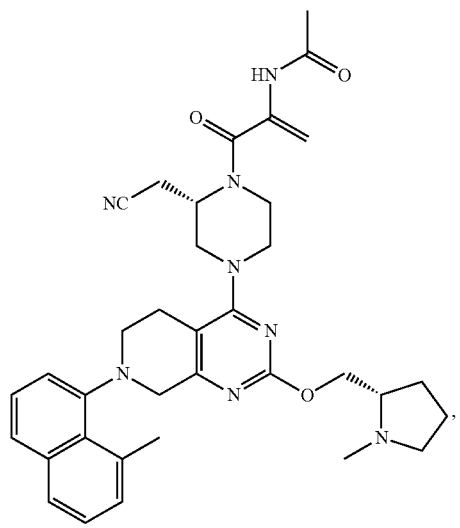
1682
-continued
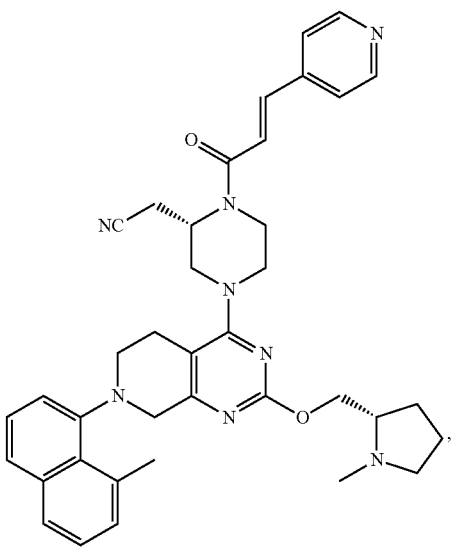
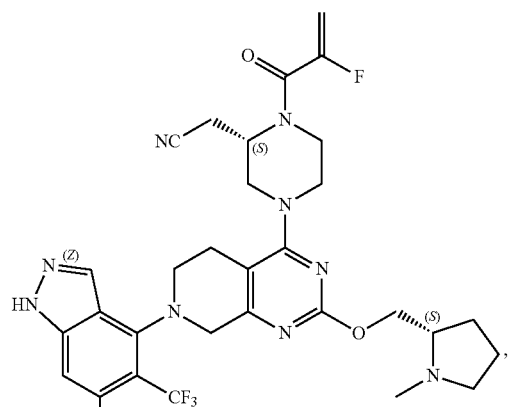
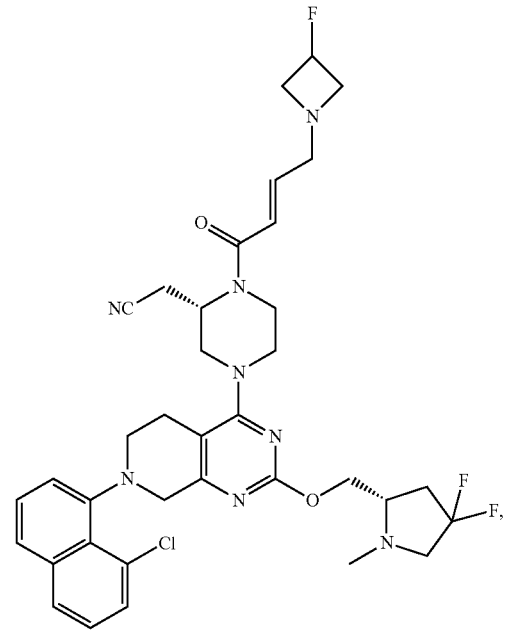

1683
-continued
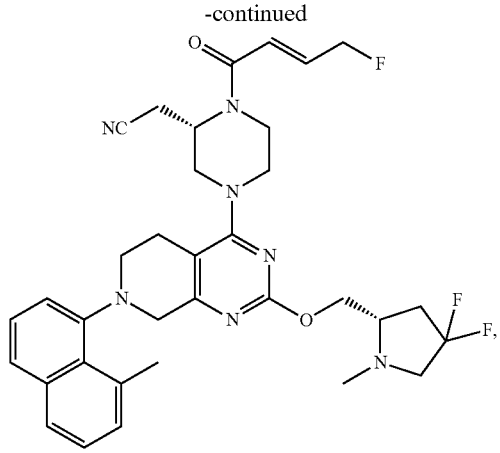
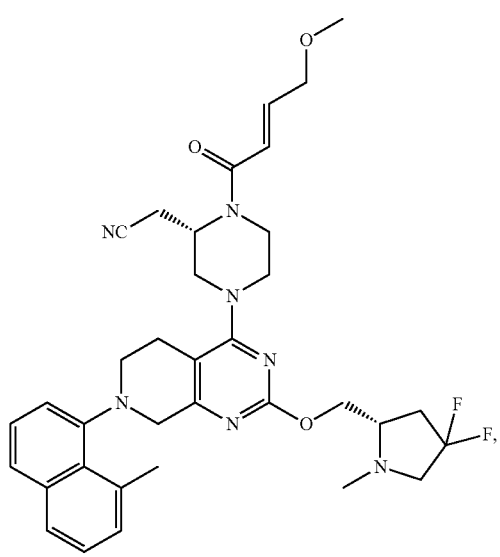
1684
-continued
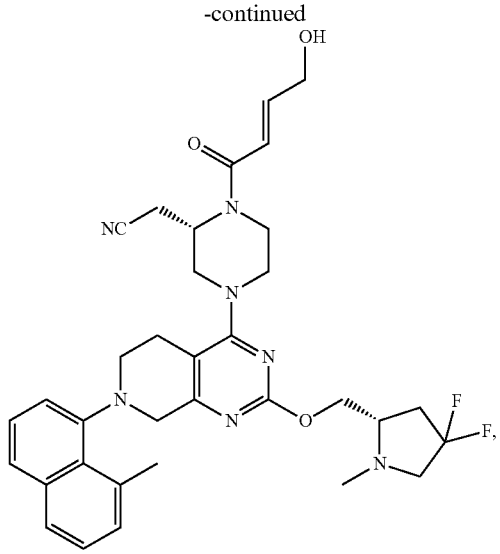
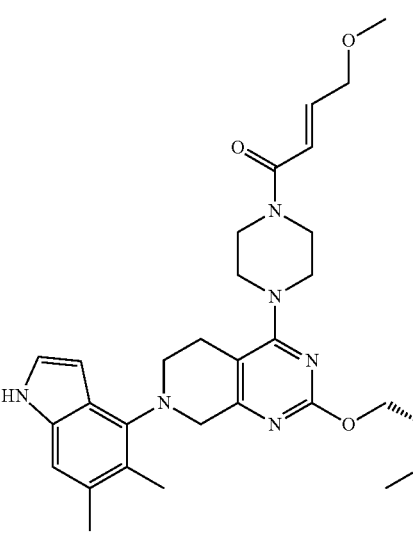

1685
-continued
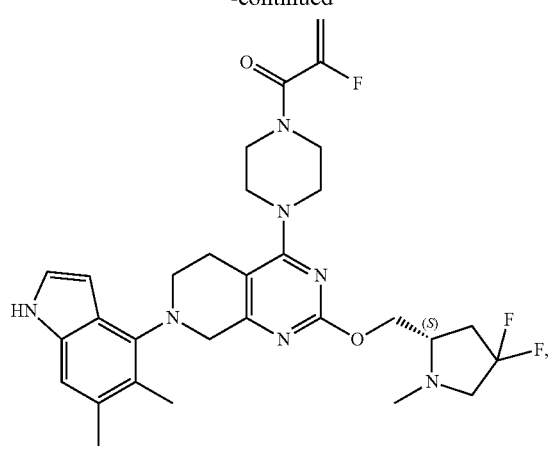
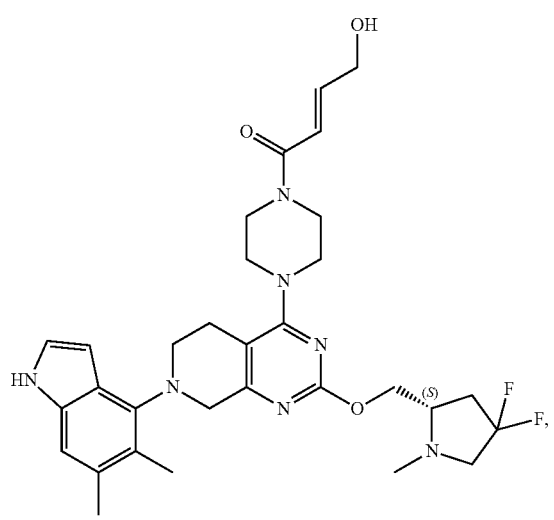
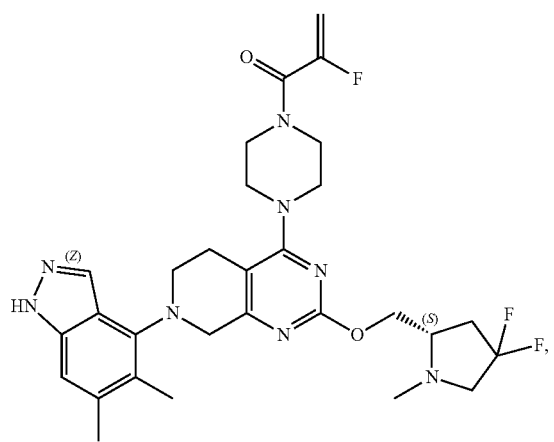
1686
-continued
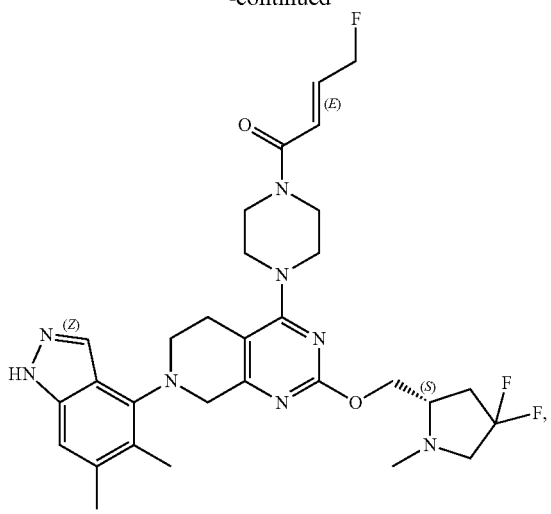
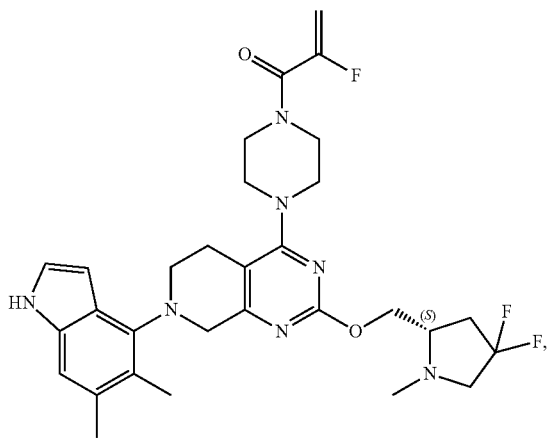
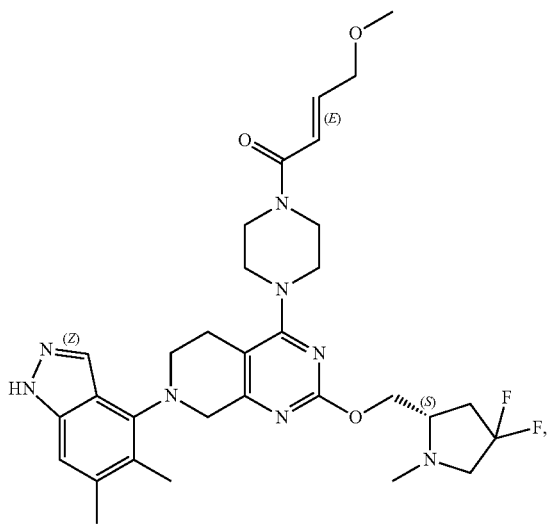

1687
-continued
1688
-continued
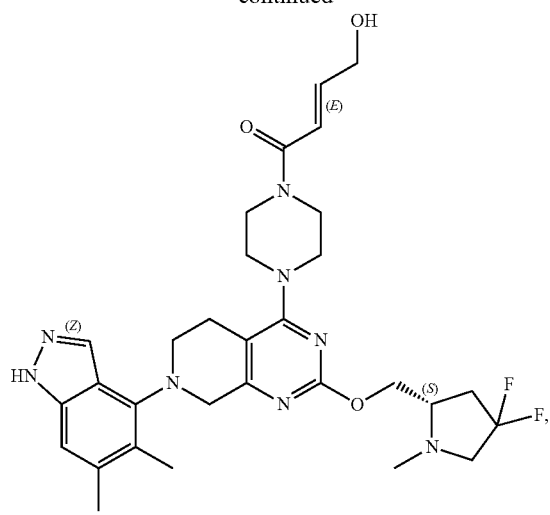
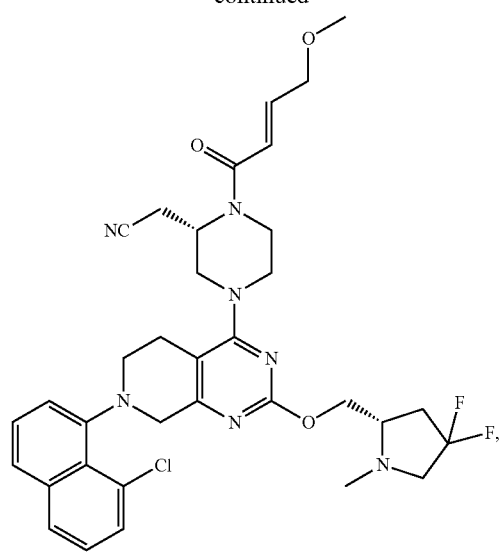
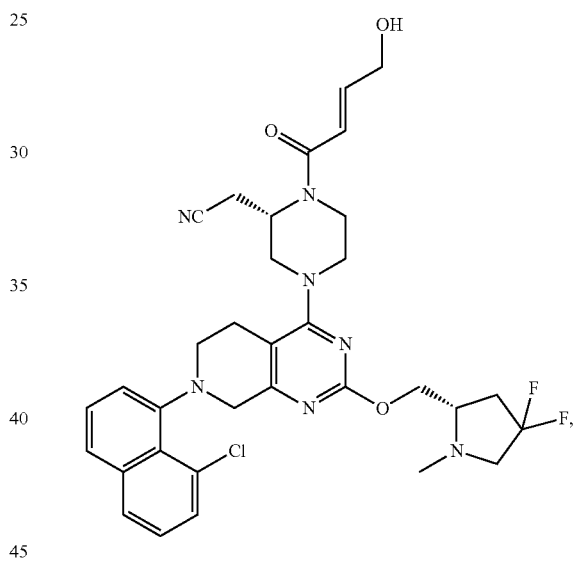
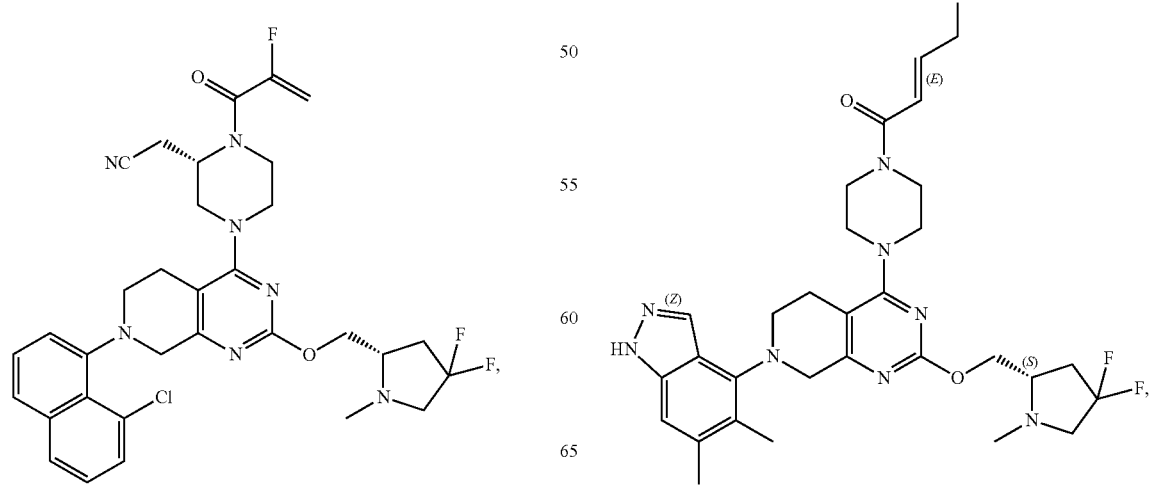

1689
-continued
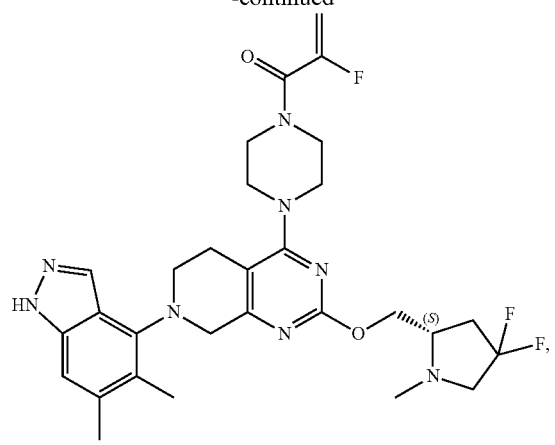
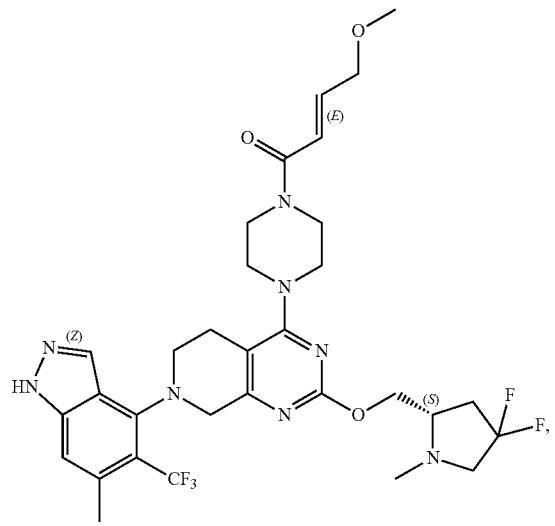
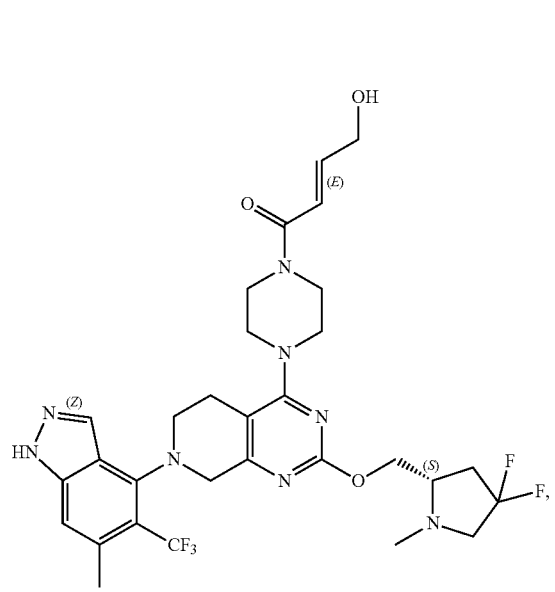
1690
-continued
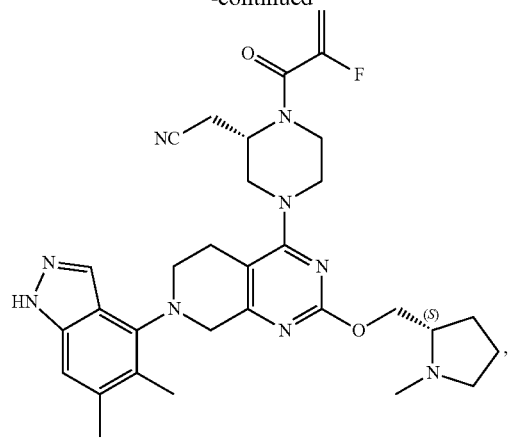
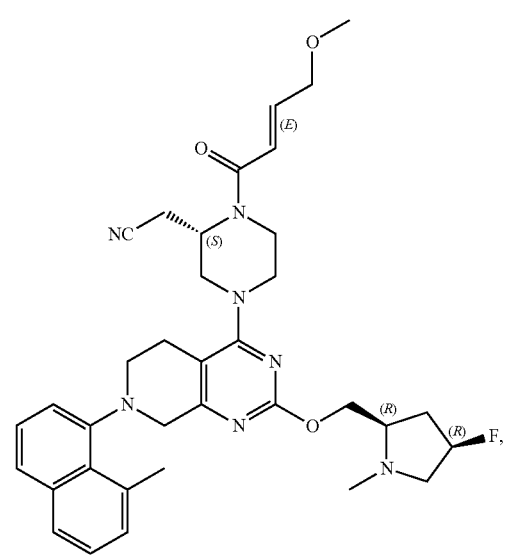
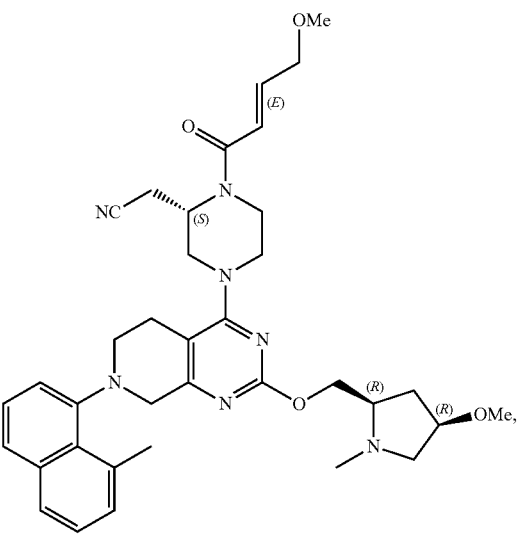

1691
-continued
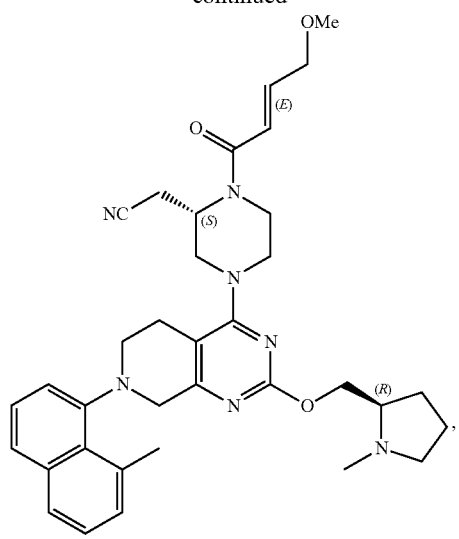
1692
-continued
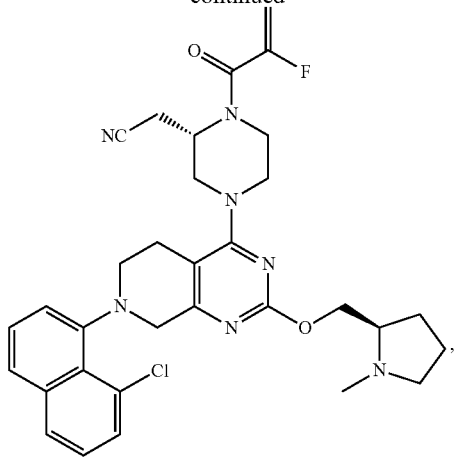
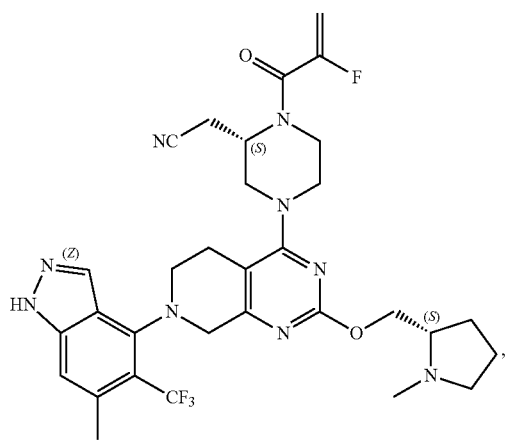
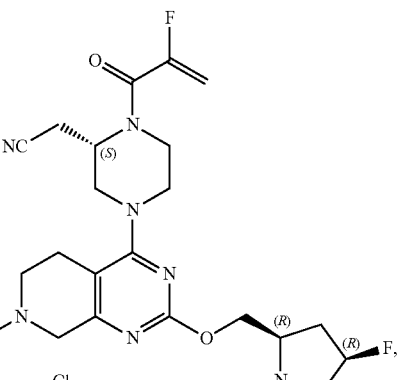
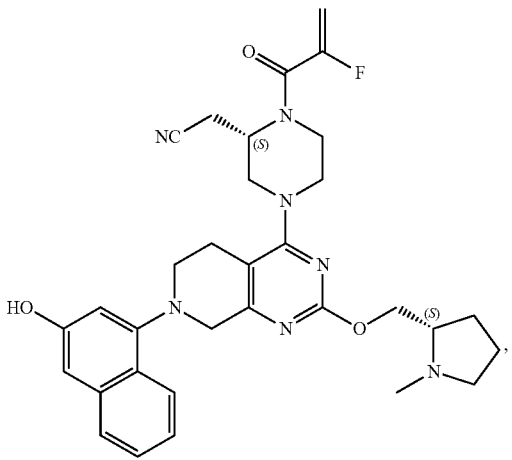
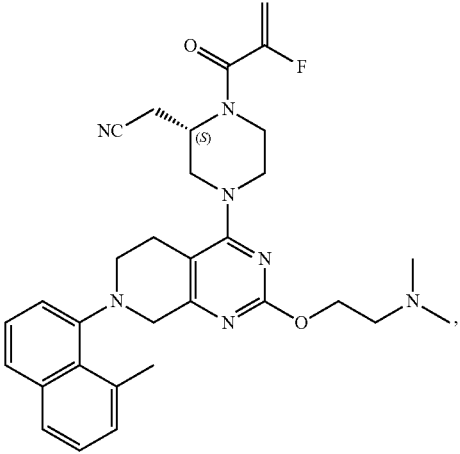

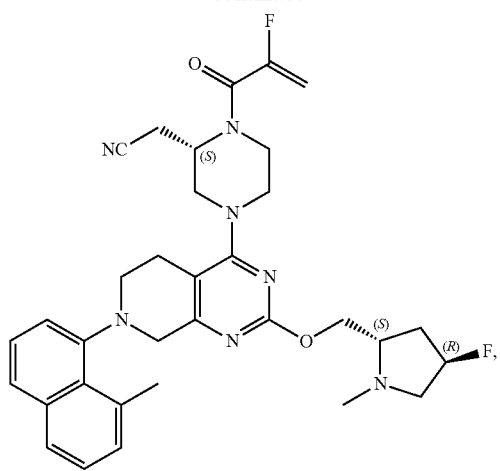
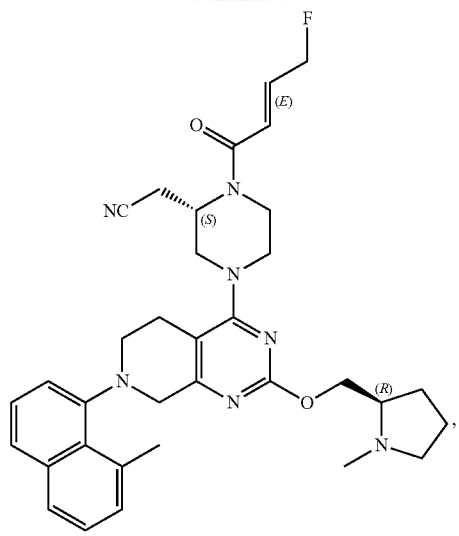
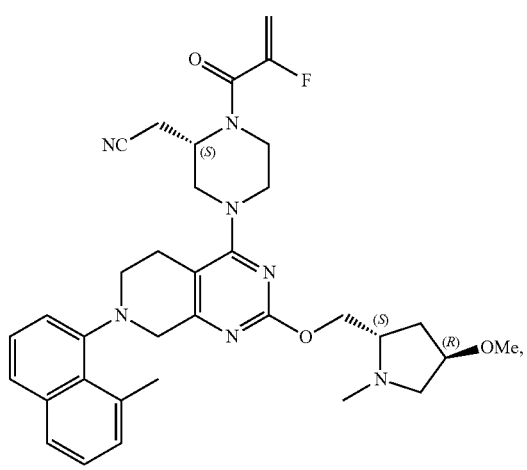
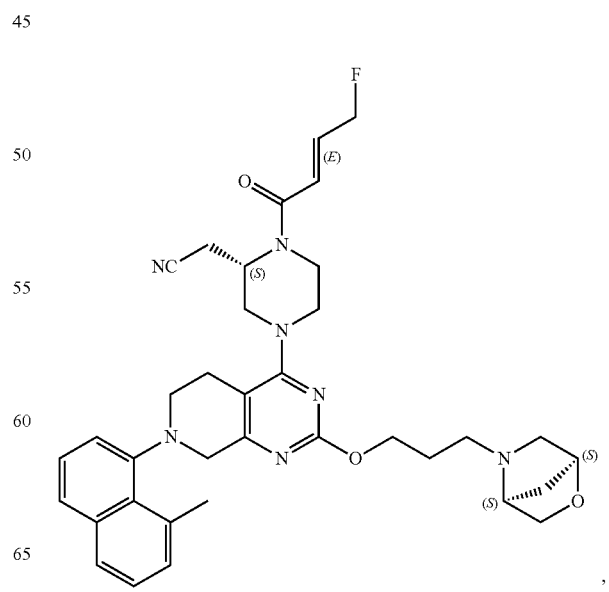

1695
-continued
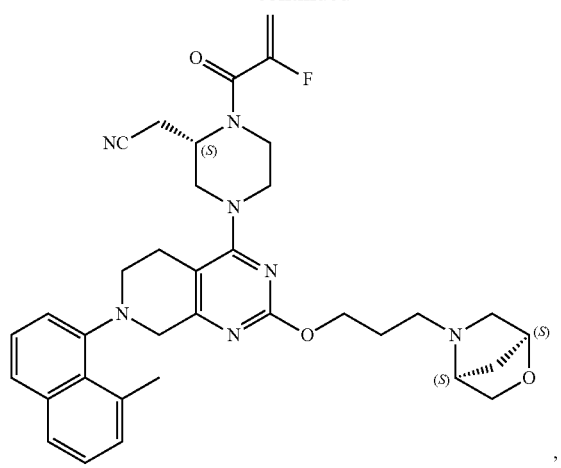,
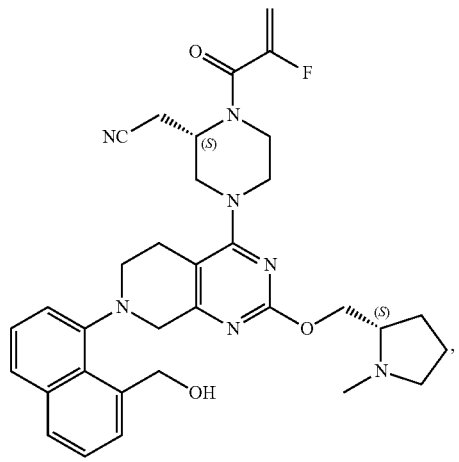,
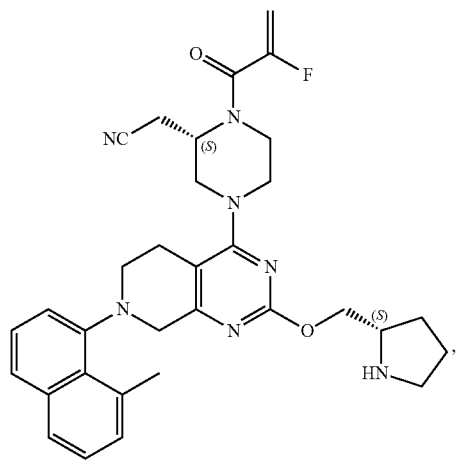,
1696
-continued
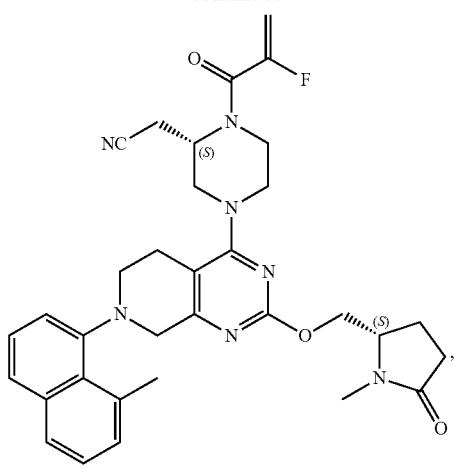,
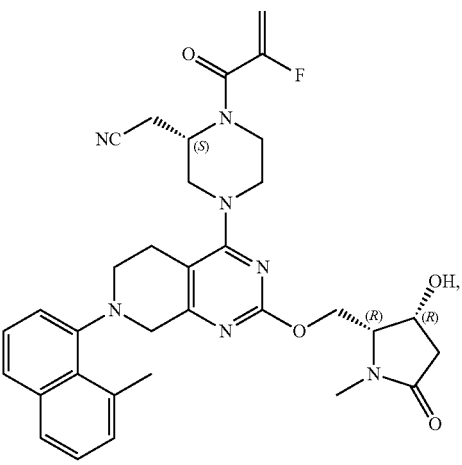,
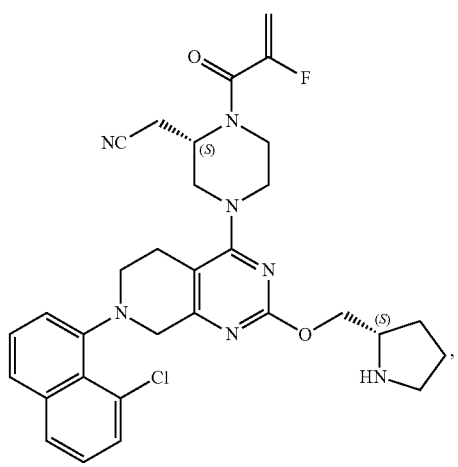, 1697
-continued
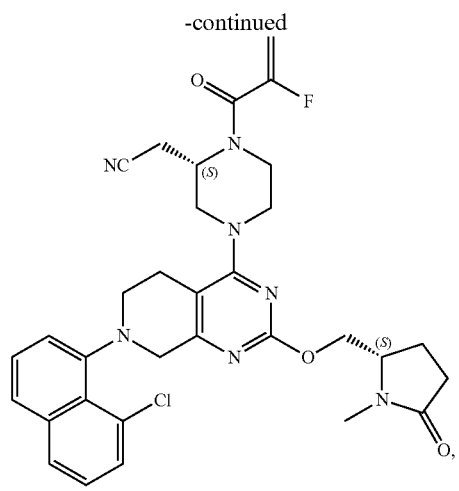
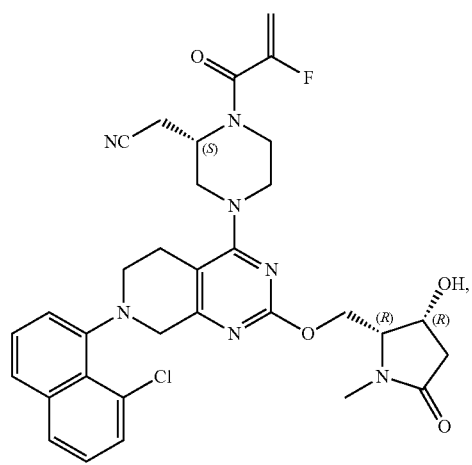
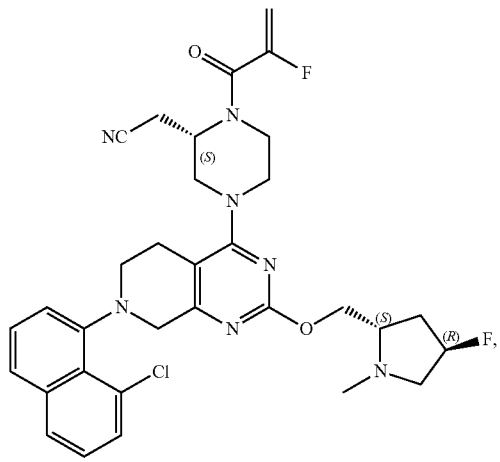
1698
-continued
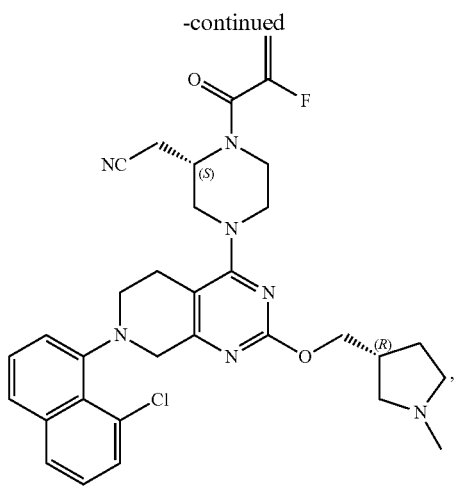
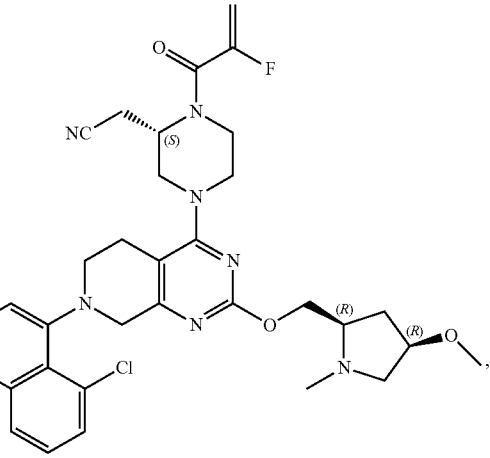
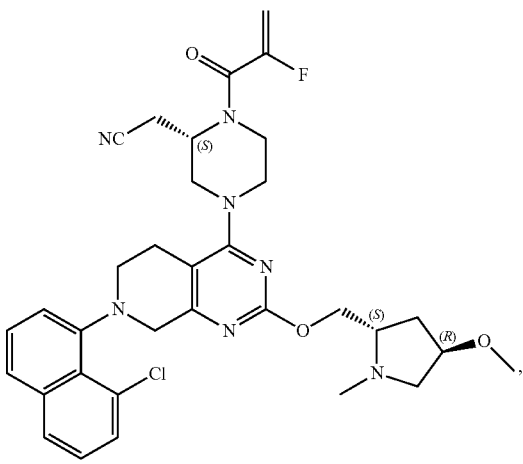

1699 1700
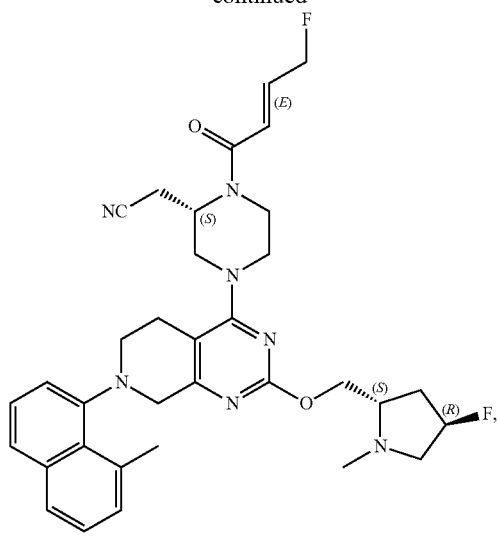,
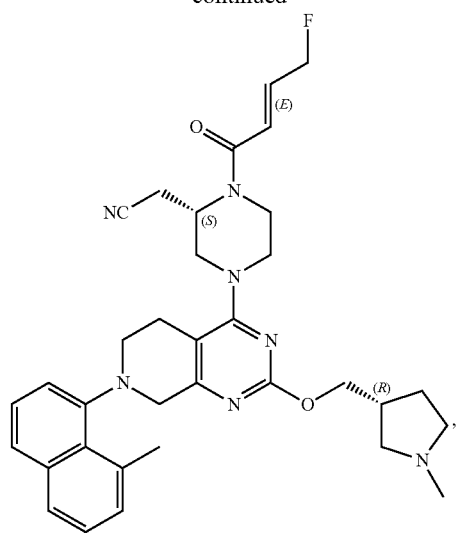,
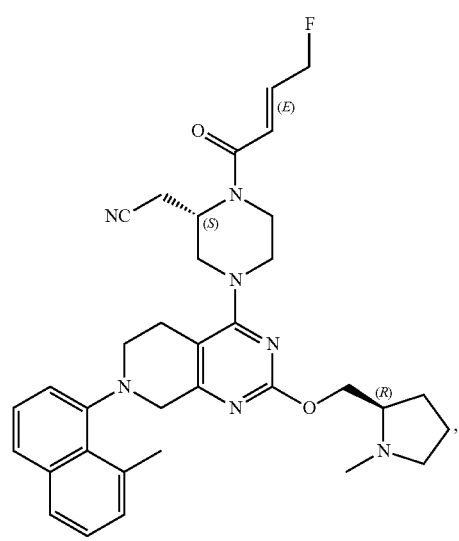,
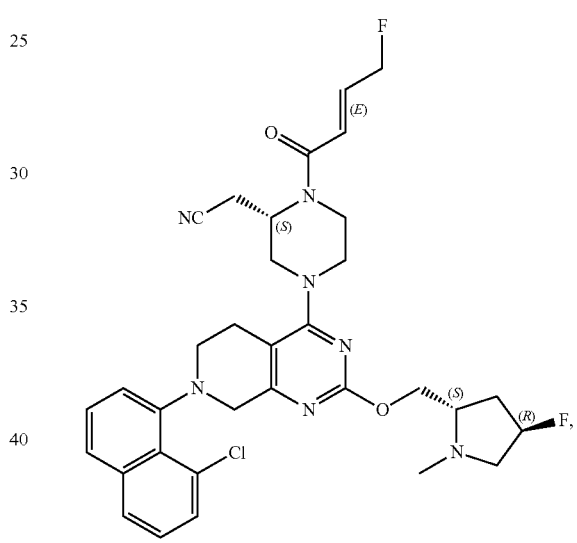,
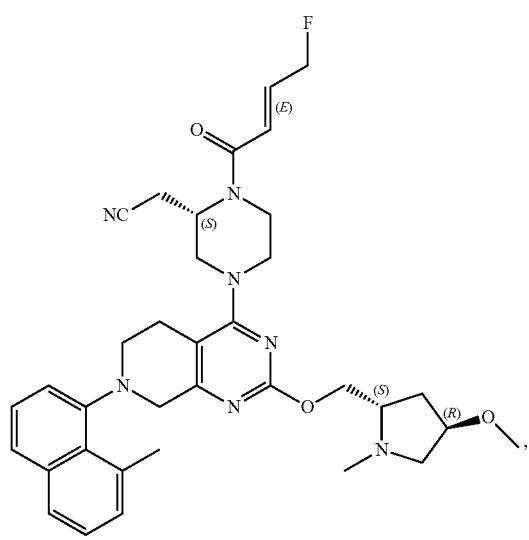,
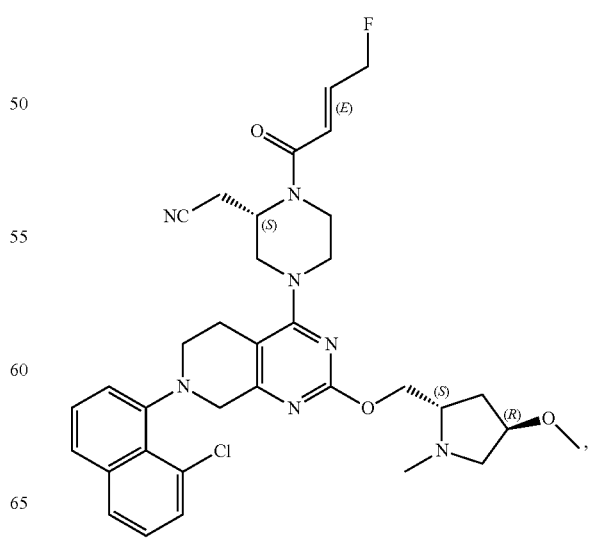, 1701
-continued
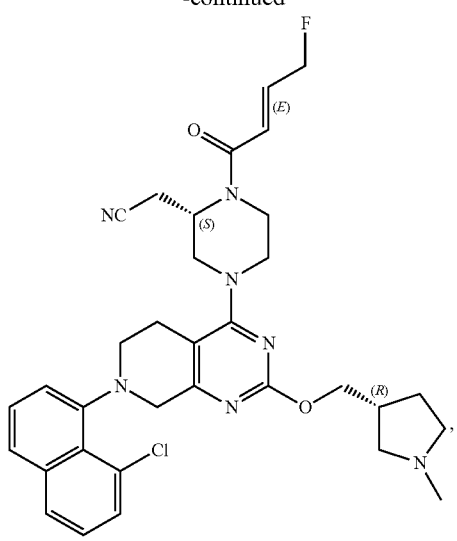
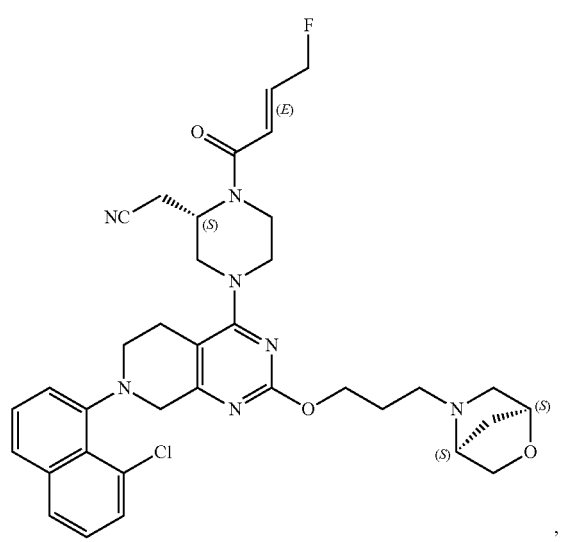
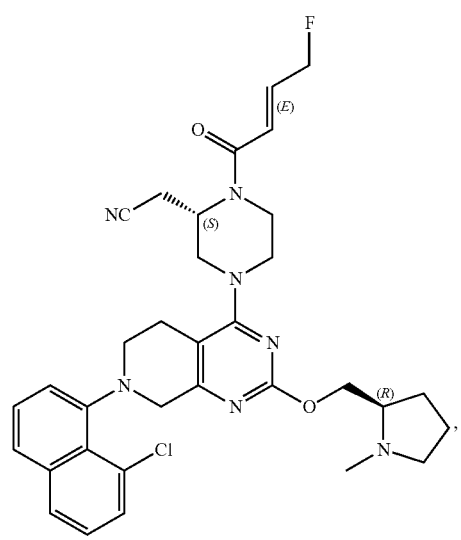
1702
-continued
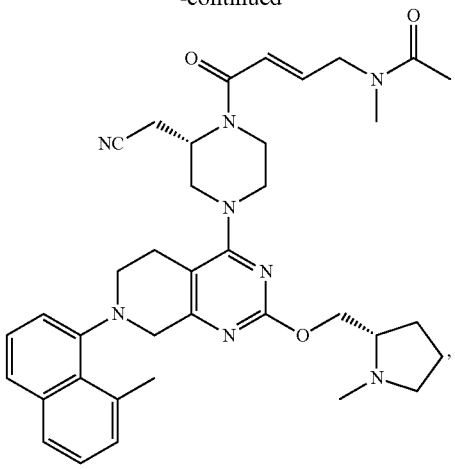
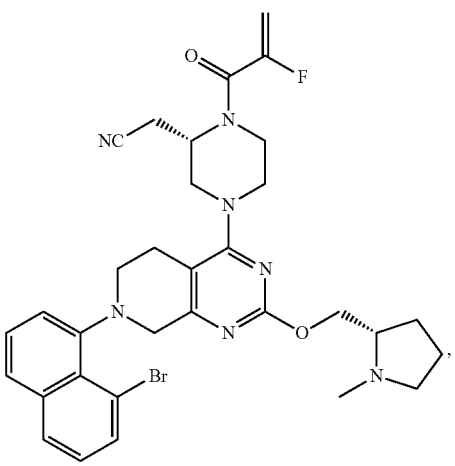
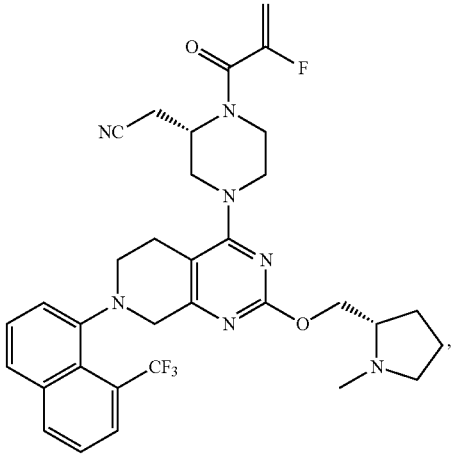

1703
-continued
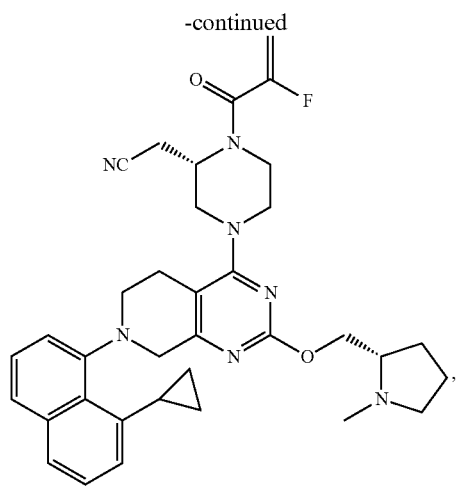
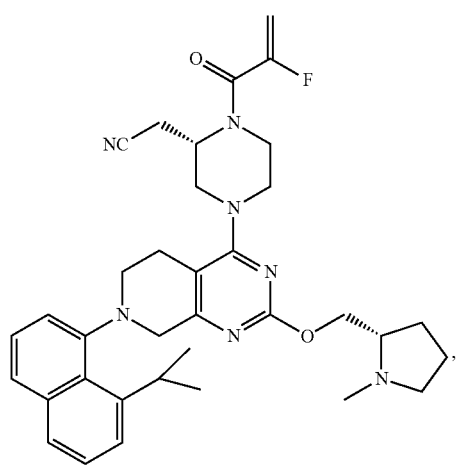
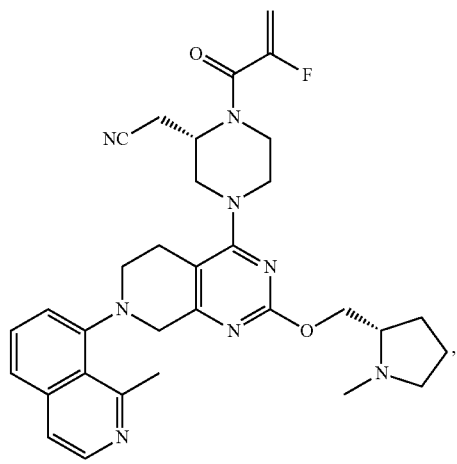
1704
-continued
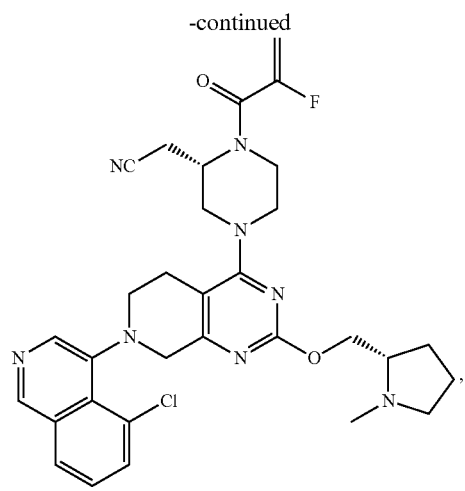
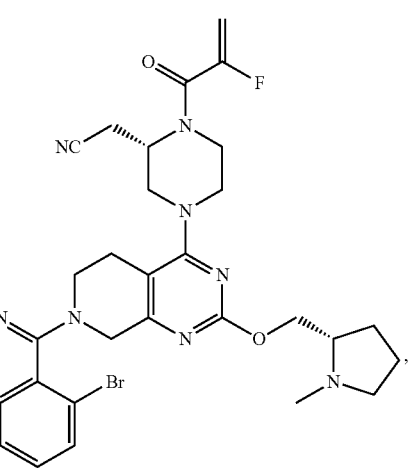
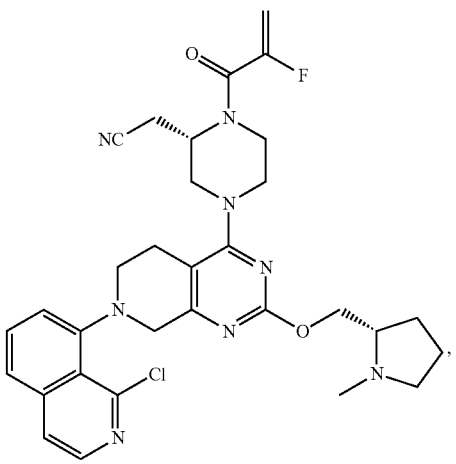

1705
-continued
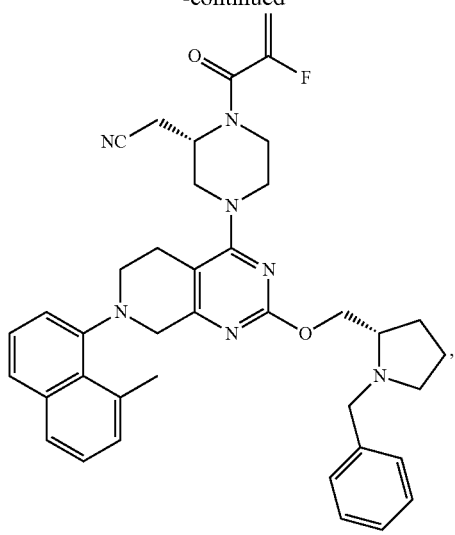
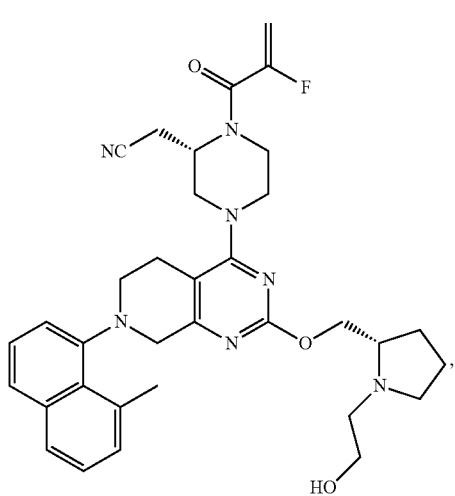
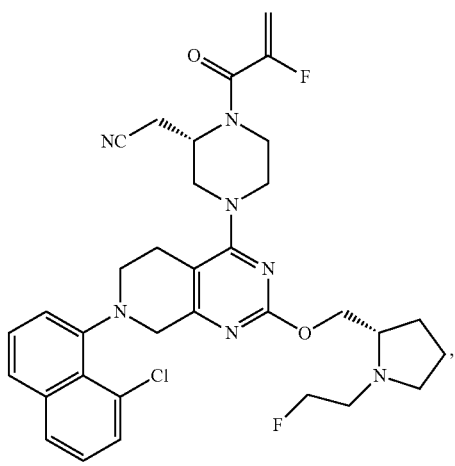
1706
-continued
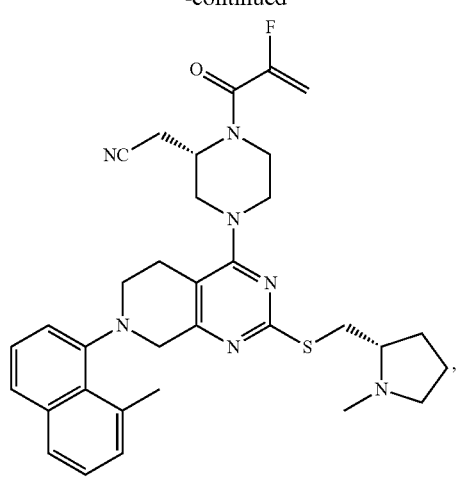
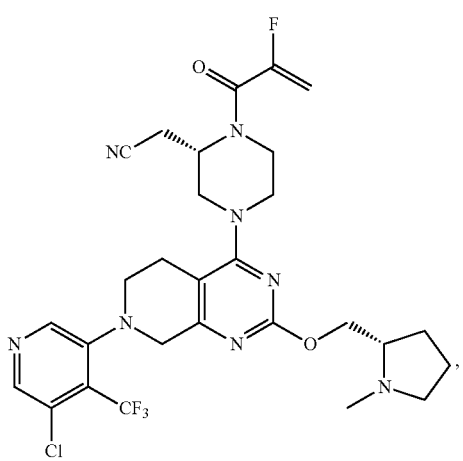
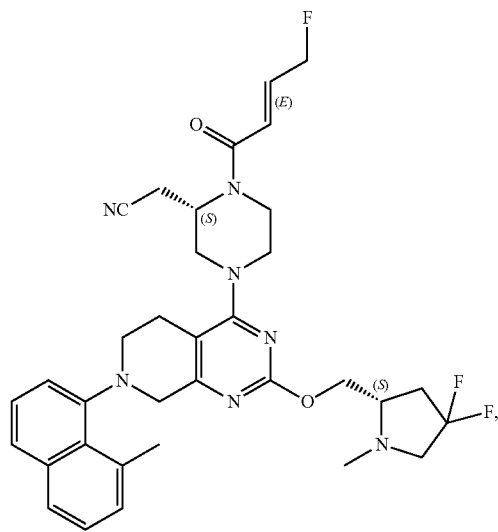

1707
-continued
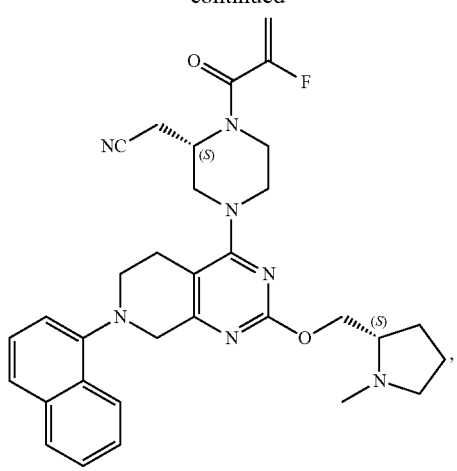
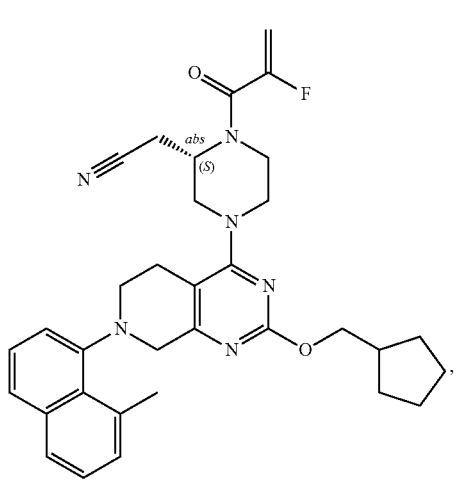
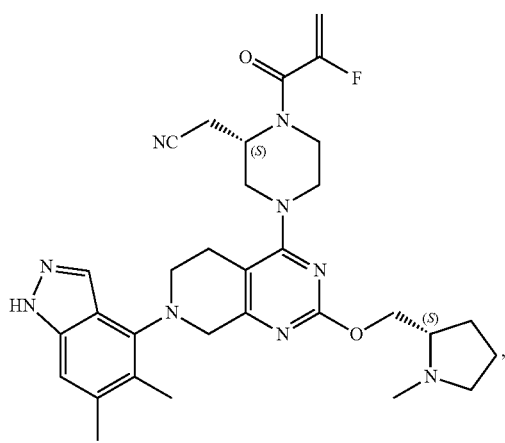
1708
-continued
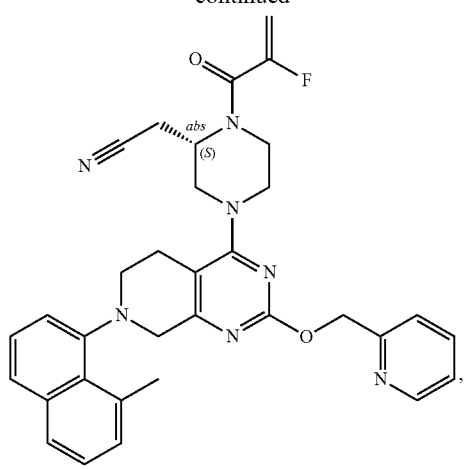
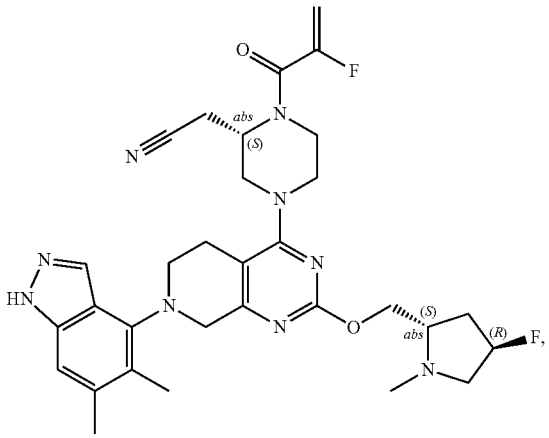
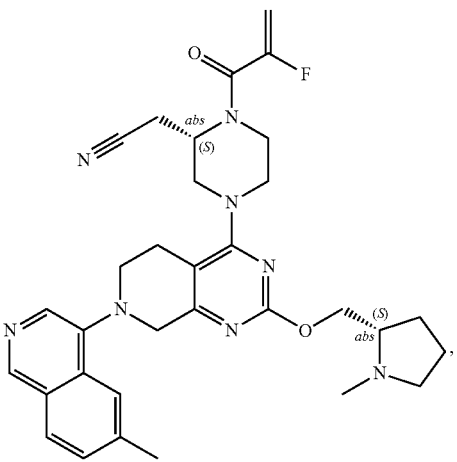

1709
-continued
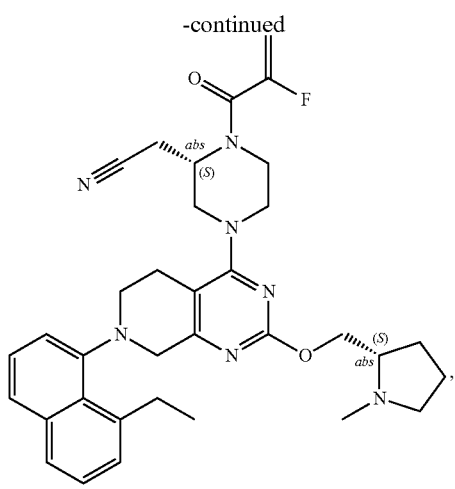
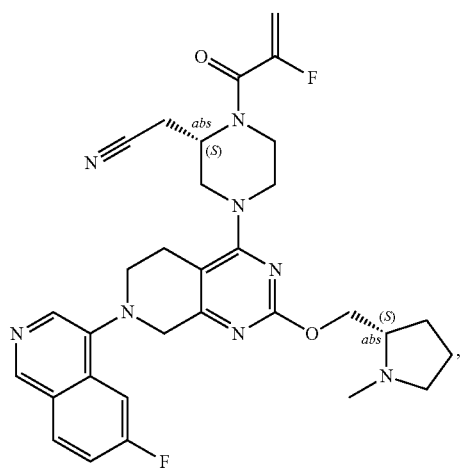
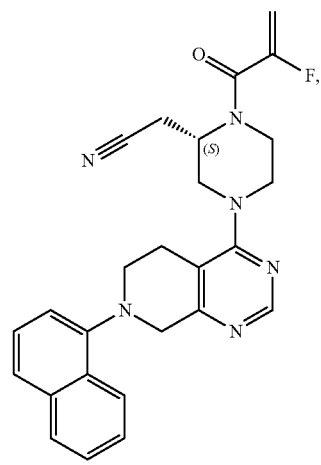
1710
-continued
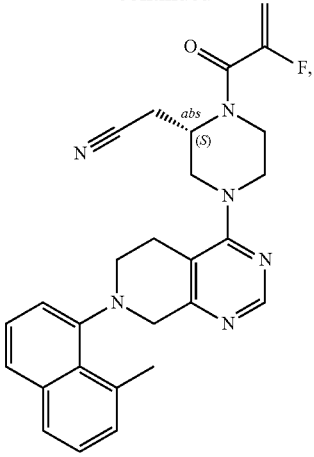
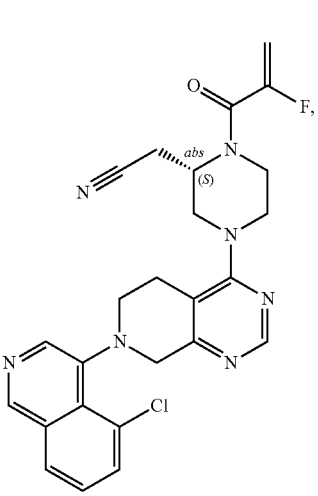
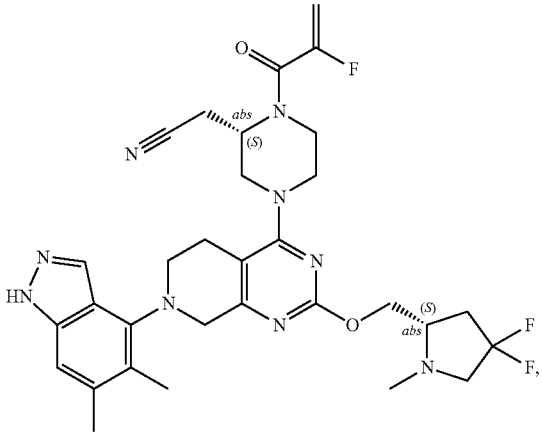

1711
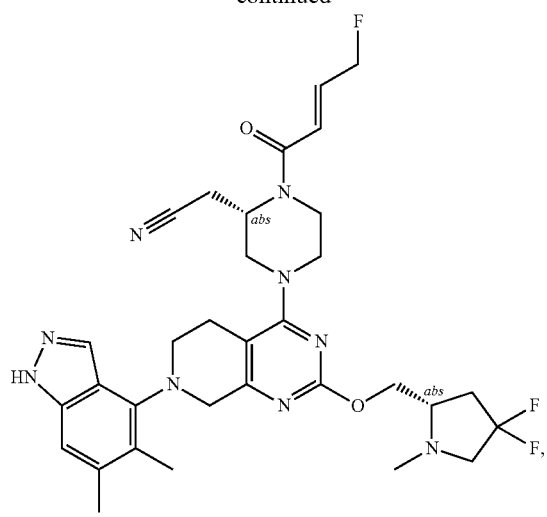
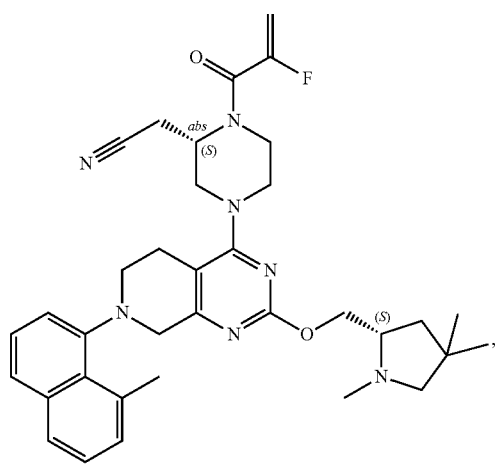
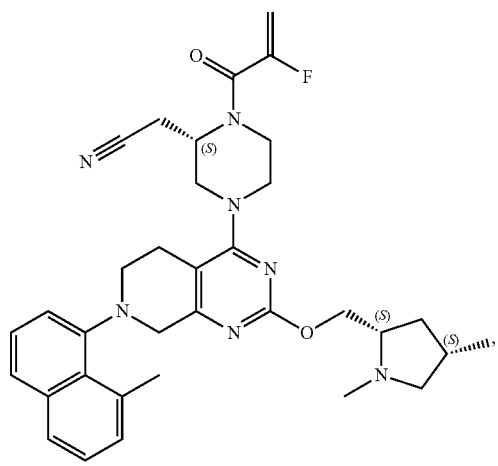
1712
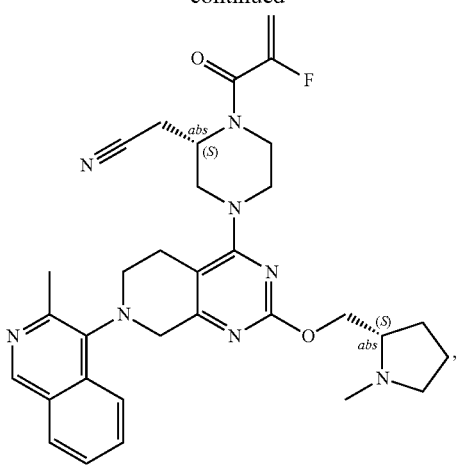
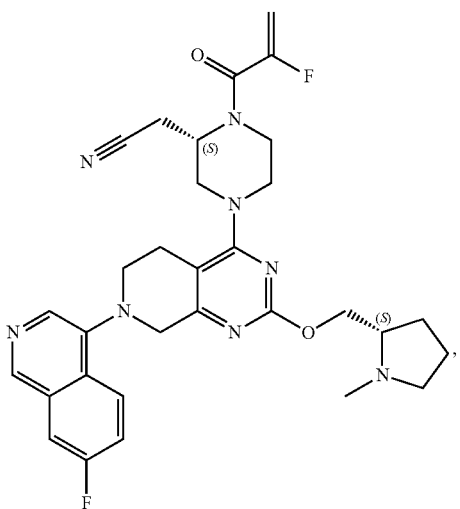
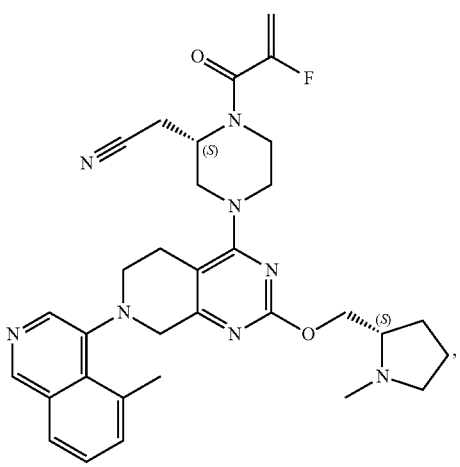

1713
-continued
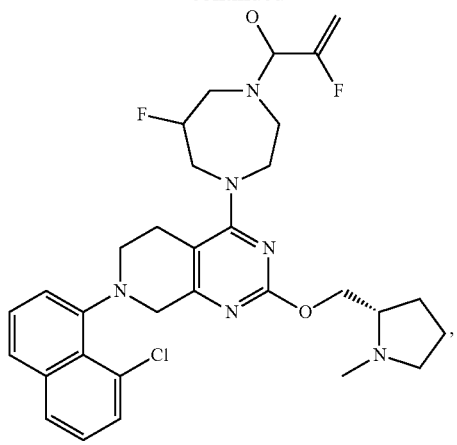
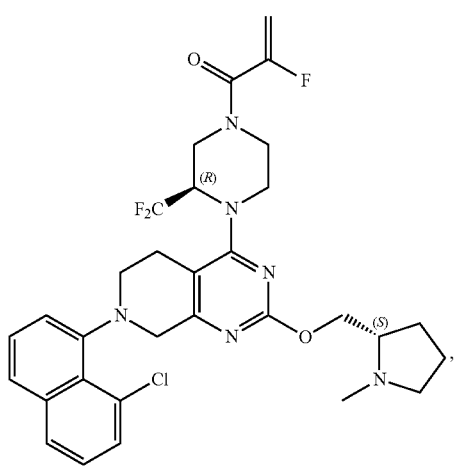
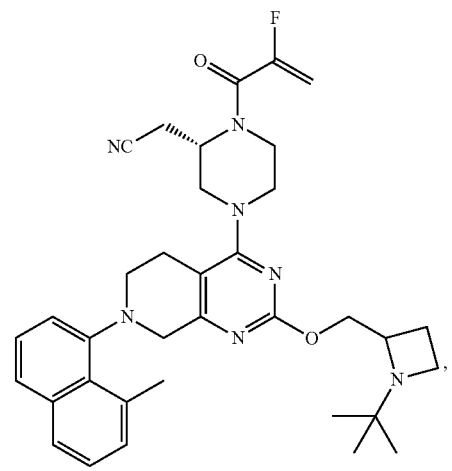
1714
-continued
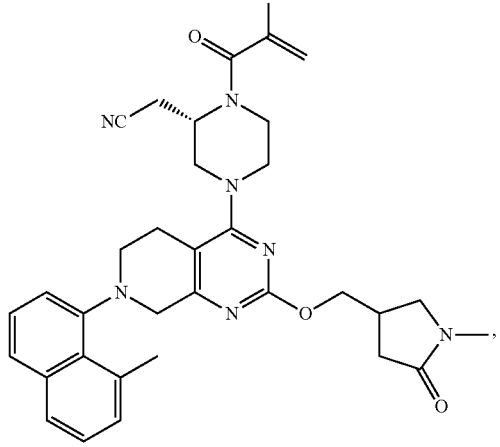
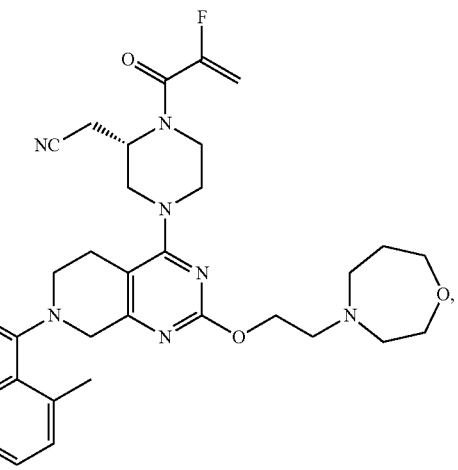
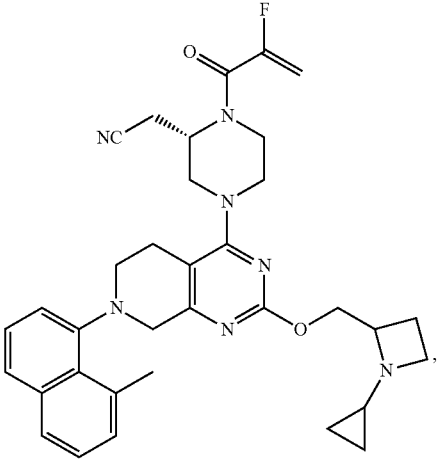

1715
-continued
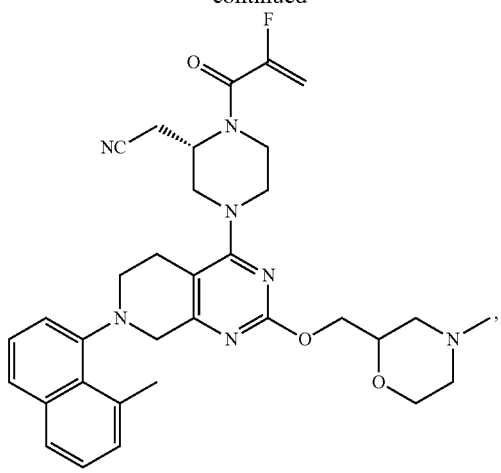
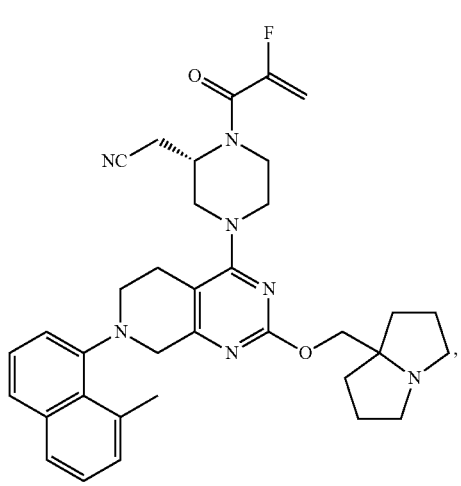
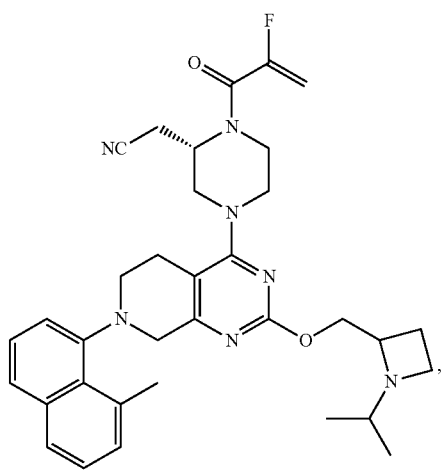
1716
-continued
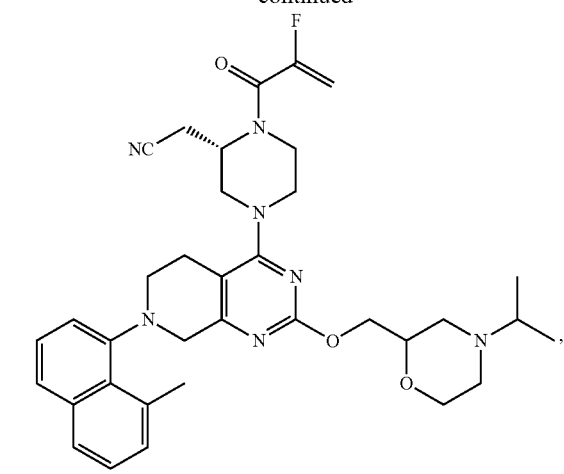
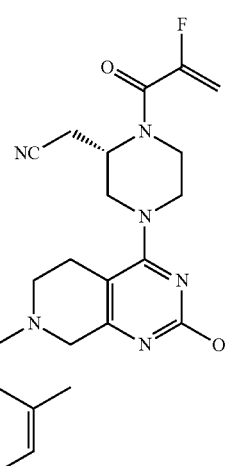
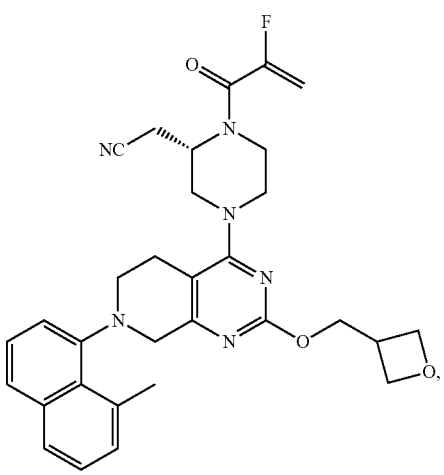

1717
-continued
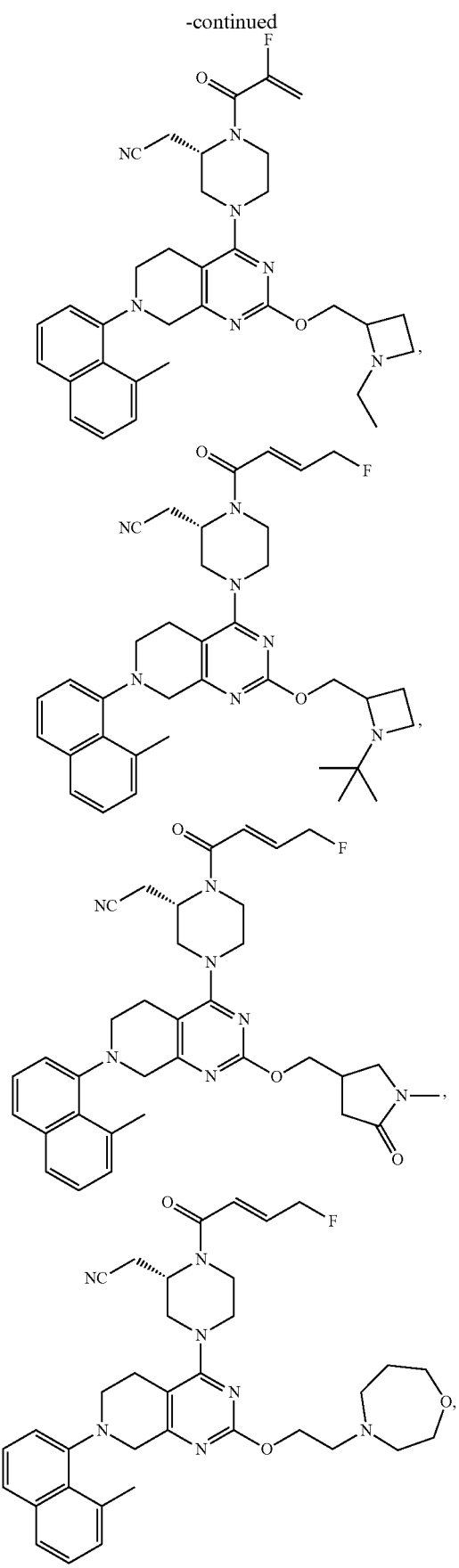
1718
-continued
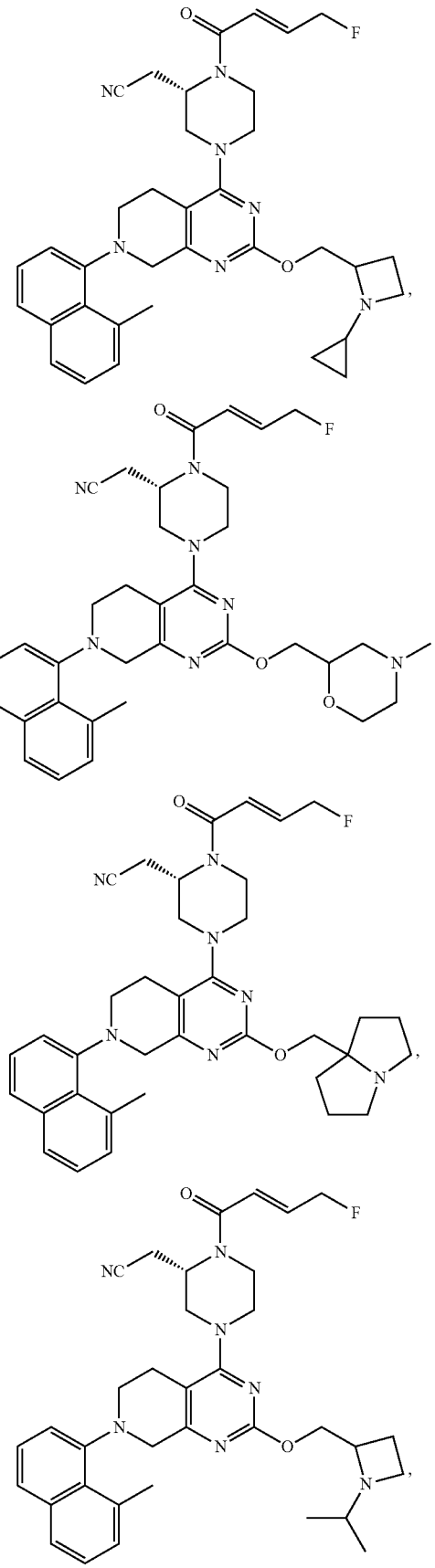

1719
-continued
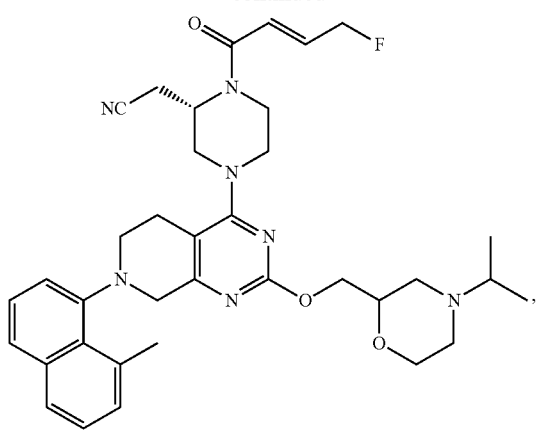
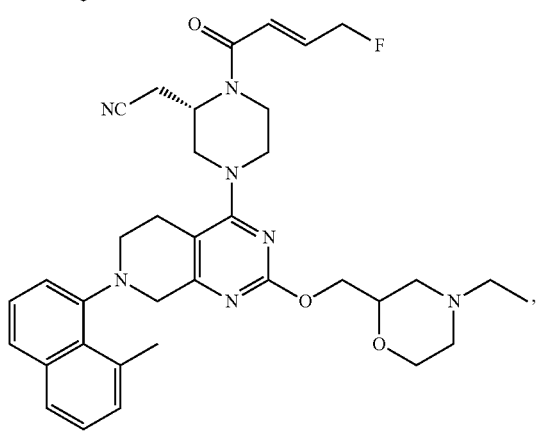
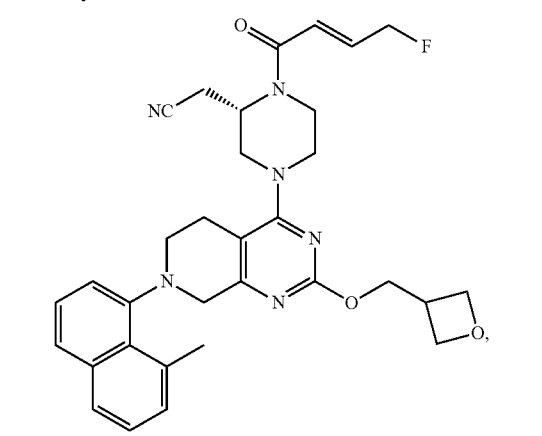
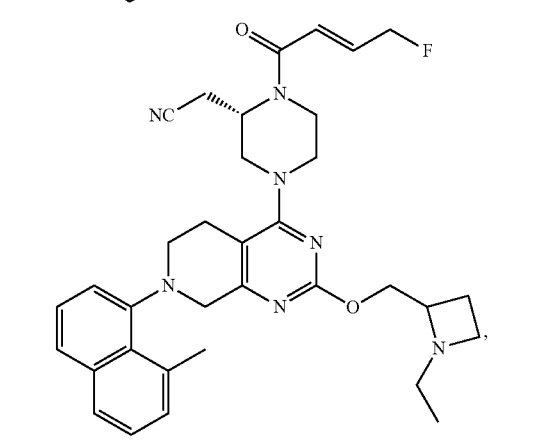
1720
-continued
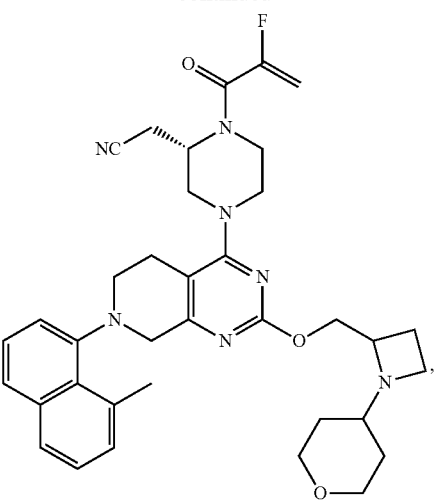
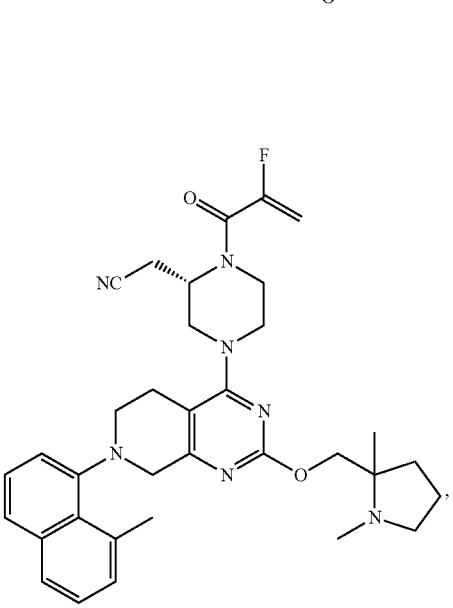
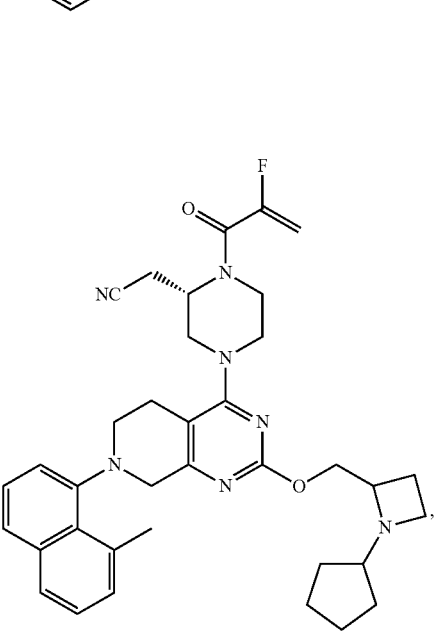

1721
-continued
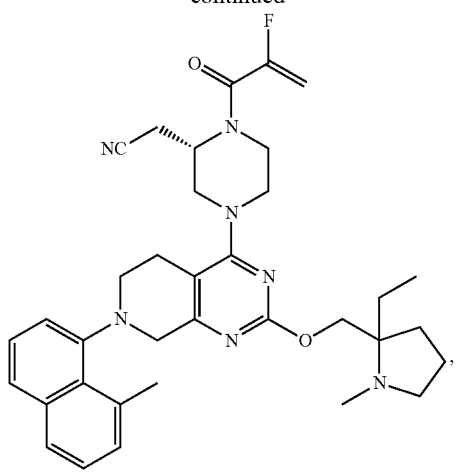
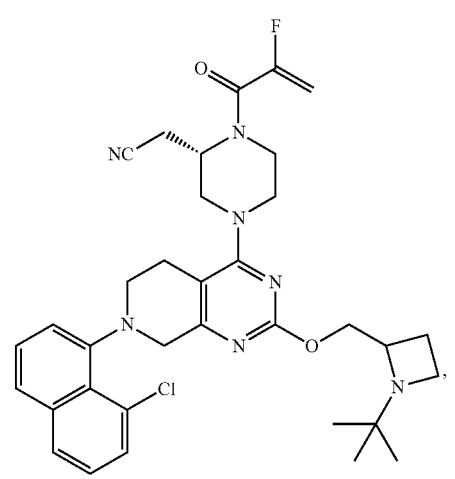
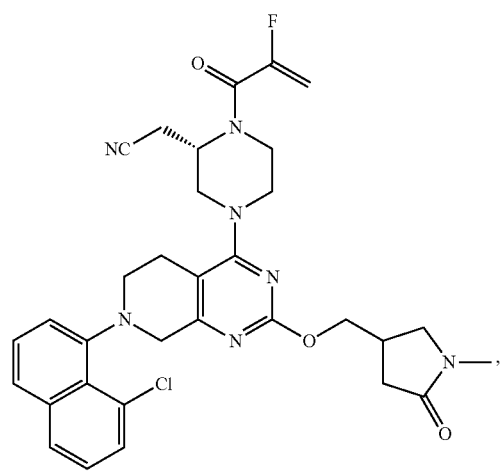
1722
-continued
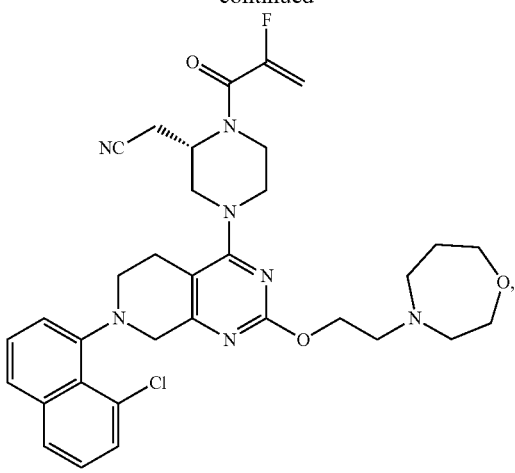
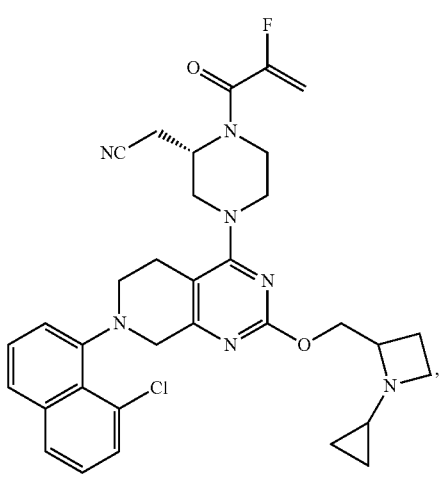
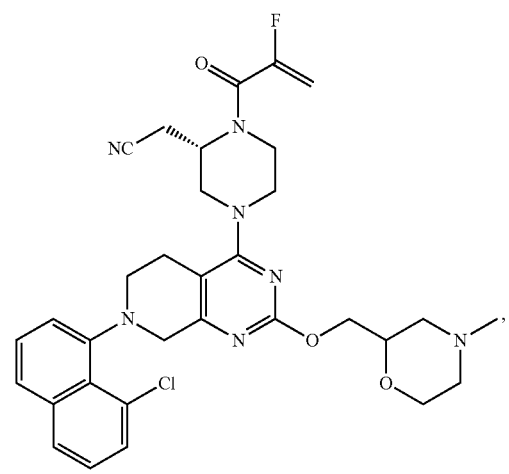

1723
-continued
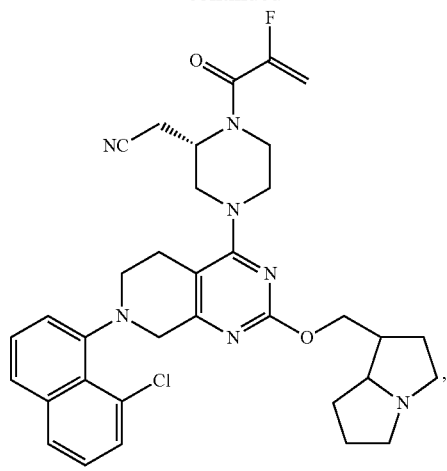
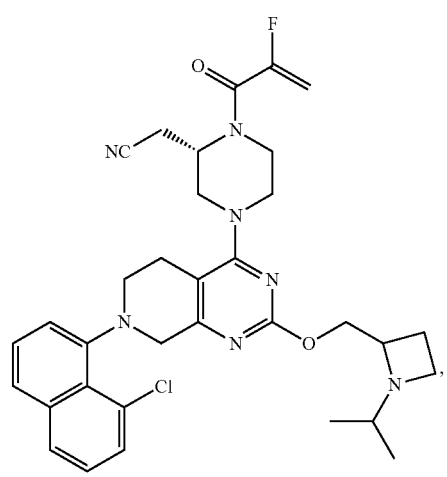
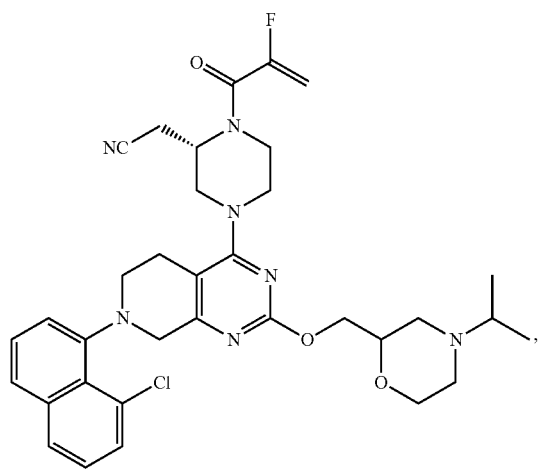
1724
-continued
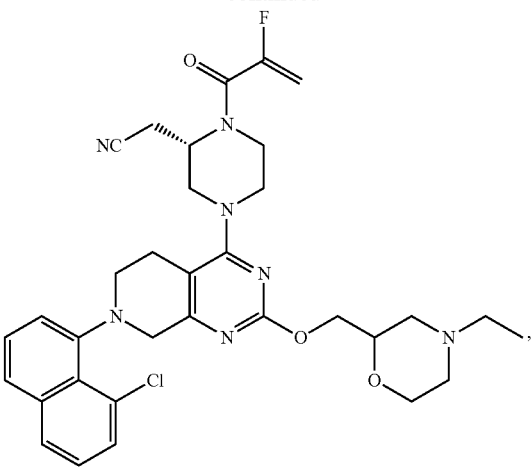
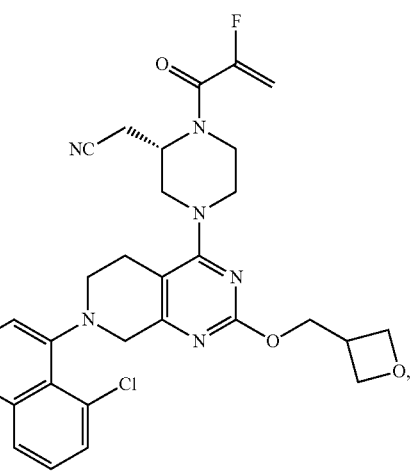
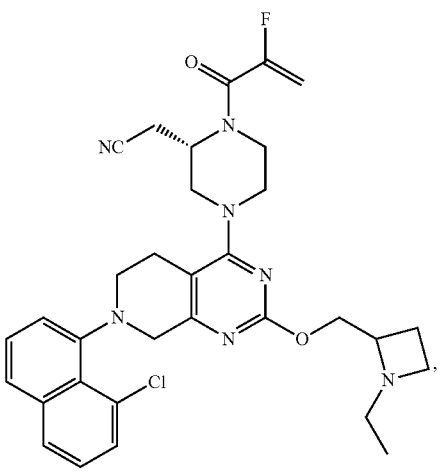

1725
-continued
1726
-continued
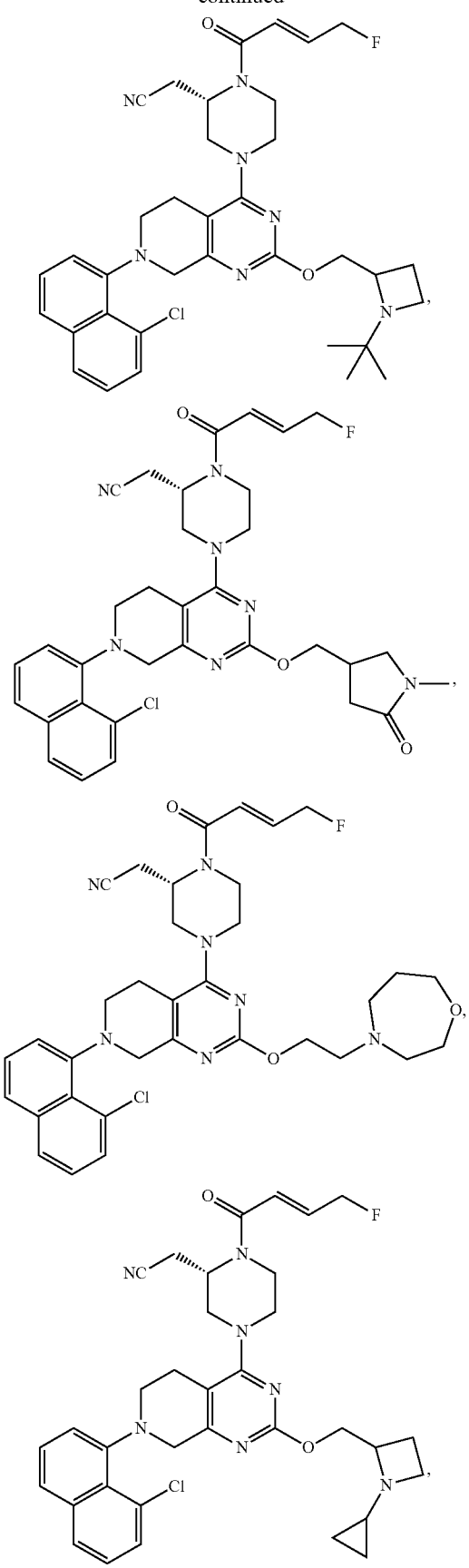
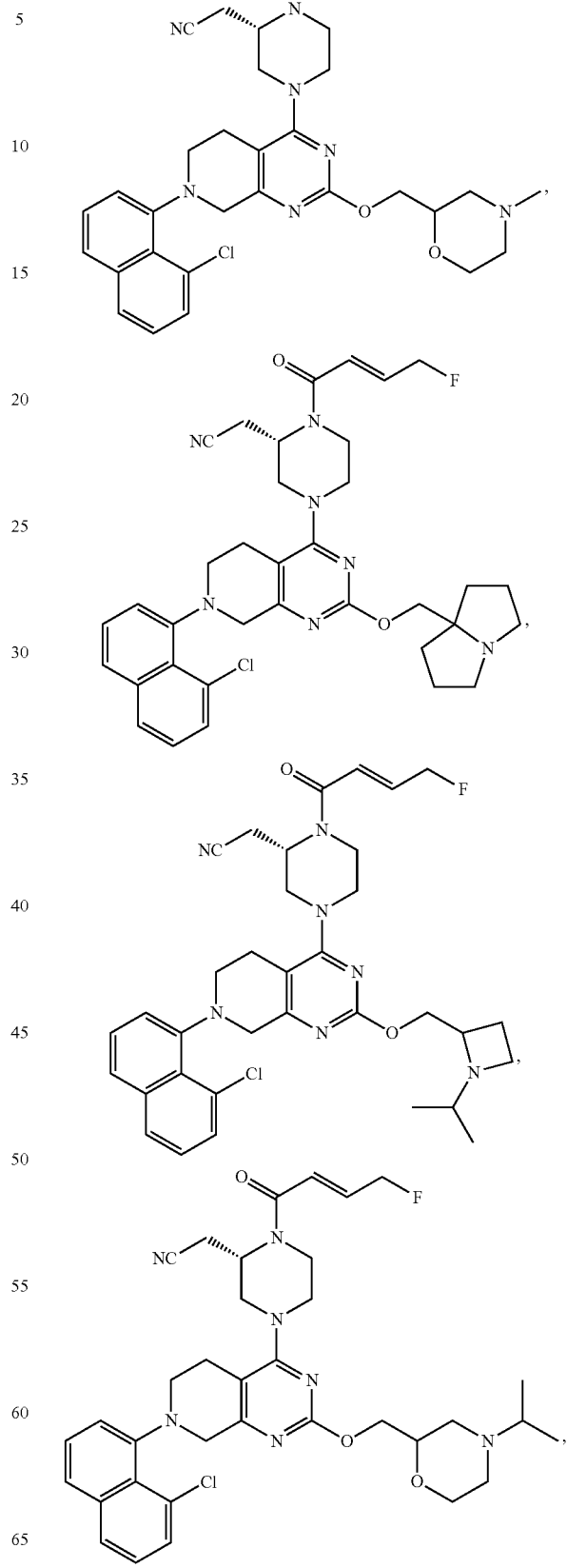

1727
-continued

1728
-continued

-continued

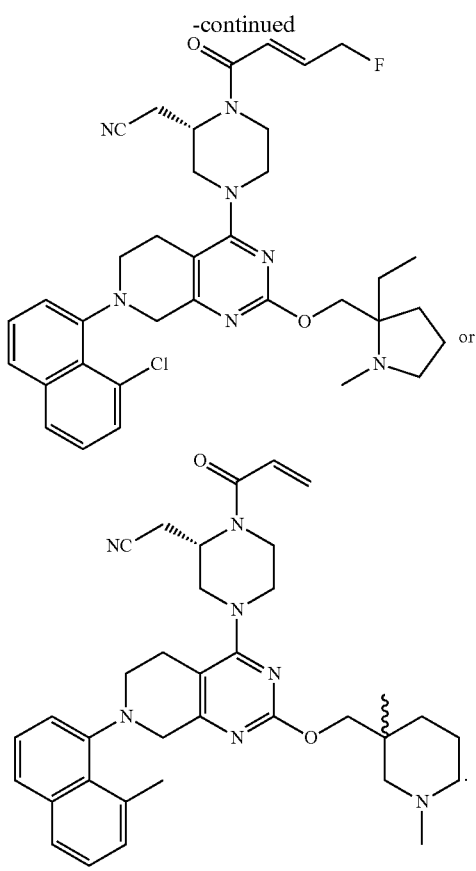

46. The compound of claim 1, wherein the compound is of Formula II-B:

Formula II-B

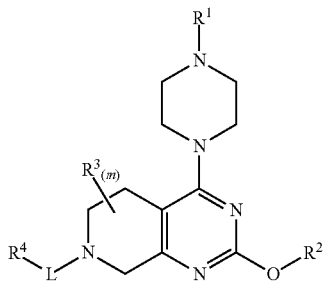

where the piperazinyl ring is optionally substituted with $R^8$, and $R^1$, $R^3$, $R^4$, $R^8$, L and m are as defined in claim 1.

47. The compound of claim 46, wherein $R^1$ is —C(O)C($R^A$)═C($R^B$)$_p$ and ═ is a double bond and $R^A$ is hydrogen, p is two and at least one $R^B$ is independently deuterium, cyano, halogen, haloalkyl, hydroxyalkyl, heteroalkyl, heteroaryl, heteroarylalkyl, —$ZNR^5R^{11}$, —C(O)N($R^5$)$_2$, —NHC(O)C1-C3 alkyl, —N(CH$_3$)C(O)C1-C3 alkyl or heterocyclylalkyl wherein the heterocyclyl portion is substituted with one or more substituents independently selected from halogen, hydroxyl, alkoxy and C1-C3 alkyl.

48. The compound of claim 46, wherein $R^1$ is —C(O)C($R^A$)═C($R^B$)$_p$ and ═ is a double bond, each $R^B$ is hydrogen, and $R^A$ is deuterium, cyano, halogen, C1-C3 alkyl, haloalkyl, heteroalkyl, —C(O)N($R^5$)$_2$, or hydroxyalkyl.

49. A pharmaceutical composition, comprising a therapeutically effective amount of a compound of Formula (II) according to claim 1, and a pharmaceutically acceptable excipient.

50. A method for inhibiting KRas G12C activity in a cell, comprising contacting the cell in which inhibition of KRas G12C activity is desired with an effective amount of a compound of Formula (II) according to claim 1, pharmaceutically acceptable salts thereof or pharmaceutical compositions containing the compound of Formula (II), or pharmaceutically acceptable salt thereof.

51. A method for treating cancer comprising administering to a patient having cancer a therapeutically effective amount of a compound of Formula (II) or a pharmaceutically acceptable salt thereof according to claim 1, alone or combined with a pharmaceutically acceptable carrier, excipient or diluents, and wherein the cancer is selected from the group consisting of Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial 'carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

52. The method of claim 51, wherein the therapeutically effective amount of the compound is between about 0.01 to 100 mg/kg per day.

53. The method of claim 52, wherein the therapeutically effective amount of the compound is between about 0.1 to 50 mg/kg per day.

54. The method of claim 51, wherein the cancer wherein the cancer is a KRas G12C-associated cancer.

55. The method of claim 51, wherein the cancer is non-small cell lung cancer.

56. The method of claim 55, wherein non-small cell lung cancer is a KRas G12C-associated cancer.

57. A compound of the following structure:

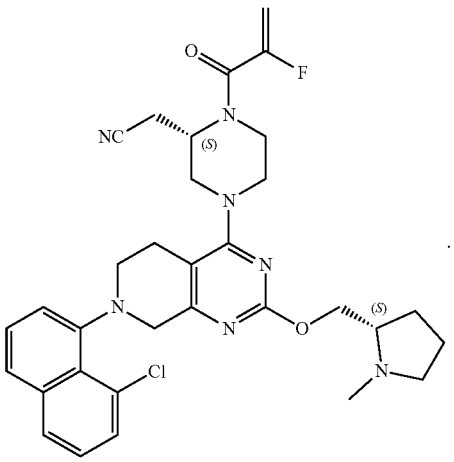

* * * * *